(12) United States Patent
Noller et al.

(10) Patent No.: US 7,133,783 B2
(45) Date of Patent: Nov. 7, 2006

(54) X-RAY CRYSTAL STRUCTURES OF FUNCTIONAL RIBOSOME COMPLEXES CONTAINING TRANSFER RNA AND MODEL MESSENGER RNAS AND METHODS OF USE

(75) Inventors: Harry F. Noller, Santa Cruz, CA (US); Jamie H. D. Cate, El Cerrito, CA (US); Marat M. Yusupov, Strasbourg (FR); Gulnara Zh. Yusupova, Strasbourg (FR); Albion E. Baucom, Santa Cruz, CA (US); Laura Lancaster, Santa Cruz, CA (US); Anne Dallas, Santa Cruz, CA (US); Kathy Lieberman, Santa Cruz, CA (US)

(73) Assignee: The Regents of the University of California, Oakland, CA (US)

( * ) Notice: Subject to any disclaimer, the term of this patent is extended or adjusted under 35 U.S.C. 154(b) by 631 days.

(21) Appl. No.: 10/013,379

(22) Filed: Dec. 10, 2001

(65) Prior Publication Data

US 2002/0188108 A1   Dec. 12, 2002

Related U.S. Application Data

(60) Provisional application No. 60/294,394, filed on May 30, 2001, provisional application No. 60/278,013, filed on Mar. 22, 2001, provisional application No. 60/254,603, filed on Dec. 9, 2000.

(51) Int. Cl.
*G06F 19/00* (2006.01)
*C12Q 1/00* (2006.01)
(52) U.S. Cl. .............................. 702/27; 435/4
(58) Field of Classification Search ................ 702/27; 435/4; 700/1
See application file for complete search history.

(56) References Cited

U.S. PATENT DOCUMENTS

| 5,835,382 A | 11/1998 | Wilson et al. |
| 5,856,116 A | 1/1999 | Wilson et al. |
| 5,888,738 A | 3/1999 | Hendry |
| 5,965,385 A | 10/1999 | Read et al. |
| 5,989,169 A | 11/1999 | Svendsen et al. |

FOREIGN PATENT DOCUMENTS

| AU | 0157846 A5 | 2/2002 |
| EP | 1172374 A1 | 1/2002 |
| EP | 1186614 A3 | 3/2002 |
| EP | 1188769 A2 | 3/2002 |
| WO | WO 00/69391 | 11/2000 |

OTHER PUBLICATIONS

Carson, M. Ribbons. Methods in Enzymology vol. 277, pp. 493-505 (1997).*
Afshar, et al., "Structure-Based and Combinatorial Search for New RNA-Binding Drugs," *Curr. Opin. Biotechnol.*, (1999) 10: 59-64.
Agrawal, R. K., et al., "Structural studies of the translational apparatus," *Curr. Opin. Struct. Biol.*, (1999a) 9:2 215-21.
Ban, N., et al., "A 9 A resolution X-ray crystallographic map of the large ribosomal subunit," *Cell*, (1998) 93:7 1105-1115.
Ban, N., et al. "Placement of protein and RNA structures into a 5 A-resolution map of the 50S ribosomal subunit," *Nature*, (1999) 400:6747 841-847.
Ban, N., et al., "The complete atomic structure of the large ribosomal subunit at 2.4 A resolution," *Science*, (2000) 289: 905-20.
Bohm H.J., "The Computer Program LUDI: A New Method for the De Novo Design of Enzyme Inhibitors," *J. Comp. Aid. Molec. Design*, (1992) 6: 61-78.
Carter, Andrew P., et al., "Functional insights from the structure of the 30s ribosomal subunit and its interactions with antibiotics," *Nature*, (Sep. 21, 2000) 407: 340-348.
Cate, J. H., et al., "X-ray crystal structures of 70S ribosome functional complexes," *Science*, (1999) 285: 2095-104.
Clemons, W. M., et al., "Structure of a bacterial 30S ribosomal subunit at 5.5 A resolution," *Nature*, (1999) 400:6747 833-840.
Correll, C.C., et al., "Metals, motifs, and recognition in the crystal structure of a 5S rRNA domain," *Cell*, (1997) 91:5 705-12.
Cohen, N.C., et al., "Molecular Modeling Software and Methods for Medicinal Chemistry," *J. Med. Chem.*, (1990) 33: 83-894.
Culver, Gloria, M., et al., "Identification of an RNA-Protein Bridge Spanning the Ribosomal Subunit Interface," *Science*, (1999) 285: 2133-2135.
Dallas, A., et al., "The loop E-loop D region of *Escherichia coli* 5S rRNA: the solution structure reveals an unusual loop that may be important for binding ribosomal proteins," *Structure*, (1997) 5:12 1639-53.
Feinberg, J., et al., Identification of molecular interactions between P site tRNA and the ribosome essential for translocation, *Proc. Nat. Acad. Sci.*, (2001) 20: 11120-5.
Frank, J., et al., A model of protein synthesis based on cryo-electron microscopy of the *E. coli* ribosome, *Nature*, (1995a) 376: 41-444.
Frank, J., et al., "A model of the translational apparatus based on a three-dimensional reconstruction of the *Escherichia coli* ribosome," *Biochem. Cell. Biol.*, (1995b) 73: 757-65.
Frank, J., et al., "A ratchet-like inter-subunit reorganization of the ribosome during translocation," *Nature*, (2000) 406: 318-22.

(Continued)

*Primary Examiner*—John S. Brusca
(74) *Attorney, Agent, or Firm*—Fenwick & West LLP

(57) ABSTRACT

5.5 Angstrom resolution x-ray crystallographic structures of 70S ribosome complexes containing messenger RNA and tranfer RNA (tRNA), or tRNA analogs, are provided. The resolution has been enhanced by fitting atomic resolution structures of 30S and 50S subunits onto the 5.5 anstrong electron density map. The enhanced structure reveals regions of structural differences between the 70S complex and the structures of the individual 30S and 50S components. Pharmacophore design to discover novel inhibitors or activators may be carried out using the enhanced 5.5 Angstrom 70S structure.

44 Claims, 31 Drawing Sheets
(26 of 31 Drawing Sheet(s) Filed in Color)

OTHER PUBLICATIONS

Gabashvili, I.S., et al., "Solution structure of the *E. coli* 70S ribosome at 11.5 A resolution," *Cell*, (2000) 100: 537-49.

Garcia, C., et al., "1H and 15N resonance assignments and structure of the N-terminal domain of *Escherichia coli* initiation factor 3," *Eur J Biochem.*, (1995a) 228: 395-402.

Garcia, C., et al., "Solution structure of the ribosome-binding domain of *E. coli* translation initiation factor IF3: homology with the U1A protein of the eukaryotic spliceosome," *J. Mol. Biol.*, (1995b) 254: 247-59.

Goodford, P.J., "A Computational Procedure for Dtermining Energetically Favorable Binding Sites on Biologically Important Macromolecules," *J. Med. Chem.*, (1985) 28: 849-857.

Hansen, H.A., et al., "Crystals of complexes mimicking protein biosynthesis are suitable for crystallographic studies," *Biochim. Biophys. Acta.*, (1990) 1050:1-3 1-7.

Hermann, T., et al., "Docking of cationic antibiotics to negatively charged pockets in RNA folds," *J. Med. Chem.*, (1999) 8:42 1250-61.

Holmberg, I., et al., "Mapping the ribosomal RNA neighborhood of protein L11 by directed hydr probing," *J. Mol. Biol.*, (1999) 289:2 223-33.

Hubbard, Roderick E., "Can drugs be designed," *Curr. Opin. Biotechnol.*, (1997) 8: 696-700.

Martin, Y.D., "3D Database Searching in Drug Design," *J. Med. Chem.*, (1992) 35:2145-2154.

Moore, P.B., et al., "The Three-Dimensional Structure Of The Ribosome And Its Components," *Annu. Rev. Biophys. Biomol. Struct.*, (1998) 27: 35-58.

Newcomb, L.R., et al., "Directed hydrolyl radical probing of 16S ribosomal RNA in 70S ribosomes positions of the RNA," *Biochemistry*, (1999) 38:3 945-51.

Newcomb, L.R., et al., "Directed hydrolyl radical probing of 16S rRNA in the ribosome: spatial pro elements of the 3' and 5' domains," *RNA*, (1999) 5:7 849-55.

Nikonov, S. V., et al., "Structural studies of ribosomal proteins," *Biol. Chem.*, (1988) 379:7 795-805.

Nissen, P., et al., "Crystal structure of the ernary complex of Phe-tRNA$^{Phe}_f$ EF-Tu, and a GTP analog," *Science*, (1995) 270: 1464-1472.

Nissen, P., et al:, "The structural basis of ribosome activity in peptide bond synthesis," *Science*, (2000) 289: 920-30.

Pioletti, M., et al. "Crystal structures of complexes of the small ribosomal subunit with tetracycline, edeine and IF3," *Embo J.*, (2001) 20: 1829-1839.

Ramakrishnan, V., et al., "Ribosomal protein structures: insights into . . . of the ribosome," *Trends Biochem. Sci.*, (1998) 23: 208212.

Samaha, R.R., et al., "Site-directed hydroxyl radical probing of 30S ribosomal subunits by using F an interruption in he 16S rRNA chain," *Proc. Nat'l. Acad. Sci. USA*, (1999), 96:2 366-70.

Schlunzen, Frank, et al., "Structural basis for the interation of antibiotics with the peptidyl transferase center ineubacteria," *Nature*, (2001) 413: 814-821.

Stark, H., et al., "Visualization of elongation factor Tu on the *Escherichia coli* ribosome," *Nature*, (1997a) 389: 03-406.

Szewczak, A.A., et al., "The sarcin/ricin loop, a modular RNA," *J. Mol. Biol.*, (1995) 247:1 81-98.

Trakhanov, S., et al., "Crystalization of 70S ribosomes and 30S ribosomal subunits form *Thermus thermophilus*," *FEBS Lett*, (1987) 220: 319.

Trakhanov, S., et al., "Preliminary X-ray investigation of 70 S ribosome crystals from *Thermus thermophilus*," *J. Mol. Biol.*, (1989) 209:1 327-8.

von Bohlen, K., et al., "Characterization and preliminary attempts for derivatization of crystals of large ribosomal subunits from Haloarcula marismortui diffracting to 3 A resolution,",*J. Mol. Biol.*, (1991) 222:1 11-5.

Wimberly, B.T., et al., "A detailed view of a ribosomal active site: the structure of the L11-RNA complex," *Cell*, (1999) 97:4 491-502.

Wimberly, B. T., et al., "Structure of the 30S ribosomal subunit," *Nature*, (2000) 407:327-39.

Yonath, A., et al., "Crystalization of the large ribosomal subunits from *Bacillus stearothermophilus*," *Biochem. Int.*, (1980) 1: 428-435.

Yusupov, M. M., et al., "*Thermus thermophilus* ribosomes for crystallographic studies," *Biochimie*, (1991) 73:7-8 887-97.

Yusupova, G. Z., et al., "Formation and crystallization of *Thermus thermophilus* 70S ribosome/tRNA complexes," *FEBS Lett.*, (1991) 290:1-2 69-72.

Yussupov, M. M. et al; "*Crystal Structure of the Risobome at 5.5 a Resolution*", Science, American Association of the Advancement of Science, vol. 292, No. 558, pp. 883-396 (May 2001).

International Search Report WO 02/046392, (2002).

\* cited by examiner

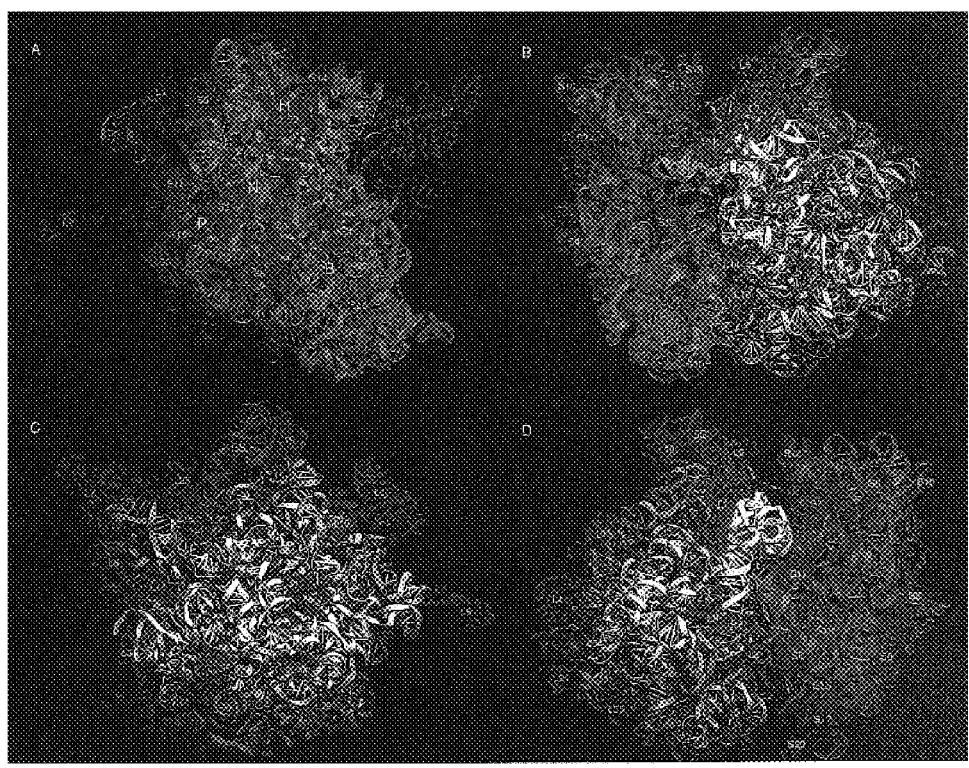
FIG. 2A-D

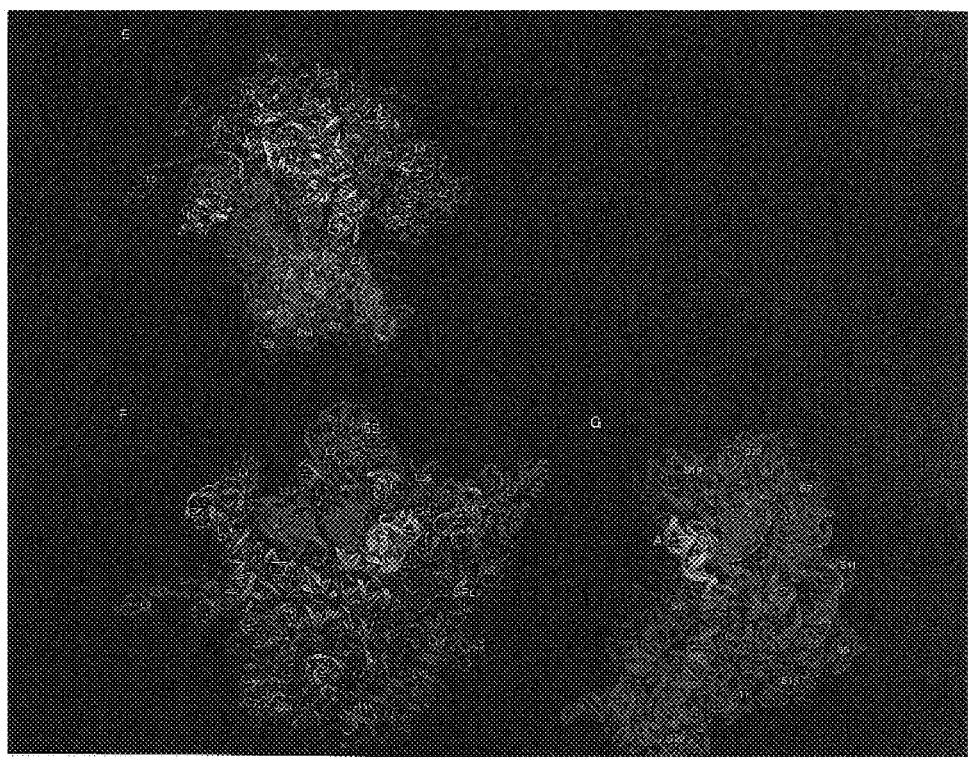
FIG. 2E-G

A

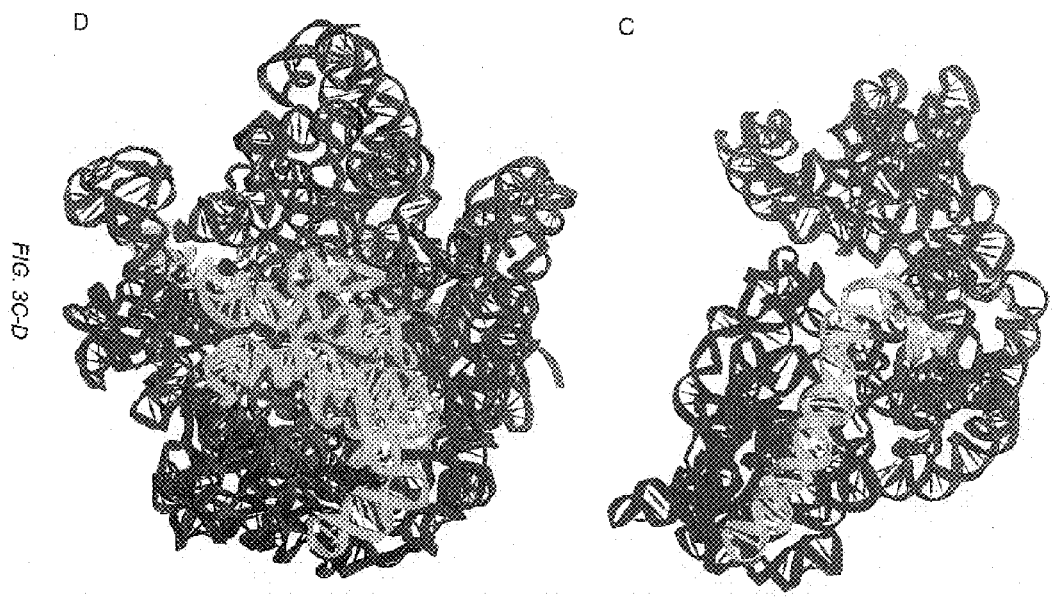
FIG. 3C-D

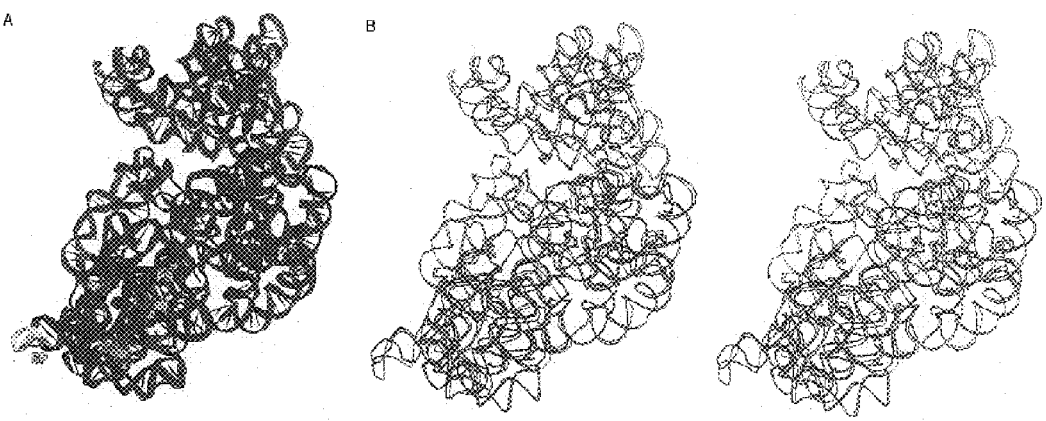
FIG. 4A-B

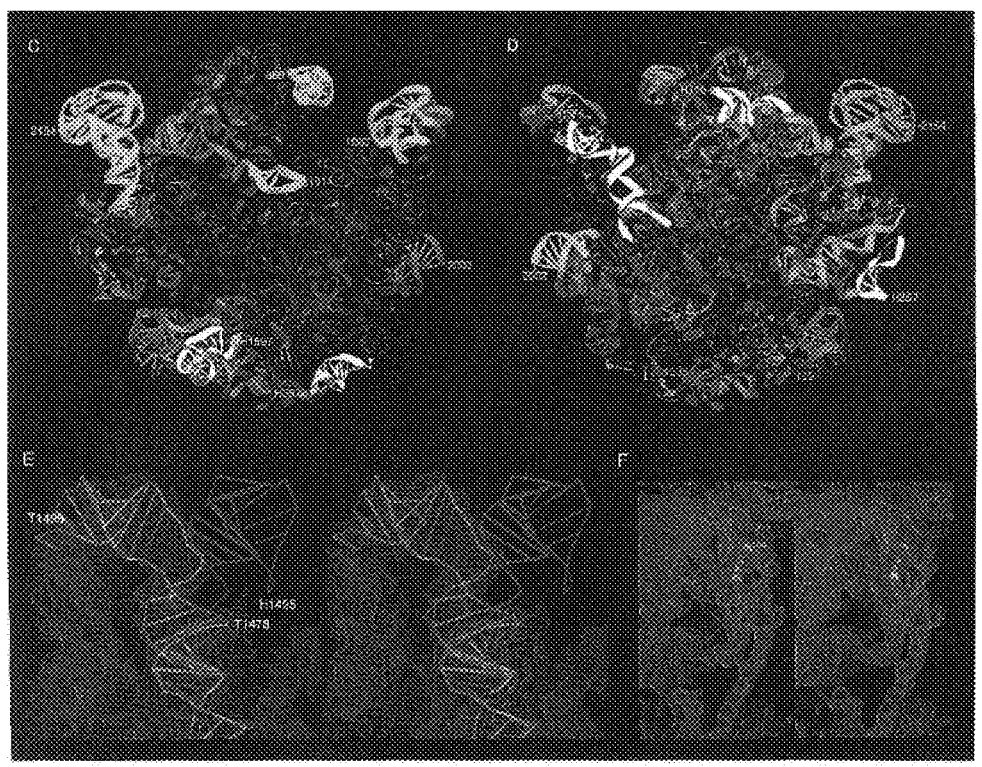
FIG. 4C-F

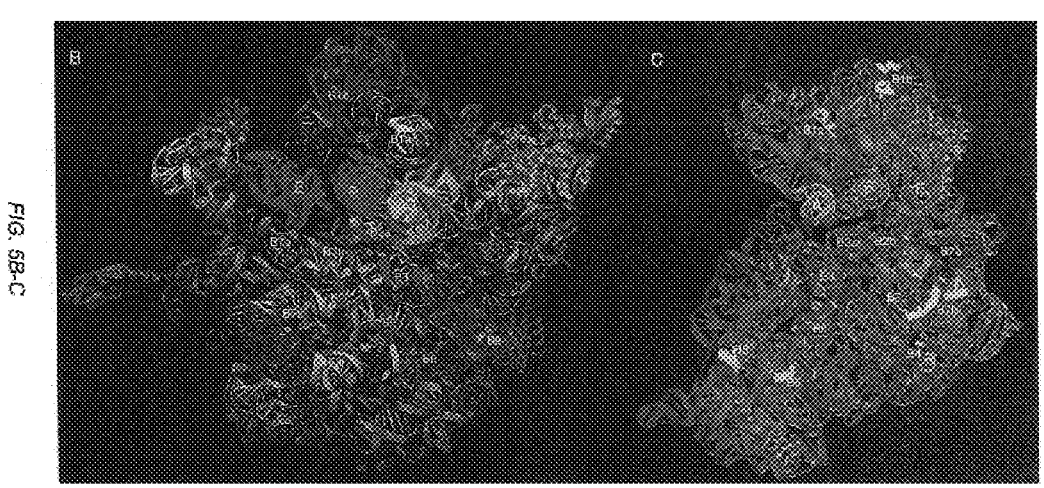
FIG. 5B-C

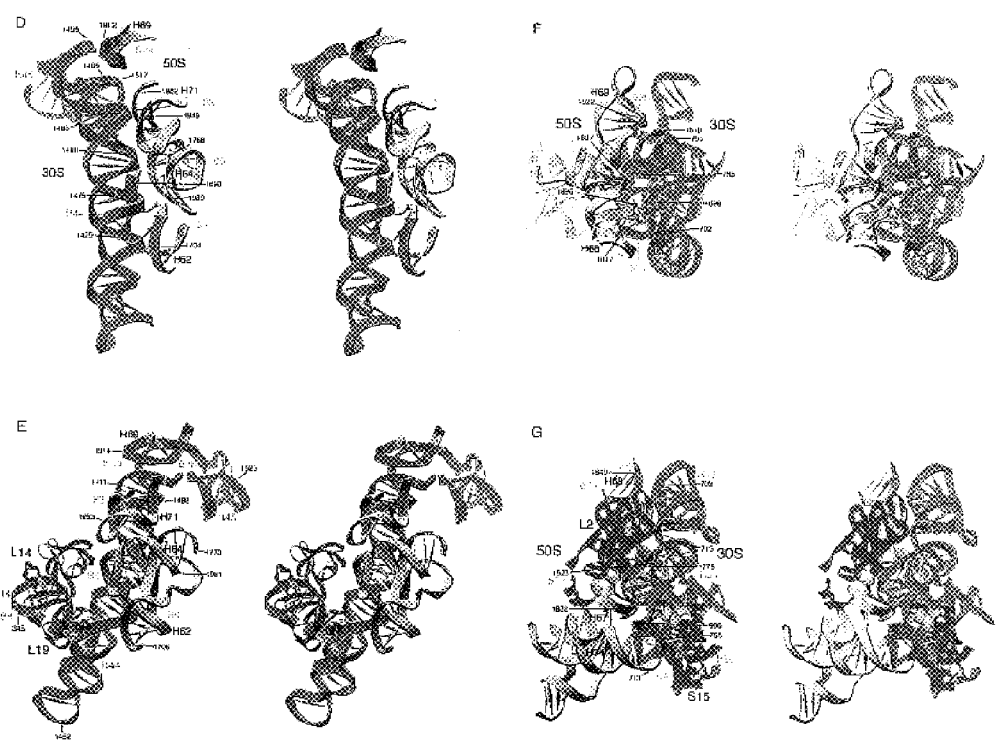
FIG. 5D-G

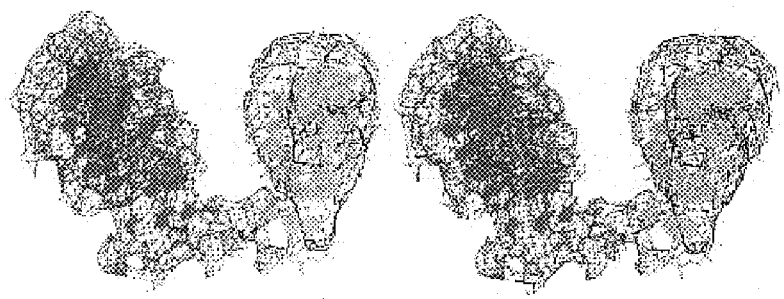
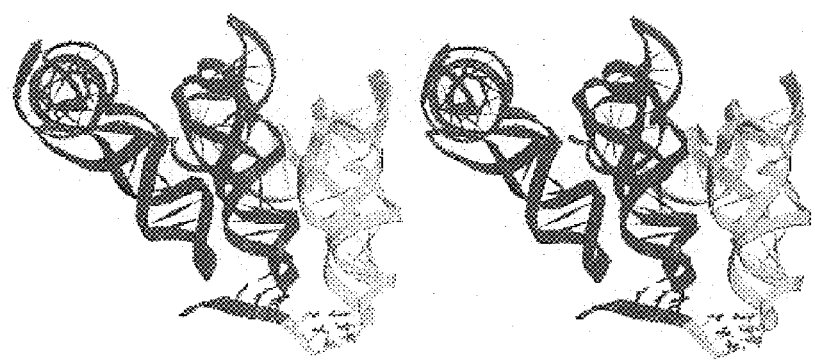
FIG. 6A-B

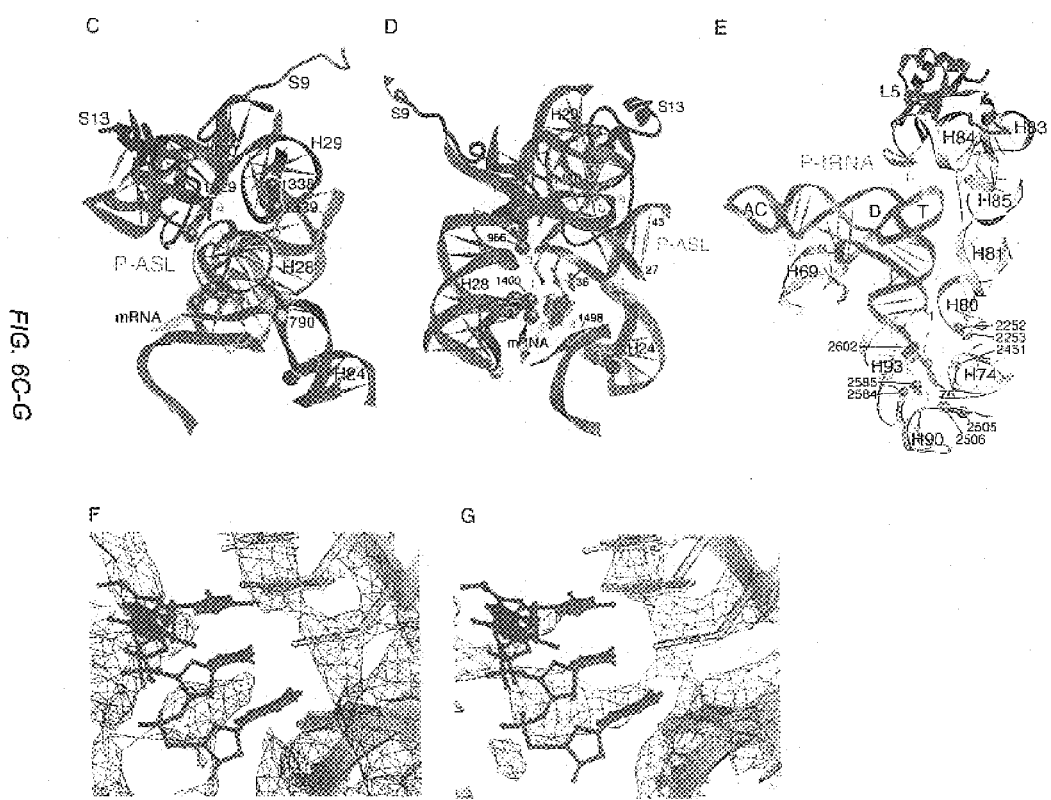
FIG. 6C-G

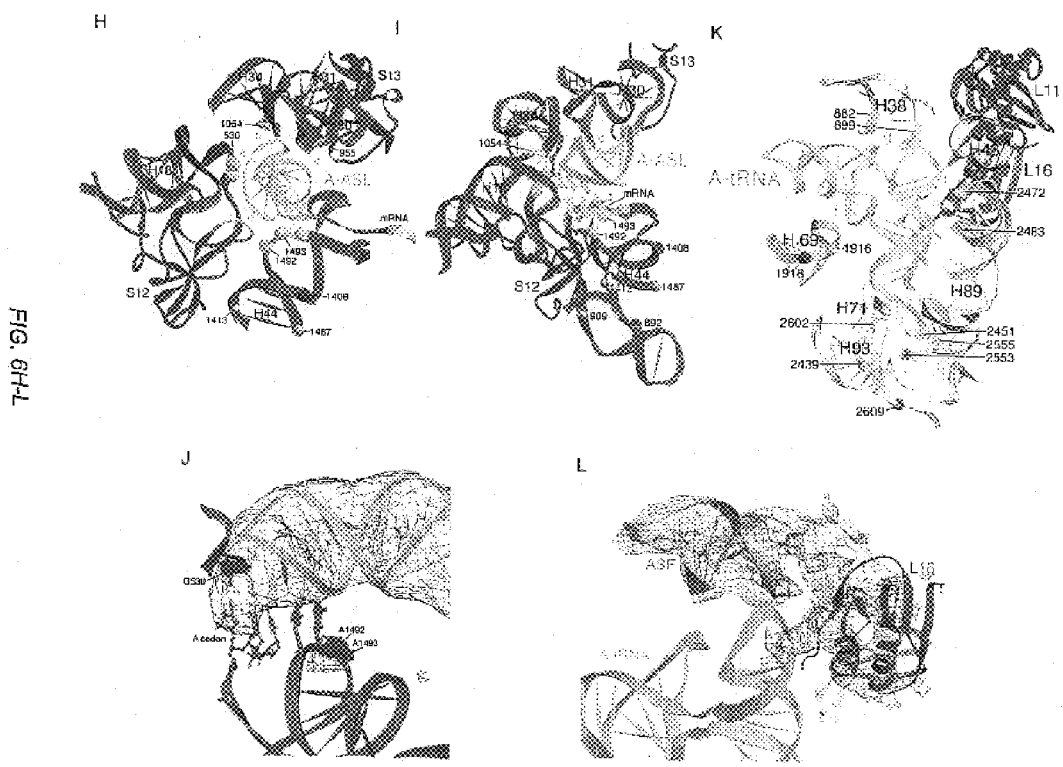
FIG. 6H-L

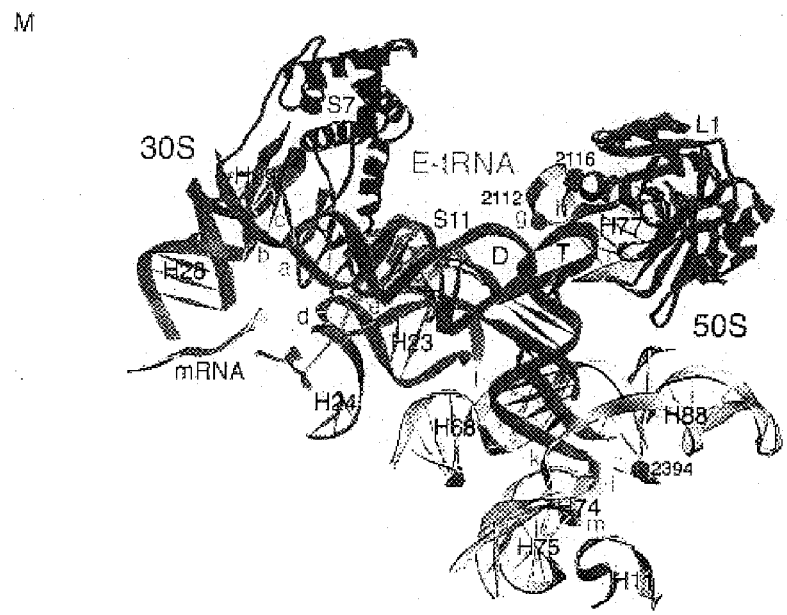
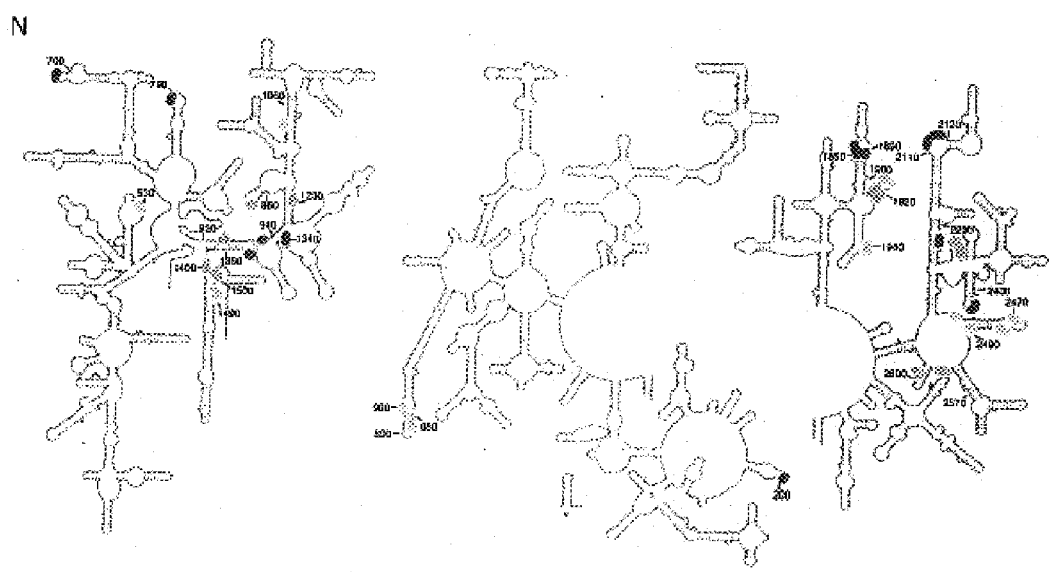
FIG. 6M-N

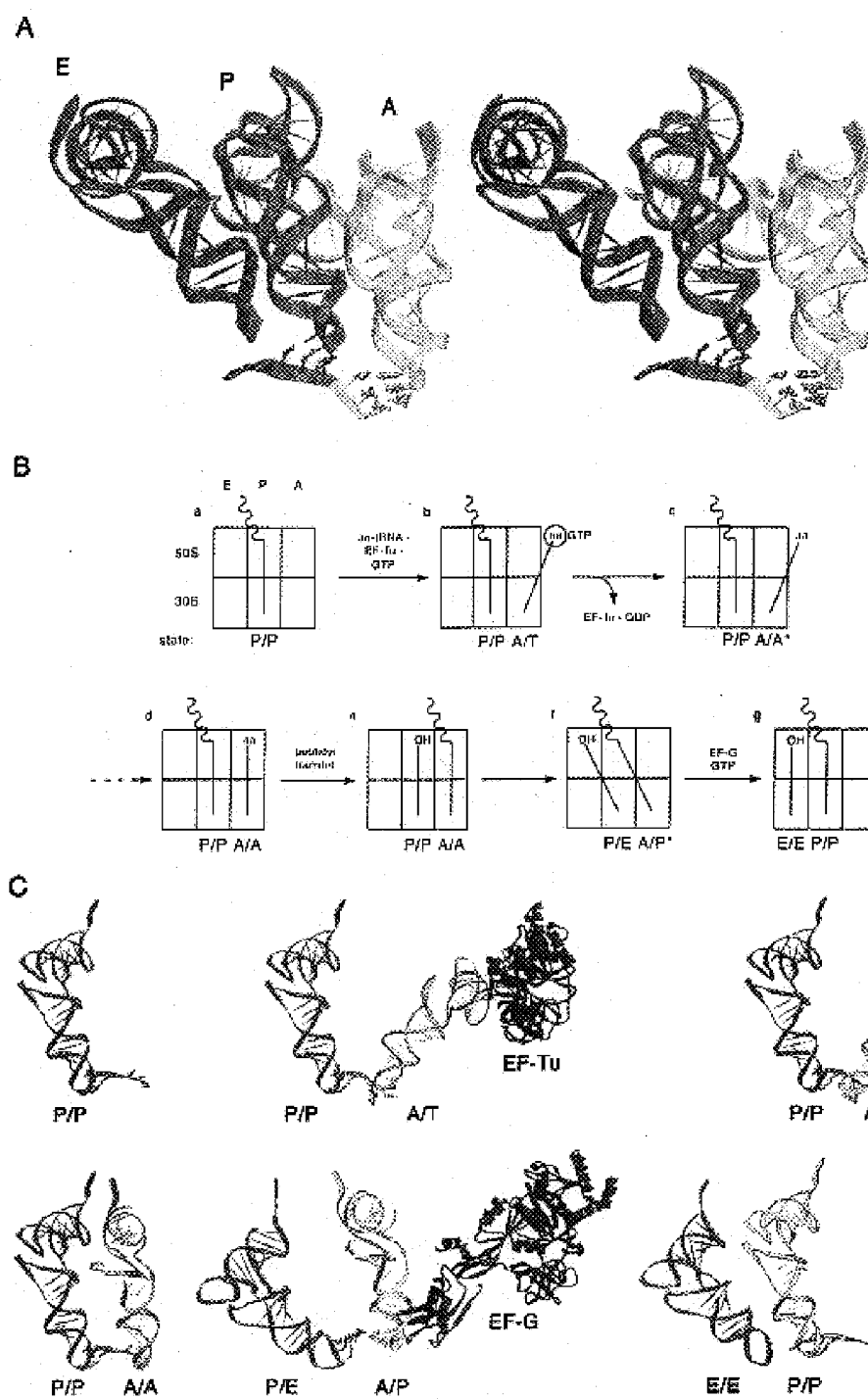
FIG. 7 A-C

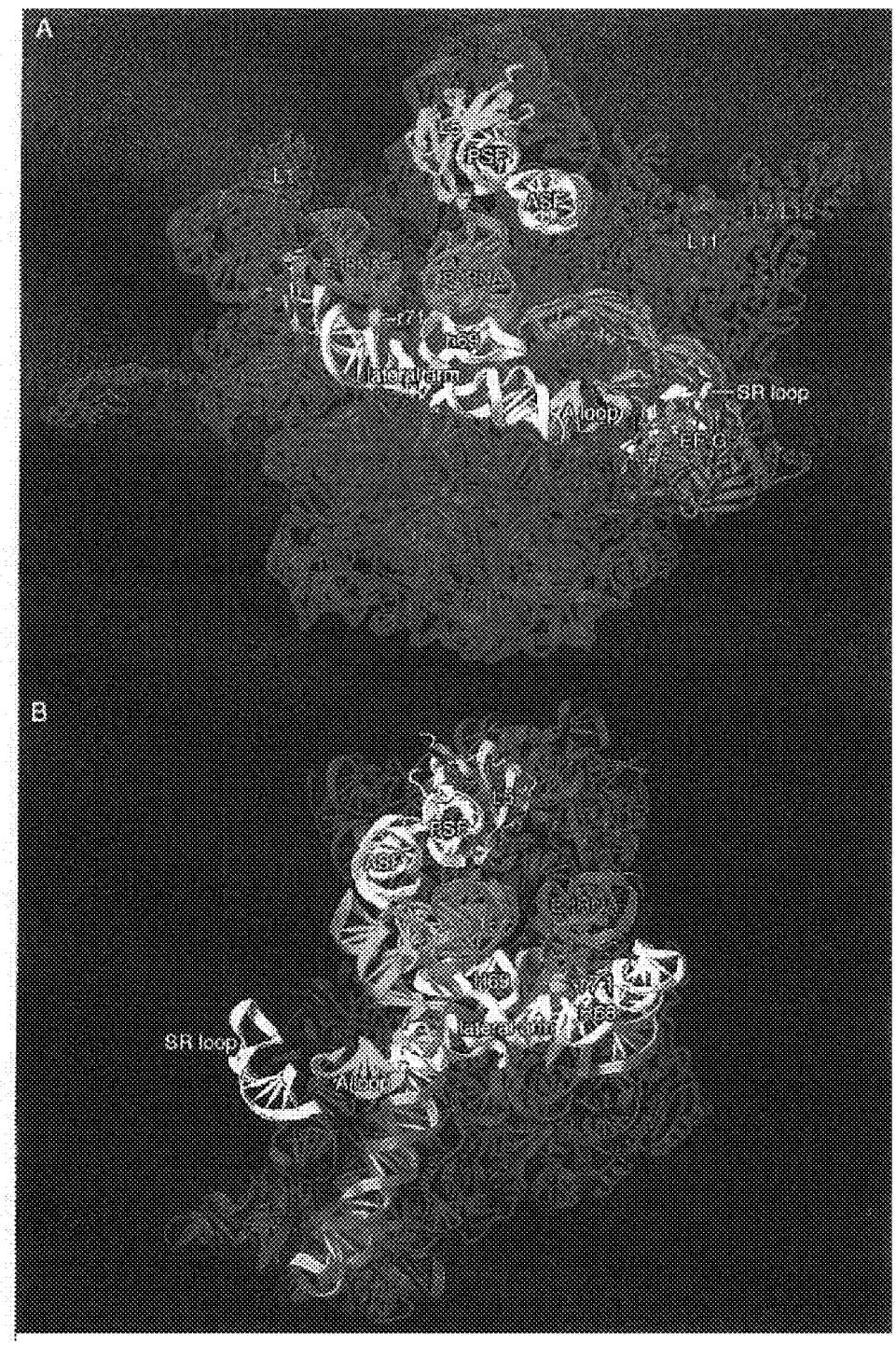
FIG. 8A-B

```
            -10        +1     ┌─  +10  ─┐      +20
MF36  (5')  GGCAAGGAGGUAAAAAUGUUUAAACGUAAAUCUACU  (3')
MV36  (5')  GGCAAGGAGGUAAAAAUGGUAAAACGUAAAUCAACU  (3')
MK27  (5')  GGCAAGGAGGUAAAAAUGAAAAAAAAA  (3')
             S/D          P   A
```

FIG. 9

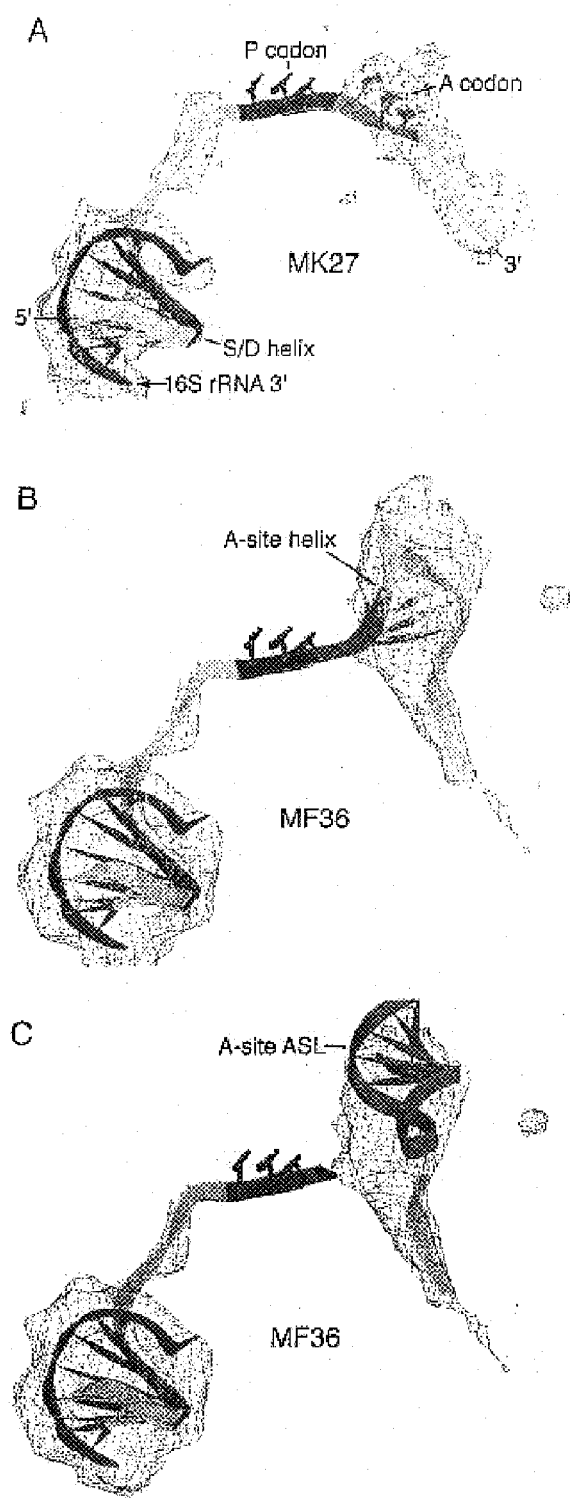
FIG. 10A-C

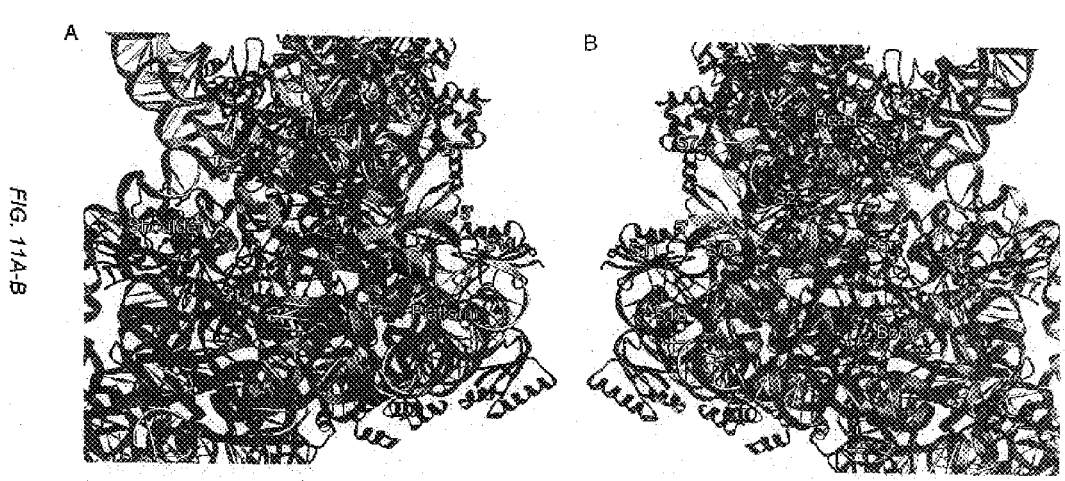
FIG. 11A-B

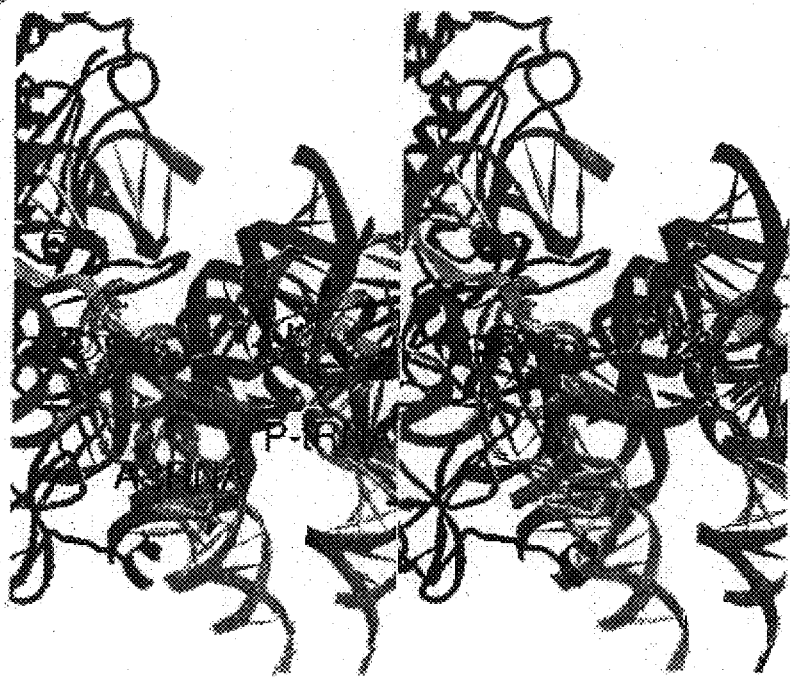
FIG. 12B-C

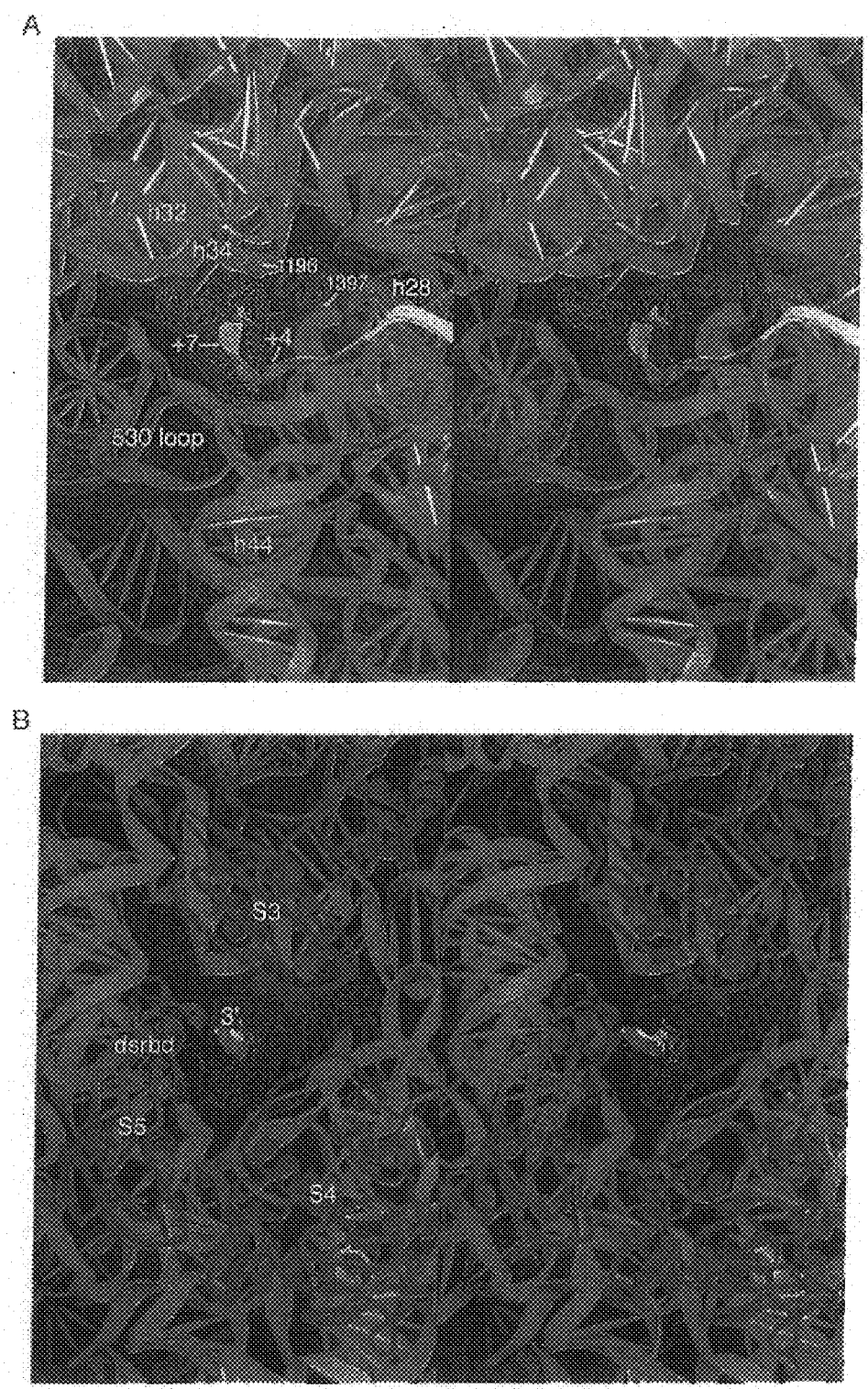
FIG. 13A-B

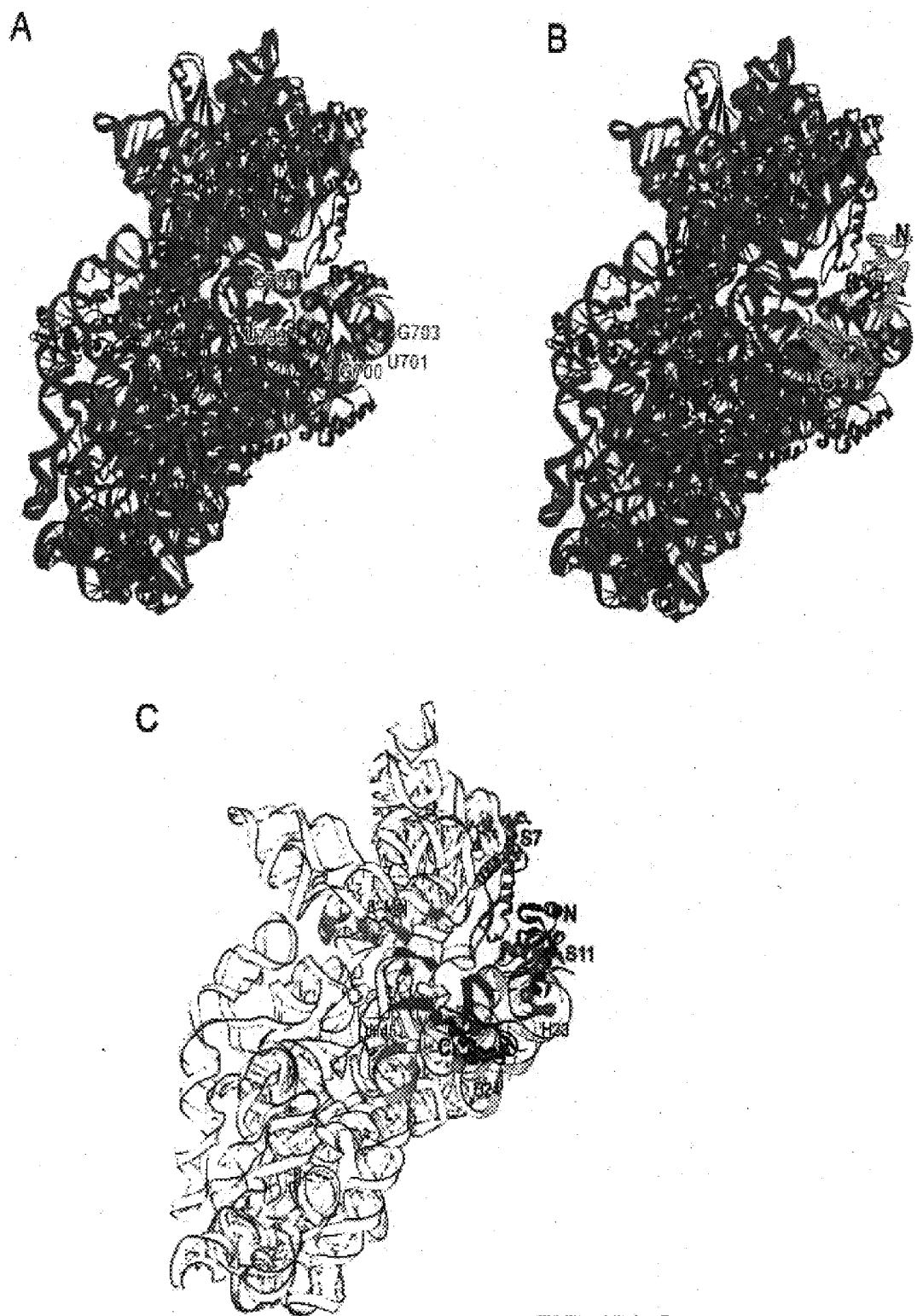
FIG. 19A-C

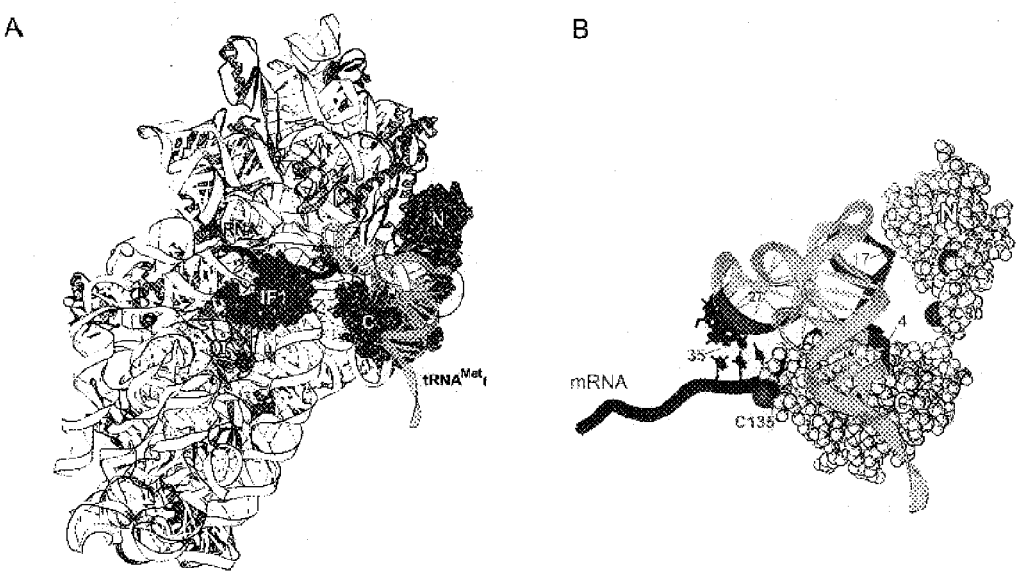
FIG. 20A-B

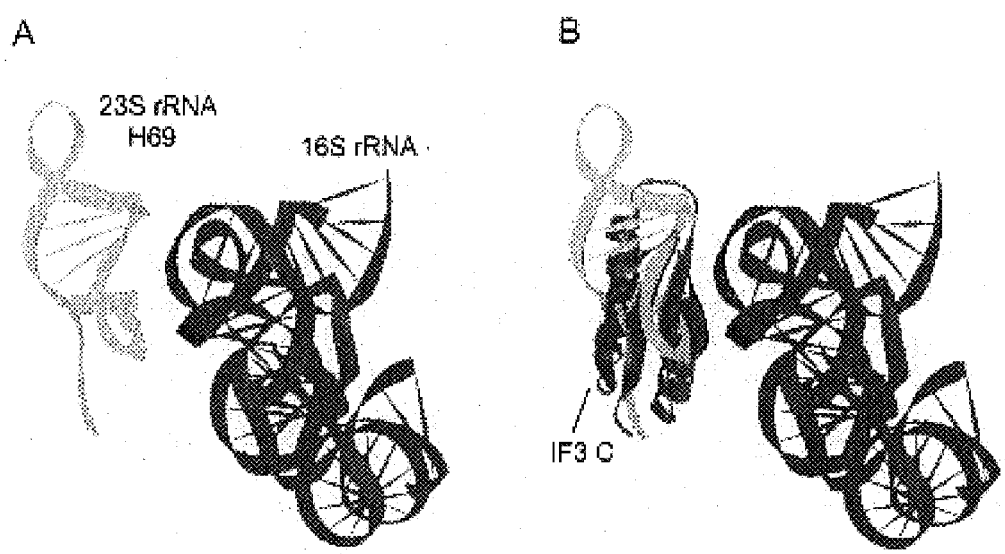
FIG. 21A-B

SEQUENCE LISTING

<160> NUMBER OF SEQ ID NOS: 54

<210> SEQ ID NO 1
<211> LENGTH: 228
<212> TYPE: PRT
<213> ORGANISM: Thermus thermophilus
<220> FEATURE:
<223> OTHER INFORMATION: 50S ribosomal protein L1
<223> OTHER INFORMATION: 1giyC

<400> SEQUENCE: 1

Pro Lys His Gly Lys Arg Tyr Arg Ala Leu Leu Glu Lys Val Asp Pro
1               5                   10                  15

Asn Lys Ile Tyr Thr Ile Asp Glu Ala Ala His Leu Val Lys Glu Leu
            20                  25                  30

Ala Thr Ala Lys Phe Asp Glu Thr Val Glu Val His Ala Lys Leu Gly
        35                  40                  45

Ile Asp Pro Arg Arg Ser Asp Gln Asn Val Arg Gly Thr Val Ser Leu
    50                  55                  60

Pro His Gly Leu Gly Lys Gln Val Arg Val Leu Ala Ile Ala Lys Gly
65                  70                  75                  80

Glu Lys Ile Lys Glu Ala Glu Ala Gly Ala Asp Tyr Val Gly Gly
                85                  90                  95

Glu Glu Ile Ile Gln Lys Ile Leu Asp Gly Trp Met Asp Phe Asp Ala
                100                 105                 110

Val Val Ala Thr Pro Asp Val Met Gly Ala Val Gly Ser Lys Leu Gly
            115                 120                 125

Arg Ile Leu Gly Pro Arg Gly Leu Leu Pro Asn Pro Lys Ala Gly Thr
    130                 135                 140

Val Gly Phe Asn Ile Gly Glu Ile Ile Arg Glu Ile Lys Ala Gly Arg
145                 150                 155                 160

Ile Glu Phe Arg Asn Asp Lys Thr Gly Ala Ile His Ala Pro Val Gly
                165                 170                 175

Lys Ala Ser Phe Pro Pro Glu Lys Leu Ala Asp Asn Ile Arg Ala Phe
            180                 185                 190

Ile Arg Ala Leu Glu Ala His Lys Pro Glu Gly Ala Lys Gly Thr Phe
        195                 200                 205

Leu Arg Ser Val Tyr Val Thr Thr Met Gly Pro Ser Val Arg Ile
    210                 215                 220

Asn Pro His Ser
225

<210> SEQ ID NO 2
<211> LENGTH: 178
<212> TYPE: PRT
<213> ORGANISM: Artificial Sequence
<220> FEATURE:
<223> OTHER INFORMATION: 50S ribosomal protein L2
<223> OTHER INFORMATION: 1giyD

<400> SEQUENCE: 2

Gln Tyr Arg Ile Ile Asp Phe Lys Arg Asp Lys Asp Gly Ile Pro Gly
1               5                   10                  15

Arg Val Ala Thr Ile Glu Tyr Asp Pro Asn Arg Ser Ala Asn Ile Ala
            20                  25                  30

Leu Ile Asn Tyr Ala Asp Gly Glu Lys Arg Tyr Ile Ile Ala Pro Lys
        35                  40                  45

```
Asn Leu Lys Val Gly Met Glu Ile Met Ser Gly Pro Asp Ala Asp Ile
 50                  55                  60

Lys Ile Gly Asn Ala Leu Pro Leu Glu Asn Ile Pro Val Gly Thr Leu
 65                  70                  75                  80

Val His Asn Ile Glu Leu Lys Pro Gly Arg Gly Gln Leu Val Arg
                 85                  90                  95

Ala Ala Gly Thr Ser Ala Gln Val Leu Gly Lys Glu Gly Lys Tyr Val
                100                 105                 110

Ile Val Arg Leu Ala Ser Gly Glu Val Arg Met Ile Leu Gly Lys Cys
                115                 120                 125

Arg Ala Thr Val Gly Glu Val Gly Asn Gly Gly Arg Thr Asp Lys Pro
                130                 135                 140

Phe Val Lys Ala Gly Asn Lys His His Lys Met Lys Ala Arg Gly Thr
145                 150                 155                 160

Lys Trp Pro Asn Val Arg Gly Val Ala Met Asn Ala Val Asp His Pro
                165                 170                 175

Phe Gly

<210> SEQ ID NO 3
<211> LENGTH: 338
<212> TYPE: PRT
<213> ORGANISM: Haloarcula marismortui
<220> FEATURE:
<223> OTHER INFORMATION: 50S ribosomal protein L3
<223> OTHER INFORMATION: 1giyE

<400> SEQUENCE: 3

Pro Gln Pro Ser Arg Pro Arg Lys Gly Ser Leu Gly Phe Gly Pro Arg
 1               5                  10                  15

Lys Arg Ser Thr Ser Glu Thr Pro Arg Phe Asn Ser Trp Pro Ser Asp
                 20                  25                  30

Asp Gly Gln Pro Gly Val Gln Gly Phe Ala Gly Tyr Lys Ala Gly Met
                 35                  40                  45

Thr His Val Val Leu Val Asn Asp Glu Pro Asn Ser Pro Arg Glu Gly
 50                  55                  60

Met Glu Glu Thr Val Pro Val Thr Val Ile Glu Thr Pro Pro Met Arg
 65                  70                  75                  80

Ala Val Ala Leu Arg Ala Tyr Glu Asp Thr Pro Tyr Gly Gln Arg Pro
                 85                  90                  95

Leu Thr Glu Val Trp Thr Asp Glu Phe His Ser Glu Leu Asp Arg Thr
                100                 105                 110

Leu Ser Asp Arg Leu Asp His Ala Leu Asp Ile Val Glu Asp Gln Ile
                115                 120                 125

Arg Asp Ala His Glu Ala Gly Asp Leu Gly Asp Leu Arg Leu Ile Thr
                130                 135                 140

His Thr Val Pro Asp Ala Val Pro Ser Val Pro Lys Lys Lys Pro Asp
145                 150                 155                 160

Val Met Glu Thr Arg Val Gly Gly Ser Val Ser Asp Arg Leu Asp
                165                 170                 175

His Ala Leu Asp Ile Val Glu Asp Gly Gly Glu His Ala Met Asn Asp
                180                 185                 190

Ile Phe Arg Ala Gly Glu Tyr Ala Asp Val Ala Gly Val Thr Lys Gly
                195                 200                 205

Lys Gly Thr Gln Gly Pro Val Lys Arg Trp Gly Val Gln Lys Arg Lys
                210                 215                 220
```

```
Gly Lys His Ala Arg Gln Gly Trp Arg Arg Ile Gly Asn Leu Gly
225                 230                 235                 240

Pro Trp Asn Pro Ser Arg Val Arg Ser Thr Val Pro Gln Gly Gln
                245                 250                 255

Thr Gly Tyr His Gln Arg Thr Glu Leu Asn Lys Arg Leu Ile Asp Ile
                260                 265                 270

Gly Glu Gly Asp Glu Pro Thr Val Asp Gly Phe Val Asn Tyr Gly
                275                 280                 285

Glu Val Asp Gly Pro Tyr Thr Leu Val Lys Gly Ser Val Pro Gly Pro
290                 295                 300

Asp Lys Arg Leu Val Pro Phe Phe Arg Pro Ala Val Arg Pro Asn Asp
305                 310                 315                 320

Gln Pro Arg Leu Asp Pro Glu Val Arg Tyr Val Ser Asn Glu Ser Asn
                325                 330                 335

Gln Gly

<210> SEQ ID NO 4
<211> LENGTH: 246
<212> TYPE: PRT
<213> ORGANISM: Haloarcula marismortui
<220> FEATURE:
<223> OTHER INFORMATION: 50s ribosomal protein L4
<223> OTHER INFORMATION: 1giyF

<400> SEQUENCE: 4

Met Glu Ala Thr Ile Tyr Asp Leu Asp Gly Asn Thr Asp Gly Glu Val
1               5                   10                  15

Asp Leu Pro Asp Val Phe Glu Thr Pro Val Arg Ser Asp Leu Ile Gly
                20                  25                  30

Lys Ala Val Arg Ala Ala Gln Ala Asn Arg Lys Gln Asp Tyr Gly Ser
                35                  40                  45

Asp Glu Tyr Ala Gly Leu Arg Thr Pro Ala Glu Ser Phe Gly Ser Gly
                50                  55                  60

Arg Gly Gln Ala His Val Pro Lys Leu Asp Gly Arg Ala Arg Arg Val
65                  70                  75                  80

Pro Gln Ala Val Lys Gly Arg Ser Ala His Pro Pro Lys Thr Glu Lys
                85                  90                  95

Asp Arg Ser Leu Asp Leu Asn Asp Lys Glu Arg Gln Leu Ala Val Arg
                100                 105                 110

Ser Ala Leu Ala Ala Thr Ala Asp Ala Asp Leu Val Ala Asp Arg Gly
                115                 120                 125

His Glu Phe Asp Arg Asp Glu Val Pro Val Val Ser Asp Asp Phe
130                 135                 140

Glu Asp Leu Val Lys Thr Gln Glu Val Val Ser Leu Leu Glu Ala Leu
145                 150                 155                 160

Asp Val His Ala Asp Ile Asp Arg Ala Asp Glu Thr Lys Ile Lys Ala
                165                 170                 175

Gly Gln Gly Ser Ala Arg Gly Arg Lys Tyr Arg Arg Pro Ala Ser Ile
                180                 185                 190

Leu Phe Val Thr Ser Asp Glu Pro Ser Thr Ala Ala Arg Asn Leu Ala
                195                 200                 205

Gly Ala Asp Val Ala Thr Ala Ser Glu Val Asn Thr Glu Asp Leu Ala
                210                 215                 220

Pro Gly Gly Ala Pro Gly Arg Leu Thr Val Phe Thr Glu Ser Ala Leu
225                 230                 235                 240
```

```
Ala Glu Val Ala Glu Arg
            245

<210> SEQ ID NO 5
<211> LENGTH: 176
<212> TYPE: PRT
<213> ORGANISM: Haloarcula marismortui
<220> FEATURE:
<223> OTHER INFORMATION: 50S ribosomal protein L5
<223> OTHER INFORMATION: 1giyG

<400> SEQUENCE: 5

Ser Ser Glu Ser Glu Ser Gly Gly Asp Phe His Glu Met Arg Glu Pro
1               5                   10                  15

Arg Ile Glu Lys Val Val Val His Met Gly Ile Gly His Gly Gly Arg
            20                  25                  30

Asp Leu Ala Asn Ala Glu Asp Ile Leu Gly Glu Ile Thr Gly Gln Met
        35                  40                  45

Pro Val Arg Thr Lys Ala Lys Arg Thr Val Gly Glu Phe Asp Ile Arg
    50                  55                  60

Glu Gly Asp Pro Ile Gly Ala Lys Val Thr Leu Arg Asp Glu Met Ala
65                  70                  75                  80

Glu Glu Phe Leu Gln Thr Ala Leu Pro Leu Ala Glu Leu Ala Thr Ser
                85                  90                  95

Gln Phe Asp Asp Thr Gly Asn Phe Ser Phe Gly Val Glu Glu His Thr
            100                 105                 110

Glu Phe Pro Ser Gln Glu Tyr Asp Pro Ser Ile Gly Ile Tyr Gly Leu
        115                 120                 125

Asp Val Thr Val Asn Leu Val Arg Pro Gly Tyr Arg Val Ala Lys Arg
    130                 135                 140

Asp Lys Ala Ser Arg Ser Ile Pro Thr Lys His Arg Leu Asn Pro Ala
145                 150                 155                 160

Asp Ala Val Ala Phe Ile Glu Ser Thr Tyr Asp Val Glu Val Ser Glu
                165                 170                 175

<210> SEQ ID NO 6
<211> LENGTH: 177
<212> TYPE: PRT
<213> ORGANISM: Bacillus stearothermophilus
<220> FEATURE:
<223> OTHER INFORMATION: 50S ribosomal protein L6
<223> OTHER INFORMATION: 1giyH

<400> SEQUENCE: 6

Ser Arg Val Gly Lys Lys Pro Ile Glu Ile Pro Ala Gly Val Thr Val
1               5                   10                  15

Thr Val Asn Gly Asn Thr Val Thr Val Lys Gly Pro Lys Gly Glu Leu
            20                  25                  30

Thr Arg Thr Phe His Pro Asp Met Thr Ile Thr Val Glu Gly Asn Val
        35                  40                  45

Ile Thr Val Thr Arg Pro Ser Asp Glu Lys His His Arg Ala Leu His
    50                  55                  60

Gly Thr Thr Arg Ser Leu Leu Ala Asn Met Val Glu Gly Val Ser Lys
65                  70                  75                  80

Gly Tyr Glu Lys Ala Leu Glu Leu Val Gly Val Gly Tyr Arg Ala Ser
                85                  90                  95

Lys Gln Gly Lys Lys Leu Val Leu Ser Val Gly Tyr Ser His Pro Val
            100                 105                 110
```

Glu Ile Glu Pro Glu Glu Gly Leu Glu Ile Val Pro Ser Gln Thr
            115                 120                 125

Lys Ile Ile Val Lys Gly Ala Asp Lys Gln Arg Val Gly Glu Leu Ala
    130                 135                 140

Ala Asn Ile Arg Ala Val Arg Pro Pro Glu Pro Tyr Lys Gly Lys Gly
145                 150                 155                 160

Ile Arg Tyr Glu Gly Glu Leu Val Arg Leu Lys Glu Gly Lys Thr Gly
                165                 170                 175

Lys

<210> SEQ ID NO 7
<211> LENGTH: 128
<212> TYPE: PRT
<213> ORGANISM: Thermotoga maritima
<220> FEATURE:
<223> OTHER INFORMATION: 50S ribosomal protein L7
<223> OTHER INFORMATION: 1giyI

<400> SEQUENCE: 7

Met Thr Ile Asp Glu Ile Ile Glu Ala Ile Glu Lys Leu Thr Val Ser
1               5                   10                  15

Glu Leu Ala Glu Leu Val Lys Lys Leu Glu Asp Lys Phe Gly Val Thr
            20                  25                  30

Ala Ala Ala Pro Val Ala Val Ala Ala Pro Val Ala Gly Ala Ala
        35                  40                  45

Ala Gly Ala Ala Gln Glu Glu Lys Thr Glu Phe Asp Val Val Leu Lys
    50                  55                  60

Ser Phe Gly Gln Asn Lys Ile Gln Val Ile Lys Val Val Arg Glu Ile
65                  70                  75                  80

Thr Gly Leu Gly Leu Lys Glu Ala Lys Asp Leu Val Glu Lys Ala Gly
                85                  90                  95

Ser Pro Asp Ala Val Ile Lys Ser Gly Val Ser Lys Glu Glu Ala Glu
                100                 105                 110

Glu Ile Lys Lys Lys Leu Glu Glu Ala Gly Ala Glu Val Glu Leu Lys
            115                 120                 125

<210> SEQ ID NO 8
<211> LENGTH: 128
<212> TYPE: PRT
<213> ORGANISM: Thermotoga maritima
<220> FEATURE:
<223> OTHER INFORMATION: 50S ribosomal protein L12
<223> OTHER INFORMATION: 1giyJ

<400> SEQUENCE: 8

Met Thr Ile Asp Glu Ile Ile Glu Ala Ile Glu Lys Leu Thr Val Ser
1               5                   10                  15

Glu Leu Ala Glu Leu Val Lys Lys Leu Glu Asp Lys Phe Gly Val Thr
            20                  25                  30

Ala Ala Ala Pro Val Ala Val Ala Ala Pro Val Ala Gly Ala Ala
        35                  40                  45

Ala Gly Ala Ala Gln Glu Glu Lys Thr Glu Phe Asp Val Val Leu Lys
    50                  55                  60

Ser Phe Gly Gln Asn Lys Ile Gln Val Ile Lys Val Val Arg Glu Ile
65                  70                  75                  80

Thr Gly Leu Gly Leu Lys Glu Ala Lys Asp Leu Val Glu Lys Ala Gly
                85                  90                  95

```
Ser Pro Asp Ala Val Ile Lys Ser Gly Val Ser Lys Glu Glu Ala Glu
            100                 105                 110

Glu Ile Lys Lys Lys Leu Glu Glu Ala Gly Ala Glu Val Glu Leu Lys
            115                 120                 125

<210> SEQ ID NO 9
<211> LENGTH: 149
<212> TYPE: PRT
<213> ORGANISM: Bacillus stearothermophilus
<220> FEATURE:
<223> OTHER INFORMATION: 50S ribosomal protein L9
<223> OTHER INFORMATION: 1giyK

<400> SEQUENCE: 9

Met Lys Val Ile Phe Leu Lys Asp Val Lys Gly Lys Gly Lys Lys Gly
  1               5                  10                  15

Glu Ile Lys Asn Val Ala Asp Gly Tyr Ala Asn Asn Phe Leu Phe Lys
             20                  25                  30

Gln Gly Leu Ala Ile Glu Ala Thr Pro Ala Asn Leu Lys Ala Leu Glu
         35                  40                  45

Ala Gln Lys Gln Lys Glu Gln Arg Gln Ala Ala Glu Glu Leu Ala Asn
 50                  55                  60

Ala Lys Lys Leu Lys Glu Gln Leu Glu Lys Leu Thr Val Thr Ile Pro
 65                  70                  75                  80

Ala Lys Ala Gly Glu Gly Gly Arg Leu Phe Gly Ser Ile Thr Ser Lys
                 85                  90                  95

Gln Ile Ala Glu Ser Leu Gln Ala Gln His Gly Leu Lys Leu Asp Lys
             100                 105                 110

Arg Lys Ile Glu Leu Ala Asp Ala Ile Arg Ala Leu Gly Tyr Thr Asn
             115                 120                 125

Val Pro Val Lys Leu His Pro Glu Val Thr Ala Thr Leu Lys Val His
         130                 135                 140

Val Thr Glu Gln Lys
145

<210> SEQ ID NO 10
<211> LENGTH: 141
<212> TYPE: PRT
<213> ORGANISM: Thermotoga maritima
<220> FEATURE:
<223> OTHER INFORMATION: 50S ribosomal protein L11
<223> OTHER INFORMATION: 1giyL

<400> SEQUENCE: 10

Met Ala Lys Lys Val Ala Ala Gln Ile Lys Leu Gln Leu Pro Ala Gly
  1               5                  10                  15

Lys Ala Thr Pro Ala Pro Pro Val Gly Pro Ala Leu Gly Gln His Gly
             20                  25                  30

Val Asn Ile Met Glu Phe Cys Lys Arg Phe Asn Ala Glu Thr Ala Asp
         35                  40                  45

Lys Ala Gly Met Ile Leu Pro Val Val Ile Thr Val Tyr Glu Asp Lys
 50                  55                  60

Ser Phe Thr Phe Ile Ile Lys Thr Pro Pro Ala Ser Phe Leu Leu Lys
 65                  70                  75                  80

Lys Ala Ala Gly Ile Glu Lys Gly Ser Ser Glu Pro Lys Arg Lys Ile
                 85                  90                  95

Val Gly Lys Val Thr Arg Lys Gln Ile Glu Glu Ile Ala Lys Thr Lys
             100                 105                 110
```

```
Met Pro Asp Leu Asn Ala Asn Ser Leu Glu Ala Ala Met Lys Ile Ile
        115                 120                 125

Glu Gly Thr Ala Lys Ser Met Gly Ile Glu Val Val Asp
        130                 135                 140

<210> SEQ ID NO 11
<211> LENGTH: 145
<212> TYPE: PRT
<213> ORGANISM: Haloarcula marismortui
<220> FEATURE:
<223> OTHER INFORMATION: 50S ribosomal protein L13
<223> OTHER INFORMATION: 1giyM

<400> SEQUENCE: 11

Met Ser Val Ala Glu Phe Asp Ala Asp Val Ile Val Asp Ala Arg Asp
  1               5                  10                  15

Cys Ile Met Gly Arg Val Ala Ser Gln Val Ala Glu Gln Ala Leu Asp
             20                  25                  30

Gly Glu Thr Val Ala Val Asn Ala Glu Arg Ala Val Ile Thr Gly
         35                  40                  45

Arg Glu Glu Gln Ile Val Glu Lys Tyr Glu Lys Arg Val Asp Ile Gly
     50                  55                  60

Asn Asp Asn Gly Tyr Phe Tyr Pro Lys Arg Pro Asp Gly Ile Phe Lys
 65                  70                  75                  80

Arg Thr Ile Arg Gly Met Leu Pro His Lys Lys Gln Arg Gly Arg Glu
                 85                  90                  95

Ala Phe Glu Ser Val Arg Val Tyr Leu Gly Asn Pro Tyr Asp Glu Asp
             100                 105                 110

Gly Glu Val Leu Asp Gly Thr Ser Leu Asp Arg Leu Ser Asn Ile Lys
         115                 120                 125

Phe Val Thr Leu Gly Glu Ile Ser Glu Thr Leu Gly Ala Asn Lys Thr
     130                 135                 140

Trp
145

<210> SEQ ID NO 12
<211> LENGTH: 122
<212> TYPE: PRT
<213> ORGANISM: Bacillus stearothermophilus
<220> FEATURE:
<223> OTHER INFORMATION: 50S ribosomal protein L14
<223> OTHER INFORMATION: 1giyN

<400> SEQUENCE: 12

Met Ile Gln Gln Glu Ser Arg Leu Lys Val Ala Asp Asn Ser Gly Ala
  1               5                  10                  15

Arg Glu Val Leu Val Ile Lys Val Leu Gly Gly Ser Gly Arg Arg Tyr
             20                  25                  30

Ala Asn Ile Gly Asp Val Val Ala Thr Val Lys Asp Ala Thr Pro
         35                  40                  45

Gly Gly Val Val Lys Lys Gly Gln Val Val Lys Ala Val Val Arg
     50                  55                  60

Thr Lys Arg Gly Val Arg Arg Pro Asp Gly Ser Tyr Ile Arg Phe Asp
 65                  70                  75                  80

Glu Asn Ala Cys Val Ile Ile Arg Asp Asp Lys Ser Pro Arg Gly Thr
                 85                  90                  95

Arg Ile Phe Gly Pro Val Ala Arg Glu Leu Arg Asp Lys Asp Phe Met
             100                 105                 110
```

-continued

```
Lys Ile Ile Ser Leu Ala Pro Glu Val Ile
        115                 120

<210> SEQ ID NO 13
<211> LENGTH: 164
<212> TYPE: PRT
<213> ORGANISM: Haloarcula marismortui
<220> FEATURE:
<223> OTHER INFORMATION: 50S ribosomal protein L15
<223> OTHER INFORMATION: 1giyO

<400> SEQUENCE: 13

Thr Ser Lys Lys Arg Gln Arg Gly Ser Arg Thr His Gly Gly Gly
1               5                   10                  15

Ser His Lys Asn Arg Arg Gly Ala Gly His Arg Gly Gly Arg Gly Asp
            20                  25                  30

Ala Gly Arg Asp Lys His Glu Phe His Asn His Glu Pro Leu Gly Lys
        35                  40                  45

Ser Gly Phe Lys Arg Pro Gln Lys Val Gln Glu Ala Ala Thr Ile
    50                  55                  60

Asp Val Arg Glu Ile Asp Glu Asn Val Thr Leu Leu Ala Ala Asp Asp
65              70                  75                  80

Val Ala Glu Val Glu Asp Gly Gly Phe Arg Val Asp Val Arg Asp Val
                85                  90                  95

Val Glu Glu Ala Asp Asp Ala Asp Tyr Val Lys Val Leu Gly Ala Gly
            100                 105                 110

Gln Val Arg His Glu Leu Thr Leu Ile Ala Asp Phe Ser Glu Gly
        115                 120                 125

Ala Arg Glu Lys Val Glu Gly Ala Gly Gly Ser Val Glu Leu Thr Asp
    130                 135                 140

Leu Gly Glu Glu Arg Gln Ala Glu Ala Glu Glu Thr Glu Asp Ala Asp
145                 150                 155                 160

Ala Asp Glu Glu

<210> SEQ ID NO 14
<211> LENGTH: 138
<212> TYPE: PRT
<213> ORGANISM: Thermus thermophilus
<220> FEATURE:
<223> OTHER INFORMATION: 50S ribosomal protein L16
<223> OTHER INFORMATION: 1giyP

<400> SEQUENCE: 14

Ser Ile Lys Pro Thr Arg Arg Glu Tyr Ile Ser Gly Ile Pro Gly Lys
1               5                   10                  15

Gly Ile Ala Gln Phe Lys Met Gly Asn Asn Thr Tyr Pro Ala Gln Val
            20                  25                  30

Glu Asn Val Val Glu Lys Pro Val Gln Ile Arg His Asn Ala Leu Glu
        35                  40                  45

Ala Ala Arg Asn Ala Ala Asn Arg Phe Val Gln Asn Ser Gly Lys Phe
    50                  55                  60

Arg Ile Arg Lys Phe Pro His Val Ile Arg Glu Gln Asp Gly Asp
65              70                  75                  80

Gly Met Arg Ala Pro Phe Gly Lys Ser Val Gly Thr Ala Ala Arg Ser
                85                  90                  95

His Gly Ala Asn His Asp Phe Ile Ala Trp Val Asn Pro Asp Pro Ala
            100                 105                 110

Val Glu Phe Ala Trp Arg Arg Ala Tyr Met Lys Val Thr Pro Thr Val
```

```
                    115                 120                 125

Asn Ile Asp Ser Ser Pro Ala Gly Asn Ala
    130                 135

<210> SEQ ID NO 15
<211> LENGTH: 186
<212> TYPE: PRT
<213> ORGANISM: Haloarcula marismortui
<220> FEATURE:
<223> OTHER INFORMATION: 50S ribosomal protein L18
<223> OTHER INFORMATION: 1giyQ

<400> SEQUENCE: 15

Ala Thr Gly Pro Arg Tyr Lys Val Pro Met Arg Arg Arg Glu Ala
1               5                   10                  15

Arg Thr Asp Tyr His Gln Arg Leu Arg Leu Leu Lys Ser Gly Lys Pro
            20                  25                  30

Arg Leu Val Ala Arg Lys Ser Asn Lys His Val Arg Ala Gln Leu Val
        35                  40                  45

Thr Leu Gly Pro Asn Gly Asp Asp Thr Leu Ala Ser Ala His Ser Ser
    50                  55                  60

Asp Leu Ala Glu Tyr Gly Trp Glu Ala Pro Thr Gly Asn Met Pro Ser
65                  70                  75                  80

Ala Tyr Leu Thr Gly Leu Leu Ala Gly Leu Arg Ala Gln Glu Ala Gly
                85                  90                  95

Val Glu Glu Ala Val Leu Asp Ile Gly Leu Asn Ser Pro Thr Pro Gly
            100                 105                 110

Ser Lys Val Phe Ala Ile Gln Glu Gly Ala Ile Asp Ala Gly Leu Asp
        115                 120                 125

Ile Pro His Asn Asp Asp Val Leu Ala Asp Trp Gln Arg Thr Arg Gly
    130                 135                 140

Ala His Ile Ala Glu Tyr Asp Glu Gln Leu Glu Glu Pro Leu Tyr Ser
145                 150                 155                 160

Gly Asp Phe Asp Ala Ala Asp Leu Pro Glu His Phe Asp Glu Leu Arg
                165                 170                 175

Glu Thr Leu Leu Asp Gly Asp Ile Glu Leu
            180                 185

<210> SEQ ID NO 16
<211> LENGTH: 66
<212> TYPE: PRT
<213> ORGANISM: Haloarcula marismortui
<220> FEATURE:
<223> OTHER INFORMATION: 50S ribosomal protein L19
<223> OTHER INFORMATION: 1giyR

<400> SEQUENCE: 16

Pro Arg Thr Arg Glu Cys Asp Tyr Cys Gly Thr Asp Ile Glu Pro Gly
1               5                   10                  15

Thr Gly Thr Met Phe Val His Lys Asp Gly Ala Thr His Phe Cys
            20                  25                  30

Ser Ser Lys Cys Glu Asn Asn Ala Asp Leu Gly Arg Glu Ala Arg Asn
        35                  40                  45

Leu Glu Trp Thr Asp Thr Ala Arg Gly Glu Ala Gly Glu Ala Glu Asp
    50                  55                  60

Glu Ala
65
```

```
<210> SEQ ID NO 17
<211> LENGTH: 113
<212> TYPE: PRT
<213> ORGANISM: Thermus thermophilus
<220> FEATURE:
<223> OTHER INFORMATION: 50S ribosomal protein L22
<223> OTHER INFORMATION: 1giyS

<400> SEQUENCE: 17

Met Glu Ala Lys Ala Ile Ala Arg Tyr Val Arg Ile Ser Pro Arg Lys
 1               5                  10                  15

Val Arg Leu Val Val Asp Leu Ile Arg Gly Lys Ser Leu Glu Glu Ala
            20                  25                  30

Arg Asn Ile Leu Arg Tyr Thr Asn Lys Arg Gly Ala Tyr Phe Val Ala
        35                  40                  45

Lys Val Leu Glu Ser Ala Ala Asn Ala Val Asn Asn His Asp Met
    50                  55                  60

Leu Glu Asp Arg Leu Tyr Val Lys Ala Ala Tyr Val Asp Glu Gly Pro
65                  70                  75                  80

Ala Leu Lys Arg Val Leu Pro Arg Ala Arg Gly Arg Ala Asp Ile Ile
                85                  90                  95

Lys Lys Arg Thr Ser His Ile Thr Val Ile Leu Gly Glu Lys His Gly
            100                 105                 110

Lys

<210> SEQ ID NO 18
<211> LENGTH: 84
<212> TYPE: PRT
<213> ORGANISM: Haloarcula marismortui
<220> FEATURE:
<223> OTHER INFORMATION: 50S ribosomal protein L23
<223> OTHER INFORMATION: 1giyT

<400> SEQUENCE: 18

Ser Trp Asp Val Ile Lys His Pro His Val Thr Glu Lys Ala Met Asn
 1               5                  10                  15

Asp Met Asp Phe Gln Asn Lys Leu Gln Phe Ala Val Asp Asp Arg Ala
            20                  25                  30

Ser Lys Gly Glu Val Ala Asp Ala Val Glu Glu Gln Tyr Asp Val Thr
        35                  40                  45

Val Glu Gln Val Asn Thr Gln Asn Thr Met Asp Gly Glu Lys Lys Ala
    50                  55                  60

Val Val Arg Leu Ser Glu Asp Asp Ala Gln Glu Val Ala Ser Arg
65                  70                  75                  80

Ile Gly Val Phe

<210> SEQ ID NO 19
<211> LENGTH: 119
<212> TYPE: PRT
<213> ORGANISM: Haloarcula marismortui
<220> FEATURE:
<223> OTHER INFORMATION: 50S ribosomal protein L24
<223> OTHER INFORMATION: 1giyU

<400> SEQUENCE: 19

Ser Lys Gln Pro Asp Lys Gln Arg Lys Ser Gln Arg Arg Ala Pro Leu
 1               5                  10                  15

His Glu Arg His Lys Gln Val Arg Ala Thr Leu Ser Ala Asp Leu Arg
            20                  25                  30

Glu Glu Tyr Gly Gln Arg Asn Val Arg Val Asn Ala Gly Asp Thr Val
```

```
                35                  40                  45
Glu Val Leu Arg Gly Asp Phe Ala Gly Glu Gly Glu Val Ile Asn
 50                  55                  60

Val Asp Leu Asp Lys Ala Val Ile His Val Glu Asp Val Thr Leu Glu
 65                  70                  75                  80

Lys Thr Asp Gly Glu Glu Val Pro Arg Pro Leu Asp Thr Ser Asn Val
                 85                  90                  95

Arg Val Thr Asp Leu Asp Leu Glu Asp Glu Lys Arg Glu Ala Arg Leu
                100                 105                 110

Glu Ser Glu Asp Asp Ser Ala
        115

<210> SEQ ID NO 20
<211> LENGTH: 94
<212> TYPE: PRT
<213> ORGANISM: Escherichia coli
<220> FEATURE:
<223> OTHER INFORMATION: 50S ribosomal protein L25
<223> OTHER INFORMATION: 1giyV

<400> SEQUENCE: 20

Met Phe Thr Ile Asn Ala Glu Val Arg Lys Glu Gln Gly Lys Gly Ala
 1               5                  10                  15

Ser Arg Arg Leu Arg Ala Ala Asn Lys Phe Pro Ala Ile Ile Tyr Gly
                 20                  25                  30

Gly Lys Glu Ala Pro Leu Ala Ile Glu Leu Asp His Asp Lys Val Met
                 35                  40                  45

Asn Met Gln Ala Lys Ala Glu Phe Tyr Ser Glu Val Leu Thr Ile Val
 50                  55                  60

Val Asp Gly Lys Glu Ile Lys Val Lys Ala Gln Asp Val Gln Arg His
 65                  70                  75                  80

Pro Tyr Lys Pro Lys Leu Gln His Ile Asp Phe Val Arg Ala
                 85                  90

<210> SEQ ID NO 21
<211> LENGTH: 70
<212> TYPE: PRT
<213> ORGANISM: Haloarcula marismortui
<220> FEATURE:
<223> OTHER INFORMATION: 50S ribosomal protein L29
<223> OTHER INFORMATION: 1giyW

<400> SEQUENCE: 21

Thr Val Leu His Val Gln Glu Ile Arg Asp Met Thr Pro Ala Glu Arg
 1               5                  10                  15

Glu Ala Glu Leu Asp Asp Leu Lys Thr Glu Leu Leu Asn Ala Arg Ala
                 20                  25                  30

Val Gln Ala Ala Gly Gly Ala Pro Glu Asn Pro Gly Arg Ile Lys Glu
                 35                  40                  45

Leu Arg Lys Ala Ile Ala Arg Ile Lys Thr Ile Gln Gly Glu Glu Gly
                 50                  55                  60

Asp Leu Gln Glu Asn Glu
 65                  70

<210> SEQ ID NO 22
<211> LENGTH: 60
<212> TYPE: PRT
<213> ORGANISM: Thermus thermophilus
<220> FEATURE:
<223> OTHER INFORMATION: 50S ribosomal protein L30
```

-continued

```
<223> OTHER INFORMATION: 1giyX

<400> SEQUENCE: 22

Met Pro Arg Leu Lys Val Lys Leu Val Lys Ser Pro Ile Gly Tyr Pro
1               5                   10                  15

Lys Asp Gln Lys Ala Ala Leu Lys Ala Leu Gly Leu Arg Arg Leu Gln
                20                  25                  30

Gln Glu Arg Val Leu Glu Asp Thr Pro Ala Ile Arg Gly Asn Val Glu
            35                  40                  45

Lys Val Ala His Leu Val Arg Val Glu Val Val Glu
            50                  55                  60

<210> SEQ ID NO 23
<211> LENGTH: 2916
<212> TYPE: RNA
<213> ORGANISM: Thermus thermophilus
<220> FEATURE:
<223> OTHER INFORMATION: 50S 23S ribosomal RNA
<223> OTHER INFORMATION: 1giyA

<400> SEQUENCE: 23
ggucaagaug guaagggccc acgguggaug ccucggcacc cgagccgaug aaggacgugg      60
cuaccugcga uaagccaggg ggagccggua gcgggcgugg aucccuggau guccgaaugg    120
gggaacccgg ccggcgggaa cgccggucac cgcgcuuuug cgcgggggga accugggaa     180 cugaaacauc ucaguaccca gaggagagga aagagaaauc gacucccuga guagcggcga    240
gcgaaagggg accagccuaa accguccggc uuguccgggc ggggucgugg ggcccucgga    300
caccgaaucc ccagccuagc cgaagcuguu gggaagcagc ccagagagg gugaaagccc     360 cguaggcgaa aggugggggg auaggugagg guacccgagu acccguggu ucguggagcc     420 auggggggaau cugggcggac caccggccua aggcuaagua ucccggguga ccgauagcgc    480
accaguaccg ugagggaaag gugaaaagaa ccccggagg ggagugaaau agagccugaa    540
accgugggcu uacaagcagu cacggccccg caagggguug uggcgugccu auugaagcau    600
gagccggcga cucacggucg ugggcgagcu uaagccguug aggcggaggc guagggaaac    660
cgaguccgaa cagggcgcaa gcgggccgca cgcggcccgc aaaguccgcg gccguggacc    720
cgaaaccggg cgagcuagcc cuggccaggu gaagcuggg gugagaccca guggaggccc    780 gaaccgguggg gggaugcaaa cccucuggau gagcuggggc uaggagugaa aagcuaaccg   840
agcccggaga uagcugguuc uccccgaaau gacuuuaggg ucagccucag gcgcugacug    900
gggccuguag agcacugaua gggcuagggg gcccaccagc cuaccaaacc cugucaaacu    960
ccgaaggguc ccagguggag ccugggagug agggcgcgag cgauaacguc cgcguccgag   1020
cgcgggaaca accgagaccg ccagcuaagg cccccaaguc ugggcuaagu gguaaaggau   1080
guggcgccgc gaagacagcc aggagguugg cuuagaagca gccauccuuu aaagagugcg   1140
uaauagcuca cuggucgagu ggcgccgcgc cgaaaaugau gcggggcuua agcccagcgc   1200
cgaagcugcg ggucuggggg augacccccag gcgguagggg agcguucccg augccgauga   1260
aggccgaccc gcgaggcggc uggagguaag ggaagugcga augccggcau gaguaacgau   1320 aaagaggggug agaaucccuc ucgccguaag cccaaggguu ccuacgcaau ggucgucagc   1380 guagggguuag gcgggaccua aggugaagcc gaaaggcgua gccgaagggc agccgguuaa   1440
uauuccggcc cuuccgcag gugcgauggg gggacgcucu aggcuagggg gaccggagcc    1500
auggacgagc ccggccagaa gcgcaggugu ggagguaggc aaauccgccu cccaacaagc   1560
```

-continued

```
ucugcguggu ggggaagccc guacggguga caaccccccg aagccaggga gccaagaaaa      1620
gccucuaagc acaaccugcg ggaacccgua ccgcaaaccg acacaggugg gcggugcaa       1680 gagcacucag gcgcgcggga gaacccucgc caaggaacuc ugcaaguugg ccccguaacu      1740
ucgggagaag gggugcuccc ugggguhgaug agccccgggg agccgcagug aacaggcucu     1800
ggcgacuguu uaccaaaaac acagcucucu gcgaacucgu aagaggaggu auagggagcg      1860
acgcuugccc ggugccggaa ggucaagggg aggggugcaa gccccgaacc gaagccccgg      1920
ugaacggcgg ccguaacuau aacgguccua agguagcgaa auuccuuguc gguaaguuc      1980 cgaccugcac gaaaagcgua acgaccggag cgcugucucg gcgagggacc cggugaaauu     2040
gaacuggccg ugaagaugcg gccuacccgu ggcaggacga aaagaccccg uggagcuuua     2100
cugcagccug guguuggcuc uuggucgcgc cugcguagga uaggugggag ccugugaacc      2160
cccgccuccg ggugggggg aggcgccggu gaaauaccac ccuggcgcgg cuggggccu       2220 aacccucgga uggggggaca gcgcuuggcg ggcaguuuga cugggcgggu cgccuccuaa      2280
aagguaacgg aggcgcccaa agguccccuc aggcgggacg gaaauccgcc ggagagcgca      2340
aggguagaag ggggccugac ugcgaggccu gcaagccgag cagggggcgaa agccgggccu     2400 agugaaccgg uggucccgug uggaagggcc aucgaucaac ggauaaaagu uaccccgggg     2460
auaacaggcu gaucuccccc gagcguccac agcggcgggg agguuuggca ccucgaugcc     2520
ggcucgucgc auccugggc ugaagaaggu cccaagggucuuuggcuguucg cccauuaaag    2580 cggcacgcga gcugguuca gaacgucgug agacaguucg gucucuaucc gccacgggcg      2640
caggaggcuu gaggggggcu cuuccuagua cgagaggacc ggaagggacg caccucuggu     2700
uucccagcug ucccuccagg ggcauaagcu ggguagccau gucggaagg gauaaccgcu       2760 gaaagcaucu aagcgggaag cccgccccaa gaugaggccu cccacggcgu caagccggua     2820
aggacccggg aagaccaccc gguggaugg ccggggugu aagcgccgcg aggcguugag      2880
ccgaccgguc ccaaucgucc gaggucuuga ccccuc                               2916
```

<210> SEQ ID NO 24
<211> LENGTH: 123
<212> TYPE: RNA
<213> ORGANISM: Thermus thermophilus
<220> FEATURE:
<223> OTHER INFORMATION: 50S 5S ribosomal RNA
<223> OTHER INFORMATION: 1giyB

<400> SEQUENCE: 24

```
aaucccccgu gcccauagcg gcguggaacc acccguuccc auuccgaaca cggaagugaa       60
acgcgccagc gccgaugggua cugggcgggc gaccgccugg gagaguaggu cggugcgggg     120
gau                                                                    123
```

<210> SEQ ID NO 25
<211> LENGTH: 256
<212> TYPE: PRT
<213> ORGANISM: Thermus thermophilus
<220> FEATURE:
<223> OTHER INFORMATION: 30S ribosomal protein S2
<223> OTHER INFORMATION: 1gixE

<400> SEQUENCE: 25

Met Pro Val Glu Ile Thr Val Lys Glu Leu Leu Glu Ala Gly Val His
 1               5                  10                  15

Phe Gly His Glu Arg Lys Arg Trp Asn Pro Lys Phe Ala Arg Tyr Ile
            20                  25                  30

-continued

```
Tyr Ala Glu Arg Asn Gly Ile His Ile Ile Asp Leu Gln Lys Thr Met
             35                  40                  45
Glu Glu Leu Glu Arg Thr Phe Arg Phe Ile Glu Asp Leu Ala Met Arg
 50                  55                  60
Gly Gly Thr Ile Leu Phe Val Gly Thr Lys Lys Gln Ala Gln Asp Ile
 65                  70                  75                  80
Val Arg Met Glu Ala Glu Arg Ala Gly Met Pro Tyr Val Asn Gln Arg
                 85                  90                  95
Trp Leu Gly Gly Met Leu Thr Asn Phe Lys Thr Ile Ser Gln Arg Val
                 100                 105                 110
His Arg Leu Glu Glu Leu Glu Ala Leu Phe Ala Ser Pro Glu Ile Glu
             115                 120                 125
Glu Arg Pro Lys Lys Glu Gln Val Arg Leu Lys His Glu Leu Glu Arg
             130                 135                 140
Leu Gln Lys Tyr Leu Ser Gly Phe Arg Leu Leu Lys Arg Leu Pro Asp
 145                 150                 155                 160
Ala Ile Phe Val Val Asp Pro Thr Lys Glu Ala Ile Ala Val Arg Glu
                 165                 170                 175
Ala Arg Lys Leu Phe Ile Pro Val Ile Ala Leu Ala Asp Thr Asp Ser
                 180                 185                 190
Asp Pro Asp Leu Val Asp Tyr Ile Ile Pro Gly Asn Asp Asp Ala Ile
             195                 200                 205
Arg Ser Ile Gln Leu Ile Leu Ser Arg Ala Val Asp Leu Ile Ile Gln
             210                 215                 220
Ala Arg Gly Gly Val Val Glu Pro Ser Pro Ser Tyr Ala Leu Val Gln
 225                 230                 235                 240
Glu Ala Glu Ala Thr Glu Thr Pro Glu Gly Ser Glu Val Glu Ala
                 245                 250                 255

<210> SEQ ID NO 26
<211> LENGTH: 239
<212> TYPE: PRT
<213> ORGANISM: Thermus thermophilus
<220> FEATURE:
<223> OTHER INFORMATION: 30S ribosomal protein S3
<223> OTHER INFORMATION: 1gixF

<400> SEQUENCE: 26

Met Gly Asn Lys Ile His Pro Ile Gly Phe Arg Leu Gly Ile Thr Arg
 1               5                  10                  15
Asp Trp Glu Ser Arg Trp Tyr Ala Gly Lys Lys Gln Tyr Arg His Leu
                 20                  25                  30
Leu Leu Glu Asp Gln Arg Ile Arg Gly Leu Leu Glu Lys Glu Leu Tyr
             35                  40                  45
Ser Ala Gly Leu Ala Arg Val Asp Ile Glu Arg Ala Ala Asp Asn Val
 50                  55                  60
Ala Val Thr Val His Val Ala Lys Pro Gly Val Val Ile Gly Arg Gly
 65                  70                  75                  80
Gly Glu Arg Ile Arg Val Leu Arg Glu Glu Leu Ala Lys Leu Thr Gly
                 85                  90                  95
Lys Asn Val Ala Leu Asn Val Gln Glu Val Gln Asn Pro Asn Leu Ser
                 100                 105                 110
Ala Pro Leu Val Ala Gln Arg Val Ala Glu Gln Ile Glu Arg Arg Phe
             115                 120                 125
Ala Val Arg Arg Ala Ile Lys Gln Ala Val Gln Arg Val Met Glu Ser
```

```
              130                 135                 140
Gly Ala Lys Gly Ala Lys Val Ile Val Ser Gly Arg Ile Gly Gly Ala
145                 150                 155                 160

Glu Gln Ala Arg Thr Glu Trp Ala Ala Gln Gly Arg Val Pro Leu His
                165                 170                 175

Thr Leu Arg Ala Asn Ile Asp Tyr Gly Phe Ala Leu Ala Arg Thr Thr
                180                 185                 190

Tyr Gly Val Leu Gly Val Lys Ala Tyr Ile Phe Leu Gly Glu Val Ile
                195                 200                 205

Gly Gly Gln Lys Pro Lys Ala Arg Pro Glu Leu Pro Lys Ala Glu Glu
    210                 215                 220

Arg Pro Arg Arg Arg Pro Ala Val Arg Val Lys Lys Glu Glu
225                 230                 235

<210> SEQ ID NO 27
<211> LENGTH: 209
<212> TYPE: PRT
<213> ORGANISM: Thermus thermophilus
<220> FEATURE:
<223> OTHER INFORMATION: 30S ribosomal protein S4
<223> OTHER INFORMATION: 1gixG

<400> SEQUENCE: 27

Met Gly Arg Tyr Ile Gly Pro Val Cys Arg Leu Cys Arg Arg Glu Gly
 1               5                  10                  15

Val Lys Leu Tyr Leu Lys Gly Glu Arg Cys Tyr Ser Pro Lys Cys Ala
                20                  25                  30

Met Glu Arg Arg Pro Tyr Pro Pro Gly Gln His Gly Gln Lys Arg Ala
            35                  40                  45

Arg Arg Pro Ser Asp Tyr Ala Val Arg Leu Arg Glu Lys Gln Lys Leu
    50                  55                  60

Arg Arg Ile Tyr Gly Ile Ser Glu Arg Gln Phe Arg Asn Leu Phe Glu
65                  70                  75                  80

Glu Ala Ser Lys Lys Lys Gly Val Thr Gly Ser Val Phe Leu Gly Leu
                85                  90                  95

Leu Glu Ser Arg Leu Asp Asn Val Val Tyr Arg Leu Gly Phe Ala Val
                100                 105                 110

Ser Arg Arg Gln Ala Arg Gln Leu Val Arg His Gly His Ile Thr Val
            115                 120                 125

Asn Gly Arg Arg Val Asp Leu Pro Ser Tyr Arg Val Arg Pro Gly Asp
130                 135                 140

Glu Ile Ala Val Ala Glu Lys Ser Arg Asn Leu Glu Leu Ile Arg Gln
145                 150                 155                 160

Asn Leu Glu Ala Met Lys Gly Arg Lys Val Gly Pro Trp Leu Ser Leu
                165                 170                 175

Asp Val Glu Gly Met Lys Gly Lys Phe Leu Arg Leu Pro Asp Arg Glu
            180                 185                 190

Asp Leu Ala Leu Pro Val Gln Glu Asn Leu Val Ile Glu Phe Tyr Ser
        195                 200                 205

Arg

<210> SEQ ID NO 28
<211> LENGTH: 162
<212> TYPE: PRT
<213> ORGANISM: Thermus thermophilus
<220> FEATURE:
<223> OTHER INFORMATION: 30S ribosomal protein S5
```

<223> OTHER INFORMATION: 1gixH

<400> SEQUENCE: 28

Met Pro Glu Thr Asp Phe Glu Lys Met Ile Leu Ile Arg Arg Thr
1               5                   10                  15

Ala Arg Met Gln Ala Gly Gly Arg Arg Phe Arg Phe Gly Ala Leu Val
            20                  25                  30

Val Val Gly Asp Arg Gln Gly Arg Val Gly Leu Gly Phe Gly Lys Ala
        35                  40                  45

Pro Glu Val Pro Leu Ala Val Gln Lys Ala Gly Tyr Tyr Ala Arg Arg
    50                  55                  60

Asn Met Val Glu Val Pro Leu Gln Asn Gly Thr Ile Pro His Glu Ile
65                  70                  75                  80

Glu Val Glu Phe Gly Ala Ser Lys Ile Val Leu Lys Pro Ala Ala Pro
                85                  90                  95

Gly Thr Gly Val Ile Ala Gly Ala Val Pro Arg Ala Ile Leu Glu Leu
            100                 105                 110

Ala Gly Val Thr Asp Ile Leu Thr Lys Glu Leu Gly Ser Arg Asn Pro
        115                 120                 125

Ile Asn Ile Ala Tyr Ala Thr Met Glu Ala Leu Arg Gln Leu Arg Thr
    130                 135                 140

Lys Ala Asp Val Glu Arg Leu Arg Lys Gly Glu Ala His Ala Gln Ala
145                 150                 155                 160

Gln Gly

<210> SEQ ID NO 29
<211> LENGTH: 101
<212> TYPE: PRT
<213> ORGANISM: Thermus thermophilus
<220> FEATURE:
<223> OTHER INFORMATION: 30S ribosomal protein S6
<223> OTHER INFORMATION: 1gixI

<400> SEQUENCE: 29

Met Arg Arg Tyr Glu Val Asn Ile Val Leu Asn Pro Asn Leu Asp Gln
1               5                   10                  15

Ser Gln Leu Ala Leu Glu Lys Glu Ile Ile Gln Arg Ala Leu Glu Asn
            20                  25                  30

Tyr Gly Ala Arg Val Glu Lys Val Glu Glu Leu Gly Leu Arg Arg Leu
        35                  40                  45

Ala Tyr Pro Ile Ala Lys Asp Pro Gln Gly Tyr Phe Leu Trp Tyr Gln
    50                  55                  60

Val Glu Met Pro Glu Asp Arg Val Asn Asp Leu Ala Arg Glu Leu Arg
65                  70                  75                  80

Ile Arg Asp Asn Val Arg Arg Val Met Val Val Lys Ser Gln Glu Pro
                85                  90                  95

Phe Leu Ala Asn Ala
            100

<210> SEQ ID NO 30
<211> LENGTH: 156
<212> TYPE: PRT
<213> ORGANISM: Thermus thermophilus
<220> FEATURE:
<223> OTHER INFORMATION: 30S ribosomal protein S7
<223> OTHER INFORMATION: 1gixJ

<400> SEQUENCE: 30

```
Met Ala Arg Arg Arg Ala Glu Val Arg Gln Leu Gln Pro Asp Leu
 1               5                  10                  15

Val Tyr Gly Asp Val Leu Val Thr Ala Phe Ile Asn Lys Ile Met Arg
            20                  25                  30

Asp Gly Lys Lys Asn Leu Ala Ala Arg Ile Phe Tyr Asp Ala Cys Lys
            35                  40                  45

Ile Ile Gln Glu Lys Thr Gly Gln Glu Pro Leu Lys Val Phe Lys Gln
 50                  55                  60

Ala Val Glu Asn Val Lys Pro Arg Met Glu Val Arg Ser Arg Arg Val
 65                  70                  75                  80

Gly Gly Ala Asn Tyr Gln Val Pro Met Glu Val Ser Pro Arg Arg Gln
            85                  90                  95

Gln Ser Leu Ala Leu Arg Trp Leu Val Gln Ala Asn Gln Arg Pro
            100                 105                 110

Glu Arg Arg Ala Ala Val Arg Ile Ala His Glu Leu Met Asp Ala Ala
            115                 120                 125

Glu Gly Lys Gly Gly Ala Val Lys Lys Lys Glu Asp Val Glu Arg Met
            130                 135                 140

Ala Glu Ala Asn Arg Ala Tyr Ala His Tyr Arg Trp
145                 150                 155
```

<210> SEQ ID NO 31
<211> LENGTH: 138
<212> TYPE: PRT
<213> ORGANISM: Thermus thermophilus
<220> FEATURE:
<223> OTHER INFORMATION: 30S ribosomal protein S8
<223> OTHER INFORMATION: 1gixK

<400> SEQUENCE: 31

```
Met Leu Thr Asp Pro Ile Ala Asp Met Leu Thr Arg Ile Arg Asn Ala
 1               5                  10                  15

Thr Arg Val Tyr Lys Glu Ser Thr Asp Val Pro Ala Ser Arg Phe Lys
            20                  25                  30

Glu Glu Ile Leu Arg Ile Leu Ala Arg Glu Gly Phe Ile Lys Gly Tyr
            35                  40                  45

Glu Arg Val Asp Val Asp Gly Lys Pro Tyr Leu Arg Val Tyr Leu Lys
 50                  55                  60

Tyr Gly Pro Arg Arg Gln Gly Pro Asp Pro Arg Pro Glu Gln Val Ile
 65                  70                  75                  80

His His Ile Arg Arg Ile Ser Lys Pro Gly Arg Arg Val Tyr Val Gly
            85                  90                  95

Val Lys Glu Ile Pro Arg Val Arg Arg Gly Leu Gly Ile Ala Ile Leu
            100                 105                 110

Ser Thr Ser Lys Gly Val Leu Thr Asp Arg Glu Ala Arg Lys Leu Gly
            115                 120                 125

Val Gly Gly Glu Leu Ile Cys Glu Val Trp
            130                 135
```

<210> SEQ ID NO 32
<211> LENGTH: 128
<212> TYPE: PRT
<213> ORGANISM: Thermus thermophilus
<220> FEATURE:
<223> OTHER INFORMATION: 30S ribosomal protein S9
<223> OTHER INFORMATION: 1gixL

<400> SEQUENCE: 32

```
Met Glu Gln Tyr Tyr Gly Thr Gly Arg Arg Lys Glu Ala Val Ala Arg
 1               5                  10                  15

Val Phe Leu Arg Pro Gly Asn Gly Lys Val Thr Val Asn Gly Gln Asp
                20                  25                  30

Phe Asn Glu Tyr Phe Gln Gly Leu Val Arg Ala Val Ala Ala Leu Glu
                35                  40                  45

Pro Leu Arg Ala Val Asp Ala Leu Gly Arg Phe Asp Ala Tyr Ile Thr
        50                  55                  60

Val Arg Gly Gly Gly Lys Ser Gly Gln Ile Asp Ala Ile Lys Leu Gly
 65                  70                  75                  80

Ile Ala Arg Ala Leu Val Gln Tyr Asn Pro Asp Tyr Arg Ala Lys Leu
                85                  90                  95

Lys Pro Leu Gly Phe Leu Thr Arg Asp Ala Arg Val Val Glu Arg Lys
                100                 105                 110

Lys Tyr Gly Lys His Lys Ala Arg Arg Ala Pro Gln Tyr Ser Lys Arg
        115                 120                 125
```

<210> SEQ ID NO 33
<211> LENGTH: 105
<212> TYPE: PRT
<213> ORGANISM: Thermus thermophilus
<220> FEATURE:
<223> OTHER INFORMATION: 30S ribosomal protein S10
<223> OTHER INFORMATION: 1gixM

<400> SEQUENCE: 33

```
Met Pro Lys Ile Arg Ile Lys Leu Arg Gly Phe Asp His Lys Thr Leu
 1               5                  10                  15

Asp Ala Ser Ala Gln Lys Ile Val Glu Ala Ala Arg Arg Ser Gly Ala
                20                  25                  30

Gln Val Ser Gly Pro Ile Pro Leu Pro Thr Arg Val Arg Arg Phe Thr
                35                  40                  45

Val Ile Arg Gly Pro Phe Lys His Lys Asp Ser Arg Glu His Phe Glu
        50                  55                  60

Leu Arg Thr His Asn Arg Leu Val Asp Ile Ile Asn Pro Asn Arg Lys
 65                  70                  75                  80

Thr Ile Glu Gln Leu Met Thr Leu Asp Leu Pro Thr Gly Val Glu Ile
                85                  90                  95

Glu Ile Lys Thr Val Gly Gly Arg
                100                 105
```

<210> SEQ ID NO 34
<211> LENGTH: 129
<212> TYPE: PRT
<213> ORGANISM: Thermus thermophilus
<220> FEATURE:
<223> OTHER INFORMATION: 30S ribosomal protein S11
<223> OTHER INFORMATION: 1gixN

<400> SEQUENCE: 34

```
Met Ala Lys Lys Pro Ser Lys Lys Val Lys Arg Gln Val Ala Ser
 1               5                  10                  15

Gly Arg Ala Tyr Ile His Ala Ser Tyr Asn Asn Thr Ile Val Thr Ile
                20                  25                  30

Thr Asp Pro Asp Gly Asn Pro Ile Thr Trp Ser Ser Gly Gly Val Ile
                35                  40                  45

Gly Tyr Lys Gly Ser Arg Lys Gly Thr Pro Tyr Ala Ala Gln Leu Ala
        50                  55                  60
```

```
Ala Leu Asp Ala Ala Lys Lys Ala Met Ala Tyr Gly Met Gln Ser Val
 65                  70                  75                  80

Asp Val Ile Val Arg Gly Thr Gly Ala Gly Arg Glu Gln Ala Ile Arg
                 85                  90                  95

Ala Leu Gln Ala Ser Gly Leu Gln Val Lys Ser Ile Val Asp Asp Thr
            100                 105                 110

Pro Val Pro His Asn Gly Cys Arg Pro Lys Lys Lys Phe Arg Lys Ala
        115                 120                 125

Ser
```

<210> SEQ ID NO 35
<211> LENGTH: 135
<212> TYPE: PRT
<213> ORGANISM: Thermus thermophilus
<220> FEATURE:
<223> OTHER INFORMATION: 30S ribosomal protein S12
<223> OTHER INFORMATION: 1gixO

<400> SEQUENCE: 35

```
Met Val Ala Leu Pro Thr Ile Asn Gln Leu Val Arg Lys Gly Arg Glu
 1               5                  10                  15

Lys Val Arg Lys Lys Ser Lys Val Pro Ala Leu Lys Gly Ala Pro Phe
                20                  25                  30

Arg Arg Gly Val Cys Thr Val Val Arg Thr Val Thr Pro Lys Lys Pro
            35                  40                  45

Asn Ser Ala Leu Arg Lys Val Ala Lys Val Arg Leu Thr Ser Gly Tyr
 50                  55                  60

Glu Val Thr Ala Tyr Ile Pro Gly Glu Gly His Asn Leu Gln Glu His
 65                  70                  75                  80

Ser Val Val Leu Ile Arg Gly Gly Arg Val Lys Asp Leu Pro Gly Val
                 85                  90                  95

Arg Tyr His Ile Val Arg Gly Val Tyr Asp Ala Ala Gly Val Lys Asp
            100                 105                 110

Arg Lys Lys Ser Arg Ser Lys Tyr Gly Thr Lys Lys Pro Lys Glu Ala
        115                 120                 125

Ala Lys Thr Ala Ala Lys Lys
130                 135
```

<210> SEQ ID NO 36
<211> LENGTH: 126
<212> TYPE: PRT
<213> ORGANISM: Thermus thermophilus
<220> FEATURE:
<223> OTHER INFORMATION: 30S ribosomal protein S13
<223> OTHER INFORMATION: 1gixP

<400> SEQUENCE: 36

```
Met Ala Arg Ile Ala Gly Val Glu Ile Pro Arg Asn Lys Arg Val Asp
 1               5                  10                  15

Val Ala Leu Thr Tyr Ile Tyr Gly Ile Gly Lys Ala Arg Ala Lys Glu
                20                  25                  30

Ala Leu Glu Lys Thr Gly Ile Asn Pro Ala Thr Arg Val Lys Asp Leu
            35                  40                  45

Thr Glu Ala Glu Val Val Arg Leu Arg Glu Tyr Val Glu Asn Thr Trp
 50                  55                  60

Lys Leu Glu Gly Glu Leu Arg Ala Glu Val Ala Ala Asn Ile Lys Arg
 65                  70                  75                  80

Leu Met Asp Ile Gly Cys Tyr Arg Gly Leu Arg His Arg Arg Gly Leu
```

```
                   85                  90                  95
Pro Val Arg Gly Gln Arg Thr Arg Thr Asn Ala Arg Thr Arg Lys Gly
            100                 105                 110

Pro Arg Lys Thr Val Ala Gly Lys Lys Ala Pro Arg Lys
        115                 120                 125

<210> SEQ ID NO 37
<211> LENGTH: 61
<212> TYPE: PRT
<213> ORGANISM: Thermus thermophilus
<220> FEATURE:
<223> OTHER INFORMATION: 30S ribosomal protein S14
<223> OTHER INFORMATION: 1gixQ

<400> SEQUENCE: 37

Met Ala Arg Lys Ala Leu Ile Glu Lys Ala Lys Arg Thr Pro Lys Phe
1               5                   10                  15

Lys Val Arg Ala Tyr Thr Arg Cys Val Arg Cys Gly Arg Ala Arg Ser
            20                  25                  30

Val Tyr Arg Phe Phe Gly Leu Cys Arg Ile Cys Leu Arg Glu Leu Ala
        35                  40                  45

His Lys Gly Gln Leu Pro Gly Val Arg Lys Ala Ser Trp
    50                  55                  60

<210> SEQ ID NO 38
<211> LENGTH: 89
<212> TYPE: PRT
<213> ORGANISM: Thermus thermophilus
<220> FEATURE:
<223> OTHER INFORMATION: 30S ribosomal protein S15
<223> OTHER INFORMATION: 1gixR

<400> SEQUENCE: 38

Met Pro Ile Thr Lys Glu Glu Lys Gln Lys Val Ile Gln Glu Phe Ala
1               5                   10                  15

Arg Phe Pro Gly Asp Thr Gly Ser Thr Glu Val Gln Val Ala Leu Leu
            20                  25                  30

Thr Leu Arg Ile Asn Arg Leu Ser Glu His Leu Lys Val His Lys Lys
        35                  40                  45

Asp His His Ser His Arg Gly Leu Leu Met Met Val Gly Gln Arg Arg
    50                  55                  60

Arg Leu Leu Arg Tyr Leu Gln Arg Glu Asp Pro Glu Arg Tyr Arg Ala
65                  70                  75                  80

Leu Ile Glu Lys Leu Gly Ile Arg Gly
                85

<210> SEQ ID NO 39
<211> LENGTH: 91
<212> TYPE: PRT
<213> ORGANISM: Thermus thermophilus
<220> FEATURE:
<223> OTHER INFORMATION: 30S ribosomal protein S16
<223> OTHER INFORMATION: 1gixS

<400> SEQUENCE: 39

Met Val Lys Ile Arg Leu Ala Arg Phe Gly Ser Lys His Asn Pro His
1               5                   10                  15

Tyr Pro His Tyr Arg Ile Val Val Thr Asp Ala Arg Arg Lys Arg Asp
            20                  25                  30

Gly Lys Tyr Ile Glu Lys Ile Gly Tyr Tyr Asp Pro Arg Lys Thr Thr
        35                  40                  45
```

```
Pro Asp Trp Leu Lys Val Asp Val Glu Arg Ala Arg Tyr Trp Leu Ser
        50                  55                  60
Val Gly Ala Gln Pro Thr Asp Thr Ala Arg Arg Leu Leu Arg Gln Ala
 65                  70                  75                  80
Gly Val Phe Arg Gln Glu Ala Arg Glu Gly Ala
                85                  90

<210> SEQ ID NO 40
<211> LENGTH: 105
<212> TYPE: PRT
<213> ORGANISM: Thermus thermophilus
<220> FEATURE:
<223> OTHER INFORMATION: 30S ribosomal protein S17
<223> OTHER INFORMATION: 1gixT

<400> SEQUENCE: 40

Met Pro Lys Lys Val Leu Thr Gly Val Val Ser Asp Lys Met Gln
  1               5                  10                  15

Lys Thr Val Thr Val Leu Val Glu Arg Gln Phe Pro His Pro Leu Tyr
                 20                  25                  30

Gly Lys Val Ile Lys Arg Ser Lys Lys Tyr Leu Ala His Asp Pro Glu
             35                  40                  45

Glu Lys Tyr Lys Leu Gly Asp Val Val Glu Ile Ile Glu Ser Arg Pro
 50                  55                  60

Ile Ser Lys Arg Lys Arg Phe Arg Val Leu Arg Leu Val Glu Ser Gly
 65                  70                  75                  80

Arg Met Asp Leu Val Glu Lys Tyr Leu Ile Arg Arg Gln Asn Tyr Gln
                 85                  90                  95

Ser Leu Ser Lys Arg Gly Gly Lys Ala
                100                 105

<210> SEQ ID NO 41
<211> LENGTH: 88
<212> TYPE: PRT
<213> ORGANISM: Thermus thermophilus
<220> FEATURE:
<223> OTHER INFORMATION: 30S ribosomal protein S18
<223> OTHER INFORMATION: 1gixU

<400> SEQUENCE: 41

Met Ser Thr Lys Asn Ala Lys Pro Lys Lys Glu Ala Gln Arg Arg Pro
  1               5                  10                  15

Ser Arg Lys Ala Lys Val Lys Ala Thr Leu Gly Glu Phe Asp Leu Arg
                 20                  25                  30

Asp Tyr Arg Asn Val Glu Val Leu Lys Arg Phe Leu Ser Glu Thr Gly
             35                  40                  45

Lys Ile Leu Pro Arg Arg Arg Thr Gly Leu Ser Gly Lys Glu Gln Arg
 50                  55                  60

Ile Leu Ala Lys Thr Ile Lys Arg Ala Arg Ile Leu Gly Leu Leu Pro
 65                  70                  75                  80

Phe Thr Glu Lys Leu Val Arg Lys
                 85

<210> SEQ ID NO 42
<211> LENGTH: 93
<212> TYPE: PRT
<213> ORGANISM: Thermus thermophilus
<220> FEATURE:
<223> OTHER INFORMATION: 30S ribosomal protein S19
<223> OTHER INFORMATION: 1gixV
```

-continued

```
<400> SEQUENCE: 42

Met Pro Arg Ser Leu Lys Lys Gly Val Phe Val Asp Asp His Leu Leu
1               5                   10                  15

Glu Lys Val Leu Glu Leu Asn Ala Lys Gly Lys Arg Leu Ile Lys
            20                  25                  30

Thr Trp Ser Arg Arg Ser Thr Ile Val Pro Glu Met Val Gly His Thr
        35                  40                  45

Ile Ala Val Tyr Asn Gly Lys Gln His Val Pro Val Tyr Ile Thr Glu
50                  55                  60

Asn Met Val Gly His Lys Leu Gly Glu Phe Ala Pro Thr Arg Thr Tyr
65                  70                  75                  80

Arg Gly His Gly Lys Glu Ala Lys Ala Thr Lys Lys Lys
                85                  90

<210> SEQ ID NO 43
<211> LENGTH: 106
<212> TYPE: PRT
<213> ORGANISM: Thermus thermophilus
<220> FEATURE:
<223> OTHER INFORMATION: 30S ribosomal protein S20
<223> OTHER INFORMATION: 1gixW

<400> SEQUENCE: 43

Met Ala Gln Lys Lys Pro Lys Arg Asn Leu Ser Ala Leu Lys Arg His
1               5                   10                  15

Arg Gln Ser Leu Lys Arg Arg Leu Arg Asn Lys Ala Lys Lys Ser Ala
            20                  25                  30

Ile Lys Thr Leu Ser Lys Lys Ala Val Gln Leu Ala Gln Glu Gly Lys
        35                  40                  45

Ala Glu Glu Ala Leu Lys Ile Met Arg Lys Ala Glu Ser Leu Ile Asp
50                  55                  60

Lys Ala Ala Lys Gly Ser Thr Leu His Lys Asn Ala Ala Arg Arg
65                  70                  75                  80

Lys Ser Arg Leu Met Arg Lys Val Arg Gln Leu Leu Glu Ala Ala Gly
                85                  90                  95

Ala Pro Leu Ile Gly Gly Gly Leu Ser Ala
            100                 105

<210> SEQ ID NO 44
<211> LENGTH: 26
<212> TYPE: PRT
<213> ORGANISM: Thermus thermophilus
<220> FEATURE:
<223> OTHER INFORMATION: 30S ribosomal protein Thx
<223> OTHER INFORMATION: 1gixX

<400> SEQUENCE: 44

Gly Lys Gly Asp Arg Arg Thr Arg Arg Gly Lys Ile Trp Arg Gly Thr
1               5                   10                  15

Tyr Gly Lys Tyr Arg Pro Arg Lys Lys Lys
            20                  25

<210> SEQ ID NO 45
<211> LENGTH: 1522
<212> TYPE: RNA
<213> ORGANISM: Thermus thermophilus
<220> FEATURE:
<223> OTHER INFORMATION: 30S 16S ribosomal RNA
<223> OTHER INFORMATION: 1gixA
```

-continued

```
<400> SEQUENCE: 45
uuuguuggag aguuugaucc uggcucaggg ugaacgcugg cggcgugccu aagacaugca      60
agucgugcgg gccgcggggu uuuacuccgu ggucagcggc ggacgggnga guaacgcgug     120
ggugaccuac ccggaagagg gggacaaccc ggggaaacuc gggcuaaucc cccaugugga     180 cccgcccuu gggugnguc caaagggcuu ugcccgcuuc cggaugggcc cgcguccau        240 cagcuaguug gugggguaau ggcccaccaa ggcgacgacg gguagccggu cugagaggau     300
ggccggccac aggggcacug agacacgggc cccacuccua cgggaggcag caguuaggaa     360
ucuuccgcaa ugggcgcaag ccugacgag cgacgccgcu uggaggaaga agcccuucgg      420 ggguaaacu ccugaacccg ggacgaaacc cccgacgagg ggacugacgg uaccgggua       480 auagcgccgg ccaacuccgu gccagcagcc gcgguaauac ggaggcgcg agcguuaccc      540 ggauucacug ggcguaaagg gcguguaggc ggccuggggc ucccaugug aaagaccacg      600 gcucaaccgu ggggggagcgu gggauacgcu caggcuagac gguggagag ggugugguggaa  660 ucccggagu agcggugaaa ugcgcagaua ccgggaggaa cgccgauggc gaaggcagcc     720
accuggucca cccgugacgc ugaggcgcga agcgugggg agcaaaccgg auuagauacc     780
cggguagucc acgcccuaaa cgaugcgcgc uaggucucug ggucccugg gggccgaagc     840 uaacgcguua agcgcgccgc cuggggagua cggccgcaag gcugaaacuc aaaggaauug    900
acgggggccc gcacaagcgg uggagcaugu gguuaauuc gaagcaacgc gaagaaccuu    960
accaggccuu gacaugcuag ggaacccggg ugaaagccug gggugccccg cgaggggagc   1020
ccuagcacag gugcugcaug gccgucguca gcucgugccg ugaggaguuug gguuaagucc    1080 cgcaacgagc gcaaccccg ccguuaguug ccagcgguuc ggccgggcac ucuaacggga     1140
cugcccgcga aagcgggagg aaggaggga cgacgucugg ucagcauggc ccuuacggcc     1200
ugggcgacac acgugcuaca augcccacua caaagcgaug ccaccggca acggggagcu    1260 aaucgcaaaa aggugggccc aguucggauu ggggucugca acccgacccc augaagccgg   1320
aaucgcuagu aaucgcggau cagccaugcc gcggugaauua cguucccggg ccuuguacac    1380
accgcccguc acgccaugggg agcgggcucu acccgaaguc gccgggagcc uacgggcagg    1440
cgccgagggu agggcccgug acugggggcga agucguaaca agguagcugu accggaaggu    1500
gcggcuggau caccuccuuu cu                                              1522

<210> SEQ ID NO 46
<211> LENGTH: 62
<212> TYPE: RNA
<213> ORGANISM: Saccharomyces cerevisiae
<220> FEATURE:
<223> OTHER INFORMATION: tRNA (Phe); A-site tRNA
<223> OTHER INFORMATION: 1gixB

<400> SEQUENCE: 46
gcggauuuac ucaggggaga gcccagauaa auggagucug ugcguccaca gaauucgcac      60
ca                                                                    62

<210> SEQ ID NO 47
<211> LENGTH: 62
<212> TYPE: RNA
<213> ORGANISM: Saccharomyces cerevisiae
<220> FEATURE:
<223> OTHER INFORMATION: tRNA (Phe); P-Site tRNA
<223> OTHER INFORMATION: 1gixC

<400> SEQUENCE: 47
```

-continued gcggauuuac ucaggggaga gcccagauaa auggagucug ugcguccaca gaauucgcac    60
ca                                                                  62

<210> SEQ ID NO 48
<211> LENGTH: 68
<212> TYPE: RNA
<213> ORGANISM: Saccharomyces cerevisiae
<220> FEATURE:
<223> OTHER INFORMATION: tRNA (Phe); E-Site tRNA
<223> OTHER INFORMATION: 1gixD

<400> SEQUENCE: 48
uccgugaaac aaagcggaug uaccggauuu uuauuccggc uaugggggcaa uuccccgucg   60 cggagcca                                                            68

<210> SEQ ID NO 49
<211> LENGTH: 6
<212> TYPE: RNA
<213> ORGANISM: Thermus thermophilus
<220> FEATURE:
<223> OTHER INFORMATION: mRNA fragment; A- and P-Site mRNA codons
<223> OTHER INFORMATION: 1gix1

<400> SEQUENCE: 49 uuuuuu                                                              6

<210> SEQ ID NO 50
<211> LENGTH: 36
<212> TYPE: RNA
<213> ORGANISM: Artificial Sequence
<220> FEATURE:
<223> OTHER INFORMATION: mRNA Mv36
<223> OTHER INFORMATION: 1jgp1

<400> SEQUENCE: 50
ggcaaggagg uaaaauuuuu uaaacguaaa ucaacu                             36

<210> SEQ ID NO 51
<211> LENGTH: 36
<212> TYPE: RNA
<213> ORGANISM: Artificial Sequence
<220> FEATURE:
<223> OTHER INFORMATION: mRNA Mf36
<223> OTHER INFORMATION: 1jgq1

<400> SEQUENCE: 51
ggcaaggagg uaaaauuuuu uaaacguaaa ucuacu                             36

<210> SEQ ID NO 52
<211> LENGTH: 27
<212> TYPE: RNA
<213> ORGANISM: Artificial Sequence
<220> FEATURE:
<223> OTHER INFORMATION: mRNA Mk27
<223> OTHER INFORMATION: 1jgo1

<400> SEQUENCE: 52
ggcaaggagg uaaaauuuuu uaaaaaa                                       27

<210> SEQ ID NO 53
<211> LENGTH: 94
<212> TYPE: PRT
<213> ORGANISM: Bacillus stearothermophilus
<220> FEATURE:

```
<223> OTHER INFORMATION: Translation initiation factor 3 (IF3)
      C-terminal domain
<223> OTHER INFORMATION: 1tig

<400> SEQUENCE: 53

Lys Gln Lys Val Ile Asn Val Lys Glu Val Arg Leu Ser Pro Thr Ile
 1               5                  10                  15

Glu Glu His Asp Phe Asn Thr Lys Leu Arg Asn Ala Arg Lys Phe Leu
            20                  25                  30

Glu Lys Gly Asp Lys Val Lys Ala Thr Ile Arg Phe Lys Gly Arg Ala
        35                  40                  45

Ile Thr His Lys Glu Ile Gly Gln Arg Val Leu Asp Arg Leu Ser Glu
    50                  55                  60

Ala Cys Ala Asp Ile Ala Val Val Glu Thr Ala Pro Lys Met Asp Gly
65                  70                  75                  80

Arg Asn Met Phe Leu Val Leu Ala Pro Lys Asn Asp Asn Lys
                85                  90

<210> SEQ ID NO 54
<211> LENGTH: 78
<212> TYPE: PRT
<213> ORGANISM: Bacillus stearothermophilus
<220> FEATURE:
<223> OTHER INFORMATION: Translation initiation factor 3 (IF3)
      N-terminal domain
<223> OTHER INFORMATION: 1tif

<400> SEQUENCE: 54

Met Ser Lys Asp Phe Ile Ile Asn Glu Gln Ile Arg Ala Arg Glu Val
 1               5                  10                  15

Arg Leu Ile Asp Gln Asn Gly Asp Gln Leu Gly Ile Lys Ser Lys Gln
            20                  25                  30

Glu Ala Leu Glu Ile Ala Ala Arg Arg Asn Leu Asp Leu Val Leu Val
        35                  40                  45

Ala Pro Asn Ala Lys Pro Pro Val Cys Arg Ile Met Asp Tyr Gly Lys
    50                  55                  60

Phe Arg Phe Glu Gln Gln Lys Lys Glu Lys Glu Ala Arg Lys
65                  70                  75
```

X-RAY CRYSTAL STRUCTURES OF FUNCTIONAL RIBOSOME COMPLEXES CONTAINING TRANSFER RNA AND MODEL MESSENGER RNAS AND METHODS OF USE

CROSS-REFERENCE TO RELATED APPLICATIONS

This application claims the benefit of U.S. Provisional Application No. 60/254,603, filed Dec. 9, 2000, U.S. Provisional Application No. 60,278,013, filed Mar. 22, 2001, and U.S. Provisional Application No. 60/294,394 filed May 30, 2001, the entire disclosure of each of which is hereby incorporated by reference in its entirety for all purposes.

STATEMENT REGARDING FEDERALLY SPONSORED RESEARCH

This invention was made with government support under GM-17129 and GM-59140 awarded by the National Institutes of Health. The government has certain rights in the invention.

REFERENCE TO A MICROFICHE APPENDIX

Not applicable.

FIELD OF THE INVENTION

The present invention relates to crystals of 70S ribosome and more particularly to model structures of the 70S ribosome obtained by X-ray diffraction analysis. This invention also relates to methods of using the structure coordinates of the 70S ribosome model to screen and design compounds that bind to sites on the 70S ribosome and that alter ribosome function.

BACKGROUND OF THE INVENTION

Translation of the RNA-encoded genetic message into the polypeptide chain of a protein links genotype to phenotype. It is carried out by the ribosome, an ancient ribonucleoprotein particle whose structural core and fundamental mechanism of action are conserved among all forms of life (C. R. Woese, et al. *Microbiol. Rev.* 47, 621 (1983); W. E. Hill, et al. Eds., *The Ribosome. Structure, Function and Evolution* (American Society for Microbiology, Washington D.C., (1990)). The smallest and best-studied examples are bacterial ribosomes, which have a molecular size of ~2.5 MD and are made up of a small (30S) and a large (50S) subunit. The 30S subunit is composed of 16S rRNA (~1500 nucleotides (nt)) and about 20 different proteins, whereas the large subunit contains 23S rRNA (~2900 nt), 5S rRNA (120 nt), and more than 30 different proteins. This degree of structural complexity is in keeping with that of its biological role.

The substrate of the ribosome is tRNA, which is commonly considered to bind to the ribosome at three different sites: A, P, and E (aminoacyl, peptidyl, and exit, respectively) (Watson 1964; Rheinberger et al. 1981). Each tRNA binding site is partitioned between the two ribosomal subunits, resulting in as many as six different sites of interaction between tRNA and the ribosome. The anticodon ends of the tRNAs bind to the 30S subunit, which also carries messenger RNA (mRNA); the 3'-acceptor, or CCA ends of the tRNAs interact with the 50S subunit, which contains the catalytic site for peptide bond formation, peptidyl transferase (Monro 1967). Thus, the tRNAs span the interface between the 30S and 50S subunits.

The translational elongation cycle depends on three fundamental processes: (i) aminoacyl-tRNA selection, (ii) peptide bond formation, and (iii) translocation of tRNAs from one site to the next within the ribosome. Although in vivo, the steps of tRNA selection and translocation involve the elongation factors EF-Tu and EF-G, respectively, in guanosine triphosphate (GTP)-dependent reactions, both steps can be carried out by the ribosome in a factor-independent manner, under appropriate ionic conditions in vitro (Pestka 1969; Gavrilova et al. 1972). Thus, all three of the fundamental steps of the translation elongation cycle must be based on the properties of the ribosome itself, and most likely on its RNA components (Green et al. 1997). The molecular mechanisms by which the ribosome accomplishes these functional processes remain largely mysterious, as does its molecular structure. While knowledge of ribosome structure may not provide immediate explanations for the complexities of translation, it is clear that deeper mechanistic insights will depend on it.

Structures of ribosomal proteins and rRNA fragments, determined by x-ray crystallography and nuclear magnetic resonance (NMR) spectroscopy, have provided atomic-resolution detail of individual components of the ribosome (Ramakrishnan et al. 1998; Moore et al. 1998; Nikonov et al. 1988; Szewcazk et al. 1995; Dallas et al. 1997; Correll et al. 1997). In recent years, great progress has been made in determining the structures of complete ribosomes, ribosomal subunits, and functional complexes of the ribosome by cryoelectron microscopy (Frank et al. 1995a; Stark et al. 1997a; reviewed in Agrawal et al. 1999a). Two major advances toward x-ray crystallography of the ribosome were the crystallization of 50S subunits (Yonath et al. 1980; von Bohlen et al. 1991) and the recent determination of their crystal structure at 9 Å resolution (Ban et al. 1998). Even more recently, two papers describing the structures of the *T. thermophilus* 30S ribosomal subunit at 5.5 Å resolution (Clemons et al. 1999) and the *Haloarcula marismortui* 50S ribosomal subunit at 5 Å resolution (Ban et al. 1999) were published. Although many of the details of the rRNA and ribosomal protein components are more clearly resolved in the subunit structures, some features seen in the 70S ribosome structure, such as protein L1 in the 50S subunit and part of the head of the 30S subunit, appear to be absent in the subunit maps, possibly because of local disorder that is not present in the 70S ribosome crystals. A 2.4 Angstrom structure of the 50S ribosomal subunit from *Haloarcula marismortui* was recently reported (Ban et at. 2000), as was a 3 Angstrom structure of the 30S ribosome subunit from *T. thermophilus* (Wimberly et al. 2000). Again, aspects of structure not visible, even in these atomic resolution structures of the subunits (such as L11, see Wimberly et al. 2000) are visible for the first time in the 5.5 Angstrom 70S structure we describe below. In addition, certain features of the 30S subunit, such as the orientation of the head and platform, differ between the isolated subunits and 70S ribosome.

Crystallization of *Thermus thermophilus* 70S ribosomes and ribosome complexes (Trakhanov et al. 1987; Trakhanov et al. 1989; Hansen et al. 1990; Yusupova et al. 1991; Yusupov et al. 1991) has provided the possibility for solving the structure of the complete ribosome in different functional states. In an earlier work, we reported the crystallization of functional complexes of the complete *T. thermophilus* 70S ribosome, containing mRNA and tRNA or tRNA analogs, and the solution of their structures by x-ray crystallography at up to 7.8 Å resolution (Cate et al. 1999). Many specific features of the rRNA were identified, and in many instances, elements of protein structure were also recognizable. The interactions of tRNA with the ribosome in the A, P, and E sites were seen in the greatest detail so far obtained, providing new insights into the mechanism of translation.

Despite these improvements in structure determination of 70S ribosome structure, certain details of the molecular interactions such as those in the interface between the 30S and 50S subunits were not clearly resolved in prior art structure determinations of the 70S ribosome. Knowledge of the details of this and other structural features of the 70S ribosome provides deeper insight into the ribosome function, as well as a structural basis for rational design of novel compounds to alter ribosome function. Thus there exists a need in the art for a higher resolution structure of the 70S ribosome. The present invention provides for these and other advantages by extending the resolution of the 70S ribosome structure to 5.5 Angstroms. Using methods described below, the 5.5 Angstrom structure provides a basis for obtaining high-resolution structural details of the 70S ribosome structure, including determination of many features not previously resolved in prior art structure determinations of the 70S ribosome or its subunits.

BRIEF SUMMARY OF THE INVENTION

A three-dimensional structure of the *Thermus thermophilus* 70S ribosome has been empirically determined at 5.5 Angstroms resolution. The 5.5 Angstrom structure has been used to obtain atomic resolution detail of aspects of the 70S ribosome not previously determined by fitting atomic resolution structures of the 30S ribosome subunit (Wimberly et al. 2000) and the 50S ribosome subunit (Ban et al. 2000) to the observed 5.5 Angstrom electron density map. On the basis of this structural analysis, it now is possible to identify structural parts or specific amino acid residues which from structural or functional considerations appear to be important for ribosome subunit association and function.

Accordingly, in a first aspect the invention relates to a method of identifying molecules which will bind to the 70S ribosome or its subunits. In another aspect, the molecules identified according to the methods of the invention are tested to determine whether they alter 70S ribosome function. Agents that bind to the 70S ribosome or its subunits and that disrupt protein synthesis (i.e. translation) have utility as antibiotic compounds. Agents that bind to the 70S ribosome or its subunits to alter tRNA binding have utility as agents for the creation of variant polypeptides, some of which will have altered functional properties.

The methods of the invention entail identification and/or design of molecules having a particular structure. The methods rely on the use of precise structural information derived from x-ray crystallographic studies of the 70S ribosome, described below.

In yet another aspect, the invention comprises a model structure of a 70S ribosome contained within a computer-readable memory. In a related aspect, the invention includes a computer system comprising a memory comprising X-ray crystallographic structure coordinates defining at least a portion of a bacterial 70S ribosome, said structure coordinates determined from a crystal of a bacterial 70S ribosome that diffracts X-rays to a resolution of at least 5.5 Angstroms and having a space group of 1422 with unit cell dimensions of a=b=507.2 Angstroms, and c=803.7 Angstroms; and a processor in electrical communication with the memory; wherein the processor generates a molecular model having a three dimensional shape representative of at least a portion of said bacterial 70S ribosome.

Another aspect pertains to 70S ribosome variants or subunit variants having altered functional properties. In one preferred embodiment, the variants have altered tRNA binding properties. In another preferred embodiment, the variant comprises a 50S subunit having one or more RNA or polypeptide sequence changes that alter the binding affinity between the 30S and the 50S subunit. Yet another preferred embodiment comprises a 30S subunit having one or more RNA or polypeptide sequence changes that alter the binding affinity between the 30S and the 50S subunit. In an especially preferred embodiment, the sequence changes affect the binding affinity by perturbing the structure of the interface between the 30S and the 50S subunits. Such variant subunits act as dominant negative inhibitors of ribosome function by altering the normal equilibrium between assembled 70S ribosomes and their component 30S and 50S subunits. Also encompassed as another preferred embodiment are polynucleotides encoding a 30S or a 50S variant, wherein said variant alters the binding affinity between the 30S and the 50S subunits.

Another aspect of the invention relates to methods of determining the structure of pharmacophores and candidate compounds having selective binding affinity for bacterial (but not eukaryotic) ribosomes, said method comprising the steps of determining phylogenetically variable regions of primary structure between at least one prokaryotic and at least one eukaryotic ribosomal protein or ribosomal RNA, locating said phylogenetically variable region within the three-dimensional structure of the bacterial 70S ribosome, and providing a pharmacophore that represents the three dimensional arrangement of a pharmacophore binding site comprising said phylogenetically variable region within the three-dimensional structure.

In another aspect, the invention provides for a method of testing candidate compounds for binding activity and or for the ability to affect ribosome function. Said method comprises using the 70S ribosome structure to determine the shape and or charge distribution of a target site, characterizing said site to define a pharmacophore designed to bind the site, obtaining or synthesizing candidate compounds having the shape and or charge distribution designed to interact with the target site, and contacting the 70S ribosome with one or more of said compounds. In this aspect, the invention encompasses use of the structure-coordinates of the 70S ribosome to design, evaluate computationally, synthesize or otherwise obtain (as e.g., from a library of compounds) and use inhibitors or activators of the 70S ribosome.

Thus, the invention encompasses use of the structure coordinates of a 70S ribosome crystal to define details, including atomic details of regions of the 70S ribosome, such as the subunit interface, the messenger RNA pathway, the tRNA binding sites, and binding sites for initiation or elongation factors, which sites are target sites for inhibitors or activators of protein translation.

The structure coordinates set out in Appendix I may be modified by mathematical manipulation including but not limited to, crystallographic permutations, fractionalizations, or inversions of the structure coordinates, integer additions or subtractions to the set of structure coordinates, and any combination of the above.

The details of the preferred embodiments of the present invention are set forth in the accompanying drawings and the description below. Once the details of the invention are known, numerous additional innovations and changes will become obvious to one skilled in the art. All references, including scientific publications, protein structure files (referenced by PDB and/or MMDB identifiers) patents, and patent applications cited in this document are explicitly incorporated by reference in their entirety for all purposes.

BRIEF DESCRIPTION OF THE DRAWINGS

This patent contains at least one drawing executed in color. Copies of this patent with color drawings will be provided by the Patent and Trademark Office upon request and payment of the necessary fee.

FIG. 2. Views of the structure of the *Thermus thermophilus* 70S ribosome. A, B, C and D are successive 90° rotations about the vertical axis; E is a 90° rotation around the horizontal axis of the view shown in A. (A) view from the back of the 30S subunit. H, head; P, platform; N, neck; B, body. (B) view from the right-hand side, showing the subunit interface cavity, with the 30S subunit on the left and the 50S on the right. The anticodon arm of the A-tRNA (gold) is visible in the interface cavity. (C) View from the back of the 50S subunit. EC, the end of the polypeptide exit channel. (D) View from the left-hand side, with the 50S subunit on the left and the 30S on the right. The anticodon arm of the E-tRNA (red) is partly visible. (E) View from the top, with the 50S subunit above and the 30S below. The E-, P- and A-tRNAs are visible in the interface cavity with their anticodon arms pointed downward into the 30S subunit. (F) Interface view of the 30S subunit (rotated 180° from A), showing the positions of the three tRNAs. (G) Interface view of the 50S subunit. ASF, A-site finger; SRL, sarcin-ricin loop. The different molecular components are colored for identification: cyan, 16S rRNA; grey, 23S rRNA; light blue, 5S rRNA (5S); dark blue, 30S proteins; magenta, 50S proteins. Proteins fitted to the electron density are numbered in orange; 50S proteins whose electron density has been identified but not fitted are numbered in magenta. A, P, E, the A-, P- and E-site tRNAs (gold, orange and red, respectively).

FIG. 4. Conformational differences between rRNAs in 70S ribosomes and 30S and 50S subunits. (A) Differences in 16S rRNA from *T. thermophilus* 30S subunits (15) and 70S ribosomes. Rmsd differences are colored yellow (>10 Å), orange (5.5 Å>rmsd>10 Å), red (3.5 Å>rmsd>5.5 Å) and blue (rmsd<3.5 Å). H, head; PS, penultimate stem; SP, spur. (B) Stereo diagram showing superimposed structures of 16S rRNA from 30S subunits ((15); red) and 70S ribosomes (blue). (C, D) Front and back views of the 23S rRNA, showing differences between the *H. marismortui* 50S subunit (14) and the *T. thermophilus* 70S ribosome. Yellow, features that were disordered in the *H. marismortui* 50S structure; cyan, features that are specific to the *T. thermophilus* structure; white, features specific to the *H. marismortui* structure. Conformational differences in the remaining regions are colored orange (rmsd>5.5 Å) and red (3.5 Å<rmsd<5.5 Å). Nucleotide numbers of *Haloarcula* -specific features are preceded by H; the remaining numbers are according to *E. coli* numbering. (E) Conformational differences between the apical stem region of domain III of 23S rRNA in *T. thermophilus* (light blue) and *H. marismortui* (red). H1495 indicates the apical nucleotide in the archaeal sequence, (nucleotide 1597, using the archaeal numbering) corresponding to T1495 in *T. thermophilus*. (F) Stereo view of the 5.5 Å electron density map, showing the crystal-packing interaction of protein L9 with the 30S subunit in another ribosome in the crystal. Contact with the C-domain of L9 around position Gly84 (G84) with the 16S rRNA of a separate ribosome around adenosine 55 (A55), and contact between the N-domain of L9 around Lys12 (K12) with the 16S rRNA around guanine 493 (G493) are shown. Shown in yellow are mutations in L9 that stimulate "hopping" of the ribosome on the phage T4 gene 60 mRNA. The backbone of L9 is shown in red, 16S rRNA is shown in magenta, and helix 5 (the main contact with the C-domain of L9) is highlighted in cyan.

FIG. 6. tRNA-Ribosome Interactions. (A) Electron density maps of the P-tRNA (left; 5.5 Å) and A-tRNA (right; 7 Å) complexed with their respective mRNA codons in the 70S ribosome. (B) Relative orientations of the A-, P- and E-tRNAs (gold, orange and red, respectively) and mRNA, showing codon-anticodon interactions and the kink between the A and P codons. (C, D) Two views of the P-tRNA anticodon stem-loop bound to the its codon in the 30S subunit P site. (E) Interactions between the D stem, elbow and acceptor arm of P-tRNA with the 50S subunit. (F) Experimental electron density (blue) for the *T. thermophilus* 70S ribosome complexed with deacylated tRNA Met f, at 5.5 Å, with the *H. marismortui* CCdAp-Puromycin transition-state analog structure model superimposed. (G) Electron density for the corresponding region of the *H. marismortui* 50S subunit (3), calculated at 5.5 Å (red). The structures of the analog and surrounding parts of the 23S rRNA (3) are shown. (H, I) Two views of the A-tRNA anticodon stem-loop bound to its codon in the 30S subunit A site. (J) Fourier difference map for the A-tRNA at 7 Å, with the A-tRNA and A-codon superimposed. The positions of bases A1492 and A1493 are shown as they are found in the presence (red) and absence (magenta) of paromomycin (17). A patch of negative density (red) can be seen near the positions of A1492 and A1493, indicating that they may rearrange to interact with the minor groove of the codon-anticodon helix when the A-tRNA is bound, as suggested by Carter et al. (17). (K) Interaction of the D stem, elbow, and acceptor end of A-tRNA with the 50S subunit. (L) Electron density, showing clash between the A-tRNA elbow and unassigned r-protein density that may correspond to part of L16. (M) Interaction of E-tRNA with the ribosome. In all panels, 16S rRNA is shown in cyan, 23S rRNA in grey, and ribosomal proteins in blue, green and magenta. Parts of the ribosome that contact the tRNAs are colored gold (A-tRNA contacts), orange (P-tRNA contacts) or red (E-tRNA contacts). rRNA helices are numbered as in FIGS. 3A, B. Bases in rRNA that are protected from chemical probes by tRNA binding (21, 45, 51) are indicated by spheres. Bases that are protected by direct interaction are colored the same as the contacts; bases that are protected as a result of conformational changes are shown in magenta or, in the case of class III sites (71) grey-blue. The different specific ribosome contacts discussed in the text and listed in Table IV are indicated by lower-case letters. (N) Secondary structures of 16S and 23S rRNA, showing molecular contacts with A-tRNA (gold), P-tRNA (orange) and E-tRNA (red).

FIG. 7. (A) Relative arrangement of the A-, P- and E-tRNAs and mRNA in the ribosome. (B) Schematic representation of an updated version of the hybrid states model (Moazed et al. 1989b) for the translational cycle. (C) A three-dimensional representation of the movements of tRNA through the hybrid states cycle.

FIG. 8. rRNA elements surrounding the A- and P-tRNAs at the subunit interface. The position of ribose 71 of the E-tRNA is shown by a red sphere. See the text for details.

FIG. 9. Nucleotide sequences of the three model mRNAs used in this study, MF36 (SEQ ID NO: 51), MV36 (SEQ ID NO: 50), and MK27 (SEQ ID NO: 52). The Shine-Dalgarno sequence (S/D), and P- and A-site codons are underlined. The self-complementary sequences forming the putative A-site helix in MF36 mRNA are overlined.

FIG. 10. (A) 7 Å Fourier difference map of MK27 mRNA with the mRNA model (yellow) docked, showing the position of the Shine-Dalgamo (S/D) helix (magenta) and the positions of the A- and P-site codons (orange and red, respectively), viewed from the top of the 30S ribosomal subunit. (B) Difference map of the MF36 mRNA, showing a four-base-pair tetraloop helix (A-site helix) fitted to the extra density at the A site. (C) Same as for (B), except that the A-tRNA anticodon stem-loop (green) is shown in the position observed experimentally in the A-tRNA difference map (Yusupov et al. 2001), in place of the A-site mRNA helix. The five-nucleotide (GGAGG/CCUCC) (SEQ. ID NO: XX) core of the Shine Dalgamo interaction is shown in magenta, and the rest of the 16S mRNA tail in cyan.

FIG. 11. (A) Interface and (B) solvent views of the mRNA in the 30S ribosomal subunit. A, P, the A- and P-site codons. 5', 3', the 5' and 3' correspond to positions –15 and +15 of the mRNA model. The head, platform, shoulder and body of the subunit, and ribosomal proteins S2, S3, S4, S5, S7, S 11, S 12 and S 18 are indicated. The ribosomal proteins are shown in dark blue, 16S rRNA in cyan and the mRNA is colored as in FIG. 2.

FIG. 13. (A) Interface stereo view of the downstream tunnel, showing the features of 16S rRNA layer surrounding mRNA positions +7 to +10. (B) Solvent-side stereo view of the downstream tunnel, showing the formation of the protein layer surrounding positions +11 to +15 of the mRNA by proteins S3, S4 and S5. The double-stranded RNA binding domain of protein S5 is shown in magenta. The MK27 difference map is shown.

FIG. 19. Positioning IF3 on the 30S subunit. (A) Hydroxyl radical footprint of IF3 mapped onto a ribbon diagram of the crystal structure of the 30S subunit from *Thermus thermophilus*. Strongest protections are colored magenta and weaker protections are lighter pink. Base-specific protections are represented as red spheres. (B) Ribbon diagram of IF3 (yellow) docked onto the 30S subunit footprint. The N- and C-domains are labeled N and C, respectively. (C) Model of the interaction of IF3 (black ribbon) with the 30S subunit as determined by directed hydroxyl radical probing and hydroxyl radical footprinting. Nucleotides cleaved by Fe(II)-IF3 are mapped onto a ribbon diagram of 16S rRNA in the 30S subunit from the crystal structure of the *T. thermophilus* ribosome (Yusupov et al. 2001). Ribosomal proteins S7 and S11 are colored green and 16S rRNA backbone is traced in white except where cleaved by Fe(II) derivatized IF3. Nucleotides cleaved from probing positions 97 and 135 are blue (strong hits) and lighter blue (weaker hits) while nucleotides cleaved from the N-domain probes are colored red (strong hits) and lighter red (weak hits). Cleavages from position 104 are shaded gold. The corresponding probing positions are represented as spheres and are colored to match their respective cleavage targets.

FIG. 20. The position of IF3 relative to initiator tRNA, mRNA, and IF1. (A) Views of the IF3–30S model with initiator tRNA bound to the P site and the location of IF1 as determined by the crystal structure (Carter et al. 2001). 16S rRNA and small subunit proteins are shaded light and dark gray, respectively. IF3 is represented in CPK and colored red. IF1 is shaded blue. Initiator tRNA is traced in yellow, and mRNA is colored purple. (B) A close-up view of IF3 and P site-bound initiator tRNA showing the cleavages from directed probing experiments. Initiator tRNA is colored yellow except where cleaved by Fe-C135(green) and Fe-C76 and Fe-C80 (blue). The corresponding probing positions are colored similarly on IF3 (gray). mRNA is represented in purple.

FIG. 21. The IF3 C-domain occupies the position of helix 69 of 23S rRNA. (A) View of the interaction of helix 69 (yellow) of 23S rRNA with helices 23, 24, and 45 of 16S rRNA (blue). The sites of contact between 23S rRNA and 16S rRNA are colored purple, (B) View showing the overlapping binding site on the 30S subunit of the C domain of IF3 (red) with helix 69 of 23S rRNA (yellow).

DETAILED DESCRIPTION OF PREFERRED EMBODIMENTS

Figure 1:
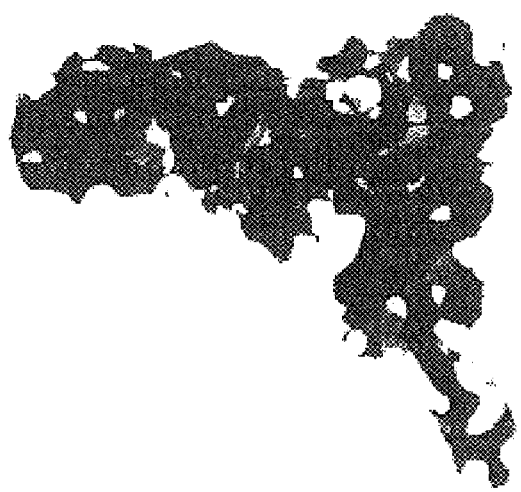
FIG. 1. Electron density of tRNA$^{Met}_f$ bound to the P site of the 70S ribosome, at 5.5 Å resolution.

The invention is based on the discovery of the 5.5 Å crystal structure of the 70S ribosome from *Thermus thermophilus*, which is disclosed herein.

Definitions

All scientific terms are to be given their ordinary meanings as understood by those of skill in the art, unless an alternate meaning is set forth below. In case of conflict, the definitions set forth in this specification shall control.

As used herein, the term "binding site" or "binding pocket" refers to a region of a protein or protein/RNA complex or RNA that binds or interacts with a particular compound.

As used herein, the term "interface" refers to the point or surface at which two or more domains of one or more molecules associate.

As used herein, the term "translatable RNA" refers to an RNA which, when incubated with factors necessary for translation can direct the synthesis of protein.

As used herein, the term "decrease" refers to a diminution of at least 10% and preferably by 20% to 50% or more.

As used herein, the term "anti-bacterial" or "antibiotic" refers to the ability of a compound to inhibit growth of bacteria by producing a statistically significant reduction in the proliferation of said bacteria measured according to any means known to one of skill in the art.

As used herein, the terms "associates with" or "interacts with" refers to a condition of proximity between a chemical entity, compound, or portions thereof, with another chemical entity, compound or portion thereof. The association or interaction may be non-covalent—wherein the juxtaposition is energetically favored by hydrogen bonding or van der Waals or electrostatic interactions—or it may be covalent.

As used herein, the term "pharmacophore" refers to an ensemble of steric and electronic features that is necessary to ensure the optimal supramolecular interactions with a specific biological target structure and to trigger or block a biological response. A pharmacophore may be used to design one or more candidate compounds that comprise all or most of the ensemble of steric and electronic features present in the pharmacophore and that are expected to bind to a site and trigger or block a biological response.

As used herein, the term "structure coordinates" refers to mathematical coordinates derived from mathematical equations related to the X-ray diffraction patterns obtained by diffracting X-rays off a crystal. The diffraction data are used to calculate an electron density map of the unit cell comprising the crystal; said maps are used to establish the positions of the atoms (i.e., the structure coordinates) within the unit cell. Those of skill in the art understand that a set of structure coordinates determined by X-ray crystallography contains standard errors. For purposes of this invention, any set of structure coordinates for a 70S ribosome that has a root mean square deviation of backbone atoms of less than 0.75 Angstroms when superimposed on the structure coordinates of Appendix I, shall be considered identical.

The phrase "fidelity of translation" refers to the accuracy with which a sequence encoded by an mRNA molecule is translated to an amino acid sequence according to the genetic code that relates three-nucleotide codons to amino acids encoded thereby.

The phrase "a residue corresponding to a residue" is intended to encompass a residue specifically identified, as by, e.g., reference to a residue along with a SEQ ID NO, as well as residues occupying analogous positions in related proteins or nucleic acids. A related protein or nucleic acid usually refers to a protein or nucleic acid having similar structural or functional properties as a reference protein or nucleic acid molecule, but which is derived from an organism different from the organism from which the reference protein or nucleic acid molecule is derived. In some instances, which will be clear based on context, a related protein or nucleic acid may be a variant protein or nucleic acid molecule derived from the same organism as that from which the reference protein or nucleic acid is derived, but which has similar structural or functional properties as the reference protein or nucleic acid molecule.

Structural similarity may be inferred from, e.g., sequence similarity, which can be determined by one of ordinary skill through visual inspection and comparison of the sequences, or through the use of well-known alignment software programs such as CLUSTAL (Wilbur, W. J. and Lipman, D. J. *Proc. Natl. Acad. Sci. USA*, 80, 726–730 (1983)) or CLUST- ALW (Thompson, J. D., Higgins, D. G. and Gibson, T. J., CLUSTAL W: improving the sensitivity of progressive multiple sequence alignment through sequence weighting, positions-specific gap penalties and weight matrix choice, *Nucleic Acids Research*, 22:4673–4680 (1994)) or BLAST® (Altschul S F, Gish W, et al., .*J Mol. Biol.*, October 5;215 (3):403–10 (1990)), a set of similarity search programs designed to explore all of the available sequence databases regardless of whether the query is protein or DNA. CLUSTAL W is available at http://www.ebi.ac.uk/clustalw/; BLAST is available at http ://www.ncbi.nlm.nih.gov/BLAST/. A residue within a first protein or nucleic acid sequence corresponds to a residue within a second protein or nucleic acid sequence if the two residues occupy the same position when the first and second sequences are aligned. Table I provides illustrative representative alignments that can be used to identify correspondence among residues derived from related proteins and nucleic acids of different organisms. The sequence alignments illustrated in Table I were generated using CLUSTAL.

TABLE I

Representative Sequence Alignments

| Species | | Aligned Sequence | | | Aligned Sequence | |
|---|---|---|---|---|---|---|
| A. 16S rRNA Alignments | | | | | | |
| Thermus_thermophilus | 702 | CCGAUG | 707 | 904 | GGGCC | 908 |
| Escherichia coli | 719 | CCGGUG | 724 | 927 | GGGCC | 932 |
| Pseudomonas aerugino | 715 | CCAGUG | 720 | 922 | GGGCC | 926 |
| Neisseria gonorrhoea | 720 | CCGAUG | 725 | 928 | GGACC | 932 |
| Bacillus subtilis | 726 | CCAGUG | 731 | 935 | GGGCC | 939 |
| Haloferax volcanii | 657 | CCGAUG | 662 | 869 | GGGAG | 873 |
| Methanococcus vannie | 651 | CCUAUG | 656 | 863 | GGGAG | 967 |
| Sulfolobus solfatari | 679 | COAGUG | 783 | 890 | GGGAG | 894 |
| Homo sapiens Mit. | 158 | CCACGG | 163 | 369 | UGACA | 363 |
| Caenorhabditis elega | 901 | CCAACA | 906 | 1116 | AAGGG | 1120 |
| Saccharomyces_cerevi | 929 | ACUACU | 934 | 1148 | AAGGG | 1152 |
| Zea_mays | 935 | ACAACU | 940 | 1156 | AAGGG | 1170 |
| Rattus_norvegicus | 991 | ACCAGA | 996 | 1212 | AAGGG | 1216 |
| Thermus_thermophilus | 1370 | CCUUGU | 1375 | 1482 | GGUAG | 1485 |
| Escherichia coli | 1388 | CCUUGU | 1393 | 1505 | GGUAA | 1508 |
| Pseudomonas aerugino | 1383 | CCUUGU | 1388 | 1500 | GGUAG | 1503 |
| Neisseria gonorrhoea | 1388 | UCUUGU | 1393 | 1505 | GGUAG | 1508 |
| Bacillus subtilis | 1393 | CCUUGU | 1398 | 1511 | GGUAG | 1514 |
| Haloferax volcanii | 1335 | CCUUGC | 1340 | 1436 | GGUAG | 1439 |
| Methanococcus varinie | 1325 | CCUUGC | 1330 | 1432 | GGUAG | 1435 |
| Sulfolobus solfatari | 1350 | CCTJUGC | 1355 | 1451 | GGUAG1454 | |
| Homo sapiens Mit. | 825 | GCGCGU | 830 | 923 | GGUAA | 926 |
| Caenorhabditis elega | 1587 | CUUUGU | 1592 | 1728 | GGUAG | 1731 |
| Saccharornyces_cerevi | 1623 | CUUUGU | 1628 | 1766 | GGUUU | 1769 |
| Zea_mays | 1631 | CUUUGU | 1636 | 1773 | GGUTJU | 1776 |
| Rattus_norvegicus | 1694 | CUUUGU | 1699 | 1842 | GGUUU | 1845 |
| Thermus_thermophilus | 1503 | GCUG | 1506 | | | |
| Escherichia coli | 1526 | GUUG | 1529 | | | |
| Pseudomonas aerugino | 1521 | GCUG | 1524 | | | |
| Neisseria gonorrhoea | 1526 | GCUG | 1529 | | | |
| Bacillus subtilis | 1532 | GCUG | 1535 | | | |
| Haloferax volcanii | 1457 | GCUG | 1460 | | | |
| Methanococcus vannie | 1453 | GCUG | 1456 | | | |
| Sulfolobus solfatari | 1480 | GCUG | 1483 | | | |
| Homo sapiens Mit. | 944 | CUUG | 947 | | | |
| Caenorhabditis elega | 1749 | GCUG | 1752 | | | |
| Saccharomyces_cerevi | 1787 | GAAG | 1790 | | | |
| Zea_mays | 1794 | GAAG | 1797 | | | |
| Rattus_norvegicus | 1863 | GAAG | 1866 | | | |

B. S18 Sequence Alignments
(SEQ ID NOS: 55–84, respectively, in order of appearance)

| Species | | Aligned Sequence | |
|---|---|---|---|
| ESCRERICHIA_COLI | 1 | -------------------------MAR-----YFRRR------------------------KFCRF | 13 |
| YERSINIA_PESTIS | 1 | -------------------------MAR-----YFRRR------------------------KFCRF | 13 |
| SALMONELLA_TYBMIMURI | 1 | -------------------------MAR-----YFRRR------------------------KFCRF | 13 |
| HAEMOPHILUS_INFLUENZ | 1 | -------------------------MAR-----YFRRR------------------------KFCRF | 13 |
| THERMOS_THERMOPHILUS | 1 | -------------------------P-------SRKA------------------------KVK-A | 9 |
| DEINCOCOOUS_RACICCUR | 1 | ------MTQQCCNSCERSSRCSCPSREEKS----RPRKP------------------------KVDPF | 28 |
| PSEUDOMONAS_AERUCINO | 1 | -------------------------MAR-----FFRRR------------------------KFCRF | 13 |

TABLE I-continued

| | | |
|---|---|---|
| HOMO_SAPIEN_MITOCHON | 1 | --MAEONPSVOLOTHLSSPRESEESAPKICIRQSYE------------------------KEPLKKCIL 67 |
| TREPNOMEA_PALLIDUM | 1 | -----------MAEHPSVDLDTHLSSPRESEESAPKKNRQFYR--------------------KKVCRF 39 |
| BACILLUS_SUBTILIS | 1 | ----------------MAGG------RRGG----RAKRR-------------------------KVCYF 18 |
| GEOBACILLUS_STEAROTH | 1 | ----------------MAG-------RRGG----RGKRR-------------------------KVCYF 17 |
| CHLAMYCOPHILIA_PREUM | 1 | ----------------MNK-P-----VHNN----EHRRKRF----------------------NKKCPF 21 |
| LISTERIA_INNOCUA | 1 | ----------------MAGG------RRGG----R-RRK-------------------------KVCYF 17 |
| CHLAMYDIA_TRAONCMATI | 1 | ----------------MNR-P-----VHN-----EHRRKRF----------------------AKKCPF 20 |
| STAPHYLCCOCCUS_AUREU | 1 | ----------------MAGGP-----RRGG----R-RRK-------------------------KVCYF 18 |
| MESORHIZOMBIUM_LOTI | 1 | ----------------MVDINQIP-TRRP----FHRRR-------------------------KTCPF 22 |
| BACILLUS_HALODURANS | 1 | ----------------MA---------RRG----RPKRR------------------------KVCYF 15 |
| AQUIFEX_AEOLICUS | 1 | --------------------------MVVR----APKK-------------------------KVCMY 13 |
| THERMOTOGA_MARITIMA | 1 | -------------------------MAYRR----------R----------KKKIKKCRL 15 |
| MYCOPLASMA_PULMONIS | 1 | ----------------MNHNKDKLKK-----KNKRK-------------------------RVSFL 20 |
| VIBRIO_CHOLERAE | 1 | -------------------------MAR----FFRRR-------------------------KFCRF 13 |
| HELIOBACTER_PYLORI | 1 | -------------------------MERKR---YSKR-------------------------YCKY 13 |
| CYANOPHORA_PARADOXA | 1 | ------------------------MS------VYRR-------------------------RLSPL 11 |
| ODONTELLA_SINENSIS_C | 1 | --------------------MLAQKQ----------------------------------KLSPI 13 |
| OENOTHERA_ELATA | 1 | ----------------MDKSKRLFLKSKR-----SFRR------------------------RLPPI 22 |
| ORYZA_SATIVA | 1 | ---------MYTSSQPFHSSKQTSMSSSQ-----TFRKSKQTFRSSSQPSESPSQPSR------RRPRI 49 |
| ZEA_MAYS | 1 | ---------MYISSQPSRKSSQPSRKSKC-----TFHKSKQPSRSPSQPSRSSSQPSRKSSQPFRESRI 56 |
| SPINACIA_OLERACRA | 1 | ----------------MDKSKRPFLKFKR-----SFRR------------------------RLPPI 22 |
| NIOCTIANA_TABACUM | 1 | ----------------MDKSKRPFLKFKR-----SFRR------------------------RLPPI 22 |
| METNANCOCOCUS_JANNAS | 1 | ------------------MASARRRRIS-----KKKQVIS---------------------KKIEF 22 |
| ESCHERICHIA_COLI | 14 | TAEGOQEIOYSCIAT--LKNYITE--SGKIV----P---SRITCTEAKYORCLAEA---IK-RARYLSL 67 |
| YERSINIA_PESTIS | 14 | TAECVVEIOYSCIAT--LSNYITE--SGKIV----P---SRITCTEASYCRQLARO---IK-SARYLSL 67 |
| SALMONELLA_TYPHIMURI | 14 | TAECVOEIDYSCIAT--LSNYITE--SGKIV----P---SRITCTRASYQROLRRA---IK-RARYLSO 67 |
| HAEMOPHILUS_INFLUENZ | 14 | TAENVVEIDYKDIAT--LSNYISE--SGKIV----P---SRITCTRAKYQRQLAEA---IK-RARYLAL 67 |
| THERMUS_THERMOPHILUS | 10 | TLCSSOLROYENOEO--LSRSLSE--TGKIL----P---RRRTCLSGSEQEILAST---IK-RARILGL 63 |
| DEINOCOCCUS_RADIODUR | 29 | SICELEITOYSOOSM--LRRFVSD--TGKIL----P---RRETGLSASICRRIACT---IK-VARQLAL 82 |
| PSEUCOMONAS_AERUGINO | 14 | TAECOSEIOYSDLNT--LKAYVSE--TGSIV----P---SRITGTSASYCRQLATA---IK-RARYLAL 67 |
| HOMO_SAPIEN_MITOCHON | 68 | CG----KHVDYKNVQL--LSQFVSPF-TGCIY----G---RHITCLOCSKCKEITSA---IK-RAQIMOS 119 |
| TREPNOMEA_PALLIDUM | 40 | CTQKL-LACYSOSOT--LRREITE--RCKIL----P---EEITCTCASHQREVALE---VK-RSRAVAL 92 |
| BACILLUS_SUBTILIS | 19 | TSNCITMIOYSOODL--LKKFVSE--RGKIL----P---RROTCTNASYORSLTAA---IK-RARQMAL 72 |
| GEOBACILLUS_STEAROTH | 18 | TANNITMIOYSOVOL--LSKPISE--RGKIL----P---RRVTCTSASYCRSLTVA---IK-RAROMAL 71 |
| CHLAMYCOPHILIA_PNEUM | 22 | VSACWSTIDYSCVET--LKKFITE--RGKVL----P---RRITCOSSRFQCVLSOA---IK-RARHLGL 75 |
| LISTERIA_INNOCUA | 18 | TSNCITHIDYSOVEL--LKKFVSE--RRVTCTSASYORSLTOA---IK-RSEQMAL 71 |
| CHLAMYDIA_TRACHOMATI | 21 | VSAGMSTIOYKDVTT--LKRFITS--RGKIL----P---RRITCVSEEFCALLAQA---VK-RARHVCL 74 |
| STAPHYLOCOCCUS_AUREU | 19 | TANCITHIOYROTEL--LSESISE--RGKIL----P---ERVTCTSASYORMLTTA---IK-RSRHMAL 72 |
| MESORHIZOMBIUM_LOTI | 23 | SGANAPSIOYSOVRL--LQRYISE--RGKIV----P---SRITAOSCSSCRELASA---IK-RARFLGL 76 |
| BACILLUS_HALODURANS | 16 | TVNKIESIOYSCODL--LSSSVSE--RGKIL----P---RROTCTEASYCRQLTTA---IK-RARCIAL 69 |
| AQUIFEX_AEOLICUS | 14 | CEQSR-EPDYKNYEE--LRNELTE--RGRIK----D---RKQTCLCASHORRLAOQ---IK-EARQLCL 66 |
| THERMOTOGA_MARITIMA | 16 | CEMKLDYVDYKDTRL--LSESLTD--KGKII----P---SELTCNCSSHORMV50A---IK-RARQMOL 69 |
| MYCOPLASMA_PULMONIS | 21 | DEQCINYIOYROOEL--LSKFINS--HGKIL----P---SKITDVSAKRQRMLTRA---IK-RARNMAL 74 |
| VIBRIO_CHOLERA | 14 | TAECVQEIOYSDOAT--LKNYITE--AGKIV----P---SRITGTSAKYQRQLARA---IK-RARYLAL 67 |
| HELICOBACTER_PYLORI | 14 | TEASISPIDYSCLDM--LKHTLSE--RYKIM----P---RRLTGNSKKWQERVEVA---IK-RARHMAL 67 |

TABLE I-continued

```
CYANOPHORA_         12 KPNQV--IDYQDVEL--LRTFITD--QGKIL----P--RRVTGLTAKQQRAVTKA---IK-QARVLAL 63
PARADOXA
ODONTELLA_          12 SVNQK--IDYKDIDL--LKLFITE--QGKIL----P--RRATGVTVQQQRQIAKA---IK-RARVLSL 63
SINENSIS_C
OENOTHERA_ELATA     23 QSGDR--IDYRNISL--ISRFISQ--QGKIL----S--RRVNRLTLKQQRLITIA---IN-QARILSL 74
ORYZA_SATIVA        50 GPGDR--IDYRNMSL--INRFISE--QGKIL----S--RRINRLTLKQQRLITLA---IK-QARILSF 101
ZEA_MAYS            57 GPGDR--IDYRNMSL--INRFISE--QGKIL----S--RRINRLTLKQQRLITLA---IK-QARILSF 108
SPINACIA_           23 QSGDR--IDYRNMSL--ISRFISE--QGKIL----S--RRVNRLTLKQQRLITSA---IK-QARILSL 74
OLERACEA
NICOTIANA_          23 QSGDR--IDYRNMSL--ISRFISE--QGKIL----S--RRVNRLTLKQQRLITLA---IK-QARILSL 74
TABACUM
METHANOCOCCUS_      23 RYRGYTLELQQMPLREFAKLLPARQRRTLLRGLTPQQKKLAMKIKKARRLLNKGEPRIIRTHCRDFVI 92
JANNAS
ESCEERICHIA_COLI    68 LP-------------YTD-------------------------------------RHQ-------------- 75
YERSINIA_PEST1S     68 LP-------------YTD-------------------------------------RHQ-------------- 75
SALMONELLA_         68 LP-------------YTD-------------------------------------RHQ-------------- 75
TYPHIMURI
HAEMOPHILUS_        68 LP-------------YTD-------------------------------------NHQ-------------- 75
INFLUENZ
THERMUS_            64 LP-------------FTEK------------------------------------LVRK------------- 73
THERMOPHILUS
DEINOCOCCUS_        83 LP-------------YTEK------------------------------------LVRK------------- 92
RADIODUR
PSEUDOMONAS_        68 LP-------------YTD-------------------------------------SHGR------------- 76
AERUGINO
HOMO_SAPIEN_       120 MPVTYKDPA--------YLKD-----------------------------------PKVCNIRYRE------- 142
MITOCHON
TREPNOMEA_          93 LP-------------FVL--------------------------------------TE-------------- 99
PALLIDUM
BACILLUS_SUBTILIS   73 LP-------------YVS--------------------------------------GE-------------- 79
GEOBACILLUS_        72 LP-------------YVA--------------------------------------DE-------------- 78
STEAROTH
CHLAMYDOPHILIA_     76 LP-------------FVG--------------------------------------ED-------------- 82
PHEUM
LISTERIA_INNOCUA    72 LP-------------FVA--------------------------------------EEK------------- 79
CHLAMYDIA_          75 LP-------------FVG--------------------------------------ED-------------- 81
TRACHOMATI
STAPHYLOCOCCUS_     73 LP-------------YVK--------------------------------------EEQ------------- 80
AUREU
MESORHIZOMBIUM_     77 LP-------------YVV--------------------------------------R--------------- 82
LOTI
BACILLUS_           70 LP-------------YVT--------------------------------------DNN------------- 77
HALODURANS
AQUIFEX_AEOLICUS    67 LP-------------YVV--------------------------------------Y--------------- 72
THERMATOGA_         70 LP-------------YLK--------------------------------------I--------------- 75
MARITIMA
MYCOPLASMA_         75 LP-------------FTQ--------------------------------------ERVRTQKPL--IVTSNS 94
PULMONIS
VIBRIO_CHOLERAE     68 LP-------------YTD--------------------------------------KHQ------------- 75
HELICOBACTER_       68 IP-------------YIV--------------------------------------DRKKVVDSP--FKQH-- 85
PYLORI
CYANOPHORA_         64 LP-------------FVN-------------------R------------------ES-------------- 71
PARADOXA
ODONTELLA_          64 LP-------------FVA--------------------------------------SNSI------------ 72
SINENSIS_C
OENOTHERA_ELATA     75 LP-------------FRP--KAQRFK-----------R------------------SQSTARTVG--LRTRNK 101
ORYZA_SATIVA       102 LP-------------FRNYENEKQFQAQSISIITGPRPRREREIPPLTQKPESERELRESEOTLRETER 157
ZEA_MAYS           109 LP-------------FREYEHEEQPQAQAISIITGPRHRREREIPQLTQKPESHRELRESEQELRNUER 164
SPINACIA_           75 LP-------------FLN--NEKQFE-----------R------------------TESTTRTAN--FRTKNK 101
OLERACRA
NICOTIANA_          75 LP-------------FLN--NEKQFE-----------R------------------TESTARTTG--FKARNK 101
TABACUM
METHANOCOCCUS_      93 TPDHVGLTPOVYEOICEEVEVKVTPEMIGHYLG---------------EFSLTREPVQHDAPGHGATRS 145
JANNAS
ESCHERICHIA_COLI    75 ----------- 75
YERSINIA_PESTIS     75 ----------- 75
SALMONELLA_         75 ----------- 75
TYPHIMURI
HAEMOPHILUS_        75 ----------- 75
INFLUENZ
THERMUS_            73 ----------- 73
THERHOPHILUS
DEINOCOCCUS_        92 ----------- 92
RADIODUR
PSEUDOMONAS_        76 ----------- 76
AERUGINO
HOMO_SAPIEN_       142 ----------- 142
MITOCHON
```

TABLE I-continued

| Species | | | |
|---|---|---|---|
| TREPNOMEA_PALLIDUM | 99 | ----------- | 99 |
| BACILLUS_SUBTILIS | 79 | ----------- | 79 |
| GEOBACILLUS_STEAROTH | 78 | ----------- | 78 |
| CHLAMYDOPHILIA_PNEUM | 82 | ----------- | 82 |
| LISTERIA_INNOCUA | 79 | ----------- | 79 |
| CHLAMYDIA_TRACHOMATI | 81 | ----------- | 81 |
| STAPHYLOCOCCUS_AUREU | 80 | ----------- | 80 |
| MESORHIZOMBIUM_LOTI | 82 | ----------- | 82 |
| BACILLUS_HALODURANS | 77 | ----------- | 77 |
| AQUIFEX_AEOLICUS | 77 | ----------- | 77 |
| THERMATOGA_MARITIMA | 75 | ----------- | 75 |
| MYCOPLASMA_PULMONIS | 95 | PKEKEAKPSAQ | 105 |
| VIBRIO_CHOLERAE | 75 | ----------- | 75 |
| HELICOBACTER_PYLORI | 85 | ----------- | 85 |
| CYANOPHORA_PARADOXA | 71 | ----------- | 71 |
| ODONTELLA_SINENSIS_C | 72 | ----------- | 72 |
| OENOTHERA_ELATA | 101 | ----------- | 101 |
| ORYZA_SATIVA | 158 | NLSSDC----- | 163 |
| ZEA_MAYS | 165 | NLSSDC----- | 170 |
| SPINACIA_OLERACEA | 101 | ----------- | 101 |
| NICOTIANA_TABACUM | 101 | ----------- | 101 |
| METHANOCOCCUS_JANNAS | 146 | SMFVPIK---- | 152 |

C. S11 Sequence Alignments
(SEQ ID NOS: 85–124,
respectively, in order of
appearance)

| Species | Aligned Sequence | |
|---|---|---|
| ESCHERICHIA_COLI | 1 -----MAKAPI-----------------------------------RARKRVRKQ----------VSDGV | 20 |
| THERMUS_THERMOPHILUS | 1 ------------------------------------------------KRQ----------VASGR | 8 |
| CAULOBACTER_CRESCENT | 1 -----MAKEPA-----------------------------------RVKRRERKN----------ITSOV | 20 |
| MESORHIZOBIUM_LOTI | 1 -----MAKEAA-----------------------------------RVRRRERKN----------ISSGV | 20 |
| HAEMOPILUS_INFLUENZ | 1 -----MAKTPV-----------------------------------RARKRVKKQ----------VVDGV | 20 |
| YERSINIA_PESTIS | 1 -----MAKAPI-----------------------------------RARKRVRKT----------VSDGV | 20 |
| GEOBACILLUS_STEAROTH | 1 ------ARRTN-----------------------------------TRKRRVRKN----------IDTGI | 19 |
| THERMUS_AQATICUS | 1 -----MAKKPS-----------------------------------KKKVKRQ----------VASGR | 18 |
| DEINOCOCCUS_RADIODUR | 1 -----MAKPTKG----------------------------------KAPRRSRRN----------ISAGR | 21 |
| STREPTOMYCES_COELICO | 1 -----MPPKGRQGAAK------------------------------KVRRKEKKN----------VAHGH | 25 |
| CLOSTRIDIUM_ACETOBUT | 1 -----MAVQKNKK---------------------------------TRRRKEKKN----------IEHGC | 22 |
| TREPONEMA_PALLIDUM | 1 -----MAVTKK-----------------------------------RKEKKN----------VYEGN | 17 |
| LEPTOSPIRA_INTERROGA | 1 -----MADDKKSVKKE------------------------------KKVKKKEKKI----------VPRGK | 26 |
| AQUIFEX_AEOLICUS | 1 -----MAKKK------------------------------------KKQKRQ----------VTKAI | 16 |
| VIBRIO_CHOLERAE | 1 -----MAKQPT-----------------------------------RARKRVRKQ----------VADGV | 20 |
| SALMONELLA_ENTERICA | 1 -----MAKAPV-----------------------------------CARKRVRKQ----------VSDGV | 20 |
| THERMOTOGA_MARITIMA | 1 -----MARKRGG----------------------------------SSKKQKKVS----------FDYGV | 21 |
| BACILLUS_HALOCURANS | 1 -----MAKKTN-----------------------------------TRKRRQRKN----------VETGV | 20 |
| CYANOPHORA_PARADOXA | 1 -----MARQIKR----------------------------------SGTTKQKKN----------IPVGV | 21 |

TABLE I-continued

```
BACILLUS_SUBTILIS      1  ---MAAARKSN----------------------------------TRKRRVKKN----------IESGI  22
LISTERIA_INNOCUA       1  -----MARKTN----------------------------------TRKRRVKKN----------IESGI  20
STREPTOCOCCUS_         1  -----MAKP------------------------------------TRKRRVKKN----------IESGI  18
PNEUMO
OENOTHERA_ELATA        1  -----MAKSIPSAGLR--LRLRLRR--------------------NARRRSRKSTRK--------IPKGV  35
SPINACIA_              1  -----MAKPIP--------KIGSRR--------------------NGRISSKKSARK--------IPKGV  29
OLERACEA
ZEA_MAYS               1  -----MTKAIPKIGSRRKVRIGLRR--------------------NARPSLRKSARR--------ITKGI  37
ORYZA_SATIVA           1  -----MTKAIPKIGSRRKVRIGLRR--------------------NARFSLRKSARR--------ITKGV  37
PINUS_                 1  -----MSKTIK----------------------------------RIGSRRNENR----------VLKGV  21
THUNBERGII_
CHL
EUGLENOPHYCEAN_        1  ------------------------------------------------------------------MAM   3
ALGA
COMMON_TOBACCO         1  -----MAKAIP--------KISSRR--------------------NGRIGSKKGARR--------IPKGV  29
CHLAMYDIA_             1  -----MVKNQAQ--K------------------------------KGVKRKQVKN----------IPSGV  23
TRACHOMATI
HOMO_SAPIENS_          1  -----MEKRTWSSEVNGSSSGQVEVG-----HWRQSIYPPIPGEESSLRWAGKKF----------EEIPI  50
MITOCHO
HALOARCULA_            1  -----MSEE------------------------------------TEDI---------------WGI    11
MARISMORT
HALOBACTERIUM_         1  -----MADD------------------------------------TK-----------------WGI     9
SALINA
METHANOCOCCUS_         1  -----MAEQ------------------------------------KKEK---------------WGI    11
JANNES
RATTUS_                1  -----MQVLT-----------------------------------KRYPKN---------CLLKVM    17
NORVEGICUS_S1
NEUROSPORA_            1  -----MPPKKAAR--------------------------------PAQEN-ISLGPQIREGELVFGV  29
CRASSA_S1
MELANOGASTER_          1  -----MAPRKAKV--------------------------------QKEEVQVQLGPQVRDGEIVFGV  30
S14
CRICETUSLUS_           1  -----MAPRKGKE--------------------------------KKEEQVTSLGPQVAEGENVFGV  30
GRISEUS_
HOMO_SAPIENS_S14       1  -----MAPGKGKE--------------------------------KKEEQVINLGPQVAEGENVFGV  30
BRUCEI_S14             1  -----MS--------------------------------------KKQE-VKYYGSSAGKOQLVYOV  23
ESCHERICHIA_COLI      21  AHIHASFNNTIVTITOEQG-NALGNATAOGSGPRGSRKSTPPAAQVAAERCAOAVKE-YGIKNLEVNVKG  95
THERMUS_               9  AYINASYNNTIVTITOPCG-NPITWSSGGVIGYKOSEKOTPYAAQLAELCAAKKEMA-YGMQSVOVIVEG  76
THERMOPHILUS
CAULOBACTER_          21  AHVNASFNNTMITITDAQG-NTISWSSAGMMGFKGSRKSTPYAAQMAAEDAGKKAAE-HGVKTLEVNVSG  88
CRESCENT
MESORMISOBIUM_        21  AHVNSTFNNTMITITDAQG-NSIAWSSAGAQGFKGSRKSTPFAAQMAAEDVAKKAQE-HGMRMLEVEVCG  88
LOTS
HAEMOPHILUS_          21  RNIRASFNNTIVTITDEGG-NALEWATAGGSGFROSRESTPPEAQVAAEECAEIVKE-FGLKNLEVMVKG  58
INFLUENZ
YERSINIA_PESTIS       21  ANIMASPNNTIVTITGKGG-NALGWATAGOSOFRGSRKSTPFAAQVAAERCAEAVKE-YGIKELEVSVKG  55
GEOBACILLUS_          20  AHIRSTFNNTIVTITOVNG-NALAWASAOSLGPKGSRKSTPFAAQMEAEAAAKASME-NGNKTVEVNVKG  87
STEAROTH
THERMUS_              19  AYTKASYNNTIVTITGPUG-NPITWSSGGVIGYKOSEKOTPYAAQLAALDAAKKANA-YGMQSVUVTVRG  56
AQUATICUS
DEINOCOCCUS_          22  AYVHASYNNTIVTITDLDG-NSVAWSSGGTIGYKGSKKGTPYAAQLAAADAVKKAQTSFGMAAVDVIVRG  90
RADIODUR
STREPTOMYCES_         26  ANSKSTFNNTIVSITOPTG-NVISNASAGHVGFKGSEKSTPPAAQMAAESAAERAGE-NGMKKVOVFVKG  93
COELICO
CLOSTRIDUM_           23  AHIKSTFNNSIVTTTOVNG-NALSSSSAGGLGPKGSEKSTPFAAQMAERTAAKTEME-HGLKSVDVPVKG  90
ACETOBUT
TREPONEMA_            15  VYIQATFNNTIITVTULQG-NALSWASSGGLGFNGAKKSTPFAAQTVAEAAVQKAQQ-CGLREVMVFVKG  85
PALLIDUM
LEPTOSPIRA_           27  VYITASFNNTIVTITOMAG-NTISWSTSGAMGFRGSKKSTPYAAQIAAGNAAEKAIQSAGLQEVOVNVSG  95
INTERROGA
AQUIFEX_AEOLICUS      17  VMIMTTFNNTIVNVTOTGG-NTIATSASGOTVGFRGTERSTPYAAQLAQKANKEAKE-HGVQEVEIWVKG  84
VIBRIO_CHOLERA        21  AHIHASFNNTIVTITOEQG-NALAWATAGGSGPEGSEKSTPPAAQVAAERCAEMAKE-YGLKNLEVMVKG  59
SALMONELLA_           21  AHIMASFNNTIVTITOEQG-NALGWATAGGSOFEGSEKSTPFAAQVAAERCAGAVK5-YGOKNLEVMVKG  88
ENTERICA
THERMOTOGA_           22  VMIXSTFNNTIITLTOKOG-NTLTWASGOTVGFEGTRKGTPYAAQLAEOKVAREALE-MGIKKVOVLVKG  89
MARITIMA
BACILLUS_             21  AHIESTFNNTSVTITOPHG-NAISWASAGALGFKGSEKSTPFAAQMAAETAAKAENE-NOMKSIEVSVRG  88
HALOCURANS
CYANOPHORA_           22  AHIQSTFNNTTISITSPTO-EVOAWASAGSSOPKGARKGTPFAAQTAAENSAEQENE-QGMEQIEVITSG  89
PARAGOXA
BACILLUS_SUBTILIS     23  AHIESTFNNTIVTITOTNG-NEIBWSSAOELGFEGSEKSTPFAAQMAAETAAKGSIE-MGLKTLEVTVKG  90
LISTERIA_INNOCUA      21  ANTESTFNNTIVMITOTNO-NALAWSSAGSLGFKGSRKSTPFAAQMAAESAAKSAQE-NGLRTLEVTVRG  88
STREPTOCOCCUS_        19  ANIMATFNNTSVMITOVMG-NAIAWSSAGALOFKGSRRSTPFAAQMASEAAAKSAQE-NOLKSVEVTVKG  86
PHEUMO
OENOTHERA_ELATA       36  IHVQASFMNTOVTVTOVEG-RVTSWSSAGTCGPKSTERGTPFAAQTAAGOAIEPVVO-QGMGRAEVEIKG  103
SPINACIA_             30  IHVQASPNNTIVTVTOVRG-RVVSWASAGTCGFROTKAGTPFARQTARONAIRTVVE-QOMQRAEVMIRG  97
OLERACEA
ZEA_MAYS              38  IHVQASFNNTIITVTOPQO-EVVFWSSAGTCOEKESRKASPYAOGRTAVOAORTV----GLQRAEVMVKG  102
ORYZA_SATIVA          38  IHVQAEFNNTIITVTOPQG-RVVFNSSAGTCGFKSSEKASPYAGQRTAVOAIRTV----GLQRAEVNVKG  102
```

TABLE I-continued

| | | |
|---|---|---|
| PINUS_THUNBERGII_CHL | 22 | IYVQASFMNTIVTATOVRG-QVLSVSSAOACGFRGTERGTPFAAQTAAENVIRALMG-RGMERVEVMISG 89 |
| EUGLENOPHYCEAN_ALGA | 4 | VYIKMSPNNTIVTVSOORA-NVLSWCSSGVCKFKGRGKTTAFATRIVITEALKSVLE-EOFNGIOIKVSG 71 |
| COMMON_TOBACCO | 30 | IHVQASPNNTIVTVTOVRG-RVVSWSSAGTSGFKGTKEGTPFAAGTEAANAIRTVVG-QGMQRAEVMIKG 97 |
| CHLAMYDIA_TRACHOMATI | 24 | VNVKATPNNTIVTTTOPAG-NVISMASAOXVGYSGSRKSSAFAATVAAQOAAKAENS-SGKLEVEVGKDG 91 |
| HOMO_SAPIENS_MITOCHO | 51 | AHIKASHNNTQTQVVSASN-EPLAFASCGTEGFRNARKGTOIAAQTAGIAAAARAKQ-KGVIMIEVVVKG 118 |
| HALOARCULA_MARISMORT | 12 | AHVHASFNNTIITITDQTGAETLAKSSGGTVVEQNEOEASPYAENQMAEVVAEKALD-RGVEGVDVRVRG 80 |
| HALOBACTERIUM_SALINA | 10 | AHVMASFNNTIMTVTOGTGAETLAKSSGOSVVRGNEOEASPYAAMQMAEGLAEEVLD-QGIEKVNVRVRG 78 |
| METHANOCOCCUS_JANNAS | 12 | VHIYSSYNNTIIKATOITGAETIARVSGGNVTENGEOEGSPYAEMQAAFRLAEVLKE-RGIENININRVRA 80 |
| RATTUS_NORVEGICUS_S1 | 18 | DRYSAVVRNNEQVVMSPSLLEDVELMGYGOSVQDGAPOLYTYFTILKSICVEVOMO-LLPREEWQAKVAG 86 |
| NEUROSPORA_CRASSA_S1 | 30 | ARIFASFNOTPVNVTOLSGRETTORVIGGIRVREGEOESSPYAEMLEAQOVAERCRE-LGITELMOKIEA 98 |
| MELANOGASTER_S14 | 31 | AHIYASFNOTFVNVTOLSGEETIAEVTGOMRVKEOROEASPYAANLAAGOVAEKCKT-LGOTALMOKLRA 99 |
| CRICETUSLUS_GRISEUS_ | 31 | CHIFASFNOTFVMVTOLSOKETICEVTOGMKVKAORGESSPYAAMLAAGOVAGRCKE-LOOTALNIKLRA 99 |
| HOMO_SAPIENS_S14 | 31 | CHIFASFNDTFVMVTDLSGKQTICRVTGGMKVKEOEOESSPYAEMLTTQOVAQECKE-LGIIALNIQLRA 99 |
| BRUCEI_S14 | 24 | VHIYASFNDTFVHVTDMSGRETFCKVTGGMKVKADRDESSPYAAMMAAQDVVARCKE-CGINALHVKMRA 92 |
| ESCHERICHIA_COLI | 89 | PG--------PGRESTI--RALNAAGFRITNITDVTPIPIHNGCRPPKKRRV------------- 129 |
| THERMUS_THERMOPHILUS | 77 | TG--------AGREQAI--RALQASGLQVKSIVOOTPVPHNGCRPKKKFRKAS----------- 119 |
| CAULOBACTER_CRESCENT | 89 | PG--------SGRESAL--RALGAAONTITTIROVTPIPHNOCRPPXRRV------------- 129 |
| MESORHIZOBIUM_LOTI | 89 | PG--------SGRESAL--RALQAAGFTITSIROVTPIPHNGCRPPKKRRV------------- 129 |
| HAEMOPHILUS_INFLUENZ | 89 | PG--------PGRESTI--RALNAAOFRITNITOVTPIPIHNGCRPPKKRRV------------- 129 |
| YERSINIA_PESTIS | 89 | PG--------PGRESTI--RALNAAOPRITNXTOVTPIPOIOCRPPKKRRV------------- 129 |
| GEOBACILLUS_STEAROTH | 88 | PG--------AGREAAI--RALQAAGLEITAIKOVTPIPHOCCRPPKRRRV------------- 128 |
| THERMUS_AQUATICUS | 87 | TG--------AGREQAI--BALQASGLQVKSIVOOTPVPMNGCRPKKKFRKAS----------- 129 |
| DEINOCOCCUS_RADIODUR | 91 | SG--------SGREQAI--RAICAEOIEVRSIMOOSPvPHNOCRPKXKPRA------------- 131 |
| STREPTOMYCES_COELICO | 94 | PG--------SGRETAI--RSLOATOLEVGSICOVTPTPHNGCRPPKRRRV------------- 134 |
| CLOSTRIDIUM_ACETOBUT | 91 | PG--------SGREAAI--RSLQAAOLEVTLIKOVTPIPIGGCRPPKRRBV------------- 131 |
| TREPONEMA_PALLIDUM | 86 | PG--------IGRESAI--RMLGTMGLRVRSIROITPIPHNGCRPRKTRRI------------- 126 |
| LEPTOSPIRA_INTERROGA | 96 | PG--------IGRESAI--RSLVARGLNIKMIKOVTPLPHNGCRPRKRRV------------- 136 |
| AQUIFEX_AEOLICUS | 69 | PG--------AGRESAV--RAVFASGVKVTAIROVTPIPHNOCRPPARRRV------------- 129 |
| VIBRIO_CHOLERAE | 89 | PG--------PGRESTV--RALNAAOPRITNIVOATPIPENOCRPPKKRRV------------- 129 |
| SALMONELLA_ENTERICA | 89 | PG--------PGRESTI--RALNAAGFRITNITDVTPIPHNGCRPPRKRRV------------- 129 |
| THERMOTOGA_MARITIMA | 90 | PG--------PGREPAI--RTLQGAGLEINQIKOVTPIPENOCRPPKKRRV------------- 130 |
| BACILLUS_HALOCURANS | 89 | PG--------AGREAAI--RSLQAVGLEVNMIKDVTPVPHNGCRPPKRRRV------------- 129 |
| CYANOPHORA_PARADOXA | 90 | PG--------SGREMAI--KALQATGLEISLIROITPVPHNGCRPPKRRRV------------- 130 |
| BACILLUS_SUBTILIS | 91 | PG--------SGREAAI--RALQAAGLEVTAIROVTPVPIHNCRPPKRRRV------------- 131 |
| LISTERIA_INNOCUA | 89 | PG--------SGREAAI--RALQAAOLEVTAIKDVTPVPHNOCRPPKRRRV------------- 129 |
| STREPTOCOCCUS_PHEUMO | 87 | PG--------SGRESAI--RALAAAOLEVTAIROVTPVPHNGARPPXRRRV------------- 127 |
| OENOTHERA_ELATA | 104 | PG--------LGROAAL--RAIRRSGORLSCIROVTPLPHNGCMPPKKRRV------------- 144 |
| SPINACIA_OLERACEA | 98 | PG--------LGRDAAL--RAIRRSGILLSPVROVTPMPHNOCRPPKKRRV------------- 118 |
| ZEA_MAYS | 103 | AG--------SGRDAAL--RAIAKEGVRLSCIROVTPNPHNOCRPPKKRRL------------- 143 |
| ORYZA_SATIVA | 103 | AG--------SGRDAAL--RAIAKSGVRLSCIRDVTPMPHNGCRPPKKRRL------------- 143 |
| PINUS_THUNBERGII_CHL | 90 | PG--------RGRDTAL--RTIRRSOILLSFVROVTPMPHNGCRPPKKRRV------------- 130 |
| EUGLENOPHYCEAN_ALGA | 72 | PG--------FGRNVAI--RAIIKMGFKVPSLKOITPLPYNGCRPRKRRRT------------- 112 |
| COMMON_TOBACCO | 98 | PG--------LGRDAAL--RAIRRSGILLTFVRDVTPMPHNGCRPPKKRRV------------- 138 |
| CHLAMYDIA_TRACHOMATI | 92 | TG--------AGRESAV--RALISSGLIVSVIRDETPVPMNOCRPRKRRRV------------- 132 |
| HOMO_SAPIENS_MITOCHO | 119 | LG--------PGRLSAM--HGLIMOGLEVIELTOMTPIPHNGCRPRKARKL------------- 169 |
| HALOARCULA_MARISMORT | 81 | PGGNLQTSPGPGAQATI--RALARAGLEIGRIEDVTPTPHDGTRAPKNSGF------------- 129 |

TABLE I-continued

| | | |
|---|---|---|
| HALOBACTERIUM_SALINA | 79 PGGHLQRSPOPGAQAAI--RALARAGLEIGRIEDVTPIPHDGTRPPKNSGY------------- | 127 |
| METHANOCOCCUS_JANNAS | 81 PGGSGQKNPOPOAQAAI--RALARAOLRIGRIEOVTPVPHOOTTPKXRPKK------------- | 129 |
| RATTUS_NORVEGICUS_S1 | 87 NEGSEAENEAASTEEAEEORLSEELOLEAQFMLHFSSLMMILTNLTQXAQEVTQKYQEMTGQVL | 150 |
| NEUROSPORA_CRASSA_S1 | 99 TGGNGTRTPGPGAQSAL--RALARSGMKIGRIEOVTPTPSOSTRRKOORRORRL---------- | 150 |
| MELANOGASTER_S14 | 100 TGGNKTXTPOPOAQSAL--RALARESMKIORIEOVTPIPSOETRRKOGRRORRL---------- | 151 |
| CRICETUSLUS_GRISEUS_ | 100 TGONRTKTPOPOAQEAL--NALARBOMXIORIEOVTPIPBOSTRRKOORRORRL---------- | 151 |
| HOMO_SAPIENS_S14 | 100 TGGNRTKTLOPGPS---------RP---------SEPLPARV--------------------- | 123 |
| BRUCEI_S14 | 93 TGGVGTKSPOPGAQAAL--RALARAGMXIGRIEOVTPVPTOSTRRKOSRRGRRL---------- | 144 |

Introduction

Ribosomes are ubiquitous supramolecular complexes that are responsible for protein synthesis in all living cells. They contain large amounts of ribosomal RNA (rRNA), in addition to more than 50 different proteins. Unlike other cellular polymerases, their mechanism of action appears to be fundamentally based on RNA—i.e., they are ribozymes. A detailed knowledge of the three-dimensional structure of rRNA and proteins in the ribosome thus is essential for a molecular understanding of translation.

Understanding the structural basis for the functional capabilities of ribosomal RNA (rRNA) thus is essential for explaining why these ancient organelles use RNA, instead of protein, for the complex and biologically crucial task of translation. Bacterial and archaeal ribosomes are comprised of small (30S) subunits which contain 16S rRNA and about 20 proteins, and large (50S) subunits, which contain 23S rRNA, 5S rRNA and over 30 proteins. The complete 70S ribosome is formed by binding of the 30S subunit to the 50S subunit via a network of intermolecular bridges. The intersubunit space formed between the two subunits is occupied by the transfer RNAs (tRNAs), whose anticodons base pair to the mRNA codons in the 30S subunit, while their 3'-CCA ends reach into the peptidyl transferase center, the site of peptide bond formation in the 50S subunit.

Uses of the Crystal Structure Coordinates of the 70S Ribosome

The 5.5 Angstrom structure of 70S ribosome we determined from *T. thermophilus* may be used as a model for rationally designing pharmacophores and/or candidate compounds, either de novo or by modification of known compounds. Pharmacophores and candidate compounds identified through the use of the crystal structure coordinates are useful for altering the rate of bacterial protein synthesis, and so have utility as antimicrobial agents, including antibiotics, and preservatives. Pharmacophores and candidate compounds may be determined according to any method known in the art, including the methods described in U.S. Pat. No. 5,888,738 to Hendry, and the methods described in U.S. Pat. No. 5,856,116 to Wilson et al. the disclosures of which both are incorporated by reference in their entirety for all purposes.

The structure data provided herein may be used in conjunction with computer-modeling techniques to develop models of sites on the 70S ribosome selected by analysis of the crystal structure data. The site models characterize the three-dimensional topography of site surface, as well as factors including van der Waals contacts, electrostatic interactions, and hydrogen-bonding opportunities. Computer simulation techniques are then used to map interaction positions for functional groups including protons, hydroxyl groups, amine groups, divalent cations, aromatic and aliphatic functional groups, amide groups, alcohol groups, etc. that are designed to interact with the model site. These groups may be designed into a pharmacophore or candidate compound with the expectation that the candidate compound will specifically bind to the site. Pharmacophore design thus involves a consideration of the ability of the candidate compounds falling within the pharmacophore to interact with a site through any or all of the available types of chemical interactions, including hydrogen bonding, van der Waals, electrostatic, and covalent interactions, although, in general, and preferably, pharmacophores interact with a site through non-covalent mechanisms.

The ability of a pharmacophore or candidate compound to bind to the 70S ribosome can be analyzed prior to actual synthesis using computer modeling techniques. Only those candidates that are indicated by computer modeling to bind the target with sufficient binding energy (i.e., binding energy corresponding to a dissociation constant with the target on the order of $10^{-2}$ M or tighter may be synthesized and tested for their ability to bind to the 70S ribosome and to inhibit ribosome function using binding assays or ribosome function assays known to those of skill in the art. The computational evaluation step thus avoids the unnecessary synthesis of compounds that are unlikely to bind the 70S ribosome with adequate affinity.

A 70S ribosome pharmacophore or candidate compound may be computationally evaluated and designed by means of a series of steps in which chemical entities or fragments are screened and selected for their ability to associate with individual binding target sites on the 70S ribosome. One skilled in the art may use one of several methods to screen chemical entities or fragments for their ability to associate with the 70S ribosome, and more particularly with target sites on the 70S ribosome. The process may begin by visual inspection of, for example a target site on a computer screen, based on the 70S ribosome coordinates, or a subset of those coordinates, as set forth in Appendix I. Selected fragments or chemical entities may then be positioned in a variety of orientations or "docked" within a target site of the 70S ribosome as defined from analysis of the crystal structure data. Docking may be accomplished using software such as Quanta (Molecular Simulations, Inc., San Diego, Calif.) and Sybyl (Tripos, Inc. St. Louis, Mo.) followed by energy minimization and molecular dynamics with standard molecular mechanics forcefields such as CHARMM (Molecular Simulations, Inc., San Diego, Calif.) and AMBER (University of California at San Francisco).

Specialized computer programs may also assist in the process of selecting fragments or chemical entities. These include but are not limited to: GRID (Goodford, P. J., "A Computational Procedure for Determining Energetically Favorable Binding Sites on Biologically Important Macromolecules," *J. Med. Chem.*, 28, pp. 849–857 (1985)); GRID is available from Oxford University, Oxford, UK; MCSS (Miranker, A. and M. Karplus, "Functionality Maps of Binding Sites: A Multiple Copy Simultaneous Search Method," Proteins: Structure, Function and Genetics, 11, pp. 29–34 (1991)); MCSS is available from Molecular Simulations, Inc., San Diego, Calif.; AUTODOCK (Goodsell, D. S. and A. J. Olsen, "Automated Docking of Substrates to Proteins by Simulated Annealing," Proteins: Structure, Function, and Genetics, 8, pp. 195–202 (1990)); AUTODOCK is available from Scripps Research Institute, La Jolla, Calif.; DOCK (Kunts, I. D., et al. "A Geometric Approach to Macromolecule-Ligand Interactions," *J. Mol. Biol.*, 161, pp. 269–288 (1982)); DOCK is available from University of California, San Francisco, Calif.; CERIUS II (available from Molecular Simulations, Inc., San Diego, Calif.); and Flexx (Raret, et al. *J. Mol. Biol.* 261, pp. 470–489 (1996)).

After selecting suitable chemical entities or fragments, they can be assembled into a single compound. Assembly may proceed by visual inspection of the relationship of the fragments to each other on a three-dimensional image of the fragments in relation to the 70S ribosome structure or portion thereof displayed on a computer screen. Visual inspection may be followed by manual model building using software such as the Quanta or Sybyl programs described above.

Software programs also may be used to aid one skilled in the art in connecting the individual chemical entities or fragments. These include, but are not limited to CAVEAT (Bartlett, P. A., et al. "CAVEAT: A Program to Facilitate the Structure-Derived Design of Biologically Active Molecules" In "Molecular Recognition in Chemical and Biological Problems," *Special Publ, Royal Chem. Soc.*, 78, pp. 182–196 (1989)); CAVEAT is available from the University of California, Berkeley, Calif.; 3D Database systems such as MACCS-3D (MDL Information Systems, San Leandro, Calif.); this area is reviewed in Martin, Y. C., "3D Database Searching in Drug Design," *J. Med. Chem.*, 35:2145–2154 (1992)); and HOOK (available from Molecular Simulations Inc., San Diego, Calif.).

As an alternative to building candidate pharmacophores or candidate compounds up from individual fragments or chemical entities, they may be designed de novo using the structure of a 70S target site, optionally, including information from co-factor(s) or known activators or inhibitor(s) that bind to the target site. De novo design may be included by programs including, but not limited to LUDI (Bohm, H. J., "The Computer Program LUDI: A New Method for the De Novo Design of Enzyme Inhibitors", *J. Comp. Aid. Molec. Design*, 6, pp. 61–78 (1992)); LUDI is available from Molecular Simulations, Inc., San Diego, Calif.; LEGEND (Nishibata, Y., and Itai, A., *Tetrahedron* 47, p. 8985 (1991); LEGEND is available from Molecular Simulations, San Diego, Calif.; and LeapFrog (available from Tripos Associates, St. Louis, Mo.).

The functional effects of known ribosome ligands also may be altered through the use of the molecular modeling and design techniques described herein. This may be carried out by docking the structure of the known ribosome ligand on a bacterial 70S ribosome model structure and modifying the shape and charge distrubution of the ligand to optimize the binding interactions with the 70S ribosome. The modified structure may be synthesized or obtained from a library of compounds and tested for its binding affinity and/or effect on ribosome function. Of course, where the crystal structure of a complex between a 70S ribosome or ribosome subunit and a ligand is known, comparisons between said complex and the 70S ribosome structures of the present invention can be made to gain additional information about alterations in ribosome conformation that occur upon ligand binding. This information can be used in design of optimized ligands. Antibiotics that interfere with ribosome function are especially well suited for the docking, co-crystallization, and optimization applications of the present invention. A list of these types of antibiotics may be found in Spahn and Prescott, *J. Mol. Med.*, 74: 423–439 (1996), which is incorporated by reference in its entirety for all purposes.

Additional molecular modeling techniques also may be employed in accordance with the invention. See, e.g., Cohen, N. C., et al. "Molecular Modeling Software and Methods for Medicinal Chemistry," *J. Med. Chem.*, 33, pp. 883–894 (1990); Hubbard, Roderick E., "Can drugs be designed?" *Curr. Opin. Biotechnol.* 8, pp. 696–700 (1997); and Afshar, et al. "Structure-Based and Combinatorial Search for New RNA-Binding Drugs," *Curr. Opin. Biotechnol.* 10, pp. 59–63 (1999).

Following pharmacophore or candidate compound design or selection according to any of the above methods or other methods known to one skilled in the art, the efficiency with which a candidate compound falling within the pharmacophore definition binds to the 70S ribosome may be tested and optimized using computational evaluation. A candidate compound may be optimized, e.g., so that in its bound state it would preferably lack repulsive electrostatic interaction with the target site. These repulsive electrostatic interactions include repulsive charge-charge, dipole-dipole, and charge-dipole interactions. It is preferred that the sum of all electrostatic interactions between the candidate compound and the 70S ribosome when the candidate compound is bound to the 70S ribosome make a neutral or favorable contribution to the binding enthalpy.

Specific computer software is available in the art to evaluate compound deformation energy and electrostatic interactions. Examples of programs designed for such uses include, but are not limited to Gaussian 92, revision C (Frisch, M. J., Gaussian, Inc., Pittsburgh, Pa. (1992)); AMBER, version 4.0 (Kollman, P. A., University of California at San Francisco, (1994)); QUANTA/CHARMM (Molecular Simulations, Inc., San Diego, Calif. (1994)); and Insight II/Discover (Biosym Technologies Inc., San Diego, Calif. (1994)). These programs may be run, using, e.g., a Silicon Graphics workstation, Indigo, 02-R10000 or IBM RISC/6000 workstation model 550. Other hardware and software combinations may be used to carry out the above described functions, and are known to those of skill in the art.

Once a pharmacophore or candidate compound has been optimally selected or designed, as described above, substitutions may then be made in some of its atoms or side groups to improve or modify its binding properties. Generally, initial substitutions are conservative in that the replacement group will have approximately the same size, shape, hydrophobicity and charge as the original group. Components known in the art to alter conformation should be avoided in making substitutions. Substituted candidates may be analyzed for efficiency of fit to the 70S ribosome using the same methods described above.

Once a candidate compound has been identified using any of the methods described above, it can be screened for biological activity. Any one of a number of assays of ribosome function known to those of skill in the art may be used. These include, but are not limited to: inhibition of bacterial growth, inhibition of in vitro protein synthesis using messenger RNA as a template, inhibition of the elongation phase of in vitro protein synthesis using polyU as a template, inhibition of GTP hydrolysis mediated by EF-G; activation of GTP hydrolysis mediated by EF-G.

Candidate compound interaction with the 70S ribosome also can be evaluated using direct binding assays including filter binding assays, such as are known to those skilled in the art. Binding assays may be modified to evaluate candidate compounds that competitively inhibit the binding of known ribosome binding compounds such as antibiotics. These and other assays are described in International Publication WO 00/69391, the entire disclosure of which is incorporated by reference in its entirety for all purposes.

Compound Libraries for Screening

Inhibitors and/or activators identified according to the methods of the invention may be provided from libraries of compounds available from a number of sources or may be derived by combinatorial chemistry approaches known in the art. Such libraries include but are not limited to the available Chemical Director, Maybridge, and natural product collections. In one embodiment of the invention libraries of compounds with known or predicted structures may be docked to the 70S ribosome structures of the invention.

The following examples are set forth so that the invention may be understood more fully. The examples are for illustrative purposes only and are not to be construed as limiting this invention in any manner.

EXAMPLE 1

Crystallization and Structure Solution of the 70S Ribosome

The three-dimensional structure of a functional complex of the 70S ribosome was determined at 5.5 Angstrom resolution using X-ray crystallography. Crystals were prepared essentially as described by Cate et al., 1999. Crystal preparation and calculation of the electron density maps and fitting of the maps proceeded as follows.

Crystals of *Thermus thermophilus* 70S ribosomes in a complex with a synthetic mRNA analogue and, $tRNA^{Met}_f$ bound to the P and E sites were grown as described (Cate et al. 1999). Ribosomes were prepared from *Thermus thermophilus* HB8 lysate as described in Gogia, Z, Yusupov, M, et al., *Mol. Biol.* (USSR) 20, 519 (1986). A 36-nt phage T4 gene 32 mRNA fragment (SEQ ID NO: 50) with a modified Shine-Dalgarno sequence and two other variant mRNAs (SEQ ID NOS: 51 and 52) were chemically synthesized (Dharmagon). $tRNA^{Met}_f$ and $tRNA^{Lys}$ were isolated from *E. coli* (Subriden). An anticodon stem loop ("ASL") of $tRNA^{Phe}$ (19 nucleotides, $ASL^{Phe}$) was synthesized by in vitro transcription with t7 polymerase. The RNAs were purified on denaturing gels, eluted, and precipitated with ethanol before use. To form a P-site ribosome complex, the shortened gene 32 mRNA and $ASL^{Phe}$ or $tRNA^{met}_f$ were incubated at 37° C. for 30 min in a solution containing 20 mM $MgCl_2$, 100 mM KCl, and 20 mM tric HCl (pH 7.4) before ribosome crystallization (Yusupov, M. M., et al., *Dokl. Akad. Nauk.* (USSR) 292, 1271 (1987); Yusupova, G. Zh, and Yusupov, M. M., et al., unpublished data. All ligands were present in a 1.1- to 1.5-fold stoichiometric excess over the concentration of ribosomes to form the complexes before crystallization. Crystals of *Thermus thermophilus* 70S ribosome complexes were grown by the vapor diffusion method in hanging and sitting drops. Crystals grew to maximum dimensions of 0.5 mm by 0.5 mm by 0.25 mm. Heavy atom derivatives were prepared by soaking crystals in solutions containing heavy-atom compound for 1 to five days. To obtain a ribosome complex with ASL in the P site and tRNA in the A site, crystals of the P-site complex (ribosome-mRNA-$ASL^{Phe}$) were soaked in a solution containing $tRNA^{Lys}$ (2 μM, Sigma) for 48 hours at room temperature. Crystals having $tRNA^{Met}_f$ in the P site diffracted at higher resolution as compared to those having ASL in the P site. As expected, there was variability in the quality of X-ray diffraction obtained from different crystals. 5.0 Angstrom resolution diffraction data could be obtained from $tRNA^{Met}_f$ P-site crystals using cryo-crystallographic techniques to minimize radiation damage to the crystal during data collection. The signal to noise properties of the diffraction data were optimized by moving the beam stop close to the crystal to minimize background scatter from air.

Crystals grew in space group 1422 with cell dimensions of a=b=507.2 Å and c=803.7 Å. Data were collected out to 5 Å resolution. Structure factor amplitudes were measured at the Advanced Light Source (ALS), essentially as described (Cate et al. 1999). Phasing began using molecular replacement obtained from an electron microscopy-derived model to provide phases out to 25 Angstroms. These phases were extended to 12 Angstroms using heavy metal clusters. Structure factor phases determined experimentally from a crystal containing an anticodon stem-loop tRNA analogue in the P site ("AS") (Cate et al. 1999) were used as a starting point for structure factor phasing of diffraction data measured from crystals containing $tRNA^{Met}_f$ in the P site. Additional MAD phasing using iridium hexamine was carried out to obtain phases for data to 7.5 Angstroms, and phase extension using solvent flipping produced the current 5.5 Angstrom electron density map. Phase extension to 5.5 Å was carried out by density modification and solvent flipping in CNS (Brunger et al. 1998). The quality of the phases was confirmed by the electron density of the bound P tRNA, which provided an internal standard of known structure (FIG. 1). Using 70S complexes crystallized with and without tRNA bound to the A site, a 7 Å Fourier difference map was obtained that provided the position of the A-site tRNA. Table II summarizes the crystallographic statistics and scaling.

TABLE II

| | Crystallographic statistics and scaling. | | | |
|---|---|---|---|---|
| Crystal: | ASL | P site | No mRNA | A site |
| High-resolution limit (Å) | 7.5 | 5 | 6.5 | 6.5 |
| $R_{sym}$, Mean I/σ (I) | 8.9<br>3.1<br>(at 7.8 Å) | 9.4<br>3.3<br>(at 5.5 Å) | 8.9<br>4.4<br>(at 7.0 Å) | 7.2<br>3<br>(at 7.0 Å) |
| Number of reflections | | | | |
| Unique | 124,437# | 209,044 | 95,127 | 95,671 |
| Observational redundancy | 4.4 | 2.8 | 3.6 | 2.3 |
| Completeness, % | 97.7 | 95.3 | 96.6 | 93.9 |
| $R_{iso}$†, % | | 23.6 | | |

TABLE II-continued

Crystallographic statistics and scaling.

| Crystal: | ASL | P site | No mRNA | A site |
|---|---|---|---|---|
| $\chi^2$, cross-crystal‡ | | 36.9 | | |
| Mean figure of merit for starting phase set (at 7.5 Å)**: | | 0.505 | | |

*$R_{sym} = \Sigma|I - <I>| / \Sigma I$
†$R_{iso} = \Sigma|F_{PH} - <F_p>| / \Sigma F_{PH}$, where $F_{PH}$ and $F_P$ are the structure factor amplitudes from the ASL-containing ribosome crystal and the P-site tRNA-containing ribosome crystal, respectively.
‡$\chi^2$, analysis, from 20 to 7.5 Å, was taken from Scalepack (Otwinoski 1993).
**The mean figure of merit, or mean cosine of the phase error, was calculated from experimental phases measured from the ASL-containing crystal (Cate et al. 1999).
Data set taken from the previously reported MAD phasing experiment (Cate et al. 1999).

At 5.5 Å, the RNA backbones can be traced with high confidence, and proteins of known structure can be fitted readily to the electron density. Three-dimensional model renderings were generated using RIBBONS (M. Carson, Methods Enzymol. 277B, 493–505 (1997)), electron density maps with RIBBONS and with O (Jones, T. A., Zou, J. Y., et al., ACTA Crystallogr. A 47, 110 (1991)), and secondary structure diagrams with XRNA. Although final interpretation of the electron density maps was greatly facilitated by the availability of the high-resolution subunit structures (Ban et al. 2000; Schluenzen et al. 2000; Wimberly et al. 2000), the quality of our maps was sufficient to allow a reasonable initial fit of the 16S rRNA chain (overall rmsd=5.7 Å) guided by biochemical and phylogenetic constraints but independent of any high-resolution structural information.

The 3 Angstrom structure of the 30S ribosomal subunit was docked onto the 70S 5.5 Angstrom resolution map we generated according to the following methods. The phosphate positions known from our 5.5 Angstrom resolution structure were used to align the phosphates of the 16S rRNA contained within the 30S structure determined by Wimberly et al. (2000), using an initial fit by eye which subsequently was refined using an ordinary least squares fitting algorithm. Such docking and fitting can be carried out, e.g., using MIDAS (University of California, San Francisco department of Biochemistry and Molecular Biophysics) running on an SGI O2 or Octane type machine.

Refinement of the docking was carried out by using the 30S structure as a rigid body to obtain the initial alignment. This was followed by successive iterations of breaking down the 30S structure into successively smaller components, eventually using each phosphate in the 16S rRNA as a pseudoatom to obtain the most precise fit between the high resolution structure of the 30S subunit and our 5.5 Angstrom 70S structure.

The Wimberly 30 S structure coordinates were obtained from the PDB (PDB ids 1FJF and 1FJG; MMDB ids 14321 and 14322). Because this 30S structure was determined from T. thermophilus, initial fits for the high resolution 30S structure to our 5.5 Angstrom were qualitatively good. After, fitting the backbone of 16S rRNA in our electron density map, high resolution structures of 30S subunits appeared (Wimberly et al. 2000; Schluenzen et al. 2000). Our model agreed more closely (overall r.m.s.d.=6.9 Å) with the structure of Wimberly et al. than with that of Schluenzen et al.

Small subunit proteins were docked initially as rigid bodies using the coordinates for the individual proteins from the T. thermophilus 30S subunit structure (Wimberly et al. 2000). Structures for most of the T. thermophilus large subunit proteins are not known; therefore, the structures of proteins from the most closely related organisms were modeled, after deleting any extra residues.

Availability of the Haloarcula marismortui 50S subunit structure (containing 23S and 5S rRNAs) (Ban et al. 2000) facilitated fitting the 50S subunit portion of our electron density in regions that are conserved between the bacterial and archaeal structures; initial rigid-body docking of large fragments of the archaeal structure was followed by detailed fitting of smaller fragments and individual phosphates to our map. Representative structures used for docking include PDB id 1FFZ; MMDB id 14060 (with puromycin), PDB id 1FG0; MMDB id 14061 (with 13 bp minihelix puromycin compound, and PDB id 1FFK; MMDB id 14164 (50S alone).

Additional refinements between the high resolution 50S subunit structure and the 50S portion of our 70S model structure, carried out according to the same methods described below, were required because there are conformational differences between the 50S subunit when crystallized without the 30S subunit, but also because of phylogenetic differences between the structures of the 23S rRNAs from Haloarcula marismortui and Thermus thermophilus. Conserved regions of primary and secondary structure were generally observed to fit well as between the 50S and 70S structures. In regions of obvious differences, especially those arising in phylogenetically diverse regions of the two structures, the Haloarcula structure was modeled onto the 70S T. thermophilus structure. Regions of phylogenetic differences among different ribosome structures are well known and are collected, e.g., at the website maintained by the lab of Robin Gutell, located at RNA.icmb.utexas.edu.

Several regions in the 50S structure determined by Ban et al. (2000) were sufficiently disordered as to not be visible, yet could be visualized in the 70S 5.5 Angstrom map. Known secondary structure aspects of the rRNAs contained within the 50S subunit were easily fit into the 5.5 Angstrom electron density map. The 5S primary structure is 60% conserved between Haloarcula and T. thermophilus, and so this region was easily fit. The remaining 40% of the 5S structure was modeled on a fragment of 5S solved from E. coli (PDB id 354D; MMDB id 6741), and this was used to model the Loop E region, containing the most significant differences between Haloarcula and T. thermophilus.

Atomic coordinates for the 70S ribosome 5.5 Angstrom model are contained in the PDB files attached to this specification as Appendix I. The components are identified as follows: File A includes coordinates for the 30S ribosome subunit and associated tRNA and mRNA molecules; File B includes coordinates for the 50S ribosome subunit; File C includes coordinates for the IF3 C-terminal domain docked to the 70S subunit; File D includes coordinates for the IF3 N-terminal domain docked to the 70S subunit; File E includes coordinates for Mk27, a 27 nucleotide synthetic mRNA modeled in the 30S subunit; File F includes coordinates for Mv36, a 36 nucleotide synthetic mRNA in the 30S subunit; and File G includes coordinates for Mf36, a 36 nucleotide synthetic mRNA in the 30S subunit. Where the coordinates have been deposited with the RCSB, a database ID for the file is indicated in Table VI (see Appendix I). Deposited coordinates may be accessed at, e.g., ncbi.nlm.nih.gov.

Overall Structure of the 70s Ribosome

FIG. 2A shows the structure of the 70S ribosome in the "standard view" from the solvent face of the 30S subunit, showing its head (H), body (B), platform (P) and neck (N) features and their corresponding 16S rRNA (cyan) and protein (blue) components. Jutting out at the lower right is the "spur" of the 30S subunit, formed by helix 6 of 16S rRNA, which makes a crystal contact with the P site of another subunit in the recently reported 30S subunit structure (Carter et al. 2000). In this view, the positions of proteins S2, S3, S9, S10 and S14 in the head; S6, S11 and S18 in the platform; and S4, S5, S8 and S16 in the body can be seen. In the background, parts of the 50S subunit are visible in the "crown" view, with its 23S rRNA (gray), 5S rRNA (top; blue) and 50S subunit proteins (magenta). Protein L9 can be seen at the left, extending more than 50 Å beyond the surface of the 50S subunit proper. On the upper left, L1 and its 23S rRNA binding site protrude outside the profile of the 30S subunit, and protein L11 and its RNA and one of the L7 dimers make up the stalk at the upper right.

From the right-hand side (FIG. 2B), the anticodon end of the A-site tRNA (gold) is visible in the near end of the subunit interface cavity, viewed through the large funnel-shaped opening where elongation factors EF-Tu and EF-G interact with the ribosome. One of the ribosomal structures that interacts with the G domains of the elongation factors is the sarcin-ricin loop (SRL) of 23S rRNA, which is visible between the A-tRNA and protein L14. Also evident in the right-hand view are proteins S9, S12, S13, S19, S20, L3, L5, L6, L7, L11, L13, L14, L19, L22, L25 and L30, as well as the positions of proteins L21 and L32 (whose structures are not known), and the positions of electron density labeled LU, LV, and LX that we ascribe to as yet unidentified large subunit ribosomal proteins (which may include the three unassigned known proteins L31, L35 and L36). 5S rRNA (5S) is visible at the top of the 50S subunit, along with two of its binding proteins, L5 and L25.

The view from the back of the 50S subunit (FIG. 2C) reveals the locations of additional 50S subunit proteins L4, L15, L16, L21, L24, L27, L28, L29, L32, L33, L34, the third 5S rRNA-binding protein L18, and unidentified proteins LW and LY. The opening of the polypeptide exit channel (EC) is at the bottom of the back side of the 50S subunit, surrounded by proteins L22, L24 and L29 in addition to elements of domains I and III of 23S rRNA.

In the left-hand view (FIG. 2D), close approach of the two subunits at the interface is much more evident. The platform of the 30S subunit, around proteins S11, S6 and S15, contacts the 50S subunit near protein L2, mainly through RNA—RNA interactions and RNA-protein interactions involving proteins S 15 and L2. The E-site tRNA (red) can be seen at the near side of the interface cavity, partly shielded from view by L1 and its RNA binding site, which appear to block the path for its exit from the ribosome. In the top view (FIG. 2E), the orientations of all three tRNAs (A, gold; P, orange; E, red) in the interface cavity can be seen more clearly. Contact between the A-site finger (ASF) in 23S rRNA and S 13 in the head of the 30S subunit (bridge B1a) is evident, as is the close approach between proteins L5 and S13 (bridge B1b), whose electron densities merge to form the single protein-protein intersubunit bridge (see below).

Viewed from the interface (FIGS. 2F, G), fewer proteins are visible on the 30S and 50S subunits, and they are located mainly around the periphery, leaving large exposed surfaces of ribosomal RNA. The three tRNAs are aligned on the 30S subunit with their anticodon ends bound in the RNA-rich groove between the head, body and platform (FIG. 2F). The rest of all three tRNAs, including their D stems, elbows and acceptor arms, interact with the 50S subunit. The acceptor arms of the A and P tRNAs point downward into the peptidyl transferase cavity, while the E-tRNA acceptor arm is directed into a separate cleft next to the L1 ridge. The tRNA binding site neighborhoods are dominated by rRNA, as are the interface contact surfaces.

Secondary and Tertiary Structural Domains of the rRNAs

The structures of the ribosomal RNAs have been the subjects of intensive investigation for more than twenty years. Their secondary structures (FIGS. 3A, B) were first established by comparative sequence analysis (Woese et al. 1980; Noller et al. 1981a), in which intramolecular base pairing was demonstrated by the existence of phylogenetic covariation of the paired bases, presently supported by 16S-like rRNA sequences from over 8000 different organisms and organelles, and over 1000 different 23 S-like rRNA sequences (http://www.ma.icmb.utexas.edu/). All of the more than 60 phylogenetically predicted helical elements of 16S rRNA are found in the structure. Most of the individual helical elements of 16S rRNA stack coaxially with adjacent helices, as first observed in the structure of tRNA, forming a total of twenty longer, quasi-continuous helical arms.

Figure 3A:
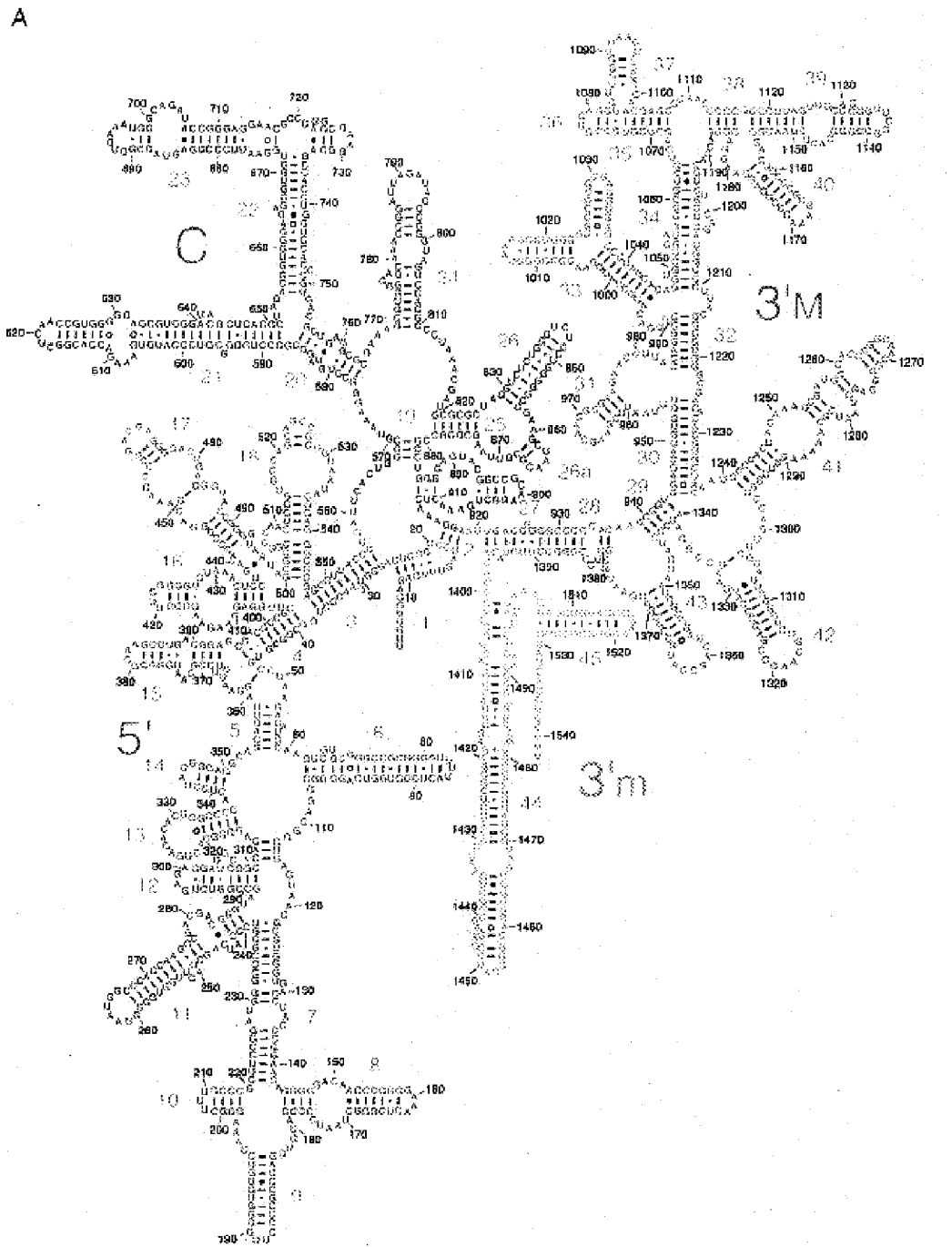
FIG. 3. Secondary and Tertiary Structures of 16S, 23S and 5S rRNAs. (A) Secondary structure of *T. thermophilus* 16S rRNA (SEQ ID NO: 45) with its 5', central, 3'-major and 3'-minor domains shaded in blue, magenta, red and yellow, respectively. (B) Secondary structures of *T. thermophilus* 23S (SEQ ID NO: 23) and 5 S rRNAs (SEQ ID NO: 24), indicating domains I (blue), II (cyan), III (green), IV (yellow), V (red) and VI (magenta) of 23S rRNA. The rRNAs are numbered according to *E. ccli* (75). (C) Three-dimensional fold of 16S rRNA in 70S ribosornes, with its domains colored as in (A). (D) Three-dimensional folds of 23S and 5S rRNAs, with their domains colored as in (B).

The secondary structure of 16S rRNA falls into four recognizable domains, called the 5', central, 3'-major and 3'-minor domains (FIG. 3A; Woese et al. 1980; Gutell 1994). A general sense of the three-dimensional fold of 16S rRNA emerged from early modeling studies (Stem 1988a; Brimacombe et al. 1988) based on chemical footprinting (Noller et al. 1990) and crosslinking (Mueller et al. 1995) experiments, as well as biophysical approaches such as immuno-electron microscopy (Stöffler-Meilecke et al.) and neutron scattering (Capel et al. 1987). Although there were differences in detail between the models deduced by different laboratories, there was general agreement that the 5' domain is located in the body of the 30S subunit, the central domain in the platform and the 3' major domain in the head of the particle (Noller et al. 1981a). As observed in the structures of the isolated ribosomal subunits (Wimberly et al. 2000; Schluenzen et al. 2000), the secondary structure domains of 16S rRNA (FIG. 3A) do indeed correspond to three-dimensional domains that are nearly structurally autonomous (FIG. 3C). The 5' domain makes up the body, the central domain of the platform (anchored to the solvent face of the body by the long, coaxial 620 stem), the 3'-major domain the head and neck of the subunit, and the 3'-minor domain the penultimate stem and adjacent 3'-terminal helix. This organization immediately suggests that the domains are designed to move relative to one another during protein synthesis. In particular, the very minimal interaction between the head and the rest of the subunit is consistent with the proposed movement of the head during translocation (Serdyuk et al. 1992; Frank et al. 2000). The four domains converge near the geometric center of the subunit, next to the sites of its functional interactions with mRNA and tRNA, further suggesting coupling of inter-domain movement with biological function.

Figure 3B:
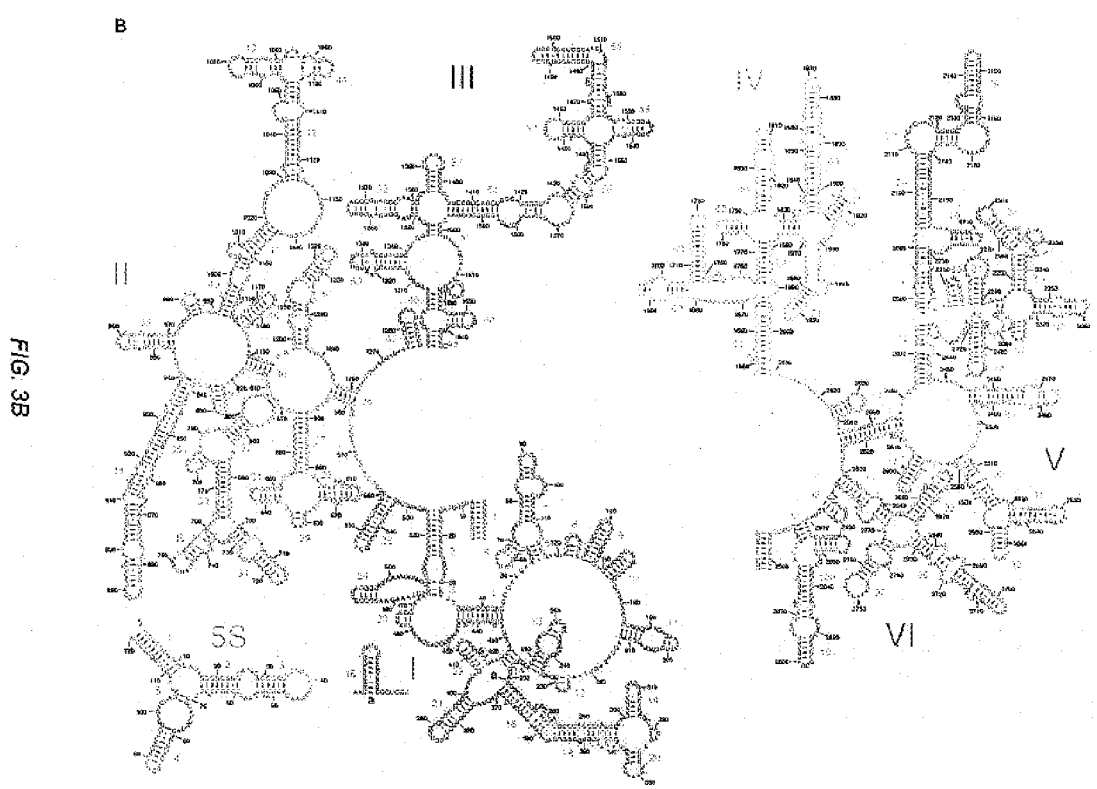

More than 130 individual helices predicted from comparative sequence analysis of 23S rRNA (Noller et al. 1981b; Gutell et al. 1993) are found in its X-ray crystal structure, forming forty coaxial arms. No electron density was found for a predicted Thermus-specific helix inserted around position 650 of 23S rRNA, relative to the *E. coli* secondary structure (http://www.ma.icmb.utexas.edu/). The 23S rRNA and 5S rRNA together form seven secondary structural domains (FIG. 3B). In contrast to the design of the 30S subunit, the domains of 23S rRNA are extensively intertwined with each other, creating the single large, hemispherical domain that forms the body of the 50S subunit (FIG. 3D), as first noted for the *H. marismortui* 50S subunit (Ban et al. 2000). From the body project a number of molecular stalks, made up of RNA elements from domains II, IV, V and VI, some of which are extended coaxial helical arms and others of which are mushroom-like globular RNA domains tethered to the body of the subunit by helical stems. Some of the stalks form bridges with the 30S subunit, while others interact with the tRNAs and elongation factors; the stalks are likely to be dynamic elements of the 50S subunit, undergoing movement in connection with their various functional interactions, as discussed below.

Differences Between the Conformations of 70S Ribosomes and Isolated Subunits

Comparison of the conformation of 16S rRNA in 70S ribosomes with that of the 30S subunit structure reported by Wimberly et al. (Wimberly et al. 2000) shows a non-uniform distribution of rmsd differences (FIGS. 4A, B). Root-mean-square deviations of the positions of phosphorus atoms were calculated after carrying out least-squares superimpositions of the respective 16S and 23S rRNAs as follows. First, a distance matrix was calculated independently for each RNA coordinate set. Then a set of the 214 atoms whose intramolecular distance values varied the least between the two comparison molecules were used to superimpose the entire molecules by a least-squares fit, using the program MIDAS [T. E. Ferrin, C. C. Huang, L. E. Jarvis, R. Langridge, *J. Mol. Graphics* 6,13–27 (1988)]. The highest rmsd values (>10 Å) are observed for the spur region (SP) in the lower left of the body; this difference can be explained by a crystal contact in which the spur helix binds to the P site of a symmetry-related subunit in the Wimberly et al. structure. The other major conformational differences (rmsds between 3.5 and 10 Å) are localized to a few regions, including the penultimate stem (PS), the top of the platform and the head of the subunit. All of these features interact with the 50S subunit, as described below, suggesting that the observed differences may include conformational changes that occur upon subunit association.

Differences between the conformations of 23S rRNA in *T. thermophilus* 70S ribosomes and *H. marismortui* 50S subunits (Ban et al. 2000) are summarized in FIGS. 4C and 4D. Features of 23S rRNA that were disordered in the 50S structure (yellow) include several of the protruding stalk elements, including the L1 RNA and L11 RNAs, the A-site finger and the 1915 stem-loop. These elements are probably stabilized by interactions with the 30S subunit and with the tRNAs in the 70S ribosome complex. It is also possible that the inherent thermal stability of the Thermus ribosome contributes to the lower degree of disorder.

Many additional conformational differences with the *Haloarcula* 50S subunit are found (FIGS. 4C, D). Some differences are explained by expected phylogenetic structural variation between corresponding regions of the bacterial and archaeal RNAs. There are examples of RNA helices and other features that are unique to the bacterial structure (FIGS. 4C, D; cyan) and conversely, ones that are uniquely present in the archaeal structure (white). These phylogenetically variable features are located at the bottom and back surfaces of the subunit, remote from the subunit interface and functional sites.

Protein L9 and the Apical Stem of Domain III

A major conformational difference is found in the apical stem region of domain III of 23S rRNA, centered at position 1495 in the bacterial RNA (FIG. 4C) and at 1597 in the archaeal numbering. In the Thermus ribosome, this helix (helix 58) folds back along the lower edge of the subunit, pointing to the left, where it interacts with protein L2; in the *Haloarcula* 50S structure, it takes a completely different path (FIG. 4E), diverging sharply around position 1478 (*Haloarcula marismortui* nucleotide 1581) to fold in the opposite direction, up and to the right, on the interface side of the subunit, placing the apical loop next to helix 34 of 23S rRNA, more than 50 Å away from the position of the corresponding loop in the Thermus 70S ribosome.

There is reason to believe that this conformational difference may not be due to phylogenetic variation. First, the bases in the 1495 loop and the amino acids in L2 with which they interact in the Thermus structure are conserved, and identical in *Haloarcula*, inconsistent with the idea that the 1495 loop makes completely different interactions in the bacterial and archaeal ribosomes. This suggests that helix 58 is rearranged in one of the two structures. Another possibility, that the helix has different conformations in 50S subunits and 70S ribosomes, seems to be ruled out by the results of directed hydroxyl radical probing from protein L9 in *E. coli* 50S subunits (Lieberman et al. 2000). These results place the loop of helix 58 near helices 10 and 79, and near the internal loop at position 1580 of helix 54, all of which are close neighbors of helix 58 in the Thermus 70S structure, but remote from the position of helix 58 in the *Haloarcula* 50S structure. A likely explanation is that helix 58 is rearranged in the archaeal 50S subunit crystal structure.

These same probing experiments further suggest that protein L9, whose linker helix and C-terminal domain protrude far into the solvent from the left-hand side of the 50S subunit, is itself rearranged in the Thermus structure. According to calibration studies (Joseph et al. 2000), the strong hydroxyl radical cleavage from position 101 of L9 at nucleotides 165, 1495, 1580, and 2220 of 23 S rRNA place it within 25 Å of these targets; instead, these nucleotides, which are clustered together on the left-hand side of the subunit, are between 70 and 80 Å away from position 101 of L9, a distance at which hydroxyl radical cleavage is virtually undetectable. We infer that the C-terminal domain of L9 must normally be located in the vicinity of the pocket formed between helices 10, 54 and 79 on the left-hand side of the 50S subunit, and that, under our crystallization conditions, it rearranges to form a crystal contact with the 16S rRNA of a neighboring ribosome (FIG. 4F).

Structures of the Intersubunit Bridges

Figure 5A:
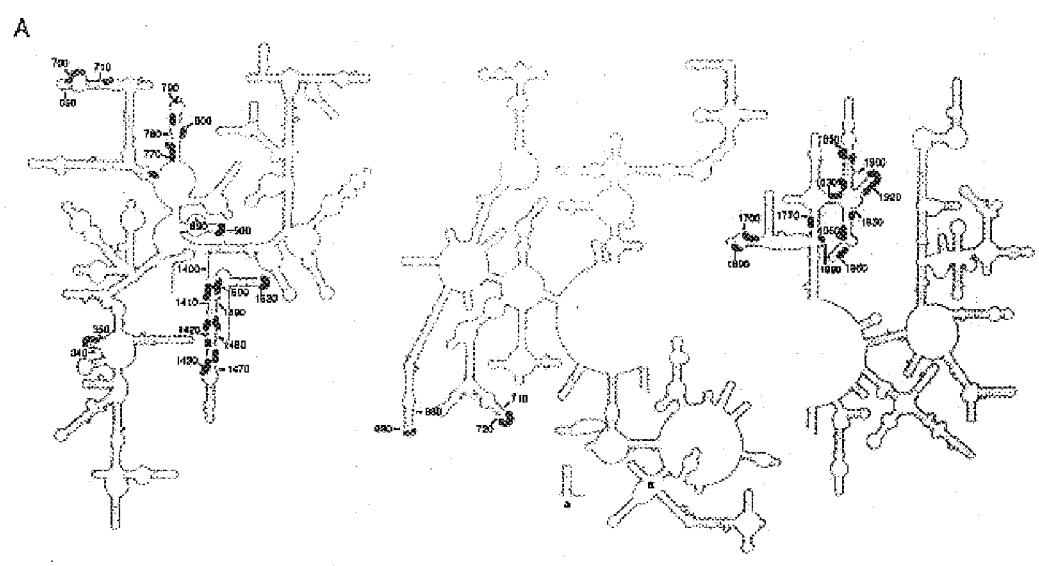
FIG. 5. Secondary structures of 16S and 23S rRNAs, showing features involved in intersubunit contacts (red). (B, C) Interface views of the 50S and 30S subunits, with the bridges numbered (Frank et at. 1995a; Cate et al. 1999). RNA—RNA contacts are shown in red (16S rRNA) and magenta (23S rRNA); protein-RNA and protein-protein contacts are shown in yellow and pink. A, P and E indicate the three tRNAs. (D–G) Detailed stereo views of the bridge interactions, viewed as in (D) FIG. 2B, (E) FIG. 2C, (F) FIG. 2D; rotated 90° around the horizontal axis, (G) FIG. 2D.

Intersubunit contacts were first visualized as discrete bridges in cryo-EM studies by Frank and co-workers (Frank et al. 1995a). At 5.5 A, all of the molecular components involved in the intersubunit contacts can be identified, including two additional protein-containing bridges. As inferred from earlier chemical probing (Merryman et al. 1999a; Merryman et al. 1999b) and modification-interference (Herr et al. 1979) studies, most of the bridge contacts involve rRNA, as summarized in FIG. 5A. FIG. 5B shows the 30S bridge contacts, viewed from the interface, with the anticodon stem-loops of the A-, P- and E-tRNAs in their respective 30S subunit binding sites. The distribution of RNA—RNA vs. RNA-protein or protein-protein contacts is striking; the RNA—RNA contacts (red) are centrally located on the platform and penultimate stem, directly abutting the tRNA binding sites. In contrast, contacts involving proteins (yellow) are peripherally located, more distal from the functional sites. On the 50S subunit side (FIG. 5C), the RNA—RNA contacts are again central, forming a triangular patch across the front surface of the interface wall that separates the peptidyl transferase and E sites from the interface cavity. Interestingly, the RNA—RNA interactions exclusively involve RNA elements from domain IV of 23S rRNA, except for a small RNA—RNA contact from helix 34 of domain II that makes up most of bridge B4 (Culver et al. 1999). The only other part of 23S rRNA involved in a bridge contact is the tip of helix 38 (the A-site finger), which forms the RNA-protein bridge B 1a. The rest of the bridge interactions from the 50S subunit are made by proteins L2, L5, L14 and L19.

The molecular contacts forming the twelve intersubunit bridges (FIG. 5B, C) are summarized in Table III. Multiple contacts can be seen in the electron density map for many of the bridges, giving a total of more than 30 individual interactions. RNA—RNA contacts are dominated by minor groove-minor groove interactions, although major groove, loop and backbone contacts are also found. The bridge proteins make use of virtually all types of RNA features for recognition, including major groove, minor groove, backbone and loop elements.

Bridges B1a and B1b connect the head of the 30S subunit to the top of 50S subunit, crossing the interface directly above, and parallel to the A- and P-tRNAs (FIG. 2E). B1a, which has been called the 'A-site finger' (Frank et al. 1995a) is mostly disordered in the *Haloarcula* 50S subunit structure (Ban et al. 2000). It consists of a long helical RNA arm (helix 38 of 23S rRNA) reaching from the right side of the central protuberance of the 50S subunit to the middle of the head of the 30S subunit, where its apical 890 loop contacts the conserved basic sequence around position 92 of protein S 13. Bridge B1b is the sole protein-protein contact between the subunits. Helix 84 of 23S rRNA reaches part-way toward the head of the 30S subunit above the P-tRNA; the remaining distance is bridged by protein LS, which contacts the N-terminal tail of S13 from a 20-amino acid loop formed by residues 134–153 of LS (*Haloarcula marismortui* positions 109–127), which are also disordered in the *H. marismortui* 50S structure.

Bridges B2a, B3, B5 and B6 (FIG. 5B, C) all involve interactions between the 50S subunit and the penultimate stem (helix 44) of 16S rRNA, the dominant structural component of the 30S subunit interface. FIG. 5D shows the arrangement of the RNA elements forming these four bridges. At the top, bridge B2a is made by the 1914 loop of helix 69 of 23S rRNA, another feature that is disordered in the *Haloarcula* 50S subunit structure. It contacts the decoding site of 16S rRNA around position 1408, as predicted from cross-linking experiments (Mitchell et al. 1992) in the first of a series of three consecutive minor groove-minor groove interactions. In the next one (B3), helix 71 of 23S rRNA contacts the penultimate stem at its two consecutive non-canonical A–G pairs around position 1418. Just below B3, a major groove contact is made by the minor groove of helix 64 of 23S rRNA, followed by the third minor-minor interaction (B6) formed by contact with helix 62. A further contact with the penultimate stem at bridge B6 is made by protein L19 (FIG. 5E). L14, which interacts with L19 by forming an intermolecular β-sheet, contacts the major groove side of the 345 loop of helix 14 of 16S rRNA to form bridge B8 (FIG. 5E).

Helices 68 and 71 of 23S rRNA form a long, largely non-canonical coaxial arm that lies horizontally along the top of the interface wall of the 50S subunit, containing the 50S components of bridges B2b and B7a, in addition to the aforementioned B3 (FIG. 5C). FIG. 5F shows the complex set of interactions that form B2b and B7a, viewed from the top of the platform. The electron density for bridge B7a suggests that A702, which is strongly protected from diethyl pyrocarbonate modification in 70S ribosomes (Merryman et al. 1999b), makes an 'A-minor' contact (Ban et al. 2000) with the minor groove of helix 68 of 23S rRNA. The two remaining protein-RNA bridges are shown in FIG. 5G. Protein L2 makes two distinct contacts with 16S rRNA (B7b), at helices 23 and 24; L2 is also very close to protein S6 (not shown), and may make transient contacts with it during translation. Bridge B4 is primarily an interaction between protein S15 and the 715 loop of helix 34 of 23S rRNA, as shown previously (Culver et al. 1999); the 715 loop also makes a modest RNA—RNA contact with helix 20 of 16S rRNA (FIG. 5G).

TABLE III

Intersubunit Bridges.

| Bridge | Type | 30S Subunit | | 50S Subunit | |
|---|---|---|---|---|---|
| B1a | Prot-RNA | S13 | 92–94 | H38-(L) | 886–888 |
| B1b | Prot-Prot | S13 | N-term | L5 | 134–153 |
| B2a | RNA-RNA | H44(m) | 1408–10, 1494–5 | H69(Lm) | 1913–4, 1918 |
| B2b | RNA-RNA | H24(m, LM) | 784–5, 794 | H67(m), H69 (M) | 1836–7, 1922 |
| | RNA-RNA | H45(LM, Lm) | 1516–9 | H71(M), H69 (B) | 1919–20, 1932 |
| B2c | RNA-RNA | H24(Bm) | 770–1 | H67(B) | 1832–3 |
| | RNA-RNA | H27(Bm) | 900–1 | " | " |
| B3 | RNA-RNA | H44(m) | 1484–6 | H71(m) | 1947–8, 1960–1 |
| B4 | RNA-RNA | H20(m) | 763–4 | H34(Lm) | 717–8 |
| | Prot-RNA | S15 | 40–4, C-term | H34(LB, LM) | 713, 717 |
| B5 | RNA-RNA | H44(m) | 1418–9 | H64(m) | 1768–9 |
| | RNA-Prot | H44(B) | 1420–2 | L14 | 44–9 |
| | RNA-RNA | H44(B) | 1474–6 | H62(Bm) | 1689–90 |
| | RNA-RNA | " | " | H64(m) | 1989 |
| B6 | RNA-RNA | H44(m) | 1429–30, 1474–6 | H62(m) | 1689, 90, 1702–5 |
| | RNA-prot | H44(B) | 1431 | L19 | (Hm24e:R44) |
| B7a | RNA-RNA | H23(L, m) | 698, 702 | H68(m) | 1848–9, 1896 |

TABLE III-continued

Intersubunit Bridges.

| Bridge | Type | | 30S Subunit | | 50S Subunit |
|---|---|---|---|---|---|
| B7b | RNA-Prot | H23(M, m) | 712–3 | L2 | 162–4, 172–4, 177–8 |
| | RNA-Prot | H24(M, m) | 773–6 | " | 177–8, 198–202 |
| B8 | RNA-Prot | H14(LM) | 345–7 | L14 | 116–9 |

Bridges are numbered B1a, B1b, etc. as shown in FIGS. 5B and 5C. rRNA contacts are to 16S rRNA for the 30S subunit and to 23S rRNA for the 50S subunit, listed by the number of the proximal helix (H44, etc.), numbered as shown in FIGS. 3A and 3B. rRNA nucleotide numbers are according to E. coli numbering. Molecular contacts are scored in parentheses as: M, major groove; m, minor groove; L, loop; B, backbone; Lm refers to the minor groove side of the loop, LB to the loop backbone, etc.

tRNA-Ribosome Interactions

Most important for understanding the translational mechanism is how the ribosome interacts with its substrates, the tRNAs. In addition to their well-known interactions with mRNA, via base pairing between the codons and anticodons, tRNAs also interact with the ribosome itself. These interactions not only help to stabilize the binding of tRNA to the ribosome, but are involved directly in functional processes such as discrimination mechanisms that increase the accuracy of aminoacyl-tRNA selection, maintaining the correct translational reading frame, translocational movement of tRNAs within the ribosome, and catalysis of peptide bond formation. Knowledge of the molecular contacts between tRNA and the ribosome thus provides a structural framework for elucidation of mechanisms for these processes. As predicted by many earlier studies (reviewed in Green et al., 1997), the tRNAs are mainly surrounded by elements of rRNA in the ribosome, most of which were identified in footprinting, cross-linking and directed hydroxyl radical probing, studies (Moazed et al. 1986b; Döring et al. 1994; Moazed et al. 1989a). Not surprisingly, we find that the ribosome contacts all three tRNAs at universally conserved parts of their structures, so that all tRNAs can be bound in the precisely same way.

FIG. 6A shows the electron density of the A- and P-tRNAs bound to their respective codons, and FIG. 6B shows the overall relative geometry of the A- P- and E-tRNAs and the mRNA as they are positioned in the 70S ribosome crystals. Their specific contacts with the ribosome indicate that they are in their "classical" (A/A, P/P and E/E), rather than hybrid binding states (Moazed et al. 1989b). All three tRNAs are shared between the two ribosomal subunits in a similar way; their anticodon stem-loops are bound by the 30S subunit, and contacts with the rest of the tRNA—D stem, elbow and acceptor arm—are made by the 50S subunit. The planes of the A- and P-tRNAs form an included angle of 260, and the P- and E-tRNAs an angle of 46°. The closest approach between the backbones of the anticodon stem-loops of the A- and P-tRNAs is about 10 Å, a surprisingly large distance, in view of the fact that these two tRNAs read adjacent codons on the mRNA.

The simultaneous reading of the two codons is accommodated by a kink in the mRNA backbone of about 45° between the A and P codons (FIG. 6B). The A- and P-tRNA backbones are closest at the acceptor stems, which approach within 5 Å of each other. At the elbow, the bases D16 of A-tRNA and U47 of P-tRNA are actually within H-bonding distance of each other, although we are not aware of prior evidence that such an interaction takes place. The CCA tails of the A- and P-tRNAs converge, as expected, at their 3' ends in the peptidyl transferase site of the 50S subunit. The closest approach of the anticodon stem backbones of the P- and E-tRNAs is about 6 Å, significantly closer than found for the A- and P-tRNAs. However, the elbow and acceptor arm of the E-tRNA are rotated significantly away from the P-tRNA, so that their respective 3' ends are nearly 50 Å apart. The distances between corresponding positions of the three tRNAs is a measure of the magnitude of the movement of tRNA during translocation. Thus, the anticodon end of tRNA moves about 28 Å between the 30S A and P sites, and 20 Å between the P and E sites. Because of the rotation of the plane of the tRNA, the elbow moves through much larger distances of 40 and 55 Å, as it transits from A to P to E.

As observed previously, the anticodon stem-loop (ASL) and P codon of P-tRNA are positioned by six sets of interactions (a–f) with the 30S subunit (Cate et al. 1999). The structural features involved in these interactions are shown in FIGS. 6C and 6D, and summarized in Table IV. At the present resolution, actual atomic interactions are not resolved. However, known RNA stereochemistry, combined with the docked high-resolution structures, strongly constrains, for example, whether interactions with RNA involve the sugar-phosphate backbone or the bases, and in many instances, allows prediction of the chemical groups most likely involved.

TABLE IV tRNA - Ribosome Contacts[1]

| | interaction | tRNA positions | ribosome positions |
|---|---|---|---|
| P-tRNA | | | |
| a | a.c. stem-16S (H30) | 28–30 bk | 16S (1229) bk |
| | a.c. stem-S13 | — | S13 (116–120) |
| b | a.c. stem-16S (L29-42) | 40 bk | 16S (1339) bk |
| | | 40 bk | 16S (1339) bs |
| | | 41 bs | 16S (1338) bs |
| c | a.c. loop-16S (790 loop) | 38 bk | 16S (790) bk |
| d | a.c. loop-16S (965 loop) | 34 bk | 16S (m²G966) bs |
| | a.c. loop-S9 | 35 bk | 59 (R128) |
| e | P codon-16S (decoding site) | P codon | 16S (926) bs |
| | | 1 bk | 16S (1498) bk |
| f | a.c. loop-16S (decoding site) | 34 bs | 16S (1400) bs |
| g | D stem-23S (H69) | 12, 13 bk | 23S (1908–9) bk |
| | | 25, 26 bk | 23S (1922–3) bk |
| h | T loop-L5 | 56–7 | L5 (55–66) |
| i | acc. stem-23S (P stem/H80) | 3 bk | 23S (2255–6) bk |
| j | acc. tail-23S (P loop) | 74 bs | 23S (2252) bs |
| k | acc. tail-23S (H93) | 75 | 23S (2602) |
| l | acc. tail-23S (L90-93) | 76 | 23S (2585) |

TABLE IV-continued tRNA - Ribosome Contacts[1]

| | interaction | tRNA positions | ribosome positions |
|---|---|---|---|
| A-Trna | | | |
| a | codon-anticodon helix - 16S (530 loop) | 34–35 bs 36 bk | 16S (530) bs 16S (530) bk |
| b | ac.-16S (H34) | 34 bk | 16S (1054) bs |
| c | a.c. stem-16S (965 loop) a.c. stem-S13 | 40 bk 40–41 bk | 16S (955) bk S13(120–2) |
| d | a.c. loop-16S (decoding site) A codon-16S (dec. site) | 38 bk A codon 1 bk | 16S (1493) bk 16S (1493) bk |
| e | A codon-S 12 | A codon 2, 3 | S12 (46–48) |
| f | D stem-23S (1169) D stem junction-23S (H69) | 11, 12 25, 26 | 23S (1914–5) 23S (1913–4) |
| g | D loop-23S (A finger/H38) | D17 bs G19 bs | 23S (881–2) bk 23S (882–3) bk |
| | T loop-23S (A finger/H38) | 56 bk | 23S (898–9) bk |
| h | T stem-23S (H89) | 50–3 bk 64–5 bk | 23S (2470–2) bk 23S (2482–4) bk |
| i | acc. stem-23S (H71) | 72–3 | 23S (1942–3) |
| j | acc. tail-23S (H89) | 74–6 bk | 23S (2452, 2494) bk |
| k | acc. tail-23S (A loop) I | 75 bs | 23S (2553) bs |
| l | T stem-loop-L16 | 55, 62 | L16 (27, 30) |
| E-tRNA | | | |
| a | a.c. loop-16S(H29) a.c. stem-16S (L29–42) | 35, 36 bk 30 bk | 16S (1339, 1340) bk bk |
| b | a.c. loop-16S (H28) | 34 bk | 16S (1382) bk |
| c | ac. loop-16S (L28–29) | 33 bk | 16S (937) bk |
| d | a.c. loop-16S (790 loop) | 37–38 bk | 16S (788–9) bk |
| e | ac. loop-16S (690 loop) | 37 bs 38–39 bk | 16 (693) bs 16S (694–5) bk |
| f | a.c. loop-S7 | 37 42 | S7 (β-hairpin) S7 (α-6) |
| g | D loop-23S (L76–77) | 19 | 23S (2112–3) |
| h | T loop-23S (L76–77) | 56 | 23S (2116–7) |
| | T loop-LI | 56–7 | L1 (124–8) |
| I | T stem-LI | G53-C61 bp | L1 (52–4) |
| | T loop-LI | 55 bk | L1 (165–9) |
| j | acc. Stem-23S (H68) | 2–71 bp 71 bk 3–5 bk | 23S (1852–3) bs 23S (1892) bk 23S (1850–3) bk |
| k | acc. Tail-23S (H75) | 73 bk | 23S (2235) bk |
| l | acc. Tail-23S (H74) | 76 bk | 23S (2433–4) |
| m | acc. Tail-23S (H11) | 76 bs | 23S (199) bs |
| n | acc. Tail-L33 | 73–74 | L33 |

[1]a.c., anticodon; acc., acceptor; D, dihydrouracil; T, thymidine; RNA contacts are indicated as bk, backbone; bs, base; bp, base pair. Where results are inconclusive, the designation is omitted. tRNA positions are numbered according to yeast tRNA$^{Phe}$, rRNA positions according to *E. coli*.

The modes of binding of the anticodon stem-loop and its contacts are very similar to those previously observed for binding of helix 6 to the 30S P site (Carter et al. 2000). All six of the 30S P-site interactions involve direct contacts with 16S rRNA, two of which (a and d) are bolstered by interactions with the extended C-terminal tails of proteins S 13 and S9, respectively. The somewhat phylogenetically variable lysine-rich tail of S 13 interacts with phosphate 36 of the P-tRNA. In contrast, the tail of S9 is precisely conserved, and its C-terminal arginine, which appears to interact with phosphate 35 in the anticodon of P-tRNA, is universally conserved. These same phosphates were identified in phosphorothioate-interference experiments to be important for binding to the 30S P site (Schnitzer et al. 1997). One of the earliest experiments implicating rRNA in ribosome function was the demonstration that kethoxal modification of a limited number of guanines in 16S rRNA caused loss of P-tRNA binding to the 30S subunit, (Noller et al. 1972). Of the five 16S rRNA bases that interact with the P-site mRNA-tRNA complex, G926, 2mG966, G1338, G1339 and C1400, no less than four are guanines, explaining the early findings. Moreover, all five bases were identified as P-site interactions based on chemical footprinting and modification-interference experiments (Moazed et al. 1986b; Ahsen et al. 1995; Moazed et al. 1990).

In addition, a set of interactions appears to stabilize P-site codon-anticodon pairing: the base G966, interacting with the anticodon backbone at position 34 of the tRNA, and the backbone of nucleotide U1498, interacting with the backbone of position 1 of the P codon, appear to clamp the codon and anticodon together. C 1400 appears to stabilize the wobble base pair by stacking on base 34 of tRNA, an arrangement that was predicted by Ofengand and co-workers nearly twenty years ago, from photochemical crosslinking studies (Prince et al. 1982). Again, many of the bases identified by tRNA footprinting experiments (Moazed et al. 1986b; Moazed et al. 1990) are found to make interactions with the tRNA; some, however, including the "class III" bases (Moazed et al. 1987) are protected indirectly, presumably by tRNA-induced conformational changes. Two proteins, S9 and S13, interact with the P-tRNA, both via their extended, basic C-terminal tails, which interact with the anticodon stem-loop in a way that suggests that they function as sophisticated polyamines, bolstering the RNA—RNA interactions.

The minor groove of helix 69 of 23S rRNA, which forms bridge B2a, interacts with the minor groove of the D stem of P-tRNA (FIG. 6E; interaction g), extending into the A site where its conserved loop interacts with almost the same features of the D stem of A-tRNA (FIG. 6K; interaction f), as well as forming the B2a bridge contact with the top of the penultimate stem (FIG. 5D). This complex set of interactions explains chemical footprinting results that showed partial protection of bases in the 1915 loop of helix 69 by the 30S subunit, which became complete upon binding of tRNA (Moazed et al. 1989a). At its elbow, a beta-hairpin loop of protein L5 (positions 54–66) interacts with the T loop of P-tRNA at the minor groove face of C56 (FIG. 6E; h). The CCA tail of the P-tRNA is positioned to allow the predicted C74-G2252 base pair with the 23S rRNA P loop (Samaha et al. 1995), observed in the recent high-resolution structure of the archaeal 50S subunit complexed with substrate analogues (Nissen et al. 2000). In addition, the acceptor end is positioned by a backbone-backbone contact between the acceptor stem and the stem of the 23S rRNA P loop (FIG. 6E; i), and interactions between the CCA tail and nucleotides A2602 and U2585, both of which have been implicated in the peptidyl transferase function of the large subunit (Moazed et al. 1989a; Barta 1984).

Recently, the atomic resolution structure of the *Haloarcula* 50S subunit has been solved in complex with the compound CCdAp-Puromycin (Nissen et al. 2000), which is believed to be a transition-state analog of the peptidyl transferase reaction (Welch 1995). This structure has led to a proposal for a mechanism for catalysis of peptide bond formation by the ribosome (Nissen et al. 2000). We have docked the peptidyl transferase region of the 50S subunit structure containing CCdAp-Puromycin, on the 70S ribosome structure, guided by superposition of surrounding elements of 23S rRNA. An electron density map, truncated at 5.5 Å resolution, was calculated for the *Haloarcula* 50S subunit complex, after removing the puromycin moiety, to allow for the fact that deacylated tRNA is bound to the P site in our structure. At 5.5 Å resolution, most of the conformation of the rRNA backbone in the vicinity of the 3'-CCA end of P-site tRNA shows few discernible differences between the two structures. The few apparent differences are localized to the P loop and at or around positions 2451, 2506, 2585 and 2602, which may move in a concerted way. In the 70S ribosome complex, the position of the 3'-CCA end of the P-tRNA, relative to nearby features of 23S rRNA, appears to differ from that of the corresponding part of the transition-state analog, possibly due to the absence of an acyl group. The CCA end of P-tRNA shows a vertical displacement relative to the binding pocket in the two structures (FIG. 6F).

Two possible models could account for the differences seen between the experimental 70S electron density map (FIG. 6F) and the 5.5 Å map calculated from the 50S structure (FIG. 6G). In one model, the CCA end is pulled up slightly in the binding pocket, accounting for the gap in density seen in the experimental map between A76 and the A2451 strand where continuous density is seen in the calculated map. A second model involves a deeper placement of C74 and C75 in the pocket, accompanied by a rotation of A76 towards U2585. The second model is also consistent with the gap in the density described above, but also explains new density appearing adjacent to U2585 in the experimental electron density of the 70S ribosome (FIG. 6F). Chemical protection experiments have shown that U2585 is strongly protected by binding either acylated or deacylated tRNA to the 50S P site but is unprotected when bound with tRNA missing its A76 (Moazed et al. 1989a). Interestingly, while the placement of A76 near U2585 involves a significant rearrangement of the CCA end of the model determined from the 50S subunit structure, the position of the ribose of A76 may not shift much at all in the binding pocket.

Surrounding the A-tRNA anticodon loop in the 30S subunit are G530, A1492 and A1493, the three universally conserved bases originally identified as A-site-specific features by chemical footprinting studies (Moazed et al 1986b; Moazed et al. 1990) and shown to affect A-site binding by mutational and biochemical studies (Powers et al. 1990; Yoshizawa et al. 1999). All three bases are positioned close to the site of codon-anticodon interaction in the 30S A site (FIGS. 6H, I; a,d). The tRNA-protected N1 positions of bases A1492 and 1493 point away from the codon-anticodon base pairs, and are separated from them by the 16S rRNA backbone, when the 30S subunit A site is vacant (Wimberly et al. 2000), consistent with the electron density of the 70S ribosome in the absence of A-tRNA. In the presence of the aminoglycoside antibiotic paromomycin, the conformations of nucleotides 1492 and 1493 have been found to rearrange (Carter et al. 2000), raising the possibility that they may also rearrange in response to binding tRNA to the 30S A site. In the 7 Å Fourier difference map of the A-site tRNA bound to the 70S ribosome (FIG. 6J), a patch of negative electron density is seen at the position of bases 1492–1493, providing support for the possibility that they rearrange to interact with the first and second base pairs in the minor groove of the A-site codon-anticodon helix, as suggested by Carter et al. (Carter et al. 2000). The N1 position of G530 is also protected upon A-tRNA binding (Moazed et al. 1986b; Moazed et al. 1990) and mutations of this base confer a dominant lethal phenotype and defective A-tRNA binding (Powers et al. 1990). G530 is also positioned in the minor groove of the codon-anticodon helix, near the second and third base pairs. The bulged base C1054, mutations in which have been shown to suppress UGA nonsense mutations (Murgola et al. 1988), projects toward the apex of the A-tRNA anticodon loop (FIG. 6I; b).

Lysine 120 of protein S13 and phosphate 955 are both close enough to interact with the tRNA backbone around position 41 (FIG. 6H, I; c). The conserved lobe of S12, which bears the universal PNSA sequence around position 50, projects into the space between the 530 loop and the 1492–1493 strand of the decoding site (FIG. 6H; e), completing the floor of the 30S subunit A site. Mutations on the right-hand side of the lobe, facing the top of the penultimate stem at nucleotides 1492 and 1493 and the switch helix, (Lodmell et al. 1997) at positions 910–912, confer restrictive (hyperaccurate) phenotypes (reviewed in Kurland et al. 1990). These mutations could have the effect of widening the space between the 530 loop and 1492-3 strands, loosening the interactions between the tRNA-mRNA complex and the 30S A site.

The elbow of A-tRNA interacts with bridge B1a (the A-site finger; H3 8) at its D and T loops (FIG. 6K; g), and with protein L16 (Noller et al. 1992). Protein L11 and its associated RNA near position 1067 of 23S rRNA (H43; Ryan et al. 1991) although not directly interacting with the A-tRNA, are close to its T loop and could contact it transiently with only modest movement of either the tRNA or 23S rRNA. Electron density from protein L16 or an as yet unidentified r-protein partially occupies the position of the A-tRNA elbow (FIG. 6L), and so must move upon A-tRNA binding, possibly as part of the "accommodation" step (Pape et al. 1999). Helix 89 of 23S rRNA runs nearly parallel to the acceptor arm of the A-tRNA, making a minor-groove interaction (h) with the T stem at the top, and contacting the backbone of the CCA tail which lies across the major groove of its non-canonical helical extension (j) at the bottom. The CCA tail is also positioned by contact with the conserved 1942 loop, which tucks into the major groove at the end of the acceptor stem (i), and by the previously predicted base pair between C75 and G2553 of 23S rRNA (63), observed in the 50S crystal structure (Nissen et al. 2000).

The E-tRNA anticodon stem-loop is wedged between the head and platform of the 30S subunit, where it is surrounded by a dense system of molecular interactions (FIG. 6M), somewhat unexpected in view of the relatively weak binding of E-tRNA (Lill et al. 1986) and the apparent absence of base protections in 16S rRNA attributable to E-tRNA binding (Moazed et al. 1986b; Moazed et al. 1990). Helices 28 and 29 of 16S rRNA as well its 690 and 790 loops contribute RNA contacts a–e (FIG. 6N). The C-terminal α-helix of protein S7 packs against the backbone of the anticodon stem, while the S7 β-hairpin is positioned at the Watson-Crick face of the E-tRNA anticodon (f). Although normal codon-anticodon interaction is absent, there may be contact between the second base of the E-tRNA anticodon and the mRNA. A possible role of S7 could be to disrupt codon-anticodon interaction in the 30S E site. Recent studies show that deletion of either the β-hairpin or C-terminal helix of S7 influences the efficiency and accuracy of EF-G-dependent translocation (K. Fredrick, unpubl.)

Protein L1 and its binding region (H76–77) on 23 S rRNA interact with the elbow of E-tRNA (contacts g-i). The E-tRNA-protected bases G2112 and G2116 may stack on the tertiary G19-C56 base pair at the top of the tRNA elbow. The acceptor stem makes a minor-groove interaction with helix 68 of 23S rRNA, which includes the backbone contacts with ribose 71 that have been shown by Joseph and co-workers to be essential for EF-G-dependent translocation (Feinberg et al. 2001). In addition, the conserved A1853 may make an A-minor interaction with the 2–71 base pair. The CCA tail is buried in a deep pocket of the 50S subunit that is separate from the peptidyl transferase cleft, making contacts with helices 11, 74 and 75 of 23S rRNA and protein L33, and the E-tRNA-protected C2394 (Moazed et al. 1989a).

Implications for the Mechanism of Translation

The structure of a complete ribosome provides the basis for understanding the mechanism of protein synthesis at the molecular level. As a molecular machine, the ribosome must have moving parts that enable its function (Spirin 1969). The translocation step of protein synthesis inescapably requires movements of 20 A or more by the tRNAs, as they move from the A to P to E sites. It seems unlikely that such movements would not be matched by corresponding structural rearrangements of the ribosome (Wilson et al. 1998). The hybrid states model, in which the tRNAs move independently with respect to the 30S and 50S subunits in two separate steps, carries the implication that the mechanism of translocation may involve relative movement of the 30S and 50S subunits, or of particular structural domains or substructures of the two subunits (Moazed et al. 1989b).

FIG. 7A shows the overall relative geometry of the A-, P- and E-tRNAs and the mRNA as they are positioned in the 70S ribosome crystals. Their specific contacts with the ribosome indicate that they are in their "classical" (A/A, P/P and E/E), rather than hybrid binding states (Moazed et al. 1989b). The planes of the A- and P-tRNAs form an included angle of 26°, and the P- and E-tRNAs an angle of 46°. Simultaneous reading of the adjacent A and P codons is accommodated by a kink in the mRNA backbone of about 45° between the A and P codons (FIG. 7A). The distances between corresponding positions of the three tRNAs is a measure of the magnitude of the movement of tRNA during translocation. Thus, the anticodon end of tRNA moves about 28 Å between the 30S A and P sites, and 20 A between the P and E sites. Because of the rotation of the plane of the tRNA, the elbow moves through much larger distances of 40 and 55 Å, as it transits from A to P to E.

Our current understanding of the hybrid-states model (Moazed et al. 1989b) is shown schematically in FIG. 7B. Experimental evidence from several laboratories over the past decade have led to the introduction of some modifications to the minimal model. First, the afore-mentioned crystallographic evidence necessitates participation of a 30S E site in the mechanism. Second, evidence for an "accommodation" step following release of EF-Tu (Pape et al. 1999) raises the possibility that proof-reading of the incoming aminoacyl-tRNA could take place during this step; possibly, the accommodation process could involve regulation of peptidyl transferase activity, permitting only the cognate aminoacyl-tRNA to participate in peptide bond formation. Third, several lines of evidence (Green et al. 1998; M. Rodnina and S. Joseph, unpublished) have convincingly demonstrated that movement from the A/A to A/P and P/P to P/E states occurs sequentially, rather than concertedly, with peptide bond formation. Therefore, a separate state in which the peptidyl-tRNA occupies the A/A state has been introduced (FIG. 7B).

Extensive evidence has by now accumulated in support of the essential feature of the hybrid-states model, that the tRNAs move independently with respect to the two ribosomal subunits, first on the 50S subunit and then, on the 30S subunit (coupled to mRNA movement). Direct structural observation of the A/P and P/E states have been observed directly in cryo-EM reconstructions (Agrawal et al. 2000). The A/T state, in which the incoming aminoacyl-tRNA is still bound to EF-Tu, has also been observed by cryo-EM studies (Stark et al. 1997a).

FIG. 7C shows a three-dimensional interpretation of the hybrid-states translocational cycle. Here, the orientations of the classical-states tRNAs (A/A, P/P and E/E) are represented by those that we have directly observed crystallographically. The positions of the A/P and P/E hybrid-states tRNAs were modeled starting with the classical-state tRNAs, fixing the positions of their anticodon ends, and rotating them as rigid bodies to dock their respective acceptor ends in the 50S subunit. The resulting models bear close resemblance to the low-resolution structures observed experimentally by cryo-EM (Agrawal et al. 2000). The A/T tRNA was modeled in two steps: First, the structure of EF-G (Czworkowski et al. 1994) was docked on the 70S ribosome structure using constraints from footprinting and directed hydroxyl radical probing. Second, the structure of the EF-Tu-tRNA-GTP ternary complex (Nissen et al. 1995) was docked on EF-G by virtue of their homologous G domains. The result is again in good agreement with the position of the ternary complex determined by cryo-EM (Stark et al. 1997a). A striking observation is that the distance traversed by the acceptor end of the aminoacyl-tRNA in going from the A/T to the A/A states is on the order of 70 A, roughly the overall dimensions of the tRNA itself.

Thus far, most of the evidence for movement has pointed mainly to the 30S subunit. Neutron scattering experiments, in which changes in the radius of gyration of the ribosome were observed between the pre-and post-translocation states, suggested movement of the head of the small subunit (Serdyuk et al. 1992). Cryo-EM comparison of ribosomes bearing mutations in the "switch helix" (helix 27) of 16S rRNA indicate conformational differences in the head, shoulder, platform and penultimate stem of the 30S subunit between the ram and restrictive forms (Gabashvili et al. 2000). Comparison of the conformation of 16S rRNA in the 70S ribosome with that of the separate 30S subunit (FIG. 3A, B) again shows differences that suggest mobility of the head, platform and penultimate stem regions of the small subunit. Recent cryo-EM studies (Agrawal et al. 1999b; Frank et al. 2000) indicate rotation of the entire 30S subunit by about 6° upon binding of EFG-GTP.

The hybrid-states implication that tRNA translocation may involve relative movement at the subunit interface was reinforced by the observation that many of the nucleotides implicated in tRNA-ribosome interactions by biochemical and genetic experiments are adjacent to nucleotides involved in subunit association (Merryman et al. 1999a, b). The crystal structure provides direct evidence for close proximity of the tRNA binding sites to interface contacts, and even shows that some of the bridges interact directly with the tRNAs. Moreover, there is evidence that some of these tRNA-bridge interactions are dynamic.

Knowledge of the 70S three-dimensional ribosome structure provides important clues to the mechanism of tRNA movement. The hybrid states model notion that the mechanism of translocation involves relative movement of the 30S and 50S subunits, or of particular structural domains or substructures of the two subunits (Moazed et al. 1989b) is reinforced by the observation that many of the nucleotides implicated in tRNA-ribosome interactions by biochemical and genetic experiments are adjacent to nucleotides involved in subunit association (Merryman et al. 1999a; Merryman et al. 1999b). The crystal structure in fact shows that the tRNAs directly contact intersubunit bridges, at least some of which are believed to be dynamic elements of the ribosome. For example, among the structural elements that are disordered in the high-resolution 50S subunit structure are the bridges B1a, B1b and B2a. Disorder is informative in that it identifies specific molecular features of the ribosome that are capable of independent motion, at least under conditions prevailing in the crystal, and so are candidates for participation in ribosomal dynamics. FIG. 8 shows the features directly surrounding the A- and P-tRNAs at the subunit interface, viewed from the two opposite interface sides. The two tRNAs are sandwiched between bridges B1b and B1b at the top, and B2a at the bottom. The intersubunit contacts for all three of these bridges are disordered in the 50S crystal structure (Ban et al. 2000), suggesting that all three are dynamic elements. On the 30S side (FIG. 5B), the tRNAs are sandwiched between the head and the tops of the penultimate stem and platform, all of which show conformational differences between the free 30S subunits and 70S ribosomes (Yusupov et al. 2001), again suggesting that they are capable of movement during translation. Moreover, the fact that these potentially dynamic elements all interact with each other across the subunit interface points to the likelihood that their respective movements are coordinated. Thus, movement of bridges B1a and B1b would be coupled to rotation of the head, and movement of bridge B 2 a to movement of the penultimate stem and platform. In fact, low-resolution cryo-EM images of the pre- and post-translocation states of *E. coli* ribosomes (Agrawal et al. 1999b) are consistent with such a coordinated movement.

A potentially important clue to the mechanism of translocation comes from tRNA modification-interference studies by Feinberg and Joseph (Feinberg et al. 2001). Their studies show that introduction of a single 2'-O-methyl group at position 71 of P-tRNA abolishes EF-G-dependent translocation. Interestingly, the sole interaction between the ribosome and position 71 of tRNA occurs in the SOS E site, indicating that the effect of the methyl group must be on the P/E state. This finding is consistent with a kinetic analysis that has shown the importance of hybrid states formation for EF-G-dependent translocation (Semenkov et al. 2000). The mechanism by which ribose 71 methylation inhibits translocation must be indirect, since the nearest approach of EF-G is about 70 A away, and its catalytic center is over 100 A away. One possibility is that the effect is mediated through 23S rRNA. Ribose 71 contacts helix 68 of 23S rRNA, which is at the far left end of the lateral arm of domain IV that lies horizontally across the top of the subunit interface surface of the 50S subunit (FIG. 8A). The lateral arm is a continuously coaxially stacked system of canonical and non-canonical helices that traverse the interface. Its far right-hand end terminates in a hairpin loop that makes an A-minor interaction with the stem of the A loop.

The single-stranded loop at the base of the A loop in turn interacts with the minor groove of the sarcin/ricin loop, which has been directly implicated in the GTPase function of EF-G (Hausner et al. 1987). In addition, helix 69, which directly contacts both the A- and P-tRNAs in their respective D stems, is connected to the conserved, non-canonical helix in the middle of the lateral arm of domain IV (FIG. 8A). These structural clues present a circumstantial case for the involvement of specific elements of ribosomal RNA in the mechanism of translocation.

Among the structural elements that are disordered in the 50S subunit structure are the bridges B1a, B1b and B2a. The disorder is informative in that it identifies specific molecular features of the ribosome that are capable of independent motion, at least under conditions prevailing in the crystal, and so are candidates for participation in ribosomal dynamics. B1a and B1b connect the central protuberance of the 50S subunit to the head of the 30S subunit (FIGS. 2E, 5B, 5C; Table III), an independent structural domain which has repeatedly been implicated in ribosomal dynamics, as discussed above. The 50S contacts for the two bridges are the 890 loop of helix 38, and the 134–153 loop of protein L5, both of which are disordered in the SOS subunit electron density map (Ban et al. 2000), and are thus flexible. Bridges B1a and B1b contact the conserved elbow regions of the A-and P-tRNAs, respectively, which undergo the largest movement (~40–50 Å) during translocation. Helix 38 of 23S rRNA, around its conserved internal loop at positions 882/898, interacts with the D and T loops of A-TRNA, and protein L5 interacts with the T loop of P-tRNA via the conserved β-hairpin centered on residue 80. Interestingly, B1a and B1b are also the bridges most strongly affected by the EF-G-dependent intersubunit rotation observed in the above-mentioned cryo-EM studies (Frank et al. 2000). Near their junctions with the body of the 50S subunit, these two bridges are straddled by 5S rRNA, which might in some way help to coordinate their movement.

The most intriguing of the flexible bridge elements is the centrally located B2a, formed by interaction of the universally conserved 1915 loop of helix 69 of 23S rRNA with the top of the penultimate stem (helix 44) of 16S rRNA at the base of the decoding site, where codon-anticodon interactions take place. The helix 69 stem-loop also contacts the A- and P-tRNAs, its loop interacting simultaneously with the penultimate stem of 16S rRNA and with the minor groove of the D stem of A-tRNA, while the minor groove of its stem contacts the minor groove surface of the D stem of the adjacent P-tRNA. The disorder of helix 69 in the 50S subunit structure can be explained by the absence of any direct stacking or other packing interactions with the SOS subunit, and its connection to the rest of 23S rRNA by only a single-stranded loop, to the conserved lateral arm of domain IV of 23S rRNA (which, in turn, embodies bridges B2b, B3 and B7a; FIG. 5C).

Continuous coaxial stacking of the lateral arm includes a non-canonical helix that occupies nearly a whole helical turn in the highly conserved region separating the Watson-Crick helices 68 and 71 (bridges B2b and 133) just below and directly parallel to helix 69. In this crucial central region of the interface, it is not difficult to see how the movement of tRNA could be coupled to perturbation of the interface contacts at bridges B2a, B2b and B3, and potentially to conformational rearrangement of the non-canonical helical segment of the lateral arm. In the post-translocation state, directed hydroxyl radical probing has placed helix 69 in proximity to the tip of the functionally dynamic domain IV of elongation factor EF-G (Wilson et al. 1998), which is believed to mimic tRNA and has been implicated in the mechanism of EF-G-catalyzed tRNA movement (Nissen et al. 1995).

Interaction of the 1915 loop of helix 69 with the minor groove of the D stem of A-site tRNA suggests a possible explanation for the mechanism of action of the Hirsch suppressor (Hirsch 1971), one of the more puzzling tRNA nonsense suppressor mutations, consisting of an A to G mutation at position 24 in the D stem of tryptophan tRNA. A24 is base paired to U11, which is nearly always a pyrimidine, whose 02 position projects into the minor groove of the D stem where it is within contact range of the 1915 loop. Creation of a G24-U11 wobble pair could thus hinder the accessibility of the pyrimidine 02 from the minor groove side. Dahlberg and co-workers have discovered that mutation of the nearby Cl 914 to U confers a nonsense-suppressor phenotype (O'Connor et al. 1995). Thus, this unanticipated bridge B2a-tRNA interaction may play an important role in translational fidelity.

The other bridges implicated in ribosomal function involve the penultimate stem (helix 44), switch helix (helix 27) and the platform (helices 23 and 24) of 16S rRNA. These three features contain five of the six class III sites, whose interesting behavior was identified in earlier chemical probing experiments (Moazed et al. 1987). These bases are all protected independently by tRNA, 50S subunits or certain antibiotics. The observation that all three kinds of ligand were independently able to protect these bases, led to the conclusion that their protection must be caused by ligand-induced conformational changes rather than direct contact between the bases and ligands. Indeed, the structural results show that none of these bases make direct contact with the 50S subunit, tRNA or antibiotics (Carter et al. 2000; Fourary et al. 1996). Three class III sites (A909, A1413, G1487) are found at the contact surface between the internal loop of the switch helix with the minor groove of the penultimate stem, where A909 makes an A-minor interaction with the non-canonical A1413–G1487 base pair (Wimberly et al. 2000).

The reactivities of the N1 positions of all three purine bases in vacant 30S subunits indicates that interaction with tRNA, 50S subunits or streptomycin or the neomycin-related antibiotics induces formation of this interhelical base-triple interaction. Protection by subunit association can be explained by the bridge interactions B2a and B3, which directly flank the 1413–1487 pair, and B2c which involves the 900 loop of the switch helix. Protection by tRNA and antibiotics is consistent with binding of the A- and P-tRNAs and drugs to the decoding site at the top of the penultimate stem. The two class III bases in the 790 loop are protected by their interactions with the 16S rRNA backbone in the decoding site at positions 1497–1498, next to the P-site codon-anticodon interaction. This interaction appears to be stabilized upon subunit association by contact of helix 24 of 16S rRNA with the 50S subunit in the adjacent bridge B2b, and as a result of tRNA binding by backbone-backbone interactions between positions 790- 1 and nucleotides 38–9 in the P-tRNA anticodon stem-loop. The sixth class III base is A1394, in the neck of the subunit (helix 28), in which a hydrogen bond is formed between the N1 position of A1394 and the 2'-hydroxyl of the decoding site nucleotide A1500 (Wimberly et al. 2000). The global result of the class III conformational changes appears to be an overall tightening of the base of the decoding site, in the channel where the mRNA is bound, and where the A- and P-site codon-anticodon interactions take place, which could help to explain the miscoding effects of streptomycin and the aminoglycoside antibiotics.

Intramolecular movement in 16S rRNA, embodied in the class III conformational changes, can be linked to at least one mobile element of 23S rRNA, the conserved 1915 stem-loop (helix 69), and the potentially mobile non-canonical helix in the middle of the lateral arm of domain IV, which is flanked by bridges B2a, B2b, B2c and B3. As just discussed, all four of these bridges are implicated in 50S-induced conformational changes in 16S rRNA that are manifested by the class III protections. It would not be surprising to find that these same conformational changes, which are also induced in 16S rRNA by tRNA and mRNA interactions in the decoding site of the 30S subunit, could reciprocally affect the conformation of this interface region of 23S rRNA, via the same set of bridge interactions. This could have interesting implications for the mechanism of translation, since the lateral arm of domain IV packs directly against the 2600 stem-loop (helix 93) and the A loop (helix 92) of 23S rRNA, both of which are directly involved in interactions in the peptidyl transferase center (Nissen et al. 2000; Moazed et al. 1989a; Kim et al. 1999; Moazed et al. 1998). Furthermore, the 2563–4 loop at the base of helix 92 interacts directly with the base of helix 95, the sarcin-ricin loop, which is directly implicated in the activities of elongation factors EF-Tu and EF-G. Finally, the far left-hand end of the lateral arm of domain IV, near bridge B7a, makes interactions with the acceptor end of the E-tRNA that have been shown to be crucial for EF-G-dependent translocation (Feinberg, J. S. and Joseph, S., personal communication). Knowledge of the complete structure of the ribosome complexed with mRNA and tRNA now provides the possibility to test these and other specific molecular models for the mechanism of translation.

EXAMPLE 2

The Path of Messenger RNA Through the Ribosome

Introduction

The path of the mRNA in the ribosome was mapped for the first time, by X-ray crystallography. Using diffraction data from crystals of 70S ribosomal complexes containing bound tRNAs and either a model mRNA fragment or no mRNA at all (Belitsina et al. 1981), we calculated Fourier difference maps of the bound mRNA. Together with the positions of the A- and P-site codons bound to their respective mRNAs in 70S complexes described above, we were able to describe the complete path of the mRNA through the ribosome, at 7 Å resolution. The mRNA is threaded through a channel that wraps around the neck of the 30S subunit, confirming the general features of the previous models (Frank et al. 1995b; Shatsky et al. 1991). The locations in the ribosome of the Shine-Dalgarno and downstream regions of the mRNA flanking the A and P sites have implications for translational initiation, frame-shifting and other functional interactions of mRNA. Unexpectedly, a model mRNA, based on gene 32 mRNA forms an electron-dense mass, most likely resulting from formation of a small hairpin loop by intramolecular base pairing of the mRNA, that appears to mimic binding of the anticodon loop of tRNA to the A site. Finally, the arrangement of ribosomes around the crystallographic four-fold axis permits direct threading of the mRNA from one ribosome to the next, suggesting how ribosomes may pack in polysomes to make efficient use of shared mRNA and tRNAs.

Experimental

Model mRNA Constructs

Model mRNAs were based initially on the phage T4 gene 32 mRNA. For all three mRNAs (FIG. 9), the Shine-Dalgarno pairing was increased to allow eight potential base pairs with 16S rRNA, and a GGC sequence added to the 5' end to facilitate transcription by T7 RNA polymerase. The mRNA samples used in these studies were made by solid-phase synthesis (Dharmacon, Inc., Boulder, Colo.), and gel-purified prior to use in crystallization.

Crystallization, Data Collection and Model Fitting

*Thermus thermophilus* 70S ribosomes were prepared and co-crystallized with purified *E. coli* initiator tRNA (Subriden, Rollingbay, Wash.) and MK27 (SEQ ID NO: 52), MF36 (SEQ ID NO: 51) or MV36 (SEQ ID NO: 50) mRNAs (Dharmacon), or without mRNA, using the same conditions reported previously (Cate et al. 1999; Yusupov et al. 2001). Diffraction data were collected using synchrotron radiation, as previously described (Cate et al. 1999), and processed using Scalepack and Denzo (Otwinowski, 1993). Fourier difference maps were calculated from measured native amplitudes (Table V) and previously calculated structure factor phases (Cate et al. 1999; Yusupov et al. 2001) using the CCP4 suite of programs (1994). mRNA models were fitted using O (Jones et al. 1997), and molecular structure figures were rendered using Ribbons (Carson 1997).

TABLE V

Crystallographic Data[a]

| Data set (model mRNA) | no mRNA | MK27 | MF36 | MV36 |
|---|---|---|---|---|
| High-resolution limit (Å) | 6.5 | 5.6 | 5.0 | 7.0 |
| $R_{sym}$* | 8.9 | 12.4 | 9.4 | 8.8 |
| Mean I/σ(I) | 2.6 at 6.5 Å | 2.1 at 5.6 | 3.3 at 5.5 | 2.3 at 7.0 |
| Number of reflections | | | | |
| Unique | 95,127 | 153,627 | 209,044 | 73,146 |
| Observational redundancy | 3.6 | 3.0 | 2.8 | 3.6 |
| Completeness (%) | 96.7 | 97.7 | 95.3 | 89.5 |

[a]Crystals of ribosomal complexes were prepared as described in Methods, using the model mRNAs MK27, MF36 and MV36 (FIG. 1). All data were collected at beamline 5.0.2, at the Berkeley Center for Structural Biology, Lawrence Berkeley National Laboratory.
*$R_{sym} = \Sigma |I - <I>| / \Sigma I$

RESULTS

The model mRNA MF36 was based on phage T4 gene 32 mRNA (FIG. 9), except that the potential for pairing of its Shine-Dalgarno sequence was increased to eight base pairs by extending its complementarity to the 3' tail of 16S rRNA. For the MV36 (SEQ ID NO: 50) and MK27 (SEQ ID NO: 52) mRNAs different coding and downstream regions were also introduced (FIG. 9). Complexes containing *Thermus thermophilus* 70S ribosomes, mRNA fragments and either full-length tRNA or an anticodon stem-loop (ASL) bound to the ribosomal P site were co-crystallized as described (Cate et al. 1999; Yusupov et al. 2001). Similar co-crystals containing 70S ribosomes and initiator tRNA, but lacking mRNA (Belitsina et al. 1981) were prepared under the same conditions. Data were collected using synchrotron radiation, and previously derived structure factor phases (Cate et al. 1999; Yusupov et al. 2001)) were used to compute Fourier difference maps (Table V).

FIG. 10A shows the 7 Å Fourier difference map computed for the MK27 mRNA fragment (SEQ ID NO: 52) using data collected from crystals containing two types of ribosomal constructs. In one construct, 70S ribosomes were bound with the MK27 mRNA (SEQ ID NO: 52) and initiator tRNA; the other construct was identical, except that mRNA was omitted. Pseudoatom models for the mRNA 27mer and the 3'-terminus of 16S rRNA, as well as the previously-determined models for the A and P codons (Yusupov et al. 2001), are shown superimposed on the difference map. The positions of the A- and P-codons provide a close check on the register of the central part of the mRNA model, while the resolution of the difference map itself allows fitting the rest of the mRNA with a precision of about +/−1 nucleotide.

A pronounced cylinder of electron density is seen at the 5' end of the mRNA, whose dimensions are in good agreement with the predicted eight base-pair Shine-Dalgarno helix. A gap of about four nucleotides in the electron density is seen at the position of the P codon and its 5' flanking nucleotide (mRNA positions −1 to +3). This can be explained by the folding back of the 3' tail of 16S rRNA in the absence of mRNA, as found in the high-resolution structure for the *T. thermophilus* 30S subunit (Wimberly et al. 2000); binding of the tail of 16S rRNA to the P codon position of the ribosome results in subtraction of the P codon from the mRNA difference map. An additional small gap is found at position −4 of the mRNA, which may be due to local disorder. The location of the A codon is close to that found in the presence of A-tRNA, even though A-tRNA was absent in these complexes. At its 3' end, the MK27 (SEQ ID NO: 52) difference density terminates in good agreement with the predicted position of the 3' end (position +12) of the mRNA model.

The difference map for the MK36 mRNA (SEQ ID NO: 50) resembles that of the MK27 mRNA (SEQ ID NO: 52), except at its 3' tail and in the A codon region, where a cylinder of density overlapping with the position normally occupied by the A-tRNA (Cate et al. 1999; Ogle et al 2001; Yusupov et al. 2001) appears (FIG. 10B). This unexpected feature can be explained by intramolecular base pairing of complementary sequences in the gene 32 mRNA (positions +4 to +7 and +12 to +15 of the MF36 mRNA (SEQ ID NO: 51)(FIG. 9). This feature is absent in the difference map for MK-27 (SEQ ID NO: 52)(FIG. 10A), in which the self-complementary sequences were replaced by poly(A). A four base-pair stem modeled from a tetraloop-containing helix (13) can be accommodated in the extra difference density (FIG. 10B). Modeled in this way, the 3' end of the MF36 mRNA (SEQ ID NO: 51) terminates close to the end of the strongest part of the electron density (FIG. 10B). Weaker density can be seen extending about six nucleotides further, suggesting that the unfolded form of the MF36 mRNA (SEQ ID NO: 51) is also present, but at lower occupancy. The weaker density extends to about position +17, implying that the very 3' end of the mRNA chain (nucleotides +18 through +21) is disordered in the unfolded mRNA conformer. The mRNA hairpin feature occupies the position of the anticodon stem-loop (ASL) of the A-site tRNA (Cate et al. 1999; Yusupov et al. 2001), as shown in FIG. 10C. The striking coincidence of these two structures suggests that the mRNA hairpin may be designed to mimic the A-site ASL, possibly playing a role in initiation of translation of gene 32 mRNA.

FIG. 11A shows the path of the mRNA in the context of the complete 30S ribosomal subunit of the 70S ribosome, as viewed from the subunit interface. The mRNA passes through upstream and downstream tunnels to access the interface, where only about eight nucleotides (−1 to +7), centered on the junction between the A and P codons, are exposed. Binding of mRNA to the 30S subunit during translational initiation requires opening one or both of the tunnels, (which are closed non-covalently), depending on the length of the upstream leader, since it has been shown by Bretscher (Bretscher, 1968) that the ribosome is able to initiate translation on a circular message. The contact point between the head and body has been described as a potential "latch", the closing of which was proposed to provide a geometry that guarantees processivity, provide directionality and prevent dissociation (Schluenzen et al. 2000). The boundaries of the ribosomal contacts with the mRNA (−15 to +16) are within experimental error of those predicted (−16 to +16) by Steitz (Steitz, 1969). The features of 16mRNA structure that surround the message agree well (P-P distances from 8 to 28 Å) with all but one (60 Å between mRNA position −1 to −8 with 16S rRNA position 1360) of the site-directed crosslinking results (Bhangu et al. 1994; Bhangu and Wollenzien, 1992; Brimacombe, 1995; Dokudovskaya et al. 1993; Dontsova et al. 1992; Greuer et al. 1999; Juzumiene et al. 1995; Rinke-Appel et al. 1993; Rinke-Appel et al. 1994; Sergiev et al. 1997).

The 5' end of the mRNA originates at the back of the platform (FIG. 11B), where it enters the groove between the head and platform, wrapping around the neck of the subunit and exiting on the opposite side between the head and shoulder. Although the ribosome-bound portion of the mRNA contains about 30 nucleotides, stretching from about position −15 to +15, the region most closely wrapped around the neck extends from around positions −3 to +10, centering on the junction between the A and P codons. The immediate molecular environment of the mRNA contains mainly 16S rRNA (SEQ ID NO: 45)(FIG. 11A), except at the extremities of its binding site, around the upstream Shine-Dalgamo interaction and in the downstream region around position +12, as well as in the A codon, where it is close to ribosomal proteins.

Upstream Interactions

Figure 12A:
FIG. 12. (A) Solvent-side stereo view of the Shine-Dalgamo (S/D) helix bound in its cleft, formed by helices 20, 28 and 37 (h20, h28, h37) and the 723 loop of 16S rRNA and proteins S 11 and S 18, and the path of mRNA nucleotides –1 to –4 through the upstream tunnel. The MV36 Fourier difference map is shown. (B) Interface stereo view of the A- and P-site codons and their flanking nucleotides (530, 790, 791-, 926, 1492, 1493 and 1498) in 16S rRNA. The locations of restrictive mutations in ribosomal protein S12 are shown in yellow (the universal PNSA sequence) and orange. The positions of the bases for G926 and U1498 are modeled from the high-resolution structure of the *T. thermophilus* 30S subunit (Wimberly et al. 2000). (C) Same as (B), but with the A- and P-tRNAs (orange and red, respectively) docked according to their experimentally observed locations (Yusupov et al. 2001).

The Shine-Dalgarno helix fits into a large cleft between the back of the platform and the head of the subunit (FIG. 12A). In the solvent-side view, The Shine-Dalgamo cleft is formed by helix 20 on the bottom, the 723 bulge loop and proteins S11 (SEQ ID NO: 34) and S18 (SEQ ID NO: 41) on the left, and the neck helix (helix 28) and helix 37 on the right. The N-terminal end of protein S18 (SEQ ID NO: 41), which is rich in basic and aromatic side-chains, is directed toward the major groove of the Shine-Dalgamo helix, at the 5' end of the mRNA (position −15). Extra density under the upstream end of the Shine-Dalgamo helix may come from the N-terminal 15 amino acids of S18 (SEQ ID NO: 41), which were disordered in the high-resolution structure of the 30S subunit (Wimberly et al. 2000). Both the N-terminal tail and the loop of S11 (SEQ ID NO: 34) that contains Arg 54 are near enough to make specific interactions with the Shine-Dalgamo helix. At the downstream end of the Shine-Dalgarno helix, the C-terminal tail of protein S11 (SEQ ID NO: 34) interacts with the backbone of the mRNA around positions −4 to −6.

Directly downstream of the Shine-Dalgarno helix, the 5' leader (positions −1 to −4) of the mRNA passes through a short tunnel between the head and the platform of the subunit to the interface side, where it is surrounded by the tip of the β-hairpin of protein S7 (SEQ ID NO: 30), the apex of the 690 loop, the minor groove side of the 790 loop, the base of helix 45 around position 1505 and the 925 region of helix 28. This region of the mRNA contains the E codon (position −1 to −3), whose fall access to the interface is hindered by its location in the tunnel.

The P and A Codons

After a sharp turn in the mRNA around position −1, the P and A codons are presented to their respective tRNAs in the middle of the interface surface of the cleft, with an approximately 45° kink between the adjacent codons that allows simultaneous pairing of the A- and P-tRNA anticodons (as described above). The two codons are centered above the axis of the penultimate stem of 16S rRNA (SEQ ID NO: 45), where they occupy the major groove of the non-canonical helical structure formed by the 1400 and 1500 strands of 16S rRNA (SEQ ID NO: 45) often referred to as the "decoding site" (FIG. 12B). As noted above, the P codon follows a path very similar to that described for the folded-back tail of 16S rRNA (SEQ ID NO: 45), which appears to mimic this region of the mRNA in the high-resolution crystal structure of the 30S subunit (Wimberly et al. 2000).

Some details of the interactions between the ribosome and the P codon can therefore be inferred from the 30S structure. Interestingly, the N1 position of G926, which was protected from kethoxal by P-tRNA binding, even in the absence of mRNA (Moazed et al., 1990; Moazed et al. 1986b), is positioned to interact with the phosphate of nucleotide +1 of the P codon. The observed tRNA-dependent protection may be due to re-positioning of the mRNA chain (or the 16S tail, in the absence of mRNA) in response to tRNA binding, since the mRNA backbone begins to diverge from the path of the 3'-tail of 16S rRNA near position −1 of the mRNA. Modification-interference experiments also indicated the importance for G926 in mRNA-independent binding of tRNA$^{Phe}$ to the 30S P site (von Ahsen and Noller, 1995); since the 3' tail does not contain a Phe codon, this result suggests that the apparent mRNA mimicry by the 16S rRNA tail, stabilized by the 926 interaction, may be important in inducing the active conformation of the 30S P site, and could help to explain the fact that initiator tRNA can bind to the 30S subunit independently of mRNA during translational initiation (Gualerzi et al. 1977).

The 1500 strand of 16S rRNA crosses at right angles to the mRNA chain, where nucleotide 1498 lies directly under nucleotide +1 of the P codon (FIG. 12B). In the high-resolution structure (Wimberly et al. 2000) the phosphate of nucleotide 1498 packs against ribose +1 and its base (m $^3$U 1498 in E. coli) against ribose +2. These interactions are evidently stabilized by interaction of the N6-amino group of A790 and the N1 of the universally conserved G791 with the non-bridging phosphate oxygens of nucleotide 1498. Both A790 and G791 were earlier identified as "class III" bases (Moazed et al. 1987), whose protection from attack by chemical probes at their N1 positions was predicted to result from a conformational change in 16S rRNA (SEQ ID NO: 45), because the same protections were conferred by P-tRNA, 50S subunits or certain antibiotics. These class III protections can now be explained by movement of the 790 stem-loop (helix 24) toward the penultimate stem in response to binding of P-tRNA or the other ligands, simultaneously resulting in interaction of the backbone of the 790 loop with the bottom of the anticodon stem of P-tRNA and packing of nucleotide 1498 against the P codon. Such a movement would be consistent with the counter-clockwise rotation of the platform of the 30 S subunit when it joins with the 50S subunit, observed in cryo-EM studies (Lata et al. 1996).

At the junction between the P and A codons, the mRNA is blocked from continuing its A-RNA-like trajectory by the phosphate of nucleotide 1401, which lies directly in its path (FIG. 12B). This redirects the mRNA, resulting in the observed kink in the mRNA between the A and P codons.

In the A site, the bases G530, A1492 and A1493 interact intimately with the minor groove of the A-site codon-anticodon helix, in a possible discriminatory mechanism for A-site tRNA selection, as shown recently by Ramakrishnan and co-workers (Ogle et al. 2001). A further interaction is made by the β-hairpin loop of protein S12 (SEQ ID NO: 35) around the conserved PNSA sequence at positions 48–51, which is directly beneath riboses +5 and +6 (Ogle et al. 2001). This part of S12 (SEQ ID NO: 35) contains-most of the mutations that confer restrictive (hyper-accurate) phenotypes.

Downstream Interactions

Immediately downstream of the A codon, the mRNA passes through a second tunnel, about 20 Å in diameter, between the head and shoulder of the subunit, leading to the solvent side of the 30S subunit, first observed in cryo-EM reconstructions (Frank et al. 1995b). It has been suggested that closing of this tunnel around the mRNA ensures processivity and directionality of mRNA movement (Schluenzen et al. 2000). From the interface side, the mRNA (positions ca. +7 to +10) passes first through a layer of RNA, where it is surrounded by helix 34 at the top, the base of the neck at nucleotide 1397 (helix 28) on the right, the 5' hairpin loop (at nucleotide 16 of 16S rRNA (SEQ ID NO: 45)) at the bottom and the 530 loop on the left (FIG. 13A). In the RNA layer, bases C 1397 and U1196 (Wimberly et al. 2000) are oriented toward the mRNA around positions +7 and +9, respectively, and may help to position the mRNA immediately downstream from the A codon.

Finally, the mRNA (positions ca. +11 to +15) passes through a layer of protein into the solvent at the back of the subunit. Viewed from the solvent side (FIG. 13B), the mRNA is encircled by protein S3 (SEQ ID NO: 26) at the top, S4 (SEQ ID NO: 27) on the right and S5 (SEQ ID NO: 28) on the lower left. These three proteins project a dense array of basic side chains into the downstream tunnel, including Arg131, Arg132, Lys135 and Arg164 from S3 (SEQ ID NO: 26), Arg47, Arg49 and Arg50 from S4, and Arg15 and Arg24 from S5 (SEQ ID NO: 28), which appear to position the downstream region of the mRNA via interactions with its backbone phosphates.

mRNA Helices, Pseudoknots and Frame-shifting

All mRNA chains have the ability to form hairpins and other intramolecularly base-paired structures, yet the codons must be read in single-stranded form. The ribosome is therefore able to unwind mRNA secondary structure, by some as-yet unknown mechanism. An mRNA hairpin would approach the ribosome surface at the back of the 30S subunit, from the view shown in FIG. 13B. Since an RNA helix is too large to pass through the narrow downstream tunnel, unwinding of mRNA structure is likely to occur at or near the entrance to the tunnel, around positions +13 to +15. Unfolding of a downstream (+11 to +17, +25 to +31) hairpin of λ cro mRNA, dependent on binding of initiator tRNA, may result from its threading through the downstream tunnel (Balakin et al. 1990).

A possible mechanistic basis for a mRNA helicase is suggested by the fact that proteins S4 (SEQ ID NO: 27) and S5 (SEQ ID NO: 28) are integral to the body of the 30S subunit, whereas S3 (SEQ ID NO: 26) is part of the head. If one strand of the incoming helix were bound to S4 (SEQ ID NO: 27) and/or S5 (SEQ ID NO: 28) and the other strand to S3 (SEQ ID NO: 26), the rotational movement of the head that is believed to occur during translocation (Agrawal et al. 1999b) could result in physical disruption of the helix, at the rate of about three base pairs (i.e., one codon) at a time, simultaneously advancing the mRNA through the ribosome.

Interestingly, the part of protein S5 (SEQ ID NO: 28) that faces the mRNA near its entry point to the downstream tunnel has the same three-dimensional fold as the double-stranded RNA binding domain (dsRBD) (Brunger et al. 1998). However, its relatively low sequence homology with the dsRBD consensus does not provide support for its potential binding to double-stranded RNA (dsRNA), at least in the way that has been observed for complexes containing the Xenopus XIrbpa protein and dsRNA (Brunger et al. 1998).

One type of structure that has been shown to perturb translation are mRNA pseudoknots. Most extensively documented is the finding that certain downstream pseudoknots promote a –1 shift of the translational reading frame when a "shifty" sequence is positioned in the decoding site, a mechanism that is exploited for translational regulation by many viruses (Alam et al. 1999; Brierley et al. 1989). The optimum position for the pseudoknot is between positions +11 and +15, which corresponds closely to the region where mRNA enters the downstream tunnel (+13 to +15), at the position of the proposed mRNA helicase. A simple explanation for the frameshifting event is that the structure of the pseudoknot is poorly matched to the geometry of the helicase, blocking entry of the mRNA into the downstream tunnel. Upon EF-G-catalyzed translocation, forward movement of the mRNA would be retarded, resulting in backlash of the mRNA and favoring slippage into the –1 reading frame.

Path of the mRNA in the Crystal Lattice

Figure 14:
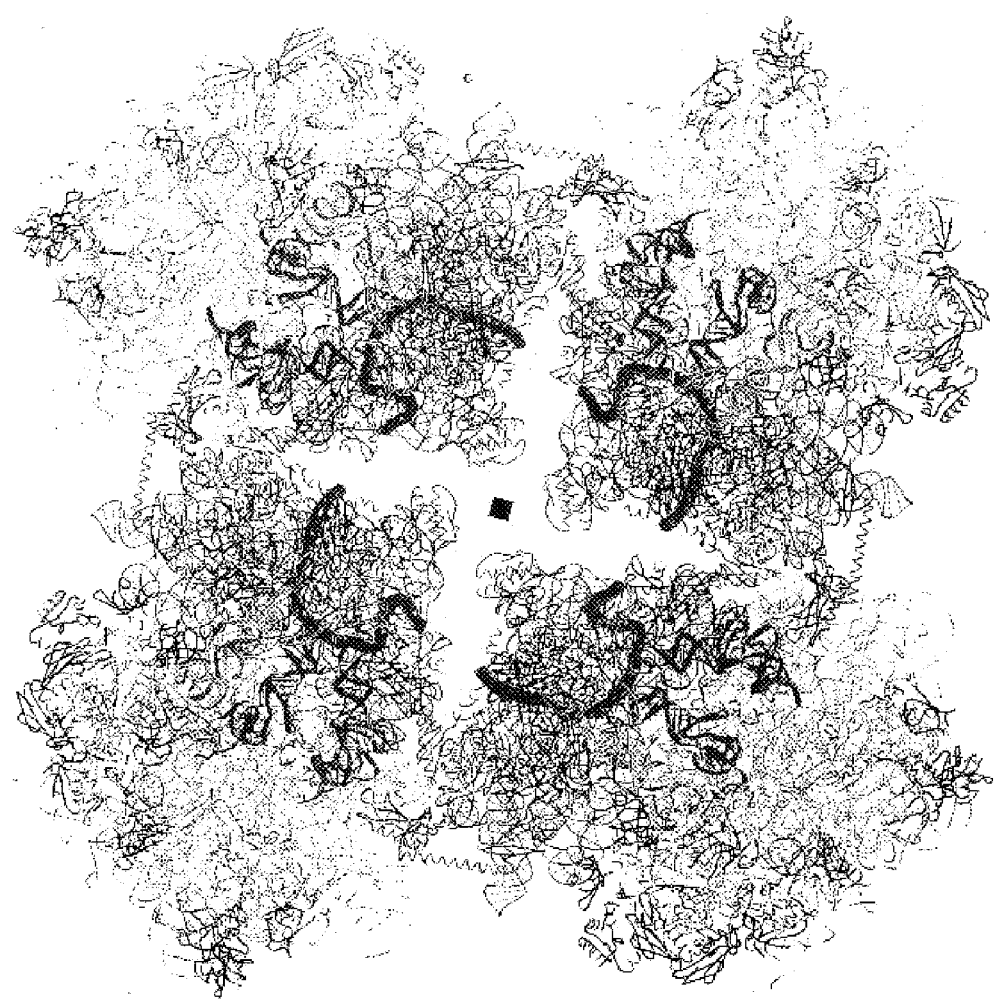
FIG. 14. View down the crystallographic four-fold axis of the 70S ribosome-mRNA-tRNA complex (Yusupov et al. 2001), showing the head-to-tail juxtaposition of the model mRNAs (red-orange) between adjacent ribosomes. The molecular components shown are 16S rRNA (cyan), 23S rRNA (grey), 5S rRNA (grey-blue), small subunit proteins (dark blue), large subunit proteins (magenta), the A-, P- and E-tRNAs (yellow, orange and red) and the mRNA (red-orange).

In our crystals, the *Thermus thermophilus* 70S ribosomes pack in the 1422 tetragonal space group (Cate et al. 1999), in which adjacent ribosomes are organized symmetrically in layers of tetramers that are centered around a four-fold axis. FIG. 14 shows the arrangement of ribosomes around the four-fold axis in the crystal lattice. A striking feature of this arrangement is that it juxtaposes the 3' end of the mRNA in one 70S monomer with the 5' end of the mRNA of the adjacent 70S monomer, in principle permitting direct threading of a single continuous mRNA through all four ribosomes in the tetramer.

The crystal packing might reflect one of the ways in which ribosomes interact with each other in polysomes in vivo. An interesting consequence is that the E site of one ribosome is directly adjacent to the A site of its neighboring ribosome, so that a tRNA exiting one ribosome would immediately be positioned to enter the next ribosome, after charging by its synthetase. Thus, a given tRNA could, in effect, follow its own codon through the polysome.

Conclusion

Our 7 difference maps clearly reveal the path of the mRNA through the ribosome and identify the molecular features of the ribosome that surround each position along the length of the mRNA. The path taken by mRNA through the *T. thermophilus* 70S ribosome is likely to be generalizable to all bacterial and archaeal ribosomes, which share all of the structural features making up the mRNA binding channel. In fact, with the exception of the Shine-Dalgarno interaction, which is absent in eukaryotic ribosomes, we would expect mRNAs to follow a very similar path in all ribosomes. A major unanswered question is how the movement of mRNA is coupled to tRNA movement during the translocation step of protein synthesis, to prevent disruption of the weak codon-anticodon interactions and loss of the translational reading frame. A possible answer is that some of the ribosomal features that contact the mRNA are themselves mobile, and that the ribosome is able to coordinate their movement with that of tRNA during translocation. A possible example, mentioned above, is the head of the 30S subunit. Another obvious candidate is the decoding site itself, a non-canonical helix that links the penultimate stem with the head of the small subunit.

The A and P codons are threaded through the major groove of this unusual helix (FIG. 12B), which is formed from the universally conserved 1400 and 1500 strands of 16S rRNA (SEQ ID NO: 45). The decoding site helix is, in turn, connected via bridge B2a to another non-canonical helix formed by the universally conserved 1935 and 1965 strands of 23S rRNA (SEQ ID NO: 23) in the lateral arm of domain IV, that has been proposed to play a role in tRNA movement and intersubunit signaling as described above.

Intriguingly, the connection between the two non-canonical helices is made by helix 69 of 23S rRNA (SEQ ID NO: 23), which not only interacts via its hairpin loop to the decoding site of 16S rRNA (SEQ ID NO: 45), but simultaneously interacts with the D stems of both the A- and P- tRNAs (FIG. 12C), suggesting a possible structural basis for coupling mRNA and tRNA translocation.

EXAMPLE 3

Use of the Ribosome Structure to Determine Interaction of Translation Initiation Factor 3 with the 30S Ribosomal Subunit In this example, we demonstrate how biochemical footprinting and structural information about the ribosome may be used to facilitate the docking of functionally significant molecules on the ribosome structure to identify and characterize a ribosome target site. While the example describes the docking of translation initiation factor 3 (IF3), the results may be generalized to any molecule that can be bound by the ribosome. The information derived from the docking can be used to identify one or more target sites for disrupting the interaction between the ribosome and a ligand such as IF3. Identification and characterization of a ribosome target site structure, informed by the docked structure to provide information as to the three-dimensional shape and charge distribution of the site, allows one of ordinary skill to design other molecules that can occupy the target site. If binding of the ligand is necessary for proper ribosome function, a molecule designed to disrupt or prevent the ribosome-ligand binding interaction can inhibit protein translation. Such molecules have utility as antibiotics, preservatives, and as agents to further define the biochemical mechanisms of ribosome function.

In this example we show how to use hydroxyl radical footprinting and directed probing from Fe(II) derivatized IF3 to map the interaction of IF3 (SEQ ID NOS: 53 and 54) relative to 16S rRNA (SEQ ID NO: 45) and tRNA$^{Met}_f$ in the 30S ribosomal subunit. Our results place the two domains of IF3 (SEQ ID NOS: 53 and 54) on opposite sides of the initiator tRNA with the C-domain at the platform interface, and the N-domain at the E site. The C-domain coincides with the location of helix 69 of 23S rRNA (SEQ ID NO: 23), explaining the ability of IF3 (SEQ ID NOS: 53 and 54) to block subunit association. The N-domain neighbors proteins S7 (SEQ ID NO: 30) and S 11 (SEQ ID NO: 34) and may interfere with E-site tRNA binding. Our model suggests that IF3 influences initiator tRNA selection indirectly.

Introduction

During initiation, the ribosome must select the correct reading frame for translation of messenger RNA. The triplet codon start signal of the message must be identified and aligned in the P site of the 30S subunit so that it basepairs with the anticodon of initiator tRNA. A complex is formed between the small ribosomal subunit, the initiator tRNA in the P site and the mRNA before the large subunit can bind and protein synthesis can begin (Gualerzi and Pon, 1990; Gualerzi et al. 2000). Both prokaryotes and eukaryotes require multiple protein factors in order to form the intermediates in this pathway although there are significant differences in the factors involved and the intermediates formed. Initiation is the rate-limiting step of translation and is the stage where translational regulation most often occurs (Sonenberg et al. 2000).

Three protein factors, IF1, IF2, and IF3, in addition to GTP co-factor are required for proper initiation in bacteria (Gualerzi and Pon, 1990). IF2, a GTPase, stimulates the binding of initiator tRNA to the P site of the 30S subunit (Canonaco et al. 1986). Chemical footprinting studies showed that IF1 protects nucleotides that are protected by tRNA bound to the A site of the 30S subunit, leading to the hypothesis that IF1 blocks binding of tRNA to the A site during initiation (Moazed et al. 1995). A recent crystal structure of IF1 bound to the 30S subunit reveals that IF1 does occupy the 30S A site (Carter et al. 2001).

Several activities have been ascribed to IF3 during initiation. IF3 dissociates 70S ribosomes by binding preferentially to 30S subunits, making them available for initiation (Subramanian and Davis, 1970; Grunberg-Manago et al. 1975). IF3 also increases the accuracy of initiator tRNA selection both in vivo and in vitro (Risuleo et al. 1976; Hartz et al. 1989; Sussman et al. 1996; Meinnel et al. 1999; Sacerdot et al. 1999). Recently, a role for IF3 in the recycling of subunits was proposed since IF3 was observed to enhance the dissociation of deacylated tRNAs from post-termination complexes (Karimi et al. 1999). The mechanisms by which IF3 accomplishes these functions are not well understood.

IF3 is a two-domain, 20 kD protein, whose N-terminal and C-terminal domain structures have been determined by both x-ray crystallography and NMR (Biou et al. 1995; Garcia et al. 1995a; Garcia et al. 1995b). The N-domain has an α/β-fold and is connected to the C-domain by an extended α-helical element rich in basic and aromatic residues. This linker helix is partially disordered in both the crystal and the NMR structures but to different extents. Dynamics studies of the intact, full-length protein by NMR support the notion that the linker is flexible in solution (Moreau et al. 1997). The C-domain of IF3 folds into a classical RNA binding domain consisting of a four-stranded (β-sheet backed by two α-helices.

The site of interaction of IF3 with the 30S subunit has been studied using many approaches, sometimes yielding conflicting results. Immunoelectron microscopy located IF3 at the cleft of the 30S subunit (Stöffler and Stöffler-Meilicke, 1984). IF3 has been crosslinked to small subunit proteins S7 (SEQ ID NO: 30), S11 (SEQ ID NO: 34), S12 (SEQ ID NO: 35), S13 (SEQ ID NO: 36), S18 (SEQ ID NO: 41), S19 (SEQ ID NO: 42), and S21 (SEQ ID NO: XX), a set of proteins that is distributed over a broad area of the 30S subunit (Cooperman et al. 1977; MacKeen et al. 1980; Cooperman et al. 1981; Boileau et al. 1983). IF3 has also been crosslinked to helices 26 and 45 of 16S rRNA (SEQ ID NO: 45) in the central and 3'-minor domains of the 30S subunit, respectively (Ehresmann et al. 1986). Chemical footprints using kethoxal, DMS, and CMCT were found in helices 23 and 24 of the central domain of 16S rRNA (Muralikrishna et al. 1989; Moazed et al. 1995). An NMR study indicated that IF3 interacts with a fragment of the 3'-end of 16S rRNA containing residues 1495–1542 (Wickstrom et al. 1986). Cryo-electron microscopy (cryo-EM) reconstruction localized the C-terminal domain of IF3 at the interface side of the small subunit (McCutcheon et al. 1999). In contrast, a recent crystallographic analysis of the C-domain of IF3 soaked into crystals of the *Thermus thermophilus* (Tth) 30S subunit revealed a binding site for the C-terminal domain on the opposite face of the 30S subunit (Pioletti et al. 2001).

Here we describe an independent approach to localize the binding site of IF3 (SEQ ID NOS: 53 and 54) on the 30S ribosomal subunit with respect to 16S rRNA (SEQ ID NO: 45), using a combination of hydroxyl radical footprinting and directed hydroxyl radical probing. Directed probing was carried out from Fe(II) tethered to 14 different positions on the surface of IF3. Sites of directed cleavage of 16S rRNA and the initiator tRNA, together with the footprinting data provided sufficient constraints to model the positions of the N- and C-domains of IF3 in the crystallographically-determined structure of the 30S subunit (Schluenzen et al. 2000; Wimberly et al 2000; Yusupov et al. 2001). Our findings explain the subunit dissociation activity of IF3, and provide clues to its other biological roles.

Experimental Procedures

Preparation of Mutant Derivatives of IF3

The gene encoding IF3 was amplified from MRE600 genomic DNA by PCR using primers that contained restriction sites for convenient cloning and that also changed the non-canonical, unique AUU start codon of IF3 to AUG to promote efficient overexpression. The PCR product was subcloned into pET-24b (Novagen) resulting in recombinant IF3 containing a C-terminal His6-Tag (SEQ ID NO: 125) for rapid purification. A cysteine-free variant of IF3 for a use as a control in probing experiments was produced by site-directed mutagenesis (Kunkel et al. 1987) where the single occurring natural cysteine residue at position 65 was mutated to alanine, a substitution tolerated in phylogenetic alignments of IF3s from various species. Single cysteine residues were introduced by site-directed mutagenesis at fifteen different positions on the surface of IF3 at sites that were not absolutely conserved and were located on the surface of the protein (R11, Q22, E44, A49, E76, K79, S80, S81, K97, E104, K123, M135, Q138, M142, and Q180). Wild-type and mutant constructs were over-expressed in E. coli BL21 (DE3) after inducing mid-log cells to over-express for 3 hours after addition of 1 mM IPTG.

Cells were resuspended in buffer containing 100 mM NaCl, 100 mM Tris-Cl, pH 7.5 and lysed by freezing and thawing in the presence of lysozyme. The cell lysate was centrifuged for 15 minutes at 10,000 rpm in a JA-20 rotor, and the supernatant transferred to Ni-NTA agarose resin (Qiagen) that had been pre-equilibrated with resuspension buffer. The resin was then extensively washed with high-salt buffer containing 1 M NaCl, 100 mM Tris-Cl, 10% glycerol, and 6 mM β-ME. IF3 was then eluted with 500 mM imidazole and dialyzed against three changes of storage buffer containing 122 mM $NH_4Cl$, 80 mM $K^+$ Cacodylate, 10 mM $MgCl_2$, 1 mM DTT, pH 7.2. The protein concentration was estimated by Bradford assay. The purified proteins were flash-frozen and stored in aliquots at $-80°$ C. IF3 derivatives purified in this manner were judged greater than 95% pure by Coomassie blue-stained SDS-PAGE.

mRNA and tRNA

A synthetic 36-nucleotide T4 gene32 mRNA derivative was purchased from Dharmacon, with sequence 5'-GGCAAGGAGGUAAAAAUGU-UUAAACGUAAAUCUACU-3' SEQ ID NO:50). E. coli tRNAMecf was purchased from Sigma. mRNA and tRNA were purified on 18% and 10% polyacrylamide denaturing gels, respectively. tRNA was treated with calf-intestinal alkaline phosphatase (Boehringer-Mannheim) and subsequently 5'-end-labeled with [$^{32}$P]-y,-ATP (ICN). tRNA was gel-purified again and renatured in buffer containing 10 mM $MgCl_2$ and 75 mM Tris-Cl, pH 7.5 at 55° C. for 3 minutes, followed by slow cooling to room temperature.

Initiation Complex Formation

Complexes of IF3 bound to 30 subunits were prepared as described (Moazed et al. 1995). Typically, 30S subunits (prepared as described in Moazed et al. (1986a) at a concentration of 0.4 μM were heat activated in buffer containing 122 mM $NH_4Cl$, 80 mM $K^+$ Cacodylate, 10 mM $MgCl_2$, and 1 mM DTT, pH 7.2 at 42° C. for 15 minutes. Purified IF3 was added to a final concentration of 4 μM and incubated for 5 minutes at 37° C. followed by 30 minutes at room temperature.

Kethoxal and Solution Fe(II)-EFTA Footprinting of IF3

Complexes of IF3 bound to 30S subunits were probed with kethoxal as follows. 40 pmol of 30S subunits were incubated with a ten-fold molar excess of IF3 in a 100 μL reaction volume. Control samples of 30S subunits alone were treated identically to those containing IF3. Kethoxal modification was performed as described (Moazed et al. 1986a), where 4 μL of 37 mg/mL kethoxal was added to each sample and incubated at 37° C. for 8 minutes. Samples were then adjusted to 25 mM potassium borate and precipitated with ethanol. Hydroxyl radical footprinting experiments were performed as described (Powers and Noller, 1995) except that the final concentrations of probing reagents added to each reaction were as follows: 1 mM Fe($NH_4$)($SO_4$)$_2$·$_6H_2O$, 2 mM EDTA, 5 mM ascorbic acid, and 0.05% $H_2O_2$. Reactions were incubated for 10 minutes on ice, quenched with an equal volume of 7.6 mg/mL thiourea, and ethanol precipitated. In both the kethoxal and hydroxyl radical footprinting experiments, the rRNA was extracted and the sites of protection from modification were identified by primer extension as described (Stem et al. 1988b).

Preparation of Fe(II)-BABE-derivatized IF3

Conjugation of Fe(I)-BABE to cysteine-containing mutants of IF3 was performed essentially as described (Culver and Noller, 2000). 2–6 mnol of each IF3 derivative were incubated with 100 nmol Fe(II) BABE in 100 μL buffer containing 122 mM $NH_4Cl$, 80 mM $K^+$ Cacodylate, 10 mM $MgCl_2$, 1 mM DTT, pH 7.2 at 37° C. for 30 minutes. Free Fe(II)-BABE was separated from derivatized protein on Microcon-10 microconcentrators using multiple washes with the incubation buffer. A mock modification reaction was also performed on the cysteine-free IF3 mutant as a control.

Directed Hydroxyl Radical Probing

IF3–30S complexes containing Fe(II) conjugated IF3 were formed as described above. Free, excess IF3 was removed by centrifuging the complex in a microcon-100 microconcentrator and washed by spinning through an additional 500 microliters of buffer. The isolated IF3–30S complexes were brought to 100 microliters and probed by initiating hydroxyl radical formation with 0.025% $H_2O_2$ and 5 mM ascorbic acid. The reactions were incubated on ice for 10 minutes and quenched with 20 mM thiourea. 16S rRNA was extracted and analyzed by primer extension as described (Stem et al. 1988b). Cleavage intensities were assigned as strong, medium, or weak according to the intensity of each band relative to control sequencing bands as described (Joseph et al. 1997).

For directed probing of initiator tRNA, 10 pmol of heat-activated 30S subunits were coincubated in 25 microliters with 20 pmol mRNA, 1 pmol 5' end-labeled initiator tRNA, and Fe(II) derivatized IF3 for 10 minutes at 37° C. followed by incubation at room temperature for 30 minutes. Unbound mRNA, tRNA and IF3 were removed by spinning in a microcon-100. The complexes were brought up to 25 microliters volume and probed as above. The reactions were ethanol precipitated, and electrophoresed on 15% denaturing PAGE.

Results

Hydroxyl Radical Footprinting

We tested the binding of recombinant wild-type IF3 to the 30S subunit by reproducing its previously determined kethoxal footprint on 16S rRNA (SEQ ID NO: 45) (Moazed et al. 1995). Lanes 3–5 in FIG. 15 (left panel) show that purified, recombinant IF3 protects nucleotides G700 and G703 from modification at N1IN2 by kethoxal. Recombinant IF3 was also able to dissociate tight-couple 70S ribosomes into subunits, by sedimentation analysis (data not shown).

Figure 16:
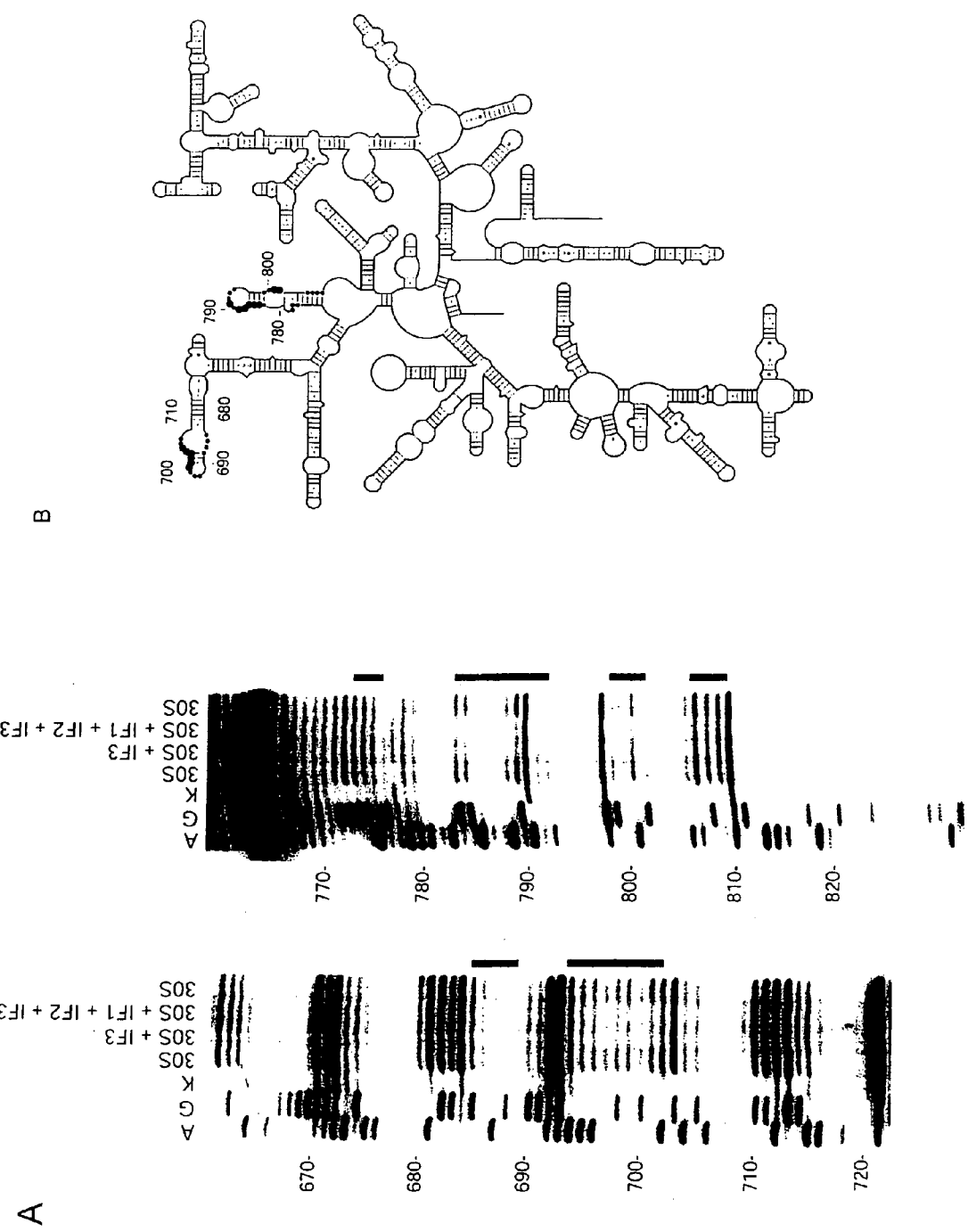
FIG. 16. Hydroxyl radical footprinting of IF3 on 16S rRNA. (A) Primer extension analysis of the hydroxyl radical footprint of IF3 on 16S rRNA in the 30S subunit. Lanes from left to right are as follows: A, G are sequencing lanes; K, unmodified 30S subunit; 30S, 30S subunits exposed to hydroxyl radicals. Subsequent lanes are initiation factor-30S complexes (as labeled) exposed to hydroxyl radicals. Bars at the right of each autoradiogram indicate regions of protection. (B) 1173-dependent protection of 16S rRNA in 30S subunits from free hydroxyl radicals mapped onto the secondary structure of 16S rRNA. Dot sizes indicated the extent of protection.

To further define the IF3 binding site, we monitored the protection of the 16S rRNA (SEQ ID NO: 45) sugar-phosphate backbone from hydroxyl radicals generated in solution with free Fe(II)-EDTA in the presence of bound IF3. Since susceptibility of the RNA backbone to hydroxyl radical attack is independent of secondary structure, these data are complementary to protection from chemical probes that specifically modify unpaired base moieties of the RNA. Protection was monitored by primer extension and classified by visual inspection of the autoradiograms (FIGS. 16A and 16B).

Protected nucleotides are clustered in helices 23 and 24 of the central domain of 16S rRNA, which are located at the subunit interface as described above. In helix 23, nucleotides 685–688 and 693–703 are protected (FIG. 16B); in addition, an extensive footprint is observed in helix 24 at positions 774–776, 783–793, 799–802, and 807–810 (FIG. 16A). These nucleotides surround the bases G700, U701, G703, G791, and U793, which are protected by IF3 from attack by kethoxal and CMCT (Muralikrishna et al. 1989; Moazed et al. 1995). The protected nucleotides in helix 24 are staggered in the 3'-direction, suggesting that IF3 interacts with the minor groove of the RNA helix at these positions. The IF3-dependent protection pattern is unchanged when IF1 and IF2 are also present in the 30S complex, except that some of the nucleotides around position 775 appear more strongly protected, indicating that the binding of IF3 is similar in the presence or absence of the other initiation factors (FIG. 16A).

Directed Hydroxyl Radical Probing Experiments of IF3–30S Complexes

Figure 15:
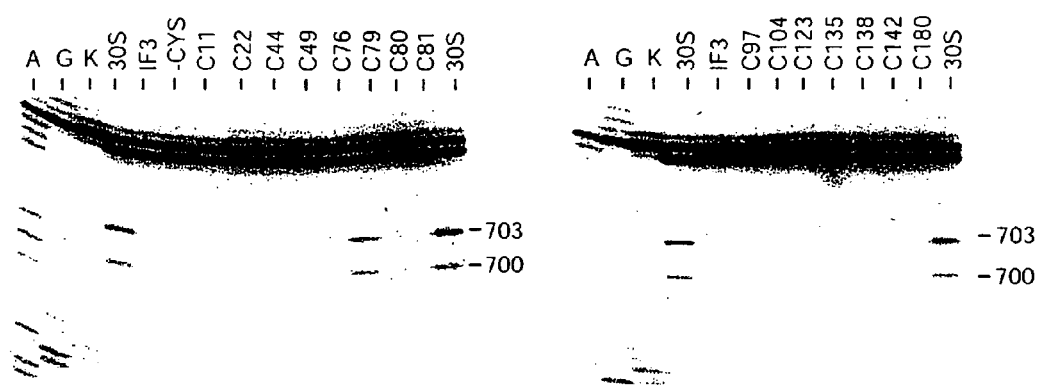
FIG. 15. Chemical footprinting of Fe(II)-derivatized IF3 variants on 16S rRNA. Primer extension showing the kethoxal footprint of IF3-HisTag (wild-type) and Fe(II) BABE-derivatized IF3 variants at positions G700 and G703 on 16S rRNA in the 30S subunit. In both panels, A and G are sequencing lanes. Lanes labeled K and 30S are unmodified 30S subunits and kethoxal-modified 30S subunits, respectively. IF3 is kethoxal-modified 30S-IF3-His6 complex (6×His tag disclosed as SEQ ID NO: 125). In the left panel -cys is kethoxal-modified cysteine-free IF3-30S and all other lanes are kethoxal-modified N-domain Fe(II)-IF3-30S complexes as indicated at the top of each lane. In the right panel, all other lanes are C-domain Fe(II)-IF3-30S complex treated with kethoxal as indicated.
Figure 17:
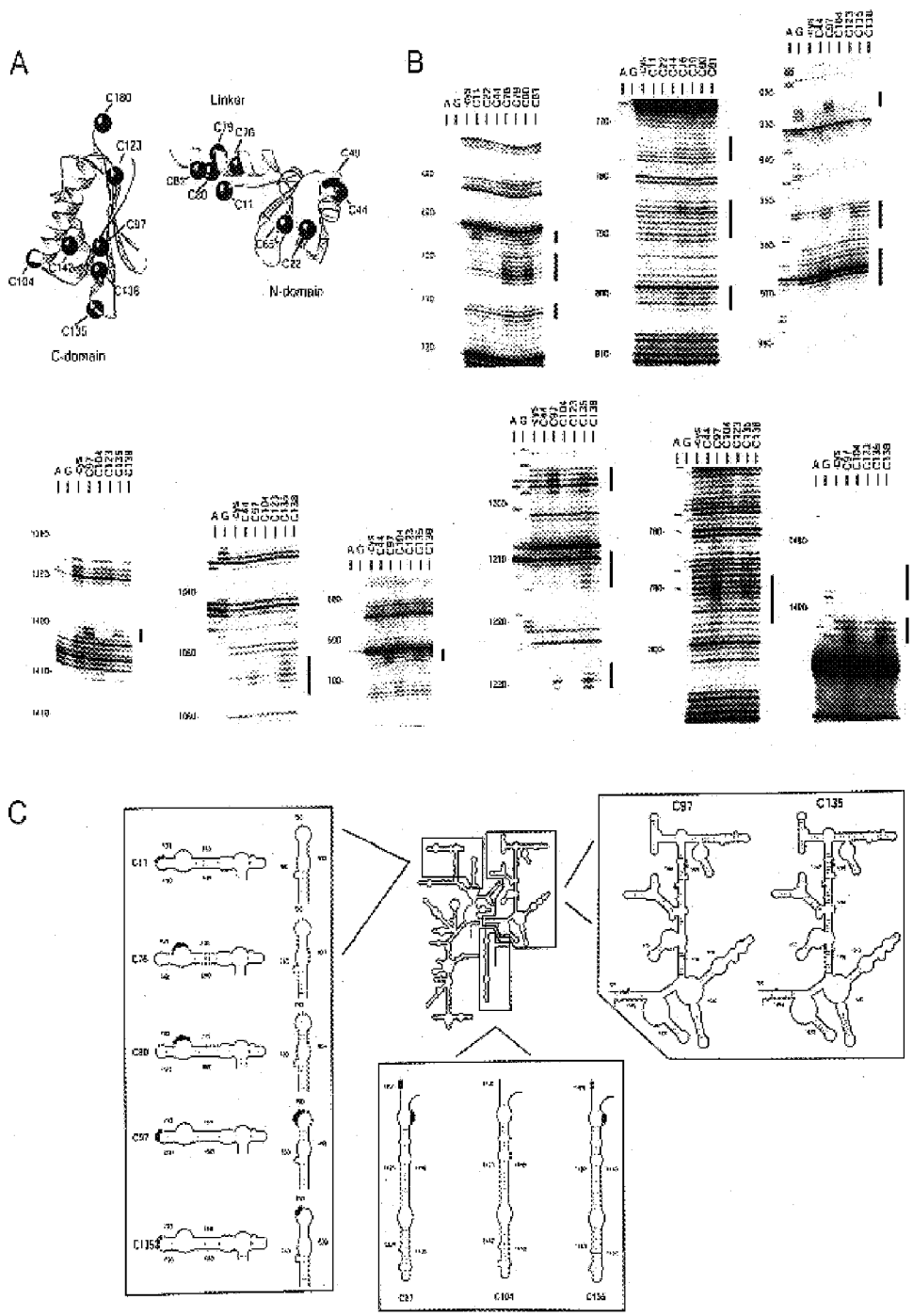
FIG. 17. Directed hydroxyl radical probing of 16S rRNA from different positions on the surface of IF3. (A) Ribbon diagrams of the crystal structures of the N- and C-domains of IF3 from *Bacillus stearothermophilus* (Biou et al. 1995). Spheres indicate the Cα positions of engineered cysteine residues used to tether Fe(II), numbered according to the corresponding residue in *Escherichia coli*. (B) Directed hydroxyl radical cleavage of 16S rRNA in 30S subunits from Fe(II)-IF3 detected by primer extension analysis. A and G are sequencing lanes. All other lanes are 30S-IF3 complexes that were probed with Fe(II) tethered to a different IF3 position, as indicated, including a cysteine-free control reaction (–cys). Labels at the left of each autoradiogram indicate the sequence of 16S rRNA. Bars at the right of each panel indicate regions of cleavage by hydroxyl radicals. (C) Summary of the location of hydroxyl radical cleavages in the central, the 3'-major, and the 3'-minor domains of 16S rRNA (shaded gray, clockwise from left) from Fe(II)-IF3 bound to 30S subunits. Cleavage strengths, assigned as strong, medium, or weak, are proportional to the size of the filled circles.

After over-expressing, purifying, and Fe(II) BABE-derivatizing cysteine-free and single-cysteine-containing IF3 variants, we tested the ability of these derivatized proteins to bind normally to 30S subunits and to promote dissociation of ribosomes. FIG. 15 shows that all of the proteins were able to protect nucleotides G700 and G703 from kethoxal modification with the exception of the Fe-C79 construct. Likewise, all except Fe-C79 were able to dissociate ribosomes into subunits as judged by sedimentation analysis (data not shown). Therefore, Fe-C79 was excluded from subsequent probing experiments. The positions of derivatization of IF3 with Fe(II)-BABE are shown in FIG. 17A.

Directed hydroxyl radical probing of Fe(II)-IF3–30S complexes was performed and scored as described in the Experimental Procedures. While the footprint is tightly localized to the 690 and 790 stem-loops in the platform, hydroxyl radicals generated from Fe(II) tethered to six of the 15 positions tested cleave three of the four domains of 16S rRNA (FIGS. 17B and 17C). Although the cleavage targets are widely distributed in the secondary structure, they are localized to an area that lines the cleft, including elements of the platform, penultimate stem, and head of the 30S subunit.

When hydroxyl radicals are generated from Fe(II) tethered to the C-terminal half of IF3, the most intense cleavages occur in the 790 loop and in the top of the penultimate stem at the subunit interface. Hydroxyl radicals generated from Fe(II) tethered to position 97, in the first (β-strand of the C-domain, and to a lesser extent position 135, in the loop connecting (β-strand 2 and α-helix 2, cleave 16S rRNA in the 690 and 790 loops and nucleotides in the 925, 1228, 1338, and 1400 regions. These features of 16S rRNA surround the P site (Moazed et al. 1990; Yusupov et al. 2001; see above). These two probing positions also cleave nucleotides at the top of the penultimate stem near the decoding site. Fe(II) tethered to position 104, at the beginning of the helix 1 of the C-domain, weakly cleaves residues 1482–1487 in the penultimate stem (FIGS. 17B and 17C).

The 690 and 790 stem-loops are also cleaved by Fe(II) tethered to positions 76 and 80 in the helical linker. The patterns of cleavage from these two probing sites are almost identical, producing their strongest hits at nucleotides 699–705 (FIG. 17B). In the globular portion of the N-domain, only the probe tethered to position 11 cleaved 16S rRNA, at the apex of the 690 loop (FIG. 17B). In the crystal structure of the N-domain of IF3 from *Bacillus stearothermophilus*, the residue that corresponds to *E. coli* position 11 resides in an extended loop that runs parallel to the linker region between the N- and C-domains. Thus, this residue, while at the N-terminus of IF3, is actually directed toward the C-domain (FIG. 17A). Probes at positions 22, 44, 49, and 65 fail to cleave 16S rRNA.

Directed Hydroxyl Radical Probing of Initiator tRNA Bound to the 30S P Site

Figure 18:
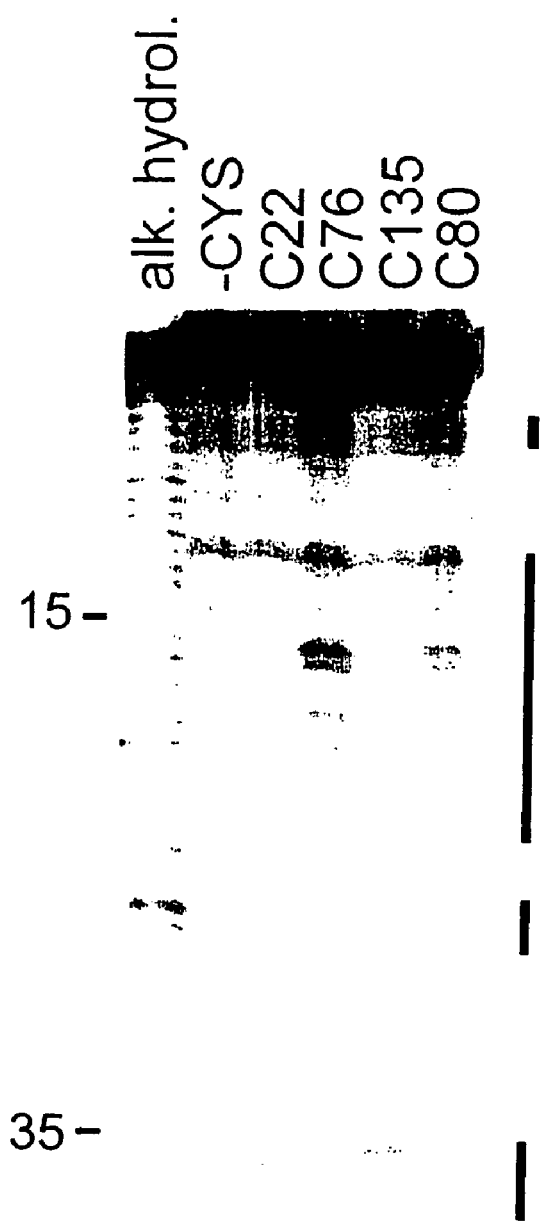
FIG. 18. Directed hydroxyl radical probing of initiator tRNA from different positions on IF3. (A) Autoradiograph of 5'-end-labeled tRNAMetf showing cleavage by hydroxyl radicals generated from Fe(II) IF3. Lanes are labeled according to the site of attachment of Fe(II)-BABE to IF3. Cleavages are indicated by bars at the right side of the gel.

To constrain the orientation of IF3 with respect to P site-bound initiator tRNA, cleavage of the tRNA backbone was examined by directed probing of 30S subunit complexes containing $^{32}$P-end-labeled initiator tRNA, mRNA, and Fe(II)-IF3. Three of the tethered Fe(II)-IF3 probes cleave the backbone of initiator tRNA bound to the 30S subunit P site, at characteristically different positions (FIG. 18). The probe at position 135 cleaves nucleotides 26–29 and 35–37 at the junction between the anticodon stem and the D stem and the anticodon of the initiator tRNA, respectively. The probes at positions 76 and 80 cleave the tRNA$^{Met}_f$ at nucleotides 3–5 and 13–24 in the D loop. The C-domain probe (135) and the linker probes (76 and 80) cleave nucleotides on opposite faces of the tRNA, indicating that the two domains of IF3 are positioned on opposite sides of the tRNA.

Modeling the IF3–30S Subunit Interaction

We modeled the position and orientation of IF3 to maximally satisfy the biochemical constraints from directed hydroxyl probing and footprinting in the context of the three-dimensional structure of the 30S subunit. While the probing and footprinting experiments were performed with full-length IF3, each domain of IF3 was modeled individually, since the structures of the N- and C-domains were solved separately.

The strongest cleavages using Fe-BABE-derivatized IF3 are from Fe-C97 at the top of the 790 loop and the top of the penultimate stem, clearly indicating the proximity of the C-domain to this region of 16S rRNA and to the interface side of the 30S subunit. Accordingly, we have modeled the C-domain bound directly to the interface surface of the platform of the 30S subunit, effectively covering the hydroxyl radical footprint of IF3 on 16S rRNA (FIG. 19). This interpretation is supported by analysis of the recent crystal structures of the ribosome (Wimberly et al. 2000; Yusupov et al. 2001; see above), which show that the overwhelming majority of hydroxyl radical footprints of the small subunit proteins on 16S rRNA (Powers et al. 1995)

reflect direct protein-rRNA interaction rather than indirect protection induced by conformational changes.

The Fe-C97 and Fe-C135 probes cleave nucleotides in the head of the 30S subunit with medium to weak intensity, and so we have oriented these residues in the C-domain to face across the cleft toward the head in the direction of the 30S A site (FIG. 19C). The orientation and position of the C-domain of IF3 were further constrained by avoidance of steric clash with the P-site-bound tRNA that is present in the 5.5Å ribosome structure. In this orientation, α-helix 1 of the C-domain interacts with the minor groove of 16S rRNA helix 24. Mutation of lysine-110 to leucine in a-helix 1 virtually abolishes binding of IF3 to 30S subunits, consistent with our placement (De Bellis et al. 1992).

A consequence of this orientation of the C-domain is that residue M135 of the C-domain faces the anticodon loop of P site-bound tRNA, consistent with the observed cleavage of the initiator tRNA anticodon by Fe-C 135. Although this orientation of the C-domain of IF3 maximizes agreement with the cleavage data, the distances between some of the probing positions and their targets in the 3' major domain are nevertheless, farther than predicted from their cleavage intensities, as discussed below.

The N-terminal half of IF3 contains the highly conserved linker region that is rich in basic and aromatic residues. Since the cleavage data from this half of the factor are dominated by hits coming from the linker region, our first step in docking the N-terminal half of IF3 was to position the linker. Probes in the linker region cleave the middle and lower portions of the 690- and 790-stems, and so it was modeled as spanning this region of the platform (FIG. 19C).

Placement of the globular portion of the N-domain is less certain since most of the probes from that domain failed to cleave 16S rRNA. The position shown in FIG. 19C, largely constrained by the position of the linker, is consistent with the cleavages that were obtained from position 11, the lone N-terminal probing site that cleaved 16S rRNA. This arrangement wedges the globular portion of the N-domain between ribosomal proteins S7 (SEQ ID NO: 30) and S11 (SEQ ID NO: 34), both of which have been crosslinked to IF3 (MacKeen et al. 1980; Boileau et al. 1983). Placement of the N-domain in a protein-rich environment accounts for the absence of hits from the N-terminal probes at positions 22, 44, 49, and 65, although this was not explicitly used as a modeling constraint.

Whereas IF1 overlaps the A site of the 30S subunit during initiation, in our model the N- and C-domains of IF3 lie on opposite faces of the initiator tRNA (FIGS. 20A and 20B), placing the N-domain at the E site. Additional support for this arrangement comes from cleavage of the D loop of initiator tRNA from Fe(II) tethered to position 76 in the linker region of IF3 (FIG. 20B). Solution scattering studies indicate that the two domains of IF3 do not interact with one another (Kycia et al. 1995), in agreement with our findings, which also support an extended conformation for IF3. A caveat is that we cannot say how our model would be affected by conformational changes that may occur in IF3 or in the 30S subunit when they interact, such as the ones observed in a cryo-EM study (McCutcheon et al. 1999).

Discussion

In our model, the C-domain of IF3 interacts with helices 23, 24, and 45 at the interface surface of the platform, a placement that is supported by extensive biochemical and biophysical studies. Immunoelectron microscopy localized IF3 on the interface surface of the 30S subunit (Stöffler and Stöffler-Meilicke, 1984). Nucleotides G700, U701, G703, G791, and U793, which are located at the interface of the small subunit, are protected from kethoxal and CMCT modification (Muralikrishna and Wickstrom, 1989; Moazed et al. 1995). Additionally, mutation of G791 to A reduces the binding affinity of IF3 for the 30S subunit by ten-fold (Tapprich et al. 1989). A crosslink between helix 45 and IF3 is also in agreement with contact between helix 45 and the C-domain in our model (Ehresmann et al. 1986). In another study, binding of IF3 to the 30S subunit interrupted an intramolecular crosslink between U793 (in helix 24) and G1517 (in helix 45) (Shapkina et al. 2000). A recent cryo-EM study of IF3 with the 30S subunit identified electron density of the same dimensions as the C-domain at the interface side of the platform (McCutcheon et al. 1999). In addition, a deletion mutant of IF3 that contains only the C-domain produces a hydroxyl radical footprint on helices 23 and 24 that is identical to that of full-length IF3 (A. D. and HEN., unpublished results).

While our positioning of the C-domain agrees with the 27 Å cryo-EM study (McCutcheon et al. 1999), positioning of the N-domain differs. In the cryo-EM study, three regions of positive difference density and one region of negative difference density were identified. The N-domain was fit into the positive difference density that spanned from the platform to the neck of the 30S subunit, while the remaining difference density was attributed to conformational changes that occurred upon IF3 binding. Our data more closely fit location of the N-domain at the unassigned region of positive density that is contiguous with the platform. We would then ascribe the remaining lobes of positive and negative difference density to a conformational change in the 30S subunit in which the head of the 30S subunit pivots from the direction of the A site toward the P site. This movement would bring some of the nucleotides cleaved in the head closer to the C-domain, helping to reconcile the discrepancy between the observed intensities of the cleavages and the probe-target distances from positions Fe-C97 and Fe-C135.

While our model for IF3 is in agreement with the cryo-EM data, our position for the C-domain of IF3 differs substantially from a recently reported analysis of crystals of 30S subunits that were soaked with the C-domain of IF3 (Pioletti et al. 2001). Pioletti et al. place the C-domain on the opposite surface of the 30S subunit, interacting with the solvent face of helix 23 as well as helix 26. Neither our footprinting data nor our directed probing data can be reconciled with this placement of the C-domain. This discrepancy can be explained by the fact that the interface surface of the platform, which we propose is the binding site for the C-domain, coincides with crystal contacts in the Tth 30S crystals (Schluenzen et al. 2000; Wimberly et al. 2000). In fact, this is the same region where the "spur" helix from the body of a neighboring 30S subunit binds to the P site, mimicking a tRNA anticodon stem-loop (Carter et al. 2000). Thus, we would expect that the C-domain of IF3 would be unable to bind to the location that we have proposed without disrupting the crystal packing. Given the documented propensity of IF3 for non specific binding (Sabol and Ochoa, 1974; Wickstrom, 1981) and in light of the abundant biochemical and biophysical evidence that IF3 interacts at the interface of the 30S subunit, it is possible that what was observed in the crystallographic study represents a secondary binding site.

Our model offers an explanation for the dissociation activity of IF3 in translation initiation. There is significant overlap between nucleotides protected by IF3 and those that are protected upon formation of the 70S ribosome (Merryman et al. 1999). Although the mass of IF3 is less than two percent of the mass of the 50S subunit, it would prevent access of 50S subunits to an extensive area comprising the intersubunit bridges B2b, B2c, and B7a (Cate et al. 1999; Yusupov et al. 2001; see above), consistent with proposals by McCutcheon et al. (1999) and Gualerzi et al. (2000). The position of the C-domain of IF3 coincides with that of helix 69 of 23S rRNA (SEQ ID NO: 23), the main large subunit component of bridge B2b (Yusupov et al. 2001; see above) (FIG. 20). Thus, IF3 may prevent subunit association by mimicking this 23S rRNA helix. That the isolated C-domain is itself capable of promoting subunit dissociation (Garcia et al. 1995b) and footprints the contact site of helix 69 supports this scheme. This mechanism contrasts with that of Pioletti et al, who propose that IF3 indirectly affects subunit interaction, despite the fact that they do not report any structural changes in the 16S rRNA regions involved in inter-subunit contact (Pioletti et al. 2001).

Our model also constrains the possible ways in which IF3 may promote initiator tRNA selection (Risuleo et al. 1976; Hartz et al 1989). It has been shown that the main discriminatory feature of the initiator tRNA is a series of three conserved G-C base pairs (nucleotides 29–31 and 39–41) adjacent to the anticodon loop, reviewed in (Mangroo et al. 1995). According to our model, IF3 would be out of reach of this feature of tRNA, suggesting that its role in promoting tRNA discrimination is indirect. In the co-crystal structure of the 70S ribosome bound with initiator tRNA, nucleotides G1338 and A1339 in the head of the 30S subunit are juxtaposed with the minor groove surface of exactly this region of the anticodon stem of initiator tRNA (Yusupov et al. 2001; see above). A possible mechanism is that the proposed IF3-dependent tilting of the head toward the platform inferred from the cryo-EM study moves these two bases of 16S rRNA into intimate contact with the minor groove of the anticodon stem of tRNAM"f, where they may perform a steric check of the tRNA identity. Such a scheme would be analogous to the mechanism proposed by Ogle and colleagues for aminoacyl-tRNA discrimination, which involves minor groove recognition (Ogle et al. 2001).

Several studies have suggested that the mRNA rearranges on the 30S subunit when initiation factors are present (Canonaco et al. 1989; La Teana et al. 1995). Interestingly, the position of the 3'-end of 16S rRNA differs between the crystal structure of the isolated 30S subunit and that of the 70S ribosome with P site tRNA and mRNA bound (Carter et al. 2000; Wimberly et al. 2000; Yusupov et al. 2001; see above). Interaction of IF3 with the 3' terminal stem-loop of 16S rRNA could promote movement of the 3' end of 16S rRNA out of the P and E sites as observed in the 30S crystal structure to make it available for binding the Shine-Dalgarno sequence of the mRNA.

Finally, there is steric clash between the position of the N-domain of IF3 and that of E-tRNA. Thus, an additional role of IF3 could be to exclude tRNA from the 30S E site during initiation. Since IF3 has been crosslinked to IF2 (Boileau et al. 1983) and IF2 also promotes the selection of initiator tRNA, it is possible that the N-domain of IF3 might interact with IF2 prior to joining with the 50S subunit. The availability of extensive structural information for the ribosome and its ligands now makes it possible to directly test these and other proposals for the mechanisms of IF3 activity during initiation.

EXAMPLE 4

Target Site Selection for 70S Ribosome

The structure coordinates of the 70S ribosome, or portions thereof are useful for designing structural features of the 70S ribosome that can be targeted to inhibit or activate ribosome function. The following regions of the 70S ribosome, defined by the structure coordinates, represent particularly useful targets for the development of inhibitory or activating compounds.

One approach to developing inhibitors or activators specific to prokaryotic ribosome target sites is to select target regions based on phylogenetically diverse regions found in the primary structures of prokaryotic and eukaryotic ribosome components and to determine, by way of mapping these regions onto the instant 5.5A 70S structure, which phylogenetically diverse regions are contained in parts of the ribosome likely to disrupt ribosome function when perturbed. Phylogenetically diverse regions can be located in the primary structures of these components by going to a protein or a nucleic acid sequence database and carrying out sequence comparisons between related sequences from different organisms using well-known sequence alignment tools such as BLAST. Carl Woese of the University of Illinois has compiled such sequence comparisons as part of a ribosomal database project (www.cme.msu.edu/RDP/html/index.html). Such databases are useful to locate non-conserved regions of 23S, L2, L5, L14, and L19, 16S,S13, and S15. Representative alignments are set forth in Table I.

Of course, there are instances in which prokaryotic or eukaryotic specificity is not needed. In such instances, a phylogenetically diverse region need not be identified.

Interface interactions provide structure regions useful for pharmacophore or candidate compound design of agents that disrupt or enhance the strength of interaction between the 30S and 50S subunits. By comparing the Ban et al. 2000 2.4 Angstrom 50S structure to the instant 50S structure, differences between the two are readily determined that provide clues as to the conformational changes occurring in the 50S structure upon binding to the 70S subunit. These conformational differences are described above. Several approaches for target selection may be used.

One approach is to target interface or bridge regions while the subunits are apart. The other is to target regions accessible to small molecules when the subunits are together.

Ribosomes exist within an organism as dissociated 30S and 50S subunits that come together during protein translation and then again separate at the end of the translation process. Any and all bridge regions are good targets for disrupting the association between 30S and 50S. Especially good targets are those found in the aforementioned phylogenetically different regions of 50S ribosome structure as between host and pathogen. These regions can be readily deduced by sequence comparisons among different rRNAS contained within 50S (interface components of 50S contain parts of 23S rRNA and parts of ribosomal proteins L2, L5, L14, and L19). 30S bridge component are comprised of 16S rRNA and parts of proteins S13 and S15. The regions of the structure involved in making bridge contacts between the subunits are set forth in Table III.

Regions of the 70S ribosome involved in binding the A site, P site, and E site tRNAs, as set forth in Table IV also may be used in target site selection.

Regions of the 70S ribosome that contact the mRNA also provide potential target sites for developing pharmacophores and candidate compounds to affect protein translation. These include those elements of the structure containing protein S3 residues 156–163; 127–132; protein S4 residues 47–52; protein S5 residues 9–30 and 46–56; 16S rRNA residues 13–17; 528–532; 1194–1198; and 1054–1056.

The Shine-Dalgamo helix (formed between the −10 region of mRNA and the 3'-terminus of 16S rRNA during initiation of translation), is absent in both cytoplasmic and mitochondrial human ribosomes, but is present in all pathogens (such as bacteria). The portion of the 16S rRNA that forms the Shine Dalgamo helix portion, as described above, therefore provides a good target site. Upon binding of mRNA a conformational shift occurs in the 30S portion of the ribosome structure. The tail of the 16S rRNA base pairs with the Shine Dalgamo sequence of the mRNA, and that helix then binds to a Shine Dalgarno binding pocket on the solvent side of the "platform" of the 30S ribosome subunit. We compared our 70S structure to the isolated 30S structure (Wimberly, et al. 2000; PDB id 1FJF) to locate the Shine Dalgarno binding pocket. The pocket also provides a target site, and is defined by regions of the structure containing the following elements: protein S11, residues 85–90; 112–129; 22–27; protein S18, residues 1–24; 16S helix 20, helix 28, helix 37, helix 45 and bulge loop 723 (including 16S residues 927–931; 1388–1393; 1526–1529; 1505–1508; and 719–724).

Additional target sites include binding sites for ribosome binding factors such as IF3, the docking of which is described above, the binding sites of EF-Tu and EF-G, and regions of the 50S subunit implicated in the GTPase and factor-related functions. These include the SRL (sarcin ricin loop, see FIG. 2 and L11). These two sites interact with EF-Tu and EF-G. Structures of EF-Tu are reported by Kjeldgaard, et al. *Structure* 15, 35 (1993) (PDB 1EFT, 847, ITTT; 5401, ITUI; 6200, IEFC; 9879) and by Czworkowski et al. *EMBO J* 13, 3661 (PDB IEFG; 845, IDAR; 4586, IELO; 4920, 2EFG; 12085, IFNM; 14532, and by Liljas (al-Karadaghi, et al. *Structure* 4, 555 (PDB 2EFG; 12085, 1FNM; 14532. )

We have docked these structures, using the techniques described above to the 70S structure based on the following criteria: (1) steric fit of EF-G to 70S; (2) footprinting of these factors onto 23S RNA (Moazed et al. 1988); and directed hydroxyl radical probing (Wilson et al., 'Mapping the position of translational elongation factor EF-G in the ribosome by directed hydroxyl radical probing.' *Cell* (1998) 92(1): 131–9). Based on the novel 70S structure and known high resolution structures of the elongation factors and the additional information detailed above EF-Tu and EF-G can be accurately docked into the 70S structure to provide a template for designing small molecules that will interfere with the ribosomal GTPase activity and consequently protein synthesis.

Our docking studies indicate the EF-Tu contacts to be on 23S rRNA residues 2651–2665, 16S rRNA residues 54–57, and 357–361, and L11 residues 20–36. The EF-G contacts are found at 23S rRNA residues 1065–1069, 1094–1097, and 2651–2665, 16S rRNA residues 54–57, 340–345 and 357–361 and at L11 residues 20–36.

Accurate docking of EF-Tu and EF-G was not possible with prior art ribosome structures such as the 50S Ban et al. (2000) structure which resolves the SRL loop but not L11, which is disordered in the 50S structure. L11 density is observable in the instant 5.5 Å structure and high resolution geometry can be deduced according to the fitting methods using high resolution structure of L11 and L11 RNA (Conn G L, Draper D E, Lattman E E, Gittis A G. *Science. May* 14, 1999;284(5417): 1171–4. (1QA6; 10294) and Wimberly B T, Guymon R, McCutcheon J P, White S W, Ramakrishnan V. *Cell*. May 14, 1999;97(4):491–502. (1EG0; 12626, IMMS; 13236, 487D; 13285) complex fit into the density as described above, and is modeled in the instant structure.

In practice we used the Ramakrishnan L11 structure referenced above to carry out the docking of L11 into the 5.5 Angstrom 70 S structure. Given this newly identified or solved aspect of the 70S ribosome structure and the docking algorithms described above, one of ordinary skill may readily deduce target sites and pharmacophores enabling the preparation of small molecules and other agents that can interfere with the binding of EF-Tu and or EF-G to the ribosome. Such agents are expected to inhibit protein synthesis by inhibiting the ribosome-associated GTPase activity. Antibiotics such as thiostrepton, and micrococcin act at the L11 protein to inhibit protein synthesis. Porse B T, Cundliffe E, Garrett R A. 'The antibiotic micrococcin acts on protein L11 at the ribosomal GTPase centre.'*J Mol Biol*. March 19;287(1):33–45 (1999); *Biochimie*. July-August;73 (7–8):1131–5 (1991). These antibiotics can be used as templates to dock onto the 70S structure we have determined, to provide additional information from which other pharmacophores or candidate compounds can be designed to target the L11 region and inhibit the GTPase activity. In this way novel agents can be discovered that will prevent binding of factor(s) to the site.

In addition there are compounds that bind to the elongation factors (as fusidic acid that binds to EF-G) that do not inhibit GTPase but prevents release of EF-G and so it remains bound and block translation by preventing extension of the nascent polypeptide chain. Laurberg M, Kristensen O, Martemyanov K, Gudkov A T, Nagaev I, Hughes D, Liljas A. Structure of a mutant EF-G reveals domain III and possibly the fusidic acid binding site. *J Mol Biol*.

November 3;303(4):593–603 (2000) (1FNM; 14532) These compounds also can be docked into the 70S 5.5 Angstrom structure to design other molecules that will act in a similar manner as fusidic acid to inhibit EF-G release.

Yet other classes of agents can be docked into the 70S 5.5 Angstrom structure for pharmacophore or candidate compound design. For example the GTPase related drug "kirromycin" binds to EF-Tu and prevents conformational change that allows EF-Tu to release from the ribosome and release tRNA.

REFERENCES

Agrawal, R. K., et al., (1996) *Science* 271: 1000–1002.

Agrawal, R. K., et al., (1999a) *Curr. Opin. Struct. Biol.* 9: 215.

Agrawal, R. K., et al., (1999b) EF-G-dependent GTP hydrolysis induces translocation accompanied by large conformational changes in the 70S ribosome. *Nat. Struct. Biol.* 6: 643–7.

Agrawal, R. K., et al., (2000) Visualization of tRNA movements on the *Escherichia coli* 70S ribosome during the elongation cycle. *J. Cell Biol.* 150: 447–60.

Ahsen, U. v., et al., (1995) *Science* 267: 234–237.

Alam, S. L., et al., (1999) Programmed ribosomal frameshifting: much ado about knotting! *Proc. Natl. Acad. Sci. USA* 96: 14177–9.

Balakin, A., et al., (1990) Transition of the mRNA sequence downstream from the initiation codon into a single-stranded conformation is strongly promoted by binding of the initiator tRNA, *Biochim. Biophys. Acta.* 1050: 119–23.

Ban, N., et al., (1998) *Cell* 93: 1105–1115.

Ban, N., et al., (1999) *Nature* 400: 841–847.

Ban, N., et al., (2000) The complete atomic structure of the large ribosomal subunit at 2.4 A resolution, *Science* 289: 905–20.

Barta, A., (1984) *Proc. Natl. Acad. Sci. USA* 81: 3607–3611.

Belitsina, N. V., et al., (1981) Template-free ribosomal synthesis of polylysine from lysyl-tRNA, *FEBS Lett.* 131: 289–92.

Bhangu, R., et al., (1994) Arrangement of messenger RNA on *Escherichia coli* ribosomes with respect to 10 16S rRNA cross-linking sites, *Biochemistry* 33: 3063–3070.

Bhangu, R., et al., (1992) The mRNA binding track in the *Escherichia coli* ribosome for mRNAs of different sequences, *Biochemistry* 31: 5937–5944.

Biou, V., et al., (1995). X-ray crystallography shows that translational initiation factor IF3 consists of two compact alpha/beta domains linked by an alpha-helix, *Embo J* 14,4056–64.

Boileau, G. et al., (1983). Direct cross-links between initiation factors 1, 2, and 3 and ribosomal proteins promoted by 2-iminothiolane, *Biochemistry* 22, 3162–70.

Bretscher, M. S. (1968) Direct translation of a circular messenger DNA, *Nature* 220: 1088–91.

Brierley, I., et al., (1989) Characterization of an efficient coronavirus ribosomal frameshifting signal: requirement for an RNA pseudoknot, *Cell,* 57:537–47.

Brimacombe, R., et al., (1988) *J. Mol. Biol.* 199:115–36.

Brimacombe, R. (1995) The structure of ribosomal mRNA: a three-dimensional jigsaw puzzle, *European JouRNAl of Biochem.* 230: 365–383.

Brosius, J., et al., (1980) *Proc. Natl. Acad. Sci. USA* 77: 201–4.

Brunger, A. T., et al., (1998) Crystallography & NMR system: A new software suite for macromolecular structure determination, *Acta. Crystallogr. D. Biol. Crystallogr.* 54: 905–21.

Canonaco, M. A., et al., (1986). Mechanism of translational initiation in prokaryotes. Evidence for a direct effect of IF2 on the activity of the 30 S ribosomal subunit, *FEBS Lett* 207:198–204.

Canonaco, M. A., et al, (1989). Alternative occupancy of a dual ribosomal binding site by mRNA affected by translation initiation factors, *Eur J Biochem* 182: 501–6.

Capel, M. S., et al., (1987) *Science* 238: 1403–6.

Carson, M. (1997) Ribbons, *Methods Enzymol.* 277B: 493–505.

Carter, A. P., et al., (2001). Crystal structure of an initiation factor bound to the 30S ribosomal subunit, *Science* 291, 498–501.

Carter, A. P., et al., (2000). Functional insights from the structure of the 30S ribosomal subunit and its interactions with antibiotics, *Nature* 407, 340–8.

Cate, J. H., et al., (1999). X-ray crystal structures of 70S ribosome functional complexes, *Science* 285, 2095–104.

Clemons, W. M., et al., (1999) *Nature* 400: 833–840.

Cooperman, B. S., et al., (1977). Photosensitized crosslinking of IF-3 to *Escherichia coli* 30 S subunits, *FEBS Lett* 76: 59–63.

Cooperman, B. S., et al., (1981). IF-3 crosslinking to *Escherichia coli* ribosomal 30 S subunits by three different light-dependent procedures: identification of 30 S proteins crosslinked to IF-3-utilization of a new two-stage crosslinking reagent, p-nitrobenzylmaleimide, *FEBS Lett* 208: 554–62

Correll, C. C., et al., (1997) *Cell* 91, 705.

Crick, F. H. (1968) The origin of the genetic code, *J. Mol. Biol.* 38: 367–79.

Culver, G. M., et al., (1999) *Science* 285: 2133–6.

Culver, G. M., et al., (2000). Directed hydroxyl radical probing of RNA from iron(II) tethered to proteins in ribonucleoprotein complexes, *Methods Enzymol* 318: 461–75.

Czworkowski, J., et al., (1994) The crystal structure of elongation factor G complexed with GDP, at 2.7 A resolution. *Embo. J.* 13: 36618.

Dallas, A., et al., (1997) *Structure* 5: 1639.

De Bellis, D., et al., (1992) Structure-function analysis of *Escherichia coli* translation initiation factor IF3: tyrosine 107 and lysine 110 are required for ribosome binding, *Biochemistry* 31: 11984–90.

Dokudovskaya, S. S., et al., (1993) mRNA-ribosome interactions, *Biotechnol. Appl. Biochem.* 18: 149–55.

Dontsova, O., et al., (1992) Three widely separated positions in the 16S RNA lie in or close to the ribosomal decoding region; a site-directed cross-linking study with mRNA analogues, *EMBO J* 11: 3105–3116.

Döring, T. et al., (1994) *EMBO J* 13: 2677–2685.

Ehresmann. C., et al., (1986). Cross-linking of initiation factor IF3 to *Escherichia coli* 30S ribosomal subunit by trans-diamminedichloro latinum(II): characterization of two cross linking sites in 16S rRNA: a possible wave of functioning for IF3. *Nucleic Acids Research* 14: 4803–4821.

Feinberg, J., et al., (2001) Identification of molecular interactions between P site tRNA and the ribosome essential for translocation, *Proc. Nat. Acad. Sci.* 20: 11120–5.

Fourmy, D., (1996) *Science* 274: 1367–71.

Frank, J., et al., (1995a) A model of protein synthesis based on cryo-electron microscopy of the *E. coli* ribosome, *Nature* 376: 441–444.

Frank, J., et al., (1995b) A model of the translational apparatus based on a three-dimensional reconstruction of the *Escherichia coli* ribosome, *Biochem. Cell. Biol.* 73: 757–65.

Frank, J., et al., (2000) *Nature* 406: 318–22.

Gabashvili, I. S., et al., (2000) Solution structure of the *E. coli* 70S ribosome at 11.5 A resolution, *Cell* 100: 537–49.

Gabashvili, I. S., et al., (1999) *Embo. J.* 18: 6501–7.

Garcia, C., et al., (1995a). 1H and 15N resonance assignments and structure of the N-terminal domain of *Escherichia coli* initiation factor 3, *Eur J Biochem* 228, 395–402.

Garcia, C., et al., (1995b). Solution structure of the ribosome-binding domain of *E. coli* translation initiation factor IF3: homology with the UIA protein of the eukaryotic spliceosome, *J Mol Biol* 254, 247–59.

Gavnlova, L. P., et al., (1976) Factor-free ("non-enzymic") and factor-dependent systems of translation of polyuridylic acid by *Escherichia coli* ribosomes, *J. Mol. Biol.* 101: 537–52.

Gomez-Lorenzo, M. G., et al., (2000) Three-dimensional cryo-electron microscopy localization of EF2 in the *Saccharomyces cerevisiae* 80S ribosome at 17.5 A resolution, *Embo. J.* 19: 2710–8.

Gorini, L., (1971) Ribosomal discrimination of tRNAs. *Nature* 234: 261–264.

Green, R., et al., (1997) Ribosomes and Translation, *Annu. Rev. Biochem.* 66: 679–716.

Green, R., et al., (1998) Ribosome-catalyzed peptide-bond formation with an A-site substrate covalently linked to 23S ribosomal RNA, *Science* 280: 286–9.

Greuer, B., et al., (1999) The cross-link from the upstream region of mRNA to ribosomal protein S7 is located in the C-terminal peptide: experimental verification of a prediction from modeling studies. *RNA* 5: 1521–5.

Grunberg-Manago, M., et al., (1975). Light-scattering studies showing the effect of initiation factors on the reversible dissociation of *Escherichia coli* ribosomes, *J Mol Biol* 94, 461–78.

Gualerzi, C., et al., (1977) Initial rate kinetic analysis of the mechanism of initiation complex formation and the role of initiation factor IF-3, *Biochemistry* 16:1684–9.

Gualerzi, C. O., et al., (1990). Initiation of mRNA translation in prokaryotes, *Biochemistry* 29, 5881–9.

Gualerzi, C., et al., (2000). in The Ribosome: Structure, Function, Antibiotics, and Cellular Interactions; R. A. Garrett, et al., eds. (Washington D.C., ASM Press).

Guerrier-Takada, C., et al., (1983) The RNA moiety of ribonuclease P is the catalytic subunit of the enzyme, *Cell* 35: 849–857.

Gutell, R. R., et al., (1993) *Nucleic Acids Res.* 21: 3055–74.

Gutell, R. R., (1994) *Nucleic Acids Res.* 22: 3 502–7.

Hansen, H. A., et al., (1990) *Biochim. Biophys. Acta.* 1050: 1.

Hartz, D., et al., (1989). Selection of the initiator tRNA by *Escherichia coli* initiation factors, *Genes Dev* 3, 1899–912.

Hausner, T. P., et al., (1987) Evidence that the G2661 region of 23S rRNA is located at the ribosomal binding sites of both elongation factors, *Biochimie* 69: 911–23.

Herr, W., et al., (1979) Mechanism of ribosomal subunit association: discrimination of specific sites in 16 S RNA essential for association activity. *J. Mo. Biol.* 130: 433–49.

Hill, W. E. et al., Eds., (1990) The Ribosome: Structure, Function and Evolution, 123–33, *American Society for Microbiology*, Washington, D.C., .

Hirsh, D., (1971) *J. Mol. Biol.* 58: 439–58.

Huttenhofer, A., et al., (1994) Footprinting mRNA-ribosome complexes with chemical probes, *EMBO. J.* 13: 3892–3901.

Jones, T. A., et al., (1997) Electron-density map interpretation, *Methods Enzymol.* 277B: 173–208.

Joseph, S., et al., (1996) *EMBO. J.* 15: 910–16.

Joseph, S., et al., (1997). Mapping the inside of the ribosome with an RNA helical ruler, *Science* 278,1093–8.

Joseph, S., et al., (2000) *Methods Enzymol* 318: 175–90.

Juzumiene, D. I., et al., (1995) Distribution of cross-links between mRNA analogues and 16S rRNA in *Escherichia coli* 70S ribosomes made under equilibrium conditions and their response to tRNA binding, *J. Biol. Chem.* 270: 12794–12800.

Karimi, R., et al., (1999). Novel roles for classical factors at the interface between translation termination and initiation, *Mol Cell* 3, 601–9.

Kim, D. F., et al., (1999) *Mol. Cell* 4: 859–64.

Kruger, K., et al., (1982) Self-splicing RNA: Autoexcision and autocyclization of the ribosomal RNA intervening sequence of *Tetrahymena, Cell* 31: 147–157.

Kunkel, T. A., et al., (1987). Rapid and efficient site-specific mutagenesis without phenotypic selection, *Methods Enzymol* 154, 367–82.

Kurland, C. G., et al., (1990) in The Ribosome: structure, function, and evolution, W. E. Hill, Ed. *American Society of Microbiology*, Washington, D.C. 513–526.

Kycia, J. H., et al., (1995). Prokaryotic translation initiation factor IF3 is an elongated protein consisting of two crystallizable domains, *Biochemistry* 34, 6183–7.

Lake, J. A., ibid., 180–193.

Lata, K. R., et al., (1996) Three-dimensional reconstruction of the *Escherichia coli* 30S ribosomal subunit in ice. *J. Mol. Biol.* 262: 43–52.

La Teana, A., et al., (1995). From stand-by to decoding site. Adjustment of the mRNA on the 30S ribosomal subunit under the influence of the initiation factors, *RNA* 1, 772–82.

Lieberman, K. R., et al., (2000) *J. Mol. Biol.* 297: 1129–43.

Lill, R. et al., (1986) *Biochemistry* 25: 3245–55.

Lodmell, J. S., et al., (1997) *Science* 277:1262–1267.

MacKeen, L. A., et al., (1980). Photochemical crosslinking of initiation factor-3 to *Escherichia coli* 30 S ribosomal subunits, *J Biol Chem* 255, 10526–31.

Makowski, I., et al., (1987) *J. Mol. Biol.* 193: 819–22.

Malhotra, A., et al., (1998) *J. Mol. Biol.* 280.

Mandal, N., et al., (1996) Role of the three consecutive G.:C base pairs conserved in the anticodon stem of initiator tRNAs in initiation of protein synthesis in *Escherichia coli*, *RNA* 2: 47382.

Mangroo, D., et al., (1995). *Escherichia coli* initiator tRNA: structure-function relationships and interactions with the translational machinery, *Biochem. Cell Biol.* 73, 1023–31.

Matheson, A. T., et al., (1995) *Biochem. Cell Biol.* 73.

McCutcheon, J. P., et al., (1999). Location of translational initiation factor IF3 on the small ribosomal subunit, *Proc Natl Acad Sci* 96, 430–16.

Meinnel, T., et al., (1999). Discrimination by *Escherichia coli* initiation factor IF3 against initiation on noncanonical codons relies on complementarity rules, *J Mol Biol* 290, 825–37.

Merryman, C., et al., (1999a) Nucleotides in 23S rRNA protected by the association of 30S and 50S ribosomal subunts, *J. Mol. Biol.* 285: 107–13.

Merryman, C., et al., (1999b) Nucleotides in 16S rRNA protected by the association of 30S and 50S ribosomal subunits, *J. Mol. Biol.* 285: 97–105.

Mitchell, P. et al., (1992) *Biochemistry* 31: 3004–3011.

Moazed, D., et al., (1986a). Rapid chemical probing of conformation in 16 S ribosomal RNA and 30 S ribosomal subunits using primer extension, *J Mol Biol* 187,399–416.

Moazed, D., et al., (1986b) Transfer RNA shields specific nucleotides in 16S ribosomal RNA from attack by chemical probes, *Cell* 47: 985–994.

Moazed, D., et al., (1987) Interaction of antibiotics with functional sites in 16S ribosomal RNA, *Nature* 327: 389–394.

Moazed, D., et al, (1989a) *Cell* 57: 585–597.

Moazed, D., et al., (1989b) *Nature* 342: 142–148.

Moazed, D., et al., (1990). Binding of tRNA to the ribosomal A and P sites protects two distinct sets of nucleotides in 16 S rRNA, *J Mol Biol* 211, 135–45.

Moazed, D., et al., (1991) *Proc. Natl. Acad. Sci. USA* 88: 3725–3728.

Moazed, D., et al., (1995). Specific protection of 16 S rRNA by translational initiation factors, *J Mol Biol* 248, 207–10.

Monro, R. E., (1967) *J. Mol. Biol.* 26,147.

Moore, P. B., et al., (1998) *Annu. Rev. Biophys. Biomol. Struct.* 27, 35.

Moreau, M., et al., (1997). Heteronuclear NMR studies of *E. coli* translation initiation factor IF3. Evidence that the inter-domain region is disordered in solution, *J Mol Biol* 266,15–22.

Mougel, M., et al., (1987) *J. Mol. Biol.* 198: 91–107.

Mueller, F., et al., (1995) *Biochem. Cell Biochem.* 73: 767–773.

Muralikrishna, P., et al., (1989). *Escherichia coli* initiation factor 3 protein binding to 30S ribosomal subunits alters the accessibility of nucleotides within the conserved central region of 16S rRNA, *Biochemistry* 28, 7505–10.

Murgola, E. J., et al, (1988) Mutant 16S ribosomal RNA: a codon-specific translational suppressor, *Proc. Natl. Acad. Sci. USA* 85: 4162–5.

Nikonov, S. V., et al., (1988) *Biol. Chem.* 379, 795.

Nissen, P., et al., (1995) Crystal structure of the teRNAry complex of Phe-tRNA$^{Phe}_t$, EF-Tu, and a GTP analog, *Science* 270: 1464–1472.

Nissen, P., et al., (2000) The structural basis of ribosome activity in peptide bond synthesis, *Science* 289: 920–30.

Noller, H. F., et al., (1972) Functional modification of 16S ribosomal RNA by kethoxal, *Proc. Natl. Acad. Sci.* 69: 3113–8.

Noller, H. F., et al, (1981a) *Nucleic Acids Res.* 9: 6167–89.

Noller, H. F., et al., (1981b) *Science* 212: 403–11.

Noller, H. F., et al., (1992) *Science* 256: 1416–1419.

Noller. H. F., et al., (1990) The Ribosome: Structure, Function, and Evolution W. E. Hill et al., Eds. *American Society of Microbiology*, Washington, D.C. 73–92.

O'Connor, M., et al., (1995) *J. Mol. Biol.* 254: 838–47.

Ogle, J. M., et al., (2001). Recognition of cognate transfer RNA by the 30S ribosomal subunit, *Science* 292, 897–902.

Otwinowski, Z. (1993) In Data Collection and Processing, L. Sawyer, et al., Eds. (Warrington, UK: SERC Daresbury Laboratory), pp. 52–62.

Pape, T., et al., (1999) Induced fit in initial selection and proofreading of aminoacyl-tRNA on the ribosome. *Embo. J.* 18: 3800–7.

Pestka, S., (1967) Studies on the formation of transfer ribonucleic acid-ribosome complexes. II. A possible site on the 50S subunit protecting aminoacyl transfer ribonucleic acid from deacylation. *J. Biol. Chem.* 242: 4939–47.

Pioletti, M., et al., (2001). Crystal structures of complexes of the small ribosomal subunit with tetracycline, edeine and IF3, *Embo J* 20, 1829–1839.

Powers, T., et al., (1995). Hydroxyl radical footprinting of ribosomal proteins on 16S rRNA, *RNA* 1, 194–209.

Powers, T., et al., (1990) Dominant lethal mutations in a conserved loop in 16S rRNA, *Proc. Natl. Acad. Sci.* 87: 1042–1046.

Prince, J. B., et al., (1982) Covalent crosslinking of tRNA1Val to 16S RNA at the ribosomal P site: identification of crosslinked residues. *Proc. Natl. Acad. Sci. USA* 79: 5450–4.

Ramakrishnan, V., et al., (1998) *Trends Biochem. Sci.* 23, 208.

Rheinberger, H., et al., *Proc. Natl. Acad. Sci.* 78, 5310 (1981).

Rinke-Appel, J., et al., (1993) Site-directed cross-linking of mRNA analogues to 16S ribosomal RNA; a complete scan of cross-links from all positions between '+1' and '+16' on the mRNA, downstream from the decoding site, *Nucl. Acids Res.* 21: 2853–2859.

Rinke-Appel, J., et al., (1994) Contacts between 16S ribosomal RNA and mRNA, within the spacer region separating the AUG initiator codon and the Shine-Dalgarno sequence; a site-directed cross-linking study, *Nucl. Acids Res.* 22: 3018–3025.

Risuleo, G., et al., (1976). Specificity and properties of the destabilization, induced by initiation factor IF3, of ternary complexes of the 30S ribosomal subunit, aminoacyl-tRNA and polynucleotides, *European Journal of Biochemistry* 67, 603–613.

Ryan, P. C., et al., (1991) *J. Mol. Biol.* 221: 1257–1268.

Sabol, S., et al., (1974). Preparation of Radioactive Initiation Factor 3, *Methods Enzymol* 30, 39–44.

Sacerdot, C., et al., (1999). Mutations that alter initiation codon discrimination by *Escherichia coli* initiation factor IF3, *J Mol Biol* 288, 803–10.

Samaha, R. R. et al., (1995) *Nature* 377: 309–14.

Schilling-Bartetzko, S., et al., (1992) *J. Biol. Chem.* 267: 4693–702.

Schluenzen, F., et al., (2000). Structure of functionally activated small ribosomal subunit at 3.3 angstroms resolution, *Cell* 102, 615–23.

Schnitzer, W., et a., (1997) *Proc. Natl. Acad. Sci.* 94: 12823–8.

Semenkov, Y. P., et al., (2000) Energetic contribution of tRNA hybrid state formation to translocation catalysis on the ribosome, *Nat. Struct. Biol.* 7: 1027–31.

SerdyukI., I., et al., (1992) *Biochimie* 74: 299–306.

Sergiev, P. V., et al., (1997) The path of mRNA through the bacterial ribosome: a site-directed crosslinking study using new photoreactive derivatives of guanosine and uridine. *RNA* 3: 464–75.

Shapkina, T. G., et al., (2000). Initiation factor 3-induced structural changes in the 30 S ribosomal subunit and in complexes containing tRNA(f)(Met) and mRNA, *J Mol Biol* 299, 615–28.

Shatsky, I. N., et al., (1991) How does the mRNA pass through the ribosome? *Biochimie* 73: 937–45.

Shine, J., et al., (1974) The 3'-terminal sequence of *E coli* 16S ribosomal RNA complementarity to nonsense triplets and ribosome binding sites. *Proc. Nat. Acad. Sci. USA* 71: 1342–1346.

Sonenberg, N., et al., (2000). Translational Control of Gene Expression (Cold Spring Harbor, N.Y., CSH Lab Press).

Spirin, A. S. (1969) A model of the functioning ribosome: locking and unlocking of the ribosome subparticles, *Cold Spring Harb. Symp. Quant. Biol.* 34: 197–207.

Stark, H., et al., (1997a) Visualization of elongation factor Tu on the *Escherichia coli* ribosome, *Nature* 389: 403–406.

Steitz, J. A. (1969) Polypeptide chain initiation: nucleotide sequences of the three ribosomal binding sites in bacteriophage R17 RNA, *Nature* 224: 957–64.

Steitz, J. A., et al., (1975) How ribosomes select initiator regions in mRNA: base pair formation between the 3' term inns of 16S rRNA and the mRNA during initiation of protein synthesis in *Escherichia coli, Proc. Nat. Acad. Sci. USA* 72: 4734–8.

Stern, S., (1988a) *J. Mol. Biol.* 204: 447–481.

Stern, S., et al., (1988b). Structural analysis of RNA using chemical and enzymatic probing monitored by primer extension, *Methods Enzymol* 164, 481–9.

Stöffler-Meilecke, et al., *The Ribosome. Structure, Function and Evolution*

Stöffler, G., et al., (1984). Immunoelectron Microscopy of Ribosomes, *Annu Rev Biophys Bioeng* 13, 303–330.

Subramanian, A. R., et al., (1970). Activity of initiation factor F3 in dissociating *Escherichia coli* ribosomes, *Nature* 228, 1273–5.

Sussman, J. K., Simons, E. L., and Simons, R. W. (1996). *Escherichia coli* translation initiation factor 3 discriminates the initiation codon in vivo, *Mol Microbiol* 21, 347–60.

Szewczak, A. A., et al., (1995) *J. Mol. Biol.* 247, 81.

Tapprich, W. E., Goss, D. J., and Dahlberg, A. E. (1989). Mutation at position 791 in *Escherichia coli* 16S ribosomal RNA affects processes involved in the initiation of protein synthesis, *Proc. Natl. Acad. Sci.* 86, 4927–31.

Tissieres, A., et al., (1958) Ribunucleoprotein particles from *E. coli, Nature* 182: 778–780.

Tocilj, A., et al., (1999) *Proc. Natl. Acad. Sci. USA* 96: 14252–7.

Trakhanov, S., et al., (1987) *FEBS Lett.* 220: 319.

Trakhanov, S., et al., (1989) *J. Mol. Biol.* 209: 327–8.

von Ahsen, U., et al., (1995) Identification of bases in 16S rRNA essential for tRNA binding at the 30S ribosomal P site, *Science* 267: 234–7.

von Bohlen, K., et al., (1991) *J. Mol. Biol.* 222:11–5.

Watson, J. D., et al., (1964) *Bull. Soc. Chim. Biol.* 46, 1399.

Welch, M., (1995) *Biochem.* 34: 385–90.

Wickstrom, E. (1981). Physical parameters of *Escherichia coli* translational initiation factor 3 binding to poly(A), *FEBS Lett* 128, 154–6.

Wickstrom, E., et al., (1986). Circular dichroism and 500-MHz proton magnetic resonance studies of the interaction of *Escherichia coli* translational initiation factor 3 protein with the 16S ribosomal RNA 3' cloacin fragment, *Biochemistry* 25, 2770–7.

Wilson, K., et al., (1998) Molecular movement inside the translational engine, *Cell* 92: 337–349.

Wimberly, B. T., et al., (1999) *Cell* 97: 491–502.

Wimberly, B. T., et al., (2000). Structure of the 30S ribosomal subunit, *Nature* 407, 327–39.

Woese, C. R., et al., (1980) *Nucleic Acids Res* 8: 2275–93.

Yarus, M., et al., (1995) tRNA: Structure, biosynthesis and function, D. Söll, et al., Eds. *American Society for Microbiology*, Washington, D.C. 20005, pp. 443–469.

Yonath, A., et al., (1980) *Biochem. Int.* 1: 428.

Yoshizawa, S., et al., (1999) Recognition of the codon-anticodon helix by ribosomal RNA, *Science* 285: 1722–5.

Yusupov, M. M., et al., (1987) Interaction of antibiotics with functional sites in 16S ribosomal RNA, *Nature* 327: 389–394.

Yusupov, M. M., et al., (1989) Intermediate states in the movement of transfer RNA in the ribosome, *Nature* 342: 142–148.

Yusupov, M. M., et al., (1990) Binding of tRNA to the ribosomal A and P sites protects two distinct sets of nucleotides in 16S rRNA, *J. Mol. Biol.* 211: 135–145.

Yusupov, M. M., et al., (1991) *Biochimie* 73: 887–97.

Yusupov, M. M., et al., (1994) Collaborative Computing Project Number 4, *Acta Crystallogr. D*50: 760–763.

Yusupov, M. M., et al., (2001) Crystal Structure of the Ribosome at 5.5 A Resolution, *Science* 292, 883–896.

Yusupova, G. Z., et al., (1991) *FEBS Lett.* 290: 69.

Yusupova, G. Z., et al., (2001) The Path of Messenger RNA Through the Ribosome. *Cell* 106: 233–241.

APPENDIX I

Table VI

| File | PDB ID[1] | Description |
|---|---|---|
| A | 1GIX | 30S ribosome subunit and associated tRNA and mRNA molecules |
| B | 1GIY | 50S ribosome subunit |
| C | [no PDB ID] | IF3 C-terminal domain docked to the 70S subunit |
| D | [no PDB ID] | IF3 N-terminal domain docked to the 70S subunit |
| E | 1JGO (nucleotide chain 1) | Mk27, a 27 nucleotide synthetic mRNA in the 30S subunit |
| F | 1JGP (nucleotide chain 1) | Mv36, a 36 nucleotide synthetic mRNA in the 30S subunit |
| G | 1JGQ (nucleotide chain 1) | Mf36, a 36 nucleotide synthetic mRNA in the 30S subunit |

[1] Structural coordinates have been deposited with the RCSB and are accessible using the indicated IDs (e.g., at www.ncbi.nlm.nih.gov).

```
File A ------------------------------------------------------------------------
    Title   Crystal Structure Of The Ribosome At 5.5 A Resolution. This File,
    1GIx, Contains The 30S Ribosome Subunit, Three tRNA, and Mrna Molecules.
    50S Ribosome Subunit Is In The File 1Giy
    Classification   Ribosome
    Compound   Mol_Id: 1; Molecule: 30S 16S Ribosomal RNA; Chain: A
    Mol_Id: 2; Molecule: tRNA(Phe); Chain: B, C; Engineered: Yes;
    Other_Details: A-Site tRNA Chain B, P-Site tRNA Chain C
    Mol_Id: 3; Molecule: tRNA(Phe); Chain: D; Engineered: Yes; Other_Details:
    E-Site tRNA
    Mol_Id: 4; Molecule: A- and P-Site Messenger RNA Codons; Chain: 1;
    Engineered: Yes; Other_Details: 6 Nt Long Mrna Fragment
    Mol_Id: 5; Molecule: 30S Ribosomal Protein S2; Chain: E
    Mol_Id: 6; Molecule: 30S Ribosomal Protein S3; Chain: F
    Mol_Id: 7; Molecule: 30S Ribosomal Protein S4; Chain: G
    Mol_Id: 8; Molecule: 30S Ribosomal Protein S5; Chain: H
    Mol_Id: 9; Molecule: 30S Ribosomal Protein S6; Chain: I
    Mol_Id: 10; Molecule: 30S Ribosomal Protein S7; Chain: J
    Mol_Id: 11; Molecule: 30S Ribosomal Protein S8; Chain: K
    Mol_Id: 12; Molecule: 30S Ribosomal Protein S9; Chain: L
    Mol_Id: 13; Molecule: 30S Ribosomal Protein S10; Chain: M
    Mol_Id: 14; Molecule: 30S Ribosomal Protein S11; Chain: N
    Mol_Id: 15; Molecule: 30S Ribosomal Protein S12; Chain: O
    Mol_Id: 16; Molecule: 30S Ribosomal Protein S13; Chain: P
    Mol_Id: 17; Molecule: 30S Ribosomal Protein S14; Chain: Q
    Mol_Id: 18; Molecule: 30S Ribosomal Protein S15; Chain: R
    Mol_Id: 19; Molecule: 30S Ribosomal Protein S16; Chain: S
    Mol_Id: 20; Molecule: 30S Ribosomal Protein S17; Chain: T
    Mol_Id: 21; Molecule: 30S Ribosomal Protein S18; Chain: U
    Mol_Id: 22; Molecule: 30S Ribosomal Protein S19; Chain: V
    Mol_Id: 23; Molecule: 30S Ribosomal Protein S20; Chain: W
    Mol_Id: 24; Molecule: 30S Ribosomal Protein Thx; Chain: X
    Exp. Method   X-ray Diffraction
HEADER    RIBOSOME                                30-MAR-01   1GIX
TITLE     CRYSTAL STRUCTURE OF THE RIBOSOME AT 5.5 A RESOLUTION. THIS
TITLE    2 FILE, 1GIX, CONTAINS THE 30S RIBOSOME SUBUNIT, THREE TRNA,
TITLE    3 AND MRNA MOLECULES. 50S RIBOSOME SUBUNIT IS IN THE FILE
TITLE    4 1GIY
COMPND    MOL_ID: 1;
COMPND   2 MOLECULE: 30S 16S RIBOSOMAL RNA;
COMPND   3 CHAIN: A;
COMPND   4 MOL_ID: 2;
COMPND   5 MOLECULE: TRNA(PHE);
COMPND   6 CHAIN: B, C;
COMPND   7 ENGINEERED: YES;
COMPND   8 OTHER_DETAILS: A-SITE TRNA CHAIN B, P-SITE TRNA CHAIN C;
```

```
COMPND   9 MOL_ID: 3;
COMPND  10 MOLECULE: TRNA(PHE);
COMPND  11 CHAIN: D;
COMPND  12 ENGINEERED: YES;
COMPND  13 OTHER_DETAILS: E-SITE TRNA;
COMPND  14 MOL_ID: 4;
COMPND  15 MOLECULE: A- AND P-SITE MESSENGER RNA CODONS;
COMPND  16 CHAIN: 1;
COMPND  17 ENGINEERED: YES;
COMPND  18 OTHER_DETAILS: 6 NT LONG MRNA FRAGMENT;
COMPND  19 MOL_ID: 5;
COMPND  20 MOLECULE: 30S RIBOSOMAL PROTEIN S2;
COMPND  21 CHAIN: E;
COMPND  22 MOL_ID: 6;
COMPND  23 MOLECULE: 30S RIBOSOMAL PROTEIN S3;
COMPND  24 CHAIN: F;
COMPND  25 MOL_ID: 7;
COMPND  26 MOLECULE: 30S RIBOSOMAL PROTEIN S4;
COMPND  27 CHAIN: G;
COMPND  28 MOL_ID: 8;
COMPND  29 MOLECULE: 30S RIBOSOMAL PROTEIN S5;
COMPND  30 CHAIN: H;
COMPND  31 MOL_ID: 9;
COMPND  32 MOLECULE: 30S RIBOSOMAL PROTEIN S6;
COMPND  33 CHAIN: I;
COMPND  34 MOL_ID: 10;
COMPND  35 MOLECULE: 30S RIBOSOMAL PROTEIN S7;
COMPND  36 CHAIN: J;
COMPND  37 MOL_ID: 11;
COMPND  38 MOLECULE: 30S RIBOSOMAL PROTEIN S8;
COMPND  39 CHAIN: K;
COMPND  40 MOL_ID: 12;
COMPND  41 MOLECULE: 30S RIBOSOMAL PROTEIN S9;
COMPND  42 CHAIN: L;
COMPND  43 MOL_ID: 13;
COMPND  44 MOLECULE: 30S RIBOSOMAL PROTEIN S10;
COMPND  45 CHAIN: M;
COMPND  46 MOL_ID: 14;
COMPND  47 MOLECULE: 30S RIBOSOMAL PROTEIN S11;
COMPND  48 CHAIN: N;
COMPND  49 MOL_ID: 15;
COMPND  50 MOLECULE: 30S RIBOSOMAL PROTEIN S12;
COMPND  51 CHAIN: O;
COMPND  52 MOL_ID: 16;
COMPND  53 MOLECULE: 30S RIBOSOMAL PROTEIN S13;
COMPND  54 CHAIN: P;
COMPND  55 MOL_ID: 17;
COMPND  56 MOLECULE: 30S RIBOSOMAL PROTEIN S14;
COMPND  57 CHAIN: Q;
COMPND  58 MOL_ID: 18;
COMPND  59 MOLECULE: 30S RIBOSOMAL PROTEIN S15;
COMPND  60 CHAIN: R;
COMPND  61 MOL_ID: 19;
COMPND  62 MOLECULE: 30S RIBOSOMAL PROTEIN S16;
COMPND  63 CHAIN: S;
COMPND  64 MOL_ID: 20;
COMPND  65 MOLECULE: 30S RIBOSOMAL PROTEIN S17;
COMPND  66 CHAIN: T;
COMPND  67 MOL_ID: 21;
COMPND  68 MOLECULE: 30S RIBOSOMAL PROTEIN S18;
COMPND  69 CHAIN: U;
COMPND  70 MOL_ID: 22;
COMPND  71 MOLECULE: 30S RIBOSOMAL PROTEIN S19;
COMPND  72 CHAIN: V;
COMPND  73 MOL_ID: 23;
COMPND  74 MOLECULE: 30S RIBOSOMAL PROTEIN S20;
COMPND  75 CHAIN: W;
COMPND  76 MOL_ID: 24;
COMPND  77 MOLECULE: 30S RIBOSOMAL PROTEIN THX;
COMPND  78 CHAIN: X
SOURCE     MOL_ID: 1;
SOURCE   2 ORGANISM_SCIENTIFIC: THERMUS THERMOPHILUS;
SOURCE   3 ORGANISM_COMMON: BACTERIA;
SOURCE   4 MOL_ID: 2;
SOURCE   5 SYNTHETIC: YES;
SOURCE   6 OTHER_DETAILS: SEQUENCE NATURALLY OCCURS IN SACCHAROMYCES
SOURCE   7 CEREVISIAE;
SOURCE   8 MOL_ID: 3;
SOURCE   9 SYNTHETIC: YES;
SOURCE  10 OTHER_DETAILS: SEQUENCE NATURALLY OCCURS IN SACCHAROMYCES
SOURCE  11 CEREVISIAE;
SOURCE  12 MOL_ID: 4;
SOURCE  13 SYNTHETIC: YES;
SOURCE  14 MOL_ID: 5;
SOURCE  15 ORGANISM_SCIENTIFIC: THERMUS THERMOPHILUS;
SOURCE  16 ORGANISM_COMMON: BACTERIA;
SOURCE  17 MOL_ID: 6;
```

```
SOURCE   18 ORGANISM_SCIENTIFIC: THERMUS THERMOPHILUS;
SOURCE   19 ORGANISM_COMMON: BACTERIA;
SOURCE   20 MOL_ID: 7;
SOURCE   21 ORGANISM_SCIENTIFIC: THERMUS THERMOPHILUS;
SOURCE   22 ORGANISM_COMMON: BACTERIA;
SOURCE   23 MOL_ID: 8;
SOURCE   24 ORGANISM_SCIENTIFIC: THERMUS THERMOPHILUS;
SOURCE   25 ORGANISM_COMMON: BACTERIA;
SOURCE   26 MOL_ID: 9;
SOURCE   27 ORGANISM_SCIENTIFIC: THERMUS THERMOPHILUS;
SOURCE   28 ORGANISM_COMMON: BACTERIA;
SOURCE   29 MOL_ID: 10;
SOURCE   30 ORGANISM_SCIENTIFIC: THERMUS THERMOPHILUS;
SOURCE   31 ORGANISM_COMMON: BACTERIA;
SOURCE   32 MOL_ID: 11;
SOURCE   33 ORGANISM_SCIENTIFIC: THERMUS THERMOPHILUS;
SOURCE   34 ORGANISM_COMMON: BACTERIA;
SOURCE   35 MOL_ID: 12;
SOURCE   36 ORGANISM_SCIENTIFIC: THERMUS THERMOPHILUS;
SOURCE   37 ORGANISM_COMMON: BACTERIA;
SOURCE   38 MOL_ID: 13;
SOURCE   39 ORGANISM_SCIENTIFIC: THERMUS THERMOPHILUS;
SOURCE   40 ORGANISM_COMMON: BACTERIA;
SOURCE   41 MOL_ID: 14;
SOURCE   42 ORGANISM_SCIENTIFIC: THERMUS THERMOPHILUS;
SOURCE   43 ORGANISM_COMMON: BACTERIA;
SOURCE   44 MOL_ID: 15;
SOURCE   45 ORGANISM_SCIENTIFIC: THERMUS THERMOPHILUS;
SOURCE   46 ORGANISM_COMMON: BACTERIA;
SOURCE   47 MOL_ID: 16;
SOURCE   48 ORGANISM_SCIENTIFIC: THERMUS THERMOPHILUS;
SOURCE   49 ORGANISM_COMMON: BACTERIA;
SOURCE   50 MOL_ID: 17;
SOURCE   51 ORGANISM_SCIENTIFIC: THERMUS THERMOPHILUS;
SOURCE   52 ORGANISM_COMMON: BACTERIA;
SOURCE   53 MOL_ID: 18;
SOURCE   54 ORGANISM_SCIENTIFIC: THERMUS THERMOPHILUS;
SOURCE   55 ORGANISM_COMMON: BACTERIA;
SOURCE   56 MOL_ID: 19;
SOURCE   57 ORGANISM_SCIENTIFIC: THERMUS THERMOPHILUS;
SOURCE   58 ORGANISM_COMMON: BACTERIA;
SOURCE   59 MOL_ID: 20;
SOURCE   60 ORGANISM_SCIENTIFIC: THERMUS THERMOPHILUS;
SOURCE   61 ORGANISM_COMMON: BACTERIA;
SOURCE   62 MOL_ID: 21;
SOURCE   63 ORGANISM_SCIENTIFIC: THERMUS THERMOPHILUS;
SOURCE   64 ORGANISM_COMMON: BACTERIA;
SOURCE   65 MOL_ID: 22;
SOURCE   66 ORGANISM_SCIENTIFIC: THERMUS THERMOPHILUS;
SOURCE   67 ORGANISM_COMMON: BACTERIA;
SOURCE   68 MOL_ID: 23;
SOURCE   69 ORGANISM_SCIENTIFIC: THERMUS THERMOPHILUS;
SOURCE   70 ORGANISM_COMMON: BACTERIA;
SOURCE   71 MOL_ID: 24;
SOURCE   72 ORGANISM_SCIENTIFIC: THERMUS THERMOPHILUS;
SOURCE   73 ORGANISM_COMMON: BACTERIA
KEYWDS      RIBOSOME ASSEMBLY, PROTEIN SYNTHESIS, LIFE
EXPDTA      X-RAY DIFFRACTION
AUTHOR      M.M.YUSUPOV,G.Z.YUSUPOVA,A.BAUCOM,K.LIEBERMAN,T.N.EARNEST,
AUTHOR    2 J.H.D.CATE,H.F.NOLLER
REVDAT    2    01-JUN-01 1GIX    1           TITLE
REVDAT    1    04-MAY-01 1GIX    0
JRNL         AUTH   M.M.YUSUPOV,G.Z.YUSUPOVA,A.BAUCOM,K.LIEBERMAN,
JRNL         AUTH 2 T.N.EARNEST,J.H.D.CATE,H.F.NOLLER
JRNL         TITL   CRYSTAL STRUCTURE OF THE RIBOSOME AT 5.5 A
JRNL         TITL 2 RESOLUTION
JRNL         REF    SCIENCE                        V. 292    883 2001
JRNL         REFN   ASTM SCIEAS  US ISSN 0036-8075
REMARK    1
REMARK    2
REMARK    2 RESOLUTION. 5.50 ANGSTROMS.
REMARK    3
REMARK    3 REFINEMENT.
REMARK    3    PROGRAM     : O
REMARK    3    AUTHORS     : JONES,ZOU,COWAN,KJELDGAARD
REMARK    3
REMARK    3  DATA USED IN REFINEMENT.
REMARK    3    RESOLUTION RANGE HIGH (ANGSTROMS) : 5.50
REMARK    3    RESOLUTION RANGE LOW  (ANGSTROMS) : 250.00
REMARK    3    DATA CUTOFF            (SIGMA(F)) : NULL
REMARK    3    DATA CUTOFF HIGH         (ABS(F)) : NULL
REMARK    3    DATA CUTOFF LOW          (ABS(F)) : NULL
REMARK    3    COMPLETENESS (WORKING+TEST)   (%) : 95.3
REMARK    3    NUMBER OF REFLECTIONS             : 209044
REMARK    3
REMARK    3
REMARK    3  FIT TO DATA USED IN REFINEMENT.
```

```
REMARK   3   CROSS-VALIDATION METHOD          : NULL
REMARK   3   FREE R VALUE TEST SET SELECTION  : NULL
REMARK   3   R VALUE           (WORKING SET)  : NULL
REMARK   3   FREE R VALUE                     : NULL
REMARK   3   FREE R VALUE TEST SET SIZE   (%) : NULL
REMARK   3   FREE R VALUE TEST SET COUNT      : NULL
REMARK   3   ESTIMATED ERROR OF FREE R VALUE  : NULL
REMARK   3
REMARK   3   FIT IN THE HIGHEST RESOLUTION BIN.
REMARK   3   TOTAL NUMBER OF BINS USED                    : NULL
REMARK   3   BIN RESOLUTION RANGE HIGH       (A)          : NULL
REMARK   3   BIN RESOLUTION RANGE LOW        (A)          : NULL
REMARK   3   BIN COMPLETENESS (WORKING+TEST) (%)          : NULL
REMARK   3   REFLECTIONS IN BIN     (WORKING SET)         : NULL
REMARK   3   BIN R VALUE            (WORKING SET)         : NULL
REMARK   3   BIN FREE R VALUE                             : NULL
REMARK   3   BIN FREE R VALUE TEST SET SIZE  (%)          : NULL
REMARK   3   BIN FREE R VALUE TEST SET COUNT              : NULL
REMARK   3   ESTIMATED ERROR OF BIN FREE R VALUE          : NULL
REMARK   3
REMARK   3   NUMBER OF NON-HYDROGEN ATOMS USED IN REFINEMENT.
REMARK   3   PROTEIN ATOMS            : 2396
REMARK   3   NUCLEIC ACID ATOMS       : 6513
REMARK   3   HETEROGEN ATOMS          : 0
REMARK   3   SOLVENT ATOMS            : 0
REMARK   3
REMARK   3   B VALUES.
REMARK   3   FROM WILSON PLOT            (A**2) : NULL
REMARK   3   MEAN B VALUE      (OVERALL, A**2) : NULL
REMARK   3   OVERALL ANISOTROPIC B VALUE.
REMARK   3    B11 (A**2) : NULL
REMARK   3    B22 (A**2) : NULL
REMARK   3    B33 (A**2) : NULL
REMARK   3    B12 (A**2) : NULL
REMARK   3    B13 (A**2) : NULL
REMARK   3    B23 (A**2) : NULL
REMARK   3
REMARK   3   ESTIMATED COORDINATE ERROR.
REMARK   3    ESD FROM LUZZATI PLOT      (A) : NULL
REMARK   3    ESD FROM SIGMAA            (A) : NULL
REMARK   3    LOW RESOLUTION CUTOFF      (A) : NULL
REMARK   3
REMARK   3   CROSS-VALIDATED ESTIMATED COORDINATE ERROR.
REMARK   3    ESD FROM C-V LUZZATI PLOT  (A) : NULL
REMARK   3    ESD FROM C-V SIGMAA        (A) : NULL
REMARK   3
REMARK   3   RMS DEVIATIONS FROM IDEAL VALUES.
REMARK   3    BOND LENGTHS              (A) : NULL
REMARK   3    BOND ANGLES         (DEGREES) : NULL
REMARK   3    DIHEDRAL ANGLES     (DEGREES) : NULL
REMARK   3    IMPROPER ANGLES     (DEGREES) : NULL
REMARK   3
REMARK   3   ISOTROPIC THERMAL MODEL : NULL
REMARK   3
REMARK   3   ISOTROPIC THERMAL FACTOR RESTRAINTS.    RMS      SIGMA
REMARK   3    MAIN-CHAIN BOND             (A**2) : NULL  ; NULL
REMARK   3    MAIN-CHAIN ANGLE            (A**2) : NULL  ; NULL
REMARK   3    SIDE-CHAIN BOND             (A**2) : NULL  ; NULL
REMARK   3    SIDE-CHAIN ANGLE            (A**2) : NULL  ; NULL
REMARK   3
REMARK   3
REMARK   3   NCS MODEL : NULL
REMARK   3
REMARK   3   NCS RESTRAINTS.                        RMS   SIGMA/WEIGHT
REMARK   3    GROUP  1  POSITIONAL    (A)    : NULL  ; NULL
REMARK   3    GROUP  1  B-FACTOR      (A**2) : NULL  ; NULL
REMARK   3
REMARK   3   PARAMETER FILE  1  : NULL
REMARK   3   TOPOLOGY FILE   1  : NULL
REMARK   3
REMARK   3   OTHER REFINEMENT REMARKS: THE MODEL WAS BUILT BY MANUAL
REMARK   3   FITTING OF INDIVIDUAL MOLECULES INTO THE EXPERIMENTAL
REMARK   3   ELECTRON DENSITY USING THE GRAPHIC PROGRAM O.
REMARK   4
REMARK   4   1GIX COMPLIES WITH FORMAT V. 2.3, 09-JULY-1998
REMARK 100
REMARK 100 THIS ENTRY HAS BEEN PROCESSED BY THE NUCLEIC ACID DATABASE
REMARK 100 ON 03-APR-2001.
REMARK 100 THE NDB ID CODE IS RR0031.
REMARK 105
REMARK 105 THE PROTEIN DATA BANK HAS ADOPTED THE SACCHARIDE CHEMISTS
REMARK 105 NOMENCLATURE FOR ATOMS OF THE DEOXYRIBOSE/RIBOSE MOIETY
REMARK 105 RATHER THAN THAT OF THE NUCLEOSIDE CHEMISTS.  THE RING
REMARK 105 OXYGEN ATOM IS LABELLED O4* INSTEAD OF O1*.
REMARK 200
REMARK 200 EXPERIMENTAL DETAILS
REMARK 200  EXPERIMENT TYPE                : X-RAY DIFFRACTION
```

```
REMARK 200  DATE OF DATA COLLECTION              : NULL
REMARK 200  TEMPERATURE            (KELVIN)      : 100.0
REMARK 200  PH                                   : NULL
REMARK 200  NUMBER OF CRYSTALS USED              : 2
REMARK 200
REMARK 200  SYNCHROTRON              (Y/N)       : Y
REMARK 200  RADIATION SOURCE                     : ALS
REMARK 200  BEAMLINE                             : 5.0.2
REMARK 200  X-RAY GENERATOR MODEL                : NULL
REMARK 200  MONOCHROMATIC OR LAUE    (M/L)       : M
REMARK 200  WAVELENGTH OR RANGE        (A)       : 1.100
REMARK 200  MONOCHROMATOR                        : NULL
REMARK 200  OPTICS                               : NULL
REMARK 200
REMARK 200  DETECTOR TYPE                        : CCD
REMARK 200  DETECTOR MANUFACTURER                : ADSC QUANTUM 4
REMARK 200  INTENSITY-INTEGRATION SOFTWARE       : DENZO
REMARK 200  DATA SCALING SOFTWARE                : SCALEPACK
REMARK 200
REMARK 200  NUMBER OF UNIQUE REFLECTIONS         : 209044
REMARK 200  RESOLUTION RANGE HIGH      (A)       : 5.000
REMARK 200  RESOLUTION RANGE LOW       (A)       : 250.000
REMARK 200  REJECTION CRITERIA  (SIGMA(I))       : 0.000
REMARK 200
REMARK 200  OVERALL.
REMARK 200   COMPLETENESS FOR RANGE    (%)       : 95.3
REMARK 200   DATA REDUNDANCY                     : 2.800
REMARK 200   R MERGE                    (I)      : NULL
REMARK 200   R SYM                      (I)      : 0.09400
REMARK 200   <I/SIGMA(I)> FOR THE DATA SET       : NULL
REMARK 200
REMARK 200  IN THE HIGHEST RESOLUTION SHELL.
REMARK 200   HIGHEST RESOLUTION SHELL, RANGE HIGH (A) : 5.50
REMARK 200   HIGHEST RESOLUTION SHELL, RANGE LOW  (A) : 5.70
REMARK 200   COMPLETENESS FOR SHELL     (%)      : 95.0
REMARK 200   DATA REDUNDANCY IN SHELL            : 2.80
REMARK 200   R MERGE FOR SHELL          (I)      : 0.30800
REMARK 200   R SYM FOR SHELL            (I)      : 0.30800
REMARK 200   <I/SIGMA(I)> FOR SHELL              : 3.300
REMARK 200
REMARK 200  DIFFRACTION PROTOCOL: SINGLE WAVELENGTH
REMARK 200  METHOD USED TO DETERMINE THE STRUCTURE: MAD
REMARK 200  SOFTWARE USED: CCP4
REMARK 200  STARTING MODEL: NULL
REMARK 200
REMARK 200  REMARK: NULL
REMARK 280
REMARK 280  CRYSTAL
REMARK 280  SOLVENT CONTENT, VS   (%): NULL
REMARK 280  MATTHEWS COEFFICIENT, VM (ANGSTROMS**3/DA): NULL
REMARK 280
REMARK 280  CRYSTALLIZATION CONDITIONS: NULL
REMARK 290
REMARK 290  CRYSTALLOGRAPHIC SYMMETRY
REMARK 290  SYMMETRY OPERATORS FOR SPACE GROUP: I 4 2 2
REMARK 290
REMARK 290        SYMOP   SYMMETRY
REMARK 290       NNNMMM   OPERATOR
REMARK 290         1555   X,Y,Z
REMARK 290         2555   -X,-Y,Z
REMARK 290         3555   -Y,X,Z
REMARK 290         4555   Y,-X,Z
REMARK 290         5555   -X,Y,-Z
REMARK 290         6555   X,-Y,-Z
REMARK 290         7555   Y,X,-Z
REMARK 290         8555   -Y,-X,-Z
REMARK 290         9555   1/2+X,1/2+Y,1/2+Z
REMARK 290        10555   1/2-X,1/2-Y,1/2+Z
REMARK 290        11555   1/2-Y,1/2+X,1/2+Z
REMARK 290        12555   1/2+Y,1/2-X,1/2+Z
REMARK 290        13555   1/2-X,1/2+Y,1/2-Z
REMARK 290        14555   1/2+X,1/2-Y,1/2-Z
REMARK 290        15555   1/2+Y,1/2+X,1/2-Z
REMARK 290        16555   1/2-Y,1/2-X,1/2-Z
REMARK 290
REMARK 290     WHERE NNN -> OPERATOR NUMBER
REMARK 290           MMM -> TRANSLATION VECTOR
REMARK 290
REMARK 290  CRYSTALLOGRAPHIC SYMMETRY TRANSFORMATIONS
REMARK 290  THE FOLLOWING TRANSFORMATIONS OPERATE ON THE ATOM/HETATM
REMARK 290  RECORDS IN THIS ENTRY TO PRODUCE CRYSTALLOGRAPHICALLY
REMARK 290  RELATED MOLECULES.
REMARK 290     SMTRY1   1  1.000000  0.000000  0.000000        0.00000
REMARK 290     SMTRY2   1  0.000000  1.000000  0.000000        0.00000
REMARK 290     SMTRY3   1  0.000000  0.000000  1.000000        0.00000
REMARK 290     SMTRY1   2 -1.000000  0.000000  0.000000        0.00000
REMARK 290     SMTRY2   2  0.000000 -1.000000  0.000000        0.00000
```

```
REMARK 290   SMTRY3    2  0.000000  0.000000  1.000000        0.00000
REMARK 290   SMTRY1    3  0.000000 -1.000000  0.000000        0.00000
REMARK 290   SMTRY2    3  1.000000  0.000000  0.000000        0.00000
REMARK 290   SMTRY3    3  0.000000  0.000000  1.000000        0.00000
REMARK 290   SMTRY1    4  0.000000  1.000000  0.000000        0.00000
REMARK 290   SMTRY2    4 -1.000000  0.000000  0.000000        0.00000
REMARK 290   SMTRY3    4  0.000000  0.000000  1.000000        0.00000
REMARK 290   SMTRY1    5 -1.000000  0.000000  0.000000        0.00000
REMARK 290   SMTRY2    5  0.000000  1.000000  0.000000        0.00000
REMARK 290   SMTRY3    5  0.000000  0.000000 -1.000000        0.00000
REMARK 290   SMTRY1    6  1.000000  0.000000  0.000000        0.00000
REMARK 290   SMTRY2    6  0.000000 -1.000000  0.000000        0.00000
REMARK 290   SMTRY3    6  0.000000  0.000000 -1.000000        0.00000
REMARK 290   SMTRY1    7  0.000000  1.000000  0.000000        0.00000
REMARK 290   SMTRY2    7  1.000000  0.000000  0.000000        0.00000
REMARK 290   SMTRY3    7  0.000000  0.000000 -1.000000        0.00000
REMARK 290   SMTRY1    8  0.000000 -1.000000  0.000000        0.00000
REMARK 290   SMTRY2    8 -1.000000  0.000000  0.000000        0.00000
REMARK 290   SMTRY3    8  0.000000  0.000000 -1.000000        0.00000
REMARK 290   SMTRY1    9  1.000000  0.000000  0.000000      253.60000
REMARK 290   SMTRY2    9  0.000000  1.000000  0.000000      253.60000
REMARK 290   SMTRY3    9  0.000000  0.000000  1.000000      401.83000
REMARK 290   SMTRY1   10 -1.000000  0.000000  0.000000      253.60000
REMARK 290   SMTRY2   10  0.000000 -1.000000  0.000000      253.60000
REMARK 290   SMTRY3   10  0.000000  0.000000  1.000000      401.83000
REMARK 290   SMTRY1   11  0.000000 -1.000000  0.000000      253.60000
REMARK 290   SMTRY2   11  1.000000  0.000000  0.000000      253.60000
REMARK 290   SMTRY3   11  0.000000  0.000000  1.000000      401.83000
REMARK 290   SMTRY1   12  0.000000  1.000000  0.000000      253.60000
REMARK 290   SMTRY2   12 -1.000000  0.000000  0.000000      253.60000
REMARK 290   SMTRY3   12  0.000000  0.000000  1.000000      401.83000
REMARK 290   SMTRY1   13 -1.000000  0.000000  0.000000      253.60000
REMARK 290   SMTRY2   13  0.000000  1.000000  0.000000      253.60000
REMARK 290   SMTRY3   13  0.000000  0.000000 -1.000000      401.83000
REMARK 290   SMTRY1   14  1.000000  0.000000  0.000000      253.60000
REMARK 290   SMTRY2   14  0.000000 -1.000000  0.000000      253.60000
REMARK 290   SMTRY3   14  0.000000  0.000000 -1.000000      401.83000
REMARK 290   SMTRY1   15  0.000000  1.000000  0.000000      253.60000
REMARK 290   SMTRY2   15  1.000000  0.000000  0.000000      253.60000
REMARK 290   SMTRY3   15  0.000000  0.000000 -1.000000      401.83000
REMARK 290   SMTRY1   16  0.000000 -1.000000  0.000000      253.60000
REMARK 290   SMTRY2   16 -1.000000  0.000000  0.000000      253.60000
REMARK 290   SMTRY3   16  0.000000  0.000000 -1.000000      401.83000
REMARK 290
REMARK 290 REMARK: NULL
REMARK 300
REMARK 300 BIOMOLECULE: 1
REMARK 300 THIS ENTRY CONTAINS THE CRYSTALLOGRAPHIC ASYMMETRIC UNIT
REMARK 300 WHICH CONSISTS OF 25CHAIN(S). SEE REMARK 350 FOR
REMARK 300 INFORMATION ON GENERATING THE BIOLOGICAL MOLECULE(S).
REMARK 350
REMARK 350 GENERATING THE BIOMOLECULE
REMARK 350 COORDINATES FOR A COMPLETE MULTIMER REPRESENTING THE KNOWN
REMARK 350 BIOLOGICALLY SIGNIFICANT OLIGOMERIZATION STATE OF THE
REMARK 350 MOLECULE CAN BE GENERATED BY APPLYING BIOMT TRANSFORMATIONS
REMARK 350 GIVEN BELOW.  BOTH NON-CRYSTALLOGRAPHIC AND
REMARK 350 CRYSTALLOGRAPHIC OPERATIONS ARE GIVEN.
REMARK 350
REMARK 350 BIOMOLECULE: 1
REMARK 350 APPLY THE FOLLOWING TO CHAINS: A, B, C, D, 1, E, F, G, H,
REMARK 350 I, J, K, L, M, N, O, P, Q, R, S, T, U, V, W, X
REMARK 350   BIOMT1   1  1.000000  0.000000  0.000000        0.00000
REMARK 350   BIOMT2   1  0.000000  1.000000  0.000000        0.00000
REMARK 350   BIOMT3   1  0.000000  0.000000  1.000000        0.00000
REMARK 400
REMARK 400 COMPOUND
REMARK 400
REMARK 400 PDB ENTRIES 1GIX AND 1GIY REPRESENT ONE CRYSTAL
REMARK 400 STRUCTURE OF THE THERMUS THERMOPHILUS 70S RIBOSOME.
REMARK 400
REMARK 400 THIS FILE, 1GIX, CONTAINS ONLY MOLECULES OF
REMARK 400 THE 30S RIBOSOMAL SUBUNIT, THREE TRNA MOLECULES
REMARK 400 AND AN MRNA FRAGMENT. THE 50S SUBUNIT IS IN THE
REMARK 400 PDB FILE 1GIY.
REMARK 400
REMARK 400    70S RIBOSOME PARTICLE ORIGINATES FROM THERMUS
REMARK 400 THERMOPHILUS. HOWEVER, INITIAL MODELS OF SOME OF
REMARK 400 ITS CONSTITUENTS WERE TAKEN FROM STRUCTURES FROM
REMARK 400 OTHER ORGANISMS.
REMARK 400
REMARK 400 THE FOLLOWING LISTS CHAIN ID (AS IN THE COMPND
REMARK 400 RECORDS ABOVE), THE PDB ID OF THE STRUCTURAL
REMARK 400 MODEL AND THE SOURCE ORGANISM OF THAT MODEL FOR
REMARK 400 EACH BIOMOLECULE IN 1GIX AND 1GIY.
REMARK 400
REMARK 400 ====================================================
REMARK 400      30S SMALL SUBUNIT, PDB FILE 1GIX
```

```
REMARK 400 ==========================================================
REMARK 400
REMARK 400 ===> 30S 16S RIBOSOMAL RNA, CHAIN A              <===
REMARK 400 1FJF       THERMUS THERMOPHILUS
REMARK 400 ===> TRNA(PHE), CHAIN B, C                       <===
REMARK 400 1EVV, 1FFZ     SACHROMYCES CEREVISIAE
REMARK 400 ===> TRNA(PHE), CHAIN D                          <===
REMARK 400 1GTR, 1B23, 3TRA NO SEQUENCE ENTRY
REMARK 400 ===> 30S RIBOSOMAL PROTEIN S2, CHAIN E           <===
REMARK 400 1FJF       THERMUS THERMOPHILUS
REMARK 400 ===> 30S RIBOSOMAL PROTEIN S3, CHAIN F           <===
REMARK 400 1FJF       THERMUS THERMOPHILUS
REMARK 400 ===> 30S RIBOSOMAL PROTEIN S4, CHAIN G           <===
REMARK 400 1FJF       THERMUS THERMOPHILUS
REMARK 400 ===> 30S RIBOSOMAL PROTEIN S5, CHAIN H           <===
REMARK 400 1FJF       THERMUS THERMOPHILUS
REMARK 400 ===> 30S RIBOSOMAL PROTEIN S6, CHAIN I           <===
REMARK 400 1FJF       THERMUS THERMOPHILUS
REMARK 400 ===> 30S RIBOSOMAL PROTEIN S7, CHAIN J           <===
REMARK 400 1FJF       THERMUS THERMOPHILUS
REMARK 400 ===> 30S RIBOSOMAL PROTEIN S8, CHAIN K           <===
REMARK 400 1FJF       THERMUS THERMOPHILUS
REMARK 400 ===> 30S RIBOSOMAL PROTEIN S9, CHAIN L           <===
REMARK 400 1FJF       THERMUS THERMOPHILUS
REMARK 400 ===> 30S RIBOSOMAL PROTEIN S10, CHAIN M          <===
REMARK 400 1FJF       THERMUS THERMOPHILUS
REMARK 400 ===> 30S RIBOSOMAL PROTEIN S11, CHAIN N          <===
REMARK 400 1FJF       THERMUS THERMOPHILUS
REMARK 400 ===> 30S RIBOSOMAL PROTEIN S12, CHAIN O          <===
REMARK 400 1FJF       THERMUS THERMOPHILUS
REMARK 400 ===> 30S RIBOSOMAL PROTEIN S13, CHAIN P          <===
REMARK 400 1FJF       THERMUS THERMOPHILUS
REMARK 400 ===> 30S RIBOSOMAL PROTEIN S14, CHAIN Q          <===
REMARK 400 1FJF       THERMUS THERMOPHILUS
REMARK 400 ===> 30S RIBOSOMAL PROTEIN S15, CHAIN R          <===
REMARK 400 1FJF       THERMUS THERMOPHILUS
REMARK 400 ===> 30S RIBOSOMAL PROTEIN S16, CHAIN S          <===
REMARK 400 1FJF       THERMUS THERMOPHILUS
REMARK 400 ===> 30S RIBOSOMAL PROTEIN S17, CHAIN T          <===
REMARK 400 1FJF       THERMUS THERMOPHILUS
REMARK 400 ===> 30S RIBOSOMAL PROTEIN S18, CHAIN U          <===
REMARK 400 1FJF       THERMUS THERMOPHILUS
REMARK 400 ===> 30S RIBOSOMAL PROTEIN S19, CHAIN V          <===
REMARK 400 1FJF       THERMUS THERMOPHILUS
REMARK 400 ===> 30S RIBOSOMAL PROTEIN S20, CHAIN W          <===
REMARK 400 1FJF       THERMUS THERMOPHILUS
REMARK 400 ===> 30S RIBOSOMAL PROTEIN THX, CHAIN X          <===
REMARK 400 1FJF       THERMUS THERMOPHILUS
REMARK 400
REMARK 400 ==========================================================
REMARK 400     50S LARGE SUBUNIT, PDB FILE 1GIY
REMARK 400 ==========================================================
REMARK 400
REMARK 400 ===> 50S 23S RIBOSOMAL RNA, CHAIN A              <===
REMARK 400 1FFK       THERMUS THERMOPHILUS
REMARK 400 ===> 50S 5S RIBOSOMAL RNA, CHAIN B               <===
REMARK 400 1FFK       THERMUS THERMOPHILUS
REMARK 400 ===> 50S RIBOSOMAL PROTEIN L1, CHAIN C           <===
REMARK 400 NO PUBLIC COORDINATES FOR THE MODEL
REMARK 400           THERMUS AQUATICUS
REMARK 400 ===> 50S RIBOSOMAL PROTEIN L2 , CHAIN D          <===
REMARK 400 1RL2 (RESIDUES  61-197), BACILLUS STEAROTHERMOPHILUS
REMARK 400 1FFK (RESIDUES 138-203), HALOARCULA MARISMORTUI
REMARK 400 ===> 50S RIBOSOMAL PROTEIN L3 , CHAIN E          <===
REMARK 400 1FFK       HALOARCULA MARISMORTUI (L3P)
REMARK 400 ===> 50S RIBOSOMAL PROTEIN L4, CHAIN F           <===
REMARK 400 1FFK       HALOARCULA MARISMORTUI (L4E)
REMARK 400 ===> 50S RIBOSOMAL PROTEIN L5, CHAIN G           <===
REMARK 400 1FFK       HALOARCULA MARISMORTUI (L5P)
REMARK 400 ===> 50S RIBOSOMAL PROTEIN L6, CHAIN H
REMARK 400 1RL6       BACILLUS STEAROTHERMOPHILUS
REMARK 400 ===> 50S RIBOSOMAL PROTEIN L7/L12, CHAIN I, J    <===
REMARK 400 1DD3       THERMOTOGA MARITIMA
REMARK 400 ===> 50S RIBOSOMAL PROTEIN L9, CHAIN K           <===
REMARK 400 1DIV       BACILLUS STEAROTHERMOPHILUS
REMARK 400 ===> 50S RIBOSOMAL PROTEIN L11, CHAIN L          <===
REMARK 400 1MMS       THERMOTOGA MARITIMA
REMARK 400 ===> 50S RIBOSOMAL PROTEIN L13, CHAIN M          <===
REMARK 400 1FFK       HALOARCULA MARISMORTUI (L13P)
REMARK 400 ===> 50S RIBOSOMAL PROTEIN L14, CHAIN N          <===
REMARK 400 1WHI       BACILLUS STEAROTHERMOPHILUS
REMARK 400 ===> 50S RIBOSOMAL PROTEIN L15, CHAIN O          <===
REMARK 400 1FFK       HALOARCULA MARISMORTUI (L15P)
REMARK 400 ===> 50S RIBOSOMAL PROTEIN L16, CHAIN P          <===
REMARK 400 1FFK       NO SEQUENCE ENTRY FOUND
REMARK 400 ===> 50S RIBOSOMAL PROTEIN L18, CHAIN Q          <===
REMARK 400 1FFK       HALOARCULA MARISMORTUI (L18P)
```

```
REMARK 400 ===> 50S RIBOSOMAL PROTEIN L19, CHAIN R        <===
REMARK 400 1FFK      HALOARCULA MARISMORTUI (L24E)
REMARK 400 ===> 50S RIBOSOMAL PROTEIN L22, CHAIN S        <===
REMARK 400 1BXE      THERMUS THERMOPHILUS
REMARK 400 ===> 50S RIBOSOMAL PROTEIN L23, CHAIN T        <===
REMARK 400 1FFK      HALOARCULA MARISMORTUI (L23P)
REMARK 400 ===> 50S RIBOSOMAL PROTEIN L24, CHAIN U        <===
REMARK 400 1FFK      HALOARCULA MARISMORTUI (L24P)
REMARK 400 ===> 50S RIBOSOMAL PROTEIN L25, CHAIN V        <===
REMARK 400 1DFU      ESCHERICHIA COLI
REMARK 400 ===> 50S RIBOSOMAL PROTEIN L29, CHAIN W        <===
REMARK 400 1FFK      HALOARCULA MARISMORTUI (L29P)
REMARK 400 ===> 50S RIBOSOMAL PROTEIN L30, CHAIN X        <===
REMARK 400 1BXY      THERMUS THERMOPHILUS
REMARK 900
REMARK 900 RELATED ENTRIES
REMARK 900 RELATED ID: 486D      RELATED DB: PDB
REMARK 900 7.5A MODEL OF 70S RIBOSOME
DBREF  1GIX A    0  1544  GB       155076   M26924           646  2167
DBREF  1GIX B    1    76  GB       176479   M10263             1    76
DBREF  1GIX C    1    76  GB       176479   M10263             1    76
DBREF  1GIX E    1   256  EMBL   13446664   CAC35061           1   256
DBREF  1GIX F    1   239  SWS    13446666   RS4_THETH          1   239
DBREF  1GIX G    1   209  SWS      P80373   RS4_THETH          1   209
DBREF  1GIX H    1   162  SWS      P27152   RS5_THETH          1   162
DBREF  1GIX I    1   101  SWS      P23370   RS6_THETH          1   101
DBREF  1GIX J    1   156  SWS      P17291   RS7_THETH          1   156
DBREF  1GIX K    1   138  SWS      P24319   RS8_THETH          1   138
DBREF  1GIX L    1   128  EMBL   13446668   CAC35063           1   128
DBREF  1GIX M    1   105  SWS      P80375   RS10_THETH         1   105
DBREF  1GIX N    1   129  GB      4519421   BAA75547           1   129
DBREF  1GIX O    1   135  SWS      P17293   RS12_THETH         1   135
DBREF  1GIX P    1   126  GB      4519420   BAA75546           1   126
DBREF  1GIX Q    1    61  SWS      P24320   RS14_THETH         1    61
DBREF  1GIX R    1    89  SWS      P80378   RS15_THETH         1    89
DBREF  1GIX S    1    91  GB     12056104   CAC21226           1    91
DBREF  1GIX T    1   105  EMBL     673503   CAA85419           1   105
DBREF  1GIX U    1    88  GB      6739549   AAF27297           1    88
DBREF  1GIX V    1    93  SWS      P80381   RS19_THETH         1    93
DBREF  1GIX W    1   106  GB     11125386   CAC15067           1   106
DBREF  1GIX X    2    27  SWS      P32193   RSHX_THETH         1    26
SEQADV 1GIX 2MG B  10  GB     176479        G    10 TRNA MODIFICATION
SEQADV 1GIX H2U B  16  GB     176479        U    16 TRNA MODIFICATION
SEQADV 1GIX H2U B  17  GB     176479        U    17 TRNA MODIFICATION
SEQADV 1GIX M2G B  26  GB     176479        G    26 TRNA MODIFICATION
SEQADV 1GIX OMC B  32  GB     176479        C    32 TRNA MODIFICATION
SEQADV 1GIX OMG B  34  GB     176479        G    34 TRNA MODIFICATION
SEQADV 1GIX  YG B  37  GB     176479        G    37 TRNA MODIFICATION
SEQADV 1GIX PSU B  39  GB     176479        U    39 TRNA MODIFICATION
SEQADV 1GIX 5MC B  40  GB     176479        C    40 TRNA MODIFICATION
SEQADV 1GIX 7MG B  46  GB     176479        G    46 TRNA MODIFICATION
SEQADV 1GIX 5MC B  49  GB     176479        C    49 TRNA MODIFICATION
SEQADV 1GIX 5MU B  54  GB     176479        U    54 TRNA MODIFICATION
SEQADV 1GIX PSU B  55  GB     176479        U    55 TRNA MODIFICATION
SEQADV 1GIX 1MA B  58  GB     176479        A    58 TRNA MODIFICATION
SEQADV 1GIX 2MG C  10  GB     176479        G    10 TRNA MODIFICATION
SEQADV 1GIX H2U C  16  GB     176479        U    16 TRNA MODIFICATION
SEQADV 1GIX H2U C  17  GB     176479        U    17 TRNA MODIFICATION
SEQADV 1GIX M2G C  26  GB     176479        G    26 TRNA MODIFICATION
SEQADV 1GIX OMC C  32  GB     176479        C    32 TRNA MODIFICATION
SEQADV 1GIX OMG C  34  GB     176479        G    34 TRNA MODIFICATION
SEQADV 1GIX  YG C  37  GB     176479        G    37 TRNA MODIFICATION
SEQADV 1GIX PSU C  39  GB     176479        U    39 TRNA MODIFICATION
SEQADV 1GIX 5MC C  40  GB     176479        C    40 TRNA MODIFICATION
SEQADV 1GIX 7MG C  46  GB     176479        G    46 TRNA MODIFICATION
SEQADV 1GIX 5MC C  49  GB     176479        C    49 TRNA MODIFICATION
SEQADV 1GIX 5MU C  54  GB     176479        U    54 TRNA MODIFICATION
SEQADV 1GIX PSU C  55  GB     176479        U    55 TRNA MODIFICATION
SEQADV 1GIX 1MA C  58  GB     176479        A    58 TRNA MODIFICATION
SEQRES   1 A 1522   U  U  U  G  U  U  G  G  A  G  A  G  U
SEQRES   2 A 1522   U  U  G  A  U  C  C  U  G  G  C  U  G
SEQRES   3 A 1522   A  G  G  U  G  A  A  C  G  C  U  G  A
SEQRES   4 A 1522   G  C  G  G  C  G  U  G  C  C  U  A  A
SEQRES   5 A 1522   G  A  C  A  U  G  C  A  A  G  U  C  G
SEQRES   6 A 1522   U  G  C  G  G  G  C  C  G  C  G  G  G
SEQRES   7 A 1522   G  U  U  U  U  A  C  U  C  C  G  U  G
SEQRES   8 A 1522   G  U  C  A  G  C  G  G  C  G  G  A  C
SEQRES   9 A 1522   G  G  G  U  G  A  G  U  A  A  C  G  C
SEQRES  10 A 1522   G  U  G  G  G  U  G  A  C  C  U  A  C
SEQRES  11 A 1522   C  C  G  G  A  A  G  A  G  G  G  G  G
SEQRES  12 A 1522   A  C  A  A  C  C  C  G  G  G  A  A  A
SEQRES  13 A 1522   A  C  U  C  G  G  C  U  A  A  U  A  C
SEQRES  14 A 1522   C  C  C  C  A  U  G  U  G  A  C  C  C
SEQRES  15 A 1522   C  G  C  C  C  C  U  U  G  G  G  G  U
SEQRES  16 A 1522   G  U  G  U  C  A  A  A  G  G  C  U  C
SEQRES  17 A 1522   U  U  U  G  C  C  G  C  U  U  C  C  C
SEQRES  18 A 1522   G  G  A  U  G  G  C  C  C  G  C  G
```

| | | | | | | | | | | | | | | | |
|---|---|---|---|---|---|---|---|---|---|---|---|---|---|---|---|
| SEQRES | 19 | A | 1522 | U | C | C | C | A | U | C | A | G | C | U | A | G |
| SEQRES | 20 | A | 1522 | U | U | G | G | U | G | G | G | G | U | A | A | U |
| SEQRES | 21 | A | 1522 | G | G | C | C | C | A | C | C | A | A | G | C | C |
| SEQRES | 22 | A | 1522 | G | A | C | G | A | C | G | G | G | U | A | G | C |
| SEQRES | 23 | A | 1522 | C | G | G | U | C | U | G | A | G | A | G | G | A |
| SEQRES | 24 | A | 1522 | U | G | G | C | C | G | G | C | C | A | C | A | G |
| SEQRES | 25 | A | 1522 | G | G | G | C | A | C | U | G | A | G | A | C | A |
| SEQRES | 26 | A | 1522 | C | G | G | G | C | C | C | C | A | C | U | C | C |
| SEQRES | 27 | A | 1522 | U | G | A | C | G | G | A | G | G | C | A | G | C |
| SEQRES | 28 | A | 1522 | A | G | U | U | A | G | G | A | A | U | C | U | U |
| SEQRES | 29 | A | 1522 | C | C | G | C | A | A | U | G | G | G | C | G | C |
| SEQRES | 30 | A | 1522 | A | A | G | C | C | U | G | A | C | G | G | A | G |
| SEQRES | 31 | A | 1522 | C | G | A | C | G | C | C | G | C | U | U | G | G |
| SEQRES | 32 | A | 1522 | A | G | G | A | A | G | A | A | G | C | C | C | U |
| SEQRES | 33 | A | 1522 | U | C | G | G | G | G | U | G | U | A | A | A | C |
| SEQRES | 34 | A | 1522 | U | C | C | U | G | A | A | C | C | C | G | G | G |
| SEQRES | 35 | A | 1522 | A | C | G | A | A | A | C | C | C | C | G | A | A |
| SEQRES | 36 | A | 1522 | C | G | A | G | G | G | C | A | C | U | G | A | C |
| SEQRES | 37 | A | 1522 | G | G | U | A | C | C | G | G | G | G | U | A | A |
| SEQRES | 38 | A | 1522 | U | A | G | C | G | C | C | G | G | C | C | A | A |
| SEQRES | 39 | A | 1522 | C | U | C | C | G | U | G | C | C | A | G | C | A |
| SEQRES | 40 | A | 1522 | G | C | C | G | C | G | G | U | A | A | U | A | C |
| SEQRES | 41 | A | 1522 | G | G | A | G | G | G | C | G | C | G | A | G | C |
| SEQRES | 42 | A | 1522 | G | U | U | A | C | C | C | G | G | A | U | U | C |
| SEQRES | 43 | A | 1522 | A | C | U | G | G | G | C | G | U | A | A | A | G |
| SEQRES | 44 | A | 1522 | G | G | C | G | U | G | U | A | G | G | C | G | G |
| SEQRES | 45 | A | 1522 | C | C | U | G | G | G | G | C | G | U | C | C | C |
| SEQRES | 46 | A | 1522 | A | U | G | U | G | A | A | A | G | A | C | C | A |
| SEQRES | 47 | A | 1522 | C | G | G | C | U | C | A | A | C | C | G | U | G |
| SEQRES | 48 | A | 1522 | G | G | G | G | A | G | C | G | U | G | G | G | A |
| SEQRES | 49 | A | 1522 | U | A | C | G | C | U | C | A | G | G | C | U | A |
| SEQRES | 50 | A | 1522 | G | A | C | G | U | G | G | G | A | G | A | G | G |
| SEQRES | 51 | A | 1522 | G | G | U | G | G | U | G | G | A | A | U | U | C |
| SEQRES | 52 | A | 1522 | C | C | G | G | A | G | U | A | G | C | G | G | U |
| SEQRES | 53 | A | 1522 | G | A | A | A | U | G | C | G | C | A | G | A | G |
| SEQRES | 54 | A | 1522 | A | C | C | G | G | G | A | G | A | A | C | A | G |
| SEQRES | 55 | A | 1522 | C | C | G | A | U | G | G | C | G | A | A | G | G |
| SEQRES | 56 | A | 1522 | C | A | G | C | C | A | C | C | U | G | G | U | C |
| SEQRES | 57 | A | 1522 | C | A | C | C | C | G | U | G | A | C | G | C | U |
| SEQRES | 58 | A | 1522 | G | A | G | G | C | G | C | G | A | A | A | G | C |
| SEQRES | 59 | A | 1522 | G | U | G | G | G | G | A | G | C | A | A | C | C |
| SEQRES | 60 | A | 1522 | C | G | G | A | U | U | A | G | A | U | A | C | C |
| SEQRES | 61 | A | 1522 | C | G | G | G | U | A | G | U | C | C | A | C | G |
| SEQRES | 62 | A | 1522 | C | C | C | U | A | A | A | C | G | A | U | G | C |
| SEQRES | 63 | A | 1522 | G | C | G | C | U | A | G | G | U | C | U | G | U |
| SEQRES | 64 | A | 1522 | G | G | G | U | C | U | C | C | U | G | G | G | G |
| SEQRES | 65 | A | 1522 | G | C | C | G | A | A | G | C | U | A | A | C | G |
| SEQRES | 66 | A | 1522 | C | G | U | U | A | A | G | C | G | C | G | C | C |
| SEQRES | 67 | A | 1522 | G | C | C | U | G | G | G | G | A | G | U | A | C |
| SEQRES | 68 | A | 1522 | G | G | C | C | G | C | A | A | G | G | C | U | G |
| SEQRES | 69 | A | 1522 | A | A | A | C | U | C | A | A | A | G | G | A | A |
| SEQRES | 70 | A | 1522 | U | U | G | A | C | G | G | G | G | G | C | C | C |
| SEQRES | 71 | A | 1522 | G | C | A | C | A | A | G | C | G | G | U | G | G |
| SEQRES | 72 | A | 1522 | A | G | C | A | U | G | U | G | G | U | U | U | A |
| SEQRES | 73 | A | 1522 | A | U | U | C | G | A | A | G | C | A | A | C | G |
| SEQRES | 74 | A | 1522 | C | G | A | A | G | A | A | C | C | U | U | A | C |
| SEQRES | 75 | A | 1522 | C | A | G | G | C | C | U | U | G | A | C | A | U |
| SEQRES | 76 | A | 1522 | G | C | U | A | G | G | A | A | C | C | C | G | G |
| SEQRES | 77 | A | 1522 | G | G | U | G | A | A | A | G | C | C | U | G | G |
| SEQRES | 78 | A | 1522 | G | G | U | G | C | C | C | C | G | C | G | A | G |
| SEQRES | 79 | A | 1522 | G | G | G | A | C | C | C | U | G | A | G | C | A |
| SEQRES | 80 | A | 1522 | C | A | G | G | U | G | C | U | G | C | A | U | G |
| SEQRES | 81 | A | 1522 | G | C | C | G | U | C | G | U | C | A | G | C | U |
| SEQRES | 82 | A | 1522 | C | G | U | G | C | C | G | U | G | A | G | U | U |
| SEQRES | 83 | A | 1522 | G | U | U | G | G | G | U | U | A | A | G | U | C |
| SEQRES | 84 | A | 1522 | C | C | G | C | A | A | C | G | A | G | C | G | C |
| SEQRES | 85 | A | 1522 | A | A | C | C | C | C | G | C | C | C | G | U | U |
| SEQRES | 86 | A | 1522 | A | G | U | U | G | C | C | A | G | C | G | G | U |
| SEQRES | 87 | A | 1522 | U | C | G | G | C | C | G | G | G | C | A | C | U |
| SEQRES | 88 | A | 1522 | C | U | A | A | C | G | G | G | A | C | U | G | C |
| SEQRES | 89 | A | 1522 | C | C | G | C | G | A | A | G | C | G | G | G | A |
| SEQRES | 90 | A | 1522 | A | G | G | A | A | G | G | A | G | G | G | G | A |
| SEQRES | 91 | A | 1522 | C | G | A | C | G | U | C | U | G | G | U | C | A |
| SEQRES | 92 | A | 1522 | G | C | A | U | G | G | C | C | C | U | U | A | C |
| SEQRES | 93 | A | 1522 | G | G | C | C | U | G | G | G | C | G | A | C | A |
| SEQRES | 94 | A | 1522 | C | A | C | G | U | G | C | U | A | C | A | A | U |
| SEQRES | 95 | A | 1522 | G | C | C | C | A | C | U | A | C | A | A | A | G |
| SEQRES | 96 | A | 1522 | C | G | A | U | G | C | C | A | C | C | C | U | G |
| SEQRES | 97 | A | 1522 | C | A | C | C | G | G | A | G | C | A | G | G | A |
| SEQRES | 98 | A | 1522 | A | U | C | G | C | A | A | A | A | G | G | U | U |
| SEQRES | 99 | A | 1522 | G | G | G | C | C | A | A | U | U | G | C | G | A |
| SEQRES | 10 | A | 1522 | A | U | U | G | G | G | G | U | C | U | G | A | G |
| SEQRES | 10 | A | 1522 | A | C | C | C | G | A | C | C | C | C | A | U | G |
| SEQRES | 10 | A | 1522 | A | A | G | C | C | G | A | A | G | U | C | G | A |
| SEQRES | 10 | A | 1522 | U | A | G | U | A | A | U | C | G | C | G | G | C |
| SEQRES | 10 | A | 1522 | U | C | A | G | C | C | A | U | G | C | C | G | C |
| SEQRES | 10 | A | 1522 | G | G | U | G | A | A | U | A | C | G | U | U | C |

| | | | | | | | | | | | | | | |
|---|---|---|---|---|---|---|---|---|---|---|---|---|---|---|
| SEQRES | 10 | A | 1522 | C | C | G | G | G | C | C | U | G | U | A | C |
| SEQRES | 10 | A | 1522 | A | C | A | C | C | G | C | C | C | G | U | C | A |
| SEQRES | 10 | A | 1522 | C | G | C | C | A | U | G | G | A | G | A | C | G |
| SEQRES | 10 | A | 1522 | G | G | C | U | C | U | A | C | C | G | A | A |
| SEQRES | 11 | A | 1522 | G | U | C | G | C | C | G | G | A | G | C | C |
| SEQRES | 11 | A | 1522 | U | A | C | G | G | G | C | A | G | G | C | G | C |
| SEQRES | 11 | A | 1522 | C | G | A | G | G | G | U | A | G | G | C | C |
| SEQRES | 11 | A | 1522 | C | G | U | G | A | C | U | G | G | G | C | G |
| SEQRES | 11 | A | 1522 | A | A | G | U | C | G | U | A | A | A | G |
| SEQRES | 11 | A | 1522 | G | U | A | G | C | U | G | U | A | C | G | G |
| SEQRES | 11 | A | 1522 | A | A | G | G | U | C | G | G | C | U | G | G |
| SEQRES | 11 | A | 1522 | A | U | C | A | C | C | U | C | C | U | U | C |
| SEQRES | 11 | A | 1522 | U | | | | | | | | | | | |
| SEQRES | 1 | B | 76 | G | C | G | G | A | U | U | U | A | 2MG | C | U | C |
| SEQRES | 2 | B | 76 | A | G | H2U | H2U | G | G | G | A | G | A | G | C | M2G |
| SEQRES | 3 | B | 76 | C | C | A | G | A | OMC | U | OMG | A | A | YG | A | PSU |
| SEQRES | 4 | B | 76 | 5MC | U | G | G | A | G | 7MG | U | C | 5MC | U | G | U |
| SEQRES | 5 | B | 76 | G | 5MU | PSU | C | G | 1MA | U | C | C | A | C | A | G |
| SEQRES | 6 | B | 76 | A | A | U | U | C | G | C | A | C | C | A |
| SEQRES | 1 | C | 76 | G | C | G | G | A | U | U | U | A | 2MG | C | U | C |
| SEQRES | 2 | C | 76 | A | G | H2U | H2U | G | G | G | A | G | A | G | C | M2G |
| SEQRES | 3 | C | 76 | C | C | A | G | A | OMC | U | OMG | A | A | YG | A | PSU |
| SEQRES | 4 | C | 76 | 5MC | U | G | G | A | G | 7MG | U | C | 5MC | U | G | U |
| SEQRES | 5 | C | 76 | G | 5MU | PSU | C | G | 1MA | U | C | C | A | C | A | G |
| SEQRES | 6 | C | 76 | A | A | U | U | C | G | C | A | C | C | A |
| SEQRES | 1 | D | 74 | U | C | C | G | U | G | A | 4SU | A | A | C | A | A |
| SEQRES | 2 | D | 74 | A | G | C | G | G | H2U | H2U | A | U | G | U | A | C |
| SEQRES | 3 | D | 74 | C | G | G | A | U | U | U | U | U | A | U | U | C |
| SEQRES | 4 | D | 74 | C | G | A | C | U | A | U | 5MC | G | G | G | G | 5MU |
| SEQRES | 5 | D | 74 | PSU | C | A | A | U | U | C | C | C | G | U | C |
| SEQRES | 6 | D | 74 | G | C | G | G | A | G | C | C | A |
| SEQRES | 1 | 1 | 6 | U | U | U | U | U | U |
| SEQRES | 1 | E | 256 | MET | PRO | VAL | GLU | ILE | THR | VAL | LYS | GLU | LEU | LEU | GLU | ALA |
| SEQRES | 2 | E | 256 | GLY | VAL | HIS | PHE | GLY | HIS | GLU | ARG | LYS | ARG | TRP | ASN | PRO |
| SEQRES | 3 | E | 256 | LYS | PHE | ALA | ARG | TYR | ILE | TYR | ALA | GLU | ARG | ASN | GLY | ILE |
| SEQRES | 4 | E | 256 | HIS | ILE | ILE | ASP | LEU | GLN | LYS | THR | MET | GLU | GLU | LEU | GLU |
| SEQRES | 5 | E | 256 | ARG | THR | PHE | ARG | PHE | ILE | GLU | ASP | LEU | ALA | MET | ARG | GLY |
| SEQRES | 6 | E | 256 | GLY | THR | ILE | LEU | PHE | VAL | GLY | THR | LYS | LYS | GLN | ALA | ALA |
| SEQRES | 7 | E | 256 | ASP | ILE | VAL | ARG | MET | GLU | ALA | GLU | ARG | ALA | GLY | MET | PRO |
| SEQRES | 8 | E | 256 | TYR | VAL | ASN | GLN | ARG | TRP | LEU | GLY | GLY | MET | LEU | THR | ASN |
| SEQRES | 9 | E | 256 | PHE | LYS | THR | ILE | SER | GLN | ARG | VAL | HIS | ARG | LEU | GLU | GLU |
| SEQRES | 10 | E | 256 | LEU | GLU | ALA | LEU | PHE | ALA | SER | PRO | GLU | ILE | GLU | GLU | ARG |
| SEQRES | 11 | E | 256 | PRO | LYS | LYS | GLU | GLN | VAL | ARG | LEU | LYS | HIS | GLU | LEU | GLU |
| SEQRES | 12 | E | 256 | ARG | LEU | GLN | LYS | TYR | LEU | SER | GLY | PHE | ARG | LEU | LEU | LYS |
| SEQRES | 13 | E | 256 | ARG | LEU | PRO | ASP | ALA | ILE | PHE | VAL | VAL | ASP | PRO | THR | LYS |
| SEQRES | 14 | E | 256 | GLU | ALA | ILE | ALA | VAL | ARG | GLU | ALA | ARG | LYS | LEU | PHE | ILE |
| SEQRES | 15 | E | 256 | PRO | VAL | ILE | ALA | LEU | ALA | ASP | THR | ASP | SER | ASP | PRO | ASP |
| SEQRES | 16 | E | 256 | LEU | VAL | ASP | TYR | ILE | ILE | PRO | GLY | ASN | ASP | ASP | ALA | ILE |
| SEQRES | 17 | E | 256 | ARG | SER | ILE | GLN | LEU | ILE | LEU | SER | ARG | ALA | VAL | ASP | LEU |
| SEQRES | 18 | E | 256 | ILE | ILE | GLN | ALA | ARG | GLY | GLY | VAL | VAL | GLU | PRO | SER | PRO |
| SEQRES | 19 | E | 256 | SER | TYR | ALA | LEU | VAL | GLN | GLU | ALA | GLU | ALA | THR | GLU | THR |
| SEQRES | 20 | E | 256 | PRO | GLU | GLY | SER | GLU | VAL | GLU | ALA |
| SEQRES | 1 | F | 239 | MET | GLY | ASN | LYS | ILE | HIS | PRO | ILE | GLY | PHE | ARG | LEU | GLY |
| SEQRES | 2 | F | 239 | ILE | THR | ARG | ASP | TRP | GLU | SER | ARG | TRP | TYR | ALA | GLY | LYS |
| SEQRES | 3 | F | 239 | LYS | GLN | TYR | ARG | HIS | LEU | LEU | LEU | GLU | ASP | ARG | GLY | ILE |
| SEQRES | 4 | F | 239 | ARG | GLY | LEU | LEU | GLU | LYS | GLU | LEU | TYR | SER | ALA | GLY | LEU |
| SEQRES | 5 | F | 239 | ALA | ARG | VAL | ASP | ILE | GLU | ARG | ALA | ALA | ASP | ASN | VAL | ALA |
| SEQRES | 6 | F | 239 | VAL | THR | VAL | HIS | VAL | ALA | LYS | PRO | GLY | VAL | VAL | ILE | GLY |
| SEQRES | 7 | F | 239 | ARG | GLY | GLY | GLU | ARG | ILE | ARG | VAL | LEU | ARG | GLU | GLU | LEU |
| SEQRES | 8 | F | 239 | ALA | LYS | LEU | THR | GLY | LYS | ASN | VAL | ALA | LEU | ASN | VAL | GLN |
| SEQRES | 9 | F | 239 | GLU | VAL | GLN | ASN | PRO | ASN | LEU | SER | ALA | PRO | LEU | VAL | ALA |
| SEQRES | 10 | F | 239 | GLN | ARG | VAL | ALA | GLU | GLN | ILE | GLU | ARG | ARG | PHE | ALA | VAL |
| SEQRES | 11 | F | 239 | ARG | ARG | ALA | ILE | LYS | GLN | ALA | VAL | GLN | ARG | ALA | MET | GLU |
| SEQRES | 12 | F | 239 | SER | GLY | ALA | LYS | GLY | ALA | LYS | VAL | ILE | VAL | SER | GLY | ARG |
| SEQRES | 13 | F | 239 | ILE | GLY | GLY | ALA | GLU | GLN | ALA | ARG | THR | GLU | TRP | ALA | ALA |
| SEQRES | 14 | F | 239 | GLN | GLY | ARG | VAL | PRO | LEU | HIS | THR | LEU | ARG | ALA | ASN | ILE |
| SEQRES | 15 | F | 239 | ASP | TYR | GLY | PHE | ALA | LEU | ALA | ARG | THR | THR | TYR | GLY | VAL |
| SEQRES | 16 | F | 239 | LEU | GLY | VAL | LYS | ALA | TYR | ILE | PHE | LEU | GLY | GLU | VAL | ILE |
| SEQRES | 17 | F | 239 | GLY | GLY | GLN | LYS | PRO | LYS | ALA | ARG | PRO | GLU | LEU | PRO | LYS |
| SEQRES | 18 | F | 239 | ALA | GLU | GLU | ARG | PRO | ARG | ARG | ARG | PRO | ALA | VAL | ARG |
| SEQRES | 19 | F | 239 | VAL | LYS | LYS | GLU | GLU |
| SEQRES | 1 | G | 209 | MET | GLY | ARG | TYR | ILE | GLY | PRO | VAL | CYS | ARG | LEU | CYS | ARG |
| SEQRES | 2 | G | 209 | ARG | GLU | GLY | VAL | LYS | LEU | TYR | LEU | LYS | GLY | GLU | ARG | CYS |
| SEQRES | 3 | G | 209 | TYR | SER | PRO | LYS | CYS | ALA | MET | GLU | ARG | ARG | PRO | TYR | PRO |
| SEQRES | 4 | G | 209 | PRO | GLY | GLN | HIS | GLY | GLN | LYS | ARG | ALA | ARG | ARG | PRO | SER |
| SEQRES | 5 | G | 209 | ASP | TYR | ALA | VAL | ARG | LEU | ARG | GLU | LYS | GLN | LYS | LEU | ARG |
| SEQRES | 6 | G | 209 | ARG | ILE | TYR | GLY | ILE | SER | GLU | ARG | GLN | PHE | ARG | ASN | LEU |
| SEQRES | 7 | G | 209 | PHE | GLU | GLU | ALA | SER | LYS | LYS | LYS | GLY | VAL | THR | GLY | SER |
| SEQRES | 8 | G | 209 | VAL | PHE | LEU | GLY | LEU | LEU | GLU | SER | ARG | LEU | ASP | ASN | VAL |
| SEQRES | 9 | G | 209 | VAL | TYR | ARG | LEU | GLY | PHE | ALA | VAL | SER | ARG | ARG | GLN | ALA |
| SEQRES | 10 | G | 209 | ARG | GLN | LEU | VAL | ARG | HIS | GLY | HIS | ILE | THR | VAL | ASN | GLY |
| SEQRES | 11 | G | 209 | ARG | ARG | VAL | ASP | LEU | PRO | SER | TYR | ARG | VAL | ARG | PRO | GLY |
| SEQRES | 12 | G | 209 | ASP | GLU | ILE | ALA | VAL | ALA | GLY | LYS | SER | ARG | ASN | LEU | GLU |
| SEQRES | 13 | G | 209 | LEU | ILE | ARG | GLN | ASN | LEU | GLU | ALA | MET | LYS | GLY | ARG | LYS |
| SEQRES | 14 | G | 209 | VAL | GLY | PRO | TRP | LEU | SER | LEU | ASP | VAL | GLU | GLY | MET | LYS |
| SEQRES | 15 | G | 209 | GLY | LYS | PHE | LEU | ARG | LEU | PRO | ASP | ARG | GLU | ASP | LEU | ALA |
| SEQRES | 16 | G | 209 | LEU | PRO | VAL | GLN | GLU | ASN | LEU | VAL | ILE | GLU | PHE | TYR | SER |

```
SEQRES  17 G  209  ARG
SEQRES   1 H  162  MET PRO GLU THR ASP PHE GLU GLU LYS MET ILE LEU ILE
SEQRES   2 H  162  ARG ARG THR ALA ARG MET GLN ALA GLY GLY ARG ARG PHE
SEQRES   3 H  162  ARG PHE GLY ALA LEU VAL VAL VAL GLY ASP ARG GLN GLY
SEQRES   4 H  162  ARG VAL GLY LEU GLY PHE GLY LYS ALA PRO GLU VAL PRO
SEQRES   5 H  162  LEU ALA VAL GLN LYS ALA GLY TYR TYR ALA ARG ARG ASN
SEQRES   6 H  162  MET VAL GLU VAL PRO LEU GLN ASN GLY THR ILE PRO HIS
SEQRES   7 H  162  GLU ILE GLU VAL GLU PHE GLY ALA SER LYS ILE VAL LEU
SEQRES   8 H  162  LYS PRO ALA ALA PRO GLY THR GLY VAL ILE GLU VAL ALA
SEQRES   9 H  162  VAL PRO ARG ALA ILE LEU GLU LEU ALA GLY VAL THR ASP
SEQRES  10 H  162  ILE LEU THR LYS GLU LEU GLY SER ARG ASN PRO ILE ASN
SEQRES  11 H  162  ILE ALA TYR ALA THR MET GLU ALA LEU ARG GLN LEU ARG
SEQRES  12 H  162  THR LYS ALA ASP VAL GLU ARG LEU ARG LYS GLY GLU ALA
SEQRES  13 H  162  HIS ALA GLN ALA GLN GLY
SEQRES   1 I  101  MET ARG ARG TYR GLU VAL ASN ILE VAL LEU ASN PRO ASN
SEQRES   2 I  101  LEU ASP GLN SER GLN LEU ALA LEU GLU LYS GLU ILE ILE
SEQRES   3 I  101  GLN ARG ALA LEU GLU ASN TYR GLY ALA ARG VAL GLU LYS
SEQRES   4 I  101  VAL GLU GLU LEU GLY LEU ARG ARG LEU ALA TYR PRO ILE
SEQRES   5 I  101  ALA LYS ASP PRO GLN GLY TYR PHE LEU TRP TYR GLN VAL
SEQRES   6 I  101  GLU MET PRO GLU ASP ARG VAL ASN ASP LEU ALA ARG GLU
SEQRES   7 I  101  LEU ARG ILE ARG ASP ASN VAL ARG ARG VAL MET VAL VAL
SEQRES   8 I  101  LYS SER GLN GLU PRO PHE LEU ALA ASN ALA
SEQRES   1 J  156  MET ALA ARG ARG ARG ARG ALA GLU VAL GLN GLN LEU GLN
SEQRES   2 J  156  PRO ASP LEU VAL TYR GLY ASP VAL LEU VAL THR ALA PHE
SEQRES   3 J  156  ILE ASN LYS ILE MET ARG ASP GLY LYS LYS ASN LEU ALA
SEQRES   4 J  156  ALA ARG ILE PHE TYR ASP ALA CYS LYS ILE ILE GLN GLU
SEQRES   5 J  156  LYS THR GLY GLN GLU PRO LEU LYS VAL PHE LYS GLN ALA
SEQRES   6 J  156  VAL GLU ASN VAL LYS PRO ARG MET GLU VAL ARG SER ARG
SEQRES   7 J  156  ARG VAL GLY GLY ALA ASN TYR GLN VAL PRO MET GLU VAL
SEQRES   8 J  156  SER PRO ARG ARG GLN GLN SER LEU ALA LEU ARG TRP LEU
SEQRES   9 J  156  VAL GLN ALA ALA ASN GLN ARG PRO GLU ARG ARG ALA ALA
SEQRES  10 J  156  VAL ARG ILE ALA HIS GLU LEU MET ASP ALA ALA GLU GLY
SEQRES  11 J  156  LYS GLY GLY ALA VAL LYS LYS LYS GLU ASP VAL GLU ARG
SEQRES  12 J  156  MET ALA GLU ALA ASN ARG ALA TYR ALA HIS TYR ARG TRP
SEQRES   1 K  138  MET LEU THR ASP PRO ILE ALA ASP MET LEU THR ARG ILE
SEQRES   2 K  138  ARG ASN ALA THR ARG VAL TYR LYS GLU SER THR ASP VAL
SEQRES   3 K  138  PRO ALA SER ARG PHE LYS GLU ILE LEU ARG ILE LEU
SEQRES   4 K  138  ALA ARG GLU GLY PHE ILE LYS GLY TYR GLU ARG VAL ASP
SEQRES   5 K  138  VAL ASP GLY LYS PRO TYR LEU ARG VAL TYR LEU LYS TYR
SEQRES   6 K  138  GLY PRO ARG ARG GLN GLY PRO ASP PRO ARG PRO GLU GLN
SEQRES   7 K  138  VAL ILE HIS HIS ILE ARG ARG ILE SER LYS PRO GLY ARG
SEQRES   8 K  138  ARG VAL TYR VAL GLY VAL LYS GLU ILE PRO ARG VAL ARG
SEQRES   9 K  138  ARG GLY LEU GLY ILE ALA ILE LEU SER THR SER LYS GLY
SEQRES  10 K  138  VAL LEU THR ASP ARG GLU ALA ARG LYS LEU GLY VAL GLY
SEQRES  11 K  138  GLY GLU LEU ILE CYS GLU VAL TRP
SEQRES   1 L  128  MET GLU GLN TYR TYR GLY THR GLY ARG ARG LYS GLU ALA
SEQRES   2 L  128  VAL ALA ARG VAL PHE LEU ARG PRO GLY ASN GLY LYS VAL
SEQRES   3 L  128  THR VAL ASN GLY GLN ASP PHE ASN GLU TYR PHE GLN GLY
SEQRES   4 L  128  LEU VAL ARG ALA ALA VAL ALA LEU GLU PRO LEU ARG ALA
SEQRES   5 L  128  VAL ASP ALA LEU GLY ARG PHE ASP ALA TYR ILE THR VAL
SEQRES   6 L  128  ARG GLY GLY GLY LYS SER GLY GLN ILE ASP ALA ILE LYS
SEQRES   7 L  128  LEU GLY ILE ALA ARG ALA LEU VAL GLN TYR ASN PRO ASP
SEQRES   8 L  128  TYR ARG ALA LYS LEU LYS PRO LEU GLY PHE LEU THR ARG
SEQRES   9 L  128  ASP ALA ARG VAL VAL GLU ARG LYS LYS TYR GLY LYS HIS
SEQRES  10 L  128  LYS ALA ARG ARG ALA PRO GLN TYR SER LYS ARG
SEQRES   1 M  105  MET PRO LYS ILE ARG ILE LYS LEU ARG GLY PHE ASP HIS
SEQRES   2 M  105  LYS THR LEU ASP ALA SER ALA GLN LYS ILE VAL GLU ALA
SEQRES   3 M  105  ALA ARG ARG SER GLY ALA GLN VAL SER GLY PRO ILE PRO
SEQRES   4 M  105  LEU PRO THR ARG VAL ARG ARG PHE THR VAL ILE ARG GLY
SEQRES   5 M  105  PRO PHE LYS HIS LYS ASP SER ARG GLU HIS PHE GLU LEU
SEQRES   6 M  105  ARG THR HIS ASN ARG LEU VAL ASP ILE ILE ASN PRO ASN
SEQRES   7 M  105  ARG LYS THR ILE GLU GLN LEU MET THR LEU ASP LEU PRO
SEQRES   8 M  105  THR GLY VAL GLU ILE GLU ILE LYS THR VAL GLY GLY GLY
SEQRES   9 M  105  ARG
SEQRES   1 N  129  MET ALA LYS LYS PRO SER LYS LYS LYS VAL LYS ARG GLN
SEQRES   2 N  129  VAL ALA SER GLY ARG ALA TYR ILE HIS ALA SER PHE ASN
SEQRES   3 N  129  ASN THR ILE VAL THR ILE THR ASP PRO ASP GLY ASN PRO
SEQRES   4 N  129  ILE THR TRP SER SER GLY GLY VAL ILE GLY TYR LYS GLY
SEQRES   5 N  129  SER ARG LYS GLY THR PRO TYR ALA ALA GLN LEU ALA ALA
SEQRES   6 N  129  LEU ASP ALA ALA LYS LYS ALA MET ALA TYR GLY MET GLN
SEQRES   7 N  129  SER VAL ASP VAL ILE VAL ARG GLY THR GLY ALA GLY ARG
SEQRES   8 N  129  GLU GLN ALA ILE ARG ALA LEU GLN ALA SER GLY LEU GLN
SEQRES   9 N  129  VAL LYS SER ILE VAL ASP ASP THR PRO VAL PRO HIS ASN
SEQRES  10 N  129  GLY CYS ARG PRO LYS LYS LYS PHE ARG LYS ALA SER
SEQRES   1 O  135  MET VAL ALA LEU PRO THR ILE ASN GLN LEU VAL ARG LYS
SEQRES   2 O  135  GLY ARG GLU LYS VAL ARG LYS LYS SER LYS VAL PRO ALA
SEQRES   3 O  135  LEU LYS GLY ALA PRO PHE ARG ARG GLY VAL CYS THR VAL
SEQRES   4 O  135  VAL ARG THR VAL THR PRO LYS LYS PRO ASN SER ALA LEU
SEQRES   5 O  135  ARG LYS VAL ALA LYS VAL ARG LEU THR SER GLY TYR GLU
SEQRES   6 O  135  VAL THR ALA TYR ILE PRO GLY GLU GLY HIS ASN LEU GLN
SEQRES   7 O  135  GLU HIS SER VAL VAL LEU ILE ARG GLY GLY ARG VAL LYS
SEQRES   8 O  135  ASP LEU PRO GLY VAL ARG TYR HIS ILE VAL ARG GLY VAL
SEQRES   9 O  135  TYR ASP ALA ALA GLY VAL LYS ASP ARG LYS LYS SER ARG
SEQRES  10 O  135  SER LYS TYR GLY THR LYS LYS PRO LYS GLU ALA ALA LYS
SEQRES  11 O  135  THR ALA ALA LYS LYS
SEQRES   1 P  126  MET ALA ARG ILE ALA GLY VAL GLU ILE PRO ARG ASN LYS
SEQRES   2 P  126  ARG VAL ASP VAL ALA LEU THR TYR ILE TYR GLY ILE GLY
```

```
SEQRES   3 P  126  LYS ALA ARG ALA LYS GLU ALA LEU GLU LYS THR GLY ILE
SEQRES   4 P  126  ASN PRO ALA THR ARG VAL LYS ASP LEU PHE GLU ALA GLU
SEQRES   5 P  126  VAL VAL ARG LEU ARG GLU TYR VAL GLU ASN THR TRP LYS
SEQRES   6 P  126  LEU GLU GLY GLU LEU ARG ALA GLU VAL ALA ALA ASN ILE
SEQRES   7 P  126  LYS ARG LEU MET ASP ILE GLY CYS TYR ARG GLY LEU ARG
SEQRES   8 P  126  HIS ARG ARG GLY LEU PRO VAL ARG GLY GLN ARG THR ARG
SEQRES   9 P  126  THR ASN ALA ARG THR ARG LYS GLY PRO ARG LYS THR VAL
SEQRES  10 P  126  ALA GLY LYS LYS LYS ALA PRO ARG LYS
SEQRES   1 Q   61  MET ALA ARG LYS ALA LEU ILE GLU LYS ALA LYS ARG THR
SEQRES   2 Q   61  PRO LYS PHE LYS VAL ARG ALA TYR THR ARG CYS VAL ARG
SEQRES   3 Q   61  CYS GLY ARG ALA ARG SER VAL TYR ARG PHE PHE GLY LEU
SEQRES   4 Q   61  CYS ARG ILE CYS LEU ARG GLU LEU ALA HIS LYS GLY GLN
SEQRES   5 Q   61  LEU PRO GLY VAL ARG LYS ALA SER TRP
SEQRES   1 R   89  MET PRO ILE THR LYS GLU GLU LYS GLN LYS VAL ILE GLN
SEQRES   2 R   89  GLU PHE ALA ARG PHE PRO GLY ASP THR GLY SER THR GLU
SEQRES   3 R   89  VAL GLN VAL ALA LEU LEU THR LEU ARG ILE ASN ARG LEU
SEQRES   4 R   89  SER GLU HIS LEU LYS VAL HIS LYS LYS ASP HIS HIS SER
SEQRES   5 R   89  HIS ARG GLY LEU LEU MET MET VAL GLY GLN ARG ARG ARG
SEQRES   6 R   89  LEU LEU ARG TYR LEU GLN ARG GLU ASP PRO GLU ARG TYR
SEQRES   7 R   89  ARG ALA LEU ILE GLU LYS LEU GLY ILE ARG GLY
SEQRES   1 S   91  MET VAL LYS ILE ARG LEU ALA ARG PHE GLY SER LYS HIS
SEQRES   2 S   91  ASN PRO HIS TYR PRO HIS TYR ARG ILE VAL VAL THR ASP
SEQRES   3 S   91  ALA ARG ARG LYS ARG ASP GLY LYS TYR ILE GLU LYS ILE
SEQRES   4 S   91  GLY TYR TYR ASP PRO ARG LYS THR THR PRO ASP TRP LEU
SEQRES   5 S   91  LYS VAL ASP VAL GLU ARG ALA ARG TYR TRP LEU SER VAL
SEQRES   6 S   91  GLY ALA GLN PRO THR ASP THR ALA ARG ARG LEU LEU ARG
SEQRES   7 S   91  GLN ALA GLY VAL PHE ARG GLN GLU ALA ARG GLU GLY ALA
SEQRES   1 T  105  MET PRO LYS LYS VAL LEU THR GLY VAL VAL VAL SER ASP
SEQRES   2 T  105  LYS MET GLN LYS THR VAL THR VAL LEU VAL GLU ARG GLN
SEQRES   3 T  105  PHE PRO HIS PRO LEU TYR GLY LYS VAL ILE LYS ARG SER
SEQRES   4 T  105  LYS LYS TYR LEU ALA HIS ASP PRO GLU GLU LYS TYR LYS
SEQRES   5 T  105  LEU GLY ASP VAL VAL GLU ILE ILE GLU SER ARG PRO ILE
SEQRES   6 T  105  SER LYS ARG LYS ARG PHE ARG VAL LEU ARG LEU VAL GLU
SEQRES   7 T  105  SER GLY ARG MET ASP LEU VAL GLU LYS TYR LEU ILE ARG
SEQRES   8 T  105  ARG GLN ASN TYR GLN SER LEU SER LYS ARG GLY GLY LYS
SEQRES   9 T  105  ALA
SEQRES   1 U   88  MET SER THR LYS ASN ALA LYS PRO LYS SER GLU LEU GLN
SEQRES   2 U   88  ARG ARG PRO SER ARG LYS ALA LYS VAL LYS ALA THR LEU
SEQRES   3 U   88  GLY GLU PHE ASP LEU ARG ASP TYR ARG ASN VAL GLU VAL
SEQRES   4 U   88  LEU LYS ARG PHE LEU SER GLU THR GLY LYS ILE LEU PRO
SEQRES   5 U   88  ARG ARG ARG THR GLY LEU SER GLY LYS LYS GLN ARG ILE
SEQRES   6 U   88  LEU ALA LYS THR ILE LYS ARG ALA ARG ILE LEU GLY LEU
SEQRES   7 U   88  LEU PRO PHE THR GLU LYS LEU VAL ARG LYS
SEQRES   1 V   93  MET PRO ARG SER LEU LYS LYS GLY VAL PHE VAL ASP ASP
SEQRES   2 V   93  HIS LEU LEU GLU LYS VAL LEU GLU LEU ASN ALA LYS GLY
SEQRES   3 V   93  GLU LYS ARG LEU ILE LYS THR TRP SER ARG ARG SER THR
SEQRES   4 V   93  ILE VAL PRO GLU MET VAL GLY HIS THR ILE ALA VAL TYR
SEQRES   5 V   93  ASN GLY LYS GLN HIS VAL PRO VAL TYR ILE THR GLU ASN
SEQRES   6 V   93  MET VAL GLY HIS LYS LEU GLY PHE ALA PRO THR ARG
SEQRES   7 V   93  THR TYR ARG GLY HIS GLY LYS GLU ALA LYS ALA THR LYS
SEQRES   8 V   93  LYS LYS
SEQRES   1 W  106  MET ALA GLN LYS LYS PRO LYS ARG ASN LEU SER ALA LEU
SEQRES   2 W  106  LYS ARG HIS ARG GLN SER LEU LYS ARG ARG LEU ARG ASN
SEQRES   3 W  106  LYS ALA LYS LYS SER ALA ILE LYS THR LEU SER LYS LYS
SEQRES   4 W  106  ALA VAL GLN LEU ALA GLN GLN GLY LYS ALA GLU GLU ALA
SEQRES   5 W  106  LEU LYS ILE MET ARG LYS ALA GLU SER LEU ILE ASP LYS
SEQRES   6 W  106  ALA ALA LYS GLY SER THR LEU HIS LYS ASN ALA ALA ALA
SEQRES   7 W  106  ARG ARG LYS SER ARG LEU MET ARG LYS VAL ARG GLN LEU
SEQRES   8 W  106  LEU GLU ALA ALA GLY ALA PRO LEU ILE GLY GLY GLY LEU
SEQRES   9 W  106  SER ALA
SEQRES   1 X   26  GLY LYS GLY ASP ARG ARG THR ARG ARG GLY LYS ILE TRP
SEQRES   2 X   26  ARG GLY THR TYR GLY LYS TYR ARG PRO ARG LYS LYS LYS
MODRES 1GIX 2MG B   10       2N-METHYLGUANOSINE-5'-MONOPHOSPHATE
MODRES 1GIX H2U B   16       5,6-DIHYDROURIDINE-5'-MONOPHOSPHATE
MODRES 1GIX H2U B   17       5,6-DIHYDROURIDINE-5'-MONOPHOSPHATE
MODRES 1GIX M2G B   26       N2-DIMETHYLGUANOSINE-5'-MONOPHOSPHATE
MODRES 1GIX OMC B   32       O2'-METHYLYCYTIDINE-5'-MONOPHOSPHATE
MODRES 1GIX OMG B   34       O2'-METHYLYGUANOSINE-5'-MONOPHOSPHATE
MODRES 1GIX  YG B   37       WYBUTOSINE
MODRES 1GIX PSU B   39       PSEUDOURIDINE-5'-MONOPHOSPHATE
MODRES 1GIX 5MC B   40       5-METHYLCYTIDINE-5'-MONOPHOSPHATE
MODRES 1GIX 7MG B   46
MODRES 1GIX 5MC B   49       5-METHYLCYTIDINE-5'-MONOPHOSPHATE
MODRES 1GIX 5MU B   54       5-METHYLURIDINE 5'-MONOPHOSPHATE
MODRES 1GIX PSU B   55       PSEUDOURIDINE-5'-MONOPHOSPHATE
MODRES 1GIX 1MA B   58
MODRES 1GIX 2MG C   10       2N-METHYLGUANOSINE-5'-MONOPHOSPHATE
MODRES 1GIX H2U C   16       5,6-DIHYDROURIDINE-5'-MONOPHOSPHATE
MODRES 1GIX H2U C   17       5,6-DIHYDROURIDINE-5'-MONOPHOSPHATE
MODRES 1GIX M2G C   26       N2-DIMETHYLGUANOSINE-5'-MONOPHOSPHATE
MODRES 1GIX OMC C   32       O2'-METHYLYCYTIDINE-5'-MONOPHOSPHATE
MODRES 1GIX OMG C   34       O2'-METHYLYGUANOSINE-5'-MONOPHOSPHATE
MODRES 1GIX  YG C   37       WYBUTOSINE
MODRES 1GIX PSU C   39       PSEUDOURIDINE-5'-MONOPHOSPHATE
MODRES 1GIX 5MC C   40       5-METHYLCYTIDINE-5'-MONOPHOSPHATE
MODRES 1GIX 7MG C   46
MODRES 1GIX 5MC C   49       5-METHYLCYTIDINE-5'-MONOPHOSPHATE
```

```
MODRES  1GIX 5MU  C   54      5-METHYLURIDINE 5'-MONOPHOSPHATE
MODRES  1GIX PSU  C   55      PSEUDOURIDINE-5'-MONOPHOSPHATE
MODRES  1GIX 1MA  C   58
MODRES  1GIX 4SU  D    8      4-THIOURIDINE-5'-MONOPHOSPHATE
MODRES  1GIX H2U  D   20      5,6-DIHYDROURIDINE-5'-MONOPHOSPHATE
MODRES  1GIX H2U  D   21      5,6-DIHYDROURIDINE-5'-MONOPHOSPHATE
MODRES  1GIX 5MC  D   49      5-METHYLCYTIDINE-5'-MONOPHOSPHATE
MODRES  1GIX 5MU  D   54      5-METHYLURIDINE 5'-MONOPHOSPHATE
MODRES  1GIX PSU  D   55      PSEUDOURIDINE-5'-MONOPHOSPHATE
HET     2MG  B   10    24
HET     H2U  B   16    20
HET     H2U  B   17    20
HET     M2G  B   26    25
HET     OMC  B   32    21
HET     OMG  B   34    24
HET      YG  B   37    39
HET     PSU  B   39    20
HET     5MC  B   40    21
HET     7MG  B   46    24
HET     5MC  B   49    21
HET     5MU  B   54    21
HET     PSU  B   55    20
HET     1MA  B   58    23
HET     2MG  C   10    24
HET     H2U  C   16    20
HET     H2U  C   17    20
HET     M2G  C   26    25
HET     OMC  C   32    21
HET     OMG  C   34    24
HET      YG  C   37    39
HET     PSU  C   39    20
HET     5MC  C   40    21
HET     7MG  C   46    24
HET     5MC  C   49    21
HET     5MU  C   54    21
HET     PSU  C   55    20
HET     1MA  C   58    23
HET     4SU  D    8    20
HET     H2U  D   20    20
HET     H2U  D   21    20
HET     5MC  D   49    21
HET     5MU  D   54    21
HET     PSU  D   55    20
HETNAM      2MG  2N-METHYLGUANOSINE-5'-MONOPHOSPHATE
HETNAM      H2U  5,6-DIHYDROURIDINE-5'-MONOPHOSPHATE
HETNAM      M2G  N2-DIMETHYLGUANOSINE-5'-MONOPHOSPHATE
HETNAM      OMC  O2'-METHYLCYTIDINE-5'-MONOPHOSPHATE
HETNAM      OMG  O2'-METHYLGUANOSINE-5'-MONOPHOSPHATE
HETNAM       YG  WYBUTOSINE
HETNAM      PSU  PSEUDOURIDINE-5'-MONOPHOSPHATE
HETNAM      5MC  5-METHYLCYTIDINE-5'-MONOPHOSPHATE
HETNAM      7MG  7N-METHYL-8-HYDROGUANOSINE-5'-MONOPHOSPHATE
HETNAM      5MU  5-METHYLURIDINE 5'-MONOPHOSPHATE
HETNAM      1MA  6-HYDRO-1-METHYLADENOSINE-5'-MONOPHOSPHATE
HETNAM      4SU  4-THIOURIDINE-5'-MONOPHOSPHATE
HETSYN       YG  Y-BASE; 1H-IMIDAZO(1,2-ALPHA)PURINE-7-BUTANOIC ACID,4,
HETSYN   2   YG  9-DIHYDRO-ALPHA-((METHOXYCARBONYL)AMINO)-4,6-DIMETHYL-
HETSYN   3   YG  9-OXO-METHYL ESTER
FORMUL   2  2MG     2(C11 H16 N5 O8 P1)
FORMUL   2  H2U     6(C9 H15 N2 O9 P1)
FORMUL   2  M2G     2(C12 H18 N5 O8 P1)
FORMUL   2  OMC     2(C10 H16 N3 O8 P1)
FORMUL   2  OMG     2(C11 H16 N5 O8 P1)
FORMUL   2   YG     2(C21 H29 N6 O12 P1)
FORMUL   2  PSU     5(C9 H13 N2 O9 P1)
FORMUL   2  5MC     5(C10 H16 N3 O8 P1)
FORMUL   2  7MG     2(C11 H18 N5 O8 P1)
FORMUL   2  5MU     3(C10 H15 N2 O9 P1)
FORMUL   2  1MA     2(C11 H18 N5 O7 P1)
FORMUL   4  4SU     C9 H13 N2 O8 P1 S1
LINK         O3*     A B   9              P    2MG B  10
LINK         O3* 2MG B  10              P      C B  11
LINK         O3*   G B  15              P    H2U B  16
LINK         O3* H2U B  16              P    H2U B  17
LINK         O3* H2U B  17              P      G B  18
LINK         O3*   C B  25              P    M2G B  26
LINK         O3* M2G B  26              P      C B  27
LINK         O3*   A B  31              P    OMC B  32
LINK         O3* OMC B  32              P      U B  33
LINK         O3*   U B  33              P    OMG B  34
LINK         O3* OMG B  34              P      A B  35
LINK         O3*   A B  36              P     YG B  37
LINK         O3*  YG B  37              P      A B  38
LINK         O3*   A B  38              P    PSU B  39
LINK         O3* PSU B  39              P    5MC B  40
LINK         O3* 5MC B  40              P      U B  41
LINK         O3*   G B  45              P    7MG B  46
```

```
LINK        O3*  7MG B  46              P    U   B  47
LINK        O3*    C B  48              P  5MC B  49
LINK        O3*  5MC B  49              P    U   B  50
LINK        O3*    G B  53              P  5MU B  54
LINK        O3*  5MU B  54              P  PSU B  55
LINK        O3*  PSU B  55              P    C   B  56
LINK        O3*    G B  57              P  1MA B  58
LINK        O3*  1MA B  58              P    U   B  59
LINK        O3*    A C   9              P  2MG C  10
LINK        O3*  2MG C  10              P    C   C  11
LINK        O3*    G C  15              P  H2U C  16
LINK        O3*  H2U C  16              P  H2U C  17
LINK        O3*  H2U C  17              P    G   C  18
LINK        O3*  M2G C  26              P    C   C  27
LINK        O3*    A C  31              P  OMC C  32
LINK        O3*  OMC C  32              P    U   C  33
LINK        O3*    U C  33              P  OMG C  34
LINK        O3*  OMG C  34              P    A   C  35
LINK        O3*    A C  36              P   YG C  37
LINK        O3*   YG C  37              P    A   C  38
LINK        O3*    A C  38              P  PSU C  39
LINK        O3*  PSU C  39              P  5MC C  40
LINK        O3*  5MC C  40              P    U   C  41
LINK        O3*    G C  45              P  7MG C  46
LINK        O3*  7MG C  46              P    U   C  47
LINK        O3*    C C  48              P  5MC C  49
LINK        O3*  5MC C  49              P    U   C  50
LINK        O3*    G C  53              P  5MU C  54
LINK        O3*  5MU C  54              P  PSU C  55
LINK        O3*  PSU C  55              P    C   C  56
LINK        O3*    G C  57              P  1MA C  58
LINK        O3*  1MA C  58              P    U   C  59
LINK        O3*  4SU D   8              P    A   D   9
LINK        O3*    G D  19              P  H2U D  20
LINK        O3*  H2U D  20              P  H2U D  21
LINK        O3*  H2U D  21              P    A   D  22
LINK        O3*  5MC D  49              P    G   D  50
LINK        O3*    G D  53              P  5MU D  54
LINK        O3*  5MU D  54              P  PSU D  55
LINK        O3*  PSU D  55              P    C   D  56
CRYST1   507.200   507.200   803.660  90.00  90.00  90.00 I 4 2 2      32
ORIGX1     1.000000  0.000000  0.000000        0.00000
ORIGX2     0.000000  1.000000  0.000000        0.00000
ORIGX3     0.000000  0.000000  1.000000        0.00000
SCALE1     0.001972  0.000000  0.000000        0.00000
SCALE2     0.000000  0.001972  0.000000        0.00000
SCALE3     0.000000  0.000000  0.001244        0.00000
ATOM     1  P    U A   1     -50.761  76.728 327.188  1.00  0.00           P
ATOM     2  P    U A   2     -50.827  73.756 332.171  1.00  0.00           P
ATOM     3  P    G A   3     -48.559  75.043 336.960  1.00  0.00           P
ATOM     4  P    U A   4     -43.808  73.431 332.621  1.00  0.00           P
ATOM     5  P    U A   5     -45.103  76.659 329.705  1.00  0.00           P
ATOM     6  P    G A   6     -44.719  80.005 327.215  1.00  0.00           P
ATOM     7  P    G A   7     -40.138  81.231 324.258  1.00  0.00           P
ATOM     8  P    A A   8     -38.842  81.559 319.106  1.00  0.00           P
ATOM     9  P    G A   9     -33.520  80.139 315.004  1.00  0.00           P
ATOM    10  P    A A  10     -32.835  81.728 308.951  1.00  0.00           P
ATOM    11  P    G A  11     -31.745  84.356 303.601  1.00  0.00           P
ATOM    12  P    U A  12     -29.194  88.147 300.052  1.00  0.00           P
ATOM    13  P    U A  13     -24.421  90.810 299.125  1.00  0.00           P
ATOM    14  P    U A  14     -19.617  92.341 297.880  1.00  0.00           P
ATOM    15  P    G A  15     -17.406  90.464 293.208  1.00  0.00           P
ATOM    16  P    A A  16     -20.868  85.834 293.212  1.00  0.00           P
ATOM    17  P    U A  17     -20.697  81.423 296.817  1.00  0.00           P
ATOM    18  P    C A  18     -20.059  79.360 301.966  1.00  0.00           P
ATOM    19  P    C A  19     -18.366  79.875 308.426  1.00  0.00           P
ATOM    20  P    U A  20     -18.024  83.254 312.572  1.00  0.00           P
ATOM    21  P    G A  21     -18.381  88.204 315.469  1.00  0.00           P
ATOM    22  P    G A  22     -21.444  93.683 315.000  1.00  0.00           P
ATOM    23  P    C A  23     -25.242  98.105 313.664  1.00  0.00           P
ATOM    24  P    U A  24     -30.594  99.347 311.733  1.00  0.00           P
ATOM    25  P    C A  25     -35.966  97.894 309.890  1.00  0.00           P
ATOM    26  P    A A  26     -40.356  94.929 309.945  1.00  0.00           P
ATOM    27  P    G A  27     -44.206  93.719 312.685  1.00  0.00           P
ATOM    28  P    G A  28     -46.833  95.377 316.896  1.00  0.00           P
ATOM    29  P    G A  29     -48.005  98.532 321.541  1.00  0.00           P
ATOM    30  P    U A  30     -47.706 103.855 324.531  1.00  0.00           P
ATOM    31  P    G A  31     -46.643 108.970 326.500  1.00  0.00           P
ATOM    32  P    A A  32     -50.015 112.703 324.128  1.00  0.00           P
ATOM    33  P    A A  33     -49.448 116.003 319.031  1.00  0.00           P
ATOM    34  P    C A  34     -48.783 118.853 313.782  1.00  0.00           P
ATOM    35  P    G A  35     -50.056 118.375 308.208  1.00  0.00           P
ATOM    36  P    C A  36     -53.160 116.665 303.946  1.00  0.00           P
ATOM    37  P    U A  37     -58.647 114.471 303.003  1.00  0.00           P
ATOM    38  P    G A  38     -62.916 113.471 304.778  1.00  0.00           P
ATOM    39  P    G A  39     -66.232 113.667 308.331  1.00  0.00           P
ATOM    40  P    C A  40     -69.587 112.075 313.927  1.00  0.00           P
```

```
ATOM   41  P   G A  41    -70.767 111.027 319.577  1.00  0.00           P
ATOM   42  P   G A  42    -70.263 108.726 325.300  1.00  0.00           P
ATOM   43  P   C A  43    -67.820 107.001 330.097  1.00  0.00           P
ATOM   44  P   G A  44    -62.785 106.603 333.510  1.00  0.00           P
ATOM   45  P   U A  45    -56.683 108.772 333.504  1.00  0.00           P
ATOM   46  P   G A  46    -52.512 112.853 331.528  1.00  0.00           P
ATOM   47  P   C A  47    -52.404 118.056 329.953  1.00  0.00           P
ATOM   48  P   C A  48    -46.522 119.671 330.790  1.00  0.00           P
ATOM   49  P   U A  49    -41.445 118.750 329.030  1.00  0.00           P
ATOM   50  P   A A  50    -37.348 124.347 327.786  1.00  0.00           P
ATOM   51  P   A A  51    -42.329 126.167 331.995  1.00  0.00           P
ATOM   52  P   G A  52    -37.609 128.074 334.232  1.00  0.00           P
ATOM   53  P   A A  53    -40.914 133.211 335.444  1.00  0.00           P
ATOM   54  P   C A  54    -44.561 137.419 335.965  1.00  0.00           P
ATOM   55  P   A A  55    -51.267 139.239 336.420  1.00  0.00           P
ATOM   56  P   U A  56    -55.342 142.281 336.837  1.00  0.00           P
ATOM   57  P   G A  57    -60.425 140.868 338.894  1.00  0.00           P
ATOM   58  P   C A  58    -63.855 137.381 341.923  1.00  0.00           P
ATOM   59  P   A A  59    -63.047 132.650 345.787  1.00  0.00           P
ATOM   60  P   A A  60    -60.712 127.894 348.416  1.00  0.00           P
ATOM   61  P   G A  61    -60.399 131.470 352.562  1.00  0.00           P
ATOM   62  P   U A  62    -66.421 130.094 355.310  1.00  0.00           P
ATOM   63  P   C A  63    -70.160 128.264 359.808  1.00  0.00           P
ATOM   64  P   G A  64    -72.625 130.575 364.248  1.00  0.00           P
ATOM   65  P   U A  65    -73.746 132.392 370.459  1.00  0.00           P
ATOM   66  P   G A  66    -68.691 129.704 372.272  1.00  0.00           P
ATOM   67  P   C A  67    -69.315 133.971 376.329  1.00  0.00           P
ATOM   68  P   G A  68    -69.755 139.550 377.233  1.00  0.00           P
ATOM   69  P   G A  69    -70.852 145.595 375.686  1.00  0.00           P
ATOM   70  P   G A  73    -71.274 148.756 368.867  1.00  0.00           P
ATOM   71  P   C A  74    -72.995 152.431 365.213  1.00  0.00           P
ATOM   72  P   C A  75    -76.845 153.289 360.856  1.00  0.00           P
ATOM   73  P   G A  76    -81.876 152.078 359.201  1.00  0.00           P
ATOM   74  P   C A  77    -87.087 149.039 360.827  1.00  0.00           P
ATOM   75  P   G A  78    -90.874 145.960 363.933  1.00  0.00           P
ATOM   76  P   G A  79    -93.599 144.674 368.689  1.00  0.00           P
ATOM   77  P   G A  80    -95.684 146.859 374.467  1.00  0.00           P
ATOM   78  P   G A  81    -94.829 151.955 378.536  1.00  0.00           P
ATOM   79  P   U A  82    -95.496 157.561 376.837  1.00  0.00           P
ATOM   80  P   U A  84    -94.636 159.374 372.662  1.00  0.00           P
ATOM   81  P   U A  85    -93.492 160.594 365.968  1.00  0.00           P
ATOM   82  P   U A  86    -88.267 160.063 363.625  1.00  0.00           P
ATOM   83  P   A A  87    -83.141 159.867 367.002  1.00  0.00           P
ATOM   84  P   C A  88    -79.605 158.113 370.962  1.00  0.00           P
ATOM   85  P   U A  89    -78.643 154.645 375.468  1.00  0.00           P
ATOM   86  P   C A  90    -78.783 149.187 378.201  1.00  0.00           P
ATOM   87  P   C A  91    -78.356 143.651 376.878  1.00  0.00           P
ATOM   88  P   G A  92    -79.318 138.685 373.949  1.00  0.00           P
ATOM   89  P   U A  93    -80.220 135.518 369.287  1.00  0.00           P
ATOM   90  P   G A  95    -79.859 135.300 363.444  1.00  0.00           P
ATOM   91  P   G A  96    -78.292 136.902 358.984  1.00  0.00           P
ATOM   92  P   U A  97    -74.998 139.429 356.894  1.00  0.00           P
ATOM   93  P   C A  99    -70.510 141.009 356.594  1.00  0.00           P
ATOM   94  P   A A 101    -65.605 141.646 357.633  1.00  0.00           P
ATOM   95  P   G A 102    -60.214 141.117 362.111  1.00  0.00           P
ATOM   96  P   C A 103    -57.423 141.338 366.680  1.00  0.00           P
ATOM   97  P   G A 104    -57.280 137.103 370.925  1.00  0.00           P
ATOM   98  P   G A 105    -57.280 131.445 371.867  1.00  0.00           P
ATOM   99  P   C A 106    -57.197 125.898 369.866  1.00  0.00           P
ATOM  100  P   G A 107    -56.384 122.359 366.367  1.00  0.00           P
ATOM  101  P   G A 108    -52.878 121.874 362.209  1.00  0.00           P
ATOM  102  P   A A 109    -48.965 123.600 358.462  1.00  0.00           P
ATOM  103  P   C A 110    -51.100 118.545 353.032  1.00  0.00           P
ATOM  104  P   G A 111    -52.502 116.515 350.592  1.00  0.00           P
ATOM  105  P   G A 112    -55.014 116.842 344.984  1.00  0.00           P
ATOM  106  P   G A 113    -51.598 117.739 341.724  1.00  0.00           P
ATOM  107  P   U A 114    -48.007 118.996 337.681  1.00  0.00           P
ATOM  108  P   G A 115    -42.506 118.659 335.544  1.00  0.00           P
ATOM  109  P   A A 116    -36.513 117.979 334.956  1.00  0.00           P
ATOM  110  P   G A 117    -31.822 119.629 336.220  1.00  0.00           P
ATOM  111  P   U A 118    -27.834 118.847 340.493  1.00  0.00           P
ATOM  112  P   A A 119    -25.960 114.340 343.606  1.00  0.00           P
ATOM  113  P   A A 120    -23.060 110.111 345.529  1.00  0.00           P
ATOM  114  P   C A 121    -24.913 108.630 351.393  1.00  0.00           P
ATOM  115  P   G A 122    -28.200 110.719 354.497  1.00  0.00           P
ATOM  116  P   C A 123    -33.674 110.648 352.558  1.00  0.00           P
ATOM  117  P   G A 124    -37.657 107.490 349.705  1.00  0.00           P
ATOM  118  P   U A 125    -40.108 102.381 349.357  1.00  0.00           P
ATOM  119  P   G A 126    -41.025  97.687 352.373  1.00  0.00           P
ATOM  120  P   G A 127    -40.347  94.658 357.820  1.00  0.00           P
ATOM  121  P   G A 128    -37.957  95.975 364.089  1.00  0.00           P
ATOM  122  P   U A 129    -35.618  97.557 369.012  1.00  0.00           P
ATOM  123  P   G A 129A   -33.832 100.900 373.672  1.00  0.00           P
ATOM  124  P   A A 130    -28.899 103.362 375.714  1.00  0.00           P
ATOM  125  P   C A 131    -35.257 109.538 373.077  1.00  0.00           P
ATOM  126  P   C A 132    -43.337 111.068 373.969  1.00  0.00           P
ATOM  127  P   U A 133    -46.422 115.094 372.012  1.00  0.00           P
```

```
ATOM  128  P  A A 134   -51.513 115.453 369.891  1.00  0.00           P
ATOM  129  P  C A 135   -56.319 117.602 370.782  1.00  0.00           P
ATOM  130  P  C A 136   -61.367 115.908 370.029  1.00  0.00           P
ATOM  131  P  C A 137   -64.253 111.556 370.921  1.00  0.00           P
ATOM  132  P  G A 138   -65.444 107.190 374.087  1.00  0.00           P
ATOM  133  P  G A 139   -64.912 104.880 378.996  1.00  0.00           P
ATOM  134  P  A A 140   -63.269 105.048 384.622  1.00  0.00           P
ATOM  135  P  A A 141   -61.810 107.588 389.280  1.00  0.00           P
ATOM  136  P  G A 142   -61.599 113.233 391.794  1.00  0.00           P
ATOM  137  P  A A 143   -63.401 119.248 391.403  1.00  0.00           P
ATOM  138  P  G A 144   -64.849 126.010 393.092  1.00  0.00           P
ATOM  139  P  G A 145   -65.350 131.638 396.053  1.00  0.00           P
ATOM  140  P  G A 146   -63.391 137.317 395.982  1.00  0.00           P
ATOM  141  P  G A 147   -60.321 142.291 393.848  1.00  0.00           P
ATOM  142  P  G A 148   -57.485 145.866 389.879  1.00  0.00           P
ATOM  143  P  A A 149   -55.523 148.022 384.667  1.00  0.00           P
ATOM  144  P  C A 150   -53.870 149.099 378.785  1.00  0.00           P
ATOM  145  P  A A 151   -54.501 148.999 372.738  1.00  0.00           P
ATOM  146  P  A A 152   -58.815 149.502 367.709  1.00  0.00           P
ATOM  147  P  C A 153   -63.871 150.392 365.964  1.00  0.00           P
ATOM  148  P  C A 154   -66.099 155.517 367.187  1.00  0.00           P
ATOM  149  P  C A 155   -64.657 160.716 368.062  1.00  0.00           P
ATOM  150  P  G A 156   -60.578 164.781 367.051  1.00  0.00           P
ATOM  151  P  G A 157   -55.831 166.840 364.623  1.00  0.00           P
ATOM  152  P  G A 158   -51.086 165.994 360.719  1.00  0.00           P
ATOM  153  P  G A 159   -47.899 164.410 356.470  1.00  0.00           P
ATOM  154  P  A A 160   -48.310 162.664 351.427  1.00  0.00           P
ATOM  155  P  A A 161   -53.449 159.249 351.533  1.00  0.00           P
ATOM  156  P  A A 162   -54.746 153.342 351.749  1.00  0.00           P
ATOM  157  P  C A 163   -54.034 148.587 354.582  1.00  0.00           P
ATOM  158  P  U A 164   -50.483 149.144 360.342  1.00  0.00           P
ATOM  159  P  C A 165   -47.591 151.818 364.917  1.00  0.00           P
ATOM  160  P  G A 166   -47.131 154.458 369.784  1.00  0.00           P
ATOM  161  P  G A 167   -49.367 156.801 374.696  1.00  0.00           P
ATOM  162  P  G A 168   -53.268 157.454 378.628  1.00  0.00           P
ATOM  163  P  C A 169   -58.221 155.396 381.237  1.00  0.00           P
ATOM  164  P  U A 170   -62.068 151.668 382.606  1.00  0.00           P
ATOM  165  P  A A 171   -64.007 145.977 382.652  1.00  0.00           P
ATOM  166  P  A A 172   -64.976 140.600 383.046  1.00  0.00           P
ATOM  167  P  U A 173   -63.487 134.707 382.394  1.00  0.00           P
ATOM  168  P  C A 174   -59.449 132.335 379.266  1.00  0.00           P
ATOM  169  P  C A 175   -54.677 133.489 378.871  1.00  0.00           P
ATOM  170  P  C A 176   -50.557 134.128 382.607  1.00  0.00           P
ATOM  171  P  C A 177   -48.220 134.581 388.210  1.00  0.00           P
ATOM  172  P  C A 178   -47.861 133.616 393.961  1.00  0.00           P
ATOM  173  P  A A 179   -48.246 130.099 397.018  1.00  0.00           P
ATOM  174  P  U A 180   -51.198 125.527 399.537  1.00  0.00           P
ATOM  175  P  G A 181   -52.753 120.277 399.254  1.00  0.00           P
ATOM  176  P  U A 182   -51.630 114.723 395.983  1.00  0.00           P
ATOM  177  P  G A 183   -52.018 110.674 394.176  1.00  0.00           P
ATOM  178  P  G A 184   -47.302 110.491 389.154  1.00  0.00           P
ATOM  179  P  A A 185   -42.585 112.628 385.996  1.00  0.00           P
ATOM  180  P  C A 186   -37.507 114.881 385.255  1.00  0.00           P
ATOM  181  P  C A 186A  -32.374 115.299 387.678  1.00  0.00           P
ATOM  182  P  C A 186B  -28.219 114.239 391.156  1.00  0.00           P
ATOM  183  P  G A 186C  -26.682 110.177 395.220  1.00  0.00           P
ATOM  184  P  C A 186D  -27.157 104.958 397.289  1.00  0.00           P
ATOM  185  P  C A 186E  -29.700  99.611 396.538  1.00  0.00           P
ATOM  186  P  C A 186F  -32.074  95.205 394.032  1.00  0.00           P
ATOM  187  P  C A 187   -34.029  92.385 389.009  1.00  0.00           P
ATOM  188  P  U A 188   -33.126  93.236 382.891  1.00  0.00           P
ATOM  189  P  U A 189   -30.261  98.498 378.579  1.00  0.00           P
ATOM  190  P  G A 190   -28.965 104.596 381.873  1.00  0.00           P
ATOM  191  P  G A 191A  -35.407 106.600 381.220  1.00  0.00           P
ATOM  192  P  G A 191B  -40.142 104.812 382.379  1.00  0.00           P
ATOM  193  P  G A 191C  -43.381 104.251 387.443  1.00  0.00           P
ATOM  194  P  U A 191D  -44.355 104.613 393.324  1.00  0.00           P
ATOM  195  P  G A 191E  -43.322 106.992 398.529  1.00  0.00           P
ATOM  196  P  U A 191F  -42.053 111.207 402.048  1.00  0.00           P
ATOM  197  P  G A 191   -40.555 116.843 403.029  1.00  0.00           P
ATOM  198  P  U A 192   -39.947 121.898 400.873  1.00  0.00           P
ATOM  199  P  C A 193   -41.029 125.788 396.520  1.00  0.00           P
ATOM  200  P  C A 194   -43.899 127.021 391.748  1.00  0.00           P
ATOM  201  P  A A 195   -48.349 127.481 388.624  1.00  0.00           P
ATOM  202  P  A A 196   -53.005 128.100 386.319  1.00  0.00           P
ATOM  203  P  A A 197   -57.722 130.160 383.506  1.00  0.00           P
ATOM  204  P  G A 198   -63.367 130.288 384.699  1.00  0.00           P
ATOM  205  P  G A 199   -69.094 132.765 381.443  1.00  0.00           P
ATOM  206  P  G A 200   -74.012 132.385 377.988  1.00  0.00           P
ATOM  207  P  C A 201   -79.174 130.483 376.350  1.00  0.00           P
ATOM  208  P  U A 208   -84.731 127.115 377.305  1.00  0.00           P
ATOM  209  P  U A 209   -85.124 124.268 382.124  1.00  0.00           P
ATOM  210  P  U A 210   -82.959 123.041 387.085  1.00  0.00           P
ATOM  211  P  G A 216   -80.916 117.871 390.067  1.00  0.00           P
ATOM  212  P  C A 217   -76.360 115.166 385.452  1.00  0.00           P
ATOM  213  P  C A 218   -74.257 115.351 379.165  1.00  0.00           P
ATOM  214  P  C A 219   -71.703 117.322 374.626  1.00  0.00           P
```

```
ATOM   215  P     G A 220     -66.698 119.633 372.562  1.00  0.00           P
ATOM   216  P     C A 221     -60.915 121.102 375.326  1.00  0.00           P
ATOM   217  P     U A 222     -56.228 121.717 378.155  1.00  0.00           P
ATOM   218  P     U A 223     -52.067 119.556 380.727  1.00  0.00           P
ATOM   219  P     C A 224     -49.089 114.906 381.554  1.00  0.00           P
ATOM   220  P     C A 225     -48.130 109.130 380.855  1.00  0.00           P
ATOM   221  P     G A 226     -48.789 103.881 378.343  1.00  0.00           P
ATOM   222  P     G A 227     -51.095 101.376 373.357  1.00  0.00           P
ATOM   223  P     A A 228     -53.111 100.436 369.326  1.00  0.00           P
ATOM   224  P     U A 229     -53.591 103.122 364.428  1.00  0.00           P
ATOM   225  P     G A 230     -51.939 105.167 360.376  1.00  0.00           P
ATOM   226  P     G A 231     -47.520 107.753 357.819  1.00  0.00           P
ATOM   227  P     G A 232     -37.004 113.058 360.229  1.00  0.00           P
ATOM   228  P     C A 233     -31.524 112.618 361.201  1.00  0.00           P
ATOM   229  P     C A 234     -27.584 108.491 361.498  1.00  0.00           P
ATOM   230  P     C A 235     -25.211 103.596 360.447  1.00  0.00           P
ATOM   231  P     G A 236     -24.795  98.296 357.470  1.00  0.00           P
ATOM   232  P     C A 237     -24.620  94.910 353.360  1.00  0.00           P
ATOM   233  P     G A 238     -25.716  95.181 347.703  1.00  0.00           P
ATOM   234  P     U A 239     -26.273  98.182 342.857  1.00  0.00           P
ATOM   235  P     C A 240     -26.809 101.782 338.437  1.00  0.00           P
ATOM   236  P     C A 241     -21.956 102.646 334.447  1.00  0.00           P
ATOM   237  P     C A 242     -15.809 104.175 332.615  1.00  0.00           P
ATOM   238  P     A A 243     -12.114 105.378 332.945  1.00  0.00           P
ATOM   239  P     U A 244      -6.723 106.326 332.964  1.00  0.00           P
ATOM   240  P     C A 245      -9.530 111.750 332.757  1.00  0.00           P
ATOM   241  P     A A 246      -6.091 110.716 338.105  1.00  0.00           P
ATOM   242  P     G A 247      -2.206 110.892 343.130  1.00  0.00           P
ATOM   243  P     C A 248      -5.127 114.947 347.254  1.00  0.00           P
ATOM   244  P     U A 249      -8.916 117.979 350.132  1.00  0.00           P
ATOM   245  P     A A 250     -10.651 119.751 354.606  1.00  0.00           P
ATOM   246  P     G A 251     -10.136 119.599 359.078  1.00  0.00           P
ATOM   247  P     U A 252     -15.773 118.159 359.044  1.00  0.00           P
ATOM   248  P     U A 253     -15.303 112.905 359.947  1.00  0.00           P
ATOM   249  P     G A 254     -15.887 110.208 364.858  1.00  0.00           P
ATOM   250  P     G A 255     -16.281 109.631 370.927  1.00  0.00           P
ATOM   251  P     U A 256     -16.263 111.050 376.493  1.00  0.00           P
ATOM   252  P     G A 257     -18.717 114.829 380.158  1.00  0.00           P
ATOM   253  P     G A 258     -22.445 119.393 381.054  1.00  0.00           P
ATOM   254  P     G A 259     -26.973 122.858 377.799  1.00  0.00           P
ATOM   255  P     G A 260     -30.853 125.311 374.063  1.00  0.00           P
ATOM   256  P     U A 261     -35.099 123.217 370.770  1.00  0.00           P
ATOM   257  P     A A 262     -39.038 119.549 369.744  1.00  0.00           P
ATOM   258  P     A A 263     -36.358 115.938 373.027  1.00  0.00           P
ATOM   259  P     U A 264     -31.378 112.938 372.633  1.00  0.00           P
ATOM   260  P     G A 265     -26.235 111.509 372.154  1.00  0.00           P
ATOM   261  P     G A 266     -21.806 113.863 369.117  1.00  0.00           P
ATOM   262  P     C A 267     -22.232 114.257 362.217  1.00  0.00           P
ATOM   263  P     C A 268     -22.312 119.764 361.722  1.00  0.00           P
ATOM   264  P     C A 269     -20.116 124.579 364.169  1.00  0.00           P
ATOM   265  P     A A 270     -16.351 127.180 368.098  1.00  0.00           P
ATOM   266  P     C A 271     -11.705 127.182 371.456  1.00  0.00           P
ATOM   267  P     C A 272      -7.233 123.775 373.432  1.00  0.00           P
ATOM   268  P     A A 273      -3.971 118.958 373.192  1.00  0.00           P
ATOM   269  P     A A 274      -1.535 114.206 370.753  1.00  0.00           P
ATOM   270  P     G A 275      -3.323 109.465 365.691  1.00  0.00           P
ATOM   271  P     G A 276      -8.829 106.710 362.855  1.00  0.00           P
ATOM   272  P     C A 277     -12.703 105.287 359.082  1.00  0.00           P
ATOM   273  P     G A 278     -12.936 103.568 353.933  1.00  0.00           P
ATOM   274  P     A A 279     -11.285 101.005 349.058  1.00  0.00           P
ATOM   275  P     C A 280     -10.491  96.728 345.065  1.00  0.00           P
ATOM   276  P     G A 281     -15.564 100.276 345.499  1.00  0.00           P
ATOM   277  P     A A 282     -15.395 105.114 343.980  1.00  0.00           P
ATOM   278  P     C A 283     -14.744 109.460 347.501  1.00  0.00           P
ATOM   279  P     G A 284     -14.171 115.915 346.159  1.00  0.00           P
ATOM   280  P     G A 285     -15.256 118.955 340.991  1.00  0.00           P
ATOM   281  P     G A 286     -18.149 118.629 335.931  1.00  0.00           P
ATOM   282  P     U A 287     -25.855 115.733 332.654  1.00  0.00           P
ATOM   283  P     A A 288     -30.448 112.295 335.702  1.00  0.00           P
ATOM   284  P     G A 289     -34.715 114.921 339.560  1.00  0.00           P
ATOM   285  P     C A 290     -35.053 109.583 341.759  1.00  0.00           P
ATOM   286  P     C A 291     -35.797 103.930 342.609  1.00  0.00           P
ATOM   287  P     G A 292     -39.346  99.037 342.346  1.00  0.00           P
ATOM   288  P     G A 293     -44.881  97.069 338.248  1.00  0.00           P
ATOM   289  P     U A 294     -46.868  96.119 333.581  1.00  0.00           P
ATOM   290  P     C A 295     -46.250  96.675 328.045  1.00  0.00           P
ATOM   291  P     U A 296     -43.661  94.476 323.623  1.00  0.00           P
ATOM   292  P     G A 297     -39.822  90.486 321.419  1.00  0.00           P
ATOM   293  P     A A 298     -38.098  85.399 322.549  1.00  0.00           P
ATOM   294  P     G A 299     -39.440  85.202 328.195  1.00  0.00           P
ATOM   295  P     A A 300     -36.265  85.844 333.838  1.00  0.00           P
ATOM   296  P     G A 301     -31.766  88.892 335.899  1.00  0.00           P
ATOM   297  P     G A 302     -29.201  94.192 332.941  1.00  0.00           P
ATOM   298  P     A A 303     -29.168  98.846 329.871  1.00  0.00           P
ATOM   299  P     U A 304     -32.452 103.855 329.317  1.00  0.00           P
ATOM   300  P     G A 305     -37.471 107.254 332.704  1.00  0.00           P
ATOM   301  P     G A 306     -42.473 107.154 335.834  1.00  0.00           P
```

```
ATOM   302  P   C A 307   -47.682 110.564 333.197  1.00  0.00           P
ATOM   303  P   C A 308   -51.833 110.700 337.027  1.00  0.00           P
ATOM   304  P   G A 309   -53.684 108.039 341.381  1.00  0.00           P
ATOM   305  P   G A 310   -51.876 106.366 347.502  1.00  0.00           P
ATOM   306  P   C A 311   -47.352 107.916 351.175  1.00  0.00           P
ATOM   307  P   C A 312   -41.994 110.900 353.091  1.00  0.00           P
ATOM   308  P   A A 313   -37.677 115.742 351.762  1.00  0.00           P
ATOM   309  P   C A 314   -36.476 121.780 349.722  1.00  0.00           P
ATOM   310  P   A A 315   -38.964 125.278 346.723  1.00  0.00           P
ATOM   311  P   G A 316   -40.811 130.636 344.260  1.00  0.00           P
ATOM   312  P   G A 317   -35.872 129.340 342.936  1.00  0.00           P
ATOM   313  P   G A 318   -31.029 128.383 345.641  1.00  0.00           P
ATOM   314  P   G A 319   -29.412 128.233 349.389  1.00  0.00           P
ATOM   315  P   C A 320   -29.128 129.144 356.904  1.00  0.00           P
ATOM   316  P   A A 321   -31.422 129.896 361.912  1.00  0.00           P
ATOM   317  P   C A 322   -36.849 132.037 365.917  1.00  0.00           P
ATOM   318  P   U A 323   -41.770 132.676 368.422  1.00  0.00           P
ATOM   319  P   G A 324   -46.522 130.085 369.243  1.00  0.00           P
ATOM   320  P   A A 325   -48.628 124.031 368.749  1.00  0.00           P
ATOM   321  P   G A 326   -44.277 122.156 367.140  1.00  0.00           P
ATOM   322  P   A A 327   -41.805 121.575 363.036  1.00  0.00           P
ATOM   323  P   C A 328   -39.394 123.400 358.840  1.00  0.00           P
ATOM   324  P   A A 329   -39.051 126.979 355.934  1.00  0.00           P
ATOM   325  P   C A 330   -44.310 126.141 353.857  1.00  0.00           P
ATOM   326  P   G A 331   -47.840 128.776 350.494  1.00  0.00           P
ATOM   327  P   G A 332   -50.639 133.375 351.391  1.00  0.00           P
ATOM   328  P   G A 333   -45.756 136.939 353.550  1.00  0.00           P
ATOM   329  P   C A 334   -42.007 140.459 355.493  1.00  0.00           P
ATOM   330  P   C A 335   -37.124 142.989 355.191  1.00  0.00           P
ATOM   331  P   C A 336   -32.215 144.282 352.445  1.00  0.00           P
ATOM   332  P   C A 337   -29.043 144.003 347.743  1.00  0.00           P
ATOM   333  P   A A 338   -31.723 144.161 342.477  1.00  0.00           P
ATOM   334  P   C A 339   -34.170 144.376 337.382  1.00  0.00           P
ATOM   335  P   U A 340   -39.391 145.113 334.484  1.00  0.00           P
ATOM   336  P   C A 341   -44.753 147.092 333.985  1.00  0.00           P
ATOM   337  P   C A 342   -49.097 150.833 336.191  1.00  0.00           P
ATOM   338  P   U A 343   -50.471 155.387 338.904  1.00  0.00           P
ATOM   339  P   A A 344   -48.638 160.221 341.423  1.00  0.00           P
ATOM   340  P   C A 345   -44.580 162.951 345.538  1.00  0.00           P
ATOM   341  P   G A 346   -38.261 160.919 346.913  1.00  0.00           P
ATOM   342  P   G A 347   -38.928 155.351 350.695  1.00  0.00           P
ATOM   343  P   G A 348   -43.094 150.541 352.374  1.00  0.00           P
ATOM   344  P   A A 349   -47.524 146.144 350.692  1.00  0.00           P
ATOM   345  P   G A 350   -49.606 141.525 348.143  1.00  0.00           P
ATOM   346  P   G A 351   -47.853 137.997 345.051  1.00  0.00           P
ATOM   347  P   C A 352   -47.076 133.448 342.657  1.00  0.00           P
ATOM   348  P   A A 353   -46.787 129.268 338.046  1.00  0.00           P
ATOM   349  P   G A 354   -49.731 126.940 340.906  1.00  0.00           P
ATOM   350  P   C A 355   -54.812 123.692 338.170  1.00  0.00           P
ATOM   351  P   A A 356   -58.713 123.450 334.342  1.00  0.00           P
ATOM   352  P   G A 357   -59.192 126.998 329.239  1.00  0.00           P
ATOM   353  P   U A 358   -56.808 131.364 325.827  1.00  0.00           P
ATOM   354  P   U A 359   -53.287 134.809 323.077  1.00  0.00           P
ATOM   355  P   A A 360   -46.921 134.492 323.217  1.00  0.00           P
ATOM   356  P   G A 361   -41.914 133.002 321.227  1.00  0.00           P
ATOM   357  P   G A 362   -39.243 128.632 318.895  1.00  0.00           P
ATOM   358  P   A A 363   -40.427 124.022 315.901  1.00  0.00           P
ATOM   359  P   A A 364   -45.785 123.348 317.126  1.00  0.00           P
ATOM   360  P   U A 365   -48.738 121.978 321.209  1.00  0.00           P
ATOM   361  P   C A 366   -52.602 122.576 325.245  1.00  0.00           P
ATOM   362  P   U A 367   -58.892 123.028 325.350  1.00  0.00           P
ATOM   363  P   U A 368   -62.521 126.322 328.669  1.00  0.00           P
ATOM   364  P   C A 369   -65.197 128.651 332.627  1.00  0.00           P
ATOM   365  P   C A 370   -70.544 127.566 333.657  1.00  0.00           P
ATOM   366  P   G A 371   -73.843 126.155 337.538  1.00  0.00           P
ATOM   367  P   C A 372   -73.963 123.783 342.383  1.00  0.00           P
ATOM   368  P   A A 373   -74.158 119.441 347.146  1.00  0.00           P
ATOM   369  P   A A 374   -73.389 115.047 349.128  1.00  0.00           P
ATOM   370  P   U A 375   -70.680 110.437 351.111  1.00  0.00           P
ATOM   371  P   G A 376   -66.100 109.275 353.939  1.00  0.00           P
ATOM   372  P   G A 377   -61.998 112.219 356.976  1.00  0.00           P
ATOM   373  P   G A 378   -59.593 116.700 359.831  1.00  0.00           P
ATOM   374  P   C A 379   -60.045 120.868 363.284  1.00  0.00           P
ATOM   375  P   G A 380   -63.406 123.771 366.902  1.00  0.00           P
ATOM   376  P   C A 381   -68.180 123.772 369.354  1.00  0.00           P
ATOM   377  P   A A 382   -71.102 119.676 365.807  1.00  0.00           P
ATOM   378  P   A A 383   -75.429 119.660 361.356  1.00  0.00           P
ATOM   379  P   G A 384   -77.798 122.248 356.944  1.00  0.00           P
ATOM   380  P   C A 385   -73.702 126.508 353.682  1.00  0.00           P
ATOM   381  P   C A 386   -69.016 128.695 351.429  1.00  0.00           P
ATOM   382  P   U A 387   -64.285 127.491 348.726  1.00  0.00           P
ATOM   383  P   G A 388   -61.561 124.191 345.663  1.00  0.00           P
ATOM   384  P   A A 389   -59.430 121.311 343.562  1.00  0.00           P
ATOM   385  P   C A 390   -59.297 116.707 342.546  1.00  0.00           P
ATOM   386  P   G A 391   -63.866 112.439 341.802  1.00  0.00           P
ATOM   387  P   G A 392   -68.349 110.610 338.892  1.00  0.00           P
ATOM   388  P   A A 393   -70.096 114.173 333.294  1.00  0.00           P
```

```
ATOM   389  P    G A 394    -69.300 116.949 327.807  1.00  0.00           P
ATOM   390  P    C A 395    -66.975 119.144 323.147  1.00  0.00           P
ATOM   391  P    G A 396    -63.174 118.503 319.257  1.00  0.00           P
ATOM   392  P    A A 397    -60.109 115.498 316.829  1.00  0.00           P
ATOM   393  P    C A 398    -55.402 113.293 317.740  1.00  0.00           P
ATOM   394  P    G A 399    -53.707 107.892 318.530  1.00  0.00           P
ATOM   395  P    C A 400    -54.352 102.353 319.998  1.00  0.00           P
ATOM   396  P    C A 401    -57.724  97.756 320.941  1.00  0.00           P
ATOM   397  P    G A 402    -62.904  95.623 320.009  1.00  0.00           P
ATOM   398  P    C A 403    -67.949  95.411 317.514  1.00  0.00           P
ATOM   399  P    U A 404    -71.069  99.121 313.886  1.00  0.00           P
ATOM   400  P    U A 405    -72.692 100.605 309.291  1.00  0.00           P
ATOM   401  P    G A 406    -73.892 101.332 302.835  1.00  0.00           P
ATOM   402  P    G A 407    -74.265  94.720 303.929  1.00  0.00           P
ATOM   403  P    A A 408    -76.111  89.538 302.943  1.00  0.00           P
ATOM   404  P    G A 409    -77.246  86.006 298.577  1.00  0.00           P
ATOM   405  P    G A 410    -80.216  86.704 292.804  1.00  0.00           P
ATOM   406  P    A A 411    -78.586  88.064 287.846  1.00  0.00           P
ATOM   407  P    A A 412    -77.504  84.963 283.865  1.00  0.00           P
ATOM   408  P    G A 413    -73.620  87.048 278.505  1.00  0.00           P
ATOM   409  P    A A 414    -70.205  93.037 280.715  1.00  0.00           P
ATOM   410  P    A A 415    -70.245  97.050 277.320  1.00  0.00           P
ATOM   411  P    G A 416    -66.880 101.786 276.465  1.00  0.00           P
ATOM   412  P    C A 417    -61.868 104.106 277.870  1.00  0.00           P
ATOM   413  P    C A 418    -56.479 102.172 279.231  1.00  0.00           P
ATOM   414  P    C A 419    -52.619  98.139 278.755  1.00  0.00           P
ATOM   415  P    U A 420    -50.904  92.979 276.076  1.00  0.00           P
ATOM   416  P    U A 421    -51.083  89.431 271.597  1.00  0.00           P
ATOM   417  P    C A 422    -54.597  86.341 267.440  1.00  0.00           P
ATOM   418  P    G A 423    -61.021  88.075 265.907  1.00  0.00           P
ATOM   419  P    G A 424    -65.154  87.020 271.234  1.00  0.00           P
ATOM   420  P    G A 425    -64.185  85.689 277.903  1.00  0.00           P
ATOM   421  P    G A 426    -62.747  86.562 283.277  1.00  0.00           P
ATOM   422  P    U A 427    -62.219  89.745 288.047  1.00  0.00           P
ATOM   423  P    G A 428    -63.770  94.165 291.786  1.00  0.00           P
ATOM   424  P    U A 429    -67.817  88.555 290.561  1.00  0.00           P
ATOM   425  P    A A 430    -69.276  91.308 295.552  1.00  0.00           P
ATOM   426  P    A A 431    -72.409  97.010 294.621  1.00  0.00           P
ATOM   427  P    A A 432    -74.773 101.759 292.450  1.00  0.00           P
ATOM   428  P    C A 433    -79.621 101.652 289.352  1.00  0.00           P
ATOM   429  P    U A 434    -84.902  98.796 289.766  1.00  0.00           P
ATOM   430  P    C A 435    -88.608  96.210 292.754  1.00  0.00           P
ATOM   431  P    C A 436    -90.480  94.753 298.600  1.00  0.00           P
ATOM   432  P    U A 437    -88.033  94.748 305.570  1.00  0.00           P
ATOM   433  P    G A 438    -86.183  95.452 311.930  1.00  0.00           P
ATOM   434  P    A A 439    -83.229 100.014 314.325  1.00  0.00           P
ATOM   435  P    A A 440    -78.644 104.660 313.585  1.00  0.00           P
ATOM   436  P    C A 442    -79.817 111.213 315.316  1.00  0.00           P
ATOM   437  P    C A 443    -84.993 114.132 315.760  1.00  0.00           P
ATOM   438  P    C A 444    -90.362 114.844 317.864  1.00  0.00           P
ATOM   439  P    G A 445    -94.003 114.094 322.177  1.00  0.00           P
ATOM   440  P    G A 446    -95.068 112.302 327.779  1.00  0.00           P
ATOM   441  P    G A 447    -91.675 109.613 332.900  1.00  0.00           P
ATOM   442  P    A A 448    -86.504 109.069 335.669  1.00  0.00           P
ATOM   443  P    C A 449    -83.151 106.511 339.954  1.00  0.00           P
ATOM   444  P    G A 450    -79.520 105.661 343.612  1.00  0.00           P
ATOM   445  P    A A 451    -75.884 110.739 346.807  1.00  0.00           P
ATOM   446  P    A A 452    -79.953 105.879 348.624  1.00  0.00           P
ATOM   447  P    A A 453    -80.290 106.121 354.111  1.00  0.00           P
ATOM   448  P    C A 454    -78.278 109.129 356.227  1.00  0.00           P
ATOM   449  P    C A 455    -78.337 114.287 362.864  1.00  0.00           P
ATOM   450  P    C A 456    -83.892 116.883 364.031  1.00  0.00           P
ATOM   451  P    C A 457    -88.425 115.958 367.315  1.00  0.00           P
ATOM   452  P    C A 458    -91.050 111.895 371.366  1.00  0.00           P
ATOM   453  P    G A 464    -90.779 107.963 374.768  1.00  0.00           P
ATOM   454  P    A A 465    -87.855 104.735 377.897  1.00  0.00           P
ATOM   455  P    C A 466    -83.180 109.227 375.561  1.00  0.00           P
ATOM   456  P    G A 467    -78.927 106.987 370.544  1.00  0.00           P
ATOM   457  P    A A 468    -77.079 102.008 368.960  1.00  0.00           P
ATOM   458  P    G A 474    -79.397  97.895 366.127  1.00  0.00           P
ATOM   459  P    G A 475    -84.670  97.698 363.397  1.00  0.00           P
ATOM   460  P    G A 476    -88.868  99.922 360.543  1.00  0.00           P
ATOM   461  P    G A 477    -91.531 104.605 357.485  1.00  0.00           P
ATOM   462  P    A A 478    -91.517 109.011 353.672  1.00  0.00           P
ATOM   463  P    C A 479    -89.798 113.646 350.344  1.00  0.00           P
ATOM   464  P    U A 480    -87.134 116.839 347.399  1.00  0.00           P
ATOM   465  P    G A 481    -83.337 117.903 343.449  1.00  0.00           P
ATOM   466  P    A A 482    -80.437 119.401 338.144  1.00  0.00           P
ATOM   467  P    C A 483    -77.481 120.256 334.287  1.00  0.00           P
ATOM   468  P    G A 484    -76.619 115.516 330.698  1.00  0.00           P
ATOM   469  P    G A 485    -81.866 119.339 331.052  1.00  0.00           P
ATOM   470  P    U A 486    -85.153 113.959 326.245  1.00  0.00           P
ATOM   471  P    A A 487    -80.051 109.773 325.754  1.00  0.00           P
ATOM   472  P    C A 488    -79.050 104.075 326.556  1.00  0.00           P
ATOM   473  P    C A 489    -83.526  99.913 326.282  1.00  0.00           P
ATOM   474  P    G A 490    -88.514  98.004 324.787  1.00  0.00           P
ATOM   475  P    G A 491    -92.694  98.173 321.087  1.00  0.00           P
```

```
ATOM    476  P     G A 492     -94.522  99.947 315.765  1.00  0.00           P
ATOM    477  P     G A 493     -93.878 102.192 310.510  1.00  0.00           P
ATOM    478  P     U A 494     -90.411 102.110 304.676  1.00  0.00           P
ATOM    479  P     A A 495     -85.536 102.929 302.479  1.00  0.00           P
ATOM    480  P     A A 496     -80.645 103.983 300.172  1.00  0.00           P
ATOM    481  P     U A 497     -74.301 105.909 300.804  1.00  0.00           P
ATOM    482  P     A A 498     -68.969 107.127 299.899  1.00  0.00           P
ATOM    483  P     G A 500     -62.542 105.736 298.333  1.00  0.00           P
ATOM    484  P     C A 501     -57.541 108.737 299.576  1.00  0.00           P
ATOM    485  P     G A 502     -51.468 107.827 300.369  1.00  0.00           P
ATOM    486  P     C A 503     -46.704 104.427 299.855  1.00  0.00           P
ATOM    487  P     C A 504     -43.853  99.679 296.976  1.00  0.00           P
ATOM    488  P     G A 505     -42.300  97.312 291.661  1.00  0.00           P
ATOM    489  P     G A 506     -39.457  92.386 293.423  1.00  0.00           P
ATOM    490  P     C A 507     -37.490  89.228 297.223  1.00  0.00           P
ATOM    491  P     C A 508     -37.737  89.104 303.063  1.00  0.00           P
ATOM    492  P     A A 509     -42.129  88.093 298.390  1.00  0.00           P
ATOM    493  P     A A 510     -46.292  87.831 295.294  1.00  0.00           P
ATOM    494  P     C A 511     -48.815  90.447 291.121  1.00  0.00           P
ATOM    495  P     U A 512     -46.175  91.097 283.761  1.00  0.00           P
ATOM    496  P     C A 513     -46.745  95.803 278.644  1.00  0.00           P
ATOM    497  P     C A 514     -47.373 100.930 275.318  1.00  0.00           P
ATOM    498  P     G A 515     -46.522 106.651 274.781  1.00  0.00           P
ATOM    499  P     U A 516     -42.631 109.633 277.447  1.00  0.00           P
ATOM    500  P     G A 517     -36.932 111.639 278.347  1.00  0.00           P
ATOM    501  P     C A 518     -30.588 109.472 279.327  1.00  0.00           P
ATOM    502  P     C A 519     -27.840 112.573 283.746  1.00  0.00           P
ATOM    503  P     A A 520     -31.888 116.651 287.121  1.00  0.00           P
ATOM    504  P     G A 521     -37.733 115.970 290.798  1.00  0.00           P
ATOM    505  P     C A 522     -39.223 111.071 295.116  1.00  0.00           P
ATOM    506  P     A A 523     -39.819 106.847 298.570  1.00  0.00           P
ATOM    507  P     G A 524     -36.801 104.915 301.056  1.00  0.00           P
ATOM    508  P     C A 525     -30.872 103.000 303.475  1.00  0.00           P
ATOM    509  P     C A 526     -26.411 100.303 301.208  1.00  0.00           P
ATOM    510  P     G A 527     -25.121  96.932 297.313  1.00  0.00           P
ATOM    511  P     C A 528     -28.782  97.980 291.471  1.00  0.00           P
ATOM    512  P     G A 529     -32.572 102.390 287.478  1.00  0.00           P
ATOM    513  P     G A 530     -30.567 102.969 281.757  1.00  0.00           P
ATOM    514  P     U A 531     -30.767 106.169 277.382  1.00  0.00           P
ATOM    515  P     A A 532     -32.946 101.108 274.091  1.00  0.00           P
ATOM    516  P     A A 533     -37.350 100.364 279.399  1.00  0.00           P
ATOM    517  P     U A 534     -39.826  96.590 282.416  1.00  0.00           P
ATOM    518  P     A A 535     -41.007  98.430 287.487  1.00  0.00           P
ATOM    519  P     C A 536     -40.591 104.173 290.769  1.00  0.00           P
ATOM    520  P     G A 537     -42.787 109.053 291.295  1.00  0.00           P
ATOM    521  P     G A 538     -48.336 109.929 290.398  1.00  0.00           P
ATOM    522  P     A A 539     -53.892 108.107 288.910  1.00  0.00           P
ATOM    523  P     G A 540     -57.640 104.213 286.744  1.00  0.00           P
ATOM    524  P     G A 541     -58.782  96.809 287.694  1.00  0.00           P
ATOM    525  P     G A 542     -57.319  92.601 291.616  1.00  0.00           P
ATOM    526  P     C A 543     -54.806  90.406 296.768  1.00  0.00           P
ATOM    527  P     G A 544     -53.253  90.796 302.157  1.00  0.00           P
ATOM    528  P     C A 545     -53.799  93.415 307.166  1.00  0.00           P
ATOM    529  P     G A 546     -58.416  96.956 309.097  1.00  0.00           P
ATOM    530  P     A A 547     -62.489  99.930 312.879  1.00  0.00           P
ATOM    531  P     G A 548     -60.039 103.622 315.941  1.00  0.00           P
ATOM    532  P     C A 549     -55.864 101.568 312.530  1.00  0.00           P
ATOM    533  P     G A 550     -51.440 100.776 308.382  1.00  0.00           P
ATOM    534  P     U A 551     -45.475 103.418 307.374  1.00  0.00           P
ATOM    535  P     U A 552     -40.622 106.744 307.622  1.00  0.00           P
ATOM    536  P     A A 553     -36.661 109.235 310.782  1.00  0.00           P
ATOM    537  P     C A 554     -33.921 109.411 315.595  1.00  0.00           P
ATOM    538  P     C A 555     -32.743 106.293 320.591  1.00  0.00           P
ATOM    539  P     C A 556     -32.201 101.598 323.658  1.00  0.00           P
ATOM    540  P     G A 557     -33.728  93.785 322.621  1.00  0.00           P
ATOM    541  P     G A 558     -34.163  88.491 321.408  1.00  0.00           P
ATOM    542  P     A A 559     -30.668  87.674 315.948  1.00  0.00           P
ATOM    543  P     U A 560     -28.925  87.271 321.707  1.00  0.00           P
ATOM    544  P     U A 561     -23.980  86.052 318.214  1.00  0.00           P
ATOM    545  P     C A 562     -23.793  91.075 321.785  1.00  0.00           P
ATOM    546  P     A A 563     -23.446  90.211 327.367  1.00  0.00           P
ATOM    547  P     C A 564     -21.625  85.319 328.812  1.00  0.00           P
ATOM    548  P     U A 565     -24.163  82.557 332.104  1.00  0.00           P
ATOM    549  P     G A 566     -27.284  80.180 327.160  1.00  0.00           P
ATOM    550  P     G A 567     -21.582  80.033 326.313  1.00  0.00           P
ATOM    551  P     G A 568     -16.484  80.312 322.411  1.00  0.00           P
ATOM    552  P     C A 569     -10.182  81.459 320.227  1.00  0.00           P
ATOM    553  P     G A 570      -4.705  80.915 318.077  1.00  0.00           P
ATOM    554  P     U A 571      -2.687  83.379 314.499  1.00  0.00           P
ATOM    555  P     A A 572      -2.823  87.011 311.861  1.00  0.00           P
ATOM    556  P     A A 573      -6.253  89.339 313.027  1.00  0.00           P
ATOM    557  P     A A 574      -6.020  89.990 317.287  1.00  0.00           P
ATOM    558  P     G A 575      -4.038  89.436 320.590  1.00  0.00           P
ATOM    559  P     G A 576       1.220  88.876 323.375  1.00  0.00           P
ATOM    560  P     G A 577       6.396  87.526 326.226  1.00  0.00           P
ATOM    561  P     C A 578       6.738  83.733 330.650  1.00  0.00           P
ATOM    562  P     G A 579       8.659  81.579 335.914  1.00  0.00           P
```

| | | | | | | | | | |
|---|---|---|---|---|---|---|---|---|---|
| ATOM | 563 | P | U A 580 | 10.773 | 82.090 | 342.204 | 1.00 | 0.00 | P |
| ATOM | 564 | P | G A 581 | 6.072 | 84.158 | 345.588 | 1.00 | 0.00 | P |
| ATOM | 565 | P | U A 582 | 3.585 | 85.910 | 349.076 | 1.00 | 0.00 | P |
| ATOM | 566 | P | A A 583 | 0.397 | 89.597 | 349.809 | 1.00 | 0.00 | P |
| ATOM | 567 | P | G A 584 | -4.881 | 89.987 | 348.494 | 1.00 | 0.00 | P |
| ATOM | 568 | P | G A 585 | -9.542 | 86.975 | 345.896 | 1.00 | 0.00 | P |
| ATOM | 569 | P | C A 586 | -12.012 | 82.028 | 344.023 | 1.00 | 0.00 | P |
| ATOM | 570 | P | G A 587 | -9.856 | 75.583 | 346.261 | 1.00 | 0.00 | P |
| ATOM | 571 | P | G A 588 | -8.095 | 70.272 | 347.602 | 1.00 | 0.00 | P |
| ATOM | 572 | P | C A 589 | -7.610 | 64.570 | 347.973 | 1.00 | 0.00 | P |
| ATOM | 573 | P | C A 590 | -9.976 | 60.726 | 351.648 | 1.00 | 0.00 | P |
| ATOM | 574 | P | U A 591 | -12.940 | 59.653 | 356.328 | 1.00 | 0.00 | P |
| ATOM | 575 | P | G A 592 | -15.997 | 61.246 | 361.114 | 1.00 | 0.00 | P |
| ATOM | 576 | P | G A 593 | -18.693 | 65.200 | 364.613 | 1.00 | 0.00 | P |
| ATOM | 577 | P | G A 594 | -21.057 | 70.119 | 366.299 | 1.00 | 0.00 | P |
| ATOM | 578 | P | G A 595 | -23.115 | 75.266 | 364.794 | 1.00 | 0.00 | P |
| ATOM | 579 | P | C A 596 | -23.622 | 80.369 | 361.113 | 1.00 | 0.00 | P |
| ATOM | 580 | P | G A 597 | -23.836 | 82.495 | 356.669 | 1.00 | 0.00 | P |
| ATOM | 581 | P | U A 598 | -25.965 | 81.585 | 352.679 | 1.00 | 0.00 | P |
| ATOM | 582 | P | C A 599 | -28.896 | 77.731 | 350.303 | 1.00 | 0.00 | P |
| ATOM | 583 | P | C A 600 | -33.730 | 74.645 | 350.451 | 1.00 | 0.00 | P |
| ATOM | 584 | P | C A 601 | -38.986 | 73.343 | 352.446 | 1.00 | 0.00 | P |
| ATOM | 585 | P | A A 602 | -43.781 | 74.455 | 355.292 | 1.00 | 0.00 | P |
| ATOM | 586 | P | U A 603 | -47.352 | 78.210 | 357.832 | 1.00 | 0.00 | P |
| ATOM | 587 | P | G A 604 | -48.459 | 83.794 | 358.793 | 1.00 | 0.00 | P |
| ATOM | 588 | P | U A 605 | -48.339 | 89.308 | 357.454 | 1.00 | 0.00 | P |
| ATOM | 589 | P | G A 606 | -47.037 | 93.182 | 353.164 | 1.00 | 0.00 | P |
| ATOM | 590 | P | A A 607 | -48.233 | 95.977 | 348.237 | 1.00 | 0.00 | P |
| ATOM | 591 | P | A A 608 | -53.213 | 94.941 | 348.916 | 1.00 | 0.00 | P |
| ATOM | 592 | P | A A 609 | -55.223 | 95.824 | 345.636 | 1.00 | 0.00 | P |
| ATOM | 593 | P | G A 610 | -55.650 | 96.410 | 340.102 | 1.00 | 0.00 | P |
| ATOM | 594 | P | A A 611 | -53.451 | 93.985 | 335.356 | 1.00 | 0.00 | P |
| ATOM | 595 | P | C A 612 | -52.313 | 89.299 | 333.222 | 1.00 | 0.00 | P |
| ATOM | 596 | P | C A 613 | -54.605 | 84.291 | 333.372 | 1.00 | 0.00 | P |
| ATOM | 597 | P | A A 614 | -59.494 | 81.359 | 334.525 | 1.00 | 0.00 | P |
| ATOM | 598 | P | C A 615 | -64.749 | 80.930 | 336.171 | 1.00 | 0.00 | P |
| ATOM | 599 | P | G A 616 | -70.115 | 83.874 | 336.935 | 1.00 | 0.00 | P |
| ATOM | 600 | P | G A 617 | -73.439 | 89.007 | 337.104 | 1.00 | 0.00 | P |
| ATOM | 601 | P | C A 618 | -75.538 | 93.912 | 335.435 | 1.00 | 0.00 | P |
| ATOM | 602 | P | U A 619 | -75.786 | 97.908 | 330.053 | 1.00 | 0.00 | P |
| ATOM | 603 | P | C A 620 | -72.924 | 93.247 | 329.814 | 1.00 | 0.00 | P |
| ATOM | 604 | P | A A 621 | -67.837 | 90.998 | 329.227 | 1.00 | 0.00 | P |
| ATOM | 605 | P | A A 622 | -62.278 | 92.792 | 328.718 | 1.00 | 0.00 | P |
| ATOM | 606 | P | C A 623 | -58.915 | 97.006 | 330.144 | 1.00 | 0.00 | P |
| ATOM | 607 | P | C A 624 | -59.625 | 99.280 | 335.540 | 1.00 | 0.00 | P |
| ATOM | 608 | P | G A 625 | -61.766 | 98.157 | 341.040 | 1.00 | 0.00 | P |
| ATOM | 609 | P | U A 626 | -63.156 | 95.240 | 345.783 | 1.00 | 0.00 | P |
| ATOM | 610 | P | G A 627 | -62.403 | 90.704 | 349.066 | 1.00 | 0.00 | P |
| ATOM | 611 | P | G A 628 | -60.351 | 85.558 | 349.706 | 1.00 | 0.00 | P |
| ATOM | 612 | P | G A 629 | -56.188 | 81.741 | 348.296 | 1.00 | 0.00 | P |
| ATOM | 613 | P | G A 630 | -51.092 | 80.273 | 345.509 | 1.00 | 0.00 | P |
| ATOM | 614 | P | G A 631 | -45.700 | 82.085 | 344.455 | 1.00 | 0.00 | P |
| ATOM | 615 | P | A A 632 | -39.476 | 83.169 | 346.168 | 1.00 | 0.00 | P |
| ATOM | 616 | P | G A 633 | -33.928 | 84.578 | 348.001 | 1.00 | 0.00 | P |
| ATOM | 617 | P | C A 634 | -31.916 | 87.658 | 351.979 | 1.00 | 0.00 | P |
| ATOM | 618 | P | G A 635 | -32.612 | 88.905 | 358.073 | 1.00 | 0.00 | P |
| ATOM | 619 | P | U A 636 | -34.079 | 88.161 | 363.320 | 1.00 | 0.00 | P |
| ATOM | 620 | P | G A 637 | -35.351 | 84.129 | 367.022 | 1.00 | 0.00 | P |
| ATOM | 621 | P | G A 638 | -35.460 | 78.706 | 368.889 | 1.00 | 0.00 | P |
| ATOM | 622 | P | G A 639 | -34.051 | 73.273 | 367.845 | 1.00 | 0.00 | P |
| ATOM | 623 | P | A A 640 | -31.063 | 68.774 | 364.710 | 1.00 | 0.00 | P |
| ATOM | 624 | P | U A 641 | -26.962 | 66.631 | 359.422 | 1.00 | 0.00 | P |
| ATOM | 625 | P | A A 642 | -21.661 | 65.607 | 355.829 | 1.00 | 0.00 | P |
| ATOM | 626 | P | C A 643 | -18.131 | 66.535 | 351.440 | 1.00 | 0.00 | P |
| ATOM | 627 | P | G A 644 | -16.189 | 72.547 | 349.515 | 1.00 | 0.00 | P |
| ATOM | 628 | P | C A 645 | -11.293 | 74.437 | 351.190 | 1.00 | 0.00 | P |
| ATOM | 629 | P | U A 646 | -9.599 | 77.571 | 355.543 | 1.00 | 0.00 | P |
| ATOM | 630 | P | C A 647 | -8.219 | 77.889 | 361.096 | 1.00 | 0.00 | P |
| ATOM | 631 | P | A A 648 | -6.395 | 74.866 | 365.490 | 1.00 | 0.00 | P |
| ATOM | 632 | P | G A 649 | -4.127 | 69.985 | 367.605 | 1.00 | 0.00 | P |
| ATOM | 633 | P | G A 650 | -1.688 | 64.724 | 366.324 | 1.00 | 0.00 | P |
| ATOM | 634 | P | C A 651 | 0.561 | 60.462 | 362.515 | 1.00 | 0.00 | P |
| ATOM | 635 | P | U A 652 | 0.657 | 58.360 | 355.011 | 1.00 | 0.00 | P |
| ATOM | 636 | P | A A 653 | 0.868 | 59.218 | 347.857 | 1.00 | 0.00 | P |
| ATOM | 637 | P | G A 654 | 2.867 | 62.948 | 343.470 | 1.00 | 0.00 | P |
| ATOM | 638 | P | A A 655 | 4.586 | 70.003 | 343.275 | 1.00 | 0.00 | P |
| ATOM | 639 | P | C A 656 | 10.260 | 71.496 | 345.058 | 1.00 | 0.00 | P |
| ATOM | 640 | P | G A 657 | 15.077 | 71.395 | 348.367 | 1.00 | 0.00 | P |
| ATOM | 641 | P | G A 658 | 19.055 | 68.390 | 351.402 | 1.00 | 0.00 | P |
| ATOM | 642 | P | U A 659 | 23.479 | 65.777 | 350.899 | 1.00 | 0.00 | P |
| ATOM | 643 | P | G A 660 | 27.163 | 62.345 | 348.712 | 1.00 | 0.00 | P |
| ATOM | 644 | P | G A 661 | 29.008 | 59.632 | 343.529 | 1.00 | 0.00 | P |
| ATOM | 645 | P | G A 662 | 29.638 | 60.109 | 337.543 | 1.00 | 0.00 | P |
| ATOM | 646 | P | A A 663 | 29.306 | 62.861 | 332.312 | 1.00 | 0.00 | P |
| ATOM | 647 | P | G A 664 | 29.230 | 66.740 | 327.875 | 1.00 | 0.00 | P |
| ATOM | 648 | P | A A 665 | 25.790 | 71.115 | 326.877 | 1.00 | 0.00 | P |
| ATOM | 649 | P | G A 666 | 27.742 | 75.819 | 327.551 | 1.00 | 0.00 | P |

```
ATOM    650  P      G A 667      26.023  80.677 328.961  1.00  0.00           P
ATOM    651  P      G A 668      27.508  85.972 330.809  1.00  0.00           P
ATOM    652  P      U A 669      31.550  89.579 332.880  1.00  0.00           P
ATOM    653  P      G A 670      37.183  90.728 334.382  1.00  0.00           P
ATOM    654  P      G A 671      42.993  88.250 333.845  1.00  0.00           P
ATOM    655  P      U A 672      46.937  86.386 329.210  1.00  0.00           P
ATOM    656  P      G A 673      47.906  82.878 324.947  1.00  0.00           P
ATOM    657  P      G A 674      49.045  80.282 319.106  1.00  0.00           P
ATOM    658  P      A A 675      48.461  80.299 312.902  1.00  0.00           P
ATOM    659  P      A A 676      46.128  83.776 308.473  1.00  0.00           P
ATOM    660  P      U A 677      43.696  88.570 305.216  1.00  0.00           P
ATOM    661  P      U A 678      44.233  93.894 302.776  1.00  0.00           P
ATOM    662  P      C A 679      47.566  99.532 303.016  1.00  0.00           P
ATOM    663  P      C A 680      51.704 102.202 304.784  1.00  0.00           P
ATOM    664  P      C A 681      56.579 102.194 306.021  1.00  0.00           P
ATOM    665  P      G A 682      62.116  99.937 304.981  1.00  0.00           P
ATOM    666  P      G A 683      65.773  96.558 301.736  1.00  0.00           P
ATOM    667  P      A A 684      67.757  92.711 297.506  1.00  0.00           P
ATOM    668  P      G A 685      66.626  90.082 292.000  1.00  0.00           P
ATOM    669  P      U A 686      63.648  90.459 287.334  1.00  0.00           P
ATOM    670  P      A A 687      58.724  92.831 283.666  1.00  0.00           P
ATOM    671  P      G A 688      52.468  95.510 281.798  1.00  0.00           P
ATOM    672  P      C A 689      48.174  92.878 285.577  1.00  0.00           P
ATOM    673  P      G A 690      44.335  92.151 289.961  1.00  0.00           P
ATOM    674  P      G A 691      38.118  92.613 292.032  1.00  0.00           P
ATOM    675  P      U A 692      33.075  92.357 290.131  1.00  0.00           P
ATOM    676  P      G A 693      28.679  90.704 286.640  1.00  0.00           P
ATOM    677  P      A A 694      30.538  90.655 281.475  1.00  0.00           P
ATOM    678  P      A A 695      32.950  95.512 279.343  1.00  0.00           P
ATOM    679  P      A A 696      35.462 100.439 281.984  1.00  0.00           P
ATOM    680  P      U A 697      36.173 105.188 285.344  1.00  0.00           P
ATOM    681  P      G A 698      39.278 106.553 290.230  1.00  0.00           P
ATOM    682  P      C A 699      43.171 105.827 293.667  1.00  0.00           P
ATOM    683  P      G A 700      49.669 105.138 294.386  1.00  0.00           P
ATOM    684  P      C A 701      52.402 104.757 289.509  1.00  0.00           P
ATOM    685  P      A A 702      58.728 105.517 286.335  1.00  0.00           P
ATOM    686  P      G A 703      58.718 103.309 292.797  1.00  0.00           P
ATOM    687  P      A A 704      56.343  98.053 293.989  1.00  0.00           P
ATOM    688  P      U A 705      51.539  95.126 296.007  1.00  0.00           P
ATOM    689  P      A A 706      49.113  90.084 295.601  1.00  0.00           P
ATOM    690  P      C A 707      51.325  85.228 296.833  1.00  0.00           P
ATOM    691  P      C A 708      54.983  83.519 300.620  1.00  0.00           P
ATOM    692  P      G A 709      57.866  83.513 305.455  1.00  0.00           P
ATOM    693  P      G A 710      59.204  86.289 310.620  1.00  0.00           P
ATOM    694  P      G A 711      57.965  90.299 314.561  1.00  0.00           P
ATOM    695  P      A A 712      54.707  94.602 317.151  1.00  0.00           P
ATOM    696  P      G A 713      50.081  97.676 318.513  1.00  0.00           P
ATOM    697  P      G A 714      43.324  95.948 318.783  1.00  0.00           P
ATOM    698  P      A A 715      37.231  93.956 318.673  1.00  0.00           P
ATOM    699  P      A A 716      33.750  90.093 317.880  1.00  0.00           P
ATOM    700  P      C A 717      31.546  85.017 317.171  1.00  0.00           P
ATOM    701  P      G A 718      33.878  79.050 314.726  1.00  0.00           P
ATOM    702  P      C A 719      33.415  75.470 311.059  1.00  0.00           P
ATOM    703  P      C A 720      34.121  69.840 311.626  1.00  0.00           P
ATOM    704  P      G A 721      30.719  67.476 315.867  1.00  0.00           P
ATOM    705  P      A A 722      26.872  69.767 309.593  1.00  0.00           P
ATOM    706  P      U A 723      20.336  68.730 311.153  1.00  0.00           P
ATOM    707  P      G A 724      19.113  70.030 316.871  1.00  0.00           P
ATOM    708  P      G A 725      19.648  68.156 322.161  1.00  0.00           P
ATOM    709  P      C A 726      19.758  70.702 327.402  1.00  0.00           P
ATOM    710  P      G A 727      18.494  74.074 330.982  1.00  0.00           P
ATOM    711  P      A A 728      15.225  77.175 332.582  1.00  0.00           P
ATOM    712  P      A A 729      12.349  78.666 327.828  1.00  0.00           P
ATOM    713  P      G A 730      13.352  83.319 323.957  1.00  0.00           P
ATOM    714  P      G A 731      16.726  86.905 322.399  1.00  0.00           P
ATOM    715  P      C A 732      22.643  85.919 321.157  1.00  0.00           P
ATOM    716  P      A A 733      27.639  83.723 321.348  1.00  0.00           P
ATOM    717  P      G A 734      31.821  80.266 320.321  1.00  0.00           P
ATOM    718  P      C A 735      36.588  76.738 321.883  1.00  0.00           P
ATOM    719  P      C A 736      39.749  74.838 326.446  1.00  0.00           P
ATOM    720  P      A A 737      40.312  73.981 333.065  1.00  0.00           P
ATOM    721  P      C A 738      40.260  76.098 339.189  1.00  0.00           P
ATOM    722  P      C A 739      36.663  79.079 343.207  1.00  0.00           P
ATOM    723  P      U A 740      30.438  80.576 345.190  1.00  0.00           P
ATOM    724  P      G A 741      24.646  78.909 343.447  1.00  0.00           P
ATOM    725  P      G A 742      19.199  77.203 340.827  1.00  0.00           P
ATOM    726  P      U A 743      15.867  73.679 338.074  1.00  0.00           P
ATOM    727  P      C A 744      14.429  68.345 336.438  1.00  0.00           P
ATOM    728  P      C A 745      13.970  62.569 335.990  1.00  0.00           P
ATOM    729  P      A A 746      14.589  57.062 337.923  1.00  0.00           P
ATOM    730  P      C A 747      15.128  53.027 341.928  1.00  0.00           P
ATOM    731  P      C A 748      13.771  53.455 346.943  1.00  0.00           P
ATOM    732  P      C A 749      11.451  54.735 351.563  1.00  0.00           P
ATOM    733  P      G A 750      10.931  58.019 356.489  1.00  0.00           P
ATOM    734  P      U A 751       9.937  62.731 359.071  1.00  0.00           P
ATOM    735  P      G A 752       5.584  69.428 357.598  1.00  0.00           P
ATOM    736  P      A A 753      -0.172  70.221 356.857  1.00  0.00           P
```

| | | | | | | | | | | |
|---|---|---|---|---|---|---|---|---|---|---|
| ATOM | 737 | P | C | A | 754 | -1.278 | 71.918 | 352.190 | 1.00 | 0.00 | P |
| ATOM | 738 | P | G | A | 755 | 3.209 | 75.504 | 350.009 | 1.00 | 0.00 | P |
| ATOM | 739 | P | C | A | 756 | 3.176 | 75.151 | 344.237 | 1.00 | 0.00 | P |
| ATOM | 740 | P | U | A | 757 | 2.347 | 76.311 | 339.057 | 1.00 | 0.00 | P |
| ATOM | 741 | P | G | A | 758 | -0.580 | 82.006 | 336.813 | 1.00 | 0.00 | P |
| ATOM | 742 | P | A | A | 759 | -0.571 | 87.810 | 337.885 | 1.00 | 0.00 | P |
| ATOM | 743 | P | G | A | 760 | -1.443 | 92.198 | 335.760 | 1.00 | 0.00 | P |
| ATOM | 744 | P | G | A | 761 | 1.038 | 97.071 | 339.057 | 1.00 | 0.00 | P |
| ATOM | 745 | P | C | A | 762 | 6.353 | 98.004 | 341.694 | 1.00 | 0.00 | P |
| ATOM | 746 | P | G | A | 763 | 12.433 | 97.055 | 340.793 | 1.00 | 0.00 | P |
| ATOM | 747 | P | C | A | 764 | 17.630 | 94.845 | 337.284 | 1.00 | 0.00 | P |
| ATOM | 748 | P | G | A | 765 | 18.886 | 92.894 | 331.407 | 1.00 | 0.00 | P |
| ATOM | 749 | P | A | A | 766 | 18.763 | 93.020 | 325.986 | 1.00 | 0.00 | P |
| ATOM | 750 | P | A | A | 767 | 22.098 | 93.745 | 321.808 | 1.00 | 0.00 | P |
| ATOM | 751 | P | A | A | 768 | 23.426 | 97.920 | 317.948 | 1.00 | 0.00 | P |
| ATOM | 752 | P | G | A | 769 | 22.202 | 103.102 | 316.583 | 1.00 | 0.00 | P |
| ATOM | 753 | P | C | A | 770 | 22.098 | 108.348 | 319.371 | 1.00 | 0.00 | P |
| ATOM | 754 | P | G | A | 771 | 23.322 | 111.947 | 323.503 | 1.00 | 0.00 | P |
| ATOM | 755 | P | U | A | 772 | 26.860 | 113.902 | 327.036 | 1.00 | 0.00 | P |
| ATOM | 756 | P | G | A | 773 | 32.479 | 112.864 | 329.169 | 1.00 | 0.00 | P |
| ATOM | 757 | P | G | A | 774 | 38.148 | 109.989 | 328.187 | 1.00 | 0.00 | P |
| ATOM | 758 | P | G | A | 775 | 39.504 | 104.617 | 325.203 | 1.00 | 0.00 | P |
| ATOM | 759 | P | G | A | 776 | 42.167 | 101.667 | 320.253 | 1.00 | 0.00 | P |
| ATOM | 760 | P | A | A | 777 | 43.869 | 100.875 | 314.676 | 1.00 | 0.00 | P |
| ATOM | 761 | P | G | A | 778 | 41.529 | 98.755 | 308.346 | 1.00 | 0.00 | P |
| ATOM | 762 | P | C | A | 779 | 36.920 | 96.619 | 304.381 | 1.00 | 0.00 | P |
| ATOM | 763 | P | A | A | 780 | 30.701 | 97.503 | 304.416 | 1.00 | 0.00 | P |
| ATOM | 764 | P | A | A | 781 | 23.481 | 101.958 | 304.145 | 1.00 | 0.00 | P |
| ATOM | 765 | P | A | A | 782 | 22.254 | 105.354 | 302.601 | 1.00 | 0.00 | P |
| ATOM | 766 | P | C | A | 783 | 22.235 | 110.810 | 301.888 | 1.00 | 0.00 | P |
| ATOM | 767 | P | C | A | 784 | 26.028 | 113.662 | 300.149 | 1.00 | 0.00 | P |
| ATOM | 768 | P | G | A | 785 | 31.085 | 115.035 | 296.014 | 1.00 | 0.00 | P |
| ATOM | 769 | P | G | A | 786 | 32.480 | 111.290 | 289.772 | 1.00 | 0.00 | P |
| ATOM | 770 | P | A | A | 787 | 31.737 | 107.569 | 285.388 | 1.00 | 0.00 | P |
| ATOM | 771 | P | U | A | 788 | 27.942 | 103.878 | 282.163 | 1.00 | 0.00 | P |
| ATOM | 772 | P | U | A | 789 | 22.982 | 102.058 | 280.252 | 1.00 | 0.00 | P |
| ATOM | 773 | P | A | A | 790 | 18.012 | 104.307 | 278.856 | 1.00 | 0.00 | P |
| ATOM | 774 | P | G | A | 791 | 19.290 | 109.347 | 281.484 | 1.00 | 0.00 | P |
| ATOM | 775 | P | A | A | 792 | 20.157 | 110.762 | 286.904 | 1.00 | 0.00 | P |
| ATOM | 776 | P | U | A | 793 | 21.189 | 108.057 | 291.375 | 1.00 | 0.00 | P |
| ATOM | 777 | P | A | A | 794 | 20.130 | 108.438 | 296.192 | 1.00 | 0.00 | P |
| ATOM | 778 | P | C | A | 795 | 20.719 | 102.213 | 295.787 | 1.00 | 0.00 | P |
| ATOM | 779 | P | C | A | 796 | 22.744 | 96.329 | 294.284 | 1.00 | 0.00 | P |
| ATOM | 780 | P | C | A | 797 | 28.735 | 95.611 | 292.716 | 1.00 | 0.00 | P |
| ATOM | 781 | P | G | A | 798 | 35.586 | 98.398 | 294.250 | 1.00 | 0.00 | P |
| ATOM | 782 | P | G | A | 799 | 38.696 | 101.206 | 298.824 | 1.00 | 0.00 | P |
| ATOM | 783 | P | G | A | 800 | 38.035 | 105.134 | 302.504 | 1.00 | 0.00 | P |
| ATOM | 784 | P | U | A | 801 | 35.421 | 107.113 | 307.476 | 1.00 | 0.00 | P |
| ATOM | 785 | P | A | A | 802 | 32.491 | 107.246 | 312.624 | 1.00 | 0.00 | P |
| ATOM | 786 | P | G | A | 803 | 29.073 | 105.660 | 316.870 | 1.00 | 0.00 | P |
| ATOM | 787 | P | U | A | 804 | 28.825 | 100.686 | 316.938 | 1.00 | 0.00 | P |
| ATOM | 788 | P | C | A | 805 | 29.191 | 96.219 | 320.129 | 1.00 | 0.00 | P |
| ATOM | 789 | P | C | A | 806 | 31.727 | 94.808 | 324.058 | 1.00 | 0.00 | P |
| ATOM | 790 | P | A | A | 807 | 34.139 | 94.486 | 330.029 | 1.00 | 0.00 | P |
| ATOM | 791 | P | C | A | 808 | 31.800 | 97.478 | 335.002 | 1.00 | 0.00 | P |
| ATOM | 792 | P | G | A | 809 | 26.352 | 101.299 | 337.237 | 1.00 | 0.00 | P |
| ATOM | 793 | P | C | A | 810 | 19.857 | 103.386 | 336.214 | 1.00 | 0.00 | P |
| ATOM | 794 | P | C | A | 811 | 14.965 | 104.124 | 332.424 | 1.00 | 0.00 | P |
| ATOM | 795 | P | C | A | 812 | 10.676 | 103.623 | 327.409 | 1.00 | 0.00 | P |
| ATOM | 796 | P | U | A | 813 | 7.775 | 97.859 | 325.716 | 1.00 | 0.00 | P |
| ATOM | 797 | P | A | A | 814 | 8.604 | 96.491 | 320.171 | 1.00 | 0.00 | P |
| ATOM | 798 | P | A | A | 815 | 7.657 | 92.934 | 316.962 | 1.00 | 0.00 | P |
| ATOM | 799 | P | A | A | 816 | 10.233 | 88.367 | 315.672 | 1.00 | 0.00 | P |
| ATOM | 800 | P | C | A | 817 | 8.871 | 85.240 | 319.962 | 1.00 | 0.00 | P |
| ATOM | 801 | P | G | A | 818 | 10.980 | 81.277 | 317.766 | 1.00 | 0.00 | P |
| ATOM | 802 | P | A | A | 819 | 4.306 | 82.195 | 316.606 | 1.00 | 0.00 | P |
| ATOM | 803 | P | U | A | 820 | 2.199 | 78.547 | 319.237 | 1.00 | 0.00 | P |
| ATOM | 804 | P | G | A | 821 | -0.978 | 80.012 | 323.736 | 1.00 | 0.00 | P |
| ATOM | 805 | P | C | A | 822 | 2.822 | 78.254 | 327.756 | 1.00 | 0.00 | P |
| ATOM | 806 | P | G | A | 823 | 3.860 | 74.843 | 332.079 | 1.00 | 0.00 | P |
| ATOM | 807 | P | C | A | 824 | 2.686 | 70.265 | 335.141 | 1.00 | 0.00 | P |
| ATOM | 808 | P | G | A | 825 | 0.074 | 65.225 | 335.807 | 1.00 | 0.00 | P |
| ATOM | 809 | P | C | A | 826 | -3.341 | 60.763 | 334.728 | 1.00 | 0.00 | P |
| ATOM | 810 | P | U | A | 827 | -6.411 | 57.917 | 329.959 | 1.00 | 0.00 | P |
| ATOM | 811 | P | A | A | 828 | -6.110 | 56.935 | 325.048 | 1.00 | 0.00 | P |
| ATOM | 812 | P | G | A | 829 | -1.355 | 53.797 | 323.094 | 1.00 | 0.00 | P |
| ATOM | 813 | P | G | A | 830 | 3.656 | 51.409 | 319.139 | 1.00 | 0.00 | P |
| ATOM | 814 | P | U | A | 831 | 8.095 | 51.187 | 315.397 | 1.00 | 0.00 | P |
| ATOM | 815 | P | C | A | 832 | 12.985 | 54.095 | 313.625 | 1.00 | 0.00 | P |
| ATOM | 816 | P | U | A | 833 | 18.017 | 57.511 | 314.689 | 1.00 | 0.00 | P |
| ATOM | 817 | P | C | A | 834 | 20.202 | 61.711 | 317.702 | 1.00 | 0.00 | P |
| ATOM | 818 | P | U | A | 835 | 23.390 | 62.418 | 323.480 | 1.00 | 0.00 | P |
| ATOM | 819 | P | G | A | 836 | 23.747 | 60.780 | 329.070 | 1.00 | 0.00 | P |
| ATOM | 820 | P | G | A | 837 | 22.801 | 56.372 | 333.430 | 1.00 | 0.00 | P |
| ATOM | 821 | P | G | A | 838 | 21.342 | 51.321 | 335.803 | 1.00 | 0.00 | P |
| ATOM | 822 | P | U | A | 841 | 20.008 | 45.411 | 336.017 | 1.00 | 0.00 | P |
| ATOM | 823 | P | C | A | 842 | 17.546 | 41.550 | 329.937 | 1.00 | 0.00 | P |

```
ATOM    824  P    U A 843     19.113  43.480 324.864  1.00  0.00           P
ATOM    825  P    C A 848     14.090  45.815 320.465  1.00  0.00           P
ATOM    826  P    C A 849      9.814  48.177 323.407  1.00  0.00           P
ATOM    827  P    U A 850      7.367  50.855 328.233  1.00  0.00           P
ATOM    828  P    G A 851      7.140  55.550 331.646  1.00  0.00           P
ATOM    829  P    G A 852      8.354  61.668 332.407  1.00  0.00           P
ATOM    830  P    G A 853     10.771  67.084 329.369  1.00  0.00           P
ATOM    831  P    G A 854     11.775  69.788 324.662  1.00  0.00           P
ATOM    832  P    G A 855     10.842  71.014 318.270  1.00  0.00           P
ATOM    833  P    C A 856      8.484  68.927 312.293  1.00  0.00           P
ATOM    834  P    C A 857      4.642  65.012 308.630  1.00  0.00           P
ATOM    835  P    G A 858     -1.812  67.298 305.113  1.00  0.00           P
ATOM    836  P    A A 859     -4.472  59.423 310.820  1.00  0.00           P
ATOM    837  P    A A 860    -10.115  57.887 313.325  1.00  0.00           P
ATOM    838  P    G A 861    -11.937  61.048 314.880  1.00  0.00           P
ATOM    839  P    C A 862    -14.523  67.337 317.300  1.00  0.00           P
ATOM    840  P    U A 863    -13.242  72.539 315.941  1.00  0.00           P
ATOM    841  P    A A 864    -14.171  76.205 311.644  1.00  0.00           P
ATOM    842  P    A A 865    -14.070  73.433 307.099  1.00  0.00           P
ATOM    843  P    C A 866     -9.056  70.935 304.548  1.00  0.00           P
ATOM    844  P    G A 867     -2.499  70.577 304.619  1.00  0.00           P
ATOM    845  P    C A 868      0.723  70.242 310.181  1.00  0.00           P
ATOM    846  P    G A 869      1.167  69.231 315.783  1.00  0.00           P
ATOM    847  P    U A 870      0.913  64.668 320.008  1.00  0.00           P
ATOM    848  P    U A 871      5.136  64.590 324.703  1.00  0.00           P
ATOM    849  P    A A 872      2.732  70.336 324.420  1.00  0.00           P
ATOM    850  P    A A 873     -2.737  74.489 321.182  1.00  0.00           P
ATOM    851  P    G A 874     -8.136  71.362 320.955  1.00  0.00           P
ATOM    852  P    C A 875    -12.482  68.753 322.587  1.00  0.00           P
ATOM    853  P    G A 876    -15.328  67.928 327.242  1.00  0.00           P
ATOM    854  P    C A 877    -14.368  71.288 332.995  1.00  0.00           P
ATOM    855  P    G A 878    -13.041  75.510 336.798  1.00  0.00           P
ATOM    856  P    C A 879    -10.837  79.920 338.750  1.00  0.00           P
ATOM    857  P    C A 880     -7.765  85.195 337.524  1.00  0.00           P
ATOM    858  P    G A 881     -5.996  89.540 334.133  1.00  0.00           P
ATOM    859  P    C A 882     -5.569  92.551 329.139  1.00  0.00           P
ATOM    860  P    C A 883     -7.483  93.107 323.845  1.00  0.00           P
ATOM    861  P    U A 884    -10.899  94.446 320.041  1.00  0.00           P
ATOM    862  P    G A 885    -14.844  96.377 315.663  1.00  0.00           P
ATOM    863  P    G A 886    -10.307  97.166 311.982  1.00  0.00           P
ATOM    864  P    G A 887     -7.103 100.653 309.166  1.00  0.00           P
ATOM    865  P    G A 888     -5.387 104.297 310.189  1.00  0.00           P
ATOM    866  P    A A 889     -5.751 108.793 314.637  1.00  0.00           P
ATOM    867  P    G A 890     -1.006 103.902 313.158  1.00  0.00           P
ATOM    868  P    U A 891      1.645 107.047 318.426  1.00  0.00           P
ATOM    869  P    A A 892     -0.403 112.261 317.986  1.00  0.00           P
ATOM    870  P    C A 893     -2.685 116.234 321.371  1.00  0.00           P
ATOM    871  P    G A 894     -1.882 118.511 326.639  1.00  0.00           P
ATOM    872  P    G A 895     -0.852 116.826 332.594  1.00  0.00           P
ATOM    873  P    C A 896      2.461 113.978 335.717  1.00  0.00           P
ATOM    874  P    C A 897      7.428 110.405 337.168  1.00  0.00           P
ATOM    875  P    G A 898     12.867 109.075 334.529  1.00  0.00           P
ATOM    876  P    C A 899     17.862 111.911 331.032  1.00  0.00           P
ATOM    877  P    A A 900     15.603 115.485 327.672  1.00  0.00           P
ATOM    878  P    A A 901     15.239 113.690 321.376  1.00  0.00           P
ATOM    879  P    G A 902     12.539 110.914 317.609  1.00  0.00           P
ATOM    880  P    G A 903      8.200 106.320 320.323  1.00  0.00           P
ATOM    881  P    C A 904      6.179 101.880 323.568  1.00  0.00           P
ATOM    882  P    U A 905      2.162 100.090 327.129  1.00  0.00           P
ATOM    883  P    G A 906     -3.452 100.943 327.820  1.00  0.00           P
ATOM    884  P    A A 907     -6.116 104.025 323.487  1.00  0.00           P
ATOM    885  P    A A 908    -11.848 106.611 321.190  1.00  0.00           P
ATOM    886  P    A A 909    -16.604 109.761 318.784  1.00  0.00           P
ATOM    887  P    C A 910    -19.497 113.093 314.437  1.00  0.00           P
ATOM    888  P    U A 911    -18.870 112.664 308.836  1.00  0.00           P
ATOM    889  P    C A 912    -19.241 109.457 304.029  1.00  0.00           P
ATOM    890  P    A A 913    -19.601 104.165 302.620  1.00  0.00           P
ATOM    891  P    A A 914    -22.449 100.113 300.576  1.00  0.00           P
ATOM    892  P    A A 915    -17.052  95.713 303.657  1.00  0.00           P
ATOM    893  P    G A 916    -10.644  93.971 303.350  1.00  0.00           P
ATOM    894  P    G A 917     -7.886  87.841 307.047  1.00  0.00           P
ATOM    895  P    A A 918     -7.360  83.148 303.538  1.00  0.00           P
ATOM    896  P    A A 919     -7.276  78.195 303.588  1.00  0.00           P
ATOM    897  P    U A 920     -8.927  74.934 298.188  1.00  0.00           P
ATOM    898  P    U A 921     -9.751  73.619 292.855  1.00  0.00           P
ATOM    899  P    G A 922     -9.769  75.132 286.363  1.00  0.00           P
ATOM    900  P    A A 923     -8.306  78.963 281.125  1.00  0.00           P
ATOM    901  P    C A 924     -3.655  84.564 280.669  1.00  0.00           P
ATOM    902  P    G A 925      2.228  87.377 281.864  1.00  0.00           P
ATOM    903  P    G A 926      6.886  86.068 281.296  1.00  0.00           P
ATOM    904  P    G A 927     10.420  87.601 285.454  1.00  0.00           P
ATOM    905  P    G A 928     10.623  81.291 285.365  1.00  0.00           P
ATOM    906  P    G A 929     13.320  75.108 285.918  1.00  0.00           P
ATOM    907  P    C A 930     13.784  70.444 283.701  1.00  0.00           P
ATOM    908  P    C A 931     12.439  66.575 279.654  1.00  0.00           P
ATOM    909  P    C A 932      9.503  65.699 274.726  1.00  0.00           P
ATOM    910  P    G A 933      7.381  68.096 268.243  1.00  0.00           P
```

```
ATOM  911  P  C A  934    4.451  71.259 263.900 1.00 0.00           P
ATOM  912  P  A A  935    4.200  77.022 263.936 1.00 0.00           P
ATOM  913  P  C A  936    7.851  83.893 264.146 1.00 0.00           P
ATOM  914  P  A A  937   15.434  83.492 265.778 1.00 0.00           P
ATOM  915  P  A A  938   18.104  80.119 261.173 1.00 0.00           P
ATOM  916  P  G A  939   21.982  79.344 257.335 1.00 0.00           P
ATOM  917  P  C A  940   21.452  81.463 250.615 1.00 0.00           P
ATOM  918  P  G A  941   18.935  85.056 245.942 1.00 0.00           P
ATOM  919  P  G A  942   14.819  90.213 244.334 1.00 0.00           P
ATOM  920  P  U A  943   10.418  94.746 245.784 1.00 0.00           P
ATOM  921  P  G A  944    9.607  99.843 247.601 1.00 0.00           P
ATOM  922  P  G A  945   10.768 105.396 249.822 1.00 0.00           P
ATOM  923  P  A A  946   11.112 109.524 246.391 1.00 0.00           P
ATOM  924  P  G A  947    9.631 111.594 241.705 1.00 0.00           P
ATOM  925  P  C A  948    5.114 111.624 238.445 1.00 0.00           P
ATOM  926  P  A A  949    0.184 108.474 235.841 1.00 0.00           P
ATOM  927  P  U A  950   -4.726 104.082 238.855 1.00 0.00           P
ATOM  928  P  G A  951   -7.905 102.238 243.867 1.00 0.00           P
ATOM  929  P  U A  952  -10.010 102.698 248.866 1.00 0.00           P
ATOM  930  P  G A  953  -10.343 105.842 254.433 1.00 0.00           P
ATOM  931  P  G A  954   -8.591 110.042 258.630 1.00 0.00           P
ATOM  932  P  U A  955   -8.566 115.551 259.147 1.00 0.00           P
ATOM  933  P  U A  956   -9.333 120.413 255.406 1.00 0.00           P
ATOM  934  P  U A  957  -12.828 122.417 250.612 1.00 0.00           P
ATOM  935  P  A A  958  -19.258 122.562 248.495 1.00 0.00           P
ATOM  936  P  A A  959  -18.783 118.386 251.266 1.00 0.00           P
ATOM  937  P  U A  960  -18.199 113.674 250.371 1.00 0.00           P
ATOM  938  P  U A  961  -17.552 110.153 248.802 1.00 0.00           P
ATOM  939  P  C A  962  -21.275 106.362 253.626 1.00 0.00           P
ATOM  940  P  G A  963  -20.969 101.746 258.058 1.00 0.00           P
ATOM  941  P  A A  964  -17.106  98.510 260.749 1.00 0.00           P
ATOM  942  P  A A  965  -10.774  98.460 259.813 1.00 0.00           P
ATOM  943  P  G A  966   -6.547  96.167 264.998 1.00 0.00           P
ATOM  944  P  C A  967   -6.582  90.497 266.748 1.00 0.00           P
ATOM  945  P  A A  968   -4.614  88.029 260.465 1.00 0.00           P
ATOM  946  P  A A  969   -7.078  92.375 258.301 1.00 0.00           P
ATOM  947  P  C A  970   -7.598  95.404 254.999 1.00 0.00           P
ATOM  948  P  G A  971   -5.977  97.444 250.744 1.00 0.00           P
ATOM  949  P  C A  972   -6.201  93.401 249.292 1.00 0.00           P
ATOM  950  P  G A  973  -10.480  90.697 249.291 1.00 0.00           P
ATOM  951  P  A A  974  -16.360  92.283 247.709 1.00 0.00           P
ATOM  952  P  A A  975  -17.515  93.544 242.337 1.00 0.00           P
ATOM  953  P  G A  976  -16.775  93.385 236.792 1.00 0.00           P
ATOM  954  P  A A  977  -19.029  99.597 238.798 1.00 0.00           P
ATOM  955  P  A A  978  -17.222 103.061 235.250 1.00 0.00           P
ATOM  956  P  C A  979  -19.574 108.155 236.531 1.00 0.00           P
ATOM  957  P  C A  980  -25.176 108.411 235.740 1.00 0.00           P
ATOM  958  P  U A  981  -27.441 103.243 237.497 1.00 0.00           P
ATOM  959  P  U A  982  -25.500 100.154 241.604 1.00 0.00           P
ATOM  960  P  A A  983  -27.179 105.242 244.731 1.00 0.00           P
ATOM  961  P  C A  984  -24.803 108.489 248.281 1.00 0.00           P
ATOM  962  P  C A  985  -25.848 114.685 249.276 1.00 0.00           P
ATOM  963  P  A A  986  -27.219 120.089 247.344 1.00 0.00           P
ATOM  964  P  G A  987  -29.953 123.708 243.889 1.00 0.00           P
ATOM  965  P  G A  988  -34.721 124.485 239.810 1.00 0.00           P
ATOM  966  P  C A  989  -39.324 122.759 237.978 1.00 0.00           P
ATOM  967  P  C A  990  -44.426 117.633 238.405 1.00 0.00           P
ATOM  968  P  U A  991  -46.630 113.974 241.036 1.00 0.00           P
ATOM  969  P  U A  992  -50.598 111.755 244.438 1.00 0.00           P
ATOM  970  P  G A  993  -51.631 106.530 243.440 1.00 0.00           P
ATOM  971  P  A A  994  -44.577 105.309 241.854 1.00 0.00           P
ATOM  972  P  C A  995  -44.185  99.810 240.421 1.00 0.00           P
ATOM  973  P  A A  996  -47.947  94.774 241.070 1.00 0.00           P
ATOM  974  P  U A  997  -50.608  93.303 244.789 1.00 0.00           P
ATOM  975  P  G A  998  -56.381  92.992 245.961 1.00 0.00           P
ATOM  976  P  C A  998A -61.651  96.614 247.265 1.00 0.00           P
ATOM  977  P  U A  999  -65.935  99.973 247.053 1.00 0.00           P
ATOM  978  P  A A1000  -69.558 103.702 244.599 1.00 0.00           P
ATOM  979  P  G A1001  -70.768 107.412 240.270 1.00 0.00           P
ATOM  980  P  G A1002  -70.283 108.927 234.658 1.00 0.00           P
ATOM  981  P  G A1003  -67.507 108.397 229.360 1.00 0.00           P
ATOM  982  P  A A1004  -63.910 104.528 225.356 1.00 0.00           P
ATOM  983  P  A A1005  -57.918 101.363 227.364 1.00 0.00           P
ATOM  984  P  C A1006  -53.816  99.107 227.887 1.00 0.00           P
ATOM  985  P  C A1007  -49.528  98.668 222.987 1.00 0.00           P
ATOM  986  P  C A1008  -46.584 101.179 218.489 1.00 0.00           P
ATOM  987  P  G A1009  -44.198 106.072 215.570 1.00 0.00           P
ATOM  988  P  G A1010  -42.979 112.644 215.375 1.00 0.00           P
ATOM  989  P  G A1011  -42.496 118.561 216.446 1.00 0.00           P
ATOM  990  P  U A1012  -40.968 122.717 219.181 1.00 0.00           P
ATOM  991  P  G A1013  -37.257 123.727 223.284 1.00 0.00           P
ATOM  992  P  A A1014  -32.660 121.283 225.775 1.00 0.00           P
ATOM  993  P  A A1015  -33.132 115.485 225.842 1.00 0.00           P
ATOM  994  P  A A1016  -36.448 110.825 228.825 1.00 0.00           P
ATOM  995  P  G A1017  -40.846 110.074 232.716 1.00 0.00           P
ATOM  996  P  C A1018  -45.873 113.713 233.926 1.00 0.00           P
ATOM  997  P  C A1019  -50.041 117.406 231.899 1.00 0.00           P
```

| | | | | | | | | | |
|---|---|---|---|---|---|---|---|---|---|
| ATOM | 998 | P | U A1020 | -53.763 | 118.745 | 227.444 | 1.00 | 0.00 | P |
| ATOM | 999 | P | G A1021 | -56.039 | 116.920 | 221.959 | 1.00 | 0.00 | P |
| ATOM | 1000 | P | G A1022 | -58.533 | 113.413 | 216.912 | 1.00 | 0.00 | P |
| ATOM | 1001 | P | G A1023 | -60.030 | 107.858 | 213.458 | 1.00 | 0.00 | P |
| ATOM | 1002 | P | G A1024 | -62.001 | 102.787 | 214.154 | 1.00 | 0.00 | P |
| ATOM | 1003 | P | U A1025 | -63.163 | 100.418 | 217.475 | 1.00 | 0.00 | P |
| ATOM | 1004 | P | G A1026 | -67.233 | 97.236 | 220.363 | 1.00 | 0.00 | P |
| ATOM | 1005 | P | C A1027 | -68.481 | 90.735 | 222.225 | 1.00 | 0.00 | P |
| ATOM | 1006 | P | C A1028 | -68.517 | 87.401 | 226.220 | 1.00 | 0.00 | P |
| ATOM | 1007 | P | C A1028A | -74.065 | 86.192 | 227.949 | 1.00 | 0.00 | P |
| ATOM | 1008 | P | C A1028B | -79.771 | 87.981 | 228.942 | 1.00 | 0.00 | P |
| ATOM | 1009 | P | G A1029 | -83.879 | 90.239 | 227.264 | 1.00 | 0.00 | P |
| ATOM | 1010 | P | C A1030 | -86.345 | 92.652 | 222.830 | 1.00 | 0.00 | P |
| ATOM | 1011 | P | G A1031 | -81.917 | 94.677 | 219.823 | 1.00 | 0.00 | P |
| ATOM | 1012 | P | A A1032 | -78.752 | 100.255 | 219.969 | 1.00 | 0.00 | P |
| ATOM | 1013 | P | G A1032A | -77.054 | 104.833 | 222.156 | 1.00 | 0.00 | P |
| ATOM | 1014 | P | G A1032B | -77.223 | 105.195 | 228.990 | 1.00 | 0.00 | P |
| ATOM | 1015 | P | G A1033 | -75.848 | 102.827 | 233.904 | 1.00 | 0.00 | P |
| ATOM | 1016 | P | G A1034 | -72.603 | 99.419 | 237.691 | 1.00 | 0.00 | P |
| ATOM | 1017 | P | A A1035 | -67.485 | 96.059 | 238.604 | 1.00 | 0.00 | P |
| ATOM | 1018 | P | G A1036 | -62.227 | 93.637 | 237.958 | 1.00 | 0.00 | P |
| ATOM | 1019 | P | C A1037 | -56.833 | 93.763 | 236.272 | 1.00 | 0.00 | P |
| ATOM | 1020 | P | C A1038 | -53.668 | 98.368 | 234.776 | 1.00 | 0.00 | P |
| ATOM | 1021 | P | C A1039 | -53.214 | 104.564 | 235.206 | 1.00 | 0.00 | P |
| ATOM | 1022 | P | U A1040 | -53.913 | 110.237 | 236.856 | 1.00 | 0.00 | P |
| ATOM | 1023 | P | A A1041 | -56.080 | 114.244 | 240.298 | 1.00 | 0.00 | P |
| ATOM | 1024 | P | G A1042 | -57.712 | 115.737 | 245.656 | 1.00 | 0.00 | P |
| ATOM | 1025 | P | C A1043 | -57.787 | 112.792 | 251.491 | 1.00 | 0.00 | P |
| ATOM | 1026 | P | A A1044 | -56.929 | 108.558 | 255.248 | 1.00 | 0.00 | P |
| ATOM | 1027 | P | C A1045 | -53.471 | 103.094 | 256.119 | 1.00 | 0.00 | P |
| ATOM | 1028 | P | A A1046 | -48.607 | 99.090 | 253.564 | 1.00 | 0.00 | P |
| ATOM | 1029 | P | G A1047 | -42.991 | 100.382 | 249.489 | 1.00 | 0.00 | P |
| ATOM | 1030 | P | G A1048 | -37.647 | 101.668 | 249.205 | 1.00 | 0.00 | P |
| ATOM | 1031 | P | U A1049 | -34.555 | 98.910 | 252.845 | 1.00 | 0.00 | P |
| ATOM | 1032 | P | G A1050 | -32.190 | 103.997 | 252.564 | 1.00 | 0.00 | P |
| ATOM | 1033 | P | C A1051 | -28.348 | 104.098 | 257.708 | 1.00 | 0.00 | P |
| ATOM | 1034 | P | U A1052 | -26.034 | 103.047 | 262.757 | 1.00 | 0.00 | P |
| ATOM | 1035 | P | G A1053 | -24.961 | 99.823 | 266.407 | 1.00 | 0.00 | P |
| ATOM | 1036 | P | C A1054 | -22.390 | 93.905 | 268.957 | 1.00 | 0.00 | P |
| ATOM | 1037 | P | A A1055 | -28.707 | 95.747 | 269.625 | 1.00 | 0.00 | P |
| ATOM | 1038 | P | U A1056 | -28.399 | 89.666 | 271.362 | 1.00 | 0.00 | P |
| ATOM | 1039 | P | G A1057 | -30.562 | 84.145 | 266.734 | 1.00 | 0.00 | P |
| ATOM | 1040 | P | G A1058 | -28.223 | 82.616 | 261.047 | 1.00 | 0.00 | P |
| ATOM | 1041 | P | C A1059 | -24.914 | 81.775 | 256.755 | 1.00 | 0.00 | P |
| ATOM | 1042 | P | C A1060 | -19.243 | 82.398 | 255.410 | 1.00 | 0.00 | P |
| ATOM | 1043 | P | G A1061 | -14.753 | 83.573 | 258.418 | 1.00 | 0.00 | P |
| ATOM | 1044 | P | U A1062 | -9.841 | 85.069 | 260.797 | 1.00 | 0.00 | P |
| ATOM | 1045 | P | C A1063 | -6.514 | 83.878 | 264.964 | 1.00 | 0.00 | P |
| ATOM | 1046 | P | G A1064 | -3.790 | 80.217 | 269.216 | 1.00 | 0.00 | P |
| ATOM | 1047 | P | U A1065 | -6.561 | 77.112 | 264.203 | 1.00 | 0.00 | P |
| ATOM | 1048 | P | C A1066 | -3.831 | 71.456 | 264.663 | 1.00 | 0.00 | P |
| ATOM | 1049 | P | A A1067 | -2.710 | 69.170 | 269.372 | 1.00 | 0.00 | P |
| ATOM | 1050 | P | G A1068 | -6.102 | 67.826 | 273.923 | 1.00 | 0.00 | P |
| ATOM | 1051 | P | C A1069 | -11.256 | 71.107 | 277.037 | 1.00 | 0.00 | P |
| ATOM | 1052 | P | U A1070 | -16.635 | 71.430 | 279.163 | 1.00 | 0.00 | P |
| ATOM | 1053 | P | C A1071 | -20.953 | 67.170 | 282.431 | 1.00 | 0.00 | P |
| ATOM | 1054 | P | G A1072 | -24.984 | 63.295 | 284.030 | 1.00 | 0.00 | P |
| ATOM | 1055 | P | U A1073 | -26.366 | 59.331 | 287.231 | 1.00 | 0.00 | P |
| ATOM | 1056 | P | G A1074 | -24.226 | 56.689 | 291.009 | 1.00 | 0.00 | P |
| ATOM | 1057 | P | C A1075 | -20.397 | 54.515 | 294.604 | 1.00 | 0.00 | P |
| ATOM | 1058 | P | C A1076 | -16.155 | 56.013 | 298.360 | 1.00 | 0.00 | P |
| ATOM | 1059 | P | G A1077 | -14.759 | 60.670 | 301.178 | 1.00 | 0.00 | P |
| ATOM | 1060 | P | U A1078 | -15.313 | 64.637 | 303.882 | 1.00 | 0.00 | P |
| ATOM | 1061 | P | G A1079 | -19.056 | 68.383 | 301.572 | 1.00 | 0.00 | P |
| ATOM | 1062 | P | A A1080 | -18.972 | 72.332 | 297.241 | 1.00 | 0.00 | P |
| ATOM | 1063 | P | G A1081 | -18.371 | 73.415 | 293.287 | 1.00 | 0.00 | P |
| ATOM | 1064 | P | G A1082 | -12.984 | 70.387 | 290.374 | 1.00 | 0.00 | P |
| ATOM | 1065 | P | U A1083 | -9.015 | 66.221 | 289.292 | 1.00 | 0.00 | P |
| ATOM | 1066 | P | G A1084 | -8.585 | 61.051 | 287.177 | 1.00 | 0.00 | P |
| ATOM | 1067 | P | U A1085 | -9.720 | 58.812 | 281.839 | 1.00 | 0.00 | P |
| ATOM | 1068 | P | U A1086 | -5.656 | 63.784 | 281.413 | 1.00 | 0.00 | P |
| ATOM | 1069 | P | G A1087 | -0.878 | 64.670 | 284.051 | 1.00 | 0.00 | P |
| ATOM | 1070 | P | G A1088 | 3.996 | 62.295 | 284.774 | 1.00 | 0.00 | P |
| ATOM | 1071 | P | G A1089 | 7.520 | 59.740 | 281.284 | 1.00 | 0.00 | P |
| ATOM | 1072 | P | U A1090 | 8.702 | 58.222 | 275.898 | 1.00 | 0.00 | P |
| ATOM | 1073 | P | U A1091 | 7.008 | 58.785 | 270.184 | 1.00 | 0.00 | P |
| ATOM | 1074 | P | A A1092 | 4.253 | 61.219 | 265.740 | 1.00 | 0.00 | P |
| ATOM | 1075 | P | A A1093 | 1.192 | 64.737 | 268.947 | 1.00 | 0.00 | P |
| ATOM | 1076 | P | G A1094 | -2.909 | 64.279 | 272.695 | 1.00 | 0.00 | P |
| ATOM | 1077 | P | U A1095 | -7.603 | 61.154 | 270.916 | 1.00 | 0.00 | P |
| ATOM | 1078 | P | C A1096 | -7.109 | 55.737 | 271.012 | 1.00 | 0.00 | P |
| ATOM | 1079 | P | C A1097 | -4.821 | 50.720 | 274.196 | 1.00 | 0.00 | P |
| ATOM | 1080 | P | C A1098 | -2.309 | 47.750 | 278.285 | 1.00 | 0.00 | P |
| ATOM | 1081 | P | G A1099 | -1.822 | 47.812 | 284.367 | 1.00 | 0.00 | P |
| ATOM | 1082 | P | C A1100 | -3.232 | 49.840 | 289.475 | 1.00 | 0.00 | P |
| ATOM | 1083 | P | A A1101 | -7.328 | 52.227 | 292.974 | 1.00 | 0.00 | P |
| ATOM | 1084 | P | A A1102 | -8.626 | 57.823 | 290.338 | 1.00 | 0.00 | P |

| | | | | | | | | | |
|---|---|---|---|---|---|---|---|---|---|
| ATOM | 1085 | P | C | A1103 | -10.097 | 52.614 | 285.679 | 1.00 | 0.00 | P |
| ATOM | 1086 | P | G | A1104 | -13.749 | 50.268 | 281.738 | 1.00 | 0.00 | P |
| ATOM | 1087 | P | A | A1105 | -17.462 | 51.721 | 277.639 | 1.00 | 0.00 | P |
| ATOM | 1088 | P | G | A1106 | -19.949 | 55.522 | 272.695 | 1.00 | 0.00 | P |
| ATOM | 1089 | P | C | A1107 | -21.443 | 59.564 | 269.351 | 1.00 | 0.00 | P |
| ATOM | 1090 | P | G | A1108 | -20.809 | 65.000 | 266.524 | 1.00 | 0.00 | P |
| ATOM | 1091 | P | C | A1109 | -14.909 | 66.488 | 264.602 | 1.00 | 0.00 | P |
| ATOM | 1092 | P | A | A1110 | -10.423 | 64.933 | 262.576 | 1.00 | 0.00 | P |
| ATOM | 1093 | P | A | A1111 | -8.958 | 60.327 | 259.585 | 1.00 | 0.00 | P |
| ATOM | 1094 | P | C | A1112 | -10.563 | 56.628 | 257.434 | 1.00 | 0.00 | P |
| ATOM | 1095 | P | C | A1113 | -14.386 | 57.192 | 253.240 | 1.00 | 0.00 | P |
| ATOM | 1096 | P | C | A1114 | -15.943 | 59.386 | 247.297 | 1.00 | 0.00 | P |
| ATOM | 1097 | P | C | A1115 | -12.455 | 61.772 | 241.656 | 1.00 | 0.00 | P |
| ATOM | 1098 | P | C | A1116 | -7.142 | 62.287 | 237.846 | 1.00 | 0.00 | P |
| ATOM | 1099 | P | G | A1117 | -2.166 | 61.362 | 238.588 | 1.00 | 0.00 | P |
| ATOM | 1100 | P | C | A1118 | 1.312 | 57.612 | 237.795 | 1.00 | 0.00 | P |
| ATOM | 1101 | P | C | A1119 | 2.124 | 52.560 | 235.110 | 1.00 | 0.00 | P |
| ATOM | 1102 | P | G | A1120 | -0.027 | 47.719 | 232.815 | 1.00 | 0.00 | P |
| ATOM | 1103 | P | U | A1121 | -4.621 | 44.144 | 230.817 | 1.00 | 0.00 | P |
| ATOM | 1104 | P | U | A1122 | -9.648 | 42.752 | 228.941 | 1.00 | 0.00 | P |
| ATOM | 1105 | P | A | A1123 | -14.550 | 44.516 | 226.633 | 1.00 | 0.00 | P |
| ATOM | 1106 | P | G | A1124 | -15.611 | 47.539 | 223.113 | 1.00 | 0.00 | P |
| ATOM | 1107 | P | U | A1125 | -15.383 | 53.551 | 218.994 | 1.00 | 0.00 | P |
| ATOM | 1108 | P | U | A1126 | -13.487 | 60.294 | 220.482 | 1.00 | 0.00 | P |
| ATOM | 1109 | P | G | A1127 | -7.485 | 62.858 | 219.387 | 1.00 | 0.00 | P |
| ATOM | 1110 | P | C | A1128 | -0.893 | 60.022 | 217.870 | 1.00 | 0.00 | P |
| ATOM | 1111 | P | C | A1129 | 3.537 | 55.692 | 215.186 | 1.00 | 0.00 | P |
| ATOM | 1112 | P | A | A1130 | 5.729 | 51.249 | 213.757 | 1.00 | 0.00 | P |
| ATOM | 1113 | P | G | A1131 | 5.967 | 47.810 | 215.343 | 1.00 | 0.00 | P |
| ATOM | 1114 | P | C | A1132 | 4.553 | 46.589 | 209.917 | 1.00 | 0.00 | P |
| ATOM | 1115 | P | G | A1133 | 2.771 | 46.664 | 204.237 | 1.00 | 0.00 | P |
| ATOM | 1116 | P | G | A1134 | 1.261 | 49.361 | 199.612 | 1.00 | 0.00 | P |
| ATOM | 1117 | P | U | A1135 | 0.173 | 54.519 | 196.788 | 1.00 | 0.00 | P |
| ATOM | 1118 | P | U | A1136 | 0.736 | 60.985 | 196.894 | 1.00 | 0.00 | P |
| ATOM | 1119 | P | C | A1137 | 1.892 | 64.838 | 200.390 | 1.00 | 0.00 | P |
| ATOM | 1120 | P | G | A1138 | 3.479 | 64.556 | 205.028 | 1.00 | 0.00 | P |
| ATOM | 1121 | P | G | A1139 | 1.198 | 62.922 | 210.279 | 1.00 | 0.00 | P |
| ATOM | 1122 | P | C | A1140 | -5.100 | 62.960 | 211.150 | 1.00 | 0.00 | P |
| ATOM | 1123 | P | C | A1141 | -8.822 | 60.520 | 207.616 | 1.00 | 0.00 | P |
| ATOM | 1124 | P | G | A1142 | -11.471 | 56.205 | 206.777 | 1.00 | 0.00 | P |
| ATOM | 1125 | P | G | A1143 | -13.061 | 50.860 | 208.570 | 1.00 | 0.00 | P |
| ATOM | 1126 | P | G | A1144 | -11.323 | 46.881 | 212.795 | 1.00 | 0.00 | P |
| ATOM | 1127 | P | C | A1145 | -9.153 | 45.821 | 216.537 | 1.00 | 0.00 | P |
| ATOM | 1128 | P | A | A1146 | -6.659 | 46.634 | 223.315 | 1.00 | 0.00 | P |
| ATOM | 1129 | P | C | A1147 | -2.086 | 48.744 | 225.494 | 1.00 | 0.00 | P |
| ATOM | 1130 | P | U | A1148 | -0.109 | 53.524 | 227.800 | 1.00 | 0.00 | P |
| ATOM | 1131 | P | C | A1149 | -1.865 | 58.236 | 230.086 | 1.00 | 0.00 | P |
| ATOM | 1132 | P | U | A1150 | -7.368 | 61.265 | 231.173 | 1.00 | 0.00 | P |
| ATOM | 1133 | P | A | A1151 | -12.682 | 61.385 | 232.941 | 1.00 | 0.00 | P |
| ATOM | 1134 | P | A | A1152 | -16.752 | 57.491 | 236.712 | 1.00 | 0.00 | P |
| ATOM | 1135 | P | C | A1153 | -16.248 | 52.434 | 240.890 | 1.00 | 0.00 | P |
| ATOM | 1136 | P | G | A1154 | -13.504 | 47.504 | 243.525 | 1.00 | 0.00 | P |
| ATOM | 1137 | P | G | A1155 | -8.847 | 44.629 | 245.381 | 1.00 | 0.00 | P |
| ATOM | 1138 | P | G | A1156 | -2.611 | 47.227 | 246.970 | 1.00 | 0.00 | P |
| ATOM | 1139 | P | A | A1157 | -0.446 | 48.478 | 251.498 | 1.00 | 0.00 | P |
| ATOM | 1140 | P | C | A1158 | -3.582 | 50.096 | 256.737 | 1.00 | 0.00 | P |
| ATOM | 1141 | P | U | A1159 | -1.313 | 47.997 | 261.998 | 1.00 | 0.00 | P |
| ATOM | 1142 | P | G | A1160 | 0.604 | 43.078 | 258.774 | 1.00 | 0.00 | P |
| ATOM | 1143 | P | C | A1161 | 5.397 | 39.230 | 258.334 | 1.00 | 0.00 | P |
| ATOM | 1144 | P | C | A1162 | 11.239 | 38.014 | 260.251 | 1.00 | 0.00 | P |
| ATOM | 1145 | P | C | A1163 | 15.475 | 39.613 | 263.503 | 1.00 | 0.00 | P |
| ATOM | 1146 | P | G | A1164 | 17.404 | 42.351 | 268.320 | 1.00 | 0.00 | P |
| ATOM | 1147 | P | C | A1165 | 16.361 | 44.892 | 273.000 | 1.00 | 0.00 | P |
| ATOM | 1148 | P | G | A1166 | 12.819 | 45.681 | 277.567 | 1.00 | 0.00 | P |
| ATOM | 1149 | P | A | A1167 | 8.234 | 44.344 | 279.953 | 1.00 | 0.00 | P |
| ATOM | 1150 | P | A | A1168 | 5.266 | 41.422 | 275.367 | 1.00 | 0.00 | P |
| ATOM | 1151 | P | A | A1169 | 1.110 | 42.886 | 271.126 | 1.00 | 0.00 | P |
| ATOM | 1152 | P | G | A1170 | -1.148 | 47.079 | 267.728 | 1.00 | 0.00 | P |
| ATOM | 1153 | P | C | A1171 | 2.516 | 52.835 | 266.856 | 1.00 | 0.00 | P |
| ATOM | 1154 | P | G | A1172 | 6.952 | 55.896 | 265.728 | 1.00 | 0.00 | P |
| ATOM | 1155 | P | G | A1173 | 11.888 | 56.705 | 263.236 | 1.00 | 0.00 | P |
| ATOM | 1156 | P | G | A1174 | 15.335 | 54.643 | 259.016 | 1.00 | 0.00 | P |
| ATOM | 1157 | P | A | A1175 | 14.504 | 49.843 | 255.282 | 1.00 | 0.00 | P |
| ATOM | 1158 | P | G | A1176 | 13.992 | 45.946 | 251.275 | 1.00 | 0.00 | P |
| ATOM | 1159 | P | G | A1177 | 11.296 | 44.128 | 246.984 | 1.00 | 0.00 | P |
| ATOM | 1160 | P | A | A1178 | 8.612 | 46.059 | 242.401 | 1.00 | 0.00 | P |
| ATOM | 1161 | P | A | A1179 | 7.668 | 51.280 | 244.926 | 1.00 | 0.00 | P |
| ATOM | 1162 | P | G | A1180 | 4.295 | 52.224 | 249.883 | 1.00 | 0.00 | P |
| ATOM | 1163 | P | G | A1181 | 4.816 | 54.807 | 256.646 | 1.00 | 0.00 | P |
| ATOM | 1164 | P | A | A1182 | 1.712 | 58.059 | 257.511 | 1.00 | 0.00 | P |
| ATOM | 1165 | P | G | A1183 | 1.616 | 58.768 | 252.817 | 1.00 | 0.00 | P |
| ATOM | 1166 | P | G | A1184 | 3.416 | 63.171 | 251.084 | 1.00 | 0.00 | P |
| ATOM | 1167 | P | G | A1185 | 0.751 | 67.193 | 249.799 | 1.00 | 0.00 | P |
| ATOM | 1168 | P | G | A1186 | -3.656 | 70.587 | 250.169 | 1.00 | 0.00 | P |
| ATOM | 1169 | P | A | A1187 | -8.483 | 71.988 | 251.359 | 1.00 | 0.00 | P |
| ATOM | 1170 | P | C | A1188 | -13.807 | 71.268 | 251.812 | 1.00 | 0.00 | P |
| ATOM | 1171 | P | G | A1189 | -15.112 | 70.409 | 258.546 | 1.00 | 0.00 | P |

```
ATOM  1172  P  A A1191  -14.712  69.306 263.509  1.00  0.00  P
ATOM  1173  P  C A1192  -18.058  71.953 266.773  1.00  0.00  P
ATOM  1174  P  G A1193  -20.068  75.719 272.481  1.00  0.00  P
ATOM  1175  P  U A1194  -18.159  81.162 275.736  1.00  0.00  P
ATOM  1176  P  C A1195  -14.918  85.295 274.395  1.00  0.00  P
ATOM  1177  P  U A1196  -14.919  90.540 272.677  1.00  0.00  P
ATOM  1178  P  G A1197  -18.754  91.588 270.270  1.00  0.00  P
ATOM  1179  P  G A1198  -16.687  94.794 267.461  1.00  0.00  P
ATOM  1180  P  U A1199  -18.853  97.083 263.272  1.00  0.00  P
ATOM  1181  P  C A1200  -22.341  94.764 259.736  1.00  0.00  P
ATOM  1182  P  A A1201  -28.086  97.587 258.884  1.00  0.00  P
ATOM  1183  P  G A1202  -27.095  95.901 253.845  1.00  0.00  P
ATOM  1184  P  C A1203  -30.824  92.540 251.685  1.00  0.00  P
ATOM  1185  P  A A1204  -34.896  89.858 252.946  1.00  0.00  P
ATOM  1186  P  U A1205  -39.112  89.934 257.773  1.00  0.00  P
ATOM  1187  P  G A1206  -38.550  91.159 264.868  1.00  0.00  P
ATOM  1188  P  G A1207  -40.190  96.454 267.734  1.00  0.00  P
ATOM  1189  P  C A1208  -39.299 102.607 268.059  1.00  0.00  P
ATOM  1190  P  C A1209  -40.005 108.058 265.421  1.00  0.00  P
ATOM  1191  P  C A1210  -39.733 112.513 260.529  1.00  0.00  P
ATOM  1192  P  U A1211  -42.823 113.558 256.238  1.00  0.00  P
ATOM  1193  P  U A1212  -45.540 115.640 251.930  1.00  0.00  P
ATOM  1194  P  A A1213  -39.657 117.957 251.136  1.00  0.00  P
ATOM  1195  P  C A1214  -36.123 112.356 254.162  1.00  0.00  P
ATOM  1196  P  G A1215  -35.564 110.334 251.024  1.00  0.00  P
ATOM  1197  P  G A1216  -36.620 106.014 247.032  1.00  0.00  P
ATOM  1198  P  C A1217  -36.665 106.194 241.040  1.00  0.00  P
ATOM  1199  P  C A1218  -34.728 107.499 236.148  1.00  0.00  P
ATOM  1200  P  U A1219  -31.303 110.488 232.477  1.00  0.00  P
ATOM  1201  P  G A1220  -26.574 113.400 230.954  1.00  0.00  P
ATOM  1202  P  G A1221  -21.379 114.791 233.567  1.00  0.00  P
ATOM  1203  P  G A1222  -17.379 114.756 237.789  1.00  0.00  P
ATOM  1204  P  C A1223  -15.665 112.107 242.380  1.00  0.00  P
ATOM  1205  P  G A1224  -12.720 109.105 244.239  1.00  0.00  P
ATOM  1206  P  A A1225  -10.123 113.198 241.943  1.00  0.00  P
ATOM  1207  P  C A1226   -6.465 115.941 243.958  1.00  0.00  P
ATOM  1208  P  A A1227   -2.213 119.237 245.421  1.00  0.00  P
ATOM  1209  P  C A1228    2.747 119.285 248.647  1.00  0.00  P
ATOM  1210  P  A A1229    5.474 115.114 252.246  1.00  0.00  P
ATOM  1211  P  C A1230    5.335 109.731 253.842  1.00  0.00  P
ATOM  1212  P  G A1231    3.488 102.491 254.700  1.00  0.00  P
ATOM  1213  P  U A1232    2.411  96.104 251.136  1.00  0.00  P
ATOM  1214  P  G A1233    2.328  93.114 246.008  1.00  0.00  P
ATOM  1215  P  C A1234    4.300  93.899 239.871  1.00  0.00  P
ATOM  1216  P  U A1235    7.333  95.573 235.015  1.00  0.00  P
ATOM  1217  P  A A1236   11.503  97.952 232.073  1.00  0.00  P
ATOM  1218  P  C A1237   17.402 100.514 232.397  1.00  0.00  P
ATOM  1219  P  A A1238   20.669  97.902 234.411  1.00  0.00  P
ATOM  1220  P  A A1239   24.379  94.612 232.885  1.00  0.00  P
ATOM  1221  P  U A1240   21.183  90.963 230.137  1.00  0.00  P
ATOM  1222  P  G A1241   16.500  88.238 230.721  1.00  0.00  P
ATOM  1223  P  C A1242   13.665  91.819 227.258  1.00  0.00  P
ATOM  1224  P  C A1243   11.720  92.941 221.856  1.00  0.00  P
ATOM  1225  P  C A1244   10.687  91.434 216.402  1.00  0.00  P
ATOM  1226  P  A A1245    9.681  87.050 212.728  1.00  0.00  P
ATOM  1227  P  C A1246    8.847  81.480 211.510  1.00  0.00  P
ATOM  1228  P  U A1247    7.548  76.179 213.288  1.00  0.00  P
ATOM  1229  P  A A1248    9.338  72.576 219.321  1.00  0.00  P
ATOM  1230  P  C A1249    6.277  70.522 223.987  1.00  0.00  P
ATOM  1231  P  A A1250    1.679  70.134 228.039  1.00  0.00  P
ATOM  1232  P  A A1251   -3.359  70.278 230.835  1.00  0.00  P
ATOM  1233  P  A A1252   -8.946  71.103 233.169  1.00  0.00  P
ATOM  1234  P  G A1253  -14.002  74.876 233.059  1.00  0.00  P
ATOM  1235  P  C A1254  -16.645  78.906 228.487  1.00  0.00  P
ATOM  1236  P  G A1255  -18.640  81.450 223.348  1.00  0.00  P
ATOM  1237  P  A A1256  -22.111  80.975 220.005  1.00  0.00  P
ATOM  1238  P  U A1257  -25.408  87.268 219.912  1.00  0.00  P
ATOM  1239  P  G A1258  -22.083  89.052 218.985  1.00  0.00  P
ATOM  1240  P  C A1259  -16.921  87.169 220.158  1.00  0.00  P
ATOM  1241  P  C A1260  -11.673  86.034 219.514  1.00  0.00  P
ATOM  1242  P  A A1261   -8.817  85.140 212.838  1.00  0.00  P
ATOM  1243  P  C A1262   -4.665  82.277 210.386  1.00  0.00  P
ATOM  1244  P  C A1263   -3.117  84.024 204.737  1.00  0.00  P
ATOM  1245  P  C A1264   -3.066  88.489 201.300  1.00  0.00  P
ATOM  1246  P  G A1265   -3.577  94.381 199.972  1.00  0.00  P
ATOM  1247  P  G A1266   -2.699  99.367 201.815  1.00  0.00  P
ATOM  1248  P  C A1267   -0.078 102.118 205.813  1.00  0.00  P
ATOM  1249  P  A A1268   -0.174  97.352 209.279  1.00  0.00  P
ATOM  1250  P  A A1269   -3.741  95.794 214.209  1.00  0.00  P
ATOM  1251  P  C A1270   -8.306  95.514 217.570  1.00  0.00  P
ATOM  1252  P  G A1271  -13.626  96.262 213.753  1.00  0.00  P
ATOM  1253  P  G A1272  -16.845  96.035 208.722  1.00  0.00  P
ATOM  1254  P  G A1273  -18.650  92.848 204.225  1.00  0.00  P
ATOM  1255  P  G A1274  -18.916  87.356 202.241  1.00  0.00  P
ATOM  1256  P  A A1275  -18.311  81.231 204.032  1.00  0.00  P
ATOM  1257  P  G A1276  -17.909  75.953 205.777  1.00  0.00  P
ATOM  1258  P  C A1277  -17.829  72.180 210.690  1.00  0.00  P
```

```
ATOM   1259  P    U A1278   -21.504  70.739 214.100  1.00  0.00           P
ATOM   1260  P    A A1279   -24.934  73.096 217.704  1.00  0.00           P
ATOM   1261  P    A A1280   -22.699  69.384 221.095  1.00  0.00           P
ATOM   1262  P    U A1281   -17.747  68.077 221.814  1.00  0.00           P
ATOM   1263  P    C A1282   -16.047  65.197 215.849  1.00  0.00           P
ATOM   1264  P    G A1283   -11.936  68.880 213.493  1.00  0.00           P
ATOM   1265  P    C A1284    -8.317  73.204 214.568  1.00  0.00           P
ATOM   1266  P    A A1285    -7.441  79.419 219.910  1.00  0.00           P
ATOM   1267  P    A A1286    -2.460  81.151 216.028  1.00  0.00           P
ATOM   1268  P    A A1287     2.736  81.521 219.390  1.00  0.00           P
ATOM   1269  P    A A1288     3.135  81.570 224.197  1.00  0.00           P
ATOM   1270  P    A A1289     6.313  82.638 229.195  1.00  0.00           P
ATOM   1271  P    G A1290    11.492  84.441 228.261  1.00  0.00           P
ATOM   1272  P    G A1291    14.268  79.371 228.715  1.00  0.00           P
ATOM   1273  P    U A1292    17.753  75.897 225.480  1.00  0.00           P
ATOM   1274  P    G A1293    21.055  76.312 221.008  1.00  0.00           P
ATOM   1275  P    G A1294    23.896  79.817 217.368  1.00  0.00           P
ATOM   1276  P    G A1295    25.547  85.116 215.416  1.00  0.00           P
ATOM   1277  P    C A1296    26.307  90.756 215.301  1.00  0.00           P
ATOM   1278  P    C A1297    25.732  96.033 219.892  1.00  0.00           P
ATOM   1279  P    C A1298    30.238  96.190 225.023  1.00  0.00           P
ATOM   1280  P    A A1299    30.043  99.006 230.957  1.00  0.00           P
ATOM   1281  P    G A1300    27.579 104.530 230.854  1.00  0.00           P
ATOM   1282  P    U A1301    22.135 105.376 228.224  1.00  0.00           P
ATOM   1283  P    U A1302    20.527 103.822 223.387  1.00  0.00           P
ATOM   1284  P    C A1303    18.832  97.955 222.150  1.00  0.00           P
ATOM   1285  P    G A1304    16.703  97.119 227.434  1.00  0.00           P
ATOM   1286  P    G A1305    12.405  99.069 229.391  1.00  0.00           P
ATOM   1287  P    A A1306     7.083 103.926 230.267  1.00  0.00           P
ATOM   1288  P    U A1307     3.502 107.823 233.812  1.00  0.00           P
ATOM   1289  P    U A1308     2.130 112.908 232.089  1.00  0.00           P
ATOM   1290  P    G A1309     0.871 116.296 226.864  1.00  0.00           P
ATOM   1291  P    G A1310    -0.624 117.518 221.494  1.00  0.00           P
ATOM   1292  P    G A1311    -2.845 115.178 216.412  1.00  0.00           P
ATOM   1293  P    G A1312    -5.303 111.244 213.057  1.00  0.00           P
ATOM   1294  P    U A1313    -8.549 105.553 213.281  1.00  0.00           P
ATOM   1295  P    C A1314   -11.320 100.470 214.244  1.00  0.00           P
ATOM   1296  P    U A1315   -16.256  99.765 218.242  1.00  0.00           P
ATOM   1297  P    G A1316   -20.833  98.575 221.471  1.00  0.00           P
ATOM   1298  P    C A1317   -25.851 101.604 222.755  1.00  0.00           P
ATOM   1299  P    A A1318   -25.174 107.313 221.601  1.00  0.00           P
ATOM   1300  P    A A1319   -20.085 109.826 220.895  1.00  0.00           P
ATOM   1301  P    C A1320   -15.398 108.969 224.823  1.00  0.00           P
ATOM   1302  P    C A1321   -13.746 111.092 229.841  1.00  0.00           P
ATOM   1303  P    C A1322   -12.881 110.184 234.449  1.00  0.00           P
ATOM   1304  P    G A1323    -8.717 107.613 231.073  1.00  0.00           P
ATOM   1305  P    A A1324    -6.335 102.690 230.933  1.00  0.00           P
ATOM   1306  P    C A1325    -2.669  98.968 227.801  1.00  0.00           P
ATOM   1307  P    C A1326     0.351  97.886 223.089  1.00  0.00           P
ATOM   1308  P    C A1327     3.659  98.705 218.595  1.00  0.00           P
ATOM   1309  P    C A1328     6.697 102.181 215.629  1.00  0.00           P
ATOM   1310  P    A A1329    10.227 106.740 215.871  1.00  0.00           P
ATOM   1311  P    U A1330    12.174 111.296 219.312  1.00  0.00           P
ATOM   1312  P    G A1331    11.290 113.474 224.315  1.00  0.00           P
ATOM   1313  P    A A1332    14.073 110.123 229.405  1.00  0.00           P
ATOM   1314  P    A A1333    15.155 111.358 235.506  1.00  0.00           P
ATOM   1315  P    G A1334    17.442 108.979 240.431  1.00  0.00           P
ATOM   1316  P    C A1335    19.480 103.976 240.398  1.00  0.00           P
ATOM   1317  P    C A1336    22.490 100.627 243.998  1.00  0.00           P
ATOM   1318  P    G A1337    19.943  97.282 247.146  1.00  0.00           P
ATOM   1319  P    G A1338    18.772 100.224 251.617  1.00  0.00           P
ATOM   1320  P    A A1339    19.559 100.886 257.004  1.00  0.00           P
ATOM   1321  P    A A1340    16.120  99.169 261.712  1.00  0.00           P
ATOM   1322  P    U A1341    10.722  95.687 261.637  1.00  0.00           P
ATOM   1323  P    C A1342     7.116  91.611 258.791  1.00  0.00           P
ATOM   1324  P    G A1343     4.648  86.914 256.123  1.00  0.00           P
ATOM   1325  P    C A1344     3.718  82.036 253.683  1.00  0.00           P
ATOM   1326  P    U A1345     5.863  76.417 252.964  1.00  0.00           P
ATOM   1327  P    A A1346     7.199  71.013 251.940  1.00  0.00           P
ATOM   1328  P    G A1347     6.767  67.324 246.694  1.00  0.00           P
ATOM   1329  P    U A1348     4.669  73.102 242.824  1.00  0.00           P
ATOM   1330  P    A A1349     4.890  78.209 245.336  1.00  0.00           P
ATOM   1331  P    A A1350     7.776  81.801 245.891  1.00  0.00           P
ATOM   1332  P    U A1351     9.895  84.894 241.793  1.00  0.00           P
ATOM   1333  P    C A1352     8.952  85.938 235.876  1.00  0.00           P
ATOM   1334  P    G A1353     5.752  86.233 231.640  1.00  0.00           P
ATOM   1335  P    C A1354    -0.070  85.228 228.194  1.00  0.00           P
ATOM   1336  P    G A1355    -5.455  83.703 227.916  1.00  0.00           P
ATOM   1337  P    G A1356   -11.281  83.170 229.156  1.00  0.00           P
ATOM   1338  P    A A1357   -16.244  83.661 232.148  1.00  0.00           P
ATOM   1339  P    U A1358   -20.408  85.431 235.558  1.00  0.00           P
ATOM   1340  P    C A1359   -22.486  90.725 236.375  1.00  0.00           P
ATOM   1341  P    A A1360   -22.477  94.006 231.272  1.00  0.00           P
ATOM   1342  P    G A1361   -17.805  93.874 227.426  1.00  0.00           P
ATOM   1343  P    C A1362   -12.879  95.887 228.359  1.00  0.00           P
ATOM   1344  P    C A1362A   -9.026  96.433 233.294  1.00  0.00           P
ATOM   1345  P    A A1363    -7.727  97.022 238.805  1.00  0.00           P
```

| | | | | | | | | | | |
|---|---|---|---|---|---|---|---|---|---|---|
| ATOM | 1346 | P | U | A1364 | -3.319 | 93.299 | 235.112 | 1.00 | 0.00 | P |
| ATOM | 1347 | P | G | A1365 | -1.645 | 90.981 | 240.881 | 1.00 | 0.00 | P |
| ATOM | 1348 | P | C | A1366 | -4.248 | 88.004 | 244.859 | 1.00 | 0.00 | P |
| ATOM | 1349 | P | C | A1367 | -7.173 | 83.304 | 245.937 | 1.00 | 0.00 | P |
| ATOM | 1350 | P | G | A1368 | -8.050 | 77.957 | 244.314 | 1.00 | 0.00 | P |
| ATOM | 1351 | P | C | A1369 | -5.435 | 73.930 | 239.635 | 1.00 | 0.00 | P |
| ATOM | 1352 | P | G | A1370 | -2.775 | 71.260 | 236.051 | 1.00 | 0.00 | P |
| ATOM | 1353 | P | G | A1371 | 3.345 | 70.120 | 233.003 | 1.00 | 0.00 | P |
| ATOM | 1354 | P | U | A1372 | 8.452 | 70.621 | 231.381 | 1.00 | 0.00 | P |
| ATOM | 1355 | P | G | A1373 | 12.073 | 73.310 | 233.054 | 1.00 | 0.00 | P |
| ATOM | 1356 | P | A | A1374 | 14.244 | 73.062 | 238.682 | 1.00 | 0.00 | P |
| ATOM | 1357 | P | A | A1375 | 18.060 | 74.196 | 243.969 | 1.00 | 0.00 | P |
| ATOM | 1358 | P | U | A1376 | 20.906 | 75.740 | 248.326 | 1.00 | 0.00 | P |
| ATOM | 1359 | P | A | A1377 | 20.774 | 74.376 | 254.120 | 1.00 | 0.00 | P |
| ATOM | 1360 | P | C | A1378 | 18.809 | 71.043 | 258.996 | 1.00 | 0.00 | P |
| ATOM | 1361 | P | G | A1379 | 21.209 | 69.293 | 264.474 | 1.00 | 0.00 | P |
| ATOM | 1362 | P | U | A1380 | 17.971 | 71.535 | 269.966 | 1.00 | 0.00 | P |
| ATOM | 1363 | P | U | A1381 | 16.513 | 75.620 | 273.985 | 1.00 | 0.00 | P |
| ATOM | 1364 | P | C | A1382 | 17.007 | 81.267 | 275.462 | 1.00 | 0.00 | P |
| ATOM | 1365 | P | C | A1383 | 12.874 | 85.431 | 273.856 | 1.00 | 0.00 | P |
| ATOM | 1366 | P | C | A1384 | 9.258 | 87.065 | 270.843 | 1.00 | 0.00 | P |
| ATOM | 1367 | P | G | A1385 | 3.079 | 86.412 | 270.638 | 1.00 | 0.00 | P |
| ATOM | 1368 | P | G | A1386 | -0.904 | 81.205 | 271.788 | 1.00 | 0.00 | P |
| ATOM | 1369 | P | G | A1387 | -2.359 | 74.979 | 276.040 | 1.00 | 0.00 | P |
| ATOM | 1370 | P | C | A1388 | -2.410 | 70.216 | 279.952 | 1.00 | 0.00 | P |
| ATOM | 1371 | P | C | A1389 | -1.598 | 68.669 | 286.921 | 1.00 | 0.00 | P |
| ATOM | 1372 | P | U | A1390 | 1.362 | 72.771 | 291.272 | 1.00 | 0.00 | P |
| ATOM | 1373 | P | U | A1391 | 2.537 | 76.511 | 294.768 | 1.00 | 0.00 | P |
| ATOM | 1374 | P | G | A1392 | 3.363 | 82.057 | 296.677 | 1.00 | 0.00 | P |
| ATOM | 1375 | P | U | A1393 | 1.069 | 87.115 | 297.250 | 1.00 | 0.00 | P |
| ATOM | 1376 | P | A | A1394 | -3.265 | 88.978 | 296.687 | 1.00 | 0.00 | P |
| ATOM | 1377 | P | C | A1395 | -6.613 | 91.511 | 294.494 | 1.00 | 0.00 | P |
| ATOM | 1378 | P | A | A1396 | -8.866 | 92.314 | 289.806 | 1.00 | 0.00 | P |
| ATOM | 1379 | P | C | A1397 | -12.513 | 90.137 | 286.516 | 1.00 | 0.00 | P |
| ATOM | 1380 | P | A | A1398 | -7.463 | 89.052 | 282.494 | 1.00 | 0.00 | P |
| ATOM | 1381 | P | C | A1399 | -1.147 | 90.476 | 282.083 | 1.00 | 0.00 | P |
| ATOM | 1382 | P | C | A1400 | -1.771 | 96.309 | 279.198 | 1.00 | 0.00 | P |
| ATOM | 1383 | P | G | A1401 | -5.070 | 96.414 | 282.635 | 1.00 | 0.00 | P |
| ATOM | 1384 | P | C | A1402 | -5.477 | 95.692 | 287.429 | 1.00 | 0.00 | P |
| ATOM | 1385 | P | C | A1403 | -2.961 | 98.400 | 291.434 | 1.00 | 0.00 | P |
| ATOM | 1386 | P | C | A1404 | -1.457 | 100.874 | 295.671 | 1.00 | 0.00 | P |
| ATOM | 1387 | P | G | A1405 | 1.518 | 105.184 | 298.607 | 1.00 | 0.00 | P |
| ATOM | 1388 | P | U | A1406 | 3.500 | 111.049 | 299.131 | 1.00 | 0.00 | P |
| ATOM | 1389 | P | C | A1407 | 2.848 | 117.468 | 298.182 | 1.00 | 0.00 | P |
| ATOM | 1390 | P | A | A1408 | 0.573 | 122.069 | 295.919 | 1.00 | 0.00 | P |
| ATOM | 1391 | P | C | A1409 | -4.022 | 125.756 | 295.258 | 1.00 | 0.00 | P |
| ATOM | 1392 | P | G | A1410 | -9.494 | 126.453 | 295.479 | 1.00 | 0.00 | P |
| ATOM | 1393 | P | C | A1411 | -14.149 | 125.675 | 298.550 | 1.00 | 0.00 | P |
| ATOM | 1394 | P | C | A1412 | -16.993 | 123.992 | 303.675 | 1.00 | 0.00 | P |
| ATOM | 1395 | P | A | A1413 | -17.578 | 122.285 | 309.184 | 1.00 | 0.00 | P |
| ATOM | 1396 | P | U | A1414 | -13.860 | 118.826 | 314.160 | 1.00 | 0.00 | P |
| ATOM | 1397 | P | G | A1415 | -8.032 | 119.211 | 317.049 | 1.00 | 0.00 | P |
| ATOM | 1398 | P | G | A1416 | -3.952 | 121.471 | 319.581 | 1.00 | 0.00 | P |
| ATOM | 1399 | P | G | A1417 | -1.433 | 125.923 | 321.730 | 1.00 | 0.00 | P |
| ATOM | 1400 | P | A | A1418 | -0.578 | 132.766 | 323.662 | 1.00 | 0.00 | P |
| ATOM | 1401 | P | G | A1419 | -4.817 | 137.132 | 327.087 | 1.00 | 0.00 | P |
| ATOM | 1402 | P | C | A1420 | -10.607 | 139.153 | 328.160 | 1.00 | 0.00 | P |
| ATOM | 1403 | P | G | A1421 | -16.269 | 137.905 | 329.476 | 1.00 | 0.00 | P |
| ATOM | 1404 | P | G | A1422 | -19.917 | 134.353 | 331.858 | 1.00 | 0.00 | P |
| ATOM | 1405 | P | G | A1423 | -20.434 | 130.405 | 336.087 | 1.00 | 0.00 | P |
| ATOM | 1406 | P | C | A1424 | -19.449 | 126.146 | 340.389 | 1.00 | 0.00 | P |
| ATOM | 1407 | P | U | A1425 | -17.268 | 125.963 | 345.304 | 1.00 | 0.00 | P |
| ATOM | 1408 | P | C | A1426 | -13.265 | 127.243 | 349.369 | 1.00 | 0.00 | P |
| ATOM | 1409 | P | U | A1427 | -9.706 | 130.290 | 352.731 | 1.00 | 0.00 | P |
| ATOM | 1410 | P | A | A1428 | -8.402 | 135.134 | 355.242 | 1.00 | 0.00 | P |
| ATOM | 1411 | P | C | A1429 | -9.656 | 140.259 | 357.043 | 1.00 | 0.00 | P |
| ATOM | 1412 | P | C | A1430 | -14.372 | 144.555 | 356.986 | 1.00 | 0.00 | P |
| ATOM | 1413 | P | C | A1431 | -19.788 | 146.306 | 356.479 | 1.00 | 0.00 | P |
| ATOM | 1414 | P | G | A1432 | -25.225 | 145.198 | 356.964 | 1.00 | 0.00 | P |
| ATOM | 1415 | P | A | A1433 | -29.392 | 140.727 | 358.392 | 1.00 | 0.00 | P |
| ATOM | 1416 | P | A | A1434 | -34.537 | 138.601 | 359.818 | 1.00 | 0.00 | P |
| ATOM | 1417 | P | G | A1435 | -33.200 | 139.490 | 361.343 | 1.00 | 0.00 | P |
| ATOM | 1418 | P | U | A1436 | -33.247 | 135.656 | 365.616 | 1.00 | 0.00 | P |
| ATOM | 1419 | P | C | A1437 | -31.223 | 132.928 | 370.764 | 1.00 | 0.00 | P |
| ATOM | 1420 | P | G | A1438 | -27.255 | 133.633 | 374.949 | 1.00 | 0.00 | P |
| ATOM | 1421 | P | C | A1439 | -24.627 | 137.194 | 378.547 | 1.00 | 0.00 | P |
| ATOM | 1422 | P | C | A1440 | -24.623 | 142.439 | 381.105 | 1.00 | 0.00 | P |
| ATOM | 1423 | P | G | A1441 | -26.953 | 147.512 | 382.313 | 1.00 | 0.00 | P |
| ATOM | 1424 | P | G | A1442 | -25.524 | 151.466 | 380.305 | 1.00 | 0.00 | P |
| ATOM | 1425 | P | G | A1443 | -26.513 | 155.725 | 383.720 | 1.00 | 0.00 | P |
| ATOM | 1426 | P | A | A1446 | -29.574 | 158.333 | 381.495 | 1.00 | 0.00 | P |
| ATOM | 1427 | P | G | A1447 | -35.863 | 158.518 | 380.103 | 1.00 | 0.00 | P |
| ATOM | 1428 | P | C | A1448 | -41.408 | 156.205 | 378.928 | 1.00 | 0.00 | P |
| ATOM | 1429 | P | C | A1449 | -45.711 | 152.797 | 380.366 | 1.00 | 0.00 | P |
| ATOM | 1430 | P | U | A1450 | -48.082 | 148.965 | 383.058 | 1.00 | 0.00 | P |
| ATOM | 1431 | P | A | A1451 | -46.812 | 146.351 | 388.492 | 1.00 | 0.00 | P |
| ATOM | 1432 | P | C | A1452 | -42.955 | 143.015 | 392.264 | 1.00 | 0.00 | P |

```
ATOM   1433  P    G A1453   -36.272 142.583 391.542  1.00  0.00           P
ATOM   1434  P    G A1454   -33.882 141.614 388.697  1.00  0.00           P
ATOM   1435  P    G A1455   -35.075 139.997 382.396  1.00  0.00           P
ATOM   1436  P    C A1459   -36.990 140.154 377.052  1.00  0.00           P
ATOM   1437  P    A A1460   -37.632 142.973 371.930  1.00  0.00           P
ATOM   1438  P    G A1461   -36.298 146.866 368.110  1.00  0.00           P
ATOM   1439  P    G A1462   -31.045 149.627 367.291  1.00  0.00           P
ATOM   1440  P    C A1463   -25.542 150.006 367.093  1.00  0.00           P
ATOM   1441  P    G A1464   -20.287 147.247 366.930  1.00  0.00           P
ATOM   1442  P    C A1465   -17.080 142.102 366.033  1.00  0.00           P
ATOM   1443  P    C A1466   -15.618 137.222 363.951  1.00  0.00           P
ATOM   1444  P    G A1467   -19.448 132.826 361.494  1.00  0.00           P
ATOM   1445  P    A A1468   -23.087 132.490 357.353  1.00  0.00           P
ATOM   1446  P    G A1469   -24.454 132.051 351.551  1.00  0.00           P
ATOM   1447  P    G A1470   -25.484 134.464 347.109  1.00  0.00           P
ATOM   1448  P    G A1471   -23.071 138.412 344.210  1.00  0.00           P
ATOM   1449  P    U A1472   -18.836 142.299 342.153  1.00  0.00           P
ATOM   1450  P    A A1473   -13.523 144.002 341.028  1.00  0.00           P
ATOM   1451  P    G A1474    -8.166 142.416 340.346  1.00  0.00           P
ATOM   1452  P    G A1475    -4.003 138.044 339.694  1.00  0.00           P
ATOM   1453  P    G A1476    -1.504 130.494 339.637  1.00  0.00           P
ATOM   1454  P    C A1477    -2.592 125.385 336.988  1.00  0.00           P
ATOM   1455  P    C A1478    -6.266 121.756 334.468  1.00  0.00           P
ATOM   1456  P    C A1479   -11.252 119.677 330.194  1.00  0.00           P
ATOM   1457  P    G A1480   -15.025 120.968 325.472  1.00  0.00           P
ATOM   1458  P    U A1481   -16.523 124.319 320.645  1.00  0.00           P
ATOM   1459  P    G A1482   -15.345 128.319 316.562  1.00  0.00           P
ATOM   1460  P    A A1483   -11.524 133.063 312.716  1.00  0.00           P
ATOM   1461  P    C A1484    -7.487 135.447 309.132  1.00  0.00           P
ATOM   1462  P    U A1485    -2.196 133.428 307.852  1.00  0.00           P
ATOM   1463  P    G A1486    -0.020 127.439 307.095  1.00  0.00           P
ATOM   1464  P    G A1487     1.393 121.195 307.703  1.00  0.00           P
ATOM   1465  P    G A1488    -0.919 114.683 307.420  1.00  0.00           P
ATOM   1466  P    G A1489    -6.053 111.268 305.325  1.00  0.00           P
ATOM   1467  P    C A1490   -10.823 109.175 302.552  1.00  0.00           P
ATOM   1468  P    G A1491   -14.643 110.866 298.353  1.00  0.00           P
ATOM   1469  P    A A1492   -13.829 112.576 292.463  1.00  0.00           P
ATOM   1470  P    A A1493   -13.955 111.862 286.730  1.00  0.00           P
ATOM   1471  P    G A1494    -7.889 112.958 285.534  1.00  0.00           P
ATOM   1472  P    U A1495    -2.725 115.480 284.879  1.00  0.00           P
ATOM   1473  P    C A1496     2.310 113.783 285.162  1.00  0.00           P
ATOM   1474  P    G A1497     6.665 111.603 286.225  1.00  0.00           P
ATOM   1475  P    U A1498     9.255 106.426 287.008  1.00  0.00           P
ATOM   1476  P    A A1499     7.526 101.442 289.278  1.00  0.00           P
ATOM   1477  P    A A1500     8.207  97.176 293.753  1.00  0.00           P
ATOM   1478  P    C A1501     5.770  93.336 295.872  1.00  0.00           P
ATOM   1479  P    A A1502     2.247  90.962 293.557  1.00  0.00           P
ATOM   1480  P    A A1503     5.006  85.700 293.070  1.00  0.00           P
ATOM   1481  P    G A1504     9.890  89.518 293.018  1.00  0.00           P
ATOM   1482  P    G A1505     9.836  94.484 290.865  1.00  0.00           P
ATOM   1483  P    U A1506    15.161  94.204 288.951  1.00  0.00           P
ATOM   1484  P    A A1507    16.027  91.381 294.670  1.00  0.00           P
ATOM   1485  P    G A1508    11.845  93.509 297.361  1.00  0.00           P
ATOM   1486  P    C A1509     7.482  95.391 301.535  1.00  0.00           P
ATOM   1487  P    U A1510     6.207  97.007 306.915  1.00  0.00           P
ATOM   1488  P    G A1511     7.654  98.426 312.156  1.00  0.00           P
ATOM   1489  P    U A1512    10.303 102.043 315.674  1.00  0.00           P
ATOM   1490  P    A A1513    15.107 105.685 316.089  1.00  0.00           P
ATOM   1491  P    C A1514    18.419 109.423 313.322  1.00  0.00           P
ATOM   1492  P    C A1515    20.493 111.754 308.279  1.00  0.00           P
ATOM   1493  P    G A1516    20.219 113.050 302.837  1.00  0.00           P
ATOM   1494  P    G A1517    16.580 114.747 298.146  1.00  0.00           P
ATOM   1495  P    A A1518    11.893 113.495 298.898  1.00  0.00           P
ATOM   1496  P    A A1519     7.672 109.360 298.515  1.00  0.00           P
ATOM   1497  P    G A1520     7.170 103.963 299.099  1.00  0.00           P
ATOM   1498  P    G A1521    12.879 100.747 298.260  1.00  0.00           P
ATOM   1499  P    U A1522    18.154  99.261 298.762  1.00  0.00           P
ATOM   1500  P    G A1523    22.405  97.471 302.612  1.00  0.00           P
ATOM   1501  P    C A1524    24.713  95.670 306.993  1.00  0.00           P
ATOM   1502  P    G A1525    23.838  92.009 311.175  1.00  0.00           P
ATOM   1503  P    G A1526    19.878  87.975 312.725  1.00  0.00           P
ATOM   1504  P    C A1527    14.697  85.034 312.950  1.00  0.00           P
ATOM   1505  P    U A1528    10.264  82.239 310.565  1.00  0.00           P
ATOM   1506  P    G A1529     5.109  81.194 306.281  1.00  0.00           P
ATOM   1507  P    G A1530     7.872  80.302 300.505  1.00  0.00           P
ATOM   1508  P    A A1531    12.974  78.318 295.881  1.00  0.00           P
ATOM   1509  P    U A1532    11.401  73.145 294.743  1.00  0.00           P
ATOM   1510  P    C A1533    13.837  71.387 289.434  1.00  0.00           P
ATOM   1511  P    A A1534    16.834  72.563 284.907  1.00  0.00           P
ATOM   1512  P    C A1535    22.783  69.584 285.036  1.00  0.00           P
ATOM   1513  P    C A1536    27.672  69.475 291.682  1.00  0.00           P
ATOM   1514  P    U A1537    30.304  67.427 297.874  1.00  0.00           P
ATOM   1515  P    C A1538    28.873  64.302 302.903  1.00  0.00           P
ATOM   1516  P    C A1539    26.322  62.460 307.086  1.00  0.00           P
ATOM   1517  P    U A1540    21.268  59.445 309.559  1.00  0.00           P
ATOM   1518  P    U A1541    18.809  53.594 308.171  1.00  0.00           P
ATOM   1519  P    U A1542    20.261  52.408 301.460  1.00  0.00           P
```

| | | | | | | | | | | |
|---|---|---|---|---|---|---|---|---|---|---|
| TER | 1520 | | U | A1542 | | | | | | |
| ATOM | 1521 | O3P | G | B | 1 | -1.228 | 162.393 | 290.854 | 1.00 | 0.00 | O |
| ATOM | 1522 | P | G | B | 1 | 0.016 | 161.519 | 290.810 | 1.00 | 0.00 | P |
| ATOM | 1523 | O1P | G | B | 1 | 0.173 | 160.766 | 289.497 | 1.00 | 0.00 | O |
| ATOM | 1524 | O2P | G | B | 1 | 0.174 | 160.633 | 292.036 | 1.00 | 0.00 | O |
| ATOM | 1525 | O5* | G | B | 1 | 1.293 | 162.522 | 290.836 | 1.00 | 0.00 | O |
| ATOM | 1526 | C5* | G | B | 1 | 2.460 | 162.198 | 290.079 | 1.00 | 0.00 | C |
| ATOM | 1527 | C4* | G | B | 1 | 3.576 | 163.153 | 290.393 | 1.00 | 0.00 | C |
| ATOM | 1528 | O4* | G | B | 1 | 3.907 | 163.108 | 291.808 | 1.00 | 0.00 | O |
| ATOM | 1529 | C3* | G | B | 1 | 4.843 | 162.814 | 289.626 | 1.00 | 0.00 | C |
| ATOM | 1530 | O3* | G | B | 1 | 4.927 | 163.707 | 288.526 | 1.00 | 0.00 | O |
| ATOM | 1531 | C2* | G | B | 1 | 5.958 | 163.021 | 290.648 | 1.00 | 0.00 | C |
| ATOM | 1532 | O2* | G | B | 1 | 6.468 | 164.338 | 290.653 | 1.00 | 0.00 | O |
| ATOM | 1533 | C1* | G | B | 1 | 5.249 | 162.705 | 291.968 | 1.00 | 0.00 | C |
| ATOM | 1534 | N9 | G | B | 1 | 5.238 | 161.293 | 292.341 | 1.00 | 0.00 | N |
| ATOM | 1535 | C8 | G | B | 1 | 4.139 | 160.558 | 292.715 | 1.00 | 0.00 | C |
| ATOM | 1536 | N7 | G | B | 1 | 4.425 | 159.320 | 293.007 | 1.00 | 0.00 | N |
| ATOM | 1537 | C5 | G | B | 1 | 5.794 | 159.227 | 292.807 | 1.00 | 0.00 | C |
| ATOM | 1538 | C6 | G | B | 1 | 6.671 | 158.124 | 292.965 | 1.00 | 0.00 | C |
| ATOM | 1539 | O6 | G | B | 1 | 6.401 | 156.972 | 293.321 | 1.00 | 0.00 | O |
| ATOM | 1540 | N1 | G | B | 1 | 7.984 | 158.469 | 292.659 | 1.00 | 0.00 | N |
| ATOM | 1541 | C2 | G | B | 1 | 8.403 | 159.713 | 292.257 | 1.00 | 0.00 | C |
| ATOM | 1542 | N2 | G | B | 1 | 9.711 | 159.848 | 292.016 | 1.00 | 0.00 | N |
| ATOM | 1543 | N3 | G | B | 1 | 7.596 | 160.749 | 292.105 | 1.00 | 0.00 | N |
| ATOM | 1544 | C4 | G | B | 1 | 6.314 | 160.438 | 292.396 | 1.00 | 0.00 | C |
| ATOM | 1545 | P | C | B | 2 | 5.956 | 163.408 | 287.338 | 1.00 | 0.00 | P |
| ATOM | 1546 | O1P | C | B | 2 | 6.208 | 164.697 | 286.647 | 1.00 | 0.00 | O |
| ATOM | 1547 | O2P | C | B | 2 | 5.458 | 162.246 | 286.561 | 1.00 | 0.00 | O |
| ATOM | 1548 | O5* | C | B | 2 | 7.290 | 162.972 | 288.084 | 1.00 | 0.00 | O |
| ATOM | 1549 | C5* | C | B | 2 | 8.544 | 163.506 | 287.683 | 1.00 | 0.00 | C |
| ATOM | 1550 | C4* | C | B | 2 | 9.474 | 162.397 | 287.259 | 1.00 | 0.00 | C |
| ATOM | 1551 | O4* | C | B | 2 | 9.720 | 161.543 | 288.406 | 1.00 | 0.00 | O |
| ATOM | 1552 | C3* | C | B | 2 | 8.956 | 161.420 | 286.211 | 1.00 | 0.00 | C |
| ATOM | 1553 | O3* | C | B | 2 | 9.095 | 161.909 | 284.879 | 1.00 | 0.00 | O |
| ATOM | 1554 | C2* | C | B | 2 | 9.885 | 160.237 | 286.435 | 1.00 | 0.00 | C |
| ATOM | 1555 | O2* | C | B | 2 | 11.162 | 160.427 | 285.860 | 1.00 | 0.00 | O |
| ATOM | 1556 | C1* | C | B | 2 | 9.991 | 160.225 | 287.961 | 1.00 | 0.00 | C |
| ATOM | 1557 | N1 | C | B | 2 | 9.003 | 159.315 | 288.555 | 1.00 | 0.00 | N |
| ATOM | 1558 | C2 | C | B | 2 | 9.352 | 157.971 | 288.726 | 1.00 | 0.00 | C |
| ATOM | 1559 | O2 | C | B | 2 | 10.498 | 157.603 | 288.411 | 1.00 | 0.00 | O |
| ATOM | 1560 | N3 | C | B | 2 | 8.441 | 157.112 | 289.229 | 1.00 | 0.00 | N |
| ATOM | 1561 | C4 | C | B | 2 | 7.226 | 157.552 | 289.563 | 1.00 | 0.00 | C |
| ATOM | 1562 | N4 | C | B | 2 | 6.358 | 156.665 | 290.049 | 1.00 | 0.00 | N |
| ATOM | 1563 | C5 | C | B | 2 | 6.850 | 158.916 | 289.415 | 1.00 | 0.00 | C |
| ATOM | 1564 | C6 | C | B | 2 | 7.763 | 159.758 | 288.915 | 1.00 | 0.00 | C |
| ATOM | 1565 | P | G | B | 3 | 8.493 | 161.059 | 283.644 | 1.00 | 0.00 | P |
| ATOM | 1566 | O1P | G | B | 3 | 8.935 | 161.710 | 282.386 | 1.00 | 0.00 | O |
| ATOM | 1567 | O2P | G | B | 3 | 7.042 | 160.839 | 283.888 | 1.00 | 0.00 | O |
| ATOM | 1568 | O5* | G | B | 3 | 9.240 | 159.655 | 283.711 | 1.00 | 0.00 | O |
| ATOM | 1569 | C5* | G | B | 3 | 10.339 | 159.396 | 282.851 | 1.00 | 0.00 | C |
| ATOM | 1570 | C4* | G | B | 3 | 10.984 | 158.081 | 283.201 | 1.00 | 0.00 | C |
| ATOM | 1571 | O4* | G | B | 3 | 10.897 | 157.838 | 284.631 | 1.00 | 0.00 | O |
| ATOM | 1572 | C3* | G | B | 3 | 10.321 | 156.858 | 282.608 | 1.00 | 0.00 | C |
| ATOM | 1573 | O3* | G | B | 3 | 10.662 | 156.676 | 281.245 | 1.00 | 0.00 | O |
| ATOM | 1574 | C2* | G | B | 3 | 10.870 | 155.755 | 283.504 | 1.00 | 0.00 | C |
| ATOM | 1575 | O2* | G | B | 3 | 12.192 | 155.359 | 283.194 | 1.00 | 0.00 | O |
| ATOM | 1576 | C1* | G | B | 3 | 10.799 | 156.439 | 284.870 | 1.00 | 0.00 | C |
| ATOM | 1577 | N9 | G | B | 3 | 9.508 | 156.176 | 285.495 | 1.00 | 0.00 | N |
| ATOM | 1578 | C8 | G | B | 3 | 8.441 | 157.036 | 285.590 | 1.00 | 0.00 | C |
| ATOM | 1579 | N7 | G | B | 3 | 7.397 | 156.494 | 286.157 | 1.00 | 0.00 | N |
| ATOM | 1580 | C5 | G | B | 3 | 7.804 | 155.202 | 286.466 | 1.00 | 0.00 | C |
| ATOM | 1581 | C6 | G | B | 3 | 7.092 | 154.137 | 287.079 | 1.00 | 0.00 | C |
| ATOM | 1582 | O6 | G | B | 3 | 5.929 | 154.126 | 287.492 | 1.00 | 0.00 | O |
| ATOM | 1583 | N1 | G | B | 3 | 7.878 | 152.994 | 287.191 | 1.00 | 0.00 | N |
| ATOM | 1584 | C2 | G | B | 3 | 9.182 | 152.886 | 286.766 | 1.00 | 0.00 | C |
| ATOM | 1585 | N2 | G | B | 3 | 9.769 | 151.697 | 286.957 | 1.00 | 0.00 | N |
| ATOM | 1586 | N3 | G | B | 3 | 9.859 | 153.876 | 286.195 | 1.00 | 0.00 | N |
| ATOM | 1587 | C4 | G | B | 3 | 9.108 | 154.994 | 286.077 | 1.00 | 0.00 | C |
| ATOM | 1588 | P | G | B | 4 | 9.562 | 156.096 | 280.241 | 1.00 | 0.00 | P |
| ATOM | 1589 | O1P | G | B | 4 | 9.957 | 156.424 | 278.849 | 1.00 | 0.00 | O |
| ATOM | 1590 | O2P | G | B | 4 | 8.264 | 156.580 | 280.768 | 1.00 | 0.00 | O |
| ATOM | 1591 | O5* | G | B | 4 | 9.651 | 154.516 | 280.430 | 1.00 | 0.00 | O |
| ATOM | 1592 | C5* | G | B | 4 | 10.783 | 153.802 | 279.968 | 1.00 | 0.00 | C |
| ATOM | 1593 | C4* | G | B | 4 | 10.853 | 152.456 | 280.636 | 1.00 | 0.00 | C |
| ATOM | 1594 | O4* | G | B | 4 | 10.699 | 152.595 | 282.072 | 1.00 | 0.00 | O |
| ATOM | 1595 | C3* | G | B | 4 | 9.735 | 151.510 | 280.276 | 1.00 | 0.00 | C |
| ATOM | 1596 | O3* | G | B | 4 | 10.028 | 150.906 | 279.044 | 1.00 | 0.00 | O |
| ATOM | 1597 | C2* | G | B | 4 | 9.814 | 150.502 | 281.409 | 1.00 | 0.00 | C |
| ATOM | 1598 | O2* | G | B | 4 | 10.880 | 149.597 | 281.267 | 1.00 | 0.00 | O |
| ATOM | 1599 | C1* | G | B | 4 | 10.073 | 151.428 | 282.590 | 1.00 | 0.00 | C |
| ATOM | 1600 | N9 | G | B | 4 | 8.814 | 151.829 | 283.208 | 1.00 | 0.00 | N |
| ATOM | 1601 | C8 | G | B | 4 | 8.247 | 153.081 | 283.221 | 1.00 | 0.00 | C |
| ATOM | 1602 | N7 | G | B | 4 | 7.113 | 153.124 | 283.869 | 1.00 | 0.00 | N |
| ATOM | 1603 | C5 | G | B | 4 | 6.924 | 151.826 | 284.308 | 1.00 | 0.00 | C |
| ATOM | 1604 | C6 | G | B | 4 | 5.874 | 151.268 | 285.063 | 1.00 | 0.00 | C |
| ATOM | 1605 | O6 | G | B | 4 | 4.869 | 151.840 | 285.530 | 1.00 | 0.00 | O |
| ATOM | 1606 | N1 | G | B | 4 | 6.066 | 149.903 | 285.272 | 1.00 | 0.00 | N |

```
ATOM   1607  C2   G B  4     7.139 149.170 284.810  1.00  0.00           C
ATOM   1608  N2   G B  4     7.146 147.864 285.098  1.00  0.00           N
ATOM   1609  N3   G B  4     8.131 149.686 284.112  1.00  0.00           N
ATOM   1610  C4   G B  4     7.960 151.009 283.901  1.00  0.00           C
ATOM   1611  P    A B  5     8.834 150.381 278.121  1.00  0.00           P
ATOM   1612  O1P  A B  5     9.456 149.733 276.937  1.00  0.00           O
ATOM   1613  O2P  A B  5     7.854 151.492 277.927  1.00  0.00           O
ATOM   1614  O5*  A B  5     8.200 149.218 278.998  1.00  0.00           O
ATOM   1615  C5*  A B  5     8.888 147.993 279.127  1.00  0.00           C
ATOM   1616  C4*  A B  5     8.049 147.020 279.888  1.00  0.00           C
ATOM   1617  O4*  A B  5     7.862 147.522 281.239  1.00  0.00           O
ATOM   1618  C3*  A B  5     6.633 146.861 279.367  1.00  0.00           C
ATOM   1619  O3*  A B  5     6.615 145.928 278.295  1.00  0.00           O
ATOM   1620  C2*  A B  5     5.948 146.316 280.614  1.00  0.00           C
ATOM   1621  O2*  A B  5     6.338 144.988 280.924  1.00  0.00           O
ATOM   1622  C1*  A B  5     6.558 147.224 281.678  1.00  0.00           C
ATOM   1623  N9   A B  5     5.826 148.479 281.807  1.00  0.00           N
ATOM   1624  C8   A B  5     6.107 149.697 281.252  1.00  0.00           C
ATOM   1625  N7   A B  5     5.249 150.634 281.578  1.00  0.00           N
ATOM   1626  C5   A B  5     4.345 149.986 282.405  1.00  0.00           C
ATOM   1627  C6   A B  5     3.199 150.434 283.099  1.00  0.00           C
ATOM   1628  N6   A B  5     2.748 151.692 283.059  1.00  0.00           N
ATOM   1629  N1   A B  5     2.524 149.532 283.838  1.00  0.00           N
ATOM   1630  C2   A B  5     2.967 148.261 283.866  1.00  0.00           C
ATOM   1631  N3   A B  5     4.029 147.722 283.262  1.00  0.00           N
ATOM   1632  C4   A B  5     4.683 148.655 282.544  1.00  0.00           C
ATOM   1633  P    U B  6     5.507 146.060 277.140  1.00  0.00           P
ATOM   1634  O1P  U B  6     5.762 144.932 276.213  1.00  0.00           O
ATOM   1635  O2P  U B  6     5.477 147.451 276.620  1.00  0.00           O
ATOM   1636  O5*  U B  6     4.134 145.758 277.883  1.00  0.00           O
ATOM   1637  C5*  U B  6     3.866 144.453 278.347  1.00  0.00           C
ATOM   1638  C4*  U B  6     2.724 144.472 279.315  1.00  0.00           C
ATOM   1639  O4*  U B  6     2.938 145.478 280.341  1.00  0.00           O
ATOM   1640  C3*  U B  6     1.421 144.907 278.699  1.00  0.00           C
ATOM   1641  O3*  U B  6     0.859 143.818 278.001  1.00  0.00           O
ATOM   1642  C2*  U B  6     0.622 145.244 279.945  1.00  0.00           C
ATOM   1643  O2*  U B  6     0.228 144.070 280.618  1.00  0.00           O
ATOM   1644  C1*  U B  6     1.680 145.962 280.778  1.00  0.00           C
ATOM   1645  N1   U B  6     1.647 147.418 280.611  1.00  0.00           N
ATOM   1646  C2   U B  6     0.557 148.072 281.146  1.00  0.00           C
ATOM   1647  O2   U B  6    -0.343 147.486 281.703  1.00  0.00           O
ATOM   1648  N3   U B  6     0.550 149.425 280.982  1.00  0.00           N
ATOM   1649  C4   U B  6     1.488 150.191 280.338  1.00  0.00           C
ATOM   1650  O4   U B  6     1.312 151.406 280.253  1.00  0.00           O
ATOM   1651  C5   U B  6     2.599 149.453 279.799  1.00  0.00           C
ATOM   1652  C6   U B  6     2.637 148.114 279.954  1.00  0.00           C
ATOM   1653  P    U B  7    -0.083 144.101 276.738  1.00  0.00           P
ATOM   1654  O1P  U B  7    -0.271 142.800 276.079  1.00  0.00           O
ATOM   1655  O2P  U B  7     0.458 145.279 275.985  1.00  0.00           O
ATOM   1656  O5*  U B  7    -1.468 144.580 277.386  1.00  0.00           O
ATOM   1657  C5*  U B  7    -2.139 143.792 278.374  1.00  0.00           C
ATOM   1658  C4*  U B  7    -3.413 144.492 278.799  1.00  0.00           C
ATOM   1659  O4*  U B  7    -3.035 145.778 279.358  1.00  0.00           O
ATOM   1660  C3*  U B  7    -4.399 144.778 277.668  1.00  0.00           C
ATOM   1661  O3*  U B  7    -5.744 144.515 278.063  1.00  0.00           O
ATOM   1662  C2*  U B  7    -4.159 146.249 277.355  1.00  0.00           C
ATOM   1663  O2*  U B  7    -5.342 146.910 276.960  1.00  0.00           O
ATOM   1664  C1*  U B  7    -3.749 146.803 278.715  1.00  0.00           C
ATOM   1665  N1   U B  7    -2.890 147.993 278.630  1.00  0.00           N
ATOM   1666  C2   U B  7    -3.406 149.182 279.101  1.00  0.00           C
ATOM   1667  O2   U B  7    -4.514 149.265 279.614  1.00  0.00           O
ATOM   1668  N3   U B  7    -2.582 150.268 278.960  1.00  0.00           N
ATOM   1669  C4   U B  7    -1.311 150.287 278.406  1.00  0.00           C
ATOM   1670  O4   U B  7    -0.682 151.364 278.334  1.00  0.00           O
ATOM   1671  C5   U B  7    -0.845 149.009 277.968  1.00  0.00           C
ATOM   1672  C6   U B  7    -1.624 147.936 278.092  1.00  0.00           C
ATOM   1673  P    U B  8    -6.468 143.132 277.637  1.00  0.00           P
ATOM   1674  O1P  U B  8    -7.909 143.267 277.999  1.00  0.00           O
ATOM   1675  O2P  U B  8    -5.675 141.977 278.116  1.00  0.00           O
ATOM   1676  O5*  U B  8    -6.424 143.126 276.040  1.00  0.00           O
ATOM   1677  C5*  U B  8    -7.368 143.894 275.307  1.00  0.00           C
ATOM   1678  C4*  U B  8    -7.835 143.155 274.082  1.00  0.00           C
ATOM   1679  O4*  U B  8    -6.735 143.053 273.126  1.00  0.00           O
ATOM   1680  C3*  U B  8    -8.323 141.715 274.230  1.00  0.00           C
ATOM   1681  O3*  U B  8    -9.676 141.642 274.684  1.00  0.00           O
ATOM   1682  C2*  U B  8    -8.217 141.267 272.781  1.00  0.00           C
ATOM   1683  O2*  U B  8    -9.147 141.905 271.909  1.00  0.00           O
ATOM   1684  C1*  U B  8    -6.834 141.827 272.427  1.00  0.00           C
ATOM   1685  N1   U B  8    -5.741 140.968 272.889  1.00  0.00           N
ATOM   1686  C2   U B  8    -5.360 139.915 272.079  1.00  0.00           C
ATOM   1687  O2   U B  8    -5.875 139.693 271.004  1.00  0.00           O
ATOM   1688  N3   U B  8    -4.354 139.143 272.579  1.00  0.00           N
ATOM   1689  C4   U B  8    -3.696 139.318 273.780  1.00  0.00           C
ATOM   1690  O4   U B  8    -2.843 138.504 274.129  1.00  0.00           O
ATOM   1691  C5   U B  8    -4.150 140.422 274.547  1.00  0.00           C
ATOM   1692  C6   U B  8    -5.127 141.194 274.086  1.00  0.00           C
ATOM   1693  P    A B  9   -10.150 140.419 275.615  1.00  0.00           P
```

```
ATOM    1694  O1P    A  B    9    -10.926 140.991 276.746  1.00  0.00           O
ATOM    1695  O2P    A  B    9     -8.987 139.505 275.908  1.00  0.00           O
ATOM    1696  O5*    A  B    9    -11.153 139.626 274.686  1.00  0.00           O
ATOM    1697  C5*    A  B    9    -12.411 140.193 274.335  1.00  0.00           C
ATOM    1698  C4*    A  B    9    -13.481 139.144 274.434  1.00  0.00           C
ATOM    1699  O4*    A  B    9    -13.230 138.195 273.356  1.00  0.00           O
ATOM    1700  C3*    A  B    9    -13.484 138.324 275.732  1.00  0.00           C
ATOM    1701  O3*    A  B    9    -14.805 137.879 276.032  1.00  0.00           O
ATOM    1702  C2*    A  B    9    -12.654 137.098 275.353  1.00  0.00           C
ATOM    1703  O2*    A  B    9    -13.061 135.944 276.040  1.00  0.00           O
ATOM    1704  C1*    A  B    9    -13.048 136.906 273.901  1.00  0.00           C
ATOM    1705  N9     A  B    9    -12.052 136.162 273.113  1.00  0.00           N
ATOM    1706  C8     A  B    9    -10.827 135.710 273.523  1.00  0.00           C
ATOM    1707  N7     A  B    9    -10.201 134.965 272.621  1.00  0.00           N
ATOM    1708  C5     A  B    9    -11.071 134.952 271.549  1.00  0.00           C
ATOM    1709  C6     A  B    9    -11.006 134.344 270.296  1.00  0.00           C
ATOM    1710  N6     A  B    9     -9.974 133.583 269.893  1.00  0.00           N
ATOM    1711  N1     A  B    9    -12.043 134.533 269.452  1.00  0.00           N
ATOM    1712  C2     A  B    9    -13.067 135.300 269.849  1.00  0.00           C
ATOM    1713  N3     A  B    9    -13.242 135.934 271.002  1.00  0.00           N
ATOM    1714  C4     A  B    9    -12.206 135.712 271.825  1.00  0.00           C
HETATM  1715  P    2MG  B   10    -15.721 138.692 277.112  1.00  0.00           P
HETATM  1716  O1P  2MG  B   10    -15.377 140.114 277.120  1.00  0.00           O
HETATM  1717  O2P  2MG  B   10    -17.132 138.290 276.877  1.00  0.00           O
HETATM  1718  O5*  2MG  B   10    -15.210 138.121 278.498  1.00  0.00           O
HETATM  1719  C5*  2MG  B   10    -15.821 138.567 279.718  1.00  0.00           C
HETATM  1720  C4*  2MG  B   10    -15.800 137.465 280.747  1.00  0.00           C
HETATM  1721  O4*  2MG  B   10    -16.540 136.330 280.219  1.00  0.00           O
HETATM  1722  C3*  2MG  B   10    -14.419 136.927 281.066  1.00  0.00           C
HETATM  1723  O3*  2MG  B   10    -13.872 137.655 282.161  1.00  0.00           O
HETATM  1724  C2*  2MG  B   10    -14.733 135.499 281.458  1.00  0.00           C
HETATM  1725  O2*  2MG  B   10    -15.307 135.482 282.758  1.00  0.00           O
HETATM  1726  C1*  2MG  B   10    -15.818 135.136 280.454  1.00  0.00           C
HETATM  1727  N9   2MG  B   10    -15.402 134.590 279.165  1.00  0.00           N
HETATM  1728  C8   2MG  B   10    -15.808 135.032 277.922  1.00  0.00           C
HETATM  1729  N7   2MG  B   10    -15.338 134.309 276.935  1.00  0.00           N
HETATM  1730  C5   2MG  B   10    -14.567 133.340 277.560  1.00  0.00           C
HETATM  1731  C6   2MG  B   10    -13.799 132.297 277.006  1.00  0.00           C
HETATM  1732  O6   2MG  B   10    -13.689 131.980 275.821  1.00  0.00           O
HETATM  1733  N1   2MG  B   10    -13.119 131.578 277.984  1.00  0.00           N
HETATM  1734  C2   2MG  B   10    -13.183 131.833 279.337  1.00  0.00           C
HETATM  1735  N2   2MG  B   10    -12.457 131.024 280.122  1.00  0.00           N
HETATM  1736  CM2  2MG  B   10    -12.501 131.039 281.588  1.00  0.00           C
HETATM  1737  N3   2MG  B   10    -13.912 132.807 279.874  1.00  0.00           N
HETATM  1738  C4   2MG  B   10    -14.575 133.513 278.938  1.00  0.00           C
ATOM    1739  P      C  B   11    -12.364 138.171 282.106  1.00  0.00           P
ATOM    1740  O1P    C  B   11    -12.102 139.061 283.246  1.00  0.00           O
ATOM    1741  O2P    C  B   11    -12.119 138.673 280.713  1.00  0.00           O
ATOM    1742  O5*    C  B   11    -11.500 136.861 282.384  1.00  0.00           O
ATOM    1743  C5*    C  B   11    -11.421 136.335 283.711  1.00  0.00           C
ATOM    1744  C4*    C  B   11    -10.576 135.085 283.749  1.00  0.00           C
ATOM    1745  O4*    C  B   11    -11.159 134.067 282.894  1.00  0.00           O
ATOM    1746  C3*    C  B   11     -9.162 135.278 283.254  1.00  0.00           C
ATOM    1747  O3*    C  B   11     -8.321 135.658 284.335  1.00  0.00           O
ATOM    1748  C2*    C  B   11     -8.787 133.914 282.679  1.00  0.00           C
ATOM    1749  O2*    C  B   11     -8.217 133.059 283.643  1.00  0.00           O
ATOM    1750  C1*    C  B   11    -10.136 133.371 282.204  1.00  0.00           C
ATOM    1751  N1     C  B   11    -10.371 133.552 280.768  1.00  0.00           N
ATOM    1752  C2     C  B   11     -9.771 132.677 279.861  1.00  0.00           C
ATOM    1753  O2     C  B   11     -9.061 131.759 280.300  1.00  0.00           O
ATOM    1754  N3     C  B   11     -9.974 132.862 278.522  1.00  0.00           N
ATOM    1755  C4     C  B   11    -10.743 133.873 278.100  1.00  0.00           C
ATOM    1756  N4     C  B   11    -10.937 134.019 276.782  1.00  0.00           N
ATOM    1757  C5     C  B   11    -11.362 134.769 279.006  1.00  0.00           C
ATOM    1758  C6     C  B   11    -11.158 134.571 280.321  1.00  0.00           C
ATOM    1759  P      U  B   12     -7.119 136.664 284.053  1.00  0.00           P
ATOM    1760  O1P    U  B   12     -6.461 137.102 285.309  1.00  0.00           O
ATOM    1761  O2P    U  B   12     -7.691 137.686 283.144  1.00  0.00           O
ATOM    1762  O5*    U  B   12     -6.100 135.767 283.217  1.00  0.00           O
ATOM    1763  C5*    U  B   12     -5.397 134.690 283.831  1.00  0.00           C
ATOM    1764  C4*    U  B   12     -4.633 133.900 282.795  1.00  0.00           C
ATOM    1765  O4*    U  B   12     -5.564 133.254 281.888  1.00  0.00           O
ATOM    1766  C3*    U  B   12     -3.780 134.731 281.851  1.00  0.00           C
ATOM    1767  O3*    U  B   12     -2.536 135.039 282.439  1.00  0.00           O
ATOM    1768  C2*    U  B   12     -3.568 133.771 280.689  1.00  0.00           C
ATOM    1769  O2*    U  B   12     -2.482 132.884 280.891  1.00  0.00           O
ATOM    1770  C1*    U  B   12     -4.918 133.053 280.630  1.00  0.00           C
ATOM    1771  N1     U  B   12     -5.755 133.641 279.579  1.00  0.00           N
ATOM    1772  C2     U  B   12     -5.556 133.213 278.280  1.00  0.00           C
ATOM    1773  O2     U  B   12     -4.711 132.411 277.974  1.00  0.00           O
ATOM    1774  N3     U  B   12     -6.377 133.781 277.355  1.00  0.00           N
ATOM    1775  C4     U  B   12     -7.358 134.729 277.592  1.00  0.00           C
ATOM    1776  O4     U  B   12     -8.065 135.114 276.668  1.00  0.00           O
ATOM    1777  C5     U  B   12     -7.484 135.127 278.953  1.00  0.00           C
ATOM    1778  C6     U  B   12     -6.690 134.576 279.877  1.00  0.00           C
ATOM    1779  P      C  B   13     -1.657 136.237 281.844  1.00  0.00           P
ATOM    1780  O1P    C  B   13     -0.460 136.483 282.692  1.00  0.00           O
```

```
ATOM   1781  O2P   C B  13      -2.592 137.349 281.555  1.00  0.00           O
ATOM   1782  O5*   C B  13      -1.113 135.610 280.493  1.00  0.00           O
ATOM   1783  C5*   C B  13      -1.071 136.360 279.302  1.00  0.00           C
ATOM   1784  C4*   C B  13      -1.100 135.434 278.122  1.00  0.00           C
ATOM   1785  O4*   C B  13      -2.460 135.003 277.851  1.00  0.00           O
ATOM   1786  C3*   C B  13      -0.673 136.114 276.843  1.00  0.00           C
ATOM   1787  O3*   C B  13       0.743 136.165 276.870  1.00  0.00           O
ATOM   1788  C2*   C B  13      -1.306 135.217 275.782  1.00  0.00           C
ATOM   1789  O2*   C B  13      -0.582 134.046 275.497  1.00  0.00           O
ATOM   1790  C1*   C B  13      -2.624 134.816 276.457  1.00  0.00           C
ATOM   1791  N1    C B  13      -3.783 135.608 276.030  1.00  0.00           N
ATOM   1792  C2    C B  13      -4.313 135.408 274.751  1.00  0.00           C
ATOM   1793  O2    C B  13      -3.741 134.613 273.984  1.00  0.00           O
ATOM   1794  N3    C B  13      -5.415 136.105 274.369  1.00  0.00           N
ATOM   1795  C4    C B  13      -5.948 137.016 275.199  1.00  0.00           C
ATOM   1796  N4    C B  13      -7.009 137.705 274.780  1.00  0.00           N
ATOM   1797  C5    C B  13      -5.413 137.257 276.502  1.00  0.00           C
ATOM   1798  C6    C B  13      -4.347 136.526 276.876  1.00  0.00           C
ATOM   1799  P     A B  14       1.527 137.037 275.783  1.00  0.00           P
ATOM   1800  O1P   A B  14       2.952 137.131 276.194  1.00  0.00           O
ATOM   1801  O2P   A B  14       0.773 138.277 275.481  1.00  0.00           O
ATOM   1802  O5*   A B  14       1.475 136.066 274.535  1.00  0.00           O
ATOM   1803  C5*   A B  14       1.074 136.536 273.282  1.00  0.00           C
ATOM   1804  C4*   A B  14       1.180 135.441 272.266  1.00  0.00           C
ATOM   1805  O4*   A B  14      -0.111 134.779 272.201  1.00  0.00           O
ATOM   1806  C3*   A B  14       1.405 135.996 270.865  1.00  0.00           C
ATOM   1807  O3*   A B  14       2.783 136.104 270.575  1.00  0.00           O
ATOM   1808  C2*   A B  14       0.699 134.980 269.992  1.00  0.00           C
ATOM   1809  O2*   A B  14       1.445 133.792 269.804  1.00  0.00           O
ATOM   1810  C1*   A B  14      -0.533 134.692 270.839  1.00  0.00           C
ATOM   1811  N9    A B  14      -1.619 135.641 270.617  1.00  0.00           N
ATOM   1812  C8    A B  14      -2.185 136.541 271.498  1.00  0.00           C
ATOM   1813  N7    A B  14      -3.222 137.183 270.992  1.00  0.00           N
ATOM   1814  C5    A B  14      -3.327 136.688 269.701  1.00  0.00           C
ATOM   1815  C6    A B  14      -4.194 136.985 268.648  1.00  0.00           C
ATOM   1816  N6    A B  14      -5.212 137.869 268.729  1.00  0.00           N
ATOM   1817  N1    A B  14      -3.991 136.344 267.482  1.00  0.00           N
ATOM   1818  C2    A B  14      -2.986 135.472 267.392  1.00  0.00           C
ATOM   1819  N3    A B  14      -2.105 135.124 268.294  1.00  0.00           N
ATOM   1820  C4    A B  14      -2.331 135.766 269.446  1.00  0.00           C
ATOM   1821  P     G B  15       3.414 137.542 270.293  1.00  0.00           P
ATOM   1822  O1P   G B  15       4.866 137.370 270.059  1.00  0.00           O
ATOM   1823  O2P   G B  15       2.951 138.522 271.275  1.00  0.00           O
ATOM   1824  O5*   G B  15       2.718 138.019 268.942  1.00  0.00           O
ATOM   1825  C5*   G B  15       2.672 137.190 267.809  1.00  0.00           C
ATOM   1826  C4*   G B  15       1.572 137.660 266.873  1.00  0.00           C
ATOM   1827  O4*   G B  15       0.276 137.290 267.416  1.00  0.00           O
ATOM   1828  C3*   G B  15       1.441 139.161 266.690  1.00  0.00           C
ATOM   1829  O3*   G B  15       2.394 139.664 265.764  1.00  0.00           O
ATOM   1830  C2*   G B  15       0.025 139.269 266.134  1.00  0.00           C
ATOM   1831  O2*   G B  15      -0.121 138.832 264.814  1.00  0.00           O
ATOM   1832  C1*   G B  15      -0.698 138.264 267.028  1.00  0.00           C
ATOM   1833  N9    G B  15      -1.147 139.026 268.185  1.00  0.00           N
ATOM   1834  C8    G B  15      -0.565 139.123 269.431  1.00  0.00           C
ATOM   1835  N7    G B  15      -1.206 139.961 270.228  1.00  0.00           N
ATOM   1836  C5    G B  15      -2.270 140.423 269.470  1.00  0.00           C
ATOM   1837  C6    G B  15      -3.306 141.382 269.782  1.00  0.00           C
ATOM   1838  O6    G B  15      -3.507 141.999 270.839  1.00  0.00           O
ATOM   1839  N1    G B  15      -4.158 141.580 268.706  1.00  0.00           N
ATOM   1840  C2    G B  15      -4.051 140.967 267.486  1.00  0.00           C
ATOM   1841  N2    G B  15      -4.977 141.320 266.596  1.00  0.00           N
ATOM   1842  N3    G B  15      -3.100 140.079 267.168  1.00  0.00           N
ATOM   1843  C4    G B  15      -2.254 139.855 268.205  1.00  0.00           C
HETATM 1844  P    H2U B  16       3.099 141.088 266.029  1.00  0.00           P
HETATM 1845  O1P  H2U B  16       1.996 142.038 266.340  1.00  0.00           O
HETATM 1846  O2P  H2U B  16       4.231 140.959 266.986  1.00  0.00           O
HETATM 1847  O5*  H2U B  16       3.642 141.483 264.573  1.00  0.00           O
HETATM 1848  C5*  H2U B  16       2.705 141.645 263.492  1.00  0.00           C
HETATM 1849  C4*  H2U B  16       3.364 141.379 262.152  1.00  0.00           C
HETATM 1850  O4*  H2U B  16       4.417 142.346 261.955  1.00  0.00           O
HETATM 1851  C3*  H2U B  16       4.089 140.052 262.033  1.00  0.00           C
HETATM 1852  O3*  H2U B  16       4.147 139.603 260.655  1.00  0.00           O
HETATM 1853  C1*  H2U B  16       5.634 141.824 262.458  1.00  0.00           C
HETATM 1854  C2*  H2U B  16       5.388 140.344 262.787  1.00  0.00           C
HETATM 1855  O2*  H2U B  16       6.479 139.503 262.482  1.00  0.00           O
HETATM 1856  N1   H2U B  16       6.020 142.645 263.615  1.00  0.00           N
HETATM 1857  C2   H2U B  16       5.832 144.016 263.500  1.00  0.00           C
HETATM 1858  O2   H2U B  16       5.221 144.516 262.572  1.00  0.00           O
HETATM 1859  N3   H2U B  16       6.381 144.786 264.496  1.00  0.00           N
HETATM 1860  C4   H2U B  16       7.137 144.373 265.575  1.00  0.00           C
HETATM 1861  O4   H2U B  16       7.535 145.213 266.386  1.00  0.00           O
HETATM 1862  C5   H2U B  16       7.551 142.926 265.537  1.00  0.00           C
HETATM 1863  C6   H2U B  16       6.560 142.031 264.844  1.00  0.00           C
HETATM 1864  P    H2U B  17       5.393 139.987 259.690  1.00  0.00           P
HETATM 1865  O1P  H2U B  17       6.617 140.338 260.437  1.00  0.00           O
HETATM 1866  O2P  H2U B  17       5.463 138.947 258.629  1.00  0.00           O
HETATM 1867  O5*  H2U B  17       4.938 141.336 258.987  1.00  0.00           O
```

```
HETATM 1868  C5*  H2U B  17      5.850 142.427 258.861  1.00  0.00           C
HETATM 1869  C4*  H2U B  17      5.292 143.461 257.908  1.00  0.00           C
HETATM 1870  O4*  H2U B  17      5.293 142.906 256.561  1.00  0.00           O
HETATM 1871  C3*  H2U B  17      3.850 143.887 258.194  1.00  0.00           C
HETATM 1872  O3*  H2U B  17      3.772 145.301 258.053  1.00  0.00           O
HETATM 1873  C1*  H2U B  17      4.028 143.087 255.981  1.00  0.00           C
HETATM 1874  C2*  H2U B  17      3.043 143.111 257.146  1.00  0.00           C
HETATM 1875  O2*  H2U B  17      1.817 143.685 256.700  1.00  0.00           O
HETATM 1876  N1   H2U B  17      3.800 142.017 255.004  1.00  0.00           N
HETATM 1877  C2   H2U B  17      3.938 142.375 253.679  1.00  0.00           C
HETATM 1878  O2   H2U B  17      3.991 143.538 253.325  1.00  0.00           O
HETATM 1879  N3   H2U B  17      4.020 141.341 252.782  1.00  0.00           N
HETATM 1880  C4   H2U B  17      4.005 139.995 253.049  1.00  0.00           C
HETATM 1881  O4   H2U B  17      4.003 139.194 252.105  1.00  0.00           O
HETATM 1882  C5   H2U B  17      4.152 139.645 254.521  1.00  0.00           C
HETATM 1883  C6   H2U B  17      3.483 140.637 255.413  1.00  0.00           C
ATOM   1884  P    G   B  18      3.794 146.217 259.359  1.00  0.00           P
ATOM   1885  O1P  G   B  18      4.070 147.627 259.059  1.00  0.00           O
ATOM   1886  O2P  G   B  18      4.640 145.499 260.329  1.00  0.00           O
ATOM   1887  O5*  G   B  18      2.299 146.088 259.865  1.00  0.00           O
ATOM   1888  C5*  G   B  18      1.457 147.169 259.790  1.00  0.00           C
ATOM   1889  C4*  G   B  18      0.100 146.753 259.294  1.00  0.00           C
ATOM   1890  O4*  G   B  18     -0.544 148.040 259.291  1.00  0.00           O
ATOM   1891  C3*  G   B  18      0.046 146.284 257.828  1.00  0.00           C
ATOM   1892  O3*  G   B  18     -1.260 145.845 257.413  1.00  0.00           O
ATOM   1893  C2*  G   B  18      0.252 147.601 257.117  1.00  0.00           C
ATOM   1894  O2*  G   B  18     -0.253 147.579 255.787  1.00  0.00           O
ATOM   1895  C1*  G   B  18     -0.662 148.485 257.962  1.00  0.00           C
ATOM   1896  N9   G   B  18     -0.298 149.891 257.901  1.00  0.00           N
ATOM   1897  C8   G   B  18      0.950 150.431 257.706  1.00  0.00           C
ATOM   1898  N7   G   B  18      0.920 151.731 257.567  1.00  0.00           N
ATOM   1899  C5   G   B  18     -0.418 152.049 257.714  1.00  0.00           C
ATOM   1900  C6   G   B  18     -1.062 153.272 257.617  1.00  0.00           C
ATOM   1901  O6   G   B  18     -0.566 154.360 257.375  1.00  0.00           O
ATOM   1902  N1   G   B  18     -2.443 153.151 257.816  1.00  0.00           N
ATOM   1903  C2   G   B  18     -3.095 151.990 258.060  1.00  0.00           C
ATOM   1904  N2   G   B  18     -4.422 152.076 258.236  1.00  0.00           N
ATOM   1905  N3   G   B  18     -2.492 150.813 258.131  1.00  0.00           N
ATOM   1906  C4   G   B  18     -1.171 150.923 257.949  1.00  0.00           C
ATOM   1907  P    G   B  19     -1.672 144.282 257.470  1.00  0.00           P
ATOM   1908  O1P  G   B  19     -1.730 143.807 258.886  1.00  0.00           O
ATOM   1909  O2P  G   B  19     -0.891 143.486 256.482  1.00  0.00           O
ATOM   1910  O5*  G   B  19     -3.153 144.319 256.913  1.00  0.00           O
ATOM   1911  C5*  G   B  19     -4.217 144.773 257.764  1.00  0.00           C
ATOM   1912  C4*  G   B  19     -5.509 144.802 257.010  1.00  0.00           C
ATOM   1913  O4*  G   B  19     -5.293 145.666 255.853  1.00  0.00           O
ATOM   1914  C3*  G   B  19     -5.950 143.451 256.441  1.00  0.00           C
ATOM   1915  O3*  G   B  19     -7.360 143.434 256.214  1.00  0.00           O
ATOM   1916  C2*  G   B  19     -5.234 143.461 255.076  1.00  0.00           C
ATOM   1917  O2*  G   B  19     -5.846 142.611 254.141  1.00  0.00           O
ATOM   1918  C1*  G   B  19     -5.417 144.917 254.647  1.00  0.00           C
ATOM   1919  N9   G   B  19     -4.419 145.487 253.761  1.00  0.00           N
ATOM   1920  C8   G   B  19     -3.113 145.087 253.595  1.00  0.00           C
ATOM   1921  N7   G   B  19     -2.404 145.943 252.895  1.00  0.00           N
ATOM   1922  C5   G   B  19     -3.312 146.941 252.536  1.00  0.00           C
ATOM   1923  C6   G   B  19     -3.138 148.144 251.779  1.00  0.00           C
ATOM   1924  O6   G   B  19     -2.137 148.575 251.249  1.00  0.00           O
ATOM   1925  N1   G   B  19     -4.311 148.868 251.678  1.00  0.00           N
ATOM   1926  C2   G   B  19     -5.512 148.514 252.215  1.00  0.00           C
ATOM   1927  N2   G   B  19     -6.535 149.384 251.973  1.00  0.00           N
ATOM   1928  N3   G   B  19     -5.707 147.402 252.923  1.00  0.00           N
ATOM   1929  C4   G   B  19     -4.566 146.663 253.038  1.00  0.00           C
ATOM   1930  P    G   B  20     -8.405 142.968 257.391  1.00  0.00           P
ATOM   1931  O1P  G   B  20     -9.741 143.488 257.024  1.00  0.00           O
ATOM   1932  O2P  G   B  20     -7.826 143.366 258.675  1.00  0.00           O
ATOM   1933  O5*  G   B  20     -8.428 141.379 257.310  1.00  0.00           O
ATOM   1934  C5*  G   B  20     -8.987 140.670 256.217  1.00  0.00           C
ATOM   1935  C4*  G   B  20     -9.319 139.248 256.636  1.00  0.00           C
ATOM   1936  O4*  G   B  20     -8.122 138.406 256.589  1.00  0.00           O
ATOM   1937  C3*  G   B  20     -9.848 139.122 258.062  1.00  0.00           C
ATOM   1938  O3*  G   B  20    -11.274 139.184 258.064  1.00  0.00           O
ATOM   1939  C2*  G   B  20     -9.365 137.753 258.495  1.00  0.00           C
ATOM   1940  O2*  G   B  20    -10.154 136.682 258.061  1.00  0.00           O
ATOM   1941  C1*  G   B  20     -8.029 137.647 257.772  1.00  0.00           C
ATOM   1942  N9   G   B  20     -6.941 138.178 258.583  1.00  0.00           N
ATOM   1943  C8   G   B  20     -6.123 139.232 258.285  1.00  0.00           C
ATOM   1944  N7   G   B  20     -5.256 139.480 259.235  1.00  0.00           N
ATOM   1945  C5   G   B  20     -5.520 138.521 260.195  1.00  0.00           C
ATOM   1946  C6   G   B  20     -4.916 138.305 261.453  1.00  0.00           C
ATOM   1947  O6   G   B  20     -3.987 138.912 261.946  1.00  0.00           O
ATOM   1948  N1   G   B  20     -5.521 137.258 262.147  1.00  0.00           N
ATOM   1949  C2   G   B  20     -6.570 136.502 261.676  1.00  0.00           C
ATOM   1950  N2   G   B  20     -7.042 135.522 262.505  1.00  0.00           N
ATOM   1951  N3   G   B  20     -7.123 136.687 260.486  1.00  0.00           N
ATOM   1952  C4   G   B  20     -6.555 137.712 259.812  1.00  0.00           C
ATOM   1953  P    A   B  21    -11.983 140.240 259.023  1.00  0.00           P
ATOM   1954  O1P  A   B  21    -13.432 140.062 258.882  1.00  0.00           O
```

| | | | | | | | | | | |
|---|---|---|---|---|---|---|---|---|---|---|
| ATOM | 1955 | O2P | A | B | 21 | -11.363 | 141.564 | 258.701 | 1.00 | 0.00 | O |
| ATOM | 1956 | O5* | A | B | 21 | -11.582 | 139.592 | 260.410 | 1.00 | 0.00 | O |
| ATOM | 1957 | C5* | A | B | 21 | -11.216 | 140.333 | 261.504 | 1.00 | 0.00 | C |
| ATOM | 1958 | C4* | A | B | 21 | -10.321 | 139.510 | 262.379 | 1.00 | 0.00 | C |
| ATOM | 1959 | O4* | A | B | 21 | -9.840 | 140.440 | 263.322 | 1.00 | 0.00 | O |
| ATOM | 1960 | C3* | A | B | 21 | -10.797 | 138.300 | 263.204 | 1.00 | 0.00 | C |
| ATOM | 1961 | O3* | A | B | 21 | -10.697 | 137.077 | 262.432 | 1.00 | 0.00 | O |
| ATOM | 1962 | C2* | A | B | 21 | -9.742 | 138.277 | 264.303 | 1.00 | 0.00 | C |
| ATOM | 1963 | O2* | A | B | 21 | -8.548 | 137.659 | 263.849 | 1.00 | 0.00 | O |
| ATOM | 1964 | C1* | A | B | 21 | -9.431 | 139.769 | 264.482 | 1.00 | 0.00 | C |
| ATOM | 1965 | N9 | A | B | 21 | -10.111 | 140.454 | 265.560 | 1.00 | 0.00 | N |
| ATOM | 1966 | C8 | A | B | 21 | -11.288 | 141.125 | 265.456 | 1.00 | 0.00 | C |
| ATOM | 1967 | N7 | A | B | 21 | -11.629 | 141.750 | 266.552 | 1.00 | 0.00 | N |
| ATOM | 1968 | C5 | A | B | 21 | -10.617 | 141.443 | 267.435 | 1.00 | 0.00 | C |
| ATOM | 1969 | C6 | A | B | 21 | -10.417 | 141.772 | 268.764 | 1.00 | 0.00 | C |
| ATOM | 1970 | N6 | A | B | 21 | -11.254 | 142.555 | 269.452 | 1.00 | 0.00 | N |
| ATOM | 1971 | N1 | A | B | 21 | -9.334 | 141.280 | 269.378 | 1.00 | 0.00 | N |
| ATOM | 1972 | C2 | A | B | 21 | -8.504 | 140.506 | 268.674 | 1.00 | 0.00 | C |
| ATOM | 1973 | N3 | A | B | 21 | -8.588 | 140.125 | 267.407 | 1.00 | 0.00 | N |
| ATOM | 1974 | C4 | A | B | 21 | -9.684 | 140.630 | 266.844 | 1.00 | 0.00 | C |
| ATOM | 1975 | P | G | B | 22 | -11.111 | 135.623 | 263.056 | 1.00 | 0.00 | P |
| ATOM | 1976 | O1P | G | B | 22 | -11.229 | 134.652 | 261.969 | 1.00 | 0.00 | O |
| ATOM | 1977 | O2P | G | B | 22 | -12.204 | 135.734 | 264.045 | 1.00 | 0.00 | O |
| ATOM | 1978 | O5* | G | B | 22 | -9.845 | 135.200 | 263.892 | 1.00 | 0.00 | O |
| ATOM | 1979 | C5* | G | B | 22 | -9.956 | 134.306 | 264.976 | 1.00 | 0.00 | C |
| ATOM | 1980 | C4* | G | B | 22 | -8.595 | 133.735 | 265.282 | 1.00 | 0.00 | C |
| ATOM | 1981 | O4* | G | B | 22 | -7.689 | 134.826 | 265.598 | 1.00 | 0.00 | O |
| ATOM | 1982 | C3* | G | B | 22 | -8.530 | 132.782 | 266.459 | 1.00 | 0.00 | C |
| ATOM | 1983 | O3* | G | B | 22 | -8.820 | 131.446 | 266.023 | 1.00 | 0.00 | O |
| ATOM | 1984 | C2* | G | B | 22 | -7.108 | 132.996 | 266.955 | 1.00 | 0.00 | C |
| ATOM | 1985 | O2* | G | B | 22 | -6.090 | 132.322 | 266.250 | 1.00 | 0.00 | O |
| ATOM | 1986 | C1* | G | B | 22 | -6.935 | 134.497 | 266.743 | 1.00 | 0.00 | C |
| ATOM | 1987 | N9 | G | B | 22 | -7.451 | 135.263 | 267.871 | 1.00 | 0.00 | N |
| ATOM | 1988 | C8 | G | B | 22 | -8.511 | 136.134 | 267.876 | 1.00 | 0.00 | C |
| ATOM | 1989 | N7 | G | B | 22 | -8.685 | 136.708 | 269.035 | 1.00 | 0.00 | N |
| ATOM | 1990 | C5 | G | B | 22 | -7.692 | 136.162 | 269.842 | 1.00 | 0.00 | C |
| ATOM | 1991 | C6 | G | B | 22 | -7.376 | 136.420 | 271.195 | 1.00 | 0.00 | C |
| ATOM | 1992 | O6 | G | B | 22 | -7.933 | 137.196 | 271.961 | 1.00 | 0.00 | O |
| ATOM | 1993 | N1 | G | B | 22 | -6.289 | 135.671 | 271.626 | 1.00 | 0.00 | N |
| ATOM | 1994 | C2 | G | B | 22 | -5.588 | 134.785 | 270.842 | 1.00 | 0.00 | C |
| ATOM | 1995 | N2 | G | B | 22 | -4.560 | 134.154 | 271.428 | 1.00 | 0.00 | N |
| ATOM | 1996 | N3 | G | B | 22 | -5.873 | 134.542 | 269.581 | 1.00 | 0.00 | N |
| ATOM | 1997 | C4 | G | B | 22 | -6.935 | 135.266 | 269.152 | 1.00 | 0.00 | C |
| ATOM | 1998 | P | A | B | 23 | -9.548 | 130.413 | 267.025 | 1.00 | 0.00 | P |
| ATOM | 1999 | O1P | A | B | 23 | -10.049 | 129.232 | 266.286 | 1.00 | 0.00 | O |
| ATOM | 2000 | O2P | A | B | 23 | -10.498 | 131.221 | 267.819 | 1.00 | 0.00 | O |
| ATOM | 2001 | O5* | A | B | 23 | -8.380 | 129.939 | 267.976 | 1.00 | 0.00 | O |
| ATOM | 2002 | C5* | A | B | 23 | -7.251 | 129.294 | 267.438 | 1.00 | 0.00 | C |
| ATOM | 2003 | C4* | A | B | 23 | -6.279 | 128.938 | 268.526 | 1.00 | 0.00 | C |
| ATOM | 2004 | O4* | A | B | 23 | -5.610 | 130.119 | 269.039 | 1.00 | 0.00 | O |
| ATOM | 2005 | C3* | A | B | 23 | -6.869 | 128.264 | 269.751 | 1.00 | 0.00 | C |
| ATOM | 2006 | O3* | A | B | 23 | -6.966 | 126.870 | 269.482 | 1.00 | 0.00 | O |
| ATOM | 2007 | C2* | A | B | 23 | -5.773 | 128.522 | 270.764 | 1.00 | 0.00 | C |
| ATOM | 2008 | O2* | A | B | 23 | -4.686 | 127.643 | 270.521 | 1.00 | 0.00 | O |
| ATOM | 2009 | C1* | A | B | 23 | -5.393 | 129.966 | 270.427 | 1.00 | 0.00 | C |
| ATOM | 2010 | N9 | A | B | 23 | -6.254 | 130.937 | 271.105 | 1.00 | 0.00 | N |
| ATOM | 2011 | C8 | A | B | 23 | -7.337 | 131.596 | 270.571 | 1.00 | 0.00 | C |
| ATOM | 2012 | N7 | A | B | 23 | -7.887 | 132.458 | 271.392 | 1.00 | 0.00 | N |
| ATOM | 2013 | C5 | A | B | 23 | -7.135 | 132.330 | 272.552 | 1.00 | 0.00 | C |
| ATOM | 2014 | C6 | A | B | 23 | -7.235 | 132.943 | 273.793 | 1.00 | 0.00 | C |
| ATOM | 2015 | N6 | A | B | 23 | -8.162 | 133.866 | 274.076 | 1.00 | 0.00 | N |
| ATOM | 2016 | N1 | A | B | 23 | -6.354 | 132.584 | 274.746 | 1.00 | 0.00 | N |
| ATOM | 2017 | C2 | A | B | 23 | -5.424 | 131.660 | 274.447 | 1.00 | 0.00 | C |
| ATOM | 2018 | N3 | A | B | 23 | -5.229 | 131.010 | 273.311 | 1.00 | 0.00 | N |
| ATOM | 2019 | C4 | A | B | 23 | -6.132 | 131.393 | 272.391 | 1.00 | 0.00 | C |
| ATOM | 2020 | P | G | B | 24 | -8.103 | 125.985 | 270.213 | 1.00 | 0.00 | P |
| ATOM | 2021 | O1P | G | B | 24 | -8.023 | 124.691 | 269.512 | 1.00 | 0.00 | O |
| ATOM | 2022 | O2P | G | B | 24 | -9.379 | 126.735 | 270.226 | 1.00 | 0.00 | O |
| ATOM | 2023 | O5* | G | B | 24 | -7.561 | 125.869 | 271.701 | 1.00 | 0.00 | O |
| ATOM | 2024 | C5* | G | B | 24 | -6.243 | 125.427 | 271.934 | 1.00 | 0.00 | C |
| ATOM | 2025 | C4* | G | B | 24 | -5.924 | 125.515 | 273.394 | 1.00 | 0.00 | C |
| ATOM | 2026 | O4* | G | B | 24 | -5.489 | 126.869 | 273.668 | 1.00 | 0.00 | O |
| ATOM | 2027 | C3* | G | B | 24 | -7.095 | 125.288 | 274.340 | 1.00 | 0.00 | C |
| ATOM | 2028 | O3* | G | B | 24 | -7.216 | 123.900 | 274.626 | 1.00 | 0.00 | O |
| ATOM | 2029 | C2* | G | B | 24 | -6.614 | 126.045 | 275.564 | 1.00 | 0.00 | C |
| ATOM | 2030 | O2* | G | B | 24 | -5.565 | 125.365 | 276.220 | 1.00 | 0.00 | O |
| ATOM | 2031 | C1* | G | B | 24 | -6.010 | 127.290 | 274.908 | 1.00 | 0.00 | C |
| ATOM | 2032 | N9 | G | B | 24 | -7.032 | 128.288 | 274.647 | 1.00 | 0.00 | N |
| ATOM | 2033 | C8 | G | B | 24 | -7.775 | 128.448 | 273.505 | 1.00 | 0.00 | C |
| ATOM | 2034 | N7 | G | B | 24 | -8.676 | 129.385 | 273.612 | 1.00 | 0.00 | N |
| ATOM | 2035 | C5 | G | B | 24 | -8.489 | 129.885 | 274.897 | 1.00 | 0.00 | C |
| ATOM | 2036 | C6 | G | B | 24 | -9.187 | 130.893 | 275.598 | 1.00 | 0.00 | C |
| ATOM | 2037 | O6 | G | B | 24 | -10.132 | 131.601 | 275.201 | 1.00 | 0.00 | O |
| ATOM | 2038 | N1 | G | B | 24 | -8.698 | 131.045 | 276.893 | 1.00 | 0.00 | N |
| ATOM | 2039 | C2 | G | B | 24 | -7.669 | 130.322 | 277.441 | 1.00 | 0.00 | C |
| ATOM | 2040 | N2 | G | B | 24 | -7.350 | 130.602 | 278.714 | 1.00 | 0.00 | N |
| ATOM | 2041 | N3 | G | B | 24 | -7.002 | 129.384 | 276.787 | 1.00 | 0.00 | N |

| | | | | | | | | | |
|---|---|---|---|---|---|---|---|---|---|
| ATOM | 2042 | C4 | G B | 24 | -7.468 | 129.221 | 275.533 | 1.00 | 0.00 | C |
| ATOM | 2043 | P | C B | 25 | -8.670 | 123.260 | 274.890 | 1.00 | 0.00 | P |
| ATOM | 2044 | O1P | C B | 25 | -8.453 | 121.798 | 275.112 | 1.00 | 0.00 | O |
| ATOM | 2045 | O2P | C B | 25 | -9.594 | 123.701 | 273.839 | 1.00 | 0.00 | O |
| ATOM | 2046 | O5* | C B | 25 | -9.139 | 123.931 | 276.253 | 1.00 | 0.00 | O |
| ATOM | 2047 | C5* | C B | 25 | -8.359 | 123.797 | 277.424 | 1.00 | 0.00 | C |
| ATOM | 2048 | C4* | C B | 25 | -8.859 | 124.727 | 278.503 | 1.00 | 0.00 | C |
| ATOM | 2049 | O4* | C B | 25 | -8.559 | 126.112 | 278.159 | 1.00 | 0.00 | O |
| ATOM | 2050 | C3* | C B | 25 | -10.355 | 124.758 | 278.788 | 1.00 | 0.00 | C |
| ATOM | 2051 | O3* | C B | 25 | -10.762 | 123.628 | 279.562 | 1.00 | 0.00 | O |
| ATOM | 2052 | C2* | C B | 25 | -10.446 | 126.053 | 279.589 | 1.00 | 0.00 | C |
| ATOM | 2053 | O2* | C B | 25 | -9.888 | 125.913 | 280.880 | 1.00 | 0.00 | O |
| ATOM | 2054 | C1* | C B | 25 | -9.514 | 126.962 | 278.778 | 1.00 | 0.00 | C |
| ATOM | 2055 | N1 | C B | 25 | -10.241 | 127.667 | 277.731 | 1.00 | 0.00 | N |
| ATOM | 2056 | C2 | C B | 25 | -10.938 | 128.809 | 278.073 | 1.00 | 0.00 | C |
| ATOM | 2057 | O2 | C B | 25 | -10.892 | 129.196 | 279.244 | 1.00 | 0.00 | O |
| ATOM | 2058 | N3 | C B | 25 | -11.647 | 129.466 | 277.126 | 1.00 | 0.00 | N |
| ATOM | 2059 | C4 | C B | 25 | -11.673 | 129.010 | 275.875 | 1.00 | 0.00 | C |
| ATOM | 2060 | N4 | C B | 25 | -12.389 | 129.689 | 274.974 | 1.00 | 0.00 | N |
| ATOM | 2061 | C5 | C B | 25 | -10.961 | 127.837 | 275.490 | 1.00 | 0.00 | C |
| ATOM | 2062 | C6 | C B | 25 | -10.254 | 127.201 | 276.446 | 1.00 | 0.00 | C |
| HETATM | 2063 | P | M2G B | 26 | -11.242 | 123.296 | 278.237 | 1.00 | 0.00 | P |
| HETATM | 2064 | O1P | M2G B | 26 | -11.682 | 122.902 | 276.883 | 1.00 | 0.00 | O |
| HETATM | 2065 | O2P | M2G B | 26 | -11.190 | 122.280 | 279.313 | 1.00 | 0.00 | O |
| HETATM | 2066 | O5* | M2G B | 26 | -12.176 | 124.481 | 278.737 | 1.00 | 0.00 | O |
| HETATM | 2067 | C5* | M2G B | 26 | -12.314 | 124.755 | 280.124 | 1.00 | 0.00 | C |
| HETATM | 2068 | C4* | M2G B | 26 | -13.298 | 125.876 | 280.337 | 1.00 | 0.00 | C |
| HETATM | 2069 | O4* | M2G B | 26 | -12.922 | 127.032 | 279.529 | 1.00 | 0.00 | O |
| HETATM | 2070 | C3* | M2G B | 26 | -14.708 | 125.580 | 279.872 | 1.00 | 0.00 | C |
| HETATM | 2071 | O3* | M2G B | 26 | -15.404 | 124.831 | 280.853 | 1.00 | 0.00 | O |
| HETATM | 2072 | C2* | M2G B | 26 | -15.278 | 126.983 | 279.740 | 1.00 | 0.00 | C |
| HETATM | 2073 | O2* | M2G B | 26 | -15.524 | 127.570 | 280.999 | 1.00 | 0.00 | O |
| HETATM | 2074 | C1* | M2G B | 26 | -14.100 | 127.697 | 279.080 | 1.00 | 0.00 | C |
| HETATM | 2075 | N9 | M2G B | 26 | -14.132 | 127.641 | 277.621 | 1.00 | 0.00 | N |
| HETATM | 2076 | C8 | M2G B | 26 | -13.398 | 126.814 | 276.798 | 1.00 | 0.00 | C |
| HETATM | 2077 | N7 | M2G B | 26 | -13.636 | 127.007 | 275.533 | 1.00 | 0.00 | N |
| HETATM | 2078 | C5 | M2G B | 26 | -14.577 | 128.028 | 275.523 | 1.00 | 0.00 | C |
| HETATM | 2079 | C6 | M2G B | 26 | -15.203 | 128.671 | 274.439 | 1.00 | 0.00 | C |
| HETATM | 2080 | O6 | M2G B | 26 | -15.044 | 128.458 | 273.231 | 1.00 | 0.00 | O |
| HETATM | 2081 | N1 | M2G B | 26 | -16.096 | 129.647 | 274.866 | 1.00 | 0.00 | N |
| HETATM | 2082 | C2 | M2G B | 26 | -16.352 | 129.960 | 276.185 | 1.00 | 0.00 | C |
| HETATM | 2083 | N2 | M2G B | 26 | -17.276 | 130.898 | 276.412 | 1.00 | 0.00 | N |
| HETATM | 2084 | N3 | M2G B | 26 | -15.766 | 129.367 | 277.210 | 1.00 | 0.00 | N |
| HETATM | 2085 | C4 | M2G B | 26 | -14.896 | 128.416 | 276.806 | 1.00 | 0.00 | C |
| HETATM | 2086 | CM1 | M2G B | 26 | -17.855 | 131.047 | 277.762 | 1.00 | 0.00 | C |
| HETATM | 2087 | CM2 | M2G B | 26 | -17.712 | 131.777 | 275.322 | 1.00 | 0.00 | C |
| ATOM | 2088 | P | C B | 27 | -16.305 | 123.587 | 280.397 | 1.00 | 0.00 | P |
| ATOM | 2089 | O1P | C B | 27 | -16.783 | 122.903 | 281.630 | 1.00 | 0.00 | O |
| ATOM | 2090 | O2P | C B | 27 | -15.521 | 122.818 | 279.393 | 1.00 | 0.00 | O |
| ATOM | 2091 | O5* | C B | 27 | -17.560 | 124.261 | 279.680 | 1.00 | 0.00 | O |
| ATOM | 2092 | C5* | C B | 27 | -18.410 | 125.139 | 280.396 | 1.00 | 0.00 | C |
| ATOM | 2093 | C4* | C B | 27 | -19.392 | 125.807 | 279.463 | 1.00 | 0.00 | C |
| ATOM | 2094 | O4* | C B | 27 | -18.678 | 126.721 | 278.585 | 1.00 | 0.00 | O |
| ATOM | 2095 | C3* | C B | 27 | -20.149 | 124.907 | 278.496 | 1.00 | 0.00 | C |
| ATOM | 2096 | O3* | C B | 27 | -21.277 | 124.280 | 279.104 | 1.00 | 0.00 | O |
| ATOM | 2097 | C2* | C B | 27 | -20.597 | 125.924 | 277.449 | 1.00 | 0.00 | C |
| ATOM | 2098 | O2* | C B | 27 | -21.697 | 126.704 | 277.880 | 1.00 | 0.00 | O |
| ATOM | 2099 | C1* | C B | 27 | -19.349 | 126.802 | 277.333 | 1.00 | 0.00 | C |
| ATOM | 2100 | N1 | C B | 27 | -18.422 | 126.366 | 276.273 | 1.00 | 0.00 | N |
| ATOM | 2101 | C2 | C B | 27 | -18.719 | 126.684 | 274.938 | 1.00 | 0.00 | C |
| ATOM | 2102 | O2 | C B | 27 | -19.768 | 127.288 | 274.681 | 1.00 | 0.00 | O |
| ATOM | 2103 | N3 | C B | 27 | -17.859 | 126.313 | 273.959 | 1.00 | 0.00 | N |
| ATOM | 2104 | C4 | C B | 27 | -16.754 | 125.641 | 274.266 | 1.00 | 0.00 | C |
| ATOM | 2105 | N4 | C B | 27 | -15.947 | 125.298 | 273.266 | 1.00 | 0.00 | N |
| ATOM | 2106 | C5 | C B | 27 | -16.431 | 125.289 | 275.616 | 1.00 | 0.00 | C |
| ATOM | 2107 | C6 | C B | 27 | -17.287 | 125.670 | 276.580 | 1.00 | 0.00 | C |
| ATOM | 2108 | P | C B | 28 | -21.739 | 122.811 | 278.621 | 1.00 | 0.00 | P |
| ATOM | 2109 | O1P | C B | 28 | -22.792 | 122.398 | 279.575 | 1.00 | 0.00 | O |
| ATOM | 2110 | O2P | C B | 28 | -20.547 | 121.949 | 278.425 | 1.00 | 0.00 | O |
| ATOM | 2111 | O5* | C B | 28 | -22.420 | 123.014 | 277.197 | 1.00 | 0.00 | O |
| ATOM | 2112 | C5* | C B | 28 | -23.690 | 123.630 | 277.092 | 1.00 | 0.00 | C |
| ATOM | 2113 | C4* | C B | 28 | -24.060 | 123.817 | 275.645 | 1.00 | 0.00 | C |
| ATOM | 2114 | O4* | C B | 28 | -23.086 | 124.693 | 275.018 | 1.00 | 0.00 | O |
| ATOM | 2115 | C3* | C B | 28 | -24.008 | 122.580 | 274.772 | 1.00 | 0.00 | C |
| ATOM | 2116 | O3* | C B | 28 | -25.179 | 121.782 | 274.909 | 1.00 | 0.00 | O |
| ATOM | 2117 | C2* | C B | 28 | -23.939 | 123.212 | 273.395 | 1.00 | 0.00 | C |
| ATOM | 2118 | O2* | C B | 28 | -25.185 | 123.759 | 272.999 | 1.00 | 0.00 | O |
| ATOM | 2119 | C1* | C B | 28 | -22.930 | 124.326 | 273.663 | 1.00 | 0.00 | C |
| ATOM | 2120 | N1 | C B | 28 | -21.538 | 123.902 | 273.468 | 1.00 | 0.00 | N |
| ATOM | 2121 | C2 | C B | 28 | -21.046 | 123.850 | 272.170 | 1.00 | 0.00 | C |
| ATOM | 2122 | O2 | C B | 28 | -21.809 | 124.143 | 271.246 | 1.00 | 0.00 | O |
| ATOM | 2123 | N3 | C B | 28 | -19.758 | 123.479 | 271.956 | 1.00 | 0.00 | N |
| ATOM | 2124 | C4 | C B | 28 | -18.974 | 123.158 | 272.989 | 1.00 | 0.00 | C |
| ATOM | 2125 | N4 | C B | 28 | -17.693 | 122.790 | 272.726 | 1.00 | 0.00 | N |
| ATOM | 2126 | C5 | C B | 28 | -19.456 | 123.193 | 274.335 | 1.00 | 0.00 | C |
| ATOM | 2127 | C6 | C B | 28 | -20.734 | 123.569 | 274.525 | 1.00 | 0.00 | C |
| ATOM | 2128 | P | A B | 29 | -25.061 | 120.188 | 274.771 | 1.00 | 0.00 | P |

```
ATOM   2129 O1P    A B  29    -26.359 119.617 275.234  1.00  0.00           O
ATOM   2130 O2P    A B  29    -23.785 119.735 275.403  1.00  0.00           O
ATOM   2131 O5*    A B  29    -24.920 119.936 273.204  1.00  0.00           O
ATOM   2132 C5*    A B  29    -25.908 120.420 272.292  1.00  0.00           C
ATOM   2133 C4*    A B  29    -25.389 120.384 270.860  1.00  0.00           C
ATOM   2134 O4*    A B  29    -24.321 121.352 270.673  1.00  0.00           O
ATOM   2135 C3*    A B  29    -24.809 119.074 270.342  1.00  0.00           C
ATOM   2136 O3*    A B  29    -25.854 118.214 269.897  1.00  0.00           O
ATOM   2137 C2*    A B  29    -23.977 119.554 269.157  1.00  0.00           C
ATOM   2138 O2*    A B  29    -24.746 119.812 267.992  1.00  0.00           O
ATOM   2139 C1*    A B  29    -23.396 120.859 269.708  1.00  0.00           C
ATOM   2140 N9     A B  29    -22.095 120.670 270.361  1.00  0.00           N
ATOM   2141 C8     A B  29    -21.809 120.625 271.707  1.00  0.00           C
ATOM   2142 N7     A B  29    -20.535 120.434 271.970  1.00  0.00           N
ATOM   2143 C5     A B  29    -19.947 120.352 270.713  1.00  0.00           C
ATOM   2144 C6     A B  29    -18.625 120.149 270.303  1.00  0.00           C
ATOM   2145 N6     A B  29    -17.598 120.002 271.141  1.00  0.00           N
ATOM   2146 N1     A B  29    -18.382 120.105 268.976  1.00  0.00           N
ATOM   2147 C2     A B  29    -19.407 120.260 268.131  1.00  0.00           C
ATOM   2148 N3     A B  29    -20.688 120.459 268.393  1.00  0.00           N
ATOM   2149 C4     A B  29    -20.896 120.496 269.719  1.00  0.00           C
ATOM   2150 P      G B  30    -25.590 116.636 269.762  1.00  0.00           P
ATOM   2151 O1P    G B  30    -26.916 116.036 269.445  1.00  0.00           O
ATOM   2152 O2P    G B  30    -24.837 116.170 270.954  1.00  0.00           O
ATOM   2153 O5*    G B  30    -24.644 116.503 268.481  1.00  0.00           O
ATOM   2154 C5*    G B  30    -25.063 116.986 267.204  1.00  0.00           C
ATOM   2155 C4*    G B  30    -24.019 116.663 266.162  1.00  0.00           C
ATOM   2156 O4*    G B  30    -22.902 117.585 266.269  1.00  0.00           O
ATOM   2157 C3*    G B  30    -23.369 115.305 266.322  1.00  0.00           C
ATOM   2158 O3*    G B  30    -24.193 114.295 265.758  1.00  0.00           O
ATOM   2159 C2*    G B  30    -22.053 115.493 265.574  1.00  0.00           C
ATOM   2160 O2*    G B  30    -22.140 115.482 264.161  1.00  0.00           O
ATOM   2161 C1*    G B  30    -21.681 116.898 266.019  1.00  0.00           C
ATOM   2162 N9     G B  30    -20.930 116.837 267.260  1.00  0.00           N
ATOM   2163 C8     G B  30    -21.434 116.936 268.529  1.00  0.00           C
ATOM   2164 N7     G B  30    -20.514 116.851 269.451  1.00  0.00           N
ATOM   2165 C5     G B  30    -19.329 116.685 268.747  1.00  0.00           C
ATOM   2166 C6     G B  30    -17.986 116.565 269.213  1.00  0.00           C
ATOM   2167 O6     G B  30    -17.572 116.571 270.382  1.00  0.00           O
ATOM   2168 N1     G B  30    -17.085 116.429 268.156  1.00  0.00           N
ATOM   2169 C2     G B  30    -17.430 116.418 266.823  1.00  0.00           C
ATOM   2170 N2     G B  30    -16.413 116.267 265.952  1.00  0.00           N
ATOM   2171 N3     G B  30    -18.676 116.541 266.377  1.00  0.00           N
ATOM   2172 C4     G B  30    -19.568 116.668 267.391  1.00  0.00           C
ATOM   2173 P      A B  31    -23.891 112.751 266.080  1.00  0.00           P
ATOM   2174 O1P    A B  31    -24.763 111.955 265.184  1.00  0.00           O
ATOM   2175 O2P    A B  31    -23.969 112.546 267.552  1.00  0.00           O
ATOM   2176 O5*    A B  31    -22.386 112.545 265.617  1.00  0.00           O
ATOM   2177 C5*    A B  31    -22.057 112.528 264.237  1.00  0.00           C
ATOM   2178 C4*    A B  31    -20.602 112.201 264.063  1.00  0.00           C
ATOM   2179 O4*    A B  31    -19.811 113.305 264.575  1.00  0.00           O
ATOM   2180 C3*    A B  31    -20.120 110.984 264.843  1.00  0.00           C
ATOM   2181 O3*    A B  31    -20.308 109.785 264.085  1.00  0.00           O
ATOM   2182 C2*    A B  31    -18.637 111.294 264.994  1.00  0.00           C
ATOM   2183 O2*    A B  31    -17.905 111.010 263.817  1.00  0.00           O
ATOM   2184 C1*    A B  31    -18.675 112.802 265.255  1.00  0.00           C
ATOM   2185 N9     A B  31    -18.837 113.070 266.676  1.00  0.00           N
ATOM   2186 C8     A B  31    -19.993 113.277 267.388  1.00  0.00           C
ATOM   2187 N7     A B  31    -19.799 113.444 268.670  1.00  0.00           N
ATOM   2188 C5     A B  31    -18.424 113.353 268.813  1.00  0.00           C
ATOM   2189 C6     A B  31    -17.584 113.460 269.930  1.00  0.00           C
ATOM   2190 N6     A B  31    -18.035 113.681 271.172  1.00  0.00           N
ATOM   2191 N1     A B  31    -16.251 113.335 269.729  1.00  0.00           N
ATOM   2192 C2     A B  31    -15.808 113.120 268.480  1.00  0.00           C
ATOM   2193 N3     A B  31    -16.503 113.001 267.347  1.00  0.00           N
ATOM   2194 C4     A B  31    -17.819 113.129 267.590  1.00  0.00           C
HETATM 2195 N1   OMC B  32    -17.972 109.325 269.070  1.00  0.00           N
HETATM 2196 C2   OMC B  32    -17.729 109.944 270.279  1.00  0.00           C
HETATM 2197 N3   OMC B  32    -18.737 110.592 270.908  1.00  0.00           N
HETATM 2198 C4   OMC B  32    -19.949 110.637 270.348  1.00  0.00           C
HETATM 2199 C5   OMC B  32    -20.217 110.027 269.089  1.00  0.00           C
HETATM 2200 C6   OMC B  32    -19.206 109.389 268.490  1.00  0.00           C
HETATM 2201 O2   OMC B  32    -16.585 109.883 270.752  1.00  0.00           O
HETATM 2202 N4   OMC B  32    -20.930 111.273 271.003  1.00  0.00           N
HETATM 2203 C1*  OMC B  32    -16.884 108.587 268.441  1.00  0.00           C
HETATM 2204 C2*  OMC B  32    -16.992 107.095 268.734  1.00  0.00           C
HETATM 2205 O2*  OMC B  32    -15.662 106.530 268.726  1.00  0.00           O
HETATM 2206 CM2  OMC B  32    -14.804 106.717 269.878  1.00  0.00           C
HETATM 2207 C3*  OMC B  32    -17.852 106.631 267.570  1.00  0.00           C
HETATM 2208 C4*  OMC B  32    -17.301 107.463 266.428  1.00  0.00           C
HETATM 2209 O4*  OMC B  32    -16.989 108.741 267.040  1.00  0.00           O
HETATM 2210 O3*  OMC B  32    -17.689 105.243 267.308  1.00  0.00           O
HETATM 2211 C5*  OMC B  32    -18.267 107.691 265.300  1.00  0.00           C
HETATM 2212 O5*  OMC B  32    -19.521 108.119 265.814  1.00  0.00           O
HETATM 2213 P    OMC B  32    -20.734 108.420 264.828  1.00  0.00           P
HETATM 2214 O1P  OMC B  32    -21.954 108.704 265.630  1.00  0.00           O
HETATM 2215 O2P  OMC B  32    -20.757 107.356 263.784  1.00  0.00           O
```

```
ATOM    2216  P      U   B  33     -18.522 104.173 268.174  1.00  0.00           P
ATOM    2217  O1P    U   B  33     -17.892 102.848 267.960  1.00  0.00           O
ATOM    2218  O2P    U   B  33     -19.975 104.358 267.900  1.00  0.00           O
ATOM    2219  O5*    U   B  33     -18.260 104.626 269.677  1.00  0.00           O
ATOM    2220  C5*    U   B  33     -17.270 103.990 270.481  1.00  0.00           C
ATOM    2221  C4*    U   B  33     -17.689 104.028 271.934  1.00  0.00           C
ATOM    2222  O4*    U   B  33     -17.833 105.416 272.337  1.00  0.00           O
ATOM    2223  C3*    U   B  33     -19.054 103.408 272.214  1.00  0.00           C
ATOM    2224  O3*    U   B  33     -18.939 102.002 272.453  1.00  0.00           O
ATOM    2225  C2*    U   B  33     -19.514 104.149 273.468  1.00  0.00           C
ATOM    2226  O2*    U   B  33     -19.042 103.564 274.661  1.00  0.00           O
ATOM    2227  C1*    U   B  33     -18.892 105.533 273.270  1.00  0.00           C
ATOM    2228  N1     U   B  33     -19.875 106.490 272.757  1.00  0.00           N
ATOM    2229  C2     U   B  33     -20.516 107.268 273.684  1.00  0.00           C
ATOM    2230  O2     U   B  33     -20.245 107.217 274.867  1.00  0.00           O
ATOM    2231  N3     U   B  33     -21.485 108.106 273.180  1.00  0.00           N
ATOM    2232  C4     U   B  33     -21.860 108.242 271.858  1.00  0.00           C
ATOM    2233  O4     U   B  33     -22.771 109.026 271.560  1.00  0.00           O
ATOM    2234  C5     U   B  33     -21.124 107.412 270.945  1.00  0.00           C
ATOM    2235  C6     U   B  33     -20.173 106.589 271.415  1.00  0.00           C
HETATM  2236  P      OMG B  34     -19.475 100.906 271.952  1.00  0.00           P
HETATM  2237  O1P    OMG B  34     -18.938 100.675 270.579  1.00  0.00           O
HETATM  2238  O2P    OMG B  34     -19.646  99.750 272.870  1.00  0.00           O
HETATM  2239  O5*    OMG B  34     -20.871 101.674 271.852  1.00  0.00           O
HETATM  2240  C5*    OMG B  34     -22.080 100.985 271.550  1.00  0.00           C
HETATM  2241  C4*    OMG B  34     -22.947 100.912 272.780  1.00  0.00           C
HETATM  2242  O4*    OMG B  34     -22.280 100.051 273.726  1.00  0.00           O
HETATM  2243  C3*    OMG B  34     -23.113 102.223 273.530  1.00  0.00           C
HETATM  2244  O3*    OMG B  34     -24.193 103.010 273.010  1.00  0.00           O
HETATM  2245  C2*    OMG B  34     -23.376 101.765 274.968  1.00  0.00           C
HETATM  2246  O2*    OMG B  34     -24.769 101.559 275.309  1.00  0.00           O
HETATM  2247  CM2    OMG B  34     -25.145 101.391 276.698  1.00  0.00           C
HETATM  2248  C1*    OMG B  34     -22.622 100.438 275.039  1.00  0.00           C
HETATM  2249  N9     OMG B  34     -21.401 100.471 275.834  1.00  0.00           N
HETATM  2250  C8     OMG B  34     -20.148 100.056 275.445  1.00  0.00           C
HETATM  2251  N7     OMG B  34     -19.252 100.157 276.391  1.00  0.00           N
HETATM  2252  C5     OMG B  34     -19.953 100.681 277.471  1.00  0.00           C
HETATM  2253  C6     OMG B  34     -19.513 100.991 278.794  1.00  0.00           C
HETATM  2254  O6     OMG B  34     -18.371 100.868 279.289  1.00  0.00           O
HETATM  2255  N1     OMG B  34     -20.563 101.494 279.574  1.00  0.00           N
HETATM  2256  C2     OMG B  34     -21.867 101.676 279.140  1.00  0.00           C
HETATM  2257  N2     OMG B  34     -22.732 102.182 280.042  1.00  0.00           N
HETATM  2258  N3     OMG B  34     -22.285 101.385 277.913  1.00  0.00           N
HETATM  2259  C4     OMG B  34     -21.283 100.895 277.138  1.00  0.00           C
ATOM    2260  P      A   B  35     -23.865 104.821 272.891  1.00  0.00           P
ATOM    2261  O1P    A   B  35     -25.205 105.204 272.371  1.00  0.00           O
ATOM    2262  O2P    A   B  35     -22.800 104.379 271.954  1.00  0.00           O
ATOM    2263  O5*    A   B  35     -23.278 106.039 273.732  1.00  0.00           O
ATOM    2264  C5*    A   B  35     -22.403 105.788 274.823  1.00  0.00           C
ATOM    2265  C4*    A   B  35     -23.035 106.169 276.142  1.00  0.00           C
ATOM    2266  O4*    A   B  35     -22.945 105.008 277.020  1.00  0.00           O
ATOM    2267  C3*    A   B  35     -22.310 107.300 276.878  1.00  0.00           C
ATOM    2268  O3*    A   B  35     -23.004 108.535 276.687  1.00  0.00           O
ATOM    2269  C2*    A   B  35     -22.371 106.851 278.337  1.00  0.00           C
ATOM    2270  O2*    A   B  35     -23.609 107.152 278.963  1.00  0.00           O
ATOM    2271  C1*    A   B  35     -22.216 105.345 278.176  1.00  0.00           C
ATOM    2272  N9     A   B  35     -20.838 104.921 277.964  1.00  0.00           N
ATOM    2273  C8     A   B  35     -20.252 104.483 276.803  1.00  0.00           C
ATOM    2274  N7     A   B  35     -18.986 104.171 276.939  1.00  0.00           N
ATOM    2275  C5     A   B  35     -18.722 104.421 278.276  1.00  0.00           C
ATOM    2276  C6     A   B  35     -17.549 104.296 279.052  1.00  0.00           C
ATOM    2277  N6     A   B  35     -16.378 103.873 278.575  1.00  0.00           N
ATOM    2278  N1     A   B  35     -17.622 104.636 280.364  1.00  0.00           N
ATOM    2279  C2     A   B  35     -18.800 105.069 280.844  1.00  0.00           C
ATOM    2280  N3     A   B  35     -19.967 105.232 280.211  1.00  0.00           N
ATOM    2281  C4     A   B  35     -19.855 104.885 278.919  1.00  0.00           C
ATOM    2282  P      A   B  36     -23.699 109.978 276.762  1.00  0.00           P
ATOM    2283  O1P    A   B  36     -25.106 110.365 277.112  1.00  0.00           O
ATOM    2284  O2P    A   B  36     -23.053 110.560 275.568  1.00  0.00           O
ATOM    2285  O5*    A   B  36     -22.784 110.265 278.021  1.00  0.00           O
ATOM    2286  C5*    A   B  36     -21.517 110.870 277.862  1.00  0.00           C
ATOM    2287  C4*    A   B  36     -20.802 110.880 279.182  1.00  0.00           C
ATOM    2288  O4*    A   B  36     -20.563 109.507 279.615  1.00  0.00           O
ATOM    2289  C3*    A   B  36     -19.404 111.474 279.156  1.00  0.00           C
ATOM    2290  O3*    A   B  36     -19.428 112.897 279.181  1.00  0.00           O
ATOM    2291  C2*    A   B  36     -18.805 110.864 280.414  1.00  0.00           C
ATOM    2292  O2*    A   B  36     -19.296 111.449 281.612  1.00  0.00           O
ATOM    2293  C1*    A   B  36     -19.310 109.427 280.283  1.00  0.00           C
ATOM    2294  N9     A   B  36     -18.407 108.638 279.454  1.00  0.00           N
ATOM    2295  C8     A   B  36     -18.588 108.217 278.163  1.00  0.00           C
ATOM    2296  N7     A   B  36     -17.567 107.552 277.678  1.00  0.00           N
ATOM    2297  C5     A   B  36     -16.658 107.529 278.724  1.00  0.00           C
ATOM    2298  C6     A   B  36     -15.362 106.992 278.844  1.00  0.00           C
ATOM    2299  N6     A   B  36     -14.734 106.337 277.861  1.00  0.00           N
ATOM    2300  N1     A   B  36     -14.722 107.160 280.023  1.00  0.00           N
ATOM    2301  C2     A   B  36     -15.349 107.826 281.004  1.00  0.00           C
ATOM    2302  N3     A   B  36     -16.559 108.375 281.009  1.00  0.00           N
```

| | | | | | | | | | | |
|---|---|---|---|---|---|---|---|---|---|---|
| ATOM | 2303 | C4 | A | B | 36 | -17.167 | 108.188 | 279.828 | 1.00 | 0.00 | C |
| HETATM | 2304 | N1 | YG | B | 37 | -12.181 | 108.343 | 275.840 | 1.00 | 0.00 | N |
| HETATM | 2305 | N2 | YG | B | 37 | -10.272 | 108.439 | 277.090 | 1.00 | 0.00 | N |
| HETATM | 2306 | C2 | YG | B | 37 | -11.605 | 108.782 | 276.987 | 1.00 | 0.00 | C |
| HETATM | 2307 | N3 | YG | B | 37 | -12.250 | 109.490 | 277.949 | 1.00 | 0.00 | N |
| HETATM | 2308 | C3 | YG | B | 37 | -11.566 | 109.960 | 279.205 | 1.00 | 0.00 | C |
| HETATM | 2309 | C4 | YG | B | 37 | -13.572 | 109.717 | 277.622 | 1.00 | 0.00 | C |
| HETATM | 2310 | C5 | YG | B | 37 | -14.249 | 109.314 | 276.480 | 1.00 | 0.00 | C |
| HETATM | 2311 | C6 | YG | B | 37 | -13.540 | 108.559 | 275.477 | 1.00 | 0.00 | C |
| HETATM | 2312 | O6 | YG | B | 37 | -13.970 | 108.103 | 274.406 | 1.00 | 0.00 | O |
| HETATM | 2313 | N7 | YG | B | 37 | -15.571 | 109.745 | 276.513 | 1.00 | 0.00 | N |
| HETATM | 2314 | C8 | YG | B | 37 | -15.678 | 110.392 | 277.646 | 1.00 | 0.00 | C |
| HETATM | 2315 | N9 | YG | B | 37 | -14.504 | 110.421 | 278.367 | 1.00 | 0.00 | N |
| HETATM | 2316 | C10 | YG | B | 37 | -8.643 | 107.143 | 275.552 | 1.00 | 0.00 | C |
| HETATM | 2317 | C11 | YG | B | 37 | -9.977 | 107.741 | 275.929 | 1.00 | 0.00 | C |
| HETATM | 2318 | C12 | YG | B | 37 | -11.146 | 107.696 | 275.188 | 1.00 | 0.00 | C |
| HETATM | 2319 | C13 | YG | B | 37 | -11.262 | 106.995 | 273.852 | 1.00 | 0.00 | C |
| HETATM | 2320 | C14 | YG | B | 37 | -11.155 | 105.492 | 273.995 | 1.00 | 0.00 | C |
| HETATM | 2321 | C15 | YG | B | 37 | -10.064 | 104.808 | 273.155 | 1.00 | 0.00 | C |
| HETATM | 2322 | C16 | YG | B | 37 | -10.475 | 103.381 | 272.775 | 1.00 | 0.00 | C |
| HETATM | 2323 | O17 | YG | B | 37 | -11.620 | 103.144 | 272.386 | 1.00 | 0.00 | O |
| HETATM | 2324 | O18 | YG | B | 37 | -9.547 | 102.404 | 272.912 | 1.00 | 0.00 | O |
| HETATM | 2325 | C19 | YG | B | 37 | -8.967 | 101.714 | 271.773 | 1.00 | 0.00 | C |
| HETATM | 2326 | N20 | YG | B | 37 | -8.784 | 104.819 | 273.864 | 1.00 | 0.00 | N |
| HETATM | 2327 | C21 | YG | B | 37 | -7.635 | 105.216 | 273.313 | 1.00 | 0.00 | C |
| HETATM | 2328 | O22 | YG | B | 37 | -7.591 | 105.702 | 272.178 | 1.00 | 0.00 | O |
| HETATM | 2329 | O23 | YG | B | 37 | -6.494 | 105.088 | 274.033 | 1.00 | 0.00 | O |
| HETATM | 2330 | C24 | YG | B | 37 | -5.223 | 105.634 | 273.603 | 1.00 | 0.00 | C |
| HETATM | 2331 | C1* | YG | B | 37 | -14.289 | 111.083 | 279.654 | 1.00 | 0.00 | C |
| HETATM | 2332 | C2* | YG | B | 37 | -13.359 | 112.301 | 279.573 | 1.00 | 0.00 | C |
| HETATM | 2333 | O2* | YG | B | 37 | -12.504 | 112.351 | 280.699 | 1.00 | 0.00 | O |
| HETATM | 2334 | C3* | YG | B | 37 | -14.358 | 113.449 | 279.535 | 1.00 | 0.00 | C |
| HETATM | 2335 | O3* | YG | B | 37 | -13.779 | 114.649 | 280.023 | 1.00 | 0.00 | O |
| HETATM | 2336 | C4* | YG | B | 37 | -15.430 | 112.952 | 280.481 | 1.00 | 0.00 | C |
| HETATM | 2337 | O4* | YG | B | 37 | -15.542 | 111.550 | 280.129 | 1.00 | 0.00 | O |
| HETATM | 2338 | C5* | YG | B | 37 | -16.769 | 113.617 | 280.325 | 1.00 | 0.00 | C |
| HETATM | 2339 | O5* | YG | B | 37 | -16.967 | 113.998 | 278.971 | 1.00 | 0.00 | O |
| HETATM | 2340 | P | YG | B | 37 | -18.375 | 113.767 | 278.267 | 1.00 | 0.00 | P |
| HETATM | 2341 | O1P | YG | B | 37 | -18.151 | 112.907 | 277.071 | 1.00 | 0.00 | O |
| HETATM | 2342 | O2P | YG | B | 37 | -19.051 | 115.085 | 278.114 | 1.00 | 0.00 | O |
| ATOM | 2343 | P | A | B | 38 | -12.918 | 115.572 | 279.032 | 1.00 | 0.00 | P |
| ATOM | 2344 | O1P | A | B | 38 | -12.108 | 116.497 | 279.863 | 1.00 | 0.00 | O |
| ATOM | 2345 | O2P | A | B | 38 | -13.861 | 116.110 | 278.020 | 1.00 | 0.00 | O |
| ATOM | 2346 | O5* | A | B | 38 | -11.910 | 114.573 | 278.316 | 1.00 | 0.00 | O |
| ATOM | 2347 | C5* | A | B | 38 | -10.613 | 114.375 | 278.843 | 1.00 | 0.00 | C |
| ATOM | 2348 | C4* | A | B | 38 | -9.822 | 113.498 | 277.922 | 1.00 | 0.00 | C |
| ATOM | 2349 | O4* | A | B | 38 | -10.573 | 112.288 | 277.660 | 1.00 | 0.00 | O |
| ATOM | 2350 | C3* | A | B | 38 | -9.621 | 114.027 | 276.517 | 1.00 | 0.00 | C |
| ATOM | 2351 | O3* | A | B | 38 | -8.656 | 115.064 | 276.461 | 1.00 | 0.00 | O |
| ATOM | 2352 | C2* | A | B | 38 | -9.198 | 112.757 | 275.792 | 1.00 | 0.00 | C |
| ATOM | 2353 | O2* | A | B | 38 | -7.875 | 112.325 | 276.050 | 1.00 | 0.00 | O |
| ATOM | 2354 | C1* | A | B | 38 | -10.189 | 111.766 | 276.393 | 1.00 | 0.00 | C |
| ATOM | 2355 | N9 | A | B | 38 | -11.372 | 111.674 | 275.550 | 1.00 | 0.00 | N |
| ATOM | 2356 | C8 | A | B | 38 | -12.638 | 112.132 | 275.798 | 1.00 | 0.00 | C |
| ATOM | 2357 | N7 | A | B | 38 | -13.484 | 111.900 | 274.822 | 1.00 | 0.00 | N |
| ATOM | 2358 | C5 | A | B | 38 | -12.720 | 111.241 | 273.865 | 1.00 | 0.00 | C |
| ATOM | 2359 | C6 | A | B | 38 | -13.028 | 110.724 | 272.581 | 1.00 | 0.00 | C |
| ATOM | 2360 | N6 | A | B | 38 | -14.242 | 110.787 | 272.017 | 1.00 | 0.00 | N |
| ATOM | 2361 | N1 | A | B | 38 | -12.028 | 110.135 | 271.888 | 1.00 | 0.00 | N |
| ATOM | 2362 | C2 | A | B | 38 | -10.807 | 110.069 | 272.452 | 1.00 | 0.00 | C |
| ATOM | 2363 | N3 | A | B | 38 | -10.397 | 110.516 | 273.641 | 1.00 | 0.00 | N |
| ATOM | 2364 | C4 | A | B | 38 | -11.415 | 111.097 | 274.303 | 1.00 | 0.00 | C |
| HETATM | 2365 | N1 | PSU | B | 39 | -12.634 | 114.294 | 272.547 | 1.00 | 0.00 | N |
| HETATM | 2366 | C2 | PSU | B | 39 | -13.593 | 114.060 | 271.596 | 1.00 | 0.00 | C |
| HETATM | 2367 | N3 | PSU | B | 39 | -13.123 | 113.467 | 270.459 | 1.00 | 0.00 | N |
| HETATM | 2368 | C4 | PSU | B | 39 | -11.813 | 113.108 | 270.215 | 1.00 | 0.00 | C |
| HETATM | 2369 | C5 | PSU | B | 39 | -10.895 | 113.405 | 271.284 | 1.00 | 0.00 | C |
| HETATM | 2370 | C6 | PSU | B | 39 | -11.353 | 113.983 | 272.395 | 1.00 | 0.00 | C |
| HETATM | 2371 | O2 | PSU | B | 39 | -14.761 | 114.355 | 271.746 | 1.00 | 0.00 | O |
| HETATM | 2372 | O4 | PSU | B | 39 | -11.527 | 112.579 | 269.143 | 1.00 | 0.00 | O |
| HETATM | 2373 | C1* | PSU | B | 39 | -9.407 | 113.277 | 271.006 | 1.00 | 0.00 | C |
| HETATM | 2374 | C2* | PSU | B | 39 | -8.873 | 114.308 | 270.010 | 1.00 | 0.00 | C |
| HETATM | 2375 | O2* | PSU | B | 39 | -7.890 | 113.723 | 269.179 | 1.00 | 0.00 | O |
| HETATM | 2376 | C3* | PSU | B | 39 | -8.282 | 115.357 | 270.944 | 1.00 | 0.00 | C |
| HETATM | 2377 | C4* | PSU | B | 39 | -7.713 | 114.501 | 272.063 | 1.00 | 0.00 | C |
| HETATM | 2378 | O3* | PSU | B | 39 | -7.244 | 116.075 | 270.289 | 1.00 | 0.00 | O |
| HETATM | 2379 | O4* | PSU | B | 39 | -8.701 | 113.454 | 272.225 | 1.00 | 0.00 | O |
| HETATM | 2380 | C5* | PSU | B | 39 | -7.509 | 115.201 | 273.388 | 1.00 | 0.00 | C |
| HETATM | 2381 | O5* | PSU | B | 39 | -8.768 | 115.514 | 273.984 | 1.00 | 0.00 | O |
| HETATM | 2382 | P | PSU | B | 39 | -8.834 | 116.255 | 275.390 | 1.00 | 0.00 | P |
| HETATM | 2383 | O1P | PSU | B | 39 | -10.195 | 116.830 | 275.555 | 1.00 | 0.00 | O |
| HETATM | 2384 | O2P | PSU | B | 39 | -7.642 | 117.131 | 275.493 | 1.00 | 0.00 | O |
| HETATM | 2385 | P | 5MC | B | 40 | -7.570 | 117.488 | 269.596 | 1.00 | 0.00 | P |
| HETATM | 2386 | O1P | 5MC | B | 40 | -8.395 | 118.279 | 270.560 | 1.00 | 0.00 | O |
| HETATM | 2387 | O2P | 5MC | B | 40 | -6.301 | 118.055 | 269.068 | 1.00 | 0.00 | O |
| HETATM | 2388 | O5* | 5MC | B | 40 | -8.484 | 117.125 | 268.341 | 1.00 | 0.00 | O |
| HETATM | 2389 | C5* | 5MC | B | 40 | -7.907 | 116.866 | 267.069 | 1.00 | 0.00 | C |

```
HETATM 2390  C4*  5MC B  40      -8.942 116.285 266.141  1.00  0.00           C
HETATM 2391  O4*  5MC B  40      -9.775 115.332 266.860  1.00  0.00           O
HETATM 2392  C3*  5MC B  40      -9.953 117.288 265.635  1.00  0.00           C
HETATM 2393  O3*  5MC B  40      -9.432 118.027 264.546  1.00  0.00           O
HETATM 2394  C2*  5MC B  40     -11.085 116.378 265.188  1.00  0.00           C
HETATM 2395  O2*  5MC B  40     -10.880 115.770 263.929  1.00  0.00           O
HETATM 2396  C1*  5MC B  40     -11.085 115.345 266.311  1.00  0.00           C
HETATM 2397  N1   5MC B  40     -12.040 115.735 267.357  1.00  0.00           N
HETATM 2398  C2   5MC B  40     -13.399 115.732 267.044  1.00  0.00           C
HETATM 2399  O2   5MC B  40     -13.746 115.447 265.891  1.00  0.00           O
HETATM 2400  N3   5MC B  40     -14.299 116.052 267.995  1.00  0.00           N
HETATM 2401  C4   5MC B  40     -13.886 116.386 269.209  1.00  0.00           C
HETATM 2402  N4   5MC B  40     -14.817 116.674 270.125  1.00  0.00           N
HETATM 2403  C5   5MC B  40     -12.510 116.433 269.548  1.00  0.00           C
HETATM 2404  C6   5MC B  40     -11.625 116.090 268.606  1.00  0.00           C
HETATM 2405  CM5  5MC B  40     -12.114 116.976 270.881  1.00  0.00           C
ATOM   2406  P    U   B  41      -9.773 119.586 264.423  1.00  0.00           P
ATOM   2407  O1P  U   B  41      -8.597 120.232 263.807  1.00  0.00           O
ATOM   2408  O2P  U   B  41     -10.256 120.037 265.746  1.00  0.00           O
ATOM   2409  O5*  U   B  41     -11.009 119.660 263.429  1.00  0.00           O
ATOM   2410  C5*  U   B  41     -12.039 118.713 263.540  1.00  0.00           C
ATOM   2411  C4*  U   B  41     -13.281 119.177 262.841  1.00  0.00           C
ATOM   2412  O4*  U   B  41     -14.323 118.328 263.373  1.00  0.00           O
ATOM   2413  C3*  U   B  41     -13.772 120.602 263.092  1.00  0.00           C
ATOM   2414  O3*  U   B  41     -13.387 121.494 262.052  1.00  0.00           O
ATOM   2415  C2*  U   B  41     -15.281 120.404 263.091  1.00  0.00           C
ATOM   2416  O2*  U   B  41     -15.831 120.138 261.815  1.00  0.00           O
ATOM   2417  C1*  U   B  41     -15.366 119.116 263.883  1.00  0.00           C
ATOM   2418  N1   U   B  41     -15.126 119.318 265.314  1.00  0.00           N
ATOM   2419  C2   U   B  41     -16.229 119.594 266.061  1.00  0.00           C
ATOM   2420  O2   U   B  41     -17.350 119.659 265.563  1.00  0.00           O
ATOM   2421  N3   U   B  41     -15.990 119.799 267.396  1.00  0.00           N
ATOM   2422  C4   U   B  41     -14.772 119.755 268.035  1.00  0.00           C
ATOM   2423  O4   U   B  41     -14.719 119.961 269.249  1.00  0.00           O
ATOM   2424  C5   U   B  41     -13.655 119.452 267.180  1.00  0.00           C
ATOM   2425  C6   U   B  41     -13.873 119.243 265.880  1.00  0.00           C
ATOM   2426  P    G   B  42     -13.192 123.061 262.381  1.00  0.00           P
ATOM   2427  O1P  G   B  42     -12.759 123.738 261.156  1.00  0.00           O
ATOM   2428  O2P  G   B  42     -12.340 123.123 263.605  1.00  0.00           O
ATOM   2429  O5*  G   B  42     -14.661 123.588 262.693  1.00  0.00           O
ATOM   2430  C5*  G   B  42     -15.707 123.455 261.747  1.00  0.00           C
ATOM   2431  C4*  G   B  42     -17.050 123.619 262.435  1.00  0.00           C
ATOM   2432  O4*  G   B  42     -17.169 122.631 263.505  1.00  0.00           O
ATOM   2433  C3*  G   B  42     -17.290 124.933 263.177  1.00  0.00           C
ATOM   2434  O3*  G   B  42     -17.728 125.979 262.311  1.00  0.00           O
ATOM   2435  C2*  G   B  42     -18.441 124.549 264.095  1.00  0.00           C
ATOM   2436  O2*  G   B  42     -19.645 124.499 263.383  1.00  0.00           O
ATOM   2437  C1*  G   B  42     -18.041 123.135 264.509  1.00  0.00           C
ATOM   2438  N9   G   B  42     -17.366 123.126 265.806  1.00  0.00           N
ATOM   2439  C8   G   B  42     -16.036 122.898 266.087  1.00  0.00           C
ATOM   2440  N7   G   B  42     -15.761 122.958 267.369  1.00  0.00           N
ATOM   2441  C5   G   B  42     -16.987 123.242 267.965  1.00  0.00           C
ATOM   2442  C6   G   B  42     -17.337 123.398 269.327  1.00  0.00           C
ATOM   2443  O6   G   B  42     -16.618 123.320 270.323  1.00  0.00           O
ATOM   2444  N1   G   B  42     -18.688 123.673 269.472  1.00  0.00           N
ATOM   2445  C2   G   B  42     -19.594 123.778 268.443  1.00  0.00           C
ATOM   2446  N2   G   B  42     -20.876 124.049 268.783  1.00  0.00           N
ATOM   2447  N3   G   B  42     -19.285 123.630 267.182  1.00  0.00           N
ATOM   2448  C4   G   B  42     -17.979 123.362 267.013  1.00  0.00           C
ATOM   2449  P    G   B  43     -17.499 127.519 262.738  1.00  0.00           P
ATOM   2450  O1P  G   B  43     -17.698 128.389 261.551  1.00  0.00           O
ATOM   2451  O2P  G   B  43     -16.219 127.553 263.463  1.00  0.00           O
ATOM   2452  O5*  G   B  43     -18.693 127.823 263.748  1.00  0.00           O
ATOM   2453  C5*  G   B  43     -20.038 127.564 263.370  1.00  0.00           C
ATOM   2454  C4*  G   B  43     -20.943 127.660 264.562  1.00  0.00           C
ATOM   2455  O4*  G   B  43     -20.617 126.624 265.525  1.00  0.00           O
ATOM   2456  C3*  G   B  43     -20.768 128.945 265.334  1.00  0.00           C
ATOM   2457  O3*  G   B  43     -21.550 129.937 264.707  1.00  0.00           O
ATOM   2458  C2*  G   B  43     -21.301 128.559 266.708  1.00  0.00           C
ATOM   2459  O2*  G   B  43     -22.709 128.552 266.735  1.00  0.00           O
ATOM   2460  C1*  G   B  43     -20.797 127.123 266.835  1.00  0.00           C
ATOM   2461  N9   G   B  43     -19.537 126.976 267.555  1.00  0.00           N
ATOM   2462  C8   G   B  43     -18.292 126.796 267.019  1.00  0.00           C
ATOM   2463  N7   G   B  43     -17.355 126.656 267.922  1.00  0.00           N
ATOM   2464  C5   G   B  43     -18.024 126.763 269.126  1.00  0.00           C
ATOM   2465  C6   G   B  43     -17.539 126.707 270.448  1.00  0.00           C
ATOM   2466  O6   G   B  43     -16.367 126.516 270.841  1.00  0.00           O
ATOM   2467  N1   G   B  43     -18.567 126.897 271.377  1.00  0.00           N
ATOM   2468  C2   G   B  43     -19.884 127.107 271.066  1.00  0.00           C
ATOM   2469  N2   G   B  43     -20.721 127.294 272.096  1.00  0.00           N
ATOM   2470  N3   G   B  43     -20.351 127.143 269.834  1.00  0.00           N
ATOM   2471  C4   G   B  43     -19.373 126.969 268.918  1.00  0.00           C
ATOM   2472  P    A   B  44     -21.103 131.470 264.797  1.00  0.00           P
ATOM   2473  O1P  A   B  44     -21.943 132.184 263.795  1.00  0.00           O
ATOM   2474  O2P  A   B  44     -19.625 131.549 264.719  1.00  0.00           O
ATOM   2475  O5*  A   B  44     -21.558 131.882 266.266  1.00  0.00           O
ATOM   2476  C5*  A   B  44     -22.938 132.036 266.560  1.00  0.00           C
```

| | | | | | | | | | | |
|---|---|---|---|---|---|---|---|---|---|---|
| ATOM | 2477 | C4* | A | B | 44 | -23.175 | 131.851 | 268.035 | 1.00 | 0.00 | C |
| ATOM | 2478 | O4* | A | B | 44 | -22.426 | 130.701 | 268.475 | 1.00 | 0.00 | O |
| ATOM | 2479 | C3* | A | B | 44 | -22.633 | 132.965 | 268.900 | 1.00 | 0.00 | C |
| ATOM | 2480 | O3* | A | B | 44 | -23.558 | 134.040 | 268.972 | 1.00 | 0.00 | O |
| ATOM | 2481 | C2* | A | B | 44 | -22.480 | 132.275 | 270.239 | 1.00 | 0.00 | C |
| ATOM | 2482 | O2* | A | B | 44 | -23.721 | 132.157 | 270.899 | 1.00 | 0.00 | O |
| ATOM | 2483 | C1* | A | B | 44 | -21.986 | 130.899 | 269.802 | 1.00 | 0.00 | C |
| ATOM | 2484 | N9 | A | B | 44 | -20.537 | 130.760 | 269.802 | 1.00 | 0.00 | N |
| ATOM | 2485 | C8 | A | B | 44 | -19.702 | 130.869 | 268.728 | 1.00 | 0.00 | C |
| ATOM | 2486 | N7 | A | B | 44 | -18.439 | 130.649 | 269.017 | 1.00 | 0.00 | N |
| ATOM | 2487 | C5 | A | B | 44 | -18.445 | 130.394 | 270.378 | 1.00 | 0.00 | C |
| ATOM | 2488 | C6 | A | B | 44 | -17.418 | 130.086 | 271.301 | 1.00 | 0.00 | C |
| ATOM | 2489 | N6 | A | B | 44 | -16.113 | 129.962 | 270.981 | 1.00 | 0.00 | N |
| ATOM | 2490 | N1 | A | B | 44 | -17.779 | 129.898 | 272.592 | 1.00 | 0.00 | N |
| ATOM | 2491 | C2 | A | B | 44 | -19.075 | 129.997 | 272.918 | 1.00 | 0.00 | C |
| ATOM | 2492 | N3 | A | B | 44 | -20.115 | 130.269 | 272.148 | 1.00 | 0.00 | N |
| ATOM | 2493 | C4 | A | B | 44 | -19.732 | 130.465 | 270.877 | 1.00 | 0.00 | C |
| ATOM | 2494 | P | G | B | 45 | -21.868 | 135.763 | 268.378 | 1.00 | 0.00 | P |
| ATOM | 2495 | O1P | G | B | 45 | -22.848 | 136.859 | 268.491 | 1.00 | 0.00 | O |
| ATOM | 2496 | O2P | G | B | 45 | -21.045 | 135.630 | 267.148 | 1.00 | 0.00 | O |
| ATOM | 2497 | O5* | G | B | 45 | -20.942 | 135.807 | 269.671 | 1.00 | 0.00 | O |
| ATOM | 2498 | C5* | G | B | 45 | -21.524 | 135.904 | 270.966 | 1.00 | 0.00 | C |
| ATOM | 2499 | C4* | G | B | 45 | -20.453 | 135.877 | 272.012 | 1.00 | 0.00 | C |
| ATOM | 2500 | O4* | G | B | 45 | -19.840 | 134.564 | 272.006 | 1.00 | 0.00 | O |
| ATOM | 2501 | C3* | G | B | 45 | -19.305 | 136.824 | 271.722 | 1.00 | 0.00 | C |
| ATOM | 2502 | O3* | G | B | 45 | -19.606 | 138.079 | 272.302 | 1.00 | 0.00 | O |
| ATOM | 2503 | C2* | G | B | 45 | -18.153 | 136.165 | 272.464 | 1.00 | 0.00 | C |
| ATOM | 2504 | O2* | G | B | 45 | -18.211 | 136.457 | 273.833 | 1.00 | 0.00 | O |
| ATOM | 2505 | C1* | G | B | 45 | -18.449 | 134.676 | 272.264 | 1.00 | 0.00 | C |
| ATOM | 2506 | N9 | G | B | 45 | -17.733 | 134.067 | 271.145 | 1.00 | 0.00 | N |
| ATOM | 2507 | C8 | G | B | 45 | -18.166 | 133.993 | 269.841 | 1.00 | 0.00 | C |
| ATOM | 2508 | N7 | G | B | 45 | -17.315 | 133.404 | 269.047 | 1.00 | 0.00 | N |
| ATOM | 2509 | C5 | G | B | 45 | -16.250 | 133.062 | 269.876 | 1.00 | 0.00 | C |
| ATOM | 2510 | C6 | G | B | 45 | -15.005 | 132.433 | 269.565 | 1.00 | 0.00 | C |
| ATOM | 2511 | O6 | G | B | 45 | -14.580 | 132.033 | 268.450 | 1.00 | 0.00 | O |
| ATOM | 2512 | N1 | G | B | 45 | -14.215 | 132.304 | 270.693 | 1.00 | 0.00 | N |
| ATOM | 2513 | C2 | G | B | 45 | -14.569 | 132.731 | 271.957 | 1.00 | 0.00 | C |
| ATOM | 2514 | N2 | G | B | 45 | -13.657 | 132.525 | 272.922 | 1.00 | 0.00 | N |
| ATOM | 2515 | N3 | G | B | 45 | -15.721 | 133.321 | 272.253 | 1.00 | 0.00 | N |
| ATOM | 2516 | C4 | G | B | 45 | -16.498 | 133.456 | 271.177 | 1.00 | 0.00 | C |
| HETATM | 2517 | P | 7MG | B | 46 | -19.521 | 139.400 | 271.405 | 1.00 | 0.00 | P |
| HETATM | 2518 | O1P | 7MG | B | 46 | -19.857 | 139.060 | 270.002 | 1.00 | 0.00 | O |
| HETATM | 2519 | O2P | 7MG | B | 46 | -20.273 | 140.479 | 272.097 | 1.00 | 0.00 | O |
| HETATM | 2520 | O5* | 7MG | B | 46 | -17.979 | 139.773 | 271.476 | 1.00 | 0.00 | O |
| HETATM | 2521 | C5* | 7MG | B | 46 | -17.343 | 139.897 | 272.740 | 1.00 | 0.00 | C |
| HETATM | 2522 | C4* | 7MG | B | 46 | -16.288 | 140.980 | 272.697 | 1.00 | 0.00 | C |
| HETATM | 2523 | O4* | 7MG | B | 46 | -15.123 | 140.460 | 271.990 | 1.00 | 0.00 | O |
| HETATM | 2524 | C3* | 7MG | B | 46 | -16.680 | 142.262 | 271.968 | 1.00 | 0.00 | C |
| HETATM | 2525 | O3* | 7MG | B | 46 | -16.049 | 143.384 | 272.595 | 1.00 | 0.00 | O |
| HETATM | 2526 | C2* | 7MG | B | 46 | -16.113 | 142.013 | 270.572 | 1.00 | 0.00 | C |
| HETATM | 2527 | O2* | 7MG | B | 46 | -15.890 | 143.174 | 269.789 | 1.00 | 0.00 | O |
| HETATM | 2528 | C1* | 7MG | B | 46 | -14.800 | 141.319 | 270.915 | 1.00 | 0.00 | C |
| HETATM | 2529 | N9 | 7MG | B | 46 | -14.268 | 140.500 | 269.834 | 1.00 | 0.00 | N |
| HETATM | 2530 | C8 | 7MG | B | 46 | -14.830 | 140.308 | 268.513 | 1.00 | 0.00 | C |
| HETATM | 2531 | N7 | 7MG | B | 46 | -13.940 | 139.466 | 267.791 | 1.00 | 0.00 | N |
| HETATM | 2532 | C5 | 7MG | B | 46 | -12.904 | 139.144 | 268.651 | 1.00 | 0.00 | C |
| HETATM | 2533 | C6 | 7MG | B | 46 | -11.776 | 138.362 | 268.430 | 1.00 | 0.00 | C |
| HETATM | 2534 | O6 | 7MG | B | 46 | -11.466 | 137.799 | 267.405 | 1.00 | 0.00 | O |
| HETATM | 2535 | N1 | 7MG | B | 46 | -10.975 | 138.267 | 269.554 | 1.00 | 0.00 | N |
| HETATM | 2536 | C2 | 7MG | B | 46 | -11.237 | 138.883 | 270.759 | 1.00 | 0.00 | C |
| HETATM | 2537 | N2 | 7MG | B | 46 | -10.341 | 138.660 | 271.751 | 1.00 | 0.00 | N |
| HETATM | 2538 | N3 | 7MG | B | 46 | -12.292 | 139.652 | 270.980 | 1.00 | 0.00 | N |
| HETATM | 2539 | C4 | 7MG | B | 46 | -13.085 | 139.739 | 269.902 | 1.00 | 0.00 | C |
| HETATM | 2540 | CM7 | 7MG | B | 46 | -14.249 | 139.108 | 266.372 | 1.00 | 0.00 | C |
| ATOM | 2541 | P | U | B | 47 | -16.888 | 144.300 | 273.649 | 1.00 | 0.00 | P |
| ATOM | 2542 | O1P | U | B | 47 | -16.366 | 144.064 | 275.008 | 1.00 | 0.00 | O |
| ATOM | 2543 | O2P | U | B | 47 | -18.339 | 144.090 | 273.365 | 1.00 | 0.00 | O |
| ATOM | 2544 | O5* | U | B | 47 | -16.527 | 145.787 | 273.205 | 1.00 | 0.00 | O |
| ATOM | 2545 | C5* | U | B | 47 | -16.515 | 146.145 | 271.815 | 1.00 | 0.00 | C |
| ATOM | 2546 | C4* | U | B | 47 | -15.652 | 147.373 | 271.595 | 1.00 | 0.00 | C |
| ATOM | 2547 | O4* | U | B | 47 | -16.239 | 148.542 | 272.244 | 1.00 | 0.00 | O |
| ATOM | 2548 | C3* | U | B | 47 | -14.239 | 147.275 | 272.161 | 1.00 | 0.00 | C |
| ATOM | 2549 | O3* | U | B | 47 | -13.417 | 148.038 | 271.316 | 1.00 | 0.00 | O |
| ATOM | 2550 | C2* | U | B | 47 | -14.379 | 147.932 | 273.526 | 1.00 | 0.00 | C |
| ATOM | 2551 | O2* | U | B | 47 | -13.182 | 148.437 | 274.091 | 1.00 | 0.00 | O |
| ATOM | 2552 | C1* | U | B | 47 | -15.324 | 149.071 | 273.185 | 1.00 | 0.00 | C |
| ATOM | 2553 | N1 | U | B | 47 | -16.058 | 149.485 | 274.375 | 1.00 | 0.00 | N |
| ATOM | 2554 | C2 | U | B | 47 | -16.049 | 150.816 | 274.670 | 1.00 | 0.00 | C |
| ATOM | 2555 | O2 | U | B | 47 | -15.490 | 151.639 | 273.965 | 1.00 | 0.00 | O |
| ATOM | 2556 | N3 | U | B | 47 | -16.707 | 151.150 | 275.822 | 1.00 | 0.00 | N |
| ATOM | 2557 | C4 | U | B | 47 | -17.363 | 150.290 | 276.687 | 1.00 | 0.00 | C |
| ATOM | 2558 | O4 | U | B | 47 | -17.884 | 150.741 | 277.709 | 1.00 | 0.00 | O |
| ATOM | 2559 | C5 | U | B | 47 | -17.334 | 148.920 | 276.292 | 1.00 | 0.00 | C |
| ATOM | 2560 | C6 | U | B | 47 | -16.701 | 148.574 | 275.175 | 1.00 | 0.00 | C |
| ATOM | 2561 | P | C | B | 48 | -12.778 | 147.340 | 270.029 | 1.00 | 0.00 | P |
| ATOM | 2562 | O1P | C | B | 48 | -12.330 | 148.413 | 269.120 | 1.00 | 0.00 | O |
| ATOM | 2563 | O2P | C | B | 48 | -13.759 | 146.325 | 269.563 | 1.00 | 0.00 | O |

```
ATOM   2564  O5*   C   B  48    -11.532 146.553 270.634  1.00  0.00           O
ATOM   2565  C5*   C   B  48    -10.466 147.263 271.185  1.00  0.00           C
ATOM   2566  C4*   C   B  48     -9.371 146.317 271.581  1.00  0.00           C
ATOM   2567  O4*   C   B  48     -9.309 145.195 270.650  1.00  0.00           O
ATOM   2568  C3*   C   B  48     -8.000 146.961 271.570  1.00  0.00           C
ATOM   2569  O3*   C   B  48     -7.332 146.483 272.732  1.00  0.00           O
ATOM   2570  C2*   C   B  48     -7.406 146.446 270.249  1.00  0.00           C
ATOM   2571  O2*   C   B  48     -6.003 146.349 270.206  1.00  0.00           O
ATOM   2572  C1*   C   B  48     -7.981 145.037 270.183  1.00  0.00           C
ATOM   2573  N1    C   B  48     -8.044 144.509 268.808  1.00  0.00           N
ATOM   2574  C2    C   B  48     -7.104 143.587 268.381  1.00  0.00           C
ATOM   2575  O2    C   B  48     -6.231 143.230 269.171  1.00  0.00           O
ATOM   2576  N3    C   B  48     -7.171 143.120 267.102  1.00  0.00           N
ATOM   2577  C4    C   B  48     -8.133 143.574 266.282  1.00  0.00           C
ATOM   2578  N4    C   B  48     -8.175 143.145 264.998  1.00  0.00           N
ATOM   2579  C5    C   B  48     -9.096 144.503 266.718  1.00  0.00           C
ATOM   2580  C6    C   B  48     -9.008 144.937 267.964  1.00  0.00           C
HETATM 2581  P     5MC B  49     -6.387 147.453 273.578  1.00  0.00           P
HETATM 2582  O1P   5MC B  49     -5.603 146.546 274.457  1.00  0.00           O
HETATM 2583  O2P   5MC B  49     -5.685 148.452 272.730  1.00  0.00           O
HETATM 2584  O5*   5MC B  49     -7.387 148.329 274.488  1.00  0.00           O
HETATM 2585  C5*   5MC B  49     -8.401 147.728 275.278  1.00  0.00           C
HETATM 2586  C4*   5MC B  49     -9.048 148.792 276.153  1.00  0.00           C
HETATM 2587  O4*   5MC B  49     -8.107 149.173 277.194  1.00  0.00           O
HETATM 2588  C3*   5MC B  49     -9.248 150.089 275.388  1.00  0.00           C
HETATM 2589  O3*   5MC B  49    -10.450 150.041 274.665  1.00  0.00           O
HETATM 2590  C2*   5MC B  49     -9.288 151.099 276.506  1.00  0.00           C
HETATM 2591  O2*   5MC B  49    -10.532 151.002 277.171  1.00  0.00           O
HETATM 2592  C1*   5MC B  49     -8.152 150.589 277.386  1.00  0.00           C
HETATM 2593  N1    5MC B  49     -6.827 151.179 277.048  1.00  0.00           N
HETATM 2594  C2    5MC B  49     -6.601 152.557 277.329  1.00  0.00           C
HETATM 2595  O2    5MC B  49     -7.502 153.232 277.897  1.00  0.00           O
HETATM 2596  N3    5MC B  49     -5.419 153.125 276.979  1.00  0.00           N
HETATM 2597  C4    5MC B  49     -4.459 152.389 276.402  1.00  0.00           C
HETATM 2598  N4    5MC B  49     -3.304 153.005 276.095  1.00  0.00           N
HETATM 2599  C5    5MC B  49     -4.639 150.998 276.119  1.00  0.00           C
HETATM 2600  C6    5MC B  49     -5.834 150.430 276.454  1.00  0.00           C
HETATM 2601  CM5   5MC B  49     -3.511 150.246 275.475  1.00  0.00           C
ATOM   2602  P     U   B  50    -10.601 150.917 273.318  1.00  0.00           P
ATOM   2603  O1P   U   B  50    -11.810 150.432 272.650  1.00  0.00           O
ATOM   2604  O2P   U   B  50     -9.272 150.981 272.590  1.00  0.00           O
ATOM   2605  O5*   U   B  50    -10.857 152.417 273.779  1.00  0.00           O
ATOM   2606  C5*   U   B  50    -11.831 152.742 274.769  1.00  0.00           C
ATOM   2607  C4*   U   B  50    -11.814 154.234 275.057  1.00  0.00           C
ATOM   2608  O4*   U   B  50    -10.715 154.550 275.957  1.00  0.00           O
ATOM   2609  C3*   U   B  50    -11.570 155.171 273.878  1.00  0.00           C
ATOM   2610  O3*   U   B  50    -12.765 155.462 273.181  1.00  0.00           O
ATOM   2611  C2*   U   B  50    -11.133 156.424 274.608  1.00  0.00           C
ATOM   2612  O2*   U   B  50    -12.240 156.994 275.273  1.00  0.00           O
ATOM   2613  C1*   U   B  50    -10.196 155.821 275.642  1.00  0.00           C
ATOM   2614  N1    U   B  50     -8.841 155.645 275.119  1.00  0.00           N
ATOM   2615  C2    U   B  50     -8.046 156.775 275.049  1.00  0.00           C
ATOM   2616  O2    U   B  50     -8.462 157.900 275.322  1.00  0.00           O
ATOM   2617  N3    U   B  50     -6.748 156.555 274.660  1.00  0.00           N
ATOM   2618  C4    U   B  50     -6.184 155.360 274.326  1.00  0.00           C
ATOM   2619  O4    U   B  50     -4.995 155.332 273.987  1.00  0.00           O
ATOM   2620  C5    U   B  50     -7.089 154.231 274.375  1.00  0.00           C
ATOM   2621  C6    U   B  50     -8.358 154.415 274.751  1.00  0.00           C
ATOM   2622  P     G   B  51    -12.712 155.766 271.603  1.00  0.00           P
ATOM   2623  O1P   G   B  51    -14.095 155.596 271.161  1.00  0.00           O
ATOM   2624  O2P   G   B  51    -11.637 154.975 270.944  1.00  0.00           O
ATOM   2625  O5*   G   B  51    -12.242 157.273 271.541  1.00  0.00           O
ATOM   2626  C5*   G   B  51    -12.762 158.236 272.443  1.00  0.00           C
ATOM   2627  C4*   G   B  51    -12.046 159.556 272.252  1.00  0.00           C
ATOM   2628  O4*   G   B  51    -10.859 159.601 273.092  1.00  0.00           O
ATOM   2629  C3*   G   B  51    -11.552 159.840 270.839  1.00  0.00           C
ATOM   2630  O3*   G   B  51    -12.559 160.465 270.043  1.00  0.00           O
ATOM   2631  C2*   G   B  51    -10.401 160.793 271.097  1.00  0.00           C
ATOM   2632  O2*   G   B  51    -10.857 162.060 271.407  1.00  0.00           O
ATOM   2633  C1*   G   B  51     -9.803 160.225 272.386  1.00  0.00           C
ATOM   2634  N9    G   B  51     -8.779 159.240 272.064  1.00  0.00           N
ATOM   2635  C8    G   B  51     -8.937 157.891 271.866  1.00  0.00           C
ATOM   2636  N7    G   B  51     -7.825 157.292 271.506  1.00  0.00           N
ATOM   2637  C5    G   B  51     -6.878 158.313 271.480  1.00  0.00           C
ATOM   2638  C6    G   B  51     -5.511 158.279 271.153  1.00  0.00           C
ATOM   2639  O6    G   B  51     -4.815 157.295 270.819  1.00  0.00           O
ATOM   2640  N1    G   B  51     -4.932 159.538 271.247  1.00  0.00           N
ATOM   2641  C2    G   B  51     -5.589 160.681 271.611  1.00  0.00           C
ATOM   2642  N2    G   B  51     -4.858 161.802 271.641  1.00  0.00           N
ATOM   2643  N3    G   B  51     -6.868 160.725 271.930  1.00  0.00           N
ATOM   2644  C4    G   B  51     -7.446 159.516 271.842  1.00  0.00           C
ATOM   2645  P     U   B  52    -12.531 160.316 268.421  1.00  0.00           P
ATOM   2646  O1P   U   B  52    -13.784 160.898 267.898  1.00  0.00           O
ATOM   2647  O2P   U   B  52    -12.182 158.928 268.041  1.00  0.00           O
ATOM   2648  O5*   U   B  52    -11.322 161.244 268.014  1.00  0.00           O
ATOM   2649  C5*   U   B  52    -11.378 162.628 268.279  1.00  0.00           C
ATOM   2650  C4*   U   B  52    -10.020 163.235 268.100  1.00  0.00           C
```

| | | | | | | | | | | |
|---|---|---|---|---|---|---|---|---|---|---|
| ATOM | 2651 | O4* | U | B | 52 | -9.116 | 162.655 | 269.056 | 1.00 | 0.00 | O |
| ATOM | 2652 | C3* | U | B | 52 | -9.345 | 162.894 | 266.788 | 1.00 | 0.00 | C |
| ATOM | 2653 | O3* | U | B | 52 | -9.827 | 163.728 | 265.741 | 1.00 | 0.00 | O |
| ATOM | 2654 | C2* | U | B | 52 | -7.918 | 163.265 | 267.124 | 1.00 | 0.00 | C |
| ATOM | 2655 | O2* | U | B | 52 | -7.757 | 164.668 | 267.132 | 1.00 | 0.00 | O |
| ATOM | 2656 | C1* | U | B | 52 | -7.792 | 162.679 | 268.532 | 1.00 | 0.00 | C |
| ATOM | 2657 | N1 | U | B | 52 | -7.287 | 161.296 | 268.422 | 1.00 | 0.00 | N |
| ATOM | 2658 | C2 | U | B | 52 | -5.954 | 161.135 | 268.185 | 1.00 | 0.00 | C |
| ATOM | 2659 | O2 | U | B | 52 | -5.201 | 162.059 | 268.107 | 1.00 | 0.00 | O |
| ATOM | 2660 | N3 | U | B | 52 | -5.532 | 159.846 | 268.025 | 1.00 | 0.00 | N |
| ATOM | 2661 | C4 | U | B | 52 | -6.308 | 158.725 | 268.054 | 1.00 | 0.00 | C |
| ATOM | 2662 | O4 | U | B | 52 | -5.796 | 157.625 | 267.835 | 1.00 | 0.00 | O |
| ATOM | 2663 | C5 | U | B | 52 | -7.696 | 158.973 | 268.316 | 1.00 | 0.00 | C |
| ATOM | 2664 | C6 | U | B | 52 | -8.117 | 160.219 | 268.500 | 1.00 | 0.00 | C |
| ATOM | 2665 | P | G | B | 53 | -9.648 | 163.270 | 264.205 | 1.00 | 0.00 | P |
| ATOM | 2666 | O1P | G | B | 53 | -10.305 | 164.306 | 263.374 | 1.00 | 0.00 | O |
| ATOM | 2667 | O2P | G | B | 53 | -10.072 | 161.861 | 264.098 | 1.00 | 0.00 | O |
| ATOM | 2668 | O5* | G | B | 53 | -8.084 | 163.293 | 263.937 | 1.00 | 0.00 | O |
| ATOM | 2669 | C5* | G | B | 53 | -7.327 | 164.481 | 264.084 | 1.00 | 0.00 | C |
| ATOM | 2670 | C4* | G | B | 53 | -5.861 | 164.161 | 263.931 | 1.00 | 0.00 | C |
| ATOM | 2671 | O4* | G | B | 53 | -5.496 | 163.219 | 264.974 | 1.00 | 0.00 | O |
| ATOM | 2672 | C3* | G | B | 53 | -5.429 | 163.421 | 262.661 | 1.00 | 0.00 | C |
| ATOM | 2673 | O3* | G | B | 53 | -5.237 | 164.320 | 261.563 | 1.00 | 0.00 | O |
| ATOM | 2674 | C2* | G | B | 53 | -4.094 | 162.817 | 263.094 | 1.00 | 0.00 | C |
| ATOM | 2675 | O2* | G | B | 53 | -3.002 | 163.704 | 263.047 | 1.00 | 0.00 | O |
| ATOM | 2676 | C1* | G | B | 53 | -4.361 | 162.469 | 264.558 | 1.00 | 0.00 | C |
| ATOM | 2677 | N9 | G | B | 53 | -4.690 | 161.054 | 264.660 | 1.00 | 0.00 | N |
| ATOM | 2678 | C8 | G | B | 53 | -5.913 | 160.504 | 264.934 | 1.00 | 0.00 | C |
| ATOM | 2679 | N7 | G | B | 53 | -5.897 | 159.193 | 264.947 | 1.00 | 0.00 | N |
| ATOM | 2680 | C5 | G | B | 53 | -4.583 | 158.869 | 264.672 | 1.00 | 0.00 | C |
| ATOM | 2681 | C6 | G | B | 53 | -3.968 | 157.597 | 264.525 | 1.00 | 0.00 | C |
| ATOM | 2682 | O6 | G | B | 53 | -4.478 | 156.473 | 264.663 | 1.00 | 0.00 | O |
| ATOM | 2683 | N1 | G | B | 53 | -2.629 | 157.717 | 264.186 | 1.00 | 0.00 | N |
| ATOM | 2684 | C2 | G | B | 53 | -1.951 | 158.917 | 264.011 | 1.00 | 0.00 | C |
| ATOM | 2685 | N2 | G | B | 53 | -0.640 | 158.810 | 263.700 | 1.00 | 0.00 | N |
| ATOM | 2686 | N3 | G | B | 53 | -2.516 | 160.115 | 264.145 | 1.00 | 0.00 | N |
| ATOM | 2687 | C4 | G | B | 53 | -3.827 | 160.011 | 264.476 | 1.00 | 0.00 | C |
| HETATM | 2688 | N1 | 5MU | B | 54 | -2.543 | 159.148 | 260.570 | 1.00 | 0.00 | N |
| HETATM | 2689 | C2 | 5MU | B | 54 | -2.321 | 157.805 | 260.684 | 1.00 | 0.00 | C |
| HETATM | 2690 | N3 | 5MU | B | 54 | -3.441 | 157.042 | 260.954 | 1.00 | 0.00 | N |
| HETATM | 2691 | C4 | 5MU | B | 54 | -4.741 | 157.490 | 261.120 | 1.00 | 0.00 | C |
| HETATM | 2692 | C5 | 5MU | B | 54 | -4.897 | 158.924 | 260.968 | 1.00 | 0.00 | C |
| HETATM | 2693 | C5M | 5MU | B | 54 | -6.272 | 159.508 | 261.077 | 1.00 | 0.00 | C |
| HETATM | 2694 | C6 | 5MU | B | 54 | -3.811 | 159.680 | 260.715 | 1.00 | 0.00 | C |
| HETATM | 2695 | O2 | 5MU | B | 54 | -1.202 | 157.322 | 260.557 | 1.00 | 0.00 | O |
| HETATM | 2696 | O4 | 5MU | B | 54 | -5.653 | 156.665 | 261.338 | 1.00 | 0.00 | O |
| HETATM | 2697 | C1* | 5MU | B | 54 | -1.361 | 159.977 | 260.267 | 1.00 | 0.00 | C |
| HETATM | 2698 | C2* | 5MU | B | 54 | -1.073 | 160.084 | 258.759 | 1.00 | 0.00 | C |
| HETATM | 2699 | O2* | 5MU | B | 54 | 0.314 | 160.230 | 258.512 | 1.00 | 0.00 | O |
| HETATM | 2700 | C3* | 5MU | B | 54 | -1.860 | 161.340 | 258.405 | 1.00 | 0.00 | C |
| HETATM | 2701 | C4* | 5MU | B | 54 | -1.543 | 162.224 | 259.599 | 1.00 | 0.00 | C |
| HETATM | 2702 | O3* | 5MU | B | 54 | -1.457 | 161.941 | 257.171 | 1.00 | 0.00 | O |
| HETATM | 2703 | O4* | 5MU | B | 54 | -1.621 | 161.294 | 260.721 | 1.00 | 0.00 | O |
| HETATM | 2704 | C5* | 5MU | B | 54 | -2.520 | 163.343 | 259.851 | 1.00 | 0.00 | C |
| HETATM | 2705 | O5* | 5MU | B | 54 | -3.809 | 162.813 | 260.039 | 1.00 | 0.00 | O |
| HETATM | 2706 | P | 5MU | B | 54 | -5.086 | 163.753 | 260.033 | 1.00 | 0.00 | P |
| HETATM | 2707 | O1P | 5MU | B | 54 | -6.271 | 162.936 | 259.654 | 1.00 | 0.00 | O |
| HETATM | 2708 | O2P | 5MU | B | 54 | -4.739 | 164.967 | 259.250 | 1.00 | 0.00 | O |
| HETATM | 2709 | N1 | PSU | B | 55 | -5.802 | 158.580 | 257.650 | 1.00 | 0.00 | N |
| HETATM | 2710 | C2 | PSU | B | 55 | -6.691 | 157.648 | 258.121 | 1.00 | 0.00 | C |
| HETATM | 2711 | N3 | PSU | B | 55 | -6.252 | 156.346 | 258.028 | 1.00 | 0.00 | N |
| HETATM | 2712 | C4 | PSU | B | 55 | -5.013 | 155.949 | 257.509 | 1.00 | 0.00 | C |
| HETATM | 2713 | C5 | PSU | B | 55 | -4.181 | 157.006 | 257.039 | 1.00 | 0.00 | C |
| HETATM | 2714 | C6 | PSU | B | 55 | -4.610 | 158.271 | 257.128 | 1.00 | 0.00 | C |
| HETATM | 2715 | O2 | PSU | B | 55 | -7.778 | 157.945 | 258.570 | 1.00 | 0.00 | O |
| HETATM | 2716 | O4 | PSU | B | 55 | -4.712 | 154.769 | 257.512 | 1.00 | 0.00 | O |
| HETATM | 2717 | C1* | PSU | B | 55 | -2.960 | 156.611 | 256.238 | 1.00 | 0.00 | C |
| HETATM | 2718 | C2* | PSU | B | 55 | -3.211 | 156.452 | 254.735 | 1.00 | 0.00 | C |
| HETATM | 2719 | O2* | PSU | B | 55 | -2.368 | 155.404 | 254.276 | 1.00 | 0.00 | O |
| HETATM | 2720 | C3* | PSU | B | 55 | -2.829 | 157.847 | 254.233 | 1.00 | 0.00 | C |
| HETATM | 2721 | C4* | PSU | B | 55 | -1.602 | 158.137 | 255.079 | 1.00 | 0.00 | C |
| HETATM | 2722 | O3* | PSU | B | 55 | -2.495 | 157.919 | 252.851 | 1.00 | 0.00 | O |
| HETATM | 2723 | O4* | PSU | B | 55 | -1.987 | 157.618 | 256.389 | 1.00 | 0.00 | O |
| HETATM | 2724 | C5* | PSU | B | 55 | -1.279 | 159.609 | 255.212 | 1.00 | 0.00 | C |
| HETATM | 2725 | O5* | PSU | B | 55 | -2.475 | 160.349 | 255.471 | 1.00 | 0.00 | O |
| HETATM | 2726 | P | PSU | B | 55 | -2.448 | 161.896 | 255.891 | 1.00 | 0.00 | P |
| HETATM | 2727 | O1P | PSU | B | 55 | -3.831 | 162.248 | 256.336 | 1.00 | 0.00 | O |
| HETATM | 2728 | O2P | PSU | B | 55 | -1.804 | 162.710 | 254.824 | 1.00 | 0.00 | O |
| ATOM | 2729 | P | C | B | 56 | -3.530 | 158.542 | 251.790 | 1.00 | 0.00 | P |
| ATOM | 2730 | O1P | C | B | 56 | -2.763 | 158.567 | 250.506 | 1.00 | 0.00 | O |
| ATOM | 2731 | O2P | C | B | 56 | -4.199 | 159.782 | 252.286 | 1.00 | 0.00 | O |
| ATOM | 2732 | O5* | C | B | 56 | -4.698 | 157.472 | 251.655 | 1.00 | 0.00 | O |
| ATOM | 2733 | C5* | C | B | 56 | -5.900 | 157.826 | 251.008 | 1.00 | 0.00 | C |
| ATOM | 2734 | C4* | C | B | 56 | -6.807 | 156.637 | 250.892 | 1.00 | 0.00 | C |
| ATOM | 2735 | O4* | C | B | 56 | -6.244 | 155.709 | 249.938 | 1.00 | 0.00 | O |
| ATOM | 2736 | C3* | C | B | 56 | -6.967 | 155.822 | 252.169 | 1.00 | 0.00 | C |
| ATOM | 2737 | O3* | C | B | 56 | -8.002 | 156.411 | 252.941 | 1.00 | 0.00 | O |

```
ATOM   2738  C2*   C   B  56      -7.397 154.477 251.614  1.00  0.00           C
ATOM   2739  O2*   C   B  56      -8.789 154.390 251.290  1.00  0.00           O
ATOM   2740  C1*   C   B  56      -6.527 154.381 250.356  1.00  0.00           C
ATOM   2741  N1    C   B  56      -5.247 153.719 250.642  1.00  0.00           N
ATOM   2742  C2    C   B  56      -5.229 152.338 250.738  1.00  0.00           C
ATOM   2743  O2    C   B  56      -6.271 151.730 250.637  1.00  0.00           O
ATOM   2744  N3    C   B  56      -4.078 151.702 250.946  1.00  0.00           N
ATOM   2745  C4    C   B  56      -2.951 152.386 251.081  1.00  0.00           C
ATOM   2746  N4    C   B  56      -1.839 151.679 251.270  1.00  0.00           N
ATOM   2747  C5    C   B  56      -2.923 153.812 251.020  1.00  0.00           C
ATOM   2748  C6    C   B  56      -4.096 154.438 250.798  1.00  0.00           C
ATOM   2749  P     G   B  57      -7.811 156.593 254.534  1.00  0.00           P
ATOM   2750  O1P   G   B  57      -9.080 157.234 254.993  1.00  0.00           O
ATOM   2751  O2P   G   B  57      -6.505 157.196 254.869  1.00  0.00           O
ATOM   2752  O5*   G   B  57      -7.768 155.097 255.079  1.00  0.00           O
ATOM   2753  C5*   G   B  57      -8.912 154.278 254.981  1.00  0.00           C
ATOM   2754  C4*   G   B  57      -8.572 152.826 255.269  1.00  0.00           C
ATOM   2755  O4*   G   B  57      -7.633 152.286 254.288  1.00  0.00           O
ATOM   2756  C3*   G   B  57      -7.906 152.551 256.607  1.00  0.00           C
ATOM   2757  O3*   G   B  57      -8.911 152.493 257.597  1.00  0.00           O
ATOM   2758  C2*   G   B  57      -7.330 151.169 256.376  1.00  0.00           C
ATOM   2759  O2*   G   B  57      -8.361 150.200 256.442  1.00  0.00           O
ATOM   2760  C1*   G   B  57      -6.840 151.292 254.923  1.00  0.00           C
ATOM   2761  N9    G   B  57      -5.452 151.716 254.824  1.00  0.00           N
ATOM   2762  C8    G   B  57      -4.972 152.983 254.551  1.00  0.00           C
ATOM   2763  N7    G   B  57      -3.661 153.018 254.457  1.00  0.00           N
ATOM   2764  C5    G   B  57      -3.264 151.700 254.701  1.00  0.00           C
ATOM   2765  C6    G   B  57      -1.944 151.091 254.713  1.00  0.00           C
ATOM   2766  O6    G   B  57      -0.838 151.630 254.531  1.00  0.00           O
ATOM   2767  N1    G   B  57      -2.015 149.730 254.994  1.00  0.00           N
ATOM   2768  C2    G   B  57      -3.186 149.047 255.259  1.00  0.00           C
ATOM   2769  N2    G   B  57      -3.078 147.757 255.581  1.00  0.00           N
ATOM   2770  N3    G   B  57      -4.402 149.596 255.230  1.00  0.00           N
ATOM   2771  C4    G   B  57      -4.360 150.899 254.948  1.00  0.00           C
HETATM 2772  P     1MA B  58      -8.580 153.031 259.050  1.00  0.00           P
HETATM 2773  O1P   1MA B  58      -7.872 154.315 259.026  1.00  0.00           O
HETATM 2774  O2P   1MA B  58      -9.820 152.889 259.829  1.00  0.00           O
HETATM 2775  O5*   1MA B  58      -7.474 152.023 259.621  1.00  0.00           O
HETATM 2776  C5*   1MA B  58      -7.750 150.653 259.771  1.00  0.00           C
HETATM 2777  C4*   1MA B  58      -6.931 150.061 260.918  1.00  0.00           C
HETATM 2778  O4*   1MA B  58      -5.520 150.401 260.764  1.00  0.00           O
HETATM 2779  C3*   1MA B  58      -7.282 150.495 262.350  1.00  0.00           C
HETATM 2780  O3*   1MA B  58      -6.843 149.463 263.242  1.00  0.00           O
HETATM 2781  C2*   1MA B  58      -6.345 151.680 262.497  1.00  0.00           C
HETATM 2782  O2*   1MA B  58      -6.070 152.093 263.809  1.00  0.00           O
HETATM 2783  C1*   1MA B  58      -5.071 151.083 261.909  1.00  0.00           C
HETATM 2784  N9    1MA B  58      -4.047 152.070 261.548  1.00  0.00           N
HETATM 2785  C8    1MA B  58      -4.233 153.406 261.351  1.00  0.00           C
HETATM 2786  N7    1MA B  58      -3.127 154.063 261.128  1.00  0.00           N
HETATM 2787  C5    1MA B  58      -2.137 153.088 261.150  1.00  0.00           C
HETATM 2788  C6    1MA B  58      -0.701 153.289 260.937  1.00  0.00           C
HETATM 2789  N6    1MA B  58      -0.146 154.639 260.712  1.00  0.00           N
HETATM 2790  N1    1MA B  58       0.048 152.052 261.019  1.00  0.00           N
HETATM 2791  CM1   1MA B  58       1.497 152.257 260.818  1.00  0.00           C
HETATM 2792  C2    1MA B  58      -0.649 150.913 261.264  1.00  0.00           C
HETATM 2793  N3    1MA B  58      -1.986 150.705 261.474  1.00  0.00           N
HETATM 2794  C4    1MA B  58      -2.693 151.861 261.397  1.00  0.00           C
ATOM   2795  P     U   B  59      -7.751 148.122 263.494  1.00  0.00           P
ATOM   2796  O1P   U   B  59      -7.589 147.061 262.480  1.00  0.00           O
ATOM   2797  O2P   U   B  59      -9.112 148.575 263.881  1.00  0.00           O
ATOM   2798  O5*   U   B  59      -7.118 147.534 264.833  1.00  0.00           O
ATOM   2799  C5*   U   B  59      -7.328 148.189 266.096  1.00  0.00           C
ATOM   2800  C4*   U   B  59      -6.236 147.783 267.067  1.00  0.00           C
ATOM   2801  O4*   U   B  59      -6.121 146.325 267.020  1.00  0.00           O
ATOM   2802  C3*   U   B  59      -4.842 148.291 266.674  1.00  0.00           C
ATOM   2803  O3*   U   B  59      -4.606 149.641 267.183  1.00  0.00           O
ATOM   2804  C2*   U   B  59      -3.916 147.232 267.291  1.00  0.00           C
ATOM   2805  O2*   U   B  59      -3.599 147.536 268.634  1.00  0.00           O
ATOM   2806  C1*   U   B  59      -4.777 145.949 267.233  1.00  0.00           C
ATOM   2807  N1    U   B  59      -4.367 144.966 266.195  1.00  0.00           N
ATOM   2808  C2    U   B  59      -3.172 144.323 266.407  1.00  0.00           C
ATOM   2809  O2    U   B  59      -2.512 144.494 267.421  1.00  0.00           O
ATOM   2810  N3    U   B  59      -2.772 143.453 265.410  1.00  0.00           N
ATOM   2811  C4    U   B  59      -3.450 143.155 264.248  1.00  0.00           C
ATOM   2812  O4    U   B  59      -2.958 142.332 263.465  1.00  0.00           O
ATOM   2813  C5    U   B  59      -4.709 143.853 264.089  1.00  0.00           C
ATOM   2814  C6    U   B  59      -5.117 144.709 265.056  1.00  0.00           C
ATOM   2815  P     C   B  60      -3.632 150.659 266.369  1.00  0.00           P
ATOM   2816  O1P   C   B  60      -3.455 151.893 267.150  1.00  0.00           O
ATOM   2817  O2P   C   B  60      -4.126 150.736 264.958  1.00  0.00           O
ATOM   2818  O5*   C   B  60      -2.259 149.865 266.215  1.00  0.00           O
ATOM   2819  C5*   C   B  60      -1.379 149.633 267.326  1.00  0.00           C
ATOM   2820  C4*   C   B  60      -0.140 148.877 266.845  1.00  0.00           C
ATOM   2821  O4*   C   B  60      -0.585 147.677 266.130  1.00  0.00           O
ATOM   2822  C3*   C   B  60       0.704 149.643 265.844  1.00  0.00           C
ATOM   2823  O3*   C   B  60       2.065 149.250 265.950  1.00  0.00           O
ATOM   2824  C2*   C   B  60       0.138 149.171 264.526  1.00  0.00           C
```

| | | | | | | | | | | | |
|---|---|---|---|---|---|---|---|---|---|---|---|
| ATOM | 2825 | O2* | C | B | 60 | 1.022 | 149.315 | 263.452 | 1.00 | 0.00 | O |
| ATOM | 2826 | C1* | C | B | 60 | -0.049 | 147.687 | 264.827 | 1.00 | 0.00 | C |
| ATOM | 2827 | N1 | C | B | 60 | -1.014 | 147.065 | 263.914 | 1.00 | 0.00 | N |
| ATOM | 2828 | C2 | C | B | 60 | -0.656 | 145.868 | 263.277 | 1.00 | 0.00 | C |
| ATOM | 2829 | O2 | C | B | 60 | 0.468 | 145.351 | 263.531 | 1.00 | 0.00 | O |
| ATOM | 2830 | N3 | C | B | 60 | -1.515 | 145.310 | 262.404 | 1.00 | 0.00 | N |
| ATOM | 2831 | C4 | C | B | 60 | -2.695 | 145.899 | 262.136 | 1.00 | 0.00 | C |
| ATOM | 2832 | N4 | C | B | 60 | -3.472 | 145.331 | 261.225 | 1.00 | 0.00 | N |
| ATOM | 2833 | C5 | C | B | 60 | -3.102 | 147.098 | 262.780 | 1.00 | 0.00 | C |
| ATOM | 2834 | C6 | C | B | 60 | -2.233 | 147.648 | 263.662 | 1.00 | 0.00 | C |
| ATOM | 2835 | P | C | B | 61 | 3.041 | 150.110 | 266.867 | 1.00 | 0.00 | P |
| ATOM | 2836 | O1P | C | B | 61 | 4.298 | 149.349 | 266.866 | 1.00 | 0.00 | O |
| ATOM | 2837 | O2P | C | B | 61 | 2.376 | 150.463 | 268.141 | 1.00 | 0.00 | O |
| ATOM | 2838 | O5* | C | B | 61 | 3.207 | 151.499 | 266.093 | 1.00 | 0.00 | O |
| ATOM | 2839 | C5* | C | B | 61 | 4.138 | 151.630 | 265.016 | 1.00 | 0.00 | C |
| ATOM | 2840 | C4* | C | B | 61 | 4.086 | 153.039 | 264.445 | 1.00 | 0.00 | C |
| ATOM | 2841 | O4* | C | B | 61 | 2.982 | 153.134 | 263.509 | 1.00 | 0.00 | O |
| ATOM | 2842 | C3* | C | B | 61 | 3.798 | 154.130 | 265.459 | 1.00 | 0.00 | C |
| ATOM | 2843 | O3* | C | B | 61 | 5.006 | 154.517 | 266.132 | 1.00 | 0.00 | O |
| ATOM | 2844 | C2* | C | B | 61 | 3.232 | 155.228 | 264.571 | 1.00 | 0.00 | C |
| ATOM | 2845 | O2* | C | B | 61 | 4.259 | 155.874 | 263.851 | 1.00 | 0.00 | O |
| ATOM | 2846 | C1* | C | B | 61 | 2.400 | 154.427 | 263.571 | 1.00 | 0.00 | C |
| ATOM | 2847 | N1 | C | B | 61 | 0.967 | 154.273 | 263.900 | 1.00 | 0.00 | N |
| ATOM | 2848 | C2 | C | B | 61 | 0.132 | 155.377 | 263.812 | 1.00 | 0.00 | C |
| ATOM | 2849 | O2 | C | B | 61 | 0.616 | 156.467 | 263.486 | 1.00 | 0.00 | O |
| ATOM | 2850 | N3 | C | B | 61 | -1.185 | 155.237 | 264.091 | 1.00 | 0.00 | N |
| ATOM | 2851 | C4 | C | B | 61 | -1.659 | 154.043 | 264.465 | 1.00 | 0.00 | C |
| ATOM | 2852 | N4 | C | B | 61 | -2.953 | 153.936 | 264.741 | 1.00 | 0.00 | N |
| ATOM | 2853 | C5 | C | B | 61 | -0.822 | 152.903 | 264.571 | 1.00 | 0.00 | C |
| ATOM | 2854 | C6 | C | B | 61 | 0.473 | 153.062 | 264.278 | 1.00 | 0.00 | C |
| ATOM | 2855 | P | A | B | 62 | 4.930 | 155.222 | 267.582 | 1.00 | 0.00 | P |
| ATOM | 2856 | O1P | A | B | 62 | 6.289 | 155.390 | 268.106 | 1.00 | 0.00 | O |
| ATOM | 2857 | O2P | A | B | 62 | 3.927 | 154.488 | 268.401 | 1.00 | 0.00 | O |
| ATOM | 2858 | O5* | A | B | 62 | 4.318 | 156.664 | 267.270 | 1.00 | 0.00 | O |
| ATOM | 2859 | C5* | A | B | 62 | 5.095 | 157.665 | 266.635 | 1.00 | 0.00 | C |
| ATOM | 2860 | C4* | A | B | 62 | 4.337 | 158.964 | 266.620 | 1.00 | 0.00 | C |
| ATOM | 2861 | O4* | A | B | 62 | 3.115 | 158.810 | 265.830 | 1.00 | 0.00 | O |
| ATOM | 2862 | C3* | A | B | 62 | 3.806 | 159.383 | 267.975 | 1.00 | 0.00 | C |
| ATOM | 2863 | O3* | A | B | 62 | 4.844 | 160.028 | 268.667 | 1.00 | 0.00 | O |
| ATOM | 2864 | C2* | A | B | 62 | 2.691 | 160.335 | 267.568 | 1.00 | 0.00 | C |
| ATOM | 2865 | O2* | A | B | 62 | 3.173 | 161.520 | 266.977 | 1.00 | 0.00 | O |
| ATOM | 2866 | C1* | A | B | 62 | 2.064 | 159.551 | 266.433 | 1.00 | 0.00 | C |
| ATOM | 2867 | N9 | A | B | 62 | 1.013 | 158.618 | 266.827 | 1.00 | 0.00 | N |
| ATOM | 2868 | C8 | A | B | 62 | 1.088 | 157.253 | 266.902 | 1.00 | 0.00 | C |
| ATOM | 2869 | N7 | A | B | 62 | -0.062 | 156.669 | 267.147 | 1.00 | 0.00 | N |
| ATOM | 2870 | C5 | A | B | 62 | -0.951 | 157.726 | 267.279 | 1.00 | 0.00 | C |
| ATOM | 2871 | C6 | A | B | 62 | -2.336 | 157.773 | 267.491 | 1.00 | 0.00 | C |
| ATOM | 2872 | N6 | A | B | 62 | -3.111 | 156.683 | 267.659 | 1.00 | 0.00 | N |
| ATOM | 2873 | N1 | A | B | 62 | -2.918 | 158.992 | 267.525 | 1.00 | 0.00 | N |
| ATOM | 2874 | C2 | A | B | 62 | -2.148 | 160.080 | 267.361 | 1.00 | 0.00 | C |
| ATOM | 2875 | N3 | A | B | 62 | -0.843 | 160.163 | 267.153 | 1.00 | 0.00 | N |
| ATOM | 2876 | C4 | A | B | 62 | -0.295 | 158.936 | 267.116 | 1.00 | 0.00 | C |
| ATOM | 2877 | P | C | B | 63 | 4.816 | 160.114 | 270.275 | 1.00 | 0.00 | P |
| ATOM | 2878 | O1P | C | B | 63 | 6.071 | 160.817 | 270.564 | 1.00 | 0.00 | O |
| ATOM | 2879 | O2P | C | B | 63 | 4.550 | 158.803 | 270.899 | 1.00 | 0.00 | O |
| ATOM | 2880 | O5* | C | B | 63 | 3.598 | 161.067 | 270.610 | 1.00 | 0.00 | O |
| ATOM | 2881 | C5* | C | B | 63 | 3.775 | 162.469 | 270.541 | 1.00 | 0.00 | C |
| ATOM | 2882 | C4* | C | B | 63 | 2.472 | 163.165 | 270.787 | 1.00 | 0.00 | C |
| ATOM | 2883 | O4* | C | B | 63 | 1.481 | 162.598 | 269.885 | 1.00 | 0.00 | O |
| ATOM | 2884 | C3* | C | B | 63 | 1.862 | 162.940 | 272.157 | 1.00 | 0.00 | C |
| ATOM | 2885 | O3* | C | B | 63 | 2.423 | 163.803 | 273.151 | 1.00 | 0.00 | O |
| ATOM | 2886 | C2* | C | B | 63 | 0.412 | 163.283 | 271.872 | 1.00 | 0.00 | C |
| ATOM | 2887 | O2* | C | B | 63 | 0.214 | 164.684 | 271.718 | 1.00 | 0.00 | O |
| ATOM | 2888 | C1* | C | B | 63 | 0.211 | 162.596 | 270.520 | 1.00 | 0.00 | C |
| ATOM | 2889 | N1 | C | B | 63 | -0.291 | 161.204 | 270.600 | 1.00 | 0.00 | N |
| ATOM | 2890 | C2 | C | B | 63 | -1.654 | 160.996 | 270.727 | 1.00 | 0.00 | C |
| ATOM | 2891 | O2 | C | B | 63 | -2.399 | 161.999 | 270.784 | 1.00 | 0.00 | O |
| ATOM | 2892 | N3 | C | B | 63 | -2.136 | 159.710 | 270.798 | 1.00 | 0.00 | N |
| ATOM | 2893 | C4 | C | B | 63 | -1.272 | 158.680 | 270.751 | 1.00 | 0.00 | C |
| ATOM | 2894 | N4 | C | B | 63 | -1.742 | 157.444 | 270.814 | 1.00 | 0.00 | N |
| ATOM | 2895 | C5 | C | B | 63 | 0.127 | 158.881 | 270.625 | 1.00 | 0.00 | C |
| ATOM | 2896 | C6 | C | B | 63 | 0.569 | 160.143 | 270.548 | 1.00 | 0.00 | C |
| ATOM | 2897 | P | A | B | 64 | 2.494 | 163.316 | 274.693 | 1.00 | 0.00 | P |
| ATOM | 2898 | O1P | A | B | 64 | 3.285 | 164.298 | 275.469 | 1.00 | 0.00 | O |
| ATOM | 2899 | O2P | A | B | 64 | 2.905 | 161.894 | 274.699 | 1.00 | 0.00 | O |
| ATOM | 2900 | O5* | A | B | 64 | 0.997 | 163.470 | 275.171 | 1.00 | 0.00 | O |
| ATOM | 2901 | C5* | A | B | 64 | 0.363 | 164.729 | 275.062 | 1.00 | 0.00 | C |
| ATOM | 2902 | C4* | A | B | 64 | -1.073 | 164.629 | 275.481 | 1.00 | 0.00 | C |
| ATOM | 2903 | O4* | A | B | 64 | -1.848 | 164.044 | 274.400 | 1.00 | 0.00 | O |
| ATOM | 2904 | C3* | A | B | 64 | -1.370 | 163.718 | 276.659 | 1.00 | 0.00 | C |
| ATOM | 2905 | O3* | A | B | 64 | -1.014 | 164.331 | 277.908 | 1.00 | 0.00 | O |
| ATOM | 2906 | C2* | A | B | 64 | -2.866 | 163.506 | 276.462 | 1.00 | 0.00 | C |
| ATOM | 2907 | O2* | A | B | 64 | -3.660 | 164.635 | 276.749 | 1.00 | 0.00 | O |
| ATOM | 2908 | C1* | A | B | 64 | -2.918 | 163.284 | 274.949 | 1.00 | 0.00 | C |
| ATOM | 2909 | N9 | A | B | 64 | -2.671 | 161.879 | 274.661 | 1.00 | 0.00 | N |
| ATOM | 2910 | C8 | A | B | 64 | -1.492 | 161.248 | 274.369 | 1.00 | 0.00 | C |
| ATOM | 2911 | N7 | A | B | 64 | -1.612 | 159.957 | 274.231 | 1.00 | 0.00 | N |

```
ATOM  2912  C5   A B 64    -2.963 159.732 274.435  1.00  0.00           C
ATOM  2913  C6   A B 64    -3.733 158.574 274.398  1.00  0.00           C
ATOM  2914  N6   A B 64    -3.224 157.368 274.158  1.00  0.00           N
ATOM  2915  N1   A B 64    -5.058 158.694 274.617  1.00  0.00           N
ATOM  2916  C2   A B 64    -5.560 159.909 274.849  1.00  0.00           C
ATOM  2917  N3   A B 64    -4.935 161.073 274.906  1.00  0.00           N
ATOM  2918  C4   A B 64    -3.623 160.905 274.690  1.00  0.00           C
ATOM  2919  P    G B 65    -0.457 163.415 279.122  1.00  0.00           P
ATOM  2920  O1P  G B 65     0.051 164.294 280.207  1.00  0.00           O
ATOM  2921  O2P  G B 65     0.423 162.356 278.581  1.00  0.00           O
ATOM  2922  O5*  G B 65    -1.768 162.704 279.672  1.00  0.00           O
ATOM  2923  C5*  G B 65    -2.971 163.431 279.801  1.00  0.00           C
ATOM  2924  C4*  G B 65    -4.159 162.500 279.804  1.00  0.00           C
ATOM  2925  O4*  G B 65    -4.338 161.924 278.489  1.00  0.00           O
ATOM  2926  C3*  G B 65    -4.132 161.273 280.706  1.00  0.00           C
ATOM  2927  O3*  G B 65    -4.452 161.612 282.047  1.00  0.00           O
ATOM  2928  C2*  G B 65    -5.283 160.487 280.112  1.00  0.00           C
ATOM  2929  O2*  G B 65    -6.524 161.053 280.437  1.00  0.00           O
ATOM  2930  C1*  G B 65    -5.040 160.698 278.614  1.00  0.00           C
ATOM  2931  N9   G B 65    -4.188 159.622 278.122  1.00  0.00           N
ATOM  2932  C8   G B 65    -2.869 159.686 277.775  1.00  0.00           C
ATOM  2933  N7   G B 65    -2.385 158.539 277.400  1.00  0.00           N
ATOM  2934  C5   G B 65    -3.459 157.668 277.507  1.00  0.00           C
ATOM  2935  C6   G B 65    -3.559 156.296 277.191  1.00  0.00           C
ATOM  2936  O6   G B 65    -2.670 155.534 276.767  1.00  0.00           O
ATOM  2937  N1   G B 65    -4.848 155.817 277.406  1.00  0.00           N
ATOM  2938  C2   G B 65    -5.908 156.578 277.862  1.00  0.00           C
ATOM  2939  N2   G B 65    -7.082 155.958 278.003  1.00  0.00           N
ATOM  2940  N3   G B 65    -5.821 157.853 278.154  1.00  0.00           N
ATOM  2941  C4   G B 65    -4.575 158.328 277.951  1.00  0.00           C
ATOM  2942  P    A B 66    -3.920 160.687 283.259  1.00  0.00           P
ATOM  2943  O1P  A B 66    -4.200 161.387 284.535  1.00  0.00           O
ATOM  2944  O2P  A B 66    -2.535 160.295 282.936  1.00  0.00           O
ATOM  2945  O5*  A B 66    -4.844 159.395 283.186  1.00  0.00           O
ATOM  2946  C5*  A B 66    -6.231 159.491 283.447  1.00  0.00           C
ATOM  2947  C4*  A B 66    -6.894 158.168 283.202  1.00  0.00           C
ATOM  2948  O4*  A B 66    -6.606 157.735 281.851  1.00  0.00           O
ATOM  2949  C3*  A B 66    -6.354 157.033 284.037  1.00  0.00           C
ATOM  2950  O3*  A B 66    -6.911 157.071 285.339  1.00  0.00           O
ATOM  2951  C2*  A B 66    -6.816 155.831 283.228  1.00  0.00           C
ATOM  2952  O2*  A B 66    -8.197 155.557 283.358  1.00  0.00           O
ATOM  2953  C1*  A B 66    -6.551 156.318 281.805  1.00  0.00           C
ATOM  2954  N9   A B 66    -5.247 155.935 281.254  1.00  0.00           N
ATOM  2955  C8   A B 66    -4.164 156.758 281.089  1.00  0.00           C
ATOM  2956  N7   A B 66    -3.123 156.166 280.546  1.00  0.00           N
ATOM  2957  C5   A B 66    -3.549 154.869 280.338  1.00  0.00           C
ATOM  2958  C6   A B 66    -2.904 153.740 279.796  1.00  0.00           C
ATOM  2959  N6   A B 66    -1.662 153.756 279.359  1.00  0.00           N
ATOM  2960  N1   A B 66    -3.590 152.585 279.741  1.00  0.00           N
ATOM  2961  C2   A B 66    -4.843 152.564 280.227  1.00  0.00           C
ATOM  2962  N3   A B 66    -5.557 153.557 280.766  1.00  0.00           N
ATOM  2963  C4   A B 66    -4.850 154.699 280.786  1.00  0.00           C
ATOM  2964  P    A B 67    -6.046 156.559 286.594  1.00  0.00           P
ATOM  2965  O1P  A B 67    -6.831 156.848 287.817  1.00  0.00           O
ATOM  2966  O2P  A B 67    -4.646 157.053 286.485  1.00  0.00           O
ATOM  2967  O5*  A B 67    -6.077 154.995 286.424  1.00  0.00           O
ATOM  2968  C5*  A B 67    -7.310 154.301 286.490  1.00  0.00           C
ATOM  2969  C4*  A B 67    -7.099 152.868 286.105  1.00  0.00           C
ATOM  2970  O4*  A B 67    -6.684 152.844 284.717  1.00  0.00           O
ATOM  2971  C3*  A B 67    -5.930 152.222 286.818  1.00  0.00           C
ATOM  2972  O3*  A B 67    -6.361 151.649 288.033  1.00  0.00           O
ATOM  2973  C2*  A B 67    -5.586 151.099 285.862  1.00  0.00           C
ATOM  2974  O2*  A B 67    -6.557 150.071 285.964  1.00  0.00           O
ATOM  2975  C1*  A B 67    -5.717 151.821 284.524  1.00  0.00           C
ATOM  2976  N9   A B 67    -4.450 152.417 284.076  1.00  0.00           N
ATOM  2977  C8   A B 67    -4.000 153.694 284.264  1.00  0.00           C
ATOM  2978  N7   A B 67    -2.816 153.923 283.723  1.00  0.00           N
ATOM  2979  C5   A B 67    -2.467 152.711 283.154  1.00  0.00           C
ATOM  2980  C6   A B 67    -1.305 152.280 282.448  1.00  0.00           C
ATOM  2981  N6   A B 67    -0.271 153.061 282.166  1.00  0.00           N
ATOM  2982  N1   A B 67    -1.253 150.997 282.044  1.00  0.00           N
ATOM  2983  C2   A B 67    -2.291 150.201 282.335  1.00  0.00           C
ATOM  2984  N3   A B 67    -3.432 150.484 282.982  1.00  0.00           N
ATOM  2985  C4   A B 67    -3.458 151.772 283.364  1.00  0.00           C
ATOM  2986  P    U B 68    -5.296 151.375 289.204  1.00  0.00           P
ATOM  2987  O1P  U B 68    -6.118 151.012 290.381  1.00  0.00           O
ATOM  2988  O2P  U B 68    -4.278 152.468 289.297  1.00  0.00           O
ATOM  2989  O5*  U B 68    -4.516 150.065 288.745  1.00  0.00           O
ATOM  2990  C5*  U B 68    -5.195 148.852 288.547  1.00  0.00           C
ATOM  2991  C4*  U B 68    -4.244 147.846 287.970  1.00  0.00           C
ATOM  2992  O4*  U B 68    -3.891 148.231 286.606  1.00  0.00           O
ATOM  2993  C3*  U B 68    -2.896 147.780 288.669  1.00  0.00           C
ATOM  2994  O3*  U B 68    -2.999 146.969 289.825  1.00  0.00           O
ATOM  2995  C2*  U B 68    -2.050 147.108 287.598  1.00  0.00           C
ATOM  2996  O2*  U B 68    -2.368 145.729 287.478  1.00  0.00           O
ATOM  2997  C1*  U B 68    -2.552 147.841 286.347  1.00  0.00           C
ATOM  2998  N1   U B 68    -1.746 149.036 286.060  1.00  0.00           N
```

```
ATOM   2999  C2    U B  68      -0.541 148.804 285.413  1.00  0.00           C
ATOM   3000  O2    U B  68      -0.169 147.669 285.099  1.00  0.00           O
ATOM   3001  N3    U B  68       0.209 149.921 285.153  1.00  0.00           N
ATOM   3002  C4    U B  68      -0.107 151.228 285.464  1.00  0.00           C
ATOM   3003  O4    U B  68       0.695 152.132 285.170  1.00  0.00           O
ATOM   3004  C5    U B  68      -1.373 151.393 286.147  1.00  0.00           C
ATOM   3005  C6    U B  68      -2.130 150.310 286.406  1.00  0.00           C
ATOM   3006  P     U B  69      -1.980 147.183 291.029  1.00  0.00           P
ATOM   3007  O1P   U B  69      -2.304 146.207 292.108  1.00  0.00           O
ATOM   3008  O2P   U B  69      -1.972 148.626 291.306  1.00  0.00           O
ATOM   3009  O5*   U B  69      -0.543 146.809 290.448  1.00  0.00           O
ATOM   3010  C5*   U B  69      -0.302 145.519 289.932  1.00  0.00           C
ATOM   3011  C4*   U B  69       1.051 145.474 289.255  1.00  0.00           C
ATOM   3012  O4*   U B  69       1.028 146.250 288.020  1.00  0.00           O
ATOM   3013  C3*   U B  69       2.187 146.084 290.054  1.00  0.00           C
ATOM   3014  O3*   U B  69       2.654 145.116 290.992  1.00  0.00           O
ATOM   3015  C2*   U B  69       3.209 146.377 288.961  1.00  0.00           C
ATOM   3016  O2*   U B  69       3.957 145.258 288.519  1.00  0.00           O
ATOM   3017  C1*   U B  69       2.294 146.831 287.826  1.00  0.00           C
ATOM   3018  N1    U B  69       2.152 148.287 287.824  1.00  0.00           N
ATOM   3019  C2    U B  69       3.199 149.006 287.283  1.00  0.00           C
ATOM   3020  O2    U B  69       4.193 148.462 286.782  1.00  0.00           O
ATOM   3021  N3    U B  69       3.046 150.368 287.344  1.00  0.00           N
ATOM   3022  C4    U B  69       1.971 151.055 287.861  1.00  0.00           C
ATOM   3023  O4    U B  69       1.977 152.282 287.850  1.00  0.00           O
ATOM   3024  C5    U B  69       0.925 150.232 288.384  1.00  0.00           C
ATOM   3025  C6    U B  69       1.050 148.911 288.346  1.00  0.00           C
ATOM   3026  P     C B  70       3.389 145.586 292.349  1.00  0.00           P
ATOM   3027  O1P   C B  70       3.400 144.382 293.251  1.00  0.00           O
ATOM   3028  O2P   C B  70       2.761 146.850 292.826  1.00  0.00           O
ATOM   3029  O5*   C B  70       4.858 145.934 291.849  1.00  0.00           O
ATOM   3030  C5*   C B  70       5.736 144.891 291.436  1.00  0.00           C
ATOM   3031  C4*   C B  70       6.950 145.468 290.746  1.00  0.00           C
ATOM   3032  O4*   C B  70       6.566 146.179 289.534  1.00  0.00           O
ATOM   3033  C3*   C B  70       7.746 146.504 291.510  1.00  0.00           C
ATOM   3034  O3*   C B  70       8.554 145.866 292.486  1.00  0.00           O
ATOM   3035  C2*   C B  70       8.575 147.092 290.373  1.00  0.00           C
ATOM   3036  O2*   C B  70       9.612 146.228 289.920  1.00  0.00           O
ATOM   3037  C1*   C B  70       7.507 147.204 289.287  1.00  0.00           C
ATOM   3038  N1    C B  70       6.799 148.489 289.338  1.00  0.00           N
ATOM   3039  C2    C B  70       7.390 149.573 288.719  1.00  0.00           C
ATOM   3040  O2    C B  70       8.475 149.397 288.149  1.00  0.00           O
ATOM   3041  N3    C B  70       6.780 150.783 288.751  1.00  0.00           N
ATOM   3042  C4    C B  70       5.604 150.918 289.378  1.00  0.00           C
ATOM   3043  N4    C B  70       5.025 152.140 289.382  1.00  0.00           N
ATOM   3044  C5    C B  70       4.966 149.810 290.023  1.00  0.00           C
ATOM   3045  C6    C B  70       5.594 148.621 289.977  1.00  0.00           C
ATOM   3046  P     G B  71       9.048 146.679 293.792  1.00  0.00           P
ATOM   3047  O1P   G B  71       9.709 145.655 294.644  1.00  0.00           O
ATOM   3048  O2P   G B  71       7.923 147.465 294.344  1.00  0.00           O
ATOM   3049  O5*   G B  71      10.103 147.750 293.230  1.00  0.00           O
ATOM   3050  C5*   G B  71      11.438 147.370 292.897  1.00  0.00           C
ATOM   3051  C4*   G B  71      12.160 148.492 292.168  1.00  0.00           C
ATOM   3052  O4*   G B  71      11.435 148.868 290.963  1.00  0.00           O
ATOM   3053  C3*   G B  71      12.368 149.820 292.888  1.00  0.00           C
ATOM   3054  O3*   G B  71      13.492 149.812 293.768  1.00  0.00           O
ATOM   3055  C2*   G B  71      12.665 150.733 291.713  1.00  0.00           C
ATOM   3056  O2*   G B  71      13.948 150.515 291.181  1.00  0.00           O
ATOM   3057  C1*   G B  71      11.610 150.260 290.716  1.00  0.00           C
ATOM   3058  N9    G B  71      10.348 150.950 290.973  1.00  0.00           N
ATOM   3059  C8    G B  71       9.269 150.482 291.682  1.00  0.00           C
ATOM   3060  N7    G B  71       8.294 151.349 291.759  1.00  0.00           N
ATOM   3061  C5    G B  71       8.755 152.449 291.047  1.00  0.00           C
ATOM   3062  C6    G B  71       8.135 153.700 290.777  1.00  0.00           C
ATOM   3063  O6    G B  71       7.009 154.110 291.130  1.00  0.00           O
ATOM   3064  N1    G B  71       8.965 154.523 290.023  1.00  0.00           N
ATOM   3065  C2    G B  71      10.224 154.190 289.593  1.00  0.00           C
ATOM   3066  N2    G B  71      10.874 155.122 288.880  1.00  0.00           N
ATOM   3067  N3    G B  71      10.807 153.038 289.841  1.00  0.00           N
ATOM   3068  C4    G B  71      10.023 152.220 290.563  1.00  0.00           C
ATOM   3069  P     C B  72      13.664 151.000 294.840  1.00  0.00           P
ATOM   3070  O1P   C B  72      15.032 150.931 295.402  1.00  0.00           O
ATOM   3071  O2P   C B  72      12.493 150.972 295.756  1.00  0.00           O
ATOM   3072  O5*   C B  72      13.599 152.326 293.973  1.00  0.00           O
ATOM   3073  C5*   C B  72      14.786 152.899 293.465  1.00  0.00           C
ATOM   3074  C4*   C B  72      14.545 154.334 293.106  1.00  0.00           C
ATOM   3075  O4*   C B  72      13.389 154.390 292.236  1.00  0.00           O
ATOM   3076  C3*   C B  72      14.131 155.235 294.253  1.00  0.00           C
ATOM   3077  O3*   C B  72      15.246 155.663 295.017  1.00  0.00           O
ATOM   3078  C2*   C B  72      13.486 156.387 293.500  1.00  0.00           C
ATOM   3079  O2*   C B  72      14.394 157.269 292.867  1.00  0.00           O
ATOM   3080  C1*   C B  72      12.715 155.619 292.433  1.00  0.00           C
ATOM   3081  N1    C B  72      11.350 155.336 292.870  1.00  0.00           N
ATOM   3082  C2    C B  72      10.400 156.335 292.719  1.00  0.00           C
ATOM   3083  O2    C B  72      10.763 157.430 292.241  1.00  0.00           O
ATOM   3084  N3    C B  72       9.121 156.100 293.092  1.00  0.00           N
ATOM   3085  C4    C B  72       8.791 154.912 293.608  1.00  0.00           C
```

| | | | | | | | | | | |
|---|---|---|---|---|---|---|---|---|---|---|
| ATOM | 3086 | N4 | C | B | 72 | 7.518 | 154.712 | 293.956 | 1.00 | 0.00 | N |
| ATOM | 3087 | C5 | C | B | 72 | 9.754 | 153.872 | 293.786 | 1.00 | 0.00 | C |
| ATOM | 3088 | C6 | C | B | 72 | 11.008 | 154.126 | 293.406 | 1.00 | 0.00 | C |
| ATOM | 3089 | P | A | B | 73 | 15.031 | 156.153 | 296.533 | 1.00 | 0.00 | P |
| ATOM | 3090 | O1P | A | B | 73 | 16.362 | 156.622 | 296.994 | 1.00 | 0.00 | O |
| ATOM | 3091 | O2P | A | B | 73 | 14.342 | 155.074 | 297.286 | 1.00 | 0.00 | O |
| ATOM | 3092 | O5* | A | B | 73 | 14.080 | 157.424 | 296.405 | 1.00 | 0.00 | O |
| ATOM | 3093 | C5* | A | B | 73 | 14.592 | 158.639 | 295.877 | 1.00 | 0.00 | C |
| ATOM | 3094 | C4* | A | B | 73 | 13.509 | 159.678 | 295.791 | 1.00 | 0.00 | C |
| ATOM | 3095 | O4* | A | B | 73 | 12.470 | 159.211 | 294.894 | 1.00 | 0.00 | O |
| ATOM | 3096 | C3* | A | B | 73 | 12.754 | 159.952 | 297.077 | 1.00 | 0.00 | C |
| ATOM | 3097 | O3* | A | B | 73 | 13.468 | 160.845 | 297.916 | 1.00 | 0.00 | O |
| ATOM | 3098 | C2* | A | B | 73 | 11.488 | 160.600 | 296.543 | 1.00 | 0.00 | C |
| ATOM | 3099 | O2* | A | B | 73 | 11.699 | 161.945 | 296.174 | 1.00 | 0.00 | O |
| ATOM | 3100 | C1* | A | B | 73 | 11.215 | 159.724 | 295.316 | 1.00 | 0.00 | C |
| ATOM | 3101 | N9 | A | B | 73 | 10.354 | 158.586 | 295.644 | 1.00 | 0.00 | N |
| ATOM | 3102 | C8 | A | B | 73 | 10.733 | 157.291 | 295.873 | 1.00 | 0.00 | C |
| ATOM | 3103 | N7 | A | B | 73 | 9.736 | 156.496 | 296.178 | 1.00 | 0.00 | N |
| ATOM | 3104 | C5 | A | B | 73 | 8.624 | 157.325 | 296.138 | 1.00 | 0.00 | C |
| ATOM | 3105 | C6 | A | B | 73 | 7.257 | 157.085 | 296.367 | 1.00 | 0.00 | C |
| ATOM | 3106 | N6 | A | B | 73 | 6.767 | 155.892 | 296.705 | 1.00 | 0.00 | N |
| ATOM | 3107 | N1 | A | B | 73 | 6.404 | 158.127 | 296.235 | 1.00 | 0.00 | N |
| ATOM | 3108 | C2 | A | B | 73 | 6.905 | 159.325 | 295.899 | 1.00 | 0.00 | C |
| ATOM | 3109 | N3 | A | B | 73 | 8.169 | 159.675 | 295.662 | 1.00 | 0.00 | N |
| ATOM | 3110 | C4 | A | B | 73 | 8.989 | 158.614 | 295.801 | 1.00 | 0.00 | C |
| ATOM | 3111 | P | C | B | 74 | 12.932 | 160.489 | 299.470 | 1.00 | 0.00 | P |
| ATOM | 3112 | O1P | C | B | 74 | 14.137 | 160.095 | 300.247 | 1.00 | 0.00 | O |
| ATOM | 3113 | O2P | C | B | 74 | 11.760 | 159.568 | 299.417 | 1.00 | 0.00 | O |
| ATOM | 3114 | O5* | C | B | 74 | 12.447 | 161.919 | 299.985 | 1.00 | 0.00 | O |
| ATOM | 3115 | C5* | C | B | 74 | 12.754 | 162.361 | 301.307 | 1.00 | 0.00 | C |
| ATOM | 3116 | C4* | C | B | 74 | 12.502 | 163.846 | 301.439 | 1.00 | 0.00 | C |
| ATOM | 3117 | O4* | C | B | 74 | 11.311 | 164.069 | 302.240 | 1.00 | 0.00 | O |
| ATOM | 3118 | C3* | C | B | 74 | 13.580 | 164.652 | 302.153 | 1.00 | 0.00 | C |
| ATOM | 3119 | O3* | C | B | 74 | 14.640 | 164.995 | 301.265 | 1.00 | 0.00 | O |
| ATOM | 3120 | C2* | C | B | 74 | 12.801 | 165.880 | 302.607 | 1.00 | 0.00 | C |
| ATOM | 3121 | O2* | C | B | 74 | 12.562 | 166.831 | 301.591 | 1.00 | 0.00 | O |
| ATOM | 3122 | C1* | C | B | 74 | 11.475 | 165.245 | 303.015 | 1.00 | 0.00 | C |
| ATOM | 3123 | N1 | C | B | 74 | 11.475 | 164.872 | 304.432 | 1.00 | 0.00 | N |
| ATOM | 3124 | C2 | C | B | 74 | 11.314 | 165.880 | 305.377 | 1.00 | 0.00 | C |
| ATOM | 3125 | O2 | C | B | 74 | 11.202 | 167.056 | 304.984 | 1.00 | 0.00 | O |
| ATOM | 3126 | N3 | C | B | 74 | 11.284 | 165.556 | 306.688 | 1.00 | 0.00 | N |
| ATOM | 3127 | C4 | C | B | 74 | 11.410 | 164.282 | 307.064 | 1.00 | 0.00 | C |
| ATOM | 3128 | N4 | C | B | 74 | 11.361 | 164.010 | 308.374 | 1.00 | 0.00 | N |
| ATOM | 3129 | C5 | C | B | 74 | 11.591 | 163.232 | 306.118 | 1.00 | 0.00 | C |
| ATOM | 3130 | C6 | C | B | 74 | 11.617 | 163.569 | 304.823 | 1.00 | 0.00 | C |
| ATOM | 3131 | P | C | B | 75 | 16.158 | 165.005 | 301.797 | 1.00 | 0.00 | P |
| ATOM | 3132 | O1P | C | B | 75 | 16.993 | 165.722 | 300.804 | 1.00 | 0.00 | O |
| ATOM | 3133 | O2P | C | B | 75 | 16.518 | 163.630 | 302.214 | 1.00 | 0.00 | O |
| ATOM | 3134 | O5* | C | B | 75 | 16.114 | 165.901 | 303.104 | 1.00 | 0.00 | O |
| ATOM | 3135 | C5* | C | B | 75 | 16.110 | 167.314 | 303.012 | 1.00 | 0.00 | C |
| ATOM | 3136 | C4* | C | B | 75 | 16.191 | 167.896 | 304.388 | 1.00 | 0.00 | C |
| ATOM | 3137 | O4* | C | B | 75 | 15.066 | 167.372 | 305.139 | 1.00 | 0.00 | O |
| ATOM | 3138 | C3* | C | B | 75 | 17.416 | 167.444 | 305.166 | 1.00 | 0.00 | C |
| ATOM | 3139 | O3* | C | B | 75 | 18.485 | 168.357 | 304.977 | 1.00 | 0.00 | O |
| ATOM | 3140 | C2* | C | B | 75 | 16.932 | 167.507 | 306.606 | 1.00 | 0.00 | C |
| ATOM | 3141 | O2* | C | B | 75 | 17.057 | 168.811 | 307.142 | 1.00 | 0.00 | O |
| ATOM | 3142 | C1* | C | B | 75 | 15.464 | 167.095 | 306.465 | 1.00 | 0.00 | C |
| ATOM | 3143 | N1 | C | B | 75 | 15.230 | 165.669 | 306.727 | 1.00 | 0.00 | N |
| ATOM | 3144 | C2 | C | B | 75 | 15.146 | 165.239 | 308.049 | 1.00 | 0.00 | C |
| ATOM | 3145 | O2 | C | B | 75 | 15.259 | 166.072 | 308.960 | 1.00 | 0.00 | O |
| ATOM | 3146 | N3 | C | B | 75 | 14.950 | 163.926 | 308.308 | 1.00 | 0.00 | N |
| ATOM | 3147 | C4 | C | B | 75 | 14.837 | 163.061 | 307.301 | 1.00 | 0.00 | C |
| ATOM | 3148 | N4 | C | B | 75 | 14.646 | 161.771 | 307.601 | 1.00 | 0.00 | N |
| ATOM | 3149 | C5 | C | B | 75 | 14.912 | 163.476 | 305.939 | 1.00 | 0.00 | C |
| ATOM | 3150 | C6 | C | B | 75 | 15.106 | 164.778 | 305.700 | 1.00 | 0.00 | C |
| ATOM | 3151 | P | A | B | 76 | 19.470 | 168.468 | 304.158 | 1.00 | 0.00 | P |
| ATOM | 3152 | O1P | A | B | 76 | 18.807 | 169.092 | 302.983 | 1.00 | 0.00 | O |
| ATOM | 3153 | O2P | A | B | 76 | 20.651 | 167.598 | 303.958 | 1.00 | 0.00 | O |
| ATOM | 3154 | O5* | A | B | 76 | 20.168 | 169.745 | 304.883 | 1.00 | 0.00 | O |
| ATOM | 3155 | C5* | A | B | 76 | 21.429 | 169.301 | 305.377 | 1.00 | 0.00 | C |
| ATOM | 3156 | C4* | A | B | 76 | 21.339 | 169.021 | 306.859 | 1.00 | 0.00 | C |
| ATOM | 3157 | O4* | A | B | 76 | 20.053 | 168.404 | 307.141 | 1.00 | 0.00 | O |
| ATOM | 3158 | C3* | A | B | 76 | 22.335 | 168.005 | 307.387 | 1.00 | 0.00 | C |
| ATOM | 3159 | O3* | A | B | 76 | 23.578 | 168.628 | 307.689 | 1.00 | 0.00 | O |
| ATOM | 3160 | C2* | A | B | 76 | 21.649 | 167.504 | 308.649 | 1.00 | 0.00 | C |
| ATOM | 3161 | O2* | A | B | 76 | 21.810 | 168.370 | 309.755 | 1.00 | 0.00 | O |
| ATOM | 3162 | C1* | A | B | 76 | 20.181 | 167.477 | 308.212 | 1.00 | 0.00 | C |
| ATOM | 3163 | N9 | A | B | 76 | 19.741 | 166.169 | 307.738 | 1.00 | 0.00 | N |
| ATOM | 3164 | C8 | A | B | 76 | 19.901 | 165.636 | 306.481 | 1.00 | 0.00 | C |
| ATOM | 3165 | N7 | A | B | 76 | 19.363 | 164.450 | 306.337 | 1.00 | 0.00 | N |
| ATOM | 3166 | C5 | A | B | 76 | 18.814 | 164.181 | 307.586 | 1.00 | 0.00 | C |
| ATOM | 3167 | C6 | A | B | 76 | 18.092 | 163.083 | 308.080 | 1.00 | 0.00 | C |
| ATOM | 3168 | N6 | A | B | 76 | 17.798 | 162.014 | 307.347 | 1.00 | 0.00 | N |
| ATOM | 3169 | N1 | A | B | 76 | 17.680 | 163.123 | 309.367 | 1.00 | 0.00 | N |
| ATOM | 3170 | C2 | A | B | 76 | 17.983 | 164.202 | 310.101 | 1.00 | 0.00 | C |
| ATOM | 3171 | N3 | A | B | 76 | 18.654 | 165.298 | 309.748 | 1.00 | 0.00 | N |
| ATOM | 3172 | C4 | A | B | 76 | 19.046 | 165.223 | 308.460 | 1.00 | 0.00 | C |

| | | | | | | | | | | |
|---|---|---|---|---|---|---|---|---|---|---|
| TER | 3173 | | A B | 76 | | | | | | |
| ATOM | 3174 | O3P | G C | 1 | 17.719 | 161.229 | 281.171 | 1.00 | 0.00 | O |
| ATOM | 3175 | P | G C | 1 | 18.250 | 159.873 | 281.605 | 1.00 | 0.00 | P |
| ATOM | 3176 | O1P | G C | 1 | 19.195 | 159.243 | 280.593 | 1.00 | 0.00 | O |
| ATOM | 3177 | O2P | G C | 1 | 17.160 | 158.923 | 282.081 | 1.00 | 0.00 | O |
| ATOM | 3178 | O5* | G C | 1 | 19.192 | 160.130 | 282.904 | 1.00 | 0.00 | O |
| ATOM | 3179 | C5* | G C | 1 | 20.370 | 159.345 | 283.086 | 1.00 | 0.00 | C |
| ATOM | 3180 | C4* | G C | 1 | 20.981 | 159.616 | 284.432 | 1.00 | 0.00 | C |
| ATOM | 3181 | O4* | G C | 1 | 20.041 | 159.303 | 285.495 | 1.00 | 0.00 | O |
| ATOM | 3182 | C3* | G C | 1 | 22.222 | 158.771 | 284.670 | 1.00 | 0.00 | C |
| ATOM | 3183 | O3* | G C | 1 | 23.352 | 159.598 | 284.437 | 1.00 | 0.00 | O |
| ATOM | 3184 | C2* | G C | 1 | 22.096 | 158.333 | 286.126 | 1.00 | 0.00 | C |
| ATOM | 3185 | O2* | G C | 1 | 22.694 | 159.237 | 287.032 | 1.00 | 0.00 | O |
| ATOM | 3186 | C1* | G C | 1 | 20.577 | 158.293 | 286.320 | 1.00 | 0.00 | C |
| ATOM | 3187 | N9 | G C | 1 | 19.940 | 157.036 | 285.938 | 1.00 | 0.00 | N |
| ATOM | 3188 | C8 | G C | 1 | 18.847 | 156.893 | 285.118 | 1.00 | 0.00 | C |
| ATOM | 3189 | N7 | G C | 1 | 18.482 | 155.652 | 284.958 | 1.00 | 0.00 | N |
| ATOM | 3190 | C5 | G C | 1 | 19.391 | 154.927 | 285.715 | 1.00 | 0.00 | C |
| ATOM | 3191 | C6 | G C | 1 | 19.499 | 153.531 | 285.927 | 1.00 | 0.00 | C |
| ATOM | 3192 | O6 | G C | 1 | 18.790 | 152.625 | 285.473 | 1.00 | 0.00 | O |
| ATOM | 3193 | N1 | G C | 1 | 20.564 | 153.223 | 286.769 | 1.00 | 0.00 | N |
| ATOM | 3194 | C2 | G C | 1 | 21.416 | 154.139 | 287.334 | 1.00 | 0.00 | C |
| ATOM | 3195 | N2 | G C | 1 | 22.379 | 153.645 | 288.121 | 1.00 | 0.00 | N |
| ATOM | 3196 | N3 | G C | 1 | 21.329 | 155.444 | 287.142 | 1.00 | 0.00 | N |
| ATOM | 3197 | C4 | G C | 1 | 20.299 | 155.767 | 286.328 | 1.00 | 0.00 | C |
| ATOM | 3198 | P | C C | 2 | 24.896 | 159.281 | 284.039 | 1.00 | 0.00 | P |
| ATOM | 3199 | O1P | C C | 2 | 25.451 | 160.500 | 283.397 | 1.00 | 0.00 | O |
| ATOM | 3200 | O2P | C C | 2 | 24.932 | 157.988 | 283.310 | 1.00 | 0.00 | O |
| ATOM | 3201 | O5* | C C | 2 | 25.618 | 159.081 | 285.441 | 1.00 | 0.00 | O |
| ATOM | 3202 | C5* | C C | 2 | 26.874 | 159.697 | 285.695 | 1.00 | 0.00 | C |
| ATOM | 3203 | C4* | C C | 2 | 27.913 | 158.651 | 286.015 | 1.00 | 0.00 | C |
| ATOM | 3204 | O4* | C C | 2 | 27.515 | 157.970 | 287.234 | 1.00 | 0.00 | O |
| ATOM | 3205 | C3* | C C | 2 | 28.076 | 157.507 | 285.022 | 1.00 | 0.00 | C |
| ATOM | 3206 | O3* | C C | 2 | 28.905 | 157.846 | 283.914 | 1.00 | 0.00 | O |
| ATOM | 3207 | C2* | C C | 2 | 28.762 | 156.465 | 285.893 | 1.00 | 0.00 | C |
| ATOM | 3208 | O2* | C C | 2 | 30.140 | 156.721 | 286.069 | 1.00 | 0.00 | O |
| ATOM | 3209 | C1* | C C | 2 | 28.018 | 156.644 | 287.216 | 1.00 | 0.00 | C |
| ATOM | 3210 | N1 | C C | 2 | 26.891 | 155.711 | 287.325 | 1.00 | 0.00 | N |
| ATOM | 3211 | C2 | C C | 2 | 27.124 | 154.442 | 287.866 | 1.00 | 0.00 | C |
| ATOM | 3212 | O2 | C C | 2 | 28.265 | 154.163 | 288.276 | 1.00 | 0.00 | O |
| ATOM | 3213 | N3 | C C | 2 | 26.107 | 153.556 | 287.930 | 1.00 | 0.00 | N |
| ATOM | 3214 | C4 | C C | 2 | 24.896 | 153.899 | 287.488 | 1.00 | 0.00 | C |
| ATOM | 3215 | N4 | C C | 2 | 23.926 | 152.989 | 287.566 | 1.00 | 0.00 | N |
| ATOM | 3216 | C5 | C C | 2 | 24.627 | 155.188 | 286.949 | 1.00 | 0.00 | C |
| ATOM | 3217 | C6 | C C | 2 | 25.643 | 156.058 | 286.889 | 1.00 | 0.00 | C |
| ATOM | 3218 | P | G C | 3 | 29.095 | 156.797 | 282.702 | 1.00 | 0.00 | P |
| ATOM | 3219 | O1P | G C | 3 | 30.136 | 157.338 | 281.792 | 1.00 | 0.00 | O |
| ATOM | 3220 | O2P | G C | 3 | 27.753 | 156.453 | 282.162 | 1.00 | 0.00 | O |
| ATOM | 3221 | O5* | G C | 3 | 29.722 | 155.497 | 283.379 | 1.00 | 0.00 | O |
| ATOM | 3222 | C5* | G C | 3 | 31.117 | 155.259 | 283.293 | 1.00 | 0.00 | C |
| ATOM | 3223 | C4* | G C | 3 | 31.501 | 154.071 | 284.136 | 1.00 | 0.00 | C |
| ATOM | 3224 | O4* | G C | 3 | 30.653 | 153.991 | 285.314 | 1.00 | 0.00 | O |
| ATOM | 3225 | C3* | G C | 3 | 31.299 | 152.722 | 283.483 | 1.00 | 0.00 | C |
| ATOM | 3226 | O3* | G C | 3 | 32.333 | 152.417 | 282.563 | 1.00 | 0.00 | O |
| ATOM | 3227 | C2* | G C | 3 | 31.299 | 151.798 | 284.693 | 1.00 | 0.00 | C |
| ATOM | 3228 | O2* | G C | 3 | 32.585 | 151.513 | 285.206 | 1.00 | 0.00 | O |
| ATOM | 3229 | C1* | G C | 3 | 30.477 | 152.627 | 285.682 | 1.00 | 0.00 | C |
| ATOM | 3230 | N9 | G C | 3 | 29.060 | 152.304 | 285.551 | 1.00 | 0.00 | N |
| ATOM | 3231 | C8 | G C | 3 | 28.094 | 153.050 | 284.923 | 1.00 | 0.00 | C |
| ATOM | 3232 | N7 | G C | 3 | 26.923 | 152.470 | 284.919 | 1.00 | 0.00 | N |
| ATOM | 3233 | C5 | G C | 3 | 27.129 | 151.276 | 285.598 | 1.00 | 0.00 | C |
| ATOM | 3234 | C6 | G C | 3 | 26.225 | 150.220 | 285.893 | 1.00 | 0.00 | C |
| ATOM | 3235 | O6 | G C | 3 | 25.025 | 150.133 | 285.614 | 1.00 | 0.00 | O |
| ATOM | 3236 | N1 | G C | 3 | 26.852 | 149.189 | 286.587 | 1.00 | 0.00 | N |
| ATOM | 3237 | C2 | G C | 3 | 28.180 | 149.172 | 286.949 | 1.00 | 0.00 | C |
| ATOM | 3238 | N2 | G C | 3 | 28.598 | 148.083 | 287.610 | 1.00 | 0.00 | N |
| ATOM | 3239 | N3 | G C | 3 | 29.031 | 150.153 | 286.681 | 1.00 | 0.00 | N |
| ATOM | 3240 | C4 | G C | 3 | 28.439 | 151.162 | 286.005 | 1.00 | 0.00 | C |
| ATOM | 3241 | P | G C | 4 | 31.974 | 151.609 | 281.231 | 1.00 | 0.00 | P |
| ATOM | 3242 | O1P | G C | 4 | 33.056 | 151.809 | 280.236 | 1.00 | 0.00 | O |
| ATOM | 3243 | O2P | G C | 4 | 30.586 | 152.010 | 280.897 | 1.00 | 0.00 | O |
| ATOM | 3244 | O5* | G C | 4 | 31.986 | 150.081 | 281.685 | 1.00 | 0.00 | O |
| ATOM | 3245 | C5* | G C | 4 | 33.204 | 149.442 | 282.021 | 1.00 | 0.00 | C |
| ATOM | 3246 | C4* | G C | 4 | 32.932 | 148.200 | 282.825 | 1.00 | 0.00 | C |
| ATOM | 3247 | O4* | G C | 4 | 32.017 | 148.491 | 283.912 | 1.00 | 0.00 | O |
| ATOM | 3248 | C3* | G C | 4 | 32.217 | 147.103 | 282.076 | 1.00 | 0.00 | C |
| ATOM | 3249 | O3* | G C | 4 | 33.150 | 146.392 | 281.305 | 1.00 | 0.00 | O |
| ATOM | 3250 | C2* | G C | 4 | 31.690 | 146.251 | 283.217 | 1.00 | 0.00 | C |
| ATOM | 3251 | O2* | G C | 4 | 32.683 | 145.456 | 283.813 | 1.00 | 0.00 | O |
| ATOM | 3252 | C1* | G C | 4 | 31.239 | 147.334 | 284.191 | 1.00 | 0.00 | C |
| ATOM | 3253 | N9 | G C | 4 | 29.837 | 147.667 | 283.967 | 1.00 | 0.00 | N |
| ATOM | 3254 | C8 | G C | 4 | 29.322 | 148.844 | 283.476 | 1.00 | 0.00 | C |
| ATOM | 3255 | N7 | G C | 4 | 28.019 | 148.842 | 283.401 | 1.00 | 0.00 | N |
| ATOM | 3256 | C5 | G C | 4 | 27.653 | 147.593 | 283.868 | 1.00 | 0.00 | C |
| ATOM | 3257 | C6 | G C | 4 | 26.376 | 147.018 | 284.020 | 1.00 | 0.00 | C |
| ATOM | 3258 | O6 | G C | 4 | 25.265 | 147.532 | 283.778 | 1.00 | 0.00 | O |
| ATOM | 3259 | N1 | G C | 4 | 26.458 | 145.715 | 284.510 | 1.00 | 0.00 | N |

| | | | | | | | | | |
|---|---|---|---|---|---|---|---|---|---|
| ATOM | 3260 | C2 | G C | 4 | 27.627 | 145.053 | 284.818 | 1.00 | 0.00 | C |
| ATOM | 3261 | N2 | G C | 4 | 27.510 | 143.798 | 285.267 | 1.00 | 0.00 | N |
| ATOM | 3262 | N3 | G C | 4 | 28.827 | 145.586 | 284.688 | 1.00 | 0.00 | N |
| ATOM | 3263 | C4 | G C | 4 | 28.765 | 146.849 | 284.211 | 1.00 | 0.00 | C |
| ATOM | 3264 | P | A C | 5 | 32.665 | 145.637 | 279.984 | 1.00 | 0.00 | P |
| ATOM | 3265 | O1P | A C | 5 | 33.848 | 144.925 | 279.437 | 1.00 | 0.00 | O |
| ATOM | 3266 | O2P | A C | 5 | 31.921 | 146.606 | 279.123 | 1.00 | 0.00 | O |
| ATOM | 3267 | O5* | A C | 5 | 31.685 | 144.526 | 280.554 | 1.00 | 0.00 | O |
| ATOM | 3268 | C5* | A C | 5 | 32.222 | 143.405 | 281.223 | 1.00 | 0.00 | C |
| ATOM | 3269 | C4* | A C | 5 | 31.129 | 142.444 | 281.559 | 1.00 | 0.00 | C |
| ATOM | 3270 | O4* | A C | 5 | 30.222 | 143.080 | 282.501 | 1.00 | 0.00 | O |
| ATOM | 3271 | C3* | A C | 5 | 30.230 | 142.075 | 280.393 | 1.00 | 0.00 | C |
| ATOM | 3272 | O3* | A C | 5 | 30.824 | 141.025 | 279.641 | 1.00 | 0.00 | O |
| ATOM | 3273 | C2* | A C | 5 | 28.992 | 141.611 | 281.148 | 1.00 | 0.00 | C |
| ATOM | 3274 | O2* | A C | 5 | 29.182 | 140.378 | 281.823 | 1.00 | 0.00 | O |
| ATOM | 3275 | C1* | A C | 5 | 28.898 | 142.699 | 282.214 | 1.00 | 0.00 | C |
| ATOM | 3276 | N9 | A C | 5 | 28.183 | 143.874 | 281.732 | 1.00 | 0.00 | N |
| ATOM | 3277 | C8 | A C | 5 | 28.691 | 145.042 | 281.229 | 1.00 | 0.00 | C |
| ATOM | 3278 | N7 | A C | 5 | 27.770 | 145.914 | 280.893 | 1.00 | 0.00 | N |
| ATOM | 3279 | C5 | A C | 5 | 26.578 | 145.274 | 281.196 | 1.00 | 0.00 | C |
| ATOM | 3280 | C6 | A C | 5 | 25.229 | 145.676 | 281.090 | 1.00 | 0.00 | C |
| ATOM | 3281 | N6 | A C | 5 | 24.839 | 146.865 | 280.617 | 1.00 | 0.00 | N |
| ATOM | 3282 | N1 | A C | 5 | 24.282 | 144.802 | 281.484 | 1.00 | 0.00 | N |
| ATOM | 3283 | C2 | A C | 5 | 24.670 | 143.597 | 281.946 | 1.00 | 0.00 | C |
| ATOM | 3284 | N3 | A C | 5 | 25.904 | 143.108 | 282.096 | 1.00 | 0.00 | N |
| ATOM | 3285 | C4 | A C | 5 | 26.819 | 144.013 | 281.703 | 1.00 | 0.00 | C |
| ATOM | 3286 | P | U C | 6 | 30.523 | 140.900 | 278.068 | 1.00 | 0.00 | P |
| ATOM | 3287 | O1P | U C | 6 | 31.269 | 139.703 | 277.615 | 1.00 | 0.00 | O |
| ATOM | 3288 | O2P | U C | 6 | 30.746 | 142.209 | 277.402 | 1.00 | 0.00 | O |
| ATOM | 3289 | O5* | U C | 6 | 28.974 | 140.543 | 277.999 | 1.00 | 0.00 | O |
| ATOM | 3290 | C5* | U C | 6 | 28.530 | 139.281 | 278.445 | 1.00 | 0.00 | C |
| ATOM | 3291 | C4* | U C | 6 | 27.044 | 139.293 | 278.634 | 1.00 | 0.00 | C |
| ATOM | 3292 | O4* | U C | 6 | 26.639 | 140.430 | 279.442 | 1.00 | 0.00 | O |
| ATOM | 3293 | C3* | U C | 6 | 26.277 | 139.509 | 277.357 | 1.00 | 0.00 | C |
| ATOM | 3294 | O3* | U C | 6 | 26.215 | 138.291 | 276.649 | 1.00 | 0.00 | O |
| ATOM | 3295 | C2* | U C | 6 | 24.921 | 139.903 | 277.910 | 1.00 | 0.00 | C |
| ATOM | 3296 | O2* | U C | 6 | 24.252 | 138.782 | 278.442 | 1.00 | 0.00 | O |
| ATOM | 3297 | C1* | U C | 6 | 25.334 | 140.824 | 279.055 | 1.00 | 0.00 | C |
| ATOM | 3298 | N1 | U C | 6 | 25.361 | 142.238 | 278.669 | 1.00 | 0.00 | N |
| ATOM | 3299 | C2 | U C | 6 | 24.139 | 142.831 | 278.426 | 1.00 | 0.00 | C |
| ATOM | 3300 | O2 | U C | 6 | 23.096 | 142.223 | 278.500 | 1.00 | 0.00 | O |
| ATOM | 3301 | N3 | U C | 6 | 24.188 | 144.146 | 278.074 | 1.00 | 0.00 | N |
| ATOM | 3302 | C4 | U C | 6 | 25.306 | 144.927 | 277.921 | 1.00 | 0.00 | C |
| ATOM | 3303 | O4 | U C | 6 | 25.174 | 146.096 | 277.564 | 1.00 | 0.00 | O |
| ATOM | 3304 | C5 | U C | 6 | 26.550 | 144.253 | 278.185 | 1.00 | 0.00 | C |
| ATOM | 3305 | C6 | U C | 6 | 26.531 | 142.953 | 278.545 | 1.00 | 0.00 | C |
| ATOM | 3306 | P | U C | 7 | 26.107 | 138.320 | 275.052 | 1.00 | 0.00 | P |
| ATOM | 3307 | O1P | U C | 7 | 26.341 | 136.938 | 274.610 | 1.00 | 0.00 | O |
| ATOM | 3308 | O2P | U C | 7 | 26.941 | 139.452 | 274.531 | 1.00 | 0.00 | O |
| ATOM | 3309 | O5* | U C | 7 | 24.582 | 138.722 | 274.773 | 1.00 | 0.00 | O |
| ATOM | 3310 | C5* | U C | 7 | 23.500 | 137.990 | 275.357 | 1.00 | 0.00 | C |
| ATOM | 3311 | C4* | U C | 7 | 22.183 | 138.594 | 274.918 | 1.00 | 0.00 | C |
| ATOM | 3312 | O4* | U C | 7 | 22.163 | 139.970 | 275.383 | 1.00 | 0.00 | O |
| ATOM | 3313 | C3* | U C | 7 | 21.967 | 138.637 | 273.406 | 1.00 | 0.00 | C |
| ATOM | 3314 | O3* | U C | 7 | 20.632 | 138.280 | 273.056 | 1.00 | 0.00 | O |
| ATOM | 3315 | C2* | U C | 7 | 22.301 | 140.078 | 273.044 | 1.00 | 0.00 | C |
| ATOM | 3316 | O2* | U C | 7 | 21.509 | 140.558 | 271.978 | 1.00 | 0.00 | O |
| ATOM | 3317 | C1* | U C | 7 | 21.889 | 140.829 | 274.305 | 1.00 | 0.00 | C |
| ATOM | 3318 | N1 | U C | 7 | 22.626 | 142.086 | 274.506 | 1.00 | 0.00 | N |
| ATOM | 3319 | C2 | U C | 7 | 21.906 | 143.260 | 274.434 | 1.00 | 0.00 | C |
| ATOM | 3320 | O2 | U C | 7 | 20.697 | 143.285 | 274.254 | 1.00 | 0.00 | O |
| ATOM | 3321 | N3 | U C | 7 | 22.646 | 144.404 | 274.586 | 1.00 | 0.00 | N |
| ATOM | 3322 | C4 | U C | 7 | 24.010 | 144.493 | 274.805 | 1.00 | 0.00 | C |
| ATOM | 3323 | O4 | U C | 7 | 24.550 | 145.615 | 274.912 | 1.00 | 0.00 | O |
| ATOM | 3324 | C5 | U C | 7 | 24.674 | 143.230 | 274.891 | 1.00 | 0.00 | C |
| ATOM | 3325 | C6 | U C | 7 | 23.980 | 142.102 | 274.745 | 1.00 | 0.00 | C |
| ATOM | 3326 | P | U C | 8 | 20.291 | 136.787 | 272.533 | 1.00 | 0.00 | P |
| ATOM | 3327 | O1P | U C | 8 | 18.884 | 136.808 | 272.041 | 1.00 | 0.00 | O |
| ATOM | 3328 | O2P | U C | 8 | 20.724 | 135.787 | 273.537 | 1.00 | 0.00 | O |
| ATOM | 3329 | O5* | U C | 8 | 21.199 | 136.597 | 271.232 | 1.00 | 0.00 | O |
| ATOM | 3330 | C5* | U C | 8 | 20.788 | 137.167 | 269.998 | 1.00 | 0.00 | C |
| ATOM | 3331 | C4* | U C | 8 | 21.085 | 136.241 | 268.847 | 1.00 | 0.00 | C |
| ATOM | 3332 | O4* | U C | 8 | 22.530 | 136.145 | 268.659 | 1.00 | 0.00 | O |
| ATOM | 3333 | C3* | U C | 8 | 20.632 | 134.786 | 268.936 | 1.00 | 0.00 | C |
| ATOM | 3334 | O3* | U C | 8 | 19.252 | 134.623 | 268.600 | 1.00 | 0.00 | O |
| ATOM | 3335 | C2* | U C | 8 | 21.522 | 134.184 | 267.860 | 1.00 | 0.00 | C |
| ATOM | 3336 | O2* | U C | 8 | 21.202 | 134.611 | 266.539 | 1.00 | 0.00 | O |
| ATOM | 3337 | C1* | U C | 8 | 22.860 | 134.843 | 268.220 | 1.00 | 0.00 | C |
| ATOM | 3338 | N1 | U C | 8 | 23.545 | 134.166 | 269.323 | 1.00 | 0.00 | N |
| ATOM | 3339 | C2 | U C | 8 | 24.333 | 133.072 | 269.020 | 1.00 | 0.00 | C |
| ATOM | 3340 | O2 | U C | 8 | 24.492 | 132.670 | 267.888 | 1.00 | 0.00 | O |
| ATOM | 3341 | N3 | U C | 8 | 24.923 | 132.476 | 270.096 | 1.00 | 0.00 | N |
| ATOM | 3342 | C4 | U C | 8 | 24.815 | 132.861 | 271.416 | 1.00 | 0.00 | C |
| ATOM | 3343 | O4 | U C | 8 | 25.360 | 132.191 | 272.292 | 1.00 | 0.00 | O |
| ATOM | 3344 | C5 | U C | 8 | 23.988 | 133.994 | 271.637 | 1.00 | 0.00 | C |
| ATOM | 3345 | C6 | U C | 8 | 23.402 | 134.596 | 270.608 | 1.00 | 0.00 | C |
| ATOM | 3346 | P | A C | 9 | 18.379 | 133.474 | 269.312 | 1.00 | 0.00 | P |

```
ATOM   3347  O1P    A C   9   17.096 134.091 269.743  1.00  0.00           O
ATOM   3348  O2P    A C   9   19.216 132.732 270.321  1.00  0.00           O
ATOM   3349  O5*    A C   9   18.064 132.475 268.128  1.00  0.00           O
ATOM   3350  C5*    A C   9   17.188 132.859 267.074  1.00  0.00           C
ATOM   3351  C4*    A C   9   16.263 131.720 266.749  1.00  0.00           C
ATOM   3352  O4*    A C   9   17.086 130.683 266.140  1.00  0.00           O
ATOM   3353  C3*    A C   9   15.574 131.063 267.954  1.00  0.00           C
ATOM   3354  O3*    A C   9   14.316 130.519 267.566  1.00  0.00           O
ATOM   3355  C2*    A C   9   16.508 129.898 268.277  1.00  0.00           C
ATOM   3356  O2*    A C   9   15.822 128.796 268.811  1.00  0.00           O
ATOM   3357  C1*    A C   9   16.974 129.494 266.892  1.00  0.00           C
ATOM   3358  N9     A C   9   18.257 128.772 266.888  1.00  0.00           N
ATOM   3359  C8     A C   9   19.073 128.506 267.955  1.00  0.00           C
ATOM   3360  N7     A C   9   20.106 127.731 267.659  1.00  0.00           N
ATOM   3361  C5     A C   9   19.963 127.498 266.305  1.00  0.00           C
ATOM   3362  C6     A C   9   20.716 126.757 265.397  1.00  0.00           C
ATOM   3363  N6     A C   9   21.819 126.068 265.734  1.00  0.00           N
ATOM   3364  N1     A C   9   20.304 126.733 264.111  1.00  0.00           N
ATOM   3365  C2     A C   9   19.209 127.426 263.771  1.00  0.00           C
ATOM   3366  N3     A C   9   18.416 128.170 264.535  1.00  0.00           N
ATOM   3367  C4     A C   9   18.841 128.160 265.808  1.00  0.00           C
HETATM 3368  P    2MG C  10   12.939 131.352 267.844  1.00  0.00           P
HETATM 3369  O1P  2MG C  10   13.185 132.794 267.811  1.00  0.00           O
HETATM 3370  O2P  2MG C  10   11.894 130.776 266.957  1.00  0.00           O
HETATM 3371  O5*  2MG C  10   12.626 131.006 269.357  1.00  0.00           O
HETATM 3372  C5*  2MG C  10   11.437 131.526 269.972  1.00  0.00           C
HETATM 3373  C4*  2MG C  10   10.922 130.563 271.011  1.00  0.00           C
HETATM 3374  O4*  2MG C  10   10.618 129.299 270.356  1.00  0.00           O
HETATM 3375  C3*  2MG C  10   11.917 130.216 272.100  1.00  0.00           C
HETATM 3376  O3*  2MG C  10   11.761 131.123 273.186  1.00  0.00           O
HETATM 3377  C2*  2MG C  10   11.478 128.820 272.482  1.00  0.00           C
HETATM 3378  O2*  2MG C  10   10.288 128.896 273.256  1.00  0.00           O
HETATM 3379  C1*  2MG C  10   11.125 128.227 271.126  1.00  0.00           C
HETATM 3380  N9   2MG C  10   12.190 127.580 270.365  1.00  0.00           N
HETATM 3381  C8   2MG C  10   12.516 127.826 269.047  1.00  0.00           C
HETATM 3382  N7   2MG C  10   13.468 127.045 268.592  1.00  0.00           N
HETATM 3383  C5   2MG C  10   13.798 126.244 269.677  1.00  0.00           C
HETATM 3384  C6   2MG C  10   14.769 125.232 269.791  1.00  0.00           C
HETATM 3385  O6   2MG C  10   15.514 124.789 268.917  1.00  0.00           O
HETATM 3386  N1   2MG C  10   14.824 124.710 271.080  1.00  0.00           N
HETATM 3387  C2   2MG C  10   14.025 125.116 272.129  1.00  0.00           C
HETATM 3388  N2   2MG C  10   14.227 124.488 273.297  1.00  0.00           N
HETATM 3389  CM2  2MG C  10   13.390 124.671 274.488  1.00  0.00           C
HETATM 3390  N3   2MG C  10   13.097 126.062 272.031  1.00  0.00           N
HETATM 3391  C4   2MG C  10   13.035 126.577 270.788  1.00  0.00           C
ATOM   3392  P      C C  11   13.042 131.788 273.867  1.00  0.00           P
ATOM   3393  O1P    C C  11   12.617 132.830 274.814  1.00  0.00           O
ATOM   3394  O2P    C C  11   13.994 132.144 272.764  1.00  0.00           O
ATOM   3395  O5*    C C  11   13.647 130.619 274.767  1.00  0.00           O
ATOM   3396  C5*    C C  11   13.003 130.267 275.993  1.00  0.00           C
ATOM   3397  C4*    C C  11   13.721 129.127 276.675  1.00  0.00           C
ATOM   3398  O4*    C C  11   13.727 127.959 275.813  1.00  0.00           O
ATOM   3399  C3*    C C  11   15.173 129.411 276.989  1.00  0.00           C
ATOM   3400  O3*    C C  11   15.278 130.003 278.276  1.00  0.00           O
ATOM   3401  C2*    C C  11   15.834 128.035 276.927  1.00  0.00           C
ATOM   3402  O2*    C C  11   15.808 127.367 278.168  1.00  0.00           O
ATOM   3403  C1*    C C  11   14.976 127.299 275.896  1.00  0.00           C
ATOM   3404  N1     C C  11   15.558 127.282 274.550  1.00  0.00           N
ATOM   3405  C2     C C  11   16.578 126.376 274.257  1.00  0.00           C
ATOM   3406  O2     C C  11   16.956 125.597 275.147  1.00  0.00           O
ATOM   3407  N3     C C  11   17.133 126.378 273.008  1.00  0.00           N
ATOM   3408  C4     C C  11   16.693 127.243 272.088  1.00  0.00           C
ATOM   3409  N4     C C  11   17.246 127.212 270.867  1.00  0.00           N
ATOM   3410  C5     C C  11   15.657 128.171 272.367  1.00  0.00           C
ATOM   3411  C6     C C  11   15.117 128.152 273.599  1.00  0.00           C
ATOM   3412  P      U C  12   16.413 131.091 278.528  1.00  0.00           P
ATOM   3413  O1P    U C  12   16.268 131.743 279.853  1.00  0.00           O
ATOM   3414  O2P    U C  12   16.402 131.932 277.306  1.00  0.00           O
ATOM   3415  O5*    U C  12   17.746 130.217 278.521  1.00  0.00           O
ATOM   3416  C5*    U C  12   18.026 129.300 279.577  1.00  0.00           C
ATOM   3417  C4*    U C  12   19.251 128.480 279.250  1.00  0.00           C
ATOM   3418  O4*    U C  12   18.982 127.636 278.101  1.00  0.00           O
ATOM   3419  C3*    U C  12   20.460 129.280 278.793  1.00  0.00           C
ATOM   3420  O3*    U C  12   21.175 129.787 279.897  1.00  0.00           O
ATOM   3421  C2*    U C  12   21.296 128.218 278.092  1.00  0.00           C
ATOM   3422  O2*    U C  12   22.117 127.482 278.982  1.00  0.00           O
ATOM   3423  C1*    U C  12   20.215 127.359 277.434  1.00  0.00           C
ATOM   3424  N1     U C  12   20.071 127.724 276.021  1.00  0.00           N
ATOM   3425  C2     U C  12   20.957 127.170 275.118  1.00  0.00           C
ATOM   3426  O2     U C  12   21.853 126.431 275.442  1.00  0.00           O
ATOM   3427  N3     U C  12   20.760 127.532 273.821  1.00  0.00           N
ATOM   3428  C4     U C  12   19.785 128.390 273.342  1.00  0.00           C
ATOM   3429  O4     U C  12   19.686 128.585 272.137  1.00  0.00           O
ATOM   3430  C5     U C  12   18.927 128.932 274.343  1.00  0.00           C
ATOM   3431  C6     U C  12   19.102 128.582 275.620  1.00  0.00           C
ATOM   3432  P      C C  13   22.205 130.994 279.685  1.00  0.00           P
ATOM   3433  O1P    C C  13   22.738 131.464 280.991  1.00  0.00           O
```

```
ATOM   3434  O2P   C C  13      21.550 131.956 278.770  1.00  0.00           O
ATOM   3435  O5*   C C  13      23.412 130.273 278.954  1.00  0.00           O
ATOM   3436  C5*   C C  13      24.078 130.877 277.870  1.00  0.00           C
ATOM   3437  C4*   C C  13      24.721 129.820 277.023  1.00  0.00           C
ATOM   3438  O4*   C C  13      23.740 129.216 276.138  1.00  0.00           O
ATOM   3439  C3*   C C  13      25.758 130.386 276.083  1.00  0.00           C
ATOM   3440  O3*   C C  13      26.930 130.590 276.854  1.00  0.00           O
ATOM   3441  C2*   C C  13      25.829 129.306 275.004  1.00  0.00           C
ATOM   3442  O2*   C C  13      26.622 128.195 275.340  1.00  0.00           O
ATOM   3443  C1*   C C  13      24.368 128.850 274.922  1.00  0.00           C
ATOM   3444  N1    C C  13      23.610 129.455 273.821  1.00  0.00           N
ATOM   3445  C2    C C  13      23.867 129.052 272.509  1.00  0.00           C
ATOM   3446  O2    C C  13      24.785 128.236 272.303  1.00  0.00           O
ATOM   3447  N3    C C  13      23.135 129.576 271.492  1.00  0.00           N
ATOM   3448  C4    C C  13      22.213 130.515 271.750  1.00  0.00           C
ATOM   3449  N4    C C  13      21.534 131.033 270.728  1.00  0.00           N
ATOM   3450  C5    C C  13      21.945 130.965 273.082  1.00  0.00           C
ATOM   3451  C6    C C  13      22.652 130.401 274.078  1.00  0.00           C
ATOM   3452  P     A C  14      28.156 131.406 276.233  1.00  0.00           P
ATOM   3453  O1P   A C  14      29.123 131.700 277.323  1.00  0.00           O
ATOM   3454  O2P   A C  14      27.658 132.514 275.384  1.00  0.00           O
ATOM   3455  O5*   A C  14      28.818 130.293 275.324  1.00  0.00           O
ATOM   3456  C5*   A C  14      29.154 130.567 273.995  1.00  0.00           C
ATOM   3457  C4*   A C  14      29.825 129.376 273.382  1.00  0.00           C
ATOM   3458  O4*   A C  14      28.795 128.577 272.741  1.00  0.00           O
ATOM   3459  C3*   A C  14      30.762 129.783 272.252  1.00  0.00           C
ATOM   3460  O3*   A C  14      32.072 130.003 272.732  1.00  0.00           O
ATOM   3461  C2*   A C  14      30.673 128.602 271.309  1.00  0.00           C
ATOM   3462  O2*   A C  14      31.431 127.487 271.740  1.00  0.00           O
ATOM   3463  C1*   A C  14      29.186 128.286 271.399  1.00  0.00           C
ATOM   3464  N9    A C  14      28.373 129.079 270.483  1.00  0.00           N
ATOM   3465  C8    A C  14      27.395 130.012 270.768  1.00  0.00           C
ATOM   3466  N7    A C  14      26.786 130.476 269.692  1.00  0.00           N
ATOM   3467  C5    A C  14      27.415 129.822 268.643  1.00  0.00           C
ATOM   3468  C6    A C  14      27.256 129.898 267.259  1.00  0.00           C
ATOM   3469  N6    A C  14      26.336 130.670 266.642  1.00  0.00           N
ATOM   3470  N1    A C  14      28.078 129.148 266.500  1.00  0.00           N
ATOM   3471  C2    A C  14      28.991 128.384 267.102  1.00  0.00           C
ATOM   3472  N3    A C  14      29.246 128.243 268.377  1.00  0.00           N
ATOM   3473  C4    A C  14      28.412 128.988 269.110  1.00  0.00           C
ATOM   3474  P     G C  15      32.718 131.456 272.608  1.00  0.00           P
ATOM   3475  O1P   G C  15      34.067 131.415 273.219  1.00  0.00           O
ATOM   3476  O2P   G C  15      31.770 132.490 273.021  1.00  0.00           O
ATOM   3477  O5*   G C  15      32.860 131.692 271.039  1.00  0.00           O
ATOM   3478  C5*   G C  15      33.460 130.735 270.206  1.00  0.00           C
ATOM   3479  C4*   G C  15      33.037 130.971 268.766  1.00  0.00           C
ATOM   3480  O4*   G C  15      31.664 130.531 268.581  1.00  0.00           O
ATOM   3481  C3*   G C  15      32.989 132.417 268.308  1.00  0.00           C
ATOM   3482  O3*   G C  15      34.279 132.906 267.970  1.00  0.00           O
ATOM   3483  C2*   G C  15      32.102 132.306 267.071  1.00  0.00           C
ATOM   3484  O2*   G C  15      32.712 131.703 265.967  1.00  0.00           O
ATOM   3485  C1*   G C  15      31.035 131.343 267.584  1.00  0.00           C
ATOM   3486  N9    G C  15      30.009 132.184 268.185  1.00  0.00           N
ATOM   3487  C8    G C  15      29.814 132.490 269.515  1.00  0.00           C
ATOM   3488  N7    G C  15      28.822 133.343 269.701  1.00  0.00           N
ATOM   3489  C5    G C  15      28.332 133.596 268.430  1.00  0.00           C
ATOM   3490  C6    G C  15      27.269 134.468 267.982  1.00  0.00           C
ATOM   3491  O6    G C  15      26.509 135.181 268.655  1.00  0.00           O
ATOM   3492  N1    G C  15      27.137 134.445 266.602  1.00  0.00           N
ATOM   3493  C2    G C  15      27.907 133.707 265.744  1.00  0.00           C
ATOM   3494  N2    G C  15      27.609 133.851 264.454  1.00  0.00           N
ATOM   3495  N3    G C  15      28.901 132.895 266.129  1.00  0.00           N
ATOM   3496  C4    G C  15      29.049 132.886 267.478  1.00  0.00           C
HETATM 3497  P     H2U C 16      34.690 134.419 268.343  1.00  0.00           P
HETATM 3498  O1P   H2U C 16      33.572 135.274 267.861  1.00  0.00           O
HETATM 3499  O2P   H2U C 16      35.119 134.526 269.763  1.00  0.00           O
HETATM 3500  O5*   H2U C 16      35.928 134.694 267.363  1.00  0.00           O
HETATM 3501  C5*   H2U C 16      35.729 134.625 265.940  1.00  0.00           C
HETATM 3502  C4*   H2U C 16      37.017 134.275 265.221  1.00  0.00           C
HETATM 3503  O4*   H2U C 16      37.984 135.320 265.469  1.00  0.00           O
HETATM 3504  C3*   H2U C 16      37.724 133.029 265.721  1.00  0.00           C
HETATM 3505  O3*   H2U C 16      38.536 132.428 264.679  1.00  0.00           O
HETATM 3506  C1*   H2U C 16      38.742 134.993 266.620  1.00  0.00           C
HETATM 3507  C2*   H2U C 16      38.394 133.544 266.995  1.00  0.00           C
HETATM 3508  O2*   H2U C 16      39.496 132.795 267.458  1.00  0.00           O
HETATM 3509  N1    H2U C 16      38.413 135.982 267.658  1.00  0.00           N
HETATM 3510  C2    H2U C 16      38.284 137.302 267.246  1.00  0.00           C
HETATM 3511  O2    H2U C 16      38.265 137.621 266.069  1.00  0.00           O
HETATM 3512  N3    H2U C 16      38.181 138.239 268.245  1.00  0.00           N
HETATM 3513  C4    H2U C 16      38.237 138.040 269.610  1.00  0.00           C
HETATM 3514  O4    H2U C 16      38.108 139.007 270.364  1.00  0.00           O
HETATM 3515  C5    H2U C 16      38.642 136.651 270.028  1.00  0.00           C
HETATM 3516  C6    H2U C 16      38.213 135.579 269.063  1.00  0.00           C
HETATM 3517  P     H2U C 17      40.096 132.827 264.483  1.00  0.00           P
HETATM 3518  O1P   H2U C 17      40.706 133.392 265.705  1.00  0.00           O
HETATM 3519  O2P   H2U C 17      40.760 131.683 263.805  1.00  0.00           O
HETATM 3520  O5*   H2U C 17      40.064 134.026 263.444  1.00  0.00           O
```

| | | | | | | | | | |
|---|---|---|---|---|---|---|---|---|---|
| HETATM | 3521 | C5* | H2U | C | 17 | 40.869 | 135.186 | 263.656 | 1.00 0.00 | C |
| HETATM | 3522 | C4* | H2U | C | 17 | 40.895 | 136.035 | 262.404 | 1.00 0.00 | C |
| HETATM | 3523 | O4* | H2U | C | 17 | 41.645 | 135.327 | 261.374 | 1.00 0.00 | O |
| HETATM | 3524 | C3* | H2U | C | 17 | 39.519 | 136.335 | 261.802 | 1.00 0.00 | C |
| HETATM | 3525 | O3* | H2U | C | 17 | 39.494 | 137.706 | 261.420 | 1.00 0.00 | O |
| HETATM | 3526 | C1* | H2U | C | 17 | 40.895 | 135.301 | 260.187 | 1.00 0.00 | C |
| HETATM | 3527 | C2* | H2U | C | 17 | 39.435 | 135.358 | 260.622 | 1.00 0.00 | C |
| HETATM | 3528 | O2* | H2U | C | 17 | 38.636 | 135.740 | 259.506 | 1.00 0.00 | O |
| HETATM | 3529 | N1 | H2U | C | 17 | 41.264 | 134.104 | 259.423 | 1.00 0.00 | N |
| HETATM | 3530 | C2 | H2U | C | 17 | 42.094 | 134.316 | 258.340 | 1.00 0.00 | C |
| HETATM | 3531 | O2 | H2U | C | 17 | 42.302 | 135.428 | 257.893 | 1.00 0.00 | O |
| HETATM | 3532 | N3 | H2U | C | 17 | 42.678 | 133.198 | 257.804 | 1.00 0.00 | N |
| HETATM | 3533 | C4 | H2U | C | 17 | 42.554 | 131.900 | 258.228 | 1.00 0.00 | C |
| HETATM | 3534 | O4 | H2U | C | 17 | 43.088 | 130.997 | 257.571 | 1.00 0.00 | O |
| HETATM | 3535 | C5 | H2U | C | 17 | 41.883 | 131.744 | 259.585 | 1.00 0.00 | C |
| HETATM | 3536 | C6 | H2U | C | 17 | 40.812 | 132.757 | 259.811 | 1.00 0.00 | C |
| ATOM | 3537 | P | G | C | 18 | 38.778 | 138.767 | 262.372 | 1.00 0.00 | P |
| ATOM | 3538 | O1P | G | C | 18 | 39.137 | 140.153 | 262.049 | 1.00 0.00 | O |
| ATOM | 3539 | O2P | G | C | 18 | 38.976 | 138.263 | 263.743 | 1.00 0.00 | O |
| ATOM | 3540 | O5* | G | C | 18 | 37.254 | 138.539 | 262.011 | 1.00 0.00 | O |
| ATOM | 3541 | C5* | G | C | 18 | 36.562 | 139.508 | 261.330 | 1.00 0.00 | C |
| ATOM | 3542 | C4* | G | C | 18 | 35.705 | 138.892 | 260.256 | 1.00 0.00 | C |
| ATOM | 3543 | O4* | G | C | 18 | 35.135 | 140.093 | 259.707 | 1.00 0.00 | O |
| ATOM | 3544 | C3* | G | C | 18 | 36.471 | 138.250 | 259.084 | 1.00 0.00 | C |
| ATOM | 3545 | O3* | G | C | 18 | 35.615 | 137.628 | 258.109 | 1.00 0.00 | O |
| ATOM | 3546 | C2* | G | C | 18 | 36.999 | 139.489 | 258.397 | 1.00 0.00 | C |
| ATOM | 3547 | O2* | G | C | 18 | 37.301 | 139.256 | 257.028 | 1.00 0.00 | O |
| ATOM | 3548 | C1* | G | C | 18 | 35.749 | 140.364 | 258.470 | 1.00 0.00 | C |
| ATOM | 3549 | N9 | G | C | 18 | 36.052 | 141.783 | 258.392 | 1.00 0.00 | N |
| ATOM | 3550 | C8 | G | C | 18 | 37.190 | 142.426 | 258.814 | 1.00 0.00 | C |
| ATOM | 3551 | N7 | G | C | 18 | 37.207 | 143.690 | 258.477 | 1.00 0.00 | N |
| ATOM | 3552 | C5 | G | C | 18 | 35.998 | 143.878 | 257.834 | 1.00 0.00 | C |
| ATOM | 3553 | C6 | G | C | 18 | 35.480 | 145.004 | 257.215 | 1.00 0.00 | C |
| ATOM | 3554 | O6 | G | C | 18 | 36.000 | 146.103 | 257.108 | 1.00 0.00 | O |
| ATOM | 3555 | N1 | G | C | 18 | 34.219 | 144.761 | 256.660 | 1.00 0.00 | N |
| ATOM | 3556 | C2 | G | C | 18 | 33.568 | 143.574 | 256.696 | 1.00 0.00 | C |
| ATOM | 3557 | N2 | G | C | 18 | 32.357 | 143.538 | 256.119 | 1.00 0.00 | N |
| ATOM | 3558 | N3 | G | C | 18 | 34.065 | 142.485 | 257.264 | 1.00 0.00 | N |
| ATOM | 3559 | C4 | G | C | 18 | 35.267 | 142.713 | 257.803 | 1.00 0.00 | C |
| ATOM | 3560 | P | G | C | 19 | 35.278 | 136.048 | 258.183 | 1.00 0.00 | P |
| ATOM | 3561 | O1P | G | C | 19 | 34.469 | 135.741 | 259.401 | 1.00 0.00 | O |
| ATOM | 3562 | O2P | G | C | 19 | 36.492 | 135.228 | 257.907 | 1.00 0.00 | O |
| ATOM | 3563 | O5* | G | C | 19 | 34.338 | 135.860 | 256.923 | 1.00 0.00 | O |
| ATOM | 3564 | C5* | G | C | 19 | 32.972 | 136.295 | 256.988 | 1.00 0.00 | C |
| ATOM | 3565 | C4* | G | C | 19 | 32.300 | 136.095 | 255.665 | 1.00 0.00 | C |
| ATOM | 3566 | O4* | G | C | 19 | 33.091 | 136.835 | 254.685 | 1.00 0.00 | O |
| ATOM | 3567 | C3* | G | C | 19 | 32.276 | 134.647 | 255.171 | 1.00 0.00 | C |
| ATOM | 3568 | O3* | G | C | 19 | 31.218 | 134.453 | 254.231 | 1.00 0.00 | O |
| ATOM | 3569 | C2* | G | C | 19 | 33.619 | 134.573 | 254.420 | 1.00 0.00 | C |
| ATOM | 3570 | O2* | G | C | 19 | 33.638 | 133.557 | 253.450 | 1.00 0.00 | O |
| ATOM | 3571 | C1* | G | C | 19 | 33.662 | 135.939 | 253.737 | 1.00 0.00 | C |
| ATOM | 3572 | N9 | G | C | 19 | 34.969 | 136.504 | 253.444 | 1.00 0.00 | N |
| ATOM | 3573 | C8 | G | C | 19 | 36.163 | 136.230 | 254.069 | 1.00 0.00 | C |
| ATOM | 3574 | N7 | G | C | 19 | 37.116 | 137.067 | 253.733 | 1.00 0.00 | N |
| ATOM | 3575 | C5 | G | C | 19 | 36.525 | 137.912 | 252.792 | 1.00 0.00 | C |
| ATOM | 3576 | C6 | G | C | 19 | 37.055 | 139.029 | 252.068 | 1.00 0.00 | C |
| ATOM | 3577 | O6 | G | C | 19 | 38.172 | 139.498 | 252.096 | 1.00 0.00 | O |
| ATOM | 3578 | N1 | G | C | 19 | 36.109 | 139.607 | 251.242 | 1.00 0.00 | N |
| ATOM | 3579 | C2 | G | C | 19 | 34.818 | 139.192 | 251.101 | 1.00 0.00 | C |
| ATOM | 3580 | N2 | G | C | 19 | 34.070 | 139.913 | 250.215 | 1.00 0.00 | N |
| ATOM | 3581 | N3 | G | C | 19 | 34.297 | 138.158 | 251.759 | 1.00 0.00 | N |
| ATOM | 3582 | C4 | G | C | 19 | 35.209 | 137.564 | 252.582 | 1.00 0.00 | C |
| ATOM | 3583 | P | G | C | 20 | 29.713 | 134.020 | 254.720 | 1.00 0.00 | P |
| ATOM | 3584 | O1P | G | C | 20 | 28.781 | 134.348 | 253.618 | 1.00 0.00 | O |
| ATOM | 3585 | O2P | G | C | 20 | 29.489 | 134.627 | 256.033 | 1.00 0.00 | O |
| ATOM | 3586 | O5* | G | C | 20 | 29.779 | 132.440 | 254.891 | 1.00 0.00 | O |
| ATOM | 3587 | C5* | G | C | 20 | 29.924 | 131.551 | 253.797 | 1.00 0.00 | C |
| ATOM | 3588 | C4* | G | C | 20 | 29.454 | 130.161 | 254.191 | 1.00 0.00 | C |
| ATOM | 3589 | O4* | G | C | 20 | 30.504 | 129.453 | 254.925 | 1.00 0.00 | O |
| ATOM | 3590 | C3* | G | C | 20 | 28.236 | 130.148 | 255.111 | 1.00 0.00 | C |
| ATOM | 3591 | O3* | G | C | 20 | 27.038 | 130.057 | 254.340 | 1.00 0.00 | O |
| ATOM | 3592 | C2* | G | C | 20 | 28.440 | 128.899 | 255.945 | 1.00 0.00 | C |
| ATOM | 3593 | O2* | G | C | 20 | 28.042 | 127.707 | 255.332 | 1.00 0.00 | O |
| ATOM | 3594 | C1* | G | C | 20 | 29.957 | 128.852 | 256.077 | 1.00 0.00 | C |
| ATOM | 3595 | N9 | G | C | 20 | 30.411 | 129.590 | 257.248 | 1.00 0.00 | N |
| ATOM | 3596 | C8 | G | C | 20 | 31.233 | 130.682 | 257.272 | 1.00 0.00 | C |
| ATOM | 3597 | N7 | G | C | 20 | 31.435 | 131.133 | 258.486 | 1.00 0.00 | N |
| ATOM | 3598 | C5 | G | C | 20 | 30.714 | 130.271 | 259.294 | 1.00 0.00 | C |
| ATOM | 3599 | C6 | G | C | 20 | 30.540 | 130.271 | 260.693 | 1.00 0.00 | C |
| ATOM | 3600 | O6 | G | C | 20 | 31.035 | 131.029 | 261.504 | 1.00 0.00 | O |
| ATOM | 3601 | N1 | G | C | 20 | 29.681 | 129.256 | 261.111 | 1.00 0.00 | N |
| ATOM | 3602 | C2 | G | C | 20 | 29.078 | 128.342 | 260.277 | 1.00 0.00 | C |
| ATOM | 3603 | N2 | G | C | 20 | 28.257 | 127.422 | 260.868 | 1.00 0.00 | N |
| ATOM | 3604 | N3 | G | C | 20 | 29.259 | 128.324 | 258.964 | 1.00 0.00 | N |
| ATOM | 3605 | C4 | G | C | 20 | 30.077 | 129.316 | 258.549 | 1.00 0.00 | C |
| ATOM | 3606 | P | A | C | 21 | 25.895 | 131.139 | 253.589 | 1.00 0.00 | P |
| ATOM | 3607 | O1P | A | C | 21 | 24.761 | 130.791 | 253.725 | 1.00 0.00 | O |

| | | | | | | | | | | |
|---|---|---|---|---|---|---|---|---|---|---|
| ATOM | 3608 | O2P | A | C | 21 | 26.556 | 132.474 | 254.445 | 1.00 | 0.00 | O
| ATOM | 3609 | O5* | A | C | 21 | 25.491 | 130.704 | 256.058 | 1.00 | 0.00 | O
| ATOM | 3610 | C5* | A | C | 21 | 25.183 | 131.605 | 257.044 | 1.00 | 0.00 | C
| ATOM | 3611 | C4* | A | C | 21 | 25.475 | 130.993 | 258.380 | 1.00 | 0.00 | C
| ATOM | 3612 | O4* | A | C | 21 | 25.341 | 132.074 | 259.272 | 1.00 | 0.00 | O
| ATOM | 3613 | C3* | A | C | 21 | 24.657 | 129.844 | 259.000 | 1.00 | 0.00 | C
| ATOM | 3614 | O3* | A | C | 21 | 25.195 | 128.556 | 258.606 | 1.00 | 0.00 | O
| ATOM | 3615 | C2* | A | C | 21 | 24.943 | 130.065 | 260.480 | 1.00 | 0.00 | C
| ATOM | 3616 | O2* | A | C | 21 | 26.206 | 129.528 | 260.840 | 1.00 | 0.00 | O
| ATOM | 3617 | C1* | A | C | 21 | 25.068 | 131.593 | 260.560 | 1.00 | 0.00 | C
| ATOM | 3618 | N9 | A | C | 21 | 23.893 | 132.322 | 260.983 | 1.00 | 0.00 | N
| ATOM | 3619 | C8 | A | C | 21 | 22.946 | 132.847 | 260.161 | 1.00 | 0.00 | C
| ATOM | 3620 | N7 | A | C | 21 | 22.048 | 133.558 | 260.788 | 1.00 | 0.00 | N
| ATOM | 3621 | C5 | A | C | 21 | 22.421 | 133.466 | 262.112 | 1.00 | 0.00 | C
| ATOM | 3622 | C6 | A | C | 21 | 21.856 | 133.972 | 263.270 | 1.00 | 0.00 | C
| ATOM | 3623 | N6 | A | C | 21 | 20.760 | 134.737 | 263.269 | 1.00 | 0.00 | N
| ATOM | 3624 | N1 | A | C | 21 | 22.441 | 133.674 | 264.436 | 1.00 | 0.00 | N
| ATOM | 3625 | C2 | A | C | 21 | 23.540 | 132.915 | 264.418 | 1.00 | 0.00 | C
| ATOM | 3626 | N3 | A | C | 21 | 24.172 | 132.381 | 263.382 | 1.00 | 0.00 | N
| ATOM | 3627 | C4 | A | C | 21 | 23.547 | 132.695 | 262.249 | 1.00 | 0.00 | C
| ATOM | 3628 | P | G | C | 22 | 24.544 | 127.150 | 259.131 | 1.00 | 0.00 | P
| ATOM | 3629 | O1P | G | C | 22 | 25.062 | 126.051 | 258.319 | 1.00 | 0.00 | O
| ATOM | 3630 | O2P | G | C | 22 | 23.086 | 127.260 | 259.349 | 1.00 | 0.00 | O
| ATOM | 3631 | O5* | G | C | 22 | 25.160 | 126.967 | 260.568 | 1.00 | 0.00 | O
| ATOM | 3632 | C5* | G | C | 22 | 24.498 | 126.202 | 261.551 | 1.00 | 0.00 | C
| ATOM | 3633 | C4* | G | C | 22 | 25.487 | 125.819 | 262.623 | 1.00 | 0.00 | C
| ATOM | 3634 | O4* | G | C | 22 | 26.046 | 127.031 | 263.198 | 1.00 | 0.00 | O
| ATOM | 3635 | C3* | G | C | 22 | 24.923 | 125.024 | 263.784 | 1.00 | 0.00 | C
| ATOM | 3636 | O3* | G | C | 22 | 24.952 | 123.625 | 263.478 | 1.00 | 0.00 | O
| ATOM | 3637 | C2* | G | C | 22 | 25.837 | 125.447 | 264.923 | 1.00 | 0.00 | C
| ATOM | 3638 | O2* | G | C | 22 | 27.093 | 124.808 | 264.989 | 1.00 | 0.00 | O
| ATOM | 3639 | C1* | G | C | 22 | 26.061 | 126.923 | 264.603 | 1.00 | 0.00 | C
| ATOM | 3640 | N9 | G | C | 22 | 24.994 | 127.757 | 265.143 | 1.00 | 0.00 | N
| ATOM | 3641 | C8 | G | C | 22 | 24.081 | 128.505 | 264.442 | 1.00 | 0.00 | C
| ATOM | 3642 | N7 | G | C | 22 | 23.288 | 129.189 | 265.221 | 1.00 | 0.00 | N
| ATOM | 3643 | C5 | G | C | 22 | 23.694 | 128.852 | 266.508 | 1.00 | 0.00 | C
| ATOM | 3644 | C6 | G | C | 22 | 23.215 | 129.301 | 267.758 | 1.00 | 0.00 | C
| ATOM | 3645 | O6 | G | C | 22 | 22.310 | 130.098 | 267.973 | 1.00 | 0.00 | O
| ATOM | 3646 | N1 | G | C | 22 | 23.909 | 128.729 | 268.816 | 1.00 | 0.00 | N
| ATOM | 3647 | C2 | G | C | 22 | 24.947 | 127.836 | 268.681 | 1.00 | 0.00 | C
| ATOM | 3648 | N2 | G | C | 22 | 25.505 | 127.393 | 269.816 | 1.00 | 0.00 | N
| ATOM | 3649 | N3 | G | C | 22 | 25.401 | 127.416 | 267.520 | 1.00 | 0.00 | N
| ATOM | 3650 | C4 | G | C | 22 | 24.727 | 127.966 | 266.480 | 1.00 | 0.00 | C
| ATOM | 3651 | P | A | C | 23 | 23.821 | 122.645 | 264.082 | 1.00 | 0.00 | P
| ATOM | 3652 | O1P | A | C | 23 | 23.835 | 121.338 | 263.386 | 1.00 | 0.00 | O
| ATOM | 3653 | O2P | A | C | 23 | 22.572 | 123.434 | 264.106 | 1.00 | 0.00 | O
| ATOM | 3654 | O5* | A | C | 23 | 24.293 | 122.414 | 265.571 | 1.00 | 0.00 | O
| ATOM | 3655 | C5* | A | C | 23 | 25.550 | 121.834 | 265.830 | 1.00 | 0.00 | C
| ATOM | 3656 | C4* | A | C | 23 | 25.780 | 121.716 | 267.310 | 1.00 | 0.00 | C
| ATOM | 3657 | O4* | A | C | 23 | 26.031 | 123.014 | 267.907 | 1.00 | 0.00 | O
| ATOM | 3658 | C3* | A | C | 23 | 24.634 | 121.133 | 268.117 | 1.00 | 0.00 | C
| ATOM | 3659 | O3* | A | C | 23 | 24.735 | 119.714 | 268.061 | 1.00 | 0.00 | O
| ATOM | 3660 | C2* | A | C | 23 | 24.994 | 121.623 | 269.504 | 1.00 | 0.00 | C
| ATOM | 3661 | O2* | A | C | 23 | 26.059 | 120.845 | 270.022 | 1.00 | 0.00 | O
| ATOM | 3662 | C1* | A | C | 23 | 25.460 | 123.052 | 269.200 | 1.00 | 0.00 | C
| ATOM | 3663 | N9 | A | C | 23 | 24.343 | 123.997 | 269.148 | 1.00 | 0.00 | N
| ATOM | 3664 | C8 | A | C | 23 | 23.710 | 124.469 | 268.022 | 1.00 | 0.00 | C
| ATOM | 3665 | N7 | A | C | 23 | 22.779 | 125.359 | 268.273 | 1.00 | 0.00 | N
| ATOM | 3666 | C5 | A | C | 23 | 22.782 | 125.450 | 269.658 | 1.00 | 0.00 | C
| ATOM | 3667 | C6 | A | C | 23 | 22.004 | 126.190 | 270.537 | 1.00 | 0.00 | C
| ATOM | 3668 | N6 | A | C | 23 | 21.051 | 127.037 | 270.130 | 1.00 | 0.00 | N
| ATOM | 3669 | N1 | A | C | 23 | 22.232 | 126.044 | 271.857 | 1.00 | 0.00 | N
| ATOM | 3670 | C2 | A | C | 23 | 23.197 | 125.196 | 272.252 | 1.00 | 0.00 | C
| ATOM | 3671 | N3 | A | C | 23 | 23.997 | 124.440 | 271.517 | 1.00 | 0.00 | N
| ATOM | 3672 | C4 | A | C | 23 | 23.733 | 124.614 | 270.209 | 1.00 | 0.00 | C
| ATOM | 3673 | P | G | C | 24 | 23.405 | 118.805 | 268.199 | 1.00 | 0.00 | P
| ATOM | 3674 | O1P | G | C | 24 | 23.889 | 117.453 | 267.863 | 1.00 | 0.00 | O
| ATOM | 3675 | O2P | G | C | 24 | 22.310 | 119.411 | 267.408 | 1.00 | 0.00 | O
| ATOM | 3676 | O5* | G | C | 24 | 23.053 | 118.925 | 269.742 | 1.00 | 0.00 | O
| ATOM | 3677 | C5* | G | C | 24 | 24.040 | 118.657 | 270.710 | 1.00 | 0.00 | C
| ATOM | 3678 | C4* | G | C | 24 | 23.510 | 118.951 | 272.079 | 1.00 | 0.00 | C
| ATOM | 3679 | O4* | G | C | 24 | 23.689 | 120.367 | 272.325 | 1.00 | 0.00 | O
| ATOM | 3680 | C3* | G | C | 24 | 22.019 | 118.714 | 272.272 | 1.00 | 0.00 | C
| ATOM | 3681 | O3* | G | C | 24 | 21.797 | 117.364 | 272.663 | 1.00 | 0.00 | O
| ATOM | 3682 | C2* | G | C | 24 | 21.735 | 119.657 | 273.427 | 1.00 | 0.00 | C
| ATOM | 3683 | O2* | G | C | 24 | 22.274 | 119.177 | 274.639 | 1.00 | 0.00 | O
| ATOM | 3684 | C1* | G | C | 24 | 22.566 | 120.874 | 273.009 | 1.00 | 0.00 | C
| ATOM | 3685 | N9 | G | C | 24 | 21.828 | 121.719 | 272.087 | 1.00 | 0.00 | N
| ATOM | 3686 | C8 | G | C | 24 | 21.824 | 121.663 | 270.718 | 1.00 | 0.00 | C
| ATOM | 3687 | N7 | G | C | 24 | 20.985 | 122.504 | 270.177 | 1.00 | 0.00 | N
| ATOM | 3688 | C5 | G | C | 24 | 20.430 | 123.169 | 271.265 | 1.00 | 0.00 | C
| ATOM | 3689 | C6 | G | C | 24 | 19.436 | 124.173 | 271.313 | 1.00 | 0.00 | C
| ATOM | 3690 | O6 | G | C | 24 | 18.844 | 124.723 | 270.367 | 1.00 | 0.00 | O
| ATOM | 3691 | N1 | G | C | 24 | 19.136 | 124.528 | 272.626 | 1.00 | 0.00 | N
| ATOM | 3692 | C2 | G | C | 24 | 19.718 | 123.988 | 273.746 | 1.00 | 0.00 | C
| ATOM | 3693 | N2 | G | C | 24 | 19.285 | 124.449 | 274.928 | 1.00 | 0.00 | N
| ATOM | 3694 | N3 | G | C | 24 | 20.659 | 123.057 | 273.709 | 1.00 | 0.00 | N

```
ATOM    3695  C4     G  C  24      20.956 122.698 272.444  1.00  0.00           C
ATOM    3696  P      C  C  25      20.450 116.609 272.204  1.00  0.00           P
ATOM    3697  O1P    C  C  25      20.548 115.215 272.737  1.00  0.00           O
ATOM    3698  O2P    C  C  25      20.238 116.821 270.769  1.00  0.00           O
ATOM    3699  O5*    C  C  25      19.297 117.383 272.980  1.00  0.00           O
ATOM    3700  C5*    C  C  25      19.316 117.472 274.390  1.00  0.00           C
ATOM    3701  C4*    C  C  25      18.285 118.464 274.872  1.00  0.00           C
ATOM    3702  O4*    C  C  25      18.688 119.823 274.528  1.00  0.00           O
ATOM    3703  C3*    C  C  25      16.875 118.367 274.302  1.00  0.00           C
ATOM    3704  O3*    C  C  25      16.140 117.302 274.905  1.00  0.00           O
ATOM    3705  C2*    C  C  25      16.329 119.732 274.714  1.00  0.00           C
ATOM    3706  O2*    C  C  25      16.096 119.808 276.107  1.00  0.00           O
ATOM    3707  C1*    C  C  25      17.529 120.632 274.397  1.00  0.00           C
ATOM    3708  N1     C  C  25      17.472 121.126 273.027  1.00  0.00           N
ATOM    3709  C2     C  C  25      16.672 122.221 272.758  1.00  0.00           C
ATOM    3710  O2     C  C  25      16.063 122.746 273.694  1.00  0.00           O
ATOM    3711  N3     C  C  25      16.578 122.681 271.490  1.00  0.00           N
ATOM    3712  C4     C  C  25      17.251 122.079 270.510  1.00  0.00           C
ATOM    3713  N4     C  C  25      17.125 122.566 269.271  1.00  0.00           N
ATOM    3714  C5     C  C  25      18.087 120.952 270.757  1.00  0.00           C
ATOM    3715  C6     C  C  25      18.174 120.514 272.027  1.00  0.00           C
HETATM  3716  P      M2G C 26      14.647 116.174 273.907  1.00  0.00           P
HETATM  3717  O1P    M2G C 26      14.713 115.473 272.608  1.00  0.00           O
HETATM  3718  O2P    M2G C 26      13.903 115.561 275.031  1.00  0.00           O
HETATM  3719  O5*    M2G C 26      14.041 117.622 273.660  1.00  0.00           O
HETATM  3720  C5*    M2G C 26      13.434 118.341 274.724  1.00  0.00           C
HETATM  3721  C4*    M2G C 26      12.885 119.651 274.219  1.00  0.00           C
HETATM  3722  O4*    M2G C 26      13.925 120.389 273.509  1.00  0.00           O
HETATM  3723  C3*    M2G C 26      11.790 119.522 273.181  1.00  0.00           C
HETATM  3724  O3*    M2G C 26      10.542 119.282 273.808  1.00  0.00           O
HETATM  3725  C2*    M2G C 26      11.829 120.898 272.536  1.00  0.00           C
HETATM  3726  O2*    M2G C 26      11.288 121.889 273.381  1.00  0.00           O
HETATM  3727  C1*    M2G C 26      13.338 121.107 272.427  1.00  0.00           C
HETATM  3728  N9     M2G C 26      13.904 120.602 271.178  1.00  0.00           N
HETATM  3729  C8     M2G C 26      14.595 119.425 270.988  1.00  0.00           C
HETATM  3730  N7     M2G C 26      14.988 119.254 269.759  1.00  0.00           N
HETATM  3731  C5     M2G C 26      14.536 120.392 269.103  1.00  0.00           C
HETATM  3732  C6     M2G C 26      14.675 120.775 267.757  1.00  0.00           C
HETATM  3733  O6     M2G C 26      15.245 120.164 266.845  1.00  0.00           O
HETATM  3734  N1     M2G C 26      14.065 121.998 267.505  1.00  0.00           N
HETATM  3735  C2     M2G C 26      13.399 122.757 268.446  1.00  0.00           C
HETATM  3736  N2     M2G C 26      12.834 123.889 268.015  1.00  0.00           N
HETATM  3737  N3     M2G C 26      13.268 122.410 269.714  1.00  0.00           N
HETATM  3738  C4     M2G C 26      13.857 121.221 269.969  1.00  0.00           C
HETATM  3739  CM1    M2G C 26      11.828 124.572 268.852  1.00  0.00           C
HETATM  3740  CM2    M2G C 26      13.214 124.450 266.714  1.00  0.00           C
ATOM    3741  P      C  C  27       9.559 118.172 273.199  1.00  0.00           P
ATOM    3742  O1P    C  C  27       8.411 118.026 274.136  1.00  0.00           O
ATOM    3743  O2P    C  C  27      10.388 116.981 272.868  1.00  0.00           O
ATOM    3744  O5*    C  C  27       9.023 118.830 271.849  1.00  0.00           O
ATOM    3745  C5*    C  C  27       8.295 120.045 271.882  1.00  0.00           C
ATOM    3746  C4*    C  C  27       8.078 120.573 270.484  1.00  0.00           C
ATOM    3747  O4*    C  C  27       9.353 120.995 269.924  1.00  0.00           O
ATOM    3748  C3*    C  C  27       7.546 119.592 269.449  1.00  0.00           C
ATOM    3749  O3*    C  C  27       6.129 119.436 269.523  1.00  0.00           O
ATOM    3750  C2*    C  C  27       7.943 120.297 268.154  1.00  0.00           C
ATOM    3751  O2*    C  C  27       7.091 121.383 267.839  1.00  0.00           O
ATOM    3752  C1*    C  C  27       9.338 120.815 268.513  1.00  0.00           C
ATOM    3753  N1     C  C  27      10.421 119.885 268.145  1.00  0.00           N
ATOM    3754  C2     C  C  27      10.835 119.820 266.806  1.00  0.00           C
ATOM    3755  O2     C  C  27      10.257 120.516 265.961  1.00  0.00           O
ATOM    3756  N3     C  C  27      11.849 118.990 266.462  1.00  0.00           N
ATOM    3757  C4     C  C  27      12.432 118.236 267.389  1.00  0.00           C
ATOM    3758  N4     C  C  27      13.419 117.436 266.997  1.00  0.00           N
ATOM    3759  C5     C  C  27      12.022 118.268 268.761  1.00  0.00           C
ATOM    3760  C6     C  C  27      11.021 119.102 269.091  1.00  0.00           C
ATOM    3761  P      C  C  28       5.454 118.019 269.148  1.00  0.00           P
ATOM    3762  O1P    C  C  28       4.027 118.155 269.515  1.00  0.00           O
ATOM    3763  O2P    C  C  28       6.258 116.912 269.723  1.00  0.00           O
ATOM    3764  O5*    C  C  28       5.543 117.900 267.563  1.00  0.00           O
ATOM    3765  C5*    C  C  28       4.718 118.700 266.738  1.00  0.00           C
ATOM    3766  C4*    C  C  28       5.074 118.494 265.290  1.00  0.00           C
ATOM    3767  O4*    C  C  28       6.450 118.906 265.079  1.00  0.00           O
ATOM    3768  C3*    C  C  28       5.074 117.062 264.794  1.00  0.00           C
ATOM    3769  O3*    C  C  28       3.762 116.609 264.477  1.00  0.00           O
ATOM    3770  C2*    C  C  28       5.919 117.199 263.542  1.00  0.00           C
ATOM    3771  O2*    C  C  28       5.213 117.840 262.493  1.00  0.00           O
ATOM    3772  C1*    C  C  28       7.029 118.107 264.068  1.00  0.00           C
ATOM    3773  N1     C  C  28       8.146 117.364 264.664  1.00  0.00           N
ATOM    3774  C2     C  C  28       9.089 116.805 263.811  1.00  0.00           C
ATOM    3775  O2     C  C  28       8.929 116.943 262.595  1.00  0.00           O
ATOM    3776  N3     C  C  28      10.144 116.127 264.329  1.00  0.00           N
ATOM    3777  C4     C  C  28      10.267 115.993 265.653  1.00  0.00           C
ATOM    3778  N4     C  C  28      11.338 115.304 266.127  1.00  0.00           N
ATOM    3779  C5     C  C  28       9.307 116.550 266.555  1.00  0.00           C
ATOM    3780  C6     C  C  28       8.272 117.223 266.020  1.00  0.00           C
ATOM    3781  P      A  C  29       3.391 115.065 264.703  1.00  0.00           P
```

| | | | | | | | | | | | |
|---|---|---|---|---|---|---|---|---|---|---|---|
| ATOM | 3782 | O1P | A | C | 29 | 1.911 | 114.951 | 264.561 | 1.00 | 0.00 | O |
| ATOM | 3783 | O2P | A | C | 29 | 4.054 | 114.580 | 265.952 | 1.00 | 0.00 | O |
| ATOM | 3784 | O5* | A | C | 29 | 4.084 | 114.308 | 263.484 | 1.00 | 0.00 | O |
| ATOM | 3785 | C5* | A | C | 29 | 3.792 | 114.674 | 262.134 | 1.00 | 0.00 | C |
| ATOM | 3786 | C4* | A | C | 29 | 4.819 | 114.082 | 261.177 | 1.00 | 0.00 | C |
| ATOM | 3787 | O4* | A | C | 29 | 6.121 | 114.698 | 261.370 | 1.00 | 0.00 | O |
| ATOM | 3788 | C3* | A | C | 29 | 5.091 | 112.585 | 261.257 | 1.00 | 0.00 | C |
| ATOM | 3789 | O3* | A | C | 29 | 4.110 | 111.865 | 260.517 | 1.00 | 0.00 | O |
| ATOM | 3790 | C2* | A | C | 29 | 6.451 | 112.484 | 260.572 | 1.00 | 0.00 | C |
| ATOM | 3791 | O2* | A | C | 29 | 6.375 | 112.515 | 259.155 | 1.00 | 0.00 | O |
| ATOM | 3792 | C1* | A | C | 29 | 7.144 | 113.746 | 261.093 | 1.00 | 0.00 | C |
| ATOM | 3793 | N9 | A | C | 29 | 7.906 | 113.507 | 262.324 | 1.00 | 0.00 | N |
| ATOM | 3794 | C8 | A | C | 29 | 7.569 | 113.830 | 263.619 | 1.00 | 0.00 | C |
| ATOM | 3795 | N7 | A | C | 29 | 8.472 | 113.472 | 264.505 | 1.00 | 0.00 | N |
| ATOM | 3796 | C5 | A | C | 29 | 9.469 | 112.879 | 263.739 | 1.00 | 0.00 | C |
| ATOM | 3797 | C6 | A | C | 29 | 10.691 | 112.288 | 264.078 | 1.00 | 0.00 | C |
| ATOM | 3798 | N6 | A | C | 29 | 11.158 | 112.203 | 265.324 | 1.00 | 0.00 | N |
| ATOM | 3799 | N1 | A | C | 29 | 11.438 | 111.778 | 263.076 | 1.00 | 0.00 | N |
| ATOM | 3800 | C2 | A | C | 29 | 10.977 | 111.868 | 261.823 | 1.00 | 0.00 | C |
| ATOM | 3801 | N3 | A | C | 29 | 9.851 | 112.400 | 261.380 | 1.00 | 0.00 | N |
| ATOM | 3802 | C4 | A | C | 29 | 9.131 | 112.895 | 262.399 | 1.00 | 0.00 | C |
| ATOM | 3803 | P | G | C | 30 | 3.866 | 110.306 | 260.816 | 1.00 | 0.00 | P |
| ATOM | 3804 | O1P | G | C | 30 | 2.679 | 109.925 | 260.000 | 1.00 | 0.00 | O |
| ATOM | 3805 | O2P | G | C | 30 | 3.848 | 110.094 | 262.285 | 1.00 | 0.00 | O |
| ATOM | 3806 | O5* | G | C | 30 | 5.158 | 109.583 | 260.215 | 1.00 | 0.00 | O |
| ATOM | 3807 | C5* | G | C | 30 | 5.500 | 109.715 | 258.835 | 1.00 | 0.00 | C |
| ATOM | 3808 | C4* | G | C | 30 | 6.712 | 108.871 | 258.520 | 1.00 | 0.00 | C |
| ATOM | 3809 | O4* | G | C | 30 | 7.917 | 109.528 | 258.996 | 1.00 | 0.00 | O |
| ATOM | 3810 | C3* | G | C | 30 | 6.744 | 107.529 | 259.220 | 1.00 | 0.00 | C |
| ATOM | 3811 | O3* | G | C | 30 | 5.949 | 106.587 | 258.515 | 1.00 | 0.00 | O |
| ATOM | 3812 | C2* | G | C | 30 | 8.232 | 107.195 | 259.198 | 1.00 | 0.00 | C |
| ATOM | 3813 | O2* | G | C | 30 | 8.747 | 106.758 | 257.954 | 1.00 | 0.00 | O |
| ATOM | 3814 | C1* | G | C | 30 | 8.826 | 108.560 | 259.508 | 1.00 | 0.00 | C |
| ATOM | 3815 | N9 | G | C | 30 | 8.920 | 108.739 | 260.946 | 1.00 | 0.00 | N |
| ATOM | 3816 | C8 | G | C | 30 | 7.995 | 109.335 | 261.760 | 1.00 | 0.00 | C |
| ATOM | 3817 | N7 | G | C | 30 | 8.357 | 109.356 | 263.014 | 1.00 | 0.00 | N |
| ATOM | 3818 | C5 | G | C | 30 | 9.599 | 108.735 | 263.028 | 1.00 | 0.00 | C |
| ATOM | 3819 | C6 | G | C | 30 | 10.499 | 108.492 | 264.108 | 1.00 | 0.00 | C |
| ATOM | 3820 | O6 | G | C | 30 | 10.361 | 108.781 | 265.306 | 1.00 | 0.00 | O |
| ATOM | 3821 | N1 | G | C | 30 | 11.658 | 107.847 | 263.677 | 1.00 | 0.00 | N |
| ATOM | 3822 | C2 | G | C | 30 | 11.922 | 107.488 | 262.374 | 1.00 | 0.00 | C |
| ATOM | 3823 | N2 | G | C | 30 | 13.097 | 106.863 | 262.160 | 1.00 | 0.00 | N |
| ATOM | 3824 | N3 | G | C | 30 | 11.097 | 107.720 | 261.358 | 1.00 | 0.00 | N |
| ATOM | 3825 | C4 | G | C | 30 | 9.960 | 108.342 | 261.759 | 1.00 | 0.00 | C |
| ATOM | 3826 | P | A | C | 31 | 5.558 | 105.196 | 259.215 | 1.00 | 0.00 | P |
| ATOM | 3827 | O1P | A | C | 31 | 4.932 | 104.357 | 258.165 | 1.00 | 0.00 | O |
| ATOM | 3828 | O2P | A | C | 31 | 4.806 | 105.486 | 260.467 | 1.00 | 0.00 | O |
| ATOM | 3829 | O5* | A | C | 31 | 6.955 | 104.547 | 259.600 | 1.00 | 0.00 | O |
| ATOM | 3830 | C5* | A | C | 31 | 7.806 | 104.029 | 258.590 | 1.00 | 0.00 | C |
| ATOM | 3831 | C4* | A | C | 31 | 9.000 | 103.370 | 259.217 | 1.00 | 0.00 | C |
| ATOM | 3832 | O4* | A | C | 31 | 9.820 | 104.390 | 259.845 | 1.00 | 0.00 | O |
| ATOM | 3833 | C3* | A | C | 31 | 8.677 | 102.388 | 260.338 | 1.00 | 0.00 | C |
| ATOM | 3834 | O3* | A | C | 31 | 8.438 | 101.078 | 259.815 | 1.00 | 0.00 | O |
| ATOM | 3835 | C2* | A | C | 31 | 9.970 | 102.416 | 261.141 | 1.00 | 0.00 | C |
| ATOM | 3836 | O2* | A | C | 31 | 10.988 | 101.630 | 260.551 | 1.00 | 0.00 | O |
| ATOM | 3837 | C1* | A | C | 31 | 10.329 | 103.903 | 261.074 | 1.00 | 0.00 | C |
| ATOM | 3838 | N9 | A | C | 31 | 9.684 | 104.632 | 262.156 | 1.00 | 0.00 | N |
| ATOM | 3839 | C8 | A | C | 31 | 8.478 | 105.288 | 262.155 | 1.00 | 0.00 | C |
| ATOM | 3840 | N7 | A | C | 31 | 8.159 | 105.806 | 263.313 | 1.00 | 0.00 | N |
| ATOM | 3841 | C5 | A | C | 31 | 9.231 | 105.482 | 264.128 | 1.00 | 0.00 | C |
| ATOM | 3842 | C6 | A | C | 31 | 9.508 | 105.759 | 265.474 | 1.00 | 0.00 | C |
| ATOM | 3843 | N6 | A | C | 31 | 8.680 | 106.449 | 266.270 | 1.00 | 0.00 | N |
| ATOM | 3844 | N1 | A | C | 31 | 10.678 | 105.304 | 265.983 | 1.00 | 0.00 | N |
| ATOM | 3845 | C2 | A | C | 31 | 11.504 | 104.620 | 265.176 | 1.00 | 0.00 | C |
| ATOM | 3846 | N3 | A | C | 31 | 11.353 | 104.296 | 263.890 | 1.00 | 0.00 | N |
| ATOM | 3847 | C4 | A | C | 31 | 10.181 | 104.764 | 263.425 | 1.00 | 0.00 | C |
| HETATM | 3848 | N1 | OMC | C | 32 | 8.170 | 101.739 | 265.293 | 1.00 | 0.00 | N |
| HETATM | 3849 | C2 | OMC | C | 32 | 8.074 | 102.643 | 266.331 | 1.00 | 0.00 | C |
| HETATM | 3850 | N3 | OMC | C | 32 | 7.173 | 103.650 | 266.253 | 1.00 | 0.00 | N |
| HETATM | 3851 | C4 | OMC | C | 32 | 6.398 | 103.766 | 265.171 | 1.00 | 0.00 | C |
| HETATM | 3852 | C5 | OMC | C | 32 | 6.497 | 102.860 | 264.077 | 1.00 | 0.00 | C |
| HETATM | 3853 | C6 | OMC | C | 32 | 7.391 | 101.871 | 264.179 | 1.00 | 0.00 | C |
| HETATM | 3854 | O2 | OMC | C | 32 | 8.822 | 102.498 | 267.308 | 1.00 | 0.00 | O |
| HETATM | 3855 | N4 | OMC | C | 32 | 5.506 | 104.765 | 265.131 | 1.00 | 0.00 | N |
| HETATM | 3856 | C1* | OMC | C | 32 | 9.108 | 100.632 | 265.426 | 1.00 | 0.00 | C |
| HETATM | 3857 | C2* | OMC | C | 32 | 8.399 | 99.365 | 265.890 | 1.00 | 0.00 | C |
| HETATM | 3858 | O2* | OMC | C | 32 | 9.339 | 98.564 | 266.640 | 1.00 | 0.00 | O |
| HETATM | 3859 | CM2 | OMC | C | 32 | 9.644 | 98.922 | 268.010 | 1.00 | 0.00 | C |
| HETATM | 3860 | C3* | OMC | C | 32 | 8.007 | 98.746 | 264.558 | 1.00 | 0.00 | C |
| HETATM | 3861 | C4* | OMC | C | 32 | 9.227 | 99.043 | 263.708 | 1.00 | 0.00 | C |
| HETATM | 3862 | O4* | OMC | C | 32 | 9.658 | 100.355 | 264.153 | 1.00 | 0.00 | O |
| HETATM | 3863 | O3* | OMC | C | 32 | 7.794 | 97.345 | 264.665 | 1.00 | 0.00 | O |
| HETATM | 3864 | C5* | OMC | C | 32 | 8.959 | 99.099 | 262.231 | 1.00 | 0.00 | C |
| HETATM | 3865 | O5* | OMC | C | 32 | 7.826 | 99.917 | 261.974 | 1.00 | 0.00 | O |
| HETATM | 3866 | P | OMC | C | 32 | 7.314 | 100.136 | 260.482 | 1.00 | 0.00 | P |
| HETATM | 3867 | O1P | OMC | C | 32 | 6.041 | 100.904 | 260.513 | 1.00 | 0.00 | O |
| HETATM | 3868 | O2P | OMC | C | 32 | 7.379 | 98.827 | 259.773 | 1.00 | 0.00 | O |

```
ATOM    3869  P     U C  33       6.372  96.799 265.183  1.00  0.00           P
ATOM    3870  O1P   U C  33       6.555  95.374 265.550  1.00  0.00           O
ATOM    3871  O2P   U C  33       5.321  97.185 264.201  1.00  0.00           O
ATOM    3872  O5*   U C  33       6.114  97.638 266.511  1.00  0.00           O
ATOM    3873  C5*   U C  33       6.402  97.097 267.798  1.00  0.00           C
ATOM    3874  C4*   U C  33       5.452  97.677 268.821  1.00  0.00           C
ATOM    3875  O4*   U C  33       5.621  99.119 268.844  1.00  0.00           O
ATOM    3876  C3*   U C  33       3.975  97.474 268.498  1.00  0.00           C
ATOM    3877  O3*   U C  33       3.506  96.223 269.011  1.00  0.00           O
ATOM    3878  C2*   U C  33       3.306  98.650 269.206  1.00  0.00           C
ATOM    3879  O2*   U C  33       3.011  98.387 270.560  1.00  0.00           O
ATOM    3880  C1*   U C  33       4.374  99.741 269.096  1.00  0.00           C
ATOM    3881  N1    U C  33       4.076 100.669 268.003  1.00  0.00           N
ATOM    3882  C2    U C  33       3.403 101.815 268.337  1.00  0.00           C
ATOM    3883  O2    U C  33       3.119 102.084 269.487  1.00  0.00           O
ATOM    3884  N3    U C  33       3.074 102.633 267.280  1.00  0.00           N
ATOM    3885  C4    U C  33       3.356 102.420 265.945  1.00  0.00           C
ATOM    3886  O4    U C  33       2.971 103.241 265.102  1.00  0.00           O
ATOM    3887  C5    U C  33       4.086 101.211 265.679  1.00  0.00           C
ATOM    3888  C6    U C  33       4.419 100.400 266.696  1.00  0.00           C
HETATM  3889  P   OMG C  34       2.652  95.106 268.984  1.00  0.00           P
HETATM  3890  O1P OMG C  34       3.505  94.260 268.100  1.00  0.00           O
HETATM  3891  O2P OMG C  34       1.795  94.455 270.008  1.00  0.00           O
HETATM  3892  O5* OMG C  34       1.728  96.047 268.085  1.00  0.00           O
HETATM  3893  C5* OMG C  34       0.533  95.561 267.484  1.00  0.00           C
HETATM  3894  C4* OMG C  34      -0.666  96.147 268.183  1.00  0.00           C
HETATM  3895  O4* OMG C  34      -0.697  95.599 269.518  1.00  0.00           O
HETATM  3896  C3* OMG C  34      -0.612  97.650 268.405  1.00  0.00           C
HETATM  3897  O3* OMG C  34      -1.112  98.380 267.277  1.00  0.00           O
HETATM  3898  C2* OMG C  34      -1.484  97.844 269.648  1.00  0.00           C
HETATM  3899  O2* OMG C  34      -2.891  98.078 269.390  1.00  0.00           O
HETATM  3900  CM2 OMG C  34      -3.745  98.539 270.466  1.00  0.00           C
HETATM  3901  C1* OMG C  34      -1.304  96.523 270.393  1.00  0.00           C
HETATM  3902  N9  OMG C  34      -0.490  96.607 271.599  1.00  0.00           N
HETATM  3903  C8  OMG C  34       0.595  95.825 271.921  1.00  0.00           C
HETATM  3904  N7  OMG C  34       1.097  96.094 273.097  1.00  0.00           N
HETATM  3905  C5  OMG C  34       0.300  97.126 273.580  1.00  0.00           C
HETATM  3906  C6  OMG C  34       0.347  97.824 274.826  1.00  0.00           C
HETATM  3907  O6  OMG C  34       1.140  97.668 275.781  1.00  0.00           O
HETATM  3908  N1  OMG C  34      -0.661  98.793 274.904  1.00  0.00           N
HETATM  3909  C2  OMG C  34      -1.595  99.059 273.915  1.00  0.00           C
HETATM  3910  N2  OMG C  34      -2.482 100.039 274.178  1.00  0.00           N
HETATM  3911  N3  OMG C  34      -1.649  98.411 272.756  1.00  0.00           N
HETATM  3912  C4  OMG C  34      -0.680  97.465 272.658  1.00  0.00           C
ATOM    3913  P     A C  35      -0.252  99.373 266.381  1.00  0.00           P
ATOM    3914  O1P   A C  35      -0.945  99.752 265.120  1.00  0.00           O
ATOM    3915  O2P   A C  35       0.757  98.281 266.380  1.00  0.00           O
ATOM    3916  O5*   A C  35       0.452 100.668 266.983  1.00  0.00           O
ATOM    3917  C5*   A C  35       0.613 100.794 268.391  1.00  0.00           C
ATOM    3918  C4*   A C  35      -0.225 101.923 268.944  1.00  0.00           C
ATOM    3919  O4*   A C  35      -1.027 101.373 270.030  1.00  0.00           O
ATOM    3920  C3*   A C  35       0.591 103.058 269.569  1.00  0.00           C
ATOM    3921  O3*   A C  35       0.681 104.157 268.657  1.00  0.00           O
ATOM    3922  C2*   A C  35      -0.229 103.429 270.804  1.00  0.00           C
ATOM    3923  O2*   A C  35      -1.321 104.288 270.513  1.00  0.00           O
ATOM    3924  C1*   A C  35      -0.737 102.058 271.227  1.00  0.00           C
ATOM    3925  N9    A C  35       0.250 101.270 271.953  1.00  0.00           N
ATOM    3926  C8    A C  35       0.964 100.184 271.512  1.00  0.00           C
ATOM    3927  N7    A C  35       1.779  99.690 272.413  1.00  0.00           N
ATOM    3928  C5    A C  35       1.588 100.503 273.519  1.00  0.00           C
ATOM    3929  C6    A C  35       2.167 100.509 274.807  1.00  0.00           C
ATOM    3930  N6    A C  35       3.092  99.637 275.213  1.00  0.00           N
ATOM    3931  N1    A C  35       1.758 101.465 275.677  1.00  0.00           N
ATOM    3932  C2    A C  35       0.832 102.346 275.267  1.00  0.00           C
ATOM    3933  N3    A C  35       0.220 102.443 274.081  1.00  0.00           N
ATOM    3934  C4    A C  35       0.649 101.482 273.248  1.00  0.00           C
ATOM    3935  P     A C  36       0.370 105.771 268.205  1.00  0.00           P
ATOM    3936  O1P   A C  36      -0.763 106.546 267.601  1.00  0.00           O
ATOM    3937  O2P   A C  36       1.648 105.649 267.475  1.00  0.00           O
ATOM    3938  O5*   A C  36       0.663 106.371 269.641  1.00  0.00           O
ATOM    3939  C5*   A C  36       1.993 106.581 270.069  1.00  0.00           C
ATOM    3940  C4*   A C  36       1.989 107.002 271.512  1.00  0.00           C
ATOM    3941  O4*   A C  36       1.445 105.923 272.330  1.00  0.00           O
ATOM    3942  C3*   A C  36       3.361 107.232 272.121  1.00  0.00           C
ATOM    3943  O3*   A C  36       3.894 108.504 271.772  1.00  0.00           O
ATOM    3944  C2*   A C  36       3.044 107.103 273.604  1.00  0.00           C
ATOM    3945  O2*   A C  36       2.352 108.225 274.132  1.00  0.00           O
ATOM    3946  C1*   A C  36       2.126 105.880 273.578  1.00  0.00           C
ATOM    3947  N9    A C  36       2.907 104.649 273.623  1.00  0.00           N
ATOM    3948  C8    A C  36       3.165 103.769 272.607  1.00  0.00           C
ATOM    3949  N7    A C  36       3.938 102.770 272.957  1.00  0.00           N
ATOM    3950  C5    A C  36       4.197 103.007 274.300  1.00  0.00           C
ATOM    3951  C6    A C  36       4.975 102.320 275.251  1.00  0.00           C
ATOM    3952  N6    A C  36       5.654 101.198 274.988  1.00  0.00           N
ATOM    3953  N1    A C  36       5.035 102.836 276.500  1.00  0.00           N
ATOM    3954  C2    A C  36       4.361 103.966 276.759  1.00  0.00           C
ATOM    3955  N3    A C  36       3.602 104.699 275.951  1.00  0.00           N
```

| | | | | | | | | | | |
|---|---|---|---|---|---|---|---|---|---|---|
| ATOM | 3956 | C4 | A | C | 36 | 3.561 | 104.158 | 274.723 | 1.00 | 0.00 | C |
| HETATM | 3957 | N1 | YG | C | 37 | 9.900 | 101.763 | 274.087 | 1.00 | 0.00 | N |
| HETATM | 3958 | N2 | YG | C | 37 | 11.021 | 101.851 | 276.075 | 1.00 | 0.00 | N |
| HETATM | 3959 | C2 | YG | C | 37 | 10.051 | 102.412 | 275.269 | 1.00 | 0.00 | C |
| HETATM | 3960 | N3 | YG | C | 37 | 9.338 | 103.505 | 275.643 | 1.00 | 0.00 | N |
| HETATM | 3961 | C3 | YG | C | 37 | 9.545 | 104.194 | 276.965 | 1.00 | 0.00 | C |
| HETATM | 3962 | C4 | YG | C | 37 | 8.433 | 103.885 | 274.672 | 1.00 | 0.00 | C |
| HETATM | 3963 | C5 | YG | C | 37 | 8.206 | 103.293 | 273.439 | 1.00 | 0.00 | C |
| HETATM | 3964 | C6 | YG | C | 37 | 8.975 | 102.130 | 273.069 | 1.00 | 0.00 | C |
| HETATM | 3965 | O6 | YG | C | 37 | 8.910 | 101.460 | 272.028 | 1.00 | 0.00 | O |
| HETATM | 3966 | N7 | YG | C | 37 | 7.218 | 103.976 | 272.738 | 1.00 | 0.00 | N |
| HETATM | 3967 | C8 | YG | C | 37 | 6.867 | 104.954 | 273.534 | 1.00 | 0.00 | C |
| HETATM | 3968 | N9 | YG | C | 37 | 7.566 | 104.966 | 274.721 | 1.00 | 0.00 | N |
| HETATM | 3969 | C10 | YG | C | 37 | 12.613 | 99.828 | 275.801 | 1.00 | 0.00 | C |
| HETATM | 3970 | C11 | YG | C | 37 | 11.526 | 100.777 | 275.357 | 1.00 | 0.00 | C |
| HETATM | 3971 | C12 | YG | C | 37 | 10.833 | 100.744 | 274.158 | 1.00 | 0.00 | C |
| HETATM | 3972 | C13 | YG | C | 37 | 11.063 | 99.698 | 273.089 | 1.00 | 0.00 | C |
| HETATM | 3973 | C14 | YG | C | 37 | 10.595 | 98.329 | 273.534 | 1.00 | 0.00 | C |
| HETATM | 3974 | C15 | YG | C | 37 | 11.642 | 97.205 | 273.479 | 1.00 | 0.00 | C |
| HETATM | 3975 | C16 | YG | C | 37 | 10.981 | 95.849 | 273.209 | 1.00 | 0.00 | C |
| HETATM | 3976 | O17 | YG | C | 37 | 10.098 | 95.744 | 272.356 | 1.00 | 0.00 | O |
| HETATM | 3977 | O18 | YG | C | 37 | 11.384 | 94.795 | 273.958 | 1.00 | 0.00 | O |
| HETATM | 3978 | C19 | YG | C | 37 | 12.123 | 93.677 | 273.398 | 1.00 | 0.00 | C |
| HETATM | 3979 | N20 | YG | C | 37 | 12.431 | 97.173 | 274.711 | 1.00 | 0.00 | N |
| HETATM | 3980 | C21 | YG | C | 37 | 13.764 | 97.129 | 274.737 | 1.00 | 0.00 | C |
| HETATM | 3981 | O22 | YG | C | 37 | 14.439 | 97.213 | 273.705 | 1.00 | 0.00 | O |
| HETATM | 3982 | O23 | YG | C | 37 | 14.384 | 97.001 | 275.935 | 1.00 | 0.00 | O |
| HETATM | 3983 | C24 | YG | C | 37 | 15.820 | 97.108 | 276.098 | 1.00 | 0.00 | C |
| HETATM | 3984 | C1* | YG | C | 37 | 7.428 | 105.940 | 275.804 | 1.00 | 0.00 | C |
| HETATM | 3985 | C2* | YG | C | 37 | 8.652 | 106.850 | 275.975 | 1.00 | 0.00 | C |
| HETATM | 3986 | O2* | YG | C | 37 | 8.919 | 107.074 | 277.346 | 1.00 | 0.00 | O |
| HETATM | 3987 | C3* | YG | C | 37 | 8.204 | 108.108 | 275.244 | 1.00 | 0.00 | C |
| HETATM | 3988 | O3* | YG | C | 37 | 8.887 | 109.253 | 275.729 | 1.00 | 0.00 | O |
| HETATM | 3989 | C4* | YG | C | 37 | 6.737 | 108.167 | 275.610 | 1.00 | 0.00 | C |
| HETATM | 3990 | O4* | YG | C | 37 | 6.325 | 106.781 | 275.507 | 1.00 | 0.00 | O |
| HETATM | 3991 | C5* | YG | C | 37 | 5.891 | 109.011 | 274.698 | 1.00 | 0.00 | C |
| HETATM | 3992 | O5* | YG | C | 37 | 5.874 | 108.449 | 273.393 | 1.00 | 0.00 | O |
| HETATM | 3993 | P | YG | C | 37 | 4.841 | 108.974 | 272.304 | 1.00 | 0.00 | P |
| HETATM | 3994 | O1P | YG | C | 37 | 5.074 | 108.207 | 271.048 | 1.00 | 0.00 | O |
| HETATM | 3995 | O2P | YG | C | 37 | 4.891 | 110.463 | 272.281 | 1.00 | 0.00 | O |
| ATOM | 3996 | P | A | C | 38 | 10.336 | 109.617 | 275.144 | 1.00 | 0.00 | P |
| ATOM | 3997 | O1P | A | C | 38 | 10.979 | 110.568 | 276.085 | 1.00 | 0.00 | O |
| ATOM | 3998 | O2P | A | C | 38 | 10.142 | 109.992 | 273.721 | 1.00 | 0.00 | O |
| ATOM | 3999 | O5* | A | C | 38 | 11.157 | 108.258 | 275.211 | 1.00 | 0.00 | O |
| ATOM | 4000 | C5* | A | C | 38 | 11.966 | 107.972 | 276.334 | 1.00 | 0.00 | C |
| ATOM | 4001 | C4* | A | C | 38 | 12.730 | 106.705 | 276.097 | 1.00 | 0.00 | C |
| ATOM | 4002 | O4* | A | C | 38 | 11.804 | 105.658 | 275.721 | 1.00 | 0.00 | O |
| ATOM | 4003 | C3* | A | C | 38 | 13.665 | 106.711 | 274.905 | 1.00 | 0.00 | C |
| ATOM | 4004 | O3* | A | C | 38 | 14.847 | 107.454 | 275.147 | 1.00 | 0.00 | O |
| ATOM | 4005 | C2* | A | C | 38 | 13.905 | 105.219 | 274.724 | 1.00 | 0.00 | C |
| ATOM | 4006 | O2* | A | C | 38 | 14.772 | 104.626 | 275.673 | 1.00 | 0.00 | O |
| ATOM | 4007 | C1* | A | C | 38 | 12.487 | 104.695 | 274.925 | 1.00 | 0.00 | C |
| ATOM | 4008 | N9 | A | C | 38 | 11.810 | 104.589 | 273.641 | 1.00 | 0.00 | N |
| ATOM | 4009 | C8 | A | C | 38 | 10.788 | 105.354 | 273.146 | 1.00 | 0.00 | C |
| ATOM | 4010 | N7 | A | C | 38 | 10.405 | 105.007 | 271.940 | 1.00 | 0.00 | N |
| ATOM | 4011 | C5 | A | C | 38 | 11.234 | 103.937 | 271.620 | 1.00 | 0.00 | C |
| ATOM | 4012 | C6 | A | C | 38 | 11.340 | 103.117 | 270.467 | 1.00 | 0.00 | C |
| ATOM | 4013 | N6 | A | C | 38 | 10.571 | 103.249 | 269.378 | 1.00 | 0.00 | N |
| ATOM | 4014 | N1 | A | C | 38 | 12.280 | 102.146 | 270.476 | 1.00 | 0.00 | N |
| ATOM | 4015 | C2 | A | C | 38 | 13.054 | 102.010 | 271.570 | 1.00 | 0.00 | C |
| ATOM | 4016 | N3 | A | C | 38 | 13.050 | 102.714 | 272.704 | 1.00 | 0.00 | N |
| ATOM | 4017 | C4 | A | C | 38 | 12.105 | 103.671 | 272.662 | 1.00 | 0.00 | C |
| HETATM | 4018 | N1 | PSU | C | 39 | 12.871 | 106.331 | 269.992 | 1.00 | 0.00 | N |
| HETATM | 4019 | C2 | PSU | C | 39 | 12.382 | 106.013 | 268.752 | 1.00 | 0.00 | C |
| HETATM | 4020 | N3 | PSU | C | 39 | 13.059 | 105.009 | 268.122 | 1.00 | 0.00 | N |
| HETATM | 4021 | C4 | PSU | C | 39 | 14.150 | 104.328 | 268.624 | 1.00 | 0.00 | C |
| HETATM | 4022 | C5 | PSU | C | 39 | 14.576 | 104.750 | 269.933 | 1.00 | 0.00 | C |
| HETATM | 4023 | C6 | PSU | C | 39 | 13.914 | 105.730 | 270.550 | 1.00 | 0.00 | C |
| HETATM | 4024 | O2 | PSU | C | 39 | 11.430 | 106.576 | 268.251 | 1.00 | 0.00 | O |
| HETATM | 4025 | O4 | PSU | C | 39 | 14.665 | 103.441 | 267.947 | 1.00 | 0.00 | O |
| HETATM | 4026 | C1* | PSU | C | 39 | 15.907 | 104.236 | 270.453 | 1.00 | 0.00 | C |
| HETATM | 4027 | C2* | PSU | C | 39 | 17.118 | 104.766 | 269.683 | 1.00 | 0.00 | C |
| HETATM | 4028 | O2* | PSU | C | 39 | 18.103 | 103.759 | 269.565 | 1.00 | 0.00 | O |
| HETATM | 4029 | C3* | PSU | C | 39 | 17.574 | 105.909 | 270.581 | 1.00 | 0.00 | C |
| HETATM | 4030 | C4* | PSU | C | 39 | 17.302 | 105.351 | 271.968 | 1.00 | 0.00 | C |
| HETATM | 4031 | O3* | PSU | C | 39 | 18.964 | 106.153 | 270.406 | 1.00 | 0.00 | O |
| HETATM | 4032 | O4* | PSU | C | 39 | 16.051 | 104.637 | 271.807 | 1.00 | 0.00 | O |
| HETATM | 4033 | C5* | PSU | C | 39 | 17.151 | 106.375 | 273.071 | 1.00 | 0.00 | C |
| HETATM | 4034 | O5* | PSU | C | 39 | 15.941 | 107.113 | 272.902 | 1.00 | 0.00 | O |
| HETATM | 4035 | P | PSU | C | 39 | 15.541 | 108.256 | 273.934 | 1.00 | 0.00 | P |
| HETATM | 4036 | O1P | PSU | C | 39 | 14.512 | 109.123 | 273.300 | 1.00 | 0.00 | O |
| HETATM | 4037 | O2P | PSU | C | 39 | 16.796 | 108.853 | 274.451 | 1.00 | 0.00 | O |
| HETATM | 4038 | P | 5MC | C | 40 | 19.448 | 107.311 | 269.402 | 1.00 | 0.00 | P |
| HETATM | 4039 | O1P | 5MC | C | 40 | 18.609 | 108.518 | 269.674 | 1.00 | 0.00 | O |
| HETATM | 4040 | O2P | 5MC | C | 40 | 20.929 | 107.407 | 269.476 | 1.00 | 0.00 | O |
| HETATM | 4041 | O5* | 5MC | C | 40 | 19.081 | 106.768 | 267.948 | 1.00 | 0.00 | O |
| HETATM | 4042 | C5* | 5MC | C | 40 | 20.016 | 106.008 | 267.196 | 1.00 | 0.00 | C |

| | | | | | | | | | |
|---|---|---|---|---|---|---|---|---|---|
| HETATM | 4043 | C4* | 5MC | C | 40 | 19.337 | 105.392 | 266.000 | 1.00 | 0.00 | C |
| HETATM | 4044 | O4* | 5MC | C | 40 | 18.016 | 104.909 | 266.373 | 1.00 | 0.00 | O |
| HETATM | 4045 | C3* | 5MC | C | 40 | 19.028 | 106.371 | 264.891 | 1.00 | 0.00 | C |
| HETATM | 4046 | O3* | 5MC | C | 40 | 20.170 | 106.604 | 264.088 | 1.00 | 0.00 | O |
| HETATM | 4047 | C2* | 5MC | C | 40 | 17.957 | 105.622 | 264.116 | 1.00 | 0.00 | C |
| HETATM | 4048 | O2* | 5MC | C | 40 | 18.456 | 104.619 | 263.254 | 1.00 | 0.00 | O |
| HETATM | 4049 | C1* | 5MC | C | 40 | 17.144 | 105.019 | 265.257 | 1.00 | 0.00 | C |
| HETATM | 4050 | N1 | 5MC | C | 40 | 16.027 | 105.907 | 265.607 | 1.00 | 0.00 | N |
| HETATM | 4051 | C2 | 5MC | C | 40 | 15.009 | 106.088 | 264.672 | 1.00 | 0.00 | C |
| HETATM | 4052 | O2 | 5MC | C | 40 | 15.104 | 105.532 | 263.570 | 1.00 | 0.00 | O |
| HETATM | 4053 | N3 | 5MC | C | 40 | 13.956 | 106.870 | 264.980 | 1.00 | 0.00 | N |
| HETATM | 4054 | C4 | 5MC | C | 40 | 13.906 | 107.476 | 266.158 | 1.00 | 0.00 | C |
| HETATM | 4055 | N4 | 5MC | C | 40 | 12.831 | 108.224 | 266.427 | 1.00 | 0.00 | N |
| HETATM | 4056 | C5 | 5MC | C | 40 | 14.943 | 107.342 | 267.116 | 1.00 | 0.00 | C |
| HETATM | 4057 | C6 | 5MC | C | 40 | 15.972 | 106.544 | 266.811 | 1.00 | 0.00 | C |
| HETATM | 4058 | CM5 | 5MC | C | 40 | 14.899 | 108.183 | 268.349 | 1.00 | 0.00 | C |
| ATOM | 4059 | P | U | C | 41 | 20.450 | 108.080 | 263.535 | 1.00 | 0.00 | P |
| ATOM | 4060 | O1P | U | C | 41 | 21.917 | 108.241 | 263.474 | 1.00 | 0.00 | O |
| ATOM | 4061 | O2P | U | C | 41 | 19.637 | 109.015 | 264.343 | 1.00 | 0.00 | O |
| ATOM | 4062 | O5* | U | C | 41 | 19.847 | 108.091 | 262.067 | 1.00 | 0.00 | O |
| ATOM | 4063 | C5* | U | C | 41 | 18.616 | 107.463 | 261.823 | 1.00 | 0.00 | C |
| ATOM | 4064 | C4* | U | C | 41 | 18.013 | 107.929 | 260.533 | 1.00 | 0.00 | C |
| ATOM | 4065 | O4* | U | C | 41 | 16.628 | 107.526 | 260.625 | 1.00 | 0.00 | O |
| ATOM | 4066 | C3* | U | C | 41 | 17.965 | 109.430 | 260.249 | 1.00 | 0.00 | C |
| ATOM | 4067 | O3* | U | C | 41 | 19.023 | 109.849 | 259.393 | 1.00 | 0.00 | O |
| ATOM | 4068 | C2* | U | C | 41 | 16.625 | 109.559 | 259.540 | 1.00 | 0.00 | C |
| ATOM | 4069 | O2* | U | C | 41 | 16.607 | 109.024 | 258.230 | 1.00 | 0.00 | O |
| ATOM | 4070 | C1* | U | C | 41 | 15.794 | 108.633 | 260.404 | 1.00 | 0.00 | C |
| ATOM | 4071 | N1 | U | C | 41 | 15.464 | 109.221 | 261.704 | 1.00 | 0.00 | N |
| ATOM | 4072 | C2 | U | C | 41 | 14.310 | 109.941 | 261.747 | 1.00 | 0.00 | C |
| ATOM | 4073 | O2 | U | C | 41 | 13.593 | 110.076 | 260.759 | 1.00 | 0.00 | O |
| ATOM | 4074 | N3 | U | C | 41 | 14.020 | 110.502 | 262.964 | 1.00 | 0.00 | N |
| ATOM | 4075 | C4 | U | C | 41 | 14.767 | 110.410 | 264.117 | 1.00 | 0.00 | C |
| ATOM | 4076 | O4 | U | C | 41 | 14.371 | 110.972 | 265.139 | 1.00 | 0.00 | O |
| ATOM | 4077 | C5 | U | C | 41 | 15.969 | 109.629 | 263.993 | 1.00 | 0.00 | C |
| ATOM | 4078 | C6 | U | C | 41 | 16.261 | 109.071 | 262.817 | 1.00 | 0.00 | C |
| ATOM | 4079 | P | G | C | 42 | 19.569 | 111.363 | 259.488 | 1.00 | 0.00 | P |
| ATOM | 4080 | O1P | G | C | 42 | 20.673 | 111.515 | 258.537 | 1.00 | 0.00 | O |
| ATOM | 4081 | O2P | G | C | 42 | 19.797 | 111.630 | 260.939 | 1.00 | 0.00 | O |
| ATOM | 4082 | O5* | G | C | 42 | 18.372 | 112.254 | 258.935 | 1.00 | 0.00 | O |
| ATOM | 4083 | C5* | G | C | 42 | 17.840 | 112.049 | 257.638 | 1.00 | 0.00 | C |
| ATOM | 4084 | C4* | G | C | 42 | 16.471 | 112.696 | 257.532 | 1.00 | 0.00 | C |
| ATOM | 4085 | O4* | G | C | 42 | 15.595 | 112.143 | 258.562 | 1.00 | 0.00 | O |
| ATOM | 4086 | C3* | G | C | 42 | 16.393 | 114.197 | 257.810 | 1.00 | 0.00 | C |
| ATOM | 4087 | O3* | G | C | 42 | 16.733 | 114.983 | 256.669 | 1.00 | 0.00 | O |
| ATOM | 4088 | C2* | G | C | 42 | 14.908 | 114.369 | 258.093 | 1.00 | 0.00 | C |
| ATOM | 4089 | O2* | G | C | 42 | 14.172 | 114.348 | 256.903 | 1.00 | 0.00 | O |
| ATOM | 4090 | C1* | G | C | 42 | 14.604 | 113.106 | 258.897 | 1.00 | 0.00 | C |
| ATOM | 4091 | N9 | G | C | 42 | 14.627 | 113.367 | 260.336 | 1.00 | 0.00 | N |
| ATOM | 4092 | C8 | G | C | 42 | 15.558 | 112.969 | 261.271 | 1.00 | 0.00 | C |
| ATOM | 4093 | N7 | G | C | 42 | 15.273 | 113.372 | 262.488 | 1.00 | 0.00 | N |
| ATOM | 4094 | C5 | G | C | 42 | 14.081 | 114.076 | 262.340 | 1.00 | 0.00 | C |
| ATOM | 4095 | C6 | G | C | 42 | 13.266 | 114.723 | 263.299 | 1.00 | 0.00 | C |
| ATOM | 4096 | O6 | G | C | 42 | 13.430 | 114.815 | 264.515 | 1.00 | 0.00 | O |
| ATOM | 4097 | N1 | G | C | 42 | 12.154 | 115.303 | 262.707 | 1.00 | 0.00 | N |
| ATOM | 4098 | C2 | G | C | 42 | 11.855 | 115.263 | 261.366 | 1.00 | 0.00 | C |
| ATOM | 4099 | N2 | G | C | 42 | 10.719 | 115.887 | 260.975 | 1.00 | 0.00 | N |
| ATOM | 4100 | N3 | G | C | 42 | 12.596 | 114.665 | 260.471 | 1.00 | 0.00 | N |
| ATOM | 4101 | C4 | G | C | 42 | 13.681 | 114.093 | 261.019 | 1.00 | 0.00 | C |
| ATOM | 4102 | P | G | C | 43 | 17.258 | 116.497 | 256.869 | 1.00 | 0.00 | P |
| ATOM | 4103 | O1P | G | C | 43 | 17.876 | 116.970 | 255.604 | 1.00 | 0.00 | O |
| ATOM | 4104 | O2P | G | C | 43 | 18.047 | 116.492 | 258.111 | 1.00 | 0.00 | O |
| ATOM | 4105 | O5* | G | C | 43 | 15.926 | 117.344 | 257.086 | 1.00 | 0.00 | O |
| ATOM | 4106 | C5* | G | C | 43 | 14.862 | 117.263 | 256.148 | 1.00 | 0.00 | C |
| ATOM | 4107 | C4* | G | C | 43 | 13.629 | 117.915 | 256.700 | 1.00 | 0.00 | C |
| ATOM | 4108 | O4* | G | C | 43 | 13.158 | 117.192 | 257.866 | 1.00 | 0.00 | O |
| ATOM | 4109 | C3* | G | C | 43 | 13.880 | 119.312 | 257.213 | 1.00 | 0.00 | C |
| ATOM | 4110 | O3* | G | C | 43 | 13.811 | 120.196 | 256.116 | 1.00 | 0.00 | O |
| ATOM | 4111 | C2* | G | C | 43 | 12.725 | 119.498 | 258.189 | 1.00 | 0.00 | C |
| ATOM | 4112 | O2* | G | C | 43 | 11.522 | 119.792 | 257.520 | 1.00 | 0.00 | O |
| ATOM | 4113 | C1* | G | C | 43 | 12.622 | 118.104 | 258.803 | 1.00 | 0.00 | C |
| ATOM | 4114 | N9 | G | C | 43 | 13.336 | 117.934 | 260.064 | 1.00 | 0.00 | N |
| ATOM | 4115 | C8 | G | C | 43 | 14.553 | 117.340 | 260.253 | 1.00 | 0.00 | C |
| ATOM | 4116 | N7 | G | C | 43 | 14.920 | 117.301 | 261.509 | 1.00 | 0.00 | N |
| ATOM | 4117 | C5 | G | C | 43 | 13.885 | 117.918 | 262.185 | 1.00 | 0.00 | C |
| ATOM | 4118 | C6 | G | C | 43 | 13.722 | 118.183 | 263.560 | 1.00 | 0.00 | C |
| ATOM | 4119 | O6 | G | C | 43 | 14.485 | 117.887 | 264.506 | 1.00 | 0.00 | O |
| ATOM | 4120 | N1 | G | C | 43 | 12.527 | 118.864 | 263.810 | 1.00 | 0.00 | N |
| ATOM | 4121 | C2 | G | C | 43 | 11.614 | 119.233 | 262.859 | 1.00 | 0.00 | C |
| ATOM | 4122 | N2 | G | C | 43 | 10.537 | 119.904 | 263.290 | 1.00 | 0.00 | N |
| ATOM | 4123 | N3 | G | C | 43 | 11.748 | 118.975 | 261.573 | 1.00 | 0.00 | N |
| ATOM | 4124 | C4 | G | C | 43 | 12.901 | 118.323 | 261.306 | 1.00 | 0.00 | C |
| ATOM | 4125 | P | A | C | 44 | 14.659 | 121.551 | 256.137 | 1.00 | 0.00 | P |
| ATOM | 4126 | O1P | A | C | 44 | 14.606 | 122.071 | 254.742 | 1.00 | 0.00 | O |
| ATOM | 4127 | O2P | A | C | 44 | 15.967 | 121.294 | 256.785 | 1.00 | 0.00 | O |
| ATOM | 4128 | O5* | A | C | 44 | 13.795 | 122.490 | 257.090 | 1.00 | 0.00 | O |
| ATOM | 4129 | C5* | A | C | 44 | 12.557 | 123.011 | 256.633 | 1.00 | 0.00 | C |

```
ATOM    4130  C4*   A C  44    11.677 123.354 257.805  1.00  0.00           C
ATOM    4131  O4*   A C  44    11.744 122.272 258.755  1.00  0.00           O
ATOM    4132  C3*   A C  44    12.142 124.546 258.608  1.00  0.00           C
ATOM    4133  O3*   A C  44    11.686 125.756 258.021  1.00  0.00           O
ATOM    4134  C2*   A C  44    11.481 124.297 259.948  1.00  0.00           C
ATOM    4135  O2*   A C  44    10.116 124.653 259.919  1.00  0.00           O
ATOM    4136  C1*   A C  44    11.625 122.782 260.066  1.00  0.00           C
ATOM    4137  N9    A C  44    12.804 122.354 260.805  1.00  0.00           N
ATOM    4138  C8    A C  44    13.996 121.943 260.283  1.00  0.00           C
ATOM    4139  N7    A C  44    14.869 121.569 261.190  1.00  0.00           N
ATOM    4140  C5    A C  44    14.209 121.763 262.392  1.00  0.00           C
ATOM    4141  C6    A C  44    14.588 121.556 263.739  1.00  0.00           C
ATOM    4142  N6    A C  44    15.784 121.070 264.132  1.00  0.00           N
ATOM    4143  N1    A C  44    13.679 121.863 264.695  1.00  0.00           N
ATOM    4144  C2    A C  44    12.480 122.326 264.315  1.00  0.00           C
ATOM    4145  N3    A C  44    12.014 122.551 263.098  1.00  0.00           N
ATOM    4146  C4    A C  44    12.935 122.253 262.170  1.00  0.00           C
ATOM    4147  P     G C  45    12.625 126.768 257.766  1.00  0.00           P
ATOM    4148  O1P   G C  45    11.715 127.758 257.164  1.00  0.00           O
ATOM    4149  O2P   G C  45    13.989 126.579 257.207  1.00  0.00           O
ATOM    4150  O5*   G C  45    12.694 127.064 259.328  1.00  0.00           O
ATOM    4151  C5*   G C  45    11.498 127.251 260.076  1.00  0.00           C
ATOM    4152  C4*   G C  45    11.827 127.462 261.522  1.00  0.00           C
ATOM    4153  O4*   G C  45    12.377 126.231 262.052  1.00  0.00           O
ATOM    4154  C3*   G C  45    12.922 128.486 261.747  1.00  0.00           C
ATOM    4155  O3*   G C  45    12.322 129.762 261.869  1.00  0.00           O
ATOM    4156  C2*   G C  45    13.499 128.046 263.082  1.00  0.00           C
ATOM    4157  O2*   G C  45    12.697 128.490 264.142  1.00  0.00           O
ATOM    4158  C1*   G C  45    13.398 126.521 262.992  1.00  0.00           C
ATOM    4159  N9    G C  45    14.623 125.863 262.542  1.00  0.00           N
ATOM    4160  C8    G C  45    14.974 125.591 261.241  1.00  0.00           C
ATOM    4161  N7    G C  45    16.135 125.006 261.131  1.00  0.00           N
ATOM    4162  C5    G C  45    16.584 124.880 262.443  1.00  0.00           C
ATOM    4163  C6    G C  45    17.812 124.355 262.950  1.00  0.00           C
ATOM    4164  O6    G C  45    18.787 123.874 262.317  1.00  0.00           O
ATOM    4165  N1    G C  45    17.864 124.447 264.330  1.00  0.00           N
ATOM    4166  C2    G C  45    16.866 124.980 265.122  1.00  0.00           C
ATOM    4167  N2    G C  45    17.109 124.988 266.443  1.00  0.00           N
ATOM    4168  N3    G C  45    15.723 125.473 264.658  1.00  0.00           N
ATOM    4169  C4    G C  45    15.657 125.396 263.328  1.00  0.00           C
HETATM  4170  P    7MG C  46    12.848 130.968 260.962  1.00  0.00           P
HETATM  4171  O1P  7MG C  46    13.341 130.430 259.672  1.00  0.00           O
HETATM  4172  O2P  7MG C  46    11.814 132.034 260.964  1.00  0.00           O
HETATM  4173  O5*  7MG C  46    14.093 131.510 261.788  1.00  0.00           O
HETATM  4174  C5*  7MG C  46    13.932 131.850 263.158  1.00  0.00           C
HETATM  4175  C4*  7MG C  46    14.812 133.027 263.516  1.00  0.00           C
HETATM  4176  O4*  7MG C  46    16.187 132.555 263.635  1.00  0.00           O
HETATM  4177  C3*  7MG C  46    14.850 134.163 262.500  1.00  0.00           C
HETATM  4178  O3*  7MG C  46    15.007 135.414 263.180  1.00  0.00           O
HETATM  4179  C2*  7MG C  46    16.092 133.813 261.684  1.00  0.00           C
HETATM  4180  O2*  7MG C  46    16.676 134.890 260.969  1.00  0.00           O
HETATM  4181  C1*  7MG C  46    17.022 133.310 262.779  1.00  0.00           C
HETATM  4182  N9   7MG C  46    18.079 132.429 262.297  1.00  0.00           N
HETATM  4183  C8   7MG C  46    18.333 132.024 260.930  1.00  0.00           C
HETATM  4184  N7   7MG C  46    19.493 131.201 260.941  1.00  0.00           N
HETATM  4185  C5   7MG C  46    19.901 131.097 262.258  1.00  0.00           C
HETATM  4186  C6   7MG C  46    20.986 130.420 262.803  1.00  0.00           C
HETATM  4187  O6   7MG C  46    21.820 129.776 262.207  1.00  0.00           O
HETATM  4188  N1   7MG C  46    21.047 130.544 264.179  1.00  0.00           N
HETATM  4189  C2   7MG C  46    20.155 131.267 264.942  1.00  0.00           C
HETATM  4190  N2   7MG C  46    20.370 131.261 266.280  1.00  0.00           N
HETATM  4191  N3   7MG C  46    19.131 131.940 264.439  1.00  0.00           N
HETATM  4192  C4   7MG C  46    19.052 131.814 263.106  1.00  0.00           C
HETATM  4193  CM7  7MG C  46    20.017 130.647 259.654  1.00  0.00           C
ATOM    4194  P     U C  47    13.707 136.352 263.462  1.00  0.00           P
ATOM    4195  O1P   U C  47    13.409 136.336 264.907  1.00  0.00           O
ATOM    4196  O2P   U C  47    12.651 135.957 262.482  1.00  0.00           O
ATOM    4197  O5*   U C  47    14.213 137.807 263.052  1.00  0.00           O
ATOM    4198  C5*   U C  47    14.972 137.996 261.849  1.00  0.00           C
ATOM    4199  C4*   U C  47    15.784 139.274 261.935  1.00  0.00           C
ATOM    4200  O4*   U C  47    14.909 140.443 261.974  1.00  0.00           O
ATOM    4201  C3*   U C  47    16.660 139.397 263.176  1.00  0.00           C
ATOM    4202  O3*   U C  47    17.791 140.137 262.795  1.00  0.00           O
ATOM    4203  C2*   U C  47    15.782 140.192 264.130  1.00  0.00           C
ATOM    4204  O2*   U C  47    16.465 140.884 265.161  1.00  0.00           O
ATOM    4205  C1*   U C  47    15.148 141.174 263.162  1.00  0.00           C
ATOM    4206  N1    U C  47    13.874 141.646 263.691  1.00  0.00           N
ATOM    4207  C2    U C  47    13.687 142.995 263.732  1.00  0.00           C
ATOM    4208  O2    U C  47    14.519 143.785 263.315  1.00  0.00           O
ATOM    4209  N3    U C  47    12.498 143.391 264.282  1.00  0.00           N
ATOM    4210  C4    U C  47    11.500 142.576 264.784  1.00  0.00           C
ATOM    4211  O4    U C  47    10.494 143.085 265.283  1.00  0.00           O
ATOM    4212  C5    U C  47    11.773 141.178 264.689  1.00  0.00           C
ATOM    4213  C6    U C  47    12.922 140.773 264.155  1.00  0.00           C
ATOM    4214  P     C C  48    19.046 139.364 262.179  1.00  0.00           P
ATOM    4215  O1P   C C  48    19.890 140.365 261.495  1.00  0.00           O
ATOM    4216  O2P   C C  48    18.504 138.203 261.426  1.00  0.00           O
```

```
ATOM    4217  O5*   C C  48      19.780 138.793 263.471  1.00  0.00           O
ATOM    4218  C5*   C C  48      20.355 139.673 264.388  1.00  0.00           C
ATOM    4219  C4*   C C  48      21.081 138.903 265.451  1.00  0.00           C
ATOM    4220  O4*   C C  48      21.669 137.691 264.888  1.00  0.00           O
ATOM    4221  C3*   C C  48      22.219 139.684 266.075  1.00  0.00           C
ATOM    4222  O3*   C C  48      22.157 139.422 267.471  1.00  0.00           O
ATOM    4223  C2*   C C  48      23.450 139.083 265.379  1.00  0.00           C
ATOM    4224  O2*   C C  48      24.652 139.133 266.108  1.00  0.00           O
ATOM    4225  C1*   C C  48      23.040 137.623 265.237  1.00  0.00           C
ATOM    4226  N1    C C  48      23.752 136.932 264.145  1.00  0.00           N
ATOM    4227  C2    C C  48      24.794 136.072 264.440  1.00  0.00           C
ATOM    4228  O2    C C  48      25.105 135.906 265.618  1.00  0.00           O
ATOM    4229  N3    C C  48      25.448 135.453 263.416  1.00  0.00           N
ATOM    4230  C4    C C  48      25.078 135.701 262.149  1.00  0.00           C
ATOM    4231  N4    C C  48      25.753 135.121 261.128  1.00  0.00           N
ATOM    4232  C5    C C  48      24.009 136.566 261.849  1.00  0.00           C
ATOM    4233  C6    C C  48      23.392 137.152 262.861  1.00  0.00           C
HETATM  4234  P    5MC C  49      22.463 140.580 268.527  1.00  0.00           P
HETATM  4235  O1P  5MC C  49      22.664 139.874 269.819  1.00  0.00           O
HETATM  4236  O2P  5MC C  49      23.488 141.541 268.042  1.00  0.00           O
HETATM  4237  O5*  5MC C  49      21.107 141.446 268.609  1.00  0.00           O
HETATM  4238  C5*  5MC C  49      19.843 140.837 268.816  1.00  0.00           C
HETATM  4239  C4*  5MC C  49      18.795 141.922 269.028  1.00  0.00           C
HETATM  4240  O4*  5MC C  49      19.006 142.523 270.335  1.00  0.00           O
HETATM  4241  C3*  5MC C  49      19.012 143.091 268.083  1.00  0.00           C
HETATM  4242  O3*  5MC C  49      18.400 142.829 266.847  1.00  0.00           O
HETATM  4243  C2*  5MC C  49      18.344 144.216 268.829  1.00  0.00           C
HETATM  4244  O2*  5MC C  49      16.940 144.066 268.731  1.00  0.00           O
HETATM  4245  C1*  5MC C  49      18.828 143.938 270.248  1.00  0.00           C
HETATM  4246  N1   5MC C  49      20.108 144.622 270.584  1.00  0.00           N
HETATM  4247  C2   5MC C  49      20.109 146.041 270.720  1.00  0.00           C
HETATM  4248  O2   5MC C  49      19.028 146.678 270.603  1.00  0.00           O
HETATM  4249  N3   5MC C  49      21.276 146.685 270.973  1.00  0.00           N
HETATM  4250  C4   5MC C  49      22.413 145.995 271.125  1.00  0.00           C
HETATM  4251  N4   5MC C  49      23.532 146.689 271.392  1.00  0.00           N
HETATM  4252  C5   5MC C  49      22.452 144.568 271.013  1.00  0.00           C
HETATM  4253  C6   5MC C  49      21.282 143.919 270.741  1.00  0.00           C
HETATM  4254  CM5  5MC C  49      23.766 143.870 271.200  1.00  0.00           C
ATOM    4255  P     U C  50      18.987 143.518 265.510  1.00  0.00           P
ATOM    4256  O1P   U C  50      18.351 142.831 264.384  1.00  0.00           O
ATOM    4257  O2P   U C  50      20.494 143.637 265.607  1.00  0.00           O
ATOM    4258  O5*   U C  50      18.482 145.027 265.519  1.00  0.00           O
ATOM    4259  C5*   U C  50      17.118 145.360 265.768  1.00  0.00           C
ATOM    4260  C4*   U C  50      16.937 146.868 265.780  1.00  0.00           C
ATOM    4261  O4*   U C  50      17.359 147.406 267.066  1.00  0.00           O
ATOM    4262  C3*   U C  50      17.761 147.681 264.785  1.00  0.00           C
ATOM    4263  O3*   U C  50      17.133 147.757 263.521  1.00  0.00           O
ATOM    4264  C2*   U C  50      17.696 149.051 265.429  1.00  0.00           C
ATOM    4265  O2*   U C  50      16.393 149.574 265.296  1.00  0.00           O
ATOM    4266  C1*   U C  50      17.934 148.678 266.882  1.00  0.00           C
ATOM    4267  N1    U C  50      19.359 148.588 267.202  1.00  0.00           N
ATOM    4268  C2    U C  50      20.034 149.780 267.391  1.00  0.00           C
ATOM    4269  O2    U C  50      19.507 150.878 267.218  1.00  0.00           O
ATOM    4270  N3    U C  50      21.339 149.656 267.797  1.00  0.00           N
ATOM    4271  C4    U C  50      22.024 148.496 268.010  1.00  0.00           C
ATOM    4272  O4    U C  50      23.206 148.555 268.370  1.00  0.00           O
ATOM    4273  C5    U C  50      21.268 147.291 267.744  1.00  0.00           C
ATOM    4274  C6    U C  50      19.995 147.382 267.348  1.00  0.00           C
ATOM    4275  P     G C  51      18.029 147.876 262.193  1.00  0.00           P
ATOM    4276  O1P   G C  51      17.115 147.508 261.112  1.00  0.00           O
ATOM    4277  O2P   G C  51      19.309 147.132 262.347  1.00  0.00           O
ATOM    4278  O5*   G C  51      18.419 149.407 262.154  1.00  0.00           O
ATOM    4279  C5*   G C  51      17.466 150.409 262.473  1.00  0.00           C
ATOM    4280  C4*   G C  51      18.136 151.765 262.491  1.00  0.00           C
ATOM    4281  O4*   G C  51      18.672 152.036 263.816  1.00  0.00           O
ATOM    4282  C3*   G C  51      19.314 151.932 261.538  1.00  0.00           C
ATOM    4283  O3*   G C  51      18.889 152.347 260.240  1.00  0.00           O
ATOM    4284  C2*   G C  51      20.115 153.026 262.217  1.00  0.00           C
ATOM    4285  O2*   G C  51      19.530 154.266 262.031  1.00  0.00           O
ATOM    4286  C1*   G C  51      19.926 152.681 263.697  1.00  0.00           C
ATOM    4287  N9    G C  51      20.985 151.782 264.133  1.00  0.00           N
ATOM    4288  C8    G C  51      20.995 150.408 264.096  1.00  0.00           C
ATOM    4289  N7    G C  51      22.137 149.895 264.488  1.00  0.00           N
ATOM    4290  C5    G C  51      22.920 150.999 264.811  1.00  0.00           C
ATOM    4291  C6    G C  51      24.244 151.074 265.278  1.00  0.00           C
ATOM    4292  O6    G C  51      25.035 150.138 265.528  1.00  0.00           O
ATOM    4293  N1    G C  51      24.646 152.390 265.468  1.00  0.00           N
ATOM    4294  C2    G C  51      23.868 153.492 265.238  1.00  0.00           C
ATOM    4295  N2    G C  51      24.435 154.679 265.477  1.00  0.00           N
ATOM    4296  N3    G C  51      22.622 153.436 264.810  1.00  0.00           N
ATOM    4297  C4    G C  51      22.216 152.169 264.619  1.00  0.00           C
ATOM    4298  P     U C  52      19.800 152.009 258.932  1.00  0.00           P
ATOM    4299  O1P   U C  52      19.021 152.389 257.735  1.00  0.00           O
ATOM    4300  O2P   U C  52      20.336 150.632 259.022  1.00  0.00           O
ATOM    4301  O5*   U C  52      21.012 153.008 259.096  1.00  0.00           O
ATOM    4302  C5*   U C  52      20.785 154.399 259.068  1.00  0.00           C
ATOM    4303  C4*   U C  52      22.005 155.124 259.549  1.00  0.00           C
```

```
ATOM   4304  O4*   U   C  52    22.255 154.760 260.917  1.00  0.00           O
ATOM   4305  C3*   U   C  52    23.295 154.702 258.876  1.00  0.00           C
ATOM   4306  O3*   U   C  52    23.441 155.351 257.618  1.00  0.00           O
ATOM   4307  C2*   U   C  52    24.299 155.262 259.860  1.00  0.00           C
ATOM   4308  O2*   U   C  52    24.392 156.665 259.732  1.00  0.00           O
ATOM   4309  C1*   U   C  52    23.650 154.863 261.189  1.00  0.00           C
ATOM   4310  N1    U   C  52    24.168 153.540 261.584  1.00  0.00           N
ATOM   4311  C2    U   C  52    25.418 153.494 262.128  1.00  0.00           C
ATOM   4312  O2    U   C  52    26.068 154.479 262.321  1.00  0.00           O
ATOM   4313  N3    U   C  52    25.893 152.249 262.423  1.00  0.00           N
ATOM   4314  C4    U   C  52    25.254 151.062 262.209  1.00  0.00           C
ATOM   4315  O4    U   C  52    25.833 150.004 262.475  1.00  0.00           O
ATOM   4316  C5    U   C  52    23.943 151.190 261.645  1.00  0.00           C
ATOM   4317  C6    U   C  52    23.458 152.396 261.376  1.00  0.00           C
ATOM   4318  P     G   C  53    24.440 154.736 256.512  1.00  0.00           P
ATOM   4319  O1P   G   C  53    24.316 155.589 255.307  1.00  0.00           O
ATOM   4320  O2P   G   C  53    24.179 153.288 256.418  1.00  0.00           O
ATOM   4321  O5*   G   C  53    25.896 154.895 257.122  1.00  0.00           O
ATOM   4322  C5*   G   C  53    26.419 156.164 257.462  1.00  0.00           C
ATOM   4323  C4*   G   C  53    27.740 155.989 258.170  1.00  0.00           C
ATOM   4324  O4*   G   C  53    27.500 155.222 259.379  1.00  0.00           O
ATOM   4325  C3*   G   C  53    28.813 155.152 257.464  1.00  0.00           C
ATOM   4326  O3*   G   C  53    29.549 155.932 256.514  1.00  0.00           O
ATOM   4327  C2*   G   C  53    29.710 154.752 258.634  1.00  0.00           C
ATOM   4328  O2*   G   C  53    30.629 155.738 259.039  1.00  0.00           O
ATOM   4329  C1*   G   C  53    28.697 154.552 259.761  1.00  0.00           C
ATOM   4330  N9    G   C  53    28.402 153.133 259.892  1.00  0.00           N
ATOM   4331  C8    G   C  53    27.241 152.491 259.551  1.00  0.00           C
ATOM   4332  N7    G   C  53    27.281 151.201 259.778  1.00  0.00           N
ATOM   4333  C5    G   C  53    28.541 150.989 260.303  1.00  0.00           C
ATOM   4334  C6    G   C  53    29.169 149.781 260.710  1.00  0.00           C
ATOM   4335  O6    G   C  53    28.696 148.634 260.729  1.00  0.00           O
ATOM   4336  N1    G   C  53    30.473 150.004 261.127  1.00  0.00           N
ATOM   4337  C2    G   C  53    31.106 151.240 261.157  1.00  0.00           C
ATOM   4338  N2    G   C  53    32.375 151.237 261.617  1.00  0.00           N
ATOM   4339  N3    G   C  53    30.528 152.378 260.777  1.00  0.00           N
ATOM   4340  C4    G   C  53    29.253 152.174 260.365  1.00  0.00           C
HETATM 4341  N1    5MU C  54    32.480 150.996 257.947  1.00  0.00           N
HETATM 4342  C2    5MU C  54    32.638 149.707 258.372  1.00  0.00           C
HETATM 4343  N3    5MU C  54    31.572 148.867 258.117  1.00  0.00           N
HETATM 4344  C4    5MU C  54    30.381 149.190 257.489  1.00  0.00           C
HETATM 4345  C5    5MU C  54    30.296 150.570 257.053  1.00  0.00           C
HETATM 4346  C5M   5MU C  54    29.070 151.012 256.316  1.00  0.00           C
HETATM 4347  C6    5MU C  54    31.325 151.404 257.305  1.00  0.00           C
HETATM 4348  O2    5MU C  54    33.657 149.336 258.942  1.00  0.00           O
HETATM 4349  O4    5MU C  54    29.519 148.305 257.312  1.00  0.00           O
HETATM 4350  C1*   5MU C  54    33.614 151.906 258.199  1.00  0.00           C
HETATM 4351  C2*   5MU C  54    34.675 151.864 257.085  1.00  0.00           C
HETATM 4352  O2*   5MU C  54    35.968 152.127 257.599  1.00  0.00           O
HETATM 4353  C3*   5MU C  54    34.177 152.978 256.170  1.00  0.00           C
HETATM 4354  C4*   5MU C  54    33.768 154.025 257.192  1.00  0.00           C
HETATM 4355  O3*   5MU C  54    35.172 153.467 255.269  1.00  0.00           O
HETATM 4356  O4*   5MU C  54    33.116 153.232 258.227  1.00  0.00           O
HETATM 4357  C5*   5MU C  54    32.784 155.055 256.703  1.00  0.00           C
HETATM 4358  O5*   5MU C  54    31.615 154.416 256.252  1.00  0.00           O
HETATM 4359  P     5MU C  54    30.524 155.207 255.414  1.00  0.00           P
HETATM 4360  O1P   5MU C  54    29.759 154.229 254.595  1.00  0.00           O
HETATM 4361  O2P   5MU C  54    31.212 156.350 254.760  1.00  0.00           O
HETATM 4362  N1    PSU C  55    31.356 149.743 253.869  1.00  0.00           N
HETATM 4363  C2    PSU C  55    30.378 148.782 253.930  1.00  0.00           C
HETATM 4364  N3    PSU C  55    30.829 147.533 254.293  1.00  0.00           N
HETATM 4365  C4    PSU C  55    32.160 147.212 254.590  1.00  0.00           C
HETATM 4366  C5    PSU C  55    33.087 148.289 254.478  1.00  0.00           C
HETATM 4367  C6    PSU C  55    32.647 149.503 254.122  1.00  0.00           C
HETATM 4368  O2    PSU C  55    29.215 149.013 253.675  1.00  0.00           O
HETATM 4369  O4    PSU C  55    32.441 146.080 254.938  1.00  0.00           O
HETATM 4370  C1*   PSU C  55    34.556 147.935 254.528  1.00  0.00           C
HETATM 4371  C2*   PSU C  55    35.171 147.573 253.171  1.00  0.00           C
HETATM 4372  O2*   PSU C  55    36.153 146.574 253.408  1.00  0.00           O
HETATM 4373  C3*   PSU C  55    35.728 148.931 252.741  1.00  0.00           C
HETATM 4374  C4*   PSU C  55    36.288 149.450 254.053  1.00  0.00           C
HETATM 4375  O3*   PSU C  55    36.761 148.875 251.760  1.00  0.00           O
HETATM 4376  O4*   PSU C  55    35.265 149.051 255.017  1.00  0.00           O
HETATM 4377  C5*   PSU C  55    36.448 150.953 254.105  1.00  0.00           C
HETATM 4378  O5*   PSU C  55    35.288 151.587 253.563  1.00  0.00           O
HETATM 4379  P     PSU C  55    35.041 153.167 253.682  1.00  0.00           P
HETATM 4380  O1P   PSU C  55    33.631 153.419 253.255  1.00  0.00           O
HETATM 4381  O2P   PSU C  55    36.142 153.911 253.014  1.00  0.00           O
ATOM   4382  P     C   C  56    36.455 149.253 250.229  1.00  0.00           P
ATOM   4383  O1P   C   C  56    37.798 149.209 249.570  1.00  0.00           O
ATOM   4384  O2P   C   C  56    35.592 150.465 250.087  1.00  0.00           O
ATOM   4385  O5*   C   C  56    35.578 148.056 249.660  1.00  0.00           O
ATOM   4386  C5*   C   C  56    34.914 148.201 248.424  1.00  0.00           C
ATOM   4387  C4*   C   C  56    34.248 146.915 248.029  1.00  0.00           C
ATOM   4388  O4*   C   C  56    35.264 145.947 247.686  1.00  0.00           O
ATOM   4389  C3*   C   C  56    33.438 146.246 249.132  1.00  0.00           C
ATOM   4390  O3*   C   C  56    32.135 146.808 249.127  1.00  0.00           O
```

```
ATOM    4391  C2*   C C  56      33.415 144.805 248.653  1.00  0.00           C
ATOM    4392  O2*   C C  56      32.428 144.532 247.653  1.00  0.00           O
ATOM    4393  C1*   C C  56      34.832 144.656 248.090  1.00  0.00           C
ATOM    4394  N1    C C  56      35.765 144.172 249.116  1.00  0.00           N
ATOM    4395  C2    C C  56      35.763 142.823 249.424  1.00  0.00           C
ATOM    4396  O2    C C  56      34.962 142.100 248.879  1.00  0.00           O
ATOM    4397  N3    C C  56      36.631 142.343 250.312  1.00  0.00           N
ATOM    4398  C4    C C  56      37.483 143.153 250.920  1.00  0.00           C
ATOM    4399  N4    C C  56      38.330 142.598 251.783  1.00  0.00           N
ATOM    4400  C5    C C  56      37.504 144.558 250.660  1.00  0.00           C
ATOM    4401  C6    C C  56      36.627 145.024 249.749  1.00  0.00           C
ATOM    4402  P     G C  57      31.422 147.196 250.521  1.00  0.00           P
ATOM    4403  O1P   G C  57      30.092 147.748 250.121  1.00  0.00           O
ATOM    4404  O2P   G C  57      32.319 147.971 251.403  1.00  0.00           O
ATOM    4405  O5*   G C  57      31.199 145.789 251.232  1.00  0.00           O
ATOM    4406  C5*   G C  57      30.314 144.846 250.667  1.00  0.00           C
ATOM    4407  C4*   G C  57      30.479 143.483 251.317  1.00  0.00           C
ATOM    4408  O4*   G C  57      31.815 142.934 251.091  1.00  0.00           O
ATOM    4409  C3*   G C  57      30.314 143.440 252.826  1.00  0.00           C
ATOM    4410  O3*   G C  57      28.934 143.393 253.119  1.00  0.00           O
ATOM    4411  C2*   G C  57      30.959 142.112 253.162  1.00  0.00           C
ATOM    4412  O2*   G C  57      30.082 141.052 252.816  1.00  0.00           O
ATOM    4413  C1*   G C  57      32.159 142.112 252.198  1.00  0.00           C
ATOM    4414  N9    G C  57      33.364 142.669 252.793  1.00  0.00           N
ATOM    4415  C8    G C  57      33.885 143.938 252.623  1.00  0.00           C
ATOM    4416  N7    G C  57      35.032 144.101 253.241  1.00  0.00           N
ATOM    4417  C5    G C  57      35.265 142.872 253.865  1.00  0.00           C
ATOM    4418  C6    G C  57      36.380 142.414 254.677  1.00  0.00           C
ATOM    4419  O6    G C  57      37.392 143.043 255.033  1.00  0.00           O
ATOM    4420  N1    G C  57      36.203 141.096 255.087  1.00  0.00           N
ATOM    4421  C2    G C  57      35.094 140.327 254.787  1.00  0.00           C
ATOM    4422  N2    G C  57      35.041 139.104 255.316  1.00  0.00           N
ATOM    4423  N3    G C  57      34.077 140.736 254.026  1.00  0.00           N
ATOM    4424  C4    G C  57      34.233 141.993 253.609  1.00  0.00           C
HETATM  4425  P     1MA C  58    28.406 144.132 254.418  1.00  0.00           P
HETATM  4426  O1P   1MA C  58    28.978 145.472 254.575  1.00  0.00           O
HETATM  4427  O2P   1MA C  58    26.946 143.952 254.423  1.00  0.00           O
HETATM  4428  O5*   1MA C  58    29.046 143.323 255.643  1.00  0.00           O
HETATM  4429  C5*   1MA C  58    28.769 141.958 255.835  1.00  0.00           C
HETATM  4430  C4*   1MA C  58    28.844 141.597 257.318  1.00  0.00           C
HETATM  4431  O4*   1MA C  58    30.103 142.066 257.892  1.00  0.00           O
HETATM  4432  C3*   1MA C  58    27.757 142.160 258.250  1.00  0.00           C
HETATM  4433  O3*   1MA C  58    27.666 141.292 259.389  1.00  0.00           O
HETATM  4434  C2*   1MA C  58    28.434 143.445 258.689  1.00  0.00           C
HETATM  4435  O2*   1MA C  58    27.938 144.039 259.859  1.00  0.00           O
HETATM  4436  C1*   1MA C  58    29.836 142.922 258.977  1.00  0.00           C
HETATM  4437  N9    1MA C  58    30.867 143.965 259.069  1.00  0.00           N
HETATM  4438  C8    1MA C  58    30.784 145.240 258.595  1.00  0.00           C
HETATM  4439  N7    1MA C  58    31.816 145.981 258.900  1.00  0.00           N
HETATM  4440  C5    1MA C  58    32.657 145.127 259.602  1.00  0.00           C
HETATM  4441  C6    1MA C  58    33.972 145.453 260.161  1.00  0.00           C
HETATM  4442  N6    1MA C  58    34.525 146.820 260.058  1.00  0.00           N
HETATM  4443  N1    1MA C  58    34.586 144.322 260.825  1.00  0.00           N
HETATM  4444  CM1   1MA C  58    35.904 144.656 261.402  1.00  0.00           C
HETATM  4445  C2    1MA C  58    33.897 143.152 260.835  1.00  0.00           C
HETATM  4446  N3    1MA C  58    32.667 142.829 260.327  1.00  0.00           N
HETATM  4447  C4    1MA C  58    32.088 143.884 259.702  1.00  0.00           C
ATOM    4448  P     U C  59      26.803 139.900 259.324  1.00  0.00           P
ATOM    4449  O1P   U C  59      27.518 138.752 258.736  1.00  0.00           O
ATOM    4450  O2P   U C  59      25.439 140.249 258.845  1.00  0.00           O
ATOM    4451  O5*   U C  59      26.617 139.546 260.866  1.00  0.00           O
ATOM    4452  C5*   U C  59      25.735 140.320 261.698  1.00  0.00           C
ATOM    4453  C4*   U C  59      26.132 140.151 263.152  1.00  0.00           C
ATOM    4454  O4*   U C  59      26.292 138.720 263.404  1.00  0.00           O
ATOM    4455  C3*   U C  59      27.502 140.756 263.493  1.00  0.00           C
ATOM    4456  O3*   U C  59      27.388 142.174 263.829  1.00  0.00           O
ATOM    4457  C2*   U C  59      27.968 139.883 264.667  1.00  0.00           C
ATOM    4458  O2*   U C  59      27.493 140.375 265.904  1.00  0.00           O
ATOM    4459  C1*   U C  59      27.311 138.517 264.361  1.00  0.00           C
ATOM    4460  N1    U C  59      28.245 137.468 263.873  1.00  0.00           N
ATOM    4461  C2    U C  59      29.147 136.986 264.791  1.00  0.00           C
ATOM    4462  O2    U C  59      29.144 137.344 265.958  1.00  0.00           O
ATOM    4463  N3    U C  59      30.047 136.052 264.314  1.00  0.00           N
ATOM    4464  C4    U C  59      30.121 135.547 263.034  1.00  0.00           C
ATOM    4465  O4    U C  59      30.980 134.695 262.777  1.00  0.00           O
ATOM    4466  C5    U C  59      29.135 136.083 262.118  1.00  0.00           C
ATOM    4467  C6    U C  59      28.244 136.999 262.566  1.00  0.00           C
ATOM    4468  P     C C  60      28.621 143.186 263.514  1.00  0.00           P
ATOM    4469  O1P   C C  60      28.312 144.517 264.063  1.00  0.00           O
ATOM    4470  O2P   C C  60      28.975 143.043 262.066  1.00  0.00           O
ATOM    4471  O5*   C C  60      29.875 142.532 264.247  1.00  0.00           O
ATOM    4472  C5*   C C  60      30.013 142.529 265.676  1.00  0.00           C
ATOM    4473  C4*   C C  60      31.332 141.858 266.059  1.00  0.00           C
ATOM    4474  O4*   C C  60      31.379 140.540 265.418  1.00  0.00           O
ATOM    4475  C3*   C C  60      32.567 142.586 265.559  1.00  0.00           C
ATOM    4476  O3*   C C  60      33.660 142.355 266.438  1.00  0.00           O
ATOM    4477  C2*   C C  60      32.822 141.902 264.237  1.00  0.00           C
```

| | | | | | | | | | |
|---|---|---|---|---|---|---|---|---|---|
| ATOM | 4478 | O2* | C | C | 60 | 34.145 | 142.013 | 263.796 | 1.00 | 0.00 | O |
| ATOM | 4479 | C1* | C | C | 60 | 32.540 | 140.453 | 264.621 | 1.00 | 0.00 | C |
| ATOM | 4480 | N1 | C | C | 60 | 32.244 | 139.628 | 263.444 | 1.00 | 0.00 | N |
| ATOM | 4481 | C2 | C | C | 60 | 32.923 | 138.410 | 263.296 | 1.00 | 0.00 | C |
| ATOM | 4482 | O2 | C | C | 60 | 33.739 | 138.049 | 264.191 | 1.00 | 0.00 | O |
| ATOM | 4483 | N3 | C | C | 60 | 32.693 | 137.664 | 262.199 | 1.00 | 0.00 | N |
| ATOM | 4484 | C4 | C | C | 60 | 31.835 | 138.087 | 261.254 | 1.00 | 0.00 | C |
| ATOM | 4485 | N4 | C | C | 60 | 31.695 | 137.336 | 260.169 | 1.00 | 0.00 | N |
| ATOM | 4486 | C5 | C | C | 60 | 31.112 | 139.304 | 261.381 | 1.00 | 0.00 | C |
| ATOM | 4487 | C6 | C | C | 60 | 31.347 | 140.045 | 262.491 | 1.00 | 0.00 | C |
| ATOM | 4488 | P | C | C | 61 | 33.954 | 143.418 | 267.587 | 1.00 | 0.00 | P |
| ATOM | 4489 | O1P | C | C | 61 | 35.027 | 142.801 | 268.379 | 1.00 | 0.00 | O |
| ATOM | 4490 | O2P | C | C | 61 | 32.693 | 143.846 | 268.232 | 1.00 | 0.00 | O |
| ATOM | 4491 | O5* | C | C | 61 | 34.480 | 144.715 | 266.814 | 1.00 | 0.00 | O |
| ATOM | 4492 | C5* | C | C | 61 | 35.844 | 144.817 | 266.398 | 1.00 | 0.00 | C |
| ATOM | 4493 | C4* | C | C | 61 | 36.076 | 146.135 | 265.674 | 1.00 | 0.00 | C |
| ATOM | 4494 | O4* | C | C | 61 | 35.659 | 145.999 | 264.291 | 1.00 | 0.00 | O |
| ATOM | 4495 | C3* | C | C | 61 | 35.253 | 147.300 | 266.189 | 1.00 | 0.00 | C |
| ATOM | 4496 | O3* | C | C | 61 | 35.889 | 147.891 | 267.333 | 1.00 | 0.00 | O |
| ATOM | 4497 | C2* | C | C | 61 | 35.236 | 148.219 | 264.976 | 1.00 | 0.00 | C |
| ATOM | 4498 | O2* | C | C | 61 | 36.473 | 148.882 | 264.827 | 1.00 | 0.00 | O |
| ATOM | 4499 | C1* | C | C | 61 | 35.105 | 147.220 | 263.827 | 1.00 | 0.00 | C |
| ATOM | 4500 | N1 | C | C | 61 | 33.728 | 146.955 | 263.358 | 1.00 | 0.00 | N |
| ATOM | 4501 | C2 | C | C | 61 | 33.048 | 147.944 | 262.664 | 1.00 | 0.00 | C |
| ATOM | 4502 | O2 | C | C | 61 | 33.604 | 149.034 | 262.480 | 1.00 | 0.00 | O |
| ATOM | 4503 | N3 | C | C | 61 | 31.797 | 147.699 | 262.213 | 1.00 | 0.00 | N |
| ATOM | 4504 | C4 | C | C | 61 | 31.226 | 146.513 | 262.457 | 1.00 | 0.00 | C |
| ATOM | 4505 | N4 | C | C | 61 | 29.995 | 146.302 | 262.010 | 1.00 | 0.00 | N |
| ATOM | 4506 | C5 | C | C | 61 | 31.898 | 145.489 | 263.174 | 1.00 | 0.00 | C |
| ATOM | 4507 | C6 | C | C | 61 | 33.139 | 145.751 | 263.598 | 1.00 | 0.00 | C |
| ATOM | 4508 | P | A | C | 62 | 35.018 | 148.751 | 268.384 | 1.00 | 0.00 | P |
| ATOM | 4509 | O1P | A | C | 62 | 35.866 | 149.124 | 269.521 | 1.00 | 0.00 | O |
| ATOM | 4510 | O2P | A | C | 62 | 33.749 | 148.016 | 268.644 | 1.00 | 0.00 | O |
| ATOM | 4511 | O5* | A | C | 62 | 34.638 | 150.072 | 267.571 | 1.00 | 0.00 | O |
| ATOM | 4512 | C5* | A | C | 62 | 35.610 | 151.069 | 267.301 | 1.00 | 0.00 | C |
| ATOM | 4513 | C4* | A | C | 62 | 34.950 | 152.269 | 266.679 | 1.00 | 0.00 | C |
| ATOM | 4514 | O4* | A | C | 62 | 34.361 | 151.892 | 265.395 | 1.00 | 0.00 | O |
| ATOM | 4515 | C3* | A | C | 62 | 33.757 | 152.785 | 267.454 | 1.00 | 0.00 | C |
| ATOM | 4516 | O3* | A | C | 62 | 34.231 | 153.616 | 268.483 | 1.00 | 0.00 | O |
| ATOM | 4517 | C2* | A | C | 62 | 33.018 | 153.557 | 266.370 | 1.00 | 0.00 | C |
| ATOM | 4518 | O2* | A | C | 62 | 33.715 | 154.708 | 265.950 | 1.00 | 0.00 | O |
| ATOM | 4519 | C1* | A | C | 62 | 33.133 | 152.582 | 265.215 | 1.00 | 0.00 | C |
| ATOM | 4520 | N9 | A | C | 62 | 32.060 | 151.594 | 265.127 | 1.00 | 0.00 | N |
| ATOM | 4521 | C8 | A | C | 62 | 32.118 | 150.265 | 265.444 | 1.00 | 0.00 | C |
| ATOM | 4522 | N7 | A | C | 62 | 31.036 | 149.593 | 265.124 | 1.00 | 0.00 | N |
| ATOM | 4523 | C5 | A | C | 62 | 30.191 | 150.558 | 264.591 | 1.00 | 0.00 | C |
| ATOM | 4524 | C6 | A | C | 62 | 28.915 | 150.482 | 264.017 | 1.00 | 0.00 | C |
| ATOM | 4525 | N6 | A | C | 62 | 28.200 | 149.342 | 263.915 | 1.00 | 0.00 | N |
| ATOM | 4526 | N1 | A | C | 62 | 28.376 | 151.625 | 263.542 | 1.00 | 0.00 | N |
| ATOM | 4527 | C2 | A | C | 62 | 29.084 | 152.763 | 263.647 | 1.00 | 0.00 | C |
| ATOM | 4528 | N3 | A | C | 62 | 30.289 | 152.961 | 264.161 | 1.00 | 0.00 | N |
| ATOM | 4529 | C4 | A | C | 62 | 30.800 | 151.804 | 264.616 | 1.00 | 0.00 | C |
| ATOM | 4530 | P | C | C | 63 | 33.329 | 153.886 | 269.788 | 1.00 | 0.00 | P |
| ATOM | 4531 | O1P | C | C | 63 | 34.205 | 154.750 | 270.589 | 1.00 | 0.00 | O |
| ATOM | 4532 | O2P | C | C | 63 | 32.799 | 152.638 | 270.369 | 1.00 | 0.00 | O |
| ATOM | 4533 | O5* | C | C | 63 | 32.102 | 154.737 | 269.263 | 1.00 | 0.00 | O |
| ATOM | 4534 | C5* | C | C | 63 | 32.253 | 156.132 | 269.080 | 1.00 | 0.00 | C |
| ATOM | 4535 | C4* | C | C | 63 | 31.008 | 156.709 | 268.477 | 1.00 | 0.00 | C |
| ATOM | 4536 | O4* | C | C | 63 | 30.684 | 155.935 | 267.288 | 1.00 | 0.00 | O |
| ATOM | 4537 | C3* | C | C | 63 | 29.755 | 156.584 | 269.324 | 1.00 | 0.00 | C |
| ATOM | 4538 | O3* | C | C | 63 | 29.662 | 157.613 | 270.313 | 1.00 | 0.00 | O |
| ATOM | 4539 | C2* | C | C | 63 | 28.687 | 156.734 | 268.257 | 1.00 | 0.00 | C |
| ATOM | 4540 | O2* | C | C | 63 | 28.570 | 158.077 | 267.802 | 1.00 | 0.00 | O |
| ATOM | 4541 | C1* | C | C | 63 | 29.273 | 155.874 | 267.136 | 1.00 | 0.00 | C |
| ATOM | 4542 | N1 | C | C | 63 | 28.846 | 154.455 | 267.152 | 1.00 | 0.00 | N |
| ATOM | 4543 | C2 | C | C | 63 | 27.638 | 154.118 | 266.561 | 1.00 | 0.00 | C |
| ATOM | 4544 | O2 | C | C | 63 | 26.959 | 155.036 | 266.050 | 1.00 | 0.00 | O |
| ATOM | 4545 | N3 | C | C | 63 | 27.229 | 152.806 | 266.565 | 1.00 | 0.00 | N |
| ATOM | 4546 | C4 | C | C | 63 | 28.005 | 151.876 | 267.150 | 1.00 | 0.00 | C |
| ATOM | 4547 | N4 | C | C | 63 | 27.609 | 150.613 | 267.146 | 1.00 | 0.00 | N |
| ATOM | 4548 | C5 | C | C | 63 | 29.240 | 152.209 | 267.762 | 1.00 | 0.00 | C |
| ATOM | 4549 | C6 | C | C | 63 | 29.621 | 153.494 | 267.736 | 1.00 | 0.00 | C |
| ATOM | 4550 | P | A | C | 64 | 28.892 | 157.323 | 271.706 | 1.00 | 0.00 | P |
| ATOM | 4551 | O1P | A | C | 64 | 29.108 | 158.468 | 272.620 | 1.00 | 0.00 | O |
| ATOM | 4552 | O2P | A | C | 64 | 29.271 | 155.964 | 272.156 | 1.00 | 0.00 | O |
| ATOM | 4553 | O5* | A | C | 64 | 27.374 | 157.372 | 271.278 | 1.00 | 0.00 | O |
| ATOM | 4554 | C5* | A | C | 64 | 26.871 | 158.534 | 270.650 | 1.00 | 0.00 | C |
| ATOM | 4555 | C4* | A | C | 64 | 25.441 | 158.331 | 270.245 | 1.00 | 0.00 | C |
| ATOM | 4556 | O4* | A | C | 64 | 25.397 | 157.541 | 269.025 | 1.00 | 0.00 | O |
| ATOM | 4557 | C3* | A | C | 64 | 24.573 | 157.539 | 271.207 | 1.00 | 0.00 | C |
| ATOM | 4558 | O3* | A | C | 64 | 24.174 | 158.329 | 272.337 | 1.00 | 0.00 | O |
| ATOM | 4559 | C2* | A | C | 64 | 23.432 | 157.145 | 270.275 | 1.00 | 0.00 | C |
| ATOM | 4560 | O2* | A | C | 64 | 22.581 | 158.210 | 269.911 | 1.00 | 0.00 | O |
| ATOM | 4561 | C1* | A | C | 64 | 24.219 | 156.742 | 269.028 | 1.00 | 0.00 | C |
| ATOM | 4562 | N9 | A | C | 64 | 24.619 | 155.348 | 269.143 | 1.00 | 0.00 | N |
| ATOM | 4563 | C8 | A | C | 64 | 25.782 | 154.817 | 269.629 | 1.00 | 0.00 | C |
| ATOM | 4564 | N7 | A | C | 64 | 25.790 | 153.512 | 269.655 | 1.00 | 0.00 | N |

```
ATOM   4565  C5    A C  64     24.553 153.169 269.136  1.00  0.00           C
ATOM   4566  C6    A C  64     23.958 151.940 268.876  1.00  0.00           C
ATOM   4567  N6    A C  64     24.545 150.777 269.139  1.00  0.00           N
ATOM   4568  N1    A C  64     22.724 151.943 268.330  1.00  0.00           N
ATOM   4569  C2    A C  64     22.147 153.115 268.061  1.00  0.00           C
ATOM   4570  N3    A C  64     22.610 154.339 268.261  1.00  0.00           N
ATOM   4571  C4    A C  64     23.831 154.287 268.809  1.00  0.00           C
ATOM   4572  P     G C  65     24.003 157.628 273.787  1.00  0.00           P
ATOM   4573  O1P   G C  65     23.815 158.679 274.820  1.00  0.00           O
ATOM   4574  O2P   G C  65     25.062 156.613 273.975  1.00  0.00           O
ATOM   4575  O5*   G C  65     22.623 156.851 273.653  1.00  0.00           O
ATOM   4576  C5*   G C  65     21.525 157.456 273.002  1.00  0.00           C
ATOM   4577  C4*   G C  65     20.553 156.410 272.516  1.00  0.00           C
ATOM   4578  O4*   G C  65     21.134 155.667 271.420  1.00  0.00           O
ATOM   4579  C3*   G C  65     20.114 155.309 273.472  1.00  0.00           C
ATOM   4580  O3*   G C  65     19.106 155.767 274.360  1.00  0.00           O
ATOM   4581  C2*   G C  65     19.494 154.339 272.486  1.00  0.00           C
ATOM   4582  O2*   G C  65     18.262 154.804 272.003  1.00  0.00           O
ATOM   4583  C1*   G C  65     20.509 154.396 271.340  1.00  0.00           C
ATOM   4584  N9    G C  65     21.519 153.367 271.558  1.00  0.00           N
ATOM   4585  C8    G C  65     22.812 153.530 271.965  1.00  0.00           C
ATOM   4586  N7    G C  65     23.450 152.405 272.094  1.00  0.00           N
ATOM   4587  C5    G C  65     22.513 151.444 271.745  1.00  0.00           C
ATOM   4588  C6    G C  65     22.639 150.041 271.646  1.00  0.00           C
ATOM   4589  O6    G C  65     23.633 149.333 271.890  1.00  0.00           O
ATOM   4590  N1    G C  65     21.452 149.455 271.210  1.00  0.00           N
ATOM   4591  C2    G C  65     20.297 150.146 270.902  1.00  0.00           C
ATOM   4592  N2    G C  65     19.251 149.426 270.488  1.00  0.00           N
ATOM   4593  N3    G C  65     20.178 151.449 270.988  1.00  0.00           N
ATOM   4594  C4    G C  65     21.320 152.028 271.414  1.00  0.00           C
ATOM   4595  P     A C  66     18.915 155.056 275.797  1.00  0.00           P
ATOM   4596  O1P   A C  66     17.967 155.867 276.594  1.00  0.00           O
ATOM   4597  O2P   A C  66     20.262 154.778 276.332  1.00  0.00           O
ATOM   4598  O5*   A C  66     18.214 153.672 275.444  1.00  0.00           O
ATOM   4599  C5*   A C  66     16.906 153.650 274.903  1.00  0.00           C
ATOM   4600  C4*   A C  66     16.518 152.242 274.555  1.00  0.00           C
ATOM   4601  O4*   A C  66     17.507 151.686 273.656  1.00  0.00           O
ATOM   4602  C3*   A C  66     16.544 151.279 275.715  1.00  0.00           C
ATOM   4603  O3*   A C  66     15.366 151.412 276.491  1.00  0.00           O
ATOM   4604  C2*   A C  66     16.629 149.948 274.986  1.00  0.00           C
ATOM   4605  O2*   A C  66     15.409 149.546 274.397  1.00  0.00           O
ATOM   4606  C1*   A C  66     17.614 150.289 273.870  1.00  0.00           C
ATOM   4607  N9    A C  66     19.017 149.985 274.171  1.00  0.00           N
ATOM   4608  C8    A C  66     19.994 150.894 274.485  1.00  0.00           C
ATOM   4609  N7    A C  66     21.177 150.357 274.684  1.00  0.00           N
ATOM   4610  C5    A C  66     20.966 149.005 274.487  1.00  0.00           C
ATOM   4611  C6    A C  66     21.831 147.896 274.560  1.00  0.00           C
ATOM   4612  N6    A C  66     23.111 147.992 274.860  1.00  0.00           N
ATOM   4613  N1    A C  66     21.316 146.676 274.330  1.00  0.00           N
ATOM   4614  C2    A C  66     20.002 146.579 274.066  1.00  0.00           C
ATOM   4615  N3    A C  66     19.084 147.545 273.975  1.00  0.00           N
ATOM   4616  C4    A C  66     19.637 148.751 274.190  1.00  0.00           C
ATOM   4617  P     A C  67     15.420 151.147 278.076  1.00  0.00           P
ATOM   4618  O1P   A C  67     14.088 151.493 278.625  1.00  0.00           O
ATOM   4619  O2P   A C  67     16.640 151.773 278.657  1.00  0.00           O
ATOM   4620  O5*   A C  67     15.526 149.580 278.165  1.00  0.00           O
ATOM   4621  C5*   A C  67     14.475 148.771 277.668  1.00  0.00           C
ATOM   4622  C4*   A C  67     14.899 147.333 277.687  1.00  0.00           C
ATOM   4623  O4*   A C  67     16.003 147.190 276.762  1.00  0.00           O
ATOM   4624  C3*   A C  67     15.505 146.904 279.007  1.00  0.00           C
ATOM   4625  O3*   A C  67     14.496 146.436 279.876  1.00  0.00           O
ATOM   4626  C2*   A C  67     16.344 145.720 278.575  1.00  0.00           C
ATOM   4627  O2*   A C  67     15.500 144.614 278.302  1.00  0.00           O
ATOM   4628  C1*   A C  67     16.945 146.259 277.281  1.00  0.00           C
ATOM   4629  N9    A C  67     18.236 146.931 277.494  1.00  0.00           N
ATOM   4630  C8    A C  67     18.478 148.262 277.690  1.00  0.00           C
ATOM   4631  N7    A C  67     19.759 148.550 277.837  1.00  0.00           N
ATOM   4632  C5    A C  67     20.393 147.324 277.743  1.00  0.00           C
ATOM   4633  C6    A C  67     21.762 146.940 277.848  1.00  0.00           C
ATOM   4634  N6    A C  67     22.761 147.787 278.044  1.00  0.00           N
ATOM   4635  N1    A C  67     22.059 145.631 277.742  1.00  0.00           N
ATOM   4636  C2    A C  67     21.051 144.768 277.553  1.00  0.00           C
ATOM   4637  N3    A C  67     19.735 145.003 277.436  1.00  0.00           N
ATOM   4638  C4    A C  67     19.472 146.316 277.536  1.00  0.00           C
ATOM   4639  P     U C  68     14.758 146.419 281.460  1.00  0.00           P
ATOM   4640  O1P   U C  68     13.436 146.113 282.054  1.00  0.00           O
ATOM   4641  O2P   U C  68     15.531 147.619 281.911  1.00  0.00           O
ATOM   4642  O5*   U C  68     15.693 145.155 281.704  1.00  0.00           O
ATOM   4643  C5*   U C  68     15.265 143.861 281.366  1.00  0.00           C
ATOM   4644  C4*   U C  68     16.401 142.902 281.554  1.00  0.00           C
ATOM   4645  O4*   U C  68     17.431 143.158 280.551  1.00  0.00           O
ATOM   4646  C3*   U C  68     17.151 143.065 282.867  1.00  0.00           C
ATOM   4647  O3*   U C  68     16.454 142.389 283.899  1.00  0.00           O
ATOM   4648  C2*   U C  68     18.461 142.363 282.536  1.00  0.00           C
ATOM   4649  O2*   U C  68     18.296 140.955 282.484  1.00  0.00           O
ATOM   4650  C1*   U C  68     18.705 142.886 281.115  1.00  0.00           C
ATOM   4651  N1    U C  68     19.506 144.119 281.119  1.00  0.00           N
```

| | | | | | | | | | |
|---|---|---|---|---|---|---|---|---|---|
| ATOM | 4652 | C2 | U C | 68 | 20.874 | 143.941 | 281.266 | 1.00 | 0.00 |
| ATOM | 4653 | O2 | U C | 68 | 21.385 | 142.824 | 281.383 | 1.00 | 0.00 |
| ATOM | 4654 | N3 | U C | 68 | 21.616 | 145.093 | 281.274 | 1.00 | 0.00 |
| ATOM | 4655 | C4 | U C | 68 | 21.148 | 146.385 | 281.157 | 1.00 | 0.00 |
| ATOM | 4656 | O4 | U C | 68 | 21.957 | 147.330 | 281.200 | 1.00 | 0.00 |
| ATOM | 4657 | C5 | U C | 68 | 19.710 | 146.495 | 281.021 | 1.00 | 0.00 |
| ATOM | 4658 | C6 | U C | 68 | 18.963 | 145.375 | 281.001 | 1.00 | 0.00 |
| ATOM | 4659 | P | U C | 69 | 16.646 | 142.852 | 285.410 | 1.00 | 0.00 |
| ATOM | 4660 | O1P | U C | 69 | 15.813 | 141.981 | 286.286 | 1.00 | 0.00 |
| ATOM | 4661 | O2P | U C | 69 | 16.465 | 144.311 | 285.418 | 1.00 | 0.00 |
| ATOM | 4662 | O5* | U C | 69 | 18.176 | 142.568 | 285.756 | 1.00 | 0.00 |
| ATOM | 4663 | C5* | U C | 69 | 18.692 | 141.258 | 285.661 | 1.00 | 0.00 |
| ATOM | 4664 | C4* | U C | 69 | 20.198 | 141.279 | 285.831 | 1.00 | 0.00 |
| ATOM | 4665 | O4* | U C | 69 | 20.831 | 141.896 | 284.671 | 1.00 | 0.00 |
| ATOM | 4666 | C3* | U C | 69 | 20.699 | 142.098 | 287.004 | 1.00 | 0.00 |
| ATOM | 4667 | O3* | U C | 69 | 20.602 | 141.302 | 288.186 | 1.00 | 0.00 |
| ATOM | 4668 | C2* | U C | 69 | 22.142 | 142.367 | 286.597 | 1.00 | 0.00 |
| ATOM | 4669 | O2* | U C | 69 | 23.039 | 141.289 | 286.808 | 1.00 | 0.00 |
| ATOM | 4670 | C1* | U C | 69 | 21.983 | 142.584 | 285.096 | 1.00 | 0.00 |
| ATOM | 4671 | N1 | U C | 69 | 21.828 | 144.006 | 284.789 | 1.00 | 0.00 |
| ATOM | 4672 | C2 | U C | 69 | 22.982 | 144.762 | 284.786 | 1.00 | 0.00 |
| ATOM | 4673 | O2 | U C | 69 | 24.102 | 144.272 | 284.989 | 1.00 | 0.00 |
| ATOM | 4674 | N3 | U C | 69 | 22.786 | 146.097 | 284.541 | 1.00 | 0.00 |
| ATOM | 4675 | C4 | U C | 69 | 21.586 | 146.722 | 284.287 | 1.00 | 0.00 |
| ATOM | 4676 | O4 | U C | 69 | 21.566 | 147.933 | 284.087 | 1.00 | 0.00 |
| ATOM | 4677 | C5 | U C | 69 | 20.446 | 145.859 | 284.289 | 1.00 | 0.00 |
| ATOM | 4678 | C6 | U C | 69 | 20.605 | 144.564 | 284.534 | 1.00 | 0.00 |
| ATOM | 4679 | P | C C | 70 | 20.466 | 142.006 | 289.631 | 1.00 | 0.00 |
| ATOM | 4680 | O1P | C C | 70 | 20.014 | 140.925 | 290.576 | 1.00 | 0.00 |
| ATOM | 4681 | O2P | C C | 70 | 19.647 | 143.243 | 289.492 | 1.00 | 0.00 |
| ATOM | 4682 | O5* | C C | 70 | 21.961 | 142.447 | 289.949 | 1.00 | 0.00 |
| ATOM | 4683 | C5* | C C | 70 | 22.948 | 141.463 | 290.240 | 1.00 | 0.00 |
| ATOM | 4684 | C4* | C C | 70 | 24.327 | 142.081 | 290.226 | 1.00 | 0.00 |
| ATOM | 4685 | O4* | C C | 70 | 24.647 | 142.598 | 288.902 | 1.00 | 0.00 |
| ATOM | 4686 | C3* | C C | 70 | 24.552 | 143.279 | 291.123 | 1.00 | 0.00 |
| ATOM | 4687 | O3* | C C | 70 | 24.712 | 142.852 | 292.465 | 1.00 | 0.00 |
| ATOM | 4688 | C2* | C C | 70 | 25.851 | 143.813 | 290.531 | 1.00 | 0.00 |
| ATOM | 4689 | O2* | C C | 70 | 26.989 | 143.019 | 290.846 | 1.00 | 0.00 |
| ATOM | 4690 | C1* | C C | 70 | 25.545 | 143.682 | 289.039 | 1.00 | 0.00 |
| ATOM | 4691 | N1 | C C | 70 | 24.892 | 144.879 | 288.501 | 1.00 | 0.00 |
| ATOM | 4692 | C2 | C C | 70 | 25.696 | 145.941 | 288.132 | 1.00 | 0.00 |
| ATOM | 4693 | O2 | C C | 70 | 26.920 | 145.815 | 288.267 | 1.00 | 0.00 |
| ATOM | 4694 | N3 | C C | 70 | 25.136 | 147.073 | 287.641 | 1.00 | 0.00 |
| ATOM | 4695 | C4 | C C | 70 | 23.806 | 147.155 | 287.511 | 1.00 | 0.00 |
| ATOM | 4696 | N4 | C C | 70 | 23.287 | 148.299 | 287.012 | 1.00 | 0.00 |
| ATOM | 4697 | C5 | C C | 70 | 22.948 | 146.069 | 287.880 | 1.00 | 0.00 |
| ATOM | 4698 | C6 | C C | 70 | 23.530 | 144.957 | 288.365 | 1.00 | 0.00 |
| ATOM | 4699 | P | G C | 71 | 24.394 | 143.863 | 293.685 | 1.00 | 0.00 |
| ATOM | 4700 | O1P | G C | 71 | 24.509 | 143.022 | 294.908 | 1.00 | 0.00 |
| ATOM | 4701 | O2P | G C | 71 | 23.129 | 144.584 | 293.417 | 1.00 | 0.00 |
| ATOM | 4702 | O5* | G C | 71 | 25.556 | 144.964 | 293.615 | 1.00 | 0.00 |
| ATOM | 4703 | C5* | G C | 71 | 26.866 | 144.695 | 294.113 | 1.00 | 0.00 |
| ATOM | 4704 | C4* | G C | 71 | 27.841 | 145.792 | 293.718 | 1.00 | 0.00 |
| ATOM | 4705 | O4* | G C | 71 | 27.880 | 145.944 | 292.270 | 1.00 | 0.00 |
| ATOM | 4706 | C3* | G C | 71 | 27.588 | 147.211 | 294.219 | 1.00 | 0.00 |
| ATOM | 4707 | O3* | G C | 71 | 28.050 | 147.428 | 295.551 | 1.00 | 0.00 |
| ATOM | 4708 | C2* | G C | 71 | 28.454 | 148.005 | 293.257 | 1.00 | 0.00 |
| ATOM | 4709 | O2* | G C | 71 | 29.825 | 147.863 | 293.537 | 1.00 | 0.00 |
| ATOM | 4710 | C1* | G C | 71 | 28.126 | 147.307 | 291.940 | 1.00 | 0.00 |
| ATOM | 4711 | N9 | G C | 71 | 26.910 | 147.883 | 291.369 | 1.00 | 0.00 |
| ATOM | 4712 | C8 | G C | 71 | 25.632 | 147.390 | 291.453 | 1.00 | 0.00 |
| ATOM | 4713 | N7 | G C | 71 | 24.752 | 148.151 | 290.859 | 1.00 | 0.00 |
| ATOM | 4714 | C5 | G C | 71 | 25.497 | 149.202 | 290.343 | 1.00 | 0.00 |
| ATOM | 4715 | C6 | G C | 71 | 25.093 | 150.338 | 289.589 | 1.00 | 0.00 |
| ATOM | 4716 | O6 | G C | 71 | 23.947 | 150.663 | 289.214 | 1.00 | 0.00 |
| ATOM | 4717 | N1 | G C | 71 | 26.181 | 151.150 | 289.277 | 1.00 | 0.00 |
| ATOM | 4718 | C2 | G C | 71 | 27.477 | 150.905 | 289.648 | 1.00 | 0.00 |
| ATOM | 4719 | N2 | G C | 71 | 28.387 | 151.809 | 289.258 | 1.00 | 0.00 |
| ATOM | 4720 | N3 | G C | 71 | 27.859 | 149.860 | 290.346 | 1.00 | 0.00 |
| ATOM | 4721 | C4 | G C | 71 | 26.830 | 149.053 | 290.654 | 1.00 | 0.00 |
| ATOM | 4722 | P | C C | 72 | 27.579 | 148.745 | 296.346 | 1.00 | 0.00 |
| ATOM | 4723 | O1P | C C | 72 | 28.421 | 148.890 | 297.554 | 1.00 | 0.00 |
| ATOM | 4724 | O2P | C C | 72 | 26.099 | 148.702 | 296.483 | 1.00 | 0.00 |
| ATOM | 4725 | O5* | C C | 72 | 27.964 | 149.945 | 295.382 | 1.00 | 0.00 |
| ATOM | 4726 | C5* | C C | 72 | 29.221 | 150.577 | 295.506 | 1.00 | 0.00 |
| ATOM | 4727 | C4* | C C | 72 | 29.178 | 151.924 | 294.854 | 1.00 | 0.00 |
| ATOM | 4728 | O4* | C C | 72 | 28.683 | 151.755 | 293.503 | 1.00 | 0.00 |
| ATOM | 4729 | C3* | C C | 72 | 28.184 | 152.906 | 295.442 | 1.00 | 0.00 |
| ATOM | 4730 | O3* | C C | 72 | 28.689 | 153.538 | 296.604 | 1.00 | 0.00 |
| ATOM | 4731 | C2* | C C | 72 | 28.022 | 153.885 | 294.290 | 1.00 | 0.00 |
| ATOM | 4732 | O2* | C C | 72 | 29.108 | 154.778 | 294.110 | 1.00 | 0.00 |
| ATOM | 4733 | C1* | C C | 72 | 27.980 | 152.919 | 293.112 | 1.00 | 0.00 |
| ATOM | 4734 | N1 | C C | 72 | 26.603 | 152.544 | 292.789 | 1.00 | 0.00 |
| ATOM | 4735 | C2 | C C | 72 | 25.865 | 153.412 | 291.997 | 1.00 | 0.00 |
| ATOM | 4736 | O2 | C C | 72 | 26.401 | 154.475 | 291.622 | 1.00 | 0.00 |
| ATOM | 4737 | N3 | C C | 72 | 24.596 | 153.086 | 291.660 | 1.00 | 0.00 |
| ATOM | 4738 | C4 | C C | 72 | 24.069 | 151.939 | 292.097 | 1.00 | 0.00 |

```
ATOM   4739  N4   C C  72     22.817 151.647 291.737  1.00  0.00           N
ATOM   4740  C5   C C  72     24.806 151.038 292.924  1.00  0.00           C
ATOM   4741  C6   C C  72     26.057 151.377 293.242  1.00  0.00           C
ATOM   4742  P    A C  73     27.640 154.178 297.310  1.00  0.00           P
ATOM   4743  O1P  A C  73     28.690 154.566 298.281  1.00  0.00           O
ATOM   4744  O2P  A C  73     26.729 153.052 297.637  1.00  0.00           O
ATOM   4745  O5*  A C  73     26.795 155.480 296.952  1.00  0.00           O
ATOM   4746  C5*  A C  73     27.456 156.724 296.777  1.00  0.00           C
ATOM   4747  C4*  A C  73     26.475 157.794 296.387  1.00  0.00           C
ATOM   4748  O4*  A C  73     25.860 157.442 295.124  1.00  0.00           O
ATOM   4749  C3*  A C  73     25.285 157.968 297.311  1.00  0.00           C
ATOM   4750  O3*  A C  73     25.617 158.760 298.441  1.00  0.00           O
ATOM   4751  C2*  A C  73     24.309 158.696 296.403  1.00  0.00           C
ATOM   4752  O2*  A C  73     24.630 160.064 296.273  1.00  0.00           O
ATOM   4753  C1*  A C  73     24.533 157.945 295.086  1.00  0.00           C
ATOM   4754  N9   A C  73     23.624 156.806 294.952  1.00  0.00           N
ATOM   4755  C8   A C  73     23.901 155.484 295.183  1.00  0.00           C
ATOM   4756  N7   A C  73     22.873 154.692 295.009  1.00  0.00           N
ATOM   4757  C5   A C  73     21.850 155.549 294.631  1.00  0.00           C
ATOM   4758  C6   A C  73     20.502 155.325 294.302  1.00  0.00           C
ATOM   4759  N6   A C  73     19.931 154.119 294.312  1.00  0.00           N
ATOM   4760  N1   A C  73     19.751 156.397 293.957  1.00  0.00           N
ATOM   4761  C2   A C  73     20.328 157.608 293.953  1.00  0.00           C
ATOM   4762  N3   A C  73     21.584 157.945 294.245  1.00  0.00           N
ATOM   4763  C4   A C  73     22.301 156.854 294.583  1.00  0.00           C
ATOM   4764  P    C C  74     24.954 158.300 299.815  1.00  0.00           P
ATOM   4765  O1P  C C  74     24.776 156.792 299.645  1.00  0.00           O
ATOM   4766  O2P  C C  74     23.740 159.189 300.091  1.00  0.00           O
ATOM   4767  O5*  C C  74     26.075 158.557 300.943  1.00  0.00           O
ATOM   4768  C5*  C C  74     26.823 157.453 301.481  1.00  0.00           C
ATOM   4769  C4*  C C  74     28.301 157.781 301.553  1.00  0.00           C
ATOM   4770  O4*  C C  74     28.873 157.960 300.223  1.00  0.00           O
ATOM   4771  C3*  C C  74     28.723 159.016 302.330  1.00  0.00           C
ATOM   4772  O3*  C C  74     28.807 158.615 303.718  1.00  0.00           O
ATOM   4773  C2*  C C  74     30.122 159.257 301.779  1.00  0.00           C
ATOM   4774  O2*  C C  74     30.982 158.296 302.347  1.00  0.00           O
ATOM   4775  C1*  C C  74     29.976 158.843 300.304  1.00  0.00           C
ATOM   4776  N1   C C  74     29.889 159.847 299.232  1.00  0.00           N
ATOM   4777  C2   C C  74     31.047 160.509 298.805  1.00  0.00           C
ATOM   4778  O2   C C  74     32.123 160.237 299.359  1.00  0.00           O
ATOM   4779  N3   C C  74     30.964 161.420 297.811  1.00  0.00           N
ATOM   4780  C4   C C  74     29.786 161.691 297.248  1.00  0.00           C
ATOM   4781  N4   C C  74     29.751 162.596 296.268  1.00  0.00           N
ATOM   4782  C5   C C  74     28.590 161.022 297.655  1.00  0.00           C
ATOM   4783  C6   C C  74     28.688 160.120 298.637  1.00  0.00           C
ATOM   4784  P    C C  75     29.257 159.585 304.427  1.00  0.00           P
ATOM   4785  O1P  C C  75     29.751 158.819 305.598  1.00  0.00           O
ATOM   4786  O2P  C C  75     27.845 160.022 304.390  1.00  0.00           O
ATOM   4787  O5*  C C  75     30.161 160.890 304.579  1.00  0.00           O
ATOM   4788  C5*  C C  75     31.225 160.944 305.584  1.00  0.00           C
ATOM   4789  C4*  C C  75     31.809 162.347 305.785  1.00  0.00           C
ATOM   4790  O4*  C C  75     32.464 162.786 304.568  1.00  0.00           O
ATOM   4791  C3*  C C  75     30.858 163.479 306.131  1.00  0.00           C
ATOM   4792  O3*  C C  75     30.531 163.462 307.503  1.00  0.00           O
ATOM   4793  C2*  C C  75     31.648 164.708 305.717  1.00  0.00           C
ATOM   4794  O2*  C C  75     32.603 164.992 306.728  1.00  0.00           O
ATOM   4795  C1*  C C  75     32.357 164.187 304.462  1.00  0.00           C
ATOM   4796  N1   C C  75     31.679 164.405 303.199  1.00  0.00           N
ATOM   4797  C2   C C  75     32.317 165.208 302.269  1.00  0.00           C
ATOM   4798  O2   C C  75     33.396 165.728 302.581  1.00  0.00           O
ATOM   4799  N3   C C  75     31.736 165.440 301.077  1.00  0.00           N
ATOM   4800  C4   C C  75     30.557 164.891 300.797  1.00  0.00           C
ATOM   4801  N4   C C  75     30.031 165.128 299.596  1.00  0.00           N
ATOM   4802  C5   C C  75     29.896 164.024 301.715  1.00  0.00           C
ATOM   4803  C6   C C  75     30.491 163.806 302.893  1.00  0.00           C
ATOM   4804  P    A C  76     29.452 163.223 308.187  1.00  0.00           P
ATOM   4805  O1P  A C  76     30.073 162.737 309.445  1.00  0.00           O
ATOM   4806  O2P  A C  76     28.545 162.340 307.454  1.00  0.00           O
ATOM   4807  O5*  A C  76     28.385 164.387 308.346  1.00  0.00           O
ATOM   4808  C5*  A C  76     28.438 165.196 309.538  1.00  0.00           C
ATOM   4809  C4*  A C  76     28.534 166.644 309.114  1.00  0.00           C
ATOM   4810  O4*  A C  76     27.768 167.477 310.012  1.00  0.00           O
ATOM   4811  C3*  A C  76     29.916 167.224 309.129  1.00  0.00           C
ATOM   4812  O3*  A C  76     30.455 166.736 307.928  1.00  0.00           O
ATOM   4813  C2*  A C  76     29.636 168.728 309.230  1.00  0.00           C
ATOM   4814  O2*  A C  76     29.273 169.076 307.820  1.00  0.00           O
ATOM   4815  C1*  A C  76     28.368 168.760 310.089  1.00  0.00           C
ATOM   4816  N9   A C  76     28.446 169.177 311.472  1.00  0.00           N
ATOM   4817  C8   A C  76     28.750 168.437 312.583  1.00  0.00           C
ATOM   4818  N7   A C  76     28.725 169.128 313.698  1.00  0.00           N
ATOM   4819  C5   A C  76     28.375 170.405 313.287  1.00  0.00           C
ATOM   4820  C6   A C  76     28.192 171.604 313.987  1.00  0.00           C
ATOM   4821  N6   A C  76     28.314 171.712 315.314  1.00  0.00           N
ATOM   4822  N1   A C  76     27.817 172.686 313.284  1.00  0.00           N
ATOM   4823  C2   A C  76     27.672 172.578 311.959  1.00  0.00           C
ATOM   4824  N3   A C  76     27.834 171.514 311.184  1.00  0.00           N
ATOM   4825  C4   A C  76     28.174 170.443 311.923  1.00  0.00           C
```

| TER | 4826 | | A | C | 76 | | | | | |
|---|---|---|---|---|---|---|---|---|---|---|
| ATOM | 4827 | O3P | U | D | 1 | 62.763 | 141.465 | 272.908 | 1.00 | 0.00 | O |
| ATOM | 4828 | P | U | D | 1 | 63.945 | 141.664 | 273.984 | 1.00 | 0.00 | P |
| ATOM | 4829 | O1P | U | D | 1 | 65.104 | 142.074 | 273.146 | 1.00 | 0.00 | O |
| ATOM | 4830 | O2P | U | D | 1 | 63.570 | 142.707 | 274.992 | 1.00 | 0.00 | O |
| ATOM | 4831 | O5* | U | D | 1 | 64.094 | 140.221 | 274.654 | 1.00 | 0.00 | O |
| ATOM | 4832 | C5* | U | D | 1 | 63.693 | 140.030 | 276.037 | 1.00 | 0.00 | C |
| ATOM | 4833 | C4* | U | D | 1 | 64.926 | 139.590 | 276.781 | 1.00 | 0.00 | C |
| ATOM | 4834 | O4* | U | D | 1 | 64.784 | 139.751 | 278.175 | 1.00 | 0.00 | O |
| ATOM | 4835 | C3* | U | D | 1 | 65.278 | 138.098 | 276.598 | 1.00 | 0.00 | C |
| ATOM | 4836 | O3* | U | D | 1 | 65.900 | 137.875 | 275.354 | 1.00 | 0.00 | O |
| ATOM | 4837 | C2* | U | D | 1 | 66.130 | 137.837 | 277.836 | 1.00 | 0.00 | C |
| ATOM | 4838 | O2* | U | D | 1 | 67.446 | 138.330 | 277.526 | 1.00 | 0.00 | O |
| ATOM | 4839 | C1* | U | D | 1 | 65.482 | 138.704 | 278.879 | 1.00 | 0.00 | C |
| ATOM | 4840 | N1 | U | D | 1 | 64.509 | 138.009 | 279.739 | 1.00 | 0.00 | N |
| ATOM | 4841 | C2 | U | D | 1 | 64.884 | 137.722 | 281.039 | 1.00 | 0.00 | C |
| ATOM | 4842 | O2 | U | D | 1 | 66.003 | 138.034 | 281.451 | 1.00 | 0.00 | O |
| ATOM | 4843 | N3 | U | D | 1 | 63.984 | 137.090 | 281.848 | 1.00 | 0.00 | N |
| ATOM | 4844 | C4 | U | D | 1 | 62.745 | 136.742 | 281.406 | 1.00 | 0.00 | C |
| ATOM | 4845 | O4 | U | D | 1 | 61.969 | 136.156 | 282.226 | 1.00 | 0.00 | O |
| ATOM | 4846 | C5 | U | D | 1 | 62.364 | 137.044 | 280.072 | 1.00 | 0.00 | C |
| ATOM | 4847 | C6 | U | D | 1 | 63.263 | 137.671 | 279.290 | 1.00 | 0.00 | C |
| ATOM | 4848 | P | C | D | 2 | 66.963 | 136.816 | 274.827 | 1.00 | 0.00 | P |
| ATOM | 4849 | O1P | C | D | 2 | 68.017 | 137.490 | 274.010 | 1.00 | 0.00 | O |
| ATOM | 4850 | O2P | C | D | 2 | 66.136 | 135.897 | 273.978 | 1.00 | 0.00 | O |
| ATOM | 4851 | O5* | C | D | 2 | 67.604 | 136.118 | 276.111 | 1.00 | 0.00 | O |
| ATOM | 4852 | C5* | C | D | 2 | 68.968 | 136.481 | 276.449 | 1.00 | 0.00 | C |
| ATOM | 4853 | C4* | C | D | 2 | 69.419 | 135.653 | 277.633 | 1.00 | 0.00 | C |
| ATOM | 4854 | O4* | C | D | 2 | 68.665 | 135.995 | 278.789 | 1.00 | 0.00 | O |
| ATOM | 4855 | C3* | C | D | 2 | 69.226 | 134.151 | 277.494 | 1.00 | 0.00 | C |
| ATOM | 4856 | O3* | C | D | 2 | 70.253 | 133.501 | 276.726 | 1.00 | 0.00 | O |
| ATOM | 4857 | C2* | C | D | 2 | 69.203 | 133.684 | 278.948 | 1.00 | 0.00 | C |
| ATOM | 4858 | O2* | C | D | 2 | 70.551 | 133.577 | 279.378 | 1.00 | 0.00 | O |
| ATOM | 4859 | C1* | C | D | 2 | 68.499 | 134.854 | 279.617 | 1.00 | 0.00 | C |
| ATOM | 4860 | N1 | C | D | 2 | 67.079 | 134.465 | 279.801 | 1.00 | 0.00 | N |
| ATOM | 4861 | C2 | C | D | 2 | 66.798 | 133.593 | 280.837 | 1.00 | 0.00 | C |
| ATOM | 4862 | O2 | C | D | 2 | 67.705 | 133.186 | 281.563 | 1.00 | 0.00 | O |
| ATOM | 4863 | N3 | C | D | 2 | 65.498 | 133.216 | 281.024 | 1.00 | 0.00 | N |
| ATOM | 4864 | C4 | C | D | 2 | 64.494 | 133.679 | 280.218 | 1.00 | 0.00 | C |
| ATOM | 4865 | N4 | C | D | 2 | 63.249 | 133.289 | 280.439 | 1.00 | 0.00 | N |
| ATOM | 4866 | C5 | C | D | 2 | 64.807 | 134.572 | 279.153 | 1.00 | 0.00 | C |
| ATOM | 4867 | C6 | C | D | 2 | 66.089 | 134.927 | 278.984 | 1.00 | 0.00 | C |
| ATOM | 4868 | P | C | D | 3 | 69.927 | 131.996 | 276.221 | 1.00 | 0.00 | P |
| ATOM | 4869 | O1P | C | D | 3 | 70.908 | 131.543 | 275.183 | 1.00 | 0.00 | O |
| ATOM | 4870 | O2P | C | D | 3 | 68.553 | 132.130 | 275.675 | 1.00 | 0.00 | O |
| ATOM | 4871 | O5* | C | D | 3 | 70.059 | 131.154 | 277.564 | 1.00 | 0.00 | O |
| ATOM | 4872 | C5* | C | D | 3 | 71.359 | 130.578 | 277.879 | 1.00 | 0.00 | C |
| ATOM | 4873 | C4* | C | D | 3 | 71.044 | 129.338 | 278.698 | 1.00 | 0.00 | C |
| ATOM | 4874 | O4* | C | D | 3 | 70.240 | 129.710 | 279.813 | 1.00 | 0.00 | O |
| ATOM | 4875 | C3* | C | D | 3 | 70.241 | 128.271 | 277.988 | 1.00 | 0.00 | C |
| ATOM | 4876 | O3* | C | D | 3 | 70.989 | 127.376 | 277.153 | 1.00 | 0.00 | O |
| ATOM | 4877 | C2* | C | D | 3 | 69.598 | 127.532 | 279.166 | 1.00 | 0.00 | C |
| ATOM | 4878 | O2* | C | D | 3 | 70.604 | 126.637 | 279.640 | 1.00 | 0.00 | O |
| ATOM | 4879 | C1* | C | D | 3 | 69.354 | 128.664 | 280.126 | 1.00 | 0.00 | C |
| ATOM | 4880 | N1 | C | D | 3 | 67.936 | 129.074 | 279.974 | 1.00 | 0.00 | N |
| ATOM | 4881 | C2 | C | D | 3 | 66.993 | 128.393 | 280.705 | 1.00 | 0.00 | C |
| ATOM | 4882 | O2 | C | D | 3 | 67.324 | 127.481 | 281.461 | 1.00 | 0.00 | O |
| ATOM | 4883 | N3 | C | D | 3 | 65.688 | 128.766 | 280.566 | 1.00 | 0.00 | N |
| ATOM | 4884 | C4 | C | D | 3 | 65.312 | 129.775 | 279.731 | 1.00 | 0.00 | C |
| ATOM | 4885 | N4 | C | D | 3 | 64.014 | 130.093 | 279.630 | 1.00 | 0.00 | N |
| ATOM | 4886 | C5 | C | D | 3 | 66.295 | 130.466 | 278.979 | 1.00 | 0.00 | C |
| ATOM | 4887 | C6 | C | D | 3 | 67.571 | 130.088 | 279.128 | 1.00 | 0.00 | C |
| ATOM | 4888 | P | G | D | 4 | 70.109 | 126.574 | 276.054 | 1.00 | 0.00 | P |
| ATOM | 4889 | O1P | G | D | 4 | 70.979 | 126.036 | 274.953 | 1.00 | 0.00 | O |
| ATOM | 4890 | O2P | G | D | 4 | 69.170 | 127.622 | 275.577 | 1.00 | 0.00 | O |
| ATOM | 4891 | O5* | G | D | 4 | 69.445 | 125.423 | 276.910 | 1.00 | 0.00 | O |
| ATOM | 4892 | C5* | G | D | 4 | 70.275 | 124.715 | 277.867 | 1.00 | 0.00 | C |
| ATOM | 4893 | C4* | G | D | 4 | 69.344 | 123.958 | 278.797 | 1.00 | 0.00 | C |
| ATOM | 4894 | O4* | G | D | 4 | 68.604 | 124.877 | 279.598 | 1.00 | 0.00 | O |
| ATOM | 4895 | C3* | G | D | 4 | 68.262 | 123.116 | 278.108 | 1.00 | 0.00 | C |
| ATOM | 4896 | O3* | G | D | 4 | 68.732 | 121.848 | 277.661 | 1.00 | 0.00 | O |
| ATOM | 4897 | C2* | G | D | 4 | 67.210 | 123.001 | 279.202 | 1.00 | 0.00 | C |
| ATOM | 4898 | O2* | G | D | 4 | 67.632 | 121.949 | 280.057 | 1.00 | 0.00 | O |
| ATOM | 4899 | C1* | G | D | 4 | 67.309 | 124.351 | 279.877 | 1.00 | 0.00 | C |
| ATOM | 4900 | N9 | G | D | 4 | 66.220 | 125.204 | 279.367 | 1.00 | 0.00 | N |
| ATOM | 4901 | C8 | G | D | 4 | 66.286 | 126.282 | 278.526 | 1.00 | 0.00 | C |
| ATOM | 4902 | N7 | G | D | 4 | 65.107 | 126.815 | 278.274 | 1.00 | 0.00 | N |
| ATOM | 4903 | C5 | G | D | 4 | 64.222 | 126.043 | 279.002 | 1.00 | 0.00 | C |
| ATOM | 4904 | C6 | G | D | 4 | 62.810 | 126.112 | 279.145 | 1.00 | 0.00 | C |
| ATOM | 4905 | O6 | G | D | 4 | 62.040 | 126.920 | 278.626 | 1.00 | 0.00 | O |
| ATOM | 4906 | N1 | G | D | 4 | 62.272 | 125.150 | 279.968 | 1.00 | 0.00 | N |
| ATOM | 4907 | C2 | G | D | 4 | 63.042 | 124.210 | 280.592 | 1.00 | 0.00 | C |
| ATOM | 4908 | N2 | G | D | 4 | 62.364 | 123.343 | 281.359 | 1.00 | 0.00 | N |
| ATOM | 4909 | N3 | G | D | 4 | 64.363 | 124.103 | 280.488 | 1.00 | 0.00 | N |
| ATOM | 4910 | C4 | G | D | 4 | 64.886 | 125.043 | 279.684 | 1.00 | 0.00 | C |
| ATOM | 4911 | P | U | D | 5 | 67.738 | 120.843 | 276.903 | 1.00 | 0.00 | P |
| ATOM | 4912 | O1P | U | D | 5 | 68.291 | 119.456 | 276.817 | 1.00 | 0.00 | O |

```
ATOM    4913  O2P   U D   5      67.570 121.471 275.566  1.00  0.00           O
ATOM    4914  O5*   U D   5      66.427 120.893 277.828  1.00  0.00           O
ATOM    4915  C5*   U D   5      66.024 119.728 278.566  1.00  0.00           C
ATOM    4916  C4*   U D   5      64.509 119.688 278.548  1.00  0.00           C
ATOM    4917  O4*   U D   5      63.988 120.942 278.981  1.00  0.00           O
ATOM    4918  C3*   U D   5      63.882 119.470 277.161  1.00  0.00           C
ATOM    4919  O3*   U D   5      63.874 118.106 276.778  1.00  0.00           O
ATOM    4920  C2*   U D   5      62.486 120.063 277.361  1.00  0.00           C
ATOM    4921  O2*   U D   5      61.713 119.057 277.995  1.00  0.00           O
ATOM    4922  C1*   U D   5      62.767 121.227 278.298  1.00  0.00           C
ATOM    4923  N1    U D   5      62.826 122.479 277.515  1.00  0.00           N
ATOM    4924  C2    U D   5      61.622 123.146 277.367  1.00  0.00           C
ATOM    4925  O2    U D   5      60.580 122.694 277.872  1.00  0.00           O
ATOM    4926  N3    U D   5      61.576 124.311 276.655  1.00  0.00           N
ATOM    4927  C4    U D   5      62.725 124.822 276.090  1.00  0.00           C
ATOM    4928  O4    U D   5      62.602 125.910 275.442  1.00  0.00           O
ATOM    4929  C5    U D   5      63.958 124.134 276.242  1.00  0.00           C
ATOM    4930  C6    U D   5      63.954 122.993 276.946  1.00  0.00           C
ATOM    4931  P     G D   6      63.308 117.466 275.428  1.00  0.00           P
ATOM    4932  O1P   G D   6      63.381 115.964 275.501  1.00  0.00           O
ATOM    4933  O2P   G D   6      64.161 118.005 274.347  1.00  0.00           O
ATOM    4934  O5*   G D   6      61.781 117.911 275.349  1.00  0.00           O
ATOM    4935  C5*   G D   6      60.801 116.841 275.279  1.00  0.00           C
ATOM    4936  C4*   G D   6      59.462 117.412 275.675  1.00  0.00           C
ATOM    4937  O4*   G D   6      59.615 118.719 276.212  1.00  0.00           O
ATOM    4938  C3*   G D   6      58.506 117.611 274.504  1.00  0.00           C
ATOM    4939  O3*   G D   6      57.844 116.392 274.123  1.00  0.00           O
ATOM    4940  C2*   G D   6      57.550 118.674 275.033  1.00  0.00           C
ATOM    4941  O2*   G D   6      56.589 117.988 275.847  1.00  0.00           O
ATOM    4942  C1*   G D   6      58.490 119.520 275.857  1.00  0.00           C
ATOM    4943  N9    G D   6      58.901 120.687 275.051  1.00  0.00           N
ATOM    4944  C8    G D   6      60.140 120.997 274.597  1.00  0.00           C
ATOM    4945  N7    G D   6      60.198 122.103 273.892  1.00  0.00           N
ATOM    4946  C5    G D   6      58.876 122.554 273.892  1.00  0.00           C
ATOM    4947  C6    G D   6      58.271 123.699 273.307  1.00  0.00           C
ATOM    4948  O6    G D   6      58.825 124.580 272.641  1.00  0.00           O
ATOM    4949  N1    G D   6      56.928 123.799 273.526  1.00  0.00           N
ATOM    4950  C2    G D   6      56.224 122.874 274.249  1.00  0.00           C
ATOM    4951  N2    G D   6      54.912 123.120 274.372  1.00  0.00           N
ATOM    4952  N3    G D   6      56.740 121.789 274.820  1.00  0.00           N
ATOM    4953  C4    G D   6      58.066 121.686 274.599  1.00  0.00           C
ATOM    4954  P     A D   7      58.188 115.928 272.608  1.00  0.00           P
ATOM    4955  O1P   A D   7      58.407 114.451 272.551  1.00  0.00           O
ATOM    4956  O2P   A D   7      59.421 116.714 272.307  1.00  0.00           O
ATOM    4957  O5*   A D   7      56.876 116.390 271.823  1.00  0.00           O
ATOM    4958  C5*   A D   7      55.660 116.495 272.610  1.00  0.00           C
ATOM    4959  C4*   A D   7      54.730 117.433 271.858  1.00  0.00           C
ATOM    4960  O4*   A D   7      55.229 118.763 271.973  1.00  0.00           O
ATOM    4961  C3*   A D   7      54.621 117.145 270.353  1.00  0.00           C
ATOM    4962  O3*   A D   7      53.298 117.446 269.870  1.00  0.00           O
ATOM    4963  C2*   A D   7      55.614 118.135 269.762  1.00  0.00           C
ATOM    4964  O2*   A D   7      55.297 118.370 268.416  1.00  0.00           O
ATOM    4965  C1*   A D   7      55.450 119.319 270.673  1.00  0.00           C
ATOM    4966  N9    A D   7      56.635 120.178 270.603  1.00  0.00           N
ATOM    4967  C8    A D   7      57.945 119.878 270.844  1.00  0.00           C
ATOM    4968  N7    A D   7      58.770 120.887 270.682  1.00  0.00           N
ATOM    4969  C5    A D   7      57.942 121.940 270.308  1.00  0.00           C
ATOM    4970  C6    A D   7      58.216 123.293 269.994  1.00  0.00           C
ATOM    4971  N6    A D   7      59.411 123.835 270.005  1.00  0.00           N
ATOM    4972  N1    A D   7      57.126 124.045 269.663  1.00  0.00           N
ATOM    4973  C2    A D   7      55.869 123.517 269.646  1.00  0.00           C
ATOM    4974  N3    A D   7      55.539 122.253 269.932  1.00  0.00           N
ATOM    4975  C4    A D   7      56.630 121.523 270.252  1.00  0.00           C
HETATM  4976  N1   4SU D   8      52.722 113.480 266.990  1.00  0.00           N
HETATM  4977  C2   4SU D   8      53.228 112.194 267.026  1.00  0.00           C
HETATM  4978  N3   4SU D   8      53.243 111.611 268.268  1.00  0.00           N
HETATM  4979  C4   4SU D   8      52.811 112.166 269.452  1.00  0.00           C
HETATM  4980  C5   4SU D   8      52.303 113.502 269.339  1.00  0.00           C
HETATM  4981  C6   4SU D   8      52.275 114.100 268.140  1.00  0.00           C
HETATM  4982  O2   4SU D   8      53.632 111.616 266.038  1.00  0.00           O
HETATM  4983  S4   4SU D   8      52.887 111.310 270.890  1.00  0.00           S
HETATM  4984  C1*  4SU D   8      52.674 114.154 265.682  1.00  0.00           C
HETATM  4985  C2*  4SU D   8      51.322 114.027 264.981  1.00  0.00           C
HETATM  4986  O2*  4SU D   8      51.527 113.963 263.586  1.00  0.00           O
HETATM  4987  C3*  4SU D   8      50.638 115.312 265.428  1.00  0.00           C
HETATM  4988  C4*  4SU D   8      51.784 116.312 265.432  1.00  0.00           C
HETATM  4989  O3*  4SU D   8      49.602 115.716 264.535  1.00  0.00           O
HETATM  4990  O4*  4SU D   8      52.924 115.536 265.881  1.00  0.00           O
HETATM  4991  C5*  4SU D   8      51.610 117.499 266.351  1.00  0.00           C
HETATM  4992  O5*  4SU D   8      51.261 117.054 267.675  1.00  0.00           O
HETATM  4993  P    4SU D   8      51.664 117.894 268.965  1.00  0.00           P
HETATM  4994  O1P  4SU D   8      50.949 119.191 268.910  1.00  0.00           O
HETATM  4995  O2P  4SU D   8      51.509 117.023 270.156  1.00  0.00           O
ATOM    4996  P     A D   9      48.749 116.638 265.350  1.00  0.00           P
ATOM    4997  O1P   A D   9      48.062 117.959 265.239  1.00  0.00           O
ATOM    4998  O2P   A D   9      48.612 115.840 266.600  1.00  0.00           O
ATOM    4999  O5*   A D   9      48.291 115.708 264.140  1.00  0.00           O
```

```
ATOM   5000  C5*  A D   9    47.917 116.260 262.855  1.00  0.00           C
ATOM   5001  C4*  A D   9    46.816 115.424 262.240  1.00  0.00           C
ATOM   5002  O4*  A D   9    47.294 114.057 262.136  1.00  0.00           O
ATOM   5003  C3*  A D   9    45.541 115.373 263.071  1.00  0.00           C
ATOM   5004  O3*  A D   9    44.412 115.285 262.202  1.00  0.00           O
ATOM   5005  C2*  A D   9    45.712 114.098 263.893  1.00  0.00           C
ATOM   5006  O2*  A D   9    44.489 113.501 264.268  1.00  0.00           O
ATOM   5007  C1*  A D   9    46.515 113.202 262.946  1.00  0.00           C
ATOM   5008  N9   A D   9    47.429 112.304 263.657  1.00  0.00           N
ATOM   5009  C8   A D   9    47.835 112.399 264.967  1.00  0.00           C
ATOM   5010  N7   A D   9    48.644 111.440 265.344  1.00  0.00           N
ATOM   5011  C5   A D   9    48.789 110.659 264.207  1.00  0.00           C
ATOM   5012  C6   A D   9    49.518 109.486 263.958  1.00  0.00           C
ATOM   5013  N6   A D   9    50.275 108.876 264.870  1.00  0.00           N
ATOM   5014  N1   A D   9    49.448 108.954 262.719  1.00  0.00           N
ATOM   5015  C2   A D   9    48.698 109.573 261.801  1.00  0.00           C
ATOM   5016  N3   A D   9    47.969 110.681 261.912  1.00  0.00           N
ATOM   5017  C4   A D   9    48.054 111.183 263.159  1.00  0.00           C
ATOM   5018  P    A D  10    43.433 116.552 262.028  1.00  0.00           P
ATOM   5019  O1P  A D  10    42.377 116.197 261.052  1.00  0.00           O
ATOM   5020  O2P  A D  10    44.269 117.759 261.791  1.00  0.00           O
ATOM   5021  O5*  A D  10    42.720 116.696 263.444  1.00  0.00           O
ATOM   5022  C5*  A D  10    41.914 117.851 263.739  1.00  0.00           C
ATOM   5023  C4*  A D  10    40.962 117.552 264.872  1.00  0.00           C
ATOM   5024  O4*  A D  10    40.090 116.467 264.475  1.00  0.00           O
ATOM   5025  C3*  A D  10    41.603 117.084 266.169  1.00  0.00           C
ATOM   5026  O3*  A D  10    41.986 118.188 266.978  1.00  0.00           O
ATOM   5027  C2*  A D  10    40.498 116.257 266.816  1.00  0.00           C
ATOM   5028  O2*  A D  10    39.556 117.029 267.534  1.00  0.00           O
ATOM   5029  C1*  A D  10    39.816 115.645 265.594  1.00  0.00           C
ATOM   5030  N9   A D  10    40.313 114.308 265.303  1.00  0.00           N
ATOM   5031  C8   A D  10    40.897 113.837 264.152  1.00  0.00           C
ATOM   5032  N7   A D  10    41.229 112.572 264.209  1.00  0.00           N
ATOM   5033  C5   A D  10    40.842 112.184 265.483  1.00  0.00           C
ATOM   5034  C6   A D  10    40.919 110.961 266.165  1.00  0.00           C
ATOM   5035  N6   A D  10    41.431 109.849 265.629  1.00  0.00           N
ATOM   5036  N1   A D  10    40.449 110.914 267.430  1.00  0.00           N
ATOM   5037  C2   A D  10    39.932 112.032 267.963  1.00  0.00           C
ATOM   5038  N3   A D  10    39.800 113.239 267.422  1.00  0.00           N
ATOM   5039  C4   A D  10    40.280 113.246 266.170  1.00  0.00           C
ATOM   5040  P    C D  11    43.424 118.189 267.693  1.00  0.00           P
ATOM   5041  O1P  C D  11    43.677 119.577 268.163  1.00  0.00           O
ATOM   5042  O2P  C D  11    44.389 117.533 266.768  1.00  0.00           O
ATOM   5043  O5*  C D  11    43.235 117.252 268.968  1.00  0.00           O
ATOM   5044  C5*  C D  11    42.403 117.661 270.071  1.00  0.00           C
ATOM   5045  C4*  C D  11    42.134 116.486 270.980  1.00  0.00           C
ATOM   5046  O4*  C D  11    41.473 115.445 270.214  1.00  0.00           O
ATOM   5047  C3*  C D  11    43.359 115.800 271.566  1.00  0.00           C
ATOM   5048  O3*  C D  11    43.799 116.407 272.772  1.00  0.00           O
ATOM   5049  C2*  C D  11    42.860 114.389 271.836  1.00  0.00           C
ATOM   5050  O2*  C D  11    42.173 114.297 273.067  1.00  0.00           O
ATOM   5051  C1*  C D  11    41.897 114.171 270.671  1.00  0.00           C
ATOM   5052  N1   C D  11    42.550 113.464 269.560  1.00  0.00           N
ATOM   5053  C2   C D  11    42.798 112.094 269.693  1.00  0.00           C
ATOM   5054  O2   C D  11    42.436 111.517 270.730  1.00  0.00           O
ATOM   5055  N3   C D  11    43.420 111.431 268.691  1.00  0.00           N
ATOM   5056  C4   C D  11    43.790 112.087 267.590  1.00  0.00           C
ATOM   5057  N4   C D  11    44.410 111.397 266.633  1.00  0.00           N
ATOM   5058  C5   C D  11    43.540 113.482 267.422  1.00  0.00           C
ATOM   5059  C6   C D  11    42.924 114.124 268.423  1.00  0.00           C
ATOM   5060  P    A D  12    45.181 115.925 273.446  1.00  0.00           P
ATOM   5061  O1P  A D  12    45.233 116.507 274.814  1.00  0.00           O
ATOM   5062  O2P  A D  12    46.280 116.202 272.481  1.00  0.00           O
ATOM   5063  O5*  A D  12    45.039 114.340 273.576  1.00  0.00           O
ATOM   5064  C5*  A D  12    44.605 113.731 274.807  1.00  0.00           C
ATOM   5065  C4*  A D  12    45.110 112.308 274.898  1.00  0.00           C
ATOM   5066  O4*  A D  12    44.551 111.524 273.814  1.00  0.00           O
ATOM   5067  C3*  A D  12    46.616 112.113 274.788  1.00  0.00           C
ATOM   5068  O3*  A D  12    47.232 112.259 276.067  1.00  0.00           O
ATOM   5069  C2*  A D  12    46.729 110.677 274.285  1.00  0.00           C
ATOM   5070  O2*  A D  12    46.645 109.741 275.344  1.00  0.00           O
ATOM   5071  C1*  A D  12    45.485 110.547 273.402  1.00  0.00           C
ATOM   5072  N9   A D  12    45.744 110.739 271.976  1.00  0.00           N
ATOM   5073  C8   A D  12    45.579 111.887 271.246  1.00  0.00           C
ATOM   5074  N7   A D  12    45.875 111.753 269.977  1.00  0.00           N
ATOM   5075  C5   A D  12    46.263 110.427 269.862  1.00  0.00           C
ATOM   5076  C6   A D  12    46.691 109.658 268.767  1.00  0.00           C
ATOM   5077  N6   A D  12    46.803 110.132 267.525  1.00  0.00           N
ATOM   5078  N1   A D  12    47.007 108.363 268.992  1.00  0.00           N
ATOM   5079  C2   A D  12    46.895 107.885 270.237  1.00  0.00           C
ATOM   5080  N3   A D  12    46.501 108.509 271.347  1.00  0.00           N
ATOM   5081  C4   A D  12    46.194 109.792 271.090  1.00  0.00           C
ATOM   5082  P    A D  13    48.827 112.465 276.177  1.00  0.00           P
ATOM   5083  O1P  A D  13    49.191 112.369 277.614  1.00  0.00           O
ATOM   5084  O2P  A D  13    49.177 113.686 275.419  1.00  0.00           O
ATOM   5085  O5*  A D  13    49.436 111.188 275.445  1.00  0.00           O
ATOM   5086  C5*  A D  13    49.471 109.916 276.117  1.00  0.00           C
```

| | | | | | | | | | | |
|---|---|---|---|---|---|---|---|---|---|---|
| ATOM | 5087 | C4* | A | D | 13 | 50.163 | 108.889 | 275.261 | 1.00 | 0.00 | C |
| ATOM | 5088 | O4* | A | D | 13 | 49.374 | 108.650 | 274.069 | 1.00 | 0.00 | O |
| ATOM | 5089 | C3* | A | D | 13 | 51.536 | 109.286 | 274.745 | 1.00 | 0.00 | C |
| ATOM | 5090 | O3* | A | D | 13 | 52.563 | 109.034 | 275.699 | 1.00 | 0.00 | O |
| ATOM | 5091 | C2* | A | D | 13 | 51.674 | 108.449 | 273.476 | 1.00 | 0.00 | C |
| ATOM | 5092 | O2* | A | D | 13 | 52.110 | 107.122 | 273.704 | 1.00 | 0.00 | O |
| ATOM | 5093 | C1* | A | D | 13 | 50.233 | 108.439 | 272.962 | 1.00 | 0.00 | C |
| ATOM | 5094 | N9 | A | D | 13 | 49.999 | 109.513 | 272.003 | 1.00 | 0.00 | N |
| ATOM | 5095 | C8 | A | D | 13 | 49.636 | 110.813 | 272.266 | 1.00 | 0.00 | C |
| ATOM | 5096 | N7 | A | D | 13 | 49.502 | 111.554 | 271.194 | 1.00 | 0.00 | N |
| ATOM | 5097 | C5 | A | D | 13 | 49.798 | 110.682 | 270.152 | 1.00 | 0.00 | C |
| ATOM | 5098 | C6 | A | D | 13 | 49.831 | 110.854 | 268.755 | 1.00 | 0.00 | C |
| ATOM | 5099 | N6 | A | D | 13 | 49.555 | 112.009 | 268.141 | 1.00 | 0.00 | N |
| ATOM | 5100 | N1 | A | D | 13 | 50.162 | 109.780 | 268.000 | 1.00 | 0.00 | N |
| ATOM | 5101 | C2 | A | D | 13 | 50.439 | 108.617 | 268.617 | 1.00 | 0.00 | C |
| ATOM | 5102 | N3 | A | D | 13 | 50.442 | 108.334 | 269.919 | 1.00 | 0.00 | N |
| ATOM | 5103 | C4 | A | D | 13 | 50.107 | 109.423 | 270.637 | 1.00 | 0.00 | C |
| ATOM | 5104 | P | A | D | 14 | 54.096 | 109.299 | 275.303 | 1.00 | 0.00 | P |
| ATOM | 5105 | O1P | A | D | 14 | 54.942 | 109.134 | 276.514 | 1.00 | 0.00 | O |
| ATOM | 5106 | O2P | A | D | 14 | 54.158 | 110.568 | 274.528 | 1.00 | 0.00 | O |
| ATOM | 5107 | O5* | A | D | 14 | 54.411 | 108.100 | 274.308 | 1.00 | 0.00 | O |
| ATOM | 5108 | C5* | A | D | 14 | 55.616 | 108.067 | 273.556 | 1.00 | 0.00 | C |
| ATOM | 5109 | C4* | A | D | 14 | 55.741 | 106.737 | 272.871 | 1.00 | 0.00 | C |
| ATOM | 5110 | O4* | A | D | 14 | 54.561 | 106.501 | 272.070 | 1.00 | 0.00 | O |
| ATOM | 5111 | C3* | A | D | 14 | 56.907 | 106.638 | 271.907 | 1.00 | 0.00 | C |
| ATOM | 5112 | O3* | A | D | 14 | 58.078 | 106.251 | 272.611 | 1.00 | 0.00 | O |
| ATOM | 5113 | C2* | A | D | 14 | 56.433 | 105.591 | 270.903 | 1.00 | 0.00 | C |
| ATOM | 5114 | O2* | A | D | 14 | 56.655 | 104.262 | 271.329 | 1.00 | 0.00 | O |
| ATOM | 5115 | C1* | A | D | 14 | 54.927 | 105.856 | 270.866 | 1.00 | 0.00 | C |
| ATOM | 5116 | N9 | A | D | 14 | 54.503 | 106.705 | 269.755 | 1.00 | 0.00 | N |
| ATOM | 5117 | C8 | A | D | 14 | 53.887 | 107.932 | 269.816 | 1.00 | 0.00 | C |
| ATOM | 5118 | N7 | A | D | 14 | 53.584 | 108.429 | 268.643 | 1.00 | 0.00 | N |
| ATOM | 5119 | C5 | A | D | 14 | 54.041 | 107.470 | 267.750 | 1.00 | 0.00 | C |
| ATOM | 5120 | C6 | A | D | 14 | 54.008 | 107.395 | 266.348 | 1.00 | 0.00 | C |
| ATOM | 5121 | N6 | A | D | 14 | 53.453 | 108.326 | 265.573 | 1.00 | 0.00 | N |
| ATOM | 5122 | N1 | A | D | 14 | 54.563 | 106.310 | 265.764 | 1.00 | 0.00 | N |
| ATOM | 5123 | C2 | A | D | 14 | 55.102 | 105.367 | 266.544 | 1.00 | 0.00 | C |
| ATOM | 5124 | N3 | A | D | 14 | 55.183 | 105.318 | 267.872 | 1.00 | 0.00 | N |
| ATOM | 5125 | C4 | A | D | 14 | 54.626 | 106.413 | 268.419 | 1.00 | 0.00 | C |
| ATOM | 5126 | P | G | D | 15 | 59.440 | 107.075 | 272.397 | 1.00 | 0.00 | P |
| ATOM | 5127 | O1P | G | D | 15 | 60.132 | 107.185 | 273.710 | 1.00 | 0.00 | O |
| ATOM | 5128 | O2P | G | D | 15 | 59.109 | 108.310 | 271.635 | 1.00 | 0.00 | O |
| ATOM | 5129 | O5* | G | D | 15 | 60.289 | 106.119 | 271.451 | 1.00 | 0.00 | O |
| ATOM | 5130 | C5* | G | D | 15 | 60.390 | 104.721 | 271.744 | 1.00 | 0.00 | C |
| ATOM | 5131 | C4* | G | D | 15 | 60.317 | 103.920 | 270.474 | 1.00 | 0.00 | C |
| ATOM | 5132 | O4* | G | D | 15 | 58.996 | 104.032 | 269.886 | 1.00 | 0.00 | O |
| ATOM | 5133 | C3* | G | D | 15 | 61.255 | 104.387 | 269.379 | 1.00 | 0.00 | C |
| ATOM | 5134 | O3* | G | D | 15 | 62.557 | 103.873 | 269.569 | 1.00 | 0.00 | O |
| ATOM | 5135 | C2* | G | D | 15 | 60.582 | 103.865 | 268.116 | 1.00 | 0.00 | C |
| ATOM | 5136 | O2* | G | D | 15 | 60.873 | 102.508 | 267.845 | 1.00 | 0.00 | O |
| ATOM | 5137 | C1* | G | D | 15 | 59.103 | 104.023 | 268.473 | 1.00 | 0.00 | C |
| ATOM | 5138 | N9 | G | D | 15 | 58.586 | 105.288 | 267.971 | 1.00 | 0.00 | N |
| ATOM | 5139 | C8 | G | D | 15 | 58.334 | 106.430 | 268.690 | 1.00 | 0.00 | C |
| ATOM | 5140 | N7 | G | D | 15 | 57.900 | 107.412 | 267.951 | 1.00 | 0.00 | N |
| ATOM | 5141 | C5 | G | D | 15 | 57.859 | 106.882 | 266.668 | 1.00 | 0.00 | C |
| ATOM | 5142 | C6 | G | D | 15 | 57.474 | 107.476 | 265.446 | 1.00 | 0.00 | C |
| ATOM | 5143 | O6 | G | D | 15 | 57.092 | 108.627 | 265.244 | 1.00 | 0.00 | O |
| ATOM | 5144 | N1 | G | D | 15 | 57.577 | 106.581 | 264.385 | 1.00 | 0.00 | N |
| ATOM | 5145 | C2 | G | D | 15 | 58.003 | 105.279 | 264.492 | 1.00 | 0.00 | C |
| ATOM | 5146 | N2 | G | D | 15 | 58.031 | 104.568 | 263.353 | 1.00 | 0.00 | N |
| ATOM | 5147 | N3 | G | D | 15 | 58.372 | 104.718 | 265.627 | 1.00 | 0.00 | N |
| ATOM | 5148 | C4 | G | D | 15 | 58.274 | 105.569 | 266.669 | 1.00 | 0.00 | C |
| ATOM | 5149 | P | C | D | 16 | 64.314 | 104.108 | 270.242 | 1.00 | 0.00 | P |
| ATOM | 5150 | O1P | C | D | 16 | 64.558 | 102.676 | 269.940 | 1.00 | 0.00 | O |
| ATOM | 5151 | O2P | C | D | 16 | 63.703 | 104.494 | 271.543 | 1.00 | 0.00 | O |
| ATOM | 5152 | O5* | C | D | 16 | 65.672 | 104.912 | 270.044 | 1.00 | 0.00 | O |
| ATOM | 5153 | C5* | C | D | 16 | 65.702 | 106.333 | 270.243 | 1.00 | 0.00 | C |
| ATOM | 5154 | C4* | C | D | 16 | 67.015 | 106.760 | 270.849 | 1.00 | 0.00 | C |
| ATOM | 5155 | O4* | C | D | 16 | 66.934 | 106.707 | 272.297 | 1.00 | 0.00 | O |
| ATOM | 5156 | C3* | C | D | 16 | 68.232 | 105.913 | 270.523 | 1.00 | 0.00 | C |
| ATOM | 5157 | O3* | C | D | 16 | 68.802 | 106.243 | 269.267 | 1.00 | 0.00 | O |
| ATOM | 5158 | C2* | C | D | 16 | 69.180 | 106.250 | 271.666 | 1.00 | 0.00 | C |
| ATOM | 5159 | O2* | C | D | 16 | 69.855 | 107.471 | 271.447 | 1.00 | 0.00 | O |
| ATOM | 5160 | C1* | C | D | 16 | 68.210 | 106.402 | 272.834 | 1.00 | 0.00 | C |
| ATOM | 5161 | N1 | C | D | 16 | 68.107 | 105.166 | 273.626 | 1.00 | 0.00 | N |
| ATOM | 5162 | C2 | C | D | 16 | 69.152 | 104.848 | 274.503 | 1.00 | 0.00 | C |
| ATOM | 5163 | O2 | C | D | 16 | 70.112 | 105.629 | 274.600 | 1.00 | 0.00 | O |
| ATOM | 5164 | N3 | C | D | 16 | 69.083 | 103.704 | 275.227 | 1.00 | 0.00 | N |
| ATOM | 5165 | C4 | C | D | 16 | 68.027 | 102.893 | 275.096 | 1.00 | 0.00 | C |
| ATOM | 5166 | N4 | C | D | 16 | 68.003 | 101.771 | 275.827 | 1.00 | 0.00 | N |
| ATOM | 5167 | C5 | C | D | 16 | 66.945 | 103.198 | 274.213 | 1.00 | 0.00 | C |
| ATOM | 5168 | C6 | C | D | 16 | 67.029 | 104.334 | 273.503 | 1.00 | 0.00 | C |
| ATOM | 5169 | P | G | D | 18 | 69.975 | 105.726 | 268.306 | 1.00 | 0.00 | P |
| ATOM | 5170 | O1P | G | D | 18 | 70.151 | 104.310 | 268.730 | 1.00 | 0.00 | O |
| ATOM | 5171 | O2P | G | D | 18 | 71.099 | 106.695 | 268.460 | 1.00 | 0.00 | O |
| ATOM | 5172 | O5* | G | D | 18 | 69.493 | 105.744 | 266.787 | 1.00 | 0.00 | O |
| ATOM | 5173 | C5* | G | D | 18 | 69.523 | 106.954 | 266.006 | 1.00 | 0.00 | C |

```
ATOM    5174  C4*   G D  18      69.099 106.655 264.593  1.00  0.00           C
ATOM    5175  O4*   G D  18      69.478 107.748 263.715  1.00  0.00           O
ATOM    5176  C3*   G D  18      69.705 105.388 263.999  1.00  0.00           C
ATOM    5177  O3*   G D  18      68.731 104.743 263.178  1.00  0.00           O
ATOM    5178  C2*   G D  18      70.817 105.935 263.110  1.00  0.00           C
ATOM    5179  O2*   G D  18      71.155 105.096 262.028  1.00  0.00           O
ATOM    5180  C1*   G D  18      70.176 107.226 262.610  1.00  0.00           C
ATOM    5181  N9    G D  18      71.098 108.231 262.091  1.00  0.00           N
ATOM    5182  C8    G D  18      72.362 108.515 262.534  1.00  0.00           C
ATOM    5183  N7    G D  18      72.962 109.431 261.819  1.00  0.00           N
ATOM    5184  C5    G D  18      72.028 109.779 260.855  1.00  0.00           C
ATOM    5185  C6    G D  18      72.112 110.716 259.781  1.00  0.00           C
ATOM    5186  O6    G D  18      73.066 111.433 259.451  1.00  0.00           O
ATOM    5187  N1    G D  18      70.927 110.760 259.049  1.00  0.00           N
ATOM    5188  C2    G D  18      69.813 110.003 259.307  1.00  0.00           C
ATOM    5189  N2    G D  18      68.767 110.187 258.486  1.00  0.00           N
ATOM    5190  N3    G D  18      69.726 109.124 260.294  1.00  0.00           N
ATOM    5191  C4    G D  18      70.863 109.064 261.019  1.00  0.00           C
ATOM    5192  P     G D  19      67.905 103.483 263.742  1.00  0.00           P
ATOM    5193  O1P   G D  19      66.830 103.988 264.635  1.00  0.00           O
ATOM    5194  O2P   G D  19      68.886 102.496 264.263  1.00  0.00           O
ATOM    5195  O5*   G D  19      67.206 102.881 262.441  1.00  0.00           O
ATOM    5196  C5*   G D  19      66.018 103.491 261.910  1.00  0.00           C
ATOM    5197  C4*   G D  19      65.812 103.090 260.468  1.00  0.00           C
ATOM    5198  O4*   G D  19      66.988 103.458 259.708  1.00  0.00           O
ATOM    5199  C3*   G D  19      65.547 101.613 260.184  1.00  0.00           C
ATOM    5200  O3*   G D  19      64.626 101.522 259.108  1.00  0.00           O
ATOM    5201  C2*   G D  19      66.901 101.096 259.703  1.00  0.00           C
ATOM    5202  O2*   G D  19      66.764 100.028 258.779  1.00  0.00           O
ATOM    5203  C1*   G D  19      67.475 102.331 259.010  1.00  0.00           C
ATOM    5204  N9    G D  19      68.933 102.400 259.019  1.00  0.00           N
ATOM    5205  C8    G D  19      69.777 102.142 260.071  1.00  0.00           C
ATOM    5206  N7    G D  19      71.035 102.316 259.768  1.00  0.00           N
ATOM    5207  C5    G D  19      71.018 102.707 258.435  1.00  0.00           C
ATOM    5208  C6    G D  19      72.082 103.045 257.559  1.00  0.00           C
ATOM    5209  O6    G D  19      73.299 103.063 257.790  1.00  0.00           O
ATOM    5210  N1    G D  19      71.611 103.392 256.292  1.00  0.00           N
ATOM    5211  C2    G D  19      70.288 103.413 255.921  1.00  0.00           C
ATOM    5212  N2    G D  19      70.030 103.791 254.660  1.00  0.00           N
ATOM    5213  N3    G D  19      69.292 103.094 256.727  1.00  0.00           N
ATOM    5214  C4    G D  19      69.723 102.756 257.957  1.00  0.00           C
HETATM  5215  P     H2U D  20     63.079 101.458 259.613  1.00  0.00           P
HETATM  5216  O1P   H2U D  20     63.452 102.803 260.123  1.00  0.00           O
HETATM  5217  O2P   H2U D  20     62.646 100.406 260.568  1.00  0.00           O
HETATM  5218  O5*   H2U D  20     61.942 101.614 258.510  1.00  0.00           O
HETATM  5219  C5*   H2U D  20     62.056 102.603 257.471  1.00  0.00           C
HETATM  5220  C4*   H2U D  20     60.712 103.238 257.215  1.00  0.00           C
HETATM  5221  O4*   H2U D  20     60.869 104.310 256.246  1.00  0.00           O
HETATM  5222  C3*   H2U D  20     59.658 102.300 256.640  1.00  0.00           C
HETATM  5223  O3*   H2U D  20     58.375 102.674 257.119  1.00  0.00           O
HETATM  5224  C1*   H2U D  20     60.057 104.054 255.119  1.00  0.00           C
HETATM  5225  C2*   H2U D  20     59.771 102.556 255.143  1.00  0.00           C
HETATM  5226  O2*   H2U D  20     58.605 102.240 254.417  1.00  0.00           O
HETATM  5227  N1    H2U D  20     60.788 104.495 253.931  1.00  0.00           N
HETATM  5228  C2    H2U D  20     60.465 105.665 253.346  1.00  0.00           C
HETATM  5229  O2    H2U D  20     59.468 106.318 253.613  1.00  0.00           O
HETATM  5230  N3    H2U D  20     61.357 106.094 252.401  1.00  0.00           N
HETATM  5231  C4    H2U D  20     62.695 105.775 252.337  1.00  0.00           C
HETATM  5232  O4    H2U D  20     63.472 106.478 251.681  1.00  0.00           O
HETATM  5233  C5    H2U D  20     63.104 104.559 253.100  1.00  0.00           C
HETATM  5234  C6    H2U D  20     61.904 103.686 253.403  1.00  0.00           C
HETATM  5235  P     H2U D  21     57.024 101.938 257.476  1.00  0.00           P
HETATM  5236  O1P   H2U D  21     57.106 102.204 258.934  1.00  0.00           O
HETATM  5237  O2P   H2U D  21     57.270 100.564 256.969  1.00  0.00           O
HETATM  5238  O5*   H2U D  21     55.598 102.417 256.949  1.00  0.00           O
HETATM  5239  C5*   H2U D  21     55.261 103.816 256.862  1.00  0.00           C
HETATM  5240  C4*   H2U D  21     54.413 104.216 258.047  1.00  0.00           C
HETATM  5241  O4*   H2U D  21     53.653 105.404 257.693  1.00  0.00           O
HETATM  5242  C3*   H2U D  21     53.387 103.183 258.491  1.00  0.00           C
HETATM  5243  O3*   H2U D  21     53.152 103.327 259.886  1.00  0.00           O
HETATM  5244  C1*   H2U D  21     52.269 105.111 257.715  1.00  0.00           C
HETATM  5245  C2*   H2U D  21     52.149 103.588 257.704  1.00  0.00           C
HETATM  5246  O2*   H2U D  21     50.946 103.149 258.307  1.00  0.00           O
HETATM  5247  N1    H2U D  21     51.662 105.772 256.543  1.00  0.00           N
HETATM  5248  C2    H2U D  21     50.518 106.492 256.727  1.00  0.00           C
HETATM  5249  O2    H2U D  21     49.689 106.251 257.592  1.00  0.00           O
HETATM  5250  N3    H2U D  21     50.332 107.530 255.852  1.00  0.00           N
HETATM  5251  C4    H2U D  21     50.786 107.584 254.565  1.00  0.00           C
HETATM  5252  O4    H2U D  21     50.432 108.501 253.823  1.00  0.00           O
HETATM  5253  C5    H2U D  21     51.704 106.490 254.171  1.00  0.00           C
HETATM  5254  C6    H2U D  21     52.519 106.025 255.358  1.00  0.00           C
ATOM    5255  P     A D  22      52.660 102.391 260.868  1.00  0.00           P
ATOM    5256  O1P   A D  22      54.013 101.858 261.183  1.00  0.00           O
ATOM    5257  O2P   A D  22      51.636 101.500 260.259  1.00  0.00           O
ATOM    5258  O5*   A D  22      52.023 102.974 262.200  1.00  0.00           O
ATOM    5259  C5*   A D  22      52.807 103.032 263.397  1.00  0.00           C
ATOM    5260  C4*   A D  22      52.757 101.708 264.090  1.00  0.00           C
```

| | | | | | | | | | | |
|---|---|---|---|---|---|---|---|---|---|---|
| ATOM | 5261 | O4* | A | D | 22 | 53.667 | 101.759 | 265.190 | 1.00 | 0.00 | O |
| ATOM | 5262 | C3* | A | D | 22 | 51.385 | 101.317 | 264.642 | 1.00 | 0.00 | C |
| ATOM | 5263 | O3* | A | D | 22 | 50.684 | 100.479 | 263.731 | 1.00 | 0.00 | O |
| ATOM | 5264 | C2* | A | D | 22 | 51.746 | 100.608 | 265.925 | 1.00 | 0.00 | C |
| ATOM | 5265 | O2* | A | D | 22 | 52.142 | 99.264 | 265.730 | 1.00 | 0.00 | O |
| ATOM | 5266 | C1* | A | D | 22 | 52.950 | 101.435 | 266.348 | 1.00 | 0.00 | C |
| ATOM | 5267 | N9 | A | D | 22 | 52.505 | 102.716 | 266.940 | 1.00 | 0.00 | N |
| ATOM | 5268 | C8 | A | D | 22 | 52.167 | 103.906 | 266.369 | 1.00 | 0.00 | C |
| ATOM | 5269 | N7 | A | D | 22 | 51.850 | 104.811 | 267.264 | 1.00 | 0.00 | N |
| ATOM | 5270 | C5 | A | D | 22 | 51.988 | 104.139 | 268.483 | 1.00 | 0.00 | C |
| ATOM | 5271 | C6 | A | D | 22 | 51.822 | 104.502 | 269.795 | 1.00 | 0.00 | C |
| ATOM | 5272 | N6 | A | D | 22 | 51.429 | 105.694 | 270.185 | 1.00 | 0.00 | N |
| ATOM | 5273 | N1 | A | D | 22 | 52.068 | 103.540 | 270.740 | 1.00 | 0.00 | N |
| ATOM | 5274 | C2 | A | D | 22 | 52.451 | 102.319 | 270.343 | 1.00 | 0.00 | C |
| ATOM | 5275 | N3 | A | D | 22 | 52.626 | 101.880 | 269.141 | 1.00 | 0.00 | N |
| ATOM | 5276 | C4 | A | D | 22 | 52.396 | 102.832 | 268.240 | 1.00 | 0.00 | C |
| ATOM | 5277 | P | U | D | 23 | 49.077 | 100.546 | 263.646 | 1.00 | 0.00 | P |
| ATOM | 5278 | O1P | U | D | 23 | 48.558 | 99.231 | 263.180 | 1.00 | 0.00 | O |
| ATOM | 5279 | O2P | U | D | 23 | 48.719 | 101.775 | 262.903 | 1.00 | 0.00 | O |
| ATOM | 5280 | O5* | U | D | 23 | 48.607 | 100.724 | 265.154 | 1.00 | 0.00 | O |
| ATOM | 5281 | C5* | U | D | 23 | 48.849 | 99.699 | 266.124 | 1.00 | 0.00 | C |
| ATOM | 5282 | C4* | U | D | 23 | 48.531 | 100.210 | 267.504 | 1.00 | 0.00 | C |
| ATOM | 5283 | O4* | U | D | 23 | 49.419 | 101.313 | 267.818 | 1.00 | 0.00 | O |
| ATOM | 5284 | C3* | U | D | 23 | 47.137 | 100.791 | 267.675 | 1.00 | 0.00 | C |
| ATOM | 5285 | O3* | U | D | 23 | 46.161 | 99.794 | 267.948 | 1.00 | 0.00 | O |
| ATOM | 5286 | C2* | U | D | 23 | 47.319 | 101.751 | 268.838 | 1.00 | 0.00 | C |
| ATOM | 5287 | O2* | U | D | 23 | 47.297 | 101.085 | 270.073 | 1.00 | 0.00 | O |
| ATOM | 5288 | C1* | U | D | 23 | 48.727 | 102.282 | 268.587 | 1.00 | 0.00 | C |
| ATOM | 5289 | N1 | U | D | 23 | 48.676 | 103.535 | 267.823 | 1.00 | 0.00 | N |
| ATOM | 5290 | C2 | U | D | 23 | 48.327 | 104.697 | 268.501 | 1.00 | 0.00 | C |
| ATOM | 5291 | O2 | U | D | 23 | 48.088 | 104.729 | 269.701 | 1.00 | 0.00 | O |
| ATOM | 5292 | N3 | U | D | 23 | 48.264 | 105.822 | 267.716 | 1.00 | 0.00 | N |
| ATOM | 5293 | C4 | U | D | 23 | 48.516 | 105.909 | 266.359 | 1.00 | 0.00 | C |
| ATOM | 5294 | O4 | U | D | 23 | 48.382 | 106.992 | 265.786 | 1.00 | 0.00 | O |
| ATOM | 5295 | C5 | U | D | 23 | 48.885 | 104.670 | 265.739 | 1.00 | 0.00 | C |
| ATOM | 5296 | C6 | U | D | 23 | 48.951 | 103.556 | 266.474 | 1.00 | 0.00 | C |
| ATOM | 5297 | P | G | D | 24 | 44.616 | 100.081 | 267.606 | 1.00 | 0.00 | P |
| ATOM | 5298 | O1P | G | D | 24 | 43.917 | 98.773 | 267.592 | 1.00 | 0.00 | O |
| ATOM | 5299 | O2P | G | D | 24 | 44.563 | 100.953 | 266.407 | 1.00 | 0.00 | O |
| ATOM | 5300 | O5* | G | D | 24 | 44.098 | 100.931 | 268.851 | 1.00 | 0.00 | O |
| ATOM | 5301 | C5* | G | D | 24 | 44.288 | 100.454 | 270.189 | 1.00 | 0.00 | C |
| ATOM | 5302 | C4* | G | D | 24 | 44.069 | 101.570 | 271.178 | 1.00 | 0.00 | C |
| ATOM | 5303 | O4* | G | D | 24 | 44.992 | 102.653 | 270.890 | 1.00 | 0.00 | O |
| ATOM | 5304 | C3* | G | D | 24 | 42.700 | 102.232 | 271.158 | 1.00 | 0.00 | C |
| ATOM | 5305 | O3* | G | D | 24 | 41.735 | 101.508 | 271.916 | 1.00 | 0.00 | O |
| ATOM | 5306 | C2* | G | D | 24 | 42.991 | 103.602 | 271.764 | 1.00 | 0.00 | C |
| ATOM | 5307 | O2* | G | D | 24 | 43.039 | 103.583 | 273.178 | 1.00 | 0.00 | O |
| ATOM | 5308 | C1* | G | D | 24 | 44.389 | 103.895 | 271.221 | 1.00 | 0.00 | C |
| ATOM | 5309 | N9 | G | D | 24 | 44.345 | 104.743 | 270.024 | 1.00 | 0.00 | N |
| ATOM | 5310 | C8 | G | D | 24 | 44.652 | 104.389 | 268.733 | 1.00 | 0.00 | C |
| ATOM | 5311 | N7 | G | D | 24 | 44.502 | 105.374 | 267.886 | 1.00 | 0.00 | N |
| ATOM | 5312 | C5 | G | D | 24 | 44.072 | 106.443 | 268.665 | 1.00 | 0.00 | C |
| ATOM | 5313 | C6 | G | D | 24 | 43.749 | 107.780 | 268.305 | 1.00 | 0.00 | C |
| ATOM | 5314 | O6 | G | D | 24 | 43.781 | 108.309 | 267.190 | 1.00 | 0.00 | O |
| ATOM | 5315 | N1 | G | D | 24 | 43.353 | 108.527 | 269.409 | 1.00 | 0.00 | N |
| ATOM | 5316 | C2 | G | D | 24 | 43.280 | 108.052 | 270.697 | 1.00 | 0.00 | C |
| ATOM | 5317 | N2 | G | D | 24 | 42.874 | 108.929 | 271.630 | 1.00 | 0.00 | N |
| ATOM | 5318 | N3 | G | D | 24 | 43.583 | 106.815 | 271.045 | 1.00 | 0.00 | N |
| ATOM | 5319 | C4 | G | D | 24 | 43.968 | 106.068 | 269.991 | 1.00 | 0.00 | C |
| ATOM | 5320 | P | U | D | 25 | 40.435 | 101.974 | 270.709 | 1.00 | 0.00 | P |
| ATOM | 5321 | O1P | U | D | 25 | 39.435 | 100.894 | 270.923 | 1.00 | 0.00 | O |
| ATOM | 5322 | O2P | U | D | 25 | 41.092 | 102.110 | 269.381 | 1.00 | 0.00 | O |
| ATOM | 5323 | O5* | U | D | 25 | 39.746 | 103.369 | 271.074 | 1.00 | 0.00 | O |
| ATOM | 5324 | C5* | U | D | 25 | 39.202 | 103.612 | 272.393 | 1.00 | 0.00 | C |
| ATOM | 5325 | C4* | U | D | 25 | 38.979 | 105.094 | 272.616 | 1.00 | 0.00 | C |
| ATOM | 5326 | O4* | U | D | 25 | 40.187 | 105.828 | 272.279 | 1.00 | 0.00 | O |
| ATOM | 5327 | C3* | U | D | 25 | 37.895 | 105.745 | 271.771 | 1.00 | 0.00 | C |
| ATOM | 5328 | O3* | U | D | 25 | 36.592 | 105.567 | 272.309 | 1.00 | 0.00 | O |
| ATOM | 5329 | C2* | U | D | 25 | 38.322 | 107.208 | 271.756 | 1.00 | 0.00 | C |
| ATOM | 5330 | O2* | U | D | 25 | 37.917 | 107.915 | 272.913 | 1.00 | 0.00 | O |
| ATOM | 5331 | C1* | U | D | 25 | 39.845 | 107.086 | 271.721 | 1.00 | 0.00 | C |
| ATOM | 5332 | N1 | U | D | 25 | 40.345 | 107.128 | 270.338 | 1.00 | 0.00 | N |
| ATOM | 5333 | C2 | U | D | 25 | 40.205 | 108.309 | 269.628 | 1.00 | 0.00 | C |
| ATOM | 5334 | O2 | U | D | 25 | 39.751 | 109.329 | 270.120 | 1.00 | 0.00 | O |
| ATOM | 5335 | N3 | U | D | 25 | 40.628 | 108.254 | 268.324 | 1.00 | 0.00 | N |
| ATOM | 5336 | C4 | U | D | 25 | 41.170 | 107.167 | 267.671 | 1.00 | 0.00 | C |
| ATOM | 5337 | O4 | U | D | 25 | 41.422 | 107.247 | 266.466 | 1.00 | 0.00 | O |
| ATOM | 5338 | C5 | U | D | 25 | 41.312 | 105.996 | 268.480 | 1.00 | 0.00 | C |
| ATOM | 5339 | C6 | U | D | 25 | 40.905 | 106.016 | 269.753 | 1.00 | 0.00 | C |
| ATOM | 5340 | P | A | D | 26 | 34.783 | 105.490 | 272.317 | 1.00 | 0.00 | P |
| ATOM | 5341 | O1P | A | D | 26 | 34.020 | 105.632 | 273.580 | 1.00 | 0.00 | O |
| ATOM | 5342 | O2P | A | D | 26 | 34.546 | 104.333 | 271.422 | 1.00 | 0.00 | O |
| ATOM | 5343 | O5* | A | D | 26 | 34.655 | 106.841 | 271.453 | 1.00 | 0.00 | O |
| ATOM | 5344 | C5* | A | D | 26 | 34.550 | 108.130 | 272.058 | 1.00 | 0.00 | C |
| ATOM | 5345 | C4* | A | D | 26 | 34.840 | 109.251 | 271.057 | 1.00 | 0.00 | C |
| ATOM | 5346 | O4* | A | D | 26 | 36.244 | 109.362 | 270.754 | 1.00 | 0.00 | O |
| ATOM | 5347 | C3* | A | D | 26 | 34.262 | 108.923 | 269.703 | 1.00 | 0.00 | C |

| | | | | | | | | | | |
|---|---|---|---|---|---|---|---|---|---|---|
| ATOM | 5348 | O3* | A | D | 26 | 32.845 | 109.126 | 269.670 | 1.00 | 0.00 | O |
| ATOM | 5349 | C2* | A | D | 26 | 34.968 | 109.927 | 268.826 | 1.00 | 0.00 | C |
| ATOM | 5350 | O2* | A | D | 26 | 34.510 | 111.273 | 269.050 | 1.00 | 0.00 | O |
| ATOM | 5351 | C1* | A | D | 26 | 36.380 | 109.797 | 269.375 | 1.00 | 0.00 | C |
| ATOM | 5352 | N9 | A | D | 26 | 37.121 | 108.815 | 268.539 | 1.00 | 0.00 | N |
| ATOM | 5353 | C8 | A | D | 26 | 37.448 | 107.513 | 268.810 | 1.00 | 0.00 | C |
| ATOM | 5354 | N7 | A | D | 26 | 38.131 | 106.921 | 267.871 | 1.00 | 0.00 | N |
| ATOM | 5355 | C5 | A | D | 26 | 38.271 | 107.903 | 266.900 | 1.00 | 0.00 | C |
| ATOM | 5356 | C6 | A | D | 26 | 38.896 | 107.918 | 265.641 | 1.00 | 0.00 | C |
| ATOM | 5357 | N6 | A | D | 26 | 39.505 | 106.859 | 265.121 | 1.00 | 0.00 | N |
| ATOM | 5358 | N1 | A | D | 26 | 38.844 | 109.046 | 264.937 | 1.00 | 0.00 | N |
| ATOM | 5359 | C2 | A | D | 26 | 38.214 | 110.087 | 265.443 | 1.00 | 0.00 | C |
| ATOM | 5360 | N3 | A | D | 26 | 37.586 | 110.211 | 266.606 | 1.00 | 0.00 | N |
| ATOM | 5361 | C4 | A | D | 26 | 37.659 | 109.059 | 267.296 | 1.00 | 0.00 | C |
| ATOM | 5362 | P | C | D | 27 | 32.199 | 108.399 | 268.756 | 1.00 | 0.00 | P |
| ATOM | 5363 | O1P | C | D | 27 | 30.822 | 108.733 | 269.182 | 1.00 | 0.00 | O |
| ATOM | 5364 | O2P | C | D | 27 | 32.709 | 107.016 | 268.885 | 1.00 | 0.00 | O |
| ATOM | 5365 | O5* | C | D | 27 | 32.399 | 108.842 | 267.224 | 1.00 | 0.00 | O |
| ATOM | 5366 | C5* | C | D | 27 | 31.996 | 110.114 | 266.706 | 1.00 | 0.00 | C |
| ATOM | 5367 | C4* | C | D | 27 | 32.595 | 110.337 | 265.319 | 1.00 | 0.00 | C |
| ATOM | 5368 | O4* | C | D | 27 | 34.032 | 110.254 | 265.341 | 1.00 | 0.00 | O |
| ATOM | 5369 | C3* | C | D | 27 | 32.215 | 109.193 | 264.404 | 1.00 | 0.00 | C |
| ATOM | 5370 | O3* | C | D | 27 | 30.890 | 109.374 | 263.893 | 1.00 | 0.00 | O |
| ATOM | 5371 | C2* | C | D | 27 | 33.262 | 109.259 | 263.320 | 1.00 | 0.00 | C |
| ATOM | 5372 | O2* | C | D | 27 | 33.066 | 110.380 | 262.440 | 1.00 | 0.00 | O |
| ATOM | 5373 | C1* | C | D | 27 | 34.492 | 109.513 | 264.186 | 1.00 | 0.00 | C |
| ATOM | 5374 | N1 | C | D | 27 | 35.121 | 108.208 | 264.569 | 1.00 | 0.00 | N |
| ATOM | 5375 | C2 | C | D | 27 | 36.014 | 107.631 | 263.673 | 1.00 | 0.00 | C |
| ATOM | 5376 | O2 | C | D | 27 | 36.290 | 108.170 | 262.602 | 1.00 | 0.00 | O |
| ATOM | 5377 | N3 | C | D | 27 | 36.590 | 106.448 | 264.008 | 1.00 | 0.00 | N |
| ATOM | 5378 | C4 | C | D | 27 | 36.317 | 105.842 | 265.165 | 1.00 | 0.00 | C |
| ATOM | 5379 | N4 | C | D | 27 | 36.918 | 104.692 | 265.458 | 1.00 | 0.00 | N |
| ATOM | 5380 | C5 | C | D | 27 | 35.405 | 106.416 | 266.099 | 1.00 | 0.00 | C |
| ATOM | 5381 | C6 | C | D | 27 | 34.840 | 107.589 | 265.758 | 1.00 | 0.00 | C |
| ATOM | 5382 | P | C | D | 28 | 30.051 | 108.043 | 263.538 | 1.00 | 0.00 | P |
| ATOM | 5383 | O1P | C | D | 28 | 28.859 | 108.927 | 263.544 | 1.00 | 0.00 | O |
| ATOM | 5384 | O2P | C | D | 28 | 30.090 | 106.825 | 264.382 | 1.00 | 0.00 | O |
| ATOM | 5385 | O5* | C | D | 28 | 30.409 | 107.618 | 262.029 | 1.00 | 0.00 | O |
| ATOM | 5386 | C5* | C | D | 28 | 30.172 | 108.456 | 260.887 | 1.00 | 0.00 | C |
| ATOM | 5387 | C4* | C | D | 28 | 30.953 | 107.939 | 259.684 | 1.00 | 0.00 | C |
| ATOM | 5388 | O4* | C | D | 28 | 32.362 | 107.856 | 259.984 | 1.00 | 0.00 | O |
| ATOM | 5389 | C3* | C | D | 28 | 30.567 | 106.501 | 259.390 | 1.00 | 0.00 | C |
| ATOM | 5390 | O3* | C | D | 28 | 29.418 | 106.408 | 258.539 | 1.00 | 0.00 | O |
| ATOM | 5391 | C2* | C | D | 28 | 31.779 | 105.957 | 258.677 | 1.00 | 0.00 | C |
| ATOM | 5392 | O2* | C | D | 28 | 31.872 | 106.424 | 257.319 | 1.00 | 0.00 | O |
| ATOM | 5393 | C1* | C | D | 28 | 32.891 | 106.601 | 259.492 | 1.00 | 0.00 | C |
| ATOM | 5394 | N1 | C | D | 28 | 33.316 | 105.687 | 260.608 | 1.00 | 0.00 | N |
| ATOM | 5395 | C2 | C | D | 28 | 34.191 | 104.645 | 260.309 | 1.00 | 0.00 | C |
| ATOM | 5396 | O2 | C | D | 28 | 34.585 | 104.439 | 259.162 | 1.00 | 0.00 | O |
| ATOM | 5397 | N3 | C | D | 28 | 34.608 | 103.842 | 261.323 | 1.00 | 0.00 | N |
| ATOM | 5398 | C4 | C | D | 28 | 34.196 | 104.034 | 262.581 | 1.00 | 0.00 | C |
| ATOM | 5399 | N4 | C | D | 28 | 34.634 | 103.235 | 263.551 | 1.00 | 0.00 | N |
| ATOM | 5400 | C5 | C | D | 28 | 33.294 | 105.092 | 262.909 | 1.00 | 0.00 | C |
| ATOM | 5401 | C6 | C | D | 28 | 32.889 | 105.881 | 261.897 | 1.00 | 0.00 | C |
| ATOM | 5402 | P | G | D | 29 | 28.246 | 105.401 | 258.969 | 1.00 | 0.00 | P |
| ATOM | 5403 | O1P | G | D | 29 | 27.827 | 105.401 | 257.550 | 1.00 | 0.00 | O |
| ATOM | 5404 | O2P | G | D | 29 | 27.335 | 105.922 | 260.016 | 1.00 | 0.00 | O |
| ATOM | 5405 | O5* | G | D | 29 | 28.728 | 103.918 | 259.385 | 1.00 | 0.00 | O |
| ATOM | 5406 | C5* | G | D | 29 | 28.578 | 102.729 | 258.597 | 1.00 | 0.00 | C |
| ATOM | 5407 | C4* | G | D | 29 | 29.538 | 102.596 | 257.419 | 1.00 | 0.00 | C |
| ATOM | 5408 | O4* | G | D | 29 | 30.849 | 103.110 | 257.697 | 1.00 | 0.00 | O |
| ATOM | 5409 | C3* | G | D | 29 | 29.772 | 101.109 | 257.215 | 1.00 | 0.00 | C |
| ATOM | 5410 | O3* | G | D | 29 | 28.829 | 100.558 | 256.283 | 1.00 | 0.00 | O |
| ATOM | 5411 | C2* | G | D | 29 | 31.186 | 101.002 | 256.698 | 1.00 | 0.00 | C |
| ATOM | 5412 | O2* | G | D | 29 | 31.301 | 101.427 | 255.336 | 1.00 | 0.00 | O |
| ATOM | 5413 | C1* | G | D | 29 | 31.836 | 102.060 | 257.588 | 1.00 | 0.00 | C |
| ATOM | 5414 | N9 | G | D | 29 | 32.156 | 101.564 | 258.964 | 1.00 | 0.00 | N |
| ATOM | 5415 | C8 | G | D | 29 | 31.807 | 102.128 | 260.171 | 1.00 | 0.00 | C |
| ATOM | 5416 | N7 | G | D | 29 | 32.255 | 101.496 | 261.213 | 1.00 | 0.00 | N |
| ATOM | 5417 | C5 | G | D | 29 | 32.957 | 100.428 | 260.674 | 1.00 | 0.00 | C |
| ATOM | 5418 | C6 | G | D | 29 | 33.663 | 99.397 | 261.339 | 1.00 | 0.00 | C |
| ATOM | 5419 | O6 | G | D | 29 | 33.816 | 99.239 | 262.547 | 1.00 | 0.00 | O |
| ATOM | 5420 | N1 | G | D | 29 | 34.233 | 98.511 | 260.441 | 1.00 | 0.00 | N |
| ATOM | 5421 | C2 | G | D | 29 | 34.137 | 98.600 | 259.071 | 1.00 | 0.00 | C |
| ATOM | 5422 | N2 | G | D | 29 | 34.759 | 97.651 | 258.382 | 1.00 | 0.00 | N |
| ATOM | 5423 | N3 | G | D | 29 | 33.472 | 99.569 | 258.436 | 1.00 | 0.00 | N |
| ATOM | 5424 | C4 | G | D | 29 | 32.906 | 100.451 | 259.300 | 1.00 | 0.00 | C |
| ATOM | 5425 | P | G | D | 30 | 27.913 | 99.325 | 256.784 | 1.00 | 0.00 | P |
| ATOM | 5426 | O1P | G | D | 30 | 26.961 | 100.435 | 256.540 | 1.00 | 0.00 | O |
| ATOM | 5427 | O2P | G | D | 30 | 28.022 | 98.758 | 258.146 | 1.00 | 0.00 | O |
| ATOM | 5428 | O5* | G | D | 30 | 27.487 | 98.125 | 255.807 | 1.00 | 0.00 | O |
| ATOM | 5429 | C5* | G | D | 30 | 28.411 | 97.383 | 255.006 | 1.00 | 0.00 | C |
| ATOM | 5430 | C4* | G | D | 30 | 29.402 | 96.497 | 255.772 | 1.00 | 0.00 | C |
| ATOM | 5431 | O4* | G | D | 30 | 30.304 | 97.262 | 256.576 | 1.00 | 0.00 | O |
| ATOM | 5432 | C3* | G | D | 30 | 28.743 | 95.669 | 256.853 | 1.00 | 0.00 | C |
| ATOM | 5433 | O3* | G | D | 30 | 27.892 | 94.620 | 256.359 | 1.00 | 0.00 | O |
| ATOM | 5434 | C2* | G | D | 30 | 29.979 | 95.076 | 257.480 | 1.00 | 0.00 | C |

| | | | | | | | | | | |
|---|---|---|---|---|---|---|---|---|---|---|
| ATOM | 5435 | O2* | G | D | 30 | 30.580 | 94.051 | 256.672 | 1.00 | 0.00 | O |
| ATOM | 5436 | C1* | G | D | 30 | 30.903 | 96.293 | 257.470 | 1.00 | 0.00 | C |
| ATOM | 5437 | N9 | G | D | 30 | 31.009 | 96.733 | 258.880 | 1.00 | 0.00 | N |
| ATOM | 5438 | C8 | G | D | 30 | 30.475 | 97.823 | 259.517 | 1.00 | 0.00 | C |
| ATOM | 5439 | N7 | G | D | 30 | 30.741 | 97.882 | 260.789 | 1.00 | 0.00 | N |
| ATOM | 5440 | C5 | G | D | 30 | 31.509 | 96.748 | 261.015 | 1.00 | 0.00 | C |
| ATOM | 5441 | C6 | G | D | 30 | 32.088 | 96.276 | 262.214 | 1.00 | 0.00 | C |
| ATOM | 5442 | O6 | G | D | 30 | 32.031 | 96.786 | 263.329 | 1.00 | 0.00 | O |
| ATOM | 5443 | N1 | G | D | 30 | 32.780 | 95.091 | 262.006 | 1.00 | 0.00 | N |
| ATOM | 5444 | C2 | G | D | 30 | 32.897 | 94.443 | 260.795 | 1.00 | 0.00 | C |
| ATOM | 5445 | N2 | G | D | 30 | 33.590 | 93.311 | 260.778 | 1.00 | 0.00 | N |
| ATOM | 5446 | N3 | G | D | 30 | 32.356 | 94.889 | 259.668 | 1.00 | 0.00 | N |
| ATOM | 5447 | C4 | G | D | 30 | 31.678 | 96.043 | 259.856 | 1.00 | 0.00 | C |
| ATOM | 5448 | P | A | D | 31 | 26.886 | 93.861 | 257.381 | 1.00 | 0.00 | P |
| ATOM | 5449 | O1P | A | D | 31 | 25.870 | 93.182 | 256.546 | 1.00 | 0.00 | O |
| ATOM | 5450 | O2P | A | D | 31 | 26.441 | 94.855 | 258.385 | 1.00 | 0.00 | O |
| ATOM | 5451 | O5* | A | D | 31 | 27.736 | 92.732 | 258.143 | 1.00 | 0.00 | O |
| ATOM | 5452 | C5* | A | D | 31 | 28.154 | 91.551 | 257.457 | 1.00 | 0.00 | C |
| ATOM | 5453 | C4* | A | D | 31 | 29.044 | 90.678 | 258.326 | 1.00 | 0.00 | C |
| ATOM | 5454 | O4* | A | D | 31 | 30.201 | 91.390 | 258.799 | 1.00 | 0.00 | O |
| ATOM | 5455 | C3* | A | D | 31 | 28.331 | 90.329 | 259.606 | 1.00 | 0.00 | C |
| ATOM | 5456 | O3* | A | D | 31 | 27.373 | 89.284 | 259.398 | 1.00 | 0.00 | O |
| ATOM | 5457 | C2* | A | D | 31 | 29.481 | 89.880 | 260.477 | 1.00 | 0.00 | C |
| ATOM | 5458 | O2* | A | D | 31 | 30.062 | 88.649 | 260.020 | 1.00 | 0.00 | O |
| ATOM | 5459 | C1* | A | D | 31 | 30.436 | 91.021 | 260.184 | 1.00 | 0.00 | C |
| ATOM | 5460 | N9 | A | D | 31 | 30.153 | 92.143 | 261.128 | 1.00 | 0.00 | N |
| ATOM | 5461 | C8 | A | D | 31 | 29.547 | 93.359 | 260.893 | 1.00 | 0.00 | C |
| ATOM | 5462 | N7 | A | D | 31 | 29.485 | 94.137 | 261.933 | 1.00 | 0.00 | N |
| ATOM | 5463 | C5 | A | D | 31 | 30.090 | 93.391 | 262.934 | 1.00 | 0.00 | C |
| ATOM | 5464 | C6 | A | D | 31 | 30.342 | 93.660 | 264.279 | 1.00 | 0.00 | C |
| ATOM | 5465 | N6 | A | D | 31 | 30.004 | 94.806 | 264.854 | 1.00 | 0.00 | N |
| ATOM | 5466 | N1 | A | D | 31 | 30.952 | 92.712 | 264.997 | 1.00 | 0.00 | N |
| ATOM | 5467 | C2 | A | D | 31 | 31.288 | 91.575 | 264.409 | 1.00 | 0.00 | C |
| ATOM | 5468 | N3 | A | D | 31 | 31.114 | 91.197 | 263.156 | 1.00 | 0.00 | N |
| ATOM | 5469 | C4 | A | D | 31 | 30.497 | 92.176 | 262.460 | 1.00 | 0.00 | C |
| ATOM | 5470 | P | U | D | 32 | 26.084 | 89.227 | 260.380 | 1.00 | 0.00 | P |
| ATOM | 5471 | O1P | U | D | 32 | 25.372 | 89.157 | 259.081 | 1.00 | 0.00 | O |
| ATOM | 5472 | O2P | U | D | 32 | 25.329 | 89.462 | 261.634 | 1.00 | 0.00 | O |
| ATOM | 5473 | O5* | U | D | 32 | 27.053 | 87.937 | 260.546 | 1.00 | 0.00 | O |
| ATOM | 5474 | C5* | U | D | 32 | 26.926 | 86.872 | 261.492 | 1.00 | 0.00 | C |
| ATOM | 5475 | C4* | U | D | 32 | 27.493 | 87.122 | 262.911 | 1.00 | 0.00 | C |
| ATOM | 5476 | O4* | U | D | 32 | 28.306 | 88.300 | 263.075 | 1.00 | 0.00 | O |
| ATOM | 5477 | C3* | U | D | 32 | 26.374 | 87.460 | 263.840 | 1.00 | 0.00 | C |
| ATOM | 5478 | O3* | U | D | 32 | 25.513 | 86.345 | 264.057 | 1.00 | 0.00 | O |
| ATOM | 5479 | C2* | U | D | 32 | 27.156 | 87.781 | 265.090 | 1.00 | 0.00 | C |
| ATOM | 5480 | O2* | U | D | 32 | 27.652 | 86.594 | 265.742 | 1.00 | 0.00 | O |
| ATOM | 5481 | C1* | U | D | 32 | 28.334 | 88.571 | 264.506 | 1.00 | 0.00 | C |
| ATOM | 5482 | N1 | U | D | 32 | 28.084 | 89.986 | 264.925 | 1.00 | 0.00 | N |
| ATOM | 5483 | C2 | U | D | 32 | 28.491 | 90.368 | 266.210 | 1.00 | 0.00 | C |
| ATOM | 5484 | O2 | U | D | 32 | 29.109 | 89.635 | 266.984 | 1.00 | 0.00 | O |
| ATOM | 5485 | N3 | U | D | 32 | 28.173 | 91.656 | 266.590 | 1.00 | 0.00 | N |
| ATOM | 5486 | C4 | U | D | 32 | 27.501 | 92.590 | 265.827 | 1.00 | 0.00 | C |
| ATOM | 5487 | O4 | U | D | 32 | 27.267 | 93.707 | 266.282 | 1.00 | 0.00 | O |
| ATOM | 5488 | C5 | U | D | 32 | 27.123 | 92.122 | 264.515 | 1.00 | 0.00 | C |
| ATOM | 5489 | C6 | U | D | 32 | 27.417 | 90.868 | 264.113 | 1.00 | 0.00 | C |
| ATOM | 5490 | P | U | D | 33 | 24.081 | 86.635 | 264.710 | 1.00 | 0.00 | P |
| ATOM | 5491 | O1P | U | D | 33 | 24.161 | 85.155 | 264.657 | 1.00 | 0.00 | O |
| ATOM | 5492 | O2P | U | D | 33 | 23.097 | 87.377 | 263.884 | 1.00 | 0.00 | O |
| ATOM | 5493 | O5* | U | D | 33 | 23.958 | 87.120 | 266.255 | 1.00 | 0.00 | O |
| ATOM | 5494 | C5* | U | D | 33 | 24.432 | 86.335 | 267.366 | 1.00 | 0.00 | C |
| ATOM | 5495 | C4* | U | D | 33 | 24.627 | 87.169 | 268.636 | 1.00 | 0.00 | C |
| ATOM | 5496 | O4* | U | D | 33 | 25.537 | 88.261 | 268.426 | 1.00 | 0.00 | O |
| ATOM | 5497 | C3* | U | D | 33 | 23.334 | 87.862 | 269.005 | 1.00 | 0.00 | C |
| ATOM | 5498 | O3* | U | D | 33 | 22.453 | 86.948 | 269.671 | 1.00 | 0.00 | O |
| ATOM | 5499 | C2* | U | D | 33 | 23.810 | 88.961 | 269.920 | 1.00 | 0.00 | C |
| ATOM | 5500 | O2* | U | D | 33 | 24.181 | 88.455 | 271.209 | 1.00 | 0.00 | O |
| ATOM | 5501 | C1* | U | D | 33 | 25.081 | 89.404 | 269.184 | 1.00 | 0.00 | C |
| ATOM | 5502 | N1 | U | D | 33 | 24.769 | 90.584 | 268.312 | 1.00 | 0.00 | N |
| ATOM | 5503 | C2 | U | D | 33 | 24.885 | 91.855 | 268.864 | 1.00 | 0.00 | C |
| ATOM | 5504 | O2 | U | D | 33 | 25.239 | 92.069 | 270.022 | 1.00 | 0.00 | O |
| ATOM | 5505 | N3 | U | D | 33 | 24.566 | 92.911 | 268.036 | 1.00 | 0.00 | N |
| ATOM | 5506 | C4 | U | D | 33 | 24.144 | 92.825 | 266.724 | 1.00 | 0.00 | C |
| ATOM | 5507 | O4 | U | D | 33 | 23.884 | 93.838 | 266.081 | 1.00 | 0.00 | O |
| ATOM | 5508 | C5 | U | D | 33 | 24.051 | 91.479 | 266.230 | 1.00 | 0.00 | C |
| ATOM | 5509 | C6 | U | D | 33 | 24.359 | 90.429 | 267.016 | 1.00 | 0.00 | C |
| ATOM | 5510 | P | U | D | 34 | 20.514 | 86.548 | 269.593 | 1.00 | 0.00 | P |
| ATOM | 5511 | O1P | U | D | 34 | 19.621 | 86.217 | 270.741 | 1.00 | 0.00 | O |
| ATOM | 5512 | O2P | U | D | 34 | 20.818 | 85.501 | 268.572 | 1.00 | 0.00 | O |
| ATOM | 5513 | O5* | U | D | 34 | 19.917 | 87.838 | 268.859 | 1.00 | 0.00 | O |
| ATOM | 5514 | C5* | U | D | 34 | 19.207 | 87.710 | 267.606 | 1.00 | 0.00 | C |
| ATOM | 5515 | C4* | U | D | 34 | 18.051 | 88.686 | 267.538 | 1.00 | 0.00 | C |
| ATOM | 5516 | O4* | U | D | 34 | 17.045 | 88.358 | 268.533 | 1.00 | 0.00 | O |
| ATOM | 5517 | C3* | U | D | 34 | 18.388 | 90.140 | 267.807 | 1.00 | 0.00 | C |
| ATOM | 5518 | O3* | U | D | 34 | 18.896 | 90.789 | 266.656 | 1.00 | 0.00 | O |
| ATOM | 5519 | C2* | U | D | 34 | 17.055 | 90.726 | 268.251 | 1.00 | 0.00 | C |
| ATOM | 5520 | O2* | U | D | 34 | 16.249 | 91.103 | 267.157 | 1.00 | 0.00 | O |
| ATOM | 5521 | C1* | U | D | 34 | 16.418 | 89.550 | 268.998 | 1.00 | 0.00 | C |

| | | | | | | | | | | |
|---|---|---|---|---|---|---|---|---|---|---|
| ATOM | 5522 | N1 | U | D | 34 | 16.568 | 89.631 | 270.465 | 1.00 | 0.00 | N |
| ATOM | 5523 | C2 | U | D | 34 | 15.965 | 90.695 | 271.135 | 1.00 | 0.00 | C |
| ATOM | 5524 | O2 | U | D | 34 | 15.287 | 91.541 | 270.574 | 1.00 | 0.00 | O |
| ATOM | 5525 | N3 | U | D | 34 | 16.184 | 90.725 | 272.491 | 1.00 | 0.00 | N |
| ATOM | 5526 | C4 | U | D | 34 | 16.919 | 89.829 | 273.236 | 1.00 | 0.00 | C |
| ATOM | 5527 | O4 | U | D | 34 | 17.064 | 90.016 | 274.441 | 1.00 | 0.00 | O |
| ATOM | 5528 | C5 | U | D | 34 | 17.490 | 88.754 | 272.486 | 1.00 | 0.00 | C |
| ATOM | 5529 | C6 | U | D | 34 | 17.301 | 88.694 | 271.163 | 1.00 | 0.00 | C |
| ATOM | 5530 | P | U | D | 35 | 20.023 | 91.916 | 266.830 | 1.00 | 0.00 | P |
| ATOM | 5531 | O1P | U | D | 35 | 20.340 | 92.497 | 265.498 | 1.00 | 0.00 | O |
| ATOM | 5532 | O2P | U | D | 35 | 21.110 | 91.336 | 267.656 | 1.00 | 0.00 | O |
| ATOM | 5533 | O5* | U | D | 35 | 19.303 | 93.031 | 267.704 | 1.00 | 0.00 | O |
| ATOM | 5534 | C5* | U | D | 35 | 18.327 | 93.889 | 267.121 | 1.00 | 0.00 | C |
| ATOM | 5535 | C4* | U | D | 35 | 17.945 | 94.959 | 268.099 | 1.00 | 0.00 | C |
| ATOM | 5536 | O4* | U | D | 35 | 17.262 | 94.355 | 269.226 | 1.00 | 0.00 | O |
| ATOM | 5537 | C3* | U | D | 35 | 19.110 | 95.699 | 268.729 | 1.00 | 0.00 | C |
| ATOM | 5538 | O3* | U | D | 35 | 19.618 | 96.725 | 267.889 | 1.00 | 0.00 | O |
| ATOM | 5539 | C2* | U | D | 35 | 18.515 | 96.205 | 270.035 | 1.00 | 0.00 | C |
| ATOM | 5540 | O2* | U | D | 35 | 17.736 | 97.377 | 269.892 | 1.00 | 0.00 | O |
| ATOM | 5541 | C1* | U | D | 35 | 17.591 | 95.049 | 270.415 | 1.00 | 0.00 | C |
| ATOM | 5542 | N1 | U | D | 35 | 18.232 | 94.113 | 271.350 | 1.00 | 0.00 | N |
| ATOM | 5543 | C2 | U | D | 35 | 18.398 | 94.540 | 272.648 | 1.00 | 0.00 | C |
| ATOM | 5544 | O2 | U | D | 35 | 18.039 | 95.652 | 273.033 | 1.00 | 0.00 | O |
| ATOM | 5545 | N3 | U | D | 35 | 19.000 | 93.630 | 273.483 | 1.00 | 0.00 | N |
| ATOM | 5546 | C4 | U | D | 35 | 19.445 | 92.367 | 273.154 | 1.00 | 0.00 | C |
| ATOM | 5547 | O4 | U | D | 35 | 19.995 | 91.681 | 274.014 | 1.00 | 0.00 | O |
| ATOM | 5548 | C5 | U | D | 35 | 19.236 | 92.000 | 271.793 | 1.00 | 0.00 | C |
| ATOM | 5549 | C6 | U | D | 35 | 18.652 | 92.863 | 270.957 | 1.00 | 0.00 | C |
| ATOM | 5550 | P | U | D | 36 | 21.209 | 96.894 | 267.736 | 1.00 | 0.00 | P |
| ATOM | 5551 | O1P | U | D | 36 | 21.455 | 97.921 | 266.690 | 1.00 | 0.00 | O |
| ATOM | 5552 | O2P | U | D | 36 | 21.786 | 95.528 | 267.576 | 1.00 | 0.00 | O |
| ATOM | 5553 | O5* | U | D | 36 | 21.659 | 97.489 | 269.148 | 1.00 | 0.00 | O |
| ATOM | 5554 | C5* | U | D | 36 | 21.145 | 98.761 | 269.596 | 1.00 | 0.00 | C |
| ATOM | 5555 | C4* | U | D | 36 | 21.392 | 98.956 | 271.074 | 1.00 | 0.00 | C |
| ATOM | 5556 | O4* | U | D | 36 | 20.696 | 97.930 | 271.834 | 1.00 | 0.00 | O |
| ATOM | 5557 | C3* | U | D | 36 | 22.825 | 98.851 | 271.564 | 1.00 | 0.00 | C |
| ATOM | 5558 | O3* | U | D | 36 | 23.614 | 100.008 | 271.323 | 1.00 | 0.00 | O |
| ATOM | 5559 | C2* | U | D | 36 | 22.631 | 98.567 | 273.047 | 1.00 | 0.00 | C |
| ATOM | 5560 | O2* | U | D | 36 | 22.323 | 99.713 | 273.818 | 1.00 | 0.00 | O |
| ATOM | 5561 | C1* | U | D | 36 | 21.420 | 97.644 | 273.020 | 1.00 | 0.00 | C |
| ATOM | 5562 | N1 | U | D | 36 | 21.852 | 96.235 | 273.011 | 1.00 | 0.00 | N |
| ATOM | 5563 | C2 | U | D | 36 | 22.400 | 95.736 | 274.190 | 1.00 | 0.00 | C |
| ATOM | 5564 | O2 | U | D | 36 | 22.522 | 96.412 | 275.202 | 1.00 | 0.00 | O |
| ATOM | 5565 | N3 | U | D | 36 | 22.792 | 94.422 | 274.142 | 1.00 | 0.00 | N |
| ATOM | 5566 | C4 | U | D | 36 | 22.704 | 93.565 | 273.067 | 1.00 | 0.00 | C |
| ATOM | 5567 | O4 | U | D | 36 | 23.057 | 92.381 | 273.205 | 1.00 | 0.00 | O |
| ATOM | 5568 | C5 | U | D | 36 | 22.137 | 94.150 | 271.880 | 1.00 | 0.00 | C |
| ATOM | 5569 | C6 | U | D | 36 | 21.738 | 95.432 | 271.893 | 1.00 | 0.00 | C |
| ATOM | 5570 | P | A | D | 37 | 25.130 | 99.829 | 270.795 | 1.00 | 0.00 | P |
| ATOM | 5571 | O1P | A | D | 37 | 25.598 | 101.158 | 270.309 | 1.00 | 0.00 | O |
| ATOM | 5572 | O2P | A | D | 37 | 25.167 | 98.647 | 269.874 | 1.00 | 0.00 | O |
| ATOM | 5573 | O5* | A | D | 37 | 25.964 | 99.428 | 272.097 | 1.00 | 0.00 | O |
| ATOM | 5574 | C5* | A | D | 37 | 26.066 | 100.319 | 273.222 | 1.00 | 0.00 | C |
| ATOM | 5575 | C4* | A | D | 37 | 26.639 | 99.587 | 274.413 | 1.00 | 0.00 | C |
| ATOM | 5576 | O4* | A | D | 37 | 25.751 | 98.504 | 274.777 | 1.00 | 0.00 | O |
| ATOM | 5577 | C3* | A | D | 37 | 27.987 | 98.919 | 274.199 | 1.00 | 0.00 | C |
| ATOM | 5578 | O3* | A | D | 37 | 29.060 | 99.832 | 274.397 | 1.00 | 0.00 | O |
| ATOM | 5579 | C2* | A | D | 37 | 27.972 | 97.803 | 275.235 | 1.00 | 0.00 | C |
| ATOM | 5580 | O2* | A | D | 37 | 28.317 | 98.239 | 276.539 | 1.00 | 0.00 | O |
| ATOM | 5581 | C1* | A | D | 37 | 26.503 | 97.386 | 275.222 | 1.00 | 0.00 | C |
| ATOM | 5582 | N9 | A | D | 37 | 26.257 | 96.276 | 274.300 | 1.00 | 0.00 | N |
| ATOM | 5583 | C8 | A | D | 37 | 25.772 | 96.350 | 273.009 | 1.00 | 0.00 | C |
| ATOM | 5584 | N7 | A | D | 37 | 25.701 | 95.190 | 272.402 | 1.00 | 0.00 | N |
| ATOM | 5585 | C5 | A | D | 37 | 26.159 | 94.290 | 273.351 | 1.00 | 0.00 | C |
| ATOM | 5586 | C6 | A | D | 37 | 26.339 | 92.905 | 273.316 | 1.00 | 0.00 | C |
| ATOM | 5587 | N6 | A | D | 37 | 26.070 | 92.160 | 272.236 | 1.00 | 0.00 | N |
| ATOM | 5588 | N1 | A | D | 37 | 26.813 | 92.303 | 274.432 | 1.00 | 0.00 | N |
| ATOM | 5589 | C2 | A | D | 37 | 27.088 | 93.064 | 275.508 | 1.00 | 0.00 | C |
| ATOM | 5590 | N3 | A | D | 37 | 26.967 | 94.380 | 275.660 | 1.00 | 0.00 | N |
| ATOM | 5591 | C4 | A | D | 37 | 26.493 | 94.943 | 274.533 | 1.00 | 0.00 | C |
| ATOM | 5592 | P | U | D | 38 | 30.326 | 99.101 | 272.653 | 1.00 | 0.00 | P |
| ATOM | 5593 | O1P | U | D | 38 | 31.264 | 100.171 | 273.066 | 1.00 | 0.00 | O |
| ATOM | 5594 | O2P | U | D | 38 | 29.922 | 98.993 | 271.234 | 1.00 | 0.00 | O |
| ATOM | 5595 | O5* | U | D | 38 | 30.925 | 97.698 | 273.142 | 1.00 | 0.00 | O |
| ATOM | 5596 | C5* | U | D | 38 | 31.467 | 97.589 | 274.459 | 1.00 | 0.00 | C |
| ATOM | 5597 | C4* | U | D | 38 | 31.544 | 96.147 | 274.892 | 1.00 | 0.00 | C |
| ATOM | 5598 | O4* | U | D | 38 | 30.272 | 95.501 | 274.726 | 1.00 | 0.00 | O |
| ATOM | 5599 | C3* | U | D | 38 | 32.478 | 95.378 | 273.993 | 1.00 | 0.00 | C |
| ATOM | 5600 | O3* | U | D | 38 | 33.848 | 95.549 | 274.394 | 1.00 | 0.00 | O |
| ATOM | 5601 | C2* | U | D | 38 | 32.021 | 93.963 | 274.232 | 1.00 | 0.00 | C |
| ATOM | 5602 | O2* | U | D | 38 | 32.450 | 93.460 | 275.500 | 1.00 | 0.00 | O |
| ATOM | 5603 | C1* | U | D | 38 | 30.509 | 94.144 | 274.293 | 1.00 | 0.00 | C |
| ATOM | 5604 | N1 | U | D | 38 | 29.882 | 93.867 | 272.955 | 1.00 | 0.00 | N |
| ATOM | 5605 | C2 | U | D | 38 | 29.814 | 92.541 | 272.523 | 1.00 | 0.00 | C |
| ATOM | 5606 | O2 | U | D | 38 | 30.228 | 91.589 | 273.184 | 1.00 | 0.00 | O |
| ATOM | 5607 | N3 | U | D | 38 | 29.223 | 92.332 | 271.287 | 1.00 | 0.00 | N |
| ATOM | 5608 | C4 | U | D | 38 | 28.701 | 93.305 | 270.451 | 1.00 | 0.00 | C |

| | | | | | | | | | | |
|---|---|---|---|---|---|---|---|---|---|---|
| ATOM | 5609 | O4 | U | D | 38 | 28.216 | 93.006 | 269.363 | 1.00 | 0.00 | O |
| ATOM | 5610 | C5 | U | D | 38 | 28.809 | 94.645 | 270.972 | 1.00 | 0.00 | C |
| ATOM | 5611 | C6 | U | D | 38 | 29.381 | 94.880 | 272.172 | 1.00 | 0.00 | C |
| ATOM | 5612 | P | U | D | 39 | 35.006 | 95.745 | 273.289 | 1.00 | 0.00 | P |
| ATOM | 5613 | O1P | U | D | 39 | 36.276 | 95.777 | 274.044 | 1.00 | 0.00 | O |
| ATOM | 5614 | O2P | U | D | 39 | 34.648 | 96.866 | 272.389 | 1.00 | 0.00 | O |
| ATOM | 5615 | O5* | U | D | 39 | 34.975 | 94.379 | 272.449 | 1.00 | 0.00 | O |
| ATOM | 5616 | C5* | U | D | 39 | 35.394 | 93.127 | 273.005 | 1.00 | 0.00 | C |
| ATOM | 5617 | C4* | U | D | 39 | 35.043 | 91.961 | 272.084 | 1.00 | 0.00 | C |
| ATOM | 5618 | O4* | U | D | 39 | 33.632 | 91.881 | 271.822 | 1.00 | 0.00 | O |
| ATOM | 5619 | C3* | U | D | 39 | 35.636 | 92.204 | 270.716 | 1.00 | 0.00 | C |
| ATOM | 5620 | O3* | U | D | 39 | 37.035 | 91.888 | 270.728 | 1.00 | 0.00 | O |
| ATOM | 5621 | C2* | U | D | 39 | 34.830 | 91.253 | 269.861 | 1.00 | 0.00 | C |
| ATOM | 5622 | O2* | U | D | 39 | 35.216 | 89.893 | 270.096 | 1.00 | 0.00 | O |
| ATOM | 5623 | C1* | U | D | 39 | 33.431 | 91.478 | 270.443 | 1.00 | 0.00 | C |
| ATOM | 5624 | N1 | U | D | 39 | 32.682 | 92.532 | 269.676 | 1.00 | 0.00 | N |
| ATOM | 5625 | C2 | U | D | 39 | 32.073 | 92.172 | 268.479 | 1.00 | 0.00 | C |
| ATOM | 5626 | O2 | U | D | 39 | 32.133 | 91.039 | 268.003 | 1.00 | 0.00 | O |
| ATOM | 5627 | N3 | U | D | 39 | 31.383 | 93.180 | 267.824 | 1.00 | 0.00 | N |
| ATOM | 5628 | C4 | U | D | 39 | 31.248 | 94.492 | 268.242 | 1.00 | 0.00 | C |
| ATOM | 5629 | O4 | U | D | 39 | 30.609 | 95.309 | 267.585 | 1.00 | 0.00 | O |
| ATOM | 5630 | C5 | U | D | 39 | 31.909 | 94.777 | 269.482 | 1.00 | 0.00 | C |
| ATOM | 5631 | C6 | U | D | 39 | 32.586 | 93.817 | 270.141 | 1.00 | 0.00 | C |
| ATOM | 5632 | P | C | D | 40 | 38.038 | 92.701 | 269.770 | 1.00 | 0.00 | P |
| ATOM | 5633 | O1P | C | D | 40 | 39.258 | 92.076 | 270.331 | 1.00 | 0.00 | O |
| ATOM | 5634 | O2P | C | D | 40 | 37.935 | 94.174 | 269.683 | 1.00 | 0.00 | O |
| ATOM | 5635 | O5* | C | D | 40 | 37.761 | 92.107 | 268.302 | 1.00 | 0.00 | O |
| ATOM | 5636 | C5* | C | D | 40 | 38.105 | 90.778 | 267.888 | 1.00 | 0.00 | C |
| ATOM | 5637 | C4* | C | D | 40 | 37.513 | 90.471 | 266.513 | 1.00 | 0.00 | C |
| ATOM | 5638 | O4* | C | D | 40 | 36.073 | 90.600 | 266.511 | 1.00 | 0.00 | O |
| ATOM | 5639 | C3* | C | D | 40 | 37.949 | 91.535 | 265.522 | 1.00 | 0.00 | C |
| ATOM | 5640 | O3* | C | D | 40 | 39.296 | 91.278 | 265.057 | 1.00 | 0.00 | O |
| ATOM | 5641 | C2* | C | D | 40 | 36.897 | 91.392 | 264.433 | 1.00 | 0.00 | C |
| ATOM | 5642 | O2* | C | D | 40 | 37.052 | 90.206 | 263.632 | 1.00 | 0.00 | O |
| ATOM | 5643 | C1* | C | D | 40 | 35.643 | 91.224 | 265.273 | 1.00 | 0.00 | C |
| ATOM | 5644 | N1 | C | D | 40 | 35.015 | 92.573 | 265.462 | 1.00 | 0.00 | N |
| ATOM | 5645 | C2 | C | D | 40 | 34.262 | 93.099 | 264.412 | 1.00 | 0.00 | C |
| ATOM | 5646 | O2 | C | D | 40 | 34.122 | 92.493 | 263.351 | 1.00 | 0.00 | O |
| ATOM | 5647 | N3 | C | D | 40 | 33.676 | 94.314 | 264.582 | 1.00 | 0.00 | N |
| ATOM | 5648 | C4 | C | D | 40 | 33.809 | 94.999 | 265.720 | 1.00 | 0.00 | C |
| ATOM | 5649 | N4 | C | D | 40 | 33.210 | 96.181 | 265.849 | 1.00 | 0.00 | N |
| ATOM | 5650 | C5 | C | D | 40 | 34.579 | 94.481 | 266.805 | 1.00 | 0.00 | C |
| ATOM | 5651 | C6 | C | D | 40 | 35.155 | 93.276 | 266.629 | 1.00 | 0.00 | C |
| ATOM | 5652 | P | C | D | 41 | 40.163 | 92.429 | 264.300 | 1.00 | 0.00 | P |
| ATOM | 5653 | O1P | C | D | 41 | 41.275 | 91.913 | 265.137 | 1.00 | 0.00 | O |
| ATOM | 5654 | O2P | C | D | 41 | 40.286 | 93.736 | 263.612 | 1.00 | 0.00 | O |
| ATOM | 5655 | O5* | C | D | 41 | 39.740 | 91.280 | 263.241 | 1.00 | 0.00 | O |
| ATOM | 5656 | C5* | C | D | 41 | 40.023 | 91.182 | 261.841 | 1.00 | 0.00 | C |
| ATOM | 5657 | C4* | C | D | 41 | 39.028 | 91.917 | 260.938 | 1.00 | 0.00 | C |
| ATOM | 5658 | O4* | C | D | 41 | 37.805 | 92.290 | 261.592 | 1.00 | 0.00 | O |
| ATOM | 5659 | C3* | C | D | 41 | 39.573 | 93.257 | 260.574 | 1.00 | 0.00 | C |
| ATOM | 5660 | O3* | C | D | 41 | 40.665 | 93.100 | 259.657 | 1.00 | 0.00 | O |
| ATOM | 5661 | C2* | C | D | 41 | 38.363 | 93.902 | 259.939 | 1.00 | 0.00 | C |
| ATOM | 5662 | O2* | C | D | 41 | 38.075 | 93.402 | 258.618 | 1.00 | 0.00 | O |
| ATOM | 5663 | C1* | C | D | 41 | 37.255 | 93.419 | 260.869 | 1.00 | 0.00 | C |
| ATOM | 5664 | N1 | C | D | 41 | 36.846 | 94.564 | 261.748 | 1.00 | 0.00 | N |
| ATOM | 5665 | C2 | C | D | 41 | 36.025 | 95.556 | 261.204 | 1.00 | 0.00 | C |
| ATOM | 5666 | O2 | C | D | 41 | 35.652 | 95.521 | 260.030 | 1.00 | 0.00 | O |
| ATOM | 5667 | N3 | C | D | 41 | 35.641 | 96.587 | 262.005 | 1.00 | 0.00 | N |
| ATOM | 5668 | C4 | C | D | 41 | 36.034 | 96.664 | 263.279 | 1.00 | 0.00 | C |
| ATOM | 5669 | N4 | C | D | 41 | 35.632 | 97.692 | 264.024 | 1.00 | 0.00 | N |
| ATOM | 5670 | C5 | C | D | 41 | 36.877 | 95.663 | 263.853 | 1.00 | 0.00 | C |
| ATOM | 5671 | C6 | C | D | 41 | 37.251 | 94.643 | 263.054 | 1.00 | 0.00 | C |
| ATOM | 5672 | P | G | D | 42 | 42.030 | 93.927 | 259.897 | 1.00 | 0.00 | P |
| ATOM | 5673 | O1P | G | D | 42 | 42.951 | 93.203 | 258.987 | 1.00 | 0.00 | O |
| ATOM | 5674 | O2P | G | D | 42 | 42.457 | 94.245 | 261.281 | 1.00 | 0.00 | O |
| ATOM | 5675 | O5* | G | D | 42 | 41.544 | 95.294 | 259.188 | 1.00 | 0.00 | O |
| ATOM | 5676 | C5* | G | D | 42 | 41.193 | 95.295 | 257.801 | 1.00 | 0.00 | C |
| ATOM | 5677 | C4* | G | D | 42 | 40.235 | 96.421 | 257.457 | 1.00 | 0.00 | C |
| ATOM | 5678 | O4* | G | D | 42 | 39.133 | 96.484 | 258.365 | 1.00 | 0.00 | O |
| ATOM | 5679 | C3* | G | D | 42 | 40.863 | 97.764 | 257.681 | 1.00 | 0.00 | C |
| ATOM | 5680 | O3* | G | D | 42 | 41.830 | 98.037 | 256.665 | 1.00 | 0.00 | O |
| ATOM | 5681 | C2* | G | D | 42 | 39.648 | 98.653 | 257.546 | 1.00 | 0.00 | C |
| ATOM | 5682 | O2* | G | D | 42 | 39.264 | 98.877 | 256.177 | 1.00 | 0.00 | O |
| ATOM | 5683 | C1* | G | D | 42 | 38.565 | 97.795 | 258.189 | 1.00 | 0.00 | C |
| ATOM | 5684 | N9 | G | D | 42 | 38.166 | 98.454 | 259.455 | 1.00 | 0.00 | N |
| ATOM | 5685 | C8 | G | D | 42 | 38.436 | 98.115 | 260.755 | 1.00 | 0.00 | C |
| ATOM | 5686 | N7 | G | D | 42 | 37.929 | 98.938 | 261.631 | 1.00 | 0.00 | N |
| ATOM | 5687 | C5 | G | D | 42 | 37.278 | 99.888 | 260.859 | 1.00 | 0.00 | C |
| ATOM | 5688 | C6 | G | D | 42 | 36.548 | 101.033 | 261.256 | 1.00 | 0.00 | C |
| ATOM | 5689 | O6 | G | D | 42 | 36.330 | 101.436 | 262.393 | 1.00 | 0.00 | O |
| ATOM | 5690 | N1 | G | D | 42 | 36.054 | 101.728 | 260.165 | 1.00 | 0.00 | N |
| ATOM | 5691 | C2 | G | D | 42 | 36.240 | 101.370 | 258.849 | 1.00 | 0.00 | C |
| ATOM | 5692 | N2 | G | D | 42 | 35.697 | 102.161 | 257.925 | 1.00 | 0.00 | N |
| ATOM | 5693 | N3 | G | D | 42 | 36.926 | 100.290 | 258.474 | 1.00 | 0.00 | N |
| ATOM | 5694 | C4 | G | D | 42 | 37.415 | 99.602 | 259.531 | 1.00 | 0.00 | C |
| ATOM | 5695 | P | G | D | 43 | 42.859 | 99.260 | 256.833 | 1.00 | 0.00 | P |

| ATOM | 5696 | O1P | G D | 43 | 43.362 | 98.842 | 255.501 | 1.00 | 0.00 | O |
|---|---|---|---|---|---|---|---|---|---|---|
| ATOM | 5697 | O2P | G D | 43 | 43.753 | 99.211 | 258.015 | 1.00 | 0.00 | O |
| ATOM | 5698 | O5* | G D | 43 | 42.225 | 100.734 | 256.727 | 1.00 | 0.00 | O |
| ATOM | 5699 | C5* | G D | 43 | 41.567 | 101.130 | 255.524 | 1.00 | 0.00 | C |
| ATOM | 5700 | C4* | G D | 43 | 40.539 | 102.211 | 255.787 | 1.00 | 0.00 | C |
| ATOM | 5701 | O4* | G D | 43 | 39.653 | 101.862 | 256.852 | 1.00 | 0.00 | O |
| ATOM | 5702 | C3* | G D | 43 | 41.190 | 103.435 | 256.344 | 1.00 | 0.00 | C |
| ATOM | 5703 | O3* | G D | 43 | 41.905 | 104.104 | 255.311 | 1.00 | 0.00 | O |
| ATOM | 5704 | C2* | G D | 43 | 39.995 | 104.231 | 256.808 | 1.00 | 0.00 | C |
| ATOM | 5705 | O2* | G D | 43 | 39.250 | 104.810 | 255.717 | 1.00 | 0.00 | O |
| ATOM | 5706 | C1* | G D | 43 | 39.166 | 103.101 | 257.408 | 1.00 | 0.00 | C |
| ATOM | 5707 | N9 | G D | 43 | 39.270 | 103.105 | 258.893 | 1.00 | 0.00 | N |
| ATOM | 5708 | C8 | G D | 43 | 39.914 | 102.228 | 259.736 | 1.00 | 0.00 | C |
| ATOM | 5709 | N7 | G D | 43 | 39.739 | 102.486 | 261.003 | 1.00 | 0.00 | N |
| ATOM | 5710 | C5 | G D | 43 | 38.927 | 103.614 | 261.004 | 1.00 | 0.00 | C |
| ATOM | 5711 | C6 | G D | 43 | 38.400 | 104.352 | 262.092 | 1.00 | 0.00 | C |
| ATOM | 5712 | O6 | G D | 43 | 38.547 | 104.153 | 263.292 | 1.00 | 0.00 | O |
| ATOM | 5713 | N1 | G D | 43 | 37.635 | 105.416 | 261.664 | 1.00 | 0.00 | N |
| ATOM | 5714 | C2 | G D | 43 | 37.396 | 105.741 | 260.352 | 1.00 | 0.00 | C |
| ATOM | 5715 | N2 | G D | 43 | 36.628 | 106.802 | 260.135 | 1.00 | 0.00 | N |
| ATOM | 5716 | N3 | G D | 43 | 37.885 | 105.051 | 259.327 | 1.00 | 0.00 | N |
| ATOM | 5717 | C4 | G D | 43 | 38.639 | 104.002 | 259.725 | 1.00 | 0.00 | C |
| ATOM | 5718 | P | C D | 44 | 43.332 | 104.744 | 255.660 | 1.00 | 0.00 | P |
| ATOM | 5719 | O1P | C D | 44 | 43.646 | 105.698 | 254.568 | 1.00 | 0.00 | O |
| ATOM | 5720 | O2P | C D | 44 | 44.171 | 103.541 | 255.878 | 1.00 | 0.00 | O |
| ATOM | 5721 | O5* | C D | 44 | 43.256 | 105.715 | 256.922 | 1.00 | 0.00 | O |
| ATOM | 5722 | C5* | C D | 44 | 43.069 | 107.100 | 256.645 | 1.00 | 0.00 | C |
| ATOM | 5723 | C4* | C D | 44 | 41.741 | 107.566 | 257.192 | 1.00 | 0.00 | C |
| ATOM | 5724 | O4* | C D | 44 | 41.293 | 106.647 | 258.234 | 1.00 | 0.00 | O |
| ATOM | 5725 | C3* | C D | 44 | 41.744 | 108.950 | 257.836 | 1.00 | 0.00 | C |
| ATOM | 5726 | O3* | C D | 44 | 40.511 | 109.616 | 257.586 | 1.00 | 0.00 | O |
| ATOM | 5727 | C2* | C D | 44 | 41.890 | 108.627 | 259.317 | 1.00 | 0.00 | C |
| ATOM | 5728 | O2* | C D | 44 | 41.369 | 109.640 | 260.155 | 1.00 | 0.00 | O |
| ATOM | 5729 | C1* | C D | 44 | 41.044 | 107.368 | 259.426 | 1.00 | 0.00 | C |
| ATOM | 5730 | N1 | C D | 44 | 41.416 | 106.513 | 260.616 | 1.00 | 0.00 | N |
| ATOM | 5731 | C2 | C D | 44 | 40.870 | 106.836 | 261.860 | 1.00 | 0.00 | C |
| ATOM | 5732 | O2 | C D | 44 | 40.099 | 107.786 | 262.016 | 1.00 | 0.00 | O |
| ATOM | 5733 | N3 | C D | 44 | 41.196 | 106.057 | 262.924 | 1.00 | 0.00 | N |
| ATOM | 5734 | C4 | C D | 44 | 42.012 | 105.005 | 262.812 | 1.00 | 0.00 | C |
| ATOM | 5735 | N4 | C D | 44 | 42.291 | 104.266 | 263.885 | 1.00 | 0.00 | N |
| ATOM | 5736 | C5 | C D | 44 | 42.582 | 104.656 | 261.553 | 1.00 | 0.00 | C |
| ATOM | 5737 | C6 | C D | 44 | 42.256 | 105.432 | 260.501 | 1.00 | 0.00 | C |
| ATOM | 5738 | P | U D | 45 | 40.823 | 110.758 | 256.442 | 1.00 | 0.00 | P |
| ATOM | 5739 | O1P | U D | 45 | 40.081 | 111.733 | 257.286 | 1.00 | 0.00 | O |
| ATOM | 5740 | O2P | U D | 45 | 40.120 | 110.050 | 255.339 | 1.00 | 0.00 | O |
| ATOM | 5741 | O5* | U D | 45 | 42.107 | 111.469 | 255.820 | 1.00 | 0.00 | O |
| ATOM | 5742 | C5* | U D | 45 | 43.221 | 111.873 | 256.646 | 1.00 | 0.00 | C |
| ATOM | 5743 | C4* | U D | 45 | 43.919 | 113.073 | 256.036 | 1.00 | 0.00 | C |
| ATOM | 5744 | O4* | U D | 45 | 42.929 | 114.024 | 255.564 | 1.00 | 0.00 | O |
| ATOM | 5745 | C3* | U D | 45 | 44.844 | 113.839 | 256.971 | 1.00 | 0.00 | C |
| ATOM | 5746 | O3* | U D | 45 | 45.963 | 114.297 | 256.216 | 1.00 | 0.00 | O |
| ATOM | 5747 | C2* | U D | 45 | 43.986 | 115.023 | 257.417 | 1.00 | 0.00 | C |
| ATOM | 5748 | O2* | U D | 45 | 44.740 | 116.168 | 257.757 | 1.00 | 0.00 | O |
| ATOM | 5749 | C1* | U D | 45 | 43.143 | 115.282 | 256.168 | 1.00 | 0.00 | C |
| ATOM | 5750 | N1 | U D | 45 | 41.825 | 115.880 | 256.444 | 1.00 | 0.00 | N |
| ATOM | 5751 | C2 | U D | 45 | 41.553 | 117.135 | 255.916 | 1.00 | 0.00 | C |
| ATOM | 5752 | O2 | U D | 45 | 42.365 | 117.775 | 255.268 | 1.00 | 0.00 | O |
| ATOM | 5753 | N3 | U D | 45 | 40.290 | 117.610 | 256.178 | 1.00 | 0.00 | N |
| ATOM | 5754 | C4 | U D | 45 | 39.298 | 116.981 | 256.904 | 1.00 | 0.00 | C |
| ATOM | 5755 | O4 | U D | 45 | 38.203 | 117.526 | 257.031 | 1.00 | 0.00 | O |
| ATOM | 5756 | C5 | U D | 45 | 39.663 | 115.700 | 257.430 | 1.00 | 0.00 | C |
| ATOM | 5757 | C6 | U D | 45 | 40.884 | 115.206 | 257.189 | 1.00 | 0.00 | C |
| ATOM | 5758 | P | A D | 46 | 47.308 | 113.675 | 256.313 | 1.00 | 0.00 | P |
| ATOM | 5759 | O1P | A D | 46 | 48.278 | 114.194 | 255.317 | 1.00 | 0.00 | O |
| ATOM | 5760 | O2P | A D | 46 | 47.021 | 112.213 | 256.371 | 1.00 | 0.00 | O |
| ATOM | 5761 | O5* | A D | 46 | 47.802 | 114.136 | 257.754 | 1.00 | 0.00 | O |
| ATOM | 5762 | C5* | A D | 46 | 48.700 | 113.317 | 258.500 | 1.00 | 0.00 | C |
| ATOM | 5763 | C4* | A D | 46 | 49.317 | 114.106 | 259.628 | 1.00 | 0.00 | C |
| ATOM | 5764 | O4* | A D | 46 | 49.219 | 113.304 | 260.828 | 1.00 | 0.00 | O |
| ATOM | 5765 | C3* | A D | 46 | 50.793 | 114.458 | 259.465 | 1.00 | 0.00 | C |
| ATOM | 5766 | O3* | A D | 46 | 50.984 | 115.745 | 258.869 | 1.00 | 0.00 | O |
| ATOM | 5767 | C2* | A D | 46 | 51.310 | 114.386 | 260.894 | 1.00 | 0.00 | C |
| ATOM | 5768 | O2* | A D | 46 | 51.045 | 115.570 | 261.622 | 1.00 | 0.00 | O |
| ATOM | 5769 | C1* | A D | 46 | 50.479 | 113.226 | 261.451 | 1.00 | 0.00 | C |
| ATOM | 5770 | N9 | A D | 46 | 51.025 | 111.916 | 261.107 | 1.00 | 0.00 | N |
| ATOM | 5771 | C8 | A D | 46 | 50.986 | 111.306 | 259.875 | 1.00 | 0.00 | C |
| ATOM | 5772 | N7 | A D | 46 | 51.543 | 110.121 | 259.855 | 1.00 | 0.00 | N |
| ATOM | 5773 | C5 | A D | 46 | 51.979 | 109.938 | 261.158 | 1.00 | 0.00 | C |
| ATOM | 5774 | C6 | A D | 46 | 52.650 | 108.881 | 261.786 | 1.00 | 0.00 | C |
| ATOM | 5775 | N6 | A D | 46 | 53.012 | 107.761 | 261.160 | 1.00 | 0.00 | N |
| ATOM | 5776 | N1 | A D | 46 | 52.940 | 109.013 | 263.097 | 1.00 | 0.00 | N |
| ATOM | 5777 | C2 | A D | 46 | 52.573 | 110.140 | 263.724 | 1.00 | 0.00 | C |
| ATOM | 5778 | N3 | A D | 46 | 51.938 | 111.205 | 263.243 | 1.00 | 0.00 | N |
| ATOM | 5779 | C4 | A D | 46 | 51.667 | 111.037 | 261.940 | 1.00 | 0.00 | C |
| ATOM | 5780 | P | U D | 48 | 52.683 | 115.971 | 258.469 | 1.00 | 0.00 | P |
| ATOM | 5781 | O1P | U D | 48 | 53.320 | 116.982 | 257.565 | 1.00 | 0.00 | O |
| ATOM | 5782 | O2P | U D | 48 | 52.621 | 114.640 | 257.799 | 1.00 | 0.00 | O |

```
ATOM    5783  O5*   U   D  48     53.317 115.932 259.925  1.00  0.00           O
ATOM    5784  C5*   U   D  48     54.587 115.359 260.302  1.00  0.00           C
ATOM    5785  C4*   U   D  48     54.473 115.012 261.779  1.00  0.00           C
ATOM    5786  O4*   U   D  48     54.460 113.592 261.903  1.00  0.00           O
ATOM    5787  C3*   U   D  48     55.630 115.482 262.668  1.00  0.00           C
ATOM    5788  O3*   U   D  48     55.151 115.819 263.998  1.00  0.00           O
ATOM    5789  C2*   U   D  48     56.526 114.263 262.763  1.00  0.00           C
ATOM    5790  O2*   U   D  48     57.312 114.351 263.918  1.00  0.00           O
ATOM    5791  C1*   U   D  48     55.509 113.171 262.793  1.00  0.00           C
ATOM    5792  N1    U   D  48     56.033 111.871 262.334  1.00  0.00           N
ATOM    5793  C2    U   D  48     56.225 110.914 263.323  1.00  0.00           C
ATOM    5794  O2    U   D  48     55.981 111.182 264.500  1.00  0.00           O
ATOM    5795  N3    U   D  48     56.693 109.691 262.951  1.00  0.00           N
ATOM    5796  C4    U   D  48     56.964 109.393 261.643  1.00  0.00           C
ATOM    5797  O4    U   D  48     57.392 108.231 261.396  1.00  0.00           O
ATOM    5798  C5    U   D  48     56.756 110.379 260.643  1.00  0.00           C
ATOM    5799  C6    U   D  48     56.297 111.588 261.031  1.00  0.00           C
HETATM  5800  P     5MC D  49     56.042 116.998 265.337  1.00  0.00           P
HETATM  5801  O1P   5MC D  49     56.739 116.399 266.485  1.00  0.00           O
HETATM  5802  O2P   5MC D  49     56.985 117.545 264.311  1.00  0.00           O
HETATM  5803  O5*   5MC D  49     54.908 118.047 265.677  1.00  0.00           O
HETATM  5804  C5*   5MC D  49     53.814 118.209 264.728  1.00  0.00           C
HETATM  5805  C4*   5MC D  49     53.490 119.690 264.706  1.00  0.00           C
HETATM  5806  O4*   5MC D  49     53.799 120.273 265.966  1.00  0.00           O
HETATM  5807  C3*   5MC D  49     54.306 120.504 263.686  1.00  0.00           C
HETATM  5808  O3*   5MC D  49     53.782 120.418 262.364  1.00  0.00           O
HETATM  5809  C2*   5MC D  49     54.208 121.900 264.286  1.00  0.00           C
HETATM  5810  O2*   5MC D  49     52.954 122.421 263.883  1.00  0.00           O
HETATM  5811  C1*   5MC D  49     54.240 121.608 265.772  1.00  0.00           C
HETATM  5812  N1    5MC D  49     55.628 121.806 266.234  1.00  0.00           N
HETATM  5813  C2    5MC D  49     56.126 123.095 266.168  1.00  0.00           C
HETATM  5814  O2    5MC D  49     55.419 124.004 265.745  1.00  0.00           O
HETATM  5815  N3    5MC D  49     57.406 123.299 266.587  1.00  0.00           N
HETATM  5816  C4    5MC D  49     58.185 122.281 267.054  1.00  0.00           C
HETATM  5817  N4    5MC D  49     59.438 122.523 267.449  1.00  0.00           N
HETATM  5818  C5    5MC D  49     57.647 120.962 267.114  1.00  0.00           C
HETATM  5819  C6    5MC D  49     56.393 120.778 266.695  1.00  0.00           C
HETATM  5820  CM5   5MC D  49     58.498 119.833 267.625  1.00  0.00           C
ATOM    5821  P     G   D  50     54.665 120.187 261.050  1.00  0.00           P
ATOM    5822  O1P   G   D  50     53.928 119.423 259.999  1.00  0.00           O
ATOM    5823  O2P   G   D  50     55.880 119.475 261.519  1.00  0.00           O
ATOM    5824  O5*   G   D  50     54.921 121.669 260.543  1.00  0.00           O
ATOM    5825  C5*   G   D  50     53.880 122.661 260.830  1.00  0.00           C
ATOM    5826  C4*   G   D  50     54.558 123.976 260.460  1.00  0.00           C
ATOM    5827  O4*   G   D  50     54.993 124.646 261.616  1.00  0.00           O
ATOM    5828  C3*   G   D  50     55.802 123.792 259.604  1.00  0.00           C
ATOM    5829  O3*   G   D  50     55.503 123.572 258.233  1.00  0.00           O
ATOM    5830  C2*   G   D  50     56.567 125.099 259.861  1.00  0.00           C
ATOM    5831  O2*   G   D  50     55.987 126.073 259.008  1.00  0.00           O
ATOM    5832  C1*   G   D  50     56.214 125.346 261.316  1.00  0.00           C
ATOM    5833  N9    G   D  50     57.292 124.873 262.207  1.00  0.00           N
ATOM    5834  C8    G   D  50     57.391 123.685 262.886  1.00  0.00           C
ATOM    5835  N7    G   D  50     58.482 123.585 263.603  1.00  0.00           N
ATOM    5836  C5    G   D  50     59.137 124.792 263.393  1.00  0.00           C
ATOM    5837  C6    G   D  50     60.367 125.307 263.886  1.00  0.00           C
ATOM    5838  O6    G   D  50     61.156 124.746 264.656  1.00  0.00           O
ATOM    5839  N1    G   D  50     60.673 126.559 263.443  1.00  0.00           N
ATOM    5840  C2    G   D  50     59.875 127.254 262.593  1.00  0.00           C
ATOM    5841  N2    G   D  50     60.299 128.480 262.234  1.00  0.00           N
ATOM    5842  N3    G   D  50     58.712 126.823 262.103  1.00  0.00           N
ATOM    5843  C4    G   D  50     58.413 125.589 262.539  1.00  0.00           C
ATOM    5844  P     G   D  51     56.656 123.127 257.236  1.00  0.00           P
ATOM    5845  O1P   G   D  51     56.103 122.461 256.013  1.00  0.00           O
ATOM    5846  O2P   G   D  51     57.483 122.202 258.058  1.00  0.00           O
ATOM    5847  O5*   G   D  51     57.361 124.503 256.872  1.00  0.00           O
ATOM    5848  C5*   G   D  51     58.512 124.474 255.979  1.00  0.00           C
ATOM    5849  C4*   G   D  51     59.381 125.639 256.404  1.00  0.00           C
ATOM    5850  O4*   G   D  51     59.276 125.845 257.807  1.00  0.00           O
ATOM    5851  C3*   G   D  51     60.873 125.435 256.166  1.00  0.00           C
ATOM    5852  O3*   G   D  51     61.214 125.691 254.807  1.00  0.00           O
ATOM    5853  C2*   G   D  51     61.502 126.406 257.157  1.00  0.00           C
ATOM    5854  O2*   G   D  51     61.446 127.693 256.570  1.00  0.00           O
ATOM    5855  C1*   G   D  51     60.541 126.313 258.331  1.00  0.00           C
ATOM    5856  N9    G   D  51     61.017 125.411 259.400  1.00  0.00           N
ATOM    5857  C8    G   D  51     60.371 124.325 259.903  1.00  0.00           C
ATOM    5858  N7    G   D  51     61.027 123.717 260.859  1.00  0.00           N
ATOM    5859  C5    G   D  51     62.190 124.467 260.994  1.00  0.00           C
ATOM    5860  C6    G   D  51     63.298 124.318 261.865  1.00  0.00           C
ATOM    5861  O6    G   D  51     63.462 123.436 262.723  1.00  0.00           O
ATOM    5862  N1    G   D  51     64.277 125.265 261.704  1.00  0.00           N
ATOM    5863  C2    G   D  51     64.173 126.263 260.790  1.00  0.00           C
ATOM    5864  N2    G   D  51     65.206 127.109 260.765  1.00  0.00           N
ATOM    5865  N3    G   D  51     63.152 126.447 259.950  1.00  0.00           N
ATOM    5866  C4    G   D  51     62.198 125.514 260.107  1.00  0.00           C
ATOM    5867  P     G   D  52     61.782 124.506 253.875  1.00  0.00           P
ATOM    5868  O1P   G   D  52     61.404 124.680 252.439  1.00  0.00           O
ATOM    5869  O2P   G   D  52     61.162 123.305 254.480  1.00  0.00           O
```

```
ATOM    5870  O5*   G D  52      63.368 124.662 254.080  1.00  0.00           O
ATOM    5871  C5*   G D  52      63.882 126.022 254.138  1.00  0.00           C
ATOM    5872  C4*   G D  52      65.177 125.985 254.906  1.00  0.00           C
ATOM    5873  O4*   G D  52      64.939 126.096 256.308  1.00  0.00           O
ATOM    5874  C3*   G D  52      65.964 124.679 254.751  1.00  0.00           C
ATOM    5875  O3*   G D  52      66.720 124.609 253.538  1.00  0.00           O
ATOM    5876  C2*   G D  52      66.845 124.700 256.005  1.00  0.00           C
ATOM    5877  O2*   G D  52      67.949 125.533 255.713  1.00  0.00           O
ATOM    5878  C1*   G D  52      65.902 125.341 257.013  1.00  0.00           C
ATOM    5879  N9    G D  52      65.284 124.252 257.795  1.00  0.00           N
ATOM    5880  C8    G D  52      64.037 123.736 257.604  1.00  0.00           C
ATOM    5881  N7    G D  52      63.733 122.770 258.434  1.00  0.00           N
ATOM    5882  C5    G D  52      64.884 122.640 259.216  1.00  0.00           C
ATOM    5883  C6    G D  52      65.188 121.764 260.293  1.00  0.00           C
ATOM    5884  O6    G D  52      64.463 120.897 260.775  1.00  0.00           O
ATOM    5885  N1    G D  52      66.439 121.943 260.822  1.00  0.00           N
ATOM    5886  C2    G D  52      67.310 122.885 260.350  1.00  0.00           C
ATOM    5887  N2    G D  52      68.487 122.927 260.972  1.00  0.00           N
ATOM    5888  N3    G D  52      67.069 123.726 259.344  1.00  0.00           N
ATOM    5889  C4    G D  52      65.838 123.551 258.824  1.00  0.00           C
ATOM    5890  P     G D  53      67.512 123.290 253.081  1.00  0.00           P
ATOM    5891  O1P   G D  53      67.516 123.172 251.578  1.00  0.00           O
ATOM    5892  O2P   G D  53      66.782 122.176 253.732  1.00  0.00           O
ATOM    5893  O5*   G D  53      68.991 123.557 253.627  1.00  0.00           O
ATOM    5894  C5*   G D  53      69.910 122.451 253.809  1.00  0.00           C
ATOM    5895  C4*   G D  53      70.513 122.601 255.188  1.00  0.00           C
ATOM    5896  O4*   G D  53      69.507 122.832 256.160  1.00  0.00           O
ATOM    5897  C3*   G D  53      71.252 121.364 255.689  1.00  0.00           C
ATOM    5898  O3*   G D  53      72.556 121.243 255.137  1.00  0.00           O
ATOM    5899  C2*   G D  53      71.235 121.563 257.212  1.00  0.00           C
ATOM    5900  O2*   G D  53      72.308 122.435 257.527  1.00  0.00           O
ATOM    5901  C1*   G D  53      69.887 122.228 257.398  1.00  0.00           C
ATOM    5902  N9    G D  53      68.885 121.225 257.822  1.00  0.00           N
ATOM    5903  C8    G D  53      67.608 121.077 257.354  1.00  0.00           C
ATOM    5904  N7    G D  53      66.949 120.101 257.908  1.00  0.00           N
ATOM    5905  C5    G D  53      67.868 119.565 258.811  1.00  0.00           C
ATOM    5906  C6    G D  53      67.751 118.470 259.727  1.00  0.00           C
ATOM    5907  O6    G D  53      66.773 117.752 259.903  1.00  0.00           O
ATOM    5908  N1    G D  53      68.882 118.238 260.466  1.00  0.00           N
ATOM    5909  C2    G D  53      70.004 118.984 260.329  1.00  0.00           C
ATOM    5910  N2    G D  53      71.034 118.635 261.120  1.00  0.00           N
ATOM    5911  N3    G D  53      70.167 120.014 259.494  1.00  0.00           N
ATOM    5912  C4    G D  53      69.059 120.252 258.768  1.00  0.00           C
HETATM  5913  N1    5MU D  54    71.979 116.832 257.972  1.00  0.00           N
HETATM  5914  C2    5MU D  54    71.372 115.904 258.801  1.00  0.00           C
HETATM  5915  N3    5MU D  54    70.093 115.554 258.515  1.00  0.00           N
HETATM  5916  C4    5MU D  54    69.396 116.056 257.464  1.00  0.00           C
HETATM  5917  C5    5MU D  54    70.037 117.011 256.623  1.00  0.00           C
HETATM  5918  C5M   5MU D  54    69.299 117.600 255.448  1.00  0.00           C
HETATM  5919  C6    5MU D  54    71.298 117.360 256.908  1.00  0.00           C
HETATM  5920  O2    5MU D  54    71.971 115.421 259.765  1.00  0.00           O
HETATM  5921  O4    5MU D  54    68.206 115.661 257.294  1.00  0.00           O
HETATM  5922  C1*   5MU D  54    73.373 117.218 258.280  1.00  0.00           C
HETATM  5923  C2*   5MU D  54    74.293 116.260 257.570  1.00  0.00           C
HETATM  5924  O2*   5MU D  54    75.511 116.072 258.278  1.00  0.00           O
HETATM  5925  C3*   5MU D  54    74.663 117.059 256.322  1.00  0.00           C
HETATM  5926  C4*   5MU D  54    74.716 118.476 256.874  1.00  0.00           C
HETATM  5927  O3*   5MU D  54    75.877 116.603 255.713  1.00  0.00           O
HETATM  5928  O4*   5MU D  54    73.669 118.527 257.836  1.00  0.00           O
HETATM  5929  C5*   5MU D  54    74.522 119.569 255.850  1.00  0.00           C
HETATM  5930  O5*   5MU D  54    73.613 119.012 254.844  1.00  0.00           O
HETATM  5931  P     5MU D  54    72.780 120.095 254.018  1.00  0.00           P
HETATM  5932  O1P   5MU D  54    71.395 119.696 253.676  1.00  0.00           O
HETATM  5933  O2P   5MU D  54    73.560 120.638 252.857  1.00  0.00           O
HETATM  5934  N1    PSU D  55    70.876 114.557 254.470  1.00  0.00           N
HETATM  5935  C2    PSU D  55    69.578 114.141 254.531  1.00  0.00           C
HETATM  5936  N3    PSU D  55    69.403 112.968 255.208  1.00  0.00           N
HETATM  5937  C4    PSU D  55    70.385 112.203 255.821  1.00  0.00           C
HETATM  5938  C5    PSU D  55    71.731 112.732 255.714  1.00  0.00           C
HETATM  5939  C6    PSU D  55    71.907 113.877 255.043  1.00  0.00           C
HETATM  5940  O2    PSU D  55    68.653 114.764 254.014  1.00  0.00           O
HETATM  5941  O4    PSU D  55    70.137 111.174 256.412  1.00  0.00           O
HETATM  5942  C1*   PSU D  55    72.870 111.984 256.337  1.00  0.00           C
HETATM  5943  C2*   PSU D  55    73.528 111.078 255.314  1.00  0.00           C
HETATM  5944  O2*   PSU D  55    74.036 109.898 255.921  1.00  0.00           O
HETATM  5945  C3*   PSU D  55    74.730 111.931 254.895  1.00  0.00           C
HETATM  5946  C4*   PSU D  55    75.098 112.614 256.204  1.00  0.00           C
HETATM  5947  O3*   PSU D  55    75.778 111.145 254.310  1.00  0.00           O
HETATM  5948  O4*   PSU D  55    73.847 112.876 256.838  1.00  0.00           O
HETATM  5949  C5*   PSU D  55    75.876 113.914 256.057  1.00  0.00           C
HETATM  5950  O5*   PSU D  55    75.786 114.295 254.658  1.00  0.00           O
HETATM  5951  P     PSU D  55    75.709 115.847 254.287  1.00  0.00           P
HETATM  5952  O1P   PSU D  55    74.342 116.280 253.856  1.00  0.00           O
HETATM  5953  O2P   PSU D  55    76.768 116.249 253.331  1.00  0.00           O
ATOM    5954  P     C D  56      75.917 110.922 252.638  1.00  0.00           P
ATOM    5955  O1P   C D  56      77.182 110.140 252.475  1.00  0.00           O
ATOM    5956  O2P   C D  56      75.733 112.211 251.902  1.00  0.00           O
```

| | | | | | | | | | |
|---|---|---|---|---|---|---|---|---|---|
| ATOM | 5957 | O5* | C D | 56 | 74.700 | 110.010 | 252.179 | 1.00 | 0.00 | O |
| ATOM | 5958 | C5* | C D | 56 | 74.387 | 109.898 | 250.807 | 1.00 | 0.00 | C |
| ATOM | 5959 | C4* | C D | 56 | 73.287 | 108.902 | 250.596 | 1.00 | 0.00 | C |
| ATOM | 5960 | O4* | C D | 56 | 73.793 | 107.578 | 250.871 | 1.00 | 0.00 | O |
| ATOM | 5961 | C3* | C D | 56 | 72.092 | 109.054 | 251.529 | 1.00 | 0.00 | C |
| ATOM | 5962 | O3* | C D | 56 | 71.206 | 110.005 | 250.959 | 1.00 | 0.00 | O |
| ATOM | 5963 | C2* | C D | 56 | 71.497 | 107.658 | 251.485 | 1.00 | 0.00 | C |
| ATOM | 5964 | O2* | C D | 56 | 70.674 | 107.403 | 250.343 | 1.00 | 0.00 | O |
| ATOM | 5965 | C1* | C D | 56 | 72.765 | 106.797 | 251.461 | 1.00 | 0.00 | C |
| ATOM | 5966 | N1 | C D | 56 | 73.194 | 106.441 | 252.820 | 1.00 | 0.00 | N |
| ATOM | 5967 | C2 | C D | 56 | 72.530 | 105.417 | 253.472 | 1.00 | 0.00 | C |
| ATOM | 5968 | O2 | C D | 56 | 71.590 | 104.887 | 252.926 | 1.00 | 0.00 | O |
| ATOM | 5969 | N3 | C D | 56 | 72.927 | 105.036 | 254.686 | 1.00 | 0.00 | N |
| ATOM | 5970 | C4 | C D | 56 | 73.941 | 105.644 | 255.278 | 1.00 | 0.00 | C |
| ATOM | 5971 | N4 | C D | 56 | 74.288 | 105.196 | 256.483 | 1.00 | 0.00 | N |
| ATOM | 5972 | C5 | C D | 56 | 74.638 | 106.726 | 254.660 | 1.00 | 0.00 | C |
| ATOM | 5973 | C6 | C D | 56 | 74.230 | 107.091 | 253.429 | 1.00 | 0.00 | C |
| ATOM | 5974 | P | A D | 57 | 70.636 | 111.075 | 252.314 | 1.00 | 0.00 | P |
| ATOM | 5975 | O1P | A D | 57 | 69.978 | 112.221 | 251.603 | 1.00 | 0.00 | O |
| ATOM | 5976 | O2P | A D | 57 | 71.842 | 111.523 | 253.055 | 1.00 | 0.00 | O |
| ATOM | 5977 | O5* | A D | 57 | 69.581 | 110.256 | 253.174 | 1.00 | 0.00 | O |
| ATOM | 5978 | C5* | A D | 57 | 68.579 | 109.499 | 252.433 | 1.00 | 0.00 | C |
| ATOM | 5979 | C4* | A D | 57 | 67.950 | 108.542 | 253.427 | 1.00 | 0.00 | C |
| ATOM | 5980 | O4* | A D | 57 | 68.885 | 107.526 | 253.760 | 1.00 | 0.00 | O |
| ATOM | 5981 | C3* | A D | 57 | 67.560 | 109.168 | 254.765 | 1.00 | 0.00 | C |
| ATOM | 5982 | O3* | A D | 57 | 66.310 | 109.831 | 254.716 | 1.00 | 0.00 | O |
| ATOM | 5983 | C2* | A D | 57 | 67.562 | 107.943 | 255.686 | 1.00 | 0.00 | C |
| ATOM | 5984 | O2* | A D | 57 | 66.306 | 107.305 | 255.500 | 1.00 | 0.00 | O |
| ATOM | 5985 | C1* | A D | 57 | 68.705 | 107.127 | 255.127 | 1.00 | 0.00 | C |
| ATOM | 5986 | N9 | A D | 57 | 69.964 | 107.314 | 255.861 | 1.00 | 0.00 | N |
| ATOM | 5987 | C8 | A D | 57 | 71.083 | 107.974 | 255.438 | 1.00 | 0.00 | C |
| ATOM | 5988 | N7 | A D | 57 | 72.063 | 107.975 | 256.306 | 1.00 | 0.00 | N |
| ATOM | 5989 | C5 | A D | 57 | 71.543 | 107.258 | 257.379 | 1.00 | 0.00 | C |
| ATOM | 5990 | C6 | A D | 57 | 72.110 | 106.905 | 258.632 | 1.00 | 0.00 | C |
| ATOM | 5991 | N6 | A D | 57 | 73.335 | 107.232 | 259.018 | 1.00 | 0.00 | N |
| ATOM | 5992 | N1 | A D | 57 | 71.294 | 106.181 | 259.450 | 1.00 | 0.00 | N |
| ATOM | 5993 | C2 | A D | 57 | 70.028 | 105.833 | 259.074 | 1.00 | 0.00 | C |
| ATOM | 5994 | N3 | A D | 57 | 69.443 | 106.128 | 257.921 | 1.00 | 0.00 | N |
| ATOM | 5995 | C4 | A D | 57 | 70.266 | 106.849 | 257.114 | 1.00 | 0.00 | C |
| ATOM | 5996 | P | A D | 58 | 65.749 | 110.971 | 255.690 | 1.00 | 0.00 | P |
| ATOM | 5997 | O1P | A D | 58 | 64.275 | 111.151 | 255.515 | 1.00 | 0.00 | O |
| ATOM | 5998 | O2P | A D | 58 | 66.515 | 112.172 | 255.271 | 1.00 | 0.00 | O |
| ATOM | 5999 | O5* | A D | 58 | 66.075 | 110.461 | 257.164 | 1.00 | 0.00 | O |
| ATOM | 6000 | C5* | A D | 58 | 65.406 | 109.278 | 257.669 | 1.00 | 0.00 | C |
| ATOM | 6001 | C4* | A D | 58 | 64.861 | 109.659 | 259.034 | 1.00 | 0.00 | C |
| ATOM | 6002 | O4* | A D | 58 | 65.954 | 110.080 | 259.852 | 1.00 | 0.00 | O |
| ATOM | 6003 | C3* | A D | 58 | 63.885 | 110.831 | 259.000 | 1.00 | 0.00 | C |
| ATOM | 6004 | O3* | A D | 58 | 62.861 | 110.658 | 260.011 | 1.00 | 0.00 | O |
| ATOM | 6005 | C2* | A D | 58 | 64.774 | 112.020 | 259.334 | 1.00 | 0.00 | C |
| ATOM | 6006 | O2* | A D | 58 | 63.963 | 113.066 | 259.808 | 1.00 | 0.00 | O |
| ATOM | 6007 | C1* | A D | 58 | 65.723 | 111.418 | 260.317 | 1.00 | 0.00 | C |
| ATOM | 6008 | N9 | A D | 58 | 66.985 | 112.176 | 260.404 | 1.00 | 0.00 | N |
| ATOM | 6009 | C8 | A D | 58 | 67.461 | 113.150 | 259.569 | 1.00 | 0.00 | C |
| ATOM | 6010 | N7 | A D | 58 | 68.614 | 113.636 | 259.925 | 1.00 | 0.00 | N |
| ATOM | 6011 | C5 | A D | 58 | 68.936 | 112.934 | 261.077 | 1.00 | 0.00 | C |
| ATOM | 6012 | C6 | A D | 58 | 70.047 | 112.990 | 261.941 | 1.00 | 0.00 | C |
| ATOM | 6013 | N6 | A D | 58 | 71.088 | 113.805 | 261.773 | 1.00 | 0.00 | N |
| ATOM | 6014 | N1 | A D | 58 | 70.017 | 112.132 | 263.001 | 1.00 | 0.00 | N |
| ATOM | 6015 | C2 | A D | 58 | 68.974 | 111.281 | 263.205 | 1.00 | 0.00 | C |
| ATOM | 6016 | N3 | A D | 58 | 67.889 | 111.175 | 262.433 | 1.00 | 0.00 | N |
| ATOM | 6017 | C4 | A D | 58 | 67.929 | 112.025 | 261.390 | 1.00 | 0.00 | C |
| ATOM | 6018 | P | U D | 59 | 61.341 | 111.149 | 259.834 | 1.00 | 0.00 | P |
| ATOM | 6019 | O1P | U D | 59 | 60.521 | 110.132 | 259.096 | 1.00 | 0.00 | O |
| ATOM | 6020 | O2P | U D | 59 | 61.481 | 112.415 | 259.049 | 1.00 | 0.00 | O |
| ATOM | 6021 | O5* | U D | 59 | 60.776 | 111.350 | 261.321 | 1.00 | 0.00 | O |
| ATOM | 6022 | C5* | U D | 59 | 60.311 | 112.694 | 261.609 | 1.00 | 0.00 | C |
| ATOM | 6023 | C4* | U D | 59 | 60.077 | 112.824 | 263.089 | 1.00 | 0.00 | C |
| ATOM | 6024 | O4* | U D | 59 | 59.328 | 111.691 | 263.545 | 1.00 | 0.00 | O |
| ATOM | 6025 | C3* | U D | 59 | 61.331 | 112.817 | 263.963 | 1.00 | 0.00 | C |
| ATOM | 6026 | O3* | U D | 59 | 61.958 | 114.082 | 264.055 | 1.00 | 0.00 | O |
| ATOM | 6027 | C2* | U D | 59 | 60.774 | 112.342 | 265.314 | 1.00 | 0.00 | C |
| ATOM | 6028 | O2* | U D | 59 | 60.210 | 113.483 | 265.945 | 1.00 | 0.00 | O |
| ATOM | 6029 | C1* | U D | 59 | 59.708 | 111.357 | 264.882 | 1.00 | 0.00 | C |
| ATOM | 6030 | N1 | U D | 59 | 60.227 | 109.976 | 264.978 | 1.00 | 0.00 | N |
| ATOM | 6031 | C2 | U D | 59 | 60.618 | 109.553 | 266.240 | 1.00 | 0.00 | C |
| ATOM | 6032 | O2 | U D | 59 | 60.533 | 110.297 | 267.213 | 1.00 | 0.00 | O |
| ATOM | 6033 | N3 | U D | 59 | 61.096 | 108.281 | 266.369 | 1.00 | 0.00 | N |
| ATOM | 6034 | C4 | U D | 59 | 61.192 | 107.436 | 265.302 | 1.00 | 0.00 | C |
| ATOM | 6035 | O4 | U D | 59 | 61.646 | 106.272 | 265.539 | 1.00 | 0.00 | O |
| ATOM | 6036 | C5 | U D | 59 | 60.778 | 107.883 | 264.015 | 1.00 | 0.00 | C |
| ATOM | 6037 | C6 | U D | 59 | 60.320 | 109.138 | 263.911 | 1.00 | 0.00 | C |
| ATOM | 6038 | P | U D | 60 | 63.499 | 114.298 | 263.615 | 1.00 | 0.00 | P |
| ATOM | 6039 | O1P | U D | 60 | 63.840 | 115.755 | 263.628 | 1.00 | 0.00 | O |
| ATOM | 6040 | O2P | U D | 60 | 63.538 | 113.720 | 262.256 | 1.00 | 0.00 | O |
| ATOM | 6041 | O5* | U D | 60 | 64.311 | 113.509 | 264.734 | 1.00 | 0.00 | O |
| ATOM | 6042 | C5* | U D | 60 | 64.052 | 113.891 | 266.104 | 1.00 | 0.00 | C |
| ATOM | 6043 | C4* | U D | 60 | 64.631 | 112.813 | 267.000 | 1.00 | 0.00 | C |

```
ATOM   6044  O4*  U D  60    64.021 111.563 266.711  1.00  0.00           O
ATOM   6045  C3*  U D  60    66.150 112.591 266.805  1.00  0.00           C
ATOM   6046  O3*  U D  60    66.749 112.316 268.105  1.00  0.00           O
ATOM   6047  C2*  U D  60    66.195 111.387 265.881  1.00  0.00           C
ATOM   6048  O2*  U D  60    67.417 110.735 266.006  1.00  0.00           O
ATOM   6049  C1*  U D  60    65.011 110.582 266.362  1.00  0.00           C
ATOM   6050  N1   U D  60    64.552 109.658 265.317  1.00  0.00           N
ATOM   6051  C2   U D  60    64.669 108.309 265.595  1.00  0.00           C
ATOM   6052  O2   U D  60    65.122 107.928 266.672  1.00  0.00           O
ATOM   6053  N3   U D  60    64.248 107.420 264.645  1.00  0.00           N
ATOM   6054  C4   U D  60    63.733 107.823 263.448  1.00  0.00           C
ATOM   6055  O4   U D  60    63.370 106.905 262.647  1.00  0.00           O
ATOM   6056  C5   U D  60    63.630 109.219 263.175  1.00  0.00           C
ATOM   6057  C6   U D  60    64.048 110.075 264.120  1.00  0.00           C
ATOM   6058  P    C D  61    67.166 113.681 268.876  1.00  0.00           P
ATOM   6059  O1P  C D  61    67.440 113.435 270.320  1.00  0.00           O
ATOM   6060  O2P  C D  61    65.985 114.558 268.642  1.00  0.00           O
ATOM   6061  O5*  C D  61    68.464 114.141 268.095  1.00  0.00           O
ATOM   6062  C5*  C D  61    69.765 113.519 268.358  1.00  0.00           C
ATOM   6063  C4*  C D  61    70.748 114.362 267.570  1.00  0.00           C
ATOM   6064  O4*  C D  61    70.782 113.923 266.233  1.00  0.00           O
ATOM   6065  C3*  C D  61    70.370 115.836 267.494  1.00  0.00           C
ATOM   6066  O3*  C D  61    70.740 116.571 268.654  1.00  0.00           O
ATOM   6067  C2*  C D  61    71.123 116.274 266.228  1.00  0.00           C
ATOM   6068  O2*  C D  61    72.468 116.511 266.627  1.00  0.00           O
ATOM   6069  C1*  C D  61    71.003 115.037 265.378  1.00  0.00           C
ATOM   6070  N1   C D  61    69.868 115.205 264.464  1.00  0.00           N
ATOM   6071  C2   C D  61    69.969 116.155 263.469  1.00  0.00           C
ATOM   6072  O2   C D  61    70.985 116.826 263.374  1.00  0.00           O
ATOM   6073  N3   C D  61    68.909 116.302 262.625  1.00  0.00           N
ATOM   6074  C4   C D  61    67.784 115.545 262.747  1.00  0.00           C
ATOM   6075  N4   C D  61    66.764 115.721 261.904  1.00  0.00           N
ATOM   6076  C5   C D  61    67.680 114.565 263.784  1.00  0.00           C
ATOM   6077  C6   C D  61    68.737 114.436 264.598  1.00  0.00           C
ATOM   6078  P    C D  62    70.417 118.127 268.851  1.00  0.00           P
ATOM   6079  O1P  C D  62    71.090 118.664 270.082  1.00  0.00           O
ATOM   6080  O2P  C D  62    68.944 118.202 268.984  1.00  0.00           O
ATOM   6081  O5*  C D  62    70.989 118.799 267.511  1.00  0.00           O
ATOM   6082  C5*  C D  62    72.234 119.534 267.609  1.00  0.00           C
ATOM   6083  C4*  C D  62    72.572 120.093 266.255  1.00  0.00           C
ATOM   6084  O4*  C D  62    72.142 119.245 265.200  1.00  0.00           O
ATOM   6085  C3*  C D  62    71.914 121.440 265.954  1.00  0.00           C
ATOM   6086  O3*  C D  62    72.567 122.561 266.580  1.00  0.00           O
ATOM   6087  C2*  C D  62    71.978 121.476 264.436  1.00  0.00           C
ATOM   6088  O2*  C D  62    73.280 121.896 264.087  1.00  0.00           O
ATOM   6089  C1*  C D  62    71.765 120.014 264.083  1.00  0.00           C
ATOM   6090  N1   C D  62    70.331 119.931 263.737  1.00  0.00           N
ATOM   6091  C2   C D  62    69.902 120.778 262.716  1.00  0.00           C
ATOM   6092  O2   C D  62    70.692 121.513 262.148  1.00  0.00           O
ATOM   6093  N3   C D  62    68.579 120.740 262.386  1.00  0.00           N
ATOM   6094  C4   C D  62    67.695 119.925 263.023  1.00  0.00           C
ATOM   6095  N4   C D  62    66.418 119.938 262.652  1.00  0.00           N
ATOM   6096  C5   C D  62    68.154 119.073 264.069  1.00  0.00           C
ATOM   6097  C6   C D  62    69.452 119.118 264.385  1.00  0.00           C
ATOM   6098  P    C D  63    71.684 123.352 267.696  1.00  0.00           P
ATOM   6099  O1P  C D  63    72.551 123.963 268.757  1.00  0.00           O
ATOM   6100  O2P  C D  63    70.826 122.284 268.266  1.00  0.00           O
ATOM   6101  O5*  C D  63    70.956 124.470 266.824  1.00  0.00           O
ATOM   6102  C5*  C D  63    71.698 125.657 266.459  1.00  0.00           C
ATOM   6103  C4*  C D  63    71.112 126.206 265.177  1.00  0.00           C
ATOM   6104  O4*  C D  63    70.737 125.127 264.326  1.00  0.00           O
ATOM   6105  C3*  C D  63    69.840 127.025 265.342  1.00  0.00           C
ATOM   6106  O3*  C D  63    70.056 128.381 265.749  1.00  0.00           O
ATOM   6107  C2*  C D  63    69.200 126.908 263.958  1.00  0.00           C
ATOM   6108  O2*  C D  63    69.857 127.880 263.132  1.00  0.00           O
ATOM   6109  C1*  C D  63    69.586 125.502 263.574  1.00  0.00           C
ATOM   6110  N1   C D  63    68.455 124.607 263.865  1.00  0.00           N
ATOM   6111  C2   C D  63    67.275 124.820 263.190  1.00  0.00           C
ATOM   6112  O2   C D  63    67.169 125.722 262.370  1.00  0.00           O
ATOM   6113  N3   C D  63    66.217 123.988 263.471  1.00  0.00           N
ATOM   6114  C4   C D  63    66.321 122.988 264.385  1.00  0.00           C
ATOM   6115  N4   C D  63    65.273 122.209 264.624  1.00  0.00           N
ATOM   6116  C5   C D  63    67.544 122.779 265.080  1.00  0.00           C
ATOM   6117  C6   C D  63    68.567 123.597 264.786  1.00  0.00           C
ATOM   6118  P    C D  64    69.204 128.940 267.008  1.00  0.00           P
ATOM   6119  O1P  C D  64    70.047 129.642 268.029  1.00  0.00           O
ATOM   6120  O2P  C D  64    68.604 127.700 267.568  1.00  0.00           O
ATOM   6121  O5*  C D  64    68.162 129.940 266.353  1.00  0.00           O
ATOM   6122  C5*  C D  64    68.436 130.581 265.072  1.00  0.00           C
ATOM   6123  C4*  C D  64    67.070 130.769 264.438  1.00  0.00           C
ATOM   6124  O4*  C D  64    66.726 129.605 263.693  1.00  0.00           O
ATOM   6125  C3*  C D  64    65.918 130.944 265.420  1.00  0.00           C
ATOM   6126  O3*  C D  64    65.755 132.273 265.952  1.00  0.00           O
ATOM   6127  C2*  C D  64    64.714 130.515 264.576  1.00  0.00           C
ATOM   6128  O2*  C D  64    64.326 131.617 263.784  1.00  0.00           O
ATOM   6129  C1*  C D  64    65.324 129.397 263.750  1.00  0.00           C
ATOM   6130  N1   C D  64    64.928 128.156 264.416  1.00  0.00           N
```

| | | | | | | | | | |
|---|---|---|---|---|---|---|---|---|---|
| ATOM | 6131 | C2 | C | D | 64 | 63.649 | 127.684 | 264.152 | 1.00 0.00 |
| ATOM | 6132 | O2 | C | D | 64 | 62.921 | 128.292 | 263.371 | 1.00 0.00 |
| ATOM | 6133 | N3 | C | D | 64 | 63.243 | 126.532 | 264.776 | 1.00 0.00 |
| ATOM | 6134 | C4 | C | D | 64 | 64.050 | 125.862 | 265.636 | 1.00 0.00 |
| ATOM | 6135 | N4 | C | D | 64 | 63.592 | 124.747 | 266.214 | 1.00 0.00 |
| ATOM | 6136 | C5 | C | D | 64 | 65.360 | 126.359 | 265.912 | 1.00 0.00 |
| ATOM | 6137 | C6 | C | D | 64 | 65.742 | 127.489 | 265.294 | 1.00 0.00 |
| ATOM | 6138 | P | G | D | 65 | 64.778 | 132.298 | 267.265 | 1.00 0.00 |
| ATOM | 6139 | O1P | G | D | 65 | 64.845 | 133.584 | 268.000 | 1.00 0.00 |
| ATOM | 6140 | O2P | G | D | 65 | 65.298 | 131.159 | 268.077 | 1.00 0.00 |
| ATOM | 6141 | O5* | G | D | 65 | 63.345 | 132.025 | 266.609 | 1.00 0.00 |
| ATOM | 6142 | C5* | G | D | 65 | 62.683 | 133.088 | 265.878 | 1.00 0.00 |
| ATOM | 6143 | C4* | G | D | 65 | 61.258 | 132.633 | 265.628 | 1.00 0.00 |
| ATOM | 6144 | O4* | G | D | 65 | 61.282 | 131.387 | 264.948 | 1.00 0.00 |
| ATOM | 6145 | C3* | G | D | 65 | 60.417 | 132.364 | 266.883 | 1.00 0.00 |
| ATOM | 6146 | O3* | G | D | 65 | 59.862 | 133.548 | 267.450 | 1.00 0.00 |
| ATOM | 6147 | C2* | G | D | 65 | 59.372 | 131.391 | 266.344 | 1.00 0.00 |
| ATOM | 6148 | O2* | G | D | 65 | 58.382 | 132.196 | 265.711 | 1.00 0.00 |
| ATOM | 6149 | C1* | G | D | 65 | 60.164 | 130.590 | 265.339 | 1.00 0.00 |
| ATOM | 6150 | N9 | G | D | 65 | 60.622 | 129.321 | 265.933 | 1.00 0.00 |
| ATOM | 6151 | C8 | G | D | 65 | 61.838 | 129.087 | 266.538 | 1.00 0.00 |
| ATOM | 6152 | N7 | G | D | 65 | 61.994 | 127.866 | 266.975 | 1.00 0.00 |
| ATOM | 6153 | C5 | G | D | 65 | 60.789 | 127.245 | 266.635 | 1.00 0.00 |
| ATOM | 6154 | C6 | G | D | 65 | 60.332 | 125.918 | 266.836 | 1.00 0.00 |
| ATOM | 6155 | O6 | G | D | 65 | 60.939 | 124.987 | 267.378 | 1.00 0.00 |
| ATOM | 6156 | N1 | G | D | 65 | 59.079 | 125.672 | 266.350 | 1.00 0.00 |
| ATOM | 6157 | C2 | G | D | 65 | 58.335 | 126.636 | 265.734 | 1.00 0.00 |
| ATOM | 6158 | N2 | G | D | 65 | 57.128 | 126.245 | 265.315 | 1.00 0.00 |
| ATOM | 6159 | N3 | G | D | 65 | 58.718 | 127.890 | 265.520 | 1.00 0.00 |
| ATOM | 6160 | C4 | G | D | 65 | 59.949 | 128.131 | 265.994 | 1.00 0.00 |
| ATOM | 6161 | P | U | D | 66 | 58.879 | 133.549 | 268.724 | 1.00 0.00 |
| ATOM | 6162 | O1P | U | D | 66 | 58.361 | 134.921 | 269.045 | 1.00 0.00 |
| ATOM | 6163 | O2P | U | D | 66 | 59.766 | 133.061 | 269.822 | 1.00 0.00 |
| ATOM | 6164 | O5* | U | D | 66 | 57.688 | 132.582 | 268.309 | 1.00 0.00 |
| ATOM | 6165 | C5* | U | D | 66 | 56.518 | 133.024 | 267.547 | 1.00 0.00 |
| ATOM | 6166 | C4* | U | D | 66 | 55.465 | 132.010 | 267.923 | 1.00 0.00 |
| ATOM | 6167 | O4* | U | D | 66 | 55.823 | 130.732 | 267.451 | 1.00 0.00 |
| ATOM | 6168 | C3* | U | D | 66 | 55.291 | 131.819 | 269.424 | 1.00 0.00 |
| ATOM | 6169 | O3* | U | D | 66 | 54.474 | 132.811 | 270.033 | 1.00 0.00 |
| ATOM | 6170 | C2* | U | D | 66 | 54.681 | 130.416 | 269.509 | 1.00 0.00 |
| ATOM | 6171 | O2* | U | D | 66 | 53.289 | 130.559 | 269.232 | 1.00 0.00 |
| ATOM | 6172 | C1* | U | D | 66 | 55.384 | 129.721 | 268.376 | 1.00 0.00 |
| ATOM | 6173 | N1 | U | D | 66 | 56.583 | 128.962 | 268.785 | 1.00 0.00 |
| ATOM | 6174 | C2 | U | D | 66 | 56.408 | 127.608 | 269.045 | 1.00 0.00 |
| ATOM | 6175 | O2 | U | D | 66 | 55.297 | 127.088 | 268.961 | 1.00 0.00 |
| ATOM | 6176 | N3 | U | D | 66 | 57.524 | 126.899 | 269.403 | 1.00 0.00 |
| ATOM | 6177 | C4 | U | D | 66 | 58.749 | 127.459 | 269.510 | 1.00 0.00 |
| ATOM | 6178 | O4 | U | D | 66 | 59.716 | 126.714 | 269.849 | 1.00 0.00 |
| ATOM | 6179 | C5 | U | D | 66 | 58.911 | 128.857 | 269.228 | 1.00 0.00 |
| ATOM | 6180 | C6 | U | D | 66 | 57.811 | 129.539 | 268.878 | 1.00 0.00 |
| ATOM | 6181 | P | C | D | 67 | 54.441 | 132.904 | 271.649 | 1.00 0.00 |
| ATOM | 6182 | O1P | C | D | 67 | 53.636 | 134.082 | 272.084 | 1.00 0.00 |
| ATOM | 6183 | O2P | C | D | 67 | 55.888 | 133.037 | 271.957 | 1.00 0.00 |
| ATOM | 6184 | O5* | C | D | 67 | 53.791 | 131.537 | 272.110 | 1.00 0.00 |
| ATOM | 6185 | C5* | C | D | 67 | 52.337 | 131.355 | 271.986 | 1.00 0.00 |
| ATOM | 6186 | C4* | C | D | 67 | 52.106 | 129.938 | 272.462 | 1.00 0.00 |
| ATOM | 6187 | O4* | C | D | 67 | 52.785 | 129.035 | 271.621 | 1.00 0.00 |
| ATOM | 6188 | C3* | C | D | 67 | 52.635 | 129.645 | 273.864 | 1.00 0.00 |
| ATOM | 6189 | O3* | C | D | 67 | 51.759 | 130.092 | 274.894 | 1.00 0.00 |
| ATOM | 6190 | C2* | C | D | 67 | 52.805 | 128.128 | 273.817 | 1.00 0.00 |
| ATOM | 6191 | O2* | C | D | 67 | 51.533 | 127.573 | 274.077 | 1.00 0.00 |
| ATOM | 6192 | C1* | C | D | 67 | 53.248 | 127.929 | 272.376 | 1.00 0.00 |
| ATOM | 6193 | N1 | C | D | 67 | 54.712 | 127.827 | 272.362 | 1.00 0.00 |
| ATOM | 6194 | C2 | C | D | 67 | 55.280 | 126.627 | 272.751 | 1.00 0.00 |
| ATOM | 6195 | O2 | C | D | 67 | 54.571 | 125.680 | 273.092 | 1.00 0.00 |
| ATOM | 6196 | N3 | C | D | 67 | 56.646 | 126.550 | 272.745 | 1.00 0.00 |
| ATOM | 6197 | C4 | C | D | 67 | 57.434 | 127.598 | 272.369 | 1.00 0.00 |
| ATOM | 6198 | N4 | C | D | 67 | 58.756 | 127.453 | 272.387 | 1.00 0.00 |
| ATOM | 6199 | C5 | C | D | 67 | 56.838 | 128.820 | 271.982 | 1.00 0.00 |
| ATOM | 6200 | C6 | C | D | 67 | 55.495 | 128.887 | 271.990 | 1.00 0.00 |
| ATOM | 6201 | P | G | D | 68 | 52.247 | 130.338 | 276.400 | 1.00 0.00 |
| ATOM | 6202 | O1P | G | D | 68 | 51.259 | 131.158 | 277.171 | 1.00 0.00 |
| ATOM | 6203 | O2P | G | D | 68 | 53.541 | 131.052 | 276.256 | 1.00 0.00 |
| ATOM | 6204 | O5* | G | D | 68 | 52.354 | 128.849 | 276.966 | 1.00 0.00 |
| ATOM | 6205 | C5* | G | D | 68 | 51.104 | 128.170 | 277.302 | 1.00 0.00 |
| ATOM | 6206 | C4* | G | D | 68 | 51.528 | 126.831 | 277.866 | 1.00 0.00 |
| ATOM | 6207 | O4* | G | D | 68 | 52.178 | 126.091 | 276.846 | 1.00 0.00 |
| ATOM | 6208 | C3* | G | D | 68 | 52.558 | 126.915 | 278.992 | 1.00 0.00 |
| ATOM | 6209 | O3* | G | D | 68 | 51.940 | 127.175 | 280.256 | 1.00 0.00 |
| ATOM | 6210 | C2* | G | D | 68 | 53.214 | 125.539 | 278.913 | 1.00 0.00 |
| ATOM | 6211 | O2* | G | D | 68 | 52.359 | 124.638 | 279.603 | 1.00 0.00 |
| ATOM | 6212 | C1* | G | D | 68 | 53.214 | 125.287 | 277.415 | 1.00 0.00 |
| ATOM | 6213 | N9 | G | D | 68 | 54.524 | 125.634 | 276.831 | 1.00 0.00 |
| ATOM | 6214 | C8 | G | D | 68 | 54.842 | 126.670 | 275.992 | 1.00 0.00 |
| ATOM | 6215 | N7 | G | D | 68 | 56.121 | 126.702 | 275.642 | 1.00 0.00 |
| ATOM | 6216 | C5 | G | D | 68 | 56.663 | 125.603 | 276.300 | 1.00 0.00 |
| ATOM | 6217 | C6 | G | D | 68 | 57.992 | 125.090 | 276.337 | 1.00 0.00 |

| | | | | | | | | | | |
|---|---|---|---|---|---|---|---|---|---|---|
| ATOM | 6218 | O6 | G | D | 68 | 59.008 | 125.513 | 275.769 | 1.00 | 0.00 | O |
| ATOM | 6219 | N1 | G | D | 68 | 58.115 | 123.975 | 277.117 | 1.00 | 0.00 | N |
| ATOM | 6220 | C2 | G | D | 68 | 57.096 | 123.403 | 277.799 | 1.00 | 0.00 | C |
| ATOM | 6221 | N2 | G | D | 68 | 57.423 | 122.318 | 278.507 | 1.00 | 0.00 | N |
| ATOM | 6222 | N3 | G | D | 68 | 55.836 | 123.840 | 277.797 | 1.00 | 0.00 | N |
| ATOM | 6223 | C4 | G | D | 68 | 55.705 | 124.946 | 277.030 | 1.00 | 0.00 | C |
| ATOM | 6224 | P | C | D | 69 | 52.734 | 127.345 | 281.641 | 1.00 | 0.00 | P |
| ATOM | 6225 | O1P | C | D | 69 | 51.837 | 127.159 | 282.815 | 1.00 | 0.00 | O |
| ATOM | 6226 | O2P | C | D | 69 | 53.293 | 128.721 | 281.572 | 1.00 | 0.00 | O |
| ATOM | 6227 | O5* | C | D | 69 | 53.823 | 126.181 | 281.571 | 1.00 | 0.00 | O |
| ATOM | 6228 | C5* | C | D | 69 | 53.475 | 124.845 | 282.030 | 1.00 | 0.00 | C |
| ATOM | 6229 | C4* | C | D | 69 | 54.799 | 124.204 | 282.409 | 1.00 | 0.00 | C |
| ATOM | 6230 | O4* | C | D | 69 | 55.586 | 124.042 | 281.246 | 1.00 | 0.00 | O |
| ATOM | 6231 | C3* | C | D | 69 | 55.670 | 125.013 | 283.367 | 1.00 | 0.00 | C |
| ATOM | 6232 | O3* | C | D | 69 | 55.285 | 124.893 | 284.746 | 1.00 | 0.00 | O |
| ATOM | 6233 | C2* | C | D | 69 | 57.048 | 124.446 | 283.075 | 1.00 | 0.00 | C |
| ATOM | 6234 | O2* | C | D | 69 | 57.178 | 123.233 | 283.800 | 1.00 | 0.00 | O |
| ATOM | 6235 | C1* | C | D | 69 | 56.968 | 124.181 | 281.577 | 1.00 | 0.00 | C |
| ATOM | 6236 | N1 | C | D | 69 | 57.621 | 125.309 | 280.882 | 1.00 | 0.00 | N |
| ATOM | 6237 | C2 | C | D | 69 | 58.978 | 125.224 | 280.676 | 1.00 | 0.00 | C |
| ATOM | 6238 | O2 | C | D | 69 | 59.615 | 124.241 | 281.055 | 1.00 | 0.00 | O |
| ATOM | 6239 | N3 | C | D | 69 | 59.593 | 126.260 | 280.038 | 1.00 | 0.00 | N |
| ATOM | 6240 | C4 | C | D | 69 | 58.901 | 127.356 | 279.617 | 1.00 | 0.00 | C |
| ATOM | 6241 | N4 | C | D | 69 | 59.564 | 128.343 | 278.993 | 1.00 | 0.00 | N |
| ATOM | 6242 | C5 | C | D | 69 | 57.498 | 127.432 | 279.834 | 1.00 | 0.00 | C |
| ATOM | 6243 | C6 | C | D | 69 | 56.913 | 126.405 | 280.466 | 1.00 | 0.00 | C |
| ATOM | 6244 | P | G | D | 70 | 55.420 | 126.191 | 285.704 | 1.00 | 0.00 | P |
| ATOM | 6245 | O1P | G | D | 70 | 54.339 | 126.262 | 286.733 | 1.00 | 0.00 | O |
| ATOM | 6246 | O2P | G | D | 70 | 55.343 | 127.315 | 284.739 | 1.00 | 0.00 | O |
| ATOM | 6247 | O5* | G | D | 70 | 56.839 | 125.955 | 286.408 | 1.00 | 0.00 | O |
| ATOM | 6248 | C5* | G | D | 70 | 57.256 | 124.570 | 286.593 | 1.00 | 0.00 | C |
| ATOM | 6249 | C4* | G | D | 70 | 58.764 | 124.568 | 286.631 | 1.00 | 0.00 | C |
| ATOM | 6250 | O4* | G | D | 70 | 59.296 | 124.274 | 285.341 | 1.00 | 0.00 | O |
| ATOM | 6251 | C3* | G | D | 70 | 59.392 | 125.916 | 286.998 | 1.00 | 0.00 | C |
| ATOM | 6252 | O3* | G | D | 70 | 59.391 | 126.162 | 288.401 | 1.00 | 0.00 | O |
| ATOM | 6253 | C2* | G | D | 70 | 60.791 | 125.787 | 286.402 | 1.00 | 0.00 | C |
| ATOM | 6254 | O2* | G | D | 70 | 61.582 | 125.052 | 287.323 | 1.00 | 0.00 | O |
| ATOM | 6255 | C1* | G | D | 70 | 60.516 | 124.987 | 285.140 | 1.00 | 0.00 | C |
| ATOM | 6256 | N9 | G | D | 70 | 60.443 | 125.921 | 284.009 | 1.00 | 0.00 | N |
| ATOM | 6257 | C8 | G | D | 70 | 59.347 | 126.444 | 283.393 | 1.00 | 0.00 | C |
| ATOM | 6258 | N7 | G | D | 70 | 59.624 | 127.258 | 282.407 | 1.00 | 0.00 | N |
| ATOM | 6259 | C5 | G | D | 70 | 61.019 | 127.279 | 282.372 | 1.00 | 0.00 | C |
| ATOM | 6260 | C6 | G | D | 70 | 61.934 | 127.970 | 281.535 | 1.00 | 0.00 | C |
| ATOM | 6261 | O6 | G | D | 70 | 61.655 | 128.739 | 280.612 | 1.00 | 0.00 | O |
| ATOM | 6262 | N1 | G | D | 70 | 63.248 | 127.729 | 281.810 | 1.00 | 0.00 | N |
| ATOM | 6263 | C2 | G | D | 70 | 63.645 | 126.893 | 282.812 | 1.00 | 0.00 | C |
| ATOM | 6264 | N2 | G | D | 70 | 64.959 | 126.763 | 282.965 | 1.00 | 0.00 | N |
| ATOM | 6265 | N3 | G | D | 70 | 62.836 | 126.227 | 283.631 | 1.00 | 0.00 | N |
| ATOM | 6266 | C4 | G | D | 70 | 61.541 | 126.460 | 283.352 | 1.00 | 0.00 | C |
| ATOM | 6267 | P | G | D | 71 | 60.054 | 127.505 | 289.012 | 1.00 | 0.00 | P |
| ATOM | 6268 | O1P | G | D | 71 | 59.786 | 127.593 | 290.482 | 1.00 | 0.00 | O |
| ATOM | 6269 | O2P | G | D | 71 | 59.371 | 128.585 | 288.248 | 1.00 | 0.00 | O |
| ATOM | 6270 | O5* | G | D | 71 | 61.593 | 127.338 | 288.673 | 1.00 | 0.00 | O |
| ATOM | 6271 | C5* | G | D | 71 | 62.552 | 126.705 | 289.558 | 1.00 | 0.00 | C |
| ATOM | 6272 | C4* | G | D | 71 | 63.913 | 127.152 | 289.044 | 1.00 | 0.00 | C |
| ATOM | 6273 | O4* | G | D | 71 | 63.955 | 126.965 | 287.632 | 1.00 | 0.00 | O |
| ATOM | 6274 | C3* | G | D | 71 | 64.239 | 128.616 | 289.241 | 1.00 | 0.00 | C |
| ATOM | 6275 | O3* | G | D | 71 | 64.742 | 128.943 | 290.539 | 1.00 | 0.00 | O |
| ATOM | 6276 | C2* | G | D | 71 | 65.282 | 128.857 | 288.139 | 1.00 | 0.00 | C |
| ATOM | 6277 | O2* | G | D | 71 | 66.520 | 128.390 | 288.656 | 1.00 | 0.00 | O |
| ATOM | 6278 | C1* | G | D | 71 | 64.758 | 127.975 | 287.036 | 1.00 | 0.00 | C |
| ATOM | 6279 | N9 | G | D | 71 | 63.974 | 128.755 | 286.060 | 1.00 | 0.00 | N |
| ATOM | 6280 | C8 | G | D | 71 | 62.608 | 128.687 | 285.853 | 1.00 | 0.00 | C |
| ATOM | 6281 | N7 | G | D | 71 | 62.182 | 129.491 | 284.915 | 1.00 | 0.00 | N |
| ATOM | 6282 | C5 | G | D | 71 | 63.338 | 130.121 | 284.464 | 1.00 | 0.00 | C |
| ATOM | 6283 | C6 | G | D | 71 | 63.541 | 131.104 | 283.455 | 1.00 | 0.00 | C |
| ATOM | 6284 | O6 | G | D | 71 | 62.689 | 131.621 | 282.736 | 1.00 | 0.00 | O |
| ATOM | 6285 | N1 | G | D | 71 | 64.850 | 131.489 | 283.298 | 1.00 | 0.00 | N |
| ATOM | 6286 | C2 | G | D | 71 | 65.860 | 130.969 | 284.052 | 1.00 | 0.00 | C |
| ATOM | 6287 | N2 | G | D | 71 | 67.078 | 131.446 | 283.784 | 1.00 | 0.00 | N |
| ATOM | 6288 | N3 | G | D | 71 | 65.725 | 130.056 | 285.008 | 1.00 | 0.00 | N |
| ATOM | 6289 | C4 | G | D | 71 | 64.444 | 129.676 | 285.157 | 1.00 | 0.00 | C |
| ATOM | 6290 | P | A | D | 72 | 65.171 | 130.470 | 290.847 | 1.00 | 0.00 | P |
| ATOM | 6291 | O1P | A | D | 72 | 65.522 | 130.679 | 292.286 | 1.00 | 0.00 | O |
| ATOM | 6292 | O2P | A | D | 72 | 63.946 | 131.225 | 290.454 | 1.00 | 0.00 | O |
| ATOM | 6293 | O5* | A | D | 72 | 66.412 | 130.706 | 289.879 | 1.00 | 0.00 | O |
| ATOM | 6294 | C5* | A | D | 72 | 67.734 | 131.016 | 290.394 | 1.00 | 0.00 | C |
| ATOM | 6295 | C4* | A | D | 72 | 68.440 | 131.845 | 289.349 | 1.00 | 0.00 | C |
| ATOM | 6296 | O4* | A | D | 72 | 68.019 | 131.461 | 288.050 | 1.00 | 0.00 | O |
| ATOM | 6297 | C3* | A | D | 72 | 68.158 | 133.341 | 289.400 | 1.00 | 0.00 | C |
| ATOM | 6298 | O3* | A | D | 72 | 68.943 | 134.051 | 290.377 | 1.00 | 0.00 | O |
| ATOM | 6299 | C2* | A | D | 72 | 68.484 | 133.790 | 287.971 | 1.00 | 0.00 | C |
| ATOM | 6300 | O2* | A | D | 72 | 69.902 | 133.931 | 287.878 | 1.00 | 0.00 | O |
| ATOM | 6301 | C1* | A | D | 72 | 68.010 | 132.594 | 287.175 | 1.00 | 0.00 | C |
| ATOM | 6302 | N9 | A | D | 72 | 66.658 | 132.842 | 286.643 | 1.00 | 0.00 | N |
| ATOM | 6303 | C8 | A | D | 72 | 65.486 | 132.207 | 287.010 | 1.00 | 0.00 | C |
| ATOM | 6304 | N7 | A | D | 72 | 64.435 | 132.641 | 286.354 | 1.00 | 0.00 | N |

| | | | | | | | | | |
|---|---|---|---|---|---|---|---|---|---|
| ATOM | 6305 | C5 | A D | 72 | 64.954 | 133.613 | 285.496 | 1.00 | 0.00 | C |
| ATOM | 6306 | C6 | A D | 72 | 64.320 | 134.434 | 284.546 | 1.00 | 0.00 | C |
| ATOM | 6307 | N6 | A D | 72 | 63.029 | 134.416 | 284.280 | 1.00 | 0.00 | N |
| ATOM | 6308 | N1 | A D | 72 | 65.147 | 135.295 | 283.873 | 1.00 | 0.00 | N |
| ATOM | 6309 | C2 | A D | 72 | 66.495 | 135.334 | 284.132 | 1.00 | 0.00 | C |
| ATOM | 6310 | N3 | A D | 72 | 67.142 | 134.582 | 285.021 | 1.00 | 0.00 | N |
| ATOM | 6311 | C4 | A D | 72 | 66.312 | 133.741 | 285.670 | 1.00 | 0.00 | C |
| ATOM | 6312 | P | G D | 73 | 69.333 | 135.677 | 290.822 | 1.00 | 0.00 | P |
| ATOM | 6313 | O1P | G D | 73 | 70.759 | 135.790 | 291.263 | 1.00 | 0.00 | O |
| ATOM | 6314 | O2P | G D | 73 | 68.379 | 135.698 | 291.962 | 1.00 | 0.00 | O |
| ATOM | 6315 | O5* | G D | 73 | 68.950 | 136.665 | 289.643 | 1.00 | 0.00 | O |
| ATOM | 6316 | C5* | G D | 73 | 69.832 | 137.771 | 289.332 | 1.00 | 0.00 | C |
| ATOM | 6317 | C4* | G D | 73 | 69.769 | 138.021 | 287.840 | 1.00 | 0.00 | C |
| ATOM | 6318 | O4* | G D | 73 | 68.951 | 137.019 | 287.228 | 1.00 | 0.00 | O |
| ATOM | 6319 | C3* | G D | 73 | 69.114 | 139.343 | 287.434 | 1.00 | 0.00 | C |
| ATOM | 6320 | O3* | G D | 73 | 69.998 | 140.465 | 287.507 | 1.00 | 0.00 | O |
| ATOM | 6321 | C2* | G D | 73 | 68.659 | 139.028 | 286.011 | 1.00 | 0.00 | C |
| ATOM | 6322 | O2* | G D | 73 | 69.802 | 139.198 | 285.177 | 1.00 | 0.00 | O |
| ATOM | 6323 | C1* | G D | 73 | 68.266 | 137.568 | 286.112 | 1.00 | 0.00 | C |
| ATOM | 6324 | N9 | G D | 73 | 66.793 | 137.496 | 286.247 | 1.00 | 0.00 | N |
| ATOM | 6325 | C8 | G D | 73 | 66.056 | 136.813 | 287.174 | 1.00 | 0.00 | C |
| ATOM | 6326 | N7 | G D | 73 | 64.763 | 136.951 | 287.040 | 1.00 | 0.00 | N |
| ATOM | 6327 | C5 | G D | 73 | 64.637 | 137.796 | 285.935 | 1.00 | 0.00 | C |
| ATOM | 6328 | C6 | G D | 73 | 63.490 | 138.320 | 285.281 | 1.00 | 0.00 | C |
| ATOM | 6329 | O6 | G D | 73 | 62.297 | 138.138 | 285.572 | 1.00 | 0.00 | O |
| ATOM | 6330 | N1 | G D | 73 | 63.769 | 139.132 | 284.211 | 1.00 | 0.00 | N |
| ATOM | 6331 | C2 | G D | 73 | 65.040 | 139.396 | 283.818 | 1.00 | 0.00 | C |
| ATOM | 6332 | N2 | G D | 73 | 65.143 | 140.206 | 282.751 | 1.00 | 0.00 | N |
| ATOM | 6333 | N3 | G D | 73 | 66.153 | 138.938 | 284.384 | 1.00 | 0.00 | N |
| ATOM | 6334 | C4 | G D | 73 | 65.865 | 138.134 | 285.443 | 1.00 | 0.00 | C |
| ATOM | 6335 | P | C D | 74 | 69.397 | 141.857 | 287.531 | 1.00 | 0.00 | P |
| ATOM | 6336 | O1P | C D | 74 | 70.494 | 142.901 | 287.693 | 1.00 | 0.00 | O |
| ATOM | 6337 | O2P | C D | 74 | 68.486 | 141.823 | 288.703 | 1.00 | 0.00 | O |
| ATOM | 6338 | O5* | C D | 74 | 68.544 | 141.891 | 286.200 | 1.00 | 0.00 | O |
| ATOM | 6339 | C5* | C D | 74 | 69.093 | 141.557 | 284.896 | 1.00 | 0.00 | C |
| ATOM | 6340 | C4* | C D | 74 | 68.140 | 142.125 | 283.870 | 1.00 | 0.00 | C |
| ATOM | 6341 | O4* | C D | 74 | 66.850 | 141.549 | 284.020 | 1.00 | 0.00 | O |
| ATOM | 6342 | C3* | C D | 74 | 67.899 | 143.626 | 284.010 | 1.00 | 0.00 | C |
| ATOM | 6343 | O3* | C D | 74 | 68.954 | 144.417 | 283.463 | 1.00 | 0.00 | O |
| ATOM | 6344 | C2* | C D | 74 | 66.562 | 143.767 | 283.263 | 1.00 | 0.00 | C |
| ATOM | 6345 | O2* | C D | 74 | 66.925 | 143.523 | 281.873 | 1.00 | 0.00 | O |
| ATOM | 6346 | C1* | C D | 74 | 65.832 | 142.554 | 283.748 | 1.00 | 0.00 | C |
| ATOM | 6347 | N1 | C D | 74 | 65.076 | 142.747 | 284.981 | 1.00 | 0.00 | N |
| ATOM | 6348 | C2 | C D | 74 | 63.925 | 143.508 | 284.949 | 1.00 | 0.00 | C |
| ATOM | 6349 | O2 | C D | 74 | 63.547 | 144.011 | 283.908 | 1.00 | 0.00 | O |
| ATOM | 6350 | N3 | C D | 74 | 63.217 | 143.663 | 286.121 | 1.00 | 0.00 | N |
| ATOM | 6351 | C4 | C D | 74 | 63.630 | 143.105 | 287.281 | 1.00 | 0.00 | C |
| ATOM | 6352 | N4 | C D | 74 | 62.914 | 143.288 | 288.393 | 1.00 | 0.00 | N |
| ATOM | 6353 | C5 | C D | 74 | 64.806 | 142.328 | 287.299 | 1.00 | 0.00 | C |
| ATOM | 6354 | C6 | C D | 74 | 65.492 | 142.175 | 286.157 | 1.00 | 0.00 | C |
| ATOM | 6355 | P | C D | 75 | 69.496 | 145.448 | 284.591 | 1.00 | 0.00 | P |
| ATOM | 6356 | O1P | C D | 75 | 70.942 | 145.572 | 284.191 | 1.00 | 0.00 | O |
| ATOM | 6357 | O2P | C D | 75 | 69.237 | 145.000 | 286.010 | 1.00 | 0.00 | O |
| ATOM | 6358 | O5* | C D | 75 | 68.617 | 146.796 | 284.396 | 1.00 | 0.00 | O |
| ATOM | 6359 | C5* | C D | 75 | 68.426 | 147.016 | 282.954 | 1.00 | 0.00 | C |
| ATOM | 6360 | C4* | C D | 75 | 67.054 | 147.644 | 282.825 | 1.00 | 0.00 | C |
| ATOM | 6361 | O4* | C D | 75 | 66.046 | 146.789 | 283.325 | 1.00 | 0.00 | O |
| ATOM | 6362 | C3* | C D | 75 | 66.884 | 148.930 | 283.621 | 1.00 | 0.00 | C |
| ATOM | 6363 | O3* | C D | 75 | 67.555 | 150.024 | 283.019 | 1.00 | 0.00 | O |
| ATOM | 6364 | C2* | C D | 75 | 65.372 | 149.044 | 283.661 | 1.00 | 0.00 | C |
| ATOM | 6365 | O2* | C D | 75 | 64.981 | 149.482 | 282.359 | 1.00 | 0.00 | O |
| ATOM | 6366 | C1* | C D | 75 | 64.977 | 147.579 | 283.820 | 1.00 | 0.00 | C |
| ATOM | 6367 | N1 | C D | 75 | 64.673 | 147.342 | 285.241 | 1.00 | 0.00 | N |
| ATOM | 6368 | C2 | C D | 75 | 63.541 | 148.018 | 285.710 | 1.00 | 0.00 | C |
| ATOM | 6369 | O2 | C D | 75 | 62.902 | 148.731 | 284.943 | 1.00 | 0.00 | O |
| ATOM | 6370 | N3 | C D | 75 | 63.200 | 147.844 | 287.015 | 1.00 | 0.00 | N |
| ATOM | 6371 | C4 | C D | 75 | 63.920 | 147.051 | 287.855 | 1.00 | 0.00 | C |
| ATOM | 6372 | N4 | C D | 75 | 63.526 | 146.926 | 289.114 | 1.00 | 0.00 | N |
| ATOM | 6373 | C5 | C D | 75 | 65.061 | 146.365 | 287.360 | 1.00 | 0.00 | C |
| ATOM | 6374 | C6 | C D | 75 | 65.384 | 146.546 | 286.063 | 1.00 | 0.00 | C |
| ATOM | 6375 | P | A D | 76 | 67.857 | 150.426 | 284.439 | 1.00 | 0.00 | P |
| ATOM | 6376 | O1P | A D | 76 | 67.773 | 151.801 | 283.916 | 1.00 | 0.00 | O |
| ATOM | 6377 | O2P | A D | 76 | 69.187 | 149.823 | 284.680 | 1.00 | 0.00 | O |
| ATOM | 6378 | O5* | A D | 76 | 66.954 | 150.120 | 285.725 | 1.00 | 0.00 | O |
| ATOM | 6379 | C5* | A D | 76 | 65.574 | 150.522 | 285.554 | 1.00 | 0.00 | C |
| ATOM | 6380 | C4* | A D | 76 | 64.966 | 150.526 | 286.920 | 1.00 | 0.00 | C |
| ATOM | 6381 | O4* | A D | 76 | 65.753 | 149.779 | 287.816 | 1.00 | 0.00 | O |
| ATOM | 6382 | C3* | A D | 76 | 64.683 | 151.858 | 287.583 | 1.00 | 0.00 | C |
| ATOM | 6383 | O3* | A D | 76 | 63.361 | 151.932 | 288.126 | 1.00 | 0.00 | O |
| ATOM | 6384 | C2* | A D | 76 | 65.756 | 151.952 | 288.670 | 1.00 | 0.00 | C |
| ATOM | 6385 | O2* | A D | 76 | 65.230 | 152.784 | 289.690 | 1.00 | 0.00 | O |
| ATOM | 6386 | C1* | A D | 76 | 65.882 | 150.503 | 289.061 | 1.00 | 0.00 | C |
| ATOM | 6387 | N9 | A D | 76 | 67.203 | 150.222 | 289.637 | 1.00 | 0.00 | N |
| ATOM | 6388 | C8 | A D | 76 | 68.295 | 149.703 | 288.994 | 1.00 | 0.00 | C |
| ATOM | 6389 | N7 | A D | 76 | 69.347 | 149.564 | 289.760 | 1.00 | 0.00 | N |
| ATOM | 6390 | C5 | A D | 76 | 68.905 | 150.029 | 290.999 | 1.00 | 0.00 | C |
| ATOM | 6391 | C6 | A D | 76 | 69.566 | 150.131 | 292.249 | 1.00 | 0.00 | C |

| | | | | | | | | | | |
|---|---|---|---|---|---|---|---|---|---|---|
| ATOM | 6392 | N6 | A | D | 76 | 70.744 | 149.807 | 292.472 | 1.00 | 0.00 | N |
| ATOM | 6393 | N1 | A | D | 76 | 68.794 | 150.641 | 293.262 | 1.00 | 0.00 | N |
| ATOM | 6394 | C2 | A | D | 76 | 67.504 | 151.005 | 293.064 | 1.00 | 0.00 | C |
| ATOM | 6395 | N3 | A | D | 76 | 66.839 | 150.926 | 291.914 | 1.00 | 0.00 | N |
| ATOM | 6396 | C4 | A | D | 76 | 67.594 | 150.427 | 290.927 | 1.00 | 0.00 | C |
| TER | 6397 | | A | D | 76 | | | | | | |
| ATOM | 6398 | P | U | 1 | 1 | 9.248 | 97.344 | 283.458 | 1.00 | 0.00 | P |
| ATOM | 6399 | O1P | U | 1 | 1 | 8.764 | 96.486 | 282.352 | 1.00 | 0.00 | O |
| ATOM | 6400 | O2P | U | 1 | 1 | 9.069 | 96.805 | 284.825 | 1.00 | 0.00 | O |
| ATOM | 6401 | O5* | U | 1 | 1 | 8.563 | 98.786 | 283.356 | 1.00 | 0.00 | O |
| ATOM | 6402 | C5* | U | 1 | 1 | 8.892 | 99.785 | 284.340 | 1.00 | 0.00 | C |
| ATOM | 6403 | C4* | U | 1 | 1 | 8.176 | 101.082 | 284.019 | 1.00 | 0.00 | C |
| ATOM | 6404 | O4* | U | 1 | 1 | 8.690 | 101.605 | 282.760 | 1.00 | 0.00 | O |
| ATOM | 6405 | C3* | U | 1 | 1 | 6.669 | 100.973 | 283.785 | 1.00 | 0.00 | C |
| ATOM | 6406 | O3* | U | 1 | 1 | 5.945 | 100.960 | 285.007 | 1.00 | 0.00 | O |
| ATOM | 6407 | C2* | U | 1 | 1 | 6.386 | 102.217 | 282.931 | 1.00 | 0.00 | C |
| ATOM | 6408 | O2* | U | 1 | 1 | 6.374 | 103.379 | 283.714 | 1.00 | 0.00 | O |
| ATOM | 6409 | C1* | U | 1 | 1 | 7.645 | 102.259 | 282.058 | 1.00 | 0.00 | C |
| ATOM | 6410 | N1 | U | 1 | 1 | 7.447 | 101.562 | 280.757 | 1.00 | 0.00 | N |
| ATOM | 6411 | C2 | U | 1 | 1 | 6.790 | 102.256 | 279.768 | 1.00 | 0.00 | C |
| ATOM | 6412 | O2 | U | 1 | 1 | 6.376 | 103.392 | 279.922 | 1.00 | 0.00 | O |
| ATOM | 6413 | N3 | U | 1 | 1 | 6.626 | 101.579 | 278.577 | 1.00 | 0.00 | N |
| ATOM | 6414 | C4 | U | 1 | 1 | 7.053 | 100.298 | 278.297 | 1.00 | 0.00 | C |
| ATOM | 6415 | O4 | U | 1 | 1 | 6.848 | 99.795 | 277.191 | 1.00 | 0.00 | O |
| ATOM | 6416 | C5 | U | 1 | 1 | 7.732 | 99.650 | 279.395 | 1.00 | 0.00 | C |
| ATOM | 6417 | C6 | U | 1 | 1 | 7.906 | 100.286 | 280.566 | 1.00 | 0.00 | C |
| ATOM | 6418 | P | U | 1 | 2 | 4.601 | 100.397 | 285.104 | 1.00 | 0.00 | P |
| ATOM | 6419 | O1P | U | 1 | 2 | 4.143 | 100.343 | 286.511 | 1.00 | 0.00 | O |
| ATOM | 6420 | O2P | U | 1 | 2 | 4.691 | 99.097 | 284.400 | 1.00 | 0.00 | O |
| ATOM | 6421 | O5* | U | 1 | 2 | 3.664 | 101.392 | 284.273 | 1.00 | 0.00 | O |
| ATOM | 6422 | C5* | U | 1 | 2 | 3.435 | 102.720 | 284.779 | 1.00 | 0.00 | C |
| ATOM | 6423 | C4* | U | 1 | 2 | 2.570 | 103.502 | 283.809 | 1.00 | 0.00 | C |
| ATOM | 6424 | O4* | U | 1 | 2 | 3.309 | 103.691 | 282.568 | 1.00 | 0.00 | O |
| ATOM | 6425 | C3* | U | 1 | 2 | 1.276 | 102.817 | 283.368 | 1.00 | 0.00 | C |
| ATOM | 6426 | O3* | U | 1 | 2 | 0.237 | 102.990 | 284.321 | 1.00 | 0.00 | O |
| ATOM | 6427 | C2* | U | 1 | 2 | 0.987 | 103.511 | 282.030 | 1.00 | 0.00 | C |
| ATOM | 6428 | O2* | U | 1 | 2 | 0.465 | 104.798 | 282.226 | 1.00 | 0.00 | O |
| ATOM | 6429 | C1* | U | 1 | 2 | 2.407 | 103.666 | 281.474 | 1.00 | 0.00 | C |
| ATOM | 6430 | N1 | U | 1 | 2 | 2.784 | 102.535 | 280.581 | 1.00 | 0.00 | N |
| ATOM | 6431 | C2 | U | 1 | 2 | 2.319 | 102.575 | 279.288 | 1.00 | 0.00 | C |
| ATOM | 6432 | O2 | U | 1 | 2 | 1.625 | 103.483 | 278.862 | 1.00 | 0.00 | O |
| ATOM | 6433 | N3 | U | 1 | 2 | 2.690 | 101.512 | 278.491 | 1.00 | 0.00 | N |
| ATOM | 6434 | C4 | U | 1 | 2 | 3.468 | 100.437 | 278.868 | 1.00 | 0.00 | C |
| ATOM | 6435 | O4 | U | 1 | 2 | 3.734 | 99.542 | 278.063 | 1.00 | 0.00 | O |
| ATOM | 6436 | C5 | U | 1 | 2 | 3.908 | 100.482 | 280.243 | 1.00 | 0.00 | C |
| ATOM | 6437 | C6 | U | 1 | 2 | 3.562 | 101.508 | 281.041 | 1.00 | 0.00 | C |
| ATOM | 6438 | P | U | 1 | 3 | -0.903 | 102.079 | 284.397 | 1.00 | 0.00 | P |
| ATOM | 6439 | O1P | U | 1 | 3 | -1.744 | 102.370 | 285.578 | 1.00 | 0.00 | O |
| ATOM | 6440 | O2P | U | 1 | 3 | -0.302 | 100.727 | 284.343 | 1.00 | 0.00 | O |
| ATOM | 6441 | O5* | U | 1 | 3 | -1.745 | 102.343 | 283.061 | 1.00 | 0.00 | O |
| ATOM | 6442 | C5* | U | 1 | 3 | -2.421 | 103.605 | 282.901 | 1.00 | 0.00 | C |
| ATOM | 6443 | C4* | U | 1 | 3 | -3.104 | 103.659 | 281.550 | 1.00 | 0.00 | C |
| ATOM | 6444 | O4* | U | 1 | 3 | -2.086 | 103.639 | 280.506 | 1.00 | 0.00 | O |
| ATOM | 6445 | C3* | U | 1 | 3 | -4.004 | 102.471 | 281.209 | 1.00 | 0.00 | C |
| ATOM | 6446 | O3* | U | 1 | 3 | -5.295 | 102.604 | 281.785 | 1.00 | 0.00 | O |
| ATOM | 6447 | C2* | U | 1 | 3 | -4.022 | 102.512 | 279.674 | 1.00 | 0.00 | C |
| ATOM | 6448 | O2* | U | 1 | 3 | -4.863 | 103.530 | 279.203 | 1.00 | 0.00 | O |
| ATOM | 6449 | C1* | U | 1 | 3 | -2.578 | 102.930 | 279.380 | 1.00 | 0.00 | C |
| ATOM | 6450 | N1 | U | 1 | 3 | -1.693 | 101.756 | 279.141 | 1.00 | 0.00 | N |
| ATOM | 6451 | C2 | U | 1 | 3 | -1.736 | 101.184 | 277.893 | 1.00 | 0.00 | C |
| ATOM | 6452 | O2 | U | 1 | 3 | -2.457 | 101.595 | 277.000 | 1.00 | 0.00 | O |
| ATOM | 6453 | N3 | U | 1 | 3 | -0.902 | 100.100 | 277.708 | 1.00 | 0.00 | N |
| ATOM | 6454 | C4 | U | 1 | 3 | -0.050 | 99.553 | 278.646 | 1.00 | 0.00 | C |
| ATOM | 6455 | O4 | U | 1 | 3 | 0.652 | 98.579 | 278.364 | 1.00 | 0.00 | O |
| ATOM | 6456 | C5 | U | 1 | 3 | -0.074 | 100.221 | 279.925 | 1.00 | 0.00 | C |
| ATOM | 6457 | C6 | U | 1 | 3 | -0.876 | 101.280 | 280.133 | 1.00 | 0.00 | C |
| ATOM | 6458 | P | U | 1 | 4 | -6.296 | 102.388 | 282.881 | 1.00 | 0.00 | P |
| ATOM | 6459 | O1P | U | 1 | 4 | -5.389 | 101.922 | 283.952 | 1.00 | 0.00 | O |
| ATOM | 6460 | O2P | U | 1 | 4 | -6.993 | 101.331 | 282.113 | 1.00 | 0.00 | O |
| ATOM | 6461 | O5* | U | 1 | 4 | -7.372 | 103.403 | 283.492 | 1.00 | 0.00 | O |
| ATOM | 6462 | C5* | U | 1 | 4 | -6.912 | 104.515 | 284.283 | 1.00 | 0.00 | C |
| ATOM | 6463 | C4* | U | 1 | 4 | -8.094 | 105.241 | 284.892 | 1.00 | 0.00 | C |
| ATOM | 6464 | O4* | U | 1 | 4 | -8.519 | 106.297 | 283.982 | 1.00 | 0.00 | O |
| ATOM | 6465 | C3* | U | 1 | 4 | -9.356 | 104.403 | 285.101 | 1.00 | 0.00 | C |
| ATOM | 6466 | O3* | U | 1 | 4 | -9.295 | 103.647 | 286.301 | 1.00 | 0.00 | O |
| ATOM | 6467 | C2* | U | 1 | 4 | -10.453 | 105.477 | 285.122 | 1.00 | 0.00 | C |
| ATOM | 6468 | O2* | U | 1 | 4 | -10.473 | 106.160 | 286.345 | 1.00 | 0.00 | O |
| ATOM | 6469 | C1* | U | 1 | 4 | -9.928 | 106.447 | 284.059 | 1.00 | 0.00 | C |
| ATOM | 6470 | N1 | U | 1 | 4 | -10.502 | 106.167 | 282.713 | 1.00 | 0.00 | N |
| ATOM | 6471 | C2 | U | 1 | 4 | -11.767 | 106.643 | 282.460 | 1.00 | 0.00 | C |
| ATOM | 6472 | O2 | U | 1 | 4 | -12.413 | 107.269 | 283.282 | 1.00 | 0.00 | O |
| ATOM | 6473 | N3 | U | 1 | 4 | -12.265 | 106.365 | 281.204 | 1.00 | 0.00 | N |
| ATOM | 6474 | C4 | U | 1 | 4 | -11.621 | 105.668 | 280.202 | 1.00 | 0.00 | C |
| ATOM | 6475 | O4 | U | 1 | 4 | -12.170 | 105.481 | 279.115 | 1.00 | 0.00 | O |
| ATOM | 6476 | C5 | U | 1 | 4 | -10.299 | 105.209 | 280.561 | 1.00 | 0.00 | C |
| ATOM | 6477 | C6 | U | 1 | 4 | -9.789 | 105.466 | 281.777 | 1.00 | 0.00 | C |
| ATOM | 6478 | P | U | 1 | 5 | -10.100 | 102.445 | 286.499 | 1.00 | 0.00 | P |

```
ATOM   6479  O1P   U 1    5     -9.722 101.746 287.749  1.00  0.00           O
ATOM   6480  O2P   U 1    5     -9.931 101.672 285.246  1.00  0.00           O
ATOM   6481  O5*   U 1    5    -11.611 102.960 286.610  1.00  0.00           O
ATOM   6482  C5*   U 1    5    -12.000 103.736 287.759  1.00  0.00           C
ATOM   6483  C4*   U 1    5    -13.449 104.163 287.628  1.00  0.00           C
ATOM   6484  O4*   U 1    5    -13.571 105.073 286.497  1.00  0.00           O
ATOM   6485  C3*   U 1    5    -14.447 103.048 287.315  1.00  0.00           C
ATOM   6486  O3*   U 1    5    -14.836 102.343 288.485  1.00  0.00           O
ATOM   6487  C2*   U 1    5    -15.602 103.824 286.668  1.00  0.00           C
ATOM   6488  O2*   U 1    5    -16.365 104.498 287.633  1.00  0.00           O
ATOM   6489  C1*   U 1    5    -14.829 104.879 285.870  1.00  0.00           C
ATOM   6490  N1    U 1    5    -14.590 104.451 284.463  1.00  0.00           N
ATOM   6491  C2    U 1    5    -15.630 104.604 283.576  1.00  0.00           C
ATOM   6492  O2    U 1    5    -16.711 105.065 283.898  1.00  0.00           O
ATOM   6493  N3    U 1    5    -15.371 104.199 282.284  1.00  0.00           N
ATOM   6494  C4    U 1    5    -14.189 103.665 281.813  1.00  0.00           C
ATOM   6495  O4    U 1    5    -14.076 103.337 280.630  1.00  0.00           O
ATOM   6496  C5    U 1    5    -13.157 103.542 282.816  1.00  0.00           C
ATOM   6497  C6    U 1    5    -13.382 103.931 284.083  1.00  0.00           C
ATOM   6498  P     U 1    6    -15.369 100.984 288.429  1.00  0.00           P
ATOM   6499  O1P   U 1    6    -15.528 100.415 289.786  1.00  0.00           O
ATOM   6500  O2P   U 1    6    -14.449 100.261 287.523  1.00  0.00           O
ATOM   6501  O5*   U 1    6    -16.805 101.121 287.735  1.00  0.00           O
ATOM   6502  C5*   U 1    6    -17.862 101.795 288.445  1.00  0.00           C
ATOM   6503  C4*   U 1    6    -19.107 101.857 287.584  1.00  0.00           C
ATOM   6504  O4*   U 1    6    -18.835 102.696 286.424  1.00  0.00           O
ATOM   6505  C3*   U 1    6    -19.567 100.531 286.979  1.00  0.00           C
ATOM   6506  O3*   U 1    6    -20.332  99.767 287.901  1.00  0.00           O
ATOM   6507  C2*   U 1    6    -20.380 100.997 285.763  1.00  0.00           C
ATOM   6508  O2*   U 1    6    -21.639 101.479 286.148  1.00  0.00           O
ATOM   6509  C1*   U 1    6    -19.546 102.197 285.302  1.00  0.00           C
ATOM   6510  N1    U 1    6    -18.560 101.821 284.250  1.00  0.00           N
ATOM   6511  C2    U 1    6    -19.030 101.708 282.965  1.00  0.00           C
ATOM   6512  O2    U 1    6    -20.196 101.898 282.666  1.00  0.00           O
ATOM   6513  N3    U 1    6    -18.088 101.360 282.017  1.00  0.00           N
ATOM   6514  C4    U 1    6    -16.748 101.121 282.244  1.00  0.00           C
ATOM   6515  O4    U 1    6    -15.999 100.816 281.314  1.00  0.00           O
ATOM   6516  C5    U 1    6    -16.349 101.265 283.624  1.00  0.00           C
ATOM   6517  C6    U 1    6    -17.245 101.603 284.567  1.00  0.00           C
TER    6518        U 1    6
ATOM   6519  CA  VAL E    7    -13.818  20.636 309.201  1.00  0.00           C
ATOM   6520  CA  LYS E    8    -11.691  21.790 312.175  1.00  0.00           C
ATOM   6521  CA  GLU E    9     -8.177  21.652 313.730  1.00  0.00           C
ATOM   6522  CA  LEU E   10     -6.126  23.223 316.528  1.00  0.00           C
ATOM   6523  CA  LEU E   11     -2.721  21.750 315.744  1.00  0.00           C
ATOM   6524  CA  GLU E   12     -2.865  24.181 312.888  1.00  0.00           C
ATOM   6525  CA  ALA E   13      0.200  25.831 314.349  1.00  0.00           C
ATOM   6526  CA  GLY E   14      1.391  23.939 311.306  1.00  0.00           C
ATOM   6527  CA  VAL E   15      0.929  27.222 309.408  1.00  0.00           C
ATOM   6528  CA  HIS E   16     -1.108  30.326 310.357  1.00  0.00           C
ATOM   6529  CA  PHE E   17     -0.438  31.667 313.851  1.00  0.00           C
ATOM   6530  CA  GLY E   18      1.747  34.765 314.154  1.00  0.00           C
ATOM   6531  CA  HIS E   19      2.629  37.038 311.244  1.00  0.00           C
ATOM   6532  CA  GLU E   20      3.674  40.664 310.405  1.00  0.00           C
ATOM   6533  CA  ARG E   21      6.794  42.161 311.977  1.00  0.00           C
ATOM   6534  CA  LYS E   22      5.803  45.119 314.185  1.00  0.00           C
ATOM   6535  CA  ARG E   23      3.991  48.255 313.060  1.00  0.00           C
ATOM   6536  CA  TRP E   24      0.728  46.382 313.587  1.00  0.00           C
ATOM   6537  CA  ASN E   25     -2.603  48.078 314.244  1.00  0.00           C
ATOM   6538  CA  PRO E   26     -3.183  48.481 318.000  1.00  0.00           C
ATOM   6539  CA  LYS E   27     -6.825  47.482 317.410  1.00  0.00           C
ATOM   6540  CA  PHE E   28     -5.853  43.936 316.447  1.00  0.00           C
ATOM   6541  CA  ALA E   29     -4.347  43.824 319.933  1.00  0.00           C
ATOM   6542  CA  ARG E   30     -6.988  41.369 321.150  1.00  0.00           C
ATOM   6543  CA  TYR E   31     -6.093  38.672 318.597  1.00  0.00           C
ATOM   6544  CA  ILE E   32     -2.374  38.824 319.375  1.00  0.00           C
ATOM   6545  CA  TYR E   33     -0.562  36.445 321.696  1.00  0.00           C
ATOM   6546  CA  ALA E   34      2.974  37.866 321.777  1.00  0.00           C
ATOM   6547  CA  GLU E   35      6.040  39.114 319.896  1.00  0.00           C
ATOM   6548  CA  ARG E   36      9.054  36.905 319.232  1.00  0.00           C
ATOM   6549  CA  ASN E   37     12.071  37.852 317.133  1.00  0.00           C
ATOM   6550  CA  GLY E   38      9.973  40.909 316.427  1.00  0.00           C
ATOM   6551  CA  ILE E   39      6.966  39.348 314.685  1.00  0.00           C
ATOM   6552  CA  HIS E   40      3.728  39.215 316.679  1.00  0.00           C
ATOM   6553  CA  ILE E   41      2.195  35.821 317.328  1.00  0.00           C
ATOM   6554  CA  ILE E   42     -1.502  35.296 316.774  1.00  0.00           C
ATOM   6555  CA  ASP E   43     -3.390  33.413 319.467  1.00  0.00           C
ATOM   6556  CA  LEU E   44     -4.989  30.510 317.581  1.00  0.00           C
ATOM   6557  CA  GLN E   45     -7.186  29.681 320.585  1.00  0.00           C
ATOM   6558  CA  LYS E   46     -8.951  32.830 319.443  1.00  0.00           C
ATOM   6559  CA  THR E   47     -8.461  32.054 315.758  1.00  0.00           C
ATOM   6560  CA  MET E   48    -10.535  29.038 316.708  1.00  0.00           C
ATOM   6561  CA  GLU E   49    -13.315  30.804 318.579  1.00  0.00           C
ATOM   6562  CA  GLU E   50    -13.626  33.062 315.557  1.00  0.00           C
ATOM   6563  CA  LEU E   51    -13.663  30.246 313.003  1.00  0.00           C
ATOM   6564  CA  GLU E   52    -16.527  28.523 314.816  1.00  0.00           C
ATOM   6565  CA  ARG E   53    -18.530  31.733 314.841  1.00  0.00           C
```

```
ATOM   6566  CA  THR E  54     -17.508  32.644 311.293  1.00  0.00           C
ATOM   6567  CA  PHE E  55     -17.929  29.239 309.647  1.00  0.00           C
ATOM   6568  CA  ARG E  56     -21.259  28.895 311.421  1.00  0.00           C
ATOM   6569  CA  PHE E  57     -22.323  32.076 309.571  1.00  0.00           C
ATOM   6570  CA  ILE E  58     -21.260  30.371 306.363  1.00  0.00           C
ATOM   6571  CA  GLU E  59     -23.415  27.193 306.586  1.00  0.00           C
ATOM   6572  CA  ASP E  60     -26.076  29.783 307.240  1.00  0.00           C
ATOM   6573  CA  LEU E  61     -25.801  31.462 303.812  1.00  0.00           C
ATOM   6574  CA  ALA E  62     -24.484  28.187 302.456  1.00  0.00           C
ATOM   6575  CA  MET E  63     -27.471  25.840 302.726  1.00  0.00           C
ATOM   6576  CA  ARG E  64     -29.616  28.932 302.289  1.00  0.00           C
ATOM   6577  CA  GLY E  65     -28.428  29.255 298.697  1.00  0.00           C
ATOM   6578  CA  GLY E  66     -26.625  32.511 299.282  1.00  0.00           C
ATOM   6579  CA  THR E  67     -23.638  33.840 297.375  1.00  0.00           C
ATOM   6580  CA  ILE E  68     -20.184  34.724 298.719  1.00  0.00           C
ATOM   6581  CA  LEU E  69     -17.987  36.906 296.538  1.00  0.00           C
ATOM   6582  CA  PHE E  70     -14.385  35.951 297.321  1.00  0.00           C
ATOM   6583  CA  VAL E  71     -11.837  38.742 296.993  1.00  0.00           C
ATOM   6584  CA  GLY E  72      -8.097  38.135 296.800  1.00  0.00           C
ATOM   6585  CA  THR E  73      -5.935  40.569 294.826  1.00  0.00           C
ATOM   6586  CA  LYS E  74      -2.885  39.967 297.055  1.00  0.00           C
ATOM   6587  CA  LYS E  75      -0.355  37.922 295.053  1.00  0.00           C
ATOM   6588  CA  GLN E  76       0.326  35.208 297.633  1.00  0.00           C
ATOM   6589  CA  ALA E  77      -3.368  34.274 297.349  1.00  0.00           C
ATOM   6590  CA  GLN E  78      -4.215  35.303 293.799  1.00  0.00           C
ATOM   6591  CA  ASP E  79      -4.241  31.767 292.373  1.00  0.00           C
ATOM   6592  CA  ILE E  80      -5.952  30.159 295.357  1.00  0.00           C
ATOM   6593  CA  VAL E  81      -8.885  32.588 295.360  1.00  0.00           C
ATOM   6594  CA  ARG E  82      -9.653  31.207 291.896  1.00  0.00           C
ATOM   6595  CA  MET E  83      -9.415  27.499 292.693  1.00  0.00           C
ATOM   6596  CA  GLU E  84     -11.429  27.573 295.904  1.00  0.00           C
ATOM   6597  CA  ALA E  85     -13.832  30.039 294.297  1.00  0.00           C
ATOM   6598  CA  GLU E  86     -14.547  27.920 291.207  1.00  0.00           C
ATOM   6599  CA  ARG E  87     -14.612  24.916 293.515  1.00  0.00           C
ATOM   6600  CA  ALA E  88     -17.974  26.366 294.588  1.00  0.00           C
ATOM   6601  CA  GLY E  89     -20.553  28.139 292.443  1.00  0.00           C
ATOM   6602  CA  MET E  90     -19.070  31.283 293.984  1.00  0.00           C
ATOM   6603  CA  PRO E  91     -17.692  34.350 292.114  1.00  0.00           C
ATOM   6604  CA  TYR E  92     -14.330  35.972 292.801  1.00  0.00           C
ATOM   6605  CA  VAL E  93     -12.205  39.041 292.090  1.00  0.00           C
ATOM   6606  CA  ASN E  94      -8.648  37.863 291.460  1.00  0.00           C
ATOM   6607  CA  GLN E  95      -6.807  40.470 289.424  1.00  0.00           C
ATOM   6608  CA  ARG E  96      -7.787  44.014 290.369  1.00  0.00           C
ATOM   6609  CA  TRP E  97     -10.917  44.945 292.254  1.00  0.00           C
ATOM   6610  CA  LEU E  98     -12.439  47.695 290.072  1.00  0.00           C
ATOM   6611  CA  GLY E  99     -13.810  50.610 292.084  1.00  0.00           C
ATOM   6612  CA  GLY E 100     -17.562  50.357 292.423  1.00  0.00           C
ATOM   6613  CA  MET E 101     -17.997  46.661 291.661  1.00  0.00           C
ATOM   6614  CA  LEU E 102     -20.473  46.548 294.541  1.00  0.00           C
ATOM   6615  CA  THR E 103     -21.295  50.189 295.024  1.00  0.00           C
ATOM   6616  CA  ASN E 104     -21.638  50.703 291.277  1.00  0.00           C
ATOM   6617  CA  PHE E 105     -22.784  47.172 290.441  1.00  0.00           C
ATOM   6618  CA  LYS E 106     -25.375  47.918 287.780  1.00  0.00           C
ATOM   6619  CA  THR E 107     -22.688  49.622 285.709  1.00  0.00           C
ATOM   6620  CA  ILE E 108     -19.816  47.193 286.134  1.00  0.00           C
ATOM   6621  CA  SER E 109     -22.499  44.677 285.210  1.00  0.00           C
ATOM   6622  CA  GLN E 110     -22.784  46.204 281.761  1.00  0.00           C
ATOM   6623  CA  ARG E 111     -19.142  45.278 281.446  1.00  0.00           C
ATOM   6624  CA  VAL E 112     -20.145  41.626 281.812  1.00  0.00           C
ATOM   6625  CA  HIS E 113     -23.022  41.986 279.350  1.00  0.00           C
ATOM   6626  CA  ARG E 114     -20.324  43.140 276.982  1.00  0.00           C
ATOM   6627  CA  LEU E 115     -18.111  40.153 277.740  1.00  0.00           C
ATOM   6628  CA  GLU E 116     -20.986  37.835 276.877  1.00  0.00           C
ATOM   6629  CA  GLU E 117     -21.911  39.815 273.795  1.00  0.00           C
ATOM   6630  CA  LEU E 118     -18.342  39.746 272.478  1.00  0.00           C
ATOM   6631  CA  GLU E 119     -17.737  36.033 273.044  1.00  0.00           C
ATOM   6632  CA  ALA E 120     -20.754  35.553 270.775  1.00  0.00           C
ATOM   6633  CA  LEU E 121     -19.216  37.424 267.849  1.00  0.00           C
ATOM   6634  CA  PHE E 122     -15.939  35.512 268.182  1.00  0.00           C
ATOM   6635  CA  ALA E 123     -17.771  32.244 267.553  1.00  0.00           C
ATOM   6636  CA  SER E 124     -20.490  33.629 265.264  1.00  0.00           C
ATOM   6637  CA  PRO E 125     -20.625  34.494 261.539  1.00  0.00           C
ATOM   6638  CA  GLU E 126     -19.759  38.199 261.547  1.00  0.00           C
ATOM   6639  CA  ILE E 127     -16.343  37.161 262.894  1.00  0.00           C
ATOM   6640  CA  GLU E 128     -14.579  37.733 259.577  1.00  0.00           C
ATOM   6641  CA  GLU E 129     -16.443  40.981 258.853  1.00  0.00           C
ATOM   6642  CA  ARG E 130     -15.477  44.659 258.945  1.00  0.00           C
ATOM   6643  CA  PRO E 131     -11.815  45.730 259.096  1.00  0.00           C
ATOM   6644  CA  LYS E 132      -9.427  43.898 261.402  1.00  0.00           C
ATOM   6645  CA  LYS E 133      -8.719  47.119 263.284  1.00  0.00           C
ATOM   6646  CA  GLU E 134     -11.836  45.943 265.096  1.00  0.00           C
ATOM   6647  CA  GLN E 135     -11.087  42.227 264.765  1.00  0.00           C
ATOM   6648  CA  VAL E 136      -8.102  43.388 266.810  1.00  0.00           C
ATOM   6649  CA  ARG E 137      -9.428  46.075 269.161  1.00  0.00           C
ATOM   6650  CA  LEU E 138     -12.352  43.844 270.034  1.00  0.00           C
ATOM   6651  CA  LYS E 139      -9.923  40.941 270.424  1.00  0.00           C
ATOM   6652  CA  HIS E 140      -8.416  43.191 273.097  1.00  0.00           C
```

```
ATOM   6653  CA  GLU E 141     -11.684  44.031 274.871  1.00  0.00           C
ATOM   6654  CA  LEU E 142     -12.300  40.346 275.479  1.00  0.00           C
ATOM   6655  CA  GLU E 143      -8.680  40.007 276.564  1.00  0.00           C
ATOM   6656  CA  ARG E 144      -9.131  42.438 279.438  1.00  0.00           C
ATOM   6657  CA  LEU E 145     -12.786  41.697 280.218  1.00  0.00           C
ATOM   6658  CA  GLN E 146     -11.723  38.104 280.654  1.00  0.00           C
ATOM   6659  CA  LYS E 147      -8.843  39.372 282.806  1.00  0.00           C
ATOM   6660  CA  TYR E 148     -10.882  41.279 285.395  1.00  0.00           C
ATOM   6661  CA  LEU E 149     -14.399  39.946 284.942  1.00  0.00           C
ATOM   6662  CA  SER E 150     -13.625  36.206 284.890  1.00  0.00           C
ATOM   6663  CA  GLY E 151     -14.675  35.629 288.505  1.00  0.00           C
ATOM   6664  CA  PHE E 152     -17.035  38.583 288.698  1.00  0.00           C
ATOM   6665  CA  ARG E 153     -18.712  36.748 285.823  1.00  0.00           C
ATOM   6666  CA  LEU E 154     -21.335  34.972 287.977  1.00  0.00           C
ATOM   6667  CA  LEU E 155     -22.621  37.783 290.207  1.00  0.00           C
ATOM   6668  CA  LYS E 156     -26.158  38.403 288.927  1.00  0.00           C
ATOM   6669  CA  ARG E 157     -27.039  40.661 291.905  1.00  0.00           C
ATOM   6670  CA  LEU E 158     -25.050  42.081 294.823  1.00  0.00           C
ATOM   6671  CA  PRO E 159     -23.572  39.180 296.831  1.00  0.00           C
ATOM   6672  CA  ASP E 160     -24.723  38.165 300.309  1.00  0.00           C
ATOM   6673  CA  ALA E 161     -21.294  38.479 301.799  1.00  0.00           C
ATOM   6674  CA  ILE E 162     -17.649  38.859 300.966  1.00  0.00           C
ATOM   6675  CA  PHE E 163     -14.807  36.559 301.853  1.00  0.00           C
ATOM   6676  CA  VAL E 164     -11.884  38.931 301.669  1.00  0.00           C
ATOM   6677  CA  VAL E 165      -8.309  37.843 302.241  1.00  0.00           C
ATOM   6678  CA  ASP E 166      -6.131  40.808 303.254  1.00  0.00           C
ATOM   6679  CA  PRO E 167      -8.783  43.427 304.228  1.00  0.00           C
ATOM   6680  CA  THR E 168      -6.157  46.122 304.571  1.00  0.00           C
ATOM   6681  CA  LYS E 169      -4.948  45.371 301.066  1.00  0.00           C
ATOM   6682  CA  GLU E 170      -8.558  44.849 299.960  1.00  0.00           C
ATOM   6683  CA  ALA E 171      -9.905  47.815 301.951  1.00  0.00           C
ATOM   6684  CA  ILE E 172     -11.722  49.424 299.018  1.00  0.00           C
ATOM   6685  CA  ALA E 173     -13.749  46.225 298.678  1.00  0.00           C
ATOM   6686  CA  VAL E 174     -14.512  46.046 302.389  1.00  0.00           C
ATOM   6687  CA  ARG E 175     -15.608  49.694 302.375  1.00  0.00           C
ATOM   6688  CA  GLU E 176     -18.068  49.114 299.534  1.00  0.00           C
ATOM   6689  CA  ALA E 177     -19.589  46.231 301.497  1.00  0.00           C
ATOM   6690  CA  ARG E 178     -20.173  48.354 304.593  1.00  0.00           C
ATOM   6691  CA  LYS E 179     -22.009  51.058 302.630  1.00  0.00           C
ATOM   6692  CA  LEU E 180     -24.164  48.354 301.110  1.00  0.00           C
ATOM   6693  CA  PHE E 181     -24.576  46.447 304.392  1.00  0.00           C
ATOM   6694  CA  ILE E 182     -23.063  43.380 302.856  1.00  0.00           C
ATOM   6695  CA  PRO E 183     -21.538  41.147 305.566  1.00  0.00           C
ATOM   6696  CA  VAL E 184     -17.753  41.015 305.590  1.00  0.00           C
ATOM   6697  CA  ILE E 185     -15.743  37.848 306.247  1.00  0.00           C
ATOM   6698  CA  ALA E 186     -11.960  38.060 306.293  1.00  0.00           C
ATOM   6699  CA  LEU E 187      -8.759  36.126 306.915  1.00  0.00           C
ATOM   6700  CA  ALA E 188      -7.047  39.064 308.573  1.00  0.00           C
ATOM   6701  CA  ASP E 189      -3.886  39.459 310.626  1.00  0.00           C
ATOM   6702  CA  THR E 190      -1.703  41.815 312.673  1.00  0.00           C
ATOM   6703  CA  ASP E 191      -1.788  44.820 310.326  1.00  0.00           C
ATOM   6704  CA  SER E 192      -5.545  45.163 309.794  1.00  0.00           C
ATOM   6705  CA  ASP E 193      -8.574  46.779 311.440  1.00  0.00           C
ATOM   6706  CA  PRO E 194     -10.587  44.009 313.142  1.00  0.00           C
ATOM   6707  CA  ASP E 195     -13.516  46.383 313.759  1.00  0.00           C
ATOM   6708  CA  LEU E 196     -14.380  46.533 310.072  1.00  0.00           C
ATOM   6709  CA  VAL E 197     -14.544  42.796 309.574  1.00  0.00           C
ATOM   6710  CA  ASP E 198     -17.884  41.257 310.481  1.00  0.00           C
ATOM   6711  CA  TYR E 199     -16.516  37.708 310.700  1.00  0.00           C
ATOM   6712  CA  ILE E 200     -12.779  37.720 311.362  1.00  0.00           C
ATOM   6713  CA  ILE E 201     -10.440  34.785 310.790  1.00  0.00           C
ATOM   6714  CA  PRO E 202      -7.352  36.124 312.622  1.00  0.00           C
ATOM   6715  CA  GLY E 203      -4.294  34.468 311.179  1.00  0.00           C
ATOM   6716  CA  ASN E 204      -1.500  34.694 308.625  1.00  0.00           C
ATOM   6717  CA  ASP E 205      -3.037  36.784 305.798  1.00  0.00           C
ATOM   6718  CA  ASP E 206       0.040  35.912 303.780  1.00  0.00           C
ATOM   6719  CA  ALA E 207       1.747  32.607 302.937  1.00  0.00           C
ATOM   6720  CA  ILE E 208      -0.008  30.111 300.685  1.00  0.00           C
ATOM   6721  CA  ARG E 209       0.266  27.269 303.199  1.00  0.00           C
ATOM   6722  CA  SER E 210      -2.184  29.373 305.258  1.00  0.00           C
ATOM   6723  CA  ILE E 211      -4.502  31.102 302.793  1.00  0.00           C
ATOM   6724  CA  GLN E 212      -4.958  27.740 301.078  1.00  0.00           C
ATOM   6725  CA  LEU E 213      -5.972  26.034 304.315  1.00  0.00           C
ATOM   6726  CA  ILE E 214      -8.620  28.444 305.539  1.00  0.00           C
ATOM   6727  CA  LEU E 215     -10.176  29.171 302.169  1.00  0.00           C
ATOM   6728  CA  SER E 216     -10.177  25.548 301.014  1.00  0.00           C
ATOM   6729  CA  ARG E 217     -12.061  24.509 304.168  1.00  0.00           C
ATOM   6730  CA  ALA E 218     -14.435  27.447 304.067  1.00  0.00           C
ATOM   6731  CA  VAL E 219     -15.298  26.078 300.607  1.00  0.00           C
ATOM   6732  CA  ASP E 220     -15.673  22.452 301.672  1.00  0.00           C
ATOM   6733  CA  LEU E 221     -18.100  23.846 304.238  1.00  0.00           C
ATOM   6734  CA  ILE E 222     -20.038  25.641 301.487  1.00  0.00           C
ATOM   6735  CA  ILE E 223     -20.495  22.384 299.557  1.00  0.00           C
ATOM   6736  CA  GLN E 224     -20.879  20.244 302.662  1.00  0.00           C
ATOM   6737  CA  ALA E 225     -23.761  22.555 303.519  1.00  0.00           C
ATOM   6738  CA  ARG E 226     -25.264  22.382 300.052  1.00  0.00           C
ATOM   6739  CA  GLY E 227     -25.205  18.605 299.882  1.00  0.00           C
```

| | | | | | | | | | | |
|---|---|---|---|---|---|---|---|---|---|---|
| ATOM | 6740 | CA | GLY | E | 228 | -22.299 | 17.966 | 297.555 | 1.00 | 0.00 | C |
| ATOM | 6741 | CA | VAL | E | 229 | -20.240 | 15.339 | 299.384 | 1.00 | 0.00 | C |
| ATOM | 6742 | CA | VAL | E | 230 | -17.290 | 16.738 | 297.439 | 1.00 | 0.00 | C |
| ATOM | 6743 | CA | GLU | E | 231 | -13.788 | 15.251 | 297.491 | 1.00 | 0.00 | C |
| ATOM | 6744 | CA | PRO | E | 232 | -10.575 | 16.964 | 298.793 | 1.00 | 0.00 | C |
| ATOM | 6745 | CA | SER | E | 233 | -9.203 | 20.244 | 297.401 | 1.00 | 0.00 | C |
| ATOM | 6746 | CA | PRO | E | 234 | -6.886 | 20.470 | 294.329 | 1.00 | 0.00 | C |
| ATOM | 6747 | CA | SER | E | 235 | -5.323 | 23.756 | 295.522 | 1.00 | 0.00 | C |
| ATOM | 6748 | CA | TYR | E | 236 | -2.857 | 22.031 | 297.854 | 1.00 | 0.00 | C |
| ATOM | 6749 | CA | ALA | E | 237 | -0.916 | 21.407 | 294.629 | 1.00 | 0.00 | C |
| ATOM | 6750 | CA | LEU | E | 238 | -0.369 | 25.172 | 294.434 | 1.00 | 0.00 | C |
| ATOM | 6751 | CA | VAL | E | 239 | 1.189 | 25.011 | 297.885 | 1.00 | 0.00 | C |
| ATOM | 6752 | CA | GLN | E | 240 | 4.433 | 23.810 | 296.264 | 1.00 | 0.00 | C |
| TER | 6753 | | GLN | E | 240 | | | | | | |
| ATOM | 6754 | CA | GLY | F | 2 | -19.153 | 80.396 | 263.877 | 1.00 | 0.00 | C |
| ATOM | 6755 | CA | ASN | F | 3 | -18.218 | 76.959 | 262.561 | 1.00 | 0.00 | C |
| ATOM | 6756 | CA | LYS | F | 4 | -19.812 | 73.682 | 261.312 | 1.00 | 0.00 | C |
| ATOM | 6757 | CA | ILE | F | 5 | -21.373 | 72.986 | 257.896 | 1.00 | 0.00 | C |
| ATOM | 6758 | CA | HIS | F | 6 | -24.973 | 72.299 | 257.040 | 1.00 | 0.00 | C |
| ATOM | 6759 | CA | PRO | F | 7 | -25.485 | 68.663 | 258.050 | 1.00 | 0.00 | C |
| ATOM | 6760 | CA | ILE | F | 8 | -27.447 | 68.068 | 254.856 | 1.00 | 0.00 | C |
| ATOM | 6761 | CA | GLY | F | 9 | -25.325 | 69.834 | 252.265 | 1.00 | 0.00 | C |
| ATOM | 6762 | CA | PHE | F | 10 | -22.434 | 68.043 | 253.911 | 1.00 | 0.00 | C |
| ATOM | 6763 | CA | ARG | F | 11 | -23.957 | 64.616 | 253.241 | 1.00 | 0.00 | C |
| ATOM | 6764 | CA | LEU | F | 12 | -25.666 | 65.162 | 249.864 | 1.00 | 0.00 | C |
| ATOM | 6765 | CA | GLY | F | 13 | -23.288 | 62.616 | 248.393 | 1.00 | 0.00 | C |
| ATOM | 6766 | CA | ILE | F | 14 | -24.757 | 60.017 | 250.730 | 1.00 | 0.00 | C |
| ATOM | 6767 | CA | THR | F | 15 | -27.401 | 59.712 | 253.472 | 1.00 | 0.00 | C |
| ATOM | 6768 | CA | ARG | F | 16 | -29.510 | 62.505 | 251.915 | 1.00 | 0.00 | C |
| ATOM | 6769 | CA | ASP | F | 17 | -30.836 | 63.205 | 248.385 | 1.00 | 0.00 | C |
| ATOM | 6770 | CA | TRP | F | 18 | -31.537 | 66.585 | 246.774 | 1.00 | 0.00 | C |
| ATOM | 6771 | CA | GLU | F | 19 | -34.836 | 68.500 | 246.856 | 1.00 | 0.00 | C |
| ATOM | 6772 | CA | SER | F | 20 | -34.743 | 69.083 | 243.081 | 1.00 | 0.00 | C |
| ATOM | 6773 | CA | ARG | F | 21 | -33.336 | 66.218 | 241.010 | 1.00 | 0.00 | C |
| ATOM | 6774 | CA | TRP | F | 22 | -33.327 | 66.930 | 237.285 | 1.00 | 0.00 | C |
| ATOM | 6775 | CA | TYR | F | 23 | -30.744 | 67.419 | 234.549 | 1.00 | 0.00 | C |
| ATOM | 6776 | CA | ALA | F | 24 | -30.480 | 70.621 | 232.499 | 1.00 | 0.00 | C |
| ATOM | 6777 | CA | GLY | F | 25 | -28.048 | 73.474 | 232.168 | 1.00 | 0.00 | C |
| ATOM | 6778 | CA | LYS | F | 26 | -26.423 | 76.193 | 230.120 | 1.00 | 0.00 | C |
| ATOM | 6779 | CA | LYS | F | 27 | -29.242 | 78.412 | 228.867 | 1.00 | 0.00 | C |
| ATOM | 6780 | CA | GLN | F | 28 | -31.968 | 76.841 | 230.978 | 1.00 | 0.00 | C |
| ATOM | 6781 | CA | TYR | F | 29 | -30.681 | 75.856 | 234.426 | 1.00 | 0.00 | C |
| ATOM | 6782 | CA | ARG | F | 30 | -30.971 | 79.375 | 235.860 | 1.00 | 0.00 | C |
| ATOM | 6783 | CA | HIS | F | 31 | -34.497 | 79.766 | 234.434 | 1.00 | 0.00 | C |
| ATOM | 6784 | CA | LEU | F | 32 | -35.523 | 76.210 | 235.254 | 1.00 | 0.00 | C |
| ATOM | 6785 | CA | LEU | F | 33 | -34.285 | 76.760 | 238.820 | 1.00 | 0.00 | C |
| ATOM | 6786 | CA | LEU | F | 34 | -35.726 | 80.174 | 239.513 | 1.00 | 0.00 | C |
| ATOM | 6787 | CA | GLU | F | 35 | -39.002 | 78.372 | 238.894 | 1.00 | 0.00 | C |
| ATOM | 6788 | CA | ASP | F | 36 | -38.494 | 75.776 | 241.638 | 1.00 | 0.00 | C |
| ATOM | 6789 | CA | GLN | F | 37 | -38.108 | 78.652 | 244.093 | 1.00 | 0.00 | C |
| ATOM | 6790 | CA | ARG | F | 38 | -41.282 | 80.301 | 242.800 | 1.00 | 0.00 | C |
| ATOM | 6791 | CA | ILE | F | 39 | -42.969 | 76.961 | 243.426 | 1.00 | 0.00 | C |
| ATOM | 6792 | CA | ARG | F | 40 | -41.624 | 76.375 | 246.939 | 1.00 | 0.00 | C |
| ATOM | 6793 | CA | GLY | F | 41 | -42.333 | 80.055 | 247.552 | 1.00 | 0.00 | C |
| ATOM | 6794 | CA | LEU | F | 42 | -46.118 | 79.628 | 247.498 | 1.00 | 0.00 | C |
| ATOM | 6795 | CA | LEU | F | 43 | -46.334 | 76.136 | 249.002 | 1.00 | 0.00 | C |
| ATOM | 6796 | CA | GLU | F | 44 | -44.567 | 77.280 | 252.161 | 1.00 | 0.00 | C |
| ATOM | 6797 | CA | LYS | F | 45 | -46.644 | 80.475 | 252.201 | 1.00 | 0.00 | C |
| ATOM | 6798 | CA | GLU | F | 46 | -49.816 | 78.386 | 251.936 | 1.00 | 0.00 | C |
| ATOM | 6799 | CA | LEU | F | 47 | -49.474 | 74.809 | 253.203 | 1.00 | 0.00 | C |
| ATOM | 6800 | CA | TYR | F | 48 | -48.191 | 76.091 | 256.545 | 1.00 | 0.00 | C |
| ATOM | 6801 | CA | SER | F | 49 | -50.964 | 74.603 | 258.708 | 1.00 | 0.00 | C |
| ATOM | 6802 | CA | ALA | F | 50 | -50.612 | 71.360 | 256.752 | 1.00 | 0.00 | C |
| ATOM | 6803 | CA | GLY | F | 51 | -47.103 | 70.995 | 258.086 | 1.00 | 0.00 | C |
| ATOM | 6804 | CA | LEU | F | 52 | -44.593 | 71.389 | 255.253 | 1.00 | 0.00 | C |
| ATOM | 6805 | CA | ALA | F | 53 | -41.473 | 69.247 | 255.477 | 1.00 | 0.00 | C |
| ATOM | 6806 | CA | ARG | F | 54 | -40.078 | 68.927 | 251.976 | 1.00 | 0.00 | C |
| ATOM | 6807 | CA | VAL | F | 55 | -40.844 | 69.702 | 248.353 | 1.00 | 0.00 | C |
| ATOM | 6808 | CA | ASP | F | 56 | -39.336 | 67.251 | 245.879 | 1.00 | 0.00 | C |
| ATOM | 6809 | CA | ILE | F | 57 | -39.366 | 68.632 | 242.340 | 1.00 | 0.00 | C |
| ATOM | 6810 | CA | GLU | F | 58 | -38.583 | 66.198 | 239.507 | 1.00 | 0.00 | C |
| ATOM | 6811 | CA | ARG | F | 59 | -38.661 | 66.989 | 235.789 | 1.00 | 0.00 | C |
| ATOM | 6812 | CA | ALA | F | 60 | -38.360 | 65.704 | 232.212 | 1.00 | 0.00 | C |
| ATOM | 6813 | CA | ALA | F | 61 | -39.843 | 68.636 | 230.231 | 1.00 | 0.00 | C |
| ATOM | 6814 | CA | ASP | F | 62 | -43.175 | 70.496 | 230.389 | 1.00 | 0.00 | C |
| ATOM | 6815 | CA | ASN | F | 63 | -44.363 | 67.814 | 232.829 | 1.00 | 0.00 | C |
| ATOM | 6816 | CA | VAL | F | 64 | -43.116 | 68.785 | 236.268 | 1.00 | 0.00 | C |
| ATOM | 6817 | CA | ALA | F | 65 | -43.387 | 66.629 | 239.403 | 1.00 | 0.00 | C |
| ATOM | 6818 | CA | VAL | F | 66 | -43.708 | 68.381 | 242.785 | 1.00 | 0.00 | C |
| ATOM | 6819 | CA | THR | F | 67 | -44.332 | 65.930 | 245.614 | 1.00 | 0.00 | C |
| ATOM | 6820 | CA | VAL | F | 68 | -45.171 | 68.024 | 248.703 | 1.00 | 0.00 | C |
| ATOM | 6821 | CA | HIS | F | 69 | -44.623 | 66.069 | 251.972 | 1.00 | 0.00 | C |
| ATOM | 6822 | CA | VAL | F | 70 | -47.000 | 66.773 | 254.852 | 1.00 | 0.00 | C |
| ATOM | 6823 | CA | ALA | F | 71 | -48.063 | 65.766 | 258.369 | 1.00 | 0.00 | C |
| ATOM | 6824 | CA | LYS | F | 72 | -51.738 | 66.577 | 257.725 | 1.00 | 0.00 | C |
| ATOM | 6825 | CA | PRO | F | 73 | -52.230 | 65.475 | 254.069 | 1.00 | 0.00 | C |
| ATOM | 6826 | CA | GLY | F | 74 | -55.841 | 66.463 | 254.564 | 1.00 | 0.00 | C |

```
ATOM  6827  CA  VAL F  75   -55.394  70.220 254.949  1.00  0.00           C
ATOM  6828  CA  VAL F  76   -53.471  69.944 251.672  1.00  0.00           C
ATOM  6829  CA  ILE F  77   -55.952  68.027 249.514  1.00  0.00           C
ATOM  6830  CA  GLY F  78   -59.050  69.871 250.666  1.00  0.00           C
ATOM  6831  CA  ARG F  79   -62.735  68.939 250.875  1.00  0.00           C
ATOM  6832  CA  GLY F  80   -63.106  65.894 248.642  1.00  0.00           C
ATOM  6833  CA  GLY F  81   -60.091  67.302 246.846  1.00  0.00           C
ATOM  6834  CA  GLU F  82   -61.262  70.845 246.133  1.00  0.00           C
ATOM  6835  CA  ARG F  83   -58.128  72.609 247.388  1.00  0.00           C
ATOM  6836  CA  ILE F  84   -55.679  70.376 245.534  1.00  0.00           C
ATOM  6837  CA  ARG F  85   -57.605  71.986 242.677  1.00  0.00           C
ATOM  6838  CA  VAL F  86   -57.046  75.600 243.700  1.00  0.00           C
ATOM  6839  CA  LEU F  87   -53.327  75.116 244.281  1.00  0.00           C
ATOM  6840  CA  ARG F  88   -52.682  72.694 241.407  1.00  0.00           C
ATOM  6841  CA  GLU F  89   -54.216  75.427 239.258  1.00  0.00           C
ATOM  6842  CA  GLU F  90   -52.608  78.376 241.061  1.00  0.00           C
ATOM  6843  CA  LEU F  91   -49.489  76.425 240.114  1.00  0.00           C
ATOM  6844  CA  ALA F  92   -49.846  76.781 236.340  1.00  0.00           C
ATOM  6845  CA  LYS F  93   -50.732  80.468 236.783  1.00  0.00           C
ATOM  6846  CA  LEU F  94   -47.058  80.530 237.740  1.00  0.00           C
ATOM  6847  CA  THR F  95   -45.574  77.922 235.412  1.00  0.00           C
ATOM  6848  CA  GLY F  96   -47.320  77.459 232.087  1.00  0.00           C
ATOM  6849  CA  LYS F  97   -45.197  74.302 232.147  1.00  0.00           C
ATOM  6850  CA  ASN F  98   -48.229  72.117 233.076  1.00  0.00           C
ATOM  6851  CA  VAL F  99   -47.345  70.229 236.264  1.00  0.00           C
ATOM  6852  CA  ALA F 100   -48.634  67.535 238.637  1.00  0.00           C
ATOM  6853  CA  LEU F 101   -48.836  67.825 242.449  1.00  0.00           C
ATOM  6854  CA  ASN F 102   -48.609  64.598 244.481  1.00  0.00           C
ATOM  6855  CA  VAL F 103   -48.872  64.506 248.294  1.00  0.00           C
ATOM  6856  CA  GLN F 104   -47.169  62.019 250.592  1.00  0.00           C
ATOM  6857  CA  GLU F 105   -47.919  61.787 254.306  1.00  0.00           C
ATOM  6858  CA  VAL F 106   -45.247  62.175 256.982  1.00  0.00           C
ATOM  6859  CA  GLN F 107   -45.100  58.976 259.047  1.00  0.00           C
ATOM  6860  CA  ASN F 108   -44.561  60.565 262.474  1.00  0.00           C
ATOM  6861  CA  PRO F 109   -43.862  64.304 262.132  1.00  0.00           C
ATOM  6862  CA  ASN F 110   -41.914  63.614 265.308  1.00  0.00           C
ATOM  6863  CA  LEU F 111   -38.893  62.628 263.240  1.00  0.00           C
ATOM  6864  CA  SER F 112   -38.983  65.559 260.822  1.00  0.00           C
ATOM  6865  CA  ALA F 113   -36.337  68.044 261.897  1.00  0.00           C
ATOM  6866  CA  PRO F 114   -38.208  70.778 259.961  1.00  0.00           C
ATOM  6867  CA  LEU F 115   -41.390  69.911 261.780  1.00  0.00           C
ATOM  6868  CA  VAL F 116   -39.871  69.511 265.250  1.00  0.00           C
ATOM  6869  CA  ALA F 117   -38.238  72.886 264.559  1.00  0.00           C
ATOM  6870  CA  GLN F 118   -41.380  74.668 263.349  1.00  0.00           C
ATOM  6871  CA  ARG F 119   -43.134  72.939 266.229  1.00  0.00           C
ATOM  6872  CA  VAL F 120   -40.800  74.707 268.665  1.00  0.00           C
ATOM  6873  CA  ALA F 121   -40.636  77.897 266.632  1.00  0.00           C
ATOM  6874  CA  GLU F 122   -44.410  78.235 267.015  1.00  0.00           C
ATOM  6875  CA  GLN F 123   -44.583  77.634 270.765  1.00  0.00           C
ATOM  6876  CA  ILE F 124   -41.917  80.299 271.174  1.00  0.00           C
ATOM  6877  CA  GLU F 125   -44.032  82.697 269.148  1.00  0.00           C
ATOM  6878  CA  ARG F 126   -46.976  81.975 271.426  1.00  0.00           C
ATOM  6879  CA  ARG F 127   -44.784  82.849 274.433  1.00  0.00           C
ATOM  6880  CA  PHE F 128   -44.038  79.427 275.947  1.00  0.00           C
ATOM  6881  CA  ALA F 129   -41.074  78.774 278.237  1.00  0.00           C
ATOM  6882  CA  VAL F 130   -38.252  78.230 275.757  1.00  0.00           C
ATOM  6883  CA  ARG F 131   -36.133  75.746 277.692  1.00  0.00           C
ATOM  6884  CA  ARG F 132   -39.264  73.666 278.384  1.00  0.00           C
ATOM  6885  CA  ALA F 133   -40.538  73.700 274.807  1.00  0.00           C
ATOM  6886  CA  ILE F 134   -37.058  72.524 273.869  1.00  0.00           C
ATOM  6887  CA  LYS F 135   -36.680  69.713 276.414  1.00  0.00           C
ATOM  6888  CA  GLN F 136   -40.203  68.596 275.492  1.00  0.00           C
ATOM  6889  CA  ALA F 137   -39.385  68.535 271.785  1.00  0.00           C
ATOM  6890  CA  VAL F 138   -36.197  66.552 272.334  1.00  0.00           C
ATOM  6891  CA  GLN F 139   -38.224  64.139 274.400  1.00  0.00           C
ATOM  6892  CA  ARG F 140   -40.981  63.688 271.800  1.00  0.00           C
ATOM  6893  CA  VAL F 141   -38.379  63.085 269.080  1.00  0.00           C
ATOM  6894  CA  MET F 142   -36.295  60.939 271.359  1.00  0.00           C
ATOM  6895  CA  GLU F 143   -39.440  59.233 272.683  1.00  0.00           C
ATOM  6896  CA  SER F 144   -40.609  58.035 269.255  1.00  0.00           C
ATOM  6897  CA  GLY F 145   -37.713  56.260 267.579  1.00  0.00           C
ATOM  6898  CA  ALA F 146   -34.555  58.261 266.832  1.00  0.00           C
ATOM  6899  CA  LYS F 147   -31.136  57.086 267.975  1.00  0.00           C
ATOM  6900  CA  GLY F 148   -30.427  60.712 268.858  1.00  0.00           C
ATOM  6901  CA  ALA F 149   -31.784  64.261 268.722  1.00  0.00           C
ATOM  6902  CA  LYS F 150   -30.960  67.864 269.645  1.00  0.00           C
ATOM  6903  CA  VAL F 151   -32.669  71.263 269.528  1.00  0.00           C
ATOM  6904  CA  ILE F 152   -31.147  74.747 269.618  1.00  0.00           C
ATOM  6905  CA  VAL F 153   -32.902  78.065 270.115  1.00  0.00           C
ATOM  6906  CA  SER F 154   -31.163  81.311 269.149  1.00  0.00           C
ATOM  6907  CA  GLY F 155   -31.276  84.313 271.446  1.00  0.00           C
ATOM  6908  CA  ARG F 156   -33.457  86.799 273.330  1.00  0.00           C
ATOM  6909  CA  ILE F 157   -34.985  83.867 275.102  1.00  0.00           C
ATOM  6910  CA  GLY F 158   -38.056  85.140 276.907  1.00  0.00           C
ATOM  6911  CA  GLY F 159   -37.611  88.529 275.295  1.00  0.00           C
ATOM  6912  CA  ALA F 160   -34.553  89.064 277.497  1.00  0.00           C
ATOM  6913  CA  GLU F 161   -32.486  92.130 276.543  1.00  0.00           C
```

```
ATOM   6914  CA  GLN F 162     -29.380  89.894 276.336  1.00  0.00           C
ATOM   6915  CA  ALA F 163     -29.459  87.314 273.538  1.00  0.00           C
ATOM   6916  CA  ARG F 164     -28.776  83.824 274.859  1.00  0.00           C
ATOM   6917  CA  THR F 165     -28.719  80.340 273.337  1.00  0.00           C
ATOM   6918  CA  GLU F 166     -30.551  77.251 274.567  1.00  0.00           C
ATOM   6919  CA  TRP F 167     -29.593  73.604 274.217  1.00  0.00           C
ATOM   6920  CA  ALA F 168     -31.045  70.103 274.792  1.00  0.00           C
ATOM   6921  CA  ALA F 169     -29.859  66.792 273.373  1.00  0.00           C
ATOM   6922  CA  GLN F 170     -30.056  62.979 273.832  1.00  0.00           C
ATOM   6923  CA  GLY F 171     -28.271  59.951 272.323  1.00  0.00           C
ATOM   6924  CA  ARG F 172     -25.636  59.965 269.568  1.00  0.00           C
ATOM   6925  CA  VAL F 173     -25.880  62.970 267.227  1.00  0.00           C
ATOM   6926  CA  PRO F 174     -22.471  62.733 265.406  1.00  0.00           C
ATOM   6927  CA  LEU F 175     -22.281  65.773 263.169  1.00  0.00           C
ATOM   6928  CA  HIS F 176     -18.799  64.642 262.222  1.00  0.00           C
ATOM   6929  CA  THR F 177     -19.589  61.123 261.103  1.00  0.00           C
ATOM   6930  CA  LEU F 178     -20.105  61.451 257.363  1.00  0.00           C
ATOM   6931  CA  ARG F 179     -22.723  58.710 257.124  1.00  0.00           C
ATOM   6932  CA  ALA F 180     -24.973  59.309 260.147  1.00  0.00           C
ATOM   6933  CA  ASN F 181     -28.137  60.464 258.419  1.00  0.00           C
ATOM   6934  CA  ILE F 182     -29.116  63.386 260.506  1.00  0.00           C
ATOM   6935  CA  ASP F 183     -32.220  65.328 259.579  1.00  0.00           C
ATOM   6936  CA  TYR F 184     -31.606  69.043 259.917  1.00  0.00           C
ATOM   6937  CA  GLY F 185     -34.403  71.512 260.295  1.00  0.00           C
ATOM   6938  CA  PHE F 186     -34.477  75.238 260.868  1.00  0.00           C
ATOM   6939  CA  ALA F 187     -37.418  77.333 261.942  1.00  0.00           C
ATOM   6940  CA  LEU F 188     -37.552  81.123 262.260  1.00  0.00           C
ATOM   6941  CA  ALA F 189     -39.852  82.838 264.804  1.00  0.00           C
ATOM   6942  CA  ARG F 190     -40.849  86.475 264.242  1.00  0.00           C
ATOM   6943  CA  THR F 191     -41.626  88.209 267.552  1.00  0.00           C
ATOM   6944  CA  THR F 192     -42.596  91.418 269.297  1.00  0.00           C
ATOM   6945  CA  TYR F 193     -38.994  91.638 270.432  1.00  0.00           C
ATOM   6946  CA  GLY F 194     -37.332  90.037 267.416  1.00  0.00           C
ATOM   6947  CA  VAL F 195     -36.404  87.019 265.311  1.00  0.00           C
ATOM   6948  CA  LEU F 196     -35.203  83.858 267.069  1.00  0.00           C
ATOM   6949  CA  GLY F 197     -33.894  80.957 265.001  1.00  0.00           C
ATOM   6950  CA  VAL F 198     -34.708  77.347 265.876  1.00  0.00           C
ATOM   6951  CA  LYS F 199     -32.615  74.341 264.955  1.00  0.00           C
ATOM   6952  CA  ALA F 200     -33.664  70.703 265.105  1.00  0.00           C
ATOM   6953  CA  TYR F 201     -31.281  67.763 264.647  1.00  0.00           C
ATOM   6954  CA  ILE F 202     -32.509  64.176 264.445  1.00  0.00           C
ATOM   6955  CA  PHE F 203     -30.337  61.090 264.186  1.00  0.00           C
ATOM   6956  CA  LEU F 204     -31.634  57.823 262.690  1.00  0.00           C
ATOM   6957  CA  GLY F 205     -29.824  54.550 262.101  1.00  0.00           C
ATOM   6958  CA  GLU F 206     -26.469  55.080 260.433  1.00  0.00           C
ATOM   6959  CA  VAL F 207     -25.036  53.000 257.521  1.00  0.00           C
TER    6960          VAL F 207
ATOM   6961  CA  GLY G   2     -66.665  98.917 308.983  1.00  0.00           C
ATOM   6962  CA  ARG G   3     -66.266  95.251 308.066  1.00  0.00           C
ATOM   6963  CA  TYR G   4     -65.305  95.121 304.398  1.00  0.00           C
ATOM   6964  CA  ILE G   5     -68.513  95.734 302.431  1.00  0.00           C
ATOM   6965  CA  GLY G   6     -67.692  95.373 298.746  1.00  0.00           C
ATOM   6966  CA  PRO G   7     -67.760  92.791 295.950  1.00  0.00           C
ATOM   6967  CA  VAL G   8     -67.628  89.467 297.775  1.00  0.00           C
ATOM   6968  CA  CYS G   9     -67.793  86.706 295.184  1.00  0.00           C
ATOM   6969  CA  ARG G  10     -64.404  88.186 294.224  1.00  0.00           C
ATOM   6970  CA  LEU G  11     -62.888  86.905 297.473  1.00  0.00           C
ATOM   6971  CA  CYS G  12     -64.464  83.515 296.726  1.00  0.00           C
ATOM   6972  CA  ARG G  13     -62.353  83.718 293.546  1.00  0.00           C
ATOM   6973  CA  ARG G  14     -59.030  84.935 295.010  1.00  0.00           C
ATOM   6974  CA  GLU G  15     -59.059  82.082 297.520  1.00  0.00           C
ATOM   6975  CA  GLY G  16     -59.938  79.852 294.595  1.00  0.00           C
ATOM   6976  CA  VAL G  17     -62.203  78.123 297.097  1.00  0.00           C
ATOM   6977  CA  LYS G  18     -65.942  78.515 297.527  1.00  0.00           C
ATOM   6978  CA  LEU G  19     -66.969  80.947 300.222  1.00  0.00           C
ATOM   6979  CA  TYR G  20     -70.504  81.139 301.452  1.00  0.00           C
ATOM   6980  CA  LEU G  21     -70.735  84.894 301.816  1.00  0.00           C
ATOM   6981  CA  LYS G  22     -74.240  84.975 300.372  1.00  0.00           C
ATOM   6982  CA  GLY G  23     -76.034  81.931 301.712  1.00  0.00           C
ATOM   6983  CA  GLU G  24     -78.388  81.401 298.771  1.00  0.00           C
ATOM   6984  CA  ARG G  25     -77.077  81.798 295.213  1.00  0.00           C
ATOM   6985  CA  CYS G  26     -73.692  80.535 296.363  1.00  0.00           C
ATOM   6986  CA  TYR G  27     -75.478  77.359 295.209  1.00  0.00           C
ATOM   6987  CA  SER G  28     -77.409  78.409 292.118  1.00  0.00           C
ATOM   6988  CA  PRO G  29     -74.780  78.147 289.284  1.00  0.00           C
ATOM   6989  CA  LYS G  30     -73.502  81.646 290.000  1.00  0.00           C
ATOM   6990  CA  CYS G  31     -71.124  81.683 293.012  1.00  0.00           C
ATOM   6991  CA  ALA G  32     -68.830  82.472 290.082  1.00  0.00           C
ATOM   6992  CA  MET G  33     -66.662  79.668 291.425  1.00  0.00           C
ATOM   6993  CA  GLU G  34     -68.869  77.930 288.926  1.00  0.00           C
ATOM   6994  CA  ARG G  35     -67.121  78.238 285.556  1.00  0.00           C
ATOM   6995  CA  ARG G  36     -64.718  81.048 286.609  1.00  0.00           C
ATOM   6996  CA  PRO G  37     -62.793  79.933 289.784  1.00  0.00           C
ATOM   6997  CA  TYR G  38     -59.744  81.947 288.821  1.00  0.00           C
ATOM   6998  CA  PRO G  39     -58.721  85.110 290.732  1.00  0.00           C
ATOM   6999  CA  PRO G  40     -60.235  88.518 289.826  1.00  0.00           C
ATOM   7000  CA  GLY G  41     -58.509  91.113 287.665  1.00  0.00           C
```

```
ATOM  7001  CA  GLN G  42   -56.638  91.618 284.413  1.00  0.00           C
ATOM  7002  CA  HIS G  43   -54.369  88.700 285.307  1.00  0.00           C
ATOM  7003  CA  GLY G  44   -56.677  86.047 286.736  1.00  0.00           C
ATOM  7004  CA  GLN G  45   -56.307  83.706 283.769  1.00  0.00           C
ATOM  7005  CA  LYS G  46   -52.501  83.892 283.592  1.00  0.00           C
ATOM  7006  CA  ARG G  47   -50.452  81.020 285.047  1.00  0.00           C
ATOM  7007  CA  ALA G  48   -49.783  81.096 288.795  1.00  0.00           C
ATOM  7008  CA  ARG G  49   -46.250  80.929 290.201  1.00  0.00           C
ATOM  7009  CA  ARG G  50   -45.031  78.796 293.100  1.00  0.00           C
ATOM  7010  CA  PRO G  51   -46.252  80.801 296.145  1.00  0.00           C
ATOM  7011  CA  SER G  52   -43.828  81.758 298.921  1.00  0.00           C
ATOM  7012  CA  ASP G  53   -44.177  80.291 302.409  1.00  0.00           C
ATOM  7013  CA  TYR G  54   -45.473  83.751 303.294  1.00  0.00           C
ATOM  7014  CA  ALA G  55   -47.972  83.795 300.419  1.00  0.00           C
ATOM  7015  CA  VAL G  56   -49.341  80.439 301.519  1.00  0.00           C
ATOM  7016  CA  ARG G  57   -49.691  81.395 305.191  1.00  0.00           C
ATOM  7017  CA  LEU G  58   -51.024  84.749 304.134  1.00  0.00           C
ATOM  7018  CA  ARG G  59   -53.657  83.243 301.835  1.00  0.00           C
ATOM  7019  CA  GLU G  60   -54.664  80.685 304.443  1.00  0.00           C
ATOM  7020  CA  LYS G  61   -55.373  83.296 307.129  1.00  0.00           C
ATOM  7021  CA  GLN G  62   -57.198  85.631 304.724  1.00  0.00           C
ATOM  7022  CA  LYS G  63   -59.457  82.699 303.967  1.00  0.00           C
ATOM  7023  CA  LEU G  64   -60.321  81.621 307.513  1.00  0.00           C
ATOM  7024  CA  ARG G  65   -60.915  85.315 308.151  1.00  0.00           C
ATOM  7025  CA  ARG G  66   -62.965  86.412 305.156  1.00  0.00           C
ATOM  7026  CA  ILE G  67   -65.169  83.449 305.988  1.00  0.00           C
ATOM  7027  CA  TYR G  68   -66.396  85.288 309.071  1.00  0.00           C
ATOM  7028  CA  GLY G  69   -66.285  88.703 307.411  1.00  0.00           C
ATOM  7029  CA  ILE G  70   -64.206  89.966 310.335  1.00  0.00           C
ATOM  7030  CA  SER G  71   -61.585  92.723 310.558  1.00  0.00           C
ATOM  7031  CA  GLU G  72   -57.964  91.728 310.978  1.00  0.00           C
ATOM  7032  CA  ARG G  73   -58.003  93.903 314.087  1.00  0.00           C
ATOM  7033  CA  GLN G  74   -60.698  91.800 315.818  1.00  0.00           C
ATOM  7034  CA  PHE G  75   -59.537  88.567 314.215  1.00  0.00           C
ATOM  7035  CA  ARG G  76   -56.004  88.997 315.618  1.00  0.00           C
ATOM  7036  CA  ASN G  77   -57.186  89.644 319.174  1.00  0.00           C
ATOM  7037  CA  LEU G  78   -59.257  86.456 319.094  1.00  0.00           C
ATOM  7038  CA  PHE G  79   -56.160  84.595 317.996  1.00  0.00           C
ATOM  7039  CA  GLU G  80   -53.953  86.057 320.731  1.00  0.00           C
ATOM  7040  CA  GLU G  81   -56.769  84.991 323.048  1.00  0.00           C
ATOM  7041  CA  ALA G  82   -56.815  81.439 321.792  1.00  0.00           C
ATOM  7042  CA  SER G  83   -53.040  81.481 322.177  1.00  0.00           C
ATOM  7043  CA  LYS G  84   -53.027  82.176 325.895  1.00  0.00           C
ATOM  7044  CA  LYS G  85   -55.922  79.937 326.871  1.00  0.00           C
ATOM  7045  CA  LYS G  86   -55.131  76.263 327.452  1.00  0.00           C
ATOM  7046  CA  GLY G  87   -55.651  73.778 324.635  1.00  0.00           C
ATOM  7047  CA  VAL G  88   -54.577  73.422 321.034  1.00  0.00           C
ATOM  7048  CA  THR G  89   -54.537  77.058 320.024  1.00  0.00           C
ATOM  7049  CA  GLY G  90   -55.659  76.058 316.542  1.00  0.00           C
ATOM  7050  CA  SER G  91   -59.078  74.720 317.445  1.00  0.00           C
ATOM  7051  CA  VAL G  92   -59.582  76.892 320.536  1.00  0.00           C
ATOM  7052  CA  PHE G  93   -59.307  79.767 318.057  1.00  0.00           C
ATOM  7053  CA  LEU G  94   -61.982  78.312 315.792  1.00  0.00           C
ATOM  7054  CA  GLY G  95   -64.182  77.754 318.830  1.00  0.00           C
ATOM  7055  CA  LEU G  96   -64.169  81.460 319.616  1.00  0.00           C
ATOM  7056  CA  LEU G  97   -64.793  82.366 316.000  1.00  0.00           C
ATOM  7057  CA  GLU G  98   -67.883  80.142 316.018  1.00  0.00           C
ATOM  7058  CA  SER G  99   -69.104  81.709 319.287  1.00  0.00           C
ATOM  7059  CA  ARG G 100   -69.796  85.108 317.755  1.00  0.00           C
ATOM  7060  CA  LEU G 101   -73.474  85.864 318.237  1.00  0.00           C
ATOM  7061  CA  ASP G 102   -73.610  86.994 314.632  1.00  0.00           C
ATOM  7062  CA  ASN G 103   -72.090  83.680 313.536  1.00  0.00           C
ATOM  7063  CA  VAL G 104   -74.429  81.574 315.628  1.00  0.00           C
ATOM  7064  CA  VAL G 105   -77.457  83.326 314.150  1.00  0.00           C
ATOM  7065  CA  TYR G 106   -76.120  82.300 310.726  1.00  0.00           C
ATOM  7066  CA  ARG G 107   -75.401  78.801 311.999  1.00  0.00           C
ATOM  7067  CA  LEU G 108   -78.979  78.538 313.340  1.00  0.00           C
ATOM  7068  CA  GLY G 109   -80.510  79.364 309.970  1.00  0.00           C
ATOM  7069  CA  PHE G 110   -82.107  82.631 311.053  1.00  0.00           C
ATOM  7070  CA  ALA G 111   -80.106  84.458 308.395  1.00  0.00           C
ATOM  7071  CA  VAL G 112   -79.095  83.161 304.981  1.00  0.00           C
ATOM  7072  CA  SER G 113   -75.579  84.583 305.150  1.00  0.00           C
ATOM  7073  CA  ARG G 114   -73.126  85.728 307.807  1.00  0.00           C
ATOM  7074  CA  ARG G 115   -73.541  89.312 306.667  1.00  0.00           C
ATOM  7075  CA  GLN G 116   -77.341  89.108 306.897  1.00  0.00           C
ATOM  7076  CA  ALA G 117   -77.076  87.648 310.391  1.00  0.00           C
ATOM  7077  CA  ARG G 118   -74.741  90.492 311.314  1.00  0.00           C
ATOM  7078  CA  GLN G 119   -77.503  92.939 310.386  1.00  0.00           C
ATOM  7079  CA  LEU G 120   -80.264  91.010 312.128  1.00  0.00           C
ATOM  7080  CA  VAL G 121   -78.230  91.109 315.320  1.00  0.00           C
ATOM  7081  CA  ARG G 122   -77.405  94.766 314.650  1.00  0.00           C
ATOM  7082  CA  HIS G 123   -80.959  95.940 313.885  1.00  0.00           C
ATOM  7083  CA  GLY G 124   -82.116  94.320 317.159  1.00  0.00           C
ATOM  7084  CA  HIS G 125   -84.022  91.418 315.559  1.00  0.00           C
ATOM  7085  CA  ILE G 126   -82.153  89.005 317.873  1.00  0.00           C
ATOM  7086  CA  THR G 127   -82.299  87.792 321.472  1.00  0.00           C
ATOM  7087  CA  VAL G 128   -80.032  86.062 323.992  1.00  0.00           C
```

```
ATOM   7088  CA  ASN G 129     -81.812  84.640 327.033  1.00  0.00           C
ATOM   7089  CA  GLY G 130     -84.508  87.219 326.550  1.00  0.00           C
ATOM   7090  CA  ARG G 131     -82.471  90.442 326.701  1.00  0.00           C
ATOM   7091  CA  ARG G 132     -81.866  91.555 323.133  1.00  0.00           C
ATOM   7092  CA  VAL G 133     -78.278  91.939 321.972  1.00  0.00           C
ATOM   7093  CA  ASP G 134     -77.229  94.004 318.937  1.00  0.00           C
ATOM   7094  CA  LEU G 135     -73.496  93.300 319.277  1.00  0.00           C
ATOM   7095  CA  PRO G 136     -72.261  91.006 316.477  1.00  0.00           C
ATOM   7096  CA  SER G 137     -69.017  90.419 318.332  1.00  0.00           C
ATOM   7097  CA  TYR G 138     -71.041  89.244 321.322  1.00  0.00           C
ATOM   7098  CA  ARG G 139     -69.648  85.954 322.621  1.00  0.00           C
ATOM   7099  CA  VAL G 140     -72.308  83.265 323.019  1.00  0.00           C
ATOM   7100  CA  ARG G 141     -71.574  80.823 325.865  1.00  0.00           C
ATOM   7101  CA  PRO G 142     -72.761  77.201 326.164  1.00  0.00           C
ATOM   7102  CA  GLY G 143     -76.300  77.187 327.501  1.00  0.00           C
ATOM   7103  CA  ASP G 144     -77.659  80.318 325.883  1.00  0.00           C
ATOM   7104  CA  GLU G 145     -80.935  80.499 323.958  1.00  0.00           C
ATOM   7105  CA  ILE G 146     -80.762  82.512 320.764  1.00  0.00           C
ATOM   7106  CA  ALA G 147     -84.269  83.506 319.779  1.00  0.00           C
ATOM   7107  CA  VAL G 148     -85.587  85.776 317.082  1.00  0.00           C
ATOM   7108  CA  ALA G 149     -87.016  89.061 318.334  1.00  0.00           C
ATOM   7109  CA  GLU G 150     -90.744  88.774 318.948  1.00  0.00           C
ATOM   7110  CA  LYS G 151     -91.500  92.007 317.136  1.00  0.00           C
ATOM   7111  CA  SER G 152     -89.574  90.579 314.181  1.00  0.00           C
ATOM   7112  CA  ARG G 153     -91.019  87.052 314.326  1.00  0.00           C
ATOM   7113  CA  ASN G 154     -93.542  88.440 311.859  1.00  0.00           C
ATOM   7114  CA  LEU G 155     -90.887  89.853 309.534  1.00  0.00           C
ATOM   7115  CA  GLU G 156     -91.181  88.447 306.029  1.00  0.00           C
ATOM   7116  CA  LEU G 157     -87.454  87.684 305.959  1.00  0.00           C
ATOM   7117  CA  ILE G 158     -87.458  85.748 309.221  1.00  0.00           C
ATOM   7118  CA  ARG G 159     -90.484  83.685 308.225  1.00  0.00           C
ATOM   7119  CA  GLN G 160     -88.942  82.603 304.900  1.00  0.00           C
ATOM   7120  CA  ASN G 161     -85.608  81.509 306.390  1.00  0.00           C
ATOM   7121  CA  LEU G 162     -87.153  79.803 309.396  1.00  0.00           C
ATOM   7122  CA  GLU G 163     -89.531  78.087 306.973  1.00  0.00           C
ATOM   7123  CA  ALA G 164     -86.940  76.604 304.615  1.00  0.00           C
ATOM   7124  CA  MET G 165     -85.238  75.807 307.889  1.00  0.00           C
ATOM   7125  CA  LYS G 166     -87.863  73.091 308.300  1.00  0.00           C
ATOM   7126  CA  GLY G 167     -86.069  69.769 308.047  1.00  0.00           C
ATOM   7127  CA  ARG G 168     -82.589  71.276 307.726  1.00  0.00           C
ATOM   7128  CA  LYS G 169     -80.464  69.690 310.451  1.00  0.00           C
ATOM   7129  CA  VAL G 170     -78.194  71.696 312.753  1.00  0.00           C
ATOM   7130  CA  GLY G 171     -74.622  71.469 314.034  1.00  0.00           C
ATOM   7131  CA  PRO G 172     -74.105  68.849 316.802  1.00  0.00           C
ATOM   7132  CA  TRP G 173     -73.081  71.675 319.168  1.00  0.00           C
ATOM   7133  CA  LEU G 174     -76.350  73.484 318.533  1.00  0.00           C
ATOM   7134  CA  SER G 175     -80.102  72.742 318.440  1.00  0.00           C
ATOM   7135  CA  LEU G 176     -83.175  74.741 317.497  1.00  0.00           C
ATOM   7136  CA  ASP G 177     -86.920  74.848 318.128  1.00  0.00           C
ATOM   7137  CA  VAL G 178     -88.214  76.123 314.778  1.00  0.00           C
ATOM   7138  CA  GLU G 179     -91.531  76.694 316.579  1.00  0.00           C
ATOM   7139  CA  GLY G 180     -90.786  79.643 318.835  1.00  0.00           C
ATOM   7140  CA  MET G 181     -87.830  80.319 316.567  1.00  0.00           C
ATOM   7141  CA  LYS G 182     -85.403  79.509 319.370  1.00  0.00           C
ATOM   7142  CA  GLY G 183     -82.110  77.643 319.447  1.00  0.00           C
ATOM   7143  CA  LYS G 184     -79.383  76.722 321.918  1.00  0.00           C
ATOM   7144  CA  PHE G 185     -75.598  76.884 321.965  1.00  0.00           C
ATOM   7145  CA  LEU G 186     -74.922  73.437 323.444  1.00  0.00           C
ATOM   7146  CA  ARG G 187     -71.126  73.451 323.481  1.00  0.00           C
ATOM   7147  CA  LEU G 188     -68.036  74.990 321.866  1.00  0.00           C
ATOM   7148  CA  PRO G 189     -67.632  73.304 318.480  1.00  0.00           C
ATOM   7149  CA  ASP G 190     -64.478  71.245 318.019  1.00  0.00           C
ATOM   7150  CA  ARG G 191     -62.198  71.295 315.000  1.00  0.00           C
ATOM   7151  CA  GLU G 192     -63.970  68.152 313.714  1.00  0.00           C
ATOM   7152  CA  ASP G 193     -67.432  69.767 313.976  1.00  0.00           C
ATOM   7153  CA  LEU G 194     -66.438  72.365 311.381  1.00  0.00           C
ATOM   7154  CA  ALA G 195     -65.883  71.425 307.749  1.00  0.00           C
ATOM   7155  CA  LEU G 196     -63.791  74.524 307.187  1.00  0.00           C
ATOM   7156  CA  PRO G 197     -61.603  74.590 304.052  1.00  0.00           C
ATOM   7157  CA  VAL G 198     -59.056  75.997 306.485  1.00  0.00           C
ATOM   7158  CA  GLN G 199     -55.803  74.709 307.918  1.00  0.00           C
ATOM   7159  CA  GLU G 200     -55.289  76.671 311.120  1.00  0.00           C
ATOM   7160  CA  ASN G 201     -51.797  75.199 311.423  1.00  0.00           C
ATOM   7161  CA  LEU G 202     -50.808  77.662 308.720  1.00  0.00           C
ATOM   7162  CA  VAL G 203     -52.794  80.403 310.453  1.00  0.00           C
ATOM   7163  CA  ILE G 204     -50.916  79.859 313.686  1.00  0.00           C
ATOM   7164  CA  GLU G 205     -47.668  79.787 311.766  1.00  0.00           C
ATOM   7165  CA  PHE G 206     -48.527  83.067 310.056  1.00  0.00           C
ATOM   7166  CA  TYR G 207     -48.901  84.834 313.378  1.00  0.00           C
ATOM   7167  CA  SER G 208     -45.581  83.264 314.381  1.00  0.00           C
ATOM   7168  CA  ARG G 209     -43.457  85.283 311.953  1.00  0.00           C
TER    7169          ARG G 209
ATOM   7170  CA  ASP H   5     -46.299  58.401 300.350  1.00  0.00           C
ATOM   7171  CA  PHE H   6     -43.226  60.690 300.298  1.00  0.00           C
ATOM   7172  CA  GLU H   7     -43.847  64.443 300.274  1.00  0.00           C
ATOM   7173  CA  GLU H   8     -40.923  66.424 298.882  1.00  0.00           C
ATOM   7174  CA  LYS H   9     -39.741  69.819 300.193  1.00  0.00           C
```

```
ATOM   7175  CA  MET H   10     -36.801  71.687 298.625  1.00  0.00           C
ATOM   7176  CA  ILE H   11     -34.584  73.465 301.189  1.00  0.00           C
ATOM   7177  CA  LEU H   12     -32.325  75.514 298.918  1.00  0.00           C
ATOM   7178  CA  ILE H   13     -30.886  75.562 295.425  1.00  0.00           C
ATOM   7179  CA  ARG H   14     -27.735  77.547 294.693  1.00  0.00           C
ATOM   7180  CA  ARG H   15     -25.963  78.378 291.489  1.00  0.00           C
ATOM   7181  CA  THR H   16     -22.267  77.786 292.369  1.00  0.00           C
ATOM   7182  CA  ALA H   17     -19.366  78.336 289.909  1.00  0.00           C
ATOM   7183  CA  ARG H   18     -16.104  77.226 288.374  1.00  0.00           C
ATOM   7184  CA  MET H   19     -13.376  78.751 286.177  1.00  0.00           C
ATOM   7185  CA  GLN H   20     -11.866  77.765 282.860  1.00  0.00           C
ATOM   7186  CA  ALA H   21     -10.164  80.040 280.419  1.00  0.00           C
ATOM   7187  CA  GLY H   22     -12.844  81.801 278.500  1.00  0.00           C
ATOM   7188  CA  GLY H   23     -14.916  82.102 281.653  1.00  0.00           C
ATOM   7189  CA  ARG H   24     -17.295  80.932 284.349  1.00  0.00           C
ATOM   7190  CA  ARG H   25     -19.071  77.596 284.217  1.00  0.00           C
ATOM   7191  CA  PHE H   26     -21.878  76.933 286.655  1.00  0.00           C
ATOM   7192  CA  ARG H   27     -23.483  73.938 288.342  1.00  0.00           C
ATOM   7193  CA  PHE H   28     -26.528  73.801 290.582  1.00  0.00           C
ATOM   7194  CA  GLY H   29     -26.908  72.184 293.926  1.00  0.00           C
ATOM   7195  CA  ALA H   30     -30.219  71.388 295.508  1.00  0.00           C
ATOM   7196  CA  LEU H   31     -30.931  70.294 299.051  1.00  0.00           C
ATOM   7197  CA  VAL H   32     -34.079  68.230 299.214  1.00  0.00           C
ATOM   7198  CA  VAL H   33     -36.042  66.790 302.122  1.00  0.00           C
ATOM   7199  CA  VAL H   34     -38.293  63.811 301.657  1.00  0.00           C
ATOM   7200  CA  GLY H   35     -40.724  62.494 304.213  1.00  0.00           C
ATOM   7201  CA  ASP H   36     -44.008  60.688 304.749  1.00  0.00           C
ATOM   7202  CA  ARG H   37     -44.908  62.787 307.786  1.00  0.00           C
ATOM   7203  CA  GLN H   38     -45.204  59.414 309.481  1.00  0.00           C
ATOM   7204  CA  GLY H   39     -41.723  59.064 310.908  1.00  0.00           C
ATOM   7205  CA  ARG H   40     -39.523  58.759 307.854  1.00  0.00           C
ATOM   7206  CA  VAL H   41     -37.305  61.578 306.538  1.00  0.00           C
ATOM   7207  CA  GLY H   42     -34.443  61.673 304.131  1.00  0.00           C
ATOM   7208  CA  LEU H   43     -32.072  64.464 303.175  1.00  0.00           C
ATOM   7209  CA  GLY H   44     -30.304  64.551 299.865  1.00  0.00           C
ATOM   7210  CA  PHE H   45     -27.908  66.991 298.278  1.00  0.00           C
ATOM   7211  CA  GLY H   46     -27.707  66.620 294.537  1.00  0.00           C
ATOM   7212  CA  LYS H   47     -25.735  68.651 292.038  1.00  0.00           C
ATOM   7213  CA  ALA H   48     -26.136  68.813 288.292  1.00  0.00           C
ATOM   7214  CA  PRO H   49     -25.597  71.123 285.292  1.00  0.00           C
ATOM   7215  CA  GLU H   50     -29.276  72.075 285.502  1.00  0.00           C
ATOM   7216  CA  VAL H   51     -31.688  73.005 288.277  1.00  0.00           C
ATOM   7217  CA  PRO H   52     -34.139  70.157 287.509  1.00  0.00           C
ATOM   7218  CA  LEU H   53     -31.642  67.332 287.108  1.00  0.00           C
ATOM   7219  CA  ALA H   54     -30.302  68.651 290.401  1.00  0.00           C
ATOM   7220  CA  VAL H   55     -33.578  68.587 292.329  1.00  0.00           C
ATOM   7221  CA  GLN H   56     -34.318  65.208 290.800  1.00  0.00           C
ATOM   7222  CA  LYS H   57     -30.859  63.936 291.704  1.00  0.00           C
ATOM   7223  CA  ALA H   58     -31.323  65.207 295.267  1.00  0.00           C
ATOM   7224  CA  GLY H   59     -34.818  63.757 295.614  1.00  0.00           C
ATOM   7225  CA  TYR H   60     -33.436  60.394 294.558  1.00  0.00           C
ATOM   7226  CA  TYR H   61     -30.485  60.781 296.930  1.00  0.00           C
ATOM   7227  CA  ALA H   62     -32.733  61.767 299.820  1.00  0.00           C
ATOM   7228  CA  ARG H   63     -34.985  58.754 299.253  1.00  0.00           C
ATOM   7229  CA  ARG H   64     -31.935  56.595 299.839  1.00  0.00           C
ATOM   7230  CA  ASN H   65     -30.647  57.405 303.344  1.00  0.00           C
ATOM   7231  CA  MET H   66     -33.839  57.773 305.385  1.00  0.00           C
ATOM   7232  CA  VAL H   67     -34.079  58.176 309.146  1.00  0.00           C
ATOM   7233  CA  GLU H   68     -36.654  56.667 311.489  1.00  0.00           C
ATOM   7234  CA  VAL H   69     -37.936  59.428 313.778  1.00  0.00           C
ATOM   7235  CA  PRO H   70     -39.213  58.031 317.132  1.00  0.00           C
ATOM   7236  CA  LEU H   71     -42.239  60.334 317.201  1.00  0.00           C
ATOM   7237  CA  GLN H   72     -44.374  60.393 320.338  1.00  0.00           C
ATOM   7238  CA  ASN H   73     -47.615  62.305 320.160  1.00  0.00           C
ATOM   7239  CA  GLY H   74     -46.190  64.480 317.382  1.00  0.00           C
ATOM   7240  CA  THR H   75     -43.224  65.468 319.524  1.00  0.00           C
ATOM   7241  CA  ILE H   76     -39.851  63.999 320.352  1.00  0.00           C
ATOM   7242  CA  PRO H   77     -38.658  61.795 323.268  1.00  0.00           C
ATOM   7243  CA  HIS H   78     -35.923  64.093 324.533  1.00  0.00           C
ATOM   7244  CA  GLU H   79     -33.639  67.024 323.817  1.00  0.00           C
ATOM   7245  CA  ILE H   80     -30.501  66.469 321.779  1.00  0.00           C
ATOM   7246  CA  GLU H   81     -27.943  69.034 320.769  1.00  0.00           C
ATOM   7247  CA  VAL H   82     -25.833  68.198 317.779  1.00  0.00           C
ATOM   7248  CA  GLU H   83     -22.814  69.918 316.301  1.00  0.00           C
ATOM   7249  CA  PHE H   84     -21.912  69.302 312.685  1.00  0.00           C
ATOM   7250  CA  GLY H   85     -19.026  71.368 311.452  1.00  0.00           C
ATOM   7251  CA  ALA H   86     -19.555  74.738 313.085  1.00  0.00           C
ATOM   7252  CA  SER H   87     -23.312  74.231 312.996  1.00  0.00           C
ATOM   7253  CA  LYS H   88     -25.042  73.300 316.212  1.00  0.00           C
ATOM   7254  CA  ILE H   89     -28.726  72.350 316.220  1.00  0.00           C
ATOM   7255  CA  VAL H   90     -30.829  72.096 319.347  1.00  0.00           C
ATOM   7256  CA  LEU H   91     -34.079  70.169 319.654  1.00  0.00           C
ATOM   7257  CA  LYS H   92     -36.379  70.210 322.686  1.00  0.00           C
ATOM   7258  CA  PRO H   93     -39.720  68.361 322.965  1.00  0.00           C
ATOM   7259  CA  ALA H   94     -42.938  70.367 323.283  1.00  0.00           C
ATOM   7260  CA  ALA H   95     -46.562  69.806 324.286  1.00  0.00           C
ATOM   7261  CA  PRO H   96     -49.363  69.844 321.704  1.00  0.00           C
```

```
ATOM   7262  CA  GLY H  97     -50.408  73.222 320.349  1.00  0.00           C
ATOM   7263  CA  THR H  98     -46.837  74.475 320.484  1.00  0.00           C
ATOM   7264  CA  GLY H  99     -46.189  74.048 316.757  1.00  0.00           C
ATOM   7265  CA  VAL H 100     -42.984  73.335 314.888  1.00  0.00           C
ATOM   7266  CA  ILE H 101     -40.962  76.293 316.134  1.00  0.00           C
ATOM   7267  CA  ALA H 102     -37.765  76.366 314.135  1.00  0.00           C
ATOM   7268  CA  GLY H 103     -36.002  78.124 311.292  1.00  0.00           C
ATOM   7269  CA  ALA H 104     -36.843  76.990 307.758  1.00  0.00           C
ATOM   7270  CA  VAL H 105     -34.197  74.325 307.094  1.00  0.00           C
ATOM   7271  CA  PRO H 106     -34.744  72.641 310.498  1.00  0.00           C
ATOM   7272  CA  ARG H 107     -38.516  72.989 310.196  1.00  0.00           C
ATOM   7273  CA  ALA H 108     -38.868  71.611 306.668  1.00  0.00           C
ATOM   7274  CA  ILE H 109     -37.183  68.445 307.860  1.00  0.00           C
ATOM   7275  CA  LEU H 110     -39.026  68.192 311.159  1.00  0.00           C
ATOM   7276  CA  GLU H 111     -42.370  68.557 309.317  1.00  0.00           C
ATOM   7277  CA  LEU H 112     -41.926  65.828 306.725  1.00  0.00           C
ATOM   7278  CA  ALA H 113     -40.347  64.037 309.635  1.00  0.00           C
ATOM   7279  CA  GLY H 114     -43.862  63.913 311.009  1.00  0.00           C
ATOM   7280  CA  VAL H 115     -43.011  66.088 313.975  1.00  0.00           C
ATOM   7281  CA  THR H 116     -45.715  68.566 314.776  1.00  0.00           C
ATOM   7282  CA  ASP H 117     -44.648  70.137 318.072  1.00  0.00           C
ATOM   7283  CA  ILE H 118     -41.046  71.120 318.920  1.00  0.00           C
ATOM   7284  CA  LEU H 119     -38.786  73.822 320.337  1.00  0.00           C
ATOM   7285  CA  THR H 120     -35.719  74.396 318.176  1.00  0.00           C
ATOM   7286  CA  LYS H 121     -32.568  76.483 317.965  1.00  0.00           C
ATOM   7287  CA  GLU H 122     -29.735  76.993 315.493  1.00  0.00           C
ATOM   7288  CA  LEU H 123     -26.443  77.875 317.085  1.00  0.00           C
ATOM   7289  CA  GLY H 124     -22.991  78.485 315.611  1.00  0.00           C
ATOM   7290  CA  SER H 125     -22.608  78.355 311.849  1.00  0.00           C
ATOM   7291  CA  ARG H 126     -25.979  78.693 310.208  1.00  0.00           C
ATOM   7292  CA  ASN H 127     -25.065  77.230 306.864  1.00  0.00           C
ATOM   7293  CA  PRO H 128     -28.373  75.688 305.801  1.00  0.00           C
ATOM   7294  CA  ILE H 129     -26.516  72.733 304.348  1.00  0.00           C
ATOM   7295  CA  ASN H 130     -24.651  72.131 307.588  1.00  0.00           C
ATOM   7296  CA  ILE H 131     -27.656  72.841 309.792  1.00  0.00           C
ATOM   7297  CA  ALA H 132     -29.508  70.275 307.688  1.00  0.00           C
ATOM   7298  CA  TYR H 133     -26.911  67.518 308.187  1.00  0.00           C
ATOM   7299  CA  ALA H 134     -26.797  68.583 311.835  1.00  0.00           C
ATOM   7300  CA  THR H 135     -30.540  68.135 312.142  1.00  0.00           C
ATOM   7301  CA  MET H 136     -30.624  64.707 310.510  1.00  0.00           C
ATOM   7302  CA  GLU H 137     -27.843  63.572 312.835  1.00  0.00           C
ATOM   7303  CA  ALA H 138     -29.795  64.895 315.786  1.00  0.00           C
ATOM   7304  CA  LEU H 139     -32.795  62.872 314.651  1.00  0.00           C
ATOM   7305  CA  ARG H 140     -30.736  59.709 314.147  1.00  0.00           C
ATOM   7306  CA  GLN H 141     -29.492  59.920 317.722  1.00  0.00           C
ATOM   7307  CA  LEU H 142     -32.956  60.100 319.294  1.00  0.00           C
ATOM   7308  CA  ARG H 143     -33.628  57.156 321.595  1.00  0.00           C
ATOM   7309  CA  THR H 144     -36.619  55.811 323.485  1.00  0.00           C
ATOM   7310  CA  LYS H 145     -37.081  54.657 327.064  1.00  0.00           C
ATOM   7311  CA  ALA H 146     -37.487  51.393 325.168  1.00  0.00           C
ATOM   7312  CA  ASP H 147     -34.119  51.472 323.376  1.00  0.00           C
ATOM   7313  CA  VAL H 148     -32.458  52.793 326.508  1.00  0.00           C
ATOM   7314  CA  GLU H 149     -33.983  50.079 328.693  1.00  0.00           C
ATOM   7315  CA  ARG H 150     -32.999  47.600 326.005  1.00  0.00           C
ATOM   7316  CA  LEU H 151     -29.419  48.957 325.907  1.00  0.00           C
ATOM   7317  CA  ARG H 152     -28.996  48.637 329.643  1.00  0.00           C
ATOM   7318  CA  LYS H 153     -30.450  45.132 330.169  1.00  0.00           C
ATOM   7319  CA  GLY H 154     -27.608  42.611 330.140  1.00  0.00           C
TER    7320      GLY H 154
ATOM   7321  CA  MET I   1      41.345  72.165 348.582  1.00  0.00           C
ATOM   7322  CA  ARG I   2      40.973  70.883 345.019  1.00  0.00           C
ATOM   7323  CA  ARG I   3      43.310  68.732 342.894  1.00  0.00           C
ATOM   7324  CA  TYR I   4      44.639  70.496 339.759  1.00  0.00           C
ATOM   7325  CA  GLU I   5      47.061  70.088 336.856  1.00  0.00           C
ATOM   7326  CA  VAL I   6      49.610  72.787 336.109  1.00  0.00           C
ATOM   7327  CA  ASN I   7      51.098  72.960 332.617  1.00  0.00           C
ATOM   7328  CA  ILE I   8      54.036  75.203 331.892  1.00  0.00           C
ATOM   7329  CA  VAL I   9      55.759  75.780 328.569  1.00  0.00           C
ATOM   7330  CA  LEU I  10      59.023  77.695 328.751  1.00  0.00           C
ATOM   7331  CA  ASN I  11      61.849  78.668 326.393  1.00  0.00           C
ATOM   7332  CA  PRO I  12      63.608  75.644 324.794  1.00  0.00           C
ATOM   7333  CA  ASN I  13      66.912  77.516 324.734  1.00  0.00           C
ATOM   7334  CA  LEU I  14      67.747  77.524 328.420  1.00  0.00           C
ATOM   7335  CA  ASP I  15      71.072  76.053 329.535  1.00  0.00           C
ATOM   7336  CA  GLN I  16      71.280  73.417 332.273  1.00  0.00           C
ATOM   7337  CA  SER I  17      71.508  76.239 334.823  1.00  0.00           C
ATOM   7338  CA  GLN I  18      69.116  78.876 333.425  1.00  0.00           C
ATOM   7339  CA  LEU I  19      66.449  76.180 333.220  1.00  0.00           C
ATOM   7340  CA  ALA I  20      66.836  74.769 336.731  1.00  0.00           C
ATOM   7341  CA  LEU I  21      66.617  78.399 337.906  1.00  0.00           C
ATOM   7342  CA  GLU I  22      63.156  78.921 336.435  1.00  0.00           C
ATOM   7343  CA  LYS I  23      62.026  75.626 337.953  1.00  0.00           C
ATOM   7344  CA  GLU I  24      63.289  77.073 341.215  1.00  0.00           C
ATOM   7345  CA  ILE I  25      60.932  80.053 341.104  1.00  0.00           C
ATOM   7346  CA  ILE I  26      58.104  77.686 340.116  1.00  0.00           C
ATOM   7347  CA  GLN I  27      58.525  75.268 343.028  1.00  0.00           C
ATOM   7348  CA  ARG I  28      59.054  78.366 345.149  1.00  0.00           C
```

| | | | | | | | | | | |
|---|---|---|---|---|---|---|---|---|---|---|
| ATOM | 7349 | CA | ALA | I | 29 | 55.910 | 79.984 | 343.759 | 1.00 | 0.00 | C |
| ATOM | 7350 | CA | LEU | I | 30 | 53.836 | 76.857 | 344.244 | 1.00 | 0.00 | C |
| ATOM | 7351 | CA | GLU | I | 31 | 54.432 | 76.630 | 347.987 | 1.00 | 0.00 | C |
| ATOM | 7352 | CA | ASN | I | 32 | 53.910 | 80.386 | 348.240 | 1.00 | 0.00 | C |
| ATOM | 7353 | CA | TYR | I | 33 | 50.325 | 79.658 | 347.228 | 1.00 | 0.00 | C |
| ATOM | 7354 | CA | GLY | I | 34 | 49.718 | 76.327 | 348.929 | 1.00 | 0.00 | C |
| ATOM | 7355 | CA | ALA | I | 35 | 50.589 | 74.100 | 345.995 | 1.00 | 0.00 | C |
| ATOM | 7356 | CA | ARG | I | 36 | 51.171 | 70.636 | 347.470 | 1.00 | 0.00 | C |
| ATOM | 7357 | CA | VAL | I | 37 | 53.074 | 68.926 | 344.619 | 1.00 | 0.00 | C |
| ATOM | 7358 | CA | GLU | I | 38 | 51.404 | 65.507 | 344.297 | 1.00 | 0.00 | C |
| ATOM | 7359 | CA | LYS | I | 39 | 53.632 | 64.642 | 341.345 | 1.00 | 0.00 | C |
| ATOM | 7360 | CA | VAL | I | 40 | 55.396 | 65.697 | 338.172 | 1.00 | 0.00 | C |
| ATOM | 7361 | CA | GLU | I | 41 | 56.339 | 64.845 | 334.596 | 1.00 | 0.00 | C |
| ATOM | 7362 | CA | GLU | I | 42 | 58.838 | 66.566 | 332.319 | 1.00 | 0.00 | C |
| ATOM | 7363 | CA | LEU | I | 43 | 58.405 | 65.699 | 328.635 | 1.00 | 0.00 | C |
| ATOM | 7364 | CA | GLY | I | 44 | 60.769 | 68.629 | 328.218 | 1.00 | 0.00 | C |
| ATOM | 7365 | CA | LEU | I | 45 | 61.255 | 69.570 | 324.574 | 1.00 | 0.00 | C |
| ATOM | 7366 | CA | ARG | I | 46 | 58.504 | 69.169 | 321.983 | 1.00 | 0.00 | C |
| ATOM | 7367 | CA | ARG | I | 47 | 57.869 | 70.394 | 318.427 | 1.00 | 0.00 | C |
| ATOM | 7368 | CA | LEU | I | 48 | 54.932 | 72.812 | 318.727 | 1.00 | 0.00 | C |
| ATOM | 7369 | CA | ALA | I | 49 | 52.132 | 72.718 | 316.160 | 1.00 | 0.00 | C |
| ATOM | 7370 | CA | TYR | I | 50 | 52.768 | 76.402 | 315.558 | 1.00 | 0.00 | C |
| ATOM | 7371 | CA | PRO | I | 51 | 55.484 | 78.785 | 316.793 | 1.00 | 0.00 | C |
| ATOM | 7372 | CA | ILE | I | 52 | 55.241 | 80.301 | 320.265 | 1.00 | 0.00 | C |
| ATOM | 7373 | CA | ALA | I | 53 | 57.262 | 83.477 | 320.739 | 1.00 | 0.00 | C |
| ATOM | 7374 | CA | LYS | I | 54 | 58.788 | 82.933 | 317.285 | 1.00 | 0.00 | C |
| ATOM | 7375 | CA | ASP | I | 55 | 60.377 | 79.785 | 318.732 | 1.00 | 0.00 | C |
| ATOM | 7376 | CA | PRO | I | 56 | 58.953 | 76.607 | 317.043 | 1.00 | 0.00 | C |
| ATOM | 7377 | CA | GLN | I | 57 | 59.723 | 74.386 | 320.055 | 1.00 | 0.00 | C |
| ATOM | 7378 | CA | GLY | I | 58 | 58.922 | 74.364 | 323.742 | 1.00 | 0.00 | C |
| ATOM | 7379 | CA | TYR | I | 59 | 60.024 | 72.898 | 327.073 | 1.00 | 0.00 | C |
| ATOM | 7380 | CA | PHE | I | 60 | 57.254 | 71.278 | 329.113 | 1.00 | 0.00 | C |
| ATOM | 7381 | CA | LEU | I | 61 | 56.603 | 70.924 | 332.821 | 1.00 | 0.00 | C |
| ATOM | 7382 | CA | TRP | I | 62 | 53.552 | 69.124 | 334.223 | 1.00 | 0.00 | C |
| ATOM | 7383 | CA | TYR | I | 63 | 52.662 | 69.370 | 337.914 | 1.00 | 0.00 | C |
| ATOM | 7384 | CA | GLN | I | 64 | 49.643 | 67.751 | 339.542 | 1.00 | 0.00 | C |
| ATOM | 7385 | CA | VAL | I | 65 | 48.969 | 69.757 | 342.709 | 1.00 | 0.00 | C |
| ATOM | 7386 | CA | GLU | I | 66 | 46.478 | 70.187 | 345.522 | 1.00 | 0.00 | C |
| ATOM | 7387 | CA | MET | I | 67 | 45.800 | 73.723 | 346.750 | 1.00 | 0.00 | C |
| ATOM | 7388 | CA | PRO | I | 68 | 43.326 | 76.410 | 347.918 | 1.00 | 0.00 | C |
| ATOM | 7389 | CA | GLU | I | 69 | 41.170 | 77.162 | 344.876 | 1.00 | 0.00 | C |
| ATOM | 7390 | CA | ASP | I | 70 | 40.754 | 80.712 | 346.188 | 1.00 | 0.00 | C |
| ATOM | 7391 | CA | ARG | I | 71 | 44.325 | 81.317 | 344.978 | 1.00 | 0.00 | C |
| ATOM | 7392 | CA | VAL | I | 72 | 44.675 | 79.183 | 341.840 | 1.00 | 0.00 | C |
| ATOM | 7393 | CA | ASN | I | 73 | 44.162 | 82.308 | 339.781 | 1.00 | 0.00 | C |
| ATOM | 7394 | CA | ASP | I | 74 | 46.988 | 84.165 | 341.568 | 1.00 | 0.00 | C |
| ATOM | 7395 | CA | LEU | I | 75 | 49.229 | 81.109 | 341.398 | 1.00 | 0.00 | C |
| ATOM | 7396 | CA | ALA | I | 76 | 49.141 | 81.546 | 337.631 | 1.00 | 0.00 | C |
| ATOM | 7397 | CA | ARG | I | 77 | 49.430 | 85.351 | 337.584 | 1.00 | 0.00 | C |
| ATOM | 7398 | CA | GLU | I | 78 | 52.651 | 84.608 | 339.384 | 1.00 | 0.00 | C |
| ATOM | 7399 | CA | LEU | I | 79 | 53.725 | 81.797 | 337.095 | 1.00 | 0.00 | C |
| ATOM | 7400 | CA | ARG | I | 80 | 53.211 | 84.000 | 334.018 | 1.00 | 0.00 | C |
| ATOM | 7401 | CA | ILE | I | 81 | 55.459 | 86.798 | 335.363 | 1.00 | 0.00 | C |
| ATOM | 7402 | CA | ARG | I | 82 | 58.598 | 84.931 | 334.322 | 1.00 | 0.00 | C |
| ATOM | 7403 | CA | ASP | I | 83 | 59.958 | 85.972 | 330.911 | 1.00 | 0.00 | C |
| ATOM | 7404 | CA | ASN | I | 84 | 61.019 | 82.434 | 330.018 | 1.00 | 0.00 | C |
| ATOM | 7405 | CA | VAL | I | 85 | 57.511 | 81.254 | 330.853 | 1.00 | 0.00 | C |
| ATOM | 7406 | CA | ARG | I | 86 | 55.545 | 81.372 | 327.624 | 1.00 | 0.00 | C |
| ATOM | 7407 | CA | ARG | I | 87 | 52.456 | 79.327 | 328.628 | 1.00 | 0.00 | C |
| ATOM | 7408 | CA | VAL | I | 88 | 50.644 | 78.391 | 331.818 | 1.00 | 0.00 | C |
| ATOM | 7409 | CA | MET | I | 89 | 47.490 | 76.293 | 331.994 | 1.00 | 0.00 | C |
| ATOM | 7410 | CA | VAL | I | 90 | 46.009 | 75.185 | 335.326 | 1.00 | 0.00 | C |
| ATOM | 7411 | CA | VAL | I | 91 | 43.264 | 72.589 | 335.001 | 1.00 | 0.00 | C |
| ATOM | 7412 | CA | LYS | I | 92 | 40.904 | 70.862 | 337.452 | 1.00 | 0.00 | C |
| ATOM | 7413 | CA | SER | I | 93 | 41.986 | 67.236 | 337.543 | 1.00 | 0.00 | C |
| ATOM | 7414 | CA | GLN | I | 94 | 39.357 | 64.961 | 336.057 | 1.00 | 0.00 | C |
| ATOM | 7415 | CA | GLU | I | 95 | 38.573 | 61.254 | 336.091 | 1.00 | 0.00 | C |
| ATOM | 7416 | CA | PRO | I | 96 | 39.861 | 59.840 | 332.798 | 1.00 | 0.00 | C |
| ATOM | 7417 | CA | PHE | I | 97 | 36.763 | 59.557 | 330.607 | 1.00 | 0.00 | C |
| ATOM | 7418 | CA | LEU | I | 98 | 37.604 | 56.428 | 328.570 | 1.00 | 0.00 | C |
| ATOM | 7419 | CA | ALA | I | 99 | 36.307 | 55.569 | 325.101 | 1.00 | 0.00 | C |
| ATOM | 7420 | CA | ASN | I | 100 | 36.329 | 52.842 | 322.448 | 1.00 | 0.00 | C |
| ATOM | 7421 | CA | ALA | I | 101 | 36.648 | 50.208 | 325.187 | 1.00 | 0.00 | C |
| TER | 7422 | | ALA | I | 101 | | | | | | |
| ATOM | 7423 | CA | ALA | J | 2 | 13.214 | 71.655 | 262.779 | 1.00 | 0.00 | |
| ATOM | 7424 | CA | ARG | J | 3 | 11.964 | 70.902 | 266.332 | 1.00 | 0.00 | C |
| ATOM | 7425 | CA | ARG | J | 4 | 11.286 | 67.193 | 265.750 | 1.00 | 0.00 | C |
| ATOM | 7426 | CA | ARG | J | 5 | 13.541 | 65.323 | 263.296 | 1.00 | 0.00 | C |
| ATOM | 7427 | CA | ARG | J | 6 | 17.100 | 66.172 | 262.371 | 1.00 | 0.00 | C |
| ATOM | 7428 | CA | ALA | J | 7 | 16.195 | 67.111 | 258.783 | 1.00 | 0.00 | C |
| ATOM | 7429 | CA | GLU | J | 8 | 18.308 | 64.829 | 256.597 | 1.00 | 0.00 | C |
| ATOM | 7430 | CA | VAL | J | 9 | 20.284 | 66.272 | 253.699 | 1.00 | 0.00 | C |
| ATOM | 7431 | CA | ARG | J | 10 | 18.689 | 66.181 | 250.244 | 1.00 | 0.00 | C |
| ATOM | 7432 | CA | GLN | J | 11 | 20.951 | 63.907 | 248.164 | 1.00 | 0.00 | C |
| ATOM | 7433 | CA | LEU | J | 12 | 21.646 | 65.353 | 244.713 | 1.00 | 0.00 | C |
| ATOM | 7434 | CA | GLN | J | 13 | 21.818 | 63.544 | 241.375 | 1.00 | 0.00 | C |
| ATOM | 7435 | CA | PRO | J | 14 | 25.441 | 63.548 | 240.108 | 1.00 | 0.00 | C |

```
ATOM   7436  CA  ASP J  15      26.757  65.722 237.276  1.00  0.00           C
ATOM   7437  CA  LEU J  16      25.680  64.986 233.690  1.00  0.00           C
ATOM   7438  CA  VAL J  17      29.350  65.153 232.666  1.00  0.00           C
ATOM   7439  CA  TYR J  18      31.560  64.459 235.674  1.00  0.00           C
ATOM   7440  CA  GLY J  19      28.906  62.475 237.526  1.00  0.00           C
ATOM   7441  CA  ASP J  20      30.107  64.426 240.533  1.00  0.00           C
ATOM   7442  CA  VAL J  21      27.407  65.520 242.973  1.00  0.00           C
ATOM   7443  CA  LEU J  22      29.502  68.353 244.406  1.00  0.00           C
ATOM   7444  CA  VAL J  23      29.345  69.867 240.942  1.00  0.00           C
ATOM   7445  CA  THR J  24      25.548  69.779 240.744  1.00  0.00           C
ATOM   7446  CA  ALA J  25      25.521  71.513 244.086  1.00  0.00           C
ATOM   7447  CA  PHE J  26      27.715  74.335 242.727  1.00  0.00           C
ATOM   7448  CA  ILE J  27      25.552  74.539 239.617  1.00  0.00           C
ATOM   7449  CA  ASN J  28      22.469  74.849 241.809  1.00  0.00           C
ATOM   7450  CA  LYS J  29      24.126  77.748 243.597  1.00  0.00           C
ATOM   7451  CA  ILE J  30      24.669  79.480 240.263  1.00  0.00           C
ATOM   7452  CA  MET J  31      21.113  78.826 239.115  1.00  0.00           C
ATOM   7453  CA  ARG J  32      18.446  81.464 239.653  1.00  0.00           C
ATOM   7454  CA  ASP J  33      14.697  81.216 238.962  1.00  0.00           C
ATOM   7455  CA  GLY J  34      15.214  77.525 238.342  1.00  0.00           C
ATOM   7456  CA  LYS J  35      16.773  78.264 234.949  1.00  0.00           C
ATOM   7457  CA  LYS J  36      18.995  75.237 235.557  1.00  0.00           C
ATOM   7458  CA  ASN J  37      20.036  75.013 231.894  1.00  0.00           C
ATOM   7459  CA  LEU J  38      21.690  78.425 231.754  1.00  0.00           C
ATOM   7460  CA  ALA J  39      23.179  77.463 235.115  1.00  0.00           C
ATOM   7461  CA  ALA J  40      24.687  74.201 233.840  1.00  0.00           C
ATOM   7462  CA  ARG J  41      25.984  75.905 230.725  1.00  0.00           C
ATOM   7463  CA  ILE J  42      27.739  78.682 232.608  1.00  0.00           C
ATOM   7464  CA  PHE J  43      29.585  76.130 234.718  1.00  0.00           C
ATOM   7465  CA  TYR J  44      30.617  74.001 231.767  1.00  0.00           C
ATOM   7466  CA  ASP J  45      31.611  76.948 229.560  1.00  0.00           C
ATOM   7467  CA  ALA J  46      33.708  77.934 232.555  1.00  0.00           C
ATOM   7468  CA  CYS J  47      35.269  74.484 232.800  1.00  0.00           C
ATOM   7469  CA  LYS J  48      36.340  74.898 229.196  1.00  0.00           C
ATOM   7470  CA  ILE J  49      37.800  78.293 230.106  1.00  0.00           C
ATOM   7471  CA  ILE J  50      39.752  76.534 232.834  1.00  0.00           C
ATOM   7472  CA  GLN J  51      41.033  74.178 230.133  1.00  0.00           C
ATOM   7473  CA  GLU J  52      42.318  76.854 227.810  1.00  0.00           C
ATOM   7474  CA  LYS J  53      43.913  79.451 230.089  1.00  0.00           C
ATOM   7475  CA  THR J  54      45.085  76.561 232.335  1.00  0.00           C
ATOM   7476  CA  GLY J  55      46.462  73.236 231.147  1.00  0.00           C
ATOM   7477  CA  GLN J  56      44.834  71.495 234.101  1.00  0.00           C
ATOM   7478  CA  GLU J  57      41.660  69.397 234.229  1.00  0.00           C
ATOM   7479  CA  PRO J  58      38.802  71.699 235.272  1.00  0.00           C
ATOM   7480  CA  LEU J  59      37.285  69.203 237.745  1.00  0.00           C
ATOM   7481  CA  LYS J  60      40.474  69.252 239.848  1.00  0.00           C
ATOM   7482  CA  VAL J  61      40.823  73.048 239.698  1.00  0.00           C
ATOM   7483  CA  PHE J  62      37.269  73.261 241.008  1.00  0.00           C
ATOM   7484  CA  LYS J  63      37.671  70.875 243.923  1.00  0.00           C
ATOM   7485  CA  GLN J  64      40.958  72.545 244.826  1.00  0.00           C
ATOM   7486  CA  ALA J  65      39.117  75.871 244.979  1.00  0.00           C
ATOM   7487  CA  VAL J  66      36.312  74.625 247.221  1.00  0.00           C
ATOM   7488  CA  GLU J  67      39.068  73.367 249.491  1.00  0.00           C
ATOM   7489  CA  ASN J  68      40.780  76.735 250.003  1.00  0.00           C
ATOM   7490  CA  VAL J  69      37.411  78.444 250.487  1.00  0.00           C
ATOM   7491  CA  LYS J  70      36.059  76.181 253.252  1.00  0.00           C
ATOM   7492  CA  PRO J  71      36.291  77.967 256.609  1.00  0.00           C
ATOM   7493  CA  ARG J  72      37.387  75.679 259.443  1.00  0.00           C
ATOM   7494  CA  MET J  73      36.452  78.055 262.276  1.00  0.00           C
ATOM   7495  CA  GLU J  74      33.631  80.576 262.305  1.00  0.00           C
ATOM   7496  CA  VAL J  75      32.117  82.912 264.849  1.00  0.00           C
ATOM   7497  CA  ARG J  76      28.531  82.419 266.058  1.00  0.00           C
ATOM   7498  CA  SER J  77      26.807  85.092 268.117  1.00  0.00           C
ATOM   7499  CA  ARG J  78      25.324  84.344 271.539  1.00  0.00           C
ATOM   7500  CA  ARG J  79      23.886  86.293 274.454  1.00  0.00           C
ATOM   7501  CA  VAL J  80      25.876  85.563 277.594  1.00  0.00           C
ATOM   7502  CA  GLY J  81      25.189  87.613 280.699  1.00  0.00           C
ATOM   7503  CA  GLY J  82      24.343  90.875 278.965  1.00  0.00           C
ATOM   7504  CA  ALA J  83      26.409  91.537 275.842  1.00  0.00           C
ATOM   7505  CA  ASN J  84      26.165  89.265 272.799  1.00  0.00           C
ATOM   7506  CA  TYR J  85      29.612  87.663 272.718  1.00  0.00           C
ATOM   7507  CA  GLN J  86      30.693  86.178 269.377  1.00  0.00           C
ATOM   7508  CA  VAL J  87      31.681  82.608 270.247  1.00  0.00           C
ATOM   7509  CA  PRO J  88      34.210  80.957 267.869  1.00  0.00           C
ATOM   7510  CA  MET J  89      33.731  77.349 266.891  1.00  0.00           C
ATOM   7511  CA  GLU J  90      34.378  74.591 264.384  1.00  0.00           C
ATOM   7512  CA  VAL J  91      32.344  74.257 261.225  1.00  0.00           C
ATOM   7513  CA  SER J  92      30.475  71.099 260.293  1.00  0.00           C
ATOM   7514  CA  PRO J  93      31.788  69.277 257.247  1.00  0.00           C
ATOM   7515  CA  ARG J  94      28.333  69.906 255.798  1.00  0.00           C
ATOM   7516  CA  ARG J  95      28.250  73.649 256.491  1.00  0.00           C
ATOM   7517  CA  GLN J  96      31.794  74.099 255.171  1.00  0.00           C
ATOM   7518  CA  GLN J  97      30.663  73.068 251.724  1.00  0.00           C
ATOM   7519  CA  SER J  98      27.494  75.171 251.695  1.00  0.00           C
ATOM   7520  CA  LEU J  99      29.589  78.204 252.607  1.00  0.00           C
ATOM   7521  CA  ALA J 100      32.429  77.434 250.195  1.00  0.00           C
ATOM   7522  CA  LEU J 101      30.196  77.007 247.148  1.00  0.00           C
```

```
ATOM   7523  CA  ARG J 102      28.038  79.950 248.143  1.00  0.00           C
ATOM   7524  CA  TRP J 103      31.058  82.188 248.665  1.00  0.00           C
ATOM   7525  CA  LEU J 104      32.532  81.197 245.312  1.00  0.00           C
ATOM   7526  CA  VAL J 105      29.436  82.080 243.299  1.00  0.00           C
ATOM   7527  CA  GLN J 106      29.103  85.278 245.312  1.00  0.00           C
ATOM   7528  CA  ALA J 107      32.659  86.513 244.788  1.00  0.00           C
ATOM   7529  CA  ALA J 108      32.451  85.281 241.224  1.00  0.00           C
ATOM   7530  CA  ASN J 109      29.467  87.505 240.570  1.00  0.00           C
ATOM   7531  CA  GLN J 110      31.468  90.189 242.333  1.00  0.00           C
ATOM   7532  CA  ARG J 111      34.117  90.181 239.606  1.00  0.00           C
ATOM   7533  CA  PRO J 112      34.237  92.634 236.657  1.00  0.00           C
ATOM   7534  CA  GLU J 113      34.428  90.567 233.435  1.00  0.00           C
ATOM   7535  CA  ARG J 114      31.099  91.083 231.648  1.00  0.00           C
ATOM   7536  CA  ARG J 115      30.605  87.321 231.009  1.00  0.00           C
ATOM   7537  CA  ALA J 116      28.987  85.200 233.702  1.00  0.00           C
ATOM   7538  CA  ALA J 117      30.747  82.024 232.554  1.00  0.00           C
ATOM   7539  CA  VAL J 118      34.101  83.810 232.831  1.00  0.00           C
ATOM   7540  CA  ARG J 119      33.671  85.250 236.299  1.00  0.00           C
ATOM   7541  CA  ILE J 120      33.164  81.695 237.444  1.00  0.00           C
ATOM   7542  CA  ALA J 121      36.090  80.434 235.412  1.00  0.00           C
ATOM   7543  CA  HIS J 122      38.472  83.074 236.730  1.00  0.00           C
ATOM   7544  CA  GLU J 123      37.141  82.976 240.292  1.00  0.00           C
ATOM   7545  CA  LEU J 124      37.705  79.230 240.566  1.00  0.00           C
ATOM   7546  CA  MET J 125      41.301  79.564 239.351  1.00  0.00           C
ATOM   7547  CA  ASP J 126      42.088  82.471 241.688  1.00  0.00           C
ATOM   7548  CA  ALA J 127      40.567  80.408 244.489  1.00  0.00           C
ATOM   7549  CA  ALA J 128      42.799  77.483 243.580  1.00  0.00           C
ATOM   7550  CA  GLU J 129      45.901  79.710 243.730  1.00  0.00           C
ATOM   7551  CA  GLY J 130      44.786  80.955 247.130  1.00  0.00           C
ATOM   7552  CA  LYS J 131      43.715  84.417 246.015  1.00  0.00           C
ATOM   7553  CA  GLY J 132      40.380  85.976 245.090  1.00  0.00           C
ATOM   7554  CA  GLY J 133      37.293  87.400 246.758  1.00  0.00           C
ATOM   7555  CA  ALA J 134      36.148  83.925 247.748  1.00  0.00           C
ATOM   7556  CA  VAL J 135      39.195  83.042 249.805  1.00  0.00           C
ATOM   7557  CA  LYS J 136      39.132  86.523 251.296  1.00  0.00           C
ATOM   7558  CA  LYS J 137      35.832  85.867 253.078  1.00  0.00           C
ATOM   7559  CA  LYS J 138      37.074  82.448 254.142  1.00  0.00           C
ATOM   7560  CA  GLU J 139      40.239  83.832 255.704  1.00  0.00           C
ATOM   7561  CA  ASP J 140      38.232  86.784 257.067  1.00  0.00           C
ATOM   7562  CA  VAL J 141      35.990  84.363 258.930  1.00  0.00           C
ATOM   7563  CA  GLU J 142      38.831  82.446 260.541  1.00  0.00           C
ATOM   7564  CA  ARG J 143      40.413  85.791 261.437  1.00  0.00           C
ATOM   7565  CA  MET J 144      37.145  86.860 263.073  1.00  0.00           C
ATOM   7566  CA  ALA J 145      37.246  83.664 265.141  1.00  0.00           C
ATOM   7567  CA  GLU J 146      40.582  83.203 266.888  1.00  0.00           C
ATOM   7568  CA  ALA J 147      40.254  86.981 267.429  1.00  0.00           C
ATOM   7569  CA  ASN J 148      37.370  86.454 269.824  1.00  0.00           C
ATOM   7570  CA  ARG J 149      39.131  83.330 270.993  1.00  0.00           C
ATOM   7571  CA  ALA J 150      38.733  84.556 274.568  1.00  0.00           C
ATOM   7572  CA  TYR J 151      34.980  84.046 274.665  1.00  0.00           C
ATOM   7573  CA  ALA J 152      35.667  80.544 273.358  1.00  0.00           C
ATOM   7574  CA  HIS J 153      35.016  79.050 276.783  1.00  0.00           C
ATOM   7575  CA  TYR J 154      31.348  79.386 275.845  1.00  0.00           C
ATOM   7576  CA  ARG J 155      32.162  76.485 273.507  1.00  0.00           C
ATOM   7577  CA  TRP J 156      28.501  75.842 272.654  1.00  0.00           C
TER    7578          TRP J 156
ATOM   7579  CA  MET K   1      -1.510  70.638 341.704  1.00  0.00           C
ATOM   7580  CA  LEU K   2      -4.785  68.717 341.350  1.00  0.00           C
ATOM   7581  CA  THR K   3      -7.090  71.722 341.321  1.00  0.00           C
ATOM   7582  CA  ASP K   4     -10.464  69.896 341.105  1.00  0.00           C
ATOM   7583  CA  PRO K   5     -10.600  66.221 342.213  1.00  0.00           C
ATOM   7584  CA  ILE K   6     -14.243  65.818 341.176  1.00  0.00           C
ATOM   7585  CA  ALA K   7     -13.754  67.325 337.763  1.00  0.00           C
ATOM   7586  CA  ASP K   8     -10.642  65.233 337.416  1.00  0.00           C
ATOM   7587  CA  MET K   9     -12.730  62.114 337.889  1.00  0.00           C
ATOM   7588  CA  LEU K  10     -15.520  63.000 335.483  1.00  0.00           C
ATOM   7589  CA  THR K  11     -12.871  63.670 332.878  1.00  0.00           C
ATOM   7590  CA  ARG K  12     -10.915  60.482 333.502  1.00  0.00           C
ATOM   7591  CA  ILE K  13     -14.263  58.731 332.929  1.00  0.00           C
ATOM   7592  CA  ARG K  14     -15.152  60.814 329.889  1.00  0.00           C
ATOM   7593  CA  ASN K  15     -11.665  60.185 328.507  1.00  0.00           C
ATOM   7594  CA  ALA K  16     -11.584  56.418 329.141  1.00  0.00           C
ATOM   7595  CA  THR K  17     -15.022  55.764 327.768  1.00  0.00           C
ATOM   7596  CA  ARG K  18     -14.167  57.594 324.548  1.00  0.00           C
ATOM   7597  CA  VAL K  19     -11.535  54.967 323.842  1.00  0.00           C
ATOM   7598  CA  TYR K  20     -13.661  52.238 325.344  1.00  0.00           C
ATOM   7599  CA  LYS K  21     -11.539  51.200 328.279  1.00  0.00           C
ATOM   7600  CA  GLU K  22     -13.077  48.371 330.296  1.00  0.00           C
ATOM   7601  CA  SER K  23     -11.855  49.691 333.675  1.00  0.00           C
ATOM   7602  CA  THR K  24     -10.234  53.062 334.654  1.00  0.00           C
ATOM   7603  CA  ASP K  25      -8.659  54.235 337.929  1.00  0.00           C
ATOM   7604  CA  VAL K  26      -9.170  57.484 339.849  1.00  0.00           C
ATOM   7605  CA  PRO K  27      -7.600  58.409 343.212  1.00  0.00           C
ATOM   7606  CA  ALA K  28     -10.091  57.591 345.971  1.00  0.00           C
ATOM   7607  CA  SER K  29     -11.868  60.186 348.088  1.00  0.00           C
ATOM   7608  CA  ARG K  30     -14.972  59.624 350.244  1.00  0.00           C
ATOM   7609  CA  PHE K  31     -16.813  62.228 348.173  1.00  0.00           C
```

```
ATOM  7610  CA  LYS K  32   -15.780  60.745 344.812  1.00  0.00           C
ATOM  7611  CA  GLU K  33   -16.969  57.340 345.985  1.00  0.00           C
ATOM  7612  CA  GLU K  34   -20.257  58.968 346.955  1.00  0.00           C
ATOM  7613  CA  ILE K  35   -20.701  60.183 343.397  1.00  0.00           C
ATOM  7614  CA  LEU K  36   -19.789  56.852 341.826  1.00  0.00           C
ATOM  7615  CA  ARG K  37   -22.527  55.280 344.011  1.00  0.00           C
ATOM  7616  CA  ILE K  38   -25.095  57.261 341.986  1.00  0.00           C
ATOM  7617  CA  LEU K  39   -23.361  56.648 338.686  1.00  0.00           C
ATOM  7618  CA  ALA K  40   -23.856  52.956 339.265  1.00  0.00           C
ATOM  7619  CA  ARG K  41   -27.391  53.084 340.652  1.00  0.00           C
ATOM  7620  CA  GLU K  42   -28.477  55.292 337.768  1.00  0.00           C
ATOM  7621  CA  GLY K  43   -26.953  52.636 335.548  1.00  0.00           C
ATOM  7622  CA  PHE K  44   -24.210  54.749 333.928  1.00  0.00           C
ATOM  7623  CA  ILE K  45   -21.376  52.477 334.978  1.00  0.00           C
ATOM  7624  CA  LYS K  46   -21.157  48.744 335.539  1.00  0.00           C
ATOM  7625  CA  GLY K  47   -19.986  49.767 338.986  1.00  0.00           C
ATOM  7626  CA  TYR K  48   -16.715  50.518 340.758  1.00  0.00           C
ATOM  7627  CA  GLU K  49   -14.473  49.112 343.496  1.00  0.00           C
ATOM  7628  CA  ARG K  50   -11.732  50.175 345.901  1.00  0.00           C
ATOM  7629  CA  VAL K  51    -8.257  49.134 344.794  1.00  0.00           C
ATOM  7630  CA  ASP K  52    -4.652  49.914 345.738  1.00  0.00           C
ATOM  7631  CA  VAL K  53    -2.316  51.312 343.071  1.00  0.00           C
ATOM  7632  CA  ASP K  54     1.338  51.615 344.083  1.00  0.00           C
ATOM  7633  CA  GLY K  55     0.144  51.488 347.669  1.00  0.00           C
ATOM  7634  CA  LYS K  56    -2.298  54.338 347.358  1.00  0.00           C
ATOM  7635  CA  PRO K  57    -6.123  54.090 347.323  1.00  0.00           C
ATOM  7636  CA  TYR K  58    -7.976  54.246 344.012  1.00  0.00           C
ATOM  7637  CA  LEU K  59   -11.419  53.519 342.711  1.00  0.00           C
ATOM  7638  CA  ARG K  60   -11.692  51.221 339.704  1.00  0.00           C
ATOM  7639  CA  VAL K  61   -14.520  52.454 337.573  1.00  0.00           C
ATOM  7640  CA  TYR K  62   -16.068  49.783 335.390  1.00  0.00           C
ATOM  7641  CA  LEU K  63   -17.247  51.400 332.199  1.00  0.00           C
ATOM  7642  CA  LYS K  64   -20.358  50.392 330.277  1.00  0.00           C
ATOM  7643  CA  TYR K  65   -21.222  50.751 326.589  1.00  0.00           C
ATOM  7644  CA  GLY K  66   -23.976  49.928 324.166  1.00  0.00           C
ATOM  7645  CA  PRO K  67   -23.647  47.006 321.765  1.00  0.00           C
ATOM  7646  CA  ARG K  68   -21.527  46.787 318.618  1.00  0.00           C
ATOM  7647  CA  ARG K  69   -23.032  48.528 315.587  1.00  0.00           C
ATOM  7648  CA  GLN K  70   -23.666  48.035 311.858  1.00  0.00           C
ATOM  7649  CA  GLY K  71   -22.106  49.723 308.852  1.00  0.00           C
ATOM  7650  CA  PRO K  72   -18.769  51.567 309.058  1.00  0.00           C
ATOM  7651  CA  ASP K  73   -17.465  52.376 312.538  1.00  0.00           C
ATOM  7652  CA  PRO K  74   -18.947  49.549 314.639  1.00  0.00           C
ATOM  7653  CA  ARG K  75   -18.068  51.483 317.782  1.00  0.00           C
ATOM  7654  CA  PRO K  76   -20.710  51.091 320.503  1.00  0.00           C
ATOM  7655  CA  GLU K  77   -22.972  53.983 321.474  1.00  0.00           C
ATOM  7656  CA  GLN K  78   -21.842  55.389 324.813  1.00  0.00           C
ATOM  7657  CA  VAL K  79   -24.056  54.935 327.846  1.00  0.00           C
ATOM  7658  CA  ILE K  80   -22.544  58.173 329.112  1.00  0.00           C
ATOM  7659  CA  HIS K  81   -23.132  60.475 326.157  1.00  0.00           C
ATOM  7660  CA  HIS K  82   -22.444  63.401 328.424  1.00  0.00           C
ATOM  7661  CA  ILE K  83   -21.001  64.294 331.811  1.00  0.00           C
ATOM  7662  CA  ARG K  84   -20.068  67.930 332.525  1.00  0.00           C
ATOM  7663  CA  ARG K  85   -18.838  69.639 335.733  1.00  0.00           C
ATOM  7664  CA  ILE K  86   -20.883  72.603 336.849  1.00  0.00           C
ATOM  7665  CA  SER K  87   -20.067  73.925 340.262  1.00  0.00           C
ATOM  7666  CA  LYS K  88   -16.298  74.513 340.096  1.00  0.00           C
ATOM  7667  CA  PRO K  89   -13.866  76.258 342.437  1.00  0.00           C
ATOM  7668  CA  GLY K  90   -13.945  79.977 341.814  1.00  0.00           C
ATOM  7669  CA  ARG K  91   -17.536  79.682 340.562  1.00  0.00           C
ATOM  7670  CA  ARG K  92   -19.448  77.577 343.013  1.00  0.00           C
ATOM  7671  CA  VAL K  93   -23.028  76.848 341.974  1.00  0.00           C
ATOM  7672  CA  TYR K  94   -25.850  76.205 344.431  1.00  0.00           C
ATOM  7673  CA  VAL K  95   -29.571  75.778 343.814  1.00  0.00           C
ATOM  7674  CA  GLY K  96   -32.779  75.911 345.810  1.00  0.00           C
ATOM  7675  CA  VAL K  97   -35.109  72.932 345.599  1.00  0.00           C
ATOM  7676  CA  LYS K  98   -37.222  75.006 343.214  1.00  0.00           C
ATOM  7677  CA  GLU K  99   -34.200  75.592 340.926  1.00  0.00           C
ATOM  7678  CA  ILE K 100   -32.930  72.007 340.575  1.00  0.00           C
ATOM  7679  CA  PRO K 101   -32.630  71.650 336.781  1.00  0.00           C
ATOM  7680  CA  ARG K 102   -34.461  69.064 334.688  1.00  0.00           C
ATOM  7681  CA  VAL K 103   -31.649  67.453 332.718  1.00  0.00           C
ATOM  7682  CA  ARG K 104   -32.280  66.260 329.169  1.00  0.00           C
ATOM  7683  CA  ARG K 105   -36.056  66.491 329.593  1.00  0.00           C
ATOM  7684  CA  GLY K 106   -35.782  63.884 332.318  1.00  0.00           C
ATOM  7685  CA  LEU K 107   -33.673  61.333 330.423  1.00  0.00           C
ATOM  7686  CA  GLY K 108   -30.497  62.614 332.025  1.00  0.00           C
ATOM  7687  CA  ILE K 109   -29.618  63.372 335.599  1.00  0.00           C
ATOM  7688  CA  ALA K 110   -27.906  65.953 337.725  1.00  0.00           C
ATOM  7689  CA  ILE K 111   -25.909  65.143 340.811  1.00  0.00           C
ATOM  7690  CA  LEU K 112   -26.321  67.525 343.723  1.00  0.00           C
ATOM  7691  CA  SER K 113   -24.617  67.600 347.085  1.00  0.00           C
ATOM  7692  CA  THR K 114   -27.131  68.400 349.839  1.00  0.00           C
ATOM  7693  CA  SER K 115   -26.942  68.554 353.621  1.00  0.00           C
ATOM  7694  CA  LYS K 116   -28.913  65.320 353.218  1.00  0.00           C
ATOM  7695  CA  GLY K 117   -26.092  63.752 351.181  1.00  0.00           C
ATOM  7696  CA  VAL K 118   -25.256  63.308 347.495  1.00  0.00           C
```

```
ATOM   7697  CA  LEU K 119     -28.477  62.743 345.537  1.00  0.00           C
ATOM   7698  CA  THR K 120     -29.759  62.943 341.992  1.00  0.00           C
ATOM   7699  CA  ASP K 121     -32.119  65.733 340.943  1.00  0.00           C
ATOM   7700  CA  ARG K 122     -35.115  63.453 341.402  1.00  0.00           C
ATOM   7701  CA  GLU K 123     -33.924  62.232 344.811  1.00  0.00           C
ATOM   7702  CA  ALA K 124     -33.291  65.799 345.940  1.00  0.00           C
ATOM   7703  CA  ARG K 125     -36.677  67.025 344.802  1.00  0.00           C
ATOM   7704  CA  LYS K 126     -38.280  64.141 346.682  1.00  0.00           C
ATOM   7705  CA  LEU K 127     -36.406  64.908 349.914  1.00  0.00           C
ATOM   7706  CA  GLY K 128     -37.265  68.520 349.039  1.00  0.00           C
ATOM   7707  CA  VAL K 129     -33.758  69.984 349.312  1.00  0.00           C
ATOM   7708  CA  GLY K 130     -31.185  71.868 347.287  1.00  0.00           C
ATOM   7709  CA  GLY K 131     -27.427  72.398 347.322  1.00  0.00           C
ATOM   7710  CA  GLU K 132     -24.190  72.630 345.313  1.00  0.00           C
ATOM   7711  CA  LEU K 133     -24.807  71.454 341.742  1.00  0.00           C
ATOM   7712  CA  ILE K 134     -21.886  69.031 341.329  1.00  0.00           C
ATOM   7713  CA  CYS K 135     -22.532  67.893 337.772  1.00  0.00           C
ATOM   7714  CA  GLU K 136     -24.834  66.810 334.951  1.00  0.00           C
ATOM   7715  CA  VAL K 137     -24.905  63.396 333.272  1.00  0.00           C
ATOM   7716  CA  TRP K 138     -26.885  61.918 330.380  1.00  0.00           C
TER    7717      TRP K 138
ATOM   7718  CA  GLU L   2      11.018  41.203 218.087  1.00  0.00           C
ATOM   7719  CA  GLN L   3       9.818  44.235 220.056  1.00  0.00           C
ATOM   7720  CA  TYR L   4       9.467  45.569 223.605  1.00  0.00           C
ATOM   7721  CA  TYR L   5       7.227  48.052 225.392  1.00  0.00           C
ATOM   7722  CA  GLY L   6       7.082  50.271 228.452  1.00  0.00           C
ATOM   7723  CA  THR L   7       5.014  53.416 228.858  1.00  0.00           C
ATOM   7724  CA  GLY L   8       6.340  55.905 231.389  1.00  0.00           C
ATOM   7725  CA  ARG L   9       4.673  58.983 232.854  1.00  0.00           C
ATOM   7726  CA  ARG L  10       6.126  62.025 234.624  1.00  0.00           C
ATOM   7727  CA  LYS L  11       4.766  65.346 235.843  1.00  0.00           C
ATOM   7728  CA  GLU L  12       1.965  64.898 233.305  1.00  0.00           C
ATOM   7729  CA  ALA L  13       3.757  63.386 230.310  1.00  0.00           C
ATOM   7730  CA  VAL L  14       3.269  60.077 228.509  1.00  0.00           C
ATOM   7731  CA  ALA L  15       6.028  58.362 226.557  1.00  0.00           C
ATOM   7732  CA  ARG L  16       5.538  55.260 224.424  1.00  0.00           C
ATOM   7733  CA  VAL L  17       8.842  53.394 224.536  1.00  0.00           C
ATOM   7734  CA  PHE L  18       9.479  50.724 221.905  1.00  0.00           C
ATOM   7735  CA  LEU L  19      12.804  48.910 222.113  1.00  0.00           C
ATOM   7736  CA  ARG L  20      14.022  46.678 219.274  1.00  0.00           C
ATOM   7737  CA  PRO L  21      17.363  44.823 219.077  1.00  0.00           C
ATOM   7738  CA  GLY L  22      19.461  46.974 216.768  1.00  0.00           C
ATOM   7739  CA  ASN L  23      22.034  49.774 216.499  1.00  0.00           C
ATOM   7740  CA  GLY L  24      21.086  52.061 219.378  1.00  0.00           C
ATOM   7741  CA  LYS L  25      19.457  55.001 217.633  1.00  0.00           C
ATOM   7742  CA  VAL L  26      16.299  56.684 218.896  1.00  0.00           C
ATOM   7743  CA  THR L  27      13.418  58.198 216.986  1.00  0.00           C
ATOM   7744  CA  VAL L  28      11.512  60.528 219.274  1.00  0.00           C
ATOM   7745  CA  ASN L  29       8.298  61.538 217.512  1.00  0.00           C
ATOM   7746  CA  GLY L  30      10.091  61.267 214.212  1.00  0.00           C
ATOM   7747  CA  GLN L  31      13.053  63.529 214.889  1.00  0.00           C
ATOM   7748  CA  ASP L  32      16.296  62.010 216.121  1.00  0.00           C
ATOM   7749  CA  PHE L  33      16.781  61.782 219.892  1.00  0.00           C
ATOM   7750  CA  ASN L  34      19.298  64.613 219.542  1.00  0.00           C
ATOM   7751  CA  GLU L  35      16.925  66.395 217.187  1.00  0.00           C
ATOM   7752  CA  TYR L  36      13.807  66.657 219.381  1.00  0.00           C
ATOM   7753  CA  PHE L  37      15.944  67.568 222.415  1.00  0.00           C
ATOM   7754  CA  GLN L  38      18.127  69.941 220.413  1.00  0.00           C
ATOM   7755  CA  GLY L  39      20.202  71.580 223.126  1.00  0.00           C
ATOM   7756  CA  LEU L  40      19.020  70.424 226.556  1.00  0.00           C
ATOM   7757  CA  VAL L  41      21.814  69.508 228.971  1.00  0.00           C
ATOM   7758  CA  ARG L  42      19.383  67.040 230.593  1.00  0.00           C
ATOM   7759  CA  ALA L  43      18.327  64.932 227.589  1.00  0.00           C
ATOM   7760  CA  VAL L  44      21.168  62.504 228.272  1.00  0.00           C
ATOM   7761  CA  ALA L  45      19.121  61.394 231.283  1.00  0.00           C
ATOM   7762  CA  ALA L  46      16.348  59.525 229.423  1.00  0.00           C
ATOM   7763  CA  LEU L  47      18.758  56.844 228.148  1.00  0.00           C
ATOM   7764  CA  GLU L  48      20.400  56.373 231.539  1.00  0.00           C
ATOM   7765  CA  PRO L  49      18.345  53.220 232.187  1.00  0.00           C
ATOM   7766  CA  LEU L  50      20.100  51.754 229.134  1.00  0.00           C
ATOM   7767  CA  ARG L  51      23.700  52.431 230.189  1.00  0.00           C
ATOM   7768  CA  ALA L  52      22.315  50.968 233.390  1.00  0.00           C
ATOM   7769  CA  VAL L  53      22.635  47.451 231.981  1.00  0.00           C
ATOM   7770  CA  ASP L  54      24.879  48.169 228.972  1.00  0.00           C
ATOM   7771  CA  ALA L  55      22.213  48.730 226.334  1.00  0.00           C
ATOM   7772  CA  LEU L  56      21.973  51.349 223.576  1.00  0.00           C
ATOM   7773  CA  GLY L  57      24.698  49.711 221.504  1.00  0.00           C
ATOM   7774  CA  ARG L  58      22.583  46.586 221.654  1.00  0.00           C
ATOM   7775  CA  PHE L  59      19.043  47.971 221.329  1.00  0.00           C
ATOM   7776  CA  ASP L  60      17.193  50.681 219.447  1.00  0.00           C
ATOM   7777  CA  ALA L  61      14.156  52.786 220.327  1.00  0.00           C
ATOM   7778  CA  TYR L  62      11.095  54.230 218.647  1.00  0.00           C
ATOM   7779  CA  ILE L  63       9.362  56.677 220.957  1.00  0.00           C
ATOM   7780  CA  THR L  64       6.092  58.601 220.909  1.00  0.00           C
ATOM   7781  CA  VAL L  65       5.890  61.444 223.396  1.00  0.00           C
ATOM   7782  CA  ARG L  66       2.934  63.755 224.015  1.00  0.00           C
ATOM   7783  CA  GLY L  67       2.075  65.867 227.050  1.00  0.00           C
```

```
ATOM   7784  CA   GLY L   68      3.766  68.376 229.327  1.00  0.00           C
ATOM   7785  CA   GLY L   69      7.187  69.780 228.517  1.00  0.00           C
ATOM   7786  CA   LYS L   70     10.394  68.452 226.985  1.00  0.00           C
ATOM   7787  CA   SER L   71     11.711  68.094 230.522  1.00  0.00           C
ATOM   7788  CA   GLY L   72      8.831  65.994 231.784  1.00  0.00           C
ATOM   7789  CA   GLN L   73      8.967  64.012 228.586  1.00  0.00           C
ATOM   7790  CA   ILE L   74     12.657  63.356 229.242  1.00  0.00           C
ATOM   7791  CA   ASP L   75     11.642  61.696 232.515  1.00  0.00           C
ATOM   7792  CA   ALA L   76      8.647  59.830 231.087  1.00  0.00           C
ATOM   7793  CA   ILE L   77     10.859  58.504 228.312  1.00  0.00           C
ATOM   7794  CA   LYS L   78     13.475  57.633 230.921  1.00  0.00           C
ATOM   7795  CA   LEU L   79     10.815  55.554 232.716  1.00  0.00           C
ATOM   7796  CA   GLY L   80      9.584  54.038 229.475  1.00  0.00           C
ATOM   7797  CA   ILE L   81     13.042  52.799 228.504  1.00  0.00           C
ATOM   7798  CA   ALA L   82     13.287  51.551 232.089  1.00  0.00           C
ATOM   7799  CA   ARG L   83     10.038  49.558 231.962  1.00  0.00           C
ATOM   7800  CA   ALA L   84     10.546  48.127 228.494  1.00  0.00           C
ATOM   7801  CA   LEU L   85     14.046  47.008 229.450  1.00  0.00           C
ATOM   7802  CA   VAL L   86     12.224  44.734 231.924  1.00  0.00           C
ATOM   7803  CA   GLN L   87      9.688  43.062 229.613  1.00  0.00           C
ATOM   7804  CA   TYR L   88     12.710  42.144 227.533  1.00  0.00           C
ATOM   7805  CA   ASN L   89     14.687  40.661 230.404  1.00  0.00           C
ATOM   7806  CA   PRO L   90     12.874  40.647 233.777  1.00  0.00           C
ATOM   7807  CA   ASP L   91     16.138  39.693 235.480  1.00  0.00           C
ATOM   7808  CA   TYR L   92     17.233  43.332 235.094  1.00  0.00           C
ATOM   7809  CA   ARG L   93     15.259  44.865 237.976  1.00  0.00           C
ATOM   7810  CA   ALA L   94     17.899  43.710 240.469  1.00  0.00           C
ATOM   7811  CA   LYS L   95     20.154  46.509 239.164  1.00  0.00           C
ATOM   7812  CA   LEU L   96     17.663  48.718 237.344  1.00  0.00           C
ATOM   7813  CA   LYS L   97     15.624  49.391 240.513  1.00  0.00           C
ATOM   7814  CA   PRO L   98     18.236  50.081 243.189  1.00  0.00           C
ATOM   7815  CA   LEU L   99     18.658  53.240 241.082  1.00  0.00           C
ATOM   7816  CA   GLY L  100     14.919  53.805 241.169  1.00  0.00           C
ATOM   7817  CA   PHE L  101     14.327  54.181 237.445  1.00  0.00           C
ATOM   7818  CA   LEU L  102     11.235  52.002 237.904  1.00  0.00           C
ATOM   7819  CA   THR L  103      9.451  54.589 240.027  1.00  0.00           C
ATOM   7820  CA   ARG L  104      6.885  57.103 238.815  1.00  0.00           C
ATOM   7821  CA   ASP L  105      7.855  60.475 240.273  1.00  0.00           C
ATOM   7822  CA   ALA L  106      4.448  61.553 241.616  1.00  0.00           C
ATOM   7823  CA   ARG L  107      5.453  65.219 242.014  1.00  0.00           C
ATOM   7824  CA   VAL L  108      2.758  67.253 240.233  1.00  0.00           C
ATOM   7825  CA   VAL L  109      1.744  70.928 240.187  1.00  0.00           C
ATOM   7826  CA   GLU L  110     -0.071  71.959 243.367  1.00  0.00           C
ATOM   7827  CA   ARG L  111     -3.614  73.271 243.081  1.00  0.00           C
ATOM   7828  CA   LYS L  112     -3.994  77.050 243.329  1.00  0.00           C
ATOM   7829  CA   LYS L  113     -5.954  77.637 246.550  1.00  0.00           C
ATOM   7830  CA   TYR L  114     -8.119  80.718 246.982  1.00  0.00           C
ATOM   7831  CA   GLY L  115     -7.141  83.545 249.288  1.00  0.00           C
ATOM   7832  CA   LYS L  116     -3.562  82.883 248.253  1.00  0.00           C
ATOM   7833  CA   HIS L  117     -1.606  84.014 245.203  1.00  0.00           C
ATOM   7834  CA   LYS L  118     -0.180  80.685 244.177  1.00  0.00           C
ATOM   7835  CA   ALA L  119     -1.322  77.731 246.309  1.00  0.00           C
ATOM   7836  CA   ARG L  120      1.017  78.884 249.030  1.00  0.00           C
ATOM   7837  CA   ARG L  121      2.478  82.279 248.195  1.00  0.00           C
ATOM   7838  CA   ALA L  122      0.288  84.238 250.618  1.00  0.00           C
ATOM   7839  CA   PRO L  123     -0.420  87.753 250.096  1.00  0.00           C
ATOM   7840  CA   GLN L  124      1.777  90.712 251.499  1.00  0.00           C
ATOM   7841  CA   TYR L  125      1.192  93.944 253.416  1.00  0.00           C
ATOM   7842  CA   SER L  126      1.886  96.159 256.148  1.00  0.00           C
ATOM   7843  CA   LYS L  127      0.156  97.400 259.493  1.00  0.00           C
ATOM   7844  CA   ARG L  128      0.229  96.557 263.254  1.00  0.00           C
TER    7845       ARG L  128
ATOM   7846  CA   LYS M    3    -24.631  52.193 212.554  1.00  0.00           C
ATOM   7847  CA   ILE M    4    -26.736  54.182 215.009  1.00  0.00           C
ATOM   7848  CA   ARG M    5    -24.447  56.235 217.260  1.00  0.00           C
ATOM   7849  CA   ILE M    6    -26.135  57.038 220.560  1.00  0.00           C
ATOM   7850  CA   LYS M    7    -24.694  59.566 223.016  1.00  0.00           C
ATOM   7851  CA   LEU M    8    -26.162  59.519 226.519  1.00  0.00           C
ATOM   7852  CA   ARG M    9    -25.416  62.247 229.053  1.00  0.00           C
ATOM   7853  CA   GLY M   10    -26.686  62.761 232.578  1.00  0.00           C
ATOM   7854  CA   PHE M   11    -25.948  64.010 236.074  1.00  0.00           C
ATOM   7855  CA   ASP M   12    -26.528  60.739 237.904  1.00  0.00           C
ATOM   7856  CA   HIS M   13    -23.964  58.050 237.111  1.00  0.00           C
ATOM   7857  CA   LYS M   14    -26.695  55.494 237.818  1.00  0.00           C
ATOM   7858  CA   THR M   15    -29.523  57.128 235.914  1.00  0.00           C
ATOM   7859  CA   LEU M   16    -27.294  56.507 232.886  1.00  0.00           C
ATOM   7860  CA   ASP M   17    -25.819  53.097 233.596  1.00  0.00           C
ATOM   7861  CA   ALA M   18    -29.480  52.217 234.114  1.00  0.00           C
ATOM   7862  CA   SER M   19    -30.698  54.097 231.044  1.00  0.00           C
ATOM   7863  CA   ALA M   20    -27.895  53.222 228.614  1.00  0.00           C
ATOM   7864  CA   GLN M   21    -27.934  49.636 229.890  1.00  0.00           C
ATOM   7865  CA   LYS M   22    -31.573  49.217 228.868  1.00  0.00           C
ATOM   7866  CA   ILE M   23    -30.719  50.383 225.368  1.00  0.00           C
ATOM   7867  CA   VAL M   24    -28.063  47.655 225.227  1.00  0.00           C
ATOM   7868  CA   GLU M   25    -30.205  44.687 226.301  1.00  0.00           C
ATOM   7869  CA   ALA M   26    -33.076  45.847 224.099  1.00  0.00           C
ATOM   7870  CA   ALA M   27    -31.463  46.169 220.663  1.00  0.00           C
```

```
ATOM   7871  CA  ARG M  28     -29.376  43.056 221.474  1.00  0.00           C
ATOM   7872  CA  ARG M  29     -32.319  41.183 219.956  1.00  0.00           C
ATOM   7873  CA  SER M  30     -33.035  43.078 216.729  1.00  0.00           C
ATOM   7874  CA  GLY M  31     -29.746  44.353 215.302  1.00  0.00           C
ATOM   7875  CA  ALA M  32     -26.013  43.727 215.681  1.00  0.00           C
ATOM   7876  CA  GLN M  33     -24.702  43.058 219.190  1.00  0.00           C
ATOM   7877  CA  VAL M  34     -23.924  46.609 220.310  1.00  0.00           C
ATOM   7878  CA  SER M  35     -20.463  48.021 221.148  1.00  0.00           C
ATOM   7879  CA  GLY M  36     -21.299  47.858 224.849  1.00  0.00           C
ATOM   7880  CA  PRO M  37     -21.968  51.101 226.736  1.00  0.00           C
ATOM   7881  CA  ILE M  38     -18.580  52.808 226.447  1.00  0.00           C
ATOM   7882  CA  PRO M  39     -17.982  55.346 229.288  1.00  0.00           C
ATOM   7883  CA  LEU M  40     -16.314  58.599 228.149  1.00  0.00           C
ATOM   7884  CA  PRO M  41     -14.648  61.264 230.353  1.00  0.00           C
ATOM   7885  CA  THR M  42     -16.771  63.370 232.696  1.00  0.00           C
ATOM   7886  CA  ARG M  43     -16.680  67.178 232.557  1.00  0.00           C
ATOM   7887  CA  VAL M  44     -16.781  68.838 235.986  1.00  0.00           C
ATOM   7888  CA  ARG M  45     -17.858  72.415 236.737  1.00  0.00           C
ATOM   7889  CA  ARG M  46     -16.463  73.994 239.928  1.00  0.00           C
ATOM   7890  CA  PHE M  47     -18.127  76.936 241.655  1.00  0.00           C
ATOM   7891  CA  THR M  48     -15.943  78.237 244.425  1.00  0.00           C
ATOM   7892  CA  VAL M  49     -17.971  80.625 246.524  1.00  0.00           C
ATOM   7893  CA  ILE M  50     -17.257  82.697 249.639  1.00  0.00           C
ATOM   7894  CA  ARG M  51     -19.296  81.140 252.457  1.00  0.00           C
ATOM   7895  CA  GLY M  52     -20.879  84.161 254.040  1.00  0.00           C
ATOM   7896  CA  PRO M  53     -21.932  87.566 252.723  1.00  0.00           C
ATOM   7897  CA  PHE M  54     -19.801  90.611 253.573  1.00  0.00           C
ATOM   7898  CA  LYS M  55     -16.034  89.896 253.793  1.00  0.00           C
ATOM   7899  CA  HIS M  56     -14.402  86.776 255.275  1.00  0.00           C
ATOM   7900  CA  LYS M  57     -12.448  86.282 252.017  1.00  0.00           C
ATOM   7901  CA  ASP M  58     -11.291  82.867 253.219  1.00  0.00           C
ATOM   7902  CA  SER M  59     -14.604  81.088 253.791  1.00  0.00           C
ATOM   7903  CA  ARG M  60     -15.254  79.362 250.456  1.00  0.00           C
ATOM   7904  CA  GLU M  61     -16.733  75.815 250.251  1.00  0.00           C
ATOM   7905  CA  HIS M  62     -16.777  74.076 246.829  1.00  0.00           C
ATOM   7906  CA  PHE M  63     -19.631  73.082 244.507  1.00  0.00           C
ATOM   7907  CA  GLU M  64     -19.250  70.937 241.379  1.00  0.00           C
ATOM   7908  CA  LEU M  65     -21.755  69.994 238.645  1.00  0.00           C
ATOM   7909  CA  ARG M  66     -20.285  66.869 237.018  1.00  0.00           C
ATOM   7910  CA  THR M  67     -21.696  65.785 233.643  1.00  0.00           C
ATOM   7911  CA  HIS M  68     -21.368  62.126 232.649  1.00  0.00           C
ATOM   7912  CA  ASN M  69     -21.389  60.599 229.171  1.00  0.00           C
ATOM   7913  CA  ARG M  70     -22.143  57.233 227.519  1.00  0.00           C
ATOM   7914  CA  LEU M  71     -22.055  55.992 223.919  1.00  0.00           C
ATOM   7915  CA  VAL M  72     -23.049  52.384 223.114  1.00  0.00           C
ATOM   7916  CA  ASP M  73     -23.127  52.316 219.267  1.00  0.00           C
ATOM   7917  CA  ILE M  74     -25.423  49.950 217.329  1.00  0.00           C
ATOM   7918  CA  ILE M  75     -24.034  49.127 213.891  1.00  0.00           C
ATOM   7919  CA  ASN M  76     -26.351  47.203 211.540  1.00  0.00           C
ATOM   7920  CA  PRO M  77     -29.797  48.622 212.493  1.00  0.00           C
ATOM   7921  CA  ASN M  78     -32.836  46.452 211.822  1.00  0.00           C
ATOM   7922  CA  ARG M  79     -36.378  47.853 212.191  1.00  0.00           C
ATOM   7923  CA  LYS M  80     -37.052  45.762 215.325  1.00  0.00           C
ATOM   7924  CA  THR M  81     -34.002  47.508 216.790  1.00  0.00           C
ATOM   7925  CA  ILE M  82     -35.678  50.851 216.156  1.00  0.00           C
ATOM   7926  CA  GLU M  83     -38.642  49.053 217.726  1.00  0.00           C
ATOM   7927  CA  GLN M  84     -37.275  47.836 221.056  1.00  0.00           C
ATOM   7928  CA  LEU M  85     -35.832  51.331 221.513  1.00  0.00           C
ATOM   7929  CA  MET M  86     -37.957  53.880 219.626  1.00  0.00           C
ATOM   7930  CA  THR M  87     -40.578  53.941 222.383  1.00  0.00           C
ATOM   7931  CA  LEU M  88     -39.355  52.169 225.518  1.00  0.00           C
ATOM   7932  CA  ASP M  89     -37.374  54.581 227.723  1.00  0.00           C
ATOM   7933  CA  LEU M  90     -37.706  55.452 231.422  1.00  0.00           C
ATOM   7934  CA  PRO M  91     -35.282  57.811 233.304  1.00  0.00           C
ATOM   7935  CA  THR M  92     -35.948  61.549 233.815  1.00  0.00           C
ATOM   7936  CA  GLY M  93     -32.491  62.782 234.774  1.00  0.00           C
ATOM   7937  CA  VAL M  94     -31.262  61.776 231.331  1.00  0.00           C
ATOM   7938  CA  GLU M  95     -31.311  63.358 227.882  1.00  0.00           C
ATOM   7939  CA  ILE M  96     -30.163  61.561 224.728  1.00  0.00           C
ATOM   7940  CA  GLU M  97     -28.827  62.564 221.345  1.00  0.00           C
ATOM   7941  CA  ILE M  98     -28.541  60.092 218.492  1.00  0.00           C
ATOM   7942  CA  LYS M  99     -27.031  60.376 215.031  1.00  0.00           C
ATOM   7943  CA  THR M 100     -27.020  57.184 212.977  1.00  0.00           C
TER    7944          THR M 100
ATOM   7945  CA  LYS N  11      69.076  86.058 284.864  1.00  0.00           C
ATOM   7946  CA  ARG N  12      70.362  84.044 287.835  1.00  0.00           C
ATOM   7947  CA  GLN N  13      69.677  80.483 286.679  1.00  0.00           C
ATOM   7948  CA  VAL N  14      67.417  78.755 289.195  1.00  0.00           C
ATOM   7949  CA  ALA N  15      66.170  75.545 287.575  1.00  0.00           C
ATOM   7950  CA  SER N  16      64.071  74.022 290.379  1.00  0.00           C
ATOM   7951  CA  GLY N  17      61.179  76.072 291.750  1.00  0.00           C
ATOM   7952  CA  ARG N  18      57.512  76.662 292.596  1.00  0.00           C
ATOM   7953  CA  ALA N  19      54.537  77.667 290.436  1.00  0.00           C
ATOM   7954  CA  TYR N  20      51.536  79.288 292.097  1.00  0.00           C
ATOM   7955  CA  ILE N  21      48.299  79.072 290.170  1.00  0.00           C
ATOM   7956  CA  HIS N  22      45.716  81.484 291.535  1.00  0.00           C
ATOM   7957  CA  ALA N  23      42.360  80.793 289.847  1.00  0.00           C
```

| | | | | | | | | | | |
|---|---|---|---|---|---|---|---|---|---|---|
| ATOM | 7958 | CA | SER | N | 24 | 39.135 | 82.801 | 290.298 | 1.00 | 0.00 | C |
| ATOM | 7959 | CA | TYR | N | 25 | 35.846 | 83.347 | 288.508 | 1.00 | 0.00 | C |
| ATOM | 7960 | CA | ASN | N | 26 | 37.355 | 86.534 | 287.085 | 1.00 | 0.00 | C |
| ATOM | 7961 | CA | ASN | N | 27 | 40.962 | 85.840 | 286.133 | 1.00 | 0.00 | C |
| ATOM | 7962 | CA | THR | N | 28 | 43.929 | 83.518 | 286.481 | 1.00 | 0.00 | C |
| ATOM | 7963 | CA | ILE | N | 29 | 47.361 | 84.626 | 287.552 | 1.00 | 0.00 | C |
| ATOM | 7964 | CA | VAL | N | 30 | 50.431 | 82.397 | 287.665 | 1.00 | 0.00 | C |
| ATOM | 7965 | CA | THR | N | 31 | 53.547 | 83.303 | 289.604 | 1.00 | 0.00 | C |
| ATOM | 7966 | CA | ILE | N | 32 | 56.747 | 81.258 | 289.347 | 1.00 | 0.00 | C |
| ATOM | 7967 | CA | THR | N | 33 | 59.088 | 81.116 | 292.336 | 1.00 | 0.00 | C |
| ATOM | 7968 | CA | ASP | N | 34 | 62.434 | 79.860 | 293.591 | 1.00 | 0.00 | C |
| ATOM | 7969 | CA | PRO | N | 35 | 62.970 | 76.854 | 295.924 | 1.00 | 0.00 | C |
| ATOM | 7970 | CA | ASP | N | 36 | 61.853 | 79.002 | 298.851 | 1.00 | 0.00 | C |
| ATOM | 7971 | CA | GLY | N | 37 | 59.156 | 81.402 | 297.696 | 1.00 | 0.00 | C |
| ATOM | 7972 | CA | ASN | N | 38 | 60.526 | 84.580 | 296.118 | 1.00 | 0.00 | C |
| ATOM | 7973 | CA | PRO | N | 39 | 58.958 | 85.181 | 292.694 | 1.00 | 0.00 | C |
| ATOM | 7974 | CA | ILE | N | 40 | 61.005 | 85.007 | 289.520 | 1.00 | 0.00 | C |
| ATOM | 7975 | CA | THR | N | 41 | 58.277 | 86.001 | 287.046 | 1.00 | 0.00 | C |
| ATOM | 7976 | CA | TRP | N | 42 | 54.492 | 86.285 | 286.881 | 1.00 | 0.00 | C |
| ATOM | 7977 | CA | SER | N | 43 | 51.722 | 86.288 | 284.265 | 1.00 | 0.00 | C |
| ATOM | 7978 | CA | SER | N | 44 | 47.953 | 86.657 | 284.132 | 1.00 | 0.00 | C |
| ATOM | 7979 | CA | GLY | N | 45 | 44.939 | 87.156 | 281.905 | 1.00 | 0.00 | C |
| ATOM | 7980 | CA | GLY | N | 46 | 45.751 | 90.831 | 281.773 | 1.00 | 0.00 | C |
| ATOM | 7981 | CA | VAL | N | 47 | 49.507 | 90.460 | 281.330 | 1.00 | 0.00 | C |
| ATOM | 7982 | CA | ILE | N | 48 | 48.585 | 89.043 | 277.961 | 1.00 | 0.00 | C |
| ATOM | 7983 | CA | GLY | N | 49 | 46.016 | 90.508 | 275.590 | 1.00 | 0.00 | C |
| ATOM | 7984 | CA | TYR | N | 50 | 42.633 | 90.015 | 277.307 | 1.00 | 0.00 | C |
| ATOM | 7985 | CA | LYS | N | 51 | 41.167 | 92.877 | 279.330 | 1.00 | 0.00 | C |
| ATOM | 7986 | CA | GLY | N | 52 | 37.718 | 92.252 | 280.819 | 1.00 | 0.00 | C |
| ATOM | 7987 | CA | SER | N | 53 | 35.671 | 89.120 | 280.947 | 1.00 | 0.00 | C |
| ATOM | 7988 | CA | ARG | N | 54 | 38.041 | 87.360 | 278.512 | 1.00 | 0.00 | C |
| ATOM | 7989 | CA | LYS | N | 55 | 40.728 | 87.598 | 281.200 | 1.00 | 0.00 | C |
| ATOM | 7990 | CA | GLY | N | 56 | 39.129 | 84.732 | 283.131 | 1.00 | 0.00 | C |
| ATOM | 7991 | CA | THR | N | 57 | 38.443 | 82.117 | 280.441 | 1.00 | 0.00 | C |
| ATOM | 7992 | CA | PRO | N | 58 | 40.544 | 78.904 | 280.526 | 1.00 | 0.00 | C |
| ATOM | 7993 | CA | TYR | N | 59 | 42.239 | 79.906 | 277.298 | 1.00 | 0.00 | C |
| ATOM | 7994 | CA | ALA | N | 60 | 43.713 | 82.953 | 279.016 | 1.00 | 0.00 | C |
| ATOM | 7995 | CA | ALA | N | 61 | 44.672 | 80.765 | 281.963 | 1.00 | 0.00 | C |
| ATOM | 7996 | CA | GLN | N | 62 | 46.480 | 78.647 | 279.394 | 1.00 | 0.00 | C |
| ATOM | 7997 | CA | LEU | N | 63 | 48.289 | 81.494 | 277.682 | 1.00 | 0.00 | C |
| ATOM | 7998 | CA | ALA | N | 64 | 49.213 | 82.991 | 281.061 | 1.00 | 0.00 | C |
| ATOM | 7999 | CA | ALA | N | 65 | 50.522 | 79.642 | 282.295 | 1.00 | 0.00 | C |
| ATOM | 8000 | CA | LEU | N | 66 | 52.765 | 79.379 | 279.251 | 1.00 | 0.00 | C |
| ATOM | 8001 | CA | ASP | N | 67 | 53.898 | 83.014 | 279.417 | 1.00 | 0.00 | C |
| ATOM | 8002 | CA | ALA | N | 68 | 54.818 | 82.284 | 283.026 | 1.00 | 0.00 | C |
| ATOM | 8003 | CA | ALA | N | 69 | 56.889 | 79.222 | 282.139 | 1.00 | 0.00 | C |
| ATOM | 8004 | CA | LYS | N | 70 | 58.517 | 80.644 | 278.991 | 1.00 | 0.00 | C |
| ATOM | 8005 | CA | LYS | N | 71 | 59.675 | 83.745 | 280.901 | 1.00 | 0.00 | C |
| ATOM | 8006 | CA | ALA | N | 72 | 60.869 | 81.503 | 283.724 | 1.00 | 0.00 | C |
| ATOM | 8007 | CA | MET | N | 73 | 62.728 | 79.349 | 281.196 | 1.00 | 0.00 | C |
| ATOM | 8008 | CA | ALA | N | 74 | 65.016 | 82.374 | 280.851 | 1.00 | 0.00 | C |
| ATOM | 8009 | CA | TYR | N | 75 | 66.059 | 82.252 | 284.511 | 1.00 | 0.00 | C |
| ATOM | 8010 | CA | GLY | N | 76 | 66.937 | 78.691 | 283.526 | 1.00 | 0.00 | C |
| ATOM | 8011 | CA | MET | N | 77 | 63.940 | 77.060 | 285.238 | 1.00 | 0.00 | C |
| ATOM | 8012 | CA | GLN | N | 78 | 63.262 | 73.406 | 284.482 | 1.00 | 0.00 | C |
| ATOM | 8013 | CA | SER | N | 79 | 61.409 | 71.604 | 287.283 | 1.00 | 0.00 | C |
| ATOM | 8014 | CA | VAL | N | 80 | 58.532 | 73.119 | 289.268 | 1.00 | 0.00 | C |
| ATOM | 8015 | CA | ASP | N | 81 | 56.032 | 72.256 | 292.009 | 1.00 | 0.00 | C |
| ATOM | 8016 | CA | VAL | N | 82 | 52.558 | 73.517 | 291.221 | 1.00 | 0.00 | C |
| ATOM | 8017 | CA | ILE | N | 83 | 50.317 | 75.015 | 293.880 | 1.00 | 0.00 | C |
| ATOM | 8018 | CA | VAL | N | 84 | 46.693 | 75.692 | 293.073 | 1.00 | 0.00 | C |
| ATOM | 8019 | CA | ARG | N | 85 | 44.809 | 78.292 | 295.056 | 1.00 | 0.00 | C |
| ATOM | 8020 | CA | GLY | N | 86 | 41.112 | 78.909 | 294.552 | 1.00 | 0.00 | C |
| ATOM | 8021 | CA | THR | N | 87 | 38.594 | 77.603 | 292.065 | 1.00 | 0.00 | C |
| ATOM | 8022 | CA | GLY | N | 88 | 37.647 | 79.321 | 288.869 | 1.00 | 0.00 | C |
| ATOM | 8023 | CA | ALA | N | 89 | 37.326 | 79.736 | 285.138 | 1.00 | 0.00 | C |
| ATOM | 8024 | CA | GLY | N | 90 | 39.879 | 77.231 | 283.874 | 1.00 | 0.00 | C |
| ATOM | 8025 | CA | ARG | N | 91 | 42.308 | 76.457 | 286.670 | 1.00 | 0.00 | C |
| ATOM | 8026 | CA | GLU | N | 92 | 42.971 | 73.015 | 285.249 | 1.00 | 0.00 | C |
| ATOM | 8027 | CA | GLN | N | 93 | 43.950 | 74.468 | 281.872 | 1.00 | 0.00 | C |
| ATOM | 8028 | CA | ALA | N | 94 | 46.695 | 76.368 | 283.669 | 1.00 | 0.00 | C |
| ATOM | 8029 | CA | ILE | N | 95 | 47.852 | 73.222 | 285.440 | 1.00 | 0.00 | C |
| ATOM | 8030 | CA | ARG | N | 96 | 47.989 | 71.669 | 281.969 | 1.00 | 0.00 | C |
| ATOM | 8031 | CA | ALA | N | 97 | 49.709 | 74.430 | 280.023 | 1.00 | 0.00 | C |
| ATOM | 8032 | CA | LEU | N | 98 | 52.444 | 74.056 | 282.624 | 1.00 | 0.00 | C |
| ATOM | 8033 | CA | GLN | N | 99 | 52.866 | 70.323 | 282.319 | 1.00 | 0.00 | C |
| ATOM | 8034 | CA | ALA | N | 100 | 53.305 | 70.963 | 278.601 | 1.00 | 0.00 | C |
| ATOM | 8035 | CA | SER | N | 101 | 55.096 | 74.340 | 278.636 | 1.00 | 0.00 | C |
| ATOM | 8036 | CA | GLY | N | 102 | 58.368 | 72.464 | 278.856 | 1.00 | 0.00 | C |
| ATOM | 8037 | CA | LEU | N | 103 | 58.878 | 72.522 | 282.591 | 1.00 | 0.00 | C |
| ATOM | 8038 | CA | GLN | N | 104 | 58.784 | 69.165 | 284.274 | 1.00 | 0.00 | C |
| ATOM | 8039 | CA | VAL | N | 105 | 55.957 | 69.425 | 286.805 | 1.00 | 0.00 | C |
| ATOM | 8040 | CA | LYS | N | 106 | 57.033 | 67.613 | 289.984 | 1.00 | 0.00 | C |
| ATOM | 8041 | CA | SER | N | 107 | 53.668 | 67.864 | 291.696 | 1.00 | 0.00 | C |
| ATOM | 8042 | CA | ILE | N | 108 | 50.317 | 69.592 | 291.765 | 1.00 | 0.00 | C |
| ATOM | 8043 | CA | VAL | N | 109 | 48.854 | 70.612 | 295.123 | 1.00 | 0.00 | C |
| ATOM | 8044 | CA | ASP | N | 110 | 45.625 | 72.323 | 296.127 | 1.00 | 0.00 | C |

```
ATOM   8045  CA  ASP N 111      46.328   74.754 298.962  1.00  0.00           C
ATOM   8046  CA  THR N 112      43.269   76.943 298.451  1.00  0.00           C
ATOM   8047  CA  PRO N 113      42.727   78.796 301.762  1.00  0.00           C
ATOM   8048  CA  VAL N 114      39.558   78.334 303.777  1.00  0.00           C
ATOM   8049  CA  PRO N 115      38.552   79.921 307.062  1.00  0.00           C
ATOM   8050  CA  HIS N 116      37.470   77.881 310.016  1.00  0.00           C
ATOM   8051  CA  ASN N 117      34.677   80.452 309.916  1.00  0.00           C
ATOM   8052  CA  GLY N 118      36.059   83.850 310.751  1.00  0.00           C
ATOM   8053  CA  CYS N 119      34.897   86.915 308.814  1.00  0.00           C
ATOM   8054  CA  ARG N 120      31.342   87.565 307.678  1.00  0.00           C
ATOM   8055  CA  PRO N 121      31.622   87.450 303.919  1.00  0.00           C
ATOM   8056  CA  LYS N 122      30.119   90.200 301.773  1.00  0.00           C
ATOM   8057  CA  LYS N 123      26.453   89.757 300.883  1.00  0.00           C
ATOM   8058  CA  LYS N 124      27.442   88.463 297.459  1.00  0.00           C
ATOM   8059  CA  PHE N 125      28.905   85.384 299.172  1.00  0.00           C
ATOM   8060  CA  ARG N 126      26.545   84.874 302.099  1.00  0.00           C
ATOM   8061  CA  LYS N 127      23.154   83.209 301.585  1.00  0.00           C
ATOM   8062  CA  ALA N 128      24.401   79.899 302.938  1.00  0.00           C
ATOM   8063  CA  SER N 129      24.591   77.980 306.243  1.00  0.00           C
TER    8064      SER N 129
ATOM   8065  CA  PRO O   5     -11.822   85.392 329.943  1.00  0.00           C
ATOM   8066  CA  THR O   6     -11.837   83.256 333.096  1.00  0.00           C
ATOM   8067  CA  ILE O   7     -14.812   83.377 335.440  1.00  0.00           C
ATOM   8068  CA  ASN O   8     -12.646   85.016 338.068  1.00  0.00           C
ATOM   8069  CA  GLN O   9     -11.554   87.517 335.427  1.00  0.00           C
ATOM   8070  CA  LEU O  10     -15.161   88.253 334.544  1.00  0.00           C
ATOM   8071  CA  VAL O  11     -15.728   88.839 338.218  1.00  0.00           C
ATOM   8072  CA  ARG O  12     -12.842   91.281 338.337  1.00  0.00           C
ATOM   8073  CA  LYS O  13     -13.175   93.292 335.147  1.00  0.00           C
ATOM   8074  CA  GLY O  14     -16.526   92.130 333.808  1.00  0.00           C
ATOM   8075  CA  ARG O  15     -18.151   92.826 330.447  1.00  0.00           C
ATOM   8076  CA  GLU O  16     -18.339   96.389 329.129  1.00  0.00           C
ATOM   8077  CA  LYS O  17     -21.723   97.415 327.715  1.00  0.00           C
ATOM   8078  CA  VAL O  18     -21.852   98.874 324.203  1.00  0.00           C
ATOM   8079  CA  ARG O  19     -22.633  102.588 323.702  1.00  0.00           C
ATOM   8080  CA  LYS O  20     -24.556  103.544 320.555  1.00  0.00           C
ATOM   8081  CA  LYS O  21     -23.742  106.987 319.100  1.00  0.00           C
ATOM   8082  CA  SER O  22     -26.504  109.137 317.633  1.00  0.00           C
ATOM   8083  CA  LYS O  23     -26.571  109.801 313.925  1.00  0.00           C
ATOM   8084  CA  VAL O  24     -28.779  112.843 314.233  1.00  0.00           C
ATOM   8085  CA  PRO O  25     -27.757  115.573 316.661  1.00  0.00           C
ATOM   8086  CA  ALA O  26     -31.120  117.268 316.028  1.00  0.00           C
ATOM   8087  CA  LEU O  27     -30.175  117.990 319.645  1.00  0.00           C
ATOM   8088  CA  LYS O  28     -32.751  117.565 322.382  1.00  0.00           C
ATOM   8089  CA  GLY O  29     -32.891  114.136 320.771  1.00  0.00           C
ATOM   8090  CA  ALA O  30     -36.046  115.688 319.349  1.00  0.00           C
ATOM   8091  CA  PRO O  31     -38.208  114.191 316.572  1.00  0.00           C
ATOM   8092  CA  PHE O  32     -37.933  117.365 314.511  1.00  0.00           C
ATOM   8093  CA  ARG O  33     -36.223  120.711 314.658  1.00  0.00           C
ATOM   8094  CA  ARG O  34     -37.024  123.937 312.834  1.00  0.00           C
ATOM   8095  CA  GLY O  35     -34.347  126.143 311.340  1.00  0.00           C
ATOM   8096  CA  VAL O  36     -33.844  128.995 308.928  1.00  0.00           C
ATOM   8097  CA  CYS O  37     -32.504  128.588 305.417  1.00  0.00           C
ATOM   8098  CA  THR O  38     -29.172  130.240 304.677  1.00  0.00           C
ATOM   8099  CA  VAL O  39     -28.172  128.904 301.296  1.00  0.00           C
ATOM   8100  CA  VAL O  40     -30.311  127.022 298.816  1.00  0.00           C
ATOM   8101  CA  ARG O  41     -27.375  125.510 296.901  1.00  0.00           C
ATOM   8102  CA  THR O  42     -27.277  122.372 294.738  1.00  0.00           C
ATOM   8103  CA  VAL O  43     -24.673  119.695 295.337  1.00  0.00           C
ATOM   8104  CA  THR O  44     -23.525  116.929 293.025  1.00  0.00           C
ATOM   8105  CA  PRO O  45     -23.699  113.158 293.822  1.00  0.00           C
ATOM   8106  CA  LYS O  46     -20.853  110.808 294.765  1.00  0.00           C
ATOM   8107  CA  LYS O  47     -19.079  107.661 293.487  1.00  0.00           C
ATOM   8108  CA  PRO O  48     -21.366  106.751 290.554  1.00  0.00           C
ATOM   8109  CA  ASN O  49     -24.537  108.813 290.656  1.00  0.00           C
ATOM   8110  CA  SER O  50     -24.802  112.170 288.914  1.00  0.00           C
ATOM   8111  CA  ALA O  51     -27.420  114.960 289.106  1.00  0.00           C
ATOM   8112  CA  LEU O  52     -28.188  118.256 290.832  1.00  0.00           C
ATOM   8113  CA  ARG O  53     -29.351  117.410 294.332  1.00  0.00           C
ATOM   8114  CA  LYS O  54     -31.231  120.343 295.876  1.00  0.00           C
ATOM   8115  CA  VAL O  55     -29.873  121.106 299.333  1.00  0.00           C
ATOM   8116  CA  ALA O  56     -30.093  123.835 301.993  1.00  0.00           C
ATOM   8117  CA  LYS O  57     -27.909  125.135 304.836  1.00  0.00           C
ATOM   8118  CA  VAL O  58     -30.102  125.542 307.910  1.00  0.00           C
ATOM   8119  CA  ARG O  59     -29.620  127.439 311.161  1.00  0.00           C
ATOM   8120  CA  LEU O  60     -31.398  125.296 313.766  1.00  0.00           C
ATOM   8121  CA  THR O  61     -33.099  126.442 316.949  1.00  0.00           C
ATOM   8122  CA  SER O  62     -30.892  123.787 318.508  1.00  0.00           C
ATOM   8123  CA  GLY O  63     -27.900  126.022 317.879  1.00  0.00           C
ATOM   8124  CA  TYR O  64     -26.581  123.799 315.072  1.00  0.00           C
ATOM   8125  CA  GLU O  65     -26.005  124.889 311.459  1.00  0.00           C
ATOM   8126  CA  VAL O  66     -26.692  121.959 309.124  1.00  0.00           C
ATOM   8127  CA  THR O  67     -27.238  120.862 305.512  1.00  0.00           C
ATOM   8128  CA  ALA O  68     -30.555  119.226 304.630  1.00  0.00           C
ATOM   8129  CA  TYR O  69     -31.998  117.454 301.603  1.00  0.00           C
ATOM   8130  CA  ILE O  70     -35.099  118.891 299.918  1.00  0.00           C
ATOM   8131  CA  PRO O  71     -37.175  115.940 298.604  1.00  0.00           C
```

```
ATOM   8132  CA  GLY O   72     -39.612 116.338 295.750  1.00  0.00           C
ATOM   8133  CA  GLU O   73     -39.810 117.147 292.041  1.00  0.00           C
ATOM   8134  CA  GLY O   74     -39.540 120.895 292.640  1.00  0.00           C
ATOM   8135  CA  HIS O   75     -39.288 123.250 295.640  1.00  0.00           C
ATOM   8136  CA  ASN O   76     -39.827 126.898 296.644  1.00  0.00           C
ATOM   8137  CA  LEU O   77     -37.183 127.388 299.351  1.00  0.00           C
ATOM   8138  CA  GLN O   78     -35.293 130.688 299.560  1.00  0.00           C
ATOM   8139  CA  GLU O   79     -32.603 132.539 301.468  1.00  0.00           C
ATOM   8140  CA  HIS O   80     -34.502 133.076 304.729  1.00  0.00           C
ATOM   8141  CA  SER O   81     -37.304 130.541 304.640  1.00  0.00           C
ATOM   8142  CA  VAL O   82     -38.321 128.847 307.881  1.00  0.00           C
ATOM   8143  CA  VAL O   83     -38.200 125.070 307.612  1.00  0.00           C
ATOM   8144  CA  LEU O   84     -38.601 121.804 309.562  1.00  0.00           C
ATOM   8145  CA  ILE O   85     -35.876 119.117 309.667  1.00  0.00           C
ATOM   8146  CA  ARG O   86     -36.692 115.436 310.101  1.00  0.00           C
ATOM   8147  CA  GLY O   87     -33.464 113.494 310.153  1.00  0.00           C
ATOM   8148  CA  GLY O   88     -32.486 110.989 307.512  1.00  0.00           C
ATOM   8149  CA  ARG O   89     -29.247 111.075 305.594  1.00  0.00           C
ATOM   8150  CA  VAL O   90     -28.802 110.901 301.801  1.00  0.00           C
ATOM   8151  CA  LYS O   91     -26.406 108.180 300.638  1.00  0.00           C
ATOM   8152  CA  ASP O   92     -25.035 110.287 297.742  1.00  0.00           C
ATOM   8153  CA  LEU O   93     -24.539 113.621 299.419  1.00  0.00           C
ATOM   8154  CA  PRO O   94     -21.740 113.401 301.950  1.00  0.00           C
ATOM   8155  CA  GLY O   95     -22.603 115.847 304.693  1.00  0.00           C
ATOM   8156  CA  VAL O   96     -26.373 115.818 304.484  1.00  0.00           C
ATOM   8157  CA  ARG O   97     -27.897 114.164 307.534  1.00  0.00           C
ATOM   8158  CA  TYR O   98     -31.483 115.358 307.551  1.00  0.00           C
ATOM   8159  CA  HIS O   99     -34.347 115.789 305.112  1.00  0.00           C
ATOM   8160  CA  ILE O  100     -36.591 118.831 304.987  1.00  0.00           C
ATOM   8161  CA  VAL O  101     -40.229 118.266 305.816  1.00  0.00           C
ATOM   8162  CA  ARG O  102     -42.285 119.377 302.867  1.00  0.00           C
ATOM   8163  CA  GLY O  103     -45.615 120.934 303.718  1.00  0.00           C
ATOM   8164  CA  VAL O  104     -44.483 122.611 306.918  1.00  0.00           C
ATOM   8165  CA  TYR O  105     -43.683 126.291 307.510  1.00  0.00           C
ATOM   8166  CA  ASP O  106     -42.164 127.871 304.376  1.00  0.00           C
ATOM   8167  CA  ALA O  107     -41.407 124.702 302.441  1.00  0.00           C
ATOM   8168  CA  ALA O  108     -44.438 124.235 300.232  1.00  0.00           C
ATOM   8169  CA  GLY O  109     -45.535 120.747 299.284  1.00  0.00           C
ATOM   8170  CA  VAL O  110     -44.816 119.189 295.915  1.00  0.00           C
ATOM   8171  CA  LYS O  111     -47.185 120.305 293.167  1.00  0.00           C
ATOM   8172  CA  ASP O  112     -48.865 117.580 291.106  1.00  0.00           C
ATOM   8173  CA  ARG O  113     -47.994 114.825 293.561  1.00  0.00           C
ATOM   8174  CA  LYS O  114     -50.613 112.151 292.994  1.00  0.00           C
ATOM   8175  CA  LYS O  115     -49.022 109.289 294.928  1.00  0.00           C
ATOM   8176  CA  SER O  116     -46.929 109.128 298.081  1.00  0.00           C
ATOM   8177  CA  ARG O  117     -48.367 112.506 299.132  1.00  0.00           C
ATOM   8178  CA  SER O  118     -48.132 111.713 302.866  1.00  0.00           C
ATOM   8179  CA  LYS O  119     -44.474 112.522 302.239  1.00  0.00           C
ATOM   8180  CA  TYR O  120     -44.043 115.658 300.078  1.00  0.00           C
ATOM   8181  CA  GLY O  121     -46.895 117.105 302.146  1.00  0.00           C
ATOM   8182  CA  THR O  122     -49.500 117.604 299.394  1.00  0.00           C
ATOM   8183  CA  LYS O  123     -53.238 117.739 300.163  1.00  0.00           C
ATOM   8184  CA  LYS O  124     -55.758 115.391 298.565  1.00  0.00           C
ATOM   8185  CA  PRO O  125     -56.474 116.451 294.975  1.00  0.00           C
ATOM   8186  CA  LYS O  126     -60.217 116.855 294.402  1.00  0.00           C
ATOM   8187  CA  GLU O  127     -61.004 114.544 291.491  1.00  0.00           C
ATOM   8188  CA  ALA O  128     -63.379 116.376 289.151  1.00  0.00           C
TER    8189      ALA O  128
ATOM   8190  CA  ALA P    2      30.769 112.665 212.975  1.00  0.00           C
ATOM   8191  CA  ARG P    3      29.445 116.130 213.808  1.00  0.00           C
ATOM   8192  CA  ILE P    4      25.974 116.609 212.344  1.00  0.00           C
ATOM   8193  CA  ALA P    5      23.345 119.115 213.527  1.00  0.00           C
ATOM   8194  CA  GLY P    6      24.001 122.242 215.554  1.00  0.00           C
ATOM   8195  CA  VAL P    7      27.115 121.179 217.472  1.00  0.00           C
ATOM   8196  CA  GLU P    8      26.080 117.507 217.300  1.00  0.00           C
ATOM   8197  CA  ILE P    9      28.799 114.891 217.793  1.00  0.00           C
ATOM   8198  CA  PRO P   10      27.409 111.366 218.423  1.00  0.00           C
ATOM   8199  CA  ARG P   11      30.251 108.846 218.373  1.00  0.00           C
ATOM   8200  CA  ASN P   12      31.459 105.247 218.774  1.00  0.00           C
ATOM   8201  CA  LYS P   13      28.061 103.190 218.809  1.00  0.00           C
ATOM   8202  CA  ARG P   14      25.745 101.565 216.298  1.00  0.00           C
ATOM   8203  CA  VAL P   15      24.305 104.268 214.017  1.00  0.00           C
ATOM   8204  CA  ASP P   16      20.711 103.438 214.941  1.00  0.00           C
ATOM   8205  CA  VAL P   17      21.443 103.580 218.676  1.00  0.00           C
ATOM   8206  CA  ALA P   18      23.474 106.714 218.068  1.00  0.00           C
ATOM   8207  CA  LEU P   19      20.809 108.539 216.075  1.00  0.00           C
ATOM   8208  CA  THR P   20      18.590 107.925 219.108  1.00  0.00           C
ATOM   8209  CA  TYR P   21      20.777 110.430 220.945  1.00  0.00           C
ATOM   8210  CA  ILE P   22      19.021 113.129 218.923  1.00  0.00           C
ATOM   8211  CA  TYR P   23      16.003 114.969 220.312  1.00  0.00           C
ATOM   8212  CA  GLY P   24      13.423 113.910 217.757  1.00  0.00           C
ATOM   8213  CA  ILE P   25      14.758 110.446 216.975  1.00  0.00           C
ATOM   8214  CA  GLY P   26      13.662 107.213 218.596  1.00  0.00           C
ATOM   8215  CA  LYS P   27      14.375 103.519 217.984  1.00  0.00           C
ATOM   8216  CA  ALA P   28      11.705 103.869 215.306  1.00  0.00           C
ATOM   8217  CA  ARG P   29      13.027 106.691 213.134  1.00  0.00           C
ATOM   8218  CA  ALA P   30      16.415 105.041 213.694  1.00  0.00           C
```

```
ATOM   8219  CA  LYS P  31      15.840 101.938 211.542  1.00  0.00           C
ATOM   8220  CA  GLU P  32      13.954 104.058 209.017  1.00  0.00           C
ATOM   8221  CA  ALA P  33      16.505 106.821 208.409  1.00  0.00           C
ATOM   8222  CA  LEU P  34      18.957 103.944 208.004  1.00  0.00           C
ATOM   8223  CA  GLU P  35      16.412 101.949 206.008  1.00  0.00           C
ATOM   8224  CA  LYS P  36      15.809 104.655 203.394  1.00  0.00           C
ATOM   8225  CA  THR P  37      19.351 106.029 203.310  1.00  0.00           C
ATOM   8226  CA  GLY P  38      20.369 102.392 202.917  1.00  0.00           C
ATOM   8227  CA  ILE P  39      23.082 102.073 205.557  1.00  0.00           C
ATOM   8228  CA  ASN P  40      23.859  99.135 207.789  1.00  0.00           C
ATOM   8229  CA  PRO P  41      22.427 100.053 211.177  1.00  0.00           C
ATOM   8230  CA  ALA P  42      25.101  97.990 212.871  1.00  0.00           C
ATOM   8231  CA  THR P  43      28.025 100.022 211.542  1.00  0.00           C
ATOM   8232  CA  ARG P  44      29.825 101.832 214.375  1.00  0.00           C
ATOM   8233  CA  VAL P  45      29.296 105.576 213.898  1.00  0.00           C
ATOM   8234  CA  LYS P  46      33.074 105.892 213.592  1.00  0.00           C
ATOM   8235  CA  ASP P  47      33.358 103.231 210.872  1.00  0.00           C
ATOM   8236  CA  LEU P  48      30.743 105.127 208.840  1.00  0.00           C
ATOM   8237  CA  THR P  49      31.421 106.690 205.420  1.00  0.00           C
ATOM   8238  CA  GLU P  50      31.500 110.549 204.410  1.00  0.00           C
ATOM   8239  CA  ALA P  51      29.442 110.280 201.249  1.00  0.00           C
ATOM   8240  CA  GLU P  52      26.527 108.603 203.042  1.00  0.00           C
ATOM   8241  CA  VAL P  53      26.762 111.031 205.941  1.00  0.00           C
ATOM   8242  CA  VAL P  54      26.257 113.830 203.423  1.00  0.00           C
ATOM   8243  CA  ARG P  55      23.275 112.340 201.573  1.00  0.00           C
ATOM   8244  CA  LEU P  56      21.778 111.601 205.007  1.00  0.00           C
ATOM   8245  CA  ARG P  57      22.739 114.938 206.494  1.00  0.00           C
ATOM   8246  CA  GLU P  58      21.245 116.666 203.457  1.00  0.00           C
ATOM   8247  CA  TYR P  59      18.210 114.485 202.832  1.00  0.00           C
ATOM   8248  CA  VAL P  60      17.103 114.567 206.471  1.00  0.00           C
ATOM   8249  CA  GLU P  61      17.882 118.158 207.433  1.00  0.00           C
ATOM   8250  CA  ASN P  62      15.979 119.159 204.309  1.00  0.00           C
ATOM   8251  CA  THR P  63      12.836 117.027 204.076  1.00  0.00           C
ATOM   8252  CA  TRP P  64      11.580 117.258 207.671  1.00  0.00           C
ATOM   8253  CA  LYS P  65      11.183 119.968 210.308  1.00  0.00           C
ATOM   8254  CA  LEU P  66      10.919 116.108 211.502  1.00  0.00           C
ATOM   8255  CA  GLU P  67      11.927 116.387 215.159  1.00  0.00           C
ATOM   8256  CA  GLY P  68      14.258 119.061 216.502  1.00  0.00           C
ATOM   8257  CA  GLU P  69      13.125 123.755 216.576  1.00  0.00           C
ATOM   8258  CA  LEU P  70      11.052 120.889 217.993  1.00  0.00           C
ATOM   8259  CA  ARG P  71      11.330 121.866 221.674  1.00  0.00           C
ATOM   8260  CA  ALA P  72      10.314 125.231 220.296  1.00  0.00           C
ATOM   8261  CA  GLU P  73       7.137 123.730 218.848  1.00  0.00           C
ATOM   8262  CA  VAL P  74       6.171 121.641 221.875  1.00  0.00           C
ATOM   8263  CA  ALA P  75       6.820 124.560 224.210  1.00  0.00           C
ATOM   8264  CA  ALA P  76       4.813 126.646 221.763  1.00  0.00           C
ATOM   8265  CA  ASN P  77       1.900 124.182 221.946  1.00  0.00           C
ATOM   8266  CA  ILE P  78       1.652 124.123 225.740  1.00  0.00           C
ATOM   8267  CA  LYS P  79       1.842 127.922 225.797  1.00  0.00           C
ATOM   8268  CA  ARG P  80      -1.283 127.922 223.613  1.00  0.00           C
ATOM   8269  CA  LEU P  81      -3.704 125.656 225.492  1.00  0.00           C
ATOM   8270  CA  MET P  82      -2.318 127.546 228.455  1.00  0.00           C
ATOM   8271  CA  ASP P  83      -3.212 131.005 227.138  1.00  0.00           C
ATOM   8272  CA  ILE P  84      -6.770 129.989 226.421  1.00  0.00           C
ATOM   8273  CA  GLY P  85      -8.899 129.027 229.427  1.00  0.00           C
ATOM   8274  CA  CYS P  86      -8.260 125.459 228.291  1.00  0.00           C
ATOM   8275  CA  TYR P  87      -8.593 123.246 231.390  1.00  0.00           C
ATOM   8276  CA  ARG P  88      -5.775 121.136 230.005  1.00  0.00           C
ATOM   8277  CA  GLY P  89      -3.825 124.385 229.976  1.00  0.00           C
ATOM   8278  CA  LEU P  90      -4.645 125.141 233.594  1.00  0.00           C
ATOM   8279  CA  ARG P  91      -3.312 121.712 234.527  1.00  0.00           C
ATOM   8280  CA  HIS P  92      -0.032 122.962 233.136  1.00  0.00           C
ATOM   8281  CA  ARG P  93      -0.123 126.217 235.107  1.00  0.00           C
ATOM   8282  CA  ARG P  94      -1.119 124.498 238.353  1.00  0.00           C
ATOM   8283  CA  GLY P  95       1.542 121.950 237.510  1.00  0.00           C
ATOM   8284  CA  LEU P  96      -0.705 118.903 238.018  1.00  0.00           C
ATOM   8285  CA  PRO P  97      -1.133 115.873 235.754  1.00  0.00           C
ATOM   8286  CA  VAL P  98      -3.009 116.664 232.560  1.00  0.00           C
ATOM   8287  CA  ARG P  99      -4.102 113.302 231.161  1.00  0.00           C
ATOM   8288  CA  GLY P 100      -6.747 112.888 233.854  1.00  0.00           C
ATOM   8289  CA  GLN P 101      -5.033 110.806 236.507  1.00  0.00           C
ATOM   8290  CA  ARG P 102      -5.617 110.685 240.266  1.00  0.00           C
ATOM   8291  CA  THR P 103      -4.113 113.526 242.255  1.00  0.00           C
ATOM   8292  CA  ARG P 104      -4.922 112.204 245.729  1.00  0.00           C
ATOM   8293  CA  THR P 105      -1.929 109.907 245.563  1.00  0.00           C
ATOM   8294  CA  ASN P 106       0.715 109.095 242.919  1.00  0.00           C
ATOM   8295  CA  ALA P 107       1.575 112.750 241.706  1.00  0.00           C
ATOM   8296  CA  ARG P 108       5.109 113.569 242.688  1.00  0.00           C
ATOM   8297  CA  THR P 109       6.275 113.795 239.097  1.00  0.00           C
ATOM   8298  CA  ARG P 110       3.872 116.736 238.779  1.00  0.00           C
ATOM   8299  CA  LYS P 111       3.913 118.108 242.341  1.00  0.00           C
ATOM   8300  CA  GLY P 112       7.627 117.932 243.054  1.00  0.00           C
ATOM   8301  CA  PRO P 113       9.165 116.716 246.346  1.00  0.00           C
ATOM   8302  CA  ARG P 114       6.884 115.699 249.204  1.00  0.00           C
ATOM   8303  CA  LYS P 115       5.916 118.689 251.309  1.00  0.00           C
ATOM   8304  CA  THR P 116       5.336 116.941 254.646  1.00  0.00           C
ATOM   8305  CA  VAL P 117       3.049 118.544 257.266  1.00  0.00           C
```

```
ATOM   8306  CA  ALA P 118     2.057 117.713 260.855  1.00  0.00           C
ATOM   8307  CA  GLY P 119    -0.703 115.109 261.198  1.00  0.00           C
ATOM   8308  CA  LYS P 120    -3.000 112.734 263.092  1.00  0.00           C
ATOM   8309  CA  LYS P 121    -1.392 109.608 264.599  1.00  0.00           C
ATOM   8310  CA  LYS P 122    -3.532 106.987 266.405  1.00  0.00           C
ATOM   8311  CA  ALA P 123    -6.138 106.389 263.706  1.00  0.00           C
ATOM   8312  CA  PRO P 124    -4.462 103.503 261.795  1.00  0.00           C
ATOM   8313  CA  ARG P 125    -3.373 105.566 258.797  1.00  0.00           C
ATOM   8314  CA  LYS P 126    -1.407 102.455 257.857  1.00  0.00           C
TER    8315      LYS P 126
ATOM   8316  CA  ALA Q   2   -33.208  97.367 246.064  1.00  0.00           C
ATOM   8317  CA  ARG Q   3   -36.370  99.440 246.068  1.00  0.00           C
ATOM   8318  CA  LYS Q   4   -39.275  98.327 243.879  1.00  0.00           C
ATOM   8319  CA  ALA Q   5   -38.974 101.784 242.361  1.00  0.00           C
ATOM   8320  CA  LEU Q   6   -35.360 101.096 241.357  1.00  0.00           C
ATOM   8321  CA  ILE Q   7   -36.226  97.848 239.629  1.00  0.00           C
ATOM   8322  CA  GLU Q   8   -37.084  99.808 236.511  1.00  0.00           C
ATOM   8323  CA  LYS Q   9   -34.177  97.771 235.207  1.00  0.00           C
ATOM   8324  CA  ALA Q  10   -36.646  95.303 233.749  1.00  0.00           C
ATOM   8325  CA  LYS Q  11   -38.000  98.292 231.794  1.00  0.00           C
ATOM   8326  CA  ARG Q  12   -35.830  97.493 228.755  1.00  0.00           C
ATOM   8327  CA  THR Q  13   -36.303 101.045 227.460  1.00  0.00           C
ATOM   8328  CA  PRO Q  14   -32.653 101.865 228.004  1.00  0.00           C
ATOM   8329  CA  LYS Q  15   -33.220 104.810 225.665  1.00  0.00           C
ATOM   8330  CA  PHE Q  16   -29.615 103.750 224.977  1.00  0.00           C
ATOM   8331  CA  LYS Q  17   -28.612 100.128 225.687  1.00  0.00           C
ATOM   8332  CA  VAL Q  18   -25.708 101.097 227.942  1.00  0.00           C
ATOM   8333  CA  ARG Q  19   -28.027 101.983 230.818  1.00  0.00           C
ATOM   8334  CA  ALA Q  20   -28.889  98.269 231.208  1.00  0.00           C
ATOM   8335  CA  TYR Q  21   -27.839  96.447 234.402  1.00  0.00           C
ATOM   8336  CA  THR Q  22   -27.989  92.821 235.597  1.00  0.00           C
ATOM   8337  CA  ARG Q  23   -29.729  92.993 239.043  1.00  0.00           C
ATOM   8338  CA  CYS Q  24   -30.425  89.945 241.182  1.00  0.00           C
ATOM   8339  CA  VAL Q  25   -33.353  87.924 239.954  1.00  0.00           C
ATOM   8340  CA  ARG Q  26   -34.291  87.207 243.561  1.00  0.00           C
ATOM   8341  CA  CYS Q  27   -33.128  89.957 245.930  1.00  0.00           C
ATOM   8342  CA  GLY Q  28   -32.318  92.721 243.460  1.00  0.00           C
ATOM   8343  CA  ARG Q  29   -28.742  92.764 244.685  1.00  0.00           C
ATOM   8344  CA  ALA Q  30   -27.365  94.754 241.751  1.00  0.00           C
ATOM   8345  CA  ARG Q  31   -23.874  94.786 243.297  1.00  0.00           C
ATOM   8346  CA  SER Q  32   -22.429  91.376 242.465  1.00  0.00           C
ATOM   8347  CA  VAL Q  33   -24.811  89.468 240.225  1.00  0.00           C
ATOM   8348  CA  TYR Q  34   -23.374  86.476 238.404  1.00  0.00           C
ATOM   8349  CA  ARG Q  35   -24.602  86.061 234.795  1.00  0.00           C
ATOM   8350  CA  PHE Q  36   -24.866  82.283 234.513  1.00  0.00           C
ATOM   8351  CA  PHE Q  37   -27.440  82.390 237.307  1.00  0.00           C
ATOM   8352  CA  GLY Q  38   -29.082  85.807 237.327  1.00  0.00           C
ATOM   8353  CA  LEU Q  39   -28.363  85.569 241.040  1.00  0.00           C
ATOM   8354  CA  CYS Q  40   -26.114  87.710 243.291  1.00  0.00           C
ATOM   8355  CA  ARG Q  41   -23.112  86.262 245.173  1.00  0.00           C
ATOM   8356  CA  ILE Q  42   -25.323  85.753 248.237  1.00  0.00           C
ATOM   8357  CA  CYS Q  43   -28.385  83.999 246.798  1.00  0.00           C
ATOM   8358  CA  LEU Q  44   -26.031  81.919 244.653  1.00  0.00           C
ATOM   8359  CA  ARG Q  45   -24.463  80.711 247.927  1.00  0.00           C
ATOM   8360  CA  GLU Q  46   -27.816  80.269 249.711  1.00  0.00           C
ATOM   8361  CA  LEU Q  47   -29.251  78.124 246.917  1.00  0.00           C
ATOM   8362  CA  ALA Q  48   -26.069  76.153 246.355  1.00  0.00           C
ATOM   8363  CA  HIS Q  49   -26.497  75.080 249.981  1.00  0.00           C
ATOM   8364  CA  LYS Q  50   -30.079  73.930 249.483  1.00  0.00           C
ATOM   8365  CA  GLY Q  51   -29.384  71.952 246.317  1.00  0.00           C
ATOM   8366  CA  GLN Q  52   -31.656  74.056 244.161  1.00  0.00           C
ATOM   8367  CA  LEU Q  53   -28.704  74.766 241.882  1.00  0.00           C
ATOM   8368  CA  PRO Q  54   -28.620  71.701 239.561  1.00  0.00           C
ATOM   8369  CA  GLY Q  55   -25.223  70.054 239.600  1.00  0.00           C
ATOM   8370  CA  VAL Q  56   -23.637  72.891 241.592  1.00  0.00           C
ATOM   8371  CA  ARG Q  57   -21.625  70.986 244.201  1.00  0.00           C
ATOM   8372  CA  LYS Q  58   -19.027  72.460 246.572  1.00  0.00           C
ATOM   8373  CA  ALA Q  59   -15.551  72.929 245.106  1.00  0.00           C
ATOM   8374  CA  SER Q  60   -12.339  71.693 246.704  1.00  0.00           C
ATOM   8375  CA  TRP Q  61    -8.913  70.640 245.450  1.00  0.00           C
TER    8376      TRP Q  61
ATOM   8377  CA  PRO R   2    31.158  77.128 347.740  1.00  0.00           C
ATOM   8378  CA  ILE R   3    29.545  75.254 350.619  1.00  0.00           C
ATOM   8379  CA  THR R   4    31.264  72.012 351.643  1.00  0.00           C
ATOM   8380  CA  LYS R   5    29.240  68.894 352.495  1.00  0.00           C
ATOM   8381  CA  GLU R   6    30.601  69.680 355.955  1.00  0.00           C
ATOM   8382  CA  GLU R   7    29.404  73.274 355.973  1.00  0.00           C
ATOM   8383  CA  LYS R   8    26.103  71.861 354.743  1.00  0.00           C
ATOM   8384  CA  GLN R   9    25.336  68.965 357.060  1.00  0.00           C
ATOM   8385  CA  LYS R  10    26.613  71.133 359.911  1.00  0.00           C
ATOM   8386  CA  VAL R  11    23.582  73.346 359.264  1.00  0.00           C
ATOM   8387  CA  ILE R  12    21.264  70.450 358.540  1.00  0.00           C
ATOM   8388  CA  GLN R  13    22.032  68.806 361.867  1.00  0.00           C
ATOM   8389  CA  GLU R  14    22.004  72.180 363.612  1.00  0.00           C
ATOM   8390  CA  PHE R  15    18.378  72.706 362.591  1.00  0.00           C
ATOM   8391  CA  ALA R  16    16.827  69.281 362.103  1.00  0.00           C
ATOM   8392  CA  ARG R  17    13.697  68.736 364.222  1.00  0.00           C
```

| | | | | | | | | | | |
|---|---|---|---|---|---|---|---|---|---|---|
| ATOM | 8393 | CA | PHE | R | 18 | 14.961 | 65.274 | 365.123 | 1.00 | 0.00 | C |
| ATOM | 8394 | CA | PRO | R | 19 | 17.685 | 62.690 | 364.331 | 1.00 | 0.00 | C |
| ATOM | 8395 | CA | GLY | R | 20 | 17.582 | 62.282 | 360.571 | 1.00 | 0.00 | C |
| ATOM | 8396 | CA | ASP | R | 21 | 15.460 | 65.315 | 359.766 | 1.00 | 0.00 | C |
| ATOM | 8397 | CA | THR | R | 22 | 16.559 | 66.455 | 356.311 | 1.00 | 0.00 | C |
| ATOM | 8398 | CA | GLY | R | 23 | 13.552 | 68.355 | 354.975 | 1.00 | 0.00 | C |
| ATOM | 8399 | CA | SER | R | 24 | 11.786 | 70.170 | 357.787 | 1.00 | 0.00 | C |
| ATOM | 8400 | CA | THR | R | 25 | 10.812 | 73.716 | 356.966 | 1.00 | 0.00 | C |
| ATOM | 8401 | CA | GLU | R | 26 | 13.297 | 74.829 | 359.600 | 1.00 | 0.00 | C |
| ATOM | 8402 | CA | VAL | R | 27 | 16.099 | 72.993 | 357.800 | 1.00 | 0.00 | C |
| ATOM | 8403 | CA | GLN | R | 28 | 15.200 | 74.117 | 354.304 | 1.00 | 0.00 | C |
| ATOM | 8404 | CA | VAL | R | 29 | 14.905 | 77.709 | 355.440 | 1.00 | 0.00 | C |
| ATOM | 8405 | CA | ALA | R | 30 | 18.285 | 77.365 | 357.137 | 1.00 | 0.00 | C |
| ATOM | 8406 | CA | LEU | R | 31 | 20.005 | 75.967 | 354.025 | 1.00 | 0.00 | C |
| ATOM | 8407 | CA | LEU | R | 32 | 18.438 | 78.720 | 351.892 | 1.00 | 0.00 | C |
| ATOM | 8408 | CA | THR | R | 33 | 19.513 | 81.388 | 354.332 | 1.00 | 0.00 | C |
| ATOM | 8409 | CA | LEU | R | 34 | 22.972 | 79.947 | 353.908 | 1.00 | 0.00 | C |
| ATOM | 8410 | CA | ARG | R | 35 | 22.953 | 79.931 | 350.110 | 1.00 | 0.00 | C |
| ATOM | 8411 | CA | ILE | R | 36 | 21.438 | 83.411 | 350.080 | 1.00 | 0.00 | C |
| ATOM | 8412 | CA | ASN | R | 37 | 24.074 | 84.929 | 352.292 | 1.00 | 0.00 | C |
| ATOM | 8413 | CA | ARG | R | 38 | 26.893 | 83.450 | 350.228 | 1.00 | 0.00 | C |
| ATOM | 8414 | CA | LEU | R | 39 | 25.211 | 84.746 | 347.070 | 1.00 | 0.00 | C |
| ATOM | 8415 | CA | SER | R | 40 | 24.364 | 88.109 | 348.603 | 1.00 | 0.00 | C |
| ATOM | 8416 | CA | GLU | R | 41 | 28.066 | 88.164 | 349.430 | 1.00 | 0.00 | C |
| ATOM | 8417 | CA | HIS | R | 42 | 29.336 | 87.127 | 346.002 | 1.00 | 0.00 | C |
| ATOM | 8418 | CA | LEU | R | 43 | 27.092 | 89.892 | 344.700 | 1.00 | 0.00 | C |
| ATOM | 8419 | CA | LYS | R | 44 | 28.414 | 92.642 | 346.991 | 1.00 | 0.00 | C |
| ATOM | 8420 | CA | VAL | R | 45 | 31.280 | 92.366 | 344.550 | 1.00 | 0.00 | C |
| ATOM | 8421 | CA | HIS | R | 46 | 30.305 | 91.413 | 340.986 | 1.00 | 0.00 | C |
| ATOM | 8422 | CA | LYS | R | 47 | 27.442 | 93.889 | 340.902 | 1.00 | 0.00 | C |
| ATOM | 8423 | CA | LYS | R | 48 | 27.237 | 93.105 | 337.172 | 1.00 | 0.00 | C |
| ATOM | 8424 | CA | ASP | R | 49 | 26.620 | 89.360 | 337.505 | 1.00 | 0.00 | C |
| ATOM | 8425 | CA | HIS | R | 50 | 22.893 | 89.931 | 337.043 | 1.00 | 0.00 | C |
| ATOM | 8426 | CA | HIS | R | 51 | 22.403 | 86.381 | 335.895 | 1.00 | 0.00 | C |
| ATOM | 8427 | CA | SER | R | 52 | 23.310 | 85.104 | 339.335 | 1.00 | 0.00 | C |
| ATOM | 8428 | CA | HIS | R | 53 | 21.142 | 87.789 | 340.905 | 1.00 | 0.00 | C |
| ATOM | 8429 | CA | ARG | R | 54 | 17.995 | 86.228 | 339.465 | 1.00 | 0.00 | C |
| ATOM | 8430 | CA | GLY | R | 55 | 19.068 | 83.060 | 341.219 | 1.00 | 0.00 | C |
| ATOM | 8431 | CA | LEU | R | 56 | 19.010 | 85.072 | 344.440 | 1.00 | 0.00 | C |
| ATOM | 8432 | CA | LEU | R | 57 | 15.605 | 86.607 | 343.733 | 1.00 | 0.00 | C |
| ATOM | 8433 | CA | MET | R | 58 | 14.384 | 83.053 | 343.562 | 1.00 | 0.00 | C |
| ATOM | 8434 | CA | MET | R | 59 | 16.137 | 81.750 | 346.686 | 1.00 | 0.00 | C |
| ATOM | 8435 | CA | VAL | R | 60 | 14.814 | 84.682 | 348.663 | 1.00 | 0.00 | C |
| ATOM | 8436 | CA | GLY | R | 61 | 11.504 | 83.978 | 347.018 | 1.00 | 0.00 | C |
| ATOM | 8437 | CA | GLN | R | 62 | 11.251 | 80.291 | 347.897 | 1.00 | 0.00 | C |
| ATOM | 8438 | CA | ARG | R | 63 | 12.336 | 81.132 | 351.414 | 1.00 | 0.00 | C |
| ATOM | 8439 | CA | ARG | R | 64 | 9.906 | 83.915 | 352.202 | 1.00 | 0.00 | C |
| ATOM | 8440 | CA | ARG | R | 65 | 7.306 | 81.515 | 350.882 | 1.00 | 0.00 | C |
| ATOM | 8441 | CA | LEU | R | 66 | 8.257 | 78.589 | 353.165 | 1.00 | 0.00 | C |
| ATOM | 8442 | CA | LEU | R | 67 | 8.384 | 80.949 | 356.133 | 1.00 | 0.00 | C |
| ATOM | 8443 | CA | ARG | R | 68 | 4.951 | 82.237 | 355.221 | 1.00 | 0.00 | C |
| ATOM | 8444 | CA | TYR | R | 69 | 3.863 | 78.613 | 355.533 | 1.00 | 0.00 | C |
| ATOM | 8445 | CA | LEU | R | 70 | 5.432 | 78.338 | 358.993 | 1.00 | 0.00 | C |
| ATOM | 8446 | CA | GLN | R | 71 | 3.434 | 81.168 | 360.622 | 1.00 | 0.00 | C |
| ATOM | 8447 | CA | ARG | R | 72 | 0.206 | 79.849 | 359.184 | 1.00 | 0.00 | C |
| ATOM | 8448 | CA | GLU | R | 73 | 0.961 | 76.440 | 360.743 | 1.00 | 0.00 | C |
| ATOM | 8449 | CA | ASP | R | 74 | 3.086 | 76.763 | 363.875 | 1.00 | 0.00 | C |
| ATOM | 8450 | CA | PRO | R | 75 | 3.401 | 80.502 | 364.717 | 1.00 | 0.00 | C |
| ATOM | 8451 | CA | GLU | R | 76 | 5.832 | 79.487 | 367.480 | 1.00 | 0.00 | C |
| ATOM | 8452 | CA | ARG | R | 77 | 8.466 | 77.539 | 365.521 | 1.00 | 0.00 | C |
| ATOM | 8453 | CA | TYR | R | 78 | 8.251 | 80.503 | 363.183 | 1.00 | 0.00 | C |
| ATOM | 8454 | CA | ARG | R | 79 | 9.367 | 83.216 | 365.607 | 1.00 | 0.00 | C |
| ATOM | 8455 | CA | ALA | R | 80 | 11.820 | 80.551 | 366.724 | 1.00 | 0.00 | C |
| ATOM | 8456 | CA | LEU | R | 81 | 13.375 | 80.018 | 363.298 | 1.00 | 0.00 | C |
| ATOM | 8457 | CA | ILE | R | 82 | 13.605 | 83.735 | 362.549 | 1.00 | 0.00 | C |
| ATOM | 8458 | CA | GLU | R | 83 | 15.313 | 84.760 | 365.794 | 1.00 | 0.00 | C |
| ATOM | 8459 | CA | LYS | R | 84 | 17.747 | 81.873 | 365.379 | 1.00 | 0.00 | C |
| ATOM | 8460 | CA | LEU | R | 85 | 18.634 | 82.243 | 361.682 | 1.00 | 0.00 | C |
| ATOM | 8461 | CA | GLY | R | 86 | 18.390 | 85.975 | 362.260 | 1.00 | 0.00 | C |
| ATOM | 8462 | CA | ILE | R | 87 | 15.974 | 86.719 | 359.392 | 1.00 | 0.00 | C |
| ATOM | 8463 | CA | ARG | R | 88 | 14.084 | 89.969 | 358.634 | 1.00 | 0.00 | C |
| ATOM | 8464 | CA | GLY | R | 89 | 15.826 | 93.284 | 359.274 | 1.00 | 0.00 | C |
| TER | 8465 | | GLY | R | 89 | | | | | | |
| ATOM | 8466 | CA | MET | S | 1 | -57.923 | 109.347 | 364.728 | 1.00 | 0.00 | C |
| ATOM | 8467 | CA | VAL | S | 2 | -58.641 | 105.926 | 363.234 | 1.00 | 0.00 | C |
| ATOM | 8468 | CA | LYS | S | 3 | -61.892 | 105.700 | 361.312 | 1.00 | 0.00 | C |
| ATOM | 8469 | CA | ILE | S | 4 | -64.238 | 103.258 | 359.583 | 1.00 | 0.00 | C |
| ATOM | 8470 | CA | ARG | S | 5 | -65.432 | 104.932 | 356.412 | 1.00 | 0.00 | C |
| ATOM | 8471 | CA | LEU | S | 6 | -66.128 | 104.636 | 352.705 | 1.00 | 0.00 | C |
| ATOM | 8472 | CA | ALA | S | 7 | -63.520 | 104.855 | 349.917 | 1.00 | 0.00 | C |
| ATOM | 8473 | CA | ARG | S | 8 | -64.551 | 105.781 | 346.392 | 1.00 | 0.00 | C |
| ATOM | 8474 | CA | PHE | S | 9 | -63.507 | 102.978 | 344.095 | 1.00 | 0.00 | C |
| ATOM | 8475 | CA | GLY | S | 10 | -66.163 | 102.967 | 341.436 | 1.00 | 0.00 | C |
| ATOM | 8476 | CA | SER | S | 11 | -65.834 | 105.065 | 338.311 | 1.00 | 0.00 | C |
| ATOM | 8477 | CA | LYS | S | 12 | -67.871 | 107.847 | 336.758 | 1.00 | 0.00 | C |
| ATOM | 8478 | CA | HIS | S | 13 | -71.509 | 107.347 | 337.668 | 1.00 | 0.00 | C |
| ATOM | 8479 | CA | ASN | S | 14 | -70.544 | 103.853 | 338.750 | 1.00 | 0.00 | C |

```
ATOM  8480  CA  PRO S  15   -69.439 104.521 342.359  1.00  0.00           C
ATOM  8481  CA  HIS S  16   -68.410 101.542 344.491  1.00  0.00           C
ATOM  8482  CA  TYR S  17   -67.181 102.200 348.010  1.00  0.00           C
ATOM  8483  CA  ARG S  18   -64.971 100.113 350.283  1.00  0.00           C
ATOM  8484  CA  ILE S  19   -65.859 100.129 353.976  1.00  0.00           C
ATOM  8485  CA  VAL S  20   -62.367 100.718 355.314  1.00  0.00           C
ATOM  8486  CA  VAL S  21   -60.355 101.199 358.514  1.00  0.00           C
ATOM  8487  CA  THR S  22   -57.976 104.097 357.860  1.00  0.00           C
ATOM  8488  CA  ASP S  23   -56.399 107.022 359.726  1.00  0.00           C
ATOM  8489  CA  ALA S  24   -58.613 110.153 359.652  1.00  0.00           C
ATOM  8490  CA  ARG S  25   -55.817 112.068 357.932  1.00  0.00           C
ATOM  8491  CA  ARG S  26   -55.409 110.022 354.714  1.00  0.00           C
ATOM  8492  CA  LYS S  27   -56.763 110.813 351.287  1.00  0.00           C
ATOM  8493  CA  ARG S  28   -60.217 109.270 351.188  1.00  0.00           C
ATOM  8494  CA  ASP S  29   -58.914 107.047 348.420  1.00  0.00           C
ATOM  8495  CA  GLY S  30   -55.522 106.589 350.029  1.00  0.00           C
ATOM  8496  CA  LYS S  31   -53.866 103.665 351.781  1.00  0.00           C
ATOM  8497  CA  TYR S  32   -56.145 102.140 354.390  1.00  0.00           C
ATOM  8498  CA  ILE S  33   -55.274  99.960 357.383  1.00  0.00           C
ATOM  8499  CA  GLU S  34   -57.687  97.180 356.478  1.00  0.00           C
ATOM  8500  CA  LYS S  35   -60.701  96.513 354.300  1.00  0.00           C
ATOM  8501  CA  ILE S  36   -63.747  95.217 356.140  1.00  0.00           C
ATOM  8502  CA  GLY S  37   -66.536  95.579 353.648  1.00  0.00           C
ATOM  8503  CA  TYR S  38   -67.846  97.117 350.471  1.00  0.00           C
ATOM  8504  CA  TYR S  39   -70.959  98.951 349.378  1.00  0.00           C
ATOM  8505  CA  ASP S  40   -72.751  99.365 346.044  1.00  0.00           C
ATOM  8506  CA  PRO S  41   -74.858 102.564 346.295  1.00  0.00           C
ATOM  8507  CA  ARG S  42   -77.036 101.548 343.386  1.00  0.00           C
ATOM  8508  CA  LYS S  43   -77.600  97.948 344.408  1.00  0.00           C
ATOM  8509  CA  THR S  44   -76.763  96.910 340.824  1.00  0.00           C
ATOM  8510  CA  THR S  45   -76.499  93.332 342.074  1.00  0.00           C
ATOM  8511  CA  PRO S  46   -78.278  91.199 344.732  1.00  0.00           C
ATOM  8512  CA  ASP S  47   -75.092  91.393 346.736  1.00  0.00           C
ATOM  8513  CA  TRP S  48   -74.694  95.141 347.213  1.00  0.00           C
ATOM  8514  CA  LEU S  49   -73.357  95.213 350.765  1.00  0.00           C
ATOM  8515  CA  LYS S  50   -71.007  92.838 352.577  1.00  0.00           C
ATOM  8516  CA  VAL S  51   -69.648  93.842 355.974  1.00  0.00           C
ATOM  8517  CA  ASP S  52   -67.723  91.183 357.900  1.00  0.00           C
ATOM  8518  CA  VAL S  53   -69.254  92.303 361.176  1.00  0.00           C
ATOM  8519  CA  GLU S  54   -66.621  90.256 362.963  1.00  0.00           C
ATOM  8520  CA  ARG S  55   -63.758  92.638 362.190  1.00  0.00           C
ATOM  8521  CA  ALA S  56   -65.734  95.870 362.484  1.00  0.00           C
ATOM  8522  CA  ARG S  57   -66.563  95.069 366.101  1.00  0.00           C
ATOM  8523  CA  TYR S  58   -62.853  94.587 366.538  1.00  0.00           C
ATOM  8524  CA  TRP S  59   -61.953  98.014 365.222  1.00  0.00           C
ATOM  8525  CA  LEU S  60   -64.719  99.707 367.198  1.00  0.00           C
ATOM  8526  CA  SER S  61   -63.259  97.670 370.040  1.00  0.00           C
ATOM  8527  CA  VAL S  62   -60.376 100.144 369.852  1.00  0.00           C
ATOM  8528  CA  GLY S  63   -61.415 103.652 368.891  1.00  0.00           C
ATOM  8529  CA  ALA S  64   -62.509 103.164 365.303  1.00  0.00           C
ATOM  8530  CA  GLN S  65   -64.980 105.988 364.740  1.00  0.00           C
ATOM  8531  CA  PRO S  66   -67.364 105.380 361.840  1.00  0.00           C
ATOM  8532  CA  THR S  67   -68.421 108.040 359.355  1.00  0.00           C
ATOM  8533  CA  ASP S  68   -72.142 108.504 359.642  1.00  0.00           C
ATOM  8534  CA  THR S  69   -72.909 106.758 356.329  1.00  0.00           C
ATOM  8535  CA  ALA S  70   -70.401 104.055 357.243  1.00  0.00           C
ATOM  8536  CA  ARG S  71   -72.177 103.399 360.548  1.00  0.00           C
ATOM  8537  CA  ARG S  72   -75.541 103.224 358.802  1.00  0.00           C
ATOM  8538  CA  LEU S  73   -74.217 100.416 356.596  1.00  0.00           C
ATOM  8539  CA  LEU S  74   -72.599  98.721 359.543  1.00  0.00           C
ATOM  8540  CA  ARG S  75   -75.958  98.883 361.292  1.00  0.00           C
ATOM  8541  CA  GLN S  76   -77.640  97.260 358.287  1.00  0.00           C
ATOM  8542  CA  ALA S  77   -75.280  94.294 358.597  1.00  0.00           C
ATOM  8543  CA  GLY S  78   -76.212  94.349 362.241  1.00  0.00           C
ATOM  8544  CA  VAL S  79   -72.818  95.234 363.637  1.00  0.00           C
ATOM  8545  CA  PHE S  80   -74.592  96.884 366.526  1.00  0.00           C
ATOM  8546  CA  ARG S  81   -77.642  94.657 367.029  1.00  0.00           C
ATOM  8547  CA  GLN S  82   -76.780  93.379 370.490  1.00  0.00           C
ATOM  8548  CA  GLU S  83   -79.830  91.097 370.789  1.00  0.00           C
TER   8549      GLU S  83
ATOM  8550  CA  PRO T   2   -33.085  92.739 367.029  1.00  0.00           C
ATOM  8551  CA  LYS T   3   -30.149  95.033 367.471  1.00  0.00           C
ATOM  8552  CA  LYS T   4   -27.857  93.682 364.737  1.00  0.00           C
ATOM  8553  CA  VAL T   5   -24.855  91.730 366.018  1.00  0.00           C
ATOM  8554  CA  LEU T   6   -21.675  91.317 363.971  1.00  0.00           C
ATOM  8555  CA  THR T   7   -18.292  89.585 364.241  1.00  0.00           C
ATOM  8556  CA  GLY T   8   -15.012  90.909 362.968  1.00  0.00           C
ATOM  8557  CA  VAL T   9   -11.415  91.641 363.847  1.00  0.00           C
ATOM  8558  CA  VAL T  10    -9.923  94.662 365.508  1.00  0.00           C
ATOM  8559  CA  VAL T  11    -7.622  96.003 362.832  1.00  0.00           C
ATOM  8560  CA  SER T  12    -6.990  99.245 364.705  1.00  0.00           C
ATOM  8561  CA  ASP T  13    -6.479 100.303 368.319  1.00  0.00           C
ATOM  8562  CA  LYS T  14    -5.181 103.763 367.420  1.00  0.00           C
ATOM  8563  CA  MET T  15    -8.077 105.740 368.923  1.00  0.00           C
ATOM  8564  CA  GLN T  16    -9.295 106.531 372.435  1.00  0.00           C
ATOM  8565  CA  LYS T  17   -12.136 104.302 373.691  1.00  0.00           C
ATOM  8566  CA  THR T  18   -12.712 103.272 370.062  1.00  0.00           C
```

```
ATOM  8567  CA  VAL T  19   -11.597 100.344 367.882  1.00  0.00           C
ATOM  8568  CA  THR T  20   -11.861  99.525 364.192  1.00  0.00           C
ATOM  8569  CA  VAL T  21   -13.541  96.192 363.616  1.00  0.00           C
ATOM  8570  CA  LEU T  22   -13.285  94.641 360.184  1.00  0.00           C
ATOM  8571  CA  VAL T  23   -16.460  92.617 359.608  1.00  0.00           C
ATOM  8572  CA  GLU T  24   -16.357  90.145 356.706  1.00  0.00           C
ATOM  8573  CA  ARG T  25   -19.456  89.150 354.709  1.00  0.00           C
ATOM  8574  CA  GLN T  26   -20.378  86.660 351.983  1.00  0.00           C
ATOM  8575  CA  PHE T  27   -23.218  86.216 349.528  1.00  0.00           C
ATOM  8576  CA  PRO T  28   -24.192  85.197 346.008  1.00  0.00           C
ATOM  8577  CA  HIS T  29   -23.631  87.650 343.246  1.00  0.00           C
ATOM  8578  CA  PRO T  30   -27.090  88.824 342.120  1.00  0.00           C
ATOM  8579  CA  LEU T  31   -26.421  87.940 338.470  1.00  0.00           C
ATOM  8580  CA  TYR T  32   -23.437  85.581 338.235  1.00  0.00           C
ATOM  8581  CA  GLY T  33   -24.323  83.714 341.392  1.00  0.00           C
ATOM  8582  CA  LYS T  34   -20.831  82.785 342.590  1.00  0.00           C
ATOM  8583  CA  VAL T  35   -20.306  83.463 346.286  1.00  0.00           C
ATOM  8584  CA  ILE T  36   -18.309  86.658 346.537  1.00  0.00           C
ATOM  8585  CA  LYS T  37   -16.912  88.090 349.737  1.00  0.00           C
ATOM  8586  CA  ARG T  38   -16.914  91.779 350.618  1.00  0.00           C
ATOM  8587  CA  SER T  39   -15.955  93.483 353.883  1.00  0.00           C
ATOM  8588  CA  LYS T  40   -16.584  96.651 355.896  1.00  0.00           C
ATOM  8589  CA  LYS T  41   -14.926  98.457 358.818  1.00  0.00           C
ATOM  8590  CA  TYR T  42   -16.975  99.576 361.804  1.00  0.00           C
ATOM  8591  CA  LEU T  43   -15.768 101.869 364.577  1.00  0.00           C
ATOM  8592  CA  ALA T  44   -16.892 100.273 367.832  1.00  0.00           C
ATOM  8593  CA  HIS T  45   -16.965 101.778 371.279  1.00  0.00           C
ATOM  8594  CA  ASP T  46   -14.337 100.375 373.664  1.00  0.00           C
ATOM  8595  CA  PRO T  47   -14.710 102.278 376.995  1.00  0.00           C
ATOM  8596  CA  GLU T  48   -12.475 100.069 379.111  1.00  0.00           C
ATOM  8597  CA  GLU T  49    -9.868 100.263 376.316  1.00  0.00           C
ATOM  8598  CA  LYS T  50   -10.133  96.503 376.789  1.00  0.00           C
ATOM  8599  CA  TYR T  51   -10.014  95.033 373.265  1.00  0.00           C
ATOM  8600  CA  LYS T  52    -6.606  94.889 371.610  1.00  0.00           C
ATOM  8601  CA  LEU T  53    -5.276  94.709 368.058  1.00  0.00           C
ATOM  8602  CA  GLY T  54    -5.880  91.198 366.766  1.00  0.00           C
ATOM  8603  CA  ASP T  55    -8.975  90.349 368.816  1.00  0.00           C
ATOM  8604  CA  VAL T  56   -12.065  88.851 367.224  1.00  0.00           C
ATOM  8605  CA  VAL T  57   -15.105  90.580 368.650  1.00  0.00           C
ATOM  8606  CA  GLU T  58   -18.886  90.695 368.447  1.00  0.00           C
ATOM  8607  CA  ILE T  59   -20.227  94.131 367.557  1.00  0.00           C
ATOM  8608  CA  ILE T  60   -23.717  95.183 368.580  1.00  0.00           C
ATOM  8609  CA  GLU T  61   -26.008  97.838 367.071  1.00  0.00           C
ATOM  8610  CA  SER T  62   -26.102 100.687 369.562  1.00  0.00           C
ATOM  8611  CA  ARG T  63   -27.271 104.246 370.075  1.00  0.00           C
ATOM  8612  CA  PRO T  64   -24.991 106.760 368.360  1.00  0.00           C
ATOM  8613  CA  ILE T  65   -21.854 107.395 370.398  1.00  0.00           C
ATOM  8614  CA  SER T  66   -20.016 109.501 367.890  1.00  0.00           C
ATOM  8615  CA  LYS T  67   -20.543 110.501 364.260  1.00  0.00           C
ATOM  8616  CA  ARG T  68   -19.748 107.460 362.198  1.00  0.00           C
ATOM  8617  CA  LYS T  69   -19.902 105.206 365.305  1.00  0.00           C
ATOM  8618  CA  ARG T  70   -23.053 103.201 366.045  1.00  0.00           C
ATOM  8619  CA  PHE T  71   -21.633  99.977 367.484  1.00  0.00           C
ATOM  8620  CA  ARG T  72   -20.362  98.718 370.817  1.00  0.00           C
ATOM  8621  CA  VAL T  73   -18.028  95.797 371.424  1.00  0.00           C
ATOM  8622  CA  LEU T  74   -20.454  93.219 372.729  1.00  0.00           C
ATOM  8623  CA  ARG T  75   -17.761  90.676 373.548  1.00  0.00           C
ATOM  8624  CA  LEU T  76   -14.581  88.820 372.702  1.00  0.00           C
ATOM  8625  CA  VAL T  77   -14.824  85.643 370.618  1.00  0.00           C
ATOM  8626  CA  GLU T  78   -11.167  84.654 370.356  1.00  0.00           C
ATOM  8627  CA  SER T  79    -8.093  86.641 371.337  1.00  0.00           C
ATOM  8628  CA  GLY T  80    -4.961  87.264 369.307  1.00  0.00           C
ATOM  8629  CA  ARG T  81    -4.571  86.369 365.649  1.00  0.00           C
ATOM  8630  CA  MET T  82    -2.716  88.883 363.522  1.00  0.00           C
ATOM  8631  CA  ASP T  83    -2.898  86.525 360.564  1.00  0.00           C
ATOM  8632  CA  LEU T  84    -6.019  88.569 359.752  1.00  0.00           C
ATOM  8633  CA  VAL T  85    -4.752  92.006 360.662  1.00  0.00           C
ATOM  8634  CA  GLU T  86    -1.923  91.177 358.224  1.00  0.00           C
ATOM  8635  CA  LYS T  87    -4.181  90.738 355.212  1.00  0.00           C
ATOM  8636  CA  TYR T  88    -5.841  94.049 355.988  1.00  0.00           C
ATOM  8637  CA  LEU T  89    -2.496  95.838 356.504  1.00  0.00           C
ATOM  8638  CA  ILE T  90    -0.757  94.269 353.526  1.00  0.00           C
ATOM  8639  CA  ARG T  91    -3.715  95.351 351.421  1.00  0.00           C
ATOM  8640  CA  ARG T  92    -3.382  98.887 352.747  1.00  0.00           C
ATOM  8641  CA  GLN T  93     0.301  98.695 351.829  1.00  0.00           C
ATOM  8642  CA  ASN T  94    -0.436  97.906 348.168  1.00  0.00           C
ATOM  8643  CA  TYR T  95    -2.317 101.186 347.963  1.00  0.00           C
ATOM  8644  CA  GLN T  96     0.982 102.901 348.805  1.00  0.00           C
ATOM  8645  CA  SER T  97     1.838 101.900 345.291  1.00  0.00           C
ATOM  8646  CA  LEU T  98    -0.679 101.585 342.379  1.00  0.00           C
ATOM  8647  CA  SER T  99    -0.942 105.392 341.720  1.00  0.00           C
ATOM  8648  CA  LYS T 100     1.757 107.424 339.896  1.00  0.00           C
ATOM  8649  CA  ARG T 101     4.453 104.797 340.535  1.00  0.00           C
ATOM  8650  CA  GLY T 102     2.474 101.531 340.582  1.00  0.00           C
ATOM  8651  CA  GLY T 103     1.551  98.719 343.005  1.00  0.00           C
ATOM  8652  CA  LYS T 104     3.827  95.792 344.137  1.00  0.00           C
ATOM  8653  CA  ALA T 105     3.527  92.030 343.363  1.00  0.00           C
```

| | | | | | | | | | | |
|---|---|---|---|---|---|---|---|---|---|---|
| TER | 8654 | | ALA | T | 105 | | | | | |
| ATOM | 8655 | CA | PRO | U | 16 | 30.799 | 55.905 | 299.873 | 1.00 | 0.00 | C |
| ATOM | 8656 | CA | SER | U | 17 | 32.620 | 56.483 | 303.185 | 1.00 | 0.00 | C |
| ATOM | 8657 | CA | ARG | U | 18 | 33.187 | 52.959 | 304.527 | 1.00 | 0.00 | C |
| ATOM | 8658 | CA | LYS | U | 19 | 36.993 | 52.845 | 304.563 | 1.00 | 0.00 | C |
| ATOM | 8659 | CA | ALA | U | 20 | 37.130 | 51.973 | 308.288 | 1.00 | 0.00 | C |
| ATOM | 8660 | CA | LYS | U | 21 | 35.907 | 53.568 | 311.522 | 1.00 | 0.00 | C |
| ATOM | 8661 | CA | VAL | U | 22 | 38.703 | 55.311 | 313.429 | 1.00 | 0.00 | C |
| ATOM | 8662 | CA | LYS | U | 23 | 37.141 | 53.932 | 316.624 | 1.00 | 0.00 | C |
| ATOM | 8663 | CA | ALA | U | 24 | 37.240 | 50.263 | 315.589 | 1.00 | 0.00 | C |
| ATOM | 8664 | CA | THR | U | 25 | 40.778 | 50.607 | 314.259 | 1.00 | 0.00 | C |
| ATOM | 8665 | CA | LEU | U | 26 | 41.978 | 51.267 | 317.817 | 1.00 | 0.00 | C |
| ATOM | 8666 | CA | GLY | U | 27 | 41.868 | 50.224 | 321.475 | 1.00 | 0.00 | C |
| ATOM | 8667 | CA | GLU | U | 28 | 39.955 | 51.591 | 324.468 | 1.00 | 0.00 | C |
| ATOM | 8668 | CA | PHE | U | 29 | 41.128 | 55.124 | 325.142 | 1.00 | 0.00 | C |
| ATOM | 8669 | CA | ASP | U | 30 | 40.188 | 57.875 | 327.539 | 1.00 | 0.00 | C |
| ATOM | 8670 | CA | LEU | U | 31 | 38.336 | 60.286 | 325.278 | 1.00 | 0.00 | C |
| ATOM | 8671 | CA | ARG | U | 32 | 38.980 | 62.868 | 328.006 | 1.00 | 0.00 | C |
| ATOM | 8672 | CA | ASP | U | 33 | 42.791 | 62.636 | 327.811 | 1.00 | 0.00 | C |
| ATOM | 8673 | CA | TYR | U | 34 | 44.102 | 65.723 | 326.050 | 1.00 | 0.00 | C |
| ATOM | 8674 | CA | ARG | U | 35 | 47.720 | 64.594 | 325.806 | 1.00 | 0.00 | C |
| ATOM | 8675 | CA | ASN | U | 36 | 47.517 | 61.273 | 323.971 | 1.00 | 0.00 | C |
| ATOM | 8676 | CA | VAL | U | 37 | 48.805 | 62.774 | 320.723 | 1.00 | 0.00 | C |
| ATOM | 8677 | CA | GLU | U | 38 | 49.333 | 59.162 | 319.773 | 1.00 | 0.00 | C |
| ATOM | 8678 | CA | VAL | U | 39 | 45.638 | 58.336 | 319.694 | 1.00 | 0.00 | C |
| ATOM | 8679 | CA | LEU | U | 40 | 44.000 | 61.773 | 319.303 | 1.00 | 0.00 | C |
| ATOM | 8680 | CA | LYS | U | 41 | 45.953 | 62.429 | 316.074 | 1.00 | 0.00 | C |
| ATOM | 8681 | CA | ARG | U | 42 | 43.924 | 59.489 | 314.737 | 1.00 | 0.00 | C |
| ATOM | 8682 | CA | PHE | U | 43 | 40.694 | 61.506 | 314.602 | 1.00 | 0.00 | C |
| ATOM | 8683 | CA | LEU | U | 44 | 42.095 | 64.264 | 312.428 | 1.00 | 0.00 | C |
| ATOM | 8684 | CA | SER | U | 45 | 41.609 | 64.661 | 308.699 | 1.00 | 0.00 | C |
| ATOM | 8685 | CA | GLU | U | 46 | 44.569 | 64.916 | 306.355 | 1.00 | 0.00 | C |
| ATOM | 8686 | CA | THR | U | 47 | 44.368 | 68.422 | 307.841 | 1.00 | 0.00 | C |
| ATOM | 8687 | CA | GLY | U | 48 | 44.016 | 69.586 | 311.441 | 1.00 | 0.00 | C |
| ATOM | 8688 | CA | LYS | U | 49 | 40.292 | 69.107 | 310.889 | 1.00 | 0.00 | C |
| ATOM | 8689 | CA | ILE | U | 50 | 38.309 | 66.940 | 313.275 | 1.00 | 0.00 | C |
| ATOM | 8690 | CA | LEU | U | 51 | 36.650 | 64.079 | 311.453 | 1.00 | 0.00 | C |
| ATOM | 8691 | CA | PRO | U | 52 | 32.836 | 63.677 | 311.290 | 1.00 | 0.00 | C |
| ATOM | 8692 | CA | ARG | U | 53 | 31.191 | 60.851 | 313.194 | 1.00 | 0.00 | C |
| ATOM | 8693 | CA | ARG | U | 54 | 30.747 | 59.158 | 309.824 | 1.00 | 0.00 | C |
| ATOM | 8694 | CA | ARG | U | 55 | 34.495 | 58.507 | 309.928 | 1.00 | 0.00 | C |
| ATOM | 8695 | CA | THR | U | 56 | 35.253 | 58.688 | 313.639 | 1.00 | 0.00 | C |
| ATOM | 8696 | CA | GLY | U | 57 | 32.760 | 55.935 | 314.388 | 1.00 | 0.00 | C |
| ATOM | 8697 | CA | LEU | U | 58 | 32.124 | 57.724 | 317.671 | 1.00 | 0.00 | C |
| ATOM | 8698 | CA | SER | U | 59 | 28.679 | 58.588 | 319.001 | 1.00 | 0.00 | C |
| ATOM | 8699 | CA | GLY | U | 60 | 27.041 | 61.948 | 319.576 | 1.00 | 0.00 | C |
| ATOM | 8700 | CA | LYS | U | 61 | 28.197 | 61.996 | 323.179 | 1.00 | 0.00 | C |
| ATOM | 8701 | CA | GLU | U | 62 | 31.651 | 60.486 | 322.634 | 1.00 | 0.00 | C |
| ATOM | 8702 | CA | GLN | U | 63 | 32.283 | 62.663 | 319.558 | 1.00 | 0.00 | C |
| ATOM | 8703 | CA | ARG | U | 64 | 31.282 | 65.689 | 321.559 | 1.00 | 0.00 | C |
| ATOM | 8704 | CA | ILE | U | 65 | 33.911 | 65.024 | 324.236 | 1.00 | 0.00 | C |
| ATOM | 8705 | CA | LEU | U | 66 | 36.569 | 64.378 | 321.616 | 1.00 | 0.00 | C |
| ATOM | 8706 | CA | ALA | U | 67 | 36.211 | 67.838 | 320.145 | 1.00 | 0.00 | C |
| ATOM | 8707 | CA | LYS | U | 68 | 37.018 | 69.493 | 323.470 | 1.00 | 0.00 | C |
| ATOM | 8708 | CA | THR | U | 69 | 39.981 | 67.184 | 323.920 | 1.00 | 0.00 | C |
| ATOM | 8709 | CA | ILE | U | 70 | 41.267 | 67.703 | 320.384 | 1.00 | 0.00 | C |
| ATOM | 8710 | CA | LYS | U | 71 | 40.862 | 71.449 | 320.876 | 1.00 | 0.00 | C |
| ATOM | 8711 | CA | ARG | U | 72 | 42.661 | 71.441 | 324.232 | 1.00 | 0.00 | C |
| ATOM | 8712 | CA | ALA | U | 73 | 45.484 | 69.485 | 322.622 | 1.00 | 0.00 | C |
| ATOM | 8713 | CA | ARG | U | 74 | 45.686 | 72.159 | 319.937 | 1.00 | 0.00 | C |
| ATOM | 8714 | CA | ILE | U | 75 | 46.305 | 74.993 | 322.362 | 1.00 | 0.00 | C |
| ATOM | 8715 | CA | LEU | U | 76 | 49.064 | 73.027 | 324.135 | 1.00 | 0.00 | C |
| ATOM | 8716 | CA | GLY | U | 77 | 50.691 | 72.714 | 320.720 | 1.00 | 0.00 | C |
| ATOM | 8717 | CA | LEU | U | 78 | 50.482 | 68.918 | 320.591 | 1.00 | 0.00 | C |
| ATOM | 8718 | CA | LEU | U | 79 | 47.847 | 68.870 | 317.842 | 1.00 | 0.00 | C |
| ATOM | 8719 | CA | PRO | U | 80 | 47.571 | 71.087 | 314.738 | 1.00 | 0.00 | C |
| ATOM | 8720 | CA | PHE | U | 81 | 44.796 | 73.484 | 313.879 | 1.00 | 0.00 | C |
| ATOM | 8721 | CA | THR | U | 82 | 45.252 | 72.967 | 310.154 | 1.00 | 0.00 | C |
| ATOM | 8722 | CA | GLU | U | 83 | 47.538 | 71.183 | 307.664 | 1.00 | 0.00 | C |
| ATOM | 8723 | CA | LYS | U | 84 | 48.311 | 71.724 | 303.958 | 1.00 | 0.00 | C |
| ATOM | 8724 | CA | LEU | U | 85 | 46.918 | 69.383 | 301.286 | 1.00 | 0.00 | C |
| ATOM | 8725 | CA | VAL | U | 86 | 49.287 | 67.334 | 299.130 | 1.00 | 0.00 | C |
| ATOM | 8726 | CA | ARG | U | 87 | 48.620 | 66.195 | 295.527 | 1.00 | 0.00 | C |
| ATOM | 8727 | CA | LYS | U | 88 | 45.927 | 68.204 | 293.695 | 1.00 | 0.00 | C |
| TER | 8728 | | LYS | U | 88 | | | | | |
| ATOM | 8729 | CA | PRO | V | 2 | -5.007 | 111.085 | 221.536 | 1.00 | 0.00 | C |
| ATOM | 8730 | CA | ARG | V | 3 | -8.826 | 111.340 | 221.763 | 1.00 | 0.00 | C |
| ATOM | 8731 | CA | SER | V | 4 | -11.273 | 109.576 | 219.410 | 1.00 | 0.00 | C |
| ATOM | 8732 | CA | LEU | V | 5 | -14.910 | 109.098 | 218.414 | 1.00 | 0.00 | C |
| ATOM | 8733 | CA | LYS | V | 6 | -14.576 | 107.744 | 214.822 | 1.00 | 0.00 | C |
| ATOM | 8734 | CA | LYS | V | 7 | -16.943 | 108.716 | 212.000 | 1.00 | 0.00 | C |
| ATOM | 8735 | CA | GLY | V | 8 | -19.774 | 111.016 | 213.096 | 1.00 | 0.00 | C |
| ATOM | 8736 | CA | VAL | V | 9 | -18.675 | 113.882 | 215.413 | 1.00 | 0.00 | C |
| ATOM | 8737 | CA | PHE | V | 10 | -21.366 | 113.692 | 218.083 | 1.00 | 0.00 | C |
| ATOM | 8738 | CA | VAL | V | 11 | -23.311 | 116.757 | 219.271 | 1.00 | 0.00 | C |
| ATOM | 8739 | CA | ASP | V | 12 | -26.649 | 116.676 | 221.105 | 1.00 | 0.00 | C |
| ATOM | 8740 | CA | ASP | V | 13 | -29.253 | 118.520 | 219.057 | 1.00 | 0.00 | C |

```
ATOM   8741  CA  HIS V  14    -30.809 120.325 222.019  1.00  0.00           C
ATOM   8742  CA  LEU V  15    -28.344 123.151 221.580  1.00  0.00           C
ATOM   8743  CA  LEU V  16    -27.447 122.288 217.995  1.00  0.00           C
ATOM   8744  CA  GLU V  17    -30.815 122.860 216.369  1.00  0.00           C
ATOM   8745  CA  LYS V  18    -31.109 125.676 218.927  1.00  0.00           C
ATOM   8746  CA  VAL V  19    -27.765 127.314 218.222  1.00  0.00           C
ATOM   8747  CA  LEU V  20    -28.190 127.481 214.453  1.00  0.00           C
ATOM   8748  CA  GLU V  21    -31.761 128.739 214.816  1.00  0.00           C
ATOM   8749  CA  LEU V  22    -30.060 131.752 216.364  1.00  0.00           C
ATOM   8750  CA  ASN V  23    -27.664 131.764 213.410  1.00  0.00           C
ATOM   8751  CA  ALA V  24    -30.634 132.848 211.311  1.00  0.00           C
ATOM   8752  CA  LYS V  25    -31.096 136.121 213.239  1.00  0.00           C
ATOM   8753  CA  GLY V  26    -27.332 136.286 213.651  1.00  0.00           C
ATOM   8754  CA  GLU V  27    -26.675 135.282 217.252  1.00  0.00           C
ATOM   8755  CA  LYS V  28    -28.344 135.612 220.650  1.00  0.00           C
ATOM   8756  CA  ARG V  29    -27.660 136.428 224.296  1.00  0.00           C
ATOM   8757  CA  LEU V  30    -26.934 133.170 226.149  1.00  0.00           C
ATOM   8758  CA  ILE V  31    -27.864 129.504 226.042  1.00  0.00           C
ATOM   8759  CA  LYS V  32    -27.763 126.759 228.666  1.00  0.00           C
ATOM   8760  CA  THR V  33    -27.591 123.026 228.155  1.00  0.00           C
ATOM   8761  CA  TRP V  34    -26.837 119.993 230.286  1.00  0.00           C
ATOM   8762  CA  SER V  35    -25.290 118.545 227.136  1.00  0.00           C
ATOM   8763  CA  ARG V  36    -21.659 118.857 228.172  1.00  0.00           C
ATOM   8764  CA  ARG V  37    -21.508 115.513 226.325  1.00  0.00           C
ATOM   8765  CA  SER V  38    -21.466 117.305 222.964  1.00  0.00           C
ATOM   8766  CA  THR V  39    -18.538 118.183 220.711  1.00  0.00           C
ATOM   8767  CA  ILE V  40    -18.215 121.785 219.564  1.00  0.00           C
ATOM   8768  CA  VAL V  41    -18.868 122.636 215.934  1.00  0.00           C
ATOM   8769  CA  PRO V  42    -17.980 125.901 214.088  1.00  0.00           C
ATOM   8770  CA  GLU V  43    -21.567 127.187 214.152  1.00  0.00           C
ATOM   8771  CA  MET V  44    -21.071 127.432 217.908  1.00  0.00           C
ATOM   8772  CA  VAL V  45    -18.189 129.889 217.574  1.00  0.00           C
ATOM   8773  CA  GLY V  46    -18.887 133.454 218.667  1.00  0.00           C
ATOM   8774  CA  HIS V  47    -21.761 132.148 220.783  1.00  0.00           C
ATOM   8775  CA  THR V  48    -21.858 131.965 224.566  1.00  0.00           C
ATOM   8776  CA  ILE V  49    -23.193 128.668 225.860  1.00  0.00           C
ATOM   8777  CA  ALA V  50    -23.519 128.254 229.616  1.00  0.00           C
ATOM   8778  CA  VAL V  51    -22.693 124.676 230.696  1.00  0.00           C
ATOM   8779  CA  TYR V  52    -23.770 122.823 233.854  1.00  0.00           C
ATOM   8780  CA  ASN V  53    -21.276 122.101 236.663  1.00  0.00           C
ATOM   8781  CA  GLY V  54    -23.769 119.576 237.909  1.00  0.00           C
ATOM   8782  CA  LYS V  55    -24.782 122.447 240.154  1.00  0.00           C
ATOM   8783  CA  GLN V  56    -24.295 125.691 238.182  1.00  0.00           C
ATOM   8784  CA  HIS V  57    -24.632 127.112 234.696  1.00  0.00           C
ATOM   8785  CA  VAL V  58    -21.286 128.633 233.769  1.00  0.00           C
ATOM   8786  CA  PRO V  59    -20.976 131.087 230.836  1.00  0.00           C
ATOM   8787  CA  VAL V  60    -18.477 129.762 228.278  1.00  0.00           C
ATOM   8788  CA  TYR V  61    -17.535 132.001 225.335  1.00  0.00           C
ATOM   8789  CA  ILE V  62    -16.836 129.586 222.467  1.00  0.00           C
ATOM   8790  CA  THR V  63    -13.971 130.733 220.223  1.00  0.00           C
ATOM   8791  CA  GLU V  64    -12.372 129.091 217.194  1.00  0.00           C
ATOM   8792  CA  ASN V  65     -9.221 127.863 218.973  1.00  0.00           C
ATOM   8793  CA  MET V  66    -11.488 125.701 221.155  1.00  0.00           C
ATOM   8794  CA  VAL V  67    -13.670 124.020 218.535  1.00  0.00           C
ATOM   8795  CA  GLY V  68    -12.978 120.281 218.451  1.00  0.00           C
ATOM   8796  CA  HIS V  69    -13.248 120.160 222.267  1.00  0.00           C
ATOM   8797  CA  LYS V  70    -16.388 119.221 224.227  1.00  0.00           C
ATOM   8798  CA  LEU V  71    -17.946 122.073 226.246  1.00  0.00           C
ATOM   8799  CA  GLY V  72    -17.688 120.191 229.527  1.00  0.00           C
ATOM   8800  CA  GLU V  73    -13.943 120.663 229.170  1.00  0.00           C
ATOM   8801  CA  PHE V  74    -14.735 124.313 229.967  1.00  0.00           C
ATOM   8802  CA  ALA V  75    -17.116 123.807 232.877  1.00  0.00           C
ATOM   8803  CA  PRO V  76    -15.052 122.346 235.754  1.00  0.00           C
ATOM   8804  CA  THR V  77    -16.801 119.971 238.161  1.00  0.00           C
ATOM   8805  CA  ARG V  78    -14.852 119.609 241.374  1.00  0.00           C
ATOM   8806  CA  THR V  79    -13.865 122.485 243.623  1.00  0.00           C
ATOM   8807  CA  TYR V  80    -10.262 122.172 244.912  1.00  0.00           C
ATOM   8808  CA  ARG V  81     -7.820 124.051 247.152  1.00  0.00           C
TER    8809      ARG V  81
ATOM   8810  CA  ARG W   8    -57.711 141.419 349.076  1.00  0.00           C
ATOM   8811  CA  ASN W   9    -58.711 140.938 352.709  1.00  0.00           C
ATOM   8812  CA  LEU W  10    -58.627 137.439 354.198  1.00  0.00           C
ATOM   8813  CA  SER W  11    -59.966 138.508 357.595  1.00  0.00           C
ATOM   8814  CA  ALA W  12    -57.966 135.631 359.088  1.00  0.00           C
ATOM   8815  CA  LEU W  13    -55.118 138.218 359.200  1.00  0.00           C
ATOM   8816  CA  LYS W  14    -56.382 138.097 362.749  1.00  0.00           C
ATOM   8817  CA  ARG W  15    -54.096 135.082 363.079  1.00  0.00           C
ATOM   8818  CA  HIS W  16    -51.030 137.183 362.437  1.00  0.00           C
ATOM   8819  CA  ARG W  17    -52.575 139.800 364.683  1.00  0.00           C
ATOM   8820  CA  GLN W  18    -52.643 137.255 367.513  1.00  0.00           C
ATOM   8821  CA  SER W  19    -49.320 135.646 366.669  1.00  0.00           C
ATOM   8822  CA  LEU W  20    -47.647 138.917 367.548  1.00  0.00           C
ATOM   8823  CA  LYS W  21    -49.300 138.972 370.940  1.00  0.00           C
ATOM   8824  CA  ARG W  22    -48.455 135.377 371.800  1.00  0.00           C
ATOM   8825  CA  ARG W  23    -44.957 136.072 370.540  1.00  0.00           C
ATOM   8826  CA  LEU W  24    -44.687 138.932 372.981  1.00  0.00           C
ATOM   8827  CA  ARG W  25    -46.313 136.954 375.777  1.00  0.00           C
```

```
ATOM  8828 CA ASN W  26   -43.870 134.054 375.303 1.00 0.00           C
ATOM  8829 CA LYS W  27   -40.805 136.174 374.808 1.00 0.00           C
ATOM  8830 CA ALA W  28   -41.578 137.738 378.206 1.00 0.00           C
ATOM  8831 CA LYS W  29   -41.870 134.451 380.043 1.00 0.00           C
ATOM  8832 CA LYS W  30   -38.590 133.072 378.776 1.00 0.00           C
ATOM  8833 CA SER W  31   -36.481 136.148 379.436 1.00 0.00           C
ATOM  8834 CA ALA W  32   -37.678 136.065 383.053 1.00 0.00           C
ATOM  8835 CA ILE W  33   -36.784 132.395 383.127 1.00 0.00           C
ATOM  8836 CA LYS W  34   -33.237 132.915 381.856 1.00 0.00           C
ATOM  8837 CA THR W  35   -32.648 135.845 384.181 1.00 0.00           C
ATOM  8838 CA LEU W  36   -33.645 133.879 387.253 1.00 0.00           C
ATOM  8839 CA SER W  37   -31.779 130.778 386.081 1.00 0.00           C
ATOM  8840 CA LYS W  38   -28.461 132.616 385.853 1.00 0.00           C
ATOM  8841 CA LYS W  39   -29.278 134.633 388.960 1.00 0.00           C
ATOM  8842 CA ALA W  40   -29.544 131.319 390.782 1.00 0.00           C
ATOM  8843 CA VAL W  41   -26.608 129.559 389.108 1.00 0.00           C
ATOM  8844 CA GLN W  42   -24.522 132.599 389.913 1.00 0.00           C
ATOM  8845 CA LEU W  43   -25.567 132.576 393.588 1.00 0.00           C
ATOM  8846 CA ALA W  44   -24.734 128.887 393.931 1.00 0.00           C
ATOM  8847 CA GLN W  45   -21.652 129.824 391.948 1.00 0.00           C
ATOM  8848 CA GLU W  46   -20.433 132.166 394.713 1.00 0.00           C
ATOM  8849 CA GLY W  47   -21.306 129.443 397.214 1.00 0.00           C
ATOM  8850 CA LYS W  48   -24.262 131.260 398.860 1.00 0.00           C
ATOM  8851 CA ALA W  49   -26.509 128.324 399.790 1.00 0.00           C
ATOM  8852 CA GLU W  50   -29.843 129.805 400.916 1.00 0.00           C
ATOM  8853 CA GLU W  51   -30.552 132.548 398.380 1.00 0.00           C
ATOM  8854 CA ALA W  52   -29.123 130.374 395.591 1.00 0.00           C
ATOM  8855 CA LEU W  53   -31.826 127.768 396.195 1.00 0.00           C
ATOM  8856 CA LYS W  54   -34.543 130.332 397.027 1.00 0.00           C
ATOM  8857 CA ILE W  55   -34.108 131.787 393.586 1.00 0.00           C
ATOM  8858 CA MET W  56   -33.714 128.365 391.997 1.00 0.00           C
ATOM  8859 CA ARG W  57   -37.200 127.401 393.267 1.00 0.00           C
ATOM  8860 CA LYS W  58   -38.641 130.457 391.484 1.00 0.00           C
ATOM  8861 CA ALA W  59   -36.829 129.468 388.327 1.00 0.00           C
ATOM  8862 CA GLU W  60   -38.183 125.945 388.695 1.00 0.00           C
ATOM  8863 CA SER W  61   -41.667 127.419 389.107 1.00 0.00           C
ATOM  8864 CA LEU W  62   -41.651 129.867 386.222 1.00 0.00           C
ATOM  8865 CA ILE W  63   -40.378 127.053 384.042 1.00 0.00           C
ATOM  8866 CA ASP W  64   -43.103 124.554 384.889 1.00 0.00           C
ATOM  8867 CA LYS W  65   -45.667 127.325 384.428 1.00 0.00           C
ATOM  8868 CA ALA W  66   -44.080 128.239 381.129 1.00 0.00           C
ATOM  8869 CA ALA W  67   -44.810 124.632 380.157 1.00 0.00           C
ATOM  8870 CA LYS W  68   -48.349 125.064 381.475 1.00 0.00           C
ATOM  8871 CA GLY W  69   -49.417 127.008 378.405 1.00 0.00           C
ATOM  8872 CA SER W  70   -47.558 126.610 375.114 1.00 0.00           C
ATOM  8873 CA THR W  71   -44.438 128.640 375.907 1.00 0.00           C
ATOM  8874 CA LEU W  72   -41.689 126.253 376.954 1.00 0.00           C
ATOM  8875 CA HIS W  73   -43.923 123.223 376.836 1.00 0.00           C
ATOM  8876 CA LYS W  74   -42.909 119.528 376.880 1.00 0.00           C
ATOM  8877 CA ASN W  75   -39.506 118.225 377.916 1.00 0.00           C
ATOM  8878 CA ALA W  76   -38.332 121.751 377.168 1.00 0.00           C
ATOM  8879 CA ALA W  77   -39.311 122.415 380.758 1.00 0.00           C
ATOM  8880 CA ALA W  78   -37.707 119.177 381.926 1.00 0.00           C
ATOM  8881 CA ARG W  79   -34.364 120.029 380.279 1.00 0.00           C
ATOM  8882 CA ARG W  80   -34.366 123.488 381.828 1.00 0.00           C
ATOM  8883 CA LYS W  81   -34.986 122.223 385.333 1.00 0.00           C
ATOM  8884 CA SER W  82   -32.382 119.460 385.250 1.00 0.00           C
ATOM  8885 CA ARG W  83   -29.654 121.597 383.606 1.00 0.00           C
ATOM  8886 CA LEU W  84   -30.498 124.085 386.388 1.00 0.00           C
ATOM  8887 CA MET W  85   -30.665 121.920 389.539 1.00 0.00           C
ATOM  8888 CA ARG W  86   -27.556 120.223 388.199 1.00 0.00           C
ATOM  8889 CA LYS W  87   -25.448 123.356 387.655 1.00 0.00           C
ATOM  8890 CA VAL W  88   -26.665 124.664 391.026 1.00 0.00           C
ATOM  8891 CA ARG W  89   -25.939 121.669 393.245 1.00 0.00           C
ATOM  8892 CA GLN W  90   -22.501 121.193 391.696 1.00 0.00           C
ATOM  8893 CA LEU W  91   -21.440 124.839 391.980 1.00 0.00           C
ATOM  8894 CA LEU W  92   -22.606 124.460 395.554 1.00 0.00           C
ATOM  8895 CA GLU W  93   -19.700 122.035 396.025 1.00 0.00           C
ATOM  8896 CA ALA W  94   -17.539 124.769 397.490 1.00 0.00           C
ATOM  8897 CA ALA W  95   -18.546 124.060 401.106 1.00 0.00           C
ATOM  8898 CA GLY W  96   -22.193 124.425 400.155 1.00 0.00           C
ATOM  8899 CA ALA W  97   -24.445 122.321 402.351 1.00 0.00           C
ATOM  8900 CA PRO W  98   -27.886 122.926 400.750 1.00 0.00           C
ATOM  8901 CA LEU W  99   -29.674 124.750 403.563 1.00 0.00           C
ATOM  8902 CA ILE W 100   -33.111 125.501 402.126 1.00 0.00           C
ATOM  8903 CA GLY W 101   -32.599 122.372 400.046 1.00 0.00           C
ATOM  8904 CA GLY W 102   -35.563 123.706 398.110 1.00 0.00           C
ATOM  8905 CA GLY W 103   -35.371 122.260 394.636 1.00 0.00           C
ATOM  8906 CA LEU W 104   -32.852 119.725 395.925 1.00 0.00           C
ATOM  8907 CA SER W 105   -33.627 116.265 397.235 1.00 0.00           C
ATOM  8908 CA ALA W 106   -30.758 116.020 399.709 1.00 0.00           C
TER   8909          ALA W 106
ATOM  8910 CA GLY X   2    10.635  94.532 228.653 1.00 0.00           C
ATOM  8911 CA LYS X   3     7.154  93.237 229.443 1.00 0.00           C
ATOM  8912 CA GLY X   4     6.312  96.914 229.480 1.00 0.00           C
ATOM  8913 CA ASP X   5     7.402  98.142 226.019 1.00 0.00           C
ATOM  8914 CA ARG X   6     4.163  97.972 224.065 1.00 0.00           C
```

```
ATOM   8915  CA  ARG X   7       6.146  97.938 220.828  1.00  0.00           C
ATOM   8916  CA  THR X   8       8.175  94.743 221.265  1.00  0.00           C
ATOM   8917  CA  ARG X   9       7.484  90.987 221.265  1.00  0.00           C
ATOM   8918  CA  ARG X  10       7.126  90.730 225.061  1.00  0.00           C
ATOM   8919  CA  GLY X  11       5.363  94.058 225.314  1.00  0.00           C
ATOM   8920  CA  LYS X  12       2.704  92.626 223.003  1.00  0.00           C
ATOM   8921  CA  ILE X  13       2.532  89.203 224.628  1.00  0.00           C
ATOM   8922  CA  TRP X  14       2.221  90.812 228.055  1.00  0.00           C
ATOM   8923  CA  ARG X  15      -0.590  93.031 226.866  1.00  0.00           C
ATOM   8924  CA  GLY X  16      -2.068  90.001 225.119  1.00  0.00           C
ATOM   8925  CA  THR X  17      -2.221  91.594 221.683  1.00  0.00           C
ATOM   8926  CA  TYR X  18      -0.932  91.565 218.127  1.00  0.00           C
ATOM   8927  CA  GLY X  19       0.419  94.212 215.813  1.00  0.00           C
ATOM   8928  CA  LYS X  20       3.484  95.086 213.798  1.00  0.00           C
ATOM   8929  CA  TYR X  21       5.509  93.654 216.678  1.00  0.00           C
ATOM   8930  CA  ARG X  22       3.737  90.354 217.276  1.00  0.00           C
ATOM   8931  CA  PRO X  23       1.865  89.514 214.077  1.00  0.00           C
ATOM   8932  CA  ARG X  24      -0.482  86.531 213.864  1.00  0.00           C
ATOM   8933  CA  LYS X  25       1.926  84.491 211.659  1.00  0.00           C
TER    8934      LYS X  25
CONECT 1701 1715
CONECT 1715 1701 1716 1717 1718
CONECT 1716 1715
CONECT 1717 1715
CONECT 1718 1715 1719
CONECT 1719 1718 1720
CONECT 1720 1719 1721 1722
CONECT 1721 1720 1726
CONECT 1722 1720 1723 1724
CONECT 1723 1722 1739
CONECT 1724 1722 1725 1726
CONECT 1725 1724
CONECT 1726 1721 1724 1727
CONECT 1727 1726 1728 1738
CONECT 1728 1727 1729
CONECT 1729 1728 1730
CONECT 1730 1729 1731 1738
CONECT 1731 1730 1732 1733
CONECT 1732 1731
CONECT 1733 1731 1734
CONECT 1734 1733 1735 1737
CONECT 1735 1734 1736
CONECT 1736 1735
CONECT 1737 1734 1738
CONECT 1738 1727 1730 1737
CONECT 1739 1723
CONECT 1829 1844
CONECT 1844 1829 1845 1846 1847
CONECT 1845 1844
CONECT 1846 1844
CONECT 1847 1844 1848
CONECT 1848 1847 1849
CONECT 1849 1848 1850 1851
CONECT 1850 1849 1853
CONECT 1851 1849 1852 1854
CONECT 1852 1851 1864
CONECT 1853 1850 1854 1856
CONECT 1854 1851 1853 1855
CONECT 1855 1854
CONECT 1856 1853 1857 1863
CONECT 1857 1856 1858 1859
CONECT 1858 1857
CONECT 1859 1857 1860
CONECT 1860 1859 1861 1862
CONECT 1861 1860
CONECT 1862 1860 1863
CONECT 1863 1856 1862
CONECT 1864 1852 1865 1866 1867
CONECT 1865 1864
CONECT 1866 1864
CONECT 1867 1864 1868
CONECT 1868 1867 1869
CONECT 1869 1868 1870 1871
CONECT 1870 1869 1873
CONECT 1871 1869 1872 1874
CONECT 1872 1871 1884
CONECT 1873 1870 1874 1876
CONECT 1874 1871 1873 1875
CONECT 1875 1874
CONECT 1876 1873 1877 1883
CONECT 1877 1876 1878 1879
CONECT 1878 1877
CONECT 1879 1877 1880
CONECT 1880 1879 1881 1882
CONECT 1881 1880
CONECT 1882 1880 1883
CONECT 1883 1876 1882
```

```
CONECT 1884 1872
CONECT 2051 2063
CONECT 2063 2051 2064 2065 2066
CONECT 2064 2063
CONECT 2065 2063
CONECT 2066 2063 2067
CONECT 2067 2066 2068
CONECT 2068 2067 2069 2070
CONECT 2069 2068 2074
CONECT 2070 2068 2071 2072
CONECT 2071 2070 2088
CONECT 2072 2070 2073 2074
CONECT 2073 2072
CONECT 2074 2069 2072 2075
CONECT 2075 2074 2076 2085
CONECT 2076 2075 2077
CONECT 2077 2076 2078
CONECT 2078 2077 2079 2085
CONECT 2079 2078 2080 2081
CONECT 2080 2079
CONECT 2081 2079 2082
CONECT 2082 2081 2083 2084
CONECT 2083 2082 2086 2087
CONECT 2084 2082 2085
CONECT 2085 2075 2078 2084
CONECT 2086 2083
CONECT 2087 2083
CONECT 2088 2071
CONECT 2181 2213
CONECT 2195 2196 2200 2203
CONECT 2196 2195 2197 2201
CONECT 2197 2196 2198
CONECT 2198 2197 2199 2202
CONECT 2199 2198 2200
CONECT 2200 2195 2199
CONECT 2201 2196
CONECT 2202 2198
CONECT 2203 2195 2204 2209
CONECT 2204 2203 2205 2207
CONECT 2205 2204 2206
CONECT 2206 2205
CONECT 2207 2204 2208 2210
CONECT 2208 2207 2209 2211
CONECT 2209 2203 2208
CONECT 2210 2207 2216
CONECT 2211 2208 2212
CONECT 2212 2211 2213
CONECT 2213 2181 2212 2214 2215
CONECT 2214 2213
CONECT 2215 2213
CONECT 2216 2210
CONECT 2224 2236
CONECT 2236 2224 2237 2238 2239
CONECT 2237 2236
CONECT 2238 2236
CONECT 2239 2236 2240
CONECT 2240 2239 2241
CONECT 2241 2240 2242 2243
CONECT 2242 2241 2248
CONECT 2243 2241 2244 2245
CONECT 2244 2243 2260
CONECT 2245 2243 2246 2248
CONECT 2246 2245 2247
CONECT 2247 2246
CONECT 2248 2242 2245 2249
CONECT 2249 2248 2250 2259
CONECT 2250 2249 2251
CONECT 2251 2250 2252
CONECT 2252 2251 2253 2259
CONECT 2253 2252 2254 2255
CONECT 2254 2253
CONECT 2255 2253 2256
CONECT 2256 2255 2257 2258
CONECT 2257 2256
CONECT 2258 2256 2259
CONECT 2259 2249 2252 2258
CONECT 2260 2244
CONECT 2290 2340
CONECT 2304 2306 2311 2318
CONECT 2305 2306 2317
CONECT 2306 2304 2305 2307
CONECT 2307 2306 2308 2309
CONECT 2308 2307
CONECT 2309 2307 2310 2315
CONECT 2310 2309 2311 2313
CONECT 2311 2304 2310 2312
CONECT 2312 2311
```

```
CONECT 2313 2310 2314
CONECT 2314 2313 2315
CONECT 2315 2309 2314 2331
CONECT 2316 2317
CONECT 2317 2305 2316 2318
CONECT 2318 2304 2317 2319
CONECT 2319 2318 2320
CONECT 2320 2319 2321
CONECT 2321 2320 2322 2326
CONECT 2322 2321 2323 2324
CONECT 2323 2322
CONECT 2324 2322 2325
CONECT 2325 2324
CONECT 2326 2321 2327
CONECT 2327 2326 2328 2329
CONECT 2328 2327
CONECT 2329 2327 2330
CONECT 2330 2329
CONECT 2331 2315 2332 2337
CONECT 2332 2331 2333 2334
CONECT 2333 2332
CONECT 2334 2332 2335 2336
CONECT 2335 2334 2343
CONECT 2336 2334 2337 2338
CONECT 2337 2331 2336
CONECT 2338 2336 2339
CONECT 2339 2338 2340
CONECT 2340 2290 2339 2341 2342
CONECT 2341 2340
CONECT 2342 2340
CONECT 2343 2335
CONECT 2351 2382
CONECT 2365 2366 2370
CONECT 2366 2365 2367 2371
CONECT 2367 2366 2368
CONECT 2368 2367 2369 2372
CONECT 2369 2368 2370 2373
CONECT 2370 2365 2369
CONECT 2371 2366
CONECT 2372 2368
CONECT 2373 2369 2374 2379
CONECT 2374 2373 2375 2376
CONECT 2375 2374
CONECT 2376 2374 2377 2378
CONECT 2377 2376 2379 2380
CONECT 2378 2376 2385
CONECT 2379 2373 2377
CONECT 2380 2377 2381
CONECT 2381 2380 2382
CONECT 2382 2351 2381 2383 2384
CONECT 2383 2382
CONECT 2384 2382
CONECT 2385 2378 2386 2387 2388
CONECT 2386 2385
CONECT 2387 2385
CONECT 2388 2385 2389
CONECT 2389 2388 2390
CONECT 2390 2389 2391 2392
CONECT 2391 2390 2396
CONECT 2392 2390 2393 2394
CONECT 2393 2392 2406
CONECT 2394 2392 2395 2396
CONECT 2395 2394
CONECT 2396 2391 2394 2397
CONECT 2397 2396 2398 2404
CONECT 2398 2397 2399 2400
CONECT 2399 2398
CONECT 2400 2398 2401
CONECT 2401 2400 2402 2403
CONECT 2402 2401
CONECT 2403 2401 2404 2405
CONECT 2404 2397 2403
CONECT 2405 2403
CONECT 2406 2393
CONECT 2502 2517
CONECT 2517 2502 2518 2519 2520
CONECT 2518 2517
CONECT 2519 2517
CONECT 2520 2517 2521
CONECT 2521 2520 2522
CONECT 2522 2521 2523 2524
CONECT 2523 2522 2528
CONECT 2524 2522 2525 2526
CONECT 2525 2524 2541
CONECT 2526 2524 2527 2528
CONECT 2527 2526
CONECT 2528 2523 2526 2529
```

```
CONECT 2529 2528 2530 2539
CONECT 2530 2529 2531
CONECT 2531 2530 2532 2540
CONECT 2532 2531 2533 2539
CONECT 2533 2532 2534 2535
CONECT 2534 2533
CONECT 2535 2533 2536
CONECT 2536 2535 2537 2538
CONECT 2537 2536
CONECT 2538 2536 2539
CONECT 2539 2529 2532 2538
CONECT 2540 2531
CONECT 2541 2525
CONECT 2569 2581
CONECT 2581 2569 2582 2583 2584
CONECT 2582 2581
CONECT 2583 2581
CONECT 2584 2581 2585
CONECT 2585 2584 2586
CONECT 2586 2585 2587 2588
CONECT 2587 2586 2592
CONECT 2588 2586 2589 2590
CONECT 2589 2588 2602
CONECT 2590 2588 2591 2592
CONECT 2591 2590
CONECT 2592 2587 2590 2593
CONECT 2593 2592 2594 2600
CONECT 2594 2593 2595 2596
CONECT 2595 2594
CONECT 2596 2594 2597
CONECT 2597 2596 2598 2599
CONECT 2598 2597
CONECT 2599 2597 2600 2601
CONECT 2600 2593 2599
CONECT 2601 2599
CONECT 2602 2589
CONECT 2673 2706
CONECT 2688 2689 2694 2697
CONECT 2689 2688 2690 2695
CONECT 2690 2689 2691
CONECT 2691 2690 2692 2696
CONECT 2692 2691 2693 2694
CONECT 2693 2692
CONECT 2694 2688 2692
CONECT 2695 2689
CONECT 2696 2691
CONECT 2697 2688 2698 2703
CONECT 2698 2697 2699 2700
CONECT 2699 2698
CONECT 2700 2698 2701 2702
CONECT 2701 2700 2703 2704
CONECT 2702 2700 2726
CONECT 2703 2697 2701
CONECT 2704 2701 2705
CONECT 2705 2704 2706
CONECT 2706 2673 2705 2707 2708
CONECT 2707 2706
CONECT 2708 2706
CONECT 2709 2710 2714
CONECT 2710 2709 2711 2715
CONECT 2711 2710 2712
CONECT 2712 2711 2713 2716
CONECT 2713 2712 2714 2717
CONECT 2714 2709 2713
CONECT 2715 2710
CONECT 2716 2712
CONECT 2717 2713 2718 2723
CONECT 2718 2717 2719 2720
CONECT 2719 2718
CONECT 2720 2718 2721 2722
CONECT 2721 2720 2723 2724
CONECT 2722 2720 2729
CONECT 2723 2717 2721
CONECT 2724 2721 2725
CONECT 2725 2724 2726
CONECT 2726 2702 2725 2727 2728
CONECT 2727 2726
CONECT 2728 2726
CONECT 2729 2722
CONECT 2757 2772
CONECT 2772 2757 2773 2774 2775
CONECT 2773 2772
CONECT 2774 2772
CONECT 2775 2772 2776
CONECT 2776 2775 2777
CONECT 2777 2776 2778 2779
CONECT 2778 2777 2783
```

```
CONECT 2779 2777 2780 2781
CONECT 2780 2779 2795
CONECT 2781 2779 2782 2783
CONECT 2782 2781
CONECT 2783 2778 2781 2784
CONECT 2784 2783 2785 2794
CONECT 2785 2784 2786
CONECT 2786 2785 2787
CONECT 2787 2786 2788 2794
CONECT 2788 2787 2789 2790
CONECT 2789 2788
CONECT 2790 2788 2791 2792
CONECT 2791 2790
CONECT 2792 2790 2793
CONECT 2793 2792 2794
CONECT 2794 2784 2787 2793
CONECT 2795 2780
CONECT 3354 3368
CONECT 3368 3354 3369 3370 3371
CONECT 3369 3368
CONECT 3370 3368
CONECT 3371 3368 3372
CONECT 3372 3371 3373
CONECT 3373 3372 3374 3375
CONECT 3374 3373 3379
CONECT 3375 3373 3376 3377
CONECT 3376 3375 3392
CONECT 3377 3375 3378 3379
CONECT 3378 3377
CONECT 3379 3374 3377 3380
CONECT 3380 3379 3381 3391
CONECT 3381 3380 3382
CONECT 3382 3381 3383
CONECT 3383 3382 3384 3391
CONECT 3384 3383 3385 3386
CONECT 3385 3384
CONECT 3386 3384 3387
CONECT 3387 3386 3388 3390
CONECT 3388 3387 3389
CONECT 3389 3388
CONECT 3390 3387 3391
CONECT 3391 3380 3383 3390
CONECT 3392 3376
CONECT 3482 3497
CONECT 3497 3482 3498 3499 3500
CONECT 3498 3497
CONECT 3499 3497
CONECT 3500 3497 3501
CONECT 3501 3500 3502
CONECT 3502 3501 3503 3504
CONECT 3503 3502 3506
CONECT 3504 3502 3505 3507
CONECT 3505 3504 3517
CONECT 3506 3503 3507 3509
CONECT 3507 3504 3506 3508
CONECT 3508 3507
CONECT 3509 3506 3510 3516
CONECT 3510 3509 3511 3512
CONECT 3511 3510
CONECT 3512 3510 3513
CONECT 3513 3512 3514 3515
CONECT 3514 3513
CONECT 3515 3513 3516
CONECT 3516 3509 3515
CONECT 3517 3505 3518 3519 3520
CONECT 3518 3517
CONECT 3519 3517
CONECT 3520 3517 3521
CONECT 3521 3520 3522
CONECT 3522 3521 3523 3524
CONECT 3523 3522 3526
CONECT 3524 3522 3525 3527
CONECT 3525 3524 3537
CONECT 3526 3523 3527 3529
CONECT 3527 3524 3526 3528
CONECT 3528 3527
CONECT 3529 3526 3530 3536
CONECT 3530 3529 3531 3532
CONECT 3531 3530
CONECT 3532 3530 3533
CONECT 3533 3532 3534 3535
CONECT 3534 3533
CONECT 3535 3533 3536
CONECT 3536 3529 3535
CONECT 3537 3525
CONECT 3716 3717 3718 3719
CONECT 3717 3716
```

```
CONECT 3718 3716
CONECT 3719 3716 3720
CONECT 3720 3719 3721
CONECT 3721 3720 3722 3723
CONECT 3722 3721 3727
CONECT 3723 3721 3724 3725
CONECT 3724 3723 3741
CONECT 3725 3723 3726 3727
CONECT 3726 3725
CONECT 3727 3722 3725 3728
CONECT 3728 3727 3729 3738
CONECT 3729 3728 3730
CONECT 3730 3729 3731
CONECT 3731 3730 3732 3738
CONECT 3732 3731 3733 3734
CONECT 3733 3732
CONECT 3734 3732 3735
CONECT 3735 3734 3736 3737
CONECT 3736 3735 3739 3740
CONECT 3737 3735 3738
CONECT 3738 3728 3731 3737
CONECT 3739 3736
CONECT 3740 3736
CONECT 3741 3724
CONECT 3834 3866
CONECT 3848 3849 3853 3856
CONECT 3849 3848 3850 3854
CONECT 3850 3849 3851
CONECT 3851 3850 3852 3855
CONECT 3852 3851 3853
CONECT 3853 3848 3852
CONECT 3854 3849
CONECT 3855 3851
CONECT 3856 3848 3857 3862
CONECT 3857 3856 3858 3860
CONECT 3858 3857 3859
CONECT 3859 3858
CONECT 3860 3857 3861 3863
CONECT 3861 3860 3862 3864
CONECT 3862 3856 3861
CONECT 3863 3860 3869
CONECT 3864 3861 3865
CONECT 3865 3864 3866
CONECT 3866 3834 3865 3867 3868
CONECT 3867 3866
CONECT 3868 3866
CONECT 3869 3863
CONECT 3877 3889
CONECT 3889 3877 3890 3891 3892
CONECT 3890 3889
CONECT 3891 3889
CONECT 3892 3889 3893
CONECT 3893 3892 3894
CONECT 3894 3893 3895 3896
CONECT 3895 3894 3901
CONECT 3896 3894 3897 3898
CONECT 3897 3896 3913
CONECT 3898 3896 3899 3901
CONECT 3899 3898 3900
CONECT 3900 3899
CONECT 3901 3895 3898 3902
CONECT 3902 3901 3903 3912
CONECT 3903 3902 3904
CONECT 3904 3903 3905
CONECT 3905 3904 3906 3912
CONECT 3906 3905 3907 3908
CONECT 3907 3906
CONECT 3908 3906 3909
CONECT 3909 3908 3910 3911
CONECT 3910 3909
CONECT 3911 3909 3912
CONECT 3912 3902 3905 3911
CONECT 3913 3897
CONECT 3943 3993
CONECT 3957 3959 3964 3971
CONECT 3958 3959 3970
CONECT 3959 3957 3958 3960
CONECT 3960 3959 3961 3962
CONECT 3961 3960
CONECT 3962 3960 3963 3968
CONECT 3963 3962 3964 3966
CONECT 3964 3957 3963 3965
CONECT 3965 3964
CONECT 3966 3963 3967
CONECT 3967 3966 3968
CONECT 3968 3962 3967 3984
CONECT 3969 3970
```

```
CONECT 3970 3958 3969 3971
CONECT 3971 3957 3970 3972
CONECT 3972 3971 3973
CONECT 3973 3972 3974
CONECT 3974 3973 3975 3979
CONECT 3975 3974 3976 3977
CONECT 3976 3975
CONECT 3977 3975 3978
CONECT 3978 3977
CONECT 3979 3974 3980
CONECT 3980 3979 3981 3982
CONECT 3981 3980
CONECT 3982 3980 3983
CONECT 3983 3982
CONECT 3984 3968 3985 3990
CONECT 3985 3984 3986 3987
CONECT 3986 3985
CONECT 3987 3985 3988 3989
CONECT 3988 3987 3996
CONECT 3989 3987 3990 3991
CONECT 3990 3984 3989
CONECT 3991 3989 3992
CONECT 3992 3991 3993
CONECT 3993 3943 3992 3994 3995
CONECT 3994 3993
CONECT 3995 3993
CONECT 3996 3988
CONECT 4004 4035
CONECT 4018 4019 4023
CONECT 4019 4018 4020 4024
CONECT 4020 4019 4021
CONECT 4021 4020 4022 4025
CONECT 4022 4021 4023 4026
CONECT 4023 4018 4022
CONECT 4024 4019
CONECT 4025 4021
CONECT 4026 4022 4027 4032
CONECT 4027 4026 4028 4029
CONECT 4028 4027
CONECT 4029 4027 4030 4031
CONECT 4030 4029 4032 4033
CONECT 4031 4029 4038
CONECT 4032 4026 4030
CONECT 4033 4030 4034
CONECT 4034 4033 4035
CONECT 4035 4004 4034 4036 4037
CONECT 4036 4035
CONECT 4037 4035
CONECT 4038 4031 4039 4040 4041
CONECT 4039 4038
CONECT 4040 4038
CONECT 4041 4038 4042
CONECT 4042 4041 4043
CONECT 4043 4042 4044 4045
CONECT 4044 4043 4049
CONECT 4045 4043 4046 4047
CONECT 4046 4045 4059
CONECT 4047 4045 4048 4049
CONECT 4048 4047
CONECT 4049 4044 4047 4050
CONECT 4050 4049 4051 4057
CONECT 4051 4050 4052 4053
CONECT 4052 4051
CONECT 4053 4051 4054
CONECT 4054 4053 4055 4056
CONECT 4055 4054
CONECT 4056 4054 4057 4058
CONECT 4057 4050 4056
CONECT 4058 4056
CONECT 4059 4046
CONECT 4155 4170
CONECT 4170 4155 4171 4172 4173
CONECT 4171 4170
CONECT 4172 4170
CONECT 4173 4170 4174
CONECT 4174 4173 4175
CONECT 4175 4174 4176 4177
CONECT 4176 4175 4181
CONECT 4177 4175 4178 4179
CONECT 4178 4177 4194
CONECT 4179 4177 4180 4181
CONECT 4180 4179
CONECT 4181 4176 4179 4182
CONECT 4182 4181 4183 4192
CONECT 4183 4182 4184
CONECT 4184 4183 4185 4193
CONECT 4185 4184 4186 4192
```

```
CONECT 4186 4185 4187 4188
CONECT 4187 4186
CONECT 4188 4186 4189
CONECT 4189 4188 4190 4191
CONECT 4190 4189
CONECT 4191 4189 4192
CONECT 4192 4182 4185 4191
CONECT 4193 4184
CONECT 4194 4178
CONECT 4222 4234
CONECT 4234 4222 4235 4236 4237
CONECT 4235 4234
CONECT 4236 4234
CONECT 4237 4234 4238
CONECT 4238 4237 4239
CONECT 4239 4238 4240 4241
CONECT 4240 4239 4245
CONECT 4241 4239 4242 4243
CONECT 4242 4241 4255
CONECT 4243 4241 4244 4245
CONECT 4244 4243
CONECT 4245 4240 4243 4246
CONECT 4246 4245 4247 4253
CONECT 4247 4246 4248 4249
CONECT 4248 4247
CONECT 4249 4247 4250
CONECT 4250 4249 4251 4252
CONECT 4251 4250
CONECT 4252 4250 4253 4254
CONECT 4253 4246 4252
CONECT 4254 4252
CONECT 4255 4242
CONECT 4326 4359
CONECT 4341 4342 4347 4350
CONECT 4342 4341 4343 4348
CONECT 4343 4342 4344
CONECT 4344 4343 4345 4349
CONECT 4345 4344 4346 4347
CONECT 4346 4345
CONECT 4347 4341 4345
CONECT 4348 4342
CONECT 4349 4344
CONECT 4350 4341 4351 4356
CONECT 4351 4350 4352 4353
CONECT 4352 4351
CONECT 4353 4351 4354 4355
CONECT 4354 4353 4356 4357
CONECT 4355 4353 4379
CONECT 4356 4350 4354
CONECT 4357 4354 4358
CONECT 4358 4357 4359
CONECT 4359 4326 4358 4360 4361
CONECT 4360 4359
CONECT 4361 4359
CONECT 4362 4363 4367
CONECT 4363 4362 4364 4368
CONECT 4364 4363 4365
CONECT 4365 4364 4366 4369
CONECT 4366 4365 4367 4370
CONECT 4367 4362 4366
CONECT 4368 4363
CONECT 4369 4365
CONECT 4370 4366 4371 4376
CONECT 4371 4370 4372 4373
CONECT 4372 4371
CONECT 4373 4371 4374 4375
CONECT 4374 4373 4376 4377
CONECT 4375 4373 4382
CONECT 4376 4370 4374
CONECT 4377 4374 4378
CONECT 4378 4377 4379
CONECT 4379 4355 4378 4380 4381
CONECT 4380 4379
CONECT 4381 4379
CONECT 4382 4375
CONECT 4410 4425
CONECT 4425 4410 4426 4427 4428
CONECT 4426 4425
CONECT 4427 4425
CONECT 4428 4425 4429
CONECT 4429 4428 4430
CONECT 4430 4429 4431 4432
CONECT 4431 4430 4436
CONECT 4432 4430 4433 4434
CONECT 4433 4432 4448
CONECT 4434 4432 4435 4436
CONECT 4435 4434
```

```
CONECT 4436 4431 4434 4437
CONECT 4437 4436 4438 4447
CONECT 4438 4437 4439
CONECT 4439 4438 4440
CONECT 4440 4439 4441 4447
CONECT 4441 4440 4442 4443
CONECT 4442 4441
CONECT 4443 4441 4444 4445
CONECT 4444 4443
CONECT 4445 4443 4446
CONECT 4446 4445 4447
CONECT 4447 4437 4440 4446
CONECT 4448 4433
CONECT 4976 4977 4981 4984
CONECT 4977 4976 4978 4982
CONECT 4978 4977 4979
CONECT 4979 4978 4980 4983
CONECT 4980 4979 4981
CONECT 4981 4976 4980
CONECT 4982 4977
CONECT 4983 4979
CONECT 4984 4976 4985 4990
CONECT 4985 4984 4986 4987
CONECT 4986 4985
CONECT 4987 4985 4988 4989
CONECT 4988 4987 4990 4991
CONECT 4989 4987 4996
CONECT 4990 4984 4988
CONECT 4991 4988 4992
CONECT 4992 4991 4993
CONECT 4993 4992 4994 4995
CONECT 4994 4993
CONECT 4995 4993
CONECT 4996 4989
CONECT 5200 5215
CONECT 5215 5200 5216 5217 5218
CONECT 5216 5215
CONECT 5217 5215
CONECT 5218 5215 5219
CONECT 5219 5218 5220
CONECT 5220 5219 5221 5222
CONECT 5221 5220 5224
CONECT 5222 5220 5223 5225
CONECT 5223 5222 5235
CONECT 5224 5221 5225 5227
CONECT 5225 5222 5224 5226
CONECT 5226 5225
CONECT 5227 5224 5228 5234
CONECT 5228 5227 5229 5230
CONECT 5229 5228
CONECT 5230 5228 5231
CONECT 5231 5230 5232 5233
CONECT 5232 5231
CONECT 5233 5231 5234
CONECT 5234 5227 5233
CONECT 5235 5223 5236 5237 5238
CONECT 5236 5235
CONECT 5237 5235
CONECT 5238 5235 5239
CONECT 5239 5238 5240
CONECT 5240 5239 5241 5242
CONECT 5241 5240 5244
CONECT 5242 5240 5243 5245
CONECT 5243 5242 5255
CONECT 5244 5241 5245 5247
CONECT 5245 5242 5244 5246
CONECT 5246 5245
CONECT 5247 5244 5248 5254
CONECT 5248 5247 5249 5250
CONECT 5249 5248
CONECT 5250 5248 5251
CONECT 5251 5250 5252 5253
CONECT 5252 5251
CONECT 5253 5251 5254
CONECT 5254 5247 5253
CONECT 5255 5243
CONECT 5800 5801 5802 5803
CONECT 5801 5800
CONECT 5802 5800
CONECT 5803 5800 5804
CONECT 5804 5803 5805
CONECT 5805 5804 5806 5807
CONECT 5806 5805 5811
CONECT 5807 5805 5808 5809
CONECT 5808 5807 5821
CONECT 5809 5807 5810 5811
CONECT 5810 5809
```

```
CONECT 5811 5806 5809 5812
CONECT 5812 5811 5813 5819
CONECT 5813 5812 5814 5815
CONECT 5814 5813
CONECT 5815 5813 5816
CONECT 5816 5815 5817 5818
CONECT 5817 5816
CONECT 5818 5816 5819 5820
CONECT 5819 5812 5818
CONECT 5820 5818
CONECT 5821 5808
CONECT 5898 5931
CONECT 5913 5914 5919 5922
CONECT 5914 5913 5915 5920
CONECT 5915 5914 5916
CONECT 5916 5915 5917 5921
CONECT 5917 5916 5918 5919
CONECT 5918 5917
CONECT 5919 5913 5917
CONECT 5920 5914
CONECT 5921 5916
CONECT 5922 5913 5923 5928
CONECT 5923 5922 5924 5925
CONECT 5924 5923
CONECT 5925 5923 5926 5927
CONECT 5926 5925 5928 5929
CONECT 5927 5925 5951
CONECT 5928 5922 5926
CONECT 5929 5926 5930
CONECT 5930 5929 5931
CONECT 5931 5898 5930 5932 5933
CONECT 5932 5931
CONECT 5933 5931
CONECT 5934 5935 5939
CONECT 5935 5934 5936 5940
CONECT 5936 5935 5937
CONECT 5937 5936 5938 5941
CONECT 5938 5937 5939 5942
CONECT 5939 5934 5938
CONECT 5940 5935
CONECT 5941 5937
CONECT 5942 5938 5943 5948
CONECT 5943 5942 5944 5945
CONECT 5944 5943
CONECT 5945 5943 5946 5947
CONECT 5946 5945 5948 5949
CONECT 5947 5945 5954
CONECT 5948 5942 5946
CONECT 5949 5946 5950
CONECT 5950 5949 5951
CONECT 5951 5927 5950 5952 5953
CONECT 5952 5951
CONECT 5953 5951
CONECT 5954 5947
MASTER      384    0   34    0    0    0    0    6 8909   25  817  341
END
```

File B ----------------------------------------------------------------------
Title Crystal Structure Of The Ribosome At 5.5 A Resolution. This File,
1GIy, Contains The 50S Ribosome Subunit. The 30S Ribosome Subunit, Three
tRNA, and Mrna Molecules Are In The File 1GIx
Classification   Ribosome
Compound    Mol_Id: 1; Molecule: 50S 23S Ribosomal RNA; Chain: A
Mol_Id: 2; Molecule: 50S 5S Ribosomal RNA; Chain: B
Mol_Id: 3; Molecule: 50S Ribosomal Protein L1; Chain: C
Mol_Id: 4; Molecule: 50S Ribosomal Protein L2; Chain: D
Mol_Id: 5; Molecule: 50S Ribosomal Protein L3; Chain: E
Mol_Id: 6; Molecule: 50S Ribosomal Protein L4; Chain: F
Mol_Id: 7; Molecule: 50S Ribosomal Protein L5; Chain: G
Mol_Id: 8; Molecule: 50S Ribosomal Protein L6; Chain: H
Mol_Id: 9; Molecule: 50S Ribosomal Protein L7/L12; Chain: I, J
Mol_Id: 10; Molecule: 50S Ribosomal Protein L9; Chain: K
Mol_Id: 11; Molecule: 50S Ribosomal Protein L11; Chain: L
Mol_Id: 12; Molecule: 50S Ribosomal Protein L13; Chain: M
Mol_Id: 13; Molecule: 50S Ribosomal Protein L14; Chain: N
Mol_Id: 14; Molecule: 50S Ribosomal Protein L15; Chain: O
Mol_Id: 15; Molecule: 50S Ribosomal Protein L16; Chain: P
Mol_Id: 16; Molecule: 50S Ribosomal Protein L18; Chain: Q
Mol_Id: 17; Molecule: 50S Ribosomal Protein L19; Chain: R
Mol_Id: 18; Molecule: 50S Ribosomal Protein L22; Chain: S
Mol_Id: 19; Molecule: 50S Ribosomal Protein L23; Chain: T
Mol_Id: 20; Molecule: 50S Ribosomal Protein L24; Chain: U
Mol_Id: 21; Molecule: 50S Ribosomal Protein L25; Chain: V
Mol_Id: 22; Molecule: 50S Ribosomal Protein L29; Chain: W
Mol_Id: 23; Molecule: 50S Ribosomal Protein L30; Chain: X

```
HEADER    RIBOSOME                                30-MAR-01   1GIY
TITLE     CRYSTAL STRUCTURE OF THE RIBOSOME AT 5.5 A RESOLUTION. THIS
TITLE    2 FILE, 1GIY, CONTAINS THE 50S RIBOSOME SUBUNIT. THE 30S
TITLE    3 RIBOSOME SUBUNIT, THREE TRNA, AND MRNA MOLECULES ARE IN THE
TITLE    4 FILE 1GIX
COMPND    MOL_ID: 1;
COMPND   2 MOLECULE: 50S 23S RIBOSOMAL RNA;
COMPND   3 CHAIN: A;
COMPND   4 MOL_ID: 2;
COMPND   5 MOLECULE: 50S 5S RIBOSOMAL RNA;
COMPND   6 CHAIN: B;
COMPND   7 MOL_ID: 3;
COMPND   8 MOLECULE: 50S RIBOSOMAL PROTEIN L1;
COMPND   9 CHAIN: C;
COMPND  10 MOL_ID: 4;
COMPND  11 MOLECULE: 50S RIBOSOMAL PROTEIN L2;
COMPND  12 CHAIN: D;
COMPND  13 MOL_ID: 5;
COMPND  14 MOLECULE: 50S RIBOSOMAL PROTEIN L3;
COMPND  15 CHAIN: E;
COMPND  16 MOL_ID: 6;
COMPND  17 MOLECULE: 50S RIBOSOMAL PROTEIN L4;
COMPND  18 CHAIN: F;
COMPND  19 MOL_ID: 7;
COMPND  20 MOLECULE: 50S RIBOSOMAL PROTEIN L5;
COMPND  21 CHAIN: G;
COMPND  22 MOL_ID: 8;
COMPND  23 MOLECULE: 50S RIBOSOMAL PROTEIN L6;
COMPND  24 CHAIN: H;
COMPND  25 MOL_ID: 9;
COMPND  26 MOLECULE: 50S RIBOSOMAL PROTEIN L7/L12;
COMPND  27 CHAIN: I, J;
COMPND  28 MOL_ID: 10;
COMPND  29 MOLECULE: 50S RIBOSOMAL PROTEIN L9;
COMPND  30 CHAIN: K;
COMPND  31 MOL_ID: 11;
COMPND  32 MOLECULE: 50S RIBOSOMAL PROTEIN L11;
COMPND  33 CHAIN: L;
COMPND  34 MOL_ID: 12;
COMPND  35 MOLECULE: 50S RIBOSOMAL PROTEIN L13;
COMPND  36 CHAIN: M;
COMPND  37 MOL_ID: 13;
COMPND  38 MOLECULE: 50S RIBOSOMAL PROTEIN L14;
COMPND  39 CHAIN: N;
COMPND  40 MOL_ID: 14;
COMPND  41 MOLECULE: 50S RIBOSOMAL PROTEIN L15;
COMPND  42 CHAIN: O;
COMPND  43 MOL_ID: 15;
COMPND  44 MOLECULE: 50S RIBOSOMAL PROTEIN L16;
COMPND  45 CHAIN: P;
COMPND  46 MOL_ID: 16;
COMPND  47 MOLECULE: 50S RIBOSOMAL PROTEIN L18;
COMPND  48 CHAIN: Q;
COMPND  49 MOL_ID: 17;
COMPND  50 MOLECULE: 50S RIBOSOMAL PROTEIN L19;
COMPND  51 CHAIN: R;
COMPND  52 MOL_ID: 18;
COMPND  53 MOLECULE: 50S RIBOSOMAL PROTEIN L22;
COMPND  54 CHAIN: S;
COMPND  55 MOL_ID: 19;
COMPND  56 MOLECULE: 50S RIBOSOMAL PROTEIN L23;
COMPND  57 CHAIN: T;
COMPND  58 MOL_ID: 20;
COMPND  59 MOLECULE: 50S RIBOSOMAL PROTEIN L24;
COMPND  60 CHAIN: U;
COMPND  61 MOL_ID: 21;
COMPND  62 MOLECULE: 50S RIBOSOMAL PROTEIN L25;
COMPND  63 CHAIN: V;
COMPND  64 MOL_ID: 22;
COMPND  65 MOLECULE: 50S RIBOSOMAL PROTEIN L29;
COMPND  66 CHAIN: W;
COMPND  67 MOL_ID: 23;
COMPND  68 MOLECULE: 50S RIBOSOMAL PROTEIN L30;
COMPND  69 CHAIN: X
SOURCE    MOL_ID: 1;
SOURCE   2 ORGANISM_SCIENTIFIC: THERMUS THERMOPHILUS;
SOURCE   3 ORGANISM_COMMON: BACTERIA;
SOURCE   4 MOL_ID: 2;
SOURCE   5 ORGANISM_SCIENTIFIC: THERMUS THERMOPHILUS;
SOURCE   6 ORGANISM_COMMON: BACTERIA;
SOURCE   7 MOL_ID: 3;
SOURCE   8 ORGANISM_SCIENTIFIC: THERMUS THERMOPHILUS;
SOURCE   9 ORGANISM_COMMON: BACTERIA;
SOURCE  10 MOL_ID: 4;
SOURCE  11 ORGANISM_SCIENTIFIC: THERMUS THERMOPHILUS;
SOURCE  12 ORGANISM_COMMON: BACTERIA;
SOURCE  13 MOL_ID: 5;
```

```
SOURCE   14 ORGANISM_SCIENTIFIC: THERMUS THERMOPHILUS;
SOURCE   15 ORGANISM_COMMON: BACTERIA;
SOURCE   16 MOL_ID: 6;
SOURCE   17 ORGANISM_SCIENTIFIC: THERMUS THERMOPHILUS;
SOURCE   18 ORGANISM_COMMON: BACTERIA;
SOURCE   19 MOL_ID: 7;
SOURCE   20 ORGANISM_SCIENTIFIC: THERMUS THERMOPHILUS;
SOURCE   21 ORGANISM_COMMON: BACTERIA;
SOURCE   22 MOL_ID: 8;
SOURCE   23 ORGANISM_SCIENTIFIC: THERMUS THERMOPHILUS;
SOURCE   24 ORGANISM_COMMON: BACTERIA;
SOURCE   25 MOL_ID: 9;
SOURCE   26 ORGANISM_SCIENTIFIC: THERMUS THERMOPHILUS;
SOURCE   27 ORGANISM_COMMON: BACTERIA;
SOURCE   28 MOL_ID: 10;
SOURCE   29 ORGANISM_SCIENTIFIC: THERMUS THERMOPHILUS;
SOURCE   30 ORGANISM_COMMON: BACTERIA;
SOURCE   31 MOL_ID: 11;
SOURCE   32 ORGANISM_SCIENTIFIC: THERMUS THERMOPHILUS;
SOURCE   33 ORGANISM_COMMON: BACTERIA;
SOURCE   34 MOL_ID: 12;
SOURCE   35 ORGANISM_SCIENTIFIC: THERMUS THERMOPHILUS;
SOURCE   36 ORGANISM_COMMON: BACTERIA;
SOURCE   37 MOL_ID: 13;
SOURCE   38 ORGANISM_SCIENTIFIC: THERMUS THERMOPHILUS;
SOURCE   39 ORGANISM_COMMON: BACTERIA;
SOURCE   40 MOL_ID: 14;
SOURCE   41 ORGANISM_SCIENTIFIC: THERMUS THERMOPHILUS;
SOURCE   42 ORGANISM_COMMON: BACTERIA;
SOURCE   43 MOL_ID: 15;
SOURCE   44 ORGANISM_SCIENTIFIC: THERMUS THERMOPHILUS;
SOURCE   45 ORGANISM_COMMON: BACTERIA;
SOURCE   46 MOL_ID: 16;
SOURCE   47 ORGANISM_SCIENTIFIC: THERMUS THERMOPHILUS;
SOURCE   48 ORGANISM_COMMON: BACTERIA;
SOURCE   49 MOL_ID: 17;
SOURCE   50 ORGANISM_SCIENTIFIC: THERMUS THERMOPHILUS;
SOURCE   51 ORGANISM_COMMON: BACTERIA;
SOURCE   52 MOL_ID: 18;
SOURCE   53 ORGANISM_SCIENTIFIC: THERMUS THERMOPHILUS;
SOURCE   54 ORGANISM_COMMON: BACTERIA;
SOURCE   55 MOL_ID: 19;
SOURCE   56 ORGANISM_SCIENTIFIC: THERMUS THERMOPHILUS;
SOURCE   57 ORGANISM_COMMON: BACTERIA;
SOURCE   58 MOL_ID: 20;
SOURCE   59 ORGANISM_SCIENTIFIC: THERMUS THERMOPHILUS;
SOURCE   60 ORGANISM_COMMON: BACTERIA;
SOURCE   61 MOL_ID: 21;
SOURCE   62 ORGANISM_SCIENTIFIC: THERMUS THERMOPHILUS;
SOURCE   63 ORGANISM_COMMON: BACTERIA;
SOURCE   64 MOL_ID: 22;
SOURCE   65 ORGANISM_SCIENTIFIC: THERMUS THERMOPHILUS;
SOURCE   66 ORGANISM_COMMON: BACTERIA;
SOURCE   67 MOL_ID: 23;
SOURCE   68 ORGANISM_SCIENTIFIC: THERMUS THERMOPHILUS;
SOURCE   69 ORGANISM_COMMON: BACTERIA
KEYWDS      RIBOSOME ASSEMBLY, PROTEIN SYNTHESIS, LIFE
EXPDTA      X-RAY DIFFRACTION
AUTHOR      M.M.YUSUPOV,G.Z.YUSUPOVA,A.BAUCOM,K.LIEBERMAN,T.N.EARNEST,
AUTHOR    2 J.H.D.CATE,H.F.NOLLER
REVDAT    1   04-MAY-01 1GIY     0
JRNL        AUTH   M.M.YUSUPOV,G.Z.YUSUPOVA,A.BAUCOM,K.LIEBERMAN,
JRNL        AUTH 2 T.N.EARNEST,J.H.D.CATE,H.F.NOLLER
JRNL        TITL   CRYSTAL STRUCTURE OF THE RIBOSOME AT 5.5 A
JRNL        TITL 2 RESOLUTION
JRNL        REF    SCIENCE                       V. 292    883 2001
JRNL        REFN   ASTM SCIEAS   US ISSN 0036-8075
REMARK   1
REMARK   2
REMARK   2 RESOLUTION. 5.50 ANGSTROMS.
REMARK   3
REMARK   3 REFINEMENT.
REMARK   3   PROGRAM    : O
REMARK   3   AUTHORS    : JONES,ZOU,COWAN,KJELDGAARD
REMARK   3
REMARK   3  DATA USED IN REFINEMENT.
REMARK   3   RESOLUTION RANGE HIGH (ANGSTROMS) : 5.50
REMARK   3   RESOLUTION RANGE LOW  (ANGSTROMS) : 250.00
REMARK   3   DATA CUTOFF            (SIGMA(F)) : NULL
REMARK   3   DATA CUTOFF HIGH         (ABS(F)) : NULL
REMARK   3   DATA CUTOFF LOW          (ABS(F)) : NULL
REMARK   3   COMPLETENESS (WORKING+TEST)   (%) : 95.3
REMARK   3   NUMBER OF REFLECTIONS             : 209044
REMARK   3
REMARK   3
REMARK   3  FIT TO DATA USED IN REFINEMENT.
REMARK   3   CROSS-VALIDATION METHOD           : NULL
```

```
REMARK   3   FREE R VALUE TEST SET SELECTION  : NULL
REMARK   3   R VALUE            (WORKING SET) : NULL
REMARK   3   FREE R VALUE                     : NULL
REMARK   3   FREE R VALUE TEST SET SIZE   (%) : NULL
REMARK   3   FREE R VALUE TEST SET COUNT      : NULL
REMARK   3   ESTIMATED ERROR OF FREE R VALUE  : NULL
REMARK   3
REMARK   3  FIT IN THE HIGHEST RESOLUTION BIN.
REMARK   3   TOTAL NUMBER OF BINS USED            : NULL
REMARK   3   BIN RESOLUTION RANGE HIGH      (A)   : NULL
REMARK   3   BIN RESOLUTION RANGE LOW       (A)   : NULL
REMARK   3   BIN COMPLETENESS (WORKING+TEST) (%)  : NULL
REMARK   3   REFLECTIONS IN BIN    (WORKING SET)  : NULL
REMARK   3   BIN R VALUE           (WORKING SET)  : NULL
REMARK   3   BIN FREE R VALUE                     : NULL
REMARK   3   BIN FREE R VALUE TEST SET SIZE  (%)  : NULL
REMARK   3   BIN FREE R VALUE TEST SET COUNT      : NULL
REMARK   3   ESTIMATED ERROR OF BIN FREE R VALUE  : NULL
REMARK   3
REMARK   3  NUMBER OF NON-HYDROGEN ATOMS USED IN REFINEMENT.
REMARK   3   PROTEIN ATOMS            : 2735
REMARK   3   NUCLEIC ACID ATOMS       : 3012
REMARK   3   HETEROGEN ATOMS          : 0
REMARK   3   SOLVENT ATOMS            : 0
REMARK   3
REMARK   3  B VALUES.
REMARK   3   FROM WILSON PLOT           (A**2) : NULL
REMARK   3   MEAN B VALUE      (OVERALL, A**2) : NULL
REMARK   3   OVERALL ANISOTROPIC B VALUE.
REMARK   3    B11 (A**2) : NULL
REMARK   3    B22 (A**2) : NULL
REMARK   3    B33 (A**2) : NULL
REMARK   3    B12 (A**2) : NULL
REMARK   3    B13 (A**2) : NULL
REMARK   3    B23 (A**2) : NULL
REMARK   3
REMARK   3  ESTIMATED COORDINATE ERROR.
REMARK   3   ESD FROM LUZZATI PLOT       (A) : NULL
REMARK   3   ESD FROM SIGMAA             (A) : NULL
REMARK   3   LOW RESOLUTION CUTOFF       (A) : NULL
REMARK   3
REMARK   3  CROSS-VALIDATED ESTIMATED COORDINATE ERROR.
REMARK   3   ESD FROM C-V LUZZATI PLOT   (A) : NULL
REMARK   3   ESD FROM C-V SIGMAA         (A) : NULL
REMARK   3
REMARK   3  RMS DEVIATIONS FROM IDEAL VALUES.
REMARK   3   BOND LENGTHS              (A) : NULL
REMARK   3   BOND ANGLES         (DEGREES) : NULL
REMARK   3   DIHEDRAL ANGLES     (DEGREES) : NULL
REMARK   3   IMPROPER ANGLES     (DEGREES) : NULL
REMARK   3
REMARK   3  ISOTROPIC THERMAL MODEL : NULL
REMARK   3
REMARK   3  ISOTROPIC THERMAL FACTOR RESTRAINTS.    RMS      SIGMA
REMARK   3   MAIN-CHAIN BOND              (A**2) : NULL  ; NULL
REMARK   3   MAIN-CHAIN ANGLE             (A**2) : NULL  ; NULL
REMARK   3   SIDE-CHAIN BOND              (A**2) : NULL  ; NULL
REMARK   3   SIDE-CHAIN ANGLE             (A**2) : NULL  ; NULL
REMARK   3
REMARK   3
REMARK   3  NCS MODEL : NULL
REMARK   3
REMARK   3  NCS RESTRAINTS.                         RMS    SIGMA/WEIGHT
REMARK   3   GROUP  1  POSITIONAL         (A)    : NULL  ; NULL
REMARK   3   GROUP  1  B-FACTOR           (A**2) : NULL  ; NULL
REMARK   3
REMARK   3  PARAMETER FILE  1  : NULL
REMARK   3  TOPOLOGY FILE  1   : NULL
REMARK   3
REMARK   3  OTHER REFINEMENT REMARKS: THE MODEL WAS BUILT BY MANUAL
REMARK   3  FITTING OF INDIVIDUAL MOLECULES INTO THE EXPERIMENTAL
REMARK   3  ELECTRON DENSITY USING THE GRAPHIC PROGRAM O.
REMARK   4
REMARK   4 1GIY COMPLIES WITH FORMAT V. 2.3, 09-JULY-1998
REMARK 100
REMARK 100 THIS ENTRY HAS BEEN PROCESSED BY THE NUCLEIC ACID DATABASE
REMARK 100 ON 03-APR-2001.
REMARK 100 THE NDB ID CODE IS RR0032.
REMARK 105
REMARK 105 THE PROTEIN DATA BANK HAS ADOPTED THE SACCHARIDE CHEMISTS
REMARK 105 NOMENCLATURE FOR ATOMS OF THE DEOXYRIBOSE/RIBOSE MOIETY
REMARK 105 RATHER THAN THAT OF THE NUCLEOSIDE CHEMISTS.  THE RING
REMARK 105 OXYGEN ATOM IS LABELLED O4* INSTEAD OF O1*.
REMARK 200
REMARK 200 EXPERIMENTAL DETAILS
REMARK 200  EXPERIMENT TYPE                : X-RAY DIFFRACTION
REMARK 200  DATE OF DATA COLLECTION        : NULL
```

```
REMARK 200  TEMPERATURE           (KELVIN) : 100.0
REMARK 200  PH                             : NULL
REMARK 200  NUMBER OF CRYSTALS USED        : 2
REMARK 200
REMARK 200  SYNCHROTRON              (Y/N) : Y
REMARK 200  RADIATION SOURCE               : ALS
REMARK 200  BEAMLINE                       : 5.0.2
REMARK 200  X-RAY GENERATOR MODEL          : NULL
REMARK 200  MONOCHROMATIC OR LAUE    (M/L) : M
REMARK 200  WAVELENGTH OR RANGE        (A) : 1.100
REMARK 200  MONOCHROMATOR                  : NULL
REMARK 200  OPTICS                         : NULL
REMARK 200
REMARK 200  DETECTOR TYPE                  : CCD
REMARK 200  DETECTOR MANUFACTURER          : ADSC QUANTUM 4
REMARK 200  INTENSITY-INTEGRATION SOFTWARE : DENZO
REMARK 200  DATA SCALING SOFTWARE          : SCALEPACK
REMARK 200
REMARK 200  NUMBER OF UNIQUE REFLECTIONS   : 209044
REMARK 200  RESOLUTION RANGE HIGH      (A) : 5.000
REMARK 200  RESOLUTION RANGE LOW       (A) : 250.000
REMARK 200  REJECTION CRITERIA  (SIGMA(I)) : 0.000
REMARK 200
REMARK 200 OVERALL.
REMARK 200  COMPLETENESS FOR RANGE     (%) : 95.3
REMARK 200  DATA REDUNDANCY                : 2.800
REMARK 200  R MERGE                    (I) : NULL
REMARK 200  R SYM                      (I) : 0.09400
REMARK 200  <I/SIGMA(I)> FOR THE DATA SET  : NULL
REMARK 200
REMARK 200 IN THE HIGHEST RESOLUTION SHELL.
REMARK 200  HIGHEST RESOLUTION SHELL, RANGE HIGH (A) : 5.50
REMARK 200  HIGHEST RESOLUTION SHELL, RANGE LOW  (A) : 5.70
REMARK 200  COMPLETENESS FOR SHELL     (%) : 95.0
REMARK 200  DATA REDUNDANCY IN SHELL       : 2.80
REMARK 200  R MERGE FOR SHELL          (I) : 0.30800
REMARK 200  R SYM FOR SHELL            (I) : 0.30800
REMARK 200  <I/SIGMA(I)> FOR SHELL         : 3.300
REMARK 200
REMARK 200 DIFFRACTION PROTOCOL: SINGLE WAVELENGTH
REMARK 200 METHOD USED TO DETERMINE THE STRUCTURE: MAD
REMARK 200 SOFTWARE USED: CCP4
REMARK 200 STARTING MODEL: NULL
REMARK 200
REMARK 200 REMARK: NULL
REMARK 280
REMARK 280 CRYSTAL
REMARK 280 SOLVENT CONTENT, VS   (%): NULL
REMARK 280 MATTHEWS COEFFICIENT, VM (ANGSTROMS**3/DA): NULL
REMARK 280
REMARK 280 CRYSTALLIZATION CONDITIONS: NULL
REMARK 290
REMARK 290 CRYSTALLOGRAPHIC SYMMETRY
REMARK 290 SYMMETRY OPERATORS FOR SPACE GROUP: I 4 2 2
REMARK 290
REMARK 290       SYMOP   SYMMETRY
REMARK 290       NNNMMM  OPERATOR
REMARK 290        1555   X,Y,Z
REMARK 290        2555   -X,-Y,Z
REMARK 290        3555   -Y,X,Z
REMARK 290        4555   Y,-X,Z
REMARK 290        5555   -X,Y,-Z
REMARK 290        6555   X,-Y,-Z
REMARK 290        7555   Y,X,-Z
REMARK 290        8555   -Y,-X,-Z
REMARK 290        9555   1/2+X,1/2+Y,1/2+Z
REMARK 290       10555   1/2-X,1/2-Y,1/2+Z
REMARK 290       11555   1/2-Y,1/2+X,1/2+Z
REMARK 290       12555   1/2+Y,1/2-X,1/2+Z
REMARK 290       13555   1/2-X,1/2+Y,1/2-Z
REMARK 290       14555   1/2+X,1/2-Y,1/2-Z
REMARK 290       15555   1/2+Y,1/2+X,1/2-Z
REMARK 290       16555   1/2-Y,1/2-X,1/2-Z
REMARK 290
REMARK 290     WHERE NNN -> OPERATOR NUMBER
REMARK 290           MMM -> TRANSLATION VECTOR
REMARK 290
REMARK 290 CRYSTALLOGRAPHIC SYMMETRY TRANSFORMATIONS
REMARK 290 THE FOLLOWING TRANSFORMATIONS OPERATE ON THE ATOM/HETATM
REMARK 290 RECORDS IN THIS ENTRY TO PRODUCE CRYSTALLOGRAPHICALLY
REMARK 290 RELATED MOLECULES.
REMARK 290     SMTRY1   1  1.000000  0.000000  0.000000        0.00000
REMARK 290     SMTRY2   1  0.000000  1.000000  0.000000        0.00000
REMARK 290     SMTRY3   1  0.000000  0.000000  1.000000        0.00000
REMARK 290     SMTRY1   2 -1.000000  0.000000  0.000000        0.00000
REMARK 290     SMTRY2   2  0.000000 -1.000000  0.000000        0.00000
REMARK 290     SMTRY3   2  0.000000  0.000000  1.000000        0.00000
```

```
REMARK 290   SMTRY1   3  0.000000 -1.000000  0.000000        0.00000
REMARK 290   SMTRY2   3  1.000000  0.000000  0.000000        0.00000
REMARK 290   SMTRY3   3  0.000000  0.000000  1.000000        0.00000
REMARK 290   SMTRY1   4  0.000000  1.000000  0.000000        0.00000
REMARK 290   SMTRY2   4 -1.000000  0.000000  0.000000        0.00000
REMARK 290   SMTRY3   4  0.000000  0.000000  1.000000        0.00000
REMARK 290   SMTRY1   5 -1.000000  0.000000  0.000000        0.00000
REMARK 290   SMTRY2   5  0.000000  1.000000  0.000000        0.00000
REMARK 290   SMTRY3   5  0.000000  0.000000 -1.000000        0.00000
REMARK 290   SMTRY1   6  1.000000  0.000000  0.000000        0.00000
REMARK 290   SMTRY2   6  0.000000 -1.000000  0.000000        0.00000
REMARK 290   SMTRY3   6  0.000000  0.000000 -1.000000        0.00000
REMARK 290   SMTRY1   7  0.000000  1.000000  0.000000        0.00000
REMARK 290   SMTRY2   7  1.000000  0.000000  0.000000        0.00000
REMARK 290   SMTRY3   7  0.000000  0.000000 -1.000000        0.00000
REMARK 290   SMTRY1   8  0.000000 -1.000000  0.000000        0.00000
REMARK 290   SMTRY2   8 -1.000000  0.000000  0.000000        0.00000
REMARK 290   SMTRY3   8  0.000000  0.000000 -1.000000        0.00000
REMARK 290   SMTRY1   9  1.000000  0.000000  0.000000      253.60000
REMARK 290   SMTRY2   9  0.000000  1.000000  0.000000      253.60000
REMARK 290   SMTRY3   9  0.000000  0.000000  1.000000      401.83000
REMARK 290   SMTRY1  10 -1.000000  0.000000  0.000000      253.60000
REMARK 290   SMTRY2  10  0.000000 -1.000000  0.000000      253.60000
REMARK 290   SMTRY3  10  0.000000  0.000000  1.000000      401.83000
REMARK 290   SMTRY1  11  0.000000 -1.000000  0.000000      253.60000
REMARK 290   SMTRY2  11  1.000000  0.000000  0.000000      253.60000
REMARK 290   SMTRY3  11  0.000000  0.000000  1.000000      401.83000
REMARK 290   SMTRY1  12  0.000000  1.000000  0.000000      253.60000
REMARK 290   SMTRY2  12 -1.000000  0.000000  0.000000      253.60000
REMARK 290   SMTRY3  12  0.000000  0.000000  1.000000      401.83000
REMARK 290   SMTRY1  13 -1.000000  0.000000  0.000000      253.60000
REMARK 290   SMTRY2  13  0.000000  1.000000  0.000000      253.60000
REMARK 290   SMTRY3  13  0.000000  0.000000 -1.000000      401.83000
REMARK 290   SMTRY1  14  1.000000  0.000000  0.000000      253.60000
REMARK 290   SMTRY2  14  0.000000 -1.000000  0.000000      253.60000
REMARK 290   SMTRY3  14  0.000000  0.000000 -1.000000      401.83000
REMARK 290   SMTRY1  15  0.000000  1.000000  0.000000      253.60000
REMARK 290   SMTRY2  15  1.000000  0.000000  0.000000      253.60000
REMARK 290   SMTRY3  15  0.000000  0.000000 -1.000000      401.83000
REMARK 290   SMTRY1  16  0.000000 -1.000000  0.000000      253.60000
REMARK 290   SMTRY2  16 -1.000000  0.000000  0.000000      253.60000
REMARK 290   SMTRY3  16  0.000000  0.000000 -1.000000      401.83000
REMARK 290
REMARK 290 REMARK: NULL
REMARK 300
REMARK 300 BIOMOLECULE: 1
REMARK 300 THIS ENTRY CONTAINS THE CRYSTALLOGRAPHIC ASYMMETRIC UNIT
REMARK 300 WHICH CONSISTS OF 24CHAIN(S). SEE REMARK 350 FOR
REMARK 300 INFORMATION ON GENERATING THE BIOLOGICAL MOLECULE(S).
REMARK 350
REMARK 350 GENERATING THE BIOMOLECULE
REMARK 350 COORDINATES FOR A COMPLETE MULTIMER REPRESENTING THE KNOWN
REMARK 350 BIOLOGICALLY SIGNIFICANT OLIGOMERIZATION STATE OF THE
REMARK 350 MOLECULE CAN BE GENERATED BY APPLYING BIOMT TRANSFORMATIONS
REMARK 350 GIVEN BELOW.  BOTH NON-CRYSTALLOGRAPHIC AND
REMARK 350 CRYSTALLOGRAPHIC OPERATIONS ARE GIVEN.
REMARK 350
REMARK 350 BIOMOLECULE: 1
REMARK 350 APPLY THE FOLLOWING TO CHAINS: A, B, C, D, E, F, G, H, I,
REMARK 350 J, K, L, M, N, O, P, Q, R, S, T, U, V, W, X
REMARK 350   BIOMT1   1  1.000000  0.000000  0.000000        0.00000
REMARK 350   BIOMT2   1  0.000000  1.000000  0.000000        0.00000
REMARK 350   BIOMT3   1  0.000000  0.000000  1.000000        0.00000
REMARK 400
REMARK 400 COMPOUND
REMARK 400
REMARK 400 PDB ENTRIES 1GIX AND 1GIY REPRESENT ONE CRYSTAL
REMARK 400 STRUCTURE OF THE THERMUS THERMOPHILUS 70S RIBOSOME.
REMARK 400
REMARK 400 THIS FILE, 1GIY, CONTAINS ONLY MOLECULES OF
REMARK 400 THE 50S RIBOSOMAL SUBUNIT. THE 30S SUBUNIT,
REMARK 400 THREE TRNA MOLECULES AND AN MRNA FRAGMENT
REMARK 400 ARE IN THE PDB FILE 1GIX.
REMARK 400
REMARK 400    70S RIBOSOME PARTICLE ORIGINATES FROM THERMUS
REMARK 400 THERMOPHILUS. HOWEVER, INITIAL MODELS OF SOME OF
REMARK 400 ITS CONSTITUENTS WERE TAKEN FROM STRUCTURES FROM
REMARK 400 OTHER ORGANISMS.
REMARK 400
REMARK 400 THE FOLLOWING LISTS CHAIN ID (AS IN THE COMPND
REMARK 400 RECORDS ABOVE), THE PDB ID OF THE STRUCTURAL
REMARK 400 MODEL AND THE SOURCE ORGANISM OF THAT MODEL FOR
REMARK 400 EACH BIOMOLECULE IN 1GIX AND 1GIY.
REMARK 400
REMARK 400 ==================================================
REMARK 400      30S SMALL SUBUNIT, PDB FILE 1GIX
REMARK 400 ==================================================
```

```
REMARK 400
REMARK 400 ===> 30S 16S RIBOSOMAL RNA, CHAIN A           <===
REMARK 400 1FJF       THERMUS THERMOPHILUS
REMARK 400 ===> TRNA(PHE), CHAIN B, C                    <===
REMARK 400 1EVV, 1FFZ       SACHROMYCES CEREVISIAE
REMARK 400 ===> TRNA(PHE), CHAIN D                       <===
REMARK 400 1GTR, 1B23, 3TRA NO SEQUENCE ENTRY
REMARK 400 ===> 30S RIBOSOMAL PROTEIN S2, CHAIN E        <===
REMARK 400 1FJF       THERMUS THERMOPHILUS
REMARK 400 ===> 30S RIBOSOMAL PROTEIN S3, CHAIN F        <===
REMARK 400 1FJF       THERMUS THERMOPHILUS
REMARK 400 ===> 30S RIBOSOMAL PROTEIN S4, CHAIN G        <===
REMARK 400 1FJF       THERMUS THERMOPHILUS
REMARK 400 ===> 30S RIBOSOMAL PROTEIN S5, CHAIN H        <===
REMARK 400 1FJF       THERMUS THERMOPHILUS
REMARK 400 ===> 30S RIBOSOMAL PROTEIN S6, CHAIN I        <===
REMARK 400 1FJF       THERMUS THERMOPHILUS
REMARK 400 ===> 30S RIBOSOMAL PROTEIN S7, CHAIN J        <===
REMARK 400 1FJF       THERMUS THERMOPHILUS
REMARK 400 ===> 30S RIBOSOMAL PROTEIN S8, CHAIN K        <===
REMARK 400 1FJF       THERMUS THERMOPHILUS
REMARK 400 ===> 30S RIBOSOMAL PROTEIN S9, CHAIN L        <===
REMARK 400 1FJF       THERMUS THERMOPHILUS
REMARK 400 ===> 30S RIBOSOMAL PROTEIN S10, CHAIN M       <===
REMARK 400 1FJF       THERMUS THERMOPHILUS
REMARK 400 ===> 30S RIBOSOMAL PROTEIN S11, CHAIN N       <===
REMARK 400 1FJF       THERMUS THERMOPHILUS
REMARK 400 ===> 30S RIBOSOMAL PROTEIN S12, CHAIN O       <===
REMARK 400 1FJF       THERMUS THERMOPHILUS
REMARK 400 ===> 30S RIBOSOMAL PROTEIN S13, CHAIN P       <===
REMARK 400 1FJF       THERMUS THERMOPHILUS
REMARK 400 ===> 30S RIBOSOMAL PROTEIN S14, CHAIN Q       <===
REMARK 400 1FJF       THERMUS THERMOPHILUS
REMARK 400 ===> 30S RIBOSOMAL PROTEIN S15, CHAIN R       <===
REMARK 400 1FJF       THERMUS THERMOPHILUS
REMARK 400 ===> 30S RIBOSOMAL PROTEIN S16, CHAIN S       <===
REMARK 400 1FJF       THERMUS THERMOPHILUS
REMARK 400 ===> 30S RIBOSOMAL PROTEIN S17, CHAIN T       <===
REMARK 400 1FJF       THERMUS THERMOPHILUS
REMARK 400 ===> 30S RIBOSOMAL PROTEIN S18, CHAIN U       <===
REMARK 400 1FJF       THERMUS THERMOPHILUS
REMARK 400 ===> 30S RIBOSOMAL PROTEIN S19, CHAIN V       <===
REMARK 400 1FJF       THERMUS THERMOPHILUS
REMARK 400 ===> 30S RIBOSOMAL PROTEIN S20, CHAIN W       <===
REMARK 400 1FJF       THERMUS THERMOPHILUS
REMARK 400 ===> 30S RIBOSOMAL PROTEIN THX, CHAIN X       <===
REMARK 400 1FJF       THERMUS THERMOPHILUS
REMARK 400
REMARK 400 =================================================
REMARK 400       50S LARGE SUBUNIT, PDB FILE 1GIY
REMARK 400 =================================================
REMARK 400
REMARK 400 ===> 50S 23S RIBOSOMAL RNA, CHAIN A           <===
REMARK 400 1FFK      THERMUS THERMOPHILUS
REMARK 400 ===> 50S 5S RIBOSOMAL RNA, CHAIN B            <===
REMARK 400 1FFK      THERMUS THERMOPHILUS
REMARK 400 ===> 50S RIBOSOMAL PROTEIN L1, CHAIN C        <===
REMARK 400 NO PUBLIC COORDINATES FOR THE MODEL
REMARK 400             THERMUS AQUATICUS
REMARK 400 ===> 50S RIBOSOMAL PROTEIN L2 , CHAIN D       <===
REMARK 400 1RL2 (RESIDUES  61-197), BACILLUS STEAROTHERMOPHILUS
REMARK 400 1FFK (RESIDUES 138-203), HALOARCULA MARISMORTUI
REMARK 400 ===> 50S RIBOSOMAL PROTEIN L3 , CHAIN E       <===
REMARK 400 1FFK       HALOARCULA MARISMORTUI (L3P)
REMARK 400 ===> 50S RIBOSOMAL PROTEIN L4, CHAIN F        <===
REMARK 400 1FFK       HALOARCULA MARISMORTUI (L4E)
REMARK 400 ===> 50S RIBOSOMAL PROTEIN L5, CHAIN G        <===
REMARK 400 1FFK       HALOARCULA MARISMORTUI (L5P)
REMARK 400 ===> 50S RIBOSOMAL PROTEIN L6, CHAIN H
REMARK 400 1RL6       BACILLUS STEAROTHERMOPHILUS
REMARK 400 ===> 50S RIBOSOMAL PROTEIN L7/L12, CHAIN I, J <===
REMARK 400 1DD3       THERMOTOGA MARITIMA
REMARK 400 ===> 50S RIBOSOMAL PROTEIN L9, CHAIN K        <===
REMARK 400 1DIV       BACILLUS STEAROTHERMOPHILUS
REMARK 400 ===> 50S RIBOSOMAL PROTEIN L11, CHAIN L       <===
REMARK 400 1MMS       THERMOTOGA MARITIMA
REMARK 400 ===> 50S RIBOSOMAL PROTEIN L13, CHAIN M       <===
REMARK 400 1FFK       HALOARCULA MARISMORTUI (L13P)
REMARK 400 ===> 50S RIBOSOMAL PROTEIN L14, CHAIN N       <===
REMARK 400 1WHI       BACILLUS STEAROTHERMOPHILUS
REMARK 400 ===> 50S RIBOSOMAL PROTEIN L15, CHAIN O       <===
REMARK 400 1FFK       HALOARCULA MARISMORTUI (L15P)
REMARK 400 ===> 50S RIBOSOMAL PROTEIN L16, CHAIN P       <===
REMARK 400 1FFK       NO SEQUENCE ENTRY FOUND
REMARK 400 ===> 50S RIBOSOMAL PROTEIN L18, CHAIN Q       <===
REMARK 400 1FFK       HALOARCULA MARISMORTUI (L18P)
REMARK 400 ===> 50S RIBOSOMAL PROTEIN L19, CHAIN R
```

```
REMARK 400 1FFK        HALOARCULA MARISMORTUI (L24E)
REMARK 400 ===> 50S RIBOSOMAL PROTEIN L22, CHAIN S        <===
REMARK 400 1BXE        THERMUS THERMOPHILUS
REMARK 400 ===> 50S RIBOSOMAL PROTEIN L23, CHAIN T        <===
REMARK 400 1FFK        HALOARCULA MARISMORTUI (L23P)
REMARK 400 ===> 50S RIBOSOMAL PROTEIN L24, CHAIN U        <===
REMARK 400 1FFK        HALOARCULA MARISMORTUI (L24P)
REMARK 400 ===> 50S RIBOSOMAL PROTEIN L25, CHAIN V        <===
REMARK 400 1DFU        ESCHERICHIA COLI
REMARK 400 ===> 50S RIBOSOMAL PROTEIN L29, CHAIN W        <===
REMARK 400 1FFK        HALOARCULA MARISMORTUI (L29P)
REMARK 400 ===> 50S RIBOSOMAL PROTEIN L30, CHAIN X        <===
REMARK 400 1BXY        THERMUS THERMOPHILUS
REMARK 900
REMARK 900 RELATED ENTRIES
REMARK 900 RELATED ID: 486D    RELATED DB: PDB
REMARK 900 7.5A MODEL OF 70S RIBOSOME
DBREF  1GIY A    1  2906  EMBL   48268      X12612           1  2915
DBREF  1GIY B    0   121  GB     176261     K01305           0   121
DBREF  1GIY C    1   228  SWS    P27150     RL1_THETH        1   228
DBREF  1GIY D   60   196  SWS    P04257     RL2_BACST       60   196
DBREF  1GIY D  197   237  SWS    P20276     RL2_HALMA      197   237
DBREF  1GIY E    1   338  SWS    P20279     RL3_HALMA        1   338
DBREF  1GIY F    1   246  SWS    P12735     RL4_HALMA        1   246
DBREF  1GIY G    1   176  SWS    P14124     RL5_HALMA        1   176
DBREF  1GIY H    1   177  SWS    P02391     RL6_BACST        1   177
DBREF  1GIY I    1   128  SWS    P29396     RL7_THEMA        1   128
DBREF  1GIY J    1   128  SWS    P29396     RL7_THEMA        1   128
DBREF  1GIY K    1   149  SWS    P02417     RL9_BACST        1   149
DBREF  1GIY L    1   141  SWS    P29395     RL11_THEMA       1   141
DBREF  1GIY M    1   145  SWS    P29198     RL13_HALMA       1   145
DBREF  1GIY N    1   122  SWS    P04450     RL14_BACST       1   122
DBREF  1GIY O    1   164  SWS    P12737     RL15_HALMA       1   164
DBREF  1GIY Q    1   186  SWS    P14123     RL18_HALMA       1   186
DBREF  1GIY R    1    66  SWS    P14116     R24E_HALMA       1    66
DBREF  1GIY S    1   113  SWS    P48286     RL22_THETH       1   113
DBREF  1GIY T    1    84  SWS    P12732     RL23_HALMA       1    84
DBREF  1GIY U    1   119  SWS    P10972     RL24_HALMA       1   119
DBREF  1GIY V    1    94  SWS    P02426     RL25_ECOLI       1    94
DBREF  1GIY W    1    70  SWS    P10971     RL29_HALMA       1    70
DBREF  1GIY X    1    60  SWS    P74909     RL30_THETH       1    60
SEQADV 1GIY     G A  519        48268                 INSERTION
SEQADV 1GIY     A B   -1  GB    176261                INSERTION
SEQADV 1GIY SER E  114  SWS    P20279     ASP    114 CONFLICT
SEQADV 1GIY ASP E  115  SWS    P20279     VAL    115 CONFLICT
SEQADV 1GIY ARG E  116  SWS    P20279     PRO    116 CONFLICT
SEQADV 1GIY LEU E  117  SWS    P20279     GLU    117 CONFLICT
SEQADV 1GIY ALA E  120  SWS    P20279     ASP    120 CONFLICT
SEQADV 1GIY LEU E  121  SWS    P20279     PRO    121 CONFLICT
SEQADV 1GIY ILE E  123  SWS    P20279     ALA    123 CONFLICT
SEQADV 1GIY VAL E  124  SWS    P20279     ALA    124 CONFLICT
SEQADV 1GIY ASP E  126  SWS    P20279     GLU    126 CONFLICT
SEQADV 1GIY GLU F    2  SWS    P12735     GLN      2 CONFLICT
SEQRES   1 A 2916  G  G  U  C  A  A  G  A  U  G  G  U  A
SEQRES   2 A 2916  A  G  G  C  C  C  A  C  G  G  U  U  C
SEQRES   3 A 2916  G  A  U  G  C  C  U  C  G  G  C  A  C
SEQRES   4 A 2916  C  C  G  A  G  C  C  G  A  U  G  A  A
SEQRES   5 A 2916  G  G  A  C  G  U  G  G  C  U  A  C  C
SEQRES   6 A 2916  U  G  C  G  A  U  A  A  G  C  C  A  G
SEQRES   7 A 2916  G  G  G  G  A  G  C  C  G  G  U  A  C
SEQRES   8 A 2916  C  G  G  G  C  G  U  G  G  A  U  C  C
SEQRES   9 A 2916  C  U  G  G  A  U  G  U  C  C  G  A  A
SEQRES  10 A 2916  U  G  G  G  G  A  A  C  C  C  G  G  C
SEQRES  11 A 2916  C  C  G  C  G  G  G  A  A  C  C  G  C
SEQRES  12 A 2916  C  G  G  U  C  A  C  C  G  C  G  C  U
SEQRES  13 A 2916  U  U  U  G  C  G  C  G  G  G  G  G  U
SEQRES  14 A 2916  A  A  C  C  U  G  G  G  A  G  A  C  U
SEQRES  15 A 2916  G  A  A  A  C  A  U  C  U  C  A  G  U
SEQRES  16 A 2916  A  C  C  A  G  A  G  G  A  G  A  A  G
SEQRES  17 A 2916  G  A  A  A  G  A  A  A  A  U  C  C  G
SEQRES  18 A 2916  A  C  U  C  C  U  G  A  G  U  A  G  G
SEQRES  19 A 2916  C  G  G  C  G  A  G  C  G  A  A  A  G
SEQRES  20 A 2916  G  G  A  C  C  A  C  G  G  A  U  U  A
SEQRES  21 A 2916  A  C  C  G  U  C  C  G  G  C  U  U  G
SEQRES  22 A 2916  U  C  C  G  G  G  C  C  C  U  C  U  G
SEQRES  23 A 2916  G  U  G  G  G  A  A  U  C  C  C  C  C
SEQRES  24 A 2916  A  C  A  C  C  G  A  A  U  C  C  C  C
SEQRES  25 A 2916  A  G  C  C  U  A  G  C  C  G  A  A  G
SEQRES  26 A 2916  C  U  G  U  U  G  G  G  A  A  G  C  A
SEQRES  27 A 2916  G  C  G  C  C  A  G  A  G  A  G  G  G
SEQRES  28 A 2916  U  G  A  A  A  G  C  C  C  C  G  U  A
SEQRES  29 A 2916  G  C  G  A  A  A  G  C  G  U  G  G  G
SEQRES  30 A 2916  G  G  G  A  U  A  G  G  U  G  A  G  G
SEQRES  31 A 2916  G  U  A  C  C  G  A  G  U  A  C  C  G
SEQRES  32 A 2916  C  C  G  U  G  U  U  C  G  U  G  G  C
SEQRES  33 A 2916  A  G  C  C  A  U  G  G  G  G  A  A  A
SEQRES  34 A 2916  U  C  U  G  G  C  G  G  A  C  C  A
```

| SEQRES | 35 | A | 2916 | C | C | G | G | C | C | U | A | A | G | G | C | U |
| --- | --- | --- | --- | --- | --- | --- | --- | --- | --- | --- | --- | --- | --- | --- | --- | --- |
| SEQRES | 36 | A | 2916 | A | A | G | U | A | C | U | C | C | G | G | G | U |
| SEQRES | 37 | A | 2916 | G | A | C | C | G | A | U | A | G | C | G | C | A |
| SEQRES | 38 | A | 2916 | C | C | A | G | U | A | C | C | G | U | G | A | G |
| SEQRES | 39 | A | 2916 | G | G | A | A | A | G | G | U | G | A | A | A | A |
| SEQRES | 40 | A | 2916 | G | A | A | C | C | C | C | G | G | A | A | G | G |
| SEQRES | 41 | A | 2916 | G | G | A | G | U | G | A | A | A | U | A | G | A |
| SEQRES | 42 | A | 2916 | G | C | C | U | G | A | A | A | C | C | G | U | G |
| SEQRES | 43 | A | 2916 | G | G | C | U | U | A | A | C | A | C | G | A | A |
| SEQRES | 44 | A | 2916 | U | C | A | C | G | G | C | C | C | C | G | C | G |
| SEQRES | 45 | A | 2916 | A | G | G | G | G | U | U | G | U | G | A | C | C |
| SEQRES | 46 | A | 2916 | U | G | C | C | U | A | U | U | G | A | G | A | C |
| SEQRES | 47 | A | 2916 | A | U | G | A | G | C | C | G | G | C | G | G | G |
| SEQRES | 48 | A | 2916 | U | C | A | C | G | G | U | C | G | U | G | G | G |
| SEQRES | 49 | A | 2916 | C | G | A | G | C | U | U | C | A | G | C | C | C |
| SEQRES | 50 | A | 2916 | U | U | G | A | G | G | C | G | G | A | G | G | C |
| SEQRES | 51 | A | 2916 | G | U | A | G | G | G | A | A | A | C | G | G | A |
| SEQRES | 52 | A | 2916 | G | U | C | C | G | A | C | A | A | C | G | G | C |
| SEQRES | 53 | A | 2916 | G | C | A | A | G | C | G | G | G | C | C | G | A |
| SEQRES | 54 | A | 2916 | A | C | G | C | G | G | C | C | G | C | C | A | U |
| SEQRES | 55 | A | 2916 | A | G | U | C | C | G | C | C | A | C | C | G | G |
| SEQRES | 56 | A | 2916 | G | G | A | C | C | C | G | A | A | C | C | C | C |
| SEQRES | 57 | A | 2916 | G | G | C | G | A | G | C | U | G | A | G | C | A |
| SEQRES | 58 | A | 2916 | U | G | G | C | C | A | G | G | U | U | A | A | C |
| SEQRES | 59 | A | 2916 | G | C | U | G | G | G | U | G | A | G | A | A | C |
| SEQRES | 60 | A | 2916 | C | C | A | G | U | G | G | A | G | G | C | C | G |
| SEQRES | 61 | A | 2916 | G | A | A | C | C | G | A | U | G | C | C | G | C |
| SEQRES | 62 | A | 2916 | A | U | G | C | A | A | A | C | C | C | C | U | C |
| SEQRES | 63 | A | 2916 | G | G | A | U | G | A | G | C | U | G | A | G | A |
| SEQRES | 64 | A | 2916 | C | U | A | G | G | A | G | U | G | A | A | A | C |
| SEQRES | 65 | A | 2916 | G | C | U | A | A | C | C | G | A | G | C | C | U |
| SEQRES | 66 | A | 2916 | G | G | A | A | G | U | A | A | C | U | G | G | G |
| SEQRES | 67 | A | 2916 | U | C | U | C | C | C | C | G | A | A | A | U | G |
| SEQRES | 68 | A | 2916 | A | C | U | U | U | A | G | G | G | U | C | A | A |
| SEQRES | 69 | A | 2916 | C | C | U | C | A | G | G | C | G | C | U | G | A |
| SEQRES | 70 | A | 2916 | C | U | G | G | G | G | C | C | U | G | U | A | G |
| SEQRES | 71 | A | 2916 | A | G | C | A | C | U | G | A | U | A | G | G | G |
| SEQRES | 72 | A | 2916 | C | U | A | G | G | G | G | G | C | C | A | A | C |
| SEQRES | 73 | A | 2916 | C | A | G | C | C | U | A | C | C | A | A | C | C |
| SEQRES | 74 | A | 2916 | C | C | U | G | U | C | A | A | C | U | C | C | C |
| SEQRES | 75 | A | 2916 | G | A | A | G | G | G | U | C | C | A | G | G | G |
| SEQRES | 76 | A | 2916 | U | G | G | A | G | C | C | U | G | G | A | G | C |
| SEQRES | 77 | A | 2916 | U | G | A | G | G | G | C | G | C | G | A | G | C |
| SEQRES | 78 | A | 2916 | G | A | U | A | A | C | G | U | C | C | G | C | G |
| SEQRES | 79 | A | 2916 | U | C | C | G | A | G | C | C | C | G | G | C | A |
| SEQRES | 80 | A | 2916 | A | C | A | A | C | C | G | A | G | A | C | C | G |
| SEQRES | 81 | A | 2916 | C | C | C | G | C | U | A | A | G | G | C | C | C |
| SEQRES | 82 | A | 2916 | C | C | A | A | G | U | C | U | G | G | G | G | U |
| SEQRES | 83 | A | 2916 | A | A | G | U | G | G | U | A | A | A | G | G | A |
| SEQRES | 84 | A | 2916 | U | G | U | G | G | C | G | C | C | G | C | C | A |
| SEQRES | 85 | A | 2916 | A | G | A | C | A | G | C | C | A | G | G | A | G |
| SEQRES | 86 | A | 2916 | G | U | U | G | G | C | U | U | A | G | U | A | G |
| SEQRES | 87 | A | 2916 | C | A | A | G | C | A | U | G | C | C | U | A | U |
| SEQRES | 88 | A | 2916 | A | A | G | C | G | U | G | C | G | U | A | C | G |
| SEQRES | 89 | A | 2916 | A | G | C | U | C | A | C | U | C | G | C | G | C |
| SEQRES | 90 | A | 2916 | A | G | U | G | C | A | G | C | G | G | U | G | G |
| SEQRES | 91 | A | 2916 | C | G | A | A | A | U | G | A | U | G | C | C | G |
| SEQRES | 92 | A | 2916 | G | G | G | C | U | U | A | A | G | C | C | G | A |
| SEQRES | 93 | A | 2916 | G | C | C | C | C | U | G | G | G | G | U | G | C |
| SEQRES | 94 | A | 2916 | G | G | G | U | C | U | A | G | G | G | G | A | U |
| SEQRES | 95 | A | 2916 | G | A | C | C | C | C | A | G | G | C | U | G | C |
| SEQRES | 96 | A | 2916 | A | G | G | G | G | A | C | C | G | C | U | C | A |
| SEQRES | 97 | A | 2916 | C | G | A | U | A | C | C | G | A | U | G | A | A |
| SEQRES | 98 | A | 2916 | G | G | C | C | G | C | C | C | C | G | A | G | U |
| SEQRES | 99 | A | 2916 | G | G | C | G | G | C | U | G | G | A | C | G | A |
| SEQRES | 10 | A | 2916 | A | A | G | G | G | A | A | G | U | G | C | G | A |
| SEQRES | 10 | A | 2916 | A | U | G | C | C | A | G | C | A | U | A | A | G |
| SEQRES | 10 | A | 2916 | U | A | A | C | G | A | U | A | A | G | C | C | U |
| SEQRES | 10 | A | 2916 | G | G | U | G | A | G | A | A | U | C | C | C | G |
| SEQRES | 10 | A | 2916 | C | U | C | G | C | C | G | A | A | A | C | A | C |
| SEQRES | 10 | A | 2916 | C | A | A | G | G | G | U | U | C | C | U | C | A |
| SEQRES | 10 | A | 2916 | G | C | A | A | U | G | G | U | C | G | U | C | G |
| SEQRES | 10 | A | 2916 | G | C | G | U | A | G | G | C | U | A | A | G | U |
| SEQRES | 10 | A | 2916 | C | G | G | G | C | C | G | A | A | A | G | G | C |
| SEQRES | 11 | A | 2916 | G | A | A | G | C | C | G | A | A | G | G | A | U |
| SEQRES | 11 | A | 2916 | A | G | C | C | G | G | U | U | A | A | U | C | C |
| SEQRES | 11 | A | 2916 | U | C | C | G | G | C | G | C | U | G | C | C | G |
| SEQRES | 11 | A | 2916 | G | C | A | G | G | C | G | C | U | C | A | A | G |
| SEQRES | 11 | A | 2916 | G | C | U | A | G | G | C | G | G | A | A | C | G |
| SEQRES | 11 | A | 2916 | G | A | G | C | A | G | U | C | G | A | A | A | G |
| SEQRES | 11 | A | 2916 | C | G | C | A | G | G | G | C | U | G | G | C | G |
| SEQRES | 11 | A | 2916 | C | G | U | G | G | A | A | A | G | U | A | G | C |
| SEQRES | 12 | A | 2916 | C | C | U | C | C | C | A | A | C | U | G | G | G |
| SEQRES | 12 | A | 2916 | U | C | U | G | G | U | G | G | A | U | G | G | G |

| | | | | | | | | | | | | | |
|---|---|---|---|---|---|---|---|---|---|---|---|---|---|
| SEQRES | 12 | A | 2916 | G | A | A | G | C | C | C | G | U | A | C | G | G |
| SEQRES | 12 | A | 2916 | G | U | G | A | C | A | A | C | C | C | A | C | C |
| SEQRES | 12 | A | 2916 | G | A | A | G | C | C | A | G | G | G | A | G | C |
| SEQRES | 12 | A | 2916 | C | A | A | G | A | A | A | A | G | C | C | U | C |
| SEQRES | 12 | A | 2916 | U | A | A | G | C | A | A | C | C | C | C | U | G |
| SEQRES | 12 | A | 2916 | C | G | G | G | A | A | C | C | C | G | U | A | C |
| SEQRES | 12 | A | 2916 | C | G | C | A | A | A | C | C | G | A | C | A | C |
| SEQRES | 12 | A | 2916 | A | G | G | U | G | G | G | C | G | G | G | U | G |
| SEQRES | 13 | A | 2916 | C | A | A | G | A | G | C | A | C | U | C | A | G |
| SEQRES | 13 | A | 2916 | G | C | G | C | G | C | G | G | A | G | A | A | A |
| SEQRES | 13 | A | 2916 | C | C | C | U | C | G | C | C | A | A | A | G | U | U | G |
| SEQRES | 13 | A | 2916 | A | C | U | C | U | G | C | A | A | G | U | U | C |
| SEQRES | 13 | A | 2916 | G | C | C | C | C | G | U | A | A | C | U | U | C |
| SEQRES | 13 | A | 2916 | G | G | G | A | G | A | A | G | G | G | G | U | A |
| SEQRES | 13 | A | 2916 | C | U | C | C | C | U | G | G | G | U | G | G | A |
| SEQRES | 13 | A | 2916 | U | G | A | G | C | C | C | C | G | G | G | G | A |
| SEQRES | 13 | A | 2916 | G | C | C | G | C | A | G | U | G | A | A | C | A |
| SEQRES | 13 | A | 2916 | G | G | C | U | C | U | G | G | C | G | A | C | U |
| SEQRES | 14 | A | 2916 | G | U | U | U | A | C | C | A | A | A | A | A | C |
| SEQRES | 14 | A | 2916 | A | C | A | G | C | U | C | U | C | U | G | C | G |
| SEQRES | 14 | A | 2916 | A | A | C | U | C | G | U | A | A | G | A | G | G |
| SEQRES | 14 | A | 2916 | A | G | G | U | A | U | A | G | G | G | A | G | C |
| SEQRES | 14 | A | 2916 | G | A | C | G | C | U | U | G | C | C | C | G | G |
| SEQRES | 14 | A | 2916 | U | G | C | C | G | G | A | A | G | G | U | C | A |
| SEQRES | 14 | A | 2916 | A | G | G | G | G | A | G | G | G | U | A | G | C |
| SEQRES | 14 | A | 2916 | A | A | C | C | C | C | G | A | A | A | C | C | G |
| SEQRES | 14 | A | 2916 | A | A | G | C | C | C | G | G | U | G | A | A | A |
| SEQRES | 14 | A | 2916 | C | G | G | C | G | G | C | C | G | U | A | A | C |
| SEQRES | 15 | A | 2916 | U | A | U | A | C | G | G | U | C | C | U | A | A |
| SEQRES | 15 | A | 2916 | A | G | G | U | A | G | C | G | A | A | A | U | U |
| SEQRES | 15 | A | 2916 | C | C | U | U | G | U | C | G | G | G | U | A | A |
| SEQRES | 15 | A | 2916 | G | U | U | C | C | G | A | C | C | U | G | C | A |
| SEQRES | 15 | A | 2916 | C | G | A | A | A | A | G | C | C | U | A | A | C |
| SEQRES | 15 | A | 2916 | G | A | C | C | G | G | A | G | C | G | C | U | G |
| SEQRES | 15 | A | 2916 | U | C | U | C | G | G | C | G | A | G | G | U | G |
| SEQRES | 15 | A | 2916 | C | C | C | G | G | U | G | A | A | A | U | U | G |
| SEQRES | 15 | A | 2916 | A | A | C | U | G | G | C | C | G | U | G | A | A |
| SEQRES | 15 | A | 2916 | G | A | A | U | G | G | C | C | C | U | A | C | C |
| SEQRES | 16 | A | 2916 | C | G | U | G | G | C | A | G | G | A | C | G | A |
| SEQRES | 16 | A | 2916 | A | A | A | G | A | C | C | C | C | G | U | G | G |
| SEQRES | 16 | A | 2916 | A | G | C | U | U | U | A | C | U | C | A | G | G |
| SEQRES | 16 | A | 2916 | C | C | U | G | G | U | G | U | U | G | G | C | U |
| SEQRES | 16 | A | 2916 | C | U | U | G | G | U | C | G | C | G | C | C | U |
| SEQRES | 16 | A | 2916 | G | C | G | U | A | G | G | A | U | A | G | A | A |
| SEQRES | 16 | A | 2916 | G | G | G | A | G | C | C | U | G | U | G | A | A |
| SEQRES | 16 | A | 2916 | C | C | C | C | C | G | C | C | U | C | C | G | G |
| SEQRES | 16 | A | 2916 | G | U | G | G | G | U | G | G | A | A | U | A | C |
| SEQRES | 16 | A | 2916 | G | C | C | G | G | U | G | A | A | A | G | A | C |
| SEQRES | 17 | A | 2916 | C | A | C | C | C | U | G | G | C | G | C | G | G |
| SEQRES | 17 | A | 2916 | C | U | G | G | G | G | C | C | U | A | A | A | C |
| SEQRES | 17 | A | 2916 | C | C | U | C | G | G | A | U | G | G | G | G | G |
| SEQRES | 17 | A | 2916 | G | A | C | A | G | C | G | C | U | U | G | G | C |
| SEQRES | 17 | A | 2916 | G | G | G | C | A | G | U | U | U | G | A | C | U |
| SEQRES | 17 | A | 2916 | G | G | G | G | C | G | G | U | C | G | C | C | U |
| SEQRES | 17 | A | 2916 | C | C | U | A | A | A | A | G | G | U | A | A | C |
| SEQRES | 17 | A | 2916 | G | G | A | G | G | C | G | C | C | A | A | A | C |
| SEQRES | 17 | A | 2916 | G | G | U | C | C | C | C | U | C | A | G | G | C |
| SEQRES | 17 | A | 2916 | G | G | G | A | C | G | G | A | A | A | U | C | C |
| SEQRES | 18 | A | 2916 | G | C | C | G | G | A | A | G | A | C | G | C | A |
| SEQRES | 18 | A | 2916 | A | G | G | G | U | A | G | A | C | G | G | G | G |
| SEQRES | 18 | A | 2916 | G | C | C | U | G | A | C | U | G | C | G | A | G |
| SEQRES | 18 | A | 2916 | G | C | C | U | G | C | A | A | G | C | C | A | G |
| SEQRES | 18 | A | 2916 | G | C | A | G | G | G | G | C | G | A | A | A | G |
| SEQRES | 18 | A | 2916 | C | C | G | G | G | C | C | U | A | G | U | G | A |
| SEQRES | 18 | A | 2916 | A | C | C | G | G | U | G | G | U | C | C | C | G |
| SEQRES | 18 | A | 2916 | U | G | U | G | G | A | A | G | G | G | C | C | A |
| SEQRES | 18 | A | 2916 | U | C | G | A | U | C | A | A | C | G | G | A | U |
| SEQRES | 18 | A | 2916 | A | A | A | A | G | U | U | A | C | C | C | C | G |
| SEQRES | 19 | A | 2916 | G | G | G | A | U | A | A | C | A | G | G | C | U |
| SEQRES | 19 | A | 2916 | G | A | U | C | U | C | C | C | C | C | G | A | G |
| SEQRES | 19 | A | 2916 | C | G | U | C | C | A | C | A | C | C | G | G | C |
| SEQRES | 19 | A | 2916 | G | G | G | G | A | G | G | U | U | U | G | G | C |
| SEQRES | 19 | A | 2916 | A | C | C | U | C | G | A | U | G | U | C | G | G |
| SEQRES | 19 | A | 2916 | C | U | C | G | U | G | C | A | A | U | C | C | U |
| SEQRES | 19 | A | 2916 | G | G | G | G | C | U | G | A | A | G | A | A | G |
| SEQRES | 19 | A | 2916 | G | U | C | C | C | A | A | G | G | G | U | U | G |
| SEQRES | 19 | A | 2916 | G | G | C | U | G | U | U | C | G | C | C | C | A |
| SEQRES | 19 | A | 2916 | U | U | A | A | A | G | C | G | G | C | A | C | G |
| SEQRES | 20 | A | 2916 | C | G | A | G | C | U | G | G | G | U | U | C | A |
| SEQRES | 20 | A | 2916 | G | A | A | C | G | U | C | G | G | U | G | C | A |
| SEQRES | 20 | A | 2916 | C | A | G | U | U | C | G | G | U | C | U | C | U |
| SEQRES | 20 | A | 2916 | A | U | C | C | G | C | C | A | C | G | G | G | C |
| SEQRES | 20 | A | 2916 | G | C | A | G | G | A | G | C | C | U | U | C | A |
| SEQRES | 20 | A | 2916 | G | G | G | G | G | G | C | U | C | U | G | C | C |
| SEQRES | 20 | A | 2916 | U | A | G | U | A | C | G | A | G | A | G | G | A |
| SEQRES | 20 | A | 2916 | C | C | C | G | C | A | G | G | A | A | C | G | C |
| SEQRES | 20 | A | 2916 | A | C | C | U | C | U | G | G | U | U | U | C | C |

| | | | | | | | | | | | | | | |
|---|---|---|---|---|---|---|---|---|---|---|---|---|---|---|
| SEQRES | 20 | A | 2916 | C | A | G | C | U | G | U | C | C | U | C | C |
| SEQRES | 21 | A | 2916 | A | G | G | G | G | C | A | U | A | A | G | C | U |
| SEQRES | 21 | A | 2916 | G | G | G | U | A | G | C | C | A | U | G | U | G |
| SEQRES | 21 | A | 2916 | C | G | G | A | A | G | G | G | A | U | A | A | C |
| SEQRES | 21 | A | 2916 | C | G | C | U | G | A | A | A | G | C | A | U | C |
| SEQRES | 21 | A | 2916 | U | A | A | G | C | G | G | G | A | A | G | C | C |
| SEQRES | 21 | A | 2916 | C | G | C | C | C | C | A | A | G | A | U | G | A |
| SEQRES | 21 | A | 2916 | G | G | C | C | U | C | C | C | A | C | G | G | C |
| SEQRES | 21 | A | 2916 | G | U | C | A | A | G | C | C | G | G | U | A | A |
| SEQRES | 21 | A | 2916 | G | G | A | C | C | C | G | G | G | A | A | G | A |
| SEQRES | 21 | A | 2916 | C | C | A | C | C | C | G | G | U | G | G | A | U |
| SEQRES | 22 | A | 2916 | G | G | G | C | C | G | G | G | G | G | U | G | U |
| SEQRES | 22 | A | 2916 | A | A | G | C | G | C | C | G | C | G | A | G | G |
| SEQRES | 22 | A | 2916 | C | G | U | U | G | A | G | C | C | G | A | C | C |
| SEQRES | 22 | A | 2916 | G | G | U | C | C | C | A | A | U | C | G | U | C |
| SEQRES | 22 | A | 2916 | C | G | A | G | G | U | C | U | U | G | A | C | C |
| SEQRES | 22 | A | 2916 | C | C | U | C | | | | | | | | | |
| SEQRES | 1 | B | 123 | A | A | U | C | C | C | C | C | G | U | G | C | C |
| SEQRES | 2 | B | 123 | C | A | U | A | G | C | G | G | C | G | U | G | G |
| SEQRES | 3 | B | 123 | A | A | C | C | A | C | C | C | G | U | U | C | C |
| SEQRES | 4 | B | 123 | C | A | U | U | C | C | G | A | A | C | A | C | G |
| SEQRES | 5 | B | 123 | G | A | A | G | U | G | A | A | A | C | G | C | G |
| SEQRES | 6 | B | 123 | C | C | A | G | C | G | C | C | G | A | U | G | G |
| SEQRES | 7 | B | 123 | U | A | C | U | G | G | G | C | G | G | G | C | G |
| SEQRES | 8 | B | 123 | A | C | C | G | C | C | U | G | G | G | A | G | A |
| SEQRES | 9 | B | 123 | G | U | A | G | G | U | C | G | G | U | G | C | G |
| SEQRES | 10 | B | 123 | G | G | G | G | A | U | | | | | | | |
| SEQRES | 1 | C | 228 | PRO | LYS | HIS | GLY | LYS | ARG | TYR | ARG | ALA | LEU | LEU | GLU | LYS |
| SEQRES | 2 | C | 228 | VAL | ASP | PRO | ASN | LYS | ILE | TYR | THR | ILE | ASP | GLU | ALA | ALA |
| SEQRES | 3 | C | 228 | HIS | LEU | VAL | LYS | GLU | LEU | ALA | THR | ALA | LYS | PHE | ASP | GLU |
| SEQRES | 4 | C | 228 | THR | VAL | GLU | VAL | HIS | ALA | LYS | LEU | GLY | ILE | ASP | PRO | ARG |
| SEQRES | 5 | C | 228 | ARG | SER | ASP | GLN | ASN | VAL | ARG | GLY | THR | VAL | SER | LEU | PRO |
| SEQRES | 6 | C | 228 | HIS | GLY | LEU | GLY | LYS | GLN | VAL | ARG | VAL | LEU | ALA | ILE | ALA |
| SEQRES | 7 | C | 228 | LYS | GLY | GLU | LYS | ILE | LYS | GLU | ALA | GLU | GLU | ALA | GLY | ALA |
| SEQRES | 8 | C | 228 | ASP | TYR | VAL | GLY | GLY | GLU | GLU | ILE | ILE | GLN | LYS | ILE | LEU |
| SEQRES | 9 | C | 228 | ASP | GLY | TRP | MET | ASP | PHE | ASP | ALA | VAL | VAL | ALA | THR | PRO |
| SEQRES | 10 | C | 228 | ASP | VAL | MET | GLY | ALA | VAL | GLY | SER | LYS | LEU | GLY | ARG | ILE |
| SEQRES | 11 | C | 228 | LEU | GLY | PRO | ARG | GLY | LEU | LEU | PRO | ASN | PRO | LYS | ALA | GLY |
| SEQRES | 12 | C | 228 | THR | VAL | GLY | PHE | ASN | ILE | GLY | GLU | ILE | ILE | ARG | GLU | ILE |
| SEQRES | 13 | C | 228 | LYS | ALA | GLY | ARG | ILE | GLU | PHE | ARG | ASN | ASP | LYS | THR | GLY |
| SEQRES | 14 | C | 228 | ALA | ILE | HIS | ALA | PRO | VAL | GLY | LYS | ALA | SER | PHE | PRO | PRO |
| SEQRES | 15 | C | 228 | GLU | LYS | LEU | ALA | ASP | ASN | ILE | ARG | ALA | PHE | ILE | ARG | ALA |
| SEQRES | 16 | C | 228 | LEU | GLU | ALA | HIS | LYS | PRO | GLU | GLY | ALA | LYS | GLY | THR | PHE |
| SEQRES | 17 | C | 228 | LEU | ARG | SER | VAL | TYR | VAL | THR | THR | THR | MET | GLY | PRO | SER |
| SEQRES | 18 | C | 228 | VAL | ARG | ILE | ASN | PRO | HIS | SER | | | | | | |
| SEQRES | 1 | D | 178 | GLN | TYR | ARG | ILE | ILE | ASP | PHE | LYS | ARG | ASP | LYS | ASP | GLY |
| SEQRES | 2 | D | 178 | ILE | PRO | GLY | ARG | VAL | ALA | THR | ILE | GLU | TYR | ASP | PRO | ASN |
| SEQRES | 3 | D | 178 | ARG | SER | ALA | ASN | ILE | ALA | LEU | ILE | ASN | TYR | ALA | ASP | GLY |
| SEQRES | 4 | D | 178 | GLU | LYS | ARG | TYR | ILE | ILE | ALA | PRO | LYS | ASN | LEU | LYS | VAL |
| SEQRES | 5 | D | 178 | GLY | MET | GLU | ILE | MET | SER | GLY | PRO | ASP | ALA | ASP | ILE | LYS |
| SEQRES | 6 | D | 178 | ILE | GLY | ASN | ALA | LEU | PRO | LEU | GLU | ASN | ILE | PRO | VAL | GLY |
| SEQRES | 7 | D | 178 | THR | LEU | VAL | HIS | ASN | ILE | GLU | LEU | LYS | PRO | GLY | ARG | GLY |
| SEQRES | 8 | D | 178 | GLY | GLN | LEU | VAL | ARG | ALA | ALA | GLY | THR | SER | ALA | GLN | VAL |
| SEQRES | 9 | D | 178 | LEU | GLY | LYS | GLU | GLY | LYS | TYR | VAL | ILE | VAL | ARG | LEU | ALA |
| SEQRES | 10 | D | 178 | SER | GLY | GLU | VAL | ARG | MET | ILE | LEU | GLY | LYS | CYS | ARG | ALA |
| SEQRES | 11 | D | 178 | THR | VAL | GLY | GLU | VAL | GLY | ASN | GLY | GLY | ARG | THR | ASP | LYS |
| SEQRES | 12 | D | 178 | PRO | PHE | VAL | LYS | ALA | GLY | ASN | LYS | HIS | HIS | LYS | MET | LYS |
| SEQRES | 13 | D | 178 | ALA | ARG | GLY | THR | LYS | TRP | PRO | ASN | VAL | ARG | GLY | VAL | ALA |
| SEQRES | 14 | D | 178 | MET | ASN | ALA | VAL | ASP | HIS | PRO | PHE | GLY | | | | |
| SEQRES | 1 | E | 338 | PRO | GLN | PRO | SER | ARG | PRO | ARG | LYS | GLY | SER | LEU | GLY | PHE |
| SEQRES | 2 | E | 338 | GLY | PRO | ARG | LYS | ARG | SER | THR | SER | GLU | THR | PRO | ARG | PHE |
| SEQRES | 3 | E | 338 | ASN | SER | TRP | PRO | SER | ASP | ASP | GLY | GLN | PRO | GLY | VAL | GLN |
| SEQRES | 4 | E | 338 | GLY | PHE | ALA | GLY | TYR | LYS | ALA | GLY | MET | THR | HIS | VAL | VAL |
| SEQRES | 5 | E | 338 | LEU | VAL | ASN | ASP | GLU | PRO | ASN | SER | PRO | ARG | GLU | GLY | MET |
| SEQRES | 6 | E | 338 | GLU | GLU | THR | VAL | PRO | VAL | THR | VAL | ILE | GLU | THR | PRO | PRO |
| SEQRES | 7 | E | 338 | MET | ARG | ALA | VAL | ALA | LEU | ARG | ALA | TYR | GLU | ALA | THR | PRO |
| SEQRES | 8 | E | 338 | TYR | GLY | GLN | ARG | PRO | LEU | THR | GLU | VAL | TRP | THR | ASP | GLU |
| SEQRES | 9 | E | 338 | PHE | HIS | SER | GLU | LEU | ASP | ARG | THR | LEU | SER | ASP | ARG | LEU |
| SEQRES | 10 | E | 338 | ASP | HIS | ALA | LEU | ASP | ILE | VAL | GLU | ASP | GLN | ILE | ARG | ASP |
| SEQRES | 11 | E | 338 | ALA | HIS | GLU | ALA | GLY | ASP | LEU | GLY | ASP | LEU | ARG | LEU | ILE |
| SEQRES | 12 | E | 338 | THR | HIS | THR | VAL | PRO | ASP | ALA | VAL | PRO | SER | VAL | PRO | LYS |
| SEQRES | 13 | E | 338 | LYS | LYS | PRO | ASP | VAL | MET | GLU | THR | ARG | VAL | GLY | GLY | GLY |
| SEQRES | 14 | E | 338 | SER | VAL | SER | ASP | ARG | LEU | ASP | HIS | ALA | LEU | ASP | ILE | VAL |
| SEQRES | 15 | E | 338 | GLU | ASP | GLY | GLY | GLU | HIS | ALA | MET | ASN | ASP | ILE | PHE | ARG |
| SEQRES | 16 | E | 338 | ALA | GLY | GLU | GLY | TYR | ALA | ASP | VAL | ALA | GLY | VAL | THR | LYS | GLY |
| SEQRES | 17 | E | 338 | LYS | GLY | THR | GLN | GLY | PRO | VAL | LYS | ARG | TRP | GLY | VAL | GLN |
| SEQRES | 18 | E | 338 | LYS | ARG | LYS | GLY | LYS | HIS | ALA | ARG | GLN | GLY | TRP | ARG | ARG |
| SEQRES | 19 | E | 338 | ARG | ILE | GLY | ASN | LEU | GLY | PRO | TRP | ASN | PRO | SER | ARG | VAL |
| SEQRES | 20 | E | 338 | ARG | SER | THR | VAL | PRO | GLN | GLN | GLY | GLN | THR | GLY | TYR | HIS |
| SEQRES | 21 | E | 338 | GLN | ARG | THR | GLU | LEU | ASN | LYS | ARG | LEU | ILE | ASP | ILE | GLY |
| SEQRES | 22 | E | 338 | GLU | GLY | ASP | GLU | PRO | THR | VAL | ASP | GLY | PHE | VAL | THR | ASN |
| SEQRES | 23 | E | 338 | TYR | GLY | GLU | VAL | ASP | GLY | PRO | TYR | THR | LEU | VAL | LYS | GLY |
| SEQRES | 24 | E | 338 | SER | VAL | PRO | GLY | PRO | ASP | LYS | ARG | LEU | VAL | PRO | PHE | PHE |
| SEQRES | 25 | E | 338 | ARG | PRO | ALA | VAL | ARG | PRO | ASN | ASP | GLN | PRO | ARG | LEU | ASP |
| SEQRES | 26 | E | 338 | PRO | GLU | VAL | ARG | TYR | VAL | SER | ASN | GLU | SER | ASN | GLN | GLY |
| SEQRES | 1 | F | 246 | MET | GLU | ALA | THR | ILE | TYR | ASP | LEU | ASP | GLY | ASN | THR | ASP |
| SEQRES | 2 | F | 246 | GLY | GLU | VAL | ASP | LEU | PRO | ASP | VAL | PHE | GLU | THR | PRO | VAL |

```
SEQRES   3 F  246  ARG SER ASP LEU ILE GLY LYS ALA VAL ARG ALA ALA GLN
SEQRES   4 F  246  ALA ASN ARG LYS GLN ASP TYR GLY SER ASP GLU TYR ALA
SEQRES   5 F  246  GLY LEU ARG THR PRO ALA GLU SER PHE GLY SER GLY ARG
SEQRES   6 F  246  GLY GLN ALA HIS VAL PRO LYS LEU ASP GLY ARG ALA ARG
SEQRES   7 F  246  ARG VAL PRO GLN ALA VAL LYS GLY ARG SER ALA HIS PRO
SEQRES   8 F  246  PRO LYS THR GLU LYS ASP ARG SER LEU ASP SER LEU ASN ASP
SEQRES   9 F  246  LYS GLU ARG GLN LEU ALA VAL ARG SER ALA LEU ALA ALA
SEQRES  10 F  246  THR ALA ASP ALA ASP LEU VAL ALA ASP ARG GLY HIS GLU
SEQRES  11 F  246  PHE ASP ARG ASP GLU VAL PRO VAL VAL VAL SER ASP ASP
SEQRES  12 F  246  PHE GLU ASP LEU VAL LYS THR GLN GLU VAL VAL SER LEU
SEQRES  13 F  246  LEU GLU ALA LEU ASP VAL HIS ALA ASP ILE ASP ARG ALA
SEQRES  14 F  246  ASP GLU THR LYS ILE LYS ALA GLY GLN GLY SER ALA ARG
SEQRES  15 F  246  GLY ARG LYS TYR ARG ARG PRO ALA SER ILE LEU PHE VAL
SEQRES  16 F  246  THR SER ASP GLU PRO SER THR ALA ALA ARG ASN LEU ALA
SEQRES  17 F  246  GLY ALA ASP VAL ALA THR ALA SER GLU VAL ALA ASN THR GLU
SEQRES  18 F  246  ASP LEU ALA PRO GLY GLY ALA PRO GLY ARG LEU THR VAL
SEQRES  19 F  246  PHE THR GLU SER ALA LEU ALA GLU VAL ALA GLU ARG
SEQRES   1 G  176  SER SER GLU SER GLU SER GLY GLY GLU ASP PHE HIS GLY MET
SEQRES   2 G  176  ARG GLU PRO ARG ILE GLU LYS VAL VAL VAL HIS MET GLY
SEQRES   3 G  176  ILE GLY HIS GLY GLY ARG ASP LEU ALA ASN ALA GLU ASP
SEQRES   4 G  176  ILE LEU GLY GLU ILE THR GLY GLN MET PRO VAL ARG THR
SEQRES   5 G  176  LYS ALA LYS ARG THR VAL GLY GLU PHE ASP ILE ARG GLU
SEQRES   6 G  176  GLY ASP PRO ILE GLY ALA LYS VAL THR LEU ARG ASP GLU
SEQRES   7 G  176  MET ALA GLU GLU PHE LEU GLN THR ALA LEU PRO LEU ALA
SEQRES   8 G  176  GLU LEU ALA THR SER GLN PHE ASP ASP THR GLY ASN PHE
SEQRES   9 G  176  SER PHE GLY VAL GLU GLU HIS THR GLU PHE PRO SER GLN
SEQRES  10 G  176  GLU TYR ASP PRO SER ILE GLY ILE TYR GLY LEU ASP VAL
SEQRES  11 G  176  THR VAL ASN LEU VAL ARG PRO GLY TYR ARG VAL ALA LYS
SEQRES  12 G  176  ARG ASP LYS ALA SER ARG SER ILE PRO THR LYS HIS ARG
SEQRES  13 G  176  LEU ASN PRO ALA ASP ALA VAL ALA PHE ILE GLU SER THR
SEQRES  14 G  176  TYR ASP VAL GLU VAL SER GLU
SEQRES   1 H  177  SER ARG VAL GLY LYS LYS PRO ILE GLU ILE PRO ALA GLY
SEQRES   2 H  177  VAL THR VAL THR VAL ASN GLY ASN THR VAL THR VAL LYS
SEQRES   3 H  177  GLY PRO LYS GLY GLU LEU THR ARG THR PHE HIS PRO ASP
SEQRES   4 H  177  MET THR ILE THR VAL GLU GLY ASN VAL ILE THR VAL THR
SEQRES   5 H  177  ARG PRO SER ASP GLU LYS HIS HIS ARG ALA LEU HIS GLY
SEQRES   6 H  177  THR THR ARG SER LEU LEU ALA ASN MET VAL GLU GLY VAL
SEQRES   7 H  177  SER LYS GLY TYR GLU LYS LYS LEU GLU LEU VAL GLY VAL
SEQRES   8 H  177  GLY TYR ARG ALA SER LYS GLN GLY LYS LYS LEU VAL LEU
SEQRES   9 H  177  SER VAL GLY TYR SER HIS PRO VAL GLU ILE GLU PRO GLU
SEQRES  10 H  177  GLU GLY LEU GLU ILE GLU VAL PRO SER GLN THR LYS ILE
SEQRES  11 H  177  ILE VAL LYS GLY ALA ASP LYS GLN ARG VAL GLY GLU LEU
SEQRES  12 H  177  ALA ALA ASN ILE ARG ALA VAL ARG PRO PRO GLU PRO TYR
SEQRES  13 H  177  LYS GLY LYS GLY ILE ARG TYR GLY GLY GLU LEU VAL ARG
SEQRES  14 H  177  LEU LYS GLU GLY LYS THR GLY LYS
SEQRES   1 I  128  MET THR ILE ASP GLU ILE ILE GLU ALA ILE GLU LYS LEU
SEQRES   2 I  128  THR VAL SER GLU LEU ALA GLU LEU VAL LYS LYS LEU GLU
SEQRES   3 I  128  ASP LYS PHE GLY VAL THR ALA ALA ALA PRO VAL ALA VAL
SEQRES   4 I  128  ALA ALA ALA PRO VAL ALA GLY ALA ALA ALA GLY ALA ALA
SEQRES   5 I  128  GLN GLU GLU LYS THR GLU PHE ASP VAL VAL LEU LYS SER
SEQRES   6 I  128  PHE GLY GLN ASN LYS ILE GLN VAL ILE LYS VAL VAL ARG
SEQRES   7 I  128  GLU ILE THR GLY LEU GLY LEU LYS GLU ALA LYS ASP LEU
SEQRES   8 I  128  VAL GLU LYS ALA GLY SER PRO ASP ALA VAL ILE LYS SER
SEQRES   9 I  128  GLY VAL SER LYS GLU GLU ALA GLU GLU ILE LYS LYS LYS
SEQRES  10 I  128  LEU GLU GLU ALA GLY ALA GLU VAL GLU LEU LYS
SEQRES   1 J  128  MET THR ILE ASP GLU ILE ILE GLU ALA ILE GLU LYS LEU
SEQRES   2 J  128  THR VAL SER GLU LEU ALA GLU LEU VAL LYS LYS LEU GLU
SEQRES   3 J  128  ASP LYS PHE GLY VAL THR ALA ALA ALA PRO VAL ALA VAL
SEQRES   4 J  128  ALA ALA ALA PRO VAL ALA GLY ALA ALA ALA GLY ALA ALA
SEQRES   5 J  128  GLN GLU GLU LYS THR GLU PHE ASP VAL VAL LEU LYS SER
SEQRES   6 J  128  PHE GLY GLN ASN LYS ILE GLN VAL ILE LYS VAL VAL ARG
SEQRES   7 J  128  GLU ILE THR GLY LEU GLY LEU LYS GLU ALA LYS ASP LEU
SEQRES   8 J  128  VAL GLU LYS ALA GLY SER PRO ASP ALA VAL ILE LYS SER
SEQRES   9 J  128  GLY VAL SER LYS GLU GLU ALA GLU GLU ILE LYS LYS LYS
SEQRES  10 J  128  LEU GLU GLU ALA GLY ALA GLU VAL GLU LEU LYS
SEQRES   1 K  149  MET LYS VAL ILE PHE LEU LYS ASP VAL LYS GLY LYS GLY
SEQRES   2 K  149  LYS LYS GLY GLU ILE LYS ASN VAL ALA ASP GLY TYR ALA
SEQRES   3 K  149  ASN ASN PHE LEU PHE LYS GLN GLY LEU ALA ILE GLU ALA
SEQRES   4 K  149  THR PRO ALA ASN LEU LYS ALA LEU GLU ALA GLN LYS GLN
SEQRES   5 K  149  LYS GLU GLN ARG GLN ALA ALA GLU GLU LEU ALA ASN ALA
SEQRES   6 K  149  LYS LYS LEU LYS GLU GLN LEU GLU LYS LEU THR VAL THR
SEQRES   7 K  149  ILE PRO ALA LYS ALA GLY GLU GLY GLY ARG LEU PHE GLY
SEQRES   8 K  149  SER ILE THR SER LYS GLN ILE ALA GLU SER LEU GLU ALA
SEQRES   9 K  149  GLN HIS GLY LEU LYS LEU ASP LYS ARG LYS ILE GLU LEU
SEQRES  10 K  149  ALA ASP ALA ILE ARG ALA LEU GLY TYR THR VAL ASN PRO
SEQRES  11 K  149  VAL LYS LEU HIS PRO GLU VAL THR ALA THR LEU LYS VAL
SEQRES  12 K  149  HIS VAL THR GLU GLN LYS
SEQRES   1 L  141  MET ALA LYS LYS VAL ALA ALA ALA GLN ILE LYS LEU GLN LEU
SEQRES   2 L  141  PRO ALA GLY LYS ALA THR PRO ALA PRO PRO VAL GLY PRO
SEQRES   3 L  141  ALA LEU GLY GLN HIS GLY VAL ASN ILE MET GLU PHE CYS
SEQRES   4 L  141  LYS ARG PHE ASN ALA GLU THR ALA ASP LYS ALA GLY MET
SEQRES   5 L  141  ILE LEU PRO VAL VAL ILE THR VAL TYR GLU ASP LYS SER
SEQRES   6 L  141  PHE THR PHE ILE ILE LYS THR PRO PRO ALA SER PHE LEU
SEQRES   7 L  141  LEU LYS LYS ALA ALA GLY ILE GLU LYS GLY SER SER GLU
SEQRES   8 L  141  PRO LYS ARG LYS ILE VAL GLY LYS VAL THR ARG LYS GLN
SEQRES   9 L  141  ILE GLU GLU ILE ALA LYS THR LYS MET PRO ASP LEU ASN
SEQRES  10 L  141  ALA ASN SER LEU GLU ALA ALA MET LYS ILE ILE GLU GLY
```

```
SEQRES   11 L  141  THR ALA LYS SER MET GLY ILE GLU VAL VAL ASP
SEQRES    1 M  145  MET SER VAL ALA GLU PHE ASP ALA ASP VAL ILE VAL ASP
SEQRES    2 M  145  ALA ARG ASP CYS ILE MET GLY ARG VAL ALA SER GLN VAL
SEQRES    3 M  145  ALA GLU GLN ALA LEU ASP GLY GLU THR VAL ALA VAL VAL
SEQRES    4 M  145  ASN ALA GLU ARG ALA VAL ILE THR GLY ARG GLU GLU GLN
SEQRES    5 M  145  ILE VAL GLU LYS TYR GLU LYS ARG VAL ASP ILE GLY ASN
SEQRES    6 M  145  ASP ASN GLY TYR PHE TYR PRO LYS ARG PRO ASP VAL ILE
SEQRES    7 M  145  PHE LYS ARG THR ILE ARG GLY MET LEU PRO HIS LYS LYS
SEQRES    8 M  145  GLN ARG GLY ARG GLU ALA PHE GLU SER VAL ARG VAL TYR
SEQRES    9 M  145  LEU GLY ASN PRO TYR ASP GLU ASP GLY VAL VAL LEU ASP
SEQRES   10 M  145  GLY THR SER LEU ASP ARG LEU SER ASN ILE LYS PHE VAL
SEQRES   11 M  145  THR LEU GLY GLU ILE SER GLU THR LEU GLY ALA ASN LYS
SEQRES   12 M  145  THR TRP
SEQRES    1 N  122  MET ILE GLN GLN GLU SER ARG LEU LYS VAL ALA ASP ASN
SEQRES    2 N  122  SER GLY ALA ARG GLU VAL LEU VAL ILE LYS VAL LEU GLY
SEQRES    3 N  122  GLY SER ARG ARG TYR ALA ASN ILE GLY VAL VAL VAL
SEQRES    4 N  122  VAL ALA THR VAL LYS ASP ALA THR PRO GLY GLY VAL VAL
SEQRES    5 N  122  LYS LYS GLY GLN VAL VAL LYS ALA VAL VAL VAL ARG THR
SEQRES    6 N  122  LYS ARG GLY VAL ARG ARG PRO ASP GLY SER TYR ILE ARG
SEQRES    7 N  122  PHE ASP GLU ASN ALA CYS VAL ILE ILE ARG ASP ASP LYS
SEQRES    8 N  122  SER PRO ARG GLY THR ARG ILE PHE GLY PRO VAL ALA ARG
SEQRES    9 N  122  GLU LEU ARG ASP LYS ASP PHE MET LYS ILE ILE SER LEU
SEQRES   10 N  122  ALA PRO GLU VAL ILE
SEQRES    1 O  164  THR SER LYS LYS LYS ARG GLN ARG GLY SER ARG THR HIS
SEQRES    2 O  164  GLY GLY GLY SER HIS LYS ASN ARG ARG GLY ALA GLY HIS
SEQRES    3 O  164  ARG GLY GLY ARG GLY ASP ALA GLY ARG ASP LYS HIS GLU
SEQRES    4 O  164  PHE HIS ASN HIS GLU PRO LEU GLY LYS SER GLU PHE LYS
SEQRES    5 O  164  ARG PRO GLN LYS VAL GLN GLU GLU ALA ALA THR ILE ASP
SEQRES    6 O  164  VAL ARG GLU ILE ASP GLU ASN VAL THR LEU LEU ALA ALA
SEQRES    7 O  164  ASP ASP VAL ALA GLU VAL GLU ASP GLY GLY PHE ARG VAL
SEQRES    8 O  164  ASP VAL ARG ASP VAL VAL GLU GLU ALA ASP ASP ALA ASP
SEQRES    9 O  164  TYR VAL LYS VAL LEU GLY ALA GLY GLN VAL ARG HIS GLU
SEQRES   10 O  164  LEU THR LEU ILE ALA ASP ASP PHE SER ER GLU GLY VAL ALA ARG
SEQRES   11 O  164  GLU LYS VAL GLU GLY ALA GLY GLY SER VAL GLU LEU THR
SEQRES   12 O  164  ASP LEU GLY GLU GLU ARG GLN ALA GLU ALA GLU GLU THR
SEQRES   13 O  164  GLU ASP ALA ASP ALA ASP GLU GLU
SEQRES    1 P  138  SER ILE LYS PRO THR ARG ARG GLU TYR ILE SER GLY ILE
SEQRES    2 P  138  PRO GLY LYS GLY ILE ALA GLN PHE LYS MET GLY ASN ASN
SEQRES    3 P  138  THR TYR PRO ALA GLN VAL GLU ASN VAL VAL GLU LYS PRO
SEQRES    4 P  138  VAL GLN ILE ARG HIS ASN ALA LEU GLU ALA ALA ARG ASN
SEQRES    5 P  138  ALA ALA ASN ARG PHE VAL GLN ASN SER GLY LYS PHE ARG
SEQRES    6 P  138  ILE ARG LYS PHE PRO PHE HIS VAL ILE ARG GLU GLU LYS ASP
SEQRES    7 P  138  GLY ASP GLY MET ARG ALA PRO PHE GLY LYS SER VAL GLY
SEQRES    8 P  138  THR ALA ALA ARG SER HIS GLY ALA ASN HIS ASP PHE ILE
SEQRES    9 P  138  ALA TRP VAL ASN PRO ASP PRO ALA VAL GLU PHE ALA TRP
SEQRES   10 P  138  ARG ARG ALA TYR MET LYS VAL THR PRO THR VAL ASN ILE
SEQRES   11 P  138  ASP SER SER PRO ALA GLY ASN ALA
SEQRES    1 Q  186  ALA THR GLY PRO ARG TYR LYS VAL PRO MET ARG ARG ARG
SEQRES    2 Q  186  ARG GLU ALA ARG THR ASP TYR HIS GLN ARG LEU ARG LEU
SEQRES    3 Q  186  LEU LYS SER GLY LYS PRO ARG LEU VAL ALA ARG LYS SER
SEQRES    4 Q  186  ASN LYS HIS VAL ARG ALA GLN LEU VAL THR LEU GLY PRO
SEQRES    5 Q  186  ASN GLY ASP ASP THR LEU ALA SER ALA HIS SER SER ASP ASP
SEQRES    6 Q  186  LEU ALA GLU TYR GLY LEU ALA PRO THR GLY ASN MET
SEQRES    7 Q  186  PRO SER ALA TYR LEU THR GLY LEU LEU ALA GLY LEU ARG
SEQRES    8 Q  186  ALA GLN GLU ALA GLY VAL GLU GLU ALA VAL LEU ASP ILE
SEQRES    9 Q  186  GLY LEU ASN SER PRO THR PRO GLY SER LYS VAL PHE ALA
SEQRES   10 Q  186  ILE GLN GLU GLY ALA ILE ASP ALA GLY LEU ASP ILE PRO
SEQRES   11 Q  186  HIS ASN ASP ASP VAL LEU ALA ASP TRP GLN ARG THR ARG
SEQRES   12 Q  186  GLY ALA HIS ILE ALA GLU TYR ASP GLN GLN LEU GLU GLU GLU
SEQRES   13 Q  186  PRO LEU TYR SER GLY ASP PHE ASP ALA ALA ASP LEU PRO
SEQRES   14 Q  186  GLU HIS PHE ASP GLU LEU ARG GLU THR LEU LEU ASP GLY
SEQRES   15 Q  186  ASP ILE GLU LEU
SEQRES    1 R   66  PRO ARG THR ARG GLU CYS ASP TYR CYS GLY THR ASP ILE
SEQRES    2 R   66  GLU PRO GLY THR GLY THR MET PHE VAL HIS LYS ASP GLY
SEQRES    3 R   66  ALA THR THR HIS PHE CYS SER SER LYS CYS GLU ALA ASN
SEQRES    4 R   66  ALA ASP LEU GLY ARG GLU ALA ARG ASN LEU GLU TRP THR
SEQRES    5 R   66  ASP THR ALA ARG GLY GLU ALA GLY GLU ALA GLU ASP GLU
SEQRES    6 R   66  ALA
SEQRES    1 S  113  MET GLU ALA LYS ALA ILE ALA ARG TYR VAL ARG ILE SER
SEQRES    2 S  113  PRO ARG LYS VAL ARG LEU VAL VAL ASP LEU ILE ARG GLY
SEQRES    3 S  113  LYS SER LEU GLU GLU ALA ARG ASN ILE LEU GLU TYR THR
SEQRES    4 S  113  ASN LYS ARG GLY ALA TYR PHE VAL ALA LYS VAL LEU GLU
SEQRES    5 S  113  SER ALA ALA ALA ASN ALA VAL ASN ASN HIS ASP MET LEU
SEQRES    6 S  113  GLU ASP ARG LEU TYR VAL LYS ALA ALA TYR VAL ASP GLU
SEQRES    7 S  113  GLY PRO ALA LEU LYS ARG VAL LEU PRO ARG ALA ARG GLY
SEQRES    8 S  113  ARG ALA ASP ILE ILE LYS LYS ARG THR SER HIS ILE THR
SEQRES    9 S  113  VAL ILE LEU GLY GLU LYS HIS GLY LYS
SEQRES    1 T   84  SER TRP ASP VAL ILE LYS HIS PRO HIS VAL THR GLU LYS
SEQRES    2 T   84  ALA MET ASN ASP MET ASP PHE GLN ASN LYS LEU GLN PHE
SEQRES    3 T   84  ALA VAL ASP ASP ARG ALA SER LYS GLY GLU VAL ALA ASP
SEQRES    4 T   84  ALA VAL GLU GLU GLN TYR ASP VAL THR VAL GLU GLN VAL
SEQRES    5 T   84  ASN THR GLN ASN THR MET GLY GLU VAL LYS LYS ALA VAL
SEQRES    6 T   84  VAL ARG LEU SER GLU ASP ASP ASP ALA GLN GLU VAL ALA
SEQRES    7 T   84  SER ARG ILE GLY VAL PHE
SEQRES    1 U  119  SER LYS GLN PRO ASP LYS GLU ARG LYS SER GLN ARG ARG
SEQRES    2 U  119  ALA PRO LEU HIS GLU ARG HIS LYS GLN VAL ARG ALA THR
SEQRES    3 U  119  LEU SER ALA ASP LEU ARG GLU GLU TYR GLY GLN ARG ASN
```

```
SEQRES   4 U  119  VAL ARG VAL ASN ALA GLY ASP THR VAL GLU VAL LEU ARG
SEQRES   5 U  119  GLY ASP PHE ALA GLY GLU GLU GLY VAL ILE GLU ASN VAL
SEQRES   6 U  119  ASP LEU ASP LYS ALA VAL ILE HIS VAL GLU ASP VAL THR
SEQRES   7 U  119  LEU GLU LYS THR ASP GLY GLU GLU VAL PRO ARG PRO LEU
SEQRES   8 U  119  ASP THR SER ASN VAL ARG VAL THR ASP GLU ASP LEU GLU
SEQRES   9 U  119  ASP GLY LYS ARG GLU ALA ARG LEU GLU SER GLU ASP ASP
SEQRES  10 U  119  SER ALA
SEQRES   1 V   94  MET PHE THR ILE ASN ALA GLU VAL ARG LYS GLU GLN GLY
SEQRES   2 V   94  LYS GLY ALA SER ARG ARG LEU ARG ALA ALA ASN LYS PHE
SEQRES   3 V   94  PRO ALA ILE ILE TYR GLY GLY LYS GLU ALA PRO LEU ALA
SEQRES   4 V   94  ILE GLU LEU ASP HIS ASP LYS VAL MET ASN MET GLN ALA
SEQRES   5 V   94  LYS ALA GLU PHE TYR SER GLU VAL LEU THR ILE VAL VAL
SEQRES   6 V   94  ASP GLY LYS GLU ILE LYS VAL LYS ALA GLN ASP VAL GLN
SEQRES   7 V   94  ARG HIS PRO TYR LYS PRO LYS LEU GLN HIS ILE ASP PHE
SEQRES   8 V   94  VAL ARG ALA
SEQRES   1 W   70  THR VAL LEU HIS VAL GLN GLU ILE ARG ASP MET THR PRO
SEQRES   2 W   70  ALA GLU ARG GLU ALA GLU LEU ASP LEU LYS THR GLU GLU
SEQRES   3 W   70  LEU LEU ASN ALA ARG ALA VAL GLN ALA ALA GLY GLY ALA
SEQRES   4 W   70  PRO GLU ASN PRO GLY ARG ILE LYS GLU LEU ARG LYS ALA
SEQRES   5 W   70  ILE ALA ARG ILE LYS THR ILE GLN GLY GLU GLU GLY ASP
SEQRES   6 W   70  LEU GLN GLU ASN GLU
SEQRES   1 X   60  MET PRO ARG LEU LYS VAL LYS LEU VAL LYS SER PRO ILE
SEQRES   2 X   60  GLY TYR PRO LYS ASP GLN LYS ALA ALA LEU LYS ALA LEU
SEQRES   3 X   60  GLY LEU ARG ARG LEU GLN GLN GLU ARG VAL LEU GLU ASP
SEQRES   4 X   60  THR PRO ALA ILE ARG GLY ASN VAL GLU LYS VAL ALA HIS
SEQRES   5 X   60  LEU VAL ARG VAL GLU VAL VAL GLU
CRYST1  507.200  507.200  803.660  90.00  90.00  90.00 I 4 2 2     32
ORIGX1       1.000000  0.000000  0.000000        0.00000
ORIGX2       0.000000  1.000000  0.000000        0.00000
ORIGX3       0.000000  0.000000  1.000000        0.00000
SCALE1       0.001972  0.000000  0.000000        0.00000
SCALE2       0.000000  0.001972  0.000000        0.00000
SCALE3       0.000000  0.000000  0.001244        0.00000
ATOM      1  P     G A   1       6.074 250.096 338.055  1.00  0.00           P
ATOM      2  P     G A   2       2.777 245.724 338.490  1.00  0.00           P
ATOM      3  P     U A   3      -0.019 241.353 337.355  1.00  0.00           P
ATOM      4  P     C A   4      -1.598 238.589 334.091  1.00  0.00           P
ATOM      5  P     A A   5      -2.738 235.412 330.650  1.00  0.00           P
ATOM      6  P     A A   6      -1.985 233.518 325.989  1.00  0.00           P
ATOM      7  P     G A   7       1.432 232.379 321.517  1.00  0.00           P
ATOM      8  P     A A   8       6.740 232.282 318.548  1.00  0.00           P
ATOM      9  P     U A   9      13.635 232.591 317.975  1.00  0.00           P
ATOM     10  P     G A  10      17.391 233.621 321.732  1.00  0.00           P
ATOM     11  P     G A  11      21.730 232.769 327.058  1.00  0.00           P
ATOM     12  P     U A  12      24.781 229.383 330.400  1.00  0.00           P
ATOM     13  P     A A  13      24.197 227.292 336.868  1.00  0.00           P
ATOM     14  P     A A  14      26.815 221.716 339.404  1.00  0.00           P
ATOM     15  P     G A  15      29.228 215.877 341.517  1.00  0.00           P
ATOM     16  P     G A  16      31.524 213.557 335.399  1.00  0.00           P
ATOM     17  P     G A  17      34.730 212.685 331.372  1.00  0.00           P
ATOM     18  P     C A  18      37.946 214.809 327.403  1.00  0.00           P
ATOM     19  P     C A  19      42.747 217.872 326.507  1.00  0.00           P
ATOM     20  P     C A  20      47.725 220.122 328.824  1.00  0.00           P
ATOM     21  P     A A  21      50.817 223.237 333.819  1.00  0.00           P
ATOM     22  P     C A  22      52.832 222.224 339.983  1.00  0.00           P
ATOM     23  P     G A  23      53.692 217.719 344.370  1.00  0.00           P
ATOM     24  P     G A  24      54.850 211.654 345.624  1.00  0.00           P
ATOM     25  P     U A  25      55.085 206.696 346.780  1.00  0.00           P
ATOM     26  P     G A  26      53.885 202.122 344.320  1.00  0.00           P
ATOM     27  P     G A  27      57.649 199.760 340.680  1.00  0.00           P
ATOM     28  P     A A  28      62.861 201.212 336.072  1.00  0.00           P
ATOM     29  P     U A  29      65.059 203.638 331.489  1.00  0.00           P
ATOM     30  P     G A  30      70.855 207.312 329.198  1.00  0.00           P
ATOM     31  P     C A  31      76.301 208.408 330.589  1.00  0.00           P
ATOM     32  P     C A  32      80.530 207.348 334.367  1.00  0.00           P
ATOM     33  P     U A  33      82.648 204.010 337.274  1.00  0.00           P
ATOM     34  P     C A  34      83.177 199.238 340.236  1.00  0.00           P
ATOM     35  P     G A  35      84.744 193.271 341.582  1.00  0.00           P
ATOM     36  P     G A  36      81.984 187.159 337.587  1.00  0.00           P
ATOM     37  P     C A  37      81.455 184.903 330.829  1.00  0.00           P
ATOM     38  P     A A  38      82.409 184.830 325.248  1.00  0.00           P
ATOM     39  P     C A  39      86.877 185.296 321.143  1.00  0.00           P
ATOM     40  P     C A  40      92.405 185.956 319.039  1.00  0.00           P
ATOM     41  P     C A  41      98.180 185.367 319.894  1.00  0.00           P
ATOM     42  P     G A  43     102.713 182.931 323.654  1.00  0.00           P
ATOM     43  P     A A  44     104.694 180.943 329.344  1.00  0.00           P
ATOM     44  P     G A  45     104.094 176.230 334.296  1.00  0.00           P
ATOM     45  P     C A  46     100.208 172.081 335.402  1.00  0.00           P
ATOM     46  P     C A  47      98.311 167.658 339.932  1.00  0.00           P
ATOM     47  P     G A  48      98.533 164.015 343.686  1.00  0.00           P
ATOM     48  P     A A  49      96.569 159.453 346.436  1.00  0.00           P
ATOM     49  P     U A  50      97.424 154.491 349.803  1.00  0.00           P
ATOM     50  P     G A  51      95.225 160.238 351.944  1.00  0.00           P
ATOM     51  P     A A  52      90.258 162.841 350.046  1.00  0.00           P
ATOM     52  P     A A  53      90.157 167.772 347.072  1.00  0.00           P
ATOM     53  P     G A  54      85.975 170.810 344.683  1.00  0.00           P
ATOM     54  P     G A  55      80.355 171.204 346.167  1.00  0.00           P
```

```
ATOM   55  P  A A  56   75.852 170.205 350.308  1.00  0.00           P
ATOM   56  P  C A  57   73.851 169.276 355.792  1.00  0.00           P
ATOM   57  P  G A  58   74.282 170.772 361.313  1.00  0.00           P
ATOM   58  P  U A  59   78.247 173.426 365.927  1.00  0.00           P
ATOM   59  P  G A  60   81.504 177.302 367.876  1.00  0.00           P
ATOM   60  P  G A  61   83.957 182.469 371.215  1.00  0.00           P
ATOM   61  P  C A  62   78.264 181.779 372.533  1.00  0.00           P
ATOM   62  P  U A  63   75.012 183.934 369.385  1.00  0.00           P
ATOM   63  P  A A  64   72.858 182.755 365.007  1.00  0.00           P
ATOM   64  P  C A  65   72.323 181.581 359.669  1.00  0.00           P
ATOM   65  P  C A  66   74.095 181.302 354.351  1.00  0.00           P
ATOM   66  P  U A  67   79.491 180.385 352.250  1.00  0.00           P
ATOM   67  P  G A  68   85.634 179.588 350.726  1.00  0.00           P
ATOM   68  P  C A  69   89.976 177.288 353.797  1.00  0.00           P
ATOM   69  P  G A  70   91.206 172.573 357.963  1.00  0.00           P
ATOM   70  P  A A  71   90.154 169.242 363.579  1.00  0.00           P
ATOM   71  P  U A  72   90.270 167.777 368.875  1.00  0.00           P
ATOM   72  P  A A  73   89.994 174.457 367.794  1.00  0.00           P
ATOM   73  P  A A  74   87.332 178.314 363.979  1.00  0.00           P
ATOM   74  P  G A  75   90.929 183.749 362.089  1.00  0.00           P
ATOM   75  P  C A  76   95.502 180.668 365.350  1.00  0.00           P
ATOM   76  P  C A  77  100.217 179.151 367.253  1.00  0.00           P
ATOM   77  P  A A  78  106.029 178.831 366.600  1.00  0.00           P
ATOM   78  P  G A  79  110.789 180.449 364.209  1.00  0.00           P
ATOM   79  P  G A  80  113.418 184.102 360.644  1.00  0.00           P
ATOM   80  P  G A  81  113.201 188.933 357.113  1.00  0.00           P
ATOM   81  P  G A  82  110.253 193.870 355.540  1.00  0.00           P
ATOM   82  P  G A  83  106.749 197.973 357.038  1.00  0.00           P
ATOM   83  P  A A  84  104.101 201.199 361.951  1.00  0.00           P
ATOM   84  P  G A  85   97.737 202.096 365.029  1.00  0.00           P
ATOM   85  P  C A  86   93.703 197.770 361.651  1.00  0.00           P
ATOM   86  P  C A  87   91.101 192.819 361.608  1.00  0.00           P
ATOM   87  P  G A  88   88.559 188.090 362.975  1.00  0.00           P
ATOM   88  P  G A  89   87.848 191.064 358.416  1.00  0.00           P
ATOM   89  P  U A  90   83.878 192.699 355.526  1.00  0.00           P
ATOM   90  P  A A  91   82.259 197.791 360.174  1.00  0.00           P
ATOM   91  P  G A  92   80.616 199.752 365.415  1.00  0.00           P
ATOM   92  P  C A  93   78.133 199.858 369.985  1.00  0.00           P
ATOM   93  P  G A  94   79.016 198.246 375.385  1.00  0.00           P
ATOM   94  P  G A  95   82.833 195.185 378.969  1.00  0.00           P
ATOM   95  P  G A  96   88.416 190.997 378.995  1.00  0.00           P
ATOM   96  P  C A  97   94.198 190.013 376.023  1.00  0.00           P
ATOM   97  P  G A  98  100.900 190.283 373.822  1.00  0.00           P
ATOM   98  P  U A  99  102.880 195.061 369.933  1.00  0.00           P
ATOM   99  P  G A 101  109.311 195.511 370.315  1.00  0.00           P
ATOM  100  P  G A 102  109.131 190.382 364.197  1.00  0.00           P
ATOM  101  P  A A 103  103.326 190.702 365.178  1.00  0.00           P
ATOM  102  P  U A 104   99.086 186.962 363.684  1.00  0.00           P
ATOM  103  P  C A 105   95.068 187.578 360.130  1.00  0.00           P
ATOM  104  P  C A 106   96.254 187.490 354.539  1.00  0.00           P
ATOM  105  P  C A 107   99.548 184.745 350.537  1.00  0.00           P
ATOM  106  P  U A 108  102.703 180.862 348.573  1.00  0.00           P
ATOM  107  P  G A 109  105.202 175.568 349.369  1.00  0.00           P
ATOM  108  P  G A 110  105.015 170.705 353.026  1.00  0.00           P
ATOM  109  P  A A 111  102.602 167.520 357.843  1.00  0.00           P
ATOM  110  P  U A 112   98.973 165.481 361.314  1.00  0.00           P
ATOM  111  P  G A 113   93.517 164.510 362.325  1.00  0.00           P
ATOM  112  P  U A 114   88.861 163.760 358.976  1.00  0.00           P
ATOM  113  P  C A 115   85.134 159.956 359.748  1.00  0.00           P
ATOM  114  P  C A 116   81.528 157.335 356.088  1.00  0.00           P
ATOM  115  P  G A 117   79.552 156.313 350.386  1.00  0.00           P
ATOM  116  P  A A 118   84.355 155.454 347.153  1.00  0.00           P
ATOM  117  P  A A 119   83.440 151.193 349.943  1.00  0.00           P
ATOM  118  P  U A 120   87.314 151.459 351.183  1.00  0.00           P
ATOM  119  P  G A 121   90.426 149.045 353.684  1.00  0.00           P
ATOM  120  P  G A 122   86.223 144.266 352.594  1.00  0.00           P
ATOM  121  P  G A 123   80.046 143.509 353.907  1.00  0.00           P
ATOM  122  P  G A 124   75.815 146.546 353.188  1.00  0.00           P
ATOM  123  P  G A 125   76.356 151.129 351.146  1.00  0.00           P
ATOM  124  P  A A 126   76.691 155.273 353.474  1.00  0.00           P
ATOM  125  P  A A 127   75.678 157.654 356.871  1.00  0.00           P
ATOM  126  P  C A 128   74.859 157.052 362.694  1.00  0.00           P
ATOM  127  P  C A 129   76.679 153.276 365.586  1.00  0.00           P
ATOM  128  P  C A 130   78.637 147.317 367.038  1.00  0.00           P
ATOM  129  P  G A 131   82.248 143.680 367.623  1.00  0.00           P
ATOM  130  P  G A 132   86.444 139.951 368.308  1.00  0.00           P
ATOM  131  P  C A 133   92.260 139.212 370.304  1.00  0.00           P
ATOM  132  P  C A 134   97.256 141.670 372.833  1.00  0.00           P
ATOM  133  P  G A 135  100.201 145.174 375.394  1.00  0.00           P
ATOM  134  P  G A 136  100.128 150.121 378.141  1.00  0.00           P
ATOM  135  P  C A 137   97.341 153.932 381.047  1.00  0.00           P
ATOM  136  P  G A 137A  93.230 156.631 384.357  1.00  0.00           P
ATOM  137  P  G A 138   88.074 154.271 387.416  1.00  0.00           P
ATOM  138  P  G A 139   86.529 150.146 389.235  1.00  0.00           P
ATOM  139  P  A A 140   87.059 144.699 385.753  1.00  0.00           P
ATOM  140  P  A A 141   86.155 142.211 380.453  1.00  0.00           P
ATOM  141  P  C A 141A  81.145 143.367 377.118  1.00  0.00           P
```

| | | | | | | | | | |
|---|---|---|---|---|---|---|---|---|---|
| ATOM | 142 | P | G | A | 142 | 80.312 148.129 374.850 | 1.00 | 0.00 | P |
| ATOM | 143 | P | C | A | 143 | 81.704 152.716 372.168 | 1.00 | 0.00 | P |
| ATOM | 144 | P | C | A | 144 | 85.389 157.382 369.905 | 1.00 | 0.00 | P |
| ATOM | 145 | P | G | A | 145 | 90.547 157.816 367.922 | 1.00 | 0.00 | P |
| ATOM | 146 | P | G | A | 146 | 95.489 156.792 364.857 | 1.00 | 0.00 | P |
| ATOM | 147 | P | U | A | 147 | 97.792 153.322 361.520 | 1.00 | 0.00 | P |
| ATOM | 148 | P | C | A | 148 | 96.738 148.429 357.648 | 1.00 | 0.00 | P |
| ATOM | 149 | P | A | A | 149 | 92.533 144.331 354.830 | 1.00 | 0.00 | P |
| ATOM | 150 | P | C | A | 150 | 90.099 141.849 351.028 | 1.00 | 0.00 | P |
| ATOM | 151 | P | C | A | 151 | 90.017 140.260 345.672 | 1.00 | 0.00 | P |
| ATOM | 152 | P | G | A | 152 | 92.731 139.303 340.816 | 1.00 | 0.00 | P |
| ATOM | 153 | P | C | A | 153 | 97.935 140.416 337.711 | 1.00 | 0.00 | P |
| ATOM | 154 | P | G | A | 154 | 103.971 140.730 336.685 | 1.00 | 0.00 | P |
| ATOM | 155 | P | C | A | 155 | 108.481 138.609 338.875 | 1.00 | 0.00 | P |
| ATOM | 156 | P | U | A | 161 | 110.649 138.519 342.116 | 1.00 | 0.00 | P |
| ATOM | 157 | P | U | A | 162 | 111.980 135.689 344.029 | 1.00 | 0.00 | P |
| ATOM | 158 | P | U | A | 163 | 111.829 133.943 348.561 | 1.00 | 0.00 | P |
| ATOM | 159 | P | U | A | 164 | 105.209 133.401 349.692 | 1.00 | 0.00 | P |
| ATOM | 160 | P | G | A | 171 | 102.428 138.271 353.060 | 1.00 | 0.00 | P |
| ATOM | 161 | P | C | A | 172 | 104.515 144.685 354.087 | 1.00 | 0.00 | P |
| ATOM | 162 | P | G | A | 173 | 106.982 148.957 350.890 | 1.00 | 0.00 | P |
| ATOM | 163 | P | C | A | 174 | 106.197 152.131 346.257 | 1.00 | 0.00 | P |
| ATOM | 164 | P | G | A | 175 | 101.671 153.380 341.218 | 1.00 | 0.00 | P |
| ATOM | 165 | P | G | A | 176 | 96.674 154.676 339.432 | 1.00 | 0.00 | P |
| ATOM | 166 | P | G | A | 177 | 90.520 153.750 337.844 | 1.00 | 0.00 | P |
| ATOM | 167 | P | G | A | 178 | 86.666 157.158 338.812 | 1.00 | 0.00 | P |
| ATOM | 168 | P | G | A | 179 | 86.259 163.250 336.832 | 1.00 | 0.00 | P |
| ATOM | 169 | P | G | A | 180 | 85.875 167.015 334.158 | 1.00 | 0.00 | P |
| ATOM | 170 | P | A | A | 181 | 85.163 171.731 334.003 | 1.00 | 0.00 | P |
| ATOM | 171 | P | A | A | 182 | 83.868 171.779 328.906 | 1.00 | 0.00 | P |
| ATOM | 172 | P | C | A | 183 | 86.702 170.166 322.968 | 1.00 | 0.00 | P |
| ATOM | 173 | P | C | A | 184 | 91.233 168.337 319.878 | 1.00 | 0.00 | P |
| ATOM | 174 | P | U | A | 185 | 94.071 163.701 318.781 | 1.00 | 0.00 | P |
| ATOM | 175 | P | G | A | 186 | 94.137 157.904 318.309 | 1.00 | 0.00 | P |
| ATOM | 176 | P | G | A | 187 | 91.563 152.634 318.119 | 1.00 | 0.00 | P |
| ATOM | 177 | P | G | A | 188 | 85.371 149.997 317.772 | 1.00 | 0.00 | P |
| ATOM | 178 | P | G | A | 189 | 79.988 149.744 316.536 | 1.00 | 0.00 | P |
| ATOM | 179 | P | A | A | 190 | 75.927 153.084 313.258 | 1.00 | 0.00 | P |
| ATOM | 180 | P | A | A | 191 | 71.399 157.328 312.165 | 1.00 | 0.00 | P |
| ATOM | 181 | P | C | A | 192 | 66.596 160.114 310.372 | 1.00 | 0.00 | P |
| ATOM | 182 | P | U | A | 193 | 64.950 164.735 309.000 | 1.00 | 0.00 | P |
| ATOM | 183 | P | G | A | 194 | 66.992 168.666 304.992 | 1.00 | 0.00 | P |
| ATOM | 184 | P | A | A | 195 | 68.103 169.621 300.069 | 1.00 | 0.00 | P |
| ATOM | 185 | P | A | A | 196 | 67.268 167.676 294.027 | 1.00 | 0.00 | P |
| ATOM | 186 | P | A | A | 197 | 64.651 166.719 298.654 | 1.00 | 0.00 | P |
| ATOM | 187 | P | C | A | 198 | 62.656 163.397 301.632 | 1.00 | 0.00 | P |
| ATOM | 188 | P | A | A | 199 | 64.228 157.601 301.534 | 1.00 | 0.00 | P |
| ATOM | 189 | P | U | A | 200 | 68.351 153.384 300.483 | 1.00 | 0.00 | P |
| ATOM | 190 | P | C | A | 201 | 74.044 153.184 299.801 | 1.00 | 0.00 | P |
| ATOM | 191 | P | U | A | 202 | 77.519 157.937 300.134 | 1.00 | 0.00 | P |
| ATOM | 192 | P | C | A | 203 | 80.041 160.690 303.743 | 1.00 | 0.00 | P |
| ATOM | 193 | P | A | A | 204 | 77.493 165.196 309.120 | 1.00 | 0.00 | P |
| ATOM | 194 | P | G | A | 205 | 82.705 161.361 307.672 | 1.00 | 0.00 | P |
| ATOM | 195 | P | U | A | 206 | 81.899 161.249 312.881 | 1.00 | 0.00 | P |
| ATOM | 196 | P | A | A | 207 | 80.786 165.656 316.746 | 1.00 | 0.00 | P |
| ATOM | 197 | P | C | A | 208 | 77.558 165.829 321.722 | 1.00 | 0.00 | P |
| ATOM | 198 | P | C | A | 209 | 77.157 161.715 325.818 | 1.00 | 0.00 | P |
| ATOM | 199 | P | C | A | 210 | 79.300 157.448 329.112 | 1.00 | 0.00 | P |
| ATOM | 200 | P | A | A | 211 | 83.261 153.892 331.112 | 1.00 | 0.00 | P |
| ATOM | 201 | P | G | A | 212 | 89.372 153.864 332.374 | 1.00 | 0.00 | P |
| ATOM | 202 | P | A | A | 213 | 94.958 156.056 332.219 | 1.00 | 0.00 | P |
| ATOM | 203 | P | G | A | 214 | 98.948 160.523 332.029 | 1.00 | 0.00 | P |
| ATOM | 204 | P | G | A | 215 | 102.424 165.386 332.159 | 1.00 | 0.00 | P |
| ATOM | 205 | P | A | A | 216 | 103.251 171.526 329.129 | 1.00 | 0.00 | P |
| ATOM | 206 | P | G | A | 217 | 100.491 167.510 325.540 | 1.00 | 0.00 | P |
| ATOM | 207 | P | A | A | 218 | 102.626 163.548 322.364 | 1.00 | 0.00 | P |
| ATOM | 208 | P | G | A | 219 | 105.339 160.858 317.741 | 1.00 | 0.00 | P |
| ATOM | 209 | P | G | A | 220 | 107.517 158.773 312.764 | 1.00 | 0.00 | P |
| ATOM | 210 | P | A | A | 221 | 113.252 157.071 312.934 | 1.00 | 0.00 | P |
| ATOM | 211 | P | A | A | 222 | 114.881 152.331 309.794 | 1.00 | 0.00 | P |
| ATOM | 212 | P | A | A | 223 | 109.791 152.699 307.052 | 1.00 | 0.00 | P |
| ATOM | 213 | P | G | A | 224 | 109.208 149.597 301.354 | 1.00 | 0.00 | P |
| ATOM | 214 | P | A | A | 225 | 106.246 154.577 300.010 | 1.00 | 0.00 | P |
| ATOM | 215 | P | G | A | 226 | 104.567 158.265 295.781 | 1.00 | 0.00 | P |
| ATOM | 216 | P | A | A | 227 | 105.859 160.677 290.346 | 1.00 | 0.00 | P |
| ATOM | 217 | P | A | A | 228 | 108.811 159.758 285.181 | 1.00 | 0.00 | P |
| ATOM | 218 | P | A | A | 229 | 115.394 159.988 285.827 | 1.00 | 0.00 | P |
| ATOM | 219 | P | U | A | 230 | 117.811 161.766 290.445 | 1.00 | 0.00 | P |
| ATOM | 220 | P | C | A | 231 | 116.772 163.765 296.629 | 1.00 | 0.00 | P |
| ATOM | 221 | P | G | A | 232 | 114.983 165.361 300.321 | 1.00 | 0.00 | P |
| ATOM | 222 | P | A | A | 233 | 114.998 162.829 304.972 | 1.00 | 0.00 | P |
| ATOM | 223 | P | C | A | 234 | 111.620 160.491 306.261 | 1.00 | 0.00 | P |
| ATOM | 224 | P | U | A | 235 | 106.304 160.876 308.569 | 1.00 | 0.00 | P |
| ATOM | 225 | P | C | A | 236 | 101.228 164.683 310.666 | 1.00 | 0.00 | P |
| ATOM | 226 | P | C | A | 237 | 98.885 170.635 309.996 | 1.00 | 0.00 | P |
| ATOM | 227 | P | C | A | 238 | 97.559 176.616 307.095 | 1.00 | 0.00 | P |
| ATOM | 228 | P | U | A | 239 | 96.647 178.736 301.858 | 1.00 | 0.00 | P |

| | | | | | | | | | | |
|---|---|---|---|---|---|---|---|---|---|---|
| ATOM | 229 | P | G | A | 240 | 96.603 176.792 295.618 | 1.00 | 0.00 | | P |
| ATOM | 230 | P | A | A | 241 | 96.584 172.440 291.483 | 1.00 | 0.00 | | P |
| ATOM | 231 | P | G | A | 242 | 91.215 174.982 293.753 | 1.00 | 0.00 | | P |
| ATOM | 232 | P | U | A | 243 | 88.661 170.235 291.251 | 1.00 | 0.00 | | P |
| ATOM | 233 | P | A | A | 244 | 91.303 167.321 287.228 | 1.00 | 0.00 | | P |
| ATOM | 234 | P | G | A | 245 | 93.424 162.858 291.017 | 1.00 | 0.00 | | P |
| ATOM | 235 | P | C | A | 246 | 86.609 161.211 291.825 | 1.00 | 0.00 | | P |
| ATOM | 236 | P | G | A | 247 | 82.841 155.805 292.403 | 1.00 | 0.00 | | P |
| ATOM | 237 | P | G | A | 248 | 76.895 155.337 292.152 | 1.00 | 0.00 | | P |
| ATOM | 238 | P | C | A | 249 | 73.330 156.563 287.839 | 1.00 | 0.00 | | P |
| ATOM | 239 | P | G | A | 250 | 76.042 162.403 286.485 | 1.00 | 0.00 | | P |
| ATOM | 240 | P | A | A | 251 | 74.547 166.561 291.048 | 1.00 | 0.00 | | P |
| ATOM | 241 | P | G | A | 252 | 75.000 169.527 296.247 | 1.00 | 0.00 | | P |
| ATOM | 242 | P | C | A | 253 | 80.184 168.119 300.566 | 1.00 | 0.00 | | P |
| ATOM | 243 | P | G | A | 254 | 84.887 165.661 302.644 | 1.00 | 0.00 | | P |
| ATOM | 244 | P | A | A | 255 | 90.676 166.461 301.652 | 1.00 | 0.00 | | P |
| ATOM | 245 | P | A | A | 256 | 97.037 165.742 301.695 | 1.00 | 0.00 | | P |
| ATOM | 246 | P | A | A | 257 | 102.058 163.692 300.244 | 1.00 | 0.00 | | P |
| ATOM | 247 | P | G | A | 258 | 107.337 164.665 298.840 | 1.00 | 0.00 | | P |
| ATOM | 248 | P | G | A | 259 | 110.598 169.563 296.230 | 1.00 | 0.00 | | P |
| ATOM | 249 | P | G | A | 260 | 111.686 175.921 297.970 | 1.00 | 0.00 | | P |
| ATOM | 250 | P | G | A | 261 | 111.604 177.705 303.572 | 1.00 | 0.00 | | P |
| ATOM | 251 | P | A | A | 262 | 112.293 177.994 309.391 | 1.00 | 0.00 | | P |
| ATOM | 252 | P | C | A | 263 | 112.516 176.558 314.694 | 1.00 | 0.00 | | P |
| ATOM | 253 | P | C | A | 264 | 115.154 172.448 317.117 | 1.00 | 0.00 | | P |
| ATOM | 254 | P | A | A | 265 | 118.166 167.533 317.545 | 1.00 | 0.00 | | P |
| ATOM | 255 | P | G | A | 266 | 118.733 162.287 313.432 | 1.00 | 0.00 | | P |
| ATOM | 256 | P | C | A | 267 | 122.107 156.952 316.667 | 1.00 | 0.00 | | P |
| ATOM | 257 | P | C | A | 268 | 120.306 152.206 321.291 | 1.00 | 0.00 | | P |
| ATOM | 258 | P | U | A | 269 | 118.302 147.904 324.113 | 1.00 | 0.00 | | P |
| ATOM | 259 | P | A | A | 270 | 118.212 142.384 324.172 | 1.00 | 0.00 | | P |
| ATOM | 260 | P | A | A | 270A | 114.475 138.441 321.492 | 1.00 | 0.00 | | P |
| ATOM | 261 | P | A | A | 270B | 116.381 133.884 318.309 | 1.00 | 0.00 | | P |
| ATOM | 262 | P | C | A | 270C | 120.767 130.072 315.634 | 1.00 | 0.00 | | P |
| ATOM | 263 | P | C | A | 270D | 126.669 128.399 317.072 | 1.00 | 0.00 | | P |
| ATOM | 264 | P | G | A | 270E | 130.592 127.658 321.848 | 1.00 | 0.00 | | P |
| ATOM | 265 | P | U | A | 270F | 131.014 127.442 327.489 | 1.00 | 0.00 | | P |
| ATOM | 266 | P | C | A | 270G | 129.011 125.930 333.365 | 1.00 | 0.00 | | P |
| ATOM | 267 | P | C | A | 270H | 123.952 125.147 337.082 | 1.00 | 0.00 | | P |
| ATOM | 268 | P | G | A | 270I | 118.757 123.482 338.017 | 1.00 | 0.00 | | P |
| ATOM | 269 | P | G | A | 270J | 116.009 119.852 337.543 | 1.00 | 0.00 | | P |
| ATOM | 270 | P | C | A | 270K | 112.877 116.907 332.874 | 1.00 | 0.00 | | P |
| ATOM | 271 | P | U | A | 270L | 114.180 111.676 330.796 | 1.00 | 0.00 | | P |
| ATOM | 272 | P | U | A | 270M | 120.325 111.577 330.603 | 1.00 | 0.00 | | P |
| ATOM | 273 | P | G | A | 270N | 124.160 111.638 325.174 | 1.00 | 0.00 | | P |
| ATOM | 274 | P | U | A | 270O | 121.739 115.071 319.956 | 1.00 | 0.00 | | P |
| ATOM | 275 | P | C | A | 270P | 118.355 119.485 318.235 | 1.00 | 0.00 | | P |
| ATOM | 276 | P | C | A | 270Q | 115.289 122.662 320.399 | 1.00 | 0.00 | | P |
| ATOM | 277 | P | G | A | 270R | 112.629 126.879 323.289 | 1.00 | 0.00 | | P |
| ATOM | 278 | P | G | A | 270S | 112.163 131.320 326.656 | 1.00 | 0.00 | | P |
| ATOM | 279 | P | G | A | 270T | 114.390 135.639 330.066 | 1.00 | 0.00 | | P |
| ATOM | 280 | P | C | A | 270U | 119.552 138.541 332.196 | 1.00 | 0.00 | | P |
| ATOM | 281 | P | G | A | 270V | 123.862 141.514 330.747 | 1.00 | 0.00 | | P |
| ATOM | 282 | P | G | A | 270W | 128.062 142.992 326.576 | 1.00 | 0.00 | | P |
| ATOM | 283 | P | G | A | 270X | 129.463 142.709 320.939 | 1.00 | 0.00 | | P |
| ATOM | 284 | P | G | A | 270Y | 126.796 142.468 315.245 | 1.00 | 0.00 | | P |
| ATOM | 285 | P | U | A | 270Z | 122.868 145.846 314.753 | 1.00 | 0.00 | | P |
| ATOM | 286 | P | C | A | 271A | 120.880 149.696 312.393 | 1.00 | 0.00 | | P |
| ATOM | 287 | P | G | A | 271B | 122.330 150.379 307.922 | 1.00 | 0.00 | | P |
| ATOM | 288 | P | U | A | 271C | 122.457 147.562 304.880 | 1.00 | 0.00 | | P |
| ATOM | 289 | P | G | A | 271 | 126.161 144.285 303.637 | 1.00 | 0.00 | | P |
| ATOM | 290 | P | G | A | 272 | 127.382 144.618 308.430 | 1.00 | 0.00 | | P |
| ATOM | 291 | P | G | A | 273 | 129.021 141.501 313.464 | 1.00 | 0.00 | | P |
| ATOM | 292 | P | G | A | 273A | 131.289 137.684 315.260 | 1.00 | 0.00 | | P |
| ATOM | 293 | P | C | A | 273B | 134.172 132.851 316.383 | 1.00 | 0.00 | | P |
| ATOM | 294 | P | C | A | 273C | 139.370 131.204 314.129 | 1.00 | 0.00 | | P |
| ATOM | 295 | P | C | A | 273D | 143.783 132.485 312.163 | 1.00 | 0.00 | | P |
| ATOM | 296 | P | U | A | 273E | 147.595 136.532 308.936 | 1.00 | 0.00 | | P |
| ATOM | 297 | P | C | A | 273F | 148.985 143.798 308.597 | 1.00 | 0.00 | | P |
| ATOM | 298 | P | G | A | 274 | 147.809 149.584 311.628 | 1.00 | 0.00 | | P |
| ATOM | 299 | P | G | A | 275 | 145.243 152.651 316.316 | 1.00 | 0.00 | | P |
| ATOM | 300 | P | A | A | 276 | 144.347 155.973 322.009 | 1.00 | 0.00 | | P |
| ATOM | 301 | P | C | A | 277 | 139.478 160.698 320.577 | 1.00 | 0.00 | | P |
| ATOM | 302 | P | A | A | 278 | 133.233 163.947 321.512 | 1.00 | 0.00 | | P |
| ATOM | 303 | P | C | A | 279 | 126.809 162.339 323.683 | 1.00 | 0.00 | | P |
| ATOM | 304 | P | C | A | 280 | 121.108 164.326 324.560 | 1.00 | 0.00 | | P |
| ATOM | 305 | P | G | A | 281 | 115.721 163.771 323.492 | 1.00 | 0.00 | | P |
| ATOM | 306 | P | A | A | 282 | 113.567 162.897 327.975 | 1.00 | 0.00 | | P |
| ATOM | 307 | P | A | A | 283 | 114.962 161.481 333.006 | 1.00 | 0.00 | | P |
| ATOM | 308 | P | U | A | 284 | 119.275 162.490 338.335 | 1.00 | 0.00 | | P |
| ATOM | 309 | P | C | A | 285 | 123.637 165.384 340.933 | 1.00 | 0.00 | | P |
| ATOM | 310 | P | C | A | 286 | 126.405 171.350 342.377 | 1.00 | 0.00 | | P |
| ATOM | 311 | P | C | A | 287 | 125.255 176.919 342.233 | 1.00 | 0.00 | | P |
| ATOM | 312 | P | C | A | 288 | 121.772 182.216 340.817 | 1.00 | 0.00 | | P |
| ATOM | 313 | P | A | A | 289 | 116.460 183.893 336.648 | 1.00 | 0.00 | | P |
| ATOM | 314 | P | G | A | 290 | 110.526 184.818 335.833 | 1.00 | 0.00 | | P |
| ATOM | 315 | P | C | A | 291 | 105.430 184.250 338.698 | 1.00 | 0.00 | | P |

```
ATOM  316  P  C A 292  102.731 184.527 343.676  1.00  0.00           P
ATOM  317  P  U A 293  102.738 187.345 347.938  1.00  0.00           P
ATOM  318  P  A A 294  105.068 191.689 348.486  1.00  0.00           P
ATOM  319  P  G A 295  106.711 195.460 348.696  1.00  0.00           P
ATOM  320  P  C A 296  109.476 200.864 348.775  1.00  0.00           P
ATOM  321  P  C A 297  111.770 205.890 348.286  1.00  0.00           P
ATOM  322  P  G A 298  112.144 206.762 342.558  1.00  0.00           P
ATOM  323  P  A A 299  110.108 211.580 341.350  1.00  0.00           P
ATOM  324  P  A A 300  109.676 217.195 341.652  1.00  0.00           P
ATOM  325  P  G A 301  106.307 221.165 344.494  1.00  0.00           P
ATOM  326  P  C A 302  102.718 225.935 347.919  1.00  0.00           P
ATOM  327  P  U A 303   98.140 229.829 350.328  1.00  0.00           P
ATOM  328  P  G A 304   94.298 234.130 350.149  1.00  0.00           P
ATOM  329  P  U A 305   89.274 236.554 348.553  1.00  0.00           P
ATOM  330  P  U A 306   84.060 235.744 346.493  1.00  0.00           P
ATOM  331  P  G A 307   79.657 232.372 345.890  1.00  0.00           P
ATOM  332  P  G A 308   77.652 227.650 348.027  1.00  0.00           P
ATOM  333  P  G A 309   82.714 225.485 349.839  1.00  0.00           P
ATOM  334  P  A A 310   87.722 223.119 348.467  1.00  0.00           P
ATOM  335  P  A A 311   92.306 221.502 343.188  1.00  0.00           P
ATOM  336  P  G A 312   91.286 223.386 337.447  1.00  0.00           P
ATOM  337  P  C A 313   90.406 227.604 333.941  1.00  0.00           P
ATOM  338  P  A A 314   92.067 232.757 332.886  1.00  0.00           P
ATOM  339  P  G A 315   96.691 236.115 334.526  1.00  0.00           P
ATOM  340  P  C A 316  101.969 236.158 336.694  1.00  0.00           P
ATOM  341  P  G A 317  106.855 233.672 338.162  1.00  0.00           P
ATOM  342  P  C A 318  110.185 227.918 338.300  1.00  0.00           P
ATOM  343  P  C A 319  112.242 222.439 337.481  1.00  0.00           P
ATOM  344  P  A A 320  113.615 217.143 335.586  1.00  0.00           P
ATOM  345  P  G A 321  114.113 213.971 331.747  1.00  0.00           P
ATOM  346  P  A A 322  109.901 211.201 328.755  1.00  0.00           P
ATOM  347  P  G A 323  103.642 210.428 331.153  1.00  0.00           P
ATOM  348  P  A A 324  101.355 210.701 326.776  1.00  0.00           P
ATOM  349  P  G A 325   96.582 206.769 329.598  1.00  0.00           P
ATOM  350  P  G A 326   91.751 204.654 332.823  1.00  0.00           P
ATOM  351  P  G A 327   88.278 204.444 337.589  1.00  0.00           P
ATOM  352  P  U A 328   86.793 206.530 342.936  1.00  0.00           P
ATOM  353  P  G A 329   85.781 211.797 345.380  1.00  0.00           P
ATOM  354  P  A A 330   79.350 212.656 342.759  1.00  0.00           P
ATOM  355  P  A A 331   82.276 216.672 337.916  1.00  0.00           P
ATOM  356  P  A A 332   86.640 216.723 335.301  1.00  0.00           P
ATOM  357  P  G A 333   90.817 216.739 337.914  1.00  0.00           P
ATOM  358  P  C A 334   96.945 214.331 338.314  1.00  0.00           P
ATOM  359  P  C A 335   97.750 218.216 343.252  1.00  0.00           P
ATOM  360  P  C A 336   98.028 214.136 347.096  1.00  0.00           P
ATOM  361  P  C A 337   99.787 208.076 348.780  1.00  0.00           P
ATOM  362  P  G A 338  101.423 202.530 346.800  1.00  0.00           P
ATOM  363  P  U A 339  102.783 201.816 342.739  1.00  0.00           P
ATOM  364  P  A A 340  102.302 201.423 336.770  1.00  0.00           P
ATOM  365  P  G A 341  105.043 201.472 332.841  1.00  0.00           P
ATOM  366  P  G A 342  110.247 201.587 330.676  1.00  0.00           P
ATOM  367  P  C A 343  115.746 200.410 332.389  1.00  0.00           P
ATOM  368  P  G A 344  117.732 197.511 337.039  1.00  0.00           P
ATOM  369  P  A A 345  118.497 193.640 340.928  1.00  0.00           P
ATOM  370  P  A A 346  118.206 190.341 344.208  1.00  0.00           P
ATOM  371  P  A A 347  119.174 186.495 346.727  1.00  0.00           P
ATOM  372  P  G A 348  118.711 180.932 349.854  1.00  0.00           P
ATOM  373  P  G A 349  115.924 175.873 351.020  1.00  0.00           P
ATOM  374  P  U A 350  113.245 172.603 348.857  1.00  0.00           P
ATOM  375  P  G A 351  110.940 169.818 343.212  1.00  0.00           P
ATOM  376  P  G A 352  109.348 170.264 337.458  1.00  0.00           P
ATOM  377  P  G A 353  111.154 173.332 332.097  1.00  0.00           P
ATOM  378  P  G A 354  114.475 176.906 327.555  1.00  0.00           P
ATOM  379  P  G A 355  119.809 177.382 326.057  1.00  0.00           P
ATOM  380  P  G A 356  125.345 176.267 326.293  1.00  0.00           P
ATOM  381  P  A A 357  129.244 171.477 330.372  1.00  0.00           P
ATOM  382  P  U A 358  131.528 165.497 331.127  1.00  0.00           P
ATOM  383  P  A A 359  130.339 159.745 332.720  1.00  0.00           P
ATOM  384  P  G A 360  126.236 155.783 330.323  1.00  0.00           P
ATOM  385  P  G A 361  127.911 154.532 325.947  1.00  0.00           P
ATOM  386  P  U A 362  130.699 154.353 321.591  1.00  0.00           P
ATOM  387  P  G A 363  132.064 153.680 316.857  1.00  0.00           P
ATOM  388  P  A A 363A 134.682 151.399 313.143  1.00  0.00           P
ATOM  389  P  G A 363B 136.190 150.178 307.895  1.00  0.00           P
ATOM  390  P  G A 363C 136.270 146.480 303.985  1.00  0.00           P
ATOM  391  P  G A 363D 136.680 142.763 299.673  1.00  0.00           P
ATOM  392  P  U A 363E 135.886 135.279 298.668  1.00  0.00           P
ATOM  393  P  A A 363F 133.274 129.576 299.517  1.00  0.00           P
ATOM  394  P  C A 364  126.507 127.852 300.892  1.00  0.00           P
ATOM  395  P  C A 365  122.427 126.651 304.719  1.00  0.00           P
ATOM  396  P  C A 366  118.595 129.384 307.970  1.00  0.00           P
ATOM  397  P  G A 370  117.367 134.375 312.358  1.00  0.00           P
ATOM  398  P  A A 371  110.541 137.319 312.346  1.00  0.00           P
ATOM  399  P  G A 372  104.021 133.414 314.717  1.00  0.00           P
ATOM  400  P  U A 373   99.182 132.375 310.467  1.00  0.00           P
ATOM  401  P  A A 374  100.281 137.510 308.022  1.00  0.00           P
ATOM  402  P  C A 375  101.557 139.852 303.523  1.00  0.00           P
```

| | | | | | | | | | | |
|---|---|---|---|---|---|---|---|---|---|---|
| ATOM | 403 | P | C | A | 376 | 98.766 138.090 298.456 | 1.00 | 0.00 | P |
| ATOM | 404 | P | C | A | 377 | 94.510 135.602 295.567 | 1.00 | 0.00 | P |
| ATOM | 405 | P | C | A | 378 | 89.240 133.967 294.253 | 1.00 | 0.00 | P |
| ATOM | 406 | P | G | A | 379 | 84.265 135.025 297.616 | 1.00 | 0.00 | P |
| ATOM | 407 | P | U | A | 380 | 80.086 137.999 301.567 | 1.00 | 0.00 | P |
| ATOM | 408 | P | G | A | 381 | 80.922 143.091 304.088 | 1.00 | 0.00 | P |
| ATOM | 409 | P | G | A | 382 | 81.755 148.336 304.832 | 1.00 | 0.00 | P |
| ATOM | 410 | P | U | A | 383 | 84.123 151.763 307.187 | 1.00 | 0.00 | P |
| ATOM | 411 | P | U | A | 384 | 87.846 154.217 306.813 | 1.00 | 0.00 | P |
| ATOM | 412 | P | C | A | 385 | 89.462 158.351 303.384 | 1.00 | 0.00 | P |
| ATOM | 413 | P | G | A | 386 | 90.022 155.992 298.789 | 1.00 | 0.00 | P |
| ATOM | 414 | P | U | A | 387 | 92.788 152.243 296.174 | 1.00 | 0.00 | P |
| ATOM | 415 | P | G | A | 388 | 94.902 152.032 290.988 | 1.00 | 0.00 | P |
| ATOM | 416 | P | G | A | 389 | 92.077 148.121 292.382 | 1.00 | 0.00 | P |
| ATOM | 417 | P | A | A | 390 | 96.007 146.456 294.130 | 1.00 | 0.00 | P |
| ATOM | 418 | P | G | A | 391 | 98.136 148.189 299.878 | 1.00 | 0.00 | P |
| ATOM | 419 | P | C | A | 392 | 98.243 147.888 303.787 | 1.00 | 0.00 | P |
| ATOM | 420 | P | C | A | 393 | 96.999 146.294 307.796 | 1.00 | 0.00 | P |
| ATOM | 421 | P | A | A | 394 | 95.583 142.864 312.208 | 1.00 | 0.00 | P |
| ATOM | 422 | P | U | A | 395 | 92.882 138.738 313.462 | 1.00 | 0.00 | P |
| ATOM | 423 | P | G | A | 396 | 91.364 133.935 313.696 | 1.00 | 0.00 | P |
| ATOM | 424 | P | G | A | 397 | 90.113 128.405 311.949 | 1.00 | 0.00 | P |
| ATOM | 425 | P | G | A | 398 | 91.579 123.831 308.249 | 1.00 | 0.00 | P |
| ATOM | 426 | P | G | A | 399 | 95.499 122.115 304.059 | 1.00 | 0.00 | P |
| ATOM | 427 | P | G | A | 400 | 100.112 124.667 303.014 | 1.00 | 0.00 | P |
| ATOM | 428 | P | A | A | 401 | 104.004 127.313 303.028 | 1.00 | 0.00 | P |
| ATOM | 429 | P | A | A | 402 | 109.215 127.015 302.098 | 1.00 | 0.00 | P |
| ATOM | 430 | P | U | A | 403 | 114.341 130.345 303.977 | 1.00 | 0.00 | P |
| ATOM | 431 | P | C | A | 404 | 118.569 135.265 303.563 | 1.00 | 0.00 | P |
| ATOM | 432 | P | U | A | 405 | 121.344 136.843 298.241 | 1.00 | 0.00 | P |
| ATOM | 433 | P | G | A | 406 | 115.967 135.844 294.964 | 1.00 | 0.00 | P |
| ATOM | 434 | P | G | A | 407 | 110.816 136.944 297.357 | 1.00 | 0.00 | P |
| ATOM | 435 | P | G | A | 408 | 106.396 140.918 299.611 | 1.00 | 0.00 | P |
| ATOM | 436 | P | C | A | 409 | 103.815 142.867 296.502 | 1.00 | 0.00 | P |
| ATOM | 437 | P | G | A | 410 | 101.132 147.282 293.605 | 1.00 | 0.00 | P |
| ATOM | 438 | P | G | A | 411 | 99.953 150.230 289.428 | 1.00 | 0.00 | P |
| ATOM | 439 | P | A | A | 412 | 95.605 146.050 288.206 | 1.00 | 0.00 | P |
| ATOM | 440 | P | C | A | 413 | 100.014 140.189 286.292 | 1.00 | 0.00 | P |
| ATOM | 441 | P | C | A | 414 | 104.723 137.558 283.968 | 1.00 | 0.00 | P |
| ATOM | 442 | P | A | A | 415 | 110.690 139.562 283.054 | 1.00 | 0.00 | P |
| ATOM | 443 | P | C | A | 416 | 114.655 144.167 283.574 | 1.00 | 0.00 | P |
| ATOM | 444 | P | C | A | 417 | 117.401 149.229 287.252 | 1.00 | 0.00 | P |
| ATOM | 445 | P | G | A | 418 | 117.523 153.296 292.585 | 1.00 | 0.00 | P |
| ATOM | 446 | P | C | A | 419 | 118.431 154.521 298.402 | 1.00 | 0.00 | P |
| ATOM | 447 | P | C | A | 420 | 119.492 152.312 304.058 | 1.00 | 0.00 | P |
| ATOM | 448 | P | U | A | 421 | 119.270 147.492 309.781 | 1.00 | 0.00 | P |
| ATOM | 449 | P | A | A | 422 | 115.712 141.568 310.939 | 1.00 | 0.00 | P |
| ATOM | 450 | P | A | A | 423 | 109.359 140.165 310.849 | 1.00 | 0.00 | P |
| ATOM | 451 | P | G | A | 424 | 106.168 140.165 314.880 | 1.00 | 0.00 | P |
| ATOM | 452 | P | G | A | 425 | 105.905 145.559 318.351 | 1.00 | 0.00 | P |
| ATOM | 453 | P | C | A | 426 | 106.527 150.377 321.528 | 1.00 | 0.00 | P |
| ATOM | 454 | P | U | A | 427 | 107.422 155.560 324.052 | 1.00 | 0.00 | P |
| ATOM | 455 | P | A | A | 428 | 108.820 161.397 323.186 | 1.00 | 0.00 | P |
| ATOM | 456 | P | A | A | 429 | 108.365 167.087 324.733 | 1.00 | 0.00 | P |
| ATOM | 457 | P | G | A | 430 | 107.064 171.947 322.234 | 1.00 | 0.00 | P |
| ATOM | 458 | P | U | A | 431 | 103.691 174.346 318.691 | 1.00 | 0.00 | P |
| ATOM | 459 | P | A | A | 432 | 98.794 175.729 316.715 | 1.00 | 0.00 | P |
| ATOM | 460 | P | C | A | 433 | 92.577 174.365 317.974 | 1.00 | 0.00 | P |
| ATOM | 461 | P | U | A | 434 | 87.654 176.125 322.024 | 1.00 | 0.00 | P |
| ATOM | 462 | P | C | A | 435 | 87.229 177.211 329.177 | 1.00 | 0.00 | P |
| ATOM | 463 | P | C | A | 436 | 91.639 176.602 334.453 | 1.00 | 0.00 | P |
| ATOM | 464 | P | G | A | 438 | 94.843 181.287 337.064 | 1.00 | 0.00 | P |
| ATOM | 465 | P | G | A | 439 | 96.984 186.611 337.496 | 1.00 | 0.00 | P |
| ATOM | 466 | P | G | A | 440 | 97.571 191.450 334.934 | 1.00 | 0.00 | P |
| ATOM | 467 | P | U | A | 441 | 96.209 195.803 331.136 | 1.00 | 0.00 | P |
| ATOM | 468 | P | G | A | 442 | 92.531 197.558 324.786 | 1.00 | 0.00 | P |
| ATOM | 469 | P | A | A | 443 | 89.197 197.958 319.564 | 1.00 | 0.00 | P |
| ATOM | 470 | P | C | A | 444 | 85.008 195.514 321.620 | 1.00 | 0.00 | P |
| ATOM | 471 | P | C | A | 445 | 80.007 197.210 323.743 | 1.00 | 0.00 | P |
| ATOM | 472 | P | G | A | 446 | 76.792 198.842 327.089 | 1.00 | 0.00 | P |
| ATOM | 473 | P | A | A | 447 | 73.622 199.879 332.929 | 1.00 | 0.00 | P |
| ATOM | 474 | P | U | A | 448 | 68.427 195.935 333.969 | 1.00 | 0.00 | P |
| ATOM | 475 | P | A | A | 449 | 69.293 191.334 329.069 | 1.00 | 0.00 | P |
| ATOM | 476 | P | G | A | 450 | 73.893 190.755 326.259 | 1.00 | 0.00 | P |
| ATOM | 477 | P | C | A | 451 | 78.029 187.537 327.520 | 1.00 | 0.00 | P |
| ATOM | 478 | P | G | A | 452 | 73.873 183.411 329.675 | 1.00 | 0.00 | P |
| ATOM | 479 | P | C | A | 453 | 72.381 186.412 334.164 | 1.00 | 0.00 | P |
| ATOM | 480 | P | A | A | 454 | 74.430 189.045 338.438 | 1.00 | 0.00 | P |
| ATOM | 481 | P | C | A | 455 | 77.618 190.008 344.317 | 1.00 | 0.00 | P |
| ATOM | 482 | P | C | A | 456 | 73.176 188.616 349.262 | 1.00 | 0.00 | P |
| ATOM | 483 | P | A | A | 457 | 74.440 183.923 346.551 | 1.00 | 0.00 | P |
| ATOM | 484 | P | G | A | 458 | 76.360 179.556 342.907 | 1.00 | 0.00 | P |
| ATOM | 485 | P | U | A | 459 | 70.809 175.758 343.848 | 1.00 | 0.00 | P |
| ATOM | 486 | P | A | A | 460 | 67.142 177.178 347.982 | 1.00 | 0.00 | P |
| ATOM | 487 | P | C | A | 461 | 61.875 177.571 347.007 | 1.00 | 0.00 | P |
| ATOM | 488 | P | C | A | 462 | 58.013 174.877 343.522 | 1.00 | 0.00 | P |
| ATOM | 489 | P | G | A | 463 | 55.343 170.984 341.322 | 1.00 | 0.00 | P |

| | | | | | | | | | |
|---|---|---|---|---|---|---|---|---|---|
| ATOM | 490 | P | U | A | 464 | 55.279 | 165.594 | 340.272 | 1.00 | 0.00 | P |
| ATOM | 491 | P | G | A | 465 | 60.826 | 164.832 | 341.974 | 1.00 | 0.00 | P |
| ATOM | 492 | P | A | A | 466 | 66.273 | 164.191 | 339.343 | 1.00 | 0.00 | P |
| ATOM | 493 | P | G | A | 467 | 70.095 | 165.193 | 335.398 | 1.00 | 0.00 | P |
| ATOM | 494 | P | G | A | 468 | 68.720 | 170.910 | 332.204 | 1.00 | 0.00 | P |
| ATOM | 495 | P | G | A | 469 | 66.446 | 176.211 | 331.916 | 1.00 | 0.00 | P |
| ATOM | 496 | P | A | A | 470 | 67.323 | 181.161 | 334.536 | 1.00 | 0.00 | P |
| ATOM | 497 | P | A | A | 471 | 65.513 | 185.526 | 337.982 | 1.00 | 0.00 | P |
| ATOM | 498 | P | A | A | 472 | 66.107 | 190.790 | 341.831 | 1.00 | 0.00 | P |
| ATOM | 499 | P | G | A | 473 | 68.192 | 196.027 | 341.424 | 1.00 | 0.00 | P |
| ATOM | 500 | P | G | A | 474 | 71.216 | 199.266 | 345.344 | 1.00 | 0.00 | P |
| ATOM | 501 | P | U | A | 475 | 72.957 | 204.848 | 347.368 | 1.00 | 0.00 | P |
| ATOM | 502 | P | G | A | 476 | 73.673 | 209.999 | 347.087 | 1.00 | 0.00 | P |
| ATOM | 503 | P | A | A | 477 | 78.461 | 212.502 | 348.321 | 1.00 | 0.00 | P |
| ATOM | 504 | P | A | A | 478 | 81.740 | 210.481 | 352.148 | 1.00 | 0.00 | P |
| ATOM | 505 | P | A | A | 479 | 80.259 | 208.286 | 357.149 | 1.00 | 0.00 | P |
| ATOM | 506 | P | A | A | 480 | 77.703 | 207.790 | 361.598 | 1.00 | 0.00 | P |
| ATOM | 507 | P | G | A | 481 | 73.159 | 210.913 | 361.782 | 1.00 | 0.00 | P |
| ATOM | 508 | P | A | A | 482 | 69.231 | 206.956 | 360.799 | 1.00 | 0.00 | P |
| ATOM | 509 | P | A | A | 483 | 66.810 | 211.559 | 365.029 | 1.00 | 0.00 | P |
| ATOM | 510 | P | C | A | 484 | 66.056 | 212.412 | 370.754 | 1.00 | 0.00 | P |
| ATOM | 511 | P | C | A | 485 | 61.259 | 213.149 | 373.460 | 1.00 | 0.00 | P |
| ATOM | 512 | P | C | A | 486 | 55.697 | 214.822 | 373.352 | 1.00 | 0.00 | P |
| ATOM | 513 | P | C | A | 487 | 50.294 | 213.867 | 372.125 | 1.00 | 0.00 | P |
| ATOM | 514 | P | G | A | 488 | 47.252 | 209.876 | 368.683 | 1.00 | 0.00 | P |
| ATOM | 515 | P | G | A | 489 | 46.491 | 204.559 | 368.458 | 1.00 | 0.00 | P |
| ATOM | 516 | P | G | A | 491 | 50.843 | 201.935 | 365.322 | 1.00 | 0.00 | P |
| ATOM | 517 | P | A | A | 492 | 53.386 | 203.159 | 360.898 | 1.00 | 0.00 | P |
| ATOM | 518 | P | G | A | 493 | 54.983 | 205.570 | 355.419 | 1.00 | 0.00 | P |
| ATOM | 519 | P | G | A | 494 | 55.896 | 210.218 | 355.873 | 1.00 | 0.00 | P |
| ATOM | 520 | P | G | A | 495 | 55.629 | 216.842 | 356.853 | 1.00 | 0.00 | P |
| ATOM | 521 | P | G | A | 496 | 58.908 | 221.047 | 360.854 | 1.00 | 0.00 | P |
| ATOM | 522 | P | A | A | 497 | 63.923 | 222.571 | 363.829 | 1.00 | 0.00 | P |
| ATOM | 523 | P | G | A | 498 | 69.860 | 222.261 | 363.018 | 1.00 | 0.00 | P |
| ATOM | 524 | P | U | A | 499 | 74.788 | 220.645 | 360.335 | 1.00 | 0.00 | P |
| ATOM | 525 | P | G | A | 500 | 77.978 | 219.595 | 356.034 | 1.00 | 0.00 | P |
| ATOM | 526 | P | A | A | 501 | 78.056 | 221.105 | 350.677 | 1.00 | 0.00 | P |
| ATOM | 527 | P | A | A | 502 | 72.626 | 222.246 | 350.660 | 1.00 | 0.00 | P |
| ATOM | 528 | P | A | A | 503 | 67.151 | 220.464 | 350.446 | 1.00 | 0.00 | P |
| ATOM | 529 | P | U | A | 504 | 62.687 | 216.434 | 351.462 | 1.00 | 0.00 | P |
| ATOM | 530 | P | A | A | 505 | 63.867 | 216.994 | 344.595 | 1.00 | 0.00 | P |
| ATOM | 531 | P | G | A | 506 | 64.729 | 212.003 | 347.731 | 1.00 | 0.00 | P |
| ATOM | 532 | P | A | A | 507 | 63.791 | 207.860 | 353.351 | 1.00 | 0.00 | P |
| ATOM | 533 | P | G | A | 508 | 63.436 | 201.238 | 352.288 | 1.00 | 0.00 | P |
| ATOM | 534 | P | C | A | 509 | 60.823 | 203.334 | 346.698 | 1.00 | 0.00 | P |
| ATOM | 535 | P | C | A | 510 | 63.966 | 204.933 | 340.697 | 1.00 | 0.00 | P |
| ATOM | 536 | P | U | A | 511 | 67.671 | 208.332 | 344.744 | 1.00 | 0.00 | P |
| ATOM | 537 | P | G | A | 512 | 65.824 | 211.900 | 340.850 | 1.00 | 0.00 | P |
| ATOM | 538 | P | A | A | 513 | 60.628 | 209.246 | 337.311 | 1.00 | 0.00 | P |
| ATOM | 539 | P | A | A | 514 | 57.428 | 210.621 | 332.897 | 1.00 | 0.00 | P |
| ATOM | 540 | P | A | A | 515 | 53.016 | 208.697 | 329.714 | 1.00 | 0.00 | P |
| ATOM | 541 | P | C | A | 516 | 48.268 | 205.720 | 329.979 | 1.00 | 0.00 | P |
| ATOM | 542 | P | C | A | 517 | 44.374 | 205.106 | 334.285 | 1.00 | 0.00 | P |
| ATOM | 543 | P | G | A | 518 | 41.652 | 206.490 | 338.616 | 1.00 | 0.00 | P |
| ATOM | 544 | P | U | A | 519 | 41.487 | 211.668 | 342.803 | 1.00 | 0.00 | P |
| ATOM | 545 | P | G | A | 520 | 40.026 | 217.174 | 344.696 | 1.00 | 0.00 | P |
| ATOM | 546 | P | G | A | 521 | 40.301 | 223.618 | 343.981 | 1.00 | 0.00 | P |
| ATOM | 547 | P | G | A | 522 | 38.746 | 228.092 | 340.156 | 1.00 | 0.00 | P |
| ATOM | 548 | P | C | A | 523 | 35.876 | 230.622 | 334.040 | 1.00 | 0.00 | P |
| ATOM | 549 | P | U | A | 524 | 33.969 | 228.051 | 327.601 | 1.00 | 0.00 | P |
| ATOM | 550 | P | U | A | 525 | 31.706 | 221.387 | 328.842 | 1.00 | 0.00 | P |
| ATOM | 551 | P | A | A | 526 | 27.128 | 221.003 | 332.257 | 1.00 | 0.00 | P |
| ATOM | 552 | P | C | A | 527 | 24.950 | 221.186 | 327.800 | 1.00 | 0.00 | P |
| ATOM | 553 | P | A | A | 528 | 19.487 | 220.631 | 326.286 | 1.00 | 0.00 | P |
| ATOM | 554 | P | A | A | 529 | 19.571 | 217.490 | 321.759 | 1.00 | 0.00 | P |
| ATOM | 555 | P | G | A | 530 | 24.223 | 214.857 | 318.292 | 1.00 | 0.00 | P |
| ATOM | 556 | P | C | A | 531 | 28.547 | 212.344 | 316.206 | 1.00 | 0.00 | P |
| ATOM | 557 | P | A | A | 532 | 34.324 | 212.108 | 316.608 | 1.00 | 0.00 | P |
| ATOM | 558 | P | G | A | 533 | 38.751 | 213.619 | 317.715 | 1.00 | 0.00 | P |
| ATOM | 559 | P | U | A | 534 | 40.587 | 217.158 | 313.716 | 1.00 | 0.00 | P |
| ATOM | 560 | P | C | A | 535 | 40.797 | 221.670 | 309.264 | 1.00 | 0.00 | P |
| ATOM | 561 | P | A | A | 536 | 38.425 | 226.733 | 307.162 | 1.00 | 0.00 | P |
| ATOM | 562 | P | C | A | 537 | 36.047 | 230.844 | 308.304 | 1.00 | 0.00 | P |
| ATOM | 563 | P | G | A | 539 | 35.049 | 234.366 | 312.089 | 1.00 | 0.00 | P |
| ATOM | 564 | P | G | A | 540 | 32.513 | 235.564 | 316.582 | 1.00 | 0.00 | P |
| ATOM | 565 | P | C | A | 541 | 32.043 | 236.010 | 323.283 | 1.00 | 0.00 | P |
| ATOM | 566 | P | C | A | 542 | 35.323 | 236.887 | 328.961 | 1.00 | 0.00 | P |
| ATOM | 567 | P | C | A | 543 | 40.450 | 238.289 | 331.629 | 1.00 | 0.00 | P |
| ATOM | 568 | P | C | A | 544 | 46.256 | 239.766 | 331.582 | 1.00 | 0.00 | P |
| ATOM | 569 | P | G | A | 545 | 50.891 | 242.913 | 328.199 | 1.00 | 0.00 | P |
| ATOM | 570 | P | C | A | 546 | 53.246 | 246.237 | 324.951 | 1.00 | 0.00 | P |
| ATOM | 571 | P | A | A | 547 | 48.613 | 247.391 | 321.710 | 1.00 | 0.00 | P |
| ATOM | 572 | P | A | A | 548 | 46.241 | 245.562 | 316.265 | 1.00 | 0.00 | P |
| ATOM | 573 | P | G | A | 549 | 45.335 | 241.633 | 312.386 | 1.00 | 0.00 | P |
| ATOM | 574 | P | G | A | 550 | 47.034 | 235.479 | 314.760 | 1.00 | 0.00 | P |
| ATOM | 575 | P | G | A | 551 | 49.276 | 231.089 | 319.279 | 1.00 | 0.00 | P |
| ATOM | 576 | P | G | A | 552 | 46.891 | 228.116 | 323.677 | 1.00 | 0.00 | P |

| | | | | | | | | | |
|---|---|---|---|---|---|---|---|---|---|
| ATOM | 577 | P | U | A | 553 | 42.925 223.519 323.542 | 1.00 | 0.00 | P |
| ATOM | 578 | P | U | A | 554 | 36.871 222.899 324.436 | 1.00 | 0.00 | P |
| ATOM | 579 | P | G | A | 556 | 31.213 223.053 323.868 | 1.00 | 0.00 | P |
| ATOM | 580 | P | U | A | 557 | 26.247 223.453 320.633 | 1.00 | 0.00 | P |
| ATOM | 581 | P | G | A | 558 | 23.584 223.711 315.002 | 1.00 | 0.00 | P |
| ATOM | 582 | P | G | A | 559 | 23.670 222.986 309.707 | 1.00 | 0.00 | P |
| ATOM | 583 | P | C | A | 560 | 25.659 220.212 304.968 | 1.00 | 0.00 | P |
| ATOM | 584 | P | G | A | 561 | 30.569 217.422 303.961 | 1.00 | 0.00 | P |
| ATOM | 585 | P | U | A | 562 | 33.164 210.954 305.122 | 1.00 | 0.00 | P |
| ATOM | 586 | P | G | A | 563 | 37.190 204.879 307.162 | 1.00 | 0.00 | P |
| ATOM | 587 | P | C | A | 564 | 41.476 203.984 310.676 | 1.00 | 0.00 | P |
| ATOM | 588 | P | C | A | 565 | 47.307 200.785 311.689 | 1.00 | 0.00 | P |
| ATOM | 589 | P | U | A | 566 | 49.743 196.675 308.553 | 1.00 | 0.00 | P |
| ATOM | 590 | P | A | A | 567 | 49.728 191.839 305.121 | 1.00 | 0.00 | P |
| ATOM | 591 | P | U | A | 568 | 46.284 189.301 300.644 | 1.00 | 0.00 | P |
| ATOM | 592 | P | U | A | 569 | 43.770 191.723 296.318 | 1.00 | 0.00 | P |
| ATOM | 593 | P | G | A | 570 | 41.404 195.421 298.837 | 1.00 | 0.00 | P |
| ATOM | 594 | P | A | A | 571 | 38.767 197.168 303.248 | 1.00 | 0.00 | P |
| ATOM | 595 | P | A | A | 572 | 36.861 198.615 308.500 | 1.00 | 0.00 | P |
| ATOM | 596 | P | G | A | 573 | 36.263 194.720 311.498 | 1.00 | 0.00 | P |
| ATOM | 597 | P | C | A | 574 | 31.892 190.980 309.057 | 1.00 | 0.00 | P |
| ATOM | 598 | P | A | A | 575 | 35.847 188.059 306.938 | 1.00 | 0.00 | P |
| ATOM | 599 | P | U | A | 576 | 39.447 187.944 310.724 | 1.00 | 0.00 | P |
| ATOM | 600 | P | G | A | 577 | 42.789 187.382 313.833 | 1.00 | 0.00 | P |
| ATOM | 601 | P | A | A | 578 | 45.785 189.585 319.025 | 1.00 | 0.00 | P |
| ATOM | 602 | P | G | A | 579 | 46.159 191.241 324.901 | 1.00 | 0.00 | P |
| ATOM | 603 | P | C | A | 580 | 45.677 196.715 323.204 | 1.00 | 0.00 | P |
| ATOM | 604 | P | C | A | 581 | 48.586 201.295 323.227 | 1.00 | 0.00 | P |
| ATOM | 605 | P | G | A | 582 | 54.017 204.119 324.741 | 1.00 | 0.00 | P |
| ATOM | 606 | P | G | A | 583 | 59.989 203.572 325.645 | 1.00 | 0.00 | P |
| ATOM | 607 | P | C | A | 584 | 64.697 199.133 324.740 | 1.00 | 0.00 | P |
| ATOM | 608 | P | G | A | 585 | 65.961 194.369 321.197 | 1.00 | 0.00 | P |
| ATOM | 609 | P | A | A | 586 | 65.817 191.661 316.682 | 1.00 | 0.00 | P |
| ATOM | 610 | P | C | A | 587 | 67.561 191.895 310.819 | 1.00 | 0.00 | P |
| ATOM | 611 | P | U | A | 588 | 72.709 191.860 307.050 | 1.00 | 0.00 | P |
| ATOM | 612 | P | C | A | 589 | 78.081 191.083 308.464 | 1.00 | 0.00 | P |
| ATOM | 613 | P | A | A | 590 | 83.315 189.049 307.470 | 1.00 | 0.00 | P |
| ATOM | 614 | P | C | A | 591 | 87.417 186.035 304.798 | 1.00 | 0.00 | P |
| ATOM | 615 | P | G | A | 592 | 88.826 183.271 299.967 | 1.00 | 0.00 | P |
| ATOM | 616 | P | G | A | 593 | 87.247 182.062 294.428 | 1.00 | 0.00 | P |
| ATOM | 617 | P | U | A | 594 | 84.302 183.238 289.614 | 1.00 | 0.00 | P |
| ATOM | 618 | P | C | A | 595 | 80.612 187.992 286.239 | 1.00 | 0.00 | P |
| ATOM | 619 | P | G | A | 596 | 79.772 193.248 284.771 | 1.00 | 0.00 | P |
| ATOM | 620 | P | U | A | 597 | 79.295 198.903 285.348 | 1.00 | 0.00 | P |
| ATOM | 621 | P | G | A | 598 | 81.160 203.973 287.280 | 1.00 | 0.00 | P |
| ATOM | 622 | P | G | A | 599 | 85.713 207.281 289.359 | 1.00 | 0.00 | P |
| ATOM | 623 | P | G | A | 600 | 92.740 206.171 290.876 | 1.00 | 0.00 | P |
| ATOM | 624 | P | C | A | 601 | 99.080 203.854 290.521 | 1.00 | 0.00 | P |
| ATOM | 625 | P | G | A | 602 | 102.121 200.747 285.340 | 1.00 | 0.00 | P |
| ATOM | 626 | P | A | A | 603 | 103.777 198.133 279.869 | 1.00 | 0.00 | P |
| ATOM | 627 | P | G | A | 604 | 104.748 192.706 281.990 | 1.00 | 0.00 | P |
| ATOM | 628 | P | C | A | 605 | 101.564 196.356 287.746 | 1.00 | 0.00 | P |
| ATOM | 629 | P | U | A | 606 | 99.242 196.521 292.754 | 1.00 | 0.00 | P |
| ATOM | 630 | P | U | A | 607 | 100.054 195.062 298.553 | 1.00 | 0.00 | P |
| ATOM | 631 | P | A | A | 608 | 100.733 189.385 301.354 | 1.00 | 0.00 | P |
| ATOM | 632 | P | A | A | 609 | 98.881 186.637 305.793 | 1.00 | 0.00 | P |
| ATOM | 633 | P | G | A | 609A | 102.684 181.879 307.936 | 1.00 | 0.00 | P |
| ATOM | 634 | P | C | A | 610 | 107.983 181.142 312.304 | 1.00 | 0.00 | P |
| ATOM | 635 | P | C | A | 611 | 112.681 184.823 314.311 | 1.00 | 0.00 | P |
| ATOM | 636 | P | G | A | 612 | 113.762 190.204 315.570 | 1.00 | 0.00 | P |
| ATOM | 637 | P | U | A | 613 | 112.865 195.686 317.027 | 1.00 | 0.00 | P |
| ATOM | 638 | P | U | A | 614 | 108.364 198.686 320.361 | 1.00 | 0.00 | P |
| ATOM | 639 | P | G | A | 615 | 103.457 200.268 320.560 | 1.00 | 0.00 | P |
| ATOM | 640 | P | A | A | 616 | 102.663 200.986 315.193 | 1.00 | 0.00 | P |
| ATOM | 641 | P | G | A | 617 | 102.852 199.501 309.285 | 1.00 | 0.00 | P |
| ATOM | 642 | P | G | A | 618 | 107.691 199.087 305.730 | 1.00 | 0.00 | P |
| ATOM | 643 | P | C | A | 618A | 110.157 195.708 302.253 | 1.00 | 0.00 | P |
| ATOM | 644 | P | G | A | 619 | 112.433 190.431 300.791 | 1.00 | 0.00 | P |
| ATOM | 645 | P | G | A | 620 | 111.555 186.250 297.560 | 1.00 | 0.00 | P |
| ATOM | 646 | P | A | A | 621 | 110.250 180.980 295.275 | 1.00 | 0.00 | P |
| ATOM | 647 | P | G | A | 622 | 104.990 179.844 293.223 | 1.00 | 0.00 | P |
| ATOM | 648 | P | G | A | 623 | 99.945 178.796 291.876 | 1.00 | 0.00 | P |
| ATOM | 649 | P | C | A | 624 | 95.240 180.056 289.413 | 1.00 | 0.00 | P |
| ATOM | 650 | P | G | A | 625 | 93.514 185.126 286.408 | 1.00 | 0.00 | P |
| ATOM | 651 | P | U | A | 626 | 95.567 186.287 281.750 | 1.00 | 0.00 | P |
| ATOM | 652 | P | A | A | 627 | 97.748 185.945 275.149 | 1.00 | 0.00 | P |
| ATOM | 653 | P | A | A | 628 | 94.620 179.744 275.095 | 1.00 | 0.00 | P |
| ATOM | 654 | P | G | A | 629 | 88.927 176.605 272.485 | 1.00 | 0.00 | P |
| ATOM | 655 | P | G | A | 630 | 86.990 171.650 270.967 | 1.00 | 0.00 | P |
| ATOM | 656 | P | A | A | 631 | 87.757 166.278 271.525 | 1.00 | 0.00 | P |
| ATOM | 657 | P | A | A | 632 | 93.278 166.079 273.891 | 1.00 | 0.00 | P |
| ATOM | 658 | P | A | A | 633 | 99.046 165.184 271.688 | 1.00 | 0.00 | P |
| ATOM | 659 | P | C | A | 634 | 102.880 165.760 267.578 | 1.00 | 0.00 | P |
| ATOM | 660 | P | C | A | 635 | 102.129 170.755 263.586 | 1.00 | 0.00 | P |
| ATOM | 661 | P | G | A | 636 | 105.755 176.366 263.731 | 1.00 | 0.00 | P |
| ATOM | 662 | P | A | A | 637 | 101.491 181.165 263.537 | 1.00 | 0.00 | P |
| ATOM | 663 | P | G | A | 638 | 97.969 179.895 260.186 | 1.00 | 0.00 | P |

```
ATOM    664  P    U A 639      97.391 175.760 264.301  1.00  0.00           P
ATOM    665  P    C A 640      95.124 171.237 266.419  1.00  0.00           P
ATOM    666  P    C A 641      90.528 167.132 265.797  1.00  0.00           P
ATOM    667  P    G A 642      86.620 164.528 262.898  1.00  0.00           P
ATOM    668  P    A A 643      85.605 163.422 257.542  1.00  0.00           P
ATOM    669  P    A A 644      90.506 163.124 253.688  1.00  0.00           P
ATOM    670  P    C A 645      90.950 168.884 250.669  1.00  0.00           P
ATOM    671  P    A A 646      89.046 175.536 250.081  1.00  0.00           P
ATOM    672  P    G A 647      83.814 179.200 253.157  1.00  0.00           P
ATOM    673  P    G A 648      80.788 179.366 259.174  1.00  0.00           P
ATOM    674  P    G A 649      79.714 179.360 264.256  1.00  0.00           P
ATOM    675  P    C A 650      81.946 180.714 269.338  1.00  0.00           P
ATOM    676  P    G A 651      85.358 183.551 273.760  1.00  0.00           P
ATOM    677  P    C A 652      88.583 186.864 269.262  1.00  0.00           P
ATOM    678  P    A A 653      93.284 188.082 266.819  1.00  0.00           P
ATOM    679  P    A A 654      93.294 193.069 268.043  1.00  0.00           P
ATOM    680  P    A A 655      91.493 194.432 275.187  1.00  0.00           P
ATOM    681  P    G A 656      89.823 192.062 280.713  1.00  0.00           P
ATOM    682  P    U A 657      92.236 189.421 285.725  1.00  0.00           P
ATOM    683  P    C A 658      93.359 189.868 291.416  1.00  0.00           P
ATOM    684  P    C A 659      92.190 192.740 296.608  1.00  0.00           P
ATOM    685  P    G A 660      89.392 196.095 300.233  1.00  0.00           P
ATOM    686  P    C A 661      84.063 197.633 301.856  1.00  0.00           P
ATOM    687  P    G A 662      78.147 197.544 301.589  1.00  0.00           P
ATOM    688  P    G A 663      73.313 194.813 298.820  1.00  0.00           P
ATOM    689  P    C A 664      70.245 190.721 296.815  1.00  0.00           P
ATOM    690  P    C A 665      71.402 184.771 294.820  1.00  0.00           P
ATOM    691  P    G A 666      73.102 179.151 295.071  1.00  0.00           P
ATOM    692  P    U A 667      74.847 175.513 299.879  1.00  0.00           P
ATOM    693  P    G A 668      75.716 173.134 304.298  1.00  0.00           P
ATOM    694  P    G A 669      74.359 176.849 311.455  1.00  0.00           P
ATOM    695  P    A A 670      69.408 179.189 305.789  1.00  0.00           P
ATOM    696  P    C A 671      67.809 186.262 304.394  1.00  0.00           P
ATOM    697  P    C A 672      67.601 186.162 310.174  1.00  0.00           P
ATOM    698  P    C A 673      64.117 184.098 314.505  1.00  0.00           P
ATOM    699  P    G A 674      61.847 180.357 317.829  1.00  0.00           P
ATOM    700  P    A A 675      58.069 175.025 317.315  1.00  0.00           P
ATOM    701  P    A A 676      54.009 167.666 316.948  1.00  0.00           P
ATOM    702  P    A A 677      56.681 162.211 315.058  1.00  0.00           P
ATOM    703  P    C A 678      61.601 158.274 314.904  1.00  0.00           P
ATOM    704  P    C A 679      66.252 155.672 316.821  1.00  0.00           P
ATOM    705  P    G A 680      70.885 154.919 320.737  1.00  0.00           P
ATOM    706  P    G A 681      73.841 154.867 325.508  1.00  0.00           P
ATOM    707  P    G A 682      72.102 155.588 331.323  1.00  0.00           P
ATOM    708  P    C A 683      69.061 156.860 336.694  1.00  0.00           P
ATOM    709  P    G A 684      64.903 157.417 340.017  1.00  0.00           P
ATOM    710  P    A A 685      60.316 155.014 339.855  1.00  0.00           P
ATOM    711  P    G A 686      57.094 152.359 343.666  1.00  0.00           P
ATOM    712  P    C A 687      53.224 155.123 346.227  1.00  0.00           P
ATOM    713  P    U A 688      47.936 154.507 342.878  1.00  0.00           P
ATOM    714  P    A A 689      46.442 149.997 339.849  1.00  0.00           P
ATOM    715  P    G A 690      46.121 145.238 337.955  1.00  0.00           P
ATOM    716  P    C A 691      48.942 140.432 338.848  1.00  0.00           P
ATOM    717  P    C A 692      52.655 136.840 341.443  1.00  0.00           P
ATOM    718  P    C A 693      55.906 135.185 346.697  1.00  0.00           P
ATOM    719  P    U A 694      57.228 134.591 352.855  1.00  0.00           P
ATOM    720  P    G A 695      55.395 136.085 358.562  1.00  0.00           P
ATOM    721  P    G A 696      49.523 137.946 361.022  1.00  0.00           P
ATOM    722  P    C A 697      44.143 140.145 362.171  1.00  0.00           P
ATOM    723  P    C A 698      37.300 142.350 360.829  1.00  0.00           P
ATOM    724  P    A A 699      31.792 141.749 357.987  1.00  0.00           P
ATOM    725  P    G A 700      28.436 140.129 363.381  1.00  0.00           P
ATOM    726  P    G A 701      22.528 137.413 362.953  1.00  0.00           P
ATOM    727  P    G A 702      18.088 133.939 360.558  1.00  0.00           P
ATOM    728  P    U A 703      14.824 130.877 355.386  1.00  0.00           P
ATOM    729  P    G A 704      15.012 126.481 351.657  1.00  0.00           P
ATOM    730  P    A A 705      19.329 120.954 351.723  1.00  0.00           P
ATOM    731  P    A A 706      21.731 116.509 349.747  1.00  0.00           P
ATOM    732  P    G A 707      25.869 113.610 351.401  1.00  0.00           P
ATOM    733  P    C A 708      27.292 110.389 355.838  1.00  0.00           P
ATOM    734  P    U A 709      24.649 107.644 360.351  1.00  0.00           P
ATOM    735  P    G A 710      20.443 105.390 363.708  1.00  0.00           P
ATOM    736  P    G A 711      15.101 102.858 364.079  1.00  0.00           P
ATOM    737  P    G A 712      10.788 100.387 361.257  1.00  0.00           P
ATOM    738  P    G A 713       8.765  97.771 356.406  1.00  0.00           P
ATOM    739  P    U A 714       9.691  95.262 351.350  1.00  0.00           P
ATOM    740  P    G A 715      13.402  91.859 349.373  1.00  0.00           P
ATOM    741  P    A A 716      18.519  91.771 350.096  1.00  0.00           P
ATOM    742  P    G A 717      20.504  96.884 346.969  1.00  0.00           P
ATOM    743  P    A A 718      19.673 102.161 345.760  1.00  0.00           P
ATOM    744  P    C A 719      19.475 107.025 346.386  1.00  0.00           P
ATOM    745  P    C A 720      14.349 109.668 346.807  1.00  0.00           P
ATOM    746  P    C A 721      10.571 112.520 349.922  1.00  0.00           P
ATOM    747  P    A A 722       8.816 115.244 354.779  1.00  0.00           P
ATOM    748  P    G A 723      10.472 117.829 359.821  1.00  0.00           P
ATOM    749  P    U A 724      15.069 119.531 363.893  1.00  0.00           P
ATOM    750  P    G A 725      20.901 120.446 364.344  1.00  0.00           P
```

```
ATOM    751  P    G A 726      25.676 121.936 361.732  1.00  0.00           P
ATOM    752  P    A A 727      28.707 125.075 356.700  1.00  0.00           P
ATOM    753  P    G A 728      32.020 126.156 351.632  1.00  0.00           P
ATOM    754  P    G A 729      30.361 129.229 345.705  1.00  0.00           P
ATOM    755  P    C A 730      27.853 133.314 344.104  1.00  0.00           P
ATOM    756  P    C A 731      22.730 134.317 345.756  1.00  0.00           P
ATOM    757  P    C A 732      19.389 137.796 347.969  1.00  0.00           P
ATOM    758  P    G A 733      19.590 142.876 349.974  1.00  0.00           P
ATOM    759  P    A A 734      22.502 147.089 353.035  1.00  0.00           P
ATOM    760  P    A A 735      26.256 150.468 355.718  1.00  0.00           P
ATOM    761  P    C A 736      32.574 152.580 356.369  1.00  0.00           P
ATOM    762  P    C A 737      36.516 152.274 351.395  1.00  0.00           P
ATOM    763  P    G A 738      36.959 151.598 345.221  1.00  0.00           P
ATOM    764  P    G A 739      34.685 151.893 339.590  1.00  0.00           P
ATOM    765  P    U A 740      29.942 153.595 336.081  1.00  0.00           P
ATOM    766  P    G A 741      25.040 154.702 333.266  1.00  0.00           P
ATOM    767  P    G A 742      20.525 158.465 332.888  1.00  0.00           P
ATOM    768  P    G A 743      19.806 165.276 334.734  1.00  0.00           P
ATOM    769  P    G A 744      20.896 171.606 337.091  1.00  0.00           P
ATOM    770  P    G A 745      25.156 174.584 339.388  1.00  0.00           P
ATOM    771  P    A A 746      29.487 177.056 337.312  1.00  0.00           P
ATOM    772  P    U A 747      33.008 177.897 333.498  1.00  0.00           P
ATOM    773  P    G A 748      36.422 180.389 339.371  1.00  0.00           P
ATOM    774  P    C A 749      33.223 177.424 343.526  1.00  0.00           P
ATOM    775  P    A A 750      37.537 173.460 344.376  1.00  0.00           P
ATOM    776  P    A A 751      41.381 172.175 340.733  1.00  0.00           P
ATOM    777  P    A A 752      40.080 166.947 338.543  1.00  0.00           P
ATOM    778  P    C A 753      36.151 163.430 341.184  1.00  0.00           P
ATOM    779  P    C A 754      32.527 164.687 345.899  1.00  0.00           P
ATOM    780  P    C A 755      27.816 164.837 348.676  1.00  0.00           P
ATOM    781  P    C A 756      22.606 162.358 349.291  1.00  0.00           P
ATOM    782  P    U A 757      18.636 158.080 348.030  1.00  0.00           P
ATOM    783  P    C A 758      17.905 152.799 345.381  1.00  0.00           P
ATOM    784  P    G A 759      21.330 148.274 342.977  1.00  0.00           P
ATOM    785  P    G A 760      24.443 143.037 343.753  1.00  0.00           P
ATOM    786  P    A A 761      28.830 140.529 347.734  1.00  0.00           P
ATOM    787  P    U A 762      30.534 135.958 349.679  1.00  0.00           P
ATOM    788  P    G A 763      32.461 132.956 346.636  1.00  0.00           P
ATOM    789  P    A A 764      36.529 134.751 343.005  1.00  0.00           P
ATOM    790  P    G A 765      38.972 137.667 345.698  1.00  0.00           P
ATOM    791  P    C A 766      39.179 143.401 346.419  1.00  0.00           P
ATOM    792  P    U A 767      42.466 147.150 348.359  1.00  0.00           P
ATOM    793  P    G A 768      47.086 149.310 351.405  1.00  0.00           P
ATOM    794  P    G A 769      52.344 151.330 352.768  1.00  0.00           P
ATOM    795  P    G A 770      58.322 150.328 352.438  1.00  0.00           P
ATOM    796  P    G A 771      62.639 147.962 350.216  1.00  0.00           P
ATOM    797  P    C A 772      64.034 145.727 344.164  1.00  0.00           P
ATOM    798  P    U A 773      64.521 145.747 338.646  1.00  0.00           P
ATOM    799  P    A A 774      63.737 147.197 333.488  1.00  0.00           P
ATOM    800  P    G A 775      63.993 150.649 328.822  1.00  0.00           P
ATOM    801  P    G A 776      61.806 153.158 323.869  1.00  0.00           P
ATOM    802  P    A A 777      61.237 146.994 321.402  1.00  0.00           P
ATOM    803  P    G A 778      57.808 144.406 326.527  1.00  0.00           P
ATOM    804  P    U A 779      55.381 142.922 332.055  1.00  0.00           P
ATOM    805  P    G A 780      49.528 141.667 332.849  1.00  0.00           P
ATOM    806  P    A A 781      44.647 140.688 332.131  1.00  0.00           P
ATOM    807  P    A A 782      40.137 142.768 329.286  1.00  0.00           P
ATOM    808  P    A A 783      37.939 144.055 323.051  1.00  0.00           P
ATOM    809  P    A A 784      39.322 148.192 320.573  1.00  0.00           P
ATOM    810  P    G A 785      40.694 153.000 323.331  1.00  0.00           P
ATOM    811  P    C A 786      43.399 154.984 328.694  1.00  0.00           P
ATOM    812  P    U A 787      47.522 156.465 332.394  1.00  0.00           P
ATOM    813  P    A A 788      52.431 158.163 334.139  1.00  0.00           P
ATOM    814  P    A A 789      47.853 162.068 333.604  1.00  0.00           P
ATOM    815  P    C A 790      45.362 160.135 329.055  1.00  0.00           P
ATOM    816  P    C A 791      47.775 158.601 325.191  1.00  0.00           P
ATOM    817  P    G A 792      48.668 155.892 319.166  1.00  0.00           P
ATOM    818  P    A A 793      55.252 154.594 318.720  1.00  0.00           P
ATOM    819  P    G A 794      58.554 156.051 323.431  1.00  0.00           P
ATOM    820  P    C A 795      56.623 160.283 326.422  1.00  0.00           P
ATOM    821  P    C A 796      59.084 164.792 329.338  1.00  0.00           P
ATOM    822  P    C A 797      63.247 168.255 330.123  1.00  0.00           P
ATOM    823  P    G A 798      68.525 170.345 327.734  1.00  0.00           P
ATOM    824  P    G A 799      72.816 170.216 323.661  1.00  0.00           P
ATOM    825  P    A A 800      74.252 169.594 318.130  1.00  0.00           P
ATOM    826  P    G A 801      70.935 174.486 321.182  1.00  0.00           P
ATOM    827  P    A A 802      69.460 171.258 316.031  1.00  0.00           P
ATOM    828  P    U A 803      66.871 173.259 312.225  1.00  0.00           P
ATOM    829  P    A A 804      64.095 173.950 306.701  1.00  0.00           P
ATOM    830  P    G A 805      60.196 176.181 303.795  1.00  0.00           P
ATOM    831  P    C A 806      54.976 177.361 300.523  1.00  0.00           P
ATOM    832  P    U A 807      50.887 179.765 303.893  1.00  0.00           P
ATOM    833  P    G A 808      49.354 184.422 307.370  1.00  0.00           P
ATOM    834  P    G A 809      50.619 189.229 310.090  1.00  0.00           P
ATOM    835  P    U A 810      54.370 193.971 310.913  1.00  0.00           P
ATOM    836  P    U A 811      58.334 198.316 310.636  1.00  0.00           P
ATOM    837  P    C A 812      60.703 203.569 309.774  1.00  0.00           P
```

| | | | | | | | | | | |
|---|---|---|---|---|---|---|---|---|---|---|
| ATOM | 838 | P | U | A | 813 | 61.812 | 208.182 | 306.909 | 1.00 | 0.00 | P |
| ATOM | 839 | P | C | A | 814 | 60.085 | 211.793 | 302.244 | 1.00 | 0.00 | P |
| ATOM | 840 | P | C | A | 815 | 59.720 | 213.709 | 296.868 | 1.00 | 0.00 | P |
| ATOM | 841 | P | C | A | 816 | 59.967 | 212.990 | 290.742 | 1.00 | 0.00 | P |
| ATOM | 842 | P | C | A | 817 | 59.204 | 210.055 | 286.250 | 1.00 | 0.00 | P |
| ATOM | 843 | P | G | A | 818 | 55.442 | 206.969 | 284.836 | 1.00 | 0.00 | P |
| ATOM | 844 | P | A | A | 819 | 54.161 | 200.782 | 286.697 | 1.00 | 0.00 | P |
| ATOM | 845 | P | A | A | 820 | 53.069 | 195.104 | 286.016 | 1.00 | 0.00 | P |
| ATOM | 846 | P | A | A | 821 | 50.572 | 191.350 | 284.787 | 1.00 | 0.00 | P |
| ATOM | 847 | P | U | A | 822 | 47.794 | 187.811 | 284.427 | 1.00 | 0.00 | P |
| ATOM | 848 | P | G | A | 823 | 48.075 | 184.226 | 280.485 | 1.00 | 0.00 | P |
| ATOM | 849 | P | A | A | 824 | 49.826 | 180.438 | 277.990 | 1.00 | 0.00 | P |
| ATOM | 850 | P | C | A | 825 | 53.225 | 175.931 | 276.877 | 1.00 | 0.00 | P |
| ATOM | 851 | P | U | A | 826 | 56.190 | 171.601 | 279.202 | 1.00 | 0.00 | P |
| ATOM | 852 | P | U | A | 827 | 57.983 | 168.786 | 283.864 | 1.00 | 0.00 | P |
| ATOM | 853 | P | U | A | 828 | 55.959 | 167.024 | 289.185 | 1.00 | 0.00 | P |
| ATOM | 854 | P | A | A | 829 | 54.136 | 171.473 | 291.907 | 1.00 | 0.00 | P |
| ATOM | 855 | P | G | A | 830 | 50.823 | 176.047 | 294.003 | 1.00 | 0.00 | P |
| ATOM | 856 | P | G | A | 831 | 55.017 | 179.362 | 295.201 | 1.00 | 0.00 | P |
| ATOM | 857 | P | G | A | 832 | 61.298 | 180.418 | 292.879 | 1.00 | 0.00 | P |
| ATOM | 858 | P | U | A | 833 | 65.671 | 180.375 | 288.529 | 1.00 | 0.00 | P |
| ATOM | 859 | P | C | A | 834 | 65.948 | 183.556 | 283.007 | 1.00 | 0.00 | P |
| ATOM | 860 | P | A | A | 835 | 64.094 | 187.044 | 278.295 | 1.00 | 0.00 | P |
| ATOM | 861 | P | G | A | 836 | 59.065 | 191.402 | 277.248 | 1.00 | 0.00 | P |
| ATOM | 862 | P | C | A | 837 | 57.681 | 194.721 | 280.101 | 1.00 | 0.00 | P |
| ATOM | 863 | P | C | A | 838 | 58.829 | 199.383 | 281.662 | 1.00 | 0.00 | P |
| ATOM | 864 | P | U | A | 839 | 62.095 | 202.919 | 284.164 | 1.00 | 0.00 | P |
| ATOM | 865 | P | C | A | 840 | 67.508 | 205.339 | 285.175 | 1.00 | 0.00 | P |
| ATOM | 866 | P | A | A | 841 | 73.072 | 206.047 | 283.775 | 1.00 | 0.00 | P |
| ATOM | 867 | P | G | A | 842 | 77.542 | 205.814 | 280.001 | 1.00 | 0.00 | P |
| ATOM | 868 | P | G | A | 843 | 79.661 | 205.243 | 274.664 | 1.00 | 0.00 | P |
| ATOM | 869 | P | C | A | 844 | 77.507 | 205.098 | 268.762 | 1.00 | 0.00 | P |
| ATOM | 870 | P | G | A | 845 | 72.625 | 208.053 | 265.348 | 1.00 | 0.00 | P |
| ATOM | 871 | P | C | A | 846 | 67.943 | 208.615 | 263.199 | 1.00 | 0.00 | P |
| ATOM | 872 | P | U | A | 847 | 63.967 | 205.383 | 264.591 | 1.00 | 0.00 | P |
| ATOM | 873 | P | G | A | 848 | 58.042 | 203.073 | 266.792 | 1.00 | 0.00 | P |
| ATOM | 874 | P | A | A | 849 | 52.284 | 201.116 | 266.471 | 1.00 | 0.00 | P |
| ATOM | 875 | P | C | A | 850 | 47.859 | 204.024 | 265.394 | 1.00 | 0.00 | P |
| ATOM | 876 | P | U | A | 851 | 45.510 | 206.386 | 260.448 | 1.00 | 0.00 | P |
| ATOM | 877 | P | G | A | 852 | 46.102 | 208.265 | 255.139 | 1.00 | 0.00 | P |
| ATOM | 878 | P | G | A | 853 | 46.495 | 205.565 | 249.283 | 1.00 | 0.00 | P |
| ATOM | 879 | P | G | A | 854 | 47.931 | 200.234 | 245.374 | 1.00 | 0.00 | P |
| ATOM | 880 | P | G | A | 855 | 50.136 | 194.446 | 243.882 | 1.00 | 0.00 | P |
| ATOM | 881 | P | C | A | 856 | 50.616 | 188.951 | 246.442 | 1.00 | 0.00 | P |
| ATOM | 882 | P | C | A | 857 | 47.783 | 185.708 | 249.132 | 1.00 | 0.00 | P |
| ATOM | 883 | P | U | A | 858 | 44.659 | 182.912 | 252.265 | 1.00 | 0.00 | P |
| ATOM | 884 | P | G | A | 859 | 39.852 | 181.805 | 255.994 | 1.00 | 0.00 | P |
| ATOM | 885 | P | U | A | 860 | 34.476 | 182.813 | 257.203 | 1.00 | 0.00 | P |
| ATOM | 886 | P | A | A | 861 | 29.223 | 185.686 | 258.460 | 1.00 | 0.00 | P |
| ATOM | 887 | P | G | A | 862 | 24.649 | 188.193 | 257.362 | 1.00 | 0.00 | P |
| ATOM | 888 | P | A | A | 863 | 21.468 | 188.011 | 252.431 | 1.00 | 0.00 | P |
| ATOM | 889 | P | G | A | 864 | 21.766 | 182.785 | 247.118 | 1.00 | 0.00 | P |
| ATOM | 890 | P | C | A | 865 | 24.066 | 177.488 | 245.198 | 1.00 | 0.00 | P |
| ATOM | 891 | P | A | A | 866 | 27.540 | 173.174 | 242.790 | 1.00 | 0.00 | P |
| ATOM | 892 | P | C | A | 867 | 29.455 | 168.027 | 245.918 | 1.00 | 0.00 | P |
| ATOM | 893 | P | U | A | 868 | 27.114 | 165.193 | 251.429 | 1.00 | 0.00 | P |
| ATOM | 894 | P | G | A | 869 | 21.918 | 164.535 | 254.840 | 1.00 | 0.00 | P |
| ATOM | 895 | P | A | A | 870 | 16.150 | 166.313 | 256.042 | 1.00 | 0.00 | P |
| ATOM | 896 | P | U | A | 871 | 10.981 | 169.473 | 254.959 | 1.00 | 0.00 | P |
| ATOM | 897 | P | A | A | 872 | 6.858 | 171.134 | 252.763 | 1.00 | 0.00 | P |
| ATOM | 898 | P | G | A | 873 | 3.461 | 169.933 | 247.818 | 1.00 | 0.00 | P |
| ATOM | 899 | P | G | A | 874 | 2.141 | 167.761 | 242.532 | 1.00 | 0.00 | P |
| ATOM | 900 | P | G | A | 875 | 2.788 | 166.178 | 236.972 | 1.00 | 0.00 | P |
| ATOM | 901 | P | C | A | 876 | 5.604 | 162.036 | 234.339 | 1.00 | 0.00 | P |
| ATOM | 902 | P | U | A | 877 | 8.095 | 157.137 | 234.306 | 1.00 | 0.00 | P |
| ATOM | 903 | P | A | A | 878 | 11.128 | 153.911 | 236.724 | 1.00 | 0.00 | P |
| ATOM | 904 | P | G | A | 879 | 12.842 | 150.339 | 239.810 | 1.00 | 0.00 | P |
| ATOM | 905 | P | G | A | 880 | 10.516 | 146.667 | 244.071 | 1.00 | 0.00 | P |
| ATOM | 906 | P | G | A | 881 | 6.482 | 145.893 | 248.025 | 1.00 | 0.00 | P |
| ATOM | 907 | P | G | A | 882 | 0.359 | 146.450 | 249.043 | 1.00 | 0.00 | P |
| ATOM | 908 | P | G | A | 883 | -4.522 | 144.378 | 246.540 | 1.00 | 0.00 | P |
| ATOM | 909 | P | C | A | 884 | -8.626 | 143.029 | 242.779 | 1.00 | 0.00 | P |
| ATOM | 910 | P | C | A | 885 | -7.856 | 140.090 | 236.699 | 1.00 | 0.00 | P |
| ATOM | 911 | P | C | A | 886 | -6.287 | 134.097 | 235.270 | 1.00 | 0.00 | P |
| ATOM | 912 | P | A | A | 887 | -2.995 | 131.441 | 234.239 | 1.00 | 0.00 | P |
| ATOM | 913 | P | C | A | 888 | 1.627 | 129.867 | 235.507 | 1.00 | 0.00 | P |
| ATOM | 914 | P | C | A | 889 | 5.111 | 133.476 | 234.262 | 1.00 | 0.00 | P |
| ATOM | 915 | P | A | A | 890 | 6.091 | 137.211 | 232.531 | 1.00 | 0.00 | P |
| ATOM | 916 | P | G | A | 892 | 6.919 | 141.413 | 232.614 | 1.00 | 0.00 | P |
| ATOM | 917 | P | C | A | 893 | 3.709 | 145.620 | 230.406 | 1.00 | 0.00 | P |
| ATOM | 918 | P | C | A | 894 | -0.160 | 150.754 | 230.690 | 1.00 | 0.00 | P |
| ATOM | 919 | P | U | A | 895 | -2.507 | 153.510 | 235.069 | 1.00 | 0.00 | P |
| ATOM | 920 | P | A | A | 896 | -5.910 | 153.587 | 238.034 | 1.00 | 0.00 | P |
| ATOM | 921 | P | C | A | 897 | -5.047 | 157.165 | 241.226 | 1.00 | 0.00 | P |
| ATOM | 922 | P | C | A | 898 | -4.459 | 159.717 | 245.529 | 1.00 | 0.00 | P |
| ATOM | 923 | P | A | A | 899 | 1.145 | 158.961 | 250.587 | 1.00 | 0.00 | P |
| ATOM | 924 | P | A | A | 900 | 7.808 | 158.730 | 249.175 | 1.00 | 0.00 | P |

| | | | | | | | | | | |
|---|---|---|---|---|---|---|---|---|---|---|
| ATOM | 925 | P | A | A | 901 | 14.410 | 159.841 | 247.432 | 1.00 | 0.00 | P |
| ATOM | 926 | P | C | A | 902 | 17.209 | 161.026 | 242.342 | 1.00 | 0.00 | P |
| ATOM | 927 | P | C | A | 903 | 18.341 | 165.655 | 238.821 | 1.00 | 0.00 | P |
| ATOM | 928 | P | C | A | 904 | 16.958 | 171.708 | 237.555 | 1.00 | 0.00 | P |
| ATOM | 929 | P | U | A | 905 | 14.338 | 176.198 | 238.288 | 1.00 | 0.00 | P |
| ATOM | 930 | P | G | A | 906 | 10.037 | 178.946 | 242.252 | 1.00 | 0.00 | P |
| ATOM | 931 | P | U | A | 907 | 10.620 | 180.779 | 247.955 | 1.00 | 0.00 | P |
| ATOM | 932 | P | C | A | 908 | 13.909 | 181.672 | 252.840 | 1.00 | 0.00 | P |
| ATOM | 933 | P | A | A | 909 | 20.346 | 180.487 | 255.839 | 1.00 | 0.00 | P |
| ATOM | 934 | P | A | A | 910 | 25.331 | 180.476 | 258.756 | 1.00 | 0.00 | P |
| ATOM | 935 | P | A | A | 911 | 28.762 | 176.802 | 259.177 | 1.00 | 0.00 | P |
| ATOM | 936 | P | C | A | 912 | 31.790 | 172.368 | 257.963 | 1.00 | 0.00 | P |
| ATOM | 937 | P | U | A | 913 | 33.550 | 175.179 | 252.911 | 1.00 | 0.00 | P |
| ATOM | 938 | P | C | A | 914 | 34.151 | 176.677 | 246.352 | 1.00 | 0.00 | P |
| ATOM | 939 | P | C | A | 915 | 35.494 | 180.988 | 242.713 | 1.00 | 0.00 | P |
| ATOM | 940 | P | G | A | 916 | 34.626 | 186.882 | 244.278 | 1.00 | 0.00 | P |
| ATOM | 941 | P | A | A | 917 | 36.081 | 190.477 | 248.463 | 1.00 | 0.00 | P |
| ATOM | 942 | P | A | A | 918 | 37.138 | 195.577 | 251.479 | 1.00 | 0.00 | P |
| ATOM | 943 | P | G | A | 919 | 37.629 | 199.829 | 255.659 | 1.00 | 0.00 | P |
| ATOM | 944 | P | G | A | 920 | 40.529 | 198.118 | 260.717 | 1.00 | 0.00 | P |
| ATOM | 945 | P | G | A | 921 | 45.164 | 195.352 | 263.161 | 1.00 | 0.00 | P |
| ATOM | 946 | P | U | A | 922 | 50.619 | 193.059 | 261.804 | 1.00 | 0.00 | P |
| ATOM | 947 | P | C | A | 923 | 55.907 | 192.366 | 260.660 | 1.00 | 0.00 | P |
| ATOM | 948 | P | C | A | 924 | 60.069 | 195.038 | 257.426 | 1.00 | 0.00 | P |
| ATOM | 949 | P | C | A | 925 | 62.219 | 199.571 | 254.090 | 1.00 | 0.00 | P |
| ATOM | 950 | P | A | A | 926 | 61.795 | 205.714 | 252.386 | 1.00 | 0.00 | P |
| ATOM | 951 | P | G | A | 928 | 58.902 | 211.435 | 254.585 | 1.00 | 0.00 | P |
| ATOM | 952 | P | G | A | 929 | 57.079 | 212.884 | 260.654 | 1.00 | 0.00 | P |
| ATOM | 953 | P | U | A | 930 | 58.799 | 214.568 | 266.658 | 1.00 | 0.00 | P |
| ATOM | 954 | P | G | A | 931 | 60.953 | 214.746 | 272.186 | 1.00 | 0.00 | P |
| ATOM | 955 | P | G | A | 932 | 58.546 | 212.680 | 277.083 | 1.00 | 0.00 | P |
| ATOM | 956 | P | A | A | 933 | 58.404 | 208.154 | 277.781 | 1.00 | 0.00 | P |
| ATOM | 957 | P | G | A | 934 | 59.421 | 204.547 | 273.250 | 1.00 | 0.00 | P |
| ATOM | 958 | P | C | A | 935 | 61.910 | 200.747 | 270.017 | 1.00 | 0.00 | P |
| ATOM | 959 | P | C | A | 936 | 66.100 | 196.023 | 269.653 | 1.00 | 0.00 | P |
| ATOM | 960 | P | U | A | 937 | 70.375 | 192.682 | 271.274 | 1.00 | 0.00 | P |
| ATOM | 961 | P | G | A | 938 | 73.745 | 190.618 | 275.504 | 1.00 | 0.00 | P |
| ATOM | 962 | P | G | A | 939 | 74.993 | 190.686 | 281.680 | 1.00 | 0.00 | P |
| ATOM | 963 | P | G | A | 940 | 73.971 | 191.068 | 287.260 | 1.00 | 0.00 | P |
| ATOM | 964 | P | A | A | 941 | 69.445 | 190.513 | 291.480 | 1.00 | 0.00 | P |
| ATOM | 965 | P | G | A | 942 | 63.681 | 191.275 | 294.244 | 1.00 | 0.00 | P |
| ATOM | 966 | P | U | A | 943 | 58.450 | 190.541 | 294.833 | 1.00 | 0.00 | P |
| ATOM | 967 | P | G | A | 944 | 54.271 | 188.128 | 292.047 | 1.00 | 0.00 | P |
| ATOM | 968 | P | A | A | 945 | 50.369 | 183.293 | 290.132 | 1.00 | 0.00 | P |
| ATOM | 969 | P | G | A | 946 | 44.685 | 184.197 | 288.033 | 1.00 | 0.00 | P |
| ATOM | 970 | P | G | A | 947 | 39.736 | 187.238 | 286.616 | 1.00 | 0.00 | P |
| ATOM | 971 | P | G | A | 948 | 34.795 | 190.205 | 286.639 | 1.00 | 0.00 | P |
| ATOM | 972 | P | C | A | 949 | 30.848 | 193.957 | 284.154 | 1.00 | 0.00 | P |
| ATOM | 973 | P | G | A | 950 | 28.429 | 196.550 | 279.859 | 1.00 | 0.00 | P |
| ATOM | 974 | P | C | A | 951 | 27.884 | 196.608 | 274.265 | 1.00 | 0.00 | P |
| ATOM | 975 | P | G | A | 952 | 28.316 | 193.352 | 269.667 | 1.00 | 0.00 | P |
| ATOM | 976 | P | A | A | 953 | 28.486 | 188.374 | 268.193 | 1.00 | 0.00 | P |
| ATOM | 977 | P | G | A | 954 | 29.060 | 182.794 | 269.482 | 1.00 | 0.00 | P |
| ATOM | 978 | P | C | A | 955 | 27.826 | 177.751 | 271.804 | 1.00 | 0.00 | P |
| ATOM | 979 | P | G | A | 956 | 26.937 | 174.097 | 277.484 | 1.00 | 0.00 | P |
| ATOM | 980 | P | A | A | 957 | 22.002 | 175.054 | 279.064 | 1.00 | 0.00 | P |
| ATOM | 981 | P | U | A | 958 | 18.704 | 177.583 | 276.594 | 1.00 | 0.00 | P |
| ATOM | 982 | P | A | A | 959 | 19.355 | 183.013 | 277.215 | 1.00 | 0.00 | P |
| ATOM | 983 | P | A | A | 960 | 22.971 | 185.217 | 282.605 | 1.00 | 0.00 | P |
| ATOM | 984 | P | C | A | 961 | 26.224 | 188.324 | 285.411 | 1.00 | 0.00 | P |
| ATOM | 985 | P | G | A | 962 | 29.347 | 186.882 | 288.247 | 1.00 | 0.00 | P |
| ATOM | 986 | P | U | A | 963 | 32.704 | 183.197 | 287.316 | 1.00 | 0.00 | P |
| ATOM | 987 | P | C | A | 964 | 37.042 | 180.645 | 284.928 | 1.00 | 0.00 | P |
| ATOM | 988 | P | C | A | 965 | 40.541 | 181.219 | 279.845 | 1.00 | 0.00 | P |
| ATOM | 989 | P | G | A | 966 | 42.655 | 184.939 | 275.093 | 1.00 | 0.00 | P |
| ATOM | 990 | P | C | A | 967 | 43.783 | 189.856 | 272.215 | 1.00 | 0.00 | P |
| ATOM | 991 | P | G | A | 968 | 44.267 | 195.589 | 272.089 | 1.00 | 0.00 | P |
| ATOM | 992 | P | U | A | 969 | 43.638 | 200.818 | 275.069 | 1.00 | 0.00 | P |
| ATOM | 993 | P | C | A | 970 | 42.381 | 204.746 | 279.407 | 1.00 | 0.00 | P |
| ATOM | 994 | P | C | A | 971 | 42.993 | 204.125 | 286.959 | 1.00 | 0.00 | P |
| ATOM | 995 | P | G | A | 972 | 42.380 | 201.054 | 291.923 | 1.00 | 0.00 | P |
| ATOM | 996 | P | A | A | 973 | 44.762 | 196.388 | 294.483 | 1.00 | 0.00 | P |
| ATOM | 997 | P | G | A | 974 | 49.158 | 199.755 | 294.093 | 1.00 | 0.00 | P |
| ATOM | 998 | P | C | A | 974A | 45.811 | 203.853 | 293.347 | 1.00 | 0.00 | P |
| ATOM | 999 | P | G | A | 975 | 41.364 | 206.418 | 292.706 | 1.00 | 0.00 | P |
| ATOM | 1000 | P | C | A | 976 | 39.830 | 211.697 | 296.195 | 1.00 | 0.00 | P |
| ATOM | 1001 | P | G | A | 977 | 36.248 | 215.084 | 293.715 | 1.00 | 0.00 | P |
| ATOM | 1002 | P | G | A | 978 | 31.275 | 216.367 | 292.524 | 1.00 | 0.00 | P |
| ATOM | 1003 | P | G | A | 979 | 26.049 | 213.550 | 291.160 | 1.00 | 0.00 | P |
| ATOM | 1004 | P | A | A | 980 | 22.677 | 208.664 | 291.941 | 1.00 | 0.00 | P |
| ATOM | 1005 | P | A | A | 981 | 27.074 | 209.307 | 295.492 | 1.00 | 0.00 | P |
| ATOM | 1006 | P | C | A | 982 | 30.516 | 206.015 | 299.028 | 1.00 | 0.00 | P |
| ATOM | 1007 | P | A | A | 983 | 34.604 | 202.735 | 297.670 | 1.00 | 0.00 | P |
| ATOM | 1008 | P | A | A | 984 | 34.593 | 201.683 | 291.356 | 1.00 | 0.00 | P |
| ATOM | 1009 | P | C | A | 985 | 34.972 | 199.536 | 285.095 | 1.00 | 0.00 | P |
| ATOM | 1010 | P | C | A | 986 | 32.465 | 203.382 | 282.098 | 1.00 | 0.00 | P |
| ATOM | 1011 | P | G | A | 987 | 33.572 | 209.334 | 279.548 | 1.00 | 0.00 | P |

| | | | | | | | | | |
|---|---|---|---|---|---|---|---|---|---|
| ATOM | 1012 | P | A | A 988 | 38.434 | 213.674 | 280.754 | 1.00 | 0.00 | P |
| ATOM | 1013 | P | G | A 989 | 42.827 | 214.892 | 282.604 | 1.00 | 0.00 | P |
| ATOM | 1014 | P | A | A 990 | 47.520 | 216.030 | 287.486 | 1.00 | 0.00 | P |
| ATOM | 1015 | P | C | A 991 | 49.687 | 216.962 | 293.658 | 1.00 | 0.00 | P |
| ATOM | 1016 | P | C | A 992 | 49.475 | 221.138 | 298.440 | 1.00 | 0.00 | P |
| ATOM | 1017 | P | G | A 993 | 46.575 | 226.175 | 300.870 | 1.00 | 0.00 | P |
| ATOM | 1018 | P | C | A 994 | 42.666 | 230.603 | 299.596 | 1.00 | 0.00 | P |
| ATOM | 1019 | P | C | A 995 | 39.283 | 233.013 | 301.369 | 1.00 | 0.00 | P |
| ATOM | 1020 | P | A | A 996 | 39.726 | 234.304 | 296.042 | 1.00 | 0.00 | P |
| ATOM | 1021 | P | G | A 997 | 35.890 | 235.228 | 291.182 | 1.00 | 0.00 | P |
| ATOM | 1022 | P | C | A 998 | 33.208 | 233.068 | 285.709 | 1.00 | 0.00 | P |
| ATOM | 1023 | P | U | A 999 | 32.345 | 229.089 | 281.539 | 1.00 | 0.00 | P |
| ATOM | 1024 | P | A | A1000 | 32.735 | 224.044 | 280.860 | 1.00 | 0.00 | P |
| ATOM | 1025 | P | A | A1001 | 30.160 | 219.281 | 279.282 | 1.00 | 0.00 | P |
| ATOM | 1026 | P | G | A1002 | 27.618 | 215.114 | 281.525 | 1.00 | 0.00 | P |
| ATOM | 1027 | P | G | A1003 | 22.622 | 215.685 | 285.214 | 1.00 | 0.00 | P |
| ATOM | 1028 | P | C | A1004 | 18.459 | 219.790 | 288.084 | 1.00 | 0.00 | P |
| ATOM | 1029 | P | C | A1005 | 14.817 | 223.945 | 288.792 | 1.00 | 0.00 | P |
| ATOM | 1030 | P | C | A1006 | 15.108 | 225.463 | 294.350 | 1.00 | 0.00 | P |
| ATOM | 1031 | P | C | A1007 | 16.615 | 224.687 | 299.492 | 1.00 | 0.00 | P |
| ATOM | 1032 | P | C | A1008 | 20.189 | 221.292 | 302.506 | 1.00 | 0.00 | P |
| ATOM | 1033 | P | A | A1009 | 21.134 | 225.613 | 298.102 | 1.00 | 0.00 | P |
| ATOM | 1034 | P | A | A1010 | 22.406 | 227.435 | 292.975 | 1.00 | 0.00 | P |
| ATOM | 1035 | P | G | A1011 | 18.961 | 232.042 | 289.852 | 1.00 | 0.00 | P |
| ATOM | 1036 | P | U | A1012 | 13.223 | 231.182 | 288.679 | 1.00 | 0.00 | P |
| ATOM | 1037 | P | C | A1013 | 9.116 | 229.348 | 285.883 | 1.00 | 0.00 | P |
| ATOM | 1038 | P | U | A1014 | 9.123 | 230.736 | 281.433 | 1.00 | 0.00 | P |
| ATOM | 1039 | P | G | A1015 | 7.081 | 231.577 | 276.190 | 1.00 | 0.00 | P |
| ATOM | 1040 | P | G | A1016 | 4.756 | 229.630 | 272.115 | 1.00 | 0.00 | P |
| ATOM | 1041 | P | G | A1017 | 2.033 | 224.532 | 270.129 | 1.00 | 0.00 | P |
| ATOM | 1042 | P | C | A1018 | 0.363 | 218.740 | 272.122 | 1.00 | 0.00 | P |
| ATOM | 1043 | P | U | A1019 | -1.009 | 213.118 | 273.485 | 1.00 | 0.00 | P |
| ATOM | 1044 | P | A | A1020 | -3.272 | 211.269 | 277.628 | 1.00 | 0.00 | P |
| ATOM | 1045 | P | A | A1021 | -5.127 | 210.921 | 283.696 | 1.00 | 0.00 | P |
| ATOM | 1046 | P | G | A1022 | -1.929 | 207.357 | 287.969 | 1.00 | 0.00 | P |
| ATOM | 1047 | P | U | A1023 | 2.578 | 207.735 | 290.745 | 1.00 | 0.00 | P |
| ATOM | 1048 | P | G | A1024 | 8.128 | 209.099 | 291.215 | 1.00 | 0.00 | P |
| ATOM | 1049 | P | G | A1025 | 8.656 | 207.571 | 285.711 | 1.00 | 0.00 | P |
| ATOM | 1050 | P | U | A1026 | 7.426 | 203.319 | 289.647 | 1.00 | 0.00 | P |
| ATOM | 1051 | P | A | A1027 | 8.458 | 198.823 | 287.162 | 1.00 | 0.00 | P |
| ATOM | 1052 | P | A | A1028 | 6.522 | 196.143 | 281.510 | 1.00 | 0.00 | P |
| ATOM | 1053 | P | A | A1029 | 5.069 | 192.864 | 278.022 | 1.00 | 0.00 | P |
| ATOM | 1054 | P | G | A1030 | 2.144 | 188.843 | 273.901 | 1.00 | 0.00 | P |
| ATOM | 1055 | P | G | A1031 | -4.689 | 189.393 | 273.140 | 1.00 | 0.00 | P |
| ATOM | 1056 | P | A | A1032 | -9.570 | 192.528 | 273.042 | 1.00 | 0.00 | P |
| ATOM | 1057 | P | U | A1033 | -11.841 | 197.644 | 271.026 | 1.00 | 0.00 | P |
| ATOM | 1058 | P | G | A1034 | -11.572 | 202.171 | 275.171 | 1.00 | 0.00 | P |
| ATOM | 1059 | P | U | A1035 | -12.000 | 209.339 | 274.878 | 1.00 | 0.00 | P |
| ATOM | 1060 | P | G | A1036 | -8.493 | 214.051 | 272.509 | 1.00 | 0.00 | P |
| ATOM | 1061 | P | G | A1037 | -5.437 | 216.655 | 267.586 | 1.00 | 0.00 | P |
| ATOM | 1062 | P | C | A1038 | -2.570 | 215.748 | 261.605 | 1.00 | 0.00 | P |
| ATOM | 1063 | P | G | A1039 | -2.076 | 212.291 | 256.450 | 1.00 | 0.00 | P |
| ATOM | 1064 | P | C | A1040 | -5.780 | 209.924 | 251.916 | 1.00 | 0.00 | P |
| ATOM | 1065 | P | C | A1041 | -9.310 | 206.309 | 248.407 | 1.00 | 0.00 | P |
| ATOM | 1066 | P | G | A1042 | -14.427 | 204.446 | 246.773 | 1.00 | 0.00 | P |
| ATOM | 1067 | P | C | A1043 | -20.489 | 204.553 | 247.266 | 1.00 | 0.00 | P |
| ATOM | 1068 | P | G | A1044 | -23.772 | 205.055 | 252.670 | 1.00 | 0.00 | P |
| ATOM | 1069 | P | A | A1045 | -26.059 | 210.423 | 251.958 | 1.00 | 0.00 | P |
| ATOM | 1070 | P | A | A1046 | -30.092 | 211.135 | 247.559 | 1.00 | 0.00 | P |
| ATOM | 1071 | P | G | A1047 | -32.791 | 210.622 | 253.374 | 1.00 | 0.00 | P |
| ATOM | 1072 | P | A | A1048 | -31.325 | 205.129 | 256.508 | 1.00 | 0.00 | P |
| ATOM | 1073 | P | C | A1049 | -26.421 | 203.360 | 260.347 | 1.00 | 0.00 | P |
| ATOM | 1074 | P | A | A1050 | -27.496 | 203.336 | 264.860 | 1.00 | 0.00 | P |
| ATOM | 1075 | P | G | A1051 | -30.350 | 203.395 | 268.236 | 1.00 | 0.00 | P |
| ATOM | 1076 | P | C | A1052 | -35.817 | 203.079 | 269.954 | 1.00 | 0.00 | P |
| ATOM | 1077 | P | C | A1053 | -40.976 | 202.105 | 268.831 | 1.00 | 0.00 | P |
| ATOM | 1078 | P | A | A1054 | -45.033 | 199.364 | 265.525 | 1.00 | 0.00 | P |
| ATOM | 1079 | P | G | A1055 | -45.520 | 195.097 | 260.970 | 1.00 | 0.00 | P |
| ATOM | 1080 | P | G | A1056 | -43.317 | 190.792 | 257.479 | 1.00 | 0.00 | P |
| ATOM | 1081 | P | A | A1057 | -39.412 | 186.541 | 257.562 | 1.00 | 0.00 | .P |
| ATOM | 1082 | P | G | A1058 | -43.105 | 182.713 | 254.552 | 1.00 | 0.00 | P |
| ATOM | 1083 | P | G | A1059 | -43.117 | 178.180 | 252.124 | 1.00 | 0.00 | P |
| ATOM | 1084 | P | U | A1060 | -41.193 | 172.900 | 250.591 | 1.00 | 0.00 | P |
| ATOM | 1085 | P | U | A1061 | -41.404 | 175.295 | 257.052 | 1.00 | 0.00 | P |
| ATOM | 1086 | P | G | A1062 | -35.373 | 173.490 | 257.873 | 1.00 | 0.00 | P |
| ATOM | 1087 | P | G | A1063 | -34.944 | 168.886 | 254.865 | 1.00 | 0.00 | P |
| ATOM | 1088 | P | C | A1064 | -32.483 | 163.763 | 254.861 | 1.00 | 0.00 | P |
| ATOM | 1089 | P | U | A1065 | -29.750 | 160.223 | 258.415 | 1.00 | 0.00 | P |
| ATOM | 1090 | P | U | A1066 | -29.101 | 158.496 | 264.368 | 1.00 | 0.00 | P |
| ATOM | 1091 | P | A | A1067 | -32.314 | 158.611 | 268.955 | 1.00 | 0.00 | P |
| ATOM | 1092 | P | G | A1068 | -36.337 | 161.460 | 266.520 | 1.00 | 0.00 | P |
| ATOM | 1093 | P | A | A1069 | -37.088 | 166.266 | 264.537 | 1.00 | 0.00 | P |
| ATOM | 1094 | P | A | A1070 | -33.044 | 170.791 | 262.206 | 1.00 | 0.00 | P |
| ATOM | 1095 | P | G | A1071 | -36.635 | 177.114 | 261.531 | 1.00 | 0.00 | P |
| ATOM | 1096 | P | C | A1072 | -31.438 | 175.365 | 263.276 | 1.00 | 0.00 | P |
| ATOM | 1097 | P | A | A1073 | -29.604 | 174.494 | 267.877 | 1.00 | 0.00 | P |
| ATOM | 1098 | P | G | A1074 | -23.986 | 173.839 | 268.344 | 1.00 | 0.00 | P |

| | | | | | | | | | |
|---|---|---|---|---|---|---|---|---|---|
| ATOM | 1099 | P | C | A1075 | -20.152 | 171.165 | 264.420 | 1.00 | 0.00 | P |
| ATOM | 1100 | P | C | A1076 | -18.789 | 170.610 | 258.996 | 1.00 | 0.00 | P |
| ATOM | 1101 | P | A | A1077 | -19.248 | 171.576 | 253.849 | 1.00 | 0.00 | P |
| ATOM | 1102 | P | U | A1078 | -21.717 | 175.734 | 249.822 | 1.00 | 0.00 | P |
| ATOM | 1103 | P | C | A1079 | -24.491 | 178.742 | 248.965 | 1.00 | 0.00 | P |
| ATOM | 1104 | P | C | A1080 | -28.198 | 181.565 | 243.628 | 1.00 | 0.00 | P |
| ATOM | 1105 | P | U | A1081 | -33.054 | 183.484 | 241.545 | 1.00 | 0.00 | P |
| ATOM | 1106 | P | U | A1082 | -38.824 | 185.439 | 240.793 | 1.00 | 0.00 | P |
| ATOM | 1107 | P | U | A1083 | -41.424 | 190.009 | 242.020 | 1.00 | 0.00 | P |
| ATOM | 1108 | P | A | A1084 | -39.721 | 195.625 | 244.528 | 1.00 | 0.00 | P |
| ATOM | 1109 | P | A | A1085 | -34.611 | 194.907 | 247.014 | 1.00 | 0.00 | P |
| ATOM | 1110 | P | A | A1086 | -32.280 | 191.703 | 250.321 | 1.00 | 0.00 | P |
| ATOM | 1111 | P | G | A1087 | -32.022 | 186.521 | 253.134 | 1.00 | 0.00 | P |
| ATOM | 1112 | P | A | A1088 | -28.350 | 182.472 | 252.572 | 1.00 | 0.00 | P |
| ATOM | 1113 | P | G | A1089 | -25.934 | 179.434 | 257.816 | 1.00 | 0.00 | P |
| ATOM | 1114 | P | U | A1090 | -24.506 | 183.673 | 260.929 | 1.00 | 0.00 | P |
| ATOM | 1115 | P | G | A1091 | -24.698 | 183.712 | 267.340 | 1.00 | 0.00 | P |
| ATOM | 1116 | P | C | A1092 | -27.544 | 182.627 | 273.306 | 1.00 | 0.00 | P |
| ATOM | 1117 | P | G | A1093 | -31.466 | 181.458 | 277.100 | 1.00 | 0.00 | P |
| ATOM | 1118 | P | U | A1094 | -35.805 | 178.233 | 278.133 | 1.00 | 0.00 | P |
| ATOM | 1119 | P | A | A1095 | -37.910 | 173.257 | 277.935 | 1.00 | 0.00 | P |
| ATOM | 1120 | P | A | A1096 | -35.413 | 172.119 | 272.884 | 1.00 | 0.00 | P |
| ATOM | 1121 | P | U | A1097 | -36.610 | 173.160 | 267.359 | 1.00 | 0.00 | P |
| ATOM | 1122 | P | A | A1098 | -40.764 | 177.850 | 265.472 | 1.00 | 0.00 | P |
| ATOM | 1123 | P | G | A1099 | -44.095 | 182.273 | 266.394 | 1.00 | 0.00 | P |
| ATOM | 1124 | P | C | A1100 | -42.715 | 187.493 | 268.342 | 1.00 | 0.00 | P |
| ATOM | 1125 | P | U | A1101 | -39.091 | 191.873 | 269.436 | 1.00 | 0.00 | P |
| ATOM | 1126 | P | C | A1102 | -34.032 | 194.182 | 267.402 | 1.00 | 0.00 | P |
| ATOM | 1127 | P | A | A1103 | -30.082 | 195.374 | 263.829 | 1.00 | 0.00 | P |
| ATOM | 1128 | P | C | A1104 | -27.276 | 195.490 | 258.743 | 1.00 | 0.00 | P |
| ATOM | 1129 | P | U | A1105 | -29.951 | 197.258 | 254.337 | 1.00 | 0.00 | P |
| ATOM | 1130 | P | G | A1106 | -34.893 | 201.260 | 252.188 | 1.00 | 0.00 | P |
| ATOM | 1131 | P | G | A1107 | -37.812 | 205.915 | 252.361 | 1.00 | 0.00 | P |
| ATOM | 1132 | P | U | A1108 | -40.194 | 210.570 | 254.255 | 1.00 | 0.00 | P |
| ATOM | 1133 | P | C | A1109 | -39.540 | 215.440 | 256.150 | 1.00 | 0.00 | P |
| ATOM | 1134 | P | G | A1110 | -35.719 | 218.789 | 258.945 | 1.00 | 0.00 | P |
| ATOM | 1135 | P | A | A1111 | -29.132 | 220.386 | 259.614 | 1.00 | 0.00 | P |
| ATOM | 1136 | P | G | A1112 | -21.949 | 218.645 | 260.319 | 1.00 | 0.00 | P |
| ATOM | 1137 | P | U | A1113 | -20.512 | 212.439 | 262.341 | 1.00 | 0.00 | P |
| ATOM | 1138 | P | G | A1114 | -20.695 | 206.687 | 262.952 | 1.00 | 0.00 | P |
| ATOM | 1139 | P | G | A1115 | -18.156 | 201.230 | 262.078 | 1.00 | 0.00 | P |
| ATOM | 1140 | P | C | A1116 | -13.798 | 197.817 | 260.856 | 1.00 | 0.00 | P |
| ATOM | 1141 | P | G | A1117 | -7.535 | 197.575 | 260.468 | 1.00 | 0.00 | P |
| ATOM | 1142 | P | C | A1118 | -2.003 | 198.809 | 261.012 | 1.00 | 0.00 | P |
| ATOM | 1143 | P | C | A1119 | 2.142 | 201.765 | 263.890 | 1.00 | 0.00 | P |
| ATOM | 1144 | P | G | A1120 | 4.850 | 205.620 | 267.541 | 1.00 | 0.00 | P |
| ATOM | 1145 | P | C | A1121 | 5.526 | 207.967 | 272.372 | 1.00 | 0.00 | P |
| ATOM | 1146 | P | G | A1122 | 2.924 | 206.931 | 278.093 | 1.00 | 0.00 | P |
| ATOM | 1147 | P | C | A1123 | -0.559 | 204.592 | 282.964 | 1.00 | 0.00 | P |
| ATOM | 1148 | P | C | A1124 | -4.029 | 200.833 | 285.824 | 1.00 | 0.00 | P |
| ATOM | 1149 | P | G | A1125 | -5.092 | 195.508 | 287.147 | 1.00 | 0.00 | P |
| ATOM | 1150 | P | A | A1126 | -2.076 | 189.596 | 285.394 | 1.00 | 0.00 | P |
| ATOM | 1151 | P | A | A1127 | -2.389 | 192.944 | 291.290 | 1.00 | 0.00 | P |
| ATOM | 1152 | P | A | A1128 | 2.471 | 191.919 | 295.566 | 1.00 | 0.00 | P |
| ATOM | 1153 | P | A | A1129 | 5.969 | 191.021 | 300.723 | 1.00 | 0.00 | P |
| ATOM | 1154 | P | U | A1130 | 8.016 | 190.299 | 306.875 | 1.00 | 0.00 | P |
| ATOM | 1155 | P | G | A1131 | 6.330 | 194.797 | 309.629 | 1.00 | 0.00 | P |
| ATOM | 1156 | P | A | A1132 | 7.464 | 199.226 | 306.137 | 1.00 | 0.00 | P |
| ATOM | 1157 | P | U | A1133 | 7.388 | 202.579 | 300.643 | 1.00 | 0.00 | P |
| ATOM | 1158 | P | G | A1134 | 9.895 | 205.477 | 295.547 | 1.00 | 0.00 | P |
| ATOM | 1159 | P | C | A1135 | 15.989 | 207.193 | 295.720 | 1.00 | 0.00 | P |
| ATOM | 1160 | P | G | A1136 | 13.770 | 209.642 | 299.198 | 1.00 | 0.00 | P |
| ATOM | 1161 | P | G | A1137 | 9.343 | 212.768 | 302.028 | 1.00 | 0.00 | P |
| ATOM | 1162 | P | G | A1138 | 5.972 | 217.110 | 302.860 | 1.00 | 0.00 | P |
| ATOM | 1163 | P | G | A1139 | 6.380 | 216.819 | 296.876 | 1.00 | 0.00 | P |
| ATOM | 1164 | P | C | A1140 | 3.979 | 219.639 | 293.518 | 1.00 | 0.00 | P |
| ATOM | 1165 | P | U | A1141 | 1.486 | 214.219 | 289.742 | 1.00 | 0.00 | P |
| ATOM | 1166 | P | U | A1142 | -0.263 | 218.546 | 286.180 | 1.00 | 0.00 | P |
| ATOM | 1167 | P | A | A1142A | 5.213 | 221.893 | 285.371 | 1.00 | 0.00 | P |
| ATOM | 1168 | P | A | A1143 | 9.208 | 223.125 | 288.970 | 1.00 | 0.00 | P |
| ATOM | 1169 | P | G | A1144 | 11.107 | 217.402 | 285.028 | 1.00 | 0.00 | P |
| ATOM | 1170 | P | C | A1145 | 12.439 | 213.438 | 281.637 | 1.00 | 0.00 | P |
| ATOM | 1171 | P | C | A1146 | 13.161 | 212.479 | 276.008 | 1.00 | 0.00 | P |
| ATOM | 1172 | P | C | A1147 | 13.202 | 214.966 | 270.732 | 1.00 | 0.00 | P |
| ATOM | 1173 | P | A | A1148 | 16.707 | 219.483 | 268.366 | 1.00 | 0.00 | P |
| ATOM | 1174 | P | G | A1149 | 19.606 | 224.753 | 269.407 | 1.00 | 0.00 | P |
| ATOM | 1175 | P | C | A1150 | 20.974 | 229.906 | 272.241 | 1.00 | 0.00 | P |
| ATOM | 1176 | P | G | A1151 | 22.896 | 233.468 | 276.364 | 1.00 | 0.00 | P |
| ATOM | 1177 | P | C | A1152 | 24.819 | 234.857 | 282.148 | 1.00 | 0.00 | P |
| ATOM | 1178 | P | C | A1153 | 27.181 | 231.996 | 287.837 | 1.00 | 0.00 | P |
| ATOM | 1179 | P | G | A1154 | 29.271 | 226.939 | 291.163 | 1.00 | 0.00 | P |
| ATOM | 1180 | P | A | A1155 | 32.143 | 222.028 | 290.839 | 1.00 | 0.00 | P |
| ATOM | 1181 | P | A | A1156 | 36.603 | 221.117 | 293.103 | 1.00 | 0.00 | P |
| ATOM | 1182 | P | G | A1157 | 40.349 | 219.907 | 290.291 | 1.00 | 0.00 | P |
| ATOM | 1183 | P | C | A1158 | 43.837 | 219.304 | 285.270 | 1.00 | 0.00 | P |
| ATOM | 1184 | P | U | A1159 | 44.951 | 223.600 | 281.782 | 1.00 | 0.00 | P |
| ATOM | 1185 | P | G | A1160 | 46.408 | 229.005 | 281.242 | 1.00 | 0.00 | P |

| | | | | | | | |
|---|---|---|---|---|---|---|---|
| ATOM | 1186 | P | C A1161 | 49.034 233.151 284.470 | 1.00 | 0.00 | P |
| ATOM | 1187 | P | G A1162 | 52.725 235.575 287.834 | 1.00 | 0.00 | P |
| ATOM | 1188 | P | G A1163 | 56.593 234.667 292.106 | 1.00 | 0.00 | P |
| ATOM | 1189 | P | G A1164 | 59.933 229.857 295.600 | 1.00 | 0.00 | P |
| ATOM | 1190 | P | U A1165 | 63.777 223.733 295.461 | 1.00 | 0.00 | P |
| ATOM | 1191 | P | C A1166 | 66.875 217.925 292.492 | 1.00 | 0.00 | P |
| ATOM | 1192 | P | U A1167 | 69.232 215.327 287.226 | 1.00 | 0.00 | P |
| ATOM | 1193 | P | G A1168 | 70.007 217.704 281.324 | 1.00 | 0.00 | P |
| ATOM | 1194 | P | G A1169 | 73.118 222.246 277.339 | 1.00 | 0.00 | P |
| ATOM | 1195 | P | G A1170 | 75.305 227.362 276.460 | 1.00 | 0.00 | P |
| ATOM | 1196 | P | G A1171 | 78.465 231.221 278.498 | 1.00 | 0.00 | P |
| ATOM | 1197 | P | G A1173 | 81.495 232.437 284.945 | 1.00 | 0.00 | P |
| ATOM | 1198 | P | A A1174 | 84.465 228.040 286.898 | 1.00 | 0.00 | P |
| ATOM | 1199 | P | U A1175 | 80.386 223.064 287.081 | 1.00 | 0.00 | P |
| ATOM | 1200 | P | G A1176 | 77.861 224.407 292.594 | 1.00 | 0.00 | P |
| ATOM | 1201 | P | A A1177 | 72.598 225.586 295.089 | 1.00 | 0.00 | P |
| ATOM | 1202 | P | C A1178 | 69.988 231.063 294.059 | 1.00 | 0.00 | P |
| ATOM | 1203 | P | C A1179 | 67.257 234.299 290.267 | 1.00 | 0.00 | P |
| ATOM | 1204 | P | C A1180 | 64.394 234.561 285.148 | 1.00 | 0.00 | P |
| ATOM | 1205 | P | C A1181 | 62.840 230.934 280.225 | 1.00 | 0.00 | P |
| ATOM | 1206 | P | A A1182 | 60.130 225.194 276.846 | 1.00 | 0.00 | P |
| ATOM | 1207 | P | G A1183 | 54.952 221.159 278.887 | 1.00 | 0.00 | P |
| ATOM | 1208 | P | G A1184 | 57.416 218.007 282.949 | 1.00 | 0.00 | P |
| ATOM | 1209 | P | C A1185 | 55.446 215.335 284.441 | 1.00 | 0.00 | P |
| ATOM | 1210 | P | G A1186 | 51.934 213.440 288.603 | 1.00 | 0.00 | P |
| ATOM | 1211 | P | G A1187 | 52.933 210.070 291.260 | 1.00 | 0.00 | P |
| ATOM | 1212 | P | U A1188 | 52.670 205.933 291.800 | 1.00 | 0.00 | P |
| ATOM | 1213 | P | A A1189 | 53.546 202.786 295.610 | 1.00 | 0.00 | P |
| ATOM | 1214 | P | G A1190 | 56.506 198.648 297.490 | 1.00 | 0.00 | P |
| ATOM | 1215 | P | G A1191 | 60.214 195.490 296.624 | 1.00 | 0.00 | P |
| ATOM | 1216 | P | G A1192 | 65.246 196.133 293.537 | 1.00 | 0.00 | P |
| ATOM | 1217 | P | G A1193 | 70.159 199.507 292.022 | 1.00 | 0.00 | P |
| ATOM | 1218 | P | A A1194 | 72.996 204.530 291.945 | 1.00 | 0.00 | P |
| ATOM | 1219 | P | G A1195 | 74.201 210.078 294.715 | 1.00 | 0.00 | P |
| ATOM | 1220 | P | C A1196 | 74.722 213.921 299.817 | 1.00 | 0.00 | P |
| ATOM | 1221 | P | G A1197 | 73.220 215.115 306.317 | 1.00 | 0.00 | P |
| ATOM | 1222 | P | U A1198 | 71.469 214.937 310.682 | 1.00 | 0.00 | P |
| ATOM | 1223 | P | U A1199 | 71.657 211.460 315.444 | 1.00 | 0.00 | P |
| ATOM | 1224 | P | C A1200 | 74.255 207.761 319.436 | 1.00 | 0.00 | P |
| ATOM | 1225 | P | C A1201 | 78.415 206.352 322.244 | 1.00 | 0.00 | P |
| ATOM | 1226 | P | C A1202 | 84.931 205.515 321.657 | 1.00 | 0.00 | P |
| ATOM | 1227 | P | G A1203 | 89.335 206.628 318.474 | 1.00 | 0.00 | P |
| ATOM | 1228 | P | A A1204 | 91.325 209.888 315.561 | 1.00 | 0.00 | P |
| ATOM | 1229 | P | U A1205 | 94.747 214.685 317.403 | 1.00 | 0.00 | P |
| ATOM | 1230 | P | G A1206 | 93.998 219.116 315.874 | 1.00 | 0.00 | P |
| ATOM | 1231 | P | C A1207 | 90.311 223.641 318.006 | 1.00 | 0.00 | P |
| ATOM | 1232 | P | C A1208 | 86.071 225.857 322.891 | 1.00 | 0.00 | P |
| ATOM | 1233 | P | G A1209 | 82.299 227.275 326.856 | 1.00 | 0.00 | P |
| ATOM | 1234 | P | A A1210 | 81.024 227.574 332.100 | 1.00 | 0.00 | P |
| ATOM | 1235 | P | U A1211 | 80.602 232.362 335.950 | 1.00 | 0.00 | P |
| ATOM | 1236 | P | G A1212 | 75.320 230.525 332.204 | 1.00 | 0.00 | P |
| ATOM | 1237 | P | A A1213 | 74.127 224.275 330.743 | 1.00 | 0.00 | P |
| ATOM | 1238 | P | A A1214 | 73.203 219.065 327.742 | 1.00 | 0.00 | P |
| ATOM | 1239 | P | G A1215 | 69.563 214.693 327.901 | 1.00 | 0.00 | P |
| ATOM | 1240 | P | G A1216 | 63.282 213.562 328.602 | 1.00 | 0.00 | P |
| ATOM | 1241 | P | C A1217 | 57.447 216.824 329.126 | 1.00 | 0.00 | P |
| ATOM | 1242 | P | C A1218 | 54.594 222.250 326.419 | 1.00 | 0.00 | P |
| ATOM | 1243 | P | G A1219 | 54.430 227.721 322.026 | 1.00 | 0.00 | P |
| ATOM | 1244 | P | A A1220 | 55.587 230.859 317.980 | 1.00 | 0.00 | P |
| ATOM | 1245 | P | C A1221 | 59.330 233.135 313.516 | 1.00 | 0.00 | P |
| ATOM | 1246 | P | C A1222 | 63.247 231.515 308.703 | 1.00 | 0.00 | P |
| ATOM | 1247 | P | C A1223 | 64.508 226.981 304.226 | 1.00 | 0.00 | P |
| ATOM | 1248 | P | G A1224 | 62.839 222.708 301.698 | 1.00 | 0.00 | P |
| ATOM | 1249 | P | C A1225 | 58.954 221.257 305.848 | 1.00 | 0.00 | P |
| ATOM | 1250 | P | G A1226 | 59.057 216.761 310.406 | 1.00 | 0.00 | P |
| ATOM | 1251 | P | A A1227 | 61.150 213.360 314.337 | 1.00 | 0.00 | P |
| ATOM | 1252 | P | G A1228 | 67.250 217.100 315.281 | 1.00 | 0.00 | P |
| ATOM | 1253 | P | G A1229 | 70.069 222.336 315.652 | 1.00 | 0.00 | P |
| ATOM | 1254 | P | C A1230 | 70.448 226.086 319.479 | 1.00 | 0.00 | P |
| ATOM | 1255 | P | G A1231 | 68.727 229.922 325.002 | 1.00 | 0.00 | P |
| ATOM | 1256 | P | G A1232 | 67.407 231.301 329.305 | 1.00 | 0.00 | P |
| ATOM | 1257 | P | C A1233 | 65.115 230.275 334.124 | 1.00 | 0.00 | P |
| ATOM | 1258 | P | U A1234 | 64.428 225.992 338.621 | 1.00 | 0.00 | P |
| ATOM | 1259 | P | G A1235 | 65.841 221.328 341.015 | 1.00 | 0.00 | P |
| ATOM | 1260 | P | G A1236 | 70.172 217.910 341.082 | 1.00 | 0.00 | P |
| ATOM | 1261 | P | A A1237 | 76.758 215.616 340.075 | 1.00 | 0.00 | P |
| ATOM | 1262 | P | G A1238 | 80.361 213.238 336.010 | 1.00 | 0.00 | P |
| ATOM | 1263 | P | G A1239 | 78.681 212.167 329.334 | 1.00 | 0.00 | P |
| ATOM | 1264 | P | U A1240 | 78.787 213.607 323.537 | 1.00 | 0.00 | P |
| ATOM | 1265 | P | A A1241 | 80.472 215.675 317.281 | 1.00 | 0.00 | P |
| ATOM | 1266 | P | A A1242 | 78.965 219.085 313.436 | 1.00 | 0.00 | P |
| ATOM | 1267 | P | G A1243 | 81.360 217.978 307.516 | 1.00 | 0.00 | P |
| ATOM | 1268 | P | G A1244 | 84.755 213.880 304.911 | 1.00 | 0.00 | P |
| ATOM | 1269 | P | G A1245 | 86.815 208.148 304.528 | 1.00 | 0.00 | P |
| ATOM | 1270 | P | A A1246 | 85.195 202.578 307.213 | 1.00 | 0.00 | P |
| ATOM | 1271 | P | A A1247 | 81.466 199.027 311.354 | 1.00 | 0.00 | P |
| ATOM | 1272 | P | G A1248 | 77.941 195.595 317.558 | 1.00 | 0.00 | P |

```
ATOM   1273  P    U A1249      72.634 195.971 315.391  1.00  0.00           P
ATOM   1274  P    G A1250      67.653 198.483 314.183  1.00  0.00           P
ATOM   1275  P    C A1251      62.265 202.685 316.404  1.00  0.00           P
ATOM   1276  P    G A1252      56.560 201.834 316.536  1.00  0.00           P
ATOM   1277  P    A A1253      55.373 197.084 319.165  1.00  0.00           P
ATOM   1278  P    A A1254      50.676 192.845 317.962  1.00  0.00           P
ATOM   1279  P    U A1255      48.942 188.351 317.138  1.00  0.00           P
ATOM   1280  P    G A1256      51.702 186.681 322.264  1.00  0.00           P
ATOM   1281  P    C A1257      55.700 185.715 325.254  1.00  0.00           P
ATOM   1282  P    C A1258      58.211 187.446 329.650  1.00  0.00           P
ATOM   1283  P    G A1259      57.837 190.448 334.587  1.00  0.00           P
ATOM   1284  P    G A1260      55.739 195.005 337.892  1.00  0.00           P
ATOM   1285  P    C A1261      52.176 199.093 338.813  1.00  0.00           P
ATOM   1286  P    A A1262      45.810 200.091 337.669  1.00  0.00           P
ATOM   1287  P    U A1263      39.461 199.199 334.552  1.00  0.00           P
ATOM   1288  P    G A1264      34.759 196.129 335.010  1.00  0.00           P
ATOM   1289  P    A A1265      33.148 195.281 339.083  1.00  0.00           P
ATOM   1290  P    G A1266      32.957 197.491 343.519  1.00  0.00           P
ATOM   1291  P    U A1267      29.383 196.226 345.094  1.00  0.00           P
ATOM   1292  P    A A1268      27.305 191.059 343.102  1.00  0.00           P
ATOM   1293  P    A A1269      31.394 187.003 343.445  1.00  0.00           P
ATOM   1294  P    C A1270      31.722 183.952 348.220  1.00  0.00           P
ATOM   1295  P    G A1271      33.421 180.708 354.772  1.00  0.00           P
ATOM   1296  P    A A1272      28.275 176.070 353.689  1.00  0.00           P
ATOM   1297  P    U A1273      22.431 175.262 354.051  1.00  0.00           P
ATOM   1298  P    A A1274      23.893 174.877 359.399  1.00  0.00           P
ATOM   1299  P    A A1275      24.087 177.850 362.956  1.00  0.00           P
ATOM   1300  P    A A1276      25.318 180.256 365.348  1.00  0.00           P
ATOM   1301  P    G A1277      24.143 186.510 368.757  1.00  0.00           P
ATOM   1302  P    A A1278      21.983 190.073 372.891  1.00  0.00           P
ATOM   1303  P    G A1279      22.468 193.083 377.831  1.00  0.00           P
ATOM   1304  P    G A1280      27.355 193.591 382.565  1.00  0.00           P
ATOM   1305  P    G A1281      33.307 194.691 383.197  1.00  0.00           P
ATOM   1306  P    U A1282      38.688 195.385 382.540  1.00  0.00           P
ATOM   1307  P    G A1283      42.684 197.482 379.693  1.00  0.00           P
ATOM   1308  P    A A1284      44.160 201.175 375.924  1.00  0.00           P
ATOM   1309  P    G A1285      38.832 201.780 373.999  1.00  0.00           P
ATOM   1310  P    A A1286      34.534 199.482 370.997  1.00  0.00           P
ATOM   1311  P    A A1287      31.507 195.136 368.073  1.00  0.00           P
ATOM   1312  P    U A1288      32.822 190.632 369.825  1.00  0.00           P
ATOM   1313  P    C A1289      36.717 185.494 368.252  1.00  0.00           P
ATOM   1314  P    C A1290      39.325 183.199 373.034  1.00  0.00           P
ATOM   1315  P    C A1291      38.141 181.757 378.401  1.00  0.00           P
ATOM   1316  P    U A1292      34.013 180.189 382.864  1.00  0.00           P
ATOM   1317  P    C A1293      28.605 178.765 384.541  1.00  0.00           P
ATOM   1318  P    U A1294      23.076 177.641 383.626  1.00  0.00           P
ATOM   1319  P    C A1295      19.728 177.094 378.138  1.00  0.00           P
ATOM   1320  P    G A1296      18.115 173.686 373.913  1.00  0.00           P
ATOM   1321  P    C A1297      19.591 169.927 367.984  1.00  0.00           P
ATOM   1322  P    C A1298      24.400 165.510 365.496  1.00  0.00           P
ATOM   1323  P    G A1299      27.710 159.196 366.418  1.00  0.00           P
ATOM   1324  P    U A1300      32.627 158.798 366.616  1.00  0.00           P
ATOM   1325  P    A A1301      30.698 165.962 363.021  1.00  0.00           P
ATOM   1326  P    A A1302      35.042 163.234 362.759  1.00  0.00           P
ATOM   1327  P    G A1303      37.884 164.258 367.405  1.00  0.00           P
ATOM   1328  P    C A1304      40.764 162.888 371.951  1.00  0.00           P
ATOM   1329  P    C A1305      45.154 160.031 373.360  1.00  0.00           P
ATOM   1330  P    C A1306      50.068 156.947 371.904  1.00  0.00           P
ATOM   1331  P    A A1307      53.079 154.562 367.131  1.00  0.00           P
ATOM   1332  P    A A1308      55.418 154.590 361.355  1.00  0.00           P
ATOM   1333  P    G A1309      57.105 157.101 356.639  1.00  0.00           P
ATOM   1334  P    G A1310      55.948 163.019 354.778  1.00  0.00           P
ATOM   1335  P    G A1311      58.479 168.112 355.694  1.00  0.00           P
ATOM   1336  P    U A1312      60.835 172.011 361.285  1.00  0.00           P
ATOM   1337  P    U A1313      57.472 175.839 364.832  1.00  0.00           P
ATOM   1338  P    C A1314      53.937 175.292 368.471  1.00  0.00           P
ATOM   1339  P    C A1315      52.410 174.045 372.832  1.00  0.00           P
ATOM   1340  P    U A1316      52.506 177.389 377.311  1.00  0.00           P
ATOM   1341  P    A A1317      53.078 182.629 379.504  1.00  0.00           P
ATOM   1342  P    C A1318      53.547 188.442 378.738  1.00  0.00           P
ATOM   1343  P    G A1319      53.132 193.167 375.315  1.00  0.00           P
ATOM   1344  P    C A1320      51.803 194.246 368.513  1.00  0.00           P
ATOM   1345  P    A A1321      50.207 196.455 363.375  1.00  0.00           P
ATOM   1346  P    A A1322      50.663 195.848 357.845  1.00  0.00           P
ATOM   1347  P    U A1323      50.078 191.174 352.912  1.00  0.00           P
ATOM   1348  P    G A1324      46.480 185.743 352.462  1.00  0.00           P
ATOM   1349  P    G A1325      40.484 184.003 354.495  1.00  0.00           P
ATOM   1350  P    U A1326      42.139 190.595 355.153  1.00  0.00           P
ATOM   1351  P    C A1327      40.635 192.933 358.280  1.00  0.00           P
ATOM   1352  P    G A1328      42.326 194.036 362.353  1.00  0.00           P
ATOM   1353  P    U A1329      45.069 192.336 368.669  1.00  0.00           P
ATOM   1354  P    C A1330      46.099 185.173 371.541  1.00  0.00           P
ATOM   1355  P    A A1331      48.575 180.180 369.294  1.00  0.00           P
ATOM   1356  P    G A1332      50.878 177.056 366.267  1.00  0.00           P
ATOM   1357  P    C A1333      53.751 179.044 363.428  1.00  0.00           P
ATOM   1358  P    G A1334      56.275 183.144 361.090  1.00  0.00           P
ATOM   1359  P    U A1335      60.442 186.012 362.605  1.00  0.00           P
```

| | | | | | | | | | |
|---|---|---|---|---|---|---|---|---|---|
| ATOM | 1360 | P | A | A1336 | 64.632 | 186.085 | 366.578 | 1.00 | 0.00 | P |
| ATOM | 1361 | P | G | A1337 | 67.161 | 184.136 | 371.705 | 1.00 | 0.00 | P |
| ATOM | 1362 | P | G | A1338 | 66.803 | 179.195 | 376.793 | 1.00 | 0.00 | P |
| ATOM | 1363 | P | G | A1339 | 64.359 | 174.575 | 377.848 | 1.00 | 0.00 | P |
| ATOM | 1364 | P | U | A1340 | 61.776 | 168.901 | 376.635 | 1.00 | 0.00 | P |
| ATOM | 1365 | P | U | A1341 | 61.313 | 162.395 | 376.181 | 1.00 | 0.00 | P |
| ATOM | 1366 | P | A | A1342 | 67.511 | 159.898 | 376.695 | 1.00 | 0.00 | P |
| ATOM | 1367 | P | G | A1343 | 66.650 | 154.283 | 378.129 | 1.00 | 0.00 | P |
| ATOM | 1368 | P | G | A1344 | 65.112 | 148.030 | 378.012 | 1.00 | 0.00 | P |
| ATOM | 1369 | P | C | A1345 | 58.420 | 147.204 | 377.045 | 1.00 | 0.00 | P |
| ATOM | 1370 | P | G | A1346 | 56.487 | 147.521 | 372.799 | 1.00 | 0.00 | P |
| ATOM | 1371 | P | G | A1347 | 59.167 | 147.496 | 367.331 | 1.00 | 0.00 | P |
| ATOM | 1372 | P | G | A1348 | 65.092 | 148.028 | 364.731 | 1.00 | 0.00 | P |
| ATOM | 1373 | P | A | A1349 | 70.048 | 145.507 | 364.714 | 1.00 | 0.00 | P |
| ATOM | 1374 | P | C | A1350 | 72.039 | 140.106 | 365.682 | 1.00 | 0.00 | P |
| ATOM | 1375 | P | C | A1351 | 71.451 | 134.987 | 363.080 | 1.00 | 0.00 | P |
| ATOM | 1376 | P | U | A1352 | 69.459 | 133.759 | 357.992 | 1.00 | 0.00 | P |
| ATOM | 1377 | P | A | A1353 | 65.281 | 133.540 | 352.516 | 1.00 | 0.00 | P |
| ATOM | 1378 | P | A | A1354 | 63.773 | 133.213 | 348.962 | 1.00 | 0.00 | P |
| ATOM | 1379 | P | G | A1355 | 61.706 | 136.412 | 343.459 | 1.00 | 0.00 | P |
| ATOM | 1380 | P | G | A1356 | 66.622 | 141.123 | 341.736 | 1.00 | 0.00 | P |
| ATOM | 1381 | P | U | A1357 | 71.182 | 144.464 | 342.454 | 1.00 | 0.00 | P |
| ATOM | 1382 | P | G | A1358 | 76.404 | 143.259 | 344.274 | 1.00 | 0.00 | P |
| ATOM | 1383 | P | A | A1359 | 80.325 | 140.244 | 344.640 | 1.00 | 0.00 | P |
| ATOM | 1384 | P | A | A1360 | 82.987 | 134.445 | 344.681 | 1.00 | 0.00 | P |
| ATOM | 1385 | P | G | A1361 | 85.703 | 130.895 | 341.097 | 1.00 | 0.00 | P |
| ATOM | 1386 | P | C | A1362 | 84.233 | 129.908 | 335.165 | 1.00 | 0.00 | P |
| ATOM | 1387 | P | C | A1363 | 82.121 | 130.440 | 329.626 | 1.00 | 0.00 | P |
| ATOM | 1388 | P | G | A1364 | 81.303 | 135.004 | 327.105 | 1.00 | 0.00 | P |
| ATOM | 1389 | P | A | A1365 | 80.791 | 138.775 | 323.280 | 1.00 | 0.00 | P |
| ATOM | 1390 | P | A | A1366 | 82.091 | 141.778 | 327.922 | 1.00 | 0.00 | P |
| ATOM | 1391 | P | A | A1367 | 78.753 | 144.491 | 332.044 | 1.00 | 0.00 | P |
| ATOM | 1392 | P | G | A1368 | 73.658 | 145.209 | 335.140 | 1.00 | 0.00 | P |
| ATOM | 1393 | P | G | A1369 | 70.281 | 141.573 | 335.058 | 1.00 | 0.00 | P |
| ATOM | 1394 | P | C | A1370 | 68.500 | 136.245 | 337.141 | 1.00 | 0.00 | P |
| ATOM | 1395 | P | G | A1371 | 72.357 | 132.887 | 341.792 | 1.00 | 0.00 | P |
| ATOM | 1396 | P | U | A1372 | 75.450 | 129.176 | 344.991 | 1.00 | 0.00 | P |
| ATOM | 1397 | P | A | A1373 | 76.910 | 128.896 | 350.676 | 1.00 | 0.00 | P |
| ATOM | 1398 | P | G | A1374 | 76.907 | 132.467 | 355.246 | 1.00 | 0.00 | P |
| ATOM | 1399 | P | C | A1375 | 75.083 | 137.480 | 357.894 | 1.00 | 0.00 | P |
| ATOM | 1400 | P | C | A1376 | 71.523 | 142.764 | 357.872 | 1.00 | 0.00 | P |
| ATOM | 1401 | P | G | A1377 | 66.577 | 145.346 | 356.411 | 1.00 | 0.00 | P |
| ATOM | 1402 | P | A | A1378 | 61.391 | 145.097 | 357.035 | 1.00 | 0.00 | P |
| ATOM | 1403 | P | A | A1379 | 56.985 | 147.263 | 359.844 | 1.00 | 0.00 | P |
| ATOM | 1404 | P | G | A1380 | 55.553 | 141.616 | 361.771 | 1.00 | 0.00 | P |
| ATOM | 1405 | P | G | A1381 | 54.461 | 136.694 | 363.550 | 1.00 | 0.00 | P |
| ATOM | 1406 | P | G | A1382 | 56.714 | 133.330 | 367.200 | 1.00 | 0.00 | P |
| ATOM | 1407 | P | C | A1383 | 61.019 | 133.766 | 371.868 | 1.00 | 0.00 | P |
| ATOM | 1408 | P | A | A1384 | 60.488 | 137.631 | 377.262 | 1.00 | 0.00 | P |
| ATOM | 1409 | P | G | A1385 | 58.927 | 141.775 | 380.254 | 1.00 | 0.00 | P |
| ATOM | 1410 | P | C | A1386 | 55.221 | 145.854 | 380.233 | 1.00 | 0.00 | P |
| ATOM | 1411 | P | C | A1387 | 50.447 | 149.633 | 383.226 | 1.00 | 0.00 | P |
| ATOM | 1412 | P | G | A1388 | 47.769 | 153.666 | 386.418 | 1.00 | 0.00 | P |
| ATOM | 1413 | P | G | A1389 | 47.811 | 159.068 | 389.098 | 1.00 | 0.00 | P |
| ATOM | 1414 | P | U | A1390 | 49.875 | 164.544 | 389.927 | 1.00 | 0.00 | P |
| ATOM | 1415 | P | U | A1391 | 52.829 | 169.430 | 388.165 | 1.00 | 0.00 | P |
| ATOM | 1416 | P | A | A1392 | 53.940 | 173.929 | 385.153 | 1.00 | 0.00 | P |
| ATOM | 1417 | P | A | A1393 | 52.634 | 171.171 | 380.235 | 1.00 | 0.00 | P |
| ATOM | 1418 | P | U | A1394 | 55.150 | 167.385 | 376.913 | 1.00 | 0.00 | P |
| ATOM | 1419 | P | A | A1395 | 56.448 | 162.511 | 375.238 | 1.00 | 0.00 | P |
| ATOM | 1420 | P | U | A1396 | 55.956 | 156.853 | 377.639 | 1.00 | 0.00 | P |
| ATOM | 1421 | P | U | A1397 | 59.069 | 155.168 | 382.737 | 1.00 | 0.00 | P |
| ATOM | 1422 | P | C | A1398 | 64.847 | 157.378 | 383.733 | 1.00 | 0.00 | P |
| ATOM | 1423 | P | C | A1399 | 65.113 | 159.646 | 388.799 | 1.00 | 0.00 | P |
| ATOM | 1424 | P | G | A1400 | 62.869 | 158.614 | 394.063 | 1.00 | 0.00 | P |
| ATOM | 1425 | P | G | A1401 | 60.643 | 154.611 | 397.134 | 1.00 | 0.00 | P |
| ATOM | 1426 | P | C | A1402 | 59.309 | 148.853 | 397.334 | 1.00 | 0.00 | P |
| ATOM | 1427 | P | C | A1403 | 57.187 | 143.091 | 394.775 | 1.00 | 0.00 | P |
| ATOM | 1428 | P | C | A1404 | 58.722 | 138.593 | 390.490 | 1.00 | 0.00 | P |
| ATOM | 1429 | P | U | A1405 | 62.429 | 136.872 | 385.038 | 1.00 | 0.00 | P |
| ATOM | 1430 | P | U | A1406 | 66.630 | 133.940 | 380.346 | 1.00 | 0.00 | P |
| ATOM | 1431 | P | C | A1407 | 73.301 | 133.057 | 378.011 | 1.00 | 0.00 | P |
| ATOM | 1432 | P | C | A1408 | 79.018 | 135.925 | 378.800 | 1.00 | 0.00 | P |
| ATOM | 1433 | P | C | A1409 | 84.428 | 136.100 | 382.990 | 1.00 | 0.00 | P |
| ATOM | 1434 | P | G | A1410 | 85.804 | 134.597 | 388.052 | 1.00 | 0.00 | P |
| ATOM | 1435 | P | C | A1411 | 85.340 | 131.373 | 393.269 | 1.00 | 0.00 | P |
| ATOM | 1436 | P | A | A1412 | 83.316 | 126.903 | 396.758 | 1.00 | 0.00 | P |
| ATOM | 1437 | P | G | A1413 | 80.231 | 121.765 | 397.807 | 1.00 | 0.00 | P |
| ATOM | 1438 | P | G | A1414 | 77.571 | 118.742 | 393.321 | 1.00 | 0.00 | P |
| ATOM | 1439 | P | U | A1415 | 76.898 | 115.564 | 388.696 | 1.00 | 0.00 | P |
| ATOM | 1440 | P | G | A1416 | 78.113 | 112.111 | 383.496 | 1.00 | 0.00 | P |
| ATOM | 1441 | P | C | A1417 | 77.642 | 117.707 | 381.249 | 1.00 | 0.00 | P |
| ATOM | 1442 | P | G | A1418 | 78.307 | 121.976 | 377.072 | 1.00 | 0.00 | P |
| ATOM | 1443 | P | A | A1419 | 80.212 | 121.860 | 371.878 | 1.00 | 0.00 | P |
| ATOM | 1444 | P | U | A1420 | 76.696 | 125.894 | 368.675 | 1.00 | 0.00 | P |
| ATOM | 1445 | P | G | A1421 | 77.015 | 128.535 | 363.852 | 1.00 | 0.00 | P |
| ATOM | 1446 | P | G | A1422 | 75.729 | 123.755 | 360.842 | 1.00 | 0.00 | P |

| | | | | | | | | | |
|---|---|---|---|---|---|---|---|---|---|
| ATOM | 1447 | P | G | A1423 | 73.034 | 118.475 | 359.745 | 1.00 | 0.00 | P |
| ATOM | 1448 | P | G | A1424 | 68.154 | 114.943 | 360.337 | 1.00 | 0.00 | P |
| ATOM | 1449 | P | G | A1425 | 62.608 | 116.946 | 364.617 | 1.00 | 0.00 | P |
| ATOM | 1450 | P | G | A1426 | 59.038 | 122.837 | 365.310 | 1.00 | 0.00 | P |
| ATOM | 1451 | P | A | A1427 | 53.321 | 124.481 | 362.619 | 1.00 | 0.00 | P |
| ATOM | 1452 | P | C | A1428 | 48.103 | 128.288 | 358.665 | 1.00 | 0.00 | P |
| ATOM | 1453 | P | G | A1429 | 43.102 | 130.555 | 356.298 | 1.00 | 0.00 | P |
| ATOM | 1454 | P | C | A1430 | 37.112 | 131.159 | 355.350 | 1.00 | 0.00 | P |
| ATOM | 1455 | P | U | A1431 | 32.017 | 129.822 | 357.609 | 1.00 | 0.00 | P |
| ATOM | 1456 | P | C | A1432 | 29.306 | 127.259 | 362.899 | 1.00 | 0.00 | P |
| ATOM | 1457 | P | U | A1433 | 31.084 | 126.448 | 368.311 | 1.00 | 0.00 | P |
| ATOM | 1458 | P | A | A1434 | 30.617 | 123.853 | 373.744 | 1.00 | 0.00 | P |
| ATOM | 1459 | P | G | A1435 | 32.324 | 124.400 | 379.091 | 1.00 | 0.00 | P |
| ATOM | 1460 | P | G | A1436 | 35.563 | 127.574 | 382.674 | 1.00 | 0.00 | P |
| ATOM | 1461 | P | C | A1437 | 37.665 | 132.350 | 384.424 | 1.00 | 0.00 | P |
| ATOM | 1462 | P | U | A1438 | 38.131 | 137.807 | 382.942 | 1.00 | 0.00 | P |
| ATOM | 1463 | P | A | A1439 | 40.120 | 142.741 | 381.422 | 1.00 | 0.00 | P |
| ATOM | 1464 | P | G | A1440 | 36.023 | 146.836 | 379.273 | 1.00 | 0.00 | P |
| ATOM | 1465 | P | G | A1441 | 29.503 | 149.068 | 378.423 | 1.00 | 0.00 | P |
| ATOM | 1466 | P | G | A1442 | 23.328 | 149.465 | 380.636 | 1.00 | 0.00 | P |
| ATOM | 1467 | P | G | A1443 | 19.170 | 149.289 | 384.999 | 1.00 | 0.00 | P |
| ATOM | 1468 | P | G | A1444 | 17.033 | 149.385 | 390.699 | 1.00 | 0.00 | P |
| ATOM | 1469 | P | A | A1444A | 19.249 | 146.959 | 395.973 | 1.00 | 0.00 | P |
| ATOM | 1470 | P | C | A1445 | 22.445 | 147.720 | 398.909 | 1.00 | 0.00 | P |
| ATOM | 1471 | P | C | A1446 | 25.729 | 150.234 | 402.611 | 1.00 | 0.00 | P |
| ATOM | 1472 | P | G | A1447 | 28.453 | 155.024 | 404.143 | 1.00 | 0.00 | P |
| ATOM | 1473 | P | G | A1448 | 28.840 | 160.151 | 404.491 | 1.00 | 0.00 | P |
| ATOM | 1474 | P | A | A1449 | 28.799 | 165.049 | 403.590 | 1.00 | 0.00 | P |
| ATOM | 1475 | P | G | A1449A | 25.195 | 169.094 | 400.776 | 1.00 | 0.00 | P |
| ATOM | 1476 | P | C | A1450 | 19.157 | 170.955 | 398.591 | 1.00 | 0.00 | P |
| ATOM | 1477 | P | C | A1451 | 13.272 | 170.501 | 398.086 | 1.00 | 0.00 | P |
| ATOM | 1478 | P | A | A1453 | 9.866 | 172.781 | 395.278 | 1.00 | 0.00 | P |
| ATOM | 1479 | P | U | A1454 | 5.493 | 174.693 | 392.128 | 1.00 | 0.00 | P |
| ATOM | 1480 | P | G | A1455 | 0.385 | 172.765 | 393.331 | 1.00 | 0.00 | P |
| ATOM | 1481 | P | G | A1456 | 1.295 | 168.550 | 394.455 | 1.00 | 0.00 | P |
| ATOM | 1482 | P | A | A1457 | 4.420 | 165.694 | 393.596 | 1.00 | 0.00 | P |
| ATOM | 1483 | P | C | A1458 | 4.193 | 163.234 | 398.001 | 1.00 | 0.00 | P |
| ATOM | 1484 | P | G | A1459 | 6.542 | 160.685 | 400.899 | 1.00 | 0.00 | P |
| ATOM | 1485 | P | A | A1460 | 10.352 | 158.597 | 400.946 | 1.00 | 0.00 | P |
| ATOM | 1486 | P | G | A1461 | 12.494 | 156.297 | 396.413 | 1.00 | 0.00 | P |
| ATOM | 1487 | P | C | A1462 | 14.770 | 156.420 | 390.720 | 1.00 | 0.00 | P |
| ATOM | 1488 | P | C | A1463 | 18.851 | 159.794 | 388.138 | 1.00 | 0.00 | P |
| ATOM | 1489 | P | C | A1464 | 25.056 | 160.210 | 387.518 | 1.00 | 0.00 | P |
| ATOM | 1490 | P | G | A1465 | 30.145 | 158.104 | 388.080 | 1.00 | 0.00 | P |
| ATOM | 1491 | P | G | A1466 | 30.440 | 152.487 | 389.947 | 1.00 | 0.00 | P |
| ATOM | 1492 | P | C | A1467 | 33.192 | 147.213 | 391.174 | 1.00 | 0.00 | P |
| ATOM | 1493 | P | C | A1468 | 38.128 | 146.163 | 387.395 | 1.00 | 0.00 | P |
| ATOM | 1494 | P | A | A1469 | 44.283 | 144.261 | 387.335 | 1.00 | 0.00 | P |
| ATOM | 1495 | P | G | A1470 | 48.899 | 141.250 | 387.422 | 1.00 | 0.00 | P |
| ATOM | 1496 | P | A | A1471 | 53.632 | 139.792 | 390.381 | 1.00 | 0.00 | P |
| ATOM | 1497 | P | A | A1472 | 57.120 | 134.300 | 390.668 | 1.00 | 0.00 | P |
| ATOM | 1498 | P | G | A1473 | 55.821 | 129.215 | 393.181 | 1.00 | 0.00 | P |
| ATOM | 1499 | P | C | A1474 | 51.577 | 125.689 | 394.663 | 1.00 | 0.00 | P |
| ATOM | 1500 | P | G | A1475 | 46.637 | 123.403 | 394.161 | 1.00 | 0.00 | P |
| ATOM | 1501 | P | C | A1476 | 41.564 | 123.142 | 390.853 | 1.00 | 0.00 | P |
| ATOM | 1502 | P | A | A1477 | 38.430 | 123.715 | 386.818 | 1.00 | 0.00 | P |
| ATOM | 1503 | P | G | A1478 | 38.756 | 122.905 | 379.913 | 1.00 | 0.00 | P |
| ATOM | 1504 | P | G | A1479 | 43.503 | 122.960 | 376.558 | 1.00 | 0.00 | P |
| ATOM | 1505 | P | G | A1480 | 48.903 | 119.752 | 374.967 | 1.00 | 0.00 | P |
| ATOM | 1506 | P | U | A1482 | 52.239 | 114.190 | 374.280 | 1.00 | 0.00 | P |
| ATOM | 1507 | P | G | A1483 | 56.431 | 111.827 | 371.540 | 1.00 | 0.00 | P |
| ATOM | 1508 | P | G | A1484 | 60.713 | 111.328 | 373.922 | 1.00 | 0.00 | P |
| ATOM | 1509 | P | G | A1485 | 64.968 | 108.293 | 376.941 | 1.00 | 0.00 | P |
| ATOM | 1510 | P | A | A1486 | 68.237 | 103.497 | 377.632 | 1.00 | 0.00 | P |
| ATOM | 1511 | P | G | A1487 | 70.018 | 98.045 | 375.831 | 1.00 | 0.00 | P |
| ATOM | 1512 | P | G | A1488 | 71.755 | 94.258 | 372.215 | 1.00 | 0.00 | P |
| ATOM | 1513 | P | U | A1489 | 71.825 | 93.725 | 366.516 | 1.00 | 0.00 | P |
| ATOM | 1514 | P | A | A1490 | 71.703 | 97.880 | 362.471 | 1.00 | 0.00 | P |
| ATOM | 1515 | P | G | A1491 | 73.203 | 98.781 | 357.802 | 1.00 | 0.00 | P |
| ATOM | 1516 | P | G | A1492 | 74.895 | 104.060 | 355.788 | 1.00 | 0.00 | P |
| ATOM | 1517 | P | C | A1493 | 70.294 | 107.492 | 356.399 | 1.00 | 0.00 | P |
| ATOM | 1518 | P | A | A1494 | 73.546 | 113.233 | 355.997 | 1.00 | 0.00 | P |
| ATOM | 1519 | P | A | A1495 | 79.649 | 110.280 | 356.848 | 1.00 | 0.00 | P |
| ATOM | 1520 | P | A | A1496 | 79.678 | 108.730 | 363.431 | 1.00 | 0.00 | P |
| ATOM | 1521 | P | U | A1497 | 77.058 | 106.432 | 367.268 | 1.00 | 0.00 | P |
| ATOM | 1522 | P | C | A1498 | 73.217 | 106.726 | 373.052 | 1.00 | 0.00 | P |
| ATOM | 1523 | P | C | A1499 | 67.629 | 108.993 | 370.547 | 1.00 | 0.00 | P |
| ATOM | 1524 | P | G | A1500 | 63.129 | 109.226 | 364.131 | 1.00 | 0.00 | P |
| ATOM | 1525 | P | C | A1501 | 59.535 | 104.817 | 360.593 | 1.00 | 0.00 | P |
| ATOM | 1526 | P | C | A1502 | 58.559 | 97.614 | 362.778 | 1.00 | 0.00 | P |
| ATOM | 1527 | P | U | A1503 | 57.819 | 93.324 | 366.666 | 1.00 | 0.00 | P |
| ATOM | 1528 | P | C | A1504 | 56.916 | 92.689 | 371.247 | 1.00 | 0.00 | P |
| ATOM | 1529 | P | C | A1505 | 55.659 | 93.673 | 376.142 | 1.00 | 0.00 | P |
| ATOM | 1530 | P | C | A1506 | 54.595 | 96.997 | 381.282 | 1.00 | 0.00 | P |
| ATOM | 1531 | P | A | A1507 | 50.399 | 101.722 | 381.977 | 1.00 | 0.00 | P |
| ATOM | 1532 | P | A | A1508 | 48.250 | 106.426 | 380.751 | 1.00 | 0.00 | P |
| ATOM | 1533 | P | C | A1509 | 44.547 | 108.580 | 381.159 | 1.00 | 0.00 | P |

| | | | | | | | |
|---|---|---|---|---|---|---|---|
| ATOM | 1534 | P | A A1510 | 46.188 111.515 384.704 | 1.00 | 0.00 | P |
| ATOM | 1535 | P | A A1511 | 49.501 112.992 389.140 | 1.00 | 0.00 | P |
| ATOM | 1536 | P | G A1512 | 54.921 115.017 389.149 | 1.00 | 0.00 | P |
| ATOM | 1537 | P | C A1513 | 58.616 118.917 386.418 | 1.00 | 0.00 | P |
| ATOM | 1538 | P | U A1514 | 58.475 125.593 383.918 | 1.00 | 0.00 | P |
| ATOM | 1539 | P | C A1515 | 55.235 130.475 380.891 | 1.00 | 0.00 | P |
| ATOM | 1540 | P | U A1516 | 49.733 134.506 379.503 | 1.00 | 0.00 | P |
| ATOM | 1541 | P | G A1517 | 43.737 135.492 382.012 | 1.00 | 0.00 | P |
| ATOM | 1542 | P | C A1518 | 39.783 134.965 386.057 | 1.00 | 0.00 | P |
| ATOM | 1543 | P | G A1519 | 39.838 134.855 391.267 | 1.00 | 0.00 | P |
| ATOM | 1544 | P | U A1520 | 42.150 136.930 396.097 | 1.00 | 0.00 | P |
| ATOM | 1545 | P | G A1521 | 45.776 138.296 399.430 | 1.00 | 0.00 | P |
| ATOM | 1546 | P | G A1522 | 49.108 143.763 401.615 | 1.00 | 0.00 | P |
| ATOM | 1547 | P | U A1523 | 49.431 149.218 400.414 | 1.00 | 0.00 | P |
| ATOM | 1548 | P | G A1524 | 49.999 154.917 397.911 | 1.00 | 0.00 | P |
| ATOM | 1549 | P | G A1525 | 48.584 158.299 393.800 | 1.00 | 0.00 | P |
| ATOM | 1550 | P | G A1526 | 43.833 159.893 391.214 | 1.00 | 0.00 | P |
| ATOM | 1551 | P | G A1527 | 38.579 162.388 392.080 | 1.00 | 0.00 | P |
| ATOM | 1552 | P | A A1528 | 33.450 163.119 388.950 | 1.00 | 0.00 | P |
| ATOM | 1553 | P | A A1529 | 28.768 166.217 387.762 | 1.00 | 0.00 | P |
| ATOM | 1554 | P | G A1530 | 26.013 170.475 391.203 | 1.00 | 0.00 | P |
| ATOM | 1555 | P | C A1531 | 27.763 175.593 394.871 | 1.00 | 0.00 | P |
| ATOM | 1556 | P | C A1532 | 31.460 179.616 395.495 | 1.00 | 0.00 | P |
| ATOM | 1557 | P | C A1533 | 35.890 182.138 395.021 | 1.00 | 0.00 | P |
| ATOM | 1558 | P | G A1534 | 40.193 183.621 390.621 | 1.00 | 0.00 | P |
| ATOM | 1559 | P | U A1535 | 41.250 184.515 386.030 | 1.00 | 0.00 | P |
| ATOM | 1560 | P | A A1536 | 40.625 179.471 382.458 | 1.00 | 0.00 | P |
| ATOM | 1561 | P | C A1537 | 42.143 173.715 382.736 | 1.00 | 0.00 | P |
| ATOM | 1562 | P | G A1538 | 45.535 169.383 384.433 | 1.00 | 0.00 | P |
| ATOM | 1563 | P | G A1539 | 46.169 170.067 389.248 | 1.00 | 0.00 | P |
| ATOM | 1564 | P | G A1540 | 44.380 168.648 394.483 | 1.00 | 0.00 | P |
| ATOM | 1565 | P | U A1541 | 41.030 169.870 399.073 | 1.00 | 0.00 | P |
| ATOM | 1566 | P | G A1542 | 37.355 167.475 403.383 | 1.00 | 0.00 | P |
| ATOM | 1567 | P | A A1543 | 37.130 161.673 405.900 | 1.00 | 0.00 | P |
| ATOM | 1568 | P | C A1544 | 39.426 156.452 405.527 | 1.00 | 0.00 | P |
| ATOM | 1569 | P | A A1545 | 36.004 153.562 402.158 | 1.00 | 0.00 | P |
| ATOM | 1570 | P | A A1545A | 31.268 153.451 401.297 | 1.00 | 0.00 | P |
| ATOM | 1571 | P | C A1546 | 35.760 155.098 397.282 | 1.00 | 0.00 | P |
| ATOM | 1572 | P | C A1547 | 34.963 150.376 397.406 | 1.00 | 0.00 | P |
| ATOM | 1573 | P | C A1548 | 32.426 144.750 397.394 | 1.00 | 0.00 | P |
| ATOM | 1574 | P | C A1549 | 29.061 139.619 395.428 | 1.00 | 0.00 | P |
| ATOM | 1575 | P | C A1550 | 25.273 137.063 391.956 | 1.00 | 0.00 | P |
| ATOM | 1576 | P | C A1551 | 22.362 136.226 388.388 | 1.00 | 0.00 | P |
| ATOM | 1577 | P | G A1552 | 20.632 136.852 384.419 | 1.00 | 0.00 | P |
| ATOM | 1578 | P | A A1553 | 22.057 137.015 380.233 | 1.00 | 0.00 | P |
| ATOM | 1579 | P | A A1554 | 25.291 136.404 378.303 | 1.00 | 0.00 | P |
| ATOM | 1580 | P | G A1555 | 29.118 135.950 374.708 | 1.00 | 0.00 | P |
| ATOM | 1581 | P | C A1556 | 33.354 136.231 370.357 | 1.00 | 0.00 | P |
| ATOM | 1582 | P | C A1557 | 38.090 138.254 368.675 | 1.00 | 0.00 | P |
| ATOM | 1583 | P | A A1558 | 42.954 136.251 371.708 | 1.00 | 0.00 | P |
| ATOM | 1584 | P | G A1559 | 47.386 131.446 372.580 | 1.00 | 0.00 | P |
| ATOM | 1585 | P | G A1560 | 49.305 127.723 368.648 | 1.00 | 0.00 | P |
| ATOM | 1586 | P | G A1561 | 46.264 121.800 367.945 | 1.00 | 0.00 | P |
| ATOM | 1587 | P | A A1562 | 42.296 118.153 367.119 | 1.00 | 0.00 | P |
| ATOM | 1588 | P | G A1563 | 38.061 115.134 363.688 | 1.00 | 0.00 | P |
| ATOM | 1589 | P | C A1564 | 35.191 114.975 357.708 | 1.00 | 0.00 | P |
| ATOM | 1590 | P | C A1565 | 36.265 117.454 350.582 | 1.00 | 0.00 | P |
| ATOM | 1591 | P | A A1566 | 40.029 121.142 345.757 | 1.00 | 0.00 | P |
| ATOM | 1592 | P | A A1567 | 45.687 121.719 349.332 | 1.00 | 0.00 | P |
| ATOM | 1593 | P | G A1568 | 48.782 125.298 353.315 | 1.00 | 0.00 | P |
| ATOM | 1594 | P | A A1569 | 54.140 128.681 355.683 | 1.00 | 0.00 | P |
| ATOM | 1595 | P | A A1570 | 60.507 130.594 357.306 | 1.00 | 0.00 | P |
| ATOM | 1596 | P | A A1571 | 66.494 129.857 361.788 | 1.00 | 0.00 | P |
| ATOM | 1597 | P | A A1572 | 69.417 130.357 366.495 | 1.00 | 0.00 | P |
| ATOM | 1598 | P | G A1573 | 66.949 130.988 370.799 | 1.00 | 0.00 | P |
| ATOM | 1599 | P | C A1574 | 65.874 126.344 374.986 | 1.00 | 0.00 | P |
| ATOM | 1600 | P | C A1575 | 67.694 121.110 377.900 | 1.00 | 0.00 | P |
| ATOM | 1601 | P | U A1576 | 69.963 116.739 376.616 | 1.00 | 0.00 | P |
| ATOM | 1602 | P | C A1577 | 74.504 113.449 375.866 | 1.00 | 0.00 | P |
| ATOM | 1603 | P | U A1578 | 78.180 112.934 372.556 | 1.00 | 0.00 | P |
| ATOM | 1604 | P | A A1579 | 81.109 112.863 369.252 | 1.00 | 0.00 | P |
| ATOM | 1605 | P | A A1580 | 84.049 116.130 368.649 | 1.00 | 0.00 | P |
| ATOM | 1606 | P | G A1581 | 88.513 117.191 367.829 | 1.00 | 0.00 | P |
| ATOM | 1607 | P | C A1582 | 90.392 119.308 372.484 | 1.00 | 0.00 | P |
| ATOM | 1608 | P | A A1583 | 90.192 119.259 376.894 | 1.00 | 0.00 | P |
| ATOM | 1609 | P | C A1585 | 90.014 118.805 381.918 | 1.00 | 0.00 | P |
| ATOM | 1610 | P | A A1586 | 87.412 122.365 381.988 | 1.00 | 0.00 | P |
| ATOM | 1611 | P | A A1587 | 85.519 127.050 381.784 | 1.00 | 0.00 | P |
| ATOM | 1612 | P | C A1588 | 79.841 127.272 379.428 | 1.00 | 0.00 | P |
| ATOM | 1613 | P | C A1589 | 73.069 125.221 380.821 | 1.00 | 0.00 | P |
| ATOM | 1614 | P | U A1590 | 69.709 125.107 384.582 | 1.00 | 0.00 | P |
| ATOM | 1615 | P | G A1591 | 67.710 126.348 389.322 | 1.00 | 0.00 | P |
| ATOM | 1616 | P | C A1592 | 67.936 130.178 393.922 | 1.00 | 0.00 | P |
| ATOM | 1617 | P | G A1593 | 70.351 135.242 396.157 | 1.00 | 0.00 | P |
| ATOM | 1618 | P | G A1594 | 74.442 140.911 396.227 | 1.00 | 0.00 | P |
| ATOM | 1619 | P | G A1595 | 77.397 145.585 392.467 | 1.00 | 0.00 | P |
| ATOM | 1620 | P | A A1596 | 77.385 147.366 386.023 | 1.00 | 0.00 | P |

```
ATOM   1621  P     A A1597      75.004 148.816 380.488  1.00  0.00           P
ATOM   1622  P     C A1598      73.077 152.156 378.147  1.00  0.00           P
ATOM   1623  P     C A1599      73.869 155.289 374.238  1.00  0.00           P
ATOM   1624  P     C A1600      72.158 157.797 369.795  1.00  0.00           P
ATOM   1625  P     G A1601      67.502 160.446 367.697  1.00  0.00           P
ATOM   1626  P     U A1602      61.576 160.924 368.459  1.00  0.00           P
ATOM   1627  P     A A1603      56.462 162.187 371.455  1.00  0.00           P
ATOM   1628  P     C A1604      53.142 165.418 372.880  1.00  0.00           P
ATOM   1629  P     C A1605      48.564 166.923 369.211  1.00  0.00           P
ATOM   1630  P     G A1606      44.546 166.153 365.717  1.00  0.00           P
ATOM   1631  P     C A1607      45.356 161.950 362.814  1.00  0.00           P
ATOM   1632  P     A A1608      40.009 162.218 360.085  1.00  0.00           P
ATOM   1633  P     A A1609      41.858 167.167 359.096  1.00  0.00           P
ATOM   1634  P     A A1610      46.546 170.269 358.134  1.00  0.00           P
ATOM   1635  P     C A1611      51.270 169.188 356.311  1.00  0.00           P
ATOM   1636  P     C A1612      53.283 166.043 352.532  1.00  0.00           P
ATOM   1637  P     G A1613      52.158 165.913 347.192  1.00  0.00           P
ATOM   1638  P     A A1614      48.012 170.320 343.202  1.00  0.00           P
ATOM   1639  P     C A1615      49.610 173.204 348.158  1.00  0.00           P
ATOM   1640  P     A A1616      47.395 177.261 352.503  1.00  0.00           P
ATOM   1641  P     C A1617      42.386 173.323 353.552  1.00  0.00           P
ATOM   1642  P     A A1618      37.608 172.199 350.927  1.00  0.00           P
ATOM   1643  P     G A1619      36.227 165.260 351.331  1.00  0.00           P
ATOM   1644  P     G A1620      37.671 160.516 348.995  1.00  0.00           P
ATOM   1645  P     U A1621      41.157 157.657 350.752  1.00  0.00           P
ATOM   1646  P     G A1622      43.407 154.886 353.776  1.00  0.00           P
ATOM   1647  P     G A1623      43.924 150.074 358.206  1.00  0.00           P
ATOM   1648  P     G A1624      42.469 146.904 362.159  1.00  0.00           P
ATOM   1649  P     C A1625      39.595 146.527 367.051  1.00  0.00           P
ATOM   1650  P     G A1626      35.638 149.398 371.352  1.00  0.00           P
ATOM   1651  P     G A1627      31.169 145.957 369.161  1.00  0.00           P
ATOM   1652  P     G A1628      31.664 150.189 371.623  1.00  0.00           P
ATOM   1653  P     U A1629      27.379 149.833 375.642  1.00  0.00           P
ATOM   1654  P     G A1630      22.282 149.736 377.650  1.00  0.00           P
ATOM   1655  P     C A1630A     16.782 149.411 375.733  1.00  0.00           P
ATOM   1656  P     A A1631      13.732 149.680 371.357  1.00  0.00           P
ATOM   1657  P     A A1632      14.779 144.820 367.756  1.00  0.00           P
ATOM   1658  P     G A1633      17.495 143.940 363.454  1.00  0.00           P
ATOM   1659  P     A A1634      20.059 149.650 363.140  1.00  0.00           P
ATOM   1660  P     G A1635      22.523 153.610 360.697  1.00  0.00           P
ATOM   1661  P     C A1636      18.718 158.475 362.156  1.00  0.00           P
ATOM   1662  P     A A1637      17.497 162.229 366.205  1.00  0.00           P
ATOM   1663  P     C A1638      19.645 164.438 371.246  1.00  0.00           P
ATOM   1664  P     U A1639      24.126 164.713 375.344  1.00  0.00           P
ATOM   1665  P     C A1640      29.850 164.215 377.925  1.00  0.00           P
ATOM   1666  P     A A1641      34.089 163.228 379.977  1.00  0.00           P
ATOM   1667  P     G A1642      36.606 166.429 376.824  1.00  0.00           P
ATOM   1668  P     G A1643      36.687 169.336 371.761  1.00  0.00           P
ATOM   1669  P     C A1644      34.558 173.058 367.528  1.00  0.00           P
ATOM   1670  P     G A1645      32.719 176.611 364.276  1.00  0.00           P
ATOM   1671  P     C A1646      33.463 176.467 358.614  1.00  0.00           P
ATOM   1672  P     G A1647      36.076 181.227 359.352  1.00  0.00           P
ATOM   1673  P     C A1648      31.264 184.569 359.745  1.00  0.00           P
ATOM   1674  P     G A1649      26.388 188.723 361.754  1.00  0.00           P
ATOM   1675  P     G A1650      19.824 190.992 362.156  1.00  0.00           P
ATOM   1676  P     G A1651      15.307 193.950 359.913  1.00  0.00           P
ATOM   1677  P     A A1652      11.060 193.114 356.482  1.00  0.00           P
ATOM   1678  P     G A1653       8.708 190.050 352.121  1.00  0.00           P
ATOM   1679  P     A A1654       8.893 188.164 347.813  1.00  0.00           P
ATOM   1680  P     A A1655       9.027 185.957 343.268  1.00  0.00           P
ATOM   1681  P     C A1656      10.689 182.940 339.049  1.00  0.00           P
ATOM   1682  P     C A1657      14.528 178.144 339.406  1.00  0.00           P
ATOM   1683  P     C A1658      16.300 173.712 343.073  1.00  0.00           P
ATOM   1684  P     U A1659      17.095 169.841 346.990  1.00  0.00           P
ATOM   1685  P     C A1660      12.672 166.904 350.022  1.00  0.00           P
ATOM   1686  P     G A1661       6.182 166.779 350.977  1.00  0.00           P
ATOM   1687  P     C A1662       0.384 167.056 350.004  1.00  0.00           P
ATOM   1688  P     C A1663      -3.688 168.124 346.829  1.00  0.00           P
ATOM   1689  P     A A1664      -6.963 167.581 342.745  1.00  0.00           P
ATOM   1690  P     A A1665     -11.320 165.339 341.905  1.00  0.00           P
ATOM   1691  P     G A1666     -11.382 162.358 337.063  1.00  0.00           P
ATOM   1692  P     G A1667      -8.338 159.023 334.242  1.00  0.00           P
ATOM   1693  P     A A1668      -3.681 158.524 334.867  1.00  0.00           P
ATOM   1694  P     A A1669      -1.130 159.054 332.174  1.00  0.00           P
ATOM   1695  P     C A1670      -1.715 162.653 329.671  1.00  0.00           P
ATOM   1696  P     U A1671       1.907 166.069 326.172  1.00  0.00           P
ATOM   1697  P     C A1672       6.512 163.952 324.535  1.00  0.00           P
ATOM   1698  P     U A1673       7.612 159.283 324.600  1.00  0.00           P
ATOM   1699  P     G A1674       8.680 156.398 327.641  1.00  0.00           P
ATOM   1700  P     C A1675       8.296 156.823 332.363  1.00  0.00           P
ATOM   1701  P     A A1676      12.672 157.814 336.108  1.00  0.00           P
ATOM   1702  P     A A1677      12.477 161.297 340.379  1.00  0.00           P
ATOM   1703  P     G A1678      10.281 162.011 344.432  1.00  0.00           P
ATOM   1704  P     U A1679       5.489 158.792 345.195  1.00  0.00           P
ATOM   1705  P     U A1680       4.360 153.667 348.139  1.00  0.00           P
ATOM   1706  P     G A1681       5.672 148.416 352.167  1.00  0.00           P
ATOM   1707  P     G A1682      10.473 144.819 354.968  1.00  0.00           P
```

```
ATOM   1708  P   C A1683    12.068 140.508 359.490  1.00  0.00           P
ATOM   1709  P   C A1684     8.981 135.770 361.286  1.00  0.00           P
ATOM   1710  P   C A1685     4.557 131.980 361.070  1.00  0.00           P
ATOM   1711  P   C A1686     0.111 129.719 358.291  1.00  0.00           P
ATOM   1712  P   G A1687    -2.973 128.624 353.556  1.00  0.00           P
ATOM   1713  P   U A1688    -2.198 129.016 347.604  1.00  0.00           P
ATOM   1714  P   A A1689     0.898 129.669 342.613  1.00  0.00           P
ATOM   1715  P   A A1690     1.266 128.613 336.751  1.00  0.00           P
ATOM   1716  P   C A1691     3.710 126.724 331.965  1.00  0.00           P
ATOM   1717  P   U A1692     9.616 124.513 331.595  1.00  0.00           P
ATOM   1718  P   U A1693    14.236 120.675 332.543  1.00  0.00           P
ATOM   1719  P   C A1694    17.248 119.912 336.971  1.00  0.00           P
ATOM   1720  P   G A1695    16.037 119.874 342.378  1.00  0.00           P
ATOM   1721  P   G A1696    15.972 125.842 344.937  1.00  0.00           P
ATOM   1722  P   G A1697    13.340 129.755 341.542  1.00  0.00           P
ATOM   1723  P   A A1698    11.018 135.120 341.159  1.00  0.00           P
ATOM   1724  P   G A1699    12.519 134.126 346.586  1.00  0.00           P
ATOM   1725  P   A A1700     5.944 132.712 345.809  1.00  0.00           P
ATOM   1726  P   A A1701     5.927 139.576 346.282  1.00  0.00           P
ATOM   1727  P   G A1702     1.371 141.831 346.154  1.00  0.00           P
ATOM   1728  P   G A1703    -4.019 142.864 349.103  1.00  0.00           P
ATOM   1729  P   G A1704    -6.416 143.103 354.326  1.00  0.00           P
ATOM   1730  P   G A1705    -4.834 142.373 360.860  1.00  0.00           P
ATOM   1731  P   U A1706    -2.959 144.089 365.861  1.00  0.00           P
ATOM   1732  P   G A1707     1.150 144.711 368.925  1.00  0.00           P
ATOM   1733  P   C A1708     2.995 147.863 373.134  1.00  0.00           P
ATOM   1734  P   U A1709     1.492 149.383 378.660  1.00  0.00           P
ATOM   1735  P   C A1710    -1.358 147.786 383.550  1.00  0.00           P
ATOM   1736  P   C A1711    -3.060 143.690 386.825  1.00  0.00           P
ATOM   1737  P   C A1712    -3.108 137.687 388.345  1.00  0.00           P
ATOM   1738  P   U A1716    -0.949 132.459 386.752  1.00  0.00           P
ATOM   1739  P   G A1717     1.985 126.379 384.199  1.00  0.00           P
ATOM   1740  P   G A1718     6.364 124.294 382.393  1.00  0.00           P
ATOM   1741  P   G A1725    12.344 123.771 380.418  1.00  0.00           P
ATOM   1742  P   G A1726    17.053 125.192 379.836  1.00  0.00           P
ATOM   1743  P   U A1727    22.088 126.908 381.910  1.00  0.00           P
ATOM   1744  P   G A1728    25.179 128.729 385.751  1.00  0.00           P
ATOM   1745  P   A A1729    22.235 126.374 389.406  1.00  0.00           P
ATOM   1746  P   U A1730    18.951 124.701 392.563  1.00  0.00           P
ATOM   1747  P   G A1731    16.070 129.021 395.888  1.00  0.00           P
ATOM   1748  P   A A1732    14.960 134.421 396.059  1.00  0.00           P
ATOM   1749  P   G A1733    14.164 137.764 392.404  1.00  0.00           P
ATOM   1750  P   C A1734    16.288 140.377 386.501  1.00  0.00           P
ATOM   1751  P   C A1735    16.678 139.770 379.848  1.00  0.00           P
ATOM   1752  P   C A1741    14.577 138.943 375.256  1.00  0.00           P
ATOM   1753  P   C A1742    10.535 136.376 372.164  1.00  0.00           P
ATOM   1754  P   G A1743     6.673 134.434 370.315  1.00  0.00           P
ATOM   1755  P   G A1746     2.163 132.932 370.429  1.00  0.00           P
ATOM   1756  P   G A1747    -3.677 132.279 372.010  1.00  0.00           P
ATOM   1757  P   G A1748    -8.725 134.213 372.821  1.00  0.00           P
ATOM   1758  P   A A1749   -12.775 138.078 374.325  1.00  0.00           P
ATOM   1759  P   G A1750   -14.373 143.620 375.720  1.00  0.00           P
ATOM   1760  P   C A1751   -14.081 149.395 376.014  1.00  0.00           P
ATOM   1761  P   C A1752   -11.564 155.071 373.897  1.00  0.00           P
ATOM   1762  P   G A1753   -10.046 159.042 369.766  1.00  0.00           P
ATOM   1763  P   C A1754    -8.852 160.312 364.534  1.00  0.00           P
ATOM   1764  P   A A1755    -6.610 155.300 362.803  1.00  0.00           P
ATOM   1765  P   G A1756    -1.668 151.960 362.903  1.00  0.00           P
ATOM   1766  P   U A1757     3.238 149.504 363.157  1.00  0.00           P
ATOM   1767  P   G A1758     7.287 151.366 363.631  1.00  0.00           P
ATOM   1768  P   A A1759    11.443 155.369 364.816  1.00  0.00           P
ATOM   1769  P   A A1760    12.865 157.691 361.069  1.00  0.00           P
ATOM   1770  P   C A1761    15.859 156.435 357.586  1.00  0.00           P
ATOM   1771  P   A A1762    15.038 152.662 354.438  1.00  0.00           P
ATOM   1772  P   G A1763    12.977 149.106 350.417  1.00  0.00           P
ATOM   1773  P   G A1764    10.239 149.738 345.411  1.00  0.00           P
ATOM   1774  P   C A1765     8.176 145.099 341.920  1.00  0.00           P
ATOM   1775  P   U A1766     5.976 140.297 339.381  1.00  0.00           P
ATOM   1776  P   C A1767     5.020 137.131 334.889  1.00  0.00           P
ATOM   1777  P   U A1768     5.665 135.336 329.266  1.00  0.00           P
ATOM   1778  P   G A1769     7.985 135.179 324.103  1.00  0.00           P
ATOM   1779  P   G A1770    12.959 135.705 320.903  1.00  0.00           P
ATOM   1780  P   C A1771    18.381 136.406 319.879  1.00  0.00           P
ATOM   1781  P   G A1772    23.844 135.957 321.444  1.00  0.00           P
ATOM   1782  P   A A1773    26.868 133.886 325.464  1.00  0.00           P
ATOM   1783  P   C A1774    26.556 135.682 330.661  1.00  0.00           P
ATOM   1784  P   U A1775    25.579 137.198 336.000  1.00  0.00           P
ATOM   1785  P   G A1776    28.996 139.930 339.379  1.00  0.00           P
ATOM   1786  P   U A1777    34.791 142.232 338.930  1.00  0.00           P
ATOM   1787  P   U A1778    38.405 145.721 336.280  1.00  0.00           P
ATOM   1788  P   U A1779    38.376 150.466 332.944  1.00  0.00           P
ATOM   1789  P   A A1780    37.919 156.206 331.337  1.00  0.00           P
ATOM   1790  P   C A1781    37.598 157.555 336.742  1.00  0.00           P
ATOM   1791  P   C A1782    36.532 159.767 330.986  1.00  0.00           P
ATOM   1792  P   A A1783    32.115 157.306 330.910  1.00  0.00           P
ATOM   1793  P   A A1784    29.241 153.401 330.884  1.00  0.00           P
ATOM   1794  P   A A1785    25.415 148.813 332.100  1.00  0.00           P
```

```
ATOM   1795  P    A A1786      26.071 142.937 328.484  1.00  0.00           P
ATOM   1796  P    A A1787      29.460 140.316 323.820  1.00  0.00           P
ATOM   1797  P    C A1788      34.473 139.685 323.219  1.00  0.00           P
ATOM   1798  P    A A1789      38.387 136.778 325.862  1.00  0.00           P
ATOM   1799  P    C A1790      38.539 132.175 329.541  1.00  0.00           P
ATOM   1800  P    A A1791      37.378 127.453 331.771  1.00  0.00           P
ATOM   1801  P    G A1792      35.806 121.798 331.833  1.00  0.00           P
ATOM   1802  P    C A1793      33.890 118.984 327.322  1.00  0.00           P
ATOM   1803  P    U A1794      34.859 117.784 322.124  1.00  0.00           P
ATOM   1804  P    C A1795      38.639 118.471 317.658  1.00  0.00           P
ATOM   1805  P    U A1796      43.425 118.454 314.509  1.00  0.00           P
ATOM   1806  P    C A1797      49.004 119.218 313.599  1.00  0.00           P
ATOM   1807  P    U A1798      54.102 117.987 314.958  1.00  0.00           P
ATOM   1808  P    G A1799      59.155 117.124 318.918  1.00  0.00           P
ATOM   1809  P    C A1800      60.836 114.785 322.872  1.00  0.00           P
ATOM   1810  P    G A1801      61.869 117.547 329.080  1.00  0.00           P
ATOM   1811  P    A A1802      64.345 121.859 327.018  1.00  0.00           P
ATOM   1812  P    A A1803      62.135 121.103 322.693  1.00  0.00           P
ATOM   1813  P    C A1804      58.878 123.755 320.056  1.00  0.00           P
ATOM   1814  P    U A1805      58.796 129.540 321.047  1.00  0.00           P
ATOM   1815  P    C A1806      58.588 134.661 322.950  1.00  0.00           P
ATOM   1816  P    G A1807      62.325 138.418 324.369  1.00  0.00           P
ATOM   1817  P    U A1808      66.814 140.457 322.969  1.00  0.00           P
ATOM   1818  P    A A1809      70.779 136.231 321.430  1.00  0.00           P
ATOM   1819  P    A A1810      75.186 132.903 324.169  1.00  0.00           P
ATOM   1820  P    G A1811      76.412 130.574 328.674  1.00  0.00           P
ATOM   1821  P    A A1812      71.265 129.045 332.990  1.00  0.00           P
ATOM   1822  P    G A1813      65.579 129.044 335.234  1.00  0.00           P
ATOM   1823  P    G A1814      59.567 128.891 335.842  1.00  0.00           P
ATOM   1824  P    A A1815      55.839 123.733 333.406  1.00  0.00           P
ATOM   1825  P    G A1816      59.985 123.321 338.030  1.00  0.00           P
ATOM   1826  P    G A1817      59.348 118.132 338.802  1.00  0.00           P
ATOM   1827  P    U A1818      55.018 115.749 335.960  1.00  0.00           P
ATOM   1828  P    A A1819      54.122 111.277 331.267  1.00  0.00           P
ATOM   1829  P    U A1820      47.576 111.082 328.749  1.00  0.00           P
ATOM   1830  P    A A1821      47.059 115.425 332.129  1.00  0.00           P
ATOM   1831  P    G A1822      49.961 120.315 332.808  1.00  0.00           P
ATOM   1832  P    G A1823      50.796 125.966 329.247  1.00  0.00           P
ATOM   1833  P    G A1824      51.137 129.840 324.685  1.00  0.00           P
ATOM   1834  P    A A1825      48.057 132.529 320.833  1.00  0.00           P
ATOM   1835  P    G A1826      42.250 133.759 318.533  1.00  0.00           P
ATOM   1836  P    C A1827      36.531 132.467 317.514  1.00  0.00           P
ATOM   1837  P    G A1828      30.817 132.303 321.174  1.00  0.00           P
ATOM   1838  P    A A1829      29.035 128.239 325.746  1.00  0.00           P
ATOM   1839  P    C A1830      28.204 123.197 327.525  1.00  0.00           P
ATOM   1840  P    G A1831      24.272 118.835 328.048  1.00  0.00           P
ATOM   1841  P    C A1832      21.354 116.048 324.756  1.00  0.00           P
ATOM   1842  P    U A1833      20.855 115.384 318.832  1.00  0.00           P
ATOM   1843  P    U A1834      24.723 118.278 313.470  1.00  0.00           P
ATOM   1844  P    G A1835      27.427 119.158 308.120  1.00  0.00           P
ATOM   1845  P    C A1836      29.635 116.538 303.014  1.00  0.00           P
ATOM   1846  P    C A1837      30.917 117.371 298.041  1.00  0.00           P
ATOM   1847  P    C A1838      37.226 119.050 296.113  1.00  0.00           P
ATOM   1848  P    G A1839      42.167 119.762 293.024  1.00  0.00           P
ATOM   1849  P    G A1840      44.475 123.925 291.774  1.00  0.00           P
ATOM   1850  P    U A1841      47.985 127.501 294.454  1.00  0.00           P
ATOM   1851  P    G A1842      50.689 129.330 299.987  1.00  0.00           P
ATOM   1852  P    C A1843      49.957 125.480 305.177  1.00  0.00           P
ATOM   1853  P    C A1844      53.439 121.866 309.761  1.00  0.00           P
ATOM   1854  P    G A1845      55.989 117.037 308.615  1.00  0.00           P
ATOM   1855  P    G A1846      58.229 111.697 305.422  1.00  0.00           P
ATOM   1856  P    A A1847      61.742 108.896 300.410  1.00  0.00           P
ATOM   1857  P    A A1848      63.916 109.378 295.255  1.00  0.00           P
ATOM   1858  P    G A1849      65.731 111.092 290.726  1.00  0.00           P
ATOM   1859  P    G A1850      66.585 114.301 286.185  1.00  0.00           P
ATOM   1860  P    U A1851      67.101 119.580 283.903  1.00  0.00           P
ATOM   1861  P    C A1852      68.242 124.923 285.144  1.00  0.00           P
ATOM   1862  P    A A1853      70.881 127.954 288.273  1.00  0.00           P
ATOM   1863  P    A A1854      76.166 130.215 292.077  1.00  0.00           P
ATOM   1864  P    G A1855      80.592 127.922 295.396  1.00  0.00           P
ATOM   1865  P    G A1856      84.290 123.959 296.105  1.00  0.00           P
ATOM   1866  P    G A1857      86.592 119.633 293.406  1.00  0.00           P
ATOM   1867  P    G A1858      88.140 118.333 289.207  1.00  0.00           P
ATOM   1868  P    A A1859      90.030 119.331 283.768  1.00  0.00           P
ATOM   1869  P    G A1860      90.185 120.192 277.942  1.00  0.00           P
ATOM   1870  P    G A1861      91.306 125.184 275.042  1.00  0.00           P
ATOM   1871  P    G A1862      93.976 131.517 273.422  1.00  0.00           P
ATOM   1872  P    G A1863      97.356 137.095 272.910  1.00  0.00           P
ATOM   1873  P    U A1864     101.808 141.502 274.650  1.00  0.00           P
ATOM   1874  P    G A1869     108.241 138.396 276.134  1.00  0.00           P
ATOM   1875  P    C A1870     113.104 134.547 275.964  1.00  0.00           P
ATOM   1876  P    A A1871     110.673 129.519 276.527  1.00  0.00           P
ATOM   1877  P    A A1872     108.987 127.120 281.664  1.00  0.00           P
ATOM   1878  P    G A1878     106.603 128.042 285.199  1.00  0.00           P
ATOM   1879  P    C A1879     103.776 131.881 288.372  1.00  0.00           P
ATOM   1880  P    C A1880      98.593 133.808 289.448  1.00  0.00           P
ATOM   1881  P    C A1881      92.801 135.349 287.445  1.00  0.00           P
```

```
ATOM   1882  P   C A1882    87.020 133.993 287.344  1.00  0.00           P
ATOM   1883  P   G A1883    84.119 131.565 283.276  1.00  0.00           P
ATOM   1884  P   A A1884    81.452 127.362 280.651  1.00  0.00           P
ATOM   1885  P   A A1885    79.382 123.399 279.009  1.00  0.00           P
ATOM   1886  P   C A1886    76.323 118.769 281.456  1.00  0.00           P
ATOM   1887  P   C A1887    74.850 115.757 286.101  1.00  0.00           P
ATOM   1888  P   G A1888    73.700 116.518 292.185  1.00  0.00           P
ATOM   1889  P   A A1889    70.261 118.533 296.696  1.00  0.00           P
ATOM   1890  P   A A1890    65.385 121.571 299.149  1.00  0.00           P
ATOM   1891  P   G A1891    60.510 124.789 299.680  1.00  0.00           P
ATOM   1892  P   C A1892    56.862 126.557 295.950  1.00  0.00           P
ATOM   1893  P   C A1893    54.121 125.002 290.921  1.00  0.00           P
ATOM   1894  P   C A1894    53.744 119.544 288.348  1.00  0.00           P
ATOM   1895  P   C A1895    50.426 114.939 289.040  1.00  0.00           P
ATOM   1896  P   G A1896    47.164 113.009 292.400  1.00  0.00           P
ATOM   1897  P   G A1897    44.187 112.616 297.428  1.00  0.00           P
ATOM   1898  P   U A1898    42.481 113.998 303.209  1.00  0.00           P
ATOM   1899  P   G A1899    39.368 118.253 305.638  1.00  0.00           P
ATOM   1900  P   A A1900    36.114 120.788 309.443  1.00  0.00           P
ATOM   1901  P   A A1901    38.888 125.120 310.704  1.00  0.00           P
ATOM   1902  P   C A1902    39.757 129.437 307.067  1.00  0.00           P
ATOM   1903  P   G A1903    36.879 131.582 302.868  1.00  0.00           P
ATOM   1904  P   G A1904    31.788 131.652 299.214  1.00  0.00           P
ATOM   1905  P   C A1905    28.123 129.825 295.996  1.00  0.00           P
ATOM   1906  P   G A1906    23.328 129.252 292.457  1.00  0.00           P
ATOM   1907  P   G A1907    20.356 133.584 289.902  1.00  0.00           P
ATOM   1908  P   C A1908    17.360 135.351 286.748  1.00  0.00           P
ATOM   1909  P   C A1909    13.894 133.985 282.764  1.00  0.00           P
ATOM   1910  P   G A1910     9.996 131.168 280.797  1.00  0.00           P
ATOM   1911  P   U A1911     5.769 126.704 279.970  1.00  0.00           P
ATOM   1912  P   A A1912     0.405 123.716 282.448  1.00  0.00           P
ATOM   1913  P   A A1913    -5.011 124.299 283.726  1.00  0.00           P
ATOM   1914  P   C A1914    -9.263 128.019 285.991  1.00  0.00           P
ATOM   1915  P   U A1915    -5.757 131.898 287.676  1.00  0.00           P
ATOM   1916  P   A A1916    -1.064 132.679 289.535  1.00  0.00           P
ATOM   1917  P   U A1917     2.304 129.183 290.942  1.00  0.00           P
ATOM   1918  P   A A1918     6.573 125.995 290.845  1.00  0.00           P
ATOM   1919  P   A A1919     7.575 118.836 291.813  1.00  0.00           P
ATOM   1920  P   C A1920     9.986 116.802 287.916  1.00  0.00           P
ATOM   1921  P   G A1921    12.762 116.806 284.056  1.00  0.00           P
ATOM   1922  P   G A1922    14.991 117.636 280.431  1.00  0.00           P
ATOM   1923  P   U A1923    18.696 119.292 278.520  1.00  0.00           P
ATOM   1924  P   C A1924    22.441 122.784 278.351  1.00  0.00           P
ATOM   1925  P   C A1925    26.660 125.166 278.715  1.00  0.00           P
ATOM   1926  P   U A1926    29.913 126.051 282.811  1.00  0.00           P
ATOM   1927  P   A A1927    32.983 124.919 287.097  1.00  0.00           P
ATOM   1928  P   A A1928    34.539 122.139 291.101  1.00  0.00           P
ATOM   1929  P   G A1929    28.826 120.038 292.109  1.00  0.00           P
ATOM   1930  P   G A1930    24.913 122.222 296.652  1.00  0.00           P
ATOM   1931  P   U A1931    21.104 125.976 301.102  1.00  0.00           P
ATOM   1932  P   A A1932    17.871 121.286 304.517  1.00  0.00           P
ATOM   1933  P   G A1933    15.567 121.031 309.494  1.00  0.00           P
ATOM   1934  P   C A1934    13.476 126.036 313.339  1.00  0.00           P
ATOM   1935  P   G A1935    11.921 131.789 313.608  1.00  0.00           P
ATOM   1936  P   A A1936    11.754 136.818 309.347  1.00  0.00           P
ATOM   1937  P   A A1937    11.091 142.519 311.533  1.00  0.00           P
ATOM   1938  P   A A1938    15.467 141.675 315.324  1.00  0.00           P
ATOM   1939  P   U A1939    18.374 143.427 312.564  1.00  0.00           P
ATOM   1940  P   U A1940    18.898 144.137 306.695  1.00  0.00           P
ATOM   1941  P   C A1941    14.290 147.540 305.600  1.00  0.00           P
ATOM   1942  P   C A1942    14.299 147.761 298.659  1.00  0.00           P
ATOM   1943  P   U A1943     9.975 152.184 300.371  1.00  0.00           P
ATOM   1944  P   U A1944     8.794 152.301 305.376  1.00  0.00           P
ATOM   1945  P   G A1945     6.322 147.184 306.155  1.00  0.00           P
ATOM   1946  P   U A1946     1.567 146.431 303.112  1.00  0.00           P
ATOM   1947  P   C A1947    -3.337 143.703 304.044  1.00  0.00           P
ATOM   1948  P   G A1948    -6.558 141.524 308.105  1.00  0.00           P
ATOM   1949  P   G A1949    -7.626 140.649 313.977  1.00  0.00           P
ATOM   1950  P   G A1950    -7.470 141.323 319.547  1.00  0.00           P
ATOM   1951  P   U A1951    -7.311 145.891 322.891  1.00  0.00           P
ATOM   1952  P   A A1952    -9.082 151.158 322.562  1.00  0.00           P
ATOM   1953  P   A A1953    -8.313 151.189 317.117  1.00  0.00           P
ATOM   1954  P   G A1954    -3.634 151.663 313.786  1.00  0.00           P
ATOM   1955  P   U A1955     1.911 150.218 312.562  1.00  0.00           P
ATOM   1956  P   U A1956     6.609 150.211 312.206  1.00  0.00           P
ATOM   1957  P   C A1957     9.313 147.440 316.988  1.00  0.00           P
ATOM   1958  P   C A1958     9.016 141.696 319.348  1.00  0.00           P
ATOM   1959  P   G A1959     6.290 135.423 317.735  1.00  0.00           P
ATOM   1960  P   A A1960     4.412 131.919 313.901  1.00  0.00           P
ATOM   1961  P   C A1961     3.566 130.425 308.258  1.00  0.00           P
ATOM   1962  P   C A1962     5.260 130.364 303.506  1.00  0.00           P
ATOM   1963  P   U A1963     9.243 132.530 299.192  1.00  0.00           P
ATOM   1964  P   G A1964    12.160 135.921 298.035  1.00  0.00           P
ATOM   1965  P   C A1965    15.635 137.614 301.898  1.00  0.00           P
ATOM   1966  P   A A1966    20.394 139.357 302.101  1.00  0.00           P
ATOM   1967  P   C A1967    20.257 136.679 307.147  1.00  0.00           P
ATOM   1968  P   G A1968    25.305 134.800 308.039  1.00  0.00           P
```

| | | | | | | | | | |
|---|---|---|---|---|---|---|---|---|---|
| ATOM | 1969 | P | A | A1969 | 25.312 | 130.023 | 307.254 | 1.00 | 0.00 | P |
| ATOM | 1970 | P | A | A1970 | 28.509 | 126.202 | 310.404 | 1.00 | 0.00 | P |
| ATOM | 1971 | P | A | A1971 | 32.575 | 128.543 | 312.878 | 1.00 | 0.00 | P |
| ATOM | 1972 | P | A | A1972 | 32.121 | 132.814 | 315.309 | 1.00 | 0.00 | P |
| ATOM | 1973 | P | G | A1973 | 26.278 | 130.882 | 315.297 | 1.00 | 0.00 | P |
| ATOM | 1974 | P | C | A1974 | 20.979 | 130.524 | 314.568 | 1.00 | 0.00 | P |
| ATOM | 1975 | P | G | A1975 | 15.769 | 129.485 | 317.397 | 1.00 | 0.00 | P |
| ATOM | 1976 | P | U | A1976 | 13.310 | 129.035 | 322.818 | 1.00 | 0.00 | P |
| ATOM | 1977 | P | A | A1977 | 13.591 | 129.953 | 328.742 | 1.00 | 0.00 | P |
| ATOM | 1978 | P | A | A1978 | 14.919 | 129.784 | 334.721 | 1.00 | 0.00 | P |
| ATOM | 1979 | P | C | A1979 | 16.984 | 134.433 | 338.533 | 1.00 | 0.00 | P |
| ATOM | 1980 | P | G | A1980 | 18.963 | 139.779 | 338.242 | 1.00 | 0.00 | P |
| ATOM | 1981 | P | A | A1981 | 22.710 | 144.839 | 336.332 | 1.00 | 0.00 | P |
| ATOM | 1982 | P | C | A1982 | 19.563 | 146.806 | 332.861 | 1.00 | 0.00 | P |
| ATOM | 1983 | P | C | A1983 | 18.844 | 149.523 | 327.814 | 1.00 | 0.00 | P |
| ATOM | 1984 | P | G | A1984 | 15.079 | 150.687 | 324.108 | 1.00 | 0.00 | P |
| ATOM | 1985 | P | G | A1985 | 9.419 | 150.748 | 322.743 | 1.00 | 0.00 | P |
| ATOM | 1986 | P | A | A1986 | 3.677 | 149.795 | 323.732 | 1.00 | 0.00 | P |
| ATOM | 1987 | P | G | A1987 | -1.146 | 148.998 | 326.888 | 1.00 | 0.00 | P |
| ATOM | 1988 | P | C | A1988 | -3.435 | 147.018 | 332.532 | 1.00 | 0.00 | P |
| ATOM | 1989 | P | G | A1989 | -4.631 | 148.877 | 338.193 | 1.00 | 0.00 | P |
| ATOM | 1990 | P | C | A1990 | -2.114 | 153.495 | 342.251 | 1.00 | 0.00 | P |
| ATOM | 1991 | P | U | A1991 | 0.101 | 157.998 | 343.017 | 1.00 | 0.00 | P |
| ATOM | 1992 | P | G | A1992 | -1.068 | 163.415 | 341.588 | 1.00 | 0.00 | P |
| ATOM | 1993 | P | U | A1993 | 2.753 | 167.483 | 340.924 | 1.00 | 0.00 | P |
| ATOM | 1994 | P | C | A1994 | 6.050 | 166.739 | 335.328 | 1.00 | 0.00 | P |
| ATOM | 1995 | P | U | A1995 | 3.380 | 168.859 | 330.665 | 1.00 | 0.00 | P |
| ATOM | 1996 | P | C | A1996 | -3.324 | 172.668 | 329.430 | 1.00 | 0.00 | P |
| ATOM | 1997 | P | G | A1997 | 3.768 | 174.302 | 331.688 | 1.00 | 0.00 | P |
| ATOM | 1998 | P | G | A1998 | 2.443 | 178.090 | 336.226 | 1.00 | 0.00 | P |
| ATOM | 1999 | P | C | A1999 | 1.080 | 181.880 | 341.450 | 1.00 | 0.00 | P |
| ATOM | 2000 | P | G | A2000 | 1.614 | 182.839 | 347.204 | 1.00 | 0.00 | P |
| ATOM | 2001 | P | A | A2001 | 3.603 | 181.785 | 352.893 | 1.00 | 0.00 | P |
| ATOM | 2002 | P | G | A2002 | 7.251 | 180.778 | 356.622 | 1.00 | 0.00 | P |
| ATOM | 2003 | P | G | A2003 | 12.779 | 180.192 | 357.711 | 1.00 | 0.00 | P |
| ATOM | 2004 | P | G | A2004 | 18.460 | 180.051 | 355.929 | 1.00 | 0.00 | P |
| ATOM | 2005 | P | A | A2005 | 22.268 | 181.866 | 350.447 | 1.00 | 0.00 | P |
| ATOM | 2006 | P | C | A2006 | 23.128 | 186.959 | 346.646 | 1.00 | 0.00 | P |
| ATOM | 2007 | P | C | A2007 | 21.215 | 192.982 | 345.027 | 1.00 | 0.00 | P |
| ATOM | 2008 | P | C | A2008 | 20.889 | 198.331 | 347.459 | 1.00 | 0.00 | P |
| ATOM | 2009 | P | G | A2009 | 23.785 | 200.943 | 351.328 | 1.00 | 0.00 | P |
| ATOM | 2010 | P | G | A2010 | 28.540 | 200.974 | 354.654 | 1.00 | 0.00 | P |
| ATOM | 2011 | P | U | A2011 | 33.894 | 199.279 | 356.111 | 1.00 | 0.00 | P |
| ATOM | 2012 | P | G | A2012 | 38.482 | 194.783 | 351.872 | 1.00 | 0.00 | P |
| ATOM | 2013 | P | A | A2013 | 42.042 | 194.341 | 345.968 | 1.00 | 0.00 | P |
| ATOM | 2014 | P | A | A2014 | 40.022 | 191.605 | 340.487 | 1.00 | 0.00 | P |
| ATOM | 2015 | P | A | A2015 | 42.331 | 187.508 | 335.090 | 1.00 | 0.00 | P |
| ATOM | 2016 | P | U | A2016 | 39.510 | 187.146 | 328.818 | 1.00 | 0.00 | P |
| ATOM | 2017 | P | U | A2017 | 40.214 | 189.100 | 323.133 | 1.00 | 0.00 | P |
| ATOM | 2018 | P | G | A2018 | 41.077 | 193.734 | 323.275 | 1.00 | 0.00 | P |
| ATOM | 2019 | P | A | A2019 | 40.996 | 199.545 | 321.222 | 1.00 | 0.00 | P |
| ATOM | 2020 | P | A | A2020 | 37.945 | 204.738 | 323.040 | 1.00 | 0.00 | P |
| ATOM | 2021 | P | C | A2021 | 31.818 | 207.099 | 322.827 | 1.00 | 0.00 | P |
| ATOM | 2022 | P | U | A2022 | 26.642 | 206.309 | 320.677 | 1.00 | 0.00 | P |
| ATOM | 2023 | P | G | A2023 | 22.196 | 203.133 | 320.315 | 1.00 | 0.00 | P |
| ATOM | 2024 | P | G | A2024 | 18.239 | 198.843 | 316.710 | 1.00 | 0.00 | P |
| ATOM | 2025 | P | C | A2025 | 14.449 | 197.365 | 312.625 | 1.00 | 0.00 | P |
| ATOM | 2026 | P | C | A2026 | 11.617 | 197.603 | 307.040 | 1.00 | 0.00 | P |
| ATOM | 2027 | P | G | A2027 | 14.636 | 198.570 | 301.221 | 1.00 | 0.00 | P |
| ATOM | 2028 | P | U | A2028 | 20.496 | 198.227 | 297.717 | 1.00 | 0.00 | P |
| ATOM | 2029 | P | G | A2029 | 26.325 | 198.754 | 296.525 | 1.00 | 0.00 | P |
| ATOM | 2030 | P | A | A2030 | 31.485 | 196.617 | 297.450 | 1.00 | 0.00 | P |
| ATOM | 2031 | P | A | A2031 | 29.252 | 193.730 | 301.197 | 1.00 | 0.00 | P |
| ATOM | 2032 | P | G | A2032 | 24.830 | 189.277 | 302.284 | 1.00 | 0.00 | P |
| ATOM | 2033 | P | A | A2033 | 24.705 | 193.002 | 306.948 | 1.00 | 0.00 | P |
| ATOM | 2034 | P | U | A2034 | 24.468 | 198.021 | 312.535 | 1.00 | 0.00 | P |
| ATOM | 2035 | P | G | A2035 | 24.398 | 201.756 | 311.800 | 1.00 | 0.00 | P |
| ATOM | 2036 | P | C | A2036 | 27.469 | 206.828 | 310.572 | 1.00 | 0.00 | P |
| ATOM | 2037 | P | G | A2037 | 27.699 | 208.031 | 305.471 | 1.00 | 0.00 | P |
| ATOM | 2038 | P | G | A2038 | 22.298 | 210.453 | 302.677 | 1.00 | 0.00 | P |
| ATOM | 2039 | P | C | A2039 | 16.644 | 213.132 | 304.236 | 1.00 | 0.00 | P |
| ATOM | 2040 | P | C | A2040 | 11.662 | 212.470 | 308.692 | 1.00 | 0.00 | P |
| ATOM | 2041 | P | U | A2041 | 9.006 | 210.740 | 313.575 | 1.00 | 0.00 | P |
| ATOM | 2042 | P | A | A2042 | 9.564 | 210.069 | 320.096 | 1.00 | 0.00 | P |
| ATOM | 2043 | P | C | A2043 | 16.269 | 211.957 | 324.594 | 1.00 | 0.00 | P |
| ATOM | 2044 | P | C | A2044 | 22.409 | 211.867 | 328.066 | 1.00 | 0.00 | P |
| ATOM | 2045 | P | C | A2045 | 25.075 | 208.462 | 332.897 | 1.00 | 0.00 | P |
| ATOM | 2046 | P | G | A2046 | 25.293 | 205.136 | 337.016 | 1.00 | 0.00 | P |
| ATOM | 2047 | P | U | A2047 | 23.973 | 199.793 | 339.182 | 1.00 | 0.00 | P |
| ATOM | 2048 | P | G | A2048 | 20.806 | 194.777 | 340.443 | 1.00 | 0.00 | P |
| ATOM | 2049 | P | G | A2049 | 18.200 | 190.192 | 338.408 | 1.00 | 0.00 | P |
| ATOM | 2050 | P | C | A2050 | 17.568 | 185.501 | 334.052 | 1.00 | 0.00 | P |
| ATOM | 2051 | P | A | A2051 | 17.768 | 184.070 | 328.690 | 1.00 | 0.00 | P |
| ATOM | 2052 | P | G | A2052 | 18.081 | 185.176 | 322.503 | 1.00 | 0.00 | P |
| ATOM | 2053 | P | G | A2053 | 21.399 | 187.206 | 317.309 | 1.00 | 0.00 | P |
| ATOM | 2054 | P | A | A2054 | 26.078 | 188.789 | 316.211 | 1.00 | 0.00 | P |
| ATOM | 2055 | P | C | A2055 | 31.339 | 191.026 | 315.980 | 1.00 | 0.00 | P |

```
ATOM   2056  P    G A2056     30.928 185.198 316.885  1.00  0.00           P
ATOM   2057  P    A A2057     35.107 186.519 320.297  1.00  0.00           P
ATOM   2058  P    A A2058     36.632 183.494 323.784  1.00  0.00           P
ATOM   2059  P    A A2059     40.552 180.265 322.959  1.00  0.00           P
ATOM   2060  P    A A2060     45.761 179.532 321.706  1.00  0.00           P
ATOM   2061  P    G A2061     43.969 177.818 315.226  1.00  0.00           P
ATOM   2062  P    A A2062     42.773 173.259 312.673  1.00  0.00           P
ATOM   2063  P    C A2063     39.894 169.426 314.375  1.00  0.00           P
ATOM   2064  P    C A2064     35.899 166.493 309.061  1.00  0.00           P
ATOM   2065  P    C A2065     37.431 166.785 303.853  1.00  0.00           P
ATOM   2066  P    C A2066     41.584 167.742 299.420  1.00  0.00           P
ATOM   2067  P    G A2067     47.317 168.993 298.042  1.00  0.00           P
ATOM   2068  P    U A2068     53.325 170.208 299.527  1.00  0.00           P
ATOM   2069  P    G A2069     55.636 165.213 300.957  1.00  0.00           P
ATOM   2070  P    G A2070     55.136 163.103 305.957  1.00  0.00           P
ATOM   2071  P    A A2071     55.251 161.314 310.690  1.00  0.00           P
ATOM   2072  P    G A2072     54.019 157.589 314.039  1.00  0.00           P
ATOM   2073  P    C A2073     51.553 152.830 315.031  1.00  0.00           P
ATOM   2074  P    U A2074     49.304 147.578 312.688  1.00  0.00           P
ATOM   2075  P    U A2075     48.568 142.889 308.299  1.00  0.00           P
ATOM   2076  P    U A2076     50.792 140.011 300.749  1.00  0.00           P
ATOM   2077  P    A A2077     53.696 143.733 297.770  1.00  0.00           P
ATOM   2078  P    C A2078     59.108 144.613 296.212  1.00  0.00           P
ATOM   2079  P    U A2079     64.231 142.571 295.586  1.00  0.00           P
ATOM   2080  P    G A2080     68.268 145.246 300.037  1.00  0.00           P
ATOM   2081  P    C A2081     69.076 142.108 304.670  1.00  0.00           P
ATOM   2082  P    A A2082     69.688 141.139 309.650  1.00  0.00           P
ATOM   2083  P    G A2083     66.908 137.664 313.871  1.00  0.00           P
ATOM   2084  P    C A2084     66.761 131.390 314.416  1.00  0.00           P
ATOM   2085  P    C A2085     65.997 126.084 312.048  1.00  0.00           P
ATOM   2086  P    U A2086     67.008 123.028 307.500  1.00  0.00           P
ATOM   2087  P    G A2087     71.600 121.406 303.212  1.00  0.00           P
ATOM   2088  P    G A2088     77.667 120.270 302.729  1.00  0.00           P
ATOM   2089  P    U A2089     83.179 121.673 303.501  1.00  0.00           P
ATOM   2090  P    G A2090     87.519 122.821 307.057  1.00  0.00           P
ATOM   2091  P    U A2091     89.792 121.992 312.360  1.00  0.00           P
ATOM   2092  P    U A2092     88.091 118.475 316.151  1.00  0.00           P
ATOM   2093  P    G A2093     91.703 115.093 311.474  1.00  0.00           P
ATOM   2094  P    G A2094     92.309 108.880 311.746  1.00  0.00           P
ATOM   2095  P    C A2095     91.945 103.140 309.813  1.00  0.00           P
ATOM   2096  P    U A2096     89.986  98.807 305.851  1.00  0.00           P
ATOM   2097  P    C A2097     86.643  96.284 303.199  1.00  0.00           P
ATOM   2098  P    U A2098     81.909  96.909 301.189  1.00  0.00           P
ATOM   2099  P    U A2099     79.316  97.053 297.319  1.00  0.00           P
ATOM   2100  P    G A2100     76.185  99.252 293.223  1.00  0.00           P
ATOM   2101  P    G A2101     75.640 102.261 289.124  1.00  0.00           P
ATOM   2102  P    U A2102     77.375 106.749 285.219  1.00  0.00           P
ATOM   2103  P    C A2103     79.672 109.187 280.658  1.00  0.00           P
ATOM   2104  P    G A2104     84.295 110.955 277.571  1.00  0.00           P
ATOM   2105  P    C A2105     89.349 109.179 276.593  1.00  0.00           P
ATOM   2106  P    G A2106     93.109 105.299 275.604  1.00  0.00           P
ATOM   2107  P    C A2107     94.833 100.141 274.905  1.00  0.00           P
ATOM   2108  P    C A2108     93.233  95.064 271.911  1.00  0.00           P
ATOM   2109  P    U A2109     86.961  92.524 271.607  1.00  0.00           P
ATOM   2110  P    G A2110     82.055  90.786 267.806  1.00  0.00           P
ATOM   2111  P    C A2111     77.416  93.836 265.228  1.00  0.00           P
ATOM   2112  P    G A2112     71.964  96.382 262.057  1.00  0.00           P
ATOM   2113  P    U A2113     67.764  96.364 256.354  1.00  0.00           P
ATOM   2114  P    A A2114     69.975  96.952 250.687  1.00  0.00           P
ATOM   2115  P    G A2115     75.817  96.437 246.611  1.00  0.00           P
ATOM   2116  P    G A2116     74.470 102.798 245.214  1.00  0.00           P
ATOM   2117  P    A A2117     74.204 101.006 251.732  1.00  0.00           P
ATOM   2118  P    U A2118     77.757  96.398 251.056  1.00  0.00           P
ATOM   2119  P    A A2119     76.915  95.354 256.573  1.00  0.00           P
ATOM   2120  P    G A2120     79.255  95.868 262.309  1.00  0.00           P
ATOM   2121  P    G A2121     78.850  98.845 257.945  1.00  0.00           P
ATOM   2122  P    U A2122     79.623 102.746 254.538  1.00  0.00           P
ATOM   2123  P    G A2123     82.822 106.163 252.014  1.00  0.00           P
ATOM   2124  P    G A2124     86.411 104.710 247.908  1.00  0.00           P
ATOM   2125  P    G A2125     83.565  99.138 246.969  1.00  0.00           P
ATOM   2126  P    A A2126     83.239  93.177 247.083  1.00  0.00           P
ATOM   2127  P    G A2127     86.864  89.698 246.957  1.00  0.00           P
ATOM   2128  P    C A2128     92.718  92.325 245.754  1.00  0.00           P
ATOM   2129  P    C A2129     98.830  91.477 243.942  1.00  0.00           P
ATOM   2130  P    U A2130    102.080  89.685 249.688  1.00  0.00           P
ATOM   2131  P    G A2131     99.544  88.356 256.095  1.00  0.00           P
ATOM   2132  P    U A2132    100.562  85.415 262.598  1.00  0.00           P
ATOM   2133  P    G A2133    104.852  80.259 263.389  1.00  0.00           P
ATOM   2134  P    A A2134    102.779  75.428 262.030  1.00  0.00           P
ATOM   2135  P    A A2135     97.750  76.686 261.603  1.00  0.00           P
ATOM   2136  P    C A2136     93.392  78.713 259.302  1.00  0.00           P
ATOM   2137  P    C A2137     89.473  77.735 255.868  1.00  0.00           P
ATOM   2138  P    C A2138     85.239  74.142 254.622  1.00  0.00           P
ATOM   2139  P    C A2139     81.452  70.044 256.298  1.00  0.00           P
ATOM   2140  P    C A2140     79.879  66.392 262.084  1.00  0.00           P
ATOM   2141  P    G A2141     79.069  66.860 268.103  1.00  0.00           P
ATOM   2142  P    C A2142     79.740  69.489 273.178  1.00  0.00           P
```

```
ATOM   2143  P    C A2143      79.300  74.106 276.448  1.00  0.00           P
ATOM   2144  P    U A2144      78.534  80.777 276.316  1.00  0.00           P
ATOM   2145  P    C A2145      75.918  84.191 274.617  1.00  0.00           P
ATOM   2146  P    C A2146      76.853  85.529 268.788  1.00  0.00           P
ATOM   2147  P    G A2147      81.391  85.730 265.176  1.00  0.00           P
ATOM   2148  P    G A2148      87.307  86.263 263.659  1.00  0.00           P
ATOM   2149  P    G A2149      89.249  83.106 265.635  1.00  0.00           P
ATOM   2150  P    U A2150      91.956  80.301 268.918  1.00  0.00           P
ATOM   2151  P    G A2151      92.909  75.911 270.458  1.00  0.00           P
ATOM   2152  P    G A2152      93.931  69.866 270.268  1.00  0.00           P
ATOM   2153  P    G A2153      93.470  64.333 267.739  1.00  0.00           P
ATOM   2154  P    G A2154      93.319  61.215 262.756  1.00  0.00           P
ATOM   2155  P    G A2155      93.904  61.003 256.785  1.00  0.00           P
ATOM   2156  P    G A2156      95.340  64.619 251.833  1.00  0.00           P
ATOM   2157  P    G A2157      93.730  67.338 247.400  1.00  0.00           P
ATOM   2158  P    A A2158      91.408  72.361 249.446  1.00  0.00           P
ATOM   2159  P    G A2159      96.165  74.786 248.325  1.00  0.00           P
ATOM   2160  P    G A2160      98.931  76.773 252.707  1.00  0.00           P
ATOM   2161  P    C A2161      98.472  81.343 256.551  1.00  0.00           P
ATOM   2162  P    G A2162      94.239  77.167 253.479  1.00  0.00           P
ATOM   2163  P    C A2163      89.465  78.234 251.066  1.00  0.00           P
ATOM   2164  P    C A2164      89.208  83.562 248.550  1.00  0.00           P
ATOM   2165  P    G A2165      90.821  86.320 243.110  1.00  0.00           P
ATOM   2166  P    G A2166      86.192  89.301 239.536  1.00  0.00           P
ATOM   2167  P    U A2167      79.336  91.076 239.802  1.00  0.00           P
ATOM   2168  P    G A2168      72.519  94.436 241.672  1.00  0.00           P
ATOM   2169  P    A A2169      70.999  90.967 247.414  1.00  0.00           P
ATOM   2170  P    A A2170      75.018  87.903 250.709  1.00  0.00           P
ATOM   2171  P    A A2171      79.716  92.303 248.547  1.00  0.00           P
ATOM   2172  P    U A2172      85.799  91.704 252.516  1.00  0.00           P
ATOM   2173  P    A A2173      92.449  92.974 253.443  1.00  0.00           P
ATOM   2174  P    C A2174      97.417  95.182 258.915  1.00  0.00           P
ATOM   2175  P    C A2175      98.188  99.752 261.963  1.00  0.00           P
ATOM   2176  P    A A2176      94.520 104.656 264.475  1.00  0.00           P
ATOM   2177  P    C A2177      90.115 108.213 265.981  1.00  0.00           P
ATOM   2178  P    C A2178      84.210 107.721 267.896  1.00  0.00           P
ATOM   2179  P    C A2179      77.850 105.837 270.853  1.00  0.00           P
ATOM   2180  P    U A2180      75.549 101.435 274.443  1.00  0.00           P
ATOM   2181  P    G A2181      77.169  98.016 278.089  1.00  0.00           P
ATOM   2182  P    G A2182      78.841  95.310 281.805  1.00  0.00           P
ATOM   2183  P    C A2183      82.830  94.236 285.372  1.00  0.00           P
ATOM   2184  P    G A2184      87.901  95.241 287.051  1.00  0.00           P
ATOM   2185  P    C A2185      92.463  97.934 289.308  1.00  0.00           P
ATOM   2186  P    G A2186      94.541 102.988 290.061  1.00  0.00           P
ATOM   2187  P    G A2187      93.619 108.885 291.142  1.00  0.00           P
ATOM   2188  P    C A2188      89.804 113.207 291.784  1.00  0.00           P
ATOM   2189  P    U A2189      85.872 114.158 293.876  1.00  0.00           P
ATOM   2190  P    G A2190      80.497 113.582 294.148  1.00  0.00           P
ATOM   2191  P    G A2191      76.104 112.873 296.901  1.00  0.00           P
ATOM   2192  P    G A2192      74.954 109.026 299.746  1.00  0.00           P
ATOM   2193  P    G A2193      73.534 105.259 303.208  1.00  0.00           P
ATOM   2194  P    G A2194      73.613 102.405 307.983  1.00  0.00           P
ATOM   2195  P    C A2195      76.377 100.940 312.921  1.00  0.00           P
ATOM   2196  P    C A2196      79.881 100.483 317.869  1.00  0.00           P
ATOM   2197  P    U A2197      84.015 104.066 321.883  1.00  0.00           P
ATOM   2198  P    A A2198      88.062 108.757 323.761  1.00  0.00           P
ATOM   2199  P    A A2199      87.819 114.659 323.597  1.00  0.00           P
ATOM   2200  P    C A2205      82.684 119.499 322.614  1.00  0.00           P
ATOM   2201  P    C A2206      77.755 121.372 325.716  1.00  0.00           P
ATOM   2202  P    C A2207      73.225 118.162 329.056  1.00  0.00           P
ATOM   2203  P    U A2208      71.161 115.786 333.441  1.00  0.00           P
ATOM   2204  P    C A2209      72.052 113.011 338.340  1.00  0.00           P
ATOM   2205  P    G A2210      76.301 110.793 339.286  1.00  0.00           P
ATOM   2206  P    G A2211      79.021 110.167 343.286  1.00  0.00           P
ATOM   2207  P    A A2212      83.431 113.537 341.783  1.00  0.00           P
ATOM   2208  P    U A2213      87.400 111.848 338.626  1.00  0.00           P
ATOM   2209  P    G A2215      88.855 111.953 333.771  1.00  0.00           P
ATOM   2210  P    G A2216      86.925 106.820 333.733  1.00  0.00           P
ATOM   2211  P    G A2217      82.038 103.132 332.454  1.00  0.00           P
ATOM   2212  P    G A2218      76.900 101.907 329.483  1.00  0.00           P
ATOM   2213  P    G A2219      74.068 103.949 324.175  1.00  0.00           P
ATOM   2214  P    G A2224      75.025 107.981 318.686  1.00  0.00           P
ATOM   2215  P    A A2225      77.931 111.914 313.944  1.00  0.00           P
ATOM   2216  P    C A2226      80.663 115.995 311.016  1.00  0.00           P
ATOM   2217  P    A A2227      74.632 117.806 313.194  1.00  0.00           P
ATOM   2218  P    G A2228      72.960 122.410 315.918  1.00  0.00           P
ATOM   2219  P    C A2229      73.841 126.956 318.330  1.00  0.00           P
ATOM   2220  P    G A2230      77.066 131.610 317.462  1.00  0.00           P
ATOM   2221  P    C A2231      80.339 135.158 313.311  1.00  0.00           P
ATOM   2222  P    U A2232      81.090 136.360 307.379  1.00  0.00           P
ATOM   2223  P    U A2233      78.644 135.763 301.683  1.00  0.00           P
ATOM   2224  P    G A2234      74.145 133.993 298.039  1.00  0.00           P
ATOM   2225  P    A A2235      67.828 133.488 296.604  1.00  0.00           P
ATOM   2226  P    C A2236      62.672 133.034 298.444  1.00  0.00           P
ATOM   2227  P    G A2237      58.356 133.567 302.277  1.00  0.00           P
ATOM   2228  P    G A2238      56.537 136.680 306.029  1.00  0.00           P
ATOM   2229  P    G A2239      57.396 138.457 311.742  1.00  0.00           P
```

| | | | | | | | |
|---|---|---|---|---|---|---|---|
| ATOM | 2230 | P | C A2240 | 56.666 144.687 314.901 | 1.00 | 0.00 | P |
| ATOM | 2231 | P | A A2241 | 61.048 149.329 313.868 | 1.00 | 0.00 | P |
| ATOM | 2232 | P | G A2242 | 61.713 154.241 311.807 | 1.00 | 0.00 | P |
| ATOM | 2233 | P | U A2243 | 62.775 158.259 306.669 | 1.00 | 0.00 | P |
| ATOM | 2234 | P | U A2244 | 58.878 157.446 300.856 | 1.00 | 0.00 | P |
| ATOM | 2235 | P | U A2245 | 54.363 158.796 296.441 | 1.00 | 0.00 | P |
| ATOM | 2236 | P | G A2246 | 50.321 161.289 293.790 | 1.00 | 0.00 | P |
| ATOM | 2237 | P | A A2247 | 47.570 166.491 294.023 | 1.00 | 0.00 | P |
| ATOM | 2238 | P | C A2248 | 44.358 170.134 290.256 | 1.00 | 0.00 | P |
| ATOM | 2239 | P | U A2249 | 40.266 172.366 288.263 | 1.00 | 0.00 | P |
| ATOM | 2240 | P | G A2250 | 35.445 172.651 287.598 | 1.00 | 0.00 | P |
| ATOM | 2241 | P | G A2251 | 33.853 173.059 292.149 | 1.00 | 0.00 | P |
| ATOM | 2242 | P | G A2252 | 35.210 168.789 294.932 | 1.00 | 0.00 | P |
| ATOM | 2243 | P | G A2253 | 34.442 162.425 294.873 | 1.00 | 0.00 | P |
| ATOM | 2244 | P | C A2254 | 37.761 158.013 292.537 | 1.00 | 0.00 | P |
| ATOM | 2245 | P | G A2255 | 36.564 155.872 286.805 | 1.00 | 0.00 | P |
| ATOM | 2246 | P | G A2256 | 37.620 158.046 281.299 | 1.00 | 0.00 | P |
| ATOM | 2247 | P | U A2257 | 42.154 160.734 279.199 | 1.00 | 0.00 | P |
| ATOM | 2248 | P | C A2258 | 46.885 162.738 279.046 | 1.00 | 0.00 | P |
| ATOM | 2249 | P | G A2259 | 52.942 165.702 278.514 | 1.00 | 0.00 | P |
| ATOM | 2250 | P | C A2260 | 53.586 166.168 272.213 | 1.00 | 0.00 | P |
| ATOM | 2251 | P | C A2261 | 52.633 166.926 266.331 | 1.00 | 0.00 | P |
| ATOM | 2252 | P | U A2262 | 48.556 169.111 261.797 | 1.00 | 0.00 | P |
| ATOM | 2253 | P | C A2263 | 43.212 172.098 259.131 | 1.00 | 0.00 | P |
| ATOM | 2254 | P | C A2264 | 38.173 175.817 259.927 | 1.00 | 0.00 | P |
| ATOM | 2255 | P | U A2265 | 35.690 178.480 264.804 | 1.00 | 0.00 | P |
| ATOM | 2256 | P | A A2266 | 38.657 183.995 266.278 | 1.00 | 0.00 | P |
| ATOM | 2257 | P | A A2267 | 39.841 184.725 261.430 | 1.00 | 0.00 | P |
| ATOM | 2258 | P | A A2268 | 38.902 189.033 261.003 | 1.00 | 0.00 | P |
| ATOM | 2259 | P | A A2269 | 43.119 188.037 259.597 | 1.00 | 0.00 | P |
| ATOM | 2260 | P | G A2270 | 47.322 184.241 259.718 | 1.00 | 0.00 | P |
| ATOM | 2261 | P | G A2271 | 50.082 182.289 264.159 | 1.00 | 0.00 | P |
| ATOM | 2262 | P | U A2272 | 49.005 180.141 268.501 | 1.00 | 0.00 | P |
| ATOM | 2263 | P | A A2273 | 45.274 178.720 272.322 | 1.00 | 0.00 | P |
| ATOM | 2264 | P | A A2274 | 42.859 175.520 276.615 | 1.00 | 0.00 | P |
| ATOM | 2265 | P | C A2275 | 39.803 172.349 278.940 | 1.00 | 0.00 | P |
| ATOM | 2266 | P | G A2276 | 35.720 173.650 276.835 | 1.00 | 0.00 | P |
| ATOM | 2267 | P | G A2277 | 32.857 170.095 273.047 | 1.00 | 0.00 | P |
| ATOM | 2268 | P | A A2278 | 30.842 167.342 268.800 | 1.00 | 0.00 | P |
| ATOM | 2269 | P | G A2279 | 32.146 163.260 265.432 | 1.00 | 0.00 | P |
| ATOM | 2270 | P | G A2280 | 37.137 159.260 264.416 | 1.00 | 0.00 | P |
| ATOM | 2271 | P | C A2281 | 43.383 156.780 263.991 | 1.00 | 0.00 | P |
| ATOM | 2272 | P | G A2282 | 48.835 155.491 265.022 | 1.00 | 0.00 | P |
| ATOM | 2273 | P | C A2283 | 54.018 152.211 266.606 | 1.00 | 0.00 | P |
| ATOM | 2274 | P | C A2284 | 53.697 148.352 259.779 | 1.00 | 0.00 | P |
| ATOM | 2275 | P | C A2285 | 54.999 144.953 253.918 | 1.00 | 0.00 | P |
| ATOM | 2276 | P | A A2286 | 57.716 145.996 249.859 | 1.00 | 0.00 | P |
| ATOM | 2277 | P | A A2287 | 61.034 145.148 246.701 | 1.00 | 0.00 | P |
| ATOM | 2278 | P | A A2288 | 61.251 150.626 245.324 | 1.00 | 0.00 | P |
| ATOM | 2279 | P | G A2289 | 62.651 153.362 241.442 | 1.00 | 0.00 | P |
| ATOM | 2280 | P | G A2290 | 64.661 159.101 241.548 | 1.00 | 0.00 | P |
| ATOM | 2281 | P | U A2291 | 64.437 162.732 235.968 | 1.00 | 0.00 | P |
| ATOM | 2282 | P | C A2292 | 63.615 162.098 229.896 | 1.00 | 0.00 | P |
| ATOM | 2283 | P | C A2293 | 59.116 159.408 225.627 | 1.00 | 0.00 | P |
| ATOM | 2284 | P | C A2294 | 52.985 158.155 224.276 | 1.00 | 0.00 | P |
| ATOM | 2285 | P | C A2295 | 46.514 157.455 228.341 | 1.00 | 0.00 | P |
| ATOM | 2286 | P | U A2296 | 40.058 158.427 230.801 | 1.00 | 0.00 | P |
| ATOM | 2287 | P | C A2297 | 37.441 156.178 235.140 | 1.00 | 0.00 | P |
| ATOM | 2288 | P | A A2298 | 34.133 156.604 238.329 | 1.00 | 0.00 | P |
| ATOM | 2289 | P | G A2299 | 29.343 156.807 239.475 | 1.00 | 0.00 | P |
| ATOM | 2290 | P | G A2300 | 24.096 156.910 236.717 | 1.00 | 0.00 | P |
| ATOM | 2291 | P | C A2301 | 21.084 156.390 231.854 | 1.00 | 0.00 | P |
| ATOM | 2292 | P | G A2302 | 19.984 153.661 226.818 | 1.00 | 0.00 | P |
| ATOM | 2293 | P | G A2303 | 20.100 149.776 223.800 | 1.00 | 0.00 | P |
| ATOM | 2294 | P | G A2304 | 22.060 143.999 223.018 | 1.00 | 0.00 | P |
| ATOM | 2295 | P | A A2305 | 24.284 137.999 222.861 | 1.00 | 0.00 | P |
| ATOM | 2296 | P | C A2306 | 22.542 135.155 228.477 | 1.00 | 0.00 | P |
| ATOM | 2297 | P | G A2307 | 22.999 134.250 233.413 | 1.00 | 0.00 | P |
| ATOM | 2298 | P | G A2308 | 22.310 138.811 237.583 | 1.00 | 0.00 | P |
| ATOM | 2299 | P | A A2309 | 21.711 145.298 240.384 | 1.00 | 0.00 | P |
| ATOM | 2300 | P | A A2310 | 24.687 146.916 236.961 | 1.00 | 0.00 | P |
| ATOM | 2301 | P | A A2311 | 28.348 145.840 237.287 | 1.00 | 0.00 | P |
| ATOM | 2302 | P | U A2312 | 33.992 144.811 236.480 | 1.00 | 0.00 | P |
| ATOM | 2303 | P | C A2313 | 36.144 143.321 231.488 | 1.00 | 0.00 | P |
| ATOM | 2304 | P | C A2314 | 36.646 147.145 226.265 | 1.00 | 0.00 | P |
| ATOM | 2305 | P | G A2315 | 35.591 151.297 222.388 | 1.00 | 0.00 | P |
| ATOM | 2306 | P | C A2316 | 34.338 156.467 221.097 | 1.00 | 0.00 | P |
| ATOM | 2307 | P | C A2317 | 32.118 161.740 222.138 | 1.00 | 0.00 | P |
| ATOM | 2308 | P | G A2318 | 31.351 164.993 227.137 | 1.00 | 0.00 | P |
| ATOM | 2309 | P | G A2319 | 34.133 167.139 231.246 | 1.00 | 0.00 | P |
| ATOM | 2310 | P | A A2320 | 36.005 168.749 236.614 | 1.00 | 0.00 | P |
| ATOM | 2311 | P | G A2321 | 34.468 166.700 242.476 | 1.00 | 0.00 | P |
| ATOM | 2312 | P | A A2322 | 35.978 160.767 244.027 | 1.00 | 0.00 | P |
| ATOM | 2313 | P | G A2323 | 39.845 155.840 243.907 | 1.00 | 0.00 | P |
| ATOM | 2314 | P | C A2324 | 44.600 154.351 246.213 | 1.00 | 0.00 | P |
| ATOM | 2315 | P | G A2325 | 48.801 155.909 249.057 | 1.00 | 0.00 | P |
| ATOM | 2316 | P | C A2326 | 45.457 154.645 253.046 | 1.00 | 0.00 | P |

```
ATOM   2317  P    A A2327     42.884 157.732 257.676  1.00  0.00           P
ATOM   2318  P    A A2328     39.847 162.569 257.368  1.00  0.00           P
ATOM   2319  P    G A2329     39.809 168.187 255.586  1.00  0.00           P
ATOM   2320  P    G A2330     41.323 171.753 250.894  1.00  0.00           P
ATOM   2321  P    G A2331     45.317 172.461 246.035  1.00  0.00           P
ATOM   2322  P    U A2332     46.429 169.609 240.454  1.00  0.00           P
ATOM   2323  P    A A2333     44.502 165.091 237.015  1.00  0.00           P
ATOM   2324  P    G A2334     42.016 167.466 234.322  1.00  0.00           P
ATOM   2325  P    A A2335     47.625 168.288 233.746  1.00  0.00           P
ATOM   2326  P    A A2336     52.023 166.265 237.549  1.00  0.00           P
ATOM   2327  P    G A2337     52.277 162.359 240.431  1.00  0.00           P
ATOM   2328  P    G A2338     50.098 156.591 240.771  1.00  0.00           P
ATOM   2329  P    G A2339     50.163 150.735 239.230  1.00  0.00           P
ATOM   2330  P    G A2340     52.607 146.976 235.519  1.00  0.00           P
ATOM   2331  P    G A2341     57.267 145.357 232.403  1.00  0.00           P
ATOM   2332  P    C A2342     63.443 146.081 230.765  1.00  0.00           P
ATOM   2333  P    C A2343     68.653 147.384 233.814  1.00  0.00           P
ATOM   2334  P    U A2344     71.560 149.798 238.452  1.00  0.00           P
ATOM   2335  P    G A2345     72.138 151.248 244.567  1.00  0.00           P
ATOM   2336  P    A A2346     72.883 156.588 249.322  1.00  0.00           P
ATOM   2337  P    C A2347     73.558 158.533 253.344  1.00  0.00           P
ATOM   2338  P    U A2348     77.748 159.672 255.253  1.00  0.00           P
ATOM   2339  P    G A2349     81.463 163.408 257.287  1.00  0.00           P
ATOM   2340  P    C A2350     82.534 168.947 258.386  1.00  0.00           P
ATOM   2341  P    G A2351     77.220 173.932 257.258  1.00  0.00           P
ATOM   2342  P    A A2352     75.655 179.766 257.304  1.00  0.00           P
ATOM   2343  P    G A2353     70.806 183.365 256.727  1.00  0.00           P
ATOM   2344  P    G A2354     64.711 184.188 257.389  1.00  0.00           P
ATOM   2345  P    C A2355     59.437 182.745 260.451  1.00  0.00           P
ATOM   2346  P    C A2356     57.510 180.520 266.005  1.00  0.00           P
ATOM   2347  P    U A2357     61.124 180.501 268.880  1.00  0.00           P
ATOM   2348  P    G A2358     59.821 181.794 273.597  1.00  0.00           P
ATOM   2349  P    C A2359     63.014 181.109 277.729  1.00  0.00           P
ATOM   2350  P    A A2360     65.890 179.025 275.180  1.00  0.00           P
ATOM   2351  P    A A2361     66.980 175.135 273.769  1.00  0.00           P
ATOM   2352  P    G A2362     66.995 170.799 271.128  1.00  0.00           P
ATOM   2353  P    C A2363     64.479 168.019 266.189  1.00  0.00           P
ATOM   2354  P    C A2364     62.152 167.381 260.857  1.00  0.00           P
ATOM   2355  P    G A2365     61.277 169.842 255.636  1.00  0.00           P
ATOM   2356  P    A A2366     64.348 171.498 249.470  1.00  0.00           P
ATOM   2357  P    G A2367     67.405 173.510 245.949  1.00  0.00           P
ATOM   2358  P    C A2368     73.740 175.297 244.650  1.00  0.00           P
ATOM   2359  P    A A2369     80.335 174.334 244.131  1.00  0.00           P
ATOM   2360  P    G A2370     84.314 170.225 243.273  1.00  0.00           P
ATOM   2361  P    G A2371     85.450 163.866 243.078  1.00  0.00           P
ATOM   2362  P    G A2372     83.838 157.614 241.498  1.00  0.00           P
ATOM   2363  P    G A2373     78.439 154.261 239.320  1.00  0.00           P
ATOM   2364  P    C A2374     73.766 152.616 236.019  1.00  0.00           P
ATOM   2365  P    G A2375     69.899 153.879 232.921  1.00  0.00           P
ATOM   2366  P    A A2376     68.074 156.473 228.586  1.00  0.00           P
ATOM   2367  P    A A2377     71.214 160.933 227.885  1.00  0.00           P
ATOM   2368  P    A A2378     70.990 166.306 231.157  1.00  0.00           P
ATOM   2369  P    G A2379     68.620 170.291 234.372  1.00  0.00           P
ATOM   2370  P    C A2380     66.328 168.539 239.460  1.00  0.00           P
ATOM   2371  P    C A2381     65.568 165.702 244.068  1.00  0.00           P
ATOM   2372  P    G A2382     67.835 164.109 249.611  1.00  0.00           P
ATOM   2373  P    G A2383     63.748 161.612 250.618  1.00  0.00           P
ATOM   2374  P    G A2384     58.385 161.201 248.342  1.00  0.00           P
ATOM   2375  P    C A2385     55.825 158.516 245.130  1.00  0.00           P
ATOM   2376  P    C A2386     52.574 162.015 246.424  1.00  0.00           P
ATOM   2377  P    U A2387     52.729 165.315 252.010  1.00  0.00           P
ATOM   2378  P    A A2388     52.521 166.423 258.546  1.00  0.00           P
ATOM   2379  P    G A2389     50.275 164.496 263.578  1.00  0.00           P
ATOM   2380  P    U A2390     53.925 159.693 263.697  1.00  0.00           P
ATOM   2381  P    G A2391     57.875 157.514 265.838  1.00  0.00           P
ATOM   2382  P    A A2392     62.000 159.178 270.593  1.00  0.00           P
ATOM   2383  P    A A2393     64.950 161.677 274.529  1.00  0.00           P
ATOM   2384  P    C A2394     70.605 163.227 274.697  1.00  0.00           P
ATOM   2385  P    C A2395     75.357 163.114 279.703  1.00  0.00           P
ATOM   2386  P    G A2396     76.925 156.771 281.276  1.00  0.00           P
ATOM   2387  P    G A2397     77.573 150.539 280.907  1.00  0.00           P
ATOM   2388  P    U A2398     78.002 145.320 277.111  1.00  0.00           P
ATOM   2389  P    G A2399     79.120 142.692 272.400  1.00  0.00           P
ATOM   2390  P    G A2400     82.506 143.130 267.535  1.00  0.00           P
ATOM   2391  P    U A2401     86.283 146.198 263.778  1.00  0.00           P
ATOM   2392  P    C A2402     89.243 149.611 262.458  1.00  0.00           P
ATOM   2393  P    C A2403     93.414 152.455 262.414  1.00  0.00           P
ATOM   2394  P    C A2404     96.546 155.141 265.937  1.00  0.00           P
ATOM   2395  P    G A2405     99.435 155.419 269.542  1.00  0.00           P
ATOM   2396  P    U A2406    100.534 157.156 274.555  1.00  0.00           P
ATOM   2397  P    G A2407     99.629 153.615 279.193  1.00  0.00           P
ATOM   2398  P    U A2408    105.649 155.410 281.601  1.00  0.00           P
ATOM   2399  P    G A2409    105.317 153.245 275.721  1.00  0.00           P
ATOM   2400  P    G A2410    103.394 148.333 272.015  1.00  0.00           P
ATOM   2401  P    A A2411     97.281 145.340 274.267  1.00  0.00           P
ATOM   2402  P    A A2412     91.365 144.964 278.239  1.00  0.00           P
ATOM   2403  P    G A2413     88.136 149.156 279.538  1.00  0.00           P
```

```
ATOM   2404  P     G A2414      85.537 154.983 277.827  1.00  0.00           P
ATOM   2405  P     G A2415      84.199 160.403 274.232  1.00  0.00           P
ATOM   2406  P     C A2416      82.576 161.496 269.222  1.00  0.00           P
ATOM   2407  P     C A2417      79.783 159.017 264.407  1.00  0.00           P
ATOM   2408  P     A A2418      75.771 155.437 263.483  1.00  0.00           P
ATOM   2409  P     U A2419      70.894 152.393 266.184  1.00  0.00           P
ATOM   2410  P     C A2420      68.295 148.088 270.355  1.00  0.00           P
ATOM   2411  P     G A2421      62.599 148.332 273.786  1.00  0.00           P
ATOM   2412  P     A A2422      57.185 150.746 276.318  1.00  0.00           P
ATOM   2413  P     U A2423      52.911 153.028 279.127  1.00  0.00           P
ATOM   2414  P     C A2424      55.667 158.579 281.596  1.00  0.00           P
ATOM   2415  P     A A2425      49.848 159.793 282.296  1.00  0.00           P
ATOM   2416  P     A A2426      54.268 164.228 281.658  1.00  0.00           P
ATOM   2417  P     C A2427      57.660 167.004 279.681  1.00  0.00           P
ATOM   2418  P     G A2428      60.685 164.679 279.318  1.00  0.00           P
ATOM   2419  P     G A2429      64.506 162.054 277.656  1.00  0.00           P
ATOM   2420  P     A A2430      61.741 157.696 279.270  1.00  0.00           P
ATOM   2421  P     U A2431      59.395 160.470 284.347  1.00  0.00           P
ATOM   2422  P     A A2432      61.171 160.802 290.978  1.00  0.00           P
ATOM   2423  P     A A2433      64.064 156.797 289.974  1.00  0.00           P
ATOM   2424  P     A A2434      60.614 151.846 292.183  1.00  0.00           P
ATOM   2425  P     A A2435      54.267 150.341 293.207  1.00  0.00           P
ATOM   2426  P     G A2436      48.533 151.639 295.464  1.00  0.00           P
ATOM   2427  P     U A2437      43.682 152.057 300.664  1.00  0.00           P
ATOM   2428  P     U A2438      39.696 153.866 305.209  1.00  0.00           P
ATOM   2429  P     A A2439      38.946 156.561 309.848  1.00  0.00           P
ATOM   2430  P     C A2440      39.579 157.450 316.119  1.00  0.00           P
ATOM   2431  P     C A2441      40.021 163.319 316.304  1.00  0.00           P
ATOM   2432  P     C A2442      44.372 165.839 317.314  1.00  0.00           P
ATOM   2433  P     C A2443      48.227 169.523 315.984  1.00  0.00           P
ATOM   2434  P     G A2444      50.413 174.038 313.820  1.00  0.00           P
ATOM   2435  P     G A2445      51.190 178.502 310.301  1.00  0.00           P
ATOM   2436  P     G A2446      46.447 180.484 305.399  1.00  0.00           P
ATOM   2437  P     G A2447      42.209 182.651 303.899  1.00  0.00           P
ATOM   2438  P     A A2448      38.110 182.470 299.541  1.00  0.00           P
ATOM   2439  P     U A2449      35.117 176.779 298.020  1.00  0.00           P
ATOM   2440  P     A A2450      33.822 171.131 298.014  1.00  0.00           P
ATOM   2441  P     A A2451      29.651 170.767 301.573  1.00  0.00           P
ATOM   2442  P     C A2452      25.486 171.605 303.169  1.00  0.00           P
ATOM   2443  P     A A2453      21.548 174.856 304.733  1.00  0.00           P
ATOM   2444  P     G A2454      19.448 179.812 302.966  1.00  0.00           P
ATOM   2445  P     G A2455      20.570 186.482 300.132  1.00  0.00           P
ATOM   2446  P     C A2456      20.042 188.245 293.748  1.00  0.00           P
ATOM   2447  P     U A2457      18.804 186.378 288.932  1.00  0.00           P
ATOM   2448  P     G A2458      15.509 181.235 288.967  1.00  0.00           P
ATOM   2449  P     A A2459      15.397 177.987 284.898  1.00  0.00           P
ATOM   2450  P     U A2460      12.428 174.286 283.812  1.00  0.00           P
ATOM   2451  P     C A2461       8.725 170.484 288.016  1.00  0.00           P
ATOM   2452  P     U A2462       4.922 171.418 292.266  1.00  0.00           P
ATOM   2453  P     C A2463       0.061 174.706 293.369  1.00  0.00           P
ATOM   2454  P     C A2464      -4.001 178.949 291.991  1.00  0.00           P
ATOM   2455  P     C A2465      -4.541 183.700 287.082  1.00  0.00           P
ATOM   2456  P     C A2466      -5.789 185.737 281.279  1.00  0.00           P
ATOM   2457  P     C A2467      -7.815 184.741 275.332  1.00  0.00           P
ATOM   2458  P     G A2468     -10.578 182.423 271.286  1.00  0.00           P
ATOM   2459  P     A A2469     -12.278 176.865 270.988  1.00  0.00           P
ATOM   2460  P     G A2470     -12.246 170.532 268.633  1.00  0.00           P
ATOM   2461  P     C A2471     -16.455 166.798 272.146  1.00  0.00           P
ATOM   2462  P     G A2472     -20.348 165.038 278.099  1.00  0.00           P
ATOM   2463  P     U A2473     -26.221 165.742 278.538  1.00  0.00           P
ATOM   2464  P     C A2474     -24.936 167.090 273.912  1.00  0.00           P
ATOM   2465  P     C A2475     -26.157 172.786 272.582  1.00  0.00           P
ATOM   2466  P     A A2476     -21.708 176.336 272.049  1.00  0.00           P
ATOM   2467  P     C A2477     -19.770 177.717 276.746  1.00  0.00           P
ATOM   2468  P     A A2478     -19.775 179.026 282.697  1.00  0.00           P
ATOM   2469  P     G A2479     -18.584 177.105 287.137  1.00  0.00           P
ATOM   2470  P     C A2480     -14.492 173.177 287.960  1.00  0.00           P
ATOM   2471  P     G A2481     -10.736 171.787 284.409  1.00  0.00           P
ATOM   2472  P     G A2482      -6.697 172.259 280.336  1.00  0.00           P
ATOM   2473  P     C A2483      -4.848 169.596 275.953  1.00  0.00           P
ATOM   2474  P     G A2484       1.404 170.513 273.699  1.00  0.00           P
ATOM   2475  P     G A2485       5.650 175.739 273.714  1.00  0.00           P
ATOM   2476  P     G A2486       6.675 182.614 275.872  1.00  0.00           P
ATOM   2477  P     G A2487       7.575 186.874 279.980  1.00  0.00           P
ATOM   2478  P     A A2488       7.684 188.290 286.479  1.00  0.00           P
ATOM   2479  P     G A2489       7.123 187.820 292.347  1.00  0.00           P
ATOM   2480  P     G A2490       9.562 186.338 297.543  1.00  0.00           P
ATOM   2481  P     U A2491      12.262 182.234 300.898  1.00  0.00           P
ATOM   2482  P     U A2492      12.405 177.183 300.741  1.00  0.00           P
ATOM   2483  P     U A2493      14.120 172.054 299.242  1.00  0.00           P
ATOM   2484  P     G A2494      17.586 169.316 296.449  1.00  0.00           P
ATOM   2485  P     G A2495      22.195 170.394 291.494  1.00  0.00           P
ATOM   2486  P     C A2496      26.990 173.184 289.318  1.00  0.00           P
ATOM   2487  P     A A2497      30.444 177.221 290.578  1.00  0.00           P
ATOM   2488  P     C A2498      33.212 182.272 294.568  1.00  0.00           P
ATOM   2489  P     C A2499      33.157 185.373 298.082  1.00  0.00           P
ATOM   2490  P     U A2500      35.065 186.436 302.436  1.00  0.00           P
```

```
ATOM   2491  P    C A2501      34.845 184.034 307.076  1.00  0.00           P
ATOM   2492  P    G A2502      37.198 182.405 311.927  1.00  0.00           P
ATOM   2493  P    A A2503      32.083 182.542 314.089  1.00  0.00           P
ATOM   2494  P    U A2504      28.999 179.449 313.606  1.00  0.00           P
ATOM   2495  P    G A2505      24.650 175.816 313.391  1.00  0.00           P
ATOM   2496  P    U A2506      20.813 172.302 312.122  1.00  0.00           P
ATOM   2497  P    C A2507      16.426 172.830 312.015  1.00  0.00           P
ATOM   2498  P    G A2508      14.204 169.148 311.964  1.00  0.00           P
ATOM   2499  P    G A2509       9.659 168.842 315.490  1.00  0.00           P
ATOM   2500  P    C A2510       6.557 170.854 320.189  1.00  0.00           P
ATOM   2501  P    U A2511       5.015 174.430 324.768  1.00  0.00           P
ATOM   2502  P    C A2512       4.672 180.437 326.422  1.00  0.00           P
ATOM   2503  P    G A2513       4.738 184.067 323.990  1.00  0.00           P
ATOM   2504  P    U A2514       4.174 187.796 319.862  1.00  0.00           P
ATOM   2505  P    C A2515       2.593 190.774 314.609  1.00  0.00           P
ATOM   2506  P    G A2516       2.313 191.999 308.388  1.00  0.00           P
ATOM   2507  P    C A2517       0.328 191.335 303.028  1.00  0.00           P
ATOM   2508  P    A A2518      -3.186 187.856 299.005  1.00  0.00           P
ATOM   2509  P    U A2519      -4.927 183.832 298.672  1.00  0.00           P
ATOM   2510  P    C A2520      -8.876 179.356 300.909  1.00  0.00           P
ATOM   2511  P    C A2521     -13.490 177.613 303.880  1.00  0.00           P
ATOM   2512  P    U A2522     -14.789 180.182 308.183  1.00  0.00           P
ATOM   2513  P    G A2523     -18.502 184.510 309.168  1.00  0.00           P
ATOM   2514  P    G A2524     -20.848 189.360 307.203  1.00  0.00           P
ATOM   2515  P    G A2525     -22.749 192.184 302.443  1.00  0.00           P
ATOM   2516  P    G A2526     -23.526 191.244 294.192  1.00  0.00           P
ATOM   2517  P    C A2527     -24.585 188.590 289.321  1.00  0.00           P
ATOM   2518  P    U A2528     -25.564 183.905 285.965  1.00  0.00           P
ATOM   2519  P    G A2529     -27.171 176.790 285.576  1.00  0.00           P
ATOM   2520  P    A A2530     -26.489 175.135 290.405  1.00  0.00           P
ATOM   2521  P    A A2531     -32.032 176.564 292.740  1.00  0.00           P
ATOM   2522  P    G A2532     -35.669 174.819 297.891  1.00  0.00           P
ATOM   2523  P    A A2533     -31.803 176.440 300.852  1.00  0.00           P
ATOM   2524  P    A A2534     -27.753 175.210 302.813  1.00  0.00           P
ATOM   2525  P    G A2535     -22.238 173.303 302.125  1.00  0.00           P
ATOM   2526  P    G A2536     -17.576 173.422 297.487  1.00  0.00           P
ATOM   2527  P    U A2537     -14.177 174.989 293.615  1.00  0.00           P
ATOM   2528  P    C A2538     -11.687 180.167 291.530  1.00  0.00           P
ATOM   2529  P    C A2539     -11.623 186.561 292.297  1.00  0.00           P
ATOM   2530  P    C A2540      -9.435 190.961 294.296  1.00  0.00           P
ATOM   2531  P    A A2541      -9.166 192.096 300.026  1.00  0.00           P
ATOM   2532  P    A A2542      -8.504 192.147 304.373  1.00  0.00           P
ATOM   2533  P    G A2543      -3.866 191.984 309.024  1.00  0.00           P
ATOM   2534  P    G A2544      -7.061 191.704 315.055  1.00  0.00           P
ATOM   2535  P    G A2545      -6.898 185.312 317.774  1.00  0.00           P
ATOM   2536  P    U A2546      -6.672 179.284 317.686  1.00  0.00           P
ATOM   2537  P    U A2547      -5.230 174.469 317.094  1.00  0.00           P
ATOM   2538  P    G A2548      -2.693 170.724 321.611  1.00  0.00           P
ATOM   2539  P    G A2549      -1.461 165.635 324.242  1.00  0.00           P
ATOM   2540  P    G A2550      -0.509 159.839 322.955  1.00  0.00           P
ATOM   2541  P    C A2551       1.842 154.969 320.306  1.00  0.00           P
ATOM   2542  P    U A2552       5.677 155.325 317.915  1.00  0.00           P
ATOM   2543  P    G A2553      10.266 157.306 316.346  1.00  0.00           P
ATOM   2544  P    U A2554      12.052 161.431 316.067  1.00  0.00           P
ATOM   2545  P    U A2555       9.622 165.693 313.481  1.00  0.00           P
ATOM   2546  P    C A2556       6.425 167.751 309.666  1.00  0.00           P
ATOM   2547  P    G A2557       1.196 167.393 305.532  1.00  0.00           P
ATOM   2548  P    C A2558      -2.120 162.150 304.894  1.00  0.00           P
ATOM   2549  P    C A2559      -5.330 157.946 306.728  1.00  0.00           P
ATOM   2550  P    C A2560      -8.862 156.299 311.314  1.00  0.00           P
ATOM   2551  P    A A2561     -13.335 158.076 315.025  1.00  0.00           P
ATOM   2552  P    U A2562     -14.971 162.784 317.245  1.00  0.00           P
ATOM   2553  P    U A2563     -16.485 169.154 317.858  1.00  0.00           P
ATOM   2554  P    A A2564     -17.656 171.933 312.475  1.00  0.00           P
ATOM   2555  P    A A2565     -12.752 172.083 309.971  1.00  0.00           P
ATOM   2556  P    A A2566      -7.687 172.549 311.598  1.00  0.00           P
ATOM   2557  P    G A2567      -3.226 173.106 309.813  1.00  0.00           P
ATOM   2558  P    C A2568      -0.803 174.363 304.966  1.00  0.00           P
ATOM   2559  P    G A2569       3.721 177.396 303.191  1.00  0.00           P
ATOM   2560  P    G A2570       8.968 180.145 303.735  1.00  0.00           P
ATOM   2561  P    C A2571      13.449 182.882 305.910  1.00  0.00           P
ATOM   2562  P    A A2572      15.955 187.586 311.230  1.00  0.00           P
ATOM   2563  P    C A2573      20.577 182.471 309.351  1.00  0.00           P
ATOM   2564  P    G A2574      15.426 177.131 310.326  1.00  0.00           P
ATOM   2565  P    C A2575      16.047 180.154 314.475  1.00  0.00           P
ATOM   2566  P    G A2576      19.085 179.870 319.020  1.00  0.00           P
ATOM   2567  P    A A2577      23.430 182.122 321.419  1.00  0.00           P
ATOM   2568  P    G A2578      23.469 182.168 326.717  1.00  0.00           P
ATOM   2569  P    C A2579      18.563 177.388 327.264  1.00  0.00           P
ATOM   2570  P    U A2580      19.037 171.854 327.988  1.00  0.00           P
ATOM   2571  P    G A2581      19.117 165.517 325.187  1.00  0.00           P
ATOM   2572  P    G A2582      20.205 160.651 322.672  1.00  0.00           P
ATOM   2573  P    G A2583      19.797 159.540 317.803  1.00  0.00           P
ATOM   2574  P    U A2584      21.614 159.347 313.165  1.00  0.00           P
ATOM   2575  P    U A2585      25.766 160.989 311.708  1.00  0.00           P
ATOM   2576  P    C A2586      29.199 160.320 315.931  1.00  0.00           P
ATOM   2577  P    A A2587      34.496 158.748 317.334  1.00  0.00           P
```

| | | | | | | | | |
|---|---|---|---|---|---|---|---|---|
| ATOM | 2578 | P | G | A2588 | 36.629 | 153.104 | 318.610 | 1.00 | 0.00 | P |
| ATOM | 2579 | P | A | A2589 | 36.369 | 147.274 | 319.659 | 1.00 | 0.00 | P |
| ATOM | 2580 | P | A | A2590 | 33.104 | 142.453 | 318.265 | 1.00 | 0.00 | P |
| ATOM | 2581 | P | C | A2591 | 27.319 | 142.267 | 314.922 | 1.00 | 0.00 | P |
| ATOM | 2582 | P | G | A2592 | 24.902 | 140.108 | 310.100 | 1.00 | 0.00 | P |
| ATOM | 2583 | P | U | A2593 | 25.645 | 141.143 | 303.313 | 1.00 | 0.00 | P |
| ATOM | 2584 | P | C | A2594 | 30.002 | 141.313 | 299.764 | 1.00 | 0.00 | P |
| ATOM | 2585 | P | G | A2595 | 35.086 | 141.393 | 297.792 | 1.00 | 0.00 | P |
| ATOM | 2586 | P | U | A2596 | 40.101 | 140.516 | 298.504 | 1.00 | 0.00 | P |
| ATOM | 2587 | P | G | A2597 | 40.909 | 139.893 | 303.890 | 1.00 | 0.00 | P |
| ATOM | 2588 | P | A | A2598 | 42.250 | 143.479 | 308.804 | 1.00 | 0.00 | P |
| ATOM | 2589 | P | G | A2599 | 42.163 | 149.423 | 311.450 | 1.00 | 0.00 | P |
| ATOM | 2590 | P | A | A2600 | 38.337 | 152.346 | 308.562 | 1.00 | 0.00 | P |
| ATOM | 2591 | P | C | A2601 | 32.993 | 153.898 | 305.630 | 1.00 | 0.00 | P |
| ATOM | 2592 | P | A | A2602 | 27.342 | 156.263 | 305.342 | 1.00 | 0.00 | P |
| ATOM | 2593 | P | G | A2603 | 22.832 | 154.107 | 302.653 | 1.00 | 0.00 | P |
| ATOM | 2594 | P | U | A2604 | 19.910 | 152.158 | 308.047 | 1.00 | 0.00 | P |
| ATOM | 2595 | P | U | A2605 | 18.740 | 149.948 | 313.978 | 1.00 | 0.00 | P |
| ATOM | 2596 | P | C | A2606 | 19.182 | 151.097 | 320.077 | 1.00 | 0.00 | P |
| ATOM | 2597 | P | G | A2607 | 21.509 | 152.920 | 323.946 | 1.00 | 0.00 | P |
| ATOM | 2598 | P | G | A2608 | 25.723 | 157.138 | 326.421 | 1.00 | 0.00 | P |
| ATOM | 2599 | P | U | A2609 | 25.647 | 161.486 | 326.773 | 1.00 | 0.00 | P |
| ATOM | 2600 | P | C | A2610 | 27.510 | 166.526 | 327.920 | 1.00 | 0.00 | P |
| ATOM | 2601 | P | U | A2611 | 26.039 | 172.227 | 328.028 | 1.00 | 0.00 | P |
| ATOM | 2602 | P | C | A2612 | 28.147 | 175.734 | 331.997 | 1.00 | 0.00 | P |
| ATOM | 2603 | P | U | A2613 | 26.835 | 180.347 | 335.002 | 1.00 | 0.00 | P |
| ATOM | 2604 | P | A | A2614 | 27.429 | 186.030 | 334.270 | 1.00 | 0.00 | P |
| ATOM | 2605 | P | U | A2615 | 27.167 | 192.752 | 334.020 | 1.00 | 0.00 | P |
| ATOM | 2606 | P | C | A2616 | 28.382 | 197.418 | 330.719 | 1.00 | 0.00 | P |
| ATOM | 2607 | P | C | A2617 | 26.370 | 200.378 | 326.386 | 1.00 | 0.00 | P |
| ATOM | 2608 | P | G | A2618 | 22.139 | 199.943 | 322.235 | 1.00 | 0.00 | P |
| ATOM | 2609 | P | C | A2619 | 16.906 | 198.639 | 322.001 | 1.00 | 0.00 | P |
| ATOM | 2610 | P | C | A2620 | 11.128 | 197.691 | 325.097 | 1.00 | 0.00 | P |
| ATOM | 2611 | P | A | A2621 | 6.888 | 196.859 | 329.791 | 1.00 | 0.00 | P |
| ATOM | 2612 | P | C | A2622 | 7.468 | 200.064 | 336.458 | 1.00 | 0.00 | P |
| ATOM | 2613 | P | G | A2623 | 9.594 | 204.562 | 340.572 | 1.00 | 0.00 | P |
| ATOM | 2614 | P | G | A2624 | 13.652 | 208.878 | 341.875 | 1.00 | 0.00 | P |
| ATOM | 2615 | P | G | A2625 | 18.044 | 212.909 | 342.426 | 1.00 | 0.00 | P |
| ATOM | 2616 | P | C | A2626 | 20.591 | 218.133 | 338.632 | 1.00 | 0.00 | P |
| ATOM | 2617 | P | G | A2627 | 17.379 | 222.216 | 335.405 | 1.00 | 0.00 | P |
| ATOM | 2618 | P | C | A2628 | 14.146 | 225.578 | 332.859 | 1.00 | 0.00 | P |
| ATOM | 2619 | P | A | A2629 | 8.610 | 225.732 | 331.398 | 1.00 | 0.00 | P |
| ATOM | 2620 | P | G | A2630 | 9.385 | 231.211 | 332.798 | 1.00 | 0.00 | P |
| ATOM | 2621 | P | G | A2631 | 10.259 | 231.492 | 338.549 | 1.00 | 0.00 | P |
| ATOM | 2622 | P | A | A2632 | 9.904 | 228.305 | 343.258 | 1.00 | 0.00 | P |
| ATOM | 2623 | P | G | A2633 | 7.499 | 224.911 | 346.081 | 1.00 | 0.00 | P |
| ATOM | 2624 | P | G | A2634 | 4.119 | 221.015 | 348.247 | 1.00 | 0.00 | P |
| ATOM | 2625 | P | C | A2635 | -1.380 | 218.028 | 346.333 | 1.00 | 0.00 | P |
| ATOM | 2626 | P | U | A2636 | -5.398 | 215.362 | 343.830 | 1.00 | 0.00 | P |
| ATOM | 2627 | P | U | A2637 | -8.872 | 215.592 | 338.029 | 1.00 | 0.00 | P |
| ATOM | 2628 | P | G | A2638 | -8.607 | 215.559 | 330.712 | 1.00 | 0.00 | P |
| ATOM | 2629 | P | A | A2639 | -5.997 | 213.398 | 324.147 | 1.00 | 0.00 | P |
| ATOM | 2630 | P | G | A2640 | -2.293 | 213.859 | 317.790 | 1.00 | 0.00 | P |
| ATOM | 2631 | P | G | A2641 | 0.840 | 208.180 | 317.737 | 1.00 | 0.00 | P |
| ATOM | 2632 | P | G | A2642 | 1.457 | 201.615 | 319.991 | 1.00 | 0.00 | P |
| ATOM | 2633 | P | G | A2643 | -0.896 | 196.274 | 321.692 | 1.00 | 0.00 | P |
| ATOM | 2634 | P | G | A2644 | -7.657 | 193.305 | 321.775 | 1.00 | 0.00 | P |
| ATOM | 2635 | P | G | A2645 | -12.419 | 192.383 | 319.460 | 1.00 | 0.00 | P |
| ATOM | 2636 | P | C | A2646 | -14.283 | 188.017 | 317.388 | 1.00 | 0.00 | P |
| ATOM | 2637 | P | U | A2647 | -16.591 | 183.673 | 313.541 | 1.00 | 0.00 | P |
| ATOM | 2638 | P | C | A2648 | -20.716 | 178.957 | 314.289 | 1.00 | 0.00 | P |
| ATOM | 2639 | P | U | A2649 | -24.966 | 174.961 | 316.923 | 1.00 | 0.00 | P |
| ATOM | 2640 | P | U | A2650 | -30.804 | 174.140 | 318.109 | 1.00 | 0.00 | P |
| ATOM | 2641 | P | C | A2651 | -35.754 | 175.660 | 319.481 | 1.00 | 0.00 | P |
| ATOM | 2642 | P | C | A2652 | -39.628 | 178.511 | 319.886 | 1.00 | 0.00 | P |
| ATOM | 2643 | P | U | A2653 | -42.266 | 181.229 | 315.764 | 1.00 | 0.00 | P |
| ATOM | 2644 | P | A | A2654 | -43.855 | 183.227 | 310.643 | 1.00 | 0.00 | P |
| ATOM | 2645 | P | G | A2655 | -44.058 | 177.274 | 313.254 | 1.00 | 0.00 | P |
| ATOM | 2646 | P | U | A2656 | -43.223 | 179.659 | 307.077 | 1.00 | 0.00 | P |
| ATOM | 2647 | P | A | A2657 | -42.163 | 181.168 | 301.738 | 1.00 | 0.00 | P |
| ATOM | 2648 | P | C | A2658 | -43.186 | 178.650 | 296.112 | 1.00 | 0.00 | P |
| ATOM | 2649 | P | G | A2659 | -42.448 | 173.966 | 292.970 | 1.00 | 0.00 | P |
| ATOM | 2650 | P | A | A2660 | -43.773 | 168.876 | 293.763 | 1.00 | 0.00 | P |
| ATOM | 2651 | P | G | A2661 | -44.704 | 168.582 | 299.929 | 1.00 | 0.00 | P |
| ATOM | 2652 | P | A | A2662 | -40.252 | 165.366 | 300.293 | 1.00 | 0.00 | P |
| ATOM | 2653 | P | G | A2663 | -37.277 | 165.665 | 305.021 | 1.00 | 0.00 | P |
| ATOM | 2654 | P | G | A2664 | -35.431 | 170.521 | 303.872 | 1.00 | 0.00 | P |
| ATOM | 2655 | P | A | A2665 | -33.862 | 175.849 | 306.518 | 1.00 | 0.00 | P |
| ATOM | 2656 | P | C | A2666 | -34.009 | 181.806 | 306.223 | 1.00 | 0.00 | P |
| ATOM | 2657 | P | C | A2667 | -33.216 | 186.443 | 306.603 | 1.00 | 0.00 | P |
| ATOM | 2658 | P | G | A2668 | -30.908 | 190.608 | 309.272 | 1.00 | 0.00 | P |
| ATOM | 2659 | P | G | A2669 | -31.579 | 192.067 | 314.307 | 1.00 | 0.00 | P |
| ATOM | 2660 | P | A | A2670 | -32.661 | 191.939 | 320.079 | 1.00 | 0.00 | P |
| ATOM | 2661 | P | A | A2671 | -31.582 | 188.423 | 325.335 | 1.00 | 0.00 | P |
| ATOM | 2662 | P | G | A2672 | -29.331 | 184.712 | 328.970 | 1.00 | 0.00 | P |
| ATOM | 2663 | P | G | A2673 | -24.820 | 180.155 | 329.949 | 1.00 | 0.00 | P |
| ATOM | 2664 | P | G | A2674 | -20.220 | 176.490 | 329.256 | 1.00 | 0.00 | P |

| | | | | | | | | | |
|---|---|---|---|---|---|---|---|---|---|
| ATOM | 2665 | P | A | A2675 | -13.857 | 175.281 | 326.419 | 1.00 | 0.00 | P |
| ATOM | 2666 | P | C | A2676 | -9.420 | 178.662 | 326.709 | 1.00 | 0.00 | P |
| ATOM | 2667 | P | G | A2677 | -6.093 | 183.591 | 327.636 | 1.00 | 0.00 | P |
| ATOM | 2668 | P | C | A2678 | -5.183 | 188.382 | 330.056 | 1.00 | 0.00 | P |
| ATOM | 2669 | P | A | A2679 | -4.921 | 192.915 | 334.426 | 1.00 | 0.00 | P |
| ATOM | 2670 | P | C | A2680 | -6.777 | 194.332 | 341.153 | 1.00 | 0.00 | P |
| ATOM | 2671 | P | C | A2681 | -9.686 | 191.132 | 346.462 | 1.00 | 0.00 | P |
| ATOM | 2672 | P | U | A2682 | -13.149 | 187.026 | 348.585 | 1.00 | 0.00 | P |
| ATOM | 2673 | P | C | A2683 | -17.812 | 184.385 | 350.294 | 1.00 | 0.00 | P |
| ATOM | 2674 | P | U | A2684 | -18.389 | 178.822 | 349.526 | 1.00 | 0.00 | P |
| ATOM | 2675 | P | G | A2685 | -15.654 | 173.770 | 348.839 | 1.00 | 0.00 | P |
| ATOM | 2676 | P | G | A2686 | -9.193 | 171.355 | 347.839 | 1.00 | 0.00 | P |
| ATOM | 2677 | P | U | A2687 | -4.704 | 172.299 | 350.064 | 1.00 | 0.00 | P |
| ATOM | 2678 | P | U | A2688 | -0.854 | 174.877 | 351.991 | 1.00 | 0.00 | P |
| ATOM | 2679 | P | U | A2689 | -2.216 | 177.493 | 355.440 | 1.00 | 0.00 | P |
| ATOM | 2680 | P | C | A2690 | 2.083 | 177.206 | 358.274 | 1.00 | 0.00 | P |
| ATOM | 2681 | P | C | A2691 | 3.511 | 178.526 | 364.090 | 1.00 | 0.00 | P |
| ATOM | 2682 | P | C | A2692 | -1.097 | 178.254 | 368.698 | 1.00 | 0.00 | P |
| ATOM | 2683 | P | A | A2693 | -3.600 | 173.310 | 370.135 | 1.00 | 0.00 | P |
| ATOM | 2684 | P | G | A2694 | -4.200 | 166.728 | 371.597 | 1.00 | 0.00 | P |
| ATOM | 2685 | P | C | A2695 | -1.949 | 161.409 | 372.011 | 1.00 | 0.00 | P |
| ATOM | 2686 | P | U | A2696 | 3.342 | 157.340 | 371.769 | 1.00 | 0.00 | P |
| ATOM | 2687 | P | G | A2697 | 7.848 | 155.348 | 372.848 | 1.00 | 0.00 | P |
| ATOM | 2688 | P | U | A2698 | 13.139 | 155.421 | 374.547 | 1.00 | 0.00 | P |
| ATOM | 2689 | P | C | A2699 | 17.864 | 158.388 | 377.067 | 1.00 | 0.00 | P |
| ATOM | 2690 | P | C | A2700 | 19.598 | 163.407 | 379.943 | 1.00 | 0.00 | P |
| ATOM | 2691 | P | C | A2701 | 19.020 | 167.838 | 384.303 | 1.00 | 0.00 | P |
| ATOM | 2692 | P | U | A2702 | 15.526 | 167.174 | 387.816 | 1.00 | 0.00 | P |
| ATOM | 2693 | P | C | A2703 | 10.904 | 162.271 | 387.976 | 1.00 | 0.00 | P |
| ATOM | 2694 | P | C | A2704 | 4.998 | 161.535 | 387.430 | 1.00 | 0.00 | P |
| ATOM | 2695 | P | A | A2705 | 1.186 | 163.222 | 384.254 | 1.00 | 0.00 | P |
| ATOM | 2696 | P | G | A2706 | 0.691 | 166.941 | 382.348 | 1.00 | 0.00 | P |
| ATOM | 2697 | P | G | A2707 | 4.129 | 170.764 | 378.086 | 1.00 | 0.00 | P |
| ATOM | 2698 | P | G | A2708 | 9.218 | 172.662 | 373.745 | 1.00 | 0.00 | P |
| ATOM | 2699 | P | G | A2709 | 12.930 | 172.706 | 370.112 | 1.00 | 0.00 | P |
| ATOM | 2700 | P | C | A2710 | 15.716 | 170.737 | 366.270 | 1.00 | 0.00 | P |
| ATOM | 2701 | P | A | A2711 | 17.157 | 166.521 | 362.599 | 1.00 | 0.00 | P |
| ATOM | 2702 | P | U | A2712 | 13.873 | 165.838 | 359.495 | 1.00 | 0.00 | P |
| ATOM | 2703 | P | A | A2712A | 14.972 | 170.444 | 357.064 | 1.00 | 0.00 | P |
| ATOM | 2704 | P | A | A2713 | 11.078 | 172.823 | 359.405 | 1.00 | 0.00 | P |
| ATOM | 2705 | P | G | A2714 | 10.718 | 168.082 | 362.139 | 1.00 | 0.00 | P |
| ATOM | 2706 | P | C | A2715 | 8.089 | 163.288 | 359.409 | 1.00 | 0.00 | P |
| ATOM | 2707 | P | U | A2716 | 3.125 | 162.217 | 357.915 | 1.00 | 0.00 | P |
| ATOM | 2708 | P | G | A2717 | -2.750 | 162.379 | 358.251 | 1.00 | 0.00 | P |
| ATOM | 2709 | P | G | A2718 | -7.424 | 165.782 | 357.139 | 1.00 | 0.00 | P |
| ATOM | 2710 | P | G | A2719 | -8.191 | 170.810 | 358.054 | 1.00 | 0.00 | P |
| ATOM | 2711 | P | U | A2720 | -7.493 | 176.411 | 357.195 | 1.00 | 0.00 | P |
| ATOM | 2712 | P | A | A2721 | -8.170 | 182.911 | 356.344 | 1.00 | 0.00 | P |
| ATOM | 2713 | P | G | A2722 | -5.933 | 187.347 | 355.180 | 1.00 | 0.00 | P |
| ATOM | 2714 | P | C | A2723 | -3.538 | 188.832 | 349.753 | 1.00 | 0.00 | P |
| ATOM | 2715 | P | C | A2724 | -1.902 | 185.774 | 344.176 | 1.00 | 0.00 | P |
| ATOM | 2716 | P | A | A2725 | -3.892 | 180.866 | 338.721 | 1.00 | 0.00 | P |
| ATOM | 2717 | P | U | A2726 | -7.930 | 177.187 | 336.868 | 1.00 | 0.00 | P |
| ATOM | 2718 | P | G | A2727 | -13.350 | 176.733 | 339.032 | 1.00 | 0.00 | P |
| ATOM | 2719 | P | U | A2728 | -17.380 | 179.530 | 340.611 | 1.00 | 0.00 | P |
| ATOM | 2720 | P | G | A2729 | -20.030 | 185.034 | 339.780 | 1.00 | 0.00 | P |
| ATOM | 2721 | P | C | A2730 | -21.325 | 189.108 | 336.338 | 1.00 | 0.00 | P |
| ATOM | 2722 | P | G | A2731 | -19.107 | 192.043 | 332.086 | 1.00 | 0.00 | P |
| ATOM | 2723 | P | G | A2732 | -16.715 | 192.700 | 327.853 | 1.00 | 0.00 | P |
| ATOM | 2724 | P | A | A2733 | -16.754 | 194.089 | 323.080 | 1.00 | 0.00 | P |
| ATOM | 2725 | P | A | A2734 | -19.466 | 194.946 | 319.631 | 1.00 | 0.00 | P |
| ATOM | 2726 | P | G | A2735 | -24.648 | 198.155 | 317.276 | 1.00 | 0.00 | P |
| ATOM | 2727 | P | G | A2736 | -25.590 | 203.313 | 313.631 | 1.00 | 0.00 | P |
| ATOM | 2728 | P | G | A2737 | -23.772 | 207.300 | 309.789 | 1.00 | 0.00 | P |
| ATOM | 2729 | P | A | A2738 | -20.386 | 209.513 | 306.008 | 1.00 | 0.00 | P |
| ATOM | 2730 | P | U | A2739 | -16.632 | 208.710 | 301.191 | 1.00 | 0.00 | P |
| ATOM | 2731 | P | A | A2740 | -14.620 | 203.160 | 299.191 | 1.00 | 0.00 | P |
| ATOM | 2732 | P | A | A2741 | -12.799 | 199.089 | 295.718 | 1.00 | 0.00 | P |
| ATOM | 2733 | P | C | A2742 | -15.011 | 195.035 | 291.365 | 1.00 | 0.00 | P |
| ATOM | 2734 | P | C | A2743 | -21.043 | 193.571 | 290.610 | 1.00 | 0.00 | P |
| ATOM | 2735 | P | G | A2744 | -26.916 | 195.936 | 289.835 | 1.00 | 0.00 | P |
| ATOM | 2736 | P | C | A2745 | -30.053 | 202.255 | 289.328 | 1.00 | 0.00 | P |
| ATOM | 2737 | P | U | A2746 | -31.469 | 208.253 | 287.642 | 1.00 | 0.00 | P |
| ATOM | 2738 | P | G | A2747 | -30.185 | 210.491 | 283.434 | 1.00 | 0.00 | P |
| ATOM | 2739 | P | A | A2748 | -27.256 | 212.136 | 279.678 | 1.00 | 0.00 | P |
| ATOM | 2740 | P | A | A2749 | -23.500 | 214.662 | 276.826 | 1.00 | 0.00 | P |
| ATOM | 2741 | P | A | A2750 | -19.664 | 211.470 | 271.497 | 1.00 | 0.00 | P |
| ATOM | 2742 | P | G | A2751 | -25.480 | 210.930 | 269.369 | 1.00 | 0.00 | P |
| ATOM | 2743 | P | C | A2752 | -30.644 | 209.885 | 273.102 | 1.00 | 0.00 | P |
| ATOM | 2744 | P | A | A2753 | -29.300 | 204.380 | 273.995 | 1.00 | 0.00 | P |
| ATOM | 2745 | P | U | A2754 | -28.916 | 201.929 | 279.072 | 1.00 | 0.00 | P |
| ATOM | 2746 | P | C | A2755 | -25.404 | 200.616 | 283.825 | 1.00 | 0.00 | P |
| ATOM | 2747 | P | U | A2756 | -20.907 | 203.480 | 283.620 | 1.00 | 0.00 | P |
| ATOM | 2748 | P | A | A2757 | -16.134 | 207.335 | 284.631 | 1.00 | 0.00 | P |
| ATOM | 2749 | P | A | A2758 | -15.167 | 211.412 | 287.002 | 1.00 | 0.00 | P |
| ATOM | 2750 | P | G | A2759 | -17.521 | 215.084 | 290.148 | 1.00 | 0.00 | P |
| ATOM | 2751 | P | C | A2760 | -21.558 | 214.769 | 294.755 | 1.00 | 0.00 | P |

| | | | | | | | | | |
|---|---|---|---|---|---|---|---|---|---|
| ATOM | 2752 | P | G | A2761 | -25.228 | 210.558 | 297.084 | 1.00 | 0.00 | P |
| ATOM | 2753 | P | G | A2762 | -27.114 | 206.094 | 299.678 | 1.00 | 0.00 | P |
| ATOM | 2754 | P | G | A2763 | -24.531 | 201.344 | 304.241 | 1.00 | 0.00 | P |
| ATOM | 2755 | P | A | A2764 | -20.863 | 196.797 | 305.776 | 1.00 | 0.00 | P |
| ATOM | 2756 | P | A | A2765 | -18.301 | 195.221 | 308.901 | 1.00 | 0.00 | P |
| ATOM | 2757 | P | G | A2766 | -13.184 | 195.645 | 312.661 | 1.00 | 0.00 | P |
| ATOM | 2758 | P | C | A2767 | -7.797 | 199.056 | 311.308 | 1.00 | 0.00 | P |
| ATOM | 2759 | P | C | A2768 | -7.623 | 204.619 | 312.630 | 1.00 | 0.00 | P |
| ATOM | 2760 | P | C | A2769 | -9.090 | 208.429 | 315.735 | 1.00 | 0.00 | P |
| ATOM | 2761 | P | G | A2770 | -12.519 | 208.106 | 320.052 | 1.00 | 0.00 | P |
| ATOM | 2762 | P | C | A2771 | -15.539 | 205.631 | 323.691 | 1.00 | 0.00 | P |
| ATOM | 2763 | P | C | A2772 | -13.542 | 202.798 | 328.386 | 1.00 | 0.00 | P |
| ATOM | 2764 | P | C | A2773 | -9.143 | 201.568 | 331.895 | 1.00 | 0.00 | P |
| ATOM | 2765 | P | C | A2774 | -3.911 | 203.097 | 333.200 | 1.00 | 0.00 | P |
| ATOM | 2766 | P | A | A2775 | 0.900 | 206.366 | 333.411 | 1.00 | 0.00 | P |
| ATOM | 2767 | P | A | A2776 | 0.492 | 209.788 | 331.044 | 1.00 | 0.00 | P |
| ATOM | 2768 | P | G | A2777 | 2.438 | 214.751 | 330.919 | 1.00 | 0.00 | P |
| ATOM | 2769 | P | A | A2778 | 5.888 | 215.348 | 328.489 | 1.00 | 0.00 | P |
| ATOM | 2770 | P | U | A2779 | 5.128 | 216.853 | 323.803 | 1.00 | 0.00 | P |
| ATOM | 2771 | P | G | A2780 | 8.856 | 221.399 | 323.084 | 1.00 | 0.00 | P |
| ATOM | 2772 | P | A | A2781 | 4.811 | 223.523 | 327.638 | 1.00 | 0.00 | P |
| ATOM | 2773 | P | G | A2782 | 0.523 | 225.309 | 328.284 | 1.00 | 0.00 | P |
| ATOM | 2774 | P | G | A2783 | -4.270 | 225.730 | 331.250 | 1.00 | 0.00 | P |
| ATOM | 2775 | P | C | A2784 | -8.354 | 227.081 | 335.514 | 1.00 | 0.00 | P |
| ATOM | 2776 | P | C | A2785 | -9.269 | 229.884 | 340.582 | 1.00 | 0.00 | P |
| ATOM | 2777 | P | U | A2786 | -7.619 | 231.269 | 345.867 | 1.00 | 0.00 | P |
| ATOM | 2778 | P | C | A2787 | -3.627 | 233.696 | 350.802 | 1.00 | 0.00 | P |
| ATOM | 2779 | P | C | A2788 | 2.115 | 236.005 | 351.339 | 1.00 | 0.00 | P |
| ATOM | 2780 | P | C | A2789 | 5.747 | 238.745 | 349.511 | 1.00 | 0.00 | P |
| ATOM | 2781 | P | A | A2790 | 6.542 | 235.969 | 344.440 | 1.00 | 0.00 | P |
| ATOM | 2782 | P | C | A2791 | 11.777 | 235.757 | 342.608 | 1.00 | 0.00 | P |
| ATOM | 2783 | P | G | A2792 | 12.611 | 239.704 | 345.810 | 1.00 | 0.00 | P |
| ATOM | 2784 | P | G | A2793 | 14.149 | 243.126 | 350.476 | 1.00 | 0.00 | P |
| ATOM | 2785 | P | C | A2794 | 18.498 | 245.893 | 352.838 | 1.00 | 0.00 | P |
| ATOM | 2786 | P | G | A2795 | 24.232 | 245.977 | 352.424 | 1.00 | 0.00 | P |
| ATOM | 2787 | P | U | A2797 | 27.244 | 246.927 | 348.903 | 1.00 | 0.00 | P |
| ATOM | 2788 | P | C | A2798 | 28.483 | 244.842 | 344.257 | 1.00 | 0.00 | P |
| ATOM | 2789 | P | A | A2799 | 24.213 | 242.495 | 343.182 | 1.00 | 0.00 | P |
| ATOM | 2790 | P | A | A2801 | 24.816 | 237.070 | 342.243 | 1.00 | 0.00 | P |
| ATOM | 2791 | P | G | A2802 | 26.820 | 232.254 | 344.894 | 1.00 | 0.00 | P |
| ATOM | 2792 | P | C | A2803 | 27.305 | 231.363 | 349.781 | 1.00 | 0.00 | P |
| ATOM | 2793 | P | C | A2804 | 24.827 | 231.281 | 356.047 | 1.00 | 0.00 | P |
| ATOM | 2794 | P | G | A2805 | 19.481 | 230.849 | 358.635 | 1.00 | 0.00 | P |
| ATOM | 2795 | P | G | A2807 | 14.950 | 232.159 | 357.198 | 1.00 | 0.00 | P |
| ATOM | 2796 | P | U | A2808 | 10.628 | 232.033 | 356.914 | 1.00 | 0.00 | P |
| ATOM | 2797 | P | A | A2809 | 6.953 | 231.667 | 355.060 | 1.00 | 0.00 | P |
| ATOM | 2798 | P | A | A2810 | 6.592 | 227.330 | 357.574 | 1.00 | 0.00 | P |
| ATOM | 2799 | P | G | A2811 | 3.362 | 225.488 | 353.323 | 1.00 | 0.00 | P |
| ATOM | 2800 | P | G | A2812 | 6.166 | 220.107 | 351.304 | 1.00 | 0.00 | P |
| ATOM | 2801 | P | A | A2813 | 10.236 | 216.538 | 351.642 | 1.00 | 0.00 | P |
| ATOM | 2802 | P | C | A2814 | 13.400 | 213.883 | 353.562 | 1.00 | 0.00 | P |
| ATOM | 2803 | P | C | A2815 | 16.603 | 210.528 | 355.443 | 1.00 | 0.00 | P |
| ATOM | 2804 | P | C | A2816 | 15.627 | 209.052 | 360.625 | 1.00 | 0.00 | P |
| ATOM | 2805 | P | G | A2817 | 12.507 | 205.391 | 363.840 | 1.00 | 0.00 | P |
| ATOM | 2806 | P | G | A2818 | 7.976 | 201.866 | 363.988 | 1.00 | 0.00 | P |
| ATOM | 2807 | P | G | A2819 | 3.582 | 198.656 | 359.764 | 1.00 | 0.00 | P |
| ATOM | 2808 | P | A | A2820 | 0.763 | 196.542 | 353.717 | 1.00 | 0.00 | P |
| ATOM | 2809 | P | A | A2821 | 0.901 | 196.685 | 347.112 | 1.00 | 0.00 | P |
| ATOM | 2810 | P | G | A2822 | 5.746 | 196.552 | 344.157 | 1.00 | 0.00 | P |
| ATOM | 2811 | P | A | A2823 | 11.724 | 193.915 | 343.837 | 1.00 | 0.00 | P |
| ATOM | 2812 | P | C | A2824 | 14.584 | 196.214 | 347.482 | 1.00 | 0.00 | P |
| ATOM | 2813 | P | C | A2825 | 17.007 | 201.658 | 348.150 | 1.00 | 0.00 | P |
| ATOM | 2814 | P | A | A2826 | 14.128 | 207.749 | 346.062 | 1.00 | 0.00 | P |
| ATOM | 2815 | P | C | A2827 | 8.977 | 208.874 | 344.898 | 1.00 | 0.00 | P |
| ATOM | 2816 | P | C | A2828 | 3.599 | 207.740 | 346.015 | 1.00 | 0.00 | P |
| ATOM | 2817 | P | C | A2829 | -0.242 | 208.164 | 349.489 | 1.00 | 0.00 | P |
| ATOM | 2818 | P | G | A2830 | -2.028 | 209.898 | 355.528 | 1.00 | 0.00 | P |
| ATOM | 2819 | P | G | A2831 | -1.304 | 211.679 | 360.745 | 1.00 | 0.00 | P |
| ATOM | 2820 | P | U | A2832 | 1.114 | 213.098 | 366.272 | 1.00 | 0.00 | P |
| ATOM | 2821 | P | G | A2833 | -1.165 | 216.970 | 370.309 | 1.00 | 0.00 | P |
| ATOM | 2822 | P | G | A2834 | -3.652 | 212.760 | 368.549 | 1.00 | 0.00 | P |
| ATOM | 2823 | P | A | A2835 | -4.769 | 209.127 | 365.395 | 1.00 | 0.00 | P |
| ATOM | 2824 | P | U | A2836 | -4.046 | 204.799 | 362.696 | 1.00 | 0.00 | P |
| ATOM | 2825 | P | G | A2837 | -0.663 | 200.045 | 361.940 | 1.00 | 0.00 | P |
| ATOM | 2826 | P | G | A2838 | 1.978 | 195.940 | 364.569 | 1.00 | 0.00 | P |
| ATOM | 2827 | P | G | A2839 | 2.352 | 193.500 | 369.920 | 1.00 | 0.00 | P |
| ATOM | 2828 | P | C | A2840 | 0.736 | 191.588 | 374.656 | 1.00 | 0.00 | P |
| ATOM | 2829 | P | C | A2841 | -2.775 | 190.504 | 378.283 | 1.00 | 0.00 | P |
| ATOM | 2830 | P | G | A2842 | -9.079 | 190.375 | 378.153 | 1.00 | 0.00 | P |
| ATOM | 2831 | P | G | A2843 | -14.112 | 188.955 | 375.118 | 1.00 | 0.00 | P |
| ATOM | 2832 | P | G | A2844 | -15.567 | 188.386 | 368.063 | 1.00 | 0.00 | P |
| ATOM | 2833 | P | G | A2845 | -15.600 | 184.777 | 363.545 | 1.00 | 0.00 | P |
| ATOM | 2834 | P | G | A2846 | -13.544 | 179.790 | 362.049 | 1.00 | 0.00 | P |
| ATOM | 2835 | P | U | A2847 | -10.633 | 175.576 | 362.975 | 1.00 | 0.00 | P |
| ATOM | 2836 | P | G | A2848 | -9.889 | 169.743 | 365.089 | 1.00 | 0.00 | P |
| ATOM | 2837 | P | U | A2849 | -10.932 | 167.817 | 371.695 | 1.00 | 0.00 | P |
| ATOM | 2838 | P | A | A2850 | -9.735 | 168.409 | 378.019 | 1.00 | 0.00 | P |

| | | | | | | | | | | |
|---|---|---|---|---|---|---|---|---|---|---|
| ATOM | 2839 | P | A | A2851 | -4.900 | 168.337 | 380.240 | 1.00 | 0.00 | P |
| ATOM | 2840 | P | G | A2852 | -2.465 | 169.234 | 385.280 | 1.00 | 0.00 | P |
| ATOM | 2841 | P | C | A2853 | -4.819 | 168.357 | 390.669 | 1.00 | 0.00 | P |
| ATOM | 2842 | P | G | A2854 | -10.075 | 164.670 | 393.602 | 1.00 | 0.00 | P |
| ATOM | 2843 | P | C | A2855 | -14.508 | 160.869 | 393.624 | 1.00 | 0.00 | P |
| ATOM | 2844 | P | C | A2856 | -16.624 | 155.855 | 391.668 | 1.00 | 0.00 | P |
| ATOM | 2845 | P | G | A2857 | -14.572 | 148.614 | 389.357 | 1.00 | 0.00 | P |
| ATOM | 2846 | P | C | A2858 | -9.546 | 146.146 | 388.557 | 1.00 | 0.00 | P |
| ATOM | 2847 | P | G | A2859 | -6.938 | 151.180 | 387.161 | 1.00 | 0.00 | P |
| ATOM | 2848 | P | A | A2860 | -4.710 | 152.986 | 381.588 | 1.00 | 0.00 | P |
| ATOM | 2849 | P | G | A2861 | -4.189 | 155.595 | 379.139 | 1.00 | 0.00 | P |
| ATOM | 2850 | P | G | A2862 | -8.923 | 157.624 | 377.111 | 1.00 | 0.00 | P |
| ATOM | 2851 | P | C | A2863 | -14.195 | 159.072 | 377.344 | 1.00 | 0.00 | P |
| ATOM | 2852 | P | G | A2864 | -18.290 | 162.438 | 379.897 | 1.00 | 0.00 | P |
| ATOM | 2853 | P | U | A2865 | -19.233 | 167.690 | 383.256 | 1.00 | 0.00 | P |
| ATOM | 2854 | P | U | A2866 | -17.684 | 173.929 | 381.919 | 1.00 | 0.00 | P |
| ATOM | 2855 | P | G | A2867 | -16.944 | 172.217 | 375.805 | 1.00 | 0.00 | P |
| ATOM | 2856 | P | A | A2868 | -16.864 | 177.059 | 375.458 | 1.00 | 0.00 | P |
| ATOM | 2857 | P | G | A2869 | -13.214 | 176.537 | 377.399 | 1.00 | 0.00 | P |
| ATOM | 2858 | P | C | A2870 | -7.335 | 177.122 | 376.610 | 1.00 | 0.00 | P |
| ATOM | 2859 | P | C | A2871 | -3.156 | 179.239 | 373.145 | 1.00 | 0.00 | P |
| ATOM | 2860 | P | G | A2872 | -1.063 | 183.211 | 369.196 | 1.00 | 0.00 | P |
| ATOM | 2861 | P | A | A2873 | -1.353 | 187.921 | 365.674 | 1.00 | 0.00 | P |
| ATOM | 2862 | P | C | A2874 | -2.969 | 190.680 | 361.170 | 1.00 | 0.00 | P |
| ATOM | 2863 | P | C | A2875 | -8.457 | 193.524 | 360.514 | 1.00 | 0.00 | P |
| ATOM | 2864 | P | G | A2876 | -11.575 | 197.168 | 364.009 | 1.00 | 0.00 | P |
| ATOM | 2865 | P | G | A2877 | -11.780 | 201.751 | 368.896 | 1.00 | 0.00 | P |
| ATOM | 2866 | P | U | A2878 | -9.913 | 204.864 | 373.215 | 1.00 | 0.00 | P |
| ATOM | 2867 | P | C | A2879 | -4.692 | 206.943 | 376.311 | 1.00 | 0.00 | P |
| ATOM | 2868 | P | C | A2880 | -0.916 | 205.734 | 378.824 | 1.00 | 0.00 | P |
| ATOM | 2869 | P | C | A2881 | 4.437 | 204.468 | 378.715 | 1.00 | 0.00 | P |
| ATOM | 2870 | P | A | A2882 | 8.721 | 204.377 | 375.374 | 1.00 | 0.00 | P |
| ATOM | 2871 | P | A | A2883 | 8.135 | 206.761 | 370.138 | 1.00 | 0.00 | P |
| ATOM | 2872 | P | U | A2884 | 8.492 | 211.557 | 367.454 | 1.00 | 0.00 | P |
| ATOM | 2873 | P | C | A2885 | 10.768 | 216.276 | 370.292 | 1.00 | 0.00 | P |
| ATOM | 2874 | P | G | A2886 | 14.854 | 219.218 | 367.909 | 1.00 | 0.00 | P |
| ATOM | 2875 | P | U | A2887 | 17.257 | 220.242 | 363.477 | 1.00 | 0.00 | P |
| ATOM | 2876 | P | C | A2888 | 20.984 | 222.618 | 359.834 | 1.00 | 0.00 | P |
| ATOM | 2877 | P | C | A2889 | 21.641 | 224.395 | 353.924 | 1.00 | 0.00 | P |
| ATOM | 2878 | P | G | A2890 | 19.835 | 227.740 | 347.580 | 1.00 | 0.00 | P |
| ATOM | 2879 | P | A | A2892 | 22.222 | 232.062 | 343.807 | 1.00 | 0.00 | P |
| ATOM | 2880 | P | G | A2893 | 25.139 | 233.007 | 338.532 | 1.00 | 0.00 | P |
| ATOM | 2881 | P | G | A2894 | 20.733 | 236.450 | 335.330 | 1.00 | 0.00 | P |
| ATOM | 2882 | P | U | A2895 | 16.091 | 240.887 | 331.614 | 1.00 | 0.00 | P |
| ATOM | 2883 | P | C | A2896 | 13.391 | 244.501 | 325.862 | 1.00 | 0.00 | P |
| ATOM | 2884 | P | U | A2897 | 9.223 | 246.632 | 320.632 | 1.00 | 0.00 | P |
| ATOM | 2885 | P | U | A2898 | 2.987 | 246.911 | 318.540 | 1.00 | 0.00 | P |
| ATOM | 2886 | P | G | A2899 | -2.742 | 248.466 | 320.233 | 1.00 | 0.00 | P |
| ATOM | 2887 | P | A | A2900 | -5.920 | 249.564 | 324.018 | 1.00 | 0.00 | P |
| ATOM | 2888 | P | C | A2901 | -8.768 | 249.731 | 328.187 | 1.00 | 0.00 | P |
| ATOM | 2889 | P | C | A2902 | -8.869 | 251.524 | 334.493 | 1.00 | 0.00 | P |
| TER | 2890 | | C | A2902 | | | | | | |
| ATOM | 2891 | P | A | B -1 | 68.027 | 193.032 | 202.621 | 1.00 | 0.00 | P |
| ATOM | 2892 | P | A | B 0 | 62.623 | 194.187 | 206.460 | 1.00 | 0.00 | P |
| ATOM | 2893 | P | U | B 1 | 58.668 | 196.836 | 208.198 | 1.00 | 0.00 | P |
| ATOM | 2894 | P | C | B 2 | 50.789 | 197.944 | 208.216 | 1.00 | 0.00 | P |
| ATOM | 2895 | P | C | B 3 | 46.559 | 193.194 | 207.534 | 1.00 | 0.00 | P |
| ATOM | 2896 | P | C | B 4 | 44.402 | 186.559 | 206.866 | 1.00 | 0.00 | P |
| ATOM | 2897 | P | C | B 5 | 44.241 | 180.738 | 207.132 | 1.00 | 0.00 | P |
| ATOM | 2898 | P | C | B 6 | 47.054 | 176.068 | 209.187 | 1.00 | 0.00 | P |
| ATOM | 2899 | P | G | B 7 | 51.649 | 174.417 | 212.380 | 1.00 | 0.00 | P |
| ATOM | 2900 | P | U | B 8 | 54.701 | 175.190 | 217.173 | 1.00 | 0.00 | P |
| ATOM | 2901 | P | G | B 9 | 55.841 | 177.164 | 222.875 | 1.00 | 0.00 | P |
| ATOM | 2902 | P | C | B 10 | 53.078 | 181.488 | 227.090 | 1.00 | 0.00 | P |
| ATOM | 2903 | P | C | B 11 | 50.985 | 185.122 | 230.493 | 1.00 | 0.00 | P |
| ATOM | 2904 | P | C | B 12 | 45.983 | 186.068 | 232.835 | 1.00 | 0.00 | P |
| ATOM | 2905 | P | A | B 13 | 41.033 | 182.949 | 232.475 | 1.00 | 0.00 | P |
| ATOM | 2906 | P | U | B 14 | 36.348 | 185.634 | 229.082 | 1.00 | 0.00 | P |
| ATOM | 2907 | P | A | B 15 | 35.541 | 183.834 | 224.841 | 1.00 | 0.00 | P |
| ATOM | 2908 | P | G | B 16 | 35.065 | 178.693 | 225.599 | 1.00 | 0.00 | P |
| ATOM | 2909 | P | C | B 17 | 33.983 | 173.363 | 223.918 | 1.00 | 0.00 | P |
| ATOM | 2910 | P | G | B 18 | 30.459 | 169.755 | 221.858 | 1.00 | 0.00 | P |
| ATOM | 2911 | P | G | B 19 | 26.961 | 169.328 | 217.267 | 1.00 | 0.00 | P |
| ATOM | 2912 | P | C | B 20 | 24.676 | 171.566 | 212.627 | 1.00 | 0.00 | P |
| ATOM | 2913 | P | G | B 21 | 25.261 | 173.687 | 206.809 | 1.00 | 0.00 | P |
| ATOM | 2914 | P | U | B 22 | 28.514 | 175.960 | 202.201 | 1.00 | 0.00 | P |
| ATOM | 2915 | P | G | B 23 | 33.560 | 177.383 | 199.334 | 1.00 | 0.00 | P |
| ATOM | 2916 | P | G | B 24 | 38.459 | 176.790 | 197.549 | 1.00 | 0.00 | P |
| ATOM | 2917 | P | A | B 25 | 42.949 | 175.475 | 195.149 | 1.00 | 0.00 | P |
| ATOM | 2918 | P | A | B 26 | 49.564 | 175.359 | 195.482 | 1.00 | 0.00 | P |
| ATOM | 2919 | P | C | B 27 | 52.900 | 173.721 | 199.849 | 1.00 | 0.00 | P |
| ATOM | 2920 | P | C | B 28 | 52.049 | 172.424 | 204.941 | 1.00 | 0.00 | P |
| ATOM | 2921 | P | A | B 29 | 49.734 | 169.122 | 208.960 | 1.00 | 0.00 | P |
| ATOM | 2922 | P | C | B 30 | 45.154 | 164.143 | 209.282 | 1.00 | 0.00 | P |
| ATOM | 2923 | P | C | B 31 | 41.796 | 159.812 | 206.812 | 1.00 | 0.00 | P |
| ATOM | 2924 | P | C | B 32 | 42.716 | 156.272 | 202.383 | 1.00 | 0.00 | P |
| ATOM | 2925 | P | G | B 33 | 45.735 | 152.177 | 200.490 | 1.00 | 0.00 | P |

| | | | | | | | | | | |
|---|---|---|---|---|---|---|---|---|---|---|
| ATOM | 2926 | P | U | B | 34 | 50.295 | 148.284 | 202.424 | 1.00 | 0.00 | P |
| ATOM | 2927 | P | U | B | 35 | 55.813 | 145.204 | 204.660 | 1.00 | 0.00 | P |
| ATOM | 2928 | P | C | B | 36 | 61.348 | 145.135 | 207.563 | 1.00 | 0.00 | P |
| ATOM | 2929 | P | C | B | 37 | 64.427 | 148.372 | 211.606 | 1.00 | 0.00 | P |
| ATOM | 2930 | P | C | B | 38 | 63.920 | 149.912 | 216.602 | 1.00 | 0.00 | P |
| ATOM | 2931 | P | A | B | 39 | 59.111 | 149.726 | 219.971 | 1.00 | 0.00 | P |
| ATOM | 2932 | P | U | B | 40 | 53.929 | 147.878 | 221.726 | 1.00 | 0.00 | P |
| ATOM | 2933 | P | U | B | 41 | 47.346 | 146.992 | 223.506 | 1.00 | 0.00 | P |
| ATOM | 2934 | P | C | B | 42 | 49.494 | 140.880 | 222.941 | 1.00 | 0.00 | P |
| ATOM | 2935 | P | C | B | 43 | 48.878 | 142.486 | 217.234 | 1.00 | 0.00 | P |
| ATOM | 2936 | P | G | B | 44 | 48.268 | 145.929 | 212.490 | 1.00 | 0.00 | P |
| ATOM | 2937 | P | A | B | 45 | 46.037 | 151.085 | 210.871 | 1.00 | 0.00 | P |
| ATOM | 2938 | P | A | B | 46 | 45.336 | 156.262 | 212.688 | 1.00 | 0.00 | P |
| ATOM | 2939 | P | C | B | 47 | 48.509 | 159.328 | 216.079 | 1.00 | 0.00 | P |
| ATOM | 2940 | P | A | B | 48 | 54.068 | 159.654 | 217.018 | 1.00 | 0.00 | P |
| ATOM | 2941 | P | C | B | 49 | 58.861 | 159.213 | 213.050 | 1.00 | 0.00 | P |
| ATOM | 2942 | P | G | B | 50 | 60.925 | 158.953 | 207.229 | 1.00 | 0.00 | P |
| ATOM | 2943 | P | G | B | 51 | 59.872 | 159.953 | 201.814 | 1.00 | 0.00 | P |
| ATOM | 2944 | P | A | B | 52 | 56.403 | 161.279 | 196.540 | 1.00 | 0.00 | P |
| ATOM | 2945 | P | A | B | 53 | 51.389 | 161.327 | 192.520 | 1.00 | 0.00 | P |
| ATOM | 2946 | P | G | B | 54 | 46.188 | 161.470 | 191.712 | 1.00 | 0.00 | P |
| ATOM | 2947 | P | U | B | 55 | 40.282 | 164.856 | 192.545 | 1.00 | 0.00 | P |
| ATOM | 2948 | P | G | B | 56 | 35.663 | 167.600 | 195.435 | 1.00 | 0.00 | P |
| ATOM | 2949 | P | A | B | 57 | 31.515 | 168.672 | 200.721 | 1.00 | 0.00 | P |
| ATOM | 2950 | P | A | B | 58 | 30.682 | 168.047 | 207.670 | 1.00 | 0.00 | P |
| ATOM | 2951 | P | A | B | 59 | 35.192 | 168.559 | 212.990 | 1.00 | 0.00 | P |
| ATOM | 2952 | P | C | B | 60 | 39.982 | 171.994 | 215.137 | 1.00 | 0.00 | P |
| ATOM | 2953 | P | G | B | 61 | 41.908 | 177.364 | 214.630 | 1.00 | 0.00 | P |
| ATOM | 2954 | P | C | B | 62 | 40.703 | 182.760 | 212.479 | 1.00 | 0.00 | P |
| ATOM | 2955 | P | G | B | 63 | 36.603 | 186.415 | 211.146 | 1.00 | 0.00 | P |
| ATOM | 2956 | P | C | B | 64 | 30.992 | 188.004 | 211.941 | 1.00 | 0.00 | P |
| ATOM | 2957 | P | C | B | 65 | 25.549 | 186.519 | 214.706 | 1.00 | 0.00 | P |
| ATOM | 2958 | P | A | B | 66 | 21.032 | 185.237 | 218.225 | 1.00 | 0.00 | P |
| ATOM | 2959 | P | G | B | 67 | 18.025 | 182.931 | 223.211 | 1.00 | 0.00 | P |
| ATOM | 2960 | P | C | B | 68 | 18.919 | 178.224 | 227.467 | 1.00 | 0.00 | P |
| ATOM | 2961 | P | G | B | 69 | 24.160 | 178.401 | 232.140 | 1.00 | 0.00 | P |
| ATOM | 2962 | P | C | B | 70 | 31.336 | 180.185 | 234.274 | 1.00 | 0.00 | P |
| ATOM | 2963 | P | C | B | 71 | 34.575 | 185.246 | 234.207 | 1.00 | 0.00 | P |
| ATOM | 2964 | P | G | B | 72 | 33.396 | 191.015 | 236.391 | 1.00 | 0.00 | P |
| ATOM | 2965 | P | A | B | 73 | 30.926 | 195.926 | 237.745 | 1.00 | 0.00 | P |
| ATOM | 2966 | P | U | B | 74 | 28.554 | 201.234 | 238.510 | 1.00 | 0.00 | P |
| ATOM | 2967 | P | G | B | 75 | 25.614 | 204.844 | 240.765 | 1.00 | 0.00 | P |
| ATOM | 2968 | P | G | B | 76 | 22.563 | 205.632 | 245.858 | 1.00 | 0.00 | P |
| ATOM | 2969 | P | U | B | 77 | 20.773 | 203.526 | 251.030 | 1.00 | 0.00 | P |
| ATOM | 2970 | P | A | B | 78 | 20.531 | 198.986 | 254.531 | 1.00 | 0.00 | P |
| ATOM | 2971 | P | C | B | 79 | 22.721 | 195.441 | 257.897 | 1.00 | 0.00 | P |
| ATOM | 2972 | P | U | B | 80 | 27.795 | 194.945 | 261.099 | 1.00 | 0.00 | P |
| ATOM | 2973 | P | G | B | 81 | 33.218 | 197.414 | 262.989 | 1.00 | 0.00 | P |
| ATOM | 2974 | P | G | B | 82 | 35.974 | 200.544 | 266.733 | 1.00 | 0.00 | P |
| ATOM | 2975 | P | G | B | 83 | 35.660 | 204.541 | 270.232 | 1.00 | 0.00 | P |
| ATOM | 2976 | P | C | B | 84 | 32.242 | 208.046 | 272.842 | 1.00 | 0.00 | P |
| ATOM | 2977 | P | G | B | 85 | 26.791 | 208.356 | 275.507 | 1.00 | 0.00 | P |
| ATOM | 2978 | P | G | B | 86 | 21.029 | 206.996 | 277.269 | 1.00 | 0.00 | P |
| ATOM | 2979 | P | G | B | 87 | 15.008 | 203.425 | 277.587 | 1.00 | 0.00 | P |
| ATOM | 2980 | P | C | B | 88 | 13.375 | 198.739 | 279.762 | 1.00 | 0.00 | P |
| ATOM | 2981 | P | G | B | 89 | 18.431 | 195.616 | 278.872 | 1.00 | 0.00 | P |
| ATOM | 2982 | P | A | B | 89A | 19.904 | 190.895 | 274.804 | 1.00 | 0.00 | P |
| ATOM | 2983 | P | C | B | 90 | 19.614 | 189.208 | 269.416 | 1.00 | 0.00 | P |
| ATOM | 2984 | P | C | B | 91 | 17.302 | 194.369 | 265.832 | 1.00 | 0.00 | P |
| ATOM | 2985 | P | G | B | 92 | 18.123 | 199.490 | 263.250 | 1.00 | 0.00 | P |
| ATOM | 2986 | P | C | B | 93 | 18.888 | 205.924 | 261.967 | 1.00 | 0.00 | P |
| ATOM | 2987 | P | C | B | 94 | 22.076 | 210.963 | 261.518 | 1.00 | 0.00 | P |
| ATOM | 2988 | P | U | B | 95 | 26.803 | 212.741 | 259.766 | 1.00 | 0.00 | P |
| ATOM | 2989 | P | G | B | 96 | 31.517 | 211.858 | 256.903 | 1.00 | 0.00 | P |
| ATOM | 2990 | P | G | B | 97 | 34.845 | 208.729 | 253.525 | 1.00 | 0.00 | P |
| ATOM | 2991 | P | G | B | 98 | 35.207 | 203.836 | 250.278 | 1.00 | 0.00 | P |
| ATOM | 2992 | P | A | B | 99 | 32.284 | 199.734 | 247.071 | 1.00 | 0.00 | P |
| ATOM | 2993 | P | G | B | 100 | 31.333 | 194.103 | 246.013 | 1.00 | 0.00 | P |
| ATOM | 2994 | P | A | B | 101 | 29.087 | 189.537 | 245.925 | 1.00 | 0.00 | P |
| ATOM | 2995 | P | G | B | 102 | 24.451 | 187.266 | 243.796 | 1.00 | 0.00 | P |
| ATOM | 2996 | P | U | B | 103 | 20.003 | 188.696 | 239.820 | 1.00 | 0.00 | P |
| ATOM | 2997 | P | A | B | 104 | 18.109 | 191.842 | 235.068 | 1.00 | 0.00 | P |
| ATOM | 2998 | P | G | B | 105 | 19.083 | 191.992 | 230.234 | 1.00 | 0.00 | P |
| ATOM | 2999 | P | G | B | 106 | 22.854 | 193.354 | 225.940 | 1.00 | 0.00 | P |
| ATOM | 3000 | P | U | B | 107 | 28.527 | 192.332 | 223.929 | 1.00 | 0.00 | P |
| ATOM | 3001 | P | C | B | 108 | 31.400 | 188.655 | 221.465 | 1.00 | 0.00 | P |
| ATOM | 3002 | P | G | B | 109 | 36.207 | 186.869 | 220.388 | 1.00 | 0.00 | P |
| ATOM | 3003 | P | G | B | 110 | 40.021 | 190.788 | 218.772 | 1.00 | 0.00 | P |
| ATOM | 3004 | P | U | B | 111 | 44.730 | 192.599 | 218.027 | 1.00 | 0.00 | P |
| ATOM | 3005 | P | G | B | 112 | 50.744 | 192.861 | 218.759 | 1.00 | 0.00 | P |
| ATOM | 3006 | P | C | B | 113 | 57.395 | 191.097 | 217.190 | 1.00 | 0.00 | P |
| ATOM | 3007 | P | G | B | 114 | 60.858 | 186.618 | 212.633 | 1.00 | 0.00 | P |
| ATOM | 3008 | P | G | B | 115 | 62.632 | 183.077 | 208.778 | 1.00 | 0.00 | P |
| ATOM | 3009 | P | G | B | 116 | 61.303 | 181.249 | 203.723 | 1.00 | 0.00 | P |
| ATOM | 3010 | P | G | B | 117 | 58.376 | 180.545 | 198.988 | 1.00 | 0.00 | P |
| ATOM | 3011 | P | G | B | 118 | 54.186 | 182.741 | 195.209 | 1.00 | 0.00 | P |
| ATOM | 3012 | P | A | B | 119 | 51.214 | 188.031 | 193.787 | 1.00 | 0.00 | P |

```
ATOM  3013  P       U B 120    50.410 193.321 194.061 1.00 0.00    P
TER   3014          U B 120
ATOM  3015  CA LYS C   5      101.841  85.750 263.044 1.00 0.00    C
ATOM  3016  CA ARG C   6      103.954  88.132 260.689 1.00 0.00    C
ATOM  3017  CA TYR C   7      104.776  91.071 262.942 1.00 0.00    C
ATOM  3018  CA ARG C   8      106.693  90.450 266.217 1.00 0.00    C
ATOM  3019  CA ALA C   9      109.811  91.904 264.677 1.00 0.00    C
ATOM  3020  CA LEU C  10      107.764  94.750 263.245 1.00 0.00    C
ATOM  3021  CA LEU C  11      106.525  95.693 266.763 1.00 0.00    C
ATOM  3022  CA GLU C  12      110.009  95.959 268.292 1.00 0.00    C
ATOM  3023  CA LYS C  13      111.175  98.856 266.084 1.00 0.00    C
ATOM  3024  CA VAL C  14      108.385 101.238 267.131 1.00 0.00    C
ATOM  3025  CA ASP C  15      107.979 102.853 270.547 1.00 0.00    C
ATOM  3026  CA PRO C  16      104.181 103.405 270.874 1.00 0.00    C
ATOM  3027  CA ASN C  17      104.530 106.117 273.549 1.00 0.00    C
ATOM  3028  CA LYS C  18      107.026 108.206 271.550 1.00 0.00    C
ATOM  3029  CA ILE C  19      106.046 111.256 269.415 1.00 0.00    C
ATOM  3030  CA TYR C  20      108.496 111.071 266.487 1.00 0.00    C
ATOM  3031  CA THR C  21      109.734 114.022 264.450 1.00 0.00    C
ATOM  3032  CA ILE C  22      108.709 113.861 260.772 1.00 0.00    C
ATOM  3033  CA ASP C  23      112.318 113.083 259.730 1.00 0.00    C
ATOM  3034  CA GLU C  24      112.639 110.181 262.186 1.00 0.00    C
ATOM  3035  CA ALA C  25      109.294 108.722 261.020 1.00 0.00    C
ATOM  3036  CA ALA C  26      110.311 109.135 257.370 1.00 0.00    C
ATOM  3037  CA HIS C  27      113.389 106.984 258.040 1.00 0.00    C
ATOM  3038  CA LEU C  28      111.575 104.563 260.342 1.00 0.00    C
ATOM  3039  CA VAL C  29      108.577 103.987 258.097 1.00 0.00    C
ATOM  3040  CA LYS C  30      110.788 102.583 255.352 1.00 0.00    C
ATOM  3041  CA GLU C  31      111.872  99.778 257.738 1.00 0.00    C
ATOM  3042  CA LEU C  32      108.239  98.818 258.557 1.00 0.00    C
ATOM  3043  CA ALA C  33      107.329  98.417 254.913 1.00 0.00    C
ATOM  3044  CA THR C  34      109.372  95.245 254.510 1.00 0.00    C
ATOM  3045  CA ALA C  35      106.629  93.516 252.507 1.00 0.00    C
ATOM  3046  CA LYS C  36      105.953  92.652 248.890 1.00 0.00    C
ATOM  3047  CA PHE C  37      105.839  95.408 246.233 1.00 0.00    C
ATOM  3048  CA ASP C  38      106.004  99.163 246.903 1.00 0.00    C
ATOM  3049  CA GLU C  39      103.870  99.988 249.930 1.00 0.00    C
ATOM  3050  CA THR C  40      101.895 103.226 249.998 1.00 0.00    C
ATOM  3051  CA VAL C  41      102.709 105.573 252.881 1.00 0.00    C
ATOM  3052  CA GLU C  42       99.819 107.566 254.398 1.00 0.00    C
ATOM  3053  CA VAL C  43       99.378 110.280 256.995 1.00 0.00    C
ATOM  3054  CA HIS C  44       96.315 109.952 259.248 1.00 0.00    C
ATOM  3055  CA ALA C  45       94.944 112.483 261.715 1.00 0.00    C
ATOM  3056  CA LYS C  46       92.238 112.760 264.360 1.00 0.00    C
ATOM  3057  CA LEU C  47       90.677 116.239 263.999 1.00 0.00    C
ATOM  3058  CA GLY C  48       89.034 118.415 266.579 1.00 0.00    C
ATOM  3059  CA ILE C  49       85.743 118.802 264.714 1.00 0.00    C
ATOM  3060  CA ASP C  50       82.115 117.739 264.970 1.00 0.00    C
ATOM  3061  CA PRO C  51       81.857 115.419 261.924 1.00 0.00    C
ATOM  3062  CA ARG C  52       78.033 115.808 261.854 1.00 0.00    C
ATOM  3063  CA ARG C  53       78.305 119.604 261.275 1.00 0.00    C
ATOM  3064  CA SER C  54       78.590 120.681 257.673 1.00 0.00    C
ATOM  3065  CA ASP C  55       80.251 124.010 258.619 1.00 0.00    C
ATOM  3066  CA GLN C  56       83.080 122.105 260.351 1.00 0.00    C
ATOM  3067  CA ASN C  57       83.873 119.662 257.572 1.00 0.00    C
ATOM  3068  CA VAL C  58       87.352 119.640 255.992 1.00 0.00    C
ATOM  3069  CA ARG C  59       87.775 119.207 252.245 1.00 0.00    C
ATOM  3070  CA GLY C  60       90.609 120.499 250.087 1.00 0.00    C
ATOM  3071  CA THR C  61       93.601 119.727 247.909 1.00 0.00    C
ATOM  3072  CA VAL C  62       97.352 119.561 248.448 1.00 0.00    C
ATOM  3073  CA SER C  63       99.990 119.985 245.742 1.00 0.00    C
ATOM  3074  CA LEU C  64      102.655 117.523 246.945 1.00 0.00    C
ATOM  3075  CA PRO C  65      104.883 115.293 245.792 1.00 0.00    C
ATOM  3076  CA HIS C  66      104.691 112.575 243.065 1.00 0.00    C
ATOM  3077  CA GLY C  67      102.698 111.699 239.826 1.00 0.00    C
ATOM  3078  CA LEU C  68      100.790 114.091 237.666 1.00 0.00    C
ATOM  3079  CA GLY C  69       99.983 114.475 233.968 1.00 0.00    C
ATOM  3080  CA LYS C  70       99.737 111.627 231.465 1.00 0.00    C
ATOM  3081  CA GLN C  71      100.779 108.761 233.693 1.00 0.00    C
ATOM  3082  CA VAL C  72       97.782 109.422 235.989 1.00 0.00    C
ATOM  3083  CA ARG C  73       95.040 106.902 235.169 1.00 0.00    C
ATOM  3084  CA VAL C  74       91.751 108.786 235.522 1.00 0.00    C
ATOM  3085  CA LEU C  75       88.448 107.061 236.210 1.00 0.00    C
ATOM  3086  CA ALA C  76       85.400 109.188 235.233 1.00 0.00    C
ATOM  3087  CA ILE C  77       81.906 108.266 236.535 1.00 0.00    C
ATOM  3088  CA ALA C  78       79.077 110.009 234.738 1.00 0.00    C
ATOM  3089  CA LYS C  79       75.598 109.786 233.147 1.00 0.00    C
ATOM  3090  CA GLY C  80       73.932 110.512 229.809 1.00 0.00    C
ATOM  3091  CA GLU C  81       75.859 112.404 227.193 1.00 0.00    C
ATOM  3092  CA LYS C  82       78.479 113.193 229.859 1.00 0.00    C
ATOM  3093  CA ILE C  83       79.960 109.697 229.404 1.00 0.00    C
ATOM  3094  CA LYS C  84       80.674 110.656 225.775 1.00 0.00    C
ATOM  3095  CA GLU C  85       82.258 113.935 226.881 1.00 0.00    C
ATOM  3096  CA ALA C  86       84.498 112.035 229.312 1.00 0.00    C
ATOM  3097  CA GLU C  87       85.539 109.590 226.561 1.00 0.00    C
ATOM  3098  CA GLU C  88       86.268 112.449 224.145 1.00 0.00    C
ATOM  3099  CA ALA C  89       88.428 114.194 226.805 1.00 0.00    C
```

```
ATOM  3100  CA  GLY C  90      90.612 111.113 227.154  1.00  0.00           C
ATOM  3101  CA  ALA C  91      89.794 109.753 230.608  1.00  0.00           C
ATOM  3102  CA  ASP C  92      91.505 106.355 231.043  1.00  0.00           C
ATOM  3103  CA  TYR C  93      88.387 104.609 232.337  1.00  0.00           C
ATOM  3104  CA  VAL C  94      84.816 105.771 231.923  1.00  0.00           C
ATOM  3105  CA  GLY C  95      81.615 104.279 233.227  1.00  0.00           C
ATOM  3106  CA  GLY C  96      78.149 105.017 234.549  1.00  0.00           C
ATOM  3107  CA  GLU C  97      77.028 103.849 238.018  1.00  0.00           C
ATOM  3108  CA  GLU C  98      77.417 100.230 236.846  1.00  0.00           C
ATOM  3109  CA  ILE C  99      81.151 100.645 237.372  1.00  0.00           C
ATOM  3110  CA  ILE C 100      80.728 101.035 241.166  1.00  0.00           C
ATOM  3111  CA  GLN C 101      80.209  97.203 241.479  1.00  0.00           C
ATOM  3112  CA  LYS C 102      83.539  96.707 239.693  1.00  0.00           C
ATOM  3113  CA  ILE C 103      85.320  98.814 242.326  1.00  0.00           C
ATOM  3114  CA  LEU C 104      83.356  96.957 245.058  1.00  0.00           C
ATOM  3115  CA  ASP C 105      84.655  93.597 243.708  1.00  0.00           C
ATOM  3116  CA  GLY C 106      88.246  94.760 244.027  1.00  0.00           C
ATOM  3117  CA  TRP C 107      89.035  96.808 240.895  1.00  0.00           C
ATOM  3118  CA  MET C 108      91.300  99.665 241.874  1.00  0.00           C
ATOM  3119  CA  ASP C 109      93.768 100.392 239.026  1.00  0.00           C
ATOM  3120  CA  PHE C 110      93.236 104.095 238.810  1.00  0.00           C
ATOM  3121  CA  ASP C 111      94.976 107.015 240.449  1.00  0.00           C
ATOM  3122  CA  ALA C 112      92.181 109.598 240.437  1.00  0.00           C
ATOM  3123  CA  VAL C 113      88.399 109.757 240.247  1.00  0.00           C
ATOM  3124  CA  VAL C 114      86.223 112.519 238.825  1.00  0.00           C
ATOM  3125  CA  ALA C 115      82.441 112.530 238.637  1.00  0.00           C
ATOM  3126  CA  THR C 116      79.383 114.506 237.687  1.00  0.00           C
ATOM  3127  CA  PRO C 117      77.065 115.867 240.461  1.00  0.00           C
ATOM  3128  CA  ASP C 118      74.306 113.417 239.531  1.00  0.00           C
ATOM  3129  CA  VAL C 119      76.095 110.135 240.328  1.00  0.00           C
ATOM  3130  CA  MET C 120      77.485 111.362 243.666  1.00  0.00           C
ATOM  3131  CA  GLY C 121      74.651 110.176 245.888  1.00  0.00           C
ATOM  3132  CA  ALA C 122      75.346 106.605 244.864  1.00  0.00           C
ATOM  3133  CA  VAL C 123      79.122 107.189 244.702  1.00  0.00           C
ATOM  3134  CA  GLY C 124      79.457 108.804 248.121  1.00  0.00           C
ATOM  3135  CA  SER C 125      77.024 106.310 249.574  1.00  0.00           C
ATOM  3136  CA  LYS C 126      78.559 103.093 248.183  1.00  0.00           C
ATOM  3137  CA  LEU C 127      82.246 104.088 248.034  1.00  0.00           C
ATOM  3138  CA  GLY C 128      82.728 106.730 250.720  1.00  0.00           C
ATOM  3139  CA  ARG C 129      84.032 103.937 252.941  1.00  0.00           C
ATOM  3140  CA  ILE C 130      86.705 102.601 250.526  1.00  0.00           C
ATOM  3141  CA  LEU C 131      87.716 105.742 248.605  1.00  0.00           C
ATOM  3142  CA  GLY C 132      87.278 108.301 251.402  1.00  0.00           C
ATOM  3143  CA  PRO C 133      90.337 107.306 253.503  1.00  0.00           C
ATOM  3144  CA  ARG C 134      92.483 106.607 250.409  1.00  0.00           C
ATOM  3145  CA  GLY C 135      91.836 110.190 249.320  1.00  0.00           C
ATOM  3146  CA  LEU C 136      90.027 109.069 246.156  1.00  0.00           C
ATOM  3147  CA  LEU C 137      86.489 110.473 246.739  1.00  0.00           C
ATOM  3148  CA  PRO C 138      85.385 113.167 244.223  1.00  0.00           C
ATOM  3149  CA  ASN C 139      84.866 116.404 246.128  1.00  0.00           C
ATOM  3150  CA  PRO C 140      83.569 119.821 245.021  1.00  0.00           C
ATOM  3151  CA  LYS C 141      86.523 121.895 246.361  1.00  0.00           C
ATOM  3152  CA  ALA C 142      89.142 119.356 245.408  1.00  0.00           C
ATOM  3153  CA  GLY C 143      87.787 120.238 241.945  1.00  0.00           C
ATOM  3154  CA  THR C 144      86.904 116.627 241.073  1.00  0.00           C
ATOM  3155  CA  VAL C 145      83.071 116.981 240.811  1.00  0.00           C
ATOM  3156  CA  GLY C 146      81.379 119.107 238.143  1.00  0.00           C
ATOM  3157  CA  PHE C 147      79.205 119.052 235.007  1.00  0.00           C
ATOM  3158  CA  ASN C 148      82.138 120.319 232.903  1.00  0.00           C
ATOM  3159  CA  ILE C 149      83.744 116.915 233.245  1.00  0.00           C
ATOM  3160  CA  GLY C 150      85.801 117.156 230.052  1.00  0.00           C
ATOM  3161  CA  GLU C 151      87.574 120.224 231.437  1.00  0.00           C
ATOM  3162  CA  ILE C 152      88.348 118.507 234.766  1.00  0.00           C
ATOM  3163  CA  ILE C 153      89.972 115.530 233.000  1.00  0.00           C
ATOM  3164  CA  ARG C 154      92.131 117.699 230.718  1.00  0.00           C
ATOM  3165  CA  GLU C 155      93.480 119.693 233.704  1.00  0.00           C
ATOM  3166  CA  ILE C 156      94.835 116.628 235.552  1.00  0.00           C
ATOM  3167  CA  LYS C 157      97.377 117.870 235.890  1.00  0.00           C
ATOM  3168  CA  ALA C 158      97.905 120.566 238.511  1.00  0.00           C
ATOM  3169  CA  GLY C 159      98.295 117.825 241.118  1.00  0.00           C
ATOM  3170  CA  ARG C 160      96.730 117.363 243.601  1.00  0.00           C
ATOM  3171  CA  ILE C 161      95.264 115.256 245.449  1.00  0.00           C
ATOM  3172  CA  GLU C 162      91.995 115.811 247.337  1.00  0.00           C
ATOM  3173  CA  PHE C 163      91.270 115.200 251.002  1.00  0.00           C
ATOM  3174  CA  ARG C 164      88.197 115.147 253.190  1.00  0.00           C
ATOM  3175  CA  ASN C 165      87.359 113.939 256.670  1.00  0.00           C
ATOM  3176  CA  ASP C 166      85.340 110.766 257.139  1.00  0.00           C
ATOM  3177  CA  LYS C 167      82.349 110.251 259.466  1.00  0.00           C
ATOM  3178  CA  THR C 168      84.589 109.332 262.418  1.00  0.00           C
ATOM  3179  CA  GLY C 169      86.339 112.705 262.318  1.00  0.00           C
ATOM  3180  CA  ALA C 170      89.511 111.177 260.899  1.00  0.00           C
ATOM  3181  CA  ILE C 171      91.220 112.201 257.666  1.00  0.00           C
ATOM  3182  CA  HIS C 172      94.113 110.847 255.688  1.00  0.00           C
ATOM  3183  CA  ALA C 173      95.938 110.739 252.408  1.00  0.00           C
ATOM  3184  CA  PRO C 174      98.758 108.869 250.639  1.00  0.00           C
ATOM  3185  CA  VAL C 175     102.024 110.817 250.594  1.00  0.00           C
ATOM  3186  CA  GLY C 176     104.414 108.477 248.808  1.00  0.00           C
```

```
ATOM   3187  CA  LYS C 177     105.659 104.919 248.585  1.00  0.00           C
ATOM   3188  CA  ALA C 178     108.011 103.136 250.995  1.00  0.00           C
ATOM   3189  CA  SER C 179     110.829 103.190 248.447  1.00  0.00           C
ATOM   3190  CA  PHE C 180     110.957 107.018 248.318  1.00  0.00           C
ATOM   3191  CA  PRO C 181     114.150 108.597 249.701  1.00  0.00           C
ATOM   3192  CA  PRO C 182     113.358 109.738 253.304  1.00  0.00           C
ATOM   3193  CA  GLU C 183     113.839 113.460 252.570  1.00  0.00           C
ATOM   3194  CA  LYS C 184     111.208 113.384 249.811  1.00  0.00           C
ATOM   3195  CA  LEU C 185     108.852 111.476 252.067  1.00  0.00           C
ATOM   3196  CA  ALA C 186     109.521 114.011 254.794  1.00  0.00           C
ATOM   3197  CA  ASP C 187     108.839 116.889 252.369  1.00  0.00           C
ATOM   3198  CA  ASN C 188     105.504 115.371 251.284  1.00  0.00           C
ATOM   3199  CA  ILE C 189     104.371 114.715 254.910  1.00  0.00           C
ATOM   3200  CA  ARG C 190     105.075 118.350 255.909  1.00  0.00           C
ATOM   3201  CA  ALA C 191     103.239 119.535 252.778  1.00  0.00           C
ATOM   3202  CA  PHE C 192     100.084 117.605 253.738  1.00  0.00           C
ATOM   3203  CA  ILE C 193     100.148 118.945 257.332  1.00  0.00           C
ATOM   3204  CA  ARG C 194     100.586 122.577 256.126  1.00  0.00           C
ATOM   3205  CA  ALA C 195      97.658 122.119 253.706  1.00  0.00           C
ATOM   3206  CA  LEU C 196      95.483 120.547 256.360  1.00  0.00           C
ATOM   3207  CA  GLU C 197      96.081 123.415 258.895  1.00  0.00           C
ATOM   3208  CA  ALA C 198      95.249 126.063 256.295  1.00  0.00           C
ATOM   3209  CA  HIS C 199      91.846 124.291 256.076  1.00  0.00           C
ATOM   3210  CA  LYS C 200      90.943 124.494 259.770  1.00  0.00           C
ATOM   3211  CA  PRO C 201      87.239 125.517 259.828  1.00  0.00           C
ATOM   3212  CA  GLU C 202      86.278 128.975 261.204  1.00  0.00           C
ATOM   3213  CA  GLY C 203      84.357 127.851 264.252  1.00  0.00           C
ATOM   3214  CA  ALA C 204      86.349 124.719 265.079  1.00  0.00           C
ATOM   3215  CA  LYS C 205      87.179 125.211 268.736  1.00  0.00           C
ATOM   3216  CA  GLY C 206      89.998 123.671 270.677  1.00  0.00           C
ATOM   3217  CA  THR C 207      92.892 121.703 269.263  1.00  0.00           C
ATOM   3218  CA  PHE C 208      92.495 120.963 265.540  1.00  0.00           C
ATOM   3219  CA  LEU C 209      95.159 118.255 265.050  1.00  0.00           C
ATOM   3220  CA  ARG C 210      94.641 116.072 268.152  1.00  0.00           C
ATOM   3221  CA  SER C 211      97.083 113.369 267.053  1.00  0.00           C
ATOM   3222  CA  VAL C 212      98.842 112.648 263.756  1.00  0.00           C
ATOM   3223  CA  TYR C 213     100.225 109.327 262.408  1.00  0.00           C
ATOM   3224  CA  VAL C 214     102.264 108.002 259.512  1.00  0.00           C
ATOM   3225  CA  THR C 215     101.525 104.399 258.435  1.00  0.00           C
ATOM   3226  CA  THR C 216     101.972 101.852 255.651  1.00  0.00           C
ATOM   3227  CA  THR C 217      99.439  99.466 254.069  1.00  0.00           C
ATOM   3228  CA  MET C 218      99.480  96.853 256.837  1.00  0.00           C
ATOM   3229  CA  GLY C 219     101.969  98.046 259.453  1.00  0.00           C
ATOM   3230  CA  PRO C 220     102.079  99.678 262.923  1.00  0.00           C
ATOM   3231  CA  SER C 221     101.414 103.412 263.114  1.00  0.00           C
ATOM   3232  CA  VAL C 222     104.071 105.888 264.152  1.00  0.00           C
ATOM   3233  CA  ARG C 223     102.868 108.968 266.051  1.00  0.00           C
ATOM   3234  CA  ILE C 224     104.471 112.202 264.844  1.00  0.00           C
ATOM   3235  CA  ASN C 225     104.948 115.792 265.893  1.00  0.00           C
ATOM   3236  CA  PRO C 226     103.096 117.832 263.192  1.00  0.00           C
ATOM   3237  CA  HIS C 227     105.269 120.826 263.937  1.00  0.00           C
ATOM   3238  CA  SER C 228     108.670 119.294 263.191  1.00  0.00           C
TER    3239      SER C 228
ATOM   3240  CA  GLN D  60      51.892 122.772 350.656  1.00  0.00           C
ATOM   3241  CA  TYR D  61      53.424 121.379 347.422  1.00  0.00           C
ATOM   3242  CA  ARG D  62      55.140 118.169 348.526  1.00  0.00           C
ATOM   3243  CA  ILE D  63      58.474 116.963 347.219  1.00  0.00           C
ATOM   3244  CA  ILE D  64      58.034 113.980 344.900  1.00  0.00           C
ATOM   3245  CA  ASP D  65      60.667 111.379 344.180  1.00  0.00           C
ATOM   3246  CA  PHE D  66      60.810 110.800 340.401  1.00  0.00           C
ATOM   3247  CA  LYS D  67      64.344 109.383 340.644  1.00  0.00           C
ATOM   3248  CA  ARG D  68      63.339 106.194 342.442  1.00  0.00           C
ATOM   3249  CA  ASP D  69      66.985 105.525 343.267  1.00  0.00           C
ATOM   3250  CA  LYS D  70      66.854 103.796 346.683  1.00  0.00           C
ATOM   3251  CA  ASP D  71      67.882 100.464 345.177  1.00  0.00           C
ATOM   3252  CA  GLY D  72      67.862  97.487 347.500  1.00  0.00           C
ATOM   3253  CA  ILE D  73      66.153  99.308 350.329  1.00  0.00           C
ATOM   3254  CA  PRO D  74      62.631  98.008 351.074  1.00  0.00           C
ATOM   3255  CA  GLY D  75      59.938 100.591 351.489  1.00  0.00           C
ATOM   3256  CA  ARG D  76      56.376 100.509 352.677  1.00  0.00           C
ATOM   3257  CA  VAL D  77      53.369 102.460 351.568  1.00  0.00           C
ATOM   3258  CA  ALA D  78      52.419 104.466 354.652  1.00  0.00           C
ATOM   3259  CA  THR D  79      49.576 106.489 353.161  1.00  0.00           C
ATOM   3260  CA  ILE D  80      47.899 107.548 349.921  1.00  0.00           C
ATOM   3261  CA  GLU D  81      46.645 111.119 349.525  1.00  0.00           C
ATOM   3262  CA  TYR D  82      45.545 113.531 346.824  1.00  0.00           C
ATOM   3263  CA  ASP D  83      47.911 116.205 345.637  1.00  0.00           C
ATOM   3264  CA  PRO D  84      46.011 119.240 344.217  1.00  0.00           C
ATOM   3265  CA  ASN D  85      49.175 120.681 342.712  1.00  0.00           C
ATOM   3266  CA  ARG D  86      49.707 117.588 340.632  1.00  0.00           C
ATOM   3267  CA  SER D  87      46.023 116.611 340.373  1.00  0.00           C
ATOM   3268  CA  ALA D  88      46.822 112.945 341.162  1.00  0.00           C
ATOM   3269  CA  ASN D  89      47.343 110.675 344.137  1.00  0.00           C
ATOM   3270  CA  ILE D  90      50.717 110.449 345.880  1.00  0.00           C
ATOM   3271  CA  ALA D  91      51.975 107.965 348.445  1.00  0.00           C
ATOM   3272  CA  LEU D  92      54.234 108.473 351.436  1.00  0.00           C
ATOM   3273  CA  ILE D  93      56.835 105.726 351.509  1.00  0.00           C
```

```
ATOM  3274  CA  ASN D  94    58.681 104.708 354.666  1.00  0.00           C
ATOM  3275  CA  TYR D  95    61.991 103.091 353.853  1.00  0.00           C
ATOM  3276  CA  ALA D  96    63.672 100.560 356.152  1.00  0.00           C
ATOM  3277  CA  ASP D  97    66.733 102.781 356.460  1.00  0.00           C
ATOM  3278  CA  GLY D  98    64.381 105.353 357.943  1.00  0.00           C
ATOM  3279  CA  GLU D  99    64.167 107.691 354.980  1.00  0.00           C
ATOM  3280  CA  LYS D 100    60.816 108.934 353.740  1.00  0.00           C
ATOM  3281  CA  ARG D 101    59.736 110.020 350.292  1.00  0.00           C
ATOM  3282  CA  TYR D 102    56.583 110.578 348.292  1.00  0.00           C
ATOM  3283  CA  ILE D 103    55.999 108.968 344.899  1.00  0.00           C
ATOM  3284  CA  ILE D 104    53.173 109.235 342.413  1.00  0.00           C
ATOM  3285  CA  ALA D 105    50.588 106.698 343.493  1.00  0.00           C
ATOM  3286  CA  PRO D 106    49.708 104.151 340.818  1.00  0.00           C
ATOM  3287  CA  LYS D 107    46.217 102.848 340.225  1.00  0.00           C
ATOM  3288  CA  ASN D 108    45.441 100.201 342.843  1.00  0.00           C
ATOM  3289  CA  LEU D 109    48.465 100.874 345.073  1.00  0.00           C
ATOM  3290  CA  LYS D 110    47.306 100.497 348.650  1.00  0.00           C
ATOM  3291  CA  VAL D 111    48.471 101.218 352.172  1.00  0.00           C
ATOM  3292  CA  GLY D 112    50.593  98.324 353.360  1.00  0.00           C
ATOM  3293  CA  MET D 113    54.830  98.773 350.925  1.00  0.00           C
ATOM  3294  CA  GLU D 114    55.914  96.998 349.827  1.00  0.00           C
ATOM  3295  CA  ILE D 115    57.843  99.001 347.253  1.00  0.00           C
ATOM  3296  CA  MET D 116    63.555  99.357 345.816  1.00  0.00           C
ATOM  3297  CA  SER D 117    63.380  99.729 342.941  1.00  0.00           C
ATOM  3298  CA  GLY D 118    66.331  98.475 340.931  1.00  0.00           C
ATOM  3299  CA  PRO D 119    67.225  95.369 338.804  1.00  0.00           C
ATOM  3300  CA  ASP D 120    65.972  92.947 341.453  1.00  0.00           C
ATOM  3301  CA  ALA D 121    62.546  94.275 342.319  1.00  0.00           C
ATOM  3302  CA  ASP D 122    59.572  92.052 341.517  1.00  0.00           C
ATOM  3303  CA  ILE D 123    57.124  93.220 338.851  1.00  0.00           C
ATOM  3304  CA  LYS D 124    54.428  94.949 340.878  1.00  0.00           C
ATOM  3305  CA  ILE D 125    52.868  98.375 340.842  1.00  0.00           C
ATOM  3306  CA  GLY D 126    54.956 101.064 342.482  1.00  0.00           C
ATOM  3307  CA  ASN D 127    58.190  99.242 341.805  1.00  0.00           C
ATOM  3308  CA  ALA D 128    60.714 100.981 339.573  1.00  0.00           C
ATOM  3309  CA  LEU D 129    63.243  99.136 337.400  1.00  0.00           C
ATOM  3310  CA  PRO D 130    65.450  99.631 334.338  1.00  0.00           C
ATOM  3311  CA  LEU D 131    63.257  99.012 331.285  1.00  0.00           C
ATOM  3312  CA  GLU D 132    65.501  96.091 330.255  1.00  0.00           C
ATOM  3313  CA  ASN D 133    64.327  94.283 333.402  1.00  0.00           C
ATOM  3314  CA  ILE D 134    60.641  94.832 332.644  1.00  0.00           C
ATOM  3315  CA  PRO D 135    58.463  92.143 330.979  1.00  0.00           C
ATOM  3316  CA  VAL D 136    57.001  92.894 327.558  1.00  0.00           C
ATOM  3317  CA  GLY D 137    53.337  93.811 327.985  1.00  0.00           C
ATOM  3318  CA  THR D 138    53.840  95.770 331.213  1.00  0.00           C
ATOM  3319  CA  LEU D 139    52.105  99.133 331.618  1.00  0.00           C
ATOM  3320  CA  VAL D 140    54.549 101.711 332.968  1.00  0.00           C
ATOM  3321  CA  HIS D 141    54.912 105.379 333.848  1.00  0.00           C
ATOM  3322  CA  ASN D 142    57.469 107.940 335.100  1.00  0.00           C
ATOM  3323  CA  ILE D 143    59.834 106.952 332.335  1.00  0.00           C
ATOM  3324  CA  GLU D 144    63.467 108.069 332.181  1.00  0.00           C
ATOM  3325  CA  LEU D 145    64.923 109.164 328.830  1.00  0.00           C
ATOM  3326  CA  LYS D 146    68.512 109.338 330.103  1.00  0.00           C
ATOM  3327  CA  PRO D 147    69.633 106.793 332.735  1.00  0.00           C
ATOM  3328  CA  GLY D 148    69.966 108.574 336.073  1.00  0.00           C
ATOM  3329  CA  ARG D 149    68.274 111.813 335.000  1.00  0.00           C
ATOM  3330  CA  GLY D 150    64.964 110.763 336.570  1.00  0.00           C
ATOM  3331  CA  GLY D 151    61.554 110.207 334.981  1.00  0.00           C
ATOM  3332  CA  GLN D 152    60.556 112.580 332.195  1.00  0.00           C
ATOM  3333  CA  LEU D 153    57.580 110.895 330.487  1.00  0.00           C
ATOM  3334  CA  VAL D 154    54.178 110.204 332.074  1.00  0.00           C
ATOM  3335  CA  ARG D 155    55.445 111.535 335.421  1.00  0.00           C
ATOM  3336  CA  ALA D 156    51.836 111.721 336.570  1.00  0.00           C
ATOM  3337  CA  ALA D 157    49.097 113.183 334.389  1.00  0.00           C
ATOM  3338  CA  GLY D 158    48.297 111.177 331.260  1.00  0.00           C
ATOM  3339  CA  THR D 159    47.996 107.453 330.544  1.00  0.00           C
ATOM  3340  CA  SER D 160    50.703 104.877 331.162  1.00  0.00           C
ATOM  3341  CA  ALA D 161    52.828 103.582 328.331  1.00  0.00           C
ATOM  3342  CA  GLN D 162    53.406  99.897 327.521  1.00  0.00           C
ATOM  3343  CA  VAL D 163    56.547  97.818 326.923  1.00  0.00           C
ATOM  3344  CA  LEU D 164    56.201  96.291 323.431  1.00  0.00           C
ATOM  3345  CA  GLY D 165    59.571  94.627 322.934  1.00  0.00           C
ATOM  3346  CA  LYS D 166    63.247  94.537 323.895  1.00  0.00           C
ATOM  3347  CA  GLU D 167    66.116  94.595 321.450  1.00  0.00           C
ATOM  3348  CA  GLY D 168    69.804  94.895 322.166  1.00  0.00           C
ATOM  3349  CA  LYS D 169    70.450  97.818 324.484  1.00  0.00           C
ATOM  3350  CA  TYR D 170    67.003  99.213 323.708  1.00  0.00           C
ATOM  3351  CA  VAL D 171    63.441  98.672 324.861  1.00  0.00           C
ATOM  3352  CA  ILE D 172    60.483  99.597 322.648  1.00  0.00           C
ATOM  3353  CA  VAL D 173    57.575 101.299 324.384  1.00  0.00           C
ATOM  3354  CA  ARG D 174    54.198 102.447 323.124  1.00  0.00           C
ATOM  3355  CA  LEU D 175    53.026 105.726 324.602  1.00  0.00           C
ATOM  3356  CA  ALA D 176    49.302 106.157 325.273  1.00  0.00           C
ATOM  3357  CA  SER D 177    48.584 108.169 322.110  1.00  0.00           C
ATOM  3358  CA  GLY D 178    50.043 105.289 320.134  1.00  0.00           C
ATOM  3359  CA  GLU D 179    53.404 106.991 319.728  1.00  0.00           C
ATOM  3360  CA  VAL D 180    56.225 104.400 319.730  1.00  0.00           C
```

```
ATOM  3361  CA  ARG D 181    59.713 105.026 321.126  1.00  0.00           C
ATOM  3362  CA  MET D 182    63.281 103.468 321.445  1.00  0.00           C
ATOM  3363  CA  ILE D 183    64.553 103.822 324.818  1.00  0.00           C
ATOM  3364  CA  LEU D 184    67.813 102.698 326.418  1.00  0.00           C
ATOM  3365  CA  GLY D 185    67.197  99.595 328.493  1.00  0.00           C
ATOM  3366  CA  LYS D 186    69.149 101.241 331.342  1.00  0.00           C
ATOM  3367  CA  CYS D 187    66.463 103.907 331.525  1.00  0.00           C
ATOM  3368  CA  ARG D 188    64.084 103.368 334.443  1.00  0.00           C
ATOM  3369  CA  ALA D 189    60.314 103.186 334.625  1.00  0.00           C
ATOM  3370  CA  THR D 190    57.735 102.459 337.314  1.00  0.00           C
ATOM  3371  CA  VAL D 191    55.257  99.624 336.942  1.00  0.00           C
ATOM  3372  CA  GLY D 192    51.573 100.482 336.851  1.00  0.00           C
ATOM  3373  CA  GLU D 193    49.063 102.990 335.563  1.00  0.00           C
ATOM  3374  CA  VAL D 194    49.245 106.455 336.995  1.00  0.00           C
ATOM  3375  CA  GLY D 195    46.076 105.878 339.011  1.00  0.00           C
ATOM  3376  CA  ASN D 196    42.913 107.901 338.535  1.00  0.00           C
ATOM  3377  CA  GLY D 197    41.245 108.092 337.342  1.00  0.00           C
ATOM  3378  CA  GLY D 198    39.394 110.241 334.920  1.00  0.00           C
ATOM  3379  CA  ARG D 199    40.196 113.516 336.607  1.00  0.00           C
ATOM  3380  CA  THR D 200    39.338 114.910 333.191  1.00  0.00           C
ATOM  3381  CA  ASP D 201    35.999 113.050 333.087  1.00  0.00           C
ATOM  3382  CA  LYS D 202    34.173 115.553 335.275  1.00  0.00           C
ATOM  3383  CA  PRO D 203    33.454 119.066 333.992  1.00  0.00           C
ATOM  3384  CA  PHE D 204    34.507 122.180 335.876  1.00  0.00           C
ATOM  3385  CA  VAL D 205    30.677 123.483 336.284  1.00  0.00           C
ATOM  3386  CA  LYS D 206    31.548 126.955 337.551  1.00  0.00           C
ATOM  3387  CA  ALA D 207    33.433 129.964 336.487  1.00  0.00           C
ATOM  3388  CA  GLY D 208    33.755 131.742 340.028  1.00  0.00           C
ATOM  3389  CA  ASN D 209    35.198 128.293 340.512  1.00  0.00           C
ATOM  3390  CA  LYS D 210    37.299 128.879 337.417  1.00  0.00           C
ATOM  3391  CA  HIS D 211    38.468 132.116 338.954  1.00  0.00           C
ATOM  3392  CA  HIS D 212    39.678 130.443 342.135  1.00  0.00           C
ATOM  3393  CA  LYS D 213    41.555 127.754 340.212  1.00  0.00           C
ATOM  3394  CA  MET D 214    43.603 129.991 338.786  1.00  0.00           C
ATOM  3395  CA  LYS D 215    46.346 131.314 336.547  1.00  0.00           C
ATOM  3396  CA  ALA D 216    43.969 132.587 333.946  1.00  0.00           C
ATOM  3397  CA  PRO D 222    40.879 133.882 332.590  1.00  0.00           C
ATOM  3398  CA  ASN D 223    42.418 133.666 329.128  1.00  0.00           C
ATOM  3399  CA  VAL D 224    41.687 135.918 326.201  1.00  0.00           C
ATOM  3400  CA  ARG D 225    42.630 134.462 322.822  1.00  0.00           C
ATOM  3401  CA  GLY D 226    45.222 136.309 320.810  1.00  0.00           C
ATOM  3402  CA  VAL D 227    42.921 136.272 317.819  1.00  0.00           C
ATOM  3403  CA  ALA D 228    40.380 138.231 319.837  1.00  0.00           C
ATOM  3404  CA  MET D 229    42.976 140.871 320.652  1.00  0.00           C
ATOM  3405  CA  ASN D 230    43.967 144.209 318.730  1.00  0.00           C
ATOM  3406  CA  ALA D 231    46.956 143.756 316.418  1.00  0.00           C
ATOM  3407  CA  VAL D 232    49.046 146.019 318.641  1.00  0.00           C
ATOM  3408  CA  ASP D 233    48.433 143.573 321.470  1.00  0.00           C
ATOM  3409  CA  HIS D 234    49.371 140.253 319.894  1.00  0.00           C
ATOM  3410  CA  PRO D 235    50.862 138.774 316.736  1.00  0.00           C
ATOM  3411  CA  PHE D 236    47.451 137.183 316.097  1.00  0.00           C
ATOM  3412  CA  GLY D 237    45.490 140.328 316.854  1.00  0.00           C
TER   3413      GLY D 237
ATOM  3414  CA  VAL E  38   -21.031 215.644 337.968  1.00  0.00           C
ATOM  3415  CA  GLN E  39   -20.033 212.567 335.984  1.00  0.00           C
ATOM  3416  CA  GLY E  40   -18.474 210.677 338.883  1.00  0.00           C
ATOM  3417  CA  PHE E  41   -17.864 209.952 342.555  1.00  0.00           C
ATOM  3418  CA  ALA E  42   -15.531 207.926 344.815  1.00  0.00           C
ATOM  3419  CA  GLY E  43   -15.408 205.723 347.897  1.00  0.00           C
ATOM  3420  CA  TYR E  44   -13.325 203.161 349.760  1.00  0.00           C
ATOM  3421  CA  LYS E  45   -13.286 199.376 349.503  1.00  0.00           C
ATOM  3422  CA  ALA E  46   -14.381 197.392 352.555  1.00  0.00           C
ATOM  3423  CA  GLY E  47   -15.089 193.820 351.538  1.00  0.00           C
ATOM  3424  CA  MET E  48   -17.649 191.388 350.195  1.00  0.00           C
ATOM  3425  CA  THR E  49   -20.860 189.531 351.015  1.00  0.00           C
ATOM  3426  CA  PRO E  61   -23.719 187.339 349.537  1.00  0.00           C
ATOM  3427  CA  ARG E  62   -27.347 186.921 348.530  1.00  0.00           C
ATOM  3428  CA  GLU E  63   -30.854 186.883 348.264  1.00  0.00           C
ATOM  3429  CA  GLY E  64   -33.333 186.647 345.376  1.00  0.00           C
ATOM  3430  CA  MET E  65   -35.315 183.547 344.254  1.00  0.00           C
ATOM  3431  CA  GLU E  66   -31.330 184.145 343.173  1.00  0.00           C
ATOM  3432  CA  THR E  67   -27.574 184.326 344.054  1.00  0.00           C
ATOM  3433  CA  VAL E  68   -25.637 187.772 343.919  1.00  0.00           C
ATOM  3434  CA  PRO E  69   -22.042 188.545 345.024  1.00  0.00           C
ATOM  3435  CA  VAL E  70   -21.382 192.089 346.211  1.00  0.00           C
ATOM  3436  CA  THR E  71   -18.484 194.411 347.140  1.00  0.00           C
ATOM  3437  CA  VAL E  72   -19.295 197.018 349.775  1.00  0.00           C
ATOM  3438  CA  ILE E  73   -17.378 200.312 349.332  1.00  0.00           C
ATOM  3439  CA  GLU E  74   -18.131 203.191 351.677  1.00  0.00           C
ATOM  3440  CA  THR E  75   -19.533 206.191 349.809  1.00  0.00           C
ATOM  3441  CA  PRO E  76   -19.426 209.185 352.204  1.00  0.00           C
ATOM  3442  CA  PRO E  77   -20.284 212.588 350.712  1.00  0.00           C
ATOM  3443  CA  MET E  78   -17.456 214.234 348.800  1.00  0.00           C
ATOM  3444  CA  ARG E  79   -16.657 217.870 348.194  1.00  0.00           C
ATOM  3445  CA  ALA E  80   -16.134 219.697 344.895  1.00  0.00           C
ATOM  3446  CA  VAL E  81   -13.210 221.326 344.882  1.00  0.00           C
ATOM  3447  CA  ALA E  82   -13.658 222.863 341.444  1.00  0.00           C
```

```
ATOM  3448  CA  LEU E  83   -16.136 222.664 338.552  1.00  0.00           C
ATOM  3449  CA  ARG E  84   -14.442 222.963 335.180  1.00  0.00           C
ATOM  3450  CA  ALA E  85   -15.259 222.730 331.720  1.00  0.00           C
ATOM  3451  CA  TYR E  86   -15.476 225.599 329.261  1.00  0.00           C
ATOM  3452  CA  GLU E  87   -16.999 229.137 330.119  1.00  0.00           C
ATOM  3453  CA  GLN E  93   -15.520 230.572 327.877  1.00  0.00           C
ATOM  3454  CA  ARG E  94   -12.450 229.077 327.265  1.00  0.00           C
ATOM  3455  CA  PRO E  95   -11.199 226.224 329.457  1.00  0.00           C
ATOM  3456  CA  LEU E  96   -12.500 226.984 332.971  1.00  0.00           C
ATOM  3457  CA  THR E  97   -11.094 224.264 335.267  1.00  0.00           C
ATOM  3458  CA  GLU E  98    -9.665 224.639 337.575  1.00  0.00           C
ATOM  3459  CA  VAL E  99   -10.394 227.621 339.846  1.00  0.00           C
ATOM  3460  CA  TRP E 100   -10.105 226.730 343.524  1.00  0.00           C
ATOM  3461  CA  THR E 101   -11.180 228.491 346.695  1.00  0.00           C
ATOM  3462  CA  ASP E 102   -12.013 227.908 349.924  1.00  0.00           C
ATOM  3463  CA  GLU E 103   -15.278 226.696 352.890  1.00  0.00           C
ATOM  3464  CA  PHE E 104   -12.505 224.144 353.365  1.00  0.00           C
ATOM  3465  CA  HIS E 105   -12.496 220.717 354.959  1.00  0.00           C
ATOM  3466  CA  SER E 106   -10.535 220.930 358.215  1.00  0.00           C
ATOM  3467  CA  GLU E 107    -7.971 218.575 356.790  1.00  0.00           C
ATOM  3468  CA  LEU E 108    -7.403 219.545 353.202  1.00  0.00           C
ATOM  3469  CA  ASP E 109    -4.094 221.124 354.314  1.00  0.00           C
ATOM  3470  CA  ARG E 110    -2.548 217.667 354.486  1.00  0.00           C
ATOM  3471  CA  THR E 111    -2.593 217.479 350.701  1.00  0.00           C
ATOM  3472  CA  LEU E 112    -3.112 220.975 349.286  1.00  0.00           C
ATOM  3473  CA  SER E 171   -25.276 218.945 329.951  1.00  0.00           C
ATOM  3474  CA  ASP E 172   -27.880 217.592 332.327  1.00  0.00           C
ATOM  3475  CA  ARG E 173   -25.494 215.973 334.815  1.00  0.00           C
ATOM  3476  CA  LEU E 174   -23.221 218.971 334.370  1.00  0.00           C
ATOM  3477  CA  ASP E 175   -25.980 221.037 335.933  1.00  0.00           C
ATOM  3478  CA  HIS E 176   -26.540 218.392 338.603  1.00  0.00           C
ATOM  3479  CA  ALA E 177   -22.886 218.817 339.520  1.00  0.00           C
ATOM  3480  CA  LEU E 178   -22.792 222.590 339.951  1.00  0.00           C
ATOM  3481  CA  ASP E 179   -25.936 222.324 342.079  1.00  0.00           C
ATOM  3482  CA  ILE E 180   -24.491 220.062 344.767  1.00  0.00           C
ATOM  3483  CA  VAL E 181   -21.185 221.922 344.793  1.00  0.00           C
ATOM  3484  CA  GLU E 182   -22.987 225.268 344.865  1.00  0.00           C
ATOM  3485  CA  ASP E 183   -24.727 224.390 348.142  1.00  0.00           C
ATOM  3486  CA  GLY E 184   -21.508 223.192 349.720  1.00  0.00           C
ATOM  3487  CA  GLY E 185   -19.456 222.618 348.486  1.00  0.00           C
ATOM  3488  CA  GLU E 186   -20.656 219.029 349.261  1.00  0.00           C
ATOM  3489  CA  HIS E 187   -22.468 216.154 347.483  1.00  0.00           C
ATOM  3490  CA  ALA E 188   -23.241 212.431 347.778  1.00  0.00           C
ATOM  3491  CA  MET E 189   -23.591 209.217 345.760  1.00  0.00           C
ATOM  3492  CA  ASN E 190   -27.374 209.753 345.489  1.00  0.00           C
ATOM  3493  CA  ILE E 192   -25.212 211.176 340.797  1.00  0.00           C
ATOM  3494  CA  PHE E 193   -26.248 207.536 340.824  1.00  0.00           C
ATOM  3495  CA  ARG E 194   -29.328 205.390 341.359  1.00  0.00           C
ATOM  3496  CA  ALA E 195   -29.584 201.722 342.369  1.00  0.00           C
ATOM  3497  CA  GLY E 196   -29.868 199.743 339.156  1.00  0.00           C
ATOM  3498  CA  GLU E 197   -27.712 201.985 337.014  1.00  0.00           C
ATOM  3499  CA  TYR E 198   -24.544 200.704 335.390  1.00  0.00           C
ATOM  3500  CA  ALA E 199   -21.237 202.330 336.265  1.00  0.00           C
ATOM  3501  CA  ASP E 200   -17.618 201.899 335.283  1.00  0.00           C
ATOM  3502  CA  VAL E 201   -15.384 201.453 338.323  1.00  0.00           C
ATOM  3503  CA  ALA E 202   -11.660 202.193 338.313  1.00  0.00           C
ATOM  3504  CA  GLY E 203    -8.871 201.375 340.747  1.00  0.00           C
ATOM  3505  CA  VAL E 204    -5.260 200.316 341.272  1.00  0.00           C
ATOM  3506  CA  THR E 205    -4.915 196.532 341.374  1.00  0.00           C
ATOM  3507  CA  LYS E 206    -3.669 194.796 344.505  1.00  0.00           C
ATOM  3508  CA  GLY E 207     0.129 194.790 344.629  1.00  0.00           C
ATOM  3509  CA  LYS E 208     2.340 191.767 344.061  1.00  0.00           C
ATOM  3510  CA  GLY E 209     5.833 193.122 343.391  1.00  0.00           C
ATOM  3511  CA  THR E 210     7.614 191.193 340.647  1.00  0.00           C
ATOM  3512  CA  GLN E 211     6.262 187.766 339.771  1.00  0.00           C
ATOM  3513  CA  GLY E 212     7.282 185.256 337.121  1.00  0.00           C
ATOM  3514  CA  PRO E 213     5.896 184.695 333.578  1.00  0.00           C
ATOM  3515  CA  VAL E 214     3.527 181.957 334.707  1.00  0.00           C
ATOM  3516  CA  LYS E 215     1.620 184.214 337.089  1.00  0.00           C
ATOM  3517  CA  ARG E 216     2.223 187.450 335.236  1.00  0.00           C
ATOM  3518  CA  TRP E 217     1.375 186.292 331.714  1.00  0.00           C
ATOM  3519  CA  GLY E 218    -0.185 182.880 332.166  1.00  0.00           C
ATOM  3520  CA  VAL E 219     2.630 180.960 330.462  1.00  0.00           C
ATOM  3521  CA  GLN E 220     2.790 177.207 331.107  1.00  0.00           C
ATOM  3522  CA  LYS E 221     5.109 175.528 333.582  1.00  0.00           C
ATOM  3523  CA  ARG E 222     7.688 173.090 332.283  1.00  0.00           C
ATOM  3524  CA  LYS E 223     5.747 169.883 331.721  1.00  0.00           C
ATOM  3525  CA  GLY E 224     6.851 166.425 332.839  1.00  0.00           C
ATOM  3526  CA  LYS E 225    10.534 165.470 332.689  1.00  0.00           C
ATOM  3527  CA  HIS E 226    11.332 169.000 331.685  1.00  0.00           C
ATOM  3528  CA  ALA E 227    10.021 170.090 335.071  1.00  0.00           C
ATOM  3529  CA  ARG E 228    12.743 168.017 336.731  1.00  0.00           C
ATOM  3530  CA  GLN E 229    15.808 169.191 334.790  1.00  0.00           C
ATOM  3531  CA  GLY E 230    16.457 172.416 336.653  1.00  0.00           C
ATOM  3532  CA  TRP E 231    13.729 174.349 334.906  1.00  0.00           C
ATOM  3533  CA  ARG E 232    10.228 175.277 336.094  1.00  0.00           C
ATOM  3534  CA  ARG E 233     8.536 178.641 335.909  1.00  0.00           C
```

| | | | | | | | | | |
|---|---|---|---|---|---|---|---|---|---|
| ATOM | 3535 | CA | ARG | E | 234 | 10.750 | 179.517 | 332.896 | 1.00 | 0.00 | C |
| ATOM | 3536 | CA | ILE | E | 235 | 9.744 | 180.086 | 329.282 | 1.00 | 0.00 | C |
| ATOM | 3537 | CA | GLY | E | 236 | 11.393 | 178.035 | 326.558 | 1.00 | 0.00 | C |
| ATOM | 3538 | CA | ASN | E | 237 | 13.263 | 180.756 | 324.725 | 1.00 | 0.00 | C |
| ATOM | 3539 | CA | LEU | E | 238 | 13.426 | 184.517 | 324.565 | 1.00 | 0.00 | C |
| ATOM | 3540 | CA | GLY | E | 239 | 12.972 | 184.471 | 320.822 | 1.00 | 0.00 | C |
| ATOM | 3541 | CA | PRO | E | 240 | 14.176 | 183.391 | 317.339 | 1.00 | 0.00 | C |
| ATOM | 3542 | CA | TRP | E | 241 | 17.759 | 183.441 | 316.186 | 1.00 | 0.00 | C |
| ATOM | 3543 | CA | ASN | E | 242 | 17.767 | 186.291 | 313.765 | 1.00 | 0.00 | C |
| ATOM | 3544 | CA | PRO | E | 243 | 15.316 | 188.865 | 314.721 | 1.00 | 0.00 | C |
| ATOM | 3545 | CA | SER | E | 244 | 18.364 | 188.872 | 317.012 | 1.00 | 0.00 | C |
| ATOM | 3546 | CA | ARG | E | 245 | 17.045 | 190.680 | 320.064 | 1.00 | 0.00 | C |
| ATOM | 3547 | CA | VAL | E | 246 | 14.341 | 190.164 | 322.647 | 1.00 | 0.00 | C |
| ATOM | 3548 | CA | ARG | E | 247 | 10.980 | 191.532 | 321.561 | 1.00 | 0.00 | C |
| ATOM | 3549 | CA | SER | E | 248 | 8.975 | 193.361 | 324.211 | 1.00 | 0.00 | C |
| ATOM | 3550 | CA | THR | E | 249 | 6.161 | 190.952 | 323.356 | 1.00 | 0.00 | C |
| ATOM | 3551 | CA | VAL | E | 250 | 7.889 | 188.035 | 325.077 | 1.00 | 0.00 | C |
| ATOM | 3552 | CA | PRO | E | 251 | 6.520 | 187.131 | 328.556 | 1.00 | 0.00 | C |
| ATOM | 3553 | CA | GLN | E | 252 | 8.992 | 188.208 | 331.202 | 1.00 | 0.00 | C |
| ATOM | 3554 | CA | GLN | E | 253 | 9.414 | 188.619 | 334.933 | 1.00 | 0.00 | C |
| ATOM | 3555 | CA | GLY | E | 254 | 8.409 | 191.965 | 336.407 | 1.00 | 0.00 | C |
| ATOM | 3556 | CA | GLN | E | 255 | 6.013 | 194.119 | 338.423 | 1.00 | 0.00 | C |
| ATOM | 3557 | CA | THR | E | 256 | 2.544 | 192.626 | 338.487 | 1.00 | 0.00 | C |
| ATOM | 3558 | CA | GLY | E | 257 | 0.111 | 194.251 | 340.892 | 1.00 | 0.00 | C |
| ATOM | 3559 | CA | TYR | E | 258 | -0.532 | 197.967 | 341.468 | 1.00 | 0.00 | C |
| ATOM | 3560 | CA | HIS | E | 259 | -2.089 | 198.853 | 338.110 | 1.00 | 0.00 | C |
| ATOM | 3561 | CA | GLN | E | 260 | -4.923 | 201.163 | 337.154 | 1.00 | 0.00 | C |
| ATOM | 3562 | CA | ARG | E | 261 | -7.894 | 199.312 | 335.751 | 1.00 | 0.00 | C |
| ATOM | 3563 | CA | THR | E | 262 | -11.292 | 200.518 | 334.595 | 1.00 | 0.00 | C |
| ATOM | 3564 | CA | GLU | E | 263 | -13.889 | 197.769 | 334.703 | 1.00 | 0.00 | C |
| ATOM | 3565 | CA | LEU | E | 264 | -16.979 | 198.510 | 332.660 | 1.00 | 0.00 | C |
| ATOM | 3566 | CA | ASN | E | 265 | -20.646 | 197.909 | 333.375 | 1.00 | 0.00 | C |
| ATOM | 3567 | CA | LYS | E | 266 | -20.699 | 197.297 | 337.108 | 1.00 | 0.00 | C |
| ATOM | 3568 | CA | ARG | E | 267 | -24.348 | 197.306 | 338.181 | 1.00 | 0.00 | C |
| ATOM | 3569 | CA | LEU | E | 268 | -24.962 | 199.329 | 341.346 | 1.00 | 0.00 | C |
| ATOM | 3570 | CA | ILE | E | 269 | -27.463 | 197.000 | 343.077 | 1.00 | 0.00 | C |
| ATOM | 3571 | CA | ASP | E | 270 | -28.102 | 199.320 | 346.045 | 1.00 | 0.00 | C |
| ATOM | 3572 | CA | ILE | E | 271 | -27.139 | 202.695 | 347.547 | 1.00 | 0.00 | C |
| ATOM | 3573 | CA | GLY | E | 272 | -27.859 | 203.488 | 351.165 | 1.00 | 0.00 | C |
| ATOM | 3574 | CA | GLU | E | 273 | -26.230 | 204.226 | 354.483 | 1.00 | 0.00 | C |
| ATOM | 3575 | CA | GLY | E | 274 | -25.750 | 203.660 | 358.176 | 1.00 | 0.00 | C |
| ATOM | 3576 | CA | GLY | E | 291 | -22.582 | 205.191 | 356.945 | 1.00 | 0.00 | C |
| ATOM | 3577 | CA | PRO | E | 292 | -23.075 | 206.081 | 353.271 | 1.00 | 0.00 | C |
| ATOM | 3578 | CA | TYR | E | 293 | -22.478 | 202.940 | 351.249 | 1.00 | 0.00 | C |
| ATOM | 3579 | CA | THR | E | 294 | -22.875 | 201.444 | 347.780 | 1.00 | 0.00 | C |
| ATOM | 3580 | CA | LEU | E | 295 | -23.181 | 197.776 | 346.867 | 1.00 | 0.00 | C |
| ATOM | 3581 | CA | VAL | E | 296 | -21.424 | 196.990 | 343.597 | 1.00 | 0.00 | C |
| ATOM | 3582 | CA | LYS | E | 297 | -22.695 | 193.958 | 341.705 | 1.00 | 0.00 | C |
| ATOM | 3583 | CA | GLY | E | 298 | -20.433 | 191.095 | 340.835 | 1.00 | 0.00 | C |
| ATOM | 3584 | CA | SER | E | 299 | -17.922 | 193.027 | 342.786 | 1.00 | 0.00 | C |
| ATOM | 3585 | CA | VAL | E | 300 | -14.487 | 193.303 | 341.262 | 1.00 | 0.00 | C |
| ATOM | 3586 | CA | PRO | E | 301 | -13.525 | 196.833 | 342.101 | 1.00 | 0.00 | C |
| ATOM | 3587 | CA | GLY | E | 302 | -10.297 | 196.893 | 340.178 | 1.00 | 0.00 | C |
| ATOM | 3588 | CA | PRO | E | 303 | -8.059 | 197.023 | 343.314 | 1.00 | 0.00 | C |
| ATOM | 3589 | CA | ASP | E | 304 | -8.988 | 196.130 | 346.845 | 1.00 | 0.00 | C |
| ATOM | 3590 | CA | LYS | E | 305 | -9.577 | 196.851 | 350.567 | 1.00 | 0.00 | C |
| ATOM | 3591 | CA | ARG | E | 306 | -9.040 | 200.374 | 351.862 | 1.00 | 0.00 | C |
| ATOM | 3592 | CA | LEU | E | 307 | -8.230 | 201.614 | 348.364 | 1.00 | 0.00 | C |
| ATOM | 3593 | CA | VAL | E | 308 | -9.979 | 204.463 | 346.542 | 1.00 | 0.00 | C |
| ATOM | 3594 | CA | PRO | E | 309 | -12.296 | 203.266 | 343.771 | 1.00 | 0.00 | C |
| ATOM | 3595 | CA | PHE | E | 310 | -13.603 | 205.967 | 341.406 | 1.00 | 0.00 | C |
| ATOM | 3596 | CA | PHE | E | 311 | -17.194 | 205.644 | 340.086 | 1.00 | 0.00 | C |
| ATOM | 3597 | CA | ARG | E | 312 | -18.388 | 206.860 | 336.679 | 1.00 | 0.00 | C |
| ATOM | 3598 | CA | ALA | E | 314 | -21.108 | 203.594 | 332.324 | 1.00 | 0.00 | C |
| ATOM | 3599 | CA | VAL | E | 315 | -19.785 | 204.771 | 328.956 | 1.00 | 0.00 | C |
| ATOM | 3600 | CA | ARG | E | 316 | -20.574 | 201.645 | 326.916 | 1.00 | 0.00 | C |
| ATOM | 3601 | CA | PRO | E | 317 | -23.573 | 199.870 | 328.525 | 1.00 | 0.00 | C |
| ATOM | 3602 | CA | ASN | E | 318 | -24.840 | 196.586 | 327.099 | 1.00 | 0.00 | C |
| ATOM | 3603 | CA | ASP | E | 319 | -28.231 | 196.890 | 328.803 | 1.00 | 0.00 | C |
| ATOM | 3604 | CA | GLN | E | 320 | -30.637 | 199.581 | 329.939 | 1.00 | 0.00 | C |
| TER | 3605 | | GLN | E | 320 | | | | | | |
| ATOM | 3606 | CA | MET | F | 1 | 115.555 | 218.930 | 298.319 | 1.00 | 0.00 | C |
| ATOM | 3607 | CA | GLU | F | 2 | 115.602 | 221.689 | 300.939 | 1.00 | 0.00 | C |
| ATOM | 3608 | CA | ALA | F | 3 | 116.334 | 219.715 | 304.097 | 1.00 | 0.00 | C |
| ATOM | 3609 | CA | THR | F | 4 | 118.171 | 221.786 | 306.706 | 1.00 | 0.00 | C |
| ATOM | 3610 | CA | ILE | F | 5 | 120.282 | 219.636 | 309.027 | 1.00 | 0.00 | C |
| ATOM | 3611 | CA | TYR | F | 6 | 120.551 | 220.744 | 312.650 | 1.00 | 0.00 | C |
| ATOM | 3612 | CA | ASP | F | 7 | 121.829 | 220.019 | 315.403 | 1.00 | 0.00 | C |
| ATOM | 3613 | CA | ASN | F | 11 | 120.208 | 223.700 | 313.684 | 1.00 | 0.00 | C |
| ATOM | 3614 | CA | THR | F | 12 | 122.129 | 224.864 | 311.291 | 1.00 | 0.00 | C |
| ATOM | 3615 | CA | ASP | F | 13 | 125.004 | 222.737 | 310.046 | 1.00 | 0.00 | C |
| ATOM | 3616 | CA | GLY | F | 14 | 124.127 | 222.464 | 306.393 | 1.00 | 0.00 | C |
| ATOM | 3617 | CA | GLU | F | 15 | 121.486 | 221.118 | 304.051 | 1.00 | 0.00 | C |
| ATOM | 3618 | CA | VAL | F | 16 | 120.712 | 217.921 | 302.185 | 1.00 | 0.00 | C |
| ATOM | 3619 | CA | ASP | F | 17 | 118.408 | 216.896 | 299.361 | 1.00 | 0.00 | C |
| ATOM | 3620 | CA | LEU | F | 18 | 114.926 | 216.029 | 300.581 | 1.00 | 0.00 | C |
| ATOM | 3621 | CA | PRO | F | 19 | 114.257 | 212.683 | 298.832 | 1.00 | 0.00 | C |

```
ATOM  3622  CA  ASP F  20   111.642 212.535 296.073  1.00  0.00           C
ATOM  3623  CA  VAL F  21   109.485 210.179 298.116  1.00  0.00           C
ATOM  3624  CA  PHE F  22   108.356 213.201 300.117  1.00  0.00           C
ATOM  3625  CA  GLU F  23   106.835 214.520 296.904  1.00  0.00           C
ATOM  3626  CA  THR F  24   104.433 211.594 296.729  1.00  0.00           C
ATOM  3627  CA  PRO F  25   101.620 212.045 294.572  1.00  0.00           C
ATOM  3628  CA  VAL F  26    99.788 211.790 297.903  1.00  0.00           C
ATOM  3629  CA  ARG F  27    97.058 209.179 297.699  1.00  0.00           C
ATOM  3630  CA  SER F  28    95.142 209.121 300.989  1.00  0.00           C
ATOM  3631  CA  ASP F  29    92.535 206.498 300.116  1.00  0.00           C
ATOM  3632  CA  LEU F  30    95.153 203.767 299.856  1.00  0.00           C
ATOM  3633  CA  ILE F  31    96.837 205.142 302.969  1.00  0.00           C
ATOM  3634  CA  GLY F  32    93.399 204.904 304.543  1.00  0.00           C
ATOM  3635  CA  LYS F  33    93.109 201.166 303.940  1.00  0.00           C
ATOM  3636  CA  ALA F  34    96.638 200.539 305.183  1.00  0.00           C
ATOM  3637  CA  VAL F  35    96.028 202.225 308.532  1.00  0.00           C
ATOM  3638  CA  ARG F  36    92.451 200.989 308.843  1.00  0.00           C
ATOM  3639  CA  ALA F  37    93.641 197.426 308.285  1.00  0.00           C
ATOM  3640  CA  ALA F  38    96.409 197.684 310.853  1.00  0.00           C
ATOM  3641  CA  GLN F  39    94.105 199.072 313.526  1.00  0.00           C
ATOM  3642  CA  ALA F  40    91.630 196.273 312.956  1.00  0.00           C
ATOM  3643  CA  ASN F  41    94.219 193.509 313.092  1.00  0.00           C
ATOM  3644  CA  ARG F  42    95.099 194.259 316.706  1.00  0.00           C
ATOM  3645  CA  LYS F  43    91.534 194.217 318.043  1.00  0.00           C
ATOM  3646  CA  GLN F  44    90.818 191.291 320.369  1.00  0.00           C
ATOM  3647  CA  ASP F  45    88.120 188.640 320.028  1.00  0.00           C
ATOM  3648  CA  TYR F  46    85.169 188.887 322.379  1.00  0.00           C
ATOM  3649  CA  GLY F  47    81.700 187.499 322.850  1.00  0.00           C
ATOM  3650  CA  SER F  48    79.191 186.688 325.541  1.00  0.00           C
ATOM  3651  CA  ASP F  49    79.025 183.300 327.221  1.00  0.00           C
ATOM  3652  CA  GLU F  50    77.495 180.894 324.730  1.00  0.00           C
ATOM  3653  CA  TYR F  51    75.293 179.642 327.534  1.00  0.00           C
ATOM  3654  CA  ALA F  52    74.296 182.922 329.140  1.00  0.00           C
ATOM  3655  CA  GLY F  53    71.539 182.372 326.354  1.00  0.00           C
ATOM  3656  CA  LEU F  54    71.494 178.598 325.919  1.00  0.00           C
ATOM  3657  CA  ARG F  55    71.566 177.401 329.531  1.00  0.00           C
ATOM  3658  CA  THR F  56    67.840 176.735 329.736  1.00  0.00           C
ATOM  3659  CA  PRO F  57    65.488 173.813 329.179  1.00  0.00           C
ATOM  3660  CA  ALA F  58    62.911 176.243 327.818  1.00  0.00           C
ATOM  3661  CA  GLU F  59    60.278 174.584 325.661  1.00  0.00           C
ATOM  3662  CA  SER F  60    57.459 175.825 323.488  1.00  0.00           C
ATOM  3663  CA  PHE F  61    53.939 174.838 324.544  1.00  0.00           C
ATOM  3664  CA  GLY F  62    53.062 174.830 320.866  1.00  0.00           C
ATOM  3665  CA  SER F  63    49.576 175.989 319.983  1.00  0.00           C
ATOM  3666  CA  GLY F  64    46.486 175.809 322.162  1.00  0.00           C
ATOM  3667  CA  ARG F  65    46.934 178.665 324.597  1.00  0.00           C
ATOM  3668  CA  GLY F  66    46.844 181.653 322.272  1.00  0.00           C
ATOM  3669  CA  GLN F  67    50.585 182.037 322.690  1.00  0.00           C
ATOM  3670  CA  ALA F  68    53.291 182.397 320.061  1.00  0.00           C
ATOM  3671  CA  HIS F  69    55.410 179.267 319.635  1.00  0.00           C
ATOM  3672  CA  ARG F  79    66.986 180.953 324.084  1.00  0.00           C
ATOM  3673  CA  VAL F  80    65.685 182.247 320.759  1.00  0.00           C
ATOM  3674  CA  PRO F  81    67.330 185.379 319.279  1.00  0.00           C
ATOM  3675  CA  GLN F  82    64.188 187.514 319.458  1.00  0.00           C
ATOM  3676  CA  ALA F  83    63.857 186.836 323.163  1.00  0.00           C
ATOM  3677  CA  VAL F  84    65.336 189.021 325.861  1.00  0.00           C
ATOM  3678  CA  LYS F  85    68.149 186.964 327.419  1.00  0.00           C
ATOM  3679  CA  GLY F  86    68.280 184.883 324.275  1.00  0.00           C
ATOM  3680  CA  ARG F  87    71.361 183.869 322.285  1.00  0.00           C
ATOM  3681  CA  SER F  88    70.708 187.680 323.907  1.00  0.00           C
ATOM  3682  CA  ALA F  89    69.387 186.817 320.439  1.00  0.00           C
ATOM  3683  CA  HIS F  90    72.415 187.802 318.343  1.00  0.00           C
ATOM  3684  CA  PRO F  91    75.365 188.577 320.625  1.00  0.00           C
ATOM  3685  CA  PRO F  92    79.000 189.289 319.737  1.00  0.00           C
ATOM  3686  CA  LYS F  93    80.703 186.026 318.891  1.00  0.00           C
ATOM  3687  CA  THR F  94    84.226 184.898 319.636  1.00  0.00           C
ATOM  3688  CA  GLU F  95    84.191 183.082 316.282  1.00  0.00           C
ATOM  3689  CA  LYS F  96    83.881 186.313 314.285  1.00  0.00           C
ATOM  3690  CA  ASP F  97    86.864 187.105 312.066  1.00  0.00           C
ATOM  3691  CA  ARG F  98    87.681 190.642 313.155  1.00  0.00           C
ATOM  3692  CA  SER F  99    90.763 191.013 310.964  1.00  0.00           C
ATOM  3693  CA  LEU F 100    91.249 192.590 307.533  1.00  0.00           C
ATOM  3694  CA  ASP F 101    93.031 192.500 307.274  1.00  0.00           C
ATOM  3695  CA  LEU F 102    95.070 194.671 304.934  1.00  0.00           C
ATOM  3696  CA  ASN F 103    97.008 193.750 301.823  1.00  0.00           C
ATOM  3697  CA  ASP F 104   100.798 194.910 301.408  1.00  0.00           C
ATOM  3698  CA  LYS F 105   101.344 197.300 298.514  1.00  0.00           C
ATOM  3699  CA  GLU F 106    98.286 199.346 299.405  1.00  0.00           C
ATOM  3700  CA  ARG F 107    99.387 199.526 303.044  1.00  0.00           C
ATOM  3701  CA  GLN F 108   103.024 200.351 302.270  1.00  0.00           C
ATOM  3702  CA  LEU F 109   101.886 202.982 299.796  1.00  0.00           C
ATOM  3703  CA  ALA F 110    99.904 204.576 302.604  1.00  0.00           C
ATOM  3704  CA  VAL F 111   102.925 204.524 304.902  1.00  0.00           C
ATOM  3705  CA  ARG F 112   104.925 206.415 302.295  1.00  0.00           C
ATOM  3706  CA  SER F 113   102.033 208.784 301.696  1.00  0.00           C
ATOM  3707  CA  ALA F 114   101.376 209.677 305.329  1.00  0.00           C
ATOM  3708  CA  LEU F 115   105.137 209.916 305.607  1.00  0.00           C
```

```
ATOM   3709  CA   ALA F 116     105.233 212.491 302.828  1.00  0.00           C
ATOM   3710  CA   ALA F 117     102.294 214.435 304.223  1.00  0.00           C
ATOM   3711  CA   THR F 118     104.667 215.051 307.128  1.00  0.00           C
ATOM   3712  CA   ALA F 119     106.749 217.392 304.979  1.00  0.00           C
ATOM   3713  CA   ASP F 120     103.926 219.826 304.208  1.00  0.00           C
ATOM   3714  CA   VAL F 138     112.919 218.219 311.001  1.00  0.00           C
ATOM   3715  CA   VAL F 139     116.276 216.650 310.154  1.00  0.00           C
ATOM   3716  CA   VAL F 140     119.028 216.207 312.739  1.00  0.00           C
ATOM   3717  CA   SER F 141     122.645 215.022 312.701  1.00  0.00           C
ATOM   3718  CA   ASP F 142     123.274 211.298 313.151  1.00  0.00           C
ATOM   3719  CA   ASP F 143     124.755 212.211 316.530  1.00  0.00           C
ATOM   3720  CA   PHE F 144     121.208 212.158 317.827  1.00  0.00           C
ATOM   3721  CA   GLU F 145     121.386 208.386 318.231  1.00  0.00           C
ATOM   3722  CA   ASP F 146     123.945 208.911 320.977  1.00  0.00           C
ATOM   3723  CA   LEU F 147     121.943 211.029 323.376  1.00  0.00           C
ATOM   3724  CA   VAL F 148     121.146 208.994 326.455  1.00  0.00           C
ATOM   3725  CA   LYS F 149     119.269 211.252 328.846  1.00  0.00           C
ATOM   3726  CA   THR F 150     115.760 212.362 327.961  1.00  0.00           C
ATOM   3727  CA   GLN F 151     116.216 215.940 329.074  1.00  0.00           C
ATOM   3728  CA   GLU F 152     119.090 216.338 326.642  1.00  0.00           C
ATOM   3729  CA   VAL F 153     116.462 215.727 323.975  1.00  0.00           C
ATOM   3730  CA   VAL F 154     114.134 218.161 325.696  1.00  0.00           C
ATOM   3731  CA   SER F 155     116.574 221.037 325.380  1.00  0.00           C
ATOM   3732  CA   LEU F 156     117.215 220.157 321.737  1.00  0.00           C
ATOM   3733  CA   LEU F 157     113.484 220.154 321.012  1.00  0.00           C
ATOM   3734  CA   GLU F 158     113.095 223.453 322.833  1.00  0.00           C
ATOM   3735  CA   ALA F 159     115.948 224.692 320.657  1.00  0.00           C
ATOM   3736  CA   LEU F 160     114.097 223.595 317.532  1.00  0.00           C
ATOM   3737  CA   ASP F 161     110.946 225.108 319.028  1.00  0.00           C
ATOM   3738  CA   VAL F 162     107.386 225.163 317.994  1.00  0.00           C
ATOM   3739  CA   HIS F 163     103.931 223.565 318.033  1.00  0.00           C
ATOM   3740  CA   ALA F 164     105.204 220.810 315.738  1.00  0.00           C
ATOM   3741  CA   ASP F 165     106.712 219.104 318.781  1.00  0.00           C
ATOM   3742  CA   ILE F 166     103.397 218.877 320.588  1.00  0.00           C
ATOM   3743  CA   ASP F 167     102.081 217.180 317.477  1.00  0.00           C
ATOM   3744  CA   ARG F 168     104.867 214.672 318.039  1.00  0.00           C
ATOM   3745  CA   LEU F 193     107.883 210.748 315.839  1.00  0.00           C
ATOM   3746  CA   PHE F 194     111.635 210.219 316.051  1.00  0.00           C
ATOM   3747  CA   VAL F 195     112.946 208.246 313.100  1.00  0.00           C
ATOM   3748  CA   THR F 196     116.498 206.943 313.421  1.00  0.00           C
ATOM   3749  CA   SER F 197     118.530 204.157 311.823  1.00  0.00           C
ATOM   3750  CA   ASP F 198     119.340 200.742 313.263  1.00  0.00           C
ATOM   3751  CA   GLU F 199     118.390 201.834 316.810  1.00  0.00           C
ATOM   3752  CA   PRO F 200     115.158 203.397 318.143  1.00  0.00           C
ATOM   3753  CA   SER F 201     115.888 206.416 320.318  1.00  0.00           C
ATOM   3754  CA   THR F 202     115.902 205.310 323.958  1.00  0.00           C
ATOM   3755  CA   ALA F 203     116.464 208.896 325.087  1.00  0.00           C
ATOM   3756  CA   ALA F 204     113.301 210.219 323.452  1.00  0.00           C
ATOM   3757  CA   ARG F 205     110.808 207.350 323.696  1.00  0.00           C
ATOM   3758  CA   ASN F 206     109.474 208.256 327.143  1.00  0.00           C
ATOM   3759  CA   LEU F 207     108.527 211.767 326.033  1.00  0.00           C
ATOM   3760  CA   ALA F 208     104.805 212.543 326.167  1.00  0.00           C
ATOM   3761  CA   GLY F 209     102.994 211.196 323.117  1.00  0.00           C
ATOM   3762  CA   ALA F 210     106.336 210.522 321.478  1.00  0.00           C
ATOM   3763  CA   ASP F 211     106.889 207.415 319.361  1.00  0.00           C
ATOM   3764  CA   VAL F 212     110.260 206.144 318.172  1.00  0.00           C
ATOM   3765  CA   ALA F 213     111.081 204.228 315.008  1.00  0.00           C
ATOM   3766  CA   THR F 214     113.672 203.319 312.397  1.00  0.00           C
ATOM   3767  CA   ALA F 215     113.665 204.201 308.703  1.00  0.00           C
ATOM   3768  CA   SER F 216     114.129 200.492 308.034  1.00  0.00           C
ATOM   3769  CA   GLU F 217     110.676 199.522 309.251  1.00  0.00           C
ATOM   3770  CA   VAL F 218     108.689 202.711 309.929  1.00  0.00           C
ATOM   3771  CA   ASN F 219     105.061 202.088 309.036  1.00  0.00           C
ATOM   3772  CA   THR F 220     101.945 204.014 308.091  1.00  0.00           C
ATOM   3773  CA   GLU F 221     100.651 204.047 311.659  1.00  0.00           C
ATOM   3774  CA   ASP F 222     103.499 205.751 313.482  1.00  0.00           C
ATOM   3775  CA   LEU F 223     103.831 207.937 310.401  1.00  0.00           C
ATOM   3776  CA   ALA F 224     100.489 207.873 308.797  1.00  0.00           C
ATOM   3777  CA   PRO F 225      98.486 209.635 311.552  1.00  0.00           C
ATOM   3778  CA   GLY F 230      99.735 212.542 309.996  1.00  0.00           C
ATOM   3779  CA   ARG F 231     102.655 213.899 311.921  1.00  0.00           C
ATOM   3780  CA   LEU F 232     105.368 216.162 313.306  1.00  0.00           C
ATOM   3781  CA   THR F 233     108.463 214.058 312.601  1.00  0.00           C
ATOM   3782  CA   VAL F 234     112.232 214.271 313.059  1.00  0.00           C
ATOM   3783  CA   PHE F 235     114.591 212.291 310.866  1.00  0.00           C
ATOM   3784  CA   THR F 236     118.216 211.560 311.562  1.00  0.00           C
ATOM   3785  CA   GLU F 237     120.601 212.751 308.851  1.00  0.00           C
ATOM   3786  CA   SER F 238     120.935 209.203 307.546  1.00  0.00           C
ATOM   3787  CA   ALA F 239     117.450 208.263 308.717  1.00  0.00           C
ATOM   3788  CA   LEU F 240     116.493 209.761 305.368  1.00  0.00           C
ATOM   3789  CA   ALA F 241     117.408 206.299 304.057  1.00  0.00           C
ATOM   3790  CA   GLU F 242     113.683 205.689 303.812  1.00  0.00           C
ATOM   3791  CA   VAL F 243     114.098 207.262 300.410  1.00  0.00           C
ATOM   3792  CA   ALA F 244     114.125 203.768 299.014  1.00  0.00           C
ATOM   3793  CA   GLU F 245     111.930 202.001 301.610  1.00  0.00           C
ATOM   3794  CA   ARG F 246     109.184 203.202 299.315  1.00  0.00           C
TER    3795       ARG F 246
```

```
ATOM  3796  CA  PHE G  10    27.932 165.346 201.155  1.00  0.00           C
ATOM  3797  CA  HIS G  11    28.295 161.584 201.483  1.00  0.00           C
ATOM  3798  CA  GLU G  12    31.499 159.507 201.654  1.00  0.00           C
ATOM  3799  CA  MET G  13    30.847 160.911 205.118  1.00  0.00           C
ATOM  3800  CA  ARG G  14    27.433 160.054 206.580  1.00  0.00           C
ATOM  3801  CA  GLU G  15    28.075 156.555 205.222  1.00  0.00           C
ATOM  3802  CA  PRO G  16    28.525 153.725 207.785  1.00  0.00           C
ATOM  3803  CA  ARG G  17    31.781 151.936 208.574  1.00  0.00           C
ATOM  3804  CA  ILE G  18    33.313 149.402 210.936  1.00  0.00           C
ATOM  3805  CA  GLU G  19    34.780 150.775 214.129  1.00  0.00           C
ATOM  3806  CA  LYS G  20    35.715 148.185 216.734  1.00  0.00           C
ATOM  3807  CA  VAL G  21    34.615 144.547 216.382  1.00  0.00           C
ATOM  3808  CA  VAL G  22    35.848 143.160 219.712  1.00  0.00           C
ATOM  3809  CA  VAL G  23    35.395 139.439 220.325  1.00  0.00           C
ATOM  3810  CA  HIS G  24    35.144 138.069 223.853  1.00  0.00           C
ATOM  3811  CA  MET G  25    34.263 134.935 225.822  1.00  0.00           C
ATOM  3812  CA  GLY G  26    32.632 135.374 229.222  1.00  0.00           C
ATOM  3813  CA  ILE G  27    33.559 132.485 231.503  1.00  0.00           C
ATOM  3814  CA  GLY G  28    33.420 132.329 235.296  1.00  0.00           C
ATOM  3815  CA  HIS G  29    37.114 131.973 236.067  1.00  0.00           C
ATOM  3816  CA  ALA G  35    42.561 131.674 230.771  1.00  0.00           C
ATOM  3817  CA  ASN G  36    43.308 128.973 228.212  1.00  0.00           C
ATOM  3818  CA  ALA G  37    40.429 129.924 225.982  1.00  0.00           C
ATOM  3819  CA  GLU G  38    42.504 132.999 225.224  1.00  0.00           C
ATOM  3820  CA  ASP G  39    44.922 130.936 223.150  1.00  0.00           C
ATOM  3821  CA  ILE G  40    42.040 130.393 220.724  1.00  0.00           C
ATOM  3822  CA  LEU G  41    41.317 134.117 220.540  1.00  0.00           C
ATOM  3823  CA  GLY G  42    44.846 134.478 219.230  1.00  0.00           C
ATOM  3824  CA  GLU G  43    44.784 132.744 215.856  1.00  0.00           C
ATOM  3825  CA  ILE G  44    41.116 133.692 215.603  1.00  0.00           C
ATOM  3826  CA  THR G  45    41.755 137.434 215.401  1.00  0.00           C
ATOM  3827  CA  GLY G  46    45.370 138.585 215.534  1.00  0.00           C
ATOM  3828  CA  GLN G  47    45.976 140.178 218.935  1.00  0.00           C
ATOM  3829  CA  MET G  48    45.577 139.253 222.618  1.00  0.00           C
ATOM  3830  CA  PRO G  49    42.794 140.088 225.184  1.00  0.00           C
ATOM  3831  CA  VAL G  50    42.557 139.923 229.014  1.00  0.00           C
ATOM  3832  CA  ARG G  51    39.568 141.448 230.983  1.00  0.00           C
ATOM  3833  CA  THR G  52    38.503 141.115 234.666  1.00  0.00           C
ATOM  3834  CA  LYS G  53    35.182 141.456 236.586  1.00  0.00           C
ATOM  3835  CA  ALA G  54    33.954 143.857 239.281  1.00  0.00           C
ATOM  3836  CA  LYS G  55    31.474 142.078 241.548  1.00  0.00           C
ATOM  3837  CA  ARG G  56    31.299 139.710 244.508  1.00  0.00           C
ATOM  3838  CA  THR G  57    28.467 137.220 244.939  1.00  0.00           C
ATOM  3839  CA  VAL G  58    29.893 133.695 245.093  1.00  0.00           C
ATOM  3840  CA  GLY G  59    26.722 132.728 243.239  1.00  0.00           C
ATOM  3841  CA  GLU G  60    29.073 131.193 240.717  1.00  0.00           C
ATOM  3842  CA  PHE G  61    31.456 131.096 243.700  1.00  0.00           C
ATOM  3843  CA  ASP G  62    32.536 134.479 242.432  1.00  0.00           C
ATOM  3844  CA  ILE G  63    33.106 136.938 245.278  1.00  0.00           C
ATOM  3845  CA  ARG G  64    36.395 137.523 243.510  1.00  0.00           C
ATOM  3846  CA  GLU G  65    36.227 141.313 243.142  1.00  0.00           C
ATOM  3847  CA  GLY G  66    39.509 141.309 241.228  1.00  0.00           C
ATOM  3848  CA  ASP G  67    39.269 138.364 238.858  1.00  0.00           C
ATOM  3849  CA  PRO G  68    40.723 136.989 235.625  1.00  0.00           C
ATOM  3850  CA  ILE G  69    37.329 135.808 234.358  1.00  0.00           C
ATOM  3851  CA  GLY G  70    37.534 136.269 230.616  1.00  0.00           C
ATOM  3852  CA  ALA G  71    39.138 138.166 227.783  1.00  0.00           C
ATOM  3853  CA  LYS G  72    38.135 140.426 224.877  1.00  0.00           C
ATOM  3854  CA  VAL G  73    39.862 141.467 221.649  1.00  0.00           C
ATOM  3855  CA  THR G  74    38.900 144.731 219.953  1.00  0.00           C
ATOM  3856  CA  LEU G  75    39.557 144.619 216.207  1.00  0.00           C
ATOM  3857  CA  ARG G  76    39.814 147.546 213.800  1.00  0.00           C
ATOM  3858  CA  ASP G  77    40.446 148.597 210.213  1.00  0.00           C
ATOM  3859  CA  GLU G  78    41.480 145.441 208.370  1.00  0.00           C
ATOM  3860  CA  MET G  79    41.675 143.235 211.466  1.00  0.00           C
ATOM  3861  CA  ALA G  80    37.993 144.032 211.784  1.00  0.00           C
ATOM  3862  CA  GLU G  81    37.319 143.106 208.157  1.00  0.00           C
ATOM  3863  CA  GLU G  82    39.519 140.015 207.897  1.00  0.00           C
ATOM  3864  CA  PHE G  83    37.613 138.793 210.951  1.00  0.00           C
ATOM  3865  CA  LEU G  84    33.989 139.538 210.053  1.00  0.00           C
ATOM  3866  CA  GLN G  85    34.832 137.916 206.734  1.00  0.00           C
ATOM  3867  CA  THR G  86    34.091 134.302 207.793  1.00  0.00           C
ATOM  3868  CA  ALA G  87    32.641 135.376 211.139  1.00  0.00           C
ATOM  3869  CA  LEU G  88    29.355 136.758 209.812  1.00  0.00           C
ATOM  3870  CA  PRO G  89    28.723 133.560 207.781  1.00  0.00           C
ATOM  3871  CA  LEU G  90    28.910 131.430 210.928  1.00  0.00           C
ATOM  3872  CA  ALA G  91    25.814 133.233 212.221  1.00  0.00           C
ATOM  3873  CA  GLU G  92    22.362 133.905 210.801  1.00  0.00           C
ATOM  3874  CA  LEU G  93    21.863 137.077 212.875  1.00  0.00           C
ATOM  3875  CA  ALA G  94    19.799 140.109 211.824  1.00  0.00           C
ATOM  3876  CA  THR G  95    16.770 142.060 213.086  1.00  0.00           C
ATOM  3877  CA  SER G  96    15.417 142.333 216.648  1.00  0.00           C
ATOM  3878  CA  GLN G  97    19.035 141.555 217.452  1.00  0.00           C
ATOM  3879  CA  PHE G  98    20.332 144.914 216.274  1.00  0.00           C
ATOM  3880  CA  ASP G  99    20.921 147.968 218.442  1.00  0.00           C
ATOM  3881  CA  ASP G 100    19.341 151.404 218.308  1.00  0.00           C
ATOM  3882  CA  THR G 101    22.732 153.001 218.069  1.00  0.00           C
```

```
ATOM   3883  CA   GLY G 102      22.966 150.867 214.967  1.00  0.00           C
ATOM   3884  CA   ASN G 103      24.954 147.832 216.088  1.00  0.00           C
ATOM   3885  CA   PHE G 104      24.157 144.148 216.262  1.00  0.00           C
ATOM   3886  CA   SER G 105      25.829 141.356 218.198  1.00  0.00           C
ATOM   3887  CA   PHE G 106      25.754 137.573 217.827  1.00  0.00           C
ATOM   3888  CA   GLY G 107      27.298 134.552 219.510  1.00  0.00           C
ATOM   3889  CA   LEU G 128      31.570 133.255 222.430  1.00  0.00           C
ATOM   3890  CA   ASP G 129      30.296 136.728 221.508  1.00  0.00           C
ATOM   3891  CA   VAL G 130      31.024 138.973 218.520  1.00  0.00           C
ATOM   3892  CA   THR G 131      29.747 142.554 218.687  1.00  0.00           C
ATOM   3893  CA   VAL G 132      29.797 144.916 215.731  1.00  0.00           C
ATOM   3894  CA   ASN G 133      29.844 148.572 216.724  1.00  0.00           C
ATOM   3895  CA   LEU G 134      28.830 150.534 213.641  1.00  0.00           C
ATOM   3896  CA   VAL G 135      29.246 154.279 213.189  1.00  0.00           C
ATOM   3897  CA   ARG G 136      29.965 157.094 210.717  1.00  0.00           C
ATOM   3898  CA   PRO G 137      32.885 159.505 209.848  1.00  0.00           C
ATOM   3899  CA   GLY G 138      32.189 162.117 212.502  1.00  0.00           C
ATOM   3900  CA   TYR G 139      32.820 159.794 215.439  1.00  0.00           C
ATOM   3901  CA   ARG G 140      36.360 160.989 216.147  1.00  0.00           C
ATOM   3902  CA   VAL G 141      34.564 163.966 217.717  1.00  0.00           C
ATOM   3903  CA   ALA G 142      32.818 162.151 220.569  1.00  0.00           C
ATOM   3904  CA   LYS G 143      36.009 160.213 221.258  1.00  0.00           C
ATOM   3905  CA   ARG G 144      38.502 163.075 221.085  1.00  0.00           C
ATOM   3906  CA   ASP G 145      40.268 164.240 224.200  1.00  0.00           C
ATOM   3907  CA   LYS G 146      39.623 167.955 223.692  1.00  0.00           C
ATOM   3908  CA   ALA G 147      36.718 170.003 222.339  1.00  0.00           C
ATOM   3909  CA   SER G 148      34.865 166.697 222.277  1.00  0.00           C
ATOM   3910  CA   ARG G 149      31.106 166.618 221.845  1.00  0.00           C
ATOM   3911  CA   SER G 150      28.521 163.858 221.788  1.00  0.00           C
ATOM   3912  CA   ILE G 151      27.321 162.769 218.335  1.00  0.00           C
ATOM   3913  CA   PRO G 152      24.031 164.543 217.439  1.00  0.00           C
ATOM   3914  CA   THR G 153      21.031 162.226 217.582  1.00  0.00           C
ATOM   3915  CA   LYS G 154      20.671 162.892 213.853  1.00  0.00           C
ATOM   3916  CA   HIS G 155      24.149 161.884 212.776  1.00  0.00           C
ATOM   3917  CA   ARG G 156      23.569 158.735 214.815  1.00  0.00           C
TER    3918       ARG G 156
ATOM   3919  CA   PRO H   7     -27.787 226.793 273.145  1.00  0.00           C
ATOM   3920  CA   ILE H   8     -30.751 225.660 275.293  1.00  0.00           C
ATOM   3921  CA   GLU H   9     -34.113 227.122 274.484  1.00  0.00           C
ATOM   3922  CA   ILE H  10     -35.908 228.694 277.476  1.00  0.00           C
ATOM   3923  CA   PRO H  11     -39.557 227.704 277.059  1.00  0.00           C
ATOM   3924  CA   ALA H  12     -42.370 229.939 278.211  1.00  0.00           C
ATOM   3925  CA   GLY H  13     -43.087 230.231 281.898  1.00  0.00           C
ATOM   3926  CA   VAL H  14     -39.483 229.312 282.614  1.00  0.00           C
ATOM   3927  CA   THR H  15     -37.131 231.748 284.391  1.00  0.00           C
ATOM   3928  CA   VAL H  16     -33.345 231.030 284.297  1.00  0.00           C
ATOM   3929  CA   THR H  17     -30.920 232.779 286.642  1.00  0.00           C
ATOM   3930  CA   VAL H  18     -27.121 232.489 286.531  1.00  0.00           C
ATOM   3931  CA   ASN H  19     -24.712 233.641 289.216  1.00  0.00           C
ATOM   3932  CA   GLY H  20     -21.165 232.495 288.652  1.00  0.00           C
ATOM   3933  CA   ASN H  21     -21.289 228.713 288.474  1.00  0.00           C
ATOM   3934  CA   THR H  22     -24.698 228.286 290.097  1.00  0.00           C
ATOM   3935  CA   VAL H  23     -27.789 228.119 287.899  1.00  0.00           C
ATOM   3936  CA   THR H  24     -31.394 228.424 289.087  1.00  0.00           C
ATOM   3937  CA   VAL H  25     -34.265 227.377 286.801  1.00  0.00           C
ATOM   3938  CA   LYS H  26     -37.908 227.871 287.828  1.00  0.00           C
ATOM   3939  CA   GLY H  27     -41.029 226.722 286.046  1.00  0.00           C
ATOM   3940  CA   PRO H  28     -44.580 225.428 286.536  1.00  0.00           C
ATOM   3941  CA   LYS H  29     -43.372 222.011 287.659  1.00  0.00           C
ATOM   3942  CA   GLY H  30     -40.762 223.199 290.169  1.00  0.00           C
ATOM   3943  CA   GLU H  31     -37.498 225.074 290.827  1.00  0.00           C
ATOM   3944  CA   LEU H  32     -33.964 223.621 290.664  1.00  0.00           C
ATOM   3945  CA   THR H  33     -30.564 225.087 291.521  1.00  0.00           C
ATOM   3946  CA   ARG H  34     -27.396 223.482 290.278  1.00  0.00           C
ATOM   3947  CA   THR H  35     -23.679 224.263 290.302  1.00  0.00           C
ATOM   3948  CA   PHE H  36     -21.466 223.463 287.300  1.00  0.00           C
ATOM   3949  CA   HIS H  37     -17.779 223.004 286.578  1.00  0.00           C
ATOM   3950  CA   PRO H  38     -15.933 226.339 287.104  1.00  0.00           C
ATOM   3951  CA   ASP H  39     -14.279 226.153 283.689  1.00  0.00           C
ATOM   3952  CA   MET H  40     -17.643 226.371 281.946  1.00  0.00           C
ATOM   3953  CA   THR H  41     -19.247 229.786 281.275  1.00  0.00           C
ATOM   3954  CA   ILE H  42     -23.033 229.808 281.276  1.00  0.00           C
ATOM   3955  CA   THR H  43     -25.004 232.800 280.011  1.00  0.00           C
ATOM   3956  CA   VAL H  44     -28.660 233.598 279.338  1.00  0.00           C
ATOM   3957  CA   GLU H  45     -28.477 235.074 275.824  1.00  0.00           C
ATOM   3958  CA   GLY H  46     -31.933 236.680 275.793  1.00  0.00           C
ATOM   3959  CA   ASN H  47     -34.151 233.662 275.048  1.00  0.00           C
ATOM   3960  CA   VAL H  48     -31.498 230.849 275.135  1.00  0.00           C
ATOM   3961  CA   ILE H  49     -28.896 229.537 277.568  1.00  0.00           C
ATOM   3962  CA   THR H  50     -25.475 229.303 276.033  1.00  0.00           C
ATOM   3963  CA   VAL H  51     -22.482 227.258 277.372  1.00  0.00           C
ATOM   3964  CA   THR H  52     -18.926 228.409 276.427  1.00  0.00           C
ATOM   3965  CA   ARG H  53     -15.926 226.183 277.157  1.00  0.00           C
ATOM   3966  CA   PRO H  54     -12.470 227.823 277.679  1.00  0.00           C
ATOM   3967  CA   SER H  55     -10.595 225.726 275.083  1.00  0.00           C
ATOM   3968  CA   ASP H  56     -10.913 223.022 272.429  1.00  0.00           C
ATOM   3969  CA   GLU H  57      -9.045 220.281 274.208  1.00  0.00           C
```

| | | | | | | | | | |
|---|---|---|---|---|---|---|---|---|---|
| ATOM | 3970 | CA | LYS | H | 58 | -10.896 | 217.010 | 274.799 | 1.00 | 0.00 | C |
| ATOM | 3971 | CA | HIS | H | 59 | -11.722 | 217.308 | 278.496 | 1.00 | 0.00 | C |
| ATOM | 3972 | CA | HIS | H | 60 | -13.394 | 220.629 | 277.792 | 1.00 | 0.00 | C |
| ATOM | 3973 | CA | ARG | H | 61 | -15.315 | 219.338 | 274.799 | 1.00 | 0.00 | C |
| ATOM | 3974 | CA | ALA | H | 62 | -16.594 | 216.534 | 277.062 | 1.00 | 0.00 | C |
| ATOM | 3975 | CA | LEU | H | 63 | -17.353 | 218.957 | 279.897 | 1.00 | 0.00 | C |
| ATOM | 3976 | CA | HIS | H | 64 | -19.235 | 221.188 | 277.430 | 1.00 | 0.00 | C |
| ATOM | 3977 | CA | GLY | H | 65 | -21.650 | 218.476 | 276.235 | 1.00 | 0.00 | C |
| ATOM | 3978 | CA | THR | H | 66 | -22.145 | 217.153 | 279.797 | 1.00 | 0.00 | C |
| ATOM | 3979 | CA | THR | H | 67 | -22.956 | 220.693 | 281.130 | 1.00 | 0.00 | C |
| ATOM | 3980 | CA | ARG | H | 68 | -25.332 | 221.253 | 278.198 | 1.00 | 0.00 | C |
| ATOM | 3981 | CA | SER | H | 69 | -27.234 | 218.033 | 278.886 | 1.00 | 0.00 | C |
| ATOM | 3982 | CA | LEU | H | 70 | -27.674 | 218.800 | 282.600 | 1.00 | 0.00 | C |
| ATOM | 3983 | CA | LEU | H | 71 | -29.121 | 222.182 | 281.730 | 1.00 | 0.00 | C |
| ATOM | 3984 | CA | ALA | H | 72 | -31.436 | 220.707 | 279.117 | 1.00 | 0.00 | C |
| ATOM | 3985 | CA | ASN | H | 73 | -32.786 | 218.227 | 281.685 | 1.00 | 0.00 | C |
| ATOM | 3986 | CA | MET | H | 74 | -33.149 | 220.991 | 284.324 | 1.00 | 0.00 | C |
| ATOM | 3987 | CA | VAL | H | 75 | -35.232 | 222.877 | 281.765 | 1.00 | 0.00 | C |
| ATOM | 3988 | CA | GLU | H | 76 | -37.265 | 219.721 | 280.962 | 1.00 | 0.00 | C |
| ATOM | 3989 | CA | GLY | H | 77 | -37.950 | 219.019 | 284.666 | 1.00 | 0.00 | C |
| ATOM | 3990 | CA | VAL | H | 78 | -39.475 | 222.376 | 285.629 | 1.00 | 0.00 | C |
| ATOM | 3991 | CA | SER | H | 79 | -41.423 | 222.638 | 282.411 | 1.00 | 0.00 | C |
| ATOM | 3992 | CA | LYS | H | 80 | -42.533 | 219.103 | 281.690 | 1.00 | 0.00 | C |
| ATOM | 3993 | CA | GLY | H | 81 | -42.160 | 218.038 | 285.447 | 1.00 | 0.00 | C |
| ATOM | 3994 | CA | TYR | H | 82 | -40.338 | 214.675 | 285.549 | 1.00 | 0.00 | C |
| ATOM | 3995 | CA | GLU | H | 83 | -41.251 | 211.302 | 287.018 | 1.00 | 0.00 | C |
| ATOM | 3996 | CA | LYS | H | 84 | -39.958 | 207.811 | 287.677 | 1.00 | 0.00 | C |
| ATOM | 3997 | CA | ALA | H | 85 | -42.198 | 204.815 | 288.524 | 1.00 | 0.00 | C |
| ATOM | 3998 | CA | LEU | H | 86 | -41.391 | 201.749 | 290.696 | 1.00 | 0.00 | C |
| ATOM | 3999 | CA | GLU | H | 87 | -43.420 | 198.587 | 291.314 | 1.00 | 0.00 | C |
| ATOM | 4000 | CA | LEU | H | 88 | -43.698 | 196.202 | 294.290 | 1.00 | 0.00 | C |
| ATOM | 4001 | CA | VAL | H | 89 | -43.553 | 192.478 | 293.619 | 1.00 | 0.00 | C |
| ATOM | 4002 | CA | GLY | H | 90 | -44.307 | 190.038 | 296.366 | 1.00 | 0.00 | C |
| ATOM | 4003 | CA | VAL | H | 91 | -47.279 | 188.788 | 298.304 | 1.00 | 0.00 | C |
| ATOM | 4004 | CA | GLY | H | 92 | -48.091 | 191.188 | 301.164 | 1.00 | 0.00 | C |
| ATOM | 4005 | CA | TYR | H | 93 | -45.829 | 193.856 | 299.665 | 1.00 | 0.00 | C |
| ATOM | 4006 | CA | ARG | H | 94 | -47.655 | 197.152 | 299.576 | 1.00 | 0.00 | C |
| ATOM | 4007 | CA | ALA | H | 95 | -47.237 | 200.920 | 299.660 | 1.00 | 0.00 | C |
| ATOM | 4008 | CA | SER | H | 96 | -49.517 | 203.635 | 301.040 | 1.00 | 0.00 | C |
| ATOM | 4009 | CA | LYS | H | 97 | -49.461 | 207.366 | 301.554 | 1.00 | 0.00 | C |
| ATOM | 4010 | CA | GLN | H | 98 | -49.714 | 208.584 | 305.168 | 1.00 | 0.00 | C |
| ATOM | 4011 | CA | GLY | H | 99 | -49.307 | 212.341 | 304.987 | 1.00 | 0.00 | C |
| ATOM | 4012 | CA | LYS | H | 100 | -46.312 | 213.453 | 302.953 | 1.00 | 0.00 | C |
| ATOM | 4013 | CA | LYS | H | 101 | -44.819 | 210.084 | 303.922 | 1.00 | 0.00 | C |
| ATOM | 4014 | CA | LEU | H | 102 | -44.499 | 206.928 | 301.821 | 1.00 | 0.00 | C |
| ATOM | 4015 | CA | VAL | H | 103 | -45.134 | 203.839 | 304.004 | 1.00 | 0.00 | C |
| ATOM | 4016 | CA | LEU | H | 104 | -43.669 | 200.580 | 302.702 | 1.00 | 0.00 | C |
| ATOM | 4017 | CA | SER | H | 105 | -44.591 | 197.076 | 303.845 | 1.00 | 0.00 | C |
| ATOM | 4018 | CA | VAL | H | 106 | -41.876 | 194.974 | 302.160 | 1.00 | 0.00 | C |
| ATOM | 4019 | CA | GLY | H | 107 | -41.297 | 191.863 | 304.241 | 1.00 | 0.00 | C |
| ATOM | 4020 | CA | TYR | H | 108 | -39.478 | 193.237 | 307.311 | 1.00 | 0.00 | C |
| ATOM | 4021 | CA | SER | H | 109 | -40.939 | 193.010 | 310.806 | 1.00 | 0.00 | C |
| ATOM | 4022 | CA | HIS | H | 110 | -42.053 | 196.672 | 310.569 | 1.00 | 0.00 | C |
| ATOM | 4023 | CA | PRO | H | 111 | -42.805 | 199.202 | 307.792 | 1.00 | 0.00 | C |
| ATOM | 4024 | CA | VAL | H | 112 | -40.277 | 201.553 | 306.187 | 1.00 | 0.00 | C |
| ATOM | 4025 | CA | GLU | H | 113 | -41.353 | 205.223 | 306.061 | 1.00 | 0.00 | C |
| ATOM | 4026 | CA | ILE | H | 114 | -39.815 | 207.670 | 303.592 | 1.00 | 0.00 | C |
| ATOM | 4027 | CA | GLU | H | 115 | -40.415 | 211.356 | 303.529 | 1.00 | 0.00 | C |
| ATOM | 4028 | CA | PRO | H | 116 | -39.421 | 213.226 | 300.375 | 1.00 | 0.00 | C |
| ATOM | 4029 | CA | GLU | H | 117 | -37.301 | 216.314 | 300.642 | 1.00 | 0.00 | C |
| ATOM | 4030 | CA | GLU | H | 118 | -38.396 | 219.726 | 299.491 | 1.00 | 0.00 | C |
| ATOM | 4031 | CA | GLY | H | 119 | -39.241 | 219.889 | 295.807 | 1.00 | 0.00 | C |
| ATOM | 4032 | CA | LEU | H | 120 | -40.094 | 216.114 | 295.593 | 1.00 | 0.00 | C |
| ATOM | 4033 | CA | GLU | H | 121 | -43.418 | 214.255 | 295.595 | 1.00 | 0.00 | C |
| ATOM | 4034 | CA | ILE | H | 122 | -44.248 | 210.591 | 295.834 | 1.00 | 0.00 | C |
| ATOM | 4035 | CA | GLU | H | 123 | -47.575 | 209.296 | 294.648 | 1.00 | 0.00 | C |
| ATOM | 4036 | CA | VAL | H | 124 | -49.009 | 205.810 | 295.245 | 1.00 | 0.00 | C |
| ATOM | 4037 | CA | PRO | H | 125 | -51.872 | 205.297 | 292.714 | 1.00 | 0.00 | C |
| ATOM | 4038 | CA | SER | H | 126 | -52.263 | 201.591 | 293.536 | 1.00 | 0.00 | C |
| ATOM | 4039 | CA | GLN | H | 127 | -50.718 | 199.590 | 296.381 | 1.00 | 0.00 | C |
| ATOM | 4040 | CA | THR | H | 128 | -48.022 | 198.158 | 294.178 | 1.00 | 0.00 | C |
| ATOM | 4041 | CA | LYS | H | 129 | -47.028 | 201.273 | 292.236 | 1.00 | 0.00 | C |
| ATOM | 4042 | CA | ILE | H | 130 | -44.984 | 204.232 | 293.451 | 1.00 | 0.00 | C |
| ATOM | 4043 | CA | ILE | H | 131 | -44.365 | 207.398 | 291.360 | 1.00 | 0.00 | C |
| ATOM | 4044 | CA | VAL | H | 132 | -41.660 | 209.929 | 292.271 | 1.00 | 0.00 | C |
| ATOM | 4045 | CA | LYS | H | 133 | -41.945 | 213.358 | 290.694 | 1.00 | 0.00 | C |
| ATOM | 4046 | CA | GLY | H | 134 | -40.432 | 216.774 | 290.707 | 1.00 | 0.00 | C |
| ATOM | 4047 | CA | ALA | H | 135 | -38.760 | 219.461 | 288.605 | 1.00 | 0.00 | C |
| ATOM | 4048 | CA | ASP | H | 136 | -35.209 | 218.249 | 288.968 | 1.00 | 0.00 | C |
| ATOM | 4049 | CA | LYS | H | 137 | -34.667 | 215.107 | 286.810 | 1.00 | 0.00 | C |
| ATOM | 4050 | CA | GLN | H | 138 | -31.605 | 214.207 | 288.844 | 1.00 | 0.00 | C |
| ATOM | 4051 | CA | ARG | H | 139 | -33.194 | 214.475 | 292.264 | 1.00 | 0.00 | C |
| ATOM | 4052 | CA | VAL | H | 140 | -36.126 | 212.423 | 290.970 | 1.00 | 0.00 | C |
| ATOM | 4053 | CA | GLY | H | 141 | -33.729 | 209.755 | 289.717 | 1.00 | 0.00 | C |
| ATOM | 4054 | CA | GLU | H | 142 | -31.856 | 209.737 | 293.045 | 1.00 | 0.00 | C |
| ATOM | 4055 | CA | LEU | H | 143 | -34.903 | 209.383 | 295.348 | 1.00 | 0.00 | C |
| ATOM | 4056 | CA | ALA | H | 144 | -36.358 | 206.557 | 293.201 | 1.00 | 0.00 | C |

```
ATOM   4057  CA  ALA H 145     -32.979 204.713 293.430  1.00  0.00           C
ATOM   4058  CA  ASN H 146     -33.021 205.161 297.191  1.00  0.00           C
ATOM   4059  CA  ILE H 147     -36.546 203.760 297.473  1.00  0.00           C
ATOM   4060  CA  ARG H 148     -35.673 200.725 295.334  1.00  0.00           C
ATOM   4061  CA  ALA H 149     -32.566 200.216 297.523  1.00  0.00           C
ATOM   4062  CA  VAL H 150     -34.803 199.651 300.595  1.00  0.00           C
ATOM   4063  CA  ARG H 151     -35.440 196.203 299.202  1.00  0.00           C
ATOM   4064  CA  PRO H 152     -34.191 195.516 295.664  1.00  0.00           C
ATOM   4065  CA  PRO H 153     -35.499 192.446 293.637  1.00  0.00           C
ATOM   4066  CA  GLU H 154     -34.285 189.040 294.890  1.00  0.00           C
ATOM   4067  CA  PRO H 155     -33.011 186.557 292.271  1.00  0.00           C
ATOM   4068  CA  TYR H 156     -35.077 183.493 292.989  1.00  0.00           C
ATOM   4069  CA  LYS H 157     -38.514 185.000 292.687  1.00  0.00           C
ATOM   4070  CA  GLY H 158     -38.058 188.669 291.820  1.00  0.00           C
ATOM   4071  CA  LYS H 159     -39.607 189.953 295.045  1.00  0.00           C
ATOM   4072  CA  GLY H 160     -38.732 193.432 296.208  1.00  0.00           C
ATOM   4073  CA  ILE H 161     -38.985 196.855 294.599  1.00  0.00           C
ATOM   4074  CA  ARG H 162     -38.015 197.316 290.934  1.00  0.00           C
ATOM   4075  CA  TYR H 163     -38.206 200.189 288.495  1.00  0.00           C
ATOM   4076  CA  GLU H 164     -41.397 200.024 286.376  1.00  0.00           C
ATOM   4077  CA  GLY H 165     -39.725 198.467 283.335  1.00  0.00           C
ATOM   4078  CA  GLU H 166     -36.988 196.555 285.206  1.00  0.00           C
ATOM   4079  CA  LEU H 167     -35.916 193.345 283.502  1.00  0.00           C
ATOM   4080  CA  VAL H 168     -35.276 190.994 286.383  1.00  0.00           C
ATOM   4081  CA  ARG H 169     -35.606 187.467 285.144  1.00  0.00           C
ATOM   4082  CA  LEU H 170     -35.907 184.925 287.949  1.00  0.00           C
TER    4083      LEU H 170
ATOM   4084  CA  MET I   1     -47.603 181.775 253.283  1.00  0.00           C
ATOM   4085  CA  THR I   2     -46.921 180.136 249.948  1.00  0.00           C
ATOM   4086  CA  ILE I   3     -45.535 182.193 247.030  1.00  0.00           C
ATOM   4087  CA  ASP I   4     -48.676 181.173 245.146  1.00  0.00           C
ATOM   4088  CA  GLU I   5     -50.428 182.288 248.325  1.00  0.00           C
ATOM   4089  CA  ILE I   6     -48.608 185.596 248.572  1.00  0.00           C
ATOM   4090  CA  ILE I   7     -49.412 186.087 244.910  1.00  0.00           C
ATOM   4091  CA  GLU I   8     -53.084 185.404 245.505  1.00  0.00           C
ATOM   4092  CA  ALA I   9     -53.174 188.000 248.279  1.00  0.00           C
ATOM   4093  CA  ILE I  10     -51.622 190.652 246.050  1.00  0.00           C
ATOM   4094  CA  GLU I  11     -54.237 189.958 243.377  1.00  0.00           C
ATOM   4095  CA  LYS I  12     -56.799 190.666 246.100  1.00  0.00           C
ATOM   4096  CA  LEU I  13     -55.407 194.112 246.899  1.00  0.00           C
ATOM   4097  CA  THR I  14     -56.927 197.414 245.810  1.00  0.00           C
ATOM   4098  CA  VAL I  15     -55.019 199.781 243.547  1.00  0.00           C
ATOM   4099  CA  SER I  16     -54.404 201.915 246.603  1.00  0.00           C
ATOM   4100  CA  GLU I  17     -53.185 199.011 248.677  1.00  0.00           C
ATOM   4101  CA  LEU I  18     -50.744 197.814 246.004  1.00  0.00           C
ATOM   4102  CA  ALA I  19     -49.539 201.400 245.635  1.00  0.00           C
ATOM   4103  CA  GLU I  20     -48.944 201.686 249.370  1.00  0.00           C
ATOM   4104  CA  LEU I  21     -47.378 198.198 249.487  1.00  0.00           C
ATOM   4105  CA  VAL I  22     -44.853 199.075 246.805  1.00  0.00           C
ATOM   4106  CA  LYS I  23     -44.036 202.441 248.445  1.00  0.00           C
ATOM   4107  CA  LYS I  24     -43.425 200.826 251.846  1.00  0.00           C
ATOM   4108  CA  LEU I  25     -41.016 198.366 250.277  1.00  0.00           C
ATOM   4109  CA  GLU I  26     -39.227 201.284 248.598  1.00  0.00           C
ATOM   4110  CA  ASP I  27     -38.927 203.196 251.877  1.00  0.00           C
ATOM   4111  CA  LYS I  28     -37.920 199.992 253.557  1.00  0.00           C
ATOM   4112  CA  PHE I  29     -35.598 198.503 250.910  1.00  0.00           C
ATOM   4113  CA  GLY I  30     -34.664 201.391 248.646  1.00  0.00           C
ATOM   4114  CA  VAL I  31     -35.675 201.944 245.013  1.00  0.00           C
ATOM   4115  CA  THR I  32     -33.076 199.488 243.732  1.00  0.00           C
ATOM   4116  CA  ALA I  33     -33.993 196.460 245.848  1.00  0.00           C
ATOM   4117  CA  ALA I  34     -37.713 197.277 245.847  1.00  0.00           C
ATOM   4118  CA  ALA I  35     -37.681 197.707 242.067  1.00  0.00           C
ATOM   4119  CA  PRO I  36     -38.582 194.045 241.370  1.00  0.00           C
ATOM   4120  CA  VAL I  37     -41.896 194.326 243.285  1.00  0.00           C
ATOM   4121  CA  ALA I  38     -42.531 197.772 241.882  1.00  0.00           C
ATOM   4122  CA  VAL I  39     -42.320 196.532 238.298  1.00  0.00           C
ATOM   4123  CA  ALA I  40     -44.056 193.199 238.921  1.00  0.00           C
ATOM   4124  CA  ALA I  41     -46.951 194.813 240.793  1.00  0.00           C
ATOM   4125  CA  ALA I  42     -47.787 197.697 238.458  1.00  0.00           C
ATOM   4126  CA  PRO I  43     -49.647 195.389 236.058  1.00  0.00           C
ATOM   4127  CA  VAL I  44     -51.507 193.914 239.035  1.00  0.00           C
ATOM   4128  CA  ALA I  45     -52.595 197.419 240.016  1.00  0.00           C
ATOM   4129  CA  GLY I  46     -53.322 198.274 236.381  1.00  0.00           C
ATOM   4130  CA  ALA I  47     -55.635 195.247 236.224  1.00  0.00           C
ATOM   4131  CA  ALA I  48     -57.306 196.386 239.463  1.00  0.00           C
ATOM   4132  CA  ALA I  49     -57.705 199.917 238.105  1.00  0.00           C
ATOM   4133  CA  GLY I  50     -59.457 198.497 235.073  1.00  0.00           C
ATOM   4134  CA  ALA I  51     -61.527 196.222 237.276  1.00  0.00           C
ATOM   4135  CA  ALA I  52     -62.708 199.174 239.410  1.00  0.00           C
ATOM   4136  CA  GLN I  53     -63.839 200.981 236.282  1.00  0.00           C
ATOM   4137  CA  GLU I  54     -65.812 197.930 235.125  1.00  0.00           C
ATOM   4138  CA  GLU I  55     -67.419 197.269 238.493  1.00  0.00           C
ATOM   4139  CA  LYS I  56     -68.370 200.919 238.865  1.00  0.00           C
ATOM   4140  CA  THR I  57     -66.422 201.287 242.107  1.00  0.00           C
ATOM   4141  CA  GLU I  58     -64.544 204.105 240.386  1.00  0.00           C
ATOM   4142  CA  PHE I  59     -65.632 206.492 237.688  1.00  0.00           C
ATOM   4143  CA  ASP I  60     -64.187 208.438 234.779  1.00  0.00           C
```

```
ATOM   4144  CA  VAL I  61     -65.210 211.636 233.038  1.00  0.00           C
ATOM   4145  CA  VAL I  62     -65.576 211.485 229.266  1.00  0.00           C
ATOM   4146  CA  LEU I  63     -65.813 214.529 226.988  1.00  0.00           C
ATOM   4147  CA  LYS I  64     -68.714 214.216 224.510  1.00  0.00           C
ATOM   4148  CA  SER I  65     -68.175 217.698 223.126  1.00  0.00           C
ATOM   4149  CA  PHE I  66     -66.659 221.102 223.792  1.00  0.00           C
ATOM   4150  CA  GLY I  67     -68.845 223.090 221.400  1.00  0.00           C
ATOM   4151  CA  GLN I  68     -67.944 226.640 220.455  1.00  0.00           C
ATOM   4152  CA  ASN I  69     -65.832 226.873 223.591  1.00  0.00           C
ATOM   4153  CA  LYS I  70     -62.842 224.761 222.601  1.00  0.00           C
ATOM   4154  CA  ILE I  71     -60.547 227.322 224.309  1.00  0.00           C
ATOM   4155  CA  GLN I  72     -62.357 227.666 227.636  1.00  0.00           C
ATOM   4156  CA  VAL I  73     -62.892 223.888 227.777  1.00  0.00           C
ATOM   4157  CA  ILE I  74     -59.157 223.325 227.216  1.00  0.00           C
ATOM   4158  CA  LYS I  75     -58.598 225.775 230.039  1.00  0.00           C
ATOM   4159  CA  VAL I  76     -60.560 223.553 232.449  1.00  0.00           C
ATOM   4160  CA  VAL I  77     -58.936 220.349 231.248  1.00  0.00           C
ATOM   4161  CA  ARG I  78     -55.532 222.006 231.786  1.00  0.00           C
ATOM   4162  CA  GLU I  79     -56.780 223.041 235.234  1.00  0.00           C
ATOM   4163  CA  ILE I  80     -57.932 219.557 236.180  1.00  0.00           C
ATOM   4164  CA  THR I  81     -55.102 217.576 234.545  1.00  0.00           C
ATOM   4165  CA  GLY I  82     -52.062 219.869 234.432  1.00  0.00           C
ATOM   4166  CA  LEU I  83     -51.625 218.864 230.812  1.00  0.00           C
ATOM   4167  CA  GLY I  84     -49.886 221.531 228.788  1.00  0.00           C
ATOM   4168  CA  LEU I  85     -51.521 223.401 225.905  1.00  0.00           C
ATOM   4169  CA  LYS I  86     -50.564 221.055 223.014  1.00  0.00           C
ATOM   4170  CA  GLU I  87     -51.554 217.944 224.973  1.00  0.00           C
ATOM   4171  CA  ALA I  88     -54.686 219.495 226.440  1.00  0.00           C
ATOM   4172  CA  LYS I  89     -55.780 220.637 222.940  1.00  0.00           C
ATOM   4173  CA  ASP I  90     -55.092 217.125 221.662  1.00  0.00           C
ATOM   4174  CA  LEU I  91     -57.378 215.449 224.222  1.00  0.00           C
ATOM   4175  CA  VAL I  92     -60.163 218.020 223.996  1.00  0.00           C
ATOM   4176  CA  GLU I  93     -60.142 217.671 220.198  1.00  0.00           C
ATOM   4177  CA  LYS I  94     -60.779 213.975 220.772  1.00  0.00           C
ATOM   4178  CA  ALA I  95     -64.217 214.889 222.103  1.00  0.00           C
ATOM   4179  CA  GLY I  96     -66.897 212.405 221.199  1.00  0.00           C
ATOM   4180  CA  SER I  97     -64.211 209.756 221.216  1.00  0.00           C
ATOM   4181  CA  PRO I  98     -64.235 206.886 223.731  1.00  0.00           C
ATOM   4182  CA  ASP I  99     -60.763 207.840 224.827  1.00  0.00           C
ATOM   4183  CA  ALA I 100     -61.611 211.467 225.415  1.00  0.00           C
ATOM   4184  CA  VAL I 101     -61.215 210.533 229.079  1.00  0.00           C
ATOM   4185  CA  ILE I 102     -60.276 213.673 231.010  1.00  0.00           C
ATOM   4186  CA  LYS I 103     -60.001 211.850 234.332  1.00  0.00           C
ATOM   4187  CA  SER I 104     -60.640 208.383 235.715  1.00  0.00           C
ATOM   4188  CA  GLY I 105     -60.199 206.448 238.918  1.00  0.00           C
ATOM   4189  CA  VAL I 106     -62.139 209.159 240.720  1.00  0.00           C
ATOM   4190  CA  SER I 107     -65.110 208.899 243.069  1.00  0.00           C
ATOM   4191  CA  LYS I 108     -68.668 209.634 241.911  1.00  0.00           C
ATOM   4192  CA  GLU I 109     -68.573 212.947 243.778  1.00  0.00           C
ATOM   4193  CA  GLU I 110     -65.219 213.905 242.326  1.00  0.00           C
ATOM   4194  CA  ALA I 111     -66.445 212.730 238.931  1.00  0.00           C
ATOM   4195  CA  GLU I 112     -69.593 214.843 239.414  1.00  0.00           C
ATOM   4196  CA  GLU I 113     -67.523 217.809 240.570  1.00  0.00           C
ATOM   4197  CA  ILE I 114     -65.355 217.513 237.437  1.00  0.00           C
ATOM   4198  CA  LYS I 115     -68.354 217.034 235.138  1.00  0.00           C
ATOM   4199  CA  LYS I 116     -69.811 220.236 236.594  1.00  0.00           C
ATOM   4200  CA  LYS I 117     -66.741 222.432 235.919  1.00  0.00           C
ATOM   4201  CA  LEU I 118     -66.412 221.116 232.355  1.00  0.00           C
ATOM   4202  CA  GLU I 119     -70.085 221.601 231.555  1.00  0.00           C
ATOM   4203  CA  GLU I 120     -69.643 225.055 232.952  1.00  0.00           C
ATOM   4204  CA  ALA I 121     -67.070 225.948 230.265  1.00  0.00           C
ATOM   4205  CA  GLY I 122     -69.282 224.726 227.429  1.00  0.00           C
ATOM   4206  CA  ALA I 123     -68.632 221.014 227.289  1.00  0.00           C
ATOM   4207  CA  GLU I 124     -70.891 217.974 227.103  1.00  0.00           C
ATOM   4208  CA  VAL I 125     -69.706 215.359 229.568  1.00  0.00           C
ATOM   4209  CA  GLU I 126     -70.543 211.738 230.253  1.00  0.00           C
ATOM   4210  CA  LEU I 127     -69.714 209.983 233.499  1.00  0.00           C
ATOM   4211  CA  LYS I 128     -68.838 206.305 233.232  1.00  0.00           C
TER    4212      LYS I 128
ATOM   4213  CA  MET J   1     -44.471 219.963 228.446  1.00  0.00           C
ATOM   4214  CA  THR J   2     -41.583 220.667 230.789  1.00  0.00           C
ATOM   4215  CA  ILE J   3     -40.182 217.850 232.922  1.00  0.00           C
ATOM   4216  CA  ASP J   4     -41.599 219.800 235.876  1.00  0.00           C
ATOM   4217  CA  GLU J   5     -44.821 220.320 233.929  1.00  0.00           C
ATOM   4218  CA  ILE J   6     -45.032 216.542 233.410  1.00  0.00           C
ATOM   4219  CA  ILE J   7     -44.255 215.932 237.063  1.00  0.00           C
ATOM   4220  CA  GLU J   8     -47.152 218.126 238.165  1.00  0.00           C
ATOM   4221  CA  ALA J   9     -49.460 216.353 235.685  1.00  0.00           C
ATOM   4222  CA  ILE J  10     -48.331 212.996 237.091  1.00  0.00           C
ATOM   4223  CA  GLU J  11     -48.934 214.466 240.536  1.00  0.00           C
ATOM   4224  CA  LYS J  12     -52.571 215.121 239.633  1.00  0.00           C
ATOM   4225  CA  LEU J  13     -53.360 211.577 238.500  1.00  0.00           C
ATOM   4226  CA  THR J  14     -55.601 209.309 240.503  1.00  0.00           C
ATOM   4227  CA  VAL J  15     -54.011 206.200 242.034  1.00  0.00           C
ATOM   4228  CA  SER J  16     -55.769 204.215 239.290  1.00  0.00           C
ATOM   4229  CA  GLU J  17     -54.496 206.401 236.424  1.00  0.00           C
ATOM   4230  CA  LEU J  18     -50.923 206.140 237.705  1.00  0.00           C
```

```
ATOM  4231  CA  ALA J  19   -51.282 202.351 237.884  1.00  0.00           C
ATOM  4232  CA  GLU J  20   -52.687 202.231 234.348  1.00  0.00           C
ATOM  4233  CA  LEU J  21   -50.029 204.633 233.090  1.00  0.00           C
ATOM  4234  CA  VAL J  22   -47.250 202.458 234.424  1.00  0.00           C
ATOM  4235  CA  LYS J  23   -48.852 199.242 233.261  1.00  0.00           C
ATOM  4236  CA  LYS J  24   -49.153 200.898 229.878  1.00  0.00           C
ATOM  4237  CA  LEU J  25   -45.416 201.807 229.866  1.00  0.00           C
ATOM  4238  CA  GLU J  26   -44.401 198.253 230.813  1.00  0.00           C
ATOM  4239  CA  ASP J  27   -46.405 196.771 227.912  1.00  0.00           C
ATOM  4240  CA  LYS J  28   -45.107 199.301 225.407  1.00  0.00           C
ATOM  4241  CA  PHE J  29   -41.482 199.550 226.591  1.00  0.00           C
ATOM  4242  CA  GLY J  30   -40.878 196.273 228.423  1.00  0.00           C
ATOM  4243  CA  VAL J  31   -40.411 195.808 232.194  1.00  0.00           C
ATOM  4244  CA  THR J  32   -36.748 196.763 232.064  1.00  0.00           C
ATOM  4245  CA  ALA J  33   -36.975 200.000 230.146  1.00  0.00           C
ATOM  4246  CA  ALA J  34   -40.207 201.012 231.868  1.00  0.00           C
ATOM  4247  CA  ALA J  35   -38.867 200.245 235.343  1.00  0.00           C
ATOM  4248  CA  PRO J  36   -37.635 203.819 235.926  1.00  0.00           C
ATOM  4249  CA  VAL J  37   -41.170 205.196 235.800  1.00  0.00           C
ATOM  4250  CA  ALA J  38   -42.546 202.244 237.760  1.00  0.00           C
ATOM  4251  CA  VAL J  39   -40.276 202.905 240.752  1.00  0.00           C
ATOM  4252  CA  ALA J  40   -40.424 206.710 240.298  1.00  0.00           C
ATOM  4253  CA  ALA J  41   -44.231 206.771 240.317  1.00  0.00           C
ATOM  4254  CA  ALA J  42   -44.983 204.261 243.083  1.00  0.00           C
ATOM  4255  CA  PRO J  43   -44.254 206.868 245.753  1.00  0.00           C
ATOM  4256  CA  VAL J  44   -46.558 209.295 243.972  1.00  0.00           C
ATOM  4257  CA  ALA J  45   -49.347 206.688 243.827  1.00  0.00           C
ATOM  4258  CA  GLY J  46   -48.613 205.801 247.449  1.00  0.00           C
ATOM  4259  CA  ALA J  47   -49.122 209.482 248.271  1.00  0.00           C
ATOM  4260  CA  ALA J  48   -52.369 209.579 246.296  1.00  0.00           C
ATOM  4261  CA  ALA J  49   -53.477 206.434 248.091  1.00  0.00           C
ATOM  4262  CA  GLY J  50   -52.932 208.171 251.420  1.00  0.00           C
ATOM  4263  CA  ALA J  51   -54.483 211.427 250.309  1.00  0.00           C
ATOM  4264  CA  ALA J  52   -57.585 209.501 249.292  1.00  0.00           C
ATOM  4265  CA  GLN J  53   -57.924 207.947 252.752  1.00  0.00           C
ATOM  4266  CA  GLU J  54   -57.684 211.398 254.404  1.00  0.00           C
ATOM  4267  CA  GLU J  55   -60.081 213.077 252.002  1.00  0.00           C
ATOM  4268  CA  LYS J  56   -62.568 210.240 252.371  1.00  0.00           C
ATOM  4269  CA  THR J  57   -62.581 209.575 248.619  1.00  0.00           C
ATOM  4270  CA  GLU J  58   -61.786 205.983 249.603  1.00  0.00           C
ATOM  4271  CA  PHE J  59   -62.275 204.216 252.879  1.00  0.00           C
ATOM  4272  CA  ASP J  60   -60.891 201.315 254.825  1.00  0.00           C
ATOM  4273  CA  VAL J  61   -62.290 198.718 257.204  1.00  0.00           C
ATOM  4274  CA  VAL J  62   -60.717 198.758 260.662  1.00  0.00           C
ATOM  4275  CA  LEU J  63   -61.389 195.821 263.000  1.00  0.00           C
ATOM  4276  CA  LYS J  64   -62.454 197.117 266.431  1.00  0.00           C
ATOM  4277  CA  SER J  65   -62.983 193.643 267.838  1.00  0.00           C
ATOM  4278  CA  PHE J  66   -63.238 190.019 266.674  1.00  0.00           C
ATOM  4279  CA  GLY J  67   -65.911 189.279 269.302  1.00  0.00           C
ATOM  4280  CA  GLN J  68   -66.763 185.739 270.378  1.00  0.00           C
ATOM  4281  CA  ASN J  69   -66.034 184.155 266.984  1.00  0.00           C
ATOM  4282  CA  LYS J  70   -62.399 185.034 266.357  1.00  0.00           C
ATOM  4283  CA  ILE J  71   -62.156 182.040 264.014  1.00  0.00           C
ATOM  4284  CA  GLN J  72   -65.296 183.095 262.099  1.00  0.00           C
ATOM  4285  CA  VAL J  73   -63.974 186.656 261.748  1.00  0.00           C
ATOM  4286  CA  ILE J  74   -60.662 185.266 260.475  1.00  0.00           C
ATOM  4287  CA  LYS J  75   -62.587 183.226 257.883  1.00  0.00           C
ATOM  4288  CA  VAL J  76   -64.108 186.328 256.325  1.00  0.00           C
ATOM  4289  CA  VAL J  77   -60.730 188.035 256.485  1.00  0.00           C
ATOM  4290  CA  ARG J  78   -59.109 185.219 254.544  1.00  0.00           C
ATOM  4291  CA  GLU J  79   -61.936 185.188 252.028  1.00  0.00           C
ATOM  4292  CA  ILE J  80   -61.480 188.909 251.548  1.00  0.00           C
ATOM  4293  CA  THR J  81   -57.713 189.303 251.646  1.00  0.00           C
ATOM  4294  CA  GLY J  82   -56.415 185.866 250.674  1.00  0.00           C
ATOM  4295  CA  LEU J  83   -54.023 185.786 253.583  1.00  0.00           C
ATOM  4296  CA  GLY J  84   -52.847 182.402 254.789  1.00  0.00           C
ATOM  4297  CA  LEU J  85   -53.938 181.201 258.215  1.00  0.00           C
ATOM  4298  CA  LYS J  86   -51.115 182.371 260.464  1.00  0.00           C
ATOM  4299  CA  GLU J  87   -51.088 185.858 258.966  1.00  0.00           C
ATOM  4300  CA  ALA J  88   -54.882 186.178 258.995  1.00  0.00           C
ATOM  4301  CA  LYS J  89   -55.115 185.244 262.700  1.00  0.00           C
ATOM  4302  CA  ASP J  90   -52.275 187.695 263.241  1.00  0.00           C
ATOM  4303  CA  LEU J  91   -54.215 190.525 261.578  1.00  0.00           C
ATOM  4304  CA  VAL J  92   -57.562 189.680 263.252  1.00  0.00           C
ATOM  4305  CA  GLU J  93   -55.973 189.337 266.704  1.00  0.00           C
ATOM  4306  CA  LYS J  94   -54.682 192.915 266.298  1.00  0.00           C
ATOM  4307  CA  ALA J  95   -58.265 194.137 266.613  1.00  0.00           C
ATOM  4308  CA  GLY J  96   -58.800 197.335 268.506  1.00  0.00           C
ATOM  4309  CA  SER J  97   -55.456 198.490 267.172  1.00  0.00           C
ATOM  4310  CA  PRO J  98   -55.506 201.304 264.574  1.00  0.00           C
ATOM  4311  CA  ASP J  99   -53.693 199.151 262.051  1.00  0.00           C
ATOM  4312  CA  ALA J 100   -56.077 196.214 262.314  1.00  0.00           C
ATOM  4313  CA  VAL J 101   -57.044 197.340 258.776  1.00  0.00           C
ATOM  4314  CA  ILE J 102   -58.635 194.530 256.832  1.00  0.00           C
ATOM  4315  CA  LYS J 103   -58.916 196.512 253.641  1.00  0.00           C
ATOM  4316  CA  SER J 104   -58.476 200.051 252.367  1.00  0.00           C
ATOM  4317  CA  GLY J 105   -58.816 201.949 249.095  1.00  0.00           C
```

```
ATOM   4318  CA  VAL J 106     -62.391 200.713 248.723  1.00  0.00           C
ATOM   4319  CA  SER J 107     -65.643 202.568 247.984  1.00  0.00           C
ATOM   4320  CA  LYS J 108     -68.047 203.360 250.841  1.00  0.00           C
ATOM   4321  CA  GLU J 109     -70.366 200.841 249.217  1.00  0.00           C
ATOM   4322  CA  GLU J 110     -67.689 198.144 249.172  1.00  0.00           C
ATOM   4323  CA  ALA J 111     -66.585 199.167 252.658  1.00  0.00           C
ATOM   4324  CA  GLU J 112     -70.196 198.731 253.804  1.00  0.00           C
ATOM   4325  CA  GLU J 113     -70.350 195.321 252.118  1.00  0.00           C
ATOM   4326  CA  ILE J 114     -67.169 194.317 253.982  1.00  0.00           C
ATOM   4327  CA  LYS J 115     -68.157 195.896 257.311  1.00  0.00           C
ATOM   4328  CA  LYS J 116     -71.357 193.843 257.233  1.00  0.00           C
ATOM   4329  CA  LYS J 117     -69.820 190.547 256.118  1.00  0.00           C
ATOM   4330  CA  LEU J 118     -67.447 191.044 259.084  1.00  0.00           C
ATOM   4331  CA  GLU J 119     -70.128 191.986 261.564  1.00  0.00           C
ATOM   4332  CA  GLU J 120     -72.094 188.941 260.499  1.00  0.00           C
ATOM   4333  CA  ALA J 121     -69.145 187.142 262.070  1.00  0.00           C
ATOM   4334  CA  GLY J 122     -69.616 188.853 265.399  1.00  0.00           C
ATOM   4335  CA  ALA J 123     -66.872 191.442 265.072  1.00  0.00           C
ATOM   4336  CA  GLU J 124     -67.010 195.180 265.506  1.00  0.00           C
ATOM   4337  CA  VAL J 125     -65.938 197.128 262.459  1.00  0.00           C
ATOM   4338  CA  GLU J 126     -65.349 200.803 261.883  1.00  0.00           C
ATOM   4339  CA  LEU J 127     -65.275 202.405 258.437  1.00  0.00           C
ATOM   4340  CA  LYS J 128     -62.641 205.131 258.196  1.00  0.00           C
TER    4341      LYS J 128
ATOM   4342  CA  MET K   1     100.629 119.047 308.237  1.00  0.00           C
ATOM   4343  CA  LYS K   2     103.598 116.705 307.691  1.00  0.00           C
ATOM   4344  CA  VAL K   3     103.865 114.029 310.364  1.00  0.00           C
ATOM   4345  CA  ILE K   4     106.370 111.345 311.459  1.00  0.00           C
ATOM   4346  CA  PHE K   5     104.400 108.137 312.055  1.00  0.00           C
ATOM   4347  CA  LEU K   6     105.497 106.413 315.268  1.00  0.00           C
ATOM   4348  CA  LYS K   7     103.188 103.373 315.160  1.00  0.00           C
ATOM   4349  CA  ASP K   8      99.968 102.582 313.228  1.00  0.00           C
ATOM   4350  CA  VAL K   9     101.312 101.891 309.712  1.00  0.00           C
ATOM   4351  CA  LYS K  10     102.398  98.528 308.257  1.00  0.00           C
ATOM   4352  CA  GLY K  11     102.774  97.299 311.805  1.00  0.00           C
ATOM   4353  CA  LYS K  12     105.202  99.887 313.200  1.00  0.00           C
ATOM   4354  CA  GLY K  13     105.937 102.637 310.672  1.00  0.00           C
ATOM   4355  CA  LYS K  14     108.225 104.077 313.327  1.00  0.00           C
ATOM   4356  CA  LYS K  15     111.034 103.556 310.778  1.00  0.00           C
ATOM   4357  CA  GLY K  16     110.121 106.992 309.518  1.00  0.00           C
ATOM   4358  CA  GLU K  17     106.868 106.943 307.591  1.00  0.00           C
ATOM   4359  CA  ILE K  18     106.635 110.701 306.996  1.00  0.00           C
ATOM   4360  CA  LYS K  19     103.156 111.598 305.734  1.00  0.00           C
ATOM   4361  CA  ASN K  20     101.276 114.893 305.526  1.00  0.00           C
ATOM   4362  CA  VAL K  21      98.288 114.461 307.847  1.00  0.00           C
ATOM   4363  CA  ALA K  22      95.474 116.957 308.386  1.00  0.00           C
ATOM   4364  CA  ASP K  23      96.519 119.504 311.002  1.00  0.00           C
ATOM   4365  CA  GLY K  24      94.262 119.539 314.052  1.00  0.00           C
ATOM   4366  CA  TYR K  25      92.974 115.970 313.522  1.00  0.00           C
ATOM   4367  CA  ALA K  26      96.623 115.032 313.694  1.00  0.00           C
ATOM   4368  CA  ASN K  27      97.130 116.908 316.961  1.00  0.00           C
ATOM   4369  CA  ASN K  28      93.734 115.700 318.208  1.00  0.00           C
ATOM   4370  CA  PHE K  29      93.950 111.954 317.499  1.00  0.00           C
ATOM   4371  CA  LEU K  30      97.311 110.761 316.102  1.00  0.00           C
ATOM   4372  CA  PHE K  31      99.273 113.125 318.338  1.00  0.00           C
ATOM   4373  CA  LYS K  32      96.864 112.007 321.030  1.00  0.00           C
ATOM   4374  CA  GLN K  33      97.464 108.264 320.872  1.00  0.00           C
ATOM   4375  CA  GLY K  34     101.210 108.618 320.294  1.00  0.00           C
ATOM   4376  CA  LEU K  35     100.670 107.409 316.713  1.00  0.00           C
ATOM   4377  CA  ALA K  36     102.488 110.291 315.007  1.00  0.00           C
ATOM   4378  CA  ILE K  37     104.704 113.256 315.831  1.00  0.00           C
ATOM   4379  CA  GLU K  38     105.460 116.771 314.534  1.00  0.00           C
ATOM   4380  CA  ALA K  39     107.607 116.644 311.387  1.00  0.00           C
ATOM   4381  CA  THR K  40     109.578 119.637 312.380  1.00  0.00           C
ATOM   4382  CA  PRO K  41     113.157 120.265 311.171  1.00  0.00           C
ATOM   4383  CA  ALA K  42     114.213 119.866 314.826  1.00  0.00           C
ATOM   4384  CA  ASN K  43     112.438 116.598 315.581  1.00  0.00           C
ATOM   4385  CA  LEU K  44     113.781 115.459 312.197  1.00  0.00           C
ATOM   4386  CA  LYS K  45     117.422 116.137 312.947  1.00  0.00           C
ATOM   4387  CA  ALA K  46     116.862 114.930 316.515  1.00  0.00           C
ATOM   4388  CA  LEU K  47     115.565 111.698 315.007  1.00  0.00           C
ATOM   4389  CA  GLU K  48     118.596 111.410 312.746  1.00  0.00           C
ATOM   4390  CA  ALA K  49     120.835 111.611 315.792  1.00  0.00           C
ATOM   4391  CA  GLN K  50     119.105 108.652 317.518  1.00  0.00           C
ATOM   4392  CA  LYS K  51     119.265 106.544 314.382  1.00  0.00           C
ATOM   4393  CA  GLN K  52     122.911 107.468 314.106  1.00  0.00           C
ATOM   4394  CA  LYS K  53     124.496 106.020 317.000  1.00  0.00           C
ATOM   4395  CA  GLU K  54     122.724 102.765 316.097  1.00  0.00           C
ATOM   4396  CA  GLN K  55     124.558 102.952 312.753  1.00  0.00           C
ATOM   4397  CA  ARG K  56     127.934 103.561 314.420  1.00  0.00           C
ATOM   4398  CA  GLN K  57     127.442 100.662 316.793  1.00  0.00           C
ATOM   4399  CA  ALA K  58     126.423  98.215 314.132  1.00  0.00           C
ATOM   4400  CA  ALA K  59     129.672  99.129 312.432  1.00  0.00           C
ATOM   4401  CA  GLU K  60     131.849  98.748 315.487  1.00  0.00           C
ATOM   4402  CA  GLU K  61     130.406  95.358 316.037  1.00  0.00           C
ATOM   4403  CA  LEU K  62     131.069  94.198 312.511  1.00  0.00           C
ATOM   4404  CA  ALA K  63     134.579  95.547 312.680  1.00  0.00           C
```

```
ATOM   4405  CA  ASN K  64     135.133  93.730 315.952  1.00  0.00           C
ATOM   4406  CA  ALA K  65     133.788  90.381 314.688  1.00  0.00           C
ATOM   4407  CA  LYS K  66     136.213  90.778 311.835  1.00  0.00           C
ATOM   4408  CA  LYS K  67     139.294  91.359 313.990  1.00  0.00           C
ATOM   4409  CA  LEU K  68     138.152  88.609 316.304  1.00  0.00           C
ATOM   4410  CA  LYS K  69     137.883  86.219 313.368  1.00  0.00           C
ATOM   4411  CA  GLU K  70     141.560  86.911 312.685  1.00  0.00           C
ATOM   4412  CA  GLN K  71     142.657  86.188 316.198  1.00  0.00           C
ATOM   4413  CA  LEU K  72     140.764  82.847 316.242  1.00  0.00           C
ATOM   4414  CA  GLU K  73     142.079  81.500 312.970  1.00  0.00           C
ATOM   4415  CA  LYS K  74     145.633  81.640 314.298  1.00  0.00           C
ATOM   4416  CA  LEU K  75     144.825  79.564 317.496  1.00  0.00           C
ATOM   4417  CA  THR K  76     144.450  75.875 318.230  1.00  0.00           C
ATOM   4418  CA  VAL K  77     142.429  74.802 321.246  1.00  0.00           C
ATOM   4419  CA  THR K  78     143.897  71.780 323.033  1.00  0.00           C
ATOM   4420  CA  ILE K  79     141.424  69.641 324.910  1.00  0.00           C
ATOM   4421  CA  PRO K  80     142.984  66.491 326.419  1.00  0.00           C
ATOM   4422  CA  ALA K  81     140.724  63.582 327.136  1.00  0.00           C
ATOM   4423  CA  LYS K  82     140.432  59.995 328.298  1.00  0.00           C
ATOM   4424  CA  ALA K  83     140.128  57.673 325.299  1.00  0.00           C
ATOM   4425  CA  GLY K  84     140.469  53.992 324.742  1.00  0.00           C
ATOM   4426  CA  GLU K  85     138.537  52.068 322.090  1.00  0.00           C
ATOM   4427  CA  GLY K  86     140.586  52.992 318.992  1.00  0.00           C
ATOM   4428  CA  ARG K  88     137.314  56.770 320.884  1.00  0.00           C
ATOM   4429  CA  LEU K  89     136.543  58.956 323.907  1.00  0.00           C
ATOM   4430  CA  PHE K  90     134.882  57.961 327.176  1.00  0.00           C
ATOM   4431  CA  GLY K  91     132.737  61.083 327.252  1.00  0.00           C
ATOM   4432  CA  SER K  92     132.278  63.893 324.721  1.00  0.00           C
ATOM   4433  CA  ILE K  93     133.875  67.240 324.136  1.00  0.00           C
ATOM   4434  CA  THR K  94     131.176  69.851 323.695  1.00  0.00           C
ATOM   4435  CA  SER K  95     130.811  73.623 323.206  1.00  0.00           C
ATOM   4436  CA  LYS K  96     131.292  74.478 326.893  1.00  0.00           C
ATOM   4437  CA  GLN K  97     134.599  72.692 327.150  1.00  0.00           C
ATOM   4438  CA  ILE K  98     135.796  74.270 323.922  1.00  0.00           C
ATOM   4439  CA  ALA K  99     134.650  77.671 325.116  1.00  0.00           C
ATOM   4440  CA  GLU K 100     136.488  77.109 328.451  1.00  0.00           C
ATOM   4441  CA  SER K 101     139.771  75.898 327.007  1.00  0.00           C
ATOM   4442  CA  LEU K 102     139.623  78.887 324.743  1.00  0.00           C
ATOM   4443  CA  GLN K 103     139.291  81.303 327.649  1.00  0.00           C
ATOM   4444  CA  ALA K 104     141.833  79.481 329.783  1.00  0.00           C
ATOM   4445  CA  GLN K 105     144.473  79.174 327.084  1.00  0.00           C
ATOM   4446  CA  HIS K 106     143.980  82.124 324.826  1.00  0.00           C
ATOM   4447  CA  GLY K 107     142.364  84.760 326.965  1.00  0.00           C
ATOM   4448  CA  LEU K 108     139.245  84.894 324.843  1.00  0.00           C
ATOM   4449  CA  LYS K 109     135.816  84.831 326.475  1.00  0.00           C
ATOM   4450  CA  LEU K 110     133.390  83.648 323.727  1.00  0.00           C
ATOM   4451  CA  ASP K 111     129.737  82.627 324.182  1.00  0.00           C
ATOM   4452  CA  LYS K 112     129.416  78.920 323.691  1.00  0.00           C
ATOM   4453  CA  ARG K 113     126.307  79.666 321.566  1.00  0.00           C
ATOM   4454  CA  LYS K 114     128.570  80.892 318.786  1.00  0.00           C
ATOM   4455  CA  ILE K 115     130.522  77.632 318.624  1.00  0.00           C
ATOM   4456  CA  GLU K 116     128.531  75.907 315.942  1.00  0.00           C
ATOM   4457  CA  LEU K 117     129.372  72.342 317.025  1.00  0.00           C
ATOM   4458  CA  ALA K 118     126.792  69.836 315.750  1.00  0.00           C
ATOM   4459  CA  ASP K 119     127.365  66.403 317.172  1.00  0.00           C
ATOM   4460  CA  ALA K 120     129.672  66.311 320.255  1.00  0.00           C
ATOM   4461  CA  ILE K 121     133.293  65.338 319.446  1.00  0.00           C
ATOM   4462  CA  ARG K 122     133.793  61.716 320.608  1.00  0.00           C
ATOM   4463  CA  ALA K 123     137.226  60.873 319.212  1.00  0.00           C
ATOM   4464  CA  LEU K 124     140.895  61.863 319.459  1.00  0.00           C
ATOM   4465  CA  GLY K 125     142.288  64.146 316.694  1.00  0.00           C
ATOM   4466  CA  TYR K 126     141.751  67.539 315.011  1.00  0.00           C
ATOM   4467  CA  THR K 127     138.402  69.202 314.289  1.00  0.00           C
ATOM   4468  CA  ASN K 128     137.740  72.529 312.581  1.00  0.00           C
ATOM   4469  CA  VAL K 129     134.658  73.995 314.315  1.00  0.00           C
ATOM   4470  CA  PRO K 130     132.762  77.006 312.757  1.00  0.00           C
ATOM   4471  CA  VAL K 131     132.184  80.059 314.959  1.00  0.00           C
ATOM   4472  CA  LYS K 132     129.374  82.461 314.161  1.00  0.00           C
ATOM   4473  CA  LEU K 133     130.772  85.700 315.429  1.00  0.00           C
ATOM   4474  CA  HIS K 134     128.208  87.779 313.556  1.00  0.00           C
ATOM   4475  CA  PRO K 135     125.357  87.472 310.933  1.00  0.00           C
ATOM   4476  CA  GLU K 136     127.941  87.746 308.233  1.00  0.00           C
ATOM   4477  CA  VAL K 137     131.167  86.745 310.050  1.00  0.00           C
ATOM   4478  CA  THR K 138     132.128  83.087 310.731  1.00  0.00           C
ATOM   4479  CA  ALA K 139     135.613  81.872 311.661  1.00  0.00           C
ATOM   4480  CA  THR K 140     137.152  78.419 311.749  1.00  0.00           C
ATOM   4481  CA  LEU K 141     138.338  77.297 315.197  1.00  0.00           C
ATOM   4482  CA  LYS K 142     140.848  74.426 315.115  1.00  0.00           C
ATOM   4483  CA  VAL K 143     140.193  72.133 317.993  1.00  0.00           C
ATOM   4484  CA  HIS K 144     142.757  69.471 319.028  1.00  0.00           C
ATOM   4485  CA  VAL K 145     141.670  66.568 321.286  1.00  0.00           C
ATOM   4486  CA  THR K 146     144.645  64.739 322.854  1.00  0.00           C
ATOM   4487  CA  GLU K 147     144.590  61.541 324.970  1.00  0.00           C
ATOM   4488  CA  GLN K 148     145.334  62.167 328.604  1.00  0.00           C
ATOM   4489  CA  LYS K 149     146.273  60.038 331.660  1.00  0.00           C
TER    4490      LYS K 149
ATOM   4491  CA  GLN L   8     -52.589 177.148 263.906  1.00  0.00           C
```

```
ATOM   4492  CA   ILE L   9     -50.457 174.013 263.543  1.00  0.00           C
ATOM   4493  CA   LYS L  10     -48.589 172.624 260.536  1.00  0.00           C
ATOM   4494  CA   LEU L  11     -47.144 169.211 259.725  1.00  0.00           C
ATOM   4495  CA   GLN L  12     -46.250 166.871 256.868  1.00  0.00           C
ATOM   4496  CA   LEU L  13     -48.559 163.847 256.849  1.00  0.00           C
ATOM   4497  CA   PRO L  14     -48.329 161.019 254.271  1.00  0.00           C
ATOM   4498  CA   ALA L  15     -51.042 160.751 251.608  1.00  0.00           C
ATOM   4499  CA   GLY L  16     -53.626 158.185 252.694  1.00  0.00           C
ATOM   4500  CA   LYS L  17     -52.762 157.702 256.370  1.00  0.00           C
ATOM   4501  CA   ALA L  18     -53.331 159.403 259.747  1.00  0.00           C
ATOM   4502  CA   THR L  19     -54.312 158.899 263.420  1.00  0.00           C
ATOM   4503  CA   PRO L  20     -51.085 157.504 264.935  1.00  0.00           C
ATOM   4504  CA   ALA L  21     -50.133 158.884 268.345  1.00  0.00           C
ATOM   4505  CA   PRO L  22     -46.400 159.438 267.737  1.00  0.00           C
ATOM   4506  CA   PRO L  23     -46.796 161.052 264.252  1.00  0.00           C
ATOM   4507  CA   VAL L  24     -50.079 163.005 264.557  1.00  0.00           C
ATOM   4508  CA   GLY L  25     -52.120 162.677 267.757  1.00  0.00           C
ATOM   4509  CA   PRO L  26     -50.027 164.349 270.522  1.00  0.00           C
ATOM   4510  CA   ALA L  27     -48.931 167.132 268.152  1.00  0.00           C
ATOM   4511  CA   LEU L  28     -52.107 169.066 267.342  1.00  0.00           C
ATOM   4512  CA   GLY L  29     -54.015 166.819 269.719  1.00  0.00           C
ATOM   4513  CA   GLN L  30     -52.631 169.094 272.428  1.00  0.00           C
ATOM   4514  CA   HIS L  31     -53.891 172.315 270.830  1.00  0.00           C
ATOM   4515  CA   GLY L  32     -57.549 171.304 270.930  1.00  0.00           C
ATOM   4516  CA   VAL L  33     -57.919 169.421 267.650  1.00  0.00           C
ATOM   4517  CA   ASN L  34     -60.038 166.253 267.522  1.00  0.00           C
ATOM   4518  CA   ILE L  35     -57.752 163.728 265.796  1.00  0.00           C
ATOM   4519  CA   MET L  36     -60.392 161.308 264.407  1.00  0.00           C
ATOM   4520  CA   GLU L  37     -62.125 164.077 262.429  1.00  0.00           C
ATOM   4521  CA   PHE L  38     -58.835 165.177 260.837  1.00  0.00           C
ATOM   4522  CA   CYS L  39     -57.537 161.670 260.045  1.00  0.00           C
ATOM   4523  CA   LYS L  40     -60.609 160.758 257.994  1.00  0.00           C
ATOM   4524  CA   ARG L  41     -60.895 164.310 256.629  1.00  0.00           C
ATOM   4525  CA   PHE L  42     -57.221 164.615 255.676  1.00  0.00           C
ATOM   4526  CA   ASN L  43     -57.112 161.114 254.209  1.00  0.00           C
ATOM   4527  CA   ALA L  44     -60.239 162.066 252.276  1.00  0.00           C
ATOM   4528  CA   GLU L  45     -58.858 164.575 249.763  1.00  0.00           C
ATOM   4529  CA   THR L  46     -55.336 163.186 250.115  1.00  0.00           C
ATOM   4530  CA   ALA L  47     -56.781 160.354 248.019  1.00  0.00           C
ATOM   4531  CA   ASP L  48     -56.402 162.249 244.740  1.00  0.00           C
ATOM   4532  CA   LYS L  49     -52.670 162.323 245.522  1.00  0.00           C
ATOM   4533  CA   ALA L  50     -51.633 159.144 247.348  1.00  0.00           C
ATOM   4534  CA   GLY L  51     -48.227 157.713 248.193  1.00  0.00           C
ATOM   4535  CA   MET L  52     -46.593 161.118 248.557  1.00  0.00           C
ATOM   4536  CA   ILE L  53     -45.859 163.035 251.748  1.00  0.00           C
ATOM   4537  CA   LEU L  54     -47.896 166.244 251.659  1.00  0.00           C
ATOM   4538  CA   PRO L  55     -47.699 169.165 254.150  1.00  0.00           C
ATOM   4539  CA   VAL L  56     -50.985 170.452 255.570  1.00  0.00           C
ATOM   4540  CA   VAL L  57     -51.624 173.596 257.608  1.00  0.00           C
ATOM   4541  CA   ILE L  58     -54.233 172.899 260.273  1.00  0.00           C
ATOM   4542  CA   THR L  59     -56.007 175.883 261.836  1.00  0.00           C
ATOM   4543  CA   VAL L  60     -57.914 175.526 265.117  1.00  0.00           C
ATOM   4544  CA   TYR L  61     -60.559 178.084 266.122  1.00  0.00           C
ATOM   4545  CA   GLU L  62     -61.308 178.995 269.748  1.00  0.00           C
ATOM   4546  CA   ASP L  63     -64.151 176.448 269.646  1.00  0.00           C
ATOM   4547  CA   LYS L  64     -61.693 173.567 269.026  1.00  0.00           C
ATOM   4548  CA   SER L  65     -63.077 173.233 265.486  1.00  0.00           C
ATOM   4549  CA   PHE L  66     -60.651 173.363 262.565  1.00  0.00           C
ATOM   4550  CA   THR L  67     -59.852 173.580 258.851  1.00  0.00           C
ATOM   4551  CA   PHE L  68     -56.663 172.854 256.942  1.00  0.00           C
ATOM   4552  CA   ILE L  69     -55.058 173.601 253.608  1.00  0.00           C
ATOM   4553  CA   ILE L  70     -53.207 170.854 251.753  1.00  0.00           C
ATOM   4554  CA   LYS L  71     -50.101 171.954 249.854  1.00  0.00           C
ATOM   4555  CA   THR L  72     -47.708 170.354 247.391  1.00  0.00           C
ATOM   4556  CA   PRO L  73     -45.117 167.923 248.830  1.00  0.00           C
ATOM   4557  CA   PRO L  74     -41.767 169.363 250.014  1.00  0.00           C
ATOM   4558  CA   ALA L  75     -39.024 169.991 247.474  1.00  0.00           C
ATOM   4559  CA   SER L  76     -36.614 167.738 249.329  1.00  0.00           C
ATOM   4560  CA   PHE L  77     -39.256 164.987 249.169  1.00  0.00           C
ATOM   4561  CA   LEU L  78     -40.027 165.292 245.473  1.00  0.00           C
ATOM   4562  CA   LEU L  79     -36.262 165.469 244.870  1.00  0.00           C
ATOM   4563  CA   LYS L  80     -35.621 162.299 246.863  1.00  0.00           C
ATOM   4564  CA   LYS L  81     -38.305 160.573 244.819  1.00  0.00           C
ATOM   4565  CA   ALA L  82     -36.929 161.887 241.531  1.00  0.00           C
ATOM   4566  CA   ALA L  83     -33.375 160.778 242.327  1.00  0.00           C
ATOM   4567  CA   GLY L  84     -34.853 157.458 243.384  1.00  0.00           C
ATOM   4568  CA   ILE L  85     -33.103 157.742 246.741  1.00  0.00           C
ATOM   4569  CA   GLU L  86     -34.430 157.432 250.301  1.00  0.00           C
ATOM   4570  CA   LYS L  87     -32.345 160.048 252.105  1.00  0.00           C
ATOM   4571  CA   GLY L  88     -30.338 163.155 251.352  1.00  0.00           C
ATOM   4572  CA   SER L  89     -26.568 163.225 251.619  1.00  0.00           C
ATOM   4573  CA   SER L  90     -25.335 163.340 255.201  1.00  0.00           C
ATOM   4574  CA   GLU L  91     -22.853 165.890 253.902  1.00  0.00           C
ATOM   4575  CA   PRO L  92     -24.363 167.879 250.988  1.00  0.00           C
ATOM   4576  CA   LYS L  93     -21.936 168.889 248.244  1.00  0.00           C
ATOM   4577  CA   ARG L  94     -19.178 166.898 249.952  1.00  0.00           C
ATOM   4578  CA   LYS L  95     -20.957 163.652 249.054  1.00  0.00           C
```

```
ATOM   4579  CA  ILE L  96    -23.440 163.285 246.231  1.00  0.00           C
ATOM   4580  CA  VAL L  97    -25.980 160.556 246.935  1.00  0.00           C
ATOM   4581  CA  GLY L  98    -28.066 160.956 243.816  1.00  0.00           C
ATOM   4582  CA  LYS L  99    -28.868 162.969 240.721  1.00  0.00           C
ATOM   4583  CA  VAL L 100    -31.697 164.288 238.580  1.00  0.00           C
ATOM   4584  CA  THR L 101    -32.028 165.611 235.056  1.00  0.00           C
ATOM   4585  CA  ARG L 102    -32.692 169.269 234.289  1.00  0.00           C
ATOM   4586  CA  LYS L 103    -36.069 168.173 232.965  1.00  0.00           C
ATOM   4587  CA  GLN L 104    -36.824 166.615 236.349  1.00  0.00           C
ATOM   4588  CA  ILE L 105    -36.077 169.916 238.061  1.00  0.00           C
ATOM   4589  CA  GLU L 106    -38.576 171.371 235.598  1.00  0.00           C
ATOM   4590  CA  GLU L 107    -41.189 168.791 236.624  1.00  0.00           C
ATOM   4591  CA  ILE L 108    -40.788 169.410 240.335  1.00  0.00           C
ATOM   4592  CA  ALA L 109    -40.713 173.176 239.873  1.00  0.00           C
ATOM   4593  CA  LYS L 110    -43.935 172.796 237.900  1.00  0.00           C
ATOM   4594  CA  THR L 111    -45.460 170.550 240.558  1.00  0.00           C
ATOM   4595  CA  LYS L 112    -44.629 172.924 243.401  1.00  0.00           C
ATOM   4596  CA  MET L 113    -45.483 176.055 241.396  1.00  0.00           C
ATOM   4597  CA  PRO L 114    -48.724 176.745 243.298  1.00  0.00           C
ATOM   4598  CA  ASP L 115    -46.596 177.018 246.440  1.00  0.00           C
ATOM   4599  CA  LEU L 116    -43.652 178.766 244.768  1.00  0.00           C
ATOM   4600  CA  ASN L 117    -43.380 182.536 244.365  1.00  0.00           C
ATOM   4601  CA  ALA L 118    -41.343 182.531 241.149  1.00  0.00           C
ATOM   4602  CA  ASN L 119    -42.583 184.681 238.274  1.00  0.00           C
ATOM   4603  CA  SER L 120    -41.082 182.330 235.692  1.00  0.00           C
ATOM   4604  CA  LEU L 121    -40.537 178.597 235.247  1.00  0.00           C
ATOM   4605  CA  GLU L 122    -36.841 179.447 235.173  1.00  0.00           C
ATOM   4606  CA  ALA L 123    -36.971 181.091 238.589  1.00  0.00           C
ATOM   4607  CA  ALA L 124    -38.983 178.116 239.852  1.00  0.00           C
ATOM   4608  CA  MET L 125    -36.319 175.667 238.721  1.00  0.00           C
ATOM   4609  CA  LYS L 126    -33.641 177.842 240.277  1.00  0.00           C
ATOM   4610  CA  ILE L 127    -35.546 177.509 243.542  1.00  0.00           C
ATOM   4611  CA  ILE L 128    -35.805 173.728 243.295  1.00  0.00           C
ATOM   4612  CA  GLU L 129    -32.123 173.481 242.369  1.00  0.00           C
ATOM   4613  CA  GLY L 130    -31.279 175.334 245.533  1.00  0.00           C
ATOM   4614  CA  THR L 131    -32.919 172.557 247.528  1.00  0.00           C
ATOM   4615  CA  ALA L 132    -31.275 169.769 245.533  1.00  0.00           C
ATOM   4616  CA  LYS L 133    -27.914 171.430 246.113  1.00  0.00           C
ATOM   4617  CA  SER L 134    -28.675 171.242 249.822  1.00  0.00           C
ATOM   4618  CA  MET L 135    -29.310 167.494 249.903  1.00  0.00           C
ATOM   4619  CA  GLY L 136    -26.439 166.154 247.829  1.00  0.00           C
ATOM   4620  CA  ILE L 137    -28.510 165.670 244.687  1.00  0.00           C
ATOM   4621  CA  GLU L 138    -26.857 166.681 241.419  1.00  0.00           C
ATOM   4622  CA  VAL L 139    -28.452 167.899 238.195  1.00  0.00           C
ATOM   4623  CA  VAL L 140    -27.591 166.512 234.747  1.00  0.00           C
TER    4624      VAL L 140
ATOM   4625  CA  ALA M   4     -0.952 234.624 319.843  1.00  0.00           C
ATOM   4626  CA  GLU M   5      1.116 237.638 318.754  1.00  0.00           C
ATOM   4627  CA  PHE M   6      4.000 237.052 316.369  1.00  0.00           C
ATOM   4628  CA  ASP M   7      6.365 239.741 315.061  1.00  0.00           C
ATOM   4629  CA  ALA M   8      5.447 239.310 311.453  1.00  0.00           C
ATOM   4630  CA  ASP M   9      8.369 240.412 309.348  1.00  0.00           C
ATOM   4631  CA  VAL M  10      6.814 239.113 306.178  1.00  0.00           C
ATOM   4632  CA  ILE M  11      3.196 237.980 306.342  1.00  0.00           C
ATOM   4633  CA  VAL M  12      2.694 235.593 303.411  1.00  0.00           C
ATOM   4634  CA  ASP M  13     -0.653 234.717 301.808  1.00  0.00           C
ATOM   4635  CA  ALA M  14     -0.785 231.111 300.688  1.00  0.00           C
ATOM   4636  CA  ARG M  15     -4.208 230.784 299.050  1.00  0.00           C
ATOM   4637  CA  ASP M  16     -4.015 229.401 295.514  1.00  0.00           C
ATOM   4638  CA  CYS M  17     -0.248 229.173 295.914  1.00  0.00           C
ATOM   4639  CA  ILE M  18      1.988 226.153 295.427  1.00  0.00           C
ATOM   4640  CA  MET M  19      3.044 224.888 298.844  1.00  0.00           C
ATOM   4641  CA  GLY M  20      6.738 224.171 298.562  1.00  0.00           C
ATOM   4642  CA  ARG M  21      7.415 226.924 296.060  1.00  0.00           C
ATOM   4643  CA  VAL M  22      6.405 229.055 299.006  1.00  0.00           C
ATOM   4644  CA  ALA M  23      7.932 226.794 301.625  1.00  0.00           C
ATOM   4645  CA  SER M  24     11.187 226.932 299.708  1.00  0.00           C
ATOM   4646  CA  GLN M  25     11.273 230.722 299.789  1.00  0.00           C
ATOM   4647  CA  VAL M  26     10.045 230.969 303.358  1.00  0.00           C
ATOM   4648  CA  ALA M  27     12.859 228.627 304.393  1.00  0.00           C
ATOM   4649  CA  GLU M  28     15.453 230.721 302.563  1.00  0.00           C
ATOM   4650  CA  GLN M  29     14.201 233.887 304.289  1.00  0.00           C
ATOM   4651  CA  ALA M  30     13.938 232.312 307.724  1.00  0.00           C
ATOM   4652  CA  LEU M  31     17.623 231.418 307.499  1.00  0.00           C
ATOM   4653  CA  ASP M  32     18.243 235.023 306.541  1.00  0.00           C
ATOM   4654  CA  GLY M  33     16.912 235.944 309.949  1.00  0.00           C
ATOM   4655  CA  GLU M  34     13.392 236.841 308.910  1.00  0.00           C
ATOM   4656  CA  THR M  35     10.338 236.252 311.083  1.00  0.00           C
ATOM   4657  CA  VAL M  36      7.723 234.782 308.761  1.00  0.00           C
ATOM   4658  CA  ALA M  37      4.059 233.921 309.049  1.00  0.00           C
ATOM   4659  CA  VAL M  38      2.219 231.975 306.367  1.00  0.00           C
ATOM   4660  CA  VAL M  39     -1.524 232.536 306.253  1.00  0.00           C
ATOM   4661  CA  ASN M  40     -4.520 230.758 304.722  1.00  0.00           C
ATOM   4662  CA  ALA M  41     -2.651 227.433 304.831  1.00  0.00           C
ATOM   4663  CA  GLU M  42     -6.049 225.821 304.483  1.00  0.00           C
ATOM   4664  CA  ARG M  43     -6.168 227.331 301.003  1.00  0.00           C
ATOM   4665  CA  ALA M  44     -2.616 226.546 299.908  1.00  0.00           C
```

```
ATOM   4666  CA  VAL M   45      -2.289 224.327 296.845  1.00  0.00           C
ATOM   4667  CA  ILE M   46      -0.381 221.282 295.595  1.00  0.00           C
ATOM   4668  CA  THR M   47      -0.337 220.223 291.942  1.00  0.00           C
ATOM   4669  CA  GLY M   48      -1.293 216.795 290.701  1.00  0.00           C
ATOM   4670  CA  ARG M   49      -3.853 214.026 290.755  1.00  0.00           C
ATOM   4671  CA  GLU M   50      -5.868 213.893 293.979  1.00  0.00           C
ATOM   4672  CA  GLU M   51      -5.713 210.259 295.022  1.00  0.00           C
ATOM   4673  CA  GLN M   52      -2.057 209.868 294.186  1.00  0.00           C
ATOM   4674  CA  ILE M   53      -1.382 212.875 296.392  1.00  0.00           C
ATOM   4675  CA  VAL M   54      -3.871 211.646 298.996  1.00  0.00           C
ATOM   4676  CA  GLU M   55      -2.271 208.213 299.079  1.00  0.00           C
ATOM   4677  CA  LYS M   56       1.136 209.692 299.791  1.00  0.00           C
ATOM   4678  CA  TYR M   57      -0.132 211.549 302.828  1.00  0.00           C
ATOM   4679  CA  GLU M   58      -2.266 208.657 304.041  1.00  0.00           C
ATOM   4680  CA  LYS M   59       0.824 206.497 303.965  1.00  0.00           C
ATOM   4681  CA  ARG M   60       2.584 209.114 306.058  1.00  0.00           C
ATOM   4682  CA  VAL M   61      -0.191 209.072 308.607  1.00  0.00           C
ATOM   4683  CA  ASP M   62      -0.087 205.312 308.734  1.00  0.00           C
ATOM   4684  CA  ILE M   63       3.650 204.893 309.126  1.00  0.00           C
ATOM   4685  CA  GLY M   64       3.629 203.887 312.781  1.00  0.00           C
ATOM   4686  CA  ASN M   65       6.198 202.929 315.416  1.00  0.00           C
ATOM   4687  CA  ASP M   66       6.790 202.881 319.141  1.00  0.00           C
ATOM   4688  CA  ASN M   67       9.655 205.263 318.303  1.00  0.00           C
ATOM   4689  CA  GLY M   68       7.020 207.317 316.537  1.00  0.00           C
ATOM   4690  CA  TYR M   69       6.348 209.165 313.309  1.00  0.00           C
ATOM   4691  CA  PHE M   70       4.195 212.154 314.228  1.00  0.00           C
ATOM   4692  CA  TYR M   71       2.904 213.246 310.864  1.00  0.00           C
ATOM   4693  CA  PRO M   72       0.461 216.195 311.030  1.00  0.00           C
ATOM   4694  CA  LYS M   73      -3.059 216.086 309.594  1.00  0.00           C
ATOM   4695  CA  ARG M   74      -4.194 219.710 309.789  1.00  0.00           C
ATOM   4696  CA  PRO M   75      -3.041 222.192 307.142  1.00  0.00           C
ATOM   4697  CA  ASP M   76      -1.075 224.131 309.787  1.00  0.00           C
ATOM   4698  CA  GLY M   77       1.134 221.170 310.419  1.00  0.00           C
ATOM   4699  CA  ILE M   78       1.295 219.674 306.951  1.00  0.00           C
ATOM   4700  CA  PHE M   79       2.615 223.029 305.834  1.00  0.00           C
ATOM   4701  CA  LYS M   80       5.036 223.563 308.685  1.00  0.00           C
ATOM   4702  CA  ARG M   81       6.326 220.020 308.175  1.00  0.00           C
ATOM   4703  CA  THR M   82       7.000 220.883 304.537  1.00  0.00           C
ATOM   4704  CA  ILE M   83       9.077 223.829 305.660  1.00  0.00           C
ATOM   4705  CA  ARG M   84      11.017 221.791 308.225  1.00  0.00           C
ATOM   4706  CA  GLY M   85      12.047 219.426 305.462  1.00  0.00           C
ATOM   4707  CA  MET M   86      13.837 222.368 303.856  1.00  0.00           C
ATOM   4708  CA  LEU M   87      15.715 223.471 306.941  1.00  0.00           C
ATOM   4709  CA  PRO M   88      18.452 221.799 308.996  1.00  0.00           C
ATOM   4710  CA  LYS M   90      18.528 219.966 314.104  1.00  0.00           C
ATOM   4711  CA  LYS M   91      21.220 222.637 314.024  1.00  0.00           C
ATOM   4712  CA  GLN M   92      20.949 225.875 316.000  1.00  0.00           C
ATOM   4713  CA  ARG M   93      20.748 228.017 312.893  1.00  0.00           C
ATOM   4714  CA  GLY M   94      18.104 225.599 311.666  1.00  0.00           C
ATOM   4715  CA  ARG M   95      15.952 225.375 314.767  1.00  0.00           C
ATOM   4716  CA  GLU M   96      16.249 229.152 315.124  1.00  0.00           C
ATOM   4717  CA  ALA M   97      14.944 229.894 311.651  1.00  0.00           C
ATOM   4718  CA  PHE M   98      12.267 227.233 311.899  1.00  0.00           C
ATOM   4719  CA  GLU M   99      11.243 228.512 315.310  1.00  0.00           C
ATOM   4720  CA  SER M  100      10.804 231.987 313.849  1.00  0.00           C
ATOM   4721  CA  VAL M  101       8.234 230.733 311.352  1.00  0.00           C
ATOM   4722  CA  ARG M  102       4.581 229.950 312.011  1.00  0.00           C
ATOM   4723  CA  VAL M  103       1.679 228.808 309.873  1.00  0.00           C
ATOM   4724  CA  TYR M  104      -1.835 230.062 310.508  1.00  0.00           C
ATOM   4725  CA  LEU M  105      -5.051 228.220 309.811  1.00  0.00           C
ATOM   4726  CA  GLY M  106      -6.419 231.502 308.488  1.00  0.00           C
ATOM   4727  CA  ASN M  107      -5.141 235.085 308.448  1.00  0.00           C
ATOM   4728  CA  PRO M  108      -5.301 236.157 312.136  1.00  0.00           C
ATOM   4729  CA  TYR M  109      -3.503 239.386 311.143  1.00  0.00           C
ATOM   4730  CA  ASP M  110      -5.066 242.572 309.776  1.00  0.00           C
ATOM   4731  CA  THR M  131      -6.167 222.186 298.589  1.00  0.00           C
ATOM   4732  CA  LEU M  132      -4.309 221.403 301.791  1.00  0.00           C
ATOM   4733  CA  GLY M  133      -7.747 221.926 303.271  1.00  0.00           C
ATOM   4734  CA  GLU M  134      -9.209 219.055 301.296  1.00  0.00           C
ATOM   4735  CA  ILE M  135      -6.269 216.800 302.085  1.00  0.00           C
ATOM   4736  CA  SER M  136      -6.692 217.323 305.831  1.00  0.00           C
ATOM   4737  CA  GLU M  137     -10.391 216.631 305.434  1.00  0.00           C
ATOM   4738  CA  THR M  138      -9.665 213.248 303.897  1.00  0.00           C
ATOM   4739  CA  LEU M  139      -7.066 212.512 306.558  1.00  0.00           C
ATOM   4740  CA  GLY M  140      -9.806 212.770 309.169  1.00  0.00           C
ATOM   4741  CA  ALA M  141      -8.881 216.188 310.541  1.00  0.00           C
TER    4742          ALA M  141
ATOM   4743  CA  MET N    1     -11.775 167.255 336.057  1.00  0.00           C
ATOM   4744  CA  ILE N    2     -13.254 164.757 333.614  1.00  0.00           C
ATOM   4745  CA  GLN N    3     -11.292 165.092 330.356  1.00  0.00           C
ATOM   4746  CA  GLN N    4      -9.905 162.880 327.573  1.00  0.00           C
ATOM   4747  CA  GLU N    5      -8.842 159.481 328.904  1.00  0.00           C
ATOM   4748  CA  SER N    6     -10.747 159.874 332.168  1.00  0.00           C
ATOM   4749  CA  ARG N    7     -12.435 156.619 333.264  1.00  0.00           C
ATOM   4750  CA  LEU N    8     -16.114 156.806 334.174  1.00  0.00           C
ATOM   4751  CA  LYS N    9     -18.294 154.270 335.990  1.00  0.00           C
ATOM   4752  CA  VAL N   10     -21.509 153.402 334.158  1.00  0.00           C
```

```
ATOM   4753  CA  ALA N   11     -24.643 153.960 336.263  1.00  0.00           C
ATOM   4754  CA  ASP N   12     -27.040 151.855 334.187  1.00  0.00           C
ATOM   4755  CA  ASN N   13     -27.764 148.270 333.212  1.00  0.00           C
ATOM   4756  CA  SER N   14     -26.717 148.645 329.555  1.00  0.00           C
ATOM   4757  CA  GLY N   15     -23.916 146.110 330.052  1.00  0.00           C
ATOM   4758  CA  ALA N   16     -21.058 148.622 330.030  1.00  0.00           C
ATOM   4759  CA  ARG N   17     -19.146 148.741 333.307  1.00  0.00           C
ATOM   4760  CA  GLU N   18     -16.563 151.461 332.639  1.00  0.00           C
ATOM   4761  CA  VAL N   19     -15.799 153.836 329.761  1.00  0.00           C
ATOM   4762  CA  LEU N   20     -12.799 155.908 328.750  1.00  0.00           C
ATOM   4763  CA  VAL N   21     -13.450 159.486 327.567  1.00  0.00           C
ATOM   4764  CA  ILE N   22     -12.375 160.370 324.035  1.00  0.00           C
ATOM   4765  CA  LYS N   23     -13.893 163.839 323.719  1.00  0.00           C
ATOM   4766  CA  VAL N   24     -16.396 166.226 325.303  1.00  0.00           C
ATOM   4767  CA  LEU N   25     -19.160 167.237 322.917  1.00  0.00           C
ATOM   4768  CA  GLY N   26     -20.350 170.817 322.526  1.00  0.00           C
ATOM   4769  CA  GLY N   27     -17.947 172.599 320.212  1.00  0.00           C
ATOM   4770  CA  SER N   28     -14.295 173.279 319.489  1.00  0.00           C
ATOM   4771  CA  GLY N   29     -12.520 174.135 322.715  1.00  0.00           C
ATOM   4772  CA  ARG N   30     -14.541 171.979 325.102  1.00  0.00           C
ATOM   4773  CA  ARG N   31     -12.172 169.938 327.261  1.00  0.00           C
ATOM   4774  CA  TYR N   32     -13.852 169.242 330.608  1.00  0.00           C
ATOM   4775  CA  ALA N   33     -17.120 167.537 331.372  1.00  0.00           C
ATOM   4776  CA  ASN N   34     -19.417 168.009 334.317  1.00  0.00           C
ATOM   4777  CA  ILE N   35     -23.011 166.981 335.036  1.00  0.00           C
ATOM   4778  CA  GLY N   36     -25.191 167.175 331.965  1.00  0.00           C
ATOM   4779  CA  ASP N   37     -22.393 167.113 329.419  1.00  0.00           C
ATOM   4780  CA  VAL N   38     -22.222 164.399 326.786  1.00  0.00           C
ATOM   4781  CA  VAL N   39     -19.000 162.558 326.049  1.00  0.00           C
ATOM   4782  CA  VAL N   40     -17.904 160.200 323.304  1.00  0.00           C
ATOM   4783  CA  ALA N   41     -16.172 157.228 324.938  1.00  0.00           C
ATOM   4784  CA  THR N   42     -14.867 153.721 324.380  1.00  0.00           C
ATOM   4785  CA  VAL N   43     -16.240 150.851 326.479  1.00  0.00           C
ATOM   4786  CA  LYS N   44     -13.374 149.699 328.680  1.00  0.00           C
ATOM   4787  CA  ASP N   45     -15.176 146.904 330.525  1.00  0.00           C
ATOM   4788  CA  ALA N   46     -18.534 145.270 329.869  1.00  0.00           C
ATOM   4789  CA  THR N   47     -20.431 142.121 330.924  1.00  0.00           C
ATOM   4790  CA  PRO N   48     -19.695 139.336 328.387  1.00  0.00           C
ATOM   4791  CA  GLY N   49     -22.322 138.370 325.843  1.00  0.00           C
ATOM   4792  CA  GLY N   50     -24.178 141.673 326.115  1.00  0.00           C
ATOM   4793  CA  VAL N   51     -25.509 144.339 323.711  1.00  0.00           C
ATOM   4794  CA  VAL N   52     -22.595 146.647 324.467  1.00  0.00           C
ATOM   4795  CA  LYS N   53     -19.068 145.341 323.925  1.00  0.00           C
ATOM   4796  CA  LYS N   54     -15.506 146.216 324.931  1.00  0.00           C
ATOM   4797  CA  GLY N   55     -13.805 148.521 322.463  1.00  0.00           C
ATOM   4798  CA  GLN N   56     -17.068 149.952 321.126  1.00  0.00           C
ATOM   4799  CA  VAL N   57     -17.573 153.711 320.934  1.00  0.00           C
ATOM   4800  CA  VAL N   58     -20.655 155.095 322.668  1.00  0.00           C
ATOM   4801  CA  LYS N   59     -22.124 158.460 323.711  1.00  0.00           C
ATOM   4802  CA  ALA N   60     -22.860 158.959 327.408  1.00  0.00           C
ATOM   4803  CA  VAL N   61     -24.194 161.760 329.606  1.00  0.00           C
ATOM   4804  CA  VAL N   62     -22.357 162.538 332.875  1.00  0.00           C
ATOM   4805  CA  VAL N   63     -24.733 162.177 335.838  1.00  0.00           C
ATOM   4806  CA  ARG N   64     -22.413 162.328 338.868  1.00  0.00           C
ATOM   4807  CA  THR N   65     -19.047 164.016 339.301  1.00  0.00           C
ATOM   4808  CA  LYS N   66     -16.532 164.387 342.112  1.00  0.00           C
ATOM   4809  CA  ARG N   67     -16.069 168.043 341.050  1.00  0.00           C
ATOM   4810  CA  GLY N   68     -19.766 168.790 341.567  1.00  0.00           C
ATOM   4811  CA  VAL N   69     -21.807 171.901 340.783  1.00  0.00           C
ATOM   4812  CA  ARG N   70     -22.518 175.229 342.478  1.00  0.00           C
ATOM   4813  CA  ARG N   71     -26.217 176.056 342.544  1.00  0.00           C
ATOM   4814  CA  PRO N   72     -28.163 179.383 342.281  1.00  0.00           C
ATOM   4815  CA  ASP N   73     -29.468 178.941 345.858  1.00  0.00           C
ATOM   4816  CA  GLY N   74     -25.967 178.877 347.358  1.00  0.00           C
ATOM   4817  CA  SER N   75     -25.731 175.109 347.691  1.00  0.00           C
ATOM   4818  CA  TYR N   76     -22.960 172.980 346.215  1.00  0.00           C
ATOM   4819  CA  ILE N   77     -23.469 169.298 345.435  1.00  0.00           C
ATOM   4820  CA  ARG N   78     -20.794 166.711 344.595  1.00  0.00           C
ATOM   4821  CA  PHE N   79     -20.531 162.931 344.537  1.00  0.00           C
ATOM   4822  CA  ASP N   80     -17.950 160.327 345.445  1.00  0.00           C
ATOM   4823  CA  GLU N   81     -17.505 159.099 341.854  1.00  0.00           C
ATOM   4824  CA  ASN N   82     -17.600 160.188 338.214  1.00  0.00           C
ATOM   4825  CA  ALA N   83     -20.414 158.267 336.525  1.00  0.00           C
ATOM   4826  CA  CYS N   84     -22.307 158.352 333.240  1.00  0.00           C
ATOM   4827  CA  VAL N   85     -25.326 156.804 331.507  1.00  0.00           C
ATOM   4828  CA  ILE N   86     -25.053 155.475 327.940  1.00  0.00           C
ATOM   4829  CA  ILE N   87     -27.516 157.229 325.667  1.00  0.00           C
ATOM   4830  CA  ARG N   88     -28.973 157.072 322.180  1.00  0.00           C
ATOM   4831  CA  ASP N   89     -28.864 160.099 319.861  1.00  0.00           C
ATOM   4832  CA  ASP N   90     -32.277 161.311 321.099  1.00  0.00           C
ATOM   4833  CA  LYS N   91     -30.904 161.472 324.707  1.00  0.00           C
ATOM   4834  CA  SER N   92     -32.872 158.396 325.832  1.00  0.00           C
ATOM   4835  CA  PRO N   93     -30.886 155.847 327.858  1.00  0.00           C
ATOM   4836  CA  ARG N   94     -29.897 152.583 326.182  1.00  0.00           C
ATOM   4837  CA  GLY N   95     -30.411 150.664 329.439  1.00  0.00           C
ATOM   4838  CA  THR N   96     -33.650 150.350 331.402  1.00  0.00           C
ATOM   4839  CA  ARG N   97     -32.422 151.068 334.923  1.00  0.00           C
```

```
ATOM   4840  CA  ILE N  98     -30.348 153.850 336.442  1.00  0.00           C
ATOM   4841  CA  PHE N  99     -28.375 153.205 339.640  1.00  0.00           C
ATOM   4842  CA  GLY N 100     -27.637 155.713 342.352  1.00  0.00           C
ATOM   4843  CA  PRO N 101     -28.700 159.345 342.791  1.00  0.00           C
ATOM   4844  CA  VAL N 102     -28.461 161.812 339.896  1.00  0.00           C
ATOM   4845  CA  ALA N 103     -28.224 165.618 339.903  1.00  0.00           C
ATOM   4846  CA  ARG N 104     -31.309 167.707 339.125  1.00  0.00           C
ATOM   4847  CA  GLU N 105     -29.204 169.757 336.659  1.00  0.00           C
ATOM   4848  CA  LEU N 106     -29.935 166.996 334.120  1.00  0.00           C
ATOM   4849  CA  ARG N 107     -33.517 168.293 333.972  1.00  0.00           C
ATOM   4850  CA  ASP N 108     -32.323 171.580 332.353  1.00  0.00           C
ATOM   4851  CA  LYS N 109     -30.548 169.731 329.537  1.00  0.00           C
ATOM   4852  CA  ASP N 110     -33.643 167.696 328.635  1.00  0.00           C
ATOM   4853  CA  PHE N 111     -32.553 164.296 329.970  1.00  0.00           C
ATOM   4854  CA  MET N 112     -36.130 163.611 331.045  1.00  0.00           C
ATOM   4855  CA  LYS N 113     -36.110 159.804 330.746  1.00  0.00           C
ATOM   4856  CA  ILE N 114     -33.025 159.495 332.951  1.00  0.00           C
ATOM   4857  CA  ILE N 115     -34.572 161.823 335.556  1.00  0.00           C
ATOM   4858  CA  SER N 116     -37.734 159.678 335.562  1.00  0.00           C
ATOM   4859  CA  LEU N 117     -35.789 156.395 335.914  1.00  0.00           C
ATOM   4860  CA  ALA N 118     -33.406 157.657 338.618  1.00  0.00           C
ATOM   4861  CA  PRO N 119     -33.820 156.156 342.135  1.00  0.00           C
ATOM   4862  CA  GLU N 120     -33.467 159.675 343.513  1.00  0.00           C
ATOM   4863  CA  VAL N 121     -32.715 163.135 342.167  1.00  0.00           C
ATOM   4864  CA  ILE N 122     -30.731 165.525 344.401  1.00  0.00           C
TER    4865      ILE N 122
ATOM   4866  CA  PHE O  51      86.139 161.411 279.469  1.00  0.00           C
ATOM   4867  CA  LYS O  52      89.014 162.704 281.563  1.00  0.00           C
ATOM   4868  CA  ARG O  53      92.399 161.069 282.031  1.00  0.00           C
ATOM   4869  CA  PRO O  54      93.800 161.026 285.552  1.00  0.00           C
ATOM   4870  CA  GLN O  55      95.343 164.329 286.587  1.00  0.00           C
ATOM   4871  CA  LYS O  56      98.710 162.701 287.345  1.00  0.00           C
ATOM   4872  CA  VAL O  57      99.085 161.184 283.901  1.00  0.00           C
ATOM   4873  CA  GLN O  58      98.881 164.320 281.846  1.00  0.00           C
ATOM   4874  CA  GLU O  59     102.084 166.084 280.773  1.00  0.00           C
ATOM   4875  CA  GLU O  60     102.327 169.881 280.750  1.00  0.00           C
ATOM   4876  CA  ALA O  61     104.485 171.440 278.037  1.00  0.00           C
ATOM   4877  CA  ALA O  62     103.941 175.452 278.111  1.00  0.00           C
ATOM   4878  CA  THR O  63     103.176 177.699 275.114  1.00  0.00           C
ATOM   4879  CA  ILE O  64     105.023 180.807 273.833  1.00  0.00           C
ATOM   4880  CA  ASP O  65     104.587 182.807 270.628  1.00  0.00           C
ATOM   4881  CA  VAL O  66     107.455 184.317 268.676  1.00  0.00           C
ATOM   4882  CA  ARG O  67     106.068 187.832 269.190  1.00  0.00           C
ATOM   4883  CA  GLU O  68     106.702 188.096 272.925  1.00  0.00           C
ATOM   4884  CA  ILE O  69     110.229 186.768 272.554  1.00  0.00           C
ATOM   4885  CA  ASP O  70     111.351 188.843 269.587  1.00  0.00           C
ATOM   4886  CA  GLU O  71     109.381 191.721 271.089  1.00  0.00           C
ATOM   4887  CA  ASN O  72     111.422 191.620 274.303  1.00  0.00           C
ATOM   4888  CA  VAL O  73     114.794 190.364 273.071  1.00  0.00           C
ATOM   4889  CA  THR O  74     116.754 193.465 274.017  1.00  0.00           C
ATOM   4890  CA  LEU O  75     114.741 193.852 277.216  1.00  0.00           C
ATOM   4891  CA  LEU O  76     115.986 190.374 278.191  1.00  0.00           C
ATOM   4892  CA  ALA O  77     119.425 191.812 278.991  1.00  0.00           C
ATOM   4893  CA  ALA O  78     120.067 188.906 281.379  1.00  0.00           C
ATOM   4894  CA  ASP O  79     119.854 186.415 278.494  1.00  0.00           C
ATOM   4895  CA  ASP O  80     123.060 185.868 276.494  1.00  0.00           C
ATOM   4896  CA  VAL O  81     124.167 187.523 273.236  1.00  0.00           C
ATOM   4897  CA  ALA O  82     126.080 186.451 270.125  1.00  0.00           C
ATOM   4898  CA  GLU O  83     127.053 187.311 266.545  1.00  0.00           C
ATOM   4899  CA  ASP O  92     120.515 186.146 270.820  1.00  0.00           C
ATOM   4900  CA  VAL O  93     119.544 183.142 272.988  1.00  0.00           C
ATOM   4901  CA  ARG O  94     116.719 180.894 274.222  1.00  0.00           C
ATOM   4902  CA  ASP O  95     115.402 179.116 277.346  1.00  0.00           C
ATOM   4903  CA  VAL O  96     113.244 180.079 280.337  1.00  0.00           C
ATOM   4904  CA  ALA O 100     111.986 182.352 281.852  1.00  0.00           C
ATOM   4905  CA  ASP O 101     109.043 184.202 282.533  1.00  0.00           C
ATOM   4906  CA  ASP O 102     105.878 183.512 282.706  1.00  0.00           C
ATOM   4907  CA  ALA O 103     104.490 180.210 282.356  1.00  0.00           C
ATOM   4908  CA  ASP O 104     105.115 176.773 282.763  1.00  0.00           C
ATOM   4909  CA  TYR O 105     106.757 174.314 280.420  1.00  0.00           C
ATOM   4910  CA  VAL O 106     107.896 174.023 276.643  1.00  0.00           C
ATOM   4911  CA  LYS O 107     106.893 174.758 273.055  1.00  0.00           C
ATOM   4912  CA  VAL O 108     107.472 177.772 270.819  1.00  0.00           C
ATOM   4913  CA  LEU O 109     104.723 178.788 268.410  1.00  0.00           C
ATOM   4914  CA  GLY O 110     105.013 180.872 265.272  1.00  0.00           C
ATOM   4915  CA  ALA O 111     102.793 183.956 265.565  1.00  0.00           C
ATOM   4916  CA  GLY O 112     104.012 187.407 264.764  1.00  0.00           C
ATOM   4917  CA  GLN O 113     107.257 188.408 263.093  1.00  0.00           C
ATOM   4918  CA  VAL O 114     110.860 187.573 263.920  1.00  0.00           C
ATOM   4919  CA  ARG O 115     112.851 190.778 263.563  1.00  0.00           C
ATOM   4920  CA  HIS O 116     116.046 189.837 265.381  1.00  0.00           C
ATOM   4921  CA  GLU O 117     118.431 186.960 264.618  1.00  0.00           C
ATOM   4922  CA  LEU O 118     117.390 184.328 267.131  1.00  0.00           C
ATOM   4923  CA  THR O 119     118.623 181.010 268.445  1.00  0.00           C
ATOM   4924  CA  LEU O 120     115.966 179.177 270.422  1.00  0.00           C
ATOM   4925  CA  ILE O 121     115.909 176.028 272.526  1.00  0.00           C
ATOM   4926  CA  ALA O 122     112.717 174.368 273.624  1.00  0.00           C
```

```
ATOM   4927  CA  ASP O 123     111.181 170.923 273.549  1.00  0.00           C
ATOM   4928  CA  ASP O 124     109.293 171.444 270.305  1.00  0.00           C
ATOM   4929  CA  PHE O 125     108.531 173.910 267.528  1.00  0.00           C
ATOM   4930  CA  SER O 126     105.683 174.499 265.108  1.00  0.00           C
ATOM   4931  CA  GLU O 127     106.692 174.482 261.434  1.00  0.00           C
ATOM   4932  CA  GLY O 128     105.537 178.087 261.426  1.00  0.00           C
ATOM   4933  CA  ALA O 129     107.923 179.005 264.239  1.00  0.00           C
ATOM   4934  CA  ARG O 130     110.970 177.303 262.664  1.00  0.00           C
ATOM   4935  CA  GLU O 131     110.445 179.046 259.353  1.00  0.00           C
ATOM   4936  CA  LYS O 132     110.154 182.539 260.781  1.00  0.00           C
ATOM   4937  CA  VAL O 133     113.188 181.957 263.045  1.00  0.00           C
ATOM   4938  CA  GLU O 134     115.298 180.073 260.517  1.00  0.00           C
ATOM   4939  CA  GLY O 135     114.395 182.847 258.080  1.00  0.00           C
ATOM   4940  CA  ALA O 136     116.696 185.006 260.186  1.00  0.00           C
ATOM   4941  CA  GLY O 137     118.957 182.460 261.882  1.00  0.00           C
ATOM   4942  CA  GLY O 138     118.499 180.149 264.892  1.00  0.00           C
ATOM   4943  CA  SER O 139     116.459 176.961 265.464  1.00  0.00           C
ATOM   4944  CA  VAL O 140     117.999 174.432 267.959  1.00  0.00           C
ATOM   4945  CA  GLU O 141     116.172 171.753 269.967  1.00  0.00           C
ATOM   4946  CA  LEU O 142     116.227 170.959 273.714  1.00  0.00           C
ATOM   4947  CA  THR O 143     116.714 167.739 275.712  1.00  0.00           C
ATOM   4948  CA  ASP O 144     113.831 166.181 273.847  1.00  0.00           C
ATOM   4949  CA  LEU O 145     114.489 165.410 270.200  1.00  0.00           C
TER    4950          LEU O 145
ATOM   4951  CA  SER P   9      24.549 181.269 269.626  1.00  0.00           C
ATOM   4952  CA  ILE P  10      25.694 178.494 271.944  1.00  0.00           C
ATOM   4953  CA  LYS P  11      24.245 175.355 270.377  1.00  0.00           C
ATOM   4954  CA  PRO P  12      25.304 173.654 267.097  1.00  0.00           C
ATOM   4955  CA  THR P  15      29.126 173.481 265.909  1.00  0.00           C
ATOM   4956  CA  ARG P  16      30.036 170.663 263.506  1.00  0.00           C
ATOM   4957  CA  ARG P  17      26.559 169.223 262.950  1.00  0.00           C
ATOM   4958  CA  GLU P  18      28.156 166.314 261.101  1.00  0.00           C
ATOM   4959  CA  TYR P  19      29.185 166.757 264.852  1.00  0.00           C
ATOM   4960  CA  ILE P  20      25.818 166.217 266.535  1.00  0.00           C
ATOM   4961  CA  SER P  21      24.369 162.735 266.840  1.00  0.00           C
ATOM   4962  CA  GLY P  22      21.001 161.486 268.047  1.00  0.00           C
ATOM   4963  CA  ILE P  23      18.760 164.344 266.980  1.00  0.00           C
ATOM   4964  CA  PRO P  24      15.048 163.465 267.370  1.00  0.00           C
ATOM   4965  CA  GLY P  25      12.713 163.643 264.397  1.00  0.00           C
ATOM   4966  CA  LYS P  26      10.488 166.624 263.677  1.00  0.00           C
ATOM   4967  CA  GLY P  27       6.867 166.723 264.784  1.00  0.00           C
ATOM   4968  CA  ILE P  28       6.003 169.095 261.950  1.00  0.00           C
ATOM   4969  CA  ALA P  29       3.831 167.136 259.525  1.00  0.00           C
ATOM   4970  CA  GLN P  30       3.843 169.455 256.513  1.00  0.00           C
ATOM   4971  CA  PHE P  31       5.033 172.918 255.520  1.00  0.00           C
ATOM   4972  CA  LYS P  32       2.934 173.241 252.397  1.00  0.00           C
ATOM   4973  CA  MET P  33      -0.799 173.121 253.073  1.00  0.00           C
ATOM   4974  CA  GLY P  34      -3.987 173.670 251.114  1.00  0.00           C
ATOM   4975  CA  ASN P  35      -6.347 175.209 247.154  1.00  0.00           C
ATOM   4976  CA  ASN P  36      -5.282 178.000 244.820  1.00  0.00           C
ATOM   4977  CA  THR P  41      -5.459 181.767 243.930  1.00  0.00           C
ATOM   4978  CA  TYR P  42      -4.166 184.963 243.080  1.00  0.00           C
ATOM   4979  CA  PRO P  43      -4.299 187.103 245.561  1.00  0.00           C
ATOM   4980  CA  ALA P  44      -5.393 188.553 249.665  1.00  0.00           C
ATOM   4981  CA  GLN P  45      -2.273 187.511 251.570  1.00  0.00           C
ATOM   4982  CA  VAL P  46      -2.184 187.591 255.360  1.00  0.00           C
ATOM   4983  CA  GLU P  47       0.892 186.715 257.415  1.00  0.00           C
ATOM   4984  CA  ASN P  48       1.636 185.649 260.985  1.00  0.00           C
ATOM   4985  CA  VAL P  49       4.394 187.987 262.178  1.00  0.00           C
ATOM   4986  CA  VAL P  50       6.292 187.161 265.374  1.00  0.00           C
ATOM   4987  CA  GLU P  51       7.153 190.208 267.493  1.00  0.00           C
ATOM   4988  CA  LYS P  52      10.124 188.923 269.525  1.00  0.00           C
ATOM   4989  CA  PRO P  53      13.254 186.884 268.716  1.00  0.00           C
ATOM   4990  CA  VAL P  54      12.692 183.503 270.291  1.00  0.00           C
ATOM   4991  CA  GLN P  55      13.106 179.809 269.708  1.00  0.00           C
ATOM   4992  CA  ILE P  56      10.085 177.707 268.851  1.00  0.00           C
ATOM   4993  CA  ARG P  57      10.399 173.947 269.357  1.00  0.00           C
ATOM   4994  CA  HIS P  58       8.888 171.744 266.647  1.00  0.00           C
ATOM   4995  CA  ASN P  59       6.815 170.804 269.681  1.00  0.00           C
ATOM   4996  CA  ALA P  60       5.079 174.158 269.305  1.00  0.00           C
ATOM   4997  CA  LEU P  61       5.448 174.583 265.534  1.00  0.00           C
ATOM   4998  CA  GLU P  62       3.200 171.609 264.940  1.00  0.00           C
ATOM   4999  CA  ALA P  63       0.090 172.007 267.114  1.00  0.00           C
ATOM   5000  CA  ALA P  64       0.371 175.746 266.505  1.00  0.00           C
ATOM   5001  CA  ARG P  65       0.209 175.093 262.788  1.00  0.00           C
ATOM   5002  CA  ASN P  66      -2.012 172.078 263.225  1.00  0.00           C
ATOM   5003  CA  ALA P  67      -4.452 174.239 265.182  1.00  0.00           C
ATOM   5004  CA  ALA P  68      -4.322 176.617 262.221  1.00  0.00           C
ATOM   5005  CA  ASN P  69      -5.021 174.155 259.433  1.00  0.00           C
ATOM   5006  CA  ARG P  70      -7.736 172.470 261.497  1.00  0.00           C
ATOM   5007  CA  PHE P  71      -9.843 175.612 261.592  1.00  0.00           C
ATOM   5008  CA  VAL P  72      -8.885 176.497 258.034  1.00  0.00           C
ATOM   5009  CA  GLN P  73     -11.143 173.552 256.735  1.00  0.00           C
ATOM   5010  CA  ASN P  74     -10.763 175.614 253.905  1.00  0.00           C
ATOM   5011  CA  SER P  75      -9.471 177.696 251.024  1.00  0.00           C
ATOM   5012  CA  GLY P  76      -5.874 176.679 251.604  1.00  0.00           C
ATOM   5013  CA  LYS P  82      -2.605 177.495 250.946  1.00  0.00           C
```

```
ATOM   5014  CA  PHE P   83    -0.742 177.576 253.868  1.00  0.00           C
ATOM   5015  CA  ARG P   84     3.028 177.890 254.240  1.00  0.00           C
ATOM   5016  CA  ILE P   85     5.178 177.794 257.369  1.00  0.00           C
ATOM   5017  CA  ARG P   86     8.489 179.408 256.423  1.00  0.00           C
ATOM   5018  CA  LYS P   87    10.797 178.309 259.255  1.00  0.00           C
ATOM   5019  CA  PHE P   88    12.402 174.918 259.929  1.00  0.00           C
ATOM   5020  CA  PRO P   89    13.766 173.580 263.273  1.00  0.00           C
ATOM   5021  CA  PHE P   90    17.539 173.727 262.793  1.00  0.00           C
ATOM   5022  CA  HIS P   91    18.612 174.493 266.311  1.00  0.00           C
ATOM   5023  CA  VAL P   92    19.396 171.381 268.331  1.00  0.00           C
ATOM   5024  CA  ILE P   93    18.661 171.697 272.048  1.00  0.00           C
ATOM   5025  CA  ARG P   94    20.111 169.768 275.032  1.00  0.00           C
ATOM   5026  CA  GLU P   95    19.367 168.989 278.701  1.00  0.00           C
ATOM   5027  CA  GLN P   96    20.710 167.869 282.104  1.00  0.00           C
ATOM   5028  CA  ASP P   97    23.517 165.415 281.269  1.00  0.00           C
ATOM   5029  CA  GLY P   98    25.146 166.190 284.614  1.00  0.00           C
ATOM   5030  CA  ASP P   99    25.507 163.739 287.520  1.00  0.00           C
ATOM   5031  CA  GLY P  100    25.087 167.072 289.249  1.00  0.00           C
ATOM   5032  CA  MET P  101    26.868 169.866 287.407  1.00  0.00           C
ATOM   5033  CA  ARG P  102    29.772 167.646 286.447  1.00  0.00           C
ATOM   5034  CA  ALA P  103    30.270 166.858 282.770  1.00  0.00           C
ATOM   5035  CA  PRO P  104    26.908 168.450 281.874  1.00  0.00           C
ATOM   5036  CA  PHE P  105    26.548 169.521 278.269  1.00  0.00           C
ATOM   5037  CA  GLY P  106    23.088 168.059 277.863  1.00  0.00           C
ATOM   5038  CA  LYS P  107    21.977 165.081 275.839  1.00  0.00           C
ATOM   5039  CA  SER P  108    20.188 165.822 272.561  1.00  0.00           C
ATOM   5040  CA  VAL P  109    16.465 166.113 273.234  1.00  0.00           C
ATOM   5041  CA  GLY P  110    14.955 168.295 270.526  1.00  0.00           C
ATOM   5042  CA  THR P  111    15.005 171.011 267.876  1.00  0.00           C
ATOM   5043  CA  ALA P  112    13.856 174.626 267.485  1.00  0.00           C
ATOM   5044  CA  ALA P  113    13.479 177.300 264.804  1.00  0.00           C
ATOM   5045  CA  ARG P  114    14.562 180.793 265.943  1.00  0.00           C
ATOM   5046  CA  SER P  115    12.824 183.914 264.645  1.00  0.00           C
ATOM   5047  CA  HIS P  116    13.296 187.651 265.045  1.00  0.00           C
ATOM   5048  CA  GLY P  117    11.511 190.935 265.567  1.00  0.00           C
ATOM   5049  CA  ALA P  118     9.423 190.680 262.410  1.00  0.00           C
ATOM   5050  CA  ASN P  119     9.957 187.424 260.538  1.00  0.00           C
ATOM   5051  CA  HIS P  120     6.701 186.236 259.017  1.00  0.00           C
ATOM   5052  CA  ASP P  121     6.271 182.755 260.467  1.00  0.00           C
ATOM   5053  CA  PHE P  122     3.094 181.747 258.620  1.00  0.00           C
ATOM   5054  CA  ILE P  123     1.871 182.980 255.243  1.00  0.00           C
ATOM   5055  CA  ALA P  124    -1.616 182.298 253.933  1.00  0.00           C
ATOM   5056  CA  TRP P  125    -3.183 183.097 250.571  1.00  0.00           C
ATOM   5057  CA  VAL P  126    -6.904 183.450 249.958  1.00  0.00           C
ATOM   5058  CA  ASN P  127    -9.767 185.336 248.309  1.00  0.00           C
ATOM   5059  CA  PRO P  128   -12.064 187.453 250.537  1.00  0.00           C
ATOM   5060  CA  ASP P  129   -12.498 184.543 252.934  1.00  0.00           C
ATOM   5061  CA  PRO P  130   -10.497 185.671 256.047  1.00  0.00           C
ATOM   5062  CA  ALA P  131   -11.528 182.899 258.404  1.00  0.00           C
ATOM   5063  CA  VAL P  132    -7.768 182.439 258.285  1.00  0.00           C
ATOM   5064  CA  GLU P  133    -7.360 185.692 260.187  1.00  0.00           C
ATOM   5065  CA  PHE P  134    -8.933 183.593 262.934  1.00  0.00           C
ATOM   5066  CA  ALA P  135    -6.908 180.518 262.003  1.00  0.00           C
ATOM   5067  CA  TRP P  136    -4.099 182.544 263.509  1.00  0.00           C
ATOM   5068  CA  ARG P  137    -5.804 183.874 266.585  1.00  0.00           C
ATOM   5069  CA  ARG P  138    -5.350 180.182 267.352  1.00  0.00           C
ATOM   5070  CA  ALA P  139    -1.891 180.005 265.787  1.00  0.00           C
ATOM   5071  CA  TYR P  140    -0.407 182.767 267.907  1.00  0.00           C
ATOM   5072  CA  MET P  141    -1.618 181.087 271.061  1.00  0.00           C
ATOM   5073  CA  LYS P  142     0.495 177.959 271.167  1.00  0.00           C
ATOM   5074  CA  VAL P  143     3.705 179.857 270.510  1.00  0.00           C
ATOM   5075  CA  THR P  144     5.642 181.844 273.110  1.00  0.00           C
ATOM   5076  CA  PRO P  145     5.600 185.160 271.176  1.00  0.00           C
ATOM   5077  CA  THR P  146     2.967 187.851 271.049  1.00  0.00           C
ATOM   5078  CA  VAL P  147     2.263 187.751 267.336  1.00  0.00           C
ATOM   5079  CA  ASN P  148     1.227 190.247 264.657  1.00  0.00           C
ATOM   5080  CA  ILE P  149    -1.495 189.318 262.144  1.00  0.00           C
ATOM   5081  CA  ASP P  150    -0.351 191.362 259.155  1.00  0.00           C
ATOM   5082  CA  SER P  151    -2.603 191.767 256.134  1.00  0.00           C
ATOM   5083  CA  SER P  152    -0.738 192.220 252.861  1.00  0.00           C
ATOM   5084  CA  PRO P  153    -2.234 192.431 249.320  1.00  0.00           C
ATOM   5085  CA  ALA P  154    -5.761 193.298 250.476  1.00  0.00           C
ATOM   5086  CA  GLY P  155    -7.237 196.764 250.104  1.00  0.00           C
ATOM   5087  CA  ASN P  156   -10.407 194.782 249.537  1.00  0.00           C
ATOM   5088  CA  ALA P  157   -11.150 195.109 253.246  1.00  0.00           C
TER    5089      ALA P  157
ATOM   5090  CA  PRO Q    9    44.924 171.369 234.405  1.00  0.00           C
ATOM   5091  CA  MET Q   10    47.399 173.893 233.041  1.00  0.00           C
ATOM   5092  CA  ARG Q   11    46.484 175.145 229.571  1.00  0.00           C
ATOM   5093  CA  ARG Q   12    49.471 173.465 227.942  1.00  0.00           C
ATOM   5094  CA  ARG Q   13    48.356 170.183 229.496  1.00  0.00           C
ATOM   5095  CA  ARG Q   14    44.762 170.260 228.289  1.00  0.00           C
ATOM   5096  CA  GLU Q   15    46.092 170.855 224.792  1.00  0.00           C
ATOM   5097  CA  ALA Q   16    48.321 167.824 225.280  1.00  0.00           C
ATOM   5098  CA  ARG Q   17    51.355 169.772 224.128  1.00  0.00           C
ATOM   5099  CA  THR Q   18    53.643 169.991 227.139  1.00  0.00           C
ATOM   5100  CA  ASP Q   19    54.882 167.206 229.391  1.00  0.00           C
```

```
ATOM   5101  CA  TYR Q  20      55.718 173.495 230.409  1.00  0.00           C
ATOM   5102  CA  HIS Q  21      57.009 170.507 232.350  1.00  0.00           C
ATOM   5103  CA  GLN Q  22      59.955 170.080 230.016  1.00  0.00           C
ATOM   5104  CA  ARG Q  23      60.323 173.849 229.826  1.00  0.00           C
ATOM   5105  CA  LEU Q  24      60.969 174.265 233.533  1.00  0.00           C
ATOM   5106  CA  ARG Q  25      63.653 171.578 233.612  1.00  0.00           C
ATOM   5107  CA  LEU Q  26      65.131 173.420 230.650  1.00  0.00           C
ATOM   5108  CA  LEU Q  27      65.160 176.833 232.312  1.00  0.00           C
ATOM   5109  CA  LYS Q  28      67.005 175.302 235.272  1.00  0.00           C
ATOM   5110  CA  SER Q  29      70.328 175.244 233.427  1.00  0.00           C
ATOM   5111  CA  GLY Q  30      72.192 173.195 232.066  1.00  0.00           C
ATOM   5112  CA  LYS Q  31      71.441 174.904 229.244  1.00  0.00           C
ATOM   5113  CA  PRO Q  32      69.361 175.679 226.115  1.00  0.00           C
ATOM   5114  CA  ARG Q  33      66.959 173.115 224.706  1.00  0.00           C
ATOM   5115  CA  LEU Q  34      67.084 171.763 221.168  1.00  0.00           C
ATOM   5116  CA  VAL Q  35      63.379 171.458 220.443  1.00  0.00           C
ATOM   5117  CA  ALA Q  36      62.735 168.804 217.807  1.00  0.00           C
ATOM   5118  CA  ARG Q  37      59.136 168.863 216.598  1.00  0.00           C
ATOM   5119  CA  LYS Q  38      57.669 166.841 213.739  1.00  0.00           C
ATOM   5120  CA  SER Q  39      54.832 167.492 211.320  1.00  0.00           C
ATOM   5121  CA  ASN Q  40      53.195 165.415 208.599  1.00  0.00           C
ATOM   5122  CA  LYS Q  41      54.999 167.372 205.894  1.00  0.00           C
ATOM   5123  CA  HIS Q  42      57.742 169.167 207.817  1.00  0.00           C
ATOM   5124  CA  VAL Q  43      60.319 169.273 210.593  1.00  0.00           C
ATOM   5125  CA  ARG Q  44      61.044 171.993 213.158  1.00  0.00           C
ATOM   5126  CA  ALA Q  45      64.226 172.696 215.135  1.00  0.00           C
ATOM   5127  CA  GLN Q  46      64.370 175.467 217.730  1.00  0.00           C
ATOM   5128  CA  LEU Q  47      66.911 176.358 220.397  1.00  0.00           C
ATOM   5129  CA  VAL Q  48      65.096 177.721 223.427  1.00  0.00           C
ATOM   5130  CA  THR Q  49      66.245 179.691 225.804  1.00  0.00           C
ATOM   5131  CA  PRO Q  52      63.756 181.891 226.639  1.00  0.00           C
ATOM   5132  CA  ASN Q  53      62.895 184.446 228.256  1.00  0.00           C
ATOM   5133  CA  GLY Q  54      60.987 185.312 226.497  1.00  0.00           C
ATOM   5134  CA  ASP Q  55      61.117 184.019 222.947  1.00  0.00           C
ATOM   5135  CA  ASP Q  56      63.742 183.952 220.758  1.00  0.00           C
ATOM   5136  CA  THR Q  57      62.700 182.134 217.606  1.00  0.00           C
ATOM   5137  CA  LEU Q  58      65.288 182.228 214.818  1.00  0.00           C
ATOM   5138  CA  ALA Q  59      63.647 180.021 212.207  1.00  0.00           C
ATOM   5139  CA  SER Q  60      65.139 178.818 211.296  1.00  0.00           C
ATOM   5140  CA  ALA Q  61      65.236 176.077 211.143  1.00  0.00           C
ATOM   5141  CA  HIS Q  62      62.128 174.806 209.386  1.00  0.00           C
ATOM   5142  CA  SER Q  63      62.663 172.229 206.637  1.00  0.00           C
ATOM   5143  CA  SER Q  64      60.352 174.329 204.449  1.00  0.00           C
ATOM   5144  CA  ASP Q  65      62.923 177.125 204.200  1.00  0.00           C
ATOM   5145  CA  LEU Q  66      65.472 174.445 203.360  1.00  0.00           C
ATOM   5146  CA  ALA Q  67      64.312 173.752 200.383  1.00  0.00           C
ATOM   5147  CA  GLU Q  68      63.629 170.328 200.318  1.00  0.00           C
ATOM   5148  CA  TYR Q  69      65.641 168.641 198.042  1.00  0.00           C
ATOM   5149  CA  GLY Q  70      63.326 165.654 197.753  1.00  0.00           C
ATOM   5150  CA  TRP Q  71      64.576 163.251 200.404  1.00  0.00           C
ATOM   5151  CA  GLU Q  72      62.246 160.816 201.887  1.00  0.00           C
ATOM   5152  CA  PRO Q  74      62.165 162.142 204.761  1.00  0.00           C
ATOM   5153  CA  THR Q  75      65.513 161.385 206.358  1.00  0.00           C
ATOM   5154  CA  GLY Q  76      67.492 164.164 204.717  1.00  0.00           C
ATOM   5155  CA  SER Q  80      65.482 166.309 205.344  1.00  0.00           C
ATOM   5156  CA  ALA Q  81      65.208 166.298 209.143  1.00  0.00           C
ATOM   5157  CA  TYR Q  82      68.973 165.961 209.546  1.00  0.00           C
ATOM   5158  CA  LEU Q  83      69.644 168.946 207.308  1.00  0.00           C
ATOM   5159  CA  THR Q  84      67.154 170.941 209.353  1.00  0.00           C
ATOM   5160  CA  GLY Q  85      68.962 170.151 212.575  1.00  0.00           C
ATOM   5161  CA  LEU Q  86      72.266 171.057 210.975  1.00  0.00           C
ATOM   5162  CA  LEU Q  87      70.867 174.296 209.567  1.00  0.00           C
ATOM   5163  CA  ALA Q  88      69.587 175.296 212.991  1.00  0.00           C
ATOM   5164  CA  GLY Q  89      72.827 174.173 214.582  1.00  0.00           C
ATOM   5165  CA  LEU Q  90      74.718 176.599 212.379  1.00  0.00           C
ATOM   5166  CA  ARG Q  91      72.451 179.548 213.117  1.00  0.00           C
ATOM   5167  CA  ALA Q  92      72.830 178.471 216.726  1.00  0.00           C
ATOM   5168  CA  GLN Q  93      76.580 178.920 216.501  1.00  0.00           C
ATOM   5169  CA  GLU Q  94      76.094 182.399 215.066  1.00  0.00           C
ATOM   5170  CA  ALA Q  95      73.893 183.385 217.994  1.00  0.00           C
ATOM   5171  CA  GLY Q  96      76.638 182.425 220.423  1.00  0.00           C
ATOM   5172  CA  VAL Q  97      75.223 179.068 221.477  1.00  0.00           C
ATOM   5173  CA  GLU Q  98      77.576 176.141 222.089  1.00  0.00           C
ATOM   5174  CA  GLU Q  99      75.517 173.396 223.703  1.00  0.00           C
ATOM   5175  CA  ALA Q 100      72.005 172.236 224.517  1.00  0.00           C
ATOM   5176  CA  VAL Q 101      69.856 169.321 225.662  1.00  0.00           C
ATOM   5177  CA  LEU Q 102      67.514 167.412 223.361  1.00  0.00           C
ATOM   5178  CA  ASP Q 103      63.799 168.102 223.781  1.00  0.00           C
ATOM   5179  CA  ILE Q 104      61.760 165.612 221.745  1.00  0.00           C
ATOM   5180  CA  GLY Q 105      58.533 166.660 223.430  1.00  0.00           C
ATOM   5181  CA  LEU Q 106      55.778 164.067 223.187  1.00  0.00           C
ATOM   5182  CA  ASN Q 107      54.946 161.144 221.907  1.00  0.00           C
ATOM   5183  CA  SER Q 108      57.429 158.758 220.314  1.00  0.00           C
ATOM   5184  CA  PRO Q 109      60.919 159.444 218.853  1.00  0.00           C
ATOM   5185  CA  THR Q 110      60.117 158.266 215.336  1.00  0.00           C
ATOM   5186  CA  PRO Q 111      62.539 159.265 212.589  1.00  0.00           C
ATOM   5187  CA  LYS Q 114      63.929 161.843 212.940  1.00  0.00           C
```

```
ATOM   5188  CA  VAL Q 115      64.105 163.492 216.357  1.00  0.00           C
ATOM   5189  CA  PHE Q 116      67.541 161.922 216.656  1.00  0.00           C
ATOM   5190  CA  ALA Q 117      68.505 162.830 213.110  1.00  0.00           C
ATOM   5191  CA  ILE Q 118      67.636 166.412 214.012  1.00  0.00           C
ATOM   5192  CA  GLN Q 119      70.032 165.961 216.897  1.00  0.00           C
ATOM   5193  CA  GLU Q 120      72.829 164.513 214.770  1.00  0.00           C
ATOM   5194  CA  GLY Q 121      72.895 167.345 212.257  1.00  0.00           C
ATOM   5195  CA  ALA Q 122      72.834 169.724 215.205  1.00  0.00           C
ATOM   5196  CA  ILE Q 123      75.970 168.170 216.674  1.00  0.00           C
ATOM   5197  CA  ASP Q 124      77.800 168.161 213.350  1.00  0.00           C
ATOM   5198  CA  ALA Q 125      77.092 171.889 213.331  1.00  0.00           C
ATOM   5199  CA  GLY Q 126      79.548 172.103 216.214  1.00  0.00           C
ATOM   5200  CA  LEU Q 127      76.929 172.038 218.956  1.00  0.00           C
ATOM   5201  CA  ASP Q 128      77.817 169.914 221.997  1.00  0.00           C
ATOM   5202  CA  ILE Q 129      74.734 167.924 222.981  1.00  0.00           C
TER    5203          ILE Q 129
ATOM   5204  CA  ARG R   4     -28.549 168.308 358.412  1.00  0.00           C
ATOM   5205  CA  GLU R   5     -26.698 165.770 360.509  1.00  0.00           C
ATOM   5206  CA  CYS R   6     -23.816 163.922 358.947  1.00  0.00           C
ATOM   5207  CA  ASP R   7     -25.106 160.525 357.910  1.00  0.00           C
ATOM   5208  CA  TYR R   8     -22.149 158.699 359.446  1.00  0.00           C
ATOM   5209  CA  CYS R   9     -20.512 160.626 362.277  1.00  0.00           C
ATOM   5210  CA  GLY R  10     -23.657 162.344 363.538  1.00  0.00           C
ATOM   5211  CA  THR R  11     -22.487 165.910 364.164  1.00  0.00           C
ATOM   5212  CA  ASP R  12     -24.294 168.761 362.431  1.00  0.00           C
ATOM   5213  CA  ILE R  13     -23.139 169.781 358.964  1.00  0.00           C
ATOM   5214  CA  GLU R  14     -22.146 173.438 358.872  1.00  0.00           C
ATOM   5215  CA  PRO R  15     -24.420 174.999 356.242  1.00  0.00           C
ATOM   5216  CA  GLY R  16     -22.808 175.761 352.904  1.00  0.00           C
ATOM   5217  CA  THR R  17     -20.443 172.960 353.843  1.00  0.00           C
ATOM   5218  CA  GLY R  18     -21.337 169.419 353.447  1.00  0.00           C
ATOM   5219  CA  THR R  19     -21.742 167.007 350.572  1.00  0.00           C
ATOM   5220  CA  MET R  20     -23.958 163.673 349.293  1.00  0.00           C
ATOM   5221  CA  PHE R  21     -22.266 160.694 347.704  1.00  0.00           C
ATOM   5222  CA  VAL R  22     -24.450 158.090 345.993  1.00  0.00           C
ATOM   5223  CA  HIS R  23     -22.979 154.579 345.959  1.00  0.00           C
ATOM   5224  CA  LYS R  24     -24.002 153.033 342.608  1.00  0.00           C
ATOM   5225  CA  ASP R  25     -26.375 150.603 344.307  1.00  0.00           C
ATOM   5226  CA  GLY R  26     -28.268 153.724 345.256  1.00  0.00           C
ATOM   5227  CA  ALA R  27     -26.639 153.822 348.673  1.00  0.00           C
ATOM   5228  CA  THR R  28     -26.108 157.284 350.087  1.00  0.00           C
ATOM   5229  CA  THR R  29     -23.360 158.718 352.277  1.00  0.00           C
ATOM   5230  CA  HIS R  30     -23.659 162.184 353.804  1.00  0.00           C
ATOM   5231  CA  PHE R  31     -20.270 163.754 354.517  1.00  0.00           C
ATOM   5232  CA  CYS R  32     -19.763 166.759 356.768  1.00  0.00           C
ATOM   5233  CA  SER R  33     -16.094 166.203 355.928  1.00  0.00           C
ATOM   5234  CA  SER R  34     -13.475 164.326 353.931  1.00  0.00           C
ATOM   5235  CA  LYS R  35     -12.403 162.594 357.134  1.00  0.00           C
ATOM   5236  CA  CYS R  36     -15.752 160.853 357.419  1.00  0.00           C
ATOM   5237  CA  GLU R  37     -15.998 159.940 353.718  1.00  0.00           C
ATOM   5238  CA  ASN R  38     -12.553 158.339 353.820  1.00  0.00           C
ATOM   5239  CA  ASN R  39     -13.351 156.389 356.950  1.00  0.00           C
ATOM   5240  CA  ALA R  40     -16.489 155.174 355.226  1.00  0.00           C
ATOM   5241  CA  ASP R  41     -14.504 154.179 352.117  1.00  0.00           C
ATOM   5242  CA  LEU R  42     -12.325 151.990 354.310  1.00  0.00           C
ATOM   5243  CA  ARG R  44     -15.409 151.278 358.786  1.00  0.00           C
ATOM   5244  CA  GLU R  45     -18.743 151.879 360.513  1.00  0.00           C
ATOM   5245  CA  ALA R  46     -19.069 155.095 362.510  1.00  0.00           C
ATOM   5246  CA  ARG R  47     -20.533 153.192 365.448  1.00  0.00           C
ATOM   5247  CA  ASN R  48     -17.130 151.600 366.048  1.00  0.00           C
ATOM   5248  CA  LEU R  49     -15.327 154.956 366.076  1.00  0.00           C
ATOM   5249  CA  GLU R  50     -14.980 156.578 369.485  1.00  0.00           C
ATOM   5250  CA  TRP R  51     -14.748 160.140 368.145  1.00  0.00           C
ATOM   5251  CA  THR R  52     -18.059 159.714 366.363  1.00  0.00           C
ATOM   5252  CA  ASP R  53     -21.107 161.398 367.856  1.00  0.00           C
ATOM   5253  CA  THR R  54     -22.847 158.254 366.629  1.00  0.00           C
ATOM   5254  CA  ALA R  55     -20.699 155.847 368.688  1.00  0.00           C
ATOM   5255  CA  ARG R  56     -20.821 158.265 371.611  1.00  0.00           C
TER    5256          ARG R  56
ATOM   5257  CA  MET S   1      46.946 231.411 354.196  1.00  0.00           C
ATOM   5258  CA  GLU S   2      46.332 227.380 354.333  1.00  0.00           C
ATOM   5259  CA  ALA S   3      47.554 224.319 356.227  1.00  0.00           C
ATOM   5260  CA  LYS S   4      47.979 220.806 354.836  1.00  0.00           C
ATOM   5261  CA  ALA S   5      48.309 217.262 356.213  1.00  0.00           C
ATOM   5262  CA  ILE S   6      48.673 213.900 354.493  1.00  0.00           C
ATOM   5263  CA  ALA S   7      48.230 210.304 355.561  1.00  0.00           C
ATOM   5264  CA  ARG S   8      49.927 207.644 353.439  1.00  0.00           C
ATOM   5265  CA  TYR S   9      49.454 203.904 352.980  1.00  0.00           C
ATOM   5266  CA  VAL S  10      46.034 203.793 354.631  1.00  0.00           C
ATOM   5267  CA  ARG S  11      44.803 200.203 354.363  1.00  0.00           C
ATOM   5268  CA  ILE S  12      41.367 201.017 352.954  1.00  0.00           C
ATOM   5269  CA  SER S  13      40.461 201.106 349.289  1.00  0.00           C
ATOM   5270  CA  PRO S  14      40.379 204.646 347.782  1.00  0.00           C
ATOM   5271  CA  ARG S  15      36.703 204.380 346.848  1.00  0.00           C
ATOM   5272  CA  LYS S  16      35.500 203.898 350.408  1.00  0.00           C
ATOM   5273  CA  VAL S  17      37.635 206.751 351.798  1.00  0.00           C
ATOM   5274  CA  ARG S  18      36.501 209.101 349.010  1.00  0.00           C
```

```
ATOM   5275  CA  LEU S  19      32.927 208.614 350.186  1.00  0.00           C
ATOM   5276  CA  VAL S  20      34.101 209.937 353.536  1.00  0.00           C
ATOM   5277  CA  VAL S  21      36.106 213.001 352.390  1.00  0.00           C
ATOM   5278  CA  ASP S  22      33.105 213.882 350.189  1.00  0.00           C
ATOM   5279  CA  LEU S  23      31.091 214.567 353.351  1.00  0.00           C
ATOM   5280  CA  ILE S  24      33.534 217.131 354.734  1.00  0.00           C
ATOM   5281  CA  ARG S  25      34.702 219.017 351.617  1.00  0.00           C
ATOM   5282  CA  GLY S  26      34.018 222.721 352.081  1.00  0.00           C
ATOM   5283  CA  LYS S  27      32.705 222.417 355.643  1.00  0.00           C
ATOM   5284  CA  SER S  28      33.942 224.433 358.595  1.00  0.00           C
ATOM   5285  CA  LEU S  29      36.353 222.592 360.903  1.00  0.00           C
ATOM   5286  CA  GLU S  30      33.728 222.239 363.634  1.00  0.00           C
ATOM   5287  CA  GLU S  31      31.172 220.843 361.183  1.00  0.00           C
ATOM   5288  CA  ALA S  32      33.674 218.419 359.625  1.00  0.00           C
ATOM   5289  CA  ARG S  33      34.635 217.130 363.090  1.00  0.00           C
ATOM   5290  CA  ASN S  34      31.046 216.305 363.931  1.00  0.00           C
ATOM   5291  CA  ILE S  35      30.272 214.632 360.616  1.00  0.00           C
ATOM   5292  CA  LEU S  36      33.333 212.428 361.085  1.00  0.00           C
ATOM   5293  CA  ARG S  37      32.429 211.647 364.665  1.00  0.00           C
ATOM   5294  CA  TYR S  38      28.908 210.455 363.842  1.00  0.00           C
ATOM   5295  CA  THR S  39      29.338 208.962 360.388  1.00  0.00           C
ATOM   5296  CA  ASN S  40      28.760 205.232 359.951  1.00  0.00           C
ATOM   5297  CA  LYS S  41      31.107 205.005 356.968  1.00  0.00           C
ATOM   5298  CA  ARG S  42      34.230 202.898 357.177  1.00  0.00           C
ATOM   5299  CA  GLY S  43      37.467 204.853 357.273  1.00  0.00           C
ATOM   5300  CA  ALA S  44      36.068 207.856 359.132  1.00  0.00           C
ATOM   5301  CA  TYR S  45      38.675 207.534 361.869  1.00  0.00           C
ATOM   5302  CA  PHE S  46      41.548 207.901 359.381  1.00  0.00           C
ATOM   5303  CA  VAL S  47      40.100 211.045 357.797  1.00  0.00           C
ATOM   5304  CA  ALA S  48      39.432 212.451 361.305  1.00  0.00           C
ATOM   5305  CA  LYS S  49      43.104 211.863 362.210  1.00  0.00           C
ATOM   5306  CA  VAL S  50      44.306 213.683 359.082  1.00  0.00           C
ATOM   5307  CA  LEU S  51      41.800 216.494 359.817  1.00  0.00           C
ATOM   5308  CA  GLU S  52      43.201 217.030 363.321  1.00  0.00           C
ATOM   5309  CA  SER S  53      46.768 216.909 361.983  1.00  0.00           C
ATOM   5310  CA  ALA S  54      45.909 219.676 359.507  1.00  0.00           C
ATOM   5311  CA  ALA S  55      44.285 221.689 362.350  1.00  0.00           C
ATOM   5312  CA  ALA S  56      47.416 221.277 364.522  1.00  0.00           C
ATOM   5313  CA  ASN S  57      49.528 222.492 361.559  1.00  0.00           C
ATOM   5314  CA  ALA S  58      47.262 225.511 360.965  1.00  0.00           C
ATOM   5315  CA  VAL S  59      46.906 226.567 364.607  1.00  0.00           C
ATOM   5316  CA  ASN S  60      50.285 225.682 366.074  1.00  0.00           C
ATOM   5317  CA  ASN S  61      52.652 226.026 363.115  1.00  0.00           C
ATOM   5318  CA  HIS S  62      50.896 228.742 361.134  1.00  0.00           C
ATOM   5319  CA  ASP S  63      49.210 230.659 363.955  1.00  0.00           C
ATOM   5320  CA  MET S  64      45.775 230.852 362.131  1.00  0.00           C
ATOM   5321  CA  LEU S  65      42.718 231.151 364.289  1.00  0.00           C
ATOM   5322  CA  GLU S  66      40.925 227.855 364.827  1.00  0.00           C
ATOM   5323  CA  ASP S  67      37.487 229.472 364.566  1.00  0.00           C
ATOM   5324  CA  ARG S  68      38.127 230.559 360.971  1.00  0.00           C
ATOM   5325  CA  LEU S  69      39.190 227.208 359.565  1.00  0.00           C
ATOM   5326  CA  TYR S  70      37.195 225.321 356.970  1.00  0.00           C
ATOM   5327  CA  VAL S  71      38.022 222.342 354.757  1.00  0.00           C
ATOM   5328  CA  LYS S  72      39.291 224.043 351.596  1.00  0.00           C
ATOM   5329  CA  ALA S  73      40.307 220.745 349.955  1.00  0.00           C
ATOM   5330  CA  ALA S  74      40.003 217.095 350.917  1.00  0.00           C
ATOM   5331  CA  TYR S  75      40.799 214.282 348.502  1.00  0.00           C
ATOM   5332  CA  VAL S  76      42.050 210.740 348.141  1.00  0.00           C
ATOM   5333  CA  ASP S  77      44.741 209.561 345.722  1.00  0.00           C
ATOM   5334  CA  GLU S  78      45.454 205.936 344.880  1.00  0.00           C
ATOM   5335  CA  GLY S  79      48.516 204.785 346.842  1.00  0.00           C
ATOM   5336  CA  PRO S  80      50.765 202.360 346.391  1.00  0.00           C
ATOM   5337  CA  ALA S  81      49.030 198.998 346.669  1.00  0.00           C
ATOM   5338  CA  LEU S  82      50.601 195.703 347.674  1.00  0.00           C
ATOM   5339  CA  LYS S  83      49.513 192.790 345.447  1.00  0.00           C
ATOM   5340  CA  ARG S  84      49.087 189.853 347.875  1.00  0.00           C
ATOM   5341  CA  VAL S  85      49.315 186.468 346.148  1.00  0.00           C
ATOM   5342  CA  LEU S  86      46.785 183.855 347.273  1.00  0.00           C
ATOM   5343  CA  PRO S  87      46.813 180.122 346.547  1.00  0.00           C
ATOM   5344  CA  ARG S  88      45.603 179.078 343.093  1.00  0.00           C
ATOM   5345  CA  ALA S  89      41.826 178.865 342.978  1.00  0.00           C
ATOM   5346  CA  ARG S  90      40.185 176.444 340.546  1.00  0.00           C
ATOM   5347  CA  GLY S  91      43.216 176.705 338.304  1.00  0.00           C
ATOM   5348  CA  ARG S  92      43.349 180.481 338.386  1.00  0.00           C
ATOM   5349  CA  ALA S  93      45.522 183.250 339.815  1.00  0.00           C
ATOM   5350  CA  ASP S  94      44.078 184.805 342.957  1.00  0.00           C
ATOM   5351  CA  ILE S  95      45.519 188.304 343.628  1.00  0.00           C
ATOM   5352  CA  ILE S  96      44.136 190.892 346.041  1.00  0.00           C
ATOM   5353  CA  LYS S  97      45.307 194.506 346.357  1.00  0.00           C
ATOM   5354  CA  LYS S  98      46.095 195.815 349.794  1.00  0.00           C
ATOM   5355  CA  ARG S  99      46.362 199.610 349.895  1.00  0.00           C
ATOM   5356  CA  THR S 100      46.606 202.839 350.414  1.00  0.00           C
ATOM   5357  CA  SER S 101      44.836 205.287 350.130  1.00  0.00           C
ATOM   5358  CA  HIS S 102      46.721 208.550 350.171  1.00  0.00           C
ATOM   5359  CA  ILE S 103      44.638 211.132 352.060  1.00  0.00           C
ATOM   5360  CA  THR S 104      45.066 214.908 351.854  1.00  0.00           C
ATOM   5361  CA  VAL S 105      43.215 217.553 353.839  1.00  0.00           C
```

```
ATOM   5362  CA  ILE S 106      43.871 221.272 353.385  1.00  0.00           C
ATOM   5363  CA  LEU S 107      42.509 223.834 355.814  1.00  0.00           C
ATOM   5364  CA  GLY S 108      42.070 227.471 354.817  1.00  0.00           C
ATOM   5365  CA  GLU S 109      40.573 230.648 356.325  1.00  0.00           C
ATOM   5366  CA  LYS S 110      37.071 231.623 355.346  1.00  0.00           C
TER    5367          LYS S 110
ATOM   5368  CA  SER T   1      90.505 164.084 369.282  1.00  0.00           C
ATOM   5369  CA  TRP T   2      86.853 164.827 370.167  1.00  0.00           C
ATOM   5370  CA  ASP T   3      85.879 165.596 373.778  1.00  0.00           C
ATOM   5371  CA  VAL T   4      82.984 164.044 375.696  1.00  0.00           C
ATOM   5372  CA  ILE T   5      81.490 166.991 377.562  1.00  0.00           C
ATOM   5373  CA  LYS T   6      80.817 170.102 375.453  1.00  0.00           C
ATOM   5374  CA  HIS T   7      79.269 172.449 377.993  1.00  0.00           C
ATOM   5375  CA  PRO T   8      76.546 172.578 380.626  1.00  0.00           C
ATOM   5376  CA  HIS T   9      73.043 172.580 379.194  1.00  0.00           C
ATOM   5377  CA  VAL T  10      71.541 175.305 381.321  1.00  0.00           C
ATOM   5378  CA  THR T  11      67.813 175.900 381.041  1.00  0.00           C
ATOM   5379  CA  GLU T  12      64.879 176.371 383.389  1.00  0.00           C
ATOM   5380  CA  LYS T  13      64.100 172.665 383.171  1.00  0.00           C
ATOM   5381  CA  ALA T  14      67.724 171.775 383.894  1.00  0.00           C
ATOM   5382  CA  MET T  15      67.627 173.992 386.963  1.00  0.00           C
ATOM   5383  CA  ASN T  16      64.659 172.046 388.311  1.00  0.00           C
ATOM   5384  CA  ASP T  17      66.374 168.675 387.887  1.00  0.00           C
ATOM   5385  CA  MET T  18      69.435 170.179 389.521  1.00  0.00           C
ATOM   5386  CA  ASP T  19      67.370 171.495 392.447  1.00  0.00           C
ATOM   5387  CA  PHE T  20      64.866 168.710 393.045  1.00  0.00           C
ATOM   5388  CA  ASN T  22      70.227 166.387 392.015  1.00  0.00           C
ATOM   5389  CA  LYS T  23      70.759 166.116 388.262  1.00  0.00           C
ATOM   5390  CA  LEU T  24      73.192 167.985 386.018  1.00  0.00           C
ATOM   5391  CA  GLN T  25      72.473 168.387 382.306  1.00  0.00           C
ATOM   5392  CA  PHE T  26      75.199 168.706 379.672  1.00  0.00           C
ATOM   5393  CA  ALA T  27      75.560 168.972 375.924  1.00  0.00           C
ATOM   5394  CA  VAL T  28      77.795 166.089 374.904  1.00  0.00           C
ATOM   5395  CA  ASP T  29      79.281 164.602 371.773  1.00  0.00           C
ATOM   5396  CA  ASP T  30      76.673 162.377 370.173  1.00  0.00           C
ATOM   5397  CA  ARG T  31      79.350 159.749 369.686  1.00  0.00           C
ATOM   5398  CA  ALA T  32      79.627 159.347 373.469  1.00  0.00           C
ATOM   5399  CA  SER T  33      77.850 156.590 375.374  1.00  0.00           C
ATOM   5400  CA  LYS T  34      76.206 156.838 378.768  1.00  0.00           C
ATOM   5401  CA  GLY T  35      79.198 155.177 380.408  1.00  0.00           C
ATOM   5402  CA  GLU T  36      81.558 157.645 378.756  1.00  0.00           C
ATOM   5403  CA  VAL T  37      79.531 160.568 380.023  1.00  0.00           C
ATOM   5404  CA  ALA T  38      79.288 158.962 383.439  1.00  0.00           C
ATOM   5405  CA  ASP T  39      83.063 158.790 383.598  1.00  0.00           C
ATOM   5406  CA  ALA T  40      84.008 162.096 381.988  1.00  0.00           C
ATOM   5407  CA  VAL T  41      81.646 163.926 384.307  1.00  0.00           C
ATOM   5408  CA  GLU T  42      83.153 162.150 387.300  1.00  0.00           C
ATOM   5409  CA  GLU T  43      86.711 162.820 386.177  1.00  0.00           C
ATOM   5410  CA  GLN T  44      86.092 166.552 385.876  1.00  0.00           C
ATOM   5411  CA  TYR T  45      84.199 167.068 389.113  1.00  0.00           C
ATOM   5412  CA  ASP T  46      84.628 165.514 392.544  1.00  0.00           C
ATOM   5413  CA  VAL T  47      81.306 163.700 392.104  1.00  0.00           C
ATOM   5414  CA  THR T  48      79.880 160.181 391.898  1.00  0.00           C
ATOM   5415  CA  VAL T  49      77.545 159.557 388.959  1.00  0.00           C
ATOM   5416  CA  GLU T  50      74.555 157.406 389.812  1.00  0.00           C
ATOM   5417  CA  GLN T  51      72.625 157.446 386.554  1.00  0.00           C
ATOM   5418  CA  VAL T  52      72.764 158.940 383.076  1.00  0.00           C
ATOM   5419  CA  ASN T  53      69.904 159.555 380.668  1.00  0.00           C
ATOM   5420  CA  THR T  54      70.473 160.275 377.006  1.00  0.00           C
ATOM   5421  CA  GLN T  55      68.710 162.174 374.271  1.00  0.00           C
ATOM   5422  CA  ASN T  56      69.798 162.968 370.726  1.00  0.00           C
ATOM   5423  CA  THR T  57      68.432 166.502 370.492  1.00  0.00           C
ATOM   5424  CA  MET T  58      66.584 168.131 367.611  1.00  0.00           C
ATOM   5425  CA  ASP T  59      69.472 170.545 367.814  1.00  0.00           C
ATOM   5426  CA  GLY T  60      71.976 168.112 366.352  1.00  0.00           C
ATOM   5427  CA  GLU T  61      73.673 167.800 369.758  1.00  0.00           C
ATOM   5428  CA  LYS T  62      73.379 164.997 372.340  1.00  0.00           C
ATOM   5429  CA  LYS T  63      71.938 165.865 375.727  1.00  0.00           C
ATOM   5430  CA  ALA T  64      72.764 163.985 378.910  1.00  0.00           C
ATOM   5431  CA  VAL T  65      70.922 164.200 382.227  1.00  0.00           C
ATOM   5432  CA  VAL T  66      73.287 162.883 384.891  1.00  0.00           C
ATOM   5433  CA  ARG T  67      71.805 162.104 388.325  1.00  0.00           C
ATOM   5434  CA  LEU T  68      74.377 162.697 391.060  1.00  0.00           C
ATOM   5435  CA  SER T  69      74.985 160.734 394.248  1.00  0.00           C
ATOM   5436  CA  GLU T  70      73.141 161.587 397.424  1.00  0.00           C
ATOM   5437  CA  ASP T  71      76.528 163.001 398.462  1.00  0.00           C
ATOM   5438  CA  ASP T  72      76.887 165.710 395.801  1.00  0.00           C
ATOM   5439  CA  ASP T  73      75.027 169.009 394.991  1.00  0.00           C
ATOM   5440  CA  GLN T  75      77.440 172.373 391.128  1.00  0.00           C
ATOM   5441  CA  GLU T  76      77.113 175.422 388.911  1.00  0.00           C
ATOM   5442  CA  VAL T  77      79.801 177.902 390.012  1.00  0.00           C
ATOM   5443  CA  ALA T  78      81.842 174.684 390.123  1.00  0.00           C
TER    5444          ALA T  78
ATOM   5445  CA  SER U   1     101.138 196.710 338.094  1.00  0.00           C
ATOM   5446  CA  LYS U   2      99.836 199.217 335.521  1.00  0.00           C
ATOM   5447  CA  GLN U   3      96.287 197.801 335.588  1.00  0.00           C
ATOM   5448  CA  PRO U   4      93.949 199.958 337.739  1.00  0.00           C
```

```
ATOM   5449  CA  ASP U   5      92.260 197.020 339.441  1.00  0.00           C
ATOM   5450  CA  LYS U   6      95.533 195.535 340.623  1.00  0.00           C
ATOM   5451  CA  GLN U   7      96.868 198.862 341.884  1.00  0.00           C
ATOM   5452  CA  ARG U   8      93.715 199.539 343.893  1.00  0.00           C
ATOM   5453  CA  LYS U   9      93.689 195.969 345.103  1.00  0.00           C
ATOM   5454  CA  SER U  10      97.307 195.858 346.253  1.00  0.00           C
ATOM   5455  CA  GLN U  11      96.501 198.991 348.273  1.00  0.00           C
ATOM   5456  CA  ARG U  12      93.434 197.826 350.222  1.00  0.00           C
ATOM   5457  CA  ARG U  13      95.044 194.427 350.764  1.00  0.00           C
ATOM   5458  CA  ALA U  14      98.435 195.687 351.857  1.00  0.00           C
ATOM   5459  CA  PRO U  15      99.568 193.995 355.103  1.00  0.00           C
ATOM   5460  CA  LEU U  16      99.808 196.174 358.219  1.00  0.00           C
ATOM   5461  CA  HIS U  17     103.541 196.902 358.011  1.00  0.00           C
ATOM   5462  CA  GLU U  18     102.950 198.027 354.449  1.00  0.00           C
ATOM   5463  CA  ARG U  19     100.366 200.644 355.311  1.00  0.00           C
ATOM   5464  CA  HIS U  20     102.736 203.000 357.079  1.00  0.00           C
ATOM   5465  CA  LYS U  21     103.334 204.421 353.631  1.00  0.00           C
ATOM   5466  CA  GLN U  22      99.655 205.163 353.174  1.00  0.00           C
ATOM   5467  CA  VAL U  23      99.973 207.382 356.213  1.00  0.00           C
ATOM   5468  CA  ARG U  24     102.797 209.602 354.939  1.00  0.00           C
ATOM   5469  CA  ALA U  25     102.543 213.396 354.709  1.00  0.00           C
ATOM   5470  CA  THR U  26     104.670 216.275 353.422  1.00  0.00           C
ATOM   5471  CA  LEU U  27     107.151 217.915 355.750  1.00  0.00           C
ATOM   5472  CA  SER U  28     107.923 221.704 358.241  1.00  0.00           C
ATOM   5473  CA  ALA U  29     109.790 222.811 355.120  1.00  0.00           C
ATOM   5474  CA  ASP U  30     113.022 222.059 356.946  1.00  0.00           C
ATOM   5475  CA  LEU U  31     112.005 218.709 358.354  1.00  0.00           C
ATOM   5476  CA  ARG U  32     110.822 217.704 354.872  1.00  0.00           C
ATOM   5477  CA  GLU U  33     114.278 218.536 353.567  1.00  0.00           C
ATOM   5478  CA  GLU U  34     116.020 216.987 356.538  1.00  0.00           C
ATOM   5479  CA  TYR U  35     114.315 213.605 356.253  1.00  0.00           C
ATOM   5480  CA  GLY U  36     112.931 213.313 352.737  1.00  0.00           C
ATOM   5481  CA  VAL U  40     111.075 210.579 354.798  1.00  0.00           C
ATOM   5482  CA  ARG U  41     110.314 207.500 356.870  1.00  0.00           C
ATOM   5483  CA  VAL U  42     106.777 208.314 357.980  1.00  0.00           C
ATOM   5484  CA  ASN U  43     106.572 208.502 361.767  1.00  0.00           C
ATOM   5485  CA  ALA U  44     103.637 207.994 364.134  1.00  0.00           C
ATOM   5486  CA  GLY U  45     103.694 211.723 364.808  1.00  0.00           C
ATOM   5487  CA  ASP U  46     103.505 214.992 365.558  1.00  0.00           C
ATOM   5488  CA  THR U  47     101.811 218.313 364.881  1.00  0.00           C
ATOM   5489  CA  VAL U  48     100.236 219.014 361.533  1.00  0.00           C
ATOM   5490  CA  GLU U  49      98.459 221.672 359.475  1.00  0.00           C
ATOM   5491  CA  VAL U  50      95.493 221.005 357.204  1.00  0.00           C
ATOM   5492  CA  LEU U  51      95.888 222.128 353.600  1.00  0.00           C
ATOM   5493  CA  ARG U  52      92.745 220.979 351.808  1.00  0.00           C
ATOM   5494  CA  GLY U  53      89.660 219.851 353.724  1.00  0.00           C
ATOM   5495  CA  ASP U  54      86.931 222.146 355.048  1.00  0.00           C
ATOM   5496  CA  PHE U  55      89.384 222.686 357.910  1.00  0.00           C
ATOM   5497  CA  ALA U  56      91.606 224.058 355.170  1.00  0.00           C
ATOM   5498  CA  GLY U  57      94.115 226.053 357.171  1.00  0.00           C
ATOM   5499  CA  GLU U  58      94.351 224.785 360.719  1.00  0.00           C
ATOM   5500  CA  GLU U  59      96.912 223.222 362.994  1.00  0.00           C
ATOM   5501  CA  GLY U  60      96.674 220.667 365.725  1.00  0.00           C
ATOM   5502  CA  GLU U  61      98.303 217.609 367.224  1.00  0.00           C
ATOM   5503  CA  VAL U  62      97.853 214.165 365.713  1.00  0.00           C
ATOM   5504  CA  ILE U  63      95.603 212.342 368.169  1.00  0.00           C
ATOM   5505  CA  ASN U  64      95.225 208.981 366.424  1.00  0.00           C
ATOM   5506  CA  VAL U  65      96.461 206.963 363.463  1.00  0.00           C
ATOM   5507  CA  ASP U  66      94.590 203.991 362.018  1.00  0.00           C
ATOM   5508  CA  LEU U  67      96.668 201.917 359.616  1.00  0.00           C
ATOM   5509  CA  ASP U  68      93.654 199.821 358.622  1.00  0.00           C
ATOM   5510  CA  LYS U  69      91.544 202.720 357.385  1.00  0.00           C
ATOM   5511  CA  ALA U  70      94.733 204.652 356.632  1.00  0.00           C
ATOM   5512  CA  VAL U  71      93.487 207.741 358.426  1.00  0.00           C
ATOM   5513  CA  ILE U  72      94.434 210.013 361.329  1.00  0.00           C
ATOM   5514  CA  HIS U  73      92.701 212.226 363.898  1.00  0.00           C
ATOM   5515  CA  VAL U  74      93.798 215.823 364.550  1.00  0.00           C
ATOM   5516  CA  GLU U  75      92.925 217.867 367.650  1.00  0.00           C
ATOM   5517  CA  ASP U  76      89.829 220.001 367.181  1.00  0.00           C
ATOM   5518  CA  VAL U  77      89.188 218.712 363.647  1.00  0.00           C
ATOM   5519  CA  THR U  78      85.843 217.339 364.773  1.00  0.00           C
ATOM   5520  CA  LEU U  79      82.218 216.917 363.719  1.00  0.00           C
ATOM   5521  CA  GLU U  80      79.176 217.642 365.865  1.00  0.00           C
ATOM   5522  CA  LYS U  81      76.883 214.678 366.466  1.00  0.00           C
ATOM   5523  CA  THR U  82      73.130 215.013 366.883  1.00  0.00           C
ATOM   5524  CA  ASP U  83      73.337 214.380 370.620  1.00  0.00           C
ATOM   5525  CA  GLY U  84      75.849 217.205 370.838  1.00  0.00           C
ATOM   5526  CA  GLU U  85      78.924 214.999 371.088  1.00  0.00           C
ATOM   5527  CA  GLU U  86      82.105 216.108 369.362  1.00  0.00           C
ATOM   5528  CA  VAL U  87      83.554 213.255 367.334  1.00  0.00           C
ATOM   5529  CA  PRO U  88      86.745 213.441 365.271  1.00  0.00           C
ATOM   5530  CA  ARG U  89      86.627 213.940 361.510  1.00  0.00           C
ATOM   5531  CA  PRO U  90      89.109 211.498 359.829  1.00  0.00           C
ATOM   5532  CA  LEU U  91      91.740 212.894 357.474  1.00  0.00           C
ATOM   5533  CA  ASP U  92      93.803 211.497 354.621  1.00  0.00           C
ATOM   5534  CA  THR U  93      97.483 212.331 355.097  1.00  0.00           C
ATOM   5535  CA  SER U  94      97.627 213.649 351.524  1.00  0.00           C
```

```
ATOM   5536  CA  ASN U  95      95.808 216.768 352.733  1.00  0.00           C
ATOM   5537  CA  VAL U  96      98.061 217.353 355.697  1.00  0.00           C
ATOM   5538  CA  ARG U  97     101.487 218.825 356.462  1.00  0.00           C
ATOM   5539  CA  VAL U  98     103.758 218.049 359.409  1.00  0.00           C
ATOM   5540  CA  THR U  99     104.967 221.249 361.047  1.00  0.00           C
ATOM   5541  CA  ASP U 100     106.443 219.517 364.091  1.00  0.00           C
ATOM   5542  CA  LEU U 101     107.745 216.034 364.879  1.00  0.00           C
ATOM   5543  CA  ASP U 102     107.545 213.835 367.954  1.00  0.00           C
ATOM   5544  CA  LEU U 103     111.042 212.401 368.259  1.00  0.00           C
ATOM   5545  CA  GLU U 104     110.757 210.697 371.642  1.00  0.00           C
ATOM   5546  CA  ASP U 105     111.718 207.461 369.907  1.00  0.00           C
ATOM   5547  CA  GLU U 106     115.391 206.858 369.202  1.00  0.00           C
ATOM   5548  CA  LYS U 107     114.725 204.581 366.248  1.00  0.00           C
ATOM   5549  CA  ARG U 108     112.472 207.063 364.465  1.00  0.00           C
ATOM   5550  CA  GLU U 109     114.921 209.943 364.874  1.00  0.00           C
ATOM   5551  CA  ALA U 110     117.659 207.615 363.683  1.00  0.00           C
ATOM   5552  CA  ARG U 111     115.868 206.987 360.373  1.00  0.00           C
ATOM   5553  CA  LEU U 112     114.966 210.646 359.919  1.00  0.00           C
ATOM   5554  CA  GLU U 113     118.503 211.811 360.592  1.00  0.00           C
TER    5555      GLU U 113
ATOM   5556  CA  MET V   1      -2.370 203.275 232.321  1.00  0.00           C
ATOM   5557  CA  PHE V   2      -0.281 204.245 235.346  1.00  0.00           C
ATOM   5558  CA  THR V   3       1.222 207.717 235.074  1.00  0.00           C
ATOM   5559  CA  ILE V   4       4.012 208.561 237.505  1.00  0.00           C
ATOM   5560  CA  ASN V   5       5.442 212.051 237.852  1.00  0.00           C
ATOM   5561  CA  ALA V   6       9.114 212.319 238.665  1.00  0.00           C
ATOM   5562  CA  GLU V   7      12.073 214.686 238.627  1.00  0.00           C
ATOM   5563  CA  VAL V   8      15.729 214.062 237.832  1.00  0.00           C
ATOM   5564  CA  ARG V   9      17.860 213.848 240.978  1.00  0.00           C
ATOM   5565  CA  GLN V  12      22.938 210.985 244.779  1.00  0.00           C
ATOM   5566  CA  GLY V  13      24.387 208.772 247.497  1.00  0.00           C
ATOM   5567  CA  LYS V  14      23.426 207.774 251.040  1.00  0.00           C
ATOM   5568  CA  GLY V  15      23.034 211.305 252.362  1.00  0.00           C
ATOM   5569  CA  ALA V  16      20.886 212.539 249.487  1.00  0.00           C
ATOM   5570  CA  SER V  17      18.690 209.428 249.543  1.00  0.00           C
ATOM   5571  CA  ARG V  19      17.084 213.410 252.766  1.00  0.00           C
ATOM   5572  CA  LEU V  20      14.458 212.427 250.176  1.00  0.00           C
ATOM   5573  CA  ARG V  21      12.899 209.821 252.449  1.00  0.00           C
ATOM   5574  CA  ALA V  22      12.793 212.230 255.401  1.00  0.00           C
ATOM   5575  CA  ALA V  23      10.894 214.577 253.088  1.00  0.00           C
ATOM   5576  CA  ASN V  24       8.153 212.132 252.051  1.00  0.00           C
ATOM   5577  CA  LYS V  25       9.843 211.099 248.789  1.00  0.00           C
ATOM   5578  CA  PHE V  26      12.176 208.314 247.701  1.00  0.00           C
ATOM   5579  CA  PRO V  27      14.782 207.575 245.008  1.00  0.00           C
ATOM   5580  CA  ALA V  28      14.393 205.333 241.960  1.00  0.00           C
ATOM   5581  CA  ILE V  29      16.379 204.479 238.831  1.00  0.00           C
ATOM   5582  CA  ILE V  30      15.459 204.019 235.178  1.00  0.00           C
ATOM   5583  CA  TYR V  31      17.789 201.821 233.133  1.00  0.00           C
ATOM   5584  CA  GLY V  32      17.863 199.608 230.062  1.00  0.00           C
ATOM   5585  CA  LYS V  34      20.037 201.367 226.339  1.00  0.00           C
ATOM   5586  CA  GLU V  35      20.212 205.663 226.843  1.00  0.00           C
ATOM   5587  CA  ALA V  36      22.163 206.186 230.053  1.00  0.00           C
ATOM   5588  CA  PRO V  37      20.482 205.380 233.388  1.00  0.00           C
ATOM   5589  CA  LEU V  38      18.281 208.146 234.759  1.00  0.00           C
ATOM   5590  CA  ALA V  39      18.242 208.712 238.524  1.00  0.00           C
ATOM   5591  CA  ILE V  40      14.881 210.104 239.660  1.00  0.00           C
ATOM   5592  CA  GLU V  41      12.880 210.964 242.786  1.00  0.00           C
ATOM   5593  CA  LEU V  42       9.254 210.098 243.451  1.00  0.00           C
ATOM   5594  CA  ASP V  43       6.401 211.109 245.743  1.00  0.00           C
ATOM   5595  CA  HIS V  44       6.214 208.289 248.286  1.00  0.00           C
ATOM   5596  CA  ASP V  45       2.507 208.195 249.117  1.00  0.00           C
ATOM   5597  CA  LYS V  46       1.272 208.581 245.539  1.00  0.00           C
ATOM   5598  CA  VAL V  47       3.423 205.741 244.198  1.00  0.00           C
ATOM   5599  CA  MET V  48       2.717 203.594 247.269  1.00  0.00           C
ATOM   5600  CA  ASN V  49      -1.029 203.788 246.587  1.00  0.00           C
ATOM   5601  CA  MET V  50      -0.432 203.060 242.913  1.00  0.00           C
ATOM   5602  CA  GLN V  51       1.712 199.986 243.556  1.00  0.00           C
ATOM   5603  CA  ALA V  52      -0.943 198.628 245.915  1.00  0.00           C
ATOM   5604  CA  LYS V  53      -2.641 197.333 242.748  1.00  0.00           C
ATOM   5605  CA  ALA V  54      -1.054 194.157 241.357  1.00  0.00           C
ATOM   5606  CA  GLU V  55      -1.142 195.556 237.806  1.00  0.00           C
ATOM   5607  CA  PHE V  56       1.547 198.025 238.868  1.00  0.00           C
ATOM   5608  CA  TYR V  57       4.018 195.164 238.583  1.00  0.00           C
ATOM   5609  CA  SER V  58       2.829 193.650 235.300  1.00  0.00           C
ATOM   5610  CA  GLU V  59       1.915 196.645 233.146  1.00  0.00           C
ATOM   5611  CA  VAL V  60       4.064 198.997 231.142  1.00  0.00           C
ATOM   5612  CA  LEU V  61       3.967 202.249 233.123  1.00  0.00           C
ATOM   5613  CA  THR V  62       4.524 205.848 232.052  1.00  0.00           C
ATOM   5614  CA  ILE V  63       6.936 208.035 233.995  1.00  0.00           C
ATOM   5615  CA  VAL V  64       6.685 211.737 233.293  1.00  0.00           C
ATOM   5616  CA  VAL V  65      10.039 213.355 234.011  1.00  0.00           C
ATOM   5617  CA  ASP V  66      11.419 216.498 232.410  1.00  0.00           C
ATOM   5618  CA  GLY V  67       8.746 216.990 229.754  1.00  0.00           C
ATOM   5619  CA  LYS V  68       8.437 213.599 228.058  1.00  0.00           C
ATOM   5620  CA  GLU V  69       7.050 210.150 228.877  1.00  0.00           C
ATOM   5621  CA  ILE V  70       9.406 207.180 229.158  1.00  0.00           C
ATOM   5622  CA  LYS V  71       7.526 203.813 229.230  1.00  0.00           C
```

| | | | | | | | | | |
|---|---|---|---|---|---|---|---|---|---|
| ATOM | 5623 | CA | VAL | V | 72 | 8.920 | 201.335 | 231.730 | 1.00 | 0.00 | C |
| ATOM | 5624 | CA | LYS | V | 73 | 8.100 | 198.270 | 233.808 | 1.00 | 0.00 | C |
| ATOM | 5625 | CA | ALA | V | 74 | 8.752 | 197.799 | 237.525 | 1.00 | 0.00 | C |
| ATOM | 5626 | CA | GLN | V | 75 | 11.516 | 195.747 | 236.544 | 1.00 | 0.00 | C |
| ATOM | 5627 | CA | ASP | V | 76 | 12.318 | 194.860 | 240.131 | 1.00 | 0.00 | C |
| ATOM | 5628 | CA | VAL | V | 77 | 11.362 | 195.653 | 243.698 | 1.00 | 0.00 | C |
| ATOM | 5629 | CA | GLN | V | 78 | 13.190 | 195.301 | 246.989 | 1.00 | 0.00 | C |
| ATOM | 5630 | CA | ARG | V | 79 | 10.905 | 195.003 | 250.011 | 1.00 | 0.00 | C |
| ATOM | 5631 | CA | HIS | V | 80 | 11.857 | 195.415 | 253.662 | 1.00 | 0.00 | C |
| ATOM | 5632 | CA | TYR | V | 82 | 10.955 | 192.375 | 256.457 | 1.00 | 0.00 | C |
| ATOM | 5633 | CA | LYS | V | 83 | 8.339 | 195.339 | 257.493 | 1.00 | 0.00 | C |
| ATOM | 5634 | CA | PRO | V | 84 | 5.485 | 196.168 | 255.062 | 1.00 | 0.00 | C |
| ATOM | 5635 | CA | LYS | V | 85 | 7.542 | 198.775 | 253.210 | 1.00 | 0.00 | C |
| ATOM | 5636 | CA | LEU | V | 86 | 9.215 | 199.333 | 249.847 | 1.00 | 0.00 | C |
| ATOM | 5637 | CA | GLN | V | 87 | 13.024 | 199.628 | 249.973 | 1.00 | 0.00 | C |
| ATOM | 5638 | CA | HIS | V | 88 | 13.876 | 200.264 | 246.305 | 1.00 | 0.00 | C |
| ATOM | 5639 | CA | ILE | V | 89 | 12.453 | 199.888 | 242.789 | 1.00 | 0.00 | C |
| ATOM | 5640 | CA | ASP | V | 90 | 14.077 | 199.389 | 239.369 | 1.00 | 0.00 | C |
| ATOM | 5641 | CA | PHE | V | 91 | 12.386 | 200.697 | 236.451 | 1.00 | 0.00 | C |
| ATOM | 5642 | CA | VAL | V | 92 | 13.449 | 199.057 | 233.206 | 1.00 | 0.00 | C |
| ATOM | 5643 | CA | ARG | V | 93 | 12.750 | 200.796 | 229.893 | 1.00 | 0.00 | C |
| ATOM | 5644 | CA | ALA | V | 94 | 10.109 | 199.087 | 227.772 | 1.00 | 0.00 | C |
| TER | 5645 | | ALA | V | 94 | | | | | |
| ATOM | 5646 | CA | THR | W | 1 | 103.013 | 183.684 | 375.047 | 1.00 | 0.00 | C |
| ATOM | 5647 | CA | VAL | W | 2 | 103.550 | 182.107 | 378.456 | 1.00 | 0.00 | C |
| ATOM | 5648 | CA | LEU | W | 3 | 104.233 | 178.544 | 377.279 | 1.00 | 0.00 | C |
| ATOM | 5649 | CA | HIS | W | 4 | 107.159 | 178.353 | 374.809 | 1.00 | 0.00 | C |
| ATOM | 5650 | CA | VAL | W | 5 | 108.288 | 175.676 | 372.358 | 1.00 | 0.00 | C |
| ATOM | 5651 | CA | GLN | W | 6 | 111.688 | 175.161 | 373.991 | 1.00 | 0.00 | C |
| ATOM | 5652 | CA | GLU | W | 7 | 110.013 | 174.775 | 377.377 | 1.00 | 0.00 | C |
| ATOM | 5653 | CA | ILE | W | 8 | 107.894 | 172.101 | 375.701 | 1.00 | 0.00 | C |
| ATOM | 5654 | CA | ARG | W | 9 | 110.796 | 170.264 | 374.095 | 1.00 | 0.00 | C |
| ATOM | 5655 | CA | ASP | W | 10 | 112.583 | 170.269 | 377.461 | 1.00 | 0.00 | C |
| ATOM | 5656 | CA | MET | W | 11 | 109.687 | 168.290 | 378.872 | 1.00 | 0.00 | C |
| ATOM | 5657 | CA | THR | W | 12 | 109.621 | 164.514 | 379.269 | 1.00 | 0.00 | C |
| ATOM | 5658 | CA | PRO | W | 13 | 106.779 | 162.768 | 377.441 | 1.00 | 0.00 | C |
| ATOM | 5659 | CA | ALA | W | 14 | 105.186 | 162.231 | 380.862 | 1.00 | 0.00 | C |
| ATOM | 5660 | CA | GLU | W | 15 | 105.529 | 165.933 | 381.635 | 1.00 | 0.00 | C |
| ATOM | 5661 | CA | ARG | W | 16 | 103.881 | 166.827 | 378.317 | 1.00 | 0.00 | C |
| ATOM | 5662 | CA | GLU | W | 17 | 101.119 | 164.369 | 379.201 | 1.00 | 0.00 | C |
| ATOM | 5663 | CA | ALA | W | 18 | 100.733 | 165.983 | 382.620 | 1.00 | 0.00 | C |
| ATOM | 5664 | CA | GLU | W | 19 | 100.902 | 169.531 | 381.252 | 1.00 | 0.00 | C |
| ATOM | 5665 | CA | LEU | W | 20 | 98.451 | 168.673 | 378.492 | 1.00 | 0.00 | C |
| ATOM | 5666 | CA | ASP | W | 21 | 95.692 | 167.531 | 380.844 | 1.00 | 0.00 | C |
| ATOM | 5667 | CA | ASP | W | 22 | 96.334 | 170.551 | 383.033 | 1.00 | 0.00 | C |
| ATOM | 5668 | CA | LEU | W | 23 | 95.715 | 172.836 | 380.083 | 1.00 | 0.00 | C |
| ATOM | 5669 | CA | LYS | W | 24 | 92.569 | 171.017 | 378.957 | 1.00 | 0.00 | C |
| ATOM | 5670 | CA | THR | W | 25 | 91.161 | 171.596 | 382.435 | 1.00 | 0.00 | C |
| ATOM | 5671 | CA | GLU | W | 26 | 91.954 | 175.325 | 382.398 | 1.00 | 0.00 | C |
| ATOM | 5672 | CA | LEU | W | 27 | 90.178 | 175.312 | 379.041 | 1.00 | 0.00 | C |
| ATOM | 5673 | CA | LEU | W | 28 | 87.273 | 173.244 | 380.320 | 1.00 | 0.00 | C |
| ATOM | 5674 | CA | ASN | W | 29 | 86.979 | 175.736 | 383.179 | 1.00 | 0.00 | C |
| ATOM | 5675 | CA | ALA | W | 30 | 87.272 | 178.951 | 381.188 | 1.00 | 0.00 | C |
| ATOM | 5676 | CA | ARG | W | 31 | 84.459 | 177.585 | 379.034 | 1.00 | 0.00 | C |
| ATOM | 5677 | CA | VAL | W | 33 | 82.666 | 177.912 | 382.442 | 1.00 | 0.00 | C |
| ATOM | 5678 | CA | GLN | W | 34 | 83.195 | 181.411 | 383.738 | 1.00 | 0.00 | C |
| ATOM | 5679 | CA | ALA | W | 35 | 81.759 | 183.115 | 380.659 | 1.00 | 0.00 | C |
| ATOM | 5680 | CA | ALA | W | 36 | 78.903 | 180.616 | 380.633 | 1.00 | 0.00 | C |
| ATOM | 5681 | CA | GLY | W | 37 | 77.824 | 181.392 | 384.179 | 1.00 | 0.00 | C |
| ATOM | 5682 | CA | GLY | W | 38 | 80.212 | 184.526 | 384.809 | 1.00 | 0.00 | C |
| ATOM | 5683 | CA | ALA | W | 39 | 82.130 | 188.251 | 383.645 | 1.00 | 0.00 | C |
| ATOM | 5684 | CA | PRO | W | 40 | 85.713 | 187.698 | 382.359 | 1.00 | 0.00 | C |
| ATOM | 5685 | CA | GLU | W | 41 | 85.964 | 188.099 | 378.953 | 1.00 | 0.00 | C |
| ATOM | 5686 | CA | ASN | W | 42 | 87.633 | 185.366 | 377.126 | 1.00 | 0.00 | C |
| ATOM | 5687 | CA | PRO | W | 43 | 90.220 | 186.299 | 375.930 | 1.00 | 0.00 | C |
| ATOM | 5688 | CA | GLY | W | 44 | 93.722 | 185.668 | 374.744 | 1.00 | 0.00 | C |
| ATOM | 5689 | CA | ARG | W | 45 | 93.688 | 182.955 | 377.387 | 1.00 | 0.00 | C |
| ATOM | 5690 | CA | ILE | W | 46 | 90.950 | 180.715 | 376.030 | 1.00 | 0.00 | C |
| ATOM | 5691 | CA | LYS | W | 47 | 92.834 | 181.256 | 372.776 | 1.00 | 0.00 | C |
| ATOM | 5692 | CA | GLU | W | 48 | 96.291 | 180.780 | 374.306 | 1.00 | 0.00 | C |
| ATOM | 5693 | CA | LEU | W | 49 | 95.117 | 177.497 | 375.769 | 1.00 | 0.00 | C |
| ATOM | 5694 | CA | ARG | W | 50 | 94.131 | 176.319 | 372.296 | 1.00 | 0.00 | C |
| ATOM | 5695 | CA | LYS | W | 51 | 97.520 | 177.174 | 370.833 | 1.00 | 0.00 | C |
| ATOM | 5696 | CA | ALA | W | 52 | 99.142 | 175.794 | 373.966 | 1.00 | 0.00 | C |
| ATOM | 5697 | CA | ILE | W | 53 | 97.434 | 172.435 | 373.482 | 1.00 | 0.00 | C |
| ATOM | 5698 | CA | ALA | W | 54 | 98.084 | 172.465 | 369.744 | 1.00 | 0.00 | C |
| ATOM | 5699 | CA | ARG | W | 55 | 101.776 | 173.073 | 370.452 | 1.00 | 0.00 | C |
| ATOM | 5700 | CA | ILE | W | 56 | 102.098 | 170.219 | 372.906 | 1.00 | 0.00 | C |
| ATOM | 5701 | CA | LYS | W | 57 | 100.467 | 167.683 | 370.582 | 1.00 | 0.00 | C |
| ATOM | 5702 | CA | THR | W | 58 | 102.588 | 168.996 | 367.749 | 1.00 | 0.00 | C |
| ATOM | 5703 | CA | ILE | W | 59 | 105.662 | 168.179 | 369.828 | 1.00 | 0.00 | C |
| ATOM | 5704 | CA | GLN | W | 60 | 104.177 | 164.871 | 371.015 | 1.00 | 0.00 | C |
| ATOM | 5705 | CA | GLY | W | 61 | 104.322 | 163.714 | 367.434 | 1.00 | 0.00 | C |
| ATOM | 5706 | CA | GLU | W | 62 | 107.703 | 165.177 | 366.598 | 1.00 | 0.00 | C |
| ATOM | 5707 | CA | GLU | W | 63 | 109.256 | 163.394 | 369.583 | 1.00 | 0.00 | C |
| ATOM | 5708 | CA | GLY | W | 64 | 107.419 | 160.128 | 369.089 | 1.00 | 0.00 | C |
| ATOM | 5709 | CA | ASP | W | 65 | 105.559 | 161.068 | 372.303 | 1.00 | 0.00 | C |

```
TER    5710        ASP W  65
ATOM   5711   CA   MET X   1      49.979 222.885 254.021  1.00  0.00           C
ATOM   5712   CA   PRO X   2      46.478 223.608 254.052  1.00  0.00           C
ATOM   5713   CA   ARG X   3      46.364 223.131 257.755  1.00  0.00           C
ATOM   5714   CA   LEU X   4      44.147 222.226 260.661  1.00  0.00           C
ATOM   5715   CA   LYS X   5      44.305 223.951 264.038  1.00  0.00           C
ATOM   5716   CA   VAL X   6      43.499 221.367 266.696  1.00  0.00           C
ATOM   5717   CA   LYS X   7      42.858 222.310 270.357  1.00  0.00           C
ATOM   5718   CA   LEU X   8      42.701 219.731 273.193  1.00  0.00           C
ATOM   5719   CA   VAL X   9      39.526 220.745 275.043  1.00  0.00           C
ATOM   5720   CA   LYS X  10      38.683 217.558 277.111  1.00  0.00           C
ATOM   5721   CA   SER X  11      40.776 215.510 279.473  1.00  0.00           C
ATOM   5722   CA   PRO X  12      42.231 212.273 277.902  1.00  0.00           C
ATOM   5723   CA   ILE X  13      43.089 210.885 281.434  1.00  0.00           C
ATOM   5724   CA   GLY X  14      42.339 207.180 281.430  1.00  0.00           C
ATOM   5725   CA   TYR X  15      41.651 207.003 277.681  1.00  0.00           C
ATOM   5726   CA   PRO X  16      42.606 203.969 275.530  1.00  0.00           C
ATOM   5727   CA   LYS X  17      46.243 203.711 274.321  1.00  0.00           C
ATOM   5728   CA   ASP X  18      45.117 204.294 270.673  1.00  0.00           C
ATOM   5729   CA   GLN X  19      43.560 207.549 271.555  1.00  0.00           C
ATOM   5730   CA   LYS X  20      46.405 208.583 273.793  1.00  0.00           C
ATOM   5731   CA   ALA X  21      48.781 207.685 270.883  1.00  0.00           C
ATOM   5732   CA   ALA X  22      46.758 209.828 268.448  1.00  0.00           C
ATOM   5733   CA   LEU X  23      47.185 212.785 270.892  1.00  0.00           C
ATOM   5734   CA   LYS X  24      50.876 212.060 270.990  1.00  0.00           C
ATOM   5735   CA   ALA X  25      51.026 212.157 267.244  1.00  0.00           C
ATOM   5736   CA   LEU X  26      49.113 215.470 267.190  1.00  0.00           C
ATOM   5737   CA   GLY X  27      51.491 216.810 269.872  1.00  0.00           C
ATOM   5738   CA   LEU X  28      48.638 217.681 272.229  1.00  0.00           C
ATOM   5739   CA   ARG X  29      49.956 217.294 275.751  1.00  0.00           C
ATOM   5740   CA   ARG X  30      47.915 219.558 278.057  1.00  0.00           C
ATOM   5741   CA   LEU X  31      44.470 220.975 278.164  1.00  0.00           C
ATOM   5742   CA   GLN X  32      43.651 223.868 275.903  1.00  0.00           C
ATOM   5743   CA   GLN X  33      46.941 223.592 273.984  1.00  0.00           C
ATOM   5744   CA   GLU X  34      46.475 224.381 270.257  1.00  0.00           C
ATOM   5745   CA   ARG X  35      48.575 223.039 267.359  1.00  0.00           C
ATOM   5746   CA   VAL X  36      48.569 223.817 263.646  1.00  0.00           C
ATOM   5747   CA   LEU X  37      49.193 220.663 261.708  1.00  0.00           C
ATOM   5748   CA   GLU X  38      49.238 219.981 257.973  1.00  0.00           C
ATOM   5749   CA   ASP X  39      45.951 218.729 256.806  1.00  0.00           C
ATOM   5750   CA   THR X  40      46.996 215.280 255.472  1.00  0.00           C
ATOM   5751   CA   PRO X  41      44.976 211.981 255.321  1.00  0.00           C
ATOM   5752   CA   ALA X  42      47.176 210.714 258.137  1.00  0.00           C
ATOM   5753   CA   ILE X  43      46.792 213.793 260.349  1.00  0.00           C
ATOM   5754   CA   ARG X  44      43.047 213.617 259.667  1.00  0.00           C
ATOM   5755   CA   GLY X  45      42.986 209.957 260.781  1.00  0.00           C
ATOM   5756   CA   ASN X  46      44.500 210.905 264.126  1.00  0.00           C
ATOM   5757   CA   VAL X  47      42.101 213.823 264.672  1.00  0.00           C
ATOM   5758   CA   GLU X  48      39.240 211.467 263.890  1.00  0.00           C
ATOM   5759   CA   LYS X  49      40.367 209.036 266.666  1.00  0.00           C
ATOM   5760   CA   VAL X  50      40.260 211.848 269.251  1.00  0.00           C
ATOM   5761   CA   ALA X  51      37.230 213.774 267.916  1.00  0.00           C
ATOM   5762   CA   HIS X  52      35.506 213.858 271.409  1.00  0.00           C
ATOM   5763   CA   LEU X  53      38.551 215.450 272.905  1.00  0.00           C
ATOM   5764   CA   VAL X  54      39.446 218.125 270.400  1.00  0.00           C
ATOM   5765   CA   ARG X  55      38.185 221.225 268.741  1.00  0.00           C
ATOM   5766   CA   VAL X  56      39.204 221.543 264.939  1.00  0.00           C
ATOM   5767   CA   GLU X  57      39.433 224.694 262.704  1.00  0.00           C
ATOM   5768   CA   VAL X  58      40.448 224.821 259.104  1.00  0.00           C
ATOM   5769   CA   VAL X  59      43.404 227.242 258.642  1.00  0.00           C
ATOM   5770   CA   GLU X  60      46.084 227.656 255.893  1.00  0.00           C
TER    5771        GLU X  60
MASTER       384    0    0    0    0    0    0  6 5747   24    0  495
END

File C -----------------------------------------------------------------------------
REMARK PDB coordinates for model of IF3 C-terminal domain bound to the 30S subunit
REMARK Written by O version 7.0.1
REMARK Fri Jan  5 15:05:12 2001
CRYST1   72.500   30.200   43.400  90.00 100.11  90.00
ORIGX1      1.000000  0.000000  0.000000        0.00000
ORIGX2      0.000000  1.000000  0.000000        0.00000
ORIGX3      0.000000  0.000000  1.000000        0.00000
SCALE1      0.013793  0.000000  0.002459        0.00000
SCALE2      0.000000  0.033113 -0.000001        0.00000
SCALE3      0.000000  0.000000  0.023405        0.00000
ATOM      1  N   ILE    83      41.988 123.220 288.159  1.00 34.37           7
ATOM      2  CA  ILE    83      42.207 122.910 286.691  1.00 30.46           6
ATOM      3  C   ILE    83      41.105 121.946 286.218  1.00 27.05           6
ATOM      4  O   ILE    83      40.654 121.971 285.073  1.00 26.58           8
ATOM      5  CB  ILE    83      43.622 122.294 286.454  1.00 31.10           6
ATOM      6  CG1 ILE    83      43.798 121.945 284.968  1.00 31.10           6
ATOM      7  CG2 ILE    83      43.837 121.084 287.375  1.00 32.09           6
ATOM      8  CD1 ILE    83      45.076 121.180 284.672  1.00 36.44           6
ATOM      9  1H  ILE    83      42.038 122.343 288.713  1.00  0.00           6
ATOM     10  2H  ILE    83      42.707 123.883 288.537  1.00  0.00           6
```

```
ATOM    11  3H   ILE    83      41.055 123.682 288.305  1.00  0.00      6
ATOM    12  N    ASN    84      40.532 121.277 287.203  1.00 21.89      7
ATOM    13  CA   ASN    84      39.426 120.367 287.000  1.00 17.82      6
ATOM    14  C    ASN    84      38.104 121.129 286.867  1.00 15.32      6
ATOM    15  O    ASN    84      37.981 122.287 287.305  1.00 11.88      8
ATOM    16  CB   ASN    84      39.348 119.424 288.201  1.00 15.37      6
ATOM    17  CG   ASN    84      40.672 118.725 288.496  1.00 16.97      6
ATOM    18  OD1  ASN    84      41.216 118.042 287.631  1.00 18.16      8
ATOM    19  ND2  ASN    84      41.194 118.907 289.691  1.00 13.80      7
ATOM    20  H    ASN    84      40.850 121.397 288.111  1.00  0.00      1
ATOM    21  1HD  ASN    84      42.070 118.474 289.867  1.00  0.00      6
ATOM    22  2HD  ASN    84      40.738 119.426 290.363  1.00  0.00      6
ATOM    23  N    VAL    85      37.081 120.415 286.419  1.00 13.79      7
ATOM    24  CA   VAL    85      35.708 120.903 286.486  1.00 12.64      6
ATOM    25  C    VAL    85      34.930 119.945 287.369  1.00 10.07      6
ATOM    26  O    VAL    85      34.685 118.815 286.991  1.00 10.76      8
ATOM    27  CB   VAL    85      35.082 120.935 285.093  1.00 12.63      6
ATOM    28  CG1  VAL    85      33.627 121.394 285.184  1.00 11.38      6
ATOM    29  CG2  VAL    85      35.900 121.840 284.191  1.00 10.89      6
ATOM    30  H    VAL    85      37.269 119.478 286.183  1.00  0.00      1
ATOM    31  N    LYS    86      34.681 120.346 288.612  1.00 10.36      7
ATOM    32  CA   LYS    86      33.977 119.474 289.548  1.00  9.43      6
ATOM    33  C    LYS    86      32.463 119.677 289.464  1.00 11.32      6
ATOM    34  O    LYS    86      31.986 120.752 289.115  1.00 14.21      8
ATOM    35  CB   LYS    86      34.466 119.703 290.965  1.00  8.00      6
ATOM    36  CG   LYS    86      35.963 119.468 291.130  1.00  7.74      6
ATOM    37  CD   LYS    86      36.283 117.997 291.087  1.00  7.78      6
ATOM    38  CE   LYS    86      37.764 117.767 291.351  1.00  9.88      6
ATOM    39  NZ   LYS    86      38.071 116.340 291.173  1.00  9.13      7
ATOM    40  H    LYS    86      35.011 121.214 288.941  1.00  0.00      1
ATOM    41  1HZ  LYS    86      37.494 115.749 291.803  1.00  0.00      6
ATOM    42  2HZ  LYS    86      37.898 116.100 290.178  1.00  0.00      6
ATOM    43  3HZ  LYS    86      39.074 116.157 291.399  1.00  0.00      6
ATOM    44  N    GLU    87      31.725 118.592 289.593  1.00 12.09      7
ATOM    45  CA   GLU    87      30.292 118.650 289.457  1.00 13.73      6
ATOM    46  C    GLU    87      29.575 118.656 290.813  1.00 14.69      6
ATOM    47  O    GLU    87      29.793 117.795 291.664  1.00 15.03      8
ATOM    48  CB   GLU    87      29.816 117.462 288.639  1.00 14.47      6
ATOM    49  CG   GLU    87      28.335 117.457 288.462  1.00 21.02      6
ATOM    50  CD   GLU    87      27.881 116.362 287.553  1.00 23.80      6
ATOM    51  OE1  GLU    87      27.977 115.177 287.945  1.00 24.97      8
ATOM    52  OE2  GLU    87      27.438 116.698 286.442  1.00 28.59      8
ATOM    53  H    GLU    87      32.170 117.750 289.853  1.00  0.00      1
ATOM    54  N    VAL    88      28.654 119.600 290.967  1.00 14.27      7
ATOM    55  CA   VAL    88      27.795 119.691 292.140  1.00 14.07      6
ATOM    56  C    VAL    88      26.352 119.529 291.657  1.00 13.32      6
ATOM    57  O    VAL    88      25.906 120.252 290.761  1.00 10.69      8
ATOM    58  CB   VAL    88      28.004 121.076 292.815  1.00 17.77      6
ATOM    59  CG1  VAL    88      26.927 121.339 293.848  1.00 18.13      6
ATOM    60  CG2  VAL    88      29.413 121.130 293.443  1.00 14.95      6
ATOM    61  H    VAL    88      28.541 120.236 290.241  1.00  0.00      1
ATOM    62  N    ARG    89      25.728 118.414 292.023  1.00 12.94      7
ATOM    63  CA   ARG    89      24.376 118.173 291.539  1.00 17.69      6
ATOM    64  C    ARG    89      23.295 118.617 292.527  1.00 18.67      6
ATOM    65  O    ARG    89      23.377 118.387 293.732  1.00 17.23      8
ATOM    66  CB   ARG    89      24.200 116.720 291.151  1.00 20.15      6
ATOM    67  CG   ARG    89      24.921 116.383 289.874  1.00 28.06      6
ATOM    68  CD   ARG    89      24.552 115.005 289.363  1.00 36.25      6
ATOM    69  NE   ARG    89      24.821 113.971 290.359  1.00 43.16      7
ATOM    70  CZ   ARG    89      26.038 113.537 290.706  1.00 48.12      6
ATOM    71  NH1  ARG    89      27.141 114.104 290.211  1.00 48.74      7
ATOM    72  NH2  ARG    89      26.153 112.550 291.591  1.00 50.70      7
ATOM    73  H    ARG    89      26.184 117.770 292.629  1.00  0.00      1
ATOM    74  HE   ARG    89      24.058 113.502 290.742  1.00  0.00      1
ATOM    75  1HH  ARG    89      27.064 114.837 289.548  1.00  0.00      6
ATOM    76  2HH  ARG    89      28.051 113.785 290.498  1.00  0.00      6
ATOM    77  1HH  ARG    89      25.337 112.103 291.955  1.00  0.00      6
ATOM    78  2HH  ARG    89      27.060 112.231 291.873  1.00  0.00      6
ATOM    79  N    LEU    90      22.333 119.380 292.011  1.00 18.93      7
ATOM    80  CA   LEU    90      21.243 119.891 292.826  1.00 20.82      6
ATOM    81  C    LEU    90      19.897 119.351 292.348  1.00 22.36      6
ATOM    82  O    LEU    90      19.684 119.101 291.165  1.00 19.75      8
ATOM    83  CB   LEU    90      21.210 121.431 292.806  1.00 17.38      6
ATOM    84  CG   LEU    90      22.280 122.309 293.480  1.00 18.81      6
ATOM    85  CD1  LEU    90      22.825 121.662 294.704  1.00 20.73      6
ATOM    86  CD2  LEU    90      23.392 122.588 292.511  1.00 19.00      6
ATOM    87  H    LEU    90      22.361 119.542 291.062  1.00  0.00      1
ATOM    88  N    SER    91      19.011 119.121 293.315  1.00 27.34      7
ATOM    89  CA   SER    91      17.644 118.653 293.061  1.00 29.05      6
ATOM    90  C    SER    91      16.718 119.849 292.925  1.00 28.58      6
ATOM    91  O    SER    91      16.922 120.882 293.559  1.00 31.27      8
ATOM    92  CB   SER    91      17.176 117.757 294.225  1.00 31.74      6
ATOM    93  OG   SER    91      15.829 117.324 294.069  1.00 35.17      8
ATOM    94  H    SER    91      19.278 119.343 294.232  1.00  0.00      1
ATOM    95  HG   SER    91      15.639 116.700 294.794  1.00  0.00      1
ATOM    96  N    PRO    92      15.659 119.722 292.130  1.00 29.39      7
ATOM    97  CA   PRO    92      14.720 120.849 292.022  1.00 28.18      6
```

```
ATOM   98  C    PRO   92     13.901 120.966 293.309  1.00 27.24      6
ATOM   99  O    PRO   92     13.486 122.050 293.715  1.00 27.45      8
ATOM  100  CB   PRO   92     13.850 120.470 290.830  1.00 28.57      6
ATOM  101  CG   PRO   92     13.907 118.974 290.792  1.00 29.69      6
ATOM  102  CD   PRO   92     15.295 118.606 291.228  1.00 30.07      6
ATOM  103  N    THR   93     13.844 119.855 294.029  1.00 26.58      7
ATOM  104  CA   THR   93     13.133 119.779 295.299  1.00 25.17      6
ATOM  105  C    THR   93     14.067 119.924 296.514  1.00 23.59      6
ATOM  106  O    THR   93     13.817 119.334 297.573  1.00 23.00      8
ATOM  107  CB   THR   93     12.390 118.436 295.374  1.00 25.38      6
ATOM  108  OG1  THR   93     13.339 117.366 295.501  1.00 29.33      8
ATOM  109  CG2  THR   93     11.587 118.224 294.118  1.00 25.02      6
ATOM  110  H    THR   93     14.310 119.052 293.713  1.00  0.00      1
ATOM  111  HG1  THR   93     13.922 117.376 294.740  1.00  0.00      1
ATOM  112  N    ILE   94     15.172 120.669 296.343  1.00 20.79      7
ATOM  113  CA   ILE   94     16.278 120.612 297.300  1.00 17.52      6
ATOM  114  C    ILE   94     15.949 121.328 298.615  1.00 13.82      6
ATOM  115  O    ILE   94     15.388 122.416 298.624  1.00 13.64      8
ATOM  116  CB   ILE   94     17.620 121.174 296.663  1.00 15.53      6
ATOM  117  CG1  ILE   94     18.831 120.721 297.491  1.00 18.24      6
ATOM  118  CG2  ILE   94     17.584 122.669 296.532  1.00 14.79      6
ATOM  119  CD1  ILE   94     20.179 121.173 296.971  1.00 10.77      6
ATOM  120  H    ILE   94     15.344 121.085 295.476  1.00  0.00      1
ATOM  121  N    GLU   95     16.188 120.641 299.730  1.00 12.67      7
ATOM  122  CA   GLU   95     15.832 121.164 301.046  1.00 13.51      6
ATOM  123  C    GLU   95     17.033 121.893 301.610  1.00 14.26      6
ATOM  124  O    GLU   95     18.131 121.774 301.087  1.00 14.29      8
ATOM  125  CB   GLU   95     15.395 120.026 301.969  1.00 14.34      6
ATOM  126  CG   GLU   95     14.193 119.268 301.423  1.00 17.04      6
ATOM  127  CD   GLU   95     13.637 118.211 302.371  1.00 18.21      6
ATOM  128  OE1  GLU   95     14.354 117.714 303.260  1.00 22.70      8
ATOM  129  OE2  GLU   95     12.494 117.776 302.128  1.00 22.88      8
ATOM  130  H    GLU   95     16.557 119.737 299.653  1.00  0.00      1
ATOM  131  N    GLU   96     16.832 122.625 302.700  1.00 12.57      7
ATOM  132  CA   GLU   96     17.821 123.564 303.173  1.00 16.13      6
ATOM  133  C    GLU   96     19.181 122.936 303.511  1.00 16.28      6
ATOM  134  O    GLU   96     20.223 123.481 303.108  1.00 15.87      8
ATOM  135  CB   GLU   96     17.266 124.341 304.365  1.00 18.20      6
ATOM  136  CG   GLU   96     18.145 125.484 304.865  1.00 24.25      6
ATOM  137  CD   GLU   96     18.407 126.567 303.815  1.00 29.91      6
ATOM  138  OE1  GLU   96     17.484 126.941 303.055  1.00 30.06      8
ATOM  139  OE2  GLU   96     19.537 127.104 303.812  1.00 33.54      8
ATOM  140  H    GLU   96     15.979 122.677 303.078  1.00  0.00      1
ATOM  141  N    HIS   97     19.198 121.786 304.197  1.00 16.60      7
ATOM  142  CA   HIS   97     20.485 121.238 304.623  1.00 17.70      6
ATOM  143  C    HIS   97     21.289 120.698 303.461  1.00 16.41      6
ATOM  144  O    HIS   97     22.500 120.835 303.443  1.00 14.48      8
ATOM  145  CB   HIS   97     20.351 120.162 305.697  1.00 18.32      6
ATOM  146  CG   HIS   97     21.665 119.810 306.358  1.00 24.04      6
ATOM  147  ND1  HIS   97     22.448 120.757 307.003  1.00 25.36      7
ATOM  148  CD2  HIS   97     22.348 118.645 306.451  1.00 23.61      6
ATOM  149  CE1  HIS   97     23.539 120.177 307.477  1.00 28.70      6
ATOM  150  NE2  HIS   97     23.510 118.896 307.157  1.00 29.67      7
ATOM  151  H    HIS   97     18.377 121.399 304.524  1.00  0.00      1
ATOM  152  HD1  HIS   97     22.225 121.685 307.099  1.00  0.00      1
ATOM  153  HE2  HIS   97     24.227 118.246 307.347  1.00  0.00      1
ATOM  154  N    ASP   98     20.634 119.986 302.559  1.00 16.43      7
ATOM  155  CA   ASP   98     21.281 119.531 301.348  1.00 17.39      6
ATOM  156  C    ASP   98     21.840 120.692 300.519  1.00 16.10      6
ATOM  157  O    ASP   98     22.977 120.637 300.047  1.00 16.81      8
ATOM  158  CB   ASP   98     20.313 118.685 300.520  1.00 22.11      6
ATOM  159  CG   ASP   98     20.967 118.100 299.269  1.00 33.06      6
ATOM  160  OD1  ASP   98     22.027 117.431 299.374  1.00 35.85      8
ATOM  161  OD2  ASP   98     20.411 118.304 298.162  1.00 36.78      8
ATOM  162  H    ASP   98     19.671 119.872 302.653  1.00  0.00      1
ATOM  163  N    PHE   99     21.095 121.785 300.415  1.00 13.86      7
ATOM  164  CA   PHE   99     21.614 122.981 299.760  1.00 13.48      6
ATOM  165  C    PHE   99     22.912 123.473 300.411  1.00 15.99      6
ATOM  166  O    PHE   99     23.903 123.730 299.725  1.00 13.07      8
ATOM  167  CB   PHE   99     20.574 124.104 299.779  1.00 12.85      6
ATOM  168  CG   PHE   99     20.999 125.338 299.044  1.00 12.59      6
ATOM  169  CD1  PHE   99     20.877 125.412 297.660  1.00 14.89      6
ATOM  170  CD2  PHE   99     21.667 126.348 299.712  1.00 11.05      6
ATOM  171  CE1  PHE   99     21.433 126.468 296.941  1.00 16.24      6
ATOM  172  CE2  PHE   99     22.240 127.403 299.022  1.00 14.21      6
ATOM  173  CZ   PHE   99     22.129 127.464 297.624  1.00 16.11      6
ATOM  174  H    PHE   99     20.239 121.785 300.881  1.00  0.00      1
ATOM  175  N    ASN  100     22.917 123.569 301.746  1.00 16.35      7
ATOM  176  CA   ASN  100     24.088 124.071 302.458  1.00 16.67      6
ATOM  177  C    ASN  100     25.267 123.108 302.306  1.00 14.60      6
ATOM  178  O    ASN  100     26.381 123.548 302.087  1.00 15.24      8
ATOM  179  CB   ASN  100     23.772 124.297 303.952  1.00 17.28      6
ATOM  180  CG   ASN  100     22.794 125.441 304.164  1.00 19.76      6
ATOM  181  OD1  ASN  100     22.603 126.291 303.299  1.00 19.27      8
ATOM  182  ND2  ASN  100     22.152 125.454 305.329  1.00 18.99      7
ATOM  183  H    ASN  100     22.125 123.357 302.273  1.00  0.00      1
ATOM  184  1HD  ASN  100     21.559 126.211 305.468  1.00  0.00      6
```

| | | | | | | | | | |
|---|---|---|---|---|---|---|---|---|---|
| ATOM | 185 | 2HD | ASN | 100 | 22.316 | 124.762 | 305.989 | 1.00 0.00 | 6 |
| ATOM | 186 | N | THR | 101 | 24.977 | 121.809 | 302.287 | 1.00 14.11 | 7 |
| ATOM | 187 | CA | THR | 101 | 25.974 | 120.756 | 302.079 | 1.00 17.24 | 6 |
| ATOM | 188 | C | THR | 101 | 26.639 | 120.834 | 300.698 | 1.00 17.16 | 6 |
| ATOM | 189 | O | THR | 101 | 27.863 | 120.873 | 300.563 | 1.00 15.27 | 8 |
| ATOM | 190 | CB | THR | 101 | 25.302 | 119.385 | 302.226 | 1.00 19.98 | 6 |
| ATOM | 191 | OG1 | THR | 101 | 24.795 | 119.255 | 303.568 | 1.00 24.61 | 8 |
| ATOM | 192 | CG2 | THR | 101 | 26.271 | 118.259 | 301.898 | 1.00 21.27 | 6 |
| ATOM | 193 | H | THR | 101 | 24.060 | 121.524 | 302.459 | 1.00 0.00 | 1 |
| ATOM | 194 | HG1 | THR | 101 | 24.216 | 119.972 | 303.794 | 1.00 0.00 | 1 |
| ATOM | 195 | N | LYS | 102 | 25.800 | 121.062 | 299.688 | 1.00 14.58 | 7 |
| ATOM | 196 | CA | LYS | 102 | 26.249 | 121.300 | 298.328 | 1.00 14.65 | 6 |
| ATOM | 197 | C | LYS | 102 | 26.979 | 122.623 | 298.166 | 1.00 14.28 | 6 |
| ATOM | 198 | O | LYS | 102 | 27.958 | 122.707 | 297.416 | 1.00 12.85 | 8 |
| ATOM | 199 | CB | LYS | 102 | 25.063 | 121.268 | 297.363 | 1.00 15.44 | 6 |
| ATOM | 200 | CG | LYS | 102 | 24.342 | 119.954 | 297.347 | 1.00 17.00 | 6 |
| ATOM | 201 | CD | LYS | 102 | 25.118 | 118.883 | 296.638 | 1.00 19.77 | 6 |
| ATOM | 202 | CE | LYS | 102 | 24.506 | 117.537 | 296.956 | 1.00 21.08 | 6 |
| ATOM | 203 | NZ | LYS | 102 | 23.076 | 117.568 | 296.606 | 1.00 25.00 | 7 |
| ATOM | 204 | H | LYS | 102 | 24.860 | 121.106 | 299.929 | 1.00 0.00 | 1 |
| ATOM | 205 | 1HZ | LYS | 102 | 22.959 | 117.820 | 295.605 | 1.00 0.00 | 6 |
| ATOM | 206 | 2HZ | LYS | 102 | 22.656 | 116.645 | 296.814 | 1.00 0.00 | 6 |
| ATOM | 207 | 3HZ | LYS | 102 | 22.621 | 118.274 | 297.218 | 1.00 0.00 | 6 |
| ATOM | 208 | N | LEU | 103 | 26.517 | 123.650 | 298.879 | 1.00 12.68 | 7 |
| ATOM | 209 | CA | LEU | 103 | 27.187 | 124.947 | 298.898 | 1.00 13.69 | 6 |
| ATOM | 210 | C | LEU | 103 | 28.597 | 124.868 | 299.527 | 1.00 14.12 | 6 |
| ATOM | 211 | O | LEU | 103 | 29.561 | 125.399 | 298.976 | 1.00 14.32 | 8 |
| ATOM | 212 | CB | LEU | 103 | 26.329 | 125.976 | 299.632 | 1.00 12.02 | 6 |
| ATOM | 213 | CG | LEU | 103 | 27.034 | 127.287 | 299.997 | 1.00 15.48 | 6 |
| ATOM | 214 | CD1 | LEU | 103 | 27.567 | 127.993 | 298.756 | 1.00 14.27 | 6 |
| ATOM | 215 | CD2 | LEU | 103 | 26.073 | 128.185 | 300.733 | 1.00 15.88 | 6 |
| ATOM | 216 | H | LEU | 103 | 25.789 | 123.466 | 299.498 | 1.00 0.00 | 1 |
| ATOM | 217 | N | ARG | 104 | 28.713 | 124.109 | 300.616 | 1.00 16.05 | 7 |
| ATOM | 218 | CA | ARG | 104 | 29.981 | 123.847 | 301.301 | 1.00 16.08 | 6 |
| ATOM | 219 | C | ARG | 104 | 30.954 | 123.186 | 300.320 | 1.00 15.03 | 6 |
| ATOM | 220 | O | ARG | 104 | 32.067 | 123.668 | 300.103 | 1.00 15.16 | 8 |
| ATOM | 221 | CB | ARG | 104 | 29.722 | 122.936 | 302.520 | 1.00 17.62 | 6 |
| ATOM | 222 | CG | ARG | 104 | 30.939 | 122.652 | 303.403 | 1.00 26.00 | 6 |
| ATOM | 223 | CD | ARG | 104 | 30.571 | 121.817 | 304.635 | 1.00 31.23 | 6 |
| ATOM | 224 | NE | ARG | 104 | 30.142 | 120.463 | 304.281 | 1.00 36.14 | 7 |
| ATOM | 225 | CZ | ARG | 104 | 29.068 | 119.861 | 304.786 | 1.00 37.65 | 6 |
| ATOM | 226 | NH1 | ARG | 104 | 28.170 | 120.555 | 305.479 | 1.00 38.49 | 7 |
| ATOM | 227 | NH2 | ARG | 104 | 28.846 | 118.580 | 304.519 | 1.00 38.11 | 7 |
| ATOM | 228 | H | ARG | 104 | 27.940 | 123.651 | 300.992 | 1.00 0.00 | 1 |
| ATOM | 229 | HE | ARG | 104 | 30.790 | 119.919 | 303.785 | 1.00 0.00 | 1 |
| ATOM | 230 | 1HH | ARG | 104 | 28.379 | 121.496 | 305.753 | 1.00 0.00 | 6 |
| ATOM | 231 | 2HH | ARG | 104 | 27.359 | 120.103 | 305.834 | 1.00 0.00 | 6 |
| ATOM | 232 | 1HH | ARG | 104 | 29.508 | 118.061 | 303.976 | 1.00 0.00 | 6 |
| ATOM | 233 | 2HH | ARG | 104 | 27.999 | 118.143 | 304.822 | 1.00 0.00 | 6 |
| ATOM | 234 | N | ASN | 105 | 30.490 | 122.123 | 299.662 | 1.00 13.07 | 7 |
| ATOM | 235 | CA | ASN | 105 | 31.286 | 121.389 | 298.679 | 1.00 14.70 | 6 |
| ATOM | 236 | C | ASN | 105 | 31.792 | 122.229 | 297.494 | 1.00 12.81 | 6 |
| ATOM | 237 | O | ASN | 105 | 32.960 | 122.135 | 297.103 | 1.00 13.12 | 8 |
| ATOM | 238 | CB | ASN | 105 | 30.489 | 120.207 | 298.131 | 1.00 15.23 | 6 |
| ATOM | 239 | CG | ASN | 105 | 30.169 | 119.177 | 299.183 | 1.00 18.33 | 6 |
| ATOM | 240 | OD1 | ASN | 105 | 29.489 | 118.205 | 298.893 | 1.00 23.72 | 8 |
| ATOM | 241 | ND2 | ASN | 105 | 30.732 | 119.320 | 300.362 | 1.00 16.81 | 7 |
| ATOM | 242 | H | ASN | 105 | 29.613 | 121.783 | 299.926 | 1.00 0.00 | 1 |
| ATOM | 243 | 1HD | ASN | 105 | 30.595 | 118.594 | 301.009 | 1.00 0.00 | 6 |
| ATOM | 244 | 2HD | ASN | 105 | 31.347 | 120.045 | 300.582 | 1.00 0.00 | 6 |
| ATOM | 245 | N | ALA | 106 | 30.887 | 123.009 | 296.906 | 1.00 10.81 | 7 |
| ATOM | 246 | CA | ALA | 106 | 31.220 | 124.010 | 295.891 | 1.00 9.36 | 6 |
| ATOM | 247 | C | ALA | 106 | 32.289 | 125.006 | 296.342 | 1.00 10.75 | 6 |
| ATOM | 248 | O | ALA | 106 | 33.250 | 125.237 | 295.644 | 1.00 11.66 | 8 |
| ATOM | 249 | CB | ALA | 106 | 29.961 | 124.776 | 295.468 | 1.00 8.06 | 6 |
| ATOM | 250 | H | ALA | 106 | 30.013 | 123.028 | 297.351 | 1.00 0.00 | 1 |
| ATOM | 251 | N | ARG | 107 | 32.128 | 125.606 | 297.504 | 1.00 9.63 | 7 |
| ATOM | 252 | CA | ARG | 107 | 33.144 | 126.507 | 298.018 | 1.00 12.30 | 6 |
| ATOM | 253 | C | ARG | 107 | 34.472 | 125.784 | 298.238 | 1.00 14.05 | 6 |
| ATOM | 254 | O | ARG | 107 | 35.517 | 126.316 | 297.906 | 1.00 15.70 | 8 |
| ATOM | 255 | CB | ARG | 107 | 32.656 | 127.164 | 299.314 | 1.00 10.47 | 6 |
| ATOM | 256 | CG | ARG | 107 | 31.474 | 128.125 | 299.070 | 1.00 7.95 | 6 |
| ATOM | 257 | CD | ARG | 107 | 31.028 | 128.896 | 300.322 | 1.00 11.93 | 6 |
| ATOM | 258 | NE | ARG | 107 | 32.050 | 129.779 | 300.880 | 1.00 10.74 | 7 |
| ATOM | 259 | CZ | ARG | 107 | 32.256 | 131.031 | 300.501 | 1.00 11.18 | 6 |
| ATOM | 260 | NH1 | ARG | 107 | 31.439 | 131.578 | 299.613 | 1.00 9.91 | 7 |
| ATOM | 261 | NH2 | ARG | 107 | 33.294 | 131.716 | 300.973 | 1.00 11.82 | 7 |
| ATOM | 262 | H | ARG | 107 | 31.379 | 125.393 | 298.090 | 1.00 0.00 | 1 |
| ATOM | 263 | HE | ARG | 107 | 32.694 | 129.435 | 301.569 | 1.00 0.00 | 1 |
| ATOM | 264 | 1HH | ARG | 107 | 30.720 | 131.036 | 299.204 | 1.00 0.00 | 6 |
| ATOM | 265 | 2HH | ARG | 107 | 31.609 | 132.506 | 299.375 | 1.00 0.00 | 6 |
| ATOM | 266 | 1HH | ARG | 107 | 33.927 | 131.309 | 301.647 | 1.00 0.00 | 6 |
| ATOM | 267 | 2HH | ARG | 107 | 33.477 | 132.660 | 300.744 | 1.00 0.00 | 6 |
| ATOM | 268 | N | LYS | 108 | 34.425 | 124.524 | 298.678 | 1.00 16.05 | 7 |
| ATOM | 269 | CA | LYS | 108 | 35.638 | 123.733 | 298.878 | 1.00 16.95 | 6 |
| ATOM | 270 | C | LYS | 108 | 36.397 | 123.465 | 297.561 | 1.00 15.87 | 6 |
| ATOM | 271 | O | LYS | 108 | 37.613 | 123.617 | 297.478 | 1.00 14.99 | 8 |

```
ATOM  272  CB   LYS  108    35.293 122.422 299.575  1.00 19.50   6
ATOM  273  CG   LYS  108    36.494 121.511 299.767  1.00 26.98   6
ATOM  274  CD   LYS  108    36.090 120.131 300.268  1.00 32.74   6
ATOM  275  CE   LYS  108    36.973 119.038 299.651  1.00 36.59   6
ATOM  276  NZ   LYS  108    36.871 118.965 298.157  1.00 36.43   7
ATOM  277  H    LYS  108    33.578 124.123 298.928  1.00  0.00   1
ATOM  278  1HZ  LYS  108    35.895 118.757 297.895  1.00  0.00   6
ATOM  279  2HZ  LYS  108    37.184 119.866 297.748  1.00  0.00   6
ATOM  280  3HZ  LYS  108    37.486 118.195 297.826  1.00  0.00   6
ATOM  281  N    PHE  109    35.658 123.162 296.502  1.00 13.80   7
ATOM  282  CA   PHE  109    36.262 122.977 295.183  1.00 11.07   6
ATOM  283  C    PHE  109    36.860 124.258 294.642  1.00  9.79   6
ATOM  284  O    PHE  109    37.974 124.268 294.166  1.00  9.05   8
ATOM  285  CB   PHE  109    35.237 122.442 294.186  1.00  9.30   6
ATOM  286  CG   PHE  109    34.817 121.049 294.476  1.00 11.63   6
ATOM  287  CD1  PHE  109    35.757 120.074 294.774  1.00 12.62   6
ATOM  288  CD2  PHE  109    33.485 120.693 294.369  1.00 14.50   6
ATOM  289  CE1  PHE  109    35.376 118.758 294.936  1.00 12.77   6
ATOM  290  CE2  PHE  109    33.080 119.381 294.532  1.00 13.93   6
ATOM  291  CZ   PHE  109    34.036 118.401 294.809  1.00 14.10   6
ATOM  292  H    PHE  109    34.702 123.093 296.670  1.00  0.00   1
ATOM  293  N    LEU  110    36.150 125.371 294.827  1.00  8.43   7
ATOM  294  CA   LEU  110    36.599 126.656 294.321  1.00  8.86   6
ATOM  295  C    LEU  110    37.831 127.151 295.054  1.00 10.22   6
ATOM  296  O    LEU  110    38.727 127.725 294.424  1.00  8.99   8
ATOM  297  CB   LEU  110    35.495 127.705 294.419  1.00  7.98   6
ATOM  298  CG   LEU  110    34.360 127.466 293.429  1.00  7.05   6
ATOM  299  CD1  LEU  110    33.117 128.163 293.960  1.00 10.45   6
ATOM  300  CD2  LEU  110    34.731 127.981 292.056  1.00  3.62   6
ATOM  301  H    LEU  110    35.337 125.307 295.352  1.00  0.00   1
ATOM  302  N    GLU  111    37.852 126.971 296.378  1.00  9.94   7
ATOM  303  CA   GLU  111    39.014 127.315 297.201  1.00 13.93   6
ATOM  304  C    GLU  111    40.239 126.486 296.805  1.00 14.78   6
ATOM  305  O    GLU  111    41.360 126.950 296.942  1.00 16.10   8
ATOM  306  CB   GLU  111    38.724 127.078 298.688  1.00 16.04   6
ATOM  307  CG   GLU  111    37.724 128.038 299.356  1.00 21.14   6
ATOM  308  CD   GLU  111    38.276 129.447 299.536  1.00 27.14   6
ATOM  309  OE1  GLU  111    39.157 129.848 298.751  1.00 31.29   8
ATOM  310  OE2  GLU  111    37.802 130.170 300.446  1.00 27.84   8
ATOM  311  H    GLU  111    37.156 126.509 296.878  1.00  0.00   1
ATOM  312  N    LYS  112    40.023 125.263 296.334  1.00 15.55   7
ATOM  313  CA   LYS  112    41.107 124.420 295.828  1.00 18.18   6
ATOM  314  C    LYS  112    41.560 124.791 294.406  1.00 18.07   6
ATOM  315  O    LYS  112    42.450 124.157 293.861  1.00 18.96   8
ATOM  316  CB   LYS  112    40.716 122.931 295.857  1.00 20.33   6
ATOM  317  CG   LYS  112    40.209 122.401 297.205  1.00 26.65   6
ATOM  318  CD   LYS  112    41.038 122.908 298.400  1.00 29.55   6
ATOM  319  CE   LYS  112    40.255 122.845 299.730  1.00 31.52   6
ATOM  320  NZ   LYS  112    39.350 124.023 299.963  1.00 26.10   7
ATOM  321  H    LYS  112    39.119 124.954 296.264  1.00  0.00   1
ATOM  322  1HZ  LYS  112    39.919 124.894 299.965  1.00  0.00   6
ATOM  323  2HZ  LYS  112    38.656 124.048 299.193  1.00  0.00   6
ATOM  324  3HZ  LYS  112    38.887 123.908 300.878  1.00  0.00   6
ATOM  325  N    GLY  113    40.866 125.739 293.770  1.00 16.98   7
ATOM  326  CA   GLY  113    41.274 126.233 292.455  1.00 13.36   6
ATOM  327  C    GLY  113    40.540 125.573 291.297  1.00 14.55   6
ATOM  328  O    GLY  113    40.859 125.769 290.107  1.00 14.78   8
ATOM  329  H    GLY  113    40.199 126.226 294.285  1.00  0.00   1
ATOM  330  N    ASP  114    39.570 124.717 291.625  1.00 12.53   7
ATOM  331  CA   ASP  114    38.844 124.014 290.588  1.00 11.88   6
ATOM  332  C    ASP  114    37.558 124.698 290.217  1.00 13.53   6
ATOM  333  O    ASP  114    37.018 125.488 290.981  1.00 13.62   8
ATOM  334  CB   ASP  114    38.549 122.581 290.987  1.00 12.76   6
ATOM  335  CG   ASP  114    39.801 121.714 290.980  1.00 14.48   6
ATOM  336  OD1  ASP  114    40.766 121.983 290.223  1.00 19.52   8
ATOM  337  OD2  ASP  114    39.811 120.770 291.767  1.00 18.28   8
ATOM  338  H    ASP  114    39.412 124.580 292.600  1.00  0.00   1
ATOM  339  N    LYS  115    37.166 124.538 288.962  1.00 13.84   7
ATOM  340  CA   LYS  115    35.911 125.122 288.530  1.00 12.52   6
ATOM  341  C    LYS  115    34.761 124.229 288.953  1.00  9.34   6
ATOM  342  O    LYS  115    34.956 123.070 289.312  1.00  9.03   8
ATOM  343  CB   LYS  115    35.894 125.341 287.025  1.00 11.39   6
ATOM  344  CG   LYS  115    36.823 126.434 286.588  1.00 13.85   6
ATOM  345  CD   LYS  115    36.766 126.572 285.095  1.00 14.94   6
ATOM  346  CE   LYS  115    37.738 127.616 284.657  1.00 15.10   6
ATOM  347  NZ   LYS  115    37.701 127.745 283.196  1.00 16.84   7
ATOM  348  H    LYS  115    37.712 123.969 288.383  1.00  0.00   1
ATOM  349  1HZ  LYS  115    37.970 126.854 282.749  1.00  0.00   6
ATOM  350  2HZ  LYS  115    36.765 128.074 282.892  1.00  0.00   6
ATOM  351  3HZ  LYS  115    38.371 128.484 282.929  1.00  0.00   6
ATOM  352  N    VAL  116    33.584 124.814 289.030  1.00 10.84   7
ATOM  353  CA   VAL  116    32.412 124.077 289.500  1.00 10.14   6
ATOM  354  C    VAL  116    31.262 124.178 288.486  1.00  7.46   6
ATOM  355  O    VAL  116    30.830 125.256 288.111  1.00  7.64   8
ATOM  356  CB   VAL  116    31.940 124.581 290.925  1.00 10.98   6
ATOM  357  CG1  VAL  116    30.642 123.906 291.303  1.00 11.74   6
ATOM  358  CG2  VAL  116    32.999 124.245 292.007  1.00  9.84   6
```

| | | | | | | | | | |
|---|---|---|---|---|---|---|---|---|---|
| ATOM | 359 | H | VAL | 116 | 33.518 125.749 288.786 | 1.00 | 0.00 | 1 |
| ATOM | 360 | N | LYS | 117 | 30.775 123.024 288.051 | 1.00 | 9.26 | 7 |
| ATOM | 361 | CA | LYS | 117 | 29.595 122.973 287.212 | 1.00 | 9.73 | 6 |
| ATOM | 362 | C | LYS | 117 | 28.450 122.477 288.083 | 1.00 | 9.31 | 6 |
| ATOM | 363 | O | LYS | 117 | 28.530 121.391 288.633 | 1.00 | 8.75 | 8 |
| ATOM | 364 | CB | LYS | 117 | 29.798 122.035 286.026 | 1.00 | 11.26 | 6 |
| ATOM | 365 | CG | LYS | 117 | 28.570 121.945 285.120 | 1.00 | 13.83 | 6 |
| ATOM | 366 | CD | LYS | 117 | 28.661 120.792 284.135 | 1.00 | 16.84 | 6 |
| ATOM | 367 | CE | LYS | 117 | 27.429 120.742 283.214 | 1.00 | 20.32 | 6 |
| ATOM | 368 | NZ | LYS | 117 | 27.419 119.690 282.133 | 1.00 | 23.52 | 7 |
| ATOM | 369 | H | LYS | 117 | 31.194 122.196 288.390 | 1.00 | 0.00 | 1 |
| ATOM | 370 | 1HZ | LYS | 117 | 27.506 118.747 282.577 | 1.00 | 0.00 | 6 |
| ATOM | 371 | 2HZ | LYS | 117 | 26.511 119.710 281.622 | 1.00 | 0.00 | 6 |
| ATOM | 372 | 3HZ | LYS | 117 | 28.213 119.807 281.468 | 1.00 | 0.00 | 6 |
| ATOM | 373 | N | ALA | 118 | 27.504 123.378 288.375 | 1.00 | 9.50 | 7 |
| ATOM | 374 | CA | ALA | 118 | 26.341 123.070 289.219 | 1.00 | 9.35 | 6 |
| ATOM | 375 | C | ALA | 118 | 25.199 122.686 288.314 | 1.00 | 10.32 | 6 |
| ATOM | 376 | O | ALA | 118 | 24.807 123.472 287.464 | 1.00 | 10.40 | 8 |
| ATOM | 377 | CB | ALA | 118 | 25.941 124.282 290.041 | 1.00 | 6.15 | 6 |
| ATOM | 378 | H | ALA | 118 | 27.641 124.283 288.024 | 1.00 | 0.00 | 1 |
| ATOM | 379 | N | THR | 119 | 24.709 121.467 288.464 | 1.00 | 9.87 | 7 |
| ATOM | 380 | CA | THR | 119 | 23.693 120.960 287.556 | 1.00 | 13.42 | 6 |
| ATOM | 381 | C | THR | 119 | 22.391 120.510 288.234 | 1.00 | 13.24 | 6 |
| ATOM | 382 | O | THR | 119 | 22.396 119.934 289.301 | 1.00 | 12.28 | 8 |
| ATOM | 383 | CB | THR | 119 | 24.237 119.784 286.695 | 1.00 | 14.57 | 6 |
| ATOM | 384 | OG1 | THR | 119 | 25.529 120.130 286.177 | 1.00 | 19.60 | 8 |
| ATOM | 385 | CG2 | THR | 119 | 23.323 119.544 285.515 | 1.00 | 18.23 | 6 |
| ATOM | 386 | H | THR | 119 | 25.083 120.896 289.182 | 1.00 | 0.00 | 1 |
| ATOM | 387 | HG1 | THR | 119 | 26.171 120.252 286.888 | 1.00 | 0.00 | 1 |
| ATOM | 388 | N | ILE | 120 | 21.276 120.808 287.585 | 1.00 | 13.58 | 7 |
| ATOM | 389 | CA | ILE | 120 | 19.958 120.341 287.990 | 1.00 | 14.88 | 6 |
| ATOM | 390 | C | ILE | 120 | 19.363 119.504 286.852 | 1.00 | 15.47 | 6 |
| ATOM | 391 | O | ILE | 120 | 19.215 119.993 285.738 | 1.00 | 13.40 | 8 |
| ATOM | 392 | CB | ILE | 120 | 19.018 121.547 288.278 | 1.00 | 16.52 | 6 |
| ATOM | 393 | CG1 | ILE | 120 | 19.523 122.341 289.495 | 1.00 | 14.87 | 6 |
| ATOM | 394 | CG2 | ILE | 120 | 17.584 121.056 288.495 | 1.00 | 16.03 | 6 |
| ATOM | 395 | CD1 | ILE | 120 | 18.822 123.648 289.649 | 1.00 | 14.91 | 6 |
| ATOM | 396 | H | ILE | 120 | 21.374 121.241 286.712 | 1.00 | 0.00 | 1 |
| ATOM | 397 | N | ARG | 121 | 19.104 118.223 287.107 | 1.00 | 15.44 | 7 |
| ATOM | 398 | CA | ARG | 121 | 18.483 117.384 286.095 | 1.00 | 20.43 | 6 |
| ATOM | 399 | C | ARG | 121 | 16.987 117.289 286.403 | 1.00 | 21.42 | 6 |
| ATOM | 400 | O | ARG | 121 | 16.573 116.824 287.481 | 1.00 | 23.74 | 8 |
| ATOM | 401 | CB | ARG | 121 | 19.123 115.985 286.017 | 1.00 | 23.44 | 6 |
| ATOM | 402 | CG | ARG | 121 | 18.651 115.154 284.796 | 1.00 | 32.86 | 6 |
| ATOM | 403 | CD | ARG | 121 | 19.364 113.783 284.623 | 1.00 | 38.52 | 6 |
| ATOM | 404 | NE | ARG | 121 | 20.746 113.886 284.128 | 1.00 | 42.58 | 7 |
| ATOM | 405 | CZ | ARG | 121 | 21.094 114.078 282.856 | 1.00 | 43.58 | 6 |
| ATOM | 406 | NH1 | ARG | 121 | 20.183 114.405 281.943 | 1.00 | 45.56 | 7 |
| ATOM | 407 | NH2 | ARG | 121 | 22.376 114.091 282.525 | 1.00 | 45.51 | 7 |
| ATOM | 408 | H | ARG | 121 | 19.288 117.866 288.002 | 1.00 | 0.00 | 1 |
| ATOM | 409 | HE | ARG | 121 | 21.465 113.682 284.754 | 1.00 | 0.00 | 1 |
| ATOM | 410 | 1HH | ARG | 121 | 19.208 114.386 282.151 | 1.00 | 0.00 | 6 |
| ATOM | 411 | 2HH | ARG | 121 | 20.473 114.593 280.997 | 1.00 | 0.00 | 6 |
| ATOM | 412 | 1HH | ARG | 121 | 23.083 113.955 283.220 | 1.00 | 0.00 | 6 |
| ATOM | 413 | 2HH | ARG | 121 | 22.650 114.352 281.596 | 1.00 | 0.00 | 6 |
| ATOM | 414 | N | PHE | 122 | 16.190 117.890 285.524 | 1.00 | 20.48 | 7 |
| ATOM | 415 | CA | PHE | 122 | 14.758 117.978 285.725 | 1.00 | 22.57 | 6 |
| ATOM | 416 | C | PHE | 122 | 14.033 116.687 285.374 | 1.00 | 24.27 | 6 |
| ATOM | 417 | O | PHE | 122 | 14.350 116.041 284.380 | 1.00 | 24.79 | 8 |
| ATOM | 418 | CB | PHE | 122 | 14.210 119.121 284.896 | 1.00 | 20.89 | 6 |
| ATOM | 419 | CG | PHE | 122 | 14.655 120.451 285.368 | 1.00 | 21.85 | 6 |
| ATOM | 420 | CD1 | PHE | 122 | 14.363 120.862 286.670 | 1.00 | 23.46 | 6 |
| ATOM | 421 | CD2 | PHE | 122 | 15.355 121.304 284.538 | 1.00 | 22.65 | 6 |
| ATOM | 422 | CE1 | PHE | 122 | 14.759 122.104 287.126 | 1.00 | 22.80 | 6 |
| ATOM | 423 | CE2 | PHE | 122 | 15.745 122.552 284.983 | 1.00 | 22.50 | 6 |
| ATOM | 424 | CZ | PHE | 122 | 15.447 122.949 286.285 | 1.00 | 21.54 | 6 |
| ATOM | 425 | H | PHE | 122 | 16.602 118.274 284.722 | 1.00 | 0.00 | 1 |
| ATOM | 426 | N | LYS | 123 | 13.147 116.258 286.269 | 1.00 | 24.63 | 7 |
| ATOM | 427 | CA | LYS | 123 | 12.257 115.117 286.028 | 1.00 | 26.47 | 6 |
| ATOM | 428 | C | LYS | 123 | 10.871 115.658 285.699 | 1.00 | 23.52 | 6 |
| ATOM | 429 | O | LYS | 123 | 10.433 116.645 286.280 | 1.00 | 23.92 | 8 |
| ATOM | 430 | CB | LYS | 123 | 12.198 114.200 287.261 | 1.00 | 29.47 | 6 |
| ATOM | 431 | CG | LYS | 123 | 13.563 113.689 287.738 | 1.00 | 35.55 | 6 |
| ATOM | 432 | CD | LYS | 123 | 14.373 113.024 286.594 | 1.00 | 39.61 | 6 |
| ATOM | 433 | CE | LYS | 123 | 15.764 112.558 287.056 | 1.00 | 41.09 | 6 |
| ATOM | 434 | NZ | LYS | 123 | 16.603 113.672 287.596 | 1.00 | 43.78 | 7 |
| ATOM | 435 | H | LYS | 123 | 13.009 116.781 287.067 | 1.00 | 0.00 | 1 |
| ATOM | 436 | 1HZ | LYS | 123 | 16.133 114.119 288.415 | 1.00 | 0.00 | 6 |
| ATOM | 437 | 2HZ | LYS | 123 | 17.525 113.311 287.918 | 1.00 | 0.00 | 6 |
| ATOM | 438 | 3HZ | LYS | 123 | 16.743 114.389 286.859 | 1.00 | 0.00 | 6 |
| ATOM | 439 | N | GLY | 124 | 10.283 115.149 284.631 | 1.00 | 21.81 | 7 |
| ATOM | 440 | CA | GLY | 124 | 8.982 115.629 284.220 | 1.00 | 21.52 | 6 |
| ATOM | 441 | C | GLY | 124 | 8.971 117.029 283.641 | 1.00 | 19.66 | 6 |
| ATOM | 442 | O | GLY | 124 | 10.006 117.670 283.504 | 1.00 | 20.79 | 8 |
| ATOM | 443 | H | GLY | 124 | 10.710 114.422 284.126 | 1.00 | 0.00 | 1 |
| ATOM | 444 | N | ARG | 125 | 7.781 117.537 283.365 | 1.00 | 19.55 | 7 |
| ATOM | 445 | CA | ARG | 125 | 7.649 118.793 282.663 | 1.00 | 19.50 | 6 |

```
ATOM    446  C   ARG   125       6.855 119.841 283.454  1.00 18.92           6
ATOM    447  O   ARG   125       5.981 120.520 282.915  1.00 19.08           8
ATOM    448  CB  ARG   125       6.973 118.555 281.305  1.00 21.13           6
ATOM    449  CG  ARG   125       7.756 117.647 280.362  1.00 23.44           6
ATOM    450  CD  ARG   125       9.059 118.309 279.899  1.00 23.21           6
ATOM    451  NE  ARG   125       9.843 117.431 279.027  1.00 23.41           7
ATOM    452  CZ  ARG   125      10.647 117.863 278.065  1.00 23.80           6
ATOM    453  NH1 ARG   125      10.783 119.158 277.857  1.00 21.64           7
ATOM    454  NH2 ARG   125      11.311 117.004 277.307  1.00 23.26           7
ATOM    455  H   ARG   125       7.006 116.989 283.567  1.00  0.00           1
ATOM    456  HE  ARG   125       9.746 116.482 279.143  1.00  0.00           1
ATOM    457  1HH ARG   125      10.242 119.798 278.385  1.00  0.00           6
ATOM    458  2HH ARG   125      11.333 119.444 277.082  1.00  0.00           6
ATOM    459  1HH ARG   125      11.189 116.034 277.458  1.00  0.00           6
ATOM    460  2HH ARG   125      11.869 117.279 276.526  1.00  0.00           6
ATOM    461  N   ALA   126       7.181 120.019 284.726  1.00 19.60           7
ATOM    462  CA  ALA   126       6.508 121.081 285.490  1.00 18.39           6
ATOM    463  C   ALA   126       6.664 122.441 284.825  1.00 18.32           6
ATOM    464  O   ALA   126       7.739 122.795 284.344  1.00 18.35           8
ATOM    465  CB  ALA   126       7.024 121.128 286.900  1.00 18.37           6
ATOM    466  H   ALA   126       7.847 119.431 285.140  1.00  0.00           1
ATOM    467  N   ILE   127       5.608 123.235 284.890  1.00 18.86           7
ATOM    468  CA  ILE   127       5.569 124.544 284.230  1.00 18.16           6
ATOM    469  C   ILE   127       6.514 125.532 284.913  1.00 17.38           6
ATOM    470  O   ILE   127       6.799 126.610 284.401  1.00 17.14           8
ATOM    471  CB  ILE   127       4.109 125.134 284.215  1.00 19.15           6
ATOM    472  CG1 ILE   127       3.580 125.305 285.635  1.00 19.12           6
ATOM    473  CG2 ILE   127       3.153 124.205 283.436  1.00 18.62           6
ATOM    474  CD1 ILE   127       2.186 125.897 285.668  1.00 21.49           6
ATOM    475  H   ILE   127       4.769 122.865 285.274  1.00  0.00           1
ATOM    476  N   THR   128       6.994 125.149 286.092  1.00 16.32           7
ATOM    477  CA  THR   128       7.730 126.061 286.962  1.00 17.71           6
ATOM    478  C   THR   128       9.231 125.695 287.079  1.00 16.65           6
ATOM    479  O   THR   128      10.017 126.410 287.698  1.00 14.61           8
ATOM    480  CB  THR   128       7.055 126.085 288.348  1.00 19.38           6
ATOM    481  OG1 THR   128       7.484 127.241 289.067  1.00 28.80           8
ATOM    482  CG2 THR   128       7.362 124.835 289.126  1.00 16.08           6
ATOM    483  H   THR   128       6.710 124.268 286.417  1.00  0.00           1
ATOM    484  HG1 THR   128       6.987 127.297 289.893  1.00  0.00           1
ATOM    485  N   HIS   129       9.628 124.646 286.358  1.00 16.16           7
ATOM    486  CA  HIS   129      10.988 124.106 286.425  1.00 17.55           6
ATOM    487  C   HIS   129      12.103 125.082 286.117  1.00 16.53           6
ATOM    488  O   HIS   129      13.059 125.153 286.886  1.00 15.50           8
ATOM    489  CB  HIS   129      11.114 122.880 285.518  1.00 19.04           6
ATOM    490  CG  HIS   129      10.812 121.592 286.204  1.00 18.62           6
ATOM    491  ND1 HIS   129      10.615 120.407 285.528  1.00 20.43           7
ATOM    492  CD2 HIS   129      10.668 121.299 287.524  1.00 19.29           6
ATOM    493  CE1 HIS   129      10.362 119.445 286.390  1.00 20.17           6
ATOM    494  NE2 HIS   129      10.390 119.957 287.617  1.00 18.64           7
ATOM    495  H   HIS   129       8.936 124.164 285.845  1.00  0.00           1
ATOM    496  HD1 HIS   129      10.580 120.292 284.548  1.00  0.00           1
ATOM    497  HE2 HIS   129      10.278 119.448 288.451  1.00  0.00           1
ATOM    498  N   LYS   130      11.994 125.802 285.005  1.00 18.33           7
ATOM    499  CA  LYS   130      13.025 126.765 284.609  1.00 22.86           6
ATOM    500  C   LYS   130      13.177 127.884 285.642  1.00 23.79           6
ATOM    501  O   LYS   130      14.265 128.393 285.889  1.00 23.74           8
ATOM    502  CB  LYS   130      12.684 127.379 283.260  1.00 26.05           6
ATOM    503  CG  LYS   130      13.909 127.778 282.439  1.00 34.58           6
ATOM    504  CD  LYS   130      13.775 129.182 281.849  1.00 39.92           6
ATOM    505  CE  LYS   130      13.757 130.269 282.945  1.00 44.10           6
ATOM    506  NZ  LYS   130      14.998 130.282 283.791  1.00 45.20           7
ATOM    507  H   LYS   130      11.182 125.727 284.454  1.00  0.00           1
ATOM    508  1HZ LYS   130      15.850 130.439 283.212  1.00  0.00           6
ATOM    509  2HZ LYS   130      14.923 131.039 284.497  1.00  0.00           6
ATOM    510  3HZ LYS   130      15.086 129.370 284.283  1.00  0.00           6
ATOM    511  N   GLU   131      12.052 128.274 286.233  1.00 25.14           7
ATOM    512  CA  GLU   131      12.027 129.298 287.257  1.00 24.65           6
ATOM    513  C   GLU   131      12.697 128.855 288.541  1.00 22.21           6
ATOM    514  O   GLU   131      13.507 129.577 289.098  1.00 24.73           8
ATOM    515  CB  GLU   131      10.570 129.718 287.530  1.00 28.35           6
ATOM    516  CG  GLU   131       9.845 130.222 286.267  1.00 33.32           6
ATOM    517  CD  GLU   131       8.876 129.198 285.665  1.00 36.51           6
ATOM    518  OE1 GLU   131       9.311 128.302 284.890  1.00 28.77           8
ATOM    519  OE2 GLU   131       7.658 129.335 285.969  1.00 37.56           8
ATOM    520  H   GLU   131      11.222 127.817 285.990  1.00  0.00           1
ATOM    521  N   ILE   132      12.451 127.630 288.982  1.00 20.03           7
ATOM    522  CA  ILE   132      13.047 127.209 290.237  1.00 19.85           6
ATOM    523  C   ILE   132      14.483 126.739 290.059  1.00 18.77           6
ATOM    524  O   ILE   132      15.287 126.884 290.964  1.00 15.39           8
ATOM    525  CB  ILE   132      12.199 126.111 290.941  1.00 20.80           6
ATOM    526  CG1 ILE   132      12.507 124.726 290.379  1.00 21.27           6
ATOM    527  CG2 ILE   132      10.734 126.355 290.690  1.00 24.64           6
ATOM    528  CD1 ILE   132      13.403 123.898 291.244  1.00 22.62           6
ATOM    529  H   ILE   132      11.814 127.062 288.495  1.00  0.00           1
ATOM    530  N   GLY   133      14.804 126.200 288.881  1.00 16.53           7
ATOM    531  CA  GLY   133      16.179 125.839 288.582  1.00 13.57           6
ATOM    532  C   GLY   133      17.051 127.075 288.543  1.00 13.03           6
```

| | | | | | | | | | |
|---|---|---|---|---|---|---|---|---|---|
| ATOM | 533 | O | GLY | 133 | 18.086 | 127.152 | 289.193 | 1.00 14.39 | 8 |
| ATOM | 534 | H | GLY | 133 | 14.118 | 126.113 | 288.185 | 1.00  0.00 | 1 |
| ATOM | 535 | N | GLN | 134 | 16.478 | 128.129 | 287.999 | 1.00 13.02 | 7 |
| ATOM | 536 | CA | GLN | 134 | 17.135 | 129.421 | 287.927 | 1.00 15.27 | 6 |
| ATOM | 537 | C | GLN | 134 | 17.384 | 129.947 | 289.330 | 1.00 17.80 | 6 |
| ATOM | 538 | O | GLN | 134 | 18.483 | 130.380 | 289.677 | 1.00 18.56 | 8 |
| ATOM | 539 | CB | GLN | 134 | 16.223 | 130.384 | 287.162 | 1.00 20.66 | 6 |
| ATOM | 540 | CG | GLN | 134 | 16.689 | 131.796 | 287.123 | 1.00 28.12 | 6 |
| ATOM | 541 | CD | GLN | 134 | 17.638 | 132.037 | 285.983 | 1.00 33.09 | 6 |
| ATOM | 542 | OE1 | GLN | 134 | 17.455 | 131.488 | 284.892 | 1.00 37.15 | 8 |
| ATOM | 543 | NE2 | GLN | 134 | 18.668 | 132.821 | 286.218 | 1.00 35.52 | 7 |
| ATOM | 544 | H | GLN | 134 | 15.606 | 128.025 | 287.567 | 1.00  0.00 | 1 |
| ATOM | 545 | 1HE | GLN | 134 | 19.260 | 132.938 | 285.458 | 1.00  0.00 | 6 |
| ATOM | 546 | 2HE | GLN | 134 | 18.781 | 133.189 | 287.106 | 1.00  0.00 | 6 |
| ATOM | 547 | N | ARG | 135 | 16.349 | 129.861 | 290.156 | 1.00 17.42 | 7 |
| ATOM | 548 | CA | ARG | 135 | 16.402 | 130.379 | 291.508 | 1.00 16.03 | 6 |
| ATOM | 549 | C | ARG | 135 | 17.366 | 129.612 | 292.393 | 1.00 12.99 | 6 |
| ATOM | 550 | O | ARG | 135 | 18.034 | 130.199 | 293.231 | 1.00 15.02 | 8 |
| ATOM | 551 | CB | ARG | 135 | 15.023 | 130.370 | 292.143 | 1.00 19.85 | 6 |
| ATOM | 552 | CG | ARG | 135 | 14.054 | 131.399 | 291.554 | 1.00 27.17 | 6 |
| ATOM | 553 | CD | ARG | 135 | 14.537 | 132.836 | 291.750 | 1.00 32.96 | 6 |
| ATOM | 554 | NE | ARG | 135 | 14.857 | 133.207 | 293.141 | 1.00 37.72 | 7 |
| ATOM | 555 | CZ | ARG | 135 | 13.947 | 133.609 | 294.035 | 1.00 39.03 | 6 |
| ATOM | 556 | NH1 | ARG | 135 | 12.794 | 134.105 | 293.607 | 1.00 38.05 | 7 |
| ATOM | 557 | NH2 | ARG | 135 | 14.239 | 133.638 | 295.334 | 1.00 39.67 | 7 |
| ATOM | 558 | H | ARG | 135 | 15.485 | 129.544 | 289.815 | 1.00  0.00 | 1 |
| ATOM | 559 | HE | ARG | 135 | 15.760 | 132.991 | 293.508 | 1.00  0.00 | 1 |
| ATOM | 560 | 1HH | ARG | 135 | 12.554 | 133.917 | 292.633 | 1.00  0.00 | 6 |
| ATOM | 561 | 2HH | ARG | 135 | 12.104 | 134.403 | 294.226 | 1.00  0.00 | 6 |
| ATOM | 562 | 1HH | ARG | 135 | 15.127 | 133.308 | 295.659 | 1.00  0.00 | 6 |
| ATOM | 563 | 2HH | ARG | 135 | 13.588 | 134.050 | 295.972 | 1.00  0.00 | 6 |
| ATOM | 564 | N | VAL | 136 | 17.407 | 128.291 | 292.253 | 1.00 11.93 | 7 |
| ATOM | 565 | CA | VAL | 136 | 18.364 | 127.497 | 293.028 | 1.00 12.89 | 6 |
| ATOM | 566 | C | VAL | 136 | 19.838 | 127.813 | 292.640 | 1.00 13.10 | 6 |
| ATOM | 567 | O | VAL | 136 | 20.703 | 128.020 | 293.490 | 1.00 10.34 | 8 |
| ATOM | 568 | CB | VAL | 136 | 18.078 | 125.985 | 292.851 | 1.00 13.57 | 6 |
| ATOM | 569 | CG1 | VAL | 136 | 19.179 | 125.147 | 293.476 | 1.00 12.69 | 6 |
| ATOM | 570 | CG2 | VAL | 136 | 16.759 | 125.634 | 293.499 | 1.00 14.24 | 6 |
| ATOM | 571 | H | VAL | 136 | 16.808 | 127.861 | 291.613 | 1.00  0.00 | 1 |
| ATOM | 572 | N | LEU | 137 | 20.101 | 127.907 | 291.336 | 1.00 13.10 | 7 |
| ATOM | 573 | CA | LEU | 137 | 21.438 | 128.195 | 290.837 | 1.00 12.37 | 6 |
| ATOM | 574 | C | LEU | 137 | 21.874 | 129.650 | 291.102 | 1.00 11.49 | 6 |
| ATOM | 575 | O | LEU | 137 | 23.030 | 129.898 | 291.465 | 1.00 12.22 | 8 |
| ATOM | 576 | CB | LEU | 137 | 21.530 | 127.857 | 289.340 | 1.00 10.54 | 6 |
| ATOM | 577 | CG | LEU | 137 | 21.297 | 126.386 | 288.971 | 1.00  9.76 | 6 |
| ATOM | 578 | CD1 | LEU | 137 | 21.411 | 126.215 | 287.465 | 1.00 11.00 | 6 |
| ATOM | 579 | CD2 | LEU | 137 | 22.302 | 125.507 | 289.680 | 1.00 10.16 | 6 |
| ATOM | 580 | H | LEU | 137 | 19.382 | 127.730 | 290.694 | 1.00  0.00 | 1 |
| ATOM | 581 | N | ASP | 138 | 20.940 | 130.597 | 291.032 | 1.00  9.25 | 7 |
| ATOM | 582 | CA | ASP | 138 | 21.254 | 131.975 | 291.382 | 1.00 10.41 | 6 |
| ATOM | 583 | C | ASP | 138 | 21.633 | 132.115 | 292.848 | 1.00  9.95 | 6 |
| ATOM | 584 | O | ASP | 138 | 22.508 | 132.903 | 293.202 | 1.00 10.99 | 8 |
| ATOM | 585 | CB | ASP | 138 | 20.073 | 132.897 | 291.090 | 1.00 13.68 | 6 |
| ATOM | 586 | CG | ASP | 138 | 19.963 | 133.254 | 289.632 | 1.00 18.96 | 6 |
| ATOM | 587 | OD1 | ASP | 138 | 20.935 | 133.075 | 288.869 | 1.00 21.79 | 8 |
| ATOM | 588 | OD2 | ASP | 138 | 18.883 | 133.739 | 289.245 | 1.00 22.42 | 8 |
| ATOM | 589 | H | ASP | 138 | 20.018 | 130.363 | 290.807 | 1.00  0.00 | 1 |
| ATOM | 590 | N | ARG | 139 | 20.960 | 131.344 | 293.710 | 1.00 11.07 | 7 |
| ATOM | 591 | CA | ARG | 139 | 21.291 | 131.308 | 295.136 | 1.00 11.88 | 6 |
| ATOM | 592 | C | ARG | 139 | 22.716 | 130.766 | 295.365 | 1.00 10.66 | 6 |
| ATOM | 593 | O | ARG | 139 | 23.458 | 131.289 | 296.200 | 1.00  7.98 | 8 |
| ATOM | 594 | CB | ARG | 139 | 20.298 | 130.456 | 295.935 | 1.00 10.69 | 6 |
| ATOM | 595 | CG | ARG | 139 | 20.540 | 130.567 | 297.442 | 1.00 16.80 | 6 |
| ATOM | 596 | CD | ARG | 139 | 19.675 | 129.660 | 298.299 | 1.00 22.40 | 6 |
| ATOM | 597 | NE | ARG | 139 | 20.065 | 129.688 | 299.714 | 1.00 25.91 | 7 |
| ATOM | 598 | CZ | ARG | 139 | 19.577 | 128.861 | 300.643 | 1.00 31.03 | 6 |
| ATOM | 599 | NH1 | ARG | 139 | 18.627 | 127.997 | 300.332 | 1.00 32.34 | 7 |
| ATOM | 600 | NH2 | ARG | 139 | 20.062 | 128.876 | 301.884 | 1.00 29.77 | 7 |
| ATOM | 601 | H | ARG | 139 | 20.304 | 130.722 | 293.378 | 1.00  0.00 | 1 |
| ATOM | 602 | HE | ARG | 139 | 20.799 | 130.278 | 300.004 | 1.00  0.00 | 1 |
| ATOM | 603 | 1HH | ARG | 139 | 18.298 | 127.944 | 299.390 | 1.00  0.00 | 6 |
| ATOM | 604 | 2HH | ARG | 139 | 18.242 | 127.380 | 301.021 | 1.00  0.00 | 6 |
| ATOM | 605 | 1HH | ARG | 139 | 20.793 | 129.487 | 302.158 | 1.00  0.00 | 6 |
| ATOM | 606 | 2HH | ARG | 139 | 19.638 | 128.284 | 302.546 | 1.00  0.00 | 6 |
| ATOM | 607 | N | LEU | 140 | 23.072 | 129.699 | 294.647 | 1.00  9.23 | 7 |
| ATOM | 608 | CA | LEU | 140 | 24.419 | 129.140 | 294.711 | 1.00  9.95 | 6 |
| ATOM | 609 | C | LEU | 140 | 25.475 | 130.119 | 294.204 | 1.00  9.94 | 6 |
| ATOM | 610 | O | LEU | 140 | 26.515 | 130.291 | 294.804 | 1.00 10.20 | 8 |
| ATOM | 611 | CB | LEU | 140 | 24.511 | 127.854 | 293.899 | 1.00 10.43 | 6 |
| ATOM | 612 | CG | LEU | 140 | 25.845 | 127.112 | 294.049 | 1.00 14.84 | 6 |
| ATOM | 613 | CD1 | LEU | 140 | 26.001 | 126.548 | 295.471 | 1.00 14.02 | 6 |
| ATOM | 614 | CD2 | LEU | 140 | 25.901 | 126.002 | 293.027 | 1.00 13.19 | 6 |
| ATOM | 615 | H | LEU | 140 | 22.444 | 129.341 | 294.002 | 1.00  0.00 | 1 |
| ATOM | 616 | N | SER | 141 | 25.187 | 130.748 | 293.074 | 1.00  8.26 | 7 |
| ATOM | 617 | CA | SER | 141 | 26.077 | 131.714 | 292.462 | 1.00 13.49 | 6 |
| ATOM | 618 | C | SER | 141 | 26.389 | 132.937 | 293.352 | 1.00 15.46 | 6 |
| ATOM | 619 | O | SER | 141 | 27.547 | 133.351 | 293.486 | 1.00 14.77 | 8 |

```
ATOM    620  CB  SER   141     25.474 132.182 291.124  1.00 14.73     6
ATOM    621  OG  SER   141     26.299 133.155 290.521  1.00 24.92     8
ATOM    622  H   SER   141     24.348 130.525 292.644  1.00  0.00     1
ATOM    623  HG  SER   141     27.180 132.809 290.342  1.00  0.00     1
ATOM    624  N   GLU   142     25.334 133.536 293.913  1.00 14.75     7
ATOM    625  CA  GLU   142     25.442 134.645 294.851  1.00 15.96     6
ATOM    626  C   GLU   142     26.108 134.230 296.168  1.00 12.04     6
ATOM    627  O   GLU   142     26.844 134.988 296.757  1.00 14.75     8
ATOM    628  CB  GLU   142     24.036 135.239 295.126  1.00 21.10     6
ATOM    629  CG  GLU   142     24.045 136.669 295.691  1.00 30.24     6
ATOM    630  CD  GLU   142     22.878 136.933 296.656  1.00 37.44     6
ATOM    631  OE1 GLU   142     21.795 136.324 296.451  1.00 39.92     8
ATOM    632  OE2 GLU   142     23.053 137.730 297.625  1.00 38.61     8
ATOM    633  H   GLU   142     24.446 133.174 293.738  1.00  0.00     1
ATOM    634  N   ALA   143     25.865 133.019 296.635  1.00 11.86     7
ATOM    635  CA  ALA   143     26.518 132.539 297.836  1.00 12.41     6
ATOM    636  C   ALA   143     28.035 132.276 297.665  1.00 14.41     6
ATOM    637  O   ALA   143     28.765 132.192 298.653  1.00 12.04     8
ATOM    638  CB  ALA   143     25.835 131.286 298.304  1.00 11.32     6
ATOM    639  H   ALA   143     25.270 132.420 296.163  1.00  0.00     1
ATOM    640  N   CYS   144     28.497 132.194 296.403  1.00 11.42     7
ATOM    641  CA  CYS   144     29.914 131.985 296.070  1.00 10.19     6
ATOM    642  C   CYS   144     30.578 133.216 295.436  1.00  9.60     6
ATOM    643  O   CYS   144     31.734 133.175 295.028  1.00  9.81     8
ATOM    644  CB  CYS   144     30.065 130.804 295.106  1.00  6.23     6
ATOM    645  SG  CYS   144     29.563 129.253 295.761  1.00 12.25    16
ATOM    646  H   CYS   144     27.874 132.288 295.675  1.00  0.00     1
ATOM    647  N   ALA   145     29.850 134.321 295.356  1.00  8.78     7
ATOM    648  CA  ALA   145     30.349 135.525 294.724  1.00  9.83     6
ATOM    649  C   ALA   145     31.634 136.062 295.329  1.00 12.54     6
ATOM    650  O   ALA   145     32.386 136.758 294.657  1.00  9.95     8
ATOM    651  CB  ALA   145     29.290 136.622 294.752  1.00 11.57     6
ATOM    652  H   ALA   145     28.961 134.347 295.724  1.00  0.00     1
ATOM    653  N   ASP   146     31.854 135.799 296.621  1.00 14.76     7
ATOM    654  CA  ASP   146     33.071 136.264 297.292  1.00 15.14     6
ATOM    655  C   ASP   146     34.335 135.579 296.764  1.00 15.15     6
ATOM    656  O   ASP   146     35.372 136.203 296.674  1.00 15.22     8
ATOM    657  CB  ASP   146     32.953 136.122 298.835  1.00 14.61     6
ATOM    658  CG  ASP   146     32.721 134.692 299.308  1.00 17.04     6
ATOM    659  OD1 ASP   146     32.180 133.897 298.533  1.00 19.51     8
ATOM    660  OD2 ASP   146     33.052 134.349 300.466  1.00 17.60     8
ATOM    661  H   ASP   146     31.245 135.271 297.135  1.00  0.00     1
ATOM    662  N   ILE   147     34.207 134.357 296.247  1.00 13.01     7
ATOM    663  CA  ILE   147     35.364 133.601 295.791  1.00 12.44     6
ATOM    664  C   ILE   147     35.306 133.126 294.332  1.00 13.07     6
ATOM    665  O   ILE   147     36.233 132.480 293.845  1.00 12.14     8
ATOM    666  CB  ILE   147     35.639 132.378 296.702  1.00 12.78     6
ATOM    667  CG1 ILE   147     34.438 131.436 296.734  1.00 11.63     6
ATOM    668  CG2 ILE   147     35.999 132.847 298.115  1.00 12.49     6
ATOM    669  CD1 ILE   147     34.673 130.177 297.616  1.00 12.49     6
ATOM    670  H   ILE   147     33.336 133.954 296.282  1.00  0.00     1
ATOM    671  N   ALA   148     34.181 133.364 293.656  1.00  9.88     7
ATOM    672  CA  ALA   148     34.026 132.854 292.293  1.00 10.25     6
ATOM    673  C   ALA   148     33.461 133.857 291.316  1.00 10.67     6
ATOM    674  O   ALA   148     32.764 134.787 291.672  1.00 13.69     8
ATOM    675  CB  ALA   148     33.189 131.603 292.278  1.00 10.60     6
ATOM    676  H   ALA   148     33.503 133.907 294.091  1.00  0.00     1
ATOM    677  N   VAL   149     33.739 133.633 290.047  1.00 10.18     7
ATOM    678  CA  VAL   149     33.053 134.343 288.988  1.00  8.98     6
ATOM    679  C   VAL   149     32.152 133.372 288.218  1.00  9.89     6
ATOM    680  O   VAL   149     32.381 132.151 288.160  1.00  7.50     8
ATOM    681  CB  VAL   149     34.071 135.027 288.030  1.00  8.86     6
ATOM    682  CG1 VAL   149     34.889 136.069 288.797  1.00 11.09     6
ATOM    683  CG2 VAL   149     34.995 133.977 287.387  1.00  9.98     6
ATOM    684  H   VAL   149     34.327 132.899 289.811  1.00  0.00     1
ATOM    685  N   VAL   150     31.083 133.912 287.645  1.00  7.97     7
ATOM    686  CA  VAL   150     30.248 133.111 286.785  1.00  9.95     6
ATOM    687  C   VAL   150     30.846 133.049 285.365  1.00 10.50     6
ATOM    688  O   VAL   150     31.048 134.066 284.702  1.00 11.82     8
ATOM    689  CB  VAL   150     28.831 133.667 286.716  1.00  9.08     6
ATOM    690  CG1 VAL   150     28.004 132.795 285.836  1.00  8.00     6
ATOM    691  CG2 VAL   150     28.236 133.725 288.123  1.00 12.72     6
ATOM    692  H   VAL   150     30.885 134.867 287.764  1.00  0.00     1
ATOM    693  N   GLU   151     31.233 131.847 284.960  1.00 10.55     7
ATOM    694  CA  GLU   151     31.825 131.641 283.663  1.00  8.65     6
ATOM    695  C   GLU   151     30.717 131.349 282.681  1.00 10.27     6
ATOM    696  O   GLU   151     30.749 131.819 281.547  1.00 12.55     8
ATOM    697  CB  GLU   151     32.776 130.459 283.709  1.00  9.27     6
ATOM    698  CG  GLU   151     33.505 130.230 282.420  1.00 12.64     6
ATOM    699  CD  GLU   151     34.573 129.198 282.580  1.00 14.16     6
ATOM    700  OE1 GLU   151     35.500 129.438 283.375  1.00 17.04     8
ATOM    701  OE2 GLU   151     34.416 128.100 282.028  1.00 14.19     8
ATOM    702  H   GLU   151     31.120 131.098 285.579  1.00  0.00     1
ATOM    703  N   THR   152     29.732 130.580 283.138  1.00  9.91     7
ATOM    704  CA  THR   152     28.538 130.297 282.353  1.00  9.16     6
ATOM    705  C   THR   152     27.287 130.424 283.220  1.00  9.09     6
ATOM    706  O   THR   152     27.105 129.680 284.178  1.00  7.59     8
```

```
ATOM  707  CB   THR 152   28.622 128.879 281.696  1.00  8.76   6
ATOM  708  OG1  THR 152   29.721 128.862 280.778  1.00 13.35   8
ATOM  709  CG2  THR 152   27.366 128.558 280.897  1.00 10.31   6
ATOM  710  H    THR 152   29.794 130.281 284.080  1.00  0.00   1
ATOM  711  HG1  THR 152   29.871 127.981 280.423  1.00  0.00   1
ATOM  712  N    ALA 153   26.509 131.473 282.962  1.00 10.81   7
ATOM  713  CA   ALA 153   25.287 131.762 283.714  1.00 11.70   6
ATOM  714  C    ALA 153   24.228 130.684 283.450  1.00 13.04   6
ATOM  715  O    ALA 153   24.345 129.935 282.485  1.00 13.34   8
ATOM  716  CB   ALA 153   24.749 133.139 283.302  1.00 13.51   6
ATOM  717  H    ALA 153   26.788 132.098 282.279  1.00  0.00   1
ATOM  718  N    PRO 154   23.270 130.488 284.400  1.00 13.01   7
ATOM  719  CA   PRO 154   22.321 129.372 284.251  1.00 13.93   6
ATOM  720  C    PRO 154   21.708 129.219 282.851  1.00 15.70   6
ATOM  721  O    PRO 154   21.297 130.188 282.207  1.00 14.86   8
ATOM  722  CB   PRO 154   21.267 129.680 285.317  1.00 13.63   6
ATOM  723  CG   PRO 154   22.040 130.374 286.389  1.00  9.94   6
ATOM  724  CD   PRO 154   23.066 131.207 285.668  1.00 11.22   6
ATOM  725  N    LYS 155   21.763 127.995 282.339  1.00 17.84   7
ATOM  726  CA   LYS 155   21.295 127.700 281.002  1.00 21.51   6
ATOM  727  C    LYS 155   20.882 126.246 280.866  1.00 21.52   6
ATOM  728  O    LYS 155   21.331 125.380 281.612  1.00 18.10   8
ATOM  729  CB   LYS 155   22.376 128.043 279.956  1.00 25.60   6
ATOM  730  CG   LYS 155   23.599 127.140 279.939  1.00 27.83   6
ATOM  731  CD   LYS 155   24.551 127.553 278.826  1.00 34.89   6
ATOM  732  CE   LYS 155   23.998 127.252 277.416  1.00 41.28   6
ATOM  733  NZ   LYS 155   24.110 125.806 276.957  1.00 44.82   7
ATOM  734  H    LYS 155   22.198 127.288 282.860  1.00  0.00   1
ATOM  735  1HZ  LYS 155   25.096 125.488 276.979  1.00  0.00   6
ATOM  736  2HZ  LYS 155   23.548 125.226 277.615  1.00  0.00   6
ATOM  737  3HZ  LYS 155   23.712 125.706 275.998  1.00  0.00   6
ATOM  738  N    MET 156   19.994 125.999 279.913  1.00 24.88   7
ATOM  739  CA   MET 156   19.462 124.670 279.635  1.00 28.64   6
ATOM  740  C    MET 156   20.374 123.897 278.704  1.00 30.34   6
ATOM  741  O    MET 156   21.026 124.476 277.840  1.00 31.10   8
ATOM  742  CB   MET 156   18.074 124.783 278.996  1.00 31.78   6
ATOM  743  CG   MET 156   17.041 125.556 279.826  1.00 33.29   6
ATOM  744  SD   MET 156   16.653 124.830 281.447  1.00 39.73  16
ATOM  745  CE   MET 156   15.620 123.443 280.983  1.00 38.29   6
ATOM  746  H    MET 156   19.698 126.739 279.353  1.00  0.00   1
ATOM  747  N    ASP 157   20.436 122.588 278.927  1.00 30.88   7
ATOM  748  CA   ASP 157   21.191 121.656 278.104  1.00 33.80   6
ATOM  749  C    ASP 157   20.334 120.382 278.003  1.00 33.30   6
ATOM  750  O    ASP 157   20.478 119.449 278.788  1.00 33.60   8
ATOM  751  CB   ASP 157   22.564 121.373 278.753  1.00 38.57   6
ATOM  752  CG   ASP 157   23.377 120.274 278.029  1.00 43.15   6
ATOM  753  OD1  ASP 157   23.374 120.186 276.771  1.00 43.36   8
ATOM  754  OD2  ASP 157   24.097 119.543 278.747  1.00 45.49   8
ATOM  755  H    ASP 157   19.854 122.229 279.619  1.00  0.00   1
ATOM  756  N    GLY 158   19.272 120.473 277.217  1.00 32.91   7
ATOM  757  CA   GLY 158   18.329 119.375 277.164  1.00 31.93   6
ATOM  758  C    GLY 158   17.368 119.431 278.334  1.00 31.16   6
ATOM  759  O    GLY 158   16.632 120.409 278.498  1.00 30.43   8
ATOM  760  H    GLY 158   19.110 121.287 276.710  1.00  0.00   1
ATOM  761  N    ARG 159   17.454 118.431 279.205  1.00 31.04   7
ATOM  762  CA   ARG 159   16.585 118.334 280.394  1.00 30.44   6
ATOM  763  C    ARG 159   17.387 118.673 281.664  1.00 29.46   6
ATOM  764  O    ARG 159   17.093 118.210 282.770  1.00 29.12   8
ATOM  765  CB   ARG 159   16.005 116.922 280.497  1.00 31.54   6
ATOM  766  CG   ARG 159   15.240 116.458 279.238  1.00 35.42   6
ATOM  767  CD   ARG 159   13.829 117.004 279.149  1.00 35.88   6
ATOM  768  NE   ARG 159   12.963 116.501 280.214  1.00 40.26   7
ATOM  769  CZ   ARG 159   12.683 117.204 281.314  1.00 41.20   6
ATOM  770  NH1  ARG 159   12.818 118.521 281.301  1.00 42.30   7
ATOM  771  NH2  ARG 159   12.190 116.620 282.399  1.00 40.62   7
ATOM  772  H    ARG 159   18.117 117.727 279.033  1.00  0.00   1
ATOM  773  HE   ARG 159   12.805 115.531 280.304  1.00  0.00   1
ATOM  774  1HH  ARG 159   13.358 119.017 280.558  1.00  0.00   6
ATOM  775  2HH  ARG 159   12.563 119.014 282.178  1.00  0.00   6
ATOM  776  1HH  ARG 159   12.043 115.647 282.440  1.00  0.00   6
ATOM  777  2HH  ARG 159   11.810 117.183 283.186  1.00  0.00   6
ATOM  778  N    ASN 160   18.444 119.450 281.462  1.00 26.74   7
ATOM  779  CA   ASN 160   19.307 119.877 282.532  1.00 24.33   6
ATOM  780  C    ASN 160   19.434 121.372 282.456  1.00 21.78   6
ATOM  781  O    ASN 160   19.374 121.970 281.387  1.00 20.81   8
ATOM  782  CB   ASN 160   20.695 119.258 282.372  1.00 28.32   6
ATOM  783  CG   ASN 160   20.642 117.814 281.967  1.00 31.40   6
ATOM  784  OD1  ASN 160   20.037 116.995 282.655  1.00 34.15   8
ATOM  785  ND2  ASN 160   21.245 117.493 280.840  1.00 33.16   7
ATOM  786  H    ASN 160   18.596 119.807 280.564  1.00  0.00   1
ATOM  787  1HD  ASN 160   21.243 116.547 280.560  1.00  0.00   6
ATOM  788  2HD  ASN 160   21.724 118.163 280.329  1.00  0.00   6
ATOM  789  N    MET 161   19.703 121.970 283.601  1.00 18.88   7
ATOM  790  CA   MET 161   20.090 123.363 283.679  1.00 16.97   6
ATOM  791  C    MET 161   21.430 123.400 284.401  1.00 14.13   6
ATOM  792  O    MET 161   21.641 122.656 285.349  1.00 13.81   8
ATOM  793  CB   MET 161   19.035 124.149 284.437  1.00 18.10   6
```

```
ATOM    794  CG  MET  161      19.163 125.626 284.229  1.00 20.27      6
ATOM    795  SD  MET  161      18.072 126.585 285.252  1.00 22.18     16
ATOM    796  CE  MET  161      17.587 127.857 284.111  1.00 22.11      6
ATOM    797  H   MET  161      19.791 121.421 284.406  1.00  0.00      1
ATOM    798  N   PHE  162      22.373 124.188 283.910  1.00 10.76      7
ATOM    799  CA  PHE  162      23.665 124.253 284.587  1.00 11.14      6
ATOM    800  C   PHE  162      24.260 125.658 284.663  1.00  9.91      6
ATOM    801  O   PHE  162      23.864 126.591 283.951  1.00 11.49      8
ATOM    802  CB  PHE  162      24.684 123.290 283.953  1.00  9.92      6
ATOM    803  CG  PHE  162      25.174 123.732 282.600  1.00 12.29      6
ATOM    804  CD1 PHE  162      24.443 123.444 281.465  1.00 13.79      6
ATOM    805  CD2 PHE  162      26.359 124.444 282.465  1.00 14.83      6
ATOM    806  CE1 PHE  162      24.880 123.838 280.222  1.00 14.63      6
ATOM    807  CE2 PHE  162      26.803 124.840 281.218  1.00 16.54      6
ATOM    808  CZ  PHE  162      26.056 124.531 280.096  1.00 15.27      6
ATOM    809  H   PHE  162      22.226 124.738 283.119  1.00  0.00      1
ATOM    810  N   LEU  163      25.206 125.779 285.568  1.00  8.04      7
ATOM    811  CA  LEU  163      25.918 127.006 285.839  1.00  8.48      6
ATOM    812  C   LEU  163      27.370 126.547 286.018  1.00  7.21      6
ATOM    813  O   LEU  163      27.610 125.449 286.517  1.00  7.95      8
ATOM    814  CB  LEU  163      25.380 127.592 287.159  1.00 10.26      6
ATOM    815  CG  LEU  163      26.245 128.528 287.978  1.00 13.41      6
ATOM    816  CD1 LEU  163      26.081 129.901 287.406  1.00 18.36      6
ATOM    817  CD2 LEU  163      25.821 128.527 289.445  1.00 15.83      6
ATOM    818  H   LEU  163      25.486 124.969 286.065  1.00  0.00      1
ATOM    819  N   VAL  164      28.310 127.333 285.532  1.00  8.63      7
ATOM    820  CA  VAL  164      29.721 127.079 285.791  1.00  8.41      6
ATOM    821  C   VAL  164      30.286 128.262 286.553  1.00  6.24      6
ATOM    822  O   VAL  164      30.122 129.401 286.136  1.00  5.99      8
ATOM    823  CB  VAL  164      30.525 126.857 284.466  1.00  8.23      6
ATOM    824  CG1 VAL  164      32.016 126.571 284.770  1.00  6.26      6
ATOM    825  CG2 VAL  164      29.922 125.697 283.704  1.00  6.76      6
ATOM    826  H   VAL  164      28.082 128.214 285.180  1.00  0.00      1
ATOM    827  N   LEU  165      30.909 127.971 287.681  1.00  7.52      7
ATOM    828  CA  LEU  165      31.609 128.970 288.469  1.00  7.69      6
ATOM    829  C   LEU  165      33.105 128.695 288.338  1.00  7.71      6
ATOM    830  O   LEU  165      33.524 127.539 288.387  1.00  6.75      8
ATOM    831  CB  LEU  165      31.234 128.838 289.946  1.00  7.50      6
ATOM    832  CG  LEU  165      29.755 128.981 290.299  1.00  8.61      6
ATOM    833  CD1 LEU  165      29.596 128.633 291.759  1.00  9.02      6
ATOM    834  CD2 LEU  165      29.281 130.400 289.994  1.00  9.25      6
ATOM    835  H   LEU  165      31.068 127.047 287.950  1.00  0.00      1
ATOM    836  N   ALA  166      33.902 129.753 288.206  1.00  9.73      7
ATOM    837  CA  ALA  166      35.361 129.649 288.190  1.00  9.55      6
ATOM    838  C   ALA  166      35.908 130.424 289.388  1.00 10.40      6
ATOM    839  O   ALA  166      35.344 131.437 289.774  1.00 10.14      8
ATOM    840  CB  ALA  166      35.913 130.245 286.872  1.00  7.76      6
ATOM    841  H   ALA  166      33.534 130.658 288.236  1.00  0.00      1
ATOM    842  N   PRO  167      37.035 129.963 289.974  1.00 13.38      7
ATOM    843  CA  PRO  167      37.650 130.719 291.075  1.00 13.73      6
ATOM    844  C   PRO  167      38.113 132.099 290.623  1.00 17.06      6
ATOM    845  O   PRO  167      38.502 132.272 289.463  1.00 16.58      8
ATOM    846  CB  PRO  167      38.819 129.832 291.497  1.00 16.22      6
ATOM    847  CG  PRO  167      39.087 128.989 290.320  1.00 14.96      6
ATOM    848  CD  PRO  167      37.777 128.732 289.679  1.00 10.94      6
ATOM    849  N   LYS  168      37.908 133.088 291.483  1.00 18.17      7
ATOM    850  CA  LYS  168      38.396 134.438 291.244  1.00 22.83      6
ATOM    851  C   LYS  168      39.915 134.486 291.084  1.00 27.01      6
ATOM    852  O   LYS  168      40.429 135.219 290.247  1.00 27.84      8
ATOM    853  CB  LYS  168      37.972 135.351 292.384  1.00 22.25      6
ATOM    854  CG  LYS  168      36.645 136.010 292.159  1.00 22.55      6
ATOM    855  CD  LYS  168      36.296 136.915 293.299  1.00 26.09      6
ATOM    856  CE  LYS  168      35.232 137.909 292.876  1.00 32.24      6
ATOM    857  NZ  LYS  168      33.962 137.225 292.506  1.00 35.82      7
ATOM    858  H   LYS  168      37.561 132.887 292.380  1.00  0.00      1
ATOM    859  1HZ LYS  168      34.064 136.576 291.704  1.00  0.00      6
ATOM    860  2HZ LYS  168      33.579 136.708 293.321  1.00  0.00      6
ATOM    861  3HZ LYS  168      33.324 137.988 292.266  1.00  0.00      6
ATOM    862  N   ASN  169      40.624 133.752 291.942  1.00 31.31      7
ATOM    863  CA  ASN  169      42.086 133.697 291.920  1.00 36.93      6
ATOM    864  C   ASN  169      42.539 132.251 292.000  1.00 40.16      6
ATOM    865  O   ASN  169      41.786 131.393 292.436  1.00 39.66      8
ATOM    866  CB  ASN  169      42.677 134.480 293.101  1.00 38.00      6
ATOM    867  CG  ASN  169      42.417 135.971 293.001  1.00 39.49      6
ATOM    868  OD1 ASN  169      41.485 136.487 293.620  1.00 39.65      8
ATOM    869  ND2 ASN  169      43.230 136.671 292.217  1.00 39.53      7
ATOM    870  H   ASN  169      40.175 133.202 292.614  1.00  0.00      1
ATOM    871  1HD ASN  169      43.063 137.630 292.155  1.00  0.00      6
ATOM    872  2HD ASN  169      43.939 136.225 291.739  1.00  0.00      6
ATOM    873  N   ASP  170      43.778 131.991 291.595  1.00 46.80      7
ATOM    874  CA  ASP  170      44.324 130.632 291.616  1.00 52.01      6
ATOM    875  C   ASP  170      45.852 130.645 291.636  1.00 54.08      6
ATOM    876  O   ASP  170      46.419 131.659 292.100  1.00 54.66      8
ATOM    877  CB  ASP  170      43.798 129.814 290.416  1.00 55.20      6
ATOM    878  CG  ASP  170      43.789 130.607 289.101  1.00 57.56      6
ATOM    879  OD1 ASP  170      44.886 130.952 288.597  1.00 57.39      8
ATOM    880  OD2 ASP  170      42.681 130.827 288.544  1.00 58.11      8
```

```
ATOM    881  OXT ASP   170      46.460 129.636 291.200  1.00 56.26      8
ATOM    882  H   ASP   170      44.372 132.697 291.301  1.00  0.00      1
END
```

File D

```
REMARK PDB coordinates for the N-terminal domain of IF3 bound to 30S subunits
REMARK Written by O version 7.0.1
REMARK Fri Jan  5 15:04:16 2001
CRYST1   27.600   39.200   65.900  90.00  90.00  90.00
ORIGX1      1.000000  0.000000  0.000000        0.00000
ORIGX2      0.000000  1.000000  0.000000        0.00000
ORIGX3      0.000000  0.000000  1.000000        0.00000
SCALE1      0.036232 -0.000001 -0.000001        0.00000
SCALE2      0.000000  0.025510 -0.000001        0.00000
SCALE3      0.000000  0.000000  0.015175        0.00000
ATOM      1  N   LYS     3      50.423  96.339 279.886  0.00 28.91      7
ATOM      2  CA  LYS     3      51.114  97.391 279.095  0.00 27.20      6
ATOM      3  C   LYS     3      52.218  96.762 278.253  0.00 26.43      6
ATOM      4  O   LYS     3      51.988  96.400 277.103  0.00 27.31      8
ATOM      5  CB  LYS     3      51.697  98.467 280.017  0.00 28.63      6
ATOM      6  CG  LYS     3      50.654  99.287 280.758  0.00 28.67      6
ATOM      7  CD  LYS     3      51.312 100.344 281.632  0.00 28.27      6
ATOM      8  CE  LYS     3      50.278 101.220 282.322  0.00 27.73      6
ATOM      9  NZ  LYS     3      49.475 102.005 281.344  0.00 28.05      7
ATOM     10  1H  LYS     3      50.100  95.617 279.209  1.00  0.00      6
ATOM     11  2H  LYS     3      51.136  95.883 280.495  1.00  0.00      6
ATOM     12  3H  LYS     3      49.639  96.709 280.443  1.00  0.00      6
ATOM     13  1HZ LYS     3      48.988 101.358 280.696  1.00  0.00      6
ATOM     14  2HZ LYS     3      48.780 102.578 281.860  1.00  0.00      6
ATOM     15  3HZ LYS     3      50.113 102.627 280.812  1.00  0.00      6
ATOM     16  N   ASP     4      53.399  96.604 278.842  0.00 24.64      7
ATOM     17  CA  ASP     4      54.541  96.014 278.151  0.00 23.14      6
ATOM     18  C   ASP     4      54.220  94.614 277.640  0.00 20.81      6
ATOM     19  O   ASP     4      53.638  93.796 278.357  0.00 20.42      8
ATOM     20  CB  ASP     4      55.754  95.968 279.085  0.00 22.97      6
ATOM     21  CG  ASP     4      56.969  95.317 278.441  0.00 23.79      6
ATOM     22  OD1 ASP     4      57.621  95.970 277.599  0.00 23.63      8
ATOM     23  OD2 ASP     4      57.275  94.154 278.783  0.00 24.00      8
ATOM     24  H   ASP     4      53.570  96.884 279.762  1.00  0.00      1
ATOM     25  N   PHE     5      54.578  94.365 276.385  1.00 18.06      7
ATOM     26  CA  PHE     5      54.365  93.076 275.745  1.00 15.46      6
ATOM     27  C   PHE     5      55.728  92.571 275.293  1.00 13.85      6
ATOM     28  O   PHE     5      56.625  93.376 275.022  1.00 12.97      8
ATOM     29  CB  PHE     5      53.514  93.232 274.476  1.00 14.88      6
ATOM     30  CG  PHE     5      52.095  93.649 274.725  1.00 16.80      6
ATOM     31  CD1 PHE     5      51.213  92.811 275.395  1.00 16.48      6
ATOM     32  CD2 PHE     5      51.631  94.869 274.255  1.00 17.03      6
ATOM     33  CE1 PHE     5      49.883  93.185 275.595  1.00 17.30      6
ATOM     34  CE2 PHE     5      50.303  95.254 274.450  1.00 17.29      6
ATOM     35  CZ  PHE     5      49.430  94.411 275.118  1.00 16.97      6
ATOM     36  H   PHE     5      55.035  95.058 275.857  1.00  0.00      1
ATOM     37  N   ILE     6      55.913  91.256 275.235  1.00 10.75      7
ATOM     38  CA  ILE     6      57.179  90.744 274.731  1.00  9.65      6
ATOM     39  C   ILE     6      56.984  90.638 273.226  1.00  8.87      6
ATOM     40  O   ILE     6      55.879  90.364 272.752  1.00  7.82      8
ATOM     41  CB  ILE     6      57.600  89.405 275.357  1.00 11.31      6
ATOM     42  CG1 ILE     6      56.532  88.334 275.154  1.00 10.95      6
ATOM     43  CG2 ILE     6      57.929  89.605 276.833  1.00 11.04      6
ATOM     44  CD1 ILE     6      57.010  86.944 275.567  1.00 12.18      6
ATOM     45  H   ILE     6      55.192  90.650 275.512  1.00  0.00      1
ATOM     46  N   ILE     7      58.040  90.888 272.470  1.00  7.30      7
ATOM     47  CA  ILE     7      57.930  90.888 271.021  1.00  6.36      6
ATOM     48  C   ILE     7      59.027  90.126 270.308  1.00  6.56      6
ATOM     49  O   ILE     7      60.064  89.797 270.887  1.00  5.65      8
ATOM     50  CB  ILE     7      57.975  92.350 270.473  1.00  7.35      6
ATOM     51  CG1 ILE     7      59.381  92.953 270.681  1.00  7.34      6
ATOM     52  CG2 ILE     7      56.928  93.211 271.167  1.00  6.62      6
ATOM     53  CD1 ILE     7      59.585  94.331 270.051  1.00  6.89      6
ATOM     54  H   ILE     7      58.904  91.085 272.897  1.00  0.00      1
ATOM     55  N   ASN     8      58.781  89.876 269.029  1.00  6.34      7
ATOM     56  CA  ASN     8      59.732  89.217 268.151  1.00  6.82      6
ATOM     57  C   ASN     8      60.439  87.983 268.730  1.00  8.40      6
ATOM     58  O   ASN     8      59.775  87.034 269.136  1.00  7.68      8
ATOM     59  CB  ASN     8      60.707  90.274 267.618  1.00  6.94      6
ATOM     60  CG  ASN     8      59.983  91.396 266.876  1.00  6.71      6
ATOM     61  OD1 ASN     8      58.970  91.155 266.221  1.00  6.07      8
ATOM     62  ND2 ASN     8      60.462  92.624 267.018  1.00  6.41      7
ATOM     63  H   ASN     8      57.916  90.138 268.668  1.00  0.00      1
ATOM     64  1HD ASN     8      60.023  93.322 266.496  1.00  0.00      6
ATOM     65  2HD ASN     8      61.235  92.780 267.598  1.00  0.00      6
ATOM     66  N   GLU     9      61.768  87.993 268.792  1.00  9.30      7
ATOM     67  CA  GLU     9      62.506  86.835 269.300  1.00 11.33      6
ATOM     68  C   GLU     9      62.348  86.528 270.796  1.00 11.22      6
ATOM     69  O   GLU     9      62.827  85.498 271.261  1.00 10.80      8
ATOM     70  CB  GLU     9      63.996  86.950 268.947  1.00 14.73      6
ATOM     71  CG  GLU     9      64.312  86.840 267.453  1.00 20.58      6
```

| | | | | | | | | | |
|---|---|---|---|---|---|---|---|---|---|
| ATOM | 72 | CD | GLU | 9 | 64.387 | 85.399 | 266.957 | 1.00 23.88 | 6 |
| ATOM | 73 | OE1 | GLU | 9 | 63.352 | 84.702 | 266.969 | 1.00 25.05 | 8 |
| ATOM | 74 | OE2 | GLU | 9 | 65.491 | 84.972 | 266.551 | 1.00 25.25 | 8 |
| ATOM | 75 | H | GLU | 9 | 62.302 | 88.775 | 268.543 | 1.00 0.00 | 1 |
| ATOM | 76 | N | GLN | 10 | 61.732 | 87.433 | 271.553 | 1.00 10.33 | 7 |
| ATOM | 77 | CA | GLN | 10 | 61.530 | 87.203 | 272.986 | 1.00 9.64 | 6 |
| ATOM | 78 | C | GLN | 10 | 60.434 | 86.158 | 273.197 | 1.00 9.84 | 6 |
| ATOM | 79 | O | GLN | 10 | 60.327 | 85.565 | 274.277 | 1.00 9.60 | 8 |
| ATOM | 80 | CB | GLN | 10 | 61.105 | 88.493 | 273.690 | 1.00 9.70 | 6 |
| ATOM | 81 | CG | GLN | 10 | 62.105 | 89.639 | 273.626 | 1.00 10.42 | 6 |
| ATOM | 82 | CD | GLN | 10 | 61.587 | 90.880 | 274.328 | 1.00 11.52 | 6 |
| ATOM | 83 | OE1 | GLN | 10 | 60.431 | 91.268 | 274.164 | 1.00 10.18 | 8 |
| ATOM | 84 | NE2 | GLN | 10 | 62.435 | 91.500 | 275.128 | 1.00 12.60 | 7 |
| ATOM | 85 | H | GLN | 10 | 61.388 | 88.259 | 271.155 | 1.00 0.00 | 1 |
| ATOM | 86 | 1HE | GLN | 10 | 62.100 | 92.304 | 275.575 | 1.00 0.00 | 6 |
| ATOM | 87 | 2HE | GLN | 10 | 63.329 | 91.126 | 275.224 | 1.00 0.00 | 6 |
| ATOM | 88 | N | ILE | 11 | 59.590 | 85.982 | 272.183 | 1.00 8.88 | 7 |
| ATOM | 89 | CA | ILE | 11 | 58.485 | 85.035 | 272.237 | 1.00 8.68 | 6 |
| ATOM | 90 | C | ILE | 11 | 59.022 | 83.608 | 272.232 | 1.00 9.84 | 6 |
| ATOM | 91 | O | ILE | 11 | 59.870 | 83.263 | 271.415 | 1.00 9.28 | 8 |
| ATOM | 92 | CB | ILE | 11 | 57.522 | 85.241 | 271.043 | 1.00 8.95 | 6 |
| ATOM | 93 | CG1 | ILE | 11 | 56.905 | 86.643 | 271.108 | 1.00 9.35 | 6 |
| ATOM | 94 | CG2 | ILE | 11 | 56.425 | 84.181 | 271.049 | 1.00 8.91 | 6 |
| ATOM | 95 | CD1 | ILE | 11 | 56.105 | 87.021 | 269.871 | 1.00 9.61 | 6 |
| ATOM | 96 | H | ILE | 11 | 59.731 | 86.465 | 271.338 | 1.00 0.00 | 1 |
| ATOM | 97 | N | ARG | 12 | 58.524 | 82.788 | 273.153 | 1.00 10.71 | 7 |
| ATOM | 98 | CA | ARG | 12 | 58.967 | 81.405 | 273.263 | 1.00 12.20 | 6 |
| ATOM | 99 | C | ARG | 12 | 57.976 | 80.368 | 272.715 | 1.00 11.29 | 6 |
| ATOM | 100 | O | ARG | 12 | 58.344 | 79.209 | 272.510 | 1.00 10.76 | 8 |
| ATOM | 101 | CB | ARG | 12 | 59.300 | 81.082 | 274.721 | 1.00 15.18 | 6 |
| ATOM | 102 | CG | ARG | 12 | 60.325 | 82.014 | 275.369 | 1.00 19.02 | 6 |
| ATOM | 103 | CD | ARG | 12 | 61.773 | 81.666 | 275.015 | 1.00 24.56 | 6 |
| ATOM | 104 | NE | ARG | 12 | 62.109 | 81.938 | 273.619 | 1.00 30.08 | 7 |
| ATOM | 105 | CZ | ARG | 12 | 63.074 | 82.762 | 273.221 | 1.00 31.90 | 6 |
| ATOM | 106 | NH1 | ARG | 12 | 63.816 | 83.415 | 274.106 | 1.00 33.73 | 7 |
| ATOM | 107 | NH2 | ARG | 12 | 63.314 | 82.914 | 271.925 | 1.00 33.53 | 7 |
| ATOM | 108 | H | ARG | 12 | 57.864 | 83.126 | 273.790 | 1.00 0.00 | 1 |
| ATOM | 109 | HE | ARG | 12 | 61.590 | 81.496 | 272.920 | 1.00 0.00 | 1 |
| ATOM | 110 | 1HH | ARG | 12 | 63.665 | 83.287 | 275.085 | 1.00 0.00 | 6 |
| ATOM | 111 | 2HH | ARG | 12 | 64.546 | 84.023 | 273.790 | 1.00 0.00 | 6 |
| ATOM | 112 | 1HH | ARG | 12 | 62.773 | 82.409 | 271.252 | 1.00 0.00 | 6 |
| ATOM | 113 | 2HH | ARG | 12 | 64.041 | 83.531 | 271.615 | 1.00 0.00 | 6 |
| ATOM | 114 | N | ALA | 13 | 56.732 | 80.777 | 272.481 | 1.00 10.47 | 7 |
| ATOM | 115 | CA | ALA | 13 | 55.703 | 79.871 | 271.966 | 1.00 10.40 | 6 |
| ATOM | 116 | C | ALA | 13 | 56.071 | 79.223 | 270.631 | 1.00 10.05 | 6 |
| ATOM | 117 | O | ALA | 13 | 56.545 | 79.895 | 269.714 | 1.00 9.93 | 8 |
| ATOM | 118 | CB | ALA | 13 | 54.364 | 80.609 | 271.838 | 1.00 8.58 | 6 |
| ATOM | 119 | H | ALA | 13 | 56.509 | 81.710 | 272.642 | 1.00 0.00 | 1 |
| ATOM | 120 | N | ARG | 14 | 55.835 | 77.915 | 270.526 | 1.00 10.11 | 7 |
| ATOM | 121 | CA | ARG | 14 | 56.129 | 77.165 | 269.303 | 1.00 10.67 | 6 |
| ATOM | 122 | C | ARG | 14 | 55.176 | 77.580 | 268.182 | 1.00 9.87 | 6 |
| ATOM | 123 | O | ARG | 14 | 55.580 | 77.706 | 267.019 | 1.00 9.60 | 8 |
| ATOM | 124 | CB | ARG | 14 | 55.983 | 75.665 | 269.552 | 1.00 13.19 | 6 |
| ATOM | 125 | CG | ARG | 14 | 56.253 | 74.807 | 268.328 | 1.00 14.83 | 6 |
| ATOM | 126 | CD | ARG | 14 | 55.793 | 73.380 | 268.555 | 1.00 16.32 | 6 |
| ATOM | 127 | NE | ARG | 14 | 56.137 | 72.505 | 267.437 | 1.00 18.40 | 7 |
| ATOM | 128 | CZ | ARG | 14 | 55.425 | 71.441 | 267.074 | 1.00 19.14 | 6 |
| ATOM | 129 | NH1 | ARG | 14 | 54.317 | 71.118 | 267.731 | 1.00 18.63 | 7 |
| ATOM | 130 | NH2 | ARG | 14 | 55.845 | 70.676 | 266.079 | 1.00 18.96 | 7 |
| ATOM | 131 | H | ARG | 14 | 55.462 | 77.439 | 271.308 | 1.00 0.00 | 1 |
| ATOM | 132 | HE | ARG | 14 | 56.935 | 72.717 | 266.911 | 1.00 0.00 | 1 |
| ATOM | 133 | 1HH | ARG | 14 | 54.008 | 71.665 | 268.507 | 1.00 0.00 | 6 |
| ATOM | 134 | 2HH | ARG | 14 | 53.797 | 70.308 | 267.454 | 1.00 0.00 | 6 |
| ATOM | 135 | 1HH | ARG | 14 | 56.694 | 70.903 | 265.595 | 1.00 0.00 | 6 |
| ATOM | 136 | 2HH | ARG | 14 | 55.312 | 69.873 | 265.810 | 1.00 0.00 | 6 |
| ATOM | 137 | N | GLU | 15 | 53.903 | 77.721 | 268.527 | 1.00 9.10 | 7 |
| ATOM | 138 | CA | GLU | 15 | 52.878 | 78.131 | 267.581 | 1.00 9.59 | 6 |
| ATOM | 139 | C | GLU | 15 | 52.021 | 79.211 | 268.213 | 1.00 8.53 | 6 |
| ATOM | 140 | O | GLU | 15 | 51.820 | 79.225 | 269.431 | 1.00 7.89 | 8 |
| ATOM | 141 | CB | GLU | 15 | 52.003 | 76.953 | 267.163 | 1.00 12.89 | 6 |
| ATOM | 142 | CG | GLU | 15 | 52.680 | 76.027 | 266.174 | 1.00 17.65 | 6 |
| ATOM | 143 | CD | GLU | 15 | 51.717 | 75.044 | 265.552 | 1.00 19.34 | 6 |
| ATOM | 144 | OE1 | GLU | 15 | 50.828 | 74.541 | 266.275 | 1.00 20.42 | 8 |
| ATOM | 145 | OE2 | GLU | 15 | 51.853 | 74.786 | 264.334 | 1.00 22.07 | 8 |
| ATOM | 146 | H | GLU | 15 | 53.630 | 77.580 | 269.458 | 1.00 0.00 | 1 |
| ATOM | 147 | N | VAL | 16 | 51.528 | 80.121 | 267.378 | 1.00 7.40 | 7 |
| ATOM | 148 | CA | VAL | 16 | 50.701 | 81.230 | 267.835 | 1.00 6.58 | 6 |
| ATOM | 149 | C | VAL | 16 | 49.545 | 81.458 | 266.864 | 1.00 6.56 | 6 |
| ATOM | 150 | O | VAL | 16 | 49.583 | 80.981 | 265.727 | 1.00 7.67 | 8 |
| ATOM | 151 | CB | VAL | 16 | 51.536 | 82.553 | 267.906 | 1.00 5.91 | 6 |
| ATOM | 152 | CG1 | VAL | 16 | 52.671 | 82.431 | 268.908 | 1.00 5.58 | 6 |
| ATOM | 153 | CG2 | VAL | 16 | 52.105 | 82.908 | 266.528 | 1.00 5.58 | 6 |
| ATOM | 154 | H | VAL | 16 | 51.701 | 80.059 | 266.411 | 1.00 0.00 | 1 |
| ATOM | 155 | N | ARG | 17 | 48.492 | 82.122 | 267.327 | 1.00 6.26 | 7 |
| ATOM | 156 | CA | ARG | 17 | 47.373 | 82.466 | 266.459 | 1.00 6.68 | 6 |
| ATOM | 157 | C | ARG | 17 | 47.746 | 83.883 | 266.029 | 1.00 6.70 | 6 |
| ATOM | 158 | O | ARG | 17 | 47.971 | 84.754 | 266.874 | 1.00 8.67 | 8 |

| | | | | | | | | | |
|---|---|---|---|---|---|---|---|---|---|
| ATOM | 159 | CB | ARG | 17 | 46.037 | 82.457 | 267.209 | 1.00 7.79 | 6 |
| ATOM | 160 | CG | ARG | 17 | 44.860 | 82.871 | 266.324 | 1.00 10.12 | 6 |
| ATOM | 161 | CD | ARG | 17 | 43.527 | 82.382 | 266.851 | 1.00 11.33 | 6 |
| ATOM | 162 | NE | ARG | 17 | 43.203 | 82.929 | 268.163 | 1.00 13.10 | 7 |
| ATOM | 163 | CZ | ARG | 17 | 42.425 | 83.986 | 268.369 | 1.00 13.44 | 6 |
| ATOM | 164 | NH1 | ARG | 17 | 41.882 | 84.631 | 267.343 | 1.00 14.30 | 7 |
| ATOM | 165 | NH2 | ARG | 17 | 42.149 | 84.374 | 269.606 | 1.00 12.59 | 7 |
| ATOM | 166 | H | ARG | 17 | 48.487 | 82.432 | 268.257 | 1.00 0.00 | 1 |
| ATOM | 167 | HE | ARG | 17 | 43.598 | 82.485 | 268.929 | 1.00 0.00 | 1 |
| ATOM | 168 | 1HH | ARG | 17 | 42.035 | 84.336 | 266.404 | 1.00 0.00 | 6 |
| ATOM | 169 | 2HH | ARG | 17 | 41.302 | 85.429 | 267.525 | 1.00 0.00 | 6 |
| ATOM | 170 | 1HH | ARG | 17 | 42.504 | 83.876 | 270.398 | 1.00 0.00 | 6 |
| ATOM | 171 | 2HH | ARG | 17 | 41.566 | 85.174 | 269.760 | 1.00 0.00 | 6 |
| ATOM | 172 | N | LEU | 18 | 47.815 | 84.107 | 264.722 | 1.00 5.80 | 7 |
| ATOM | 173 | CA | LEU | 18 | 48.238 | 85.389 | 264.181 | 1.00 6.39 | 6 |
| ATOM | 174 | C | LEU | 18 | 47.147 | 86.304 | 263.637 | 1.00 6.74 | 6 |
| ATOM | 175 | O | LEU | 18 | 46.290 | 85.870 | 262.870 | 1.00 6.51 | 8 |
| ATOM | 176 | CB | LEU | 18 | 49.269 | 85.125 | 263.083 | 1.00 6.48 | 6 |
| ATOM | 177 | CG | LEU | 18 | 50.050 | 86.292 | 262.490 | 1.00 6.50 | 6 |
| ATOM | 178 | CD1 | LEU | 18 | 50.822 | 86.991 | 263.595 | 1.00 6.27 | 6 |
| ATOM | 179 | CD2 | LEU | 18 | 50.997 | 85.768 | 261.408 | 1.00 6.11 | 6 |
| ATOM | 180 | H | LEU | 18 | 47.554 | 83.395 | 264.104 | 1.00 0.00 | 1 |
| ATOM | 181 | N | ILE | 19 | 47.184 | 87.571 | 264.050 | 1.00 6.96 | 7 |
| ATOM | 182 | CA | ILE | 19 | 46.244 | 88.595 | 263.584 | 1.00 7.25 | 6 |
| ATOM | 183 | C | ILE | 19 | 47.138 | 89.685 | 262.985 | 1.00 8.10 | 6 |
| ATOM | 184 | O | ILE | 19 | 48.089 | 90.140 | 263.641 | 1.00 6.98 | 8 |
| ATOM | 185 | CB | ILE | 19 | 45.419 | 89.215 | 264.742 | 1.00 7.45 | 6 |
| ATOM | 186 | CG1 | ILE | 19 | 44.657 | 88.136 | 265.512 | 1.00 6.93 | 6 |
| ATOM | 187 | CG2 | ILE | 19 | 44.419 | 90.231 | 264.191 | 1.00 6.44 | 6 |
| ATOM | 188 | CD1 | ILE | 19 | 43.900 | 88.666 | 266.720 | 1.00 8.08 | 6 |
| ATOM | 189 | H | ILE | 19 | 47.867 | 87.850 | 264.697 | 1.00 0.00 | 1 |
| ATOM | 190 | N | ASP | 20 | 46.876 | 90.090 | 261.744 | 1.00 9.72 | 7 |
| ATOM | 191 | CA | ASP | 20 | 47.728 | 91.105 | 261.130 | 1.00 12.10 | 6 |
| ATOM | 192 | C | ASP | 20 | 47.372 | 92.530 | 261.543 | 1.00 13.32 | 6 |
| ATOM | 193 | O | ASP | 20 | 46.392 | 92.747 | 262.250 | 1.00 11.63 | 8 |
| ATOM | 194 | CB | ASP | 20 | 47.826 | 90.926 | 259.606 | 1.00 13.68 | 6 |
| ATOM | 195 | CG | ASP | 20 | 46.682 | 91.569 | 258.837 | 1.00 13.58 | 6 |
| ATOM | 196 | OD1 | ASP | 20 | 45.691 | 92.040 | 259.431 | 1.00 14.79 | 8 |
| ATOM | 197 | OD2 | ASP | 20 | 46.789 | 91.593 | 257.596 | 1.00 14.97 | 8 |
| ATOM | 198 | H | ASP | 20 | 46.110 | 89.702 | 261.275 | 1.00 0.00 | 1 |
| ATOM | 199 | N | GLN | 21 | 48.126 | 93.499 | 261.030 | 1.00 15.68 | 7 |
| ATOM | 200 | CA | GLN | 21 | 47.927 | 94.905 | 261.379 | 1.00 17.59 | 6 |
| ATOM | 201 | C | GLN | 21 | 46.542 | 95.488 | 261.083 | 1.00 17.56 | 6 |
| ATOM | 202 | O | GLN | 21 | 46.152 | 96.490 | 261.682 | 1.00 17.31 | 8 |
| ATOM | 203 | CB | GLN | 21 | 49.038 | 95.789 | 260.772 | 1.00 17.68 | 6 |
| ATOM | 204 | CG | GLN | 21 | 48.959 | 96.064 | 259.267 | 1.00 20.00 | 6 |
| ATOM | 205 | CD | GLN | 21 | 49.587 | 94.983 | 258.391 | 1.00 20.94 | 6 |
| ATOM | 206 | OE1 | GLN | 21 | 49.692 | 95.151 | 257.180 | 1.00 21.25 | 8 |
| ATOM | 207 | NE2 | GLN | 21 | 50.028 | 93.893 | 258.994 | 1.00 21.96 | 7 |
| ATOM | 208 | H | GLN | 21 | 48.800 | 93.228 | 260.395 | 1.00 0.00 | 1 |
| ATOM | 209 | 1HE | GLN | 21 | 50.371 | 93.212 | 258.374 | 1.00 0.00 | 6 |
| ATOM | 210 | 2HE | GLN | 21 | 50.031 | 93.788 | 259.959 | 1.00 0.00 | 6 |
| ATOM | 211 | N | ASN | 22 | 45.786 | 94.837 | 260.200 | 1.00 16.94 | 7 |
| ATOM | 212 | CA | ASN | 22 | 44.447 | 95.307 | 259.844 | 1.00 17.64 | 6 |
| ATOM | 213 | C | ASN | 22 | 43.291 | 94.507 | 260.456 | 1.00 17.12 | 6 |
| ATOM | 214 | O | ASN | 22 | 42.120 | 94.795 | 260.197 | 1.00 17.27 | 8 |
| ATOM | 215 | CB | ASN | 22 | 44.306 | 95.359 | 258.323 | 1.00 18.95 | 6 |
| ATOM | 216 | CG | ASN | 22 | 45.249 | 96.357 | 257.695 | 1.00 21.80 | 6 |
| ATOM | 217 | OD1 | ASN | 22 | 45.462 | 97.440 | 258.236 | 1.00 22.14 | 8 |
| ATOM | 218 | ND2 | ASN | 22 | 45.848 | 95.989 | 256.572 | 1.00 22.37 | 7 |
| ATOM | 219 | H | ASN | 22 | 46.150 | 94.052 | 259.768 | 1.00 0.00 | 1 |
| ATOM | 220 | 1HD | ASN | 22 | 46.441 | 96.637 | 256.141 | 1.00 0.00 | 6 |
| ATOM | 221 | 2HD | ASN | 22 | 45.660 | 95.099 | 256.214 | 1.00 0.00 | 6 |
| ATOM | 222 | N | GLY | 23 | 43.616 | 93.505 | 261.269 | 1.00 15.70 | 7 |
| ATOM | 223 | CA | GLY | 23 | 42.578 | 92.708 | 261.897 | 1.00 12.72 | 6 |
| ATOM | 224 | C | GLY | 23 | 42.262 | 91.400 | 261.198 | 1.00 11.40 | 6 |
| ATOM | 225 | O | GLY | 23 | 41.342 | 90.686 | 261.596 | 1.00 11.12 | 8 |
| ATOM | 226 | H | GLY | 23 | 44.547 | 93.302 | 261.501 | 1.00 0.00 | 1 |
| ATOM | 227 | N | ASP | 24 | 43.019 | 91.080 | 260.155 | 1.00 9.54 | 7 |
| ATOM | 228 | CA | ASP | 24 | 42.824 | 89.840 | 259.408 | 1.00 9.48 | 6 |
| ATOM | 229 | C | ASP | 24 | 43.344 | 88.680 | 260.259 | 1.00 9.36 | 6 |
| ATOM | 230 | O | ASP | 24 | 44.475 | 88.725 | 260.748 | 1.00 9.59 | 8 |
| ATOM | 231 | CB | ASP | 24 | 43.579 | 89.906 | 258.071 | 1.00 10.31 | 6 |
| ATOM | 232 | CG | ASP | 24 | 43.212 | 88.775 | 257.120 | 1.00 11.38 | 6 |
| ATOM | 233 | OD1 | ASP | 24 | 42.178 | 88.111 | 257.326 | 1.00 10.36 | 8 |
| ATOM | 234 | OD2 | ASP | 24 | 43.962 | 88.563 | 256.145 | 1.00 12.15 | 8 |
| ATOM | 235 | H | ASP | 24 | 43.712 | 91.697 | 259.885 | 1.00 0.00 | 1 |
| ATOM | 236 | N | GLN | 25 | 42.494 | 87.676 | 260.471 | 1.00 8.68 | 7 |
| ATOM | 237 | CA | GLN | 25 | 42.851 | 86.500 | 261.262 | 1.00 9.35 | 6 |
| ATOM | 238 | C | GLN | 25 | 43.605 | 85.525 | 260.361 | 1.00 10.25 | 6 |
| ATOM | 239 | O | GLN | 25 | 42.997 | 84.821 | 259.549 | 1.00 10.63 | 8 |
| ATOM | 240 | CB | GLN | 25 | 41.583 | 85.842 | 261.814 | 1.00 10.83 | 6 |
| ATOM | 241 | CG | GLN | 25 | 40.766 | 86.723 | 262.757 | 1.00 9.56 | 6 |
| ATOM | 242 | CD | GLN | 25 | 41.282 | 86.706 | 264.193 | 1.00 11.13 | 6 |
| ATOM | 243 | OE1 | GLN | 25 | 42.031 | 85.815 | 264.587 | 1.00 11.15 | 8 |
| ATOM | 244 | NE2 | GLN | 25 | 40.868 | 87.687 | 264.980 | 1.00 11.75 | 7 |
| ATOM | 245 | H | GLN | 25 | 41.602 | 87.706 | 260.066 | 1.00 0.00 | 1 |

| | | | | | | | | | |
|---|---|---|---|---|---|---|---|---|---|
| ATOM | 246 | 1HE | GLN | 25 | 41.188 | 87.711 | 265.906 | 1.00 0.00 | 6 |
| ATOM | 247 | 2HE | GLN | 25 | 40.271 | 88.355 | 264.591 | 1.00 0.00 | 6 |
| ATOM | 248 | N | LEU | 26 | 44.925 | 85.497 | 260.498 | 1.00 11.29 | 7 |
| ATOM | 249 | CA | LEU | 26 | 45.778 | 84.634 | 259.685 | 1.00 12.21 | 6 |
| ATOM | 250 | C | LEU | 26 | 45.821 | 83.160 | 260.103 | 1.00 12.72 | 6 |
| ATOM | 251 | O | LEU | 26 | 46.365 | 82.324 | 259.376 | 1.00 13.15 | 8 |
| ATOM | 252 | CB | LEU | 26 | 47.190 | 85.225 | 259.607 | 1.00 14.89 | 6 |
| ATOM | 253 | CG | LEU | 26 | 47.526 | 86.137 | 258.415 | 1.00 16.13 | 6 |
| ATOM | 254 | CD1 | LEU | 26 | 46.334 | 86.954 | 257.970 | 1.00 18.50 | 6 |
| ATOM | 255 | CD2 | LEU | 26 | 48.694 | 87.043 | 258.754 | 1.00 17.06 | 6 |
| ATOM | 256 | H | LEU | 26 | 45.332 | 86.059 | 261.191 | 1.00 0.00 | 1 |
| ATOM | 257 | N | GLY | 27 | 45.232 | 82.841 | 261.250 | 1.00 11.93 | 7 |
| ATOM | 258 | CA | GLY | 27 | 45.214 | 81.465 | 261.708 | 1.00 11.71 | 6 |
| ATOM | 259 | C | GLY | 27 | 46.415 | 81.079 | 262.546 | 1.00 10.86 | 6 |
| ATOM | 260 | O | GLY | 27 | 47.210 | 81.930 | 262.954 | 1.00 10.75 | 8 |
| ATOM | 261 | H | GLY | 27 | 44.808 | 83.519 | 261.819 | 1.00 0.00 | 1 |
| ATOM | 262 | N | ILE | 28 | 46.538 | 79.783 | 262.813 | 1.00 10.58 | 7 |
| ATOM | 263 | CA | ILE | 28 | 47.633 | 79.265 | 263.620 | 1.00 10.71 | 6 |
| ATOM | 264 | C | ILE | 28 | 48.876 | 79.125 | 262.760 | 1.00 10.57 | 6 |
| ATOM | 265 | O | ILE | 28 | 48.848 | 78.481 | 261.711 | 1.00 11.09 | 8 |
| ATOM | 266 | CB | ILE | 28 | 47.268 | 77.898 | 264.266 | 1.00 12.27 | 6 |
| ATOM | 267 | CG1 | ILE | 28 | 46.037 | 78.044 | 265.167 | 1.00 12.42 | 6 |
| ATOM | 268 | CG2 | ILE | 28 | 48.435 | 77.368 | 265.097 | 1.00 11.34 | 6 |
| ATOM | 269 | CD1 | ILE | 28 | 44.717 | 78.075 | 264.425 | 1.00 13.46 | 6 |
| ATOM | 270 | H | ILE | 28 | 45.879 | 79.165 | 262.443 | 1.00 0.00 | 1 |
| ATOM | 271 | N | LYS | 29 | 49.960 | 79.747 | 263.205 | 1.00 10.46 | 7 |
| ATOM | 272 | CA | LYS | 29 | 51.225 | 79.720 | 262.487 | 1.00 11.09 | 6 |
| ATOM | 273 | C | LYS | 29 | 52.363 | 79.354 | 263.427 | 1.00 9.35 | 6 |
| ATOM | 274 | O | LYS | 29 | 52.280 | 79.579 | 264.635 | 1.00 8.95 | 8 |
| ATOM | 275 | CB | LYS | 29 | 51.535 | 81.109 | 261.913 | 1.00 12.29 | 6 |
| ATOM | 276 | CG | LYS | 29 | 50.487 | 81.691 | 260.976 | 1.00 14.90 | 6 |
| ATOM | 277 | CD | LYS | 29 | 50.514 | 80.987 | 259.648 | 1.00 16.65 | 6 |
| ATOM | 278 | CE | LYS | 29 | 49.642 | 81.692 | 258.633 | 1.00 18.42 | 6 |
| ATOM | 279 | NZ | LYS | 29 | 49.789 | 81.055 | 257.298 | 1.00 21.12 | 7 |
| ATOM | 280 | H | LYS | 29 | 49.937 | 80.242 | 264.048 | 1.00 0.00 | 1 |
| ATOM | 281 | 1HZ | LYS | 29 | 50.782 | 81.118 | 257.011 | 1.00 0.00 | 6 |
| ATOM | 282 | 2HZ | LYS | 29 | 49.498 | 80.057 | 257.333 | 1.00 0.00 | 6 |
| ATOM | 283 | 3HZ | LYS | 29 | 49.195 | 81.568 | 256.612 | 1.00 0.00 | 6 |
| ATOM | 284 | N | SER | 30 | 53.427 | 78.790 | 262.869 | 1.00 8.52 | 7 |
| ATOM | 285 | CA | SER | 30 | 54.598 | 78.476 | 263.668 | 1.00 8.28 | 6 |
| ATOM | 286 | C | SER | 30 | 55.185 | 79.852 | 263.993 | 1.00 8.23 | 6 |
| ATOM | 287 | O | SER | 30 | 54.952 | 80.813 | 263.249 | 1.00 7.88 | 8 |
| ATOM | 288 | CB | SER | 30 | 55.612 | 77.661 | 262.858 | 1.00 8.27 | 6 |
| ATOM | 289 | OG | SER | 30 | 56.050 | 78.355 | 261.695 | 1.00 6.54 | 8 |
| ATOM | 290 | H | SER | 30 | 53.402 | 78.571 | 261.919 | 1.00 0.00 | 1 |
| ATOM | 291 | HG | SER | 30 | 55.324 | 78.304 | 261.052 | 1.00 0.00 | 1 |
| ATOM | 292 | N | LYS | 31 | 55.910 | 79.961 | 265.098 | 1.00 8.39 | 7 |
| ATOM | 293 | CA | LYS | 31 | 56.527 | 81.227 | 265.470 | 1.00 9.33 | 6 |
| ATOM | 294 | C | LYS | 31 | 57.431 | 81.716 | 264.338 | 1.00 8.85 | 6 |
| ATOM | 295 | O | LYS | 31 | 57.469 | 82.908 | 264.036 | 1.00 7.99 | 8 |
| ATOM | 296 | CB | LYS | 31 | 57.343 | 81.074 | 266.754 | 1.00 10.57 | 6 |
| ATOM | 297 | CG | LYS | 31 | 57.961 | 82.378 | 267.227 | 1.00 13.93 | 6 |
| ATOM | 298 | CD | LYS | 31 | 58.827 | 82.195 | 268.462 | 1.00 17.94 | 6 |
| ATOM | 299 | CE | LYS | 31 | 60.069 | 81.380 | 268.176 | 1.00 19.35 | 6 |
| ATOM | 300 | NZ | LYS | 31 | 60.995 | 81.391 | 269.346 | 1.00 21.96 | 7 |
| ATOM | 301 | H | LYS | 31 | 55.997 | 79.190 | 265.702 | 1.00 0.00 | 1 |
| ATOM | 302 | 1HZ | LYS | 31 | 60.509 | 80.996 | 270.182 | 1.00 0.00 | 6 |
| ATOM | 303 | 2HZ | LYS | 31 | 61.832 | 80.814 | 269.132 | 1.00 0.00 | 6 |
| ATOM | 304 | 3HZ | LYS | 31 | 61.284 | 82.371 | 269.543 | 1.00 0.00 | 6 |
| ATOM | 305 | N | GLN | 32 | 58.153 | 80.787 | 263.715 | 1.00 8.07 | 7 |
| ATOM | 306 | CA | GLN | 32 | 59.054 | 81.098 | 262.607 | 1.00 8.90 | 6 |
| ATOM | 307 | C | GLN | 32 | 58.330 | 81.791 | 261.441 | 1.00 8.16 | 6 |
| ATOM | 308 | O | GLN | 32 | 58.792 | 82.820 | 260.939 | 1.00 7.08 | 8 |
| ATOM | 309 | CB | GLN | 32 | 59.736 | 79.815 | 262.110 | 1.00 10.88 | 6 |
| ATOM | 310 | CG | GLN | 32 | 60.620 | 79.998 | 260.877 | 1.00 12.55 | 6 |
| ATOM | 311 | CD | GLN | 32 | 61.812 | 80.909 | 261.119 | 1.00 13.03 | 6 |
| ATOM | 312 | OE1 | GLN | 32 | 62.241 | 81.109 | 262.260 | 1.00 15.52 | 8 |
| ATOM | 313 | NE2 | GLN | 32 | 62.352 | 81.466 | 260.045 | 1.00 14.99 | 7 |
| ATOM | 314 | H | GLN | 32 | 58.080 | 79.864 | 264.023 | 1.00 0.00 | 1 |
| ATOM | 315 | 1HE | GLN | 32 | 63.143 | 82.032 | 260.177 | 1.00 0.00 | 6 |
| ATOM | 316 | 2HE | GLN | 32 | 61.950 | 81.290 | 259.172 | 1.00 0.00 | 6 |
| ATOM | 317 | N | GLU | 33 | 57.204 | 81.225 | 261.010 | 1.00 7.32 | 7 |
| ATOM | 318 | CA | GLU | 33 | 56.444 | 81.812 | 259.908 | 1.00 7.40 | 6 |
| ATOM | 319 | C | GLU | 33 | 55.852 | 83.162 | 260.312 | 1.00 7.28 | 6 |
| ATOM | 320 | O | GLU | 33 | 55.811 | 84.094 | 259.508 | 1.00 5.58 | 8 |
| ATOM | 321 | CB | GLU | 33 | 55.333 | 80.874 | 259.424 | 1.00 8.23 | 6 |
| ATOM | 322 | CG | GLU | 33 | 54.613 | 81.413 | 258.187 | 1.00 10.30 | 6 |
| ATOM | 323 | CD | GLU | 33 | 53.498 | 80.521 | 257.671 | 1.00 11.21 | 6 |
| ATOM | 324 | OE1 | GLU | 33 | 53.402 | 79.351 | 258.089 | 1.00 10.57 | 8 |
| ATOM | 325 | OE2 | GLU | 33 | 52.714 | 81.000 | 256.825 | 1.00 10.63 | 8 |
| ATOM | 326 | H | GLU | 33 | 56.877 | 80.407 | 261.449 | 1.00 0.00 | 1 |
| ATOM | 327 | N | ALA | 34 | 55.408 | 83.267 | 261.562 | 1.00 6.39 | 7 |
| ATOM | 328 | CA | ALA | 34 | 54.833 | 84.511 | 262.069 | 1.00 6.12 | 6 |
| ATOM | 329 | C | ALA | 34 | 55.891 | 85.613 | 262.027 | 1.00 6.17 | 6 |
| ATOM | 330 | O | ALA | 34 | 55.604 | 86.749 | 261.641 | 1.00 5.58 | 8 |
| ATOM | 331 | CB | ALA | 34 | 54.314 | 84.316 | 263.484 | 1.00 5.90 | 6 |
| ATOM | 332 | H | ALA | 34 | 55.465 | 82.490 | 262.164 | 1.00 0.00 | 1 |

```
ATOM    333  N   LEU    35      57.119  85.258 262.403  1.00  5.95      7
ATOM    334  CA  LEU    35      58.239  86.195 262.396  1.00  6.73      6
ATOM    335  C   LEU    35      58.582  86.624 260.961  1.00  6.22      6
ATOM    336  O   LEU    35      58.975  87.769 260.719  1.00  5.86      8
ATOM    337  CB  LEU    35      59.461  85.569 263.080  1.00  7.16      6
ATOM    338  CG  LEU    35      59.354  85.396 264.603  1.00  8.14      6
ATOM    339  CD1 LEU    35      60.436  84.463 265.112  1.00  8.57      6
ATOM    340  CD2 LEU    35      59.431  86.758 265.296  1.00  8.91      6
ATOM    341  H   LEU    35      57.277  84.341 262.699  1.00  0.00      1
ATOM    342  N   GLU    36      58.436  85.701 260.017  1.00  5.79      7
ATOM    343  CA  GLU    36      58.703  86.009 258.611  1.00  6.95      6
ATOM    344  C   GLU    36      57.686  87.012 258.074  1.00  6.00      6
ATOM    345  O   GLU    36      58.054  87.971 257.391  1.00  5.80      8
ATOM    346  CB  GLU    36      58.659  84.737 257.774  1.00  5.96      6
ATOM    347  CG  GLU    36      59.789  83.797 258.092  1.00  6.19      6
ATOM    348  CD  GLU    36      59.664  82.459 257.403  1.00  8.34      6
ATOM    349  OE1 GLU    36      58.596  82.141 256.834  1.00  7.19      8
ATOM    350  OE2 GLU    36      60.660  81.722 257.452  1.00  7.79      8
ATOM    351  H   GLU    36      58.159  84.797 260.283  1.00  0.00      1
ATOM    352  N   ILE    37      56.411  86.784 258.378  1.00  5.98      7
ATOM    353  CA  ILE    37      55.344  87.680 257.930  1.00  7.06      6
ATOM    354  C   ILE    37      55.544  89.085 258.502  1.00  7.03      6
ATOM    355  O   ILE    37      55.382  90.075 257.794  1.00  7.37      8
ATOM    356  CB  ILE    37      53.950  87.148 258.332  1.00  7.01      6
ATOM    357  CG1 ILE    37      53.697  85.792 257.664  1.00  6.53      6
ATOM    358  CG2 ILE    37      52.869  88.144 257.911  1.00  6.84      6
ATOM    359  CD1 ILE    37      52.408  85.108 258.103  1.00  6.26      6
ATOM    360  H   ILE    37      56.183  85.988 258.905  1.00  0.00      1
ATOM    361  N   ALA    38      55.903  89.173 259.777  1.00  6.53      7
ATOM    362  CA  ALA    38      56.133  90.469 260.412  1.00  7.16      6
ATOM    363  C   ALA    38      57.285  91.187 259.717  1.00  8.30      6
ATOM    364  O   ALA    38      57.182  92.366 259.381  1.00  8.62      8
ATOM    365  CB  ALA    38      56.450  90.288 261.898  1.00  7.14      6
ATOM    366  H   ALA    38      55.998  88.349 260.303  1.00  0.00      1
ATOM    367  N   ALA    39      58.358  90.448 259.463  1.00  7.57      7
ATOM    368  CA  ALA    39      59.549  90.994 258.829  1.00  8.02      6
ATOM    369  C   ALA    39      59.302  91.518 257.423  1.00  8.67      6
ATOM    370  O   ALA    39      59.788  92.598 257.073  1.00  8.55      8
ATOM    371  CB  ALA    39      60.656  89.968 258.825  1.00  8.94      6
ATOM    372  H   ALA    39      58.365  89.498 259.699  1.00  0.00      1
ATOM    373  N   ARG    40      58.548  90.780 256.613  1.00  9.27      7
ATOM    374  CA  ARG    40      58.292  91.239 255.252  1.00 10.16      6
ATOM    375  C   ARG    40      57.463  92.517 255.233  1.00  9.75      6
ATOM    376  O   ARG    40      57.543  93.298 254.284  1.00  9.76      8
ATOM    377  CB  ARG    40      57.667  90.144 254.377  1.00 10.73      6
ATOM    378  CG  ARG    40      56.294  89.656 254.783  1.00 12.71      6
ATOM    379  CD  ARG    40      55.876  88.429 253.949  1.00 12.88      6
ATOM    380  NE  ARG    40      55.584  88.761 252.554  1.00 13.75      7
ATOM    381  CZ  ARG    40      56.103  88.132 251.501  1.00 13.55      6
ATOM    382  NH1 ARG    40      56.955  87.125 251.665  1.00 13.50      7
ATOM    383  NH2 ARG    40      55.758  88.505 250.276  1.00 11.85      7
ATOM    384  H   ARG    40      58.185  89.920 256.925  1.00  0.00      1
ATOM    385  HE  ARG    40      54.963  89.499 252.376  1.00  0.00      1
ATOM    386  1HH ARG    40      57.218  86.830 252.581  1.00  0.00      6
ATOM    387  2HH ARG    40      57.339  86.664 250.867  1.00  0.00      6
ATOM    388  1HH ARG    40      55.108  89.251 250.137  1.00  0.00      6
ATOM    389  2HH ARG    40      56.155  88.035 249.491  1.00  0.00      6
ATOM    390  N   ARG    41      56.704  92.749 256.301  1.00  9.31      7
ATOM    391  CA  ARG    41      55.875  93.940 256.412  1.00 10.44      6
ATOM    392  C   ARG    41      56.559  95.057 257.188  1.00  9.89      6
ATOM    393  O   ARG    41      55.967  96.116 257.403  1.00  9.31      8
ATOM    394  CB  ARG    41      54.543  93.592 257.066  1.00 10.83      6
ATOM    395  CG  ARG    41      53.764  92.590 256.262  1.00 12.25      6
ATOM    396  CD  ARG    41      52.376  92.393 256.802  1.00 13.86      6
ATOM    397  NE  ARG    41      51.677  91.378 256.027  1.00 16.23      7
ATOM    398  CZ  ARG    41      50.358  91.252 255.973  1.00 16.53      6
ATOM    399  NH1 ARG    41      49.576  92.081 256.650  1.00 17.37      7
ATOM    400  NH2 ARG    41      49.817  90.284 255.245  1.00 17.65      7
ATOM    401  H   ARG    41      56.676  92.099 257.038  1.00  0.00      1
ATOM    402  HE  ARG    41      52.223  90.741 255.519  1.00  0.00      1
ATOM    403  1HH ARG    41      49.990  92.809 257.188  1.00  0.00      6
ATOM    404  2HH ARG    41      48.587  91.990 256.593  1.00  0.00      6
ATOM    405  1HH ARG    41      50.411  89.658 254.742  1.00  0.00      6
ATOM    406  2HH ARG    41      48.821  90.200 255.190  1.00  0.00      6
ATOM    407  N   ASN    42      57.796  94.811 257.608  1.00 10.09      7
ATOM    408  CA  ASN    42      58.575  95.780 258.370  1.00 10.83      6
ATOM    409  C   ASN    42      57.844  96.204 259.642  1.00 10.08      6
ATOM    410  O   ASN    42      57.806  97.387 259.999  1.00  8.78      8
ATOM    411  CB  ASN    42      58.908  97.003 257.513  1.00 13.43      6
ATOM    412  CG  ASN    42      60.379  97.102 257.202  1.00 17.22      6
ATOM    413  OD1 ASN    42      61.134  97.753 257.928  1.00 19.53      8
ATOM    414  ND2 ASN    42      60.807  96.445 256.132  1.00 19.06      7
ATOM    415  H   ASN    42      58.212  93.945 257.418  1.00  0.00      1
ATOM    416  1HD ASN    42      61.769  96.469 255.961  1.00  0.00      6
ATOM    417  2HD ASN    42      60.170  95.958 255.565  1.00  0.00      6
ATOM    418  N   LEU    43      57.238  95.220 260.299  1.00  7.86      7
ATOM    419  CA  LEU    43      56.495  95.420 261.535  1.00  7.40      6
```

```
ATOM  420  C    LEU  43   57.021  94.435 262.585  1.00  6.83  6
ATOM  421  O    LEU  43   57.906  93.621 262.303  1.00  6.50  8
ATOM  422  CB   LEU  43   55.004  95.168 261.282  1.00  6.97  6
ATOM  423  CG   LEU  43   54.018  96.323 261.071  1.00  8.67  6
ATOM  424  CD1  LEU  43   54.698  97.622 260.722  1.00  7.64  6
ATOM  425  CD2  LEU  43   52.999  95.938 260.031  1.00  6.81  6
ATOM  426  H    LEU  43   57.319  94.298 259.973  1.00  0.00  1
ATOM  427  N    ASP  44   56.466  94.506 263.789  1.00  5.77  7
ATOM  428  CA   ASP  44   56.882  93.628 264.879  1.00  5.91  6
ATOM  429  C    ASP  44   55.811  92.581 265.146  1.00  5.58  6
ATOM  430  O    ASP  44   54.641  92.782 264.820  1.00  5.64  8
ATOM  431  CB   ASP  44   57.080  94.429 266.172  1.00  5.98  6
ATOM  432  CG   ASP  44   58.132  95.513 266.044  1.00  6.05  6
ATOM  433  OD1  ASP  44   59.312  95.183 265.846  1.00  5.58  8
ATOM  434  OD2  ASP  44   57.771  96.698 266.161  1.00  6.49  8
ATOM  435  H    ASP  44   55.719  95.116 263.957  1.00  0.00  1
ATOM  436  N    LEU  45   56.229  91.468 265.737  1.00  5.66  7
ATOM  437  CA   LEU  45   55.324  90.389 266.121  1.00  5.77  6
ATOM  438  C    LEU  45   55.157  90.627 267.621  1.00  5.67  6
ATOM  439  O    LEU  45   56.118  90.510 268.377  1.00  5.69  8
ATOM  440  CB   LEU  45   55.973  89.026 265.875  1.00  6.27  6
ATOM  441  CG   LEU  45   55.081  87.804 266.127  1.00  7.35  6
ATOM  442  CD1  LEU  45   53.933  87.787 265.142  1.00  7.25  6
ATOM  443  CD2  LEU  45   55.900  86.536 265.996  1.00  7.76  6
ATOM  444  H    LEU  45   57.177  91.383 265.943  1.00  0.00  1
ATOM  445  N    VAL  46   53.957  91.002 268.043  1.00  5.58  7
ATOM  446  CA   VAL  46   53.713  91.304 269.448  1.00  5.58  6
ATOM  447  C    VAL  46   52.793  90.292 270.132  1.00  5.58  6
ATOM  448  O    VAL  46   51.700  90.004 269.644  1.00  5.58  8
ATOM  449  CB   VAL  46   53.119  92.730 269.589  1.00  5.58  6
ATOM  450  CG1  VAL  46   52.943  93.100 271.049  1.00  6.30  6
ATOM  451  CG2  VAL  46   54.015  93.738 268.877  1.00  6.25  6
ATOM  452  H    VAL  46   53.222  91.080 267.404  1.00  0.00  1
ATOM  453  N    LEU  47   53.241  89.763 271.266  1.00  5.58  7
ATOM  454  CA   LEU  47   52.450  88.795 272.013  1.00  6.29  6
ATOM  455  C    LEU  47   51.401  89.555 272.826  1.00  5.74  6
ATOM  456  O    LEU  47   51.664  89.992 273.944  1.00  5.76  8
ATOM  457  CB   LEU  47   53.364  87.962 272.924  1.00  7.05  6
ATOM  458  CG   LEU  47   52.726  86.772 273.653  1.00  7.11  6
ATOM  459  CD1  LEU  47   52.080  85.831 272.642  1.00  7.12  6
ATOM  460  CD2  LEU  47   53.776  86.028 274.478  1.00  8.11  6
ATOM  461  H    LEU  47   54.113  90.045 271.615  1.00  0.00  1
ATOM  462  N    VAL  48   50.213  89.724 272.258  1.00  5.92  7
ATOM  463  CA   VAL  48   49.148  90.464 272.929  1.00  6.65  6
ATOM  464  C    VAL  48   48.301  89.654 273.905  1.00  6.57  6
ATOM  465  O    VAL  48   47.662  90.230 274.782  1.00  7.39  8
ATOM  466  CB   VAL  48   48.234  91.207 271.915  1.00  5.75  6
ATOM  467  CG1  VAL  48   49.052  92.233 271.146  1.00  5.85  6
ATOM  468  CG2  VAL  48   47.575  90.218 270.952  1.00  5.75  6
ATOM  469  H    VAL  48   50.070  89.341 271.365  1.00  0.00  1
ATOM  470  N    ALA  49   48.280  88.335 273.748  1.00  6.18  7
ATOM  471  CA   ALA  49   47.511  87.476 274.645  1.00  6.65  6
ATOM  472  C    ALA  49   48.356  86.246 274.966  1.00  7.16  6
ATOM  473  O    ALA  49   48.130  85.162 274.424  1.00  6.49  8
ATOM  474  CB   ALA  49   46.188  87.075 274.001  1.00  6.22  6
ATOM  475  H    ALA  49   48.776  87.938 273.002  1.00  0.00  1
ATOM  476  N    PRO  50   49.312  86.394 275.897  1.00  8.35  7
ATOM  477  CA   PRO  50   50.228  85.338 276.330  1.00  8.58  6
ATOM  478  C    PRO  50   49.565  84.076 276.841  1.00  9.39  6
ATOM  479  O    PRO  50   50.055  82.976 276.597  1.00  9.26  8
ATOM  480  CB   PRO  50   51.024  86.006 277.456  1.00  8.84  6
ATOM  481  CG   PRO  50   50.954  87.448 277.124  1.00  9.22  6
ATOM  482  CD   PRO  50   49.524  87.613 276.697  1.00  7.93  6
ATOM  483  N    ASN  51   48.443  84.231 277.534  1.00  9.48  7
ATOM  484  CA   ASN  51   47.756  83.085 278.109  1.00 10.67  6
ATOM  485  C    ASN  51   46.613  82.478 277.301  1.00 11.09  6
ATOM  486  O    ASN  51   45.917  81.586 277.786  1.00 10.91  8
ATOM  487  CB   ASN  51   47.309  83.407 279.538  1.00 12.24  6
ATOM  488  CG   ASN  51   48.478  83.753 280.443  1.00 13.54  6
ATOM  489  OD1  ASN  51   48.519  84.825 281.043  1.00 14.69  8
ATOM  490  ND2  ASN  51   49.449  82.860 280.525  1.00 13.61  7
ATOM  491  H    ASN  51   48.059  85.127 277.661  1.00  0.00  1
ATOM  492  1HD  ASN  51   50.227  83.046 281.089  1.00  0.00  6
ATOM  493  2HD  ASN  51   49.353  82.035 280.007  1.00  0.00  6
ATOM  494  N    ALA  52   46.422  82.953 276.072  1.00 11.13  7
ATOM  495  CA   ALA  52   45.374  82.414 275.214  1.00  9.83  6
ATOM  496  C    ALA  52   45.880  81.090 274.654  1.00  9.44  6
ATOM  497  O    ALA  52   47.080  80.808 274.714  1.00  9.05  8
ATOM  498  CB   ALA  52   45.056  83.378 274.085  1.00  9.53  6
ATOM  499  H    ALA  52   47.013  83.653 275.729  1.00  0.00  1
ATOM  500  N    LYS  53   44.974  80.274 274.123  1.00  9.03  7
ATOM  501  CA   LYS  53   45.347  78.971 273.574  1.00  9.84  6
ATOM  502  C    LYS  53   44.936  78.801 272.113  1.00  8.68  6
ATOM  503  O    LYS  53   43.747  78.730 271.812  1.00  9.64  8
ATOM  504  CB   LYS  53   44.723  77.840 274.399  1.00 12.61  6
ATOM  505  CG   LYS  53   45.207  77.748 275.833  1.00 15.82  6
ATOM  506  CD   LYS  53   44.700  76.464 276.477  1.00 19.19  6
```

| ATOM | 507 | CE | LYS | 53 | 45.014 | 76.413 | 277.964 | 1.00 | 21.22 | 6 |
|---|---|---|---|---|---|---|---|---|---|---|
| ATOM | 508 | NZ | LYS | 53 | 44.276 | 77.474 | 278.715 | 1.00 | 24.52 | 7 |
| ATOM | 509 | H | LYS | 53 | 44.028 | 80.547 | 274.087 | 1.00 | 0.00 | 1 |
| ATOM | 510 | 1HZ | LYS | 53 | 43.257 | 77.363 | 278.563 | 1.00 | 0.00 | 6 |
| ATOM | 511 | 2HZ | LYS | 53 | 44.488 | 77.396 | 279.731 | 1.00 | 0.00 | 6 |
| ATOM | 512 | 3HZ | LYS | 53 | 44.583 | 78.407 | 278.367 | 1.00 | 0.00 | 6 |
| ATOM | 513 | N | PRO | 54 | 45.902 | 78.876 | 271.180 | 1.00 | 8.46 | 7 |
| ATOM | 514 | CA | PRO | 54 | 47.324 | 79.113 | 271.440 | 1.00 | 7.53 | 6 |
| ATOM | 515 | C | PRO | 54 | 47.534 | 80.622 | 271.672 | 1.00 | 6.52 | 6 |
| ATOM | 516 | O | PRO | 54 | 46.606 | 81.415 | 271.466 | 1.00 | 7.03 | 8 |
| ATOM | 517 | CB | PRO | 54 | 47.983 | 78.626 | 270.148 | 1.00 | 8.59 | 6 |
| ATOM | 518 | CG | PRO | 54 | 46.965 | 78.926 | 269.119 | 1.00 | 8.26 | 6 |
| ATOM | 519 | CD | PRO | 54 | 45.681 | 78.508 | 269.767 | 1.00 | 8.30 | 6 |
| ATOM | 520 | N | PRO | 55 | 48.721 | 81.029 | 272.156 | 1.00 | 6.14 | 7 |
| ATOM | 521 | CA | PRO | 55 | 48.993 | 82.454 | 272.409 | 1.00 | 6.03 | 6 |
| ATOM | 522 | C | PRO | 55 | 48.718 | 83.317 | 271.176 | 1.00 | 5.80 | 6 |
| ATOM | 523 | O | PRO | 55 | 49.042 | 82.928 | 270.057 | 1.00 | 5.81 | 8 |
| ATOM | 524 | CB | PRO | 55 | 50.471 | 82.449 | 272.779 | 1.00 | 6.37 | 6 |
| ATOM | 525 | CG | PRO | 55 | 50.637 | 81.108 | 273.453 | 1.00 | 7.29 | 6 |
| ATOM | 526 | CD | PRO | 55 | 49.888 | 80.203 | 272.517 | 1.00 | 6.34 | 6 |
| ATOM | 527 | N | VAL | 56 | 48.108 | 84.480 | 271.389 | 1.00 | 6.26 | 7 |
| ATOM | 528 | CA | VAL | 56 | 47.773 | 85.375 | 270.281 | 1.00 | 5.82 | 6 |
| ATOM | 529 | C | VAL | 56 | 48.813 | 86.464 | 270.048 | 1.00 | 6.12 | 6 |
| ATOM | 530 | O | VAL | 56 | 49.243 | 87.148 | 270.979 | 1.00 | 5.58 | 8 |
| ATOM | 531 | CB | VAL | 56 | 46.388 | 86.032 | 270.480 | 1.00 | 6.85 | 6 |
| ATOM | 532 | CG1 | VAL | 56 | 46.032 | 86.904 | 269.276 | 1.00 | 6.85 | 6 |
| ATOM | 533 | CG2 | VAL | 56 | 45.319 | 84.965 | 270.686 | 1.00 | 6.33 | 6 |
| ATOM | 534 | H | VAL | 56 | 47.886 | 84.747 | 272.303 | 1.00 | 0.00 | 1 |
| ATOM | 535 | N | CYS | 57 | 49.222 | 86.594 | 268.791 | 1.00 | 6.48 | 7 |
| ATOM | 536 | CA | CYS | 57 | 50.193 | 87.599 | 268.382 | 1.00 | 6.96 | 6 |
| ATOM | 537 | C | CYS | 57 | 49.550 | 88.536 | 267.375 | 1.00 | 7.88 | 6 |
| ATOM | 538 | O | CYS | 57 | 48.751 | 88.114 | 266.533 | 1.00 | 7.58 | 8 |
| ATOM | 539 | CB | CYS | 57 | 51.420 | 86.943 | 267.742 | 1.00 | 7.53 | 6 |
| ATOM | 540 | SG | CYS | 57 | 52.550 | 86.169 | 268.914 | 1.00 | 7.31 | 16 |
| ATOM | 541 | H | CYS | 57 | 48.826 | 86.017 | 268.107 | 1.00 | 0.00 | 1 |
| ATOM | 542 | N | ARG | 58 | 49.907 | 89.809 | 267.458 | 1.00 | 8.78 | 7 |
| ATOM | 543 | CA | ARG | 58 | 49.383 | 90.806 | 266.543 | 1.00 | 10.37 | 6 |
| ATOM | 544 | C | ARG | 58 | 50.563 | 91.450 | 265.832 | 1.00 | 10.39 | 6 |
| ATOM | 545 | O | ARG | 58 | 51.614 | 91.687 | 266.441 | 1.00 | 9.83 | 8 |
| ATOM | 546 | CB | ARG | 58 | 48.602 | 91.871 | 267.314 | 1.00 | 14.50 | 6 |
| ATOM | 547 | CG | ARG | 58 | 47.924 | 92.911 | 266.433 | 1.00 | 18.88 | 6 |
| ATOM | 548 | CD | ARG | 58 | 47.286 | 94.003 | 267.282 | 1.00 | 22.75 | 6 |
| ATOM | 549 | NE | ARG | 58 | 46.431 | 93.452 | 268.331 | 1.00 | 26.96 | 7 |
| ATOM | 550 | CZ | ARG | 58 | 45.238 | 92.909 | 268.114 | 1.00 | 29.11 | 6 |
| ATOM | 551 | NH1 | ARG | 58 | 44.748 | 92.847 | 266.879 | 1.00 | 29.98 | 7 |
| ATOM | 552 | NH2 | ARG | 58 | 44.535 | 92.427 | 269.133 | 1.00 | 31.25 | 7 |
| ATOM | 553 | H | ARG | 58 | 50.544 | 90.113 | 268.134 | 1.00 | 0.00 | 1 |
| ATOM | 554 | HE | ARG | 58 | 46.762 | 93.480 | 269.255 | 1.00 | 0.00 | 1 |
| ATOM | 555 | 1HH | ARG | 58 | 45.273 | 93.226 | 266.119 | 1.00 | 0.00 | 6 |
| ATOM | 556 | 2HH | ARG | 58 | 43.862 | 92.433 | 266.696 | 1.00 | 0.00 | 6 |
| ATOM | 557 | 1HH | ARG | 58 | 44.911 | 92.468 | 270.059 | 1.00 | 0.00 | 6 |
| ATOM | 558 | 2HH | ARG | 58 | 43.635 | 92.018 | 268.977 | 1.00 | 0.00 | 6 |
| ATOM | 559 | N | ILE | 59 | 50.411 | 91.674 | 264.532 | 1.00 | 9.61 | 7 |
| ATOM | 560 | CA | ILE | 59 | 51.466 | 92.314 | 263.755 | 1.00 | 9.33 | 6 |
| ATOM | 561 | C | ILE | 59 | 51.199 | 93.811 | 263.845 | 1.00 | 9.71 | 6 |
| ATOM | 562 | O | ILE | 59 | 50.112 | 94.268 | 263.494 | 1.00 | 8.98 | 8 |
| ATOM | 563 | CB | ILE | 59 | 51.457 | 91.838 | 262.285 | 1.00 | 10.23 | 6 |
| ATOM | 564 | CG1 | ILE | 59 | 51.777 | 90.339 | 262.232 | 1.00 | 11.33 | 6 |
| ATOM | 565 | CG2 | ILE | 59 | 52.476 | 92.624 | 261.459 | 1.00 | 10.84 | 6 |
| ATOM | 566 | CD1 | ILE | 59 | 51.911 | 89.780 | 260.841 | 1.00 | 12.79 | 6 |
| ATOM | 567 | H | ILE | 59 | 49.554 | 91.438 | 264.117 | 1.00 | 0.00 | 1 |
| ATOM | 568 | N | MET | 60 | 52.179 | 94.559 | 264.343 | 1.00 | 9.85 | 7 |
| ATOM | 569 | CA | MET | 60 | 52.030 | 96.003 | 264.501 | 1.00 | 10.37 | 6 |
| ATOM | 570 | C | MET | 60 | 53.378 | 96.645 | 264.758 | 1.00 | 9.44 | 6 |
| ATOM | 571 | O | MET | 60 | 54.364 | 95.959 | 265.013 | 1.00 | 9.21 | 8 |
| ATOM | 572 | CB | MET | 60 | 51.132 | 96.313 | 265.702 | 1.00 | 12.11 | 6 |
| ATOM | 573 | CG | MET | 60 | 51.786 | 96.018 | 267.056 | 1.00 | 15.56 | 6 |
| ATOM | 574 | SD | MET | 60 | 50.816 | 96.584 | 268.481 | 1.00 | 20.80 | 16 |
| ATOM | 575 | CE | MET | 60 | 50.041 | 95.093 | 268.963 | 1.00 | 20.02 | 6 |
| ATOM | 576 | H | MET | 60 | 53.021 | 94.139 | 264.632 | 1.00 | 0.00 | 1 |
| ATOM | 577 | N | ASP | 61 | 53.420 | 97.970 | 264.681 | 1.00 | 8.51 | 7 |
| ATOM | 578 | CA | ASP | 61 | 54.652 | 98.689 | 264.969 | 1.00 | 8.66 | 6 |
| ATOM | 579 | C | ASP | 61 | 54.628 | 98.912 | 266.482 | 1.00 | 7.98 | 6 |
| ATOM | 580 | O | ASP | 61 | 53.887 | 99.758 | 266.976 | 1.00 | 7.49 | 8 |
| ATOM | 581 | CB | ASP | 61 | 54.690 | 100.027 | 264.235 | 1.00 | 9.52 | 6 |
| ATOM | 582 | CG | ASP | 61 | 56.049 | 100.704 | 264.334 | 1.00 | 10.29 | 6 |
| ATOM | 583 | OD1 | ASP | 61 | 56.536 | 100.924 | 265.465 | 1.00 | 10.36 | 8 |
| ATOM | 584 | OD2 | ASP | 61 | 56.643 | 101.004 | 263.276 | 1.00 | 10.88 | 8 |
| ATOM | 585 | H | ASP | 61 | 52.617 | 98.484 | 264.431 | 1.00 | 0.00 | 1 |
| ATOM | 586 | N | TYR | 62 | 55.450 | 98.164 | 267.205 | 1.00 | 8.04 | 7 |
| ATOM | 587 | CA | TYR | 62 | 55.504 | 98.262 | 268.661 | 1.00 | 7.38 | 6 |
| ATOM | 588 | C | TYR | 62 | 55.905 | 99.634 | 269.202 | 1.00 | 6.86 | 6 |
| ATOM | 589 | O | TYR | 62 | 55.336 | 100.101 | 270.190 | 1.00 | 6.93 | 8 |
| ATOM | 590 | CB | TYR | 62 | 56.431 | 97.188 | 269.227 | 1.00 | 8.02 | 6 |
| ATOM | 591 | CG | TYR | 62 | 56.380 | 97.080 | 270.736 | 1.00 | 8.76 | 6 |
| ATOM | 592 | CD1 | TYR | 62 | 55.177 | 96.823 | 271.393 | 1.00 | 10.61 | 6 |
| ATOM | 593 | CD2 | TYR | 62 | 57.537 | 97.226 | 271.507 | 1.00 | 8.69 | 6 |

```
ATOM    594  CE1 TYR    62      55.123  96.707 272.782  1.00  9.23      6
ATOM    595  CE2 TYR    62      57.498  97.109 272.898  1.00 10.88      6
ATOM    596  CZ  TYR    62      56.286  96.852 273.528  1.00 10.20      6
ATOM    597  OH  TYR    62      56.228  96.732 274.901  1.00 11.40      8
ATOM    598  H   TYR    62      56.001  97.508 266.751  1.00  0.00      1
ATOM    599  HH  TYR    62      57.120  96.796 275.280  1.00  0.00      1
ATOM    600  N   GLY    63      56.886 100.271 268.569  1.00  6.73      7
ATOM    601  CA  GLY    63      57.328 101.579 269.026  1.00  7.52      6
ATOM    602  C   GLY    63      56.233 102.622 268.914  1.00  7.84      6
ATOM    603  O   GLY    63      55.965 103.363 269.863  1.00  8.11      8
ATOM    604  H   GLY    63      57.331  99.880 267.787  1.00  0.00      1
ATOM    605  N   LYS    64      55.566 102.652 267.765  1.00  8.78      7
ATOM    606  CA  LYS    64      54.492 103.605 267.525  1.00 10.43      6
ATOM    607  C   LYS    64      53.343 103.355 268.499  1.00  9.91      6
ATOM    608  O   LYS    64      52.760 104.298 269.036  1.00  9.90      8
ATOM    609  CB  LYS    64      54.019 103.511 266.071  1.00 10.91      6
ATOM    610  CG  LYS    64      53.149 104.680 265.628  1.00 13.09      6
ATOM    611  CD  LYS    64      53.015 104.755 264.108  1.00 13.70      6
ATOM    612  CE  LYS    64      52.166 103.631 263.558  1.00 14.53      6
ATOM    613  NZ  LYS    64      51.934 103.806 262.101  1.00 14.56      7
ATOM    614  H   LYS    64      55.805 102.012 267.074  1.00  0.00      1
ATOM    615  1HZ LYS    64      52.849 103.858 261.605  1.00  0.00      6
ATOM    616  2HZ LYS    64      51.383 103.004 261.741  1.00  0.00      6
ATOM    617  3HZ LYS    64      51.410 104.682 261.951  1.00  0.00      6
ATOM    618  N   PHE    65      53.042 102.079 268.740  1.00 10.75      7
ATOM    619  CA  PHE    65      51.981 101.689 269.671  1.00 12.06      6
ATOM    620  C   PHE    65      52.313 102.174 271.088  1.00 11.60      6
ATOM    621  O   PHE    65      51.500 102.834 271.742  1.00 11.65      8
ATOM    622  CB  PHE    65      51.806 100.159 269.652  1.00 11.25      6
ATOM    623  CG  PHE    65      50.973  99.619 270.793  1.00 12.58      6
ATOM    624  CD1 PHE    65      49.587  99.574 270.702  1.00 13.57      6
ATOM    625  CD2 PHE    65      51.581  99.156 271.961  1.00 14.32      6
ATOM    626  CE1 PHE    65      48.819  99.081 271.761  1.00 14.62      6
ATOM    627  CE2 PHE    65      50.821  98.665 273.020  1.00 13.76      6
ATOM    628  CZ  PHE    65      49.438  98.627 272.917  1.00 14.12      6
ATOM    629  H   PHE    65      53.534 101.371 268.269  1.00  0.00      1
ATOM    630  N   ARG    66      53.513 101.851 271.557  1.00 11.94      7
ATOM    631  CA  ARG    66      53.951 102.234 272.891  1.00 13.65      6
ATOM    632  C   ARG    66      54.011 103.747 273.094  1.00 12.90      6
ATOM    633  O   ARG    66      53.633 104.248 274.152  1.00 13.60      8
ATOM    634  CB  ARG    66      55.295 101.592 273.205  1.00 15.17      6
ATOM    635  CG  ARG    66      55.182 100.135 273.614  1.00 17.08      6
ATOM    636  CD  ARG    66      54.966 100.019 275.113  1.00 19.72      6
ATOM    637  NE  ARG    66      56.115 100.573 275.822  1.00 21.82      7
ATOM    638  CZ  ARG    66      56.040 101.316 276.921  1.00 23.10      6
ATOM    639  NH1 ARG    66      54.864 101.600 277.466  1.00 23.15      7
ATOM    640  NH2 ARG    66      57.148 101.818 277.446  1.00 23.88      7
ATOM    641  H   ARG    66      54.133 101.354 270.988  1.00  0.00      1
ATOM    642  HE  ARG    66      57.009 100.385 275.471  1.00  0.00      1
ATOM    643  1HH ARG    66      54.019 101.262 277.056  1.00  0.00      6
ATOM    644  2HH ARG    66      54.814 102.155 278.293  1.00  0.00      6
ATOM    645  1HH ARG    66      58.035 101.646 277.019  1.00  0.00      6
ATOM    646  2HH ARG    66      57.091 102.378 278.275  1.00  0.00      6
ATOM    647  N   PHE    67      54.491 104.471 272.088  1.00 12.51      7
ATOM    648  CA  PHE    67      54.567 105.928 272.180  1.00 13.85      6
ATOM    649  C   PHE    67      53.168 106.511 272.360  1.00 13.26      6
ATOM    650  O   PHE    67      52.951 107.353 273.222  1.00 13.62      8
ATOM    651  CB  PHE    67      55.220 106.536 270.930  1.00 15.01      6
ATOM    652  CG  PHE    67      55.090 108.035 270.851  1.00 16.91      6
ATOM    653  CD1 PHE    67      55.858 108.859 271.671  1.00 16.62      6
ATOM    654  CD2 PHE    67      54.173 108.622 269.985  1.00 17.21      6
ATOM    655  CE1 PHE    67      55.709 110.252 271.629  1.00 17.77      6
ATOM    656  CE2 PHE    67      54.017 110.012 269.937  1.00 18.71      6
ATOM    657  CZ  PHE    67      54.790 110.825 270.760  1.00 18.06      6
ATOM    658  H   PHE    67      54.815 104.023 271.279  1.00  0.00      1
ATOM    659  N   GLU    68      52.222 106.050 271.551  1.00 13.73      7
ATOM    660  CA  GLU    68      50.848 106.529 271.628  1.00 15.44      6
ATOM    661  C   GLU    68      50.196 106.233 272.975  1.00 16.54      6
ATOM    662  O   GLU    68      49.442 107.053 273.497  1.00 16.45      8
ATOM    663  CB  GLU    68      50.004 105.936 270.499  1.00 16.57      6
ATOM    664  CG  GLU    68      50.309 106.514 269.120  1.00 18.15      6
ATOM    665  CD  GLU    68      50.018 108.008 269.028  1.00 18.24      6
ATOM    666  OE1 GLU    68      48.965 108.446 269.533  1.00 19.42      8
ATOM    667  OE2 GLU    68      50.846 108.742 268.449  1.00 19.45      8
ATOM    668  H   GLU    68      52.454 105.366 270.877  1.00  0.00      1
ATOM    669  N   GLN    69      50.491 105.063 273.536  1.00 18.12      7
ATOM    670  CA  GLN    69      49.930 104.674 274.827  1.00 20.47      6
ATOM    671  C   GLN    69      50.438 105.590 275.930  1.00 19.88      6
ATOM    672  O   GLN    69      49.665 106.043 276.777  1.00 20.05      8
ATOM    673  CB  GLN    69      50.278 103.220 275.158  1.00 22.75      6
ATOM    674  CG  GLN    69      49.676 102.198 274.202  1.00 24.65      6
ATOM    675  CD  GLN    69      48.178 102.369 274.026  1.00 26.82      6
ATOM    676  OE1 GLN    69      47.683 102.489 272.903  1.00 28.73      8
ATOM    677  NE2 GLN    69      47.449 102.389 275.132  1.00 27.98      7
ATOM    678  H   GLN    69      51.070 104.446 273.047  1.00  0.00      1
ATOM    679  1HE GLN    69      46.485 102.495 275.000  1.00  0.00      6
ATOM    680  2HE GLN    69      47.888 102.303 276.001  1.00  0.00      6
```

| | | | | | | | | | |
|---|---|---|---|---|---|---|---|---|---|
| ATOM | 681 | N | GLN | 70 | 51.739 | 105.865 | 275.916 | 1.00 | 20.05 | 7 |
| ATOM | 682 | CA | GLN | 70 | 52.347 | 106.732 | 276.918 | 1.00 | 21.72 | 6 |
| ATOM | 683 | C | GLN | 70 | 51.884 | 108.168 | 276.737 | 1.00 | 22.64 | 6 |
| ATOM | 684 | O | GLN | 70 | 51.697 | 108.897 | 277.709 | 1.00 | 21.75 | 8 |
| ATOM | 685 | CB | GLN | 70 | 53.863 | 106.657 | 276.832 | 1.00 | 22.55 | 6 |
| ATOM | 686 | CG | GLN | 70 | 54.409 | 105.301 | 277.211 | 1.00 | 25.02 | 6 |
| ATOM | 687 | CD | GLN | 70 | 55.898 | 105.228 | 277.041 | 1.00 | 26.22 | 6 |
| ATOM | 688 | OE1 | GLN | 70 | 56.627 | 104.937 | 277.990 | 1.00 | 27.03 | 8 |
| ATOM | 689 | NE2 | GLN | 70 | 56.369 | 105.499 | 275.832 | 1.00 | 26.76 | 7 |
| ATOM | 690 | H | GLN | 70 | 52.303 | 105.469 | 275.218 | 1.00 | 0.00 | 1 |
| ATOM | 691 | 1HE | GLN | 70 | 57.342 | 105.540 | 275.725 | 1.00 | 0.00 | 6 |
| ATOM | 692 | 2HE | GLN | 70 | 55.742 | 105.683 | 275.108 | 1.00 | 0.00 | 6 |
| ATOM | 693 | N | LYS | 71 | 51.714 | 108.566 | 275.483 | 1.00 | 23.61 | 7 |
| ATOM | 694 | CA | LYS | 71 | 51.252 | 109.904 | 275.148 | 1.00 | 24.80 | 6 |
| ATOM | 695 | C | LYS | 71 | 49.881 | 110.074 | 275.800 | 1.00 | 25.43 | 6 |
| ATOM | 696 | O | LYS | 71 | 49.660 | 110.998 | 276.580 | 1.00 | 23.88 | 8 |
| ATOM | 697 | CB | LYS | 71 | 51.123 | 110.019 | 273.628 | 1.00 | 25.01 | 6 |
| ATOM | 698 | CG | LYS | 71 | 50.893 | 111.415 | 273.088 | 1.00 | 25.92 | 6 |
| ATOM | 699 | CD | LYS | 71 | 50.632 | 111.352 | 271.587 | 1.00 | 27.18 | 6 |
| ATOM | 700 | CE | LYS | 71 | 50.863 | 112.695 | 270.922 | 1.00 | 27.36 | 6 |
| ATOM | 701 | NZ | LYS | 71 | 52.288 | 113.119 | 271.078 | 1.00 | 28.59 | 7 |
| ATOM | 702 | H | LYS | 71 | 51.909 | 107.941 | 274.757 | 1.00 | 0.00 | 1 |
| ATOM | 703 | 1HZ | LYS | 71 | 52.917 | 112.419 | 270.639 | 1.00 | 0.00 | 6 |
| ATOM | 704 | 2HZ | LYS | 71 | 52.437 | 114.047 | 270.635 | 1.00 | 0.00 | 6 |
| ATOM | 705 | 3HZ | LYS | 71 | 52.511 | 113.201 | 272.091 | 1.00 | 0.00 | 6 |
| ATOM | 706 | N | LYS | 72 | 48.986 | 109.137 | 275.504 | 1.00 | 26.73 | 7 |
| ATOM | 707 | CA | LYS | 72 | 47.623 | 109.134 | 276.033 | 1.00 | 28.43 | 6 |
| ATOM | 708 | C | LYS | 72 | 47.581 | 109.281 | 277.551 | 1.00 | 28.72 | 6 |
| ATOM | 709 | O | LYS | 72 | 46.865 | 110.138 | 278.078 | 1.00 | 28.22 | 8 |
| ATOM | 710 | CB | LYS | 72 | 46.916 | 107.847 | 275.592 | 1.00 | 28.25 | 6 |
| ATOM | 711 | CG | LYS | 72 | 45.594 | 107.557 | 276.289 | 1.00 | 29.22 | 6 |
| ATOM | 712 | CD | LYS | 72 | 44.859 | 106.408 | 275.608 | 1.00 | 30.32 | 6 |
| ATOM | 713 | CE | LYS | 72 | 45.741 | 105.170 | 275.457 | 1.00 | 30.98 | 6 |
| ATOM | 714 | NZ | LYS | 72 | 46.170 | 104.575 | 276.754 | 1.00 | 30.82 | 7 |
| ATOM | 715 | H | LYS | 72 | 49.250 | 108.408 | 274.902 | 1.00 | 0.00 | 1 |
| ATOM | 716 | 1HZ | LYS | 72 | 45.331 | 104.290 | 277.303 | 1.00 | 0.00 | 6 |
| ATOM | 717 | 2HZ | LYS | 72 | 46.764 | 103.740 | 276.585 | 1.00 | 0.00 | 6 |
| ATOM | 718 | 3HZ | LYS | 72 | 46.717 | 105.286 | 277.282 | 1.00 | 0.00 | 6 |
| ATOM | 719 | N | GLU | 73 | 48.360 | 108.459 | 278.246 | 1.00 | 29.32 | 7 |
| ATOM | 720 | CA | GLU | 73 | 48.416 | 108.495 | 279.703 | 1.00 | 30.37 | 6 |
| ATOM | 721 | C | GLU | 73 | 48.877 | 109.847 | 280.237 | 1.00 | 29.33 | 6 |
| ATOM | 722 | O | GLU | 73 | 48.274 | 110.395 | 281.162 | 1.00 | 28.80 | 8 |
| ATOM | 723 | CB | GLU | 73 | 49.336 | 107.389 | 280.225 | 1.00 | 31.22 | 6 |
| ATOM | 724 | CG | GLU | 73 | 48.617 | 106.095 | 280.590 | 1.00 | 36.06 | 6 |
| ATOM | 725 | CD | GLU | 73 | 47.843 | 105.494 | 279.432 | 1.00 | 36.84 | 6 |
| ATOM | 726 | OE1 | GLU | 73 | 46.695 | 105.931 | 279.190 | 1.00 | 37.81 | 8 |
| ATOM | 727 | OE2 | GLU | 73 | 48.376 | 104.570 | 278.776 | 1.00 | 37.81 | 8 |
| ATOM | 728 | H | GLU | 73 | 48.906 | 107.805 | 277.761 | 1.00 | 0.00 | 1 |
| ATOM | 729 | N | LYS | 74 | 49.950 | 110.374 | 279.656 | 1.00 | 29.32 | 7 |
| ATOM | 730 | CA | LYS | 74 | 50.505 | 111.659 | 280.068 | 1.00 | 28.96 | 6 |
| ATOM | 731 | C | LYS | 74 | 49.545 | 112.821 | 279.851 | 1.00 | 28.87 | 6 |
| ATOM | 732 | O | LYS | 74 | 49.299 | 113.607 | 280.764 | 1.00 | 28.01 | 8 |
| ATOM | 733 | CB | LYS | 74 | 51.816 | 111.941 | 279.323 | 1.00 | 29.93 | 6 |
| ATOM | 734 | CG | LYS | 74 | 53.106 | 111.552 | 280.059 | 1.00 | 31.80 | 6 |
| ATOM | 735 | CD | LYS | 74 | 53.340 | 110.046 | 280.142 | 1.00 | 33.29 | 6 |
| ATOM | 736 | CE | LYS | 74 | 52.601 | 109.410 | 281.312 | 1.00 | 34.15 | 6 |
| ATOM | 737 | NZ | LYS | 74 | 53.033 | 109.983 | 282.620 | 1.00 | 35.54 | 7 |
| ATOM | 738 | H | LYS | 74 | 50.382 | 109.894 | 278.918 | 1.00 | 0.00 | 1 |
| ATOM | 739 | 1HZ | LYS | 74 | 52.848 | 111.005 | 282.638 | 1.00 | 0.00 | 6 |
| ATOM | 740 | 2HZ | LYS | 74 | 52.493 | 109.513 | 283.377 | 1.00 | 0.00 | 6 |
| ATOM | 741 | 3HZ | LYS | 74 | 54.048 | 109.802 | 282.753 | 1.00 | 0.00 | 6 |
| ATOM | 742 | N | GLU | 75 | 48.995 | 112.918 | 278.646 | 1.00 | 28.34 | 7 |
| ATOM | 743 | CA | GLU | 75 | 48.083 | 114.002 | 278.297 | 1.00 | 28.46 | 6 |
| ATOM | 744 | C | GLU | 75 | 46.859 | 114.075 | 279.210 | 1.00 | 27.72 | 6 |
| ATOM | 745 | O | GLU | 75 | 46.487 | 115.155 | 279.671 | 1.00 | 27.78 | 8 |
| ATOM | 746 | CB | GLU | 75 | 47.625 | 113.885 | 276.837 | 1.00 | 30.56 | 6 |
| ATOM | 747 | CG | GLU | 75 | 48.723 | 113.590 | 275.818 | 1.00 | 31.98 | 6 |
| ATOM | 748 | CD | GLU | 75 | 49.934 | 114.500 | 275.934 | 1.00 | 33.83 | 6 |
| ATOM | 749 | OE1 | GLU | 75 | 49.796 | 115.718 | 275.676 | 1.00 | 34.62 | 8 |
| ATOM | 750 | OE2 | GLU | 75 | 51.031 | 113.989 | 276.265 | 1.00 | 34.75 | 8 |
| ATOM | 751 | H | GLU | 75 | 49.215 | 112.228 | 277.986 | 1.00 | 0.00 | 1 |
| ATOM | 752 | N | ALA | 76 | 46.251 | 112.924 | 279.485 | 1.00 | 26.74 | 7 |
| ATOM | 753 | CA | ALA | 76 | 45.059 | 112.860 | 280.330 | 1.00 | 25.83 | 6 |
| ATOM | 754 | C | ALA | 76 | 45.322 | 113.183 | 281.801 | 1.00 | 25.52 | 6 |
| ATOM | 755 | O | ALA | 76 | 44.385 | 113.280 | 282.594 | 1.00 | 27.76 | 8 |
| ATOM | 756 | CB | ALA | 76 | 44.409 | 111.493 | 280.210 | 1.00 | 27.26 | 6 |
| ATOM | 757 | H | ALA | 76 | 46.614 | 112.085 | 279.124 | 1.00 | 0.00 | 1 |
| ATOM | 758 | N | ARG | 77 | 46.587 | 113.348 | 282.168 | 1.00 | 24.81 | 7 |
| ATOM | 759 | CA | ARG | 77 | 46.918 | 113.637 | 283.556 | 1.00 | 24.99 | 6 |
| ATOM | 760 | C | ARG | 77 | 47.592 | 114.986 | 283.803 | 1.00 | 24.57 | 6 |
| ATOM | 761 | O | ARG | 77 | 48.004 | 115.275 | 284.933 | 1.00 | 24.84 | 8 |
| ATOM | 762 | CB | ARG | 77 | 47.748 | 112.493 | 284.142 | 1.00 | 25.57 | 6 |
| ATOM | 763 | CG | ARG | 77 | 46.963 | 111.190 | 284.266 | 1.00 | 25.24 | 6 |
| ATOM | 764 | CD | ARG | 77 | 47.855 | 110.038 | 284.695 | 1.00 | 26.13 | 6 |
| ATOM | 765 | NE | ARG | 77 | 47.096 | 108.835 | 285.038 | 1.00 | 27.33 | 7 |
| ATOM | 766 | CZ | ARG | 77 | 46.433 | 108.079 | 284.167 | 1.00 | 27.87 | 6 |
| ATOM | 767 | NH1 | ARG | 77 | 46.416 | 108.393 | 282.876 | 1.00 | 28.29 | 7 |

```
ATOM    768  NH2 ARG    77      45.809 106.984 284.583  1.00 28.36      7
ATOM    769  H   ARG    77      47.312 113.294 281.513  1.00  0.00      1
ATOM    770  HE  ARG    77      47.082 108.554 285.980  1.00  0.00      1
ATOM    771  1HH ARG    77      46.917 109.193 282.552  1.00  0.00      6
ATOM    772  2HH ARG    77      45.926 107.816 282.218  1.00  0.00      6
ATOM    773  1HH ARG    77      45.850 106.721 285.547  1.00  0.00      6
ATOM    774  2HH ARG    77      45.310 106.424 283.921  1.00  0.00      6
ATOM    775  N   LYS    78      47.666 115.821 282.766  1.00 24.47      7
ATOM    776  CA  LYS    78      48.277 117.146 282.885  1.00 24.36      6
ATOM    777  C   LYS    78      47.355 118.219 282.294  1.00 24.43      6
ATOM    778  O   LYS    78      47.459 119.393 282.710  1.00 24.46      8
ATOM    779  CB  LYS    78      49.645 117.189 282.180  1.00 23.92      6
ATOM    780  CG  LYS    78      49.565 117.250 280.657  1.00 24.59      6
ATOM    781  CD  LYS    78      50.938 117.454 280.036  1.00 25.41      6
ATOM    782  CE  LYS    78      50.854 117.542 278.517  1.00 25.81      6
ATOM    783  NZ  LYS    78      52.203 117.484 277.881  1.00 27.25      7
ATOM    784  OXT LYS    78      46.545 117.880 281.408  1.00 25.02      8
ATOM    785  H   LYS    78      47.276 115.613 281.889  1.00  0.00      1
ATOM    786  1HZ LYS    78      52.690 116.609 278.156  1.00  0.00      6
ATOM    787  2HZ LYS    78      52.095 117.496 276.844  1.00  0.00      6
ATOM    788  3HZ LYS    78      52.775 118.298 278.189  1.00  0.00      6
END
```

File E ----------------------------------------------------------------------------

```
Mol_Id: 4; Molecule: Messenger RNA Mk27; Chain: 1; Engineered: Yes;
Other_Details: 27 Nt Long Mrna Fragment. The Actual Sequence
Ggcaaggagguaaaa Augaaa Aaaaaa Modeled As Ggcaaggagguaaaa Uuuuuu Aaaaaa
COMPND  14 MOL_ID: 4;
COMPND  15 MOLECULE: MESSENGER RNA MK27;
COMPND  16 CHAIN: 1;
COMPND  17 ENGINEERED: YES;
COMPND  18 OTHER_DETAILS: 27 NT LONG MRNA FRAGMENT. THE ACTUAL
COMPND  19 SEQUENCE GGCAAGGAGGUAAAA AUGAAA AAAAAA MODELED AS
COMPND  20 GGCAAGGAGGUAAAA UUUUUU AAAAAA;
SOURCE  12 MOL_ID: 4;
SOURCE  13 SYNTHETIC: YES;
KEYWDS     RIBOSOME ASSEMBLY, PROTEIN SYNTHESIS, LIFE
EXPDTA     X-RAY DIFFRACTION
AUTHOR     G.Z.YUSUPOVA,M.M.YUSUPOV,J.H.D.CATE,H.F.NOLLER
REVDAT   2 14-SEP-01 1JGO    1                   JRNL
REVDAT   1 20-JUL-01 1JGO    0
JRNL        AUTH   G.Z.YUSUPOVA,M.M.YUSUPOV,J.H.D.CATE,H.F.NOLLER
JRNL        TITL   THE PATH OF MESSENGER RNA THROUGH THE RIBOSOME
JRNL        REF    CELL (CAMBRIDGE,MASS.)        V. 106   233 2001
JRNL        REFN   ASTM CELLB5  US ISSN 0092-8674
REMARK   1
REMARK   2
REMARK   2 RESOLUTION. 5.60 ANGSTROMS.
REMARK   3
REMARK   3 REFINEMENT.
REMARK   3   PROGRAM     : O
REMARK   3   AUTHORS     : JONES,ZOU,COWAN,KJELDGAARD
REMARK   3
REMARK   3  DATA USED IN REFINEMENT.
REMARK   3   RESOLUTION RANGE HIGH (ANGSTROMS) : 5.60
REMARK   3   RESOLUTION RANGE LOW  (ANGSTROMS) : 250.00
REMARK   3   DATA CUTOFF            (SIGMA(F)) : NULL
REMARK   3   DATA CUTOFF HIGH         (ABS(F)) : NULL
REMARK   3   DATA CUTOFF LOW          (ABS(F)) : NULL
REMARK   3   COMPLETENESS (WORKING+TEST)   (%) : 97.7
REMARK   3   NUMBER OF REFLECTIONS             : 153627
REMARK   3
REMARK   3
REMARK   3  FIT TO DATA USED IN REFINEMENT.
REMARK   3   CROSS-VALIDATION METHOD           : NULL
REMARK   3   FREE R VALUE TEST SET SELECTION   : NULL
REMARK   3   R VALUE            (WORKING SET)  : NULL
REMARK   3   FREE R VALUE                      : NULL
REMARK   3   FREE R VALUE TEST SET SIZE   (%)  : NULL
REMARK   3   FREE R VALUE TEST SET COUNT       : NULL
REMARK   3   ESTIMATED ERROR OF FREE R VALUE   : NULL
REMARK   3
REMARK   3  FIT IN THE HIGHEST RESOLUTION BIN.
REMARK   3   TOTAL NUMBER OF BINS USED              : NULL
REMARK   3   BIN RESOLUTION RANGE HIGH       (A)    : NULL
REMARK   3   BIN RESOLUTION RANGE LOW        (A)    : NULL
REMARK   3   BIN COMPLETENESS (WORKING+TEST) (%)    : NULL
REMARK   3   REFLECTIONS IN BIN    (WORKING SET)    : NULL
REMARK   3   BIN R VALUE           (WORKING SET)    : NULL
REMARK   3   BIN FREE R VALUE                       : NULL
REMARK   3   BIN FREE R VALUE TEST SET SIZE   (%)   : NULL
REMARK   3   BIN FREE R VALUE TEST SET COUNT        : NULL
REMARK   3   ESTIMATED ERROR OF BIN FREE R VALUE    : NULL
REMARK   3
REMARK   3  NUMBER OF NON-HYDROGEN ATOMS USED IN REFINEMENT.
REMARK   3   PROTEIN ATOMS            : 2396
```

```
REMARK   3   NUCLEIC ACID ATOMS       : 6534
REMARK   3   HETEROGEN ATOMS          : 0
REMARK   3   SOLVENT ATOMS            : 0
REMARK   3
REMARK   3   B VALUES.
REMARK   3    FROM WILSON PLOT           (A**2) : NULL
REMARK   3    MEAN B VALUE      (OVERALL, A**2) : NULL
REMARK   3    OVERALL ANISOTROPIC B VALUE.
REMARK   3     B11 (A**2) : NULL
REMARK   3     B22 (A**2) : NULL
REMARK   3     B33 (A**2) : NULL
REMARK   3     B12 (A**2) : NULL
REMARK   3     B13 (A**2) : NULL
REMARK   3     B23 (A**2) : NULL
REMARK   3
REMARK   3   ESTIMATED COORDINATE ERROR.
REMARK   3    ESD FROM LUZZATI PLOT       (A) : NULL
REMARK   3    ESD FROM SIGMAA             (A) : NULL
REMARK   3    LOW RESOLUTION CUTOFF       (A) : NULL
REMARK   3
REMARK   3   CROSS-VALIDATED ESTIMATED COORDINATE ERROR.
REMARK   3    ESD FROM C-V LUZZATI PLOT   (A) : NULL
REMARK   3    ESD FROM C-V SIGMAA         (A) : NULL
REMARK   3
REMARK   3   RMS DEVIATIONS FROM IDEAL VALUES.
REMARK   3    BOND LENGTHS            (A) : NULL
REMARK   3    BOND ANGLES       (DEGREES) : NULL
REMARK   3    DIHEDRAL ANGLES   (DEGREES) : NULL
REMARK   3    IMPROPER ANGLES   (DEGREES) : NULL
REMARK   3
REMARK   3   ISOTROPIC THERMAL MODEL : NULL
REMARK   3
REMARK   3   ISOTROPIC THERMAL FACTOR RESTRAINTS.    RMS      SIGMA
REMARK   3    MAIN-CHAIN BOND         (A**2) : NULL  ; NULL
REMARK   3    MAIN-CHAIN ANGLE        (A**2) : NULL  ; NULL
REMARK   3    SIDE-CHAIN BOND         (A**2) : NULL  ; NULL
REMARK   3    SIDE-CHAIN ANGLE        (A**2) : NULL  ; NULL
REMARK   3
REMARK   3
REMARK   3   NCS MODEL : NULL
REMARK   3
REMARK   3   NCS RESTRAINTS.                         RMS   SIGMA/WEIGHT
REMARK   3    GROUP  1 POSITIONAL        (A) : NULL  ; NULL
REMARK   3    GROUP  1 B-FACTOR       (A**2) : NULL  ; NULL
REMARK   3
REMARK   3   PARAMETER FILE  1  : NULL
REMARK   3   TOPOLOGY FILE  1   : NULL
REMARK   3
REMARK   3   OTHER REFINEMENT REMARKS: THE MODEL WAS BUILT BY MANUAL
REMARK   3   FITTING OF INDIVIDUAL MOLECULES INTO THE EXPERIMENTAL
REMARK   3   ELECTRON DENSITY USING THE GRAPHIC PROGRAM O.
REMARK   4
REMARK   4 1JGO COMPLIES WITH FORMAT V. 2.3, 09-JULY-1998
REMARK 100
REMARK 100 THIS ENTRY HAS BEEN PROCESSED BY THE NUCLEIC ACID DATABASE
REMARK 100 ON 12-JUL-2001.
REMARK 100 THE NDB ID CODE IS RR0034.
REMARK 105
REMARK 105 THE PROTEIN DATA BANK HAS ADOPTED THE SACCHARIDE CHEMISTS
REMARK 105 NOMENCLATURE FOR ATOMS OF THE DEOXYRIBOSE/RIBOSE MOIETY
REMARK 105 RATHER THAN THAT OF THE NUCLEOSIDE CHEMISTS.  THE RING
REMARK 105 OXYGEN ATOM IS LABELLED O4* INSTEAD OF O1*.
REMARK 106
REMARK 106 ALL HYDROGEN BONDS BETWEEN BASE PAIRS NOT MENTIONED IN
REMARK 106 REMARKS 102 AND 103 FOLLOW THE CONVENTIONAL WATSON-CRICK
REMARK 106 HYDROGEN BONDING PATTERN. THEY HAVE NOT BEEN PRESENTED ON
REMARK 106 *CONECT* RECORDS IN THIS ENTRY.
REMARK 200
REMARK 200 EXPERIMENTAL DETAILS
REMARK 200  EXPERIMENT TYPE              : X-RAY DIFFRACTION
REMARK 200  DATE OF DATA COLLECTION      : NULL
REMARK 200  TEMPERATURE        (KELVIN)  : 100.0
REMARK 200  PH                           : 7.40
REMARK 200  NUMBER OF CRYSTALS USED      : 2
REMARK 200
REMARK 200  SYNCHROTRON             (Y/N) : Y
REMARK 200  RADIATION SOURCE              : ALS
REMARK 200  BEAMLINE                      : 5.0.2
REMARK 200  X-RAY GENERATOR MODEL         : NULL
REMARK 200  MONOCHROMATIC OR LAUE   (M/L) : M
REMARK 200  WAVELENGTH OR RANGE       (A) : 1.100
REMARK 200  MONOCHROMATOR                 : NULL
REMARK 200  OPTICS                        : NULL
REMARK 200
REMARK 200  DETECTOR TYPE                 : CCD
REMARK 200  DETECTOR MANUFACTURER         : ADSC QUANTUM 4
REMARK 200  INTENSITY-INTEGRATION SOFTWARE : DENZO
```

```
REMARK 200 DATA SCALING SOFTWARE          : SCALEPACK
REMARK 200
REMARK 200 NUMBER OF UNIQUE REFLECTIONS   : 153627
REMARK 200 RESOLUTION RANGE HIGH      (A) : 5.600
REMARK 200 RESOLUTION RANGE LOW       (A) : 250.000
REMARK 200 REJECTION CRITERIA  (SIGMA(I)) : 0.000
REMARK 200
REMARK 200 OVERALL.
REMARK 200  COMPLETENESS FOR RANGE    (%) : 97.7
REMARK 200  DATA REDUNDANCY               : 3.000
REMARK 200  R MERGE                   (I) : NULL
REMARK 200  R SYM                     (I) : 12.40000
REMARK 200  <I/SIGMA(I)> FOR THE DATA SET : NULL
REMARK 200
REMARK 200 IN THE HIGHEST RESOLUTION SHELL.
REMARK 200  HIGHEST RESOLUTION SHELL, RANGE HIGH (A) : NULL
REMARK 200  HIGHEST RESOLUTION SHELL, RANGE LOW  (A) : NULL
REMARK 200  COMPLETENESS FOR SHELL    (%) : NULL
REMARK 200  DATA REDUNDANCY IN SHELL      : NULL
REMARK 200  R MERGE FOR SHELL         (I) : NULL
REMARK 200  R SYM FOR SHELL           (I) : NULL
REMARK 200  <I/SIGMA(I)> FOR SHELL        : NULL
REMARK 200
REMARK 200 DIFFRACTION PROTOCOL: SINGLE WAVELENGTH
REMARK 200 METHOD USED TO DETERMINE THE STRUCTURE: FOURIER SYNTHESIS
REMARK 200 SOFTWARE USED: CCP4
REMARK 200 STARTING MODEL: NULL
REMARK 200
REMARK 200 REMARK: NULL
REMARK 280
REMARK 280 CRYSTAL
REMARK 280 SOLVENT CONTENT, VS   (%): NULL
REMARK 280 MATTHEWS COEFFICIENT, VM (ANGSTROMS**3/DA): NULL
REMARK 280
REMARK 280 CRYSTALLIZATION CONDITIONS: 20 MM MGCL2, 100 MM KCL, 20 MM
REMARK 280  TRIS HCL, PH 7.4, VAPOR DIFFUSION AT 237K
REMARK 290
REMARK 290 CRYSTALLOGRAPHIC SYMMETRY
REMARK 290 SYMMETRY OPERATORS FOR SPACE GROUP: I 4 2 2
REMARK 290
REMARK 290      SYMOP   SYMMETRY
REMARK 290     NNNMMM   OPERATOR
REMARK 290       1555   X,Y,Z
REMARK 290       2555   -X,-Y,Z
REMARK 290       3555   -Y,X,Z
REMARK 290       4555   Y,-X,Z
REMARK 290       5555   -X,Y,-Z
REMARK 290       6555   X,-Y,-Z
REMARK 290       7555   Y,X,-Z
REMARK 290       8555   -Y,-X,-Z
REMARK 290       9555   1/2+X,1/2+Y,1/2+Z
REMARK 290      10555   1/2-X,1/2-Y,1/2+Z
REMARK 290      11555   1/2-Y,1/2+X,1/2+Z
REMARK 290      12555   1/2+Y,1/2-X,1/2+Z
REMARK 290      13555   1/2-X,1/2+Y,1/2-Z
REMARK 290      14555   1/2+X,1/2-Y,1/2-Z
REMARK 290      15555   1/2+Y,1/2+X,1/2-Z
REMARK 290      16555   1/2-Y,1/2-X,1/2-Z
REMARK 290
REMARK 290     WHERE NNN -> OPERATOR NUMBER
REMARK 290           MMM -> TRANSLATION VECTOR
REMARK 290
REMARK 290 CRYSTALLOGRAPHIC SYMMETRY TRANSFORMATIONS
REMARK 290 THE FOLLOWING TRANSFORMATIONS OPERATE ON THE ATOM/HETATM
REMARK 290 RECORDS IN THIS ENTRY TO PRODUCE CRYSTALLOGRAPHICALLY
REMARK 290 RELATED MOLECULES.
REMARK 290    SMTRY1   1  1.000000  0.000000  0.000000        0.00000
REMARK 290    SMTRY2   1  0.000000  1.000000  0.000000        0.00000
REMARK 290    SMTRY3   1  0.000000  0.000000  1.000000        0.00000
REMARK 290    SMTRY1   2 -1.000000  0.000000  0.000000        0.00000
REMARK 290    SMTRY2   2  0.000000 -1.000000  0.000000        0.00000
REMARK 290    SMTRY3   2  0.000000  0.000000  1.000000        0.00000
REMARK 290    SMTRY1   3  0.000000 -1.000000  0.000000        0.00000
REMARK 290    SMTRY2   3  1.000000  0.000000  0.000000        0.00000
REMARK 290    SMTRY3   3  0.000000  0.000000  1.000000        0.00000
REMARK 290    SMTRY1   4  0.000000  1.000000  0.000000        0.00000
REMARK 290    SMTRY2   4 -1.000000  0.000000  0.000000        0.00000
REMARK 290    SMTRY3   4  0.000000  0.000000  1.000000        0.00000
REMARK 290    SMTRY1   5 -1.000000  0.000000  0.000000        0.00000
REMARK 290    SMTRY2   5  0.000000  1.000000  0.000000        0.00000
REMARK 290    SMTRY3   5  0.000000  0.000000 -1.000000        0.00000
REMARK 290    SMTRY1   6  1.000000  0.000000  0.000000        0.00000
REMARK 290    SMTRY2   6  0.000000 -1.000000  0.000000        0.00000
REMARK 290    SMTRY3   6  0.000000  0.000000 -1.000000        0.00000
REMARK 290    SMTRY1   7  0.000000  1.000000  0.000000        0.00000
REMARK 290    SMTRY2   7  1.000000  0.000000  0.000000        0.00000
REMARK 290    SMTRY3   7  0.000000  0.000000 -1.000000        0.00000
```

```
REMARK 290   SMTRY1    8  0.000000 -1.000000  0.000000        0.00000
REMARK 290   SMTRY2    8 -1.000000  0.000000  0.000000        0.00000
REMARK 290   SMTRY3    8  0.000000  0.000000 -1.000000        0.00000
REMARK 290   SMTRY1    9  1.000000  0.000000  0.000000      253.60000
REMARK 290   SMTRY2    9  0.000000  1.000000  0.000000      253.60000
REMARK 290   SMTRY3    9  0.000000  0.000000  1.000000      401.83000
REMARK 290   SMTRY1   10 -1.000000  0.000000  0.000000      253.60000
REMARK 290   SMTRY2   10  0.000000 -1.000000  0.000000      253.60000
REMARK 290   SMTRY3   10  0.000000  0.000000  1.000000      401.83000
REMARK 290   SMTRY1   11  0.000000 -1.000000  0.000000      253.60000
REMARK 290   SMTRY2   11  1.000000  0.000000  0.000000      253.60000
REMARK 290   SMTRY3   11  0.000000  0.000000  1.000000      401.83000
REMARK 290   SMTRY1   12  0.000000  1.000000  0.000000      253.60000
REMARK 290   SMTRY2   12 -1.000000  0.000000  0.000000      253.60000
REMARK 290   SMTRY3   12  0.000000  0.000000  1.000000      401.83000
REMARK 290   SMTRY1   13 -1.000000  0.000000  0.000000      253.60000
REMARK 290   SMTRY2   13  0.000000  1.000000  0.000000      253.60000
REMARK 290   SMTRY3   13  0.000000  0.000000 -1.000000      401.83000
REMARK 290   SMTRY1   14  1.000000  0.000000  0.000000      253.60000
REMARK 290   SMTRY2   14  0.000000 -1.000000  0.000000      253.60000
REMARK 290   SMTRY3   14  0.000000  0.000000 -1.000000      401.83000
REMARK 290   SMTRY1   15  0.000000  1.000000  0.000000      253.60000
REMARK 290   SMTRY2   15  1.000000  0.000000  0.000000      253.60000
REMARK 290   SMTRY3   15  0.000000  0.000000 -1.000000      401.83000
REMARK 290   SMTRY1   16  0.000000 -1.000000  0.000000      253.60000
REMARK 290   SMTRY2   16 -1.000000  0.000000  0.000000      253.60000
REMARK 290   SMTRY3   16  0.000000  0.000000 -1.000000      401.83000
REMARK 290
REMARK 290 REMARK: NULL
REMARK 300
REMARK 300 BIOMOLECULE: 1
REMARK 300 THIS ENTRY CONTAINS THE CRYSTALLOGRAPHIC ASYMMETRIC UNIT
REMARK 300 WHICH CONSISTS OF 25CHAIN(S). SEE REMARK 350 FOR
REMARK 300 INFORMATION ON GENERATING THE BIOLOGICAL MOLECULE(S).
REMARK 350
REMARK 350 GENERATING THE BIOMOLECULE
REMARK 350 COORDINATES FOR A COMPLETE MULTIMER REPRESENTING THE KNOWN
REMARK 350 BIOLOGICALLY SIGNIFICANT OLIGOMERIZATION STATE OF THE
REMARK 350 MOLECULE CAN BE GENERATED BY APPLYING BIOMT TRANSFORMATIONS
REMARK 350 GIVEN BELOW.  BOTH NON-CRYSTALLOGRAPHIC AND
REMARK 350 CRYSTALLOGRAPHIC OPERATIONS ARE GIVEN.
REMARK 350
REMARK 350 BIOMOLECULE: 1
REMARK 350 APPLY THE FOLLOWING TO CHAINS: A, B, C, D, 1, E, F, G, H,
REMARK 350                                I, J, K, L, M, N, O, P, Q, R, S, T, U, V, W, X
REMARK 350   BIOMT1   1  1.000000  0.000000  0.000000        0.00000
REMARK 350   BIOMT2   1  0.000000  1.000000  0.000000        0.00000
REMARK 350   BIOMT3   1  0.000000  0.000000  1.000000        0.00000
REMARK 400
REMARK 400 COMPOUND
REMARK 400
REMARK 400 THIS FILE, 1JGO, CONTAINS ONLY MOLECULES OF
REMARK 400 THE 30S RIBOSOMAL SUBUNIT, THREE TRNA MOLECULES
REMARK 400 AND AN MRNA FRAGMENT. THE CORRESPONDING 50S SUBUNIT
REMARK 400 IS IN THE PDB FILE 1GIY.
REMARK 400
REMARK 400 THE DIFFERENCE BETWEEN THIS FILE, 1JGO, AND 1GIX,
REMARK 400 BOTH 30S RIBOSOME SUBUNITS, IS IN THE MRNA MOLECULE.
REMARK 400 IN BOTH FILES, MRNA HAS CHAIN ID '1'
REMARK 400
REMARK 400 ==================================================
REMARK 400
REMARK 400    70S RIBOSOME PARTICLE ORIGINATES FROM THERMUS
REMARK 400 THERMOPHILUS. HOWEVER, INITIAL MODELS OF SOME OF
REMARK 400 ITS CONSTITUENTS WERE TAKEN FROM STRUCTURES FROM
REMARK 400 OTHER ORGANISMS AS INITIAL MODELS.
REMARK 400
REMARK 400 THE FOLLOWING LISTS CHAIN ID (AS IN THE COMPND
REMARK 400 RECORDS ABOVE), THE PDB ID OF THE STRUCTURAL
REMARK 400 MODEL AND THE SOURCE ORGANISM OF THAT MODEL FOR
REMARK 400 EACH BIOMOLECULE.
REMARK 400
REMARK 400 ==================================================
REMARK 400      30S SMALL SUBUNIT, PDB FILE 1JGO
REMARK 400 ==================================================
REMARK 400
REMARK 400 ===> 30S 16S RIBOSOMAL RNA, CHAIN A            <===
REMARK 400 1FJF         THERMUS THERMOPHILUS
REMARK 400 ===> TRNA(PHE), CHAIN B, C                     <===
REMARK 400 1EVV, 1FFZ       SACHROMYCES CEREVISIAE
REMARK 400 ===> TRNA(PHE), CHAIN D                        <===
REMARK 400 1GTR, 1B23, 3TRA NO SEQUENCE ENTRY
REMARK 400 ===> 30S RIBOSOMAL PROTEIN S2, CHAIN E         <===
REMARK 400 1FJF         THERMUS THERMOPHILUS
REMARK 400 ===> 30S RIBOSOMAL PROTEIN S3, CHAIN F         <===
REMARK 400 1FJF         THERMUS THERMOPHILUS
REMARK 400 ===> 30S RIBOSOMAL PROTEIN S4, CHAIN G         <===
```

```
REMARK 400 1FJF       THERMUS THERMOPHILUS
REMARK 400 ===> 30S RIBOSOMAL PROTEIN S5, CHAIN H        <===
REMARK 400 1FJF       THERMUS THERMOPHILUS
REMARK 400 ===> 30S RIBOSOMAL PROTEIN S6, CHAIN I        <===
REMARK 400 1FJF       THERMUS THERMOPHILUS
REMARK 400 ===> 30S RIBOSOMAL PROTEIN S7, CHAIN J        <===
REMARK 400 1FJF       THERMUS THERMOPHILUS
REMARK 400 ===> 30S RIBOSOMAL PROTEIN S8, CHAIN K        <===
REMARK 400 1FJF       THERMUS THERMOPHILUS
REMARK 400 ===> 30S RIBOSOMAL PROTEIN S9, CHAIN L        <===
REMARK 400 1FJF       THERMUS THERMOPHILUS
REMARK 400 ===> 30S RIBOSOMAL PROTEIN S10, CHAIN M       <===
REMARK 400 1FJF       THERMUS THERMOPHILUS
REMARK 400 ===> 30S RIBOSOMAL PROTEIN S11, CHAIN N       <===
REMARK 400 1FJF       THERMUS THERMOPHILUS
REMARK 400 ===> 30S RIBOSOMAL PROTEIN S12, CHAIN O       <===
REMARK 400 1FJF       THERMUS THERMOPHILUS
REMARK 400 ===> 30S RIBOSOMAL PROTEIN S13, CHAIN P       <===
REMARK 400 1FJF       THERMUS THERMOPHILUS
REMARK 400 ===> 30S RIBOSOMAL PROTEIN S14, CHAIN Q       <===
REMARK 400 1FJF       THERMUS THERMOPHILUS
REMARK 400 ===> 30S RIBOSOMAL PROTEIN S15, CHAIN R       <===
REMARK 400 1FJF       THERMUS THERMOPHILUS
REMARK 400 ===> 30S RIBOSOMAL PROTEIN S16, CHAIN S       <===
REMARK 400 1FJF       THERMUS THERMOPHILUS
REMARK 400 ===> 30S RIBOSOMAL PROTEIN S17, CHAIN T       <===
REMARK 400 1FJF       THERMUS THERMOPHILUS
REMARK 400 ===> 30S RIBOSOMAL PROTEIN S18, CHAIN U       <===
REMARK 400 1FJF       THERMUS THERMOPHILUS
REMARK 400 ===> 30S RIBOSOMAL PROTEIN S19, CHAIN V       <===
REMARK 400 1FJF       THERMUS THERMOPHILUS
REMARK 400 ===> 30S RIBOSOMAL PROTEIN S20, CHAIN W       <===
REMARK 400 1FJF       THERMUS THERMOPHILUS
REMARK 400 ===> 30S RIBOSOMAL PROTEIN THX, CHAIN X       <===
REMARK 400 1FJF       THERMUS THERMOPHILUS
REMARK 400
REMARK 400 ==================================================
REMARK 400      50S LARGE SUBUNIT, PDB FILE 1GIY
REMARK 400 ==================================================
REMARK 400
REMARK 400 ===> 50S 23S RIBOSOMAL RNA, CHAIN A           <===
REMARK 400 1FFK       THERMUS THERMOPHILUS
REMARK 400 ===> 50S 5S RIBOSOMAL RNA, CHAIN B            <===
REMARK 400 1FFK       THERMUS THERMOPHILUS
REMARK 400 ===> 50S RIBOSOMAL PROTEIN L1, CHAIN C        <===
REMARK 400 NO PUBLIC COORDINATES FOR THE MODEL
REMARK 400            THERMUS AQUATICUS
REMARK 400 ===> 50S RIBOSOMAL PROTEIN L2 , CHAIN D       <===
REMARK 400 1RL2 (RESIDUES  61-197), BACILLUS STEAROTHERMOPHILUS
REMARK 400 1FFK (RESIDUES 138-203), HALOARCULA MARISMORTUI
REMARK 400 ===> 50S RIBOSOMAL PROTEIN L3 , CHAIN E       <===
REMARK 400 1FFK        HALOARCULA MARISMORTUI (L3P)
REMARK 400 ===> 50S RIBOSOMAL PROTEIN L4, CHAIN F        <===
REMARK 400 1FFK        HALOARCULA MARISMORTUI (L4E)
REMARK 400 ===> 50S RIBOSOMAL PROTEIN L5, CHAIN G        <===
REMARK 400 1FFK        HALOARCULA MARISMORTUI (L5P)
REMARK 400 ===> 50S RIBOSOMAL PROTEIN L6, CHAIN H
REMARK 400 1RL6       BACILLUS STEAROTHERMOPHILUS
REMARK 400 ===> 50S RIBOSOMAL PROTEIN L7/L12, CHAIN I, J <===
REMARK 400 1DD3       THERMOTOGA MARITIMA
REMARK 400 ===> 50S RIBOSOMAL PROTEIN L9, CHAIN K        <===
REMARK 400 1DIV       BACILLUS STEAROTHERMOPHILUS
REMARK 400 ===> 50S RIBOSOMAL PROTEIN L11, CHAIN L       <===
REMARK 400 1MMS       THERMOTOGA MARITIMA
REMARK 400 ===> 50S RIBOSOMAL PROTEIN L13, CHAIN M       <===
REMARK 400 1FFK        HALOARCULA MARISMORTUI (L13P)
REMARK 400 ===> 50S RIBOSOMAL PROTEIN L14, CHAIN N       <===
REMARK 400 1WHI       BACILLUS STEAROTHERMOPHILUS
REMARK 400 ===> 50S RIBOSOMAL PROTEIN L15, CHAIN O       <===
REMARK 400 1FFK        HALOARCULA MARISMORTUI (L15P)
REMARK 400 ===> 50S RIBOSOMAL PROTEIN L16, CHAIN P       <===
REMARK 400 1FFK       NO SEQUENCE ENTRY FOUND
REMARK 400 ===> 50S RIBOSOMAL PROTEIN L18, CHAIN Q       <===
REMARK 400 1FFK        HALOARCULA MARISMORTUI (L18P)
REMARK 400 ===> 50S RIBOSOMAL PROTEIN L19, CHAIN R       <===
REMARK 400 1FFK        HALOARCULA MARISMORTUI (L24E)
REMARK 400 ===> 50S RIBOSOMAL PROTEIN L22, CHAIN S       <===
REMARK 400 1BXE       THERMUS THERMOPHILUS
REMARK 400 ===> 50S RIBOSOMAL PROTEIN L23, CHAIN T       <===
REMARK 400 1FFK        HALOARCULA MARISMORTUI (L23P)
REMARK 400 ===> 50S RIBOSOMAL PROTEIN L24, CHAIN U       <===
REMARK 400 1FFK        HALOARCULA MARISMORTUI (L24P)
REMARK 400 ===> 50S RIBOSOMAL PROTEIN L25, CHAIN V       <===
REMARK 400 1DFU       ESCHERICHIA COLI
REMARK 400 ===> 50S RIBOSOMAL PROTEIN L29, CHAIN W       <===
REMARK 400 1FFK        HALOARCULA MARISMORTUI (L29P)
REMARK 400 ===> 50S RIBOSOMAL PROTEIN L30, CHAIN X       <===
```

```
REMARK 400 1BXY     THERMUS THERMOPHILUS
REMARK 900
REMARK 900 RELATED ENTRIES
REMARK 900 RELATED ID: 1GIX     RELATED DB: PDB
REMARK 900 CRYSTAL STRUCTURE OF THE RIBOSOME AT 5.5 A RESOLUTION, 30S
REMARK 900 PART
REMARK 900 RELATED ID: 1GIY     RELATED DB: PDB
REMARK 900 CRYSTAL STRUCTURE OF THE RIBOSOME AT 5.5 A RESOLUTION, 50S
REMARK 900 PART
REMARK 900 RELATED ID: 1JGP     RELATED DB: PDB
REMARK 900 CRYSTAL STRUCTURE OF THE RIBOSOME AT 7.0 A RESOLUTION, 30S
REMARK 900 PART, DIFFERENT MRNA
REMARK 900 RELATED ID: 1JGQ     RELATED DB: PDB
REMARK 900 CRYSTAL STRUCTURE OF THE RIBOSOME AT 5.0 A RESOLUTION, 30S
REMARK 900 PART, DIFFERENT MRNA
DBREF  1JGO A    0  1544  GB       155076   M26924         646  2167
DBREF  1JGO B    1    76  GB       176479   M10263           1    76
DBREF  1JGO C    1    76  GB       176479   M10263           1    76
DBREF  1JGO E    1   256  EMBL   13446664   CAC35061         1   256
DBREF  1JGO F    1   239  SWS    13446666   RS4_THETH        1   239
DBREF  1JGO G    1   209  SWS       P80373  RS4_THETH        1   209
DBREF  1JGO H    1   162  SWS       P27152  RS5_THETH        1   162
DBREF  1JGO I    1   101  SWS       P23370  RS6_THETH        1   101
DBREF  1JGO J    1   156  SWS       P17291  RS7_THETH        1   156
DBREF  1JGO K    1   138  SWS       P24319  RS8_THETH        1   138
DBREF  1JGO L    1   128  EMBL   13446668   CAC35063         1   128
DBREF  1JGO M    1   105  SWS       P80375  RS10_THETH       1   105
DBREF  1JGO N    1   129  GB      4519421   BAA75547         1   129
DBREF  1JGO O    1   135  SWS       P17293  RS12_THETH       1   135
DBREF  1JGO P    1   126  GB      4519420   BAA75546         1   126
DBREF  1JGO Q    1    61  SWS       P24320  RS14_THETH       1    61
DBREF  1JGO R    1    89  SWS       P80378  RS15_THETH       1    89
DBREF  1JGO S    1    91  GB     12056104   CAC21226         1    91
DBREF  1JGO T    1   105  EMBL     673503   CAA85419         1   105
DBREF  1JGO U    1    88  GB      6739549   AAF27297         1    88
DBREF  1JGO V    1    93  SWS       P80381  RS19_THETH       1    93
DBREF  1JGO W    1   106  GB     11125386   CAC15067         1   106
DBREF  1JGO X    2    27  SWS       P32193  RSHX_THETH       1    26
SEQADV 1JGO 2MG B   10  GB      176479              G   10 TRNA MODIFICATION
SEQADV 1JGO H2U B   16  GB      176479              U   16 TRNA MODIFICATION
SEQADV 1JGO H2U B   17  GB      176479              U   17 TRNA MODIFICATION
SEQADV 1JGO M2G B   26  GB      176479              G   26 TRNA MODIFICATION
SEQADV 1JGO OMC B   32  GB      176479              C   32 TRNA MODIFICATION
SEQADV 1JGO OMG B   34  GB      176479              G   34 TRNA MODIFICATION
SEQADV 1JGO  YG B   37  GB      176479              G   37 TRNA MODIFICATION
SEQADV 1JGO PSU B   39  GB      176479              U   39 TRNA MODIFICATION
SEQADV 1JGO 5MC B   40  GB      176479              C   40 TRNA MODIFICATION
SEQADV 1JGO 7MG B   46  GB      176479              G   46 TRNA MODIFICATION
SEQADV 1JGO 5MC B   49  GB      176479              C   49 TRNA MODIFICATION
SEQADV 1JGO 5MU B   54  GB      176479              U   54 TRNA MODIFICATION
SEQADV 1JGO PSU B   55  GB      176479              U   55 TRNA MODIFICATION
SEQADV 1JGO 1MA B   58  GB      176479              A   58 TRNA MODIFICATION
SEQADV 1JGO 2MG C   10  GB      176479              G   10 TRNA MODIFICATION
SEQADV 1JGO H2U C   16  GB      176479              U   16 TRNA MODIFICATION
SEQADV 1JGO H2U C   17  GB      176479              U   17 TRNA MODIFICATION
SEQADV 1JGO M2G C   26  GB      176479              G   26 TRNA MODIFICATION
SEQADV 1JGO OMC C   32  GB      176479              C   32 TRNA MODIFICATION
SEQADV 1JGO OMG C   34  GB      176479              G   34 TRNA MODIFICATION
SEQADV 1JGO  YG C   37  GB      176479              G   37 TRNA MODIFICATION
SEQADV 1JGO PSU C   39  GB      176479              U   39 TRNA MODIFICATION
SEQADV 1JGO 5MC C   40  GB      176479              C   40 TRNA MODIFICATION
SEQADV 1JGO 7MG C   46  GB      176479              G   46 TRNA MODIFICATION
SEQADV 1JGO 5MC C   49  GB      176479              C   49 TRNA MODIFICATION
SEQADV 1JGO 5MU C   54  GB      176479              U   54 TRNA MODIFICATION
SEQADV 1JGO PSU C   55  GB      176479              U   55 TRNA MODIFICATION
SEQADV 1JGO 1MA C   58  GB      176479              A   58 TRNA MODIFICATION

SEQRES   1 1   27    G  G  C  A  G  G  A  G  U  A  A
SEQRES   2 1   27    A  A  U  U  U  U  U  U  A  A  A  A  A
SEQRES   3 1   27    A

MODRES 1JGO 2MG B   10     2N-METHYLGUANOSINE-5'-MONOPHOSPHATE
MODRES 1JGO H2U B   16     5,6-DIHYDROURIDINE-5'-MONOPHOSPHATE
MODRES 1JGO H2U B   17     5,6-DIHYDROURIDINE-5'-MONOPHOSPHATE
MODRES 1JGO M2G B   26     N2-DIMETHYLGUANOSINE-5'-MONOPHOSPHATE
MODRES 1JGO OMC B   32     O2'-METHYLCYTIDINE-5'-MONOPHOSPHATE
MODRES 1JGO OMG B   34     O2'-METHYLGUANOSINE-5'-MONOPHOSPHATE
MODRES 1JGO  YG B   37     WYBUTOSINE
MODRES 1JGO PSU B   39     PSEUDOURIDINE-5'-MONOPHOSPHATE
MODRES 1JGO 5MC B   40     5-METHYLCYTIDINE-5'-MONOPHOSPHATE
MODRES 1JGO 7MG B   46
MODRES 1JGO 5MC B   49     5-METHYLCYTIDINE-5'-MONOPHOSPHATE
MODRES 1JGO 5MU B   54     5-METHYLURIDINE 5'-MONOPHOSPHATE
MODRES 1JGO PSU B   55     PSEUDOURIDINE-5'-MONOPHOSPHATE
MODRES 1JGO 1MA B   58
MODRES 1JGO 2MG C   10     2N-METHYLGUANOSINE-5'-MONOPHOSPHATE
MODRES 1JGO H2U C   16     5,6-DIHYDROURIDINE-5'-MONOPHOSPHATE
```

```
MODRES 1JGO H2U C  17     5,6-DIHYDROURIDINE-5'-MONOPHOSPHATE
MODRES 1JGO M2G C  26     N2-DIMETHYLGUANOSINE-5'-MONOPHOSPHATE
MODRES 1JGO OMC C  32     O2'-METHYLYCYTIDINE-5'-MONOPHOSPHATE
MODRES 1JGO OMG C  34     O2'-METHYLGUANOSINE-5'-MONOPHOSPHATE
MODRES 1JGO  YG C  37     WYBUTOSINE
MODRES 1JGO PSU C  39     PSEUDOURIDINE-5'-MONOPHOSPHATE
MODRES 1JGO 5MC C  40     5-METHYLCYTIDINE-5'-MONOPHOSPHATE
MODRES 1JGO 7MG C  46
MODRES 1JGO 5MC C  49     5-METHYLCYTIDINE-5'-MONOPHOSPHATE
MODRES 1JGO 5MU C  54     5-METHYLURIDINE 5'-MONOPHOSPHATE
MODRES 1JGO PSU C  55     PSEUDOURIDINE-5'-MONOPHOSPHATE
MODRES 1JGO 1MA C  58
MODRES 1JGO 4SU D   8     4-THIOURIDINE-5'-MONOPHOSPHATE
MODRES 1JGO H2U D  20     5,6-DIHYDROURIDINE-5'-MONOPHOSPHATE
MODRES 1JGO H2U D  21     5,6-DIHYDROURIDINE-5'-MONOPHOSPHATE
MODRES 1JGO 5MC D  49     5-METHYLCYTIDINE-5'-MONOPHOSPHATE
MODRES 1JGO 5MU D  54     5-METHYLURIDINE 5'-MONOPHOSPHATE
MODRES 1JGO PSU D  55     PSEUDOURIDINE-5'-MONOPHOSPHATE
HET     2MG  B  10      24
HET     H2U  B  16      20
HET     H2U  B  17      20
HET     M2G  B  26      25
HET     OMC  B  32      21
HET     OMG  B  34      24
HET      YG  B  37      39
HET     PSU  B  39      20
HET     5MC  B  40      21
HET     7MG  B  46      24
HET     5MC  B  49      21
HET     5MU  B  54      21
HET     PSU  B  55      20
HET     1MA  B  58      23
HET     2MG  C  10      24
HET     H2U  C  16      20
HET     H2U  C  17      20
HET     M2G  C  26      25
HET     OMC  C  32      21
HET     OMG  C  34      24
HET      YG  C  37      39
HET     PSU  C  39      20
HET     5MC  C  40      21
HET     7MG  C  46      24
HET     5MC  C  49      21
HET     5MU  C  54      21
HET     PSU  C  55      20
HET     1MA  C  58      23
HET     4SU  D   8      20
HET     H2U  D  20      20
HET     H2U  D  21      20
HET     5MC  D  49      21
HET     5MU  D  54      21
HET     PSU  D  55      20
HETNAM       2MG 2N-METHYLGUANOSINE-5'-MONOPHOSPHATE
HETNAM       H2U 5,6-DIHYDROURIDINE-5'-MONOPHOSPHATE
HETNAM       M2G N2-DIMETHYLGUANOSINE-5'-MONOPHOSPHATE
HETNAM       OMC O2'-METHYLYCYTIDINE-5'-MONOPHOSPHATE
HETNAM       OMG O2'-METHYLGUANOSINE-5'-MONOPHOSPHATE
HETNAM        YG WYBUTOSINE
HETNAM       PSU PSEUDOURIDINE-5'-MONOPHOSPHATE
HETNAM       5MC 5-METHYLCYTIDINE-5'-MONOPHOSPHATE
HETNAM       7MG 7N-METHYL-8-HYDROGUANOSINE-5'-MONOPHOSPHATE
HETNAM       5MU 5-METHYLURIDINE 5'-MONOPHOSPHATE
HETNAM       1MA 6-HYDRO-1-METHYLADENOSINE-5'-MONOPHOSPHATE
HETNAM       4SU 4-THIOURIDINE-5'-MONOPHOSPHATE
HETSYN        YG Y-BASE; 1H-IMIDAZO(1,2-ALPHA)PURINE-7-BUTANOIC ACID,4,
HETSYN     2  YG 9-DIHYDRO-ALPHA-((METHOXYCARBONYL)AMINO)-4,6-DIMETHYL-
HETSYN     3  YG 9-OXO-METHYL ESTER
FORMUL     2 2MG    2(C11 H16 N5 O8 P1)
FORMUL     2 H2U    6(C9 H15 N2 O9 P1)
FORMUL     2 M2G    2(C12 H18 N5 O8 P1)
FORMUL     2 OMC    2(C10 H16 N3 O8 P1)
FORMUL     2 OMG    2(C11 H16 N5 O8 P1)
FORMUL     2  YG    2(C21 H29 N6 O12 P1)
FORMUL     2 PSU    5(C9 H13 N2 O9 P1)
FORMUL     2 5MC    5(C10 H16 N3 O8 P1)
FORMUL     2 7MG    2(C11 H18 N5 O8 P1)
FORMUL     2 5MU    3(C10 H15 N2 O9 P1)
FORMUL     2 1MA    2(C11 H18 N5 O7 P1)
FORMUL     4 4SU     C9 H13 N2 O8 P1 S1
LINK         O3*     A B   9              P  2MG B  10
LINK         O3* 2MG B  10              P    C B  11
LINK         O3*     G B  15              P  H2U B  16
LINK         O3* H2U B  16              P  H2U B  17
LINK         O3* H2U B  17              P    G B  18
LINK         O3*     C B  25              P  M2G B  26
LINK         O3* M2G B  26              P    C B  27
LINK         O3*     A B  31              P  OMC B  32
```

```
LINK    O3*  OMC B  32        P    U   B  33
LINK    O3*    U B  33        P   OMG  B  34
LINK    O3*  OMG B  34        P    A   B  35
LINK    O3*    A B  36        P   YG   B  37
LINK    O3*   YG B  37        P    A   B  38
LINK    O3*    A B  38        P   PSU  B  39
LINK    O3*  PSU B  39        P   5MC  B  40
LINK    O3*  5MC B  40        P    U   B  41
LINK    O3*    G B  45        P   7MG  B  46
LINK    O3*  7MG B  46        P    U   B  47
LINK    O3*    C B  48        P   5MC  B  49
LINK    O3*  5MC B  49        P    U   B  50
LINK    O3*    G B  53        P   5MU  B  54
LINK    O3*  5MU B  54        P   PSU  B  55
LINK    O3*  PSU B  55        P    C   B  56
LINK    O3*    G B  57        P   1MA  B  58
LINK    O3*  1MA B  58        P    U   B  59
LINK    O3*    A C   9        P   2MG  C  10
LINK    O3*  2MG C  10        P    C   C  11
LINK    O3*    G C  15        P   H2U  C  16
LINK    O3*  H2U C  16        P   H2U  C  17
LINK    O3*  H2U C  17        P    G   C  18
LINK    O3*  M2G C  26        P    C   C  27
LINK    O3*    A C  31        P   OMC  C  32
LINK    O3*  OMC C  32        P    U   C  33
LINK    O3*    U C  33        P   OMG  C  34
LINK    O3*  OMG C  34        P    A   C  35
LINK    O3*    A C  36        P   YG   C  37
LINK    O3*   YG C  37        P    A   C  38
LINK    O3*    A C  38        P   PSU  C  39
LINK    O3*  PSU C  39        P   5MC  C  40
LINK    O3*  5MC C  40        P    U   C  41
LINK    O3*    G C  45        P   7MG  C  46
LINK    O3*  7MG C  46        P    U   C  47
LINK    O3*    C C  48        P   5MC  C  49
LINK    O3*  5MC C  49        P    U   C  50
LINK    O3*    G C  53        P   5MU  C  54
LINK    O3*  5MU C  54        P   PSU  C  55
LINK    O3*  PSU C  55        P    C   C  56
LINK    O3*    G C  57        P   1MA  C  58
LINK    O3*  1MA C  58        P    U   C  59
LINK    O3*  4SU D   8        P    A   D   9
LINK    O3*    G D  19        P   H2U  D  20
LINK    O3*  H2U D  20        P   H2U  D  21
LINK    O3*  H2U D  21        P    A   D  22
LINK    O3*  5MC D  49        P    G   D  50
LINK    O3*    G D  53        P   5MU  D  54
LINK    O3*  5MU D  54        P   PSU  D  55
LINK    O3*  PSU D  55        P    C   D  56

CRYST1   507.200  507.200  803.660  90.00  90.00  90.00 I 4 2 2    32
ORIGX1      1.000000  0.000000  0.000000        0.00000
ORIGX2      0.000000  1.000000  0.000000        0.00000
ORIGX3      0.000000  0.000000  1.000000        0.00000
SCALE1      0.001972 -0.000000  0.000000        0.00000
SCALE2      0.000000  0.001972  0.000000        0.00000
SCALE3      0.000000  0.000000  0.001244        0.00000

ATOM   6398  P       G 1    1      30.267  55.984 290.530  1.00  0.00           P
ATOM   6399  P       G 1    2      25.835  58.943 289.316  1.00  0.00           P
ATOM   6400  P       C 1    3      21.497  59.562 288.241  1.00  0.00           P
ATOM   6401  P       A 1    4      17.507  58.928 289.509  1.00  0.00           P
ATOM   6402  P       A 1    5      13.282  58.665 293.068  1.00  0.00           P
ATOM   6403  P       G 1    6      10.612  61.237 296.929  1.00  0.00           P
ATOM   6404  P       G 1    7      10.047  64.944 301.531  1.00  0.00           P
ATOM   6405  P       A 1    8      12.353  69.634 304.279  1.00  0.00           P
ATOM   6406  P       G 1    9      16.376  73.641 304.829  1.00  0.00           P
ATOM   6407  P       G 1   10      21.109  76.064 302.978  1.00  0.00           P
ATOM   6408  P       U 1   11      24.950  79.364 299.517  1.00  0.00           P
ATOM   6409  P       A 1   12      23.270  83.350 293.009  1.00  0.00           P
ATOM   6410  P       A 1   13      19.013  87.856 290.519  1.00  0.00           P
ATOM   6411  P       A 1   14      15.794  90.173 284.650  1.00  0.00           P
ATOM   6412  P       A 1   15      14.404  94.510 279.074  1.00  0.00           P
ATOM   6413  P       U 1   16       9.248  97.344 283.458  1.00  0.00           P
ATOM   6414  O1P     U 1   16       8.764  96.486 282.352  1.00  0.00           O
ATOM   6415  O2P     U 1   16       9.069  96.805 284.825  1.00  0.00           O
ATOM   6416  O5*     U 1   16       8.563  98.786 283.356  1.00  0.00           O
ATOM   6417  C5*     U 1   16       8.892  99.785 284.340  1.00  0.00           C
ATOM   6418  C4*     U 1   16       8.176 101.082 284.019  1.00  0.00           C
ATOM   6419  O4*     U 1   16       8.690 101.605 282.760  1.00  0.00           O
ATOM   6420  C3*     U 1   16       6.669 100.973 283.785  1.00  0.00           C
ATOM   6421  O3*     U 1   16       5.945 100.960 285.007  1.00  0.00           O
ATOM   6422  C2*     U 1   16       6.386 102.217 282.931  1.00  0.00           C
ATOM   6423  O2*     U 1   16       6.374 103.379 283.714  1.00  0.00           O
ATOM   6424  C1*     U 1   16       7.645 102.259 282.058  1.00  0.00           C
ATOM   6425  N1      U 1   16       7.447 101.562 280.757  1.00  0.00           N
ATOM   6426  C2      U 1   16       6.790 102.256 279.768  1.00  0.00           C
```

```
ATOM   6427  O2   U 1  16    6.376 103.392 279.922  1.00  0.00           O
ATOM   6428  N3   U 1  16    6.626 101.579 278.577  1.00  0.00           N
ATOM   6429  C4   U 1  16    7.053 100.298 278.297  1.00  0.00           C
ATOM   6430  O4   U 1  16    6.848  99.795 277.191  1.00  0.00           O
ATOM   6431  C5   U 1  16    7.732  99.650 279.395  1.00  0.00           C
ATOM   6432  C6   U 1  16    7.906 100.286 280.566  1.00  0.00           C
ATOM   6433  P    U 1  17    4.601 100.397 285.104  1.00  0.00           P
ATOM   6434  O1P  U 1  17    4.143 100.343 286.511  1.00  0.00           O
ATOM   6435  O2P  U 1  17    4.691  99.097 284.400  1.00  0.00           O
ATOM   6436  O5*  U 1  17    3.664 101.392 284.273  1.00  0.00           O
ATOM   6437  C5*  U 1  17    3.435 102.720 284.779  1.00  0.00           C
ATOM   6438  C4*  U 1  17    2.570 103.502 283.809  1.00  0.00           C
ATOM   6439  O4*  U 1  17    3.309 103.691 282.568  1.00  0.00           O
ATOM   6440  C3*  U 1  17    1.276 102.817 283.368  1.00  0.00           C
ATOM   6441  O3*  U 1  17    0.237 102.990 284.321  1.00  0.00           O
ATOM   6442  C2*  U 1  17    0.987 103.511 282.030  1.00  0.00           C
ATOM   6443  O2*  U 1  17    0.465 104.798 282.226  1.00  0.00           O
ATOM   6444  C1*  U 1  17    2.407 103.666 281.474  1.00  0.00           C
ATOM   6445  N1   U 1  17    2.784 102.535 280.581  1.00  0.00           N
ATOM   6446  C2   U 1  17    2.319 102.575 279.288  1.00  0.00           C
ATOM   6447  O2   U 1  17    1.625 103.483 278.862  1.00  0.00           O
ATOM   6448  N3   U 1  17    2.690 101.512 278.491  1.00  0.00           N
ATOM   6449  C4   U 1  17    3.468 100.437 278.868  1.00  0.00           C
ATOM   6450  O4   U 1  17    3.734  99.542 278.063  1.00  0.00           O
ATOM   6451  C5   U 1  17    3.908 100.482 280.243  1.00  0.00           C
ATOM   6452  C6   U 1  17    3.562 101.508 281.041  1.00  0.00           C
ATOM   6453  P    U 1  18   -0.903 102.079 284.397  1.00  0.00           P
ATOM   6454  O1P  U 1  18   -1.744 102.370 285.578  1.00  0.00           O
ATOM   6455  O2P  U 1  18   -0.302 100.727 284.343  1.00  0.00           O
ATOM   6456  O5*  U 1  18   -1.745 102.343 283.061  1.00  0.00           O
ATOM   6457  C5*  U 1  18   -2.421 103.605 282.901  1.00  0.00           C
ATOM   6458  C4*  U 1  18   -3.104 103.659 281.550  1.00  0.00           C
ATOM   6459  O4*  U 1  18   -2.086 103.639 280.506  1.00  0.00           O
ATOM   6460  C3*  U 1  18   -4.004 102.471 281.209  1.00  0.00           C
ATOM   6461  O3*  U 1  18   -5.295 102.604 281.785  1.00  0.00           O
ATOM   6462  C2*  U 1  18   -4.022 102.512 279.674  1.00  0.00           C
ATOM   6463  O2*  U 1  18   -4.863 103.530 279.203  1.00  0.00           O
ATOM   6464  C1*  U 1  18   -2.578 102.930 279.380  1.00  0.00           C
ATOM   6465  N1   U 1  18   -1.693 101.756 279.141  1.00  0.00           N
ATOM   6466  C2   U 1  18   -1.736 101.184 277.893  1.00  0.00           C
ATOM   6467  O2   U 1  18   -2.457 101.595 277.000  1.00  0.00           O
ATOM   6468  N3   U 1  18   -0.902 100.100 277.708  1.00  0.00           N
ATOM   6469  C4   U 1  18   -0.050  99.553 278.646  1.00  0.00           C
ATOM   6470  O4   U 1  18    0.652  98.579 278.364  1.00  0.00           O
ATOM   6471  C5   U 1  18   -0.074 100.221 279.925  1.00  0.00           C
ATOM   6472  C6   U 1  18   -0.876 101.280 280.133  1.00  0.00           C
ATOM   6473  P    U 1  19   -6.296 102.388 282.881  1.00  0.00           P
ATOM   6474  O1P  U 1  19   -5.389 101.922 283.952  1.00  0.00           O
ATOM   6475  O2P  U 1  19   -6.993 101.331 282.113  1.00  0.00           O
ATOM   6476  O5*  U 1  19   -7.372 103.403 283.492  1.00  0.00           O
ATOM   6477  C5*  U 1  19   -6.912 104.515 284.283  1.00  0.00           C
ATOM   6478  C4*  U 1  19   -8.094 105.241 284.892  1.00  0.00           C
ATOM   6479  O4*  U 1  19   -8.519 106.297 283.982  1.00  0.00           O
ATOM   6480  C3*  U 1  19   -9.356 104.403 285.101  1.00  0.00           C
ATOM   6481  O3*  U 1  19   -9.295 103.647 286.301  1.00  0.00           O
ATOM   6482  C2*  U 1  19  -10.453 105.477 285.122  1.00  0.00           C
ATOM   6483  O2*  U 1  19  -10.473 106.160 286.345  1.00  0.00           O
ATOM   6484  C1*  U 1  19   -9.928 106.447 284.059  1.00  0.00           C
ATOM   6485  N1   U 1  19  -10.502 106.167 282.713  1.00  0.00           N
ATOM   6486  C2   U 1  19  -11.767 106.643 282.460  1.00  0.00           C
ATOM   6487  O2   U 1  19  -12.413 107.269 283.282  1.00  0.00           O
ATOM   6488  N3   U 1  19  -12.265 106.365 281.204  1.00  0.00           N
ATOM   6489  C4   U 1  19  -11.621 105.668 280.202  1.00  0.00           C
ATOM   6490  O4   U 1  19  -12.170 105.481 279.115  1.00  0.00           O
ATOM   6491  C5   U 1  19  -10.299 105.209 280.561  1.00  0.00           C
ATOM   6492  C6   U 1  19   -9.789 105.466 281.777  1.00  0.00           C
ATOM   6493  P    U 1  20  -10.100 102.445 286.499  1.00  0.00           P
ATOM   6494  O1P  U 1  20   -9.722 101.746 287.749  1.00  0.00           O
ATOM   6495  O2P  U 1  20   -9.931 101.672 285.246  1.00  0.00           O
ATOM   6496  O5*  U 1  20  -11.611 102.960 286.610  1.00  0.00           O
ATOM   6497  C5*  U 1  20  -12.000 103.736 287.759  1.00  0.00           C
ATOM   6498  C4*  U 1  20  -13.449 104.163 287.628  1.00  0.00           C
ATOM   6499  O4*  U 1  20  -13.571 105.073 286.497  1.00  0.00           O
ATOM   6500  C3*  U 1  20  -14.447 103.048 287.315  1.00  0.00           C
ATOM   6501  O3*  U 1  20  -14.836 102.343 288.485  1.00  0.00           O
ATOM   6502  C2*  U 1  20  -15.602 103.824 286.668  1.00  0.00           C
ATOM   6503  O2*  U 1  20  -16.365 104.498 287.633  1.00  0.00           O
ATOM   6504  C1*  U 1  20  -14.829 104.879 285.870  1.00  0.00           C
ATOM   6505  N1   U 1  20  -14.590 104.451 284.463  1.00  0.00           N
ATOM   6506  C2   U 1  20  -15.630 104.604 283.576  1.00  0.00           C
ATOM   6507  O2   U 1  20  -16.711 105.065 283.898  1.00  0.00           O
ATOM   6508  N3   U 1  20  -15.371 104.199 282.284  1.00  0.00           N
ATOM   6509  C4   U 1  20  -14.189 103.665 281.813  1.00  0.00           C
ATOM   6510  O4   U 1  20  -14.076 103.337 280.630  1.00  0.00           O
ATOM   6511  C5   U 1  20  -13.157 103.542 282.816  1.00  0.00           C
ATOM   6512  C6   U 1  20  -13.382 103.931 284.083  1.00  0.00           C
ATOM   6513  P    U 1  21  -15.369 100.984 288.429  1.00  0.00           P
```

```
ATOM   6514  O1P  U 1  21     -15.528 100.415 289.786  1.00  0.00           O
ATOM   6515  O2P  U 1  21     -14.449 100.261 287.523  1.00  0.00           O
ATOM   6516  O5*  U 1  21     -16.805 101.121 287.735  1.00  0.00           O
ATOM   6517  C5*  U 1  21     -17.862 101.795 288.445  1.00  0.00           C
ATOM   6518  C4*  U 1  21     -19.107 101.857 287.584  1.00  0.00           C
ATOM   6519  O4*  U 1  21     -18.835 102.696 286.424  1.00  0.00           O
ATOM   6520  C3*  U 1  21     -19.567 100.531 286.979  1.00  0.00           C
ATOM   6521  O3*  U 1  21     -20.332  99.767 287.901  1.00  0.00           O
ATOM   6522  C2*  U 1  21     -20.380 100.997 285.763  1.00  0.00           C
ATOM   6523  O2*  U 1  21     -21.639 101.479 286.148  1.00  0.00           O
ATOM   6524  C1*  U 1  21     -19.546 102.197 285.302  1.00  0.00           C
ATOM   6525  N1   U 1  21     -18.560 101.821 284.250  1.00  0.00           N
ATOM   6526  C2   U 1  21     -19.030 101.708 282.965  1.00  0.00           C
ATOM   6527  O2   U 1  21     -20.196 101.898 282.666  1.00  0.00           O
ATOM   6528  N3   U 1  21     -18.088 101.360 282.017  1.00  0.00           N
ATOM   6529  C4   U 1  21     -16.748 101.121 282.244  1.00  0.00           C
ATOM   6530  O4   U 1  21     -15.999 100.816 281.314  1.00  0.00           O
ATOM   6531  C5   U 1  21     -16.349 101.265 283.624  1.00  0.00           C
ATOM   6532  C6   U 1  21     -17.245 101.603 284.567  1.00  0.00           C
ATOM   6533  P    A 1  22     -20.867  98.259 284.192  1.00  0.00           P
ATOM   6534  P    A 1  23     -23.533  94.810 282.803  1.00  0.00           P
ATOM   6535  P    A 1  24     -24.587  91.038 281.755  1.00  0.00           P
ATOM   6536  P    A 1  25     -26.516  87.512 282.046  1.00  0.00           P
ATOM   6537  P    A 1  26     -29.863  83.982 285.539  1.00  0.00           P
ATOM   6538  P    A 1  27     -35.135  81.032 288.053  1.00  0.00           P
TER    6539       A 1  27
CONECT 1701 1715
CONECT 1715 1701 1716 1717 1718
CONECT 1716 1715
CONECT 1717 1715
CONECT 1718 1715 1719
CONECT 1719 1718 1720
CONECT 1720 1719 1721 1722
CONECT 1721 1720 1726
CONECT 1722 1720 1723 1724
CONECT 1723 1722 1739
CONECT 1724 1722 1725 1726
CONECT 1725 1724
CONECT 1726 1721 1724 1727
CONECT 1727 1726 1728 1738
CONECT 1728 1727 1729
CONECT 1729 1728 1730
CONECT 1730 1729 1731 1738
CONECT 1731 1730 1732 1733
CONECT 1732 1731
CONECT 1733 1731 1734
CONECT 1734 1733 1735 1737
CONECT 1735 1734 1736
CONECT 1736 1735
CONECT 1737 1734 1738
CONECT 1738 1727 1730 1737
CONECT 1739 1723
CONECT 1829 1844
CONECT 1844 1829 1845 1846 1847
CONECT 1845 1844
CONECT 1846 1844
CONECT 1847 1844 1848
CONECT 1848 1847 1849
CONECT 1849 1848 1850 1851
CONECT 1850 1849 1853
CONECT 1851 1849 1852 1854
CONECT 1852 1851 1864
CONECT 1853 1850 1854 1856
CONECT 1854 1851 1853 1855
CONECT 1855 1854
CONECT 1856 1853 1857 1863
CONECT 1857 1856 1858 1859
CONECT 1858 1857
CONECT 1859 1857 1860
CONECT 1860 1859 1861 1862
CONECT 1861 1860
CONECT 1862 1860 1863
CONECT 1863 1856 1862
CONECT 1864 1852 1865 1866 1867
CONECT 1865 1864
CONECT 1866 1864
CONECT 1867 1864 1868
CONECT 1868 1867 1869
CONECT 1869 1868 1870 1871
CONECT 1870 1869 1873
CONECT 1871 1869 1872 1874
CONECT 1872 1871 1884
CONECT 1873 1870 1874 1876
CONECT 1874 1871 1873 1875
CONECT 1875 1874
CONECT 1876 1873 1877 1883
```

```
CONECT 1877 1876 1878 1879
CONECT 1878 1877
CONECT 1879 1877 1880
CONECT 1880 1879 1881 1882
CONECT 1881 1880
CONECT 1882 1880 1883
CONECT 1883 1876 1882
CONECT 1884 1872
CONECT 2051 2063
CONECT 2063 2051 2064 2065 2066
CONECT 2064 2063
CONECT 2065 2063
CONECT 2066 2063 2067
CONECT 2067 2066 2068
CONECT 2068 2067 2069 2070
CONECT 2069 2068 2074
CONECT 2070 2068 2071 2072
CONECT 2071 2070 2088
CONECT 2072 2070 2073 2074
CONECT 2073 2072
CONECT 2074 2069 2072 2075
CONECT 2075 2074 2076 2085
CONECT 2076 2075 2077
CONECT 2077 2076 2078
CONECT 2078 2077 2079 2085
CONECT 2079 2078 2080 2081
CONECT 2080 2079
CONECT 2081 2079 2082
CONECT 2082 2081 2083 2084
CONECT 2083 2082 2086 2087
CONECT 2084 2082 2085
CONECT 2085 2075 2078 2084
CONECT 2086 2083
CONECT 2087 2083
CONECT 2088 2071
CONECT 2181 2213
CONECT 2195 2196 2200 2203
CONECT 2196 2195 2197 2201
CONECT 2197 2196 2198
CONECT 2198 2197 2199 2202
CONECT 2199 2198 2200
CONECT 2200 2195 2199
CONECT 2201 2196
CONECT 2202 2198
CONECT 2203 2195 2204 2209
CONECT 2204 2203 2205 2207
CONECT 2205 2204 2206
CONECT 2206 2205
CONECT 2207 2204 2208 2210
CONECT 2208 2207 2209 2211
CONECT 2209 2203 2208
CONECT 2210 2207 2216
CONECT 2211 2208 2212
CONECT 2212 2211 2213
CONECT 2213 2181 2212 2214 2215
CONECT 2214 2213
CONECT 2215 2213
CONECT 2216 2210
CONECT 2224 2236
CONECT 2236 2224 2237 2238 2239
CONECT 2237 2236
CONECT 2238 2236
CONECT 2239 2236 2240
CONECT 2240 2239 2241
CONECT 2241 2240 2242 2243
CONECT 2242 2241 2248
CONECT 2243 2241 2244 2245
CONECT 2244 2243 2260
CONECT 2245 2243 2246 2248
CONECT 2246 2245 2247
CONECT 2247 2246
CONECT 2248 2242 2245 2249
CONECT 2249 2248 2250 2259
CONECT 2250 2249 2251
CONECT 2251 2250 2252
CONECT 2252 2251 2253 2259
CONECT 2253 2252 2254 2255
CONECT 2254 2253
CONECT 2255 2253 2256
CONECT 2256 2255 2257 2258
CONECT 2257 2256
CONECT 2258 2256 2259
CONECT 2259 2249 2252 2258
CONECT 2260 2244
CONECT 2290 2340
CONECT 2304 2306 2311 2318
CONECT 2305 2306 2317
```

```
CONECT 2306 2304 2305 2307
CONECT 2307 2306 2308 2309
CONECT 2308 2307
CONECT 2309 2307 2310 2315
CONECT 2310 2309 2311 2313
CONECT 2311 2304 2310 2312
CONECT 2312 2311
CONECT 2313 2310 2314
CONECT 2314 2313 2315
CONECT 2315 2309 2314 2331
CONECT 2316 2317
CONECT 2317 2305 2316 2318
CONECT 2318 2304 2317 2319
CONECT 2319 2318 2320
CONECT 2320 2319 2321
CONECT 2321 2320 2322 2326
CONECT 2322 2321 2323 2324
CONECT 2323 2322
CONECT 2324 2322 2325
CONECT 2325 2324
CONECT 2326 2321 2327
CONECT 2327 2326 2328 2329
CONECT 2328 2327
CONECT 2329 2327 2330
CONECT 2330 2329
CONECT 2331 2315 2332 2337
CONECT 2332 2331 2333 2334
CONECT 2333 2332
CONECT 2334 2332 2335 2336
CONECT 2335 2334 2343
CONECT 2336 2334 2337 2338
CONECT 2337 2331 2336
CONECT 2338 2336 2339
CONECT 2339 2338 2340
CONECT 2340 2290 2339 2341 2342
CONECT 2341 2340
CONECT 2342 2340
CONECT 2343 2335
CONECT 2351 2382
CONECT 2365 2366 2370
CONECT 2366 2365 2367 2371
CONECT 2367 2366 2368
CONECT 2368 2367 2369 2372
CONECT 2369 2368 2370 2373
CONECT 2370 2365 2369
CONECT 2371 2366
CONECT 2372 2368
CONECT 2373 2369 2374 2379
CONECT 2374 2373 2375 2376
CONECT 2375 2374
CONECT 2376 2374 2377 2378
CONECT 2377 2376 2379 2380
CONECT 2378 2376 2385
CONECT 2379 2373 2377
CONECT 2380 2377 2381
CONECT 2381 2380 2382
CONECT 2382 2351 2381 2383 2384
CONECT 2383 2382
CONECT 2384 2382
CONECT 2385 2378 2386 2387 2388
CONECT 2386 2385
CONECT 2387 2385
CONECT 2388 2385 2389
CONECT 2389 2388 2390
CONECT 2390 2389 2391 2392
CONECT 2391 2390 2396
CONECT 2392 2390 2393 2394
CONECT 2393 2392 2406
CONECT 2394 2392 2395 2396
CONECT 2395 2394
CONECT 2396 2391 2394 2397
CONECT 2397 2396 2398 2404
CONECT 2398 2397 2399 2400
CONECT 2399 2398
CONECT 2400 2398 2401
CONECT 2401 2400 2402 2403
CONECT 2402 2401
CONECT 2403 2401 2404 2405
CONECT 2404 2397 2403
CONECT 2405 2403
CONECT 2406 2393
CONECT 2502 2517
CONECT 2517 2502 2518 2519 2520
CONECT 2518 2517
CONECT 2519 2517
CONECT 2520 2517 2521
CONECT 2521 2520 2522
```

```
CONECT 2522 2521 2523 2524
CONECT 2523 2522 2528
CONECT 2524 2522 2525 2526
CONECT 2525 2524 2541
CONECT 2526 2524 2527 2528
CONECT 2527 2526
CONECT 2528 2523 2526 2529
CONECT 2529 2528 2530 2539
CONECT 2530 2529 2531
CONECT 2531 2530 2532 2540
CONECT 2532 2531 2533 2539
CONECT 2533 2532 2534 2535
CONECT 2534 2533
CONECT 2535 2533 2536
CONECT 2536 2535 2537 2538
CONECT 2537 2536
CONECT 2538 2536 2539
CONECT 2539 2529 2532 2538
CONECT 2540 2531
CONECT 2541 2525
CONECT 2569 2581
CONECT 2581 2569 2582 2583 2584
CONECT 2582 2581
CONECT 2583 2581
CONECT 2584 2581 2585
CONECT 2585 2584 2586
CONECT 2586 2585 2587 2588
CONECT 2587 2586 2592
CONECT 2588 2586 2589 2590
CONECT 2589 2588 2602
CONECT 2590 2588 2591 2592
CONECT 2591 2590
CONECT 2592 2587 2590 2593
CONECT 2593 2592 2594 2600
CONECT 2594 2593 2595 2596
CONECT 2595 2594
CONECT 2596 2594 2597
CONECT 2597 2596 2598 2599
CONECT 2598 2597
CONECT 2599 2597 2600 2601
CONECT 2600 2593 2599
CONECT 2601 2599
CONECT 2602 2589
CONECT 2673 2706
CONECT 2688 2689 2694 2697
CONECT 2689 2688 2690 2695
CONECT 2690 2689 2691
CONECT 2691 2690 2692 2696
CONECT 2692 2691 2693 2694
CONECT 2693 2692
CONECT 2694 2688 2692
CONECT 2695 2689
CONECT 2696 2691
CONECT 2697 2688 2698 2703
CONECT 2698 2697 2699 2700
CONECT 2699 2698
CONECT 2700 2698 2701 2702
CONECT 2701 2700 2703 2704
CONECT 2702 2700 2726
CONECT 2703 2697 2701
CONECT 2704 2701 2705
CONECT 2705 2704 2706
CONECT 2706 2673 2705 2707 2708
CONECT 2707 2706
CONECT 2708 2706
CONECT 2709 2710 2714
CONECT 2710 2709 2711 2715
CONECT 2711 2710 2712
CONECT 2712 2711 2713 2716
CONECT 2713 2712 2714 2717
CONECT 2714 2709 2713
CONECT 2715 2710
CONECT 2716 2712
CONECT 2717 2713 2718 2723
CONECT 2718 2717 2719 2720
CONECT 2719 2718
CONECT 2720 2718 2721 2722
CONECT 2721 2720 2723 2724
CONECT 2722 2720 2729
CONECT 2723 2717 2721
CONECT 2724 2721 2725
CONECT 2725 2724 2726
CONECT 2726 2702 2725 2727 2728
CONECT 2727 2726
CONECT 2728 2726
CONECT 2729 2722
CONECT 2757 2772
```

```
CONECT 2772 2757 2773 2774 2775
CONECT 2773 2772
CONECT 2774 2772
CONECT 2775 2772 2776
CONECT 2776 2775 2777
CONECT 2777 2776 2778 2779
CONECT 2778 2777 2783
CONECT 2779 2777 2780 2781
CONECT 2780 2779 2795
CONECT 2781 2779 2782 2783
CONECT 2782 2781
CONECT 2783 2778 2781 2784
CONECT 2784 2783 2785 2794
CONECT 2785 2784 2786
CONECT 2786 2785 2787
CONECT 2787 2786 2788 2794
CONECT 2788 2787 2789 2790
CONECT 2789 2788
CONECT 2790 2788 2791 2792
CONECT 2791 2790
CONECT 2792 2790 2793
CONECT 2793 2792 2794
CONECT 2794 2784 2787 2793
CONECT 2795 2780
CONECT 3354 3368
CONECT 3368 3354 3369 3370 3371
CONECT 3369 3368
CONECT 3370 3368
CONECT 3371 3368 3372
CONECT 3372 3371 3373
CONECT 3373 3372 3374 3375
CONECT 3374 3373 3379
CONECT 3375 3373 3376 3377
CONECT 3376 3375 3392
CONECT 3377 3375 3378 3379
CONECT 3378 3377
CONECT 3379 3374 3377 3380
CONECT 3380 3379 3381 3391
CONECT 3381 3380 3382
CONECT 3382 3381 3383
CONECT 3383 3382 3384 3391
CONECT 3384 3383 3385 3386
CONECT 3385 3384
CONECT 3386 3384 3387
CONECT 3387 3386 3388 3390
CONECT 3388 3387 3389
CONECT 3389 3388
CONECT 3390 3387 3391
CONECT 3391 3380 3383 3390
CONECT 3392 3376
CONECT 3482 3497
CONECT 3497 3482 3498 3499 3500
CONECT 3498 3497
CONECT 3499 3497
CONECT 3500 3497 3501
CONECT 3501 3500 3502
CONECT 3502 3501 3503 3504
CONECT 3503 3502 3506
CONECT 3504 3502 3505 3507
CONECT 3505 3504 3517
CONECT 3506 3503 3507 3509
CONECT 3507 3504 3506 3508
CONECT 3508 3507
CONECT 3509 3506 3510 3516
CONECT 3510 3509 3511 3512
CONECT 3511 3510
CONECT 3512 3510 3513
CONECT 3513 3512 3514 3515
CONECT 3514 3513
CONECT 3515 3513 3516
CONECT 3516 3509 3515
CONECT 3517 3505 3518 3519 3520
CONECT 3518 3517
CONECT 3519 3517
CONECT 3520 3517 3521
CONECT 3521 3520 3522
CONECT 3522 3521 3523 3524
CONECT 3523 3522 3526
CONECT 3524 3522 3525 3527
CONECT 3525 3524 3537
CONECT 3526 3523 3527 3529
CONECT 3527 3524 3526 3528
CONECT 3528 3527
CONECT 3529 3526 3530 3536
CONECT 3530 3529 3531 3532
CONECT 3531 3530
CONECT 3532 3530 3533
```

```
CONECT 3533 3532 3534 3535
CONECT 3534 3533
CONECT 3535 3533 3536
CONECT 3536 3529 3535
CONECT 3537 3525
CONECT 3716 3717 3718 3719
CONECT 3717 3716
CONECT 3718 3716
CONECT 3719 3716 3720
CONECT 3720 3719 3721
CONECT 3721 3720 3722 3723
CONECT 3722 3721 3727
CONECT 3723 3721 3724 3725
CONECT 3724 3723 3741
CONECT 3725 3723 3726 3727
CONECT 3726 3725
CONECT 3727 3722 3725 3728
CONECT 3728 3727 3729 3738
CONECT 3729 3728 3730
CONECT 3730 3729 3731
CONECT 3731 3730 3732 3738
CONECT 3732 3731 3733 3734
CONECT 3733 3732
CONECT 3734 3732 3735
CONECT 3735 3734 3736 3737
CONECT 3736 3735 3739 3740
CONECT 3737 3735 3738
CONECT 3738 3728 3731 3737
CONECT 3739 3736
CONECT 3740 3736
CONECT 3741 3724
CONECT 3834 3866
CONECT 3848 3849 3853 3856
CONECT 3849 3848 3850 3854
CONECT 3850 3849 3851
CONECT 3851 3850 3852 3855
CONECT 3852 3851 3853
CONECT 3853 3848 3852
CONECT 3854 3849
CONECT 3855 3851
CONECT 3856 3848 3857 3862
CONECT 3857 3856 3858 3860
CONECT 3858 3857 3859
CONECT 3859 3858
CONECT 3860 3857 3861 3863
CONECT 3861 3860 3862 3864
CONECT 3862 3856 3861
CONECT 3863 3860 3869
CONECT 3864 3861 3865
CONECT 3865 3864 3866
CONECT 3866 3834 3865 3867 3868
CONECT 3867 3866
CONECT 3868 3866
CONECT 3869 3863
CONECT 3877 3889
CONECT 3889 3877 3890 3891 3892
CONECT 3890 3889
CONECT 3891 3889
CONECT 3892 3889 3893
CONECT 3893 3892 3894
CONECT 3894 3893 3895 3896
CONECT 3895 3894 3901
CONECT 3896 3894 3897 3898
CONECT 3897 3896 3913
CONECT 3898 3896 3899 3901
CONECT 3899 3898 3900
CONECT 3900 3899
CONECT 3901 3895 3898 3902
CONECT 3902 3901 3903 3912
CONECT 3903 3902 3904
CONECT 3904 3903 3905
CONECT 3905 3904 3906 3912
CONECT 3906 3905 3907 3908
CONECT 3907 3906
CONECT 3908 3906 3909
CONECT 3909 3908 3910 3911
CONECT 3910 3909
CONECT 3911 3909 3912
CONECT 3912 3902 3905 3911
CONECT 3913 3897
CONECT 3943 3993
CONECT 3957 3959 3964 3971
CONECT 3958 3959 3970
CONECT 3959 3957 3958 3960
CONECT 3960 3959 3961 3962
CONECT 3961 3960
CONECT 3962 3960 3963 3968
```

```
CONECT 3963 3962 3964 3966
CONECT 3964 3957 3963 3965
CONECT 3965 3964
CONECT 3966 3963 3967
CONECT 3967 3966 3968
CONECT 3968 3962 3967 3984
CONECT 3969 3970
CONECT 3970 3958 3969 3971
CONECT 3971 3957 3970 3972
CONECT 3972 3971 3973
CONECT 3973 3972 3974
CONECT 3974 3973 3975 3979
CONECT 3975 3974 3976 3977
CONECT 3976 3975
CONECT 3977 3975 3978
CONECT 3978 3977
CONECT 3979 3974 3980
CONECT 3980 3979 3981 3982
CONECT 3981 3980
CONECT 3982 3980 3983
CONECT 3983 3982
CONECT 3984 3968 3985 3990
CONECT 3985 3984 3986 3987
CONECT 3986 3985
CONECT 3987 3985 3988 3989
CONECT 3988 3987 3996
CONECT 3989 3987 3990 3991
CONECT 3990 3984 3989
CONECT 3991 3989 3992
CONECT 3992 3991 3993
CONECT 3993 3943 3992 3994 3995
CONECT 3994 3993
CONECT 3995 3993
CONECT 3996 3988
CONECT 4004 4035
CONECT 4018 4019 4023
CONECT 4019 4018 4020 4024
CONECT 4020 4019 4021
CONECT 4021 4020 4022 4025
CONECT 4022 4021 4023 4026
CONECT 4023 4018 4022
CONECT 4024 4019
CONECT 4025 4021
CONECT 4026 4022 4027 4032
CONECT 4027 4026 4028 4029
CONECT 4028 4027
CONECT 4029 4027 4030 4031
CONECT 4030 4029 4032 4033
CONECT 4031 4029 4038
CONECT 4032 4026 4030
CONECT 4033 4030 4034
CONECT 4034 4033 4035
CONECT 4035 4004 4034 4036 4037
CONECT 4036 4035
CONECT 4037 4035
CONECT 4038 4031 4039 4040 4041
CONECT 4039 4038
CONECT 4040 4038
CONECT 4041 4038 4042
CONECT 4042 4041 4043
CONECT 4043 4042 4044 4045
CONECT 4044 4043 4049
CONECT 4045 4043 4046 4047
CONECT 4046 4045 4059
CONECT 4047 4045 4048 4049
CONECT 4048 4047
CONECT 4049 4044 4047 4050
CONECT 4050 4049 4051 4057
CONECT 4051 4050 4052 4053
CONECT 4052 4051
CONECT 4053 4051 4054
CONECT 4054 4053 4055 4056
CONECT 4055 4054
CONECT 4056 4054 4057 4058
CONECT 4057 4050 4056
CONECT 4058 4056
CONECT 4059 4046
CONECT 4155 4170
CONECT 4170 4155 4171 4172 4173
CONECT 4171 4170
CONECT 4172 4170
CONECT 4173 4170 4174
CONECT 4174 4173 4175
CONECT 4175 4174 4176 4177
CONECT 4176 4175 4181
CONECT 4177 4175 4178 4179
CONECT 4178 4177 4194
```

```
CONECT 4179 4177 4180 4181
CONECT 4180 4179
CONECT 4181 4176 4179 4182
CONECT 4182 4181 4183 4192
CONECT 4183 4182 4184
CONECT 4184 4183 4185 4193
CONECT 4185 4184 4186 4192
CONECT 4186 4185 4187 4188
CONECT 4187 4186
CONECT 4188 4186 4189
CONECT 4189 4188 4190 4191
CONECT 4190 4189
CONECT 4191 4189 4192
CONECT 4192 4182 4185 4191
CONECT 4193 4184
CONECT 4194 4178
CONECT 4222 4234
CONECT 4234 4222 4235 4236 4237
CONECT 4235 4234
CONECT 4236 4234
CONECT 4237 4234 4238
CONECT 4238 4237 4239
CONECT 4239 4238 4240 4241
CONECT 4240 4239 4245
CONECT 4241 4239 4242 4243
CONECT 4242 4241 4255
CONECT 4243 4241 4244 4245
CONECT 4244 4243
CONECT 4245 4240 4243 4246
CONECT 4246 4245 4247 4253
CONECT 4247 4246 4248 4249
CONECT 4248 4247
CONECT 4249 4247 4250
CONECT 4250 4249 4251 4252
CONECT 4251 4250
CONECT 4252 4250 4253 4254
CONECT 4253 4246 4252
CONECT 4254 4252
CONECT 4255 4242
CONECT 4326 4359
CONECT 4341 4342 4347 4350
CONECT 4342 4341 4343 4348
CONECT 4343 4342 4344
CONECT 4344 4343 4345 4349
CONECT 4345 4344 4346 4347
CONECT 4346 4345
CONECT 4347 4341 4345
CONECT 4348 4342
CONECT 4349 4344
CONECT 4350 4341 4351 4356
CONECT 4351 4350 4352 4353
CONECT 4352 4351
CONECT 4353 4351 4354 4355
CONECT 4354 4353 4356 4357
CONECT 4355 4353 4379
CONECT 4356 4350 4354
CONECT 4357 4354 4358
CONECT 4358 4357 4359
CONECT 4359 4326 4358 4360 4361
CONECT 4360 4359
CONECT 4361 4359
CONECT 4362 4363 4367
CONECT 4363 4362 4364 4368
CONECT 4364 4363 4365
CONECT 4365 4364 4366 4369
CONECT 4366 4365 4367 4370
CONECT 4367 4362 4366
CONECT 4368 4363
CONECT 4369 4365
CONECT 4370 4366 4371 4376
CONECT 4371 4370 4372 4373
CONECT 4372 4371
CONECT 4373 4371 4374 4375
CONECT 4374 4373 4376 4377
CONECT 4375 4373 4382
CONECT 4376 4370 4374
CONECT 4377 4374 4378
CONECT 4378 4377 4379
CONECT 4379 4355 4378 4380 4381
CONECT 4380 4379
CONECT 4381 4379
CONECT 4382 4375
CONECT 4410 4425
CONECT 4425 4410 4426 4427 4428
CONECT 4426 4425
CONECT 4427 4425
CONECT 4428 4425 4429
```

```
CONECT 4429 4428 4430
CONECT 4430 4429 4431 4432
CONECT 4431 4430 4436
CONECT 4432 4430 4433 4434
CONECT 4433 4432 4448
CONECT 4434 4432 4435 4436
CONECT 4435 4434
CONECT 4436 4431 4434 4437
CONECT 4437 4436 4438 4447
CONECT 4438 4437 4439
CONECT 4439 4438 4440
CONECT 4440 4439 4441 4447
CONECT 4441 4440 4442 4443
CONECT 4442 4441
CONECT 4443 4441 4444 4445
CONECT 4444 4443
CONECT 4445 4443 4446
CONECT 4446 4445 4447
CONECT 4447 4437 4440 4446
CONECT 4448 4433
CONECT 4976 4977 4981 4984
CONECT 4977 4976 4978 4982
CONECT 4978 4977 4979
CONECT 4979 4978 4980 4983
CONECT 4980 4979 4981
CONECT 4981 4976 4980
CONECT 4982 4977
CONECT 4983 4979
CONECT 4984 4976 4985 4990
CONECT 4985 4984 4986 4987
CONECT 4986 4985
CONECT 4987 4985 4988 4989
CONECT 4988 4987 4990 4991
CONECT 4989 4987 4996
CONECT 4990 4984 4988
CONECT 4991 4988 4992
CONECT 4992 4991 4993
CONECT 4993 4992 4994 4995
CONECT 4994 4993
CONECT 4995 4993
CONECT 4996 4989
CONECT 5200 5215
CONECT 5215 5200 5216 5217 5218
CONECT 5216 5215
CONECT 5217 5215
CONECT 5218 5215 5219
CONECT 5219 5218 5220
CONECT 5220 5219 5221 5222
CONECT 5221 5220 5224
CONECT 5222 5220 5223 5225
CONECT 5223 5222 5235
CONECT 5224 5221 5225 5227
CONECT 5225 5222 5224 5226
CONECT 5226 5225
CONECT 5227 5224 5228 5234
CONECT 5228 5227 5229 5230
CONECT 5229 5228
CONECT 5230 5228 5231
CONECT 5231 5230 5232 5233
CONECT 5232 5231
CONECT 5233 5231 5234
CONECT 5234 5227 5233
CONECT 5235 5223 5236 5237 5238
CONECT 5236 5235
CONECT 5237 5235
CONECT 5238 5235 5239
CONECT 5239 5238 5240
CONECT 5240 5239 5241 5242
CONECT 5241 5240 5244
CONECT 5242 5240 5243 5245
CONECT 5243 5242 5255
CONECT 5244 5241 5245 5247
CONECT 5245 5242 5244 5246
CONECT 5246 5245
CONECT 5247 5244 5248 5254
CONECT 5248 5247 5249 5250
CONECT 5249 5248
CONECT 5250 5248 5251
CONECT 5251 5250 5252 5253
CONECT 5252 5251
CONECT 5253 5251 5254
CONECT 5254 5247 5253
CONECT 5255 5243
CONECT 5800 5801 5802 5803
CONECT 5801 5800
CONECT 5802 5800
CONECT 5803 5800 5804
```

```
CONECT 5804 5803 5805
CONECT 5805 5804 5806 5807
CONECT 5806 5805 5811
CONECT 5807 5805 5808 5809
CONECT 5808 5807 5821
CONECT 5809 5807 5810 5811
CONECT 5810 5809
CONECT 5811 5806 5809 5812
CONECT 5812 5811 5813 5819
CONECT 5813 5812 5814 5815
CONECT 5814 5813
CONECT 5815 5813 5816
CONECT 5816 5815 5817 5818
CONECT 5817 5816
CONECT 5818 5816 5819 5820
CONECT 5819 5812 5818
CONECT 5820 5818
CONECT 5821 5808
CONECT 5898 5931
CONECT 5913 5914 5919 5922
CONECT 5914 5913 5915 5920
CONECT 5915 5914 5916
CONECT 5916 5915 5917 5921
CONECT 5917 5916 5918 5919
CONECT 5918 5917
CONECT 5919 5913 5917
CONECT 5920 5914
CONECT 5921 5916
CONECT 5922 5913 5923 5928
CONECT 5923 5922 5924 5925
CONECT 5924 5923
CONECT 5925 5923 5926 5927
CONECT 5926 5925 5928 5929
CONECT 5927 5925 5951
CONECT 5928 5922 5926
CONECT 5929 5926 5930
CONECT 5930 5929 5931
CONECT 5931 5898 5930 5932 5933
CONECT 5932 5931
CONECT 5933 5931
CONECT 5934 5935 5939
CONECT 5935 5934 5936 5940
CONECT 5936 5935 5937
CONECT 5937 5936 5938 5941
CONECT 5938 5937 5939 5942
CONECT 5939 5934 5938
CONECT 5940 5935
CONECT 5941 5937
CONECT 5942 5938 5943 5948
CONECT 5943 5942 5944 5945
CONECT 5944 5943
CONECT 5945 5943 5946 5947
CONECT 5946 5945 5948 5949
CONECT 5947 5945 5954
CONECT 5948 5942 5946
CONECT 5949 5946 5950
CONECT 5950 5949 5951
CONECT 5951 5927 5950 5952 5953
CONECT 5952 5951
CONECT 5953 5951
CONECT 5954 5947
MASTER      403    0   34    0    0    0    0    6 8930   25  817  343
END
```

File F

```
Mol_Id: 4; Molecule: Messenger RNA Mv36; Chain: 1; Engineered: Yes;
Other_Details: 36 Nt Long Mrna Fragment. The Actual Sequence
Ggcaaggagguaaaa Auggua Aaacguaaaucaacu Modeled As Ggcaaggagguaaaa Uuuuuu
Aaacguaaaucaacu
COMPND  14 MOL_ID: 4;
COMPND  15 MOLECULE: MESSENGER RNA MV36;
COMPND  16 CHAIN: 1;
COMPND  17 ENGINEERED: YES;
COMPND  18 OTHER_DETAILS: 36 NT LONG MRNA FRAGMENT. THE ACTUAL
COMPND  19 SEQUENCE GGCAAGGAGGUAAAA AUGGUA AAACGUAAAUCAACU MODELED AS
COMPND  20 GGCAAGGAGGUAAAA UUUUUU AAACGUAAAUCAACU;
SOURCE  12 MOL_ID: 4;
SOURCE  13 SYNTHETIC: YES;
KEYWDS     RIBOSOME ASSEMBLY, PROTEIN SYNTHESIS, LIFE
EXPDTA     X-RAY DIFFRACTION
AUTHOR     G.Z.YUSUPOVA,M.M.YUSUPOV,J.H.D.CATE,H.F.NOLLER
REVDAT   2  14-SEP-01 1JGP    1       JRNL
REVDAT   1  20-JUL-01 1JGP    0
JRNL        AUTH   G.Z.YUSUPOVA,M.M.YUSUPOV,J.H.D.CATE,H.F.NOLLER
JRNL        TITL   THE PATH OF MESSENGER RNA THROUGH THE RIBOSOME
```

```
JRNL        REF    CELL (CAMBRIDGE,MASS.)      V. 106   233 2001
JRNL        REFN   ASTM CELLB5   US ISSN 0092-8674
REMARK   1
REMARK   2
REMARK   2 RESOLUTION. 7.00 ANGSTROMS.
REMARK   3
REMARK   3 REFINEMENT.
REMARK   3   PROGRAM     : O
REMARK   3   AUTHORS     : JONES,ZOU,COWAN,KJELDGAARD
REMARK   3
REMARK   3  DATA USED IN REFINEMENT.
REMARK   3   RESOLUTION RANGE HIGH (ANGSTROMS) : 7.00
REMARK   3   RESOLUTION RANGE LOW  (ANGSTROMS) : 250.00
REMARK   3   DATA CUTOFF            (SIGMA(F)) : NULL
REMARK   3   DATA CUTOFF HIGH         (ABS(F)) : NULL
REMARK   3   DATA CUTOFF LOW          (ABS(F)) : NULL
REMARK   3   COMPLETENESS (WORKING+TEST)   (%) : 89.5
REMARK   3   NUMBER OF REFLECTIONS             : 73146
REMARK   3
REMARK   3  FIT TO DATA USED IN REFINEMENT.
REMARK   3   CROSS-VALIDATION METHOD          : NULL
REMARK   3   FREE R VALUE TEST SET SELECTION  : NULL
REMARK   3   R VALUE            (WORKING SET) : NULL
REMARK   3   FREE R VALUE                     : NULL
REMARK   3   FREE R VALUE TEST SET SIZE   (%) : NULL
REMARK   3   FREE R VALUE TEST SET COUNT      : NULL
REMARK   3   ESTIMATED ERROR OF FREE R VALUE  : NULL
REMARK   3
REMARK   3  FIT IN THE HIGHEST RESOLUTION BIN.
REMARK   3   TOTAL NUMBER OF BINS USED            : NULL
REMARK   3   BIN RESOLUTION RANGE HIGH       (A)  : NULL
REMARK   3   BIN RESOLUTION RANGE LOW        (A)  : NULL
REMARK   3   BIN COMPLETENESS (WORKING+TEST) (%)  : NULL
REMARK   3   REFLECTIONS IN BIN    (WORKING SET)  : NULL
REMARK   3   BIN R VALUE           (WORKING SET)  : NULL
REMARK   3   BIN FREE R VALUE                     : NULL
REMARK   3   BIN FREE R VALUE TEST SET SIZE  (%)  : NULL
REMARK   3   BIN FREE R VALUE TEST SET COUNT      : NULL
REMARK   3   ESTIMATED ERROR OF BIN FREE R VALUE  : NULL
REMARK   3
REMARK   3  NUMBER OF NON-HYDROGEN ATOMS USED IN REFINEMENT.
REMARK   3   PROTEIN ATOMS            : 2396
REMARK   3   NUCLEIC ACID ATOMS       : 6539
REMARK   3   HETEROGEN ATOMS          : 0
REMARK   3   SOLVENT ATOMS            : 0
REMARK   3
REMARK   3  B VALUES.
REMARK   3   FROM WILSON PLOT           (A**2) : NULL
REMARK   3   MEAN B VALUE      (OVERALL, A**2) : NULL
REMARK   3   OVERALL ANISOTROPIC B VALUE.
REMARK   3    B11 (A**2) : NULL
REMARK   3    B22 (A**2) : NULL
REMARK   3    B33 (A**2) : NULL
REMARK   3    B12 (A**2) : NULL
REMARK   3    B13 (A**2) : NULL
REMARK   3    B23 (A**2) : NULL
REMARK   3
REMARK   3  ESTIMATED COORDINATE ERROR.
REMARK   3   ESD FROM LUZZATI PLOT        (A) : NULL
REMARK   3   ESD FROM SIGMAA              (A) : NULL
REMARK   3   LOW RESOLUTION CUTOFF        (A) : NULL
REMARK   3
REMARK   3  CROSS-VALIDATED ESTIMATED COORDINATE ERROR.
REMARK   3   ESD FROM C-V LUZZATI PLOT    (A) : NULL
REMARK   3   ESD FROM C-V SIGMAA          (A) : NULL
REMARK   3
REMARK   3  RMS DEVIATIONS FROM IDEAL VALUES.
REMARK   3   BOND LENGTHS             (A) : NULL
REMARK   3   BOND ANGLES        (DEGREES) : NULL
REMARK   3   DIHEDRAL ANGLES    (DEGREES) : NULL
REMARK   3   IMPROPER ANGLES    (DEGREES) : NULL
REMARK   3
REMARK   3  ISOTROPIC THERMAL MODEL : NULL
REMARK   3
REMARK   3  ISOTROPIC THERMAL FACTOR RESTRAINTS.    RMS      SIGMA
REMARK   3   MAIN-CHAIN BOND              (A**2) : NULL  ;  NULL
REMARK   3   MAIN-CHAIN ANGLE             (A**2) : NULL  ;  NULL
REMARK   3   SIDE-CHAIN BOND              (A**2) : NULL  ;  NULL
REMARK   3   SIDE-CHAIN ANGLE             (A**2) : NULL  ;  NULL
REMARK   3
REMARK   3  NCS MODEL : NULL
REMARK   3
REMARK   3  NCS RESTRAINTS.                         RMS    SIGMA/WEIGHT
REMARK   3   GROUP  1  POSITIONAL            (A) : NULL  ;  NULL
REMARK   3   GROUP  1  B-FACTOR           (A**2) : NULL  ;  NULL
```

```
REMARK   3
REMARK   3 PARAMETER FILE  1   : NULL
REMARK   3 TOPOLOGY FILE   1   : NULL
REMARK   3
REMARK   3 OTHER REFINEMENT REMARKS: THE MODEL WAS BUILT BY MANUAL
REMARK   3 FITTING OF INDIVIDUAL MOLECULES INTO THE EXPERIMENTAL
REMARK   3 ELECTRON DENSITY USING THE GRAPHIC PROGRAM O.
REMARK   4
REMARK   4 1JGP COMPLIES WITH FORMAT V. 2.3, 09-JULY-1998
REMARK 100
REMARK 100 THIS ENTRY HAS BEEN PROCESSED BY THE NUCLEIC ACID DATABASE
REMARK 100 ON 16-JUL-2001.
REMARK 100 THE NDB ID CODE IS RR0035.
REMARK 105
REMARK 105 THE PROTEIN DATA BANK HAS ADOPTED THE SACCHARIDE CHEMISTS
REMARK 105 NOMENCLATURE FOR ATOMS OF THE DEOXYRIBOSE/RIBOSE MOIETY
REMARK 105 RATHER THAN THAT OF THE NUCLEOSIDE CHEMISTS.  THE RING
REMARK 105 OXYGEN ATOM IS LABELLED O4* INSTEAD OF O1*.
REMARK 106
REMARK 106 ALL HYDROGEN BONDS BETWEEN BASE PAIRS NOT MENTIONED IN
REMARK 106 REMARKS 102 AND 103 FOLLOW THE CONVENTIONAL WATSON-CRICK
REMARK 106 HYDROGEN BONDING PATTERN. THEY HAVE NOT BEEN PRESENTED ON
REMARK 106 *CONECT* RECORDS IN THIS ENTRY.
REMARK 200
REMARK 200 EXPERIMENTAL DETAILS
REMARK 200  EXPERIMENT TYPE                : X-RAY DIFFRACTION
REMARK 200  DATE OF DATA COLLECTION        : NULL
REMARK 200  TEMPERATURE          (KELVIN)  : 100.0
REMARK 200  PH                             : 7.40
REMARK 200  NUMBER OF CRYSTALS USED        : 2
REMARK 200
REMARK 200  SYNCHROTRON             (Y/N)  : Y
REMARK 200  RADIATION SOURCE               : ALS
REMARK 200  BEAMLINE                       : 5.0.2
REMARK 200  X-RAY GENERATOR MODEL          : NULL
REMARK 200  MONOCHROMATIC OR LAUE   (M/L)  : M
REMARK 200  WAVELENGTH OR RANGE      (A)   : 1.100
REMARK 200  MONOCHROMATOR                  : NULL
REMARK 200  OPTICS                         : NULL
REMARK 200
REMARK 200  DETECTOR TYPE                  : CCD
REMARK 200  DETECTOR MANUFACTURER          : ADSC QUANTUM 4
REMARK 200  INTENSITY-INTEGRATION SOFTWARE : DENZO
REMARK 200  DATA SCALING SOFTWARE          : SCALEPACK
REMARK 200
REMARK 200  NUMBER OF UNIQUE REFLECTIONS   : 73146
REMARK 200  RESOLUTION RANGE HIGH    (A)   : 7.000
REMARK 200  RESOLUTION RANGE LOW     (A)   : 250.000
REMARK 200  REJECTION CRITERIA  (SIGMA(I)) : 0.000
REMARK 200
REMARK 200 OVERALL.
REMARK 200  COMPLETENESS FOR RANGE    (%)  : 89.5
REMARK 200  DATA REDUNDANCY                : 3.600
REMARK 200  R MERGE                   (I)  : NULL
REMARK 200  R SYM                     (I)  : 8.80000
REMARK 200  <I/SIGMA(I)> FOR THE DATA SET  : NULL
REMARK 200
REMARK 200 IN THE HIGHEST RESOLUTION SHELL.
REMARK 200  HIGHEST RESOLUTION SHELL, RANGE HIGH (A) : NULL
REMARK 200  HIGHEST RESOLUTION SHELL, RANGE LOW  (A) : NULL
REMARK 200  COMPLETENESS FOR SHELL    (%)  : NULL
REMARK 200  DATA REDUNDANCY IN SHELL       : NULL
REMARK 200  R MERGE FOR SHELL         (I)  : NULL
REMARK 200  R SYM FOR SHELL           (I)  : NULL
REMARK 200  <I/SIGMA(I)> FOR SHELL         : NULL
REMARK 200
REMARK 200 DIFFRACTION PROTOCOL: SINGLE WAVELENGTH
REMARK 200 METHOD USED TO DETERMINE THE STRUCTURE: FOURIER SYNTHESIS
REMARK 200 SOFTWARE USED: CCP4
REMARK 200 STARTING MODEL: NULL
REMARK 200
REMARK 200 REMARK: NULL
REMARK 280
REMARK 280 CRYSTAL
REMARK 280 SOLVENT CONTENT, VS   (%): NULL
REMARK 280 MATTHEWS COEFFICIENT, VM (ANGSTROMS**3/DA): NULL
REMARK 280
REMARK 280 CRYSTALLIZATION CONDITIONS: 20 MM MGCL2, 100 MM KCL, 20 MM
REMARK 280  TRIS HCL, PH 7.4, VAPOR DIFFUSION AT 237K
REMARK 290
REMARK 290 CRYSTALLOGRAPHIC SYMMETRY
REMARK 290 SYMMETRY OPERATORS FOR SPACE GROUP: I 4 2 2
REMARK 290
REMARK 290       SYMOP   SYMMETRY
REMARK 290      NNNMMM   OPERATOR
REMARK 290        1555   X,Y,Z
REMARK 290        2555   -X,-Y,Z
```

```
REMARK 290       3555    -Y,X,Z
REMARK 290       4555    Y,-X,Z
REMARK 290       5555    -X,Y,-Z
REMARK 290       6555    X,-Y,-Z
REMARK 290       7555    Y,X,-Z
REMARK 290       8555    -Y,-X,-Z
REMARK 290       9555    1/2+X,1/2+Y,1/2+Z
REMARK 290      10555    1/2-X,1/2-Y,1/2+Z
REMARK 290      11555    1/2-Y,1/2+X,1/2+Z
REMARK 290      12555    1/2+Y,1/2-X,1/2+Z
REMARK 290      13555    1/2-X,1/2+Y,1/2-Z
REMARK 290      14555    1/2+X,1/2-Y,1/2-Z
REMARK 290      15555    1/2+Y,1/2+X,1/2-Z
REMARK 290      16555    1/2-Y,1/2-X,1/2-Z
REMARK 290
REMARK 290     WHERE NNN -> OPERATOR NUMBER
REMARK 290           MMM -> TRANSLATION VECTOR
REMARK 290
REMARK 290 CRYSTALLOGRAPHIC SYMMETRY TRANSFORMATIONS
REMARK 290 THE FOLLOWING TRANSFORMATIONS OPERATE ON THE ATOM/HETATM
REMARK 290 RECORDS IN THIS ENTRY TO PRODUCE CRYSTALLOGRAPHICALLY
REMARK 290 RELATED MOLECULES.
REMARK 290     SMTRY1   1  1.000000  0.000000  0.000000        0.00000
REMARK 290     SMTRY2   1  0.000000  1.000000  0.000000        0.00000
REMARK 290     SMTRY3   1  0.000000  0.000000  1.000000        0.00000
REMARK 290     SMTRY1   2 -1.000000  0.000000  0.000000        0.00000
REMARK 290     SMTRY2   2  0.000000 -1.000000  0.000000        0.00000
REMARK 290     SMTRY3   2  0.000000  0.000000  1.000000        0.00000
REMARK 290     SMTRY1   3  0.000000 -1.000000  0.000000        0.00000
REMARK 290     SMTRY2   3  1.000000  0.000000  0.000000        0.00000
REMARK 290     SMTRY3   3  0.000000  0.000000  1.000000        0.00000
REMARK 290     SMTRY1   4  0.000000  1.000000  0.000000        0.00000
REMARK 290     SMTRY2   4 -1.000000  0.000000  0.000000        0.00000
REMARK 290     SMTRY3   4  0.000000  0.000000  1.000000        0.00000
REMARK 290     SMTRY1   5 -1.000000  0.000000  0.000000        0.00000
REMARK 290     SMTRY2   5  0.000000  1.000000  0.000000        0.00000
REMARK 290     SMTRY3   5  0.000000  0.000000 -1.000000        0.00000
REMARK 290     SMTRY1   6  1.000000  0.000000  0.000000        0.00000
REMARK 290     SMTRY2   6  0.000000 -1.000000  0.000000        0.00000
REMARK 290     SMTRY3   6  0.000000  0.000000 -1.000000        0.00000
REMARK 290     SMTRY1   7  0.000000  1.000000  0.000000        0.00000
REMARK 290     SMTRY2   7  1.000000  0.000000  0.000000        0.00000
REMARK 290     SMTRY3   7  0.000000  0.000000 -1.000000        0.00000
REMARK 290     SMTRY1   8  0.000000 -1.000000  0.000000        0.00000
REMARK 290     SMTRY2   8 -1.000000  0.000000  0.000000        0.00000
REMARK 290     SMTRY3   8  0.000000  0.000000 -1.000000        0.00000
REMARK 290     SMTRY1   9  1.000000  0.000000  0.000000      253.60000
REMARK 290     SMTRY2   9  0.000000  1.000000  0.000000      253.60000
REMARK 290     SMTRY3   9  0.000000  0.000000  1.000000      401.83000
REMARK 290     SMTRY1  10 -1.000000  0.000000  0.000000      253.60000
REMARK 290     SMTRY2  10  0.000000 -1.000000  0.000000      253.60000
REMARK 290     SMTRY3  10  0.000000  0.000000  1.000000      401.83000
REMARK 290     SMTRY1  11  0.000000 -1.000000  0.000000      253.60000
REMARK 290     SMTRY2  11  1.000000  0.000000  0.000000      253.60000
REMARK 290     SMTRY3  11  0.000000  0.000000  1.000000      401.83000
REMARK 290     SMTRY1  12  0.000000  1.000000  0.000000      253.60000
REMARK 290     SMTRY2  12 -1.000000  0.000000  0.000000      253.60000
REMARK 290     SMTRY3  12  0.000000  0.000000  1.000000      401.83000
REMARK 290     SMTRY1  13 -1.000000  0.000000  0.000000      253.60000
REMARK 290     SMTRY2  13  0.000000  1.000000  0.000000      253.60000
REMARK 290     SMTRY3  13  0.000000  0.000000 -1.000000      401.83000
REMARK 290     SMTRY1  14  1.000000  0.000000  0.000000      253.60000
REMARK 290     SMTRY2  14  0.000000 -1.000000  0.000000      253.60000
REMARK 290     SMTRY3  14  0.000000  0.000000 -1.000000      401.83000
REMARK 290     SMTRY1  15  0.000000  1.000000  0.000000      253.60000
REMARK 290     SMTRY2  15  1.000000  0.000000  0.000000      253.60000
REMARK 290     SMTRY3  15  0.000000  0.000000 -1.000000      401.83000
REMARK 290     SMTRY1  16  0.000000 -1.000000  0.000000      253.60000
REMARK 290     SMTRY2  16 -1.000000  0.000000  0.000000      253.60000
REMARK 290     SMTRY3  16  0.000000  0.000000 -1.000000      401.83000
REMARK 290
REMARK 290 REMARK: NULL
REMARK 300
REMARK 300 BIOMOLECULE: 1
REMARK 300 THIS ENTRY CONTAINS THE CRYSTALLOGRAPHIC ASYMMETRIC UNIT
REMARK 300 WHICH CONSISTS OF 25CHAIN(S). SEE REMARK 350 FOR
REMARK 300 INFORMATION ON GENERATING THE BIOLOGICAL MOLECULE(S).
REMARK 350
REMARK 350 GENERATING THE BIOMOLECULE
REMARK 350 COORDINATES FOR A COMPLETE MULTIMER REPRESENTING THE KNOWN
REMARK 350 BIOLOGICALLY SIGNIFICANT OLIGOMERIZATION STATE OF THE
REMARK 350 MOLECULE CAN BE GENERATED BY APPLYING BIOMT TRANSFORMATIONS
REMARK 350 GIVEN BELOW.  BOTH NON-CRYSTALLOGRAPHIC AND
REMARK 350 CRYSTALLOGRAPHIC OPERATIONS ARE GIVEN.
REMARK 350
REMARK 350 BIOMOLECULE: 1
REMARK 350 APPLY THE FOLLOWING TO CHAINS: A, B, C, D, 1, E, F, G, H,
```

```
REMARK 350    I, J, K, L, M, N, O, P, Q, R, S, T, U, V, W, X
REMARK 350    BIOMT1   1  1.000000  0.000000  0.000000       0.00000
REMARK 350    BIOMT2   1  0.000000  1.000000  0.000000       0.00000
REMARK 350    BIOMT3   1  0.000000  0.000000  1.000000       0.00000
REMARK 400
REMARK 400 COMPOUND
REMARK 400
REMARK 400 THIS FILE, 1JGP, CONTAINS ONLY MOLECULES OF
REMARK 400 THE 30S RIBOSOMAL SUBUNIT, THREE TRNA MOLECULES
REMARK 400 AND AN MRNA FRAGMENT. THE CORRESPONDING 50S SUBUNIT
REMARK 400 IS IN THE PDB FILE 1GIY.
REMARK 400
REMARK 400 THE DIFFERENCE BETWEEN THIS FILE, 1JGP, AND 1GIX,
REMARK 400 BOTH 30S RIBOSOME SUBUNITS, IS IN THE MRNA MOLECULE.
REMARK 400 IN BOTH FILES, MRNA HAS CHAIN ID '1'
REMARK 400
REMARK 400 ==================================================
REMARK 400
REMARK 400     70S RIBOSOME PARTICLE ORIGINATES FROM THERMUS
REMARK 400 THERMOPHILUS. HOWEVER, INITIAL MODELS OF SOME OF
REMARK 400 ITS CONSTITUENTS WERE TAKEN FROM STRUCTURES FROM
REMARK 400 OTHER ORGANISMS AS INITIAL MODELS.
REMARK 400
REMARK 400 THE FOLLOWING LISTS CHAIN ID (AS IN THE COMPND
REMARK 400 RECORDS ABOVE), THE PDB ID OF THE STRUCTURAL
REMARK 400 MODEL AND THE SOURCE ORGANISM OF THAT MODEL FOR
REMARK 400 EACH BIOMOLECULE.
REMARK 400
REMARK 400 ==================================================
REMARK 400       30S SMALL SUBUNIT, PDB FILE 1JGP
REMARK 400 ==================================================
REMARK 400
REMARK 400 ===> 30S 16S RIBOSOMAL RNA, CHAIN A              <===
REMARK 400 1FJF       THERMUS THERMOPHILUS
REMARK 400 ===> TRNA(PHE), CHAIN B, C                       <===
REMARK 400 1EVV, 1FFZ      SACHROMYCES CEREVISIAE
REMARK 400 ===> TRNA(PHE), CHAIN D                          <===
REMARK 400 1GTR, 1B23, 3TRA NO SEQUENCE ENTRY
REMARK 400 ===> 30S RIBOSOMAL PROTEIN S2, CHAIN E           <===
REMARK 400 1FJF       THERMUS THERMOPHILUS
REMARK 400 ===> 30S RIBOSOMAL PROTEIN S3, CHAIN F           <===
REMARK 400 1FJF       THERMUS THERMOPHILUS
REMARK 400 ===> 30S RIBOSOMAL PROTEIN S4, CHAIN G           <===
REMARK 400 1FJF       THERMUS THERMOPHILUS
REMARK 400 ===> 30S RIBOSOMAL PROTEIN S5, CHAIN H           <===
REMARK 400 1FJF       THERMUS THERMOPHILUS
REMARK 400 ===> 30S RIBOSOMAL PROTEIN S6, CHAIN I           <===
REMARK 400 1FJF       THERMUS THERMOPHILUS
REMARK 400 ===> 30S RIBOSOMAL PROTEIN S7, CHAIN J           <===
REMARK 400 1FJF       THERMUS THERMOPHILUS
REMARK 400 ===> 30S RIBOSOMAL PROTEIN S8, CHAIN K           <===
REMARK 400 1FJF       THERMUS THERMOPHILUS
REMARK 400 ===> 30S RIBOSOMAL PROTEIN S9, CHAIN L           <===
REMARK 400 1FJF       THERMUS THERMOPHILUS
REMARK 400 ===> 30S RIBOSOMAL PROTEIN S10, CHAIN M          <===
REMARK 400 1FJF       THERMUS THERMOPHILUS
REMARK 400 ===> 30S RIBOSOMAL PROTEIN S11, CHAIN N          <===
REMARK 400 1FJF       THERMUS THERMOPHILUS
REMARK 400 ===> 30S RIBOSOMAL PROTEIN S12, CHAIN O          <===
REMARK 400 1FJF       THERMUS THERMOPHILUS
REMARK 400 ===> 30S RIBOSOMAL PROTEIN S13, CHAIN P          <===
REMARK 400 1FJF       THERMUS THERMOPHILUS
REMARK 400 ===> 30S RIBOSOMAL PROTEIN S14, CHAIN Q          <===
REMARK 400 1FJF       THERMUS THERMOPHILUS
REMARK 400 ===> 30S RIBOSOMAL PROTEIN S15, CHAIN R          <===
REMARK 400 1FJF       THERMUS THERMOPHILUS
REMARK 400 ===> 30S RIBOSOMAL PROTEIN S16, CHAIN S          <===
REMARK 400 1FJF       THERMUS THERMOPHILUS
REMARK 400 ===> 30S RIBOSOMAL PROTEIN S17, CHAIN T          <===
REMARK 400 1FJF       THERMUS THERMOPHILUS
REMARK 400 ===> 30S RIBOSOMAL PROTEIN S18, CHAIN U          <===
REMARK 400 1FJF       THERMUS THERMOPHILUS
REMARK 400 ===> 30S RIBOSOMAL PROTEIN S19, CHAIN V          <===
REMARK 400 1FJF       THERMUS THERMOPHILUS
REMARK 400 ===> 30S RIBOSOMAL PROTEIN S20, CHAIN W          <===
REMARK 400 1FJF       THERMUS THERMOPHILUS
REMARK 400 ===> 30S RIBOSOMAL PROTEIN THX, CHAIN X          <===
REMARK 400 1FJF       THERMUS THERMOPHILUS
REMARK 400
REMARK 400 ==================================================
REMARK 400       50S LARGE SUBUNIT, PDB FILE 1GIY
REMARK 400 ==================================================
REMARK 400
REMARK 400 ===> 50S 23S RIBOSOMAL RNA, CHAIN A              <===
REMARK 400 1FFK       THERMUS THERMOPHILUS
REMARK 400 ===> 50S 5S RIBOSOMAL RNA, CHAIN B               <===
REMARK 400 1FFK       THERMUS THERMOPHILUS
```

```
REMARK 400 ===> 50S RIBOSOMAL PROTEIN L1, CHAIN C            <===
REMARK 400 NO PUBLIC COORDINATES FOR THE MODEL
REMARK 400             THERMUS AQUATICUS
REMARK 400 ===> 50S RIBOSOMAL PROTEIN L2 , CHAIN D           <===
REMARK 400 1RL2 (RESIDUES  61-197), BACILLUS STEAROTHERMOPHILUS
REMARK 400 1FFK (RESIDUES 138-203), HALOARCULA MARISMORTUI
REMARK 400 ===> 50S RIBOSOMAL PROTEIN L3 , CHAIN E           <===
REMARK 400 1FFK       HALOARCULA MARISMORTUI (L3P)
REMARK 400 ===> 50S RIBOSOMAL PROTEIN L4, CHAIN F            <===
REMARK 400 1FFK       HALOARCULA MARISMORTUI (L4E)
REMARK 400 ===> 50S RIBOSOMAL PROTEIN L5, CHAIN G            <===
REMARK 400 1FFK       HALOARCULA MARISMORTUI (L5P)
REMARK 400 ===> 50S RIBOSOMAL PROTEIN L6, CHAIN H            <===
REMARK 400 1RL6       BACILLUS STEAROTHERMOPHILUS
REMARK 400 ===> 50S RIBOSOMAL PROTEIN L7/L12, CHAIN I, J     <===
REMARK 400 1DD3       THERMOTOGA MARITIMA
REMARK 400 ===> 50S RIBOSOMAL PROTEIN L9, CHAIN K            <===
REMARK 400 1DIV       BACILLUS STEAROTHERMOPHILUS
REMARK 400 ===> 50S RIBOSOMAL PROTEIN L11, CHAIN L           <===
REMARK 400 1MMS       THERMOTOGA MARITIMA
REMARK 400 ===> 50S RIBOSOMAL PROTEIN L13, CHAIN M           <===
REMARK 400 1FFK       HALOARCULA MARISMORTUI (L13P)
REMARK 400 ===> 50S RIBOSOMAL PROTEIN L14, CHAIN N           <===
REMARK 400 1WHI       BACILLUS STEAROTHERMOPHILUS
REMARK 400 ===> 50S RIBOSOMAL PROTEIN L15, CHAIN O           <===
REMARK 400 1FFK       HALOARCULA MARISMORTUI (L15P)
REMARK 400 ===> 50S RIBOSOMAL PROTEIN L16, CHAIN P           <===
REMARK 400 1FFK       NO SEQUENCE ENTRY FOUND
REMARK 400 ===> 50S RIBOSOMAL PROTEIN L18, CHAIN Q           <===
REMARK 400 1FFK       HALOARCULA MARISMORTUI (L18P)
REMARK 400 ===> 50S RIBOSOMAL PROTEIN L19, CHAIN R           <===
REMARK 400 1FFK       HALOARCULA MARISMORTUI (L24E)
REMARK 400 ===> 50S RIBOSOMAL PROTEIN L22, CHAIN S           <===
REMARK 400 1BXE       THERMUS THERMOPHILUS
REMARK 400 ===> 50S RIBOSOMAL PROTEIN L23, CHAIN T           <===
REMARK 400 1FFK       HALOARCULA MARISMORTUI (L23P)
REMARK 400 ===> 50S RIBOSOMAL PROTEIN L24, CHAIN U           <===
REMARK 400 1FFK       HALOARCULA MARISMORTUI (L24P)
REMARK 400 ===> 50S RIBOSOMAL PROTEIN L25, CHAIN V           <===
REMARK 400 1DFU       ESCHERICHIA COLI
REMARK 400 ===> 50S RIBOSOMAL PROTEIN L29, CHAIN W           <===
REMARK 400 1FFK       HALOARCULA MARISMORTUI (L29P)
REMARK 400 ===> 50S RIBOSOMAL PROTEIN L30, CHAIN X           <===
REMARK 400 1BXY       THERMUS THERMOPHILUS
REMARK 900
REMARK 900 RELATED ENTRIES
REMARK 900 RELATED ID: 1GIX    RELATED DB: PDB
REMARK 900 CRYSTAL STRUCTURE OF THE RIBOSOME AT 5.5 A RESOLUTION, 30S
REMARK 900 PART
REMARK 900 RELATED ID: 1GIY    RELATED DB: PDB
REMARK 900 CRYSTAL STRUCTURE OF THE RIBOSOME AT 5.5 A RESOLUTION, 50S
REMARK 900 PART
REMARK 900 RELATED ID: 1JGO    RELATED DB: PDB
REMARK 900 CRYSTAL STRUCTURE OF THE RIBOSOME AT 5.6 A RESOLUTION, 30S
REMARK 900 PART, DIFFERENT MRNA
REMARK 900 RELATED ID: 1JGQ    RELATED DB: PDB
REMARK 900 CRYSTAL STRUCTURE OF THE RIBOSOME AT 5.0 A RESOLUTION, 30S
REMARK 900 PART, DIFFERENT MRNA
DBREF  1JGP A    0  1544  GB      155076   M26924         646  2167
DBREF  1JGP B    1    76  GB      176479   M10263           1    76
DBREF  1JGP C    1    76  GB      176479   M10263           1    76
DBREF  1JGP E    1   256  EMBL  13446664 CAC35061           1   256
DBREF  1JGP F    1   239  SWS   13446666 RS4_THETH          1   239
DBREF  1JGP G    1   209  SWS     P80373 RS4_THETH          1   209
DBREF  1JGP H    1   162  SWS     P27152 RS5_THETH          1   162
DBREF  1JGP I    1   101  SWS     P23370 RS6_THETH          1   101
DBREF  1JGP J    1   156  SWS     P17291 RS7_THETH          1   156
DBREF  1JGP K    1   138  SWS     P24319 RS8_THETH          1   138
DBREF  1JGP L    1   128  EMBL  13446668 CAC35063           1   128
DBREF  1JGP M    1   105  SWS     P80375 RS10_THETH         1   105
DBREF  1JGP N    1   129  GB     4519421 BAA75547           1   129
DBREF  1JGP O    1   135  SWS     P17293 RS12_THETH         1   135
DBREF  1JGP P    1   126  GB     4519420 BAA75546           1   126
DBREF  1JGP Q    1    61  SWS     P24320 RS14_THETH         1    61
DBREF  1JGP R    1    89  SWS     P80378 RS15_THETH         1    89
DBREF  1JGP S    1    91  GB    12056104 CAC21226           1    91
DBREF  1JGP T    1   105  EMBL    673503 CAA85419           1   105
DBREF  1JGP U    1    88  GB     6739549 AAF27297           1    88
DBREF  1JGP V    1    93  SWS     P80381 RS19_THETH         1    93
DBREF  1JGP W    1   106  GB    11125386 CAC15067           1   106
DBREF  1JGP X    2    27  SWS     P32193 RSHX_THETH         1    26
SEQADV 1JGP 2MG B   10  GB     176479       G   10 TRNA MODIFICATION
SEQADV 1JGP H2U B   16  GB     176479       U   16 TRNA MODIFICATION
SEQADV 1JGP H2U B   17  GB     176479       U   17 TRNA MODIFICATION
SEQADV 1JGP M2G B   26  GB     176479       G   26 TRNA MODIFICATION
SEQADV 1JGP OMC B   32  GB     176479       C   32 TRNA MODIFICATION
SEQADV 1JGP OMG B   34  GB     176479       G   34 TRNA MODIFICATION
```

```
SEQADV 1JGP  YG  B   37 GB  176479     G   37 TRNA MODIFICATION
SEQADV 1JGP  PSU B   39 GB  176479     U   39 TRNA MODIFICATION
SEQADV 1JGP  5MC B   40 GB  176479     C   40 TRNA MODIFICATION
SEQADV 1JGP  7MG B   46 GB  176479     G   46 TRNA MODIFICATION
SEQADV 1JGP  5MC B   49 GB  176479     C   49 TRNA MODIFICATION
SEQADV 1JGP  5MU B   54 GB  176479     U   54 TRNA MODIFICATION
SEQADV 1JGP  PSU B   55 GB  176479     U   55 TRNA MODIFICATION
SEQADV 1JGP  1MA B   58 GB  176479     A   58 TRNA MODIFICATION
SEQADV 1JGP  2MG C   10 GB  176479     G   10 TRNA MODIFICATION
SEQADV 1JGP  H2U C   16 GB  176479     U   16 TRNA MODIFICATION
SEQADV 1JGP  H2U C   17 GB  176479     U   17 TRNA MODIFICATION
SEQADV 1JGP  M2G C   26 GB  176479     G   26 TRNA MODIFICATION
SEQADV 1JGP  OMC C   32 GB  176479     C   32 TRNA MODIFICATION
SEQADV 1JGP  OMG C   34 GB  176479     G   34 TRNA MODIFICATION
SEQADV 1JGP  YG  C   37 GB  176479     G   37 TRNA MODIFICATION
SEQADV 1JGP  PSU C   39 GB  176479     U   39 TRNA MODIFICATION
SEQADV 1JGP  5MC C   40 GB  176479     C   40 TRNA MODIFICATION
SEQADV 1JGP  7MG C   46 GB  176479     G   46 TRNA MODIFICATION
SEQADV 1JGP  5MC C   49 GB  176479     C   49 TRNA MODIFICATION
SEQADV 1JGP  5MU C   54 GB  176479     U   54 TRNA MODIFICATION
SEQADV 1JGP  PSU C   55 GB  176479     U   55 TRNA MODIFICATION
SEQADV 1JGP  1MA C   58 GB  176479     A   58 TRNA MODIFICATION

SEQRES  1 1  36   G   G   C   A   G   G   A   G   U   A   A
SEQRES  2 1  36   A   A   U   U   U   U   U   U   A   A   C   G
SEQRES  3 1  36   U   A   A   A   U   C   A   A   C   U

MODRES 1JGP 2MG B  10       2N-METHYLGUANOSINE-5'-MONOPHOSPHATE
MODRES 1JGP H2U B  16       5,6-DIHYDROURIDINE-5'-MONOPHOSPHATE
MODRES 1JGP H2U B  17       5,6-DIHYDROURIDINE-5'-MONOPHOSPHATE
MODRES 1JGP M2G B  26       N2-DIMETHYLGUANOSINE-5'-MONOPHOSPHATE
MODRES 1JGP OMC B  32       O2'-METHYLYCYTIDINE-5'-MONOPHOSPHATE
MODRES 1JGP OMG B  34       O2'-METHYLGUANOSINE-5'-MONOPHOSPHATE
MODRES 1JGP YG  B  37       WYBUTOSINE
MODRES 1JGP PSU B  39       PSEUDOURIDINE-5'-MONOPHOSPHATE
MODRES 1JGP 5MC B  40       5-METHYLCYTIDINE-5'-MONOPHOSPHATE
MODRES 1JGP 7MG B  46
MODRES 1JGP 5MC B  49       5-METHYLCYTIDINE-5'-MONOPHOSPHATE
MODRES 1JGP 5MU B  54       5-METHYLURIDINE 5'-MONOPHOSPHATE
MODRES 1JGP PSU B  55       PSEUDOURIDINE-5'-MONOPHOSPHATE
MODRES 1JGP 1MA B  58
MODRES 1JGP 2MG C  10       2N-METHYLGUANOSINE-5'-MONOPHOSPHATE
MODRES 1JGP H2U C  16       5,6-DIHYDROURIDINE-5'-MONOPHOSPHATE
MODRES 1JGP H2U C  17       5,6-DIHYDROURIDINE-5'-MONOPHOSPHATE
MODRES 1JGP M2G C  26       N2-DIMETHYLGUANOSINE-5'-MONOPHOSPHATE
MODRES 1JGP OMC C  32       O2'-METHYLYCYTIDINE-5'-MONOPHOSPHATE
MODRES 1JGP OMG C  34       O2'-METHYLGUANOSINE-5'-MONOPHOSPHATE
MODRES 1JGP YG  C  37       WYBUTOSINE
MODRES 1JGP PSU C  39       PSEUDOURIDINE-5'-MONOPHOSPHATE
MODRES 1JGP 5MC C  40       5-METHYLCYTIDINE-5'-MONOPHOSPHATE
MODRES 1JGP 7MG C  46
MODRES 1JGP 5MC C  49       5-METHYLCYTIDINE-5'-MONOPHOSPHATE
MODRES 1JGP 5MU C  54       5-METHYLURIDINE 5'-MONOPHOSPHATE
MODRES 1JGP PSU C  55       PSEUDOURIDINE-5'-MONOPHOSPHATE
MODRES 1JGP 1MA C  58
MODRES 1JGP 4SU D   8       4-THIOURIDINE-5'-MONOPHOSPHATE
MODRES 1JGP H2U D  20       5,6-DIHYDROURIDINE-5'-MONOPHOSPHATE
MODRES 1JGP H2U D  21       5,6-DIHYDROURIDINE-5'-MONOPHOSPHATE
MODRES 1JGP 5MC D  49       5-METHYLCYTIDINE-5'-MONOPHOSPHATE
MODRES 1JGP 5MU D  54       5-METHYLURIDINE 5'-MONOPHOSPHATE
MODRES 1JGP PSU D  55       PSEUDOURIDINE-5'-MONOPHOSPHATE
HET    2MG  B  10       24
HET    H2U  B  16       20
HET    H2U  B  17       20
HET    M2G  B  26       25
HET    OMC  B  32       21
HET    OMG  B  34       24
HET    YG   B  37       39
HET    PSU  B  39       20
HET    5MC  B  40       21
HET    7MG  B  46       24
HET    5MC  B  49       21
HET    5MU  B  54       21
HET    PSU  B  55       20
HET    1MA  B  58       23
HET    2MG  C  10       24
HET    H2U  C  16       20
HET    H2U  C  17       20
HET    M2G  C  26       25
HET    OMC  C  32       21
HET    OMG  C  34       24
HET    YG   C  37       39
HET    PSU  C  39       20
HET    5MC  C  40       21
HET    7MG  C  46       24
HET    5MC  C  49       21
HET    5MU  C  54       21
```

```
HET     PSU  C  55      20
HET     1MA  C  58      23
HET     4SU  D   8      20
HET     H2U  D  20      20
HET     H2U  D  21      20
HET     5MC  D  49      21
HET     5MU  D  54      21
HET     PSU  D  55      20
HETNAM       2MG  2N-METHYLGUANOSINE-5'-MONOPHOSPHATE
HETNAM       H2U  5,6-DIHYDROURIDINE-5'-MONOPHOSPHATE
HETNAM       M2G  N2-DIMETHYLGUANOSINE-5'-MONOPHOSPHATE
HETNAM       OMC  O2'-METHYLCYTIDINE-5'-MONOPHOSPHATE
HETNAM       OMG  O2'-METHYLGUANOSINE-5'-MONOPHOSPHATE
HETNAM       YG   WYBUTOSINE
HETNAM       PSU  PSEUDOURIDINE-5'-MONOPHOSPHATE
HETNAM       5MC  5-METHYLCYTIDINE-5'-MONOPHOSPHATE
HETNAM       7MG  7N-METHYL-8-HYDROGUANOSINE-5'-MONOPHOSPHATE
HETNAM       5MU  5-METHYLURIDINE 5'-MONOPHOSPHATE
HETNAM       1MA  6-HYDRO-1-METHYLADENOSINE-5'-MONOPHOSPHATE
HETNAM       4SU  4-THIOURIDINE-5'-MONOPHOSPHATE
HETSYN       YG   Y-BASE; 1H-IMIDAZO(1,2-ALPHA)PURINE-7-BUTANOIC ACID,4,
HETSYN   2   YG   9-DIHYDRO-ALPHA-((METHOXYCARBONYL)AMINO)-4,6-DIMETHYL-
HETSYN   3   YG   9-OXO-METHYL ESTER
FORMUL   2   2MG       2(C11 H16 N5 O8 P1)
FORMUL   2   H2U       6(C9 H15 N2 O9 P1)
FORMUL   2   M2G       2(C12 H18 N5 O8 P1)
FORMUL   2   OMC       2(C10 H16 N3 O8 P1)
FORMUL   2   OMG       2(C11 H16 N5 O8 P1)
FORMUL   2   YG        2(C21 H29 N6 O12 P1)
FORMUL   2   PSU       5(C9 H13 N2 O9 P1)
FORMUL   2   5MC       5(C10 H16 N3 O8 P1)
FORMUL   2   7MG       2(C11 H18 N5 O8 P1)
FORMUL   2   5MU       3(C10 H15 N2 O9 P1)
FORMUL   2   1MA       2(C11 H18 N5 O7 P1)
FORMUL   4   4SU        C9 H13 N2 O8 P1 S1
LINK         O3*   A  B   9                P   2MG B  10
LINK         O3* 2MG B  10                 P     C B  11
LINK         O3*   G  B  15                P   H2U B  16
LINK         O3* H2U B  16                 P   H2U B  17
LINK         O3* H2U B  17                 P     G B  18
LINK         O3*   C  B  25                P   M2G B  26
LINK         O3* M2G B  26                 P     C B  27
LINK         O3*   A  B  31                P   OMC B  32
LINK         O3* OMC B  32                 P     U B  33
LINK         O3*   U  B  33                P   OMG B  34
LINK         O3* OMG B  34                 P     A B  35
LINK         O3*   A  B  36                P    YG B  37
LINK         O3*  YG B  37                 P     A B  38
LINK         O3*   A  B  38                P   PSU B  39
LINK         O3* PSU B  39                 P   5MC B  40
LINK         O3* 5MC B  40                 P     U B  41
LINK         O3*   G  B  45                P   7MG B  46
LINK         O3* 7MG B  46                 P     U B  47
LINK         O3*   C  B  48                P   5MC B  49
LINK         O3* 5MC B  49                 P     U B  50
LINK         O3*   G  B  53                P   5MU B  54
LINK         O3* 5MU B  54                 P   PSU B  55
LINK         O3* PSU B  55                 P     C B  56
LINK         O3*   G  B  57                P   1MA B  58
LINK         O3* 1MA B  58                 P     U B  59
LINK         O3*   A  C   9                P   2MG C  10
LINK         O3* 2MG C  10                 P     C C  11
LINK         O3*   G  C  15                P   H2U C  16
LINK         O3* H2U C  16                 P   H2U C  17
LINK         O3* H2U C  17                 P     G C  18
LINK         O3* M2G C  26                 P     C C  27
LINK         O3*   A  C  31                P   OMC C  32
LINK         O3* OMC C  32                 P     U C  33
LINK         O3*   U  C  33                P   OMG C  34
LINK         O3* OMG C  34                 P     A C  35
LINK         O3*   A  C  36                P    YG C  37
LINK         O3*  YG C  37                 P     A C  38
LINK         O3*   A  C  38                P   PSU C  39
LINK         O3* PSU C  39                 P   5MC C  40
LINK         O3* 5MC C  40                 P     U C  41
LINK         O3*   G  C  45                P   7MG C  46
LINK         O3* 7MG C  46                 P     U C  47
LINK         O3*   C  C  48                P   5MC C  49
LINK         O3* 5MC C  49                 P     U C  50
LINK         O3*   G  C  53                P   5MU C  54
LINK         O3* 5MU C  54                 P   PSU C  55
LINK         O3* PSU C  55                 P     C C  56
LINK         O3*   G  C  57                P   1MA C  58
LINK         O3* 1MA C  58                 P     U C  59
LINK         O3* 4SU D   8                 P     A D   9
LINK         O3*   G  D  19                P   H2U D  20
LINK         O3* H2U D  20                 P   H2U D  21
```

```
LINK        O3*  H2U  D  21                P     A   D  22
LINK        O3*  5MC  D  49                P     G   D  50
LINK        O3*   G   D  53                P    5MU  D  54
LINK        O3*  5MU  D  54                P    PSU  D  55
LINK        O3*  PSU  D  55                P     C   D  56

CRYST1   507.200  507.200  803.660  90.00  90.00  90.00 I 4 2 2      32
ORIGX1      1.000000  0.000000  0.000000        0.00000
ORIGX2      0.000000  1.000000  0.000000        0.00000
ORIGX3      0.000000  0.000000  1.000000        0.00000
SCALE1      0.001972 -0.000000  0.000000        0.00000
SCALE2      0.000000  0.001972  0.000000        0.00000
SCALE3      0.000000  0.000000  0.001244        0.00000
ATOM   6398   P    G 1    1      30.267  55.984 290.530  1.00  0.00           P
ATOM   6399   P    G 1    2      25.835  58.943 289.316  1.00  0.00           P
ATOM   6400   P    C 1    3      21.497  59.562 288.241  1.00  0.00           P
ATOM   6401   P    A 1    4      17.507  58.928 289.509  1.00  0.00           P
ATOM   6402   P    A 1    5      13.282  58.665 293.068  1.00  0.00           P
ATOM   6403   P    G 1    6      10.612  61.237 296.929  1.00  0.00           P
ATOM   6404   P    G 1    7      10.047  64.944 301.531  1.00  0.00           P
ATOM   6405   P    A 1    8      12.353  69.634 304.279  1.00  0.00           P
ATOM   6406   P    G 1    9      16.376  73.641 304.829  1.00  0.00           P
ATOM   6407   P    G 1   10      21.109  76.064 302.978  1.00  0.00           P
ATOM   6408   P    U 1   11      24.950  79.364 299.517  1.00  0.00           P
ATOM   6409   P    A 1   12      23.270  83.350 293.009  1.00  0.00           P
ATOM   6410   P    A 1   13      19.013  87.856 290.519  1.00  0.00           P
ATOM   6411   P    A 1   14      15.794  90.173 284.650  1.00  0.00           P
ATOM   6412   P    A 1   15      14.404  94.510 279.074  1.00  0.00           P
ATOM   6413   P    U 1   16       9.248  97.344 283.458  1.00  0.00           P
ATOM   6414  O1P   U 1   16       9.069  96.805 284.825  1.00  0.00           O
ATOM   6415  O2P   U 1   16       8.764  96.486 282.352  1.00  0.00           O
ATOM   6416  O5*   U 1   16       8.563  98.786 283.356  1.00  0.00           O
ATOM   6417  C5*   U 1   16       8.892  99.785 284.340  1.00  0.00           C
ATOM   6418  C4*   U 1   16       8.176 101.082 284.019  1.00  0.00           C
ATOM   6419  O4*   U 1   16       8.690 101.605 282.760  1.00  0.00           O
ATOM   6420  C3*   U 1   16       6.669 100.973 283.785  1.00  0.00           C
ATOM   6421  O3*   U 1   16       5.945 100.960 285.007  1.00  0.00           O
ATOM   6422  C2*   U 1   16       6.386 102.217 282.931  1.00  0.00           C
ATOM   6423  O2*   U 1   16       6.374 103.379 283.714  1.00  0.00           O
ATOM   6424  C1*   U 1   16       7.645 102.259 282.058  1.00  0.00           C
ATOM   6425  N1    U 1   16       7.447 101.562 280.757  1.00  0.00           N
ATOM   6426  C2    U 1   16       6.790 102.256 279.768  1.00  0.00           C
ATOM   6427  O2    U 1   16       6.376 103.392 279.922  1.00  0.00           O
ATOM   6428  N3    U 1   16       6.626 101.579 278.577  1.00  0.00           N
ATOM   6429  C4    U 1   16       7.053 100.298 278.297  1.00  0.00           C
ATOM   6430  O4    U 1   16       6.848  99.795 277.191  1.00  0.00           O
ATOM   6431  C5    U 1   16       7.732  99.650 279.395  1.00  0.00           C
ATOM   6432  C6    U 1   16       7.906 100.286 280.566  1.00  0.00           C
ATOM   6433   P    U 1   17       4.601 100.397 285.104  1.00  0.00           P
ATOM   6434  O1P   U 1   17       4.143 100.343 286.511  1.00  0.00           O
ATOM   6435  O2P   U 1   17       4.691  99.097 284.400  1.00  0.00           O
ATOM   6436  O5*   U 1   17       3.664 101.392 284.273  1.00  0.00           O
ATOM   6437  C5*   U 1   17       3.435 102.720 284.779  1.00  0.00           C
ATOM   6438  C4*   U 1   17       2.570 103.502 283.809  1.00  0.00           C
ATOM   6439  O4*   U 1   17       3.309 103.691 282.568  1.00  0.00           O
ATOM   6440  C3*   U 1   17       1.276 102.817 283.368  1.00  0.00           C
ATOM   6441  O3*   U 1   17       0.237 102.990 284.321  1.00  0.00           O
ATOM   6442  C2*   U 1   17       0.987 103.511 282.030  1.00  0.00           C
ATOM   6443  O2*   U 1   17       0.465 104.798 282.226  1.00  0.00           O
ATOM   6444  C1*   U 1   17       2.407 103.666 281.474  1.00  0.00           C
ATOM   6445  N1    U 1   17       2.784 102.535 280.581  1.00  0.00           N
ATOM   6446  C2    U 1   17       2.319 102.575 279.288  1.00  0.00           C
ATOM   6447  O2    U 1   17       1.625 103.483 278.862  1.00  0.00           O
ATOM   6448  N3    U 1   17       2.690 101.512 278.491  1.00  0.00           N
ATOM   6449  C4    U 1   17       3.468 100.437 278.868  1.00  0.00           C
ATOM   6450  O4    U 1   17       3.734  99.542 278.063  1.00  0.00           O
ATOM   6451  C5    U 1   17       3.908 100.482 280.243  1.00  0.00           C
ATOM   6452  C6    U 1   17       3.562 101.508 281.041  1.00  0.00           C
ATOM   6453   P    U 1   18      -0.903 102.079 284.397  1.00  0.00           P
ATOM   6454  O1P   U 1   18      -1.744 102.370 285.578  1.00  0.00           O
ATOM   6455  O2P   U 1   18      -0.302 100.727 284.343  1.00  0.00           O
ATOM   6456  O5*   U 1   18      -1.745 102.343 283.061  1.00  0.00           O
ATOM   6457  C5*   U 1   18      -2.421 103.605 282.901  1.00  0.00           C
ATOM   6458  C4*   U 1   18      -3.104 103.659 281.550  1.00  0.00           C
ATOM   6459  O4*   U 1   18      -2.086 103.639 280.506  1.00  0.00           O
ATOM   6460  C3*   U 1   18      -4.004 102.471 281.209  1.00  0.00           C
ATOM   6461  O3*   U 1   18      -5.295 102.604 281.785  1.00  0.00           O
ATOM   6462  C2*   U 1   18      -4.022 102.512 279.674  1.00  0.00           C
ATOM   6463  O2*   U 1   18      -4.863 103.530 279.203  1.00  0.00           O
ATOM   6464  C1*   U 1   18      -2.578 102.930 279.380  1.00  0.00           C
ATOM   6465  N1    U 1   18      -1.693 101.756 279.141  1.00  0.00           N
ATOM   6466  C2    U 1   18      -1.736 101.184 277.893  1.00  0.00           C
ATOM   6467  O2    U 1   18      -2.457 101.595 277.000  1.00  0.00           O
ATOM   6468  N3    U 1   18      -0.902 100.100 277.708  1.00  0.00           N
ATOM   6469  C4    U 1   18      -0.050  99.553 278.646  1.00  0.00           C
ATOM   6470  O4    U 1   18       0.652  98.579 278.364  1.00  0.00           O
```

```
ATOM   6471  C5    U 1  18    -0.074 100.221 279.925  1.00  0.00           C
ATOM   6472  C6    U 1  18    -0.876 101.280 280.133  1.00  0.00           C
ATOM   6473  P     U 1  19    -6.296 102.388 282.881  1.00  0.00           P
ATOM   6474  O1P   U 1  19    -5.389 101.922 283.952  1.00  0.00           O
ATOM   6475  O2P   U 1  19    -6.993 101.331 282.113  1.00  0.00           O
ATOM   6476  O5*   U 1  19    -7.372 103.403 283.492  1.00  0.00           O
ATOM   6477  C5*   U 1  19    -6.912 104.515 284.283  1.00  0.00           C
ATOM   6478  C4*   U 1  19    -8.094 105.241 284.892  1.00  0.00           C
ATOM   6479  O4*   U 1  19    -8.519 106.297 283.982  1.00  0.00           O
ATOM   6480  C3*   U 1  19    -9.356 104.403 285.101  1.00  0.00           C
ATOM   6481  O3*   U 1  19    -9.295 103.647 286.301  1.00  0.00           O
ATOM   6482  C2*   U 1  19   -10.453 105.477 285.122  1.00  0.00           C
ATOM   6483  O2*   U 1  19   -10.473 106.160 286.345  1.00  0.00           O
ATOM   6484  C1*   U 1  19    -9.928 106.447 284.059  1.00  0.00           C
ATOM   6485  N1    U 1  19   -10.502 106.167 282.713  1.00  0.00           N
ATOM   6486  C2    U 1  19   -11.767 106.643 282.460  1.00  0.00           C
ATOM   6487  O2    U 1  19   -12.413 107.269 283.282  1.00  0.00           O
ATOM   6488  N3    U 1  19   -12.265 106.365 281.204  1.00  0.00           N
ATOM   6489  C4    U 1  19   -11.621 105.668 280.202  1.00  0.00           C
ATOM   6490  O4    U 1  19   -12.170 105.481 279.115  1.00  0.00           O
ATOM   6491  C5    U 1  19   -10.299 105.209 280.561  1.00  0.00           C
ATOM   6492  C6    U 1  19    -9.789 105.466 281.777  1.00  0.00           C
ATOM   6493  P     U 1  20   -10.100 102.445 286.499  1.00  0.00           P
ATOM   6494  O1P   U 1  20    -9.722 101.746 287.749  1.00  0.00           O
ATOM   6495  O2P   U 1  20    -9.931 101.672 285.246  1.00  0.00           O
ATOM   6496  O5*   U 1  20   -11.611 102.960 286.610  1.00  0.00           O
ATOM   6497  C5*   U 1  20   -12.000 103.736 287.759  1.00  0.00           C
ATOM   6498  C4*   U 1  20   -13.449 104.163 287.628  1.00  0.00           C
ATOM   6499  O4*   U 1  20   -13.571 105.073 286.497  1.00  0.00           O
ATOM   6500  C3*   U 1  20   -14.447 103.048 287.315  1.00  0.00           C
ATOM   6501  O3*   U 1  20   -14.836 102.343 288.485  1.00  0.00           O
ATOM   6502  C2*   U 1  20   -15.602 103.824 286.668  1.00  0.00           C
ATOM   6503  O2*   U 1  20   -16.365 104.498 287.633  1.00  0.00           O
ATOM   6504  C1*   U 1  20   -14.829 104.879 285.870  1.00  0.00           C
ATOM   6505  N1    U 1  20   -14.590 104.451 284.463  1.00  0.00           N
ATOM   6506  C2    U 1  20   -15.630 104.604 283.576  1.00  0.00           C
ATOM   6507  O2    U 1  20   -16.711 105.065 283.898  1.00  0.00           O
ATOM   6508  N3    U 1  20   -15.371 104.199 282.284  1.00  0.00           N
ATOM   6509  C4    U 1  20   -14.189 103.665 281.813  1.00  0.00           C
ATOM   6510  O4    U 1  20   -14.076 103.337 280.630  1.00  0.00           O
ATOM   6511  C5    U 1  20   -13.157 103.542 282.816  1.00  0.00           C
ATOM   6512  C6    U 1  20   -13.382 103.931 284.083  1.00  0.00           C
ATOM   6513  P     U 1  21   -15.369 100.984 288.429  1.00  0.00           P
ATOM   6514  O1P   U 1  21   -15.528 100.415 289.786  1.00  0.00           O
ATOM   6515  O2P   U 1  21   -14.449 100.261 287.523  1.00  0.00           O
ATOM   6516  O5*   U 1  21   -16.805 101.121 287.735  1.00  0.00           O
ATOM   6517  C5*   U 1  21   -17.862 101.795 288.445  1.00  0.00           C
ATOM   6518  C4*   U 1  21   -19.107 101.857 287.584  1.00  0.00           C
ATOM   6519  O4*   U 1  21   -18.835 102.696 286.424  1.00  0.00           O
ATOM   6520  C3*   U 1  21   -19.567 100.531 286.979  1.00  0.00           C
ATOM   6521  O3*   U 1  21   -20.332  99.767 287.901  1.00  0.00           O
ATOM   6522  C2*   U 1  21   -20.380 100.997 285.763  1.00  0.00           C
ATOM   6523  O2*   U 1  21   -21.639 101.479 286.148  1.00  0.00           O
ATOM   6524  C1*   U 1  21   -19.546 102.197 285.302  1.00  0.00           C
ATOM   6525  N1    U 1  21   -18.560 101.821 284.250  1.00  0.00           N
ATOM   6526  C2    U 1  21   -19.030 101.708 282.965  1.00  0.00           C
ATOM   6527  O2    U 1  21   -20.196 101.898 282.666  1.00  0.00           O
ATOM   6528  N3    U 1  21   -18.088 101.360 282.017  1.00  0.00           N
ATOM   6529  C4    U 1  21   -16.748 101.121 282.244  1.00  0.00           C
ATOM   6530  O4    U 1  21   -15.999 100.816 281.314  1.00  0.00           O
ATOM   6531  C5    U 1  21   -16.349 101.265 283.624  1.00  0.00           C
ATOM   6532  C6    U 1  21   -17.245 101.603 284.567  1.00  0.00           C
ATOM   6533  P     A 1  22   -20.867  98.259 284.192  1.00  0.00           P
ATOM   6534  P     A 1  23   -23.533  94.810 282.803  1.00  0.00           P
ATOM   6535  P     A 1  24   -24.587  91.038 281.755  1.00  0.00           P
ATOM   6536  P     C 1  25   -26.516  87.512 282.046  1.00  0.00           P
ATOM   6537  P     G 1  26   -29.863  83.982 285.539  1.00  0.00           P
ATOM   6538  P     U 1  27   -34.674  80.935 288.468  1.00  0.00           P
ATOM   6539  P     A 1  28   -36.170  79.126 288.839  1.00  0.00           P
ATOM   6540  P     A 1  29   -39.149  75.366 288.578  1.00  0.00           P
ATOM   6541  P     A 1  30   -43.068  70.687 290.226  1.00  0.00           P
ATOM   6542  P     U 1  31   -45.755  65.402 289.799  1.00  0.00           P
ATOM   6543  P     C 1  32   -45.612  57.683 288.158  1.00  0.00           P
TER    6544        C 1  32
```

File G ------------------------------------------------------------------------
Mol_Id: 4; Molecule: Messenger RNA Mf36; Chain: 1; Engineered: Yes;
Other_Details: 36 Nt Long Mrna Fragment. The Actual Sequence
Ggcaaggagguaaaa Aug Uuuaaacguaaaucuacu Modeled As Ggcaaggagguaaaa Uuu
Uuuaaacguaaaucuacu
COMPND   14 MOL_ID: 4;
COMPND   15 MOLECULE: MESSENGER RNA MF36;
COMPND   16 CHAIN: 1;
COMPND   17 ENGINEERED: YES;
COMPND   18 OTHER_DETAILS: 36 NT LONG MRNA FRAGMENT. THE ACTUAL
COMPND   19 SEQUENCE GGCAAGGAGGUAAAA AUG UUUAAACGUAAAUCUACU MODELED AS

```
COMPND   20 GGCAAGGAGGUAAAA UUU UUUAAACGUAAAUCUACU;
SOURCE   12 MOL_ID: 4;
SOURCE   13 SYNTHETIC: YES;
KEYWDS      RIBOSOME ASSEMBLY, PROTEIN SYNTHESIS, LIFE
EXPDTA      X-RAY DIFFRACTION
AUTHOR      G.Z.YUSUPOVA,M.M.YUSUPOV,J.H.D.CATE,H.F.NOLLER
REVDAT    2 14-SEP-01 1JGQ    1         JRNL
REVDAT    1 20-JUL-01 1JGQ    0
JRNL         AUTH   G.Z.YUSUPOVA,M.M.YUSUPOV,J.H.D.CATE,H.F.NOLLER
JRNL         TITL   THE PATH OF MESSENGER RNA THROUGH THE RIBOSOME
JRNL         REF    CELL (CAMBRIDGE,MASS.)        V. 106    233 2001
JRNL         REFN   ASTM CELLB5   US ISSN 0092-8674
REMARK   1
REMARK   2
REMARK   2 RESOLUTION. 5.00 ANGSTROMS.
REMARK   3
REMARK   3 REFINEMENT.
REMARK   3   PROGRAM     : O
REMARK   3   AUTHORS     : JONES,ZOU,COWAN,KJELDGAARD
REMARK   3
REMARK   3  DATA USED IN REFINEMENT.
REMARK   3   RESOLUTION RANGE HIGH (ANGSTROMS) : 5.00
REMARK   3   RESOLUTION RANGE LOW  (ANGSTROMS) : 250.00
REMARK   3   DATA CUTOFF            (SIGMA(F)) : NULL
REMARK   3   DATA CUTOFF HIGH         (ABS(F)) : NULL
REMARK   3   DATA CUTOFF LOW          (ABS(F)) : NULL
REMARK   3   COMPLETENESS (WORKING+TEST)   (%) : 95.3
REMARK   3   NUMBER OF REFLECTIONS             : 209044
REMARK   3
REMARK   3
REMARK   3  FIT TO DATA USED IN REFINEMENT.
REMARK   3   CROSS-VALIDATION METHOD          : NULL
REMARK   3   FREE R VALUE TEST SET SELECTION  : NULL
REMARK   3   R VALUE            (WORKING SET) : NULL
REMARK   3   FREE R VALUE                     : NULL
REMARK   3   FREE R VALUE TEST SET SIZE   (%) : NULL
REMARK   3   FREE R VALUE TEST SET COUNT      : NULL
REMARK   3   ESTIMATED ERROR OF FREE R VALUE  : NULL
REMARK   3
REMARK   3  FIT IN THE HIGHEST RESOLUTION BIN.
REMARK   3   TOTAL NUMBER OF BINS USED                : NULL
REMARK   3   BIN RESOLUTION RANGE HIGH       (A)      : NULL
REMARK   3   BIN RESOLUTION RANGE LOW        (A)      : NULL
REMARK   3   BIN COMPLETENESS (WORKING+TEST) (%)      : NULL
REMARK   3   REFLECTIONS IN BIN    (WORKING SET)      : NULL
REMARK   3   BIN R VALUE           (WORKING SET)      : NULL
REMARK   3   BIN FREE R VALUE                         : NULL
REMARK   3   BIN FREE R VALUE TEST SET SIZE  (%)      : NULL
REMARK   3   BIN FREE R VALUE TEST SET COUNT          : NULL
REMARK   3   ESTIMATED ERROR OF BIN FREE R VALUE      : NULL
REMARK   3
REMARK   3  NUMBER OF NON-HYDROGEN ATOMS USED IN REFINEMENT.
REMARK   3   PROTEIN ATOMS          : 2396
REMARK   3   NUCLEIC ACID ATOMS     : 6486
REMARK   3   HETEROGEN ATOMS        : 0
REMARK   3   SOLVENT ATOMS          : 0
REMARK   3
REMARK   3  B VALUES.
REMARK   3   FROM WILSON PLOT           (A**2) : NULL
REMARK   3   MEAN B VALUE      (OVERALL, A**2) : NULL
REMARK   3   OVERALL ANISOTROPIC B VALUE.
REMARK   3    B11 (A**2) : NULL
REMARK   3    B22 (A**2) : NULL
REMARK   3    B33 (A**2) : NULL
REMARK   3    B12 (A**2) : NULL
REMARK   3    B13 (A**2) : NULL
REMARK   3    B23 (A**2) : NULL
REMARK   3
REMARK   3  ESTIMATED COORDINATE ERROR.
REMARK   3   ESD FROM LUZZATI PLOT        (A) : NULL
REMARK   3   ESD FROM SIGMAA              (A) : NULL
REMARK   3   LOW RESOLUTION CUTOFF        (A) : NULL
REMARK   3
REMARK   3  CROSS-VALIDATED ESTIMATED COORDINATE ERROR.
REMARK   3   ESD FROM C-V LUZZATI PLOT    (A) : NULL
REMARK   3   ESD FROM C-V SIGMAA          (A) : NULL
REMARK   3
REMARK   3  RMS DEVIATIONS FROM IDEAL VALUES.
REMARK   3   BOND LENGTHS                 (A) : NULL
REMARK   3   BOND ANGLES            (DEGREES) : NULL
REMARK   3   DIHEDRAL ANGLES        (DEGREES) : NULL
REMARK   3   IMPROPER ANGLES        (DEGREES) : NULL
REMARK   3
REMARK   3  ISOTROPIC THERMAL MODEL : NULL
REMARK   3
REMARK   3  ISOTROPIC THERMAL FACTOR RESTRAINTS.    RMS      SIGMA
REMARK   3   MAIN-CHAIN BOND              (A**2) : NULL  ; NULL
```

```
REMARK   3  MAIN-CHAIN ANGLE            (A**2) : NULL  ; NULL
REMARK   3  SIDE-CHAIN BOND             (A**2) : NULL  ; NULL
REMARK   3  SIDE-CHAIN ANGLE            (A**2) : NULL  ; NULL
REMARK   3
REMARK   3
REMARK   3  NCS MODEL : NULL
REMARK   3
REMARK   3  NCS RESTRAINTS.                       RMS   SIGMA/WEIGHT
REMARK   3   GROUP  1  POSITIONAL         (A) : NULL  ; NULL
REMARK   3   GROUP  1  B-FACTOR        (A**2) : NULL  ; NULL
REMARK   3
REMARK   3  PARAMETER FILE  1  : NULL
REMARK   3  TOPOLOGY FILE   1  : NULL
REMARK   3
REMARK   3  OTHER REFINEMENT REMARKS: THE MODEL WAS BUILT BY MANUAL
REMARK   3  FITTING OF INDIVIDUAL MOLECULES INTO THE EXPERIMENTAL
REMARK   3  ELECTRON DENSITY USING THE GRAPHIC PROGRAM O.
REMARK   4
REMARK   4 1JGQ COMPLIES WITH FORMAT V. 2.3, 09-JULY-1998
REMARK 100
REMARK 100 THIS ENTRY HAS BEEN PROCESSED BY THE NUCLEIC ACID DATABASE
REMARK 100 ON 16-JUL-2001.
REMARK 100 THE NDB ID CODE IS RR0036.
REMARK 105
REMARK 105 THE PROTEIN DATA BANK HAS ADOPTED THE SACCHARIDE CHEMISTS
REMARK 105 NOMENCLATURE FOR ATOMS OF THE DEOXYRIBOSE/RIBOSE MOIETY
REMARK 105 RATHER THAN THAT OF THE NUCLEOSIDE CHEMISTS.  THE RING
REMARK 105 OXYGEN ATOM IS LABELLED O4* INSTEAD OF O1*.
REMARK 106
REMARK 106 ALL HYDROGEN BONDS BETWEEN BASE PAIRS NOT MENTIONED IN
REMARK 106 REMARKS 102 AND 103 FOLLOW THE CONVENTIONAL WATSON-CRICK
REMARK 106 HYDROGEN BONDING PATTERN. THEY HAVE NOT BEEN PRESENTED ON
REMARK 106 *CONECT* RECORDS IN THIS ENTRY.
REMARK 200
REMARK 200 EXPERIMENTAL DETAILS
REMARK 200  EXPERIMENT TYPE                : X-RAY DIFFRACTION
REMARK 200  DATE OF DATA COLLECTION        : NULL
REMARK 200  TEMPERATURE           (KELVIN) : 100.0
REMARK 200  PH                             : 7.40
REMARK 200  NUMBER OF CRYSTALS USED        : 2
REMARK 200
REMARK 200  SYNCHROTRON              (Y/N) : Y
REMARK 200  RADIATION SOURCE               : ALS
REMARK 200  BEAMLINE                       : 5.0.2
REMARK 200  X-RAY GENERATOR MODEL          : NULL
REMARK 200  MONOCHROMATIC OR LAUE    (M/L) : M
REMARK 200  WAVELENGTH OR RANGE        (A) : 1.100
REMARK 200  MONOCHROMATOR                  : NULL
REMARK 200  OPTICS                         : NULL
REMARK 200
REMARK 200  DETECTOR TYPE                  : CCD
REMARK 200  DETECTOR MANUFACTURER          : ADSC QUANTUM 4
REMARK 200  INTENSITY-INTEGRATION SOFTWARE : DENZO
REMARK 200  DATA SCALING SOFTWARE          : SCALEPACK
REMARK 200
REMARK 200  NUMBER OF UNIQUE REFLECTIONS   : 209044
REMARK 200  RESOLUTION RANGE HIGH      (A) : 5.000
REMARK 200  RESOLUTION RANGE LOW       (A) : 250.000
REMARK 200  REJECTION CRITERIA  (SIGMA(I)) : 0.000
REMARK 200
REMARK 200 OVERALL.
REMARK 200  COMPLETENESS FOR RANGE     (%) : 95.3
REMARK 200  DATA REDUNDANCY                : 2.800
REMARK 200  R MERGE                    (I) : NULL
REMARK 200  R SYM                      (I) : 9.40000
REMARK 200  <I/SIGMA(I)> FOR THE DATA SET  : NULL
REMARK 200
REMARK 200 IN THE HIGHEST RESOLUTION SHELL.
REMARK 200  HIGHEST RESOLUTION SHELL, RANGE HIGH (A) : NULL
REMARK 200  HIGHEST RESOLUTION SHELL, RANGE LOW  (A) : NULL
REMARK 200  COMPLETENESS FOR SHELL     (%) : NULL
REMARK 200  DATA REDUNDANCY IN SHELL       : NULL
REMARK 200  R MERGE FOR SHELL          (I) : NULL
REMARK 200  R SYM FOR SHELL            (I) : NULL
REMARK 200  <I/SIGMA(I)> FOR SHELL         : NULL
REMARK 200
REMARK 200 DIFFRACTION PROTOCOL: SINGLE WAVELENGTH
REMARK 200 METHOD USED TO DETERMINE THE STRUCTURE: FOURIER SYNTHESIS
REMARK 200 SOFTWARE USED: CCP4
REMARK 200 STARTING MODEL: NULL
REMARK 200
REMARK 200 REMARK: NULL
REMARK 280
REMARK 280 CRYSTAL
REMARK 280 SOLVENT CONTENT, VS   (%): NULL
REMARK 280 MATTHEWS COEFFICIENT, VM (ANGSTROMS**3/DA): NULL
REMARK 280
```

```
REMARK 280 CRYSTALLIZATION CONDITIONS: 20 MM MGCL2, 100 MM KCL, 20 MM
REMARK 280  TRIS HCL, PH 7.4, VAPOR DIFFUSION AT 237K
REMARK 290
REMARK 290 CRYSTALLOGRAPHIC SYMMETRY
REMARK 290 SYMMETRY OPERATORS FOR SPACE GROUP: I 4 2 2
REMARK 290
REMARK 290      SYMOP    SYMMETRY
REMARK 290      NNNMMM   OPERATOR
REMARK 290       1555    X,Y,Z
REMARK 290       2555    -X,-Y,Z
REMARK 290       3555    -Y,X,Z
REMARK 290       4555    Y,-X,Z
REMARK 290       5555    -X,Y,-Z
REMARK 290       6555    X,-Y,-Z
REMARK 290       7555    Y,X,-Z
REMARK 290       8555    -Y,-X,-Z
REMARK 290       9555    1/2+X,1/2+Y,1/2+Z
REMARK 290      10555    1/2-X,1/2-Y,1/2+Z
REMARK 290      11555    1/2-Y,1/2+X,1/2+Z
REMARK 290      12555    1/2+Y,1/2-X,1/2+Z
REMARK 290      13555    1/2-X,1/2+Y,1/2-Z
REMARK 290      14555    1/2+X,1/2-Y,1/2-Z
REMARK 290      15555    1/2+Y,1/2+X,1/2-Z
REMARK 290      16555    1/2-Y,1/2-X,1/2-Z
REMARK 290
REMARK 290     WHERE NNN -> OPERATOR NUMBER
REMARK 290           MMM -> TRANSLATION VECTOR
REMARK 290
REMARK 290 CRYSTALLOGRAPHIC SYMMETRY TRANSFORMATIONS
REMARK 290 THE FOLLOWING TRANSFORMATIONS OPERATE ON THE ATOM/HETATM
REMARK 290 RECORDS IN THIS ENTRY TO PRODUCE CRYSTALLOGRAPHICALLY
REMARK 290 RELATED MOLECULES.
REMARK 290     SMTRY1   1  1.000000  0.000000  0.000000        0.00000
REMARK 290     SMTRY2   1  0.000000  1.000000  0.000000        0.00000
REMARK 290     SMTRY3   1  0.000000  0.000000  1.000000        0.00000
REMARK 290     SMTRY1   2 -1.000000  0.000000  0.000000        0.00000
REMARK 290     SMTRY2   2  0.000000 -1.000000  0.000000        0.00000
REMARK 290     SMTRY3   2  0.000000  0.000000  1.000000        0.00000
REMARK 290     SMTRY1   3  0.000000 -1.000000  0.000000        0.00000
REMARK 290     SMTRY2   3  1.000000  0.000000  0.000000        0.00000
REMARK 290     SMTRY3   3  0.000000  0.000000  1.000000        0.00000
REMARK 290     SMTRY1   4  0.000000  1.000000  0.000000        0.00000
REMARK 290     SMTRY2   4 -1.000000  0.000000  0.000000        0.00000
REMARK 290     SMTRY3   4  0.000000  0.000000  1.000000        0.00000
REMARK 290     SMTRY1   5 -1.000000  0.000000  0.000000        0.00000
REMARK 290     SMTRY2   5  0.000000  1.000000  0.000000        0.00000
REMARK 290     SMTRY3   5  0.000000  0.000000 -1.000000        0.00000
REMARK 290     SMTRY1   6  1.000000  0.000000  0.000000        0.00000
REMARK 290     SMTRY2   6  0.000000 -1.000000  0.000000        0.00000
REMARK 290     SMTRY3   6  0.000000  0.000000 -1.000000        0.00000
REMARK 290     SMTRY1   7  0.000000  1.000000  0.000000        0.00000
REMARK 290     SMTRY2   7  1.000000  0.000000  0.000000        0.00000
REMARK 290     SMTRY3   7  0.000000  0.000000 -1.000000        0.00000
REMARK 290     SMTRY1   8  0.000000 -1.000000  0.000000        0.00000
REMARK 290     SMTRY2   8 -1.000000  0.000000  0.000000        0.00000
REMARK 290     SMTRY3   8  0.000000  0.000000 -1.000000        0.00000
REMARK 290     SMTRY1   9  1.000000  0.000000  0.000000      253.60000
REMARK 290     SMTRY2   9  0.000000  1.000000  0.000000      253.60000
REMARK 290     SMTRY3   9  0.000000  0.000000  1.000000      401.83000
REMARK 290     SMTRY1  10 -1.000000  0.000000  0.000000      253.60000
REMARK 290     SMTRY2  10  0.000000 -1.000000  0.000000      253.60000
REMARK 290     SMTRY3  10  0.000000  0.000000  1.000000      401.83000
REMARK 290     SMTRY1  11  0.000000 -1.000000  0.000000      253.60000
REMARK 290     SMTRY2  11  1.000000  0.000000  0.000000      253.60000
REMARK 290     SMTRY3  11  0.000000  0.000000  1.000000      401.83000
REMARK 290     SMTRY1  12  0.000000  1.000000  0.000000      253.60000
REMARK 290     SMTRY2  12 -1.000000  0.000000  0.000000      253.60000
REMARK 290     SMTRY3  12  0.000000  0.000000  1.000000      401.83000
REMARK 290     SMTRY1  13 -1.000000  0.000000  0.000000      253.60000
REMARK 290     SMTRY2  13  0.000000  1.000000  0.000000      253.60000
REMARK 290     SMTRY3  13  0.000000  0.000000 -1.000000      401.83000
REMARK 290     SMTRY1  14  1.000000  0.000000  0.000000      253.60000
REMARK 290     SMTRY2  14  0.000000 -1.000000  0.000000      253.60000
REMARK 290     SMTRY3  14  0.000000  0.000000 -1.000000      401.83000
REMARK 290     SMTRY1  15  0.000000  1.000000  0.000000      253.60000
REMARK 290     SMTRY2  15  1.000000  0.000000  0.000000      253.60000
REMARK 290     SMTRY3  15  0.000000  0.000000 -1.000000      401.83000
REMARK 290     SMTRY1  16  0.000000 -1.000000  0.000000      253.60000
REMARK 290     SMTRY2  16 -1.000000  0.000000  0.000000      253.60000
REMARK 290     SMTRY3  16  0.000000  0.000000 -1.000000      401.83000
REMARK 290
REMARK 290 REMARK: NULL
REMARK 300
REMARK 300 BIOMOLECULE: 1
REMARK 300 THIS ENTRY CONTAINS THE CRYSTALLOGRAPHIC ASYMMETRIC UNIT
REMARK 300 WHICH CONSISTS OF 25CHAIN(S). SEE REMARK 350 FOR
REMARK 300 INFORMATION ON GENERATING THE BIOLOGICAL MOLECULE(S).
```

```
REMARK 350
REMARK 350 GENERATING THE BIOMOLECULE
REMARK 350 COORDINATES FOR A COMPLETE MULTIMER REPRESENTING THE KNOWN
REMARK 350 BIOLOGICALLY SIGNIFICANT OLIGOMERIZATION STATE OF THE
REMARK 350 MOLECULE CAN BE GENERATED BY APPLYING BIOMT TRANSFORMATIONS
REMARK 350 GIVEN BELOW.  BOTH NON-CRYSTALLOGRAPHIC AND
REMARK 350 CRYSTALLOGRAPHIC OPERATIONS ARE GIVEN.
REMARK 350
REMARK 350 BIOMOLECULE: 1
REMARK 350 APPLY THE FOLLOWING TO CHAINS: A, B, C, D, 1, E, F, G, H,
REMARK 350 I, J, K, L, M, N, O, P, Q, R, S, T, U, V, W, X
REMARK 350   BIOMT1   1  1.000000  0.000000  0.000000        0.00000
REMARK 350   BIOMT2   1  0.000000  1.000000  0.000000        0.00000
REMARK 350   BIOMT3   1  0.000000  0.000000  1.000000        0.00000
REMARK 400
REMARK 400 COMPOUND
REMARK 400
REMARK 400 THIS FILE, 1JGQ, CONTAINS ONLY MOLECULES OF
REMARK 400 THE 30S RIBOSOMAL SUBUNIT, THREE TRNA MOLECULES
REMARK 400 AND AN MRNA FRAGMENT. THE CORRESPONDING 50S SUBUNIT
REMARK 400 IS IN THE PDB FILE 1GIY.
REMARK 400
REMARK 400 THE DIFFERENCE BETWEEN THIS FILE, 1JGQ, AND 1GIX,
REMARK 400 BOTH 30S RIBOSOME SUBUNITS, IS IN THE MRNA MOLECULE.
REMARK 400 IN BOTH FILES, MRNA HAS CHAIN ID '1'
REMARK 400
REMARK 400 =====================================================
REMARK 400
REMARK 400    70S RIBOSOME PARTICLE ORIGINATES FROM THERMUS
REMARK 400 THERMOPHILUS. HOWEVER, INITIAL MODELS OF SOME OF
REMARK 400 ITS CONSTITUENTS WERE TAKEN FROM STRUCTURES FROM
REMARK 400 OTHER ORGANISMS AS INITIAL MODELS.
REMARK 400
REMARK 400 THE FOLLOWING LISTS CHAIN ID (AS IN THE COMPND
REMARK 400 RECORDS ABOVE), THE PDB ID OF THE STRUCTURAL
REMARK 400 MODEL AND THE SOURCE ORGANISM OF THAT MODEL FOR
REMARK 400 EACH BIOMOLECULE.
REMARK 400
REMARK 400 =====================================================
REMARK 400       30S SMALL SUBUNIT, PDB FILE 1JGQ
REMARK 400 =====================================================
REMARK 400
REMARK 400 ===> 30S 16S RIBOSOMAL RNA, CHAIN A            <===
REMARK 400 1FJF        THERMUS THERMOPHILUS
REMARK 400 ===> TRNA(PHE), CHAIN B, C                     <===
REMARK 400 1EVV, 1FFZ       SACHROMYCES CEREVISIAE
REMARK 400 ===> TRNA(PHE), CHAIN D                        <===
REMARK 400 1GTR, 1B23, 3TRA NO SEQUENCE ENTRY
REMARK 400 ===> 30S RIBOSOMAL PROTEIN S2, CHAIN E         <===
REMARK 400 1FJF        THERMUS THERMOPHILUS
REMARK 400 ===> 30S RIBOSOMAL PROTEIN S3, CHAIN F         <===
REMARK 400 1FJF        THERMUS THERMOPHILUS
REMARK 400 ===> 30S RIBOSOMAL PROTEIN S4, CHAIN G         <===
REMARK 400 1FJF        THERMUS THERMOPHILUS
REMARK 400 ===> 30S RIBOSOMAL PROTEIN S5, CHAIN H         <===
REMARK 400 1FJF        THERMUS THERMOPHILUS
REMARK 400 ===> 30S RIBOSOMAL PROTEIN S6, CHAIN I         <===
REMARK 400 1FJF        THERMUS THERMOPHILUS
REMARK 400 ===> 30S RIBOSOMAL PROTEIN S7, CHAIN J         <===
REMARK 400 1FJF        THERMUS THERMOPHILUS
REMARK 400 ===> 30S RIBOSOMAL PROTEIN S8, CHAIN K         <===
REMARK 400 1FJF        THERMUS THERMOPHILUS
REMARK 400 ===> 30S RIBOSOMAL PROTEIN S9, CHAIN L         <===
REMARK 400 1FJF        THERMUS THERMOPHILUS
REMARK 400 ===> 30S RIBOSOMAL PROTEIN S10, CHAIN M        <===
REMARK 400 1FJF        THERMUS THERMOPHILUS
REMARK 400 ===> 30S RIBOSOMAL PROTEIN S11, CHAIN N        <===
REMARK 400 1FJF        THERMUS THERMOPHILUS
REMARK 400 ===> 30S RIBOSOMAL PROTEIN S12, CHAIN O        <===
REMARK 400 1FJF        THERMUS THERMOPHILUS
REMARK 400 ===> 30S RIBOSOMAL PROTEIN S13, CHAIN P        <===
REMARK 400 1FJF        THERMUS THERMOPHILUS
REMARK 400 ===> 30S RIBOSOMAL PROTEIN S14, CHAIN Q        <===
REMARK 400 1FJF        THERMUS THERMOPHILUS
REMARK 400 ===> 30S RIBOSOMAL PROTEIN S15, CHAIN R        <===
REMARK 400 1FJF        THERMUS THERMOPHILUS
REMARK 400 ===> 30S RIBOSOMAL PROTEIN S16, CHAIN S        <===
REMARK 400 1FJF        THERMUS THERMOPHILUS
REMARK 400 ===> 30S RIBOSOMAL PROTEIN S17, CHAIN T        <===
REMARK 400 1FJF        THERMUS THERMOPHILUS
REMARK 400 ===> 30S RIBOSOMAL PROTEIN S18, CHAIN U        <===
REMARK 400 1FJF        THERMUS THERMOPHILUS
REMARK 400 ===> 30S RIBOSOMAL PROTEIN S19, CHAIN V        <===
REMARK 400 1FJF        THERMUS THERMOPHILUS
REMARK 400 ===> 30S RIBOSOMAL PROTEIN S20, CHAIN W        <===
REMARK 400 1FJF        THERMUS THERMOPHILUS
REMARK 400 ===> 30S RIBOSOMAL PROTEIN THX, CHAIN X        <===
```

```
REMARK 400 1FJF      THERMUS THERMOPHILUS
REMARK 400
REMARK 400 =======================================================
REMARK 400      50S LARGE SUBUNIT, PDB FILE 1GIY
REMARK 400 =======================================================
REMARK 400
REMARK 400 ===> 50S 23S RIBOSOMAL RNA, CHAIN A            <===
REMARK 400 1FFK       THERMUS THERMOPHILUS
REMARK 400 ===> 50S 5S RIBOSOMAL RNA, CHAIN B             <===
REMARK 400 1FFK       THERMUS THERMOPHILUS
REMARK 400 ===> 50S RIBOSOMAL PROTEIN L1, CHAIN C         <===
REMARK 400 NO PUBLIC COORDINATES FOR THE MODEL
REMARK 400            THERMUS AQUATICUS
REMARK 400 ===> 50S RIBOSOMAL PROTEIN L2 , CHAIN D        <===
REMARK 400 1RL2 (RESIDUES   61-197), BACILLUS STEAROTHERMOPHILUS
REMARK 400 1FFK (RESIDUES 138-203), HALOARCULA MARISMORTUI
REMARK 400 ===> 50S RIBOSOMAL PROTEIN L3 , CHAIN E        <===
REMARK 400 1FFK       HALOARCULA MARISMORTUI (L3P)
REMARK 400 ===> 50S RIBOSOMAL PROTEIN L4, CHAIN F         <===
REMARK 400 1FFK       HALOARCULA MARISMORTUI (L4E)
REMARK 400 ===> 50S RIBOSOMAL PROTEIN L5, CHAIN G         <===
REMARK 400 1FFK       HALOARCULA MARISMORTUI (L5P)
REMARK 400 ===> 50S RIBOSOMAL PROTEIN L6, CHAIN H
REMARK 400 1RL6       BACILLUS STEAROTHERMOPHILUS
REMARK 400 ===> 50S RIBOSOMAL PROTEIN L7/L12, CHAIN I, J  <===
REMARK 400 1DD3       THERMOTOGA MARITIMA
REMARK 400 ===> 50S RIBOSOMAL PROTEIN L9, CHAIN K         <===
REMARK 400 1DIV       BACILLUS STEAROTHERMOPHILUS
REMARK 400 ===> 50S RIBOSOMAL PROTEIN L11, CHAIN L        <===
REMARK 400 1MMS       THERMOTOGA MARITIMA
REMARK 400 ===> 50S RIBOSOMAL PROTEIN L13, CHAIN M        <===
REMARK 400 1FFK       HALOARCULA MARISMORTUI (L13P)
REMARK 400 ===> 50S RIBOSOMAL PROTEIN L14, CHAIN N        <===
REMARK 400 1WHI       BACILLUS STEAROTHERMOPHILUS
REMARK 400 ===> 50S RIBOSOMAL PROTEIN L15, CHAIN O        <===
REMARK 400 1FFK       HALOARCULA MARISMORTUI (L15P)
REMARK 400 ===> 50S RIBOSOMAL PROTEIN L16, CHAIN P
REMARK 400 1FFK       NO SEQUENCE ENTRY FOUND
REMARK 400 ===> 50S RIBOSOMAL PROTEIN L18, CHAIN Q        <===
REMARK 400 1FFK       HALOARCULA MARISMORTUI (L18P)
REMARK 400 ===> 50S RIBOSOMAL PROTEIN L19, CHAIN R        <===
REMARK 400 1FFK       HALOARCULA MARISMORTUI (L24E)
REMARK 400 ===> 50S RIBOSOMAL PROTEIN L22, CHAIN S        <===
REMARK 400 1BXE       THERMUS THERMOPHILUS
REMARK 400 ===> 50S RIBOSOMAL PROTEIN L23, CHAIN T        <===
REMARK 400 1FFK       HALOARCULA MARISMORTUI (L23P)
REMARK 400 ===> 50S RIBOSOMAL PROTEIN L24, CHAIN U        <===
REMARK 400 1FFK       HALOARCULA MARISMORTUI (L24P)
REMARK 400 ===> 50S RIBOSOMAL PROTEIN L25, CHAIN V        <===
REMARK 400 1DFU       ESCHERICHIA COLI
REMARK 400 ===> 50S RIBOSOMAL PROTEIN L29, CHAIN W        <===
REMARK 400 1FFK       HALOARCULA MARISMORTUI (L29P)
REMARK 400 ===> 50S RIBOSOMAL PROTEIN L30, CHAIN X        <===
REMARK 400 1BXY       THERMUS THERMOPHILUS
REMARK 900
REMARK 900 RELATED ENTRIES
REMARK 900 RELATED ID: 1GIX   RELATED DB: PDB
REMARK 900 CRYSTAL STRUCTURE OF THE RIBOSOME AT 5.5 A RESOLUTION, 30S
REMARK 900 PART
REMARK 900 RELATED ID: 1GIY   RELATED DB: PDB
REMARK 900 CRYSTAL STRUCTURE OF THE RIBOSOME AT 5.5 A RESOLUTION, 50S
REMARK 900 PART
REMARK 900 RELATED ID: 1JGO   RELATED DB: PDB
REMARK 900 CRYSTAL STRUCTURE OF THE RIBOSOME AT 5.6 A RESOLUTION, 30S
REMARK 900 PART, DIFFERENT MRNA
REMARK 900 RELATED ID: 1JGP   RELATED DB: PDB
REMARK 900 CRYSTAL STRUCTURE OF THE RIBOSOME AT 7.0 A RESOLUTION, 30S
REMARK 900 PART, DIFFERENT MRNA
DBREF  1JGQ A    0  1544  GB      155076   M26924          646  2167
DBREF  1JGQ B    1    76  GB      176479   M10263            1    76
DBREF  1JGQ C    1    76  GB      176479   M10263            1    76
DBREF  1JGQ E    1   256  EMBL  13446664   CAC35061          1   256
DBREF  1JGQ F    1   239  SWS     13446666 RS4_THETH         1   239
DBREF  1JGQ G    1   209  SWS      P80373  RS4_THETH         1   209
DBREF  1JGQ H    1   162  SWS      P27152  RS5_THETH         1   162
DBREF  1JGQ I    1   101  SWS      P23370  RS6_THETH         1   101
DBREF  1JGQ J    1   156  SWS      P17291  RS7_THETH         1   156
DBREF  1JGQ K    1   138  SWS      P24319  RS8_THETH         1   138
DBREF  1JGQ L    1   128  EMBL  13446668   CAC35063          1   128
DBREF  1JGQ M    1   105  SWS      P80375  RS10_THETH        1   105
DBREF  1JGQ N    1   129  GB     4519421   BAA75547          1   129
DBREF  1JGQ O    1   135  SWS      P17293  RS12_THETH        1   135
DBREF  1JGQ P    1   126  GB     4519420   BAA75546          1   126
DBREF  1JGQ Q    1    61  SWS      P24320  RS14_THETH        1    61
DBREF  1JGQ R    1    89  SWS      P80378  RS15_THETH        1    89
DBREF  1JGQ S    1    91  GB    12056104   CAC21226          1    91
DBREF  1JGQ T    1   105  EMBL    673503   CAA85419          1   105
```

```
DBREF   1JGQ U    1    88  GB    6739549    AAF27297          1    88
DBREF   1JGQ V    1    93  SWS   P80381     RS19_THETH        1    93
DBREF   1JGQ W    1   106  GB    11125386   CAC15067          1   106
DBREF   1JGQ X    2    27  SWS   P32193     RSHX_THETH        1    26
SEQADV  1JGQ 2MG  B    10  GB    176479         G    10 TRNA MODIFICATION
SEQADV  1JGQ H2U  B    16  GB    176479         U    16 TRNA MODIFICATION
SEQADV  1JGQ H2U  B    17  GB    176479         U    17 TRNA MODIFICATION
SEQADV  1JGQ M2G  B    26  GB    176479         G    26 TRNA MODIFICATION
SEQADV  1JGQ OMC  B    32  GB    176479         C    32 TRNA MODIFICATION
SEQADV  1JGQ OMG  B    34  GB    176479         G    34 TRNA MODIFICATION
SEQADV  1JGQ  YG  B    37  GB    176479         G    37 TRNA MODIFICATION
SEQADV  1JGQ PSU  B    39  GB    176479         U    39 TRNA MODIFICATION
SEQADV  1JGQ 5MC  B    40  GB    176479         C    40 TRNA MODIFICATION
SEQADV  1JGQ 7MG  B    46  GB    176479         G    46 TRNA MODIFICATION
SEQADV  1JGQ 5MC  B    49  GB    176479         C    49 TRNA MODIFICATION
SEQADV  1JGQ 5MU  B    54  GB    176479         U    54 TRNA MODIFICATION
SEQADV  1JGQ PSU  B    55  GB    176479         U    55 TRNA MODIFICATION
SEQADV  1JGQ 1MA  B    58  GB    176479         A    58 TRNA MODIFICATION
SEQADV  1JGQ 2MG  C    10  GB    176479         G    10 TRNA MODIFICATION
SEQADV  1JGQ H2U  C    16  GB    176479         U    16 TRNA MODIFICATION
SEQADV  1JGQ H2U  C    17  GB    176479         U    17 TRNA MODIFICATION
SEQADV  1JGQ M2G  C    26  GB    176479         G    26 TRNA MODIFICATION
SEQADV  1JGQ OMC  C    32  GB    176479         C    32 TRNA MODIFICATION
SEQADV  1JGQ OMG  C    34  GB    176479         G    34 TRNA MODIFICATION
SEQADV  1JGQ  YG  C    37  GB    176479         G    37 TRNA MODIFICATION
SEQADV  1JGQ PSU  C    39  GB    176479         U    39 TRNA MODIFICATION
SEQADV  1JGQ 5MC  C    40  GB    176479         C    40 TRNA MODIFICATION
SEQADV  1JGQ 7MG  C    46  GB    176479         G    46 TRNA MODIFICATION
SEQADV  1JGQ 5MC  C    49  GB    176479         C    49 TRNA MODIFICATION
SEQADV  1JGQ 5MU  C    54  GB    176479         U    54 TRNA MODIFICATION
SEQADV  1JGQ PSU  C    55  GB    176479         U    55 TRNA MODIFICATION
SEQADV  1JGQ 1MA  C    58  GB    176479         A    58 TRNA MODIFICATION

SEQRES   1 1   36    G  G  C  A  G  A  G  G  U  A  A
SEQRES   2 1   36    A  A  U  U  U  U  A  A  A  C  G
SEQRES   3 1   36    U  A  A  A  U  C  U  A  C  U

MODRES  1JGQ 2MG  B    10       2N-METHYLGUANOSINE-5'-MONOPHOSPHATE
MODRES  1JGQ H2U  B    16       5,6-DIHYDROURIDINE-5'-MONOPHOSPHATE
MODRES  1JGQ H2U  B    17       5,6-DIHYDROURIDINE-5'-MONOPHOSPHATE
MODRES  1JGQ M2G  B    26       N2-DIMETHYLGUANOSINE-5'-MONOPHOSPHATE
MODRES  1JGQ OMC  B    32       O2'-METHYLCYTIDINE-5'-MONOPHOSPHATE
MODRES  1JGQ OMG  B    34       O2'-METHYLGUANOSINE-5'-MONOPHOSPHATE
MODRES  1JGQ  YG  B    37       WYBUTOSINE
MODRES  1JGQ PSU  B    39       PSEUDOURIDINE-5'-MONOPHOSPHATE
MODRES  1JGQ 5MC  B    40       5-METHYLCYTIDINE-5'-MONOPHOSPHATE
MODRES  1JGQ 7MG  B    46
MODRES  1JGQ 5MC  B    49       5-METHYLCYTIDINE-5'-MONOPHOSPHATE
MODRES  1JGQ 5MU  B    54       5-METHYLURIDINE 5'-MONOPHOSPHATE
MODRES  1JGQ PSU  B    55       PSEUDOURIDINE-5'-MONOPHOSPHATE
MODRES  1JGQ 1MA  B    58
MODRES  1JGQ 2MG  C    10       2N-METHYLGUANOSINE-5'-MONOPHOSPHATE
MODRES  1JGQ H2U  C    16       5,6-DIHYDROURIDINE-5'-MONOPHOSPHATE
MODRES  1JGQ H2U  C    17       5,6-DIHYDROURIDINE-5'-MONOPHOSPHATE
MODRES  1JGQ M2G  C    26       N2-DIMETHYLGUANOSINE-5'-MONOPHOSPHATE
MODRES  1JGQ OMC  C    32       O2'-METHYLCYTIDINE-5'-MONOPHOSPHATE
MODRES  1JGQ OMG  C    34       O2'-METHYLGUANOSINE-5'-MONOPHOSPHATE
MODRES  1JGQ  YG  C    37       WYBUTOSINE
MODRES  1JGQ PSU  C    39       PSEUDOURIDINE-5'-MONOPHOSPHATE
MODRES  1JGQ 5MC  C    40       5-METHYLCYTIDINE-5'-MONOPHOSPHATE
MODRES  1JGQ 7MG  C    46
MODRES  1JGQ 5MC  C    49       5-METHYLCYTIDINE-5'-MONOPHOSPHATE
MODRES  1JGQ 5MU  C    54       5-METHYLURIDINE 5'-MONOPHOSPHATE
MODRES  1JGQ PSU  C    55       PSEUDOURIDINE-5'-MONOPHOSPHATE
MODRES  1JGQ 1MA  C    58
MODRES  1JGQ 4SU  D     8       4-THIOURIDINE-5'-MONOPHOSPHATE
MODRES  1JGQ H2U  D    20       5,6-DIHYDROURIDINE-5'-MONOPHOSPHATE
MODRES  1JGQ H2U  D    21       5,6-DIHYDROURIDINE-5'-MONOPHOSPHATE
MODRES  1JGQ 5MC  D    49       5-METHYLCYTIDINE-5'-MONOPHOSPHATE
MODRES  1JGQ 5MU  D    54       5-METHYLURIDINE 5'-MONOPHOSPHATE
MODRES  1JGQ PSU  D    55       PSEUDOURIDINE-5'-MONOPHOSPHATE
HET     2MG  B  10       24
HET     H2U  B  16       20
HET     H2U  B  17       20
HET     M2G  B  26       25
HET     OMC  B  32       21
HET     OMG  B  34       24
HET      YG  B  37       39
HET     PSU  B  39       20
HET     5MC  B  40       21
HET     7MG  B  46       24
HET     5MC  B  49       21
HET     5MU  B  54       21
HET     PSU  B  55       20
HET     1MA  B  58       23
HET     2MG  C  10       24
HET     H2U  C  16       20
```

```
HET     H2U   C  17    20
HET     M2G   C  26    25
HET     OMC   C  32    21
HET     OMG   C  34    24
HET     YG    C  37    39
HET     PSU   C  39    20
HET     5MC   C  40    21
HET     7MG   C  46    24
HET     5MC   C  49    21
HET     5MU   C  54    21
HET     PSU   C  55    20
HET     1MA   C  58    23
HET     4SU   D   8    20
HET     H2U   D  20    20
HET     H2U   D  21    20
HET     5MC   D  49    21
HET     5MU   D  54    21
HET     PSU   D  55    20
HETNAM       2MG  2N-METHYLGUANOSINE-5'-MONOPHOSPHATE
HETNAM       H2U  5,6-DIHYDROURIDINE-5'-MONOPHOSPHATE
HETNAM       M2G  N2-DIMETHYLGUANOSINE-5'-MONOPHOSPHATE
HETNAM       OMC  O2'-METHYLCYTIDINE-5'-MONOPHOSPHATE
HETNAM       OMG  O2'-METHYLGUANOSINE-5'-MONOPHOSPHATE
HETNAM       YG   WYBUTOSINE
HETNAM       PSU  PSEUDOURIDINE-5'-MONOPHOSPHATE
HETNAM       5MC  5-METHYLCYTIDINE-5'-MONOPHOSPHATE
HETNAM       7MG  7N-METHYL-8-HYDROGUANOSINE-5'-MONOPHOSPHATE
HETNAM       5MU  5-METHYLURIDINE 5'-MONOPHOSPHATE
HETNAM       1MA  6-HYDRO-1-METHYLADENOSINE-5'-MONOPHOSPHATE
HETNAM       4SU  4-THIOURIDINE-5'-MONOPHOSPHATE
HETSYN       YG   Y-BASE; 1H-IMIDAZO(1,2-ALPHA)PURINE-7-BUTANOIC ACID,4,
HETSYN   2   YG   9-DIHYDRO-ALPHA-((METHOXYCARBONYL)AMINO)-4,6-DIMETHYL-
HETSYN   3   YG   9-OXO-METHYL ESTER
FORMUL   2   2MG      2(C11 H16 N5 O8 P1)
FORMUL   2   H2U      6(C9 H15 N2 O9 P1)
FORMUL   2   M2G      2(C12 H18 N5 O8 P1)
FORMUL   2   OMC      2(C10 H16 N3 O8 P1)
FORMUL   2   OMG      2(C11 H16 N5 O8 P1)
FORMUL   2   YG       2(C21 H29 N6 O12 P1)
FORMUL   2   PSU      5(C9 H13 N2 O9 P1)
FORMUL   2   5MC      5(C10 H16 N3 O8 P1)
FORMUL   2   7MG      2(C11 H18 N5 O8 P1)
FORMUL   2   5MU      3(C10 H15 N2 O9 P1)
FORMUL   2   1MA      2(C11 H18 N5 O7 P1)
FORMUL   4   4SU      C9 H13 N2 O8 P1 S1
LINK         O3*    A B    9              P    2MG B   10
LINK         O3*  2MG B   10              P      C B   11
LINK         O3*    G B   15              P    H2U B   16
LINK         O3*  H2U B   16              P    H2U B   17
LINK         O3*  H2U B   17              P      G B   18
LINK         O3*    C B   25              P    M2G B   26
LINK         O3*  M2G B   26              P      C B   27
LINK         O3*    A B   31              P    OMC B   32
LINK         O3*  OMC B   32              P      U B   33
LINK         O3*    U B   33              P    OMG B   34
LINK         O3*  OMG B   34              P      A B   35
LINK         O3*    A B   36              P     YG B   37
LINK         O3*   YG B   37              P      A B   38
LINK         O3*    A B   38              P    PSU B   39
LINK         O3*  PSU B   39              P    5MC B   40
LINK         O3*  5MC B   40              P      U B   41
LINK         O3*    G B   45              P    7MG B   46
LINK         O3*  7MG B   46              P      U B   47
LINK         O3*    C B   48              P    5MC B   49
LINK         O3*  5MC B   49              P      U B   50
LINK         O3*    G B   53              P    5MU B   54
LINK         O3*  5MU B   54              P    PSU B   55
LINK         O3*  PSU B   55              P      C B   56
LINK         O3*    G B   57              P    1MA B   58
LINK         O3*  1MA B   58              P      U B   59
LINK         O3*    A C    9              P    2MG C   10
LINK         O3*  2MG C   10              P      C C   11
LINK         O3*    G C   15              P    H2U C   16
LINK         O3*  H2U C   16              P    H2U C   17
LINK         O3*  H2U C   17              P      G C   18
LINK         O3*  M2G C   26              P      C C   27
LINK         O3*    A C   31              P    OMC C   32
LINK         O3*  OMC C   32              P      U C   33
LINK         O3*    U C   33              P    OMG C   34
LINK         O3*  OMG C   34              P      A C   35
LINK         O3*    A C   36              P     YG C   37
LINK         O3*   YG C   37              P      A C   38
LINK         O3*    A C   38              P    PSU C   39
LINK         O3*  PSU C   39              P    5MC C   40
LINK         O3*  5MC C   40              P      U C   41
LINK         O3*    G C   45              P    7MG C   46
LINK         O3*  7MG C   46              P      U C   47
```

```
LINK         O3*   C C  48              P   5MC C  49
LINK         O3* 5MC C  49              P     U C  50
LINK         O3*   G C  53              P   5MU C  54
LINK         O3* 5MU C  54              P   PSU C  55
LINK         O3* PSU C  55              P     C C  56
LINK         O3*   G C  57              P   1MA C  58
LINK         O3* 1MA C  58              P     U C  59
LINK         O3* 4SU D   8              P     A D   9
LINK         O3*   G D  19              P   H2U D  20
LINK         O3* H2U D  20              P   H2U D  21
LINK         O3* H2U D  21              P     A D  22
LINK         O3* 5MC D  49              P     G D  50
LINK         O3*   G D  53              P   5MU D  54
LINK         O3* 5MU D  54              P   PSU D  55
LINK         O3* PSU D  55              P     C D  56
CRYST1  507.200  507.200  803.660  90.00  90.00  90.00 I 4 2 2      32
ORIGX1     1.000000  0.000000  0.000000      0.00000
ORIGX2     0.000000  1.000000  0.000000      0.00000
ORIGX3     0.000000  0.000000  1.000000      0.00000
SCALE1     0.001972 -0.000000  0.000000      0.00000
SCALE2     0.000000  0.001972  0.000000      0.00000
SCALE3     0.000000  0.000000  0.001244      0.00000
ATOM     1  P     U A   1     -50.761  76.728 327.188  1.00  0.00           P
ATOM     2  P     U A   2     -50.827  73.756 332.171  1.00  0.00           P
ATOM     3  P     G A   3     -48.559  75.043 336.960  1.00  0.00           P
ATOM     4  P     U A   4     -43.808  73.431 332.621  1.00  0.00           P
ATOM     5  P     U A   5     -45.103  76.659 329.705  1.00  0.00           P
ATOM     6  P     G A   6     -44.719  80.005 327.215  1.00  0.00           P
ATOM     7  P     G A   7     -40.138  81.231 324.258  1.00  0.00           P
ATOM     8  P     A A   8     -38.842  81.559 319.106  1.00  0.00           P
ATOM     9  P     G A   9     -33.520  80.139 315.004  1.00  0.00           P
ATOM    10  P     A A  10     -32.835  81.728 308.951  1.00  0.00           P
ATOM    11  P     G A  11     -31.745  84.356 303.601  1.00  0.00           P
ATOM    12  P     U A  12     -29.194  88.147 300.052  1.00  0.00           P
ATOM    13  P     U A  13     -24.421  90.810 299.125  1.00  0.00           P
ATOM    14  P     U A  14     -19.617  92.341 297.880  1.00  0.00           P
ATOM    15  P     G A  15     -17.406  90.464 293.208  1.00  0.00           P
ATOM    16  P     A A  16     -20.868  85.834 293.212  1.00  0.00           P
ATOM    17  P     U A  17     -20.697  81.423 296.817  1.00  0.00           P
ATOM    18  P     C A  18     -20.059  79.360 301.966  1.00  0.00           P
ATOM    19  P     C A  19     -18.366  79.875 308.426  1.00  0.00           P
ATOM    20  P     U A  20     -18.024  83.254 312.572  1.00  0.00           P
ATOM    21  P     G A  21     -18.381  88.204 315.469  1.00  0.00           P
ATOM    22  P     G A  22     -21.444  93.683 315.000  1.00  0.00           P
ATOM    23  P     C A  23     -25.242  98.105 313.664  1.00  0.00           P
ATOM    24  P     U A  24     -30.594  99.347 311.733  1.00  0.00           P
ATOM    25  P     C A  25     -35.966  97.894 309.890  1.00  0.00           P
ATOM    26  P     A A  26     -40.356  94.929 309.945  1.00  0.00           P
ATOM    27  P     G A  27     -44.206  93.719 312.685  1.00  0.00           P
ATOM    28  P     G A  28     -46.833  95.377 316.896  1.00  0.00           P
ATOM    29  P     G A  29     -48.005  98.532 321.541  1.00  0.00           P
ATOM    30  P     U A  30     -47.706 103.855 324.531  1.00  0.00           P
ATOM    31  P     G A  31     -46.643 108.970 326.500  1.00  0.00           P
ATOM    32  P     A A  32     -50.015 112.703 324.128  1.00  0.00           P
ATOM    33  P     A A  33     -49.448 116.003 319.031  1.00  0.00           P
ATOM    34  P     C A  34     -48.783 118.853 313.782  1.00  0.00           P
ATOM    35  P     G A  35     -50.056 118.375 308.208  1.00  0.00           P
ATOM    36  P     C A  36     -53.160 116.665 303.946  1.00  0.00           P
ATOM    37  P     U A  37     -58.647 114.471 303.003  1.00  0.00           P
ATOM    38  P     G A  38     -62.916 113.471 304.778  1.00  0.00           P
ATOM    39  P     G A  39     -66.232 113.667 308.331  1.00  0.00           P
ATOM    40  P     C A  40     -69.587 112.075 313.927  1.00  0.00           P
ATOM    41  P     G A  41     -70.767 111.027 319.577  1.00  0.00           P
ATOM    42  P     G A  42     -70.263 108.726 325.300  1.00  0.00           P
ATOM    43  P     C A  43     -67.820 107.001 330.097  1.00  0.00           P
ATOM    44  P     G A  44     -62.785 106.603 333.510  1.00  0.00           P
ATOM    45  P     U A  45     -56.683 108.772 333.504  1.00  0.00           P
ATOM    46  P     G A  46     -52.512 112.853 331.528  1.00  0.00           P
ATOM    47  P     C A  47     -52.404 118.056 329.953  1.00  0.00           P
ATOM    48  P     C A  48     -46.522 119.671 330.790  1.00  0.00           P
ATOM    49  P     U A  49     -41.445 118.750 329.030  1.00  0.00           P
ATOM    50  P     A A  50     -37.348 124.347 327.786  1.00  0.00           P
ATOM    51  P     A A  51     -42.329 126.167 331.995  1.00  0.00           P
ATOM    52  P     G A  52     -37.609 128.074 334.232  1.00  0.00           P
ATOM    53  P     A A  53     -40.914 133.211 335.444  1.00  0.00           P
ATOM    54  P     C A  54     -44.561 137.419 335.965  1.00  0.00           P
ATOM    55  P     A A  55     -51.267 139.239 336.420  1.00  0.00           P
ATOM    56  P     U A  56     -55.342 142.281 336.837  1.00  0.00           P
ATOM    57  P     G A  57     -60.425 140.868 338.894  1.00  0.00           P
ATOM    58  P     C A  58     -63.855 137.381 341.923  1.00  0.00           P
ATOM    59  P     A A  59     -63.047 132.650 345.787  1.00  0.00           P
ATOM    60  P     A A  60     -60.712 127.894 348.416  1.00  0.00           P
ATOM    61  P     G A  61     -60.399 131.470 352.562  1.00  0.00           P
ATOM    62  P     U A  62     -66.421 130.094 355.310  1.00  0.00           P
ATOM    63  P     C A  63     -70.160 128.264 359.808  1.00  0.00           P
ATOM    64  P     G A  64     -72.625 130.575 364.248  1.00  0.00           P
ATOM    65  P     U A  65     -73.746 132.392 370.459  1.00  0.00           P
```

| | | | | | | | | | |
|---|---|---|---|---|---|---|---|---|---|
| ATOM | 66 | P | G | A | 66 | -68.691 | 129.704 | 372.272 | 1.00 0.00 | P |
| ATOM | 67 | P | C | A | 67 | -69.315 | 133.971 | 376.329 | 1.00 0.00 | P |
| ATOM | 68 | P | G | A | 68 | -69.755 | 139.550 | 377.233 | 1.00 0.00 | P |
| ATOM | 69 | P | G | A | 69 | -70.852 | 145.595 | 375.686 | 1.00 0.00 | P |
| ATOM | 70 | P | G | A | 73 | -71.274 | 148.756 | 368.867 | 1.00 0.00 | P |
| ATOM | 71 | P | C | A | 74 | -72.995 | 152.431 | 365.213 | 1.00 0.00 | P |
| ATOM | 72 | P | C | A | 75 | -76.845 | 153.289 | 360.856 | 1.00 0.00 | P |
| ATOM | 73 | P | G | A | 76 | -81.876 | 152.078 | 359.201 | 1.00 0.00 | P |
| ATOM | 74 | P | C | A | 77 | -87.087 | 149.039 | 360.827 | 1.00 0.00 | P |
| ATOM | 75 | P | G | A | 78 | -90.874 | 145.960 | 363.933 | 1.00 0.00 | P |
| ATOM | 76 | P | G | A | 79 | -93.599 | 144.674 | 368.689 | 1.00 0.00 | P |
| ATOM | 77 | P | G | A | 80 | -95.684 | 146.859 | 374.467 | 1.00 0.00 | P |
| ATOM | 78 | P | G | A | 81 | -94.829 | 151.955 | 378.536 | 1.00 0.00 | P |
| ATOM | 79 | P | U | A | 82 | -95.496 | 157.561 | 376.837 | 1.00 0.00 | P |
| ATOM | 80 | P | U | A | 84 | -94.636 | 159.374 | 372.662 | 1.00 0.00 | P |
| ATOM | 81 | P | U | A | 85 | -93.492 | 160.594 | 365.968 | 1.00 0.00 | P |
| ATOM | 82 | P | U | A | 86 | -88.267 | 160.063 | 363.625 | 1.00 0.00 | P |
| ATOM | 83 | P | A | A | 87 | -83.141 | 159.867 | 367.002 | 1.00 0.00 | P |
| ATOM | 84 | P | C | A | 88 | -79.605 | 158.113 | 370.962 | 1.00 0.00 | P |
| ATOM | 85 | P | U | A | 89 | -78.643 | 154.645 | 375.468 | 1.00 0.00 | P |
| ATOM | 86 | P | C | A | 90 | -78.783 | 149.187 | 378.201 | 1.00 0.00 | P |
| ATOM | 87 | P | C | A | 91 | -78.356 | 143.651 | 376.878 | 1.00 0.00 | P |
| ATOM | 88 | P | G | A | 92 | -79.318 | 138.685 | 373.949 | 1.00 0.00 | P |
| ATOM | 89 | P | U | A | 93 | -80.220 | 135.518 | 369.287 | 1.00 0.00 | P |
| ATOM | 90 | P | G | A | 95 | -79.859 | 135.300 | 363.444 | 1.00 0.00 | P |
| ATOM | 91 | P | G | A | 96 | -78.292 | 136.902 | 358.984 | 1.00 0.00 | P |
| ATOM | 92 | P | U | A | 97 | -74.998 | 139.429 | 356.894 | 1.00 0.00 | P |
| ATOM | 93 | P | C | A | 99 | -70.510 | 141.009 | 356.594 | 1.00 0.00 | P |
| ATOM | 94 | P | A | A | 101 | -65.605 | 141.646 | 357.633 | 1.00 0.00 | P |
| ATOM | 95 | P | G | A | 102 | -60.214 | 141.117 | 362.111 | 1.00 0.00 | P |
| ATOM | 96 | P | C | A | 103 | -57.423 | 141.338 | 366.680 | 1.00 0.00 | P |
| ATOM | 97 | P | G | A | 104 | -57.280 | 137.103 | 370.925 | 1.00 0.00 | P |
| ATOM | 98 | P | G | A | 105 | -57.280 | 131.445 | 371.867 | 1.00 0.00 | P |
| ATOM | 99 | P | C | A | 106 | -57.197 | 125.898 | 369.866 | 1.00 0.00 | P |
| ATOM | 100 | P | G | A | 107 | -56.384 | 122.359 | 366.367 | 1.00 0.00 | P |
| ATOM | 101 | P | G | A | 108 | -52.878 | 121.874 | 362.209 | 1.00 0.00 | P |
| ATOM | 102 | P | A | A | 109 | -48.965 | 123.600 | 358.462 | 1.00 0.00 | P |
| ATOM | 103 | P | C | A | 110 | -51.100 | 118.545 | 353.032 | 1.00 0.00 | P |
| ATOM | 104 | P | G | A | 111 | -52.502 | 116.515 | 350.592 | 1.00 0.00 | P |
| ATOM | 105 | P | G | A | 112 | -55.014 | 116.842 | 344.984 | 1.00 0.00 | P |
| ATOM | 106 | P | G | A | 113 | -51.598 | 117.739 | 341.724 | 1.00 0.00 | P |
| ATOM | 107 | P | U | A | 114 | -48.007 | 118.996 | 337.681 | 1.00 0.00 | P |
| ATOM | 108 | P | G | A | 115 | -42.506 | 118.659 | 335.544 | 1.00 0.00 | P |
| ATOM | 109 | P | A | A | 116 | -36.513 | 117.979 | 334.956 | 1.00 0.00 | P |
| ATOM | 110 | P | G | A | 117 | -31.822 | 119.629 | 336.220 | 1.00 0.00 | P |
| ATOM | 111 | P | U | A | 118 | -27.834 | 118.847 | 340.493 | 1.00 0.00 | P |
| ATOM | 112 | P | A | A | 119 | -25.960 | 114.340 | 343.606 | 1.00 0.00 | P |
| ATOM | 113 | P | A | A | 120 | -23.060 | 110.111 | 345.529 | 1.00 0.00 | P |
| ATOM | 114 | P | C | A | 121 | -24.913 | 108.630 | 351.393 | 1.00 0.00 | P |
| ATOM | 115 | P | G | A | 122 | -28.200 | 110.719 | 354.497 | 1.00 0.00 | P |
| ATOM | 116 | P | C | A | 123 | -33.674 | 110.648 | 352.558 | 1.00 0.00 | P |
| ATOM | 117 | P | G | A | 124 | -37.657 | 107.490 | 349.705 | 1.00 0.00 | P |
| ATOM | 118 | P | U | A | 125 | -40.108 | 102.381 | 349.357 | 1.00 0.00 | P |
| ATOM | 119 | P | G | A | 126 | -41.025 | 97.687 | 352.373 | 1.00 0.00 | P |
| ATOM | 120 | P | G | A | 127 | -40.347 | 94.658 | 357.820 | 1.00 0.00 | P |
| ATOM | 121 | P | G | A | 128 | -37.957 | 95.975 | 364.089 | 1.00 0.00 | P |
| ATOM | 122 | P | U | A | 129 | -35.618 | 97.557 | 369.012 | 1.00 0.00 | P |
| ATOM | 123 | P | G | A | 129A | -33.832 | 100.900 | 373.672 | 1.00 0.00 | P |
| ATOM | 124 | P | A | A | 130 | -28.899 | 103.362 | 375.714 | 1.00 0.00 | P |
| ATOM | 125 | P | C | A | 131 | -35.257 | 109.538 | 373.077 | 1.00 0.00 | P |
| ATOM | 126 | P | C | A | 132 | -43.337 | 111.068 | 373.969 | 1.00 0.00 | P |
| ATOM | 127 | P | U | A | 133 | -46.422 | 115.094 | 372.012 | 1.00 0.00 | P |
| ATOM | 128 | P | A | A | 134 | -51.513 | 115.453 | 369.891 | 1.00 0.00 | P |
| ATOM | 129 | P | C | A | 135 | -56.319 | 117.602 | 370.782 | 1.00 0.00 | P |
| ATOM | 130 | P | C | A | 136 | -61.367 | 115.908 | 370.029 | 1.00 0.00 | P |
| ATOM | 131 | P | C | A | 137 | -64.253 | 111.556 | 370.921 | 1.00 0.00 | P |
| ATOM | 132 | P | G | A | 138 | -65.444 | 107.190 | 374.087 | 1.00 0.00 | P |
| ATOM | 133 | P | G | A | 139 | -64.912 | 104.880 | 378.996 | 1.00 0.00 | P |
| ATOM | 134 | P | A | A | 140 | -63.269 | 105.048 | 384.622 | 1.00 0.00 | P |
| ATOM | 135 | P | A | A | 141 | -61.810 | 107.588 | 389.280 | 1.00 0.00 | P |
| ATOM | 136 | P | G | A | 142 | -61.599 | 113.233 | 391.794 | 1.00 0.00 | P |
| ATOM | 137 | P | A | A | 143 | -63.401 | 119.248 | 391.403 | 1.00 0.00 | P |
| ATOM | 138 | P | G | A | 144 | -64.849 | 126.010 | 393.092 | 1.00 0.00 | P |
| ATOM | 139 | P | G | A | 145 | -65.350 | 131.638 | 396.053 | 1.00 0.00 | P |
| ATOM | 140 | P | G | A | 146 | -63.391 | 137.317 | 395.982 | 1.00 0.00 | P |
| ATOM | 141 | P | G | A | 147 | -60.321 | 142.291 | 393.848 | 1.00 0.00 | P |
| ATOM | 142 | P | G | A | 148 | -57.485 | 145.866 | 389.879 | 1.00 0.00 | P |
| ATOM | 143 | P | A | A | 149 | -55.523 | 148.022 | 384.667 | 1.00 0.00 | P |
| ATOM | 144 | P | C | A | 150 | -53.870 | 149.099 | 378.785 | 1.00 0.00 | P |
| ATOM | 145 | P | A | A | 151 | -54.501 | 148.999 | 372.738 | 1.00 0.00 | P |
| ATOM | 146 | P | A | A | 152 | -58.815 | 149.502 | 367.709 | 1.00 0.00 | P |
| ATOM | 147 | P | C | A | 153 | -63.871 | 150.392 | 365.964 | 1.00 0.00 | P |
| ATOM | 148 | P | C | A | 154 | -66.099 | 155.517 | 367.187 | 1.00 0.00 | P |
| ATOM | 149 | P | C | A | 155 | -64.657 | 160.716 | 368.062 | 1.00 0.00 | P |
| ATOM | 150 | P | G | A | 156 | -60.578 | 164.781 | 367.051 | 1.00 0.00 | P |
| ATOM | 151 | P | G | A | 157 | -55.831 | 166.840 | 364.623 | 1.00 0.00 | P |
| ATOM | 152 | P | G | A | 158 | -51.086 | 165.994 | 360.719 | 1.00 0.00 | P |

| | | | | | | | | | |
|---|---|---|---|---|---|---|---|---|---|
| ATOM | 153 | P | G | A | 159 | -47.899 164.410 356.470 | 1.00 | 0.00 | P |
| ATOM | 154 | P | A | A | 160 | -48.310 162.664 351.427 | 1.00 | 0.00 | P |
| ATOM | 155 | P | A | A | 161 | -53.449 159.249 351.533 | 1.00 | 0.00 | P |
| ATOM | 156 | P | A | A | 162 | -54.746 153.342 351.749 | 1.00 | 0.00 | P |
| ATOM | 157 | P | C | A | 163 | -54.034 148.587 354.582 | 1.00 | 0.00 | P |
| ATOM | 158 | P | U | A | 164 | -50.483 149.144 360.342 | 1.00 | 0.00 | P |
| ATOM | 159 | P | C | A | 165 | -47.591 151.818 364.917 | 1.00 | 0.00 | P |
| ATOM | 160 | P | G | A | 166 | -47.131 154.458 369.784 | 1.00 | 0.00 | P |
| ATOM | 161 | P | G | A | 167 | -49.367 156.801 374.696 | 1.00 | 0.00 | P |
| ATOM | 162 | P | G | A | 168 | -53.268 157.454 378.628 | 1.00 | 0.00 | P |
| ATOM | 163 | P | C | A | 169 | -58.221 155.396 381.237 | 1.00 | 0.00 | P |
| ATOM | 164 | P | U | A | 170 | -62.068 151.668 382.606 | 1.00 | 0.00 | P |
| ATOM | 165 | P | A | A | 171 | -64.007 145.977 382.652 | 1.00 | 0.00 | P |
| ATOM | 166 | P | A | A | 172 | -64.976 140.600 383.046 | 1.00 | 0.00 | P |
| ATOM | 167 | P | U | A | 173 | -63.487 134.707 382.394 | 1.00 | 0.00 | P |
| ATOM | 168 | P | C | A | 174 | -59.449 132.335 379.266 | 1.00 | 0.00 | P |
| ATOM | 169 | P | C | A | 175 | -54.677 133.489 378.871 | 1.00 | 0.00 | P |
| ATOM | 170 | P | C | A | 176 | -50.557 134.128 382.607 | 1.00 | 0.00 | P |
| ATOM | 171 | P | C | A | 177 | -48.220 134.581 388.210 | 1.00 | 0.00 | P |
| ATOM | 172 | P | C | A | 178 | -47.861 133.616 393.961 | 1.00 | 0.00 | P |
| ATOM | 173 | P | A | A | 179 | -48.246 130.099 397.018 | 1.00 | 0.00 | P |
| ATOM | 174 | P | U | A | 180 | -51.198 125.527 399.537 | 1.00 | 0.00 | P |
| ATOM | 175 | P | G | A | 181 | -52.753 120.277 399.254 | 1.00 | 0.00 | P |
| ATOM | 176 | P | U | A | 182 | -51.630 114.723 395.983 | 1.00 | 0.00 | P |
| ATOM | 177 | P | G | A | 183 | -52.018 110.674 394.176 | 1.00 | 0.00 | P |
| ATOM | 178 | P | G | A | 184 | -47.302 110.491 389.154 | 1.00 | 0.00 | P |
| ATOM | 179 | P | A | A | 185 | -42.585 112.628 385.996 | 1.00 | 0.00 | P |
| ATOM | 180 | P | C | A | 186 | -37.507 114.881 385.255 | 1.00 | 0.00 | P |
| ATOM | 181 | P | C | A | 186A | -32.374 115.299 387.678 | 1.00 | 0.00 | P |
| ATOM | 182 | P | C | A | 186B | -28.219 114.239 391.156 | 1.00 | 0.00 | P |
| ATOM | 183 | P | G | A | 186C | -26.682 110.177 395.220 | 1.00 | 0.00 | P |
| ATOM | 184 | P | C | A | 186D | -27.157 104.958 397.289 | 1.00 | 0.00 | P |
| ATOM | 185 | P | C | A | 186E | -29.700 99.611 396.538 | 1.00 | 0.00 | P |
| ATOM | 186 | P | C | A | 186F | -32.074 95.205 394.032 | 1.00 | 0.00 | P |
| ATOM | 187 | P | C | A | 187 | -34.029 92.385 389.009 | 1.00 | 0.00 | P |
| ATOM | 188 | P | U | A | 188 | -33.126 93.236 382.891 | 1.00 | 0.00 | P |
| ATOM | 189 | P | U | A | 189 | -30.261 98.498 378.579 | 1.00 | 0.00 | P |
| ATOM | 190 | P | G | A | 190 | -28.965 104.596 381.873 | 1.00 | 0.00 | P |
| ATOM | 191 | P | G | A | 191A | -35.407 106.600 381.220 | 1.00 | 0.00 | P |
| ATOM | 192 | P | G | A | 191B | -40.142 104.812 382.379 | 1.00 | 0.00 | P |
| ATOM | 193 | P | G | A | 191C | -43.381 104.251 387.443 | 1.00 | 0.00 | P |
| ATOM | 194 | P | U | A | 191D | -44.355 104.613 393.324 | 1.00 | 0.00 | P |
| ATOM | 195 | P | G | A | 191E | -43.322 106.992 398.529 | 1.00 | 0.00 | P |
| ATOM | 196 | P | U | A | 191F | -42.053 111.207 402.048 | 1.00 | 0.00 | P |
| ATOM | 197 | P | G | A | 191 | -40.555 116.843 403.029 | 1.00 | 0.00 | P |
| ATOM | 198 | P | U | A | 192 | -39.947 121.898 400.873 | 1.00 | 0.00 | P |
| ATOM | 199 | P | C | A | 193 | -41.029 125.788 396.520 | 1.00 | 0.00 | P |
| ATOM | 200 | P | C | A | 194 | -43.899 127.021 391.748 | 1.00 | 0.00 | P |
| ATOM | 201 | P | A | A | 195 | -48.349 127.481 388.624 | 1.00 | 0.00 | P |
| ATOM | 202 | P | A | A | 196 | -53.005 128.100 386.319 | 1.00 | 0.00 | P |
| ATOM | 203 | P | A | A | 197 | -57.722 130.160 383.506 | 1.00 | 0.00 | P |
| ATOM | 204 | P | G | A | 198 | -63.367 130.288 384.699 | 1.00 | 0.00 | P |
| ATOM | 205 | P | G | A | 199 | -69.094 132.765 381.443 | 1.00 | 0.00 | P |
| ATOM | 206 | P | G | A | 200 | -74.012 132.385 377.988 | 1.00 | 0.00 | P |
| ATOM | 207 | P | C | A | 201 | -79.174 130.483 376.350 | 1.00 | 0.00 | P |
| ATOM | 208 | P | U | A | 208 | -84.731 127.115 377.305 | 1.00 | 0.00 | P |
| ATOM | 209 | P | U | A | 209 | -85.124 124.268 382.124 | 1.00 | 0.00 | P |
| ATOM | 210 | P | U | A | 210 | -82.959 123.041 387.085 | 1.00 | 0.00 | P |
| ATOM | 211 | P | G | A | 216 | -80.916 117.871 390.067 | 1.00 | 0.00 | P |
| ATOM | 212 | P | C | A | 217 | -76.360 115.166 385.452 | 1.00 | 0.00 | P |
| ATOM | 213 | P | C | A | 218 | -74.257 115.351 379.165 | 1.00 | 0.00 | P |
| ATOM | 214 | P | C | A | 219 | -71.703 117.322 374.626 | 1.00 | 0.00 | P |
| ATOM | 215 | P | G | A | 220 | -66.698 119.633 372.562 | 1.00 | 0.00 | P |
| ATOM | 216 | P | C | A | 221 | -60.915 121.102 375.326 | 1.00 | 0.00 | P |
| ATOM | 217 | P | U | A | 222 | -56.228 121.717 378.155 | 1.00 | 0.00 | P |
| ATOM | 218 | P | U | A | 223 | -52.067 119.556 380.727 | 1.00 | 0.00 | P |
| ATOM | 219 | P | C | A | 224 | -49.089 114.906 381.554 | 1.00 | 0.00 | P |
| ATOM | 220 | P | C | A | 225 | -48.130 109.130 380.855 | 1.00 | 0.00 | P |
| ATOM | 221 | P | G | A | 226 | -48.789 103.881 378.343 | 1.00 | 0.00 | P |
| ATOM | 222 | P | G | A | 227 | -51.095 101.376 373.357 | 1.00 | 0.00 | P |
| ATOM | 223 | P | A | A | 228 | -53.111 100.436 369.326 | 1.00 | 0.00 | P |
| ATOM | 224 | P | U | A | 229 | -53.591 103.122 364.428 | 1.00 | 0.00 | P |
| ATOM | 225 | P | G | A | 230 | -51.939 105.167 360.376 | 1.00 | 0.00 | P |
| ATOM | 226 | P | G | A | 231 | -47.520 107.753 357.819 | 1.00 | 0.00 | P |
| ATOM | 227 | P | G | A | 232 | -37.004 113.058 360.229 | 1.00 | 0.00 | P |
| ATOM | 228 | P | C | A | 233 | -31.524 112.618 361.201 | 1.00 | 0.00 | P |
| ATOM | 229 | P | C | A | 234 | -27.584 108.491 361.498 | 1.00 | 0.00 | P |
| ATOM | 230 | P | C | A | 235 | -25.211 103.596 360.447 | 1.00 | 0.00 | P |
| ATOM | 231 | P | G | A | 236 | -24.795 98.296 357.470 | 1.00 | 0.00 | P |
| ATOM | 232 | P | C | A | 237 | -24.620 94.910 353.360 | 1.00 | 0.00 | P |
| ATOM | 233 | P | G | A | 238 | -25.716 95.181 347.703 | 1.00 | 0.00 | P |
| ATOM | 234 | P | U | A | 239 | -26.273 98.182 342.857 | 1.00 | 0.00 | P |
| ATOM | 235 | P | C | A | 240 | -26.809 101.782 338.437 | 1.00 | 0.00 | P |
| ATOM | 236 | P | C | A | 241 | -21.956 102.646 334.447 | 1.00 | 0.00 | P |
| ATOM | 237 | P | C | A | 242 | -15.809 104.175 332.615 | 1.00 | 0.00 | P |
| ATOM | 238 | P | A | A | 243 | -12.114 105.378 332.945 | 1.00 | 0.00 | P |
| ATOM | 239 | P | U | A | 244 | -6.723 106.326 332.964 | 1.00 | 0.00 | P |

```
ATOM    240  P    C A 245     -9.530 111.750 332.757  1.00  0.00           P
ATOM    241  P    A A 246     -6.091 110.716 338.105  1.00  0.00           P
ATOM    242  P    G A 247     -2.206 110.892 343.130  1.00  0.00           P
ATOM    243  P    C A 248     -5.127 114.947 347.254  1.00  0.00           P
ATOM    244  P    U A 249     -8.916 117.979 350.132  1.00  0.00           P
ATOM    245  P    A A 250    -10.651 119.751 354.606  1.00  0.00           P
ATOM    246  P    G A 251    -10.136 119.599 359.078  1.00  0.00           P
ATOM    247  P    U A 252    -15.773 118.159 359.044  1.00  0.00           P
ATOM    248  P    U A 253    -15.303 112.905 359.947  1.00  0.00           P
ATOM    249  P    G A 254    -15.887 110.208 364.858  1.00  0.00           P
ATOM    250  P    G A 255    -16.281 109.631 370.927  1.00  0.00           P
ATOM    251  P    U A 256    -16.263 111.050 376.493  1.00  0.00           P
ATOM    252  P    G A 257    -18.717 114.829 380.158  1.00  0.00           P
ATOM    253  P    G A 258    -22.445 119.393 381.054  1.00  0.00           P
ATOM    254  P    G A 259    -26.973 122.858 377.799  1.00  0.00           P
ATOM    255  P    G A 260    -30.853 125.311 374.063  1.00  0.00           P
ATOM    256  P    U A 261    -35.099 123.217 370.770  1.00  0.00           P
ATOM    257  P    A A 262    -39.038 119.549 369.744  1.00  0.00           P
ATOM    258  P    A A 263    -36.358 115.938 373.027  1.00  0.00           P
ATOM    259  P    U A 264    -31.378 112.938 372.633  1.00  0.00           P
ATOM    260  P    G A 265    -26.235 111.509 372.154  1.00  0.00           P
ATOM    261  P    G A 266    -21.806 113.863 369.117  1.00  0.00           P
ATOM    262  P    C A 267    -22.232 114.257 362.217  1.00  0.00           P
ATOM    263  P    C A 268    -22.312 119.764 361.722  1.00  0.00           P
ATOM    264  P    C A 269    -20.116 124.579 364.169  1.00  0.00           P
ATOM    265  P    A A 270    -16.351 127.180 368.098  1.00  0.00           P
ATOM    266  P    C A 271    -11.705 127.182 371.456  1.00  0.00           P
ATOM    267  P    C A 272     -7.233 123.775 373.432  1.00  0.00           P
ATOM    268  P    A A 273     -3.971 118.958 373.192  1.00  0.00           P
ATOM    269  P    A A 274     -1.535 114.206 370.753  1.00  0.00           P
ATOM    270  P    G A 275     -3.323 109.465 365.691  1.00  0.00           P
ATOM    271  P    G A 276     -8.829 106.710 362.855  1.00  0.00           P
ATOM    272  P    C A 277    -12.703 105.287 359.082  1.00  0.00           P
ATOM    273  P    G A 278    -12.936 103.568 353.933  1.00  0.00           P
ATOM    274  P    A A 279    -11.285 101.005 349.058  1.00  0.00           P
ATOM    275  P    C A 280    -10.491  96.728 345.065  1.00  0.00           P
ATOM    276  P    G A 281    -15.564 100.276 345.499  1.00  0.00           P
ATOM    277  P    A A 282    -15.395 105.114 343.980  1.00  0.00           P
ATOM    278  P    C A 283    -14.744 109.460 347.501  1.00  0.00           P
ATOM    279  P    G A 284    -14.171 115.915 346.159  1.00  0.00           P
ATOM    280  P    G A 285    -15.256 118.955 340.991  1.00  0.00           P
ATOM    281  P    G A 286    -18.149 118.629 335.931  1.00  0.00           P
ATOM    282  P    U A 287    -25.855 115.733 332.654  1.00  0.00           P
ATOM    283  P    A A 288    -30.448 112.295 335.702  1.00  0.00           P
ATOM    284  P    G A 289    -34.715 114.921 339.560  1.00  0.00           P
ATOM    285  P    C A 290    -35.053 109.583 341.759  1.00  0.00           P
ATOM    286  P    C A 291    -35.797 103.930 342.609  1.00  0.00           P
ATOM    287  P    G A 292    -39.346  99.037 342.346  1.00  0.00           P
ATOM    288  P    G A 293    -44.881  97.069 338.248  1.00  0.00           P
ATOM    289  P    U A 294    -46.868  96.119 333.581  1.00  0.00           P
ATOM    290  P    C A 295    -46.250  96.675 328.045  1.00  0.00           P
ATOM    291  P    U A 296    -43.661  94.476 323.623  1.00  0.00           P
ATOM    292  P    G A 297    -39.822  90.486 321.419  1.00  0.00           P
ATOM    293  P    A A 298    -38.098  85.399 322.549  1.00  0.00           P
ATOM    294  P    G A 299    -39.440  85.202 328.195  1.00  0.00           P
ATOM    295  P    A A 300    -36.265  85.844 333.838  1.00  0.00           P
ATOM    296  P    G A 301    -31.766  88.892 335.899  1.00  0.00           P
ATOM    297  P    G A 302    -29.201  94.192 332.941  1.00  0.00           P
ATOM    298  P    A A 303    -29.168  98.846 329.871  1.00  0.00           P
ATOM    299  P    U A 304    -32.452 103.855 329.317  1.00  0.00           P
ATOM    300  P    G A 305    -37.471 107.254 332.704  1.00  0.00           P
ATOM    301  P    G A 306    -42.473 107.154 335.834  1.00  0.00           P
ATOM    302  P    C A 307    -47.682 110.564 333.197  1.00  0.00           P
ATOM    303  P    C A 308    -51.833 110.700 337.027  1.00  0.00           P
ATOM    304  P    G A 309    -53.684 108.039 341.381  1.00  0.00           P
ATOM    305  P    G A 310    -51.876 106.366 347.502  1.00  0.00           P
ATOM    306  P    C A 311    -47.352 107.916 351.175  1.00  0.00           P
ATOM    307  P    C A 312    -41.994 110.900 353.091  1.00  0.00           P
ATOM    308  P    A A 313    -37.677 115.742 351.762  1.00  0.00           P
ATOM    309  P    C A 314    -36.476 121.780 349.722  1.00  0.00           P
ATOM    310  P    A A 315    -38.964 125.278 346.723  1.00  0.00           P
ATOM    311  P    G A 316    -40.811 130.636 344.260  1.00  0.00           P
ATOM    312  P    G A 317    -35.872 129.340 342.936  1.00  0.00           P
ATOM    313  P    G A 318    -31.029 128.383 345.641  1.00  0.00           P
ATOM    314  P    G A 319    -29.412 128.233 349.389  1.00  0.00           P
ATOM    315  P    C A 320    -29.128 129.144 356.904  1.00  0.00           P
ATOM    316  P    A A 321    -31.422 129.896 361.912  1.00  0.00           P
ATOM    317  P    C A 322    -36.849 132.037 365.917  1.00  0.00           P
ATOM    318  P    U A 323    -41.770 132.676 368.422  1.00  0.00           P
ATOM    319  P    G A 324    -46.522 130.085 369.243  1.00  0.00           P
ATOM    320  P    A A 325    -48.628 124.031 368.749  1.00  0.00           P
ATOM    321  P    G A 326    -44.277 122.156 367.140  1.00  0.00           P
ATOM    322  P    A A 327    -41.805 121.575 363.036  1.00  0.00           P
ATOM    323  P    C A 328    -39.394 123.400 358.840  1.00  0.00           P
ATOM    324  P    A A 329    -39.051 126.979 355.934  1.00  0.00           P
ATOM    325  P    C A 330    -44.310 126.141 353.857  1.00  0.00           P
ATOM    326  P    G A 331    -47.840 128.776 350.494  1.00  0.00           P
```

```
ATOM  327  P   G A 332   -50.639 133.375 351.391  1.00  0.00           P
ATOM  328  P   G A 333   -45.756 136.939 353.550  1.00  0.00           P
ATOM  329  P   C A 334   -42.007 140.459 355.493  1.00  0.00           P
ATOM  330  P   C A 335   -37.124 142.989 355.191  1.00  0.00           P
ATOM  331  P   C A 336   -32.215 144.282 352.445  1.00  0.00           P
ATOM  332  P   C A 337   -29.043 144.003 347.743  1.00  0.00           P
ATOM  333  P   A A 338   -31.723 144.161 342.477  1.00  0.00           P
ATOM  334  P   C A 339   -34.170 144.376 337.382  1.00  0.00           P
ATOM  335  P   U A 340   -39.391 145.113 334.484  1.00  0.00           P
ATOM  336  P   C A 341   -44.753 147.092 333.985  1.00  0.00           P
ATOM  337  P   C A 342   -49.097 150.833 336.191  1.00  0.00           P
ATOM  338  P   U A 343   -50.471 155.387 338.904  1.00  0.00           P
ATOM  339  P   A A 344   -48.638 160.221 341.423  1.00  0.00           P
ATOM  340  P   C A 345   -44.580 162.951 345.538  1.00  0.00           P
ATOM  341  P   G A 346   -38.261 160.919 346.913  1.00  0.00           P
ATOM  342  P   G A 347   -38.928 155.351 350.695  1.00  0.00           P
ATOM  343  P   G A 348   -43.094 150.541 352.374  1.00  0.00           P
ATOM  344  P   A A 349   -47.524 146.144 350.692  1.00  0.00           P
ATOM  345  P   G A 350   -49.606 141.525 348.143  1.00  0.00           P
ATOM  346  P   G A 351   -47.853 137.997 345.051  1.00  0.00           P
ATOM  347  P   C A 352   -47.076 133.448 342.657  1.00  0.00           P
ATOM  348  P   A A 353   -46.787 129.268 338.046  1.00  0.00           P
ATOM  349  P   G A 354   -49.731 126.940 340.906  1.00  0.00           P
ATOM  350  P   C A 355   -54.812 123.692 338.170  1.00  0.00           P
ATOM  351  P   A A 356   -58.713 123.450 334.342  1.00  0.00           P
ATOM  352  P   G A 357   -59.192 126.998 329.239  1.00  0.00           P
ATOM  353  P   U A 358   -56.808 131.364 325.827  1.00  0.00           P
ATOM  354  P   U A 359   -53.287 134.809 323.077  1.00  0.00           P
ATOM  355  P   A A 360   -46.921 134.492 323.217  1.00  0.00           P
ATOM  356  P   G A 361   -41.914 133.002 321.227  1.00  0.00           P
ATOM  357  P   G A 362   -39.243 128.632 318.895  1.00  0.00           P
ATOM  358  P   A A 363   -40.427 124.022 315.901  1.00  0.00           P
ATOM  359  P   A A 364   -45.785 123.348 317.126  1.00  0.00           P
ATOM  360  P   U A 365   -48.738 121.978 321.209  1.00  0.00           P
ATOM  361  P   C A 366   -52.602 122.576 325.245  1.00  0.00           P
ATOM  362  P   U A 367   -58.892 123.028 325.350  1.00  0.00           P
ATOM  363  P   U A 368   -62.521 126.322 328.669  1.00  0.00           P
ATOM  364  P   C A 369   -65.197 128.651 332.627  1.00  0.00           P
ATOM  365  P   C A 370   -70.544 127.566 333.657  1.00  0.00           P
ATOM  366  P   G A 371   -73.843 126.155 337.538  1.00  0.00           P
ATOM  367  P   C A 372   -73.963 123.783 342.383  1.00  0.00           P
ATOM  368  P   A A 373   -74.158 119.441 347.146  1.00  0.00           P
ATOM  369  P   A A 374   -73.389 115.047 349.128  1.00  0.00           P
ATOM  370  P   U A 375   -70.680 110.437 351.111  1.00  0.00           P
ATOM  371  P   G A 376   -66.100 109.275 353.939  1.00  0.00           P
ATOM  372  P   G A 377   -61.998 112.219 356.976  1.00  0.00           P
ATOM  373  P   G A 378   -59.593 116.700 359.831  1.00  0.00           P
ATOM  374  P   C A 379   -60.045 120.868 363.284  1.00  0.00           P
ATOM  375  P   G A 380   -63.406 123.771 366.902  1.00  0.00           P
ATOM  376  P   C A 381   -68.180 123.772 369.354  1.00  0.00           P
ATOM  377  P   A A 382   -71.102 119.676 365.807  1.00  0.00           P
ATOM  378  P   A A 383   -75.429 119.660 361.356  1.00  0.00           P
ATOM  379  P   G A 384   -77.798 122.248 356.944  1.00  0.00           P
ATOM  380  P   C A 385   -73.702 126.508 353.682  1.00  0.00           P
ATOM  381  P   C A 386   -69.016 128.695 351.429  1.00  0.00           P
ATOM  382  P   U A 387   -64.285 127.491 348.726  1.00  0.00           P
ATOM  383  P   G A 388   -61.561 124.191 345.663  1.00  0.00           P
ATOM  384  P   A A 389   -59.430 121.311 343.562  1.00  0.00           P
ATOM  385  P   C A 390   -59.297 116.707 342.546  1.00  0.00           P
ATOM  386  P   G A 391   -63.866 112.439 341.802  1.00  0.00           P
ATOM  387  P   G A 392   -68.349 110.610 338.892  1.00  0.00           P
ATOM  388  P   A A 393   -70.096 114.173 333.294  1.00  0.00           P
ATOM  389  P   G A 394   -69.300 116.949 327.807  1.00  0.00           P
ATOM  390  P   C A 395   -66.975 119.144 323.147  1.00  0.00           P
ATOM  391  P   G A 396   -63.174 118.503 319.257  1.00  0.00           P
ATOM  392  P   A A 397   -60.109 115.498 316.829  1.00  0.00           P
ATOM  393  P   C A 398   -55.402 113.293 317.740  1.00  0.00           P
ATOM  394  P   G A 399   -53.707 107.892 318.530  1.00  0.00           P
ATOM  395  P   C A 400   -54.352 102.353 319.998  1.00  0.00           P
ATOM  396  P   C A 401   -57.724  97.756 320.941  1.00  0.00           P
ATOM  397  P   G A 402   -62.904  95.623 320.009  1.00  0.00           P
ATOM  398  P   C A 403   -67.949  95.411 317.514  1.00  0.00           P
ATOM  399  P   U A 404   -71.069  99.121 313.886  1.00  0.00           P
ATOM  400  P   U A 405   -72.692 100.605 309.291  1.00  0.00           P
ATOM  401  P   G A 406   -73.892 101.332 302.835  1.00  0.00           P
ATOM  402  P   G A 407   -74.265  94.720 303.929  1.00  0.00           P
ATOM  403  P   A A 408   -76.111  89.538 302.943  1.00  0.00           P
ATOM  404  P   G A 409   -77.246  86.006 298.577  1.00  0.00           P
ATOM  405  P   G A 410   -80.216  86.704 292.804  1.00  0.00           P
ATOM  406  P   A A 411   -78.586  88.064 287.846  1.00  0.00           P
ATOM  407  P   A A 412   -77.504  84.963 283.865  1.00  0.00           P
ATOM  408  P   G A 413   -73.620  87.048 278.505  1.00  0.00           P
ATOM  409  P   A A 414   -70.205  93.037 280.715  1.00  0.00           P
ATOM  410  P   A A 415   -70.245  97.050 277.320  1.00  0.00           P
ATOM  411  P   G A 416   -66.880 101.786 276.465  1.00  0.00           P
ATOM  412  P   C A 417   -61.868 104.106 277.870  1.00  0.00           P
ATOM  413  P   C A 418   -56.479 102.172 279.231  1.00  0.00           P
```

```
ATOM    414  P    C A 419    -52.619  98.139 278.755  1.00  0.00           P
ATOM    415  P    U A 420    -50.904  92.979 276.076  1.00  0.00           P
ATOM    416  P    U A 421    -51.083  89.431 271.597  1.00  0.00           P
ATOM    417  P    C A 422    -54.597  86.341 267.440  1.00  0.00           P
ATOM    418  P    G A 423    -61.021  88.075 265.907  1.00  0.00           P
ATOM    419  P    G A 424    -65.154  87.020 271.234  1.00  0.00           P
ATOM    420  P    G A 425    -64.185  85.689 277.903  1.00  0.00           P
ATOM    421  P    G A 426    -62.747  86.562 283.277  1.00  0.00           P
ATOM    422  P    U A 427    -62.219  89.745 288.047  1.00  0.00           P
ATOM    423  P    G A 428    -63.770  94.165 291.786  1.00  0.00           P
ATOM    424  P    U A 429    -67.817  88.555 290.561  1.00  0.00           P
ATOM    425  P    A A 430    -69.276  91.308 295.552  1.00  0.00           P
ATOM    426  P    A A 431    -72.409  97.010 294.621  1.00  0.00           P
ATOM    427  P    A A 432    -74.773 101.759 292.450  1.00  0.00           P
ATOM    428  P    C A 433    -79.621 101.652 289.352  1.00  0.00           P
ATOM    429  P    U A 434    -84.902  98.796 289.766  1.00  0.00           P
ATOM    430  P    C A 435    -88.608  96.210 292.754  1.00  0.00           P
ATOM    431  P    C A 436    -90.480  94.753 298.600  1.00  0.00           P
ATOM    432  P    U A 437    -88.033  94.748 305.570  1.00  0.00           P
ATOM    433  P    G A 438    -86.183  95.452 311.930  1.00  0.00           P
ATOM    434  P    A A 439    -83.229 100.014 314.325  1.00  0.00           P
ATOM    435  P    A A 440    -78.644 104.660 313.585  1.00  0.00           P
ATOM    436  P    C A 442    -79.817 111.213 315.316  1.00  0.00           P
ATOM    437  P    C A 443    -84.993 114.132 315.760  1.00  0.00           P
ATOM    438  P    C A 444    -90.362 114.844 317.864  1.00  0.00           P
ATOM    439  P    G A 445    -94.003 114.094 322.177  1.00  0.00           P
ATOM    440  P    G A 446    -95.068 112.302 327.779  1.00  0.00           P
ATOM    441  P    G A 447    -91.675 109.613 332.900  1.00  0.00           P
ATOM    442  P    A A 448    -86.504 109.069 335.669  1.00  0.00           P
ATOM    443  P    C A 449    -83.151 106.511 339.954  1.00  0.00           P
ATOM    444  P    G A 450    -79.520 105.661 343.612  1.00  0.00           P
ATOM    445  P    A A 451    -75.884 110.739 346.807  1.00  0.00           P
ATOM    446  P    A A 452    -79.953 105.879 348.624  1.00  0.00           P
ATOM    447  P    A A 453    -80.290 106.121 354.111  1.00  0.00           P
ATOM    448  P    C A 454    -78.278 109.129 356.227  1.00  0.00           P
ATOM    449  P    C A 455    -78.337 114.287 362.864  1.00  0.00           P
ATOM    450  P    C A 456    -83.892 116.883 364.031  1.00  0.00           P
ATOM    451  P    C A 457    -88.425 115.958 367.315  1.00  0.00           P
ATOM    452  P    C A 458    -91.050 111.895 371.366  1.00  0.00           P
ATOM    453  P    G A 464    -90.779 107.963 374.768  1.00  0.00           P
ATOM    454  P    A A 465    -87.855 104.735 377.897  1.00  0.00           P
ATOM    455  P    C A 466    -83.180 109.227 375.561  1.00  0.00           P
ATOM    456  P    G A 467    -78.927 106.987 370.544  1.00  0.00           P
ATOM    457  P    A A 468    -77.079 102.008 368.960  1.00  0.00           P
ATOM    458  P    G A 474    -79.397  97.895 366.127  1.00  0.00           P
ATOM    459  P    G A 475    -84.670  97.698 363.397  1.00  0.00           P
ATOM    460  P    G A 476    -88.868  99.922 360.543  1.00  0.00           P
ATOM    461  P    G A 477    -91.531 104.605 357.485  1.00  0.00           P
ATOM    462  P    A A 478    -91.517 109.011 353.672  1.00  0.00           P
ATOM    463  P    C A 479    -89.798 113.646 350.344  1.00  0.00           P
ATOM    464  P    U A 480    -87.134 116.839 347.399  1.00  0.00           P
ATOM    465  P    G A 481    -83.337 117.903 343.449  1.00  0.00           P
ATOM    466  P    A A 482    -80.437 119.401 338.144  1.00  0.00           P
ATOM    467  P    C A 483    -77.481 120.256 334.287  1.00  0.00           P
ATOM    468  P    G A 484    -76.619 115.516 330.698  1.00  0.00           P
ATOM    469  P    G A 485    -81.866 119.339 331.052  1.00  0.00           P
ATOM    470  P    U A 486    -85.153 113.959 326.245  1.00  0.00           P
ATOM    471  P    A A 487    -80.051 109.773 325.754  1.00  0.00           P
ATOM    472  P    C A 488    -79.050 104.075 326.556  1.00  0.00           P
ATOM    473  P    C A 489    -83.526  99.913 326.282  1.00  0.00           P
ATOM    474  P    G A 490    -88.514  98.004 324.787  1.00  0.00           P
ATOM    475  P    G A 491    -92.694  98.173 321.087  1.00  0.00           P
ATOM    476  P    G A 492    -94.522  99.947 315.765  1.00  0.00           P
ATOM    477  P    G A 493    -93.878 102.192 310.510  1.00  0.00           P
ATOM    478  P    U A 494    -90.411 102.110 304.676  1.00  0.00           P
ATOM    479  P    A A 495    -85.536 102.929 302.479  1.00  0.00           P
ATOM    480  P    A A 496    -80.645 103.983 300.172  1.00  0.00           P
ATOM    481  P    U A 497    -74.301 105.909 300.804  1.00  0.00           P
ATOM    482  P    A A 498    -68.969 107.127 299.899  1.00  0.00           P
ATOM    483  P    G A 500    -62.542 105.736 298.333  1.00  0.00           P
ATOM    484  P    C A 501    -57.541 108.737 299.576  1.00  0.00           P
ATOM    485  P    G A 502    -51.468 107.827 300.369  1.00  0.00           P
ATOM    486  P    C A 503    -46.704 104.427 299.855  1.00  0.00           P
ATOM    487  P    C A 504    -43.853  99.679 296.976  1.00  0.00           P
ATOM    488  P    G A 505    -42.300  97.312 291.661  1.00  0.00           P
ATOM    489  P    G A 506    -39.457  92.386 293.423  1.00  0.00           P
ATOM    490  P    C A 507    -37.490  89.228 297.223  1.00  0.00           P
ATOM    491  P    C A 508    -37.737  89.104 303.063  1.00  0.00           P
ATOM    492  P    A A 509    -42.129  88.093 298.390  1.00  0.00           P
ATOM    493  P    A A 510    -46.292  87.831 295.294  1.00  0.00           P
ATOM    494  P    C A 511    -48.815  90.447 291.121  1.00  0.00           P
ATOM    495  P    U A 512    -46.175  91.097 283.761  1.00  0.00           P
ATOM    496  P    C A 513    -46.745  95.803 278.644  1.00  0.00           P
ATOM    497  P    C A 514    -47.373 100.930 275.318  1.00  0.00           P
ATOM    498  P    G A 515    -46.522 106.651 274.781  1.00  0.00           P
ATOM    499  P    U A 516    -42.631 109.633 277.447  1.00  0.00           P
ATOM    500  P    G A 517    -36.932 111.639 278.347  1.00  0.00           P
```

| | | | | | | | | | |
|---|---|---|---|---|---|---|---|---|---|
| ATOM | 501 | P | C | A | 518 | -30.588 | 109.472 | 279.327 | 1.00 | 0.00 | P |
| ATOM | 502 | P | C | A | 519 | -27.840 | 112.573 | 283.746 | 1.00 | 0.00 | P |
| ATOM | 503 | P | A | A | 520 | -31.888 | 116.651 | 287.121 | 1.00 | 0.00 | P |
| ATOM | 504 | P | G | A | 521 | -37.733 | 115.970 | 290.798 | 1.00 | 0.00 | P |
| ATOM | 505 | P | C | A | 522 | -39.223 | 111.071 | 295.116 | 1.00 | 0.00 | P |
| ATOM | 506 | P | A | A | 523 | -39.819 | 106.847 | 298.570 | 1.00 | 0.00 | P |
| ATOM | 507 | P | G | A | 524 | -36.801 | 104.915 | 301.056 | 1.00 | 0.00 | P |
| ATOM | 508 | P | C | A | 525 | -30.872 | 103.000 | 303.475 | 1.00 | 0.00 | P |
| ATOM | 509 | P | C | A | 526 | -26.411 | 100.303 | 301.208 | 1.00 | 0.00 | P |
| ATOM | 510 | P | G | A | 527 | -25.121 | 96.932 | 297.313 | 1.00 | 0.00 | P |
| ATOM | 511 | P | C | A | 528 | -28.782 | 97.980 | 291.471 | 1.00 | 0.00 | P |
| ATOM | 512 | P | G | A | 529 | -32.572 | 102.390 | 287.478 | 1.00 | 0.00 | P |
| ATOM | 513 | P | G | A | 530 | -30.567 | 102.969 | 281.757 | 1.00 | 0.00 | P |
| ATOM | 514 | P | U | A | 531 | -30.767 | 106.169 | 277.382 | 1.00 | 0.00 | P |
| ATOM | 515 | P | A | A | 532 | -32.946 | 101.108 | 274.091 | 1.00 | 0.00 | P |
| ATOM | 516 | P | A | A | 533 | -37.350 | 100.364 | 279.399 | 1.00 | 0.00 | P |
| ATOM | 517 | P | U | A | 534 | -39.826 | 96.590 | 282.416 | 1.00 | 0.00 | P |
| ATOM | 518 | P | A | A | 535 | -41.007 | 98.430 | 287.487 | 1.00 | 0.00 | P |
| ATOM | 519 | P | C | A | 536 | -40.591 | 104.173 | 290.769 | 1.00 | 0.00 | P |
| ATOM | 520 | P | G | A | 537 | -42.787 | 109.053 | 291.295 | 1.00 | 0.00 | P |
| ATOM | 521 | P | G | A | 538 | -48.336 | 109.929 | 290.398 | 1.00 | 0.00 | P |
| ATOM | 522 | P | A | A | 539 | -53.892 | 108.107 | 288.910 | 1.00 | 0.00 | P |
| ATOM | 523 | P | G | A | 540 | -57.640 | 104.213 | 286.744 | 1.00 | 0.00 | P |
| ATOM | 524 | P | G | A | 541 | -58.782 | 96.809 | 287.694 | 1.00 | 0.00 | P |
| ATOM | 525 | P | G | A | 542 | -57.319 | 92.601 | 291.616 | 1.00 | 0.00 | P |
| ATOM | 526 | P | C | A | 543 | -54.806 | 90.406 | 296.768 | 1.00 | 0.00 | P |
| ATOM | 527 | P | G | A | 544 | -53.253 | 90.796 | 302.157 | 1.00 | 0.00 | P |
| ATOM | 528 | P | C | A | 545 | -53.799 | 93.415 | 307.166 | 1.00 | 0.00 | P |
| ATOM | 529 | P | G | A | 546 | -58.416 | 96.956 | 309.097 | 1.00 | 0.00 | P |
| ATOM | 530 | P | A | A | 547 | -62.489 | 99.930 | 312.879 | 1.00 | 0.00 | P |
| ATOM | 531 | P | G | A | 548 | -60.039 | 103.622 | 315.941 | 1.00 | 0.00 | P |
| ATOM | 532 | P | C | A | 549 | -55.864 | 101.568 | 312.530 | 1.00 | 0.00 | P |
| ATOM | 533 | P | G | A | 550 | -51.440 | 100.776 | 308.382 | 1.00 | 0.00 | P |
| ATOM | 534 | P | U | A | 551 | -45.475 | 103.418 | 307.374 | 1.00 | 0.00 | P |
| ATOM | 535 | P | U | A | 552 | -40.622 | 106.744 | 307.622 | 1.00 | 0.00 | P |
| ATOM | 536 | P | A | A | 553 | -36.661 | 109.235 | 310.782 | 1.00 | 0.00 | P |
| ATOM | 537 | P | C | A | 554 | -33.921 | 109.411 | 315.595 | 1.00 | 0.00 | P |
| ATOM | 538 | P | C | A | 555 | -32.743 | 106.293 | 320.591 | 1.00 | 0.00 | P |
| ATOM | 539 | P | C | A | 556 | -32.201 | 101.598 | 323.658 | 1.00 | 0.00 | P |
| ATOM | 540 | P | G | A | 557 | -33.728 | 93.785 | 322.621 | 1.00 | 0.00 | P |
| ATOM | 541 | P | G | A | 558 | -34.163 | 88.491 | 321.408 | 1.00 | 0.00 | P |
| ATOM | 542 | P | A | A | 559 | -30.668 | 87.674 | 315.948 | 1.00 | 0.00 | P |
| ATOM | 543 | P | U | A | 560 | -28.925 | 87.271 | 321.707 | 1.00 | 0.00 | P |
| ATOM | 544 | P | U | A | 561 | -23.980 | 86.052 | 318.214 | 1.00 | 0.00 | P |
| ATOM | 545 | P | C | A | 562 | -23.793 | 91.075 | 321.785 | 1.00 | 0.00 | P |
| ATOM | 546 | P | A | A | 563 | -23.446 | 90.211 | 327.367 | 1.00 | 0.00 | P |
| ATOM | 547 | P | C | A | 564 | -21.625 | 85.319 | 328.812 | 1.00 | 0.00 | P |
| ATOM | 548 | P | U | A | 565 | -24.163 | 82.557 | 332.104 | 1.00 | 0.00 | P |
| ATOM | 549 | P | G | A | 566 | -27.284 | 80.180 | 327.160 | 1.00 | 0.00 | P |
| ATOM | 550 | P | G | A | 567 | -21.582 | 80.033 | 326.313 | 1.00 | 0.00 | P |
| ATOM | 551 | P | G | A | 568 | -16.484 | 80.312 | 322.411 | 1.00 | 0.00 | P |
| ATOM | 552 | P | C | A | 569 | -10.182 | 81.459 | 320.227 | 1.00 | 0.00 | P |
| ATOM | 553 | P | G | A | 570 | -4.705 | 80.915 | 318.077 | 1.00 | 0.00 | P |
| ATOM | 554 | P | U | A | 571 | -2.687 | 83.379 | 314.499 | 1.00 | 0.00 | P |
| ATOM | 555 | P | A | A | 572 | -2.823 | 87.011 | 311.861 | 1.00 | 0.00 | P |
| ATOM | 556 | P | A | A | 573 | -6.253 | 89.339 | 313.027 | 1.00 | 0.00 | P |
| ATOM | 557 | P | A | A | 574 | -6.020 | 89.990 | 317.287 | 1.00 | 0.00 | P |
| ATOM | 558 | P | G | A | 575 | -4.038 | 89.436 | 320.590 | 1.00 | 0.00 | P |
| ATOM | 559 | P | G | A | 576 | 1.220 | 88.876 | 323.375 | 1.00 | 0.00 | P |
| ATOM | 560 | P | G | A | 577 | 6.396 | 87.526 | 326.226 | 1.00 | 0.00 | P |
| ATOM | 561 | P | C | A | 578 | 6.738 | 83.733 | 330.650 | 1.00 | 0.00 | P |
| ATOM | 562 | P | G | A | 579 | 8.659 | 81.579 | 335.914 | 1.00 | 0.00 | P |
| ATOM | 563 | P | U | A | 580 | 10.773 | 82.090 | 342.204 | 1.00 | 0.00 | P |
| ATOM | 564 | P | G | A | 581 | 6.072 | 84.158 | 345.588 | 1.00 | 0.00 | P |
| ATOM | 565 | P | U | A | 582 | 3.585 | 85.910 | 349.076 | 1.00 | 0.00 | P |
| ATOM | 566 | P | A | A | 583 | 0.397 | 89.597 | 349.809 | 1.00 | 0.00 | P |
| ATOM | 567 | P | G | A | 584 | -4.881 | 89.987 | 348.494 | 1.00 | 0.00 | P |
| ATOM | 568 | P | G | A | 585 | -9.542 | 86.975 | 345.896 | 1.00 | 0.00 | P |
| ATOM | 569 | P | C | A | 586 | -12.012 | 82.028 | 344.023 | 1.00 | 0.00 | P |
| ATOM | 570 | P | G | A | 587 | -9.856 | 75.583 | 346.261 | 1.00 | 0.00 | P |
| ATOM | 571 | P | G | A | 588 | -8.095 | 70.272 | 347.602 | 1.00 | 0.00 | P |
| ATOM | 572 | P | C | A | 589 | -7.610 | 64.570 | 347.973 | 1.00 | 0.00 | P |
| ATOM | 573 | P | C | A | 590 | -9.976 | 60.726 | 351.648 | 1.00 | 0.00 | P |
| ATOM | 574 | P | U | A | 591 | -12.940 | 59.653 | 356.328 | 1.00 | 0.00 | P |
| ATOM | 575 | P | G | A | 592 | -15.997 | 61.246 | 361.114 | 1.00 | 0.00 | P |
| ATOM | 576 | P | G | A | 593 | -18.693 | 65.200 | 364.613 | 1.00 | 0.00 | P |
| ATOM | 577 | P | G | A | 594 | -21.057 | 70.119 | 366.299 | 1.00 | 0.00 | P |
| ATOM | 578 | P | G | A | 595 | -23.115 | 75.266 | 364.794 | 1.00 | 0.00 | P |
| ATOM | 579 | P | C | A | 596 | -23.622 | 80.369 | 361.113 | 1.00 | 0.00 | P |
| ATOM | 580 | P | G | A | 597 | -23.836 | 82.495 | 356.669 | 1.00 | 0.00 | P |
| ATOM | 581 | P | U | A | 598 | -25.965 | 81.585 | 352.679 | 1.00 | 0.00 | P |
| ATOM | 582 | P | C | A | 599 | -28.896 | 77.731 | 350.303 | 1.00 | 0.00 | P |
| ATOM | 583 | P | C | A | 600 | -33.730 | 74.645 | 350.451 | 1.00 | 0.00 | P |
| ATOM | 584 | P | C | A | 601 | -38.986 | 73.343 | 352.446 | 1.00 | 0.00 | P |
| ATOM | 585 | P | A | A | 602 | -43.781 | 74.455 | 355.292 | 1.00 | 0.00 | P |
| ATOM | 586 | P | U | A | 603 | -47.352 | 78.210 | 357.832 | 1.00 | 0.00 | P |
| ATOM | 587 | P | G | A | 604 | -48.459 | 83.794 | 358.793 | 1.00 | 0.00 | P |

```
ATOM    588  P    U A 605     -48.339  89.308 357.454  1.00  0.00           P
ATOM    589  P    G A 606     -47.037  93.182 353.164  1.00  0.00           P
ATOM    590  P    A A 607     -48.233  95.977 348.237  1.00  0.00           P
ATOM    591  P    A A 608     -53.213  94.941 348.916  1.00  0.00           P
ATOM    592  P    A A 609     -55.223  95.824 345.636  1.00  0.00           P
ATOM    593  P    G A 610     -55.650  96.410 340.102  1.00  0.00           P
ATOM    594  P    A A 611     -53.451  93.985 335.356  1.00  0.00           P
ATOM    595  P    C A 612     -52.313  89.299 333.222  1.00  0.00           P
ATOM    596  P    C A 613     -54.605  84.291 333.372  1.00  0.00           P
ATOM    597  P    A A 614     -59.494  81.359 334.525  1.00  0.00           P
ATOM    598  P    C A 615     -64.749  80.930 336.171  1.00  0.00           P
ATOM    599  P    G A 616     -70.115  83.874 336.935  1.00  0.00           P
ATOM    600  P    G A 617     -73.439  89.007 337.104  1.00  0.00           P
ATOM    601  P    C A 618     -75.538  93.912 335.435  1.00  0.00           P
ATOM    602  P    U A 619     -75.786  97.908 330.053  1.00  0.00           P
ATOM    603  P    C A 620     -72.924  93.247 329.814  1.00  0.00           P
ATOM    604  P    A A 621     -67.837  90.998 329.227  1.00  0.00           P
ATOM    605  P    A A 622     -62.278  92.792 328.718  1.00  0.00           P
ATOM    606  P    C A 623     -58.915  97.006 330.144  1.00  0.00           P
ATOM    607  P    C A 624     -59.625  99.280 335.540  1.00  0.00           P
ATOM    608  P    G A 625     -61.766  98.157 341.040  1.00  0.00           P
ATOM    609  P    U A 626     -63.156  95.240 345.783  1.00  0.00           P
ATOM    610  P    G A 627     -62.403  90.704 349.066  1.00  0.00           P
ATOM    611  P    G A 628     -60.351  85.558 349.706  1.00  0.00           P
ATOM    612  P    G A 629     -56.188  81.741 348.296  1.00  0.00           P
ATOM    613  P    G A 630     -51.092  80.273 345.509  1.00  0.00           P
ATOM    614  P    G A 631     -45.700  82.085 344.455  1.00  0.00           P
ATOM    615  P    A A 632     -39.476  83.169 346.168  1.00  0.00           P
ATOM    616  P    G A 633     -33.928  84.578 348.001  1.00  0.00           P
ATOM    617  P    C A 634     -31.916  87.658 351.979  1.00  0.00           P
ATOM    618  P    G A 635     -32.612  88.905 358.073  1.00  0.00           P
ATOM    619  P    U A 636     -34.079  88.161 363.320  1.00  0.00           P
ATOM    620  P    G A 637     -35.351  84.129 367.022  1.00  0.00           P
ATOM    621  P    G A 638     -35.460  78.706 368.889  1.00  0.00           P
ATOM    622  P    G A 639     -34.051  73.273 367.845  1.00  0.00           P
ATOM    623  P    A A 640     -31.063  68.774 364.710  1.00  0.00           P
ATOM    624  P    U A 641     -26.962  66.631 359.422  1.00  0.00           P
ATOM    625  P    A A 642     -21.661  65.607 355.829  1.00  0.00           P
ATOM    626  P    C A 643     -18.131  66.535 351.440  1.00  0.00           P
ATOM    627  P    G A 644     -16.189  72.547 349.515  1.00  0.00           P
ATOM    628  P    C A 645     -11.293  74.437 351.190  1.00  0.00           P
ATOM    629  P    U A 646      -9.599  77.571 355.543  1.00  0.00           P
ATOM    630  P    C A 647      -8.219  77.889 361.096  1.00  0.00           P
ATOM    631  P    A A 648      -6.395  74.866 365.490  1.00  0.00           P
ATOM    632  P    G A 649      -4.127  69.985 367.605  1.00  0.00           P
ATOM    633  P    G A 650      -1.688  64.724 366.324  1.00  0.00           P
ATOM    634  P    C A 651       0.561  60.462 362.515  1.00  0.00           P
ATOM    635  P    U A 652       0.657  58.360 355.011  1.00  0.00           P
ATOM    636  P    A A 653       0.868  59.218 347.857  1.00  0.00           P
ATOM    637  P    G A 654       2.867  62.948 343.470  1.00  0.00           P
ATOM    638  P    A A 655       4.586  70.003 343.275  1.00  0.00           P
ATOM    639  P    C A 656      10.260  71.496 345.058  1.00  0.00           P
ATOM    640  P    G A 657      15.077  71.395 348.367  1.00  0.00           P
ATOM    641  P    G A 658      19.055  68.390 351.402  1.00  0.00           P
ATOM    642  P    U A 659      23.479  65.777 350.899  1.00  0.00           P
ATOM    643  P    G A 660      27.163  62.345 348.712  1.00  0.00           P
ATOM    644  P    G A 661      29.008  59.632 343.529  1.00  0.00           P
ATOM    645  P    G A 662      29.638  60.109 337.543  1.00  0.00           P
ATOM    646  P    A A 663      29.306  62.861 332.312  1.00  0.00           P
ATOM    647  P    G A 664      29.230  66.740 327.875  1.00  0.00           P
ATOM    648  P    A A 665      25.790  71.115 326.877  1.00  0.00           P
ATOM    649  P    G A 666      27.742  75.819 327.551  1.00  0.00           P
ATOM    650  P    G A 667      26.023  80.677 328.961  1.00  0.00           P
ATOM    651  P    G A 668      27.508  85.972 330.809  1.00  0.00          'P
ATOM    652  P    U A 669      31.550  89.579 332.880  1.00  0.00           P
ATOM    653  P    G A 670      37.183  90.728 334.382  1.00  0.00           P
ATOM    654  P    G A 671      42.993  88.250 333.845  1.00  0.00           P
ATOM    655  P    U A 672      46.937  86.386 329.210  1.00  0.00           P
ATOM    656  P    G A 673      47.906  82.878 324.947  1.00  0.00           P
ATOM    657  P    G A 674      49.045  80.282 319.106  1.00  0.00           P
ATOM    658  P    A A 675      48.461  80.299 312.902  1.00  0.00           P
ATOM    659  P    A A 676      46.128  83.776 308.473  1.00  0.00           P
ATOM    660  P    U A 677      43.696  88.570 305.216  1.00  0.00           P
ATOM    661  P    U A 678      44.233  93.894 302.776  1.00  0.00           P
ATOM    662  P    C A 679      47.566  99.532 303.016  1.00  0.00           P
ATOM    663  P    C A 680      51.704 102.202 304.784  1.00  0.00           P
ATOM    664  P    C A 681      56.579 102.194 306.021  1.00  0.00           P
ATOM    665  P    G A 682      62.116  99.937 304.981  1.00  0.00           P
ATOM    666  P    G A 683      65.773  96.558 301.736  1.00  0.00           P
ATOM    667  P    A A 684      67.757  92.711 297.506  1.00  0.00           P
ATOM    668  P    G A 685      66.626  90.082 292.000  1.00  0.00           P
ATOM    669  P    U A 686      63.648  90.459 287.334  1.00  0.00           P
ATOM    670  P    A A 687      58.724  92.831 283.666  1.00  0.00           P
ATOM    671  P    G A 688      52.468  95.510 281.798  1.00  0.00           P
ATOM    672  P    C A 689      48.174  92.878 285.577  1.00  0.00           P
ATOM    673  P    G A 690      44.335  92.151 289.961  1.00  0.00           P
ATOM    674  P    G A 691      38.118  92.613 292.032  1.00  0.00           P
```

| | | | | | | | | | | |
|---|---|---|---|---|---|---|---|---|---|---|
| ATOM | 675 | P | U | A | 692 | 33.075 | 92.357 | 290.131 | 1.00 | 0.00 | P |
| ATOM | 676 | P | G | A | 693 | 28.679 | 90.704 | 286.640 | 1.00 | 0.00 | P |
| ATOM | 677 | P | A | A | 694 | 30.538 | 90.655 | 281.475 | 1.00 | 0.00 | P |
| ATOM | 678 | P | A | A | 695 | 32.950 | 95.512 | 279.343 | 1.00 | 0.00 | P |
| ATOM | 679 | P | A | A | 696 | 35.462 | 100.439 | 281.984 | 1.00 | 0.00 | P |
| ATOM | 680 | P | U | A | 697 | 36.173 | 105.188 | 285.344 | 1.00 | 0.00 | P |
| ATOM | 681 | P | G | A | 698 | 39.278 | 106.553 | 290.230 | 1.00 | 0.00 | P |
| ATOM | 682 | P | C | A | 699 | 43.171 | 105.827 | 293.667 | 1.00 | 0.00 | P |
| ATOM | 683 | P | G | A | 700 | 49.669 | 105.138 | 294.386 | 1.00 | 0.00 | P |
| ATOM | 684 | P | C | A | 701 | 52.402 | 104.757 | 289.509 | 1.00 | 0.00 | P |
| ATOM | 685 | P | A | A | 702 | 58.728 | 105.517 | 286.335 | 1.00 | 0.00 | P |
| ATOM | 686 | P | G | A | 703 | 58.718 | 103.309 | 292.797 | 1.00 | 0.00 | P |
| ATOM | 687 | P | A | A | 704 | 56.343 | 98.053 | 293.989 | 1.00 | 0.00 | P |
| ATOM | 688 | P | U | A | 705 | 51.539 | 95.126 | 296.007 | 1.00 | 0.00 | P |
| ATOM | 689 | P | A | A | 706 | 49.113 | 90.084 | 295.601 | 1.00 | 0.00 | P |
| ATOM | 690 | P | C | A | 707 | 51.325 | 85.228 | 296.833 | 1.00 | 0.00 | P |
| ATOM | 691 | P | C | A | 708 | 54.983 | 83.519 | 300.620 | 1.00 | 0.00 | P |
| ATOM | 692 | P | G | A | 709 | 57.866 | 83.513 | 305.455 | 1.00 | 0.00 | P |
| ATOM | 693 | P | G | A | 710 | 59.204 | 86.289 | 310.620 | 1.00 | 0.00 | P |
| ATOM | 694 | P | G | A | 711 | 57.965 | 90.299 | 314.561 | 1.00 | 0.00 | P |
| ATOM | 695 | P | A | A | 712 | 54.707 | 94.602 | 317.151 | 1.00 | 0.00 | P |
| ATOM | 696 | P | G | A | 713 | 50.081 | 97.676 | 318.513 | 1.00 | 0.00 | P |
| ATOM | 697 | P | G | A | 714 | 43.324 | 95.948 | 318.783 | 1.00 | 0.00 | P |
| ATOM | 698 | P | A | A | 715 | 37.231 | 93.956 | 318.673 | 1.00 | 0.00 | P |
| ATOM | 699 | P | A | A | 716 | 33.750 | 90.093 | 317.880 | 1.00 | 0.00 | P |
| ATOM | 700 | P | C | A | 717 | 31.546 | 85.017 | 317.171 | 1.00 | 0.00 | P |
| ATOM | 701 | P | G | A | 718 | 33.878 | 79.050 | 314.726 | 1.00 | 0.00 | P |
| ATOM | 702 | P | C | A | 719 | 33.415 | 75.470 | 311.059 | 1.00 | 0.00 | P |
| ATOM | 703 | P | C | A | 720 | 34.121 | 69.840 | 311.626 | 1.00 | 0.00 | P |
| ATOM | 704 | P | G | A | 721 | 30.719 | 67.476 | 315.867 | 1.00 | 0.00 | P |
| ATOM | 705 | P | A | A | 722 | 26.872 | 69.767 | 309.593 | 1.00 | 0.00 | P |
| ATOM | 706 | P | U | A | 723 | 20.336 | 68.730 | 311.153 | 1.00 | 0.00 | P |
| ATOM | 707 | P | G | A | 724 | 19.113 | 70.030 | 316.871 | 1.00 | 0.00 | P |
| ATOM | 708 | P | G | A | 725 | 19.648 | 68.156 | 322.161 | 1.00 | 0.00 | P |
| ATOM | 709 | P | C | A | 726 | 19.758 | 70.702 | 327.402 | 1.00 | 0.00 | P |
| ATOM | 710 | P | G | A | 727 | 18.494 | 74.074 | 330.982 | 1.00 | 0.00 | P |
| ATOM | 711 | P | A | A | 728 | 15.225 | 77.175 | 332.582 | 1.00 | 0.00 | P |
| ATOM | 712 | P | A | A | 729 | 12.349 | 78.666 | 327.828 | 1.00 | 0.00 | P |
| ATOM | 713 | P | G | A | 730 | 13.352 | 83.319 | 323.957 | 1.00 | 0.00 | P |
| ATOM | 714 | P | G | A | 731 | 16.726 | 86.905 | 322.399 | 1.00 | 0.00 | P |
| ATOM | 715 | P | C | A | 732 | 22.643 | 85.919 | 321.157 | 1.00 | 0.00 | P |
| ATOM | 716 | P | A | A | 733 | 27.639 | 83.723 | 321.348 | 1.00 | 0.00 | P |
| ATOM | 717 | P | G | A | 734 | 31.821 | 80.266 | 320.321 | 1.00 | 0.00 | P |
| ATOM | 718 | P | C | A | 735 | 36.588 | 76.738 | 321.883 | 1.00 | 0.00 | P |
| ATOM | 719 | P | C | A | 736 | 39.749 | 74.838 | 326.446 | 1.00 | 0.00 | P |
| ATOM | 720 | P | A | A | 737 | 40.312 | 73.981 | 333.065 | 1.00 | 0.00 | P |
| ATOM | 721 | P | C | A | 738 | 40.260 | 76.098 | 339.189 | 1.00 | 0.00 | P |
| ATOM | 722 | P | C | A | 739 | 36.663 | 79.079 | 343.207 | 1.00 | 0.00 | P |
| ATOM | 723 | P | U | A | 740 | 30.438 | 80.576 | 345.190 | 1.00 | 0.00 | P |
| ATOM | 724 | P | G | A | 741 | 24.646 | 78.909 | 343.447 | 1.00 | 0.00 | P |
| ATOM | 725 | P | G | A | 742 | 19.199 | 77.203 | 340.827 | 1.00 | 0.00 | P |
| ATOM | 726 | P | U | A | 743 | 15.867 | 73.679 | 338.074 | 1.00 | 0.00 | P |
| ATOM | 727 | P | C | A | 744 | 14.429 | 68.345 | 336.438 | 1.00 | 0.00 | P |
| ATOM | 728 | P | C | A | 745 | 13.970 | 62.569 | 335.990 | 1.00 | 0.00 | P |
| ATOM | 729 | P | A | A | 746 | 14.589 | 57.062 | 337.923 | 1.00 | 0.00 | P |
| ATOM | 730 | P | C | A | 747 | 15.128 | 53.027 | 341.928 | 1.00 | 0.00 | P |
| ATOM | 731 | P | C | A | 748 | 13.771 | 53.455 | 346.943 | 1.00 | 0.00 | P |
| ATOM | 732 | P | C | A | 749 | 11.451 | 54.735 | 351.563 | 1.00 | 0.00 | P |
| ATOM | 733 | P | G | A | 750 | 10.931 | 58.019 | 356.489 | 1.00 | 0.00 | P |
| ATOM | 734 | P | U | A | 751 | 9.937 | 62.731 | 359.071 | 1.00 | 0.00 | P |
| ATOM | 735 | P | G | A | 752 | 5.584 | 69.428 | 357.598 | 1.00 | 0.00 | P |
| ATOM | 736 | P | A | A | 753 | -0.172 | 70.221 | 356.857 | 1.00 | 0.00 | P |
| ATOM | 737 | P | C | A | 754 | -1.278 | 71.918 | 352.190 | 1.00 | 0.00 | P |
| ATOM | 738 | P | G | A | 755 | 3.209 | 75.504 | 350.009 | 1.00 | 0.00 | P |
| ATOM | 739 | P | C | A | 756 | 3.176 | 75.151 | 344.237 | 1.00 | 0.00 | P |
| ATOM | 740 | P | U | A | 757 | 2.347 | 76.311 | 339.057 | 1.00 | 0.00 | P |
| ATOM | 741 | P | G | A | 758 | -0.580 | 82.006 | 336.813 | 1.00 | 0.00 | P |
| ATOM | 742 | P | A | A | 759 | -0.571 | 87.810 | 337.885 | 1.00 | 0.00 | P |
| ATOM | 743 | P | G | A | 760 | -1.443 | 92.198 | 335.760 | 1.00 | 0.00 | P |
| ATOM | 744 | P | G | A | 761 | 1.038 | 97.071 | 339.057 | 1.00 | 0.00 | P |
| ATOM | 745 | P | C | A | 762 | 6.353 | 98.004 | 341.694 | 1.00 | 0.00 | P |
| ATOM | 746 | P | G | A | 763 | 12.433 | 97.055 | 340.793 | 1.00 | 0.00 | P |
| ATOM | 747 | P | C | A | 764 | 17.630 | 94.845 | 337.284 | 1.00 | 0.00 | P |
| ATOM | 748 | P | G | A | 765 | 18.886 | 92.894 | 331.407 | 1.00 | 0.00 | P |
| ATOM | 749 | P | A | A | 766 | 18.763 | 93.020 | 325.986 | 1.00 | 0.00 | P |
| ATOM | 750 | P | A | A | 767 | 22.098 | 93.745 | 321.808 | 1.00 | 0.00 | P |
| ATOM | 751 | P | A | A | 768 | 23.426 | 97.920 | 317.948 | 1.00 | 0.00 | P |
| ATOM | 752 | P | G | A | 769 | 22.202 | 103.102 | 316.583 | 1.00 | 0.00 | P |
| ATOM | 753 | P | C | A | 770 | 22.098 | 108.348 | 319.371 | 1.00 | 0.00 | P |
| ATOM | 754 | P | G | A | 771 | 23.322 | 111.947 | 323.503 | 1.00 | 0.00 | P |
| ATOM | 755 | P | U | A | 772 | 26.860 | 113.902 | 327.036 | 1.00 | 0.00 | P |
| ATOM | 756 | P | G | A | 773 | 32.479 | 112.864 | 329.169 | 1.00 | 0.00 | P |
| ATOM | 757 | P | G | A | 774 | 38.148 | 109.989 | 328.187 | 1.00 | 0.00 | P |
| ATOM | 758 | P | G | A | 775 | 39.504 | 104.617 | 325.203 | 1.00 | 0.00 | P |
| ATOM | 759 | P | G | A | 776 | 42.167 | 101.667 | 320.253 | 1.00 | 0.00 | P |
| ATOM | 760 | P | A | A | 777 | 43.869 | 100.875 | 314.676 | 1.00 | 0.00 | P |
| ATOM | 761 | P | G | A | 778 | 41.529 | 98.755 | 308.346 | 1.00 | 0.00 | P |

| | | | | | | | | | | |
|---|---|---|---|---|---|---|---|---|---|---|
| ATOM | 762 | P | C | A | 779 | 36.920 | 96.619 | 304.381 | 1.00 | 0.00 | P |
| ATOM | 763 | P | A | A | 780 | 30.701 | 97.503 | 304.416 | 1.00 | 0.00 | P |
| ATOM | 764 | P | A | A | 781 | 23.481 | 101.958 | 304.145 | 1.00 | 0.00 | P |
| ATOM | 765 | P | A | A | 782 | 22.254 | 105.354 | 302.601 | 1.00 | 0.00 | P |
| ATOM | 766 | P | C | A | 783 | 22.235 | 110.810 | 301.888 | 1.00 | 0.00 | P |
| ATOM | 767 | P | C | A | 784 | 26.028 | 113.662 | 300.149 | 1.00 | 0.00 | P |
| ATOM | 768 | P | G | A | 785 | 31.085 | 115.035 | 296.014 | 1.00 | 0.00 | P |
| ATOM | 769 | P | G | A | 786 | 32.480 | 111.290 | 289.772 | 1.00 | 0.00 | P |
| ATOM | 770 | P | A | A | 787 | 31.737 | 107.569 | 285.388 | 1.00 | 0.00 | P |
| ATOM | 771 | P | U | A | 788 | 27.942 | 103.878 | 282.163 | 1.00 | 0.00 | P |
| ATOM | 772 | P | U | A | 789 | 22.982 | 102.058 | 280.252 | 1.00 | 0.00 | P |
| ATOM | 773 | P | A | A | 790 | 18.012 | 104.307 | 278.856 | 1.00 | 0.00 | P |
| ATOM | 774 | P | G | A | 791 | 19.290 | 109.347 | 281.484 | 1.00 | 0.00 | P |
| ATOM | 775 | P | A | A | 792 | 20.157 | 110.762 | 286.904 | 1.00 | 0.00 | P |
| ATOM | 776 | P | U | A | 793 | 21.189 | 108.057 | 291.375 | 1.00 | 0.00 | P |
| ATOM | 777 | P | A | A | 794 | 20.130 | 108.438 | 296.192 | 1.00 | 0.00 | P |
| ATOM | 778 | P | C | A | 795 | 20.719 | 102.213 | 295.787 | 1.00 | 0.00 | P |
| ATOM | 779 | P | C | A | 796 | 22.744 | 96.329 | 294.284 | 1.00 | 0.00 | P |
| ATOM | 780 | P | C | A | 797 | 28.735 | 95.611 | 292.716 | 1.00 | 0.00 | P |
| ATOM | 781 | P | G | A | 798 | 35.586 | 98.398 | 294.250 | 1.00 | 0.00 | P |
| ATOM | 782 | P | G | A | 799 | 38.696 | 101.206 | 298.824 | 1.00 | 0.00 | P |
| ATOM | 783 | P | G | A | 800 | 38.035 | 105.134 | 302.504 | 1.00 | 0.00 | P |
| ATOM | 784 | P | U | A | 801 | 35.421 | 107.113 | 307.476 | 1.00 | 0.00 | P |
| ATOM | 785 | P | A | A | 802 | 32.491 | 107.246 | 312.624 | 1.00 | 0.00 | P |
| ATOM | 786 | P | G | A | 803 | 29.073 | 105.660 | 316.870 | 1.00 | 0.00 | P |
| ATOM | 787 | P | U | A | 804 | 28.825 | 100.686 | 316.938 | 1.00 | 0.00 | P |
| ATOM | 788 | P | C | A | 805 | 29.191 | 96.219 | 320.129 | 1.00 | 0.00 | P |
| ATOM | 789 | P | C | A | 806 | 31.727 | 94.808 | 324.058 | 1.00 | 0.00 | P |
| ATOM | 790 | P | A | A | 807 | 34.139 | 94.486 | 330.029 | 1.00 | 0.00 | P |
| ATOM | 791 | P | C | A | 808 | 31.800 | 97.478 | 335.002 | 1.00 | 0.00 | P |
| ATOM | 792 | P | G | A | 809 | 26.352 | 101.299 | 337.237 | 1.00 | 0.00 | P |
| ATOM | 793 | P | C | A | 810 | 19.857 | 103.386 | 336.214 | 1.00 | 0.00 | P |
| ATOM | 794 | P | C | A | 811 | 14.965 | 104.124 | 332.424 | 1.00 | 0.00 | P |
| ATOM | 795 | P | C | A | 812 | 10.676 | 103.623 | 327.409 | 1.00 | 0.00 | P |
| ATOM | 796 | P | U | A | 813 | 7.775 | 97.859 | 325.716 | 1.00 | 0.00 | P |
| ATOM | 797 | P | A | A | 814 | 8.604 | 96.491 | 320.171 | 1.00 | 0.00 | P |
| ATOM | 798 | P | A | A | 815 | 7.657 | 92.934 | 316.962 | 1.00 | 0.00 | P |
| ATOM | 799 | P | A | A | 816 | 10.233 | 88.367 | 315.672 | 1.00 | 0.00 | P |
| ATOM | 800 | P | C | A | 817 | 8.871 | 85.240 | 319.962 | 1.00 | 0.00 | P |
| ATOM | 801 | P | G | A | 818 | 10.980 | 81.277 | 317.766 | 1.00 | 0.00 | P |
| ATOM | 802 | P | A | A | 819 | 4.306 | 82.195 | 316.606 | 1.00 | 0.00 | P |
| ATOM | 803 | P | U | A | 820 | 2.199 | 78.547 | 319.237 | 1.00 | 0.00 | P |
| ATOM | 804 | P | G | A | 821 | -0.978 | 80.012 | 323.736 | 1.00 | 0.00 | P |
| ATOM | 805 | P | C | A | 822 | 2.822 | 78.254 | 327.756 | 1.00 | 0.00 | P |
| ATOM | 806 | P | G | A | 823 | 3.860 | 74.843 | 332.079 | 1.00 | 0.00 | P |
| ATOM | 807 | P | C | A | 824 | 2.686 | 70.265 | 335.141 | 1.00 | 0.00 | P |
| ATOM | 808 | P | G | A | 825 | 0.074 | 65.225 | 335.807 | 1.00 | 0.00 | P |
| ATOM | 809 | P | C | A | 826 | -3.341 | 60.763 | 334.728 | 1.00 | 0.00 | P |
| ATOM | 810 | P | U | A | 827 | -6.411 | 57.917 | 329.959 | 1.00 | 0.00 | P |
| ATOM | 811 | P | A | A | 828 | -6.110 | 56.935 | 325.048 | 1.00 | 0.00 | P |
| ATOM | 812 | P | G | A | 829 | -1.355 | 53.797 | 323.094 | 1.00 | 0.00 | P |
| ATOM | 813 | P | G | A | 830 | 3.656 | 51.409 | 319.139 | 1.00 | 0.00 | P |
| ATOM | 814 | P | U | A | 831 | 8.095 | 51.187 | 315.397 | 1.00 | 0.00 | P |
| ATOM | 815 | P | C | A | 832 | 12.985 | 54.095 | 313.625 | 1.00 | 0.00 | P |
| ATOM | 816 | P | U | A | 833 | 18.017 | 57.511 | 314.689 | 1.00 | 0.00 | P |
| ATOM | 817 | P | C | A | 834 | 20.202 | 61.711 | 317.702 | 1.00 | 0.00 | P |
| ATOM | 818 | P | U | A | 835 | 23.390 | 62.418 | 323.480 | 1.00 | 0.00 | P |
| ATOM | 819 | P | G | A | 836 | 23.747 | 60.780 | 329.070 | 1.00 | 0.00 | P |
| ATOM | 820 | P | G | A | 837 | 22.801 | 56.372 | 333.430 | 1.00 | 0.00 | P |
| ATOM | 821 | P | G | A | 838 | 21.342 | 51.321 | 335.803 | 1.00 | 0.00 | P |
| ATOM | 822 | P | U | A | 841 | 20.008 | 45.411 | 336.017 | 1.00 | 0.00 | P |
| ATOM | 823 | P | C | A | 842 | 17.546 | 41.550 | 329.937 | 1.00 | 0.00 | P |
| ATOM | 824 | P | U | A | 843 | 19.113 | 43.480 | 324.864 | 1.00 | 0.00 | P |
| ATOM | 825 | P | C | A | 848 | 14.090 | 45.815 | 320.465 | 1.00 | 0.00 | P |
| ATOM | 826 | P | C | A | 849 | 9.814 | 48.177 | 323.407 | 1.00 | 0.00 | P |
| ATOM | 827 | P | U | A | 850 | 7.367 | 50.855 | 328.233 | 1.00 | 0.00 | P |
| ATOM | 828 | P | G | A | 851 | 7.140 | 55.550 | 331.646 | 1.00 | 0.00 | P |
| ATOM | 829 | P | G | A | 852 | 8.354 | 61.668 | 332.407 | 1.00 | 0.00 | P |
| ATOM | 830 | P | G | A | 853 | 10.771 | 67.084 | 329.369 | 1.00 | 0.00 | P |
| ATOM | 831 | P | G | A | 854 | 11.775 | 69.788 | 324.662 | 1.00 | 0.00 | P |
| ATOM | 832 | P | G | A | 855 | 10.842 | 71.014 | 318.270 | 1.00 | 0.00 | P |
| ATOM | 833 | P | C | A | 856 | 8.484 | 68.927 | 312.293 | 1.00 | 0.00 | P |
| ATOM | 834 | P | C | A | 857 | 4.642 | 65.012 | 308.630 | 1.00 | 0.00 | P |
| ATOM | 835 | P | G | A | 858 | -1.812 | 67.298 | 305.113 | 1.00 | 0.00 | P |
| ATOM | 836 | P | A | A | 859 | -4.472 | 59.423 | 310.820 | 1.00 | 0.00 | P |
| ATOM | 837 | P | A | A | 860 | -10.115 | 57.887 | 313.325 | 1.00 | 0.00 | P |
| ATOM | 838 | P | G | A | 861 | -11.937 | 61.048 | 314.880 | 1.00 | 0.00 | P |
| ATOM | 839 | P | C | A | 862 | -14.523 | 67.337 | 317.300 | 1.00 | 0.00 | P |
| ATOM | 840 | P | U | A | 863 | -13.242 | 72.539 | 315.941 | 1.00 | 0.00 | P |
| ATOM | 841 | P | A | A | 864 | -14.171 | 76.205 | 311.644 | 1.00 | 0.00 | P |
| ATOM | 842 | P | A | A | 865 | -14.070 | 73.433 | 307.099 | 1.00 | 0.00 | P |
| ATOM | 843 | P | C | A | 866 | -9.056 | 70.935 | 304.548 | 1.00 | 0.00 | P |
| ATOM | 844 | P | G | A | 867 | -2.499 | 70.577 | 304.619 | 1.00 | 0.00 | P |
| ATOM | 845 | P | C | A | 868 | 0.723 | 70.242 | 310.181 | 1.00 | 0.00 | P |
| ATOM | 846 | P | G | A | 869 | 1.167 | 69.231 | 315.783 | 1.00 | 0.00 | P |
| ATOM | 847 | P | U | A | 870 | 0.913 | 64.668 | 320.008 | 1.00 | 0.00 | P |
| ATOM | 848 | P | U | A | 871 | 5.136 | 64.590 | 324.703 | 1.00 | 0.00 | P |

```
ATOM    849  P     A A  872      2.732  70.336 324.420  1.00  0.00           P
ATOM    850  P     A A  873     -2.737  74.489 321.182  1.00  0.00           P
ATOM    851  P     G A  874     -8.136  71.362 320.955  1.00  0.00           P
ATOM    852  P     C A  875    -12.482  68.753 322.587  1.00  0.00           P
ATOM    853  P     G A  876    -15.328  67.928 327.242  1.00  0.00           P
ATOM    854  P     C A  877    -14.368  71.288 332.995  1.00  0.00           P
ATOM    855  P     G A  878    -13.041  75.510 336.798  1.00  0.00           P
ATOM    856  P     C A  879    -10.837  79.920 338.750  1.00  0.00           P
ATOM    857  P     C A  880     -7.765  85.195 337.524  1.00  0.00           P
ATOM    858  P     G A  881     -5.996  89.540 334.133  1.00  0.00           P
ATOM    859  P     C A  882     -5.569  92.551 329.139  1.00  0.00           P
ATOM    860  P     C A  883     -7.483  93.107 323.845  1.00  0.00           P
ATOM    861  P     U A  884    -10.899  94.446 320.041  1.00  0.00           P
ATOM    862  P     G A  885    -14.844  96.377 315.663  1.00  0.00           P
ATOM    863  P     G A  886    -10.307  97.166 311.982  1.00  0.00           P
ATOM    864  P     G A  887     -7.103 100.653 309.166  1.00  0.00           P
ATOM    865  P     G A  888     -5.387 104.297 310.189  1.00  0.00           P
ATOM    866  P     A A  889     -5.751 108.793 314.637  1.00  0.00           P
ATOM    867  P     G A  890     -1.006 103.902 313.158  1.00  0.00           P
ATOM    868  P     U A  891      1.645 107.047 318.426  1.00  0.00           P
ATOM    869  P     A A  892     -0.403 112.261 317.986  1.00  0.00           P
ATOM    870  P     C A  893     -2.685 116.234 321.371  1.00  0.00           P
ATOM    871  P     G A  894     -1.882 118.511 326.639  1.00  0.00           P
ATOM    872  P     G A  895     -0.852 116.826 332.594  1.00  0.00           P
ATOM    873  P     C A  896      2.461 113.978 335.717  1.00  0.00           P
ATOM    874  P     C A  897      7.428 110.405 337.168  1.00  0.00           P
ATOM    875  P     G A  898     12.867 109.075 334.529  1.00  0.00           P
ATOM    876  P     C A  899     17.862 111.911 331.032  1.00  0.00           P
ATOM    877  P     A A  900     15.603 115.485 327.672  1.00  0.00           P
ATOM    878  P     A A  901     15.239 113.690 321.376  1.00  0.00           P
ATOM    879  P     G A  902     12.539 110.914 317.609  1.00  0.00           P
ATOM    880  P     G A  903      8.200 106.320 320.323  1.00  0.00           P
ATOM    881  P     C A  904      6.179 101.880 323.568  1.00  0.00           P
ATOM    882  P     U A  905      2.162 100.090 327.129  1.00  0.00           P
ATOM    883  P     G A  906     -3.452 100.943 327.820  1.00  0.00           P
ATOM    884  P     A A  907     -6.116 104.025 323.487  1.00  0.00           P
ATOM    885  P     A A  908    -11.848 106.611 321.190  1.00  0.00           P
ATOM    886  P     A A  909    -16.604 109.761 318.784  1.00  0.00           P
ATOM    887  P     C A  910    -19.497 113.093 314.437  1.00  0.00           P
ATOM    888  P     U A  911    -18.870 112.664 308.836  1.00  0.00           P
ATOM    889  P     C A  912    -19.241 109.457 304.029  1.00  0.00           P
ATOM    890  P     A A  913    -19.601 104.165 302.620  1.00  0.00           P
ATOM    891  P     A A  914    -22.449 100.113 300.576  1.00  0.00           P
ATOM    892  P     A A  915    -17.052  95.713 303.657  1.00  0.00           P
ATOM    893  P     G A  916    -10.644  93.971 303.350  1.00  0.00           P
ATOM    894  P     G A  917     -7.886  87.841 307.047  1.00  0.00           P
ATOM    895  P     A A  918     -7.360  83.148 303.538  1.00  0.00           P
ATOM    896  P     A A  919     -7.276  78.195 303.588  1.00  0.00           P
ATOM    897  P     U A  920     -8.927  74.934 298.188  1.00  0.00           P
ATOM    898  P     U A  921     -9.751  73.619 292.855  1.00  0.00           P
ATOM    899  P     G A  922     -9.769  75.132 286.363  1.00  0.00           P
ATOM    900  P     A A  923     -8.306  78.963 281.125  1.00  0.00           P
ATOM    901  P     C A  924     -3.655  84.564 280.669  1.00  0.00           P
ATOM    902  P     G A  925      2.228  87.377 281.864  1.00  0.00           P
ATOM    903  P     G A  926      6.886  86.068 281.296  1.00  0.00           P
ATOM    904  P     G A  927     10.420  87.601 285.454  1.00  0.00           P
ATOM    905  P     G A  928     10.623  81.291 285.365  1.00  0.00           P
ATOM    906  P     G A  929     13.320  75.108 285.918  1.00  0.00           P
ATOM    907  P     C A  930     13.784  70.444 283.701  1.00  0.00           P
ATOM    908  P     C A  931     12.439  66.575 279.654  1.00  0.00           P
ATOM    909  P     C A  932      9.503  65.699 274.726  1.00  0.00           P
ATOM    910  P     G A  933      7.381  68.096 268.243  1.00  0.00           P
ATOM    911  P     C A  934      4.451  71.259 263.900  1.00  0.00           P
ATOM    912  P     A A  935      4.200  77.022 263.936  1.00  0.00           P
ATOM    913  P     C A  936      7.851  83.893 264.146  1.00  0.00           P
ATOM    914  P     A A  937     15.434  83.492 265.778  1.00  0.00           P
ATOM    915  P     A A  938     18.104  80.119 261.173  1.00  0.00           P
ATOM    916  P     G A  939     21.982  79.344 257.335  1.00  0.00           P
ATOM    917  P     C A  940     21.452  81.463 250.615  1.00  0.00           P
ATOM    918  P     G A  941     18.935  85.056 245.942  1.00  0.00           P
ATOM    919  P     G A  942     14.819  90.213 244.334  1.00  0.00           P
ATOM    920  P     U A  943     10.418  94.746 245.784  1.00  0.00           P
ATOM    921  P     G A  944      9.607  99.843 247.601  1.00  0.00           P
ATOM    922  P     G A  945     10.768 105.396 249.822  1.00  0.00           P
ATOM    923  P     A A  946     11.112 109.524 246.391  1.00  0.00           P
ATOM    924  P     G A  947      9.631 111.594 241.705  1.00  0.00           P
ATOM    925  P     C A  948      5.114 111.624 238.445  1.00  0.00           P
ATOM    926  P     A A  949      0.184 108.474 235.841  1.00  0.00           P
ATOM    927  P     U A  950     -4.726 104.082 238.855  1.00  0.00           P
ATOM    928  P     G A  951     -7.905 102.238 243.867  1.00  0.00           P
ATOM    929  P     U A  952    -10.010 102.698 248.866  1.00  0.00           P
ATOM    930  P     G A  953    -10.343 105.842 254.433  1.00  0.00           P
ATOM    931  P     G A  954     -8.591 110.042 258.630  1.00  0.00           P
ATOM    932  P     U A  955     -8.566 115.551 259.147  1.00  0.00           P
ATOM    933  P     U A  956     -9.333 120.413 255.406  1.00  0.00           P
ATOM    934  P     U A  957    -12.828 122.417 250.612  1.00  0.00           P
ATOM    935  P     A A  958    -19.258 122.562 248.495  1.00  0.00           P
```

| | | | | | | | | | |
|---|---|---|---|---|---|---|---|---|---|
| ATOM | 936 | P | A | A | 959 | -18.783 | 118.386 | 251.266 | 1.00 | 0.00 | P |
| ATOM | 937 | P | U | A | 960 | -18.199 | 113.674 | 250.371 | 1.00 | 0.00 | P |
| ATOM | 938 | P | U | A | 961 | -17.552 | 110.153 | 248.802 | 1.00 | 0.00 | P |
| ATOM | 939 | P | C | A | 962 | -21.275 | 106.362 | 253.626 | 1.00 | 0.00 | P |
| ATOM | 940 | P | G | A | 963 | -20.969 | 101.746 | 258.058 | 1.00 | 0.00 | P |
| ATOM | 941 | P | A | A | 964 | -17.106 | 98.510 | 260.749 | 1.00 | 0.00 | P |
| ATOM | 942 | P | A | A | 965 | -10.774 | 98.460 | 259.813 | 1.00 | 0.00 | P |
| ATOM | 943 | P | G | A | 966 | -6.547 | 96.167 | 264.998 | 1.00 | 0.00 | P |
| ATOM | 944 | P | C | A | 967 | -6.582 | 90.497 | 266.748 | 1.00 | 0.00 | P |
| ATOM | 945 | P | A | A | 968 | -4.614 | 88.029 | 260.465 | 1.00 | 0.00 | P |
| ATOM | 946 | P | A | A | 969 | -7.078 | 92.375 | 258.301 | 1.00 | 0.00 | P |
| ATOM | 947 | P | C | A | 970 | -7.598 | 95.404 | 254.999 | 1.00 | 0.00 | P |
| ATOM | 948 | P | G | A | 971 | -5.977 | 97.444 | 250.744 | 1.00 | 0.00 | P |
| ATOM | 949 | P | C | A | 972 | -6.201 | 93.401 | 249.292 | 1.00 | 0.00 | P |
| ATOM | 950 | P | G | A | 973 | -10.480 | 90.697 | 249.291 | 1.00 | 0.00 | P |
| ATOM | 951 | P | A | A | 974 | -16.360 | 92.283 | 247.709 | 1.00 | 0.00 | P |
| ATOM | 952 | P | A | A | 975 | -17.515 | 93.544 | 242.337 | 1.00 | 0.00 | P |
| ATOM | 953 | P | G | A | 976 | -16.775 | 93.385 | 236.792 | 1.00 | 0.00 | P |
| ATOM | 954 | P | A | A | 977 | -19.029 | 99.597 | 238.798 | 1.00 | 0.00 | P |
| ATOM | 955 | P | A | A | 978 | -17.222 | 103.061 | 235.250 | 1.00 | 0.00 | P |
| ATOM | 956 | P | C | A | 979 | -19.574 | 108.155 | 236.531 | 1.00 | 0.00 | P |
| ATOM | 957 | P | C | A | 980 | -25.176 | 108.411 | 235.740 | 1.00 | 0.00 | P |
| ATOM | 958 | P | U | A | 981 | -27.441 | 103.243 | 237.497 | 1.00 | 0.00 | P |
| ATOM | 959 | P | U | A | 982 | -25.500 | 100.154 | 241.604 | 1.00 | 0.00 | P |
| ATOM | 960 | P | A | A | 983 | -27.179 | 105.242 | 244.731 | 1.00 | 0.00 | P |
| ATOM | 961 | P | C | A | 984 | -24.803 | 108.489 | 248.281 | 1.00 | 0.00 | P |
| ATOM | 962 | P | C | A | 985 | -25.848 | 114.685 | 249.276 | 1.00 | 0.00 | P |
| ATOM | 963 | P | A | A | 986 | -27.219 | 120.089 | 247.344 | 1.00 | 0.00 | P |
| ATOM | 964 | P | G | A | 987 | -29.953 | 123.708 | 243.889 | 1.00 | 0.00 | P |
| ATOM | 965 | P | G | A | 988 | -34.721 | 124.485 | 239.810 | 1.00 | 0.00 | P |
| ATOM | 966 | P | C | A | 989 | -39.324 | 122.759 | 237.978 | 1.00 | 0.00 | P |
| ATOM | 967 | P | C | A | 990 | -44.426 | 117.633 | 238.405 | 1.00 | 0.00 | P |
| ATOM | 968 | P | U | A | 991 | -46.630 | 113.974 | 241.036 | 1.00 | 0.00 | P |
| ATOM | 969 | P | U | A | 992 | -50.598 | 111.755 | 244.438 | 1.00 | 0.00 | P |
| ATOM | 970 | P | G | A | 993 | -51.631 | 106.530 | 243.440 | 1.00 | 0.00 | P |
| ATOM | 971 | P | A | A | 994 | -44.577 | 105.309 | 241.854 | 1.00 | 0.00 | P |
| ATOM | 972 | P | C | A | 995 | -44.185 | 99.810 | 240.421 | 1.00 | 0.00 | P |
| ATOM | 973 | P | A | A | 996 | -47.947 | 94.774 | 241.070 | 1.00 | 0.00 | P |
| ATOM | 974 | P | U | A | 997 | -50.608 | 93.303 | 244.789 | 1.00 | 0.00 | P |
| ATOM | 975 | P | G | A | 998 | -56.381 | 92.992 | 245.961 | 1.00 | 0.00 | P |
| ATOM | 976 | P | C | A | 998A | -61.651 | 96.614 | 247.265 | 1.00 | 0.00 | P |
| ATOM | 977 | P | U | A | 999 | -65.935 | 99.973 | 247.053 | 1.00 | 0.00 | P |
| ATOM | 978 | P | A | A1000 | | -69.558 | 103.702 | 244.599 | 1.00 | 0.00 | P |
| ATOM | 979 | P | G | A1001 | | -70.768 | 107.412 | 240.270 | 1.00 | 0.00 | P |
| ATOM | 980 | P | G | A1002 | | -70.283 | 108.927 | 234.658 | 1.00 | 0.00 | P |
| ATOM | 981 | P | G | A1003 | | -67.507 | 108.397 | 229.360 | 1.00 | 0.00 | P |
| ATOM | 982 | P | A | A1004 | | -63.910 | 104.528 | 225.356 | 1.00 | 0.00 | P |
| ATOM | 983 | P | A | A1005 | | -57.918 | 101.363 | 227.364 | 1.00 | 0.00 | P |
| ATOM | 984 | P | C | A1006 | | -53.816 | 99.107 | 227.887 | 1.00 | 0.00 | P |
| ATOM | 985 | P | C | A1007 | | -49.528 | 98.668 | 222.987 | 1.00 | 0.00 | P |
| ATOM | 986 | P | C | A1008 | | -46.584 | 101.179 | 218.489 | 1.00 | 0.00 | P |
| ATOM | 987 | P | G | A1009 | | -44.198 | 106.072 | 215.570 | 1.00 | 0.00 | P |
| ATOM | 988 | P | G | A1010 | | -42.979 | 112.644 | 215.375 | 1.00 | 0.00 | P |
| ATOM | 989 | P | G | A1011 | | -42.496 | 118.561 | 216.446 | 1.00 | 0.00 | P |
| ATOM | 990 | P | U | A1012 | | -40.968 | 122.717 | 219.181 | 1.00 | 0.00 | P |
| ATOM | 991 | P | G | A1013 | | -37.257 | 123.727 | 223.284 | 1.00 | 0.00 | P |
| ATOM | 992 | P | A | A1014 | | -32.660 | 121.283 | 225.775 | 1.00 | 0.00 | P |
| ATOM | 993 | P | A | A1015 | | -33.132 | 115.485 | 225.842 | 1.00 | 0.00 | P |
| ATOM | 994 | P | A | A1016 | | -36.448 | 110.825 | 228.825 | 1.00 | 0.00 | P |
| ATOM | 995 | P | G | A1017 | | -40.846 | 110.074 | 232.716 | 1.00 | 0.00 | P |
| ATOM | 996 | P | C | A1018 | | -45.873 | 113.713 | 233.926 | 1.00 | 0.00 | P |
| ATOM | 997 | P | C | A1019 | | -50.041 | 117.406 | 231.899 | 1.00 | 0.00 | P |
| ATOM | 998 | P | U | A1020 | | -53.763 | 118.745 | 227.444 | 1.00 | 0.00 | P |
| ATOM | 999 | P | G | A1021 | | -56.039 | 116.920 | 221.959 | 1.00 | 0.00 | P |
| ATOM | 1000 | P | G | A1022 | | -58.533 | 113.413 | 216.912 | 1.00 | 0.00 | P |
| ATOM | 1001 | P | G | A1023 | | -60.030 | 107.858 | 213.458 | 1.00 | 0.00 | P |
| ATOM | 1002 | P | G | A1024 | | -62.001 | 102.787 | 214.154 | 1.00 | 0.00 | P |
| ATOM | 1003 | P | U | A1025 | | -63.163 | 100.418 | 217.475 | 1.00 | 0.00 | P |
| ATOM | 1004 | P | G | A1026 | | -67.233 | 97.236 | 220.363 | 1.00 | 0.00 | P |
| ATOM | 1005 | P | C | A1027 | | -68.481 | 90.735 | 222.225 | 1.00 | 0.00 | P |
| ATOM | 1006 | P | C | A1028 | | -68.517 | 87.401 | 226.220 | 1.00 | 0.00 | P |
| ATOM | 1007 | P | C | A1028A | | -74.065 | 86.192 | 227.949 | 1.00 | 0.00 | P |
| ATOM | 1008 | P | C | A1028B | | -79.771 | 87.981 | 228.942 | 1.00 | 0.00 | P |
| ATOM | 1009 | P | G | A1029 | | -83.879 | 90.239 | 227.264 | 1.00 | 0.00 | P |
| ATOM | 1010 | P | C | A1030 | | -86.345 | 92.652 | 222.830 | 1.00 | 0.00 | P |
| ATOM | 1011 | P | G | A1031 | | -81.917 | 94.677 | 219.823 | 1.00 | 0.00 | P |
| ATOM | 1012 | P | A | A1032 | | -78.752 | 100.255 | 219.969 | 1.00 | 0.00 | P |
| ATOM | 1013 | P | G | A1032A | | -77.054 | 104.833 | 222.156 | 1.00 | 0.00 | P |
| ATOM | 1014 | P | G | A1032B | | -77.223 | 105.195 | 228.990 | 1.00 | 0.00 | P |
| ATOM | 1015 | P | G | A1033 | | -75.848 | 102.827 | 233.904 | 1.00 | 0.00 | P |
| ATOM | 1016 | P | G | A1034 | | -72.603 | 99.419 | 237.691 | 1.00 | 0.00 | P |
| ATOM | 1017 | P | A | A1035 | | -67.485 | 96.059 | 238.604 | 1.00 | 0.00 | P |
| ATOM | 1018 | P | G | A1036 | | -62.227 | 93.637 | 237.958 | 1.00 | 0.00 | P |
| ATOM | 1019 | P | C | A1037 | | -56.833 | 93.763 | 236.272 | 1.00 | 0.00 | P |
| ATOM | 1020 | P | C | A1038 | | -53.668 | 98.368 | 234.776 | 1.00 | 0.00 | P |
| ATOM | 1021 | P | C | A1039 | | -53.214 | 104.564 | 235.206 | 1.00 | 0.00 | P |
| ATOM | 1022 | P | U | A1040 | | -53.913 | 110.237 | 236.856 | 1.00 | 0.00 | P |

| | | | | | | | | | |
|---|---|---|---|---|---|---|---|---|---|
| ATOM | 1023 | P | A | A1041 | -56.080 | 114.244 | 240.298 | 1.00 | 0.00 | P |
| ATOM | 1024 | P | G | A1042 | -57.712 | 115.737 | 245.656 | 1.00 | 0.00 | P |
| ATOM | 1025 | P | C | A1043 | -57.787 | 112.792 | 251.491 | 1.00 | 0.00 | P |
| ATOM | 1026 | P | A | A1044 | -56.929 | 108.558 | 255.248 | 1.00 | 0.00 | P |
| ATOM | 1027 | P | C | A1045 | -53.471 | 103.094 | 256.119 | 1.00 | 0.00 | P |
| ATOM | 1028 | P | A | A1046 | -48.607 | 99.090 | 253.564 | 1.00 | 0.00 | P |
| ATOM | 1029 | P | G | A1047 | -42.991 | 100.382 | 249.489 | 1.00 | 0.00 | P |
| ATOM | 1030 | P | G | A1048 | -37.647 | 101.668 | 249.205 | 1.00 | 0.00 | P |
| ATOM | 1031 | P | U | A1049 | -34.555 | 98.910 | 252.845 | 1.00 | 0.00 | P |
| ATOM | 1032 | P | G | A1050 | -32.190 | 103.997 | 252.564 | 1.00 | 0.00 | P |
| ATOM | 1033 | P | C | A1051 | -28.348 | 104.098 | 257.708 | 1.00 | 0.00 | P |
| ATOM | 1034 | P | U | A1052 | -26.034 | 103.047 | 262.757 | 1.00 | 0.00 | P |
| ATOM | 1035 | P | G | A1053 | -24.961 | 99.823 | 266.407 | 1.00 | 0.00 | P |
| ATOM | 1036 | P | C | A1054 | -22.390 | 93.905 | 268.957 | 1.00 | 0.00 | P |
| ATOM | 1037 | P | A | A1055 | -28.707 | 95.747 | 269.625 | 1.00 | 0.00 | P |
| ATOM | 1038 | P | U | A1056 | -28.399 | 89.666 | 271.362 | 1.00 | 0.00 | P |
| ATOM | 1039 | P | G | A1057 | -30.562 | 84.145 | 266.734 | 1.00 | 0.00 | P |
| ATOM | 1040 | P | G | A1058 | -28.223 | 82.616 | 261.047 | 1.00 | 0.00 | P |
| ATOM | 1041 | P | C | A1059 | -24.914 | 81.775 | 256.755 | 1.00 | 0.00 | P |
| ATOM | 1042 | P | C | A1060 | -19.243 | 82.398 | 255.410 | 1.00 | 0.00 | P |
| ATOM | 1043 | P | G | A1061 | -14.753 | 83.573 | 258.418 | 1.00 | 0.00 | P |
| ATOM | 1044 | P | U | A1062 | -9.841 | 85.069 | 260.797 | 1.00 | 0.00 | P |
| ATOM | 1045 | P | C | A1063 | -6.514 | 83.878 | 264.964 | 1.00 | 0.00 | P |
| ATOM | 1046 | P | G | A1064 | -3.790 | 80.217 | 269.216 | 1.00 | 0.00 | P |
| ATOM | 1047 | P | U | A1065 | -6.561 | 77.112 | 264.203 | 1.00 | 0.00 | P |
| ATOM | 1048 | P | C | A1066 | -3.831 | 71.456 | 264.663 | 1.00 | 0.00 | P |
| ATOM | 1049 | P | A | A1067 | -2.710 | 69.170 | 269.372 | 1.00 | 0.00 | P |
| ATOM | 1050 | P | G | A1068 | -6.102 | 67.826 | 273.923 | 1.00 | 0.00 | P |
| ATOM | 1051 | P | C | A1069 | -11.256 | 71.107 | 277.037 | 1.00 | 0.00 | P |
| ATOM | 1052 | P | U | A1070 | -16.635 | 71.430 | 279.163 | 1.00 | 0.00 | P |
| ATOM | 1053 | P | C | A1071 | -20.953 | 67.170 | 282.431 | 1.00 | 0.00 | P |
| ATOM | 1054 | P | G | A1072 | -24.984 | 63.295 | 284.030 | 1.00 | 0.00 | P |
| ATOM | 1055 | P | U | A1073 | -26.366 | 59.331 | 287.231 | 1.00 | 0.00 | P |
| ATOM | 1056 | P | G | A1074 | -24.226 | 56.689 | 291.009 | 1.00 | 0.00 | P |
| ATOM | 1057 | P | C | A1075 | -20.397 | 54.515 | 294.604 | 1.00 | 0.00 | P |
| ATOM | 1058 | P | C | A1076 | -16.155 | 56.013 | 298.360 | 1.00 | 0.00 | P |
| ATOM | 1059 | P | G | A1077 | -14.759 | 60.670 | 301.178 | 1.00 | 0.00 | P |
| ATOM | 1060 | P | U | A1078 | -15.313 | 64.637 | 303.882 | 1.00 | 0.00 | P |
| ATOM | 1061 | P | G | A1079 | -19.056 | 68.383 | 301.572 | 1.00 | 0.00 | P |
| ATOM | 1062 | P | A | A1080 | -18.972 | 72.332 | 297.241 | 1.00 | 0.00 | P |
| ATOM | 1063 | P | G | A1081 | -18.371 | 73.415 | 293.287 | 1.00 | 0.00 | P |
| ATOM | 1064 | P | G | A1082 | -12.984 | 70.387 | 290.374 | 1.00 | 0.00 | P |
| ATOM | 1065 | P | U | A1083 | -9.015 | 66.221 | 289.292 | 1.00 | 0.00 | P |
| ATOM | 1066 | P | G | A1084 | -8.585 | 61.051 | 287.177 | 1.00 | 0.00 | P |
| ATOM | 1067 | P | U | A1085 | -9.720 | 58.812 | 281.839 | 1.00 | 0.00 | P |
| ATOM | 1068 | P | U | A1086 | -5.656 | 63.784 | 281.413 | 1.00 | 0.00 | P |
| ATOM | 1069 | P | G | A1087 | -0.878 | 64.670 | 284.051 | 1.00 | 0.00 | P |
| ATOM | 1070 | P | G | A1088 | 3.996 | 62.295 | 284.774 | 1.00 | 0.00 | P |
| ATOM | 1071 | P | G | A1089 | 7.520 | 59.740 | 281.284 | 1.00 | 0.00 | P |
| ATOM | 1072 | P | U | A1090 | 8.702 | 58.222 | 275.898 | 1.00 | 0.00 | P |
| ATOM | 1073 | P | U | A1091 | 7.008 | 58.785 | 270.184 | 1.00 | 0.00 | P |
| ATOM | 1074 | P | A | A1092 | 4.253 | 61.219 | 265.740 | 1.00 | 0.00 | P |
| ATOM | 1075 | P | A | A1093 | 1.192 | 64.737 | 268.947 | 1.00 | 0.00 | P |
| ATOM | 1076 | P | G | A1094 | -2.909 | 64.279 | 272.695 | 1.00 | 0.00 | P |
| ATOM | 1077 | P | U | A1095 | -7.603 | 61.154 | 270.916 | 1.00 | 0.00 | P |
| ATOM | 1078 | P | C | A1096 | -7.109 | 55.737 | 271.012 | 1.00 | 0.00 | P |
| ATOM | 1079 | P | C | A1097 | -4.821 | 50.720 | 274.196 | 1.00 | 0.00 | P |
| ATOM | 1080 | P | C | A1098 | -2.309 | 47.750 | 278.285 | 1.00 | 0.00 | P |
| ATOM | 1081 | P | G | A1099 | -1.822 | 47.812 | 284.367 | 1.00 | 0.00 | P |
| ATOM | 1082 | P | C | A1100 | -3.232 | 49.840 | 289.475 | 1.00 | 0.00 | P |
| ATOM | 1083 | P | A | A1101 | -7.328 | 52.227 | 292.974 | 1.00 | 0.00 | P |
| ATOM | 1084 | P | A | A1102 | -8.626 | 57.823 | 290.338 | 1.00 | 0.00 | P |
| ATOM | 1085 | P | C | A1103 | -10.097 | 52.614 | 285.679 | 1.00 | 0.00 | P |
| ATOM | 1086 | P | G | A1104 | -13.749 | 50.268 | 281.738 | 1.00 | 0.00 | P |
| ATOM | 1087 | P | A | A1105 | -17.462 | 51.721 | 277.639 | 1.00 | 0.00 | P |
| ATOM | 1088 | P | G | A1106 | -19.949 | 55.522 | 272.695 | 1.00 | 0.00 | P |
| ATOM | 1089 | P | C | A1107 | -21.443 | 59.564 | 269.351 | 1.00 | 0.00 | P |
| ATOM | 1090 | P | G | A1108 | -20.809 | 65.000 | 266.524 | 1.00 | 0.00 | P |
| ATOM | 1091 | P | C | A1109 | -14.909 | 66.488 | 264.602 | 1.00 | 0.00 | P |
| ATOM | 1092 | P | A | A1110 | -10.423 | 64.933 | 262.576 | 1.00 | 0.00 | P |
| ATOM | 1093 | P | A | A1111 | -8.958 | 60.327 | 259.585 | 1.00 | 0.00 | P |
| ATOM | 1094 | P | C | A1112 | -10.563 | 56.628 | 257.434 | 1.00 | 0.00 | P |
| ATOM | 1095 | P | C | A1113 | -14.386 | 57.192 | 253.240 | 1.00 | 0.00 | P |
| ATOM | 1096 | P | C | A1114 | -15.943 | 59.386 | 247.297 | 1.00 | 0.00 | P |
| ATOM | 1097 | P | C | A1115 | -12.455 | 61.772 | 241.656 | 1.00 | 0.00 | P |
| ATOM | 1098 | P | C | A1116 | -7.142 | 62.287 | 237.846 | 1.00 | 0.00 | P |
| ATOM | 1099 | P | G | A1117 | -2.166 | 61.362 | 238.588 | 1.00 | 0.00 | P |
| ATOM | 1100 | P | C | A1118 | 1.312 | 57.612 | 237.795 | 1.00 | 0.00 | P |
| ATOM | 1101 | P | C | A1119 | 2.124 | 52.560 | 235.110 | 1.00 | 0.00 | P |
| ATOM | 1102 | P | G | A1120 | -0.027 | 47.719 | 232.815 | 1.00 | 0.00 | P |
| ATOM | 1103 | P | U | A1121 | -4.621 | 44.144 | 230.817 | 1.00 | 0.00 | P |
| ATOM | 1104 | P | U | A1122 | -9.648 | 42.752 | 228.941 | 1.00 | 0.00 | P |
| ATOM | 1105 | P | A | A1123 | -14.550 | 44.516 | 226.633 | 1.00 | 0.00 | P |
| ATOM | 1106 | P | G | A1124 | -15.611 | 47.539 | 223.113 | 1.00 | 0.00 | P |
| ATOM | 1107 | P | U | A1125 | -15.383 | 53.551 | 218.994 | 1.00 | 0.00 | P |
| ATOM | 1108 | P | U | A1126 | -13.487 | 60.294 | 220.482 | 1.00 | 0.00 | P |
| ATOM | 1109 | P | G | A1127 | -7.485 | 62.858 | 219.387 | 1.00 | 0.00 | P |

| | | | | | | | | | |
|---|---|---|---|---|---|---|---|---|---|
| ATOM | 1110 | P | C | A1128 | -0.893 | 60.022 | 217.870 | 1.00 | 0.00 | P |
| ATOM | 1111 | P | C | A1129 | 3.537 | 55.692 | 215.186 | 1.00 | 0.00 | P |
| ATOM | 1112 | P | A | A1130 | 5.729 | 51.249 | 213.757 | 1.00 | 0.00 | P |
| ATOM | 1113 | P | G | A1131 | 5.967 | 47.810 | 215.343 | 1.00 | 0.00 | P |
| ATOM | 1114 | P | C | A1132 | 4.553 | 46.589 | 209.917 | 1.00 | 0.00 | P |
| ATOM | 1115 | P | G | A1133 | 2.771 | 46.664 | 204.237 | 1.00 | 0.00 | P |
| ATOM | 1116 | P | G | A1134 | 1.261 | 49.361 | 199.612 | 1.00 | 0.00 | P |
| ATOM | 1117 | P | U | A1135 | 0.173 | 54.519 | 196.788 | 1.00 | 0.00 | P |
| ATOM | 1118 | P | U | A1136 | 0.736 | 60.985 | 196.894 | 1.00 | 0.00 | P |
| ATOM | 1119 | P | C | A1137 | 1.892 | 64.838 | 200.390 | 1.00 | 0.00 | P |
| ATOM | 1120 | P | G | A1138 | 3.479 | 64.556 | 205.028 | 1.00 | 0.00 | P |
| ATOM | 1121 | P | G | A1139 | 1.198 | 62.922 | 210.279 | 1.00 | 0.00 | P |
| ATOM | 1122 | P | C | A1140 | -5.100 | 62.960 | 211.150 | 1.00 | 0.00 | P |
| ATOM | 1123 | P | C | A1141 | -8.822 | 60.520 | 207.616 | 1.00 | 0.00 | P |
| ATOM | 1124 | P | G | A1142 | -11.471 | 56.205 | 206.777 | 1.00 | 0.00 | P |
| ATOM | 1125 | P | G | A1143 | -13.061 | 50.860 | 208.570 | 1.00 | 0.00 | P |
| ATOM | 1126 | P | G | A1144 | -11.323 | 46.881 | 212.795 | 1.00 | 0.00 | P |
| ATOM | 1127 | P | C | A1145 | -9.153 | 45.821 | 216.537 | 1.00 | 0.00 | P |
| ATOM | 1128 | P | A | A1146 | -6.659 | 46.634 | 223.315 | 1.00 | 0.00 | P |
| ATOM | 1129 | P | C | A1147 | -2.086 | 48.744 | 225.494 | 1.00 | 0.00 | P |
| ATOM | 1130 | P | U | A1148 | -0.109 | 53.524 | 227.800 | 1.00 | 0.00 | P |
| ATOM | 1131 | P | C | A1149 | -1.865 | 58.236 | 230.086 | 1.00 | 0.00 | P |
| ATOM | 1132 | P | U | A1150 | -7.368 | 61.265 | 231.173 | 1.00 | 0.00 | P |
| ATOM | 1133 | P | A | A1151 | -12.682 | 61.385 | 232.941 | 1.00 | 0.00 | P |
| ATOM | 1134 | P | A | A1152 | -16.752 | 57.491 | 236.712 | 1.00 | 0.00 | P |
| ATOM | 1135 | P | C | A1153 | -16.248 | 52.434 | 240.890 | 1.00 | 0.00 | P |
| ATOM | 1136 | P | G | A1154 | -13.504 | 47.504 | 243.525 | 1.00 | 0.00 | P |
| ATOM | 1137 | P | G | A1155 | -8.847 | 44.629 | 245.381 | 1.00 | 0.00 | P |
| ATOM | 1138 | P | G | A1156 | -2.611 | 47.227 | 246.970 | 1.00 | 0.00 | P |
| ATOM | 1139 | P | A | A1157 | -0.446 | 48.478 | 251.498 | 1.00 | 0.00 | P |
| ATOM | 1140 | P | C | A1158 | -3.582 | 50.096 | 256.737 | 1.00 | 0.00 | P |
| ATOM | 1141 | P | U | A1159 | -1.313 | 47.997 | 261.998 | 1.00 | 0.00 | P |
| ATOM | 1142 | P | G | A1160 | 0.604 | 43.078 | 258.774 | 1.00 | 0.00 | P |
| ATOM | 1143 | P | C | A1161 | 5.397 | 39.230 | 258.334 | 1.00 | 0.00 | P |
| ATOM | 1144 | P | C | A1162 | 11.239 | 38.014 | 260.251 | 1.00 | 0.00 | P |
| ATOM | 1145 | P | C | A1163 | 15.475 | 39.613 | 263.503 | 1.00 | 0.00 | P |
| ATOM | 1146 | P | G | A1164 | 17.404 | 42.351 | 268.320 | 1.00 | 0.00 | P |
| ATOM | 1147 | P | C | A1165 | 16.361 | 44.892 | 273.000 | 1.00 | 0.00 | P |
| ATOM | 1148 | P | G | A1166 | 12.819 | 45.681 | 277.567 | 1.00 | 0.00 | P |
| ATOM | 1149 | P | A | A1167 | 8.234 | 44.344 | 279.953 | 1.00 | 0.00 | P |
| ATOM | 1150 | P | A | A1169 | 5.266 | 41.422 | 275.367 | 1.00 | 0.00 | P |
| ATOM | 1151 | P | A | A1170 | 1.110 | 42.886 | 271.126 | 1.00 | 0.00 | P |
| ATOM | 1152 | P | G | A1171 | -1.148 | 47.079 | 267.728 | 1.00 | 0.00 | P |
| ATOM | 1153 | P | C | A1172 | 2.516 | 52.835 | 266.856 | 1.00 | 0.00 | P |
| ATOM | 1154 | P | G | A1173 | 6.952 | 55.896 | 265.728 | 1.00 | 0.00 | P |
| ATOM | 1155 | P | G | A1174 | 11.888 | 56.705 | 263.236 | 1.00 | 0.00 | P |
| ATOM | 1156 | P | G | A1175 | 15.335 | 54.643 | 259.016 | 1.00 | 0.00 | P |
| ATOM | 1157 | P | A | A1176 | 14.504 | 49.843 | 255.282 | 1.00 | 0.00 | P |
| ATOM | 1158 | P | G | A1177 | 13.992 | 45.946 | 251.275 | 1.00 | 0.00 | P |
| ATOM | 1159 | P | G | A1178 | 11.296 | 44.128 | 246.984 | 1.00 | 0.00 | P |
| ATOM | 1160 | P | A | A1179 | 8.612 | 46.059 | 242.401 | 1.00 | 0.00 | P |
| ATOM | 1161 | P | A | A1180 | 7.668 | 51.280 | 244.926 | 1.00 | 0.00 | P |
| ATOM | 1162 | P | G | A1181 | 4.295 | 52.224 | 249.883 | 1.00 | 0.00 | P |
| ATOM | 1163 | P | G | A1182 | 4.816 | 54.807 | 256.646 | 1.00 | 0.00 | P |
| ATOM | 1164 | P | A | A1183 | 1.712 | 58.059 | 257.511 | 1.00 | 0.00 | P |
| ATOM | 1165 | P | G | A1184 | 1.616 | 58.768 | 252.817 | 1.00 | 0.00 | P |
| ATOM | 1166 | P | G | A1185 | 3.416 | 63.171 | 251.084 | 1.00 | 0.00 | P |
| ATOM | 1167 | P | G | A1186 | 0.751 | 67.193 | 249.799 | 1.00 | 0.00 | P |
| ATOM | 1168 | P | G | A1187 | -3.656 | 70.587 | 250.169 | 1.00 | 0.00 | P |
| ATOM | 1169 | P | A | A1188 | -8.483 | 71.988 | 251.359 | 1.00 | 0.00 | P |
| ATOM | 1170 | P | C | A1189 | -13.807 | 71.268 | 251.812 | 1.00 | 0.00 | P |
| ATOM | 1171 | P | G | A1190 | -15.112 | 70.409 | 258.546 | 1.00 | 0.00 | P |
| ATOM | 1172 | P | A | A1191 | -14.712 | 69.306 | 263.509 | 1.00 | 0.00 | P |
| ATOM | 1173 | P | C | A1192 | -18.058 | 71.953 | 266.773 | 1.00 | 0.00 | P |
| ATOM | 1174 | P | G | A1193 | -20.068 | 75.719 | 272.481 | 1.00 | 0.00 | P |
| ATOM | 1175 | P | U | A1194 | -18.159 | 81.162 | 275.736 | 1.00 | 0.00 | P |
| ATOM | 1176 | P | C | A1195 | -14.918 | 85.295 | 274.395 | 1.00 | 0.00 | P |
| ATOM | 1177 | P | U | A1196 | -14.919 | 90.540 | 272.677 | 1.00 | 0.00 | P |
| ATOM | 1178 | P | G | A1197 | -18.754 | 91.588 | 270.270 | 1.00 | 0.00 | P |
| ATOM | 1179 | P | G | A1198 | -16.687 | 94.794 | 267.461 | 1.00 | 0.00 | P |
| ATOM | 1180 | P | U | A1199 | -18.853 | 97.083 | 263.272 | 1.00 | 0.00 | P |
| ATOM | 1181 | P | C | A1200 | -22.341 | 94.764 | 259.736 | 1.00 | 0.00 | P |
| ATOM | 1182 | P | A | A1201 | -28.086 | 97.587 | 258.884 | 1.00 | 0.00 | P |
| ATOM | 1183 | P | G | A1202 | -27.095 | 95.901 | 253.845 | 1.00 | 0.00 | P |
| ATOM | 1184 | P | C | A1203 | -30.824 | 92.540 | 251.685 | 1.00 | 0.00 | P |
| ATOM | 1185 | P | A | A1204 | -34.896 | 89.858 | 252.946 | 1.00 | 0.00 | P |
| ATOM | 1186 | P | U | A1205 | -39.112 | 89.934 | 257.773 | 1.00 | 0.00 | P |
| ATOM | 1187 | P | G | A1206 | -38.550 | 91.159 | 264.868 | 1.00 | 0.00 | P |
| ATOM | 1188 | P | G | A1207 | -40.190 | 96.454 | 267.734 | 1.00 | 0.00 | P |
| ATOM | 1189 | P | C | A1208 | -39.299 | 102.607 | 268.059 | 1.00 | 0.00 | P |
| ATOM | 1190 | P | C | A1209 | -40.005 | 108.058 | 265.421 | 1.00 | 0.00 | P |
| ATOM | 1191 | P | C | A1210 | -39.733 | 112.513 | 260.529 | 1.00 | 0.00 | P |
| ATOM | 1192 | P | U | A1211 | -42.823 | 113.558 | 256.238 | 1.00 | 0.00 | P |
| ATOM | 1193 | P | U | A1212 | -45.540 | 115.640 | 251.930 | 1.00 | 0.00 | P |
| ATOM | 1194 | P | A | A1213 | -39.657 | 117.957 | 251.136 | 1.00 | 0.00 | P |
| ATOM | 1195 | P | C | A1214 | -36.123 | 112.356 | 254.162 | 1.00 | 0.00 | P |
| ATOM | 1196 | P | G | A1215 | -35.564 | 110.334 | 251.024 | 1.00 | 0.00 | P |

```
ATOM   1197  P    G A1216     -36.620 106.014 247.032  1.00  0.00           P
ATOM   1198  P    C A1217     -36.665 106.194 241.040  1.00  0.00           P
ATOM   1199  P    C A1218     -34.728 107.499 236.148  1.00  0.00           P
ATOM   1200  P    U A1219     -31.303 110.488 232.477  1.00  0.00           P
ATOM   1201  P    G A1220     -26.574 113.400 230.954  1.00  0.00           P
ATOM   1202  P    G A1221     -21.379 114.791 233.567  1.00  0.00           P
ATOM   1203  P    G A1222     -17.379 114.756 237.789  1.00  0.00           P
ATOM   1204  P    C A1223     -15.665 112.107 242.380  1.00  0.00           P
ATOM   1205  P    G A1224     -12.720 109.105 244.239  1.00  0.00           P
ATOM   1206  P    A A1225     -10.123 113.198 241.943  1.00  0.00           P
ATOM   1207  P    C A1226      -6.465 115.941 243.958  1.00  0.00           P
ATOM   1208  P    A A1227      -2.213 119.237 245.421  1.00  0.00           P
ATOM   1209  P    C A1228       2.747 119.285 248.647  1.00  0.00           P
ATOM   1210  P    A A1229       5.474 115.114 252.246  1.00  0.00           P
ATOM   1211  P    C A1230       5.335 109.731 253.842  1.00  0.00           P
ATOM   1212  P    G A1231       3.488 102.491 254.700  1.00  0.00           P
ATOM   1213  P    U A1232       2.411  96.104 251.136  1.00  0.00           P
ATOM   1214  P    G A1233       2.328  93.114 246.008  1.00  0.00           P
ATOM   1215  P    C A1234       4.300  93.899 239.871  1.00  0.00           P
ATOM   1216  P    U A1235       7.333  95.573 235.015  1.00  0.00           P
ATOM   1217  P    A A1236      11.503  97.952 232.073  1.00  0.00           P
ATOM   1218  P    C A1237      17.402 100.514 232.397  1.00  0.00           P
ATOM   1219  P    A A1238      20.669  97.902 234.411  1.00  0.00           P
ATOM   1220  P    A A1239      24.379  94.612 232.885  1.00  0.00           P
ATOM   1221  P    U A1240      21.183  90.963 230.137  1.00  0.00           P
ATOM   1222  P    G A1241      16.500  88.238 230.721  1.00  0.00           P
ATOM   1223  P    C A1242      13.665  91.819 227.258  1.00  0.00           P
ATOM   1224  P    C A1243      11.720  92.941 221.856  1.00  0.00           P
ATOM   1225  P    C A1244      10.687  91.434 216.402  1.00  0.00           P
ATOM   1226  P    A A1245       9.681  87.050 212.728  1.00  0.00           P
ATOM   1227  P    C A1246       8.847  81.480 211.510  1.00  0.00           P
ATOM   1228  P    U A1247       7.548  76.179 213.288  1.00  0.00           P
ATOM   1229  P    A A1248       9.338  72.576 219.321  1.00  0.00           P
ATOM   1230  P    C A1249       6.277  70.522 223.987  1.00  0.00           P
ATOM   1231  P    A A1250       1.679  70.134 228.039  1.00  0.00           P
ATOM   1232  P    A A1251      -3.359  70.278 230.835  1.00  0.00           P
ATOM   1233  P    A A1252      -8.946  71.103 233.169  1.00  0.00           P
ATOM   1234  P    G A1253     -14.002  74.876 233.059  1.00  0.00           P
ATOM   1235  P    C A1254     -16.645  78.906 228.487  1.00  0.00           P
ATOM   1236  P    G A1255     -18.640  81.450 223.348  1.00  0.00           P
ATOM   1237  P    A A1256     -22.111  80.975 220.005  1.00  0.00           P
ATOM   1238  P    U A1257     -25.408  87.268 219.912  1.00  0.00           P
ATOM   1239  P    G A1258     -22.083  89.052 218.985  1.00  0.00           P
ATOM   1240  P    C A1259     -16.921  87.169 220.158  1.00  0.00           P
ATOM   1241  P    C A1260     -11.673  86.034 219.514  1.00  0.00           P
ATOM   1242  P    A A1261      -8.817  85.140 212.838  1.00  0.00           P
ATOM   1243  P    C A1262      -4.665  82.277 210.386  1.00  0.00           P
ATOM   1244  P    C A1263      -3.117  84.024 204.737  1.00  0.00           P
ATOM   1245  P    C A1264      -3.066  88.489 201.300  1.00  0.00           P
ATOM   1246  P    G A1265      -3.577  94.381 199.972  1.00  0.00           P
ATOM   1247  P    G A1266      -2.699  99.367 201.815  1.00  0.00           P
ATOM   1248  P    C A1267      -0.078 102.118 205.813  1.00  0.00           P
ATOM   1249  P    A A1268      -0.174  97.352 209.279  1.00  0.00           P
ATOM   1250  P    A A1269      -3.741  95.794 214.209  1.00  0.00           P
ATOM   1251  P    C A1270      -8.306  95.514 217.570  1.00  0.00           P
ATOM   1252  P    G A1271     -13.626  96.262 213.753  1.00  0.00           P
ATOM   1253  P    G A1272     -16.845  96.035 208.722  1.00  0.00           P
ATOM   1254  P    G A1273     -18.650  92.848 204.225  1.00  0.00           P
ATOM   1255  P    G A1274     -18.916  87.356 202.241  1.00  0.00           P
ATOM   1256  P    A A1275     -18.311  81.231 204.032  1.00  0.00           P
ATOM   1257  P    G A1276     -17.909  75.953 205.777  1.00  0.00           P
ATOM   1258  P    C A1277     -17.829  72.180 210.690  1.00  0.00           P
ATOM   1259  P    U A1278     -21.504  70.739 214.100  1.00  0.00           P
ATOM   1260  P    A A1279     -24.934  73.096 217.704  1.00  0.00           P
ATOM   1261  P    A A1280     -22.699  69.384 221.095  1.00  0.00           P
ATOM   1262  P    U A1281     -17.747  68.077 221.814  1.00  0.00           P
ATOM   1263  P    C A1282     -16.047  65.197 215.849  1.00  0.00           P
ATOM   1264  P    G A1283     -11.936  68.880 213.493  1.00  0.00           P
ATOM   1265  P    C A1284      -8.317  73.204 214.568  1.00  0.00           P
ATOM   1266  P    A A1285      -7.441  79.419 219.910  1.00  0.00           P
ATOM   1267  P    A A1286      -2.460  81.151 216.028  1.00  0.00           P
ATOM   1268  P    A A1287       2.736  81.521 219.390  1.00  0.00           P
ATOM   1269  P    A A1288       3.135  81.570 224.197  1.00  0.00           P
ATOM   1270  P    A A1289       6.313  82.638 229.195  1.00  0.00           P
ATOM   1271  P    G A1290      11.492  84.441 228.261  1.00  0.00           P
ATOM   1272  P    G A1291      14.268  79.371 228.715  1.00  0.00           P
ATOM   1273  P    U A1292      17.753  75.897 225.480  1.00  0.00           P
ATOM   1274  P    G A1293      21.055  76.312 221.008  1.00  0.00           P
ATOM   1275  P    G A1294      23.896  79.817 217.368  1.00  0.00           P
ATOM   1276  P    G A1295      25.547  85.116 215.416  1.00  0.00           P
ATOM   1277  P    C A1296      26.307  90.756 215.301  1.00  0.00           P
ATOM   1278  P    C A1297      25.732  96.033 219.892  1.00  0.00           P
ATOM   1279  P    C A1298      30.238  96.190 225.023  1.00  0.00           P
ATOM   1280  P    A A1299      30.043  99.006 230.957  1.00  0.00           P
ATOM   1281  P    G A1300      27.579 104.530 230.854  1.00  0.00           P
ATOM   1282  P    U A1301      22.135 105.376 228.224  1.00  0.00           P
ATOM   1283  P    U A1302      20.527 103.822 223.387  1.00  0.00           P
```

| | | | | | | | | | |
|---|---|---|---|---|---|---|---|---|---|
| ATOM | 1284 | P | C | A1303 | 18.832 | 97.955 | 222.150 | 1.00 | 0.00 | P |
| ATOM | 1285 | P | G | A1304 | 16.703 | 97.119 | 227.434 | 1.00 | 0.00 | P |
| ATOM | 1286 | P | G | A1305 | 12.405 | 99.069 | 229.391 | 1.00 | 0.00 | P |
| ATOM | 1287 | P | A | A1306 | 7.083 | 103.926 | 230.267 | 1.00 | 0.00 | P |
| ATOM | 1288 | P | U | A1307 | 3.502 | 107.823 | 233.812 | 1.00 | 0.00 | P |
| ATOM | 1289 | P | U | A1308 | 2.130 | 112.908 | 232.089 | 1.00 | 0.00 | P |
| ATOM | 1290 | P | G | A1309 | 0.871 | 116.296 | 226.864 | 1.00 | 0.00 | P |
| ATOM | 1291 | P | G | A1310 | -0.624 | 117.518 | 221.494 | 1.00 | 0.00 | P |
| ATOM | 1292 | P | G | A1311 | -2.845 | 115.178 | 216.412 | 1.00 | 0.00 | P |
| ATOM | 1293 | P | G | A1312 | -5.303 | 111.244 | 213.057 | 1.00 | 0.00 | P |
| ATOM | 1294 | P | U | A1313 | -8.549 | 105.553 | 213.281 | 1.00 | 0.00 | P |
| ATOM | 1295 | P | C | A1314 | -11.320 | 100.470 | 214.244 | 1.00 | 0.00 | P |
| ATOM | 1296 | P | U | A1315 | -16.256 | 99.765 | 218.242 | 1.00 | 0.00 | P |
| ATOM | 1297 | P | G | A1316 | -20.833 | 98.575 | 221.471 | 1.00 | 0.00 | P |
| ATOM | 1298 | P | C | A1317 | -25.851 | 101.604 | 222.755 | 1.00 | 0.00 | P |
| ATOM | 1299 | P | A | A1318 | -25.174 | 107.313 | 221.601 | 1.00 | 0.00 | P |
| ATOM | 1300 | P | A | A1319 | -20.085 | 109.826 | 220.895 | 1.00 | 0.00 | P |
| ATOM | 1301 | P | C | A1320 | -15.398 | 108.969 | 224.823 | 1.00 | 0.00 | P |
| ATOM | 1302 | P | C | A1321 | -13.746 | 111.092 | 229.841 | 1.00 | 0.00 | P |
| ATOM | 1303 | P | C | A1322 | -12.881 | 110.184 | 234.449 | 1.00 | 0.00 | P |
| ATOM | 1304 | P | G | A1323 | -8.717 | 107.613 | 231.073 | 1.00 | 0.00 | P |
| ATOM | 1305 | P | A | A1324 | -6.335 | 102.690 | 230.933 | 1.00 | 0.00 | P |
| ATOM | 1306 | P | C | A1325 | -2.669 | 98.968 | 227.801 | 1.00 | 0.00 | P |
| ATOM | 1307 | P | C | A1326 | 0.351 | 97.886 | 223.089 | 1.00 | 0.00 | P |
| ATOM | 1308 | P | C | A1327 | 3.659 | 98.705 | 218.595 | 1.00 | 0.00 | P |
| ATOM | 1309 | P | C | A1328 | 6.697 | 102.181 | 215.629 | 1.00 | 0.00 | P |
| ATOM | 1310 | P | A | A1329 | 10.227 | 106.740 | 215.871 | 1.00 | 0.00 | P |
| ATOM | 1311 | P | U | A1330 | 12.174 | 111.296 | 219.312 | 1.00 | 0.00 | P |
| ATOM | 1312 | P | G | A1331 | 11.290 | 113.474 | 224.315 | 1.00 | 0.00 | P |
| ATOM | 1313 | P | A | A1332 | 14.073 | 110.123 | 229.405 | 1.00 | 0.00 | P |
| ATOM | 1314 | P | A | A1333 | 15.155 | 111.358 | 235.506 | 1.00 | 0.00 | P |
| ATOM | 1315 | P | G | A1334 | 17.442 | 108.979 | 240.431 | 1.00 | 0.00 | P |
| ATOM | 1316 | P | C | A1335 | 19.480 | 103.976 | 240.398 | 1.00 | 0.00 | P |
| ATOM | 1317 | P | C | A1336 | 22.490 | 100.627 | 243.998 | 1.00 | 0.00 | P |
| ATOM | 1318 | P | G | A1337 | 19.943 | 97.282 | 247.146 | 1.00 | 0.00 | P |
| ATOM | 1319 | P | G | A1338 | 18.772 | 100.224 | 251.617 | 1.00 | 0.00 | P |
| ATOM | 1320 | P | A | A1339 | 19.559 | 100.886 | 257.004 | 1.00 | 0.00 | P |
| ATOM | 1321 | P | A | A1340 | 16.120 | 99.169 | 261.712 | 1.00 | 0.00 | P |
| ATOM | 1322 | P | U | A1341 | 10.722 | 95.687 | 261.637 | 1.00 | 0.00 | P |
| ATOM | 1323 | P | C | A1342 | 7.116 | 91.611 | 258.791 | 1.00 | 0.00 | P |
| ATOM | 1324 | P | G | A1343 | 4.648 | 86.914 | 256.123 | 1.00 | 0.00 | P |
| ATOM | 1325 | P | C | A1344 | 3.718 | 82.036 | 253.683 | 1.00 | 0.00 | P |
| ATOM | 1326 | P | U | A1345 | 5.863 | 76.417 | 252.964 | 1.00 | 0.00 | P |
| ATOM | 1327 | P | A | A1346 | 7.199 | 71.013 | 251.940 | 1.00 | 0.00 | P |
| ATOM | 1328 | P | G | A1347 | 6.767 | 67.324 | 246.694 | 1.00 | 0.00 | P |
| ATOM | 1329 | P | U | A1348 | 4.669 | 73.102 | 242.824 | 1.00 | 0.00 | P |
| ATOM | 1330 | P | A | A1349 | 4.890 | 78.209 | 245.336 | 1.00 | 0.00 | P |
| ATOM | 1331 | P | A | A1350 | 7.776 | 81.801 | 245.891 | 1.00 | 0.00 | P |
| ATOM | 1332 | P | U | A1351 | 9.895 | 84.894 | 241.793 | 1.00 | 0.00 | P |
| ATOM | 1333 | P | C | A1352 | 8.952 | 85.938 | 235.876 | 1.00 | 0.00 | P |
| ATOM | 1334 | P | G | A1353 | 5.752 | 86.233 | 231.640 | 1.00 | 0.00 | P |
| ATOM | 1335 | P | C | A1354 | -0.070 | 85.228 | 228.194 | 1.00 | 0.00 | P |
| ATOM | 1336 | P | G | A1355 | -5.455 | 83.703 | 227.916 | 1.00 | 0.00 | P |
| ATOM | 1337 | P | G | A1356 | -11.281 | 83.170 | 229.156 | 1.00 | 0.00 | P |
| ATOM | 1338 | P | A | A1357 | -16.244 | 83.661 | 232.148 | 1.00 | 0.00 | P |
| ATOM | 1339 | P | U | A1358 | -20.408 | 85.431 | 235.558 | 1.00 | 0.00 | P |
| ATOM | 1340 | P | C | A1359 | -22.486 | 90.725 | 236.375 | 1.00 | 0.00 | P |
| ATOM | 1341 | P | A | A1360 | -22.477 | 94.006 | 231.272 | 1.00 | 0.00 | P |
| ATOM | 1342 | P | G | A1361 | -17.805 | 93.874 | 227.426 | 1.00 | 0.00 | P |
| ATOM | 1343 | P | C | A1362 | -12.879 | 95.887 | 228.359 | 1.00 | 0.00 | P |
| ATOM | 1344 | P | C | A1362A | -9.026 | 96.433 | 233.294 | 1.00 | 0.00 | P |
| ATOM | 1345 | P | A | A1363 | -7.727 | 97.022 | 238.805 | 1.00 | 0.00 | P |
| ATOM | 1346 | P | U | A1364 | -3.319 | 93.299 | 235.112 | 1.00 | 0.00 | P |
| ATOM | 1347 | P | G | A1365 | -1.645 | 90.981 | 240.881 | 1.00 | 0.00 | P |
| ATOM | 1348 | P | C | A1366 | -4.248 | 88.004 | 244.859 | 1.00 | 0.00 | P |
| ATOM | 1349 | P | C | A1367 | -7.173 | 83.304 | 245.937 | 1.00 | 0.00 | P |
| ATOM | 1350 | P | G | A1368 | -8.050 | 77.957 | 244.314 | 1.00 | 0.00 | P |
| ATOM | 1351 | P | C | A1369 | -5.435 | 73.930 | 239.635 | 1.00 | 0.00 | P |
| ATOM | 1352 | P | G | A1370 | -2.775 | 71.260 | 236.051 | 1.00 | 0.00 | P |
| ATOM | 1353 | P | G | A1371 | 3.345 | 70.120 | 233.003 | 1.00 | 0.00 | P |
| ATOM | 1354 | P | U | A1372 | 8.452 | 70.621 | 231.381 | 1.00 | 0.00 | P |
| ATOM | 1355 | P | G | A1373 | 12.073 | 73.310 | 233.054 | 1.00 | 0.00 | P |
| ATOM | 1356 | P | A | A1374 | 14.244 | 73.062 | 238.682 | 1.00 | 0.00 | P |
| ATOM | 1357 | P | A | A1375 | 18.060 | 74.196 | 243.969 | 1.00 | 0.00 | P |
| ATOM | 1358 | P | U | A1376 | 20.906 | 75.740 | 248.326 | 1.00 | 0.00 | P |
| ATOM | 1359 | P | A | A1377 | 20.774 | 74.376 | 254.120 | 1.00 | 0.00 | P |
| ATOM | 1360 | P | C | A1378 | 18.809 | 71.043 | 258.996 | 1.00 | 0.00 | P |
| ATOM | 1361 | P | G | A1379 | 21.209 | 69.293 | 264.474 | 1.00 | 0.00 | P |
| ATOM | 1362 | P | U | A1380 | 17.971 | 71.535 | 269.966 | 1.00 | 0.00 | P |
| ATOM | 1363 | P | U | A1381 | 16.513 | 75.620 | 273.985 | 1.00 | 0.00 | P |
| ATOM | 1364 | P | C | A1382 | 17.007 | 81.267 | 275.462 | 1.00 | 0.00 | P |
| ATOM | 1365 | P | C | A1383 | 12.874 | 85.431 | 273.856 | 1.00 | 0.00 | P |
| ATOM | 1366 | P | C | A1384 | 9.258 | 87.065 | 270.843 | 1.00 | 0.00 | P |
| ATOM | 1367 | P | G | A1385 | 3.079 | 86.412 | 270.638 | 1.00 | 0.00 | P |
| ATOM | 1368 | P | G | A1386 | -0.904 | 81.205 | 271.788 | 1.00 | 0.00 | P |
| ATOM | 1369 | P | G | A1387 | -2.359 | 74.979 | 276.040 | 1.00 | 0.00 | P |
| ATOM | 1370 | P | C | A1388 | -2.410 | 70.216 | 279.952 | 1.00 | 0.00 | P |

```
ATOM   1371  P    C A1389    -1.598  68.669 286.921  1.00  0.00           P
ATOM   1372  P    U A1390     1.362  72.771 291.272  1.00  0.00           P
ATOM   1373  P    U A1391     2.537  76.511 294.768  1.00  0.00           P
ATOM   1374  P    G A1392     3.363  82.057 296.677  1.00  0.00           P
ATOM   1375  P    U A1393     1.069  87.115 297.250  1.00  0.00           P
ATOM   1376  P    A A1394    -3.265  88.978 296.687  1.00  0.00           P
ATOM   1377  P    C A1395    -6.613  91.511 294.494  1.00  0.00           P
ATOM   1378  P    A A1396    -8.866  92.314 289.806  1.00  0.00           P
ATOM   1379  P    C A1397   -12.513  90.137 286.516  1.00  0.00           P
ATOM   1380  P    A A1398    -7.463  89.052 282.494  1.00  0.00           P
ATOM   1381  P    C A1399    -1.147  90.476 282.083  1.00  0.00           P
ATOM   1382  P    C A1400    -1.771  96.309 279.198  1.00  0.00           P
ATOM   1383  P    G A1401    -5.070  96.414 282.635  1.00  0.00           P
ATOM   1384  P    C A1402    -5.477  95.692 287.429  1.00  0.00           P
ATOM   1385  P    C A1403    -2.961  98.400 291.434  1.00  0.00           P
ATOM   1386  P    C A1404    -1.457 100.874 295.671  1.00  0.00           P
ATOM   1387  P    G A1405     1.518 105.184 298.607  1.00  0.00           P
ATOM   1388  P    U A1406     3.500 111.049 299.131  1.00  0.00           P
ATOM   1389  P    C A1407     2.848 117.468 298.182  1.00  0.00           P
ATOM   1390  P    A A1408     0.573 122.069 295.919  1.00  0.00           P
ATOM   1391  P    C A1409    -4.022 125.756 295.258  1.00  0.00           P
ATOM   1392  P    G A1410    -9.494 126.453 295.479  1.00  0.00           P
ATOM   1393  P    C A1411   -14.149 125.675 298.550  1.00  0.00           P
ATOM   1394  P    C A1412   -16.993 123.992 303.675  1.00  0.00           P
ATOM   1395  P    A A1413   -17.578 122.285 309.184  1.00  0.00           P
ATOM   1396  P    U A1414   -13.860 118.826 314.160  1.00  0.00           P
ATOM   1397  P    G A1415    -8.032 119.211 317.049  1.00  0.00           P
ATOM   1398  P    G A1416    -3.952 121.471 319.581  1.00  0.00           P
ATOM   1399  P    G A1417    -1.433 125.923 321.730  1.00  0.00           P
ATOM   1400  P    A A1418    -0.578 132.766 323.662  1.00  0.00           P
ATOM   1401  P    G A1419    -4.817 137.132 327.087  1.00  0.00           P
ATOM   1402  P    C A1420   -10.607 139.153 328.160  1.00  0.00           P
ATOM   1403  P    G A1421   -16.269 137.905 329.476  1.00  0.00           P
ATOM   1404  P    G A1422   -19.917 134.353 331.858  1.00  0.00           P
ATOM   1405  P    G A1423   -20.434 130.405 336.087  1.00  0.00           P
ATOM   1406  P    C A1424   -19.449 126.146 340.389  1.00  0.00           P
ATOM   1407  P    U A1425   -17.268 125.963 345.304  1.00  0.00           P
ATOM   1408  P    C A1426   -13.265 127.243 349.369  1.00  0.00           P
ATOM   1409  P    U A1427    -9.706 130.290 352.731  1.00  0.00           P
ATOM   1410  P    A A1428    -8.402 135.134 355.242  1.00  0.00           P
ATOM   1411  P    C A1429    -9.656 140.259 357.043  1.00  0.00           P
ATOM   1412  P    C A1430   -14.372 144.555 356.986  1.00  0.00           P
ATOM   1413  P    C A1431   -19.788 146.306 356.479  1.00  0.00           P
ATOM   1414  P    G A1432   -25.225 145.198 356.964  1.00  0.00           P
ATOM   1415  P    A A1433   -29.392 140.727 358.392  1.00  0.00           P
ATOM   1416  P    A A1434   -34.537 138.601 359.818  1.00  0.00           P
ATOM   1417  P    G A1435   -33.200 139.490 361.343  1.00  0.00           P
ATOM   1418  P    U A1436   -33.247 135.656 365.616  1.00  0.00           P
ATOM   1419  P    C A1437   -31.223 132.928 370.764  1.00  0.00           P
ATOM   1420  P    G A1438   -27.255 133.633 374.949  1.00  0.00           P
ATOM   1421  P    C A1439   -24.627 137.194 378.547  1.00  0.00           P
ATOM   1422  P    C A1440   -24.623 142.439 381.105  1.00  0.00           P
ATOM   1423  P    G A1441   -26.953 147.512 382.313  1.00  0.00           P
ATOM   1424  P    G A1442   -25.524 151.466 380.305  1.00  0.00           P
ATOM   1425  P    G A1443   -26.513 155.725 383.720  1.00  0.00           P
ATOM   1426  P    A A1446   -29.574 158.333 381.495  1.00  0.00           P
ATOM   1427  P    G A1447   -35.863 158.518 380.103  1.00  0.00           P
ATOM   1428  P    C A1448   -41.408 156.205 378.928  1.00  0.00           P
ATOM   1429  P    C A1449   -45.711 152.797 380.366  1.00  0.00           P
ATOM   1430  P    U A1450   -48.082 148.965 383.058  1.00  0.00           P
ATOM   1431  P    A A1451   -46.812 146.351 388.492  1.00  0.00           P
ATOM   1432  P    C A1452   -42.955 143.015 392.264  1.00  0.00           P
ATOM   1433  P    G A1453   -36.272 142.583 391.542  1.00  0.00           P
ATOM   1434  P    G A1454   -33.882 141.614 388.697  1.00  0.00           P
ATOM   1435  P    G A1455   -35.075 139.997 382.396  1.00  0.00           P
ATOM   1436  P    C A1459   -36.990 140.154 377.052  1.00  0.00           P
ATOM   1437  P    A A1460   -37.632 142.973 371.930  1.00  0.00           P
ATOM   1438  P    G A1461   -36.298 146.866 368.110  1.00  0.00           P
ATOM   1439  P    G A1462   -31.045 149.627 367.291  1.00  0.00           P
ATOM   1440  P    C A1463   -25.542 150.006 367.093  1.00  0.00           P
ATOM   1441  P    G A1464   -20.287 147.247 366.930  1.00  0.00           P
ATOM   1442  P    C A1465   -17.080 142.102 366.033  1.00  0.00           P
ATOM   1443  P    C A1466   -15.618 137.222 363.951  1.00  0.00           P
ATOM   1444  P    G A1467   -19.448 132.826 361.494  1.00  0.00           P
ATOM   1445  P    A A1468   -23.087 132.490 357.353  1.00  0.00           P
ATOM   1446  P    G A1469   -24.454 132.051 351.551  1.00  0.00           P
ATOM   1447  P    G A1470   -25.484 134.464 347.109  1.00  0.00           P
ATOM   1448  P    G A1471   -23.071 138.412 344.210  1.00  0.00           P
ATOM   1449  P    U A1472   -18.836 142.299 342.153  1.00  0.00           P
ATOM   1450  P    A A1473   -13.523 144.002 341.028  1.00  0.00           P
ATOM   1451  P    G A1474    -8.166 142.416 340.346  1.00  0.00           P
ATOM   1452  P    G A1475    -4.003 138.044 339.694  1.00  0.00           P
ATOM   1453  P    G A1476    -1.504 130.494 339.637  1.00  0.00           P
ATOM   1454  P    C A1477    -2.592 125.385 336.988  1.00  0.00           P
ATOM   1455  P    C A1478    -6.266 121.756 334.468  1.00  0.00           P
ATOM   1456  P    C A1479   -11.252 119.677 330.194  1.00  0.00           P
ATOM   1457  P    G A1480   -15.025 120.968 325.472  1.00  0.00           P
```

```
ATOM   1458  P     U A1481    -16.523 124.319 320.645  1.00  0.00           P
ATOM   1459  P     G A1482    -15.345 128.319 316.562  1.00  0.00           P
ATOM   1460  P     A A1483    -11.524 133.063 312.716  1.00  0.00           P
ATOM   1461  P     C A1484     -7.487 135.447 309.132  1.00  0.00           P
ATOM   1462  P     U A1485     -2.196 133.428 307.852  1.00  0.00           P
ATOM   1463  P     G A1486     -0.020 127.439 307.095  1.00  0.00           P
ATOM   1464  P     G A1487      1.393 121.195 307.703  1.00  0.00           P
ATOM   1465  P     G A1488     -0.919 114.683 307.420  1.00  0.00           P
ATOM   1466  P     G A1489     -6.053 111.268 305.325  1.00  0.00           P
ATOM   1467  P     C A1490    -10.823 109.175 302.552  1.00  0.00           P
ATOM   1468  P     G A1491    -14.643 110.866 298.353  1.00  0.00           P
ATOM   1469  P     A A1492    -13.829 112.576 292.463  1.00  0.00           P
ATOM   1470  P     A A1493    -13.955 111.862 286.730  1.00  0.00           P
ATOM   1471  P     G A1494     -7.889 112.958 285.534  1.00  0.00           P
ATOM   1472  P     U A1495     -2.725 115.480 284.879  1.00  0.00           P
ATOM   1473  P     C A1496      2.310 113.783 285.162  1.00  0.00           P
ATOM   1474  P     G A1497      6.665 111.603 286.225  1.00  0.00           P
ATOM   1475  P     U A1498      9.255 106.426 287.008  1.00  0.00           P
ATOM   1476  P     A A1499      7.526 101.442 289.278  1.00  0.00           P
ATOM   1477  P     A A1500      8.207  97.176 293.753  1.00  0.00           P
ATOM   1478  P     C A1501      5.770  93.336 295.872  1.00  0.00           P
ATOM   1479  P     A A1502      2.247  90.962 293.557  1.00  0.00           P
ATOM   1480  P     A A1503      5.006  85.700 293.070  1.00  0.00           P
ATOM   1481  P     G A1504      9.890  89.518 293.018  1.00  0.00           P
ATOM   1482  P     G A1505      9.836  94.484 290.865  1.00  0.00           P
ATOM   1483  P     U A1506     15.161  94.204 288.951  1.00  0.00           P
ATOM   1484  P     A A1507     16.027  91.381 294.670  1.00  0.00           P
ATOM   1485  P     G A1508     11.845  93.509 297.361  1.00  0.00           P
ATOM   1486  P     C A1509      7.482  95.391 301.535  1.00  0.00           P
ATOM   1487  P     U A1510      6.207  97.007 306.915  1.00  0.00           P
ATOM   1488  P     G A1511      7.654  98.426 312.156  1.00  0.00           P
ATOM   1489  P     U A1512     10.303 102.043 315.674  1.00  0.00           P
ATOM   1490  P     A A1513     15.107 105.685 316.089  1.00  0.00           P
ATOM   1491  P     C A1514     18.419 109.423 313.322  1.00  0.00           P
ATOM   1492  P     C A1515     20.493 111.754 308.279  1.00  0.00           P
ATOM   1493  P     G A1516     20.219 113.050 302.837  1.00  0.00           P
ATOM   1494  P     G A1517     16.580 114.747 298.146  1.00  0.00           P
ATOM   1495  P     A A1518     11.893 113.495 298.898  1.00  0.00           P
ATOM   1496  P     A A1519      7.672 109.360 298.515  1.00  0.00           P
ATOM   1497  P     G A1520      7.170 103.963 299.099  1.00  0.00           P
ATOM   1498  P     G A1521     12.879 100.747 298.260  1.00  0.00           P
ATOM   1499  P     U A1522     18.154  99.261 298.762  1.00  0.00           P
ATOM   1500  P     G A1523     22.405  97.471 302.612  1.00  0.00           P
ATOM   1501  P     C A1524     24.713  95.670 306.993  1.00  0.00           P
ATOM   1502  P     G A1525     23.838  92.009 311.175  1.00  0.00           P
ATOM   1503  P     G A1526     19.878  87.975 312.725  1.00  0.00           P
ATOM   1504  P     C A1527     14.697  85.034 312.950  1.00  0.00           P
ATOM   1505  P     U A1528     10.264  82.239 310.565  1.00  0.00           P
ATOM   1506  P     G A1529      5.109  81.194 306.281  1.00  0.00           P
ATOM   1507  P     G A1530      7.872  80.302 300.505  1.00  0.00           P
ATOM   1508  P     A A1531     12.974  78.318 295.881  1.00  0.00           P
ATOM   1509  P     U A1532     11.401  73.145 294.743  1.00  0.00           P
ATOM   1510  P     C A1533     13.837  71.387 289.434  1.00  0.00           P
ATOM   1511  P     A A1534     16.834  72.563 284.907  1.00  0.00           P
ATOM   1512  P     C A1535     22.783  69.584 285.036  1.00  0.00           P
ATOM   1513  P     C A1536     27.672  69.475 291.682  1.00  0.00           P
ATOM   1514  P     U A1537     30.304  67.427 297.874  1.00  0.00           P
ATOM   1515  P     C A1538     28.873  64.302 302.903  1.00  0.00           P
ATOM   1516  P     C A1539     26.322  62.460 307.086  1.00  0.00           P
ATOM   1517  P     U A1540     21.268  59.445 309.559  1.00  0.00           P
ATOM   1518  P     U A1541     18.809  53.594 308.171  1.00  0.00           P
ATOM   1519  P     U A1542     20.261  52.408 301.460  1.00  0.00           P
TER    1520        U A1542
ATOM   1521  O3P   G B    1    -1.228 162.393 290.854  1.00  0.00           O
ATOM   1522  P     G B    1     0.016 161.519 290.810  1.00  0.00           P
ATOM   1523  O1P   G B    1     0.173 160.766 289.497  1.00  0.00           O
ATOM   1524  O2P   G B    1     0.174 160.633 292.036  1.00  0.00           O
ATOM   1525  O5*   G B    1     1.293 162.522 290.836  1.00  0.00           O
ATOM   1526  C5*   G B    1     2.460 162.198 290.079  1.00  0.00           C
ATOM   1527  C4*   G B    1     3.576 163.153 290.393  1.00  0.00           C
ATOM   1528  O4*   G B    1     3.907 163.108 291.808  1.00  0.00           O
ATOM   1529  C3*   G B    1     4.843 162.814 289.626  1.00  0.00           C
ATOM   1530  O3*   G B    1     4.927 163.707 288.526  1.00  0.00           O
ATOM   1531  C2*   G B    1     5.958 163.021 290.648  1.00  0.00           C
ATOM   1532  O2*   G B    1     6.468 164.338 290.653  1.00  0.00           O
ATOM   1533  C1*   G B    1     5.249 162.705 291.968  1.00  0.00           C
ATOM   1534  N9    G B    1     5.238 161.293 292.341  1.00  0.00           N
ATOM   1535  C8    G B    1     4.139 160.558 292.715  1.00  0.00           C
ATOM   1536  N7    G B    1     4.425 159.320 293.007  1.00  0.00           N
ATOM   1537  C5    G B    1     5.794 159.227 292.807  1.00  0.00           C
ATOM   1538  C6    G B    1     6.671 158.124 292.965  1.00  0.00           C
ATOM   1539  O6    G B    1     6.401 156.972 293.321  1.00  0.00           O
ATOM   1540  N1    G B    1     7.984 158.469 292.659  1.00  0.00           N
ATOM   1541  C2    G B    1     8.403 159.713 292.257  1.00  0.00           C
ATOM   1542  N2    G B    1     9.711 159.848 292.016  1.00  0.00           N
ATOM   1543  N3    G B    1     7.596 160.749 292.105  1.00  0.00           N
ATOM   1544  C4    G B    1     6.314 160.438 292.396  1.00  0.00           C
```

```
ATOM   1545  P     C B   2       5.956 163.408 287.338  1.00  0.00           P
ATOM   1546  O1P   C B   2       6.208 164.697 286.647  1.00  0.00           O
ATOM   1547  O2P   C B   2       5.458 162.246 286.561  1.00  0.00           O
ATOM   1548  O5*   C B   2       7.290 162.972 288.084  1.00  0.00           O
ATOM   1549  C5*   C B   2       8.544 163.506 287.683  1.00  0.00           C
ATOM   1550  C4*   C B   2       9.474 162.397 287.259  1.00  0.00           C
ATOM   1551  O4*   C B   2       9.720 161.543 288.406  1.00  0.00           O
ATOM   1552  C3*   C B   2       8.956 161.420 286.211  1.00  0.00           C
ATOM   1553  O3*   C B   2       9.095 161.909 284.879  1.00  0.00           O
ATOM   1554  C2*   C B   2       9.885 160.237 286.435  1.00  0.00           C
ATOM   1555  O2*   C B   2      11.162 160.427 285.860  1.00  0.00           O
ATOM   1556  C1*   C B   2       9.991 160.225 287.961  1.00  0.00           C
ATOM   1557  N1    C B   2       9.003 159.315 288.555  1.00  0.00           N
ATOM   1558  C2    C B   2       9.352 157.971 288.726  1.00  0.00           C
ATOM   1559  O2    C B   2      10.498 157.603 288.411  1.00  0.00           O
ATOM   1560  N3    C B   2       8.441 157.112 289.229  1.00  0.00           N
ATOM   1561  C4    C B   2       7.226 157.552 289.563  1.00  0.00           C
ATOM   1562  N4    C B   2       6.358 156.665 290.049  1.00  0.00           N
ATOM   1563  C5    C B   2       6.850 158.916 289.415  1.00  0.00           C
ATOM   1564  C6    C B   2       7.763 159.758 288.915  1.00  0.00           C
ATOM   1565  P     G B   3       8.493 161.059 283.644  1.00  0.00           P
ATOM   1566  O1P   G B   3       8.935 161.710 282.386  1.00  0.00           O
ATOM   1567  O2P   G B   3       7.042 160.839 283.888  1.00  0.00           O
ATOM   1568  O5*   G B   3       9.240 159.655 283.711  1.00  0.00           O
ATOM   1569  C5*   G B   3      10.339 159.396 282.851  1.00  0.00           C
ATOM   1570  C4*   G B   3      10.984 158.081 283.201  1.00  0.00           C
ATOM   1571  O4*   G B   3      10.897 157.838 284.631  1.00  0.00           O
ATOM   1572  C3*   G B   3      10.321 156.858 282.608  1.00  0.00           C
ATOM   1573  O3*   G B   3      10.662 156.676 281.245  1.00  0.00           O
ATOM   1574  C2*   G B   3      10.870 155.755 283.504  1.00  0.00           C
ATOM   1575  O2*   G B   3      12.192 155.359 283.194  1.00  0.00           O
ATOM   1576  C1*   G B   3      10.799 156.439 284.870  1.00  0.00           C
ATOM   1577  N9    G B   3       9.508 156.176 285.495  1.00  0.00           N
ATOM   1578  C8    G B   3       8.441 157.036 285.590  1.00  0.00           C
ATOM   1579  N7    G B   3       7.397 156.494 286.157  1.00  0.00           N
ATOM   1580  C5    G B   3       7.804 155.202 286.466  1.00  0.00           C
ATOM   1581  C6    G B   3       7.092 154.137 287.079  1.00  0.00           C
ATOM   1582  O6    G B   3       5.929 154.126 287.492  1.00  0.00           O
ATOM   1583  N1    G B   3       7.878 152.994 287.191  1.00  0.00           N
ATOM   1584  C2    G B   3       9.182 152.886 286.766  1.00  0.00           C
ATOM   1585  N2    G B   3       9.769 151.697 286.957  1.00  0.00           N
ATOM   1586  N3    G B   3       9.859 153.876 286.195  1.00  0.00           N
ATOM   1587  C4    G B   3       9.108 154.994 286.077  1.00  0.00           C
ATOM   1588  P     G B   4       9.562 156.096 280.241  1.00  0.00           P
ATOM   1589  O1P   G B   4       9.957 156.424 278.849  1.00  0.00           O
ATOM   1590  O2P   G B   4       8.264 156.580 280.768  1.00  0.00           O
ATOM   1591  O5*   G B   4       9.651 154.516 280.430  1.00  0.00           O
ATOM   1592  C5*   G B   4      10.783 153.802 279.968  1.00  0.00           C
ATOM   1593  C4*   G B   4      10.853 152.456 280.636  1.00  0.00           C
ATOM   1594  O4*   G B   4      10.699 152.595 282.072  1.00  0.00           O
ATOM   1595  C3*   G B   4       9.735 151.510 280.276  1.00  0.00           C
ATOM   1596  O3*   G B   4      10.028 150.906 279.044  1.00  0.00           O
ATOM   1597  C2*   G B   4       9.814 150.502 281.409  1.00  0.00           C
ATOM   1598  O2*   G B   4      10.880 149.597 281.267  1.00  0.00           O
ATOM   1599  C1*   G B   4      10.073 151.428 282.590  1.00  0.00           C
ATOM   1600  N9    G B   4       8.814 151.829 283.208  1.00  0.00           N
ATOM   1601  C8    G B   4       8.247 153.081 283.221  1.00  0.00           C
ATOM   1602  N7    G B   4       7.113 153.124 283.869  1.00  0.00           N
ATOM   1603  C5    G B   4       6.924 151.826 284.308  1.00  0.00           C
ATOM   1604  C6    G B   4       5.874 151.268 285.063  1.00  0.00           C
ATOM   1605  O6    G B   4       4.869 151.840 285.530  1.00  0.00           O
ATOM   1606  N1    G B   4       6.066 149.903 285.272  1.00  0.00           N
ATOM   1607  C2    G B   4       7.139 149.170 284.810  1.00  0.00           C
ATOM   1608  N2    G B   4       7.146 147.864 285.098  1.00  0.00           N
ATOM   1609  N3    G B   4       8.131 149.686 284.112  1.00  0.00           N
ATOM   1610  C4    G B   4       7.960 151.009 283.901  1.00  0.00           C
ATOM   1611  P     A B   5       8.834 150.381 278.121  1.00  0.00           P
ATOM   1612  O1P   A B   5       9.456 149.733 276.937  1.00  0.00           O
ATOM   1613  O2P   A B   5       7.854 151.492 277.927  1.00  0.00           O
ATOM   1614  O5*   A B   5       8.200 149.218 278.998  1.00  0.00           O
ATOM   1615  C5*   A B   5       8.888 147.993 279.127  1.00  0.00           C
ATOM   1616  C4*   A B   5       8.049 147.020 279.888  1.00  0.00           C
ATOM   1617  O4*   A B   5       7.862 147.522 281.239  1.00  0.00           O
ATOM   1618  C3*   A B   5       6.633 146.861 279.367  1.00  0.00           C
ATOM   1619  O3*   A B   5       6.615 145.928 278.295  1.00  0.00           O
ATOM   1620  C2*   A B   5       5.948 146.316 280.614  1.00  0.00           C
ATOM   1621  O2*   A B   5       6.338 144.988 280.924  1.00  0.00           O
ATOM   1622  C1*   A B   5       6.558 147.224 281.678  1.00  0.00           C
ATOM   1623  N9    A B   5       5.826 148.479 281.807  1.00  0.00           N
ATOM   1624  C8    A B   5       6.107 149.697 281.252  1.00  0.00           C
ATOM   1625  N7    A B   5       5.249 150.634 281.578  1.00  0.00           N
ATOM   1626  C5    A B   5       4.345 149.986 282.405  1.00  0.00           C
ATOM   1627  C6    A B   5       3.199 150.434 283.099  1.00  0.00           C
ATOM   1628  N6    A B   5       2.748 151.692 283.059  1.00  0.00           N
ATOM   1629  N1    A B   5       2.524 149.532 283.838  1.00  0.00           N
ATOM   1630  C2    A B   5       2.967 148.261 283.866  1.00  0.00           C
ATOM   1631  N3    A B   5       4.029 147.722 283.262  1.00  0.00           N
```

```
ATOM   1632  C4      A  B   5    4.683 148.655 282.544  1.00  0.00           C
ATOM   1633  P       U  B   6    5.507 146.060 277.140  1.00  0.00           P
ATOM   1634  O1P     U  B   6    5.762 144.932 276.213  1.00  0.00           O
ATOM   1635  O2P     U  B   6    5.477 147.451 276.620  1.00  0.00           O
ATOM   1636  O5*     U  B   6    4.134 145.758 277.883  1.00  0.00           O
ATOM   1637  C5*     U  B   6    3.866 144.453 278.347  1.00  0.00           C
ATOM   1638  C4*     U  B   6    2.724 144.472 279.315  1.00  0.00           C
ATOM   1639  O4*     U  B   6    2.938 145.478 280.341  1.00  0.00           O
ATOM   1640  C3*     U  B   6    1.421 144.907 278.699  1.00  0.00           C
ATOM   1641  O3*     U  B   6    0.859 143.818 278.001  1.00  0.00           O
ATOM   1642  C2*     U  B   6    0.622 145.244 279.945  1.00  0.00           C
ATOM   1643  O2*     U  B   6    0.228 144.070 280.618  1.00  0.00           O
ATOM   1644  C1*     U  B   6    1.680 145.962 280.778  1.00  0.00           C
ATOM   1645  N1      U  B   6    1.647 147.418 280.611  1.00  0.00           N
ATOM   1646  C2      U  B   6    0.557 148.072 281.146  1.00  0.00           C
ATOM   1647  O2      U  B   6   -0.343 147.486 281.703  1.00  0.00           O
ATOM   1648  N3      U  B   6    0.550 149.425 280.982  1.00  0.00           N
ATOM   1649  C4      U  B   6    1.488 150.191 280.338  1.00  0.00           C
ATOM   1650  O4      U  B   6    1.312 151.406 280.253  1.00  0.00           O
ATOM   1651  C5      U  B   6    2.599 149.453 279.799  1.00  0.00           C
ATOM   1652  C6      U  B   6    2.637 148.114 279.954  1.00  0.00           C
ATOM   1653  P       U  B   7   -0.083 144.101 276.738  1.00  0.00           P
ATOM   1654  O1P     U  B   7   -0.271 142.800 276.079  1.00  0.00           O
ATOM   1655  O2P     U  B   7    0.458 145.279 275.985  1.00  0.00           O
ATOM   1656  O5*     U  B   7   -1.468 144.580 277.386  1.00  0.00           O
ATOM   1657  C5*     U  B   7   -2.139 143.792 278.374  1.00  0.00           C
ATOM   1658  C4*     U  B   7   -3.413 144.492 278.799  1.00  0.00           C
ATOM   1659  O4*     U  B   7   -3.035 145.778 279.358  1.00  0.00           O
ATOM   1660  C3*     U  B   7   -4.399 144.778 277.668  1.00  0.00           C
ATOM   1661  O3*     U  B   7   -5.744 144.515 278.063  1.00  0.00           O
ATOM   1662  C2*     U  B   7   -4.159 146.249 277.355  1.00  0.00           C
ATOM   1663  O2*     U  B   7   -5.342 146.910 276.960  1.00  0.00           O
ATOM   1664  C1*     U  B   7   -3.749 146.803 278.715  1.00  0.00           C
ATOM   1665  N1      U  B   7   -2.890 147.993 278.630  1.00  0.00           N
ATOM   1666  C2      U  B   7   -3.406 149.182 279.101  1.00  0.00           C
ATOM   1667  O2      U  B   7   -4.514 149.265 279.614  1.00  0.00           O
ATOM   1668  N3      U  B   7   -2.582 150.268 278.960  1.00  0.00           N
ATOM   1669  C4      U  B   7   -1.311 150.287 278.406  1.00  0.00           C
ATOM   1670  O4      U  B   7   -0.682 151.364 278.334  1.00  0.00           O
ATOM   1671  C5      U  B   7   -0.845 149.009 277.968  1.00  0.00           C
ATOM   1672  C6      U  B   7   -1.624 147.936 278.092  1.00  0.00           C
ATOM   1673  P       U  B   8   -6.468 143.132 277.637  1.00  0.00           P
ATOM   1674  O1P     U  B   8   -7.909 143.267 277.999  1.00  0.00           O
ATOM   1675  O2P     U  B   8   -5.675 141.977 278.116  1.00  0.00           O
ATOM   1676  O5*     U  B   8   -6.424 143.126 276.040  1.00  0.00           O
ATOM   1677  C5*     U  B   8   -7.368 143.894 275.307  1.00  0.00           C
ATOM   1678  C4*     U  B   8   -7.835 143.155 274.082  1.00  0.00           C
ATOM   1679  O4*     U  B   8   -6.735 143.053 273.126  1.00  0.00           O
ATOM   1680  C3*     U  B   8   -8.323 141.715 274.230  1.00  0.00           C
ATOM   1681  O3*     U  B   8   -9.676 141.642 274.684  1.00  0.00           O
ATOM   1682  C2*     U  B   8   -8.217 141.267 272.781  1.00  0.00           C
ATOM   1683  O2*     U  B   8   -9.147 141.905 271.909  1.00  0.00           O
ATOM   1684  C1*     U  B   8   -6.834 141.827 272.427  1.00  0.00           C
ATOM   1685  N1      U  B   8   -5.741 140.968 272.889  1.00  0.00           N
ATOM   1686  C2      U  B   8   -5.360 139.915 272.079  1.00  0.00           C
ATOM   1687  O2      U  B   8   -5.875 139.693 271.004  1.00  0.00           O
ATOM   1688  N3      U  B   8   -4.354 139.143 272.579  1.00  0.00           N
ATOM   1689  C4      U  B   8   -3.696 139.318 273.780  1.00  0.00           C
ATOM   1690  O4      U  B   8   -2.843 138.504 274.129  1.00  0.00           O
ATOM   1691  C5      U  B   8   -4.150 140.422 274.547  1.00  0.00           C
ATOM   1692  C6      U  B   8   -5.127 141.194 274.086  1.00  0.00           C
ATOM   1693  P       A  B   9  -10.150 140.419 275.615  1.00  0.00           P
ATOM   1694  O1P     A  B   9  -10.926 140.991 276.746  1.00  0.00           O
ATOM   1695  O2P     A  B   9   -8.987 139.505 275.908  1.00  0.00           O
ATOM   1696  O5*     A  B   9  -11.153 139.626 274.686  1.00  0.00           O
ATOM   1697  C5*     A  B   9  -12.411 140.193 274.335  1.00  0.00           C
ATOM   1698  C4*     A  B   9  -13.481 139.144 274.434  1.00  0.00           C
ATOM   1699  O4*     A  B   9  -13.230 138.195 273.356  1.00  0.00           O
ATOM   1700  C3*     A  B   9  -13.484 138.324 275.732  1.00  0.00           C
ATOM   1701  O3*     A  B   9  -14.805 137.879 276.032  1.00  0.00           O
ATOM   1702  C2*     A  B   9  -12.654 137.098 275.353  1.00  0.00           C
ATOM   1703  O2*     A  B   9  -13.061 135.944 276.040  1.00  0.00           O
ATOM   1704  C1*     A  B   9  -13.048 136.906 273.901  1.00  0.00           C
ATOM   1705  N9      A  B   9  -12.052 136.162 273.113  1.00  0.00           N
ATOM   1706  C8      A  B   9  -10.827 135.710 273.523  1.00  0.00           C
ATOM   1707  N7      A  B   9  -10.201 134.965 272.621  1.00  0.00           N
ATOM   1708  C5      A  B   9  -11.071 134.952 271.549  1.00  0.00           C
ATOM   1709  C6      A  B   9  -11.006 134.344 270.296  1.00  0.00           C
ATOM   1710  N6      A  B   9   -9.974 133.583 269.893  1.00  0.00           N
ATOM   1711  N1      A  B   9  -12.043 134.533 269.452  1.00  0.00           N
ATOM   1712  C2      A  B   9  -13.067 135.300 269.849  1.00  0.00           C
ATOM   1713  N3      A  B   9  -13.242 135.934 271.002  1.00  0.00           N
ATOM   1714  C4      A  B   9  -12.206 135.712 271.825  1.00  0.00           C
HETATM 1715  P     2MG  B  10  -15.721 138.692 277.112  1.00  0.00           P
HETATM 1716  O1P   2MG  B  10  -15.377 140.114 277.120  1.00  0.00           O
HETATM 1717  O2P   2MG  B  10  -17.132 138.290 276.877  1.00  0.00           O
HETATM 1718  O5*   2MG  B  10  -15.210 138.121 278.498  1.00  0.00           O
```

| | | | | | | | | | |
|---|---|---|---|---|---|---|---|---|---|
| HETATM | 1719 | C5* | 2MG | B | 10 | -15.821 | 138.567 | 279.718 | 1.00 | 0.00 | C |
| HETATM | 1720 | C4* | 2MG | B | 10 | -15.800 | 137.465 | 280.747 | 1.00 | 0.00 | C |
| HETATM | 1721 | O4* | 2MG | B | 10 | -16.540 | 136.330 | 280.219 | 1.00 | 0.00 | O |
| HETATM | 1722 | C3* | 2MG | B | 10 | -14.419 | 136.927 | 281.066 | 1.00 | 0.00 | C |
| HETATM | 1723 | O3* | 2MG | B | 10 | -13.872 | 137.655 | 282.161 | 1.00 | 0.00 | O |
| HETATM | 1724 | C2* | 2MG | B | 10 | -14.733 | 135.499 | 281.458 | 1.00 | 0.00 | C |
| HETATM | 1725 | O2* | 2MG | B | 10 | -15.307 | 135.482 | 282.758 | 1.00 | 0.00 | O |
| HETATM | 1726 | C1* | 2MG | B | 10 | -15.818 | 135.136 | 280.454 | 1.00 | 0.00 | C |
| HETATM | 1727 | N9 | 2MG | B | 10 | -15.402 | 134.590 | 279.165 | 1.00 | 0.00 | N |
| HETATM | 1728 | C8 | 2MG | B | 10 | -15.808 | 135.032 | 277.922 | 1.00 | 0.00 | C |
| HETATM | 1729 | N7 | 2MG | B | 10 | -15.338 | 134.309 | 276.935 | 1.00 | 0.00 | N |
| HETATM | 1730 | C5 | 2MG | B | 10 | -14.567 | 133.340 | 277.560 | 1.00 | 0.00 | C |
| HETATM | 1731 | C6 | 2MG | B | 10 | -13.799 | 132.297 | 277.006 | 1.00 | 0.00 | C |
| HETATM | 1732 | O6 | 2MG | B | 10 | -13.689 | 131.980 | 275.821 | 1.00 | 0.00 | O |
| HETATM | 1733 | N1 | 2MG | B | 10 | -13.119 | 131.578 | 277.984 | 1.00 | 0.00 | N |
| HETATM | 1734 | C2 | 2MG | B | 10 | -13.183 | 131.833 | 279.337 | 1.00 | 0.00 | C |
| HETATM | 1735 | N2 | 2MG | B | 10 | -12.457 | 131.024 | 280.122 | 1.00 | 0.00 | N |
| HETATM | 1736 | CM2 | 2MG | B | 10 | -12.501 | 131.039 | 281.588 | 1.00 | 0.00 | C |
| HETATM | 1737 | N3 | 2MG | B | 10 | -13.912 | 132.807 | 279.874 | 1.00 | 0.00 | N |
| HETATM | 1738 | C4 | 2MG | B | 10 | -14.575 | 133.513 | 278.938 | 1.00 | 0.00 | C |
| ATOM | 1739 | P | C | B | 11 | -12.364 | 138.171 | 282.106 | 1.00 | 0.00 | P |
| ATOM | 1740 | O1P | C | B | 11 | -12.102 | 139.061 | 283.246 | 1.00 | 0.00 | O |
| ATOM | 1741 | O2P | C | B | 11 | -12.119 | 138.673 | 280.713 | 1.00 | 0.00 | O |
| ATOM | 1742 | O5* | C | B | 11 | -11.500 | 136.861 | 282.384 | 1.00 | 0.00 | O |
| ATOM | 1743 | C5* | C | B | 11 | -11.421 | 136.335 | 283.711 | 1.00 | 0.00 | C |
| ATOM | 1744 | C4* | C | B | 11 | -10.576 | 135.085 | 283.749 | 1.00 | 0.00 | C |
| ATOM | 1745 | O4* | C | B | 11 | -11.159 | 134.067 | 282.894 | 1.00 | 0.00 | O |
| ATOM | 1746 | C3* | C | B | 11 | -9.162 | 135.278 | 283.254 | 1.00 | 0.00 | C |
| ATOM | 1747 | O3* | C | B | 11 | -8.321 | 135.658 | 284.335 | 1.00 | 0.00 | O |
| ATOM | 1748 | C2* | C | B | 11 | -8.787 | 133.914 | 282.679 | 1.00 | 0.00 | C |
| ATOM | 1749 | O2* | C | B | 11 | -8.217 | 133.059 | 283.643 | 1.00 | 0.00 | O |
| ATOM | 1750 | C1* | C | B | 11 | -10.136 | 133.371 | 282.204 | 1.00 | 0.00 | C |
| ATOM | 1751 | N1 | C | B | 11 | -10.371 | 133.552 | 280.768 | 1.00 | 0.00 | N |
| ATOM | 1752 | C2 | C | B | 11 | -9.771 | 132.677 | 279.861 | 1.00 | 0.00 | C |
| ATOM | 1753 | O2 | C | B | 11 | -9.061 | 131.759 | 280.300 | 1.00 | 0.00 | O |
| ATOM | 1754 | N3 | C | B | 11 | -9.974 | 132.862 | 278.522 | 1.00 | 0.00 | N |
| ATOM | 1755 | C4 | C | B | 11 | -10.743 | 133.873 | 278.100 | 1.00 | 0.00 | C |
| ATOM | 1756 | N4 | C | B | 11 | -10.937 | 134.019 | 276.782 | 1.00 | 0.00 | N |
| ATOM | 1757 | C5 | C | B | 11 | -11.362 | 134.769 | 279.006 | 1.00 | 0.00 | C |
| ATOM | 1758 | C6 | C | B | 11 | -11.158 | 134.571 | 280.321 | 1.00 | 0.00 | C |
| ATOM | 1759 | P | U | B | 12 | -7.119 | 136.664 | 284.053 | 1.00 | 0.00 | P |
| ATOM | 1760 | O1P | U | B | 12 | -6.461 | 137.102 | 285.309 | 1.00 | 0.00 | O |
| ATOM | 1761 | O2P | U | B | 12 | -7.691 | 137.686 | 283.144 | 1.00 | 0.00 | O |
| ATOM | 1762 | O5* | U | B | 12 | -6.100 | 135.767 | 283.217 | 1.00 | 0.00 | O |
| ATOM | 1763 | C5* | U | B | 12 | -5.397 | 134.690 | 283.831 | 1.00 | 0.00 | C |
| ATOM | 1764 | C4* | U | B | 12 | -4.633 | 133.900 | 282.795 | 1.00 | 0.00 | C |
| ATOM | 1765 | O4* | U | B | 12 | -5.564 | 133.254 | 281.888 | 1.00 | 0.00 | O |
| ATOM | 1766 | C3* | U | B | 12 | -3.780 | 134.731 | 281.851 | 1.00 | 0.00 | C |
| ATOM | 1767 | O3* | U | B | 12 | -2.536 | 135.039 | 282.439 | 1.00 | 0.00 | O |
| ATOM | 1768 | C2* | U | B | 12 | -3.568 | 133.771 | 280.689 | 1.00 | 0.00 | C |
| ATOM | 1769 | O2* | U | B | 12 | -2.482 | 132.884 | 280.891 | 1.00 | 0.00 | O |
| ATOM | 1770 | C1* | U | B | 12 | -4.918 | 133.053 | 280.630 | 1.00 | 0.00 | C |
| ATOM | 1771 | N1 | U | B | 12 | -5.755 | 133.641 | 279.579 | 1.00 | 0.00 | N |
| ATOM | 1772 | C2 | U | B | 12 | -5.556 | 133.213 | 278.280 | 1.00 | 0.00 | C |
| ATOM | 1773 | O2 | U | B | 12 | -4.711 | 132.411 | 277.974 | 1.00 | 0.00 | O |
| ATOM | 1774 | N3 | U | B | 12 | -6.377 | 133.781 | 277.355 | 1.00 | 0.00 | N |
| ATOM | 1775 | C4 | U | B | 12 | -7.358 | 134.729 | 277.592 | 1.00 | 0.00 | C |
| ATOM | 1776 | O4 | U | B | 12 | -8.065 | 135.114 | 276.668 | 1.00 | 0.00 | O |
| ATOM | 1777 | C5 | U | B | 12 | -7.484 | 135.127 | 278.953 | 1.00 | 0.00 | C |
| ATOM | 1778 | C6 | U | B | 12 | -6.690 | 134.576 | 279.877 | 1.00 | 0.00 | C |
| ATOM | 1779 | P | C | B | 13 | -1.657 | 136.237 | 281.844 | 1.00 | 0.00 | P |
| ATOM | 1780 | O1P | C | B | 13 | -0.460 | 136.483 | 282.692 | 1.00 | 0.00 | O |
| ATOM | 1781 | O2P | C | B | 13 | -2.592 | 137.349 | 281.555 | 1.00 | 0.00 | O |
| ATOM | 1782 | O5* | C | B | 13 | -1.113 | 135.610 | 280.493 | 1.00 | 0.00 | O |
| ATOM | 1783 | C5* | C | B | 13 | -1.071 | 136.360 | 279.302 | 1.00 | 0.00 | C |
| ATOM | 1784 | C4* | C | B | 13 | -1.100 | 135.434 | 278.122 | 1.00 | 0.00 | C |
| ATOM | 1785 | O4* | C | B | 13 | -2.460 | 135.003 | 277.851 | 1.00 | 0.00 | O |
| ATOM | 1786 | C3* | C | B | 13 | -0.673 | 136.114 | 276.843 | 1.00 | 0.00 | C |
| ATOM | 1787 | O3* | C | B | 13 | 0.743 | 136.165 | 276.870 | 1.00 | 0.00 | O |
| ATOM | 1788 | C2* | C | B | 13 | -1.306 | 135.217 | 275.782 | 1.00 | 0.00 | C |
| ATOM | 1789 | O2* | C | B | 13 | -0.582 | 134.046 | 275.497 | 1.00 | 0.00 | O |
| ATOM | 1790 | C1* | C | B | 13 | -2.624 | 134.816 | 276.457 | 1.00 | 0.00 | C |
| ATOM | 1791 | N1 | C | B | 13 | -3.783 | 135.608 | 276.030 | 1.00 | 0.00 | N |
| ATOM | 1792 | C2 | C | B | 13 | -4.313 | 135.408 | 274.751 | 1.00 | 0.00 | C |
| ATOM | 1793 | O2 | C | B | 13 | -3.741 | 134.613 | 273.984 | 1.00 | 0.00 | O |
| ATOM | 1794 | N3 | C | B | 13 | -5.415 | 136.105 | 274.369 | 1.00 | 0.00 | N |
| ATOM | 1795 | C4 | C | B | 13 | -5.948 | 137.016 | 275.199 | 1.00 | 0.00 | C |
| ATOM | 1796 | N4 | C | B | 13 | -7.009 | 137.705 | 274.780 | 1.00 | 0.00 | N |
| ATOM | 1797 | C5 | C | B | 13 | -5.413 | 137.257 | 276.502 | 1.00 | 0.00 | C |
| ATOM | 1798 | C6 | C | B | 13 | -4.347 | 136.526 | 276.876 | 1.00 | 0.00 | C |
| ATOM | 1799 | P | A | B | 14 | 1.527 | 137.037 | 275.783 | 1.00 | 0.00 | P |
| ATOM | 1800 | O1P | A | B | 14 | 2.952 | 137.131 | 276.194 | 1.00 | 0.00 | O |
| ATOM | 1801 | O2P | A | B | 14 | 0.773 | 138.277 | 275.481 | 1.00 | 0.00 | O |
| ATOM | 1802 | O5* | A | B | 14 | 1.475 | 136.066 | 274.535 | 1.00 | 0.00 | O |
| ATOM | 1803 | C5* | A | B | 14 | 1.074 | 136.536 | 273.282 | 1.00 | 0.00 | C |
| ATOM | 1804 | C4* | A | B | 14 | 1.180 | 135.441 | 272.266 | 1.00 | 0.00 | C |
| ATOM | 1805 | O4* | A | B | 14 | -0.111 | 134.779 | 272.201 | 1.00 | 0.00 | O |

| | | | | | | | | | | | |
|---|---|---|---|---|---|---|---|---|---|---|---|
| ATOM | 1806 | C3* | A | B | 14 | 1.405 | 135.996 | 270.865 | 1.00 | 0.00 | C |
| ATOM | 1807 | O3* | A | B | 14 | 2.783 | 136.104 | 270.575 | 1.00 | 0.00 | O |
| ATOM | 1808 | C2* | A | B | 14 | 0.699 | 134.980 | 269.992 | 1.00 | 0.00 | C |
| ATOM | 1809 | O2* | A | B | 14 | 1.445 | 133.792 | 269.804 | 1.00 | 0.00 | O |
| ATOM | 1810 | C1* | A | B | 14 | -0.533 | 134.692 | 270.839 | 1.00 | 0.00 | C |
| ATOM | 1811 | N9 | A | B | 14 | -1.619 | 135.641 | 270.617 | 1.00 | 0.00 | N |
| ATOM | 1812 | C8 | A | B | 14 | -2.185 | 136.541 | 271.498 | 1.00 | 0.00 | C |
| ATOM | 1813 | N7 | A | B | 14 | -3.222 | 137.183 | 270.992 | 1.00 | 0.00 | N |
| ATOM | 1814 | C5 | A | B | 14 | -3.327 | 136.688 | 269.701 | 1.00 | 0.00 | C |
| ATOM | 1815 | C6 | A | B | 14 | -4.194 | 136.985 | 268.648 | 1.00 | 0.00 | C |
| ATOM | 1816 | N6 | A | B | 14 | -5.212 | 137.869 | 268.729 | 1.00 | 0.00 | N |
| ATOM | 1817 | N1 | A | B | 14 | -3.991 | 136.344 | 267.482 | 1.00 | 0.00 | N |
| ATOM | 1818 | C2 | A | B | 14 | -2.986 | 135.472 | 267.392 | 1.00 | 0.00 | C |
| ATOM | 1819 | N3 | A | B | 14 | -2.105 | 135.124 | 268.294 | 1.00 | 0.00 | N |
| ATOM | 1820 | C4 | A | B | 14 | -2.331 | 135.766 | 269.446 | 1.00 | 0.00 | C |
| ATOM | 1821 | P | G | B | 15 | 3.414 | 137.542 | 270.293 | 1.00 | 0.00 | P |
| ATOM | 1822 | O1P | G | B | 15 | 4.866 | 137.370 | 270.059 | 1.00 | 0.00 | O |
| ATOM | 1823 | O2P | G | B | 15 | 2.951 | 138.522 | 271.275 | 1.00 | 0.00 | O |
| ATOM | 1824 | O5* | G | B | 15 | 2.718 | 138.019 | 268.942 | 1.00 | 0.00 | O |
| ATOM | 1825 | C5* | G | B | 15 | 2.672 | 137.190 | 267.809 | 1.00 | 0.00 | C |
| ATOM | 1826 | C4* | G | B | 15 | 1.572 | 137.660 | 266.873 | 1.00 | 0.00 | C |
| ATOM | 1827 | O4* | G | B | 15 | 0.276 | 137.290 | 267.416 | 1.00 | 0.00 | O |
| ATOM | 1828 | C3* | G | B | 15 | 1.441 | 139.161 | 266.690 | 1.00 | 0.00 | C |
| ATOM | 1829 | O3* | G | B | 15 | 2.394 | 139.664 | 265.764 | 1.00 | 0.00 | O |
| ATOM | 1830 | C2* | G | B | 15 | 0.025 | 139.269 | 266.134 | 1.00 | 0.00 | C |
| ATOM | 1831 | O2* | G | B | 15 | -0.121 | 138.832 | 264.814 | 1.00 | 0.00 | O |
| ATOM | 1832 | C1* | G | B | 15 | -0.698 | 138.264 | 267.028 | 1.00 | 0.00 | C |
| ATOM | 1833 | N9 | G | B | 15 | -1.147 | 139.026 | 268.185 | 1.00 | 0.00 | N |
| ATOM | 1834 | C8 | G | B | 15 | -0.565 | 139.123 | 269.431 | 1.00 | 0.00 | C |
| ATOM | 1835 | N7 | G | B | 15 | -1.206 | 139.961 | 270.228 | 1.00 | 0.00 | N |
| ATOM | 1836 | C5 | G | B | 15 | -2.270 | 140.423 | 269.470 | 1.00 | 0.00 | C |
| ATOM | 1837 | C6 | G | B | 15 | -3.306 | 141.382 | 269.782 | 1.00 | 0.00 | C |
| ATOM | 1838 | O6 | G | B | 15 | -3.507 | 141.999 | 270.839 | 1.00 | 0.00 | O |
| ATOM | 1839 | N1 | G | B | 15 | -4.158 | 141.580 | 268.706 | 1.00 | 0.00 | N |
| ATOM | 1840 | C2 | G | B | 15 | -4.051 | 140.967 | 267.486 | 1.00 | 0.00 | C |
| ATOM | 1841 | N2 | G | B | 15 | -4.977 | 141.320 | 266.596 | 1.00 | 0.00 | N |
| ATOM | 1842 | N3 | G | B | 15 | -3.100 | 140.079 | 267.168 | 1.00 | 0.00 | N |
| ATOM | 1843 | C4 | G | B | 15 | -2.254 | 139.855 | 268.205 | 1.00 | 0.00 | C |
| HETATM | 1844 | P | H2U | B | 16 | 3.099 | 141.088 | 266.029 | 1.00 | 0.00 | P |
| HETATM | 1845 | O1P | H2U | B | 16 | 1.996 | 142.038 | 266.340 | 1.00 | 0.00 | O |
| HETATM | 1846 | O2P | H2U | B | 16 | 4.231 | 140.959 | 266.986 | 1.00 | 0.00 | O |
| HETATM | 1847 | O5* | H2U | B | 16 | 3.642 | 141.483 | 264.573 | 1.00 | 0.00 | O |
| HETATM | 1848 | C5* | H2U | B | 16 | 2.705 | 141.645 | 263.492 | 1.00 | 0.00 | C |
| HETATM | 1849 | C4* | H2U | B | 16 | 3.364 | 141.379 | 262.152 | 1.00 | 0.00 | C |
| HETATM | 1850 | O4* | H2U | B | 16 | 4.417 | 142.346 | 261.955 | 1.00 | 0.00 | O |
| HETATM | 1851 | C3* | H2U | B | 16 | 4.089 | 140.052 | 262.033 | 1.00 | 0.00 | C |
| HETATM | 1852 | O3* | H2U | B | 16 | 4.147 | 139.603 | 260.655 | 1.00 | 0.00 | O |
| HETATM | 1853 | C1* | H2U | B | 16 | 5.634 | 141.824 | 262.458 | 1.00 | 0.00 | C |
| HETATM | 1854 | C2* | H2U | B | 16 | 5.388 | 140.344 | 262.787 | 1.00 | 0.00 | C |
| HETATM | 1855 | O2* | H2U | B | 16 | 6.479 | 139.503 | 262.482 | 1.00 | 0.00 | O |
| HETATM | 1856 | N1 | H2U | B | 16 | 6.020 | 142.645 | 263.615 | 1.00 | 0.00 | N |
| HETATM | 1857 | C2 | H2U | B | 16 | 5.832 | 144.016 | 263.500 | 1.00 | 0.00 | C |
| HETATM | 1858 | O2 | H2U | B | 16 | 5.221 | 144.516 | 262.572 | 1.00 | 0.00 | O |
| HETATM | 1859 | N3 | H2U | B | 16 | 6.381 | 144.786 | 264.496 | 1.00 | 0.00 | N |
| HETATM | 1860 | C4 | H2U | B | 16 | 7.137 | 144.373 | 265.575 | 1.00 | 0.00 | C |
| HETATM | 1861 | O4 | H2U | B | 16 | 7.535 | 145.213 | 266.386 | 1.00 | 0.00 | O |
| HETATM | 1862 | C5 | H2U | B | 16 | 7.551 | 142.926 | 265.537 | 1.00 | 0.00 | C |
| HETATM | 1863 | C6 | H2U | B | 16 | 6.560 | 142.031 | 264.844 | 1.00 | 0.00 | C |
| HETATM | 1864 | P | H2U | B | 17 | 5.393 | 139.987 | 259.690 | 1.00 | 0.00 | P |
| HETATM | 1865 | O1P | H2U | B | 17 | 6.617 | 140.338 | 260.437 | 1.00 | 0.00 | O |
| HETATM | 1866 | O2P | H2U | B | 17 | 5.463 | 138.947 | 258.629 | 1.00 | 0.00 | O |
| HETATM | 1867 | O5* | H2U | B | 17 | 4.938 | 141.336 | 258.987 | 1.00 | 0.00 | O |
| HETATM | 1868 | C5* | H2U | B | 17 | 5.850 | 142.427 | 258.861 | 1.00 | 0.00 | C |
| HETATM | 1869 | C4* | H2U | B | 17 | 5.292 | 143.461 | 257.908 | 1.00 | 0.00 | C |
| HETATM | 1870 | O4* | H2U | B | 17 | 5.293 | 142.906 | 256.561 | 1.00 | 0.00 | O |
| HETATM | 1871 | C3* | H2U | B | 17 | 3.850 | 143.887 | 258.194 | 1.00 | 0.00 | C |
| HETATM | 1872 | O3* | H2U | B | 17 | 3.772 | 145.301 | 258.053 | 1.00 | 0.00 | O |
| HETATM | 1873 | C1* | H2U | B | 17 | 4.028 | 143.087 | 255.981 | 1.00 | 0.00 | C |
| HETATM | 1874 | C2* | H2U | B | 17 | 3.043 | 143.111 | 257.146 | 1.00 | 0.00 | C |
| HETATM | 1875 | O2* | H2U | B | 17 | 1.817 | 143.685 | 256.700 | 1.00 | 0.00 | O |
| HETATM | 1876 | N1 | H2U | B | 17 | 3.800 | 142.017 | 255.004 | 1.00 | 0.00 | N |
| HETATM | 1877 | C2 | H2U | B | 17 | 3.938 | 142.375 | 253.679 | 1.00 | 0.00 | C |
| HETATM | 1878 | O2 | H2U | B | 17 | 3.991 | 143.538 | 253.325 | 1.00 | 0.00 | O |
| HETATM | 1879 | N3 | H2U | B | 17 | 4.020 | 141.341 | 252.782 | 1.00 | 0.00 | N |
| HETATM | 1880 | C4 | H2U | B | 17 | 4.005 | 139.995 | 253.049 | 1.00 | 0.00 | C |
| HETATM | 1881 | O4 | H2U | B | 17 | 4.003 | 139.194 | 252.105 | 1.00 | 0.00 | O |
| HETATM | 1882 | C5 | H2U | B | 17 | 4.152 | 139.645 | 254.521 | 1.00 | 0.00 | C |
| HETATM | 1883 | C6 | H2U | B | 17 | 3.483 | 140.637 | 255.413 | 1.00 | 0.00 | C |
| ATOM | 1884 | P | G | B | 18 | 3.794 | 146.217 | 259.359 | 1.00 | 0.00 | P |
| ATOM | 1885 | O1P | G | B | 18 | 4.070 | 147.627 | 259.059 | 1.00 | 0.00 | O |
| ATOM | 1886 | O2P | G | B | 18 | 4.640 | 145.499 | 260.329 | 1.00 | 0.00 | O |
| ATOM | 1887 | O5* | G | B | 18 | 2.299 | 146.088 | 259.865 | 1.00 | 0.00 | O |
| ATOM | 1888 | C5* | G | B | 18 | 1.457 | 147.169 | 259.790 | 1.00 | 0.00 | C |
| ATOM | 1889 | C4* | G | B | 18 | 0.100 | 146.753 | 259.294 | 1.00 | 0.00 | C |
| ATOM | 1890 | O4* | G | B | 18 | -0.544 | 148.040 | 259.291 | 1.00 | 0.00 | O |
| ATOM | 1891 | C3* | G | B | 18 | 0.046 | 146.284 | 257.828 | 1.00 | 0.00 | C |
| ATOM | 1892 | O3* | G | B | 18 | -1.260 | 145.845 | 257.413 | 1.00 | 0.00 | O |

```
ATOM   1893  C2*   G B  18    0.252 147.601 257.117  1.00  0.00           C
ATOM   1894  O2*   G B  18   -0.253 147.579 255.787  1.00  0.00           O
ATOM   1895  C1*   G B  18   -0.662 148.485 257.962  1.00  0.00           C
ATOM   1896  N9    G B  18   -0.298 149.891 257.901  1.00  0.00           N
ATOM   1897  C8    G B  18    0.950 150.431 257.706  1.00  0.00           C
ATOM   1898  N7    G B  18    0.920 151.731 257.567  1.00  0.00           N
ATOM   1899  C5    G B  18   -0.418 152.049 257.714  1.00  0.00           C
ATOM   1900  C6    G B  18   -1.062 153.272 257.617  1.00  0.00           C
ATOM   1901  O6    G B  18   -0.566 154.360 257.375  1.00  0.00           O
ATOM   1902  N1    G B  18   -2.443 153.151 257.816  1.00  0.00           N
ATOM   1903  C2    G B  18   -3.095 151.990 258.060  1.00  0.00           C
ATOM   1904  N2    G B  18   -4.422 152.076 258.236  1.00  0.00           N
ATOM   1905  N3    G B  18   -2.492 150.813 258.131  1.00  0.00           N
ATOM   1906  C4    G B  18   -1.171 150.923 257.949  1.00  0.00           C
ATOM   1907  P     G B  19   -1.672 144.282 257.470  1.00  0.00           P
ATOM   1908  O1P   G B  19   -1.730 143.807 258.886  1.00  0.00           O
ATOM   1909  O2P   G B  19   -0.891 143.486 256.482  1.00  0.00           O
ATOM   1910  O5*   G B  19   -3.153 144.319 256.913  1.00  0.00           O
ATOM   1911  C5*   G B  19   -4.217 144.773 257.764  1.00  0.00           C
ATOM   1912  C4*   G B  19   -5.509 144.802 257.010  1.00  0.00           C
ATOM   1913  O4*   G B  19   -5.293 145.666 255.853  1.00  0.00           O
ATOM   1914  C3*   G B  19   -5.950 143.451 256.441  1.00  0.00           C
ATOM   1915  O3*   G B  19   -7.360 143.434 256.214  1.00  0.00           O
ATOM   1916  C2*   G B  19   -5.234 143.461 255.076  1.00  0.00           C
ATOM   1917  O2*   G B  19   -5.846 142.611 254.141  1.00  0.00           O
ATOM   1918  C1*   G B  19   -5.417 144.917 254.647  1.00  0.00           C
ATOM   1919  N9    G B  19   -4.419 145.487 253.761  1.00  0.00           N
ATOM   1920  C8    G B  19   -3.113 145.087 253.595  1.00  0.00           C
ATOM   1921  N7    G B  19   -2.404 145.943 252.895  1.00  0.00           N
ATOM   1922  C5    G B  19   -3.312 146.941 252.536  1.00  0.00           C
ATOM   1923  C6    G B  19   -3.138 148.144 251.779  1.00  0.00           C
ATOM   1924  O6    G B  19   -2.137 148.575 251.249  1.00  0.00           O
ATOM   1925  N1    G B  19   -4.311 148.868 251.678  1.00  0.00           N
ATOM   1926  C2    G B  19   -5.512 148.514 252.215  1.00  0.00           C
ATOM   1927  N2    G B  19   -6.535 149.384 251.973  1.00  0.00           N
ATOM   1928  N3    G B  19   -5.707 147.402 252.923  1.00  0.00           N
ATOM   1929  C4    G B  19   -4.566 146.663 253.038  1.00  0.00           C
ATOM   1930  P     G B  20   -8.405 142.968 257.391  1.00  0.00           P
ATOM   1931  O1P   G B  20   -9.741 143.488 257.024  1.00  0.00           O
ATOM   1932  O2P   G B  20   -7.826 143.366 258.675  1.00  0.00           O
ATOM   1933  O5*   G B  20   -8.428 141.379 257.310  1.00  0.00           O
ATOM   1934  C5*   G B  20   -8.987 140.670 256.217  1.00  0.00           C
ATOM   1935  C4*   G B  20   -9.319 139.248 256.636  1.00  0.00           C
ATOM   1936  O4*   G B  20   -8.122 138.406 256.589  1.00  0.00           O
ATOM   1937  C3*   G B  20   -9.848 139.122 258.062  1.00  0.00           C
ATOM   1938  O3*   G B  20  -11.274 139.184 258.064  1.00  0.00           O
ATOM   1939  C2*   G B  20   -9.365 137.753 258.495  1.00  0.00           C
ATOM   1940  O2*   G B  20  -10.154 136.682 258.061  1.00  0.00           O
ATOM   1941  C1*   G B  20   -8.029 137.647 257.772  1.00  0.00           C
ATOM   1942  N9    G B  20   -6.941 138.178 258.583  1.00  0.00           N
ATOM   1943  C8    G B  20   -6.123 139.232 258.285  1.00  0.00           C
ATOM   1944  N7    G B  20   -5.256 139.480 259.235  1.00  0.00           N
ATOM   1945  C5    G B  20   -5.520 138.521 260.195  1.00  0.00           C
ATOM   1946  C6    G B  20   -4.916 138.305 261.453  1.00  0.00           C
ATOM   1947  O6    G B  20   -3.987 138.912 261.946  1.00  0.00           O
ATOM   1948  N1    G B  20   -5.521 137.258 262.147  1.00  0.00           N
ATOM   1949  C2    G B  20   -6.570 136.502 261.676  1.00  0.00           C
ATOM   1950  N2    G B  20   -7.042 135.522 262.505  1.00  0.00           N
ATOM   1951  N3    G B  20   -7.123 136.687 260.486  1.00  0.00           N
ATOM   1952  C4    G B  20   -6.555 137.712 259.812  1.00  0.00           C
ATOM   1953  P     A B  21  -11.983 140.240 258.023  1.00  0.00           P
ATOM   1954  O1P   A B  21  -13.432 140.062 258.882  1.00  0.00           O
ATOM   1955  O2P   A B  21  -11.363 141.564 258.701  1.00  0.00           O
ATOM   1956  O5*   A B  21  -11.582 139.592 260.410  1.00  0.00           O
ATOM   1957  C5*   A B  21  -11.216 140.333 261.504  1.00  0.00           C
ATOM   1958  C4*   A B  21  -10.321 139.510 262.379  1.00  0.00           C
ATOM   1959  O4*   A B  21   -9.840 140.440 263.322  1.00  0.00           O
ATOM   1960  C3*   A B  21  -10.797 138.300 263.204  1.00  0.00           C
ATOM   1961  O3*   A B  21  -10.697 137.077 262.432  1.00  0.00           O
ATOM   1962  C2*   A B  21   -9.742 138.277 264.303  1.00  0.00           C
ATOM   1963  O2*   A B  21   -8.548 137.659 263.849  1.00  0.00           O
ATOM   1964  C1*   A B  21   -9.431 139.769 264.482  1.00  0.00           C
ATOM   1965  N9    A B  21  -10.111 140.454 265.560  1.00  0.00           N
ATOM   1966  C8    A B  21  -11.288 141.125 265.456  1.00  0.00           C
ATOM   1967  N7    A B  21  -11.629 141.750 266.552  1.00  0.00           N
ATOM   1968  C5    A B  21  -10.617 141.443 267.435  1.00  0.00           C
ATOM   1969  C6    A B  21  -10.417 141.772 268.764  1.00  0.00           C
ATOM   1970  N6    A B  21  -11.254 142.555 269.452  1.00  0.00           N
ATOM   1971  N1    A B  21   -9.334 141.280 269.378  1.00  0.00           N
ATOM   1972  C2    A B  21   -8.504 140.506 268.674  1.00  0.00           C
ATOM   1973  N3    A B  21   -8.588 140.125 267.407  1.00  0.00           N
ATOM   1974  C4    A B  21   -9.684 140.630 266.844  1.00  0.00           C
ATOM   1975  P     G B  22  -11.111 135.623 263.056  1.00  0.00           P
ATOM   1976  O1P   G B  22  -11.229 134.652 261.969  1.00  0.00           O
ATOM   1977  O2P   G B  22  -12.204 135.734 264.045  1.00  0.00           O
ATOM   1978  O5*   G B  22   -9.845 135.200 263.892  1.00  0.00           O
ATOM   1979  C5*   G B  22   -9.956 134.306 264.976  1.00  0.00           C
```

```
ATOM   1980  C4*   G B  22    -8.595 133.735 265.282  1.00  0.00           C
ATOM   1981  O4*   G B  22    -7.689 134.826 265.598  1.00  0.00           O
ATOM   1982  C3*   G B  22    -8.530 132.782 266.459  1.00  0.00           C
ATOM   1983  O3*   G B  22    -8.820 131.446 266.023  1.00  0.00           O
ATOM   1984  C2*   G B  22    -7.108 132.996 266.955  1.00  0.00           C
ATOM   1985  O2*   G B  22    -6.090 132.322 266.250  1.00  0.00           O
ATOM   1986  C1*   G B  22    -6.935 134.497 266.743  1.00  0.00           C
ATOM   1987  N9    G B  22    -7.451 135.263 267.871  1.00  0.00           N
ATOM   1988  C8    G B  22    -8.511 136.134 267.876  1.00  0.00           C
ATOM   1989  N7    G B  22    -8.685 136.708 269.035  1.00  0.00           N
ATOM   1990  C5    G B  22    -7.692 136.162 269.842  1.00  0.00           C
ATOM   1991  C6    G B  22    -7.376 136.420 271.195  1.00  0.00           C
ATOM   1992  O6    G B  22    -7.933 137.196 271.961  1.00  0.00           O
ATOM   1993  N1    G B  22    -6.289 135.671 271.626  1.00  0.00           N
ATOM   1994  C2    G B  22    -5.588 134.785 270.842  1.00  0.00           C
ATOM   1995  N2    G B  22    -4.560 134.154 271.428  1.00  0.00           N
ATOM   1996  N3    G B  22    -5.873 134.542 269.581  1.00  0.00           N
ATOM   1997  C4    G B  22    -6.935 135.266 269.152  1.00  0.00           C
ATOM   1998  P     A B  23    -9.548 130.413 267.025  1.00  0.00           P
ATOM   1999  O1P   A B  23   -10.049 129.232 266.286  1.00  0.00           O
ATOM   2000  O2P   A B  23   -10.498 131.221 267.819  1.00  0.00           O
ATOM   2001  O5*   A B  23    -8.380 129.939 267.976  1.00  0.00           O
ATOM   2002  C5*   A B  23    -7.251 129.294 267.438  1.00  0.00           C
ATOM   2003  C4*   A B  23    -6.279 128.938 268.526  1.00  0.00           C
ATOM   2004  O4*   A B  23    -5.610 130.119 269.039  1.00  0.00           O
ATOM   2005  C3*   A B  23    -6.869 128.264 269.751  1.00  0.00           C
ATOM   2006  O3*   A B  23    -6.966 126.870 269.482  1.00  0.00           O
ATOM   2007  C2*   A B  23    -5.773 128.522 270.764  1.00  0.00           C
ATOM   2008  O2*   A B  23    -4.686 127.643 270.521  1.00  0.00           O
ATOM   2009  C1*   A B  23    -5.393 129.966 270.427  1.00  0.00           C
ATOM   2010  N9    A B  23    -6.254 130.937 271.105  1.00  0.00           N
ATOM   2011  C8    A B  23    -7.337 131.596 270.571  1.00  0.00           C
ATOM   2012  N7    A B  23    -7.887 132.458 271.392  1.00  0.00           N
ATOM   2013  C5    A B  23    -7.135 132.330 272.552  1.00  0.00           C
ATOM   2014  C6    A B  23    -7.235 132.943 273.793  1.00  0.00           C
ATOM   2015  N6    A B  23    -8.162 133.866 274.076  1.00  0.00           N
ATOM   2016  N1    A B  23    -6.354 132.584 274.746  1.00  0.00           N
ATOM   2017  C2    A B  23    -5.424 131.660 274.447  1.00  0.00           C
ATOM   2018  N3    A B  23    -5.229 131.010 273.311  1.00  0.00           N
ATOM   2019  C4    A B  23    -6.132 131.393 272.391  1.00  0.00           C
ATOM   2020  P     G B  24    -8.103 125.985 270.213  1.00  0.00           P
ATOM   2021  O1P   G B  24    -8.023 124.691 269.512  1.00  0.00           O
ATOM   2022  O2P   G B  24    -9.379 126.735 270.226  1.00  0.00           O
ATOM   2023  O5*   G B  24    -7.561 125.869 271.701  1.00  0.00           O
ATOM   2024  C5*   G B  24    -6.243 125.427 271.934  1.00  0.00           C
ATOM   2025  C4*   G B  24    -5.924 125.515 273.394  1.00  0.00           C
ATOM   2026  O4*   G B  24    -5.489 126.869 273.668  1.00  0.00           O
ATOM   2027  C3*   G B  24    -7.095 125.288 274.340  1.00  0.00           C
ATOM   2028  O3*   G B  24    -7.216 123.900 274.626  1.00  0.00           O
ATOM   2029  C2*   G B  24    -6.614 126.045 275.564  1.00  0.00           C
ATOM   2030  O2*   G B  24    -5.565 125.365 276.220  1.00  0.00           O
ATOM   2031  C1*   G B  24    -6.010 127.290 274.908  1.00  0.00           C
ATOM   2032  N9    G B  24    -7.032 128.288 274.647  1.00  0.00           N
ATOM   2033  C8    G B  24    -7.775 128.448 273.505  1.00  0.00           C
ATOM   2034  N7    G B  24    -8.676 129.385 273.612  1.00  0.00           N
ATOM   2035  C5    G B  24    -8.489 129.885 274.897  1.00  0.00           C
ATOM   2036  C6    G B  24    -9.187 130.893 275.598  1.00  0.00           C
ATOM   2037  O6    G B  24   -10.132 131.601 275.201  1.00  0.00           O
ATOM   2038  N1    G B  24    -8.698 131.045 276.893  1.00  0.00           N
ATOM   2039  C2    G B  24    -7.669 130.322 277.441  1.00  0.00           C
ATOM   2040  N2    G B  24    -7.350 130.602 278.714  1.00  0.00           N
ATOM   2041  N3    G B  24    -7.002 129.384 276.787  1.00  0.00           N
ATOM   2042  C4    G B  24    -7.468 129.221 275.533  1.00  0.00           C
ATOM   2043  P     C B  25    -8.670 123.260 274.890  1.00  0.00           P
ATOM   2044  O1P   C B  25    -8.453 121.798 275.112  1.00  0.00           O
ATOM   2045  O2P   C B  25    -9.594 123.701 273.839  1.00  0.00           O
ATOM   2046  O5*   C B  25    -9.139 123.931 276.253  1.00  0.00           O
ATOM   2047  C5*   C B  25    -8.359 123.797 277.424  1.00  0.00           C
ATOM   2048  C4*   C B  25    -8.859 124.727 278.503  1.00  0.00           C
ATOM   2049  O4*   C B  25    -8.559 126.112 278.159  1.00  0.00           O
ATOM   2050  C3*   C B  25   -10.355 124.758 278.788  1.00  0.00           C
ATOM   2051  O3*   C B  25   -10.762 123.628 279.562  1.00  0.00           O
ATOM   2052  C2*   C B  25   -10.446 126.053 279.589  1.00  0.00           C
ATOM   2053  O2*   C B  25    -9.888 125.913 280.880  1.00  0.00           O
ATOM   2054  C1*   C B  25    -9.514 126.962 278.778  1.00  0.00           C
ATOM   2055  N1    C B  25   -10.241 127.667 277.731  1.00  0.00           N
ATOM   2056  C2    C B  25   -10.938 128.809 278.073  1.00  0.00           C
ATOM   2057  O2    C B  25   -10.892 129.196 279.244  1.00  0.00           O
ATOM   2058  N3    C B  25   -11.647 129.466 277.126  1.00  0.00           N
ATOM   2059  C4    C B  25   -11.673 129.010 275.875  1.00  0.00           C
ATOM   2060  N4    C B  25   -12.389 129.689 274.974  1.00  0.00           N
ATOM   2061  C5    C B  25   -10.961 127.837 275.490  1.00  0.00           C
ATOM   2062  C6    C B  25   -10.254 127.201 276.446  1.00  0.00           C
HETATM 2063  P    M2G B  26   -11.242 123.296 278.237  1.00  0.00           P
HETATM 2064  O1P  M2G B  26   -11.682 122.902 276.883  1.00  0.00           O
HETATM 2065  O2P  M2G B  26   -11.190 122.280 279.313  1.00  0.00           O
HETATM 2066  O5*  M2G B  26   -12.176 124.481 278.737  1.00  0.00           O
```

| | | | | | | | | | | |
|---|---|---|---|---|---|---|---|---|---|---|
| HETATM | 2067 | C5* | M2G | B | 26 | -12.314 | 124.755 | 280.124 | 1.00 | 0.00 | C |
| HETATM | 2068 | C4* | M2G | B | 26 | -13.298 | 125.876 | 280.337 | 1.00 | 0.00 | C |
| HETATM | 2069 | O4* | M2G | B | 26 | -12.922 | 127.032 | 279.529 | 1.00 | 0.00 | O |
| HETATM | 2070 | C3* | M2G | B | 26 | -14.708 | 125.580 | 279.872 | 1.00 | 0.00 | C |
| HETATM | 2071 | O3* | M2G | B | 26 | -15.404 | 124.831 | 280.853 | 1.00 | 0.00 | O |
| HETATM | 2072 | C2* | M2G | B | 26 | -15.278 | 126.983 | 279.740 | 1.00 | 0.00 | C |
| HETATM | 2073 | O2* | M2G | B | 26 | -15.524 | 127.570 | 280.999 | 1.00 | 0.00 | O |
| HETATM | 2074 | C1* | M2G | B | 26 | -14.100 | 127.697 | 279.080 | 1.00 | 0.00 | C |
| HETATM | 2075 | N9 | M2G | B | 26 | -14.132 | 127.641 | 277.621 | 1.00 | 0.00 | N |
| HETATM | 2076 | C8 | M2G | B | 26 | -13.398 | 126.814 | 276.798 | 1.00 | 0.00 | C |
| HETATM | 2077 | N7 | M2G | B | 26 | -13.636 | 127.007 | 275.533 | 1.00 | 0.00 | N |
| HETATM | 2078 | C5 | M2G | B | 26 | -14.577 | 128.028 | 275.523 | 1.00 | 0.00 | C |
| HETATM | 2079 | C6 | M2G | B | 26 | -15.203 | 128.671 | 274.439 | 1.00 | 0.00 | C |
| HETATM | 2080 | O6 | M2G | B | 26 | -15.044 | 128.458 | 273.231 | 1.00 | 0.00 | O |
| HETATM | 2081 | N1 | M2G | B | 26 | -16.096 | 129.647 | 274.866 | 1.00 | 0.00 | N |
| HETATM | 2082 | C2 | M2G | B | 26 | -16.352 | 129.960 | 276.185 | 1.00 | 0.00 | C |
| HETATM | 2083 | N2 | M2G | B | 26 | -17.276 | 130.898 | 276.412 | 1.00 | 0.00 | N |
| HETATM | 2084 | N3 | M2G | B | 26 | -15.766 | 129.367 | 277.210 | 1.00 | 0.00 | N |
| HETATM | 2085 | C4 | M2G | B | 26 | -14.896 | 128.416 | 276.806 | 1.00 | 0.00 | C |
| HETATM | 2086 | CM1 | M2G | B | 26 | -17.855 | 131.047 | 277.762 | 1.00 | 0.00 | C |
| HETATM | 2087 | CM2 | M2G | B | 26 | -17.712 | 131.777 | 275.322 | 1.00 | 0.00 | C |
| ATOM | 2088 | P | C | B | 27 | -16.305 | 123.587 | 280.397 | 1.00 | 0.00 | P |
| ATOM | 2089 | O1P | C | B | 27 | -16.783 | 122.903 | 281.630 | 1.00 | 0.00 | O |
| ATOM | 2090 | O2P | C | B | 27 | -15.521 | 122.818 | 279.393 | 1.00 | 0.00 | O |
| ATOM | 2091 | O5* | C | B | 27 | -17.560 | 124.261 | 279.680 | 1.00 | 0.00 | O |
| ATOM | 2092 | C5* | C | B | 27 | -18.410 | 125.139 | 280.396 | 1.00 | 0.00 | C |
| ATOM | 2093 | C4* | C | B | 27 | -19.392 | 125.807 | 279.463 | 1.00 | 0.00 | C |
| ATOM | 2094 | O4* | C | B | 27 | -18.678 | 126.721 | 278.585 | 1.00 | 0.00 | O |
| ATOM | 2095 | C3* | C | B | 27 | -20.149 | 124.907 | 278.496 | 1.00 | 0.00 | C |
| ATOM | 2096 | O3* | C | B | 27 | -21.277 | 124.280 | 279.104 | 1.00 | 0.00 | O |
| ATOM | 2097 | C2* | C | B | 27 | -20.597 | 125.924 | 277.449 | 1.00 | 0.00 | C |
| ATOM | 2098 | O2* | C | B | 27 | -21.697 | 126.704 | 277.880 | 1.00 | 0.00 | O |
| ATOM | 2099 | C1* | C | B | 27 | -19.349 | 126.802 | 277.333 | 1.00 | 0.00 | C |
| ATOM | 2100 | N1 | C | B | 27 | -18.422 | 126.366 | 276.273 | 1.00 | 0.00 | N |
| ATOM | 2101 | C2 | C | B | 27 | -18.719 | 126.684 | 274.938 | 1.00 | 0.00 | C |
| ATOM | 2102 | O2 | C | B | 27 | -19.768 | 127.288 | 274.681 | 1.00 | 0.00 | O |
| ATOM | 2103 | N3 | C | B | 27 | -17.859 | 126.313 | 273.959 | 1.00 | 0.00 | N |
| ATOM | 2104 | C4 | C | B | 27 | -16.754 | 125.641 | 274.266 | 1.00 | 0.00 | C |
| ATOM | 2105 | N4 | C | B | 27 | -15.947 | 125.298 | 273.266 | 1.00 | 0.00 | N |
| ATOM | 2106 | C5 | C | B | 27 | -16.431 | 125.289 | 275.616 | 1.00 | 0.00 | C |
| ATOM | 2107 | C6 | C | B | 27 | -17.287 | 125.670 | 276.580 | 1.00 | 0.00 | C |
| ATOM | 2108 | P | C | B | 28 | -21.739 | 122.811 | 278.621 | 1.00 | 0.00 | P |
| ATOM | 2109 | O1P | C | B | 28 | -22.792 | 122.398 | 279.575 | 1.00 | 0.00 | O |
| ATOM | 2110 | O2P | C | B | 28 | -20.547 | 121.949 | 278.425 | 1.00 | 0.00 | O |
| ATOM | 2111 | O5* | C | B | 28 | -22.420 | 123.014 | 277.197 | 1.00 | 0.00 | O |
| ATOM | 2112 | C5* | C | B | 28 | -23.690 | 123.630 | 277.092 | 1.00 | 0.00 | C |
| ATOM | 2113 | C4* | C | B | 28 | -24.060 | 123.817 | 275.645 | 1.00 | 0.00 | C |
| ATOM | 2114 | O4* | C | B | 28 | -23.086 | 124.693 | 275.018 | 1.00 | 0.00 | O |
| ATOM | 2115 | C3* | C | B | 28 | -24.008 | 122.580 | 274.772 | 1.00 | 0.00 | C |
| ATOM | 2116 | O3* | C | B | 28 | -25.179 | 121.782 | 274.909 | 1.00 | 0.00 | O |
| ATOM | 2117 | C2* | C | B | 28 | -23.939 | 123.212 | 273.395 | 1.00 | 0.00 | C |
| ATOM | 2118 | O2* | C | B | 28 | -25.185 | 123.759 | 272.999 | 1.00 | 0.00 | O |
| ATOM | 2119 | C1* | C | B | 28 | -22.930 | 124.326 | 273.663 | 1.00 | 0.00 | C |
| ATOM | 2120 | N1 | C | B | 28 | -21.538 | 123.902 | 273.468 | 1.00 | 0.00 | N |
| ATOM | 2121 | C2 | C | B | 28 | -21.046 | 123.850 | 272.170 | 1.00 | 0.00 | C |
| ATOM | 2122 | O2 | C | B | 28 | -21.809 | 124.143 | 271.246 | 1.00 | 0.00 | O |
| ATOM | 2123 | N3 | C | B | 28 | -19.758 | 123.479 | 271.956 | 1.00 | 0.00 | N |
| ATOM | 2124 | C4 | C | B | 28 | -18.974 | 123.158 | 272.989 | 1.00 | 0.00 | C |
| ATOM | 2125 | N4 | C | B | 28 | -17.693 | 122.790 | 272.726 | 1.00 | 0.00 | N |
| ATOM | 2126 | C5 | C | B | 28 | -19.456 | 123.193 | 274.335 | 1.00 | 0.00 | C |
| ATOM | 2127 | C6 | C | B | 28 | -20.734 | 123.569 | 274.525 | 1.00 | 0.00 | C |
| ATOM | 2128 | P | A | B | 29 | -25.061 | 120.188 | 274.771 | 1.00 | 0.00 | P |
| ATOM | 2129 | O1P | A | B | 29 | -26.359 | 119.617 | 275.234 | 1.00 | 0.00 | O |
| ATOM | 2130 | O2P | A | B | 29 | -23.785 | 119.735 | 275.403 | 1.00 | 0.00 | O |
| ATOM | 2131 | O5* | A | B | 29 | -24.920 | 119.936 | 273.204 | 1.00 | 0.00 | O |
| ATOM | 2132 | C5* | A | B | 29 | -25.908 | 120.420 | 272.292 | 1.00 | 0.00 | C |
| ATOM | 2133 | C4* | A | B | 29 | -25.389 | 120.384 | 270.860 | 1.00 | 0.00 | C |
| ATOM | 2134 | O4* | A | B | 29 | -24.321 | 121.352 | 270.673 | 1.00 | 0.00 | O |
| ATOM | 2135 | C3* | A | B | 29 | -24.809 | 119.074 | 270.342 | 1.00 | 0.00 | C |
| ATOM | 2136 | O3* | A | B | 29 | -25.854 | 118.214 | 269.897 | 1.00 | 0.00 | O |
| ATOM | 2137 | C2* | A | B | 29 | -23.977 | 119.554 | 269.157 | 1.00 | 0.00 | C |
| ATOM | 2138 | O2* | A | B | 29 | -24.746 | 119.812 | 267.992 | 1.00 | 0.00 | O |
| ATOM | 2139 | C1* | A | B | 29 | -23.396 | 120.859 | 269.708 | 1.00 | 0.00 | C |
| ATOM | 2140 | N9 | A | B | 29 | -22.095 | 120.670 | 270.361 | 1.00 | 0.00 | N |
| ATOM | 2141 | C8 | A | B | 29 | -21.809 | 120.625 | 271.707 | 1.00 | 0.00 | C |
| ATOM | 2142 | N7 | A | B | 29 | -20.535 | 120.434 | 271.970 | 1.00 | 0.00 | N |
| ATOM | 2143 | C5 | A | B | 29 | -19.947 | 120.352 | 270.713 | 1.00 | 0.00 | C |
| ATOM | 2144 | C6 | A | B | 29 | -18.625 | 120.149 | 270.303 | 1.00 | 0.00 | C |
| ATOM | 2145 | N6 | A | B | 29 | -17.598 | 120.002 | 271.141 | 1.00 | 0.00 | N |
| ATOM | 2146 | N1 | A | B | 29 | -18.382 | 120.105 | 268.976 | 1.00 | 0.00 | N |
| ATOM | 2147 | C2 | A | B | 29 | -19.407 | 120.260 | 268.131 | 1.00 | 0.00 | C |
| ATOM | 2148 | N3 | A | B | 29 | -20.688 | 120.459 | 268.393 | 1.00 | 0.00 | N |
| ATOM | 2149 | C4 | A | B | 29 | -20.896 | 120.496 | 269.719 | 1.00 | 0.00 | C |
| ATOM | 2150 | P | G | B | 30 | -25.590 | 116.636 | 269.762 | 1.00 | 0.00 | P |
| ATOM | 2151 | O1P | G | B | 30 | -26.916 | 116.036 | 269.445 | 1.00 | 0.00 | O |
| ATOM | 2152 | O2P | G | B | 30 | -24.837 | 116.170 | 270.954 | 1.00 | 0.00 | O |
| ATOM | 2153 | O5* | G | B | 30 | -24.644 | 116.503 | 268.481 | 1.00 | 0.00 | O |

```
ATOM   2154  C5*  G   B  30   -25.063 116.986 267.204  1.00  0.00           C
ATOM   2155  C4*  G   B  30   -24.019 116.663 266.162  1.00  0.00           C
ATOM   2156  O4*  G   B  30   -22.902 117.585 266.269  1.00  0.00           O
ATOM   2157  C3*  G   B  30   -23.369 115.305 266.322  1.00  0.00           C
ATOM   2158  O3*  G   B  30   -24.193 114.295 265.758  1.00  0.00           O
ATOM   2159  C2*  G   B  30   -22.053 115.493 265.574  1.00  0.00           C
ATOM   2160  O2*  G   B  30   -22.140 115.482 264.161  1.00  0.00           O
ATOM   2161  C1*  G   B  30   -21.681 116.898 266.019  1.00  0.00           C
ATOM   2162  N9   G   B  30   -20.930 116.837 267.260  1.00  0.00           N
ATOM   2163  C8   G   B  30   -21.434 116.936 268.529  1.00  0.00           C
ATOM   2164  N7   G   B  30   -20.514 116.851 269.451  1.00  0.00           N
ATOM   2165  C5   G   B  30   -19.329 116.685 268.747  1.00  0.00           C
ATOM   2166  C6   G   B  30   -17.986 116.565 269.213  1.00  0.00           C
ATOM   2167  O6   G   B  30   -17.572 116.571 270.382  1.00  0.00           O
ATOM   2168  N1   G   B  30   -17.085 116.429 268.156  1.00  0.00           N
ATOM   2169  C2   G   B  30   -17.430 116.418 266.823  1.00  0.00           C
ATOM   2170  N2   G   B  30   -16.413 116.267 265.952  1.00  0.00           N
ATOM   2171  N3   G   B  30   -18.676 116.541 266.377  1.00  0.00           N
ATOM   2172  C4   G   B  30   -19.568 116.668 267.391  1.00  0.00           C
ATOM   2173  P    A   B  31   -23.891 112.751 266.080  1.00  0.00           P
ATOM   2174  O1P  A   B  31   -24.763 111.955 265.184  1.00  0.00           O
ATOM   2175  O2P  A   B  31   -23.969 112.546 267.552  1.00  0.00           O
ATOM   2176  O5*  A   B  31   -22.386 112.545 265.617  1.00  0.00           O
ATOM   2177  C5*  A   B  31   -22.057 112.528 264.237  1.00  0.00           C
ATOM   2178  C4*  A   B  31   -20.602 112.201 264.063  1.00  0.00           C
ATOM   2179  O4*  A   B  31   -19.811 113.305 264.575  1.00  0.00           O
ATOM   2180  C3*  A   B  31   -20.120 110.984 264.843  1.00  0.00           C
ATOM   2181  O3*  A   B  31   -20.308 109.785 264.085  1.00  0.00           O
ATOM   2182  C2*  A   B  31   -18.637 111.294 264.994  1.00  0.00           C
ATOM   2183  O2*  A   B  31   -17.905 111.010 263.817  1.00  0.00           O
ATOM   2184  C1*  A   B  31   -18.675 112.802 265.255  1.00  0.00           C
ATOM   2185  N9   A   B  31   -18.837 113.070 266.676  1.00  0.00           N
ATOM   2186  C8   A   B  31   -19.993 113.277 267.388  1.00  0.00           C
ATOM   2187  N7   A   B  31   -19.799 113.444 268.670  1.00  0.00           N
ATOM   2188  C5   A   B  31   -18.424 113.353 268.813  1.00  0.00           C
ATOM   2189  C6   A   B  31   -17.584 113.460 269.930  1.00  0.00           C
ATOM   2190  N6   A   B  31   -18.035 113.681 271.172  1.00  0.00           N
ATOM   2191  N1   A   B  31   -16.251 113.335 269.729  1.00  0.00           N
ATOM   2192  C2   A   B  31   -15.808 113.120 268.480  1.00  0.00           C
ATOM   2193  N3   A   B  31   -16.503 113.001 267.347  1.00  0.00           N
ATOM   2194  C4   A   B  31   -17.819 113.129 267.590  1.00  0.00           C
HETATM 2195  N1   OMC B  32   -17.972 109.325 269.070  1.00  0.00           N
HETATM 2196  C2   OMC B  32   -17.729 109.944 270.279  1.00  0.00           C
HETATM 2197  N3   OMC B  32   -18.737 110.592 270.908  1.00  0.00           N
HETATM 2198  C4   OMC B  32   -19.949 110.637 270.348  1.00  0.00           C
HETATM 2199  C5   OMC B  32   -20.217 110.027 269.089  1.00  0.00           C
HETATM 2200  C6   OMC B  32   -19.206 109.389 268.490  1.00  0.00           C
HETATM 2201  O2   OMC B  32   -16.585 109.883 270.752  1.00  0.00           O
HETATM 2202  N4   OMC B  32   -20.930 111.273 271.003  1.00  0.00           N
HETATM 2203  C1*  OMC B  32   -16.884 108.587 268.441  1.00  0.00           C
HETATM 2204  C2*  OMC B  32   -16.992 107.095 268.734  1.00  0.00           C
HETATM 2205  O2*  OMC B  32   -15.662 106.530 268.726  1.00  0.00           O
HETATM 2206  CM2  OMC B  32   -14.804 106.717 269.878  1.00  0.00           C
HETATM 2207  C3*  OMC B  32   -17.852 106.631 267.570  1.00  0.00           C
HETATM 2208  C4*  OMC B  32   -17.301 107.463 266.428  1.00  0.00           C
HETATM 2209  O4*  OMC B  32   -16.989 108.741 267.040  1.00  0.00           O
HETATM 2210  O3*  OMC B  32   -17.689 105.243 267.308  1.00  0.00           O
HETATM 2211  C5*  OMC B  32   -18.267 107.691 265.300  1.00  0.00           C
HETATM 2212  O5*  OMC B  32   -19.521 108.119 265.814  1.00  0.00           O
HETATM 2213  P    OMC B  32   -20.734 108.420 264.828  1.00  0.00           P
HETATM 2214  O1P  OMC B  32   -21.954 108.704 265.630  1.00  0.00           O
HETATM 2215  O2P  OMC B  32   -20.757 107.356 263.784  1.00  0.00           O
ATOM   2216  P    U   B  33   -18.522 104.173 268.174  1.00  0.00           P
ATOM   2217  O1P  U   B  33   -17.892 102.848 267.960  1.00  0.00           O
ATOM   2218  O2P  U   B  33   -19.975 104.358 267.900  1.00  0.00           O
ATOM   2219  O5*  U   B  33   -18.260 104.626 269.677  1.00  0.00           O
ATOM   2220  C5*  U   B  33   -17.270 103.990 270.481  1.00  0.00           C
ATOM   2221  C4*  U   B  33   -17.689 104.028 271.934  1.00  0.00           C
ATOM   2222  O4*  U   B  33   -17.833 105.416 272.337  1.00  0.00           O
ATOM   2223  C3*  U   B  33   -19.054 103.408 272.214  1.00  0.00           C
ATOM   2224  O3*  U   B  33   -18.939 102.002 272.453  1.00  0.00           O
ATOM   2225  C2*  U   B  33   -19.514 104.149 273.468  1.00  0.00           C
ATOM   2226  O2*  U   B  33   -19.042 103.564 274.661  1.00  0.00           O
ATOM   2227  C1*  U   B  33   -18.892 105.533 273.270  1.00  0.00           C
ATOM   2228  N1   U   B  33   -19.875 106.490 272.757  1.00  0.00           N
ATOM   2229  C2   U   B  33   -20.516 107.268 273.684  1.00  0.00           C
ATOM   2230  O2   U   B  33   -20.245 107.217 274.867  1.00  0.00           O
ATOM   2231  N3   U   B  33   -21.485 108.106 273.180  1.00  0.00           N
ATOM   2232  C4   U   B  33   -21.860 108.242 271.858  1.00  0.00           C
ATOM   2233  O4   U   B  33   -22.771 109.026 271.560  1.00  0.00           O
ATOM   2234  C5   U   B  33   -21.124 107.412 270.945  1.00  0.00           C
ATOM   2235  C6   U   B  33   -20.173 106.589 271.415  1.00  0.00           C
HETATM 2236  P    OMG B  34   -19.475 100.906 271.952  1.00  0.00           P
HETATM 2237  O1P  OMG B  34   -18.938 100.675 270.579  1.00  0.00           O
HETATM 2238  O2P  OMG B  34   -19.646  99.750 272.870  1.00  0.00           O
HETATM 2239  O5*  OMG B  34   -20.871 101.674 271.852  1.00  0.00           O
HETATM 2240  C5*  OMG B  34   -22.080 100.985 271.550  1.00  0.00           C
```

```
HETATM 2241  C4*  OMG B  34     -22.947 100.912 272.780  1.00  0.00           C
HETATM 2242  O4*  OMG B  34     -22.280 100.051 273.726  1.00  0.00           O
HETATM 2243  C3*  OMG B  34     -23.113 102.223 273.530  1.00  0.00           C
HETATM 2244  O3*  OMG B  34     -24.193 103.010 273.010  1.00  0.00           O
HETATM 2245  C2*  OMG B  34     -23.376 101.765 274.968  1.00  0.00           C
HETATM 2246  O2*  OMG B  34     -24.769 101.559 275.309  1.00  0.00           O
HETATM 2247  CM2  OMG B  34     -25.145 101.391 276.698  1.00  0.00           C
HETATM 2248  C1*  OMG B  34     -22.622 100.438 275.039  1.00  0.00           C
HETATM 2249  N9   OMG B  34     -21.401 100.471 275.834  1.00  0.00           N
HETATM 2250  C8   OMG B  34     -20.148 100.056 275.445  1.00  0.00           C
HETATM 2251  N7   OMG B  34     -19.252 100.157 276.391  1.00  0.00           N
HETATM 2252  C5   OMG B  34     -19.953 100.681 277.471  1.00  0.00           C
HETATM 2253  C6   OMG B  34     -19.513 100.991 278.794  1.00  0.00           C
HETATM 2254  O6   OMG B  34     -18.371 100.868 279.289  1.00  0.00           O
HETATM 2255  N1   OMG B  34     -20.563 101.494 279.574  1.00  0.00           N
HETATM 2256  C2   OMG B  34     -21.867 101.676 279.140  1.00  0.00           C
HETATM 2257  N2   OMG B  34     -22.732 102.182 280.042  1.00  0.00           N
HETATM 2258  N3   OMG B  34     -22.285 101.385 277.913  1.00  0.00           N
HETATM 2259  C4   OMG B  34     -21.283 100.895 277.138  1.00  0.00           C
ATOM   2260  P    A   B  35     -23.865 104.821 272.891  1.00  0.00           P
ATOM   2261  O1P  A   B  35     -25.205 105.204 272.371  1.00  0.00           O
ATOM   2262  O2P  A   B  35     -22.800 104.379 271.954  1.00  0.00           O
ATOM   2263  O5*  A   B  35     -23.278 106.039 273.732  1.00  0.00           O
ATOM   2264  C5*  A   B  35     -22.403 105.788 274.823  1.00  0.00           C
ATOM   2265  C4*  A   B  35     -23.035 106.169 276.142  1.00  0.00           C
ATOM   2266  O4*  A   B  35     -22.945 105.008 277.020  1.00  0.00           O
ATOM   2267  C3*  A   B  35     -22.310 107.300 276.878  1.00  0.00           C
ATOM   2268  O3*  A   B  35     -23.004 108.535 276.687  1.00  0.00           O
ATOM   2269  C2*  A   B  35     -22.371 106.851 278.337  1.00  0.00           C
ATOM   2270  O2*  A   B  35     -23.609 107.152 278.963  1.00  0.00           O
ATOM   2271  C1*  A   B  35     -22.216 105.345 278.176  1.00  0.00           C
ATOM   2272  N9   A   B  35     -20.838 104.921 277.964  1.00  0.00           N
ATOM   2273  C8   A   B  35     -20.252 104.483 276.803  1.00  0.00           C
ATOM   2274  N7   A   B  35     -18.986 104.171 276.939  1.00  0.00           N
ATOM   2275  C5   A   B  35     -18.722 104.421 278.276  1.00  0.00           C
ATOM   2276  C6   A   B  35     -17.549 104.296 279.052  1.00  0.00           C
ATOM   2277  N6   A   B  35     -16.378 103.873 278.575  1.00  0.00           N
ATOM   2278  N1   A   B  35     -17.622 104.636 280.364  1.00  0.00           N
ATOM   2279  C2   A   B  35     -18.800 105.069 280.844  1.00  0.00           C
ATOM   2280  N3   A   B  35     -19.967 105.232 280.211  1.00  0.00           N
ATOM   2281  C4   A   B  35     -19.855 104.885 278.919  1.00  0.00           C
ATOM   2282  P    A   B  36     -23.699 109.978 276.762  1.00  0.00           P
ATOM   2283  O1P  A   B  36     -25.106 110.365 277.112  1.00  0.00           O
ATOM   2284  O2P  A   B  36     -23.053 110.560 275.568  1.00  0.00           O
ATOM   2285  O5*  A   B  36     -22.784 110.265 278.021  1.00  0.00           O
ATOM   2286  C5*  A   B  36     -21.517 110.870 277.862  1.00  0.00           C
ATOM   2287  C4*  A   B  36     -20.802 110.880 279.182  1.00  0.00           C
ATOM   2288  O4*  A   B  36     -20.563 109.507 279.615  1.00  0.00           O
ATOM   2289  C3*  A   B  36     -19.404 111.474 279.156  1.00  0.00           C
ATOM   2290  O3*  A   B  36     -19.428 112.897 279.181  1.00  0.00           O
ATOM   2291  C2*  A   B  36     -18.805 110.864 280.414  1.00  0.00           C
ATOM   2292  O2*  A   B  36     -19.296 111.449 281.612  1.00  0.00           O
ATOM   2293  C1*  A   B  36     -19.310 109.427 280.283  1.00  0.00           C
ATOM   2294  N9   A   B  36     -18.407 108.638 279.454  1.00  0.00           N
ATOM   2295  C8   A   B  36     -18.588 108.217 278.163  1.00  0.00           C
ATOM   2296  N7   A   B  36     -17.567 107.552 277.678  1.00  0.00           N
ATOM   2297  C5   A   B  36     -16.658 107.529 278.724  1.00  0.00           C
ATOM   2298  C6   A   B  36     -15.362 106.992 278.844  1.00  0.00           C
ATOM   2299  N6   A   B  36     -14.734 106.337 277.861  1.00  0.00           N
ATOM   2300  N1   A   B  36     -14.722 107.160 280.023  1.00  0.00           N
ATOM   2301  C2   A   B  36     -15.349 107.826 281.004  1.00  0.00           C
ATOM   2302  N3   A   B  36     -16.559 108.375 281.009  1.00  0.00           N
ATOM   2303  C4   A   B  36     -17.167 108.188 279.828  1.00  0.00           C
HETATM 2304  N1   YG  B  37     -12.181 108.343 275.840  1.00  0.00           N
HETATM 2305  N2   YG  B  37     -10.272 108.439 277.090  1.00  0.00           N
HETATM 2306  C2   YG  B  37     -11.605 108.782 276.987  1.00  0.00           C
HETATM 2307  N3   YG  B  37     -12.250 109.490 277.949  1.00  0.00           N
HETATM 2308  C3   YG  B  37     -11.566 109.960 279.205  1.00  0.00           C
HETATM 2309  C4   YG  B  37     -13.572 109.717 277.622  1.00  0.00           C
HETATM 2310  C5   YG  B  37     -14.249 109.314 276.480  1.00  0.00           C
HETATM 2311  C6   YG  B  37     -13.540 108.559 275.477  1.00  0.00           C
HETATM 2312  O6   YG  B  37     -13.970 108.103 274.406  1.00  0.00           O
HETATM 2313  N7   YG  B  37     -15.571 109.745 276.513  1.00  0.00           N
HETATM 2314  C8   YG  B  37     -15.678 110.392 277.646  1.00  0.00           C
HETATM 2315  N9   YG  B  37     -14.504 110.421 278.367  1.00  0.00           N
HETATM 2316  C10  YG  B  37      -8.643 107.143 275.552  1.00  0.00           C
HETATM 2317  C11  YG  B  37      -9.977 107.741 275.929  1.00  0.00           C
HETATM 2318  C12  YG  B  37     -11.146 107.696 275.188  1.00  0.00           C
HETATM 2319  C13  YG  B  37     -11.262 106.995 273.852  1.00  0.00           C
HETATM 2320  C14  YG  B  37     -11.155 105.492 273.995  1.00  0.00           C
HETATM 2321  C15  YG  B  37     -10.064 104.808 273.155  1.00  0.00           C
HETATM 2322  C16  YG  B  37     -10.475 103.381 272.775  1.00  0.00           C
HETATM 2323  O17  YG  B  37     -11.620 103.144 272.386  1.00  0.00           O
HETATM 2324  O18  YG  B  37      -9.547 102.404 272.912  1.00  0.00           O
HETATM 2325  C19  YG  B  37      -8.967 101.714 271.773  1.00  0.00           C
HETATM 2326  N20  YG  B  37      -8.784 104.819 273.864  1.00  0.00           N
HETATM 2327  C21  YG  B  37      -7.635 105.216 273.313  1.00  0.00           C
```

```
HETATM 2328  O22   YG  B  37       -7.591 105.702 272.178  1.00  0.00           O
HETATM 2329  O23   YG  B  37       -6.494 105.088 274.033  1.00  0.00           O
HETATM 2330  C24   YG  B  37       -5.223 105.634 273.603  1.00  0.00           C
HETATM 2331  C1*   YG  B  37      -14.289 111.083 279.654  1.00  0.00           C
HETATM 2332  C2*   YG  B  37      -13.359 112.301 279.573  1.00  0.00           C
HETATM 2333  O2*   YG  B  37      -12.504 112.351 280.699  1.00  0.00           O
HETATM 2334  C3*   YG  B  37      -14.358 113.449 279.535  1.00  0.00           C
HETATM 2335  O3*   YG  B  37      -13.779 114.649 280.023  1.00  0.00           O
HETATM 2336  C4*   YG  B  37      -15.430 112.952 280.481  1.00  0.00           C
HETATM 2337  O4*   YG  B  37      -15.542 111.550 280.129  1.00  0.00           O
HETATM 2338  C5*   YG  B  37      -16.769 113.617 280.325  1.00  0.00           C
HETATM 2339  O5*   YG  B  37      -16.967 113.998 278.971  1.00  0.00           O
HETATM 2340  P     YG  B  37      -18.375 113.767 278.267  1.00  0.00           P
HETATM 2341  O1P   YG  B  37      -18.151 112.907 277.071  1.00  0.00           O
HETATM 2342  O2P   YG  B  37      -19.051 115.085 278.114  1.00  0.00           O
ATOM   2343  P     A   B  38      -12.918 115.572 279.032  1.00  0.00           P
ATOM   2344  O1P   A   B  38      -12.108 116.497 279.863  1.00  0.00           O
ATOM   2345  O2P   A   B  38      -13.861 116.110 278.020  1.00  0.00           O
ATOM   2346  O5*   A   B  38      -11.910 114.573 278.316  1.00  0.00           O
ATOM   2347  C5*   A   B  38      -10.613 114.375 278.843  1.00  0.00           C
ATOM   2348  C4*   A   B  38       -9.822 113.498 277.922  1.00  0.00           C
ATOM   2349  O4*   A   B  38      -10.573 112.288 277.660  1.00  0.00           O
ATOM   2350  C3*   A   B  38       -9.621 114.027 276.517  1.00  0.00           C
ATOM   2351  O3*   A   B  38       -8.656 115.064 276.461  1.00  0.00           O
ATOM   2352  C2*   A   B  38       -9.198 112.757 275.792  1.00  0.00           C
ATOM   2353  O2*   A   B  38       -7.875 112.325 276.050  1.00  0.00           O
ATOM   2354  C1*   A   B  38      -10.189 111.766 276.393  1.00  0.00           C
ATOM   2355  N9    A   B  38      -11.372 111.674 275.550  1.00  0.00           N
ATOM   2356  C8    A   B  38      -12.638 112.132 275.798  1.00  0.00           C
ATOM   2357  N7    A   B  38      -13.484 111.900 274.822  1.00  0.00           N
ATOM   2358  C5    A   B  38      -12.720 111.241 273.865  1.00  0.00           C
ATOM   2359  C6    A   B  38      -13.028 110.724 272.581  1.00  0.00           C
ATOM   2360  N6    A   B  38      -14.242 110.787 272.017  1.00  0.00           N
ATOM   2361  N1    A   B  38      -12.028 110.135 271.888  1.00  0.00           N
ATOM   2362  C2    A   B  38      -10.807 110.069 272.452  1.00  0.00           C
ATOM   2363  N3    A   B  38      -10.397 110.516 273.641  1.00  0.00           N
ATOM   2364  C4    A   B  38      -11.415 111.097 274.303  1.00  0.00           C
HETATM 2365  N1    PSU B  39      -12.634 114.294 272.547  1.00  0.00           N
HETATM 2366  C2    PSU B  39      -13.593 114.060 271.596  1.00  0.00           C
HETATM 2367  N3    PSU B  39      -13.123 113.467 270.459  1.00  0.00           N
HETATM 2368  C4    PSU B  39      -11.813 113.108 270.215  1.00  0.00           C
HETATM 2369  C5    PSU B  39      -10.895 113.405 271.284  1.00  0.00           C
HETATM 2370  C6    PSU B  39      -11.353 113.983 272.395  1.00  0.00           C
HETATM 2371  O2    PSU B  39      -14.761 114.355 271.746  1.00  0.00           O
HETATM 2372  O4    PSU B  39      -11.527 112.579 269.143  1.00  0.00           O
HETATM 2373  C1*   PSU B  39       -9.407 113.277 271.006  1.00  0.00           C
HETATM 2374  C2*   PSU B  39       -8.873 114.308 270.010  1.00  0.00           C
HETATM 2375  O2*   PSU B  39       -7.890 113.723 269.179  1.00  0.00           O
HETATM 2376  C3*   PSU B  39       -8.282 115.357 270.944  1.00  0.00           C
HETATM 2377  C4*   PSU B  39       -7.713 114.501 272.063  1.00  0.00           C
HETATM 2378  O3*   PSU B  39       -7.244 116.075 270.289  1.00  0.00           O
HETATM 2379  O4*   PSU B  39       -8.701 113.454 272.225  1.00  0.00           O
HETATM 2380  C5*   PSU B  39       -7.509 115.201 273.388  1.00  0.00           C
HETATM 2381  O5*   PSU B  39       -8.768 115.514 273.984  1.00  0.00           O
HETATM 2382  P     PSU B  39       -8.834 116.255 275.390  1.00  0.00           P
HETATM 2383  O1P   PSU B  39      -10.195 116.830 275.555  1.00  0.00           O
HETATM 2384  O2P   PSU B  39       -7.642 117.131 275.493  1.00  0.00           O
HETATM 2385  P     5MC B  40       -7.570 117.488 269.596  1.00  0.00           P
HETATM 2386  O1P   5MC B  40       -8.395 118.279 270.560  1.00  0.00           O
HETATM 2387  O2P   5MC B  40       -6.301 118.055 269.068  1.00  0.00           O
HETATM 2388  O5*   5MC B  40       -8.484 117.125 268.341  1.00  0.00           O
HETATM 2389  C5*   5MC B  40       -7.907 116.866 267.069  1.00  0.00           C
HETATM 2390  C4*   5MC B  40       -8.942 116.285 266.141  1.00  0.00           C
HETATM 2391  O4*   5MC B  40       -9.775 115.332 266.860  1.00  0.00           O
HETATM 2392  C3*   5MC B  40       -9.953 117.288 265.635  1.00  0.00           C
HETATM 2393  O3*   5MC B  40       -9.432 118.027 264.546  1.00  0.00           O
HETATM 2394  C2*   5MC B  40      -11.085 116.378 265.188  1.00  0.00           C
HETATM 2395  O2*   5MC B  40      -10.880 115.770 263.929  1.00  0.00           O
HETATM 2396  C1*   5MC B  40      -11.085 115.345 266.311  1.00  0.00           C
HETATM 2397  N1    5MC B  40      -12.040 115.735 267.357  1.00  0.00           N
HETATM 2398  C2    5MC B  40      -13.399 115.732 267.044  1.00  0.00           C
HETATM 2399  O2    5MC B  40      -13.746 115.447 265.891  1.00  0.00           O
HETATM 2400  N3    5MC B  40      -14.299 116.052 267.995  1.00  0.00           N
HETATM 2401  C4    5MC B  40      -13.886 116.386 269.209  1.00  0.00           C
HETATM 2402  N4    5MC B  40      -14.817 116.674 270.125  1.00  0.00           N
HETATM 2403  C5    5MC B  40      -12.510 116.433 269.548  1.00  0.00           C
HETATM 2404  C6    5MC B  40      -11.625 116.090 268.606  1.00  0.00           C
HETATM 2405  CM5   5MC B  40      -12.114 116.976 270.881  1.00  0.00           C
ATOM   2406  P     U   B  41       -9.773 119.586 264.423  1.00  0.00           P
ATOM   2407  O1P   U   B  41       -8.597 120.232 263.807  1.00  0.00           O
ATOM   2408  O2P   U   B  41      -10.256 120.037 265.746  1.00  0.00           O
ATOM   2409  O5*   U   B  41      -11.009 119.660 263.429  1.00  0.00           O
ATOM   2410  C5*   U   B  41      -12.039 118.713 263.540  1.00  0.00           C
ATOM   2411  C4*   U   B  41      -13.281 119.177 262.841  1.00  0.00           C
ATOM   2412  O4*   U   B  41      -14.323 118.328 263.373  1.00  0.00           O
ATOM   2413  C3*   U   B  41      -13.772 120.602 263.092  1.00  0.00           C
ATOM   2414  O3*   U   B  41      -13.387 121.494 262.052  1.00  0.00           O
```

```
ATOM  2415  C2*   U B  41   -15.281 120.404 263.091  1.00  0.00           C
ATOM  2416  O2*   U B  41   -15.831 120.138 261.815  1.00  0.00           O
ATOM  2417  C1*   U B  41   -15.366 119.116 263.883  1.00  0.00           C
ATOM  2418  N1    U B  41   -15.126 119.318 265.314  1.00  0.00           N
ATOM  2419  C2    U B  41   -16.229 119.594 266.061  1.00  0.00           C
ATOM  2420  O2    U B  41   -17.350 119.659 265.563  1.00  0.00           O
ATOM  2421  N3    U B  41   -15.990 119.799 267.396  1.00  0.00           N
ATOM  2422  C4    U B  41   -14.772 119.755 268.035  1.00  0.00           C
ATOM  2423  O4    U B  41   -14.719 119.961 269.249  1.00  0.00           O
ATOM  2424  C5    U B  41   -13.655 119.452 267.180  1.00  0.00           C
ATOM  2425  C6    U B  41   -13.873 119.243 265.880  1.00  0.00           C
ATOM  2426  P     G B  42   -13.192 123.061 262.381  1.00  0.00           P
ATOM  2427  O1P   G B  42   -12.759 123.738 261.156  1.00  0.00           O
ATOM  2428  O2P   G B  42   -12.340 123.123 263.605  1.00  0.00           O
ATOM  2429  O5*   G B  42   -14.661 123.588 262.693  1.00  0.00           O
ATOM  2430  C5*   G B  42   -15.707 123.455 261.747  1.00  0.00           C
ATOM  2431  C4*   G B  42   -17.050 123.619 262.435  1.00  0.00           C
ATOM  2432  O4*   G B  42   -17.169 122.631 263.505  1.00  0.00           O
ATOM  2433  C3*   G B  42   -17.290 124.933 263.177  1.00  0.00           C
ATOM  2434  O3*   G B  42   -17.728 125.979 262.311  1.00  0.00           O
ATOM  2435  C2*   G B  42   -18.441 124.549 264.095  1.00  0.00           C
ATOM  2436  O2*   G B  42   -19.645 124.499 263.383  1.00  0.00           O
ATOM  2437  C1*   G B  42   -18.041 123.135 264.509  1.00  0.00           C
ATOM  2438  N9    G B  42   -17.366 123.126 265.806  1.00  0.00           N
ATOM  2439  C8    G B  42   -16.036 122.898 266.087  1.00  0.00           C
ATOM  2440  N7    G B  42   -15.761 122.958 267.369  1.00  0.00           N
ATOM  2441  C5    G B  42   -16.987 123.242 267.965  1.00  0.00           C
ATOM  2442  C6    G B  42   -17.337 123.398 269.327  1.00  0.00           C
ATOM  2443  O6    G B  42   -16.618 123.320 270.323  1.00  0.00           O
ATOM  2444  N1    G B  42   -18.688 123.673 269.472  1.00  0.00           N
ATOM  2445  C2    G B  42   -19.594 123.778 268.443  1.00  0.00           C
ATOM  2446  N2    G B  42   -20.876 124.049 268.783  1.00  0.00           N
ATOM  2447  N3    G B  42   -19.285 123.630 267.182  1.00  0.00           N
ATOM  2448  C4    G B  42   -17.979 123.362 267.013  1.00  0.00           C
ATOM  2449  P     G B  43   -17.499 127.519 262.738  1.00  0.00           P
ATOM  2450  O1P   G B  43   -17.698 128.389 261.551  1.00  0.00           O
ATOM  2451  O2P   G B  43   -16.219 127.553 263.463  1.00  0.00           O
ATOM  2452  O5*   G B  43   -18.693 127.823 263.748  1.00  0.00           O
ATOM  2453  C5*   G B  43   -20.038 127.564 263.370  1.00  0.00           C
ATOM  2454  C4*   G B  43   -20.943 127.660 264.562  1.00  0.00           C
ATOM  2455  O4*   G B  43   -20.617 126.624 265.525  1.00  0.00           O
ATOM  2456  C3*   G B  43   -20.768 128.945 265.334  1.00  0.00           C
ATOM  2457  O3*   G B  43   -21.550 129.937 264.707  1.00  0.00           O
ATOM  2458  C2*   G B  43   -21.301 128.559 266.708  1.00  0.00           C
ATOM  2459  O2*   G B  43   -22.709 128.552 266.735  1.00  0.00           O
ATOM  2460  C1*   G B  43   -20.797 127.123 266.835  1.00  0.00           C
ATOM  2461  N9    G B  43   -19.537 126.976 267.555  1.00  0.00           N
ATOM  2462  C8    G B  43   -18.292 126.796 267.019  1.00  0.00           C
ATOM  2463  N7    G B  43   -17.355 126.656 267.922  1.00  0.00           N
ATOM  2464  C5    G B  43   -18.024 126.763 269.126  1.00  0.00           C
ATOM  2465  C6    G B  43   -17.539 126.707 270.448  1.00  0.00           C
ATOM  2466  O6    G B  43   -16.367 126.516 270.841  1.00  0.00           O
ATOM  2467  N1    G B  43   -18.567 126.897 271.377  1.00  0.00           N
ATOM  2468  C2    G B  43   -19.884 127.107 271.066  1.00  0.00           C
ATOM  2469  N2    G B  43   -20.721 127.294 272.096  1.00  0.00           N
ATOM  2470  N3    G B  43   -20.351 127.143 269.834  1.00  0.00           N
ATOM  2471  C4    G B  43   -19.373 126.969 268.918  1.00  0.00           C
ATOM  2472  P     A B  44   -21.103 131.470 264.797  1.00  0.00           P
ATOM  2473  O1P   A B  44   -21.943 132.184 263.795  1.00  0.00           O
ATOM  2474  O2P   A B  44   -19.625 131.549 264.719  1.00  0.00           O
ATOM  2475  O5*   A B  44   -21.558 131.882 266.266  1.00  0.00           O
ATOM  2476  C5*   A B  44   -22.938 132.036 266.560  1.00  0.00           C
ATOM  2477  C4*   A B  44   -23.175 131.851 268.035  1.00  0.00           C
ATOM  2478  O4*   A B  44   -22.426 130.701 268.475  1.00  0.00           O
ATOM  2479  C3*   A B  44   -22.633 132.965 268.900  1.00  0.00           C
ATOM  2480  O3*   A B  44   -23.558 134.040 268.972  1.00  0.00           O
ATOM  2481  C2*   A B  44   -22.480 132.275 270.239  1.00  0.00           C
ATOM  2482  O2*   A B  44   -23.721 132.157 270.899  1.00  0.00           O
ATOM  2483  C1*   A B  44   -21.986 130.899 269.802  1.00  0.00           C
ATOM  2484  N9    A B  44   -20.537 130.760 269.802  1.00  0.00           N
ATOM  2485  C8    A B  44   -19.702 130.869 268.728  1.00  0.00           C
ATOM  2486  N7    A B  44   -18.439 130.649 269.017  1.00  0.00           N
ATOM  2487  C5    A B  44   -18.445 130.394 270.378  1.00  0.00           C
ATOM  2488  C6    A B  44   -17.418 130.086 271.301  1.00  0.00           C
ATOM  2489  N6    A B  44   -16.113 129.962 270.981  1.00  0.00           N
ATOM  2490  N1    A B  44   -17.779 129.898 272.592  1.00  0.00           N
ATOM  2491  C2    A B  44   -19.075 129.997 272.918  1.00  0.00           C
ATOM  2492  N3    A B  44   -20.115 130.269 272.148  1.00  0.00           N
ATOM  2493  C4    A B  44   -19.732 130.465 270.877  1.00  0.00           C
ATOM  2494  P     G B  45   -21.868 135.763 268.378  1.00  0.00           P
ATOM  2495  O1P   G B  45   -22.848 136.859 268.491  1.00  0.00           O
ATOM  2496  O2P   G B  45   -21.045 135.630 267.148  1.00  0.00           O
ATOM  2497  O5*   G B  45   -20.942 135.807 269.671  1.00  0.00           O
ATOM  2498  C5*   G B  45   -21.524 135.904 270.966  1.00  0.00           C
ATOM  2499  C4*   G B  45   -20.453 135.877 272.012  1.00  0.00           C
ATOM  2500  O4*   G B  45   -19.840 134.564 272.006  1.00  0.00           O
ATOM  2501  C3*   G B  45   -19.305 136.824 271.722  1.00  0.00           C
```

```
ATOM   2502  O3*  G   B  45     -19.606 138.079 272.302  1.00  0.00           O
ATOM   2503  C2*  G   B  45     -18.153 136.165 272.464  1.00  0.00           C
ATOM   2504  O2*  G   B  45     -18.211 136.457 273.833  1.00  0.00           O
ATOM   2505  C1*  G   B  45     -18.449 134.676 272.264  1.00  0.00           C
ATOM   2506  N9   G   B  45     -17.733 134.067 271.145  1.00  0.00           N
ATOM   2507  C8   G   B  45     -18.166 133.993 269.841  1.00  0.00           C
ATOM   2508  N7   G   B  45     -17.315 133.404 269.047  1.00  0.00           N
ATOM   2509  C5   G   B  45     -16.250 133.062 269.876  1.00  0.00           C
ATOM   2510  C6   G   B  45     -15.005 132.433 269.565  1.00  0.00           C
ATOM   2511  O6   G   B  45     -14.580 132.033 268.450  1.00  0.00           O
ATOM   2512  N1   G   B  45     -14.215 132.304 270.693  1.00  0.00           N
ATOM   2513  C2   G   B  45     -14.569 132.731 271.957  1.00  0.00           C
ATOM   2514  N2   G   B  45     -13.657 132.525 272.922  1.00  0.00           N
ATOM   2515  N3   G   B  45     -15.721 133.321 272.253  1.00  0.00           N
ATOM   2516  C4   G   B  45     -16.498 133.456 271.177  1.00  0.00           C
HETATM 2517  P    7MG B  46     -19.521 139.400 271.405  1.00  0.00           P
HETATM 2518  O1P  7MG B  46     -19.857 139.060 270.002  1.00  0.00           O
HETATM 2519  O2P  7MG B  46     -20.273 140.479 272.097  1.00  0.00           O
HETATM 2520  O5*  7MG B  46     -17.979 139.773 271.476  1.00  0.00           O
HETATM 2521  C5*  7MG B  46     -17.343 139.897 272.740  1.00  0.00           C
HETATM 2522  C4*  7MG B  46     -16.288 140.980 272.697  1.00  0.00           C
HETATM 2523  O4*  7MG B  46     -15.123 140.460 271.990  1.00  0.00           O
HETATM 2524  C3*  7MG B  46     -16.680 142.262 271.968  1.00  0.00           C
HETATM 2525  O3*  7MG B  46     -16.049 143.384 272.595  1.00  0.00           O
HETATM 2526  C2*  7MG B  46     -16.113 142.013 270.572  1.00  0.00           C
HETATM 2527  O2*  7MG B  46     -15.890 143.174 269.789  1.00  0.00           O
HETATM 2528  C1*  7MG B  46     -14.800 141.319 270.915  1.00  0.00           C
HETATM 2529  N9   7MG B  46     -14.268 140.500 269.834  1.00  0.00           N
HETATM 2530  C8   7MG B  46     -14.830 140.308 268.513  1.00  0.00           C
HETATM 2531  N7   7MG B  46     -13.940 139.466 267.791  1.00  0.00           N
HETATM 2532  C5   7MG B  46     -12.904 139.144 268.651  1.00  0.00           C
HETATM 2533  C6   7MG B  46     -11.776 138.362 268.430  1.00  0.00           C
HETATM 2534  O6   7MG B  46     -11.466 137.799 267.405  1.00  0.00           O
HETATM 2535  N1   7MG B  46     -10.975 138.267 269.554  1.00  0.00           N
HETATM 2536  C2   7MG B  46     -11.237 138.883 270.759  1.00  0.00           C
HETATM 2537  N2   7MG B  46     -10.341 138.660 271.751  1.00  0.00           N
HETATM 2538  N3   7MG B  46     -12.292 139.652 270.980  1.00  0.00           N
HETATM 2539  C4   7MG B  46     -13.085 139.739 269.902  1.00  0.00           C
HETATM 2540  CM7  7MG B  46     -14.249 139.108 266.372  1.00  0.00           C
ATOM   2541  P    U   B  47     -16.888 144.300 273.649  1.00  0.00           P
ATOM   2542  O1P  U   B  47     -16.366 144.064 275.008  1.00  0.00           O
ATOM   2543  O2P  U   B  47     -18.339 144.090 273.365  1.00  0.00           O
ATOM   2544  O5*  U   B  47     -16.527 145.787 273.205  1.00  0.00           O
ATOM   2545  C5*  U   B  47     -16.515 146.145 271.815  1.00  0.00           C
ATOM   2546  C4*  U   B  47     -15.652 147.373 271.595  1.00  0.00           C
ATOM   2547  O4*  U   B  47     -16.239 148.542 272.244  1.00  0.00           O
ATOM   2548  C3*  U   B  47     -14.239 147.275 272.161  1.00  0.00           C
ATOM   2549  O3*  U   B  47     -13.417 148.038 271.316  1.00  0.00           O
ATOM   2550  C2*  U   B  47     -14.379 147.932 273.526  1.00  0.00           C
ATOM   2551  O2*  U   B  47     -13.182 148.437 274.091  1.00  0.00           O
ATOM   2552  C1*  U   B  47     -15.324 149.071 273.185  1.00  0.00           C
ATOM   2553  N1   U   B  47     -16.058 149.485 274.375  1.00  0.00           N
ATOM   2554  C2   U   B  47     -16.049 150.816 274.670  1.00  0.00           C
ATOM   2555  O2   U   B  47     -15.490 151.639 273.965  1.00  0.00           O
ATOM   2556  N3   U   B  47     -16.707 151.150 275.822  1.00  0.00           N
ATOM   2557  C4   U   B  47     -17.363 150.290 276.687  1.00  0.00           C
ATOM   2558  O4   U   B  47     -17.884 150.741 277.709  1.00  0.00           O
ATOM   2559  C5   U   B  47     -17.334 148.920 276.292  1.00  0.00           C
ATOM   2560  C6   U   B  47     -16.701 148.574 275.175  1.00  0.00           C
ATOM   2561  P    C   B  48     -12.778 147.340 270.029  1.00  0.00           P
ATOM   2562  O1P  C   B  48     -12.330 148.413 269.120  1.00  0.00           O
ATOM   2563  O2P  C   B  48     -13.759 146.325 269.563  1.00  0.00           O
ATOM   2564  O5*  C   B  48     -11.532 146.553 270.634  1.00  0.00           O
ATOM   2565  C5*  C   B  48     -10.466 147.263 271.185  1.00  0.00           C
ATOM   2566  C4*  C   B  48      -9.371 146.317 271.581  1.00  0.00           C
ATOM   2567  O4*  C   B  48      -9.309 145.195 270.650  1.00  0.00           O
ATOM   2568  C3*  C   B  48      -8.000 146.961 271.570  1.00  0.00           C
ATOM   2569  O3*  C   B  48      -7.332 146.483 272.732  1.00  0.00           O
ATOM   2570  C2*  C   B  48      -7.406 146.446 270.249  1.00  0.00           C
ATOM   2571  O2*  C   B  48      -6.003 146.349 270.206  1.00  0.00           O
ATOM   2572  C1*  C   B  48      -7.981 145.037 270.183  1.00  0.00           C
ATOM   2573  N1   C   B  48      -8.044 144.509 268.808  1.00  0.00           N
ATOM   2574  C2   C   B  48      -7.104 143.587 268.381  1.00  0.00           C
ATOM   2575  O2   C   B  48      -6.231 143.230 269.171  1.00  0.00           O
ATOM   2576  N3   C   B  48      -7.171 143.120 267.102  1.00  0.00           N
ATOM   2577  C4   C   B  48      -8.133 143.574 266.282  1.00  0.00           C
ATOM   2578  N4   C   B  48      -8.175 143.145 264.998  1.00  0.00           N
ATOM   2579  C5   C   B  48      -9.096 144.503 266.718  1.00  0.00           C
ATOM   2580  C6   C   B  48      -9.008 144.937 267.964  1.00  0.00           C
HETATM 2581  P    5MC B  49      -6.387 147.453 273.578  1.00  0.00           P
HETATM 2582  O1P  5MC B  49      -5.603 146.546 274.457  1.00  0.00           O
HETATM 2583  O2P  5MC B  49      -5.685 148.452 272.730  1.00  0.00           O
HETATM 2584  O5*  5MC B  49      -7.387 148.329 274.488  1.00  0.00           O
HETATM 2585  C5*  5MC B  49      -8.401 147.728 275.278  1.00  0.00           C
HETATM 2586  C4*  5MC B  49      -9.048 148.792 276.153  1.00  0.00           C
HETATM 2587  O4*  5MC B  49      -8.107 149.173 277.194  1.00  0.00           O
HETATM 2588  C3*  5MC B  49      -9.248 150.089 275.388  1.00  0.00           C
```

```
HETATM 2589  O3*  5MC B  49   -10.450 150.041 274.665  1.00  0.00           O
HETATM 2590  C2*  5MC B  49    -9.288 151.099 276.506  1.00  0.00           C
HETATM 2591  O2*  5MC B  49   -10.532 151.002 277.171  1.00  0.00           O
HETATM 2592  C1*  5MC B  49    -8.152 150.589 277.386  1.00  0.00           C
HETATM 2593  N1   5MC B  49    -6.827 151.179 277.048  1.00  0.00           N
HETATM 2594  C2   5MC B  49    -6.601 152.557 277.329  1.00  0.00           C
HETATM 2595  O2   5MC B  49    -7.502 153.232 277.897  1.00  0.00           O
HETATM 2596  N3   5MC B  49    -5.419 153.125 276.979  1.00  0.00           N
HETATM 2597  C4   5MC B  49    -4.459 152.389 276.402  1.00  0.00           C
HETATM 2598  N4   5MC B  49    -3.304 153.005 276.095  1.00  0.00           N
HETATM 2599  C5   5MC B  49    -4.639 150.998 276.119  1.00  0.00           C
HETATM 2600  C6   5MC B  49    -5.834 150.430 276.454  1.00  0.00           C
HETATM 2601  CM5  5MC B  49    -3.511 150.246 275.475  1.00  0.00           C
ATOM   2602  P    U   B  50   -10.601 150.917 273.318  1.00  0.00           P
ATOM   2603  O1P  U   B  50   -11.810 150.432 272.650  1.00  0.00           O
ATOM   2604  O2P  U   B  50    -9.272 150.981 272.590  1.00  0.00           O
ATOM   2605  O5*  U   B  50   -10.857 152.417 273.779  1.00  0.00           O
ATOM   2606  C5*  U   B  50   -11.831 152.742 274.769  1.00  0.00           C
ATOM   2607  C4*  U   B  50   -11.814 154.234 275.057  1.00  0.00           C
ATOM   2608  O4*  U   B  50   -10.715 154.550 275.957  1.00  0.00           O
ATOM   2609  C3*  U   B  50   -11.570 155.171 273.878  1.00  0.00           C
ATOM   2610  O3*  U   B  50   -12.765 155.462 273.181  1.00  0.00           O
ATOM   2611  C2*  U   B  50   -11.133 156.424 274.608  1.00  0.00           C
ATOM   2612  O2*  U   B  50   -12.240 156.994 275.273  1.00  0.00           O
ATOM   2613  C1*  U   B  50   -10.196 155.821 275.642  1.00  0.00           C
ATOM   2614  N1   U   B  50    -8.841 155.645 275.119  1.00  0.00           N
ATOM   2615  C2   U   B  50    -8.046 156.775 275.049  1.00  0.00           C
ATOM   2616  O2   U   B  50    -8.462 157.900 275.322  1.00  0.00           O
ATOM   2617  N3   U   B  50    -6.748 156.555 274.660  1.00  0.00           N
ATOM   2618  C4   U   B  50    -6.184 155.360 274.326  1.00  0.00           C
ATOM   2619  O4   U   B  50    -4.995 155.332 273.987  1.00  0.00           O
ATOM   2620  C5   U   B  50    -7.089 154.231 274.375  1.00  0.00           C
ATOM   2621  C6   U   B  50    -8.358 154.415 274.751  1.00  0.00           C
ATOM   2622  P    G   B  51   -12.712 155.766 271.603  1.00  0.00           P
ATOM   2623  O1P  G   B  51   -14.095 155.596 271.161  1.00  0.00           O
ATOM   2624  O2P  G   B  51   -11.637 154.975 270.944  1.00  0.00           O
ATOM   2625  O5*  G   B  51   -12.242 157.273 271.541  1.00  0.00           O
ATOM   2626  C5*  G   B  51   -12.762 158.236 272.443  1.00  0.00           C
ATOM   2627  C4*  G   B  51   -12.046 159.556 272.252  1.00  0.00           C
ATOM   2628  O4*  G   B  51   -10.859 159.601 273.092  1.00  0.00           O
ATOM   2629  C3*  G   B  51   -11.552 159.840 270.839  1.00  0.00           C
ATOM   2630  O3*  G   B  51   -12.559 160.465 270.043  1.00  0.00           O
ATOM   2631  C2*  G   B  51   -10.401 160.793 271.097  1.00  0.00           C
ATOM   2632  O2*  G   B  51   -10.857 162.060 271.407  1.00  0.00           O
ATOM   2633  C1*  G   B  51    -9.803 160.225 272.386  1.00  0.00           C
ATOM   2634  N9   G   B  51    -8.779 159.240 272.064  1.00  0.00           N
ATOM   2635  C8   G   B  51    -8.937 157.891 271.866  1.00  0.00           C
ATOM   2636  N7   G   B  51    -7.825 157.292 271.506  1.00  0.00           N
ATOM   2637  C5   G   B  51    -6.878 158.313 271.480  1.00  0.00           C
ATOM   2638  C6   G   B  51    -5.511 158.279 271.153  1.00  0.00           C
ATOM   2639  O6   G   B  51    -4.815 157.295 270.819  1.00  0.00           O
ATOM   2640  N1   G   B  51    -4.932 159.538 271.247  1.00  0.00           N
ATOM   2641  C2   G   B  51    -5.589 160.681 271.611  1.00  0.00           C
ATOM   2642  N2   G   B  51    -4.858 161.802 271.641  1.00  0.00           N
ATOM   2643  N3   G   B  51    -6.868 160.725 271.930  1.00  0.00           N
ATOM   2644  C4   G   B  51    -7.446 159.516 271.842  1.00  0.00           C
ATOM   2645  P    U   B  52   -12.531 160.316 268.421  1.00  0.00           P
ATOM   2646  O1P  U   B  52   -13.784 160.898 267.898  1.00  0.00           O
ATOM   2647  O2P  U   B  52   -12.182 158.928 268.041  1.00  0.00           O
ATOM   2648  O5*  U   B  52   -11.322 161.244 268.014  1.00  0.00           O
ATOM   2649  C5*  U   B  52   -11.378 162.628 268.279  1.00  0.00           C
ATOM   2650  C4*  U   B  52   -10.020 163.235 268.100  1.00  0.00           C
ATOM   2651  O4*  U   B  52    -9.116 162.655 269.056  1.00  0.00           O
ATOM   2652  C3*  U   B  52    -9.345 162.894 266.788  1.00  0.00           C
ATOM   2653  O3*  U   B  52    -9.827 163.728 265.741  1.00  0.00           O
ATOM   2654  C2*  U   B  52    -7.918 163.265 267.124  1.00  0.00           C
ATOM   2655  O2*  U   B  52    -7.757 164.668 267.132  1.00  0.00           O
ATOM   2656  C1*  U   B  52    -7.792 162.679 268.532  1.00  0.00           C
ATOM   2657  N1   U   B  52    -7.287 161.296 268.422  1.00  0.00           N
ATOM   2658  C2   U   B  52    -5.954 161.135 268.185  1.00  0.00           C
ATOM   2659  O2   U   B  52    -5.201 162.059 268.107  1.00  0.00           O
ATOM   2660  N3   U   B  52    -5.532 159.846 268.025  1.00  0.00           N
ATOM   2661  C4   U   B  52    -6.308 158.725 268.054  1.00  0.00           C
ATOM   2662  O4   U   B  52    -5.796 157.625 267.835  1.00  0.00           O
ATOM   2663  C5   U   B  52    -7.696 158.973 268.316  1.00  0.00           C
ATOM   2664  C6   U   B  52    -8.117 160.219 268.500  1.00  0.00           C
ATOM   2665  P    G   B  53    -9.648 163.270 264.205  1.00  0.00           P
ATOM   2666  O1P  G   B  53   -10.305 164.306 263.374  1.00  0.00           O
ATOM   2667  O2P  G   B  53   -10.072 161.861 264.098  1.00  0.00           O
ATOM   2668  O5*  G   B  53    -8.084 163.293 263.937  1.00  0.00           O
ATOM   2669  C5*  G   B  53    -7.327 164.481 264.084  1.00  0.00           C
ATOM   2670  C4*  G   B  53    -5.861 164.161 263.931  1.00  0.00           C
ATOM   2671  O4*  G   B  53    -5.496 163.219 264.974  1.00  0.00           O
ATOM   2672  C3*  G   B  53    -5.429 163.421 262.661  1.00  0.00           C
ATOM   2673  O3*  G   B  53    -5.237 164.320 261.563  1.00  0.00           O
ATOM   2674  C2*  G   B  53    -4.094 162.817 263.094  1.00  0.00           C
ATOM   2675  O2*  G   B  53    -3.002 163.704 263.047  1.00  0.00           O
```

```
ATOM    2676  C1*   G  B  53      -4.361 162.469 264.558  1.00  0.00           C
ATOM    2677  N9    G  B  53      -4.690 161.054 264.660  1.00  0.00           N
ATOM    2678  C8    G  B  53      -5.913 160.504 264.934  1.00  0.00           C
ATOM    2679  N7    G  B  53      -5.897 159.193 264.947  1.00  0.00           N
ATOM    2680  C5    G  B  53      -4.583 158.869 264.672  1.00  0.00           C
ATOM    2681  C6    G  B  53      -3.968 157.597 264.525  1.00  0.00           C
ATOM    2682  O6    G  B  53      -4.478 156.473 264.663  1.00  0.00           O
ATOM    2683  N1    G  B  53      -2.629 157.717 264.186  1.00  0.00           N
ATOM    2684  C2    G  B  53      -1.951 158.917 264.011  1.00  0.00           C
ATOM    2685  N2    G  B  53      -0.640 158.810 263.700  1.00  0.00           N
ATOM    2686  N3    G  B  53      -2.516 160.115 264.145  1.00  0.00           N
ATOM    2687  C4    G  B  53      -3.827 160.011 264.476  1.00  0.00           C
HETATM  2688  N1   5MU B  54      -2.543 159.148 260.570  1.00  0.00           N
HETATM  2689  C2   5MU B  54      -2.321 157.805 260.684  1.00  0.00           C
HETATM  2690  N3   5MU B  54      -3.441 157.042 260.954  1.00  0.00           N
HETATM  2691  C4   5MU B  54      -4.741 157.490 261.120  1.00  0.00           C
HETATM  2692  C5   5MU B  54      -4.897 158.924 260.968  1.00  0.00           C
HETATM  2693  C5M  5MU B  54      -6.272 159.508 261.077  1.00  0.00           C
HETATM  2694  C6   5MU B  54      -3.811 159.680 260.715  1.00  0.00           C
HETATM  2695  O2   5MU B  54      -1.202 157.322 260.557  1.00  0.00           O
HETATM  2696  O4   5MU B  54      -5.653 156.665 261.338  1.00  0.00           O
HETATM  2697  C1*  5MU B  54      -1.361 159.977 260.267  1.00  0.00           C
HETATM  2698  C2*  5MU B  54      -1.073 160.084 258.759  1.00  0.00           C
HETATM  2699  O2*  5MU B  54       0.314 160.230 258.512  1.00  0.00           O
HETATM  2700  C3*  5MU B  54      -1.860 161.340 258.405  1.00  0.00           C
HETATM  2701  C4*  5MU B  54      -1.543 162.224 259.599  1.00  0.00           C
HETATM  2702  O3*  5MU B  54      -1.457 161.941 257.171  1.00  0.00           O
HETATM  2703  O4*  5MU B  54      -1.621 161.294 260.721  1.00  0.00           O
HETATM  2704  C5*  5MU B  54      -2.520 163.343 259.851  1.00  0.00           C
HETATM  2705  O5*  5MU B  54      -3.809 162.813 260.039  1.00  0.00           O
HETATM  2706  P    5MU B  54      -5.086 163.753 260.033  1.00  0.00           P
HETATM  2707  O1P  5MU B  54      -6.271 162.936 259.654  1.00  0.00           O
HETATM  2708  O2P  5MU B  54      -4.739 164.967 259.250  1.00  0.00           O
HETATM  2709  N1   PSU B  55      -5.802 158.580 257.650  1.00  0.00           N
HETATM  2710  C2   PSU B  55      -6.691 157.648 258.121  1.00  0.00           C
HETATM  2711  N3   PSU B  55      -6.252 156.346 258.028  1.00  0.00           N
HETATM  2712  C4   PSU B  55      -5.013 155.949 257.509  1.00  0.00           C
HETATM  2713  C5   PSU B  55      -4.181 157.006 257.039  1.00  0.00           C
HETATM  2714  C6   PSU B  55      -4.610 158.271 257.128  1.00  0.00           C
HETATM  2715  O2   PSU B  55      -7.778 157.945 258.570  1.00  0.00           O
HETATM  2716  O4   PSU B  55      -4.712 154.769 257.512  1.00  0.00           O
HETATM  2717  C1*  PSU B  55      -2.960 156.611 256.238  1.00  0.00           C
HETATM  2718  C2*  PSU B  55      -3.211 156.452 254.735  1.00  0.00           C
HETATM  2719  O2*  PSU B  55      -2.368 155.404 254.276  1.00  0.00           O
HETATM  2720  C3*  PSU B  55      -2.829 157.847 254.233  1.00  0.00           C
HETATM  2721  C4*  PSU B  55      -1.602 158.137 255.079  1.00  0.00           C
HETATM  2722  O3*  PSU B  55      -2.495 157.919 252.851  1.00  0.00           O
HETATM  2723  O4*  PSU B  55      -1.987 157.618 256.389  1.00  0.00           O
HETATM  2724  C5*  PSU B  55      -1.279 159.609 255.212  1.00  0.00           C
HETATM  2725  O5*  PSU B  55      -2.475 160.349 255.471  1.00  0.00           O
HETATM  2726  P    PSU B  55      -2.448 161.896 255.891  1.00  0.00           P
HETATM  2727  O1P  PSU B  55      -3.831 162.248 256.336  1.00  0.00           O
HETATM  2728  O2P  PSU B  55      -1.804 162.710 254.824  1.00  0.00           O
ATOM    2729  P     C  B  56      -3.530 158.542 251.790  1.00  0.00           P
ATOM    2730  O1P   C  B  56      -2.763 158.567 250.506  1.00  0.00           O
ATOM    2731  O2P   C  B  56      -4.199 159.782 252.286  1.00  0.00           O
ATOM    2732  O5*   C  B  56      -4.698 157.472 251.655  1.00  0.00           O
ATOM    2733  C5*   C  B  56      -5.900 157.826 251.008  1.00  0.00           C
ATOM    2734  C4*   C  B  56      -6.807 156.637 250.892  1.00  0.00           C
ATOM    2735  O4*   C  B  56      -6.244 155.709 249.938  1.00  0.00           O
ATOM    2736  C3*   C  B  56      -6.967 155.822 252.169  1.00  0.00           C
ATOM    2737  O3*   C  B  56      -8.002 156.411 252.941  1.00  0.00           O
ATOM    2738  C2*   C  B  56      -7.397 154.477 251.614  1.00  0.00           C
ATOM    2739  O2*   C  B  56      -8.789 154.390 251.290  1.00  0.00           O
ATOM    2740  C1*   C  B  56      -6.527 154.381 250.356  1.00  0.00           C
ATOM    2741  N1    C  B  56      -5.247 153.719 250.642  1.00  0.00           N
ATOM    2742  C2    C  B  56      -5.229 152.338 250.738  1.00  0.00           C
ATOM    2743  O2    C  B  56      -6.271 151.730 250.637  1.00  0.00           O
ATOM    2744  N3    C  B  56      -4.078 151.702 250.946  1.00  0.00           N
ATOM    2745  C4    C  B  56      -2.951 152.386 251.081  1.00  0.00           C
ATOM    2746  N4    C  B  56      -1.839 151.679 251.270  1.00  0.00           N
ATOM    2747  C5    C  B  56      -2.923 153.812 251.020  1.00  0.00           C
ATOM    2748  C6    C  B  56      -4.096 154.438 250.798  1.00  0.00           C
ATOM    2749  P     G  B  57      -7.811 156.593 254.534  1.00  0.00           P
ATOM    2750  O1P   G  B  57      -9.080 157.234 254.993  1.00  0.00           O
ATOM    2751  O2P   G  B  57      -6.505 157.196 254.869  1.00  0.00           O
ATOM    2752  O5*   G  B  57      -7.768 155.097 255.079  1.00  0.00           O
ATOM    2753  C5*   G  B  57      -8.912 154.278 254.981  1.00  0.00           C
ATOM    2754  C4*   G  B  57      -8.572 152.826 255.269  1.00  0.00           C
ATOM    2755  O4*   G  B  57      -7.633 152.286 254.288  1.00  0.00           O
ATOM    2756  C3*   G  B  57      -7.906 152.551 256.607  1.00  0.00           C
ATOM    2757  O3*   G  B  57      -8.911 152.493 257.597  1.00  0.00           O
ATOM    2758  C2*   G  B  57      -7.330 151.169 256.376  1.00  0.00           C
ATOM    2759  O2*   G  B  57      -8.361 150.200 256.442  1.00  0.00           O
ATOM    2760  C1*   G  B  57      -6.840 151.292 254.923  1.00  0.00           C
ATOM    2761  N9    G  B  57      -5.452 151.716 254.824  1.00  0.00           N
ATOM    2762  C8    G  B  57      -4.972 152.983 254.551  1.00  0.00           C
```

```
ATOM   2763 N7   G   B  57   -3.661 153.018 254.457 1.00 0.00           N
ATOM   2764 C5   G   B  57   -3.264 151.700 254.701 1.00 0.00           C
ATOM   2765 C6   G   B  57   -1.944 151.091 254.713 1.00 0.00           C
ATOM   2766 O6   G   B  57   -0.838 151.630 254.531 1.00 0.00           O
ATOM   2767 N1   G   B  57   -2.015 149.730 254.994 1.00 0.00           N
ATOM   2768 C2   G   B  57   -3.186 149.047 255.259 1.00 0.00           C
ATOM   2769 N2   G   B  57   -3.078 147.757 255.581 1.00 0.00           N
ATOM   2770 N3   G   B  57   -4.402 149.596 255.230 1.00 0.00           N
ATOM   2771 C4   G   B  57   -4.360 150.899 254.948 1.00 0.00           C
HETATM 2772 P    1MA B  58   -8.580 153.031 259.050 1.00 0.00           P
HETATM 2773 O1P  1MA B  58   -7.872 154.315 259.026 1.00 0.00           O
HETATM 2774 O2P  1MA B  58   -9.820 152.889 259.829 1.00 0.00           O
HETATM 2775 O5*  1MA B  58   -7.474 152.023 259.621 1.00 0.00           O
HETATM 2776 C5*  1MA B  58   -7.750 150.653 259.771 1.00 0.00           C
HETATM 2777 C4*  1MA B  58   -6.931 150.061 260.918 1.00 0.00           C
HETATM 2778 O4*  1MA B  58   -5.520 150.401 260.764 1.00 0.00           O
HETATM 2779 C3*  1MA B  58   -7.282 150.495 262.350 1.00 0.00           C
HETATM 2780 O3*  1MA B  58   -6.843 149.463 263.242 1.00 0.00           O
HETATM 2781 C2*  1MA B  58   -6.345 151.680 262.497 1.00 0.00           C
HETATM 2782 O2*  1MA B  58   -6.070 152.093 263.809 1.00 0.00           O
HETATM 2783 C1*  1MA B  58   -5.071 151.083 261.909 1.00 0.00           C
HETATM 2784 N9   1MA B  58   -4.047 152.070 261.548 1.00 0.00           N
HETATM 2785 C8   1MA B  58   -4.233 153.406 261.351 1.00 0.00           C
HETATM 2786 N7   1MA B  58   -3.127 154.063 261.128 1.00 0.00           N
HETATM 2787 C5   1MA B  58   -2.137 153.088 261.150 1.00 0.00           C
HETATM 2788 C6   1MA B  58   -0.701 153.289 260.937 1.00 0.00           C
HETATM 2789 N6   1MA B  58   -0.146 154.639 260.712 1.00 0.00           N
HETATM 2790 N1   1MA B  58    0.048 152.052 261.019 1.00 0.00           N
HETATM 2791 CM1  1MA B  58    1.497 152.257 260.818 1.00 0.00           C
HETATM 2792 C2   1MA B  58   -0.649 150.913 261.264 1.00 0.00           C
HETATM 2793 N3   1MA B  58   -1.986 150.705 261.474 1.00 0.00           N
HETATM 2794 C4   1MA B  58   -2.693 151.861 261.397 1.00 0.00           C
ATOM   2795 P    U   B  59   -7.751 148.122 263.494 1.00 0.00           P
ATOM   2796 O1P  U   B  59   -7.589 147.061 262.480 1.00 0.00           O
ATOM   2797 O2P  U   B  59   -9.112 148.575 263.881 1.00 0.00           O
ATOM   2798 O5*  U   B  59   -7.118 147.534 264.833 1.00 0.00           O
ATOM   2799 C5*  U   B  59   -7.328 148.189 266.096 1.00 0.00           C
ATOM   2800 C4*  U   B  59   -6.236 147.783 267.067 1.00 0.00           C
ATOM   2801 O4*  U   B  59   -6.121 146.325 267.020 1.00 0.00           O
ATOM   2802 C3*  U   B  59   -4.842 148.291 266.674 1.00 0.00           C
ATOM   2803 O3*  U   B  59   -4.606 149.641 267.183 1.00 0.00           O
ATOM   2804 C2*  U   B  59   -3.916 147.232 267.291 1.00 0.00           C
ATOM   2805 O2*  U   B  59   -3.599 147.536 268.634 1.00 0.00           O
ATOM   2806 C1*  U   B  59   -4.777 145.949 267.233 1.00 0.00           C
ATOM   2807 N1   U   B  59   -4.367 144.966 266.195 1.00 0.00           N
ATOM   2808 C2   U   B  59   -3.172 144.323 266.407 1.00 0.00           C
ATOM   2809 O2   U   B  59   -2.512 144.494 267.421 1.00 0.00           O
ATOM   2810 N3   U   B  59   -2.772 143.453 265.410 1.00 0.00           N
ATOM   2811 C4   U   B  59   -3.450 143.155 264.248 1.00 0.00           C
ATOM   2812 O4   U   B  59   -2.958 142.332 263.465 1.00 0.00           O
ATOM   2813 C5   U   B  59   -4.709 143.853 264.089 1.00 0.00           C
ATOM   2814 C6   U   B  59   -5.117 144.709 265.056 1.00 0.00           C
ATOM   2815 P    C   B  60   -3.632 150.659 266.369 1.00 0.00           P
ATOM   2816 O1P  C   B  60   -3.455 151.893 267.150 1.00 0.00           O
ATOM   2817 O2P  C   B  60   -4.126 150.736 264.958 1.00 0.00           O
ATOM   2818 O5*  C   B  60   -2.259 149.865 266.215 1.00 0.00           O
ATOM   2819 C5*  C   B  60   -1.379 149.633 267.326 1.00 0.00           C
ATOM   2820 C4*  C   B  60   -0.140 148.877 266.845 1.00 0.00           C
ATOM   2821 O4*  C   B  60   -0.585 147.677 266.130 1.00 0.00           O
ATOM   2822 C3*  C   B  60    0.704 149.643 265.844 1.00 0.00           C
ATOM   2823 O3*  C   B  60    2.065 149.250 265.950 1.00 0.00           O
ATOM   2824 C2*  C   B  60    0.138 149.171 264.526 1.00 0.00           C
ATOM   2825 O2*  C   B  60    1.022 149.315 263.452 1.00 0.00           O
ATOM   2826 C1*  C   B  60   -0.049 147.687 264.827 1.00 0.00           C
ATOM   2827 N1   C   B  60   -1.014 147.065 263.914 1.00 0.00           N
ATOM   2828 C2   C   B  60   -0.656 145.868 263.277 1.00 0.00           C
ATOM   2829 O2   C   B  60    0.468 145.351 263.531 1.00 0.00           O
ATOM   2830 N3   C   B  60   -1.515 145.310 262.404 1.00 0.00           N
ATOM   2831 C4   C   B  60   -2.695 145.899 262.136 1.00 0.00           C
ATOM   2832 N4   C   B  60   -3.472 145.331 261.225 1.00 0.00           N
ATOM   2833 C5   C   B  60   -3.102 147.098 262.780 1.00 0.00           C
ATOM   2834 C6   C   B  60   -2.233 147.648 263.662 1.00 0.00           C
ATOM   2835 P    C   B  61    3.041 150.110 266.867 1.00 0.00           P
ATOM   2836 O1P  C   B  61    4.298 149.349 266.866 1.00 0.00           O
ATOM   2837 O2P  C   B  61    2.376 150.463 268.141 1.00 0.00           O
ATOM   2838 O5*  C   B  61    3.207 151.499 266.093 1.00 0.00           O
ATOM   2839 C5*  C   B  61    4.138 151.630 265.016 1.00 0.00           C
ATOM   2840 C4*  C   B  61    4.086 153.039 264.445 1.00 0.00           C
ATOM   2841 O4*  C   B  61    2.982 153.134 263.509 1.00 0.00           O
ATOM   2842 C3*  C   B  61    3.798 154.130 265.459 1.00 0.00           C
ATOM   2843 O3*  C   B  61    5.006 154.517 266.132 1.00 0.00           O
ATOM   2844 C2*  C   B  61    3.232 155.228 264.571 1.00 0.00           C
ATOM   2845 O2*  C   B  61    4.259 155.874 263.851 1.00 0.00           O
ATOM   2846 C1*  C   B  61    2.400 154.427 263.571 1.00 0.00           C
ATOM   2847 N1   C   B  61    0.967 154.273 263.900 1.00 0.00           N
ATOM   2848 C2   C   B  61    0.132 155.377 263.812 1.00 0.00           C
ATOM   2849 O2   C   B  61    0.616 156.467 263.486 1.00 0.00           O
```

```
ATOM  2850  N3   C B 61   -1.185 155.237 264.091  1.00  0.00           N
ATOM  2851  C4   C B 61   -1.659 154.043 264.465  1.00  0.00           C
ATOM  2852  N4   C B 61   -2.953 153.936 264.741  1.00  0.00           N
ATOM  2853  C5   C B 61   -0.822 152.903 264.571  1.00  0.00           C
ATOM  2854  C6   C B 61    0.473 153.062 264.278  1.00  0.00           C
ATOM  2855  P    A B 62    4.930 155.222 267.582  1.00  0.00           P
ATOM  2856  O1P  A B 62    6.289 155.390 268.106  1.00  0.00           O
ATOM  2857  O2P  A B 62    3.927 154.488 268.401  1.00  0.00           O
ATOM  2858  O5*  A B 62    4.318 156.664 267.270  1.00  0.00           O
ATOM  2859  C5*  A B 62    5.095 157.665 266.635  1.00  0.00           C
ATOM  2860  C4*  A B 62    4.337 158.964 266.620  1.00  0.00           C
ATOM  2861  O4*  A B 62    3.115 158.810 265.830  1.00  0.00           O
ATOM  2862  C3*  A B 62    3.806 159.383 267.975  1.00  0.00           C
ATOM  2863  O3*  A B 62    4.844 160.028 268.667  1.00  0.00           O
ATOM  2864  C2*  A B 62    2.691 160.335 267.568  1.00  0.00           C
ATOM  2865  O2*  A B 62    3.173 161.520 266.977  1.00  0.00           O
ATOM  2866  C1*  A B 62    2.064 159.551 266.433  1.00  0.00           C
ATOM  2867  N9   A B 62    1.013 158.618 266.827  1.00  0.00           N
ATOM  2868  C8   A B 62    1.088 157.253 266.902  1.00  0.00           C
ATOM  2869  N7   A B 62   -0.062 156.669 267.147  1.00  0.00           N
ATOM  2870  C5   A B 62   -0.951 157.726 267.279  1.00  0.00           C
ATOM  2871  C6   A B 62   -2.336 157.773 267.491  1.00  0.00           C
ATOM  2872  N6   A B 62   -3.111 156.683 267.659  1.00  0.00           N
ATOM  2873  N1   A B 62   -2.918 158.992 267.525  1.00  0.00           N
ATOM  2874  C2   A B 62   -2.148 160.080 267.361  1.00  0.00           C
ATOM  2875  N3   A B 62   -0.843 160.163 267.153  1.00  0.00           N
ATOM  2876  C4   A B 62   -0.295 158.936 267.116  1.00  0.00           C
ATOM  2877  P    C B 63    4.816 160.114 270.275  1.00  0.00           P
ATOM  2878  O1P  C B 63    6.071 160.817 270.564  1.00  0.00           O
ATOM  2879  O2P  C B 63    4.550 158.803 270.899  1.00  0.00           O
ATOM  2880  O5*  C B 63    3.598 161.067 270.610  1.00  0.00           O
ATOM  2881  C5*  C B 63    3.775 162.469 270.541  1.00  0.00           C
ATOM  2882  C4*  C B 63    2.472 163.165 270.787  1.00  0.00           C
ATOM  2883  O4*  C B 63    1.481 162.598 269.885  1.00  0.00           O
ATOM  2884  C3*  C B 63    1.862 162.940 272.157  1.00  0.00           C
ATOM  2885  O3*  C B 63    2.423 163.803 273.151  1.00  0.00           O
ATOM  2886  C2*  C B 63    0.412 163.283 271.872  1.00  0.00           C
ATOM  2887  O2*  C B 63    0.214 164.684 271.718  1.00  0.00           O
ATOM  2888  C1*  C B 63    0.211 162.596 270.520  1.00  0.00           C
ATOM  2889  N1   C B 63   -0.291 161.204 270.600  1.00  0.00           N
ATOM  2890  C2   C B 63   -1.654 160.996 270.727  1.00  0.00           C
ATOM  2891  O2   C B 63   -2.399 161.999 270.784  1.00  0.00           O
ATOM  2892  N3   C B 63   -2.136 159.710 270.798  1.00  0.00           N
ATOM  2893  C4   C B 63   -1.272 158.680 270.751  1.00  0.00           C
ATOM  2894  N4   C B 63   -1.742 157.444 270.814  1.00  0.00           N
ATOM  2895  C5   C B 63    0.127 158.881 270.625  1.00  0.00           C
ATOM  2896  C6   C B 63    0.569 160.143 270.548  1.00  0.00           C
ATOM  2897  P    A B 64    2.494 163.316 274.693  1.00  0.00           P
ATOM  2898  O1P  A B 64    3.285 164.298 275.469  1.00  0.00           O
ATOM  2899  O2P  A B 64    2.905 161.894 274.699  1.00  0.00           O
ATOM  2900  O5*  A B 64    0.997 163.470 275.171  1.00  0.00           O
ATOM  2901  C5*  A B 64    0.363 164.729 275.062  1.00  0.00           C
ATOM  2902  C4*  A B 64   -1.073 164.629 275.481  1.00  0.00           C
ATOM  2903  O4*  A B 64   -1.848 164.044 274.400  1.00  0.00           O
ATOM  2904  C3*  A B 64   -1.370 163.718 276.659  1.00  0.00           C
ATOM  2905  O3*  A B 64   -1.014 164.331 277.908  1.00  0.00           O
ATOM  2906  C2*  A B 64   -2.866 163.506 276.462  1.00  0.00           C
ATOM  2907  O2*  A B 64   -3.660 164.635 276.749  1.00  0.00           O
ATOM  2908  C1*  A B 64   -2.918 163.284 274.949  1.00  0.00           C
ATOM  2909  N9   A B 64   -2.671 161.879 274.661  1.00  0.00           N
ATOM  2910  C8   A B 64   -1.492 161.248 274.369  1.00  0.00           C
ATOM  2911  N7   A B 64   -1.612 159.957 274.231  1.00  0.00           N
ATOM  2912  C5   A B 64   -2.963 159.732 274.435  1.00  0.00           C
ATOM  2913  C6   A B 64   -3.733 158.574 274.398  1.00  0.00           C
ATOM  2914  N6   A B 64   -3.224 157.368 274.158  1.00  0.00           N
ATOM  2915  N1   A B 64   -5.058 158.694 274.617  1.00  0.00           N
ATOM  2916  C2   A B 64   -5.560 159.909 274.849  1.00  0.00           C
ATOM  2917  N3   A B 64   -4.935 161.073 274.906  1.00  0.00           N
ATOM  2918  C4   A B 64   -3.623 160.905 274.690  1.00  0.00           C
ATOM  2919  P    G B 65   -0.457 163.415 279.122  1.00  0.00           P
ATOM  2920  O1P  G B 65    0.051 164.294 280.207  1.00  0.00           O
ATOM  2921  O2P  G B 65    0.423 162.356 278.581  1.00  0.00           O
ATOM  2922  O5*  G B 65   -1.768 162.704 279.672  1.00  0.00           O
ATOM  2923  C5*  G B 65   -2.971 163.431 279.801  1.00  0.00           C
ATOM  2924  C4*  G B 65   -4.159 162.500 279.804  1.00  0.00           C
ATOM  2925  O4*  G B 65   -4.338 161.924 278.489  1.00  0.00           O
ATOM  2926  C3*  G B 65   -4.132 161.273 280.706  1.00  0.00           C
ATOM  2927  O3*  G B 65   -4.452 161.612 282.047  1.00  0.00           O
ATOM  2928  C2*  G B 65   -5.283 160.487 280.112  1.00  0.00           C
ATOM  2929  O2*  G B 65   -6.524 161.053 280.437  1.00  0.00           O
ATOM  2930  C1*  G B 65   -5.040 160.698 278.614  1.00  0.00           C
ATOM  2931  N9   G B 65   -4.188 159.622 278.122  1.00  0.00           N
ATOM  2932  C8   G B 65   -2.869 159.686 277.775  1.00  0.00           C
ATOM  2933  N7   G B 65   -2.385 158.539 277.400  1.00  0.00           N
ATOM  2934  C5   G B 65   -3.459 157.668 277.507  1.00  0.00           C
ATOM  2935  C6   G B 65   -3.559 156.296 277.191  1.00  0.00           C
ATOM  2936  O6   G B 65   -2.670 155.534 276.767  1.00  0.00           O
```

```
ATOM   2937  N1    G B  65      -4.848 155.817 277.406  1.00  0.00           N
ATOM   2938  C2    G B  65      -5.908 156.578 277.862  1.00  0.00           C
ATOM   2939  N2    G B  65      -7.082 155.958 278.003  1.00  0.00           N
ATOM   2940  N3    G B  65      -5.821 157.853 278.154  1.00  0.00           N
ATOM   2941  C4    G B  65      -4.575 158.328 277.951  1.00  0.00           C
ATOM   2942  P     A B  66      -3.920 160.687 283.259  1.00  0.00           P
ATOM   2943  O1P   A B  66      -4.200 161.387 284.535  1.00  0.00           O
ATOM   2944  O2P   A B  66      -2.535 160.295 282.936  1.00  0.00           O
ATOM   2945  O5*   A B  66      -4.844 159.395 283.186  1.00  0.00           O
ATOM   2946  C5*   A B  66      -6.231 159.491 283.447  1.00  0.00           C
ATOM   2947  C4*   A B  66      -6.894 158.168 283.202  1.00  0.00           C
ATOM   2948  O4*   A B  66      -6.606 157.735 281.851  1.00  0.00           O
ATOM   2949  C3*   A B  66      -6.354 157.033 284.037  1.00  0.00           C
ATOM   2950  O3*   A B  66      -6.911 157.071 285.339  1.00  0.00           O
ATOM   2951  C2*   A B  66      -6.816 155.831 283.228  1.00  0.00           C
ATOM   2952  O2*   A B  66      -8.197 155.557 283.358  1.00  0.00           O
ATOM   2953  C1*   A B  66      -6.551 156.318 281.805  1.00  0.00           C
ATOM   2954  N9    A B  66      -5.247 155.935 281.254  1.00  0.00           N
ATOM   2955  C8    A B  66      -4.164 156.758 281.089  1.00  0.00           C
ATOM   2956  N7    A B  66      -3.123 156.166 280.546  1.00  0.00           N
ATOM   2957  C5    A B  66      -3.549 154.869 280.338  1.00  0.00           C
ATOM   2958  C6    A B  66      -2.904 153.740 279.796  1.00  0.00           C
ATOM   2959  N6    A B  66      -1.662 153.756 279.359  1.00  0.00           N
ATOM   2960  N1    A B  66      -3.590 152.585 279.741  1.00  0.00           N
ATOM   2961  C2    A B  66      -4.843 152.564 280.227  1.00  0.00           C
ATOM   2962  N3    A B  66      -5.557 153.557 280.766  1.00  0.00           N
ATOM   2963  C4    A B  66      -4.850 154.699 280.786  1.00  0.00           C
ATOM   2964  P     A B  67      -6.046 156.559 286.594  1.00  0.00           P
ATOM   2965  O1P   A B  67      -6.831 156.848 287.817  1.00  0.00           O
ATOM   2966  O2P   A B  67      -4.646 157.053 286.485  1.00  0.00           O
ATOM   2967  O5*   A B  67      -6.077 154.995 286.424  1.00  0.00           O
ATOM   2968  C5*   A B  67      -7.310 154.301 286.490  1.00  0.00           C
ATOM   2969  C4*   A B  67      -7.099 152.868 286.105  1.00  0.00           C
ATOM   2970  O4*   A B  67      -6.684 152.844 284.717  1.00  0.00           O
ATOM   2971  C3*   A B  67      -5.930 152.222 286.818  1.00  0.00           C
ATOM   2972  O3*   A B  67      -6.361 151.649 288.033  1.00  0.00           O
ATOM   2973  C2*   A B  67      -5.586 151.099 285.862  1.00  0.00           C
ATOM   2974  O2*   A B  67      -6.557 150.071 285.964  1.00  0.00           O
ATOM   2975  C1*   A B  67      -5.717 151.821 284.524  1.00  0.00           C
ATOM   2976  N9    A B  67      -4.450 152.417 284.076  1.00  0.00           N
ATOM   2977  C8    A B  67      -4.000 153.694 284.264  1.00  0.00           C
ATOM   2978  N7    A B  67      -2.816 153.923 283.723  1.00  0.00           N
ATOM   2979  C5    A B  67      -2.467 152.711 283.154  1.00  0.00           C
ATOM   2980  C6    A B  67      -1.305 152.280 282.448  1.00  0.00           C
ATOM   2981  N6    A B  67      -0.271 153.061 282.166  1.00  0.00           N
ATOM   2982  N1    A B  67      -1.253 150.997 282.044  1.00  0.00           N
ATOM   2983  C2    A B  67      -2.291 150.201 282.335  1.00  0.00           C
ATOM   2984  N3    A B  67      -3.432 150.484 282.982  1.00  0.00           N
ATOM   2985  C4    A B  67      -3.458 151.772 283.364  1.00  0.00           C
ATOM   2986  P     U B  68      -5.296 151.375 289.204  1.00  0.00           P
ATOM   2987  O1P   U B  68      -6.118 151.012 290.381  1.00  0.00           O
ATOM   2988  O2P   U B  68      -4.278 152.468 289.297  1.00  0.00           O
ATOM   2989  O5*   U B  68      -4.516 150.065 288.745  1.00  0.00           O
ATOM   2990  C5*   U B  68      -5.195 148.852 288.547  1.00  0.00           C
ATOM   2991  C4*   U B  68      -4.244 147.846 287.970  1.00  0.00           C
ATOM   2992  O4*   U B  68      -3.891 148.231 286.606  1.00  0.00           O
ATOM   2993  C3*   U B  68      -2.896 147.780 288.669  1.00  0.00           C
ATOM   2994  O3*   U B  68      -2.999 146.969 289.825  1.00  0.00           O
ATOM   2995  C2*   U B  68      -2.050 147.108 287.598  1.00  0.00           C
ATOM   2996  O2*   U B  68      -2.368 145.729 287.478  1.00  0.00           O
ATOM   2997  C1*   U B  68      -2.552 147.841 286.347  1.00  0.00           C
ATOM   2998  N1    U B  68      -1.746 149.036 286.060  1.00  0.00           N
ATOM   2999  C2    U B  68      -0.541 148.804 285.413  1.00  0.00           C
ATOM   3000  O2    U B  68      -0.169 147.669 285.099  1.00  0.00           O
ATOM   3001  N3    U B  68       0.209 149.921 285.153  1.00  0.00           N
ATOM   3002  C4    U B  68      -0.107 151.228 285.464  1.00  0.00           C
ATOM   3003  O4    U B  68       0.695 152.132 285.170  1.00  0.00           O
ATOM   3004  C5    U B  68      -1.373 151.393 286.147  1.00  0.00           C
ATOM   3005  C6    U B  68      -2.130 150.310 286.406  1.00  0.00           C
ATOM   3006  P     U B  69      -1.980 147.183 291.029  1.00  0.00           P
ATOM   3007  O1P   U B  69      -2.304 146.207 292.108  1.00  0.00           O
ATOM   3008  O2P   U B  69      -1.972 148.626 291.306  1.00  0.00           O
ATOM   3009  O5*   U B  69      -0.543 146.809 290.448  1.00  0.00           O
ATOM   3010  C5*   U B  69      -0.302 145.519 289.932  1.00  0.00           C
ATOM   3011  C4*   U B  69       1.051 145.474 289.255  1.00  0.00           C
ATOM   3012  O4*   U B  69       1.028 146.250 288.020  1.00  0.00           O
ATOM   3013  C3*   U B  69       2.187 146.084 290.054  1.00  0.00           C
ATOM   3014  O3*   U B  69       2.654 145.116 290.992  1.00  0.00           O
ATOM   3015  C2*   U B  69       3.209 146.377 288.961  1.00  0.00           C
ATOM   3016  O2*   U B  69       3.957 145.258 288.519  1.00  0.00           O
ATOM   3017  C1*   U B  69       2.294 146.831 287.826  1.00  0.00           C
ATOM   3018  N1    U B  69       2.152 148.287 287.824  1.00  0.00           N
ATOM   3019  C2    U B  69       3.199 149.006 287.283  1.00  0.00           C
ATOM   3020  O2    U B  69       4.193 148.462 286.782  1.00  0.00           O
ATOM   3021  N3    U B  69       3.046 150.368 287.344  1.00  0.00           N
ATOM   3022  C4    U B  69       1.971 151.055 287.861  1.00  0.00           C
ATOM   3023  O4    U B  69       1.977 152.282 287.850  1.00  0.00           O
```

| | | | | | | | | | | |
|---|---|---|---|---|---|---|---|---|---|---|
| ATOM | 3024 | C5 | U B | 69 | 0.925 | 150.232 | 288.384 | 1.00 | 0.00 | C |
| ATOM | 3025 | C6 | U B | 69 | 1.050 | 148.911 | 288.346 | 1.00 | 0.00 | C |
| ATOM | 3026 | P | C B | 70 | 3.389 | 145.586 | 292.349 | 1.00 | 0.00 | P |
| ATOM | 3027 | O1P | C B | 70 | 3.400 | 144.382 | 293.251 | 1.00 | 0.00 | O |
| ATOM | 3028 | O2P | C B | 70 | 2.761 | 146.850 | 292.826 | 1.00 | 0.00 | O |
| ATOM | 3029 | O5* | C B | 70 | 4.858 | 145.934 | 291.849 | 1.00 | 0.00 | O |
| ATOM | 3030 | C5* | C B | 70 | 5.736 | 144.891 | 291.436 | 1.00 | 0.00 | C |
| ATOM | 3031 | C4* | C B | 70 | 6.950 | 145.468 | 290.746 | 1.00 | 0.00 | C |
| ATOM | 3032 | O4* | C B | 70 | 6.566 | 146.179 | 289.534 | 1.00 | 0.00 | O |
| ATOM | 3033 | C3* | C B | 70 | 7.746 | 146.504 | 291.510 | 1.00 | 0.00 | C |
| ATOM | 3034 | O3* | C B | 70 | 8.554 | 145.866 | 292.486 | 1.00 | 0.00 | O |
| ATOM | 3035 | C2* | C B | 70 | 8.575 | 147.092 | 290.373 | 1.00 | 0.00 | C |
| ATOM | 3036 | O2* | C B | 70 | 9.612 | 146.228 | 289.920 | 1.00 | 0.00 | O |
| ATOM | 3037 | C1* | C B | 70 | 7.507 | 147.204 | 289.287 | 1.00 | 0.00 | C |
| ATOM | 3038 | N1 | C B | 70 | 6.799 | 148.489 | 289.338 | 1.00 | 0.00 | N |
| ATOM | 3039 | C2 | C B | 70 | 7.390 | 149.573 | 288.719 | 1.00 | 0.00 | C |
| ATOM | 3040 | O2 | C B | 70 | 8.475 | 149.397 | 288.149 | 1.00 | 0.00 | O |
| ATOM | 3041 | N3 | C B | 70 | 6.780 | 150.783 | 288.751 | 1.00 | 0.00 | N |
| ATOM | 3042 | C4 | C B | 70 | 5.604 | 150.918 | 289.378 | 1.00 | 0.00 | C |
| ATOM | 3043 | N4 | C B | 70 | 5.025 | 152.140 | 289.382 | 1.00 | 0.00 | N |
| ATOM | 3044 | C5 | C B | 70 | 4.966 | 149.810 | 290.023 | 1.00 | 0.00 | C |
| ATOM | 3045 | C6 | C B | 70 | 5.594 | 148.621 | 289.977 | 1.00 | 0.00 | C |
| ATOM | 3046 | P | G B | 71 | 9.048 | 146.679 | 293.792 | 1.00 | 0.00 | P |
| ATOM | 3047 | O1P | G B | 71 | 9.709 | 145.655 | 294.644 | 1.00 | 0.00 | O |
| ATOM | 3048 | O2P | G B | 71 | 7.923 | 147.465 | 294.344 | 1.00 | 0.00 | O |
| ATOM | 3049 | O5* | G B | 71 | 10.103 | 147.750 | 293.230 | 1.00 | 0.00 | O |
| ATOM | 3050 | C5* | G B | 71 | 11.438 | 147.370 | 292.897 | 1.00 | 0.00 | C |
| ATOM | 3051 | C4* | G B | 71 | 12.160 | 148.492 | 292.168 | 1.00 | 0.00 | C |
| ATOM | 3052 | O4* | G B | 71 | 11.435 | 148.868 | 290.963 | 1.00 | 0.00 | O |
| ATOM | 3053 | C3* | G B | 71 | 12.368 | 149.820 | 292.888 | 1.00 | 0.00 | C |
| ATOM | 3054 | O3* | G B | 71 | 13.492 | 149.812 | 293.768 | 1.00 | 0.00 | O |
| ATOM | 3055 | C2* | G B | 71 | 12.665 | 150.733 | 291.713 | 1.00 | 0.00 | C |
| ATOM | 3056 | O2* | G B | 71 | 13.948 | 150.515 | 291.181 | 1.00 | 0.00 | O |
| ATOM | 3057 | C1* | G B | 71 | 11.610 | 150.260 | 290.716 | 1.00 | 0.00 | C |
| ATOM | 3058 | N9 | G B | 71 | 10.348 | 150.950 | 290.973 | 1.00 | 0.00 | N |
| ATOM | 3059 | C8 | G B | 71 | 9.269 | 150.482 | 291.682 | 1.00 | 0.00 | C |
| ATOM | 3060 | N7 | G B | 71 | 8.294 | 151.349 | 291.759 | 1.00 | 0.00 | N |
| ATOM | 3061 | C5 | G B | 71 | 8.755 | 152.449 | 291.047 | 1.00 | 0.00 | C |
| ATOM | 3062 | C6 | G B | 71 | 8.135 | 153.700 | 290.777 | 1.00 | 0.00 | C |
| ATOM | 3063 | O6 | G B | 71 | 7.009 | 154.110 | 291.130 | 1.00 | 0.00 | O |
| ATOM | 3064 | N1 | G B | 71 | 8.965 | 154.523 | 290.023 | 1.00 | 0.00 | N |
| ATOM | 3065 | C2 | G B | 71 | 10.224 | 154.190 | 289.593 | 1.00 | 0.00 | C |
| ATOM | 3066 | N2 | G B | 71 | 10.874 | 155.122 | 288.880 | 1.00 | 0.00 | N |
| ATOM | 3067 | N3 | G B | 71 | 10.807 | 153.038 | 289.841 | 1.00 | 0.00 | N |
| ATOM | 3068 | C4 | G B | 71 | 10.023 | 152.220 | 290.563 | 1.00 | 0.00 | C |
| ATOM | 3069 | P | C B | 72 | 13.664 | 151.000 | 294.840 | 1.00 | 0.00 | P |
| ATOM | 3070 | O1P | C B | 72 | 15.032 | 150.931 | 295.402 | 1.00 | 0.00 | O |
| ATOM | 3071 | O2P | C B | 72 | 12.493 | 150.972 | 295.756 | 1.00 | 0.00 | O |
| ATOM | 3072 | O5* | C B | 72 | 13.599 | 152.326 | 293.973 | 1.00 | 0.00 | O |
| ATOM | 3073 | C5* | C B | 72 | 14.786 | 152.899 | 293.465 | 1.00 | 0.00 | C |
| ATOM | 3074 | C4* | C B | 72 | 14.545 | 154.334 | 293.106 | 1.00 | 0.00 | C |
| ATOM | 3075 | O4* | C B | 72 | 13.389 | 154.390 | 292.236 | 1.00 | 0.00 | O |
| ATOM | 3076 | C3* | C B | 72 | 14.131 | 155.235 | 294.253 | 1.00 | 0.00 | C |
| ATOM | 3077 | O3* | C B | 72 | 15.246 | 155.663 | 295.017 | 1.00 | 0.00 | O |
| ATOM | 3078 | C2* | C B | 72 | 13.486 | 156.387 | 293.500 | 1.00 | 0.00 | C |
| ATOM | 3079 | O2* | C B | 72 | 14.394 | 157.269 | 292.867 | 1.00 | 0.00 | O |
| ATOM | 3080 | C1* | C B | 72 | 12.715 | 155.619 | 292.433 | 1.00 | 0.00 | C |
| ATOM | 3081 | N1 | C B | 72 | 11.350 | 155.336 | 292.870 | 1.00 | 0.00 | N |
| ATOM | 3082 | C2 | C B | 72 | 10.400 | 156.335 | 292.719 | 1.00 | 0.00 | C |
| ATOM | 3083 | O2 | C B | 72 | 10.763 | 157.430 | 292.241 | 1.00 | 0.00 | O |
| ATOM | 3084 | N3 | C B | 72 | 9.121 | 156.100 | 293.092 | 1.00 | 0.00 | N |
| ATOM | 3085 | C4 | C B | 72 | 8.791 | 154.912 | 293.608 | 1.00 | 0.00 | C |
| ATOM | 3086 | N4 | C B | 72 | 7.518 | 154.712 | 293.956 | 1.00 | 0.00 | N |
| ATOM | 3087 | C5 | C B | 72 | 9.754 | 153.872 | 293.786 | 1.00 | 0.00 | C |
| ATOM | 3088 | C6 | C B | 72 | 11.008 | 154.126 | 293.406 | 1.00 | 0.00 | C |
| ATOM | 3089 | P | A B | 73 | 15.031 | 156.153 | 296.533 | 1.00 | 0.00 | P |
| ATOM | 3090 | O1P | A B | 73 | 16.362 | 156.622 | 296.994 | 1.00 | 0.00 | O |
| ATOM | 3091 | O2P | A B | 73 | 14.342 | 155.074 | 297.286 | 1.00 | 0.00 | O |
| ATOM | 3092 | O5* | A B | 73 | 14.080 | 157.424 | 296.405 | 1.00 | 0.00 | O |
| ATOM | 3093 | C5* | A B | 73 | 14.592 | 158.639 | 295.877 | 1.00 | 0.00 | C |
| ATOM | 3094 | C4* | A B | 73 | 13.509 | 159.678 | 295.791 | 1.00 | 0.00 | C |
| ATOM | 3095 | O4* | A B | 73 | 12.470 | 159.211 | 294.894 | 1.00 | 0.00 | O |
| ATOM | 3096 | C3* | A B | 73 | 12.754 | 159.952 | 297.077 | 1.00 | 0.00 | C |
| ATOM | 3097 | O3* | A B | 73 | 13.468 | 160.845 | 297.916 | 1.00 | 0.00 | O |
| ATOM | 3098 | C2* | A B | 73 | 11.488 | 160.600 | 296.543 | 1.00 | 0.00 | C |
| ATOM | 3099 | O2* | A B | 73 | 11.699 | 161.945 | 296.174 | 1.00 | 0.00 | O |
| ATOM | 3100 | C1* | A B | 73 | 11.215 | 159.724 | 295.316 | 1.00 | 0.00 | C |
| ATOM | 3101 | N9 | A B | 73 | 10.354 | 158.586 | 295.644 | 1.00 | 0.00 | N |
| ATOM | 3102 | C8 | A B | 73 | 10.733 | 157.291 | 295.873 | 1.00 | 0.00 | C |
| ATOM | 3103 | N7 | A B | 73 | 9.736 | 156.496 | 296.178 | 1.00 | 0.00 | N |
| ATOM | 3104 | C5 | A B | 73 | 8.624 | 157.325 | 296.138 | 1.00 | 0.00 | C |
| ATOM | 3105 | C6 | A B | 73 | 7.257 | 157.085 | 296.367 | 1.00 | 0.00 | C |
| ATOM | 3106 | N6 | A B | 73 | 6.767 | 155.892 | 296.705 | 1.00 | 0.00 | N |
| ATOM | 3107 | N1 | A B | 73 | 6.404 | 158.127 | 296.235 | 1.00 | 0.00 | N |
| ATOM | 3108 | C2 | A B | 73 | 6.905 | 159.325 | 295.899 | 1.00 | 0.00 | C |
| ATOM | 3109 | N3 | A B | 73 | 8.169 | 159.675 | 295.662 | 1.00 | 0.00 | N |
| ATOM | 3110 | C4 | A B | 73 | 8.989 | 158.614 | 295.801 | 1.00 | 0.00 | C |

| | | | | | | | | | | |
|---|---|---|---|---|---|---|---|---|---|---|
| ATOM | 3111 | P | C | B | 74 | 12.932 | 160.489 | 299.470 | 1.00 | 0.00 | P |
| ATOM | 3112 | O1P | C | B | 74 | 14.137 | 160.095 | 300.247 | 1.00 | 0.00 | O |
| ATOM | 3113 | O2P | C | B | 74 | 11.760 | 159.568 | 299.417 | 1.00 | 0.00 | O |
| ATOM | 3114 | O5* | C | B | 74 | 12.447 | 161.919 | 299.985 | 1.00 | 0.00 | O |
| ATOM | 3115 | C5* | C | B | 74 | 12.754 | 162.361 | 301.307 | 1.00 | 0.00 | C |
| ATOM | 3116 | C4* | C | B | 74 | 12.502 | 163.846 | 301.439 | 1.00 | 0.00 | C |
| ATOM | 3117 | O4* | C | B | 74 | 11.311 | 164.069 | 302.240 | 1.00 | 0.00 | O |
| ATOM | 3118 | C3* | C | B | 74 | 13.580 | 164.652 | 302.153 | 1.00 | 0.00 | C |
| ATOM | 3119 | O3* | C | B | 74 | 14.640 | 164.995 | 301.265 | 1.00 | 0.00 | O |
| ATOM | 3120 | C2* | C | B | 74 | 12.801 | 165.880 | 302.607 | 1.00 | 0.00 | C |
| ATOM | 3121 | O2* | C | B | 74 | 12.562 | 166.831 | 301.591 | 1.00 | 0.00 | O |
| ATOM | 3122 | C1* | C | B | 74 | 11.475 | 165.245 | 303.015 | 1.00 | 0.00 | C |
| ATOM | 3123 | N1 | C | B | 74 | 11.475 | 164.872 | 304.432 | 1.00 | 0.00 | N |
| ATOM | 3124 | C2 | C | B | 74 | 11.314 | 165.880 | 305.377 | 1.00 | 0.00 | C |
| ATOM | 3125 | O2 | C | B | 74 | 11.202 | 167.056 | 304.984 | 1.00 | 0.00 | O |
| ATOM | 3126 | N3 | C | B | 74 | 11.284 | 165.556 | 306.688 | 1.00 | 0.00 | N |
| ATOM | 3127 | C4 | C | B | 74 | 11.410 | 164.282 | 307.064 | 1.00 | 0.00 | C |
| ATOM | 3128 | N4 | C | B | 74 | 11.361 | 164.010 | 308.374 | 1.00 | 0.00 | N |
| ATOM | 3129 | C5 | C | B | 74 | 11.591 | 163.232 | 306.118 | 1.00 | 0.00 | C |
| ATOM | 3130 | C6 | C | B | 74 | 11.617 | 163.569 | 304.823 | 1.00 | 0.00 | C |
| ATOM | 3131 | P | C | B | 75 | 16.158 | 165.005 | 301.797 | 1.00 | 0.00 | P |
| ATOM | 3132 | O1P | C | B | 75 | 16.993 | 165.722 | 300.804 | 1.00 | 0.00 | O |
| ATOM | 3133 | O2P | C | B | 75 | 16.518 | 163.630 | 302.214 | 1.00 | 0.00 | O |
| ATOM | 3134 | O5* | C | B | 75 | 16.114 | 165.901 | 303.104 | 1.00 | 0.00 | O |
| ATOM | 3135 | C5* | C | B | 75 | 16.110 | 167.314 | 303.012 | 1.00 | 0.00 | C |
| ATOM | 3136 | C4* | C | B | 75 | 16.191 | 167.896 | 304.388 | 1.00 | 0.00 | C |
| ATOM | 3137 | O4* | C | B | 75 | 15.066 | 167.372 | 305.139 | 1.00 | 0.00 | O |
| ATOM | 3138 | C3* | C | B | 75 | 17.416 | 167.444 | 305.166 | 1.00 | 0.00 | C |
| ATOM | 3139 | O3* | C | B | 75 | 18.485 | 168.357 | 304.977 | 1.00 | 0.00 | O |
| ATOM | 3140 | C2* | C | B | 75 | 16.932 | 167.507 | 306.606 | 1.00 | 0.00 | C |
| ATOM | 3141 | O2* | C | B | 75 | 17.057 | 168.811 | 307.142 | 1.00 | 0.00 | O |
| ATOM | 3142 | C1* | C | B | 75 | 15.464 | 167.095 | 306.465 | 1.00 | 0.00 | C |
| ATOM | 3143 | N1 | C | B | 75 | 15.230 | 165.669 | 306.727 | 1.00 | 0.00 | N |
| ATOM | 3144 | C2 | C | B | 75 | 15.146 | 165.239 | 308.049 | 1.00 | 0.00 | C |
| ATOM | 3145 | O2 | C | B | 75 | 15.259 | 166.072 | 308.960 | 1.00 | 0.00 | O |
| ATOM | 3146 | N3 | C | B | 75 | 14.950 | 163.926 | 308.308 | 1.00 | 0.00 | N |
| ATOM | 3147 | C4 | C | B | 75 | 14.837 | 163.061 | 307.301 | 1.00 | 0.00 | C |
| ATOM | 3148 | N4 | C | B | 75 | 14.646 | 161.771 | 307.601 | 1.00 | 0.00 | N |
| ATOM | 3149 | C5 | C | B | 75 | 14.912 | 163.476 | 305.939 | 1.00 | 0.00 | C |
| ATOM | 3150 | C6 | C | B | 75 | 15.106 | 164.778 | 305.700 | 1.00 | 0.00 | C |
| ATOM | 3151 | P | A | B | 76 | 19.470 | 168.468 | 304.158 | 1.00 | 0.00 | P |
| ATOM | 3152 | O1P | A | B | 76 | 18.807 | 169.092 | 302.983 | 1.00 | 0.00 | O |
| ATOM | 3153 | O2P | A | B | 76 | 20.651 | 167.598 | 303.958 | 1.00 | 0.00 | O |
| ATOM | 3154 | O5* | A | B | 76 | 20.168 | 169.745 | 304.883 | 1.00 | 0.00 | O |
| ATOM | 3155 | C5* | A | B | 76 | 21.429 | 169.301 | 305.377 | 1.00 | 0.00 | C |
| ATOM | 3156 | C4* | A | B | 76 | 21.339 | 169.021 | 306.859 | 1.00 | 0.00 | C |
| ATOM | 3157 | O4* | A | B | 76 | 20.053 | 168.404 | 307.141 | 1.00 | 0.00 | O |
| ATOM | 3158 | C3* | A | B | 76 | 22.335 | 168.005 | 307.387 | 1.00 | 0.00 | C |
| ATOM | 3159 | O3* | A | B | 76 | 23.578 | 168.628 | 307.689 | 1.00 | 0.00 | O |
| ATOM | 3160 | C2* | A | B | 76 | 21.649 | 167.504 | 308.649 | 1.00 | 0.00 | C |
| ATOM | 3161 | O2* | A | B | 76 | 21.810 | 168.370 | 309.755 | 1.00 | 0.00 | O |
| ATOM | 3162 | C1* | A | B | 76 | 20.181 | 167.477 | 308.212 | 1.00 | 0.00 | C |
| ATOM | 3163 | N9 | A | B | 76 | 19.741 | 166.169 | 307.738 | 1.00 | 0.00 | N |
| ATOM | 3164 | C8 | A | B | 76 | 19.901 | 165.636 | 306.481 | 1.00 | 0.00 | C |
| ATOM | 3165 | N7 | A | B | 76 | 19.363 | 164.450 | 306.337 | 1.00 | 0.00 | N |
| ATOM | 3166 | C5 | A | B | 76 | 18.814 | 164.181 | 307.586 | 1.00 | 0.00 | C |
| ATOM | 3167 | C6 | A | B | 76 | 18.092 | 163.083 | 308.080 | 1.00 | 0.00 | C |
| ATOM | 3168 | N6 | A | B | 76 | 17.798 | 162.014 | 307.347 | 1.00 | 0.00 | N |
| ATOM | 3169 | N1 | A | B | 76 | 17.680 | 163.123 | 309.367 | 1.00 | 0.00 | N |
| ATOM | 3170 | C2 | A | B | 76 | 17.983 | 164.202 | 310.101 | 1.00 | 0.00 | C |
| ATOM | 3171 | N3 | A | B | 76 | 18.654 | 165.298 | 309.748 | 1.00 | 0.00 | N |
| ATOM | 3172 | C4 | A | B | 76 | 19.046 | 165.223 | 308.460 | 1.00 | 0.00 | C |
| TER | 3173 | | A | B | 76 | | | | | | |
| ATOM | 3174 | O3P | G | C | 1 | 17.719 | 161.229 | 281.171 | 1.00 | 0.00 | O |
| ATOM | 3175 | P | G | C | 1 | 18.250 | 159.873 | 281.605 | 1.00 | 0.00 | P |
| ATOM | 3176 | O1P | G | C | 1 | 19.195 | 159.243 | 280.593 | 1.00 | 0.00 | O |
| ATOM | 3177 | O2P | G | C | 1 | 17.160 | 158.923 | 282.081 | 1.00 | 0.00 | O |
| ATOM | 3178 | O5* | G | C | 1 | 19.192 | 160.130 | 282.904 | 1.00 | 0.00 | O |
| ATOM | 3179 | C5* | G | C | 1 | 20.370 | 159.345 | 283.086 | 1.00 | 0.00 | C |
| ATOM | 3180 | C4* | G | C | 1 | 20.981 | 159.616 | 284.432 | 1.00 | 0.00 | C |
| ATOM | 3181 | O4* | G | C | 1 | 20.041 | 159.303 | 285.495 | 1.00 | 0.00 | O |
| ATOM | 3182 | C3* | G | C | 1 | 22.222 | 158.771 | 284.670 | 1.00 | 0.00 | C |
| ATOM | 3183 | O3* | G | C | 1 | 23.352 | 159.598 | 284.437 | 1.00 | 0.00 | O |
| ATOM | 3184 | C2* | G | C | 1 | 22.096 | 158.333 | 286.126 | 1.00 | 0.00 | C |
| ATOM | 3185 | O2* | G | C | 1 | 22.694 | 159.237 | 287.032 | 1.00 | 0.00 | O |
| ATOM | 3186 | C1* | G | C | 1 | 20.577 | 158.293 | 286.320 | 1.00 | 0.00 | C |
| ATOM | 3187 | N9 | G | C | 1 | 19.940 | 157.036 | 285.938 | 1.00 | 0.00 | N |
| ATOM | 3188 | C8 | G | C | 1 | 18.847 | 156.893 | 285.118 | 1.00 | 0.00 | C |
| ATOM | 3189 | N7 | G | C | 1 | 18.482 | 155.652 | 284.958 | 1.00 | 0.00 | N |
| ATOM | 3190 | C5 | G | C | 1 | 19.391 | 154.927 | 285.715 | 1.00 | 0.00 | C |
| ATOM | 3191 | C6 | G | C | 1 | 19.499 | 153.531 | 285.927 | 1.00 | 0.00 | C |
| ATOM | 3192 | O6 | G | C | 1 | 18.790 | 152.625 | 285.473 | 1.00 | 0.00 | O |
| ATOM | 3193 | N1 | G | C | 1 | 20.564 | 153.223 | 286.769 | 1.00 | 0.00 | N |
| ATOM | 3194 | C2 | G | C | 1 | 21.416 | 154.139 | 287.334 | 1.00 | 0.00 | C |
| ATOM | 3195 | N2 | G | C | 1 | 22.379 | 153.645 | 288.121 | 1.00 | 0.00 | N |
| ATOM | 3196 | N3 | G | C | 1 | 21.329 | 155.444 | 287.142 | 1.00 | 0.00 | N |
| ATOM | 3197 | C4 | G | C | 1 | 20.299 | 155.767 | 286.328 | 1.00 | 0.00 | C |

```
ATOM   3198  P     C C  2    24.896 159.281 284.039  1.00  0.00           P
ATOM   3199  O1P   C C  2    25.451 160.500 283.397  1.00  0.00           O
ATOM   3200  O2P   C C  2    24.932 157.988 283.310  1.00  0.00           O
ATOM   3201  O5*   C C  2    25.618 159.081 285.441  1.00  0.00           O
ATOM   3202  C5*   C C  2    26.874 159.697 285.695  1.00  0.00           C
ATOM   3203  C4*   C C  2    27.913 158.651 286.015  1.00  0.00           C
ATOM   3204  O4*   C C  2    27.515 157.970 287.234  1.00  0.00           O
ATOM   3205  C3*   C C  2    28.076 157.507 285.022  1.00  0.00           C
ATOM   3206  O3*   C C  2    28.905 157.846 283.914  1.00  0.00           O
ATOM   3207  C2*   C C  2    28.762 156.465 285.893  1.00  0.00           C
ATOM   3208  O2*   C C  2    30.140 156.721 286.069  1.00  0.00           O
ATOM   3209  C1*   C C  2    28.018 156.644 287.216  1.00  0.00           C
ATOM   3210  N1    C C  2    26.891 155.711 287.325  1.00  0.00           N
ATOM   3211  C2    C C  2    27.124 154.442 287.866  1.00  0.00           C
ATOM   3212  O2    C C  2    28.265 154.163 288.276  1.00  0.00           O
ATOM   3213  N3    C C  2    26.107 153.556 287.930  1.00  0.00           N
ATOM   3214  C4    C C  2    24.896 153.899 287.488  1.00  0.00           C
ATOM   3215  N4    C C  2    23.926 152.989 287.566  1.00  0.00           N
ATOM   3216  C5    C C  2    24.627 155.188 286.949  1.00  0.00           C
ATOM   3217  C6    C C  2    25.643 156.058 286.889  1.00  0.00           C
ATOM   3218  P     G C  3    29.095 156.797 282.702  1.00  0.00           P
ATOM   3219  O1P   G C  3    30.136 157.338 281.792  1.00  0.00           O
ATOM   3220  O2P   G C  3    27.753 156.453 282.162  1.00  0.00           O
ATOM   3221  O5*   G C  3    29.722 155.497 283.379  1.00  0.00           O
ATOM   3222  C5*   G C  3    31.117 155.259 283.293  1.00  0.00           C
ATOM   3223  C4*   G C  3    31.501 154.071 284.136  1.00  0.00           C
ATOM   3224  O4*   G C  3    30.653 153.991 285.314  1.00  0.00           O
ATOM   3225  C3*   G C  3    31.299 152.722 283.483  1.00  0.00           C
ATOM   3226  O3*   G C  3    32.333 152.417 282.563  1.00  0.00           O
ATOM   3227  C2*   G C  3    31.299 151.798 284.693  1.00  0.00           C
ATOM   3228  O2*   G C  3    32.585 151.513 285.206  1.00  0.00           O
ATOM   3229  C1*   G C  3    30.477 152.627 285.682  1.00  0.00           C
ATOM   3230  N9    G C  3    29.060 152.304 285.551  1.00  0.00           N
ATOM   3231  C8    G C  3    28.094 153.050 284.923  1.00  0.00           C
ATOM   3232  N7    G C  3    26.923 152.470 284.919  1.00  0.00           N
ATOM   3233  C5    G C  3    27.129 151.276 285.598  1.00  0.00           C
ATOM   3234  C6    G C  3    26.225 150.220 285.893  1.00  0.00           C
ATOM   3235  O6    G C  3    25.025 150.133 285.614  1.00  0.00           O
ATOM   3236  N1    G C  3    26.852 149.189 286.587  1.00  0.00           N
ATOM   3237  C2    G C  3    28.180 149.172 286.949  1.00  0.00           C
ATOM   3238  N2    G C  3    28.598 148.083 287.610  1.00  0.00           N
ATOM   3239  N3    G C  3    29.031 150.153 286.681  1.00  0.00           N
ATOM   3240  C4    G C  3    28.439 151.162 286.005  1.00  0.00           C
ATOM   3241  P     G C  4    31.974 151.609 281.231  1.00  0.00           P
ATOM   3242  O1P   G C  4    33.056 151.809 280.236  1.00  0.00           O
ATOM   3243  O2P   G C  4    30.586 152.010 280.897  1.00  0.00           O
ATOM   3244  O5*   G C  4    31.986 150.081 281.685  1.00  0.00           O
ATOM   3245  C5*   G C  4    33.204 149.442 282.021  1.00  0.00           C
ATOM   3246  C4*   G C  4    32.932 148.200 282.825  1.00  0.00           C
ATOM   3247  O4*   G C  4    32.017 148.491 283.912  1.00  0.00           O
ATOM   3248  C3*   G C  4    32.217 147.103 282.076  1.00  0.00           C
ATOM   3249  O3*   G C  4    33.150 146.392 281.305  1.00  0.00           O
ATOM   3250  C2*   G C  4    31.690 146.251 283.217  1.00  0.00           C
ATOM   3251  O2*   G C  4    32.683 145.456 283.813  1.00  0.00           O
ATOM   3252  C1*   G C  4    31.239 147.334 284.191  1.00  0.00           C
ATOM   3253  N9    G C  4    29.837 147.667 283.967  1.00  0.00           N
ATOM   3254  C8    G C  4    29.322 148.844 283.476  1.00  0.00           C
ATOM   3255  N7    G C  4    28.019 148.842 283.401  1.00  0.00           N
ATOM   3256  C5    G C  4    27.653 147.593 283.868  1.00  0.00           C
ATOM   3257  C6    G C  4    26.376 147.018 284.020  1.00  0.00           C
ATOM   3258  O6    G C  4    25.265 147.532 283.778  1.00  0.00           O
ATOM   3259  N1    G C  4    26.458 145.715 284.510  1.00  0.00           N
ATOM   3260  C2    G C  4    27.627 145.053 284.818  1.00  0.00           C
ATOM   3261  N2    G C  4    27.510 143.798 285.267  1.00  0.00           N
ATOM   3262  N3    G C  4    28.827 145.586 284.688  1.00  0.00           N
ATOM   3263  C4    G C  4    28.765 146.849 284.211  1.00  0.00           C
ATOM   3264  P     A C  5    32.665 145.637 279.984  1.00  0.00           P
ATOM   3265  O1P   A C  5    33.848 144.925 279.437  1.00  0.00           O
ATOM   3266  O2P   A C  5    31.921 146.606 279.123  1.00  0.00           O
ATOM   3267  O5*   A C  5    31.685 144.526 280.554  1.00  0.00           O
ATOM   3268  C5*   A C  5    32.222 143.405 281.223  1.00  0.00           C
ATOM   3269  C4*   A C  5    31.129 142.444 281.559  1.00  0.00           C
ATOM   3270  O4*   A C  5    30.222 143.080 282.501  1.00  0.00           O
ATOM   3271  C3*   A C  5    30.230 142.075 280.393  1.00  0.00           C
ATOM   3272  O3*   A C  5    30.824 141.025 279.641  1.00  0.00           O
ATOM   3273  C2*   A C  5    28.992 141.611 281.148  1.00  0.00           C
ATOM   3274  O2*   A C  5    29.182 140.378 281.823  1.00  0.00           O
ATOM   3275  C1*   A C  5    28.898 142.699 282.214  1.00  0.00           C
ATOM   3276  N9    A C  5    28.183 143.874 281.732  1.00  0.00           N
ATOM   3277  C8    A C  5    28.691 145.042 281.229  1.00  0.00           C
ATOM   3278  N7    A C  5    27.770 145.914 280.893  1.00  0.00           N
ATOM   3279  C5    A C  5    26.578 145.274 281.196  1.00  0.00           C
ATOM   3280  C6    A C  5    25.229 145.676 281.090  1.00  0.00           C
ATOM   3281  N6    A C  5    24.839 146.865 280.617  1.00  0.00           N
ATOM   3282  N1    A C  5    24.282 144.802 281.484  1.00  0.00           N
ATOM   3283  C2    A C  5    24.670 143.597 281.946  1.00  0.00           C
ATOM   3284  N3    A C  5    25.904 143.108 282.096  1.00  0.00           N
```

| | | | | | | | | | | |
|---|---|---|---|---|---|---|---|---|---|---|
| ATOM | 3285 | C4 | A C | 5 | 26.819 | 144.013 | 281.703 | 1.00 | 0.00 | C |
| ATOM | 3286 | P | U C | 6 | 30.523 | 140.900 | 278.068 | 1.00 | 0.00 | P |
| ATOM | 3287 | O1P | U C | 6 | 31.269 | 139.703 | 277.615 | 1.00 | 0.00 | O |
| ATOM | 3288 | O2P | U C | 6 | 30.746 | 142.209 | 277.402 | 1.00 | 0.00 | O |
| ATOM | 3289 | O5* | U C | 6 | 28.974 | 140.543 | 277.999 | 1.00 | 0.00 | O |
| ATOM | 3290 | C5* | U C | 6 | 28.530 | 139.281 | 278.445 | 1.00 | 0.00 | C |
| ATOM | 3291 | C4* | U C | 6 | 27.044 | 139.293 | 278.634 | 1.00 | 0.00 | C |
| ATOM | 3292 | O4* | U C | 6 | 26.639 | 140.430 | 279.442 | 1.00 | 0.00 | O |
| ATOM | 3293 | C3* | U C | 6 | 26.277 | 139.509 | 277.357 | 1.00 | 0.00 | C |
| ATOM | 3294 | O3* | U C | 6 | 26.215 | 138.291 | 276.649 | 1.00 | 0.00 | O |
| ATOM | 3295 | C2* | U C | 6 | 24.921 | 139.903 | 277.910 | 1.00 | 0.00 | C |
| ATOM | 3296 | O2* | U C | 6 | 24.252 | 138.782 | 278.442 | 1.00 | 0.00 | O |
| ATOM | 3297 | C1* | U C | 6 | 25.334 | 140.824 | 279.055 | 1.00 | 0.00 | C |
| ATOM | 3298 | N1 | U C | 6 | 25.361 | 142.238 | 278.669 | 1.00 | 0.00 | N |
| ATOM | 3299 | C2 | U C | 6 | 24.139 | 142.831 | 278.426 | 1.00 | 0.00 | C |
| ATOM | 3300 | O2 | U C | 6 | 23.096 | 142.223 | 278.500 | 1.00 | 0.00 | O |
| ATOM | 3301 | N3 | U C | 6 | 24.188 | 144.146 | 278.074 | 1.00 | 0.00 | N |
| ATOM | 3302 | C4 | U C | 6 | 25.306 | 144.927 | 277.921 | 1.00 | 0.00 | C |
| ATOM | 3303 | O4 | U C | 6 | 25.174 | 146.096 | 277.564 | 1.00 | 0.00 | O |
| ATOM | 3304 | C5 | U C | 6 | 26.550 | 144.253 | 278.185 | 1.00 | 0.00 | C |
| ATOM | 3305 | C6 | U C | 6 | 26.531 | 142.953 | 278.545 | 1.00 | 0.00 | C |
| ATOM | 3306 | P | U C | 7 | 26.107 | 138.320 | 275.052 | 1.00 | 0.00 | P |
| ATOM | 3307 | O1P | U C | 7 | 26.341 | 136.938 | 274.610 | 1.00 | 0.00 | O |
| ATOM | 3308 | O2P | U C | 7 | 26.941 | 139.452 | 274.531 | 1.00 | 0.00 | O |
| ATOM | 3309 | O5* | U C | 7 | 24.582 | 138.722 | 274.773 | 1.00 | 0.00 | O |
| ATOM | 3310 | C5* | U C | 7 | 23.500 | 137.990 | 275.357 | 1.00 | 0.00 | C |
| ATOM | 3311 | C4* | U C | 7 | 22.183 | 138.594 | 274.918 | 1.00 | 0.00 | C |
| ATOM | 3312 | O4* | U C | 7 | 22.163 | 139.970 | 275.383 | 1.00 | 0.00 | O |
| ATOM | 3313 | C3* | U C | 7 | 21.967 | 138.637 | 273.406 | 1.00 | 0.00 | C |
| ATOM | 3314 | O3* | U C | 7 | 20.632 | 138.280 | 273.056 | 1.00 | 0.00 | O |
| ATOM | 3315 | C2* | U C | 7 | 22.301 | 140.078 | 273.044 | 1.00 | 0.00 | C |
| ATOM | 3316 | O2* | U C | 7 | 21.509 | 140.558 | 271.978 | 1.00 | 0.00 | O |
| ATOM | 3317 | C1* | U C | 7 | 21.889 | 140.829 | 274.305 | 1.00 | 0.00 | C |
| ATOM | 3318 | N1 | U C | 7 | 22.626 | 142.086 | 274.506 | 1.00 | 0.00 | N |
| ATOM | 3319 | C2 | U C | 7 | 21.906 | 143.260 | 274.434 | 1.00 | 0.00 | C |
| ATOM | 3320 | O2 | U C | 7 | 20.697 | 143.285 | 274.254 | 1.00 | 0.00 | O |
| ATOM | 3321 | N3 | U C | 7 | 22.646 | 144.404 | 274.586 | 1.00 | 0.00 | N |
| ATOM | 3322 | C4 | U C | 7 | 24.010 | 144.493 | 274.805 | 1.00 | 0.00 | C |
| ATOM | 3323 | O4 | U C | 7 | 24.550 | 145.615 | 274.912 | 1.00 | 0.00 | O |
| ATOM | 3324 | C5 | U C | 7 | 24.674 | 143.230 | 274.891 | 1.00 | 0.00 | C |
| ATOM | 3325 | C6 | U C | 7 | 23.980 | 142.102 | 274.745 | 1.00 | 0.00 | C |
| ATOM | 3326 | P | U C | 8 | 20.291 | 136.787 | 272.533 | 1.00 | 0.00 | P |
| ATOM | 3327 | O1P | U C | 8 | 18.884 | 136.808 | 272.041 | 1.00 | 0.00 | O |
| ATOM | 3328 | O2P | U C | 8 | 20.724 | 135.787 | 273.537 | 1.00 | 0.00 | O |
| ATOM | 3329 | O5* | U C | 8 | 21.199 | 136.597 | 271.232 | 1.00 | 0.00 | O |
| ATOM | 3330 | C5* | U C | 8 | 20.788 | 137.167 | 269.998 | 1.00 | 0.00 | C |
| ATOM | 3331 | C4* | U C | 8 | 21.085 | 136.241 | 268.847 | 1.00 | 0.00 | C |
| ATOM | 3332 | O4* | U C | 8 | 22.530 | 136.145 | 268.659 | 1.00 | 0.00 | O |
| ATOM | 3333 | C3* | U C | 8 | 20.632 | 134.786 | 268.936 | 1.00 | 0.00 | C |
| ATOM | 3334 | O3* | U C | 8 | 19.252 | 134.623 | 268.600 | 1.00 | 0.00 | O |
| ATOM | 3335 | C2* | U C | 8 | 21.522 | 134.184 | 267.860 | 1.00 | 0.00 | C |
| ATOM | 3336 | O2* | U C | 8 | 21.202 | 134.611 | 266.539 | 1.00 | 0.00 | O |
| ATOM | 3337 | C1* | U C | 8 | 22.860 | 134.843 | 268.220 | 1.00 | 0.00 | C |
| ATOM | 3338 | N1 | U C | 8 | 23.545 | 134.166 | 269.323 | 1.00 | 0.00 | N |
| ATOM | 3339 | C2 | U C | 8 | 24.333 | 133.072 | 269.020 | 1.00 | 0.00 | C |
| ATOM | 3340 | O2 | U C | 8 | 24.492 | 132.670 | 267.888 | 1.00 | 0.00 | O |
| ATOM | 3341 | N3 | U C | 8 | 24.923 | 132.476 | 270.096 | 1.00 | 0.00 | N |
| ATOM | 3342 | C4 | U C | 8 | 24.815 | 132.861 | 271.416 | 1.00 | 0.00 | C |
| ATOM | 3343 | O4 | U C | 8 | 25.360 | 132.191 | 272.292 | 1.00 | 0.00 | O |
| ATOM | 3344 | C5 | U C | 8 | 23.988 | 133.994 | 271.637 | 1.00 | 0.00 | C |
| ATOM | 3345 | C6 | U C | 8 | 23.402 | 134.596 | 270.608 | 1.00 | 0.00 | C |
| ATOM | 3346 | P | A C | 9 | 18.379 | 133.474 | 269.312 | 1.00 | 0.00 | P |
| ATOM | 3347 | O1P | A C | 9 | 17.096 | 134.091 | 269.743 | 1.00 | 0.00 | O |
| ATOM | 3348 | O2P | A C | 9 | 19.216 | 132.732 | 270.321 | 1.00 | 0.00 | O |
| ATOM | 3349 | O5* | A C | 9 | 18.064 | 132.475 | 268.128 | 1.00 | 0.00 | O |
| ATOM | 3350 | C5* | A C | 9 | 17.188 | 132.859 | 267.074 | 1.00 | 0.00 | C |
| ATOM | 3351 | C4* | A C | 9 | 16.263 | 131.720 | 266.749 | 1.00 | 0.00 | C |
| ATOM | 3352 | O4* | A C | 9 | 17.086 | 130.683 | 266.140 | 1.00 | 0.00 | O |
| ATOM | 3353 | C3* | A C | 9 | 15.574 | 131.063 | 267.954 | 1.00 | 0.00 | C |
| ATOM | 3354 | O3* | A C | 9 | 14.316 | 130.519 | 267.566 | 1.00 | 0.00 | O |
| ATOM | 3355 | C2* | A C | 9 | 16.508 | 129.898 | 268.277 | 1.00 | 0.00 | C |
| ATOM | 3356 | O2* | A C | 9 | 15.822 | 128.796 | 268.811 | 1.00 | 0.00 | O |
| ATOM | 3357 | C1* | A C | 9 | 16.974 | 129.494 | 266.892 | 1.00 | 0.00 | C |
| ATOM | 3358 | N9 | A C | 9 | 18.257 | 128.772 | 266.888 | 1.00 | 0.00 | N |
| ATOM | 3359 | C8 | A C | 9 | 19.073 | 128.506 | 267.955 | 1.00 | 0.00 | C |
| ATOM | 3360 | N7 | A C | 9 | 20.106 | 127.731 | 267.659 | 1.00 | 0.00 | N |
| ATOM | 3361 | C5 | A C | 9 | 19.963 | 127.498 | 266.305 | 1.00 | 0.00 | C |
| ATOM | 3362 | C6 | A C | 9 | 20.716 | 126.757 | 265.397 | 1.00 | 0.00 | C |
| ATOM | 3363 | N6 | A C | 9 | 21.819 | 126.068 | 265.734 | 1.00 | 0.00 | N |
| ATOM | 3364 | N1 | A C | 9 | 20.304 | 126.733 | 264.111 | 1.00 | 0.00 | N |
| ATOM | 3365 | C2 | A C | 9 | 19.209 | 127.426 | 263.771 | 1.00 | 0.00 | C |
| ATOM | 3366 | N3 | A C | 9 | 18.416 | 128.170 | 264.535 | 1.00 | 0.00 | N |
| ATOM | 3367 | C4 | A C | 9 | 18.841 | 128.160 | 265.808 | 1.00 | 0.00 | C |
| HETATM | 3368 | P | 2MG C | 10 | 12.939 | 131.352 | 267.844 | 1.00 | 0.00 | P |
| HETATM | 3369 | O1P | 2MG C | 10 | 13.185 | 132.794 | 267.811 | 1.00 | 0.00 | O |
| HETATM | 3370 | O2P | 2MG C | 10 | 11.894 | 130.776 | 266.957 | 1.00 | 0.00 | O |
| HETATM | 3371 | O5* | 2MG C | 10 | 12.626 | 131.006 | 269.357 | 1.00 | 0.00 | O |

| | | | | | | | | | | |
|---|---|---|---|---|---|---|---|---|---|---|
|HETATM|3372|C5*|2MG|C|10|11.437|131.526|269.972|1.00|0.00|C|
|HETATM|3373|C4*|2MG|C|10|10.922|130.563|271.011|1.00|0.00|C|
|HETATM|3374|O4*|2MG|C|10|10.618|129.299|270.356|1.00|0.00|O|
|HETATM|3375|C3*|2MG|C|10|11.917|130.216|272.100|1.00|0.00|C|
|HETATM|3376|O3*|2MG|C|10|11.761|131.123|273.186|1.00|0.00|O|
|HETATM|3377|C2*|2MG|C|10|11.478|128.820|272.482|1.00|0.00|C|
|HETATM|3378|O2*|2MG|C|10|10.288|128.896|273.256|1.00|0.00|O|
|HETATM|3379|C1*|2MG|C|10|11.125|128.227|271.126|1.00|0.00|C|
|HETATM|3380|N9|2MG|C|10|12.190|127.580|270.365|1.00|0.00|N|
|HETATM|3381|C8|2MG|C|10|12.516|127.826|269.047|1.00|0.00|C|
|HETATM|3382|N7|2MG|C|10|13.468|127.045|268.592|1.00|0.00|N|
|HETATM|3383|C5|2MG|C|10|13.798|126.244|269.677|1.00|0.00|C|
|HETATM|3384|C6|2MG|C|10|14.769|125.232|269.791|1.00|0.00|C|
|HETATM|3385|O6|2MG|C|10|15.514|124.789|268.917|1.00|0.00|O|
|HETATM|3386|N1|2MG|C|10|14.824|124.710|271.080|1.00|0.00|N|
|HETATM|3387|C2|2MG|C|10|14.025|125.116|272.129|1.00|0.00|C|
|HETATM|3388|N2|2MG|C|10|14.227|124.488|273.297|1.00|0.00|N|
|HETATM|3389|CM2|2MG|C|10|13.390|124.671|274.488|1.00|0.00|C|
|HETATM|3390|N3|2MG|C|10|13.097|126.062|272.031|1.00|0.00|N|
|HETATM|3391|C4|2MG|C|10|13.035|126.577|270.788|1.00|0.00|C|
|ATOM|3392|P| |C|11|13.042|131.788|273.867|1.00|0.00|P|
|ATOM|3393|O1P|C|C|11|12.617|132.830|274.814|1.00|0.00|O|
|ATOM|3394|O2P|C|C|11|13.994|132.144|272.764|1.00|0.00|O|
|ATOM|3395|O5*|C|C|11|13.647|130.619|274.767|1.00|0.00|O|
|ATOM|3396|C5*|C|C|11|13.003|130.267|275.993|1.00|0.00|C|
|ATOM|3397|C4*|C|C|11|13.721|129.127|276.675|1.00|0.00|C|
|ATOM|3398|O4*|C|C|11|13.727|127.959|275.813|1.00|0.00|O|
|ATOM|3399|C3*|C|C|11|15.173|129.411|276.989|1.00|0.00|C|
|ATOM|3400|O3*|C|C|11|15.278|130.003|278.276|1.00|0.00|O|
|ATOM|3401|C2*|C|C|11|15.834|128.035|276.927|1.00|0.00|C|
|ATOM|3402|O2*|C|C|11|15.808|127.367|278.168|1.00|0.00|O|
|ATOM|3403|C1*|C|C|11|14.976|127.299|275.896|1.00|0.00|C|
|ATOM|3404|N1|C|C|11|15.558|127.282|274.550|1.00|0.00|N|
|ATOM|3405|C2|C|C|11|16.578|126.376|274.257|1.00|0.00|C|
|ATOM|3406|O2|C|C|11|16.956|125.597|275.147|1.00|0.00|O|
|ATOM|3407|N3|C|C|11|17.133|126.378|273.008|1.00|0.00|N|
|ATOM|3408|C4|C|C|11|16.693|127.243|272.088|1.00|0.00|C|
|ATOM|3409|N4|C|C|11|17.246|127.212|270.867|1.00|0.00|N|
|ATOM|3410|C5|C|C|11|15.657|128.171|272.367|1.00|0.00|C|
|ATOM|3411|C6|C|C|11|15.117|128.152|273.599|1.00|0.00|C|
|ATOM|3412|P| |U|C|12|16.413|131.091|278.528|1.00|0.00|P|
|ATOM|3413|O1P|U|C|12|16.268|131.743|279.853|1.00|0.00|O|
|ATOM|3414|O2P|U|C|12|16.402|131.932|277.306|1.00|0.00|O|
|ATOM|3415|O5*|U|C|12|17.746|130.217|278.521|1.00|0.00|O|
|ATOM|3416|C5*|U|C|12|18.026|129.300|279.577|1.00|0.00|C|
|ATOM|3417|C4*|U|C|12|19.251|128.480|279.250|1.00|0.00|C|
|ATOM|3418|O4*|U|C|12|18.982|127.636|278.101|1.00|0.00|O|
|ATOM|3419|C3*|U|C|12|20.460|129.280|278.793|1.00|0.00|C|
|ATOM|3420|O3*|U|C|12|21.175|129.787|279.897|1.00|0.00|O|
|ATOM|3421|C2*|U|C|12|21.296|128.218|278.092|1.00|0.00|C|
|ATOM|3422|O2*|U|C|12|22.117|127.482|278.982|1.00|0.00|O|
|ATOM|3423|C1*|U|C|12|20.215|127.359|277.434|1.00|0.00|C|
|ATOM|3424|N1|U|C|12|20.071|127.724|276.021|1.00|0.00|N|
|ATOM|3425|C2|U|C|12|20.957|127.170|275.118|1.00|0.00|C|
|ATOM|3426|O2|U|C|12|21.853|126.431|275.442|1.00|0.00|O|
|ATOM|3427|N3|U|C|12|20.760|127.532|273.821|1.00|0.00|N|
|ATOM|3428|C4|U|C|12|19.785|128.390|273.342|1.00|0.00|C|
|ATOM|3429|O4|U|C|12|19.686|128.585|272.137|1.00|0.00|O|
|ATOM|3430|C5|U|C|12|18.927|128.932|274.343|1.00|0.00|C|
|ATOM|3431|C6|U|C|12|19.102|128.582|275.620|1.00|0.00|C|
|ATOM|3432|P| |C|C|13|22.205|130.994|279.685|1.00|0.00|P|
|ATOM|3433|O1P|C|C|13|22.738|131.464|280.991|1.00|0.00|O|
|ATOM|3434|O2P|C|C|13|21.550|131.956|278.770|1.00|0.00|O|
|ATOM|3435|O5*|C|C|13|23.412|130.273|278.954|1.00|0.00|O|
|ATOM|3436|C5*|C|C|13|24.078|130.877|277.870|1.00|0.00|C|
|ATOM|3437|C4*|C|C|13|24.721|129.820|277.023|1.00|0.00|C|
|ATOM|3438|O4*|C|C|13|23.740|129.216|276.138|1.00|0.00|O|
|ATOM|3439|C3*|C|C|13|25.758|130.386|276.083|1.00|0.00|C|
|ATOM|3440|O3*|C|C|13|26.930|130.590|276.854|1.00|0.00|O|
|ATOM|3441|C2*|C|C|13|25.829|129.306|275.004|1.00|0.00|C|
|ATOM|3442|O2*|C|C|13|26.622|128.195|275.340|1.00|0.00|O|
|ATOM|3443|C1*|C|C|13|24.368|128.850|274.922|1.00|0.00|C|
|ATOM|3444|N1|C|C|13|23.610|129.455|273.821|1.00|0.00|N|
|ATOM|3445|C2|C|C|13|23.867|129.052|272.509|1.00|0.00|C|
|ATOM|3446|O2|C|C|13|24.785|128.236|272.303|1.00|0.00|O|
|ATOM|3447|N3|C|C|13|23.135|129.576|271.492|1.00|0.00|N|
|ATOM|3448|C4|C|C|13|22.213|130.515|271.750|1.00|0.00|C|
|ATOM|3449|N4|C|C|13|21.534|131.033|270.728|1.00|0.00|N|
|ATOM|3450|C5|C|C|13|21.945|130.965|273.082|1.00|0.00|C|
|ATOM|3451|C6|C|C|13|22.652|130.401|274.078|1.00|0.00|C|
|ATOM|3452|P| |A|C|14|28.156|131.406|276.233|1.00|0.00|P|
|ATOM|3453|O1P|A|C|14|29.123|131.700|277.323|1.00|0.00|O|
|ATOM|3454|O2P|A|C|14|27.658|132.514|275.384|1.00|0.00|O|
|ATOM|3455|O5*|A|C|14|28.818|130.293|275.324|1.00|0.00|O|
|ATOM|3456|C5*|A|C|14|29.154|130.567|273.995|1.00|0.00|C|
|ATOM|3457|C4*|A|C|14|29.825|129.376|273.382|1.00|0.00|C|
|ATOM|3458|O4*|A|C|14|28.795|128.577|272.741|1.00|0.00|O|

| | | | | | | | | | | |
|---|---|---|---|---|---|---|---|---|---|---|
| ATOM | 3459 | C3* | A | C | 14 | 30.762 | 129.783 | 272.252 | 1.00 | 0.00 | C |
| ATOM | 3460 | O3* | A | C | 14 | 32.072 | 130.003 | 272.732 | 1.00 | 0.00 | O |
| ATOM | 3461 | C2* | A | C | 14 | 30.673 | 128.602 | 271.309 | 1.00 | 0.00 | C |
| ATOM | 3462 | O2* | A | C | 14 | 31.431 | 127.487 | 271.740 | 1.00 | 0.00 | O |
| ATOM | 3463 | C1* | A | C | 14 | 29.186 | 128.286 | 271.399 | 1.00 | 0.00 | C |
| ATOM | 3464 | N9 | A | C | 14 | 28.373 | 129.079 | 270.483 | 1.00 | 0.00 | N |
| ATOM | 3465 | C8 | A | C | 14 | 27.395 | 130.012 | 270.768 | 1.00 | 0.00 | C |
| ATOM | 3466 | N7 | A | C | 14 | 26.786 | 130.476 | 269.692 | 1.00 | 0.00 | N |
| ATOM | 3467 | C5 | A | C | 14 | 27.415 | 129.822 | 268.643 | 1.00 | 0.00 | C |
| ATOM | 3468 | C6 | A | C | 14 | 27.256 | 129.898 | 267.259 | 1.00 | 0.00 | C |
| ATOM | 3469 | N6 | A | C | 14 | 26.336 | 130.670 | 266.642 | 1.00 | 0.00 | N |
| ATOM | 3470 | N1 | A | C | 14 | 28.078 | 129.148 | 266.500 | 1.00 | 0.00 | N |
| ATOM | 3471 | C2 | A | C | 14 | 28.991 | 128.384 | 267.102 | 1.00 | 0.00 | C |
| ATOM | 3472 | N3 | A | C | 14 | 29.246 | 128.243 | 268.377 | 1.00 | 0.00 | N |
| ATOM | 3473 | C4 | A | C | 14 | 28.412 | 128.988 | 269.110 | 1.00 | 0.00 | C |
| ATOM | 3474 | P | G | C | 15 | 32.718 | 131.456 | 272.608 | 1.00 | 0.00 | P |
| ATOM | 3475 | O1P | G | C | 15 | 34.067 | 131.415 | 273.219 | 1.00 | 0.00 | O |
| ATOM | 3476 | O2P | G | C | 15 | 31.770 | 132.490 | 273.021 | 1.00 | 0.00 | O |
| ATOM | 3477 | O5* | G | C | 15 | 32.860 | 131.692 | 271.039 | 1.00 | 0.00 | O |
| ATOM | 3478 | C5* | G | C | 15 | 33.460 | 130.735 | 270.206 | 1.00 | 0.00 | C |
| ATOM | 3479 | C4* | G | C | 15 | 33.037 | 130.971 | 268.766 | 1.00 | 0.00 | C |
| ATOM | 3480 | O4* | G | C | 15 | 31.664 | 130.531 | 268.581 | 1.00 | 0.00 | O |
| ATOM | 3481 | C3* | G | C | 15 | 32.989 | 132.417 | 268.308 | 1.00 | 0.00 | C |
| ATOM | 3482 | O3* | G | C | 15 | 34.279 | 132.906 | 267.970 | 1.00 | 0.00 | O |
| ATOM | 3483 | C2* | G | C | 15 | 32.102 | 132.306 | 267.071 | 1.00 | 0.00 | C |
| ATOM | 3484 | O2* | G | C | 15 | 32.712 | 131.703 | 265.967 | 1.00 | 0.00 | O |
| ATOM | 3485 | C1* | G | C | 15 | 31.035 | 131.343 | 267.584 | 1.00 | 0.00 | C |
| ATOM | 3486 | N9 | G | C | 15 | 30.009 | 132.184 | 268.185 | 1.00 | 0.00 | N |
| ATOM | 3487 | C8 | G | C | 15 | 29.814 | 132.490 | 269.515 | 1.00 | 0.00 | C |
| ATOM | 3488 | N7 | G | C | 15 | 28.822 | 133.343 | 269.701 | 1.00 | 0.00 | N |
| ATOM | 3489 | C5 | G | C | 15 | 28.332 | 133.596 | 268.430 | 1.00 | 0.00 | C |
| ATOM | 3490 | C6 | G | C | 15 | 27.269 | 134.468 | 267.982 | 1.00 | 0.00 | C |
| ATOM | 3491 | O6 | G | C | 15 | 26.509 | 135.181 | 268.655 | 1.00 | 0.00 | O |
| ATOM | 3492 | N1 | G | C | 15 | 27.137 | 134.445 | 266.602 | 1.00 | 0.00 | N |
| ATOM | 3493 | C2 | G | C | 15 | 27.907 | 133.707 | 265.744 | 1.00 | 0.00 | C |
| ATOM | 3494 | N2 | G | C | 15 | 27.609 | 133.851 | 264.454 | 1.00 | 0.00 | N |
| ATOM | 3495 | N3 | G | C | 15 | 28.901 | 132.895 | 266.129 | 1.00 | 0.00 | N |
| ATOM | 3496 | C4 | G | C | 15 | 29.049 | 132.886 | 267.478 | 1.00 | 0.00 | C |
| HETATM | 3497 | P | H2U | C | 16 | 34.690 | 134.419 | 268.343 | 1.00 | 0.00 | P |
| HETATM | 3498 | O1P | H2U | C | 16 | 33.572 | 135.274 | 267.861 | 1.00 | 0.00 | O |
| HETATM | 3499 | O2P | H2U | C | 16 | 35.119 | 134.526 | 269.763 | 1.00 | 0.00 | O |
| HETATM | 3500 | O5* | H2U | C | 16 | 35.928 | 134.694 | 267.363 | 1.00 | 0.00 | O |
| HETATM | 3501 | C5* | H2U | C | 16 | 35.729 | 134.625 | 265.940 | 1.00 | 0.00 | C |
| HETATM | 3502 | C4* | H2U | C | 16 | 37.017 | 134.275 | 265.221 | 1.00 | 0.00 | C |
| HETATM | 3503 | O4* | H2U | C | 16 | 37.984 | 135.320 | 265.469 | 1.00 | 0.00 | O |
| HETATM | 3504 | C3* | H2U | C | 16 | 37.724 | 133.029 | 265.721 | 1.00 | 0.00 | C |
| HETATM | 3505 | O3* | H2U | C | 16 | 38.536 | 132.428 | 264.679 | 1.00 | 0.00 | O |
| HETATM | 3506 | C1* | H2U | C | 16 | 38.742 | 134.993 | 266.620 | 1.00 | 0.00 | C |
| HETATM | 3507 | C2* | H2U | C | 16 | 38.394 | 133.544 | 266.995 | 1.00 | 0.00 | C |
| HETATM | 3508 | O2* | H2U | C | 16 | 39.496 | 132.795 | 267.458 | 1.00 | 0.00 | O |
| HETATM | 3509 | N1 | H2U | C | 16 | 38.413 | 135.982 | 267.658 | 1.00 | 0.00 | N |
| HETATM | 3510 | C2 | H2U | C | 16 | 38.284 | 137.302 | 267.246 | 1.00 | 0.00 | C |
| HETATM | 3511 | O2 | H2U | C | 16 | 38.265 | 137.621 | 266.069 | 1.00 | 0.00 | O |
| HETATM | 3512 | N3 | H2U | C | 16 | 38.181 | 138.239 | 268.245 | 1.00 | 0.00 | N |
| HETATM | 3513 | C4 | H2U | C | 16 | 38.237 | 138.040 | 269.610 | 1.00 | 0.00 | C |
| HETATM | 3514 | O4 | H2U | C | 16 | 38.108 | 139.007 | 270.364 | 1.00 | 0.00 | O |
| HETATM | 3515 | C5 | H2U | C | 16 | 38.642 | 136.651 | 270.028 | 1.00 | 0.00 | C |
| HETATM | 3516 | C6 | H2U | C | 16 | 38.213 | 135.579 | 269.063 | 1.00 | 0.00 | C |
| HETATM | 3517 | P | H2U | C | 17 | 40.096 | 132.827 | 264.483 | 1.00 | 0.00 | P |
| HETATM | 3518 | O1P | H2U | C | 17 | 40.706 | 133.392 | 265.705 | 1.00 | 0.00 | O |
| HETATM | 3519 | O2P | H2U | C | 17 | 40.760 | 131.683 | 263.805 | 1.00 | 0.00 | O |
| HETATM | 3520 | O5* | H2U | C | 17 | 40.064 | 134.026 | 263.444 | 1.00 | 0.00 | O |
| HETATM | 3521 | C5* | H2U | C | 17 | 40.869 | 135.186 | 263.656 | 1.00 | 0.00 | C |
| HETATM | 3522 | C4* | H2U | C | 17 | 40.895 | 136.035 | 262.404 | 1.00 | 0.00 | C |
| HETATM | 3523 | O4* | H2U | C | 17 | 41.645 | 135.327 | 261.374 | 1.00 | 0.00 | O |
| HETATM | 3524 | C3* | H2U | C | 17 | 39.519 | 136.335 | 261.802 | 1.00 | 0.00 | C |
| HETATM | 3525 | O3* | H2U | C | 17 | 39.494 | 137.706 | 261.420 | 1.00 | 0.00 | O |
| HETATM | 3526 | C1* | H2U | C | 17 | 40.895 | 135.301 | 260.187 | 1.00 | 0.00 | C |
| HETATM | 3527 | C2* | H2U | C | 17 | 39.435 | 135.358 | 260.622 | 1.00 | 0.00 | C |
| HETATM | 3528 | O2* | H2U | C | 17 | 38.636 | 135.740 | 259.506 | 1.00 | 0.00 | O |
| HETATM | 3529 | N1 | H2U | C | 17 | 41.264 | 134.104 | 259.423 | 1.00 | 0.00 | N |
| HETATM | 3530 | C2 | H2U | C | 17 | 42.094 | 134.316 | 258.340 | 1.00 | 0.00 | C |
| HETATM | 3531 | O2 | H2U | C | 17 | 42.302 | 135.428 | 257.893 | 1.00 | 0.00 | O |
| HETATM | 3532 | N3 | H2U | C | 17 | 42.678 | 133.198 | 257.804 | 1.00 | 0.00 | N |
| HETATM | 3533 | C4 | H2U | C | 17 | 42.554 | 131.900 | 258.228 | 1.00 | 0.00 | C |
| HETATM | 3534 | O4 | H2U | C | 17 | 43.088 | 130.997 | 257.571 | 1.00 | 0.00 | O |
| HETATM | 3535 | C5 | H2U | C | 17 | 41.883 | 131.744 | 259.585 | 1.00 | 0.00 | C |
| HETATM | 3536 | C6 | H2U | C | 17 | 40.812 | 132.757 | 259.811 | 1.00 | 0.00 | C |
| ATOM | 3537 | P | G | C | 18 | 38.778 | 138.767 | 262.372 | 1.00 | 0.00 | P |
| ATOM | 3538 | O1P | G | C | 18 | 39.137 | 140.153 | 262.049 | 1.00 | 0.00 | O |
| ATOM | 3539 | O2P | G | C | 18 | 38.976 | 138.263 | 263.743 | 1.00 | 0.00 | O |
| ATOM | 3540 | O5* | G | C | 18 | 37.254 | 138.539 | 262.011 | 1.00 | 0.00 | O |
| ATOM | 3541 | C5* | G | C | 18 | 36.562 | 139.508 | 261.330 | 1.00 | 0.00 | C |
| ATOM | 3542 | C4* | G | C | 18 | 35.705 | 138.892 | 260.256 | 1.00 | 0.00 | C |
| ATOM | 3543 | O4* | G | C | 18 | 35.135 | 140.093 | 259.707 | 1.00 | 0.00 | O |
| ATOM | 3544 | C3* | G | C | 18 | 36.471 | 138.250 | 259.084 | 1.00 | 0.00 | C |
| ATOM | 3545 | O3* | G | C | 18 | 35.615 | 137.628 | 258.109 | 1.00 | 0.00 | O |

```
ATOM  3546  C2*  G C  18   36.999 139.489 258.397  1.00  0.00           C
ATOM  3547  O2*  G C  18   37.301 139.256 257.028  1.00  0.00           O
ATOM  3548  C1*  G C  18   35.749 140.364 258.470  1.00  0.00           C
ATOM  3549  N9   G C  18   36.052 141.783 258.392  1.00  0.00           N
ATOM  3550  C8   G C  18   37.190 142.426 258.814  1.00  0.00           C
ATOM  3551  N7   G C  18   37.207 143.690 258.477  1.00  0.00           N
ATOM  3552  C5   G C  18   35.998 143.878 257.834  1.00  0.00           C
ATOM  3553  C6   G C  18   35.480 145.004 257.215  1.00  0.00           C
ATOM  3554  O6   G C  18   36.000 146.103 257.108  1.00  0.00           O
ATOM  3555  N1   G C  18   34.219 144.761 256.660  1.00  0.00           N
ATOM  3556  C2   G C  18   33.568 143.574 256.696  1.00  0.00           C
ATOM  3557  N2   G C  18   32.357 143.538 256.119  1.00  0.00           N
ATOM  3558  N3   G C  18   34.065 142.485 257.264  1.00  0.00           N
ATOM  3559  C4   G C  18   35.267 142.713 257.803  1.00  0.00           C
ATOM  3560  P    G C  19   35.278 136.048 258.183  1.00  0.00           P
ATOM  3561  O1P  G C  19   34.469 135.741 259.401  1.00  0.00           O
ATOM  3562  O2P  G C  19   36.492 135.228 257.907  1.00  0.00           O
ATOM  3563  O5*  G C  19   34.338 135.860 256.923  1.00  0.00           O
ATOM  3564  C5*  G C  19   32.972 136.295 256.988  1.00  0.00           C
ATOM  3565  C4*  G C  19   32.300 136.095 255.665  1.00  0.00           C
ATOM  3566  O4*  G C  19   33.091 136.835 254.685  1.00  0.00           O
ATOM  3567  C3*  G C  19   32.276 134.647 255.171  1.00  0.00           C
ATOM  3568  O3*  G C  19   31.218 134.453 254.231  1.00  0.00           O
ATOM  3569  C2*  G C  19   33.619 134.573 254.420  1.00  0.00           C
ATOM  3570  O2*  G C  19   33.638 133.557 253.450  1.00  0.00           O
ATOM  3571  C1*  G C  19   33.662 135.939 253.737  1.00  0.00           C
ATOM  3572  N9   G C  19   34.969 136.504 253.444  1.00  0.00           N
ATOM  3573  C8   G C  19   36.163 136.230 254.069  1.00  0.00           C
ATOM  3574  N7   G C  19   37.116 137.067 253.733  1.00  0.00           N
ATOM  3575  C5   G C  19   36.525 137.912 252.792  1.00  0.00           C
ATOM  3576  C6   G C  19   37.055 139.029 252.068  1.00  0.00           C
ATOM  3577  O6   G C  19   38.172 139.498 252.096  1.00  0.00           O
ATOM  3578  N1   G C  19   36.109 139.607 251.242  1.00  0.00           N
ATOM  3579  C2   G C  19   34.818 139.192 251.101  1.00  0.00           C
ATOM  3580  N2   G C  19   34.070 139.913 250.215  1.00  0.00           N
ATOM  3581  N3   G C  19   34.297 138.158 251.759  1.00  0.00           N
ATOM  3582  C4   G C  19   35.209 137.564 252.582  1.00  0.00           C
ATOM  3583  P    G C  20   29.713 134.020 254.720  1.00  0.00           P
ATOM  3584  O1P  G C  20   28.781 134.348 253.618  1.00  0.00           O
ATOM  3585  O2P  G C  20   29.489 134.627 256.033  1.00  0.00           O
ATOM  3586  O5*  G C  20   29.779 132.440 254.891  1.00  0.00           O
ATOM  3587  C5*  G C  20   29.924 131.551 253.797  1.00  0.00           C
ATOM  3588  C4*  G C  20   29.454 130.161 254.191  1.00  0.00           C
ATOM  3589  O4*  G C  20   30.504 129.453 254.925  1.00  0.00           O
ATOM  3590  C3*  G C  20   28.236 130.148 255.111  1.00  0.00           C
ATOM  3591  O3*  G C  20   27.038 130.057 254.340  1.00  0.00           O
ATOM  3592  C2*  G C  20   28.440 128.899 255.945  1.00  0.00           C
ATOM  3593  O2*  G C  20   28.042 127.707 255.332  1.00  0.00           O
ATOM  3594  C1*  G C  20   29.957 128.852 256.077  1.00  0.00           C
ATOM  3595  N9   G C  20   30.411 129.590 257.248  1.00  0.00           N
ATOM  3596  C8   G C  20   31.233 130.682 257.272  1.00  0.00           C
ATOM  3597  N7   G C  20   31.435 131.133 258.486  1.00  0.00           N
ATOM  3598  C5   G C  20   30.714 130.271 259.294  1.00  0.00           C
ATOM  3599  C6   G C  20   30.540 130.271 260.693  1.00  0.00           C
ATOM  3600  O6   G C  20   31.035 131.029 261.504  1.00  0.00           O
ATOM  3601  N1   G C  20   29.681 129.256 261.111  1.00  0.00           N
ATOM  3602  C2   G C  20   29.078 128.342 260.277  1.00  0.00           C
ATOM  3603  N2   G C  20   28.257 127.422 260.868  1.00  0.00           N
ATOM  3604  N3   G C  20   29.259 128.324 258.964  1.00  0.00           N
ATOM  3605  C4   G C  20   30.077 129.316 258.549  1.00  0.00           C
ATOM  3606  P    A C  21   25.895 131.139 254.589  1.00  0.00           P
ATOM  3607  O1P  A C  21   24.761 130.791 253.725  1.00  0.00           O
ATOM  3608  O2P  A C  21   26.556 132.474 254.445  1.00  0.00           O
ATOM  3609  O5*  A C  21   25.491 130.704 256.058  1.00  0.00           O
ATOM  3610  C5*  A C  21   25.183 131.605 257.044  1.00  0.00           C
ATOM  3611  C4*  A C  21   25.475 130.993 258.380  1.00  0.00           C
ATOM  3612  O4*  A C  21   25.341 132.074 259.272  1.00  0.00           O
ATOM  3613  C3*  A C  21   24.657 129.844 259.000  1.00  0.00           C
ATOM  3614  O3*  A C  21   25.195 128.556 258.606  1.00  0.00           O
ATOM  3615  C2*  A C  21   24.943 130.065 260.480  1.00  0.00           C
ATOM  3616  O2*  A C  21   26.206 129.528 260.840  1.00  0.00           O
ATOM  3617  C1*  A C  21   25.068 131.593 260.560  1.00  0.00           C
ATOM  3618  N9   A C  21   23.893 132.322 260.983  1.00  0.00           N
ATOM  3619  C8   A C  21   22.946 132.847 260.161  1.00  0.00           C
ATOM  3620  N7   A C  21   22.048 133.558 260.788  1.00  0.00           N
ATOM  3621  C5   A C  21   22.421 133.466 262.112  1.00  0.00           C
ATOM  3622  C6   A C  21   21.856 133.972 263.270  1.00  0.00           C
ATOM  3623  N6   A C  21   20.760 134.737 263.269  1.00  0.00           N
ATOM  3624  N1   A C  21   22.441 133.674 264.436  1.00  0.00           N
ATOM  3625  C2   A C  21   23.540 132.915 264.418  1.00  0.00           C
ATOM  3626  N3   A C  21   24.172 132.381 263.382  1.00  0.00           N
ATOM  3627  C4   A C  21   23.547 132.695 262.249  1.00  0.00           C
ATOM  3628  P    G C  22   24.544 127.150 259.131  1.00  0.00           P
ATOM  3629  O1P  G C  22   25.062 126.051 258.319  1.00  0.00           O
ATOM  3630  O2P  G C  22   23.086 127.260 259.349  1.00  0.00           O
ATOM  3631  O5*  G C  22   25.160 126.967 260.568  1.00  0.00           O
ATOM  3632  C5*  G C  22   24.498 126.202 261.551  1.00  0.00           C
```

```
ATOM   3633  C4*  G C 22    25.487 125.819 262.623  1.00  0.00           C
ATOM   3634  O4*  G C 22    26.046 127.031 263.198  1.00  0.00           O
ATOM   3635  C3*  G C 22    24.923 125.024 263.784  1.00  0.00           C
ATOM   3636  O3*  G C 22    24.952 123.625 263.478  1.00  0.00           O
ATOM   3637  C2*  G C 22    25.837 125.447 264.923  1.00  0.00           C
ATOM   3638  O2*  G C 22    27.093 124.808 264.989  1.00  0.00           O
ATOM   3639  C1*  G C 22    26.061 126.923 264.603  1.00  0.00           C
ATOM   3640  N9   G C 22    24.994 127.757 265.143  1.00  0.00           N
ATOM   3641  C8   G C 22    24.081 128.505 264.442  1.00  0.00           C
ATOM   3642  N7   G C 22    23.288 129.189 265.221  1.00  0.00           N
ATOM   3643  C5   G C 22    23.694 128.852 266.508  1.00  0.00           C
ATOM   3644  C6   G C 22    23.215 129.301 267.758  1.00  0.00           C
ATOM   3645  O6   G C 22    22.310 130.098 267.973  1.00  0.00           O
ATOM   3646  N1   G C 22    23.909 128.729 268.816  1.00  0.00           N
ATOM   3647  C2   G C 22    24.947 127.836 268.681  1.00  0.00           C
ATOM   3648  N2   G C 22    25.505 127.393 269.816  1.00  0.00           N
ATOM   3649  N3   G C 22    25.401 127.416 267.520  1.00  0.00           N
ATOM   3650  C4   G C 22    24.727 127.966 266.480  1.00  0.00           C
ATOM   3651  P    A C 23    23.821 122.645 264.082  1.00  0.00           P
ATOM   3652  O1P  A C 23    23.835 121.338 263.386  1.00  0.00           O
ATOM   3653  O2P  A C 23    22.572 123.434 264.106  1.00  0.00           O
ATOM   3654  O5*  A C 23    24.293 122.414 265.571  1.00  0.00           O
ATOM   3655  C5*  A C 23    25.550 121.834 265.830  1.00  0.00           C
ATOM   3656  C4*  A C 23    25.780 121.716 267.310  1.00  0.00           C
ATOM   3657  O4*  A C 23    26.031 123.014 267.907  1.00  0.00           O
ATOM   3658  C3*  A C 23    24.634 121.133 268.117  1.00  0.00           C
ATOM   3659  O3*  A C 23    24.735 119.714 268.061  1.00  0.00           O
ATOM   3660  C2*  A C 23    24.994 121.623 269.504  1.00  0.00           C
ATOM   3661  O2*  A C 23    26.059 120.845 270.022  1.00  0.00           O
ATOM   3662  C1*  A C 23    25.460 123.052 269.200  1.00  0.00           C
ATOM   3663  N9   A C 23    24.343 123.997 269.148  1.00  0.00           N
ATOM   3664  C8   A C 23    23.710 124.469 268.022  1.00  0.00           C
ATOM   3665  N7   A C 23    22.779 125.359 268.273  1.00  0.00           N
ATOM   3666  C5   A C 23    22.782 125.450 269.658  1.00  0.00           C
ATOM   3667  C6   A C 23    22.004 126.190 270.537  1.00  0.00           C
ATOM   3668  N6   A C 23    21.051 127.037 270.130  1.00  0.00           N
ATOM   3669  N1   A C 23    22.232 126.044 271.857  1.00  0.00           N
ATOM   3670  C2   A C 23    23.197 125.196 272.252  1.00  0.00           C
ATOM   3671  N3   A C 23    23.997 124.440 271.517  1.00  0.00           N
ATOM   3672  C4   A C 23    23.733 124.614 270.209  1.00  0.00           C
ATOM   3673  P    G C 24    23.405 118.805 268.199  1.00  0.00           P
ATOM   3674  O1P  G C 24    23.889 117.453 267.863  1.00  0.00           O
ATOM   3675  O2P  G C 24    22.310 119.411 267.408  1.00  0.00           O
ATOM   3676  O5*  G C 24    23.053 118.925 269.742  1.00  0.00           O
ATOM   3677  C5*  G C 24    24.040 118.657 270.710  1.00  0.00           C
ATOM   3678  C4*  G C 24    23.510 118.951 272.079  1.00  0.00           C
ATOM   3679  O4*  G C 24    23.689 120.367 272.325  1.00  0.00           O
ATOM   3680  C3*  G C 24    22.019 118.714 272.272  1.00  0.00           C
ATOM   3681  O3*  G C 24    21.797 117.364 272.663  1.00  0.00           O
ATOM   3682  C2*  G C 24    21.735 119.657 273.427  1.00  0.00           C
ATOM   3683  O2*  G C 24    22.274 119.177 274.639  1.00  0.00           O
ATOM   3684  C1*  G C 24    22.566 120.874 273.009  1.00  0.00           C
ATOM   3685  N9   G C 24    21.828 121.719 272.087  1.00  0.00           N
ATOM   3686  C8   G C 24    21.824 121.663 270.718  1.00  0.00           C
ATOM   3687  N7   G C 24    20.985 122.504 270.177  1.00  0.00           N
ATOM   3688  C5   G C 24    20.430 123.169 271.265  1.00  0.00           C
ATOM   3689  C6   G C 24    19.436 124.173 271.313  1.00  0.00           C
ATOM   3690  O6   G C 24    18.844 124.723 270.367  1.00  0.00           O
ATOM   3691  N1   G C 24    19.136 124.528 272.626  1.00  0.00           N
ATOM   3692  C2   G C 24    19.718 123.988 273.746  1.00  0.00           C
ATOM   3693  N2   G C 24    19.285 124.449 274.928  1.00  0.00           N
ATOM   3694  N3   G C 24    20.659 123.057 273.709  1.00  0.00           N
ATOM   3695  C4   G C 24    20.956 122.698 272.444  1.00  0.00           C
ATOM   3696  P    C C 25    20.450 116.609 272.204  1.00  0.00           P
ATOM   3697  O1P  C C 25    20.548 115.215 272.737  1.00  0.00           O
ATOM   3698  O2P  C C 25    20.238 116.821 270.769  1.00  0.00           O
ATOM   3699  O5*  C C 25    19.297 117.383 272.980  1.00  0.00           O
ATOM   3700  C5*  C C 25    19.316 117.472 274.390  1.00  0.00           C
ATOM   3701  C4*  C C 25    18.285 118.464 274.872  1.00  0.00           C
ATOM   3702  O4*  C C 25    18.688 119.823 274.528  1.00  0.00           O
ATOM   3703  C3*  C C 25    16.875 118.367 274.302  1.00  0.00           C
ATOM   3704  O3*  C C 25    16.140 117.302 274.905  1.00  0.00           O
ATOM   3705  C2*  C C 25    16.329 119.732 274.714  1.00  0.00           C
ATOM   3706  O2*  C C 25    16.096 119.808 276.107  1.00  0.00           O
ATOM   3707  C1*  C C 25    17.529 120.632 274.397  1.00  0.00           C
ATOM   3708  N1   C C 25    17.472 121.126 273.027  1.00  0.00           N
ATOM   3709  C2   C C 25    16.672 122.221 272.758  1.00  0.00           C
ATOM   3710  O2   C C 25    16.063 122.746 273.694  1.00  0.00           O
ATOM   3711  N3   C C 25    16.578 122.681 271.490  1.00  0.00           N
ATOM   3712  C4   C C 25    17.251 122.079 270.510  1.00  0.00           C
ATOM   3713  N4   C C 25    17.125 122.566 269.271  1.00  0.00           N
ATOM   3714  C5   C C 25    18.087 120.952 270.757  1.00  0.00           C
ATOM   3715  C6   C C 25    18.174 120.514 272.027  1.00  0.00           C
HETATM 3716  P    M2G C 26   14.647 116.174 273.907  1.00  0.00           P
HETATM 3717  O1P  M2G C 26   14.713 115.473 272.608  1.00  0.00           O
HETATM 3718  O2P  M2G C 26   13.903 115.561 275.031  1.00  0.00           O
HETATM 3719  O5*  M2G C 26   14.041 117.622 273.660  1.00  0.00           O
```

| | | | | | | | | | | |
|---|---|---|---|---|---|---|---|---|---|---|
| HETATM | 3720 | C5* | M2G | C | 26 | 13.434 | 118.341 | 274.724 | 1.00 | 0.00 | C |
| HETATM | 3721 | C4* | M2G | C | 26 | 12.885 | 119.651 | 274.219 | 1.00 | 0.00 | C |
| HETATM | 3722 | O4* | M2G | C | 26 | 13.925 | 120.389 | 273.509 | 1.00 | 0.00 | O |
| HETATM | 3723 | C3* | M2G | C | 26 | 11.790 | 119.522 | 273.181 | 1.00 | 0.00 | C |
| HETATM | 3724 | O3* | M2G | C | 26 | 10.542 | 119.282 | 273.808 | 1.00 | 0.00 | O |
| HETATM | 3725 | C2* | M2G | C | 26 | 11.829 | 120.898 | 272.536 | 1.00 | 0.00 | C |
| HETATM | 3726 | O2* | M2G | C | 26 | 11.288 | 121.889 | 273.381 | 1.00 | 0.00 | O |
| HETATM | 3727 | C1* | M2G | C | 26 | 13.338 | 121.107 | 272.427 | 1.00 | 0.00 | C |
| HETATM | 3728 | N9 | M2G | C | 26 | 13.904 | 120.602 | 271.178 | 1.00 | 0.00 | N |
| HETATM | 3729 | C8 | M2G | C | 26 | 14.595 | 119.425 | 270.988 | 1.00 | 0.00 | C |
| HETATM | 3730 | N7 | M2G | C | 26 | 14.988 | 119.254 | 269.759 | 1.00 | 0.00 | N |
| HETATM | 3731 | C5 | M2G | C | 26 | 14.536 | 120.392 | 269.103 | 1.00 | 0.00 | C |
| HETATM | 3732 | C6 | M2G | C | 26 | 14.675 | 120.775 | 267.757 | 1.00 | 0.00 | C |
| HETATM | 3733 | O6 | M2G | C | 26 | 15.245 | 120.164 | 266.845 | 1.00 | 0.00 | O |
| HETATM | 3734 | N1 | M2G | C | 26 | 14.065 | 121.998 | 267.505 | 1.00 | 0.00 | N |
| HETATM | 3735 | C2 | M2G | C | 26 | 13.399 | 122.757 | 268.446 | 1.00 | 0.00 | C |
| HETATM | 3736 | N2 | M2G | C | 26 | 12.834 | 123.889 | 268.015 | 1.00 | 0.00 | N |
| HETATM | 3737 | N3 | M2G | C | 26 | 13.268 | 122.410 | 269.714 | 1.00 | 0.00 | N |
| HETATM | 3738 | C4 | M2G | C | 26 | 13.857 | 121.221 | 269.969 | 1.00 | 0.00 | C |
| HETATM | 3739 | CM1 | M2G | C | 26 | 11.828 | 124.572 | 268.852 | 1.00 | 0.00 | C |
| HETATM | 3740 | CM2 | M2G | C | 26 | 13.214 | 124.450 | 266.714 | 1.00 | 0.00 | C |
| ATOM | 3741 | P | C | C | 27 | 9.559 | 118.172 | 273.199 | 1.00 | 0.00 | P |
| ATOM | 3742 | O1P | C | C | 27 | 8.411 | 118.026 | 274.136 | 1.00 | 0.00 | O |
| ATOM | 3743 | O2P | C | C | 27 | 10.388 | 116.981 | 272.868 | 1.00 | 0.00 | O |
| ATOM | 3744 | O5* | C | C | 27 | 9.023 | 118.830 | 271.849 | 1.00 | 0.00 | O |
| ATOM | 3745 | C5* | C | C | 27 | 8.295 | 120.045 | 271.882 | 1.00 | 0.00 | C |
| ATOM | 3746 | C4* | C | C | 27 | 8.078 | 120.573 | 270.484 | 1.00 | 0.00 | C |
| ATOM | 3747 | O4* | C | C | 27 | 9.353 | 120.995 | 269.924 | 1.00 | 0.00 | O |
| ATOM | 3748 | C3* | C | C | 27 | 7.546 | 119.592 | 269.449 | 1.00 | 0.00 | C |
| ATOM | 3749 | O3* | C | C | 27 | 6.129 | 119.436 | 269.523 | 1.00 | 0.00 | O |
| ATOM | 3750 | C2* | C | C | 27 | 7.943 | 120.297 | 268.154 | 1.00 | 0.00 | C |
| ATOM | 3751 | O2* | C | C | 27 | 7.091 | 121.383 | 267.839 | 1.00 | 0.00 | O |
| ATOM | 3752 | C1* | C | C | 27 | 9.338 | 120.815 | 268.513 | 1.00 | 0.00 | C |
| ATOM | 3753 | N1 | C | C | 27 | 10.421 | 119.885 | 268.145 | 1.00 | 0.00 | N |
| ATOM | 3754 | C2 | C | C | 27 | 10.835 | 119.820 | 266.806 | 1.00 | 0.00 | C |
| ATOM | 3755 | O2 | C | C | 27 | 10.257 | 120.516 | 265.961 | 1.00 | 0.00 | O |
| ATOM | 3756 | N3 | C | C | 27 | 11.849 | 118.990 | 266.462 | 1.00 | 0.00 | N |
| ATOM | 3757 | C4 | C | C | 27 | 12.432 | 118.236 | 267.389 | 1.00 | 0.00 | C |
| ATOM | 3758 | N4 | C | C | 27 | 13.419 | 117.436 | 266.997 | 1.00 | 0.00 | N |
| ATOM | 3759 | C5 | C | C | 27 | 12.022 | 118.268 | 268.761 | 1.00 | 0.00 | C |
| ATOM | 3760 | C6 | C | C | 27 | 11.021 | 119.102 | 269.091 | 1.00 | 0.00 | C |
| ATOM | 3761 | P | C | C | 28 | 5.454 | 118.019 | 269.148 | 1.00 | 0.00 | P |
| ATOM | 3762 | O1P | C | C | 28 | 4.027 | 118.155 | 269.515 | 1.00 | 0.00 | O |
| ATOM | 3763 | O2P | C | C | 28 | 6.258 | 116.912 | 269.723 | 1.00 | 0.00 | O |
| ATOM | 3764 | O5* | C | C | 28 | 5.543 | 117.900 | 267.563 | 1.00 | 0.00 | O |
| ATOM | 3765 | C5* | C | C | 28 | 4.718 | 118.700 | 266.738 | 1.00 | 0.00 | C |
| ATOM | 3766 | C4* | C | C | 28 | 5.074 | 118.494 | 265.290 | 1.00 | 0.00 | C |
| ATOM | 3767 | O4* | C | C | 28 | 6.450 | 118.906 | 265.079 | 1.00 | 0.00 | O |
| ATOM | 3768 | C3* | C | C | 28 | 5.074 | 117.062 | 264.794 | 1.00 | 0.00 | C |
| ATOM | 3769 | O3* | C | C | 28 | 3.762 | 116.609 | 264.477 | 1.00 | 0.00 | O |
| ATOM | 3770 | C2* | C | C | 28 | 5.919 | 117.199 | 263.542 | 1.00 | 0.00 | C |
| ATOM | 3771 | O2* | C | C | 28 | 5.213 | 117.840 | 262.493 | 1.00 | 0.00 | O |
| ATOM | 3772 | C1* | C | C | 28 | 7.029 | 118.107 | 264.068 | 1.00 | 0.00 | C |
| ATOM | 3773 | N1 | C | C | 28 | 8.146 | 117.364 | 264.664 | 1.00 | 0.00 | N |
| ATOM | 3774 | C2 | C | C | 28 | 9.089 | 116.805 | 263.811 | 1.00 | 0.00 | C |
| ATOM | 3775 | O2 | C | C | 28 | 8.929 | 116.943 | 262.595 | 1.00 | 0.00 | O |
| ATOM | 3776 | N3 | C | C | 28 | 10.144 | 116.127 | 264.329 | 1.00 | 0.00 | N |
| ATOM | 3777 | C4 | C | C | 28 | 10.267 | 115.993 | 265.653 | 1.00 | 0.00 | C |
| ATOM | 3778 | N4 | C | C | 28 | 11.338 | 115.304 | 266.127 | 1.00 | 0.00 | N |
| ATOM | 3779 | C5 | C | C | 28 | 9.307 | 116.550 | 266.555 | 1.00 | 0.00 | C |
| ATOM | 3780 | C6 | C | C | 28 | 8.272 | 117.223 | 266.020 | 1.00 | 0.00 | C |
| ATOM | 3781 | P | A | C | 29 | 3.391 | 115.065 | 264.703 | 1.00 | 0.00 | P |
| ATOM | 3782 | O1P | A | C | 29 | 1.911 | 114.951 | 264.561 | 1.00 | 0.00 | O |
| ATOM | 3783 | O2P | A | C | 29 | 4.054 | 114.580 | 265.952 | 1.00 | 0.00 | O |
| ATOM | 3784 | O5* | A | C | 29 | 4.084 | 114.308 | 263.484 | 1.00 | 0.00 | O |
| ATOM | 3785 | C5* | A | C | 29 | 3.792 | 114.674 | 262.134 | 1.00 | 0.00 | C |
| ATOM | 3786 | C4* | A | C | 29 | 4.819 | 114.082 | 261.177 | 1.00 | 0.00 | C |
| ATOM | 3787 | O4* | A | C | 29 | 6.121 | 114.698 | 261.370 | 1.00 | 0.00 | O |
| ATOM | 3788 | C3* | A | C | 29 | 5.091 | 112.585 | 261.257 | 1.00 | 0.00 | C |
| ATOM | 3789 | O3* | A | C | 29 | 4.110 | 111.865 | 260.517 | 1.00 | 0.00 | O |
| ATOM | 3790 | C2* | A | C | 29 | 6.451 | 112.484 | 260.572 | 1.00 | 0.00 | C |
| ATOM | 3791 | O2* | A | C | 29 | 6.375 | 112.515 | 259.155 | 1.00 | 0.00 | O |
| ATOM | 3792 | C1* | A | C | 29 | 7.144 | 113.746 | 261.093 | 1.00 | 0.00 | C |
| ATOM | 3793 | N9 | A | C | 29 | 7.906 | 113.507 | 262.324 | 1.00 | 0.00 | N |
| ATOM | 3794 | C8 | A | C | 29 | 7.569 | 113.830 | 263.619 | 1.00 | 0.00 | C |
| ATOM | 3795 | N7 | A | C | 29 | 8.472 | 113.472 | 264.505 | 1.00 | 0.00 | N |
| ATOM | 3796 | C5 | A | C | 29 | 9.469 | 112.879 | 263.739 | 1.00 | 0.00 | C |
| ATOM | 3797 | C6 | A | C | 29 | 10.691 | 112.288 | 264.078 | 1.00 | 0.00 | C |
| ATOM | 3798 | N6 | A | C | 29 | 11.158 | 112.203 | 265.324 | 1.00 | 0.00 | N |
| ATOM | 3799 | N1 | A | C | 29 | 11.438 | 111.778 | 263.076 | 1.00 | 0.00 | N |
| ATOM | 3800 | C2 | A | C | 29 | 10.977 | 111.868 | 261.823 | 1.00 | 0.00 | C |
| ATOM | 3801 | N3 | A | C | 29 | 9.851 | 112.400 | 261.380 | 1.00 | 0.00 | N |
| ATOM | 3802 | C4 | A | C | 29 | 9.131 | 112.895 | 262.399 | 1.00 | 0.00 | C |
| ATOM | 3803 | P | G | C | 30 | 3.866 | 110.306 | 260.816 | 1.00 | 0.00 | P |
| ATOM | 3804 | O1P | G | C | 30 | 2.679 | 109.925 | 260.000 | 1.00 | 0.00 | O |
| ATOM | 3805 | O2P | G | C | 30 | 3.848 | 110.094 | 262.285 | 1.00 | 0.00 | O |
| ATOM | 3806 | O5* | G | C | 30 | 5.158 | 109.583 | 260.215 | 1.00 | 0.00 | O |

| | | | | | | | | | | |
|---|---|---|---|---|---|---|---|---|---|---|
| ATOM | 3807 | C5* | G | C | 30 | 5.500 | 109.715 | 258.835 | 1.00 | 0.00 | C |
| ATOM | 3808 | C4* | G | C | 30 | 6.712 | 108.871 | 258.520 | 1.00 | 0.00 | C |
| ATOM | 3809 | O4* | G | C | 30 | 7.917 | 109.528 | 258.996 | 1.00 | 0.00 | O |
| ATOM | 3810 | C3* | G | C | 30 | 6.744 | 107.529 | 259.220 | 1.00 | 0.00 | C |
| ATOM | 3811 | O3* | G | C | 30 | 5.949 | 106.587 | 258.515 | 1.00 | 0.00 | O |
| ATOM | 3812 | C2* | G | C | 30 | 8.232 | 107.195 | 259.198 | 1.00 | 0.00 | C |
| ATOM | 3813 | O2* | G | C | 30 | 8.747 | 106.758 | 257.954 | 1.00 | 0.00 | O |
| ATOM | 3814 | C1* | G | C | 30 | 8.826 | 108.560 | 259.508 | 1.00 | 0.00 | C |
| ATOM | 3815 | N9 | G | C | 30 | 8.920 | 108.739 | 260.946 | 1.00 | 0.00 | N |
| ATOM | 3816 | C8 | G | C | 30 | 7.995 | 109.335 | 261.760 | 1.00 | 0.00 | C |
| ATOM | 3817 | N7 | G | C | 30 | 8.357 | 109.356 | 263.014 | 1.00 | 0.00 | N |
| ATOM | 3818 | C5 | G | C | 30 | 9.599 | 108.735 | 263.028 | 1.00 | 0.00 | C |
| ATOM | 3819 | C6 | G | C | 30 | 10.499 | 108.492 | 264.108 | 1.00 | 0.00 | C |
| ATOM | 3820 | O6 | G | C | 30 | 10.361 | 108.781 | 265.306 | 1.00 | 0.00 | O |
| ATOM | 3821 | N1 | G | C | 30 | 11.658 | 107.847 | 263.677 | 1.00 | 0.00 | N |
| ATOM | 3822 | C2 | G | C | 30 | 11.922 | 107.488 | 262.374 | 1.00 | 0.00 | C |
| ATOM | 3823 | N2 | G | C | 30 | 13.097 | 106.863 | 262.160 | 1.00 | 0.00 | N |
| ATOM | 3824 | N3 | G | C | 30 | 11.097 | 107.720 | 261.358 | 1.00 | 0.00 | N |
| ATOM | 3825 | C4 | G | C | 30 | 9.960 | 108.342 | 261.759 | 1.00 | 0.00 | C |
| ATOM | 3826 | P | A | C | 31 | 5.558 | 105.196 | 259.215 | 1.00 | 0.00 | P |
| ATOM | 3827 | O1P | A | C | 31 | 4.932 | 104.357 | 258.165 | 1.00 | 0.00 | O |
| ATOM | 3828 | O2P | A | C | 31 | 4.806 | 105.486 | 260.467 | 1.00 | 0.00 | O |
| ATOM | 3829 | O5* | A | C | 31 | 6.955 | 104.547 | 259.600 | 1.00 | 0.00 | O |
| ATOM | 3830 | C5* | A | C | 31 | 7.806 | 104.029 | 258.590 | 1.00 | 0.00 | C |
| ATOM | 3831 | C4* | A | C | 31 | 9.000 | 103.370 | 259.217 | 1.00 | 0.00 | C |
| ATOM | 3832 | O4* | A | C | 31 | 9.820 | 104.390 | 259.845 | 1.00 | 0.00 | O |
| ATOM | 3833 | C3* | A | C | 31 | 8.677 | 102.388 | 260.338 | 1.00 | 0.00 | C |
| ATOM | 3834 | O3* | A | C | 31 | 8.438 | 101.078 | 259.815 | 1.00 | 0.00 | O |
| ATOM | 3835 | C2* | A | C | 31 | 9.970 | 102.416 | 261.141 | 1.00 | 0.00 | C |
| ATOM | 3836 | O2* | A | C | 31 | 10.988 | 101.630 | 260.551 | 1.00 | 0.00 | O |
| ATOM | 3837 | C1* | A | C | 31 | 10.329 | 103.903 | 261.074 | 1.00 | 0.00 | C |
| ATOM | 3838 | N9 | A | C | 31 | 9.684 | 104.632 | 262.156 | 1.00 | 0.00 | N |
| ATOM | 3839 | C8 | A | C | 31 | 8.478 | 105.288 | 262.155 | 1.00 | 0.00 | C |
| ATOM | 3840 | N7 | A | C | 31 | 8.159 | 105.806 | 263.313 | 1.00 | 0.00 | N |
| ATOM | 3841 | C5 | A | C | 31 | 9.231 | 105.482 | 264.128 | 1.00 | 0.00 | C |
| ATOM | 3842 | C6 | A | C | 31 | 9.508 | 105.759 | 265.474 | 1.00 | 0.00 | C |
| ATOM | 3843 | N6 | A | C | 31 | 8.680 | 106.449 | 266.270 | 1.00 | 0.00 | N |
| ATOM | 3844 | N1 | A | C | 31 | 10.678 | 105.304 | 265.983 | 1.00 | 0.00 | N |
| ATOM | 3845 | C2 | A | C | 31 | 11.504 | 104.620 | 265.176 | 1.00 | 0.00 | C |
| ATOM | 3846 | N3 | A | C | 31 | 11.353 | 104.296 | 263.890 | 1.00 | 0.00 | N |
| ATOM | 3847 | C4 | A | C | 31 | 10.181 | 104.764 | 263.425 | 1.00 | 0.00 | C |
| HETATM | 3848 | N1 | OMC | C | 32 | 8.170 | 101.739 | 265.293 | 1.00 | 0.00 | N |
| HETATM | 3849 | C2 | OMC | C | 32 | 8.074 | 102.643 | 266.331 | 1.00 | 0.00 | C |
| HETATM | 3850 | N3 | OMC | C | 32 | 7.173 | 103.650 | 266.253 | 1.00 | 0.00 | N |
| HETATM | 3851 | C4 | OMC | C | 32 | 6.398 | 103.766 | 265.171 | 1.00 | 0.00 | C |
| HETATM | 3852 | C5 | OMC | C | 32 | 6.497 | 102.860 | 264.077 | 1.00 | 0.00 | C |
| HETATM | 3853 | C6 | OMC | C | 32 | 7.391 | 101.871 | 264.179 | 1.00 | 0.00 | C |
| HETATM | 3854 | O2 | OMC | C | 32 | 8.822 | 102.498 | 267.308 | 1.00 | 0.00 | O |
| HETATM | 3855 | N4 | OMC | C | 32 | 5.506 | 104.765 | 265.131 | 1.00 | 0.00 | N |
| HETATM | 3856 | C1* | OMC | C | 32 | 9.108 | 100.632 | 265.426 | 1.00 | 0.00 | C |
| HETATM | 3857 | C2* | OMC | C | 32 | 8.399 | 99.365 | 265.890 | 1.00 | 0.00 | C |
| HETATM | 3858 | O2* | OMC | C | 32 | 9.339 | 98.564 | 266.640 | 1.00 | 0.00 | O |
| HETATM | 3859 | CM2 | OMC | C | 32 | 9.644 | 98.922 | 268.010 | 1.00 | 0.00 | C |
| HETATM | 3860 | C3* | OMC | C | 32 | 8.007 | 98.746 | 264.558 | 1.00 | 0.00 | C |
| HETATM | 3861 | C4* | OMC | C | 32 | 9.227 | 99.043 | 263.708 | 1.00 | 0.00 | C |
| HETATM | 3862 | O4* | OMC | C | 32 | 9.658 | 100.355 | 264.153 | 1.00 | 0.00 | O |
| HETATM | 3863 | O3* | OMC | C | 32 | 7.794 | 97.345 | 264.665 | 1.00 | 0.00 | O |
| HETATM | 3864 | C5* | OMC | C | 32 | 8.959 | 99.099 | 262.231 | 1.00 | 0.00 | C |
| HETATM | 3865 | O5* | OMC | C | 32 | 7.826 | 99.917 | 261.974 | 1.00 | 0.00 | O |
| HETATM | 3866 | P | OMC | C | 32 | 7.314 | 100.136 | 260.482 | 1.00 | 0.00 | P |
| HETATM | 3867 | O1P | OMC | C | 32 | 6.041 | 100.904 | 260.513 | 1.00 | 0.00 | O |
| HETATM | 3868 | O2P | OMC | C | 32 | 7.379 | 98.827 | 259.773 | 1.00 | 0.00 | O |
| ATOM | 3869 | P | U | C | 33 | 6.372 | 96.799 | 265.183 | 1.00 | 0.00 | P |
| ATOM | 3870 | O1P | U | C | 33 | 6.555 | 95.374 | 265.550 | 1.00 | 0.00 | O |
| ATOM | 3871 | O2P | U | C | 33 | 5.321 | 97.185 | 264.201 | 1.00 | 0.00 | O |
| ATOM | 3872 | O5* | U | C | 33 | 6.114 | 97.638 | 266.511 | 1.00 | 0.00 | O |
| ATOM | 3873 | C5* | U | C | 33 | 6.402 | 97.097 | 267.798 | 1.00 | 0.00 | C |
| ATOM | 3874 | C4* | U | C | 33 | 5.452 | 97.677 | 268.821 | 1.00 | 0.00 | C |
| ATOM | 3875 | O4* | U | C | 33 | 5.621 | 99.119 | 268.844 | 1.00 | 0.00 | O |
| ATOM | 3876 | C3* | U | C | 33 | 3.975 | 97.474 | 268.498 | 1.00 | 0.00 | C |
| ATOM | 3877 | O3* | U | C | 33 | 3.506 | 96.223 | 269.011 | 1.00 | 0.00 | O |
| ATOM | 3878 | C2* | U | C | 33 | 3.306 | 98.650 | 269.206 | 1.00 | 0.00 | C |
| ATOM | 3879 | O2* | U | C | 33 | 3.011 | 98.387 | 270.560 | 1.00 | 0.00 | O |
| ATOM | 3880 | C1* | U | C | 33 | 4.374 | 99.741 | 269.096 | 1.00 | 0.00 | C |
| ATOM | 3881 | N1 | U | C | 33 | 4.076 | 100.669 | 268.003 | 1.00 | 0.00 | N |
| ATOM | 3882 | C2 | U | C | 33 | 3.403 | 101.815 | 268.337 | 1.00 | 0.00 | C |
| ATOM | 3883 | O2 | U | C | 33 | 3.119 | 102.084 | 269.487 | 1.00 | 0.00 | O |
| ATOM | 3884 | N3 | U | C | 33 | 3.074 | 102.633 | 267.280 | 1.00 | 0.00 | N |
| ATOM | 3885 | C4 | U | C | 33 | 3.356 | 102.420 | 265.945 | 1.00 | 0.00 | C |
| ATOM | 3886 | O4 | U | C | 33 | 2.971 | 103.241 | 265.102 | 1.00 | 0.00 | O |
| ATOM | 3887 | C5 | U | C | 33 | 4.086 | 101.211 | 265.679 | 1.00 | 0.00 | C |
| ATOM | 3888 | C6 | U | C | 33 | 4.419 | 100.400 | 266.696 | 1.00 | 0.00 | C |
| HETATM | 3889 | P | OMG | C | 34 | 2.652 | 95.106 | 268.984 | 1.00 | 0.00 | P |
| HETATM | 3890 | O1P | OMG | C | 34 | 3.505 | 94.260 | 268.100 | 1.00 | 0.00 | O |
| HETATM | 3891 | O2P | OMG | C | 34 | 1.795 | 94.455 | 270.008 | 1.00 | 0.00 | O |
| HETATM | 3892 | O5* | OMG | C | 34 | 1.728 | 96.047 | 268.085 | 1.00 | 0.00 | O |
| HETATM | 3893 | C5* | OMG | C | 34 | 0.533 | 95.561 | 267.484 | 1.00 | 0.00 | C |

```
HETATM 3894  C4*  OMG C  34   -0.666  96.147 268.183  1.00  0.00           C
HETATM 3895  O4*  OMG C  34   -0.697  95.599 269.518  1.00  0.00           O
HETATM 3896  C3*  OMG C  34   -0.612  97.650 268.405  1.00  0.00           C
HETATM 3897  O3*  OMG C  34   -1.112  98.380 267.277  1.00  0.00           O
HETATM 3898  C2*  OMG C  34   -1.484  97.844 269.648  1.00  0.00           C
HETATM 3899  O2*  OMG C  34   -2.891  98.078 269.390  1.00  0.00           O
HETATM 3900  CM2  OMG C  34   -3.745  98.539 270.466  1.00  0.00           C
HETATM 3901  C1*  OMG C  34   -1.304  96.523 270.393  1.00  0.00           C
HETATM 3902  N9   OMG C  34   -0.490  96.607 271.599  1.00  0.00           N
HETATM 3903  C8   OMG C  34    0.595  95.825 271.921  1.00  0.00           C
HETATM 3904  N7   OMG C  34    1.097  96.094 273.097  1.00  0.00           N
HETATM 3905  C5   OMG C  34    0.300  97.126 273.580  1.00  0.00           C
HETATM 3906  C6   OMG C  34    0.347  97.824 274.826  1.00  0.00           C
HETATM 3907  O6   OMG C  34    1.140  97.668 275.781  1.00  0.00           O
HETATM 3908  N1   OMG C  34   -0.661  98.793 274.904  1.00  0.00           N
HETATM 3909  C2   OMG C  34   -1.595  99.059 273.915  1.00  0.00           C
HETATM 3910  N2   OMG C  34   -2.482 100.039 274.178  1.00  0.00           N
HETATM 3911  N3   OMG C  34   -1.649  98.411 272.756  1.00  0.00           N
HETATM 3912  C4   OMG C  34   -0.680  97.465 272.658  1.00  0.00           C
ATOM   3913  P    A   C  35   -0.252  99.373 266.381  1.00  0.00           P
ATOM   3914  O1P  A   C  35   -0.945  99.752 265.120  1.00  0.00           O
ATOM   3915  O2P  A   C  35    0.757  98.281 266.380  1.00  0.00           O
ATOM   3916  O5*  A   C  35    0.452 100.668 266.983  1.00  0.00           O
ATOM   3917  C5*  A   C  35    0.613 100.794 268.391  1.00  0.00           C
ATOM   3918  C4*  A   C  35   -0.225 101.923 268.944  1.00  0.00           C
ATOM   3919  O4*  A   C  35   -1.027 101.373 270.030  1.00  0.00           O
ATOM   3920  C3*  A   C  35    0.591 103.058 269.569  1.00  0.00           C
ATOM   3921  O3*  A   C  35    0.681 104.157 268.657  1.00  0.00           O
ATOM   3922  C2*  A   C  35   -0.229 103.429 270.804  1.00  0.00           C
ATOM   3923  O2*  A   C  35   -1.321 104.288 270.513  1.00  0.00           O
ATOM   3924  C1*  A   C  35   -0.737 102.058 271.227  1.00  0.00           C
ATOM   3925  N9   A   C  35    0.250 101.270 271.953  1.00  0.00           N
ATOM   3926  C8   A   C  35    0.964 100.184 271.512  1.00  0.00           C
ATOM   3927  N7   A   C  35    1.779  99.690 272.413  1.00  0.00           N
ATOM   3928  C5   A   C  35    1.588 100.503 273.519  1.00  0.00           C
ATOM   3929  C6   A   C  35    2.167 100.509 274.807  1.00  0.00           C
ATOM   3930  N6   A   C  35    3.092  99.637 275.213  1.00  0.00           N
ATOM   3931  N1   A   C  35    1.758 101.465 275.677  1.00  0.00           N
ATOM   3932  C2   A   C  35    0.832 102.346 275.267  1.00  0.00           C
ATOM   3933  N3   A   C  35    0.220 102.443 274.081  1.00  0.00           N
ATOM   3934  C4   A   C  35    0.649 101.482 273.248  1.00  0.00           C
ATOM   3935  P    A   C  36    0.370 105.771 268.205  1.00  0.00           P
ATOM   3936  O1P  A   C  36   -0.763 106.546 267.601  1.00  0.00           O
ATOM   3937  O2P  A   C  36    1.648 105.649 267.475  1.00  0.00           O
ATOM   3938  O5*  A   C  36    0.663 106.371 269.641  1.00  0.00           O
ATOM   3939  C5*  A   C  36    1.993 106.581 270.069  1.00  0.00           C
ATOM   3940  C4*  A   C  36    1.989 107.002 271.512  1.00  0.00           C
ATOM   3941  O4*  A   C  36    1.445 105.923 272.330  1.00  0.00           O
ATOM   3942  C3*  A   C  36    3.361 107.232 272.121  1.00  0.00           C
ATOM   3943  O3*  A   C  36    3.894 108.504 271.772  1.00  0.00           O
ATOM   3944  C2*  A   C  36    3.044 107.103 273.604  1.00  0.00           C
ATOM   3945  O2*  A   C  36    2.352 108.225 274.132  1.00  0.00           O
ATOM   3946  C1*  A   C  36    2.126 105.880 273.578  1.00  0.00           C
ATOM   3947  N9   A   C  36    2.907 104.649 273.623  1.00  0.00           N
ATOM   3948  C8   A   C  36    3.165 103.769 272.607  1.00  0.00           C
ATOM   3949  N7   A   C  36    3.938 102.770 272.957  1.00  0.00           N
ATOM   3950  C5   A   C  36    4.197 103.007 274.300  1.00  0.00           C
ATOM   3951  C6   A   C  36    4.975 102.320 275.251  1.00  0.00           C
ATOM   3952  N6   A   C  36    5.654 101.198 274.988  1.00  0.00           N
ATOM   3953  N1   A   C  36    5.035 102.836 276.500  1.00  0.00           N
ATOM   3954  C2   A   C  36    4.361 103.966 276.759  1.00  0.00           C
ATOM   3955  N3   A   C  36    3.602 104.699 275.951  1.00  0.00           N
ATOM   3956  C4   A   C  36    3.561 104.158 274.723  1.00  0.00           C
HETATM 3957  N1   YG  C  37    9.900 101.763 274.087  1.00  0.00           N
HETATM 3958  N2   YG  C  37   11.021 101.851 276.075  1.00  0.00           N
HETATM 3959  C2   YG  C  37   10.051 102.412 275.269  1.00  0.00           C
HETATM 3960  N3   YG  C  37    9.338 103.505 275.643  1.00  0.00           N
HETATM 3961  C3   YG  C  37    9.545 104.194 276.965  1.00  0.00           C
HETATM 3962  C4   YG  C  37    8.433 103.885 274.672  1.00  0.00           C
HETATM 3963  C5   YG  C  37    8.206 103.293 273.439  1.00  0.00           C
HETATM 3964  C6   YG  C  37    8.975 102.130 273.069  1.00  0.00           C
HETATM 3965  O6   YG  C  37    8.910 101.460 272.028  1.00  0.00           O
HETATM 3966  N7   YG  C  37    7.218 103.976 272.738  1.00  0.00           N
HETATM 3967  C8   YG  C  37    6.867 104.954 273.534  1.00  0.00           C
HETATM 3968  N9   YG  C  37    7.566 104.966 274.721  1.00  0.00           N
HETATM 3969  C10  YG  C  37   12.613  99.828 275.801  1.00  0.00           C
HETATM 3970  C11  YG  C  37   11.526 100.777 275.357  1.00  0.00           C
HETATM 3971  C12  YG  C  37   10.833 100.744 274.158  1.00  0.00           C
HETATM 3972  C13  YG  C  37   11.063  99.698 273.089  1.00  0.00           C
HETATM 3973  C14  YG  C  37   10.595  98.329 273.534  1.00  0.00           C
HETATM 3974  C15  YG  C  37   11.642  97.205 273.479  1.00  0.00           C
HETATM 3975  C16  YG  C  37   10.981  95.849 273.209  1.00  0.00           C
HETATM 3976  O17  YG  C  37   10.098  95.744 272.356  1.00  0.00           O
HETATM 3977  O18  YG  C  37   11.384  94.795 273.958  1.00  0.00           O
HETATM 3978  C19  YG  C  37   12.123  93.677 273.398  1.00  0.00           C
HETATM 3979  N20  YG  C  37   12.431  97.173 274.711  1.00  0.00           N
HETATM 3980  C21  YG  C  37   13.764  97.129 274.737  1.00  0.00           C
```

| | | | | | | | | | |
|---|---|---|---|---|---|---|---|---|---|
| HETATM | 3981 | O22 | YG | C | 37 | 14.439 | 97.213 | 273.705 | 1.00 | 0.00 | O |
| HETATM | 3982 | O23 | YG | C | 37 | 14.384 | 97.001 | 275.935 | 1.00 | 0.00 | O |
| HETATM | 3983 | C24 | YG | C | 37 | 15.820 | 97.108 | 276.098 | 1.00 | 0.00 | C |
| HETATM | 3984 | C1* | YG | C | 37 | 7.428 | 105.940 | 275.804 | 1.00 | 0.00 | C |
| HETATM | 3985 | C2* | YG | C | 37 | 8.652 | 106.850 | 275.975 | 1.00 | 0.00 | C |
| HETATM | 3986 | O2* | YG | C | 37 | 8.919 | 107.074 | 277.346 | 1.00 | 0.00 | O |
| HETATM | 3987 | C3* | YG | C | 37 | 8.204 | 108.108 | 275.244 | 1.00 | 0.00 | C |
| HETATM | 3988 | O3* | YG | C | 37 | 8.887 | 109.253 | 275.729 | 1.00 | 0.00 | O |
| HETATM | 3989 | C4* | YG | C | 37 | 6.737 | 108.167 | 275.610 | 1.00 | 0.00 | C |
| HETATM | 3990 | O4* | YG | C | 37 | 6.325 | 106.781 | 275.507 | 1.00 | 0.00 | O |
| HETATM | 3991 | C5* | YG | C | 37 | 5.891 | 109.011 | 274.698 | 1.00 | 0.00 | C |
| HETATM | 3992 | O5* | YG | C | 37 | 5.874 | 108.449 | 273.393 | 1.00 | 0.00 | O |
| HETATM | 3993 | P | YG | C | 37 | 4.841 | 108.974 | 272.304 | 1.00 | 0.00 | P |
| HETATM | 3994 | O1P | YG | C | 37 | 5.074 | 108.207 | 271.048 | 1.00 | 0.00 | O |
| HETATM | 3995 | O2P | YG | C | 37 | 4.891 | 110.463 | 272.281 | 1.00 | 0.00 | O |
| ATOM | 3996 | P | A | C | 38 | 10.336 | 109.617 | 275.144 | 1.00 | 0.00 | P |
| ATOM | 3997 | O1P | A | C | 38 | 10.979 | 110.568 | 276.085 | 1.00 | 0.00 | O |
| ATOM | 3998 | O2P | A | C | 38 | 10.142 | 109.992 | 273.721 | 1.00 | 0.00 | O |
| ATOM | 3999 | O5* | A | C | 38 | 11.157 | 108.258 | 275.211 | 1.00 | 0.00 | O |
| ATOM | 4000 | C5* | A | C | 38 | 11.966 | 107.972 | 276.334 | 1.00 | 0.00 | C |
| ATOM | 4001 | C4* | A | C | 38 | 12.730 | 106.705 | 276.097 | 1.00 | 0.00 | C |
| ATOM | 4002 | O4* | A | C | 38 | 11.804 | 105.658 | 275.721 | 1.00 | 0.00 | O |
| ATOM | 4003 | C3* | A | C | 38 | 13.665 | 106.711 | 274.905 | 1.00 | 0.00 | C |
| ATOM | 4004 | O3* | A | C | 38 | 14.847 | 107.454 | 275.147 | 1.00 | 0.00 | O |
| ATOM | 4005 | C2* | A | C | 38 | 13.905 | 105.219 | 274.724 | 1.00 | 0.00 | C |
| ATOM | 4006 | O2* | A | C | 38 | 14.772 | 104.626 | 275.673 | 1.00 | 0.00 | O |
| ATOM | 4007 | C1* | A | C | 38 | 12.487 | 104.695 | 274.925 | 1.00 | 0.00 | C |
| ATOM | 4008 | N9 | A | C | 38 | 11.810 | 104.589 | 273.641 | 1.00 | 0.00 | N |
| ATOM | 4009 | C8 | A | C | 38 | 10.788 | 105.354 | 273.146 | 1.00 | 0.00 | C |
| ATOM | 4010 | N7 | A | C | 38 | 10.405 | 105.007 | 271.940 | 1.00 | 0.00 | N |
| ATOM | 4011 | C5 | A | C | 38 | 11.234 | 103.937 | 271.620 | 1.00 | 0.00 | C |
| ATOM | 4012 | C6 | A | C | 38 | 11.340 | 103.117 | 270.467 | 1.00 | 0.00 | C |
| ATOM | 4013 | N6 | A | C | 38 | 10.571 | 103.249 | 269.378 | 1.00 | 0.00 | N |
| ATOM | 4014 | N1 | A | C | 38 | 12.280 | 102.146 | 270.476 | 1.00 | 0.00 | N |
| ATOM | 4015 | C2 | A | C | 38 | 13.054 | 102.010 | 271.570 | 1.00 | 0.00 | C |
| ATOM | 4016 | N3 | A | C | 38 | 13.050 | 102.714 | 272.704 | 1.00 | 0.00 | N |
| ATOM | 4017 | C4 | A | C | 38 | 12.105 | 103.671 | 272.662 | 1.00 | 0.00 | C |
| HETATM | 4018 | N1 | PSU | C | 39 | 12.871 | 106.331 | 269.992 | 1.00 | 0.00 | N |
| HETATM | 4019 | C2 | PSU | C | 39 | 12.382 | 106.013 | 268.752 | 1.00 | 0.00 | C |
| HETATM | 4020 | N3 | PSU | C | 39 | 13.059 | 105.009 | 268.122 | 1.00 | 0.00 | N |
| HETATM | 4021 | C4 | PSU | C | 39 | 14.150 | 104.328 | 268.624 | 1.00 | 0.00 | C |
| HETATM | 4022 | C5 | PSU | C | 39 | 14.576 | 104.750 | 269.933 | 1.00 | 0.00 | C |
| HETATM | 4023 | C6 | PSU | C | 39 | 13.914 | 105.730 | 270.550 | 1.00 | 0.00 | C |
| HETATM | 4024 | O2 | PSU | C | 39 | 11.430 | 106.576 | 268.251 | 1.00 | 0.00 | O |
| HETATM | 4025 | O4 | PSU | C | 39 | 14.665 | 103.441 | 267.947 | 1.00 | 0.00 | O |
| HETATM | 4026 | C1* | PSU | C | 39 | 15.907 | 104.236 | 270.453 | 1.00 | 0.00 | C |
| HETATM | 4027 | C2* | PSU | C | 39 | 17.118 | 104.766 | 269.683 | 1.00 | 0.00 | C |
| HETATM | 4028 | O2* | PSU | C | 39 | 18.103 | 103.759 | 269.565 | 1.00 | 0.00 | O |
| HETATM | 4029 | C3* | PSU | C | 39 | 17.574 | 105.909 | 270.581 | 1.00 | 0.00 | C |
| HETATM | 4030 | C4* | PSU | C | 39 | 17.302 | 105.351 | 271.968 | 1.00 | 0.00 | C |
| HETATM | 4031 | O3* | PSU | C | 39 | 18.964 | 106.153 | 270.406 | 1.00 | 0.00 | O |
| HETATM | 4032 | O4* | PSU | C | 39 | 16.051 | 104.637 | 271.807 | 1.00 | 0.00 | O |
| HETATM | 4033 | C5* | PSU | C | 39 | 17.151 | 106.375 | 273.071 | 1.00 | 0.00 | C |
| HETATM | 4034 | O5* | PSU | C | 39 | 15.941 | 107.113 | 272.902 | 1.00 | 0.00 | O |
| HETATM | 4035 | P | PSU | C | 39 | 15.541 | 108.256 | 273.934 | 1.00 | 0.00 | P |
| HETATM | 4036 | O1P | PSU | C | 39 | 14.512 | 109.123 | 273.300 | 1.00 | 0.00 | O |
| HETATM | 4037 | O2P | PSU | C | 39 | 16.796 | 108.853 | 274.451 | 1.00 | 0.00 | O |
| HETATM | 4038 | P | 5MC | C | 40 | 19.448 | 107.311 | 269.402 | 1.00 | 0.00 | P |
| HETATM | 4039 | O1P | 5MC | C | 40 | 18.609 | 108.518 | 269.674 | 1.00 | 0.00 | O |
| HETATM | 4040 | O2P | 5MC | C | 40 | 20.929 | 107.407 | 269.476 | 1.00 | 0.00 | O |
| HETATM | 4041 | O5* | 5MC | C | 40 | 19.081 | 106.768 | 267.948 | 1.00 | 0.00 | O |
| HETATM | 4042 | C5* | 5MC | C | 40 | 20.016 | 106.008 | 267.196 | 1.00 | 0.00 | C |
| HETATM | 4043 | C4* | 5MC | C | 40 | 19.337 | 105.392 | 266.000 | 1.00 | 0.00 | C |
| HETATM | 4044 | O4* | 5MC | C | 40 | 18.016 | 104.909 | 266.373 | 1.00 | 0.00 | O |
| HETATM | 4045 | C3* | 5MC | C | 40 | 19.028 | 106.371 | 264.891 | 1.00 | 0.00 | C |
| HETATM | 4046 | O3* | 5MC | C | 40 | 20.170 | 106.604 | 264.088 | 1.00 | 0.00 | O |
| HETATM | 4047 | C2* | 5MC | C | 40 | 17.957 | 105.622 | 264.116 | 1.00 | 0.00 | C |
| HETATM | 4048 | O2* | 5MC | C | 40 | 18.456 | 104.619 | 263.254 | 1.00 | 0.00 | O |
| HETATM | 4049 | C1* | 5MC | C | 40 | 17.144 | 105.019 | 265.257 | 1.00 | 0.00 | C |
| HETATM | 4050 | N1 | 5MC | C | 40 | 16.027 | 105.907 | 265.607 | 1.00 | 0.00 | N |
| HETATM | 4051 | C2 | 5MC | C | 40 | 15.009 | 106.088 | 264.672 | 1.00 | 0.00 | C |
| HETATM | 4052 | O2 | 5MC | C | 40 | 15.104 | 105.532 | 263.570 | 1.00 | 0.00 | O |
| HETATM | 4053 | N3 | 5MC | C | 40 | 13.956 | 106.870 | 264.980 | 1.00 | 0.00 | N |
| HETATM | 4054 | C4 | 5MC | C | 40 | 13.906 | 107.476 | 266.158 | 1.00 | 0.00 | C |
| HETATM | 4055 | N4 | 5MC | C | 40 | 12.831 | 108.224 | 266.427 | 1.00 | 0.00 | N |
| HETATM | 4056 | C5 | 5MC | C | 40 | 14.943 | 107.342 | 267.116 | 1.00 | 0.00 | C |
| HETATM | 4057 | C6 | 5MC | C | 40 | 15.972 | 106.544 | 266.811 | 1.00 | 0.00 | C |
| HETATM | 4058 | CM5 | 5MC | C | 40 | 14.899 | 108.183 | 268.349 | 1.00 | 0.00 | C |
| ATOM | 4059 | P | U | C | 41 | 20.450 | 108.080 | 263.535 | 1.00 | 0.00 | P |
| ATOM | 4060 | O1P | U | C | 41 | 21.917 | 108.241 | 263.474 | 1.00 | 0.00 | O |
| ATOM | 4061 | O2P | U | C | 41 | 19.637 | 109.015 | 264.343 | 1.00 | 0.00 | O |
| ATOM | 4062 | O5* | U | C | 41 | 19.847 | 108.091 | 262.067 | 1.00 | 0.00 | O |
| ATOM | 4063 | C5* | U | C | 41 | 18.616 | 107.463 | 261.823 | 1.00 | 0.00 | C |
| ATOM | 4064 | C4* | U | C | 41 | 18.013 | 107.929 | 260.533 | 1.00 | 0.00 | C |
| ATOM | 4065 | O4* | U | C | 41 | 16.628 | 107.526 | 260.625 | 1.00 | 0.00 | O |
| ATOM | 4066 | C3* | U | C | 41 | 17.965 | 109.430 | 260.249 | 1.00 | 0.00 | C |
| ATOM | 4067 | O3* | U | C | 41 | 19.023 | 109.849 | 259.393 | 1.00 | 0.00 | O |

```
ATOM   4068  C2*  U C  41      16.625 109.559 259.540  1.00  0.00           C
ATOM   4069  O2*  U C  41      16.607 109.024 258.230  1.00  0.00           O
ATOM   4070  C1*  U C  41      15.794 108.633 260.404  1.00  0.00           C
ATOM   4071  N1   U C  41      15.464 109.221 261.704  1.00  0.00           N
ATOM   4072  C2   U C  41      14.310 109.941 261.747  1.00  0.00           C
ATOM   4073  O2   U C  41      13.593 110.076 260.759  1.00  0.00           O
ATOM   4074  N3   U C  41      14.020 110.502 262.964  1.00  0.00           N
ATOM   4075  C4   U C  41      14.767 110.410 264.117  1.00  0.00           C
ATOM   4076  O4   U C  41      14.371 110.972 265.139  1.00  0.00           O
ATOM   4077  C5   U C  41      15.969 109.629 263.993  1.00  0.00           C
ATOM   4078  C6   U C  41      16.261 109.071 262.817  1.00  0.00           C
ATOM   4079  P    G C  42      19.569 111.363 259.488  1.00  0.00           P
ATOM   4080  O1P  G C  42      20.673 111.515 258.537  1.00  0.00           O
ATOM   4081  O2P  G C  42      19.797 111.630 260.939  1.00  0.00           O
ATOM   4082  O5*  G C  42      18.372 112.254 258.935  1.00  0.00           O
ATOM   4083  C5*  G C  42      17.840 112.049 257.638  1.00  0.00           C
ATOM   4084  C4*  G C  42      16.471 112.696 257.532  1.00  0.00           C
ATOM   4085  O4*  G C  42      15.595 112.143 258.562  1.00  0.00           O
ATOM   4086  C3*  G C  42      16.393 114.197 257.810  1.00  0.00           C
ATOM   4087  O3*  G C  42      16.733 114.983 256.669  1.00  0.00           O
ATOM   4088  C2*  G C  42      14.908 114.369 258.093  1.00  0.00           C
ATOM   4089  O2*  G C  42      14.172 114.348 256.903  1.00  0.00           O
ATOM   4090  C1*  G C  42      14.604 113.106 258.897  1.00  0.00           C
ATOM   4091  N9   G C  42      14.627 113.367 260.336  1.00  0.00           N
ATOM   4092  C8   G C  42      15.558 112.969 261.271  1.00  0.00           C
ATOM   4093  N7   G C  42      15.273 113.372 262.488  1.00  0.00           N
ATOM   4094  C5   G C  42      14.081 114.076 262.340  1.00  0.00           C
ATOM   4095  C6   G C  42      13.266 114.723 263.299  1.00  0.00           C
ATOM   4096  O6   G C  42      13.430 114.815 264.515  1.00  0.00           O
ATOM   4097  N1   G C  42      12.154 115.303 262.707  1.00  0.00           N
ATOM   4098  C2   G C  42      11.855 115.263 261.366  1.00  0.00           C
ATOM   4099  N2   G C  42      10.719 115.887 260.975  1.00  0.00           N
ATOM   4100  N3   G C  42      12.596 114.665 260.471  1.00  0.00           N
ATOM   4101  C4   G C  42      13.681 114.093 261.019  1.00  0.00           C
ATOM   4102  P    G C  43      17.258 116.497 256.869  1.00  0.00           P
ATOM   4103  O1P  G C  43      17.876 116.970 255.604  1.00  0.00           O
ATOM   4104  O2P  G C  43      18.047 116.492 258.111  1.00  0.00           O
ATOM   4105  O5*  G C  43      15.926 117.344 257.086  1.00  0.00           O
ATOM   4106  C5*  G C  43      14.862 117.263 256.148  1.00  0.00           C
ATOM   4107  C4*  G C  43      13.629 117.915 256.700  1.00  0.00           C
ATOM   4108  O4*  G C  43      13.158 117.192 257.866  1.00  0.00           O
ATOM   4109  C3*  G C  43      13.880 119.312 257.213  1.00  0.00           C
ATOM   4110  O3*  G C  43      13.811 120.196 256.116  1.00  0.00           O
ATOM   4111  C2*  G C  43      12.725 119.498 258.189  1.00  0.00           C
ATOM   4112  O2*  G C  43      11.522 119.792 257.520  1.00  0.00           O
ATOM   4113  C1*  G C  43      12.622 118.104 258.803  1.00  0.00           C
ATOM   4114  N9   G C  43      13.336 117.934 260.064  1.00  0.00           N
ATOM   4115  C8   G C  43      14.553 117.340 260.253  1.00  0.00           C
ATOM   4116  N7   G C  43      14.920 117.301 261.509  1.00  0.00           N
ATOM   4117  C5   G C  43      13.885 117.918 262.185  1.00  0.00           C
ATOM   4118  C6   G C  43      13.722 118.183 263.560  1.00  0.00           C
ATOM   4119  O6   G C  43      14.485 117.887 264.506  1.00  0.00           O
ATOM   4120  N1   G C  43      12.527 118.864 263.810  1.00  0.00           N
ATOM   4121  C2   G C  43      11.614 119.233 262.859  1.00  0.00           C
ATOM   4122  N2   G C  43      10.537 119.904 263.290  1.00  0.00           N
ATOM   4123  N3   G C  43      11.748 118.975 261.573  1.00  0.00           N
ATOM   4124  C4   G C  43      12.901 118.323 261.306  1.00  0.00           C
ATOM   4125  P    A C  44      14.659 121.551 256.137  1.00  0.00           P
ATOM   4126  O1P  A C  44      14.606 122.071 254.742  1.00  0.00           O
ATOM   4127  O2P  A C  44      15.967 121.294 256.785  1.00  0.00           O
ATOM   4128  O5*  A C  44      13.795 122.490 257.090  1.00  0.00           O
ATOM   4129  C5*  A C  44      12.557 123.011 256.633  1.00  0.00           C
ATOM   4130  C4*  A C  44      11.677 123.354 257.805  1.00  0.00           C
ATOM   4131  O4*  A C  44      11.744 122.272 258.755  1.00  0.00           O
ATOM   4132  C3*  A C  44      12.142 124.546 258.608  1.00  0.00           C
ATOM   4133  O3*  A C  44      11.686 125.756 258.021  1.00  0.00           O
ATOM   4134  C2*  A C  44      11.481 124.297 259.948  1.00  0.00           C
ATOM   4135  O2*  A C  44      10.116 124.653 259.919  1.00  0.00           O
ATOM   4136  C1*  A C  44      11.625 122.782 260.066  1.00  0.00           C
ATOM   4137  N9   A C  44      12.804 122.354 260.805  1.00  0.00           N
ATOM   4138  C8   A C  44      13.996 121.943 260.283  1.00  0.00           C
ATOM   4139  N7   A C  44      14.869 121.569 261.190  1.00  0.00           N
ATOM   4140  C5   A C  44      14.209 121.763 262.392  1.00  0.00           C
ATOM   4141  C6   A C  44      14.588 121.556 263.739  1.00  0.00           C
ATOM   4142  N6   A C  44      15.784 121.070 264.132  1.00  0.00           N
ATOM   4143  N1   A C  44      13.679 121.863 264.695  1.00  0.00           N
ATOM   4144  C2   A C  44      12.480 122.326 264.315  1.00  0.00           C
ATOM   4145  N3   A C  44      12.014 122.551 263.098  1.00  0.00           N
ATOM   4146  C4   A C  44      12.935 122.253 262.170  1.00  0.00           C
ATOM   4147  P    G C  45      12.625 126.768 257.766  1.00  0.00           P
ATOM   4148  O1P  G C  45      11.715 127.758 257.164  1.00  0.00           O
ATOM   4149  O2P  G C  45      13.989 126.579 257.207  1.00  0.00           O
ATOM   4150  O5*  G C  45      12.694 127.064 259.328  1.00  0.00           O
ATOM   4151  C5*  G C  45      11.498 127.251 260.076  1.00  0.00           C
ATOM   4152  C4*  G C  45      11.827 127.462 261.522  1.00  0.00           C
ATOM   4153  O4*  G C  45      12.377 126.231 262.052  1.00  0.00           O
ATOM   4154  C3*  G C  45      12.922 128.486 261.747  1.00  0.00           C
```

```
ATOM   4155  O3*   G  C  45    12.322 129.762 261.869  1.00  0.00           O
ATOM   4156  C2*   G  C  45    13.499 128.046 263.082  1.00  0.00           C
ATOM   4157  O2*   G  C  45    12.697 128.490 264.142  1.00  0.00           O
ATOM   4158  C1*   G  C  45    13.398 126.521 262.992  1.00  0.00           C
ATOM   4159  N9    G  C  45    14.623 125.863 262.542  1.00  0.00           N
ATOM   4160  C8    G  C  45    14.974 125.591 261.241  1.00  0.00           C
ATOM   4161  N7    G  C  45    16.135 125.006 261.131  1.00  0.00           N
ATOM   4162  C5    G  C  45    16.584 124.880 262.443  1.00  0.00           C
ATOM   4163  C6    G  C  45    17.812 124.355 262.950  1.00  0.00           C
ATOM   4164  O6    G  C  45    18.787 123.874 262.317  1.00  0.00           O
ATOM   4165  N1    G  C  45    17.864 124.447 264.330  1.00  0.00           N
ATOM   4166  C2    G  C  45    16.866 124.980 265.122  1.00  0.00           C
ATOM   4167  N2    G  C  45    17.109 124.988 266.443  1.00  0.00           N
ATOM   4168  N3    G  C  45    15.723 125.473 264.658  1.00  0.00           N
ATOM   4169  C4    G  C  45    15.657 125.396 263.328  1.00  0.00           C
HETATM 4170  P    7MG C  46    12.848 130.968 260.962  1.00  0.00           P
HETATM 4171  O1P  7MG C  46    13.341 130.430 259.672  1.00  0.00           O
HETATM 4172  O2P  7MG C  46    11.814 132.034 260.964  1.00  0.00           O
HETATM 4173  O5*  7MG C  46    14.093 131.510 261.788  1.00  0.00           O
HETATM 4174  C5*  7MG C  46    13.932 131.850 263.158  1.00  0.00           C
HETATM 4175  C4*  7MG C  46    14.812 133.027 263.516  1.00  0.00           C
HETATM 4176  O4*  7MG C  46    16.187 132.555 263.635  1.00  0.00           O
HETATM 4177  C3*  7MG C  46    14.850 134.163 262.500  1.00  0.00           C
HETATM 4178  O3*  7MG C  46    15.007 135.414 263.180  1.00  0.00           O
HETATM 4179  C2*  7MG C  46    16.092 133.813 261.684  1.00  0.00           C
HETATM 4180  O2*  7MG C  46    16.676 134.890 260.969  1.00  0.00           O
HETATM 4181  C1*  7MG C  46    17.022 133.310 262.779  1.00  0.00           C
HETATM 4182  N9   7MG C  46    18.079 132.429 262.297  1.00  0.00           N
HETATM 4183  C8   7MG C  46    18.333 132.024 260.930  1.00  0.00           C
HETATM 4184  N7   7MG C  46    19.493 131.201 260.941  1.00  0.00           N
HETATM 4185  C5   7MG C  46    19.901 131.097 262.258  1.00  0.00           C
HETATM 4186  C6   7MG C  46    20.986 130.420 262.803  1.00  0.00           C
HETATM 4187  O6   7MG C  46    21.820 129.776 262.207  1.00  0.00           O
HETATM 4188  N1   7MG C  46    21.047 130.544 264.179  1.00  0.00           N
HETATM 4189  C2   7MG C  46    20.155 131.267 264.942  1.00  0.00           C
HETATM 4190  N2   7MG C  46    20.370 131.261 266.280  1.00  0.00           N
HETATM 4191  N3   7MG C  46    19.131 131.940 264.439  1.00  0.00           N
HETATM 4192  C4   7MG C  46    19.052 131.814 263.106  1.00  0.00           C
HETATM 4193  CM7  7MG C  46    20.017 130.647 259.654  1.00  0.00           C
ATOM   4194  P     U  C  47    13.707 136.352 263.462  1.00  0.00           P
ATOM   4195  O1P   U  C  47    13.409 136.336 264.907  1.00  0.00           O
ATOM   4196  O2P   U  C  47    12.651 135.957 262.482  1.00  0.00           O
ATOM   4197  O5*   U  C  47    14.213 137.807 263.052  1.00  0.00           O
ATOM   4198  C5*   U  C  47    14.972 137.996 261.849  1.00  0.00           C
ATOM   4199  C4*   U  C  47    15.784 139.274 261.935  1.00  0.00           C
ATOM   4200  O4*   U  C  47    14.909 140.443 261.974  1.00  0.00           O
ATOM   4201  C3*   U  C  47    16.660 139.397 263.176  1.00  0.00           C
ATOM   4202  O3*   U  C  47    17.791 140.137 262.795  1.00  0.00           O
ATOM   4203  C2*   U  C  47    15.782 140.192 264.130  1.00  0.00           C
ATOM   4204  O2*   U  C  47    16.465 140.884 265.161  1.00  0.00           O
ATOM   4205  C1*   U  C  47    15.148 141.174 263.162  1.00  0.00           C
ATOM   4206  N1    U  C  47    13.874 141.646 263.691  1.00  0.00           N
ATOM   4207  C2    U  C  47    13.687 142.995 263.732  1.00  0.00           C
ATOM   4208  O2    U  C  47    14.519 143.785 263.315  1.00  0.00           O
ATOM   4209  N3    U  C  47    12.498 143.391 264.282  1.00  0.00           N
ATOM   4210  C4    U  C  47    11.500 142.576 264.784  1.00  0.00           C
ATOM   4211  O4    U  C  47    10.494 143.085 265.283  1.00  0.00           O
ATOM   4212  C5    U  C  47    11.773 141.178 264.689  1.00  0.00           C
ATOM   4213  C6    U  C  47    12.922 140.773 264.155  1.00  0.00           C
ATOM   4214  P     C  C  48    19.046 139.364 262.179  1.00  0.00           P
ATOM   4215  O1P   C  C  48    19.890 140.365 261.495  1.00  0.00           O
ATOM   4216  O2P   C  C  48    18.504 138.203 261.426  1.00  0.00           O
ATOM   4217  O5*   C  C  48    19.780 138.793 263.471  1.00  0.00           O
ATOM   4218  C5*   C  C  48    20.355 139.673 264.388  1.00  0.00           C
ATOM   4219  C4*   C  C  48    21.081 138.903 265.451  1.00  0.00           C
ATOM   4220  O4*   C  C  48    21.669 137.691 264.888  1.00  0.00           O
ATOM   4221  C3*   C  C  48    22.219 139.684 266.075  1.00  0.00           C
ATOM   4222  O3*   C  C  48    22.157 139.422 267.471  1.00  0.00           O
ATOM   4223  C2*   C  C  48    23.450 139.083 265.379  1.00  0.00           C
ATOM   4224  O2*   C  C  48    24.652 139.133 266.108  1.00  0.00           O
ATOM   4225  C1*   C  C  48    23.040 137.623 265.237  1.00  0.00           C
ATOM   4226  N1    C  C  48    23.752 136.932 264.145  1.00  0.00           N
ATOM   4227  C2    C  C  48    24.794 136.072 264.440  1.00  0.00           C
ATOM   4228  O2    C  C  48    25.105 135.906 265.618  1.00  0.00           O
ATOM   4229  N3    C  C  48    25.448 135.453 263.416  1.00  0.00           N
ATOM   4230  C4    C  C  48    25.078 135.701 262.149  1.00  0.00           C
ATOM   4231  N4    C  C  48    25.753 135.121 261.128  1.00  0.00           N
ATOM   4232  C5    C  C  48    24.009 136.566 261.849  1.00  0.00           C
ATOM   4233  C6    C  C  48    23.392 137.152 262.861  1.00  0.00           C
HETATM 4234  P    5MC C  49    22.463 140.580 268.527  1.00  0.00           P
HETATM 4235  O1P  5MC C  49    22.664 139.874 269.819  1.00  0.00           O
HETATM 4236  O2P  5MC C  49    23.488 141.541 268.042  1.00  0.00           O
HETATM 4237  O5*  5MC C  49    21.107 141.446 268.609  1.00  0.00           O
HETATM 4238  C5*  5MC C  49    19.843 140.837 268.816  1.00  0.00           C
HETATM 4239  C4*  5MC C  49    18.795 141.922 269.028  1.00  0.00           C
HETATM 4240  O4*  5MC C  49    19.006 142.523 270.335  1.00  0.00           O
HETATM 4241  C3*  5MC C  49    19.012 143.091 268.083  1.00  0.00           C
```

| | | | | | | | | | | |
|---|---|---|---|---|---|---|---|---|---|---|
| HETATM | 4242 | O3* | 5MC | C | 49 | 18.400 | 142.829 | 266.847 | 1.00 | 0.00 | O |
| HETATM | 4243 | C2* | 5MC | C | 49 | 18.344 | 144.216 | 268.829 | 1.00 | 0.00 | C |
| HETATM | 4244 | O2* | 5MC | C | 49 | 16.940 | 144.066 | 268.731 | 1.00 | 0.00 | O |
| HETATM | 4245 | C1* | 5MC | C | 49 | 18.828 | 143.938 | 270.248 | 1.00 | 0.00 | C |
| HETATM | 4246 | N1 | 5MC | C | 49 | 20.108 | 144.622 | 270.584 | 1.00 | 0.00 | N |
| HETATM | 4247 | C2 | 5MC | C | 49 | 20.109 | 146.041 | 270.720 | 1.00 | 0.00 | C |
| HETATM | 4248 | O2 | 5MC | C | 49 | 19.028 | 146.678 | 270.603 | 1.00 | 0.00 | O |
| HETATM | 4249 | N3 | 5MC | C | 49 | 21.276 | 146.685 | 270.973 | 1.00 | 0.00 | N |
| HETATM | 4250 | C4 | 5MC | C | 49 | 22.413 | 145.995 | 271.125 | 1.00 | 0.00 | C |
| HETATM | 4251 | N4 | 5MC | C | 49 | 23.532 | 146.689 | 271.392 | 1.00 | 0.00 | N |
| HETATM | 4252 | C5 | 5MC | C | 49 | 22.452 | 144.568 | 271.013 | 1.00 | 0.00 | C |
| HETATM | 4253 | C6 | 5MC | C | 49 | 21.282 | 143.919 | 270.741 | 1.00 | 0.00 | C |
| HETATM | 4254 | CM5 | 5MC | C | 49 | 23.766 | 143.870 | 271.200 | 1.00 | 0.00 | C |
| ATOM | 4255 | P | U | C | 50 | 18.987 | 143.518 | 265.510 | 1.00 | 0.00 | P |
| ATOM | 4256 | O1P | U | C | 50 | 18.351 | 142.831 | 264.384 | 1.00 | 0.00 | O |
| ATOM | 4257 | O2P | U | C | 50 | 20.494 | 143.637 | 265.607 | 1.00 | 0.00 | O |
| ATOM | 4258 | O5* | U | C | 50 | 18.482 | 145.027 | 265.519 | 1.00 | 0.00 | O |
| ATOM | 4259 | C5* | U | C | 50 | 17.118 | 145.360 | 265.768 | 1.00 | 0.00 | C |
| ATOM | 4260 | C4* | U | C | 50 | 16.937 | 146.868 | 265.780 | 1.00 | 0.00 | C |
| ATOM | 4261 | O4* | U | C | 50 | 17.359 | 147.406 | 267.066 | 1.00 | 0.00 | O |
| ATOM | 4262 | C3* | U | C | 50 | 17.761 | 147.681 | 264.785 | 1.00 | 0.00 | C |
| ATOM | 4263 | O3* | U | C | 50 | 17.133 | 147.757 | 263.521 | 1.00 | 0.00 | O |
| ATOM | 4264 | C2* | U | C | 50 | 17.696 | 149.051 | 265.429 | 1.00 | 0.00 | C |
| ATOM | 4265 | O2* | U | C | 50 | 16.393 | 149.574 | 265.296 | 1.00 | 0.00 | O |
| ATOM | 4266 | C1* | U | C | 50 | 17.934 | 148.678 | 266.882 | 1.00 | 0.00 | C |
| ATOM | 4267 | N1 | U | C | 50 | 19.359 | 148.588 | 267.202 | 1.00 | 0.00 | N |
| ATOM | 4268 | C2 | U | C | 50 | 20.034 | 149.780 | 267.391 | 1.00 | 0.00 | C |
| ATOM | 4269 | O2 | U | C | 50 | 19.507 | 150.878 | 267.218 | 1.00 | 0.00 | O |
| ATOM | 4270 | N3 | U | C | 50 | 21.339 | 149.656 | 267.797 | 1.00 | 0.00 | N |
| ATOM | 4271 | C4 | U | C | 50 | 22.024 | 148.496 | 268.010 | 1.00 | 0.00 | C |
| ATOM | 4272 | O4 | U | C | 50 | 23.206 | 148.555 | 268.370 | 1.00 | 0.00 | O |
| ATOM | 4273 | C5 | U | C | 50 | 21.268 | 147.291 | 267.744 | 1.00 | 0.00 | C |
| ATOM | 4274 | C6 | U | C | 50 | 19.995 | 147.382 | 267.348 | 1.00 | 0.00 | C |
| ATOM | 4275 | P | G | C | 51 | 18.029 | 147.876 | 262.193 | 1.00 | 0.00 | P |
| ATOM | 4276 | O1P | G | C | 51 | 17.115 | 147.508 | 261.112 | 1.00 | 0.00 | O |
| ATOM | 4277 | O2P | G | C | 51 | 19.309 | 147.132 | 262.347 | 1.00 | 0.00 | O |
| ATOM | 4278 | O5* | G | C | 51 | 18.419 | 149.407 | 262.154 | 1.00 | 0.00 | O |
| ATOM | 4279 | C5* | G | C | 51 | 17.466 | 150.409 | 262.473 | 1.00 | 0.00 | C |
| ATOM | 4280 | C4* | G | C | 51 | 18.136 | 151.765 | 262.491 | 1.00 | 0.00 | C |
| ATOM | 4281 | O4* | G | C | 51 | 18.672 | 152.036 | 263.816 | 1.00 | 0.00 | O |
| ATOM | 4282 | C3* | G | C | 51 | 19.314 | 151.932 | 261.538 | 1.00 | 0.00 | C |
| ATOM | 4283 | O3* | G | C | 51 | 18.889 | 152.347 | 260.240 | 1.00 | 0.00 | O |
| ATOM | 4284 | C2* | G | C | 51 | 20.115 | 153.026 | 262.217 | 1.00 | 0.00 | C |
| ATOM | 4285 | O2* | G | C | 51 | 19.530 | 154.266 | 262.031 | 1.00 | 0.00 | O |
| ATOM | 4286 | C1* | G | C | 51 | 19.926 | 152.681 | 263.697 | 1.00 | 0.00 | C |
| ATOM | 4287 | N9 | G | C | 51 | 20.985 | 151.782 | 264.133 | 1.00 | 0.00 | N |
| ATOM | 4288 | C8 | G | C | 51 | 20.995 | 150.408 | 264.096 | 1.00 | 0.00 | C |
| ATOM | 4289 | N7 | G | C | 51 | 22.137 | 149.895 | 264.488 | 1.00 | 0.00 | N |
| ATOM | 4290 | C5 | G | C | 51 | 22.920 | 150.999 | 264.811 | 1.00 | 0.00 | C |
| ATOM | 4291 | C6 | G | C | 51 | 24.244 | 151.074 | 265.278 | 1.00 | 0.00 | C |
| ATOM | 4292 | O6 | G | C | 51 | 25.035 | 150.138 | 265.528 | 1.00 | 0.00 | O |
| ATOM | 4293 | N1 | G | C | 51 | 24.646 | 152.390 | 265.468 | 1.00 | 0.00 | N |
| ATOM | 4294 | C2 | G | C | 51 | 23.868 | 153.492 | 265.238 | 1.00 | 0.00 | C |
| ATOM | 4295 | N2 | G | C | 51 | 24.435 | 154.679 | 265.477 | 1.00 | 0.00 | N |
| ATOM | 4296 | N3 | G | C | 51 | 22.622 | 153.436 | 264.810 | 1.00 | 0.00 | N |
| ATOM | 4297 | C4 | G | C | 51 | 22.216 | 152.169 | 264.619 | 1.00 | 0.00 | C |
| ATOM | 4298 | P | U | C | 52 | 19.800 | 152.009 | 258.932 | 1.00 | 0.00 | P |
| ATOM | 4299 | O1P | U | C | 52 | 19.021 | 152.389 | 257.735 | 1.00 | 0.00 | O |
| ATOM | 4300 | O2P | U | C | 52 | 20.336 | 150.632 | 259.022 | 1.00 | 0.00 | O |
| ATOM | 4301 | O5* | U | C | 52 | 21.012 | 153.008 | 259.096 | 1.00 | 0.00 | O |
| ATOM | 4302 | C5* | U | C | 52 | 20.785 | 154.399 | 259.068 | 1.00 | 0.00 | C |
| ATOM | 4303 | C4* | U | C | 52 | 22.005 | 155.124 | 259.549 | 1.00 | 0.00 | C |
| ATOM | 4304 | O4* | U | C | 52 | 22.255 | 154.760 | 260.917 | 1.00 | 0.00 | O |
| ATOM | 4305 | C3* | U | C | 52 | 23.295 | 154.702 | 258.876 | 1.00 | 0.00 | C |
| ATOM | 4306 | O3* | U | C | 52 | 23.441 | 155.351 | 257.618 | 1.00 | 0.00 | O |
| ATOM | 4307 | C2* | U | C | 52 | 24.299 | 155.262 | 259.860 | 1.00 | 0.00 | C |
| ATOM | 4308 | O2* | U | C | 52 | 24.392 | 156.665 | 259.732 | 1.00 | 0.00 | O |
| ATOM | 4309 | C1* | U | C | 52 | 23.650 | 154.863 | 261.189 | 1.00 | 0.00 | C |
| ATOM | 4310 | N1 | U | C | 52 | 24.168 | 153.540 | 261.584 | 1.00 | 0.00 | N |
| ATOM | 4311 | C2 | U | C | 52 | 25.418 | 153.494 | 262.128 | 1.00 | 0.00 | C |
| ATOM | 4312 | O2 | U | C | 52 | 26.068 | 154.479 | 262.321 | 1.00 | 0.00 | O |
| ATOM | 4313 | N3 | U | C | 52 | 25.893 | 152.249 | 262.423 | 1.00 | 0.00 | N |
| ATOM | 4314 | C4 | U | C | 52 | 25.254 | 151.062 | 262.209 | 1.00 | 0.00 | C |
| ATOM | 4315 | O4 | U | C | 52 | 25.833 | 150.004 | 262.475 | 1.00 | 0.00 | O |
| ATOM | 4316 | C5 | U | C | 52 | 23.943 | 151.190 | 261.645 | 1.00 | 0.00 | C |
| ATOM | 4317 | C6 | U | C | 52 | 23.458 | 152.396 | 261.376 | 1.00 | 0.00 | C |
| ATOM | 4318 | P | G | C | 53 | 24.440 | 154.736 | 256.512 | 1.00 | 0.00 | P |
| ATOM | 4319 | O1P | G | C | 53 | 24.316 | 155.589 | 255.307 | 1.00 | 0.00 | O |
| ATOM | 4320 | O2P | G | C | 53 | 24.179 | 153.288 | 256.418 | 1.00 | 0.00 | O |
| ATOM | 4321 | O5* | G | C | 53 | 25.896 | 154.895 | 257.122 | 1.00 | 0.00 | O |
| ATOM | 4322 | C5* | G | C | 53 | 26.419 | 156.164 | 257.462 | 1.00 | 0.00 | C |
| ATOM | 4323 | C4* | G | C | 53 | 27.740 | 155.989 | 258.170 | 1.00 | 0.00 | C |
| ATOM | 4324 | O4* | G | C | 53 | 27.500 | 155.222 | 259.379 | 1.00 | 0.00 | O |
| ATOM | 4325 | C3* | G | C | 53 | 28.813 | 155.152 | 257.464 | 1.00 | 0.00 | C |
| ATOM | 4326 | O3* | G | C | 53 | 29.549 | 155.932 | 256.514 | 1.00 | 0.00 | O |
| ATOM | 4327 | C2* | G | C | 53 | 29.710 | 154.752 | 258.634 | 1.00 | 0.00 | C |
| ATOM | 4328 | O2* | G | C | 53 | 30.629 | 155.738 | 259.039 | 1.00 | 0.00 | O |

| | | | | | | | | | | |
|---|---|---|---|---|---|---|---|---|---|---|
| ATOM | 4329 | C1* | G | C | 53 | 28.697 | 154.552 | 259.761 | 1.00 | 0.00 | C |
| ATOM | 4330 | N9 | G | C | 53 | 28.402 | 153.133 | 259.892 | 1.00 | 0.00 | N |
| ATOM | 4331 | C8 | G | C | 53 | 27.241 | 152.491 | 259.551 | 1.00 | 0.00 | C |
| ATOM | 4332 | N7 | G | C | 53 | 27.281 | 151.201 | 259.778 | 1.00 | 0.00 | N |
| ATOM | 4333 | C5 | G | C | 53 | 28.541 | 150.989 | 260.303 | 1.00 | 0.00 | C |
| ATOM | 4334 | C6 | G | C | 53 | 29.169 | 149.781 | 260.710 | 1.00 | 0.00 | C |
| ATOM | 4335 | O6 | G | C | 53 | 28.696 | 148.634 | 260.729 | 1.00 | 0.00 | O |
| ATOM | 4336 | N1 | G | C | 53 | 30.473 | 150.004 | 261.127 | 1.00 | 0.00 | N |
| ATOM | 4337 | C2 | G | C | 53 | 31.106 | 151.240 | 261.157 | 1.00 | 0.00 | C |
| ATOM | 4338 | N2 | G | C | 53 | 32.375 | 151.237 | 261.617 | 1.00 | 0.00 | N |
| ATOM | 4339 | N3 | G | C | 53 | 30.528 | 152.378 | 260.777 | 1.00 | 0.00 | N |
| ATOM | 4340 | C4 | G | C | 53 | 29.253 | 152.174 | 260.365 | 1.00 | 0.00 | C |
| HETATM | 4341 | N1 | 5MU | C | 54 | 32.480 | 150.996 | 257.947 | 1.00 | 0.00 | N |
| HETATM | 4342 | C2 | 5MU | C | 54 | 32.638 | 149.707 | 258.372 | 1.00 | 0.00 | C |
| HETATM | 4343 | N3 | 5MU | C | 54 | 31.572 | 148.867 | 258.117 | 1.00 | 0.00 | N |
| HETATM | 4344 | C4 | 5MU | C | 54 | 30.381 | 149.190 | 257.489 | 1.00 | 0.00 | C |
| HETATM | 4345 | C5 | 5MU | C | 54 | 30.296 | 150.570 | 257.053 | 1.00 | 0.00 | C |
| HETATM | 4346 | C5M | 5MU | C | 54 | 29.070 | 151.012 | 256.316 | 1.00 | 0.00 | C |
| HETATM | 4347 | C6 | 5MU | C | 54 | 31.325 | 151.404 | 257.305 | 1.00 | 0.00 | C |
| HETATM | 4348 | O2 | 5MU | C | 54 | 33.657 | 149.336 | 258.942 | 1.00 | 0.00 | O |
| HETATM | 4349 | O4 | 5MU | C | 54 | 29.519 | 148.305 | 257.312 | 1.00 | 0.00 | O |
| HETATM | 4350 | C1* | 5MU | C | 54 | 33.614 | 151.906 | 258.199 | 1.00 | 0.00 | C |
| HETATM | 4351 | C2* | 5MU | C | 54 | 34.675 | 151.864 | 257.085 | 1.00 | 0.00 | C |
| HETATM | 4352 | O2* | 5MU | C | 54 | 35.968 | 152.127 | 257.599 | 1.00 | 0.00 | O |
| HETATM | 4353 | C3* | 5MU | C | 54 | 34.177 | 152.978 | 256.170 | 1.00 | 0.00 | C |
| HETATM | 4354 | C4* | 5MU | C | 54 | 33.768 | 154.025 | 257.192 | 1.00 | 0.00 | C |
| HETATM | 4355 | O3* | 5MU | C | 54 | 35.172 | 153.467 | 255.269 | 1.00 | 0.00 | O |
| HETATM | 4356 | O4* | 5MU | C | 54 | 33.116 | 153.232 | 258.227 | 1.00 | 0.00 | O |
| HETATM | 4357 | C5* | 5MU | C | 54 | 32.784 | 155.055 | 256.703 | 1.00 | 0.00 | C |
| HETATM | 4358 | O5* | 5MU | C | 54 | 31.615 | 154.416 | 256.252 | 1.00 | 0.00 | O |
| HETATM | 4359 | P | 5MU | C | 54 | 30.524 | 155.207 | 255.414 | 1.00 | 0.00 | P |
| HETATM | 4360 | O1P | 5MU | C | 54 | 29.759 | 154.229 | 254.595 | 1.00 | 0.00 | O |
| HETATM | 4361 | O2P | 5MU | C | 54 | 31.212 | 156.350 | 254.760 | 1.00 | 0.00 | O |
| HETATM | 4362 | N1 | PSU | C | 55 | 31.356 | 149.743 | 253.869 | 1.00 | 0.00 | N |
| HETATM | 4363 | C2 | PSU | C | 55 | 30.378 | 148.782 | 253.930 | 1.00 | 0.00 | C |
| HETATM | 4364 | N3 | PSU | C | 55 | 30.829 | 147.533 | 254.293 | 1.00 | 0.00 | N |
| HETATM | 4365 | C4 | PSU | C | 55 | 32.160 | 147.212 | 254.590 | 1.00 | 0.00 | C |
| HETATM | 4366 | C5 | PSU | C | 55 | 33.087 | 148.289 | 254.478 | 1.00 | 0.00 | C |
| HETATM | 4367 | C6 | PSU | C | 55 | 32.647 | 149.503 | 254.122 | 1.00 | 0.00 | C |
| HETATM | 4368 | O2 | PSU | C | 55 | 29.215 | 149.013 | 253.675 | 1.00 | 0.00 | O |
| HETATM | 4369 | O4 | PSU | C | 55 | 32.441 | 146.080 | 254.938 | 1.00 | 0.00 | O |
| HETATM | 4370 | C1* | PSU | C | 55 | 34.556 | 147.935 | 254.528 | 1.00 | 0.00 | C |
| HETATM | 4371 | C2* | PSU | C | 55 | 35.171 | 147.573 | 253.171 | 1.00 | 0.00 | C |
| HETATM | 4372 | O2* | PSU | C | 55 | 36.153 | 146.574 | 253.408 | 1.00 | 0.00 | O |
| HETATM | 4373 | C3* | PSU | C | 55 | 35.728 | 148.931 | 252.741 | 1.00 | 0.00 | C |
| HETATM | 4374 | C4* | PSU | C | 55 | 36.288 | 149.450 | 254.053 | 1.00 | 0.00 | C |
| HETATM | 4375 | O3* | PSU | C | 55 | 36.761 | 148.875 | 251.760 | 1.00 | 0.00 | O |
| HETATM | 4376 | O4* | PSU | C | 55 | 35.265 | 149.051 | 255.017 | 1.00 | 0.00 | O |
| HETATM | 4377 | C5* | PSU | C | 55 | 36.448 | 150.953 | 254.105 | 1.00 | 0.00 | C |
| HETATM | 4378 | O5* | PSU | C | 55 | 35.288 | 151.587 | 253.563 | 1.00 | 0.00 | O |
| HETATM | 4379 | P | PSU | C | 55 | 35.041 | 153.167 | 253.682 | 1.00 | 0.00 | P |
| HETATM | 4380 | O1P | PSU | C | 55 | 33.631 | 153.419 | 253.255 | 1.00 | 0.00 | O |
| HETATM | 4381 | O2P | PSU | C | 55 | 36.142 | 153.911 | 253.014 | 1.00 | 0.00 | O |
| ATOM | 4382 | P | C | C | 56 | 36.455 | 149.225 | 250.229 | 1.00 | 0.00 | P |
| ATOM | 4383 | O1P | C | C | 56 | 37.798 | 149.209 | 249.570 | 1.00 | 0.00 | O |
| ATOM | 4384 | O2P | C | C | 56 | 35.592 | 150.465 | 250.087 | 1.00 | 0.00 | O |
| ATOM | 4385 | O5* | C | C | 56 | 35.578 | 148.056 | 249.660 | 1.00 | 0.00 | O |
| ATOM | 4386 | C5* | C | C | 56 | 34.914 | 148.201 | 248.424 | 1.00 | 0.00 | C |
| ATOM | 4387 | C4* | C | C | 56 | 34.248 | 146.915 | 248.029 | 1.00 | 0.00 | C |
| ATOM | 4388 | O4* | C | C | 56 | 35.264 | 145.947 | 247.686 | 1.00 | 0.00 | O |
| ATOM | 4389 | C3* | C | C | 56 | 33.438 | 146.246 | 249.132 | 1.00 | 0.00 | C |
| ATOM | 4390 | O3* | C | C | 56 | 32.135 | 146.808 | 249.127 | 1.00 | 0.00 | O |
| ATOM | 4391 | C2* | C | C | 56 | 33.415 | 144.805 | 248.653 | 1.00 | 0.00 | C |
| ATOM | 4392 | O2* | C | C | 56 | 32.428 | 144.532 | 247.653 | 1.00 | 0.00 | O |
| ATOM | 4393 | C1* | C | C | 56 | 34.832 | 144.656 | 248.090 | 1.00 | 0.00 | C |
| ATOM | 4394 | N1 | C | C | 56 | 35.765 | 144.172 | 249.116 | 1.00 | 0.00 | N |
| ATOM | 4395 | C2 | C | C | 56 | 35.763 | 142.823 | 249.424 | 1.00 | 0.00 | C |
| ATOM | 4396 | O2 | C | C | 56 | 34.962 | 142.100 | 248.879 | 1.00 | 0.00 | O |
| ATOM | 4397 | N3 | C | C | 56 | 36.631 | 142.343 | 250.312 | 1.00 | 0.00 | N |
| ATOM | 4398 | C4 | C | C | 56 | 37.483 | 143.153 | 250.920 | 1.00 | 0.00 | C |
| ATOM | 4399 | N4 | C | C | 56 | 38.330 | 142.598 | 251.783 | 1.00 | 0.00 | N |
| ATOM | 4400 | C5 | C | C | 56 | 37.504 | 144.558 | 250.660 | 1.00 | 0.00 | C |
| ATOM | 4401 | C6 | C | C | 56 | 36.627 | 145.024 | 249.749 | 1.00 | 0.00 | C |
| ATOM | 4402 | P | G | C | 57 | 31.422 | 147.196 | 250.521 | 1.00 | 0.00 | P |
| ATOM | 4403 | O1P | G | C | 57 | 30.092 | 147.748 | 250.121 | 1.00 | 0.00 | O |
| ATOM | 4404 | O2P | G | C | 57 | 32.319 | 147.971 | 251.403 | 1.00 | 0.00 | O |
| ATOM | 4405 | O5* | G | C | 57 | 31.199 | 145.789 | 251.232 | 1.00 | 0.00 | O |
| ATOM | 4406 | C5* | G | C | 57 | 30.314 | 144.846 | 250.667 | 1.00 | 0.00 | C |
| ATOM | 4407 | C4* | G | C | 57 | 30.479 | 143.483 | 251.317 | 1.00 | 0.00 | C |
| ATOM | 4408 | O4* | G | C | 57 | 31.815 | 142.934 | 251.091 | 1.00 | 0.00 | O |
| ATOM | 4409 | C3* | G | C | 57 | 30.314 | 143.440 | 252.826 | 1.00 | 0.00 | C |
| ATOM | 4410 | O3* | G | C | 57 | 28.934 | 143.393 | 253.119 | 1.00 | 0.00 | O |
| ATOM | 4411 | C2* | G | C | 57 | 30.959 | 142.112 | 253.162 | 1.00 | 0.00 | C |
| ATOM | 4412 | O2* | G | C | 57 | 30.082 | 141.052 | 252.816 | 1.00 | 0.00 | O |
| ATOM | 4413 | C1* | G | C | 57 | 32.159 | 142.112 | 252.198 | 1.00 | 0.00 | C |
| ATOM | 4414 | N9 | G | C | 57 | 33.364 | 142.669 | 252.793 | 1.00 | 0.00 | N |
| ATOM | 4415 | C8 | G | C | 57 | 33.885 | 143.938 | 252.623 | 1.00 | 0.00 | C |

```
ATOM    4416  N7     G  C  57      35.032 144.101 253.241  1.00  0.00           N
ATOM    4417  C5     G  C  57      35.265 142.872 253.865  1.00  0.00           C
ATOM    4418  C6     G  C  57      36.380 142.414 254.677  1.00  0.00           C
ATOM    4419  O6     G  C  57      37.392 143.043 255.033  1.00  0.00           O
ATOM    4420  N1     G  C  57      36.203 141.096 255.087  1.00  0.00           N
ATOM    4421  C2     G  C  57      35.094 140.327 254.787  1.00  0.00           C
ATOM    4422  N2     G  C  57      35.041 139.104 255.316  1.00  0.00           N
ATOM    4423  N3     G  C  57      34.077 140.736 254.026  1.00  0.00           N
ATOM    4424  C4     G  C  57      34.233 141.993 253.609  1.00  0.00           C
HETATM  4425  P      1MA C  58     28.406 144.132 254.418  1.00  0.00           P
HETATM  4426  O1P    1MA C  58     28.978 145.472 254.575  1.00  0.00           O
HETATM  4427  O2P    1MA C  58     26.946 143.952 254.423  1.00  0.00           O
HETATM  4428  O5*    1MA C  58     29.046 143.323 255.643  1.00  0.00           O
HETATM  4429  C5*    1MA C  58     28.769 141.958 255.835  1.00  0.00           C
HETATM  4430  C4*    1MA C  58     28.844 141.597 257.318  1.00  0.00           C
HETATM  4431  O4*    1MA C  58     30.103 142.066 257.892  1.00  0.00           O
HETATM  4432  C3*    1MA C  58     27.757 142.160 258.250  1.00  0.00           C
HETATM  4433  O3*    1MA C  58     27.666 141.292 259.389  1.00  0.00           O
HETATM  4434  C2*    1MA C  58     28.434 143.445 258.689  1.00  0.00           C
HETATM  4435  O2*    1MA C  58     27.938 144.039 259.859  1.00  0.00           O
HETATM  4436  C1*    1MA C  58     29.836 142.922 258.977  1.00  0.00           C
HETATM  4437  N9     1MA C  58     30.867 143.965 259.069  1.00  0.00           N
HETATM  4438  C8     1MA C  58     30.784 145.240 258.595  1.00  0.00           C
HETATM  4439  N7     1MA C  58     31.816 145.981 258.900  1.00  0.00           N
HETATM  4440  C5     1MA C  58     32.657 145.127 259.602  1.00  0.00           C
HETATM  4441  C6     1MA C  58     33.972 145.453 260.161  1.00  0.00           C
HETATM  4442  N6     1MA C  58     34.525 146.820 260.058  1.00  0.00           N
HETATM  4443  N1     1MA C  58     34.586 144.322 260.825  1.00  0.00           N
HETATM  4444  CM1    1MA C  58     35.904 144.656 261.402  1.00  0.00           C
HETATM  4445  C2     1MA C  58     33.897 143.152 260.835  1.00  0.00           C
HETATM  4446  N3     1MA C  58     32.667 142.829 260.327  1.00  0.00           N
HETATM  4447  C4     1MA C  58     32.088 143.884 259.702  1.00  0.00           C
ATOM    4448  P      U  C  59      26.803 139.900 259.324  1.00  0.00           P
ATOM    4449  O1P    U  C  59      27.518 138.752 258.736  1.00  0.00           O
ATOM    4450  O2P    U  C  59      25.439 140.249 258.845  1.00  0.00           O
ATOM    4451  O5*    U  C  59      26.617 139.546 260.866  1.00  0.00           O
ATOM    4452  C5*    U  C  59      25.735 140.320 261.698  1.00  0.00           C
ATOM    4453  C4*    U  C  59      26.132 140.151 263.152  1.00  0.00           C
ATOM    4454  O4*    U  C  59      26.292 138.720 263.404  1.00  0.00           O
ATOM    4455  C3*    U  C  59      27.502 140.756 263.493  1.00  0.00           C
ATOM    4456  O3*    U  C  59      27.388 142.174 263.829  1.00  0.00           O
ATOM    4457  C2*    U  C  59      27.968 139.883 264.667  1.00  0.00           C
ATOM    4458  O2*    U  C  59      27.493 140.375 265.904  1.00  0.00           O
ATOM    4459  C1*    U  C  59      27.311 138.517 264.361  1.00  0.00           C
ATOM    4460  N1     U  C  59      28.245 137.468 263.873  1.00  0.00           N
ATOM    4461  C2     U  C  59      29.147 136.986 264.791  1.00  0.00           C
ATOM    4462  O2     U  C  59      29.144 137.344 265.958  1.00  0.00           O
ATOM    4463  N3     U  C  59      30.047 136.052 264.314  1.00  0.00           N
ATOM    4464  C4     U  C  59      30.121 135.547 263.034  1.00  0.00           C
ATOM    4465  O4     U  C  59      30.980 134.695 262.777  1.00  0.00           O
ATOM    4466  C5     U  C  59      29.135 136.083 262.118  1.00  0.00           C
ATOM    4467  C6     U  C  59      28.244 136.999 262.566  1.00  0.00           C
ATOM    4468  P      C  C  60      28.621 143.186 263.514  1.00  0.00           P
ATOM    4469  O1P    C  C  60      28.312 144.517 264.063  1.00  0.00           O
ATOM    4470  O2P    C  C  60      28.975 143.043 262.066  1.00  0.00           O
ATOM    4471  O5*    C  C  60      29.875 142.532 264.247  1.00  0.00           O
ATOM    4472  C5*    C  C  60      30.013 142.529 265.676  1.00  0.00           C
ATOM    4473  C4*    C  C  60      31.332 141.858 266.059  1.00  0.00           C
ATOM    4474  O4*    C  C  60      31.379 140.540 265.418  1.00  0.00           O
ATOM    4475  C3*    C  C  60      32.567 142.586 265.559  1.00  0.00           C
ATOM    4476  O3*    C  C  60      33.660 142.355 266.438  1.00  0.00           O
ATOM    4477  C2*    C  C  60      32.822 141.902 264.237  1.00  0.00           C
ATOM    4478  O2*    C  C  60      34.145 142.013 263.796  1.00  0.00           O
ATOM    4479  C1*    C  C  60      32.540 140.453 264.621  1.00  0.00           C
ATOM    4480  N1     C  C  60      32.244 139.628 263.444  1.00  0.00           N
ATOM    4481  C2     C  C  60      32.923 138.410 263.296  1.00  0.00           C
ATOM    4482  O2     C  C  60      33.739 138.049 264.191  1.00  0.00           O
ATOM    4483  N3     C  C  60      32.693 137.664 262.199  1.00  0.00           N
ATOM    4484  C4     C  C  60      31.835 138.087 261.254  1.00  0.00           C
ATOM    4485  N4     C  C  60      31.695 137.336 260.169  1.00  0.00           N
ATOM    4486  C5     C  C  60      31.112 139.304 261.381  1.00  0.00           C
ATOM    4487  C6     C  C  60      31.347 140.045 262.491  1.00  0.00           C
ATOM    4488  P      C  C  61      33.954 143.418 267.587  1.00  0.00           P
ATOM    4489  O1P    C  C  61      35.027 142.801 268.379  1.00  0.00           O
ATOM    4490  O2P    C  C  61      32.693 143.846 268.232  1.00  0.00           O
ATOM    4491  O5*    C  C  61      34.480 144.715 266.814  1.00  0.00           O
ATOM    4492  C5*    C  C  61      35.844 144.817 266.398  1.00  0.00           C
ATOM    4493  C4*    C  C  61      36.076 146.135 265.674  1.00  0.00           C
ATOM    4494  O4*    C  C  61      35.659 145.999 264.291  1.00  0.00           O
ATOM    4495  C3*    C  C  61      35.253 147.300 266.189  1.00  0.00           C
ATOM    4496  O3*    C  C  61      35.889 147.891 267.333  1.00  0.00           O
ATOM    4497  C2*    C  C  61      35.236 148.219 264.976  1.00  0.00           C
ATOM    4498  O2*    C  C  61      36.473 148.882 264.827  1.00  0.00           O
ATOM    4499  C1*    C  C  61      35.105 147.220 263.827  1.00  0.00           C
ATOM    4500  N1     C  C  61      33.728 146.955 263.358  1.00  0.00           N
ATOM    4501  C2     C  C  61      33.048 147.944 262.664  1.00  0.00           C
ATOM    4502  O2     C  C  61      33.604 149.034 262.480  1.00  0.00           O
```

```
ATOM   4503  N3    C C  61      31.797 147.699 262.213  1.00  0.00           N
ATOM   4504  C4    C C  61      31.226 146.513 262.457  1.00  0.00           C
ATOM   4505  N4    C C  61      29.995 146.302 262.010  1.00  0.00           N
ATOM   4506  C5    C C  61      31.898 145.489 263.174  1.00  0.00           C
ATOM   4507  C6    C C  61      33.139 145.751 263.598  1.00  0.00           C
ATOM   4508  P     A C  62      35.018 148.751 268.384  1.00  0.00           P
ATOM   4509  O1P   A C  62      35.866 149.124 269.521  1.00  0.00           O
ATOM   4510  O2P   A C  62      33.749 148.016 268.644  1.00  0.00           O
ATOM   4511  O5*   A C  62      34.638 150.072 267.571  1.00  0.00           O
ATOM   4512  C5*   A C  62      35.610 151.069 267.301  1.00  0.00           C
ATOM   4513  C4*   A C  62      34.950 152.269 266.679  1.00  0.00           C
ATOM   4514  O4*   A C  62      34.361 151.892 265.395  1.00  0.00           O
ATOM   4515  C3*   A C  62      33.757 152.785 267.454  1.00  0.00           C
ATOM   4516  O3*   A C  62      34.231 153.616 268.483  1.00  0.00           O
ATOM   4517  C2*   A C  62      33.018 153.557 266.370  1.00  0.00           C
ATOM   4518  O2*   A C  62      33.715 154.708 265.950  1.00  0.00           O
ATOM   4519  C1*   A C  62      33.133 152.582 265.215  1.00  0.00           C
ATOM   4520  N9    A C  62      32.060 151.594 265.127  1.00  0.00           N
ATOM   4521  C8    A C  62      32.118 150.265 265.444  1.00  0.00           C
ATOM   4522  N7    A C  62      31.036 149.593 265.124  1.00  0.00           N
ATOM   4523  C5    A C  62      30.191 150.558 264.591  1.00  0.00           C
ATOM   4524  C6    A C  62      28.915 150.482 264.017  1.00  0.00           C
ATOM   4525  N6    A C  62      28.200 149.342 263.915  1.00  0.00           N
ATOM   4526  N1    A C  62      28.376 151.625 263.542  1.00  0.00           N
ATOM   4527  C2    A C  62      29.084 152.763 263.647  1.00  0.00           C
ATOM   4528  N3    A C  62      30.289 152.961 264.161  1.00  0.00           N
ATOM   4529  C4    A C  62      30.800 151.804 264.616  1.00  0.00           C
ATOM   4530  P     C C  63      33.329 153.886 269.788  1.00  0.00           P
ATOM   4531  O1P   C C  63      34.205 154.750 270.589  1.00  0.00           O
ATOM   4532  O2P   C C  63      32.799 152.638 270.369  1.00  0.00           O
ATOM   4533  O5*   C C  63      32.102 154.737 269.263  1.00  0.00           O
ATOM   4534  C5*   C C  63      32.253 156.132 269.080  1.00  0.00           C
ATOM   4535  C4*   C C  63      31.008 156.709 268.477  1.00  0.00           C
ATOM   4536  O4*   C C  63      30.684 155.935 267.288  1.00  0.00           O
ATOM   4537  C3*   C C  63      29.755 156.584 269.324  1.00  0.00           C
ATOM   4538  O3*   C C  63      29.662 157.613 270.313  1.00  0.00           O
ATOM   4539  C2*   C C  63      28.687 156.734 268.257  1.00  0.00           C
ATOM   4540  O2*   C C  63      28.570 158.077 267.802  1.00  0.00           O
ATOM   4541  C1*   C C  63      29.273 155.874 267.136  1.00  0.00           C
ATOM   4542  N1    C C  63      28.846 154.455 267.152  1.00  0.00           N
ATOM   4543  C2    C C  63      27.638 154.118 266.561  1.00  0.00           C
ATOM   4544  O2    C C  63      26.959 155.036 266.050  1.00  0.00           O
ATOM   4545  N3    C C  63      27.229 152.806 266.565  1.00  0.00           N
ATOM   4546  C4    C C  63      28.005 151.876 267.150  1.00  0.00           C
ATOM   4547  N4    C C  63      27.609 150.613 267.146  1.00  0.00           N
ATOM   4548  C5    C C  63      29.240 152.209 267.762  1.00  0.00           C
ATOM   4549  C6    C C  63      29.621 153.494 267.736  1.00  0.00           C
ATOM   4550  P     A C  64      28.892 157.323 271.706  1.00  0.00           P
ATOM   4551  O1P   A C  64      29.108 158.468 272.620  1.00  0.00           O
ATOM   4552  O2P   A C  64      29.271 155.964 272.156  1.00  0.00           O
ATOM   4553  O5*   A C  64      27.374 157.372 271.278  1.00  0.00           O
ATOM   4554  C5*   A C  64      26.871 158.534 270.650  1.00  0.00           C
ATOM   4555  C4*   A C  64      25.441 158.331 270.245  1.00  0.00           C
ATOM   4556  O4*   A C  64      25.397 157.541 269.025  1.00  0.00           O
ATOM   4557  C3*   A C  64      24.573 157.539 271.207  1.00  0.00           C
ATOM   4558  O3*   A C  64      24.174 158.329 272.337  1.00  0.00           O
ATOM   4559  C2*   A C  64      23.432 157.145 270.275  1.00  0.00           C
ATOM   4560  O2*   A C  64      22.581 158.210 269.911  1.00  0.00           O
ATOM   4561  C1*   A C  64      24.219 156.742 269.028  1.00  0.00           C
ATOM   4562  N9    A C  64      24.619 155.348 269.143  1.00  0.00           N
ATOM   4563  C8    A C  64      25.782 154.817 269.629  1.00  0.00           C
ATOM   4564  N7    A C  64      25.790 153.512 269.655  1.00  0.00           N
ATOM   4565  C5    A C  64      24.553 153.169 269.136  1.00  0.00           C
ATOM   4566  C6    A C  64      23.958 151.940 268.876  1.00  0.00           C
ATOM   4567  N6    A C  64      24.545 150.777 269.139  1.00  0.00           N
ATOM   4568  N1    A C  64      22.724 151.943 268.330  1.00  0.00           N
ATOM   4569  C2    A C  64      22.147 153.115 268.061  1.00  0.00           C
ATOM   4570  N3    A C  64      22.610 154.339 268.261  1.00  0.00           N
ATOM   4571  C4    A C  64      23.831 154.287 268.809  1.00  0.00           C
ATOM   4572  P     G C  65      24.003 157.628 273.787  1.00  0.00           P
ATOM   4573  O1P   G C  65      23.815 158.679 274.820  1.00  0.00           O
ATOM   4574  O2P   G C  65      25.062 156.613 273.975  1.00  0.00           O
ATOM   4575  O5*   G C  65      22.623 156.851 273.653  1.00  0.00           O
ATOM   4576  C5*   G C  65      21.525 157.456 273.002  1.00  0.00           C
ATOM   4577  C4*   G C  65      20.553 156.410 272.516  1.00  0.00           C
ATOM   4578  O4*   G C  65      21.134 155.667 271.420  1.00  0.00           O
ATOM   4579  C3*   G C  65      20.114 155.309 273.472  1.00  0.00           C
ATOM   4580  O3*   G C  65      19.106 155.767 274.360  1.00  0.00           O
ATOM   4581  C2*   G C  65      19.494 154.339 272.486  1.00  0.00           C
ATOM   4582  O2*   G C  65      18.262 154.804 272.003  1.00  0.00           O
ATOM   4583  C1*   G C  65      20.509 154.396 271.340  1.00  0.00           C
ATOM   4584  N9    G C  65      21.519 153.367 271.558  1.00  0.00           N
ATOM   4585  C8    G C  65      22.812 153.530 271.965  1.00  0.00           C
ATOM   4586  N7    G C  65      23.450 152.405 272.094  1.00  0.00           N
ATOM   4587  C5    G C  65      22.513 151.444 271.745  1.00  0.00           C
ATOM   4588  C6    G C  65      22.639 150.041 271.646  1.00  0.00           C
ATOM   4589  O6    G C  65      23.633 149.333 271.890  1.00  0.00           O
```

| | | | | | | | | | | | |
|---|---|---|---|---|---|---|---|---|---|---|---|
| ATOM | 4590 | N1 | G | C | 65 | 21.452 | 149.455 | 271.210 | 1.00 | 0.00 | N |
| ATOM | 4591 | C2 | G | C | 65 | 20.297 | 150.146 | 270.902 | 1.00 | 0.00 | C |
| ATOM | 4592 | N2 | G | C | 65 | 19.251 | 149.426 | 270.488 | 1.00 | 0.00 | N |
| ATOM | 4593 | N3 | G | C | 65 | 20.178 | 151.449 | 270.988 | 1.00 | 0.00 | N |
| ATOM | 4594 | C4 | G | C | 65 | 21.320 | 152.028 | 271.414 | 1.00 | 0.00 | C |
| ATOM | 4595 | P | A | C | 66 | 18.915 | 155.056 | 275.797 | 1.00 | 0.00 | P |
| ATOM | 4596 | O1P | A | C | 66 | 17.967 | 155.867 | 276.594 | 1.00 | 0.00 | O |
| ATOM | 4597 | O2P | A | C | 66 | 20.262 | 154.778 | 276.332 | 1.00 | 0.00 | O |
| ATOM | 4598 | O5* | A | C | 66 | 18.214 | 153.672 | 275.444 | 1.00 | 0.00 | O |
| ATOM | 4599 | C5* | A | C | 66 | 16.906 | 153.650 | 274.903 | 1.00 | 0.00 | C |
| ATOM | 4600 | C4* | A | C | 66 | 16.518 | 152.242 | 274.555 | 1.00 | 0.00 | C |
| ATOM | 4601 | O4* | A | C | 66 | 17.507 | 151.686 | 273.656 | 1.00 | 0.00 | O |
| ATOM | 4602 | C3* | A | C | 66 | 16.544 | 151.279 | 275.715 | 1.00 | 0.00 | C |
| ATOM | 4603 | O3* | A | C | 66 | 15.366 | 151.412 | 276.491 | 1.00 | 0.00 | O |
| ATOM | 4604 | C2* | A | C | 66 | 16.629 | 149.948 | 274.986 | 1.00 | 0.00 | C |
| ATOM | 4605 | O2* | A | C | 66 | 15.409 | 149.546 | 274.397 | 1.00 | 0.00 | O |
| ATOM | 4606 | C1* | A | C | 66 | 17.614 | 150.289 | 273.870 | 1.00 | 0.00 | C |
| ATOM | 4607 | N9 | A | C | 66 | 19.017 | 149.985 | 274.171 | 1.00 | 0.00 | N |
| ATOM | 4608 | C8 | A | C | 66 | 19.994 | 150.894 | 274.485 | 1.00 | 0.00 | C |
| ATOM | 4609 | N7 | A | C | 66 | 21.177 | 150.357 | 274.684 | 1.00 | 0.00 | N |
| ATOM | 4610 | C5 | A | C | 66 | 20.966 | 149.005 | 274.487 | 1.00 | 0.00 | C |
| ATOM | 4611 | C6 | A | C | 66 | 21.831 | 147.896 | 274.560 | 1.00 | 0.00 | C |
| ATOM | 4612 | N6 | A | C | 66 | 23.111 | 147.992 | 274.860 | 1.00 | 0.00 | N |
| ATOM | 4613 | N1 | A | C | 66 | 21.316 | 146.676 | 274.330 | 1.00 | 0.00 | N |
| ATOM | 4614 | C2 | A | C | 66 | 20.002 | 146.579 | 274.066 | 1.00 | 0.00 | C |
| ATOM | 4615 | N3 | A | C | 66 | 19.084 | 147.545 | 273.975 | 1.00 | 0.00 | N |
| ATOM | 4616 | C4 | A | C | 66 | 19.637 | 148.751 | 274.190 | 1.00 | 0.00 | C |
| ATOM | 4617 | P | A | C | 67 | 15.420 | 151.147 | 278.076 | 1.00 | 0.00 | P |
| ATOM | 4618 | O1P | A | C | 67 | 14.088 | 151.493 | 278.625 | 1.00 | 0.00 | O |
| ATOM | 4619 | O2P | A | C | 67 | 16.640 | 151.773 | 278.657 | 1.00 | 0.00 | O |
| ATOM | 4620 | O5* | A | C | 67 | 15.526 | 149.580 | 278.165 | 1.00 | 0.00 | O |
| ATOM | 4621 | C5* | A | C | 67 | 14.475 | 148.771 | 277.668 | 1.00 | 0.00 | C |
| ATOM | 4622 | C4* | A | C | 67 | 14.899 | 147.333 | 277.687 | 1.00 | 0.00 | C |
| ATOM | 4623 | O4* | A | C | 67 | 16.003 | 147.190 | 276.762 | 1.00 | 0.00 | O |
| ATOM | 4624 | C3* | A | C | 67 | 15.505 | 146.904 | 279.007 | 1.00 | 0.00 | C |
| ATOM | 4625 | O3* | A | C | 67 | 14.496 | 146.436 | 279.876 | 1.00 | 0.00 | O |
| ATOM | 4626 | C2* | A | C | 67 | 16.344 | 145.720 | 278.575 | 1.00 | 0.00 | C |
| ATOM | 4627 | O2* | A | C | 67 | 15.500 | 144.614 | 278.302 | 1.00 | 0.00 | O |
| ATOM | 4628 | C1* | A | C | 67 | 16.945 | 146.259 | 277.281 | 1.00 | 0.00 | C |
| ATOM | 4629 | N9 | A | C | 67 | 18.236 | 146.931 | 277.494 | 1.00 | 0.00 | N |
| ATOM | 4630 | C8 | A | C | 67 | 18.478 | 148.262 | 277.690 | 1.00 | 0.00 | C |
| ATOM | 4631 | N7 | A | C | 67 | 19.759 | 148.550 | 277.837 | 1.00 | 0.00 | N |
| ATOM | 4632 | C5 | A | C | 67 | 20.393 | 147.324 | 277.743 | 1.00 | 0.00 | C |
| ATOM | 4633 | C6 | A | C | 67 | 21.762 | 146.940 | 277.848 | 1.00 | 0.00 | C |
| ATOM | 4634 | N6 | A | C | 67 | 22.761 | 147.787 | 278.044 | 1.00 | 0.00 | N |
| ATOM | 4635 | N1 | A | C | 67 | 22.059 | 145.631 | 277.742 | 1.00 | 0.00 | N |
| ATOM | 4636 | C2 | A | C | 67 | 21.051 | 144.768 | 277.553 | 1.00 | 0.00 | C |
| ATOM | 4637 | N3 | A | C | 67 | 19.735 | 145.003 | 277.436 | 1.00 | 0.00 | N |
| ATOM | 4638 | C4 | A | C | 67 | 19.472 | 146.316 | 277.536 | 1.00 | 0.00 | C |
| ATOM | 4639 | P | U | C | 68 | 14.758 | 146.419 | 281.460 | 1.00 | 0.00 | P |
| ATOM | 4640 | O1P | U | C | 68 | 13.436 | 146.113 | 282.054 | 1.00 | 0.00 | O |
| ATOM | 4641 | O2P | U | C | 68 | 15.531 | 147.619 | 281.911 | 1.00 | 0.00 | O |
| ATOM | 4642 | O5* | U | C | 68 | 15.693 | 145.155 | 281.704 | 1.00 | 0.00 | O |
| ATOM | 4643 | C5* | U | C | 68 | 15.265 | 143.861 | 281.366 | 1.00 | 0.00 | C |
| ATOM | 4644 | C4* | U | C | 68 | 16.401 | 142.902 | 281.554 | 1.00 | 0.00 | C |
| ATOM | 4645 | O4* | U | C | 68 | 17.431 | 143.158 | 280.551 | 1.00 | 0.00 | O |
| ATOM | 4646 | C3* | U | C | 68 | 17.151 | 143.065 | 282.867 | 1.00 | 0.00 | C |
| ATOM | 4647 | O3* | U | C | 68 | 16.454 | 142.389 | 283.899 | 1.00 | 0.00 | O |
| ATOM | 4648 | C2* | U | C | 68 | 18.461 | 142.363 | 282.536 | 1.00 | 0.00 | C |
| ATOM | 4649 | O2* | U | C | 68 | 18.296 | 140.955 | 282.484 | 1.00 | 0.00 | O |
| ATOM | 4650 | C1* | U | C | 68 | 18.705 | 142.886 | 281.115 | 1.00 | 0.00 | C |
| ATOM | 4651 | N1 | U | C | 68 | 19.506 | 144.119 | 281.119 | 1.00 | 0.00 | N |
| ATOM | 4652 | C2 | U | C | 68 | 20.874 | 143.941 | 281.266 | 1.00 | 0.00 | C |
| ATOM | 4653 | O2 | U | C | 68 | 21.385 | 142.824 | 281.383 | 1.00 | 0.00 | O |
| ATOM | 4654 | N3 | U | C | 68 | 21.616 | 145.093 | 281.274 | 1.00 | 0.00 | N |
| ATOM | 4655 | C4 | U | C | 68 | 21.148 | 146.385 | 281.157 | 1.00 | 0.00 | C |
| ATOM | 4656 | O4 | U | C | 68 | 21.957 | 147.330 | 281.200 | 1.00 | 0.00 | O |
| ATOM | 4657 | C5 | U | C | 68 | 19.710 | 146.495 | 281.021 | 1.00 | 0.00 | C |
| ATOM | 4658 | C6 | U | C | 68 | 18.963 | 145.375 | 281.001 | 1.00 | 0.00 | C |
| ATOM | 4659 | P | U | C | 69 | 16.646 | 142.852 | 285.410 | 1.00 | 0.00 | P |
| ATOM | 4660 | O1P | U | C | 69 | 15.813 | 141.981 | 286.286 | 1.00 | 0.00 | O |
| ATOM | 4661 | O2P | U | C | 69 | 16.465 | 144.311 | 285.418 | 1.00 | 0.00 | O |
| ATOM | 4662 | O5* | U | C | 69 | 18.176 | 142.568 | 285.756 | 1.00 | 0.00 | O |
| ATOM | 4663 | C5* | U | C | 69 | 18.692 | 141.258 | 285.661 | 1.00 | 0.00 | C |
| ATOM | 4664 | C4* | U | C | 69 | 20.198 | 141.279 | 285.831 | 1.00 | 0.00 | C |
| ATOM | 4665 | O4* | U | C | 69 | 20.831 | 141.896 | 284.671 | 1.00 | 0.00 | O |
| ATOM | 4666 | C3* | U | C | 69 | 20.699 | 142.098 | 287.004 | 1.00 | 0.00 | C |
| ATOM | 4667 | O3* | U | C | 69 | 20.602 | 141.302 | 288.186 | 1.00 | 0.00 | O |
| ATOM | 4668 | C2* | U | C | 69 | 22.142 | 142.367 | 286.597 | 1.00 | 0.00 | C |
| ATOM | 4669 | O2* | U | C | 69 | 23.039 | 141.289 | 286.808 | 1.00 | 0.00 | O |
| ATOM | 4670 | C1* | U | C | 69 | 21.983 | 142.584 | 285.096 | 1.00 | 0.00 | C |
| ATOM | 4671 | N1 | U | C | 69 | 21.828 | 144.006 | 284.789 | 1.00 | 0.00 | N |
| ATOM | 4672 | C2 | U | C | 69 | 22.982 | 144.762 | 284.786 | 1.00 | 0.00 | C |
| ATOM | 4673 | O2 | U | C | 69 | 24.102 | 144.272 | 284.989 | 1.00 | 0.00 | O |
| ATOM | 4674 | N3 | U | C | 69 | 22.786 | 146.097 | 284.541 | 1.00 | 0.00 | N |
| ATOM | 4675 | C4 | U | C | 69 | 21.586 | 146.722 | 284.287 | 1.00 | 0.00 | C |
| ATOM | 4676 | O4 | U | C | 69 | 21.566 | 147.933 | 284.087 | 1.00 | 0.00 | O |

```
ATOM   4677  C5    U C  69      20.446 145.859 284.289  1.00  0.00           C
ATOM   4678  C6    U C  69      20.605 144.564 284.534  1.00  0.00           C
ATOM   4679  P     C C  70      20.466 142.006 289.631  1.00  0.00           P
ATOM   4680  O1P   C C  70      20.014 140.925 290.576  1.00  0.00           O
ATOM   4681  O2P   C C  70      19.647 143.243 289.492  1.00  0.00           O
ATOM   4682  O5*   C C  70      21.961 142.447 289.949  1.00  0.00           O
ATOM   4683  C5*   C C  70      22.948 141.463 290.240  1.00  0.00           C
ATOM   4684  C4*   C C  70      24.327 142.081 290.226  1.00  0.00           C
ATOM   4685  O4*   C C  70      24.647 142.598 288.902  1.00  0.00           O
ATOM   4686  C3*   C C  70      24.552 143.279 291.123  1.00  0.00           C
ATOM   4687  O3*   C C  70      24.712 142.852 292.465  1.00  0.00           O
ATOM   4688  C2*   C C  70      25.851 143.813 290.531  1.00  0.00           C
ATOM   4689  O2*   C C  70      26.989 143.019 290.846  1.00  0.00           O
ATOM   4690  C1*   C C  70      25.545 143.682 289.039  1.00  0.00           C
ATOM   4691  N1    C C  70      24.892 144.879 288.501  1.00  0.00           N
ATOM   4692  C2    C C  70      25.696 145.941 288.132  1.00  0.00           C
ATOM   4693  O2    C C  70      26.920 145.815 288.267  1.00  0.00           O
ATOM   4694  N3    C C  70      25.136 147.073 287.641  1.00  0.00           N
ATOM   4695  C4    C C  70      23.806 147.155 287.511  1.00  0.00           C
ATOM   4696  N4    C C  70      23.287 148.299 287.012  1.00  0.00           N
ATOM   4697  C5    C C  70      22.948 146.069 287.880  1.00  0.00           C
ATOM   4698  C6    C C  70      23.530 144.957 288.365  1.00  0.00           C
ATOM   4699  P     G C  71      24.394 143.863 293.685  1.00  0.00           P
ATOM   4700  O1P   G C  71      24.509 143.022 294.908  1.00  0.00           O
ATOM   4701  O2P   G C  71      23.129 144.584 293.417  1.00  0.00           O
ATOM   4702  O5*   G C  71      25.556 144.964 293.615  1.00  0.00           O
ATOM   4703  C5*   G C  71      26.866 144.695 294.113  1.00  0.00           C
ATOM   4704  C4*   G C  71      27.841 145.792 293.718  1.00  0.00           C
ATOM   4705  O4*   G C  71      27.880 145.944 292.270  1.00  0.00           O
ATOM   4706  C3*   G C  71      27.588 147.211 294.219  1.00  0.00           C
ATOM   4707  O3*   G C  71      28.050 147.428 295.551  1.00  0.00           O
ATOM   4708  C2*   G C  71      28.454 148.005 293.257  1.00  0.00           C
ATOM   4709  O2*   G C  71      29.825 147.863 293.537  1.00  0.00           O
ATOM   4710  C1*   G C  71      28.126 147.307 291.940  1.00  0.00           C
ATOM   4711  N9    G C  71      26.910 147.883 291.369  1.00  0.00           N
ATOM   4712  C8    G C  71      25.632 147.390 291.453  1.00  0.00           C
ATOM   4713  N7    G C  71      24.752 148.151 290.859  1.00  0.00           N
ATOM   4714  C5    G C  71      25.497 149.202 290.343  1.00  0.00           C
ATOM   4715  C6    G C  71      25.093 150.338 289.589  1.00  0.00           C
ATOM   4716  O6    G C  71      23.947 150.663 289.214  1.00  0.00           O
ATOM   4717  N1    G C  71      26.181 151.150 289.277  1.00  0.00           N
ATOM   4718  C2    G C  71      27.477 150.905 289.648  1.00  0.00           C
ATOM   4719  N2    G C  71      28.387 151.809 289.258  1.00  0.00           N
ATOM   4720  N3    G C  71      27.859 149.860 290.346  1.00  0.00           N
ATOM   4721  C4    G C  71      26.830 149.053 290.654  1.00  0.00           C
ATOM   4722  P     C C  72      27.579 148.745 296.346  1.00  0.00           P
ATOM   4723  O1P   C C  72      28.421 148.890 297.554  1.00  0.00           O
ATOM   4724  O2P   C C  72      26.099 148.702 296.483  1.00  0.00           O
ATOM   4725  O5*   C C  72      27.964 149.945 295.382  1.00  0.00           O
ATOM   4726  C5*   C C  72      29.221 150.577 295.506  1.00  0.00           C
ATOM   4727  C4*   C C  72      29.178 151.924 294.854  1.00  0.00           C
ATOM   4728  O4*   C C  72      28.683 151.755 293.503  1.00  0.00           O
ATOM   4729  C3*   C C  72      28.184 152.906 295.442  1.00  0.00           C
ATOM   4730  O3*   C C  72      28.689 153.538 296.604  1.00  0.00           O
ATOM   4731  C2*   C C  72      28.022 153.885 294.290  1.00  0.00           C
ATOM   4732  O2*   C C  72      29.108 154.778 294.110  1.00  0.00           O
ATOM   4733  C1*   C C  72      27.980 152.919 293.112  1.00  0.00           C
ATOM   4734  N1    C C  72      26.603 152.544 292.789  1.00  0.00           N
ATOM   4735  C2    C C  72      25.865 153.412 291.997  1.00  0.00           C
ATOM   4736  O2    C C  72      26.401 154.475 291.622  1.00  0.00           O
ATOM   4737  N3    C C  72      24.596 153.086 291.660  1.00  0.00           N
ATOM   4738  C4    C C  72      24.069 151.939 292.097  1.00  0.00           C
ATOM   4739  N4    C C  72      22.817 151.647 291.737  1.00  0.00           N
ATOM   4740  C5    C C  72      24.806 151.038 292.924  1.00  0.00           C
ATOM   4741  C6    C C  72      26.057 151.377 293.242  1.00  0.00           C
ATOM   4742  P     A C  73      27.640 154.178 297.310  1.00  0.00           P
ATOM   4743  O1P   A C  73      28.690 154.566 298.281  1.00  0.00           O
ATOM   4744  O2P   A C  73      26.729 153.052 297.637  1.00  0.00           O
ATOM   4745  O5*   A C  73      26.795 155.480 296.952  1.00  0.00           O
ATOM   4746  C5*   A C  73      27.456 156.724 296.777  1.00  0.00           C
ATOM   4747  C4*   A C  73      26.475 157.794 296.387  1.00  0.00           C
ATOM   4748  O4*   A C  73      25.860 157.442 295.124  1.00  0.00           O
ATOM   4749  C3*   A C  73      25.285 157.968 297.311  1.00  0.00           C
ATOM   4750  O3*   A C  73      25.617 158.760 298.441  1.00  0.00           O
ATOM   4751  C2*   A C  73      24.309 158.696 296.403  1.00  0.00           C
ATOM   4752  O2*   A C  73      24.630 160.064 296.273  1.00  0.00           O
ATOM   4753  C1*   A C  73      24.533 157.945 295.086  1.00  0.00           C
ATOM   4754  N9    A C  73      23.624 156.806 294.952  1.00  0.00           N
ATOM   4755  C8    A C  73      23.901 155.484 295.183  1.00  0.00           C
ATOM   4756  N7    A C  73      22.873 154.692 295.009  1.00  0.00           N
ATOM   4757  C5    A C  73      21.850 155.549 294.631  1.00  0.00           C
ATOM   4758  C6    A C  73      20.502 155.325 294.302  1.00  0.00           C
ATOM   4759  N6    A C  73      19.931 154.119 294.312  1.00  0.00           N
ATOM   4760  N1    A C  73      19.751 156.397 293.957  1.00  0.00           N
ATOM   4761  C2    A C  73      20.328 157.608 293.953  1.00  0.00           C
ATOM   4762  N3    A C  73      21.584 157.945 294.245  1.00  0.00           N
ATOM   4763  C4    A C  73      22.301 156.854 294.583  1.00  0.00           C
```

```
ATOM   4764  P    C C  74    24.954 158.300 299.815  1.00  0.00           P
ATOM   4765  O1P  C C  74    24.776 156.792 299.645  1.00  0.00           O
ATOM   4766  O2P  C C  74    23.740 159.189 300.091  1.00  0.00           O
ATOM   4767  O5*  C C  74    26.075 158.557 300.943  1.00  0.00           O
ATOM   4768  C5*  C C  74    26.823 157.453 301.481  1.00  0.00           C
ATOM   4769  C4*  C C  74    28.301 157.781 301.553  1.00  0.00           C
ATOM   4770  O4*  C C  74    28.873 157.960 300.223  1.00  0.00           O
ATOM   4771  C3*  C C  74    28.723 159.016 302.330  1.00  0.00           C
ATOM   4772  O3*  C C  74    28.807 158.615 303.718  1.00  0.00           O
ATOM   4773  C2*  C C  74    30.122 159.257 301.779  1.00  0.00           C
ATOM   4774  O2*  C C  74    30.982 158.296 302.347  1.00  0.00           O
ATOM   4775  C1*  C C  74    29.976 158.843 300.304  1.00  0.00           C
ATOM   4776  N1   C C  74    29.889 159.847 299.232  1.00  0.00           N
ATOM   4777  C2   C C  74    31.047 160.509 298.805  1.00  0.00           C
ATOM   4778  O2   C C  74    32.123 160.237 299.359  1.00  0.00           O
ATOM   4779  N3   C C  74    30.964 161.420 297.811  1.00  0.00           N
ATOM   4780  C4   C C  74    29.786 161.691 297.248  1.00  0.00           C
ATOM   4781  N4   C C  74    29.751 162.596 296.268  1.00  0.00           N
ATOM   4782  C5   C C  74    28.590 161.022 297.655  1.00  0.00           C
ATOM   4783  C6   C C  74    28.688 160.120 298.637  1.00  0.00           C
ATOM   4784  P    C C  75    29.257 159.585 304.427  1.00  0.00           P
ATOM   4785  O1P  C C  75    29.751 158.819 305.598  1.00  0.00           O
ATOM   4786  O2P  C C  75    27.845 160.022 304.390  1.00  0.00           O
ATOM   4787  O5*  C C  75    30.161 160.890 304.579  1.00  0.00           O
ATOM   4788  C5*  C C  75    31.225 160.944 305.584  1.00  0.00           C
ATOM   4789  C4*  C C  75    31.809 162.347 305.785  1.00  0.00           C
ATOM   4790  O4*  C C  75    32.464 162.786 304.568  1.00  0.00           O
ATOM   4791  C3*  C C  75    30.858 163.479 306.131  1.00  0.00           C
ATOM   4792  O3*  C C  75    30.531 163.462 307.503  1.00  0.00           O
ATOM   4793  C2*  C C  75    31.648 164.708 305.717  1.00  0.00           C
ATOM   4794  O2*  C C  75    32.603 164.992 306.728  1.00  0.00           O
ATOM   4795  C1*  C C  75    32.357 164.187 304.462  1.00  0.00           C
ATOM   4796  N1   C C  75    31.679 164.405 303.199  1.00  0.00           N
ATOM   4797  C2   C C  75    32.317 165.208 302.269  1.00  0.00           C
ATOM   4798  O2   C C  75    33.396 165.728 302.581  1.00  0.00           O
ATOM   4799  N3   C C  75    31.736 165.440 301.077  1.00  0.00           N
ATOM   4800  C4   C C  75    30.557 164.891 300.797  1.00  0.00           C
ATOM   4801  N4   C C  75    30.031 165.128 299.596  1.00  0.00           N
ATOM   4802  C5   C C  75    29.896 164.024 301.715  1.00  0.00           C
ATOM   4803  C6   C C  75    30.491 163.806 302.893  1.00  0.00           C
ATOM   4804  P    A C  76    29.452 163.223 308.187  1.00  0.00           P
ATOM   4805  O1P  A C  76    30.073 162.737 309.445  1.00  0.00           O
ATOM   4806  O2P  A C  76    28.545 162.340 307.454  1.00  0.00           O
ATOM   4807  O5*  A C  76    28.385 164.387 308.346  1.00  0.00           O
ATOM   4808  C5*  A C  76    28.438 165.196 309.538  1.00  0.00           C
ATOM   4809  C4*  A C  76    28.534 166.644 309.114  1.00  0.00           C
ATOM   4810  O4*  A C  76    27.768 167.477 310.012  1.00  0.00           O
ATOM   4811  C3*  A C  76    29.916 167.224 309.129  1.00  0.00           C
ATOM   4812  O3*  A C  76    30.455 166.736 307.928  1.00  0.00           O
ATOM   4813  C2*  A C  76    29.636 168.728 309.230  1.00  0.00           C
ATOM   4814  O2*  A C  76    29.273 169.076 307.820  1.00  0.00           O
ATOM   4815  C1*  A C  76    28.368 168.760 310.089  1.00  0.00           C
ATOM   4816  N9   A C  76    28.446 169.177 311.472  1.00  0.00           N
ATOM   4817  C8   A C  76    28.750 168.437 312.583  1.00  0.00           C
ATOM   4818  N7   A C  76    28.725 169.128 313.698  1.00  0.00           N
ATOM   4819  C5   A C  76    28.375 170.405 313.287  1.00  0.00           C
ATOM   4820  C6   A C  76    28.192 171.604 313.987  1.00  0.00           C
ATOM   4821  N6   A C  76    28.314 171.712 315.314  1.00  0.00           N
ATOM   4822  N1   A C  76    27.817 172.686 313.284  1.00  0.00           N
ATOM   4823  C2   A C  76    27.672 172.578 311.959  1.00  0.00           C
ATOM   4824  N3   A C  76    27.834 171.514 311.184  1.00  0.00           N
ATOM   4825  C4   A C  76    28.174 170.443 311.923  1.00  0.00           C
TER    4826            A C  76
ATOM   4827  O3P  U D   1    62.763 141.465 272.908  1.00  0.00           O
ATOM   4828  P    U D   1    63.945 141.664 273.984  1.00  0.00           P
ATOM   4829  O1P  U D   1    65.104 142.074 273.146  1.00  0.00           O
ATOM   4830  O2P  U D   1    63.570 142.707 274.992  1.00  0.00           O
ATOM   4831  O5*  U D   1    64.094 140.221 274.654  1.00  0.00           O
ATOM   4832  C5*  U D   1    63.693 140.030 276.037  1.00  0.00           C
ATOM   4833  C4*  U D   1    64.926 139.590 276.781  1.00  0.00           C
ATOM   4834  O4*  U D   1    64.784 139.751 278.175  1.00  0.00           O
ATOM   4835  C3*  U D   1    65.278 138.098 276.598  1.00  0.00           C
ATOM   4836  O3*  U D   1    65.900 137.875 275.354  1.00  0.00           O
ATOM   4837  C2*  U D   1    66.130 137.837 277.836  1.00  0.00           C
ATOM   4838  O2*  U D   1    67.446 138.330 277.526  1.00  0.00           O
ATOM   4839  C1*  U D   1    65.482 138.704 278.879  1.00  0.00           C
ATOM   4840  N1   U D   1    64.509 138.009 279.739  1.00  0.00           N
ATOM   4841  C2   U D   1    64.884 137.722 281.039  1.00  0.00           C
ATOM   4842  O2   U D   1    66.003 138.034 281.451  1.00  0.00           O
ATOM   4843  N3   U D   1    63.984 137.090 281.848  1.00  0.00           N
ATOM   4844  C4   U D   1    62.745 136.742 281.406  1.00  0.00           C
ATOM   4845  O4   U D   1    61.969 136.156 282.226  1.00  0.00           O
ATOM   4846  C5   U D   1    62.364 137.044 280.072  1.00  0.00           C
ATOM   4847  C6   U D   1    63.263 137.671 279.290  1.00  0.00           C
ATOM   4848  P    C D   2    66.963 136.816 274.827  1.00  0.00           P
ATOM   4849  O1P  C D   2    68.017 137.490 274.010  1.00  0.00           O
ATOM   4850  O2P  C D   2    66.136 135.897 273.978  1.00  0.00           O
```

```
ATOM   4851  O5*   C D  2    67.604 136.118 276.111  1.00  0.00           O
ATOM   4852  C5*   C D  2    68.968 136.481 276.449  1.00  0.00           C
ATOM   4853  C4*   C D  2    69.419 135.653 277.633  1.00  0.00           C
ATOM   4854  O4*   C D  2    68.665 135.995 278.789  1.00  0.00           O
ATOM   4855  C3*   C D  2    69.226 134.151 277.494  1.00  0.00           C
ATOM   4856  O3*   C D  2    70.253 133.501 276.726  1.00  0.00           O
ATOM   4857  C2*   C D  2    69.203 133.684 278.948  1.00  0.00           C
ATOM   4858  O2*   C D  2    70.551 133.577 279.378  1.00  0.00           O
ATOM   4859  C1*   C D  2    68.499 134.854 279.617  1.00  0.00           C
ATOM   4860  N1    C D  2    67.079 134.465 279.801  1.00  0.00           N
ATOM   4861  C2    C D  2    66.798 133.593 280.837  1.00  0.00           C
ATOM   4862  O2    C D  2    67.705 133.186 281.563  1.00  0.00           O
ATOM   4863  N3    C D  2    65.498 133.216 281.024  1.00  0.00           N
ATOM   4864  C4    C D  2    64.494 133.679 280.218  1.00  0.00           C
ATOM   4865  N4    C D  2    63.249 133.289 280.439  1.00  0.00           N
ATOM   4866  C5    C D  2    64.807 134.572 279.153  1.00  0.00           C
ATOM   4867  C6    C D  2    66.089 134.927 278.984  1.00  0.00           C
ATOM   4868  P     C D  3    69.927 131.996 276.221  1.00  0.00           P
ATOM   4869  O1P   C D  3    70.908 131.543 275.183  1.00  0.00           O
ATOM   4870  O2P   C D  3    68.553 132.130 275.675  1.00  0.00           O
ATOM   4871  O5*   C D  3    70.059 131.154 277.564  1.00  0.00           O
ATOM   4872  C5*   C D  3    71.359 130.578 277.879  1.00  0.00           C
ATOM   4873  C4*   C D  3    71.044 129.338 278.698  1.00  0.00           C
ATOM   4874  O4*   C D  3    70.240 129.710 279.813  1.00  0.00           O
ATOM   4875  C3*   C D  3    70.241 128.271 277.988  1.00  0.00           C
ATOM   4876  O3*   C D  3    70.989 127.376 277.153  1.00  0.00           O
ATOM   4877  C2*   C D  3    69.598 127.532 279.166  1.00  0.00           C
ATOM   4878  O2*   C D  3    70.604 126.637 279.640  1.00  0.00           O
ATOM   4879  C1*   C D  3    69.354 128.664 280.126  1.00  0.00           C
ATOM   4880  N1    C D  3    67.936 129.074 279.974  1.00  0.00           N
ATOM   4881  C2    C D  3    66.993 128.393 280.705  1.00  0.00           C
ATOM   4882  O2    C D  3    67.324 127.481 281.461  1.00  0.00           O
ATOM   4883  N3    C D  3    65.688 128.766 280.566  1.00  0.00           N
ATOM   4884  C4    C D  3    65.312 129.775 279.731  1.00  0.00           C
ATOM   4885  N4    C D  3    64.014 130.093 279.630  1.00  0.00           N
ATOM   4886  C5    C D  3    66.295 130.466 278.979  1.00  0.00           C
ATOM   4887  C6    C D  3    67.571 130.088 279.128  1.00  0.00           C
ATOM   4888  P     G D  4    70.109 126.574 276.054  1.00  0.00           P
ATOM   4889  O1P   G D  4    70.979 126.036 274.953  1.00  0.00           O
ATOM   4890  O2P   G D  4    69.170 127.622 275.577  1.00  0.00           O
ATOM   4891  O5*   G D  4    69.445 125.423 276.910  1.00  0.00           O
ATOM   4892  C5*   G D  4    70.275 124.715 277.867  1.00  0.00           C
ATOM   4893  C4*   G D  4    69.344 123.958 278.797  1.00  0.00           C
ATOM   4894  O4*   G D  4    68.604 124.877 279.598  1.00  0.00           O
ATOM   4895  C3*   G D  4    68.262 123.116 278.108  1.00  0.00           C
ATOM   4896  O3*   G D  4    68.732 121.848 277.661  1.00  0.00           O
ATOM   4897  C2*   G D  4    67.210 123.001 279.202  1.00  0.00           C
ATOM   4898  O2*   G D  4    67.632 121.949 280.057  1.00  0.00           O
ATOM   4899  C1*   G D  4    67.309 124.351 279.877  1.00  0.00           C
ATOM   4900  N9    G D  4    66.220 125.204 279.367  1.00  0.00           N
ATOM   4901  C8    G D  4    66.286 126.282 278.526  1.00  0.00           C
ATOM   4902  N7    G D  4    65.107 126.815 278.274  1.00  0.00           N
ATOM   4903  C5    G D  4    64.222 126.043 279.002  1.00  0.00           C
ATOM   4904  C6    G D  4    62.810 126.112 279.145  1.00  0.00           C
ATOM   4905  O6    G D  4    62.040 126.920 278.626  1.00  0.00           O
ATOM   4906  N1    G D  4    62.272 125.150 279.968  1.00  0.00           N
ATOM   4907  C2    G D  4    63.042 124.210 280.592  1.00  0.00           C
ATOM   4908  N2    G D  4    62.364 123.343 281.359  1.00  0.00           N
ATOM   4909  N3    G D  4    64.363 124.103 280.488  1.00  0.00           N
ATOM   4910  C4    G D  4    64.886 125.043 279.684  1.00  0.00           C
ATOM   4911  P     U D  5    67.738 120.843 276.903  1.00  0.00           P
ATOM   4912  O1P   U D  5    68.291 119.456 276.817  1.00  0.00           O
ATOM   4913  O2P   U D  5    67.570 121.471 275.566  1.00  0.00           O
ATOM   4914  O5*   U D  5    66.427 120.893 277.828  1.00  0.00           O
ATOM   4915  C5*   U D  5    66.024 119.728 278.566  1.00  0.00           C
ATOM   4916  C4*   U D  5    64.509 119.688 278.548  1.00  0.00           C
ATOM   4917  O4*   U D  5    63.988 120.942 278.981  1.00  0.00           O
ATOM   4918  C3*   U D  5    63.882 119.470 277.161  1.00  0.00           C
ATOM   4919  O3*   U D  5    63.874 118.106 276.778  1.00  0.00           O
ATOM   4920  C2*   U D  5    62.486 120.063 277.361  1.00  0.00           C
ATOM   4921  O2*   U D  5    61.713 119.057 277.995  1.00  0.00           O
ATOM   4922  C1*   U D  5    62.767 121.227 278.298  1.00  0.00           C
ATOM   4923  N1    U D  5    62.826 122.479 277.515  1.00  0.00           N
ATOM   4924  C2    U D  5    61.622 123.146 277.367  1.00  0.00           C
ATOM   4925  O2    U D  5    60.580 122.694 277.872  1.00  0.00           O
ATOM   4926  N3    U D  5    61.576 124.311 276.655  1.00  0.00           N
ATOM   4927  C4    U D  5    62.725 124.822 276.090  1.00  0.00           C
ATOM   4928  O4    U D  5    62.602 125.910 275.442  1.00  0.00           O
ATOM   4929  C5    U D  5    63.958 124.134 276.242  1.00  0.00           C
ATOM   4930  C6    U D  5    63.954 122.993 276.946  1.00  0.00           C
ATOM   4931  P     G D  6    63.308 117.466 275.428  1.00  0.00           P
ATOM   4932  O1P   G D  6    63.381 115.964 275.501  1.00  0.00           O
ATOM   4933  O2P   G D  6    64.161 118.005 274.347  1.00  0.00           O
ATOM   4934  O5*   G D  6    61.781 117.911 275.349  1.00  0.00           O
ATOM   4935  C5*   G D  6    60.801 116.841 275.279  1.00  0.00           C
ATOM   4936  C4*   G D  6    59.462 117.412 275.675  1.00  0.00           C
ATOM   4937  O4*   G D  6    59.615 118.719 276.212  1.00  0.00           O
```

```
ATOM   4938 C3*   G D 6    58.506 117.611 274.504 1.00 0.00           C
ATOM   4939 O3*   G D 6    57.844 116.392 274.123 1.00 0.00           O
ATOM   4940 C2*   G D 6    57.550 118.674 275.033 1.00 0.00           C
ATOM   4941 O2*   G D 6    56.589 117.988 275.847 1.00 0.00           O
ATOM   4942 C1*   G D 6    58.490 119.520 275.857 1.00 0.00           C
ATOM   4943 N9    G D 6    58.901 120.687 275.051 1.00 0.00           N
ATOM   4944 C8    G D 6    60.140 120.997 274.597 1.00 0.00           C
ATOM   4945 N7    G D 6    60.198 122.103 273.892 1.00 0.00           N
ATOM   4946 C5    G D 6    58.876 122.554 273.892 1.00 0.00           C
ATOM   4947 C6    G D 6    58.271 123.699 273.307 1.00 0.00           C
ATOM   4948 O6    G D 6    58.825 124.580 272.641 1.00 0.00           O
ATOM   4949 N1    G D 6    56.928 123.799 273.526 1.00 0.00           N
ATOM   4950 C2    G D 6    56.224 122.874 274.249 1.00 0.00           C
ATOM   4951 N2    G D 6    54.912 123.120 274.372 1.00 0.00           N
ATOM   4952 N3    G D 6    56.740 121.789 274.820 1.00 0.00           N
ATOM   4953 C4    G D 6    58.066 121.686 274.599 1.00 0.00           C
ATOM   4954 P     A D 7    58.188 115.928 272.608 1.00 0.00           P
ATOM   4955 O1P   A D 7    58.407 114.451 272.551 1.00 0.00           O
ATOM   4956 O2P   A D 7    59.421 116.714 272.307 1.00 0.00           O
ATOM   4957 O5*   A D 7    56.876 116.390 271.823 1.00 0.00           O
ATOM   4958 C5*   A D 7    55.660 116.495 272.610 1.00 0.00           C
ATOM   4959 C4*   A D 7    54.730 117.433 271.858 1.00 0.00           C
ATOM   4960 O4*   A D 7    55.229 118.763 271.973 1.00 0.00           O
ATOM   4961 C3*   A D 7    54.621 117.145 270.353 1.00 0.00           C
ATOM   4962 O3*   A D 7    53.298 117.446 269.870 1.00 0.00           O
ATOM   4963 C2*   A D 7    55.614 118.135 269.762 1.00 0.00           C
ATOM   4964 O2*   A D 7    55.297 118.370 268.416 1.00 0.00           O
ATOM   4965 C1*   A D 7    55.450 119.319 270.673 1.00 0.00           C
ATOM   4966 N9    A D 7    56.635 120.178 270.603 1.00 0.00           N
ATOM   4967 C8    A D 7    57.945 119.878 270.844 1.00 0.00           C
ATOM   4968 N7    A D 7    58.770 120.887 270.682 1.00 0.00           N
ATOM   4969 C5    A D 7    57.942 121.940 270.308 1.00 0.00           C
ATOM   4970 C6    A D 7    58.216 123.293 269.994 1.00 0.00           C
ATOM   4971 N6    A D 7    59.411 123.835 270.005 1.00 0.00           N
ATOM   4972 N1    A D 7    57.126 124.045 269.663 1.00 0.00           N
ATOM   4973 C2    A D 7    55.869 123.517 269.646 1.00 0.00           C
ATOM   4974 N3    A D 7    55.539 122.253 269.932 1.00 0.00           N
ATOM   4975 C4    A D 7    56.630 121.523 270.252 1.00 0.00           C
HETATM 4976 N1    4SU D 8  52.722 113.480 266.990 1.00 0.00           N
HETATM 4977 C2    4SU D 8  53.228 112.194 267.026 1.00 0.00           C
HETATM 4978 N3    4SU D 8  53.243 111.611 268.268 1.00 0.00           N
HETATM 4979 C4    4SU D 8  52.811 112.166 269.452 1.00 0.00           C
HETATM 4980 C5    4SU D 8  52.303 113.502 269.339 1.00 0.00           C
HETATM 4981 C6    4SU D 8  52.275 114.100 268.140 1.00 0.00           C
HETATM 4982 O2    4SU D 8  53.632 111.616 266.038 1.00 0.00           O
HETATM 4983 S4    4SU D 8  52.887 111.310 270.890 1.00 0.00           S
HETATM 4984 C1*   4SU D 8  52.674 114.154 265.682 1.00 0.00           C
HETATM 4985 C2*   4SU D 8  51.322 114.027 264.981 1.00 0.00           C
HETATM 4986 O2*   4SU D 8  51.527 113.963 263.586 1.00 0.00           O
HETATM 4987 C3*   4SU D 8  50.638 115.312 265.428 1.00 0.00           C
HETATM 4988 C4*   4SU D 8  51.784 116.312 265.432 1.00 0.00           C
HETATM 4989 O3*   4SU D 8  49.602 115.716 264.535 1.00 0.00           O
HETATM 4990 O4*   4SU D 8  52.924 115.536 265.881 1.00 0.00           O
HETATM 4991 C5*   4SU D 8  51.610 117.499 266.351 1.00 0.00           C
HETATM 4992 O5*   4SU D 8  51.261 117.054 267.675 1.00 0.00           O
HETATM 4993 P     4SU D 8  51.664 117.894 268.965 1.00 0.00           P
HETATM 4994 O1P   4SU D 8  50.949 119.191 268.910 1.00 0.00           O
HETATM 4995 O2P   4SU D 8  51.509 117.023 270.156 1.00 0.00           O
ATOM   4996 P     A D 9    48.749 116.638 265.350 1.00 0.00           P
ATOM   4997 O1P   A D 9    48.062 117.959 265.239 1.00 0.00           O
ATOM   4998 O2P   A D 9    48.612 115.840 266.600 1.00 0.00           O
ATOM   4999 O5*   A D 9    48.291 115.708 264.140 1.00 0.00           O
ATOM   5000 C5*   A D 9    47.917 116.260 262.855 1.00 0.00           C
ATOM   5001 C4*   A D 9    46.816 115.424 262.240 1.00 0.00           C
ATOM   5002 O4*   A D 9    47.294 114.057 262.136 1.00 0.00           O
ATOM   5003 C3*   A D 9    45.541 115.373 263.071 1.00 0.00           C
ATOM   5004 O3*   A D 9    44.412 115.285 262.202 1.00 0.00           O
ATOM   5005 C2*   A D 9    45.712 114.098 263.893 1.00 0.00           C
ATOM   5006 O2*   A D 9    44.489 113.501 264.268 1.00 0.00           O
ATOM   5007 C1*   A D 9    46.515 113.202 262.946 1.00 0.00           C
ATOM   5008 N9    A D 9    47.429 112.304 263.657 1.00 0.00           N
ATOM   5009 C8    A D 9    47.835 112.399 264.967 1.00 0.00           C
ATOM   5010 N7    A D 9    48.644 111.440 265.344 1.00 0.00           N
ATOM   5011 C5    A D 9    48.789 110.659 264.207 1.00 0.00           C
ATOM   5012 C6    A D 9    49.518 109.486 263.958 1.00 0.00           C
ATOM   5013 N6    A D 9    50.275 108.876 264.870 1.00 0.00           N
ATOM   5014 N1    A D 9    49.448 108.954 262.719 1.00 0.00           N
ATOM   5015 C2    A D 9    48.698 109.573 261.801 1.00 0.00           C
ATOM   5016 N3    A D 9    47.969 110.681 261.912 1.00 0.00           N
ATOM   5017 C4    A D 9    48.054 111.183 263.159 1.00 0.00           C
ATOM   5018 P     A D 10   43.433 116.552 262.028 1.00 0.00           P
ATOM   5019 O1P   A D 10   42.377 116.197 261.052 1.00 0.00           O
ATOM   5020 O2P   A D 10   44.269 117.759 261.791 1.00 0.00           O
ATOM   5021 O5*   A D 10   42.720 116.696 263.444 1.00 0.00           O
ATOM   5022 C5*   A D 10   41.914 117.851 263.739 1.00 0.00           C
ATOM   5023 C4*   A D 10   40.962 117.552 264.872 1.00 0.00           C
ATOM   5024 O4*   A D 10   40.090 116.467 264.475 1.00 0.00           O
```

| | | | | | | | | | | |
|---|---|---|---|---|---|---|---|---|---|---|
| ATOM | 5025 | C3* | A | D | 10 | 41.603 | 117.084 | 266.169 | 1.00 | 0.00 | C |
| ATOM | 5026 | O3* | A | D | 10 | 41.986 | 118.188 | 266.978 | 1.00 | 0.00 | O |
| ATOM | 5027 | C2* | A | D | 10 | 40.498 | 116.257 | 266.816 | 1.00 | 0.00 | C |
| ATOM | 5028 | O2* | A | D | 10 | 39.556 | 117.029 | 267.534 | 1.00 | 0.00 | O |
| ATOM | 5029 | C1* | A | D | 10 | 39.816 | 115.645 | 265.594 | 1.00 | 0.00 | C |
| ATOM | 5030 | N9 | A | D | 10 | 40.313 | 114.308 | 265.303 | 1.00 | 0.00 | N |
| ATOM | 5031 | C8 | A | D | 10 | 40.897 | 113.837 | 264.152 | 1.00 | 0.00 | C |
| ATOM | 5032 | N7 | A | D | 10 | 41.229 | 112.572 | 264.209 | 1.00 | 0.00 | N |
| ATOM | 5033 | C5 | A | D | 10 | 40.842 | 112.184 | 265.483 | 1.00 | 0.00 | C |
| ATOM | 5034 | C6 | A | D | 10 | 40.919 | 110.961 | 266.165 | 1.00 | 0.00 | C |
| ATOM | 5035 | N6 | A | D | 10 | 41.431 | 109.849 | 265.629 | 1.00 | 0.00 | N |
| ATOM | 5036 | N1 | A | D | 10 | 40.449 | 110.914 | 267.430 | 1.00 | 0.00 | N |
| ATOM | 5037 | C2 | A | D | 10 | 39.932 | 112.032 | 267.963 | 1.00 | 0.00 | C |
| ATOM | 5038 | N3 | A | D | 10 | 39.800 | 113.239 | 267.422 | 1.00 | 0.00 | N |
| ATOM | 5039 | C4 | A | D | 10 | 40.280 | 113.246 | 266.170 | 1.00 | 0.00 | C |
| ATOM | 5040 | P | C | D | 11 | 43.424 | 118.189 | 267.693 | 1.00 | 0.00 | P |
| ATOM | 5041 | O1P | C | D | 11 | 43.677 | 119.577 | 268.163 | 1.00 | 0.00 | O |
| ATOM | 5042 | O2P | C | D | 11 | 44.389 | 117.533 | 266.768 | 1.00 | 0.00 | O |
| ATOM | 5043 | O5* | C | D | 11 | 43.235 | 117.252 | 268.968 | 1.00 | 0.00 | O |
| ATOM | 5044 | C5* | C | D | 11 | 42.403 | 117.661 | 270.071 | 1.00 | 0.00 | C |
| ATOM | 5045 | C4* | C | D | 11 | 42.134 | 116.486 | 270.980 | 1.00 | 0.00 | C |
| ATOM | 5046 | O4* | C | D | 11 | 41.473 | 115.445 | 270.214 | 1.00 | 0.00 | O |
| ATOM | 5047 | C3* | C | D | 11 | 43.359 | 115.800 | 271.566 | 1.00 | 0.00 | C |
| ATOM | 5048 | O3* | C | D | 11 | 43.799 | 116.407 | 272.772 | 1.00 | 0.00 | O |
| ATOM | 5049 | C2* | C | D | 11 | 42.860 | 114.389 | 271.836 | 1.00 | 0.00 | C |
| ATOM | 5050 | O2* | C | D | 11 | 42.173 | 114.297 | 273.067 | 1.00 | 0.00 | O |
| ATOM | 5051 | C1* | C | D | 11 | 41.897 | 114.171 | 270.671 | 1.00 | 0.00 | C |
| ATOM | 5052 | N1 | C | D | 11 | 42.550 | 113.464 | 269.560 | 1.00 | 0.00 | N |
| ATOM | 5053 | C2 | C | D | 11 | 42.798 | 112.094 | 269.693 | 1.00 | 0.00 | C |
| ATOM | 5054 | O2 | C | D | 11 | 42.436 | 111.517 | 270.730 | 1.00 | 0.00 | O |
| ATOM | 5055 | N3 | C | D | 11 | 43.420 | 111.431 | 268.691 | 1.00 | 0.00 | N |
| ATOM | 5056 | C4 | C | D | 11 | 43.790 | 112.087 | 267.590 | 1.00 | 0.00 | C |
| ATOM | 5057 | N4 | C | D | 11 | 44.410 | 111.397 | 266.633 | 1.00 | 0.00 | N |
| ATOM | 5058 | C5 | C | D | 11 | 43.540 | 113.482 | 267.422 | 1.00 | 0.00 | C |
| ATOM | 5059 | C6 | C | D | 11 | 42.924 | 114.124 | 268.423 | 1.00 | 0.00 | C |
| ATOM | 5060 | P | A | D | 12 | 45.181 | 115.925 | 273.446 | 1.00 | 0.00 | P |
| ATOM | 5061 | O1P | A | D | 12 | 45.233 | 116.507 | 274.814 | 1.00 | 0.00 | O |
| ATOM | 5062 | O2P | A | D | 12 | 46.280 | 116.202 | 272.481 | 1.00 | 0.00 | O |
| ATOM | 5063 | O5* | A | D | 12 | 45.039 | 114.340 | 273.576 | 1.00 | 0.00 | O |
| ATOM | 5064 | C5* | A | D | 12 | 44.605 | 113.731 | 274.807 | 1.00 | 0.00 | C |
| ATOM | 5065 | C4* | A | D | 12 | 45.110 | 112.308 | 274.898 | 1.00 | 0.00 | C |
| ATOM | 5066 | O4* | A | D | 12 | 44.551 | 111.524 | 273.814 | 1.00 | 0.00 | O |
| ATOM | 5067 | C3* | A | D | 12 | 46.616 | 112.113 | 274.788 | 1.00 | 0.00 | C |
| ATOM | 5068 | O3* | A | D | 12 | 47.232 | 112.259 | 276.067 | 1.00 | 0.00 | O |
| ATOM | 5069 | C2* | A | D | 12 | 46.729 | 110.677 | 274.285 | 1.00 | 0.00 | C |
| ATOM | 5070 | O2* | A | D | 12 | 46.645 | 109.741 | 275.344 | 1.00 | 0.00 | O |
| ATOM | 5071 | C1* | A | D | 12 | 45.485 | 110.547 | 273.402 | 1.00 | 0.00 | C |
| ATOM | 5072 | N9 | A | D | 12 | 45.744 | 110.739 | 271.976 | 1.00 | 0.00 | N |
| ATOM | 5073 | C8 | A | D | 12 | 45.579 | 111.887 | 271.246 | 1.00 | 0.00 | C |
| ATOM | 5074 | N7 | A | D | 12 | 45.875 | 111.753 | 269.977 | 1.00 | 0.00 | N |
| ATOM | 5075 | C5 | A | D | 12 | 46.263 | 110.427 | 269.862 | 1.00 | 0.00 | C |
| ATOM | 5076 | C6 | A | D | 12 | 46.691 | 109.658 | 268.767 | 1.00 | 0.00 | C |
| ATOM | 5077 | N6 | A | D | 12 | 46.803 | 110.132 | 267.525 | 1.00 | 0.00 | N |
| ATOM | 5078 | N1 | A | D | 12 | 47.007 | 108.363 | 268.992 | 1.00 | 0.00 | N |
| ATOM | 5079 | C2 | A | D | 12 | 46.895 | 107.885 | 270.237 | 1.00 | 0.00 | C |
| ATOM | 5080 | N3 | A | D | 12 | 46.501 | 108.509 | 271.347 | 1.00 | 0.00 | N |
| ATOM | 5081 | C4 | A | D | 12 | 46.194 | 109.792 | 271.090 | 1.00 | 0.00 | C |
| ATOM | 5082 | P | A | D | 13 | 48.827 | 112.465 | 276.177 | 1.00 | 0.00 | P |
| ATOM | 5083 | O1P | A | D | 13 | 49.191 | 112.369 | 277.614 | 1.00 | 0.00 | O |
| ATOM | 5084 | O2P | A | D | 13 | 49.177 | 113.686 | 275.419 | 1.00 | 0.00 | O |
| ATOM | 5085 | O5* | A | D | 13 | 49.436 | 111.188 | 275.445 | 1.00 | 0.00 | O |
| ATOM | 5086 | C5* | A | D | 13 | 49.471 | 109.916 | 276.117 | 1.00 | 0.00 | C |
| ATOM | 5087 | C4* | A | D | 13 | 50.163 | 108.889 | 275.261 | 1.00 | 0.00 | C |
| ATOM | 5088 | O4* | A | D | 13 | 49.374 | 108.650 | 274.069 | 1.00 | 0.00 | O |
| ATOM | 5089 | C3* | A | D | 13 | 51.536 | 109.286 | 274.745 | 1.00 | 0.00 | C |
| ATOM | 5090 | O3* | A | D | 13 | 52.563 | 109.034 | 275.699 | 1.00 | 0.00 | O |
| ATOM | 5091 | C2* | A | D | 13 | 51.674 | 108.449 | 273.476 | 1.00 | 0.00 | C |
| ATOM | 5092 | O2* | A | D | 13 | 52.110 | 107.122 | 273.704 | 1.00 | 0.00 | O |
| ATOM | 5093 | C1* | A | D | 13 | 50.233 | 108.439 | 272.962 | 1.00 | 0.00 | C |
| ATOM | 5094 | N9 | A | D | 13 | 49.999 | 109.513 | 272.003 | 1.00 | 0.00 | N |
| ATOM | 5095 | C8 | A | D | 13 | 49.636 | 110.813 | 272.266 | 1.00 | 0.00 | C |
| ATOM | 5096 | N7 | A | D | 13 | 49.502 | 111.554 | 271.194 | 1.00 | 0.00 | N |
| ATOM | 5097 | C5 | A | D | 13 | 49.798 | 110.682 | 270.152 | 1.00 | 0.00 | C |
| ATOM | 5098 | C6 | A | D | 13 | 49.831 | 110.854 | 268.755 | 1.00 | 0.00 | C |
| ATOM | 5099 | N6 | A | D | 13 | 49.555 | 112.009 | 268.141 | 1.00 | 0.00 | N |
| ATOM | 5100 | N1 | A | D | 13 | 50.162 | 109.780 | 268.000 | 1.00 | 0.00 | N |
| ATOM | 5101 | C2 | A | D | 13 | 50.439 | 108.617 | 268.617 | 1.00 | 0.00 | C |
| ATOM | 5102 | N3 | A | D | 13 | 50.442 | 108.334 | 269.919 | 1.00 | 0.00 | N |
| ATOM | 5103 | C4 | A | D | 13 | 50.107 | 109.423 | 270.637 | 1.00 | 0.00 | C |
| ATOM | 5104 | P | A | D | 14 | 54.096 | 109.299 | 275.303 | 1.00 | 0.00 | P |
| ATOM | 5105 | O1P | A | D | 14 | 54.942 | 109.134 | 276.514 | 1.00 | 0.00 | O |
| ATOM | 5106 | O2P | A | D | 14 | 54.158 | 110.568 | 274.528 | 1.00 | 0.00 | O |
| ATOM | 5107 | O5* | A | D | 14 | 54.411 | 108.100 | 274.308 | 1.00 | 0.00 | O |
| ATOM | 5108 | C5* | A | D | 14 | 55.616 | 108.067 | 273.556 | 1.00 | 0.00 | C |
| ATOM | 5109 | C4* | A | D | 14 | 55.741 | 106.737 | 272.871 | 1.00 | 0.00 | C |
| ATOM | 5110 | O4* | A | D | 14 | 54.561 | 106.501 | 272.070 | 1.00 | 0.00 | O |
| ATOM | 5111 | C3* | A | D | 14 | 56.907 | 106.638 | 271.907 | 1.00 | 0.00 | C |

```
ATOM   5112  O3*  A D  14    58.078 106.251 272.611  1.00  0.00           O
ATOM   5113  C2*  A D  14    56.433 105.591 270.903  1.00  0.00           C
ATOM   5114  O2*  A D  14    56.655 104.262 271.329  1.00  0.00           O
ATOM   5115  C1*  A D  14    54.927 105.856 270.866  1.00  0.00           C
ATOM   5116  N9   A D  14    54.503 106.705 269.755  1.00  0.00           N
ATOM   5117  C8   A D  14    53.887 107.932 269.816  1.00  0.00           C
ATOM   5118  N7   A D  14    53.584 108.429 268.643  1.00  0.00           N
ATOM   5119  C5   A D  14    54.041 107.470 267.750  1.00  0.00           C
ATOM   5120  C6   A D  14    54.008 107.395 266.348  1.00  0.00           C
ATOM   5121  N6   A D  14    53.453 108.326 265.573  1.00  0.00           N
ATOM   5122  N1   A D  14    54.563 106.310 265.764  1.00  0.00           N
ATOM   5123  C2   A D  14    55.102 105.367 266.544  1.00  0.00           C
ATOM   5124  N3   A D  14    55.183 105.318 267.872  1.00  0.00           N
ATOM   5125  C4   A D  14    54.626 106.413 268.419  1.00  0.00           C
ATOM   5126  P    G D  15    59.440 107.075 272.397  1.00  0.00           P
ATOM   5127  O1P  G D  15    60.132 107.185 273.710  1.00  0.00           O
ATOM   5128  O2P  G D  15    59.109 108.310 271.635  1.00  0.00           O
ATOM   5129  O5*  G D  15    60.289 106.119 271.451  1.00  0.00           O
ATOM   5130  C5*  G D  15    60.390 104.721 271.744  1.00  0.00           C
ATOM   5131  C4*  G D  15    60.317 103.920 270.474  1.00  0.00           C
ATOM   5132  O4*  G D  15    58.996 104.032 269.886  1.00  0.00           O
ATOM   5133  C3*  G D  15    61.255 104.387 269.379  1.00  0.00           C
ATOM   5134  O3*  G D  15    62.557 103.873 269.569  1.00  0.00           O
ATOM   5135  C2*  G D  15    60.582 103.865 268.116  1.00  0.00           C
ATOM   5136  O2*  G D  15    60.873 102.508 267.845  1.00  0.00           O
ATOM   5137  C1*  G D  15    59.103 104.023 268.473  1.00  0.00           C
ATOM   5138  N9   G D  15    58.586 105.288 267.971  1.00  0.00           N
ATOM   5139  C8   G D  15    58.334 106.430 268.690  1.00  0.00           C
ATOM   5140  N7   G D  15    57.900 107.412 267.951  1.00  0.00           N
ATOM   5141  C5   G D  15    57.859 106.882 266.668  1.00  0.00           C
ATOM   5142  C6   G D  15    57.474 107.476 265.446  1.00  0.00           C
ATOM   5143  O6   G D  15    57.092 108.627 265.244  1.00  0.00           O
ATOM   5144  N1   G D  15    57.577 106.581 264.385  1.00  0.00           N
ATOM   5145  C2   G D  15    58.003 105.279 264.492  1.00  0.00           C
ATOM   5146  N2   G D  15    58.031 104.568 263.353  1.00  0.00           N
ATOM   5147  N3   G D  15    58.372 104.718 265.627  1.00  0.00           N
ATOM   5148  C4   G D  15    58.274 105.569 266.669  1.00  0.00           C
ATOM   5149  P    C D  16    64.314 104.108 270.242  1.00  0.00           P
ATOM   5150  O1P  C D  16    64.558 102.676 269.940  1.00  0.00           O
ATOM   5151  O2P  C D  16    63.703 104.494 271.543  1.00  0.00           O
ATOM   5152  O5*  C D  16    65.672 104.912 270.044  1.00  0.00           O
ATOM   5153  C5*  C D  16    65.702 106.333 270.243  1.00  0.00           C
ATOM   5154  C4*  C D  16    67.015 106.760 270.849  1.00  0.00           C
ATOM   5155  O4*  C D  16    66.934 106.707 272.297  1.00  0.00           O
ATOM   5156  C3*  C D  16    68.232 105.913 270.523  1.00  0.00           C
ATOM   5157  O3*  C D  16    68.802 106.243 269.267  1.00  0.00           O
ATOM   5158  C2*  C D  16    69.180 106.250 271.666  1.00  0.00           C
ATOM   5159  O2*  C D  16    69.855 107.471 271.447  1.00  0.00           O
ATOM   5160  C1*  C D  16    68.210 106.402 272.834  1.00  0.00           C
ATOM   5161  N1   C D  16    68.107 105.166 273.626  1.00  0.00           N
ATOM   5162  C2   C D  16    69.152 104.848 274.503  1.00  0.00           C
ATOM   5163  O2   C D  16    70.112 105.629 274.600  1.00  0.00           O
ATOM   5164  N3   C D  16    69.083 103.704 275.227  1.00  0.00           N
ATOM   5165  C4   C D  16    68.027 102.893 275.096  1.00  0.00           C
ATOM   5166  N4   C D  16    68.003 101.771 275.827  1.00  0.00           N
ATOM   5167  C5   C D  16    66.945 103.198 274.213  1.00  0.00           C
ATOM   5168  C6   C D  16    67.029 104.334 273.503  1.00  0.00           C
ATOM   5169  P    G D  18    69.975 105.726 268.306  1.00  0.00           P
ATOM   5170  O1P  G D  18    70.151 104.310 268.730  1.00  0.00           O
ATOM   5171  O2P  G D  18    71.099 106.695 268.460  1.00  0.00           O
ATOM   5172  O5*  G D  18    69.493 105.744 266.787  1.00  0.00           O
ATOM   5173  C5*  G D  18    69.523 106.954 266.006  1.00  0.00           C
ATOM   5174  C4*  G D  18    69.099 106.655 264.593  1.00  0.00           C
ATOM   5175  O4*  G D  18    69.478 107.748 263.715  1.00  0.00           O
ATOM   5176  C3*  G D  18    69.705 105.388 263.999  1.00  0.00           C
ATOM   5177  O3*  G D  18    68.731 104.743 263.178  1.00  0.00           O
ATOM   5178  C2*  G D  18    70.817 105.935 263.110  1.00  0.00           C
ATOM   5179  O2*  G D  18    71.155 105.096 262.028  1.00  0.00           O
ATOM   5180  C1*  G D  18    70.176 107.226 262.610  1.00  0.00           C
ATOM   5181  N9   G D  18    71.098 108.231 262.091  1.00  0.00           N
ATOM   5182  C8   G D  18    72.362 108.515 262.534  1.00  0.00           C
ATOM   5183  N7   G D  18    72.962 109.431 261.819  1.00  0.00           N
ATOM   5184  C5   G D  18    72.028 109.779 260.855  1.00  0.00           C
ATOM   5185  C6   G D  18    72.112 110.716 259.781  1.00  0.00           C
ATOM   5186  O6   G D  18    73.066 111.433 259.451  1.00  0.00           O
ATOM   5187  N1   G D  18    70.927 110.760 259.049  1.00  0.00           N
ATOM   5188  C2   G D  18    69.813 110.003 259.307  1.00  0.00           C
ATOM   5189  N2   G D  18    68.767 110.187 258.486  1.00  0.00           N
ATOM   5190  N3   G D  18    69.726 109.124 260.294  1.00  0.00           N
ATOM   5191  C4   G D  18    70.863 109.064 261.019  1.00  0.00           C
ATOM   5192  P    G D  19    67.905 103.483 263.742  1.00  0.00           P
ATOM   5193  O1P  G D  19    66.830 103.988 264.635  1.00  0.00           O
ATOM   5194  O2P  G D  19    68.886 102.496 264.263  1.00  0.00           O
ATOM   5195  O5*  G D  19    67.206 102.881 262.441  1.00  0.00           O
ATOM   5196  C5*  G D  19    66.018 103.491 261.910  1.00  0.00           C
ATOM   5197  C4*  G D  19    65.812 103.090 260.468  1.00  0.00           C
ATOM   5198  O4*  G D  19    66.988 103.458 259.708  1.00  0.00           O
```

```
ATOM    5199  C3*   G  D  19      65.547 101.613 260.184  1.00  0.00           C
ATOM    5200  O3*   G  D  19      64.626 101.522 259.108  1.00  0.00           O
ATOM    5201  C2*   G  D  19      66.901 101.096 259.703  1.00  0.00           C
ATOM    5202  O2*   G  D  19      66.764 100.028 258.779  1.00  0.00           O
ATOM    5203  C1*   G  D  19      67.475 102.331 259.010  1.00  0.00           C
ATOM    5204  N9    G  D  19      68.933 102.400 259.019  1.00  0.00           N
ATOM    5205  C8    G  D  19      69.777 102.142 260.071  1.00  0.00           C
ATOM    5206  N7    G  D  19      71.035 102.316 259.768  1.00  0.00           N
ATOM    5207  C5    G  D  19      71.018 102.707 258.435  1.00  0.00           C
ATOM    5208  C6    G  D  19      72.082 103.045 257.559  1.00  0.00           C
ATOM    5209  O6    G  D  19      73.299 103.063 257.790  1.00  0.00           O
ATOM    5210  N1    G  D  19      71.611 103.392 256.292  1.00  0.00           N
ATOM    5211  C2    G  D  19      70.288 103.413 255.921  1.00  0.00           C
ATOM    5212  N2    G  D  19      70.030 103.791 254.660  1.00  0.00           N
ATOM    5213  N3    G  D  19      69.292 103.094 256.727  1.00  0.00           N
ATOM    5214  C4    G  D  19      69.723 102.756 257.957  1.00  0.00           C
HETATM  5215  P     H2U D  20     63.079 101.458 259.613  1.00  0.00           P
HETATM  5216  O1P   H2U D  20     63.452 102.803 260.123  1.00  0.00           O
HETATM  5217  O2P   H2U D  20     62.646 100.406 260.568  1.00  0.00           O
HETATM  5218  O5*   H2U D  20     61.942 101.614 258.510  1.00  0.00           O
HETATM  5219  C5*   H2U D  20     62.056 102.603 257.471  1.00  0.00           C
HETATM  5220  C4*   H2U D  20     60.712 103.238 257.215  1.00  0.00           C
HETATM  5221  O4*   H2U D  20     60.869 104.310 256.246  1.00  0.00           O
HETATM  5222  C3*   H2U D  20     59.658 102.300 256.640  1.00  0.00           C
HETATM  5223  O3*   H2U D  20     58.375 102.674 257.119  1.00  0.00           O
HETATM  5224  C1*   H2U D  20     60.057 104.054 255.119  1.00  0.00           C
HETATM  5225  C2*   H2U D  20     59.771 102.556 255.143  1.00  0.00           C
HETATM  5226  O2*   H2U D  20     58.605 102.240 254.417  1.00  0.00           O
HETATM  5227  N1    H2U D  20     60.788 104.495 253.931  1.00  0.00           N
HETATM  5228  C2    H2U D  20     60.465 105.665 253.346  1.00  0.00           C
HETATM  5229  O2    H2U D  20     59.468 106.318 253.613  1.00  0.00           O
HETATM  5230  N3    H2U D  20     61.357 106.094 252.401  1.00  0.00           N
HETATM  5231  C4    H2U D  20     62.695 105.775 252.337  1.00  0.00           C
HETATM  5232  O4    H2U D  20     63.472 106.478 251.681  1.00  0.00           O
HETATM  5233  C5    H2U D  20     63.104 104.559 253.100  1.00  0.00           C
HETATM  5234  C6    H2U D  20     61.904 103.686 253.403  1.00  0.00           C
HETATM  5235  P     H2U D  21     57.024 101.938 257.476  1.00  0.00           P
HETATM  5236  O1P   H2U D  21     57.106 102.204 258.934  1.00  0.00           O
HETATM  5237  O2P   H2U D  21     57.270 100.564 256.969  1.00  0.00           O
HETATM  5238  O5*   H2U D  21     55.598 102.417 256.949  1.00  0.00           O
HETATM  5239  C5*   H2U D  21     55.261 103.816 256.862  1.00  0.00           C
HETATM  5240  C4*   H2U D  21     54.413 104.216 258.047  1.00  0.00           C
HETATM  5241  O4*   H2U D  21     53.653 105.404 257.693  1.00  0.00           O
HETATM  5242  C3*   H2U D  21     53.387 103.183 258.491  1.00  0.00           C
HETATM  5243  O3*   H2U D  21     53.152 103.327 259.886  1.00  0.00           O
HETATM  5244  C1*   H2U D  21     52.269 105.111 257.715  1.00  0.00           C
HETATM  5245  C2*   H2U D  21     52.149 103.588 257.704  1.00  0.00           C
HETATM  5246  O2*   H2U D  21     50.946 103.149 258.307  1.00  0.00           O
HETATM  5247  N1    H2U D  21     51.662 105.772 256.543  1.00  0.00           N
HETATM  5248  C2    H2U D  21     50.518 106.492 256.727  1.00  0.00           C
HETATM  5249  O2    H2U D  21     49.689 106.251 257.592  1.00  0.00           O
HETATM  5250  N3    H2U D  21     50.332 107.530 255.852  1.00  0.00           N
HETATM  5251  C4    H2U D  21     50.786 107.584 254.565  1.00  0.00           C
HETATM  5252  O4    H2U D  21     50.432 108.501 253.823  1.00  0.00           O
HETATM  5253  C5    H2U D  21     51.704 106.490 254.171  1.00  0.00           C
HETATM  5254  C6    H2U D  21     52.519 106.025 255.358  1.00  0.00           C
ATOM    5255  P     A  D  22      52.660 102.391 260.868  1.00  0.00           P
ATOM    5256  O1P   A  D  22      54.013 101.858 261.183  1.00  0.00           O
ATOM    5257  O2P   A  D  22      51.636 101.500 260.259  1.00  0.00           O
ATOM    5258  O5*   A  D  22      52.023 102.974 262.200  1.00  0.00           O
ATOM    5259  C5*   A  D  22      52.807 103.032 263.397  1.00  0.00           C
ATOM    5260  C4*   A  D  22      52.757 101.708 264.090  1.00  0.00           C
ATOM    5261  O4*   A  D  22      53.667 101.759 265.190  1.00  0.00           O
ATOM    5262  C3*   A  D  22      51.385 101.317 264.642  1.00  0.00           C
ATOM    5263  O3*   A  D  22      50.684 100.479 263.731  1.00  0.00           O
ATOM    5264  C2*   A  D  22      51.746 100.608 265.925  1.00  0.00           C
ATOM    5265  O2*   A  D  22      52.142  99.264 265.730  1.00  0.00           O
ATOM    5266  C1*   A  D  22      52.950 101.435 266.348  1.00  0.00           C
ATOM    5267  N9    A  D  22      52.505 102.716 266.940  1.00  0.00           N
ATOM    5268  C8    A  D  22      52.167 103.906 266.369  1.00  0.00           C
ATOM    5269  N7    A  D  22      51.850 104.811 267.264  1.00  0.00           N
ATOM    5270  C5    A  D  22      51.988 104.139 268.483  1.00  0.00           C
ATOM    5271  C6    A  D  22      51.822 104.502 269.795  1.00  0.00           C
ATOM    5272  N6    A  D  22      51.429 105.694 270.185  1.00  0.00           N
ATOM    5273  N1    A  D  22      52.068 103.540 270.740  1.00  0.00           N
ATOM    5274  C2    A  D  22      52.451 102.319 270.343  1.00  0.00           C
ATOM    5275  N3    A  D  22      52.626 101.880 269.141  1.00  0.00           N
ATOM    5276  C4    A  D  22      52.396 102.832 268.240  1.00  0.00           C
ATOM    5277  P     U  D  23      49.077 100.546 263.646  1.00  0.00           P
ATOM    5278  O1P   U  D  23      48.558  99.231 263.180  1.00  0.00           O
ATOM    5279  O2P   U  D  23      48.719 101.775 262.903  1.00  0.00           O
ATOM    5280  O5*   U  D  23      48.607 100.724 265.154  1.00  0.00           O
ATOM    5281  C5*   U  D  23      48.849  99.699 266.124  1.00  0.00           C
ATOM    5282  C4*   U  D  23      48.531 100.210 267.504  1.00  0.00           C
ATOM    5283  O4*   U  D  23      49.419 101.313 267.818  1.00  0.00           O
ATOM    5284  C3*   U  D  23      47.137 100.791 267.675  1.00  0.00           C
ATOM    5285  O3*   U  D  23      46.161  99.794 267.948  1.00  0.00           O
```

```
ATOM   5286  C2*   U D  23    47.319 101.751 268.838  1.00  0.00           C
ATOM   5287  O2*   U D  23    47.297 101.085 270.073  1.00  0.00           O
ATOM   5288  C1*   U D  23    48.727 102.282 268.587  1.00  0.00           C
ATOM   5289  N1    U D  23    48.676 103.535 267.823  1.00  0.00           N
ATOM   5290  C2    U D  23    48.327 104.697 268.501  1.00  0.00           C
ATOM   5291  O2    U D  23    48.088 104.729 269.701  1.00  0.00           O
ATOM   5292  N3    U D  23    48.264 105.822 267.716  1.00  0.00           N
ATOM   5293  C4    U D  23    48.516 105.909 266.359  1.00  0.00           C
ATOM   5294  O4    U D  23    48.382 106.992 265.786  1.00  0.00           O
ATOM   5295  C5    U D  23    48.885 104.670 265.739  1.00  0.00           C
ATOM   5296  C6    U D  23    48.951 103.556 266.474  1.00  0.00           C
ATOM   5297  P     G D  24    44.616 100.081 267.606  1.00  0.00           P
ATOM   5298  O1P   G D  24    43.917  98.773 267.592  1.00  0.00           O
ATOM   5299  O2P   G D  24    44.563 100.953 266.407  1.00  0.00           O
ATOM   5300  O5*   G D  24    44.098 100.931 268.851  1.00  0.00           O
ATOM   5301  C5*   G D  24    44.288 100.454 270.189  1.00  0.00           C
ATOM   5302  C4*   G D  24    44.069 101.570 271.178  1.00  0.00           C
ATOM   5303  O4*   G D  24    44.992 102.653 270.890  1.00  0.00           O
ATOM   5304  C3*   G D  24    42.700 102.232 271.158  1.00  0.00           C
ATOM   5305  O3*   G D  24    41.735 101.508 271.916  1.00  0.00           O
ATOM   5306  C2*   G D  24    42.991 103.602 271.764  1.00  0.00           C
ATOM   5307  O2*   G D  24    43.039 103.583 273.178  1.00  0.00           O
ATOM   5308  C1*   G D  24    44.389 103.895 271.221  1.00  0.00           C
ATOM   5309  N9    G D  24    44.345 104.743 270.024  1.00  0.00           N
ATOM   5310  C8    G D  24    44.652 104.389 268.733  1.00  0.00           C
ATOM   5311  N7    G D  24    44.502 105.374 267.886  1.00  0.00           N
ATOM   5312  C5    G D  24    44.072 106.443 268.665  1.00  0.00           C
ATOM   5313  C6    G D  24    43.749 107.780 268.305  1.00  0.00           C
ATOM   5314  O6    G D  24    43.781 108.309 267.190  1.00  0.00           O
ATOM   5315  N1    G D  24    43.353 108.527 269.409  1.00  0.00           N
ATOM   5316  C2    G D  24    43.280 108.052 270.697  1.00  0.00           C
ATOM   5317  N2    G D  24    42.874 108.929 271.630  1.00  0.00           N
ATOM   5318  N3    G D  24    43.583 106.815 271.045  1.00  0.00           N
ATOM   5319  C4    G D  24    43.968 106.068 269.991  1.00  0.00           C
ATOM   5320  P     U D  25    40.435 101.974 270.709  1.00  0.00           P
ATOM   5321  O1P   U D  25    39.435 100.894 270.923  1.00  0.00           O
ATOM   5322  O2P   U D  25    41.092 102.110 269.381  1.00  0.00           O
ATOM   5323  O5*   U D  25    39.746 103.369 271.074  1.00  0.00           O
ATOM   5324  C5*   U D  25    39.202 103.612 272.393  1.00  0.00           C
ATOM   5325  C4*   U D  25    38.979 105.094 272.616  1.00  0.00           C
ATOM   5326  O4*   U D  25    40.187 105.828 272.279  1.00  0.00           O
ATOM   5327  C3*   U D  25    37.895 105.745 271.771  1.00  0.00           C
ATOM   5328  O3*   U D  25    36.592 105.567 272.309  1.00  0.00           O
ATOM   5329  C2*   U D  25    38.322 107.208 271.756  1.00  0.00           C
ATOM   5330  O2*   U D  25    37.917 107.915 272.913  1.00  0.00           O
ATOM   5331  C1*   U D  25    39.845 107.086 271.721  1.00  0.00           C
ATOM   5332  N1    U D  25    40.345 107.128 270.338  1.00  0.00           N
ATOM   5333  C2    U D  25    40.205 108.309 269.628  1.00  0.00           C
ATOM   5334  O2    U D  25    39.751 109.329 270.120  1.00  0.00           O
ATOM   5335  N3    U D  25    40.628 108.254 268.324  1.00  0.00           N
ATOM   5336  C4    U D  25    41.170 107.167 267.671  1.00  0.00           C
ATOM   5337  O4    U D  25    41.422 107.247 266.466  1.00  0.00           O
ATOM   5338  C5    U D  25    41.312 105.996 268.480  1.00  0.00           C
ATOM   5339  C6    U D  25    40.905 106.016 269.753  1.00  0.00           C
ATOM   5340  P     A D  26    34.783 105.490 272.317  1.00  0.00           P
ATOM   5341  O1P   A D  26    34.020 105.632 273.580  1.00  0.00           O
ATOM   5342  O2P   A D  26    34.546 104.333 271.422  1.00  0.00           O
ATOM   5343  O5*   A D  26    34.655 106.841 271.453  1.00  0.00           O
ATOM   5344  C5*   A D  26    34.550 108.130 272.058  1.00  0.00           C
ATOM   5345  C4*   A D  26    34.840 109.251 271.057  1.00  0.00           C
ATOM   5346  O4*   A D  26    36.244 109.362 270.754  1.00  0.00           O
ATOM   5347  C3*   A D  26    34.262 108.923 269.703  1.00  0.00           C
ATOM   5348  O3*   A D  26    32.845 109.126 269.670  1.00  0.00           O
ATOM   5349  C2*   A D  26    34.968 109.927 268.826  1.00  0.00           C
ATOM   5350  O2*   A D  26    34.510 111.273 269.050  1.00  0.00           O
ATOM   5351  C1*   A D  26    36.380 109.797 269.375  1.00  0.00           C
ATOM   5352  N9    A D  26    37.121 108.815 268.539  1.00  0.00           N
ATOM   5353  C8    A D  26    37.448 107.513 268.810  1.00  0.00           C
ATOM   5354  N7    A D  26    38.131 106.921 267.871  1.00  0.00           N
ATOM   5355  C5    A D  26    38.271 107.903 266.900  1.00  0.00           C
ATOM   5356  C6    A D  26    38.896 107.918 265.641  1.00  0.00           C
ATOM   5357  N6    A D  26    39.505 106.859 265.121  1.00  0.00           N
ATOM   5358  N1    A D  26    38.844 109.046 264.937  1.00  0.00           N
ATOM   5359  C2    A D  26    38.214 110.087 265.443  1.00  0.00           C
ATOM   5360  N3    A D  26    37.586 110.211 266.606  1.00  0.00           N
ATOM   5361  C4    A D  26    37.659 109.059 267.296  1.00  0.00           C
ATOM   5362  P     C D  27    32.199 108.399 268.756  1.00  0.00           P
ATOM   5363  O1P   C D  27    30.822 108.733 269.182  1.00  0.00           O
ATOM   5364  O2P   C D  27    32.709 107.016 268.885  1.00  0.00           O
ATOM   5365  O5*   C D  27    32.399 108.842 267.224  1.00  0.00           O
ATOM   5366  C5*   C D  27    31.996 110.114 266.706  1.00  0.00           C
ATOM   5367  C4*   C D  27    32.595 110.337 265.319  1.00  0.00           C
ATOM   5368  O4*   C D  27    34.032 110.254 265.341  1.00  0.00           O
ATOM   5369  C3*   C D  27    32.215 109.193 264.404  1.00  0.00           C
ATOM   5370  O3*   C D  27    30.890 109.374 263.893  1.00  0.00           O
ATOM   5371  C2*   C D  27    33.262 109.259 263.320  1.00  0.00           C
ATOM   5372  O2*   C D  27    33.066 110.380 262.440  1.00  0.00           O
```

```
ATOM   5373  C1*   C D  27    34.492 109.513 264.186  1.00  0.00           C
ATOM   5374  N1    C D  27    35.121 108.208 264.569  1.00  0.00           N
ATOM   5375  C2    C D  27    36.014 107.631 263.673  1.00  0.00           C
ATOM   5376  O2    C D  27    36.290 108.170 262.602  1.00  0.00           O
ATOM   5377  N3    C D  27    36.590 106.448 264.008  1.00  0.00           N
ATOM   5378  C4    C D  27    36.317 105.842 265.165  1.00  0.00           C
ATOM   5379  N4    C D  27    36.918 104.692 265.458  1.00  0.00           N
ATOM   5380  C5    C D  27    35.405 106.416 266.099  1.00  0.00           C
ATOM   5381  C6    C D  27    34.840 107.589 265.758  1.00  0.00           C
ATOM   5382  P     C D  28    30.051 108.043 263.538  1.00  0.00           P
ATOM   5383  O1P   C D  28    28.859 108.927 263.544  1.00  0.00           O
ATOM   5384  O2P   C D  28    30.090 106.825 264.382  1.00  0.00           O
ATOM   5385  O5*   C D  28    30.409 107.618 262.029  1.00  0.00           O
ATOM   5386  C5*   C D  28    30.172 108.456 260.887  1.00  0.00           C
ATOM   5387  C4*   C D  28    30.953 107.939 259.684  1.00  0.00           C
ATOM   5388  O4*   C D  28    32.362 107.856 259.984  1.00  0.00           O
ATOM   5389  C3*   C D  28    30.567 106.501 259.390  1.00  0.00           C
ATOM   5390  O3*   C D  28    29.418 106.408 258.539  1.00  0.00           O
ATOM   5391  C2*   C D  28    31.779 105.957 258.677  1.00  0.00           C
ATOM   5392  O2*   C D  28    31.872 106.424 257.319  1.00  0.00           O
ATOM   5393  C1*   C D  28    32.891 106.601 259.492  1.00  0.00           C
ATOM   5394  N1    C D  28    33.316 105.687 260.608  1.00  0.00           N
ATOM   5395  C2    C D  28    34.191 104.645 260.309  1.00  0.00           C
ATOM   5396  O2    C D  28    34.585 104.439 259.162  1.00  0.00           O
ATOM   5397  N3    C D  28    34.608 103.842 261.323  1.00  0.00           N
ATOM   5398  C4    C D  28    34.196 104.034 262.581  1.00  0.00           C
ATOM   5399  N4    C D  28    34.634 103.235 263.551  1.00  0.00           N
ATOM   5400  C5    C D  28    33.294 105.092 262.909  1.00  0.00           C
ATOM   5401  C6    C D  28    32.889 105.881 261.897  1.00  0.00           C
ATOM   5402  P     G D  29    28.246 105.401 258.969  1.00  0.00           P
ATOM   5403  O1P   G D  29    27.827 105.401 257.550  1.00  0.00           O
ATOM   5404  O2P   G D  29    27.335 105.922 260.016  1.00  0.00           O
ATOM   5405  O5*   G D  29    28.728 103.918 259.385  1.00  0.00           O
ATOM   5406  C5*   G D  29    28.578 102.729 258.597  1.00  0.00           C
ATOM   5407  C4*   G D  29    29.538 102.596 257.419  1.00  0.00           C
ATOM   5408  O4*   G D  29    30.849 103.110 257.697  1.00  0.00           O
ATOM   5409  C3*   G D  29    29.772 101.109 257.215  1.00  0.00           C
ATOM   5410  O3*   G D  29    28.829 100.558 256.283  1.00  0.00           O
ATOM   5411  C2*   G D  29    31.186 101.002 256.698  1.00  0.00           C
ATOM   5412  O2*   G D  29    31.301 101.427 255.336  1.00  0.00           O
ATOM   5413  C1*   G D  29    31.836 102.060 257.588  1.00  0.00           C
ATOM   5414  N9    G D  29    32.156 101.564 258.964  1.00  0.00           N
ATOM   5415  C8    G D  29    31.807 102.128 260.171  1.00  0.00           C
ATOM   5416  N7    G D  29    32.255 101.496 261.213  1.00  0.00           N
ATOM   5417  C5    G D  29    32.957 100.428 260.674  1.00  0.00           C
ATOM   5418  C6    G D  29    33.663  99.397 261.339  1.00  0.00           C
ATOM   5419  O6    G D  29    33.816  99.239 262.547  1.00  0.00           O
ATOM   5420  N1    G D  29    34.233  98.511 260.441  1.00  0.00           N
ATOM   5421  C2    G D  29    34.137  98.600 259.071  1.00  0.00           C
ATOM   5422  N2    G D  29    34.759  97.651 258.382  1.00  0.00           N
ATOM   5423  N3    G D  29    33.472  99.569 258.436  1.00  0.00           N
ATOM   5424  C4    G D  29    32.906 100.451 259.300  1.00  0.00           C
ATOM   5425  P     G D  30    27.913  99.325 256.784  1.00  0.00           P
ATOM   5426  O1P   G D  30    26.961 100.435 256.540  1.00  0.00           O
ATOM   5427  O2P   G D  30    28.022  98.758 258.146  1.00  0.00           O
ATOM   5428  O5*   G D  30    27.487  98.125 255.807  1.00  0.00           O
ATOM   5429  C5*   G D  30    28.411  97.383 255.006  1.00  0.00           C
ATOM   5430  C4*   G D  30    29.402  96.497 255.772  1.00  0.00           C
ATOM   5431  O4*   G D  30    30.304  97.262 256.576  1.00  0.00           O
ATOM   5432  C3*   G D  30    28.743  95.669 256.853  1.00  0.00           C
ATOM   5433  O3*   G D  30    27.892  94.620 256.359  1.00  0.00           O
ATOM   5434  C2*   G D  30    29.979  95.076 257.480  1.00  0.00           C
ATOM   5435  O2*   G D  30    30.580  94.051 256.672  1.00  0.00           O
ATOM   5436  C1*   G D  30    30.903  96.293 257.470  1.00  0.00           C
ATOM   5437  N9    G D  30    31.009  96.733 258.880  1.00  0.00           N
ATOM   5438  C8    G D  30    30.475  97.823 259.517  1.00  0.00           C
ATOM   5439  N7    G D  30    30.741  97.882 260.789  1.00  0.00           N
ATOM   5440  C5    G D  30    31.509  96.748 261.015  1.00  0.00           C
ATOM   5441  C6    G D  30    32.088  96.276 262.214  1.00  0.00           C
ATOM   5442  O6    G D  30    32.031  96.786 263.329  1.00  0.00           O
ATOM   5443  N1    G D  30    32.780  95.091 262.006  1.00  0.00           N
ATOM   5444  C2    G D  30    32.897  94.443 260.795  1.00  0.00           C
ATOM   5445  N2    G D  30    33.590  93.311 260.778  1.00  0.00           N
ATOM   5446  N3    G D  30    32.356  94.889 259.668  1.00  0.00           N
ATOM   5447  C4    G D  30    31.678  96.043 259.856  1.00  0.00           C
ATOM   5448  P     A D  31    26.886  93.861 257.381  1.00  0.00           P
ATOM   5449  O1P   A D  31    25.870  93.182 256.546  1.00  0.00           O
ATOM   5450  O2P   A D  31    26.441  94.855 258.385  1.00  0.00           O
ATOM   5451  O5*   A D  31    27.736  92.732 258.143  1.00  0.00           O
ATOM   5452  C5*   A D  31    28.154  91.551 257.457  1.00  0.00           C
ATOM   5453  C4*   A D  31    29.044  90.678 258.326  1.00  0.00           C
ATOM   5454  O4*   A D  31    30.201  91.390 258.799  1.00  0.00           O
ATOM   5455  C3*   A D  31    28.331  90.329 259.606  1.00  0.00           C
ATOM   5456  O3*   A D  31    27.373  89.284 259.398  1.00  0.00           O
ATOM   5457  C2*   A D  31    29.481  89.880 260.477  1.00  0.00           C
ATOM   5458  O2*   A D  31    30.062  88.649 260.020  1.00  0.00           O
ATOM   5459  C1*   A D  31    30.436  91.021 260.184  1.00  0.00           C
```

| | | | | | | | | | | |
|---|---|---|---|---|---|---|---|---|---|---|
| ATOM | 5460 | N9 | A | D | 31 | 30.153 | 92.143 | 261.128 | 1.00 | 0.00 | N |
| ATOM | 5461 | C8 | A | D | 31 | 29.547 | 93.359 | 260.893 | 1.00 | 0.00 | C |
| ATOM | 5462 | N7 | A | D | 31 | 29.485 | 94.137 | 261.933 | 1.00 | 0.00 | N |
| ATOM | 5463 | C5 | A | D | 31 | 30.090 | 93.391 | 262.934 | 1.00 | 0.00 | C |
| ATOM | 5464 | C6 | A | D | 31 | 30.342 | 93.660 | 264.279 | 1.00 | 0.00 | C |
| ATOM | 5465 | N6 | A | D | 31 | 30.004 | 94.806 | 264.854 | 1.00 | 0.00 | N |
| ATOM | 5466 | N1 | A | D | 31 | 30.952 | 92.712 | 264.997 | 1.00 | 0.00 | N |
| ATOM | 5467 | C2 | A | D | 31 | 31.288 | 91.575 | 264.409 | 1.00 | 0.00 | C |
| ATOM | 5468 | N3 | A | D | 31 | 31.114 | 91.197 | 263.156 | 1.00 | 0.00 | N |
| ATOM | 5469 | C4 | A | D | 31 | 30.497 | 92.176 | 262.460 | 1.00 | 0.00 | C |
| ATOM | 5470 | P | U | D | 32 | 26.084 | 89.227 | 260.380 | 1.00 | 0.00 | P |
| ATOM | 5471 | O1P | U | D | 32 | 25.372 | 89.157 | 259.081 | 1.00 | 0.00 | O |
| ATOM | 5472 | O2P | U | D | 32 | 25.329 | 89.462 | 261.634 | 1.00 | 0.00 | O |
| ATOM | 5473 | O5* | U | D | 32 | 27.053 | 87.937 | 260.546 | 1.00 | 0.00 | O |
| ATOM | 5474 | C5* | U | D | 32 | 26.926 | 86.872 | 261.492 | 1.00 | 0.00 | C |
| ATOM | 5475 | C4* | U | D | 32 | 27.493 | 87.122 | 262.911 | 1.00 | 0.00 | C |
| ATOM | 5476 | O4* | U | D | 32 | 28.306 | 88.300 | 263.075 | 1.00 | 0.00 | O |
| ATOM | 5477 | C3* | U | D | 32 | 26.374 | 87.460 | 263.840 | 1.00 | 0.00 | C |
| ATOM | 5478 | O3* | U | D | 32 | 25.513 | 86.345 | 264.057 | 1.00 | 0.00 | O |
| ATOM | 5479 | C2* | U | D | 32 | 27.156 | 87.781 | 265.090 | 1.00 | 0.00 | C |
| ATOM | 5480 | O2* | U | D | 32 | 27.652 | 86.594 | 265.742 | 1.00 | 0.00 | O |
| ATOM | 5481 | C1* | U | D | 32 | 28.334 | 88.571 | 264.506 | 1.00 | 0.00 | C |
| ATOM | 5482 | N1 | U | D | 32 | 28.084 | 89.986 | 264.925 | 1.00 | 0.00 | N |
| ATOM | 5483 | C2 | U | D | 32 | 28.491 | 90.368 | 266.210 | 1.00 | 0.00 | C |
| ATOM | 5484 | O2 | U | D | 32 | 29.109 | 89.635 | 266.984 | 1.00 | 0.00 | O |
| ATOM | 5485 | N3 | U | D | 32 | 28.173 | 91.656 | 266.590 | 1.00 | 0.00 | N |
| ATOM | 5486 | C4 | U | D | 32 | 27.501 | 92.590 | 265.827 | 1.00 | 0.00 | C |
| ATOM | 5487 | O4 | U | D | 32 | 27.267 | 93.707 | 266.282 | 1.00 | 0.00 | O |
| ATOM | 5488 | C5 | U | D | 32 | 27.123 | 92.122 | 264.515 | 1.00 | 0.00 | C |
| ATOM | 5489 | C6 | U | D | 32 | 27.417 | 90.868 | 264.113 | 1.00 | 0.00 | C |
| ATOM | 5490 | P | U | D | 33 | 24.081 | 86.635 | 264.710 | 1.00 | 0.00 | P |
| ATOM | 5491 | O1P | U | D | 33 | 24.161 | 85.155 | 264.657 | 1.00 | 0.00 | O |
| ATOM | 5492 | O2P | U | D | 33 | 23.097 | 87.377 | 263.884 | 1.00 | 0.00 | O |
| ATOM | 5493 | O5* | U | D | 33 | 23.958 | 87.120 | 266.255 | 1.00 | 0.00 | O |
| ATOM | 5494 | C5* | U | D | 33 | 24.432 | 86.335 | 267.366 | 1.00 | 0.00 | C |
| ATOM | 5495 | C4* | U | D | 33 | 24.627 | 87.169 | 268.636 | 1.00 | 0.00 | C |
| ATOM | 5496 | O4* | U | D | 33 | 25.537 | 88.261 | 268.426 | 1.00 | 0.00 | O |
| ATOM | 5497 | C3* | U | D | 33 | 23.334 | 87.862 | 269.005 | 1.00 | 0.00 | C |
| ATOM | 5498 | O3* | U | D | 33 | 22.453 | 86.948 | 269.671 | 1.00 | 0.00 | O |
| ATOM | 5499 | C2* | U | D | 33 | 23.810 | 88.961 | 269.920 | 1.00 | 0.00 | C |
| ATOM | 5500 | O2* | U | D | 33 | 24.181 | 88.455 | 271.209 | 1.00 | 0.00 | O |
| ATOM | 5501 | C1* | U | D | 33 | 25.081 | 89.404 | 269.184 | 1.00 | 0.00 | C |
| ATOM | 5502 | N1 | U | D | 33 | 24.769 | 90.584 | 268.312 | 1.00 | 0.00 | N |
| ATOM | 5503 | C2 | U | D | 33 | 24.885 | 91.855 | 268.864 | 1.00 | 0.00 | C |
| ATOM | 5504 | O2 | U | D | 33 | 25.239 | 92.069 | 270.022 | 1.00 | 0.00 | O |
| ATOM | 5505 | N3 | U | D | 33 | 24.566 | 92.911 | 268.036 | 1.00 | 0.00 | N |
| ATOM | 5506 | C4 | U | D | 33 | 24.144 | 92.825 | 266.724 | 1.00 | 0.00 | C |
| ATOM | 5507 | O4 | U | D | 33 | 23.884 | 93.838 | 266.081 | 1.00 | 0.00 | O |
| ATOM | 5508 | C5 | U | D | 33 | 24.051 | 91.479 | 266.230 | 1.00 | 0.00 | C |
| ATOM | 5509 | C6 | U | D | 33 | 24.359 | 90.429 | 267.016 | 1.00 | 0.00 | C |
| ATOM | 5510 | P | U | D | 34 | 20.514 | 86.548 | 269.593 | 1.00 | 0.00 | P |
| ATOM | 5511 | O1P | U | D | 34 | 19.621 | 86.217 | 270.741 | 1.00 | 0.00 | O |
| ATOM | 5512 | O2P | U | D | 34 | 20.818 | 85.501 | 268.572 | 1.00 | 0.00 | O |
| ATOM | 5513 | O5* | U | D | 34 | 19.917 | 87.838 | 268.859 | 1.00 | 0.00 | O |
| ATOM | 5514 | C5* | U | D | 34 | 19.207 | 87.710 | 267.606 | 1.00 | 0.00 | C |
| ATOM | 5515 | C4* | U | D | 34 | 18.051 | 88.686 | 267.538 | 1.00 | 0.00 | C |
| ATOM | 5516 | O4* | U | D | 34 | 17.045 | 88.358 | 268.533 | 1.00 | 0.00 | O |
| ATOM | 5517 | C3* | U | D | 34 | 18.388 | 90.140 | 267.807 | 1.00 | 0.00 | C |
| ATOM | 5518 | O3* | U | D | 34 | 18.896 | 90.789 | 266.656 | 1.00 | 0.00 | O |
| ATOM | 5519 | C2* | U | D | 34 | 17.055 | 90.726 | 268.251 | 1.00 | 0.00 | C |
| ATOM | 5520 | O2* | U | D | 34 | 16.249 | 91.103 | 267.157 | 1.00 | 0.00 | O |
| ATOM | 5521 | C1* | U | D | 34 | 16.418 | 89.550 | 268.998 | 1.00 | 0.00 | C |
| ATOM | 5522 | N1 | U | D | 34 | 16.568 | 89.631 | 270.465 | 1.00 | 0.00 | N |
| ATOM | 5523 | C2 | U | D | 34 | 15.965 | 90.695 | 271.135 | 1.00 | 0.00 | C |
| ATOM | 5524 | O2 | U | D | 34 | 15.287 | 91.541 | 270.574 | 1.00 | 0.00 | O |
| ATOM | 5525 | N3 | U | D | 34 | 16.184 | 90.725 | 272.491 | 1.00 | 0.00 | N |
| ATOM | 5526 | C4 | U | D | 34 | 16.919 | 89.829 | 273.236 | 1.00 | 0.00 | C |
| ATOM | 5527 | O4 | U | D | 34 | 17.064 | 90.016 | 274.441 | 1.00 | 0.00 | O |
| ATOM | 5528 | C5 | U | D | 34 | 17.490 | 88.754 | 272.486 | 1.00 | 0.00 | C |
| ATOM | 5529 | C6 | U | D | 34 | 17.301 | 88.694 | 271.163 | 1.00 | 0.00 | C |
| ATOM | 5530 | P | U | D | 35 | 20.023 | 91.916 | 266.830 | 1.00 | 0.00 | P |
| ATOM | 5531 | O1P | U | D | 35 | 20.340 | 92.497 | 265.498 | 1.00 | 0.00 | O |
| ATOM | 5532 | O2P | U | D | 35 | 21.110 | 91.336 | 267.656 | 1.00 | 0.00 | O |
| ATOM | 5533 | O5* | U | D | 35 | 19.303 | 93.031 | 267.704 | 1.00 | 0.00 | O |
| ATOM | 5534 | C5* | U | D | 35 | 18.327 | 93.889 | 267.121 | 1.00 | 0.00 | C |
| ATOM | 5535 | C4* | U | D | 35 | 17.945 | 94.959 | 268.099 | 1.00 | 0.00 | C |
| ATOM | 5536 | O4* | U | D | 35 | 17.262 | 94.355 | 269.226 | 1.00 | 0.00 | O |
| ATOM | 5537 | C3* | U | D | 35 | 19.110 | 95.699 | 268.729 | 1.00 | 0.00 | C |
| ATOM | 5538 | O3* | U | D | 35 | 19.618 | 96.725 | 267.889 | 1.00 | 0.00 | O |
| ATOM | 5539 | C2* | U | D | 35 | 18.515 | 96.205 | 270.035 | 1.00 | 0.00 | C |
| ATOM | 5540 | O2* | U | D | 35 | 17.736 | 97.377 | 269.892 | 1.00 | 0.00 | O |
| ATOM | 5541 | C1* | U | D | 35 | 17.591 | 95.049 | 270.415 | 1.00 | 0.00 | C |
| ATOM | 5542 | N1 | U | D | 35 | 18.232 | 94.113 | 271.350 | 1.00 | 0.00 | N |
| ATOM | 5543 | C2 | U | D | 35 | 18.398 | 94.540 | 272.648 | 1.00 | 0.00 | C |
| ATOM | 5544 | O2 | U | D | 35 | 18.039 | 95.652 | 273.033 | 1.00 | 0.00 | O |
| ATOM | 5545 | N3 | U | D | 35 | 19.000 | 93.630 | 273.483 | 1.00 | 0.00 | N |
| ATOM | 5546 | C4 | U | D | 35 | 19.445 | 92.367 | 273.154 | 1.00 | 0.00 | C |

```
ATOM  5547  O4    U D 35   19.995  91.681 274.014 1.00 0.00           O
ATOM  5548  C5    U D 35   19.236  92.000 271.793 1.00 0.00           C
ATOM  5549  C6    U D 35   18.652  92.863 270.957 1.00 0.00           C
ATOM  5550  P     U D 36   21.209  96.894 267.736 1.00 0.00           P
ATOM  5551  O1P   U D 36   21.455  97.921 266.690 1.00 0.00           O
ATOM  5552  O2P   U D 36   21.786  95.528 267.576 1.00 0.00           O
ATOM  5553  O5*   U D 36   21.659  97.489 269.148 1.00 0.00           O
ATOM  5554  C5*   U D 36   21.145  98.761 269.596 1.00 0.00           C
ATOM  5555  C4*   U D 36   21.392  98.956 271.074 1.00 0.00           C
ATOM  5556  O4*   U D 36   20.696  97.930 271.834 1.00 0.00           O
ATOM  5557  C3*   U D 36   22.825  98.851 271.564 1.00 0.00           C
ATOM  5558  O3*   U D 36   23.614 100.008 271.323 1.00 0.00           O
ATOM  5559  C2*   U D 36   22.631  98.567 273.047 1.00 0.00           C
ATOM  5560  O2*   U D 36   22.323  99.713 273.818 1.00 0.00           O
ATOM  5561  C1*   U D 36   21.420  97.644 273.020 1.00 0.00           C
ATOM  5562  N1    U D 36   21.852  96.235 273.011 1.00 0.00           N
ATOM  5563  C2    U D 36   22.400  95.736 274.190 1.00 0.00           C
ATOM  5564  O2    U D 36   22.522  96.412 275.202 1.00 0.00           O
ATOM  5565  N3    U D 36   22.792  94.422 274.142 1.00 0.00           N
ATOM  5566  C4    U D 36   22.704  93.565 273.067 1.00 0.00           C
ATOM  5567  O4    U D 36   23.057  92.381 273.205 1.00 0.00           O
ATOM  5568  C5    U D 36   22.137  94.150 271.880 1.00 0.00           C
ATOM  5569  C6    U D 36   21.738  95.432 271.893 1.00 0.00           C
ATOM  5570  P     A D 37   25.130  99.829 270.795 1.00 0.00           P
ATOM  5571  O1P   A D 37   25.598 101.158 270.309 1.00 0.00           O
ATOM  5572  O2P   A D 37   25.167  98.647 269.874 1.00 0.00           O
ATOM  5573  O5*   A D 37   25.964  99.428 272.097 1.00 0.00           O
ATOM  5574  C5*   A D 37   26.066 100.319 273.222 1.00 0.00           C
ATOM  5575  C4*   A D 37   26.639  99.587 274.413 1.00 0.00           C
ATOM  5576  O4*   A D 37   25.751  98.504 274.777 1.00 0.00           O
ATOM  5577  C3*   A D 37   27.987  98.919 274.199 1.00 0.00           C
ATOM  5578  O3*   A D 37   29.060  99.832 274.397 1.00 0.00           O
ATOM  5579  C2*   A D 37   27.972  97.803 275.235 1.00 0.00           C
ATOM  5580  O2*   A D 37   28.317  98.239 276.539 1.00 0.00           O
ATOM  5581  C1*   A D 37   26.503  97.386 275.222 1.00 0.00           C
ATOM  5582  N9    A D 37   26.257  96.276 274.300 1.00 0.00           N
ATOM  5583  C8    A D 37   25.772  96.350 273.009 1.00 0.00           C
ATOM  5584  N7    A D 37   25.701  95.190 272.402 1.00 0.00           N
ATOM  5585  C5    A D 37   26.159  94.290 273.351 1.00 0.00           C
ATOM  5586  C6    A D 37   26.339  92.905 273.316 1.00 0.00           C
ATOM  5587  N6    A D 37   26.070  92.160 272.236 1.00 0.00           N
ATOM  5588  N1    A D 37   26.813  92.303 274.432 1.00 0.00           N
ATOM  5589  C2    A D 37   27.088  93.064 275.508 1.00 0.00           C
ATOM  5590  N3    A D 37   26.967  94.380 275.660 1.00 0.00           N
ATOM  5591  C4    A D 37   26.493  94.943 274.533 1.00 0.00           C
ATOM  5592  P     U D 38   30.326  99.101 272.653 1.00 0.00           P
ATOM  5593  O1P   U D 38   31.264 100.171 273.066 1.00 0.00           O
ATOM  5594  O2P   U D 38   29.922  98.993 271.234 1.00 0.00           O
ATOM  5595  O5*   U D 38   30.925  97.698 273.142 1.00 0.00           O
ATOM  5596  C5*   U D 38   31.467  97.589 274.459 1.00 0.00           C
ATOM  5597  C4*   U D 38   31.544  96.147 274.892 1.00 0.00           C
ATOM  5598  O4*   U D 38   30.272  95.501 274.726 1.00 0.00           O
ATOM  5599  C3*   U D 38   32.478  95.378 273.993 1.00 0.00           C
ATOM  5600  O3*   U D 38   33.848  95.549 274.394 1.00 0.00           O
ATOM  5601  C2*   U D 38   32.021  93.963 274.232 1.00 0.00           C
ATOM  5602  O2*   U D 38   32.450  93.460 275.500 1.00 0.00           O
ATOM  5603  C1*   U D 38   30.509  94.144 274.293 1.00 0.00           C
ATOM  5604  N1    U D 38   29.882  93.867 272.955 1.00 0.00           N
ATOM  5605  C2    U D 38   29.814  92.541 272.523 1.00 0.00           C
ATOM  5606  O2    U D 38   30.228  91.589 273.184 1.00 0.00           O
ATOM  5607  N3    U D 38   29.223  92.332 271.287 1.00 0.00           N
ATOM  5608  C4    U D 38   28.701  93.305 270.451 1.00 0.00           C
ATOM  5609  O4    U D 38   28.216  93.006 269.363 1.00 0.00           O
ATOM  5610  C5    U D 38   28.809  94.645 270.972 1.00 0.00           C
ATOM  5611  C6    U D 38   29.381  94.880 272.172 1.00 0.00           C
ATOM  5612  P     U D 39   35.006  95.745 273.289 1.00 0.00           P
ATOM  5613  O1P   U D 39   36.276  95.777 274.044 1.00 0.00           O
ATOM  5614  O2P   U D 39   34.648  96.866 272.389 1.00 0.00           O
ATOM  5615  O5*   U D 39   34.975  94.379 272.449 1.00 0.00           O
ATOM  5616  C5*   U D 39   35.394  93.127 273.005 1.00 0.00           C
ATOM  5617  C4*   U D 39   35.043  91.961 272.084 1.00 0.00           C
ATOM  5618  O4*   U D 39   33.632  91.881 271.822 1.00 0.00           O
ATOM  5619  C3*   U D 39   35.636  92.204 270.716 1.00 0.00           C
ATOM  5620  O3*   U D 39   37.035  91.888 270.728 1.00 0.00           O
ATOM  5621  C2*   U D 39   34.830  91.253 269.861 1.00 0.00           C
ATOM  5622  O2*   U D 39   35.216  89.893 270.096 1.00 0.00           O
ATOM  5623  C1*   U D 39   33.431  91.478 270.443 1.00 0.00           C
ATOM  5624  N1    U D 39   32.682  92.532 269.676 1.00 0.00           N
ATOM  5625  C2    U D 39   32.073  92.172 268.479 1.00 0.00           C
ATOM  5626  O2    U D 39   32.133  91.039 268.003 1.00 0.00           O
ATOM  5627  N3    U D 39   31.383  93.180 267.824 1.00 0.00           N
ATOM  5628  C4    U D 39   31.248  94.492 268.242 1.00 0.00           C
ATOM  5629  O4    U D 39   30.609  95.309 267.585 1.00 0.00           O
ATOM  5630  C5    U D 39   31.909  94.777 269.482 1.00 0.00           C
ATOM  5631  C6    U D 39   32.586  93.817 270.141 1.00 0.00           C
ATOM  5632  P     C D 40   38.038  92.701 269.770 1.00 0.00           P
ATOM  5633  O1P   C D 40   39.258  92.076 270.331 1.00 0.00           O
```

```
ATOM   5634  O2P   C D  40      37.935  94.174 269.683  1.00  0.00           O
ATOM   5635  O5*   C D  40      37.761  92.107 268.302  1.00  0.00           O
ATOM   5636  C5*   C D  40      38.105  90.778 267.888  1.00  0.00           C
ATOM   5637  C4*   C D  40      37.513  90.471 266.513  1.00  0.00           C
ATOM   5638  O4*   C D  40      36.073  90.600 266.511  1.00  0.00           O
ATOM   5639  C3*   C D  40      37.949  91.535 265.522  1.00  0.00           C
ATOM   5640  O3*   C D  40      39.296  91.278 265.057  1.00  0.00           O
ATOM   5641  C2*   C D  40      36.897  91.392 264.433  1.00  0.00           C
ATOM   5642  O2*   C D  40      37.052  90.206 263.632  1.00  0.00           O
ATOM   5643  C1*   C D  40      35.643  91.224 265.273  1.00  0.00           C
ATOM   5644  N1    C D  40      35.015  92.573 265.462  1.00  0.00           N
ATOM   5645  C2    C D  40      34.262  93.099 264.412  1.00  0.00           C
ATOM   5646  O2    C D  40      34.122  92.493 263.351  1.00  0.00           O
ATOM   5647  N3    C D  40      33.676  94.314 264.582  1.00  0.00           N
ATOM   5648  C4    C D  40      33.809  94.999 265.720  1.00  0.00           C
ATOM   5649  N4    C D  40      33.210  96.181 265.849  1.00  0.00           N
ATOM   5650  C5    C D  40      34.579  94.481 266.805  1.00  0.00           C
ATOM   5651  C6    C D  40      35.155  93.276 266.629  1.00  0.00           C
ATOM   5652  P     C D  41      40.163  92.429 264.300  1.00  0.00           P
ATOM   5653  O1P   C D  41      41.275  91.913 265.137  1.00  0.00           O
ATOM   5654  O2P   C D  41      40.286  93.736 263.612  1.00  0.00           O
ATOM   5655  O5*   C D  41      39.740  91.280 263.241  1.00  0.00           O
ATOM   5656  C5*   C D  41      40.023  91.182 261.841  1.00  0.00           C
ATOM   5657  C4*   C D  41      39.028  91.917 260.938  1.00  0.00           C
ATOM   5658  O4*   C D  41      37.805  92.290 261.592  1.00  0.00           O
ATOM   5659  C3*   C D  41      39.573  93.257 260.574  1.00  0.00           C
ATOM   5660  O3*   C D  41      40.665  93.100 259.657  1.00  0.00           O
ATOM   5661  C2*   C D  41      38.363  93.902 259.939  1.00  0.00           C
ATOM   5662  O2*   C D  41      38.075  93.402 258.618  1.00  0.00           O
ATOM   5663  C1*   C D  41      37.255  93.419 260.869  1.00  0.00           C
ATOM   5664  N1    C D  41      36.846  94.564 261.748  1.00  0.00           N
ATOM   5665  C2    C D  41      36.025  95.556 261.204  1.00  0.00           C
ATOM   5666  O2    C D  41      35.652  95.521 260.030  1.00  0.00           O
ATOM   5667  N3    C D  41      35.641  96.587 262.005  1.00  0.00           N
ATOM   5668  C4    C D  41      36.034  96.664 263.279  1.00  0.00           C
ATOM   5669  N4    C D  41      35.632  97.692 264.024  1.00  0.00           N
ATOM   5670  C5    C D  41      36.877  95.663 263.853  1.00  0.00           C
ATOM   5671  C6    C D  41      37.251  94.643 263.054  1.00  0.00           C
ATOM   5672  P     G D  42      42.030  93.927 259.897  1.00  0.00           P
ATOM   5673  O1P   G D  42      42.951  93.203 258.987  1.00  0.00           O
ATOM   5674  O2P   G D  42      42.457  94.245 261.281  1.00  0.00           O
ATOM   5675  O5*   G D  42      41.544  95.294 259.188  1.00  0.00           O
ATOM   5676  C5*   G D  42      41.193  95.295 257.801  1.00  0.00           C
ATOM   5677  C4*   G D  42      40.235  96.421 257.457  1.00  0.00           C
ATOM   5678  O4*   G D  42      39.133  96.484 258.365  1.00  0.00           O
ATOM   5679  C3*   G D  42      40.863  97.764 257.681  1.00  0.00           C
ATOM   5680  O3*   G D  42      41.830  98.037 256.665  1.00  0.00           O
ATOM   5681  C2*   G D  42      39.648  98.653 257.546  1.00  0.00           C
ATOM   5682  O2*   G D  42      39.264  98.877 256.177  1.00  0.00           O
ATOM   5683  C1*   G D  42      38.565  97.795 258.189  1.00  0.00           C
ATOM   5684  N9    G D  42      38.166  98.454 259.455  1.00  0.00           N
ATOM   5685  C8    G D  42      38.436  98.115 260.755  1.00  0.00           C
ATOM   5686  N7    G D  42      37.929  98.938 261.631  1.00  0.00           N
ATOM   5687  C5    G D  42      37.278  99.888 260.859  1.00  0.00           C
ATOM   5688  C6    G D  42      36.548 101.033 261.256  1.00  0.00           C
ATOM   5689  O6    G D  42      36.330 101.436 262.393  1.00  0.00           O
ATOM   5690  N1    G D  42      36.054 101.728 260.165  1.00  0.00           N
ATOM   5691  C2    G D  42      36.240 101.370 258.849  1.00  0.00           C
ATOM   5692  N2    G D  42      35.697 102.161 257.925  1.00  0.00           N
ATOM   5693  N3    G D  42      36.926 100.290 258.474  1.00  0.00           N
ATOM   5694  C4    G D  42      37.415  99.602 259.531  1.00  0.00           C
ATOM   5695  P     G D  43      42.859  99.260 256.833  1.00  0.00           P
ATOM   5696  O1P   G D  43      43.362  98.842 255.501  1.00  0.00           O
ATOM   5697  O2P   G D  43      43.753  99.211 258.015  1.00  0.00           O
ATOM   5698  O5*   G D  43      42.225 100.734 256.727  1.00  0.00           O
ATOM   5699  C5*   G D  43      41.567 101.130 255.524  1.00  0.00           C
ATOM   5700  C4*   G D  43      40.539 102.211 255.787  1.00  0.00           C
ATOM   5701  O4*   G D  43      39.653 101.862 256.852  1.00  0.00           O
ATOM   5702  C3*   G D  43      41.190 103.435 256.344  1.00  0.00           C
ATOM   5703  O3*   G D  43      41.905 104.104 255.311  1.00  0.00           O
ATOM   5704  C2*   G D  43      39.995 104.231 256.808  1.00  0.00           C
ATOM   5705  O2*   G D  43      39.250 104.810 255.717  1.00  0.00           O
ATOM   5706  C1*   G D  43      39.166 103.101 257.408  1.00  0.00           C
ATOM   5707  N9    G D  43      39.270 103.105 258.893  1.00  0.00           N
ATOM   5708  C8    G D  43      39.914 102.228 259.736  1.00  0.00           C
ATOM   5709  N7    G D  43      39.739 102.486 261.003  1.00  0.00           N
ATOM   5710  C5    G D  43      38.927 103.614 261.004  1.00  0.00           C
ATOM   5711  C6    G D  43      38.400 104.352 262.092  1.00  0.00           C
ATOM   5712  O6    G D  43      38.547 104.153 263.292  1.00  0.00           O
ATOM   5713  N1    G D  43      37.635 105.416 261.664  1.00  0.00           N
ATOM   5714  C2    G D  43      37.396 105.741 260.352  1.00  0.00           C
ATOM   5715  N2    G D  43      36.628 106.802 260.135  1.00  0.00           N
ATOM   5716  N3    G D  43      37.885 105.051 259.327  1.00  0.00           N
ATOM   5717  C4    G D  43      38.639 104.002 259.725  1.00  0.00           C
ATOM   5718  P     C D  44      43.332 104.744 255.660  1.00  0.00           P
ATOM   5719  O1P   C D  44      43.646 105.698 254.568  1.00  0.00           O
ATOM   5720  O2P   C D  44      44.171 103.541 255.878  1.00  0.00           O
```

```
ATOM   5721  O5*   C   D   44      43.256 105.715 256.922  1.00  0.00           O
ATOM   5722  C5*   C   D   44      43.069 107.100 256.645  1.00  0.00           C
ATOM   5723  C4*   C   D   44      41.741 107.566 257.192  1.00  0.00           C
ATOM   5724  O4*   C   D   44      41.293 106.647 258.234  1.00  0.00           O
ATOM   5725  C3*   C   D   44      41.744 108.950 257.836  1.00  0.00           C
ATOM   5726  O3*   C   D   44      40.511 109.616 257.586  1.00  0.00           O
ATOM   5727  C2*   C   D   44      41.890 108.627 259.317  1.00  0.00           C
ATOM   5728  O2*   C   D   44      41.369 109.640 260.155  1.00  0.00           O
ATOM   5729  C1*   C   D   44      41.044 107.368 259.426  1.00  0.00           C
ATOM   5730  N1    C   D   44      41.416 106.513 260.616  1.00  0.00           N
ATOM   5731  C2    C   D   44      40.870 106.836 261.860  1.00  0.00           C
ATOM   5732  O2    C   D   44      40.099 107.786 262.016  1.00  0.00           O
ATOM   5733  N3    C   D   44      41.196 106.057 262.924  1.00  0.00           N
ATOM   5734  C4    C   D   44      42.012 105.005 262.812  1.00  0.00           C
ATOM   5735  N4    C   D   44      42.291 104.266 263.885  1.00  0.00           N
ATOM   5736  C5    C   D   44      42.582 104.656 261.553  1.00  0.00           C
ATOM   5737  C6    C   D   44      42.256 105.432 260.501  1.00  0.00           C
ATOM   5738  P     U   D   45      40.823 110.758 256.442  1.00  0.00           P
ATOM   5739  O1P   U   D   45      40.081 111.733 257.286  1.00  0.00           O
ATOM   5740  O2P   U   D   45      40.120 110.050 255.339  1.00  0.00           O
ATOM   5741  O5*   U   D   45      42.107 111.469 255.820  1.00  0.00           O
ATOM   5742  C5*   U   D   45      43.221 111.873 256.646  1.00  0.00           C
ATOM   5743  C4*   U   D   45      43.919 113.073 256.036  1.00  0.00           C
ATOM   5744  O4*   U   D   45      42.929 114.024 255.564  1.00  0.00           O
ATOM   5745  C3*   U   D   45      44.844 113.839 256.971  1.00  0.00           C
ATOM   5746  O3*   U   D   45      45.963 114.297 256.216  1.00  0.00           O
ATOM   5747  C2*   U   D   45      43.986 115.023 257.417  1.00  0.00           C
ATOM   5748  O2*   U   D   45      44.740 116.168 257.757  1.00  0.00           O
ATOM   5749  C1*   U   D   45      43.143 115.282 256.168  1.00  0.00           C
ATOM   5750  N1    U   D   45      41.825 115.880 256.444  1.00  0.00           N
ATOM   5751  C2    U   D   45      41.553 117.135 255.916  1.00  0.00           C
ATOM   5752  O2    U   D   45      42.365 117.775 255.268  1.00  0.00           O
ATOM   5753  N3    U   D   45      40.290 117.610 256.178  1.00  0.00           N
ATOM   5754  C4    U   D   45      39.298 116.981 256.904  1.00  0.00           C
ATOM   5755  O4    U   D   45      38.203 117.526 257.031  1.00  0.00           O
ATOM   5756  C5    U   D   45      39.663 115.700 257.430  1.00  0.00           C
ATOM   5757  C6    U   D   45      40.884 115.206 257.189  1.00  0.00           C
ATOM   5758  P     A   D   46      47.308 113.675 256.313  1.00  0.00           P
ATOM   5759  O1P   A   D   46      48.278 114.194 255.317  1.00  0.00           O
ATOM   5760  O2P   A   D   46      47.021 112.213 256.371  1.00  0.00           O
ATOM   5761  O5*   A   D   46      47.802 114.136 257.754  1.00  0.00           O
ATOM   5762  C5*   A   D   46      48.700 113.317 258.500  1.00  0.00           C
ATOM   5763  C4*   A   D   46      49.317 114.106 259.628  1.00  0.00           C
ATOM   5764  O4*   A   D   46      49.219 113.304 260.828  1.00  0.00           O
ATOM   5765  C3*   A   D   46      50.793 114.458 259.465  1.00  0.00           C
ATOM   5766  O3*   A   D   46      50.984 115.745 258.869  1.00  0.00           O
ATOM   5767  C2*   A   D   46      51.310 114.386 260.894  1.00  0.00           C
ATOM   5768  O2*   A   D   46      51.045 115.570 261.622  1.00  0.00           O
ATOM   5769  C1*   A   D   46      50.479 113.226 261.451  1.00  0.00           C
ATOM   5770  N9    A   D   46      51.025 111.916 261.107  1.00  0.00           N
ATOM   5771  C8    A   D   46      50.986 111.306 259.875  1.00  0.00           C
ATOM   5772  N7    A   D   46      51.543 110.121 259.855  1.00  0.00           N
ATOM   5773  C5    A   D   46      51.979 109.938 261.158  1.00  0.00           C
ATOM   5774  C6    A   D   46      52.650 108.881 261.786  1.00  0.00           C
ATOM   5775  N6    A   D   46      53.012 107.761 261.160  1.00  0.00           N
ATOM   5776  N1    A   D   46      52.940 109.013 263.097  1.00  0.00           N
ATOM   5777  C2    A   D   46      52.573 110.140 263.724  1.00  0.00           C
ATOM   5778  N3    A   D   46      51.938 111.205 263.243  1.00  0.00           N
ATOM   5779  C4    A   D   46      51.667 111.037 261.940  1.00  0.00           C
ATOM   5780  P     U   D   48      52.683 115.971 258.469  1.00  0.00           P
ATOM   5781  O1P   U   D   48      53.320 116.982 257.565  1.00  0.00           O
ATOM   5782  O2P   U   D   48      52.621 114.640 257.799  1.00  0.00           O
ATOM   5783  O5*   U   D   48      53.317 115.932 259.925  1.00  0.00           O
ATOM   5784  C5*   U   D   48      54.587 115.359 260.302  1.00  0.00           C
ATOM   5785  C4*   U   D   48      54.473 115.012 261.779  1.00  0.00           C
ATOM   5786  O4*   U   D   48      54.460 113.592 261.903  1.00  0.00           O
ATOM   5787  C3*   U   D   48      55.630 115.482 262.668  1.00  0.00           C
ATOM   5788  O3*   U   D   48      55.151 115.819 263.998  1.00  0.00           O
ATOM   5789  C2*   U   D   48      56.526 114.263 262.763  1.00  0.00           C
ATOM   5790  O2*   U   D   48      57.312 114.351 263.918  1.00  0.00           O
ATOM   5791  C1*   U   D   48      55.509 113.171 262.793  1.00  0.00           C
ATOM   5792  N1    U   D   48      56.033 111.871 262.334  1.00  0.00           N
ATOM   5793  C2    U   D   48      56.225 110.914 263.323  1.00  0.00           C
ATOM   5794  O2    U   D   48      55.981 111.182 264.500  1.00  0.00           O
ATOM   5795  N3    U   D   48      56.693 109.691 262.951  1.00  0.00           N
ATOM   5796  C4    U   D   48      56.964 109.393 261.643  1.00  0.00           C
ATOM   5797  O4    U   D   48      57.392 108.231 261.396  1.00  0.00           O
ATOM   5798  C5    U   D   48      56.756 110.379 260.643  1.00  0.00           C
ATOM   5799  C6    U   D   48      56.297 111.588 261.031  1.00  0.00           C
HETATM 5800  P     5MC D   49      56.042 116.998 265.337  1.00  0.00           P
HETATM 5801  O1P   5MC D   49      56.739 116.399 266.485  1.00  0.00           O
HETATM 5802  O2P   5MC D   49      56.985 117.545 264.311  1.00  0.00           O
HETATM 5803  O5*   5MC D   49      54.908 118.047 265.677  1.00  0.00           O
HETATM 5804  C5*   5MC D   49      53.814 118.209 264.728  1.00  0.00           C
HETATM 5805  C4*   5MC D   49      53.490 119.690 264.706  1.00  0.00           C
HETATM 5806  O4*   5MC D   49      53.799 120.273 265.966  1.00  0.00           O
HETATM 5807  C3*   5MC D   49      54.306 120.504 263.686  1.00  0.00           C
```

| | | | | | | | | | |
|---|---|---|---|---|---|---|---|---|---|
| HETATM | 5808 | O3* | 5MC | D | 49 | 53.782 | 120.418 | 262.364 | 1.00 0.00 | O |
| HETATM | 5809 | C2* | 5MC | D | 49 | 54.208 | 121.900 | 264.286 | 1.00 0.00 | C |
| HETATM | 5810 | O2* | 5MC | D | 49 | 52.954 | 122.421 | 263.883 | 1.00 0.00 | O |
| HETATM | 5811 | C1* | 5MC | D | 49 | 54.240 | 121.608 | 265.772 | 1.00 0.00 | C |
| HETATM | 5812 | N1 | 5MC | D | 49 | 55.628 | 121.806 | 266.234 | 1.00 0.00 | N |
| HETATM | 5813 | C2 | 5MC | D | 49 | 56.126 | 123.095 | 266.168 | 1.00 0.00 | C |
| HETATM | 5814 | O2 | 5MC | D | 49 | 55.419 | 124.004 | 265.745 | 1.00 0.00 | O |
| HETATM | 5815 | N3 | 5MC | D | 49 | 57.406 | 123.299 | 266.587 | 1.00 0.00 | N |
| HETATM | 5816 | C4 | 5MC | D | 49 | 58.185 | 122.281 | 267.054 | 1.00 0.00 | C |
| HETATM | 5817 | N4 | 5MC | D | 49 | 59.438 | 122.523 | 267.449 | 1.00 0.00 | N |
| HETATM | 5818 | C5 | 5MC | D | 49 | 57.647 | 120.962 | 267.114 | 1.00 0.00 | C |
| HETATM | 5819 | C6 | 5MC | D | 49 | 56.393 | 120.778 | 266.695 | 1.00 0.00 | C |
| HETATM | 5820 | CM5 | 5MC | D | 49 | 58.498 | 119.833 | 267.625 | 1.00 0.00 | C |
| ATOM | 5821 | P | G | D | 50 | 54.665 | 120.187 | 261.050 | 1.00 0.00 | P |
| ATOM | 5822 | O1P | G | D | 50 | 53.928 | 119.423 | 259.999 | 1.00 0.00 | O |
| ATOM | 5823 | O2P | G | D | 50 | 55.880 | 119.475 | 261.519 | 1.00 0.00 | O |
| ATOM | 5824 | O5* | G | D | 50 | 54.921 | 121.669 | 260.543 | 1.00 0.00 | O |
| ATOM | 5825 | C5* | G | D | 50 | 53.880 | 122.661 | 260.830 | 1.00 0.00 | C |
| ATOM | 5826 | C4* | G | D | 50 | 54.558 | 123.976 | 260.460 | 1.00 0.00 | C |
| ATOM | 5827 | O4* | G | D | 50 | 54.993 | 124.646 | 261.616 | 1.00 0.00 | O |
| ATOM | 5828 | C3* | G | D | 50 | 55.802 | 123.792 | 259.604 | 1.00 0.00 | C |
| ATOM | 5829 | O3* | G | D | 50 | 55.503 | 123.572 | 258.233 | 1.00 0.00 | O |
| ATOM | 5830 | C2* | G | D | 50 | 56.567 | 125.099 | 259.861 | 1.00 0.00 | C |
| ATOM | 5831 | O2* | G | D | 50 | 55.987 | 126.073 | 259.008 | 1.00 0.00 | O |
| ATOM | 5832 | C1* | G | D | 50 | 56.214 | 125.346 | 261.316 | 1.00 0.00 | C |
| ATOM | 5833 | N9 | G | D | 50 | 57.292 | 124.873 | 262.207 | 1.00 0.00 | N |
| ATOM | 5834 | C8 | G | D | 50 | 57.391 | 123.685 | 262.886 | 1.00 0.00 | C |
| ATOM | 5835 | N7 | G | D | 50 | 58.482 | 123.585 | 263.603 | 1.00 0.00 | N |
| ATOM | 5836 | C5 | G | D | 50 | 59.137 | 124.792 | 263.393 | 1.00 0.00 | C |
| ATOM | 5837 | C6 | G | D | 50 | 60.367 | 125.307 | 263.886 | 1.00 0.00 | C |
| ATOM | 5838 | O6 | G | D | 50 | 61.156 | 124.746 | 264.656 | 1.00 0.00 | O |
| ATOM | 5839 | N1 | G | D | 50 | 60.673 | 126.559 | 263.443 | 1.00 0.00 | N |
| ATOM | 5840 | C2 | G | D | 50 | 59.875 | 127.254 | 262.593 | 1.00 0.00 | C |
| ATOM | 5841 | N2 | G | D | 50 | 60.299 | 128.480 | 262.234 | 1.00 0.00 | N |
| ATOM | 5842 | N3 | G | D | 50 | 58.712 | 126.823 | 262.103 | 1.00 0.00 | N |
| ATOM | 5843 | C4 | G | D | 50 | 58.413 | 125.589 | 262.539 | 1.00 0.00 | C |
| ATOM | 5844 | P | G | D | 51 | 56.656 | 123.127 | 257.236 | 1.00 0.00 | P |
| ATOM | 5845 | O1P | G | D | 51 | 56.103 | 122.461 | 256.013 | 1.00 0.00 | O |
| ATOM | 5846 | O2P | G | D | 51 | 57.483 | 122.202 | 258.058 | 1.00 0.00 | O |
| ATOM | 5847 | O5* | G | D | 51 | 57.361 | 124.503 | 256.872 | 1.00 0.00 | O |
| ATOM | 5848 | C5* | G | D | 51 | 58.512 | 124.474 | 255.979 | 1.00 0.00 | C |
| ATOM | 5849 | C4* | G | D | 51 | 59.381 | 125.639 | 256.404 | 1.00 0.00 | C |
| ATOM | 5850 | O4* | G | D | 51 | 59.276 | 125.845 | 257.807 | 1.00 0.00 | O |
| ATOM | 5851 | C3* | G | D | 51 | 60.873 | 125.435 | 256.166 | 1.00 0.00 | C |
| ATOM | 5852 | O3* | G | D | 51 | 61.214 | 125.691 | 254.807 | 1.00 0.00 | O |
| ATOM | 5853 | C2* | G | D | 51 | 61.502 | 126.406 | 257.157 | 1.00 0.00 | C |
| ATOM | 5854 | O2* | G | D | 51 | 61.446 | 127.693 | 256.570 | 1.00 0.00 | O |
| ATOM | 5855 | C1* | G | D | 51 | 60.541 | 126.313 | 258.331 | 1.00 0.00 | C |
| ATOM | 5856 | N9 | G | D | 51 | 61.017 | 125.411 | 259.400 | 1.00 0.00 | N |
| ATOM | 5857 | C8 | G | D | 51 | 60.371 | 124.325 | 259.903 | 1.00 0.00 | C |
| ATOM | 5858 | N7 | G | D | 51 | 61.027 | 123.717 | 260.859 | 1.00 0.00 | N |
| ATOM | 5859 | C5 | G | D | 51 | 62.190 | 124.467 | 260.994 | 1.00 0.00 | C |
| ATOM | 5860 | C6 | G | D | 51 | 63.298 | 124.318 | 261.865 | 1.00 0.00 | C |
| ATOM | 5861 | O6 | G | D | 51 | 63.462 | 123.436 | 262.723 | 1.00 0.00 | O |
| ATOM | 5862 | N1 | G | D | 51 | 64.277 | 125.265 | 261.704 | 1.00 0.00 | N |
| ATOM | 5863 | C2 | G | D | 51 | 64.173 | 126.263 | 260.790 | 1.00 0.00 | C |
| ATOM | 5864 | N2 | G | D | 51 | 65.206 | 127.109 | 260.765 | 1.00 0.00 | N |
| ATOM | 5865 | N3 | G | D | 51 | 63.152 | 126.447 | 259.950 | 1.00 0.00 | N |
| ATOM | 5866 | C4 | G | D | 51 | 62.198 | 125.514 | 260.107 | 1.00 0.00 | C |
| ATOM | 5867 | P | G | D | 52 | 61.782 | 124.506 | 253.875 | 1.00 0.00 | P |
| ATOM | 5868 | O1P | G | D | 52 | 61.404 | 124.680 | 252.439 | 1.00 0.00 | O |
| ATOM | 5869 | O2P | G | D | 52 | 61.162 | 123.305 | 254.480 | 1.00 0.00 | O |
| ATOM | 5870 | O5* | G | D | 52 | 63.368 | 124.662 | 254.080 | 1.00 0.00 | O |
| ATOM | 5871 | C5* | G | D | 52 | 63.882 | 126.022 | 254.138 | 1.00 0.00 | C |
| ATOM | 5872 | C4* | G | D | 52 | 65.177 | 125.985 | 254.906 | 1.00 0.00 | C |
| ATOM | 5873 | O4* | G | D | 52 | 64.939 | 126.096 | 256.308 | 1.00 0.00 | O |
| ATOM | 5874 | C3* | G | D | 52 | 65.964 | 124.679 | 254.751 | 1.00 0.00 | C |
| ATOM | 5875 | O3* | G | D | 52 | 66.720 | 124.609 | 253.538 | 1.00 0.00 | O |
| ATOM | 5876 | C2* | G | D | 52 | 66.845 | 124.700 | 256.005 | 1.00 0.00 | C |
| ATOM | 5877 | O2* | G | D | 52 | 67.949 | 125.533 | 255.713 | 1.00 0.00 | O |
| ATOM | 5878 | C1* | G | D | 52 | 65.902 | 125.341 | 257.013 | 1.00 0.00 | C |
| ATOM | 5879 | N9 | G | D | 52 | 65.284 | 124.252 | 257.795 | 1.00 0.00 | N |
| ATOM | 5880 | C8 | G | D | 52 | 64.037 | 123.736 | 257.604 | 1.00 0.00 | C |
| ATOM | 5881 | N7 | G | D | 52 | 63.733 | 122.770 | 258.434 | 1.00 0.00 | N |
| ATOM | 5882 | C5 | G | D | 52 | 64.884 | 122.640 | 259.216 | 1.00 0.00 | C |
| ATOM | 5883 | C6 | G | D | 52 | 65.188 | 121.764 | 260.293 | 1.00 0.00 | C |
| ATOM | 5884 | O6 | G | D | 52 | 64.463 | 120.897 | 260.775 | 1.00 0.00 | O |
| ATOM | 5885 | N1 | G | D | 52 | 66.439 | 121.943 | 260.822 | 1.00 0.00 | N |
| ATOM | 5886 | C2 | G | D | 52 | 67.310 | 122.885 | 260.350 | 1.00 0.00 | C |
| ATOM | 5887 | N2 | G | D | 52 | 68.487 | 122.927 | 260.972 | 1.00 0.00 | N |
| ATOM | 5888 | N3 | G | D | 52 | 67.069 | 123.726 | 259.344 | 1.00 0.00 | N |
| ATOM | 5889 | C4 | G | D | 52 | 65.838 | 123.551 | 258.824 | 1.00 0.00 | C |
| ATOM | 5890 | P | G | D | 53 | 67.512 | 123.290 | 253.081 | 1.00 0.00 | P |
| ATOM | 5891 | O1P | G | D | 53 | 67.516 | 123.172 | 251.578 | 1.00 0.00 | O |
| ATOM | 5892 | O2P | G | D | 53 | 66.782 | 122.176 | 253.732 | 1.00 0.00 | O |
| ATOM | 5893 | O5* | G | D | 53 | 68.991 | 123.557 | 253.627 | 1.00 0.00 | O |
| ATOM | 5894 | C5* | G | D | 53 | 69.910 | 122.451 | 253.809 | 1.00 0.00 | C |

```
ATOM    5895  C4*  G   D  53      70.513 122.601 255.188  1.00  0.00           C
ATOM    5896  O4*  G   D  53      69.507 122.832 256.160  1.00  0.00           O
ATOM    5897  C3*  G   D  53      71.252 121.364 255.689  1.00  0.00           C
ATOM    5898  O3*  G   D  53      72.556 121.243 255.137  1.00  0.00           O
ATOM    5899  C2*  G   D  53      71.235 121.563 257.212  1.00  0.00           C
ATOM    5900  O2*  G   D  53      72.308 122.435 257.527  1.00  0.00           O
ATOM    5901  C1*  G   D  53      69.887 122.228 257.398  1.00  0.00           C
ATOM    5902  N9   G   D  53      68.885 121.225 257.822  1.00  0.00           N
ATOM    5903  C8   G   D  53      67.608 121.077 257.354  1.00  0.00           C
ATOM    5904  N7   G   D  53      66.949 120.101 257.908  1.00  0.00           N
ATOM    5905  C5   G   D  53      67.868 119.565 258.811  1.00  0.00           C
ATOM    5906  C6   G   D  53      67.751 118.470 259.727  1.00  0.00           C
ATOM    5907  O6   G   D  53      66.773 117.752 259.903  1.00  0.00           O
ATOM    5908  N1   G   D  53      68.882 118.238 260.466  1.00  0.00           N
ATOM    5909  C2   G   D  53      70.004 118.984 260.329  1.00  0.00           C
ATOM    5910  N2   G   D  53      71.034 118.635 261.120  1.00  0.00           N
ATOM    5911  N3   G   D  53      70.167 120.014 259.494  1.00  0.00           N
ATOM    5912  C4   G   D  53      69.059 120.252 258.768  1.00  0.00           C
HETATM  5913  N1   5MU D  54      71.979 116.832 257.972  1.00  0.00           N
HETATM  5914  C2   5MU D  54      71.372 115.904 258.801  1.00  0.00           C
HETATM  5915  N3   5MU D  54      70.093 115.554 258.515  1.00  0.00           N
HETATM  5916  C4   5MU D  54      69.396 116.056 257.464  1.00  0.00           C
HETATM  5917  C5   5MU D  54      70.037 117.011 256.623  1.00  0.00           C
HETATM  5918  C5M  5MU D  54      69.299 117.600 255.448  1.00  0.00           C
HETATM  5919  C6   5MU D  54      71.298 117.360 256.908  1.00  0.00           C
HETATM  5920  O2   5MU D  54      71.971 115.421 259.765  1.00  0.00           O
HETATM  5921  O4   5MU D  54      68.206 115.661 257.294  1.00  0.00           O
HETATM  5922  C1*  5MU D  54      73.373 117.218 258.280  1.00  0.00           C
HETATM  5923  C2*  5MU D  54      74.293 116.260 257.570  1.00  0.00           C
HETATM  5924  O2*  5MU D  54      75.511 116.072 258.278  1.00  0.00           O
HETATM  5925  C3*  5MU D  54      74.663 117.059 256.322  1.00  0.00           C
HETATM  5926  C4*  5MU D  54      74.716 118.476 256.874  1.00  0.00           C
HETATM  5927  O3*  5MU D  54      75.877 116.603 255.713  1.00  0.00           O
HETATM  5928  O4*  5MU D  54      73.669 118.527 257.836  1.00  0.00           O
HETATM  5929  C5*  5MU D  54      74.522 119.569 255.850  1.00  0.00           C
HETATM  5930  O5*  5MU D  54      73.613 119.012 254.844  1.00  0.00           O
HETATM  5931  P    5MU D  54      72.780 120.095 254.018  1.00  0.00           P
HETATM  5932  O1P  5MU D  54      71.395 119.696 253.676  1.00  0.00           O
HETATM  5933  O2P  5MU D  54      73.560 120.638 252.857  1.00  0.00           O
HETATM  5934  N1   PSU D  55      70.876 114.557 254.470  1.00  0.00           N
HETATM  5935  C2   PSU D  55      69.578 114.141 254.531  1.00  0.00           C
HETATM  5936  N3   PSU D  55      69.403 112.968 255.208  1.00  0.00           N
HETATM  5937  C4   PSU D  55      70.385 112.203 255.821  1.00  0.00           C
HETATM  5938  C5   PSU D  55      71.731 112.732 255.714  1.00  0.00           C
HETATM  5939  C6   PSU D  55      71.907 113.877 255.043  1.00  0.00           C
HETATM  5940  O2   PSU D  55      68.653 114.764 254.014  1.00  0.00           O
HETATM  5941  O4   PSU D  55      70.137 111.174 256.412  1.00  0.00           O
HETATM  5942  C1*  PSU D  55      72.870 111.984 256.337  1.00  0.00           C
HETATM  5943  C2*  PSU D  55      73.528 111.078 255.314  1.00  0.00           C
HETATM  5944  O2*  PSU D  55      74.036 109.898 255.921  1.00  0.00           O
HETATM  5945  C3*  PSU D  55      74.730 111.931 254.895  1.00  0.00           C
HETATM  5946  C4*  PSU D  55      75.098 112.614 256.204  1.00  0.00           C
HETATM  5947  O3*  PSU D  55      75.778 111.145 254.310  1.00  0.00           O
HETATM  5948  O4*  PSU D  55      73.847 112.876 256.838  1.00  0.00           O
HETATM  5949  C5*  PSU D  55      75.876 113.914 256.057  1.00  0.00           C
HETATM  5950  O5*  PSU D  55      75.786 114.295 254.658  1.00  0.00           O
HETATM  5951  P    PSU D  55      75.709 115.847 254.287  1.00  0.00           P
HETATM  5952  O1P  PSU D  55      74.342 116.280 253.856  1.00  0.00           O
HETATM  5953  O2P  PSU D  55      76.768 116.249 253.331  1.00  0.00           O
ATOM    5954  P    C   D  56      75.917 110.922 252.638  1.00  0.00           P
ATOM    5955  O1P  C   D  56      77.182 110.140 252.475  1.00  0.00           O
ATOM    5956  O2P  C   D  56      75.733 112.211 251.902  1.00  0.00           O
ATOM    5957  O5*  C   D  56      74.700 110.010 252.179  1.00  0.00           O
ATOM    5958  C5*  C   D  56      74.387 109.898 250.807  1.00  0.00           C
ATOM    5959  C4*  C   D  56      73.287 108.902 250.596  1.00  0.00           C
ATOM    5960  O4*  C   D  56      73.793 107.578 250.871  1.00  0.00           O
ATOM    5961  C3*  C   D  56      72.092 109.054 251.529  1.00  0.00           C
ATOM    5962  O3*  C   D  56      71.206 110.005 250.959  1.00  0.00           O
ATOM    5963  C2*  C   D  56      71.497 107.658 251.485  1.00  0.00           C
ATOM    5964  O2*  C   D  56      70.674 107.403 250.343  1.00  0.00           O
ATOM    5965  C1*  C   D  56      72.765 106.797 251.461  1.00  0.00           C
ATOM    5966  N1   C   D  56      73.194 106.441 252.820  1.00  0.00           N
ATOM    5967  C2   C   D  56      72.530 105.417 253.472  1.00  0.00           C
ATOM    5968  O2   C   D  56      71.590 104.887 252.926  1.00  0.00           O
ATOM    5969  N3   C   D  56      72.927 105.036 254.686  1.00  0.00           N
ATOM    5970  C4   C   D  56      73.941 105.644 255.278  1.00  0.00           C
ATOM    5971  N4   C   D  56      74.288 105.196 256.483  1.00  0.00           N
ATOM    5972  C5   C   D  56      74.638 106.726 254.660  1.00  0.00           C
ATOM    5973  C6   C   D  56      74.230 107.091 253.429  1.00  0.00           C
ATOM    5974  P    A   D  57      70.636 111.075 252.314  1.00  0.00           P
ATOM    5975  O1P  A   D  57      69.978 112.221 251.603  1.00  0.00           O
ATOM    5976  O2P  A   D  57      71.842 111.523 253.055  1.00  0.00           O
ATOM    5977  O5*  A   D  57      69.581 110.256 253.174  1.00  0.00           O
ATOM    5978  C5*  A   D  57      68.579 109.499 252.433  1.00  0.00           C
ATOM    5979  C4*  A   D  57      67.950 108.542 253.427  1.00  0.00           C
ATOM    5980  O4*  A   D  57      68.885 107.526 253.760  1.00  0.00           O
ATOM    5981  C3*  A   D  57      67.560 109.168 254.765  1.00  0.00           C
```

```
ATOM   5982  O3*  A D  57      66.310 109.831 254.716  1.00  0.00           O
ATOM   5983  C2*  A D  57      67.562 107.943 255.686  1.00  0.00           C
ATOM   5984  O2*  A D  57      66.306 107.305 255.500  1.00  0.00           O
ATOM   5985  C1*  A D  57      68.705 107.127 255.127  1.00  0.00           C
ATOM   5986  N9   A D  57      69.964 107.314 255.861  1.00  0.00           N
ATOM   5987  C8   A D  57      71.083 107.974 255.438  1.00  0.00           C
ATOM   5988  N7   A D  57      72.063 107.975 256.306  1.00  0.00           N
ATOM   5989  C5   A D  57      71.543 107.258 257.379  1.00  0.00           C
ATOM   5990  C6   A D  57      72.110 106.905 258.632  1.00  0.00           C
ATOM   5991  N6   A D  57      73.335 107.232 259.018  1.00  0.00           N
ATOM   5992  N1   A D  57      71.294 106.181 259.450  1.00  0.00           N
ATOM   5993  C2   A D  57      70.028 105.833 259.074  1.00  0.00           C
ATOM   5994  N3   A D  57      69.443 106.128 257.921  1.00  0.00           N
ATOM   5995  C4   A D  57      70.266 106.849 257.114  1.00  0.00           C
ATOM   5996  P    A D  58      65.749 110.971 255.690  1.00  0.00           P
ATOM   5997  O1P  A D  58      64.275 111.151 255.515  1.00  0.00           O
ATOM   5998  O2P  A D  58      66.515 112.172 255.271  1.00  0.00           O
ATOM   5999  O5*  A D  58      66.075 110.461 257.164  1.00  0.00           O
ATOM   6000  C5*  A D  58      65.406 109.278 257.669  1.00  0.00           C
ATOM   6001  C4*  A D  58      64.861 109.659 259.034  1.00  0.00           C
ATOM   6002  O4*  A D  58      65.954 110.080 259.852  1.00  0.00           O
ATOM   6003  C3*  A D  58      63.885 110.831 259.000  1.00  0.00           C
ATOM   6004  O3*  A D  58      62.861 110.658 260.011  1.00  0.00           O
ATOM   6005  C2*  A D  58      64.774 112.020 259.334  1.00  0.00           C
ATOM   6006  O2*  A D  58      63.963 113.066 259.808  1.00  0.00           O
ATOM   6007  C1*  A D  58      65.723 111.418 260.317  1.00  0.00           C
ATOM   6008  N9   A D  58      66.985 112.176 260.404  1.00  0.00           N
ATOM   6009  C8   A D  58      67.461 113.150 259.569  1.00  0.00           C
ATOM   6010  N7   A D  58      68.614 113.636 259.925  1.00  0.00           N
ATOM   6011  C5   A D  58      68.936 112.934 261.077  1.00  0.00           C
ATOM   6012  C6   A D  58      70.047 112.990 261.941  1.00  0.00           C
ATOM   6013  N6   A D  58      71.088 113.805 261.773  1.00  0.00           N
ATOM   6014  N1   A D  58      70.017 112.132 263.001  1.00  0.00           N
ATOM   6015  C2   A D  58      68.974 111.281 263.205  1.00  0.00           C
ATOM   6016  N3   A D  58      67.889 111.175 262.433  1.00  0.00           N
ATOM   6017  C4   A D  58      67.929 112.025 261.390  1.00  0.00           C
ATOM   6018  P    U D  59      61.341 111.149 259.834  1.00  0.00           P
ATOM   6019  O1P  U D  59      60.521 110.132 259.096  1.00  0.00           O
ATOM   6020  O2P  U D  59      61.481 112.415 259.049  1.00  0.00           O
ATOM   6021  O5*  U D  59      60.776 111.350 261.321  1.00  0.00           O
ATOM   6022  C5*  U D  59      60.311 112.694 261.609  1.00  0.00           C
ATOM   6023  C4*  U D  59      60.077 112.824 263.089  1.00  0.00           C
ATOM   6024  O4*  U D  59      59.328 111.691 263.545  1.00  0.00           O
ATOM   6025  C3*  U D  59      61.331 112.817 263.963  1.00  0.00           C
ATOM   6026  O3*  U D  59      61.958 114.082 264.055  1.00  0.00           O
ATOM   6027  C2*  U D  59      60.774 112.342 265.314  1.00  0.00           C
ATOM   6028  O2*  U D  59      60.210 113.483 265.945  1.00  0.00           O
ATOM   6029  C1*  U D  59      59.708 111.357 264.882  1.00  0.00           C
ATOM   6030  N1   U D  59      60.227 109.976 264.978  1.00  0.00           N
ATOM   6031  C2   U D  59      60.618 109.553 266.240  1.00  0.00           C
ATOM   6032  O2   U D  59      60.533 110.297 267.213  1.00  0.00           O
ATOM   6033  N3   U D  59      61.096 108.281 266.369  1.00  0.00           N
ATOM   6034  C4   U D  59      61.192 107.436 265.302  1.00  0.00           C
ATOM   6035  O4   U D  59      61.646 106.272 265.539  1.00  0.00           O
ATOM   6036  C5   U D  59      60.778 107.883 264.015  1.00  0.00           C
ATOM   6037  C6   U D  59      60.320 109.138 263.911  1.00  0.00           C
ATOM   6038  P    U D  60      63.499 114.298 263.615  1.00  0.00           P
ATOM   6039  O1P  U D  60      63.840 115.755 263.628  1.00  0.00           O
ATOM   6040  O2P  U D  60      63.538 113.720 262.256  1.00  0.00           O
ATOM   6041  O5*  U D  60      64.311 113.509 264.734  1.00  0.00           O
ATOM   6042  C5*  U D  60      64.052 113.891 266.104  1.00  0.00           C
ATOM   6043  C4*  U D  60      64.631 112.813 267.000  1.00  0.00           C
ATOM   6044  O4*  U D  60      64.021 111.563 266.711  1.00  0.00           O
ATOM   6045  C3*  U D  60      66.150 112.591 266.805  1.00  0.00           C
ATOM   6046  O3*  U D  60      66.749 112.316 268.105  1.00  0.00           O
ATOM   6047  C2*  U D  60      66.195 111.387 265.881  1.00  0.00           C
ATOM   6048  O2*  U D  60      67.417 110.735 266.006  1.00  0.00           O
ATOM   6049  C1*  U D  60      65.011 110.582 266.362  1.00  0.00           C
ATOM   6050  N1   U D  60      64.552 109.658 265.317  1.00  0.00           N
ATOM   6051  C2   U D  60      64.669 108.309 265.595  1.00  0.00           C
ATOM   6052  O2   U D  60      65.122 107.928 266.672  1.00  0.00           O
ATOM   6053  N3   U D  60      64.248 107.420 264.645  1.00  0.00           N
ATOM   6054  C4   U D  60      63.733 107.823 263.448  1.00  0.00           C
ATOM   6055  O4   U D  60      63.370 106.905 262.647  1.00  0.00           O
ATOM   6056  C5   U D  60      63.630 109.219 263.175  1.00  0.00           C
ATOM   6057  C6   U D  60      64.048 110.075 264.120  1.00  0.00           C
ATOM   6058  P    C D  61      67.166 113.681 268.876  1.00  0.00           P
ATOM   6059  O1P  C D  61      67.440 113.435 270.320  1.00  0.00           O
ATOM   6060  O2P  C D  61      65.985 114.558 268.642  1.00  0.00           O
ATOM   6061  O5*  C D  61      68.464 114.141 268.095  1.00  0.00           O
ATOM   6062  C5*  C D  61      69.765 113.519 268.358  1.00  0.00           C
ATOM   6063  C4*  C D  61      70.748 114.362 267.570  1.00  0.00           C
ATOM   6064  O4*  C D  61      70.782 113.923 266.233  1.00  0.00           O
ATOM   6065  C3*  C D  61      70.370 115.836 267.494  1.00  0.00           C
ATOM   6066  O3*  C D  61      70.740 116.571 268.654  1.00  0.00           O
ATOM   6067  C2*  C D  61      71.123 116.274 266.228  1.00  0.00           C
ATOM   6068  O2*  C D  61      72.468 116.511 266.627  1.00  0.00           O
```

```
ATOM 6069 C1*  C D 61   71.003 115.037 265.378  1.00 0.00   C
ATOM 6070 N1   C D 61   69.868 115.205 264.464  1.00 0.00   N
ATOM 6071 C2   C D 61   69.969 116.155 263.469  1.00 0.00   C
ATOM 6072 O2   C D 61   70.985 116.826 263.374  1.00 0.00   O
ATOM 6073 N3   C D 61   68.909 116.302 262.625  1.00 0.00   N
ATOM 6074 C4   C D 61   67.784 115.545 262.747  1.00 0.00   C
ATOM 6075 N4   C D 61   66.764 115.721 261.904  1.00 0.00   N
ATOM 6076 C5   C D 61   67.680 114.565 263.784  1.00 0.00   C
ATOM 6077 C6   C D 61   68.737 114.436 264.598  1.00 0.00   C
ATOM 6078 P    C D 62   70.417 118.127 268.851  1.00 0.00   P
ATOM 6079 O1P  C D 62   71.090 118.664 270.082  1.00 0.00   O
ATOM 6080 O2P  C D 62   68.944 118.202 268.984  1.00 0.00   O
ATOM 6081 O5*  C D 62   70.989 118.799 267.511  1.00 0.00   O
ATOM 6082 C5*  C D 62   72.234 119.534 267.609  1.00 0.00   C
ATOM 6083 C4*  C D 62   72.572 120.093 266.255  1.00 0.00   C
ATOM 6084 O4*  C D 62   72.142 119.245 265.200  1.00 0.00   O
ATOM 6085 C3*  C D 62   71.914 121.440 265.954  1.00 0.00   C
ATOM 6086 O3*  C D 62   72.567 122.561 266.580  1.00 0.00   O
ATOM 6087 C2*  C D 62   71.978 121.476 264.436  1.00 0.00   C
ATOM 6088 O2*  C D 62   73.280 121.896 264.087  1.00 0.00   O
ATOM 6089 C1*  C D 62   71.765 120.014 264.083  1.00 0.00   C
ATOM 6090 N1   C D 62   70.331 119.931 263.737  1.00 0.00   N
ATOM 6091 C2   C D 62   69.902 120.778 262.716  1.00 0.00   C
ATOM 6092 O2   C D 62   70.692 121.513 262.148  1.00 0.00   O
ATOM 6093 N3   C D 62   68.579 120.740 262.386  1.00 0.00   N
ATOM 6094 C4   C D 62   67.695 119.925 263.023  1.00 0.00   C
ATOM 6095 N4   C D 62   66.418 119.938 262.652  1.00 0.00   N
ATOM 6096 C5   C D 62   68.154 119.073 264.069  1.00 0.00   C
ATOM 6097 C6   C D 62   69.452 119.118 264.385  1.00 0.00   C
ATOM 6098 P    C D 63   71.684 123.352 267.696  1.00 0.00   P
ATOM 6099 O1P  C D 63   72.551 123.963 268.757  1.00 0.00   O
ATOM 6100 O2P  C D 63   70.826 122.284 268.266  1.00 0.00   O
ATOM 6101 O5*  C D 63   70.956 124.470 266.824  1.00 0.00   O
ATOM 6102 C5*  C D 63   71.698 125.657 266.459  1.00 0.00   C
ATOM 6103 C4*  C D 63   71.112 126.206 265.177  1.00 0.00   C
ATOM 6104 O4*  C D 63   70.737 125.127 264.326  1.00 0.00   O
ATOM 6105 C3*  C D 63   69.840 127.025 265.342  1.00 0.00   C
ATOM 6106 O3*  C D 63   70.056 128.381 265.749  1.00 0.00   O
ATOM 6107 C2*  C D 63   69.200 126.908 263.958  1.00 0.00   C
ATOM 6108 O2*  C D 63   69.857 127.880 263.132  1.00 0.00   O
ATOM 6109 C1*  C D 63   69.586 125.502 263.574  1.00 0.00   C
ATOM 6110 N1   C D 63   68.455 124.607 263.865  1.00 0.00   N
ATOM 6111 C2   C D 63   67.275 124.820 263.190  1.00 0.00   C
ATOM 6112 O2   C D 63   67.169 125.722 262.370  1.00 0.00   O
ATOM 6113 N3   C D 63   66.217 123.988 263.471  1.00 0.00   N
ATOM 6114 C4   C D 63   66.321 122.988 264.385  1.00 0.00   C
ATOM 6115 N4   C D 63   65.273 122.209 264.624  1.00 0.00   N
ATOM 6116 C5   C D 63   67.544 122.779 265.080  1.00 0.00   C
ATOM 6117 C6   C D 63   68.567 123.597 264.786  1.00 0.00   C
ATOM 6118 P    C D 64   69.204 128.940 267.008  1.00 0.00   P
ATOM 6119 O1P  C D 64   70.047 129.642 268.029  1.00 0.00   O
ATOM 6120 O2P  C D 64   68.604 127.700 267.568  1.00 0.00   O
ATOM 6121 O5*  C D 64   68.162 129.940 266.353  1.00 0.00   O
ATOM 6122 C5*  C D 64   68.436 130.581 265.072  1.00 0.00   C
ATOM 6123 C4*  C D 64   67.070 130.769 264.438  1.00 0.00   C
ATOM 6124 O4*  C D 64   66.726 129.605 263.693  1.00 0.00   O
ATOM 6125 C3*  C D 64   65.918 130.944 265.420  1.00 0.00   C
ATOM 6126 O3*  C D 64   65.755 132.273 265.952  1.00 0.00   O
ATOM 6127 C2*  C D 64   64.714 130.515 264.576  1.00 0.00   C
ATOM 6128 O2*  C D 64   64.326 131.617 263.784  1.00 0.00   O
ATOM 6129 C1*  C D 64   65.324 129.397 263.750  1.00 0.00   C
ATOM 6130 N1   C D 64   64.928 128.156 264.416  1.00 0.00   N
ATOM 6131 C2   C D 64   63.649 127.684 264.152  1.00 0.00   C
ATOM 6132 O2   C D 64   62.921 128.292 263.371  1.00 0.00   O
ATOM 6133 N3   C D 64   63.243 126.532 264.776  1.00 0.00   N
ATOM 6134 C4   C D 64   64.050 125.862 265.636  1.00 0.00   C
ATOM 6135 N4   C D 64   63.592 124.747 266.214  1.00 0.00   N
ATOM 6136 C5   C D 64   65.360 126.359 265.912  1.00 0.00   C
ATOM 6137 C6   C D 64   65.742 127.489 265.294  1.00 0.00   C
ATOM 6138 P    G D 65   64.778 132.298 267.265  1.00 0.00   P
ATOM 6139 O1P  G D 65   64.845 133.584 268.000  1.00 0.00   O
ATOM 6140 O2P  G D 65   65.298 131.159 268.077  1.00 0.00   O
ATOM 6141 O5*  G D 65   63.345 132.025 266.609  1.00 0.00   O
ATOM 6142 C5*  G D 65   62.683 133.088 265.878  1.00 0.00   C
ATOM 6143 C4*  G D 65   61.258 132.633 265.628  1.00 0.00   C
ATOM 6144 O4*  G D 65   61.282 131.387 264.948  1.00 0.00   O
ATOM 6145 C3*  G D 65   60.417 132.364 266.883  1.00 0.00   C
ATOM 6146 O3*  G D 65   59.862 133.548 267.450  1.00 0.00   O
ATOM 6147 C2*  G D 65   59.372 131.391 266.344  1.00 0.00   C
ATOM 6148 O2*  G D 65   58.382 132.196 265.711  1.00 0.00   O
ATOM 6149 C1*  G D 65   60.164 130.590 265.339  1.00 0.00   C
ATOM 6150 N9   G D 65   60.622 129.321 265.933  1.00 0.00   N
ATOM 6151 C8   G D 65   61.838 129.087 266.538  1.00 0.00   C
ATOM 6152 N7   G D 65   61.994 127.866 266.975  1.00 0.00   N
ATOM 6153 C5   G D 65   60.789 127.245 266.635  1.00 0.00   C
ATOM 6154 C6   G D 65   60.332 125.918 266.836  1.00 0.00   C
ATOM 6155 O6   G D 65   60.939 124.987 267.378  1.00 0.00   O
```

```
ATOM   6156  N1    G D  65      59.079 125.672 266.350  1.00  0.00           N
ATOM   6157  C2    G D  65      58.335 126.636 265.734  1.00  0.00           C
ATOM   6158  N2    G D  65      57.128 126.245 265.315  1.00  0.00           N
ATOM   6159  N3    G D  65      58.718 127.890 265.520  1.00  0.00           N
ATOM   6160  C4    G D  65      59.949 128.131 265.994  1.00  0.00           C
ATOM   6161  P     U D  66      58.879 133.549 268.724  1.00  0.00           P
ATOM   6162  O1P   U D  66      58.361 134.921 269.045  1.00  0.00           O
ATOM   6163  O2P   U D  66      59.766 133.061 269.822  1.00  0.00           O
ATOM   6164  O5*   U D  66      57.688 132.582 268.309  1.00  0.00           O
ATOM   6165  C5*   U D  66      56.518 133.024 267.547  1.00  0.00           C
ATOM   6166  C4*   U D  66      55.465 132.010 267.923  1.00  0.00           C
ATOM   6167  O4*   U D  66      55.823 130.732 267.451  1.00  0.00           O
ATOM   6168  C3*   U D  66      55.291 131.819 269.424  1.00  0.00           C
ATOM   6169  O3*   U D  66      54.474 132.811 270.033  1.00  0.00           O
ATOM   6170  C2*   U D  66      54.681 130.416 269.509  1.00  0.00           C
ATOM   6171  O2*   U D  66      53.289 130.559 269.232  1.00  0.00           O
ATOM   6172  C1*   U D  66      55.384 129.721 268.376  1.00  0.00           C
ATOM   6173  N1    U D  66      56.583 128.962 268.785  1.00  0.00           N
ATOM   6174  C2    U D  66      56.408 127.608 269.045  1.00  0.00           C
ATOM   6175  O2    U D  66      55.297 127.088 268.961  1.00  0.00           O
ATOM   6176  N3    U D  66      57.524 126.899 269.403  1.00  0.00           N
ATOM   6177  C4    U D  66      58.749 127.459 269.510  1.00  0.00           C
ATOM   6178  O4    U D  66      59.716 126.714 269.849  1.00  0.00           O
ATOM   6179  C5    U D  66      58.911 128.857 269.228  1.00  0.00           C
ATOM   6180  C6    U D  66      57.811 129.539 268.878  1.00  0.00           C
ATOM   6181  P     C D  67      54.441 132.904 271.649  1.00  0.00           P
ATOM   6182  O1P   C D  67      53.636 134.082 272.084  1.00  0.00           O
ATOM   6183  O2P   C D  67      55.888 133.037 271.957  1.00  0.00           O
ATOM   6184  O5*   C D  67      53.791 131.537 272.110  1.00  0.00           O
ATOM   6185  C5*   C D  67      52.337 131.355 271.986  1.00  0.00           C
ATOM   6186  C4*   C D  67      52.106 129.938 272.462  1.00  0.00           C
ATOM   6187  O4*   C D  67      52.785 129.035 271.621  1.00  0.00           O
ATOM   6188  C3*   C D  67      52.635 129.645 273.864  1.00  0.00           C
ATOM   6189  O3*   C D  67      51.759 130.092 274.894  1.00  0.00           O
ATOM   6190  C2*   C D  67      52.805 128.128 273.817  1.00  0.00           C
ATOM   6191  O2*   C D  67      51.533 127.573 274.077  1.00  0.00           O
ATOM   6192  C1*   C D  67      53.248 127.929 272.376  1.00  0.00           C
ATOM   6193  N1    C D  67      54.712 127.827 272.362  1.00  0.00           N
ATOM   6194  C2    C D  67      55.280 126.627 272.751  1.00  0.00           C
ATOM   6195  O2    C D  67      54.571 125.680 273.092  1.00  0.00           O
ATOM   6196  N3    C D  67      56.646 126.550 272.745  1.00  0.00           N
ATOM   6197  C4    C D  67      57.434 127.598 272.369  1.00  0.00           C
ATOM   6198  N4    C D  67      58.756 127.453 272.387  1.00  0.00           N
ATOM   6199  C5    C D  67      56.838 128.820 271.982  1.00  0.00           C
ATOM   6200  C6    C D  67      55.495 128.887 271.990  1.00  0.00           C
ATOM   6201  P     G D  68      52.247 130.338 276.400  1.00  0.00           P
ATOM   6202  O1P   G D  68      51.259 131.158 277.171  1.00  0.00           O
ATOM   6203  O2P   G D  68      53.541 131.052 276.256  1.00  0.00           O
ATOM   6204  O5*   G D  68      52.354 128.849 276.966  1.00  0.00           O
ATOM   6205  C5*   G D  68      51.104 128.170 277.302  1.00  0.00           C
ATOM   6206  C4*   G D  68      51.528 126.831 277.866  1.00  0.00           C
ATOM   6207  O4*   G D  68      52.178 126.091 276.846  1.00  0.00           O
ATOM   6208  C3*   G D  68      52.558 126.915 278.992  1.00  0.00           C
ATOM   6209  O3*   G D  68      51.940 127.175 280.256  1.00  0.00           O
ATOM   6210  C2*   G D  68      53.214 125.539 278.913  1.00  0.00           C
ATOM   6211  O2*   G D  68      52.359 124.638 279.603  1.00  0.00           O
ATOM   6212  C1*   G D  68      53.214 125.287 277.415  1.00  0.00           C
ATOM   6213  N9    G D  68      54.524 125.634 276.831  1.00  0.00           N
ATOM   6214  C8    G D  68      54.842 126.670 275.992  1.00  0.00           C
ATOM   6215  N7    G D  68      56.121 126.702 275.642  1.00  0.00           N
ATOM   6216  C5    G D  68      56.663 125.603 276.300  1.00  0.00           C
ATOM   6217  C6    G D  68      57.992 125.090 276.337  1.00  0.00           C
ATOM   6218  O6    G D  68      59.008 125.513 275.769  1.00  0.00           O
ATOM   6219  N1    G D  68      58.115 123.975 277.117  1.00  0.00           N
ATOM   6220  C2    G D  68      57.096 123.403 277.799  1.00  0.00           C
ATOM   6221  N2    G D  68      57.423 122.318 278.507  1.00  0.00           N
ATOM   6222  N3    G D  68      55.836 123.840 277.797  1.00  0.00           N
ATOM   6223  C4    G D  68      55.705 124.946 277.030  1.00  0.00           C
ATOM   6224  P     C D  69      52.734 127.345 281.641  1.00  0.00           P
ATOM   6225  O1P   C D  69      51.837 127.159 282.815  1.00  0.00           O
ATOM   6226  O2P   C D  69      53.293 128.721 281.572  1.00  0.00           O
ATOM   6227  O5*   C D  69      53.823 126.181 281.571  1.00  0.00           O
ATOM   6228  C5*   C D  69      53.475 124.845 282.030  1.00  0.00           C
ATOM   6229  C4*   C D  69      54.799 124.204 282.409  1.00  0.00           C
ATOM   6230  O4*   C D  69      55.586 124.042 281.246  1.00  0.00           O
ATOM   6231  C3*   C D  69      55.670 125.013 283.367  1.00  0.00           C
ATOM   6232  O3*   C D  69      55.285 124.893 284.746  1.00  0.00           O
ATOM   6233  C2*   C D  69      57.048 124.446 283.075  1.00  0.00           C
ATOM   6234  O2*   C D  69      57.178 123.233 283.800  1.00  0.00           O
ATOM   6235  C1*   C D  69      56.968 124.181 281.577  1.00  0.00           C
ATOM   6236  N1    C D  69      57.621 125.309 280.882  1.00  0.00           N
ATOM   6237  C2    C D  69      58.978 125.224 280.676  1.00  0.00           C
ATOM   6238  O2    C D  69      59.615 124.241 281.055  1.00  0.00           O
ATOM   6239  N3    C D  69      59.593 126.260 280.038  1.00  0.00           N
ATOM   6240  C4    C D  69      58.901 127.356 279.617  1.00  0.00           C
ATOM   6241  N4    C D  69      59.564 128.343 278.993  1.00  0.00           N
ATOM   6242  C5    C D  69      57.498 127.432 279.834  1.00  0.00           C
```

```
ATOM   6243  C6    C D  69      56.913 126.405 280.466  1.00  0.00           C
ATOM   6244  P     G D  70      55.420 126.191 285.704  1.00  0.00           P
ATOM   6245  O1P   G D  70      54.339 126.262 286.733  1.00  0.00           O
ATOM   6246  O2P   G D  70      55.343 127.315 284.739  1.00  0.00           O
ATOM   6247  O5*   G D  70      56.839 125.955 286.408  1.00  0.00           O
ATOM   6248  C5*   G D  70      57.256 124.570 286.593  1.00  0.00           C
ATOM   6249  C4*   G D  70      58.764 124.568 286.631  1.00  0.00           C
ATOM   6250  O4*   G D  70      59.296 124.274 285.341  1.00  0.00           O
ATOM   6251  C3*   G D  70      59.392 125.916 286.998  1.00  0.00           C
ATOM   6252  O3*   G D  70      59.391 126.162 288.401  1.00  0.00           O
ATOM   6253  C2*   G D  70      60.791 125.787 286.402  1.00  0.00           C
ATOM   6254  O2*   G D  70      61.582 125.052 287.323  1.00  0.00           O
ATOM   6255  C1*   G D  70      60.516 124.987 285.140  1.00  0.00           C
ATOM   6256  N9    G D  70      60.443 125.921 284.009  1.00  0.00           N
ATOM   6257  C8    G D  70      59.347 126.444 283.393  1.00  0.00           C
ATOM   6258  N7    G D  70      59.624 127.258 282.407  1.00  0.00           N
ATOM   6259  C5    G D  70      61.019 127.279 282.372  1.00  0.00           C
ATOM   6260  C6    G D  70      61.934 127.970 281.535  1.00  0.00           C
ATOM   6261  O6    G D  70      61.655 128.739 280.612  1.00  0.00           O
ATOM   6262  N1    G D  70      63.248 127.729 281.810  1.00  0.00           N
ATOM   6263  C2    G D  70      63.645 126.893 282.812  1.00  0.00           C
ATOM   6264  N2    G D  70      64.959 126.763 282.965  1.00  0.00           N
ATOM   6265  N3    G D  70      62.836 126.227 283.631  1.00  0.00           N
ATOM   6266  C4    G D  70      61.541 126.460 283.352  1.00  0.00           C
ATOM   6267  P     G D  71      60.054 127.505 289.012  1.00  0.00           P
ATOM   6268  O1P   G D  71      59.786 127.593 290.482  1.00  0.00           O
ATOM   6269  O2P   G D  71      59.371 128.585 288.248  1.00  0.00           O
ATOM   6270  O5*   G D  71      61.593 127.338 288.673  1.00  0.00           O
ATOM   6271  C5*   G D  71      62.552 126.705 289.558  1.00  0.00           C
ATOM   6272  C4*   G D  71      63.913 127.152 289.044  1.00  0.00           C
ATOM   6273  O4*   G D  71      63.955 126.965 287.632  1.00  0.00           O
ATOM   6274  C3*   G D  71      64.239 128.616 289.241  1.00  0.00           C
ATOM   6275  O3*   G D  71      64.742 128.943 290.539  1.00  0.00           O
ATOM   6276  C2*   G D  71      65.282 128.857 288.139  1.00  0.00           C
ATOM   6277  O2*   G D  71      66.520 128.390 288.656  1.00  0.00           O
ATOM   6278  C1*   G D  71      64.758 127.975 287.036  1.00  0.00           C
ATOM   6279  N9    G D  71      63.974 128.755 286.060  1.00  0.00           N
ATOM   6280  C8    G D  71      62.608 128.687 285.853  1.00  0.00           C
ATOM   6281  N7    G D  71      62.182 129.491 284.915  1.00  0.00           N
ATOM   6282  C5    G D  71      63.338 130.121 284.464  1.00  0.00           C
ATOM   6283  C6    G D  71      63.541 131.104 283.455  1.00  0.00           C
ATOM   6284  O6    G D  71      62.689 131.621 282.736  1.00  0.00           O
ATOM   6285  N1    G D  71      64.850 131.489 283.298  1.00  0.00           N
ATOM   6286  C2    G D  71      65.860 130.969 284.052  1.00  0.00           C
ATOM   6287  N2    G D  71      67.078 131.446 283.784  1.00  0.00           N
ATOM   6288  N3    G D  71      65.725 130.056 285.008  1.00  0.00           N
ATOM   6289  C4    G D  71      64.444 129.676 285.157  1.00  0.00           C
ATOM   6290  P     A D  72      65.171 130.470 290.847  1.00  0.00           P
ATOM   6291  O1P   A D  72      65.522 130.679 292.286  1.00  0.00           O
ATOM   6292  O2P   A D  72      63.946 131.225 290.454  1.00  0.00           O
ATOM   6293  O5*   A D  72      66.412 130.706 289.879  1.00  0.00           O
ATOM   6294  C5*   A D  72      67.734 131.016 290.394  1.00  0.00           C
ATOM   6295  C4*   A D  72      68.440 131.845 289.349  1.00  0.00           C
ATOM   6296  O4*   A D  72      68.019 131.461 288.050  1.00  0.00           O
ATOM   6297  C3*   A D  72      68.158 133.341 289.400  1.00  0.00           C
ATOM   6298  O3*   A D  72      68.943 134.051 290.377  1.00  0.00           O
ATOM   6299  C2*   A D  72      68.484 133.790 287.971  1.00  0.00           C
ATOM   6300  O2*   A D  72      69.902 133.931 287.878  1.00  0.00           O
ATOM   6301  C1*   A D  72      68.010 132.594 287.175  1.00  0.00           C
ATOM   6302  N9    A D  72      66.658 132.842 286.643  1.00  0.00           N
ATOM   6303  C8    A D  72      65.486 132.207 287.010  1.00  0.00           C
ATOM   6304  N7    A D  72      64.435 132.641 286.354  1.00  0.00           N
ATOM   6305  C5    A D  72      64.954 133.613 285.496  1.00  0.00           C
ATOM   6306  C6    A D  72      64.320 134.434 284.546  1.00  0.00           C
ATOM   6307  N6    A D  72      63.029 134.416 284.280  1.00  0.00           N
ATOM   6308  N1    A D  72      65.147 135.295 283.873  1.00  0.00           N
ATOM   6309  C2    A D  72      66.495 135.334 284.132  1.00  0.00           C
ATOM   6310  N3    A D  72      67.142 134.582 285.021  1.00  0.00           N
ATOM   6311  C4    A D  72      66.312 133.741 285.670  1.00  0.00           C
ATOM   6312  P     G D  73      69.333 135.677 290.822  1.00  0.00           P
ATOM   6313  O1P   G D  73      70.759 135.790 291.263  1.00  0.00           O
ATOM   6314  O2P   G D  73      68.379 135.698 291.962  1.00  0.00           O
ATOM   6315  O5*   G D  73      68.950 136.665 289.643  1.00  0.00           O
ATOM   6316  C5*   G D  73      69.832 137.771 289.332  1.00  0.00           C
ATOM   6317  C4*   G D  73      69.769 138.021 287.840  1.00  0.00           C
ATOM   6318  O4*   G D  73      68.951 137.019 287.228  1.00  0.00           O
ATOM   6319  C3*   G D  73      69.114 139.343 287.434  1.00  0.00           C
ATOM   6320  O3*   G D  73      69.998 140.465 287.507  1.00  0.00           O
ATOM   6321  C2*   G D  73      68.659 139.028 286.011  1.00  0.00           C
ATOM   6322  O2*   G D  73      69.802 139.198 285.177  1.00  0.00           O
ATOM   6323  C1*   G D  73      68.266 137.568 286.112  1.00  0.00           C
ATOM   6324  N9    G D  73      66.793 137.496 286.247  1.00  0.00           N
ATOM   6325  C8    G D  73      66.056 136.813 287.174  1.00  0.00           C
ATOM   6326  N7    G D  73      64.763 136.951 287.040  1.00  0.00           N
ATOM   6327  C5    G D  73      64.637 137.796 285.935  1.00  0.00           C
ATOM   6328  C6    G D  73      63.490 138.320 285.281  1.00  0.00           C
ATOM   6329  O6    G D  73      62.297 138.138 285.572  1.00  0.00           O
```

```
ATOM  6330  N1    G D  73   63.769 139.132 284.211  1.00  0.00           N
ATOM  6331  C2    G D  73   65.040 139.396 283.818  1.00  0.00           C
ATOM  6332  N2    G D  73   65.143 140.206 282.751  1.00  0.00           N
ATOM  6333  N3    G D  73   66.153 138.938 284.384  1.00  0.00           N
ATOM  6334  C4    G D  73   65.865 138.134 285.443  1.00  0.00           C
ATOM  6335  P     C D  74   69.397 141.857 287.531  1.00  0.00           P
ATOM  6336  O1P   C D  74   70.494 142.901 287.693  1.00  0.00           O
ATOM  6337  O2P   C D  74   68.486 141.823 288.703  1.00  0.00           O
ATOM  6338  O5*   C D  74   68.544 141.891 286.200  1.00  0.00           O
ATOM  6339  C5*   C D  74   69.093 141.557 284.896  1.00  0.00           C
ATOM  6340  C4*   C D  74   68.140 142.125 283.870  1.00  0.00           C
ATOM  6341  O4*   C D  74   66.850 141.549 284.020  1.00  0.00           O
ATOM  6342  C3*   C D  74   67.899 143.626 284.010  1.00  0.00           C
ATOM  6343  O3*   C D  74   68.954 144.417 283.463  1.00  0.00           O
ATOM  6344  C2*   C D  74   66.562 143.767 283.263  1.00  0.00           C
ATOM  6345  O2*   C D  74   66.925 143.523 281.873  1.00  0.00           O
ATOM  6346  C1*   C D  74   65.832 142.554 283.748  1.00  0.00           C
ATOM  6347  N1    C D  74   65.076 142.747 284.981  1.00  0.00           N
ATOM  6348  C2    C D  74   63.925 143.508 284.949  1.00  0.00           C
ATOM  6349  O2    C D  74   63.547 144.011 283.908  1.00  0.00           O
ATOM  6350  N3    C D  74   63.217 143.663 286.121  1.00  0.00           N
ATOM  6351  C4    C D  74   63.630 143.105 287.281  1.00  0.00           C
ATOM  6352  N4    C D  74   62.914 143.288 288.393  1.00  0.00           N
ATOM  6353  C5    C D  74   64.806 142.328 287.299  1.00  0.00           C
ATOM  6354  C6    C D  74   65.492 142.175 286.157  1.00  0.00           C
ATOM  6355  P     C D  75   69.496 145.448 284.591  1.00  0.00           P
ATOM  6356  O1P   C D  75   70.942 145.572 284.191  1.00  0.00           O
ATOM  6357  O2P   C D  75   69.237 145.000 286.010  1.00  0.00           O
ATOM  6358  O5*   C D  75   68.617 146.796 284.396  1.00  0.00           O
ATOM  6359  C5*   C D  75   68.426 147.016 282.954  1.00  0.00           C
ATOM  6360  C4*   C D  75   67.054 147.644 282.825  1.00  0.00           C
ATOM  6361  O4*   C D  75   66.046 146.789 283.325  1.00  0.00           O
ATOM  6362  C3*   C D  75   66.884 148.930 283.621  1.00  0.00           C
ATOM  6363  O3*   C D  75   67.555 150.024 283.019  1.00  0.00           O
ATOM  6364  C2*   C D  75   65.372 149.044 283.661  1.00  0.00           C
ATOM  6365  O2*   C D  75   64.981 149.482 282.359  1.00  0.00           O
ATOM  6366  C1*   C D  75   64.977 147.579 283.820  1.00  0.00           C
ATOM  6367  N1    C D  75   64.673 147.342 285.241  1.00  0.00           N
ATOM  6368  C2    C D  75   63.541 148.018 285.710  1.00  0.00           C
ATOM  6369  O2    C D  75   62.902 148.731 284.943  1.00  0.00           O
ATOM  6370  N3    C D  75   63.200 147.844 287.015  1.00  0.00           N
ATOM  6371  C4    C D  75   63.920 147.051 287.855  1.00  0.00           C
ATOM  6372  N4    C D  75   63.526 146.926 289.114  1.00  0.00           N
ATOM  6373  C5    C D  75   65.061 146.365 287.360  1.00  0.00           C
ATOM  6374  C6    C D  75   65.384 146.546 286.063  1.00  0.00           C
ATOM  6375  P     A D  76   67.857 150.426 284.439  1.00  0.00           P
ATOM  6376  O1P   A D  76   67.773 151.801 283.916  1.00  0.00           O
ATOM  6377  O2P   A D  76   69.187 149.823 284.680  1.00  0.00           O
ATOM  6378  O5*   A D  76   66.954 150.120 285.725  1.00  0.00           O
ATOM  6379  C5*   A D  76   65.574 150.522 285.554  1.00  0.00           C
ATOM  6380  C4*   A D  76   64.966 150.526 286.920  1.00  0.00           C
ATOM  6381  O4*   A D  76   65.753 149.779 287.816  1.00  0.00           O
ATOM  6382  C3*   A D  76   64.683 151.858 287.583  1.00  0.00           C
ATOM  6383  O3*   A D  76   63.361 151.932 288.126  1.00  0.00           O
ATOM  6384  C2*   A D  76   65.756 151.952 288.670  1.00  0.00           C
ATOM  6385  O2*   A D  76   65.230 152.784 289.690  1.00  0.00           O
ATOM  6386  C1*   A D  76   65.882 150.503 289.061  1.00  0.00           C
ATOM  6387  N9    A D  76   67.203 150.222 289.637  1.00  0.00           N
ATOM  6388  C8    A D  76   68.295 149.703 288.994  1.00  0.00           C
ATOM  6389  N7    A D  76   69.347 149.564 289.760  1.00  0.00           N
ATOM  6390  C5    A D  76   68.905 150.029 290.999  1.00  0.00           C
ATOM  6391  C6    A D  76   69.566 150.131 292.249  1.00  0.00           C
ATOM  6392  N6    A D  76   70.744 149.807 292.472  1.00  0.00           N
ATOM  6393  N1    A D  76   68.794 150.641 293.262  1.00  0.00           N
ATOM  6394  C2    A D  76   67.504 151.005 293.064  1.00  0.00           C
ATOM  6395  N3    A D  76   66.839 150.926 291.914  1.00  0.00           N
ATOM  6396  C4    A D  76   67.594 150.427 290.927  1.00  0.00           C
TER   6397         A D  76
ATOM  6398  P     G 1   1   30.267  55.984 290.530  1.00  0.00           P
ATOM  6399  P     G 1   2   25.835  58.943 289.316  1.00  0.00           P
ATOM  6400  P     C 1   3   21.497  59.562 288.241  1.00  0.00           P
ATOM  6401  P     A 1   4   17.507  58.928 289.509  1.00  0.00           P
ATOM  6402  P     A 1   5   13.282  58.665 293.068  1.00  0.00           P
ATOM  6403  P     G 1   6   10.612  61.237 296.929  1.00  0.00           P
ATOM  6404  P     G 1   7   10.047  64.944 301.531  1.00  0.00           P
ATOM  6405  P     A 1   8   12.353  69.634 304.279  1.00  0.00           P
ATOM  6406  P     G 1   9   16.376  73.641 304.829  1.00  0.00           P
ATOM  6407  P     G 1  10   21.109  76.064 302.978  1.00  0.00           P
ATOM  6408  P     U 1  11   24.950  79.364 299.517  1.00  0.00           P
ATOM  6409  P     A 1  12   23.270  83.350 293.009  1.00  0.00           P
ATOM  6410  P     A 1  13   19.013  87.856 290.519  1.00  0.00           P
ATOM  6411  P     A 1  14   15.794  90.173 284.650  1.00  0.00           P
ATOM  6412  P     A 1  15   14.404  94.510 279.074  1.00  0.00           P
ATOM  6413  P     U 1  16    9.248  97.344 283.458  1.00  0.00           P
ATOM  6414  O1P   U 1  16    9.069  96.805 284.825  1.00  0.00           O
ATOM  6415  O2P   U 1  16    8.764  96.486 282.352  1.00  0.00           O
ATOM  6416  O5*   U 1  16    8.563  98.786 283.356  1.00  0.00           O
```

| | | | | | | | | | | |
|---|---|---|---|---|---|---|---|---|---|---|
| ATOM | 6417 | C5* | U | 1 | 16 | 8.892 | 99.785 | 284.340 | 1.00 | 0.00 | C |
| ATOM | 6418 | C4* | U | 1 | 16 | 8.176 | 101.082 | 284.019 | 1.00 | 0.00 | C |
| ATOM | 6419 | O4* | U | 1 | 16 | 8.690 | 101.605 | 282.760 | 1.00 | 0.00 | O |
| ATOM | 6420 | C3* | U | 1 | 16 | 6.669 | 100.973 | 283.785 | 1.00 | 0.00 | C |
| ATOM | 6421 | O3* | U | 1 | 16 | 5.945 | 100.960 | 285.007 | 1.00 | 0.00 | O |
| ATOM | 6422 | C2* | U | 1 | 16 | 6.386 | 102.217 | 282.931 | 1.00 | 0.00 | C |
| ATOM | 6423 | O2* | U | 1 | 16 | 6.374 | 103.379 | 283.714 | 1.00 | 0.00 | O |
| ATOM | 6424 | C1* | U | 1 | 16 | 7.645 | 102.259 | 282.058 | 1.00 | 0.00 | C |
| ATOM | 6425 | N1 | U | 1 | 16 | 7.447 | 101.562 | 280.757 | 1.00 | 0.00 | N |
| ATOM | 6426 | C2 | U | 1 | 16 | 6.790 | 102.256 | 279.768 | 1.00 | 0.00 | C |
| ATOM | 6427 | O2 | U | 1 | 16 | 6.376 | 103.392 | 279.922 | 1.00 | 0.00 | O |
| ATOM | 6428 | N3 | U | 1 | 16 | 6.626 | 101.579 | 278.577 | 1.00 | 0.00 | N |
| ATOM | 6429 | C4 | U | 1 | 16 | 7.053 | 100.298 | 278.297 | 1.00 | 0.00 | C |
| ATOM | 6430 | O4 | U | 1 | 16 | 6.848 | 99.795 | 277.191 | 1.00 | 0.00 | O |
| ATOM | 6431 | C5 | U | 1 | 16 | 7.732 | 99.650 | 279.395 | 1.00 | 0.00 | C |
| ATOM | 6432 | C6 | U | 1 | 16 | 7.906 | 100.286 | 280.566 | 1.00 | 0.00 | C |
| ATOM | 6433 | P | U | 1 | 17 | 4.601 | 100.397 | 285.104 | 1.00 | 0.00 | P |
| ATOM | 6434 | O1P | U | 1 | 17 | 4.143 | 100.343 | 286.511 | 1.00 | 0.00 | O |
| ATOM | 6435 | O2P | U | 1 | 17 | 4.691 | 99.097 | 284.400 | 1.00 | 0.00 | O |
| ATOM | 6436 | O5* | U | 1 | 17 | 3.664 | 101.392 | 284.273 | 1.00 | 0.00 | O |
| ATOM | 6437 | C5* | U | 1 | 17 | 3.435 | 102.720 | 284.779 | 1.00 | 0.00 | C |
| ATOM | 6438 | C4* | U | 1 | 17 | 2.570 | 103.502 | 283.809 | 1.00 | 0.00 | C |
| ATOM | 6439 | O4* | U | 1 | 17 | 3.309 | 103.691 | 282.568 | 1.00 | 0.00 | O |
| ATOM | 6440 | C3* | U | 1 | 17 | 1.276 | 102.817 | 283.368 | 1.00 | 0.00 | C |
| ATOM | 6441 | O3* | U | 1 | 17 | 0.237 | 102.990 | 284.321 | 1.00 | 0.00 | O |
| ATOM | 6442 | C2* | U | 1 | 17 | 0.987 | 103.511 | 282.030 | 1.00 | 0.00 | C |
| ATOM | 6443 | O2* | U | 1 | 17 | 0.465 | 104.798 | 282.226 | 1.00 | 0.00 | O |
| ATOM | 6444 | C1* | U | 1 | 17 | 2.407 | 103.666 | 281.474 | 1.00 | 0.00 | C |
| ATOM | 6445 | N1 | U | 1 | 17 | 2.784 | 102.535 | 280.581 | 1.00 | 0.00 | N |
| ATOM | 6446 | C2 | U | 1 | 17 | 2.319 | 102.575 | 279.288 | 1.00 | 0.00 | C |
| ATOM | 6447 | O2 | U | 1 | 17 | 1.625 | 103.483 | 278.862 | 1.00 | 0.00 | O |
| ATOM | 6448 | N3 | U | 1 | 17 | 2.690 | 101.512 | 278.491 | 1.00 | 0.00 | N |
| ATOM | 6449 | C4 | U | 1 | 17 | 3.468 | 100.437 | 278.868 | 1.00 | 0.00 | C |
| ATOM | 6450 | O4 | U | 1 | 17 | 3.734 | 99.542 | 278.063 | 1.00 | 0.00 | O |
| ATOM | 6451 | C5 | U | 1 | 17 | 3.908 | 100.482 | 280.243 | 1.00 | 0.00 | C |
| ATOM | 6452 | C6 | U | 1 | 17 | 3.562 | 101.508 | 281.041 | 1.00 | 0.00 | C |
| ATOM | 6453 | P | U | 1 | 18 | -0.903 | 102.079 | 284.397 | 1.00 | 0.00 | P |
| ATOM | 6454 | O1P | U | 1 | 18 | -1.744 | 102.370 | 285.578 | 1.00 | 0.00 | O |
| ATOM | 6455 | O2P | U | 1 | 18 | -0.302 | 100.727 | 284.343 | 1.00 | 0.00 | O |
| ATOM | 6456 | O5* | U | 1 | 18 | -1.745 | 102.343 | 283.061 | 1.00 | 0.00 | O |
| ATOM | 6457 | C5* | U | 1 | 18 | -2.421 | 103.605 | 282.901 | 1.00 | 0.00 | C |
| ATOM | 6458 | C4* | U | 1 | 18 | -3.104 | 103.659 | 281.550 | 1.00 | 0.00 | C |
| ATOM | 6459 | O4* | U | 1 | 18 | -2.086 | 103.639 | 280.506 | 1.00 | 0.00 | O |
| ATOM | 6460 | C3* | U | 1 | 18 | -4.004 | 102.471 | 281.209 | 1.00 | 0.00 | C |
| ATOM | 6461 | O3* | U | 1 | 18 | -5.295 | 102.604 | 281.785 | 1.00 | 0.00 | O |
| ATOM | 6462 | C2* | U | 1 | 18 | -4.022 | 102.512 | 279.674 | 1.00 | 0.00 | C |
| ATOM | 6463 | O2* | U | 1 | 18 | -4.863 | 103.530 | 279.203 | 1.00 | 0.00 | O |
| ATOM | 6464 | C1* | U | 1 | 18 | -2.578 | 102.930 | 279.380 | 1.00 | 0.00 | C |
| ATOM | 6465 | N1 | U | 1 | 18 | -1.693 | 101.756 | 279.141 | 1.00 | 0.00 | N |
| ATOM | 6466 | C2 | U | 1 | 18 | -1.736 | 101.184 | 277.893 | 1.00 | 0.00 | C |
| ATOM | 6467 | O2 | U | 1 | 18 | -2.457 | 101.595 | 277.000 | 1.00 | 0.00 | O |
| ATOM | 6468 | N3 | U | 1 | 18 | -0.902 | 100.100 | 277.708 | 1.00 | 0.00 | N |
| ATOM | 6469 | C4 | U | 1 | 18 | -0.050 | 99.553 | 278.646 | 1.00 | 0.00 | C |
| ATOM | 6470 | O4 | U | 1 | 18 | 0.652 | 98.579 | 278.364 | 1.00 | 0.00 | O |
| ATOM | 6471 | C5 | U | 1 | 18 | -0.074 | 100.221 | 279.925 | 1.00 | 0.00 | C |
| ATOM | 6472 | C6 | U | 1 | 18 | -0.876 | 101.280 | 280.133 | 1.00 | 0.00 | C |
| ATOM | 6473 | P | U | 1 | 19 | -7.555 | 104.206 | 283.164 | 1.00 | 0.00 | P |
| ATOM | 6474 | P | U | 1 | 20 | -10.080 | 101.304 | 277.210 | 1.00 | 0.00 | P |
| ATOM | 6475 | P | U | 1 | 21 | -12.592 | 101.725 | 271.318 | 1.00 | 0.00 | P |
| ATOM | 6476 | P | A | 1 | 22 | -13.767 | 104.972 | 267.238 | 1.00 | 0.00 | P |
| ATOM | 6477 | P | A | 1 | 23 | -13.883 | 110.601 | 266.018 | 1.00 | 0.00 | P |
| ATOM | 6478 | P | A | 1 | 24 | -11.236 | 115.341 | 265.543 | 1.00 | 0.00 | P |
| ATOM | 6479 | P | C | 1 | 25 | -9.659 | 117.457 | 271.051 | 1.00 | 0.00 | P |
| ATOM | 6480 | P | G | 1 | 26 | -12.226 | 117.863 | 276.709 | 1.00 | 0.00 | P |
| ATOM | 6481 | P | U | 1 | 27 | -16.607 | 118.375 | 279.055 | 1.00 | 0.00 | P |
| ATOM | 6482 | P | A | 1 | 28 | -20.866 | 115.156 | 278.096 | 1.00 | 0.00 | P |
| ATOM | 6483 | P | A | 1 | 29 | -23.934 | 111.757 | 276.718 | 1.00 | 0.00 | P |
| ATOM | 6484 | P | A | 1 | 30 | -25.710 | 106.296 | 276.587 | 1.00 | 0.00 | P |
| ATOM | 6485 | P | U | 1 | 31 | -22.203 | 102.989 | 279.043 | 1.00 | 0.00 | P |
| ATOM | 6486 | P | C | 1 | 32 | -20.980 | 98.212 | 282.345 | 1.00 | 0.00 | P |
| ATOM | 6487 | P | U | 1 | 33 | -23.533 | 94.810 | 282.803 | 1.00 | 0.00 | P |
| ATOM | 6488 | P | A | 1 | 34 | -24.587 | 91.038 | 281.755 | 1.00 | 0.00 | P |
| ATOM | 6489 | P | C | 1 | 35 | -26.516 | 87.512 | 282.046 | 1.00 | 0.00 | P |
| ATOM | 6490 | P | U | 1 | 36 | -29.863 | 83.982 | 285.539 | 1.00 | 0.00 | P |
| TER | 6491 | | U | 1 | 36 | | | | | | |
| ATOM | 6492 | CA | VAL | E | 7 | -13.818 | 20.636 | 309.201 | 1.00 | 0.00 | C |
| ATOM | 6493 | CA | LYS | E | 8 | -11.691 | 21.790 | 312.175 | 1.00 | 0.00 | C |
| ATOM | 6494 | CA | GLU | E | 9 | -8.177 | 21.652 | 313.730 | 1.00 | 0.00 | C |
| ATOM | 6495 | CA | LEU | E | 10 | -6.126 | 23.223 | 316.528 | 1.00 | 0.00 | C |
| ATOM | 6496 | CA | LEU | E | 11 | -2.721 | 21.750 | 315.744 | 1.00 | 0.00 | C |
| ATOM | 6497 | CA | GLU | E | 12 | -2.865 | 24.181 | 312.888 | 1.00 | 0.00 | C |
| ATOM | 6498 | CA | ALA | E | 13 | 0.200 | 25.831 | 314.349 | 1.00 | 0.00 | C |
| ATOM | 6499 | CA | GLY | E | 14 | 1.391 | 23.939 | 311.306 | 1.00 | 0.00 | C |
| ATOM | 6500 | CA | VAL | E | 15 | 0.929 | 27.222 | 309.408 | 1.00 | 0.00 | C |
| ATOM | 6501 | CA | HIS | E | 16 | -1.108 | 30.326 | 310.357 | 1.00 | 0.00 | C |
| ATOM | 6502 | CA | PHE | E | 17 | -0.438 | 31.667 | 313.851 | 1.00 | 0.00 | C |
| ATOM | 6503 | CA | GLY | E | 18 | 1.747 | 34.765 | 314.154 | 1.00 | 0.00 | C |

```
ATOM   6504  CA  HIS E  19      2.629  37.038 311.244  1.00  0.00           C
ATOM   6505  CA  GLU E  20      3.674  40.664 310.405  1.00  0.00           C
ATOM   6506  CA  ARG E  21      6.794  42.161 311.977  1.00  0.00           C
ATOM   6507  CA  LYS E  22      5.803  45.119 314.185  1.00  0.00           C
ATOM   6508  CA  ARG E  23      3.991  48.255 313.060  1.00  0.00           C
ATOM   6509  CA  TRP E  24      0.728  46.382 313.587  1.00  0.00           C
ATOM   6510  CA  ASN E  25     -2.603  48.078 314.244  1.00  0.00           C
ATOM   6511  CA  PRO E  26     -3.183  48.481 318.000  1.00  0.00           C
ATOM   6512  CA  LYS E  27     -6.825  47.482 317.410  1.00  0.00           C
ATOM   6513  CA  PHE E  28     -5.853  43.936 316.447  1.00  0.00           C
ATOM   6514  CA  ALA E  29     -4.347  43.824 319.933  1.00  0.00           C
ATOM   6515  CA  ARG E  30     -6.988  41.369 321.150  1.00  0.00           C
ATOM   6516  CA  TYR E  31     -6.093  38.672 318.597  1.00  0.00           C
ATOM   6517  CA  ILE E  32     -2.374  38.824 319.375  1.00  0.00           C
ATOM   6518  CA  TYR E  33     -0.562  36.445 321.696  1.00  0.00           C
ATOM   6519  CA  ALA E  34      2.974  37.866 321.777  1.00  0.00           C
ATOM   6520  CA  GLU E  35      6.040  39.114 319.896  1.00  0.00           C
ATOM   6521  CA  ARG E  36      9.054  36.905 319.232  1.00  0.00           C
ATOM   6522  CA  ASN E  37     12.071  37.852 317.133  1.00  0.00           C
ATOM   6523  CA  GLY E  38      9.973  40.909 316.427  1.00  0.00           C
ATOM   6524  CA  ILE E  39      6.966  39.348 314.685  1.00  0.00           C
ATOM   6525  CA  HIS E  40      3.728  39.215 316.679  1.00  0.00           C
ATOM   6526  CA  ILE E  41      2.195  35.821 317.328  1.00  0.00           C
ATOM   6527  CA  ILE E  42     -1.502  35.296 316.774  1.00  0.00           C
ATOM   6528  CA  ASP E  43     -3.390  33.413 319.467  1.00  0.00           C
ATOM   6529  CA  LEU E  44     -4.989  30.510 317.581  1.00  0.00           C
ATOM   6530  CA  GLN E  45     -7.186  29.681 320.585  1.00  0.00           C
ATOM   6531  CA  LYS E  46     -8.951  32.830 319.443  1.00  0.00           C
ATOM   6532  CA  THR E  47     -8.461  32.054 315.758  1.00  0.00           C
ATOM   6533  CA  MET E  48    -10.535  29.038 316.708  1.00  0.00           C
ATOM   6534  CA  GLU E  49    -13.315  30.804 318.579  1.00  0.00           C
ATOM   6535  CA  GLU E  50    -13.626  33.062 315.557  1.00  0.00           C
ATOM   6536  CA  LEU E  51    -13.663  30.246 313.003  1.00  0.00           C
ATOM   6537  CA  GLU E  52    -16.527  28.523 314.816  1.00  0.00           C
ATOM   6538  CA  ARG E  53    -18.530  31.733 314.841  1.00  0.00           C
ATOM   6539  CA  THR E  54    -17.508  32.644 311.293  1.00  0.00           C
ATOM   6540  CA  PHE E  55    -17.929  29.239 309.647  1.00  0.00           C
ATOM   6541  CA  ARG E  56    -21.259  28.895 311.421  1.00  0.00           C
ATOM   6542  CA  PHE E  57    -22.323  32.076 309.571  1.00  0.00           C
ATOM   6543  CA  ILE E  58    -21.260  30.371 306.363  1.00  0.00           C
ATOM   6544  CA  GLU E  59    -23.415  27.193 306.586  1.00  0.00           C
ATOM   6545  CA  ASP E  60    -26.076  29.783 307.240  1.00  0.00           C
ATOM   6546  CA  LEU E  61    -25.801  31.462 303.812  1.00  0.00           C
ATOM   6547  CA  ALA E  62    -24.484  28.187 302.456  1.00  0.00           C
ATOM   6548  CA  MET E  63    -27.471  25.840 302.726  1.00  0.00           C
ATOM   6549  CA  ARG E  64    -29.616  28.932 302.289  1.00  0.00           C
ATOM   6550  CA  GLY E  65    -28.428  29.255 298.697  1.00  0.00           C
ATOM   6551  CA  GLY E  66    -26.625  32.511 299.282  1.00  0.00           C
ATOM   6552  CA  THR E  67    -23.638  33.840 297.375  1.00  0.00           C
ATOM   6553  CA  ILE E  68    -20.184  34.724 298.719  1.00  0.00           C
ATOM   6554  CA  LEU E  69    -17.987  36.906 296.538  1.00  0.00           C
ATOM   6555  CA  PHE E  70    -14.385  35.951 297.321  1.00  0.00           C
ATOM   6556  CA  VAL E  71    -11.837  38.742 296.993  1.00  0.00           C
ATOM   6557  CA  GLY E  72     -8.097  38.135 296.800  1.00  0.00           C
ATOM   6558  CA  THR E  73     -5.935  40.569 294.826  1.00  0.00           C
ATOM   6559  CA  LYS E  74     -2.885  39.967 297.055  1.00  0.00           C
ATOM   6560  CA  LYS E  75     -0.355  37.922 295.053  1.00  0.00           C
ATOM   6561  CA  GLN E  76      0.326  35.208 297.633  1.00  0.00           C
ATOM   6562  CA  ALA E  77     -3.368  34.274 297.349  1.00  0.00           C
ATOM   6563  CA  GLN E  78     -4.215  35.303 293.799  1.00  0.00           C
ATOM   6564  CA  ASP E  79     -4.241  31.767 292.373  1.00  0.00           C
ATOM   6565  CA  ILE E  80     -5.952  30.159 295.357  1.00  0.00           C
ATOM   6566  CA  VAL E  81     -8.885  32.588 295.360  1.00  0.00           C
ATOM   6567  CA  ARG E  82     -9.653  31.207 291.896  1.00  0.00           C
ATOM   6568  CA  MET E  83     -9.415  27.499 292.693  1.00  0.00           C
ATOM   6569  CA  GLU E  84    -11.429  27.573 295.904  1.00  0.00           C
ATOM   6570  CA  ALA E  85    -13.832  30.039 294.297  1.00  0.00           C
ATOM   6571  CA  GLU E  86    -14.547  27.920 291.207  1.00  0.00           C
ATOM   6572  CA  ARG E  87    -14.612  24.916 293.515  1.00  0.00           C
ATOM   6573  CA  ALA E  88    -17.974  26.366 294.588  1.00  0.00           C
ATOM   6574  CA  GLY E  89    -20.553  28.139 292.443  1.00  0.00           C
ATOM   6575  CA  MET E  90    -19.070  31.283 293.984  1.00  0.00           C
ATOM   6576  CA  PRO E  91    -17.692  34.350 292.114  1.00  0.00           C
ATOM   6577  CA  TYR E  92    -14.330  35.972 292.801  1.00  0.00           C
ATOM   6578  CA  VAL E  93    -12.205  39.041 292.090  1.00  0.00           C
ATOM   6579  CA  ASN E  94     -8.648  37.863 291.460  1.00  0.00           C
ATOM   6580  CA  GLN E  95     -6.807  40.470 289.424  1.00  0.00           C
ATOM   6581  CA  ARG E  96     -7.787  44.014 290.369  1.00  0.00           C
ATOM   6582  CA  TRP E  97    -10.917  44.945 292.254  1.00  0.00           C
ATOM   6583  CA  LEU E  98    -12.439  47.695 290.072  1.00  0.00           C
ATOM   6584  CA  GLY E  99    -13.810  50.610 292.084  1.00  0.00           C
ATOM   6585  CA  GLY E 100    -17.562  50.357 292.423  1.00  0.00           C
ATOM   6586  CA  MET E 101    -17.997  46.661 291.661  1.00  0.00           C
ATOM   6587  CA  LEU E 102    -20.473  46.548 294.541  1.00  0.00           C
ATOM   6588  CA  THR E 103    -21.295  50.189 295.024  1.00  0.00           C
ATOM   6589  CA  ASN E 104    -21.638  50.703 291.277  1.00  0.00           C
ATOM   6590  CA  PHE E 105    -22.784  47.172 290.441  1.00  0.00           C
```

| | | | | | | | | | |
|---|---|---|---|---|---|---|---|---|---|
| ATOM | 6591 | CA | LYS | E | 106 | -25.375 | 47.918 | 287.780 | 1.00 | 0.00 | C |
| ATOM | 6592 | CA | THR | E | 107 | -22.688 | 49.622 | 285.709 | 1.00 | 0.00 | C |
| ATOM | 6593 | CA | ILE | E | 108 | -19.816 | 47.193 | 286.134 | 1.00 | 0.00 | C |
| ATOM | 6594 | CA | SER | E | 109 | -22.499 | 44.677 | 285.210 | 1.00 | 0.00 | C |
| ATOM | 6595 | CA | GLN | E | 110 | -22.784 | 46.204 | 281.761 | 1.00 | 0.00 | C |
| ATOM | 6596 | CA | ARG | E | 111 | -19.142 | 45.278 | 281.446 | 1.00 | 0.00 | C |
| ATOM | 6597 | CA | VAL | E | 112 | -20.145 | 41.626 | 281.812 | 1.00 | 0.00 | C |
| ATOM | 6598 | CA | HIS | E | 113 | -23.022 | 41.986 | 279.350 | 1.00 | 0.00 | C |
| ATOM | 6599 | CA | ARG | E | 114 | -20.324 | 43.140 | 276.982 | 1.00 | 0.00 | C |
| ATOM | 6600 | CA | LEU | E | 115 | -18.111 | 40.153 | 277.740 | 1.00 | 0.00 | C |
| ATOM | 6601 | CA | GLU | E | 116 | -20.986 | 37.835 | 276.877 | 1.00 | 0.00 | C |
| ATOM | 6602 | CA | GLU | E | 117 | -21.911 | 39.815 | 273.795 | 1.00 | 0.00 | C |
| ATOM | 6603 | CA | LEU | E | 118 | -18.342 | 39.746 | 272.478 | 1.00 | 0.00 | C |
| ATOM | 6604 | CA | GLU | E | 119 | -17.737 | 36.033 | 273.044 | 1.00 | 0.00 | C |
| ATOM | 6605 | CA | ALA | E | 120 | -20.754 | 35.553 | 270.775 | 1.00 | 0.00 | C |
| ATOM | 6606 | CA | LEU | E | 121 | -19.216 | 37.424 | 267.849 | 1.00 | 0.00 | C |
| ATOM | 6607 | CA | PHE | E | 122 | -15.939 | 35.512 | 268.182 | 1.00 | 0.00 | C |
| ATOM | 6608 | CA | ALA | E | 123 | -17.771 | 32.244 | 267.553 | 1.00 | 0.00 | C |
| ATOM | 6609 | CA | SER | E | 124 | -20.490 | 33.629 | 265.264 | 1.00 | 0.00 | C |
| ATOM | 6610 | CA | PRO | E | 125 | -20.625 | 34.494 | 261.539 | 1.00 | 0.00 | C |
| ATOM | 6611 | CA | GLU | E | 126 | -19.759 | 38.199 | 261.547 | 1.00 | 0.00 | C |
| ATOM | 6612 | CA | ILE | E | 127 | -16.343 | 37.161 | 262.894 | 1.00 | 0.00 | C |
| ATOM | 6613 | CA | GLU | E | 128 | -14.579 | 37.733 | 259.577 | 1.00 | 0.00 | C |
| ATOM | 6614 | CA | GLU | E | 129 | -16.443 | 40.981 | 258.853 | 1.00 | 0.00 | C |
| ATOM | 6615 | CA | ARG | E | 130 | -15.477 | 44.659 | 258.945 | 1.00 | 0.00 | C |
| ATOM | 6616 | CA | PRO | E | 131 | -11.815 | 45.730 | 259.096 | 1.00 | 0.00 | C |
| ATOM | 6617 | CA | LYS | E | 132 | -9.427 | 43.898 | 261.402 | 1.00 | 0.00 | C |
| ATOM | 6618 | CA | LYS | E | 133 | -8.719 | 47.119 | 263.284 | 1.00 | 0.00 | C |
| ATOM | 6619 | CA | GLU | E | 134 | -11.836 | 45.943 | 265.096 | 1.00 | 0.00 | C |
| ATOM | 6620 | CA | GLN | E | 135 | -11.087 | 42.227 | 264.765 | 1.00 | 0.00 | C |
| ATOM | 6621 | CA | VAL | E | 136 | -8.102 | 43.388 | 266.810 | 1.00 | 0.00 | C |
| ATOM | 6622 | CA | ARG | E | 137 | -9.428 | 46.075 | 269.161 | 1.00 | 0.00 | C |
| ATOM | 6623 | CA | LEU | E | 138 | -12.352 | 43.844 | 270.034 | 1.00 | 0.00 | C |
| ATOM | 6624 | CA | LYS | E | 139 | -9.923 | 40.941 | 270.424 | 1.00 | 0.00 | C |
| ATOM | 6625 | CA | HIS | E | 140 | -8.416 | 43.191 | 273.097 | 1.00 | 0.00 | C |
| ATOM | 6626 | CA | GLU | E | 141 | -11.684 | 44.031 | 274.871 | 1.00 | 0.00 | C |
| ATOM | 6627 | CA | LEU | E | 142 | -12.300 | 40.346 | 275.479 | 1.00 | 0.00 | C |
| ATOM | 6628 | CA | GLU | E | 143 | -8.680 | 40.007 | 276.564 | 1.00 | 0.00 | C |
| ATOM | 6629 | CA | ARG | E | 144 | -9.131 | 42.438 | 279.438 | 1.00 | 0.00 | C |
| ATOM | 6630 | CA | LEU | E | 145 | -12.786 | 41.697 | 280.218 | 1.00 | 0.00 | C |
| ATOM | 6631 | CA | GLN | E | 146 | -11.723 | 38.104 | 280.654 | 1.00 | 0.00 | C |
| ATOM | 6632 | CA | LYS | E | 147 | -8.843 | 39.372 | 282.806 | 1.00 | 0.00 | C |
| ATOM | 6633 | CA | TYR | E | 148 | -10.882 | 41.279 | 285.395 | 1.00 | 0.00 | C |
| ATOM | 6634 | CA | LEU | E | 149 | -14.399 | 39.946 | 284.942 | 1.00 | 0.00 | C |
| ATOM | 6635 | CA | SER | E | 150 | -13.625 | 36.206 | 284.890 | 1.00 | 0.00 | C |
| ATOM | 6636 | CA | GLY | E | 151 | -14.675 | 35.629 | 288.505 | 1.00 | 0.00 | C |
| ATOM | 6637 | CA | PHE | E | 152 | -17.035 | 38.583 | 288.698 | 1.00 | 0.00 | C |
| ATOM | 6638 | CA | ARG | E | 153 | -18.712 | 36.748 | 285.823 | 1.00 | 0.00 | C |
| ATOM | 6639 | CA | LEU | E | 154 | -21.335 | 34.972 | 287.977 | 1.00 | 0.00 | C |
| ATOM | 6640 | CA | LEU | E | 155 | -22.621 | 37.783 | 290.207 | 1.00 | 0.00 | C |
| ATOM | 6641 | CA | LYS | E | 156 | -26.158 | 38.403 | 288.927 | 1.00 | 0.00 | C |
| ATOM | 6642 | CA | ARG | E | 157 | -27.039 | 40.661 | 291.905 | 1.00 | 0.00 | C |
| ATOM | 6643 | CA | LEU | E | 158 | -25.050 | 42.081 | 294.823 | 1.00 | 0.00 | C |
| ATOM | 6644 | CA | PRO | E | 159 | -23.572 | 39.180 | 296.831 | 1.00 | 0.00 | C |
| ATOM | 6645 | CA | ASP | E | 160 | -24.723 | 38.165 | 300.309 | 1.00 | 0.00 | C |
| ATOM | 6646 | CA | ALA | E | 161 | -21.294 | 38.479 | 301.799 | 1.00 | 0.00 | C |
| ATOM | 6647 | CA | ILE | E | 162 | -17.649 | 38.859 | 300.966 | 1.00 | 0.00 | C |
| ATOM | 6648 | CA | PHE | E | 163 | -14.807 | 36.559 | 301.853 | 1.00 | 0.00 | C |
| ATOM | 6649 | CA | VAL | E | 164 | -11.884 | 38.931 | 301.669 | 1.00 | 0.00 | C |
| ATOM | 6650 | CA | VAL | E | 165 | -8.309 | 37.843 | 302.241 | 1.00 | 0.00 | C |
| ATOM | 6651 | CA | ASP | E | 166 | -6.131 | 40.808 | 303.254 | 1.00 | 0.00 | C |
| ATOM | 6652 | CA | PRO | E | 167 | -8.783 | 43.427 | 304.228 | 1.00 | 0.00 | C |
| ATOM | 6653 | CA | THR | E | 168 | -6.157 | 46.122 | 304.571 | 1.00 | 0.00 | C |
| ATOM | 6654 | CA | LYS | E | 169 | -4.948 | 45.371 | 301.066 | 1.00 | 0.00 | C |
| ATOM | 6655 | CA | GLU | E | 170 | -8.558 | 44.849 | 299.960 | 1.00 | 0.00 | C |
| ATOM | 6656 | CA | ALA | E | 171 | -9.905 | 47.815 | 301.951 | 1.00 | 0.00 | C |
| ATOM | 6657 | CA | ILE | E | 172 | -11.722 | 49.424 | 299.018 | 1.00 | 0.00 | C |
| ATOM | 6658 | CA | ALA | E | 173 | -13.749 | 46.225 | 298.678 | 1.00 | 0.00 | C |
| ATOM | 6659 | CA | VAL | E | 174 | -14.512 | 46.046 | 302.389 | 1.00 | 0.00 | C |
| ATOM | 6660 | CA | ARG | E | 175 | -15.608 | 49.694 | 302.375 | 1.00 | 0.00 | C |
| ATOM | 6661 | CA | GLU | E | 176 | -18.068 | 49.114 | 299.534 | 1.00 | 0.00 | C |
| ATOM | 6662 | CA | ALA | E | 177 | -19.589 | 46.231 | 301.497 | 1.00 | 0.00 | C |
| ATOM | 6663 | CA | ARG | E | 178 | -20.173 | 48.354 | 304.593 | 1.00 | 0.00 | C |
| ATOM | 6664 | CA | LYS | E | 179 | -22.009 | 51.058 | 302.630 | 1.00 | 0.00 | C |
| ATOM | 6665 | CA | LEU | E | 180 | -24.164 | 48.354 | 301.110 | 1.00 | 0.00 | C |
| ATOM | 6666 | CA | PHE | E | 181 | -24.576 | 46.447 | 304.392 | 1.00 | 0.00 | C |
| ATOM | 6667 | CA | ILE | E | 182 | -23.063 | 43.380 | 302.856 | 1.00 | 0.00 | C |
| ATOM | 6668 | CA | PRO | E | 183 | -21.538 | 41.147 | 305.566 | 1.00 | 0.00 | C |
| ATOM | 6669 | CA | VAL | E | 184 | -17.753 | 41.015 | 305.590 | 1.00 | 0.00 | C |
| ATOM | 6670 | CA | ILE | E | 185 | -15.743 | 37.848 | 306.247 | 1.00 | 0.00 | C |
| ATOM | 6671 | CA | ALA | E | 186 | -11.960 | 38.060 | 306.293 | 1.00 | 0.00 | C |
| ATOM | 6672 | CA | LEU | E | 187 | -8.759 | 36.126 | 306.915 | 1.00 | 0.00 | C |
| ATOM | 6673 | CA | ALA | E | 188 | -7.047 | 39.064 | 308.573 | 1.00 | 0.00 | C |
| ATOM | 6674 | CA | ASP | E | 189 | -3.886 | 39.459 | 310.626 | 1.00 | 0.00 | C |
| ATOM | 6675 | CA | THR | E | 190 | -1.703 | 41.815 | 312.673 | 1.00 | 0.00 | C |
| ATOM | 6676 | CA | ASP | E | 191 | -1.788 | 44.820 | 310.326 | 1.00 | 0.00 | C |
| ATOM | 6677 | CA | SER | E | 192 | -5.545 | 45.163 | 309.794 | 1.00 | 0.00 | C |

```
ATOM   6678  CA  ASP E 193      -8.574  46.779 311.440  1.00  0.00           C
ATOM   6679  CA  PRO E 194     -10.587  44.009 313.142  1.00  0.00           C
ATOM   6680  CA  ASP E 195     -13.516  46.383 313.759  1.00  0.00           C
ATOM   6681  CA  LEU E 196     -14.380  46.533 310.072  1.00  0.00           C
ATOM   6682  CA  VAL E 197     -14.544  42.796 309.574  1.00  0.00           C
ATOM   6683  CA  ASP E 198     -17.884  41.257 310.481  1.00  0.00           C
ATOM   6684  CA  TYR E 199     -16.516  37.708 310.700  1.00  0.00           C
ATOM   6685  CA  ILE E 200     -12.779  37.720 311.362  1.00  0.00           C
ATOM   6686  CA  ILE E 201     -10.440  34.785 310.790  1.00  0.00           C
ATOM   6687  CA  PRO E 202      -7.352  36.124 312.622  1.00  0.00           C
ATOM   6688  CA  GLY E 203      -4.294  34.468 311.179  1.00  0.00           C
ATOM   6689  CA  ASN E 204      -1.500  34.694 308.625  1.00  0.00           C
ATOM   6690  CA  ASP E 205      -3.037  36.784 305.798  1.00  0.00           C
ATOM   6691  CA  ASP E 206       0.040  35.912 303.780  1.00  0.00           C
ATOM   6692  CA  ALA E 207       1.747  32.607 302.937  1.00  0.00           C
ATOM   6693  CA  ILE E 208      -0.008  30.111 300.685  1.00  0.00           C
ATOM   6694  CA  ARG E 209       0.266  27.269 303.199  1.00  0.00           C
ATOM   6695  CA  SER E 210      -2.184  29.373 305.258  1.00  0.00           C
ATOM   6696  CA  ILE E 211      -4.502  31.102 302.793  1.00  0.00           C
ATOM   6697  CA  GLN E 212      -4.958  27.740 301.078  1.00  0.00           C
ATOM   6698  CA  LEU E 213      -5.972  26.034 304.315  1.00  0.00           C
ATOM   6699  CA  ILE E 214      -8.620  28.444 305.539  1.00  0.00           C
ATOM   6700  CA  LEU E 215     -10.176  29.171 302.169  1.00  0.00           C
ATOM   6701  CA  SER E 216     -10.177  25.548 301.014  1.00  0.00           C
ATOM   6702  CA  ARG E 217     -12.061  24.509 304.168  1.00  0.00           C
ATOM   6703  CA  ALA E 218     -14.435  27.447 304.067  1.00  0.00           C
ATOM   6704  CA  VAL E 219     -15.298  26.078 300.607  1.00  0.00           C
ATOM   6705  CA  ASP E 220     -15.673  22.452 301.672  1.00  0.00           C
ATOM   6706  CA  LEU E 221     -18.100  23.846 304.238  1.00  0.00           C
ATOM   6707  CA  ILE E 222     -20.038  25.641 301.487  1.00  0.00           C
ATOM   6708  CA  ILE E 223     -20.495  22.384 299.557  1.00  0.00           C
ATOM   6709  CA  GLN E 224     -20.879  20.244 302.662  1.00  0.00           C
ATOM   6710  CA  ALA E 225     -23.761  22.555 303.519  1.00  0.00           C
ATOM   6711  CA  ARG E 226     -25.264  22.382 300.052  1.00  0.00           C
ATOM   6712  CA  GLY E 227     -25.205  18.605 299.882  1.00  0.00           C
ATOM   6713  CA  GLY E 228     -22.299  17.966 297.555  1.00  0.00           C
ATOM   6714  CA  VAL E 229     -20.240  15.339 299.384  1.00  0.00           C
ATOM   6715  CA  VAL E 230     -17.290  16.738 297.439  1.00  0.00           C
ATOM   6716  CA  GLU E 231     -13.788  15.251 297.491  1.00  0.00           C
ATOM   6717  CA  PRO E 232     -10.575  16.964 298.793  1.00  0.00           C
ATOM   6718  CA  SER E 233      -9.203  20.244 297.401  1.00  0.00           C
ATOM   6719  CA  PRO E 234      -6.886  20.470 294.329  1.00  0.00           C
ATOM   6720  CA  SER E 235      -5.323  23.756 295.522  1.00  0.00           C
ATOM   6721  CA  TYR E 236      -2.857  22.031 297.854  1.00  0.00           C
ATOM   6722  CA  ALA E 237      -0.916  21.407 294.629  1.00  0.00           C
ATOM   6723  CA  LEU E 238      -0.369  25.172 294.434  1.00  0.00           C
ATOM   6724  CA  VAL E 239       1.189  25.011 297.885  1.00  0.00           C
ATOM   6725  CA  GLN E 240       4.433  23.810 296.264  1.00  0.00           C
TER    6726      GLN E 240
ATOM   6727  CA  GLY F   2     -19.153  80.396 263.877  1.00  0.00           C
ATOM   6728  CA  ASN F   3     -18.218  76.959 262.561  1.00  0.00           C
ATOM   6729  CA  LYS F   4     -19.812  73.682 261.312  1.00  0.00           C
ATOM   6730  CA  ILE F   5     -21.373  72.986 257.896  1.00  0.00           C
ATOM   6731  CA  HIS F   6     -24.973  72.299 257.040  1.00  0.00           C
ATOM   6732  CA  PRO F   7     -25.485  68.663 258.050  1.00  0.00           C
ATOM   6733  CA  ILE F   8     -27.447  68.068 254.856  1.00  0.00           C
ATOM   6734  CA  GLY F   9     -25.325  69.834 252.265  1.00  0.00           C
ATOM   6735  CA  PHE F  10     -22.434  68.043 253.911  1.00  0.00           C
ATOM   6736  CA  ARG F  11     -23.957  64.616 253.241  1.00  0.00           C
ATOM   6737  CA  LEU F  12     -25.666  65.162 249.864  1.00  0.00           C
ATOM   6738  CA  GLY F  13     -23.288  62.616 248.393  1.00  0.00           C
ATOM   6739  CA  ILE F  14     -24.757  60.017 250.730  1.00  0.00           C
ATOM   6740  CA  THR F  15     -27.401  59.712 253.472  1.00  0.00           C
ATOM   6741  CA  ARG F  16     -29.510  62.505 251.915  1.00  0.00           C
ATOM   6742  CA  ASP F  17     -30.836  63.205 248.385  1.00  0.00           C
ATOM   6743  CA  TRP F  18     -31.537  66.585 246.774  1.00  0.00           C
ATOM   6744  CA  GLU F  19     -34.836  68.500 246.856  1.00  0.00           C
ATOM   6745  CA  SER F  20     -34.743  69.083 243.081  1.00  0.00           C
ATOM   6746  CA  ARG F  21     -33.336  66.218 241.010  1.00  0.00           C
ATOM   6747  CA  TRP F  22     -33.327  66.930 237.285  1.00  0.00           C
ATOM   6748  CA  TYR F  23     -30.744  67.419 234.549  1.00  0.00           C
ATOM   6749  CA  ALA F  24     -30.480  70.621 232.499  1.00  0.00           C
ATOM   6750  CA  GLY F  25     -28.048  73.474 232.168  1.00  0.00           C
ATOM   6751  CA  LYS F  26     -26.423  76.193 230.120  1.00  0.00           C
ATOM   6752  CA  LYS F  27     -29.242  78.412 228.867  1.00  0.00           C
ATOM   6753  CA  GLN F  28     -31.968  76.841 230.978  1.00  0.00           C
ATOM   6754  CA  TYR F  29     -30.681  75.856 234.426  1.00  0.00           C
ATOM   6755  CA  ARG F  30     -30.971  79.375 235.860  1.00  0.00           C
ATOM   6756  CA  HIS F  31     -34.497  79.766 234.434  1.00  0.00           C
ATOM   6757  CA  LEU F  32     -35.523  76.210 235.254  1.00  0.00           C
ATOM   6758  CA  LEU F  33     -34.285  76.760 238.820  1.00  0.00           C
ATOM   6759  CA  LEU F  34     -35.726  80.174 239.513  1.00  0.00           C
ATOM   6760  CA  GLU F  35     -39.002  78.372 238.894  1.00  0.00           C
ATOM   6761  CA  ASP F  36     -38.494  75.776 241.638  1.00  0.00           C
ATOM   6762  CA  GLN F  37     -38.108  78.652 244.093  1.00  0.00           C
ATOM   6763  CA  ARG F  38     -41.282  80.301 242.800  1.00  0.00           C
ATOM   6764  CA  ILE F  39     -42.969  76.961 243.426  1.00  0.00           C
```

```
ATOM   6765  CA  ARG F  40     -41.624  76.375 246.939  1.00  0.00           C
ATOM   6766  CA  GLY F  41     -42.333  80.055 247.552  1.00  0.00           C
ATOM   6767  CA  LEU F  42     -46.118  79.628 247.498  1.00  0.00           C
ATOM   6768  CA  LEU F  43     -46.334  76.136 249.002  1.00  0.00           C
ATOM   6769  CA  GLU F  44     -44.567  77.280 252.161  1.00  0.00           C
ATOM   6770  CA  LYS F  45     -46.644  80.475 252.201  1.00  0.00           C
ATOM   6771  CA  GLU F  46     -49.816  78.386 251.936  1.00  0.00           C
ATOM   6772  CA  LEU F  47     -49.474  74.809 253.203  1.00  0.00           C
ATOM   6773  CA  TYR F  48     -48.191  76.091 256.545  1.00  0.00           C
ATOM   6774  CA  SER F  49     -50.964  74.603 258.708  1.00  0.00           C
ATOM   6775  CA  ALA F  50     -50.612  71.360 256.752  1.00  0.00           C
ATOM   6776  CA  GLY F  51     -47.103  70.995 258.086  1.00  0.00           C
ATOM   6777  CA  LEU F  52     -44.593  71.389 255.253  1.00  0.00           C
ATOM   6778  CA  ALA F  53     -41.473  69.247 255.477  1.00  0.00           C
ATOM   6779  CA  ARG F  54     -40.078  68.927 251.976  1.00  0.00           C
ATOM   6780  CA  VAL F  55     -40.844  69.702 248.353  1.00  0.00           C
ATOM   6781  CA  ASP F  56     -39.336  67.251 245.879  1.00  0.00           C
ATOM   6782  CA  ILE F  57     -39.366  68.632 242.340  1.00  0.00           C
ATOM   6783  CA  GLU F  58     -38.583  66.198 239.507  1.00  0.00           C
ATOM   6784  CA  ARG F  59     -38.661  66.989 235.789  1.00  0.00           C
ATOM   6785  CA  ALA F  60     -38.360  65.704 232.212  1.00  0.00           C
ATOM   6786  CA  ALA F  61     -39.843  68.636 230.231  1.00  0.00           C
ATOM   6787  CA  ASP F  62     -43.175  70.496 230.389  1.00  0.00           C
ATOM   6788  CA  ASN F  63     -44.363  67.814 232.829  1.00  0.00           C
ATOM   6789  CA  VAL F  64     -43.116  68.785 236.268  1.00  0.00           C
ATOM   6790  CA  ALA F  65     -43.387  66.629 239.403  1.00  0.00           C
ATOM   6791  CA  VAL F  66     -43.708  68.381 242.785  1.00  0.00           C
ATOM   6792  CA  THR F  67     -44.332  65.930 245.614  1.00  0.00           C
ATOM   6793  CA  VAL F  68     -45.171  68.024 248.703  1.00  0.00           C
ATOM   6794  CA  HIS F  69     -44.623  66.069 251.972  1.00  0.00           C
ATOM   6795  CA  VAL F  70     -47.000  66.773 254.852  1.00  0.00           C
ATOM   6796  CA  ALA F  71     -48.063  65.766 258.369  1.00  0.00           C
ATOM   6797  CA  LYS F  72     -51.738  66.577 257.725  1.00  0.00           C
ATOM   6798  CA  PRO F  73     -52.230  65.475 254.069  1.00  0.00           C
ATOM   6799  CA  GLY F  74     -55.841  66.463 254.564  1.00  0.00           C
ATOM   6800  CA  VAL F  75     -55.394  70.220 254.949  1.00  0.00           C
ATOM   6801  CA  VAL F  76     -53.471  69.944 251.672  1.00  0.00           C
ATOM   6802  CA  ILE F  77     -55.952  68.027 249.514  1.00  0.00           C
ATOM   6803  CA  GLY F  78     -59.050  69.871 250.666  1.00  0.00           C
ATOM   6804  CA  ARG F  79     -62.735  68.939 250.875  1.00  0.00           C
ATOM   6805  CA  GLY F  80     -63.106  65.894 248.642  1.00  0.00           C
ATOM   6806  CA  GLY F  81     -60.091  67.302 246.846  1.00  0.00           C
ATOM   6807  CA  GLU F  82     -61.262  70.845 246.133  1.00  0.00           C
ATOM   6808  CA  ARG F  83     -58.128  72.609 247.388  1.00  0.00           C
ATOM   6809  CA  ILE F  84     -55.679  70.376 245.534  1.00  0.00           C
ATOM   6810  CA  ARG F  85     -57.605  71.986 242.677  1.00  0.00           C
ATOM   6811  CA  VAL F  86     -57.046  75.600 243.700  1.00  0.00           C
ATOM   6812  CA  LEU F  87     -53.327  75.116 244.281  1.00  0.00           C
ATOM   6813  CA  ARG F  88     -52.682  72.694 241.407  1.00  0.00           C
ATOM   6814  CA  GLU F  89     -54.216  75.427 239.258  1.00  0.00           C
ATOM   6815  CA  GLU F  90     -52.608  78.376 241.061  1.00  0.00           C
ATOM   6816  CA  LEU F  91     -49.489  76.425 240.114  1.00  0.00           C
ATOM   6817  CA  ALA F  92     -49.846  76.781 236.340  1.00  0.00           C
ATOM   6818  CA  LYS F  93     -50.732  80.468 236.783  1.00  0.00           C
ATOM   6819  CA  LEU F  94     -47.058  80.530 237.740  1.00  0.00           C
ATOM   6820  CA  THR F  95     -45.574  77.922 235.412  1.00  0.00           C
ATOM   6821  CA  GLY F  96     -47.320  77.459 232.087  1.00  0.00           C
ATOM   6822  CA  LYS F  97     -45.197  74.302 232.147  1.00  0.00           C
ATOM   6823  CA  ASN F  98     -48.229  72.117 233.076  1.00  0.00           C
ATOM   6824  CA  VAL F  99     -47.345  70.229 236.264  1.00  0.00           C
ATOM   6825  CA  ALA F 100     -48.634  67.535 238.637  1.00  0.00           C
ATOM   6826  CA  LEU F 101     -48.836  67.825 242.449  1.00  0.00           C
ATOM   6827  CA  ASN F 102     -48.609  64.598 244.481  1.00  0.00           C
ATOM   6828  CA  VAL F 103     -48.872  64.506 248.294  1.00  0.00           C
ATOM   6829  CA  GLN F 104     -47.169  62.019 250.592  1.00  0.00           C
ATOM   6830  CA  GLU F 105     -47.919  61.787 254.306  1.00  0.00           C
ATOM   6831  CA  VAL F 106     -45.247  62.175 256.982  1.00  0.00           C
ATOM   6832  CA  GLN F 107     -45.100  58.976 259.047  1.00  0.00           C
ATOM   6833  CA  ASN F 108     -44.561  60.565 262.474  1.00  0.00           C
ATOM   6834  CA  PRO F 109     -43.862  64.304 262.132  1.00  0.00           C
ATOM   6835  CA  ASN F 110     -41.914  63.614 265.308  1.00  0.00           C
ATOM   6836  CA  LEU F 111     -38.893  62.628 263.240  1.00  0.00           C
ATOM   6837  CA  SER F 112     -38.983  65.559 260.822  1.00  0.00           C
ATOM   6838  CA  ALA F 113     -36.337  68.044 261.897  1.00  0.00           C
ATOM   6839  CA  PRO F 114     -38.208  70.778 259.961  1.00  0.00           C
ATOM   6840  CA  LEU F 115     -41.390  69.911 261.780  1.00  0.00           C
ATOM   6841  CA  VAL F 116     -39.871  69.511 265.250  1.00  0.00           C
ATOM   6842  CA  ALA F 117     -38.238  72.886 264.559  1.00  0.00           C
ATOM   6843  CA  GLN F 118     -41.380  74.668 263.349  1.00  0.00           C
ATOM   6844  CA  ARG F 119     -43.134  72.939 266.229  1.00  0.00           C
ATOM   6845  CA  VAL F 120     -40.800  74.707 268.665  1.00  0.00           C
ATOM   6846  CA  ALA F 121     -40.636  77.897 266.632  1.00  0.00           C
ATOM   6847  CA  GLU F 122     -44.410  78.235 267.015  1.00  0.00           C
ATOM   6848  CA  GLN F 123     -44.583  77.634 270.765  1.00  0.00           C
ATOM   6849  CA  ILE F 124     -41.917  80.299 271.174  1.00  0.00           C
ATOM   6850  CA  GLU F 125     -44.032  82.697 269.148  1.00  0.00           C
ATOM   6851  CA  ARG F 126     -46.976  81.975 271.426  1.00  0.00           C
```

```
ATOM   6852  CA  ARG F 127     -44.784  82.849 274.433  1.00  0.00           C
ATOM   6853  CA  PHE F 128     -44.038  79.427 275.947  1.00  0.00           C
ATOM   6854  CA  ALA F 129     -41.074  78.774 278.237  1.00  0.00           C
ATOM   6855  CA  VAL F 130     -38.252  78.230 275.757  1.00  0.00           C
ATOM   6856  CA  ARG F 131     -36.133  75.746 277.692  1.00  0.00           C
ATOM   6857  CA  ARG F 132     -39.264  73.666 278.384  1.00  0.00           C
ATOM   6858  CA  ALA F 133     -40.538  73.700 274.807  1.00  0.00           C
ATOM   6859  CA  ILE F 134     -37.058  72.524 273.869  1.00  0.00           C
ATOM   6860  CA  LYS F 135     -36.680  69.713 276.414  1.00  0.00           C
ATOM   6861  CA  GLN F 136     -40.203  68.596 275.492  1.00  0.00           C
ATOM   6862  CA  ALA F 137     -39.385  68.535 271.785  1.00  0.00           C
ATOM   6863  CA  VAL F 138     -36.197  66.552 272.334  1.00  0.00           C
ATOM   6864  CA  GLN F 139     -38.224  64.139 274.400  1.00  0.00           C
ATOM   6865  CA  ARG F 140     -40.981  63.688 271.800  1.00  0.00           C
ATOM   6866  CA  VAL F 141     -38.379  63.085 269.080  1.00  0.00           C
ATOM   6867  CA  MET F 142     -36.295  60.939 271.359  1.00  0.00           C
ATOM   6868  CA  GLU F 143     -39.440  59.233 272.683  1.00  0.00           C
ATOM   6869  CA  SER F 144     -40.609  58.035 269.255  1.00  0.00           C
ATOM   6870  CA  GLY F 145     -37.713  56.260 267.579  1.00  0.00           C
ATOM   6871  CA  ALA F 146     -34.555  58.261 266.832  1.00  0.00           C
ATOM   6872  CA  LYS F 147     -31.136  57.086 267.975  1.00  0.00           C
ATOM   6873  CA  GLY F 148     -30.427  60.712 268.858  1.00  0.00           C
ATOM   6874  CA  ALA F 149     -31.784  64.261 268.722  1.00  0.00           C
ATOM   6875  CA  LYS F 150     -30.960  67.864 269.645  1.00  0.00           C
ATOM   6876  CA  VAL F 151     -32.669  71.263 269.528  1.00  0.00           C
ATOM   6877  CA  ILE F 152     -31.147  74.747 269.618  1.00  0.00           C
ATOM   6878  CA  VAL F 153     -32.902  78.065 270.115  1.00  0.00           C
ATOM   6879  CA  SER F 154     -31.163  81.311 269.149  1.00  0.00           C
ATOM   6880  CA  GLY F 155     -31.276  84.313 271.446  1.00  0.00           C
ATOM   6881  CA  ARG F 156     -33.457  86.799 273.330  1.00  0.00           C
ATOM   6882  CA  ILE F 157     -34.985  83.867 275.102  1.00  0.00           C
ATOM   6883  CA  GLY F 158     -38.056  85.140 276.907  1.00  0.00           C
ATOM   6884  CA  GLY F 159     -37.611  88.529 275.295  1.00  0.00           C
ATOM   6885  CA  ALA F 160     -34.553  89.064 277.497  1.00  0.00           C
ATOM   6886  CA  GLU F 161     -32.486  92.130 276.543  1.00  0.00           C
ATOM   6887  CA  GLN F 162     -29.380  89.894 276.336  1.00  0.00           C
ATOM   6888  CA  ALA F 163     -29.459  87.314 273.538  1.00  0.00           C
ATOM   6889  CA  ARG F 164     -28.776  83.824 274.859  1.00  0.00           C
ATOM   6890  CA  THR F 165     -28.719  80.340 273.337  1.00  0.00           C
ATOM   6891  CA  GLU F 166     -30.551  77.251 274.567  1.00  0.00           C
ATOM   6892  CA  TRP F 167     -29.593  73.604 274.217  1.00  0.00           C
ATOM   6893  CA  ALA F 168     -31.045  70.103 274.792  1.00  0.00           C
ATOM   6894  CA  ALA F 169     -29.859  66.792 273.373  1.00  0.00           C
ATOM   6895  CA  GLN F 170     -30.056  62.979 273.832  1.00  0.00           C
ATOM   6896  CA  GLY F 171     -28.271  59.951 272.323  1.00  0.00           C
ATOM   6897  CA  ARG F 172     -25.636  59.965 269.568  1.00  0.00           C
ATOM   6898  CA  VAL F 173     -25.880  62.970 267.227  1.00  0.00           C
ATOM   6899  CA  PRO F 174     -22.471  62.733 265.406  1.00  0.00           C
ATOM   6900  CA  LEU F 175     -22.281  65.773 263.169  1.00  0.00           C
ATOM   6901  CA  HIS F 176     -18.799  64.642 262.222  1.00  0.00           C
ATOM   6902  CA  THR F 177     -19.589  61.123 261.103  1.00  0.00           C
ATOM   6903  CA  LEU F 178     -20.105  61.451 257.363  1.00  0.00           C
ATOM   6904  CA  ARG F 179     -22.723  58.710 257.124  1.00  0.00           C
ATOM   6905  CA  ALA F 180     -24.973  59.309 260.147  1.00  0.00           C
ATOM   6906  CA  ASN F 181     -28.137  60.464 258.419  1.00  0.00           C
ATOM   6907  CA  ILE F 182     -29.116  63.386 260.506  1.00  0.00           C
ATOM   6908  CA  ASP F 183     -32.220  65.328 259.579  1.00  0.00           C
ATOM   6909  CA  TYR F 184     -31.606  69.043 259.917  1.00  0.00           C
ATOM   6910  CA  GLY F 185     -34.403  71.512 260.295  1.00  0.00           C
ATOM   6911  CA  PHE F 186     -34.477  75.238 260.868  1.00  0.00           C
ATOM   6912  CA  ALA F 187     -37.418  77.333 261.942  1.00  0.00           C
ATOM   6913  CA  LEU F 188     -37.552  81.123 262.260  1.00  0.00           C
ATOM   6914  CA  ALA F 189     -39.852  82.838 264.804  1.00  0.00           C
ATOM   6915  CA  ARG F 190     -40.849  86.475 264.242  1.00  0.00           C
ATOM   6916  CA  THR F 191     -41.626  88.209 267.552  1.00  0.00           C
ATOM   6917  CA  THR F 192     -42.596  91.418 269.297  1.00  0.00           C
ATOM   6918  CA  TYR F 193     -38.994  91.638 270.432  1.00  0.00           C
ATOM   6919  CA  GLY F 194     -37.332  90.037 267.416  1.00  0.00           C
ATOM   6920  CA  VAL F 195     -36.404  87.019 265.311  1.00  0.00           C
ATOM   6921  CA  LEU F 196     -35.203  83.858 267.069  1.00  0.00           C
ATOM   6922  CA  GLY F 197     -33.894  80.957 265.001  1.00  0.00           C
ATOM   6923  CA  VAL F 198     -34.708  77.347 265.876  1.00  0.00           C
ATOM   6924  CA  LYS F 199     -32.615  74.341 264.955  1.00  0.00           C
ATOM   6925  CA  ALA F 200     -33.664  70.703 265.105  1.00  0.00           C
ATOM   6926  CA  TYR F 201     -31.281  67.763 264.647  1.00  0.00           C
ATOM   6927  CA  ILE F 202     -32.509  64.176 264.445  1.00  0.00           C
ATOM   6928  CA  PHE F 203     -30.337  61.090 264.186  1.00  0.00           C
ATOM   6929  CA  LEU F 204     -31.634  57.823 262.690  1.00  0.00           C
ATOM   6930  CA  GLY F 205     -29.824  54.550 262.101  1.00  0.00           C
ATOM   6931  CA  GLU F 206     -26.469  55.080 260.433  1.00  0.00           C
ATOM   6932  CA  VAL F 207     -25.036  53.000 257.521  1.00  0.00           C
TER    6933          VAL F 207
ATOM   6934  CA  GLY G   2     -66.665  98.917 308.983  1.00  0.00           C
ATOM   6935  CA  ARG G   3     -66.266  95.251 308.066  1.00  0.00           C
ATOM   6936  CA  TYR G   4     -65.305  95.121 304.398  1.00  0.00           C
ATOM   6937  CA  ILE G   5     -68.513  95.734 302.431  1.00  0.00           C
ATOM   6938  CA  GLY G   6     -67.692  95.373 298.746  1.00  0.00           C
```

```
ATOM   6939  CA  PRO G   7     -67.760  92.791 295.950  1.00  0.00           C
ATOM   6940  CA  VAL G   8     -67.628  89.467 297.775  1.00  0.00           C
ATOM   6941  CA  CYS G   9     -67.793  86.706 295.184  1.00  0.00           C
ATOM   6942  CA  ARG G  10     -64.404  88.186 294.224  1.00  0.00           C
ATOM   6943  CA  LEU G  11     -62.888  86.905 297.473  1.00  0.00           C
ATOM   6944  CA  CYS G  12     -64.464  83.515 296.726  1.00  0.00           C
ATOM   6945  CA  ARG G  13     -62.353  83.718 293.546  1.00  0.00           C
ATOM   6946  CA  ARG G  14     -59.030  84.935 295.010  1.00  0.00           C
ATOM   6947  CA  GLU G  15     -59.059  82.082 297.520  1.00  0.00           C
ATOM   6948  CA  GLY G  16     -59.938  79.852 294.595  1.00  0.00           C
ATOM   6949  CA  VAL G  17     -62.203  78.123 297.097  1.00  0.00           C
ATOM   6950  CA  LYS G  18     -65.942  78.515 297.527  1.00  0.00           C
ATOM   6951  CA  LEU G  19     -66.969  80.947 300.222  1.00  0.00           C
ATOM   6952  CA  TYR G  20     -70.504  81.139 301.452  1.00  0.00           C
ATOM   6953  CA  LEU G  21     -70.735  84.894 301.816  1.00  0.00           C
ATOM   6954  CA  LYS G  22     -74.240  84.975 300.372  1.00  0.00           C
ATOM   6955  CA  GLY G  23     -76.034  81.931 301.712  1.00  0.00           C
ATOM   6956  CA  GLU G  24     -78.388  81.401 298.771  1.00  0.00           C
ATOM   6957  CA  ARG G  25     -77.077  81.798 295.213  1.00  0.00           C
ATOM   6958  CA  CYS G  26     -73.692  80.535 296.363  1.00  0.00           C
ATOM   6959  CA  TYR G  27     -75.478  77.359 295.209  1.00  0.00           C
ATOM   6960  CA  SER G  28     -77.409  78.409 292.118  1.00  0.00           C
ATOM   6961  CA  PRO G  29     -74.780  78.147 289.284  1.00  0.00           C
ATOM   6962  CA  LYS G  30     -73.502  81.646 290.000  1.00  0.00           C
ATOM   6963  CA  CYS G  31     -71.124  81.683 293.012  1.00  0.00           C
ATOM   6964  CA  ALA G  32     -68.830  82.472 290.082  1.00  0.00           C
ATOM   6965  CA  MET G  33     -66.662  79.668 291.425  1.00  0.00           C
ATOM   6966  CA  GLU G  34     -68.869  77.930 288.926  1.00  0.00           C
ATOM   6967  CA  ARG G  35     -67.121  78.238 285.556  1.00  0.00           C
ATOM   6968  CA  ARG G  36     -64.718  81.048 286.609  1.00  0.00           C
ATOM   6969  CA  PRO G  37     -62.793  79.933 289.784  1.00  0.00           C
ATOM   6970  CA  TYR G  38     -59.744  81.947 288.821  1.00  0.00           C
ATOM   6971  CA  PRO G  39     -58.721  85.110 290.732  1.00  0.00           C
ATOM   6972  CA  PRO G  40     -60.235  88.518 289.826  1.00  0.00           C
ATOM   6973  CA  GLY G  41     -58.509  91.113 287.665  1.00  0.00           C
ATOM   6974  CA  GLN G  42     -56.638  91.618 284.413  1.00  0.00           C
ATOM   6975  CA  HIS G  43     -54.369  88.700 285.307  1.00  0.00           C
ATOM   6976  CA  GLY G  44     -56.677  86.047 286.736  1.00  0.00           C
ATOM   6977  CA  GLN G  45     -56.307  83.706 283.769  1.00  0.00           C
ATOM   6978  CA  LYS G  46     -52.501  83.892 283.592  1.00  0.00           C
ATOM   6979  CA  ARG G  47     -50.452  81.020 285.047  1.00  0.00           C
ATOM   6980  CA  ALA G  48     -49.783  81.096 288.795  1.00  0.00           C
ATOM   6981  CA  ARG G  49     -46.250  80.929 290.201  1.00  0.00           C
ATOM   6982  CA  ARG G  50     -45.031  78.796 293.100  1.00  0.00           C
ATOM   6983  CA  PRO G  51     -46.252  80.801 296.145  1.00  0.00           C
ATOM   6984  CA  SER G  52     -43.828  81.758 298.921  1.00  0.00           C
ATOM   6985  CA  ASP G  53     -44.177  80.291 302.409  1.00  0.00           C
ATOM   6986  CA  TYR G  54     -45.473  83.751 303.294  1.00  0.00           C
ATOM   6987  CA  ALA G  55     -47.972  83.795 300.419  1.00  0.00           C
ATOM   6988  CA  VAL G  56     -49.341  80.439 301.519  1.00  0.00           C
ATOM   6989  CA  ARG G  57     -49.691  81.395 305.191  1.00  0.00           C
ATOM   6990  CA  LEU G  58     -51.024  84.749 304.134  1.00  0.00           C
ATOM   6991  CA  ARG G  59     -53.657  83.243 301.835  1.00  0.00           C
ATOM   6992  CA  GLU G  60     -54.664  80.685 304.443  1.00  0.00           C
ATOM   6993  CA  LYS G  61     -55.373  83.296 307.129  1.00  0.00           C
ATOM   6994  CA  GLN G  62     -57.198  85.631 304.724  1.00  0.00           C
ATOM   6995  CA  LYS G  63     -59.457  82.699 303.967  1.00  0.00           C
ATOM   6996  CA  LEU G  64     -60.321  81.621 307.513  1.00  0.00           C
ATOM   6997  CA  ARG G  65     -60.915  85.315 308.151  1.00  0.00           C
ATOM   6998  CA  ARG G  66     -62.965  86.412 305.156  1.00  0.00           C
ATOM   6999  CA  ILE G  67     -65.169  83.449 305.988  1.00  0.00           C
ATOM   7000  CA  TYR G  68     -66.396  85.288 309.071  1.00  0.00           C
ATOM   7001  CA  GLY G  69     -66.285  88.703 307.411  1.00  0.00           C
ATOM   7002  CA  ILE G  70     -64.206  89.966 310.335  1.00  0.00           C
ATOM   7003  CA  SER G  71     -61.585  92.723 310.558  1.00  0.00           C
ATOM   7004  CA  GLU G  72     -57.964  91.728 310.978  1.00  0.00           C
ATOM   7005  CA  ARG G  73     -58.003  93.903 314.087  1.00  0.00           C
ATOM   7006  CA  GLN G  74     -60.698  91.800 315.818  1.00  0.00           C
ATOM   7007  CA  PHE G  75     -59.537  88.567 314.215  1.00  0.00           C
ATOM   7008  CA  ARG G  76     -56.004  88.997 315.618  1.00  0.00           C
ATOM   7009  CA  ASN G  77     -57.186  89.644 319.174  1.00  0.00           C
ATOM   7010  CA  LEU G  78     -59.257  86.456 319.094  1.00  0.00           C
ATOM   7011  CA  PHE G  79     -56.160  84.595 317.996  1.00  0.00           C
ATOM   7012  CA  GLU G  80     -53.953  86.057 320.731  1.00  0.00           C
ATOM   7013  CA  GLU G  81     -56.769  84.991 323.048  1.00  0.00           C
ATOM   7014  CA  ALA G  82     -56.815  81.439 321.792  1.00  0.00           C
ATOM   7015  CA  SER G  83     -53.040  81.481 322.177  1.00  0.00           C
ATOM   7016  CA  LYS G  84     -53.027  82.176 325.895  1.00  0.00           C
ATOM   7017  CA  LYS G  85     -55.922  79.937 326.871  1.00  0.00           C
ATOM   7018  CA  LYS G  86     -55.131  76.263 327.452  1.00  0.00           C
ATOM   7019  CA  GLY G  87     -55.651  73.778 324.635  1.00  0.00           C
ATOM   7020  CA  VAL G  88     -54.577  73.422 321.034  1.00  0.00           C
ATOM   7021  CA  THR G  89     -54.537  77.058 320.024  1.00  0.00           C
ATOM   7022  CA  GLY G  90     -55.659  76.058 316.542  1.00  0.00           C
ATOM   7023  CA  SER G  91     -59.078  74.720 317.445  1.00  0.00           C
ATOM   7024  CA  VAL G  92     -59.582  76.892 320.536  1.00  0.00           C
ATOM   7025  CA  PHE G  93     -59.307  79.767 318.057  1.00  0.00           C
```

```
ATOM   7026  CA  LEU G  94     -61.982  78.312 315.792  1.00  0.00           C
ATOM   7027  CA  GLY G  95     -64.182  77.754 318.830  1.00  0.00           C
ATOM   7028  CA  LEU G  96     -64.169  81.460 319.616  1.00  0.00           C
ATOM   7029  CA  LEU G  97     -64.793  82.366 316.000  1.00  0.00           C
ATOM   7030  CA  GLU G  98     -67.883  80.142 316.018  1.00  0.00           C
ATOM   7031  CA  SER G  99     -69.104  81.709 319.287  1.00  0.00           C
ATOM   7032  CA  ARG G 100     -69.796  85.108 317.755  1.00  0.00           C
ATOM   7033  CA  LEU G 101     -73.474  85.864 318.237  1.00  0.00           C
ATOM   7034  CA  ASP G 102     -73.610  86.994 314.632  1.00  0.00           C
ATOM   7035  CA  ASN G 103     -72.090  83.680 313.536  1.00  0.00           C
ATOM   7036  CA  VAL G 104     -74.429  81.574 315.628  1.00  0.00           C
ATOM   7037  CA  VAL G 105     -77.457  83.326 314.150  1.00  0.00           C
ATOM   7038  CA  TYR G 106     -76.120  82.300 310.726  1.00  0.00           C
ATOM   7039  CA  ARG G 107     -75.401  78.801 311.999  1.00  0.00           C
ATOM   7040  CA  LEU G 108     -78.979  78.538 313.340  1.00  0.00           C
ATOM   7041  CA  GLY G 109     -80.510  79.364 309.970  1.00  0.00           C
ATOM   7042  CA  PHE G 110     -82.107  82.631 311.053  1.00  0.00           C
ATOM   7043  CA  ALA G 111     -80.106  84.458 308.395  1.00  0.00           C
ATOM   7044  CA  VAL G 112     -79.095  83.161 304.981  1.00  0.00           C
ATOM   7045  CA  SER G 113     -75.579  84.583 305.150  1.00  0.00           C
ATOM   7046  CA  ARG G 114     -73.126  85.728 307.807  1.00  0.00           C
ATOM   7047  CA  ARG G 115     -73.541  89.312 306.667  1.00  0.00           C
ATOM   7048  CA  GLN G 116     -77.341  89.108 306.897  1.00  0.00           C
ATOM   7049  CA  ALA G 117     -77.076  87.648 310.391  1.00  0.00           C
ATOM   7050  CA  ARG G 118     -74.741  90.492 311.314  1.00  0.00           C
ATOM   7051  CA  GLN G 119     -77.503  92.939 310.386  1.00  0.00           C
ATOM   7052  CA  LEU G 120     -80.264  91.010 312.128  1.00  0.00           C
ATOM   7053  CA  VAL G 121     -78.230  91.109 315.320  1.00  0.00           C
ATOM   7054  CA  ARG G 122     -77.405  94.766 314.650  1.00  0.00           C
ATOM   7055  CA  HIS G 123     -80.959  95.940 313.885  1.00  0.00           C
ATOM   7056  CA  GLY G 124     -82.116  94.320 317.159  1.00  0.00           C
ATOM   7057  CA  HIS G 125     -84.022  91.418 315.559  1.00  0.00           C
ATOM   7058  CA  ILE G 126     -82.153  89.005 317.873  1.00  0.00           C
ATOM   7059  CA  THR G 127     -82.299  87.792 321.472  1.00  0.00           C
ATOM   7060  CA  VAL G 128     -80.032  86.062 323.992  1.00  0.00           C
ATOM   7061  CA  ASN G 129     -81.812  84.640 327.033  1.00  0.00           C
ATOM   7062  CA  GLY G 130     -84.508  87.219 326.550  1.00  0.00           C
ATOM   7063  CA  ARG G 131     -82.471  90.442 326.701  1.00  0.00           C
ATOM   7064  CA  ARG G 132     -81.866  91.555 323.133  1.00  0.00           C
ATOM   7065  CA  VAL G 133     -78.278  91.939 321.972  1.00  0.00           C
ATOM   7066  CA  ASP G 134     -77.229  94.004 318.937  1.00  0.00           C
ATOM   7067  CA  LEU G 135     -73.496  93.300 319.277  1.00  0.00           C
ATOM   7068  CA  PRO G 136     -72.261  91.006 316.477  1.00  0.00           C
ATOM   7069  CA  SER G 137     -69.017  90.419 318.332  1.00  0.00           C
ATOM   7070  CA  TYR G 138     -71.041  89.244 321.322  1.00  0.00           C
ATOM   7071  CA  ARG G 139     -69.648  85.954 322.621  1.00  0.00           C
ATOM   7072  CA  VAL G 140     -72.308  83.265 323.019  1.00  0.00           C
ATOM   7073  CA  ARG G 141     -71.574  80.823 325.865  1.00  0.00           C
ATOM   7074  CA  PRO G 142     -72.761  77.201 326.164  1.00  0.00           C
ATOM   7075  CA  GLY G 143     -76.300  77.187 327.501  1.00  0.00           C
ATOM   7076  CA  ASP G 144     -77.659  80.318 325.883  1.00  0.00           C
ATOM   7077  CA  GLU G 145     -80.935  80.499 323.958  1.00  0.00           C
ATOM   7078  CA  ILE G 146     -80.762  82.512 320.764  1.00  0.00           C
ATOM   7079  CA  ALA G 147     -84.269  83.506 319.779  1.00  0.00           C
ATOM   7080  CA  VAL G 148     -85.587  85.776 317.082  1.00  0.00           C
ATOM   7081  CA  ALA G 149     -87.016  89.061 318.334  1.00  0.00           C
ATOM   7082  CA  GLU G 150     -90.744  88.774 318.948  1.00  0.00           C
ATOM   7083  CA  LYS G 151     -91.500  92.007 317.136  1.00  0.00           C
ATOM   7084  CA  SER G 152     -89.574  90.579 314.181  1.00  0.00           C
ATOM   7085  CA  ARG G 153     -91.019  87.052 314.326  1.00  0.00           C
ATOM   7086  CA  ASN G 154     -93.542  88.440 311.859  1.00  0.00           C
ATOM   7087  CA  LEU G 155     -90.887  89.853 309.534  1.00  0.00           C
ATOM   7088  CA  GLU G 156     -91.181  88.447 306.029  1.00  0.00           C
ATOM   7089  CA  LEU G 157     -87.454  87.684 305.959  1.00  0.00           C
ATOM   7090  CA  ILE G 158     -87.458  85.748 309.221  1.00  0.00           C
ATOM   7091  CA  ARG G 159     -90.484  83.685 308.225  1.00  0.00           C
ATOM   7092  CA  GLN G 160     -88.942  82.603 304.900  1.00  0.00           C
ATOM   7093  CA  ASN G 161     -85.608  81.509 306.390  1.00  0.00           C
ATOM   7094  CA  LEU G 162     -87.153  79.803 309.396  1.00  0.00           C
ATOM   7095  CA  GLU G 163     -89.531  78.087 306.973  1.00  0.00           C
ATOM   7096  CA  ALA G 164     -86.940  76.604 304.615  1.00  0.00           C
ATOM   7097  CA  MET G 165     -85.238  75.807 307.889  1.00  0.00           C
ATOM   7098  CA  LYS G 166     -87.863  73.091 308.300  1.00  0.00           C
ATOM   7099  CA  GLY G 167     -86.069  69.769 308.047  1.00  0.00           C
ATOM   7100  CA  ARG G 168     -82.589  71.276 307.726  1.00  0.00           C
ATOM   7101  CA  LYS G 169     -80.464  69.690 310.451  1.00  0.00           C
ATOM   7102  CA  VAL G 170     -78.194  71.696 312.753  1.00  0.00           C
ATOM   7103  CA  GLY G 171     -74.622  71.469 314.034  1.00  0.00           C
ATOM   7104  CA  PRO G 172     -74.105  68.849 316.802  1.00  0.00           C
ATOM   7105  CA  TRP G 173     -73.081  71.675 319.168  1.00  0.00           C
ATOM   7106  CA  LEU G 174     -76.350  73.484 318.533  1.00  0.00           C
ATOM   7107  CA  SER G 175     -80.102  72.742 318.440  1.00  0.00           C
ATOM   7108  CA  LEU G 176     -83.175  74.741 317.497  1.00  0.00           C
ATOM   7109  CA  ASP G 177     -86.920  74.848 318.128  1.00  0.00           C
ATOM   7110  CA  VAL G 178     -88.214  76.123 314.778  1.00  0.00           C
ATOM   7111  CA  GLU G 179     -91.531  76.694 316.579  1.00  0.00           C
ATOM   7112  CA  GLY G 180     -90.786  79.643 318.835  1.00  0.00           C
```

```
ATOM   7113  CA  MET G 181     -87.830  80.319 316.567  1.00  0.00           C
ATOM   7114  CA  LYS G 182     -85.403  79.509 319.370  1.00  0.00           C
ATOM   7115  CA  GLY G 183     -82.110  77.643 319.447  1.00  0.00           C
ATOM   7116  CA  LYS G 184     -79.383  76.722 321.918  1.00  0.00           C
ATOM   7117  CA  PHE G 185     -75.598  76.884 321.965  1.00  0.00           C
ATOM   7118  CA  LEU G 186     -74.922  73.437 323.444  1.00  0.00           C
ATOM   7119  CA  ARG G 187     -71.126  73.451 323.481  1.00  0.00           C
ATOM   7120  CA  LEU G 188     -68.036  74.990 321.866  1.00  0.00           C
ATOM   7121  CA  PRO G 189     -67.632  73.304 318.480  1.00  0.00           C
ATOM   7122  CA  ASP G 190     -64.478  71.245 318.019  1.00  0.00           C
ATOM   7123  CA  ARG G 191     -62.198  71.295 315.000  1.00  0.00           C
ATOM   7124  CA  GLU G 192     -63.970  68.152 313.714  1.00  0.00           C
ATOM   7125  CA  ASP G 193     -67.432  69.767 313.976  1.00  0.00           C
ATOM   7126  CA  LEU G 194     -66.438  72.365 311.381  1.00  0.00           C
ATOM   7127  CA  ALA G 195     -65.883  71.425 307.749  1.00  0.00           C
ATOM   7128  CA  LEU G 196     -63.791  74.524 307.187  1.00  0.00           C
ATOM   7129  CA  PRO G 197     -61.603  74.590 304.052  1.00  0.00           C
ATOM   7130  CA  VAL G 198     -59.056  75.997 306.485  1.00  0.00           C
ATOM   7131  CA  GLN G 199     -55.803  74.709 307.918  1.00  0.00           C
ATOM   7132  CA  GLU G 200     -55.289  76.671 311.120  1.00  0.00           C
ATOM   7133  CA  ASN G 201     -51.797  75.199 311.423  1.00  0.00           C
ATOM   7134  CA  LEU G 202     -50.808  77.662 308.720  1.00  0.00           C
ATOM   7135  CA  VAL G 203     -52.794  80.403 310.453  1.00  0.00           C
ATOM   7136  CA  ILE G 204     -50.916  79.859 313.686  1.00  0.00           C
ATOM   7137  CA  GLU G 205     -47.668  79.787 311.766  1.00  0.00           C
ATOM   7138  CA  PHE G 206     -48.527  83.067 310.056  1.00  0.00           C
ATOM   7139  CA  TYR G 207     -48.901  84.834 313.378  1.00  0.00           C
ATOM   7140  CA  SER G 208     -45.581  83.264 314.381  1.00  0.00           C
ATOM   7141  CA  ARG G 209     -43.457  85.283 311.953  1.00  0.00           C
TER    7142      ARG G 209
ATOM   7143  CA  ASP H   5     -46.299  58.401 300.350  1.00  0.00           C
ATOM   7144  CA  PHE H   6     -43.226  60.690 300.298  1.00  0.00           C
ATOM   7145  CA  GLU H   7     -43.847  64.443 300.274  1.00  0.00           C
ATOM   7146  CA  GLU H   8     -40.923  66.424 298.882  1.00  0.00           C
ATOM   7147  CA  LYS H   9     -39.741  69.819 300.193  1.00  0.00           C
ATOM   7148  CA  MET H  10     -36.801  71.687 298.625  1.00  0.00           C
ATOM   7149  CA  ILE H  11     -34.584  73.465 301.189  1.00  0.00           C
ATOM   7150  CA  LEU H  12     -32.325  75.514 298.918  1.00  0.00           C
ATOM   7151  CA  ILE H  13     -30.886  75.562 295.425  1.00  0.00           C
ATOM   7152  CA  ARG H  14     -27.735  77.547 294.693  1.00  0.00           C
ATOM   7153  CA  ARG H  15     -25.963  78.378 291.489  1.00  0.00           C
ATOM   7154  CA  THR H  16     -22.267  77.786 292.369  1.00  0.00           C
ATOM   7155  CA  ALA H  17     -19.366  78.336 289.909  1.00  0.00           C
ATOM   7156  CA  ARG H  18     -16.104  77.226 288.374  1.00  0.00           C
ATOM   7157  CA  MET H  19     -13.376  78.751 286.177  1.00  0.00           C
ATOM   7158  CA  GLN H  20     -11.866  77.765 282.860  1.00  0.00           C
ATOM   7159  CA  ALA H  21     -10.164  80.040 280.419  1.00  0.00           C
ATOM   7160  CA  GLY H  22     -12.844  81.801 278.500  1.00  0.00           C
ATOM   7161  CA  GLY H  23     -14.916  82.102 281.653  1.00  0.00           C
ATOM   7162  CA  ARG H  24     -17.295  80.932 284.349  1.00  0.00           C
ATOM   7163  CA  ARG H  25     -19.071  77.596 284.217  1.00  0.00           C
ATOM   7164  CA  PHE H  26     -21.878  76.933 286.655  1.00  0.00           C
ATOM   7165  CA  ARG H  27     -23.483  73.938 288.342  1.00  0.00           C
ATOM   7166  CA  PHE H  28     -26.528  73.801 290.582  1.00  0.00           C
ATOM   7167  CA  GLY H  29     -26.908  72.184 293.926  1.00  0.00           C
ATOM   7168  CA  ALA H  30     -30.219  71.388 295.508  1.00  0.00           C
ATOM   7169  CA  LEU H  31     -30.931  70.294 299.051  1.00  0.00           C
ATOM   7170  CA  VAL H  32     -34.079  68.230 299.214  1.00  0.00           C
ATOM   7171  CA  VAL H  33     -36.042  66.790 302.122  1.00  0.00           C
ATOM   7172  CA  VAL H  34     -38.293  63.811 301.657  1.00  0.00           C
ATOM   7173  CA  GLY H  35     -40.724  62.494 304.213  1.00  0.00           C
ATOM   7174  CA  ASP H  36     -44.008  60.688 304.749  1.00  0.00           C
ATOM   7175  CA  ARG H  37     -44.908  62.787 307.786  1.00  0.00           C
ATOM   7176  CA  GLN H  38     -45.204  59.414 309.481  1.00  0.00           C
ATOM   7177  CA  GLY H  39     -41.723  59.064 310.908  1.00  0.00           C
ATOM   7178  CA  ARG H  40     -39.523  58.759 307.854  1.00  0.00           C
ATOM   7179  CA  VAL H  41     -37.305  61.578 306.538  1.00  0.00           C
ATOM   7180  CA  GLY H  42     -34.443  61.673 304.131  1.00  0.00           C
ATOM   7181  CA  LEU H  43     -32.072  64.464 303.175  1.00  0.00           C
ATOM   7182  CA  GLY H  44     -30.304  64.551 299.865  1.00  0.00           C
ATOM   7183  CA  PHE H  45     -27.908  66.991 298.278  1.00  0.00           C
ATOM   7184  CA  GLY H  46     -27.707  66.620 294.537  1.00  0.00           C
ATOM   7185  CA  LYS H  47     -25.735  68.651 292.038  1.00  0.00           C
ATOM   7186  CA  ALA H  48     -26.136  68.813 288.292  1.00  0.00           C
ATOM   7187  CA  PRO H  49     -25.597  71.123 285.292  1.00  0.00           C
ATOM   7188  CA  GLU H  50     -29.276  72.075 285.502  1.00  0.00           C
ATOM   7189  CA  VAL H  51     -31.688  73.005 288.277  1.00  0.00           C
ATOM   7190  CA  PRO H  52     -34.139  70.157 287.509  1.00  0.00           C
ATOM   7191  CA  LEU H  53     -31.642  67.332 287.108  1.00  0.00           C
ATOM   7192  CA  ALA H  54     -30.302  68.651 290.401  1.00  0.00           C
ATOM   7193  CA  VAL H  55     -33.578  68.587 292.329  1.00  0.00           C
ATOM   7194  CA  GLN H  56     -34.318  65.208 290.800  1.00  0.00           C
ATOM   7195  CA  LYS H  57     -30.859  63.936 291.704  1.00  0.00           C
ATOM   7196  CA  ALA H  58     -31.323  65.207 295.267  1.00  0.00           C
ATOM   7197  CA  GLY H  59     -34.818  63.757 295.614  1.00  0.00           C
ATOM   7198  CA  TYR H  60     -33.436  60.394 294.558  1.00  0.00           C
ATOM   7199  CA  TYR H  61     -30.485  60.781 296.930  1.00  0.00           C
```

| | | | | | | | | | | |
|---|---|---|---|---|---|---|---|---|---|---|
|ATOM|7200|CA|ALA|H|62|-32.733|61.767|299.820|1.00|0.00|C|
|ATOM|7201|CA|ARG|H|63|-34.985|58.754|299.253|1.00|0.00|C|
|ATOM|7202|CA|ARG|H|64|-31.935|56.595|299.839|1.00|0.00|C|
|ATOM|7203|CA|ASN|H|65|-30.647|57.405|303.344|1.00|0.00|C|
|ATOM|7204|CA|MET|H|66|-33.839|57.773|305.385|1.00|0.00|C|
|ATOM|7205|CA|VAL|H|67|-34.079|58.176|309.146|1.00|0.00|C|
|ATOM|7206|CA|GLU|H|68|-36.654|56.667|311.489|1.00|0.00|C|
|ATOM|7207|CA|VAL|H|69|-37.936|59.428|313.778|1.00|0.00|C|
|ATOM|7208|CA|PRO|H|70|-39.213|58.031|317.132|1.00|0.00|C|
|ATOM|7209|CA|LEU|H|71|-42.239|60.334|317.201|1.00|0.00|C|
|ATOM|7210|CA|GLN|H|72|-44.374|60.393|320.338|1.00|0.00|C|
|ATOM|7211|CA|ASN|H|73|-47.615|62.305|320.160|1.00|0.00|C|
|ATOM|7212|CA|GLY|H|74|-46.190|64.480|317.382|1.00|0.00|C|
|ATOM|7213|CA|THR|H|75|-43.224|65.468|319.524|1.00|0.00|C|
|ATOM|7214|CA|ILE|H|76|-39.851|63.999|320.352|1.00|0.00|C|
|ATOM|7215|CA|PRO|H|77|-38.658|61.795|323.268|1.00|0.00|C|
|ATOM|7216|CA|HIS|H|78|-35.923|64.093|324.533|1.00|0.00|C|
|ATOM|7217|CA|GLU|H|79|-33.639|67.024|323.817|1.00|0.00|C|
|ATOM|7218|CA|ILE|H|80|-30.501|66.469|321.779|1.00|0.00|C|
|ATOM|7219|CA|GLU|H|81|-27.943|69.034|320.769|1.00|0.00|C|
|ATOM|7220|CA|VAL|H|82|-25.833|68.198|317.779|1.00|0.00|C|
|ATOM|7221|CA|GLU|H|83|-22.814|69.918|316.301|1.00|0.00|C|
|ATOM|7222|CA|PHE|H|84|-21.912|69.302|312.685|1.00|0.00|C|
|ATOM|7223|CA|GLY|H|85|-19.026|71.368|311.452|1.00|0.00|C|
|ATOM|7224|CA|ALA|H|86|-19.555|74.738|313.085|1.00|0.00|C|
|ATOM|7225|CA|SER|H|87|-23.312|74.231|312.996|1.00|0.00|C|
|ATOM|7226|CA|LYS|H|88|-25.042|73.300|316.212|1.00|0.00|C|
|ATOM|7227|CA|ILE|H|89|-28.726|72.350|316.220|1.00|0.00|C|
|ATOM|7228|CA|VAL|H|90|-30.829|72.096|319.347|1.00|0.00|C|
|ATOM|7229|CA|LEU|H|91|-34.079|70.169|319.654|1.00|0.00|C|
|ATOM|7230|CA|LYS|H|92|-36.379|70.210|322.686|1.00|0.00|C|
|ATOM|7231|CA|PRO|H|93|-39.720|68.361|322.965|1.00|0.00|C|
|ATOM|7232|CA|ALA|H|94|-42.938|70.367|323.283|1.00|0.00|C|
|ATOM|7233|CA|ALA|H|95|-46.562|69.806|324.286|1.00|0.00|C|
|ATOM|7234|CA|PRO|H|96|-49.363|69.844|321.704|1.00|0.00|C|
|ATOM|7235|CA|GLY|H|97|-50.408|73.222|320.349|1.00|0.00|C|
|ATOM|7236|CA|THR|H|98|-46.837|74.475|320.484|1.00|0.00|C|
|ATOM|7237|CA|GLY|H|99|-46.189|74.048|316.757|1.00|0.00|C|
|ATOM|7238|CA|VAL|H|100|-42.984|73.335|314.888|1.00|0.00|C|
|ATOM|7239|CA|ILE|H|101|-40.962|76.293|316.134|1.00|0.00|C|
|ATOM|7240|CA|ALA|H|102|-37.765|76.366|314.135|1.00|0.00|C|
|ATOM|7241|CA|GLY|H|103|-36.002|78.124|311.292|1.00|0.00|C|
|ATOM|7242|CA|ALA|H|104|-36.843|76.990|307.758|1.00|0.00|C|
|ATOM|7243|CA|VAL|H|105|-34.197|74.325|307.094|1.00|0.00|C|
|ATOM|7244|CA|PRO|H|106|-34.744|72.641|310.498|1.00|0.00|C|
|ATOM|7245|CA|ARG|H|107|-38.516|72.989|310.196|1.00|0.00|C|
|ATOM|7246|CA|ALA|H|108|-38.868|71.611|306.668|1.00|0.00|C|
|ATOM|7247|CA|ILE|H|109|-37.183|68.445|307.860|1.00|0.00|C|
|ATOM|7248|CA|LEU|H|110|-39.026|68.192|311.159|1.00|0.00|C|
|ATOM|7249|CA|GLU|H|111|-42.370|68.557|309.317|1.00|0.00|C|
|ATOM|7250|CA|LEU|H|112|-41.926|65.828|306.725|1.00|0.00|C|
|ATOM|7251|CA|ALA|H|113|-40.347|64.037|309.635|1.00|0.00|C|
|ATOM|7252|CA|GLY|H|114|-43.862|63.913|311.009|1.00|0.00|C|
|ATOM|7253|CA|VAL|H|115|-43.011|66.088|313.975|1.00|0.00|C|
|ATOM|7254|CA|THR|H|116|-45.715|68.566|314.776|1.00|0.00|C|
|ATOM|7255|CA|ASP|H|117|-44.648|70.137|318.072|1.00|0.00|C|
|ATOM|7256|CA|ILE|H|118|-41.046|71.120|318.920|1.00|0.00|C|
|ATOM|7257|CA|LEU|H|119|-38.786|73.822|320.337|1.00|0.00|C|
|ATOM|7258|CA|THR|H|120|-35.719|74.396|318.176|1.00|0.00|C|
|ATOM|7259|CA|LYS|H|121|-32.568|76.483|317.965|1.00|0.00|C|
|ATOM|7260|CA|GLU|H|122|-29.735|76.993|315.493|1.00|0.00|C|
|ATOM|7261|CA|LEU|H|123|-26.443|77.875|317.085|1.00|0.00|C|
|ATOM|7262|CA|GLY|H|124|-22.991|78.485|315.611|1.00|0.00|C|
|ATOM|7263|CA|SER|H|125|-22.608|78.355|311.849|1.00|0.00|C|
|ATOM|7264|CA|ARG|H|126|-25.979|78.693|310.208|1.00|0.00|C|
|ATOM|7265|CA|ASN|H|127|-25.065|77.230|306.864|1.00|0.00|C|
|ATOM|7266|CA|PRO|H|128|-28.373|75.688|305.801|1.00|0.00|C|
|ATOM|7267|CA|ILE|H|129|-26.516|72.733|304.348|1.00|0.00|C|
|ATOM|7268|CA|ASN|H|130|-24.651|72.131|307.588|1.00|0.00|C|
|ATOM|7269|CA|ILE|H|131|-27.656|72.841|309.792|1.00|0.00|C|
|ATOM|7270|CA|ALA|H|132|-29.508|70.275|307.688|1.00|0.00|C|
|ATOM|7271|CA|TYR|H|133|-26.911|67.518|308.187|1.00|0.00|C|
|ATOM|7272|CA|ALA|H|134|-26.797|68.583|311.835|1.00|0.00|C|
|ATOM|7273|CA|THR|H|135|-30.540|68.135|312.142|1.00|0.00|C|
|ATOM|7274|CA|MET|H|136|-30.624|64.707|310.510|1.00|0.00|C|
|ATOM|7275|CA|GLU|H|137|-27.843|63.572|312.835|1.00|0.00|C|
|ATOM|7276|CA|ALA|H|138|-29.795|64.895|315.786|1.00|0.00|C|
|ATOM|7277|CA|LEU|H|139|-32.795|62.872|314.651|1.00|0.00|C|
|ATOM|7278|CA|ARG|H|140|-30.736|59.709|314.147|1.00|0.00|C|
|ATOM|7279|CA|GLN|H|141|-29.492|59.920|317.722|1.00|0.00|C|
|ATOM|7280|CA|LEU|H|142|-32.956|60.100|319.294|1.00|0.00|C|
|ATOM|7281|CA|ARG|H|143|-33.628|57.156|321.595|1.00|0.00|C|
|ATOM|7282|CA|THR|H|144|-36.619|55.811|323.485|1.00|0.00|C|
|ATOM|7283|CA|LYS|H|145|-37.081|54.657|327.064|1.00|0.00|C|
|ATOM|7284|CA|ALA|H|146|-37.487|51.393|325.168|1.00|0.00|C|
|ATOM|7285|CA|ASP|H|147|-34.119|51.472|323.376|1.00|0.00|C|
|ATOM|7286|CA|VAL|H|148|-32.458|52.793|326.508|1.00|0.00|C|

```
ATOM   7287  CA  GLU H 149     -33.983  50.079 328.693  1.00  0.00           C
ATOM   7288  CA  ARG H 150     -32.999  47.600 326.005  1.00  0.00           C
ATOM   7289  CA  LEU H 151     -29.419  48.957 325.907  1.00  0.00           C
ATOM   7290  CA  ARG H 152     -28.996  48.637 329.643  1.00  0.00           C
ATOM   7291  CA  LYS H 153     -30.450  45.132 330.169  1.00  0.00           C
ATOM   7292  CA  GLY H 154     -27.608  42.611 330.140  1.00  0.00           C
TER    7293      GLY H 154
ATOM   7294  CA  MET I   1      41.345  72.165 348.582  1.00  0.00           C
ATOM   7295  CA  ARG I   2      40.973  70.883 345.019  1.00  0.00           C
ATOM   7296  CA  ARG I   3      43.310  68.732 342.894  1.00  0.00           C
ATOM   7297  CA  TYR I   4      44.639  70.496 339.759  1.00  0.00           C
ATOM   7298  CA  GLU I   5      47.061  70.088 336.856  1.00  0.00           C
ATOM   7299  CA  VAL I   6      49.610  72.787 336.109  1.00  0.00           C
ATOM   7300  CA  ASN I   7      51.098  72.960 332.617  1.00  0.00           C
ATOM   7301  CA  ILE I   8      54.036  75.203 331.892  1.00  0.00           C
ATOM   7302  CA  VAL I   9      55.759  75.780 328.569  1.00  0.00           C
ATOM   7303  CA  LEU I  10      59.023  77.695 328.751  1.00  0.00           C
ATOM   7304  CA  ASN I  11      61.849  78.668 326.393  1.00  0.00           C
ATOM   7305  CA  PRO I  12      63.608  75.644 324.794  1.00  0.00           C
ATOM   7306  CA  ASN I  13      66.912  77.516 324.734  1.00  0.00           C
ATOM   7307  CA  LEU I  14      67.747  77.524 328.420  1.00  0.00           C
ATOM   7308  CA  ASP I  15      71.072  76.053 329.535  1.00  0.00           C
ATOM   7309  CA  GLN I  16      71.280  73.417 332.273  1.00  0.00           C
ATOM   7310  CA  SER I  17      71.508  76.239 334.823  1.00  0.00           C
ATOM   7311  CA  GLN I  18      69.116  78.876 333.425  1.00  0.00           C
ATOM   7312  CA  LEU I  19      66.449  76.180 333.220  1.00  0.00           C
ATOM   7313  CA  ALA I  20      66.836  74.769 336.731  1.00  0.00           C
ATOM   7314  CA  LEU I  21      66.617  78.399 337.906  1.00  0.00           C
ATOM   7315  CA  GLU I  22      63.156  78.921 336.435  1.00  0.00           C
ATOM   7316  CA  LYS I  23      62.026  75.626 337.953  1.00  0.00           C
ATOM   7317  CA  GLU I  24      63.289  77.073 341.215  1.00  0.00           C
ATOM   7318  CA  ILE I  25      60.932  80.053 341.104  1.00  0.00           C
ATOM   7319  CA  ILE I  26      58.104  77.686 340.116  1.00  0.00           C
ATOM   7320  CA  GLN I  27      58.525  75.268 343.028  1.00  0.00           C
ATOM   7321  CA  ARG I  28      59.054  78.366 345.149  1.00  0.00           C
ATOM   7322  CA  ALA I  29      55.910  79.984 343.759  1.00  0.00           C
ATOM   7323  CA  LEU I  30      53.836  76.857 344.244  1.00  0.00           C
ATOM   7324  CA  GLU I  31      54.432  76.630 347.987  1.00  0.00           C
ATOM   7325  CA  ASN I  32      53.910  80.386 348.240  1.00  0.00           C
ATOM   7326  CA  TYR I  33      50.325  79.658 347.228  1.00  0.00           C
ATOM   7327  CA  GLY I  34      49.718  76.327 348.929  1.00  0.00           C
ATOM   7328  CA  ALA I  35      50.589  74.100 345.995  1.00  0.00           C
ATOM   7329  CA  ARG I  36      51.171  70.636 347.470  1.00  0.00           C
ATOM   7330  CA  VAL I  37      53.074  68.926 344.619  1.00  0.00           C
ATOM   7331  CA  GLU I  38      51.404  65.507 344.297  1.00  0.00           C
ATOM   7332  CA  LYS I  39      53.632  64.642 341.345  1.00  0.00           C
ATOM   7333  CA  VAL I  40      55.396  65.697 338.172  1.00  0.00           C
ATOM   7334  CA  GLU I  41      56.339  64.845 334.596  1.00  0.00           C
ATOM   7335  CA  GLU I  42      58.838  66.566 332.319  1.00  0.00           C
ATOM   7336  CA  LEU I  43      58.405  65.699 328.635  1.00  0.00           C
ATOM   7337  CA  GLY I  44      60.769  68.629 328.218  1.00  0.00           C
ATOM   7338  CA  LEU I  45      61.255  69.570 324.574  1.00  0.00           C
ATOM   7339  CA  ARG I  46      58.504  69.169 321.983  1.00  0.00           C
ATOM   7340  CA  ARG I  47      57.869  70.394 318.427  1.00  0.00           C
ATOM   7341  CA  LEU I  48      54.932  72.812 318.727  1.00  0.00           C
ATOM   7342  CA  ALA I  49      52.132  72.718 316.160  1.00  0.00           C
ATOM   7343  CA  TYR I  50      52.768  76.402 315.558  1.00  0.00           C
ATOM   7344  CA  PRO I  51      55.484  78.785 316.793  1.00  0.00           C
ATOM   7345  CA  ILE I  52      55.241  80.301 320.265  1.00  0.00           C
ATOM   7346  CA  ALA I  53      57.262  83.477 320.739  1.00  0.00           C
ATOM   7347  CA  LYS I  54      58.788  82.933 317.285  1.00  0.00           C
ATOM   7348  CA  ASP I  55      60.377  79.785 318.732  1.00  0.00           C
ATOM   7349  CA  PRO I  56      58.953  76.607 317.043  1.00  0.00           C
ATOM   7350  CA  GLN I  57      59.723  74.386 320.055  1.00  0.00           C
ATOM   7351  CA  GLY I  58      58.922  74.364 323.742  1.00  0.00           C
ATOM   7352  CA  TYR I  59      60.024  72.898 327.073  1.00  0.00           C
ATOM   7353  CA  PHE I  60      57.254  71.278 329.113  1.00  0.00           C
ATOM   7354  CA  LEU I  61      56.603  70.924 332.821  1.00  0.00           C
ATOM   7355  CA  TRP I  62      53.552  69.124 334.223  1.00  0.00           C
ATOM   7356  CA  TYR I  63      52.662  69.370 337.914  1.00  0.00           C
ATOM   7357  CA  GLN I  64      49.643  67.751 339.542  1.00  0.00           C
ATOM   7358  CA  VAL I  65      48.969  69.757 342.709  1.00  0.00           C
ATOM   7359  CA  GLU I  66      46.478  70.187 345.522  1.00  0.00           C
ATOM   7360  CA  MET I  67      45.800  73.723 346.750  1.00  0.00           C
ATOM   7361  CA  PRO I  68      43.326  76.410 347.918  1.00  0.00           C
ATOM   7362  CA  GLU I  69      41.170  77.162 344.876  1.00  0.00           C
ATOM   7363  CA  ASP I  70      40.754  80.712 346.188  1.00  0.00           C
ATOM   7364  CA  ARG I  71      44.325  81.317 344.978  1.00  0.00           C
ATOM   7365  CA  VAL I  72      44.675  79.183 341.840  1.00  0.00           C
ATOM   7366  CA  ASN I  73      44.162  82.308 339.781  1.00  0.00           C
ATOM   7367  CA  ASP I  74      46.988  84.165 341.568  1.00  0.00           C
ATOM   7368  CA  LEU I  75      49.229  81.109 341.398  1.00  0.00           C
ATOM   7369  CA  ALA I  76      49.141  81.546 337.631  1.00  0.00           C
ATOM   7370  CA  ARG I  77      49.430  85.351 337.584  1.00  0.00           C
ATOM   7371  CA  GLU I  78      52.651  84.608 339.384  1.00  0.00           C
ATOM   7372  CA  LEU I  79      53.725  81.797 337.095  1.00  0.00           C
ATOM   7373  CA  ARG I  80      53.211  84.000 334.018  1.00  0.00           C
```

```
ATOM   7374  CA  ILE I   81      55.459  86.798 335.363  1.00  0.00           C
ATOM   7375  CA  ARG I   82      58.598  84.931 334.322  1.00  0.00           C
ATOM   7376  CA  ASP I   83      59.958  85.972 330.911  1.00  0.00           C
ATOM   7377  CA  ASN I   84      61.019  82.434 330.018  1.00  0.00           C
ATOM   7378  CA  VAL I   85      57.511  81.254 330.853  1.00  0.00           C
ATOM   7379  CA  ARG I   86      55.545  81.372 327.624  1.00  0.00           C
ATOM   7380  CA  ARG I   87      52.456  79.327 328.628  1.00  0.00           C
ATOM   7381  CA  VAL I   88      50.644  78.391 331.818  1.00  0.00           C
ATOM   7382  CA  MET I   89      47.490  76.293 331.994  1.00  0.00           C
ATOM   7383  CA  VAL I   90      46.009  75.185 335.326  1.00  0.00           C
ATOM   7384  CA  VAL I   91      43.264  72.589 335.001  1.00  0.00           C
ATOM   7385  CA  LYS I   92      40.904  70.862 337.452  1.00  0.00           C
ATOM   7386  CA  SER I   93      41.986  67.236 337.543  1.00  0.00           C
ATOM   7387  CA  GLN I   94      39.357  64.961 336.057  1.00  0.00           C
ATOM   7388  CA  GLU I   95      38.573  61.254 336.091  1.00  0.00           C
ATOM   7389  CA  PRO I   96      39.861  59.840 332.798  1.00  0.00           C
ATOM   7390  CA  PHE I   97      36.763  59.557 330.607  1.00  0.00           C
ATOM   7391  CA  LEU I   98      37.604  56.428 328.570  1.00  0.00           C
ATOM   7392  CA  ALA I   99      36.307  55.569 325.101  1.00  0.00           C
ATOM   7393  CA  ASN I  100      36.329  52.842 322.448  1.00  0.00           C
ATOM   7394  CA  ALA I  101      36.648  50.208 325.187  1.00  0.00           C
TER    7395      ALA I  101
ATOM   7396  CA  ALA J    2      13.214  71.655 262.779  1.00  0.00           C
ATOM   7397  CA  ARG J    3      11.964  70.902 266.332  1.00  0.00           C
ATOM   7398  CA  ARG J    4      11.286  67.193 265.750  1.00  0.00           C
ATOM   7399  CA  ARG J    5      13.541  65.323 263.296  1.00  0.00           C
ATOM   7400  CA  ARG J    6      17.100  66.172 262.371  1.00  0.00           C
ATOM   7401  CA  ALA J    7      16.195  67.111 258.783  1.00  0.00           C
ATOM   7402  CA  GLU J    8      18.308  64.829 256.597  1.00  0.00           C
ATOM   7403  CA  VAL J    9      20.284  66.272 253.699  1.00  0.00           C
ATOM   7404  CA  ARG J   10      18.689  66.181 250.244  1.00  0.00           C
ATOM   7405  CA  GLN J   11      20.951  63.907 248.164  1.00  0.00           C
ATOM   7406  CA  LEU J   12      21.646  65.353 244.713  1.00  0.00           C
ATOM   7407  CA  GLN J   13      21.818  63.544 241.375  1.00  0.00           C
ATOM   7408  CA  PRO J   14      25.441  63.548 240.108  1.00  0.00           C
ATOM   7409  CA  ASP J   15      26.757  65.722 237.276  1.00  0.00           C
ATOM   7410  CA  LEU J   16      25.680  64.986 233.690  1.00  0.00           C
ATOM   7411  CA  VAL J   17      29.350  65.153 232.666  1.00  0.00           C
ATOM   7412  CA  TYR J   18      31.560  64.459 235.674  1.00  0.00           C
ATOM   7413  CA  GLY J   19      28.906  62.475 237.526  1.00  0.00           C
ATOM   7414  CA  ASP J   20      30.107  64.426 240.533  1.00  0.00           C
ATOM   7415  CA  VAL J   21      27.407  65.520 242.973  1.00  0.00           C
ATOM   7416  CA  LEU J   22      29.502  68.353 244.406  1.00  0.00           C
ATOM   7417  CA  VAL J   23      29.345  69.867 240.942  1.00  0.00           C
ATOM   7418  CA  THR J   24      25.548  69.779 240.744  1.00  0.00           C
ATOM   7419  CA  ALA J   25      25.521  71.513 244.086  1.00  0.00           C
ATOM   7420  CA  PHE J   26      27.715  74.335 242.727  1.00  0.00           C
ATOM   7421  CA  ILE J   27      25.552  74.539 239.617  1.00  0.00           C
ATOM   7422  CA  ASN J   28      22.469  74.849 241.809  1.00  0.00           C
ATOM   7423  CA  LYS J   29      24.126  77.748 243.597  1.00  0.00           C
ATOM   7424  CA  ILE J   30      24.669  79.480 240.263  1.00  0.00           C
ATOM   7425  CA  MET J   31      21.113  78.826 239.115  1.00  0.00           C
ATOM   7426  CA  ARG J   32      18.446  81.464 239.653  1.00  0.00           C
ATOM   7427  CA  ASP J   33      14.697  81.216 238.962  1.00  0.00           C
ATOM   7428  CA  GLY J   34      15.214  77.525 238.342  1.00  0.00           C
ATOM   7429  CA  LYS J   35      16.773  78.264 234.949  1.00  0.00           C
ATOM   7430  CA  LYS J   36      18.995  75.237 235.557  1.00  0.00           C
ATOM   7431  CA  ASN J   37      20.036  75.013 231.894  1.00  0.00           C
ATOM   7432  CA  LEU J   38      21.690  78.425 231.754  1.00  0.00           C
ATOM   7433  CA  ALA J   39      23.179  77.463 235.115  1.00  0.00           C
ATOM   7434  CA  ALA J   40      24.687  74.201 233.840  1.00  0.00           C
ATOM   7435  CA  ARG J   41      25.984  75.905 230.725  1.00  0.00           C
ATOM   7436  CA  ILE J   42      27.739  78.682 232.608  1.00  0.00           C
ATOM   7437  CA  PHE J   43      29.585  76.130 234.718  1.00  0.00           C
ATOM   7438  CA  TYR J   44      30.617  74.001 231.767  1.00  0.00           C
ATOM   7439  CA  ASP J   45      31.611  76.948 229.560  1.00  0.00           C
ATOM   7440  CA  ALA J   46      33.708  77.934 232.555  1.00  0.00           C
ATOM   7441  CA  CYS J   47      35.269  74.484 232.800  1.00  0.00           C
ATOM   7442  CA  LYS J   48      36.340  74.898 229.196  1.00  0.00           C
ATOM   7443  CA  ILE J   49      37.800  78.293 230.106  1.00  0.00           C
ATOM   7444  CA  ILE J   50      39.752  76.534 232.834  1.00  0.00           C
ATOM   7445  CA  GLN J   51      41.033  74.178 230.133  1.00  0.00           C
ATOM   7446  CA  GLU J   52      42.318  76.854 227.810  1.00  0.00           C
ATOM   7447  CA  LYS J   53      43.913  79.451 230.089  1.00  0.00           C
ATOM   7448  CA  THR J   54      45.085  76.561 232.335  1.00  0.00           C
ATOM   7449  CA  GLY J   55      46.462  73.236 231.147  1.00  0.00           C
ATOM   7450  CA  GLN J   56      44.834  71.495 234.101  1.00  0.00           C
ATOM   7451  CA  GLU J   57      41.660  69.397 234.229  1.00  0.00           C
ATOM   7452  CA  PRO J   58      38.802  71.699 235.272  1.00  0.00           C
ATOM   7453  CA  LEU J   59      37.285  69.203 237.745  1.00  0.00           C
ATOM   7454  CA  LYS J   60      40.474  69.252 239.848  1.00  0.00           C
ATOM   7455  CA  VAL J   61      40.823  73.048 239.698  1.00  0.00           C
ATOM   7456  CA  PHE J   62      37.269  73.261 241.008  1.00  0.00           C
ATOM   7457  CA  LYS J   63      37.671  70.875 243.923  1.00  0.00           C
ATOM   7458  CA  GLN J   64      40.958  72.545 244.826  1.00  0.00           C
ATOM   7459  CA  ALA J   65      39.117  75.871 244.979  1.00  0.00           C
ATOM   7460  CA  VAL J   66      36.312  74.625 247.221  1.00  0.00           C
```

```
ATOM   7461  CA  GLU J  67      39.068  73.367 249.491  1.00  0.00           C
ATOM   7462  CA  ASN J  68      40.780  76.735 250.003  1.00  0.00           C
ATOM   7463  CA  VAL J  69      37.411  78.444 250.487  1.00  0.00           C
ATOM   7464  CA  LYS J  70      36.059  76.181 253.252  1.00  0.00           C
ATOM   7465  CA  PRO J  71      36.291  77.967 256.609  1.00  0.00           C
ATOM   7466  CA  ARG J  72      37.387  75.679 259.443  1.00  0.00           C
ATOM   7467  CA  MET J  73      36.452  78.055 262.276  1.00  0.00           C
ATOM   7468  CA  GLU J  74      33.631  80.576 262.305  1.00  0.00           C
ATOM   7469  CA  VAL J  75      32.117  82.912 264.849  1.00  0.00           C
ATOM   7470  CA  ARG J  76      28.531  82.419 266.058  1.00  0.00           C
ATOM   7471  CA  SER J  77      26.807  85.092 268.117  1.00  0.00           C
ATOM   7472  CA  ARG J  78      25.324  84.344 271.539  1.00  0.00           C
ATOM   7473  CA  ARG J  79      23.886  86.293 274.454  1.00  0.00           C
ATOM   7474  CA  VAL J  80      25.876  85.563 277.594  1.00  0.00           C
ATOM   7475  CA  GLY J  81      25.189  87.613 280.699  1.00  0.00           C
ATOM   7476  CA  GLY J  82      24.343  90.875 278.965  1.00  0.00           C
ATOM   7477  CA  ALA J  83      26.409  91.537 275.842  1.00  0.00           C
ATOM   7478  CA  ASN J  84      26.165  89.265 272.799  1.00  0.00           C
ATOM   7479  CA  TYR J  85      29.612  87.663 272.718  1.00  0.00           C
ATOM   7480  CA  GLN J  86      30.693  86.178 269.377  1.00  0.00           C
ATOM   7481  CA  VAL J  87      31.681  82.608 270.247  1.00  0.00           C
ATOM   7482  CA  PRO J  88      34.210  80.957 267.869  1.00  0.00           C
ATOM   7483  CA  MET J  89      33.731  77.349 266.891  1.00  0.00           C
ATOM   7484  CA  GLU J  90      34.378  74.591 264.384  1.00  0.00           C
ATOM   7485  CA  VAL J  91      32.344  74.257 261.225  1.00  0.00           C
ATOM   7486  CA  SER J  92      30.475  71.099 260.293  1.00  0.00           C
ATOM   7487  CA  PRO J  93      31.788  69.277 257.247  1.00  0.00           C
ATOM   7488  CA  ARG J  94      28.333  69.906 255.798  1.00  0.00           C
ATOM   7489  CA  ARG J  95      28.250  73.649 256.491  1.00  0.00           C
ATOM   7490  CA  GLN J  96      31.794  74.099 255.171  1.00  0.00           C
ATOM   7491  CA  GLN J  97      30.663  73.068 251.724  1.00  0.00           C
ATOM   7492  CA  SER J  98      27.494  75.171 251.695  1.00  0.00           C
ATOM   7493  CA  LEU J  99      29.589  78.204 252.607  1.00  0.00           C
ATOM   7494  CA  ALA J 100      32.429  77.434 250.195  1.00  0.00           C
ATOM   7495  CA  LEU J 101      30.196  77.007 247.148  1.00  0.00           C
ATOM   7496  CA  ARG J 102      28.038  79.950 248.143  1.00  0.00           C
ATOM   7497  CA  TRP J 103      31.058  82.188 248.665  1.00  0.00           C
ATOM   7498  CA  LEU J 104      32.532  81.197 245.312  1.00  0.00           C
ATOM   7499  CA  VAL J 105      29.436  82.080 243.299  1.00  0.00           C
ATOM   7500  CA  GLN J 106      29.103  85.278 245.312  1.00  0.00           C
ATOM   7501  CA  ALA J 107      32.659  86.513 244.788  1.00  0.00           C
ATOM   7502  CA  ALA J 108      32.451  85.281 241.224  1.00  0.00           C
ATOM   7503  CA  ASN J 109      29.467  87.505 240.570  1.00  0.00           C
ATOM   7504  CA  GLN J 110      31.468  90.189 242.333  1.00  0.00           C
ATOM   7505  CA  ARG J 111      34.117  90.181 239.606  1.00  0.00           C
ATOM   7506  CA  PRO J 112      34.237  92.634 236.657  1.00  0.00           C
ATOM   7507  CA  GLU J 113      34.428  90.567 233.435  1.00  0.00           C
ATOM   7508  CA  ARG J 114      31.099  91.083 231.648  1.00  0.00           C
ATOM   7509  CA  ARG J 115      30.605  87.321 231.009  1.00  0.00           C
ATOM   7510  CA  ALA J 116      28.987  85.200 233.702  1.00  0.00           C
ATOM   7511  CA  ALA J 117      30.747  82.024 232.554  1.00  0.00           C
ATOM   7512  CA  VAL J 118      34.101  83.810 232.831  1.00  0.00           C
ATOM   7513  CA  ARG J 119      33.671  85.250 236.299  1.00  0.00           C
ATOM   7514  CA  ILE J 120      33.164  81.695 237.444  1.00  0.00           C
ATOM   7515  CA  ALA J 121      36.090  80.434 235.412  1.00  0.00           C
ATOM   7516  CA  HIS J 122      38.472  83.074 236.730  1.00  0.00           C
ATOM   7517  CA  GLU J 123      37.141  82.976 240.292  1.00  0.00           C
ATOM   7518  CA  LEU J 124      37.705  79.230 240.566  1.00  0.00           C
ATOM   7519  CA  MET J 125      41.301  79.564 239.351  1.00  0.00           C
ATOM   7520  CA  ASP J 126      42.088  82.471 241.688  1.00  0.00           C
ATOM   7521  CA  ALA J 127      40.567  80.408 244.489  1.00  0.00           C
ATOM   7522  CA  ALA J 128      42.799  77.483 243.580  1.00  0.00           C
ATOM   7523  CA  GLU J 129      45.901  79.710 243.730  1.00  0.00           C
ATOM   7524  CA  GLY J 130      44.786  80.955 247.130  1.00  0.00           C
ATOM   7525  CA  LYS J 131      43.715  84.417 246.015  1.00  0.00           C
ATOM   7526  CA  GLY J 132      40.380  85.976 245.090  1.00  0.00           C
ATOM   7527  CA  GLY J 133      37.293  87.400 246.758  1.00  0.00           C
ATOM   7528  CA  ALA J 134      36.148  83.925 247.748  1.00  0.00           C
ATOM   7529  CA  VAL J 135      39.195  83.042 249.805  1.00  0.00           C
ATOM   7530  CA  LYS J 136      39.132  86.523 251.296  1.00  0.00           C
ATOM   7531  CA  LYS J 137      35.832  85.867 253.078  1.00  0.00           C
ATOM   7532  CA  LYS J 138      37.074  82.448 254.142  1.00  0.00           C
ATOM   7533  CA  GLU J 139      40.239  83.832 255.704  1.00  0.00           C
ATOM   7534  CA  ASP J 140      38.232  86.784 257.067  1.00  0.00           C
ATOM   7535  CA  VAL J 141      35.990  84.363 258.930  1.00  0.00           C
ATOM   7536  CA  GLU J 142      38.831  82.446 260.541  1.00  0.00           C
ATOM   7537  CA  ARG J 143      40.413  85.791 261.437  1.00  0.00           C
ATOM   7538  CA  MET J 144      37.145  86.860 263.073  1.00  0.00           C
ATOM   7539  CA  ALA J 145      37.246  83.664 265.141  1.00  0.00           C
ATOM   7540  CA  GLU J 146      40.582  83.203 266.888  1.00  0.00           C
ATOM   7541  CA  ALA J 147      40.254  86.981 267.429  1.00  0.00           C
ATOM   7542  CA  ASN J 148      37.370  86.454 269.824  1.00  0.00           C
ATOM   7543  CA  ARG J 149      39.131  83.330 270.993  1.00  0.00           C
ATOM   7544  CA  ALA J 150      38.733  84.556 274.568  1.00  0.00           C
ATOM   7545  CA  TYR J 151      34.980  84.046 274.665  1.00  0.00           C
ATOM   7546  CA  ALA J 152      35.667  80.544 273.358  1.00  0.00           C
ATOM   7547  CA  HIS J 153      35.016  79.050 276.783  1.00  0.00           C
```

```
ATOM   7548  CA  TYR J 154      31.348  79.386 275.845  1.00  0.00           C
ATOM   7549  CA  ARG J 155      32.162  76.485 273.507  1.00  0.00           C
ATOM   7550  CA  TRP J 156      28.501  75.842 272.654  1.00  0.00           C
TER    7551      TRP J 156
ATOM   7552  CA  MET K   1      -1.510  70.638 341.704  1.00  0.00           C
ATOM   7553  CA  LEU K   2      -4.785  68.717 341.350  1.00  0.00           C
ATOM   7554  CA  THR K   3      -7.090  71.722 341.321  1.00  0.00           C
ATOM   7555  CA  ASP K   4     -10.464  69.896 341.105  1.00  0.00           C
ATOM   7556  CA  PRO K   5     -10.600  66.221 342.213  1.00  0.00           C
ATOM   7557  CA  ILE K   6     -14.243  65.818 341.176  1.00  0.00           C
ATOM   7558  CA  ALA K   7     -13.754  67.325 337.763  1.00  0.00           C
ATOM   7559  CA  ASP K   8     -10.642  65.233 337.416  1.00  0.00           C
ATOM   7560  CA  MET K   9     -12.730  62.114 337.889  1.00  0.00           C
ATOM   7561  CA  LEU K  10     -15.520  63.000 335.483  1.00  0.00           C
ATOM   7562  CA  THR K  11     -12.871  63.670 332.878  1.00  0.00           C
ATOM   7563  CA  ARG K  12     -10.915  60.482 333.502  1.00  0.00           C
ATOM   7564  CA  ILE K  13     -14.263  58.731 332.929  1.00  0.00           C
ATOM   7565  CA  ARG K  14     -15.152  60.814 329.889  1.00  0.00           C
ATOM   7566  CA  ASN K  15     -11.665  60.185 328.507  1.00  0.00           C
ATOM   7567  CA  ALA K  16     -11.584  56.418 329.141  1.00  0.00           C
ATOM   7568  CA  THR K  17     -15.022  55.764 327.768  1.00  0.00           C
ATOM   7569  CA  ARG K  18     -14.167  57.594 324.548  1.00  0.00           C
ATOM   7570  CA  VAL K  19     -11.535  54.967 323.842  1.00  0.00           C
ATOM   7571  CA  TYR K  20     -13.661  52.238 325.344  1.00  0.00           C
ATOM   7572  CA  LYS K  21     -11.539  51.200 328.279  1.00  0.00           C
ATOM   7573  CA  GLU K  22     -13.077  48.371 330.296  1.00  0.00           C
ATOM   7574  CA  SER K  23     -11.855  49.691 333.675  1.00  0.00           C
ATOM   7575  CA  THR K  24     -10.234  53.062 334.654  1.00  0.00           C
ATOM   7576  CA  ASP K  25      -8.659  54.235 337.929  1.00  0.00           C
ATOM   7577  CA  VAL K  26      -9.170  57.484 339.849  1.00  0.00           C
ATOM   7578  CA  PRO K  27      -7.600  58.409 343.212  1.00  0.00           C
ATOM   7579  CA  ALA K  28     -10.091  57.591 345.971  1.00  0.00           C
ATOM   7580  CA  SER K  29     -11.868  60.186 348.088  1.00  0.00           C
ATOM   7581  CA  ARG K  30     -14.972  59.624 350.244  1.00  0.00           C
ATOM   7582  CA  PHE K  31     -16.813  62.228 348.173  1.00  0.00           C
ATOM   7583  CA  LYS K  32     -15.780  60.745 344.812  1.00  0.00           C
ATOM   7584  CA  GLU K  33     -16.969  57.340 345.985  1.00  0.00           C
ATOM   7585  CA  GLU K  34     -20.257  58.968 346.955  1.00  0.00           C
ATOM   7586  CA  ILE K  35     -20.701  60.183 343.397  1.00  0.00           C
ATOM   7587  CA  LEU K  36     -19.789  56.852 341.826  1.00  0.00           C
ATOM   7588  CA  ARG K  37     -22.527  55.280 344.011  1.00  0.00           C
ATOM   7589  CA  ILE K  38     -25.095  57.261 341.986  1.00  0.00           C
ATOM   7590  CA  LEU K  39     -23.361  56.648 338.686  1.00  0.00           C
ATOM   7591  CA  ALA K  40     -23.856  52.956 339.265  1.00  0.00           C
ATOM   7592  CA  ARG K  41     -27.391  53.084 340.652  1.00  0.00           C
ATOM   7593  CA  GLU K  42     -28.477  55.292 337.768  1.00  0.00           C
ATOM   7594  CA  GLY K  43     -26.953  52.636 335.548  1.00  0.00           C
ATOM   7595  CA  PHE K  44     -24.210  54.749 333.928  1.00  0.00           C
ATOM   7596  CA  ILE K  45     -21.376  52.477 334.978  1.00  0.00           C
ATOM   7597  CA  LYS K  46     -21.157  48.744 335.539  1.00  0.00           C
ATOM   7598  CA  GLY K  47     -19.986  49.767 338.986  1.00  0.00           C
ATOM   7599  CA  TYR K  48     -16.715  50.518 340.758  1.00  0.00           C
ATOM   7600  CA  GLU K  49     -14.473  49.112 343.496  1.00  0.00           C
ATOM   7601  CA  ARG K  50     -11.732  50.175 345.901  1.00  0.00           C
ATOM   7602  CA  VAL K  51      -8.257  49.134 344.794  1.00  0.00           C
ATOM   7603  CA  ASP K  52      -4.652  49.914 345.738  1.00  0.00           C
ATOM   7604  CA  VAL K  53      -2.316  51.312 343.071  1.00  0.00           C
ATOM   7605  CA  ASP K  54       1.338  51.615 344.083  1.00  0.00           C
ATOM   7606  CA  GLY K  55       0.144  51.488 347.669  1.00  0.00           C
ATOM   7607  CA  LYS K  56      -2.298  54.338 347.358  1.00  0.00           C
ATOM   7608  CA  PRO K  57      -6.123  54.090 347.323  1.00  0.00           C
ATOM   7609  CA  TYR K  58      -7.976  54.246 344.012  1.00  0.00           C
ATOM   7610  CA  LEU K  59     -11.419  53.519 342.711  1.00  0.00           C
ATOM   7611  CA  ARG K  60     -11.692  51.221 339.704  1.00  0.00           C
ATOM   7612  CA  VAL K  61     -14.520  52.454 337.573  1.00  0.00           C
ATOM   7613  CA  TYR K  62     -16.068  49.783 335.390  1.00  0.00           C
ATOM   7614  CA  LEU K  63     -17.247  51.400 332.199  1.00  0.00           C
ATOM   7615  CA  LYS K  64     -20.358  50.392 330.277  1.00  0.00           C
ATOM   7616  CA  TYR K  65     -21.222  50.751 326.589  1.00  0.00           C
ATOM   7617  CA  GLY K  66     -23.976  49.928 324.166  1.00  0.00           C
ATOM   7618  CA  PRO K  67     -23.647  47.006 321.765  1.00  0.00           C
ATOM   7619  CA  ARG K  68     -21.527  46.787 318.618  1.00  0.00           C
ATOM   7620  CA  ARG K  69     -23.032  48.528 315.587  1.00  0.00           C
ATOM   7621  CA  GLN K  70     -23.666  48.035 311.858  1.00  0.00           C
ATOM   7622  CA  GLY K  71     -22.106  49.723 308.852  1.00  0.00           C
ATOM   7623  CA  PRO K  72     -18.769  51.567 309.058  1.00  0.00           C
ATOM   7624  CA  ASP K  73     -17.465  52.376 312.538  1.00  0.00           C
ATOM   7625  CA  PRO K  74     -18.947  49.549 314.639  1.00  0.00           C
ATOM   7626  CA  ARG K  75     -18.068  51.483 317.782  1.00  0.00           C
ATOM   7627  CA  PRO K  76     -20.710  51.091 320.503  1.00  0.00           C
ATOM   7628  CA  GLU K  77     -22.972  53.983 321.474  1.00  0.00           C
ATOM   7629  CA  GLN K  78     -21.842  55.389 324.813  1.00  0.00           C
ATOM   7630  CA  VAL K  79     -24.056  54.935 327.846  1.00  0.00           C
ATOM   7631  CA  ILE K  80     -22.544  58.173 329.112  1.00  0.00           C
ATOM   7632  CA  HIS K  81     -23.132  60.475 326.157  1.00  0.00           C
ATOM   7633  CA  HIS K  82     -22.444  63.401 328.424  1.00  0.00           C
ATOM   7634  CA  ILE K  83     -21.001  64.294 331.811  1.00  0.00           C
```

```
ATOM   7635  CA  ARG K  84    -20.068  67.930 332.525  1.00  0.00           C
ATOM   7636  CA  ARG K  85    -18.838  69.639 335.733  1.00  0.00           C
ATOM   7637  CA  ILE K  86    -20.883  72.603 336.849  1.00  0.00           C
ATOM   7638  CA  SER K  87    -20.067  73.925 340.262  1.00  0.00           C
ATOM   7639  CA  LYS K  88    -16.298  74.513 340.096  1.00  0.00           C
ATOM   7640  CA  PRO K  89    -13.866  76.258 342.437  1.00  0.00           C
ATOM   7641  CA  GLY K  90    -13.945  79.977 341.814  1.00  0.00           C
ATOM   7642  CA  ARG K  91    -17.536  79.682 340.562  1.00  0.00           C
ATOM   7643  CA  ARG K  92    -19.448  77.577 343.013  1.00  0.00           C
ATOM   7644  CA  VAL K  93    -23.028  76.848 341.974  1.00  0.00           C
ATOM   7645  CA  TYR K  94    -25.850  76.205 344.431  1.00  0.00           C
ATOM   7646  CA  VAL K  95    -29.571  75.778 343.814  1.00  0.00           C
ATOM   7647  CA  GLY K  96    -32.779  75.911 345.810  1.00  0.00           C
ATOM   7648  CA  VAL K  97    -35.109  72.932 345.599  1.00  0.00           C
ATOM   7649  CA  LYS K  98    -37.222  75.006 343.214  1.00  0.00           C
ATOM   7650  CA  GLU K  99    -34.200  75.592 340.926  1.00  0.00           C
ATOM   7651  CA  ILE K 100    -32.930  72.007 340.575  1.00  0.00           C
ATOM   7652  CA  PRO K 101    -32.630  71.650 336.781  1.00  0.00           C
ATOM   7653  CA  ARG K 102    -34.461  69.064 334.688  1.00  0.00           C
ATOM   7654  CA  VAL K 103    -31.649  67.453 332.718  1.00  0.00           C
ATOM   7655  CA  ARG K 104    -32.280  66.260 329.169  1.00  0.00           C
ATOM   7656  CA  ARG K 105    -36.056  66.491 329.593  1.00  0.00           C
ATOM   7657  CA  GLY K 106    -35.782  63.884 332.318  1.00  0.00           C
ATOM   7658  CA  LEU K 107    -33.673  61.333 330.423  1.00  0.00           C
ATOM   7659  CA  GLY K 108    -30.497  62.614 332.025  1.00  0.00           C
ATOM   7660  CA  ILE K 109    -29.618  63.372 335.599  1.00  0.00           C
ATOM   7661  CA  ALA K 110    -27.906  65.953 337.725  1.00  0.00           C
ATOM   7662  CA  ILE K 111    -25.909  65.143 340.811  1.00  0.00           C
ATOM   7663  CA  LEU K 112    -26.321  67.525 343.723  1.00  0.00           C
ATOM   7664  CA  SER K 113    -24.617  67.600 347.085  1.00  0.00           C
ATOM   7665  CA  THR K 114    -27.131  68.400 349.839  1.00  0.00           C
ATOM   7666  CA  SER K 115    -26.942  68.554 353.621  1.00  0.00           C
ATOM   7667  CA  LYS K 116    -28.913  65.320 353.218  1.00  0.00           C
ATOM   7668  CA  GLY K 117    -26.092  63.752 351.181  1.00  0.00           C
ATOM   7669  CA  VAL K 118    -25.256  63.308 347.495  1.00  0.00           C
ATOM   7670  CA  LEU K 119    -28.477  62.743 345.537  1.00  0.00           C
ATOM   7671  CA  THR K 120    -29.759  62.943 341.992  1.00  0.00           C
ATOM   7672  CA  ASP K 121    -32.119  65.733 340.943  1.00  0.00           C
ATOM   7673  CA  ARG K 122    -35.115  63.453 341.402  1.00  0.00           C
ATOM   7674  CA  GLU K 123    -33.924  62.232 344.811  1.00  0.00           C
ATOM   7675  CA  ALA K 124    -33.291  65.799 345.940  1.00  0.00           C
ATOM   7676  CA  ARG K 125    -36.677  67.025 344.802  1.00  0.00           C
ATOM   7677  CA  LYS K 126    -38.280  64.141 346.682  1.00  0.00           C
ATOM   7678  CA  LEU K 127    -36.406  64.908 349.914  1.00  0.00           C
ATOM   7679  CA  GLY K 128    -37.265  68.520 349.039  1.00  0.00           C
ATOM   7680  CA  VAL K 129    -33.758  69.984 349.312  1.00  0.00           C
ATOM   7681  CA  GLY K 130    -31.185  71.868 347.287  1.00  0.00           C
ATOM   7682  CA  GLY K 131    -27.427  72.398 347.322  1.00  0.00           C
ATOM   7683  CA  GLU K 132    -24.190  72.630 345.313  1.00  0.00           C
ATOM   7684  CA  LEU K 133    -24.807  71.454 341.742  1.00  0.00           C
ATOM   7685  CA  ILE K 134    -21.886  69.031 341.329  1.00  0.00           C
ATOM   7686  CA  CYS K 135    -22.532  67.893 337.772  1.00  0.00           C
ATOM   7687  CA  GLU K 136    -24.834  66.810 334.951  1.00  0.00           C
ATOM   7688  CA  VAL K 137    -24.905  63.396 333.272  1.00  0.00           C
ATOM   7689  CA  TRP K 138    -26.885  61.918 330.380  1.00  0.00           C
TER    7690      TRP K 138
ATOM   7691  CA  GLU L   2     11.018  41.203 218.087  1.00  0.00           C
ATOM   7692  CA  GLN L   3      9.818  44.235 220.056  1.00  0.00           C
ATOM   7693  CA  TYR L   4      9.467  45.569 223.605  1.00  0.00           C
ATOM   7694  CA  TYR L   5      7.227  48.052 225.392  1.00  0.00           C
ATOM   7695  CA  GLY L   6      7.082  50.271 228.452  1.00  0.00           C
ATOM   7696  CA  THR L   7      5.014  53.416 228.858  1.00  0.00           C
ATOM   7697  CA  GLY L   8      6.340  55.905 231.389  1.00  0.00           C
ATOM   7698  CA  ARG L   9      4.673  58.983 232.854  1.00  0.00           C
ATOM   7699  CA  ARG L  10      6.126  62.025 234.624  1.00  0.00           C
ATOM   7700  CA  LYS L  11      4.766  65.346 235.843  1.00  0.00           C
ATOM   7701  CA  GLU L  12      1.965  64.898 233.305  1.00  0.00           C
ATOM   7702  CA  ALA L  13      3.757  63.386 230.310  1.00  0.00           C
ATOM   7703  CA  VAL L  14      3.269  60.077 228.509  1.00  0.00           C
ATOM   7704  CA  ALA L  15      6.028  58.362 226.557  1.00  0.00           C
ATOM   7705  CA  ARG L  16      5.538  55.260 224.424  1.00  0.00           C
ATOM   7706  CA  VAL L  17      8.842  53.394 224.536  1.00  0.00           C
ATOM   7707  CA  PHE L  18      9.479  50.724 221.905  1.00  0.00           C
ATOM   7708  CA  LEU L  19     12.804  48.910 222.113  1.00  0.00           C
ATOM   7709  CA  ARG L  20     14.022  46.678 219.274  1.00  0.00           C
ATOM   7710  CA  PRO L  21     17.363  44.823 219.077  1.00  0.00           C
ATOM   7711  CA  GLY L  22     19.461  46.974 216.768  1.00  0.00           C
ATOM   7712  CA  ASN L  23     22.034  49.774 216.499  1.00  0.00           C
ATOM   7713  CA  GLY L  24     21.086  52.061 219.378  1.00  0.00           C
ATOM   7714  CA  LYS L  25     19.457  55.001 217.633  1.00  0.00           C
ATOM   7715  CA  VAL L  26     16.299  56.684 218.896  1.00  0.00           C
ATOM   7716  CA  THR L  27     13.418  58.198 216.986  1.00  0.00           C
ATOM   7717  CA  VAL L  28     11.512  60.528 219.274  1.00  0.00           C
ATOM   7718  CA  ASN L  29      8.298  61.538 217.512  1.00  0.00           C
ATOM   7719  CA  GLY L  30     10.091  61.267 214.212  1.00  0.00           C
ATOM   7720  CA  GLN L  31     13.053  63.529 214.889  1.00  0.00           C
ATOM   7721  CA  ASP L  32     16.296  62.010 216.121  1.00  0.00           C
```

```
ATOM   7722  CA   PHE L  33      16.781  61.782 219.892  1.00  0.00           C
ATOM   7723  CA   ASN L  34      19.298  64.613 219.542  1.00  0.00           C
ATOM   7724  CA   GLU L  35      16.925  66.395 217.187  1.00  0.00           C
ATOM   7725  CA   TYR L  36      13.807  66.657 219.381  1.00  0.00           C
ATOM   7726  CA   PHE L  37      15.944  67.568 222.415  1.00  0.00           C
ATOM   7727  CA   GLN L  38      18.127  69.941 220.413  1.00  0.00           C
ATOM   7728  CA   GLY L  39      20.202  71.580 223.126  1.00  0.00           C
ATOM   7729  CA   LEU L  40      19.020  70.424 226.556  1.00  0.00           C
ATOM   7730  CA   VAL L  41      21.814  69.508 228.971  1.00  0.00           C
ATOM   7731  CA   ARG L  42      19.383  67.040 230.593  1.00  0.00           C
ATOM   7732  CA   ALA L  43      18.327  64.932 227.589  1.00  0.00           C
ATOM   7733  CA   VAL L  44      21.168  62.504 228.272  1.00  0.00           C
ATOM   7734  CA   ALA L  45      19.121  61.394 231.283  1.00  0.00           C
ATOM   7735  CA   ALA L  46      16.348  59.525 229.423  1.00  0.00           C
ATOM   7736  CA   LEU L  47      18.758  56.844 228.148  1.00  0.00           C
ATOM   7737  CA   GLU L  48      20.400  56.373 231.539  1.00  0.00           C
ATOM   7738  CA   PRO L  49      18.345  53.220 232.187  1.00  0.00           C
ATOM   7739  CA   LEU L  50      20.100  51.754 229.134  1.00  0.00           C
ATOM   7740  CA   ARG L  51      23.700  52.431 230.189  1.00  0.00           C
ATOM   7741  CA   ALA L  52      22.315  50.968 233.390  1.00  0.00           C
ATOM   7742  CA   VAL L  53      22.635  47.451 231.981  1.00  0.00           C
ATOM   7743  CA   ASP L  54      24.879  48.169 228.972  1.00  0.00           C
ATOM   7744  CA   ALA L  55      22.213  48.730 226.334  1.00  0.00           C
ATOM   7745  CA   LEU L  56      21.973  51.349 223.576  1.00  0.00           C
ATOM   7746  CA   GLY L  57      24.698  49.711 221.504  1.00  0.00           C
ATOM   7747  CA   ARG L  58      22.583  46.586 221.654  1.00  0.00           C
ATOM   7748  CA   PHE L  59      19.043  47.971 221.329  1.00  0.00           C
ATOM   7749  CA   ASP L  60      17.193  50.681 219.447  1.00  0.00           C
ATOM   7750  CA   ALA L  61      14.156  52.786 220.327  1.00  0.00           C
ATOM   7751  CA   TYR L  62      11.095  54.230 218.647  1.00  0.00           C
ATOM   7752  CA   ILE L  63       9.362  56.677 220.957  1.00  0.00           C
ATOM   7753  CA   THR L  64       6.092  58.601 220.909  1.00  0.00           C
ATOM   7754  CA   VAL L  65       5.890  61.444 223.396  1.00  0.00           C
ATOM   7755  CA   ARG L  66       2.934  63.755 224.015  1.00  0.00           C
ATOM   7756  CA   GLY L  67       2.075  65.867 227.050  1.00  0.00           C
ATOM   7757  CA   GLY L  68       3.766  68.376 229.327  1.00  0.00           C
ATOM   7758  CA   GLY L  69       7.187  69.780 228.517  1.00  0.00           C
ATOM   7759  CA   LYS L  70      10.394  68.452 226.985  1.00  0.00           C
ATOM   7760  CA   SER L  71      11.711  68.094 230.522  1.00  0.00           C
ATOM   7761  CA   GLY L  72       8.831  65.994 231.784  1.00  0.00           C
ATOM   7762  CA   GLN L  73       8.967  64.012 228.586  1.00  0.00           C
ATOM   7763  CA   ILE L  74      12.657  63.356 229.242  1.00  0.00           C
ATOM   7764  CA   ASP L  75      11.642  61.696 232.515  1.00  0.00           C
ATOM   7765  CA   ALA L  76       8.647  59.830 231.087  1.00  0.00           C
ATOM   7766  CA   ILE L  77      10.859  58.504 228.312  1.00  0.00           C
ATOM   7767  CA   LYS L  78      13.475  57.633 230.921  1.00  0.00           C
ATOM   7768  CA   LEU L  79      10.815  55.554 232.716  1.00  0.00           C
ATOM   7769  CA   GLY L  80       9.584  54.038 229.475  1.00  0.00           C
ATOM   7770  CA   ILE L  81      13.042  52.799 228.504  1.00  0.00           C
ATOM   7771  CA   ALA L  82      13.287  51.551 232.089  1.00  0.00           C
ATOM   7772  CA   ARG L  83      10.038  49.558 231.962  1.00  0.00           C
ATOM   7773  CA   ALA L  84      10.546  48.127 228.494  1.00  0.00           C
ATOM   7774  CA   LEU L  85      14.046  47.008 229.450  1.00  0.00           C
ATOM   7775  CA   VAL L  86      12.224  44.734 231.924  1.00  0.00           C
ATOM   7776  CA   GLN L  87       9.688  43.062 229.613  1.00  0.00           C
ATOM   7777  CA   TYR L  88      12.710  42.144 227.533  1.00  0.00           C
ATOM   7778  CA   ASN L  89      14.687  40.661 230.404  1.00  0.00           C
ATOM   7779  CA   PRO L  90      12.874  40.647 233.777  1.00  0.00           C
ATOM   7780  CA   ASP L  91      16.138  39.693 235.480  1.00  0.00           C
ATOM   7781  CA   TYR L  92      17.233  43.332 235.094  1.00  0.00           C
ATOM   7782  CA   ARG L  93      15.259  44.865 237.976  1.00  0.00           C
ATOM   7783  CA   ALA L  94      17.899  43.710 240.469  1.00  0.00           C
ATOM   7784  CA   LYS L  95      20.154  46.509 239.164  1.00  0.00           C
ATOM   7785  CA   LEU L  96      17.663  48.718 237.344  1.00  0.00           C
ATOM   7786  CA   LYS L  97      15.624  49.391 240.513  1.00  0.00           C
ATOM   7787  CA   PRO L  98      18.236  50.081 243.189  1.00  0.00           C
ATOM   7788  CA   LEU L  99      18.658  53.240 241.082  1.00  0.00           C
ATOM   7789  CA   GLY L 100      14.919  53.805 241.169  1.00  0.00           C
ATOM   7790  CA   PHE L 101      14.327  54.181 237.445  1.00  0.00           C
ATOM   7791  CA   LEU L 102      11.235  52.002 237.904  1.00  0.00           C
ATOM   7792  CA   THR L 103       9.451  54.589 240.027  1.00  0.00           C
ATOM   7793  CA   ARG L 104       6.885  57.103 238.815  1.00  0.00           C
ATOM   7794  CA   ASP L 105       7.855  60.475 240.273  1.00  0.00           C
ATOM   7795  CA   ALA L 106       4.448  61.553 241.616  1.00  0.00           C
ATOM   7796  CA   ARG L 107       5.453  65.219 242.014  1.00  0.00           C
ATOM   7797  CA   VAL L 108       2.758  67.253 240.233  1.00  0.00           C
ATOM   7798  CA   VAL L 109       1.744  70.928 240.187  1.00  0.00           C
ATOM   7799  CA   GLU L 110      -0.071  71.959 243.367  1.00  0.00           C
ATOM   7800  CA   ARG L 111      -3.614  73.271 243.081  1.00  0.00           C
ATOM   7801  CA   LYS L 112      -3.994  77.050 243.329  1.00  0.00           C
ATOM   7802  CA   LYS L 113      -5.954  77.637 246.550  1.00  0.00           C
ATOM   7803  CA   TYR L 114      -8.119  80.718 246.982  1.00  0.00           C
ATOM   7804  CA   GLY L 115      -7.141  83.545 249.288  1.00  0.00           C
ATOM   7805  CA   LYS L 116      -3.562  82.883 248.253  1.00  0.00           C
ATOM   7806  CA   HIS L 117      -1.606  84.014 245.203  1.00  0.00           C
ATOM   7807  CA   LYS L 118      -0.180  80.685 244.177  1.00  0.00           C
ATOM   7808  CA   ALA L 119      -1.322  77.731 246.309  1.00  0.00           C
```

| | | | | | | | | | | |
|---|---|---|---|---|---|---|---|---|---|---|
| ATOM | 7809 | CA | ARG | L | 120 | 1.017 | 78.884 | 249.030 | 1.00 | 0.00 | C |
| ATOM | 7810 | CA | ARG | L | 121 | 2.478 | 82.279 | 248.195 | 1.00 | 0.00 | C |
| ATOM | 7811 | CA | ALA | L | 122 | 0.288 | 84.238 | 250.618 | 1.00 | 0.00 | C |
| ATOM | 7812 | CA | PRO | L | 123 | -0.420 | 87.753 | 250.096 | 1.00 | 0.00 | C |
| ATOM | 7813 | CA | GLN | L | 124 | 1.777 | 90.712 | 251.499 | 1.00 | 0.00 | C |
| ATOM | 7814 | CA | TYR | L | 125 | 1.192 | 93.944 | 253.416 | 1.00 | 0.00 | C |
| ATOM | 7815 | CA | SER | L | 126 | 1.886 | 96.159 | 256.148 | 1.00 | 0.00 | C |
| ATOM | 7816 | CA | LYS | L | 127 | 0.156 | 97.400 | 259.493 | 1.00 | 0.00 | C |
| ATOM | 7817 | CA | ARG | L | 128 | 0.229 | 96.557 | 263.254 | 1.00 | 0.00 | C |
| TER | 7818 | | ARG | L | 128 | | | | | | |
| ATOM | 7819 | CA | LYS | M | 3 | -24.631 | 52.193 | 212.554 | 1.00 | 0.00 | C |
| ATOM | 7820 | CA | ILE | M | 4 | -26.736 | 54.182 | 215.009 | 1.00 | 0.00 | C |
| ATOM | 7821 | CA | ARG | M | 5 | -24.447 | 56.235 | 217.260 | 1.00 | 0.00 | C |
| ATOM | 7822 | CA | ILE | M | 6 | -26.135 | 57.038 | 220.560 | 1.00 | 0.00 | C |
| ATOM | 7823 | CA | LYS | M | 7 | -24.694 | 59.566 | 223.016 | 1.00 | 0.00 | C |
| ATOM | 7824 | CA | LEU | M | 8 | -26.162 | 59.519 | 226.519 | 1.00 | 0.00 | C |
| ATOM | 7825 | CA | ARG | M | 9 | -25.416 | 62.247 | 229.053 | 1.00 | 0.00 | C |
| ATOM | 7826 | CA | GLY | M | 10 | -26.686 | 62.761 | 232.578 | 1.00 | 0.00 | C |
| ATOM | 7827 | CA | PHE | M | 11 | -25.948 | 64.010 | 236.074 | 1.00 | 0.00 | C |
| ATOM | 7828 | CA | ASP | M | 12 | -26.528 | 60.739 | 237.904 | 1.00 | 0.00 | C |
| ATOM | 7829 | CA | HIS | M | 13 | -23.964 | 58.050 | 237.111 | 1.00 | 0.00 | C |
| ATOM | 7830 | CA | LYS | M | 14 | -26.695 | 55.494 | 237.818 | 1.00 | 0.00 | C |
| ATOM | 7831 | CA | THR | M | 15 | -29.523 | 57.128 | 235.914 | 1.00 | 0.00 | C |
| ATOM | 7832 | CA | LEU | M | 16 | -27.294 | 56.507 | 232.886 | 1.00 | 0.00 | C |
| ATOM | 7833 | CA | ASP | M | 17 | -25.819 | 53.097 | 233.596 | 1.00 | 0.00 | C |
| ATOM | 7834 | CA | ALA | M | 18 | -29.480 | 52.217 | 234.114 | 1.00 | 0.00 | C |
| ATOM | 7835 | CA | SER | M | 19 | -30.698 | 54.097 | 231.044 | 1.00 | 0.00 | C |
| ATOM | 7836 | CA | ALA | M | 20 | -27.895 | 53.222 | 228.614 | 1.00 | 0.00 | C |
| ATOM | 7837 | CA | GLN | M | 21 | -27.934 | 49.636 | 229.890 | 1.00 | 0.00 | C |
| ATOM | 7838 | CA | LYS | M | 22 | -31.573 | 49.217 | 228.868 | 1.00 | 0.00 | C |
| ATOM | 7839 | CA | ILE | M | 23 | -30.719 | 50.383 | 225.368 | 1.00 | 0.00 | C |
| ATOM | 7840 | CA | VAL | M | 24 | -28.063 | 47.655 | 225.227 | 1.00 | 0.00 | C |
| ATOM | 7841 | CA | GLU | M | 25 | -30.205 | 44.687 | 226.301 | 1.00 | 0.00 | C |
| ATOM | 7842 | CA | ALA | M | 26 | -33.076 | 45.847 | 224.099 | 1.00 | 0.00 | C |
| ATOM | 7843 | CA | ALA | M | 27 | -31.463 | 46.169 | 220.663 | 1.00 | 0.00 | C |
| ATOM | 7844 | CA | ARG | M | 28 | -29.376 | 43.056 | 221.474 | 1.00 | 0.00 | C |
| ATOM | 7845 | CA | ARG | M | 29 | -32.319 | 41.183 | 219.956 | 1.00 | 0.00 | C |
| ATOM | 7846 | CA | SER | M | 30 | -33.035 | 43.078 | 216.729 | 1.00 | 0.00 | C |
| ATOM | 7847 | CA | GLY | M | 31 | -29.746 | 44.353 | 215.302 | 1.00 | 0.00 | C |
| ATOM | 7848 | CA | ALA | M | 32 | -26.013 | 43.727 | 215.681 | 1.00 | 0.00 | C |
| ATOM | 7849 | CA | GLN | M | 33 | -24.702 | 43.058 | 219.190 | 1.00 | 0.00 | C |
| ATOM | 7850 | CA | VAL | M | 34 | -23.924 | 46.609 | 220.310 | 1.00 | 0.00 | C |
| ATOM | 7851 | CA | SER | M | 35 | -20.463 | 48.021 | 221.148 | 1.00 | 0.00 | C |
| ATOM | 7852 | CA | GLY | M | 36 | -21.299 | 47.858 | 224.849 | 1.00 | 0.00 | C |
| ATOM | 7853 | CA | PRO | M | 37 | -21.968 | 51.101 | 226.736 | 1.00 | 0.00 | C |
| ATOM | 7854 | CA | ILE | M | 38 | -18.580 | 52.808 | 226.447 | 1.00 | 0.00 | C |
| ATOM | 7855 | CA | PRO | M | 39 | -17.982 | 55.346 | 229.288 | 1.00 | 0.00 | C |
| ATOM | 7856 | CA | LEU | M | 40 | -16.314 | 58.599 | 228.149 | 1.00 | 0.00 | C |
| ATOM | 7857 | CA | PRO | M | 41 | -14.648 | 61.264 | 230.353 | 1.00 | 0.00 | C |
| ATOM | 7858 | CA | THR | M | 42 | -16.771 | 63.370 | 232.696 | 1.00 | 0.00 | C |
| ATOM | 7859 | CA | ARG | M | 43 | -16.680 | 67.178 | 232.557 | 1.00 | 0.00 | C |
| ATOM | 7860 | CA | VAL | M | 44 | -16.781 | 68.838 | 235.986 | 1.00 | 0.00 | C |
| ATOM | 7861 | CA | ARG | M | 45 | -17.858 | 72.415 | 236.737 | 1.00 | 0.00 | C |
| ATOM | 7862 | CA | ARG | M | 46 | -16.463 | 73.994 | 239.928 | 1.00 | 0.00 | C |
| ATOM | 7863 | CA | PHE | M | 47 | -18.127 | 76.936 | 241.655 | 1.00 | 0.00 | C |
| ATOM | 7864 | CA | THR | M | 48 | -15.943 | 78.237 | 244.425 | 1.00 | 0.00 | C |
| ATOM | 7865 | CA | VAL | M | 49 | -17.971 | 80.625 | 246.524 | 1.00 | 0.00 | C |
| ATOM | 7866 | CA | ILE | M | 50 | -17.257 | 82.697 | 249.639 | 1.00 | 0.00 | C |
| ATOM | 7867 | CA | ARG | M | 51 | -19.296 | 81.140 | 252.457 | 1.00 | 0.00 | C |
| ATOM | 7868 | CA | GLY | M | 52 | -20.879 | 84.161 | 254.040 | 1.00 | 0.00 | C |
| ATOM | 7869 | CA | PRO | M | 53 | -21.932 | 87.566 | 252.723 | 1.00 | 0.00 | C |
| ATOM | 7870 | CA | PHE | M | 54 | -19.801 | 90.611 | 253.573 | 1.00 | 0.00 | C |
| ATOM | 7871 | CA | LYS | M | 55 | -16.034 | 89.896 | 253.793 | 1.00 | 0.00 | C |
| ATOM | 7872 | CA | HIS | M | 56 | -14.402 | 86.776 | 255.275 | 1.00 | 0.00 | C |
| ATOM | 7873 | CA | LYS | M | 57 | -12.448 | 86.282 | 252.017 | 1.00 | 0.00 | C |
| ATOM | 7874 | CA | ASP | M | 58 | -11.291 | 82.867 | 253.219 | 1.00 | 0.00 | C |
| ATOM | 7875 | CA | SER | M | 59 | -14.604 | 81.088 | 253.791 | 1.00 | 0.00 | C |
| ATOM | 7876 | CA | ARG | M | 60 | -15.254 | 79.362 | 250.456 | 1.00 | 0.00 | C |
| ATOM | 7877 | CA | GLU | M | 61 | -16.733 | 75.815 | 250.251 | 1.00 | 0.00 | C |
| ATOM | 7878 | CA | HIS | M | 62 | -16.777 | 74.076 | 246.829 | 1.00 | 0.00 | C |
| ATOM | 7879 | CA | PHE | M | 63 | -19.631 | 73.082 | 244.507 | 1.00 | 0.00 | C |
| ATOM | 7880 | CA | GLU | M | 64 | -19.250 | 70.937 | 241.379 | 1.00 | 0.00 | C |
| ATOM | 7881 | CA | LEU | M | 65 | -21.755 | 69.994 | 238.645 | 1.00 | 0.00 | C |
| ATOM | 7882 | CA | ARG | M | 66 | -20.285 | 66.869 | 237.018 | 1.00 | 0.00 | C |
| ATOM | 7883 | CA | THR | M | 67 | -21.696 | 65.785 | 233.643 | 1.00 | 0.00 | C |
| ATOM | 7884 | CA | HIS | M | 68 | -21.368 | 62.126 | 232.649 | 1.00 | 0.00 | C |
| ATOM | 7885 | CA | ASN | M | 69 | -21.389 | 60.599 | 229.171 | 1.00 | 0.00 | C |
| ATOM | 7886 | CA | ARG | M | 70 | -22.143 | 57.233 | 227.519 | 1.00 | 0.00 | C |
| ATOM | 7887 | CA | LEU | M | 71 | -22.055 | 55.992 | 223.919 | 1.00 | 0.00 | C |
| ATOM | 7888 | CA | VAL | M | 72 | -23.049 | 52.384 | 223.114 | 1.00 | 0.00 | C |
| ATOM | 7889 | CA | ASP | M | 73 | -23.127 | 52.316 | 219.267 | 1.00 | 0.00 | C |
| ATOM | 7890 | CA | ILE | M | 74 | -25.423 | 49.950 | 217.329 | 1.00 | 0.00 | C |
| ATOM | 7891 | CA | ILE | M | 75 | -24.034 | 49.127 | 213.891 | 1.00 | 0.00 | C |
| ATOM | 7892 | CA | ASN | M | 76 | -26.351 | 47.203 | 211.540 | 1.00 | 0.00 | C |
| ATOM | 7893 | CA | PRO | M | 77 | -29.797 | 48.622 | 212.493 | 1.00 | 0.00 | C |
| ATOM | 7894 | CA | ASN | M | 78 | -32.836 | 46.452 | 211.822 | 1.00 | 0.00 | C |
| ATOM | 7895 | CA | ARG | M | 79 | -36.378 | 47.853 | 212.191 | 1.00 | 0.00 | C |

```
ATOM   7896  CA  LYS M  80    -37.052  45.762 215.325  1.00  0.00           C
ATOM   7897  CA  THR M  81    -34.002  47.508 216.790  1.00  0.00           C
ATOM   7898  CA  ILE M  82    -35.678  50.851 216.156  1.00  0.00           C
ATOM   7899  CA  GLU M  83    -38.642  49.053 217.726  1.00  0.00           C
ATOM   7900  CA  GLN M  84    -37.275  47.836 221.056  1.00  0.00           C
ATOM   7901  CA  LEU M  85    -35.832  51.331 221.513  1.00  0.00           C
ATOM   7902  CA  MET M  86    -37.957  53.880 219.626  1.00  0.00           C
ATOM   7903  CA  THR M  87    -40.578  53.941 222.383  1.00  0.00           C
ATOM   7904  CA  LEU M  88    -39.355  52.169 225.518  1.00  0.00           C
ATOM   7905  CA  ASP M  89    -37.374  54.581 227.723  1.00  0.00           C
ATOM   7906  CA  LEU M  90    -37.706  55.452 231.422  1.00  0.00           C
ATOM   7907  CA  PRO M  91    -35.282  57.811 233.304  1.00  0.00           C
ATOM   7908  CA  THR M  92    -35.948  61.549 233.815  1.00  0.00           C
ATOM   7909  CA  GLY M  93    -32.491  62.782 234.774  1.00  0.00           C
ATOM   7910  CA  VAL M  94    -31.262  61.776 231.331  1.00  0.00           C
ATOM   7911  CA  GLU M  95    -31.311  63.358 227.882  1.00  0.00           C
ATOM   7912  CA  ILE M  96    -30.163  61.561 224.728  1.00  0.00           C
ATOM   7913  CA  GLU M  97    -28.827  62.564 221.345  1.00  0.00           C
ATOM   7914  CA  ILE M  98    -28.541  60.092 218.492  1.00  0.00           C
ATOM   7915  CA  LYS M  99    -27.031  60.376 215.031  1.00  0.00           C
ATOM   7916  CA  THR M 100    -27.020  57.184 212.977  1.00  0.00           C
TER    7917      THR M 100
ATOM   7918  CA  LYS N  11     69.076  86.058 284.864  1.00  0.00           C
ATOM   7919  CA  ARG N  12     70.362  84.044 287.835  1.00  0.00           C
ATOM   7920  CA  GLN N  13     69.677  80.483 286.679  1.00  0.00           C
ATOM   7921  CA  VAL N  14     67.417  78.755 289.195  1.00  0.00           C
ATOM   7922  CA  ALA N  15     66.170  75.545 287.575  1.00  0.00           C
ATOM   7923  CA  SER N  16     64.071  74.022 290.379  1.00  0.00           C
ATOM   7924  CA  GLY N  17     61.179  76.072 291.750  1.00  0.00           C
ATOM   7925  CA  ARG N  18     57.512  76.662 292.596  1.00  0.00           C
ATOM   7926  CA  ALA N  19     54.537  77.667 290.436  1.00  0.00           C
ATOM   7927  CA  TYR N  20     51.536  79.288 292.097  1.00  0.00           C
ATOM   7928  CA  ILE N  21     48.299  79.072 290.170  1.00  0.00           C
ATOM   7929  CA  HIS N  22     45.716  81.484 291.535  1.00  0.00           C
ATOM   7930  CA  ALA N  23     42.360  80.793 289.847  1.00  0.00           C
ATOM   7931  CA  SER N  24     39.135  82.801 290.298  1.00  0.00           C
ATOM   7932  CA  TYR N  25     35.846  83.347 288.508  1.00  0.00           C
ATOM   7933  CA  ASN N  26     37.355  86.534 287.085  1.00  0.00           C
ATOM   7934  CA  ASN N  27     40.962  85.840 286.133  1.00  0.00           C
ATOM   7935  CA  THR N  28     43.929  83.518 286.481  1.00  0.00           C
ATOM   7936  CA  ILE N  29     47.361  84.626 287.552  1.00  0.00           C
ATOM   7937  CA  VAL N  30     50.431  82.397 287.665  1.00  0.00           C
ATOM   7938  CA  THR N  31     53.547  83.303 289.604  1.00  0.00           C
ATOM   7939  CA  ILE N  32     56.747  81.258 289.347  1.00  0.00           C
ATOM   7940  CA  THR N  33     59.088  81.116 292.336  1.00  0.00           C
ATOM   7941  CA  ASP N  34     62.434  79.860 293.591  1.00  0.00           C
ATOM   7942  CA  PRO N  35     62.970  76.854 295.924  1.00  0.00           C
ATOM   7943  CA  ASP N  36     61.853  79.002 298.851  1.00  0.00           C
ATOM   7944  CA  GLY N  37     59.156  81.402 297.696  1.00  0.00           C
ATOM   7945  CA  ASN N  38     60.526  84.580 296.118  1.00  0.00           C
ATOM   7946  CA  PRO N  39     58.958  85.181 292.694  1.00  0.00           C
ATOM   7947  CA  ILE N  40     61.005  85.007 289.520  1.00  0.00           C
ATOM   7948  CA  THR N  41     58.277  86.001 287.046  1.00  0.00           C
ATOM   7949  CA  TRP N  42     54.492  86.285 286.881  1.00  0.00           C
ATOM   7950  CA  SER N  43     51.722  86.288 284.265  1.00  0.00           C
ATOM   7951  CA  SER N  44     47.953  86.657 284.132  1.00  0.00           C
ATOM   7952  CA  GLY N  45     44.939  87.156 281.905  1.00  0.00           C
ATOM   7953  CA  GLY N  46     45.751  90.831 281.773  1.00  0.00           C
ATOM   7954  CA  VAL N  47     49.507  90.460 281.330  1.00  0.00           C
ATOM   7955  CA  ILE N  48     48.585  89.043 277.961  1.00  0.00           C
ATOM   7956  CA  GLY N  49     46.016  90.508 275.590  1.00  0.00           C
ATOM   7957  CA  TYR N  50     42.633  90.015 277.307  1.00  0.00           C
ATOM   7958  CA  LYS N  51     41.167  92.877 279.330  1.00  0.00           C
ATOM   7959  CA  GLY N  52     37.718  92.252 280.819  1.00  0.00           C
ATOM   7960  CA  SER N  53     35.671  89.120 280.947  1.00  0.00           C
ATOM   7961  CA  ARG N  54     38.041  87.360 278.512  1.00  0.00           C
ATOM   7962  CA  LYS N  55     40.728  87.598 281.200  1.00  0.00           C
ATOM   7963  CA  GLY N  56     39.129  84.732 283.131  1.00  0.00           C
ATOM   7964  CA  THR N  57     38.443  82.117 280.441  1.00  0.00           C
ATOM   7965  CA  PRO N  58     40.544  78.904 280.526  1.00  0.00           C
ATOM   7966  CA  TYR N  59     42.239  79.906 277.298  1.00  0.00           C
ATOM   7967  CA  ALA N  60     43.713  82.953 279.016  1.00  0.00           C
ATOM   7968  CA  ALA N  61     44.672  80.765 281.963  1.00  0.00           C
ATOM   7969  CA  GLN N  62     46.480  78.647 279.394  1.00  0.00           C
ATOM   7970  CA  LEU N  63     48.289  81.494 277.682  1.00  0.00           C
ATOM   7971  CA  ALA N  64     49.213  82.991 281.061  1.00  0.00           C
ATOM   7972  CA  ALA N  65     50.522  79.642 282.295  1.00  0.00           C
ATOM   7973  CA  LEU N  66     52.765  79.379 279.251  1.00  0.00           C
ATOM   7974  CA  ASP N  67     53.898  83.014 279.417  1.00  0.00           C
ATOM   7975  CA  ALA N  68     54.818  82.284 283.026  1.00  0.00           C
ATOM   7976  CA  ALA N  69     56.889  79.222 282.139  1.00  0.00           C
ATOM   7977  CA  LYS N  70     58.517  80.644 278.991  1.00  0.00           C
ATOM   7978  CA  LYS N  71     59.675  83.745 280.901  1.00  0.00           C
ATOM   7979  CA  ALA N  72     60.869  81.503 283.724  1.00  0.00           C
ATOM   7980  CA  MET N  73     62.728  79.349 281.196  1.00  0.00           C
ATOM   7981  CA  ALA N  74     65.016  82.374 280.851  1.00  0.00           C
ATOM   7982  CA  TYR N  75     66.059  82.252 284.511  1.00  0.00           C
```

```
ATOM   7983  CA  GLY N  76    66.937  78.691 283.526  1.00  0.00           C
ATOM   7984  CA  MET N  77    63.940  77.060 285.238  1.00  0.00           C
ATOM   7985  CA  GLN N  78    63.262  73.406 284.482  1.00  0.00           C
ATOM   7986  CA  SER N  79    61.409  71.604 287.283  1.00  0.00           C
ATOM   7987  CA  VAL N  80    58.532  73.119 289.268  1.00  0.00           C
ATOM   7988  CA  ASP N  81    56.032  72.256 292.009  1.00  0.00           C
ATOM   7989  CA  VAL N  82    52.558  73.517 291.221  1.00  0.00           C
ATOM   7990  CA  ILE N  83    50.317  75.015 293.880  1.00  0.00           C
ATOM   7991  CA  VAL N  84    46.693  75.692 293.073  1.00  0.00           C
ATOM   7992  CA  ARG N  85    44.809  78.292 295.056  1.00  0.00           C
ATOM   7993  CA  GLY N  86    41.112  78.909 294.552  1.00  0.00           C
ATOM   7994  CA  THR N  87    38.594  77.603 292.065  1.00  0.00           C
ATOM   7995  CA  GLY N  88    37.647  79.321 288.869  1.00  0.00           C
ATOM   7996  CA  ALA N  89    37.326  79.736 285.138  1.00  0.00           C
ATOM   7997  CA  GLY N  90    39.879  77.231 283.874  1.00  0.00           C
ATOM   7998  CA  ARG N  91    42.308  76.457 286.670  1.00  0.00           C
ATOM   7999  CA  GLU N  92    42.971  73.015 285.249  1.00  0.00           C
ATOM   8000  CA  GLN N  93    43.950  74.468 281.872  1.00  0.00           C
ATOM   8001  CA  ALA N  94    46.695  76.368 283.669  1.00  0.00           C
ATOM   8002  CA  ILE N  95    47.852  73.222 285.440  1.00  0.00           C
ATOM   8003  CA  ARG N  96    47.989  71.669 281.969  1.00  0.00           C
ATOM   8004  CA  ALA N  97    49.709  74.430 280.023  1.00  0.00           C
ATOM   8005  CA  LEU N  98    52.444  74.056 282.624  1.00  0.00           C
ATOM   8006  CA  GLN N  99    52.866  70.323 282.319  1.00  0.00           C
ATOM   8007  CA  ALA N 100    53.305  70.963 278.601  1.00  0.00           C
ATOM   8008  CA  SER N 101    55.096  74.340 278.636  1.00  0.00           C
ATOM   8009  CA  GLY N 102    58.368  72.464 278.856  1.00  0.00           C
ATOM   8010  CA  LEU N 103    58.878  72.522 282.591  1.00  0.00           C
ATOM   8011  CA  GLN N 104    58.784  69.165 284.274  1.00  0.00           C
ATOM   8012  CA  VAL N 105    55.957  69.425 286.805  1.00  0.00           C
ATOM   8013  CA  LYS N 106    57.033  67.613 289.984  1.00  0.00           C
ATOM   8014  CA  SER N 107    53.668  67.864 291.696  1.00  0.00           C
ATOM   8015  CA  ILE N 108    50.317  69.592 291.765  1.00  0.00           C
ATOM   8016  CA  VAL N 109    48.854  70.612 295.123  1.00  0.00           C
ATOM   8017  CA  ASP N 110    45.625  72.323 296.127  1.00  0.00           C
ATOM   8018  CA  ASP N 111    46.328  74.754 298.962  1.00  0.00           C
ATOM   8019  CA  THR N 112    43.269  76.943 298.451  1.00  0.00           C
ATOM   8020  CA  PRO N 113    42.727  78.796 301.762  1.00  0.00           C
ATOM   8021  CA  VAL N 114    39.558  78.334 303.777  1.00  0.00           C
ATOM   8022  CA  PRO N 115    38.552  79.921 307.062  1.00  0.00           C
ATOM   8023  CA  HIS N 116    37.470  77.881 310.016  1.00  0.00           C
ATOM   8024  CA  ASN N 117    34.677  80.452 309.916  1.00  0.00           C
ATOM   8025  CA  GLY N 118    36.059  83.850 310.751  1.00  0.00           C
ATOM   8026  CA  CYS N 119    34.897  86.915 308.814  1.00  0.00           C
ATOM   8027  CA  ARG N 120    31.342  87.565 307.678  1.00  0.00           C
ATOM   8028  CA  PRO N 121    31.622  87.450 303.919  1.00  0.00           C
ATOM   8029  CA  LYS N 122    30.119  90.200 301.773  1.00  0.00           C
ATOM   8030  CA  LYS N 123    26.453  89.757 300.883  1.00  0.00           C
ATOM   8031  CA  LYS N 124    27.442  88.463 297.459  1.00  0.00           C
ATOM   8032  CA  PHE N 125    28.905  85.384 299.172  1.00  0.00           C
ATOM   8033  CA  ARG N 126    26.545  84.874 302.099  1.00  0.00           C
ATOM   8034  CA  LYS N 127    23.154  83.209 301.585  1.00  0.00           C
ATOM   8035  CA  ALA N 128    24.401  79.899 302.938  1.00  0.00           C
ATOM   8036  CA  SER N 129    24.591  77.980 306.243  1.00  0.00           C
TER    8037          SER N 129
ATOM   8038  CA  PRO O   5   -11.822  85.392 329.943  1.00  0.00           C
ATOM   8039  CA  THR O   6   -11.837  83.256 333.096  1.00  0.00           C
ATOM   8040  CA  ILE O   7   -14.812  83.377 335.440  1.00  0.00           C
ATOM   8041  CA  ASN O   8   -12.646  85.016 338.068  1.00  0.00           C
ATOM   8042  CA  GLN O   9   -11.554  87.517 335.427  1.00  0.00           C
ATOM   8043  CA  LEU O  10   -15.161  88.253 334.544  1.00  0.00           C
ATOM   8044  CA  VAL O  11   -15.728  88.839 338.218  1.00  0.00           C
ATOM   8045  CA  ARG O  12   -12.842  91.281 338.337  1.00  0.00           C
ATOM   8046  CA  LYS O  13   -13.175  93.292 335.147  1.00  0.00           C
ATOM   8047  CA  GLY O  14   -16.526  92.130 333.808  1.00  0.00           C
ATOM   8048  CA  ARG O  15   -18.151  92.826 330.447  1.00  0.00           C
ATOM   8049  CA  GLU O  16   -18.339  96.389 329.129  1.00  0.00           C
ATOM   8050  CA  LYS O  17   -21.723  97.415 327.715  1.00  0.00           C
ATOM   8051  CA  VAL O  18   -21.852  98.874 324.203  1.00  0.00           C
ATOM   8052  CA  ARG O  19   -22.633 102.588 323.702  1.00  0.00           C
ATOM   8053  CA  LYS O  20   -24.556 103.544 320.555  1.00  0.00           C
ATOM   8054  CA  LYS O  21   -23.742 106.987 319.100  1.00  0.00           C
ATOM   8055  CA  SER O  22   -26.504 109.137 317.633  1.00  0.00           C
ATOM   8056  CA  LYS O  23   -26.571 109.801 313.925  1.00  0.00           C
ATOM   8057  CA  VAL O  24   -28.779 112.843 314.233  1.00  0.00           C
ATOM   8058  CA  PRO O  25   -27.757 115.573 316.661  1.00  0.00           C
ATOM   8059  CA  ALA O  26   -31.120 117.268 316.028  1.00  0.00           C
ATOM   8060  CA  LEU O  27   -30.175 117.990 319.645  1.00  0.00           C
ATOM   8061  CA  LYS O  28   -32.751 117.565 322.382  1.00  0.00           C
ATOM   8062  CA  GLY O  29   -32.891 114.136 320.771  1.00  0.00           C
ATOM   8063  CA  ALA O  30   -36.046 115.688 319.349  1.00  0.00           C
ATOM   8064  CA  PRO O  31   -38.208 114.191 316.572  1.00  0.00           C
ATOM   8065  CA  PHE O  32   -37.933 117.365 314.511  1.00  0.00           C
ATOM   8066  CA  ARG O  33   -36.223 120.711 314.658  1.00  0.00           C
ATOM   8067  CA  ARG O  34   -37.024 123.937 312.834  1.00  0.00           C
ATOM   8068  CA  GLY O  35   -34.347 126.143 311.340  1.00  0.00           C
ATOM   8069  CA  VAL O  36   -33.844 128.995 308.928  1.00  0.00           C
```

```
ATOM  8070  CA  CYS O  37   -32.504 128.588 305.417  1.00  0.00           C
ATOM  8071  CA  THR O  38   -29.172 130.240 304.677  1.00  0.00           C
ATOM  8072  CA  VAL O  39   -28.172 128.904 301.296  1.00  0.00           C
ATOM  8073  CA  VAL O  40   -30.311 127.022 298.816  1.00  0.00           C
ATOM  8074  CA  ARG O  41   -27.375 125.510 296.901  1.00  0.00           C
ATOM  8075  CA  THR O  42   -27.277 122.372 294.738  1.00  0.00           C
ATOM  8076  CA  VAL O  43   -24.673 119.695 295.337  1.00  0.00           C
ATOM  8077  CA  THR O  44   -23.525 116.929 293.025  1.00  0.00           C
ATOM  8078  CA  PRO O  45   -23.699 113.158 293.822  1.00  0.00           C
ATOM  8079  CA  LYS O  46   -20.853 110.808 294.765  1.00  0.00           C
ATOM  8080  CA  LYS O  47   -19.079 107.661 293.487  1.00  0.00           C
ATOM  8081  CA  PRO O  48   -21.366 106.751 290.554  1.00  0.00           C
ATOM  8082  CA  ASN O  49   -24.537 108.813 290.656  1.00  0.00           C
ATOM  8083  CA  SER O  50   -24.802 112.170 288.914  1.00  0.00           C
ATOM  8084  CA  ALA O  51   -27.420 114.960 289.106  1.00  0.00           C
ATOM  8085  CA  LEU O  52   -28.188 118.256 290.832  1.00  0.00           C
ATOM  8086  CA  ARG O  53   -29.351 117.410 294.332  1.00  0.00           C
ATOM  8087  CA  LYS O  54   -31.231 120.343 295.876  1.00  0.00           C
ATOM  8088  CA  VAL O  55   -29.873 121.106 299.333  1.00  0.00           C
ATOM  8089  CA  ALA O  56   -30.093 123.835 301.993  1.00  0.00           C
ATOM  8090  CA  LYS O  57   -27.909 125.135 304.836  1.00  0.00           C
ATOM  8091  CA  VAL O  58   -30.102 125.542 307.910  1.00  0.00           C
ATOM  8092  CA  ARG O  59   -29.620 127.439 311.161  1.00  0.00           C
ATOM  8093  CA  LEU O  60   -31.398 125.296 313.766  1.00  0.00           C
ATOM  8094  CA  THR O  61   -33.099 126.442 316.949  1.00  0.00           C
ATOM  8095  CA  SER O  62   -30.892 123.787 318.508  1.00  0.00           C
ATOM  8096  CA  GLY O  63   -27.900 126.022 317.879  1.00  0.00           C
ATOM  8097  CA  TYR O  64   -26.581 123.799 315.072  1.00  0.00           C
ATOM  8098  CA  GLU O  65   -26.005 124.889 311.459  1.00  0.00           C
ATOM  8099  CA  VAL O  66   -26.692 121.959 309.124  1.00  0.00           C
ATOM  8100  CA  THR O  67   -27.238 120.862 305.512  1.00  0.00           C
ATOM  8101  CA  ALA O  68   -30.555 119.226 304.630  1.00  0.00           C
ATOM  8102  CA  TYR O  69   -31.998 117.454 301.603  1.00  0.00           C
ATOM  8103  CA  ILE O  70   -35.099 118.891 299.918  1.00  0.00           C
ATOM  8104  CA  PRO O  71   -37.175 115.940 298.604  1.00  0.00           C
ATOM  8105  CA  GLY O  72   -39.612 116.338 295.750  1.00  0.00           C
ATOM  8106  CA  GLU O  73   -39.810 117.147 292.041  1.00  0.00           C
ATOM  8107  CA  GLY O  74   -39.540 120.895 292.640  1.00  0.00           C
ATOM  8108  CA  HIS O  75   -39.288 123.250 295.640  1.00  0.00           C
ATOM  8109  CA  ASN O  76   -39.827 126.898 296.644  1.00  0.00           C
ATOM  8110  CA  LEU O  77   -37.183 127.388 299.351  1.00  0.00           C
ATOM  8111  CA  GLN O  78   -35.293 130.688 299.560  1.00  0.00           C
ATOM  8112  CA  GLU O  79   -32.603 132.539 301.468  1.00  0.00           C
ATOM  8113  CA  HIS O  80   -34.502 133.076 304.729  1.00  0.00           C
ATOM  8114  CA  SER O  81   -37.304 130.541 304.640  1.00  0.00           C
ATOM  8115  CA  VAL O  82   -38.321 128.847 307.881  1.00  0.00           C
ATOM  8116  CA  VAL O  83   -38.200 125.070 307.612  1.00  0.00           C
ATOM  8117  CA  LEU O  84   -38.601 121.804 309.562  1.00  0.00           C
ATOM  8118  CA  ILE O  85   -35.876 119.117 309.667  1.00  0.00           C
ATOM  8119  CA  ARG O  86   -36.692 115.436 310.101  1.00  0.00           C
ATOM  8120  CA  GLY O  87   -33.464 113.494 310.153  1.00  0.00           C
ATOM  8121  CA  GLY O  88   -32.486 110.989 307.512  1.00  0.00           C
ATOM  8122  CA  ARG O  89   -29.247 111.075 305.594  1.00  0.00           C
ATOM  8123  CA  VAL O  90   -28.802 110.901 301.801  1.00  0.00           C
ATOM  8124  CA  LYS O  91   -26.406 108.180 300.638  1.00  0.00           C
ATOM  8125  CA  ASP O  92   -25.035 110.287 297.742  1.00  0.00           C
ATOM  8126  CA  LEU O  93   -24.539 113.621 299.419  1.00  0.00           C
ATOM  8127  CA  PRO O  94   -21.740 113.401 301.950  1.00  0.00           C
ATOM  8128  CA  GLY O  95   -22.603 115.847 304.693  1.00  0.00           C
ATOM  8129  CA  VAL O  96   -26.373 115.818 304.484  1.00  0.00           C
ATOM  8130  CA  ARG O  97   -27.897 114.164 307.534  1.00  0.00           C
ATOM  8131  CA  TYR O  98   -31.483 115.358 307.551  1.00  0.00           C
ATOM  8132  CA  HIS O  99   -34.347 115.789 305.112  1.00  0.00           C
ATOM  8133  CA  ILE O 100   -36.591 118.831 304.987  1.00  0.00           C
ATOM  8134  CA  VAL O 101   -40.229 118.266 305.816  1.00  0.00           C
ATOM  8135  CA  ARG O 102   -42.285 119.377 302.867  1.00  0.00           C
ATOM  8136  CA  GLY O 103   -45.615 120.934 303.718  1.00  0.00           C
ATOM  8137  CA  VAL O 104   -44.483 122.611 306.918  1.00  0.00           C
ATOM  8138  CA  TYR O 105   -43.683 126.291 307.510  1.00  0.00           C
ATOM  8139  CA  ASP O 106   -42.164 127.871 304.376  1.00  0.00           C
ATOM  8140  CA  ALA O 107   -41.407 124.702 302.441  1.00  0.00           C
ATOM  8141  CA  ALA O 108   -44.438 124.235 300.232  1.00  0.00           C
ATOM  8142  CA  GLY O 109   -45.535 120.747 299.284  1.00  0.00           C
ATOM  8143  CA  VAL O 110   -44.816 119.189 295.915  1.00  0.00           C
ATOM  8144  CA  LYS O 111   -47.185 120.305 293.167  1.00  0.00           C
ATOM  8145  CA  ASP O 112   -48.865 117.580 291.106  1.00  0.00           C
ATOM  8146  CA  ARG O 113   -47.994 114.825 293.561  1.00  0.00           C
ATOM  8147  CA  LYS O 114   -50.613 112.151 292.994  1.00  0.00           C
ATOM  8148  CA  LYS O 115   -49.022 109.289 294.928  1.00  0.00           C
ATOM  8149  CA  SER O 116   -46.929 109.128 298.081  1.00  0.00           C
ATOM  8150  CA  ARG O 117   -48.367 112.506 299.132  1.00  0.00           C
ATOM  8151  CA  SER O 118   -48.132 111.713 302.866  1.00  0.00           C
ATOM  8152  CA  LYS O 119   -44.474 112.522 302.239  1.00  0.00           C
ATOM  8153  CA  TYR O 120   -44.043 115.658 300.078  1.00  0.00           C
ATOM  8154  CA  GLY O 121   -46.895 117.105 302.146  1.00  0.00           C
ATOM  8155  CA  THR O 122   -49.500 117.604 299.394  1.00  0.00           C
ATOM  8156  CA  LYS O 123   -53.238 117.739 300.163  1.00  0.00           C
```

```
ATOM   8157  CA  LYS O 124     -55.758 115.391 298.565  1.00  0.00           C
ATOM   8158  CA  PRO O 125     -56.474 116.451 294.975  1.00  0.00           C
ATOM   8159  CA  LYS O 126     -60.217 116.855 294.402  1.00  0.00           C
ATOM   8160  CA  GLU O 127     -61.004 114.544 291.491  1.00  0.00           C
ATOM   8161  CA  ALA O 128     -63.379 116.376 289.151  1.00  0.00           C
TER    8162      ALA O 128
ATOM   8163  CA  ALA P   2      30.769 112.665 212.975  1.00  0.00           C
ATOM   8164  CA  ARG P   3      29.445 116.130 213.808  1.00  0.00           C
ATOM   8165  CA  ILE P   4      25.974 116.609 212.344  1.00  0.00           C
ATOM   8166  CA  ALA P   5      23.345 119.115 213.527  1.00  0.00           C
ATOM   8167  CA  GLY P   6      24.001 122.242 215.554  1.00  0.00           C
ATOM   8168  CA  VAL P   7      27.115 121.179 217.472  1.00  0.00           C
ATOM   8169  CA  GLU P   8      26.080 117.507 217.300  1.00  0.00           C
ATOM   8170  CA  ILE P   9      28.799 114.891 217.793  1.00  0.00           C
ATOM   8171  CA  PRO P  10      27.409 111.366 218.423  1.00  0.00           C
ATOM   8172  CA  ARG P  11      30.251 108.846 218.373  1.00  0.00           C
ATOM   8173  CA  ASN P  12      31.459 105.247 218.774  1.00  0.00           C
ATOM   8174  CA  LYS P  13      28.061 103.190 218.809  1.00  0.00           C
ATOM   8175  CA  ARG P  14      25.745 101.565 216.298  1.00  0.00           C
ATOM   8176  CA  VAL P  15      24.305 104.268 214.017  1.00  0.00           C
ATOM   8177  CA  ASP P  16      20.711 103.438 214.941  1.00  0.00           C
ATOM   8178  CA  VAL P  17      21.443 103.580 218.676  1.00  0.00           C
ATOM   8179  CA  ALA P  18      23.474 106.714 218.068  1.00  0.00           C
ATOM   8180  CA  LEU P  19      20.809 108.539 216.075  1.00  0.00           C
ATOM   8181  CA  THR P  20      18.590 107.925 219.108  1.00  0.00           C
ATOM   8182  CA  TYR P  21      20.777 110.430 220.945  1.00  0.00           C
ATOM   8183  CA  ILE P  22      19.021 113.129 218.923  1.00  0.00           C
ATOM   8184  CA  TYR P  23      16.003 114.969 220.312  1.00  0.00           C
ATOM   8185  CA  GLY P  24      13.423 113.910 217.757  1.00  0.00           C
ATOM   8186  CA  ILE P  25      14.758 110.446 216.975  1.00  0.00           C
ATOM   8187  CA  GLY P  26      13.662 107.213 218.596  1.00  0.00           C
ATOM   8188  CA  LYS P  27      14.375 103.519 217.984  1.00  0.00           C
ATOM   8189  CA  ALA P  28      11.705 103.869 215.306  1.00  0.00           C
ATOM   8190  CA  ARG P  29      13.027 106.691 213.134  1.00  0.00           C
ATOM   8191  CA  ALA P  30      16.415 105.041 213.694  1.00  0.00           C
ATOM   8192  CA  LYS P  31      15.840 101.938 211.542  1.00  0.00           C
ATOM   8193  CA  GLU P  32      13.954 104.058 209.017  1.00  0.00           C
ATOM   8194  CA  ALA P  33      16.505 106.821 208.409  1.00  0.00           C
ATOM   8195  CA  LEU P  34      18.957 103.944 208.004  1.00  0.00           C
ATOM   8196  CA  GLU P  35      16.412 101.949 206.008  1.00  0.00           C
ATOM   8197  CA  LYS P  36      15.809 104.655 203.394  1.00  0.00           C
ATOM   8198  CA  THR P  37      19.351 106.029 203.310  1.00  0.00           C
ATOM   8199  CA  GLY P  38      20.369 102.392 202.917  1.00  0.00           C
ATOM   8200  CA  ILE P  39      23.082 102.073 205.557  1.00  0.00           C
ATOM   8201  CA  ASN P  40      23.859  99.135 207.789  1.00  0.00           C
ATOM   8202  CA  PRO P  41      22.427 100.053 211.177  1.00  0.00           C
ATOM   8203  CA  ALA P  42      25.101  97.990 212.871  1.00  0.00           C
ATOM   8204  CA  THR P  43      28.025 100.022 211.542  1.00  0.00           C
ATOM   8205  CA  ARG P  44      29.825 101.832 214.375  1.00  0.00           C
ATOM   8206  CA  VAL P  45      29.296 105.576 213.898  1.00  0.00           C
ATOM   8207  CA  LYS P  46      33.074 105.892 213.592  1.00  0.00           C
ATOM   8208  CA  ASP P  47      33.358 103.231 210.872  1.00  0.00           C
ATOM   8209  CA  LEU P  48      30.743 105.127 208.840  1.00  0.00           C
ATOM   8210  CA  THR P  49      31.421 106.690 205.420  1.00  0.00           C
ATOM   8211  CA  GLU P  50      31.500 110.549 204.410  1.00  0.00           C
ATOM   8212  CA  ALA P  51      29.442 110.280 201.249  1.00  0.00           C
ATOM   8213  CA  GLU P  52      26.527 108.603 203.042  1.00  0.00           C
ATOM   8214  CA  VAL P  53      26.762 111.031 205.941  1.00  0.00           C
ATOM   8215  CA  VAL P  54      26.257 113.830 203.423  1.00  0.00           C
ATOM   8216  CA  ARG P  55      23.275 112.340 201.573  1.00  0.00           C
ATOM   8217  CA  LEU P  56      21.778 111.601 205.007  1.00  0.00           C
ATOM   8218  CA  ARG P  57      22.739 114.938 206.494  1.00  0.00           C
ATOM   8219  CA  GLU P  58      21.245 116.666 203.457  1.00  0.00           C
ATOM   8220  CA  TYR P  59      18.210 114.485 202.832  1.00  0.00           C
ATOM   8221  CA  VAL P  60      17.103 114.567 206.471  1.00  0.00           C
ATOM   8222  CA  GLU P  61      17.882 118.158 207.433  1.00  0.00           C
ATOM   8223  CA  ASN P  62      15.979 119.159 204.309  1.00  0.00           C
ATOM   8224  CA  THR P  63      12.836 117.027 204.076  1.00  0.00           C
ATOM   8225  CA  TRP P  64      11.580 117.258 207.671  1.00  0.00           C
ATOM   8226  CA  LYS P  65      11.183 119.968 210.308  1.00  0.00           C
ATOM   8227  CA  LEU P  66      10.919 116.108 211.502  1.00  0.00           C
ATOM   8228  CA  GLU P  67      11.927 116.387 215.159  1.00  0.00           C
ATOM   8229  CA  GLY P  68      14.258 119.061 216.502  1.00  0.00           C
ATOM   8230  CA  GLU P  69      13.125 123.755 216.576  1.00  0.00           C
ATOM   8231  CA  LEU P  70      11.052 120.889 217.993  1.00  0.00           C
ATOM   8232  CA  ARG P  71      11.330 121.866 221.674  1.00  0.00           C
ATOM   8233  CA  ALA P  72      10.314 125.231 220.296  1.00  0.00           C
ATOM   8234  CA  GLU P  73       7.137 123.730 218.848  1.00  0.00           C
ATOM   8235  CA  VAL P  74       6.171 121.641 221.875  1.00  0.00           C
ATOM   8236  CA  ALA P  75       6.820 124.560 224.210  1.00  0.00           C
ATOM   8237  CA  ALA P  76       4.813 126.646 221.763  1.00  0.00           C
ATOM   8238  CA  ASN P  77       1.900 124.182 221.946  1.00  0.00           C
ATOM   8239  CA  ILE P  78       1.652 124.123 225.740  1.00  0.00           C
ATOM   8240  CA  LYS P  79       1.842 127.922 225.797  1.00  0.00           C
ATOM   8241  CA  ARG P  80      -1.283 127.922 223.613  1.00  0.00           C
ATOM   8242  CA  LEU P  81      -3.704 125.656 225.492  1.00  0.00           C
ATOM   8243  CA  MET P  82      -2.318 127.546 228.455  1.00  0.00           C
```

```
ATOM   8244  CA  ASP P  83      -3.212 131.005 227.138  1.00  0.00           C
ATOM   8245  CA  ILE P  84      -6.770 129.989 226.421  1.00  0.00           C
ATOM   8246  CA  GLY P  85      -8.899 129.027 229.427  1.00  0.00           C
ATOM   8247  CA  CYS P  86      -8.260 125.459 228.291  1.00  0.00           C
ATOM   8248  CA  TYR P  87      -8.593 123.246 231.390  1.00  0.00           C
ATOM   8249  CA  ARG P  88      -5.775 121.136 230.005  1.00  0.00           C
ATOM   8250  CA  GLY P  89      -3.825 124.385 229.976  1.00  0.00           C
ATOM   8251  CA  LEU P  90      -4.645 125.141 233.594  1.00  0.00           C
ATOM   8252  CA  ARG P  91      -3.312 121.712 234.527  1.00  0.00           C
ATOM   8253  CA  HIS P  92      -0.032 122.962 233.136  1.00  0.00           C
ATOM   8254  CA  ARG P  93      -0.123 126.217 235.107  1.00  0.00           C
ATOM   8255  CA  ARG P  94      -1.119 124.498 238.353  1.00  0.00           C
ATOM   8256  CA  GLY P  95       1.542 121.950 237.510  1.00  0.00           C
ATOM   8257  CA  LEU P  96      -0.705 118.903 238.018  1.00  0.00           C
ATOM   8258  CA  PRO P  97      -1.133 115.873 235.754  1.00  0.00           C
ATOM   8259  CA  VAL P  98      -3.009 116.664 232.560  1.00  0.00           C
ATOM   8260  CA  ARG P  99      -4.102 113.302 231.161  1.00  0.00           C
ATOM   8261  CA  GLY P 100      -6.747 112.888 233.854  1.00  0.00           C
ATOM   8262  CA  GLN P 101      -5.033 110.806 236.507  1.00  0.00           C
ATOM   8263  CA  ARG P 102      -5.617 110.685 240.266  1.00  0.00           C
ATOM   8264  CA  THR P 103      -4.113 113.526 242.255  1.00  0.00           C
ATOM   8265  CA  ARG P 104      -4.922 112.204 245.729  1.00  0.00           C
ATOM   8266  CA  THR P 105      -1.929 109.907 245.563  1.00  0.00           C
ATOM   8267  CA  ASN P 106       0.715 109.095 242.919  1.00  0.00           C
ATOM   8268  CA  ALA P 107       1.575 112.750 241.706  1.00  0.00           C
ATOM   8269  CA  ARG P 108       5.109 113.569 242.688  1.00  0.00           C
ATOM   8270  CA  THR P 109       6.275 113.795 239.097  1.00  0.00           C
ATOM   8271  CA  ARG P 110       3.872 116.736 238.779  1.00  0.00           C
ATOM   8272  CA  LYS P 111       3.913 118.108 242.341  1.00  0.00           C
ATOM   8273  CA  GLY P 112       7.627 117.932 243.054  1.00  0.00           C
ATOM   8274  CA  PRO P 113       9.165 116.716 246.346  1.00  0.00           C
ATOM   8275  CA  ARG P 114       6.884 115.699 249.204  1.00  0.00           C
ATOM   8276  CA  LYS P 115       5.916 118.689 251.309  1.00  0.00           C
ATOM   8277  CA  THR P 116       5.336 116.941 254.646  1.00  0.00           C
ATOM   8278  CA  VAL P 117       3.049 118.544 257.266  1.00  0.00           C
ATOM   8279  CA  ALA P 118       2.057 117.713 260.855  1.00  0.00           C
ATOM   8280  CA  GLY P 119      -0.703 115.109 261.198  1.00  0.00           C
ATOM   8281  CA  LYS P 120      -3.000 112.734 263.092  1.00  0.00           C
ATOM   8282  CA  LYS P 121      -1.392 109.608 264.599  1.00  0.00           C
ATOM   8283  CA  LYS P 122      -3.532 106.987 266.405  1.00  0.00           C
ATOM   8284  CA  ALA P 123      -6.138 106.389 263.706  1.00  0.00           C
ATOM   8285  CA  PRO P 124      -4.462 103.503 261.795  1.00  0.00           C
ATOM   8286  CA  ARG P 125      -3.373 105.566 258.797  1.00  0.00           C
ATOM   8287  CA  LYS P 126      -1.407 102.455 257.857  1.00  0.00           C
TER    8288          LYS P 126
ATOM   8289  CA  ALA Q   2     -33.208  97.367 246.064  1.00  0.00           C
ATOM   8290  CA  ARG Q   3     -36.370  99.440 246.068  1.00  0.00           C
ATOM   8291  CA  LYS Q   4     -39.275  98.327 243.879  1.00  0.00           C
ATOM   8292  CA  ALA Q   5     -38.974 101.784 242.361  1.00  0.00           C
ATOM   8293  CA  LEU Q   6     -35.360 101.096 241.357  1.00  0.00           C
ATOM   8294  CA  ILE Q   7     -36.226  97.848 239.629  1.00  0.00           C
ATOM   8295  CA  GLU Q   8     -37.084  99.808 236.511  1.00  0.00           C
ATOM   8296  CA  LYS Q   9     -34.177  97.771 235.207  1.00  0.00           C
ATOM   8297  CA  ALA Q  10     -36.646  95.303 233.749  1.00  0.00           C
ATOM   8298  CA  LYS Q  11     -38.000  98.292 231.794  1.00  0.00           C
ATOM   8299  CA  ARG Q  12     -35.830  97.493 228.755  1.00  0.00           C
ATOM   8300  CA  THR Q  13     -36.303 101.045 227.460  1.00  0.00           C
ATOM   8301  CA  PRO Q  14     -32.653 101.865 228.004  1.00  0.00           C
ATOM   8302  CA  LYS Q  15     -33.220 104.810 225.665  1.00  0.00           C
ATOM   8303  CA  PHE Q  16     -29.615 103.750 224.977  1.00  0.00           C
ATOM   8304  CA  LYS Q  17     -28.612 100.128 225.687  1.00  0.00           C
ATOM   8305  CA  VAL Q  18     -25.708 101.097 227.942  1.00  0.00           C
ATOM   8306  CA  ARG Q  19     -28.027 101.983 230.818  1.00  0.00           C
ATOM   8307  CA  ALA Q  20     -28.889  98.269 231.208  1.00  0.00           C
ATOM   8308  CA  TYR Q  21     -27.839  96.447 234.402  1.00  0.00           C
ATOM   8309  CA  THR Q  22     -27.989  92.821 235.597  1.00  0.00           C
ATOM   8310  CA  ARG Q  23     -29.729  92.993 239.043  1.00  0.00           C
ATOM   8311  CA  CYS Q  24     -30.425  89.945 241.182  1.00  0.00           C
ATOM   8312  CA  VAL Q  25     -33.353  87.924 239.954  1.00  0.00           C
ATOM   8313  CA  ARG Q  26     -34.291  87.207 243.561  1.00  0.00           C
ATOM   8314  CA  CYS Q  27     -33.128  89.957 245.930  1.00  0.00           C
ATOM   8315  CA  GLY Q  28     -32.318  92.721 243.460  1.00  0.00           C
ATOM   8316  CA  ARG Q  29     -28.742  92.764 244.685  1.00  0.00           C
ATOM   8317  CA  ALA Q  30     -27.365  94.754 241.751  1.00  0.00           C
ATOM   8318  CA  ARG Q  31     -23.874  94.786 243.297  1.00  0.00           C
ATOM   8319  CA  SER Q  32     -22.429  91.376 242.465  1.00  0.00           C
ATOM   8320  CA  VAL Q  33     -24.811  89.468 240.225  1.00  0.00           C
ATOM   8321  CA  TYR Q  34     -23.374  86.476 238.404  1.00  0.00           C
ATOM   8322  CA  ARG Q  35     -24.602  86.061 234.795  1.00  0.00           C
ATOM   8323  CA  PHE Q  36     -24.866  82.283 234.513  1.00  0.00           C
ATOM   8324  CA  PHE Q  37     -27.440  82.390 237.307  1.00  0.00           C
ATOM   8325  CA  GLY Q  38     -29.082  85.807 237.327  1.00  0.00           C
ATOM   8326  CA  LEU Q  39     -28.363  85.569 241.040  1.00  0.00           C
ATOM   8327  CA  CYS Q  40     -26.114  87.710 243.291  1.00  0.00           C
ATOM   8328  CA  ARG Q  41     -23.112  86.262 245.173  1.00  0.00           C
ATOM   8329  CA  ILE Q  42     -25.323  85.753 248.237  1.00  0.00           C
ATOM   8330  CA  CYS Q  43     -28.385  83.999 246.798  1.00  0.00           C
```

| | | | | | | | | | | |
|---|---|---|---|---|---|---|---|---|---|---|
| ATOM | 8331 | CA | LEU | Q | 44 | -26.031 | 81.919 | 244.653 | 1.00 | 0.00 | C |
| ATOM | 8332 | CA | ARG | Q | 45 | -24.463 | 80.711 | 247.927 | 1.00 | 0.00 | C |
| ATOM | 8333 | CA | GLU | Q | 46 | -27.816 | 80.269 | 249.711 | 1.00 | 0.00 | C |
| ATOM | 8334 | CA | LEU | Q | 47 | -29.251 | 78.124 | 246.917 | 1.00 | 0.00 | C |
| ATOM | 8335 | CA | ALA | Q | 48 | -26.069 | 76.153 | 246.355 | 1.00 | 0.00 | C |
| ATOM | 8336 | CA | HIS | Q | 49 | -26.497 | 75.080 | 249.981 | 1.00 | 0.00 | C |
| ATOM | 8337 | CA | LYS | Q | 50 | -30.079 | 73.930 | 249.483 | 1.00 | 0.00 | C |
| ATOM | 8338 | CA | GLY | Q | 51 | -29.384 | 71.952 | 246.317 | 1.00 | 0.00 | C |
| ATOM | 8339 | CA | GLN | Q | 52 | -31.656 | 74.056 | 244.161 | 1.00 | 0.00 | C |
| ATOM | 8340 | CA | LEU | Q | 53 | -28.704 | 74.766 | 241.882 | 1.00 | 0.00 | C |
| ATOM | 8341 | CA | PRO | Q | 54 | -28.620 | 71.701 | 239.561 | 1.00 | 0.00 | C |
| ATOM | 8342 | CA | GLY | Q | 55 | -25.223 | 70.054 | 239.600 | 1.00 | 0.00 | C |
| ATOM | 8343 | CA | VAL | Q | 56 | -23.637 | 72.891 | 241.592 | 1.00 | 0.00 | C |
| ATOM | 8344 | CA | ARG | Q | 57 | -21.625 | 70.986 | 244.201 | 1.00 | 0.00 | C |
| ATOM | 8345 | CA | LYS | Q | 58 | -19.027 | 72.460 | 246.572 | 1.00 | 0.00 | C |
| ATOM | 8346 | CA | ALA | Q | 59 | -15.551 | 72.929 | 245.106 | 1.00 | 0.00 | C |
| ATOM | 8347 | CA | SER | Q | 60 | -12.339 | 71.693 | 246.704 | 1.00 | 0.00 | C |
| ATOM | 8348 | CA | TRP | Q | 61 | -8.913 | 70.640 | 245.450 | 1.00 | 0.00 | C |
| TER | 8349 | | TRP | Q | 61 | | | | | | |
| ATOM | 8350 | CA | PRO | R | 2 | 31.158 | 77.128 | 347.740 | 1.00 | 0.00 | C |
| ATOM | 8351 | CA | ILE | R | 3 | 29.545 | 75.254 | 350.619 | 1.00 | 0.00 | C |
| ATOM | 8352 | CA | THR | R | 4 | 31.264 | 72.012 | 351.643 | 1.00 | 0.00 | C |
| ATOM | 8353 | CA | LYS | R | 5 | 29.240 | 68.894 | 352.495 | 1.00 | 0.00 | C |
| ATOM | 8354 | CA | GLU | R | 6 | 30.601 | 69.680 | 355.955 | 1.00 | 0.00 | C |
| ATOM | 8355 | CA | GLU | R | 7 | 29.404 | 73.274 | 355.973 | 1.00 | 0.00 | C |
| ATOM | 8356 | CA | LYS | R | 8 | 26.103 | 71.861 | 354.743 | 1.00 | 0.00 | C |
| ATOM | 8357 | CA | GLN | R | 9 | 25.336 | 68.965 | 357.060 | 1.00 | 0.00 | C |
| ATOM | 8358 | CA | LYS | R | 10 | 26.613 | 71.133 | 359.911 | 1.00 | 0.00 | C |
| ATOM | 8359 | CA | VAL | R | 11 | 23.582 | 73.346 | 359.264 | 1.00 | 0.00 | C |
| ATOM | 8360 | CA | ILE | R | 12 | 21.264 | 70.450 | 358.540 | 1.00 | 0.00 | C |
| ATOM | 8361 | CA | GLN | R | 13 | 22.032 | 68.806 | 361.867 | 1.00 | 0.00 | C |
| ATOM | 8362 | CA | GLU | R | 14 | 22.004 | 72.180 | 363.612 | 1.00 | 0.00 | C |
| ATOM | 8363 | CA | PHE | R | 15 | 18.378 | 72.706 | 362.591 | 1.00 | 0.00 | C |
| ATOM | 8364 | CA | ALA | R | 16 | 16.827 | 69.281 | 362.103 | 1.00 | 0.00 | C |
| ATOM | 8365 | CA | ARG | R | 17 | 13.697 | 68.736 | 364.222 | 1.00 | 0.00 | C |
| ATOM | 8366 | CA | PHE | R | 18 | 14.961 | 65.274 | 365.123 | 1.00 | 0.00 | C |
| ATOM | 8367 | CA | PRO | R | 19 | 17.685 | 62.690 | 364.331 | 1.00 | 0.00 | C |
| ATOM | 8368 | CA | GLY | R | 20 | 17.582 | 62.282 | 360.571 | 1.00 | 0.00 | C |
| ATOM | 8369 | CA | ASP | R | 21 | 15.460 | 65.315 | 359.766 | 1.00 | 0.00 | C |
| ATOM | 8370 | CA | THR | R | 22 | 16.559 | 66.455 | 356.311 | 1.00 | 0.00 | C |
| ATOM | 8371 | CA | GLY | R | 23 | 13.552 | 68.355 | 354.975 | 1.00 | 0.00 | C |
| ATOM | 8372 | CA | SER | R | 24 | 11.786 | 70.170 | 357.787 | 1.00 | 0.00 | C |
| ATOM | 8373 | CA | THR | R | 25 | 10.812 | 73.716 | 356.966 | 1.00 | 0.00 | C |
| ATOM | 8374 | CA | GLU | R | 26 | 13.297 | 74.829 | 359.600 | 1.00 | 0.00 | C |
| ATOM | 8375 | CA | VAL | R | 27 | 16.099 | 72.993 | 357.800 | 1.00 | 0.00 | C |
| ATOM | 8376 | CA | GLN | R | 28 | 15.200 | 74.117 | 354.304 | 1.00 | 0.00 | C |
| ATOM | 8377 | CA | VAL | R | 29 | 14.905 | 77.709 | 355.440 | 1.00 | 0.00 | C |
| ATOM | 8378 | CA | ALA | R | 30 | 18.285 | 77.365 | 357.137 | 1.00 | 0.00 | C |
| ATOM | 8379 | CA | LEU | R | 31 | 20.005 | 75.967 | 354.025 | 1.00 | 0.00 | C |
| ATOM | 8380 | CA | LEU | R | 32 | 18.438 | 78.720 | 351.892 | 1.00 | 0.00 | C |
| ATOM | 8381 | CA | THR | R | 33 | 19.513 | 81.388 | 354.332 | 1.00 | 0.00 | C |
| ATOM | 8382 | CA | LEU | R | 34 | 22.972 | 79.947 | 353.908 | 1.00 | 0.00 | C |
| ATOM | 8383 | CA | ARG | R | 35 | 22.953 | 79.931 | 350.110 | 1.00 | 0.00 | C |
| ATOM | 8384 | CA | ILE | R | 36 | 21.438 | 83.411 | 350.080 | 1.00 | 0.00 | C |
| ATOM | 8385 | CA | ASN | R | 37 | 24.074 | 84.929 | 352.292 | 1.00 | 0.00 | C |
| ATOM | 8386 | CA | ARG | R | 38 | 26.893 | 83.450 | 350.228 | 1.00 | 0.00 | C |
| ATOM | 8387 | CA | LEU | R | 39 | 25.211 | 84.746 | 347.070 | 1.00 | 0.00 | C |
| ATOM | 8388 | CA | SER | R | 40 | 24.364 | 88.109 | 348.603 | 1.00 | 0.00 | C |
| ATOM | 8389 | CA | GLU | R | 41 | 28.066 | 88.164 | 349.430 | 1.00 | 0.00 | C |
| ATOM | 8390 | CA | HIS | R | 42 | 29.336 | 87.127 | 346.002 | 1.00 | 0.00 | C |
| ATOM | 8391 | CA | LEU | R | 43 | 27.092 | 89.892 | 344.700 | 1.00 | 0.00 | C |
| ATOM | 8392 | CA | LYS | R | 44 | 28.414 | 92.642 | 346.991 | 1.00 | 0.00 | C |
| ATOM | 8393 | CA | VAL | R | 45 | 31.280 | 92.366 | 344.550 | 1.00 | 0.00 | C |
| ATOM | 8394 | CA | HIS | R | 46 | 30.305 | 91.413 | 340.986 | 1.00 | 0.00 | C |
| ATOM | 8395 | CA | LYS | R | 47 | 27.442 | 93.889 | 340.902 | 1.00 | 0.00 | C |
| ATOM | 8396 | CA | LYS | R | 48 | 27.237 | 93.105 | 337.172 | 1.00 | 0.00 | C |
| ATOM | 8397 | CA | ASP | R | 49 | 26.620 | 89.360 | 337.505 | 1.00 | 0.00 | C |
| ATOM | 8398 | CA | HIS | R | 50 | 22.893 | 89.931 | 337.043 | 1.00 | 0.00 | C |
| ATOM | 8399 | CA | HIS | R | 51 | 22.403 | 86.381 | 335.895 | 1.00 | 0.00 | C |
| ATOM | 8400 | CA | SER | R | 52 | 23.310 | 85.104 | 339.335 | 1.00 | 0.00 | C |
| ATOM | 8401 | CA | HIS | R | 53 | 21.142 | 87.789 | 340.905 | 1.00 | 0.00 | C |
| ATOM | 8402 | CA | ARG | R | 54 | 17.995 | 86.228 | 339.465 | 1.00 | 0.00 | C |
| ATOM | 8403 | CA | GLY | R | 55 | 19.068 | 83.060 | 341.219 | 1.00 | 0.00 | C |
| ATOM | 8404 | CA | LEU | R | 56 | 19.010 | 85.072 | 344.440 | 1.00 | 0.00 | C |
| ATOM | 8405 | CA | LEU | R | 57 | 15.605 | 86.607 | 343.733 | 1.00 | 0.00 | C |
| ATOM | 8406 | CA | MET | R | 58 | 14.384 | 83.053 | 343.562 | 1.00 | 0.00 | C |
| ATOM | 8407 | CA | MET | R | 59 | 16.137 | 81.750 | 346.686 | 1.00 | 0.00 | C |
| ATOM | 8408 | CA | VAL | R | 60 | 14.814 | 84.682 | 348.663 | 1.00 | 0.00 | C |
| ATOM | 8409 | CA | GLY | R | 61 | 11.504 | 83.978 | 347.018 | 1.00 | 0.00 | C |
| ATOM | 8410 | CA | GLN | R | 62 | 11.251 | 80.291 | 347.897 | 1.00 | 0.00 | C |
| ATOM | 8411 | CA | ARG | R | 63 | 12.336 | 81.132 | 351.414 | 1.00 | 0.00 | C |
| ATOM | 8412 | CA | ARG | R | 64 | 9.906 | 83.915 | 352.202 | 1.00 | 0.00 | C |
| ATOM | 8413 | CA | ARG | R | 65 | 7.306 | 81.515 | 350.882 | 1.00 | 0.00 | C |
| ATOM | 8414 | CA | LEU | R | 66 | 8.257 | 78.589 | 353.165 | 1.00 | 0.00 | C |
| ATOM | 8415 | CA | LEU | R | 67 | 8.384 | 80.949 | 356.133 | 1.00 | 0.00 | C |
| ATOM | 8416 | CA | ARG | R | 68 | 4.951 | 82.237 | 355.221 | 1.00 | 0.00 | C |
| ATOM | 8417 | CA | TYR | R | 69 | 3.863 | 78.613 | 355.533 | 1.00 | 0.00 | C |

| | | | | | | | | | | |
|---|---|---|---|---|---|---|---|---|---|---|
| ATOM | 8418 | CA | LEU | R | 70 | 5.432 | 78.338 | 358.993 | 1.00 | 0.00 | C |
| ATOM | 8419 | CA | GLN | R | 71 | 3.434 | 81.168 | 360.622 | 1.00 | 0.00 | C |
| ATOM | 8420 | CA | ARG | R | 72 | 0.206 | 79.849 | 359.184 | 1.00 | 0.00 | C |
| ATOM | 8421 | CA | GLU | R | 73 | 0.961 | 76.440 | 360.743 | 1.00 | 0.00 | C |
| ATOM | 8422 | CA | ASP | R | 74 | 3.086 | 76.763 | 363.875 | 1.00 | 0.00 | C |
| ATOM | 8423 | CA | PRO | R | 75 | 3.401 | 80.502 | 364.717 | 1.00 | 0.00 | C |
| ATOM | 8424 | CA | GLU | R | 76 | 5.832 | 79.487 | 367.480 | 1.00 | 0.00 | C |
| ATOM | 8425 | CA | ARG | R | 77 | 8.466 | 77.539 | 365.521 | 1.00 | 0.00 | C |
| ATOM | 8426 | CA | TYR | R | 78 | 8.251 | 80.503 | 363.183 | 1.00 | 0.00 | C |
| ATOM | 8427 | CA | ARG | R | 79 | 9.367 | 83.216 | 365.607 | 1.00 | 0.00 | C |
| ATOM | 8428 | CA | ALA | R | 80 | 11.820 | 80.551 | 366.724 | 1.00 | 0.00 | C |
| ATOM | 8429 | CA | LEU | R | 81 | 13.375 | 80.018 | 363.298 | 1.00 | 0.00 | C |
| ATOM | 8430 | CA | ILE | R | 82 | 13.605 | 83.735 | 362.549 | 1.00 | 0.00 | C |
| ATOM | 8431 | CA | GLU | R | 83 | 15.313 | 84.760 | 365.794 | 1.00 | 0.00 | C |
| ATOM | 8432 | CA | LYS | R | 84 | 17.747 | 81.873 | 365.379 | 1.00 | 0.00 | C |
| ATOM | 8433 | CA | LEU | R | 85 | 18.634 | 82.243 | 361.682 | 1.00 | 0.00 | C |
| ATOM | 8434 | CA | GLY | R | 86 | 18.390 | 85.975 | 362.260 | 1.00 | 0.00 | C |
| ATOM | 8435 | CA | ILE | R | 87 | 15.974 | 86.719 | 359.392 | 1.00 | 0.00 | C |
| ATOM | 8436 | CA | ARG | R | 88 | 14.084 | 89.969 | 358.634 | 1.00 | 0.00 | C |
| ATOM | 8437 | CA | GLY | R | 89 | 15.826 | 93.284 | 359.274 | 1.00 | 0.00 | C |
| TER | 8438 | | GLY | R | 89 | | | | | | |
| ATOM | 8439 | CA | MET | S | 1 | -57.923 | 109.347 | 364.728 | 1.00 | 0.00 | C |
| ATOM | 8440 | CA | VAL | S | 2 | -58.641 | 105.926 | 363.234 | 1.00 | 0.00 | C |
| ATOM | 8441 | CA | LYS | S | 3 | -61.892 | 105.700 | 361.312 | 1.00 | 0.00 | C |
| ATOM | 8442 | CA | ILE | S | 4 | -64.238 | 103.258 | 359.583 | 1.00 | 0.00 | C |
| ATOM | 8443 | CA | ARG | S | 5 | -65.432 | 104.932 | 356.412 | 1.00 | 0.00 | C |
| ATOM | 8444 | CA | LEU | S | 6 | -66.128 | 104.636 | 352.705 | 1.00 | 0.00 | C |
| ATOM | 8445 | CA | ALA | S | 7 | -63.520 | 104.855 | 349.917 | 1.00 | 0.00 | C |
| ATOM | 8446 | CA | ARG | S | 8 | -64.551 | 105.781 | 346.392 | 1.00 | 0.00 | C |
| ATOM | 8447 | CA | PHE | S | 9 | -63.507 | 102.978 | 344.095 | 1.00 | 0.00 | C |
| ATOM | 8448 | CA | GLY | S | 10 | -66.163 | 102.967 | 341.436 | 1.00 | 0.00 | C |
| ATOM | 8449 | CA | SER | S | 11 | -65.834 | 105.065 | 338.311 | 1.00 | 0.00 | C |
| ATOM | 8450 | CA | LYS | S | 12 | -67.871 | 107.847 | 336.758 | 1.00 | 0.00 | C |
| ATOM | 8451 | CA | HIS | S | 13 | -71.509 | 107.347 | 337.668 | 1.00 | 0.00 | C |
| ATOM | 8452 | CA | ASN | S | 14 | -70.544 | 103.853 | 338.750 | 1.00 | 0.00 | C |
| ATOM | 8453 | CA | PRO | S | 15 | -69.439 | 104.521 | 342.359 | 1.00 | 0.00 | C |
| ATOM | 8454 | CA | HIS | S | 16 | -68.410 | 101.542 | 344.491 | 1.00 | 0.00 | C |
| ATOM | 8455 | CA | TYR | S | 17 | -67.181 | 102.200 | 348.010 | 1.00 | 0.00 | C |
| ATOM | 8456 | CA | ARG | S | 18 | -64.971 | 100.113 | 350.283 | 1.00 | 0.00 | C |
| ATOM | 8457 | CA | ILE | S | 19 | -65.859 | 100.129 | 353.976 | 1.00 | 0.00 | C |
| ATOM | 8458 | CA | VAL | S | 20 | -62.367 | 100.718 | 355.314 | 1.00 | 0.00 | C |
| ATOM | 8459 | CA | VAL | S | 21 | -60.355 | 101.199 | 358.514 | 1.00 | 0.00 | C |
| ATOM | 8460 | CA | THR | S | 22 | -57.976 | 104.097 | 357.860 | 1.00 | 0.00 | C |
| ATOM | 8461 | CA | ASP | S | 23 | -56.399 | 107.022 | 359.726 | 1.00 | 0.00 | C |
| ATOM | 8462 | CA | ALA | S | 24 | -58.613 | 110.153 | 359.652 | 1.00 | 0.00 | C |
| ATOM | 8463 | CA | ARG | S | 25 | -55.817 | 112.068 | 357.932 | 1.00 | 0.00 | C |
| ATOM | 8464 | CA | ARG | S | 26 | -55.409 | 110.022 | 354.714 | 1.00 | 0.00 | C |
| ATOM | 8465 | CA | LYS | S | 27 | -56.763 | 110.813 | 351.287 | 1.00 | 0.00 | C |
| ATOM | 8466 | CA | ARG | S | 28 | -60.217 | 109.270 | 351.188 | 1.00 | 0.00 | C |
| ATOM | 8467 | CA | ASP | S | 29 | -58.914 | 107.047 | 348.420 | 1.00 | 0.00 | C |
| ATOM | 8468 | CA | GLY | S | 30 | -55.522 | 106.589 | 350.029 | 1.00 | 0.00 | C |
| ATOM | 8469 | CA | LYS | S | 31 | -53.866 | 103.665 | 351.781 | 1.00 | 0.00 | C |
| ATOM | 8470 | CA | TYR | S | 32 | -56.145 | 102.140 | 354.390 | 1.00 | 0.00 | C |
| ATOM | 8471 | CA | ILE | S | 33 | -55.274 | 99.960 | 357.383 | 1.00 | 0.00 | C |
| ATOM | 8472 | CA | GLU | S | 34 | -57.687 | 97.180 | 356.478 | 1.00 | 0.00 | C |
| ATOM | 8473 | CA | LYS | S | 35 | -60.701 | 96.513 | 354.300 | 1.00 | 0.00 | C |
| ATOM | 8474 | CA | ILE | S | 36 | -63.747 | 95.217 | 356.140 | 1.00 | 0.00 | C |
| ATOM | 8475 | CA | GLY | S | 37 | -66.536 | 95.579 | 353.648 | 1.00 | 0.00 | C |
| ATOM | 8476 | CA | TYR | S | 38 | -67.846 | 97.117 | 350.471 | 1.00 | 0.00 | C |
| ATOM | 8477 | CA | TYR | S | 39 | -70.959 | 98.951 | 349.378 | 1.00 | 0.00 | C |
| ATOM | 8478 | CA | ASP | S | 40 | -72.751 | 99.365 | 346.044 | 1.00 | 0.00 | C |
| ATOM | 8479 | CA | PRO | S | 41 | -74.858 | 102.564 | 346.295 | 1.00 | 0.00 | C |
| ATOM | 8480 | CA | ARG | S | 42 | -77.036 | 101.548 | 343.386 | 1.00 | 0.00 | C |
| ATOM | 8481 | CA | LYS | S | 43 | -77.600 | 97.948 | 344.408 | 1.00 | 0.00 | C |
| ATOM | 8482 | CA | THR | S | 44 | -76.763 | 96.910 | 340.824 | 1.00 | 0.00 | C |
| ATOM | 8483 | CA | THR | S | 45 | -76.499 | 93.332 | 342.074 | 1.00 | 0.00 | C |
| ATOM | 8484 | CA | PRO | S | 46 | -78.278 | 91.199 | 344.732 | 1.00 | 0.00 | C |
| ATOM | 8485 | CA | ASP | S | 47 | -75.092 | 91.393 | 346.736 | 1.00 | 0.00 | C |
| ATOM | 8486 | CA | TRP | S | 48 | -74.694 | 95.141 | 347.213 | 1.00 | 0.00 | C |
| ATOM | 8487 | CA | LEU | S | 49 | -73.357 | 95.213 | 350.765 | 1.00 | 0.00 | C |
| ATOM | 8488 | CA | LYS | S | 50 | -71.007 | 92.838 | 352.577 | 1.00 | 0.00 | C |
| ATOM | 8489 | CA | VAL | S | 51 | -69.648 | 93.842 | 355.974 | 1.00 | 0.00 | C |
| ATOM | 8490 | CA | ASP | S | 52 | -67.723 | 91.183 | 357.900 | 1.00 | 0.00 | C |
| ATOM | 8491 | CA | VAL | S | 53 | -69.254 | 92.303 | 361.176 | 1.00 | 0.00 | C |
| ATOM | 8492 | CA | GLU | S | 54 | -66.621 | 90.256 | 362.963 | 1.00 | 0.00 | C |
| ATOM | 8493 | CA | ARG | S | 55 | -63.758 | 92.638 | 362.190 | 1.00 | 0.00 | C |
| ATOM | 8494 | CA | ALA | S | 56 | -65.734 | 95.870 | 362.484 | 1.00 | 0.00 | C |
| ATOM | 8495 | CA | ARG | S | 57 | -66.563 | 95.069 | 366.101 | 1.00 | 0.00 | C |
| ATOM | 8496 | CA | TYR | S | 58 | -62.853 | 94.587 | 366.538 | 1.00 | 0.00 | C |
| ATOM | 8497 | CA | TRP | S | 59 | -61.953 | 98.014 | 365.222 | 1.00 | 0.00 | C |
| ATOM | 8498 | CA | LEU | S | 60 | -64.719 | 99.707 | 367.198 | 1.00 | 0.00 | C |
| ATOM | 8499 | CA | SER | S | 61 | -63.259 | 97.670 | 370.040 | 1.00 | 0.00 | C |
| ATOM | 8500 | CA | VAL | S | 62 | -60.376 | 100.144 | 369.852 | 1.00 | 0.00 | C |
| ATOM | 8501 | CA | GLY | S | 63 | -61.415 | 103.652 | 368.891 | 1.00 | 0.00 | C |
| ATOM | 8502 | CA | ALA | S | 64 | -62.509 | 103.164 | 365.303 | 1.00 | 0.00 | C |
| ATOM | 8503 | CA | GLN | S | 65 | -64.980 | 105.988 | 364.740 | 1.00 | 0.00 | C |
| ATOM | 8504 | CA | PRO | S | 66 | -67.364 | 105.380 | 361.840 | 1.00 | 0.00 | C |

```
ATOM   8505  CA  THR S  67     -68.421 108.040 359.355  1.00  0.00           C
ATOM   8506  CA  ASP S  68     -72.142 108.504 359.642  1.00  0.00           C
ATOM   8507  CA  THR S  69     -72.909 106.758 356.329  1.00  0.00           C
ATOM   8508  CA  ALA S  70     -70.401 104.055 357.243  1.00  0.00           C
ATOM   8509  CA  ARG S  71     -72.177 103.399 360.548  1.00  0.00           C
ATOM   8510  CA  ARG S  72     -75.541 103.224 358.802  1.00  0.00           C
ATOM   8511  CA  LEU S  73     -74.217 100.416 356.596  1.00  0.00           C
ATOM   8512  CA  LEU S  74     -72.599  98.721 359.543  1.00  0.00           C
ATOM   8513  CA  ARG S  75     -75.958  98.883 361.292  1.00  0.00           C
ATOM   8514  CA  GLN S  76     -77.640  97.260 358.287  1.00  0.00           C
ATOM   8515  CA  ALA S  77     -75.280  94.294 358.597  1.00  0.00           C
ATOM   8516  CA  GLY S  78     -76.212  94.349 362.241  1.00  0.00           C
ATOM   8517  CA  VAL S  79     -72.818  95.234 363.637  1.00  0.00           C
ATOM   8518  CA  PHE S  80     -74.592  96.884 366.526  1.00  0.00           C
ATOM   8519  CA  ARG S  81     -77.642  94.657 367.029  1.00  0.00           C
ATOM   8520  CA  GLN S  82     -76.780  93.379 370.490  1.00  0.00           C
ATOM   8521  CA  GLU S  83     -79.830  91.097 370.789  1.00  0.00           C
TER    8522      GLU S  83
ATOM   8523  CA  PRO T   2     -33.085  92.739 367.029  1.00  0.00           C
ATOM   8524  CA  LYS T   3     -30.149  95.033 367.471  1.00  0.00           C
ATOM   8525  CA  LYS T   4     -27.857  93.682 364.737  1.00  0.00           C
ATOM   8526  CA  VAL T   5     -24.855  91.730 366.018  1.00  0.00           C
ATOM   8527  CA  LEU T   6     -21.675  91.317 363.971  1.00  0.00           C
ATOM   8528  CA  THR T   7     -18.292  89.585 364.241  1.00  0.00           C
ATOM   8529  CA  GLY T   8     -15.012  90.909 362.968  1.00  0.00           C
ATOM   8530  CA  VAL T   9     -11.415  91.641 363.847  1.00  0.00           C
ATOM   8531  CA  VAL T  10      -9.923  94.662 365.508  1.00  0.00           C
ATOM   8532  CA  VAL T  11      -7.622  96.003 362.832  1.00  0.00           C
ATOM   8533  CA  SER T  12      -6.990  99.245 364.705  1.00  0.00           C
ATOM   8534  CA  ASP T  13      -6.479 100.303 368.319  1.00  0.00           C
ATOM   8535  CA  LYS T  14      -5.181 103.763 367.420  1.00  0.00           C
ATOM   8536  CA  MET T  15      -8.077 105.740 368.923  1.00  0.00           C
ATOM   8537  CA  GLN T  16      -9.295 106.531 372.435  1.00  0.00           C
ATOM   8538  CA  LYS T  17     -12.136 104.302 373.691  1.00  0.00           C
ATOM   8539  CA  THR T  18     -12.712 103.272 370.062  1.00  0.00           C
ATOM   8540  CA  VAL T  19     -11.597 100.344 367.882  1.00  0.00           C
ATOM   8541  CA  THR T  20     -11.861  99.525 364.192  1.00  0.00           C
ATOM   8542  CA  VAL T  21     -13.541  96.192 363.616  1.00  0.00           C
ATOM   8543  CA  LEU T  22     -13.285  94.641 360.184  1.00  0.00           C
ATOM   8544  CA  VAL T  23     -16.460  92.617 359.608  1.00  0.00           C
ATOM   8545  CA  GLU T  24     -16.357  90.145 356.706  1.00  0.00           C
ATOM   8546  CA  ARG T  25     -19.456  89.150 354.709  1.00  0.00           C
ATOM   8547  CA  GLN T  26     -20.378  86.660 351.983  1.00  0.00           C
ATOM   8548  CA  PHE T  27     -23.218  86.216 349.528  1.00  0.00           C
ATOM   8549  CA  PRO T  28     -24.192  85.197 346.008  1.00  0.00           C
ATOM   8550  CA  HIS T  29     -23.631  87.650 343.246  1.00  0.00           C
ATOM   8551  CA  PRO T  30     -27.090  88.824 342.120  1.00  0.00           C
ATOM   8552  CA  LEU T  31     -26.421  87.940 338.470  1.00  0.00           C
ATOM   8553  CA  TYR T  32     -23.437  85.581 338.235  1.00  0.00           C
ATOM   8554  CA  GLY T  33     -24.323  83.714 341.392  1.00  0.00           C
ATOM   8555  CA  LYS T  34     -20.831  82.785 342.590  1.00  0.00           C
ATOM   8556  CA  VAL T  35     -20.306  83.463 346.286  1.00  0.00           C
ATOM   8557  CA  ILE T  36     -18.309  86.658 346.537  1.00  0.00           C
ATOM   8558  CA  LYS T  37     -16.912  88.090 349.737  1.00  0.00           C
ATOM   8559  CA  ARG T  38     -16.914  91.779 350.618  1.00  0.00           C
ATOM   8560  CA  SER T  39     -15.955  93.483 353.883  1.00  0.00           C
ATOM   8561  CA  LYS T  40     -16.584  96.651 355.896  1.00  0.00           C
ATOM   8562  CA  LYS T  41     -14.926  98.457 358.818  1.00  0.00           C
ATOM   8563  CA  TYR T  42     -16.975  99.576 361.804  1.00  0.00           C
ATOM   8564  CA  LEU T  43     -15.768 101.869 364.577  1.00  0.00           C
ATOM   8565  CA  ALA T  44     -16.892 100.273 367.832  1.00  0.00           C
ATOM   8566  CA  HIS T  45     -16.965 101.778 371.279  1.00  0.00           C
ATOM   8567  CA  ASP T  46     -14.337 100.375 373.664  1.00  0.00           C
ATOM   8568  CA  PRO T  47     -14.710 102.278 376.995  1.00  0.00           C
ATOM   8569  CA  GLU T  48     -12.475 100.069 379.111  1.00  0.00           C
ATOM   8570  CA  GLU T  49      -9.868 100.263 376.316  1.00  0.00           C
ATOM   8571  CA  LYS T  50     -10.133  96.503 376.789  1.00  0.00           C
ATOM   8572  CA  TYR T  51     -10.014  95.033 373.265  1.00  0.00           C
ATOM   8573  CA  LYS T  52      -6.606  94.889 371.610  1.00  0.00           C
ATOM   8574  CA  LEU T  53      -5.276  94.709 368.058  1.00  0.00           C
ATOM   8575  CA  GLY T  54      -5.880  91.198 366.766  1.00  0.00           C
ATOM   8576  CA  ASP T  55      -8.975  90.349 368.816  1.00  0.00           C
ATOM   8577  CA  VAL T  56     -12.065  88.851 367.224  1.00  0.00           C
ATOM   8578  CA  VAL T  57     -15.105  90.580 368.650  1.00  0.00           C
ATOM   8579  CA  GLU T  58     -18.886  90.695 368.447  1.00  0.00           C
ATOM   8580  CA  ILE T  59     -20.227  94.131 367.557  1.00  0.00           C
ATOM   8581  CA  ILE T  60     -23.717  95.183 368.580  1.00  0.00           C
ATOM   8582  CA  GLU T  61     -26.008  97.838 367.071  1.00  0.00           C
ATOM   8583  CA  SER T  62     -26.102 100.687 369.562  1.00  0.00           C
ATOM   8584  CA  ARG T  63     -27.271 104.246 370.075  1.00  0.00           C
ATOM   8585  CA  PRO T  64     -24.991 106.760 368.360  1.00  0.00           C
ATOM   8586  CA  ILE T  65     -21.854 107.395 370.398  1.00  0.00           C
ATOM   8587  CA  SER T  66     -20.016 109.501 367.890  1.00  0.00           C
ATOM   8588  CA  LYS T  67     -20.543 110.501 364.260  1.00  0.00           C
ATOM   8589  CA  ARG T  68     -19.748 107.460 362.198  1.00  0.00           C
ATOM   8590  CA  LYS T  69     -19.902 105.206 365.305  1.00  0.00           C
ATOM   8591  CA  ARG T  70     -23.053 103.201 366.045  1.00  0.00           C
```

```
ATOM   8592  CA  PHE T  71    -21.633  99.977 367.484  1.00  0.00           C
ATOM   8593  CA  ARG T  72    -20.362  98.718 370.817  1.00  0.00           C
ATOM   8594  CA  VAL T  73    -18.028  95.797 371.424  1.00  0.00           C
ATOM   8595  CA  LEU T  74    -20.454  93.219 372.729  1.00  0.00           C
ATOM   8596  CA  ARG T  75    -17.761  90.676 373.548  1.00  0.00           C
ATOM   8597  CA  LEU T  76    -14.581  88.820 372.702  1.00  0.00           C
ATOM   8598  CA  VAL T  77    -14.824  85.643 370.618  1.00  0.00           C
ATOM   8599  CA  GLU T  78    -11.167  84.654 370.356  1.00  0.00           C
ATOM   8600  CA  SER T  79     -8.093  86.641 371.337  1.00  0.00           C
ATOM   8601  CA  GLY T  80     -4.961  87.264 369.307  1.00  0.00           C
ATOM   8602  CA  ARG T  81     -4.571  86.369 365.649  1.00  0.00           C
ATOM   8603  CA  MET T  82     -2.716  88.883 363.522  1.00  0.00           C
ATOM   8604  CA  ASP T  83     -2.898  86.525 360.564  1.00  0.00           C
ATOM   8605  CA  LEU T  84     -6.019  88.569 359.752  1.00  0.00           C
ATOM   8606  CA  VAL T  85     -4.752  92.006 360.662  1.00  0.00           C
ATOM   8607  CA  GLU T  86     -1.923  91.177 358.224  1.00  0.00           C
ATOM   8608  CA  LYS T  87     -4.181  90.738 355.212  1.00  0.00           C
ATOM   8609  CA  TYR T  88     -5.841  94.049 355.988  1.00  0.00           C
ATOM   8610  CA  LEU T  89     -2.496  95.838 356.504  1.00  0.00           C
ATOM   8611  CA  ILE T  90     -0.757  94.269 353.526  1.00  0.00           C
ATOM   8612  CA  ARG T  91     -3.715  95.351 351.421  1.00  0.00           C
ATOM   8613  CA  ARG T  92     -3.382  98.887 352.747  1.00  0.00           C
ATOM   8614  CA  GLN T  93      0.301  98.695 351.829  1.00  0.00           C
ATOM   8615  CA  ASN T  94     -0.436  97.906 348.168  1.00  0.00           C
ATOM   8616  CA  TYR T  95     -2.317 101.186 347.963  1.00  0.00           C
ATOM   8617  CA  GLN T  96      0.982 102.901 348.805  1.00  0.00           C
ATOM   8618  CA  SER T  97      1.838 101.900 345.291  1.00  0.00           C
ATOM   8619  CA  LEU T  98     -0.679 101.585 342.379  1.00  0.00           C
ATOM   8620  CA  SER T  99     -0.942 105.392 341.720  1.00  0.00           C
ATOM   8621  CA  LYS T 100      1.757 107.424 339.896  1.00  0.00           C
ATOM   8622  CA  ARG T 101      4.453 104.797 340.535  1.00  0.00           C
ATOM   8623  CA  GLY T 102      2.474 101.531 340.582  1.00  0.00           C
ATOM   8624  CA  GLY T 103      1.551  98.719 343.005  1.00  0.00           C
ATOM   8625  CA  LYS T 104      3.827  95.792 344.137  1.00  0.00           C
ATOM   8626  CA  ALA T 105      3.527  92.030 343.363  1.00  0.00           C
TER    8627          ALA T 105
ATOM   8628  CA  PRO U  16     30.799  55.905 299.873  1.00  0.00           C
ATOM   8629  CA  SER U  17     32.620  56.483 303.185  1.00  0.00           C
ATOM   8630  CA  ARG U  18     33.187  52.959 304.527  1.00  0.00           C
ATOM   8631  CA  LYS U  19     36.993  52.845 304.563  1.00  0.00           C
ATOM   8632  CA  ALA U  20     37.130  51.973 308.288  1.00  0.00           C
ATOM   8633  CA  LYS U  21     35.907  53.568 311.522  1.00  0.00           C
ATOM   8634  CA  VAL U  22     38.703  55.311 313.429  1.00  0.00           C
ATOM   8635  CA  LYS U  23     37.141  53.932 316.624  1.00  0.00           C
ATOM   8636  CA  ALA U  24     37.240  50.263 315.589  1.00  0.00           C
ATOM   8637  CA  THR U  25     40.778  50.607 314.259  1.00  0.00           C
ATOM   8638  CA  LEU U  26     41.978  51.267 317.817  1.00  0.00           C
ATOM   8639  CA  GLY U  27     41.868  50.224 321.475  1.00  0.00           C
ATOM   8640  CA  GLU U  28     39.955  51.591 324.468  1.00  0.00           C
ATOM   8641  CA  PHE U  29     41.128  55.124 325.142  1.00  0.00           C
ATOM   8642  CA  ASP U  30     40.188  57.875 327.539  1.00  0.00           C
ATOM   8643  CA  LEU U  31     38.336  60.286 325.278  1.00  0.00           C
ATOM   8644  CA  ARG U  32     38.980  62.868 328.006  1.00  0.00           C
ATOM   8645  CA  ASP U  33     42.791  62.636 327.811  1.00  0.00           C
ATOM   8646  CA  TYR U  34     44.102  65.723 326.050  1.00  0.00           C
ATOM   8647  CA  ARG U  35     47.720  64.594 325.806  1.00  0.00           C
ATOM   8648  CA  ASN U  36     47.517  61.273 323.971  1.00  0.00           C
ATOM   8649  CA  VAL U  37     48.805  62.774 320.723  1.00  0.00           C
ATOM   8650  CA  GLU U  38     49.333  59.162 319.773  1.00  0.00           C
ATOM   8651  CA  VAL U  39     45.638  58.336 319.694  1.00  0.00           C
ATOM   8652  CA  LEU U  40     44.000  61.773 319.303  1.00  0.00           C
ATOM   8653  CA  LYS U  41     45.953  62.429 316.074  1.00  0.00           C
ATOM   8654  CA  ARG U  42     43.924  59.489 314.737  1.00  0.00           C
ATOM   8655  CA  PHE U  43     40.694  61.506 314.602  1.00  0.00           C
ATOM   8656  CA  LEU U  44     42.095  64.264 312.428  1.00  0.00           C
ATOM   8657  CA  SER U  45     41.609  64.661 308.699  1.00  0.00           C
ATOM   8658  CA  GLU U  46     44.569  64.916 306.355  1.00  0.00           C
ATOM   8659  CA  THR U  47     44.368  68.422 307.841  1.00  0.00           C
ATOM   8660  CA  GLY U  48     44.016  69.586 311.441  1.00  0.00           C
ATOM   8661  CA  LYS U  49     40.292  69.107 310.889  1.00  0.00           C
ATOM   8662  CA  ILE U  50     38.309  66.940 313.275  1.00  0.00           C
ATOM   8663  CA  LEU U  51     36.650  64.079 311.453  1.00  0.00           C
ATOM   8664  CA  PRO U  52     32.836  63.677 311.290  1.00  0.00           C
ATOM   8665  CA  ARG U  53     31.191  60.851 313.194  1.00  0.00           C
ATOM   8666  CA  ARG U  54     30.747  59.158 309.824  1.00  0.00           C
ATOM   8667  CA  ARG U  55     34.495  58.507 309.928  1.00  0.00           C
ATOM   8668  CA  THR U  56     35.253  58.688 313.639  1.00  0.00           C
ATOM   8669  CA  GLY U  57     32.760  55.935 314.388  1.00  0.00           C
ATOM   8670  CA  LEU U  58     32.124  57.724 317.671  1.00  0.00           C
ATOM   8671  CA  SER U  59     28.679  58.588 319.001  1.00  0.00           C
ATOM   8672  CA  GLY U  60     27.041  61.948 319.576  1.00  0.00           C
ATOM   8673  CA  LYS U  61     28.197  61.996 323.179  1.00  0.00           C
ATOM   8674  CA  GLU U  62     31.651  60.486 322.634  1.00  0.00           C
ATOM   8675  CA  GLN U  63     32.283  62.663 319.558  1.00  0.00           C
ATOM   8676  CA  ARG U  64     31.282  65.689 321.559  1.00  0.00           C
ATOM   8677  CA  ILE U  65     33.911  65.024 324.236  1.00  0.00           C
ATOM   8678  CA  LEU U  66     36.569  64.378 321.616  1.00  0.00           C
```

```
ATOM   8679  CA  ALA U  67      36.211  67.838 320.145  1.00  0.00           C
ATOM   8680  CA  LYS U  68      37.018  69.493 323.470  1.00  0.00           C
ATOM   8681  CA  THR U  69      39.981  67.184 323.920  1.00  0.00           C
ATOM   8682  CA  ILE U  70      41.267  67.703 320.384  1.00  0.00           C
ATOM   8683  CA  LYS U  71      40.862  71.449 320.876  1.00  0.00           C
ATOM   8684  CA  ARG U  72      42.661  71.441 324.232  1.00  0.00           C
ATOM   8685  CA  ALA U  73      45.484  69.485 322.622  1.00  0.00           C
ATOM   8686  CA  ARG U  74      45.686  72.159 319.937  1.00  0.00           C
ATOM   8687  CA  ILE U  75      46.305  74.993 322.362  1.00  0.00           C
ATOM   8688  CA  LEU U  76      49.064  73.027 324.135  1.00  0.00           C
ATOM   8689  CA  GLY U  77      50.691  72.714 320.720  1.00  0.00           C
ATOM   8690  CA  LEU U  78      50.482  68.918 320.591  1.00  0.00           C
ATOM   8691  CA  LEU U  79      47.847  68.870 317.842  1.00  0.00           C
ATOM   8692  CA  PRO U  80      47.571  71.087 314.738  1.00  0.00           C
ATOM   8693  CA  PHE U  81      44.796  73.484 313.879  1.00  0.00           C
ATOM   8694  CA  THR U  82      45.252  72.967 310.154  1.00  0.00           C
ATOM   8695  CA  GLU U  83      47.538  71.183 307.664  1.00  0.00           C
ATOM   8696  CA  LYS U  84      48.311  71.724 303.958  1.00  0.00           C
ATOM   8697  CA  LEU U  85      46.918  69.383 301.286  1.00  0.00           C
ATOM   8698  CA  VAL U  86      49.287  67.334 299.130  1.00  0.00           C
ATOM   8699  CA  ARG U  87      48.620  66.195 295.527  1.00  0.00           C
ATOM   8700  CA  LYS U  88      45.927  68.204 293.695  1.00  0.00           C
TER    8701          LYS U  88
ATOM   8702  CA  PRO V   2      -5.007 111.085 221.536  1.00  0.00           C
ATOM   8703  CA  ARG V   3      -8.826 111.340 221.763  1.00  0.00           C
ATOM   8704  CA  SER V   4     -11.273 109.576 219.410  1.00  0.00           C
ATOM   8705  CA  LEU V   5     -14.910 109.098 218.414  1.00  0.00           C
ATOM   8706  CA  LYS V   6     -14.576 107.744 214.822  1.00  0.00           C
ATOM   8707  CA  LYS V   7     -16.943 108.716 212.000  1.00  0.00           C
ATOM   8708  CA  GLY V   8     -19.774 111.016 213.096  1.00  0.00           C
ATOM   8709  CA  VAL V   9     -18.675 113.882 215.413  1.00  0.00           C
ATOM   8710  CA  PHE V  10     -21.366 113.692 218.083  1.00  0.00           C
ATOM   8711  CA  VAL V  11     -23.311 116.757 219.271  1.00  0.00           C
ATOM   8712  CA  ASP V  12     -26.649 116.676 221.105  1.00  0.00           C
ATOM   8713  CA  ASP V  13     -29.253 118.520 219.057  1.00  0.00           C
ATOM   8714  CA  HIS V  14     -30.809 120.325 222.019  1.00  0.00           C
ATOM   8715  CA  LEU V  15     -28.344 123.151 221.580  1.00  0.00           C
ATOM   8716  CA  LEU V  16     -27.447 122.288 217.995  1.00  0.00           C
ATOM   8717  CA  GLU V  17     -30.815 122.860 216.369  1.00  0.00           C
ATOM   8718  CA  LYS V  18     -31.109 125.676 218.927  1.00  0.00           C
ATOM   8719  CA  VAL V  19     -27.765 127.314 218.222  1.00  0.00           C
ATOM   8720  CA  LEU V  20     -28.190 127.481 214.453  1.00  0.00           C
ATOM   8721  CA  GLU V  21     -31.761 128.739 214.816  1.00  0.00           C
ATOM   8722  CA  LEU V  22     -30.060 131.752 216.364  1.00  0.00           C
ATOM   8723  CA  ASN V  23     -27.664 131.764 213.410  1.00  0.00           C
ATOM   8724  CA  ALA V  24     -30.634 132.848 211.311  1.00  0.00           C
ATOM   8725  CA  LYS V  25     -31.096 136.121 213.239  1.00  0.00           C
ATOM   8726  CA  GLY V  26     -27.332 136.286 213.651  1.00  0.00           C
ATOM   8727  CA  GLU V  27     -26.675 135.282 217.252  1.00  0.00           C
ATOM   8728  CA  LYS V  28     -28.344 135.612 220.650  1.00  0.00           C
ATOM   8729  CA  ARG V  29     -27.660 136.428 224.296  1.00  0.00           C
ATOM   8730  CA  LEU V  30     -26.934 133.170 226.149  1.00  0.00           C
ATOM   8731  CA  ILE V  31     -27.864 129.504 226.042  1.00  0.00           C
ATOM   8732  CA  LYS V  32     -27.763 126.759 228.666  1.00  0.00           C
ATOM   8733  CA  THR V  33     -27.591 123.026 228.155  1.00  0.00           C
ATOM   8734  CA  TRP V  34     -26.837 119.993 230.286  1.00  0.00           C
ATOM   8735  CA  SER V  35     -25.290 118.545 227.136  1.00  0.00           C
ATOM   8736  CA  ARG V  36     -21.659 118.857 228.172  1.00  0.00           C
ATOM   8737  CA  ARG V  37     -21.508 115.513 226.325  1.00  0.00           C
ATOM   8738  CA  SER V  38     -21.466 117.305 222.964  1.00  0.00           C
ATOM   8739  CA  THR V  39     -18.538 118.183 220.711  1.00  0.00           C
ATOM   8740  CA  ILE V  40     -18.215 121.785 219.564  1.00  0.00           C
ATOM   8741  CA  VAL V  41     -18.868 122.636 215.934  1.00  0.00           C
ATOM   8742  CA  PRO V  42     -17.980 125.901 214.088  1.00  0.00           C
ATOM   8743  CA  GLU V  43     -21.567 127.187 214.152  1.00  0.00           C
ATOM   8744  CA  MET V  44     -21.071 127.432 217.908  1.00  0.00           C
ATOM   8745  CA  VAL V  45     -18.189 129.889 217.574  1.00  0.00           C
ATOM   8746  CA  GLY V  46     -18.887 133.454 218.667  1.00  0.00           C
ATOM   8747  CA  HIS V  47     -21.761 132.148 220.783  1.00  0.00           C
ATOM   8748  CA  THR V  48     -21.858 131.965 224.566  1.00  0.00           C
ATOM   8749  CA  ILE V  49     -23.193 128.668 225.860  1.00  0.00           C
ATOM   8750  CA  ALA V  50     -23.519 128.254 229.616  1.00  0.00           C
ATOM   8751  CA  VAL V  51     -22.693 124.676 230.696  1.00  0.00           C
ATOM   8752  CA  TYR V  52     -23.770 122.823 233.854  1.00  0.00           C
ATOM   8753  CA  ASN V  53     -21.276 122.101 236.663  1.00  0.00           C
ATOM   8754  CA  GLY V  54     -23.769 119.576 237.909  1.00  0.00           C
ATOM   8755  CA  LYS V  55     -24.782 122.447 240.154  1.00  0.00           C
ATOM   8756  CA  GLN V  56     -24.295 125.691 238.182  1.00  0.00           C
ATOM   8757  CA  HIS V  57     -24.632 127.112 234.696  1.00  0.00           C
ATOM   8758  CA  VAL V  58     -21.286 128.633 233.769  1.00  0.00           C
ATOM   8759  CA  PRO V  59     -20.976 131.087 230.836  1.00  0.00           C
ATOM   8760  CA  VAL V  60     -18.477 129.762 228.278  1.00  0.00           C
ATOM   8761  CA  TYR V  61     -17.535 132.001 225.335  1.00  0.00           C
ATOM   8762  CA  ILE V  62     -16.836 129.586 222.467  1.00  0.00           C
ATOM   8763  CA  THR V  63     -13.971 130.733 220.223  1.00  0.00           C
ATOM   8764  CA  GLU V  64     -12.372 129.091 217.194  1.00  0.00           C
ATOM   8765  CA  ASN V  65      -9.221 127.863 218.973  1.00  0.00           C
```

```
ATOM   8766  CA  MET V  66     -11.488 125.701 221.155  1.00  0.00           C
ATOM   8767  CA  VAL V  67     -13.670 124.020 218.535  1.00  0.00           C
ATOM   8768  CA  GLY V  68     -12.978 120.281 218.451  1.00  0.00           C
ATOM   8769  CA  HIS V  69     -13.248 120.160 222.267  1.00  0.00           C
ATOM   8770  CA  LYS V  70     -16.388 119.221 224.227  1.00  0.00           C
ATOM   8771  CA  LEU V  71     -17.946 122.073 226.246  1.00  0.00           C
ATOM   8772  CA  GLY V  72     -17.688 120.191 229.527  1.00  0.00           C
ATOM   8773  CA  GLU V  73     -13.943 120.663 229.170  1.00  0.00           C
ATOM   8774  CA  PHE V  74     -14.735 124.313 229.967  1.00  0.00           C
ATOM   8775  CA  ALA V  75     -17.116 123.807 232.877  1.00  0.00           C
ATOM   8776  CA  PRO V  76     -15.052 122.346 235.754  1.00  0.00           C
ATOM   8777  CA  THR V  77     -16.801 119.971 238.161  1.00  0.00           C
ATOM   8778  CA  ARG V  78     -14.852 119.609 241.374  1.00  0.00           C
ATOM   8779  CA  THR V  79     -13.865 122.485 243.623  1.00  0.00           C
ATOM   8780  CA  TYR V  80     -10.262 122.172 244.912  1.00  0.00           C
ATOM   8781  CA  ARG V  81      -7.820 124.051 247.152  1.00  0.00           C
TER    8782      ARG V  81
ATOM   8783  CA  ARG W   8     -57.711 141.419 349.076  1.00  0.00           C
ATOM   8784  CA  ASN W   9     -58.711 140.938 352.709  1.00  0.00           C
ATOM   8785  CA  LEU W  10     -58.627 137.439 354.198  1.00  0.00           C
ATOM   8786  CA  SER W  11     -59.966 138.508 357.595  1.00  0.00           C
ATOM   8787  CA  ALA W  12     -57.966 135.631 359.088  1.00  0.00           C
ATOM   8788  CA  LEU W  13     -55.118 138.218 359.200  1.00  0.00           C
ATOM   8789  CA  LYS W  14     -56.382 138.097 362.749  1.00  0.00           C
ATOM   8790  CA  ARG W  15     -54.096 135.082 363.079  1.00  0.00           C
ATOM   8791  CA  HIS W  16     -51.030 137.183 362.437  1.00  0.00           C
ATOM   8792  CA  ARG W  17     -52.575 139.800 364.683  1.00  0.00           C
ATOM   8793  CA  GLN W  18     -52.643 137.255 367.513  1.00  0.00           C
ATOM   8794  CA  SER W  19     -49.320 135.646 366.669  1.00  0.00           C
ATOM   8795  CA  LEU W  20     -47.647 138.917 367.548  1.00  0.00           C
ATOM   8796  CA  LYS W  21     -49.300 138.972 370.940  1.00  0.00           C
ATOM   8797  CA  ARG W  22     -48.455 135.377 371.800  1.00  0.00           C
ATOM   8798  CA  ARG W  23     -44.957 136.072 370.540  1.00  0.00           C
ATOM   8799  CA  LEU W  24     -44.687 138.932 372.981  1.00  0.00           C
ATOM   8800  CA  ARG W  25     -46.313 136.954 375.777  1.00  0.00           C
ATOM   8801  CA  ASN W  26     -43.870 134.054 375.303  1.00  0.00           C
ATOM   8802  CA  LYS W  27     -40.805 136.174 374.808  1.00  0.00           C
ATOM   8803  CA  ALA W  28     -41.578 137.738 378.206  1.00  0.00           C
ATOM   8804  CA  LYS W  29     -41.870 134.451 380.043  1.00  0.00           C
ATOM   8805  CA  LYS W  30     -38.590 133.072 378.776  1.00  0.00           C
ATOM   8806  CA  SER W  31     -36.481 136.148 379.436  1.00  0.00           C
ATOM   8807  CA  ALA W  32     -37.678 136.065 383.053  1.00  0.00           C
ATOM   8808  CA  ILE W  33     -36.784 132.395 383.127  1.00  0.00           C
ATOM   8809  CA  LYS W  34     -33.237 132.915 381.856  1.00  0.00           C
ATOM   8810  CA  THR W  35     -32.648 135.845 384.181  1.00  0.00           C
ATOM   8811  CA  LEU W  36     -33.645 133.879 387.253  1.00  0.00           C
ATOM   8812  CA  SER W  37     -31.779 130.778 386.081  1.00  0.00           C
ATOM   8813  CA  LYS W  38     -28.461 132.616 385.853  1.00  0.00           C
ATOM   8814  CA  LYS W  39     -29.278 134.633 388.960  1.00  0.00           C
ATOM   8815  CA  ALA W  40     -29.544 131.319 390.782  1.00  0.00           C
ATOM   8816  CA  VAL W  41     -26.608 129.559 389.108  1.00  0.00           C
ATOM   8817  CA  GLN W  42     -24.522 132.599 389.913  1.00  0.00           C
ATOM   8818  CA  LEU W  43     -25.567 132.576 393.588  1.00  0.00           C
ATOM   8819  CA  ALA W  44     -24.734 128.887 393.931  1.00  0.00           C
ATOM   8820  CA  GLN W  45     -21.652 129.824 391.948  1.00  0.00           C
ATOM   8821  CA  GLU W  46     -20.433 132.166 394.713  1.00  0.00           C
ATOM   8822  CA  GLY W  47     -21.306 129.443 397.214  1.00  0.00           C
ATOM   8823  CA  LYS W  48     -24.262 131.260 398.860  1.00  0.00           C
ATOM   8824  CA  ALA W  49     -26.509 128.324 399.790  1.00  0.00           C
ATOM   8825  CA  GLU W  50     -29.843 129.805 400.916  1.00  0.00           C
ATOM   8826  CA  GLU W  51     -30.552 132.548 398.380  1.00  0.00           C
ATOM   8827  CA  ALA W  52     -29.123 130.374 395.591  1.00  0.00           C
ATOM   8828  CA  LEU W  53     -31.826 127.768 396.195  1.00  0.00           C
ATOM   8829  CA  LYS W  54     -34.543 130.332 397.027  1.00  0.00           C
ATOM   8830  CA  ILE W  55     -34.108 131.787 393.586  1.00  0.00           C
ATOM   8831  CA  MET W  56     -33.714 128.365 391.997  1.00  0.00           C
ATOM   8832  CA  ARG W  57     -37.200 127.401 393.267  1.00  0.00           C
ATOM   8833  CA  LYS W  58     -38.641 130.457 391.484  1.00  0.00           C
ATOM   8834  CA  ALA W  59     -36.829 129.468 388.327  1.00  0.00           C
ATOM   8835  CA  GLU W  60     -38.183 125.945 388.695  1.00  0.00           C
ATOM   8836  CA  SER W  61     -41.667 127.419 389.107  1.00  0.00           C
ATOM   8837  CA  LEU W  62     -41.651 129.867 386.222  1.00  0.00           C
ATOM   8838  CA  ILE W  63     -40.378 127.053 384.042  1.00  0.00           C
ATOM   8839  CA  ASP W  64     -43.103 124.554 384.889  1.00  0.00           C
ATOM   8840  CA  LYS W  65     -45.667 127.325 384.428  1.00  0.00           C
ATOM   8841  CA  ALA W  66     -44.080 128.239 381.129  1.00  0.00           C
ATOM   8842  CA  ALA W  67     -44.810 124.632 380.157  1.00  0.00           C
ATOM   8843  CA  LYS W  68     -48.349 125.064 381.475  1.00  0.00           C
ATOM   8844  CA  GLY W  69     -49.417 127.008 378.405  1.00  0.00           C
ATOM   8845  CA  SER W  70     -47.558 126.610 375.114  1.00  0.00           C
ATOM   8846  CA  THR W  71     -44.438 128.640 375.907  1.00  0.00           C
ATOM   8847  CA  LEU W  72     -41.689 126.253 376.954  1.00  0.00           C
ATOM   8848  CA  HIS W  73     -43.923 123.223 376.836  1.00  0.00           C
ATOM   8849  CA  LYS W  74     -42.909 119.528 376.880  1.00  0.00           C
ATOM   8850  CA  ASN W  75     -39.506 118.225 377.916  1.00  0.00           C
ATOM   8851  CA  ALA W  76     -38.332 121.751 377.168  1.00  0.00           C
ATOM   8852  CA  ALA W  77     -39.311 122.415 380.758  1.00  0.00           C
```

```
ATOM  8853 CA ALA W  78  -37.707 119.177 381.926 1.00 0.00           C
ATOM  8854 CA ARG W  79  -34.364 120.029 380.279 1.00 0.00           C
ATOM  8855 CA ARG W  80  -34.366 123.488 381.828 1.00 0.00           C
ATOM  8856 CA LYS W  81  -34.986 122.223 385.333 1.00 0.00           C
ATOM  8857 CA SER W  82  -32.382 119.460 385.250 1.00 0.00           C
ATOM  8858 CA ARG W  83  -29.654 121.597 383.606 1.00 0.00           C
ATOM  8859 CA LEU W  84  -30.498 124.085 386.388 1.00 0.00           C
ATOM  8860 CA MET W  85  -30.665 121.920 389.539 1.00 0.00           C
ATOM  8861 CA ARG W  86  -27.556 120.223 388.199 1.00 0.00           C
ATOM  8862 CA LYS W  87  -25.448 123.356 387.655 1.00 0.00           C
ATOM  8863 CA VAL W  88  -26.665 124.664 391.026 1.00 0.00           C
ATOM  8864 CA ARG W  89  -25.939 121.669 393.245 1.00 0.00           C
ATOM  8865 CA GLN W  90  -22.501 121.193 391.696 1.00 0.00           C
ATOM  8866 CA LEU W  91  -21.440 124.839 391.980 1.00 0.00           C
ATOM  8867 CA LEU W  92  -22.606 124.460 395.554 1.00 0.00           C
ATOM  8868 CA GLU W  93  -19.700 122.035 396.025 1.00 0.00           C
ATOM  8869 CA ALA W  94  -17.539 124.769 397.490 1.00 0.00           C
ATOM  8870 CA ALA W  95  -18.546 124.060 401.106 1.00 0.00           C
ATOM  8871 CA GLY W  96  -22.193 124.425 400.155 1.00 0.00           C
ATOM  8872 CA ALA W  97  -24.445 122.321 402.351 1.00 0.00           C
ATOM  8873 CA PRO W  98  -27.886 122.926 400.750 1.00 0.00           C
ATOM  8874 CA LEU W  99  -29.674 124.750 403.563 1.00 0.00           C
ATOM  8875 CA ILE W 100  -33.111 125.501 402.126 1.00 0.00           C
ATOM  8876 CA GLY W 101  -32.599 122.372 400.046 1.00 0.00           C
ATOM  8877 CA GLY W 102  -35.563 123.706 398.110 1.00 0.00           C
ATOM  8878 CA GLY W 103  -35.371 122.260 394.636 1.00 0.00           C
ATOM  8879 CA LEU W 104  -32.852 119.725 395.925 1.00 0.00           C
ATOM  8880 CA SER W 105  -33.627 116.265 397.235 1.00 0.00           C
ATOM  8881 CA ALA W 106  -30.758 116.020 399.709 1.00 0.00           C
TER   8882       ALA W 106
ATOM  8883 CA GLY X   2   10.635  94.532 228.653 1.00 0.00           C
ATOM  8884 CA LYS X   3    7.154  93.237 229.443 1.00 0.00           C
ATOM  8885 CA GLY X   4    6.312  96.914 229.480 1.00 0.00           C
ATOM  8886 CA ASP X   5    7.402  98.142 226.019 1.00 0.00           C
ATOM  8887 CA ARG X   6    4.163  97.972 224.065 1.00 0.00           C
ATOM  8888 CA ARG X   7    6.146  97.938 220.828 1.00 0.00           C
ATOM  8889 CA THR X   8    8.175  94.743 221.265 1.00 0.00           C
ATOM  8890 CA ARG X   9    7.484  90.987 221.265 1.00 0.00           C
ATOM  8891 CA ARG X  10    7.126  90.730 225.061 1.00 0.00           C
ATOM  8892 CA GLY X  11    5.363  94.058 225.314 1.00 0.00           C
ATOM  8893 CA LYS X  12    2.704  92.626 223.003 1.00 0.00           C
ATOM  8894 CA ILE X  13    2.532  89.203 224.628 1.00 0.00           C
ATOM  8895 CA TRP X  14    2.221  90.812 228.055 1.00 0.00           C
ATOM  8896 CA ARG X  15   -0.590  93.031 226.866 1.00 0.00           C
ATOM  8897 CA GLY X  16   -2.068  90.001 225.119 1.00 0.00           C
ATOM  8898 CA THR X  17   -2.221  91.594 221.683 1.00 0.00           C
ATOM  8899 CA TYR X  18   -0.932  91.565 218.127 1.00 0.00           C
ATOM  8900 CA GLY X  19    0.419  94.212 215.813 1.00 0.00           C
ATOM  8901 CA LYS X  20    3.484  95.086 213.798 1.00 0.00           C
ATOM  8902 CA TYR X  21    5.509  93.654 216.678 1.00 0.00           C
ATOM  8903 CA ARG X  22    3.737  90.354 217.276 1.00 0.00           C
ATOM  8904 CA PRO X  23    1.865  89.514 214.077 1.00 0.00           C
ATOM  8905 CA ARG X  24   -0.482  86.531 213.864 1.00 0.00           C
ATOM  8906 CA LYS X  25    1.926  84.491 211.659 1.00 0.00           C
TER   8907       LYS X  25
CONECT 1701 1715
CONECT 1715 1701 1716 1717 1718
CONECT 1716 1715
CONECT 1717 1715
CONECT 1718 1715 1719
CONECT 1719 1718 1720
CONECT 1720 1719 1721 1722
CONECT 1721 1720 1726
CONECT 1722 1720 1723 1724
CONECT 1723 1722 1739
CONECT 1724 1722 1725 1726
CONECT 1725 1724
CONECT 1726 1721 1724 1727
CONECT 1727 1726 1728 1738
CONECT 1728 1727 1729
CONECT 1729 1728 1730
CONECT 1730 1729 1731 1738
CONECT 1731 1730 1732 1733
CONECT 1732 1731
CONECT 1733 1731 1734
CONECT 1734 1733 1735 1737
CONECT 1735 1734 1736
CONECT 1736 1735
CONECT 1737 1734 1738
CONECT 1738 1727 1730 1737
CONECT 1739 1723
CONECT 1829 1844
CONECT 1844 1829 1845 1846 1847
CONECT 1845 1844
CONECT 1846 1844
CONECT 1847 1844 1848
CONECT 1848 1847 1849
```

```
CONECT 1849 1848 1850 1851
CONECT 1850 1849 1853
CONECT 1851 1849 1852 1854
CONECT 1852 1851 1864
CONECT 1853 1850 1854 1856
CONECT 1854 1851 1853 1855
CONECT 1855 1854
CONECT 1856 1853 1857 1863
CONECT 1857 1856 1858 1859
CONECT 1858 1857
CONECT 1859 1857 1860
CONECT 1860 1859 1861 1862
CONECT 1861 1860
CONECT 1862 1860 1863
CONECT 1863 1856 1862
CONECT 1864 1852 1865 1866 1867
CONECT 1865 1864
CONECT 1866 1864
CONECT 1867 1864 1868
CONECT 1868 1867 1869
CONECT 1869 1868 1870 1871
CONECT 1870 1869 1873
CONECT 1871 1869 1872 1874
CONECT 1872 1871 1884
CONECT 1873 1870 1874 1876
CONECT 1874 1871 1873 1875
CONECT 1875 1874
CONECT 1876 1873 1877 1883
CONECT 1877 1876 1878 1879
CONECT 1878 1877
CONECT 1879 1877 1880
CONECT 1880 1879 1881 1882
CONECT 1881 1880
CONECT 1882 1880 1883
CONECT 1883 1876 1882
CONECT 1884 1872
CONECT 2051 2063
CONECT 2063 2051 2064 2065 2066
CONECT 2064 2063
CONECT 2065 2063
CONECT 2066 2063 2067
CONECT 2067 2066 2068
CONECT 2068 2067 2069 2070
CONECT 2069 2068 2074
CONECT 2070 2068 2071 2072
CONECT 2071 2070 2088
CONECT 2072 2070 2073 2074
CONECT 2073 2072
CONECT 2074 2069 2072 2075
CONECT 2075 2074 2076 2085
CONECT 2076 2075 2077
CONECT 2077 2076 2078
CONECT 2078 2077 2079 2085
CONECT 2079 2078 2080 2081
CONECT 2080 2079
CONECT 2081 2079 2082
CONECT 2082 2081 2083 2084
CONECT 2083 2082 2086 2087
CONECT 2084 2082 2085
CONECT 2085 2075 2078 2084
CONECT 2086 2083
CONECT 2087 2083
CONECT 2088 2071
CONECT 2181 2213
CONECT 2195 2196 2200 2203
CONECT 2196 2195 2197 2201
CONECT 2197 2196 2198
CONECT 2198 2197 2199 2202
CONECT 2199 2198 2200
CONECT 2200 2195 2199
CONECT 2201 2196
CONECT 2202 2198
CONECT 2203 2195 2204 2209
CONECT 2204 2203 2205 2207
CONECT 2205 2204 2206
CONECT 2206 2205
CONECT 2207 2204 2208 2210
CONECT 2208 2207 2209 2211
CONECT 2209 2203 2208
CONECT 2210 2207 2216
CONECT 2211 2208 2212
CONECT 2212 2211 2213
CONECT 2213 2181 2212 2214 2215
CONECT 2214 2213
CONECT 2215 2213
CONECT 2216 2210
CONECT 2224 2236
```

```
CONECT 2236 2224 2237 2238 2239
CONECT 2237 2236
CONECT 2238 2236
CONECT 2239 2236 2240
CONECT 2240 2239 2241
CONECT 2241 2240 2242 2243
CONECT 2242 2241 2248
CONECT 2243 2241 2244 2245
CONECT 2244 2243 2260
CONECT 2245 2243 2246 2248
CONECT 2246 2245 2247
CONECT 2247 2246
CONECT 2248 2242 2245 2249
CONECT 2249 2248 2250 2259
CONECT 2250 2249 2251
CONECT 2251 2250 2252
CONECT 2252 2251 2253 2259
CONECT 2253 2252 2254 2255
CONECT 2254 2253
CONECT 2255 2253 2256
CONECT 2256 2255 2257 2258
CONECT 2257 2256
CONECT 2258 2256 2259
CONECT 2259 2249 2252 2258
CONECT 2260 2244
CONECT 2290 2340
CONECT 2304 2306 2311 2318
CONECT 2305 2306 2317
CONECT 2306 2304 2305 2307
CONECT 2307 2306 2308 2309
CONECT 2308 2307
CONECT 2309 2307 2310 2315
CONECT 2310 2309 2311 2313
CONECT 2311 2304 2310 2312
CONECT 2312 2311
CONECT 2313 2310 2314
CONECT 2314 2313 2315
CONECT 2315 2309 2314 2331
CONECT 2316 2317
CONECT 2317 2305 2316 2318
CONECT 2318 2304 2317 2319
CONECT 2319 2318 2320
CONECT 2320 2319 2321
CONECT 2321 2320 2322 2326
CONECT 2322 2321 2323 2324
CONECT 2323 2322
CONECT 2324 2322 2325
CONECT 2325 2324
CONECT 2326 2321 2327
CONECT 2327 2326 2328 2329
CONECT 2328 2327
CONECT 2329 2327 2330
CONECT 2330 2329
CONECT 2331 2315 2332 2337
CONECT 2332 2331 2333 2334
CONECT 2333 2332
CONECT 2334 2332 2335 2336
CONECT 2335 2334 2343
CONECT 2336 2334 2337 2338
CONECT 2337 2331 2336
CONECT 2338 2336 2339
CONECT 2339 2338 2340
CONECT 2340 2290 2339 2341 2342
CONECT 2341 2340
CONECT 2342 2340
CONECT 2343 2335
CONECT 2351 2382
CONECT 2365 2366 2370
CONECT 2366 2365 2367 2371
CONECT 2367 2366 2368
CONECT 2368 2367 2369 2372
CONECT 2369 2368 2370 2373
CONECT 2370 2365 2369
CONECT 2371 2366
CONECT 2372 2368
CONECT 2373 2369 2374 2379
CONECT 2374 2373 2375 2376
CONECT 2375 2374
CONECT 2376 2374 2377 2378
CONECT 2377 2376 2379 2380
CONECT 2378 2376 2385
CONECT 2379 2373 2377
CONECT 2380 2377 2381
CONECT 2381 2380 2382
CONECT 2382 2351 2381 2383 2384
CONECT 2383 2382
CONECT 2384 2382
```

```
CONECT 2385 2378 2386 2387 2388
CONECT 2386 2385
CONECT 2387 2385
CONECT 2388 2385 2389
CONECT 2389 2388 2390
CONECT 2390 2389 2391 2392
CONECT 2391 2390 2396
CONECT 2392 2390 2393 2394
CONECT 2393 2392 2406
CONECT 2394 2392 2395 2396
CONECT 2395 2394
CONECT 2396 2391 2394 2397
CONECT 2397 2396 2398 2404
CONECT 2398 2397 2399 2400
CONECT 2399 2398
CONECT 2400 2398 2401
CONECT 2401 2400 2402 2403
CONECT 2402 2401
CONECT 2403 2401 2404 2405
CONECT 2404 2397 2403
CONECT 2405 2403
CONECT 2406 2393
CONECT 2502 2517
CONECT 2517 2502 2518 2519 2520
CONECT 2518 2517
CONECT 2519 2517
CONECT 2520 2517 2521
CONECT 2521 2520 2522
CONECT 2522 2521 2523 2524
CONECT 2523 2522 2528
CONECT 2524 2522 2525 2526
CONECT 2525 2524 2541
CONECT 2526 2524 2527 2528
CONECT 2527 2526
CONECT 2528 2523 2526 2529
CONECT 2529 2528 2530 2539
CONECT 2530 2529 2531
CONECT 2531 2530 2532 2540
CONECT 2532 2531 2533 2539
CONECT 2533 2532 2534 2535
CONECT 2534 2533
CONECT 2535 2533 2536
CONECT 2536 2535 2537 2538
CONECT 2537 2536
CONECT 2538 2536 2539
CONECT 2539 2529 2532 2538
CONECT 2540 2531
CONECT 2541 2525
CONECT 2569 2581
CONECT 2581 2569 2582 2583 2584
CONECT 2582 2581
CONECT 2583 2581
CONECT 2584 2581 2585
CONECT 2585 2584 2586
CONECT 2586 2585 2587 2588
CONECT 2587 2586 2592
CONECT 2588 2586 2589 2590
CONECT 2589 2588 2602
CONECT 2590 2588 2591 2592
CONECT 2591 2590
CONECT 2592 2587 2590 2593
CONECT 2593 2592 2594 2600
CONECT 2594 2593 2595 2596
CONECT 2595 2594
CONECT 2596 2594 2597
CONECT 2597 2596 2598 2599
CONECT 2598 2597
CONECT 2599 2597 2600 2601
CONECT 2600 2593 2599
CONECT 2601 2599
CONECT 2602 2589
CONECT 2673 2706
CONECT 2688 2689 2694 2697
CONECT 2689 2688 2690 2695
CONECT 2690 2689 2691
CONECT 2691 2690 2692 2696
CONECT 2692 2691 2693 2694
CONECT 2693 2692
CONECT 2694 2688 2692
CONECT 2695 2689
CONECT 2696 2691
CONECT 2697 2688 2698 2703
CONECT 2698 2697 2699 2700
CONECT 2699 2698
CONECT 2700 2698 2701 2702
CONECT 2701 2700 2703 2704
CONECT 2702 2700 2726
```

```
CONECT 2703 2697 2701
CONECT 2704 2701 2705
CONECT 2705 2704 2706
CONECT 2706 2673 2705 2707 2708
CONECT 2707 2706
CONECT 2708 2706
CONECT 2709 2710 2714
CONECT 2710 2709 2711 2715
CONECT 2711 2710 2712
CONECT 2712 2711 2713 2716
CONECT 2713 2712 2714 2717
CONECT 2714 2709 2713
CONECT 2715 2710
CONECT 2716 2712
CONECT 2717 2713 2718 2723
CONECT 2718 2717 2719 2720
CONECT 2719 2718
CONECT 2720 2718 2721 2722
CONECT 2721 2720 2723 2724
CONECT 2722 2720 2729
CONECT 2723 2717 2721
CONECT 2724 2721 2725
CONECT 2725 2724 2726
CONECT 2726 2702 2725 2727 2728
CONECT 2727 2726
CONECT 2728 2726
CONECT 2729 2722
CONECT 2757 2772
CONECT 2772 2757 2773 2774 2775
CONECT 2773 2772
CONECT 2774 2772
CONECT 2775 2772 2776
CONECT 2776 2775 2777
CONECT 2777 2776 2778 2779
CONECT 2778 2777 2783
CONECT 2779 2777 2780 2781
CONECT 2780 2779 2795
CONECT 2781 2779 2782 2783
CONECT 2782 2781
CONECT 2783 2778 2781 2784
CONECT 2784 2783 2785 2794
CONECT 2785 2784 2786
CONECT 2786 2785 2787
CONECT 2787 2786 2788 2794
CONECT 2788 2787 2789 2790
CONECT 2789 2788
CONECT 2790 2788 2791 2792
CONECT 2791 2790
CONECT 2792 2790 2793
CONECT 2793 2792 2794
CONECT 2794 2784 2787 2793
CONECT 2795 2780
CONECT 3354 3368
CONECT 3368 3354 3369 3370 3371
CONECT 3369 3368
CONECT 3370 3368
CONECT 3371 3368 3372
CONECT 3372 3371 3373
CONECT 3373 3372 3374 3375
CONECT 3374 3373 3379
CONECT 3375 3373 3376 3377
CONECT 3376 3375 3392
CONECT 3377 3375 3378 3379
CONECT 3378 3377
CONECT 3379 3374 3377 3380
CONECT 3380 3379 3381 3391
CONECT 3381 3380 3382
CONECT 3382 3381 3383
CONECT 3383 3382 3384 3391
CONECT 3384 3383 3385 3386
CONECT 3385 3384
CONECT 3386 3384 3387
CONECT 3387 3386 3388 3390
CONECT 3388 3387 3389
CONECT 3389 3388
CONECT 3390 3387 3391
CONECT 3391 3380 3383 3390
CONECT 3392 3376
CONECT 3482 3497
CONECT 3497 3482 3498 3499 3500
CONECT 3498 3497
CONECT 3499 3497
CONECT 3500 3497 3501
CONECT 3501 3500 3502
CONECT 3502 3501 3503 3504
CONECT 3503 3502 3506
CONECT 3504 3502 3505 3507
```

```
CONECT 3505 3504 3517
CONECT 3506 3503 3507 3509
CONECT 3507 3504 3506 3508
CONECT 3508 3507
CONECT 3509 3506 3510 3516
CONECT 3510 3509 3511 3512
CONECT 3511 3510
CONECT 3512 3510 3513
CONECT 3513 3512 3514 3515
CONECT 3514 3513
CONECT 3515 3513 3516
CONECT 3516 3509 3515
CONECT 3517 3505 3518 3519 3520
CONECT 3518 3517
CONECT 3519 3517
CONECT 3520 3517 3521
CONECT 3521 3520 3522
CONECT 3522 3521 3523 3524
CONECT 3523 3522 3526
CONECT 3524 3522 3525 3527
CONECT 3525 3524 3537
CONECT 3526 3523 3527 3529
CONECT 3527 3524 3526 3528
CONECT 3528 3527
CONECT 3529 3526 3530 3536
CONECT 3530 3529 3531 3532
CONECT 3531 3530
CONECT 3532 3530 3533
CONECT 3533 3532 3534 3535
CONECT 3534 3533
CONECT 3535 3533 3536
CONECT 3536 3529 3535
CONECT 3537 3525
CONECT 3716 3717 3718 3719
CONECT 3717 3716
CONECT 3718 3716
CONECT 3719 3716 3720
CONECT 3720 3719 3721
CONECT 3721 3720 3722 3723
CONECT 3722 3721 3727
CONECT 3723 3721 3724 3725
CONECT 3724 3723 3741
CONECT 3725 3723 3726 3727
CONECT 3726 3725
CONECT 3727 3722 3725 3728
CONECT 3728 3727 3729 3738
CONECT 3729 3728 3730
CONECT 3730 3729 3731
CONECT 3731 3730 3732 3738
CONECT 3732 3731 3733 3734
CONECT 3733 3732
CONECT 3734 3732 3735
CONECT 3735 3734 3736 3737
CONECT 3736 3735 3739 3740
CONECT 3737 3735 3738
CONECT 3738 3728 3731 3737
CONECT 3739 3736
CONECT 3740 3736
CONECT 3741 3724
CONECT 3834 3866
CONECT 3848 3849 3853 3856
CONECT 3849 3848 3850 3854
CONECT 3850 3849 3851
CONECT 3851 3850 3852 3855
CONECT 3852 3851 3853
CONECT 3853 3848 3852
CONECT 3854 3849
CONECT 3855 3851
CONECT 3856 3848 3857 3862
CONECT 3857 3856 3858 3860
CONECT 3858 3857 3859
CONECT 3859 3858
CONECT 3860 3857 3861 3863
CONECT 3861 3860 3862 3864
CONECT 3862 3856 3861
CONECT 3863 3860 3869
CONECT 3864 3861 3865
CONECT 3865 3864 3866
CONECT 3866 3834 3865 3867 3868
CONECT 3867 3866
CONECT 3868 3866
CONECT 3869 3863
CONECT 3877 3889
CONECT 3889 3877 3890 3891 3892
CONECT 3890 3889
CONECT 3891 3889
CONECT 3892 3889 3893
```

```
CONECT 3893 3892 3894
CONECT 3894 3893 3895 3896
CONECT 3895 3894 3901
CONECT 3896 3894 3897 3898
CONECT 3897 3896 3913
CONECT 3898 3896 3899 3901
CONECT 3899 3898 3900
CONECT 3900 3899
CONECT 3901 3895 3898 3902
CONECT 3902 3901 3903 3912
CONECT 3903 3902 3904
CONECT 3904 3903 3905
CONECT 3905 3904 3906 3912
CONECT 3906 3905 3907 3908
CONECT 3907 3906
CONECT 3908 3906 3909
CONECT 3909 3908 3910 3911
CONECT 3910 3909
CONECT 3911 3909 3912
CONECT 3912 3902 3905 3911
CONECT 3913 3897
CONECT 3943 3993
CONECT 3957 3959 3964 3971
CONECT 3958 3959 3970
CONECT 3959 3957 3958 3960
CONECT 3960 3959 3961 3962
CONECT 3961 3960
CONECT 3962 3960 3963 3968
CONECT 3963 3962 3964 3966
CONECT 3964 3957 3963 3965
CONECT 3965 3964
CONECT 3966 3963 3967
CONECT 3967 3966 3968
CONECT 3968 3962 3967 3984
CONECT 3969 3970
CONECT 3970 3958 3969 3971
CONECT 3971 3957 3970 3972
CONECT 3972 3971 3973
CONECT 3973 3972 3974
CONECT 3974 3973 3975 3979
CONECT 3975 3974 3976 3977
CONECT 3976 3975
CONECT 3977 3975 3978
CONECT 3978 3977
CONECT 3979 3974 3980
CONECT 3980 3979 3981 3982
CONECT 3981 3980
CONECT 3982 3980 3983
CONECT 3983 3982
CONECT 3984 3968 3985 3990
CONECT 3985 3984 3986 3987
CONECT 3986 3985
CONECT 3987 3985 3988 3989
CONECT 3988 3987 3996
CONECT 3989 3987 3990 3991
CONECT 3990 3984 3989
CONECT 3991 3989 3992
CONECT 3992 3991 3993
CONECT 3993 3943 3992 3994 3995
CONECT 3994 3993
CONECT 3995 3993
CONECT 3996 3988
CONECT 4004 4035
CONECT 4018 4019 4023
CONECT 4019 4018 4020 4024
CONECT 4020 4019 4021
CONECT 4021 4020 4022 4025
CONECT 4022 4021 4023 4026
CONECT 4023 4018 4022
CONECT 4024 4019
CONECT 4025 4021
CONECT 4026 4022 4027 4032
CONECT 4027 4026 4028 4029
CONECT 4028 4027
CONECT 4029 4027 4030 4031
CONECT 4030 4029 4032 4033
CONECT 4031 4029 4038
CONECT 4032 4026 4030
CONECT 4033 4030 4034
CONECT 4034 4033 4035
CONECT 4035 4004 4034 4036 4037
CONECT 4036 4035
CONECT 4037 4035
CONECT 4038 4031 4039 4040 4041
CONECT 4039 4038
CONECT 4040 4038
CONECT 4041 4038 4042
```

```
CONECT 4042 4041 4043
CONECT 4043 4042 4044 4045
CONECT 4044 4043 4049
CONECT 4045 4043 4046 4047
CONECT 4046 4045 4059
CONECT 4047 4045 4048 4049
CONECT 4048 4047
CONECT 4049 4044 4047 4050
CONECT 4050 4049 4051 4057
CONECT 4051 4050 4052 4053
CONECT 4052 4051
CONECT 4053 4051 4054
CONECT 4054 4053 4055 4056
CONECT 4055 4054
CONECT 4056 4054 4057 4058
CONECT 4057 4050 4056
CONECT 4058 4056
CONECT 4059 4046
CONECT 4155 4170
CONECT 4170 4155 4171 4172 4173
CONECT 4171 4170
CONECT 4172 4170
CONECT 4173 4170 4174
CONECT 4174 4173 4175
CONECT 4175 4174 4176 4177
CONECT 4176 4175 4181
CONECT 4177 4175 4178 4179
CONECT 4178 4177 4194
CONECT 4179 4177 4180 4181
CONECT 4180 4179
CONECT 4181 4176 4179 4182
CONECT 4182 4181 4183 4192
CONECT 4183 4182 4184
CONECT 4184 4183 4185 4193
CONECT 4185 4184 4186 4192
CONECT 4186 4185 4187 4188
CONECT 4187 4186
CONECT 4188 4186 4189
CONECT 4189 4188 4190 4191
CONECT 4190 4189
CONECT 4191 4189 4192
CONECT 4192 4182 4185 4191
CONECT 4193 4184
CONECT 4194 4178
CONECT 4222 4234
CONECT 4234 4222 4235 4236 4237
CONECT 4235 4234
CONECT 4236 4234
CONECT 4237 4234 4238
CONECT 4238 4237 4239
CONECT 4239 4238 4240 4241
CONECT 4240 4239 4245
CONECT 4241 4239 4242 4243
CONECT 4242 4241 4255
CONECT 4243 4241 4244 4245
CONECT 4244 4243
CONECT 4245 4240 4243 4246
CONECT 4246 4245 4247 4253
CONECT 4247 4246 4248 4249
CONECT 4248 4247
CONECT 4249 4247 4250
CONECT 4250 4249 4251 4252
CONECT 4251 4250
CONECT 4252 4250 4253 4254
CONECT 4253 4246 4252
CONECT 4254 4252
CONECT 4255 4242
CONECT 4326 4359
CONECT 4341 4342 4347 4350
CONECT 4342 4341 4343 4348
CONECT 4343 4342 4344
CONECT 4344 4343 4345 4349
CONECT 4345 4344 4346 4347
CONECT 4346 4345
CONECT 4347 4341 4345
CONECT 4348 4342
CONECT 4349 4344
CONECT 4350 4341 4351 4356
CONECT 4351 4350 4352 4353
CONECT 4352 4351
CONECT 4353 4351 4354 4355
CONECT 4354 4353 4356 4357
CONECT 4355 4353 4379
CONECT 4356 4350 4354
CONECT 4357 4354 4358
CONECT 4358 4357 4359
CONECT 4359 4326 4358 4360 4361
```

```
CONECT 4360 4359
CONECT 4361 4359
CONECT 4362 4363 4367
CONECT 4363 4362 4364 4368
CONECT 4364 4363 4365
CONECT 4365 4364 4366 4369
CONECT 4366 4365 4367 4370
CONECT 4367 4362 4366
CONECT 4368 4363
CONECT 4369 4365
CONECT 4370 4366 4371 4376
CONECT 4371 4370 4372 4373
CONECT 4372 4371
CONECT 4373 4371 4374 4375
CONECT 4374 4373 4376 4377
CONECT 4375 4373 4382
CONECT 4376 4370 4374
CONECT 4377 4374 4378
CONECT 4378 4377 4379
CONECT 4379 4355 4378 4380 4381
CONECT 4380 4379
CONECT 4381 4379
CONECT 4382 4375
CONECT 4410 4425
CONECT 4425 4410 4426 4427 4428
CONECT 4426 4425
CONECT 4427 4425
CONECT 4428 4425 4429
CONECT 4429 4428 4430
CONECT 4430 4429 4431 4432
CONECT 4431 4430 4436
CONECT 4432 4430 4433 4434
CONECT 4433 4432 4448
CONECT 4434 4432 4435 4436
CONECT 4435 4434
CONECT 4436 4431 4434 4437
CONECT 4437 4436 4438 4447
CONECT 4438 4437 4439
CONECT 4439 4438 4440
CONECT 4440 4439 4441 4447
CONECT 4441 4440 4442 4443
CONECT 4442 4441
CONECT 4443 4441 4444 4445
CONECT 4444 4443
CONECT 4445 4443 4446
CONECT 4446 4445 4447
CONECT 4447 4437 4440 4446
CONECT 4448 4433
CONECT 4976 4977 4981 4984
CONECT 4977 4976 4978 4982
CONECT 4978 4977 4979
CONECT 4979 4978 4980 4983
CONECT 4980 4979 4981
CONECT 4981 4976 4980
CONECT 4982 4977
CONECT 4983 4979
CONECT 4984 4976 4985 4990
CONECT 4985 4984 4986 4987
CONECT 4986 4985
CONECT 4987 4985 4988 4989
CONECT 4988 4987 4990 4991
CONECT 4989 4987 4996
CONECT 4990 4984 4988
CONECT 4991 4988 4992
CONECT 4992 4991 4993
CONECT 4993 4992 4994 4995
CONECT 4994 4993
CONECT 4995 4993
CONECT 4996 4989
CONECT 5200 5215
CONECT 5215 5200 5216 5217 5218
CONECT 5216 5215
CONECT 5217 5215
CONECT 5218 5215 5219
CONECT 5219 5218 5220
CONECT 5220 5219 5221 5222
CONECT 5221 5220 5224
CONECT 5222 5220 5223 5225
CONECT 5223 5222 5235
CONECT 5224 5221 5225 5227
CONECT 5225 5222 5224 5226
CONECT 5226 5225
CONECT 5227 5224 5228 5234
CONECT 5228 5227 5229 5230
CONECT 5229 5228
CONECT 5230 5228 5231
CONECT 5231 5230 5232 5233
```

```
CONECT 5232 5231
CONECT 5233 5231 5234
CONECT 5234 5227 5233
CONECT 5235 5223 5236 5237 5238
CONECT 5236 5235
CONECT 5237 5235
CONECT 5238 5235 5239
CONECT 5239 5238 5240
CONECT 5240 5239 5241 5242
CONECT 5241 5240 5244
CONECT 5242 5240 5243 5245
CONECT 5243 5242 5255
CONECT 5244 5241 5245 5247
CONECT 5245 5242 5244 5246
CONECT 5246 5245
CONECT 5247 5244 5248 5254
CONECT 5248 5247 5249 5250
CONECT 5249 5248
CONECT 5250 5248 5251
CONECT 5251 5250 5252 5253
CONECT 5252 5251
CONECT 5253 5251 5254
CONECT 5254 5247 5253
CONECT 5255 5243
CONECT 5800 5801 5802 5803
CONECT 5801 5800
CONECT 5802 5800
CONECT 5803 5800 5804
CONECT 5804 5803 5805
CONECT 5805 5804 5806 5807
CONECT 5806 5805 5811
CONECT 5807 5805 5808 5809
CONECT 5808 5807 5821
CONECT 5809 5807 5810 5811
CONECT 5810 5809
CONECT 5811 5806 5809 5812
CONECT 5812 5811 5813 5819
CONECT 5813 5812 5814 5815
CONECT 5814 5813
CONECT 5815 5813 5816
CONECT 5816 5815 5817 5818
CONECT 5817 5816
CONECT 5818 5816 5819 5820
CONECT 5819 5812 5818
CONECT 5820 5818
CONECT 5821 5808
CONECT 5898 5931
CONECT 5913 5914 5919 5922
CONECT 5914 5913 5915 5920
CONECT 5915 5914 5916
CONECT 5916 5915 5917 5921
CONECT 5917 5916 5918 5919
CONECT 5918 5917
CONECT 5919 5913 5917
CONECT 5920 5914
CONECT 5921 5916
CONECT 5922 5913 5923 5928
CONECT 5923 5922 5924 5925
CONECT 5924 5923
CONECT 5925 5923 5926 5927
CONECT 5926 5925 5928 5929
CONECT 5927 5925 5951
CONECT 5928 5922 5926
CONECT 5929 5926 5930
CONECT 5930 5929 5931
CONECT 5931 5898 5930 5932 5933
CONECT 5932 5931
CONECT 5933 5931
CONECT 5934 5935 5939
CONECT 5935 5934 5936 5940
CONECT 5936 5935 5937
CONECT 5937 5936 5938 5941
CONECT 5938 5937 5939 5942
CONECT 5939 5934 5938
CONECT 5940 5935
CONECT 5941 5937
CONECT 5942 5938 5943 5948
CONECT 5943 5942 5944 5945
CONECT 5944 5943
CONECT 5945 5943 5946 5947
CONECT 5946 5945 5948 5949
CONECT 5947 5945 5954
CONECT 5948 5942 5946
CONECT 5949 5946 5950
CONECT 5950 5949 5951
CONECT 5951 5927 5950 5952 5953
CONECT 5952 5951
```

```
CONECT 5953 5951
CONECT 5954 5947
MASTER      403   0  34   0   0   0   0   6 8882  25 817 343
END
```

What is claimed is:

1. A method of identifying a compound that binds to a bacterial 70S ribosome or portion thereof, comprising: designing a compound based upon a three-dimensional structure of the bacterial 70S ribosome said three-dimensional structure defined by structure coordinates within Appendix I; providing said compound; contacting said compound with the bacterial 70S ribosome or portion thereof; and determining whether said compound binds to the bacterial 70S ribosome or portion thereof.

2. The method of claim 1, wherein a subset of the structure coordinates within Appendix 1 is used for said designing step.

3. The method of claim 1, wherein said portion is a bacterial ribosome 30S subunit.

4. The method of claim 1, wherein said portion is a bacterial ribosome 50S subunit.

5. The method of claim 1, wherein said compound is designed de novo.

6. The method of claim 1, wherein said compound is designed from a known compound.

7. The method of claim 6 wherein said known compound is selected from the group consisting of antibiotics, initiation factors, and elongation factors.

8. The method of claim 7, wherein said antibiotics are selected from die group consisting of paromoniycin, puromycin, streptomycin, neomycin, thiostrepton, micrococcin, fusidic acid, kirromycin, chloramphenicol, clindamycin, erythromycin, clarithromycin, and roxithromycin.

9. The method of claim 7, wherein said initiation factors are selected from the group consisting of IF1, IF2, and IF3.

10. The method of claim 7, wherein said elongation factors are selected from the group consisting of EF-Tu, and EF-G.

11. The method of claim 1, thrther comprising the step of determining whether the designed compound inhibits protein translation.

12. The method of claim 1, further comprising the step of detennining whether the designed compound alters protein translation fidelity.

13. The method of claim 1, further comprising the step of determining whether the designed compound affects association between a 30S and a 50S ribosome subunit.

14. The method of claim 1, further comprising the step of determining whether the designed compound affects binding of a tRNA to a ribosomal tRNA binding site.

15. The method of claim 1, further comprising the step of determining whether the designed compound affects binding of an mRNA to a ribosomal mRNA binding site.

16. The method of claim 1, further comprising the step of determining whether the designed compound affects binding of IF3 to a ribosomal IF3 binding site.

17. The method of claim 1, further comprising the step of determining whether the designed compound affects binding of EF-Tu to a ribosomal EF-Tu ribosomal binding site.

18. The method of claim 1, further comprising the step of determining whether the designed compound affects binding of EF-G to a ribosomal EF-G ribosomal binding site.

19. A method of identifying a compound that binds to a bacterial 70S ribosome or portion thereof, comprising: obtaining a set of structure coordinates defining the three-dimensional structure of a crystal of a bacterial 70S ribosome that diffracts X-rays for the determination of the structure coordinates of the bacterial 70S ribosome to a resolution of at least 5.5 Angstroms, wherein said bacterial 70S ribosome comprises a 23S rRNA having residues 1–2916 of SEQ ID NO: 23, a 5S rRNA having residues 1–123 of SEQ ID NO: 24, and a 16S rRNA having residues 1–1522 of SEQ ID NO: 45, and wherein said crystal has a space group of I422 with unit cell dimensions of a=b=507.2 Angstroms, and c=803.7 Angstroms; designing a compound based upon the structure coordinates obtained from said crystal; providing said compound; contacting said compound with the 70S ribosome or portion thereof; and determining whether said compound binds to the bacterial 70S ribosome or portion thereof.

20. The method of claim 19, wherein a subset of the structure coordinates obtained from said crystal is used for said designing step.

21. The method of claim 19, wherein said portion is a bacterial ribosome 30S subunit.

22. The method of claim 19, wherein said portion is a bacterial ribosome 50S subunit.

23. The method of claim 19, wherein said compound is designed de novo.

24. The method of claim 19, wherein said compound is designed from a known compound.

25. The method of claim 24 wherein said known compound is selected from the group consisting of antibiotics, initiation factors, and elongation factors.

26. The method of claim 25, wherein said antibiotics are selected from the group consisting of paromomycin, puromycin, streptomycin, neomycin, thiostrepton, micrococoin, fusidic acid, kirromycin, chloramphenicol, clindamycin, erythromycin, clarithromycin, and roxithromycin.

27. The method of claim 25, wherein said initiation factors are selected from the group consisting of IF1, IF2, and IF3.

28. The method of claim 25, wherein said elongation factors are selected from the group consisting of EF-Tu and EF-G.

29. The method of claim 19, further comprising the step of determining whether the designed compound inhibits protein translation.

30. The method of claim 19, further comprising the step of determining whether the designed compound alters protein translation fidelity.

31. The method of claim 19, further comprising the step of determining whether the designed compound affects association between a 30S and a 50S ribosome subunit.

32. The method of claim 19, further comprising the step of determining whether the designed compound affects binding of a tRNA to a ribosomal tRNA binding site.

33. The method of claim 19, further comprising the step of determining whether the designed compound affects binding of an mRNA to a ribosomal mRNA binding site.

34. The method of claim 19, further comprising the step of determining whether the designed compound affects binding of IF3 to a ribosomal IF3 binding site.

35. The method of claim 19, further comprising the step of determining whether the designed compound affects binding of EF-Tu to a ribosomal EF-Tu ribosomal binding site.

36. The method of claim 19, further comprising the step of determining whether the designed compound affects binding of EF-G to a ribosomal EF-G ribosomal binding site.

37. The method of claim 1, wherein said compound is designed to form a non-covalent bond with a residue corresponding to a residue within the ranges of residues selected from the group consisting of
S13 (SEQ ID NO: 36) 92–94, 2–11,
S15 (SEQ ID NO: 38) 40–44, 85–89,
L2 (SEQ ID NO: 2) 162–164, 172–174, 177–178, 198–202,
L5 (SEQ ID NO: 5) 134–153,
L14 (SEQ ID NO: 12) 116–119,
L19 (SEQ ID NO: 16) 44,
16S tRNA (SEQ ID NO: 45) 1408–1410, 1494, 1495, 784, 785, 794, 1516–1519, 770, 771, 900, 901, 763, 764, 698, 702, 712, 713, 773–776, 345–347,
23S rRNA (SEQ ID NO: 23) 886–888, 1913–1914, 1918, 1836–1836, 1919, 1920, 1922, 1932, 1832–1833, 1947–1948, 1960–1961, 1768–1769,44–49, 1689–1690, 1989, 1689, 1690, 1702–1705, 1848–1849, and 1896.
wherein said 16S tRNA and 23S rRNA residue numbers are according to *E. coli* numbering.

38. The method of claim 37, wherein said residue, is within the ranges of residues selected from the group consisting of
S13 (SEQ ID NO: 36) 92–94, 2–11,
L5 (SEQ ID NO: 5) 134–153,
16S rRNA (SEQ ID NO: 45) 1408–1410, 1494, 1495,
23S rRNA (SEQ ID NO: 23) 886–888, 1913–1914, and 1918,
wherein said 16S rRNA and 23S rRNA residue numbers are according to *E. coli* numbering.

39. The method of claim 1, wherein said compound is designed to form a non-covalent bond with a residue corresponding to a residue within the ranges of residues selected from the group consisting of
16S rRNA (SEQ ID NO: 45) 1229, 1338, 1339, 790, 966, 926, 1498, 1400, 530, 1045, 955, 1493, 1339–1340, 1382, 937, 788–789, 693–695,
S9 (SEQ ID NO: 32) 128,
L5 (SEQ ID NO: 5) 55–66, S13 (SEQ ID NO: 36) 120–122,
S12 (SEQ ID NO: 35) 46–48,
L16 (SEQ ID NO: 14) 27, 30, S7 (SEQ ID NO: 30) 76–87, 140–152,
L1 (SEQ ID NO: 1) 124–128, 52–54, 165–169,
23S rRNA (SEQ ID NO: 23) 1908, 1909, 1922, 1923, 2255–2256, 2252, 2602, 2585, 1913–1915, 881–883, 898, 899, 2470–2472,2482–2484, 1942, 1943, 2452, 2494,2553,2112–2113,2116, 2117, 1850–1353, 1892, 2235, 2433, 2434, and 199, wherein said 16S rRNA and 23S rRNA residue numbers are according to *E. coli* numbering.

40. The method of claim 1, wherein said compound is designed to form a non-covalent bond with a residue corresponding to a residue within the ranges of residues selected from the group consisting of S3 (SEQ ID NO: 26) 127–132, 156–163,
S4 (SEQ ID NO: 27) 47–52,
S5 (SEQ ID NO: 28) 9–30, 46–56,
16S rRNA (SEQ ID NO: 45), 13–17, 528–532, 1054–1056, 1194–1197, and 1198,
wherein said 16S rRNA residue numbers are according to *E. coli* numbering.

41. The method of claim 1, wherein said compound is designed to form a non-covalent bond with a residue corresponding to a residue within the ranges of residues selected from the group consisting of 16S rRNA (SEQ ID NO: 45) 685–705, 783–795, 799–802, and 803,
wherein said 16S rRNA residue numbers are according to *E. coli* numbering.

42. The method of claim 1, wherein said compound is designed to fbrin a non-covalent bond with a residue corresponding to a residue within the ranges of residues selected from the group consisting of L1 (SEQ ID NO: 10) 20–36,
16S rRNA (SEQ ID NO: 45) 54–57, 357–361, and
23S rRNA (SEQ ID NO: 23) 2651–2664, and 2665,
wherein said 16S rRNA and said 23S rRNA residue numbers are according to *E. coli* numbering.

43. The method of claim 1, wherein said compound is designed to form a non-covalent bond with a residue corresponding to a residue within the ranges of residues selected from the group consisting of L11 (SEQ ID NO: 10)20–36,
16S rRNA (SEQ ID NO: 45) 54–57, 340–345, 357–361, and
23S rRNA (SEQ ID NO: 23)1065–1069, 1094–1097, 2651–2664, and 2665,
wherein said 16S rRNA and said 23S rRNA residue numbers are according to *E. coli* numbering.

44. The method of claim 1, wherein said compound is designed to form a non-covalent bond with a residue lining a Shine Dalgarno helix binding pocket, said residue corresponding to a residue within the ranges of residues selected from the group consisting of S11 (SEQ ID NO: 34) 85–90, 112–129, 22–27,
N8 (SEQ ID NO: 41) 1–24, and
16S rRNA (SEQ ID NO: 45) 927–93 1, 1388–1393, 1526–1529, 1505–1508, 719–723, and 724,
wherein said 165 rRNA and residue numbers are according to *E. coli* numbering.

\* \* \* \* \*

UNITED STATES PATENT AND TRADEMARK OFFICE
CERTIFICATE OF CORRECTION

PATENT NO.        : 7,133,783 B2
APPLICATION NO.   : 10/013379
DATED             : November 7, 2006
INVENTOR(S)       : Harry Noller et al.

It is certified that error appears in the above-identified patent and that said Letters Patent is hereby corrected as shown below:

Column 868, Line 51, replace "die" with --the--.

Column 868, Line 61, replace "thrther" with --further--.

Column 868, Line 66, replace "detennining" with --determining--.

Column 869, Line 53, replace "micrococoin" with --micrococcin--.

Column 870, Line 32, replace "tRNA" with --rRNA--.

Column 870, Line 40, replace "tRNA" with --rRNA--.

Column 871, Line 69, replace "1850-1353" with --1850-1853--.

Column 871, Line 26, replace "fbrin" with --form--.

Column 871, Line 30, replace "L1" with --L11--.

Column 872, Line 32, replace "165" with --16S--.

Signed and Sealed this

Fifth Day of August, 2008

JON W. DUDAS
*Director of the United States Patent and Trademark Office*